(12) United States Patent
Liu et al.

(10) Patent No.: US 11,214,780 B2
(45) Date of Patent: Jan. 4, 2022

(54) NUCLEOBASE EDITORS AND USES THEREOF

(71) Applicant: President and Fellows of Harvard College, Cambridge, MA (US)

(72) Inventors: David R. Liu, Lexington, MA (US); Alexis Christine Komor, Pasadena, CA (US); Holly A. Rees, Cambridge, MA (US); Yongjoo Kim, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 276 days.

(21) Appl. No.: 15/960,171

(22) Filed: Apr. 23, 2018

(65) Prior Publication Data

US 2018/0312825 A1   Nov. 1, 2018

Related U.S. Application Data

(63) Continuation of application No. PCT/US2016/058344, filed on Oct. 22, 2016, and a continuation of application No. 15/331,852, filed on Oct. 22, 2016, now Pat. No. 10,167,457.

(60) Provisional application No. 62/408,686, filed on Oct. 14, 2016, provisional application No. 62/398,490, filed on Sep. 22, 2016, provisional application No. 62/370,700, filed on Aug. 3, 2016, provisional application No. 62/357,332, filed on Jun. 30, 2016, provisional application No. 62/357,352, filed on Jun. 30, 2016, provisional application No. 62/322,178, filed on Apr. 13, 2016, provisional application No. 62/311,763, filed on Mar. 22, 2016, provisional application No. 62/279,346, filed on Jan. 15, 2016, provisional application No. 62/245,828, filed on Oct. 23, 2015.

(51) Int. Cl.
| | |
|---|---|
| *C12N 15/10* | (2006.01) |
| *C12N 9/78* | (2006.01) |
| *C12N 9/22* | (2006.01) |
| *C12N 15/90* | (2006.01) |
| *C12N 9/24* | (2006.01) |
| *C07K 14/32* | (2006.01) |
| *C12N 15/11* | (2006.01) |

(52) U.S. Cl.
CPC .............. *C12N 9/22* (2013.01); *C07K 14/32* (2013.01); *C12N 9/2497* (2013.01); *C12N 9/78* (2013.01); *C12N 15/11* (2013.01); *C12N 15/907* (2013.01); *C12Y 305/04005* (2013.01); *C07K 2319/00* (2013.01); *C07K 2319/09* (2013.01); *C07K 2319/80* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | |
|---|---|---|
| 4,182,449 A | 1/1980 | Kozlow |
| 4,186,183 A | 1/1980 | Steck et al. |
| 4,217,344 A | 8/1980 | Vanlerberghe et al. |
| 4,235,871 A | 11/1980 | Papahadjopoulos et al. |
| 4,261,975 A | 4/1981 | Fullerton et al. |
| 4,485,054 A | 11/1984 | Mezei et al. |
| 4,501,728 A | 2/1985 | Geho et al. |
| 4,663,290 A | 5/1987 | Weis et al. |
| 4,737,323 A | 4/1988 | Martin et al. |
| 4,774,085 A | 9/1988 | Fidler |
| 4,797,368 A | 1/1989 | Carter et al. |
| 4,837,028 A | 6/1989 | Allen |
| 4,873,316 A | 10/1989 | Meade et al. |
| 4,880,635 A | 11/1989 | Janoff et al. |
| 4,889,818 A | 12/1989 | Gelfand et al. |
| 4,897,355 A | 1/1990 | Eppstein et al. |
| 4,906,477 A | 3/1990 | Kurono et al. |
| 4,911,928 A | 3/1990 | Wallach |
| 4,917,951 A | 4/1990 | Wallach |
| 4,920,016 A | 4/1990 | Allen et al. |
| 4,921,757 A | 5/1990 | Wheatley et al. |
| 4,946,787 A | 8/1990 | Eppstein et al. |
| 4,965,185 A | 10/1990 | Grischenko et al. |
| 5,017,492 A | 5/1991 | Kotewicz et al. |
| 5,047,342 A | 9/1991 | Chatterjee |
| 5,049,386 A | 9/1991 | Eppstein et al. |
| 5,079,352 A | 1/1992 | Gelfand et al. |
| 5,139,941 A | 8/1992 | Muzyczka et al. |
| 5,173,414 A | 12/1992 | Lebkowski et al. |
| 5,223,409 A | 6/1993 | Ladner et al. |
| 5,244,797 A | 9/1993 | Kotewicz et al. |
| 5,270,179 A | 12/1993 | Chatterjee |

(Continued)

FOREIGN PATENT DOCUMENTS

| | | |
|---|---|---|
| AU | 2012244264 A1 | 11/2012 |
| AU | 2012354062 A1 | 7/2014 |

(Continued)

OTHER PUBLICATIONS

Wijesinghe et al. (Nucleic Acids Research, 2012, 40:9206-9217) (Year: 2012).*

(Continued)

*Primary Examiner* — Mark Halvorson
(74) *Attorney, Agent, or Firm* — Wolf, Greenfield & Sacks, P.C.

(57) ABSTRACT

Some aspects of this disclosure provide strategies, systems, reagents, methods, and kits that are useful for the targeted editing of nucleic acids, including editing a single site within the genome of a cell or subject, e.g., within the human genome. In some embodiments, fusion proteins of Cas9 and nucleic acid editing proteins or protein domains, e.g., deaminase domains, are provided. In some embodiments, methods for targeted nucleic acid editing are provided. In some embodiments, reagents and kits for the generation of targeted nucleic acid editing proteins, e.g., fusion proteins of Cas9 and nucleic acid editing proteins or domains, are provided.

23 Claims, 138 Drawing Sheets

Specification includes a Sequence Listing.

(56) References Cited

U.S. PATENT DOCUMENTS

| | | |
|---|---|---|
| 5,374,553 A | 12/1994 | Gelfand et al. |
| 5,405,776 A | 4/1995 | Kotewicz et al. |
| 5,436,149 A | 7/1995 | Barnes |
| 5,449,639 A | 9/1995 | Wei et al. |
| 5,496,714 A | 3/1996 | Comb et al. |
| 5,512,462 A | 4/1996 | Cheng |
| 5,580,737 A | 12/1996 | Polisky et al. |
| 5,614,365 A | 3/1997 | Tabor et al. |
| 5,658,727 A | 8/1997 | Barbas et al. |
| 5,668,005 A | 9/1997 | Kotewicz et al. |
| 5,677,152 A | 10/1997 | Birch et al. |
| 5,767,099 A | 6/1998 | Harris et al. |
| 5,780,053 A | 7/1998 | Ashley et al. |
| 5,830,430 A | 11/1998 | Unger et al. |
| 5,834,247 A | 11/1998 | Comb et al. |
| 5,835,699 A | 11/1998 | Kimura |
| 5,851,548 A | 12/1998 | Dattagupta et al. |
| 5,855,910 A | 1/1999 | Ashley et al. |
| 5,962,313 A | 10/1999 | Podsakoff et al. |
| 5,981,182 A | 11/1999 | Jacobs, Jr. et al. |
| 6,057,153 A | 5/2000 | George et al. |
| 6,063,608 A | 5/2000 | Kotewicz et al. |
| 6,156,509 A | 12/2000 | Schellenberger |
| 6,183,998 B1 | 2/2001 | Ivanov et al. |
| 6,429,298 B1 | 8/2002 | Ellington et al. |
| 6,453,242 B1 | 9/2002 | Eisenberg et al. |
| 6,479,264 B1 | 11/2002 | Louwrier |
| 6,503,717 B2 | 1/2003 | Case et al. |
| 6,534,261 B1 | 3/2003 | Cox, III et al. |
| 6,589,768 B1 | 7/2003 | Kotewicz et al. |
| 6,599,692 B1 | 7/2003 | Case et al. |
| 6,607,882 B1 | 8/2003 | Cox, III et al. |
| 6,610,522 B1 | 8/2003 | Kotewicz et al. |
| 6,689,558 B2 | 2/2004 | Case |
| 6,824,978 B1 | 11/2004 | Cox, III et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,078,208 B2 | 7/2006 | Smith et al. |
| 7,163,824 B2 | 1/2007 | Cox, III et al. |
| 7,479,573 B2 | 1/2009 | Chu et al. |
| 7,595,179 B2 | 9/2009 | Chen et al. |
| 7,670,807 B2 | 3/2010 | Lampson et al. |
| 7,794,931 B2 | 9/2010 | Breaker et al. |
| 7,919,277 B2 | 4/2011 | Russell et al. |
| 7,993,672 B2 | 8/2011 | Huang et al. |
| 8,067,556 B2 | 11/2011 | Hogrefe et al. |
| 8,361,725 B2 | 1/2013 | Russell et al. |
| 8,394,604 B2 | 3/2013 | Liu et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,492,082 B2 | 7/2013 | De Franciscis et al. |
| 8,546,553 B2 | 10/2013 | Terns et al. |
| 8,569,256 B2 | 10/2013 | Heyes et al. |
| 8,586,363 B2 | 11/2013 | Voytas et al. |
| 8,680,069 B2 | 3/2014 | de Fougerolles et al. |
| 8,691,750 B2 | 4/2014 | Constien et al. |
| 8,697,359 B1 | 4/2014 | Zhang |
| 8,697,853 B2 | 4/2014 | Voytas et al. |
| 8,709,466 B2 | 4/2014 | Coady et al. |
| 8,728,526 B2 | 5/2014 | Heller |
| 8,748,667 B2 | 6/2014 | Budzik et al. |
| 8,758,810 B2 | 6/2014 | Okada et al. |
| 8,759,103 B2 | 6/2014 | Kim et al. |
| 8,759,104 B2 | 6/2014 | Unciti-Broceta et al. |
| 8,771,728 B2 | 7/2014 | Huang et al. |
| 8,790,664 B2 | 7/2014 | Pitard et al. |
| 8,795,965 B2 | 8/2014 | Zhang |
| 8,822,663 B2 | 9/2014 | Schrum et al. |
| 8,846,578 B2 | 9/2014 | McCray et al. |
| 8,900,814 B2 | 12/2014 | Yasukawa et al. |
| 8,993,233 B2 | 3/2015 | Zhang et al. |
| 8,999,641 B2 | 4/2015 | Zhang et al. |
| 9,023,594 B2 | 5/2015 | Liu et al. |
| 9,068,179 B1 | 6/2015 | Liu et al. |
| 9,163,284 B2 | 10/2015 | Liu et al. |
| 9,181,535 B2 | 11/2015 | Liu et al. |
| 9,228,207 B2 | 1/2016 | Liu et al. |
| 9,234,213 B2 | 1/2016 | Wu |
| 9,267,127 B2 | 2/2016 | Liu et al. |
| 9,322,006 B2 | 4/2016 | Liu et al. |
| 9,322,037 B2 | 4/2016 | Liu et al. |
| 9,340,799 B2 | 5/2016 | Liu et al. |
| 9,340,800 B2 | 5/2016 | Liu et al. |
| 9,359,599 B2 | 6/2016 | Liu et al. |
| 9,388,430 B2 | 7/2016 | Liu et al. |
| 9,394,537 B2 | 7/2016 | Liu et al. |
| 9,458,484 B2 | 10/2016 | Ma et al. |
| 9,512,446 B1 | 12/2016 | Joung et al. |
| 9,526,724 B2 | 12/2016 | Oshiack et al. |
| 9,526,784 B2 | 12/2016 | Liu et al. |
| 9,534,210 B2 | 1/2017 | Park et al. |
| 9,580,698 B1 | 2/2017 | Xu et al. |
| 9,637,739 B2 | 5/2017 | Šikšnys et al. |
| 9,737,604 B2 | 8/2017 | Liu et al. |
| 9,738,693 B2 | 8/2017 | Telford et al. |
| 9,771,574 B2 | 9/2017 | Liu et al. |
| 9,783,791 B2 | 10/2017 | Hogrefe et al. |
| 9,816,093 B1 | 11/2017 | Donohoue et al. |
| 9,840,538 B2 | 12/2017 | Telford et al. |
| 9,840,690 B2 | 12/2017 | Karli et al. |
| 9,840,699 B2 | 12/2017 | Liu et al. |
| 9,840,702 B2 | 12/2017 | Collingwood et al. |
| 9,850,521 B2 | 12/2017 | Braman et al. |
| 9,873,907 B2 | 1/2018 | Zeiner et al. |
| 9,879,270 B2 | 1/2018 | Hittinger et al. |
| 9,932,567 B1 | 4/2018 | Xu et al. |
| 9,938,288 B1 | 4/2018 | Kishi et al. |
| 9,944,933 B2 | 4/2018 | Storici et al. |
| 9,982,279 B1 | 5/2018 | Gill et al. |
| 9,999,671 B2 | 6/2018 | Liu et al. |
| 10,059,940 B2 | 8/2018 | Zhong |
| 10,077,453 B2 | 9/2018 | Liu et al. |
| 10,113,163 B2 | 10/2018 | Liu et al. |
| 10,150,955 B2 | 12/2018 | Lambowitz et al. |
| 10,167,457 B2 | 1/2019 | Liu et al. |
| 10,179,911 B2 | 1/2019 | Liu et al. |
| 10,189,831 B2 | 1/2019 | Arrington et al. |
| 10,202,658 B2 | 2/2019 | Parkin et al. |
| 10,227,581 B2 | 3/2019 | Liu et al. |
| 10,323,236 B2 | 6/2019 | Liu et al. |
| 10,336,997 B2 | 7/2019 | Liu et al. |
| 10,358,670 B2 | 7/2019 | Janulaitis et al. |
| 10,392,674 B2 | 8/2019 | Liu et al. |
| 10,407,697 B2 | 9/2019 | Doudna et al. |
| 10,465,176 B2 | 11/2019 | Liu et al. |
| 10,508,298 B2 | 12/2019 | Liu et al. |
| 10,597,679 B2 | 3/2020 | Liu et al. |
| 10,612,011 B2 | 4/2020 | Liu et al. |
| 10,682,410 B2 | 6/2020 | Liu et al. |
| 10,704,062 B2 | 7/2020 | Liu et al. |
| 10,745,677 B2 | 8/2020 | Maianti et al. |
| 10,858,639 B2 | 12/2020 | Liu et al. |
| 10,912,833 B2 | 2/2021 | Liu et al. |
| 10,947,530 B2 | 3/2021 | Liu et al. |
| 10,954,548 B2 | 3/2021 | Liu et al. |
| 2003/0082575 A1 | 5/2003 | Schultz et al. |
| 2003/0087817 A1 | 5/2003 | Cox et al. |
| 2003/0096337 A1 | 5/2003 | Hillman et al. |
| 2003/0108885 A1 | 6/2003 | Schultz et al. |
| 2003/0119764 A1 | 6/2003 | Loeb et al. |
| 2003/0167533 A1 | 9/2003 | Yadav et al. |
| 2003/0203480 A1 | 10/2003 | Kovesdi et al. |
| 2004/0003420 A1 | 1/2004 | Kuhn et al. |
| 2004/0115184 A1 | 6/2004 | Smith et al. |
| 2004/0203109 A1 | 10/2004 | Lal et al. |
| 2005/0136429 A1 | 6/2005 | Guarente et al. |
| 2005/0222030 A1 | 10/2005 | Allison |
| 2006/0088864 A1 | 4/2006 | Smolke et al. |
| 2006/0104984 A1 | 5/2006 | Littlefield et al. |
| 2006/0246568 A1 | 11/2006 | Honjo et al. |
| 2007/0264692 A1 | 11/2007 | Liu et al. |
| 2007/0269817 A1 | 11/2007 | Shapero |

(56) References Cited

U.S. PATENT DOCUMENTS

| | | |
|---|---|---|
| 2008/0051317 A1 | 2/2008 | Church et al. |
| 2008/0124725 A1 | 5/2008 | Barrangou et al. |
| 2008/0182254 A1 | 7/2008 | Hall et al. |
| 2008/0220502 A1 | 9/2008 | Schellenberger et al. |
| 2009/0130718 A1 | 5/2009 | Short |
| 2009/0215878 A1 | 8/2009 | Tan et al. |
| 2009/0234109 A1 | 9/2009 | Han et al. |
| 2010/0076057 A1 | 3/2010 | Sontheimer et al. |
| 2010/0093617 A1 | 4/2010 | Barrangou et al. |
| 2010/0104690 A1 | 4/2010 | Barrangou et al. |
| 2010/0273857 A1 | 10/2010 | Thakker et al. |
| 2010/0305197 A1 | 12/2010 | Che |
| 2010/0316643 A1 | 12/2010 | Eckert et al. |
| 2011/0016540 A1 | 1/2011 | Weinstein et al. |
| 2011/0059160 A1 | 3/2011 | Essner et al. |
| 2011/0059502 A1 | 3/2011 | Chalasani |
| 2011/0104787 A1 | 5/2011 | Church et al. |
| 2011/0177495 A1 | 7/2011 | Liu et al. |
| 2011/0189776 A1 | 8/2011 | Terns et al. |
| 2011/0217739 A1 | 9/2011 | Terns et al. |
| 2011/0301073 A1 | 12/2011 | Gregory et al. |
| 2012/0129759 A1 | 5/2012 | Liu et al. |
| 2012/0141523 A1 | 6/2012 | Castado et al. |
| 2012/0244601 A1 | 9/2012 | Bertozzi et al. |
| 2012/0270273 A1 | 10/2012 | Zhang et al. |
| 2013/0059931 A1 | 3/2013 | Petersen-Mahrt et al. |
| 2013/0117869 A1 | 5/2013 | Duchateau et al. |
| 2013/0130248 A1 | 5/2013 | Haurwitz et al. |
| 2013/0158245 A1 | 6/2013 | Russell et al. |
| 2013/0165389 A1 | 6/2013 | Schellenberger et al. |
| 2013/0309720 A1 | 11/2013 | Schultz et al. |
| 2013/0344117 A1 | 12/2013 | Mirosevich et al. |
| 2013/0345064 A1 | 12/2013 | Liu et al. |
| 2014/0004280 A1 | 1/2014 | Loomis |
| 2014/0005269 A1 | 1/2014 | Ngwuluka et al. |
| 2014/0017214 A1 | 1/2014 | Cost |
| 2014/0018404 A1 | 1/2014 | Chen et al. |
| 2014/0044793 A1 | 2/2014 | Goll et al. |
| 2014/0065711 A1 | 3/2014 | Liu et al. |
| 2014/0068797 A1 | 3/2014 | Doudna et al. |
| 2014/0127752 A1 | 5/2014 | Zhou et al. |
| 2014/0141094 A1 | 5/2014 | Smyth et al. |
| 2014/0141487 A1 | 5/2014 | Feldman et al. |
| 2014/0179770 A1 | 6/2014 | Zhang et al. |
| 2014/0186843 A1 | 7/2014 | Zhang et al. |
| 2014/0186958 A1 | 7/2014 | Zhang et al. |
| 2014/0201858 A1 | 7/2014 | Ostertag et al. |
| 2014/0234289 A1 | 8/2014 | Liu et al. |
| 2014/0248702 A1 | 9/2014 | Zhang et al. |
| 2014/0273037 A1 | 9/2014 | Wu |
| 2014/0273226 A1 | 9/2014 | Wu |
| 2014/0273230 A1 | 9/2014 | Chen et al. |
| 2014/0295556 A1 | 10/2014 | Joung et al. |
| 2014/0295557 A1 | 10/2014 | Joung et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0349400 A1 | 11/2014 | Jakimo et al. |
| 2014/0356867 A1 | 12/2014 | Peter et al. |
| 2014/0356956 A1 | 12/2014 | Church et al. |
| 2014/0356958 A1 | 12/2014 | Mali et al. |
| 2014/0356959 A1 | 12/2014 | Church et al. |
| 2014/0357523 A1 | 12/2014 | Zeiner et al. |
| 2014/0377868 A1 | 12/2014 | Joung et al. |
| 2015/0010526 A1 | 1/2015 | Liu et al. |
| 2015/0031089 A1 | 1/2015 | Lindstrom |
| 2015/0031132 A1 | 1/2015 | Church et al. |
| 2015/0031133 A1 | 1/2015 | Church et al. |
| 2015/0044191 A1 | 2/2015 | Liu et al. |
| 2015/0044192 A1 | 2/2015 | Liu et al. |
| 2015/0044772 A1 | 2/2015 | Zhao |
| 2015/0050699 A1 | 2/2015 | Siksnys et al. |
| 2015/0056177 A1 | 2/2015 | Liu et al. |
| 2015/0056629 A1 | 2/2015 | Guthrie-Honea |
| 2015/0064138 A1 | 3/2015 | Lu et al. |
| 2015/0064789 A1 | 3/2015 | Paschon et al. |
| 2015/0071898 A1 | 3/2015 | Liu et al. |
| 2015/0071899 A1 | 3/2015 | Liu et al. |
| 2015/0071900 A1 | 3/2015 | Liu et al. |
| 2015/0071901 A1 | 3/2015 | Liu et al. |
| 2015/0071902 A1 | 3/2015 | Liu et al. |
| 2015/0071903 A1 | 3/2015 | Liu et al. |
| 2015/0071906 A1 | 3/2015 | Liu et al. |
| 2015/0079680 A1 | 3/2015 | Bradley et al. |
| 2015/0079681 A1 | 3/2015 | Zhang |
| 2015/0098954 A1 | 4/2015 | Hyde et al. |
| 2015/0118216 A1 | 4/2015 | Liu et al. |
| 2015/0132269 A1 | 5/2015 | Orkin et al. |
| 2015/0140664 A1 | 5/2015 | Byrne et al. |
| 2015/0159172 A1 | 6/2015 | Miller et al. |
| 2015/0165054 A1 | 6/2015 | Liu et al. |
| 2015/0166980 A1 | 6/2015 | Liu et al. |
| 2015/0166981 A1 | 6/2015 | Liu et al. |
| 2015/0166982 A1 | 6/2015 | Liu et al. |
| 2015/0166984 A1 | 6/2015 | Liu et al. |
| 2015/0166985 A1 | 6/2015 | Liu et al. |
| 2015/0191744 A1 | 7/2015 | Wolfe et al. |
| 2015/0197759 A1 | 7/2015 | Xu et al. |
| 2015/0211058 A1 | 7/2015 | Carstens |
| 2015/0218573 A1 | 8/2015 | Loque et al. |
| 2015/0225773 A1 | 8/2015 | Farmer et al. |
| 2015/0252358 A1 | 9/2015 | Maeder et al. |
| 2015/0275202 A1 | 10/2015 | Liu et al. |
| 2015/0307889 A1 | 10/2015 | Petolino et al. |
| 2015/0315252 A1 | 11/2015 | Haugwitz et al. |
| 2016/0015682 A2 | 1/2016 | Cawthorne et al. |
| 2016/0017393 A1 | 1/2016 | Jacobson et al. |
| 2016/0017396 A1 | 1/2016 | Cann et al. |
| 2016/0032292 A1 | 2/2016 | Storici et al. |
| 2016/0032353 A1 | 2/2016 | Braman et al. |
| 2016/0040155 A1 | 2/2016 | Maizels et al. |
| 2016/0046952 A1 | 2/2016 | Hittinger et al. |
| 2016/0046961 A1 | 2/2016 | Jinek et al. |
| 2016/0046962 A1 | 2/2016 | May et al. |
| 2016/0053272 A1 | 2/2016 | Wurtzel et al. |
| 2016/0053304 A1 | 2/2016 | Wurtzel et al. |
| 2016/0074535 A1 | 3/2016 | Ranganathan et al. |
| 2016/0076093 A1 | 3/2016 | Shendure et al. |
| 2016/0090603 A1 | 3/2016 | Carnes et al. |
| 2016/0090622 A1 | 3/2016 | Liu et al. |
| 2016/0115488 A1 | 4/2016 | Zhang et al. |
| 2016/0138046 A1 | 5/2016 | Wu |
| 2016/0186214 A1 | 6/2016 | Brouns et al. |
| 2016/0200779 A1 | 7/2016 | Liu et al. |
| 2016/0201040 A1 | 7/2016 | Liu et al. |
| 2016/0201089 A1 | 7/2016 | Gersbach et al. |
| 2016/0206566 A1 | 7/2016 | Lu et al. |
| 2016/0208243 A1 | 7/2016 | Zhang et al. |
| 2016/0208288 A1 | 7/2016 | Liu et al. |
| 2016/0215275 A1 | 7/2016 | Zhong |
| 2016/0215276 A1 | 7/2016 | Liu et al. |
| 2016/0215300 A1 | 7/2016 | May et al. |
| 2016/0244784 A1 | 8/2016 | Jacobson et al. |
| 2016/0244829 A1 | 8/2016 | Bang et al. |
| 2016/0264934 A1 | 9/2016 | Giallourakis et al. |
| 2016/0272965 A1 | 9/2016 | Zhang et al. |
| 2016/0281072 A1 | 9/2016 | Zhang |
| 2016/0298136 A1 | 10/2016 | Chen et al. |
| 2016/0304846 A1 | 10/2016 | Liu et al. |
| 2016/0304855 A1 | 10/2016 | Stark et al. |
| 2016/0312304 A1 | 10/2016 | Sorrentino et al. |
| 2016/0319262 A1 | 11/2016 | Doudna et al. |
| 2016/0333389 A1 | 11/2016 | Liu et al. |
| 2016/0340622 A1 | 11/2016 | Abdou |
| 2016/0340662 A1 | 11/2016 | Zhang et al. |
| 2016/0345578 A1 | 12/2016 | Barrangou et al. |
| 2016/0346360 A1 | 12/2016 | Quake et al. |
| 2016/0346361 A1 | 12/2016 | Quake et al. |
| 2016/0346362 A1 | 12/2016 | Quake et al. |
| 2016/0348074 A1 | 12/2016 | Quake et al. |
| 2016/0348096 A1 | 12/2016 | Liu et al. |
| 2016/0350476 A1 | 12/2016 | Quake et al. |
| 2016/0355796 A1 | 12/2016 | Davidson et al. |
| 2016/0369262 A1 | 12/2016 | Reik et al. |

(56) References Cited

U.S. PATENT DOCUMENTS

| | | |
|---|---|---|
| 2017/0009224 A1 | 1/2017 | Liu et al. |
| 2017/0009242 A1 | 1/2017 | McKinley et al. |
| 2017/0014449 A1 | 1/2017 | Bangera et al. |
| 2017/0020922 A1 | 1/2017 | Wagner et al. |
| 2017/0037432 A1 | 2/2017 | Donohoue et al. |
| 2017/0044520 A1 | 2/2017 | Liu et al. |
| 2017/0044592 A1 | 2/2017 | Peter et al. |
| 2017/0053729 A1 | 2/2017 | Kotani et al. |
| 2017/0058271 A1 | 3/2017 | Joung et al. |
| 2017/0058272 A1 | 3/2017 | Carter et al. |
| 2017/0058298 A1 | 3/2017 | Kennedy et al. |
| 2017/0073663 A1 | 3/2017 | Wang et al. |
| 2017/0073670 A1 | 3/2017 | Nishida et al. |
| 2017/0087224 A1 | 3/2017 | Quake |
| 2017/0087225 A1 | 3/2017 | Quake |
| 2017/0088587 A1 | 3/2017 | Quake |
| 2017/0088828 A1 | 3/2017 | Quake |
| 2017/0107536 A1 | 4/2017 | Zhang et al. |
| 2017/0107560 A1 | 4/2017 | Peter et al. |
| 2017/0114367 A1 | 4/2017 | Hu et al. |
| 2017/0121693 A1 | 5/2017 | Liu et al. |
| 2017/0145394 A1 | 5/2017 | Yeo et al. |
| 2017/0145405 A1 | 5/2017 | Tang et al. |
| 2017/0145438 A1 | 5/2017 | Kantor |
| 2017/0152528 A1 | 6/2017 | Zhang |
| 2017/0152787 A1 | 6/2017 | Kubo et al. |
| 2017/0159033 A1 | 6/2017 | Kamtekar et al. |
| 2017/0166928 A1 | 6/2017 | Vyas et al. |
| 2017/0175104 A1 | 6/2017 | Doudna et al. |
| 2017/0175142 A1 | 6/2017 | Zhang et al. |
| 2017/0191047 A1 | 7/2017 | Terns et al. |
| 2017/0191078 A1 | 7/2017 | Zhang et al. |
| 2017/0198269 A1 | 7/2017 | Zhang et al. |
| 2017/0198277 A1 | 7/2017 | Kmiec et al. |
| 2017/0198302 A1 | 7/2017 | Feng et al. |
| 2017/0226522 A1 | 8/2017 | Hu et al. |
| 2017/0233703 A1 | 8/2017 | Xie et al. |
| 2017/0233756 A1 | 8/2017 | Begemann et al. |
| 2017/0247671 A1 | 8/2017 | Yung et al. |
| 2017/0247703 A1 | 8/2017 | Sloan et al. |
| 2017/0268022 A1 | 9/2017 | Liu et al. |
| 2017/0275665 A1 | 9/2017 | Silas et al. |
| 2017/0283797 A1 | 10/2017 | Robb et al. |
| 2017/0283831 A1 | 10/2017 | Zhang et al. |
| 2017/0314016 A1 | 11/2017 | Kim et al. |
| 2017/0362635 A1 | 12/2017 | Chamberlain et al. |
| 2018/0064077 A1 | 3/2018 | Dunham et al. |
| 2018/0066258 A1 | 3/2018 | Powell |
| 2018/0068062 A1 | 3/2018 | Zhang et al. |
| 2018/0073012 A1 | 3/2018 | Liu et al. |
| 2018/0080051 A1 | 3/2018 | Sheikh et al. |
| 2018/0087046 A1 | 3/2018 | Badran et al. |
| 2018/0100147 A1 | 4/2018 | Yates et al. |
| 2018/0105867 A1 | 4/2018 | Xiao et al. |
| 2018/0119118 A1 | 5/2018 | Lu et al. |
| 2018/0127780 A1 | 5/2018 | Liu et al. |
| 2018/0155708 A1 | 6/2018 | Church et al. |
| 2018/0155720 A1 | 6/2018 | Donohoue et al. |
| 2018/0163213 A1 | 6/2018 | Aneja et al. |
| 2018/0170984 A1 | 6/2018 | Harris et al. |
| 2018/0179503 A1 | 6/2018 | Maianti et al. |
| 2018/0179547 A1 | 6/2018 | Zhang et al. |
| 2018/0201921 A1 | 7/2018 | Malcolm |
| 2018/0230464 A1 | 8/2018 | Zhong |
| 2018/0230471 A1 | 8/2018 | Storici et al. |
| 2018/0236081 A1 | 8/2018 | Liu et al. |
| 2018/0237758 A1 | 8/2018 | Liu et al. |
| 2018/0237787 A1 | 8/2018 | Maianti et al. |
| 2018/0245066 A1 | 8/2018 | Yao et al. |
| 2018/0258418 A1 | 9/2018 | Kim |
| 2018/0265864 A1 | 9/2018 | Li et al. |
| 2018/0273939 A1 | 9/2018 | Yu et al. |
| 2018/0282722 A1 | 10/2018 | Jakimo et al. |
| 2018/0298391 A1 | 10/2018 | Jakimo et al. |
| 2018/0305688 A1 | 10/2018 | Zhong |
| 2018/0305704 A1 | 10/2018 | Zhang |
| 2018/0312822 A1 | 11/2018 | Lee et al. |
| 2018/0312825 A1 | 11/2018 | Liu et al. |
| 2018/0312828 A1 | 11/2018 | Liu et al. |
| 2018/0312835 A1 | 11/2018 | Yao et al. |
| 2018/0327756 A1 | 11/2018 | Zhang et al. |
| 2019/0010481 A1 | 1/2019 | Joung et al. |
| 2019/0055543 A1 | 2/2019 | Tran et al. |
| 2019/0093099 A1 | 3/2019 | Liu et al. |
| 2019/0185883 A1 | 6/2019 | Liu et al. |
| 2019/0225955 A1 | 7/2019 | Liu et al. |
| 2019/0233847 A1 | 8/2019 | Savage et al. |
| 2019/0241633 A1 | 8/2019 | Fotin-Mleczek et al. |
| 2019/0256842 A1 | 8/2019 | Liu et al. |
| 2019/0264202 A1 | 8/2019 | Church et al. |
| 2019/0276816 A1 | 9/2019 | Liu et al. |
| 2019/0322992 A1 | 10/2019 | Liu et al. |
| 2019/0352632 A1 | 11/2019 | Liu et al. |
| 2019/0367891 A1 | 12/2019 | Liu et al. |
| 2020/0010818 A1 | 1/2020 | Liu et al. |
| 2020/0010835 A1 | 1/2020 | Maianti et al. |
| 2020/0063127 A1 | 2/2020 | Lu et al. |
| 2020/0071722 A1 | 3/2020 | Liu et al. |
| 2020/0172931 A1 | 6/2020 | Liu et al. |
| 2020/0181619 A1 | 6/2020 | Tang et al. |
| 2020/0190493 A1 | 6/2020 | Liu et al. |
| 2020/0216833 A1 | 7/2020 | Liu et al. |
| 2020/0255868 A1 | 8/2020 | Liu et al. |
| 2020/0277587 A1 | 9/2020 | Liu et al. |
| 2020/0323984 A1 | 10/2020 | Liu et al. |
| 2020/0399619 A1 | 12/2020 | Maianti et al. |
| 2020/0399626 A1 | 12/2020 | Liu et al. |
| 2021/0054416 A1 | 2/2021 | Liu et al. |

FOREIGN PATENT DOCUMENTS

| | | |
|---|---|---|
| AU | 2015252023 A1 | 11/2015 |
| AU | 2015101792 A4 | 1/2016 |
| BR | 112015013786 A2 | 7/2017 |
| CA | 2894668 A1 | 6/2014 |
| CA | 2894681 A1 | 6/2014 |
| CA | 2894684 A1 | 6/2014 |
| CA | 2 852 593 A1 | 11/2015 |
| CN | 1069962 A | 3/1993 |
| CN | 103224947 A | 7/2013 |
| CN | 103233028 A | 8/2013 |
| CN | 103388006 A | 11/2013 |
| CN | 103614415 A | 3/2014 |
| CN | 103642836 A | 3/2014 |
| CN | 103668472 A | 3/2014 |
| CN | 103820441 A | 5/2014 |
| CN | 103820454 A | 5/2014 |
| CN | 103911376 A | 7/2014 |
| CN | 103923911 A | 7/2014 |
| CN | 103981211 A | 8/2014 |
| CN | 103981212 A | 8/2014 |
| CN | 104004778 A | 8/2014 |
| CN | 104004782 A | 8/2014 |
| CN | 104017821 A | 9/2014 |
| CN | 104109687 A | 10/2014 |
| CN | 104178461 A | 12/2014 |
| CN | 104342457 A | 2/2015 |
| CN | 104404036 A | 3/2015 |
| CN | 104450774 A | 3/2015 |
| CN | 104480144 A | 4/2015 |
| CN | 104498493 A | 4/2015 |
| CN | 104504304 A | 4/2015 |
| CN | 104531704 A | 4/2015 |
| CN | 104531705 A | 4/2015 |
| CN | 104560864 A | 4/2015 |
| CN | 104561095 A | 4/2015 |
| CN | 104593418 A | 5/2015 |
| CN | 104593422 A | 5/2015 |
| CN | 104611370 A | 5/2015 |
| CN | 104651392 A | 5/2015 |
| CN | 104651398 A | 5/2015 |
| CN | 104651399 A | 5/2015 |
| CN | 104651401 A | 5/2015 |
| CN | 104673816 A | 6/2015 |

(56) References Cited

FOREIGN PATENT DOCUMENTS

| | | |
|---|---|---|
| CN | 104725626 A | 6/2015 |
| CN | 104726449 A | 6/2015 |
| CN | 104726494 A | 6/2015 |
| CN | 104745626 A | 7/2015 |
| CN | 104762321 A | 7/2015 |
| CN | 104805078 A | 7/2015 |
| CN | 104805099 A | 7/2015 |
| CN | 104805118 A | 7/2015 |
| CN | 104846010 A | 8/2015 |
| CN | 104894068 A | 9/2015 |
| CN | 104894075 A | 9/2015 |
| CN | 104928321 A | 9/2015 |
| CN | 105039339 A | 11/2015 |
| CN | 105039399 A | 11/2015 |
| CN | 105063061 A | 11/2015 |
| CN | 105087620 A | 11/2015 |
| CN | 105112422 A | 12/2015 |
| CN | 105112445 A | 12/2015 |
| CN | 105112519 A | 12/2015 |
| CN | 105121648 A | 12/2015 |
| CN | 105132427 A | 12/2015 |
| CN | 105132451 A | 12/2015 |
| CN | 105177038 A | 12/2015 |
| CN | 105177126 A | 12/2015 |
| CN | 105210981 A | 1/2016 |
| CN | 105219799 A | 1/2016 |
| CN | 105238806 A | 1/2016 |
| CN | 105255937 A | 1/2016 |
| CN | 105274144 A | 1/2016 |
| CN | 105296518 A | 2/2016 |
| CN | 105296537 A | 2/2016 |
| CN | 105316324 A | 2/2016 |
| CN | 105316327 A | 2/2016 |
| CN | 105316337 A | 2/2016 |
| CN | 105331607 A | 2/2016 |
| CN | 105331608 A | 2/2016 |
| CN | 105331609 A | 2/2016 |
| CN | 105331627 A | 2/2016 |
| CN | 105400773 A | 3/2016 |
| CN | 105400779 A | 3/2016 |
| CN | 105400810 A | 3/2016 |
| CN | 105441451 A | 3/2016 |
| CN | 105462968 A | 4/2016 |
| CN | 105463003 A | 4/2016 |
| CN | 105463027 A | 4/2016 |
| CN | 105492608 A | 4/2016 |
| CN | 105492609 A | 4/2016 |
| CN | 105505976 A | 4/2016 |
| CN | 105505979 A | 4/2016 |
| CN | 105518134 A | 4/2016 |
| CN | 105518135 A | 4/2016 |
| CN | 105518137 A | 4/2016 |
| CN | 105518138 A | 4/2016 |
| CN | 105518139 A | 4/2016 |
| CN | 105518140 A | 4/2016 |
| CN | 105543228 A | 5/2016 |
| CN | 105543266 A | 5/2016 |
| CN | 105543270 A | 5/2016 |
| CN | 105567688 A | 5/2016 |
| CN | 105567689 A | 5/2016 |
| CN | 105567734 A | 5/2016 |
| CN | 105567735 A | 5/2016 |
| CN | 105567738 A | 5/2016 |
| CN | 105593367 A | 5/2016 |
| CN | 105594664 A | 5/2016 |
| CN | 105602987 A | 5/2016 |
| CN | 105624146 A | 6/2016 |
| CN | 105624187 A | 6/2016 |
| CN | 105646719 A | 6/2016 |
| CN | 105647922 A | 6/2016 |
| CN | 105647962 A | 6/2016 |
| CN | 105647968 A | 6/2016 |
| CN | 105647969 A | 6/2016 |
| CN | 105671070 A | 6/2016 |
| CN | 105671083 A | 6/2016 |
| CN | 105695485 A | 6/2016 |
| CN | 105779448 A | 7/2016 |
| CN | 105779449 A | 7/2016 |
| CN | 105802980 A | 7/2016 |
| CN | 105821039 A | 8/2016 |
| CN | 105821040 A | 8/2016 |
| CN | 105821049 A | 8/2016 |
| CN | 105821072 A | 8/2016 |
| CN | 105821075 A | 8/2016 |
| CN | 105821116 A | 8/2016 |
| CN | 105838733 A | 8/2016 |
| CN | 105861547 A | 8/2016 |
| CN | 105861552 A | 8/2016 |
| CN | 105861554 A | 8/2016 |
| CN | 105886498 A | 8/2016 |
| CN | 105886534 A | 8/2016 |
| CN | 105886616 A | 8/2016 |
| CN | 105907758 A | 8/2016 |
| CN | 105907785 A | 8/2016 |
| CN | 105925608 A | 9/2016 |
| CN | 105950560 A | 9/2016 |
| CN | 105950626 A | 9/2016 |
| CN | 105950633 A | 9/2016 |
| CN | 105950639 A | 9/2016 |
| CN | 105985985 A | 10/2016 |
| CN | 106011104 A | 10/2016 |
| CN | 106011150 A | 10/2016 |
| CN | 106011167 A | 10/2016 |
| CN | 106011171 A | 10/2016 |
| CN | 106032540 A | 10/2016 |
| CN | 106047803 A | 10/2016 |
| CN | 106047877 A | 10/2016 |
| CN | 106047930 A | 10/2016 |
| CN | 106086008 A | 11/2016 |
| CN | 106086028 A | 11/2016 |
| CN | 106086061 A | 11/2016 |
| CN | 106086062 A | 11/2016 |
| CN | 106109417 A | 11/2016 |
| CN | 106119275 A | 11/2016 |
| CN | 106119283 A | 11/2016 |
| CN | 106148286 A | 11/2016 |
| CN | 106148370 A | 11/2016 |
| CN | 106148416 A | 11/2016 |
| CN | 106167525 A | 11/2016 |
| CN | 106167808 A | 11/2016 |
| CN | 106167810 A | 11/2016 |
| CN | 106167821 A | 11/2016 |
| CN | 106172238 A | 12/2016 |
| CN | 106190903 A | 12/2016 |
| CN | 106191057 A | 12/2016 |
| CN | 106191061 A | 12/2016 |
| CN | 106191062 A | 12/2016 |
| CN | 106191064 A | 12/2016 |
| CN | 106191071 A | 12/2016 |
| CN | 106191099 A | 12/2016 |
| CN | 106191107 A | 12/2016 |
| CN | 106191113 A | 12/2016 |
| CN | 106191114 A | 12/2016 |
| CN | 106191116 A | 12/2016 |
| CN | 106191124 A | 12/2016 |
| CN | 106222177 A | 12/2016 |
| CN | 106222193 A | 12/2016 |
| CN | 106222203 A | 12/2016 |
| CN | 106244555 A | 12/2016 |
| CN | 106244591 A | 12/2016 |
| CN | 106244609 A | 12/2016 |
| CN | 106282241 A | 1/2017 |
| CN | 106318934 A | 1/2017 |
| CN | 106318973 A | 1/2017 |
| CN | 106350540 A | 1/2017 |
| CN | 106367435 A | 2/2017 |
| CN | 106399306 A | 2/2017 |
| CN | 106399311 A | 2/2017 |
| CN | 106399360 A | 2/2017 |
| CN | 106399367 A | 2/2017 |
| CN | 106399375 A | 2/2017 |
| CN | 106399377 A | 2/2017 |
| CN | 106434651 A | 2/2017 |
| CN | 106434663 A | 2/2017 |

(56) References Cited

FOREIGN PATENT DOCUMENTS

| CN | 106434688 A | 2/2017 |
| CN | 106434737 A | 2/2017 |
| CN | 106434748 A | 2/2017 |
| CN | 106434752 A | 2/2017 |
| CN | 106434782 A | 2/2017 |
| CN | 106446600 A | 2/2017 |
| CN | 106479985 A | 3/2017 |
| CN | 106480027 A | 3/2017 |
| CN | 106480036 A | 3/2017 |
| CN | 106480067 A | 3/2017 |
| CN | 106480080 A | 3/2017 |
| CN | 106480083 A | 3/2017 |
| CN | 106480097 A | 3/2017 |
| CN | 106544351 A | 3/2017 |
| CN | 106544353 A | 3/2017 |
| CN | 106544357 A | 3/2017 |
| CN | 106554969 A | 4/2017 |
| CN | 106566838 A | 4/2017 |
| CN | 106701763 A | 5/2017 |
| CN | 106701808 A | 5/2017 |
| CN | 106701818 A | 5/2017 |
| CN | 106701823 A | 5/2017 |
| CN | 106701830 A | 5/2017 |
| CN | 106754912 A | 5/2017 |
| CN | 106755026 A | 5/2017 |
| CN | 106755077 A | 5/2017 |
| CN | 106755088 A | 5/2017 |
| CN | 106755091 A | 5/2017 |
| CN | 106755097 A | 5/2017 |
| CN | 106755424 A | 5/2017 |
| CN | 106801056 A | 6/2017 |
| CN | 106834323 A | 6/2017 |
| CN | 106834341 A | 6/2017 |
| CN | 106834347 A | 6/2017 |
| CN | 106845151 A | 6/2017 |
| CN | 106868008 A | 6/2017 |
| CN | 106868031 A | 6/2017 |
| CN | 106906240 A | 6/2017 |
| CN | 106906242 A | 6/2017 |
| CN | 106916820 A | 7/2017 |
| CN | 106916852 A | 7/2017 |
| CN | 106939303 A | 7/2017 |
| CN | 106947750 A | 7/2017 |
| CN | 106947780 A | 7/2017 |
| CN | 106957830 A | 7/2017 |
| CN | 106957831 A | 7/2017 |
| CN | 106957844 A | 7/2017 |
| CN | 106957855 A | 7/2017 |
| CN | 106957858 A | 7/2017 |
| CN | 106967697 A | 7/2017 |
| CN | 106967726 A | 7/2017 |
| CN | 106978428 A | 7/2017 |
| CN | 106987570 A | 7/2017 |
| CN | 106987757 A | 7/2017 |
| CN | 107012164 A | 8/2017 |
| CN | 107012174 A | 8/2017 |
| CN | 107012213 A | 8/2017 |
| CN | 107012250 A | 8/2017 |
| CN | 107022562 A | 8/2017 |
| CN | 107034188 A | 8/2017 |
| CN | 107034218 A | 8/2017 |
| CN | 107034229 A | 8/2017 |
| CN | 107043775 A | 8/2017 |
| CN | 107043779 A | 8/2017 |
| CN | 107043787 A | 8/2017 |
| CN | 107058320 A | 8/2017 |
| CN | 107058328 A | 8/2017 |
| CN | 107058358 A | 8/2017 |
| CN | 107058372 A | 8/2017 |
| CN | 107083392 A | 8/2017 |
| CN | 107099533 A | 8/2017 |
| CN | 107099850 A | 8/2017 |
| CN | 107119053 A | 9/2017 |
| CN | 107119071 A | 9/2017 |
| CN | 107129999 A | 9/2017 |
| CN | 107130000 A | 9/2017 |
| CN | 107142272 A | 9/2017 |
| CN | 107142282 A | 9/2017 |
| CN | 107177591 A | 9/2017 |
| CN | 107177595 A | 9/2017 |
| CN | 107177631 A | 9/2017 |
| CN | 107190006 A | 9/2017 |
| CN | 107190008 A | 9/2017 |
| CN | 107217042 A | 9/2017 |
| CN | 107217075 A | 9/2017 |
| CN | 107227307 A | 10/2017 |
| CN | 107227352 A | 10/2017 |
| CN | 107236737 A | 10/2017 |
| CN | 107236739 A | 10/2017 |
| CN | 107236741 A | 10/2017 |
| CN | 107245502 A | 10/2017 |
| CN | 107254485 A | 10/2017 |
| CN | 107266541 A | 10/2017 |
| CN | 107267515 A | 10/2017 |
| CN | 107287245 A | 10/2017 |
| CN | 107298701 A | 10/2017 |
| CN | 107299114 A | 10/2017 |
| CN | 107304435 A | 10/2017 |
| CN | 107312785 A | 11/2017 |
| CN | 107312793 A | 11/2017 |
| CN | 107312795 A | 11/2017 |
| CN | 107312798 A | 11/2017 |
| CN | 107326042 A | 11/2017 |
| CN | 107326046 A | 11/2017 |
| CN | 107354156 A | 11/2017 |
| CN | 107354173 A | 11/2017 |
| CN | 107356793 A | 11/2017 |
| CN | 107362372 A | 11/2017 |
| CN | 107365786 A | 11/2017 |
| CN | 107365804 A | 11/2017 |
| CN | 107384894 A | 11/2017 |
| CN | 107384922 A | 11/2017 |
| CN | 107384926 A | 11/2017 |
| CN | 107400677 A | 11/2017 |
| CN | 107418974 A | 12/2017 |
| CN | 107435051 A | 12/2017 |
| CN | 107435069 A | 12/2017 |
| CN | 107446922 A | 12/2017 |
| CN | 107446923 A | 12/2017 |
| CN | 107446924 A | 12/2017 |
| CN | 107446932 A | 12/2017 |
| CN | 107446951 A | 12/2017 |
| CN | 107446954 A | 12/2017 |
| CN | 107460196 A | 12/2017 |
| CN | 107474129 A | 12/2017 |
| CN | 107475300 A | 12/2017 |
| CN | 107488649 A | 12/2017 |
| CN | 107502608 A | 12/2017 |
| CN | 107502618 A | 12/2017 |
| CN | 107513531 A | 12/2017 |
| CN | 107519492 A | 12/2017 |
| CN | 107523567 A | 12/2017 |
| CN | 107523583 A | 12/2017 |
| CN | 107541525 A | 1/2018 |
| CN | 107557373 A | 1/2018 |
| CN | 107557378 A | 1/2018 |
| CN | 107557381 A | 1/2018 |
| CN | 107557390 A | 1/2018 |
| CN | 107557393 A | 1/2018 |
| CN | 107557394 A | 1/2018 |
| CN | 107557455 A | 1/2018 |
| CN | 107574179 | 1/2018 |
| CN | 107586777 | 1/2018 |
| CN | 107586779 | 1/2018 |
| CN | 107604003 | 1/2018 |
| CN | 107619829 A | 1/2018 |
| CN | 107619837 A | 1/2018 |
| CN | 107630006 A | 1/2018 |
| CN | 107630041 A | 1/2018 |
| CN | 107630042 A | 1/2018 |
| CN | 107630043 A | 1/2018 |
| CN | 107641631 A | 1/2018 |
| CN | 107653256 A | 2/2018 |
| CN | 107686848 A | 2/2018 |

(56) References Cited

FOREIGN PATENT DOCUMENTS

| | | |
|---|---|---|
| CN | 206970581 | 2/2018 |
| CN | 107760652 A | 3/2018 |
| CN | 107760663 A | 3/2018 |
| CN | 107760684 A | 3/2018 |
| CN | 107760715 A | 3/2018 |
| CN | 107784200 A | 3/2018 |
| CN | 107794272 A | 3/2018 |
| CN | 107794276 A | 3/2018 |
| CN | 107815463 A | 3/2018 |
| CN | 107828738 A | 3/2018 |
| CN | 107828794 A | 3/2018 |
| CN | 107828826 A | 3/2018 |
| CN | 107828874 A | 3/2018 |
| CN | 107858346 A | 3/2018 |
| CN | 107858373 A | 3/2018 |
| CN | 107880132 A | 4/2018 |
| CN | 107881184 A | 4/2018 |
| CN | 107893074 A | 4/2018 |
| CN | 107893075 A | 4/2018 |
| CN | 107893076 A | 4/2018 |
| CN | 107893080 A | 4/2018 |
| CN | 107893086 A | 4/2018 |
| CN | 107904261 A | 4/2018 |
| CN | 107937427 A | 4/2018 |
| CN | 107937432 A | 4/2018 |
| CN | 107937501 A | 4/2018 |
| CN | 107974466 A | 5/2018 |
| CN | 107988229 A | 5/2018 |
| CN | 107988246 A | 5/2018 |
| CN | 107988256 A | 5/2018 |
| CN | 107988268 A | 5/2018 |
| CN | 108018316 A | 5/2018 |
| CN | 108034656 A | 5/2018 |
| CN | 108048466 A | 5/2018 |
| CN | 108102940 A | 6/2018 |
| CN | 108103092 A | 6/2018 |
| CN | 108103098 A | 6/2018 |
| CN | 108103586 A | 6/2018 |
| CN | 108148835 A | 6/2018 |
| CN | 108148837 A | 6/2018 |
| CN | 108148873 A | 6/2018 |
| CN | 108192956 A | 6/2018 |
| CN | 108251423 A | 7/2018 |
| CN | 108251451 A | 7/2018 |
| CN | 108251452 A | 7/2018 |
| CN | 108342480 A | 7/2018 |
| CN | 108359691 A | 8/2018 |
| CN | 108359712 A | 8/2018 |
| CN | 108384784 A | 8/2018 |
| CN | 108396027 A | 8/2018 |
| CN | 108410877 A | 8/2018 |
| CN | 108410906 A | 8/2018 |
| CN | 108410907 A | 8/2018 |
| CN | 108410911 A | 8/2018 |
| CN | 108424931 A | 8/2018 |
| CN | 108441519 A | 8/2018 |
| CN | 108441520 A | 8/2018 |
| CN | 108486108 A | 9/2018 |
| CN | 108486111 A | 9/2018 |
| CN | 108486145 A | 9/2018 |
| CN | 108486146 A | 9/2018 |
| CN | 108486154 A | 9/2018 |
| CN | 108486159 A | 9/2018 |
| CN | 108486234 A | 9/2018 |
| CN | 108504657 A | 9/2018 |
| CN | 108504685 A | 9/2018 |
| CN | 108504693 A | 9/2018 |
| CN | 108546712 A | 9/2018 |
| CN | 108546717 A | 9/2018 |
| CN | 108546718 A | 9/2018 |
| CN | 108559730 A | 9/2018 |
| CN | 108559732 A | 9/2018 |
| CN | 108559745 A | 9/2018 |
| CN | 108559760 A | 9/2018 |
| CN | 108570479 A | 9/2018 |
| CN | 108588071 A | 9/2018 |
| CN | 108588123 A | 9/2018 |
| CN | 108588128 A | 9/2018 |
| CN | 108588182 A | 9/2018 |
| CN | 108610399 A | 10/2018 |
| CN | 108611364 A | 10/2018 |
| CN | 108624622 A | 10/2018 |
| CN | 108642053 A | 10/2018 |
| CN | 108642055 A | 10/2018 |
| CN | 108642077 A | 10/2018 |
| CN | 108642078 A | 10/2018 |
| CN | 108642090 A | 10/2018 |
| CN | 108690844 A | 10/2018 |
| CN | 108707604 A | 10/2018 |
| CN | 108707620 A | 10/2018 |
| CN | 108707621 A | 10/2018 |
| CN | 108707628 A | 10/2018 |
| CN | 108707629 A | 10/2018 |
| CN | 108715850 A | 10/2018 |
| CN | 108728476 A | 11/2018 |
| CN | 108728486 A | 11/2018 |
| CN | 108753772 A | 11/2018 |
| CN | 108753783 A | 11/2018 |
| CN | 108753813 A | 11/2018 |
| CN | 108753817 A | 11/2018 |
| CN | 108753832 A | 11/2018 |
| CN | 108753835 A | 11/2018 |
| CN | 108753836 A | 11/2018 |
| CN | 108795902 A | 11/2018 |
| CN | 108822217 A | 11/2018 |
| CN | 108823248 A | 11/2018 |
| CN | 108823249 A | 11/2018 |
| CN | 108823291 A | 11/2018 |
| CN | 108841845 A | 11/2018 |
| CN | 108853133 A | 11/2018 |
| CN | 108866093 A | 11/2018 |
| CN | 108893529 A | 11/2018 |
| CN | 108913664 A | 11/2018 |
| CN | 108913691 A | 11/2018 |
| CN | 108913714 A | 11/2018 |
| CN | 108913717 A | 11/2018 |
| CN | 109 517 841 A | 3/2019 |
| EP | 0264166 A1 | 4/1988 |
| EP | 2604255 A1 | 6/2013 |
| EP | 2840140 A1 | 2/2015 |
| EP | 2966170 A1 | 1/2016 |
| EP | 3009511 A2 | 4/2016 |
| EP | 3031921 A1 | 6/2016 |
| EP | 3045537 A1 | 7/2016 |
| EP | 3 115 457 A1 | 1/2017 |
| EP | 3144390 A1 | 3/2017 |
| EP | 3199632 A1 | 8/2017 |
| EP | 3216867 A1 | 9/2017 |
| EP | 3252160 A1 | 12/2017 |
| EP | 3450553 B1 | 12/2019 |
| ES | 2740248 T3 | 2/2020 |
| GB | 2528177 A | 1/2016 |
| GB | 2531454 A | 4/2016 |
| GB | 2542653 A | 3/2017 |
| HK | 1208045 A1 | 2/2016 |
| JP | 2007-501626 A | 2/2007 |
| JP | 2008-515405 A | 5/2008 |
| JP | 2010-539929 A | 12/2010 |
| JP | 2011-081011 A | 4/2011 |
| JP | 2011-523353 A | 8/2011 |
| JP | 2012-525146 A | 10/2012 |
| JP | 2012-531909 A | 12/2012 |
| KR | 101584933 B1 | 1/2016 |
| KR | 20160133380 A | 11/2016 |
| KR | 20170037025 A | 4/2017 |
| KR | 20170037028 A | 4/2017 |
| KR | 101748575 B1 | 6/2017 |
| KR | 2018-0022465 A | 3/2018 |
| RU | 2016104674 A | 8/2017 |
| RU | 2634395 C1 | 10/2017 |
| RU | 2652899 C1 | 5/2018 |
| RU | 2015128057 A | 3/2019 |
| RU | 2015128098 A | 3/2019 |
| RU | 2687451 C1 | 5/2019 |

(56) References Cited

FOREIGN PATENT DOCUMENTS

| | | | |
|---|---|---|---|
| RU | 2019112514 A | 6/2019 | |
| RU | 2019127300 A | 9/2019 | |
| RU | 2701850 C2 | 10/2019 | |
| TW | 1608100 B | 12/2017 | |
| TW | 2018-29773 A | 8/2018 | |
| WO | WO 90/02809 A1 | 3/1990 | |
| WO | WO 91/16024 A1 | 10/1991 | |
| WO | WO 91/17271 A1 | 11/1991 | |
| WO | WO 91/17424 A1 | 11/1991 | |
| WO | WO 92/06188 A2 | 4/1992 | |
| WO | WO 92/06200 A1 | 4/1992 | |
| WO | WO 93/24641 A2 | 12/1993 | |
| WO | WO 94/18316 A2 | 8/1994 | |
| WO | WO 94/026877 A1 | 11/1994 | |
| WO | WO 96/04403 A1 | 2/1996 | |
| WO | WO 96/10640 A1 | 4/1996 | |
| WO | WO 98/32845 A1 | 7/1998 | |
| WO | WO 2001/036452 A2 | 5/2001 | |
| WO | WO 2001/038547 A2 | 5/2001 | |
| WO | WO 2002/059296 A2 | 8/2002 | |
| WO | WO 2002/068676 A2 | 9/2002 | |
| WO | WO 2002/103028 A2 | 12/2002 | |
| WO | WO 2004/007684 A2 | 1/2004 | |
| WO | WO 05/14791 A2 | 2/2005 | |
| WO | WO 2005/014791 A2 | 2/2005 | |
| WO | WO 2005/019415 A2 | 3/2005 | |
| WO | WO 2006/002547 A1 | 1/2006 | |
| WO | WO 2006/042112 A2 | 4/2006 | |
| WO | WO 2007/025097 A2 | 3/2007 | |
| WO | WO 07/066923 A1 | 6/2007 | |
| WO | WO 2007/136815 A2 | 11/2007 | |
| WO | WO 2007/143574 A1 | 12/2007 | |
| WO | WO 08/005529 A2 | 1/2008 | |
| WO | WO 2008/108989 A2 | 9/2008 | |
| WO | WO 2009/134808 A2 | 11/2009 | |
| WO | WO 2010/011961 A2 | 1/2010 | |
| WO | WO 2010/028347 A2 | 3/2010 | |
| WO | WO 2010/054108 A2 | 5/2010 | |
| WO | WO 2010/054154 A2 | 5/2010 | |
| WO | WO 2010/068289 A2 | 6/2010 | |
| WO | WO 2010/075424 A2 | 7/2010 | |
| WO | WO 2010/102257 A2 | 9/2010 | |
| WO | WO 2010/129019 A2 | 11/2010 | |
| WO | WO 2010/129023 A2 | 11/2010 | |
| WO | WO 2010/132092 A2 | 11/2010 | |
| WO | WO 2010/144150 A2 | 12/2010 | |
| WO | WO 2011/002503 A1 | 1/2011 | |
| WO | WO 2011/017293 A2 | 2/2011 | |
| WO | WO 2011/053868 A1 | 5/2011 | |
| WO | WO 2011/053982 A2 | 5/2011 | |
| WO | WO 2011/068810 A1 | 6/2011 | |
| WO | WO 2011/075627 A1 | 6/2011 | |
| WO | WO 2011/091311 A2 | 7/2011 | |
| WO | WO 2011/109031 A1 | 9/2011 | |
| WO | WO 2011/143124 A2 | 11/2011 | |
| WO | WO 2011/147590 A2 | 12/2011 | |
| WO | WO 2011/159369 A1 | 12/2011 | |
| WO | WO 2012/054726 A1 | 4/2012 | |
| WO | WO 2012/065043 A2 | 5/2012 | |
| WO | WO 2012/088381 A2 | 6/2012 | |
| WO | WO 2012/125445 A2 | 9/2012 | |
| WO | WO 2012/138927 A2 | 10/2012 | |
| WO | WO 2012/149470 A1 | 11/2012 | |
| WO | WO 2012/158985 A2 | 11/2012 | |
| WO | WO 2012/158986 A2 | 11/2012 | |
| WO | WO 2012/164565 A1 | 12/2012 | |
| WO | WO 2012/170930 A1 | 12/2012 | |
| WO | WO 2013/012674 A1 | 1/2013 | |
| WO | WO 2013/013105 A1 | 1/2013 | |
| WO | WO 2013/013105 A2 | 1/2013 | |
| WO | WO 2013/039857 A1 | 3/2013 | |
| WO | WO 2013/039861 A2 | 3/2013 | |
| WO | WO 2013/045632 A1 | 4/2013 | |
| WO | WO 2013/047844 A1 | 4/2013 | |
| WO | WO 2013/066438 A2 | 5/2013 | |
| WO | WO 2013/098244 A1 | 7/2013 | |
| WO | WO 2013/119602 A1 | 8/2013 | |
| WO | WO 2013/126794 A1 | 8/2013 | |
| WO | WO 2013/130824 A1 | 9/2013 | |
| WO | WO 2013/141680 A1 | 9/2013 | |
| WO | WO 2013/142578 A1 | 9/2013 | |
| WO | WO 2013/152359 A1 | 10/2013 | |
| WO | WO 2013/160230 A1 | 10/2013 | |
| WO | WO 2013/166315 A1 | 11/2013 | |
| WO | WO 2013/169398 A2 | 11/2013 | |
| WO | WO 2013/169802 A1 | 11/2013 | |
| WO | WO 2013/176772 A1 | 11/2013 | |
| WO | WO 2013/176915 A1 | 11/2013 | |
| WO | WO 2013/176916 A1 | 11/2013 | |
| WO | WO 2013/181440 A1 | 12/2013 | |
| WO | WO 2013/186754 A2 | 12/2013 | |
| WO | WO 2013/188037 A2 | 12/2013 | |
| WO | WO 2013/188522 A2 | 12/2013 | |
| WO | WO 2013/188638 A2 | 12/2013 | |
| WO | WO 2013/192278 A1 | 12/2013 | |
| WO | WO 2013/142378 A9 | 1/2014 | |
| WO | WO 2014/004336 A2 | 1/2014 | |
| WO | WO 2014/005042 A2 | 1/2014 | |
| WO | WO 2014/011237 A1 | 1/2014 | |
| WO | WO 2014/011901 A2 | 1/2014 | |
| WO | WO 2014/018423 A2 | 1/2014 | |
| WO | WO 2014/020608 A1 | 2/2014 | |
| WO | WO 2014/022120 A1 | 2/2014 | |
| WO | WO 2014/022702 A2 | 2/2014 | |
| WO | WO 2014/036219 A2 | 3/2014 | |
| WO | WO 2014/039513 A2 | 3/2014 | |
| WO | WO 2014/039523 A1 | 3/2014 | |
| WO | WO 2014/039585 A2 | 3/2014 | |
| WO | WO 2014/039684 A1 | 3/2014 | |
| WO | WO 2014/039692 A2 | 3/2014 | |
| WO | WO 2014/039702 A2 | 3/2014 | |
| WO | WO 2014/039872 A1 | 3/2014 | |
| WO | WO 2014/039970 A1 | 3/2014 | |
| WO | WO 2014/041327 A1 | 3/2014 | |
| WO | WO 2014/043143 A1 | 3/2014 | |
| WO | WO 2014/047103 A2 | 3/2014 | |
| WO | WO 2014/055782 A1 | 4/2014 | |
| WO | WO 2014/059173 A2 | 4/2014 | |
| WO | WO 2014/059255 A1 | 4/2014 | |
| WO | WO 2014/065596 A1 | 5/2014 | |
| WO | WO 2014/066505 A1 | 5/2014 | |
| WO | WO 2014/068346 A2 | 5/2014 | |
| WO | WO 2014/070887 A1 | 5/2014 | |
| WO | WO 2014/071006 A1 | 5/2014 | |
| WO | WO 2014/071219 A1 | 5/2014 | |
| WO | WO 2014/071235 A1 | 5/2014 | |
| WO | WO 2014/072941 A1 | 5/2014 | |
| WO | WO 2014/081729 A1 | 5/2014 | |
| WO | WO 2014/081730 A1 | 5/2014 | |
| WO | WO 2014/081855 A1 | 5/2014 | |
| WO | WO 2014/082644 A1 | 6/2014 | |
| WO | WO 2014/085261 A1 | 6/2014 | |
| WO | WO 2014/085593 A1 | 6/2014 | |
| WO | WO 2014/085830 A2 | 6/2014 | |
| WO | WO 2014/089212 A1 | 6/2014 | |
| WO | WO 2014/089290 A1 | 6/2014 | |
| WO | WO 2014/089348 A1 | 6/2014 | |
| WO | WO 2014/089513 A1 | 6/2014 | |
| WO | WO 2014/089533 A2 | 6/2014 | |
| WO | WO 2014/089541 A2 | 6/2014 | |
| WO | WO 2014/093479 A1 | 6/2014 | |
| WO | WO 2014/093595 A1 | 6/2014 | |
| WO | WO 2014/093622 A2 | 6/2014 | |
| WO | WO 2014/093635 A1 | 6/2014 | |
| WO | WO 2014/093655 A2 | 6/2014 | |
| WO | WO 2014/093661 A2 | 6/2014 | |
| WO | WO 2014/093694 A1 | 6/2014 | |
| WO | WO 2014/093701 A1 | 6/2014 | |
| WO | WO 2014/093709 A1 | 6/2014 | |
| WO | WO 2014/093712 A1 | 6/2014 | |
| WO | WO 2014/093718 A1 | 6/2014 | |
| WO | WO 2014/093736 A1 | 6/2014 | |
| WO | WO 2014/093768 A1 | 6/2014 | |
| WO | WO 2014/093852 A1 | 6/2014 | |

(56) References Cited

FOREIGN PATENT DOCUMENTS

| | | |
|---|---|---|
| WO | WO 2014/096972 A2 | 6/2014 |
| WO | WO 2014/099744 A1 | 6/2014 |
| WO | WO 2014/099750 A2 | 6/2014 |
| WO | WO 2014/104878 A1 | 7/2014 |
| WO | WO 2014/110006 A1 | 7/2014 |
| WO | WO 2014/110552 A1 | 7/2014 |
| WO | WO 2014/113493 A1 | 7/2014 |
| WO | WO 2014/123967 A2 | 8/2014 |
| WO | WO 2014/124226 A1 | 8/2014 |
| WO | WO 2014/125668 A1 | 8/2014 |
| WO | WO 2014/127287 A1 | 8/2014 |
| WO | WO 2014/128324 A1 | 8/2014 |
| WO | WO 2014/128659 A1 | 8/2014 |
| WO | WO 2014/130706 A1 | 8/2014 |
| WO | WO 2014/130955 A1 | 8/2014 |
| WO | WO 2014/131833 A1 | 9/2014 |
| WO | WO 2014/138379 A1 | 9/2014 |
| WO | WO 2014/143381 A1 | 9/2014 |
| WO | WO 2014/144094 A1 | 9/2014 |
| WO | WO 2014/144155 A1 | 9/2014 |
| WO | WO 2014/144288 A1 | 9/2014 |
| WO | WO 2014/144592 A2 | 9/2014 |
| WO | WO 2014/144761 A2 | 9/2014 |
| WO | WO 2014/144951 A1 | 9/2014 |
| WO | WO 2014/145599 A2 | 9/2014 |
| WO | WO 2014/145736 A2 | 9/2014 |
| WO | WO 2014/150624 A1 | 9/2014 |
| WO | WO 2014/152432 A2 | 9/2014 |
| WO | WO 2014/152940 A1 | 9/2014 |
| WO | WO 2014/153118 A1 | 9/2014 |
| WO | WO 2014/153470 A2 | 9/2014 |
| WO | WO 2014/158593 A1 | 10/2014 |
| WO | WO 2014/161821 A1 | 10/2014 |
| WO | WO 2014/164466 A1 | 10/2014 |
| WO | WO 2014/165177 A1 | 10/2014 |
| WO | WO 2014/165349 A1 | 10/2014 |
| WO | WO 2014/165612 A2 | 10/2014 |
| WO | WO 2014/165707 A2 | 10/2014 |
| WO | WO 2014/165825 A2 | 10/2014 |
| WO | WO 2014/172458 A1 | 10/2014 |
| WO | WO 2014/172470 A2 | 10/2014 |
| WO | WO 2014/172489 A2 | 10/2014 |
| WO | WO 2014/173955 A1 | 10/2014 |
| WO | WO 2014/182700 A1 | 11/2014 |
| WO | WO 2014/183071 A2 | 11/2014 |
| WO | WO 2014/184143 A1 | 11/2014 |
| WO | WO 2014/184741 A1 | 11/2014 |
| WO | WO 2014/184744 A1 | 11/2014 |
| WO | WO 2014/186585 A2 | 11/2014 |
| WO | WO 2014/186686 A2 | 11/2014 |
| WO | WO 2014/190181 A1 | 11/2014 |
| WO | WO 2014/191128 A1 | 12/2014 |
| WO | WO 2014/191518 A1 | 12/2014 |
| WO | WO 2014/191521 A2 | 12/2014 |
| WO | WO 2014/191525 A1 | 12/2014 |
| WO | WO 2014/191527 A1 | 12/2014 |
| WO | WO 2014/193583 A2 | 12/2014 |
| WO | WO 2014/194190 A1 | 12/2014 |
| WO | WO 2014/197568 A2 | 12/2014 |
| WO | WO 2014/197748 A2 | 12/2014 |
| WO | WO 2014/199358 A1 | 12/2014 |
| WO | WO 2014/200659 A1 | 12/2014 |
| WO | WO 2014/201015 A2 | 12/2014 |
| WO | WO 2014/204578 A1 | 12/2014 |
| WO | WO 2014/204723 A1 | 12/2014 |
| WO | WO 2014/204724 A1 | 12/2014 |
| WO | WO 2014/204725 A1 | 12/2014 |
| WO | WO 2014/204726 A1 | 12/2014 |
| WO | WO 2014/204727 A1 | 12/2014 |
| WO | WO 2014/204728 A1 | 12/2014 |
| WO | WO 2014/204729 A1 | 12/2014 |
| WO | WO 2014/205192 A2 | 12/2014 |
| WO | WO 2014/207043 A1 | 12/2014 |
| WO | WO 2015/002780 A1 | 1/2015 |
| WO | WO 2015/004241 A2 | 1/2015 |
| WO | WO 2015/006290 A1 | 1/2015 |
| WO | WO 2015/006294 A2 | 1/2015 |
| WO | WO 2015/006437 A1 | 1/2015 |
| WO | WO 2015/006498 A2 | 1/2015 |
| WO | WO 2015/006747 A2 | 1/2015 |
| WO | WO 2015/007194 A1 | 1/2015 |
| WO | WO 2015/010114 A1 | 1/2015 |
| WO | WO 2015/011483 A1 | 1/2015 |
| WO | WO 2015/013583 A2 | 1/2015 |
| WO | WO 2015/017866 A1 | 2/2015 |
| WO | WO 2015/018503 A2 | 2/2015 |
| WO | WO 2015/021353 A1 | 2/2015 |
| WO | WO 2015/021426 A1 | 2/2015 |
| WO | WO 2015/021990 A1 | 2/2015 |
| WO | WO 2015/024017 A2 | 2/2015 |
| WO | WO 2015/024986 A1 | 2/2015 |
| WO | WO 2015/026883 A1 | 2/2015 |
| WO | WO 2015/026885 A1 | 2/2015 |
| WO | WO 2015/026886 A1 | 2/2015 |
| WO | WO 2015/026887 A1 | 2/2015 |
| WO | WO 2015/027134 A1 | 2/2015 |
| WO | WO 2015/028969 A2 | 3/2015 |
| WO | WO 2015/030881 A1 | 3/2015 |
| WO | WO 2015/031619 A1 | 3/2015 |
| WO | WO 2015/031775 A1 | 3/2015 |
| WO | WO 2015/032494 A2 | 3/2015 |
| WO | WO 2015/033293 A1 | 3/2015 |
| WO | WO 2015/034872 A2 | 3/2015 |
| WO | WO 2015/034885 A1 | 3/2015 |
| WO | WO 2015/035136 A2 | 3/2015 |
| WO | WO 2015/035139 A2 | 3/2015 |
| WO | WO 2015/035162 A2 | 3/2015 |
| WO | WO 2015/040075 A1 | 3/2015 |
| WO | WO 2015/040402 A2 | 3/2015 |
| WO | WO 2015/042585 A1 | 3/2015 |
| WO | WO 2015/048577 A2 | 4/2015 |
| WO | WO 2015/048690 A1 | 4/2015 |
| WO | WO 2015/048707 A2 | 4/2015 |
| WO | WO 2015/048801 A2 | 4/2015 |
| WO | WO 2015/049897 A1 | 4/2015 |
| WO | WO 2015/051191 A1 | 4/2015 |
| WO | WO 2015/052133 A1 | 4/2015 |
| WO | WO 2015/052231 A2 | 4/2015 |
| WO | WO 2015/052335 A1 | 4/2015 |
| WO | WO 2015/053995 A1 | 4/2015 |
| WO | WO 2015/054253 A1 | 4/2015 |
| WO | WO 2015/054315 A1 | 4/2015 |
| WO | WO 2015/057671 A1 | 4/2015 |
| WO | WO 2015/057834 A1 | 4/2015 |
| WO | WO 2015/057852 A1 | 4/2015 |
| WO | WO 2015/057976 A1 | 4/2015 |
| WO | WO 2015/057980 A1 | 4/2015 |
| WO | WO 2015/059265 A1 | 4/2015 |
| WO | WO 2015/065964 A1 | 5/2015 |
| WO | WO 2015/066119 A1 | 5/2015 |
| WO | WO 2015/066634 A2 | 5/2015 |
| WO | WO 2015/066636 A2 | 5/2015 |
| WO | WO 2015/066637 A1 | 5/2015 |
| WO | WO 2015/066638 A2 | 5/2015 |
| WO | WO 2015/066643 A1 | 5/2015 |
| WO | WO 2015/069682 A2 | 5/2015 |
| WO | WO 2015/070083 A1 | 5/2015 |
| WO | WO 2015/070193 A1 | 5/2015 |
| WO | WO 2015/070212 A1 | 5/2015 |
| WO | WO 2015/071474 A2 | 5/2015 |
| WO | WO 2015/073683 A2 | 5/2015 |
| WO | WO 2015/073867 A1 | 5/2015 |
| WO | WO 2015/073990 A1 | 5/2015 |
| WO | WO 2015/075056 A1 | 5/2015 |
| WO | WO 2015/075154 A2 | 5/2015 |
| WO | WO 2015/075175 A1 | 5/2015 |
| WO | WO 2015/075195 A1 | 5/2015 |
| WO | WO 2015/075557 A2 | 5/2015 |
| WO | WO 2015/077058 A2 | 5/2015 |
| WO | WO 2015/077290 A2 | 5/2015 |
| WO | WO 2015/077318 A1 | 5/2015 |
| WO | WO 2015/079056 A1 | 6/2015 |
| WO | WO 2015/079057 A2 | 6/2015 |
| WO | WO 2015/086795 A1 | 6/2015 |

(56) References Cited

FOREIGN PATENT DOCUMENTS

| | | |
|---|---|---|
| WO | WO 2015/086798 A2 | 6/2015 |
| WO | WO 2015/088643 A1 | 6/2015 |
| WO | WO 2015/089046 A1 | 6/2015 |
| WO | WO 2015/089077 A2 | 6/2015 |
| WO | WO 2015/089277 A1 | 6/2015 |
| WO | WO 2015/089351 A1 | 6/2015 |
| WO | WO 2015/089354 A1 | 6/2015 |
| WO | WO 2015/089364 A1 | 6/2015 |
| WO | WO 2015/089406 A1 | 6/2015 |
| WO | WO 2015/089419 A2 | 6/2015 |
| WO | WO 2015/089427 A1 | 6/2015 |
| WO | WO 2015/089462 A1 | 6/2015 |
| WO | WO 2015/089465 A1 | 6/2015 |
| WO | WO 2015/089473 A1 | 6/2015 |
| WO | WO 2015/089486 A2 | 6/2015 |
| WO | WO 2015/095804 A1 | 6/2015 |
| WO | WO 2015/099850 A1 | 7/2015 |
| WO | WO 2015/100929 A1 | 7/2015 |
| WO | WO 2015/103057 A1 | 7/2015 |
| WO | WO 2015/103153 A1 | 7/2015 |
| WO | WO 2015/105928 A1 | 7/2015 |
| WO | WO 2015/108993 A1 | 7/2015 |
| WO | WO 2015/109752 A1 | 7/2015 |
| WO | WO 2015/110474 A1 | 7/2015 |
| WO | WO 2015/112790 A2 | 7/2015 |
| WO | WO 2015/112896 A2 | 7/2015 |
| WO | WO 2015/113063 A1 | 7/2015 |
| WO | WO 2015/114365 A1 | 8/2015 |
| WO | WO 2015/115903 A1 | 8/2015 |
| WO | WO 2015/116686 A1 | 8/2015 |
| WO | WO 2015/116969 A2 | 8/2015 |
| WO | WO 2015/117021 A1 | 8/2015 |
| WO | WO 2015/117041 A1 | 8/2015 |
| WO | WO 2015/117081 A2 | 8/2015 |
| WO | WO 2015/118156 A1 | 8/2015 |
| WO | WO 2015/119941 A2 | 8/2015 |
| WO | WO 2015/121454 A1 | 8/2015 |
| WO | WO 2015/122967 A1 | 8/2015 |
| WO | WO 2015/123339 A1 | 8/2015 |
| WO | WO 2015/124715 A1 | 8/2015 |
| WO | WO 2015/124718 A1 | 8/2015 |
| WO | WO 2015/126927 A2 | 8/2015 |
| WO | WO 2015/127428 A1 | 8/2015 |
| WO | WO 2015/127439 A1 | 8/2015 |
| WO | WO 2015/129686 A1 | 9/2015 |
| WO | WO 2015/131101 A1 | 9/2015 |
| WO | WO 2015/133554 A1 | 9/2015 |
| WO | WO 2015/134121 A2 | 9/2015 |
| WO | WO 2015/134812 A1 | 9/2015 |
| WO | WO 2015/136001 A1 | 9/2015 |
| WO | WO 2015/138510 A1 | 9/2015 |
| WO | WO 2015/138739 A2 | 9/2015 |
| WO | WO 2015/138855 A1 | 9/2015 |
| WO | WO 2015/138870 A2 | 9/2015 |
| WO | WO 2015/139008 A1 | 9/2015 |
| WO | WO 2015/139139 A1 | 9/2015 |
| WO | WO 2015/143046 A2 | 9/2015 |
| WO | WO 2015/143177 A1 | 9/2015 |
| WO | WO 2015/145417 A1 | 10/2015 |
| WO | WO 2015/148431 A1 | 10/2015 |
| WO | WO 2015/148670 A1 | 10/2015 |
| WO | WO 2015/148680 A1 | 10/2015 |
| WO | WO 2015/148761 A1 | 10/2015 |
| WO | WO 2015/148860 A1 | 10/2015 |
| WO | WO 2015/148863 A2 | 10/2015 |
| WO | WO 2015/153760 A2 | 10/2015 |
| WO | WO 2015/153780 A1 | 10/2015 |
| WO | WO 2015/153789 A1 | 10/2015 |
| WO | WO 2015/153791 A1 | 10/2015 |
| WO | WO 2015/153889 A2 | 10/2015 |
| WO | WO 2015/153940 A1 | 10/2015 |
| WO | WO 2015/155341 A1 | 10/2015 |
| WO | WO 2015/155686 A2 | 10/2015 |
| WO | WO 2015/157070 A2 | 10/2015 |
| WO | WO 2015/157534 A1 | 10/2015 |
| WO | WO 2015/159068 A1 | 10/2015 |
| WO | WO 2015/159086 A1 | 10/2015 |
| WO | WO 2015/159087 A1 | 10/2015 |
| WO | WO 2015/160683 A1 | 10/2015 |
| WO | WO 2015/161276 A2 | 10/2015 |
| WO | WO 2015/163733 A1 | 10/2015 |
| WO | WO 2015/164740 A1 | 10/2015 |
| WO | WO 2015/164748 A1 | 10/2015 |
| WO | WO 2015/165274 A1 | 11/2015 |
| WO | WO 2015/165275 A1 | 11/2015 |
| WO | WO 2015/165276 A1 | 11/2015 |
| WO | WO 2015/166272 A2 | 11/2015 |
| WO | WO 2015/167766 A1 | 11/2015 |
| WO | WO 2015/167956 A1 | 11/2015 |
| WO | WO 2015/168125 A1 | 11/2015 |
| WO | WO 2015/168158 A1 | 11/2015 |
| WO | WO 2015/168404 A1 | 11/2015 |
| WO | WO 2015/168547 A2 | 11/2015 |
| WO | WO 2015/168800 A1 | 11/2015 |
| WO | WO 2015/171603 A1 | 11/2015 |
| WO | WO 2015/171894 A1 | 11/2015 |
| WO | WO 2015/171932 A1 | 11/2015 |
| WO | WO 2015/172128 A1 | 11/2015 |
| WO | WO 2015/173436 A1 | 11/2015 |
| WO | WO 2015/175642 A2 | 11/2015 |
| WO | WO 2015/179540 A1 | 11/2015 |
| WO | WO 2015/183025 A1 | 12/2015 |
| WO | WO 2015/183026 A1 | 12/2015 |
| WO | WO 2015/183885 A1 | 12/2015 |
| WO | WO 2015/184259 A1 | 12/2015 |
| WO | WO 2015/184262 A1 | 12/2015 |
| WO | WO 2015/184268 A1 | 12/2015 |
| WO | WO 2015/188056 A1 | 12/2015 |
| WO | WO 2015/188065 A1 | 12/2015 |
| WO | WO 2015/188094 A1 | 12/2015 |
| WO | WO 2015/188109 A1 | 12/2015 |
| WO | WO 2015/188132 A1 | 12/2015 |
| WO | WO 2015/188135 A1 | 12/2015 |
| WO | WO 2015/188191 A1 | 12/2015 |
| WO | WO 2015/189693 A1 | 12/2015 |
| WO | WO 2015/191693 A2 | 12/2015 |
| WO | WO 2015/191899 A1 | 12/2015 |
| WO | WO 2015/191911 A2 | 12/2015 |
| WO | WO 2015/193858 A1 | 12/2015 |
| WO | WO 2015/195547 A1 | 12/2015 |
| WO | WO 2015/195621 A1 | 12/2015 |
| WO | WO 2015/195798 A1 | 12/2015 |
| WO | WO 2015/198020 A1 | 12/2015 |
| WO | WO 2015/200334 A1 | 12/2015 |
| WO | WO 2015/200378 A1 | 12/2015 |
| WO | WO 2015/200555 A2 | 12/2015 |
| WO | WO 2015/200805 A2 | 12/2015 |
| WO | WO 2016/001978 A1 | 1/2016 |
| WO | WO 2016/004010 A1 | 1/2016 |
| WO | WO 2016/004318 A1 | 1/2016 |
| WO | WO 2016/007347 A1 | 1/2016 |
| WO | WO 2016/007604 A1 | 1/2016 |
| WO | WO 2016/007948 A1 | 1/2016 |
| WO | WO 2016/011080 A2 | 1/2016 |
| WO | WO 2016/011210 A2 | 1/2016 |
| WO | WO 2016/011428 A1 | 1/2016 |
| WO | WO 2016/012544 A2 | 1/2016 |
| WO | WO 2016/012552 A1 | 1/2016 |
| WO | WO 2016/014409 A1 | 1/2016 |
| WO | WO 2016/014565 A2 | 1/2016 |
| WO | WO 2016/014794 A1 | 1/2016 |
| WO | WO 2016/014837 A1 | 1/2016 |
| WO | WO 2016/016119 A1 | 2/2016 |
| WO | WO 2016/016358 A1 | 2/2016 |
| WO | WO 2016/019144 A2 | 2/2016 |
| WO | WO 2016/020399 A1 | 2/2016 |
| WO | WO 2016/021972 A1 | 2/2016 |
| WO | WO 2016/021973 A1 | 2/2016 |
| WO | WO 2016/022363 A2 | 2/2016 |
| WO | WO 2016/022866 A1 | 2/2016 |
| WO | WO 2016/022931 A1 | 2/2016 |
| WO | WO 2016/025131 A1 | 2/2016 |
| WO | WO 2016/025469 A1 | 2/2016 |
| WO | WO 2016/025759 A1 | 2/2016 |

(56) References Cited

FOREIGN PATENT DOCUMENTS

| | | |
|---|---|---|
| WO | WO 2016/026444 A1 | 2/2016 |
| WO | WO 2016/028682 A1 | 2/2016 |
| WO | WO 2016/028843 A2 | 2/2016 |
| WO | WO 2016/028887 A1 | 2/2016 |
| WO | WO 2016/033088 A1 | 3/2016 |
| WO | WO 2016/033230 A1 | 3/2016 |
| WO | WO 2016/033246 A1 | 3/2016 |
| WO | WO 2016/033298 A1 | 3/2016 |
| WO | WO 2016/035044 A1 | 3/2016 |
| WO | WO 2016/036754 A1 | 3/2016 |
| WO | WO 2016/037157 A2 | 3/2016 |
| WO | WO 2016/040030 A1 | 3/2016 |
| WO | WO 2016/040594 A1 | 3/2016 |
| WO | WO 2016/044182 A1 | 3/2016 |
| WO | WO 2016/044416 A1 | 3/2016 |
| WO | WO 2016/046635 A1 | 3/2016 |
| WO | WO 2016/049024 A2 | 3/2016 |
| WO | WO 2016/049163 A2 | 3/2016 |
| WO | WO 2016/049230 A1 | 3/2016 |
| WO | WO 2016/049251 A1 | 3/2016 |
| WO | WO 2016/049258 A2 | 3/2016 |
| WO | WO 2016/053397 A2 | 4/2016 |
| WO | WO 2016/054326 A1 | 4/2016 |
| WO | WO 2016/057061 A2 | 4/2016 |
| WO | WO 2016/057821 A2 | 4/2016 |
| WO | WO 2016/057835 A2 | 4/2016 |
| WO | WO 2016/057850 A1 | 4/2016 |
| WO | WO 2016/057951 A2 | 4/2016 |
| WO | WO 2016/057961 A1 | 4/2016 |
| WO | WO 2016/061073 A1 | 4/2016 |
| WO | WO 2016/061374 A1 | 4/2016 |
| WO | WO 2016/061481 A1 | 4/2016 |
| WO | WO 2016/061523 A1 | 4/2016 |
| WO | WO 2016/064894 A2 | 4/2016 |
| WO | WO 2016/069282 A1 | 5/2016 |
| WO | WO 2016/069283 A1 | 5/2016 |
| WO | WO 2016/069591 A2 | 5/2016 |
| WO | WO 2016/069774 A1 | 5/2016 |
| WO | WO 2016/069910 A1 | 5/2016 |
| WO | WO 2016/069912 A1 | 5/2016 |
| WO | WO 2016/070037 A2 | 5/2016 |
| WO | WO 2016/070070 A1 | 5/2016 |
| WO | WO 2016/070129 A1 | 5/2016 |
| WO | WO 2016/072399 A1 | 5/2016 |
| WO | WO 2016/072936 A1 | 5/2016 |
| WO | WO 2016/073433 A1 | 5/2016 |
| WO | WO 2016/073559 A1 | 5/2016 |
| WO | WO 2016/073990 A2 | 5/2016 |
| WO | WO 2016/075662 A2 | 5/2016 |
| WO | WO 2016/076672 A1 | 5/2016 |
| WO | WO 2016/077273 A1 | 5/2016 |
| WO | WO 2016/077350 A1 | 5/2016 |
| WO | WO 2016/080097 A1 | 5/2016 |
| WO | WO 2016/080795 A1 | 5/2016 |
| WO | WO 2016/081923 A2 | 5/2016 |
| WO | WO 2016/081924 A1 | 5/2016 |
| WO | WO 2016/082135 A1 | 6/2016 |
| WO | WO 2016/083811 A1 | 6/2016 |
| WO | WO 2016/084084 A1 | 6/2016 |
| WO | WO 2016/084088 A1 | 6/2016 |
| WO | WO 2016/086177 A2 | 6/2016 |
| WO | WO 2016/089433 A1 | 6/2016 |
| WO | WO 2016/089866 A1 | 6/2016 |
| WO | WO 2016/089883 A1 | 6/2016 |
| WO | WO 2016/090385 A1 | 6/2016 |
| WO | WO 2016/094679 A1 | 6/2016 |
| WO | WO 2016/094845 A2 | 6/2016 |
| WO | WO 2016/094867 A1 | 6/2016 |
| WO | WO 2016/094872 A1 | 6/2016 |
| WO | WO 2016/094874 A1 | 6/2016 |
| WO | WO 2016/094880 A1 | 6/2016 |
| WO | WO 2016/094888 A1 | 6/2016 |
| WO | WO 2016/097212 A1 | 6/2016 |
| WO | WO 2016/097231 A2 | 6/2016 |
| WO | WO 2016/097751 A1 | 6/2016 |
| WO | WO 2016/099887 A1 | 6/2016 |
| WO | WO 2016/100272 A1 | 6/2016 |
| WO | WO 2016/100389 A1 | 6/2016 |
| WO | WO 2016/100568 A1 | 6/2016 |
| WO | WO 2016/100571 A1 | 6/2016 |
| WO | WO 2016/100951 A2 | 6/2016 |
| WO | WO 2016/100955 A2 | 6/2016 |
| WO | WO 2016/100974 A1 | 6/2016 |
| WO | WO 2016/103233 A2 | 6/2016 |
| WO | WO 2016/104716 A1 | 6/2016 |
| WO | WO 2016/106236 A1 | 6/2016 |
| WO | WO 2016/106239 A1 | 6/2016 |
| WO | WO 2016/106244 A1 | 6/2016 |
| WO | WO 2016/106338 A2 | 6/2016 |
| WO | WO 2016/108926 A1 | 7/2016 |
| WO | WO 2016/109255 A1 | 7/2016 |
| WO | WO 2016/109840 A2 | 7/2016 |
| WO | WO 2016/110214 A1 | 7/2016 |
| WO | WO 2016/110453 A1 | 7/2016 |
| WO | WO 2016/110511 A1 | 7/2016 |
| WO | WO 2016/110512 A1 | 7/2016 |
| WO | WO 2016/111546 A2 | 7/2016 |
| WO | WO 2016/112242 A1 | 7/2016 |
| WO | WO 2016/112351 A1 | 7/2016 |
| WO | WO 2016/112963 A1 | 7/2016 |
| WO | WO 2016/114972 A1 | 7/2016 |
| WO | WO 2016/115179 A1 | 7/2016 |
| WO | WO 2016/115326 A1 | 7/2016 |
| WO | WO 2016/115355 A1 | 7/2016 |
| WO | WO 2016/116032 A1 | 7/2016 |
| WO | WO 2016/120480 A1 | 8/2016 |
| WO | WO 2016/123071 A1 | 8/2016 |
| WO | WO 2016/123230 A1 | 8/2016 |
| WO | WO 2016/123243 A1 | 8/2016 |
| WO | WO 2016/123578 A1 | 8/2016 |
| WO | WO 2016/126747 A1 | 8/2016 |
| WO | WO 2016/130600 A2 | 8/2016 |
| WO | WO 2016/130697 A1 | 8/2016 |
| WO | WO 2016/131009 A1 | 8/2016 |
| WO | WO 2016/132122 A1 | 8/2016 |
| WO | WO 2016/133165 A1 | 8/2016 |
| WO | WO 2016/135507 A1 | 9/2016 |
| WO | WO 2016/135557 A2 | 9/2016 |
| WO | WO 2016/135558 A2 | 9/2016 |
| WO | WO 2016/135559 A2 | 9/2016 |
| WO | WO 2016/137774 A1 | 9/2016 |
| WO | WO 2016/137949 A1 | 9/2016 |
| WO | WO 2016/141224 A1 | 9/2016 |
| WO | WO 2016/141893 A1 | 9/2016 |
| WO | WO 2016/142719 A1 | 9/2016 |
| WO | WO 2016/145150 A2 | 9/2016 |
| WO | WO 2016/148994 A1 | 9/2016 |
| WO | WO 2016/149484 A2 | 9/2016 |
| WO | WO 2016/149547 A1 | 9/2016 |
| WO | WO 2016/150336 A1 | 9/2016 |
| WO | WO 2016/150855 A1 | 9/2016 |
| WO | WO 2016/154016 A2 | 9/2016 |
| WO | WO 2016/154579 A2 | 9/2016 |
| WO | WO 2016/154596 A1 | 9/2016 |
| WO | WO 2016/155482 A1 | 10/2016 |
| WO | WO 2016/161004 A1 | 10/2016 |
| WO | WO 2016/161207 A1 | 10/2016 |
| WO | WO 2016/161260 A1 | 10/2016 |
| WO | WO 2016/161380 A1 | 10/2016 |
| WO | WO 2016/161446 A1 | 10/2016 |
| WO | WO 2016/164356 A1 | 10/2016 |
| WO | WO 2016/164797 A1 | 10/2016 |
| WO | WO 2016/166340 A1 | 10/2016 |
| WO | WO 2016/167300 A1 | 10/2016 |
| WO | WO 2016/168631 A1 | 10/2016 |
| WO | WO 2016/170484 A1 | 10/2016 |
| WO | WO 2016/172359 A2 | 10/2016 |
| WO | WO 2016/172727 A1 | 10/2016 |
| WO | WO 2016/174056 A1 | 11/2016 |
| WO | WO 2016/174151 A1 | 11/2016 |
| WO | WO 2016/174250 A1 | 11/2016 |
| WO | WO 2016/176191 A1 | 11/2016 |
| WO | WO 2016/176404 A1 | 11/2016 |
| WO | WO 2016/176690 A2 | 11/2016 |

(56) References Cited

FOREIGN PATENT DOCUMENTS

| | | |
|---|---|---|
| WO | WO 2016/177682 A1 | 11/2016 |
| WO | WO 2016/178207 A1 | 11/2016 |
| WO | WO 2016/179038 A1 | 11/2016 |
| WO | WO 2016/179112 A1 | 11/2016 |
| WO | WO 2016/181357 A1 | 11/2016 |
| WO | WO 2016/182893 A1 | 11/2016 |
| WO | WO 2016/182917 A1 | 11/2016 |
| WO | WO 2016/182959 A1 | 11/2016 |
| WO | WO 2016/183236 A1 | 11/2016 |
| WO | WO 2016/183298 A2 | 11/2016 |
| WO | WO 2016/183345 A1 | 11/2016 |
| WO | WO 2016/183402 A2 | 11/2016 |
| WO | WO 2016/183438 A1 | 11/2016 |
| WO | WO 2016/183448 A1 | 11/2016 |
| WO | WO 2016/184955 A2 | 11/2016 |
| WO | WO 2016/184989 A1 | 11/2016 |
| WO | WO 2016/185411 A1 | 11/2016 |
| WO | WO 2016/186745 A1 | 11/2016 |
| WO | WO 2016/186772 A2 | 11/2016 |
| WO | WO 2016/186946 A1 | 11/2016 |
| WO | WO 2016/186953 A1 | 11/2016 |
| WO | WO 2016/187717 A1 | 12/2016 |
| WO | WO 2016/187904 A1 | 12/2016 |
| WO | WO 2016/191684 A1 | 12/2016 |
| WO | WO 2016/191869 A1 | 12/2016 |
| WO | WO 2016/196273 A1 | 12/2016 |
| WO | WO 2016/196282 A1 | 12/2016 |
| WO | WO 2016/196308 A1 | 12/2016 |
| WO | WO 2016/196361 A1 | 12/2016 |
| WO | WO 2016/196499 A1 | 12/2016 |
| WO | WO 2016/196539 A2 | 12/2016 |
| WO | WO 2016/196655 A1 | 12/2016 |
| WO | WO 2016/196805 A1 | 12/2016 |
| WO | WO 2016/196887 A1 | 12/2016 |
| WO | WO 2016/197132 A1 | 12/2016 |
| WO | WO 2016/197133 A1 | 12/2016 |
| WO | WO 2016/197354 A1 | 12/2016 |
| WO | WO 2016/197355 A1 | 12/2016 |
| WO | WO 2016/197356 A1 | 12/2016 |
| WO | WO 2016/197357 A1 | 12/2016 |
| WO | WO 2016/197358 A1 | 12/2016 |
| WO | WO 2016/197359 A1 | 12/2016 |
| WO | WO 2016/197360 A1 | 12/2016 |
| WO | WO 2016/197361 A1 | 12/2016 |
| WO | WO 2016/197362 A1 | 12/2016 |
| WO | WO 2016/198361 A1 | 12/2016 |
| WO | WO 2016/198500 A1 | 12/2016 |
| WO | WO 2016/200263 A1 | 12/2016 |
| WO | WO 2016/201047 A1 | 12/2016 |
| WO | WO 2016/201138 A1 | 12/2016 |
| WO | WO 2016/201152 A1 | 12/2016 |
| WO | WO 2016/201153 A1 | 12/2016 |
| WO | WO 2016/201155 A1 | 12/2016 |
| WO | WO 2016/205276 A1 | 12/2016 |
| WO | WO 2016/205613 A1 | 12/2016 |
| WO | WO 2016/205623 A1 | 12/2016 |
| WO | WO 2016/205680 A1 | 12/2016 |
| WO | WO 2016/205688 A2 | 12/2016 |
| WO | WO 2016/205703 A1 | 12/2016 |
| WO | WO 2016/205711 A1 | 12/2016 |
| WO | WO 2016/205728 A1 | 12/2016 |
| WO | WO 2016/205745 A2 | 12/2016 |
| WO | WO 2016/205749 A1 | 12/2016 |
| WO | WO 2016/205759 A1 | 12/2016 |
| WO | WO 2016/205764 A1 | 12/2016 |
| WO | WO 2017/001572 A1 | 1/2017 |
| WO | WO 2017/001988 A1 | 1/2017 |
| WO | WO 2017/004261 A1 | 1/2017 |
| WO | WO 2017/004279 A2 | 1/2017 |
| WO | WO 2017/004616 A1 | 1/2017 |
| WO | WO 2017/005807 A1 | 1/2017 |
| WO | WO 2017/009399 A1 | 1/2017 |
| WO | WO 2017/010556 A1 | 1/2017 |
| WO | WO 2017/011519 A1 | 1/2017 |
| WO | WO 2017/011721 A1 | 1/2017 |
| WO | WO 2017/011804 A1 | 1/2017 |
| WO | WO 2017/015015 A1 | 1/2017 |
| WO | WO 2017/015101 A1 | 1/2017 |
| WO | WO 2017/015545 A1 | 1/2017 |
| WO | WO 2017/015567 A1 | 1/2017 |
| WO | WO 2017/015637 A1 | 1/2017 |
| WO | WO 2017/017016 A1 | 2/2017 |
| WO | WO 2017/019867 A1 | 2/2017 |
| WO | WO 2017/019895 A1 | 2/2017 |
| WO | WO 2017/023803 A1 | 2/2017 |
| WO | WO 2017/023974 A1 | 2/2017 |
| WO | WO 2017/024047 A1 | 2/2017 |
| WO | WO 2017/024319 A1 | 2/2017 |
| WO | WO 2017/024343 A1 | 2/2017 |
| WO | WO 2017/024602 A1 | 2/2017 |
| WO | WO 2017/025323 A1 | 2/2017 |
| WO | WO 2017/027423 A1 | 2/2017 |
| WO | WO 2017/028768 A1 | 2/2017 |
| WO | WO 2017/029664 A1 | 2/2017 |
| WO | WO 2017/031360 A1 | 2/2017 |
| WO | WO 2017/031483 A1 | 2/2017 |
| WO | WO 2017/035416 A2 | 3/2017 |
| WO | WO 2017/040348 A1 | 3/2017 |
| WO | WO 2017/040511 A1 | 3/2017 |
| WO | WO 2017/040709 A1 | 3/2017 |
| WO | WO 2017/040786 A1 | 3/2017 |
| WO | WO 2017/040793 A1 | 3/2017 |
| WO | WO 2017/040813 A2 | 3/2017 |
| WO | WO 2017/043573 A1 | 3/2017 |
| WO | WO 2017/043656 A1 | 3/2017 |
| WO | WO 2017/044419 A1 | 3/2017 |
| WO | WO 2017/044776 A1 | 3/2017 |
| WO | WO 2017/044857 A2 | 3/2017 |
| WO | WO 2017/048390 A1 | 3/2017 |
| WO | WO 2017/049129 A2 | 3/2017 |
| WO | WO 2017/050963 A1 | 3/2017 |
| WO | WO 2017/053312 A1 | 3/2017 |
| WO | WO 2017/053431 A2 | 3/2017 |
| WO | WO 2017/053713 A1 | 3/2017 |
| WO | WO 2017/053729 A1 | 3/2017 |
| WO | WO 2017/053753 A1 | 3/2017 |
| WO | WO 2017/053762 A1 | 3/2017 |
| WO | WO 2017/053879 A1 | 3/2017 |
| WO | WO 2017/054721 A1 | 4/2017 |
| WO | WO 2017/058658 A2 | 4/2017 |
| WO | WO 2017/059241 A1 | 4/2017 |
| WO | WO 2017/062605 A1 | 4/2017 |
| WO | WO 2017/062723 A1 | 4/2017 |
| WO | WO 2017/062754 A1 | 4/2017 |
| WO | WO 2017/062855 A1 | 4/2017 |
| WO | WO 2017/062886 A1 | 4/2017 |
| WO | WO 2017/062983 A1 | 4/2017 |
| WO | WO 2017/064439 A1 | 4/2017 |
| WO | WO 2017/064546 A1 | 4/2017 |
| WO | WO 2017/064566 A2 | 4/2017 |
| WO | WO 2017/066175 A1 | 4/2017 |
| WO | WO 2017/066497 A2 | 4/2017 |
| WO | WO 2017/066588 A2 | 4/2017 |
| WO | WO 2017/066707 A1 | 4/2017 |
| WO | WO 2017/066781 A1 | 4/2017 |
| WO | WO 2017/068077 A1 | 4/2017 |
| WO | WO 2017/068377 A1 | 4/2017 |
| WO | WO 2017/069829 A2 | 4/2017 |
| WO | WO 2017/070029 A1 | 4/2017 |
| WO | WO 2017/070032 A1 | 4/2017 |
| WO | WO 2017/070169 A1 | 4/2017 |
| WO | WO 2017/070284 A1 | 4/2017 |
| WO | WO 2017/070598 A1 | 4/2017 |
| WO | WO 2017/070605 A1 | 4/2017 |
| WO | WO 2017/070632 A2 | 4/2017 |
| WO | WO 2017/070633 A2 | 4/2017 |
| WO | WO 2017/072590 A1 | 5/2017 |
| WO | WO 2017/074526 A1 | 5/2017 |
| WO | WO 2017/074962 A1 | 5/2017 |
| WO | WO 2017/075261 A1 | 5/2017 |
| WO | WO 2017/075335 A1 | 5/2017 |
| WO | WO 2017/075475 A1 | 5/2017 |
| WO | WO 2017/077135 A1 | 5/2017 |
| WO | WO 2017/077329 A2 | 5/2017 |

(56) References Cited

FOREIGN PATENT DOCUMENTS

| | | |
|---|---|---|
| WO | WO 2017/078751 A1 | 5/2017 |
| WO | WO 2017/079400 A1 | 5/2017 |
| WO | WO 2017/079428 A1 | 5/2017 |
| WO | WO 2017/079673 A1 | 5/2017 |
| WO | WO 2017/079724 A1 | 5/2017 |
| WO | WO 2017/081097 A1 | 5/2017 |
| WO | WO 2017/081288 A1 | 5/2017 |
| WO | WO 2017/083368 A1 | 5/2017 |
| WO | WO 2017/083722 A1 | 5/2017 |
| WO | WO 2017/083766 A1 | 5/2017 |
| WO | WO 2017/087395 A1 | 5/2017 |
| WO | WO 2017/090724 A1 | 6/2017 |
| WO | WO 2017/091510 A1 | 6/2017 |
| WO | WO 2017/091630 A1 | 6/2017 |
| WO | WO 2017/092201 A1 | 6/2017 |
| WO | WO 2017/093370 A1 | 6/2017 |
| WO | WO 2017/093969 A1 | 6/2017 |
| WO | WO 2017/095111 A1 | 6/2017 |
| WO | WO 2017/096041 A1 | 6/2017 |
| WO | WO 2017/096237 A1 | 6/2017 |
| WO | WO 2017/100158 A1 | 6/2017 |
| WO | WO 2017/100431 A2 | 6/2017 |
| WO | WO 2017/104404 A1 | 6/2017 |
| WO | WO 2017/105251 A1 | 6/2017 |
| WO | WO 2017/105350 A1 | 6/2017 |
| WO | WO 2017/105991 A1 | 6/2017 |
| WO | WO 2017/106414 A1 | 6/2017 |
| WO | WO 2017/106528 A2 | 6/2017 |
| WO | WO 2017/106537 A2 | 6/2017 |
| WO | WO 2017/106569 A1 | 6/2017 |
| WO | WO 2017/106616 A1 | 6/2017 |
| WO | WO 2017/106657 A1 | 6/2017 |
| WO | WO 2017/106767 A1 | 6/2017 |
| WO | WO 2017/109134 A1 | 6/2017 |
| WO | WO 2017/109757 A1 | 6/2017 |
| WO | WO 2017/112620 A1 | 6/2017 |
| WO | WO 2017/115268 A1 | 7/2017 |
| WO | WO 2017/117395 A1 | 7/2017 |
| WO | WO 2017/118598 A1 | 7/2017 |
| WO | WO 2017/118720 A1 | 7/2017 |
| WO | WO 2017/123609 A1 | 7/2017 |
| WO | WO 2017/123910 A1 | 7/2017 |
| WO | WO 2017/124086 A1 | 7/2017 |
| WO | WO 2017/124100 A1 | 7/2017 |
| WO | WO 2017/124652 A1 | 7/2017 |
| WO | WO 2017/126987 A1 | 7/2017 |
| WO | WO 2017/127807 A1 | 7/2017 |
| WO | WO 2017/131237 A1 | 8/2017 |
| WO | WO 2017/132112 A1 | 8/2017 |
| WO | WO 2017/132580 A2 | 8/2017 |
| WO | WO 2017/136520 A1 | 8/2017 |
| WO | WO 2017/136629 A1 | 8/2017 |
| WO | WO 2017/136794 A1 | 8/2017 |
| WO | WO 2017/139264 A1 | 8/2017 |
| WO | WO 2017/139505 A2 | 8/2017 |
| WO | WO 2017/141173 A2 | 8/2017 |
| WO | WO 2017/142835 A1 | 8/2017 |
| WO | WO 2017/142999 A2 | 8/2017 |
| WO | WO 2017/143042 A2 | 8/2017 |
| WO | WO 2017/147278 A1 | 8/2017 |
| WO | WO 2017/147432 A1 | 8/2017 |
| WO | WO 2017/147446 A1 | 8/2017 |
| WO | WO 2017/147555 A1 | 8/2017 |
| WO | WO 2017/151444 A1 | 9/2017 |
| WO | WO 2017/151719 A1 | 9/2017 |
| WO | WO 2017/152015 A1 | 9/2017 |
| WO | WO 2017/155717 A1 | 9/2017 |
| WO | WO 2017/157422 A1 | 9/2017 |
| WO | WO 2017/158153 A1 | 9/2017 |
| WO | WO 2017/160689 A1 | 9/2017 |
| WO | WO 2017/160752 A1 | 9/2017 |
| WO | WO 2017/160890 A1 | 9/2017 |
| WO | WO 2017/161068 A1 | 9/2017 |
| WO | WO 2017/165826 A1 | 9/2017 |
| WO | WO 2017/165862 A1 | 9/2017 |
| WO | WO 2017/172644 A2 | 10/2017 |
| WO | WO 2017/172645 A2 | 10/2017 |
| WO | WO 2017/172860 A1 | 10/2017 |
| WO | WO 2017/173004 A1 | 10/2017 |
| WO | WO 2017/173054 A1 | 10/2017 |
| WO | WO 2017/173092 A1 | 10/2017 |
| WO | WO 2017/174329 A1 | 10/2017 |
| WO | WO 2017/176529 A1 | 10/2017 |
| WO | WO 2017/176806 A1 | 10/2017 |
| WO | WO 2017/178590 A1 | 10/2017 |
| WO | WO 2017/180694 A1 | 10/2017 |
| WO | WO 2017/180711 A1 | 10/2017 |
| WO | WO 2017/180915 A2 | 10/2017 |
| WO | WO 2017/180926 A1 | 10/2017 |
| WO | WO 2017/181107 A2 | 10/2017 |
| WO | WO 2017/181735 A2 | 10/2017 |
| WO | WO 2017/182468 A1 | 10/2017 |
| WO | WO 2017/184334 A1 | 10/2017 |
| WO | WO 2017/184768 A1 | 10/2017 |
| WO | WO 2017/184786 A1 | 10/2017 |
| WO | WO 2017/186550 A1 | 11/2017 |
| WO | WO 2017/189308 A1 | 11/2017 |
| WO | WO 2017/189336 A1 | 11/2017 |
| WO | WO 2017/190257 A1 | 11/2017 |
| WO | WO 2017/190664 A1 | 11/2017 |
| WO | WO 2017/191210 A1 | 11/2017 |
| WO | WO 2017/192172 A1 | 11/2017 |
| WO | WO 2017/192512 A2 | 11/2017 |
| WO | WO 2017/192544 A1 | 11/2017 |
| WO | WO 2017/192573 A1 | 11/2017 |
| WO | WO 2017/193029 A2 | 11/2017 |
| WO | WO 2017/193053 A1 | 11/2017 |
| WO | WO 2017/196768 A1 | 11/2017 |
| WO | WO 2017/197038 A1 | 11/2017 |
| WO | WO 2017/197238 A1 | 11/2017 |
| WO | WO 2017/197301 A1 | 11/2017 |
| WO | WO 2017/201476 A1 | 11/2017 |
| WO | WO 2017/205290 A1 | 11/2017 |
| WO | WO 2017/205423 A1 | 11/2017 |
| WO | WO 2017/207589 A1 | 12/2017 |
| WO | WO 2017/208247 A1 | 12/2017 |
| WO | WO 2017/209809 A1 | 12/2017 |
| WO | WO 2017/213896 A1 | 12/2017 |
| WO | WO 2017/213898 A2 | 12/2017 |
| WO | WO 2017/214460 A1 | 12/2017 |
| WO | WO 2017/216392 A1 | 12/2017 |
| WO | WO 2017/216771 A2 | 12/2017 |
| WO | WO 2017/218185 A1 | 12/2017 |
| WO | WO 2017/219027 A1 | 12/2017 |
| WO | WO 2017/219033 A1 | 12/2017 |
| WO | WO 2017/220751 A1 | 12/2017 |
| WO | WO 2017/222370 A1 | 12/2017 |
| WO | WO 2017/222773 A1 | 12/2017 |
| WO | WO 2017/222834 A1 | 12/2017 |
| WO | WO 2017/223107 A1 | 12/2017 |
| WO | WO 2017/223330 A1 | 12/2017 |
| WO | WO 2018/000657 A1 | 1/2018 |
| WO | WO 2018/002719 A1 | 1/2018 |
| WO | WO 2018/005117 A1 | 1/2018 |
| WO | WO 2018/005289 A2 | 1/2018 |
| WO | WO 2018/005691 A1 | 1/2018 |
| WO | WO 2018/005782 A1 | 1/2018 |
| WO | WO 2018/005873 A1 | 1/2018 |
| WO | WO 2018/06693 A1 | 1/2018 |
| WO | WO 2018/009520 A1 | 1/2018 |
| WO | WO 2018/009562 A1 | 1/2018 |
| WO | WO 2018/009822 A1 | 1/2018 |
| WO | WO 2018/013821 A1 | 1/2018 |
| WO | WO 2018/013990 A1 | 1/2018 |
| WO | WO 2018/014384 A1 | 1/2018 |
| WO | WO 2018/015444 A1 | 1/2018 |
| WO | WO 2018/015936 A2 | 1/2018 |
| WO | WO 2018/017754 A1 | 1/2018 |
| WO | WO 2018/018979 A1 | 2/2018 |
| WO | WO 2018/020248 A1 | 2/2018 |
| WO | WO 2018/021878 A1 | 2/2018 |
| WO | WO 2018/022480 A1 | 2/2018 |
| WO | WO 2018/022634 A1 | 2/2018 |
| WO | WO 2018/025206 A1 | 2/2018 |

(56) References Cited

FOREIGN PATENT DOCUMENTS

| | | |
|---|---|---|
| WO | WO 2018/026723 A1 | 2/2018 |
| WO | WO 2018/026976 A1 | 2/2018 |
| WO | WO 2018/027078 A1 | 2/2018 |
| WO | WO 2018/030608 A1 | 2/2018 |
| WO | WO 2018/031683 A1 | 2/2018 |
| WO | WO 2018/035250 A1 | 2/2018 |
| WO | WO 2018/035300 A1 | 2/2018 |
| WO | WO 2018/035423 A1 | 2/2018 |
| WO | WO 2018/035503 A1 | 2/2018 |
| WO | WO 2018/039145 A1 | 3/2018 |
| WO | WO 2018/039438 A1 | 3/2018 |
| WO | WO 2018/039440 A1 | 3/2018 |
| WO | WO 2018/039448 A1 | 3/2018 |
| WO | WO 2018/045630 A1 | 3/2018 |
| WO | WO 2018/048827 A1 | 3/2018 |
| WO | WO 2018/049168 A1 | 3/2018 |
| WO | WO 2018/051347 A1 | 3/2018 |
| WO | WO 2018/058064 A1 | 3/2018 |
| WO | WO 2018/062866 A2 | 4/2018 |
| WO | WO 2018/064352 A1 | 4/2018 |
| WO | WO 2018/064371 A1 | 4/2018 |
| WO | WO 2018/064516 A1 | 4/2018 |
| WO | WO 2018/067546 A1 | 4/2018 |
| WO | WO 2018/067846 A1 | 4/2018 |
| WO | WO 2018/068053 A2 | 4/2018 |
| WO | WO 2018/069474 A1 | 4/2018 |
| WO | WO 2018/071623 A2 | 4/2018 |
| WO | WO 2018/071663 A1 | 4/2018 |
| WO | WO 2018/071868 A1 | 4/2018 |
| WO | WO 2018/071892 A1 | 4/2018 |
| WO | WO 2018/074979 | 4/2018 |
| WO | WO 2018/079134 A1 | 5/2018 |
| WO | WO 2018/080573 A1 | 5/2018 |
| WO | WO 2018/081504 A1 | 5/2018 |
| WO | WO 2018/081535 A2 | 5/2018 |
| WO | WO 2018/081728 A1 | 5/2018 |
| WO | WO 2018/083128 A2 | 5/2018 |
| WO | WO 2018/083606 A1 | 5/2018 |
| WO | WO 2018/085288 A1 | 5/2018 |
| WO | WO 2018/086623 A1 | 5/2018 |
| WO | WO 2018/089664 A1 | 5/2018 |
| WO | WO 2018/093990 A1 | 5/2018 |
| WO | WO 2018/098383 A1 | 5/2018 |
| WO | WO 2018/098480 A1 | 5/2018 |
| WO | WO 2018/098587 A1 | 6/2018 |
| WO | WO 2018/099256 A1 | 6/2018 |
| WO | WO 2018/103686 A1 | 6/2018 |
| WO | WO 2018/106268 A1 | 6/2018 |
| WO | WO 2018/107028 A1 | 6/2018 |
| WO | WO 2018/107103 A1 | 6/2018 |
| WO | WO 2018/107129 A1 | 6/2018 |
| WO | WO 2018-108272 A1 | 6/2018 |
| WO | WO 2018/109101 A1 | 6/2018 |
| WO | WO 2018/111946 A1 | 6/2018 |
| WO | WO 2018/111947 A1 | 6/2018 |
| WO | WO 2018/112336 A1 | 6/2018 |
| WO | WO 2018/112446 A2 | 6/2018 |
| WO | WO 2018/119354 A1 | 6/2018 |
| WO | WO 2018/119359 A1 | 6/2018 |
| WO | WO 2018/120283 A1 | 7/2018 |
| WO | WO 2018/130830 A1 | 7/2018 |
| WO | WO 2018/135838 A1 | 7/2018 |
| WO | WO 2018/136396 A2 | 7/2018 |
| WO | WO 2018/138385 A1 | 8/2018 |
| WO | WO 2018/148246 A1 | 8/2018 |
| WO | WO 2018/148256 A1 | 8/2018 |
| WO | WO 2018/148647 A1 | 8/2018 |
| WO | WO 2018/149418 A1 | 8/2018 |
| WO | WO 2018/149888 A1 | 8/2018 |
| WO | WO 2018/152197 A1 | 8/2018 |
| WO | WO 2018/152418 A1 | 8/2018 |
| WO | WO 2018/154380 A1 | 8/2018 |
| WO | WO 2018/154387 A1 | 8/2018 |
| WO | WO 2018/154412 A1 | 8/2018 |
| WO | WO 2018/154413 A1 | 8/2018 |
| WO | WO 2018/154418 A1 | 8/2018 |
| WO | WO 2018/154439 A1 | 8/2018 |
| WO | WO 2018/154459 A1 | 8/2018 |
| WO | WO 2018/154462 A1 | 8/2018 |
| WO | WO 2018/156372 A1 | 8/2018 |
| WO | WO 2018/161009 A1 | 9/2018 |
| WO | WO 2018/165504 A1 | 9/2018 |
| WO | WO 2018/165629 A1 | 9/2018 |
| WO | WO 2018/170015 A1 | 9/2018 |
| WO | WO 2018/170340 A1 | 9/2018 |
| WO | WO 2018/175502 A2 | 9/2018 |
| WO | WO 2018/176009 A1 | 9/2018 |
| WO | WO 2018/177351 A1 | 10/2018 |
| WO | WO 2018/179578 A1 | 10/2018 |
| WO | WO 2018/183403 A1 | 10/2018 |
| WO | WO 2018/195402 A1 | 10/2018 |
| WO | WO 2018/195545 A2 | 10/2018 |
| WO | WO 2018/195555 A1 | 10/2018 |
| WO | WO 2018/197020 A1 | 11/2018 |
| WO | WO 2018/197495 A1 | 11/2018 |
| WO | WO 2018/202800 A1 | 11/2018 |
| WO | WO 2018/204493 A1 | 11/2018 |
| WO | WO 2018/208755 A1 | 11/2018 |
| WO | WO 2018/208998 A1 | 11/2018 |
| WO | WO 2018/209158 A2 | 11/2018 |
| WO | WO 2018/209320 A1 | 11/2018 |
| WO | WO 2018/213708 A1 | 11/2018 |
| WO | WO 2018/213726 A1 | 11/2018 |
| WO | WO 2018/213771 A1 | 11/2018 |
| WO | WO 2018/213791 A1 | 11/2018 |
| WO | WO 2018/217852 A1 | 11/2018 |
| WO | WO 2018/217981 A1 | 11/2018 |
| WO | WO 2018/218166 A1 | 11/2018 |
| WO | WO 2018/218188 A2 | 11/2018 |
| WO | WO 2018/218206 A1 | 11/2018 |
| WO | WO 2019/005886 A1 | 1/2019 |
| WO | WO 2019/010384 A1 | 1/2019 |
| WO | WO 2019/023680 A1 | 1/2019 |
| WO | WO 2019/051097 A1 | 3/2019 |
| WO | WO 2019/079347 | 4/2019 |
| WO | WO 2019/118949 A1 | 6/2019 |
| WO | WO 2019/139645 A2 | 7/2019 |
| WO | WO 2019/139951 A1 | 7/2019 |
| WO | WO 2019/226953 A1 | 11/2019 |
| WO | WO 2020/014261 A1 | 1/2020 |
| WO | WO 2020/041751 A1 | 2/2020 |
| WO | WO 2020/051360 A1 | 3/2020 |
| WO | WO 2020/086908 A1 | 4/2020 |
| WO | WO 2020/092453 A1 | 5/2020 |
| WO | WO 2020/102659 A1 | 5/2020 |
| WO | WO 2020/154500 A1 | 7/2020 |
| WO | WO 2020/181178 A1 | 9/2020 |
| WO | WO 2020/181180 A1 | 9/2020 |
| WO | WO 2020/181193 A1 | 9/2020 |
| WO | WO 2020/181195 A1 | 9/2020 |
| WO | WO 2020/181202 A1 | 9/2020 |
| WO | WO 2020/191153 A1 | 9/2020 |
| WO | WO 2020/191171 A1 | 9/2020 |
| WO | WO 2020/191233 A1 | 9/2020 |
| WO | WO 2020/191234 A1 | 9/2020 |
| WO | WO 2020/191239 A1 | 9/2020 |
| WO | WO 2020/191241 A1 | 9/2020 |
| WO | WO 2020/191242 A1 | 9/2020 |
| WO | WO 2020/191243 A1 | 9/2020 |
| WO | WO 2020/191245 A1 | 9/2020 |
| WO | WO 2020/191246 A1 | 9/2020 |
| WO | WO 2020/191248 A1 | 9/2020 |
| WO | WO 2020/191249 A1 | 9/2020 |
| WO | WO 2020/210751 A1 | 10/2020 |
| WO | WO 2020/214842 A1 | 10/2020 |
| WO | WO 2020/236982 A1 | 11/2020 |
| WO | WO 2021/025750 A1 | 2/2021 |
| WO | WO 2021/030666 A1 | 2/2021 |

OTHER PUBLICATIONS

EP 123845790.0, Mar. 18, 2015, Partial Supplementary European Search Report.

(56) References Cited

OTHER PUBLICATIONS

EP 123845790.0, Oct. 12, 2015, Supplementary European Search Report.
PCT/US2012/047778, May 30, 2013, International Search Report and Written Opinion.
PCT/US2012/047778, Feb. 6, 2014, International Preliminary Report on Patentability.
PCT/US2014/052231, Dec. 4, 2014, International Search Report and Written Opinion.
PCT/US2014/052231, Jan. 30, 2015, International Search Report and Written Opinion (Corrected Version).
PCT/US2014/052231, Mar. 3, 2016, International Preliminary Report on Patentability.
PCT/US2014/050283, Nov. 6, 2014, International Search Report and Written Opinion.
PCT/US2014/050283, Feb. 18, 2016, International Preliminary Report on Patentability.
PCT/US2014/054247, Mar. 27, 2015, International Search Report and Written Opinion.
PCT/US2014/054247, Mar. 17, 2016, International Preliminary Report on Patentability.
PCT/US2014/054291, Dec. 18, 2014, Invitation to Pay Additional Fees.
PCT/US2014/054291, Mar. 27, 2015, International Search Report and Written Opinion.
PCT/US2014/054291, Mar. 17, 2016, International Preliminary Report on Patentability.
PCT/US2014/054252, Mar. 5, 2015, International Search Report and Written Opinion.
PCT/US2014/054252, Mar. 17, 2016, International Preliminary Report on Patentability.
PCT/US2014/070038, Apr. 14, 2015, International Search Report and Written Opinion.
PCT/US2014/070038, Jun. 23, 2016, International Preliminary Report on Patentability.
EP 15830407.1, Mar. 2, 2018, Extended European Search Report.
PCT/US2015/042770, Feb. 23, 2016, International Search Report and Written Opinion.
PCT/US2015/042770, Dec. 19, 2016, International Preliminary Report on Patentability.
PCT/US2015/058479, Feb. 11, 2016, International Search Report and Written Opinion.
PCT/US2015/058479, May 11, 2017, International Preliminary Report on Patentability.
PCT/US2016/044546, Dec. 28, 2016, International Search Report and Written Opinion.
PCT/US2016/058344, Mar. 1, 2017, Invitation to Pay Additional Fees.
PCT/US2016/058344, Apr. 20, 2017, International Search Report and Written Opinion.
PCT/US2016/058344, May 3, 2018, International Preliminary Report on Patentability.
PCT/US2018/025887, Jun. 21, 2018, International Search Report and Written Opinion.
PCT/US2017/48390, Nov. 7, 2017, Invitation to Pay Additional Fees.
PCT/US2017/48390, Jan. 9, 2018, International Search Report and Written Opinion.
PCT/US2017/068114, Mar. 20, 2018, International Search Report and Written Opinion.
PCT/US2017/068105, Apr. 4, 2018, International Search Report and Written Opinion.
PCT/US2018/021880, Jun. 20, 2018, International Search Report and Written Opinion.
PCT/US2017/046144, Oct. 10, 2017, International Search Report and Written Opinion.
PCT/US2017/045381, Oct. 26, 2017, International Search Report and Written Opinion.
PCT/US2018/021664, Jun. 21, 2018, International Search Report and Written Opinion.
PCT/US2017/056671, Dec. 21, 2017, Invitation to Pay Additional Fees.
PCT/US2017/056671, Feb. 20, 2018, International Search Report and Written Opinion.
PCT/US2018/021878, Jun. 8, 2018, Invitation to Pay Additional Fees.
PCT/US2018/021878, Aug. 20, 2018, International Search Report and Written Opinion.
PCT/US2018/024208, Aug. 23, 2018, International Search Report and Written Opinion.
PCT/US2018/032460, Jul. 11, 2018, International Search Report and Written Opinion.
U.S. Appl. No. 61/838,178, filed Jun. 21, 2013, Joung et al.
U.S. Appl. No. 62/288,661, filed Jan. 29, 2016, Muir et al.
U.S. Appl. No. 62/357,332, filed Jun. 30, 2016, Liu et al.
[No Author Listed] Score result for SEQ 355 to W02017032580. Muir et al. 2016.
Bershtein et al., Advances in laboratory evolution of enzymes. Curr Opin; Chem Biol. Apr. 2008;12(2):151-8. doi: 10.1016/j.cbpa.2008.01.027. Epub Mar. 7, 2008. Review.
Böck et al., Selenocysteine: the 21st amino acid. Mol Microbiol. Mar. 1991;5(3):515-20.
Bogdanove et al., TAL effectors: customizable proteins for DNA targeting. Science. Sep. 30, 2011;333(6051):1843-6. doi: 10.1126/science.1204094.
Bohlke et al., Sense codon emancipation for proteome-wide incorporation of noncanonical amino acids: rare isoleucine codon AUA as a target for genetic code expansion. FEMS Microbiol Lett. Feb. 2014;351(2):133-44. doi: 10.1111/1574-6968.12371. Epub Jan. 27, 2014.
Budisa et al., Residue-specific bioincorporation of non-natural, biologically active amino acids into proteins as possible drug carriers: structure and stability of the per-thiaproline mutant of annexin V. Proc Natl Acad Sci U S A. Jan. 20, 1998;95(2):455-9.
Carroll, Genome engineering with zinc-finger nucleases. Genetics. Aug. 2011;188(4):773-82. doi: 10.1534/genetics.111.131433. Review.
Chavez et al., Precise Cas9 targeting enables genomic mutation prevention. bioRxiv. Jun. 14, 2016; http://dx/doi.oreg/10.1101/058974. 6 pages.
D'Adda di Fagagna et al., The Gam protein of bacteriophage Mu is an orthologue of eukaryotic Ku. EMBO Rep. Jan. 2003;4(1):47-52.
Dumas et al., Designing logical codon reassignment—Expanding the chemistry in biology. Chem Sci. Jan. 1, 2015;6(1):50-69. doi: 10.1039/c4sc01534g. Epub Jul. 14, 2014. Review.
Edwards et al., An *Escherichia coli* tyrosine transfer RNA is a leucine-specific transfer RNA in the yeast *Saccharomyces cerevisiae*. Proc Natl Acad Sci U S A. Feb. 15, 1991;88(4):1153-6.
Fagerlund et al., The Cpf1 CRISPR-Cas protein expands genome-editing tools. Genome Biology Nov. 17, 2015;16:251. https://doi.org/10.1186/s13059-015-0824-9.
Farhood et al., Codelivery to mammalian cells of a transcriptional factor with cis-acting element using cationic liposomes. Anal Biochem. Feb. 10, 1995;225(1):89-93.
Hamano-Takaku et al., A mutant *Escherichia coli* tyrosyl-tRNA synthetase utilizes the unnatural amino acid azatyrosine more efficiently than tyrosine. J Biol Chem. Dec. 22, 2000;275(51):40324-8.
Hayes et al., Stop codons preceded by rare arginine codons are efficient determinants of SsrA tagging in *Escherichia coli*. Proc Natl Acad Sci U S A. Mar. 19, 2002;99(6):3440-5. Epub Mar. 12, 2002.
Hida et al., Directed evolution for drug and nucleic acid; delivery. Adv Drug Deliv Rev. Dec. 22, 2007;59(15):1562-78. Epub Aug. 28, 2007.; Review.
Hirano et al., Structural Basis for the Altered PAM Specificities of Engineered CRISPR-Cas9. Mol Cell. Mar. 17, 2016;61(6):886-94. doi: 10.1016/j.molcel.2016.02.018.
Husimi, Selection and evolution of bacteriophages in cellstat. Adv Biophys.; 1989;25:1-43. Review.
Kakiyama et al., A peptide release system using a photo-cleavable linker in a cell array format for cell-toxicity analysis. Polymer J. Feb. 27, 2013;45:535-9.

(56) References Cited

OTHER PUBLICATIONS

Kiga et al., An engineered *Escherichia coli* tyrosyl-tRNA synthetase for site-specific incorporation of an unnatural amino acid into proteins in eukaryotic translation and its application in a wheat germ cell-free system. Proc Natl Acad Sci U S A. Jul. 23, 2002;99(15):9715-20. Epub Jul. 3, 2002.
Köhrer et al., A possible approach to site-specific insertion of two different unnatural amino acids into proteins in mammalian cells via nonsense suppression. Chem Biol. Nov. 2003;10(11):1095-102.
Köhrer et al., Complete set of orthogonal 21st aminoacyl-tRNA synthetase-amber, ochre and opal suppressor tRNA pairs: concomitant suppression of three different termination codons in an mRNA in mammalian cells. Nucleic Acids Res. Dec. 1, 2004;32(21):6200-11. Print 2004.
Kowal et al., Exploiting unassigned codons in Micrococcus luteus for tRNA-based amino acid mutagenesis. Nucleic Acids Res. Nov. 15, 1997;25(22):4685-9.
Link et al., Engineering ligand-responsive gene-control elements: lessons learned from natural riboswitches. Gene Ther. Oct. 2009;16(10):1189-201. doi: 10.1038/gt.2009.81. Epub Jul. 9, 2009. Review.
Liu et al., Engineering a tRNA and aminoacyl-tRNA synthetase for the site-specific incorporation of unnatural amino acids into proteins in vivo. Proc Natl Acad Sci U S A. Sep. 16, 1997;94(19):10092-7.
Liu et al., Fast Colorimetric Sensing of Adenosine and Cocaine Based on a General Sensor Design Involving Aptamers and Nanoparticles. Angew Chem. Dec. 16, 2006;45(1):90-4. DOI: 10.1002/anie.200502589.
Monahan et al., Site-specific incorporation of unnatural amino acids into receptors expressed in Mammalian cells. Chem Biol. Jun. 2003;10(6):573-80.
Nelson et al., Filamentous phage DNA cloning vectors: a noninfective mutant with a nonpolar deletion in gene III. Virology. 1981; 108(2): 338-50.
Oakes et al., Protein engineering of Cas9 for enhanced function. Methods Enzymol. 2014;546:491-511.
Pelletier, CRISPR-Cas systems for the study of the immune function. Nov. 15, 2016. https://doi.org/10.1002/9780470015902.a0026896.
Rakonjac et al., Roles of PIII in filamentous phage assembly. J Mol Biol. 1998; 282(1)25-41.
Riechmann et al.,. The C-terminal domain of TolA is the coreceptor for filamentous phage infection of *E. coli*. Cell. 1997; 90(2):351-60. PMID:9244308.
Rudolph et al., Synthetic riboswitches for the conditional control of gene expression in Streptomyces coelicolor. Microbiology. Jul. 2013;159(Pt 7):1416-22. doi: 10.1099/mic.0.067322-0. Epub May 15, 2013.
Sharma et al., Efficient introduction of aryl bromide functionality into proteins in vivo. FEBS Lett. Feb. 4, 2000;467(1):37-40.
Smith, Filamentous fusion phage: novel expression vectors that display cloned antigens on the virion surface. Science. Jun. 14, 1985;228(4705):1315-7.
Wals et al., Unnatural amino acid incorporation in *E. coli*: current and future applications in the design of therapeutic proteins. Front Chem. Apr. 1, 2014;2:15. doi: 10.3389/fchem.2014.00015. eCollection 2014.
Yang et al., APOBEC: From mutator to editor. J Genet Genomics. Sep. 20, 2017;44(9):423-437. doi: 10.1016/j.jgg.2017.04.009. Epub Aug. 7, 2017.
Young et al., Beyond the canonical 20 amino acids: expanding the genetic lexicon. J Biol Chem. Apr. 9, 2010;285(15):11039-44. doi:10.1074/jbc.R109.091306. Epub Feb. 10, 2010.
Yuan et al., Laboratory-directed protein evolution. Microbiol Mol Biol Rev. 2005; 69(3):373-92. PMID: 16148303.
Partial European Search Report for Application No. EP 19187331.4, dated Dec. 19, 2019.
Extended European Search Report for EP 19181479.7, dated Oct. 31, 2019.
International Preliminary Report on Patentability for PCT/US2017/068114, dated Jul. 4, 2019.
International Preliminary Report on Patentability for PCT/US2017/068105, dated Jul. 4, 2019.
International Preliminary Report on Patentability for PCT/US2018/021880, dated Sep. 19, 2019.
International Preliminary Report on Patentability for PCT/US2018/021664, dated Sep. 19, 2019.
International Preliminary Report on Patentability for PCT/US2018/021878, dated Sep. 19, 2019.
International Preliminary Report on Patentability for PCT/US2018/024208, dated Oct. 3, 2019.
International Search Report for PCT/US2018/048969, dated Jul. 31, 2019.
International Prelminary Report on Patentability for PCT/US2018/048969, dated Mar. 12, 2020.
International Preliminary Report on Patentability for PCT/US2018/032460, dated Nov. 21, 2019.
International Search Report and Written Opinion for PCT/US2018/044242, dated Nov. 21, 2019.
International Preliminary Report on Patentability for PCT/US2018/044242, dated Feb. 6, 2020.
U.S. Appl. No. 61/716,256, filed Oct. 19, 2012, Jinek et al.
U.S. Appl. No. 61/717,324, filed Oct. 23, 2012, Cho et al.
U.S. Appl. No. 61/734,256, filed Dec. 6, 2012, Chen et al.
U.S. Appl. No. 61/758,624, filed Jan. 30, 2013, Chen et al.
U.S. Appl. No. 61/761,046, filed Feb. 5, 2013, Knight et al.
U.S. Appl. No. 61/794,422, filed Mar. 15, 2013, Knight et al.
U.S. Appl. No. 61/803,599, filed Mar. 20, 2013, Kim et al.
U.S. Appl. No. 61/837,481, filed Jun. 20, 2013, Cho et al.
U.S. Appl. No. 61/874,682.
U.S. Appl. No. 61/874,746.
[No Author Listed], EMBL Accession No. Q99ZW2. Nov. 2012. 2 pages.
[No Author Listed], Invitrogen Lipofectamine™ 2000 product sheets, 2002. 2 pages.
[No Author Listed], Invitrogen Lipofectamine™ 2000 product sheets, 2005. 3 pages.
[No Author Listed], Invitrogen Lipofectamine™ LTX product sheets, 2011. 4 pages.
[No Author Listed], Thermo Fisher Scientific—How Cationic Lipid Mediated Transfection Works, retrieved from the internet Aug. 27, 2015. 2 pages.
Abudayyeh et al., C2c2 is a single-component programmable RNA-guided RNA-targeting CRISPR effector. Science Aug. 2016;353(6299):aaf5573. DOI: 10.1126/science.aaf5573.
Addgene Plasmid # 44246. pdCas9-humanized, 2017, Stanley Qi.
Addgene Plasmid # 73021. PCMV-BE3, 2017, David Liu.
Addgene Plasmid # 79620. pcDNA3.1_pCMV-nCas-PmCDA1-ugi pH1-gRNA(HPRT), 2017, Akihiko Kondo.
Adrian et al., Targeted SAINT-O-Somes for improved intracellular delivery of siRNA and cytotoxic drugs into endothelial cells. J Control Release. Jun. 15, 2010;144(3):341-9. doi: 10.1016/j.jconrel.2010.03.003. Epub Mar. 11, 2010.
Aguilera et al., Systemic in vivo distribution of activatable cell penetrating peptides is superior to that of cell penetrating peptides. Integr Biol (Camb). Jun. 2009;1(5-6):371-81. doi: 10.1039/b904878b. Epub May 11, 2009.
Aihara et al., A conformational switch controls the DNA cleavage activity of lambda integrase. Mol Cell. Jul. 2003;12(1):187-98.
Akinc et al., A combinatorial library of lipid-like materials for delivery of RNAi therapeutics. Nat Biotechnol. May 2008;26(5):561-9. doi: 10.1038/nbt1402. Epub Apr. 27, 2008.
Akopian et al., Chimeric recombinases with designed DNA sequence recognition. Proc Natl Acad Sci U S A. Jul. 22, 2003;100(15):8688-91. Epub Jul. 1, 2003.
Al-Taei et al., Intracellular traffic and fate of protein transduction domains HIV-1 TAT peptide and octaarginine. Implications for their utilization as drug delivery vectors. Bioconjug Chem. Jan.-Feb. 2006;17(1):90-100.
Alexandrov et al., Signatures of mutational processes in human cancer. Nature. Aug. 22, 2013;500(7463):415-21. doi: 10.1038/nature12477. Epub Aug. 14, 2013.

(56) References Cited

OTHER PUBLICATIONS

Ali et al., Novel genetic abnormalities in Bernard-Soulier syndrome in India. Ann Hematol. Mar. 2014;93(3):381-4. doi: 10.1007/s00277-013-1895-x. Epub Sep. 1, 2013.
Allen et al., Liposomal drug delivery systems: from concept to clinical applications. Adv Drug Deliv Rev. Jan. 2013;65(1):36-48. doi: 10.1016/j.addr.2012.09.037. Epub Oct. 1, 2012.
Ames et al., A eubacterial riboswitch class that senses the coenzyme tetrahydrofolate. Chem Biol. Jul. 30, 2010;17(7):681-5. doi: 10.1016/j.chembiol.2010.05.020.
Anders et al., Structural basis of PAM-dependent target DNA recognition by the Cas9 endonuclease. Nature. Sep. 25, 2014;513(7519):569-73. doi: 10.1038/nature13579. Epub Jul. 27, 2014.
Arnold et al., Mutants of Tn3 resolvase which do not require accessory binding sites for recombination activity. EMBO J. Mar. 1, 1999;18(5):1407-14.
Badran et al., In vivo continuous directed evolution. Curr Opin Chem Biol. Feb. 2015;24:1-10. doi: 10.1016/j.cbpa.2014.09.040. Epub Nov. 7, 2014.
Bae et al., Protective anti-tumour immune responses by murine dendritic cells pulsed with recombinant Tat-carcinoembryonic antigen derived from *Escherichia coli*. Clin Exp Immunol. Jul. 2009;157(1):128-38. doi: 10.1111/j.1365-2249.2009.03943.x.
Barnes et al., Repair and genetic consequences of endogenous DNA base damage in mammalian cells. Annu Rev Genet. 2004;38:445-76.
Barrangou et al., CRISPR provides acquired resistance against viruses in prokaryotes. Science. Mar. 23, 2007;315(5819):1709-12.
Barrangou, RNA-mediated programmable DNA cleavage. Nat Biotechnol. Sep. 2012;30(9):836-8. doi: 10.1038/nbt.2357.
Basha et al., Influence of cationic lipid composition on gene silencing properties of lipid nanoparticle formulations of siRNA in antigen-presenting cells. Mol Ther. Dec. 2011;19(12):2186-200. doi: 10.1038/mt.2011.190. Epub Oct. 4, 2011.
Batey et al., Structure of a natural guanine-responsive riboswitch complexed with the metabolite hypoxanthine. Nature. Nov. 18, 2004;432(7015):411-5.
Beale et al., Comparison of the differential context-dependence of DNA deamination by APOBEC enzymes: correlation with mutation spectra in vivo. J Mol Biol. Mar. 26, 2004;337(3):585-96.
Bedell et al., In vivo genome editing using a high-efficiency TALEN system. Nature. Nov. 1, 2012;491(7422):114-8. Doi: 10.1038/nature11537. Epub Sep. 23, 2012.
Begley, Scientists unveil the 'most clever CRISPR gadget' so far. STAT, Apr. 20, 2016. https://www.statnews.com/2016/04/20/clever-crispr-advance-unveiled/.
Beumer et al., Efficient gene targeting in *Drosophila* with zinc-finger nucleases. Genetics. Apr. 2006;172(4):2391-403. Epub Feb. 1, 2006.
Bhagwat, DNA-cytosine deaminases: from antibody maturation to antiviral defense. DNA Repair (Amst). Jan. 5, 2004;3(1):85-9.
Bibikova et al., Stimulation of homologous recombination through targeted cleavage by chimeric nucleases. Mol Cell Biol. Jan. 2001;21(1):289-97.
Bibikova et al., Targeted chromosomal cleavage and mutagenesis in *Drosophila* using zinc-finger nucleases. Genetics. Jul. 2002;161(3):1169-75.
Billon et al., CRISPR-Mediated Base Editing Enables Efficient Disruption of Eukaryotic Genes through Induction of STOP Codons. Mol Cell. Sep. 21, 2017;67(6):1068-1079.e4. doi: 10.1016/j.molcel.2017.08.008. Epub Sep. 7, 2017.
Birling et al., Site-specific recombinases for manipulation of the mouse genome. Methods Mol Biol. 2009;561:245-63. doi: 10.1007/978-1-60327-019-9_16.
Bitinaite et al., FokI dimerization is required for DNA cleavage. Proc Natl Acad Sci U S A. Sep. 1, 1998;95(18):10570-5.
Boch et al., Breaking the code of DNA binding specificity of TAL-type III effectors. Science. Dec. 11, 2009;326(5959):1509-12. Doi: 10.1126/science.1178811.

Boch, TALEs of genome targeting. Nat Biotechnol. Feb. 2011;29(2):135-6. Doi: 10.1038/nbt.1767.
Boeckle et al., Melittin analogs with high lytic activity at endosomal pH enhance transfection with purified targeted PEI polyplexes. J Control Release. May 15, 2006;112(2):240-8. Epub Mar. 20, 2006.
Bolotin et al., Clustered regularly interspaced short palindrome repeats (CRISPRs) have spacers of extrachromosomal origin. Microbiology. Aug. 2005;151(Pt 8):2551-61.
Borman, Improved route to single-base genome editing. Chemical & Engineering News, Apr. 25, 2016;94(17)p5. http://cen.acs.org/articles/94/i17/Improved-route-single-base-genome.html.
Branden and Tooze, Introduction to Protein Structure. 1999; 2nd edition. Garland Science Publisher: 3-12.
Briner et al., Guide RNA functional modules direct Cas9 activity and orthogonality. Mol Cell. Oct. 23, 2014;56(2):333-339. doi: 10.1016/j.molcel.2014.09.019.
Britt et al., Re-engineering plant gene targeting. Trends Plant Sci. Feb. 2003;8(2):90-5.
Brouns et al., Small CRISPR RNAs guide antiviral defense in prokaryotes. Science. Aug. 15, 2008;321(5891):960-4. doi: 10.1126/science.1159689.
Brown et al., Serine recombinases as tools for genome engineering. Methods. Apr. 2011;53(4):372-9. doi: 10.1016/j.ymeth.2010.12.031. Epub Dec. 30, 2010.
Brusse et al., Spinocerebellar ataxia associated with a mutation in the fibroblast growth factor 14 gene (SCA27): A new phenotype. Mov Disord. Mar. 2006;21(3):396-401.
Buchholz et al., Alteration of Cre recombinase site specificity by substrate-linked protein evolution. Nat Biotechnol. Nov. 2001;19(11):1047-52.
Buchwald et al., Long-term, continuous intravenous heparin administration by an implantable infusion pump in ambulatory patients with recurrent venous thrombosis. Surgery. Oct. 1980;88(4):507-16.
Bulow et al., Multienzyme systems obtained by gene fusion. Trends Biotechnol. Jul. 1991;9(7):226-31.
Bulyk et al., Exploring the DNA-binding specificities of zinc fingers with DNA microarrays. Proc Natl Acad Sci U S A. Jun. 19, 2001;98(13):7158-63. Epub Jun. 12, 2001.
Burke et al., Activating mutations of Tn3 resolvase marking interfaces important in recombination catalysis and its regulation. Mol Microbiol. Feb. 2004;51(4):937-48.
Burstein et al., New CRISPR-Cas systems from uncultivated microbes. Nature Feb. 2017;542(7640):237-240.
Buskirk et al., Directed evolution of ligand dependence: small-molecule-activated protein splicing. Proc Natl Acad Sci U S A. Jul. 20, 2004;101(29):10505-10. Epub Jul. 9, 2004.
Cade et al., Highly efficient generation of heritable zebrafish gene mutations using homo- and heterodimeric TALENs. Nucleic Acids Res. Sep. 2012;40(16):8001-10. Doi: 10.1093/nar/gks518. Epub Jun. 7, 2012.
Caldecott et al., Single-strand break repair and genetic disease. Nat Rev Genet. Aug. 2008;9(8):619-31. doi: 10.1038/nrg2380.
Cameron, Recent advances in transgenic technology. Mol Biotechnol. Jun. 1997;7(3):253-65.
Cargill et al. Characterization of single-nucleotide polymorphisms in coding regions of human genes. Nat Genet. Jul. 1999;22(3):231-8.
Caron et al., Intracellular delivery of a Tat-eGFP fusion protein into muscle cells. Mol Ther. Mar. 2001;3(3):310-8.
Carroll et al., Gene targeting in *Drosophila* and Caenorhabditis elegans with zinc-finger nucleases. Methods Mol Biol. 2008;435:63-77. doi: 10.1007/978-1-59745-232-8_5.
Carroll et al., Progress and prospects: zinc-finger nucleases as gene therapy agents. Gene Ther. Nov. 2008;15(22):1463-8. doi: 10.1038/gt.2008.145. Epub Sep. 11, 2008.
Carroll, A CRISPR approach to gene targeting. Mol Ther. Sep. 2012;20(9):1658-60. doi: 10.1038/mt.2012.171.
Cermak et al., Efficient design and assembly of custom TALEN and other TAL effector-based constructs for DNA targeting. Nucleic Acids Res. Jul. 2011;39(12):e82. Doi: 10.1093/nar/gkr218. Epub Apr. 14, 2011.

(56) References Cited

OTHER PUBLICATIONS

Chadwick et al., In Vivo Base Editing of PCSK9 (Proprotein Convertase Subtilisin/Kexin Type 9) as a Therapeutic Alternative to Genome Editing. Arterioscler Thromb Vasc Biol. Sep. 2017;37(9):1741-1747. doi: 10.1161/ATVBAHA.117.309881. Epub Jul. 27, 2017.

Chaikind et al., A programmable Cas9-serine recombinase fusion protein that operates on DNA sequences in mammalian cells. Nucleic Acids Res. Nov. 16, 2016;44(20):9758-9770. Epub Aug. 11, 2016.

Chang et al., Modification of DNA ends can decrease end joining relative to homologous recombination in mammalian cells. Proc Natl Acad Sci U S A. Jul. 1987;84(14):4959-63.

Charpentier et al., Biotechnology: Rewriting a genome. Nature. Mar. 7, 2013;495(7439):50-1. doi: 10.1038/495050a.

Chavez et al., Highly efficient Cas9-mediated transcriptional programming. Nat Methods. Apr. 2015;12(4):326-8. doi: 10.1038/nmeth.3312. Epub Mar. 2, 2015.

Chavez et al., Precise Cas9 targeting enables genomic mutation prevention. Jun. 14, 2016. doi:https://doi.org/10.1101/058974. [Preprint].

Chavez et al., Precise Cas9 targeting enables genomic mutation prevention. Proc Natl Acad Sci U S A. Apr. 3, 2018;115(14):3669-3673. doi: 10.1073/pnas.1718148115. Epub Mar. 19, 2018.

Chavez et al., Therapeutic applications of the ΦC31 integrase system. Curr Gene Ther. Oct. 2011;11(5):375-81. Review.

Chavez et al., Therapeutic applications of the PhiC31 integrase system. Curr Gene Ther. Oct. 2011;11(5):375-81. Review.

Chelico et al., Biochemical basis of immunological and retroviral responses to DNA-targeted cytosine deamination by activation-induced cytidine deaminase and APOBEC3G. J Biol Chem. Oct. 9, 2009;284(41):27761-5. doi: 10.1074/jbc.R109.052449. Epub Aug. 13, 2009.

Chelico et al., Stochastic properties of processive cytidine DNA deaminases AID and APOBEC3G. Philos Trans R Soc Lond B Biol Sci. Mar. 12, 2009;364(1517):583-93. doi: 10.1098/rstb.2008.0195.

Chen et al., Fusion protein linkers: property, design and functionality. Adv Drug Deliv Rev. Oct. 2013;65(10):1357-69. doi:10.1016/j.addr.2012.09.039. Epub Sep. 29, 2012.

Chen et al., Structure of the DNA deaminase domain of the HIV-1 restriction factor APOBEC3G. Nature. Mar. 6, 2008;452(7183):116-9. doi: 10.1038/nature06638. Epub Feb. 20, 2008.

Chesnoy et al., Structure and function of lipid-DNA complexes for gene delivery. Annu Rev Biophys Biomol Struct. 2000;29:27-47.

Chew et al., A multifunctional AAV-CRISPR-Cas9 and its host response. Nat Methods. Oct. 2016;13(10):868-74. doi: 10.1038/nmeth.3993. Epub Sep. 5, 2016.

Chichili et al., Linkers in the structural biology of protein-protein interactions. Protein Science. 2013;22:153-67.

Chipev et al., A leucine—proline mutation in the H1 subdomain of keratin 1 causes epidermolytic hyperkeratosis. Cell. Sep. 4, 1992;70(5):821-8.

Cho et al., Analysis of off-target effects of CRISPR/Cas-derived RNA-guided endonucleases and nickases. Genome Res. Jan. 2014;24(1):132-41. doi: 10.1101/gr.162339.113. Epub Nov. 19, 2013.

Cho et al., Targeted genome engineering in human cells with the Cas9 RNA-guided endonuclease. Nat Biotechnol. Mar. 2013;31(3):230-2. doi: 10.1038/nbt.2507. Epub Jan. 29, 2013.

Christian et al., Targeting G with TAL effectors: a comparison of activities of TALENs constructed with NN and NK repeat variable di-residues. PLoS One. 2012;7(9):e45383. doi: 10.1371/journal.pone.0045383. Epub Sep. 24, 2012.

Christian et al., Targeting DNA double-strand breaks with TAL effector nucleases. Genetics. Oct. 2010;186(2):757-61. Doi: 10.1534/genetics.110.120717. Epub Jul. 26, 2010.

Chu et al., Increasing the efficiency of homology-directed repair for CRISPR-Cas9-induced precise gene editing in mammalian cells. Nat Biotech. Feb. 13, 2015;33:543-8.

Chung-Il et al., Artificial control of gene expression in mammalian cells by modulating RNA interference through aptamer-small molecule interaction. RNA. May 2006;12(5):710-6. Epub Apr. 10, 2006.

Chylinski et al., The tracrRNA and Cas9 families of type II CRISPR-Cas immunity systems. RNA Biol. May 2013;10(5):726-37. doi: 10.4161/rna.24321. Epub Apr. 5, 2013.

Cobb et al., Directed evolution as a powerful synthetic biology tool. Methods. Mar. 15, 2013;60(1):81-90. doi: 10.1016/j.ymeth.2012.03.009. Epub Mar. 23, 2012.

Cobb et al., Directed evolution: an evolving and enabling synthetic biology tool. Curr Opin Chem Biol. Aug. 2012;16(3-4):285-91. doi:10.1016/j.cbpa.2012.05.186. Epub Jun. 4, 2012. Review.

Coelho et al., Safety and efficacy of RNAi therapy for transthyretin amyloidosis. N Engl J Med. Aug. 29, 2013;369(9):819-29. doi: 10.1056/NEJMoa1208760.

Cole-Strauss et al., Correction of the mutation responsible for sickle cell anemia by an RNA-DNA oligonucleotide. Science. Sep. 6, 1996;273(5280):1386-9.

Colletier et al., Protein encapsulation in liposomes: efficiency depends on interactions between protein and phospholipid bilayer. BMC Biotechnol. May 10, 2002;2:9.

Cong et al., Comprehensive interrogation of natural TALE DNA-binding modules and transcriptional repressor domains. Nat Commun. Jul. 24, 2012;3:968. doi: 10.1038/ncomms1962.

Cong et al., Multiplex genome engineering using CRISPR/Cas systems. Science. Feb. 15, 2013;339(6121):819-23. doi: 10.1126/science.1231143. Epub Jan. 3, 2013.

Conticello, The AID/APOBEC family of nucleic acid mutators. Genome Biol. 2008;9(6):229. doi: 10.1186/gb-2008-9-6-229. Epub Jun. 17, 2008.

Cornu et al., DNA-binding specificity is a major determinant of the activity and toxicity of zinc-finger nucleases. Mol Ther. Feb. 2008;16(2):352-8. Epub Nov. 20, 2007.

Covino et al., The CCL2/CCR2 Axis in the Pathogenesis of HIV-1 Infection: A New Cellular Target for Therapy? Current Drug Targets Dec. 2016;17(1):76-110. DOI: 10.2174/1389450117011151217110917.

Cox et al., Conditional gene expression in the mouse inner ear using Cre-loxP. J Assoc Res Otolaryngol. Jun. 2012;13(3):295-322. doi: 10.1007/s10162-012-0324-5. Epub Apr. 24, 2012.

Cox et al., Therapeutic genome editing: prospects and challenges. Nat Med. Feb. 2015;21(2):121-31. doi: 10.1038/nm.3793.

Cradick et al., CRISPR/Cas9 systems targeting B-globin and CCR5 genes have substantial off-target activity. Nucleic Acids Res. Nov. 1, 2013;41(20):9584-92. doi: 10.1093/nar/gkt714. Epub Aug. 11, 2013.

Cradick et al., ZFN-site searches genomes for zinc finger nuclease target sites and off-target sites. BMC Bioinformatics. May 13, 2011;12:152. doi: 10.1186/1471-2105-12-152.

Cradick et al., Zinc-finger nucleases as a novel therapeutic strategy for targeting hepatitis B virus DNAs. Mol Ther. May 2010;18(5):947-54. Doi: 10.1038/mt.2010.20. Epub Feb. 16, 2010.

Cronican et al., A class of human proteins that deliver functional proteins into mammalian cells in vitro and in vivo. Chem Biol. Jul. 29, 2011;18(7):833-8. doi: 10.1016/j.chembiol.2011.07.003.

Cronican et al., Potent delivery of functional proteins into mammalian cells in vitro and in vivo using a supercharged protein. ACS Chem Biol. Aug. 20, 2010;5(8):747-52. doi: 10.1021/cb1001153.

Cui et al., Targeted integration in rat and mouse embryos with zinc-finger nucleases. Nat Biotechnol. Jan. 2011;29(1):64-7. Doi: 10.1038/nbt.1731. Epub Dec. 12, 2010.

Cunningham et al., Ensembl 2015. Nucleic Acids Res. Jan. 2015;43(Database issue):D662-9. doi: 10.1093/nar/gku1010. Epub Oct. 28, 2014.

Czerwinski et al., Cytotoxic agents directed to peptide hormone receptors: defining the requirements for a successful drug. Proc Natl Acad Sci U S A. Sep. 29, 1998;95(20):11520-5.

Dahlem et al., Simple methods for generating and detecting locus-specific mutations induced with TALENs in the zebrafish genome. PLoS Genet. 2012;8(8):e1002861. doi: 10.1371/journal.pgen.1002861. Epub Aug. 16, 2012.

(56) References Cited

OTHER PUBLICATIONS

Daniels et al., Intrinsically cell-permeable miniature proteins based on a minimal cationic PPII motif. J Am Chem Soc. Nov. 28, 2007;129(47):14578-9. Epub Nov. 6, 2007.
Davis et al., DNA double strand break repair via non-homologous end-joining. Transl Cancer Res. Jun. 2013;2(3):130-143.
Davis et al., Small molecule-triggered Cas9 protein with improved genome-editing specificity. Nat Chem Biol. May 2015;11(5):316-8. doi: 10.1038/nchembio.1793. Epub Apr. 6, 2015.
De Souza, Primer: genome editing with engineered nucleases. Nat Methods. Jan. 2012;9(1):27.
Deltcheva et al., CRISPR RNA maturation by trans-encoded small RNA and host factor RNase III. Nature. Mar. 31, 2011;471(7340):602-7. doi: 10.1038/nature09886.
Dicarlo et al., Genome engineering in *Saccharomyces cerevisiae* using CRISPR-Cas systems. Nucleic Acids Research Apr. 2013;41(7):4336-43.
Ding et al., A TALEN genome-editing system for generating human stem cell-based disease models. Cell Stem Cell. Feb. 7, 2013;12(2):238-51. Doi: 10.1016/j.stem.2012.11.011. Epub Dec. 13, 2012.
Ding et al., Permanent alteration of PCSK9 with in vivo CRISPR-Cas9 genome editing. Circ Res. Aug. 15, 2014;115(5):488-92. doi: 10.1161/CIRCRESAHA.115.304351. Epub Jun. 10, 2014.
Dixon et al., Reengineering orthogonally selective riboswitches. Proc Natl Acad Sci U S A. Feb. 16, 2010;107(7):2830-5. doi: 10.1073/pnas.0911209107. Epub Jan. 26, 2010.
Doench et al., Optimized sgRNA design to maximize activity and minimize off-target effects of CRISPR-Cas9. Nat Biotechnol. Feb. 2016;34(2):184-191. doi: 10.1038/nbt.3437.
Dormiani et al., Long-term and efficient expression of human β-globin gene in a hematopoietic cell line using a new site-specific integrating non-viral system. Gene Ther. Aug. 2015;22(8):663-74. doi: 10.1038/gt.2015.30. Epub Apr. 1, 2015.
Doudna et al., Genome editing. The new frontier of genome engineering with CRISPR-Cas9. Science. Nov. 28, 2014;346(6213):1258096. doi: 10.1126/science.1258096.
Doyon et al., Enhancing zinc-finger-nuclease activity with improved obligate heterodimeric architectures. Nat Methods. Jan. 2011;8(1):74-9. Doi: 10.1038/nmeth.1539. Epub Dec. 5, 2010.
Doyon et al., Heritable targeted gene disruption in zebrafish using designed zinc-finger nucleases. Nat Biotechnol. Jun. 2008;26(6):702-8. Doi: 10.1038/nbt1409. Epub May 25, 2008.
Dunaime, Breakthrough method means CRISPR just got a lot more relevant to human health. The Verge. Apr. 20, 2016. http://www.theverge.com/2016/4/20/11450262/crispr-base-editing-single-nucleotides-dna-gene-liu-harvard.
During et al., Controlled release of dopamine from a polymeric brain implant: in vivo characterization. Ann Neurol. Apr. 1989;25(4):351-6.
East-Seletsky et al., Two distinct RNase activities of CRISPR-C2c2 enable guide-RNA processing and RNA detection. Nature Oct. 2016;538(7624):270-3.
Edwards et al., Crystal structures of the thi-box riboswitch bound to thiamine pyrophosphate analogs reveal adaptive RNA-small molecule recognition. Structure. Sep. 2006;14(9):1459-68.
Edwards et al., Structural basis for recognition of S-adenosylhomocysteine by riboswitches. RNA. Nov. 2010;16(11):2144-55. doi:10.1261/rna.2341610. Epub Sep. 23, 2010.
Ellington et al., In vitro selection of RNA molecules that bind specific ligands. Nature. Aug. 30, 1990;346(6287):818-22.
Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.
Esvelt et al., A system for the continuous directed evolution of biomolecules. Nature. Apr. 28, 2011;472(7344):499-503. doi: 10.1038/nature09929. Epub Apr. 10, 2011.
Esvelt et al., Genome-scale engineering for systems and synthetic biology. Mol Syst Biol. 2013;9:641. doi: 10.1038/msb.2012.66.
Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.
Extended European Search Report for EP 15830407.1, dated Mar. 2, 2018.
Fang et al., Synthetic Studies Towards Halichondrins: Synthesis of the Left Halves of Norhalichondrins and Homohalichondrins. Tetrahedron Letters 1992;33(12):1557-1560.
Ferry et al., Rational design of inducible CRISPR guide RNAs for de novo assembly of transcriptional programs. Nat Commun. Mar. 3, 2017;8:14633. doi: 10.1038/ncomms14633.
Fine et al., Trans-spliced Cas9 allows cleavage of HBB and CCR5 genes in human cells using compact expression cassettes. Scientific Reports 2015;5(1):Article No. 10777. doi:10.1038/srep10777. With Supplementary Information.
Fischer et al., Cryptic epitopes induce high-titer humoral immune response in patients with cancer. J Immunol. Sep. 1, 2010;185(5):3095-102. doi: 10.4049/jimmunol.0902166. Epub Jul. 26, 2010.
Fonfara et al., Phylogeny of Cas9 determines functional exchangeability of dual-RNA and Cas9 among orthologous type II CRISPR-Cas systems. Nucleic Acids Res. Feb. 2014;42(4):2577-90. doi: 10.1093/nar/gkt1074. Epub Nov. 22, 2013.
Freshney, Culture of Animal Cells. A Manual of Basic Technique. Alan R. Liss, Inc. New York. 1983;4.
Fu et al., Improving CRISPR-Cas nuclease specificity using truncated guide RNAs. Nat Biotechnol. Mar. 2014;32(3):279-84. doi: 10.1038/nbt.2808. Epub Jan. 26, 2014.
Fu et al., High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013.
Fuchs et al., Polyarginine as a multifunctional fusion tag. Protein Sci. Jun. 2005;14(6):1538-44.
Fujisawa et al., Disease-associated mutations in CIAS1 induce cathepsin B-dependent rapid cell death of human THP-1 monocytic cells. Blood. Apr. 1, 2007;109(7):2903-11.
Fukui et al., DNA Mismatch Repair in Eukaryotes and Bacteria. J Nucleic Acids. Jul. 27, 2010;2010. pii: 260512. doi: 10.4061/2010/260512.
Fung et al., Repair at single targeted DNA double-strand breaks in pluripotent and differentiated human cells. PLoS One. 2011;6(5):e20514. doi: 10.1371/journal.pone.0020514. Epub May 25, 2011.
Gabriel et al., An unbiased genome-wide analysis of zinc-finger nuclease specificity. Nat Biotechnol. Aug. 7, 2011;29(9):816-23. doi: 10.1038/nbt.1948.
Gaj et al., A comprehensive approach to zinc-finger recombinase customization enables genomic targeting in human cells. Nucleic Acids Res. Feb. 6, 2013;41(6):3937-46.
Gaj et al., Enhancing the specificity of recombinase-mediated genome engineering through dimer interface redesign. J Am Chem Soc. Apr. 2, 2014;136(13):5047-56. doi: 10.1021/ja4130059. Epub Mar. 20, 2014.
Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Gaj et al., Structure-guided reprogramming of serine recombinase DNA sequence specificity. Proc Natl Acad Sci U S A. Jan. 11, 2011;108(2):498-503. doi: 10.1073/pnas.1014214108. Epub Dec. 27, 2010.
Gaj et al., ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Gallo et al., A novel pathogenic PSEN1 mutation in a family with Alzheimer's disease: phenotypical and neuropathological features. J Alzheimers Dis. 2011;25(3):425-31. doi: 10.3233/JAD-2011-110185.
Gao et al., Crystal structure of a TALE protein reveals an extended N-terminal DNA binding region. Cell Res. Dec. 2012;22(12):1716-20. doi: 10.1038/cr.2012.156. Epub Nov. 13, 2012.
Gao et al., DNA-guided genome editing using the Natronobacterium gregoryi Argonaute. Nat Biotechnol. Jul. 2016;34(7):768-73. doi: 10.1038/nbt.3547. Epub May 2, 2016.
Gardlik et al., Vectors and delivery systems in gene therapy. Med Sci Monit. Apr. 2005;11(4):RA110-21. Epub Mar. 24, 2005.

(56) References Cited

OTHER PUBLICATIONS

Garneau et al., The CRISPR/Cas bacterial immune system cleaves bacteriophage and plasmid DNA. Nature. Nov. 4, 2010;468(7320):67-71. doi: 10.1038/nature09523.
Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012. Supplementary materials included.
Gasiunas et al., RNA-dependent DNA endonuclease Cas9 of the CRISPR system: Holy Grail of genome editing? Trends Microbiol. Nov. 2013;21(11):562-7. doi: 10.1016/j.tim.2013.09.001. Epub Oct. 1, 2013.
Genbank Submission; NIH/NCBI, Accession No. J04623. Kita et al., Apr. 26, 1993. 2 pages.
Genbank Submission; NIH/NCBI, Accession No. NC_002737.1. Ferretti et al., Jun. 27, 2013. 1 page.
Genbank Submission; NIH/NCBI, Accession No. NC_015683.1. Trost et al., Jul. 6, 2013. 1 page.
Genbank Submission; NIH/NCBI, Accession No. NC_016782.1. Trost et al., Jun. 11, 2013. 1 page.
Genbank Submission; NIH/NCBI, Accession No. NC_016786.1. Trost et al., Aug. 28, 2013. 1 page.
Genbank Submission; NIH/NCBI, Accession No. NC_017053.1. Fittipaldi et al., Jul. 6, 2013. 1 page.
Genbank Submission; NIH/NCBI, Accession No. NC_017317.1. Trost et al., Jun. 11, 2013. 1 page.
Genbank Submission; NIH/NCBI, Accession No. NC_017861.1. Heidelberg et al., Jun. 11, 2013. 1 page.
Genbank Submission; NIH/NCBI, Accession No. NC_018010.1. Lucas et al., Jun. 11, 2013. 2 pages.
Genbank Submission; NIH/NCBI, Accession No. NC_018721.1. Feng et al., Jun. 11, 2013. 1 pages.
Genbank Submission; NIH/NCBI, Accession No. NC_021284.1. Ku et al., Jul. 12, 2013. 1 page.
Genbank Submission; NIH/NCBI, Accession No. NC_021314.1. Zhang et al., Jul. 15, 2013. 1 page.
Genbank Submission; NIH/NCBI, Accession No. NC_021846.1. Lo et al., Jul. 22, 2013. 1 page.
Genbank Submission; NIH/NCBI, Accession No. NP_472073.1. Glaser et al., Jun. 27, 2013. 2 pages.
Genbank Submission; NIH/NCBI, Accession No. P42212. Prasher et al., Mar. 19, 2014. 7 pages.
Genbank Submission; NIH/NCBI, Accession No. YP_002342100.1. Bernardini et al., Jun. 10, 2013. 2 pages.
Genbank Submission; NIH/NCBI, Accession No. YP_002344900.1. Gundogdu et al., Mar. 19, 2014. 2 pages.
Genbank Submission; NIH/NCBI, Accession No. YP_820832.1. Makarova et al., Aug. 27, 2013. 2 pages.
Gerber et al., RNA editing by base deamination: more enzymes, more targets, new mysteries. Trends Biochem Sci. Jun. 2001;26(6):376-84.
Gersbach et al., Directed evolution of recombinase specificity by split gene reassembly. Nucleic Acids Res. Jul. 2010;38(12):4198-206. doi: 10.1093/nar/gkq125. Epub Mar. 1, 2010.
Gersbach et al., Targeted plasmid integration into the human genome by an engineered zinc-finger recombinase. Nucleic Acids Res. Sep. 1, 2011;39(17):7868-78. doi: 10.1093/nar/gkr421. Epub Jun. 7, 2011.
Gilbert et al., CRISPR-mediated modular RNA-guided regulation of transcription in eukaryotes. Cell. 2013 154(2):442-51.
Gilleron et al., Image-based analysis of lipid nanoparticle-mediated siRNA delivery, intracellular trafficking and endosomal escape. Nat Biotechnol. Jul. 2013;31(7):638-46. doi: 10.1038/nbt.2612. Epub Jun. 23, 2013.
Gonzalez et al., An iCRISPR platform for rapid, multiplexable, and inducible genome editing in human pluripotent stem cells. Cell Stem Cell. Aug. 7, 2014;15(2):215-26. doi: 10.1016/j.stem.2014.05.018. Epub Jun. 12, 2014.

Gordley et al., Evolution of programmable zinc finger-recombinases with activity in human cells. J Mol Biol. Mar. 30, 2007;367(3):802-13. Epub Jan. 12, 2007.
Gordley et al., Synthesis of programmable integrases. Proc Natl Acad Sci U S A. Mar. 31, 2009;106(13):5053-8. doi: 10.1073/pnas.0812502106. Epub Mar. 12, 2009.
Grundy et al., The L box regulon: lysine sensing by leader RNAs of bacterial lysine biosynthesis genes. Proc Natl Acad Sci U S A. Oct. 14, 2003;100(21):12057-62. Epub Oct. 1, 2003.
Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.
Guilinger et al., Fusion of catalytically inactive Cas9 to FokI nuclease improves the specificity of genome modification. Nat Biotechnol. Jun. 2014;32(6):577-82. doi: 10.1038/nbt.2909. Epub Apr. 25, 2014.
Guo et al., Directed evolution of an enhanced and highly efficient FokI cleavage domain for zinc finger nucleases. J Mol Biol. Jul. 2, 2010;400(1):96-107. doi: 10.1016/j.jmb.2010.04.060. Epub May 4, 2010.
Guo et al., Protein tolerance to random amino acid change. Proc Natl Acad Sci U S A. Jun. 22, 2004;101(25):9205-10. Epub Jun. 14, 2004.
Guo et al., Structure of Cre recombinase complexed with DNA in a site-specific recombination synapse. Nature. Sep. 4, 1997;389(6646):40-6.
Gupta et al., Zinc finger protein-dependent and -independent contributions to the in vivo off-target activity of zinc finger nucleases. Nucleic Acids Res. Jan. 2011;39(1):381-92. doi: 10.1093/nar/gkq787. Epub Sep. 14, 2010.
Haeussler et al., Evaluation of off-target and on-target scoring algorithms and integration into the guide RNA selection tool CRISPOR. Genome Biol. Jul. 5, 2016;17(1):148. doi: 10.1186/S13059-016-1012-2.
Hale et al., RNA-guided RNA cleavage by a CRISPR RNA-Cas protein complex. Cell. Nov. 25, 2009;139(5):945-56. doi: 10.1016/j.cell.2009.07.040.
Hampel et al., Evidence for preorganization of the glmS ribozyme ligand binding pocket. Biochemistry. 2006; 45(25):7861-71.
Han, New CRISPR/Cas9-based Tech Edits Single Nucleotides Without Breaking DNA. Genome Web, Apr. 20, 2016. https://www.genomeweb.com/gene-silencinggene-editing/new-crisprcas9-based-tech-edits-single-nucleotides-without-breaking-dna.
Harris et al., RNA editing enzyme APOBEC1 and some of its homologs can act as DNA mutators. Mol Cell. Nov. 2002;10(5):1247-53.
Hartung et al., Correction of metabolic, craniofacial, and neurologic abnormalities in MPS I mice treated at birth with adeno-associated virus vector transducing the human alpha-L-iduronidase gene. Mol Ther. Jun. 2004;9(6):866-75.
Hartung et al., Cre mutants with altered DNA binding properties. J Biol Chem. Sep. 4, 1998;273(36):22884-91.
Hasadsri et al., Functional protein delivery into neurons using polymeric nanoparticles. J Biol Chem. Mar. 13, 2009;284(11):6972-81. doi: 10.1074/jbc.M805956200. Epub Jan. 7, 2009.
Heitz et al., Twenty years of cell-penetrating peptides: from molecular mechanisms to therapeutics. Br J Pharmacol. May 2009;157(2):195-206. doi: 10.1111/j.1476-5381.2009.00057.x. Epub Mar. 20, 2009.
Heller et al., Replisome assembly and the direct restart of stalled replication forks. Nat Rev Mol Cell Biol. Dec. 2006;7(12):932-43. Epub Nov. 8, 2006.
Hess et al., Directed evolution using dCas9-targeted somatic hypermutation in mammalian cells. Nat Methods. Dec. 2016;13(12):1036-1042. doi: 10.1038/nmeth.4038. Epub Oct. 31, 2016.
Hickford et al., Antitumour polyether macrolides: four new halichondrins from the New Zealand deep-water marine sponge *Lissodendoryx* sp. Bioorg Med Chem. Mar. 15, 2009;17(6):2199-203. doi: 10.1016/j.bmc.2008.10.093. Epub Nov. 19, 2008.
Hill et al., Functional analysis of conserved histidines in ADP-glucose pyrophosphorylase from *Escherichia coli*.Biochem Biophys Res Commun. Mar. 17, 1998;244(2):573-7.

(56) References Cited

OTHER PUBLICATIONS

Hilton et al., Enabling functional genomics with genome engineering. Genome Res. Oct. 2015;25(10):1442-55. doi: 10.1101/gr.190124.115.

Hirano et al., Site-specific recombinases as tools for heterologous gene integration. Appl Microbiol Biotechnol. Oct. 2011;92(2):227-39. doi: 10.1007/s00253-011-3519-5. Epub Aug. 7, 2011. Review.

Hockemeyer et al., Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.

Hockemeyer et al., Genetic engineering of human pluripotent cells using TALE nucleases. Nat Biotechnol. Jul. 7, 2011;29(8):731-4. doi: 10.1038/nbt.1927.

Holden et al., Crystal structure of the anti-viral APOBEC3G catalytic domain and functional implications. Nature. Nov. 6, 2008;456(7218):121-4. doi: 10.1038/nature07357. Epub Oct. 12, 2008.

Hondares et al., Peroxisome Proliferator-activated Receptor α (PPARα) Induces PPARγ Coactivator 1α (PGC-1α) Gene Expression and Contributes to Thermogenic Activation of Brown Fat. J Biol. Chem Oct. 2011;286(50):43112-22. doi: 10.1074/jbc.M111.252775.

Hope et al., Cationic lipids, phosphatidylethanolamine and the intracellular delivery of polymeric, nucleic acid-based drugs (review). Mol Membr Biol. Jan.-Mar. 1998;15(1):1-14.

Horvath et al., CRISPR/Cas, the immune system of bacteria and archaea. Science. Jan. 8, 2010;327(5962):167-70. doi: 10.1126/science.1179555.

Hou et al., Efficient genome engineering in human pluripotent stem cells using Cas9 from Neisseria meningitidis. Proc Natl Acad Sci U S A. Sep. 24, 2013;110(39):15644-9. doi: 10.1073/pnas.1313587110. Epub Aug. 12, 2013.

Houdebine, The methods to generate transgenic animals and to control transgene expression. J Biotechnol. Sep. 25, 2002;98(2-3):145-60.

Howard et al., Intracerebral drug delivery in rats with lesion-induced memory deficits. J Neurosurg. Jul. 1989;71(1):105-12.

Hower et al., Shape-based peak identification for ChIP-Seq. BMC Bioinformatics. Jan. 12, 2011;12:15. doi: 10.1186/1471-2105-12-15.

Hsu et al., DNA targeting specificity of RNA-guided Cas9 nucleases. Nat Biotechnol. Sep. 2013;31(9):827-32. doi: 10.1038/nbt.2647. Epub Jul. 21, 2013.

Hu et al., Chemical Biology Approaches to Genome Editing: Understanding, Controlling, and Delivering Programmable Nucleases. Cell Chem Biol. Jan. 21, 2016;23(1):57-73. doi: 10.1016/j.chembiol.2015.12.009.

Huang et al., Heritable gene targeting in zebrafish using customized TALENs. Nat Biotechnol. Aug. 5, 2011;29(8):699-700. doi: 10.1038/nbt.1939.

Huang et al., Long-range pseudoknot interactions dictate the regulatory response in the tetrahydrofolate riboswitch. Proc Natl Acad Sci U S A. Sep. 6, 2011;108(36):14801-6. doi: 10.1073/pnas.1111701108. Epub Aug. 22, 2011.

Humbert et al., Targeted gene therapies: tools, applications, optimization. Crit Rev Biochem Mol Biol. May-Jun. 2012;47(3):264-81. doi: 10.3109/10409238.2012.658112.

Hurt et al., Highly specific zinc finger proteins obtained by directed domain shuffling and cellbased selection. Proc Natl Acad Sci U S A. Oct. 14, 2003;100(21):12271-6. Epub Oct. 3, 2003.

Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.

Hwang et al., Efficient In Vivo Genome Editing Using RNA-Guided Nucleases. Nat Biotechnol. Mar. 2013;31(3): 227-229. doi: 10.1038/nbt.2501. Epub Jan. 29, 2013.

Händel et al., Expanding or restricting the target site repertoire of zinc-finger nucleases: the inter-domain linker as a major determinant of target site selectivity. Mol Ther. Jan. 2009;17(1):104-11. doi: 10.1038/mt.2008.233. Epub Nov. 11, 2008.

Ikediobi et al., Mutation analysis of 24 known cancer genes in the NCI-60 cell line set. Mol Cancer Ther. Nov. 2006;5(11):2606-12. Epub Nov. 6, 2006.

International Preliminary Report on Patentability for PCT/US2016/058344, dated May 3, 2018.

International Preliminary Report on Patentability for PCT/US2012/047778, dated Feb. 6, 2014.

International Preliminary Report on patentability for PCT/US2014/050283, dated Feb. 18, 2016.

International Preliminary Report on Patentability for PCT/US2014/052231, dated Mar. 3, 2016.

International Preliminary Report on Patentability for PCT/US2014/054247, dated Mar. 17, 2016.

International Preliminary Report on Patentability for PCT/US2014/054291, dated Mar. 17, 2016.

International Preliminary Report on Patentability for PCT/US2014/070038, dated Jun. 23, 2016.

International Preliminary Report on Patentability for PCT/US2015/042770, dated Dec. 19, 2016.

International Preliminary Report on Patentability for PCT/US2015/058479, dated May 11, 2017.

International Preliminary Report on Patentability or PCT/US2014/054252, dated Mar. 17, 2016.

International Search Report and Written Opinion for PCT/US2012/047778, dated May 30, 2013.

International Search Report and Written Opinion for PCT/US2014/050283, dated Nov. 6, 2014.

International Search Report and Written Opinion for PCT/US2014/052231, dated Dec. 4, 2014.

International Search Report and Written Opinion for PCT/US2014/052231, dated Jan. 30, 2015 (Corrected Version).

International Search Report and Written Opinion for PCT/US2014/054247, dated Mar. 27, 2015.

International Search Report and Written Opinion for PCT/US2014/054252, dated Mar. 5, 2015.

International Search Report and Written Opinion for PCT/US2014/054291, dated Mar. 27, 2015.

International Search Report and Written Opinion for PCT/US2014/070038, dated Apr. 14, 2015.

International Search Report and Written Opinion for PCT/US2015/042770, dated Feb. 23, 2016.

International Search Report and Written Opinion for PCT/US2015/058479, dated Feb. 11, 2016.

International Search Report and Written Opinion for PCT/US2016/044546, dated Dec. 28, 2016.

International Search Report and Written Opinion for PCT/US2016/058344, dated Apr. 20, 2017.

International Search Report and Written Opinion for PCT/US2017/045381, dated Oct. 26, 2017.

International Search Report and Written Opinion for PCT/US2017/046144, dated Oct. 10, 2017.

International Search Report and Written Opinion for PCT/US2017/056671, dated Feb. 20, 2018.

International Search Report and Written Opinion for PCT/US2017/068105, dated Apr. 4, 2018.

International Search Report and Written Opinion for PCT/US2017/068114, dated Mar. 20, 2018.

International Search Report and Written Opinion for PCT/US2017/48390, dated Jan. 9, 2018.

International Search Report for PCT/US2013/032589, dated Jul. 26, 2013.

International Search Report for PCT/US2018/021664, dated Jun. 21, 2018.

International Search Report for PCT/US2018/021878, dated Aug. 20, 2018.

International Search Report for PCT/US2018/021880, dated Jun. 20, 2018.

International Search Report for PCT/US2018/024208, dated Aug. 23, 2018.

International Search Report for PCT/US2018/025887, dated Jun. 21, 2018.

International Search Report for PCT/US2018/032460, dated Jul. 11, 2018.

(56) References Cited

OTHER PUBLICATIONS

Invitation to Pay Additional Fees for PCT/US2014/054291, dated Dec. 18, 2014.
Invitation to Pay Additional Fees for PCT/US2016/058344, dated Mar. 1, 2017.
Invitation to Pay Additional Fees for PCT/US2017/056671, dated Dec. 21, 2017.
Invitation to Pay Additional Fees for PCT/US2017/48390, dated Nov. 7, 2017.
Invitation to Pay Additional Fees for PCT/US2018/021878, dated Jun. 8, 2018.
Irrthum et al., Congenital hereditary lymphedema caused by a mutation that inactivates VEGFR3 tyrosine kinase. Am J Hum Genet. Aug. 2000;67(2):295-301. Epub Jun. 9, 2000.
Ishino et al., Nucleotide sequence of the iap gene, responsible for alkaline phosphatase isozyme conversion in *Escherichia coli*, and identification of the gene product. J Bacteriol. Dec. 1987;169(12):5429-33.
Jamieson et al., Drug discovery with engineered zinc-finger proteins. Nat Rev Drug Discov. May 2003;2(5):361-8.
Jansen et al., Backbone and nucleobase contacts to glucosamine-6-phosphate in the glmS ribozyme. Nat Struct Mol Biol. Jun. 2006;13(6):517-23. Epub May 14, 2006.
Jansen et al., Identification of genes that are associated with DNA repeats in prokaryotes. Mol Microbiol. Mar. 2002;43(6): 1565-75.
Jenkins et al., Comparison of a preQ1 riboswitch aptamer in metabolite-bound and free states with implications for gene regulation. J Biol Chem. Jul. 15, 2011;286(28):24626-37. doi: 10.1074/jbc.M111.230375. Epub May 18, 2011.
Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.
Jiang et al., Structures of a CRISPR-Cas9 R-loop complex primed for DNA cleavage. Science. Feb. 19, 2016;351(6275):867-71. doi: 10.1126/science.aad8282. Epub Jan. 14, 2016.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Jinek et al., RNA-programmed genome editing in human cells. Elife. Jan. 29, 2013;2:e00471. doi: 10.7554/eLife.00471.
Jinek et al., Structures of Cas9 endonucleases reveal RNA-mediated conformational activation. Science. Mar. 14, 2014;343(6176):1247997. doi: 10.1126/science.1247997. Epub Feb. 6, 2014.
Jore et al., Structural basis for CRISPR RNA-guided DNA recognition by Cascade. Nat Struct Mol Biol. May 2011;18(5):529-36. doi: 10.1038/nsmb.2019. Epub Apr. 3, 2011.
Joung et al.,TALENs: a widely applicable technology for targeted genome editing. Nat Rev Mol Cell Biol. Jan. 2013;14(1):49-55. doi: 10.1038/nrm3486. Epub Nov. 21, 2012.
Kaiser et al., Gene therapy. Putting the fingers on gene repair. Science. Dec. 23, 2005;310(5756):1894-6.
Kandavelou et al., Targeted manipulation of mammalian genomes using designed zinc finger nucleases. Biochem Biophys Res Commun. Oct. 9, 2009;388(1):56-61. doi: 10.1016/j.bbrc.2009.07.112. Epub Jul. 25, 2009.
Kang et al., Structural Insights into riboswitch control of the biosynthesis of queuosine, a modified nucleotide found in the anticodon of tRNA. Mol Cell. Mar. 27, 2009;33(6):784-90. doi: 10.1016/j.molcel.2009.02.019. Epub Mar. 12, 2009.
Kappel et al., Regulating gene expression in transgenic animals. Curr Opin Biotechnol. Oct. 1992;3(5):548-53.
Karpenshif et al., From yeast to mammals: recent advances in genetic control of homologous recombination. DNA Repair (Amst). Oct. 1, 2012;11(10):781-8. doi: 10.1016/j.dnarep.2012.07.001. Epub Aug. 11, 2012. Review.
Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.

Kaya et al., A bacterial Argonaute with noncanonical guide RNA specificity. Proc. Natl. Acad. Sci. USA Apr. 2016;113(15):4057-62.
Kellendonk et al., Regulation of Cre recombinase activity by the synthetic steroid RU 486. Nucleic Acids Res. Apr. 15, 1996;24(8):1404-11.
Kilbride et al., Determinants of product topology in a hybrid Cre-Tn3 resolvase site-specific recombination system. J Mol Biol. Jan. 13, 2006;355(2):185-95. Epub Nov. 9, 2005.
Kim et al., A library of TAL effector nucleases spanning the human genome. Nat Biotechnol. Mar. 2013;31(3):251-8. Doi: 10.1038/nbt.2517. Epub Feb. 17, 2013.
Kim et al., Genome-wide target specificities of CRISPR RNA-guided programmable deaminases. Nat Biotechnol. May 2017;35(5):475-480. doi: 10.1038/nbt.3852. Epub Apr. 10, 2017.
Kim et al., Highly efficient RNA-guided base editing in mouse embryos. Nat Biotechnol. May 2017;35(5):435-437. doi: 10.1038/nbt.3816. Epub Feb. 27, 2017.
Kim et al., Highly efficient RNA-guided genome editing in human cells via delivery of purified Cas9 ribonucleoproteins. Genome Res. Jun. 2014;24(6):1012-9. doi: 10.1101/gr.171322.113. Epub Apr. 2, 2014.
Kim et al., Hybrid restriction enzymes: zinc finger fusions to Fok I cleavage domain. Proc Natl Acad Sci U S A. Feb. 6, 1996;93(3):1156-60.
Kim et al., Increasing the genome-targeting scope and precision of base editing with engineered Cas9-cytidine deaminase fusions. Nat Biotechnol. Apr. 2017;35(4):371-376. doi: 10.1038/nbt.3803. Epub Feb. 13, 2017.
Kim et al., TALENs and ZFNs are associated with different mutationsignatures. Nat Methods. Mar. 2013;10(3):185. doi: 10.1038/nmeth.2364. Epub Feb. 10, 2013.
Kim et al., Targeted genome editing in human cells with zinc finger nucleases constructed via modular assembly. Genome Res. Jul. 2009;19(7):1279-88. doi: 10.1101/gr.089417.108. Epub May 21, 2009.
Kim et al., The role of apolipoprotein E in Alzheimer's disease. Neuron. Aug. 13, 2009;63(3):287-303. doi: 10.1016/j.neuron.2009.06.026.
Kim et al., Transcriptional repression by zinc finger peptides. Exploring the potential for applications in gene therapy. J Biol Chem. Nov. 21, 1997;272(47):29795-800.
Kitamura et al., Uracil DNA glycosylase counteracts APOBEC3G-induced hypermutation of hepatitis B viral genomes: excision repair of covalently closed circular DNA. PLoS Pathog. 2013;9(5):e1003361. doi: 10.1371/journal.ppat.1003361. Epub May 16, 2013.
Klauser et al., An engineered small RNA-mediated genetic switch based on a ribozyme expression platform. Nucleic Acids Res. May 1, 2013;41(10):5542-52. doi: 10.1093/nar/gkt253. Epub Apr. 12, 2013.
Klein et al., Cocrystal structure of a class I preQ1 riboswitch reveals a pseudoknot recognizing an essential hypermodified nucleobase. Nat Struct Mol Biol. Mar. 2009;16(3):343-4. doi: 10.1038/nsmb.1563.Epub Feb. 22, 2009.
Kleinstiver et al., Broadening the targeting range of *Staphylococcus aureus* CRISPR-Cas9 by modifying PAM recognition. Nat Biotechnol. Dec. 2015;33(12):1293-1298. doi: 10.1038/nbt.3404. Epub Nov. 2, 2015.
Kleinstiver et al., Engineered CRISPR-Cas9 nucleases with altered PAM specificities. Nature. Jul. 23, 2015;523(7561):481-5. doi: 10.1038/nature14592. Epub Jun. 22, 2015.
Kleinstiver et al., High-fidelity CRISPR-Cas9 nucleases with no detectable genome-wide off-target effects. Nature. Jan. 28, 2016;529(7587):490-5. doi: 10.1038/nature16526. Epub Jan. 6, 2016.
Kleinstiver et al., Monomeric site-specific nucleases for genome editing. Proc Natl Acad Sci U S A. May 22, 2012;109(21):8061-6. doi: 10.1073/pnas.1117984109. Epub May 7, 2012.
Klippel et al., Isolation and characterization of unusual gin mutants. EMBO J. Dec. 1, 1988;7(12):3983-9.
Klippel et al., The DNA invertase Gin of phage Mu: formation of a covalent complex with DNA via a phosphoserine at amino acid position 9. EMBO J. Apr. 1988;7(4):1229-37.

(56) References Cited

OTHER PUBLICATIONS

Klug et al., Zinc fingers: a novel protein fold for nucleic acid recognition. Cold Spring Harb Symp Quant Biol. 1987;52:473-82.
Kohli et al., Local sequence targeting in the AID/APOBEC family differentially impacts retroviral restriction and antibody diversification. J Biol Chem. Dec. 24, 2010;285(52):40956-64. doi: 10.1074/jbc. M110.177402. Epub Oct. 6, 2010.
Komor et al., CRISPR-Based Technologies for the Manipulation of Eukaryotic Genomes. Cell. Jan. 12, 2017;168(1-2):20-36. doi: 10.1016/j.cell.2016.10.044.
Komor et al., Improved base excision repair inhibition and bacteriophage Mu Gam protein yields C:G-to-T:A base editors with higher efficiency and product purity. Sci Adv. Aug. 30, 2017;3(8):eaao4774. doi: 10.1126/sciadv.aao4774. eCollection Aug. 2017.
Komor et al., Programmable editing of a target base in genomic DNA without double-stranded DNA cleavage. Nature. Apr. 20, 2016;533(7603):420-4. doi: 10.1038/nature17946.
Kouzminova et al., Patterns of chromosomal fragmentation due to uracil-DNA incorporation reveal a novel mechanism of replication-dependent double-stranded breaks. Mol Microbiol. Apr. 2008;68(1):202-15. doi: 10.1111/j.1365-2958.2008.06149.x.
Krishna et al., Structural classification of zinc fingers: survey and summary. Nucleic Acids Res. Jan. 15, 2003;31(2):532-50.
Kumar et al., Structural and functional consequences of the mutation of a conserved arginine residue in alphaA and alphaB crystallins. J Biol Chem. Aug. 20, 1999;274(34):24137-41.
Kundu et al., Leucine to proline substitution by SNP at position 197 in Caspase-9 gene expression leads to neuroblastoma: a bioinformatics analysis. 3 Biotech. 2013; 3:225-34.
Kunz et al., DNA Repair in mammalian cells: Mismatched repair: variations on a theme. Cell Mol Life Sci. Mar. 2009;66(6):1021-38. doi: 10.1007/s00018-009-8739-9.
Kury et al., De Novo Disruption of the Proteasome Regulatory Subunit PSMD12 Causes a Syndromic Neurodevelopmental Disorder. Am J Hum Genet. Feb. 2, 2017;100(2):352-363. doi: 10.1016/j.ajhg.2017.01.003. Epub Jan. 26, 2017.
Kuscu et al., CRISPR-STOP: gene silencing through base-editing-induced nonsense mutations. Nat Methods. Jul. 2017;14(7):710-712. doi: 10.1038/nmeth.4327. Epub Jun. 5, 2017.
Kuscu et al., Genome-wide analysis reveals characteristics of off-target sites bound by the Cas9 endonuclease. Nat Biotechnol. Jul. 2014;32(7):677-83. doi: 10.1038/nbt.2916. Epub May 18, 2014.
Kwon et al., Chemical basis of glycine riboswitch cooperativity. RNA. Jan. 2008;14(1):25-34. Epub Nov. 27, 2007.
Landrum et al., ClinVar: public archive of interpretations of clinically relevant variants. Nucleic Acids Res. Jan. 4, 2016;44(D1):D862-8. doi: 10.1093/nar/gkv1222. Epub Nov. 17, 2015.
Langer et al., Chemical and Physical Structure of Polymers as Carriers for Controlled Release of Bioactive Agents: A Review. Journal of Macromolecular Science, 2006;23(1):61-126. DOI: 10.1080/07366578308079439.
Langer et al., New methods of drug delivery. Science. Sep. 28, 1990;249(4976):1527-33.
Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.
Lau et al., Molecular basis for discriminating between normal and damaged bases by the human alkyladenine glycosylase, AAG. Proc Natl Acad Sci U S A. Dec. 5, 2000;97(25):13573-8.
Lavergne et al., Defects in type IIA von Willebrand disease: a cysteine 509 to arginine substitution in the mature von Willebrand factor disrupts a disulphide loop involved in the interaction with platelet glycoprotein Ib-IX. Br J Haematol. Sep. 1992;82(1):66-72.
Lawrence et al., Supercharging proteins can impart unusual resilience. J Am Chem Soc. Aug. 22, 2007;129(33):10110-2. Epub Aug. 1, 2007.
Lazar et al., Transforming growth factor alpha: mutation of aspartic acid 47 and leucine 48 results in different biological activities. Mol Cell Biol. Mar. 1988;8(3):1247-52.

Ledford, Gene-editing hack yields pinpoint precision. Nature, Apr. 20, 2016. http://www.nature.com/news/gene-editing-hack-yields-pinpoint-precision-1.19773.
Lee et al., A chimeric thyroid hormone receptor constitutively bound to DNA requires retinoid X receptor for hormone-dependent transcriptional activation in yeast. Mol Endocrinol. Sep. 1994;8(9):1245-52.
Lee et al., An allosteric self-splicing ribozyme triggered by a bacterial second messenger. Science. Aug. 13, 2010;329(5993):845-8. doi: 10.1126/science.1190713.
Lee et al., Failure to detect DNA-guided genome editing using Natronobacterium gregoryi Argonaute. Nat Biotechnol. Nov. 28, 2016;35(1):17-18. doi: 10.1038/nbt.3753.
Lee et al., PIK3CA gene is frequently mutated in breast carcinomas and hepatocellular carcinomas. Oncogene. Feb. 17, 2005;24(8):1477-80.
Lee et al., Recognition of liposomes by cells: in vitro binding and endocytosis mediated by specific lipid headgroups and surface charge density. Biochim Biophys Acta. Jan. 31, 1992;1103(2):185-97.
Lee et al., Ribozyme Mediated gRNA Generation for In Vitro and In Vivo CRISPR/Cas9 Mutagenesis. PLoS One. Nov. 10, 2016;11(11):e0166020. doi: 10.1371/journal.pone.0166020. eCollection 2016.
Lei et al., Efficient targeted gene disruption in Xenopus embryos using engineered transcription activator-like effector nucleases (TALENs). Proc Natl Acad Sci U S A. Oct. 23, 2012;109(43):17484-9. Doi: 10.1073/pnas.1215421109. Epub Oct. 8, 2012.
Lenk et al., Pathogenic mechanism of the FIG4 mutation responsible for Charcot-Marie-Tooth disease CMT4J. PLoS Genet. Jun. 2011;7(6):e1002104. doi: 10.1371/journal.pgen.1002104. Epub Jun. 2, 2011.
Levy et al., Inhibition of calcification of bioprosthetic heart valves by local controlled-release diphosphonate. Science. Apr. 12, 1985;228(4696):190-2.
Lewis et al., A serum-resistant cytofectin for cellular delivery of antisense oligodeoxynucleotides and plasmid DNA. Proc Natl Acad Sci U S A. Apr. 16, 1996;93(8):3176-81.
Lewis et al., Codon 129 polymorphism of the human prion protein influences the kinetics of amyloid formation. J Gen Virol. Aug. 2006;87(Pt 8):2443-9.
Li et al., Base editing with a Cpf1-cytidine deaminase fusion. Nat Biotechnol. Apr. 2018;36(4):324-327. doi: 10.1038/nbt.4102. Epub Mar. 19, 2018.
Li et al., Current approaches for engineering proteins with diverse biological properties. Adv Exp Med Biol. 2007;620:18-33.
Li et al., Generation of Targeted Point Mutations in Rice by a Modified CRISPR/Cas9 System. Mol Plant. Mar. 6, 2017;10(3):526-529. doi: 10.1016/j.molp.2016.12.001. Epub Dec. 8, 2016.
Li et al., Highly efficient and precise base editing in discarded human tripronuclear embryos. Protein Cell. Aug. 19, 2017. doi: 10.1007/s13238-017-0458-7. [Epub ahead of print].
Li et al., Modularly assembled designer TAL effector nucleases for targeted gene knockout and gene replacement in eukaryotes. Nucleic Acids Res. Aug. 2011;39(14):6315-25. doi: 10.1093/nar/gkr188. Epub Mar. 31, 2011.
Li et al., Multiplex and homologous recombination-mediated genome editing in *Arabidopsis* and Nicotiana benthamiana using guide RNA and Cas9. Nat Biotechnol. Aug. 2013;31(8):688-91. doi: 10.1038/nbt.2654.
Li et al., TAL nucleases (TALNs): hybrid proteins composed of TAL effectors and FokI DNA-cleavage domain. Nucleic Acids Res. Jan. 2011;39(1):359-72. doi: 10.1093/nar/gkq704. Epub Aug. 10, 2010.
Liang et al., Rapid and highly efficient mammalian cell engineering via Cas9 protein transfection. Send to; J Biotechnol. Aug. 20, 2015;208:44-53. doi: 10.1016/j.jbiotec.2015.04.024.
Lieber et al., Mechanism and regulation of human non-homologous DNA end-joining. Nat Rev Mol Cell Biol. Sep. 2003;4(9):712-20.
Lin et al., Enhanced homology-directed human genome engineering by controlled timing of CRISPR/Cas9 delivery. Elife. Dec. 15, 2014;3:e04766. doi: 10.7554/eLife.04766.

(56) References Cited

OTHER PUBLICATIONS

Liu et al., C2c1-sgRNA Complex Structure Reveals RNA-Guided DNA Cleavage Mechanism. Molecular Cell Jan. 2017;65(2):310-22.

Liu et al., Apolipoprotein E and Alzheimer disease: risk, mechanisms and therapy. Nat Rev Neurol. Feb. 2013;9(2):106-18. doi: 10.1038/nrneurol.2012.263. Epub Jan. 8, 2013.

Liu et al., Balancing AID and DNA repair during somatic hypermutation. Trends Immunol. Apr. 2009;30(4):173-81. doi: 10.1016/j.it.2009.01.007.

Liu et al., Cell-penetrating peptide-mediated delivery of TALEN proteins via bioconjugation for genome engineering. PLoS One. Jan. 20, 2014;9(1):e85755. doi: 10.1371/journal.pone.0085755. eCollection 2014.

Liu et al., Design of polydactyl zinc-finger proteins for unique addressing within complex genomes. Proc Natl Acad Sci U S A. May 27, 1997;94(11):5525-30.

Liu et al., Distance determination by GIY-YIG intron endonucleases: discrimination between repression and cleavage functions. Nucleic Acids Res. Mar. 31, 2006;34(6):1755-64. Print 2006.

Liu et al., Fast Colorimetric Sensing of Adenosine and Cocaine Based on a General Sensor Design Involving Aptamers and Nanoparticles. Angew Chem. 2006;118(1):96-100.

Lombardo et al., Gene editing in human stem cells using zinc finger nucleases and integrasedefective lentiviral vector delivery. Nat Biotechnol. Nov. 2007;25(11):1298-306. Epub Oct. 28, 2007.

Losey et al., Crystal structure of *Staphylococcus sureus* tRNA adenosine deaminase tadA in complex with RNA. Nature Struct. Mol. Biol. Feb. 2006;13(2):153-9.

Lu et al., Precise Editing of a Target Base in the Rice Genome Using a Modified CRISPR/Cas9 System. Mol Plant. Mar. 6, 2017;10(3):523-525. doi: 10.1016/j.molp.2016.11.013. Epub Dec. 6, 2016.

Lundberg et al., Delivery of short interfering RNA using endosomolytic cell-penetrating peptides. FASEB J. Sep. 2007;21(11):2664-71. Epub Apr. 26, 2007.

Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19.

Lyons et al., Efficient Recognition of an Unpaired Lesion by a DNA Repair Glycosylase. J. Am. Chem. Soc., 2009;131(49):17742-3. DOI: 10.1021/ja908378y.

Ma et al., Targeted AID-mediated mutagenesis (TAM) enables efficient genomic diversification in mammalian cells. Nature Methods. Oct. 2016;13:1029-35. doi:10.1038/nmeth.4027.

Maeder et al., CRISPR RNA-guided activation of endogenous human genes. Nat Methods. Oct. 2013;10(10):977-9. doi: 10.1038/nmeth.2598. Epub Jul. 25, 2013.

Maeder et al., Rapid "open-source" engineering of customized zinc-finger nucleases for highly efficient gene modification. Mol Cell. Jul. 25, 2008;31(2):294-301. doi:10.1016/j.molcel.2008.06.016.

Maeder et al., Robust, synergistic regulation of human gene expression using TALE activators. Nat Methods. Mar. 2013;10(3):243-5. doi: 10.1038/nmeth.2366. Epub Feb. 10, 2013.

Mahfouz et al., De novo-engineered transcription activator-like effector (TALE) hybrid nuclease with novel DNA binding specificity creates double-strand breaks. Proc Natl Acad Sci U S A. Feb. 8, 2011;108(6):2623-8. doi: 10.1073/pnas. 1019533108. Epub Jan. 24, 2011.

Mak et al., The crystal structure of TAL effector PthXo1 bound to its DNA target. Science. Feb. 10, 2012;335(6069):716-9. doi: 10.1126/science.1216211. Epub Jan. 5, 2012.

Makarova et al., Prokaryotic homologs of Argonaute proteins are predicted to function as key components of a novel system of defense against mobile genetic elements. Biology Direct 2009;4:29.

Makarova et al., An updated evolutionary classification of CRISPR-Cas systems. Nat Rev Microbiol. Nov. 2015;13(11):722-36. doi: 10.1038/nrmicro3569. Epub Sep. 28, 2015.

Makarova et al., Evolution and classification of the CRISPR-Cas systems. Nat Rev Microbiol. Jun. 2011;9(6):467-77. doi: 10.1038/nrmicro2577. Epub May 9, 2011.

Mali et al., Cas9 as a versatile tool for engineering biology. Nat Methods. Oct. 2013;10(10):957-63. doi: 10.1038/nmeth.2649.

Mali et al., CAS9 transcriptional activators for target specificity screening and paired nickases for cooperative genome engineering. Nat Biotechnol. Sep. 2013;31(9):833-8. doi: 10.1038/nbt.2675. Epub Aug. 1, 2013.

Mali et al., RNA-guided human genome engineering via Cas9. Science. Feb. 15, 2013;339(6121):823-6. doi: 10.1126/science. 1232033. Epub Jan. 3, 2013.

Mandal et al., A glycine-dependent riboswitch that uses cooperative binding to control gene expression. Science. Oct. 8, 2004;306(5694):275-9.

Mandal et al., Adenine riboswitches and gene activation by disruption of a transcription terminator. Nat Struct Mol Biol. Jan. 2004;11(1):29-35. Epub Dec. 29, 2003.

Mani et al., Design, engineering, and characterization of zinc finger nucleases. Biochem Biophys Res Commun. Sep. 23, 2005;335(2):447-57.

Marioni et al., DNA methylation age of blood predicts all-cause mortality in later life. Genome Biol. Jan. 30, 2015;16:25. doi: 10.1186/s13059-015-0584-6.

Marraffini et al., CRISPR interference limits horizontal gene transfer in staphylococci by targeting DNA. Science. Dec. 19, 2008;322(5909):1843-5. doi: 10.1126/science.1165771.

Maruyama et al., Increasing the efficiency of precise genome editing with CRISPR-Cas9 by inhibition of nonhomologous end joining. Nat Biotechnol. May 2015;33(5):538-42. doi: 10.1038/nbt.3190. Epub Mar. 23, 2015.

McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas. 0807883106. Epub Mar. 23, 2009.

Meckler et al., Quantitative analysis of TALE-DNA interactions suggests polarity effects. Nucleic Acids Res. Apr. 2013;41(7):4118-28. doi: 10.1093/nar/gkt085. Epub Feb. 13, 2013.

Mei et al., Recent Progress in CRISPR/Cas9 Technology. J Genet Genomics. Feb. 20, 2016;43(2):63-75. doi: 10.1016/j.jgg.2016.01.001. Epub Jan. 18, 2016.

Meng et al., Profiling the DNA-binding specificities of engineered Cys2His2 zinc finger domains using a rapid cell-based method. Nucleic Acids Res. 2007;35(11):e81. Epub May 30, 2007.

Meng et al., Targeted gene inactivation in zebrafish using engineered zinc-finger nucleases. Nat Biotechnol. Jun. 2008;26(6):695-701. doi: 10.1038/nbt1398. Epub May 25, 2008.

Mercer et al., Chimeric TALE recombinases with programmable DNA sequence specificity. Nucleic Acids Res. Nov. 2012;40(21):11163-72. doi: 10.1093/nar/gks875. Epub Sep. 26, 2012.

Meyer et al., Breathing life into polycations: functionalization with pH-responsive endosomolytic peptides and polyethylene glycol enables siRNA delivery. J Am Chem Soc. Mar. 19, 2008;130(11):3272-3. doi: 10.1021/ja710344v. Epub Feb. 21, 2008.

Meyer et al., Confirmation of a second natural preQ1 aptamer class in Streptococcaceae bacteria. RNA. Apr. 2008;14(4):685-95. doi: 10.1261/rna.937308. Epub Feb. 27, 2008.

Midoux et al., Chemical vectors for gene delivery: a current review on polymers, peptides and lipids containing histidine or imidazole as nucleic acids carriers. Br J Pharmacol. May 2009;157(2):166-78. doi: 10.1111/j.1476-5381.2009.00288.x.

Miller et al., A TALE nuclease architecture for efficient genome editing. Nat Biotechnol. Feb. 2011;29(2):143-8. doi:10.1038/nbt. 1755. Epub Dec. 22, 2010.

Miller et al., An improved zinc-finger nuclease architecture for highly specific genome editing. Nat Biotechnol. Jul. 2007;25(7):778-85. Epub Jul. 1, 2007.

Minoche et al., Evaluation of genomic high-throughput sequencing data generated on Illumina HiSeq and genome analyzer systems. Genome Biol. Nov. 8, 2011;12(11):R112. doi: 10.1186/gb-2011-12-11-r112.

(56) References Cited

OTHER PUBLICATIONS

Minoretti et al., A W148R mutation in the human FOXD4 gene segregating with dilated cardiomyopathy, obsessive-compulsive disorder, and suicidality. Int J Mol Med. Mar. 2007;19(3):369-72.
Mojica et al., Intervening sequences of regularly spaced prokaryotic repeats derive from foreign genetic elements. J Mol Evol. Feb. 2005;60(2):174-82.
Mol et al., Crystal structure of human uracil-DNA glycosylase in complex with a protein inhibitor: protein mimicry of DNA. Cell. Sep. 8, 1995;82(5):701-8.
Montange et al., Structure of the S-adenosylmethionine riboswitch regulatory mRNA element. Nature. Jun. 29, 2006;441(7097):1172-5.
Moore et al., Improved somatic mutagenesis in zebrafish using transcription activator-like effector nucleases (TALENs). PloS One. 2012;7(5):e37877. Doi: 10.1371/journal.pone.0037877. Epub May 24, 2012.
Mootz et al., Conditional protein splicing: a new tool to control protein structure and function in vitro and in vivo. J Am Chem Soc. Sep. 3, 2003;125(35):10561-9.
Mootz et al., Protein splicing triggered by a small molecule. J Am Chem Soc. Aug. 7, 2002;124(31):9044-5.
Morbitzer et al., Assembly of custom TALE-type DNA binding domains by modular cloning. Nucleic Acids Res. Jul. 2011;39(13):5790-9. doi: 10.1093/nar/gkr151. Epub Mar. 18, 2011.
Morris et al., A peptide carrier for the delivery of biologically active proteins into mammalian cells. Nat Biotechnol. Dec. 2001;19(12):1173-6.
Moscou et al., A simple cipher governs DNA recognition by TAL effectors. Science. Dec. 11, 2009;326(5959):1501. doi: 10.1126/science.1178817.
Mullins et al., Transgenesis in nonmurine species. Hypertension. Oct. 1993;22(4):630-3.
Murphy, Phage recombinases and their applications. Adv Virus Res. 2012;83:367-414. doi: 10.1016/B978-0-12-394438-2.00008-6. Review.
Mussolino et al., A novel TALE nuclease scaffold enables high genome editing activity in combination with low toxicity. Nucleic Acids Res. Nov. 2011;39(21):9283-93. Doi: 10.1093/nar/gkr597. Epub Aug. 3, 2011.
Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.
Nahvi et al., Coenzyme B12 riboswitches are widespread genetic control elements in prokaryotes. Nucleic Acids Res. Jan. 2, 2004;32(1):143-50.
Narayanan et al., Clamping down on weak terminal base pairs: oligonucleotides with molecular caps as fidelity-enhancing elements at the 5'- and 3'-terminal residues. Nucleic Acids Res. May 20, 2004;32(9):2901-11. Print 2004.
Navaratnam et al., An overview of cytidine deaminases. Int J Hematol. Apr. 2006;83(3):195-200.
NCBI Reference Sequence: NM_002427.3. Wu et al., May 3, 2014. 5 pages.
Neel et al., Riboswitches: Classification, function and in silico approach, International Journal of Pharma Sciences and Research. 2010;1(9):409-420.
Ni et al., Nucleic acid aptamers: clinical applications and promising new horizons. Curr Med Chem. 2011;18(27):4206-14. Review.
Nishida et al., Targeted nucleotide editing using hybrid prokaryotic and vertebrate adaptive immune systems. Science. Sep. 16, 2016;353(6305). pii: aaf8729. doi: 10.1126/science.aaf8729. Epub Aug. 4, 2016.
Nishida et al., Targeted nucleotide editing using hybrid prokaryotic and vertebrate adaptive immune systems. Science. Sep. 16, 2016;353(6305):1248. pii: aaf8729. doi: 10.1126/science.aaf8729. Epub Aug. 4, 2016.
Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.

Nomura et al., Synthetic mammalian riboswitches based on guanine aptazyme. Chem Commun (Camb). Jul. 21, 2012;48(57):7215-7. doi: 10.1039/c2cc33140c. Epub Jun. 13, 2012.
Noris et al., A phenylalanine-55 to serine amino-acid substitution in the human glycoprotein IX leucine-rich repeat is associated with Bernard-Soulier syndrome. Br J Haematol. May 1997;97(2):312-20.
O'Connell et al., Programmable RNA recognition and cleavage by CRISPR/Cas9. Nature. Dec. 11, 2014;516(7530):263-6. doi: 10.1038/nature13769. Epub Sep. 28, 2014.
Offord, Advances in Genome Editing. The Scientist, Apr. 20, 2016. http://www.the-scientist.com/7articles.view/articleNo/45903/title/Advances-in-Genome-Editing/.
Olorunniji et al., Synapsis and catalysis by activated Tn3 resolvase mutants. Nucleic Acids Res. Dec. 2008;36(22):7181-91. doi: 10.1093/nar/gkn885. Epub Nov. 10, 2008.
Osborn et al., TALEN-based gene correction for epidermolysis bullosa. Mol Ther. Jun. 2013;21(6):1151-9. doi: 10.1038/mt.2013.56. Epub Apr. 2, 2013.
Pabo et al., Design and selection of novel Cys2His2 zinc finger proteins. Annu Rev Biochem. 2001;70:313-40.
Pan et al., Biological and biomedical applications of engineered nucleases. Mol Biotechnol. Sep. 2013;55(1):54-62. doi: 10.1007/s12033-012-9613-9.
Parker et al., Admixture mapping identifies a quantitative trait locus associated with FEV1/FVC in the COPDGene Study. Genet Epidemiol. Nov. 2014;38(7):652-9. doi: 10.1002/gepi.21847. Epub Aug. 11, 2014.
Partial Supplementary European Search Report for Application No. EP 12845790.0, dated Mar. 18, 2015.
Pattanayak et al., Determining the specificities of TALENs, Cas9, and other genomeediting enzymes. Methods Enzymol. 2014;546:47-78. doi: 10.1016/B978-0-12-801185-0.00003-9.
Pattanayak et al., High-throughput profiling of off-target DNA cleavage reveals RNA-programmed Cas9 nuclease specificity. Nat Biotechnol. Sep. 2013;31(9):839-43. doi: 10.1038/nbt.2673. Epub Aug. 11, 2013.
Pattanayak et al., Revealing off-target cleavage specificities of zinc-finger nucleases by in vitro selection. Nat Methods. Aug. 7, 2011;8(9):765-70. doi: 10.1038/nmeth.1670.
Pavletich et al., Zinc finger-DNA recognition: crystal structure of a Zif268-DNA complex at 2.1 A. Science. May 10, 1991;252(5007):809-17.
Pearl, Structure and function in the uracil-DNA glycosylase superfamily. Mutat Res. Aug. 30, 2000;460(3-4):165-81.
Peck et al., Directed evolution of a small-molecule-triggered intein with improved splicing properties in mammalian cells. Chem Biol. May 27, 2011;18(5):619-30. doi: 10.1016/j.chembiol.2011.02.014.
Pennisi et al., The CRISPR craze. Science. Aug. 23, 2013;341(6148):833-6. doi: 10.1126/science.341.6148.833.
Pennisi et al., The tale of the TALEs. Science. Dec. 14, 2012;338(6113):1408-11. doi: 10.1126/science.338.6113.1408.
Perez et al., Establishment of HIV-1 resistance in CD4+ T cells by genome editing using zinc-finger nucleases. Nat Biotechnol. Jul. 2008;26(7):808-16. Doi: 10.1038/nbt1410. Epub Jun. 29, 2008.
Perez-Pinera et al., Advances in targeted genome editing. Curr Opin Chem Biol. Aug. 2012;16(3-4):268-77. doi: 10.1016/j.cbpa.2012.06.007. Epub Jul. 20, 2012.
Perez-Pinera et al., RNA-guided gene activation by CRISPR-Cas9-based transcription factors. Nat Methods. Oct. 2013;10(10):973-6. doi: 10.1038/nmeth.2600. Epub Jul. 25, 2013.
Petek et al., Frequent endonuclease cleavage at off-target locations in vivo. Mol Ther. May 2010;18(5):983-6. Doi: 10.1038/mt.2010.35. Epub Mar. 9, 2010.
Petolino et al., Editing Plant Genomes: a new era of crop improvement. Plant Biotechnol J. Feb. 2016;14(2):435-6. doi: 10.1111/pbi.12542.
Pham et al., Reward versus risk: DNA cytidine deaminases triggering immunity and disease. Biochemistry. Mar. 1, 2005;44(8):2703-15.
Phillips, The challenge of gene therapy and DNA delivery. J Pharm Pharmacol. Sep. 2001;53(9):1169-74.

(56) References Cited

OTHER PUBLICATIONS

Plasterk et al., DNA inversions in the chromosome of *Escherichia coli* and in bacteriophage Mu: relationship to other site-specific recombination systems. Proc Natl Acad Sci U S A. Sep. 1983;80(17):5355-8.
Plosky et al., CRISPR-Mediated Base Editing without DNA Double-Strand Breaks. Mol Cell. May 19, 2016;62(4):477-8. doi: 10.1016/j.molcel.2016.05.006.
Pluciennik et al., PCNA function in the activation and strand direction of MutLα endonuclease in mismatch repair. Proc Natl Acad Sci U S A. Sep. 14, 2010;107(37):16066-71. doi: 10.1073/pnas.1010662107. Epub Aug. 16, 2010.
Poller et al., A leucine-to-proline substitution causes a defective alpha 1-antichymotrypsin allele associated with familial obstructive lung disease. Genomics. Sep. 1993;17(3):740-3.
Porteus, Design and testing of zinc finger nucleases for use in mammalian cells. Methods Mol Biol. 2008;435:47-61. doi: 10.1007/978-1-59745-232-8_4.
Pourcel et al., CRISPR elements in Yersinia pestis acquire new repeats by preferential uptake of bacteriophage DNA, and provide additional tools for evolutionary studies. Microbiology. Mar. 2005;151(Pt 3):653-63.
Prashant et al., CAS9 transcriptional activators for target specificity screening and paired nickases for cooperative genome engineering. Nature Biotechnology 2013;31(9):833-8.
Prorocic et al., Zinc-finger recombinase activities in vitro. Nucleic Acids Res. Nov. 2011;39(21):9316-28. doi: 10.1093/nar/gkr652. Epub Aug. 17, 2011.
Proudfoot et al., Zinc finger recombinases with adaptable DNA sequence specificity. PLoS One. Apr. 29, 2011;6(4):e19537. doi: 10.1371/journal.pone.0019537.
Prykhozhij et al., CRISPR multitargeter: a web tool to find common and unique CRISPR single guide RNA targets in a set of similar sequences. PLoS One. Mar. 5, 2015;10(3):e0119372. doi: 10.1371/journal.pone.0119372. eCollection 2015.
Putnam et al., Protein mimicry of DNA from crystal structures of the uracil-DNA glycosylase inhibitor protein and its complex with *Escherichia coli* uracil-DNA glycosylase. J Mol Biol. Mar. 26, 1999;287(2):331-46.
Putney et al., Improving protein therapeutics with sustained-release formulations. Nat Biotechnol. Feb. 1998;16(2):153-7.
Qi et al., Engineering naturally occurring trans-acting non-coding RNAs to sense molecular signals. Nucleic Acids Res. Jul. 2012;40(12):5775-86. doi: 10.1093/nar/gks168. Epub Mar. 1, 2012.
Qi et al., Repurposing CRISPR as an RNA-guided platform for sequence-specific control of gene expression. Cell. Feb. 28, 2013;152(5):1173-83. doi: 10.1016/j.cell.2013.02.022.
Ramakrishna et al., Gene disruption by cell-penetrating peptide-mediated delivery of Cas9 protein and guide RNA. Genome Res. Jun. 2014;24(6):1020-7. doi: 10.1101/gr.171264.113. Epub Apr. 2, 2014.
Ramirez et al., Engineered zinc finger nickases induce homology-directed repair with reduced mutagenic effects. Nucleic Acids Res. Jul. 2012;40(12):5560-8. doi: 10.1093/nar/ks179. Epub Feb. 28, 2012.
Ramirez et al., Unexpected failure rates for modular assembly of engineered zinc fingers. Nat Methods. May 2008;5(5):374-5. Doi: 10.1038/nmeth0508-374.
Ran et al., Double nicking by RNA-guided CRISPR Cas9 for enhanced genome editing specificity. Cell. Sep. 12, 2013;154(6):1380-9. doi: 10.1016/j.cell.2013.08.021. Epub Aug. 29, 2013.
Ran et al., Genome engineering using the CRISPR-Cas9 system. Nat Protoc. Nov. 2013;8(11):2281-308. doi: 10.1038/nprot.2013.143. Epub Oct. 24, 2013.
Ran et al., In vivo genome editing using *Staphylococcus aureus* Cas9. Nature. Apr. 9, 2015;520(7546):186-91. doi: 10.1038/nature14299. Epub Apr. 1, 2015.
Rath et al., Fidelity of end joining in mammalian episomes and the impact of Metnase on joint processing. BMC Mol Biol. Mar. 22, 2014;15:6. doi: 10.1186/1471-2199-15-6.
Ravishankar et al., X-ray analysis of a complex of *Escherichia coli* uracil DNA glycosylase (EcUDG) with a proteinaceous inhibitor. The structure elucidation of a prokaryotic UDG. Nuclei Acids Res. 26 (21): 4880-4887 (1998).
Ray et al., Homologous recombination: ends as the means. Trends Plant Sci. Oct. 2002;7(10):435-40.
Rebuzzini et al., New mammalian cellular systems to study mutations introduced at the break site by non-homologous end-joining. DNA Repair (Amst). May 2, 2005;4(5):546-55.
Rees et al., Improving the DNA specificity and applicability of base editing through protein engineering and protein delivery. Nat Commun. Jun. 6, 2017;8:15790. doi: 10.1038/ncomms15790.
Reynaud et al., What role for AID: mutator, or assembler of the immunoglobulin mutasome? Nat Immunol. Jul. 2003;4(7):631-8.
Richardson et al., Enhancing homology-directed genome editing by catalytically active and inactive CRISPR-Cas9 using asymmetric donor DNA. Nat Biotechnol. Mar. 2016;34(3):339-44. doi: 10.1038/nbt.3481. Epub Jan. 20, 2016.
Richter et al., Function and regulation of clustered regularly interspaced short palindromic repeats (CRISPR) / CRISPR associated (Cas) systems. Viruses. Oct. 19, 2012;4(10):2291-311. doi: 10.3390/v4102291.
Rizk et al., An engineered substance P variant for receptor-mediated delivery of synthetic antibodies into tumor cells. Proc Natl Acad Sci U S A. Jul. 7, 2009; 106(27):11011-5. doi: 10.1073/pnas.0904907106. Epub Jun. 22, 2009.
Rong et al., Homologous recombination in human embryonic stem cells using CRISPR/Cas9 nickase and a long DNA donor template. Protein Cell. Apr. 2014;5(4):258-60. doi: 10.1007/s13238-014-0032-5.
Rongrong et al., Effect of deletion mutation on the recombination activity of Cre recombinase. Acta Biochim Pol. 2005;52(2):541-4. Epub May 15, 2005.
Roth et al., A riboswitch selective for the queuosine precursor preQ1 contains an unusually small aptamer domain. Nat Struct Mol Biol. Apr. 2007;14(4):308-17. Epub Mar. 25, 2007.
Rowland et al., Regulatory mutations in Sin recombinase support a structure-based model of the synaptosome. Mol Microbiol. Oct. 2009;74(2):282-98. doi: 10.1111/j.1365-2958.2009.06756.x. Epub Jun. 8, 2009.
Sadelain et al., Safe harbours for the integration of new DNA in the human genome. Nat Rev Cancer. Dec. 1, 2011;12(1):51-8. doi: 10.1038/nrc3179.
Sage et al., Proliferation of functional hair cells in vivo in the absence of the retinoblastoma protein. Science. Feb. 18, 2005;307(5712):1114-8. Epub Jan. 13, 2005.
Saleh-Gohari et al., Conservative homologous recombination preferentially repairs DNA double-strand breaks in the S phase of the cell cycle in human cells. Nucleic Acids Res. Jul. 13, 2004;32(12):3683-8. Print 2004.
Samal et al., Cationic polymers and their therapeutic potential. Chem Soc Rev. Nov. 7, 2012;41(21):7147-94. doi: 10.1039/c2cs35094g. Epub Aug. 10, 2012.
Sander et al., CRISPR-Cas systems for editing, regulating and targeting genomes. Nat Biotechnol. Apr. 2014;32(4):347-55. doi: 10.1038/nbt.2842. Epub Mar. 2, 2014.
Sander et al., In silico abstraction of zinc finger nuclease cleavage profiles reveals an expanded landscape of off-target sites. Nucleic Acids Res. Oct. 2013;41(19):e181. doi: 10.1093/nar/gkt716. Epub Aug. 14, 2013.
Sander et al., Targeted gene disruption in somatic zebrafish cells using engineered TALENs. Nat Biotechnol. Aug. 5, 2011;29(8):697-8. doi: 10.1038/nbt.1934.
Sang, Prospects for transgenesis in the chick. Meeh Dev. Sep. 2004;121(9):1179-86.
Sanjana et al., A transcription activator-like effector toolbox for genome engineering. Nat Protoc. Jan. 5, 2012;7(1):171-92. doi: 10.1038/nprot.2011.431.
Santiago et al., Targeted gene knockout in mammalian cells by using engineered zinc-finger nucleases. Proc Natl Acad Sci U S A. Apr. 15, 2008;105(15):5809-14. doi: 10.1073/pnas.0800940105. Epub Mar. 21, 2008.

(56) References Cited

OTHER PUBLICATIONS

Sapranauskas et al., The *Streptococcus thermophilus* CRISPR/Cas system provides immunity in *Escherichia coli*. Nucleic Acids Res. Nov. 2011;39(21):9275-82. doi: 10.1093/nar/gkr606. Epub Aug. 3, 2011.
Saraconi et al., The RNA editing enzyme APOBEC1 induces somatic mutations and a compatible mutational signature is present in esophageal adenocarcinomas. Genome Biol. Jul. 31, 2014;15(7):417. doi: 10.1186/s13059-014-0417-z.
Sashital et al., Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.
Saudek et al., A preliminary trial of the programmable implantable medication system for insulin delivery. N Engl J Med. Aug. 31, 1989;321(9):574-9.
Schellenberger et al., A recombinant polypeptide extends the in vivo half-life of peptides and proteins in a tunable manner. Nat Biotechnol. Dec. 2009;27(12):1186-90. doi: 10.1038/nbt.1588.
Schriefer et al., Low pressure DNA shearing: a method for random DNA sequence analysis. Nucleic Acids Res. Dec. 25, 1990;18(24):7455-6.
Schwank et al., Functional repair of CFTR by CRISPR/Cas9 in intestinal stem cell organoids of cystic fibrosis patients. Cell Stem Cell. Dec. 5, 2013;13(6):653-8. doi: 10.1016/j.stem.2013.11.002.
Schwartz et al., Post-translational enzyme activation in an animal via optimized conditional protein splicing. Nat Chem Biol. Jan. 2007;3(1):50-4. Epub Nov. 26, 2006.
Schwarze et al., In vivo protein transduction: delivery of a biologically active protein into the mouse. Science. Sep. 3, 1999;285(5433):1569-72.
Sclimenti et al., Directed evolution of a recombinase for improved genomic integration at a native human sequence. Nucleic Acids Res. Dec. 15, 2001;29(24):5044-51.
Sefton et al., Implantable pumps. Crit Rev Biomed Eng. 1987;14(3):201-40.
Segal et al., Evaluation of a modular strategy for the construction of novel polydactyl zinc finger DNA-binding proteins. Biochemistry. Feb. 25, 2003;42(7):2137-48.
Segal et al., Toward controlling gene expression at will: selection and design of zinc finger domains recognizing each of the 5'-GNN-3' DNA target sequences. Proc Natl Acad Sci U S A. Mar. 16, 1999;96(6):2758-63.
Sells et al., Delivery of protein into cells using polycationic liposomes. Biotechniques. Jul. 1995;19(1):72-6, 78.
Semenova et al., Interference by clustered regularly interspaced short palindromic repeat (CRISPR) RNA is governed by a seed sequence. Proc Natl Acad Sci U S A. Jun. 21, 2011;108(25):10098-103. doi: 10.1073/pnas.1104144108. Epub Jun. 6, 2011.
Semple et al., Rational design of cationic lipids for siRNA delivery. Nat Biotechnol. Feb. 2010;28(2):172-6. doi: 10.1038/nbt.1602. Epub Jan. 17, 2010.
Serganov et al., Coenzyme recognition and gene regulation by a flavin mononucleotide riboswitch. Nature. Mar. 12, 2009;458(7235):233-7. doi: 10.1038/nature07642. Epub Jan. 25, 2009.
Serganov et al., Structural basis for discriminative regulation of gene expression by adenine-and guanine-sensing mRNAs. Chem Biol. Dec. 2004;11(12):1729-41.
Serganov et al., Structural basis for gene regulation by a thiamine pyrophosphate-sensing riboswitch. Nature. Jun. 29, 2006;441(7097):1167-71. Epub May 21, 2006.
Seripa et al., The missing ApoE allele. Ann Hum Genet. Jul. 2007;71(Pt 4):496-500. Epub Jan. 22, 2007.
Shah et al., Inteins: nature's gift to protein chemists. Chem Sci. 2014;5(1):446-461.
Shah et al., Kinetic control of one-pot trans-splicing reactions by using a wild-type and designed split intein. Angew Chem Int Ed Engl. Jul. 11, 2011;50(29):6511-5. doi: 10.1002/anie.201102909. Epub Jun. 8, 2011.
Shah et al., Target-specific variants of Flp recombinase mediate genome engineering reactions in mammalian cells. FEBS J. Sep. 2015;282(17):3323-33. doi: 10.1111/febs.13345. Epub Jul. 1, 2015.
Shaikh et al., Chimeras of the Flp and Cre recombinases: tests of the mode of cleavage by Flp and Cre. J Mol Biol. Sep. 8, 2000;302(1):27-48.
Shalem et al., Genome-scale CRISPR-Cas9 knockout screening in human cells. Science. Jan. 3, 2014;343(6166):84-7. doi: 10.1126/science.1247005. Epub Dec. 12, 2013.
Sharbeen et al., Ectopic restriction of DNA repair reveals that UNG2 excises AID-induced uracils predominantly or exclusively during G1 phase. J Exp Med. May 7, 2012;209(5):965-74. doi: 10.1084/jem.20112379. Epub Apr. 23, 2012.
Shcherbakova et al., Near-infrared fluorescent proteins for multicolor in vivo imaging. Nat Methods. Aug. 2013;10(8):751-4. doi: 10.1038/nmeth.2521. Epub Jun. 16, 2013.
Shee et al., Engineered proteins detect spontaneous DNA breakage in human and bacterial cells. Elife. Oct. 29, 2013;2:e01222. doi: 10.7554/eLife.01222.
Sheridan, First CRISPR-Cas patent opens race to stake out intellectual property. Nat Biotechnol. 2014;32(7):599-601.
Sheridan, Gene therapy finds its niche. Nat Biotechnol. Feb. 2011;29(2):121-8. doi: 10.1038/nbt.1769.
Shimantani et al., Targeted base editing in rice and tomato using a CRISPR-Cas9 cytidine deaminase fusion. Nat Biotechnol. May 2017;35(5):441-443. doi: 10.1038/nbt.3833. Epub Mar. 27, 2017.
Shimizu et al., Adding fingers to an engineered zinc finger nuclease can reduce activity. Biochemistry. Jun. 7, 2011;50(22):5033-41. doi: 10.1021/bi200393g. Epub May 11, 2011.
Shimojima et al., Spinocerebellar ataxias type 27 derived from a disruption of the fibroblast growth factor 14 gene with mimicking phenotype of paroxysmal non-kinesigenic dyskinesia. Brain Dev. Mar. 2012;34(3):230-3. doi: 10.1016/j.braindev.2011.04.014. Epub May 19, 2011.
Shmakov et al., Discovery and Functional Characterization of Diverse Class 2 CRISPR Cas Systems. Molecular Cell Nov. 2015;60(3):385-97.
Siebert et al., An improved PCR method for walking in uncloned genomic DNA. Nucleic Acids Res. Mar. 25, 1995;23(6): 1087-8.
Simonelli et al., Base excision repair intermediates are mutagenic in mammalian cells. Nucleic Acids Res. Aug. 2, 2005;33(14):4404-11. Print 2005.
Sirk et al., Expanding the zinc-finger recombinase repertoire: directed evolution and mutational analysis of serine recombinase specificity determinants. Nucleic Acids Res. Apr. 2014;42(7):4755-66. doi: 10.1093/nar/gkt1389. Epub Jan. 21, 2014.
Sjoblom et al., The consensus coding sequences of human breast and colorectal cancers. Science. Oct. 13, 2006;314(5797):268-74. Epub Sep. 7, 2006.
Skretas et al., Regulation of protein activity with small-molecule-controlled inteins. Protein Sci. Feb. 2005;14(2):523-32. Epub Jan. 4, 2005.
Slaymaker et al., Rationally engineered Cas9 nucleases with improved specificity. Science. Jan. 1, 2016;351(6268):84-8. doi: 10.1126/science.aad5227. Epub Dec. 1, 2015.
Smith et al., Diversity in the serine recombinases. Mol Microbiol. Apr. 2002;44(2):299-307. Review.
Smith et al., Expression of a dominant negative retinoic acid receptor γ in Xenopus embryos leads to partial resistance to retinoic acid. Roux Arch Dev Biol. Mar. 1994;203(5):254-265. doi: 10.1007/BF00360521.
Song et al., Antibody mediated in vivo delivery of small interfering RNAs via cell-surface receptors. Nat Biotechnol. Jun. 2005;23(6):709-17. Epub May 22, 2005.
Stenglein et al., APOBEC3 proteins mediate the clearance of foreign DNA from human cells. Nat Struct Mol Biol. Feb. 2010;17(2):222-9. doi: 10.1038/nsmb.1744. Epub Jan. 10, 2010.
Stephens et al., The landscape of cancer genes and mutational processes in breast cancer. Nature Jun. 2012;486:400-404. doi:10.1038/nature11017.
Sternberg et al., DNA interrogation by the CRISPR RNA-guided endonuclease Cas9. Nature.Mar. 6, 2014;507(7490):62-7. doi: 10.1038/nature13011. Epub Jan. 29, 2014.

(56) References Cited

OTHER PUBLICATIONS

Stevens et al., Design of a Split Intein with Exceptional Protein-Splicing Activity. J Am Chem Soc. Feb. 24, 2016; 138(7):2162-5. doi: 10.1021/jacs.5b13528. Epub Feb. 8, 2016.

Sudarsan et al., An mRNA structure in bacteria that controls gene expression by binding lysine. Genes Dev. Nov. 1, 2003 ;17(21):2688-97.

Sudarsan et al., Riboswitches in eubacteria sense the second messenger cyclic di-GMP. Science. Jul. 18, 2008;321(5887):411-3. doi: 10.1126/science.1159519.

Suess et al., A theophylline responsive riboswitch based on helix slipping controls gene expression in vivo. Nucleic Acids Res. Mar. 5, 2004;32(4):1610-4.

Sun et al., Optimized TAL effector nucleases (TALENs) for use in treatment of sickle cell disease. Mol Biosyst. Apr. 2012;8(4):1255-63. doi: 10.1039/c2mb05461b. Epub Feb. 3, 2012.

Supplementary European Search Report for Application No. EP 12845790.0, dated Oct. 12, 2015.

Swarts et al., Argonaute of the archaeon Pyrococcus furiosus is a DNA-guided nuclease that targets cognate DNA. Nucleic Acids Res. May 26, 2015;43(10):5120-9. doi: 10.1093/nar/gkv415. Epub Apr. 29, 2015.

Swarts et al., DNA-guided DNA interference by a prokaryotic Argonaute. Nature. Mar. 13, 2014;507(7491):258-61. doi: 10.1038/nature12971. Epub Feb. 16, 2014.

Swarts et al., The evolutionary journey of Argonaute proteins. Nat Struct Mol Biol. Sep. 2014;21(9):743-53. doi: 10.1038/nsmb.2879.

Szczepek et al., Structure-based redesign of the dimerization interface reduces the toxicity of zinc-finger nucleases. Nat Biotechnol. Jul. 2007;25(7):786-93. Epub Jul. 1, 2007.

Tagalakis et al., Lack of RNA-DNA oligonucleotide (chimeraplast) mutagenic activity in mouse embryos. Mol Reprod Dev. Jun. 2005;71(2):140-4.

Tang et al., Aptazyme-embedded guide RNAs enable ligand-responsive genome editing and transcriptional activation. Nat Commun. Jun. 28, 2017;8:15939. doi: 10.1038/ncomms15939.

Tebas et al., Gene editing of CCR5 in autologous CD4 T cells of persons infected with HIV. N Engl J Med. Mar. 6, 2014;370(10):901-10. doi: 10.1056/NEJMoa1300662.

Tessarollo et al., Targeted mutation in the neurotrophin-3 gene results in loss of muscle sensory neurons. Proc Natl Acad Sci U S A. Dec. 6, 1994;91(25):11844-8.

Tesson et al., Knockout rats generated by embryo microinjection of TALENs. Nat Biotechnol. Aug. 5, 2011;29(8):695-6. doi: 10.1038/nbt.1940.

Thompson et al., Cellular uptake mechanisms and endosomal trafficking of supercharged proteins. Chem Biol. Jul. 27, 2012;19(7):831-43. doi: 10.1016/j.chembiol.2012.06.014.

Thompson et al., Engineering and identifying supercharged proteins for macromolecule delivery into mammalian cells. Methods Enzymol. 2012;503:293-319. doi: 10.1016/B978-0-12-396962-0.00012-4.

Thorpe et al., Functional correction of episomal mutations with short DNA fragments and RNA-DNA oligonucleotides. J Gene Med. Mar.-Apr. 2002;4(2):195-204.

Thyagarajan et al., Mammalian genomes contain active recombinase recognition sites. Gene. Feb. 22, 2000;244(1-2):47-54.

Thyagarajan et al., Site-specific genomic integration in mammalian cells mediated by phage phiC31 integrase. Mol Cell Biol. Jun. 2001;21(12):3926-34.

Tirumalai et al., Recognition of core-type DNA sites by lambda integrase. J Mol Biol. Jun. 12, 1998;279(3):513-27.

Trausch et al., The structure of a tetrahydrofolate-sensing riboswitch reveals two ligand binding sites in a single aptamer. Structure. Oct. 12, 2011;19(10):1413-23. doi: 10.1016/j.str.2011.06.019. Epub Sep. 8, 2011.

Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.

Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015. With Supplementary Data.

Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.

Tsai et al., GUIDE-seq enables genome-wide profiling of off-target cleavage by CRISPR-Cas nucleases. Nat Biotechnol. Feb. 2015;33(2):187-97. doi: 10.1038/nbt.3117. Epub Dec. 16, 2014.

Turan et al., Recombinase-mediated cassette exchange (RMCE)—a rapidly-expanding toolbox for targeted genomic modifications. Gene. Feb. 15, 2013;515(1):1-27. doi: 10.1016/j.gene.2012.11.016. Epub Nov. 29, 2012.

Turan et al., Recombinase-mediated cassette exchange (RMCE): traditional concepts and current challenges. J Mol Biol. Mar. 25, 2011;407(2):193-221. doi: 10.1016/j.jmb.2011.01.004. Epub Jan. 15, 2011.

Turan et al., Site-specific recombinases: from tag-and-target- to tag-and-exchange-based genomic modifications. FASEB J. Dec. 2011;25(12):4088-107. doi: 10.1096/fj.11-186940. Epub Sep. 2, 2011. Review.

Tyszkiewicz et al., Activation of protein splicing with light in yeast. Nat Methods. Apr. 2008;5(4):303-5. doi: 10.1038/nmeth.1189. Epub Feb. 13, 2008.

UniProt Submission; UniProt, Accession No. P01011. Last modified Jun. 11, 2014, version 2. 15 pages.

UniProt Submission; UniProt, Accession No. P01011. Last modified Sep. 18, 2013, version 2. 15 pages.

UniProt Submission; UniProt, Accession No. P04264. Last modified Jun. 11, 2014, version 6. 15 pages.

UniProt Submission; UniProt, Accession No. P04275. Last modified Jul. 9, 2014, version 107. 29 pages.

Urnov et al., Genome editing with engineered zinc finger nucleases. Nat Rev Genet. Sep. 2010;11(9):636-46. doi: 10.1038/nrg2842.

Urnov et al., Highly efficient endogenous human gene correction using designed zinc-finger nucleases. Nature. Jun. 2, 2005;435(7042):646-51. Epub Apr. 3, 2005.

Vagner et al., Efficiency of homologous DNA recombination varies along the Bacillus subtilis chromosome. J Bacteriol. Sep. 1988;170(9):3978-82.

Van Duyne et al., Teaching Cre to follow directions. Proc Natl Acad Sci U S A. Jan. 6, 2009;106(1):4-5. doi: 10.1073/pnas.0811624106. Epub Dec. 31, 2008.

Van Swieten et al., A mutation in the fibroblast growth factor 14 gene is associated with autosomal dominant cerebellar ataxia [corrected]. Am J Hum Genet. Jan. 2003;72(1):191-9. Epub Dec. 13, 2002.

Vanamee et al., FokI requires two specific DNA sites for cleavage. J Mol Biol. May 25, 2001;309(1):69-78.

Venken et al., Genome-wide manipulations of *Drosophila melanogaster* with transposons, Flp recombinase, and ΦC31 integrase. Methods Mol Biol. 2012;859:203-28. doi: 10.1007/978-1-61779-603-6_12.

Vitreschak et al., Regulation of the vitamin B12 metabolism and transport in bacteria by a conserved RNA structural element. RNA. Sep. 2003;9(9):1084-97.

Wacey et al., Disentangling the perturbational effects of amino acid substitutions in the DNA-binding domain of p53. Hum Genet. Jan. 1999;104(1):15-22.

Wadia et al., Modulation of cellular function by TAT mediated transduction of full length proteins. Curr Protein Pept Sci. Apr. 2003;4(2):97-104.

Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.

Wah et al., Structure of FokI has implications for DNA cleavage. Proc Natl Acad Sci U S A. Sep. 1, 1998;95(18):10564-9.

Wang et al., CRISPR-Cas9 Targeting of PCSK9 in Human Hepatocytes In Vivo-Brief Report. Arterioscler Thromb Vasc Biol. May 2016;36(5):783-6. doi: 10.1161/ATVBAHA.116.307227. Epub Mar. 3, 2016.

(56) References Cited

OTHER PUBLICATIONS

Wang et al., Efficient delivery of genome-editing proteins using bioreducible lipid nanoparticles. Proc Natl Acad Sci U S A. Feb. 29, 2016. pii: 201520244. [Epub ahead of print].
Wang et al., Genetic screens in human cells using the CRISPR-Cas9 system. Science. Jan. 3, 2014;343(6166):80-4. doi: 10.1126/science. 1246981. Epub Dec. 12, 2013.
Wang et al., Nucleation, propagation and cleavage of target RNAs in Ago silencing complexes. Nature. Oct. 8, 2009;461(7265):754-61. doi: 10.1038/nature08434.
Wang et al., One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.
Wang et al., Recombinase technology: applications and possibilities. Plant Cell Rep. Mar. 2011;30(3):267-85. doi: 10.1007/s00299-010-0938-1. Epub Oct. 24, 2010.
Wang et al., Riboswitches that sense S-adenosylhomocysteine and activate genes involved in coenzyme recycling. Mol Cell. Mar. 28, 2008;29(6):691-702. doi: 10.1016/j.molcel.2008.01.012.
Wang et al., Targeted gene addition to a predetermined site in the human genome using a ZFN-based nicking enzyme. Genome Res. Jul. 2012;22(7):1316-26. doi: 10.1101/gr.122879.111. Epub Mar. 20, 2012.
Wang et al., Uracil-DNA glycosylase inhibitor gene of bacteriophage PBS2 encodes a binding protein specific for uracil-DNA glycosylase. J Biol Chem. Jan. 15, 1989;264(2):1163-71.
Warren et al., A chimeric Cre recombinase with regulated directionality. Proc Natl Acad Sci U S A. Nov. 25, 2008;105(47):18278-83. doi: 10.1073/pnas.0809949105. Epub Nov. 14, 2008.
Warren et al., Mutations in the amino-terminal domain of lambda-integrase have differential effects on integrative and excisive recombination. Mol Microbiol. Feb. 2005;55(4):1104-12.
Weber et al., Assembly of designer TAL effectors by Golden Gate cloning. PLoS One. 2011;6(5):e19722. doi:10.1371/journal.pone. 0019722. Epub May 19, 2011.
Weinberg et al., The aptamer core of SAM-IV riboswitches mimics the ligand-binding site of SAM-I riboswitches. RNA. May 2008;14(5):822-8. doi: 10.1261/rna.988608. Epub Mar. 27, 2008.
Weinberger et al., Disease-causing mutations C277R and C277Y modify gating of human C1C-1 chloride channels in myotonia congenita. J Physiol. Aug. 1, 2012;590(Pt 15):3449-64. doi: 0.1113/jphysiol.2012.232785. Epub May 28, 2012.
Wiedenheft et al., RNA-guided genetic silencing systems in bacteria and archaea. Nature. Feb. 15, 2012;482(7385):331-8. doi: 10.1038/nature10886. Review.
Wijnker et al., Managing meiotic recombination in plant breeding. Trends Plant Sci. Dec. 2008;13(12):640-6. doi: 10.1016/j.tplants. 2008.09.004. Epub Oct. 22, 2008.
Winkler et al., An mRNA structure that controls gene expression by binding FMN. Proc Natl Acad Sci U S A. Dec. 10, 2002;99(25):15908-13. Epub Nov. 27, 2002.
Winkler et al., An mRNA structure that controls gene expression by binding S-adenosylmethionine. Nat Struct Biol.Sep. 2003;10(9):701-7. Epub Aug. 10, 2003.
Winkler et al., Control of gene expression by a natural metabolite-responsive ribozyme. Nature. Mar. 18, 2004;428(6980):281-6.
Winkler et al., Thiamine derivatives bind messenger RNAs directly to regulate bacterial gene expression. Nature. Oct. 31, 2002;419(6910):952-6. Epub Oct. 16, 2002.
Wolf et al., tadA, an essential tRNA-specific adenosine deaminase from *Escherichia coli*. EMBO J. Jul. 15, 2002;21(14):3841-51.
Wolfe et al., Analysis of zinc fingers optimized via phage display: evaluating the utility of a recognition code. J Mol Biol. Feb. 5, 1999;285(5):1917-34.
Wood et al., Targeted genome editing across species using ZFNs and TALENs. Science. Jul. 15, 2011;333(6040):307. doi: 10.1126/science. 1207773. Epub Jun. 23, 2011.
Wu et al., Correction of a genetic disease in mouse via use of CRISPR-Cas9. Cell Stem Cell. Dec. 5, 2013;13(6):659-62. doi: 10.1016/j.stem.2013.10.016.
Wu et al., Genome-wide binding of the CRISPR endonuclease Cas9 in mammalian cells. Nat Biotechnol. Jul. 2014;32(7):670-6. doi: 10.1038/nbt.2889. Epub Apr. 20, 2014.
Xu et al., Sequence determinants of improved CRISPR sgRNA design. Genome Res. Aug. 2015;25(8):1147-57. doi: 10.1101/gr. 191452.115. Epub Jun. 10, 2015.
Yahata et al., Unified, Efficient, and Scalable Synthesis of Halichondrins: Zirconium/Nickel-Mediated One-Pot Ketone Synthesis as the Final Coupling Reaction. Angew Chem Int Ed Engl. Aug. 28, 2017;56(36):10796-10800. doi: 10.1002/anie.201705523. Epub Jul. 28, 2017.
Yamamoto et al., Virological and immunological bases for HIV-1 vaccine design. Uirusu 2007;57(2):133-139. https://doi.org/10.2222/jsv.57.133.
Yamano et al., Crystal Structure of Cpf1 in Complex with Guide RNA and Target DNA. Cell May 2016;165(4)949-62.
Yang et al., Engineering and optimising deaminase fusions for genome editing. Nat Commun. Nov. 2, 2016;7:13330. doi: 10.1038/ncomms13330.
Yang et al., Genome editing with targeted deaminases. BioRxiv. Preprint. First posted online Jul. 28, 2016.
Yang et al., New CRISPR-Cas systems discovered. Cell Res. Mar. 2017;27(3):313-314. doi: 10.1038/cr.2017.21. Epub Feb. 21, 2017.
Yang et al., PAM-dependent Target DNA Recognition and Cleavage by C2C1 CRISPR-Cas endonuclease. Cell Dec. 2016;167(7):1814-28.
Yanover et al., Extensive protein and DNA backbone sampling improves structure-based specificity prediction for C2H2 zinc fingers. Nucleic Acids Res. Jun. 2011;39(11):4564-76. doi: 10.1093/nar/gkr048. Epub Feb. 22, 2011.
Yazaki et al., Hereditary systemic amyloidosis associated with a new apolipoprotein AII stop codon mutation Stop78Arg. Kidney Int. Jul. 2003;64(1):11-6.
Yin et al., Genome editing with Cas9 in adult mice corrects a disease mutation and phenotype. Nat Biotechnol. Jun. 2014;32(6):551-3. doi: 10.1038/nbt.2884. Epub Mar. 30, 2014.
Yuan et al., Tetrameric structure of a serine integrase catalytic domain. Structure. Aug. 6, 2008;16(8):1275-86. doi: 10.1016/j.str. 2008.04.018.
Yuen et al., Control of transcription factor activity and osteoblast differentiation in mammalian cells using an evolved small-molecule-dependent intein. J Am Chem Soc. Jul. 12, 2006;128(27):8939-46.
Zelphati et al., Intracellular delivery of proteins with a new lipid-mediated delivery system. J Biol Chem. Sep. 14, 2001;276(37):35103-10. Epub Jul. 10, 2001.
Zetsche et al., A split-Cas9 architecture for inducible genome editing and transcription modulation. Nat Biotechnol. Feb. 2015;33(2):139-42. doi: 10.1038/nbt.3149.
Zetsche et al., Cpf1 is a single RNA-guided endonuclease of a class 2 CRISPR-Cas system. Cell. Oct. 22, 2015;163(3):759-71. doi: 10.1016/j.cell.2015.09.038. Epub Sep. 25, 2015.
Zhang et al., Comparison of non-canonical PAMs for CRISPR/Cas9-mediated DNA cleavage in human cells. Sci Rep. Jun. 2014;4:5405.
Zhang et al., Conditional gene manipulation: Cre-ating a new biological era. J Zhejiang Univ Sci B. Jul. 2012;13(7):511-24. doi: 10.1631/jzus.B1200042. Review.
Zhang et al., CRISPR/Cas9 for genome editing: progress, implications and challenges. Hum Mol Genet. Sep. 15, 2014;23(R1):R40-6. doi: 10.1093/hmg/ddu125. Epub Mar. 20, 2014.
Zhang et al., Efficient construction of sequence-specific TAL effectors for modulating mammalian transcription. Nat Biotechnol. Feb. 2011;29(2):149-53. doi: 10.1038/nbt.1775. Epub Jan. 19, 2011.
Zhang et al., Programmable base editing of zebrafish genome using a modified CRISPR-Cas9 system. Nat Commun. Jul. 25, 2017;8(1):118. doi: 10.1038/s41467-017-00175-6.
Zhang et al., Stabilized plasmid-lipid particles for regional gene therapy: formulation and transfection properties. Gene Ther. Aug. 1999;6(8):1438-47.

(56) References Cited

OTHER PUBLICATIONS

Zheng et al., DNA editing in DNA/RNA hybrids by adenosine deaminases that act on RNA. Nucleic Acids Res. Apr. 7, 2017;45(6):3369-3377. doi: 10.1093/nar/gkx050.
Zimmermann et al., Molecular interactions and metal binding in the theophylline-binding core of an RNA aptamer. RNA. May 2000;6(5):659-67.
Zong et al., Precise base editing in rice, wheat and maize with a Cas9-cytidine deaminase fusion. Nat Biotechnol. May 2017;35(5):438-440. doi: 10.1038/nbt.3811. Epub Feb. 27, 2017.
Zorko et al., Cell-penetrating peptides: mechanism and kinetics of cargo delivery. Adv Drug Deliv Rev. Feb. 28, 2005;57(4):529-45. Epub Jan. 22, 2005.
Zou et al., Gene targeting of a disease-related gene in human induced pluripotent stem and embryonic stem cells. Cell Stem Cell. Jul. 2, 2009;5(1):97-110. doi: 10.1016/j.stem.2009.05.023. Epub Jun. 18, 2009.
Zuris et al., Cationic lipid-mediated delivery of proteins enables efficient protein-based genome editing in vitro and in vivo. Nat Biotechnol. 2015;33:73-80.
EP 19181479.7, Oct. 31, 2019, Extended European Search Report.
EP 19187331.4, Dec. 19, 2019, Partial European Search Report.
PCT/US2017/068114, Jul. 4, 2019, International Preliminary Report on Patentability.
PCT/US2017/068105, Jul. 4, 2019, International Preliminary Report on Patentability.
PCT/US2018/021880, Sep. 19, 2019, International Preliminary Report on Patentability.
PCT/US2018/021664, Sep. 19, 2019, International Preliminary Report on Patentability.
PCT/US2018/021878, Sep. 19, 2019, International Preliminary Report on Patentability.
PCT/US2018/024208, Oct. 3, 2019, International Preliminary Report on Patentability.
PCT/US2018/048969, Jul. 31, 2019, International Search Report and Written Opinion.
PCT/US2018/048969, Mar. 12, 2020, International Preliminary Report on Patentability.
PCT/US2018/032460, Nov. 21, 2019, International Preliminary Report on Patentability.
PCT/US2018/044242, Nov. 21, 2019, International Search Report and Written Opinion.
PCT/US2018/044242, Feb. 6, 2020, International Preliminary Report on Patentability.
U.S. Appl. No. 16/374,634, filed Apr. 30, 2019, Liu et al.
U.S. Appl. No. 16/492,548, filed Sep. 9, 2019, Liu et al.
Banerjee et al., Cadmium inhibits mismatch repair by blocking the ATPase activity of the MSH2-MSH6 complex [published correction appears in Nucleic Acids Res. 2005;33(5):1738]. Nucleic Acids Res. 2005;33(4):1410-1419. Published Mar. 3, 2005. doi:10.1093/nar/gki291.
Burke et al., RNA Aptamers to the Adenosine Moiety of S-adenosyl Methionine: Structural Inferences From Variations on a Theme and the Reproducibility of SELEX. Nucleic Acids Res. May 15, 1997;25(10):2020-4. doi: 10.1093/nar/25.10.2020.
Eiler et al., Structural Basis for the Fast Self-Cleavage Reaction Catalyzed by the Twister Ribozyme. Proc Natl Acad Sci U S A. Sep. 9, 2014; 111(36):13028-33. doi: 10.1073/pnas.1414571111. Epub Aug. 25, 2014.
Endo et al., Toward establishing an efficient and versatile gene targeting system in higher plants. Biocatalysis and Agricultural Biotechnology 2014;3,(1):2-6.
Felletti et al., Twister Ribozymes as Highly Versatile Expression Platforms for Artificial Riboswitches. Nat Commun. Sep. 27, 2016;7:12834. doi: 10.1038/ncomms12834.
Genbank Submission; NIH/NCBI, Accession No. NM_174936. Guo et al., Oct. 28, 2015. 6 pages.
Harrington et al., Recent developments and current status of gene therapy using viral vectors in the United Kingdom. BMJ. 2004;329(7470):839?842. doi:10.1136/bmj.329.7470.839.

Horvath et al., Diversity, Activity, and Evolution of CRISPR Loci in *Streptococcus thermophilus*. J Bacteriol. Feb. 2008;190(4):1401-12. doi: 10.1128/JB.01415-07. Epub Dec. 7, 2007.
Jiang et al., Structural Biology. A Cas9-guide RNA Complex Preorganized for Target DNA Recognition. Science. Jun. 26, 2015;348(6242):1477-81. doi: 10.1126/science.aab1452.
Kobori et al., Deep Sequencing Analysis of Aptazyme Variants Based on a Pistol Ribozyme. ACS Synth Biol. Jul. 21, 2017;6(7):1283-1288. doi: 10.1021/acssynbio.7b00057. Epub Apr. 14, 2017.
Koonin et al., Diversity, classification and evolution of CRISPR-Cas systems. Curr Opin Microbiol. 2017;37:67?78. doi:10.1016/j.mib.2017.05.008.
Lewis et al., Building the Class 2 CRISPR-Cas Arsenal. Mol Cell 2017;65(3);377-379.
Lilley, D.M. The Varkud Satellite Ribozyme. RNA. Feb. 2004;10(2):151-8.doi: 10.1261/rna.5217104.
Liu et al., Functional Nucleic Acid Sensors. Chem Rev. May 2009;109(5):1948-98. doi: 10.1021/cr030183i.
Ma et al., Single-Stranded DNA Cleavage by Divergent CRISPR-Cas9 Enzymes. Mol Cell. Nov. 5, 2015;60(3):398-407. doi: 10.1016/j.molcel.2015.10.030.
Mandal et al., Riboswitches Control Fundamental Biochemical Pathways in Bacillus Subtilis and Other Bacteria. Cell. May 30, 2003;113(5):577-86. doi: 10.1016/s0092-8674(03)00391-x.
Mir et al., Two Active Site Divalent Ions in the Crystal Structure of the Hammerhead Ribozyme Bound to a Transition State Analogue. Biochemistry... Feb. 2, 2016;55(4):633-6. doi: 10.1021/acs.biochem.5b01139. Epub Jan. 19, 2016.
Ni et al., A PCSK9-binding antibody that structurally mimics the EGF(A) domain of LDL-receptor reduces LDL cholesterol in vivo. J Lipid Res. 2011;52:76-86.
Nishikura, Functions and regulation of RNA editing by ADAR deaminases. Annu Rev Biochem. 2010;79:321-349. doi:10.1146/annurev-biochem-060208-105251.
Nishimasu et al., Crystal Structure of *Staphylococcus aureus* Cas9. Cell. Aug. 27, 2015;162(5):1113-26. doi: 10.1016/j.cell.2015.08.007.
Nomura et al., Controlling Mammalian Gene Expression by Allosteric Hepatitis Delta Virus Ribozymes. ACS Synth Biol. Dec. 20, 2013;2(12):684-9. doi: 10.1021/sb400037a. Epub May 22, 2013.
Nowak et al., Guide RNA Engineering for Versatile Cas9 Functionality. Nucleic Acids Res. Nov. 16, 2016;44(20):9555-9564. doi: 10.1093/nar/gkw908. Epub Oct. 12, 2016.
Pospsílová et al., Hydrolytic cleavage of N6-substituted adenine derivatives by eukaryotic adenine and adenosine deaminases. Biosci Rep. 2008;28(6):335-347. doi:10.1042/BSR20080081.
Ren et al., In-line Alignment and $Mg^{2?}$ Coordination at the Cleavage Site of the env22 Twister Ribozyme. Nat Commun. Nov. 20, 2014;5:5534. doi: 10.1038/ncomms6534.
Ren et al., Pistol Ribozyme Adopts a Pseudoknot Fold Facilitating Site-Specific In-Line Cleavage. Nat Chem Biol. Sep. 2016;12(9):702-8. doi: 10.1038/nchembio.2125. Epub Jul. 11, 2016.
Sasidharan et al., The selection of acceptable protein mutations. PNAS; Jun. 12, 2007;104(24):10080-5. www.pnas.org/cgi/doi/10.1073.pnas.0703737104.
Tourdot et al., A general strategy to enhance immunogenicity of low-affinity HLA-A2. 1-associated peptides: implication in the identification of cryptic tumor epitopes. Eur J Immunol. Dec. 2000;30(12):3411-21.
Wang et al. CRISPR-Cas9 and CRISPR-Assisted Cytidine Deaminase Enable Precise and Efficient Genome Editing in Klebsiella pneumoniae. Appl Environ Microbiol. 2018;84(23):e01834-18. Published Nov. 15, 2018. doi:10.1128/AEM.01834-18.
Wang et al., Enhanced base editing by co-expression of free uracil DNA glycosylase inhibitor. Cell Res. Oct. 2017;27(1): 1289-92. doi: 10.1038/cr.2017.111. Epub Aug. 29, 2017.
Weinberg et al., New Classes of Self-Cleaving Ribozymes Revealed by Comparative Genomics Analysis. Nat Chem Biol. Aug. 2015;11(8):606-10. doi: 10.1038/nchembio.1846. Epub Jul. 13, 2015.

(56) References Cited

OTHER PUBLICATIONS

Wijesinghe et al., Efficient deamination of 5-methylcytosines in DNA by human APOBEC3A, but not by AID or APOBEC3G. Nucleic Acids Res. Oct. 2012;40(18):9206-17. doi: 10.1093/nar/gks685. Epub Jul. 13, 2012.

Wilson et al., Assessing annotation transfer for genomics: quantifying the relations between protein sequence, structure and function through traditional and probabilistic scores. J Mol Biol 2000;297:233-49.

Wilson et al., In Vitro Selection of Functional Nucleic Acids. Annu Rev Biochem. 1999;68:611-47. doi: 10.1146/annurev.biochem.68.1.611.

Zhang et al., Ribozymes and Riboswitches: Modulation of RNA Function by Small Molecules. Biochemistry. Nov. 2, 2010;49(43):9123-31. doi: 10.1021/bi1012645.

Zhong et al., Rational Design of Aptazyme Riboswitches for Efficient Control of Gene Expression in Mammalian Cells. Elife. Nov. 2, 2016;5:e18858. doi: 10.7554/eLife.18858.

Rogozin et al., Evolution and diversification of lamprey antigen receptors: evidence for involvement of an AID-APOBEC family cytosine deaminase. Nat Immunol. Jun. 2007;8(6):647-56. doi: 10.1038/ni1463. Epub Apr. 29, 2007.

[No Author Listed] "FokI" from New England Biolabs Inc. Last accessed online via https://www.neb.com/products/r0109-foki#Product%20Information on Mar. 19, 2021. 1 page.

[No Author Listed] "Nucleic Acids Sizes and Molecular Weights." Printed Mar. 19, 2021. 2 pages.

[No Author Listed] "Zinc Finger Nuclease" from Wikipedia. Retrieved from https://en.wikipedia.org/w/index.php?title=Zinc_finger_nuclease&oldid= 1007053318. Page last edited Feb. 16, 2021. Printed on Mar. 19, 2021.

[No Author Listed] HyPhy—Hypothesis testing using Phylogenies. Last modified Apr. 21, 2017. Accessed online via http://hyphy.org/w/index.php/Main_Page on Apr. 28, 2021.

[No Author Listed] Theoretical Biochemistry Group. Institute for Theoretical Chemistry. The ViennaRNA Package. Universitat Wien. https://www.tbi.univie.ac.at/RNA/. Last accessed Apr. 28, 2021.

Abremski et al., Bacteriophage P1 site-specific recombination. Purification and properties of the Cre recombinase protein. J Biol Chem. Feb. 10, 1984;259(3):1509-14.

Abudayyeh et al., RNA targeting with CRISPR-Cas13. Nature. Oct. 12, 2017;550(7675):280-284. doi: 10.1038/nature24049. Epub Oct. 4, 2017.

Ada et al., Carbohydrate-protein conjugate vaccines. Clin Microbiol Infect. Feb. 2003;9(2):79-85. doi: 10.1046/j.1469-0691.2003.00530.x.

Adamala et al., Programmable RNA-binding protein composed of repeats of a single modular unit. Proc Natl Acad Sci U S A. May 10, 2016;113(19):E2579-88. doi: 10.1073/pnas.1519368113. Epub Apr. 26, 2016.

Adli, The CRISPR tool kit for genome editing and beyond. Nat Commun. May 15, 2018;9(1):1911. doi: 10.1038/s41467-018-04252-2.

Aguilo et al., Coordination of m(6)A mRNA Methylation and Gene Transcription by ZFP217 Regulates Pluripotency and Reprogramming. Cell Stem Cell. Dec. 3, 2015;17(6):689-704. doi: 10.1016/j.stem.2015.09.005. Epub Oct. 29, 2015.

Ahmad et al., Antibody-mediated specific binding and cytotoxicity of liposome-entrapped doxorubicin to lung cancer cells in vitro. Cancer Res. Sep. 1, 1992;52(17):4817-20.

Aik et al., Structure of human RNA N?-methyladenine demethylase ALKBH5 provides insights into its mechanisms of nucleic acid recognition and demethylation. Nucleic Acids Res. Apr. 2014;42(7):4741-54. doi: 10.1093/nar/gku085. Epub Jan. 30, 2014.

Akinsheye et al., Fetal hemoglobin in sickle cell anemia. Blood. Jul. 7, 2011;118(1):19-27. doi: 10.1182/blood-2011-03-325258. Epub Apr. 13, 2011.

Alarcón et al., HNRNPA2B1 Is a Mediator of m(6)A-Dependent Nuclear RNA Processing Events. Cell. Sep. 10, 2015;162(6):1299-308. doi: 10.1016/j.cell.2015.08.011. Epub Aug. 27, 2015.

Alarcón et al., N6-methyladenosine marks primary microRNAs for processing. Nature. Mar. 26, 2015;519(7544):482-5. doi: 10.1038/nature14281. Epub Mar. 18, 2015.

Alexander, HFE-associated hereditary hemochromatosis. Genet Med. May 2009;11(5):307-13. doi: 10.1097/GIM.0b013e31819d30f2.

Altschul et al., Basic local alignment search tool. J Mol Biol. Oct. 5, 1990;215(3):403-10. doi: 10.1016/S0022-2836(05)80360-2.

Amato et al., Interpreting elevated fetal hemoglobin in pathology and health at the basic laboratory level: new and known ?- gene mutations associated with hereditary persistence of fetal hemoglobin. Int J Lab Hematol. Feb. 2014;36(1):13-9. doi: 10.1111/ijlh.12094. Epub Apr. 29, 2013.

Anzalone et al., Reprogramming eukaryotic translation with ligand-responsive synthetic RNA switches. Nat Methods. May 2016;13(5):453-8. doi: 10.1038/nmeth.3807. Epub Mar. 21, 2016.

Anzalone et al., Search-and-replace genome editing without double-strand breaks or donor DNA. Nature. Dec. 2019;576(7785):149-157. doi: 10.1038/s41586-019-1711-4. Epub Oct. 21, 2019.

Aplan, Causes of oncogenic chromosomal translocation. Trends Genet. Jan. 2006;22(1):46-55. doi: 10.1016/j.tig.2005.10.002. Epub Oct. 28, 2005.

Arakawa et al., A method to convert mRNA into a gRNA library for CRISPR/Cas9 editing of any organism. Sci Adv. Aug. 24, 2016;2(8):e1600699. doi: 10.1126/sciadv.1600699.

Araki et al., Comparative analysis of right element mutant lox sites on recombination efficiency in embryonic stem cells. BMC Biotechnol. Mar. 31, 2010;10:29. doi: 10.1186/1472-6750-10-29.

Araki et al., Targeted integration of DNA using mutant lox sites in embryonic stem cells. Nucleic Acids Res. Feb. 15, 1997;25(4):868-72. doi: 10.1093/nar/25.4.868.

Arambula et al., Surface display of a massively variable lipoprotein by a Legionella diversity-generating retroelement. Proc Natl Acad Sci U S A. May 14, 2013;110(20):8212-7. doi: 10.1073/pnas.1301366110. Epub Apr. 30, 2013.

Arazoe et al., Targeted Nucleotide Editing Technologies for Microbial Metabolic Engineering. Biotechnol J. Sep. 2018;13(9):e1700596. doi: 10.1002/biot.201700596. Epub Jun. 19, 2018.

Arbab et al., Cloning-free CRISPR. Stem Cell Reports. Nov. 10, 2015;5(5):908-917. doi: 10.1016/j.stemcr.2015.09.022. Epub Oct. 29, 2015.

Arezi et al., Novel mutations in Moloney Murine Leukemia Virus reverse transcriptase increase thermostability through tighter binding to template-primer. Nucleic Acids Res. Feb. 2009;37(2):473-81. doi: 10.1093/nar/gkn952. Epub Dec. 4, 2008.

Asante et al., A naturally occurring variant of the human prion protein completely prevents prion disease. Nature. Jun. 25, 2015;522(7557):478-81. doi: 10.1038/nature14510. Epub Jun. 10, 2015.

Belshaw et al., Controlling protein association and subcellular localization with a synthetic ligand that induces heterodimerization of proteins. Proc Natl Acad Sci U S A. May 14, 1996;93(10):4604-7. doi: 10.1073/pnas.93.10.4604.

Berkhout et al., Identification of an active reverse transcriptase enzyme encoded by a human endogenous HERV-K retrovirus. J Virol. Mar. 1999;73(3):2365-75. doi: 10.1128/JVI.73.3.2365-2375.1999.

Bernhart et al., Local RNA base pairing probabilities in large sequences. Bioinformatics. Mar. 1, 2006;22(5):614-5. doi: 10.1093/bioinformatics/btk014. Epub Dec. 20, 2005.

Bertolotti et al., Toward genosafe endonuclease-boosted gene targeting using breakthrough CRISP/Cas9 for next generation stem cell gene therapy culminating in efficient ex VIVO in VIVO gene repair/genomic editing. Molecular Therapy. May 2015;23(Suppl1):S139. Abstract 350. 18th Ann Meeting of the American Society of Gene and Cell Therapy. ASGCT 2015. New Orleans, LA. May 13, 2015-May 16, 2015.

Bertrand et al., Localization of ASH1 mRNA particles in living yeast. Mol Cell. Oct. 1998;2(4):437-45. doi: 10.1016/s1097-2765(00)80143-4.

Bi et al., Pseudo attP sites in favor of transgene integration and expression in cultured porcine cells identified by Streptomyces phage phiC31 integrase. BMC Mol Biol. Sep. 8, 2013;14:20. doi: 10.1186/1471-2199-14-20.

(56) References Cited

OTHER PUBLICATIONS

Bibb et al., Integration and excision by the large serine recombinase phiRv1 integrase. Mol Microbiol. Mar. 2005;55(6): 1896-910. doi: 10.1111/j.1365-2958.2005.04517.x.

Biehs et al., DNA Double-Strand Break Resection Occurs during Non-homologous End Joining in G1 but Is Distinct from Resection during Homologous Recombination. Mol Cell. Feb. 16, 2017;65(4):671-684.e5. doi: 10.1016/j.molcel.2016.12.016. Epub Jan. 26, 2017.

Biswas et al., A structural basis for allosteric control of DNA recombination by lambda integrase. Nature. Jun. 23, 2005;435(7045):1059-66. doi: 10.1038/nature03657.

Blain et al., Nuclease activities of Moloney murine leukemia virus reverse transcriptase. Mutants with altered substrate specificities. J Biol Chem. Nov. 5, 1993;268(31):23585-92.

Blau et al., A proliferation switch for genetically?modified?cells. PNAS Apr. 1, 1997 94 (7) 3076-3081; https://doi.org/10.1073/pnas.94.7.3076.

Bodi et al., Yeast m6A Methylated mRNAs Are Enriched on Translating Ribosomes during Meiosis, and under Rapamycin Treatment. PLoS One. Jul. 17, 2015;10(7):e0132090. doi: 10.1371/journal.pone.0132090.

Bogdanove et al., Engineering altered protein-DNA recognition specificity. Nucleic Acids Res. Jun. 1, 2018;46(10):4845-4871. doi: 10.1093/nar/gky289.

Borchardt et al., Controlling mRNA stability and translation with the CRISPR endoribonuclease Csy4. RNA. Nov. 2015;21(11):1921-30. doi: 10.1261/rna.051227.115. Epub Sep. 9, 2015.

Boutabout et al., DNA synthesis fidelity by the reverse transcriptase of the yeast retrotransposon Ty1. Nucleic Acids Res. Jun. 1, 2001;29(11):2217-22. doi: 10.1093/nar/29.11.2217.

Box et al., A multi-domain protein system based on the HC fragment of tetanus toxin for targeting DNA to neuronal cells. J Drug Target. Jul. 2003;11(6):333-43. doi: 10.1080/10611863 10001634667.

Braun et al., Immunogenic duplex nucleic acids are nuclease resistant. J Immunol. Sep. 15, 1988;141(6):2084-9.

Brown et al., Characterization of the genetic elements required for site-specific integration of plasmid pSE211 in Saccharopolyspora erythraea. J Bacteriol. Apr. 1990;172(4):1877-88. doi: 10.1128/jb.172.4.1877-1888.1990.

Brown et al., Structural insights into the stabilization of MALAT1 noncoding RNA by a bipartite triple helix. Nat Struct Mol Biol. Jul. 2014;21(7):633-40. doi: 10.1038/nsmb.2844. Epub Jun. 22, 2014.

Brzezicha et al., Identification of human tRNA:m5C methyltransferase catalysing intron-dependent m5C formation in the first position of the anticodon of the pre-tRNA Leu (CAA). Nucleic Acids Res. 2006;34(20):6034-43. doi: 10.1093/nar/gkl765. Epub Oct. 27, 2006.

Buchschacher et al., Human immunodeficiency virus vectors for inducible expression of foreign genes. J Virol. May 1992;66(5):2731-9. doi: 10.1128/JVI.66.5.2731-2739.1992.

Budker et al., Protein/amphipathic polyamine complexes enable highly efficient transfection with minimal toxicity. Biotechniques. Jul. 1997;23(1):139, 142-7. doi: 10.2144/97231rr02.

Budworth et al., A brief history of triplet repeat diseases. Methods Mol Biol. 2013; 1010:3-17. doi: 10.1007/978-1-62703-411-1_1.

Byrne et al., Multiplex gene regulation: a two-tiered approach to transgene regulation in transgenic mice. Proc Natl Acad Sci U S A. Jul. 1989;86(14):5473-7. doi: 10.1073/pnas.86.14.5473.

Cadwell et al., Randomization of genes by PCR mutagenesis. PCR Methods Appl. Aug. 1992;2(1):28-33. doi: 10.1101/gr.2.1.28.

Cai et al., Reconstruction of ancestral protein sequences and its applications. BMC Evol Biol. Sep. 17, 2004;4:33. doi: 10.1186/1471-2148-4-33.

Camper et al., Postnatal repression of the alpha-fetoprotein gene is enhancer independent. Genes Dev. Apr. 1989;3(4):537-46. doi: 10.1101/gad.3.4.537.

Camps et al., Targeted gene evolution in *Escherichia coli* using a highly error-prone DNA polymerase I. Proc Natl Acad Sci U S A. Aug. 19, 2003;100(17):9727-32. Epub Aug. 8, 2003.

Canchaya et al., Genome analysis of an inducible prophage and prophage remnants integrated in the *Streptococcus pyogenes* strain SF370. Virology. Oct. 25, 2002;302(2):245-58. doi: 10.1006/viro.2002.1570.

Canver et al., Customizing the genome as therapy for the ?-hemoglobinopathies. Blood. May 26, 2016;127(21):2536-45. doi: 10.1182/blood-2016-01-678128. Epub Apr. 6, 2016.

Carlson et al., Negative selection and stringency modulation in phage-assisted continuous evolution. Nat Chem Biol. Mar. 2014;10(3):216-22. doi: 10.1038/nchembio.1453. Epub Feb. 2, 2014. With Supplementary Results.

Carvalho et al., Evolution in health and medicine Sackler colloquium: Genomic disorders: a window into human gene and genome evolution. Proc Natl Acad Sci U S A. Jan. 26, 2010;107 Suppl 1(Suppl 1):1765-71. doi: 10.1073/pnas.0906222107. Epub Jan. 13, 2010.

Caspi et al., Distribution of split DnaE inteins in cyanobacteria. Mol Microbiol. Dec. 2003;50(5):1569-77. doi: 10.1046/j.1365-2958.2003.03825.x.

Cattaneo et al., SEL1L affects human pancreatic cancer cell cycle and invasiveness through modulation of PTEN and genes related to cell-matrix interactions. Neoplasia. 2005;7(11):1030-1038.

Ceccaldi et al., Repair Pathway Choices and Consequences at the Double-Strand Break. Trends Cell Biol. Jan. 2016;26(1):52-64. doi: 10.1016/j.tcb.2015.07.009. Epub Oct. 1, 2015.

Chadalavada et al., Wild-type is the optimal sequence of the HDV ribozyme under cotranscriptional conditions. RNA. Dec. 2007;13(12):2189-201. doi: 10.1261/rna.778107. Epub Oct. 23, 2007.

Chalberg et al., phiC31 integrase confers genomic integration and long-term transgene expression in rat retina. Invest Ophthalmol Vis Sci. Jun. 2005;46(6):2140-6. doi: 10.1167/iovs.04-1252.

Chan et al., Molecular recording of mammalian embryogenesis. Nature. Jun. 2019;570(7759):77-82. doi: 10.1038/s41586-019-1184-5. Epub May 13, 2019.

Chapman et al., Playing the end game: DNA double-strand break repair pathway choice. Mol Cell. Aug. 24, 2012;47(4):497-510. doi: 10.1016/j.molcel.2012.07.029.

Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.

Chen et al., Enhanced proofreading governs CRISPR-Cas9 targeting accuracy. Nature. Oct. 19, 2017;550(7676):407-410. doi: 10.1038/nature24268. Epub Sep. 20, 2017.

Chen et al., Highly Efficient Mouse Genome Editing by CRISPR Ribonucleoprotein Electroporation of Zygotes. J Biol Chem. Jul. 8, 2016;291(28):14457-67. doi: 10.1074/jbc.M116.733154. Epub May 5, 2016.

Chen et al., m(6)A RNA methylation is regulated by microRNAs and promotes reprogramming to pluripotency. Cell Stem Cell. Mar. 5, 2015;16(3):289-301. doi: 10.1016/j.stem.2015.01.016. Epub Feb. 12, 2015.

Chew et al., A multifunctional AAV-CRISPR-Cas9 and its host response. Nat Methods. Oct. 2016;13(10):868-74. doi: 10.1038/nmeth.3993. Epub Sep. 5, 2016. Supplementary Information.

Chin, Expanding and reprogramming the genetic code of cells and animals. Annu Rev Biochem. 2014;83:379-408. doi: 10.1146/annurev-biochem-060713-035737. Epub Feb. 10, 2014.

Cho et al., Site-specific recombination of bacteriophage P22 does not require integration host factor. J Bacteriol. Jul. 1999;181(14):4245-9. doi: 10.1128/JB.181.14.4245-4249.1999.

Choe et al., Forging Ahead through Darkness: PCNA, Still the Principal Conductor at the Replication Fork. Mol Cell. Feb. 2, 2017;65(3):380-392. doi: 10.1016/j.molcel.2016.12.020.

Choi et al., N(6)-methyladenosine in mRNA disrupts tRNA selection and translation-elongation dynamics. Nat Struct Mol Biol. Feb. 2016;23(2):110-5. doi: 10.1038/nsmb.3148. Epub Jan. 11, 2016.

Chong et al., Modulation of protein splicing of the *Saccharomyces cerevisiae* vacuolar membrane ATPase intein. J Biol Chem. Apr. 24, 1998;273(17):10567-77. doi: 10.1074/jbc.273.17.10567.

(56) References Cited

OTHER PUBLICATIONS

Chong et al., Utilizing the C-terminal cleavage activity of a protein splicing element to purify recombinant proteins in a single chromatographic step. Nucleic Acids Res. Nov. 15, 1998;26(22):5109-15. doi: 10.1093/nar/26.22.5109.

Chong et al., Protein splicing involving the *Saccharomyces cerevisiae* VMA intein. The steps in the splicing pathway, side reactions leading to protein cleavage, and establishment of an in vitro splicing system. J Biol Chem. Sep. 6, 1996;271(36):22159-68. doi: 10.1074/jbc.271.36.22159.

Chong et al., Protein splicing of the *Saccharomyces cerevisiae* VMA intein without the endonuclease motifs. J Biol Chem. Jun. 20, 1997;272(25):15587-90. doi: 10.1074/jbc.272.25.15587.

Choudhury et al., Engineering RNA endonucleases with customized sequence specificities. Nat Commun. 2012;3:1147. doi: 10.1038/ncomms2154.

Christiansen et al., Characterization of the lactococcal temperate phage TP901-1 and its site-specific integration. J Bacteriol. Feb. 1994;176(4):1069-76. doi: 10.1128/jb.176.4.1069-1076.1994.

Chuai et al., DeepCRISPR: optimized CRISPR guide RNA design by deep learning. Genome Biol. Jun. 26, 2018;19(1):80. doi: 10.1186/s13059-018-1459-4.

Chuai et al., In Silico Meets In Vivo: Towards Computational CRISPR-Based sgRNA Design. Trends Biotechnol. Jan. 2017;35(1):12-21. doi: 10.1016/j.tibtech.2016.06.008. Epub Jul. 11, 2016.

Chuang et al., Novel Heterotypic Rox Sites for Combinatorial Dre Recombination Strategies. G3 (Bethesda). Dec. 29, 2015;6(3):559-71. doi: 10.1534/g3.115.025841.

Chujo et al., Trmt61B is a methyltransferase responsible for 1-methyladenosine at position 58 of human mitochondrial tRNAs. RNA. Dec. 2012;18(12):2269-76. doi: 10.1261/rna.035600.112. Epub Oct. 24, 2012.

Clackson et al., Redesigning an FKBP-ligand interface to generate chemical dimerizers with novel specificity. Proc Natl Acad Sci U S A. Sep. 1, 1998;95(18):10437-42. doi: 10.1073/pnas.95.18.10437.

Clement et al., CRISPResso2 provides accurate and rapid genome editing sequence analysis. Nat Biotechnol. Mar. 2019;37(3):224-226. doi: 10.1038/s41587-019-0032-3.

Coffey et al., The Economic Impact of BSE on the U.S. Beef Industry: Product Value Losses, Regulatory Costs, and Consumer Reactions. Kansas State University Agricultural Experiment Station and Cooperative Extension Service. MF-2678. May 2005. 68 pages. Accessed via https://bookstore.ksre.ksu.edu/pubs/MF2678.pdf.

Cokol et al., Finding nuclear localization signals. EMBO Rep. Nov. 2000;1(5):411-5. doi: 10.1093/embo-reports/kvd092.

Conrad et al., A Kaposi's sarcoma virus RNA element that increases the nuclear abundance of intronless transcripts. EMBO J. May 18, 2005;24(10):1831-41. doi: 10.1038/sj.emboj.7600662. Epub Apr. 28, 2005.

Cornu et al., Refining strategies to translate genome editing to the clinic. Nat Med. Apr. 3, 2017;23(4):415-423. doi: 10.1038/nm.4313.

Costa et al., Frequent use of the same tertiary motif by self-folding RNAs. EMBO J. Mar. 15, 1995;14(6):1276-85.

Cui et al., Consequences of Cas9 cleavage in the chromosome of *Escherichia coli*. Nucleic Acids Res. May 19, 2016;44(9):4243-51. doi: 10.1093/nar/gkw223. Epub Apr. 8, 2016.

Cui et al., m6A RNA Methylation Regulates the Self-Renewal and Tumorigenesis of Glioblastoma Stem Cells. Cell Rep. Mar. 14, 2017;18(11):2622-2634. doi: 10.1016/j.celrep.2017.02.059.

Cui et al., Review of CRISPR/Cas9 sgRNA Design Tools. Interdiscip Sci. Jun. 2018;10(2):455-465. doi: 10.1007/s12539-018-0298-z. Epub Apr. 11, 2018.

Cupples et al., A set of lacZ mutations in *Escherichia coli* that allow rapid detection of each of the six base substitutions. Proc Natl Acad Sci U S A. Jul. 1989;86(14):5345-9.

Dahlgren et al., A novel mutation in ribosomal protein S4 that affects the function of a mutated RF1. Biochimie. Aug. 2000;82(8):683-91.

Dahlman et al., Orthogonal gene knockout and activation with a catalytically active Cas9 nuclease. Nat Biotechnol. Nov. 2015;33(11):1159-61. doi: 10.1038/nbt.3390.

Dang et al., Optimizing sgRNA structure to improve CRISPR-Cas9 knockout efficiency. Genome Biol. Dec. 15, 2015;16:280. doi: 10.1186/s13059-015-0846-3.

Das et al.,The crystal structure of the monomeric reverse transcriptase from Moloney murine leukemia virus. Structure. May 2004;12(5):819-29. doi: 10.1016/j.str.2004.02.032.

Dassa et al., Fractured genes: a novel genomic arrangement involving new split inteins and a new homing endonuclease family. Nucleic Acids Res. May 2009;37(8):2560-73. doi: 10.1093/nar/gkp095. Epub Mar. 5, 2009.

Datsenko et al., One-step inactivation of chromosomal genes in *Escherichia coli* K-12 using PCR products. Proc Natl Acad Sci U S A. Jun. 6, 2000;97(12):6640-5.

De Felipe et al., Co-translational, intraribosomal cleavage of polypeptides by the foot-and-mouth disease virus 2A peptide. J Biol Chem. Mar. 28, 2003;278(13):11441-8. doi: 10.1074/jbc.M211644200. Epub Jan. 8, 2003.

De Wit et al., The Human CD4+ T Cell Response against Mumps Virus Targets a Broadly Recognized Nucleoprotein Epitope. J Virol. Mar. 5, 2019;93(6):e01883-18. doi: 10.1128/JVI.01883-18.

Dean et al., Genetic restriction of HIV-1 infection and progression to AIDS by a deletion allele of the CKR5 structural gene. Hemophilia Growth and Development Study, Multicenter AIDS Cohort Study, Multicenter Hemophilia Cohort Study, San Francisco City Cohort, ALIVE Study. Science. Sep. 27, 1996;273(5283):1856-62. doi: 10.1126/science.273.5283.1856.

Deng et al., Widespread occurrence of N6-methyladenosine in bacterial mRNA. Nucleic Acids Res. Jul. 27, 2015;43(13):6557-67. doi: 10.1093/nar/gkv596. Epub Jun. 11, 2015.

Deriano et al., Modernizing the nonhomologous end-joining repertoire: alternative and classical NHEJ share the stage. Annu Rev Genet. 2013;47:433-55. doi: 10.1146/annurev-genet-110711-155540. Epub Sep. 11, 2013.

Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.

Dever et al., CRISPR/Cas9 ?-globin gene targeting in human haematopoietic stem cells. Nature. Nov. 17, 2016;539(7629):384-389. doi: 10.1038/nature20134. Epub Nov. 7, 2016.

Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.

Dicarlo et al., Safeguarding CRISPR-Cas9 gene drives in yeast. Nat Biotechnol. Dec. 2015;33(12):1250-1255. doi: 10.1038/nbt.3412. Epub Nov. 16, 2015.

Dickinson et al., Experimental interrogation of the path dependence and stochasticity of protein evolution using phage-assisted continuous evolution. Proc Natl Acad Sci USA. May 2013;110(22):9007-12.

Doman et al., Evaluation and minimization of Cas9-independent off-target DNA editing by cytosine base editors. Nat Biotechnol. May 2020;38(5):620-628. doi: 10.1038/s41587-020-0414-6. Epub Feb. 10, 2020.

Dove et al., Conversion of the omega subunit of *Escherichia coli* RNA polymerase into a transcriptional activator or an activation target. Genes Dev. Mar. 1, 1998;12(5):745-54.

Doyon et al., Directed evolution and substrate specificity profile of homing endonuclease I-SceI. J Am Chem Soc. Feb. 22, 2006;128(7):2477-84.

Drake, A constant rate of spontaneous mutation in DNA-based microbes. Proc Natl Acad Sci U S A. Aug. 15, 1991;88(16):7160-4.

Dubois et al., Retroviral RNA Dimerization: From Structure to Functions. Front Microbiol. Mar. 22, 2018;9:527. doi: 10.3389/fmicb.2018.00527.

Durai et al., A bacterial one-hybrid selection system for interrogating zinc finger-DNA interactions. Comb Chem High Throughput Screen. May 2006;9(4):301-11.

(56) References Cited

OTHER PUBLICATIONS

Durai et al., Zinc finger nucleases: custom-designed molecular scissors for genome engineering of plant and mammalian cells. Nucleic Acids Res. Oct. 26, 2005;33(18):5978-90. doi: 10.1093/nar/gki912.

Eick et al., Robustness of Reconstructed Ancestral Protein Functions to Statistical Uncertainty. Mol Biol Evol. Feb. 1, 2017;34(2):247-261. doi: 10.1093/molbev/msw223.

Engel et al., The emerging role of mRNA methylation in normal and pathological behavior. Genes Brain Behav. Mar. 2018;17(3):e12428. doi: 10.1111/gbb.12428. Epub Nov. 17, 2017.

Engelward et al., Base excision repair deficient mice lacking the Aag alkyladenine DNA glycosylase. Proc Natl Acad Sci U S A. Nov. 25, 1997;94(24):13087-92.

Enyeart et al., Biotechnological applications of mobile group II introns and their reverse transcriptases: gene targeting, RNA-seq, and non-coding RNA analysis. Mobile DNA 5, 2 (2014). https://doi.org/10.1186/1759-8753-5-2. https://doi.org/10.1186/1759-8753-5-2.

Evans et al., Protein trans-splicing and cyclization by a naturally split intein from the dnaE gene of *Synechocystis* species PCC6803. J Biol Chem. Mar. 31, 2000;275(13):9091-4. doi: 10.1074/jbc.275.13.9091.

Evans et al., Semisynthesis of cytotoxic proteins using a modified protein splicing element. Protein Sci. Nov. 1998;7(11):2256-64. doi: 10.1002/pro.5560071103.

Evans et al., The cyclization and polymerization of bacterially expressed proteins using modified self-splicing inteins. J Biol Chem. Jun. 25, 1999;274(26):18359-63. doi: 10.1074/jbc.274.26.18359.

Evans et al., The in vitro ligation of bacterially expressed proteins using an intein from Methanobacterium thermoautotrophicum. J Biol Chem. Feb. 12, 1999;274(7):3923-6. doi: 10.1074/jbc.274.7.3923.

Evers et al., CRISPR knockout screening outperforms shRNA and CRISPRi in identifying essential genes. Nat Biotechnol. Jun. 2016;34(6):631-3. doi: 10.1038/nbt.3536. Epub Apr. 25, 2016.

Falnes et al., DNA repair by bacterial AlkB proteins. Res Microbiol. Oct. 2003;154(8):531-8. doi: 10.1016/S0923-2508(03)00150-5.

Falnes et al., Repair of methyl lesions in DNA and RNA by oxidative demethylation. Neuroscience. Apr. 14, 2007;145(4):1222-32. doi: 10.1016/j.neuroscience.2006.11.018. Epub Dec. 18, 2006.

Feng et al., Crystal structures of the human RNA demethylase Alkbh5 reveal basis for substrate recognition. J Biol Chem. Apr. 25, 2014;289(17):11571-11583. doi: 10.1074/jbc.M113.546168. Epub Mar. 10, 2014.

Feng et al., Human L1 retrotransposon encodes a conserved endonuclease required for retrotransposition. Cell. Nov. 29, 1996;87(5):905-16. doi: 10.1016/s0092-8674(00)81997-2.

Feuk, Inversion variants in the human genome: role in disease and genome architecture. Genome Med. Feb. 12, 2010;2(2):11. doi: 10.1186/gm132.

Fitzjohn, Diversitree: comparative phylogenetic analyses of diversification in R. Methods in Evology and Evolution. Dec. 2012;3(6):1084-92 .doi: 10.1111/j.2041-210X.2012.00234.x.

Flajolet et al., Woodchuck hepatitis virus enhancer I and enhancer II are both involved in N-myc2 activation in woodchuck liver tumors. J Virol. Jul. 1998;72(7):6175-80. doi: 10.1128/JVI.72.7.6175-6180.1998.

Flaman et al., A rapid PCR fidelity assay. Nucleic Acids Res. Aug. 11, 1994;22(15):3259-60. doi: 10.1093/nar/22.15.3259.

Fogg et al., New applications for phage integrases. J Mol Biol. Jul. 29, 2014;426(15):2703-16. doi: 10.1016/j.jmb.2014.05.014. Epub May 22, 2014.

Fogg et al., Genome Integration and Excision by a New Streptomyces Bacteriophage, ?Joe. Appl Environ Microbiol. Feb. 15, 2017;83(5):e02767-16. doi: 10.1128/AEM.02767-16.

Fouts et al., Sequencing Bacillus anthracis typing phages gamma and cherry reveals a common ancestry. J Bacteriol. May 2006;188(9):3402-8. doi: 10.1128/JB.188.9.3402-3408.2006.

Freitas et al., Mechanisms and signals for the nuclear import of proteins. Curr Genomics. Dec. 2009;10(8):550-7. doi: 10.2174/138920209789503941.

Fu et al., Promises and Pitfalls of Intracellular Delivery of Proteins. Bioconjugate Chemistry. Aug. 2014;25:1602-8.

Furukawa et al., In vitro selection of allosteric ribozymes that sense the bacterial second messenger c-di-GMP. Methods Mol Biol. 2014;1111:209-20. doi: 10.1007/978-1-62703-755-6_15.

Gajula, Designing an Elusive CoG?GoC CRISPR Base Editor. Trends Biochem Sci. Feb. 2019;44(2):91-94. doi: 10.1016/j.tibs.2018.10.004. Epub Nov. 13, 2018.

Gao et al., Treatment of autosomal dominant hearing loss by in vivo delivery of genome editing agents. Nature. Jan. 11, 2018;553(7687):217-221. doi: 10.1038/nature25164. Epub Dec. 20, 2017.

Garcia et al., Transglycosylation: a mechanism for RNA modification (and editing?). Bioorg Chem. Jun. 2005;33(3):229-51. doi: 10.1016/j.bioorg.2005.01.001. Epub Feb. 23, 2005.

Garibyan et al., Use of the rpoB gene to determine the specificity of base substitution mutations on the *Escherichia coli* chromosome. DNA Repair (Amst). May 13, 2003;2(5):593-608.

Gaudelli et al., Programmable base editing of AoT to GoC in genomic DNA without DNA cleavage. Nature. Nov. 23, 2017;551(7681):464-471. doi: 10.1038/nature24644. Epub Oct. 25, 2017. Erratum in: Nature. May 2, 2018.

Gehrke et al., An APOBEC3A-Cas9 base editor with minimized bystander and off-target activities. Nat Biotechnol. Nov. 2018;36(10):977-982. doi: 10.1038/nbt.4199. Epub Jul. 30, 2018.

GenBank Accession No. J01600.1. Brooks et al., *E.coli* dam gene coding for DNA adenine methylase. Apr. 26, 1993.

GenBank Submission; NIH/NCBI Accession No. NM_001319224.2. Umar et al., Apr. 21, 2021. 7 pages.

GenBank Submission; NIH/NCBI Accession No. NM_006027.4. Umar et al., Apr. 10, 2021. 7 pages.

GenBank Submission; NIH/NCBI, Accession No. AAA66622.1. Martinelli et al., May 18, 1995. 2 pages.

GenBank Submission; NIH/NCBI, Accession No. AGT42196. Farzadfar et al., Nov. 2, 2013. 2 pages.

GenBank Submission; NIH/NCBI, Accession No. APG80656.1. Burstein et al., Dec. 10, 2016. 1 pages.

GenBank Submission; NIH/NCBI, Accession No. AYD60528.1. Ram et al., Oct. 2, 2018. 1 page.

GenBank Submission; NIH/NCBI, Accession No. BDB43378. Zhang et al., Aug. 11, 2016. 2 pages.

GenBank Submission; NIH/NCBI, Accession No. KR710351.1. Sahni et al., Jun. 1, 2015. 2 pages.

GenBank Submission; NIH/NCBI, Accession No. NC 002737.2. Nasser et al., Feb. 7, 2021. 2 pages.

GenBank Submission; NIH/NCBI, Accession No. NM_000311.5. Alves et al., Mar. 7, 2021. 5 pages.

GenBank Submission; NIH/NCBI, Accession No. NM_001319224. Umar et al., Apr. 21, 2021. 7 pages.

GenBank Submission; NIH/NCBI, Accession No. NM_003686.4. Umar et al., Apr. 9, 2021. 7 pages.

GenBank Submission; NIH/NCBI, Accession No. NM_006027. Umar et al., Apr. 10, 2021. 7 pages.

GenBank Submission; NIH/NCBI, Accession No. NM_174936.3. Bernardini et al., Oct. 28, 2015. 2 pages.

GenBank Submission; NIH/NCBI, Accession No. NP_000302.1. Alves et al., Mar. 7, 2021. 4 pages.

GenBank Submission; NIH/NCBI, Accession No. NP_955579.1. Chen et al., Aug. 13, 2018. 5 pages.

GenBank Submission; NIH/NCBI, Accession No. QBJ66766. Duan et al. Aug. 12, 2020. 2 pages.

GenBank Submission; NIH/NCBI, Accession No. RFF81513.1. Zhou et al., Aug. 21, 2018. 2 pages.

GenBank Submission; NIH/NCBI, Accession No. SNX31424.1. Weckx, S., Feb. 16, 2018. 2 pages.

GenBank Submission; NIH/NCBI, Accession No. TGH57013. Xu et al., Apr. 9, 2019. 2 pages.

GenBank Submission; NIH/NCBI, Accession No. WP_016631044.1. Haft et al., Sep. 22, 2020. 1 page.

GenBank Submission; NIH/NCBI, Accession No. WP_031386437. No Author Listed., Sep. 23, 2019. 1 page.

(56) References Cited

OTHER PUBLICATIONS

GenBank Submission; NIH/NCBI, Accession No. WP_0315 89969. 1. Haft et al., Oct. 9, 2019. 2 pages.
GenBank Submission; NIH/NCBI, Accession No. WP_044924278. 1. Haft et al., Oct. 9, 2019. 2 pages.
GenBank Submission; NIH/NCBI, Accession No. WP_047338501. 1. Haft et al., Oct. 9, 2019. 2 pages.
GenBank Submission; NIH/NCBI, Accession No. WP_060798984. 1. Haft et al., Oct. 9, 2019. 2 pages.
GenBank Submission; NIH/NCBI, Accession No. WP_062913273. 1. Haft et al., Oct. 9, 2019, 2 pages.
GenBank Submission; NIH/NCBI, Accession No. WP_072754838. No Author Listed., Sep. 23, 2019. 1 page.
GenBank Submission; NIH/NCBI, Accession No. WP_095142515. 1. No Author Listed., Sep. 23, 2019. 1 page.
GenBank Submission; NIH/NCBI, Accession No. WP_118538418. 1. No Author Listed., Oct. 13, 2019. 1 page.
GenBank Submission; NIH/NCBI, Accession No. WP_119223642. 1. No Author Listed., Oct. 13, 2019. 1 page.
GenBank Submission; NIH/NCBI, Accession No. WP_119227726. 1. No Author Listed., Oct. 13, 2019. 1 page.
GenBank Submission; NIH/NCBI, Accession No. WP_119623382. 1. No Author Listed., Oct. 13, 2019. 1 page.
GenBank Submission; NIH/NCBI, Accession No. WP_132221894. 1. No Author Listed., Sep. 23, 2019. 1 page.
GenBank Submission; NIH/NCBI, Accession No. WP_133478044. 1. Haft et al., Oct. 9, 2019. 2 pages.
GenBank Submission; NIH/NCBI, Accession No. YP_009283008. 1. Bernardini et al., Sep. 23, 2016. 2 pages.
George et al., Adenosine deaminases acting on RNA, RNA editing, and interferon action. J Interferon Cytokine Res. Jan. 2011;31(1):99-117. doi: 10.1089/jir.2010.0097. Epub Dec. 23, 2010. PMID: 21182352; PMCID: PMC3034097.
Gerard et al., Purification and characterization of the DNA polymerase and RNase H activities in Moloney murine sarcoma-leukemia virus. J Virol. Apr. 1975;15(4):785-97. doi: 10.1128/JVI.15.4.785-797.1975.
Gerard et al., The role of template-primer in protection of reverse transcriptase from thermal inactivation. Nucleic Acids Res. Jul. 15, 2002;30(14):3118-29. doi: 10.1093/nar/gkf417.
Gerber et al., An adenosine deaminase that generates inosine at the wobble position of tRNAs. Science. Nov. 5, 1999;286(5442):1146-9. doi: 10.1126/science.286.5442.1146.
Ghahfarokhi et al., Blastocyst Formation Rate and Transgene Expression are Associated with Gene Insertion into Safe and Non-Safe Harbors in the Cattle Genome. Sci Rep. Nov. 13, 2017;7(1):15432. doi: 10.1038/s41598-017-15648-3.
Glasgow et al.,DNA-binding properties of the Hin recombinase. J Biol Chem. Jun. 15, 1989;264(17):10072-82.
Glassner et al., Generation of a strong mutator phenotype in yeast by imbalanced base excision repair. Proc Natl Acad Sci U S A. Aug. 18, 1998;95(17):9997-10002.
Goldberg et al., Epigenetics: a landscape takes shape. Cell. Feb. 23, 2007;128(4):635-8. doi: 10.1016/j.cell.2007.02.006.
Gong et al., Active DNA demethylation by oxidation and repair. Cell Res. Dec. 2011;21(12):1649-51. doi: 10.1038/cr.2011.140. Epub Aug. 23, 2011.
Goodnough et al., Development of a delivery vehicle for intracellular transport of botulinum neurotoxin antagonists. FEBS Lett. Feb. 27, 2002;513(2-3):163-8.
Grainge et al., The integrase family of recombinase: organization and function of the active site. Mol Microbiol. Aug. 1999;33(3):449-56.
Gregory et al., Integration site for Streptomyces phage phiBT1 and development of sitespecific integrating vectors. J Bacteriol. Sep. 2003;185(17):5320-3. doi: 10.1128/jb.185.17.5320-5323.2003.
Griffiths, Endogenous retroviruses in the human genome sequence. Genome Biol. 2001;2(6):REVIEWS1017. doi: 10.1186/gb-2001-2-6-reviews1017. Epub Jun. 5, 2001.
Grishok et al., Genes and Mechanisms Related to RNA Interference Regulate Expression of the Small Temporal RNAs that Control C. elegans Developmental Timing. Jul. 13, 2001:106(1):P23-4.
Groth et al., Construction of transgenic *Drosophila* by using the site-specific integrase from phage phiC31. Genetics. Apr. 2004;166(4):1775-82. doi: 10.1534/genetics.166.4.1775.
Gruber et al., Strategies for measuring evolutionary conservation of RNA secondary structures. BMC Bioinformatics. Feb. 26, 2008;9:122. doi: 10.1186/1471-2105-9-122.
Grunebaum et al., Recent advances in understanding and managing adenosine deaminase and purine nucleoside phosphorylase deficiencies. Curr Opin Allergy Clin Immunol. Dec. 2013;13(6):630-8. doi: 10.1097/ACI.0000000000000006.
Grünewald et al., Transcriptome-wide off-target RNA editing induced by CRISPR-guided DNA base editors. Nature. May 2019;569(7756):433-437. doi: 10.1038/s41586-019-1161-z. Epub Apr. 17, 2019.
Gupta et al., Sequences in attB that affect the ability of phiC31 integrase to synapse and to activate DNA cleavage. Nucleic Acids Res. 2007;35(10):3407-19. doi: 10.1093/nar/gkm206. Epub May 3, 2007.
Guzman et al., Tight regulation, modulation, and high-level expression by vectors containing the arabinose PBAD promoter. J Bacteriol. 1995;177(14):4121-4130.
Halmai et al., Targeted CRIPSR/dCas9-mediated reactivation of epigenetically silenced genes suggests limited escape from the inactive X chromosome. 2nd Inti Conf on Epigenetics and Bioengineering. Oct. 4, 2018; Retrieved from the Internet: https://aiche.confex.com/aiche/epibiol8/webprogram/paper544785.html. Retrieved Jun. 29, 2020.
Halperin et al., CRISPR-guided DNA polymerases enable diversification of all nucleotides in a tunable window. Nature. Aug. 2018;560(7717):248-252. doi: 10.1038/s41586-018-0384-8. Epub Aug. 1, 2018.
Halvas et al., Role of murine leukemia virus reverse transcriptase deoxyribonucleoside triphosphate-binding site in retroviral replication and in vivo fidelity. J Virol. Nov. 2000;74(22):10349-58. doi: 10.1128/jvi.74.22.10349-10358.2000.
Handa et al., Template-assisted synthesis of adenine-mutagenized cDNA by a retroelement protein complex. Nucleic Acids Res. Oct. 12, 2018;46(18):9711-9725. doi: 10.1093/nar/gky620.
Hanson et al., Codon optimality, bias and usage in translation and mRNA decay. Nat Rev Mol Cell Biol. Jan. 2018;19(1):20-30. doi: 10.1038/nrm.2017.91. Epub Oct. 11, 2017.
Harms et al., Evolutionary biochemistry: revealing the historical and physical causes of protein properties. Nat Rev Genet. Aug. 2013;14(8):559-71. doi: 10.1038/nrg3540.
Harrington et al., A thermostable Cas9 with increased lifetime in human plasma. Nat Commun. Nov. 10, 2017;8(1):1424. doi: 10.1038/s41467-017-01408-4.
Hasegawa et al., Spontaneous mutagenesis associated with nucleotide excision repair in *Escherichia coli*. Genes Cells. May 2008;13(5):459-69. doi: 10.1111/j.1365-2443.2008.01185.x.
Heidenreich et al., Non-homologous end joining as an important mutagenic process in cell cycle-arrested cells. EMBO J. May 1, 2003;22(9):2274-83. doi: 10.1093/emboj/cdg203.
Held et al., In vivo correction of murine hereditary tyrosinemia type I by phiC31 integrase-mediated gene delivery. Mol Ther. Mar. 2005;11(3):399-408. doi: 10.1016/j.ymthe.2004.11.001.
Hermonat et al., Use of adeno-associated virus as a mammalian DNA cloning vector: transduction of neomycin resistance into mammalian tissue culture cells. Proc Natl Acad Sci U S A. Oct. 1984;81(20):6466-70. doi: 10.1073/pnas.81.20.6466.
Herzig et al., A Novel Leu92 Mutant of HIV-1 Reverse Transcriptase with a Selective Deficiency in Strand Transfer Causes a Loss of Viral Replication. J Virol. Aug. 2015;89(16):8119-29. doi: 10.1128/JVI.00809-15. Epub May 20, 2015.
Hille et al., The Biology of CRISPR-Cas: Backward and Forward. Cell. Mar. 8, 2018;172(6):1239-1259. doi: 10.1016/j.cell.2017.11.032.
Hoang et al., UFBoot2: Improving the Ultrafast Bootstrap Approximation. Mol Biol Evol. Feb. 1, 2018;35(2):518-522. doi: 10.1093/molbev/msx281.

(56) References Cited

OTHER PUBLICATIONS

Hoernes et al., Translating the epitranscriptome. Wiley Interdiscip Rev RNA. Jan. 2017;8(1):e1375. doi: 10.1002/wrna.1375. Epub Jun. 27, 2016.
Hollis et al., Phage integrases for the construction and manipulation of transgenic mammals. Reprod Biol Endocrinol. Nov. 7, 2003;1:79. doi: 10.1186/1477-7827-1-79.
Holsinger et al., Signal transduction in T lymphocytes using a conditional allele of Sos. Proc Natl Acad Sci U S A. Oct. 10, 1995;92(21):9810-4. doi: 10.1073/pnas.92.21.9810.
Hoogenboom et al., Natural and designer binding sites made by phage display technology. Immunol Today. Aug. 2000;21(8):371-8.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013. Supplementary Information. 27 pages.
Hu et al., Evolved Cas9 variants with broad PAM compatibility and high DNA specificity. Nature. Apr. 5, 2018;556(7699):57-63. doi: 10.1038/nature26155. Epub Feb. 28, 2018.
Huang et al., Circularly permuted and PAM-modified Cas9 variants broaden the targeting scope of base editors. Nat Biotechnol. Jun. 2019;37(6):626-631. doi: 10.1038/s41587-019-0134-y. Epub May 20, 2019. Including Supplementary Information.
Hung et al., Protein localization in disease and therapy. J Cell Sci. Oct. 15, 2011;124(Pt 20):3381-92. doi: 10.1242/jcs.089110.
Hwang et al., Web-based design and analysis tools for CRISPR base editing. BMC Bioinformatics. Dec. 27, 2018;19(1):542. doi: 10.1186/s12859-018-2585-4.
Iida et al., A site-specific, conservative recombination system carried by bacteriophage P1. Mapping the recombinase gene cin and the cross-over sites cix for the inversion of the C segment. EMBO J. 1982;1(11):1445-53.
Imburgio et al., Studies of promoter recognition and start site selection by T7 RNA polymerase using a comprehensive collection of promoter variants. Biochemistry. Aug. 29, 2000;39(34):10419-30.
Iwai et al., Circular beta-lactamase: stability enhancement by cyclizing the backbone. FEBS Lett. Oct. 8, 1999;459(2): 166-72. doi: 10.1016/s0014-5793(99)01220-x.
Iwai et al., Highly efficient protein trans-splicing by a naturally split DnaE intein from Nostoc punctiforme. FEBS Lett. Mar. 20, 2006;580(7):1853-8. doi: 10.1016/j.febslet.2006.02.045. Epub Feb. 24, 2006.
Jaffrey et al., Emerging links between m6A and misregulated mRNA methylation in cancer. Genome Med. Jan. 12, 2017;9(1):2. doi: 10.1186/s13073-016-0395-8.
Jasin et al., Repair of strand breaks by homologous recombination. Cold Spring Harb Perspect Biol. Nov. 1, 2013;5(11):a012740. doi: 10.1101/cshperspect.a012740.
Jemielity et al., Novel "anti-reverse" cap analogs with superior translational properties. RNA. Sep. 2003;9(9): 1108-22. doi: 10.1261/rna.5430403.
Jiang et al., CRISPR-Cas9 Structures and Mechanisms. Annu Rev Biophys. May 22, 2017;46:505-529. doi: 10.1146/annurev-biophys-062215-010822. Epub Mar. 30, 2017.
Johann et al., GLVR1, a receptor for gibbon ape leukemia virus, is homologous to a phosphate permease of Neurospora crassa and is expressed at high levels in the brain and thymus. J Virol. Mar. 1992;66(3):1635-40. doi: 10.1128/JVI.66.3.1635-1640.1992.
Johns et al., The promise and peril of continuous in vitro evolution. J Mol Evol. Aug. 2005;61(2):253-63. Epub Jun. 27, 2005.
Joho et al., Identification of a region of the bacteriophage T3 and T7 RNA polymerases that determines promoter specificity. J Mol Biol. Sep. 5, 1990;215(1):31-9.
Joyce et al., Amplification, mutation and selection of catalytic RNA. Gene. Oct. 15, 1989;82(1):83-7. doi: 10.1016/0378-1119(89)90033-4.
Kaczmarczyk et al., Manipulating the Prion Protein Gene Sequence and Expression Levels with CRISPR/Cas9. PLoS One. Apr. 29, 2016;11(4):e0154604. doi: 10.1371/journal.pone.0154604.
Kadoch et al., Reversible disruption of mSWI/SNF (BAF) complexes by the SS18-SSX oncogenic fusion in synovial sarcoma. Cell. Mar. 28, 2013; 153(1):71-85. doi: 10.1016/j.cell.2013.02.036.
Kahmann et al., G inversion in bacteriophage Mu DNA is stimulated by a site within the invertase gene and a host factor. Cell. Jul. 1985;41(3):771-80. doi: 10.1016/s0092-8674(85)80058-1.
Kalyaanamoorthy et al., ModelFinder: fast model selection for accurate phylogenetic estimates. Nat Methods. Jun. 2017;14(6):587-589. doi: 10.1038/nmeth.4285. Epub May 8, 2017.
Karimova et al., Discovery of Nigri/nox and Panto/pox site-specific recombinase systems facilitates advanced genome engineering. Sci Rep. Jul. 22, 2016;6:30130. doi: 10.1038/srep30130.
Karimova et al., Vika/vox, a novel efficient and specific Cre/loxP-like site-specific recombination system. Nucleic Acids Res. Jan. 2013;41(2):e37. doi: 10.1093/nar/gks1037. Epub Nov. 9, 2012.
Kaufman et al., Translational efficiency of polycistronic mRNAs and their utilization to express heterologous genes in mammalian cells. EMBO J. Jan. 1987;6(1):187-93.
Kawarasaki et al., Enhanced crossover SCRATCHY: construction and high-throughput screening of a combinatorial library containing multiple non-homologous crossovers. Nucleic Acids Res. Nov. 1, 2003;31(21):e126.
Keijzers et al., Human exonuclease 1 (EXO1) activity characterization and its function on flap structures. Biosci Rep. Apr. 25, 2015;35(3):e00206. doi: 10.1042/BSR20150058.
Kelman, PCNA: structure, functions and interactions. Oncogene. Feb. 13, 1997;14(6):629-40. doi: 10.1038/sj.onc.1200886.
Kessler et al., Gene delivery to skeletal muscle results in sustained expression and systemic delivery of a therapeutic protein. Proc Natl Acad Sci U S A. Nov. 26, 1996;93(24):14082-7. doi: 10.1073/pnas.93.24.14082.
Kilcher et al., Brochothrix thermosphacta bacteriophages feature heterogeneous and highly mosaic genomes and utilize unique prophage insertion sites. J Bacteriol. Oct. 2010;192(20):5441-53. doi: 10.1128/JB.00709-10. Epub Aug. 13, 2010.
Kim et al., DJ-1, a novel regulator of the tumor suppressor PTEN. Cancer Cell. 2005;7(3):263-273.
Kim et al., High cleavage efficiency of a 2A peptide derived from porcine teschovirus-1 in human cell lines, zebrafish and mice. PLoS One. 2011;6(4):e18556. doi: 10.1371/journal.pone.0018556. Epub Apr. 29, 2011.
Kim et al., In vivo high-throughput profiling of CRISPR-Cpf1 activity. Nat Methods. Feb. 2017;14(2):153-159. doi: 10.1038/nmeth.4104. Epub Dec. 19, 2016.
Kim et al., Mycobacteriophage Bxb1 integrates into the *Mycobacterium smegmatis* groEL1 gene. Mol Microbiol. Oct. 2003;50(2):463-73. doi: 10.1046/j.1365-2958.2003.03723.x.
Kim et al., Rescue of high-specificity Cas9 variants using sgRNAs with matched 5' nucleotides. Genome Biol. Nov. 15, 2017;18(1):218. doi: 10.1186/s13059-017-1355-3.
Kim et al., Structural and kinetic characterization of *Escherichia coli* TadA, the wobble-specific tRNA deaminase. Biochemistry. May 23, 2006;45(20):6407-16. doi: 10.1021/bi0522394. PMID: 16700551.
Klapacz et al., Frameshift mutagenesis and micro satellite instability induced by human alkyladenine DNA glycosylase. Mol Cell. Mar. 26, 2010;37(6):843-53. doi: 10.1016/j.molcel.2010.01.038.
Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.
Knott et al., Guide-bound structures of an RNA-targeting A-cleaving CRISPR-Cas13a enzyme. Nat Struct Mol Biol. Oct. 2017;24(10):825-833. doi: 10.1038/nsmb.3466. Epub Sep. 11, 2017.
Koblan et al., Improving cytidine and adenine base editors by expression optimization and ancestral reconstruction. Nat Biotechnol. Oct. 2018;36(9):843-846. doi: 10.1038/nbt.4172. Epub May 29, 2018.
Kohli et al., A portable hot spot recognition loop transfers sequence preferences from APOBEC family members to activation-induced cytidine deaminase. J Biol Chem. Aug. 21, 2009;284(34):22898-904. doi: 10.1074/jbc.M109.025536. Epub Jun. 26, 2009.

(56) References Cited

OTHER PUBLICATIONS

Koike-Yusa et al., Genome-wide recessive genetic screening in mammalian cells with a lentiviral CRISPR-guide RNA library. Nat Biotechnol. Mar. 2014;32(3):267-73. doi: 10.1038/nbt.2800. Epub Dec. 23, 2013.
Komor, Editing the Genome Without Double-Stranded DNA Breaks. ACS Chem Biol. Feb. 16, 2018;13(2):383-388. doi: 10.1021/acschembio.7b00710. Epub Oct. 9, 2017.
Kosicki et al., Repair of double-strand breaks induced by CRISPR-Cas9 leads to large deletions and complex rearrangements. Nat Biotechnol. Sep. 2018;36(8):765-771. doi: 10.1038/nbt.4192. Epub Jul. 16, 2018.
Kotewicz et al., Isolation of cloned Moloney murine leukemia virus reverse transcriptase lacking ribonuclease H activity. Nucleic Acids Res. Jan. 11, 1988;16(1):265-77. doi: 10.1093/nar/16.1.265.
Kowalski et al., Delivering the Messenger: Advances in Technologies for Therapeutic mRNA Delivery. Mol Ther. Apr. 10, 2019;27(4):710-728. doi: 10.1016/j.ymthe.2019.02.012. Epub Feb. 19, 2019.
Kozak, An analysis of 5'-noncoding sequences from 699 vertebrate messenger RNAs. Nucleic Acids Res. Oct. 26, 1987;15(20):8125-48. doi: 10.1093/nar/15.20.8125.
Kraft et al., Deletions, Inversions, Duplications: Engineering of Structural Variants using CRISPR/Cas in Mice. Cell Rep. Feb. 10, 2015;10(5):833-839. doi: 10.1016/j.celrep.2015.01.016. Epub Feb. 7, 2015.
Krokan et al., Base excision repair. Cold Spring Harb Perspect Biol. Apr. 1, 2013;5(4):a012583. doi: 10.1101/cshperspect.a012583.
Krokan et al., Uracil in DNA—occurrence, consequences and repair. Oncogene. Dec. 16, 2002;21(58):8935-48. doi: 10.1038/sj.onc.1205996.
Krzywkowski et al., Limited reverse transcriptase activity of phi29 DNA polymerase. Nucleic Acids Res. Apr. 20, 2018;46(7):3625-3632. doi: 10.1093/nar/gky190.
Kuscu et al., CRISPR-Cas9-AID base editor is a powerful gain-of-function screening tool. Nat Methods. Nov. 29, 2016; 13(12):983-984. doi: 10.1038/nmeth.4076.
Kwart et al., Precise and efficient scarless genome editing in stem cells using CORRECT. Nat Protoc. Feb. 2017;12(2):329-354. doi: 10.1038/nprot.2016.171. Epub Jan. 19, 2017.
Lada et al., Mutator effects and mutation signatures of editing deaminases produced in bacteria and yeast. Biochemistry (Mose). Jan. 2011;76(1):131-46.
Lauer et al., Construction, characterization, and use of two Listeria monocytogenes site-specific phage integration vectors. J Bacteriol. Aug. 2002;184(15):4177-86. doi: 10.1128/jb.184.15.4177-4186.2002.
Lawyer et al., High-level expression, purification, and enzymatic characterization of full-length Thermus aquaticus DNA polymerase and a truncated form deficient in 5' to 3' exonuclease activity. PCR Methods Appl. May 1993;2(4):275-87. doi: 10.1101/gr.2.4.275.
Lazarevic et al., Nucleotide sequence of the Bacillus subtilis temperate bacteriophage SPbetac2. Microbiology (Reading). May 1999;145 ( Pt 5):1055-1067. doi: 10.1099/13500872-145-5-1055.
Le Grice et al., Purification and characterization of recombinant equine infectious anemia virus reverse transcriptase. J Virol. Dec. 1991;65(12):7004-7. doi: 10.1128/JVI.65.12.7004-7007.1991.
Leaver-Fay et al., ROSETTA3: an object-oriented software suite for the simulation and design of macromolecules. Methods Enzymol. 2011;487:545-74. doi: 10.1016/B978-0-12-381270-4.00019-6.
Leconte et al., A population-based experimental model for protein evolution: effects of mutation rate and selection stringency on evolutionary outcomes. Biochemistry. Feb. 26, 2013;52(8):1490-9. doi: 10.1021/bi3016185. Epub Feb. 14, 2013.
Lee et al., Site-specific integration of my cobacteriophage L5: integration-proficient vectors for *Mycobacterium smegmatis*, *Mycobacterium tuberculosis*, and bacille Calmette-Guerin. Proc Natl Acad Sci U S A. Apr. 15, 1991;88(8):3111-5. doi: 10.1073/pnas.88.8.3111.
Lee et al., Synthetically modified guide RNA and donor DNA are a versatile platform for CRISPR-Cas9 engineering. Elife. May 2, 2017;6:e25312. doi: 10.7554/eLife.25312.
Lee et al., Transcriptional regulation and its misregulation in disease. Cell. Mar. 14, 2013;152(6):1237-51. doi: 10.1016/j.cell.2013.02.014.
Lemos et al., CRISPR/Cas9 cleavages in budding yeast reveal templated insertions and strandspecific insertion/deletion profiles. Proc Natl Acad Sci U S A. Feb. 27, 2018;115(9):E2040-E2047. doi: 10.1073/pnas.1716855115. Epub Feb. 13, 2018.
Levy et al., Cytosine and adenine base editing of the brain, liver, retina, heart and skeletal muscle of mice via adeno-associated viruses. Nat Biomed Eng. 2020;4(1):97-110. doi:10.1038/s41551-019-0501-5.
Levy et al., Membrane-associated guanylate kinase dynamics reveal regional and developmental specificity of synapse stability. J Physiol. Mar. 1, 2017;595(5):1699-1709. doi: 10.1113/JP273147. Epub Jan. 18, 2017.
Lew et al., Protein splicing in vitro with a semisynthetic two-component minimal intein. J Biol Chem. Jun. 26, 1998;273(26):15887-90. doi: 10.1074/jbc.273.26.15887.
Lewis et al., Cytosine deamination and the precipitous decline of spontaneous mutation during Earth's history. Proc Natl Acad Sci U S A. Jul. 19, 2016;113(29):8194-9. doi: 10.1073/pnas.1607580113. Epub Jul. 5, 2016.
Li et al., A Radioactivity-Based Assay for Screening Human m6A-RNA Methyltransferase, METTL3-METTL14 Complex, and Demethylase ALKBH5. J Biomol Screen. Mar. 2016;21(3):290-7. doi: 10.1177/1087057115623264. Epub Dec. 23, 2015.
Li et al., Fast and accurate short read alignment with Burrows-Wheeler transform. Bioinformatics. Jul. 15, 2009;25(14):1754-60. doi: 10.1093/bioinformatics/btp324. Epub May 18, 2009.
Li et al., Lagging strand DNA synthesis at the eukaryotic replication fork involves binding and stimulation of FEN-1 by proliferating cell nuclear antigen. J Biol Chem. Sep. 22, 1995;270(38):22109-12. doi: 10.1074/jbc.270.38.22109.
Li et al., Protein trans-splicing as a means for viral vector-mediated in vivo gene therapy. Hum Gene Ther. Sep. 2008;19(9):958-64. doi: 10.1089/hum.2008.009.
Liang et al., Correction of ?-thalassemia mutant by base editor in human embryos. Protein Cell. Nov. 2017;8(11):811-822. doi: 10.1007/s13238-017-0475-6. Epub Sep. 23, 2017.
Lienert et al., Two- and three-input TALE-based and logic computation in embryonic stem cells. Nucleic Acids Res. Nov. 2013;41(21):9967-75. doi: 10.1093/nar/gkt758. Epub Aug. 27, 2013.
Lim et al., Crystal structure of the moloney murine leukemia virus RNase H domain. J Virol. Sep. 2006;80(17):8379-89. doi: 10.1128/JVI.00750-06.
Liu et al., Split dnaE genes encoding multiple novel inteins in Trichodesmium erythraeum. J Biol Chem. Jul. 18, 2003;278(29):26315-8. doi: 10.1074/jbc.C300202200. Epub May 24, 2003.
Liu et al., A METTL3-METTL14 complex mediates mammalian nuclear RNA N6-adenosine methylation. Nat Chem Biol. Feb. 2014;10(2):93-5. doi: 10.1038/nchembio.1432. Epub Dec. 6, 2013.
Liu et al., CasX enzymes comprise a distinct family of RNA-guided genome editors. Nature. Feb. 2019;566(7743):218-223. doi: 10.1038/s41586-019-0908-x. Epub Feb. 4, 2019.
Liu et al., Direct Promoter Repression by BCL11A Controls the Fetal to Adult Hemoglobin Switch. Cell. Apr. 5, 2018;173(2):430-442.e17. doi: 10.1016/j.cell.2018.03.016. Epub Mar. 29, 2018.
Liu et al., Editing DNA Methylation in the Mammalian Genome. Cell. Sep. 22, 2016;167(1):233-247.e17. doi: 10.1016/j.cell.2016.08.056.
Liu et al., Highly efficient RNA-guided base editing in rabbit. Nat Commun. Jul. 13, 2018;9(1):2717. doi: 10.1038/s41467-018-05232-2.
Liu et al., N(6)-methyladenosine-dependent RNA structural switches regulate RNA-protein interactions. Nature. Feb. 26, 2015;518(7540):560-4. doi: 10.1038/nature14234.
Liu et al., Probing N6-methyladenosine RNA modification status at single nucleotide resolution in mRNA and long noncoding RNA. RNA. Dec. 2013;19(12):1848-56. doi: 10.1261/ma.041178.113. Epub Oct. 18, 2013.

(56) References Cited

OTHER PUBLICATIONS

Liu et al., The Molecular Architecture for RNA-Guided RNA Cleavage by Cas13a. Cell. Aug. 10, 2017;170(4):714-726.e10. doi: 10.1016/j.cell.2017.06.050. Epub Jul. 27, 2017.

Loessner et al., Complete nucleotide sequence, molecular analysis and genome structure of bacteriophage A118 of Listeria monocytogenes: implications for phage evolution. Mol Microbiol. Jan. 2000;35(2):324-40. doi: 10.1046/j.1365-2958.2000.01720.x.

Long et al., Postnatal genome editing partially restores dystrophin expression in a mouse model of muscular dystrophy. Science. Jan. 22, 2016;351(6271):400-3. doi: 10.1126/science.aad5725. Epub Dec. 31, 2015.

Lynch, Evolution of the mutation rate. Trends Genet. Aug. 2010;26(8):345-52. doi: 10.1016/j.tig.2010.05.003. Epub Jun. 30, 2010.

Maas et al., Identification and characterization of a human tRNA-specific adenosine deaminase related to the ADAR family of pre-mRNA editing enzymes. Proc Natl Acad Sci U S A. Aug. 3, 1999;96(16):8895-900. doi: 10.1073/pnas.96.16.8895.

Macbeth et al., Inositol hexakisphosphate is bound in the ADAR2 core and required for RNA editing. Science. Sep. 2, 2005;309(5740):1534-9. doi: 10.1126/science.1113150.

Magin et al., Corf, the Rev/Rex homologue of HTDV/HERV-K, encodes an arginine-rich nuclear localization signal that exerts a trans-dominant phenotype when mutated. Virology. Aug. 15, 2000;274(1):11-6. doi: 10.1006/viro.2000.0438.

Makarova et al., Classification and Nomenclature of CRISPR-Cas Systems: Where from Here? CRISPR J. Oct. 2018;1(5):325-336. doi: 10.1089/crispr.2018.0033.

Makeyev et al., Evolutionary potential of an RNA virus. J Virol. Feb. 2004;78(4):2114-20.

Malashkevich et al., Crystal structure of tRNA adenosine deaminase TadA from *Escherichia coli*. Deposited: Mar. 10, 2005 Released: Feb. 21, 2006 doi:10.2210/pdb1z3a/pdb (2006).

Malito et al., Structural basis for lack of toxicity of the diphtheria toxin mutant CRM197. Proc Natl Acad Sci U S A. Apr. 3, 2012;109(14):5229-34. doi: 10.1073/pnas.1201964109. Epub Mar. 19, 2012.

Mandal et al., Efficient ablation of genes in human hematopoietic stem and effector cells using CRISPR/Cas9. Cell Stem Cell. Nov. 6, 2014;15(5):643-52. doi: 10.1016/j.stem.2014.10.004. Epub Nov. 6, 2014.

Martinez et al., Hypermutagenesis of RNA using human immunodeficiency virus type 1 reverse transcriptase and biased dN'IP concentrations. Proc Natl Acad Sci U S A. Dec. 6, 1994;91(25):11787-91. doi: 10.1073/pnas.91.25.11787.

Mascola et al., HIV-1 neutralizing antibodies: understanding nature's pathways. Immunol Rev. Jul. 2013;254(1):225-44. doi: 10.1111/imr.12075.

Matthews, Structures of human ADAR2 bound to dsRNA reveal base-flipping mechanism and basis for site selectivity. Nat Struct Mol Biol. May 2016;23(5):426-33. doi: 10.1038/nsmb.3203. Epub Apr. 11, 2016.

May et al., Emergent lineages of mumps virus suggest the need for a polyvalent vaccine. Int J Infect Dis. Jan. 2018;66:1-4. doi: 10.1016/j.ijid.2017.09.024. Epub Oct. 4, 2017.

McInerney et al., Error Rate Comparison during Polymerase Chain Reaction by DNA Polymerase. Mol Biol Int. 2014;2014:287430. doi: 10.1155/2014/287430. Epub Aug. 17, 2014.

McKenna et al., Recording development with single cell dynamic lineage tracing. Development. Jun. 27, 2019;146(12):dev169730. doi: 10.1242/dev.169730.

McKenna et al., Whole-organism lineage tracing by combinatorial and cumulative genome editing. Science. Jul. 29, 2016;353(6298):aaf7907. doi: 10.1126/science.aaf7907. Epub May 26, 2016.

McVey et al., MMEJ repair of double-strand breaks (director's cut): deleted sequences and alternative endings. Trends Genet. Nov. 2008;24(11):529-38. doi: 10.1016/j.tig.2008.08.007. Epub Sep. 21, 2008.

Menéndez-Arias, Mutation rates and intrinsic fidelity of retroviral reverse transcriptases. Viruses. Dec. 2009;1(3):1137-65. doi: 10.3390/v1031137. Epub Dec. 4, 2009.

Mertens et al., Site-specific recombination in bacteriophage Mu: characterization of binding sites for the DNA invertase Gin. EMBO J. Apr. 1988;7(4):1219-27.

Meyer et al., Comprehensive analysis of mRNA methylation reveals enrichment in 3' UTRs and near stop codons. Cell. Jun. 22, 2012;149(7):1635-46. doi: 10.1016/j.cell.2012.05.003. Epub May 17, 2012.

Meyer et al., Library generation by gene shuffling. Curr Protoc Mol Biol. Jan. 6, 2014;105:Unit 15.12.. doi: 10.1002/0471142727. mb1512s105.

Meyer et al., The dynamic epitranscriptome: N6-methyladenosine and gene expression control. Nat Rev Mol Cell Biol. May 2014;15(5):313-26. doi: 10.1038/nrm3785. Epub Apr. 9, 2014.

Mihai et al., PTEN inhibition improves wound healing in lung epithelia through changes in cellular mechanics that enhance migration. Am J Physiol Lung Cell Mol Physiol. 2012;302(3):L287-L299.

Miller et al., Construction and properties of retrovirus packaging cells based on gibbon ape leukemia virus. J Virol. May 1991;65(5):2220-4. doi: 10.1128/JVI.65.5.2220-2224.1991.

Mishina et al., Conditional gene targeting on the pure C57BL/6 genetic background. Neurosci Res. Jun. 2007;58(2):105-12. doi: 10.1016/j.neures.2007.01.004. Epub Jan. 18, 2007.

Mitton-Fry et al., Poly(A) tail recognition by a viral RNA element through assembly of a triple helix. Science. Nov. 26, 2010;330(6008):1244-7. doi: 10.1126/science.1195858.

Moede et al., Identification of a nuclear localization signal, RRMKWKK, in the homeodomain transcription factor PDX-1. FEBS Lett. Nov. 19, 1999;461(3):229-34. doi: 10.1016/s0014-5793(99)01446-5.

Mohr et al., A Reverse Transcriptase-Cas1 Fusion Protein Contains a Cas6 Domain Required for Both CRISPR RNA Biogenesis and RNA Spacer Acquisition. Mol Cell. Nov. 15, 2018;72(4):700-714. e8. doi: 10.1016/j.molcel.2018.09.013. Epub Oct. 18, 2018.

Mohr et al., Thermostable group II intron reverse transcriptase fusion proteins and their use in cDNA synthesis and next-generation RNA sequencing. RNA. Jul. 2013;19(7):958-70. doi: 10.1261/ma.039743.113. Epub May 22, 2013.

Monot et al., The specificity and flexibility of l1 reverse transcription priming at imperfect T-tracts. PLoS Genet. May 2013;9(5):e1003499. doi: 10.1371/journal.pgen.1003499. Epub May 9, 2013.

Morita et al., The site-specific recombination system of actinophage TGI. FEMS Microbiol Lett. Aug. 2009;297(2):234-40. doi: 10.1111/j.1574-6968.2009.01683.x.

Muller et al., Nucleotide exchange and excision technology (NExT) DNA shuffling: a robust method for DNA fragmentation and directed evolution. Nucleic Acids Res. Aug. 1, 2005;33(13):e117. doi: 10.1093/nar/gni116. PMID: 16061932; PMCID: PMC1182171.

Muzyczka et al., Adeno-associated virus (AAV) vectors: will they work? J Clin Invest. Oct. 1994;94(4):1351. doi: 10.1172/JCI117468.

Myerowiiz et al., The major defect in Ashkenazi Jews with Tay-Sachs disease is an insertion in the gene for the alpha-chain of beta-hexosaminidase. J Biol Chem. Dec. 15, 1988;263(35):18587-9.

Nakade et al., Microhomology-mediated end-joining-dependent integration of donor DNA in cells and animals using TALENs and CRISPR/Cas9. Nat Commun. Nov. 20, 2014;5:5560. doi: 10.1038/ncomms6560.

Nakamura et al., Codon usage tabulated from international DNA sequence databases: status for the year 2000. Nucleic Acids Res. Jan. 1, 2000;28(1):292. doi: 10.1093/nar/28.1.292.

Naorem et al., DGR mutagenic transposition occurs via hypermutagenic reverse transcription primed by nicked template RNA. Proc Natl Acad Sci U S A. Nov. 21, 2017;114(47):E10187-E10195. doi: 10.1073/pnas. 1715952114. Epub Nov. 6, 2017.

Nern et al., Multiple new site-specific recombinases for use in manipulating animal genomes. Proc Natl Acad Sci U S A. Aug. 23, 2011;108(34):14198-203. doi: 10.1073/pnas.1111704108. Epub Aug. 9, 2011.

(56) References Cited

OTHER PUBLICATIONS

Nguyen et al., Evolutionary drivers of thermoadaptation in enzyme catalysis. Science. Jan. 20, 2017;355(6322):289-294. doi: 10.1126/science.aah3717. Epub Dec. 22, 2016.

Nguyen et al., IQ-TREE: a fast and effective stochastic algorithm for estimating maximumlikelihood phylogenies. Mol Biol Evol. Jan. 2015;32(1):268-74. doi: 10.1093/molbev/msu300. Epub Nov. 3, 2014.

Nishimasu et al., Engineered CRISPR-Cas9 nuclease with expanded targeting space. Science. Sep. 21, 2018;361(6408):1259-1262. doi: 10.1126/science.aas9129. Epub Aug. 30, 2018.

Nottingham et al., RNA-seq of human reference RNA samples using a thermostable group II intron reverse transcriptase. RNA. Apr. 2016;22(4):597-613. doi: 10.1261/ma.055558.115. Epub Jan. 29, 2016.

Nowak et al., Structural analysis of monomeric retroviral reverse transcriptase in complex with an RNA/DNA hybrid. Nucleic Acids Res. Apr. 1, 2013;41(6):3874-87. doi: 10.1093/nar/gkt053. Epub Feb. 4, 2013.

Numrych et al., A comparison of the effects of single-base and triple-base changes in the integrase arm-type binding sites on the site-specific recombination of bacteriophage lambda. Nucleic Acids Res. Jul. 11, 1990;18(13):3953-9. doi: 10.1093/nar/18.13.3953.

Nyerges et al., A highly precise and portable genome engineering method allows comparison of mutational effects across bacterial species. Proc Natl Acad Sci U S A. Mar. 1, 2016;113(9):2502-7. doi: 10.1073/pnas.1520040113. Epub Feb. 16, 2016.

Oakes et al., CRISPR-Cas9 Circular Permutants as Programmable Scaffolds for Genome Modification. Cell. Jan. 10, 2019; 176(1-2):254-267.e16. doi: 10.1016/j.cell.2018.11.052.

Odsbu et al., Specific N-terminal interactions of the *Escherichia coli* SeqA protein are required to form multimers that restrain negative supercoils and form foci. Genes Cells. Nov. 2005;10(11):1039-49.

Oeemig et al., Solution structure of DnaE intein from Nostoc punctiforme: structural basis for the design of a new split intein suitable for site-specific chemical modification. FEBS Lett. May 6, 2009;583(9):1451-6.

Oh et al., Positional cloning of a gene for Hermansky-Pudlak syndrome, a disorder of cytoplasmic organelles. Nat Genet. Nov. 1996;14(3):300-6. doi: 10.1038/ng1196-300.

O'Maille et al., Structure-based combinatorial protein engineering (SCOPE). J Mol Biol. Aug. 23, 2002;321(4):677-91.

Orlando et al., Zinc-finger nuclease-driven targeted integration into mammalian genomes using donors with limited chromosomal homology. Nucleic Acids Res. Aug. 2010;38(15):e152. doi: 10.1093/nar/gkq512. Epub Jun. 8, 2010.

Orthwein et al., A mechanism for the suppression of homologous recombination in G1 cells. Nature. Dec. 17, 2015;528(7582):422-6. doi: 10.1038/nature16142. Epub Dec. 9, 2015.

Ostermeier et al., A combinatorial approach to hybrid enzymes independent of DNA homology. Nat Biotechnol. Dec. 1999;17(12):1205-9.

Otto et al., The probability of fixation in populations of changing size. Genetics. Jun. 1997;146(2):723-33.

Paige et al., RNA mimics of green fluorescent protein. Science. Jul. 29, 2011;333(6042):642-6. doi: 10.1126/science.1207339.

Paquet et al., Efficient introduction of specific homozygous and heterozygous mutations using CRISPR/Cas9. Nature. May 5, 2016;533(7601):125-9. doi: 10.1038/nature17664. Epub Apr. 27, 2016.

Park et al., Digenome-seq web tool for profiling CRISPR specificity. Nat Methods. May 30, 2017;14(6):548-549. doi: 10.1038/nmeth.4262.

Park et al., Highly efficient editing of the ?-globin gene in patient-derived hematopoietic stem and progenitor cells to treat sickle cell disease. Nucleic Acids Res. Sep. 5, 2019;47(15):7955-7972. doi: 10.1093/nar/gkz475.

Park et al., Sendai virus, an RNA virus with no risk of genomic integration, delivers CRISPR/Cas9 for efficient gene editing. Mol Ther Methods Clin Dev. Aug. 24, 2016;3:16057. doi: 10.1038/mtm.2016.57.

Patel et al., Flap endonucleases pass 5'-flaps through a flexible arch using a disorder-thread-order mechanism to confer specificity for free 5'-ends. Nucleic Acids Res. May 2012;40(10):4507-19. doi: 10.1093/nar/gks051. Epub Feb. 8, 2012.

Pawson et al., Protein phosphorylation in signaling—50 years and counting. Trends Biochem Sci. Jun. 2005;30(6):286-90. doi: 10.1016/j.tibs.2005.04.013.

Pellenz et al., New human chromosomal safe harbor sites for genome engineering with CRISPR/Cas9, TAL effector and homing endonucleases. Aug. 20, 2018. bioRxiv doi: https://doi.org/10.1101/396390.

Perach et al., Catalytic features of the recombinant reverse transcriptase of bovine leukemia virus expressed in bacteria. Virology. Jun. 20, 1999;259(1):176-89. doi: 10.1006/viro.1999.9761.

Perler et al., Protein splicing elements: inteins and exteins—a definition of terms and recommended nomenclature. Nucleic Acids Res. Apr. 11, 1994;22(7):1125-7. doi: 10.1093/nar/22.7.1125.

Perler, InBase, the New England Biolabs Intein Database. Nucleic Acids Res. Jan. 1, 1999;27(1):346-7. doi: 10.1093/nar/27.1.346.

Perler, Protein splicing of inteins and hedgehog autoproteolysis: structure, function, and evolution. Cell. Jan. 9, 1998;92(1):1-4. doi: 10.1016/s0092-8674(00)80892-2.

Petersen-Mahrt et al., AID mutates *E. coli* suggesting a DNA deamination mechanism for antibody diversification. Nature. Jul. 4, 2002;418(6893):99-103.

Peyroties et al., Oligodeoxynucleoside phosphoramidates (P-NH2): synthesis and thermal stability of duplexes with DNA and RNA targets. Nucleic Acids Res. May 15, 1996;24(10):1841-8.

Pfeiffer et al., Mechanisms of DNA double-strand break repair and their potential to induce chromosomal aberrations. Mutagenesis. Jul. 2000;15(4):289-302. doi: 10.1093/mutage/15.4.289.

Pickart et al., Ubiquitin: structures, functions, mechanisms. Biochim Biophys Acta. Nov. 29, 2004;1695(1-3):55-72. doi: 10.1016/j.bbamcr.2004.09.019.

Pinkert et al., An albumin enhancer located 10 kb upstream functions along with its promoter to direct efficient, liver-specific expression in transgenic mice. Genes Dev. May 1987;1(3):268-76. doi: 10.1101/gad.1.3.268.

Pirakitikulr et al., PCRless library mutagenesis via oligonucleotide recombination in yeast. Protein Sci. Dec. 2010;19(12):2336-46. doi: 10.1002/pro.513.

Posnick et al., Imbalanced base excision repair increases spontaneous mutation and alkylation sensitivity in *Escherichia coli*. J Bacteriol. Nov. 1999;181(21):6763-71.

Pu et al., Evolution of a split RNA polymerase as a versatile biosensor platform. Nat Chem Biol. Apr. 2017;13(4):432-438. doi: 10.1038/nchembio.2299. Epub Feb. 13, 2017.

Qu et al., Global mapping of binding sites for phic31 integrase in transgenic maden-darby bovine kidney cells using ChIP-seq. Hereditas. Jan. 14, 2019;156:3. doi: 10.1186/s41065-018-0079-z.

Radany et al., Increased spontaneous mutation frequency in human cells expressing the phage PBS2-encoded inhibitor of uracil-DNA glycosylase. Mutat Res. Sep. 15, 2000;461(1):41-58. doi: 10.1016/s0921-8777(00)00040-9.

Ranzau et al., Genome, Epigenome, and Transcriptome Editing via Chemical Modification of Nucleobases in Living Cells. Biochemistry. Feb. 5, 2019;58(5):330-335. doi: 10.1021/acs.biochem.8b00958. Epub Dec. 12, 2018.

Rasila et al., Critical evaluation of random mutagenesis by error-prone polymerase chain reaction protocols, *Escherichia coli* mutator strain, and hydroxylamine treatment. Anal Biochem. May 1, 2009;388(1):71-80. doi: 10.1016/j.ab.2009.02.008. Epub Feb. 10, 2009.

Raskin et al., Substitution of a single bacteriophage T3 residue in bacteriophage T7 RNA polymerase at position 748 results in a switch in promoter specificity. J Mol Biol. Nov. 20, 1992;228(2):506-15.

(56) References Cited

OTHER PUBLICATIONS

Raskin et al., T7 RNA polymerase mutants with altered promoter specificities. Proc Natl Acad Sci U S A. Apr. 15, 1993;90(8):3147-51.
Rauch et al., Programmable RNA Binding Proteins for Imaging and Therapeutics. Biochemistry. Jan. 30, 2018;57(4):363-364. doi: 10.1021/acs.biochem.7b01101. Epub Nov. 17, 2017.
Ray et al., A compendium of RNA-binding motifs for decoding gene regulation. Nature. Jul. 11, 2013;499(7457):172-7. doi: 10.1038/nature12311.
Rebar et al., Phage display methods for selecting zinc finger proteins with novel DNA-binding specificities. Methods Enzymol. 1996;267:129-49.
Rees et al., Analysis and minimization of cellular RNA editing by DNA adenine base editors. Sci Adv. May 8, 2019;5(5):eaax5717. doi: 10.1126/sciadv.aax5717.
Rees et al., Base editing: precision chemistry on the genome and transcriptome of living cells. Nat Rev Genet. Dec. 2018;19(12):770-788. doi: 10.1038/s41576-018-0059-1.
Rees et al., Development of hRad51-Cas9 nickase fusions that mediate HDR without doublestranded breaks. Nat Commun. May 17, 2019;10(1):2212. doi: 10.1038/s41467-019-09983-4.
Reyon et al., FLASH assembly of TALENs for high-throughput genome editing. Nat Biotechnol. May 2012;30(5):460-5. doi: 10.1038/nbt.2170.
Ribeiro et al., Protein Engineering Strategies to Expand CRISPR-Cas9 Applications. Int J Genomics. Aug. 2, 2018;2018:1652567. doi: 10.1155/2018/1652567.
Ringrose et al., The Kw recombinase, an integrase from Kluyveromyces waltii. Eur J Biochem. Sep. 15, 1997;248(3):903-12. doi: 10.1111/j.1432-1033.1997.00903.x.
Roth et al., Purification and characterization of murine retroviral reverse transcriptase expressed in *Escherichia coli*. J Biol Chem. Aug. 5, 1985;260(16):9326-35.
Rouet et al., Expression of a site-specific endonuclease stimulates homologous recombination in mammalian cells. Proc Natl Acad Sci U S A. Jun. 21, 1994;91(13):6064-8. doi: 10.1073/pnas.91.13.6064.
Rouet et al., Introduction of double-strand breaks into the genome of mouse cells by expression of a rare-cutting endonuclease. Mol Cell Biol. Dec. 1994;14(12):8096-106. doi: 10.1128/mcb.14.12.8096.
Rouet et al., Receptor-Mediated Delivery of CRISPR-Cas9 Endonuclease for Cell-Type-Specific Gene Editing. J Am Chem Soc. May 30, 2018;140(21):6596-6603. doi: 10.1021/jacs.8b01551. Epub May 18, 2018.
Roundtree et al.,YTHDC1 mediates nuclear export of N6-methyladenosine methylated mRNAs. Elife. Oct. 6, 2017;6:e31311. doi: 10.7554/eLife.31311.
Rowland et al., Sin recombinase from Staphylococcus aureus: synaptic complex architecture and transposon targeting. Mol Microbiol. May 2002;44(3):607-19. doi: 10.1046/j.1365-2958.2002.02897.x.
Rubio et al., An adenosine-to-inosine tRNA-editing enzyme that can perform C-to-U deamination of DNA. Proc Natl Acad Sci U S A. May 8, 2007;104(19):7821-6. doi: 10.1073/pnas.0702394104. Epub May 1, 2007. PMID: 17483465; PMCID: PMC1876531.
Rüfer et al., Non-contact positions impose site selectivity on Cre recombinase. Nucleic Acids Res. Jul. 1, 2002;30(13):2764-71. doi: 10.1093/nar/gkf399.
Rutherford et al., Attachment site recognition and regulation of directionality by the serine integrases. Nucleic Acids Res. Sep. 2013;41(17):8341-56. doi: 10.1093/nar/gkt580. Epub Jul. 2, 2013.
Sakuma et al., MMEJ-assisted gene knock-in using TALENs and CRISPR-Cas9 with the PITCh systems. Nat Protoc Jan. 2016;11(1):118-33. doi: 10.1038/nprot.2015.140. Epub Dec. 17, 2015.
Samulski et al., Helper-free stocks of recombinant adeno-associated viruses: normal integration does not require viral gene expression. J Virol. Sep. 1989;63(9):3822-8. doi: 10.1128/JVI.63.9.3822-3828.1989.

Santoro et al., Directed evolution of the site specificity of Cre recombinase. Proc Natl Acad Sci U S A. Apr. 2, 2002;99(7):4185-90. Epub Mar. 19, 2002.
Saparbaev et al., Excision of hypoxanthine from DNA containing dIMP residues by the *Escherichia coli*, yeast, rat, and human alkylpurine DNA glycosylases. Proc Natl Acad Sci U S A. Jun. 21, 1994;91(13):5873-7. doi: 10.1073/pnas.91.13.5873.
Satomura et al., Precise genome-wide base editing by the CRISPR Nickase system in yeast. Sci Rep. May 18, 2017;7(1):2095. doi: 10.1038/s41598-017-02013-7.
Sauer et al., DNA recombination with a heterospecific Cre homolog identified from comparison of the pac-c1 regions of P1-related phages. Nucleic Acids Res. Nov. 18, 2004;32(20):6086-95. doi: 10.1093/nar/gkh941.
Schaaper et al., Base selection, proofreading, and mismatch repair during DNA replication in *Escherichia coli*. J Biol Chem. Nov. 15, 1993;268(32):23762-5.
Schaaper et al., Spectra of spontaneous mutations in *Escherichia coli* strains defective in mismatch correction: the nature of in vivo DNA replication errors. Proc Natl Acad Sci U S A. Sep. 1987;84(17):6220-4.
Schaefer et al., Understanding RNA modifications: the promises and technological bottlenecks of the 'epitranscriptome'. Open Biol. May 2017;7(5):170077. doi: 10.1098/rsob.170077.
Schechner et al., Multiplexable, locus-specific targeting of long RNAs with CRISPR-Display. Nat Methods. Jul. 2015;12(7):664-70. doi: 10.1038/nmeth.3433. Epub Jun. 1, 2015.
Schek et al., Definition of the upstream efficiency element of the simian virus 40 late polyadenylation signal by using in vitro analyses. Mol Cell Biol. Dec. 1992;12(12):5386-93. doi: 10.1128/mcb.12.12.5386.
Schenk et al., MPDU1 mutations underlie a novel human congenital disorder of glycosylation, designated type If. J Clin Invest. Dec. 2001;108(11):1687-95. doi: 10.1172/JCI13419.
Schmitz et al., Behavioral abnormalities in prion protein knockout mice and the potential relevance of PrP(C) for the cytoskeleton. Prion. 2014;8(6):381-6. doi: 10.4161/19336896.2014.983746.
Schöller et al., Interactions, localization, and phosphorylation of the m6A generating METTL3-METTL14-WTAP complex. RNA. Apr. 2018;24(4):499-512. doi: 10.1261/ma.064063.117. Epub Jan. 18, 2018.
Schultz et al., Oligo-2'-fluoro-2'-deoxynucleotide N3'—>P5' phosphoramidates: synthesis and properties. Nucleic Acids Res. Aug. 1, 1996;24(15):2966-73.
Scott et al., Production of cyclic peptides and proteins in vivo. Proc Natl Acad Sci U S A. Nov. 23, 1999;96(24):13638-43. doi: 10.1073/pnas.96.24.13638.
Sebastián-Martín et al., Transcriptional inaccuracy threshold attenuates differences in RNA-dependent DNA synthesis fidelity between retroviral reverse transcriptases. Sci Rep. Jan. 12, 2018;8(1):627. doi: 10.1038/s41598-017-18974-8.
Serrano-Heras et al., Protein p56 from the Bacillus subtilis phage phi29 inhibits DNA-binding ability of uracil-DNA glycosylase. Nucleic Acids Res. 2007;35(16):5393-401. Epub Aug. 13, 2007.
Severinov et al., Expressed protein ligation, a novel method for studying protein-protein interactions in transcription. J Biol Chem. Jun. 26, 1998;273(26):16205-9. doi: 10.1074/jbc.273.26.16205.
Shah et al., Protospacer recognition motifs: mixed identities and functional diversity. RNA Biol. May 2013;10(5):891-9. doi: 10.4161/rna.23764. Epub Feb. 12, 2013.
Shalem et al., High-throughput functional genomics using CRISPR-Cas9. Nat Rev Genet. May 2015;16(5):299-311. doi: 10.1038/nrg3899. Epub Apr. 9, 2015.
Sharer et al., The ARF-like 2 (ARL2)-binding protein, BART. Purification, cloning, and initial characterization. J Biol Chem. Sep. 24, 1999;274(39):27553-61. doi: 10.1074/jbc.274.39.27553.
Sharon et al., Functional Genetic Variants Revealed by Massively Parallel Precise Genome Editing. Cell. Oct. 4, 2018;175(2):544-557.e16. doi: 10.1016/j.cell.2018.08.057. Epub Sep. 20, 2018.
Shaw et al., Implications of human genome architecture for rearrangement-based disorders: the genomic basis of disease. Hum Mol Genet. Apr. 1, 2004 ;13 Spec No. 1:R57-64. doi: 10.1093/hmg/ddh073. Epub Feb. 5, 2004.

(56) References Cited

OTHER PUBLICATIONS

Shen et al., Predictable and precise template-free CRISPR editing of pathogenic variants. Nature. Nov. 2018;563(7733):646-651. doi: 10.1038/s41586-018-0686-x. Epub Nov. 7, 2018. Erratum in: Nature. Mar. 2019;567(7746):E1-E2.

Sherwood et al., Discovery of directional and nondirectional pioneer transcription factors by modeling DNase profile magnitude and shape. Nat Biotechnol. Feb. 2014;32(2):171-178. doi: 10.1038/nbt. 2798. Epub Jan. 19, 2014.

Shi et al., Structural basis for targeted DNA cytosine deamination and mutagenesis by APOBEC3A and APOBEC3B. Nat Struct Mol Biol. Feb. 2017;24(2):131-139. doi: 10.1038/nsmb.3344. Epub Dec. 19, 2016.

Shi et al., YTHDF3 facilitates translation and decay of N6-methyladenosine-modified RNA. Cell Res. Mar. 2017;27(3):315-328. doi: 10.1038/cr.2017.15. Epub Jan. 20, 2017.

Shindo et al., A Comparison of Two Single-Stranded DNA Binding Models by Mutational Analysis of APOBEC3G. Biology (Basel). Aug. 2, 2012;1(2):260-76. doi: 10.3390/biology1020260.

Shmakov et al., Diversity and evolution of class 2 CRISPR-Cas systems. Nat Rev Microbiol. Mar. 2017;15(3):169-182. doi: 10.1038/nrmicro.2016.184. Epub Jan. 23, 2017.

Shultz et al., A genome-wide analysis of FRT-like sequences in the human genome. PLoS One. Mar. 23, 2011;6(3):e18077. doi: 10.1371/journal.pone.0018077.

Silas et al., Direct CRISPR spacer acquisition from RNA by a natural reverse transcriptase-Cas1 fusion protein. Science. Feb. 26, 2016;351(6276):aad4234. doi: 10.1126/science.aad4234.

Silva et al., Selective disruption of the DNA polymerase III α-β complex by the umuD gene products. Nucleic Acids Res. Jul. 2012;40(12):5511-22. doi: 10.1093/nar/gks229. Epub Mar. 9, 2012.

Sivalingam et al., Biosafety assessment of site-directed transgene integration in human umbilical cord-lining cells. Mol Ther. Jul. 2010;18(7):1346-56. doi: 10.1038/mt.2010.61. Epub Apr. 27, 2010.

Sledz et al., Structural insights into the molecular mechanism of the m(6)A writer complex. Elife. Sep. 14, 2016;5:e18434. doi: 10.7554/eLife.18434.

Smargon et al., Cas13b Is a Type VI-B CRISPR-Associated RNA-Guided RNase Differentially Regulated by Accessory Proteins Csx27 and Csx28. Mol Cell. Feb. 16, 2017;65(4):618-630.e7. doi: 10.1016/j.molcel.2016.12.023. Epub Jan. 5, 2017.

Smith et al., Production of human beta interferon in insect cells infected with a baculovirus expression vector. Mol Cell Biol. Dec. 1983;3(12):2156-65. doi: 10.1128/mcb.3.12.2156.

Smith, Phage-encoded Serine Integrases and Other Large Serine Recombinases. Microbiol Spectr. Aug. 2015;3(4). doi: 10.1128/microbiolspec.MDNA3-0059-2014.

Southworth et al., Control of protein splicing by intein fragment reassembly. EMBO J. Feb. 16, 1998;17(4):918-26. doi: 10.1093/emboj/17.4.918.

Southworth et al., Purification of proteins fused to either the amino or carboxy terminus of the *Mycobacterium xenopi* gyrase A intein. Biotechniques. Jul. 1999;27(1):110-4, 116, 118-20. doi: 10.2144/99271st04.

Spencer et al., A general strategy for producing conditional alleles of Src-like tyrosine kinases. Proc Natl Acad Sci U S A. Oct. 10, 1995;92(21):9805-9. doi: 10.1073/pnas.92.21.9805.

Spencer et al., Functional analysis of Fas signaling in vivo using synthetic inducers of dimerization. CurrBiol. Jul. 1, 1996;6(7):839-47. doi: 10.1016/s0960-9822(02)00607-3.

Srivastava et al., An inhibitor of nonhomologous end-joining abrogates double-strand break repair and impedes cancer progression. Cell. Dec. 21, 2012;151(7):1474-87. doi: 10.1016Zj.cell.2012.11. 054.

Stamos et al., Structure of a Thermostable Group II Intron Reverse Transcriptase with Template-Primer and Its Functional and Evolutionary Implications. Mol Cell. Dec. 7, 2017;68(5):926-939.e4. doi: 10.1016/j.molcel.2017.10.024. Epub Nov. 16, 2017.

Steele et al., The prion protein knockout mouse: a phenotype under challenge. Prion. Apr.-Jun. 2007;1(2):83-93. doi: 10.4161/pri.1.2. 4346. Epub Apr. 25, 2007.

Sterne-Weiler et al., Exon identity crisis: disease-causing mutations that disrupt the splicing code. Genome Biol. Jan. 23, 2014;15(1):201. doi: 10.1186/gb4150.

Stevens et al., A promiscuous split intein with expanded protein engineering applications. Proc Natl Acad Sci U S A. Aug. 8, 2017; 114(32):8538-8543. doi: 10.1073/pnas.1701083114. Epub Jul. 24, 2017.

Stockwell et al., Probing the role of homomeric and heteromeric receptor interactions in TGF-beta signaling using small molecule dimerizers. Curr Biol. Jun. 18, 1998;8(13):761-70. doi: 10.1016/s0960-9822(98)70299-4.

Strecker et al., RNA-guided DNA insertion with CRISPR-associated transposases. Science. Jul. 5, 2019;365(6448):48-53. doi: 10.1126/science.aax9181. Epub Jun. 6, 2019.

Strutt et al., RNA-dependent RNA targeting by CRISPR-Cas9. Elife. Jan. 5, 2018;7:e32724. doi: 10.7554/eLife.32724.

Su et al., Human DNA polymerase ? has reverse transcriptase activity in cellular environments. J Biol Chem. Apr. 12, 2019;294(15):6073-6081. doi: 10.1074/jbc.RA119.007925. Epub Mar. 6, 2019.

Sun et al., The CRISPR/Cas9 system for gene editing and its potential application in pain research. Transl Periop & Pain Med. Aug. 3, 2016;1(3):22-33.

Surun et al., High Efficiency Gene Correction in Hematopoietic Cells by Donor-Template-Free CRISPR/Cas9 Genome Editing. Mol Ther Nucleic Acids. Mar. 2, 2018;10:1-8. doi: 10.1016/j.omtn.2017. 11.001. Epub Nov. 10, 2017.

Suzuki et al., In vivo genome editing via CRISPR/Cas9 mediated homology-independent targeted integration. Nature. Dec. 1, 2016;540(7631):144-149. doi: 10.1038/nature20565. Epub Nov. 16, 2016.

Suzuki et al., VCre/VloxP and SCre/SloxP: new site-specific recombination systems for genome engineering. Nucleic Acids Res. Apr. 2011;39(8):e49. doi: 10.1093/nar/gkq1280. Epub Feb. 1, 2011.

Tabebordbar et al., In vivo gene editing in dystrophic mouse muscle and muscle stem cells. Science. Jan. 22, 2016;351(6271):407-411. doi: 10.1126/science.aad5177. Epub Dec. 31, 2015.

Tahara et al., Potent and Selective Inhibitors of 8-Oxoguanine DNA Glycosylase. J Am Chem Soc. Feb. 14, 2018;140(6):2105-2114. doi: 10.1021/jacs.7b09316. Epub Feb. 5, 2018.

Tajiri et al., Functional cooperation of MutT, MutM and MutY proteins in preventing mutations caused by spontaneous oxidation of guanine nucleotide in *Escherichia coli*. Mutat Res. May 1995;336(3):257-67. doi: 10.1016/0921-8777(94)00062-b.

Tambunan et al., Vaccine Design for H5N1 Based on B- and T-cell Epitope Predictions. Bioinform Biol Insights. Apr. 28, 2016;10:27-35. doi: 10.4137/BBI.S38378.

Tang et al., Evaluation of Bioinformatic Programmes for the Analysis of Variants within Splice Site Consensus Regions. Adv Bioinformatics. 2016;2016:5614058. doi: 10.1155/2016/5614058. Epub May 24, 2016.

Tang et al., Rewritable multi-event analog recording in bacterial and mammalian cells. Science. Apr. 13, 2018;360(6385):eaap8992. doi: 10.1126/science.aap8992. Epub Feb. 15, 2018.

Tassabehji, Williams-Beuren syndrome: a challenge for genotype-phenotype correlations. Hum Mol Genet. Oct. 15, 2003;12 Spec No. 2:R229-37. doi: 10.1093/hmg/ddg299. Epub Sep. 2, 2003.

Taube et al., Reverse transcriptase of mouse mammary tumour virus: expression in bacteria, purification and biochemical characterization. Biochem J. Feb. 1, 1998;329 ( Pt 3)(Pt 3):579-87. doi: 10.1042/bj3290579. Erratum in: Biochem J Jun. 15, 1998;332(Pt 3):808.

Tee et al., Polishing the craft of genetic diversity creation in directed evolution. Biotechnol Adv. Dec. 2013;31(8):1707-21. doi: 10.1016/j.biotechadv.2013.08.021. Epub Sep. 6, 2013.

Telenti et al., The *Mycobacterium xenopi* GyrA protein splicing element: characterization of a minimal intein. J Bacteriol. Oct. 1997;179(20):6378-82. doi: 10.1128/jb.179.20.6378-6382.1997.

(56) References Cited

OTHER PUBLICATIONS

Telesnitsky et al., RNase H domain mutations affect the interaction between Moloney murine leukemia virus reverse transcriptase and its primer-template. Proc Natl Acad Sci U S A. Feb. 15, 1993;90(4):1276-80. doi: 10.1073/pnas.90.4.1276.

Thuronyi et al., Continuous evolution of base editors with expanded target compatibility and improved activity. Nat Biotechnol. Sep. 2019;37(9):1070-1079. doi: 10.1038/s41587-019-0193-0. Epub Jul. 22, 2019.

Thyagarajan et al., Creation of engineered human embryonic stem cell lines using phiC31 integrase. Stem Cells. Jan. 2008;26(1):119-26. doi: 10.1634/stemcells.2007-0283. Epub Oct. 25, 2007.

Tinland et al., The T-DNA-linked VirD2 protein contains two distinct functional nuclear localization signals. Proc Natl Acad Sci U S A. Aug. 15, 1992;89(16):7442-6. doi: 10.1073/pnas.89.16.7442.

Tom et al., Mechanism whereby proliferating cell nuclear antigen stimulates flap endonuclease 1. J Biol Chem. Apr. 7, 2000;275(14):10498-505. doi: 10.1074/jbc.275.14.10498.

Toor et al., Crystal structure of a self-spliced group II intron. Science. Apr. 4, 2008;320(5872):77-82. doi: 10.1126/science.1153803.

Torres et al., Non-integrative lentivirus drives high-frequency cre-mediated cassette exchange in human cells. PLoS One. 2011;6(5):e19794. doi: 10.1371/journal.pone.0019794. Epub May 23, 2011.

Townsend et al., Role of HFE in iron metabolism, hereditary haemochromatosis, anaemia of chronic disease, and secondary iron overload. Lancet. Mar. 2, 2002;359(9308):786-90. doi: 10.1016/S0140-6736(02)07885-6. Erratum in: Lancet Jul. 13, 2002;360(9327):176.

Tracewell et al., Directed enzyme evolution: climbing fitness peaks one amino acid at a time. Curr Opin Chem Biol. Feb. 2009;13(1):3-9. doi: 10.1016/j.cbpa.2009.01.017. Epub Feb. 25, 2009.

Tratschin et al., A human parvovirus, adeno-associated virus, as a eucaryotic vector: transient expression and encapsidation of the procaryotic gene for chloramphenicol acetyltransferase. Mol Cell Biol. Oct. 1984;4(10):2072-81. doi: 10.1128/mcb.4.10.2072.

Tratschin et al., Adeno-associated virus vector for high-frequency integration, expression, and rescue of genes in mammalian cells. Mol Cell Biol. Nov. 1985;5(11):3251-60. doi: 10.1128/mcb.5.11.3251.

Traxler et al., A genome-editing strategy to treat ?-hemoglobinopathies that recapitulates a mutation associated with a benign genetic condition. Nat Med. Sep. 2016;22(9):987-90. doi: 10.1038/nm.4170. Epub Aug. 15, 2016.

Trudeau et al., On the Potential Origins of the High Stability of Reconstructed Ancestral Proteins. Mol Biol Evol. Oct. 2016;33(10):2633-41. doi: 10.1093/molbev/msw138. Epub Jul. 12, 2016.

Tsai et al., CIRCLE-seq: a highly sensitive in vitro screen for genome-wide CRISPR-Cas9 nuclease off-targets. Nat Methods. Jun. 2017;14(6):607-614. doi: 10.1038/nmeth.4278. Epub May 1, 2017.

Tsang et al., Specialization of the DNA-cleaving activity of a group I ribozyme through in vitro evolution. J Mol Biol. Sep. 13, 1996;262(1):31-42. doi: 10.1006/jmbi.1996.0496.

Tsutakawa et al., Human flap endonuclease structures, DNA double-base flipping, and a unified understanding of the FEN1 superfamily. Cell. Apr. 15, 2011;145(2):198-211. doi: 10.1016/j.cell.2011.03.004.

Tycko et al., Pairwise library screen systematically interrogates *Staphylococcus aureus* Cas9 specificity in human cells. bioRxiv. doi: https://doi.org/10.1101/269399 Posted Feb. 22, 2018.

UniProt Consortium, UniProt: the universal protein knowledgebase. Nucleic Acids Res. Mar. 16, 2018;46(5):2699. doi: 10.1093/nar/gky092.

UniProtKB Submission; Accession No. F0NH53. May 3, 2011. 4 pages.

UniProtKB Submission; Accession No. F0NN87. May 3, 2011. 4 pages.

UniProTKB Submission; Accession No. G3ECR1.2. No Author Listed., Aug. 12, 2020, 8 pages.

UniProTKB Submission; Accession No. P04264. No Author Listed., Apr. 7, 2021. 12 pages.

UniProTKB Submission; Accession No. T0D7A2. Oct. 16, 2013. 10 pages.

UniProTKB Submission; Accession No. U2UMQ6. No Author Listed., Apr. 7, 2021, 11 pages.

Urasaki et al., Functional dissection of the Tol2 transposable element identified the minimal cis-sequence and a highly repetitive sequence in the subterminal region essential for transposition. Genetics. Oct. 2006;174(2):639-49. doi: 10.1534/genetics.106.060244. Epub Sep. 7, 2006.

Van Brunt et al., Molecular Farming: Transgenic Animals as Bioreactors. Biotechnology (N Y). 1988;6(10):1149-1154. doi: 10.1038/nbt1088-1149.

Van Overbeek et al., DNA Repair Profiling Reveals Nonrandom Outcomes at Cas9-Mediated Breaks. Mol Cell. Aug. 18, 2016;63(4):633-646. doi: 10.1016/j.molcel.2016.06.037. Epub Aug. 4, 2016.

Vik et al., Endonuclease V cleaves at inosines in RNA. Nat Commun. 2013;4:2271. doi: 10.1038/ncomms3271.

Voigt et al., Rational evolutionary design: the theory of in vitro protein evolution. Adv Protein Chem. 2000;55:79-160.

Wang et al., AID upmutants isolated using a high-throughput screen highlight the immunity/cancer balance limiting DNA deaminase activity. Nat Struct Mol Biol. Jul. 2009;16(7):769-76. doi: 10.1038/nsmb.1623. Epub Jun. 21, 2009.

Wang et al., Continuous directed evolutions of proteins with improved soluble expression. Nature Chemical Biology. Nat Publishing Group. Aug. 20, 2018; 14(10):972-980.

Wang et al., Evolution of new nonantibody proteins via iterative somatic hypermutation. Proc Natl Acad Sci U S A. Nov. 30, 2004;101(48):16745-9. Epub Nov. 19, 2004.

Wang et al., N(6)-methyladenosine Modulates Messenger RNA Translation Efficiency. Cell. Jun. 4, 2015;161(6):1388-99. doi: 10.1016/j.cell.2015.05.014.

Wang et al., Programming cells by multiplex genome engineering and accelerated evolution. Nature. Aug. 13, 2009;460(7257):894-8. Epub Jul. 26, 2009.

Wang et al., Reading RNA methylation codes through methyl-specific binding proteins. RNA Biol. 2014;11(6):669-72. doi: 10.4161/rna.28829. Epub Apr. 24, 2014.

Wang et al., *Staphylococcus aureus* protein SAUGI acts as a uracil-DNA glycosylase inhibitor. Nucleic Acids Res. Jan. 2014;42(2):1354-64. doi: 10.1093/nar/gkt964. Epub Oct. 22, 2013.

Watowich, The erythropoietin receptor: molecular structure and hematopoietic signaling pathways. J Investig Med. Oct. 2011;59(7):1067-72. doi: 10.2310/JIM.0b013e31820fb28c.

Wharton et al., A new-specificity mutant of 434 repressor that defines an amino acid-base pair contact. Nature. Apr. 30-May 6, 1987;326(6116):888-91.

Wharton et al., Changing the binding specificity of a repressor by redesigning an alpha-helix. Nature. Aug. 15-21, 1985;316(6029):601-5.

Wheeler et al., The thermostability and specificity of ancient proteins. Curr Opin Struct Biol. Jun. 2016;38:37-43. doi: 10.1016/j.sbi.2016.05.015. Epub Jun. 9, 2016.

Wienert et al., KLF1 drives the expression of fetal hemoglobin in British HPFH. Blood. Aug. 10, 2017;130(6):803-807. doi: 10.1182/blood-2017-02-767400. Epub Jun. 28, 2017.

Williams et al., Assessing the accuracy of ancestral protein reconstruction methods. PLoS Comput Biol. Jun. 23, 2006;2(6):e69. doi: 10.1371/journal.pcbi.0020069. Epub Jun. 23, 2006.

Wilson et al., Formation of infectious hybrid virions with gibbon ape leukemia virus and human T-cell leukemia virus retroviral envelope glycoproteins and the gag and pol proteins of Moloney murine leukemia virus. J Virol. May 1989;63(5):2374-8. doi: 10.1128/JVI.63.5.2374-2378.1989.

Wilson et al., Kinase dynamics. Using ancient protein kinases to unravel a modern cancer drug's mechanism. Science. Feb. 20, 2015;347(6224):882-6. doi: 10.1126/science.aaa1823.

(56) References Cited

OTHER PUBLICATIONS

Winoto et al., A novel, inducible and T cell-specific enhancer located at the 3' end of the T cell receptor alpha locus. EMBO J. Mar. 1989;8(3):729-33.

Wong et al., A statistical analysis of random mutagenesis methods used for directed protein evolution. J Mol Biol. Jan. 27, 2006;355(4):858-71. Epub Nov. 17, 2005.

Wong et al., The Diversity Challenge in Directed Protein Evolution. Comb Chem High Throughput Screen. May 2006;9(4):271-88.

Wright et al., Continuous in vitro evolution of catalytic function. Science. Apr. 25, 1997;276(5312):614-7.

Wright et al., Rational design of a split-Cas9 enzyme complex. Proc Natl Acad Sci U S A. Mar. 10, 2015;112(10):2984-9. doi: 10.1073/pnas.1501698112. Epub Feb. 23, 2015.

Wu et al., Protein trans-splicing by a split intein encoded in a split DnaE gene of Synechocystis sp. PCC6803. Proc Natl Acad Sci U S A. Aug. 4, 1998;95(16):9226-31. doi: 10.1073/pnas.95.16.9226.

Xiang et al., RNA m6A methylation regulates the ultraviolet-induced DNA damage response. Nature. Mar. 23, 2017;543(7646):573-576. doi: 10.1038/nature21671. Epub Mar. 15, 2017.

Xiao et al., Nuclear m(6)A Reader YTHDC1 Regulates mRNA Splicing. Mol Cell. Feb. 18, 2016;61(4):507-519. doi: 10.1016/j.molcel.2016.01.012. Epub Feb. 11, 2016.

Xiong et al., Origin and evolution of retroelements based upon their reverse transcriptase sequences. EMBO J. Oct. 1990;9(10):3353-62.

Xu et al., Chemical ligation of folded recombinant proteins: segmental isotopic labeling of domains for NMR studies. Proc Natl Acad Sci U S A. Jan. 19, 1999;96(2):388-93. doi: 10.1073/pnas.96.2.388.

Xu et al., Accuracy and efficiency define Bxb1 integrase as the best of fifteen candidate serine recombinases for the integration of DNA into the human genome. BMC Biotechnol. Oct. 20, 2013;13:87. doi: 10.1186/1472-6750-13-87.

Xu et al., Protein splicing: an analysis of the branched intermediate and its resolution by succinimide formation. EMBO J. Dec. 1, 1994;13(23):5517-22.

Xu et al., Structures of human ALKBH5 demethylase reveal a unique binding mode for specific single-stranded N6-methyladenosine RNA demethylation. J Biol Chem. Jun. 20, 2014;289(25):17299-311. doi: 10.1074/jbc.M114.550350. Epub Apr. 28, 2014.

Xu et al., The mechanism of protein splicing and its modulation by mutation. EMBO J. Oct. 1, 1996;15(19):5146-53.

Yamamoto et al., The ons and offs of inducible transgenic technology: a review. Neurobiol Dis. Dec. 2001;8(6):923-32.

Yan et al., Cas13d Is a Compact RNA-Targeting Type VI CRISPR Effector Positively Modulated by a WYL-Domain-Containing Accessory Protein. Mol Cell. Apr. 19, 2018;70(2):327-339.e5. doi: 10.1016/j.molcel.2018.02.028. Epub Mar. 15, 2018.

Yang et al., Construction of an integration-proficient vector based on the site-specific recombination mechanism of enterococcal temperate phage phiFC1. J Bacteriol. Apr. 2002;184(7):1859-64. doi: 10.1128/jb.184.7.1859-1864.2002.

Yang et al., Increasing targeting scope of adenosine base editors in mouse and rat embryos through fusion of TadA deaminase with Cas9 variants. Protein Cell. Sep. 2018;9(9):814-819. doi: 10.1007/s13238-018-0568-x.

Yang et al., One-step generation of mice carrying reporter and conditional alleles by CRISPR/Cas-mediated genome engineering. Cell. Sep. 12, 2013;154(6):1370-9. doi: 10.1016/j.cell.2013.08.022. Epub Aug. 29, 2013.

Yang et al., Permanent genetic memory with >1-byte capacity. Nat Methods. Dec. 2014;11(12):1261-6. doi: 10.1038/nmeth.3147. Epub Oct. 26, 2014.

Yang et al., Small-molecule control of insulin and PDGF receptor signaling and the role of membrane attachment. CurrBiol. Jan. 1, 1998;8(1):11-8. doi: 10.1016/s0960-9822(98)70015-6.

Yang, PAML 4: phylogenetic analysis by maximum likelihood. Mol Biol Evol. Aug. 2007;24(8):1586-91. doi: 10.1093/molbev/msm088. Epub May 4, 2007.

Yang, Phylogenetic Analysis by Maximum Likelihood (PAML). //abacus.gene.ucl.ac.uk/software/paml.html Last accessed Apr. 28, 2021.

Yasui et al., Miscoding Properties of 2'-Deoxyinosine, a Nitric Oxide-Derived DNA Adduct, during Translesion Synthesis Catalyzed by Human DNA Polymerases. J Molec Biol. Apr. 4, 2008;377(4):1015-23.

Yasukawa et al., Characterization of Moloney murine leukaemia virus/avian myeloblastosis virus chimeric reverse transcriptases. J Biochem. Mar. 2009;145(3):315-24. doi: 10.1093/jb/mvn166. Epub Dec. 6, 2008.

Yu et al., Circular permutation: a different way to engineer enzyme structure and function. Trends Biotechnol. Jan. 2011;29(1):18-25. doi: 10.1016/j.tibtech.2010.10.004. Epub Nov. 17, 2010.

Yu et al., Liposome-mediated in vivo E1A gene transfer suppressed dissemination of ovarian cancer cells that overexpress HER-2/neu. Oncogene. Oct. 5, 1995;11(7):1383-8.

Yu et al., Small molecules enhance CRISPR genome editing in pluripotent stem cells. Cell Stem Cell. Feb. 5, 2015;16(2): 142-7. doi: 10.1016/j.stem.2015.01.003.

Yu et al., Synthesis-dependent microhomology-mediated end joining accounts for multiple types of repair junctions. Nucleic Acids Res. Sep. 2010;38(17):5706-17. doi: 10.1093/nar/gkq379. Epub May 11, 2010.

Zakas et al., Enhancing the pharmaceutical properties of protein drugs by ancestral sequence reconstruction. Nat Biotechnol. Jan. 2017;35(1):35-37. doi: 10.1038/nbt.3677. Epub Sep. 26, 2016.

Zalatan et al., Engineering complex synthetic transcriptional programs with CRISPR RNA scaffolds. Cell. Jan. 15, 2015;160(1-2):339-50. doi: 10.1016/j.cell.2014.11.052. Epub Dec. 18, 2014.

Zettler et al., The naturally split Npu DnaE intein exhibits an extraordinarily high rate in the protein trans-splicing reaction. FEBS Lett. Mar. 4, 2009;583(5):909-14. doi: 10.1016/j.febslet.2009.02.003. Epub Feb. 10, 2009.

Zhang et al., Circular intronic long noncoding RNAs. Mol Cell. Sep. 26, 2013;51(6):792-806. doi: 10.1016/j.molcel.2013.08.017. Epub Sep. 12, 2013.

Zhang et al., Copy number variation in human health, disease, and evolution. Annu Rev Genomics Hum Genet. 2009;10:451-81. doi: 10.1146/annurev.genom.9.081307.164217.

Zhang et al., II-Clamp-mediated cysteine conjugation. Nat Chem. Feb. 2016;8(2):120-8. doi: 10.1038/nchem.2413. Epub Dec. 21, 2015.

Zhao et al., An ultraprocessive, accurate reverse transcriptase encoded by a metazoan group II intron. RNA. Feb. 2018;24(2):183-195. doi: 10.1261/ma.063479.117. Epub Nov. 6, 2017.

Zhao et al., Crystal structures of a group II intron maturase reveal a missing link in spliceosome evolution. Nat Struct Mol Biol. Jun. 2016;23(6):558-65. doi: 10.1038/nsmb.3224. Epub May 2, 2016.

Zhao et al., Post-transcriptional gene regulation by mRNA modifications. Nat Rev Mol Cell Biol. Jan. 2017;18(1):31-42. doi: 10.1038/nrm.2016.132. Epub Nov. 3, 2016.

Zheng et al., ALKBH5 is a mammalian RNA demethylase that impacts RNA metabolism and mouse fertility. Mol Cell. Jan. 10, 2013;49(1):18-29. doi: 10.1016/j.molcel.2012.10.015. Epub Nov. 21, 2012.

Zheng et al., Highly efficient base editing in bacteria using a Cas9-cytidine deaminase fusion. CommunBiol. Apr. 19, 2018;1:32. doi: 10.1038/s42003-018-0035-5.

Zhou et al., Dynamic m(6)A mRNA methylation directs translational control of heat shock response. Nature. Oct. 22, 2015;526(7574):591-4. doi: 10.1038/nature15377. Epub Oct. 12, 2015.

Zhou et al., Protective VI27 prion variant prevents prion disease by interrupting the formation of dimer and fibril from molecular dynamics simulations. Sci Rep. Feb. 24, 2016;6:21804. doi: 10.1038/srep21804.

Zimmerly et al., An Unexplored Diversity of Reverse Transcriptases in Bacteria. Microbiol Spectr. Apr. 2015;3(2):MDNA3-0058-2014. doi: 10.1128/microbiolspec.MDNA3-0058-2014.

Zlmmerly et al., Group II intron mobility occurs by target DNA-primed reverse transcription. Cell. Aug. 25, 1995;82(4):545-54. doi: 10.1016/0092-8674(95)90027-6.

(56) References Cited

OTHER PUBLICATIONS

Zufferey et al., Woodchuck hepatitis virus posttranscriptional regulatory element enhances expression of transgenes delivered by retroviral vectors. J Virol. Apr. 1999;73(4):2886-92. doi: 10.1128/JVI.73.4.2886-2892.1999.

Zuker et al., Optimal computer folding of large RNA sequences using thermodynamics and auxiliary information. Nucleic Acids Res. Jan. 10, 1981;9(1):133-48. doi: 10.1093/nar/9.1.133.

Zuo et al., Cytosine base editor generates substantial off-target single-nucleotide variants in mouse embryos. Science. Apr. 19, 2019;364(6437):289-292. doi: 10.1126/science.aav9973. Epub Feb. 28, 2019.

Atkins et al., Ribosomal frameshifting and transcriptional slippage: From genetic steganography and cryptography to adventitious use. Nucleic Acids Res. Sep. 6, 2016;44(15):7007-78. doi: 10.1093/nar/gkw530. Epub Jul. 19, 2016.

Autieri et al., IRT-1, a novel interferon-gamma-responsive transcript encoding a growth-suppressing basic leucine zipper protein. J Biol Chem. Jun. 12, 1998;273(24):14731-7. doi: 10.1074/jbc.273.24.14731.

Avidan et al., The processivity and fidelity of DNA synthesis exhibited by the reverse transcriptase of bovine leukemia virus. Eur J Biochem. Feb. 2002;269(3):859-67. doi: 10.1046/j.0014-2956.2001.02719.x.

Babacic et al., CRISPR-cas gene-editing as plausible treatment of neuromuscular and nucleotide-repeat-expansion diseases: a systematic review. PLoS One. Feb. 22, 2019;14(2):e0212198. doi: 10.1371/journal.pone.0212198.
Badran et al., Continuous evolution of Bacillus thuringiensis toxins overcomes insect resistance. Nature. May 5, 2016;533(7601):58-63. doi: 10.1038/nature17938. Epub Apr. 27, 2016.
Badran et al., Development of potent in vivo mutagenesis plasmids with broad mutational spectra. Nat Commun. Oct. 7, 2015;6:8425. doi: 10.1038/ncomms9425.
Bae et al., Microhomology-based choice of Cas9 nuclease target sites. Nat Methods. Jul. 2014;11(7):705-6. doi: 10.1038/nmeth.3015.
Bagyinszky et al., Characterization of mutations in PRNP (prion) gene and their possible roles in neurodegenerative diseases. Neuropsychiatr Dis Treat. Aug. 14, 2018;14:2067-2085. doi: 10.2147/NDT.S165445.
Balakrishnan et al., Flap endonuclease 1. Annu Rev Biochem. 2013;82:119-38. doi: 10.1146/annurev-biochem-072511-122603. Epub Feb. 28, 2013.
Baranauskas et al., Generation and characterization of new highly thermostable and processive M-MuLV reverse transcriptase variants. Protein Eng Des Sel. Oct. 2012;25(10):657-68. doi: 10.1093/protein/gzs034. Epub Jun. 12, 2012.
Bartlett et al., Efficient expression of protein coding genes from the murine U1 small nuclear RNA promoters. Proc Natl Acad Sci U S A. Aug. 20, 1996;93(17):8852-7. doi: 10.1073/pnas.93.17.8852.
Bartosovic et al., N6-methyladenosine demethylase FTO targets pre-mRNAs and regulates alternative splicing and 3'-end processing. Nucleic Acids Res. Nov. 2, 2017;45(19):11356-11370. doi: 10.1093/nar/gkx778.
Basturea et al., Substrate specificity and properties of the *Escherichia coli* 16S rRNA methyltransferase, RsmE. RNA. Nov. 2007;13(11):1969-76. doi: 10.1261/rna.700507. Epub Sep. 13, 2007.
Bebenek et al., Error-prone polymerization by HIV-1 reverse transcriptase. Contribution of template-primer misalignment, miscoding, and termination probability to mutational hot spots. J Biol Chem. May 15, 1993;268(14):10324-34.
Belshaw et al., Controlling programmed cell death with a cyclophilin-cyclosporin-based chemical inducer of dimerization. Chem Biol. Sep. 1996;3(9):731-8. doi: 10.1016/s1074-5521(96)90249-5.
U.S. Appl. No. 14/234,031, filed Mar. 24, 2014, Liu et al.
U.S. Appl. No. 14/320,271, filed Jun. 30, 2014, Liu et al.
U.S. Appl. No. 16/441,751, filed Jun. 14, 2019, Liu et al.
U.S. Appl. No. 14/320,519, filed Jun. 30, 2014, Liu et al.
U.S. Appl. No. 14/913,458, filed Feb. 22, 2016, Liu et al.
U.S. Appl. No. 16/266,937, filed Feb. 4, 2019, Liu et al.
U.S. Appl. No. 14/320,370, filed Jun. 30, 2014, Liu et al.
U.S. Appl. No. 14/320,413, filed Jun. 30, 2014, Liu et al.
U.S. Appl. No. 14/874,123, filed Oct. 2, 2015, Liu et al.
U.S. Appl. No. 14/911,117, filed Feb. 9, 2016, Liu et al.
U.S. Appl. No. 17/160,329, filed Jan. 27, 2021, Liu et al.
U.S. Appl. No. 14/462,163, filed Aug. 18, 2014, Liu et al.
U.S. Appl. No. 14/462,189, filed Aug. 18, 2014, Liu et al.
U.S. Appl. No. 14/916,679, filed Mar. 4, 2016, Liu et al.
U.S. Appl. No. 16/860,639, filed Apr. 28, 2020, Liu et al.
U.S. Appl. No. 14/320,498, filed Jun. 30, 2014, Liu et al.
U.S. Appl. No. 14/320,467, filed Jun. 30, 2014, Liu et al.
U.S. Appl. No. 14/916,681, filed Mar. 4, 2016, Liu et al.
U.S. Appl. No. 17/103,233, filed Nov. 24, 2020, Liu et al.
U.S. Appl. No. 14/326,329, filed Jul. 8, 2014, Liu et al.
U.S. Appl. No. 14/326,340, filed Jul. 8, 2014, Liu et al.
U.S. Appl. No. 14/326,361, filed Jul. 8, 2014, Liu et al.
U.S. Appl. No. 14/916,683, filed Mar. 4, 2016, Liu et al.
U.S. Appl. No. 16/796,323, filed Feb. 20, 2020, Liu et al.
U.S. Appl. No. 14/325,815, filed Jul. 8, 2014, Liu et al.
U.S. Appl. No. 14/326,109, filed Jul. 8, 2014, Liu et al.
U.S. Appl. No. 14/326,140, filed Jul. 8, 2014, Liu et al.
U.S. Appl. No. 14/326,269, filed Jul. 8, 2014, Liu et al.
U.S. Appl. No. 14/326,290, filed Jul. 8, 2014, Liu et al.
U.S. Appl. No. 14/326,318, filed Jul. 8, 2014, Liu et al.
U.S. Appl. No. 14/326,303, filed Jul. 8, 2014, Liu et al.
U.S. Appl. No. 15/103,608, filed Jun. 10, 2016, Liu et al.
U.S. Appl. No. 16/374,634, filed Apr. 3, 2019, Liu et al.
U.S. Appl. No. 15/329,925, filed Jan. 27, 2017, Liu et al.
U.S. Appl. No. 16/132,276, filed Sep. 14, 2018, Liu et al.
U.S. Appl. No. 16/888,646, filed May 29, 2020, Liu et al.
U.S. Appl. No. 14/529,010, filed Oct. 30, 2014, Liu et al.
U.S. Appl. No. 15/958,721, filed Apr. 20, 2018, Liu et al.
U.S. Appl. No. 17/130,812, filed Dec. 22, 2020, Liu et al.
U.S. Appl. No. 15/331,852, filed Oct. 22, 2016, Liu et al.
U.S. Appl. No. 15/770,076, filed Apr. 20, 2018, Liu et al.
U.S. Appl. No. 16/327,744, filed Feb. 22, 2019, Maianti et al.
U.S. Appl. No. 15/852,891, filed Dec. 22, 2017, Maianti et al.
U.S. Appl. No. 16/926,436, filed Jul. 10, 2020, Maianti et al.
U.S. Appl. No. 15/852,526, filed Dec. 22, 2017, Maianti et al.
U.S. Appl. No. 16/492,534, filed Sep. 9, 2019, Liu et al.
U.S. Appl. No. 16/324,476, filed Feb. 8, 2019, Liu et al.
U.S. Appl. No. 15/791,085, filed Oct. 23, 2017, Liu et al.
U.S. Appl. No. 16/143,370, filed Sep. 26, 2018, Liu et al.
U.S. Appl. No. 17/148,059, filed Jan. 13, 2021, Liu et al.
U.S. Appl. No. 16/492,548, filed Sep. 9, 2019, Maianti et al.
U.S. Appl. No. 15/784,033, filed Oct. 13, 2017, Liu et al.
U.S. Appl. No. 16/492,553, filed Sep. 9, 2019, Liu et al.
U.S. Appl. No. 15/934,945, filed Mar. 23, 2018, Liu et al.
U.S. Appl. No. 16/643,376, filed Feb. 28, 2020, Liu et al.
U.S. Appl. No. 16/612,988, filed Nov. 12, 2019, Liu et al.
U.S. Appl. No. 16/634,405, filed Jan. 27, 2020, Liu et al.
U.S. Appl. No. 16/976,047, filed Aug. 26, 2020, Liu et al.
U.S. Appl. No. 17/289,665, filed Apr. 28, 2021, Liu et al.
U.S. Appl. No. 16/756,432, filed Apr. 15, 2020, Liu et al.
U.S. Appl. No. 16/772,747, filed Jun. 12, 2020, Shen et al.
U.S. Appl. No. 17/057,398, filed Nov. 20, 2020, Liu et al.
U.S. Appl. No. 17/259,147, filed Jan. 8, 2021, Liu et al.
U.S. Appl. No. 17/270,396, filed Feb. 22, 2021, Liu et al.
U.S. Appl. No. 17/273,688, filed Mar. 4, 2021, Liu et al.
U.S. Appl. No. 17/288,504, filed Apr. 23, 2021, Liu et al.
U.S. Appl. No. 17/219,590, filed Mar. 31, 2021, Liu et al.
U.S. Appl. No. 17/219,635, filed Mar. 31, 2021, Liu et al.
U.S. Appl. No. 17/219,672, filed Mar. 31, 2021, Liu et al.

* cited by examiner

EMX1:          GAGTC$_5$C$_8$GAGCAGAAGAAGAAGGG
FANCF:         GGAATC$_6$C$_7$C$_8$TTC$_{11}$TGCAGCACCTGG
HEK293 site 2: GAAC$_4$AC$_6$AAAGCATAGACTGCGGG
HEK293 site 3: GGCC$_4$C$_5$AGACTGAGCACGTGATGG
HEK293 site 4: GGCAC$_5$TGCGGCTGGAGGTCCGGG
RNF2:          GTC$_3$ATC$_6$TTAGTC$_{12}$ATTACCTGAGG

APOE4 Cys112Arg:    5'-GGAGGACGTGC$_{11}$GCGGCCGCCTGG
APOE4 Cys158Arg:    5'-GAAGC$_5$GCCTGGCAGTGTACCAGG
CTNNB1 Thr41Ala:    5'-CTGTGGC$_7$AGTGGCACCAGAATGG
HRAS Gln61Arg:      5'-CCTCCC$_6$GGCCGGCGGTATCCAGG
p53 Tyr163Cys:      5'-GCTTGC$_6$AGATGGCCATGGCGCGG
p53 Tyr236Cys:      5'-ACACATGC$_8$AGTTGTAGTGGATGG
p53 Asn239Asp:      5'-TGTC$_4$ACACATGTAGTTGTAGTGG

FIGURE 16A

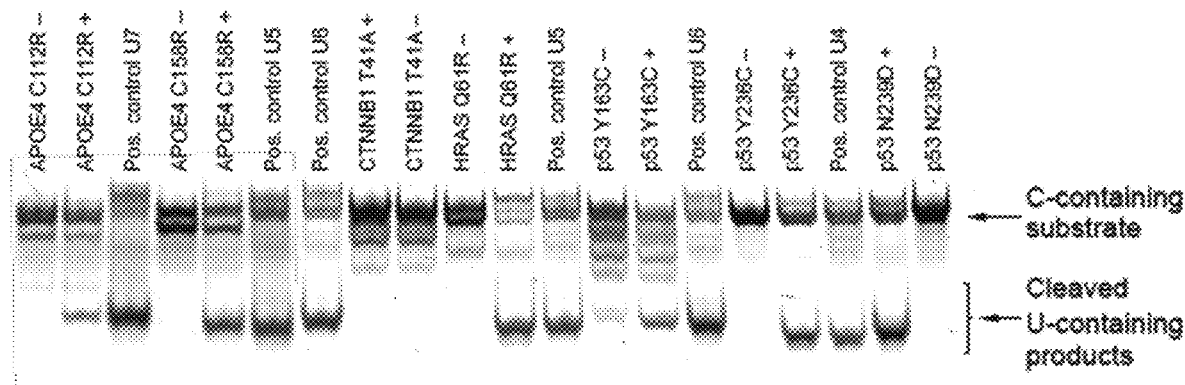

FIGURE 16B

Protospacer and PAM sequence:   5'-TTCCCCCCCCGATTTATTTATGG-3'

| Sequence | % of total reads |
|----------|------------------|
| CCCCCCCC | 62.4 |
| TTTTTTCC | 18.2 |
| TTTTTTTC | 13.4 |
| TTTTTTTT | 3.3 |
| TCCCCCCC | 0.8 |
| CCCCTTCC | 0.3 |
| CCGTTTCC | 0.3 |
| TTTTTCCC | 0.3 |
| CCCCTCCC | 0.3 |

FIGURE 17

EMX1:          GAGTC$_5$C$_6$GAGCAGAAGAAGAAGGG
FANCF:         GGAATC$_6$C$_7$C$_8$TTC$_{11}$TGCAGCACCTGG
HEK293 site 2: GAAC$_4$AC$_6$AAAGCATAGACTGCGGG
HEK293 site 3: GGCC$_4$C$_5$AGACTGAGCACGTGATGG
HEK293 site 4: GGCAC$_5$TGCGGCTGGAGGTCCGGG
RNF2:          GTC$_3$ATC$_6$TTAGTCATTACCTGAGG

FIGURE 18A

| EMX1 | C$_5$ | C$_6$ |
|---|---|---|
| NBE1 | 6.2% | 6.5% |
| NBE1 + UGI | 9.7% | 10.1% |
| NBE2 | 8.0% | 8.7% |

FIGURE 18B

| FANCF | C$_6$ | C$_7$ | C$_8$ | C$_{10}$ |
|---|---|---|---|---|
| NBE1 | 3.7% | 3.2% | 3.4% | 2.4% |
| NBE1 + UGI | 7.5% | 7.6% | 7.5% | 1.6% |
| NBE2 | 4.7% | 4.6% | 4.6% | 0.8% |

FIGURE 18C

| HEK293 site 2 | C$_4$ | C$_6$ |
|---|---|---|
| NBE1 | 0.4% | 0.4% |
| NBE1 + UGI | 1.6% | 2.6% |
| NBE2 | 3.4% | 5.9% |

FIGURE 18D

| HEK293 site 3 | $C_4$ | $C_6$ |
|---|---|---|
| NBE1 | 2.0% | 1.9% |
| NBE1 + UGI | 6.5% | 6.7% |
| NBE2 | 10.0% | 12.5% |

FIGURE 18E

| HEK293 site 4 | $C_5$ |
|---|---|
| NBE1 | 1.4% |
| NBE1 + UGI | 5.4% |
| NBE2 | 8.2% |

FIGURE 18F

| RNF2 | $C_3$ | $C_6$ |
|---|---|---|
| NBE1 | 0.7% | 1.4% |
| NBE1 + UGI | 3.4% | 3.9% |
| NBE2 | 2.5% | 3.7% |

FIGURE 18G

| Non-protospacer Cs | C | T |
|---|---|---|
| untreated | 99.93% | 0.03% |
| NBE1 | 99.95% | 0.03% |
| NBE1 + UGI | 99.91% | 0.06% |
| NBE2 | 99.92% | 0.04% |

| EMX1 off target 3 | G | A | G | C | C | G | A | C | A | G | A | A | A | G | A | C | G | |
|---|---|---|---|---|---|---|---|---|---|---|---|---|---|---|---|---|---|---|
| untreated | | | | 0.0 | 0.0 | | | 0.0 | | | | | | | | 0.0 | | 700 |
| NBE1 | | | | 0.0 | 0.0 | | | 0.0 | | | | | | | | 0.0 | | |
| NBE2 | | | | 0.8 | 0.9 | | | 0.0 | | | | | | | | 0.0 | | |
| NBE3 | | | | 5.1 | 5.2 | | | 0.0 | | | | | | | | 0.0 | | |

| EMX1 off target 4 | G | A | G | T | C | A | G | C | A | G | A | A | G | A | A | G | A | G |
|---|---|---|---|---|---|---|---|---|---|---|---|---|---|---|---|---|---|---|
| untreated | | | | | 0.0 | | | 0.0 | | | | | | | | | | 390 |
| NBE1 | | | | | 0.2 | | | 0.0 | | | | | | | | | | |
| NBE2 | | | | | 0.5 | | | 0.5 | | | | | | | | | | |
| NBE3 | | | | | 2.2 | | | 0.0 | | | | | | | | | | |

| EMX1 off target 8 | G | A | G | T | C | C | G | A | A | G | G | A | G | A | A | A | A | G |
|---|---|---|---|---|---|---|---|---|---|---|---|---|---|---|---|---|---|---|
| untreated | | | | | 0.0 | 0.0 | | | | | | | | | | | | 210 |
| NBE1 | | | | | 0.1 | 0.1 | | | | | | | | | | | | |
| NBE2 | | | | | 0.2 | 0.3 | | | | | | | | | | | | |
| NBE3 | | | | | 1.0 | 1.0 | | | | | | | | | | | | |

| Non-protospacer Cs | C (%) | T (%) |
|---|---|---|
| untreated | 99.94 | 0.04 |
| NBE1 | 99.92 | 0.05 |
| NBE2 | 99.92 | 0.05 |
| NBE3 | 99.94 | 0.03 |

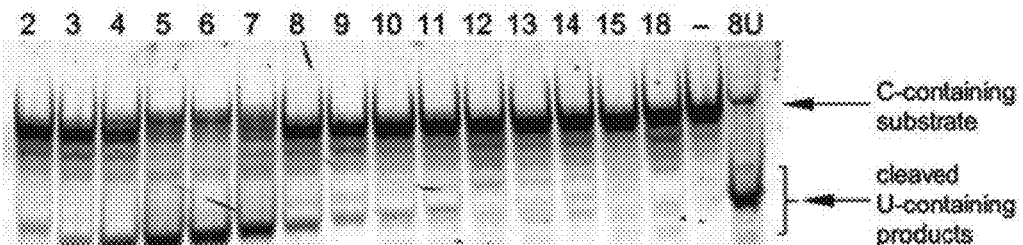
FIGURE 36D
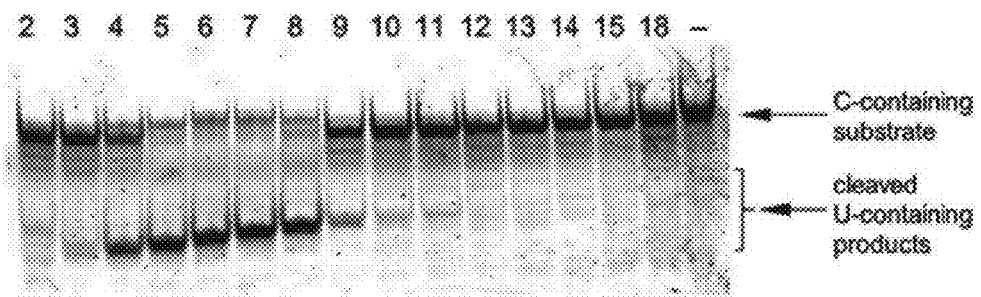
FIGURE 36E
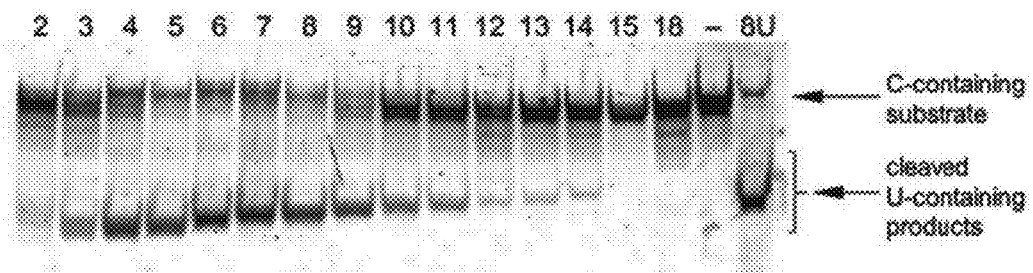
FIGURE 36F
EMX1:            GAGTC$_5$C$_6$GAGCAGAAGAAGAAGGG
FANCF:           GGAATC$_6$C$_7$C$_8$TTC$_{11}$TGCAGCACCTGG
HEK293 site 2:   GAAC$_4$AC$_6$AAAGCATAGACTGCGGG
HEK293 site 3:   GGCC$_4$C$_5$AGACTGAGCACGTGATGG
HEK293 site 4:   GGCAC$_5$TGCGGCTGGAGGTCCGGG
RNF2:            GTC$_3$ATC$_6$TTAGTC$_{12}$ATTACCTGAGG
FIGURE 37A

FIGURE 37B

| non-protospacer C/Gs | average C/G (%) | average T/A (%) | lowest T/A (%) | highest T/A (%) |
|---|---|---|---|---|
| untreated | 99.95 ± 0.14 | 0.02 ± 0.02 | 0.00 | 2.44 |
| BE1 | 99.95 ± 0.24 | 0.03 ± 0.03 | 0.00 | 1.64 |
| BE2 | 99.95 ± 0.13 | 0.03 ± 0.03 | 0.00 | 1.92 |
| BE3 | 99.97 ± 0.09 | 0.02 ± 0.02 | 0.00 | 2.52 |

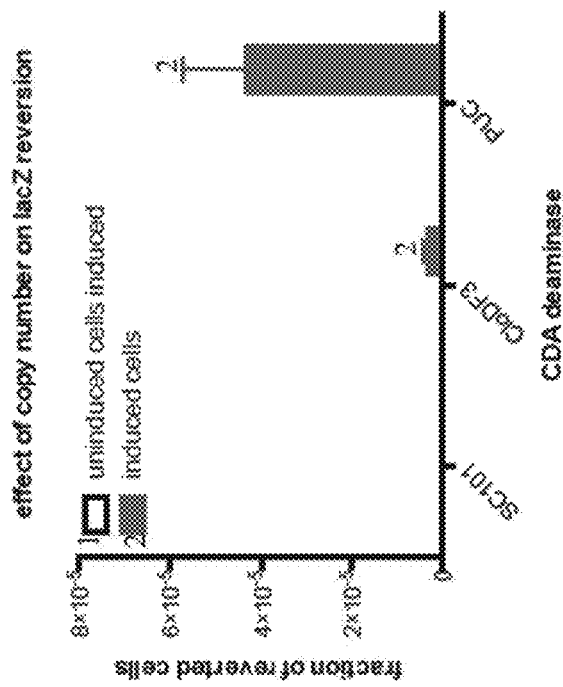
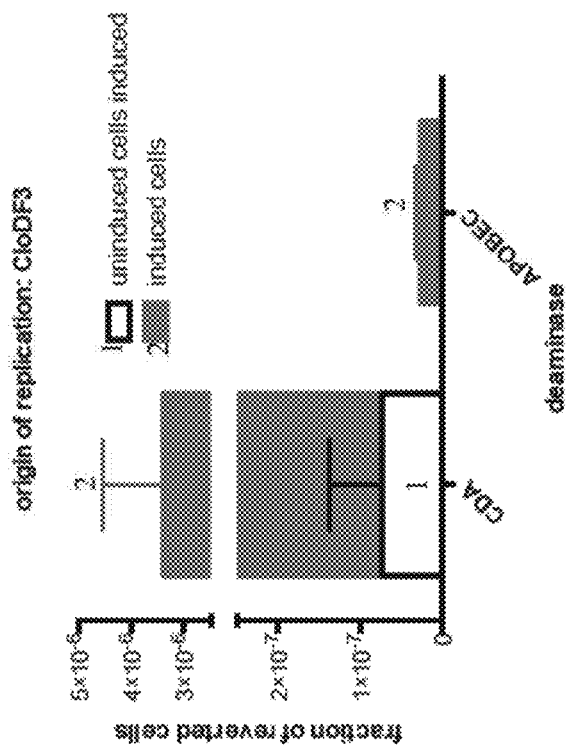
FIGURE 49 (CONTINUED)

Row 1: CDA-dCas9 + selection plasmid (chlor$^S$)

Row 2: CDA-dCas9 + pos. control selection (chlor$^R$)

Row 3: rAPOBEC-dCas9 + selection plasmid (chlor$^S$)

Row 4: rAPOBEC-dCas9 + pos. control selection (chlor$^R$)

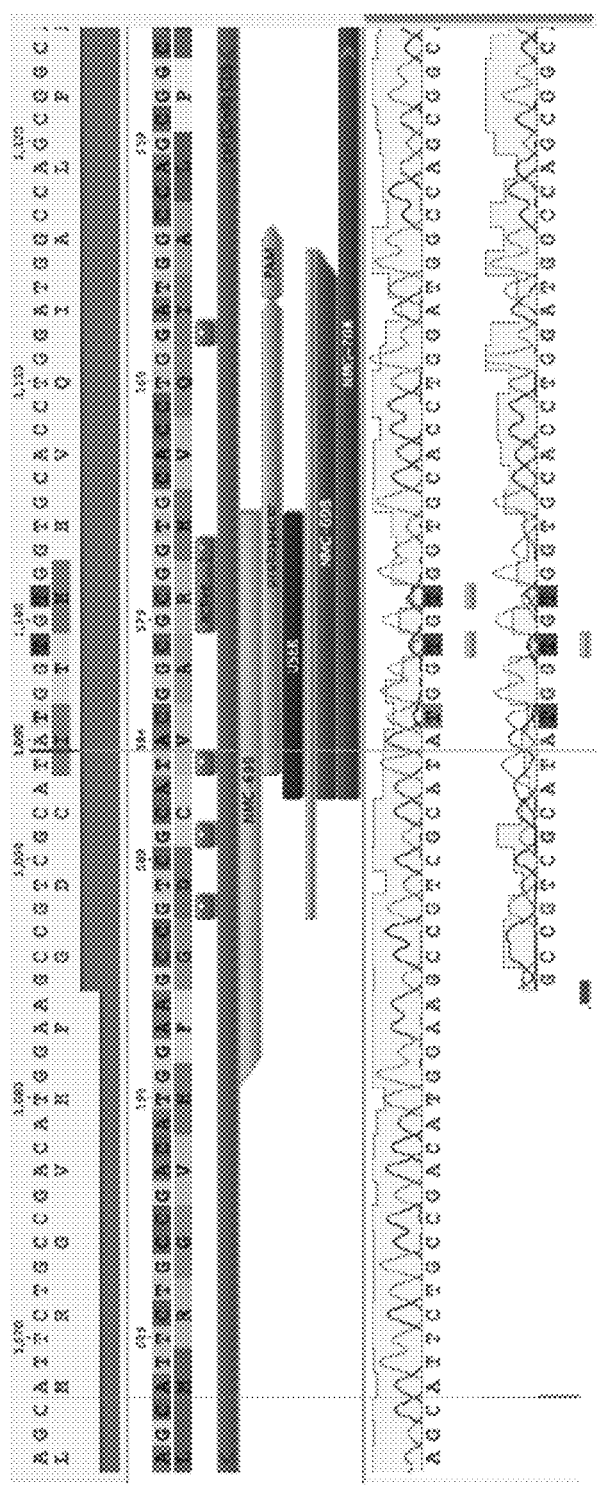
FIGURE S3B

FIGURE 56

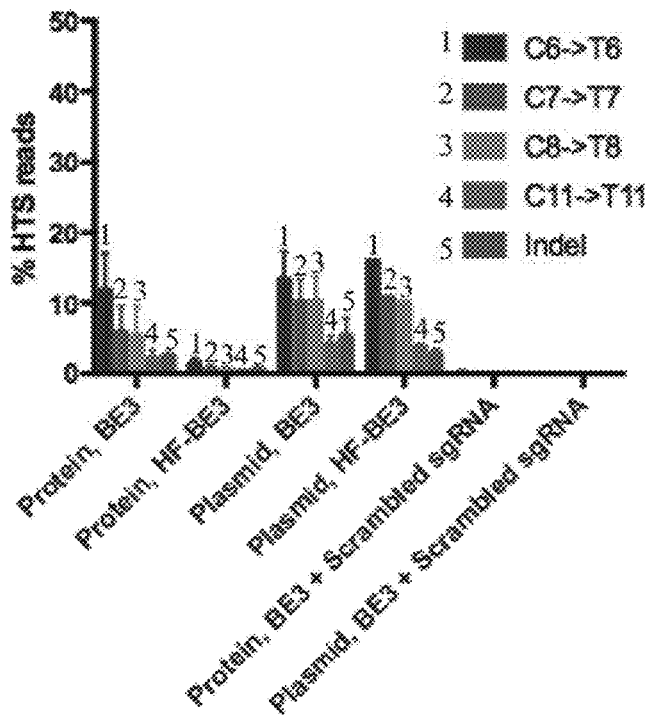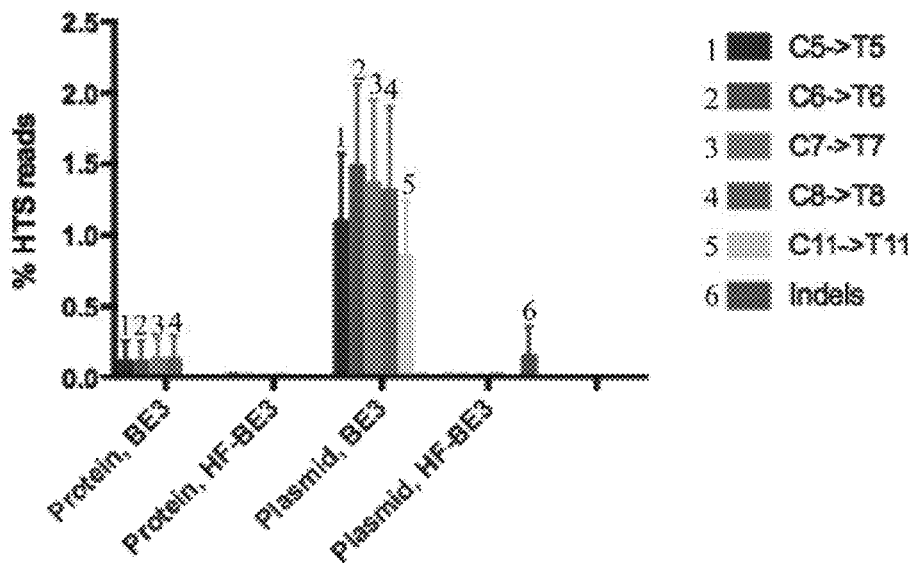
FIGURE 78

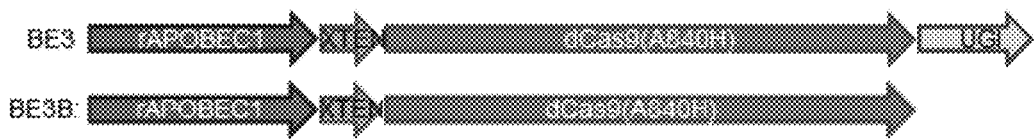
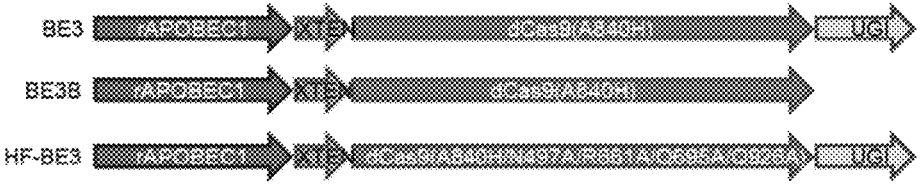
FIGURE 91

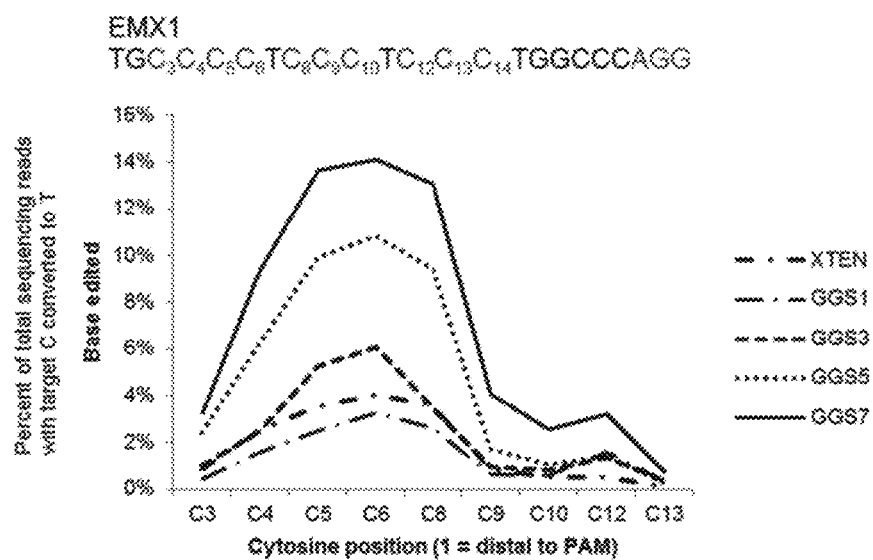
FIGURE 96
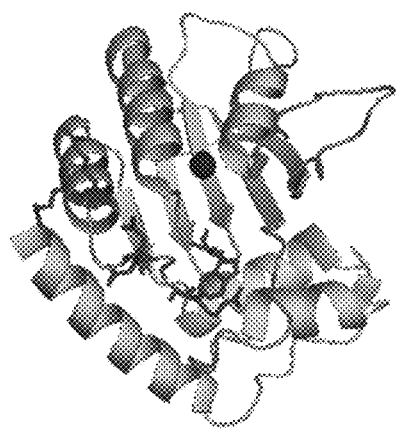
FIGURE 97A
| APOBEC1 mutation | APOBEC3G mutation | Reference |
|---|---|---|
| R126A | R320A | #9,10 |
| R126E | R320E | #9,10 |
| W90A | W285A | #9,10 |
| W90Y | W285Y | This work |
| R132E | R326E | This work |
FIGURE 97B

NUCLEOBASE EDITORS AND USES THEREOF

RELATED APPLICATIONS

This application is a continuation of and claims priority under 35 U.S.C. § 120 to international PCT Application, PCT/US2016/058344, filed Oct. 22, 2016, and is a continuation of and claims priority under 35 U.S.C. § 120 to U.S. Application, U.S. Ser. No. 15/331,852, filed Oct. 22, 2016, which claims priority under 35 U.S.C. § 119(e) to U.S. provisional patent applications, U.S. Ser. No. 62/245,828 filed Oct. 23, 2015, U.S. Ser. No. 62/279,346 filed Jan. 15, 2016, U.S. Ser. No. 62/311,763 filed Mar. 22, 2016, U.S. Ser. No. 62/322,178 filed Apr. 13, 2016, U.S. Ser. No. 62/357,352 filed Jun. 30, 2016, U.S. Ser. No. 62/370,700 filed Aug. 3, 2016, U.S. Ser. No. 62/398,490 filed Sep. 22, 2016, U.S. Ser. No. 62/408,686 filed Oct. 14, 2016, and U.S. Ser. No. 62/357,332 filed Jun. 30, 2016; each of which is incorporated herein by reference.

GOVERNMENT SUPPORT

This invention was made with government support under grant number R01 EB022376 (formerly R01 GM065400) awarded by the National Institutes of Health, under training grant numbers F32 GM 112366-2 and F32 GM 106601-2 awarded by the National Institutes of Health, and Harvard Biophysics NIH training grant T32 GM008313 awarded by the National Institutes of Health. The government has certain rights in the invention.

BACKGROUND OF THE INVENTION

Targeted editing of nucleic acid sequences, for example, the targeted cleavage or the targeted introduction of a specific modification into genomic DNA, is a highly promising approach for the study of gene function and also has the potential to provide new therapies for human genetic diseases.[1] An ideal nucleic acid editing technology possesses three characteristics: (1) high efficiency of installing the desired modification; (2) minimal off-target activity; and (3) the ability to be programmed to edit precisely any site in a given nucleic acid, e.g., any site within the human genome.[2] Current genome engineering tools, including engineered zinc finger nucleases (ZFNs),[3] transcription activator like effector nucleases (TALENs),[4] and most recently, the RNA-guided DNA endonuclease Cas9,[5] effect sequence-specific DNA cleavage in a genome. This programmable cleavage can result in mutation of the DNA at the cleavage site via non-homologous end joining (NHEJ) or replacement of the DNA surrounding the cleavage site via homology-directed repair (HDR).[6,7]

One drawback to the current technologies is that both NHEJ and HDR are stochastic processes that typically result in modest gene editing efficiencies as well as unwanted gene alterations that can compete with the desired alteration.[8] Since many genetic diseases in principle can be treated by effecting a specific nucleotide change at a specific location in the genome (for example, a C to T change in a specific codon of a gene associated with a disease),[9] the development of a programmable way to achieve such precision gene editing would represent both a powerful new research tool, as well as a potential new approach to gene editing-based human therapeutics.

SUMMARY OF THE INVENTION

The clustered regularly interspaced short palindromic repeat (CRISPR) system is a recently discovered prokaryotic adaptive immune system[10] that has been modified to enable robust and general genome engineering in a variety of organisms and cell lines.[11] CRISPR-Cas (CRISPR associated) systems are protein-RNA complexes that use an RNA molecule (sgRNA) as a guide to localize the complex to a target DNA sequence via base-pairing.[12] In the natural systems, a Cas protein then acts as an endonuclease to cleave the targeted DNA sequence.[13] The target DNA sequence must be both complementary to the sgRNA, and also contain a "protospacer-adjacent motif" (PAM) at the 3'-end of the complementary region in order for the system to function.[14]

Among the known Cas proteins, *S. pyogenes* Cas9 has been mostly widely used as a tool for genome engineering.[15] This Cas9 protein is a large, multi-domain protein containing two distinct nuclease domains. Point mutations can be introduced into Cas9 to abolish nuclease activity, resulting in a dead Cas9 (dCas9) that still retains its ability to bind DNA in a sgRNA-programmed manner.[16] In principle, when fused to another protein or domain, dCas9 can target that protein to virtually any DNA sequence simply by co-expression with an appropriate sgRNA.

The potential of the dCas9 complex for genome engineering purposes is immense. Its unique ability to bring proteins to specific sites in a genome programmed by the sgRNA in theory can be developed into a variety of site-specific genome engineering tools beyond nucleases, including transcriptional activators, transcriptional repressors, histone-modifying proteins, integrases, and recombinases.[11] Some of these potential applications have recently been implemented through dCas9 fusions with transcriptional activators to afford RNA-guided transcriptional activators,[17,18] transcriptional repressors,[16,19,20] and chromatin modification enzymes.[21] Simple co-expression of these fusions with a variety of sgRNAs results in specific expression of the target genes. These seminal studies have paved the way for the design and construction of readily programmable sequence-specific effectors for the precise manipulation of genomes.

Significantly, 80-90% of protein mutations responsible for human disease arise from the substitution, deletion, or insertion of only a single nucleotide.[6] Most current strategies for single-base gene correction include engineered nucleases (which rely on the creation of double-strand breaks, DSBs, followed by stochastic, inefficient homology-directed repair, HDR), and DNA-RNA chimeric oligonucleotides.[22] The latter strategy involves the design of a RNA/DNA sequence to base pair with a specific sequence in genomic DNA except at the nucleotide to be edited. The resulting mismatch is recognized by the cell's endogenous repair system and fixed, leading to a change in the sequence of either the chimera or the genome. Both of these strategies suffer from low gene editing efficiencies and unwanted gene alterations, as they are subject to both the stochasticity of HDR and the competition between HDR and non-homologous end-joining, NHEJ.[23-25] HDR efficiencies vary according to the location of the target gene within the genome,[26] the state of the cell cycle,[27] and the type of cell/tissue.[28] The development of a direct, programmable way to install a specific type of base modification at a precise location in genomic DNA with enzyme-like efficiency and no stochasticity therefore represents a powerful new approach to gene editing-based research tools and human therapeutics.

Some aspects of the disclosure are based on the recognition that certain configurations of a dCas9 domain, and a cytidine deaminase domain fused by a linker are useful for efficiently deaminating target cytidine residues. Other aspects of this disclosure relate to the recognition that a nucleobase editing fusion protein with a cytidine deaminase domain fused to the N-terminus of a nuclease inactive Cas9 (dCas9) via a linker was capable of efficiently deaminating target nucleic acids in a double stranded DNA target molecule. See for example, Examples 3 and 4 below, which demonstrate that the fusion proteins, which are also referred to herein as base editors, generate less indels and more efficiently deaminate target nucleic acids than other base editors, such as base editors without a UGI domain. In some embodiments, the fusion protein comprises a nuclease-inactive Cas9 (dCas9) domain and an apolipoprotein B mRNA-editing complex 1 (APOBEC1) deaminase domain, where the deaminase domain is fused to the N-terminus of the dCas9 domain via a linker comprising the amino acid sequence SGSETPGTSESATPES (SEQ ID NO: 7). In some embodiments, the nuclease-inactive Cas9 (dCas9) domain of comprises the amino acid sequence set forth in SEQ ID NO: 263. In some embodiments, the deaminase is rat APOBEC1 (SEQ ID NO: 284). In some embodiments, the deaminase is human APOBEC1 (SEQ ID NO: 282). In some embodiments, the deaminase is pmCDA1 (SEQ ID NO: 5738). In some embodiments, the deaminase is human APOBEC3G (SEQ ID NO: 275). In some embodiments, the deaminase is a human APOBEC3G variant of any one of (SEQ ID NOs: 5739-5741).

Some aspects of the disclosure are based on the recognition that certain configurations of a dCas9 domain, and a cytidine deaminase domain fused by a linker are useful for efficiently deaminating target cytidine residues. Other aspects of this disclosure relate to the recognition that a nucleobase editing fusion protein with an apolipoprotein B mRNA-editing complex 1 (APOBEC1) deaminase domain fused to the N-terminus of a nuclease inactive Cas9 (dCas9) via a linker comprising the amino acid sequence SGSETPGTSESATPES (SEQ ID NO: 7) was capable of efficiently deaminating target nucleic acids in a double stranded DNA target molecule. In some embodiments, the fusion protein comprises a nuclease-inactive Cas9 (dCas9) domain and an apolipoprotein B mRNA-editing complex 1 (APOBEC1) deaminase domain, where the deaminase domain is fused to the N-terminus of the dCas9 domain via a linker comprising the amino acid sequence SGSETPGT-SESATPES (SEQ ID NO: 7).

In some embodiments, the fusion protein comprises the amino acid residues 11-1629 of the amino acid sequence set forth in SEQ ID NO: 591. In some embodiments, the fusion protein comprises the amino acid sequence set forth in SEQ ID NO: 591. In some embodiments, the fusion protein comprises the amino acid sequence of any one of SEQ ID NOs: 5737, 5743, 5745, and 5746.

Some aspects of this disclosure provide strategies, systems, reagents, methods, and kits that are useful for the targeted editing of nucleic acids, including editing a single site within a subject's genome, e.g., a human's genome. In some embodiments, fusion proteins of Cas9 (e.g., dCas9, nuclease active Cas9, or Cas9 nickase) and deaminases or deaminase domains, are provided. In some embodiments, methods for targeted nucleic acid editing are provided. In some embodiments, reagents and kits for the generation of targeted nucleic acid editing proteins, e.g., fusion proteins of Cas9 and deaminases or deaminase domains, are provided.

Some aspects of this disclosure provide fusion proteins comprising a Cas9 protein as provided herein that is fused to a second protein (e.g., an enzymatic domain such as a cytidine deaminase domain), thus forming a fusion protein. In some embodiments, the second protein comprises an enzymatic domain, or a binding domain. In some embodiments, the enzymatic domain is a nuclease, a nickase, a recombinase, a deaminase, a methyltransferase, a methylase, an acetylase, an acetyltransferase, a transcriptional activator, or a transcriptional repressor domain. In some embodiments, the enzymatic domain is a nucleic acid editing domain. In some embodiments, the nucleic acid editing domain is a deaminase domain. In some embodiments, the deaminase is a cytosine deaminase or a cytidine deaminase. In some embodiments, the deaminase is an apolipoprotein B mRNA-editing complex (APOBEC) family deaminase. In some embodiments, the deaminase is an APOBEC1 deaminase. In some embodiments, the deaminase is an APOBEC2 deaminase. In some embodiments, the deaminase is an APOBEC3 deaminase. In some embodiments, the deaminase is an APOBEC3A deaminase. In some embodiments, the deaminase is an APOBEC3B deaminase. In some embodiments, the deaminase is an APOBEC3C deaminase. In some embodiments, the deaminase is an APOBEC3D deaminase. In some embodiments, the deaminase is an APOBEC3E deaminase. In some embodiments, the deaminase is an APOBEC3F deaminase. In some embodiments, the deaminase is an APOBEC3G deaminase. In some embodiments, the deaminase is an APOBEC3H deaminase. In some embodiments, the deaminase is an APOBEC4 deaminase. In some embodiments, the deaminase is an activation-induced deaminase (AID). It should be appreciated that the deaminase may be from any suitable organism (e.g., a human or a rat). In some embodiments, the deaminase is from a human, chimpanzee, gorilla, monkey, cow, dog, rat, or mouse. In some embodiments, the deaminase is rat APOBEC1 (SEQ ID NO: 284). In some embodiments, the deaminase is human APOBEC1 (SEQ ID NO: 282). In some embodiments, the deaminase is pmCDA1.

Some aspects of this disclosure provide fusion proteins comprising: (i) a nuclease-inactive Cas9 (dCas9) domain comprising the amino acid sequence of SEQ ID NO: 263; and (ii) an apolipoprotein B mRNA-editing complex 1 (APOBEC1) deaminase domain, wherein the deaminase domain is fused to the N-terminus of the dCas9 domain via a linker comprising the amino acid sequence of SGSETPGT-SESATPES (SEQ ID NO: 7). In some embodiments, the deaminase is rat APOBEC1 (SEQ ID NO: 284). In some embodiments, the deaminase is human APOBEC1 (SEQ ID NO: 282). In some embodiments, the fusion protein comprises the amino acid sequence of SEQ ID NO: 591. In some embodiments, the fusion protein comprises the amino acid sequence of SEQ ID NO: 5737. In some embodiments, the deaminase is pmCDA1 (SEQ ID NO: 5738). In some embodiments, the deaminase is human APOBEC3G (SEQ ID NO: 275). In some embodiments, the deaminase is a human APOBEC3G variant of any one of SEQ ID NOs: 5739-5741.

Some aspects of this disclosure provide fusion proteins comprising: (i) a Cas9 nickase domain and (ii) an apolipoprotein B mRNA-editing complex 1 (APOBEC1) deaminase domain, wherein the deaminase domain is fused to the N-terminus of the Cas9 nickase domain. In some embodiments, the Cas9 nickase domain comprises a D10X mutation of the amino acid sequence provided in SEQ ID NO: 10, or a corresponding mutation in any of the amino acid sequences provided in SEQ ID NOs: 11-260, wherein X is any amino acid except for D. In some embodiments, the amino acid sequence of the Cas9 nickase domain comprises a D10A mutation of the amino acid sequence provided in SEQ ID NO: 10, or a corresponding mutation in any of the amino acid sequences provided in SEQ ID NOs: 11-260. In some embodiments, the amino acid sequence of the Cas9 nickase domain comprises a histidine at amino acid position 840 of the amino acid sequence provided in SEQ ID NO: 10, or a corresponding amino acid position in any of the amino acid sequences provided in SEQ ID NOs: 11-260. In some embodiments, the amino acid sequence of the Cas9 nickase domain comprises the amino acid sequence as set forth in SEQ ID NO: 267. In some embodiments, the deaminase is rat APOBEC1 (SEQ ID NO: 284). In some embodiments, the deaminase is human APOBEC1 (SEQ ID NO: 282). In some embodiments, the deaminase is pmCDA1.

Some aspects of this disclosure provide fusion proteins comprising: (i) a Cas9 nickase domain and (ii) an apolipoprotein B mRNA-editing complex 1 (APOBEC1) deaminase domain, wherein the deaminase domain is fused to the N-terminus of the Cas9 nickase domain. In some embodiments, the Cas9 nickase domain comprises a D10X mutation of the amino acid sequence provided in SEQ ID NO: 10, or a corresponding mutation in any of the amino acid sequences provided in SEQ ID NOs: 11-260, wherein X is any amino acid except for D. In some embodiments, the amino acid sequence of the Cas9 nickase domain comprises a D10A mutation of the amino acid sequence provided in SEQ ID NO: 10, or a corresponding mutation in any of the amino acid sequences provided in SEQ ID NOs: 11-260. In some embodiments, the amino acid sequence of the Cas9 nickase domain comprises a histidine at amino acid position 840 of the amino acid sequence provided in SEQ ID NO: 10, or a corresponding amino acid position in any of the amino acid sequences provided in SEQ ID NOs: 11-260. In some embodiments, the amino acid sequence of the Cas9 nickase domain comprises the amino acid sequence as set forth in SEQ ID NO: 267. In some embodiments, the deaminase is rat APOBEC1 (SEQ ID NO: 284). In some embodiments, the deaminase is human APOBEC1 (SEQ ID NO: 282). In some embodiments, the deaminase is pmCDA1.

Other aspects of this disclosure relate to the recognition that fusion proteins comprising a deaminase domain, a dCas9 domain and a uracil glycosylase inhibitor (UGI) domain demonstrate improved efficiency for deaminating target nucleotides in a nucleic acid molecule. Without wishing to be bound by any particular theory, cellular DNA-repair response to the presence of U:G heteroduplex DNA may be responsible for a decrease in nucleobase editing efficiency in cells. Uracil DNA glycosylase (UDG) catalyzes removal of U from DNA in cells, which may initiate base excision repair, with reversion of the U:G pair to a C:G pair as the most common outcome. As demonstrated herein, Uracil DNA Glycosylase Inhibitor (UGI) may inhibit human UDG activity. Without wishing to be bound by any particular theory, base excision repair may be inhibited by molecules that bind the single strand, block the edited base, inhibit UGI, inhibit base excision repair, protect the edited base, and/or promote "fixing" of the non-edited strand, etc. Thus, this disclosure contemplates fusion proteins comprising a dCas9-cytidine deaminase domain that is fused to a UGI domain.

In some embodiments, the fusion protein comprises a nuclease-inactive Cas9 (dCas9) domain; a nucleic acid editing domain; and a uracil glycosylase inhibitor (UGI) domain. In some embodiments, the dCas9 domain comprises a D10X mutation of the amino acid sequence provided in SEQ ID NO: 10, or a corresponding mutation in any of the amino acid sequences provided in SEQ ID NOs: 11-260, wherein X is any amino acid except for D. In some embodiments, the amino acid sequence of the dCas9 domain comprises a D10A mutation of the amino acid sequence provided in SEQ ID NO: 10, or a corresponding mutation in any of the amino acid sequences provided in SEQ ID NOs: 11-260. In some embodiments, the amino acid sequence of the dCas9 domain comprises an H840X mutation of the amino acid sequence provided in SEQ ID NO: 10, or a corresponding mutation in any of the amino acid sequences provided in SEQ ID NOs: 11-260, wherein X is any amino acid except for H. In some embodiments, the amino acid sequence of the dCas9 domain comprises an H840A mutation of the amino acid sequence provided in SEQ ID NO: 10, or a corresponding mutation in any of the amino acid sequences provided in SEQ ID NOs: 11-260. In some embodiments, the dCas9 domain comprises the amino acid sequence as set forth in SEQ ID NO: 263.

Further aspects of this disclosure relate to the recognition that fusion proteins using a Cas9 nickase as the Cas9 domain demonstrate improved efficiency for editing nucleic acids. For example, aspects of this disclosure relate to the recognition that fusion proteins comprising a Cas9 nickase, a deaminase domain and a UGI domain demonstrate improved efficiency for editing nucleic acids. For example, the improved efficiency for editing nucleotides is described below in the Examples section.

Some aspects of the disclosure are based on the recognition that any of the base editors provided herein are capable of modifying a specific nucleotide base without generating a significant proportion of indels. An "indel", as used herein, refers to the insertion or deletion of a nucleotide base within a nucleic acid. Such insertions or deletions can lead to frame shift mutations within a coding region of a gene. In some embodiments, it is desirable to generate base editors that efficiently modify (e.g. mutate or deaminate) a specific nucleotide within a nucleic acid, without generating a large number of insertions or deletions (i.e., indels) in the nucleic acid. In certain embodiments, any of the base editors provided herein are capable of generating a greater proportion of intended modifications (e.g., point mutations or deaminations) versus indels.

Some aspects of the disclosure are based on the recognition that any of the base editors provided herein are capable of efficiently generating an intended mutation, such as a point mutation, in a nucleic acid (e.g. a nucleic acid within a genome of a subject) without generating a significant number of unintended mutations, such as unintended point mutations.

In some embodiments, a fusion protein comprises a Cas9 nickase domain, a nucleic acid editing domain; and a uracil glycosylase inhibitor (UGI) domain. In some embodiments, the amino acid sequence of the Cas9 nickase domain comprises a D10X mutation of the amino acid sequence provided in SEQ ID NO: 10, or a corresponding mutation in any of the amino acid sequences provided in SEQ ID NOs: 11-260, wherein X is any amino acid except for D. In some embodiments, the amino acid sequence of the Cas9 nickase domain comprises a D10A mutation of the amino acid sequence provided in SEQ ID NO: 10, or a corresponding mutation in any of the amino acid sequences provided in SEQ ID NOs: 11-260. In some embodiments, the amino acid sequence of the Cas9 nickase domain comprises a histidine at amino acid position 840 of the amino acid sequence provided in SEQ ID NO: 10, or a corresponding amino acid position in any of the amino acid sequences provided in SEQ ID NOs: 11-260. In some embodiments, the amino acid sequence of the Cas9 nickase domain comprises the amino acid sequence as set forth in SEQ ID NO: 267.

In some embodiments, the deaminase domain of the fusion protein is fused to the N-terminus of the dCas9 domain or the Cas9 nickase. In some embodiments, the UGI domain is fused to the C-terminus of the dCas9 domain or the Cas9 nickase. In some embodiments, the dCas9 domain or the Cas9 nickase and the nucleic acid editing domain are fused via a linker. In some embodiments, the dCas9 domain or the Cas9 nickase and the UGI domain are fused via a linker.

In certain embodiments, linkers may be used to link any of the peptides or peptide domains of the invention. The linker may be as simple as a covalent bond, or it may be a polymeric linker many atoms in length. In certain embodiments, the linker is a polpeptide or based on amino acids. In other embodiments, the linker is not peptide-like. In certain embodiments, the linker is a covalent bond (e.g., a carbon-carbon bond, disulfide bond, carbon-heteroatom bond, etc.). In certain embodiments, the linker is a carbon-nitrogen bond of an amide linkage. In certain embodiments, the linker is a cyclic or acyclic, substituted or unsubstituted, branched or unbranched aliphatic or heteroaliphatic linker. In certain embodiments, the linker is polymeric (e.g., polyethylene, polyethylene glycol, polyamide, polyester, etc.). In certain embodiments, the linker comprises a monomer, dimer, or polymer of aminoalkanoic acid. In certain embodiments, the linker comprises an aminoalkanoic acid (e.g., glycine, ethanoic acid, alanine, beta-alanine, 3-aminopropanoic acid, 4-aminobutanoic acid, 5-pentanoic acid, etc.). In certain embodiments, the linker comprises a monomer, dimer, or polymer of aminohexanoic acid (Ahx). In certain embodiments, the linker is based on a carbocyclic moiety (e.g., cyclopentane, cyclohexane). In other embodiments, the linker comprises a polyethylene glycol moiety (PEG). In other embodiments, the linker comprises amino acids. In certain embodiments, the linker comprises a peptide. In certain embodiments, the linker comprises an aryl or heteroaryl moiety. In certain embodiments, the linker is based on a phenyl ring. The linker may included functionalized moieties to facilitate attachment of a nucleophile (e.g., thiol, amino) from the peptide to the linker. Any electrophile may be used as part of the linker. Exemplary electrophiles include, but are not limited to, activated esters, activated amides, Michael acceptors, alkyl halides, aryl halides, acyl halides, and isothiocyanates.

In some embodiments, the linker comprises the amino acid sequence (GGGGS)$_n$ (SEQ ID NO: 5), (G)$_n$, (EAAAK)$_n$ (SEQ ID NO: 6), (GGS)$_n$, (SGGS)$_n$ (SEQ ID NO: 4288), SGSETPGTSESATPES (SEQ ID NO: 7), (XP)$_n$, or any combination thereof, wherein n is independently an integer between 1 and 30, and wherein X is any amino acid. In some embodiments, the linker comprises the amino acid sequence (GGS)$_n$, wherein n is 1, 3, or 7. In some embodiments, the linker comprises the amino acid sequence SGSETPGTSESATPES (SEQ ID NO: 7).

In some embodiments, the fusion protein comprises the structure [nucleic acid editing domain]-[optional linker sequence]-[dCas9 or Cas9 nickase]-[optional linker sequence]-[UGI]. In some embodiments, the fusion protein comprises the structure [nucleic acid editing domain]-[optional linker sequence]-[UGI]-[optional linker sequence]-[dCas9 or Cas9 nickase]; [UGI]-[optional linker sequence]-[nucleic acid editing domain]-[optional linker sequence]-[dCas9 or Cas9 nickase]; [UGI]-[optional linker sequence]-[dCas9 or Cas9 nickase]-[optional linker sequence]-[nucleic acid editing domain]; [dCas9 or Cas9 nickase]-[optional linker sequence]-[UGI]-[optional linker sequence]-[nucleic acid editing domain]; or [dCas9 or Cas9 nickase]-[optional linker sequence]-[nucleic acid editing domain]-[optional linker sequence]-[UGI].

In some embodiments, the nucleic acid editing domain comprises a deaminase. In some embodiments, the nucleic acid editing domain comprises a deaminase. In some embodiments, the deaminase is a cytidine deaminase. In some embodiments, the deaminase is an apolipoprotein B mRNA-editing complex (APOBEC) family deaminase. In some embodiments, the deaminase is an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, or an APOBEC4 deaminase. In some embodiments, the deaminase is an activation-induced deaminase (AID). In some embodiments, the deaminase is a Lamprey CDA1 (pmCDA1) deaminase.

In some embodiments, the deaminase is from a human, chimpanzee, gorilla, monkey, cow, dog, rat, or mouse. In some embodiments, the deaminase is from a human. In some embodiments the deaminase is from a rat. In some embodiments, the deaminase is a rat APOBEC1 deaminase comprising the amino acid sequence set forth in (SEQ ID NO: 284). In some embodiments, the deaminase is a human APOBEC1 deaminase comprising the amino acid sequence set forth in (SEQ ID NO: 282). In some embodiments, the deaminase is pmCDA1 (SEQ ID NO: 5738). In some embodiments, the deaminase is human APOBEC3G (SEQ ID NO: 275). In some embodiments, the deaminase is a human APOBEC3G variant of any one of (SEQ ID NOs: 5739-5741). In some embodiments, the deaminase is at least 80%, at least 85%, at least 90%, at least 92%, at least 95%, at least 96%, at least 97%, at least 98%, at least 99%, or at least 99.5% identical to any one of the amino acid sequences set forth in SEQ ID NOs: 266-284 or 5725-5741.

In some embodiments, the UGI domain comprises an amino acid sequence that is at least 80%, at least 85%, at least 90%, at least 92%, at least 95%, at least 96%, at least 97%, at least 98%, at least 99%, or at least 99.5% identical to SEQ ID NO: 600. In some embodiments, the UGI domain comprises the amino acid sequence as set forth in SEQ ID NO: 600.

Some aspects of this disclosure provide complexes comprising a Cas9 protein or a Cas9 fusion protein as provided herein, and a guide RNA bound to the Cas9 protein or the Cas9 fusion protein.

Some aspects of this disclosure provide methods of using the Cas9 proteins, fusion proteins, or complexes provided herein. For example, some aspects of this disclosure provide methods comprising contacting a DNA molecule (a) with a Cas9 protein or a fusion protein as provided herein and with a guide RNA, wherein the guide RNA is about 15-100 nucleotides long and comprises a sequence of at least 10 contiguous nucleotides that is complementary to a target sequence; or (b) with a Cas9 protein, a Cas9 fusion protein, or a Cas9 protein or fusion protein complex with a gRNA as provided herein.

Some aspects of this disclosure provide kits comprising a nucleic acid construct, comprising (a) a nucleotide sequence encoding a Cas9 protein or a Cas9 fusion protein as provided herein; and (b) a heterologous promoter that drives expression of the sequence of (a). In some embodiments, the kit further comprises an expression construct encoding a guide RNA backbone, wherein the construct comprises a cloning site positioned to allow the cloning of a nucleic acid sequence identical or complementary to a target sequence into the guide RNA backbone.

Some aspects of this disclosure provide polynucleotides encoding a Cas9 protein of a fusion protein as provided herein. Some aspects of this disclosure provide vectors comprising such polynucleotides. In some embodiments, the vector comprises a heterologous promoter driving expression of polynucleotide.

Some aspects of this disclosure provide cells comprising a Cas9 protein, a fusion protein, a nucleic acid molecule, and/or a vector as provided herein.

The description of exemplary embodiments of the reporter systems above is provided for illustration purposes only and not meant to be limiting. Additional reporter systems, e.g., variations of the exemplary systems described in detail above, are also embraced by this disclosure.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

FIG. 11A: Nucleobase editing strategy. DNA with a target C (red) at a locus specified by a guide RNA (green) is bound by dCas9 (blue), which mediates the local denaturation of the DNA substrate. Cytidine deamination by a tethered APOBEC1 enzyme (orange) converts the target C to U. The resulting G:U heteroduplex can be permanently converted to an A:T base pair following DNA replication or repair. If the U is in the template DNA strand, it will also result in an RNA transcript containing a G to A mutation following transcription. FIG. 11B: Deamination assay showing an activity window of approximately five nucleotides. Following incubation of NBE1-sgRNA complexes with dsDNA substrates at 37° C. for 2 h, the 5' fluorophore-labeled DNA was isolated and incubated with USER enzyme (uracil DNA glycosylase and endonuclease VIII) at 37° C. for 1 h to induce DNA cleavage at the site of any uracils. The resulting DNA was resolved on a denaturing polyacrylamide gel, and any fluorophore-linked strands were visualized. Each lane is labeled according to the position of the target C within the protospacer, or with "-" if no target C is present, counting the base distal from the PAM as position 1. FIG. 11C: Deaminase assay showing the sequence specificity and sgRNA-dependence of NBE1. The DNA substrate with a target C at position 7 was incubated with NBE1 as in FIG. 11B with either the correct sgRNA, a mismatched sgRNA, or no sgRNA. No C to U editing is observed with the mismatched sgRNA or with no sgRNA. The positive control sample contains a DNA sequence with a U synthetically incorporated at position 7.

FIG. 12A: Effect of changing the sequence surrounding the target C on editing efficiency in vitro. The deamination yield of 80% of targeted strands (40% of total sequencing reads from both strands) for $C_7$ in the protospacer sequence 5'-TTATTTCGTGGATTTATTTA-3'(SEQ ID NO: 264) was defined as 1.0, and the relative deamination efficiencies of substrates containing all possible single-base mutations at positions 1-6 and 8-13 are shown. Values and error bars reflect the mean and standard deviation of two or more independent biological replicates performed on different days. FIG. 12B: Positional effect of each NC motif on editing efficiency in vitro. Each NC target motif was varied from positions 1 to 8 within the protospacer as indicated in the sequences shown on the right (the PAM shown in red, the protospacer plus one base 5' to the protospacer are also shown). The percentage of total sequence reads containing T at each of the numbered target C positions following incubation with NBE1 is shown in the graph. Note that the maximum possible deamination yield in vitro is 50% of total sequencing reads (100% of targeted strands). Values and error bars reflect the mean and standard deviation of two or three independent biological replicates performed on different days. FIG. 12B depicts SEQ ID NOs: 285 through 292 from top to bottom, respectively.

FIG. 13A: Protospacer (black) and PAM (red) sequences of the six mammalian cell genomic loci targeted by nucleobase editors. Target Cs are indicated with sub-scripted numbers corresponding to their positions within the protospacer. FIG. 13A depicts SEQ ID NOs: 293 through 298 from top to bottom, respectively. FIG. 13B: HEK293T cells were transfected with plasmids expressing NBE1, NBE2, or NBE3 and an appropriate sgRNA. Three days after transfection, genomic DNA was extracted and analyzed by high-throughput DNA sequencing at the six loci. Cellular C to T conversion percentages, defined as the percentage of total DNA sequencing reads with Ts at the target positions indicated, are shown for NBE1, NBE2, and NBE3 at all six genomic loci, and for wt Cas9 with a donor HDR template at three of the six sites (EMX1, HEK293 site 3, and HEK293 site 4). Values and error bars reflect the mean and standard deviation of three independent biological replicates performed on different days. FIG. 13C: Frequency of indel formation, calculated as described in the Methods, is shown following treatment of HEK293T cells with NBE2 and NBE3 for all six genomic loci, or with wt Cas9 and a single-stranded DNA template for HDR at three of the six sites (EMX1, HEK293 site 3, and HEK293 site 4). Values reflect the mean of at least three independent biological replicates performed on different days.

Figures 14A, 14B, 14C:
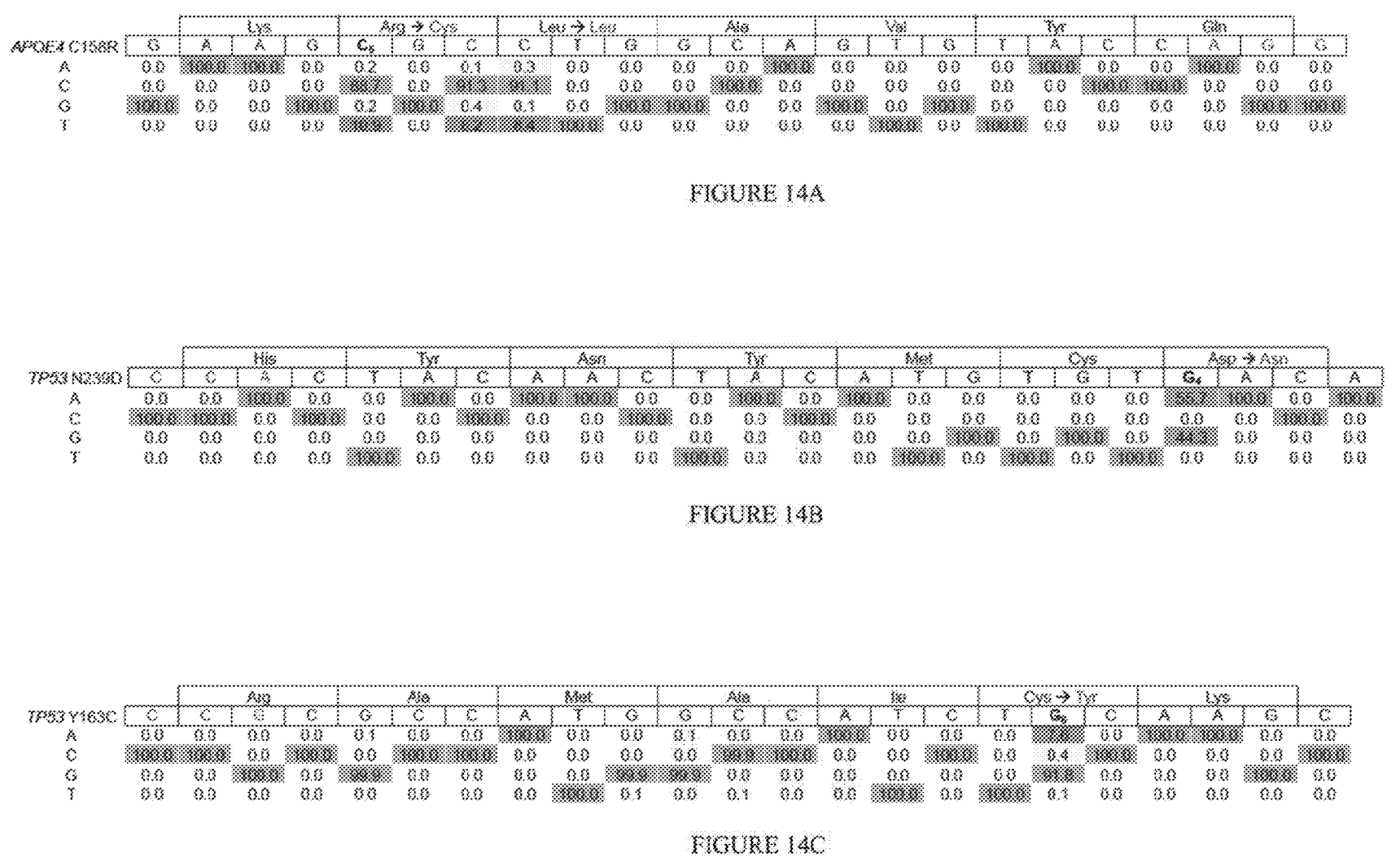

FIGS. 14A to 14C show NBE2- and NBE3-mediated correction of three disease-relevant mutations in mammalian cells. For each site, the sequence of the protospacer is indicated to the right of the name of the mutation, with the PAM highlighted in green and the base responsible for the mutation indicated in bold with a subscripted number corresponding to its position within the protospacer. The amino acid sequence above each disease-associated allele is shown, together with the corrected amino acid sequence following nucleobase editing in red. Underneath each sequence are the percentages of total sequencing reads with the corresponding base. Cells were nucleofected with plasmids encoding NBE2 or NBE3 and an appropriate sgRNA. Two days after nucleofection, genomic DNA was extracted and analyzed by HTS to assess pathogenic mutation correction. FIG. 14A: The Alzheimer's disease-associated APOE4 allele is converted to APOE3' in mouse astrocytes by NBE3 in 11% of total reads (44% of nucleofected astrocytes). Two nearby Cs are also converted to Ts, but with no change to the predicted sequence of the resulting protein (SEQ ID NO: 299). FIG. 14B The cancer-associated p53 N239D mutation is corrected by NBE2 in 11% of treated human lymphoma cells (12% of nucleofected cells) that are heterozygous for the mutation (SEQ ID NO: 300). FIG. 14C The p53 Y163C mutation is corrected by NBE3 in 7.6% of nucleofected human breast cancer cells (SEQ ID NO: 301).

FIGS. 16A to 16B show NBE1 is capable of correcting disease-relevant mutations in vitro. FIG. 16A: Protospacer and PAM sequences (red) of seven disease-relevant mutations. The disease-associated target C in each case is indicated with a subscripted number reflecting its position within the protospacer. For all mutations except both APOE4 SNPs, the target C resides in the template (non-coding) strand. FIG. 16A depicts SEQ ID NOs: 302 through 308 from top to bottom, respectively. FIG. 16B: Deaminase assay showing each dsDNA oligonucleotide before (−) and after (+) incubation with NBE1, DNA isolation, and incubation with USER enzymes to cleave DNA at positions containing U. Positive control lanes from incubation of synthetic oligonucleotides containing U at various positions within the protospacer with USER enzymes are shown with the corresponding number indicating the position of the U.

FIG. 17 shows processivity of NBE1. The protospacer and PAM (red) of a 60-mer DNA oligonucleotide containing eight consecutive Cs is shown at the top. The oligonucleotide (125 nM) was incubated with NBE1 (2 μM) for 2 h at 37° C. The DNA was isolated and analyzed by high-throughput sequencing. Shown are the percent of total reads for the most frequent nine sequences observed. The vast majority of edited strands (>93%) have more than one C converted to T. This figure depicts SEQ ID NO: 309.

FIGS. 18A to 18H show the effect of fusing UGI to NBE1 to generate NBE2. FIG. 18A: Protospacer and PAM (red) sequences of the six mammalian cell genomic loci targeted with nucleobase editors. Editable Cs are indicated with labels corresponding to their positions within the protospacer. FIG. 18A depicts SEQ ID NOs: 293 through 298 from top to bottom, respectively. FIGS. 18B to 18G: HEK293T cells were transfected with plasmids expressing NBE1, NBE2, or NBE1 and UGI, and an appropriate sgRNA. Three days after transfection, genomic DNA was extracted and analyzed by high-throughput DNA sequencing at the six loci. Cellular C to T conversion percentages, defined as the percentage of total DNA sequencing reads with Ts at the target positions indicated, are shown for NBE1, NBE1 and UGI, and NBE2 at all six genomic loci. FIG. 18H: C to T mutation rates at 510 Cs surrounding the protospacers of interest for NBE1, NBE1 plus UGI on a separate plasmid, NBE2, and untreated cells are shown. The data show the results of 3,000,000 DNA sequencing reads from 1.5×106 cells. Values reflect the mean of at least two biological experiments conducted on different days.

Figure 22:
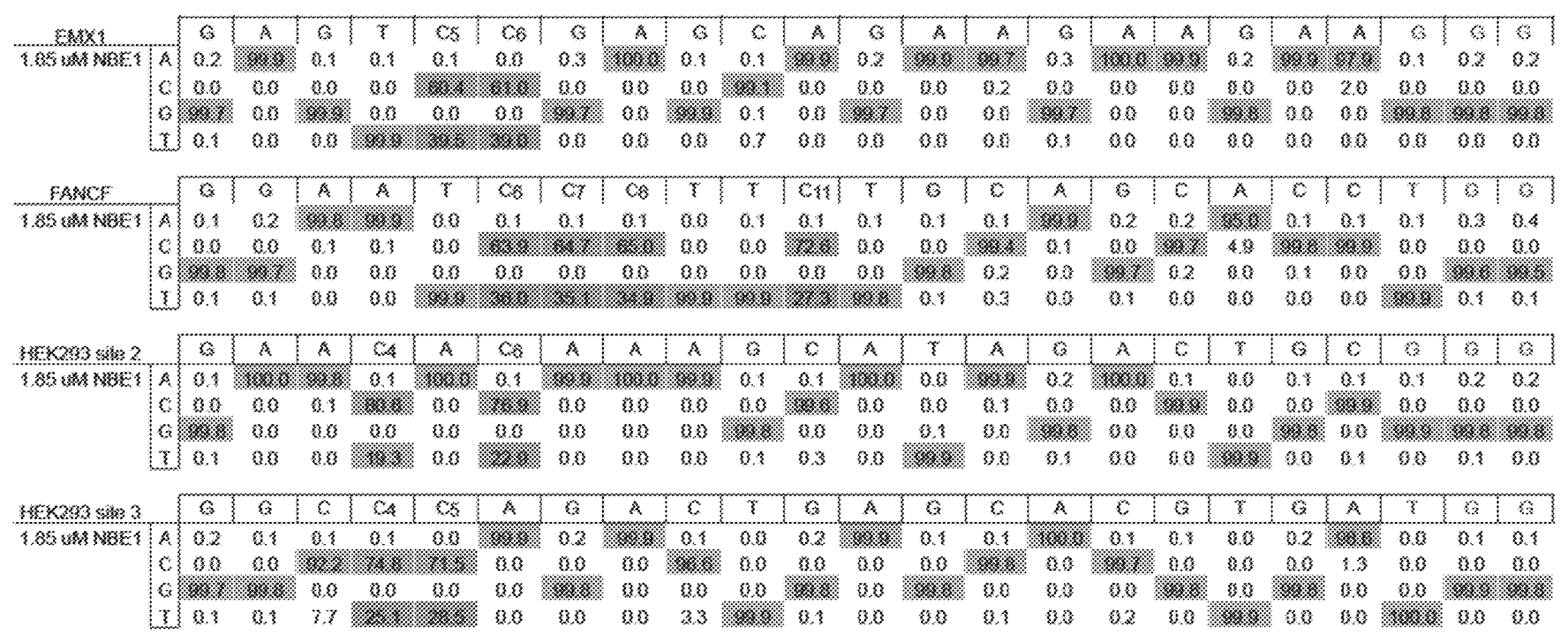
Figure 22:
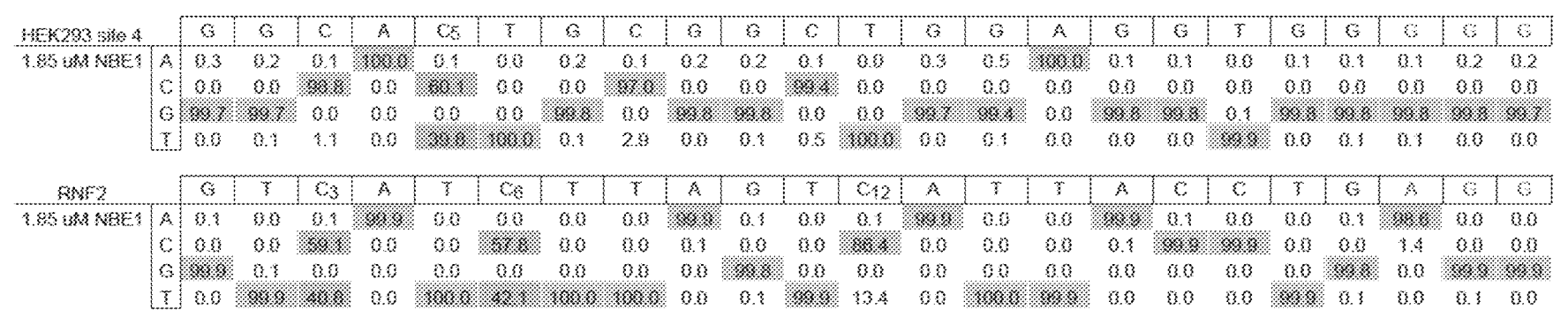

FIG. 22 shows in vitro identification of editable Cs in six genomic loci. Synthetic 80-mers with sequences matching six different genomic sites were incubated with NBE1 then analyzed for nucleobase editing via HTS. For each site, the sequence of the protospacer is indicated to the right of the name of the site, with the PAM highlighted in red. Underneath each sequence are the percentages of total DNA sequencing reads with the corresponding base. A target C was considered as "editable" if the in vitro conversion efficiency is >10%. Note that maximum yields are 50% of total DNA sequencing reads since the non-targeted strand is not a substrate for nucleobase editing. This figure depicts SEQ ID NOs: 293 through 298 from top to bottom, respectively.

Figure 24:
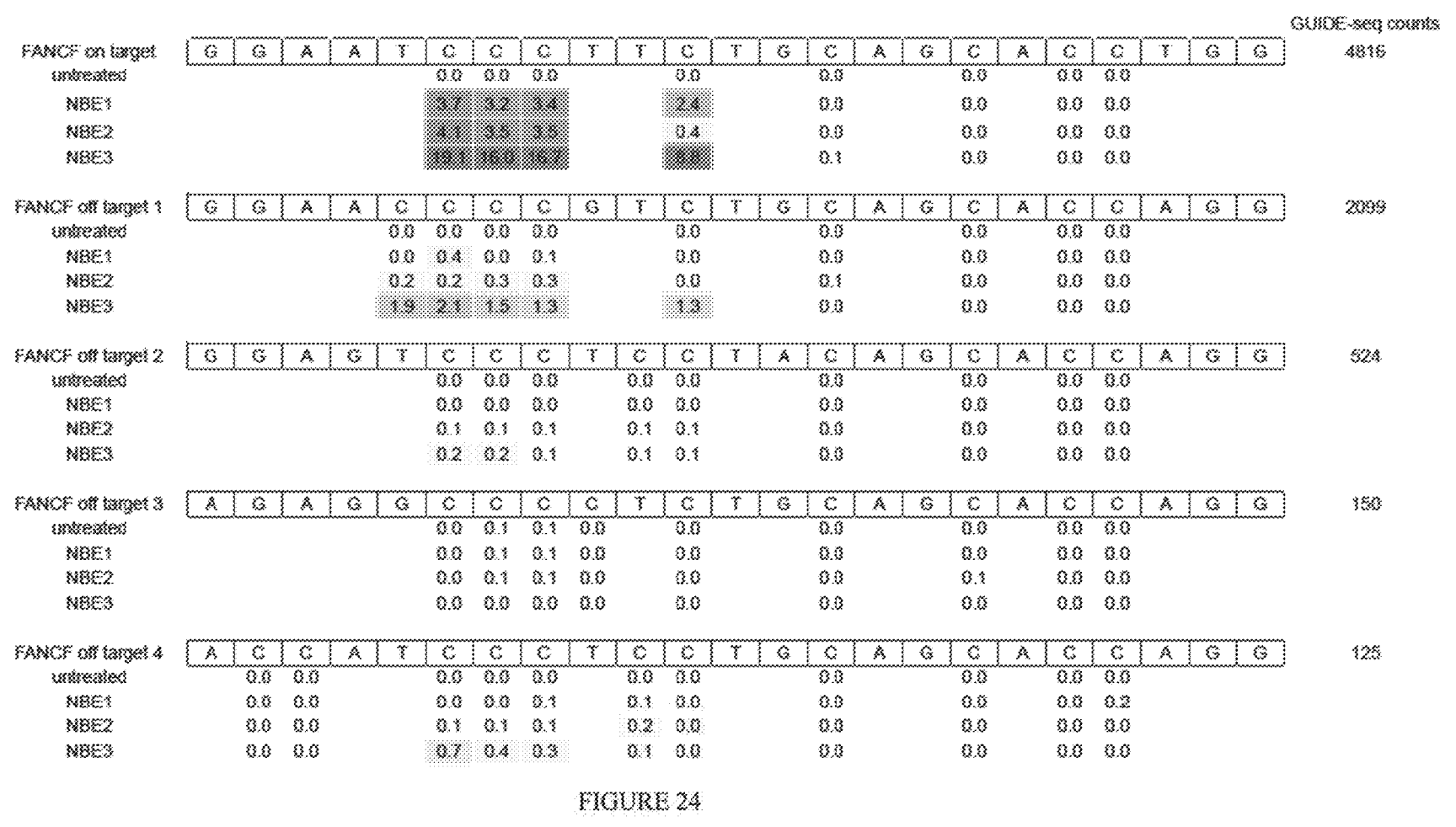
Figure 24:
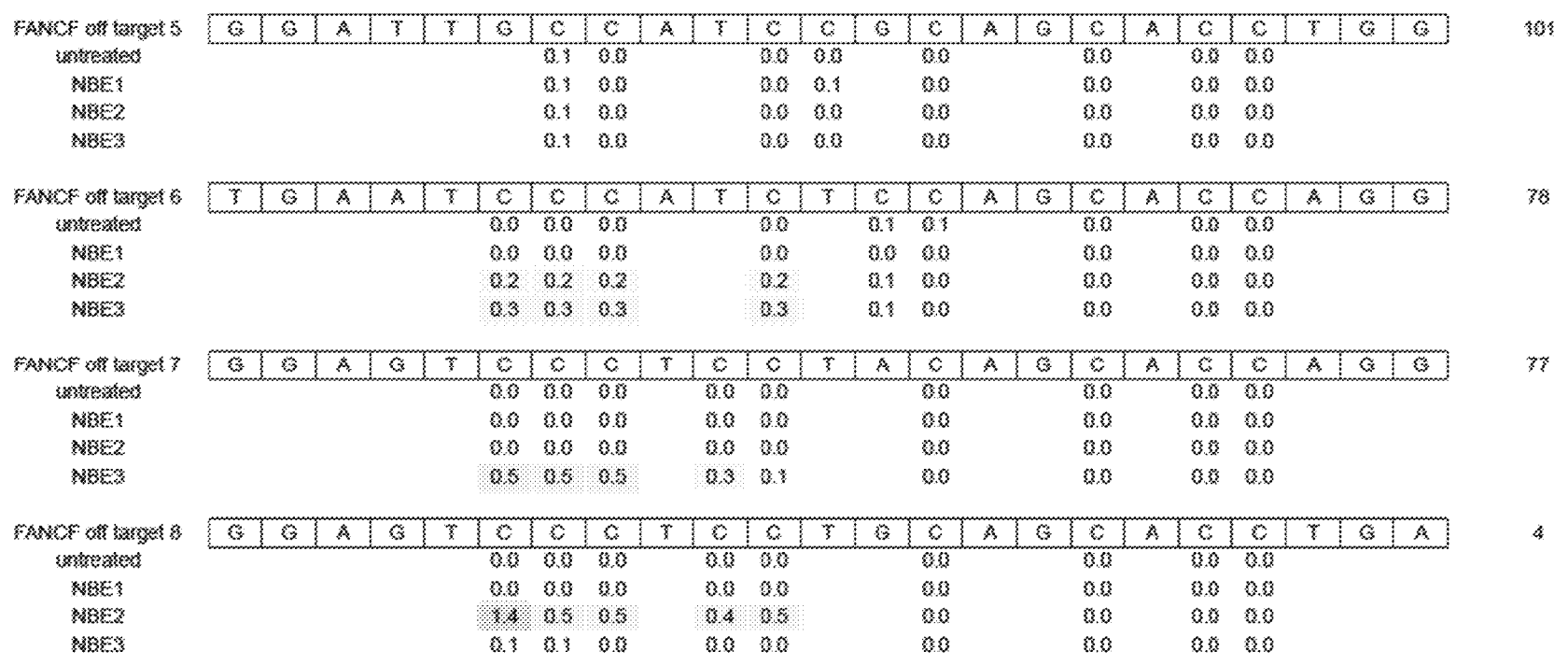

FIG. 24 shows activities of NBE1, NBE2, and NBE3 at FANCF off-targets. HEK293T cells were transfected with plasmids expressing NBE1, NBE2, or NBE3 and a sgRNA matching the FANCF sequence using Lipofectamine 2000. Three days after transfection, genomic DNA was extracted, amplified by PCR, and analyzed by high-throughput DNA sequencing at the on-target loci, plus all of the known Cas9 off-target loci for the FANCF sgRNA, as previously determined using the GUIDE-seq method[55]. Sequences of the on-target and off-target protospacers and protospacer adjacent motifs (PAMs) are displayed. Cellular C to T conversion percentages, defined as the percentage of total DNA sequencing reads with T at each position of an original C within the protospacer, are shown for NBE1, NBE2, and NBE3. On the far right are displayed the total number of sequencing reads reported for each sequence. This figure depicts SEQ ID NOs: 294 and 319 through 326 from top to bottom, respectively.

Figure 26:
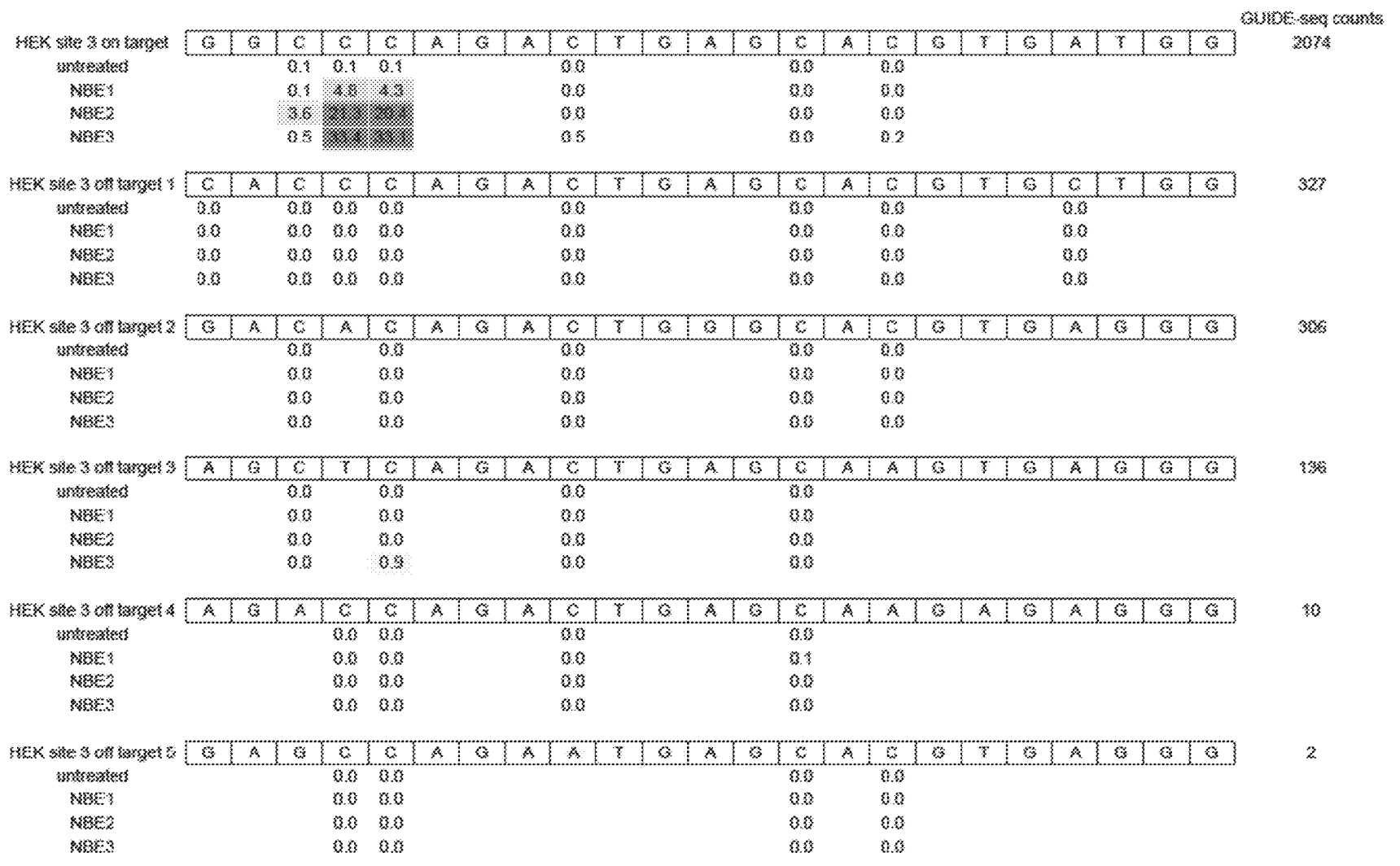

FIG. 26 shows activities of NBE1, NBE2, and NBE3 at HEK293 site 3 off-targets. HEK293T cells were transfected with plasmids expressing NBE1, NBE2, or NBE3 and a sgRNA matching the HEK293 site 3 sequence using Lipofectamine 2000. Three days after transfection, genomic DNA was extracted, amplified by PCR, and analyzed by high-throughput DNA sequencing at the on-target loci, plus all of the known Cas9 off-target loci for the HEK293 site 3 sgRNA, as previously determined using the GUIDE-seq method[55]. Sequences of the on-target and off-target protospacers and protospacer adjacent motifs (PAMs) are displayed. Cellular C to T conversion percentages, defined as the percentage of total DNA sequencing reads with T at each position of an original C within the protospacer, are shown for NBE1, NBE2, and NBE3. On the far right are displayed the total number of sequencing reads reported for each sequence. This figure depicts SEQ ID NOs: 296 and 659 through 663 from top to bottom, respectively.

Figure 27:
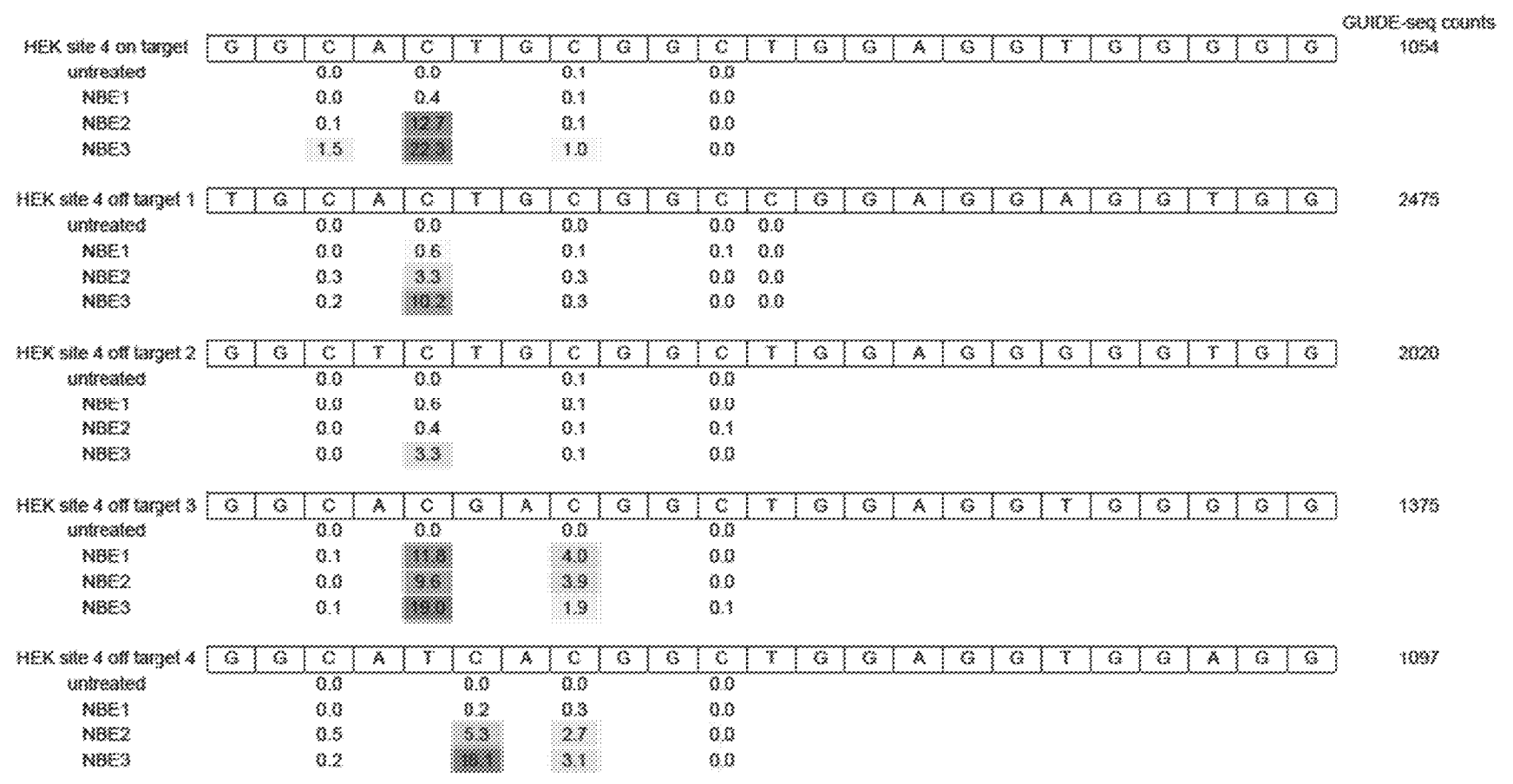
Figure 27:
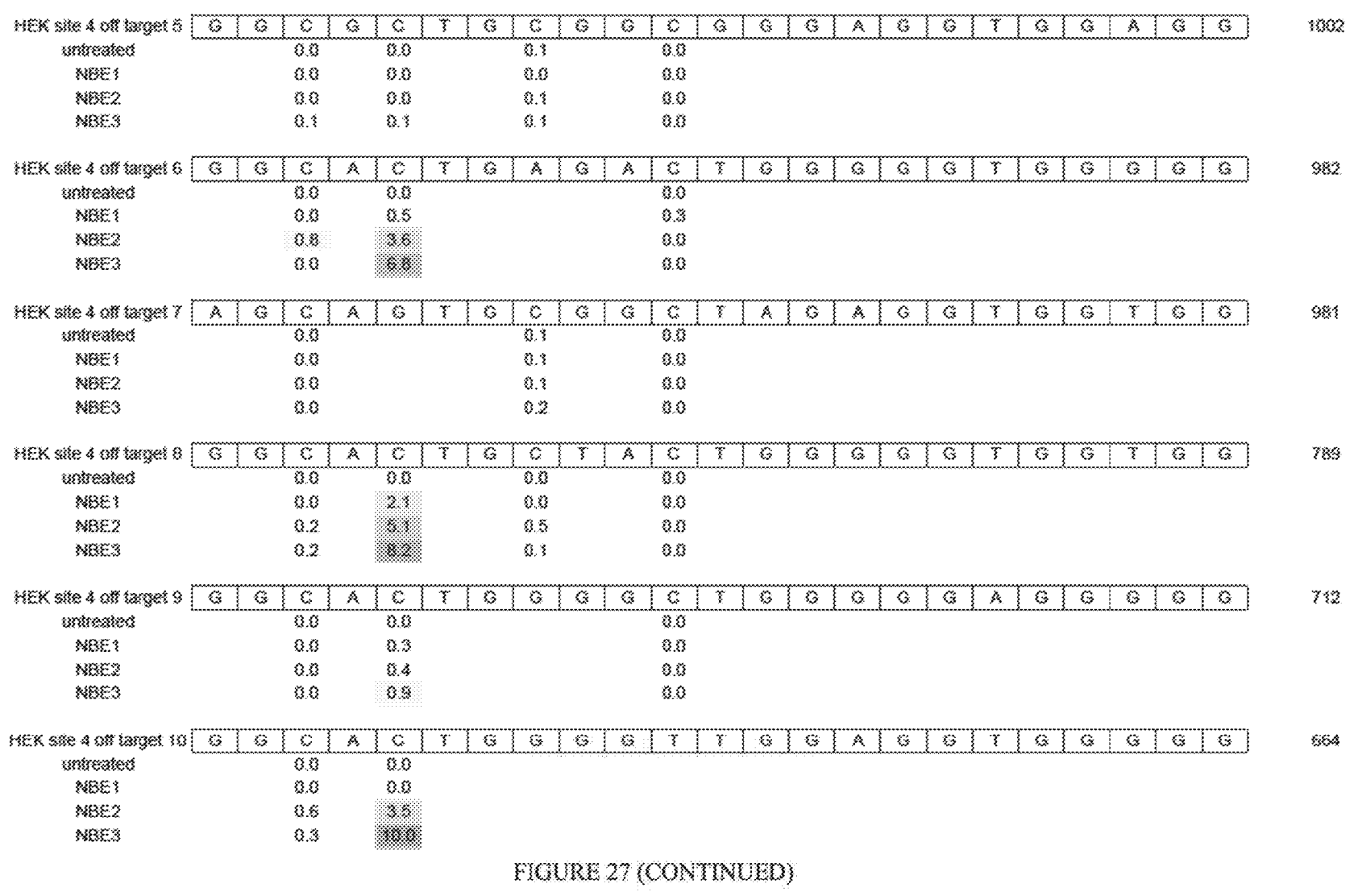

FIG. 27 shows activities of NBE1, NBE2, and NBE3 at HEK293 site 4 off-targets. HEK293T cells were transfected with plasmids expressing NBE1, NBE2, or NBE3 and a sgRNA matching the HEK293 site 4 sequence using Lipofectamine 2000. Three days after transfection, genomic DNA was extracted, amplified by PCR, and analyzed by high-throughput DNA sequencing at the on-target loci, plus the top ten known Cas9 off-target loci for the HEK293 site 4 sgRNA, as previously determined using the GUIDE-seq method[55]. Sequences of the on-target and off-target protospacers and protospacer adjacent motifs (PAMs) are displayed. Cellular C to T conversion percentages, defined as the percentage of total DNA sequencing reads with T at each position of an original C within the protospacer, are shown for NBE1, NBE2, and NBE3. On the far right are displayed the total number of sequencing reads reported for each sequence. This figure depicts SEQ ID NOs: 297 and 664 through 673 from top to bottom, respectively.

FIG. 29A shows possible base editing outcomes in mammalian cells. Initial editing resulted in a U:G mismatch. Recognition and excision of the U by uracil DNA glycosylase (UDG) initiated base excision repair (BER), which lead to reversion to the C:G starting state. BER was impeded by BE2 and BE3, which inhibited UDG. The U:G mismatch was also processed by mismatch repair (MMR), which preferentially repaired the nicked strand of a mismatch. BE3 nicked the non-edited strand containing the G, favoring resolution of the U:G mismatch to the desired U:A or T:A outcome. FIG. 29B shows HEK293T cells treated as described in the Materials and Methods in the Examples below. The percentage of total DNA sequencing read with Ts at the target positions indicated show treatment with BE1, BE2, or BE3, or for treatment with wt Cas9 with a donor HDR template. FIG. 29C shows frequency of indel formation following the treatment in FIG. 29B. Values are listed in FIG. 34. For FIGS. 29B and 29C, values and error bars reflect the mean and s.d. of three independent biological replicates performed on different days.

FIG. 30A shows the Alzheimer's disease-associated APOE4 allele converted to APOE3r in mouse astrocytes by BE3 in 74.9% of total reads. Two nearby Cs were also converted to Ts, but with no change to the predicted sequence of the resulting protein. Identical treatment of these cells with wt Cas9 and donor ssDNA results in only 0.3% correction, with 26.1% indel formation. FIG. 30B shows the cancer associated p53 Y163C mutation corrected by BE3 in 7.6% of nucleofected human breast cancer cells with 0.7% indel formation. Identical treatment of these cells with wt Cas9 and donor ssDNA results in no mutation correction with 6.1% indel formation. This figure depicts SEQ ID NOs: 675 to 680 from top to bottom, respectively.

Figure 32:
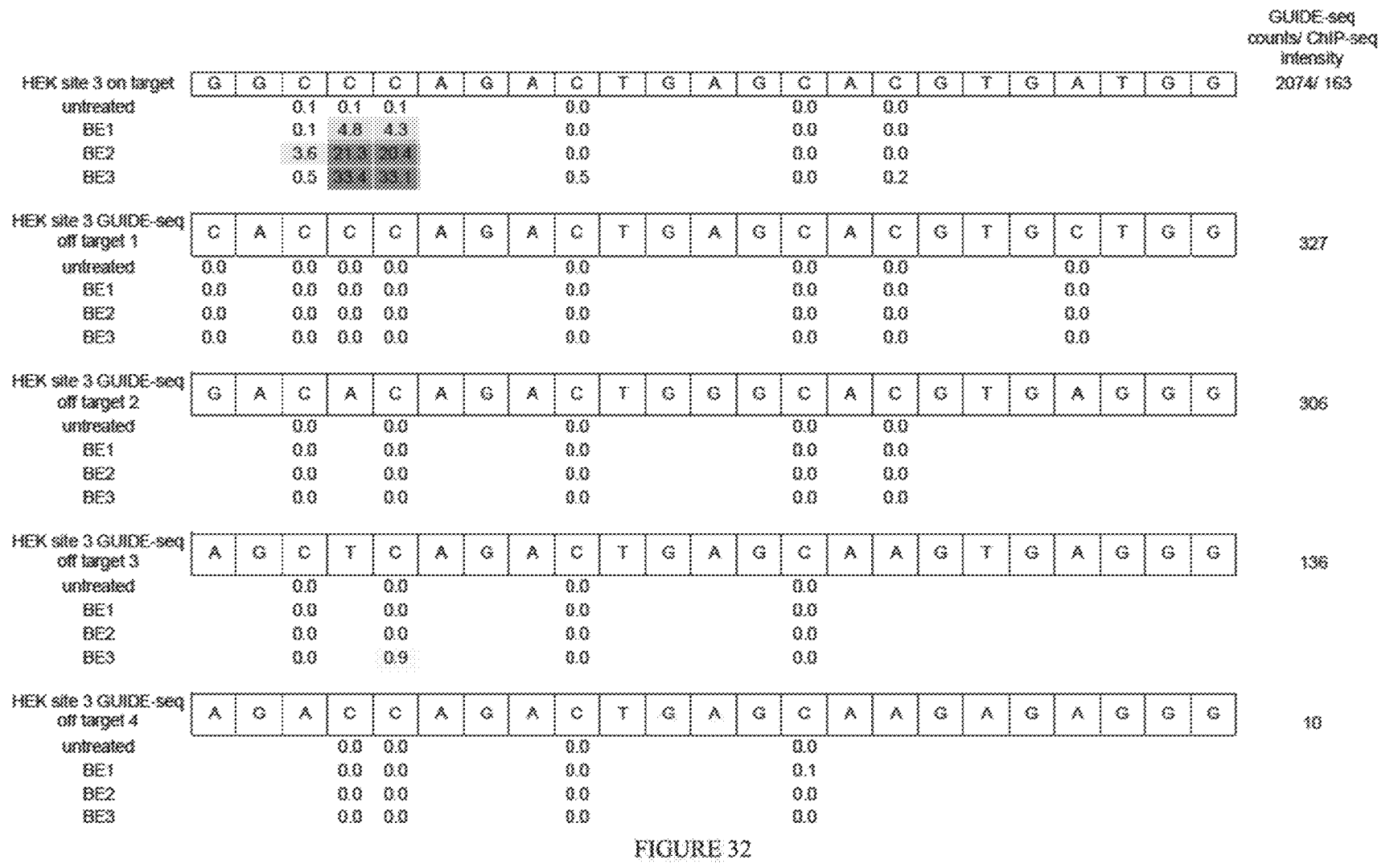
Figure 32:
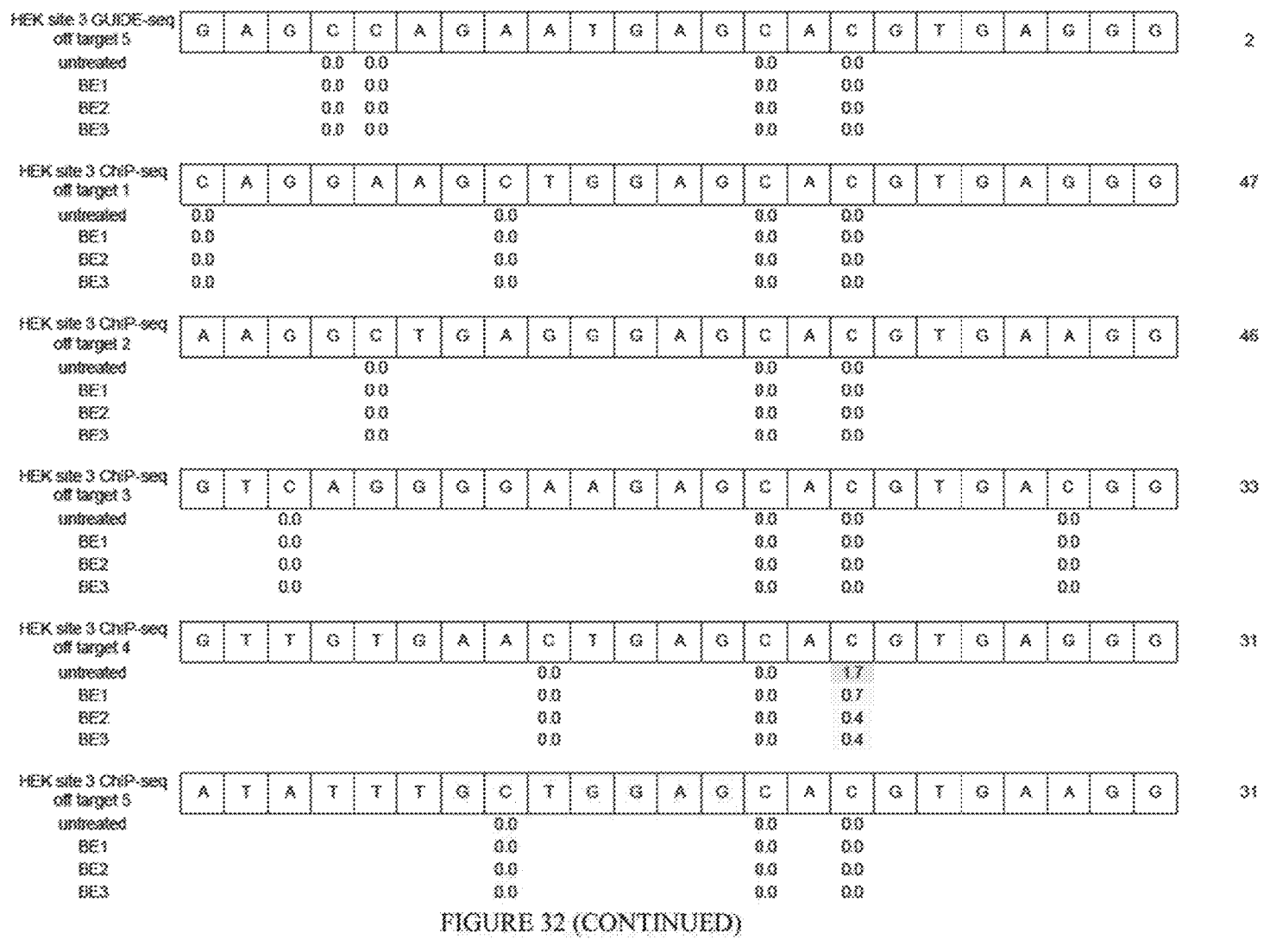

FIG. 32 shows activities of BE1, BE2, and BE3 at HEK293 site 3 off-targets. HEK293T cells were transfected with plasmids expressing BE1, BE2, or BE3 and a sgRNA matching the HEK293 site 3 sequence using Lipofectamine 2000. Three days after transfection, genomic DNA was extracted, amplified by PCR, and analyzed by high-throughput DNA sequencing at the on-target loci, plus all of the known Cas9 off-target loci and the top five known dCas9 off-target loci for the HEK293 site 3 sgRNA, as previously determined by Joung and coworkers using the GUIDE-seq method[54], and using chromatin immunoprecipitation high-throughput sequencing (ChIP-seq) experiments[61]. Sequences of the on-target and off-target protospacers and protospacer adjacent motifs (PAMs) are displayed. Cellular C to T conversion percentages, defined as the percentage of total DNA sequencing reads with T at each position of an original C within the protospacer, are shown for BE1, BE2, and BE3. On the far right are displayed the total number of sequencing reads reported, and the ChIP-seq signal intensity reported for each sequence. This figure depicts SEQ ID NOs: 689 to 699 from top to bottom, respectively.

Figure 33:
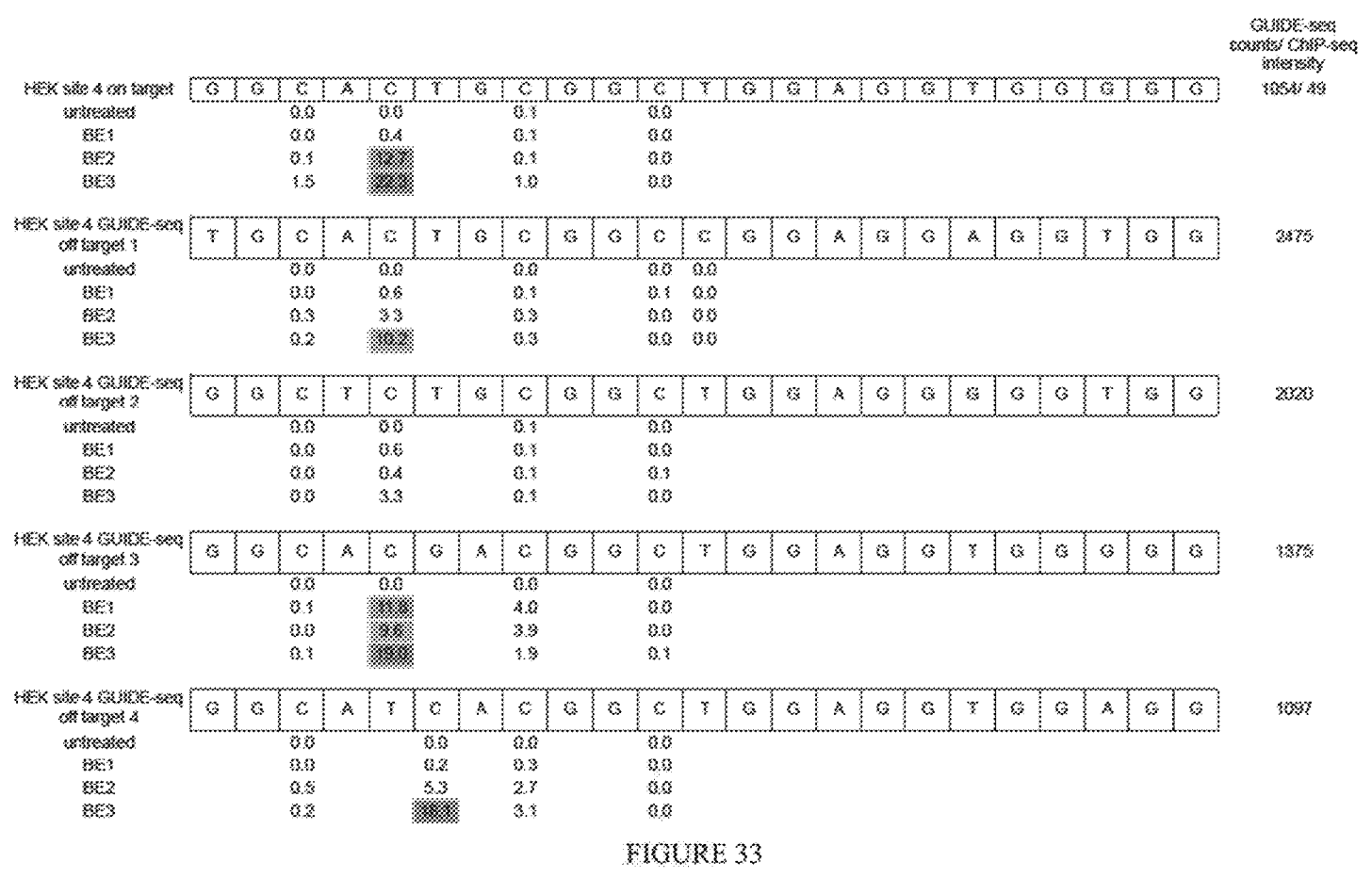
Figure 33:
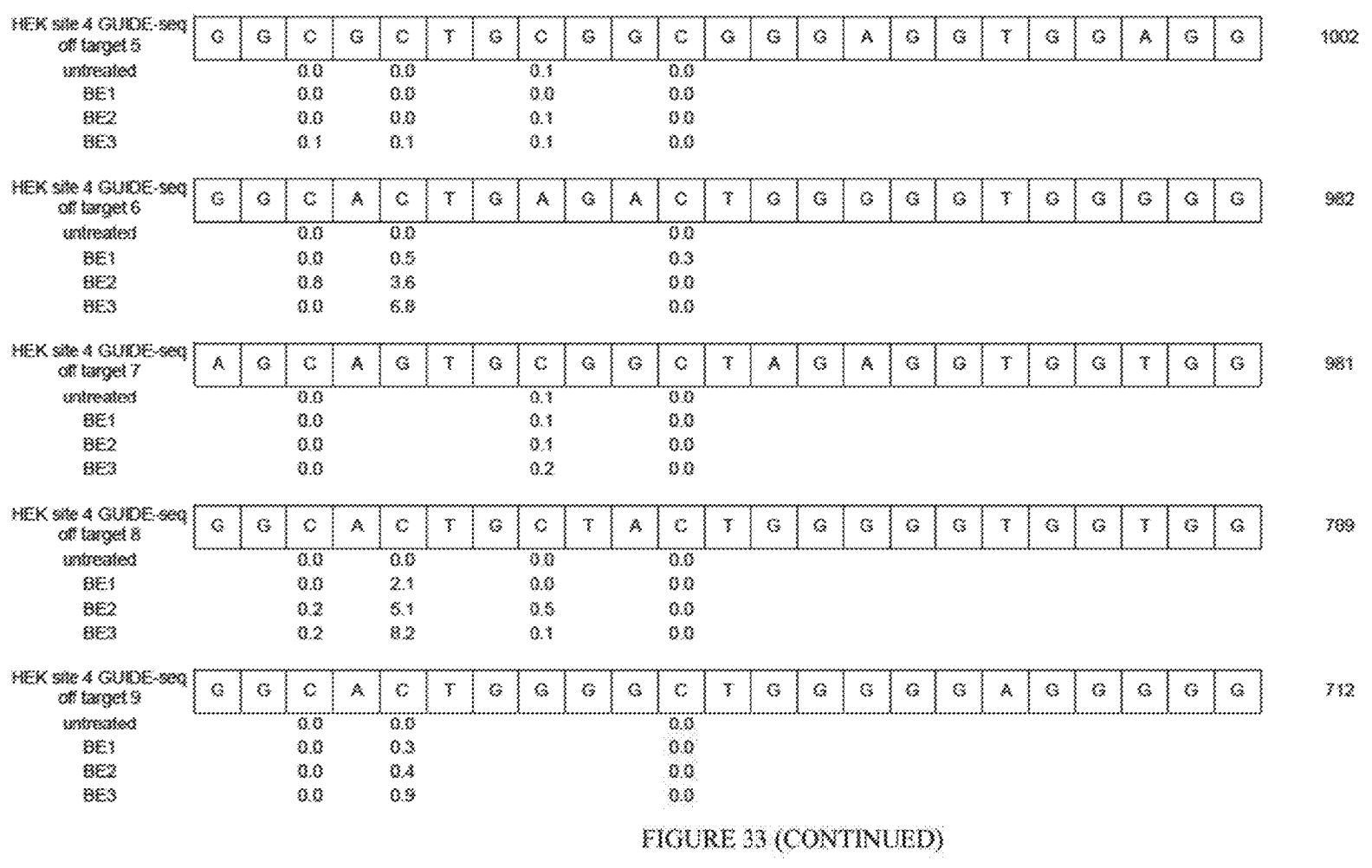
Figure 33:
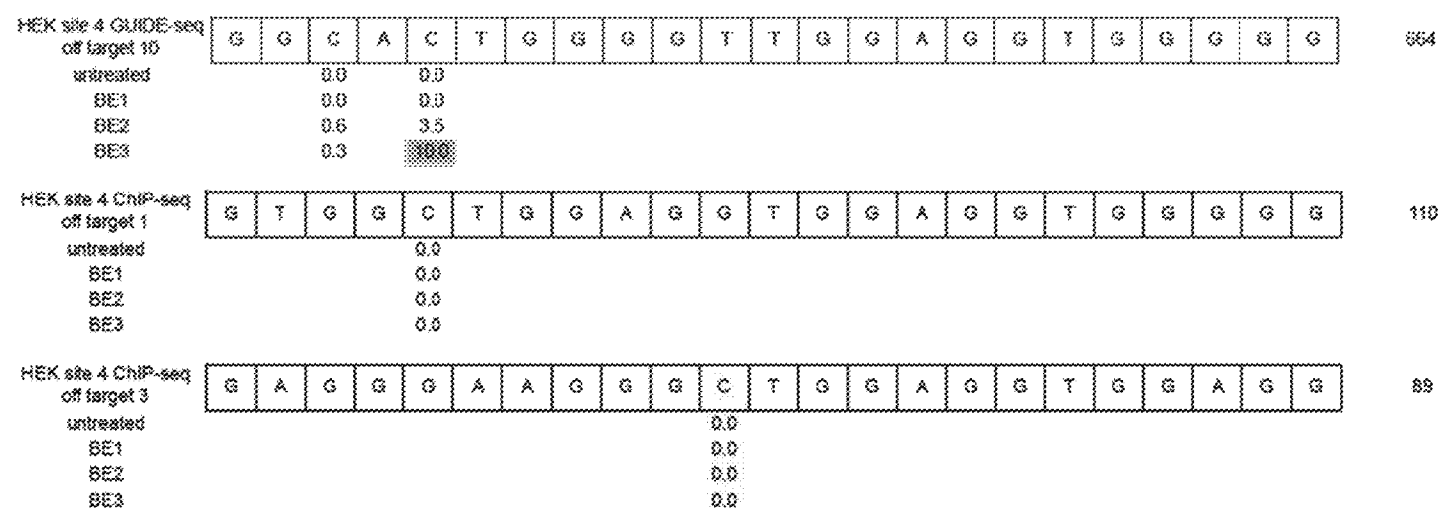

FIG. 33 shows activities of BE1, BE2, and BE3 at HEK293 site 4 off-targets. HEK293T cells were transfected with plasmids expressing BE1, BE2, or BE3 and a sgRNA matching the HEK293 site 4 sequence using Lipofectamine 2000. Three days after transfection, genomic DNA was extracted, amplified by PCR, and analyzed by high-throughput DNA sequencing at the on-target loci, plus the top ten known Cas9 off-target loci and the top five known dCas9 off-target loci for the HEK293 site 4 sgRNA, as previously determined using the GUIDE-seq method[54], and using chromatin immunoprecipitation high-throughput sequencing (ChIP-seq) experiments[61]. Sequences of the on-target and off-target protospacers and protospacer adjacent motifs (PAMs) are displayed. Cellular C to T conversion percentages, defined as the percentage of total DNA sequencing reads with T at each position of an original C within the protospacer, are shown for BE1, BE2, and BE3. On the far right are displayed the total number of sequencing reads reported, and the ChIP-seq signal intensity reported for each sequence. This figure depicts SEQ ID NOs: 700 to 712 from top to bottom, respectively.

FIG. 34 shows mutation rates of non-protospacer bases following BE3-mediated correction of the Alzheimer's disease-associated APOE4 allele to APOE3r in mouse astrocytes. The DNA sequence of the 50 bases on either side of the protospacer from FIG. 30A and FIG. 34B is shown with each base's position relative to the protospacer. The side of the protospacer distal to the PAM is designated with positive numbers, while the side that includes the PAM is designated with negative numbers, with the PAM shown in blue. Underneath each sequence are the percentages of total DNA sequencing reads with the corresponding base for untreated cells, for cells treated with BE3 and an sgRNA targeting the APOE4 C158R mutation, or for cells treated with BE3 and an sgRNA targeting the VEGFA locus. Neither BE3-treated sample resulted in mutation rates above those of untreated controls. This figure depicts SEQ ID NOs: 713 to 716 from top to bottom, respectively.

FIG. 35 shows mutation rates of non-protospacer bases following BE3-mediated correction of the cancer-associated p53 Y163C mutation in HCC1954 human cells. The DNA sequence of the 50 bases on either side of the protospacer from FIG. 30B and FIG. 39B is shown with each base's position relative to the protospacer. The side of the protospacer distal to the PAM is designated with positive numbers, while the side that includes the PAM is designated with negative numbers, with the PAM shown in blue. Underneath each sequence are the percentages of total sequencing reads with the corresponding base for untreated cells, for cells treated with BE3 and an sgRNA targeting the TP53 Y163C mutation, or for cells treated with BE3 and an sgRNA targeting the VEGFA locus. Neither BE3-treated sample resulted in mutational rates above those of untreated controls. This figure depicts SEQ ID NOs: 717 to 720 from top to bottom, respectively.

FIGS. 36A to 36F show the effects of deaminase, linker length, and linker composition on base editing. FIG. 36A shows a gel-based deaminase assay showing activity of rAPOBEC1, pmCDA1, hAID, hAPOBEC3G, rAPOBEC1-GGS-dCas9, rAPOBEC1-(GGS)$_3$(SEQ ID NO: 596)-dCas9, and dCas9-(GGS)$_3$(SEQ ID NO: 596)-rAPOBEC1 on ssDNA. Enzymes were expressed in a mammalian cell lysate-derived in vitro transcription-translation system and incubated with 1.8 µM dye-conjugated ssDNA and USER enzyme (uracil DNA glycosylase and endonuclease VIII) at 37° C. for 2 hours. The resulting DNA was resolved on a denaturing polyacrylamide gel and imaged. The positive control is a sequence with a U synthetically incorporated at the same position as the target C. FIG. 36B shows coomassie-stained denaturing PAGE gel of the expressed and purified proteins used in FIGS. 36C to 36F. FIGS. 36C to 36F show gel-based deaminase assay showing the deamination window of base editors with deaminase-Cas9 linkers of GGS (FIG. 36C), (GGS)$_3$ (SEQ ID NO: 596) (FIG. 36D), XTEN (FIG. 36E), or (GGS)$_7$ (SEQ ID NO: 597) (FIG. 36F). Following incubation of 1.85 µM deaminase-dCas9 fusions complexed with sgRNA with 125 nM dsDNA substrates at 37° C. for 2 hours, the dye-conjugated DNA was isolated and incubated with USER enzyme at 37° C. for 1 hour to cleave the DNA backbone at the site of any uracils. The resulting DNA was resolved on a denaturing polyacrylamide gel, and the dye-conjugated strand was imaged. Each lane is numbered according to the position of the target C within the protospacer, or with—if no target C is present. 8U is a positive control sequence with a U synthetically incorporated at position 8.

FIGS. 37A to 37C show BE1 base editing efficiencies are dramatically decreased in mammalian cells. FIG. 37A Protospacer (black and red) and PAM (blue) sequences of the six mammalian cell genomic loci targeted by base editors. Target Cs are indicated in red with subscripted numbers corresponding to their positions within the protospacer. FIG. 37B shows synthetic 80-mers with sequences matching six different genomic sites were incubated with BE1 then analyzed for base editing by HTS. For each site, the sequence of the protospacer is indicated to the right of the name of the site, with the PAM highlighted in blue. Underneath each sequence are the percentages of total DNA sequencing reads with the corresponding base. We considered a target C as "editable" if the in vitro conversion efficiency is >10%. Note that maximum yields are 50% of total DNA sequencing reads since the non-targeted strand is unaffected by BEL Values are shown from a single experiment. FIG. 37C shows HEK293T cells were transfected with plasmids expressing BE1 and an appropriate sgRNA. Three days after transfection, genomic DNA was extracted and analyzed by high-throughput DNA sequencing at the six loci. Cellular C to T conversion percentages, defined as the percentage of total DNA sequencing reads with Ts at the target positions indicated, are shown for BE1 at all six genomic loci. Values and error bars of all data from HEK293T cells reflect the mean and standard deviation of three independent biological replicates performed on different days. FIG. 37A depicts SEQ ID NOs: 721 to 726 from top to bottom, respectively. FIG. 37B depicts SEQ ID NOs: 727 to 732 from top to bottom, respectively.

FIGS. 39A to 39C show non-target C/G mutation rates. Shown here are the C to T and G to A mutation rates at 2,500 distinct cytosines and guanines surrounding the six on-target and 34 off-target loci tested, representing a total of 14,700,000 sequence reads derived from approximately 1.8×10⁶ cells. FIGS. 39A and 39B show cellular non-target C to T and G to A conversion percentages by BE1, BE2, and BE3 are plotted individually against their positions relative to a protospacer for all 2,500 cytosines/guanines. The side of the protospacer distal to the PAM is designated with positive numbers, while the side that includes the PAM is designated with negative numbers. FIG. 39C shows average non-target cellular C to T and G to A conversion percentages by BE1, BE2, and BE3 are shown, as well as the highest and lowest individual conversion percentages.

FIG. 40A shows the Alzheimer's disease-associated APOE4 allele is converted to APOE3r in mouse astrocytes by BE3 in 58.3% of total reads only when treated with the correct sgRNA. Two nearby Cs are also converted to Ts, but with no change to the predicted sequence of the resulting protein. Identical treatment of these cells with wt Cas9 and donor ssDNA results in 0.2% correction, with 26.7% indel formation. FIG. 40B shows the cancer-associated p53 Y163C mutation is corrected by BE3 in 3.3% of nucleofected human breast cancer cells only when treated with the correct sgRNA. Identical treatment of these cells with wt Cas9 and donor ssDNA results in no detectable mutation correction with 8.0% indel formation. FIGS. 40A to 40B depict SEQ ID NOs: 733 to 740 from top to bottom, respectively.

FIGS. 53A to 53B demonstrated DNA correction induction of two constructs.

Figure 56:
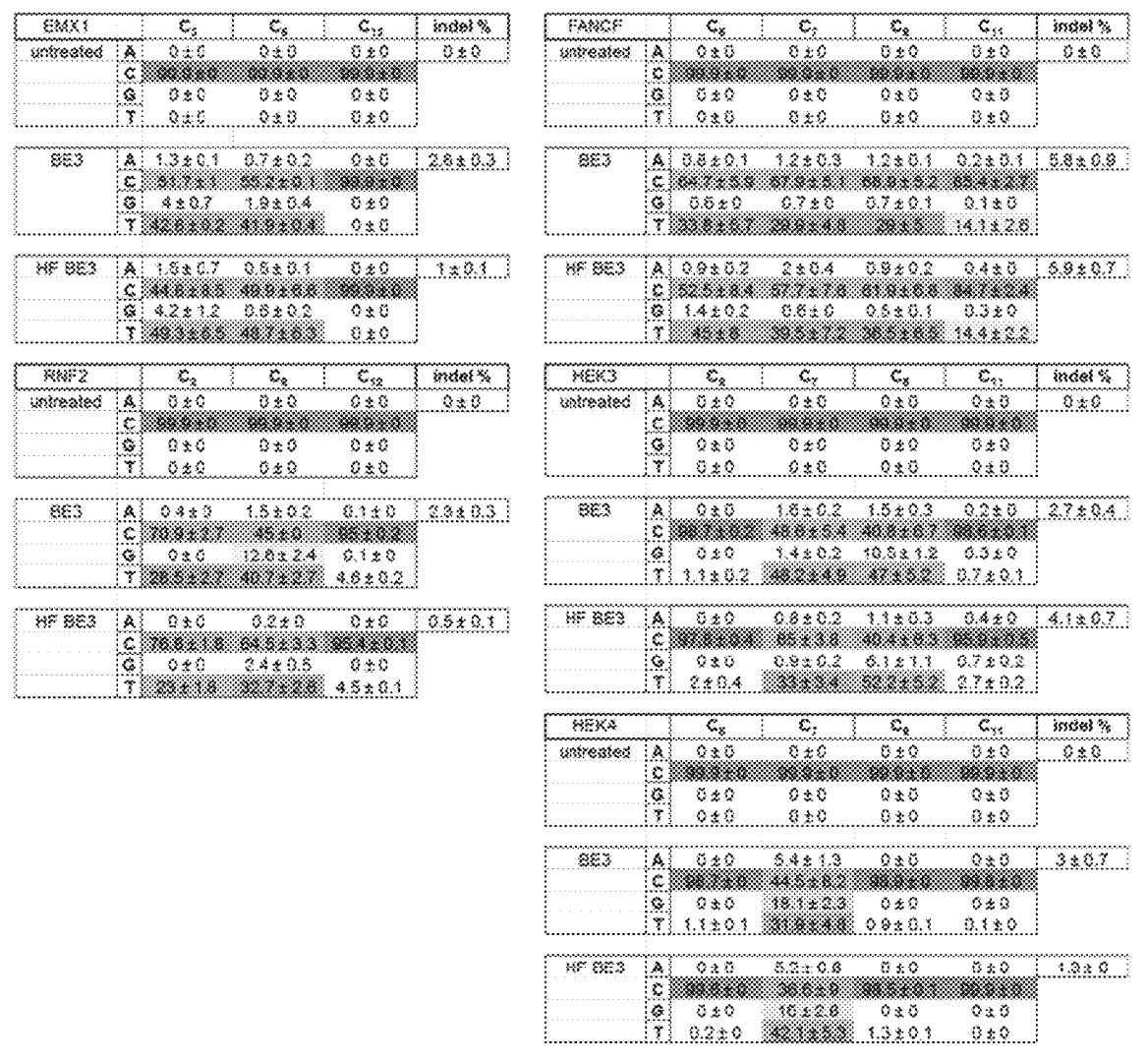

FIG. 56 shows on-target base editing efficiencies of BE3 and HF-BE3.

$$\text{TTTCCTC}_3\text{C}_4\text{C}_5\text{C}_6\text{C}_7\text{C}_8\text{C}_9\text{AC}_{11}\text{AGGTAGAACAT}, \quad \text{(FIG. 64A, SEQ ID NO: 305)}$$

$$\text{TTTCC}_1\text{C}_2\text{TC}_4\text{TGTC}_8\text{C}_9\text{AC}_{11}\text{ACCCTCATCCTG}, \quad \text{(FIG. 64B, SEQ ID NO: 306)}$$
and $$\text{TTTCC}_1\text{C}_2\text{C}_3\text{AGTC}_7\text{C}_8\text{TC}_{10}\text{C}_{11}\text{AC}_{13}\text{AC}_{15}\text{C}_{16}\text{C}_{17}\text{TGAAAC}. \quad \text{(FIG. 64C, SEQ ID NO: 307)}$$

Figure 65:
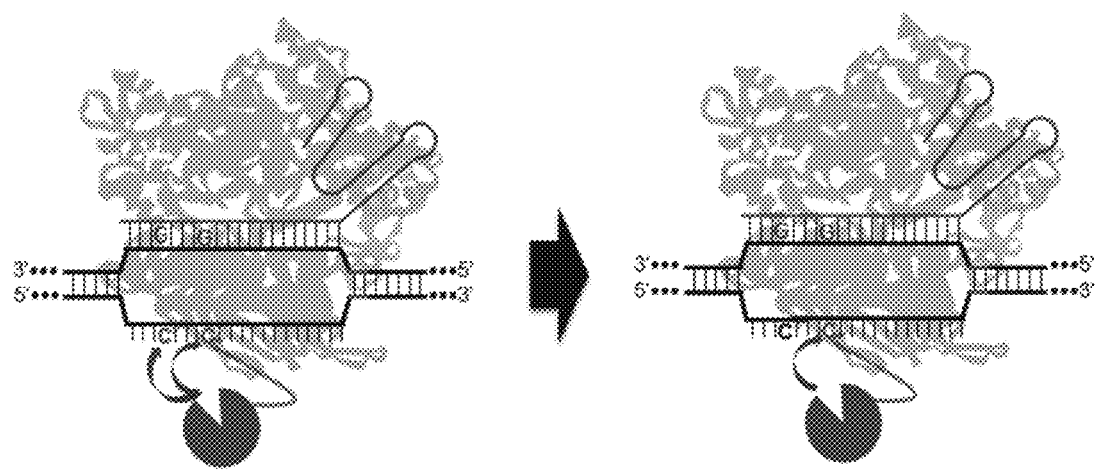

FIG. 65 is a schematic depicting selective deamination as achieved through kinetic modulation of cytidine deaminase point mutagenesis.

Figure 66:
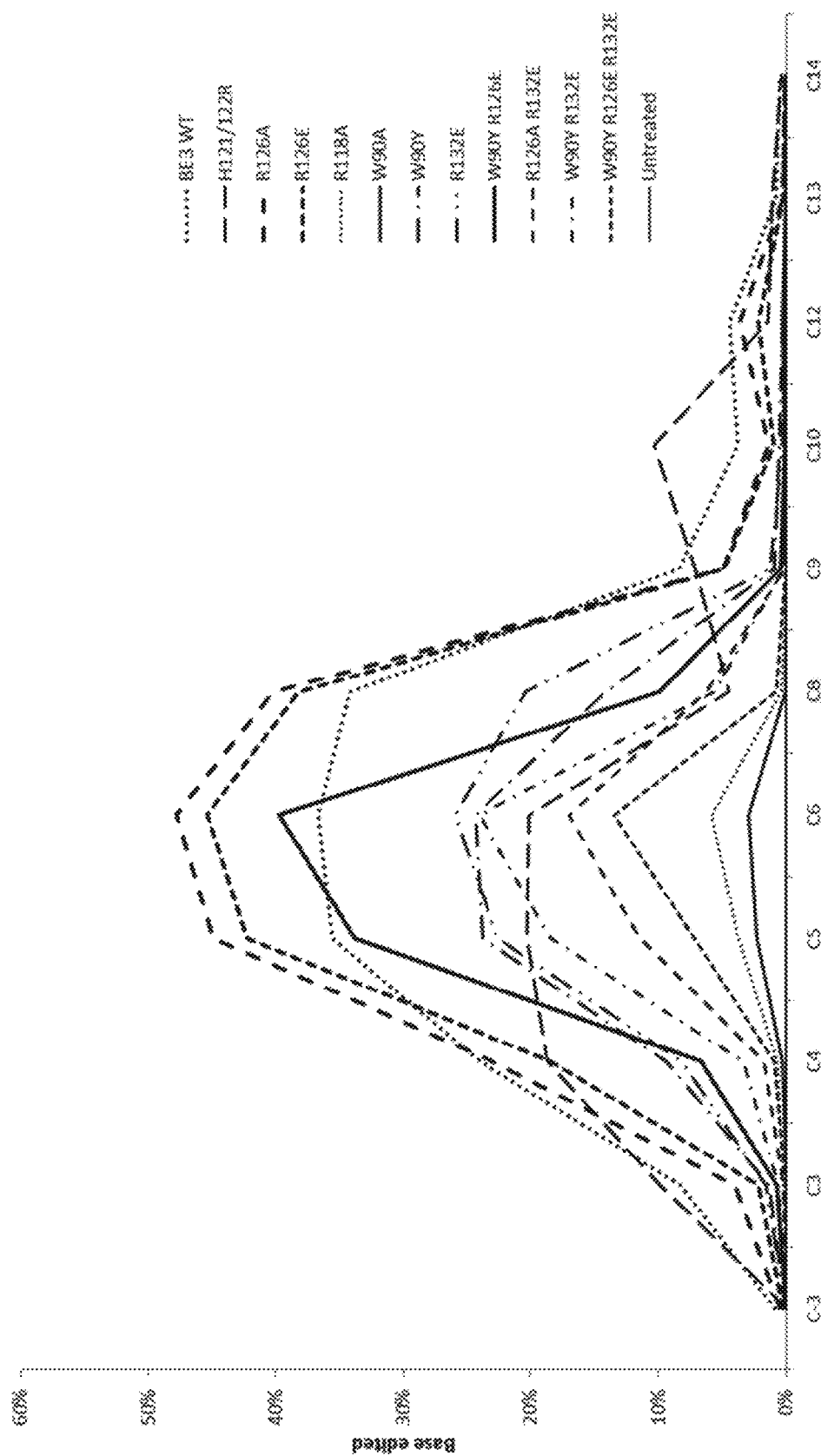

FIG. 66 is a graph showing the effect of various mutations on the deamination window probed in cell culture with multiple cytidines in the spacer. The spacer used was:

$$\text{TGC}_3\text{C}_4\text{C}_5\text{C}_6\text{TC}_8\text{C}_9\text{C}_{10}\text{TC}_{12}\text{C}_{13}\text{C}_{14}\text{TGGCCC}. \quad \text{(SEQ ID NO: 308)}$$

Figure 67:
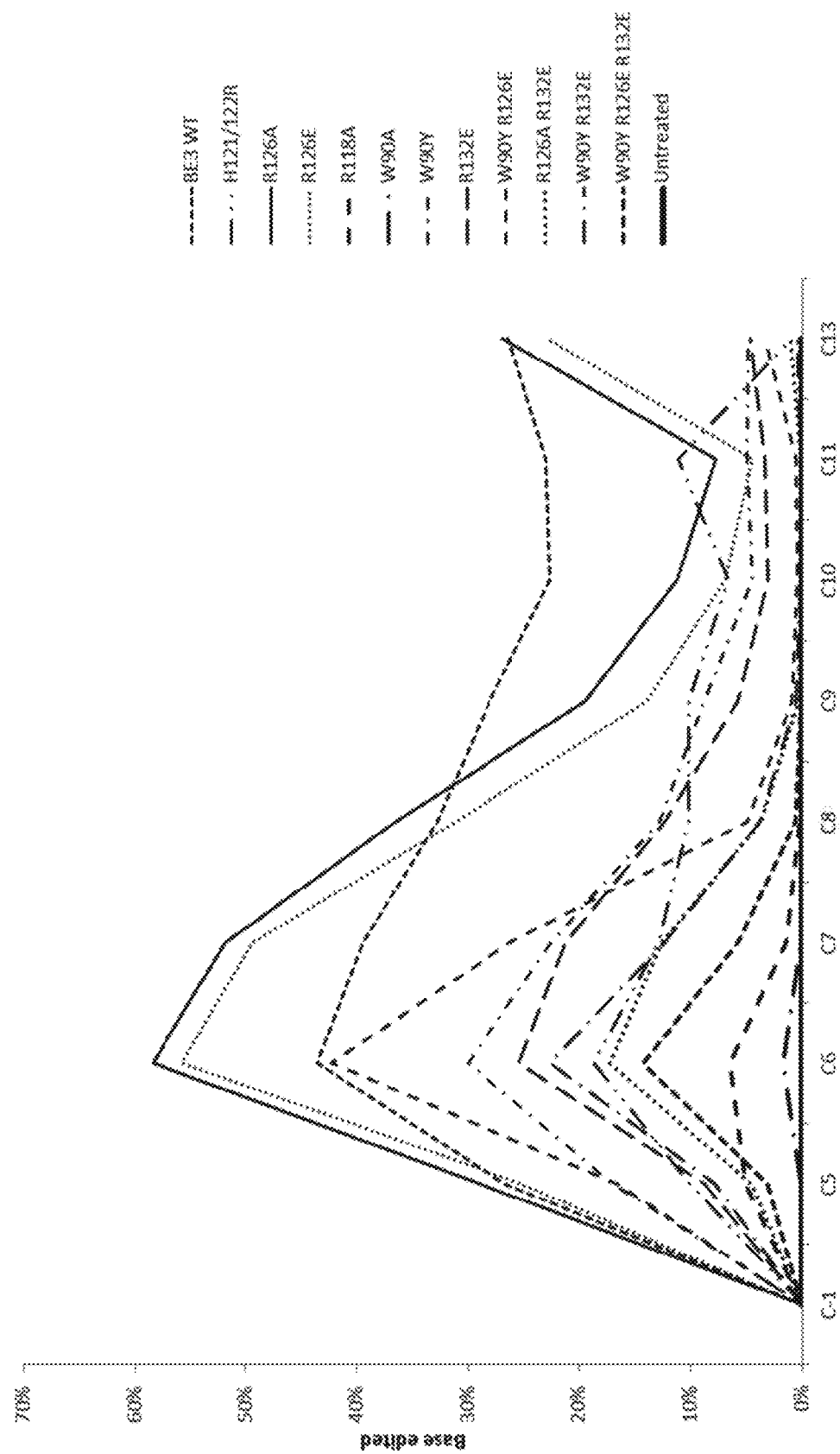

FIG. 67 is a graph showing the effect of various mutations on the deamination window probed in cell culture with multiple cytidines in the spacer. The spacer used was:

$$\text{AGAGC}_5\text{C}_6\text{C}_7\text{C}_8\text{C}_9\text{C}_{10}\text{C}_{11}\text{TC}_{13}\text{AAAGAGA}. \quad \text{(SEQ ID NO: 309)}$$

Figure 68:
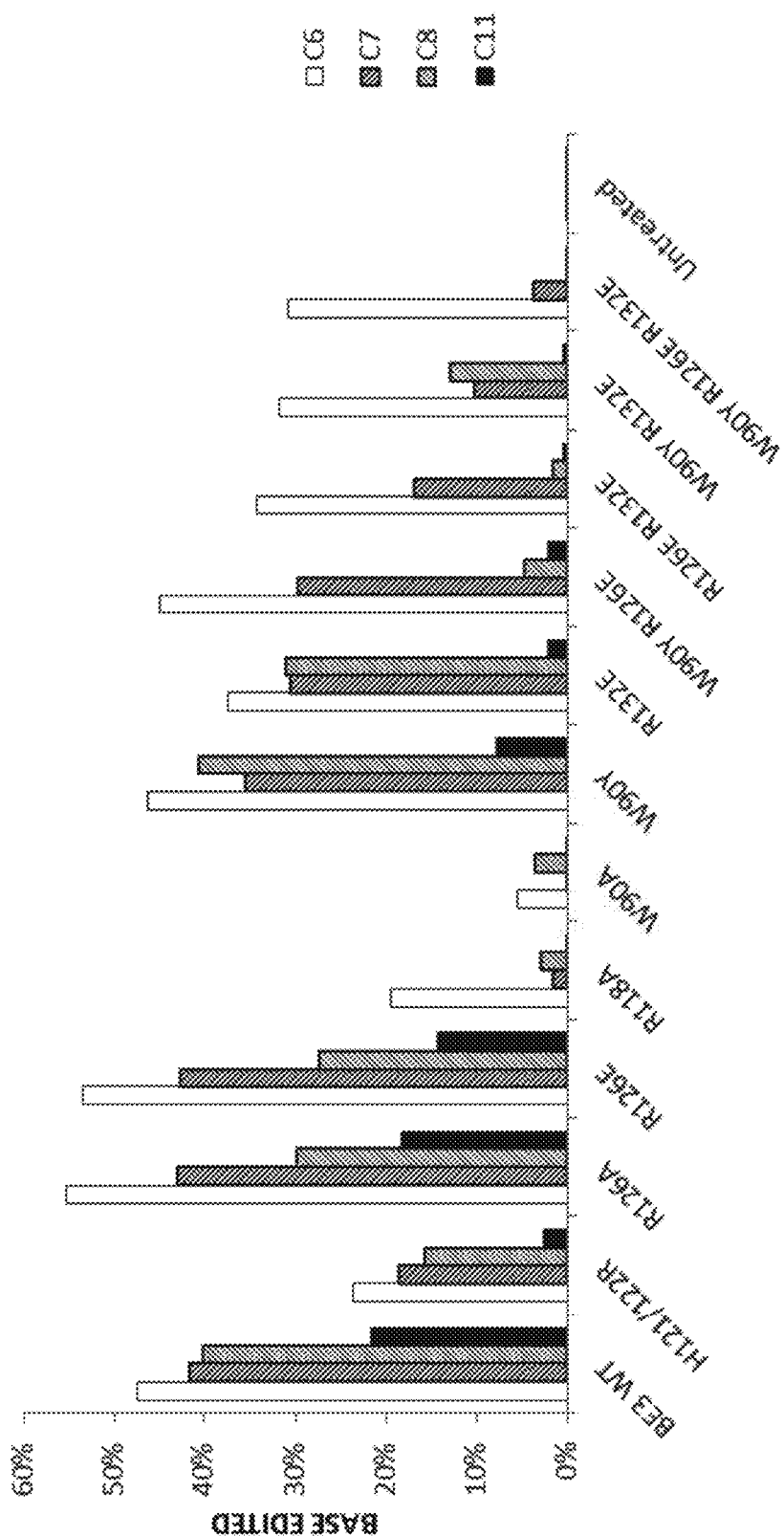

FIG. 68 is a graph showing the effect of various mutations on the FANCF site with a limited number of cytidines. The spacer used was: $GGAATC_6C_7C_8TTC_{11}TGCAGCACCTGG$ (SEQ ID NO: 303). Note that the triple mutant (W90Y, R126E, R132E) preferentially edits the cytidine at the sixth position.

Figure 69:
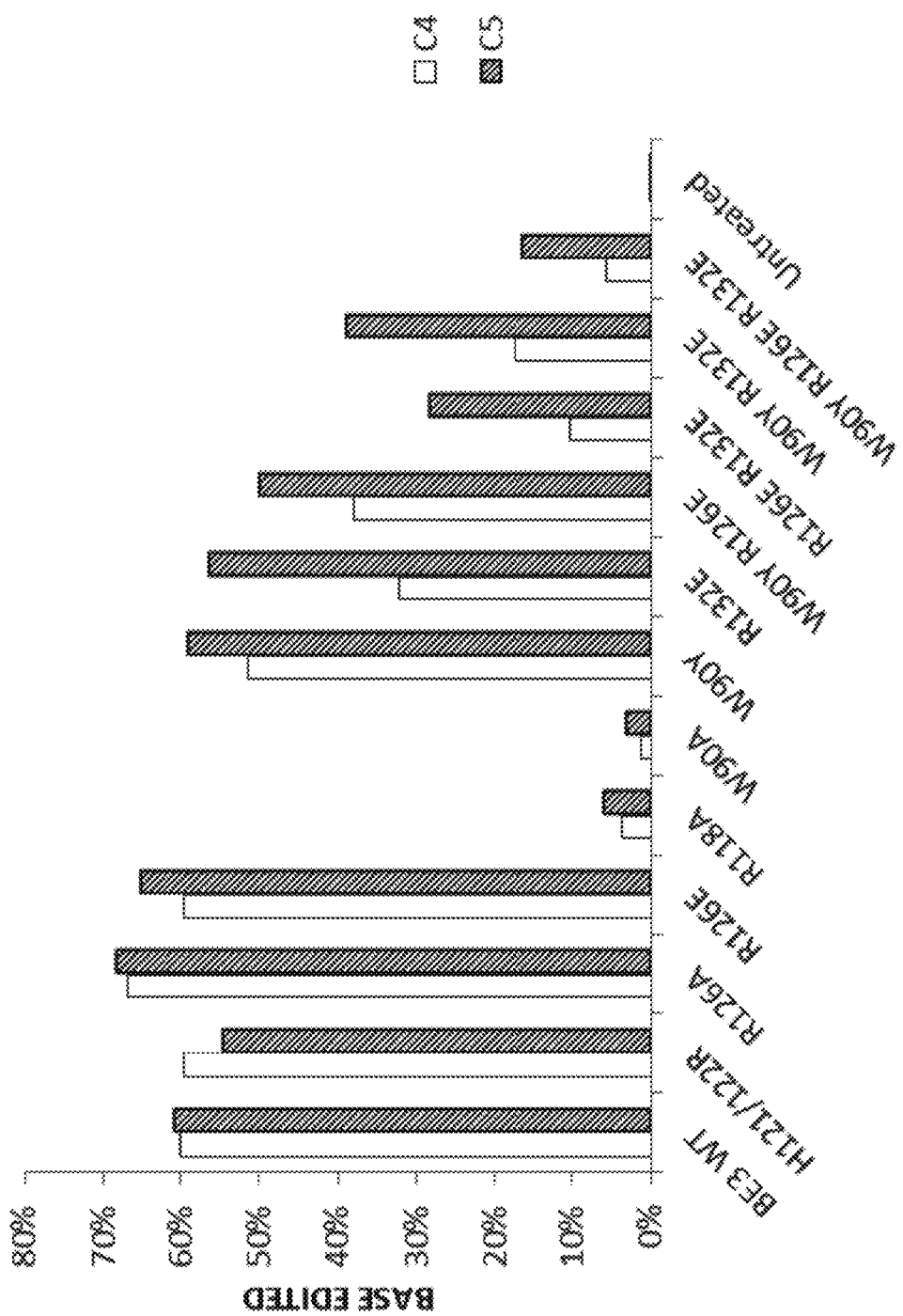

FIG. 69 is a graph showing the effect of various mutations on the HEK3 site with a limited number of cytidines. The spacer used was: $GGCC_4C_5AGACTGAGCACGTGATGG$ (SEQ ID NO: 310). Note that the double and triple mutants preferentially edit the cytidine at the fifth position over the cytidine in the fourth position.

Figure 70:
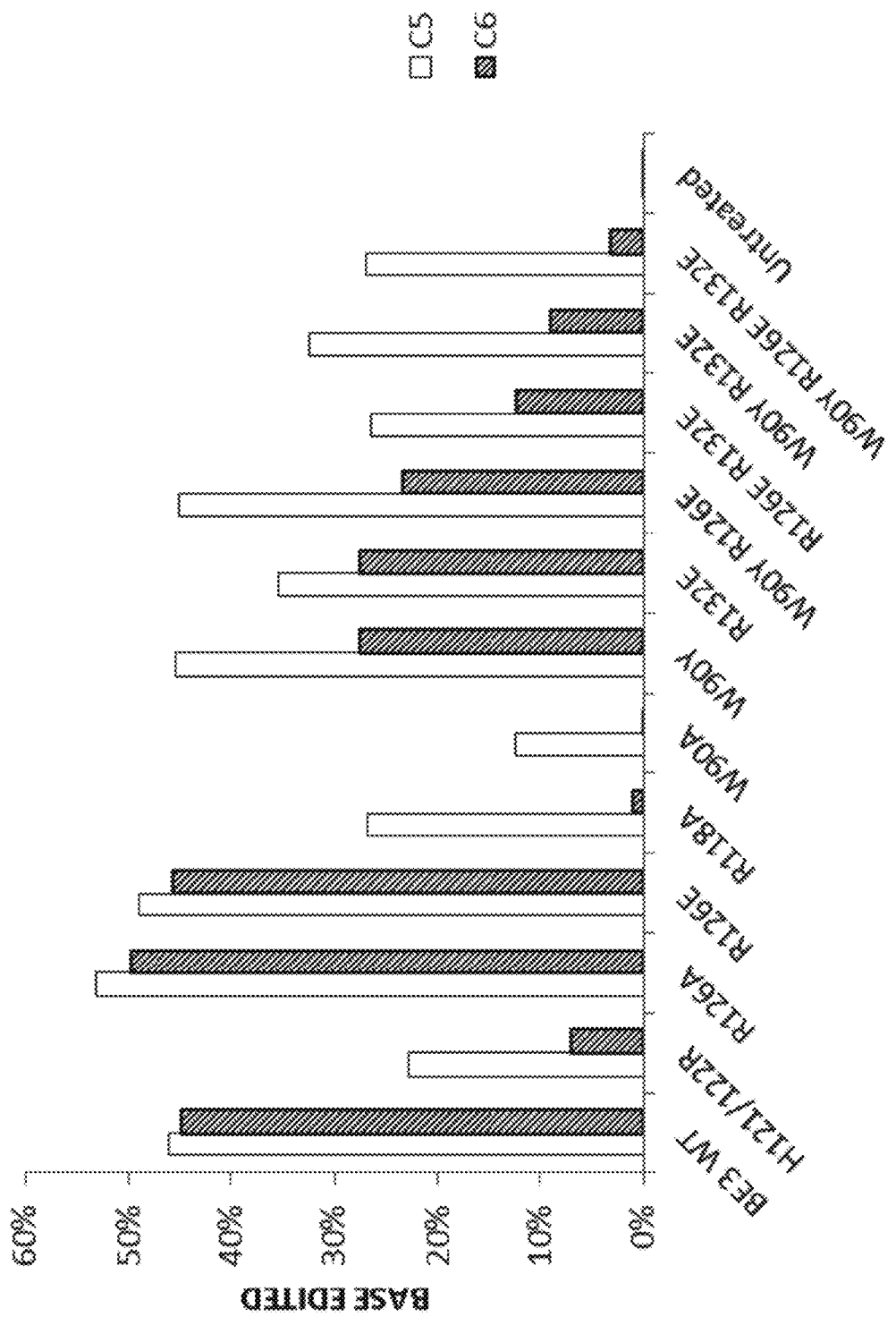

FIG. 70 is a graph showing the effect of various mutations on the EMX1 site with a limited number of cytidines. The spacer used was: $GAGTC_5C_6GAGCAGAAGAAGAAGGG$ (SEQ ID NO: 311). Note that the triple mutant only edits the cytidine at the fifth position, not the sixth.

Figure 71:
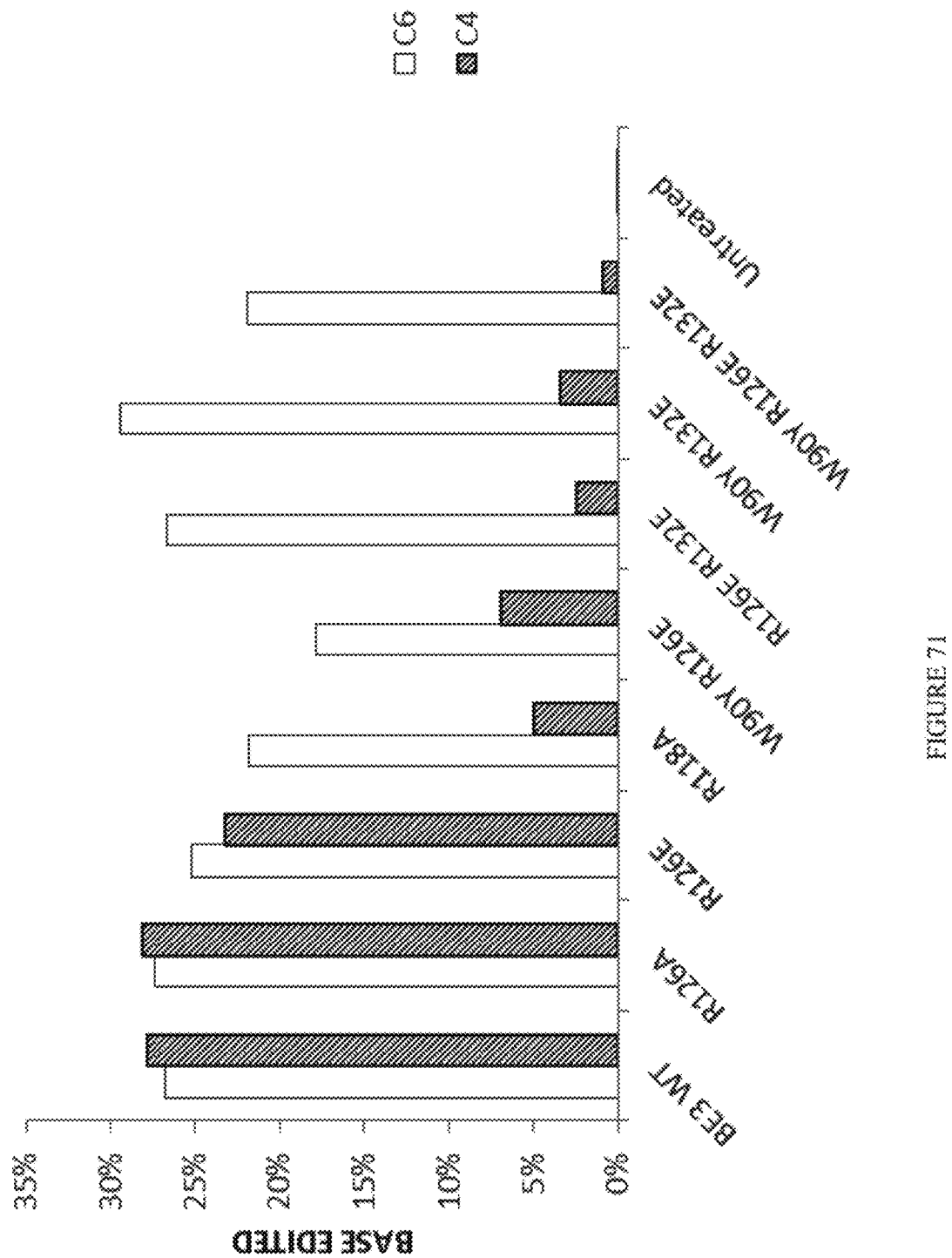

FIG. 71 is a graph showing the effect of various mutations on the HEK2 site with a limited number of cytidines. The spacer used was:

$$\text{GAAC}_4\text{AC}_6\text{AAAGCATAGACTGCGGG}. \quad \text{(SEQ ID NO: 312)}$$

Figure 72:
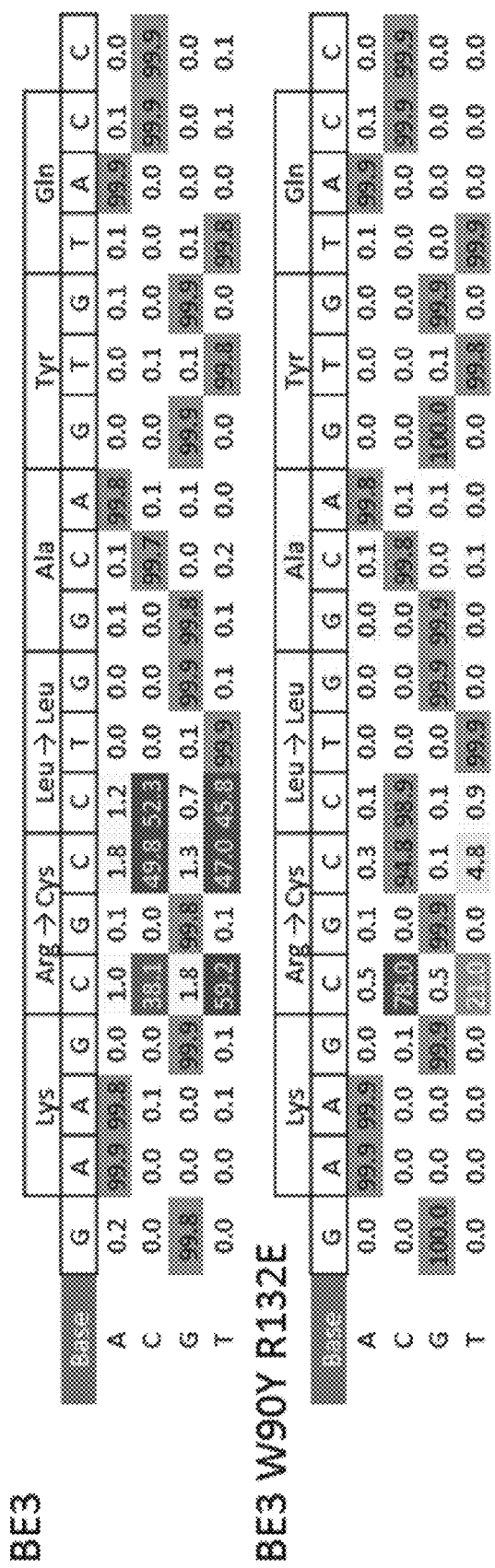

FIG. 72 shows on-target base editing efficiencies of BE3 and BE3 comprising mutations W90Y R132E in immortalized astrocytes.

Figure 73:
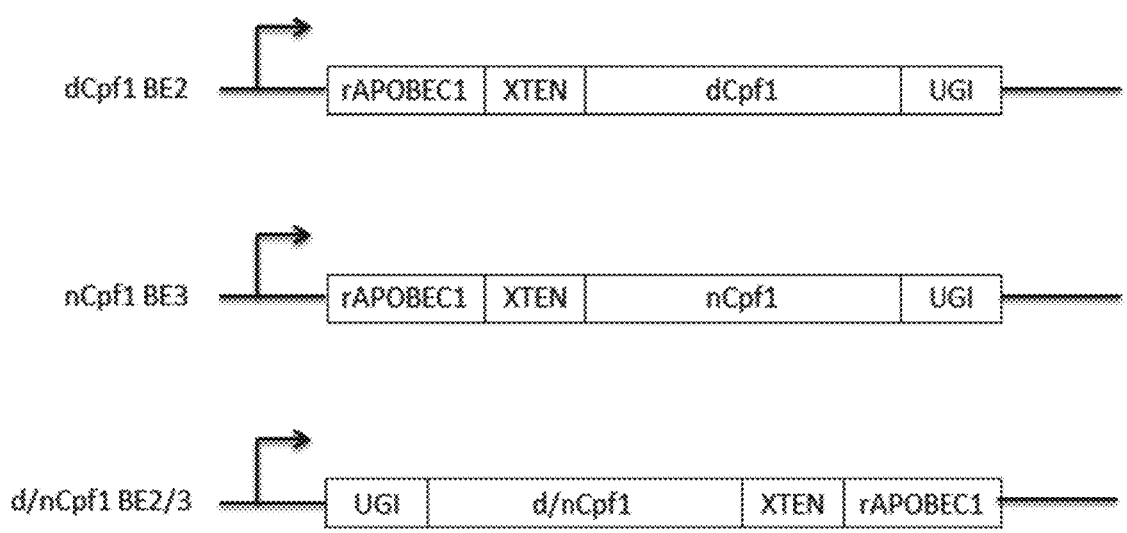

FIG. 73 depicts a schematic of three Cpf1 fusion constructs.

Figure 74:
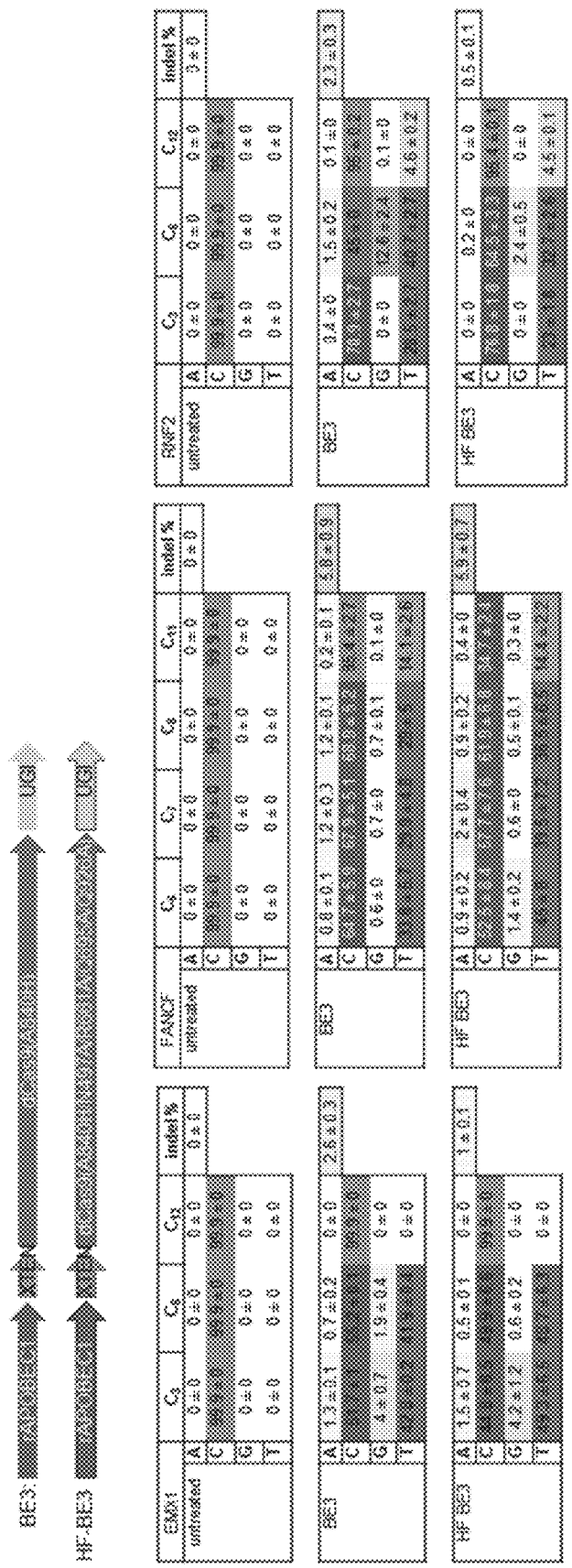

FIG. 74 shows a comparison of plasmid delivery of BE3 and HF-BE3 (EMX1, FANCF, and RNF2).

Figure 75:
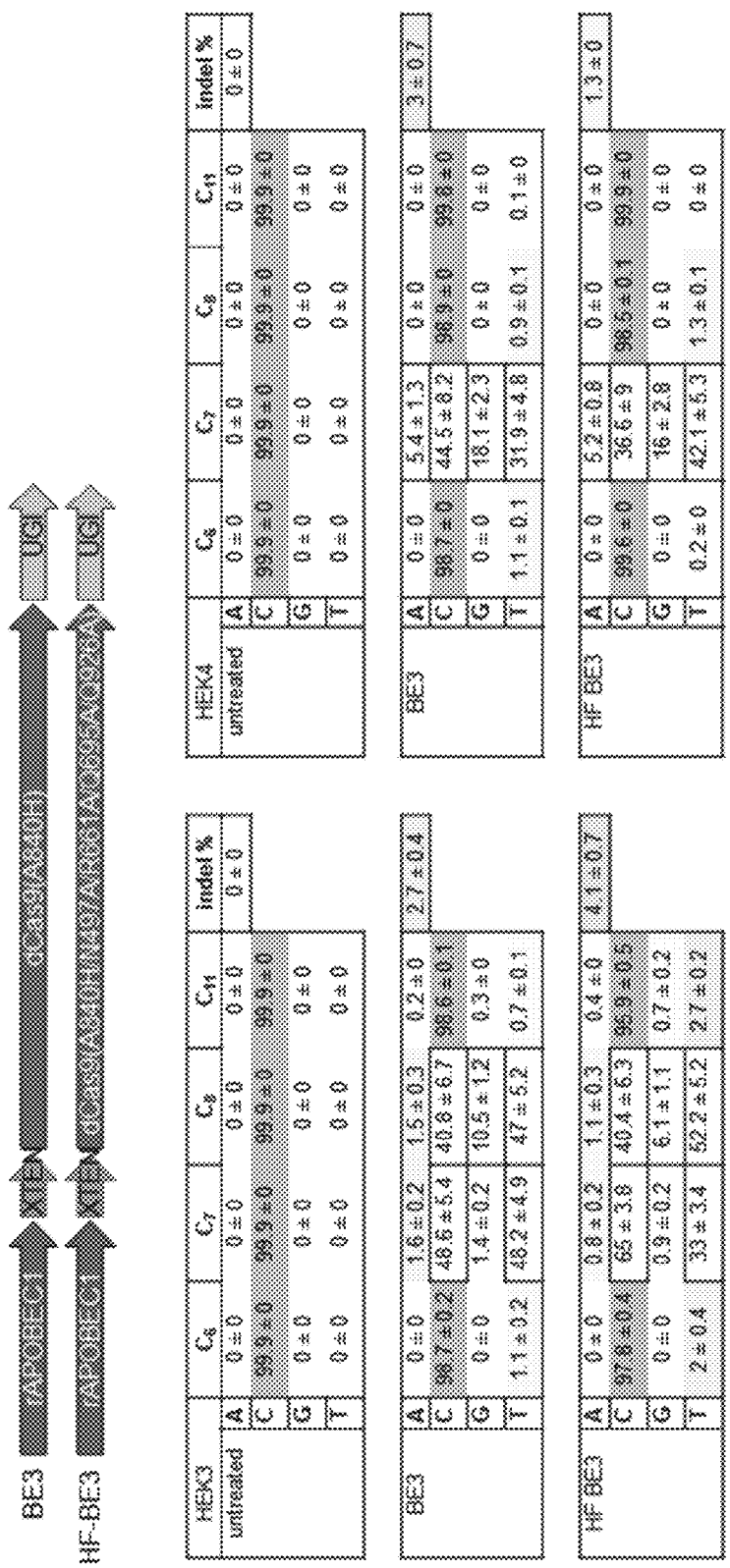

FIG. 75 shows a comparison of plasmid delivery of BE3 and HF-BE3 (HEK3 and HEK 4).

Figure 76:
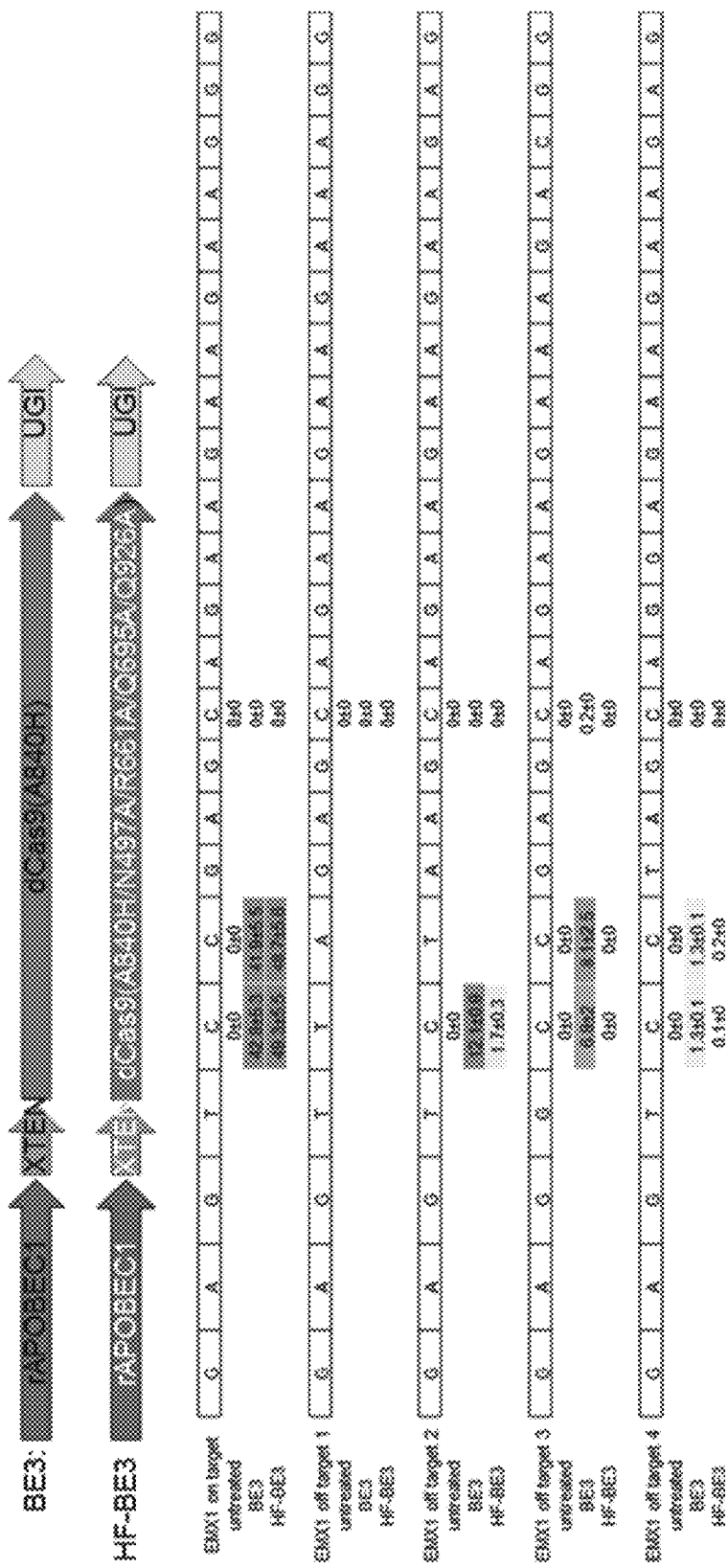
Figure 76:
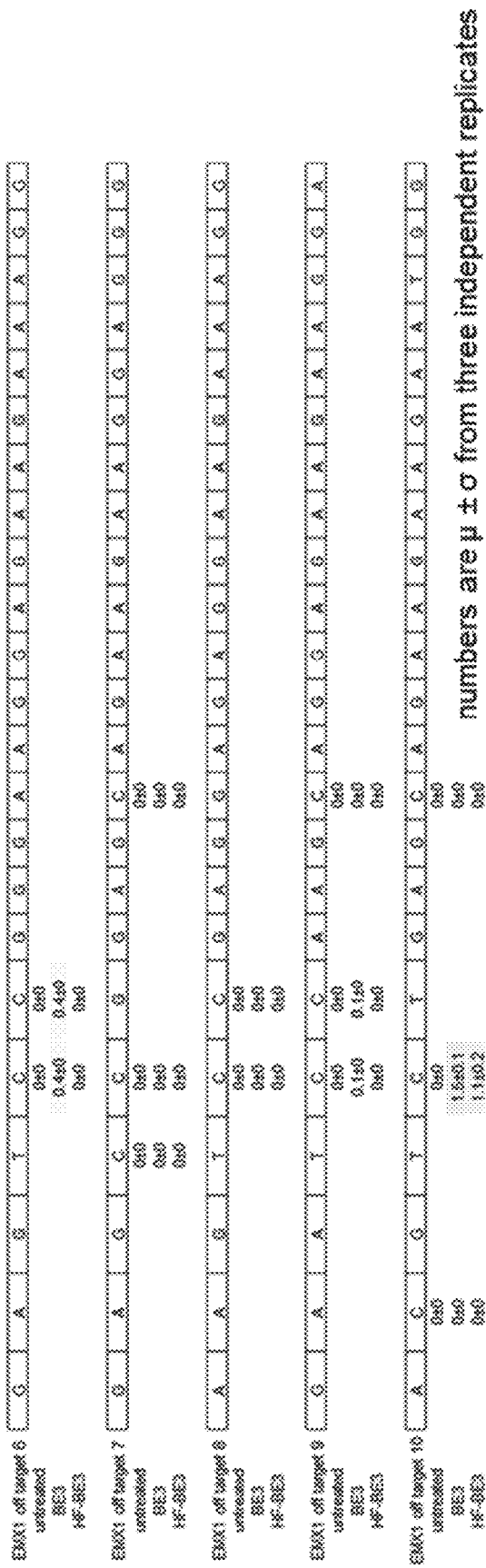

FIG. 76 shows off-target editing of EMX-1 at all 10 sites.

Figure 77:
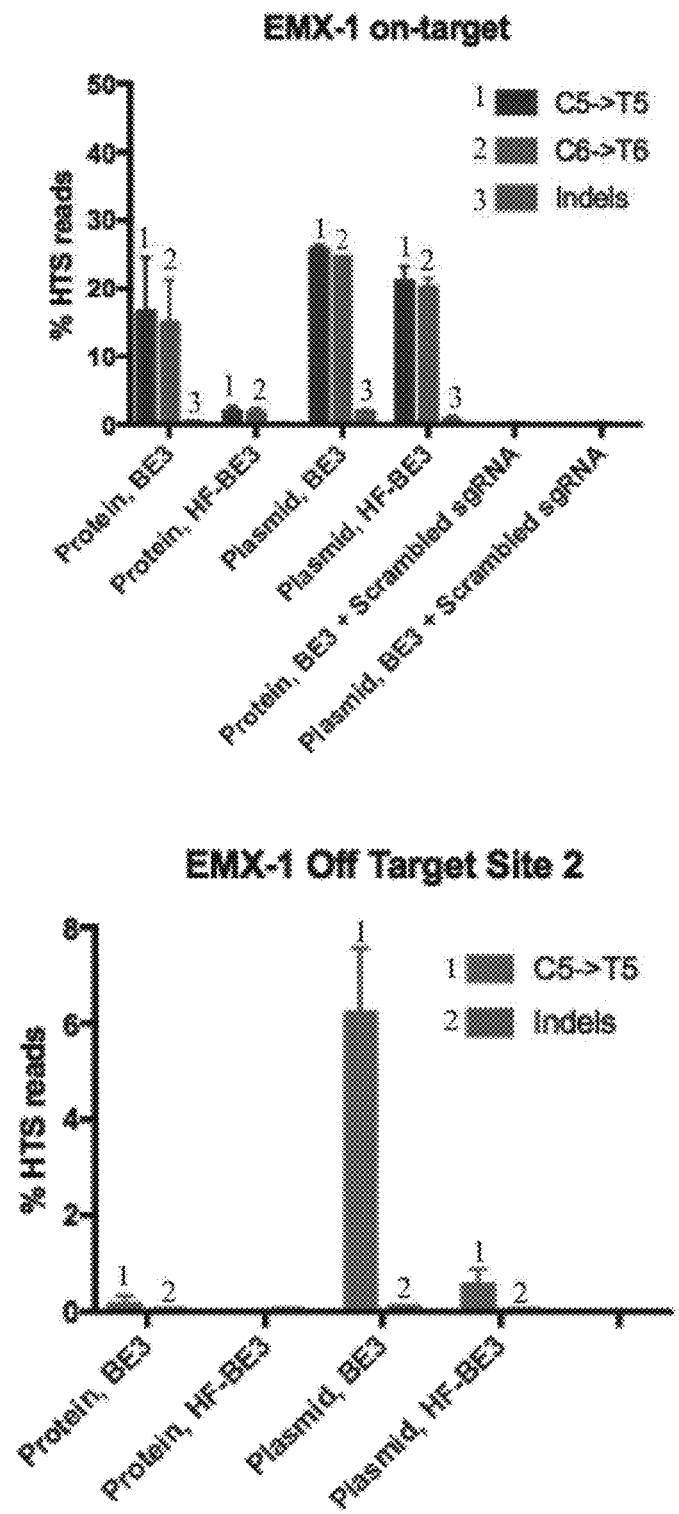

FIG. 77 shows deaminase protein lipofection to HEK cells using a GAGTCCGAGCAGAAGAAGAAG (SEQ ID NO: 313) spacer. The EMX-1 on-target and EMX-1 off target site 2 were examined.

FIG. 78 shows deaminase protein lipofection to HEK cells using a GGAATCCCTTCTGCAGCACCTGG (SEQ ID NO: 314) spacer. The FANCF on target and FANCF off target site 1 were examined.

Figure 79:
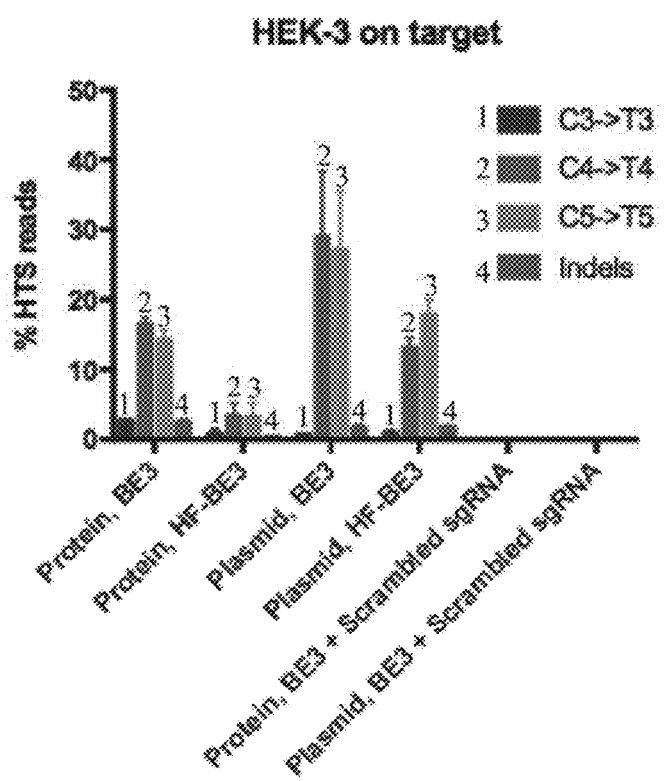

FIG. 79 shows deaminase protein lipofection to HEK cells using a GGCCCAGACTGAGCACGTGA (SEQ ID NO: 315) spacer. The HEK-3 on target site was examined.

Figure 80:
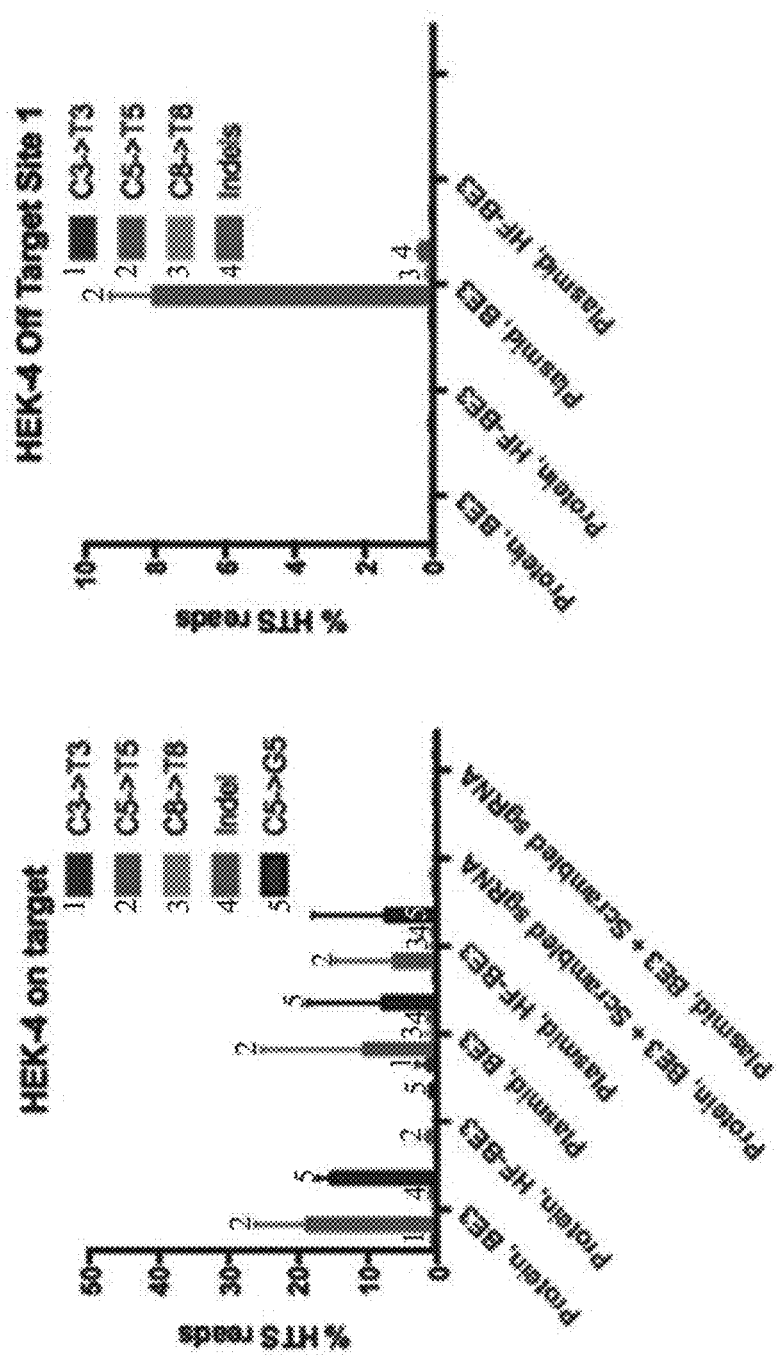
Figure 80:
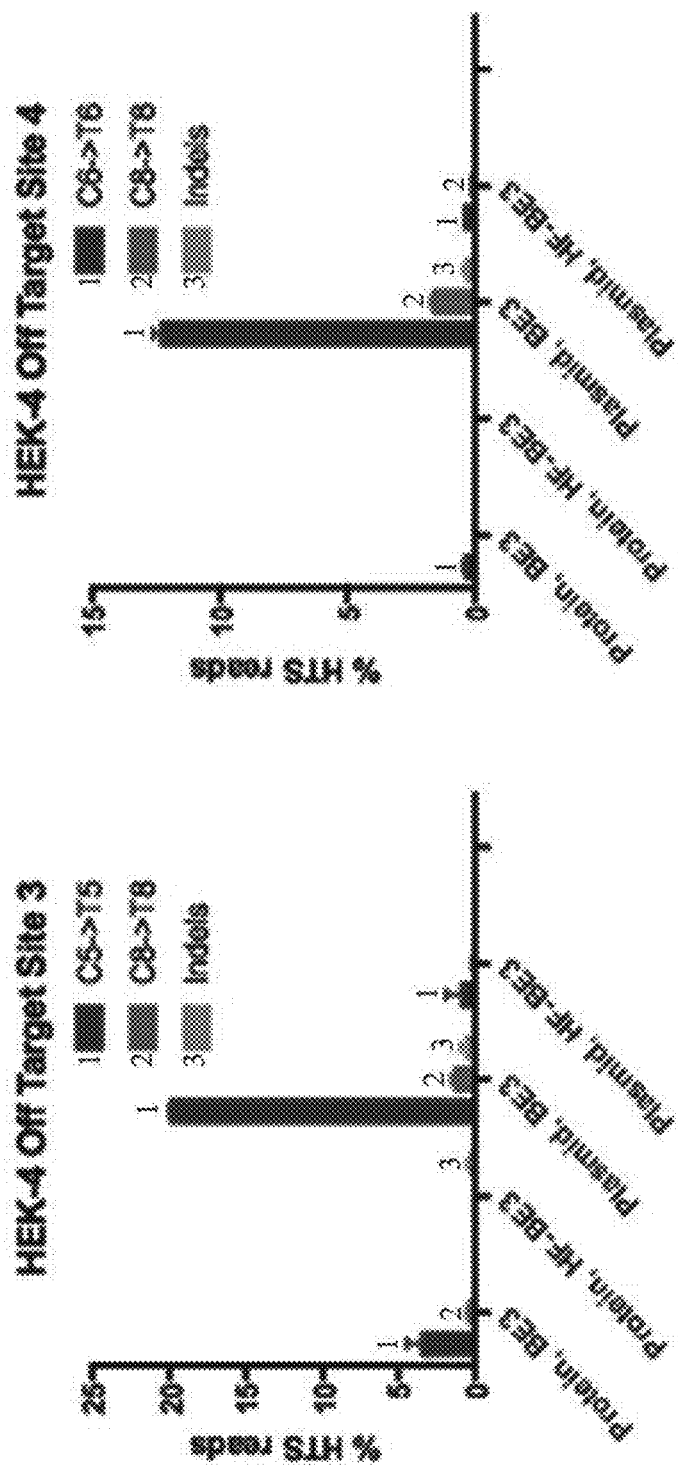

FIG. 80 shows deaminase protein lipofection to HEK cells using a GGCACTGCGGCTGGAGGTGGGGG (SEQ ID NO: 316) spacer. The HEK-4 on target, off target site 1, site 3, and site 4.

Figure 81:
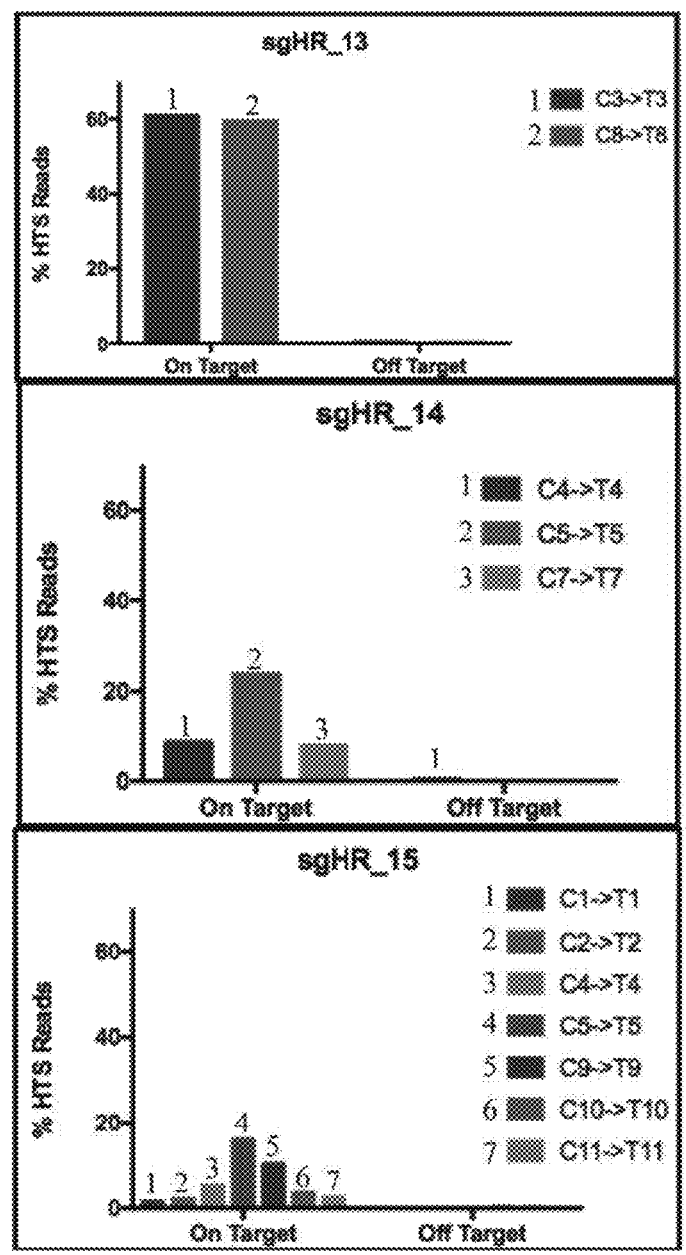

FIG. 81 shows the results of an in vitro assay for sgRNA activity for sgHR_13 (GTCAGGTCGAGGGTTCTGTC (SEQ ID NO: 317) spacer; C8 target: G51 to STOP), sgHR_14 (GGGCCGCAGTATCCTCACTC (SEQ ID NO: 318) spacer; C7 target; C7 target: Q68 to STOP), and sgHR_15 (CCGCCAGTCCCAGTACGGGA (SEQ ID NO: 319) spacer; C10 and C11 are targets: W239 or W237 to STOP).

Figure 82:
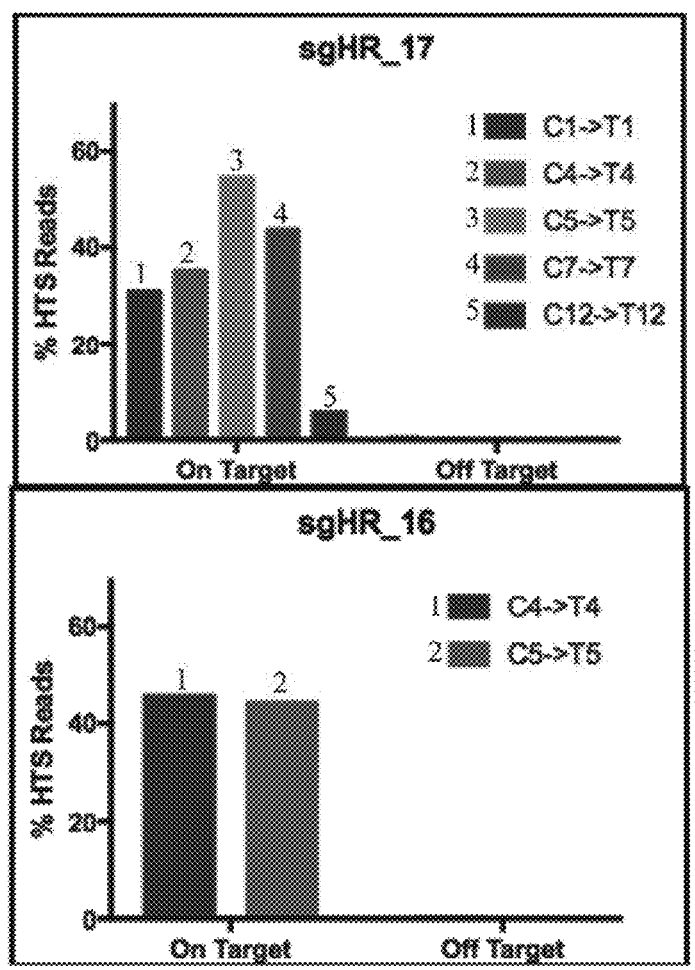

FIG. 82 shows the results of an in vitro assay for sgHR_17 (CAACCACTGCTCAAAGATGC (SEQ ID NO: 320) spacer; C4 and C5 are targets: W410 to STOP), and sgHR_16 (CTTCCAGGATGAGAACACAG (SEQ ID NO: 321) spacer; C4 and C5 are targets: W273 to STOP).

Figure 83:
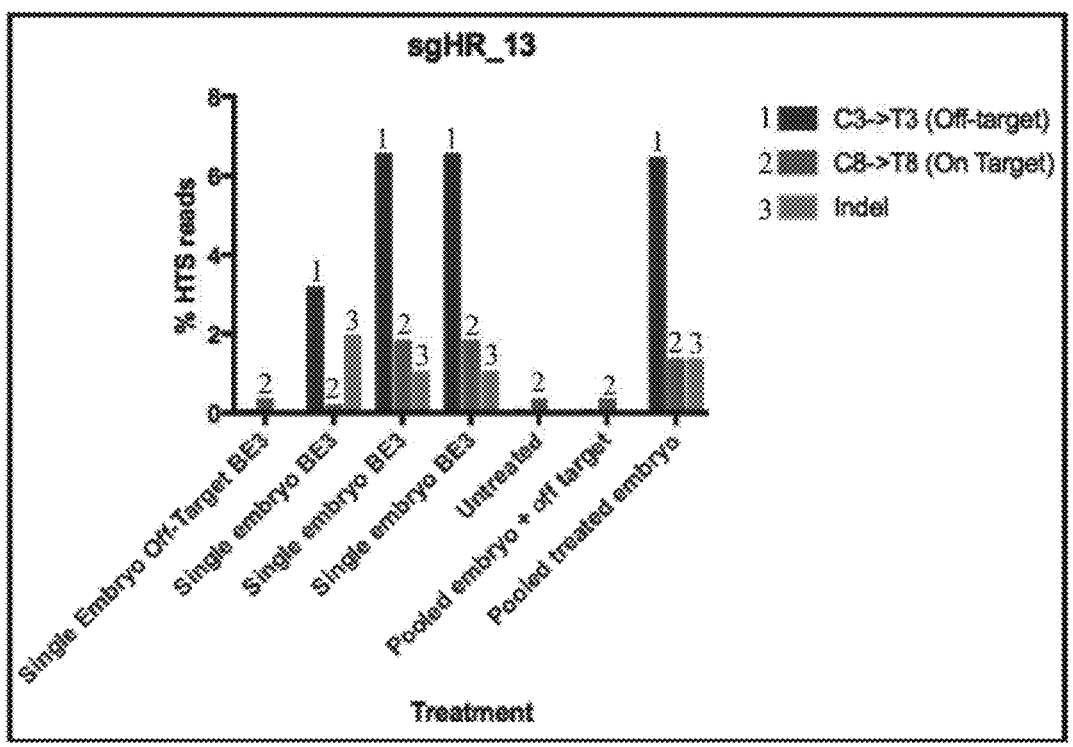

FIG. 83 shows the direct injection of BE3 protein complexed with sgHR_13 in zebrafish embryos.

Figure 84:
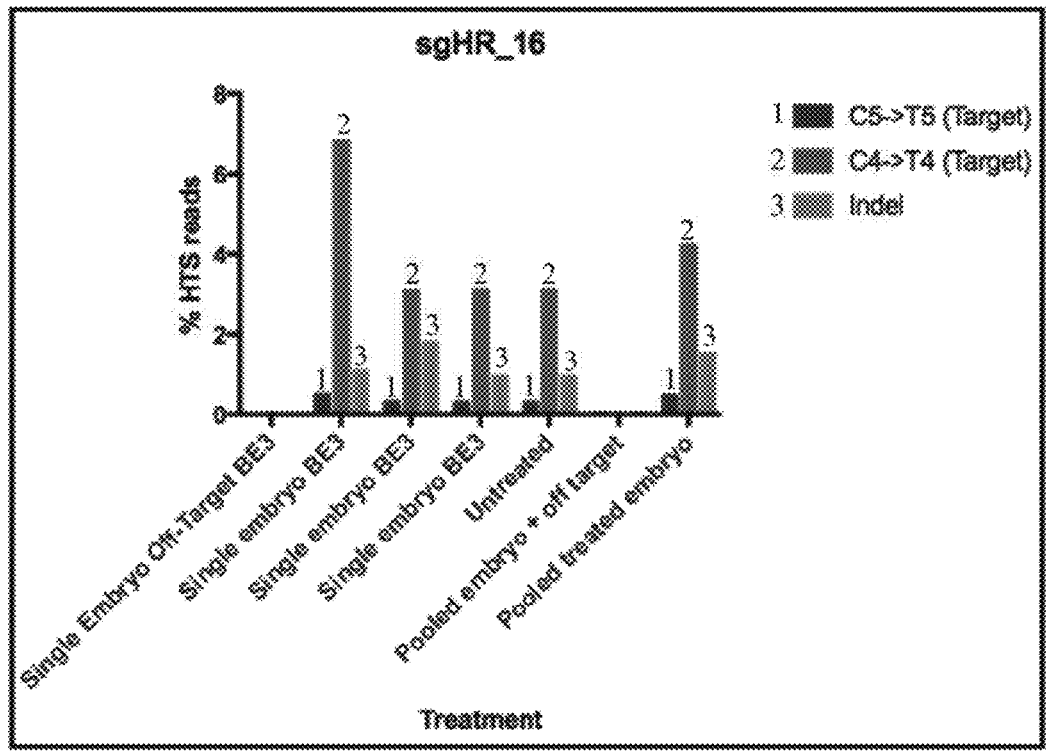

FIG. 84 shows the direct injection of BE3 protein complexed with sgHR_16 in zebrafish embryos.

Figure 85:
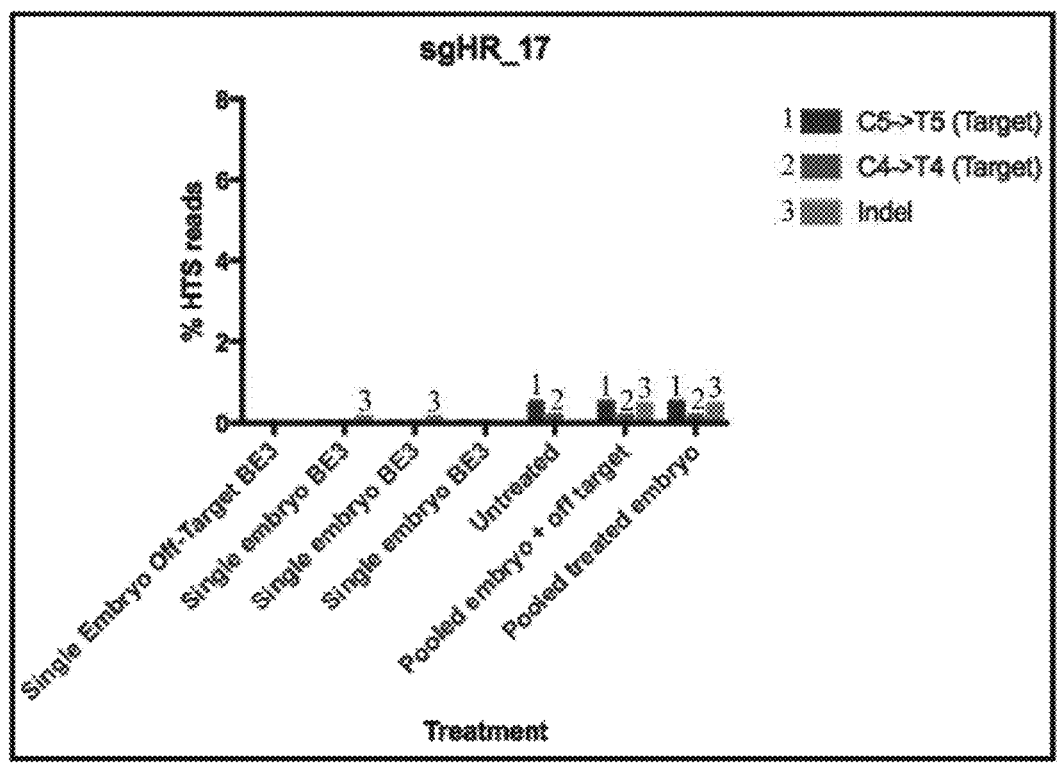

FIG. 85 shows the direct injection of BE3 protein complexed with sgHR_17 in zebrafish embryos.

Figure 86:
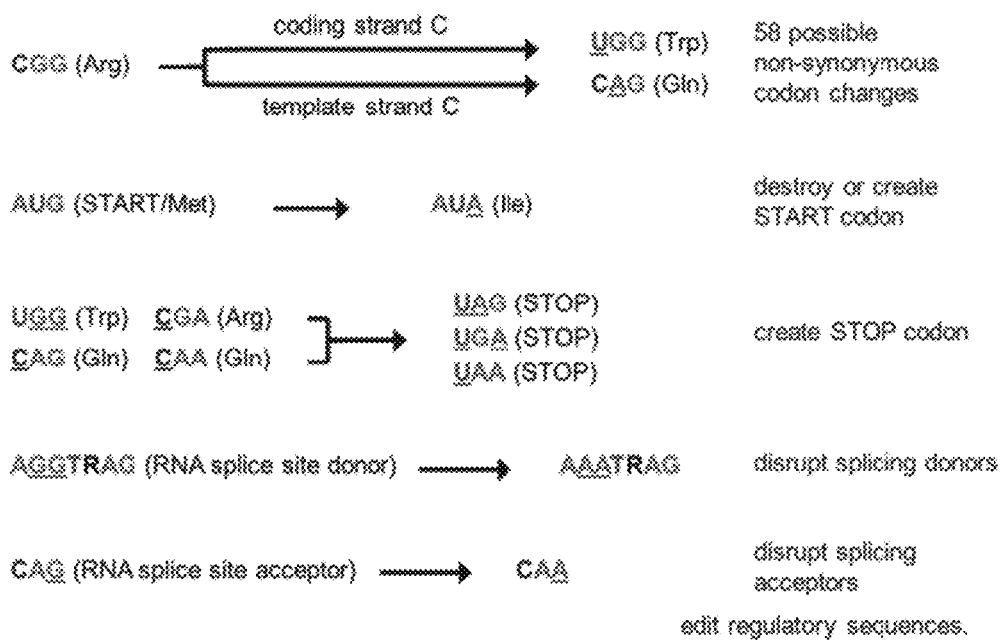

FIG. 86 shows exemplary nucleic acid changes that may be made using base editors that are capable of making a cytosine to thymine change.

Figure 87:
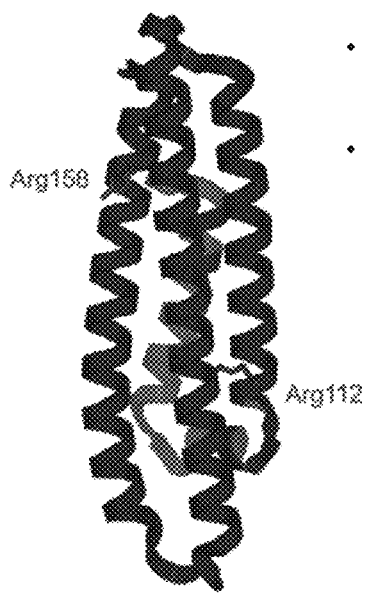

FIG. 87 shows an illustration of apolipoprotein E (APOE) isoforms, demonstrating how a base editor (e.g., BE3) may be used to edit one APOE isoform (e.g., APOE4) into another APOE isoform (e.g., APOE3r) that is associated with a decreased risk of Alzheimer's disease.

Figure 88:
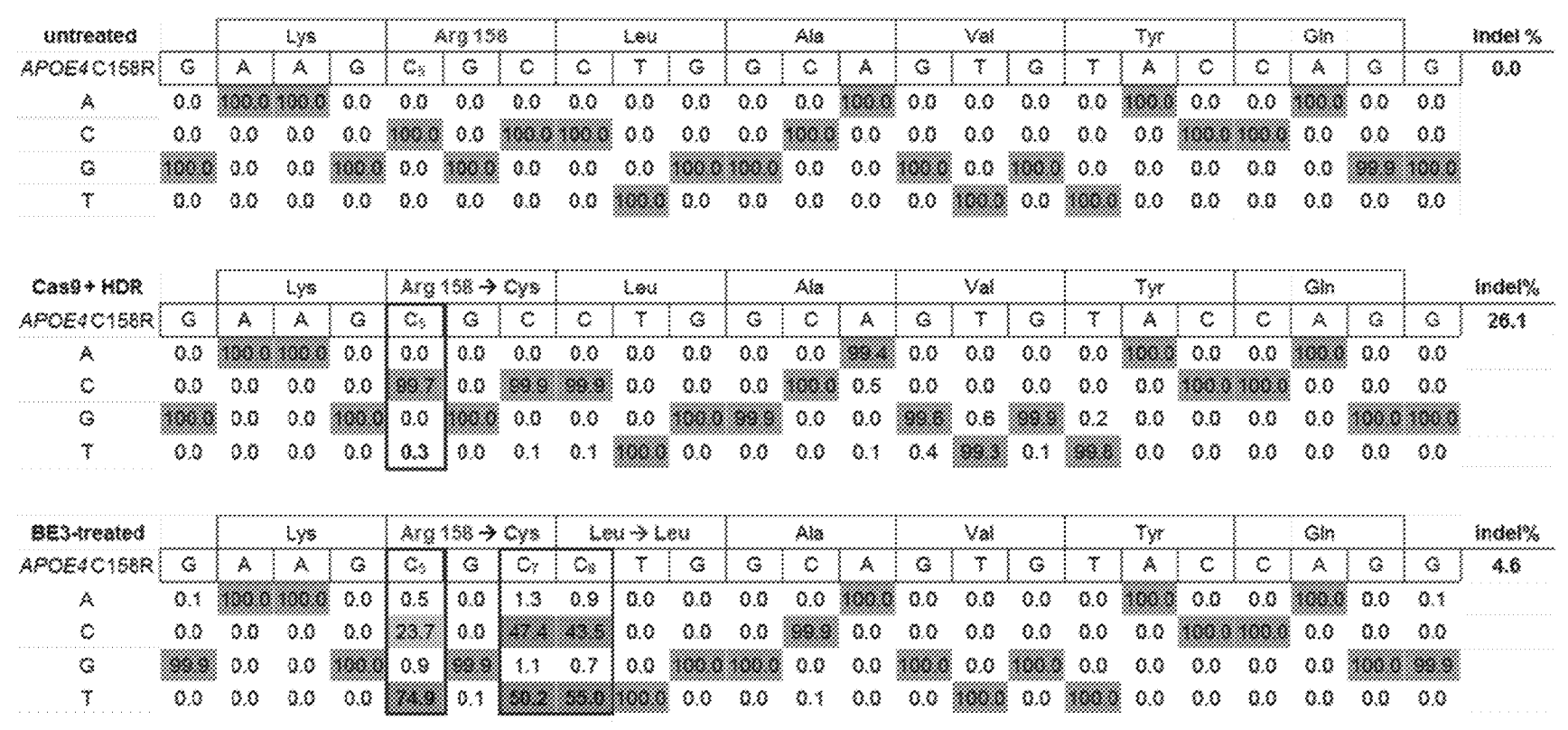

FIG. 88 shows base editing of APOE4 to APOE3r in mouse astrocytes.

Figure 89:
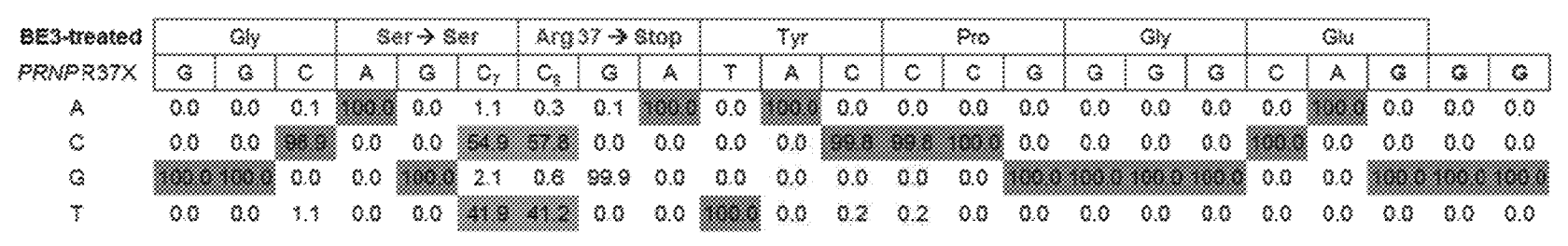

FIG. 89 shows base editing of PRNP to cause early truncation of the protein at arginine residue 37.

Figure 90:
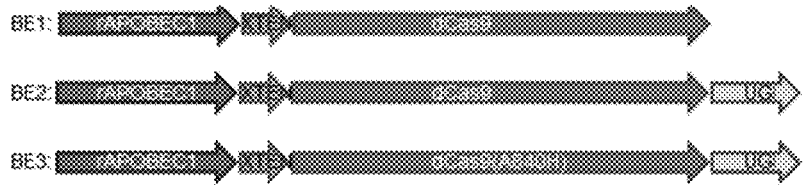

FIG. 90 shows that knocking out UDG (which UGI inhibits) dramatically improves the cleanliness of efficiency of C to T base editing.

FIG. 91 shows that use of a base editor with the nickase but without UGI leads to a mixture of outcomes, with very high indel rates.

Figures 92A, 92B:
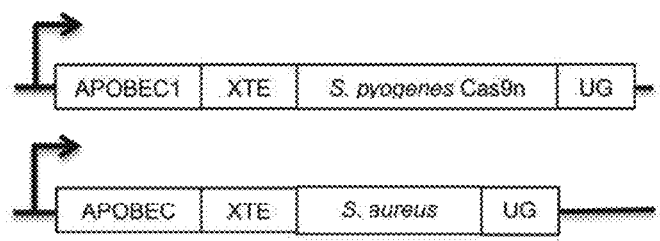
Figure 92C:
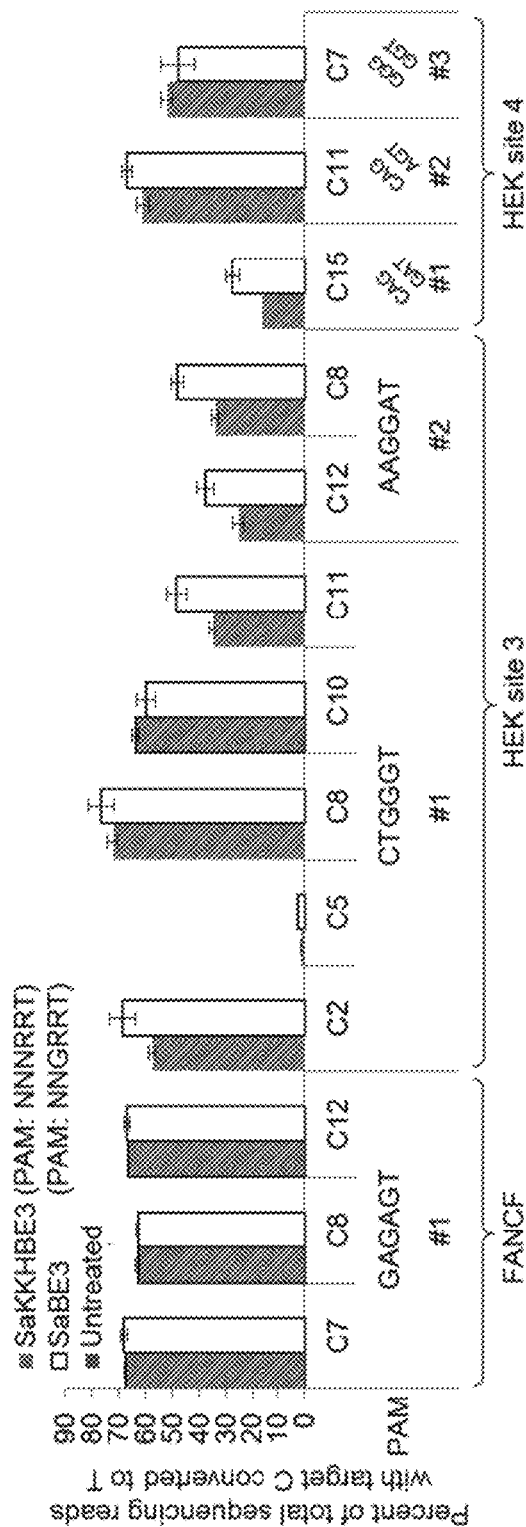
Figure 92D:
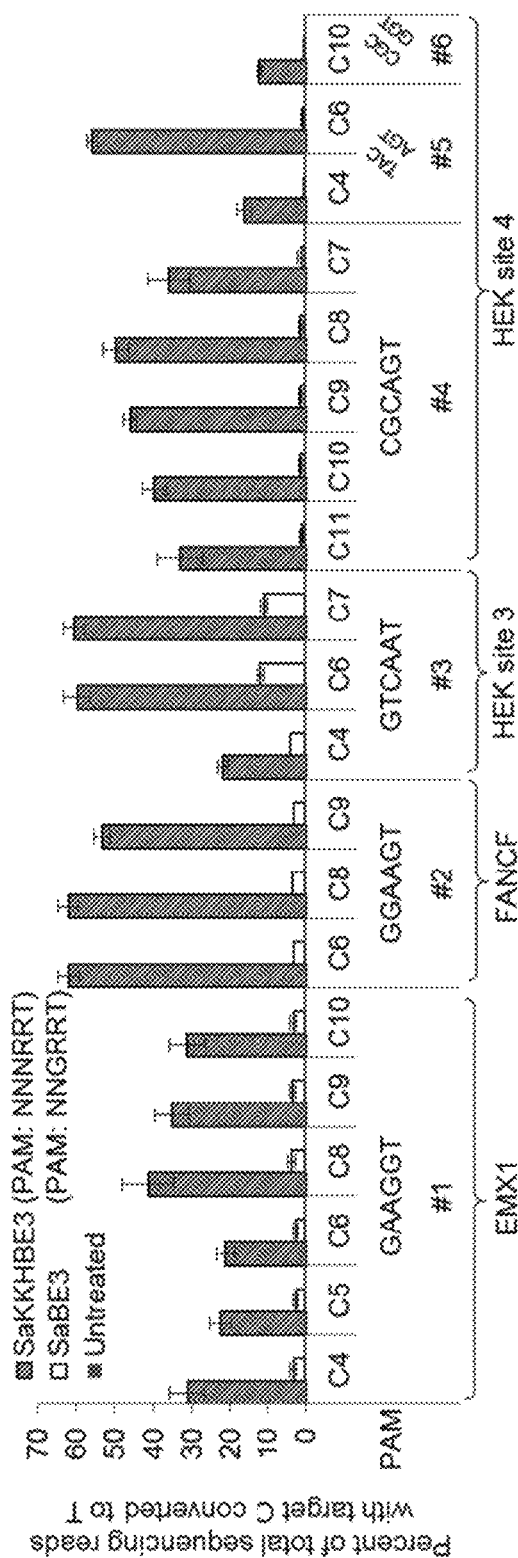
Figure 92E:
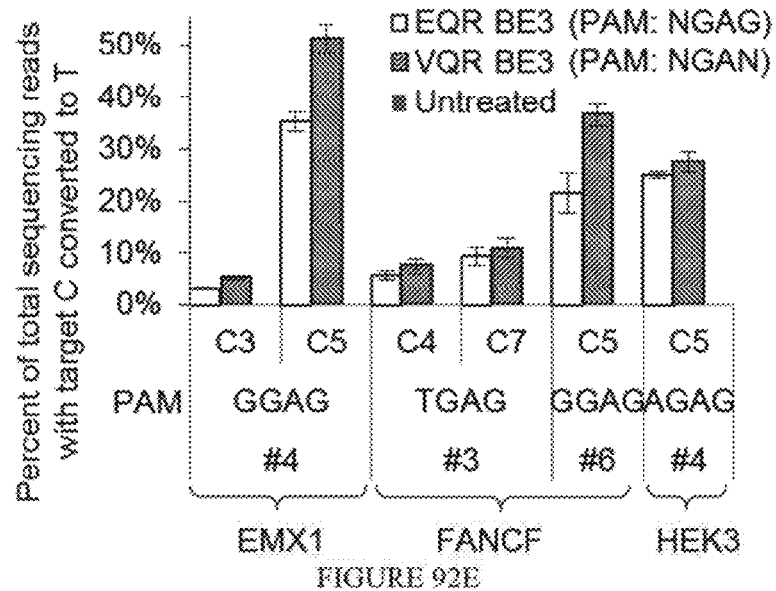
Figure 92F:
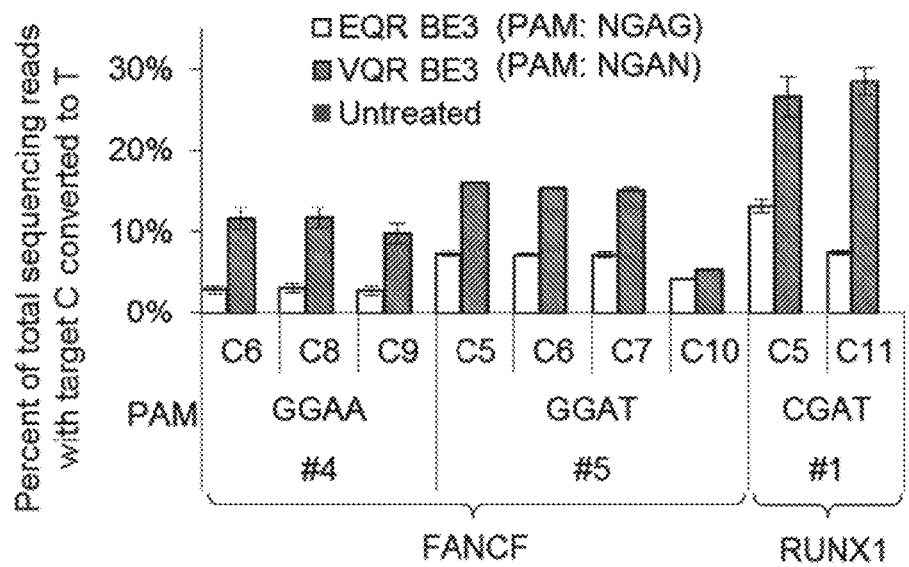
Figure 92G:
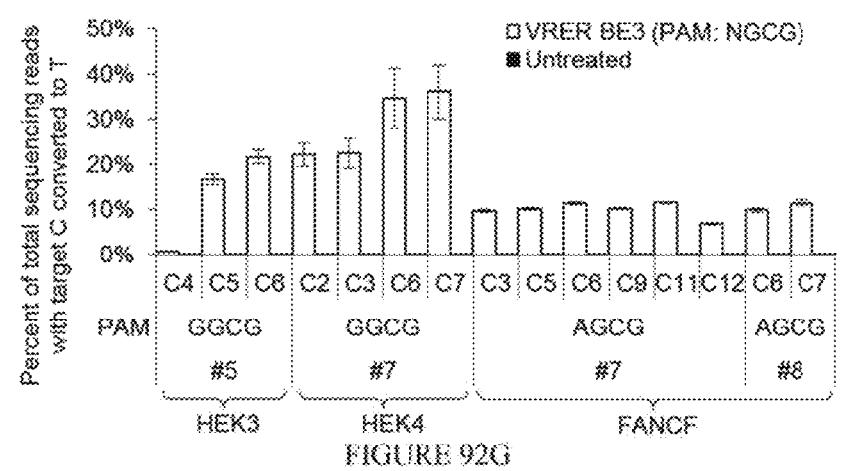

FIGS. 92A to 92G show that SaBE3, SaKKH-BE3, VQR-BE3, EQR-BE3, and VRER-BE3 mediate efficient base editing at target sites containing non-NGG PAMs in human cells. FIG. 92A shows base editor architectures using *S. pyogenes* and *S. aureus* Cas9. FIG. 92B shows recently characterized Cas9 variants with alternate or relaxed PAM requirements. FIGS. 92C and 92D show HEK293T cells treated with the base editor variants shown as described in Example 12. The percentage of total DNA sequencing reads (with no enrichment for transfected cells) with C converted to T at the target positions indicated are shown. The PAM sequence of each target tested is shown below the X-axis. The charts show the results for SaBE3 and SaKKH-BE3 at genomic loci with NNGRRT PAMs (FIG. 92C), SaBE3 and SaKKH-BE3 at genomic loci with NNNRRT PAMs (FIG. 92D), VQR-BE3 and EQR-BE3 at genomic loci with NGAG PAMs (FIG. 92E), and with NGAH PAMs (FIG. 92F), and VRER-BE3 at genomic loci with NGCG PAMs (FIG. 92G). Values and error bars reflect the mean and standard deviation of at least two biological replicates.

Figure 93A:
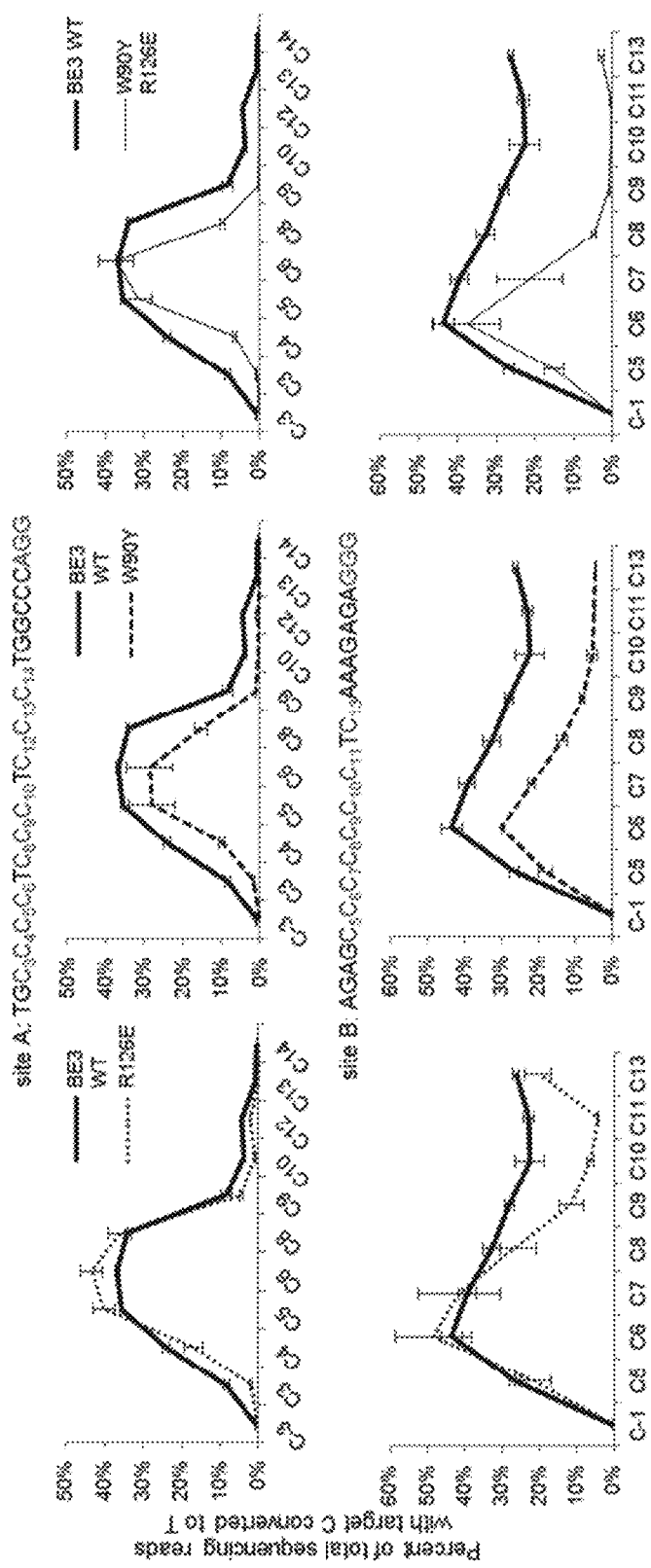
Figure 93B:
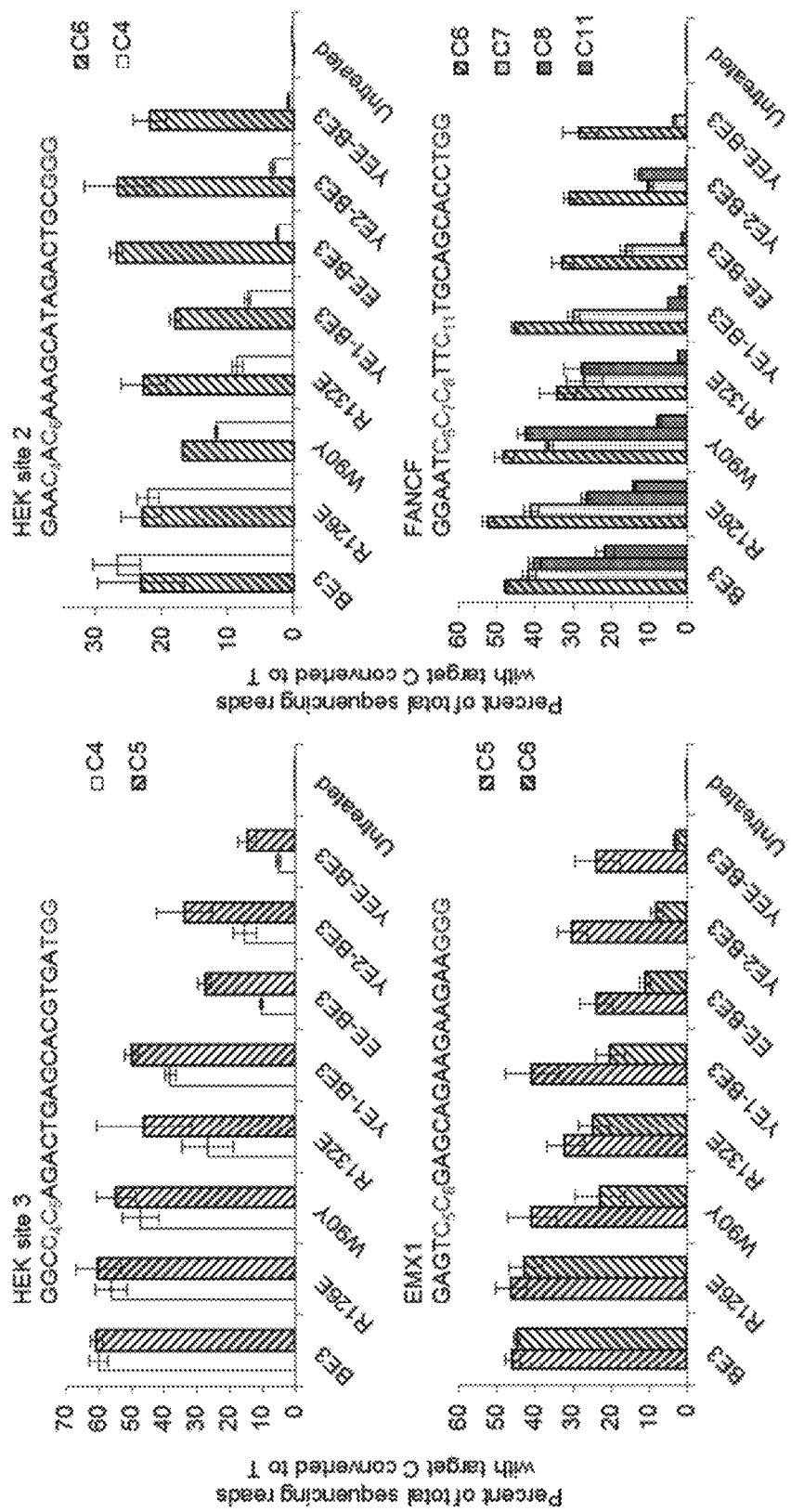
Figure 93C:
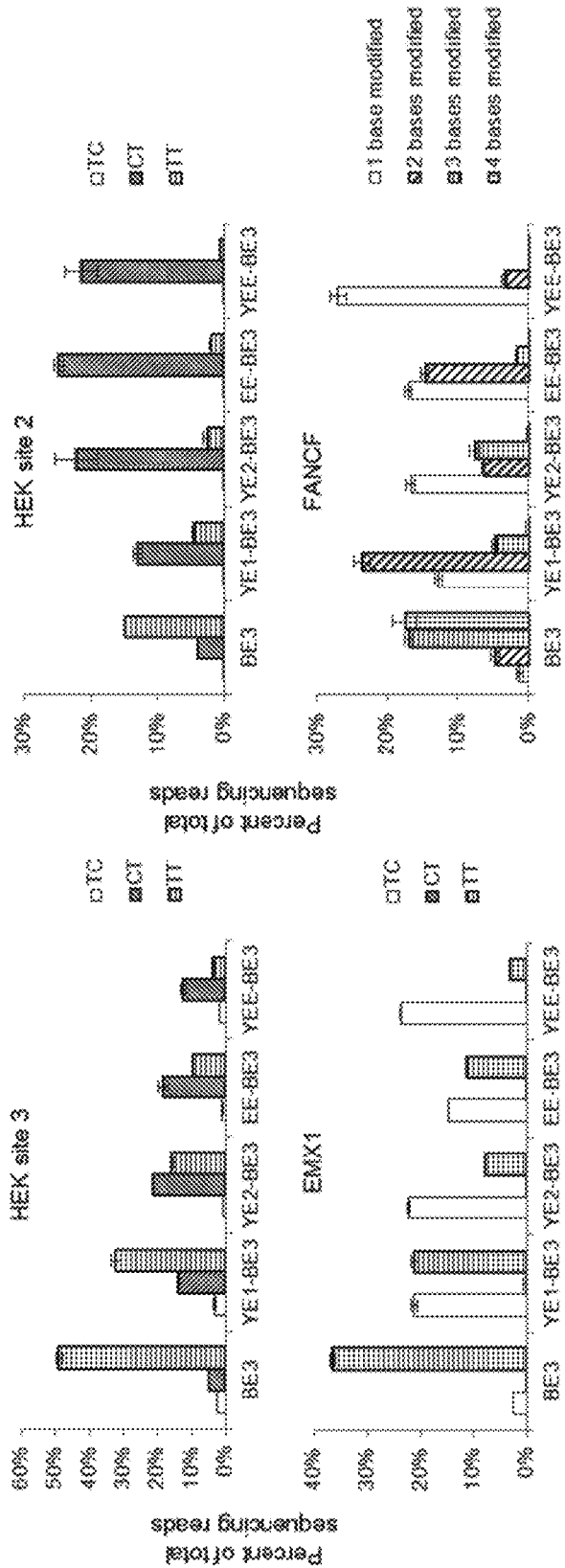

FIGS. 93A to 93C demonstrate that base editors with mutations in the cytidine deaminase domain exhibit narrowed editing windows. FIGS. 93A to 93C show HEK293T cells transfected with plasmids expressing mutant base editors and an appropriate sgRNA. Three days after transfection, genomic DNA was extracted and analyzed by high-throughput DNA sequencing at the indicated loci. The percentage of total DNA sequencing reads (without enrichment for transfected cells) with C changed to T at the target positions indicated are shown for the EMX1 site, HEK293 site 3, FANCF site, HEK293 site 2, site A, and site B loci. FIG. 93A illustrates certain cytidine deaminase mutations which narrow the base editing window. See FIG. 98 for the characterization of additional mutations. FIG. 93B shows the effect of cytidine deaminase mutations which effect the editing window width on genomic loci. Combining beneficial mutations has an additive effect on narrowing the editing window. FIG. 93C shows that YE1-BE3, YE2-BE3, EE-BE3, and YEE-BE3 effect the product distribution of base editing, producing predominantly singly-modified products in contrast with BE3. Values and error bars reflect the mean and standard deviation of at least two biological replicates.

Figure 94A:
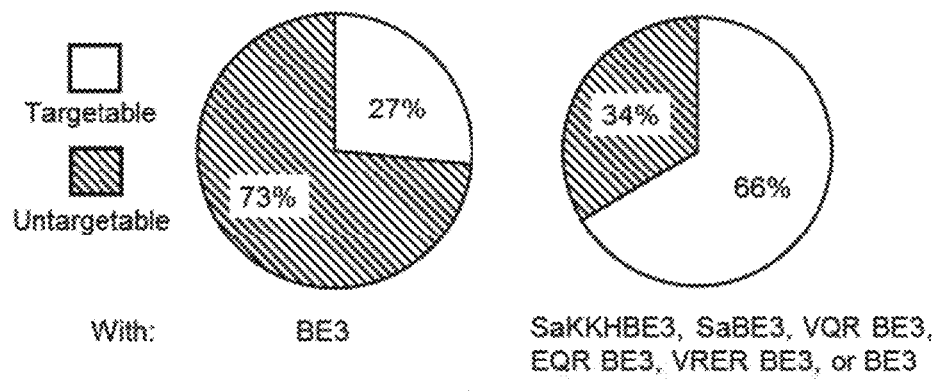
Figure 94B:
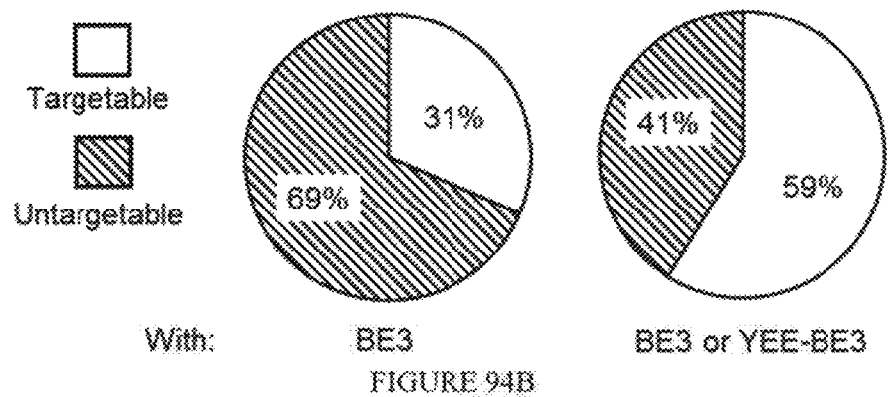

FIGS. 94A and 94B show genetic variants from ClinVar that in principle can be corrected by the base editors developed in this work. The NCBI ClinVar database of human genetic variations and their corresponding phenotypes was searched for genetic diseases that in theory can be corrected by base editing. FIG. 94A demonstrates improvement in base editing targeting scope among all pathogenic T→C mutations in the ClinVar database through the use of base editors with altered PAM specificities. The white fractions denote the proportion of pathogenic T→C mutations accessible on the basis of the PAM requirements of either BE3, or BE3 together with the five modified-PAM base editors developed in this work. FIG. 94B shows improvement in base editing targeting scope among all pathogenic T→C mutations in the ClinVar database through the use of base editors with narrowed activity windows. BE3 was assumed to edit Cs in positions 4-8 with comparable efficiency as shown in FIGS. 93A to 93C. YEE-BE3 was assumed to edit with C5>C6>C7>others preference within its activity window. The white fractions denote the proportion of pathogenic T→C mutations that can be edited BE3 without comparable editing of other Cs (left), or that can be edited BE3 or YEE-BE3 without comparable editing of other Cs (right).

Figure 95A:
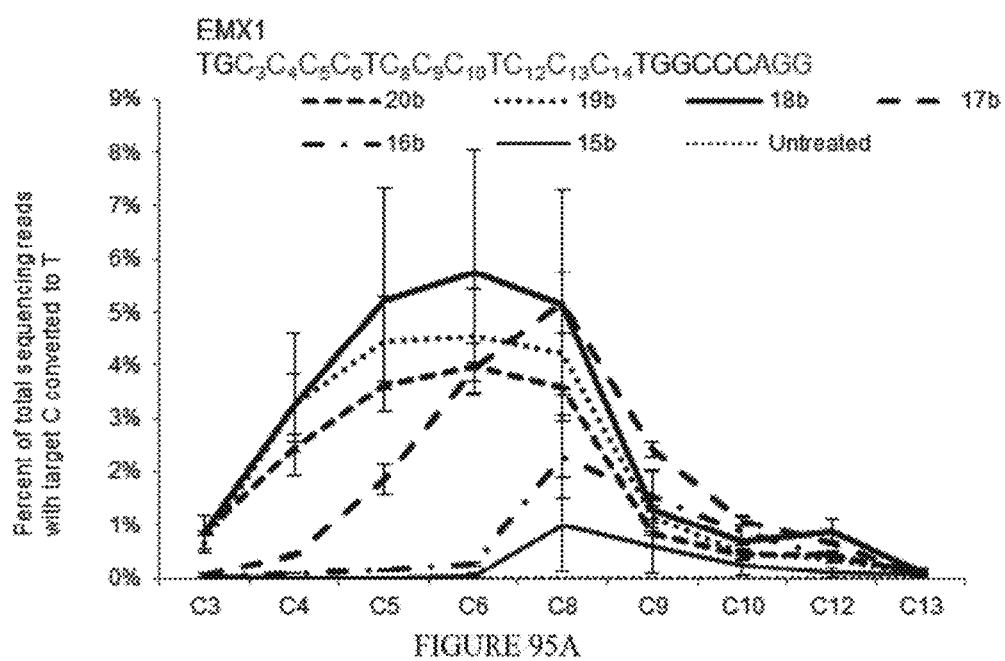
Figure 95B:
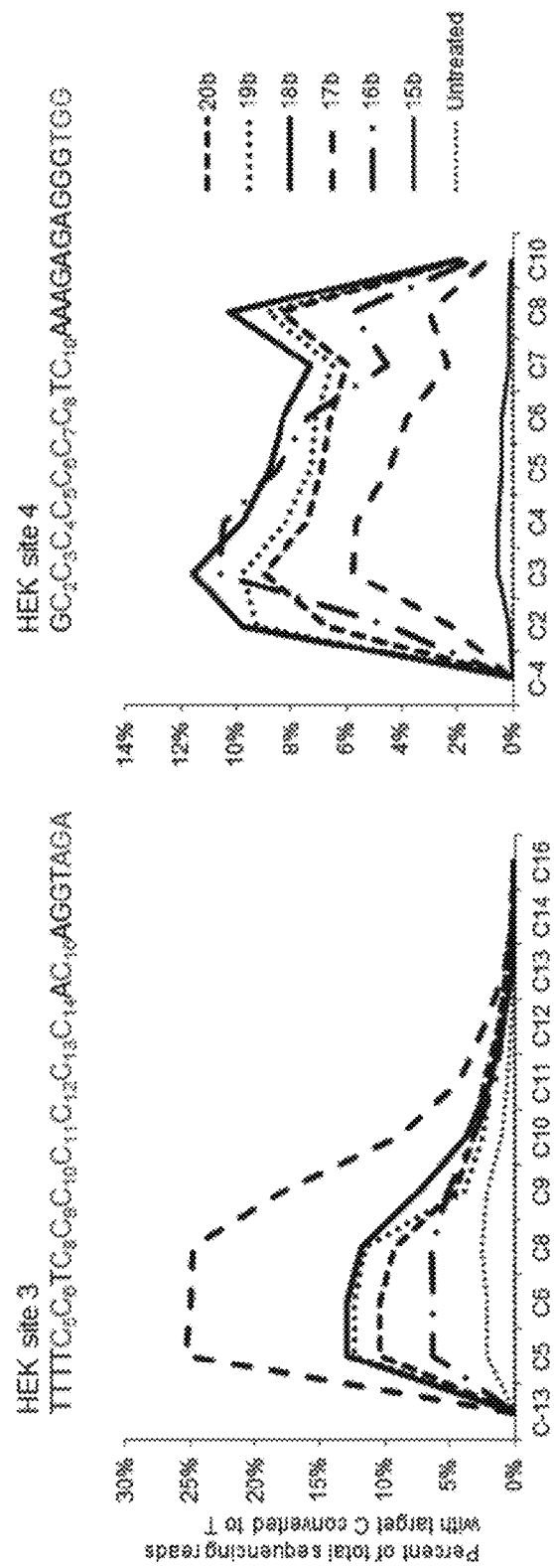

FIGS. 95A and 95B show the effect of truncated guide RNAs on base editing window width. HEK293T cells were transfected with plasmids expressing BE3 and sgRNAs of different 5' truncation lengths. The treated cells were analyzed as described in the Examples. FIG. 95A shows protospacer and PAM sequence (top, SEQ ID NO: 4270) and cellular C to T conversion percentages, defined as the percentage of total DNA sequencing reads with Ts at the target positions indicated, at a site within the EMX1 genomic locus. At this site, the base editing window was altered through the use of a 17-nt truncated gRNA. FIG. 95B shows protospacer and PAM sequences (top, SEQ ID NO: 4270) and cellular C to T conversion percentages, defined as the percentage of total DNA sequencing reads with Ts at the target positions indicated, at sites within the HEK site 3 and site 4 genomic loci. At these sites, no change in the base editing window was observed, but a linear decrease in editing efficiency for all substrate bases as the sgRNA is truncated was noted.

FIG. 96 shows the effect of APOBEC1-Cas9 linker lengths on base editing window width. HEK293T cells were transfected with plasmids expressing base editors with rAPOBEC1-Cas9 linkers of XTEN, GGS, (GGS)$_3$ (SEQ ID NO: 596), (GGS)$_5$ (SEQ ID NO: 4271), or (GGS)$_7$ (SEQ ID NO: 597) and an sgRNA. The treated cells were analyzed as described in the Examples. Cellular C to T conversion percentages, defined as the percentage of total DNA sequencing reads with Ts at the target positions indicated, are shown for the various base editors with different linkers.

Figure 97C:
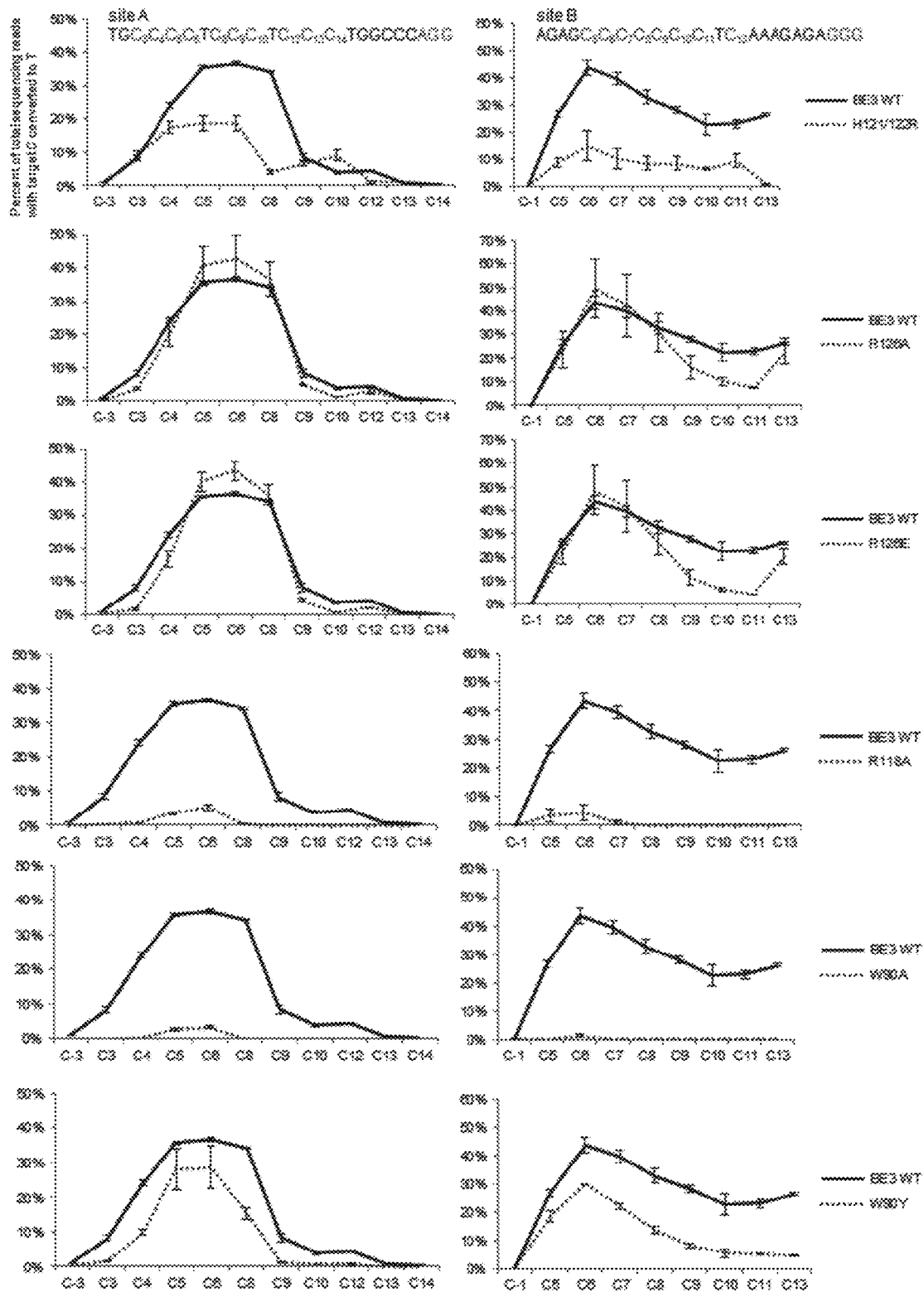
Figure 97C:
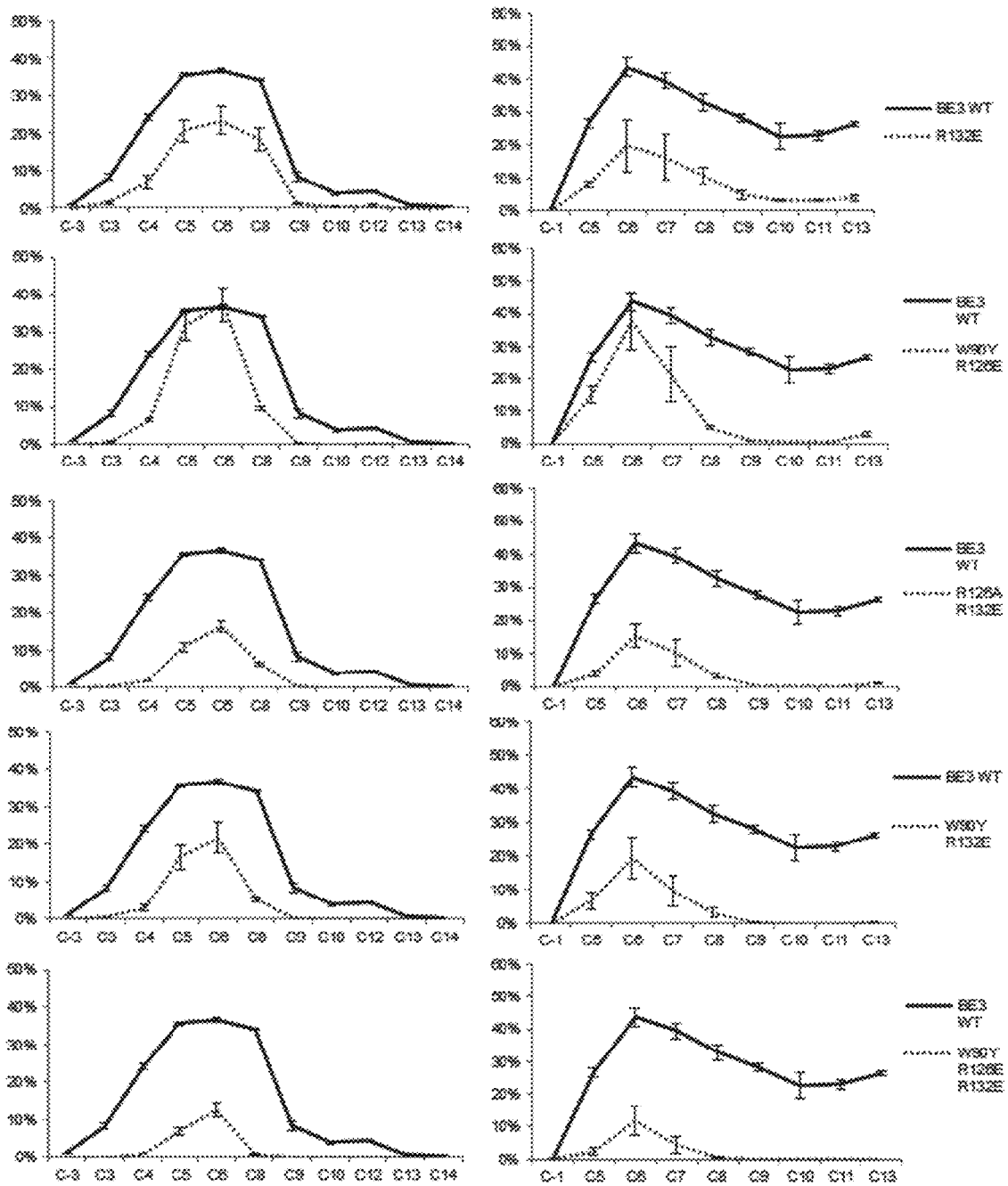

FIGS. 97A to 97C show the effect of rAPOBEC mutations on base editing window width. FIG. 97C shows HEK293T cells transfected with plasmids expressing an sgRNA targeting either Site A or Site B and the BE3 point mutants indicated. The treated cells were analyzed as described in the Examples. All C's in the protospacer and within three basepairs of the protospacer are displayed and the cellular C to T conversion percentages are shown. The 'editing window widths', defined as the calculated number of nucleotides within which editing efficiency exceeds the half-maximal value, are displayed for all tested mutants.

Figure 98:
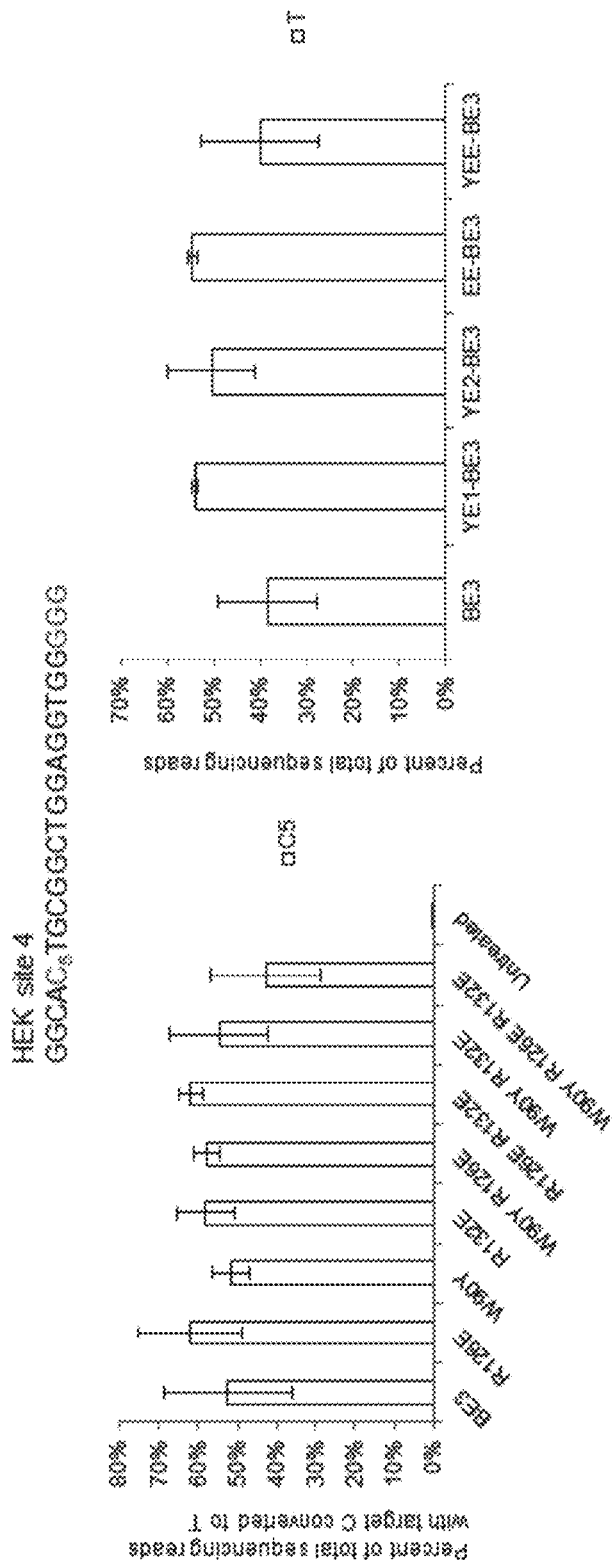

FIG. 98 shows the effect of APOBEC1 mutation son product distributions of base editing in mammalian cells. HEK293T cells were transfected with plasmids expressing BE3 or its mutants and an appropriate sgRNAs. The treated cells were analyzed as described in the Examples. Cellular C to T conversion percentages, defined as the percentage of total DNA sequencing reads with Ts at the target positions indicated, are shown (left). Percent of total sequencing reads containing the C to T conversion is shown on the right. The BE3 point mutants do not significantly affect base editing efficiencies at HEK site 4, a site with only one target cytidine.

Figure 99:
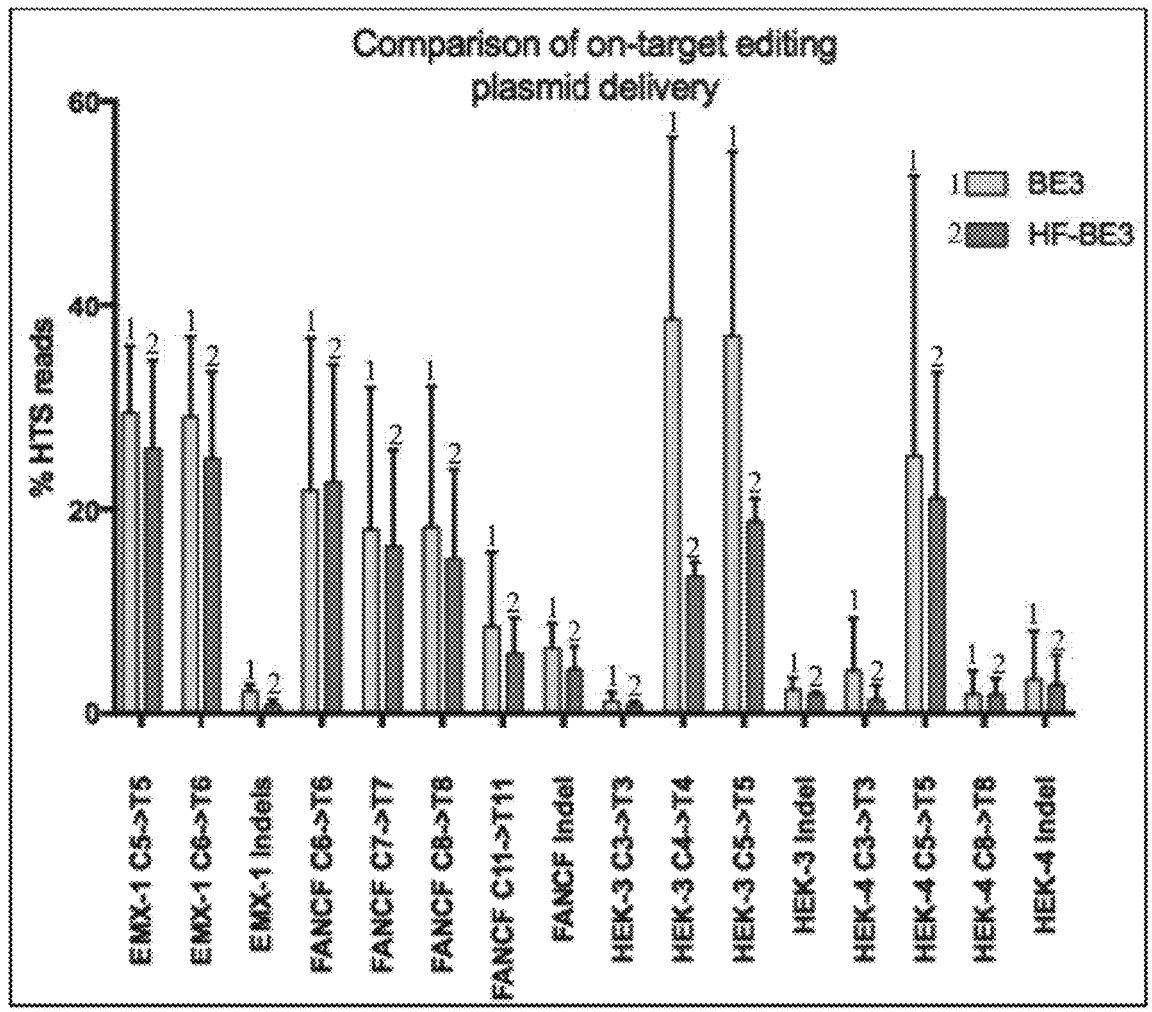

FIG. 99 shows a comparison of on-target editing plasma delivery in BE3 and HF-BE3.

Figure 100:
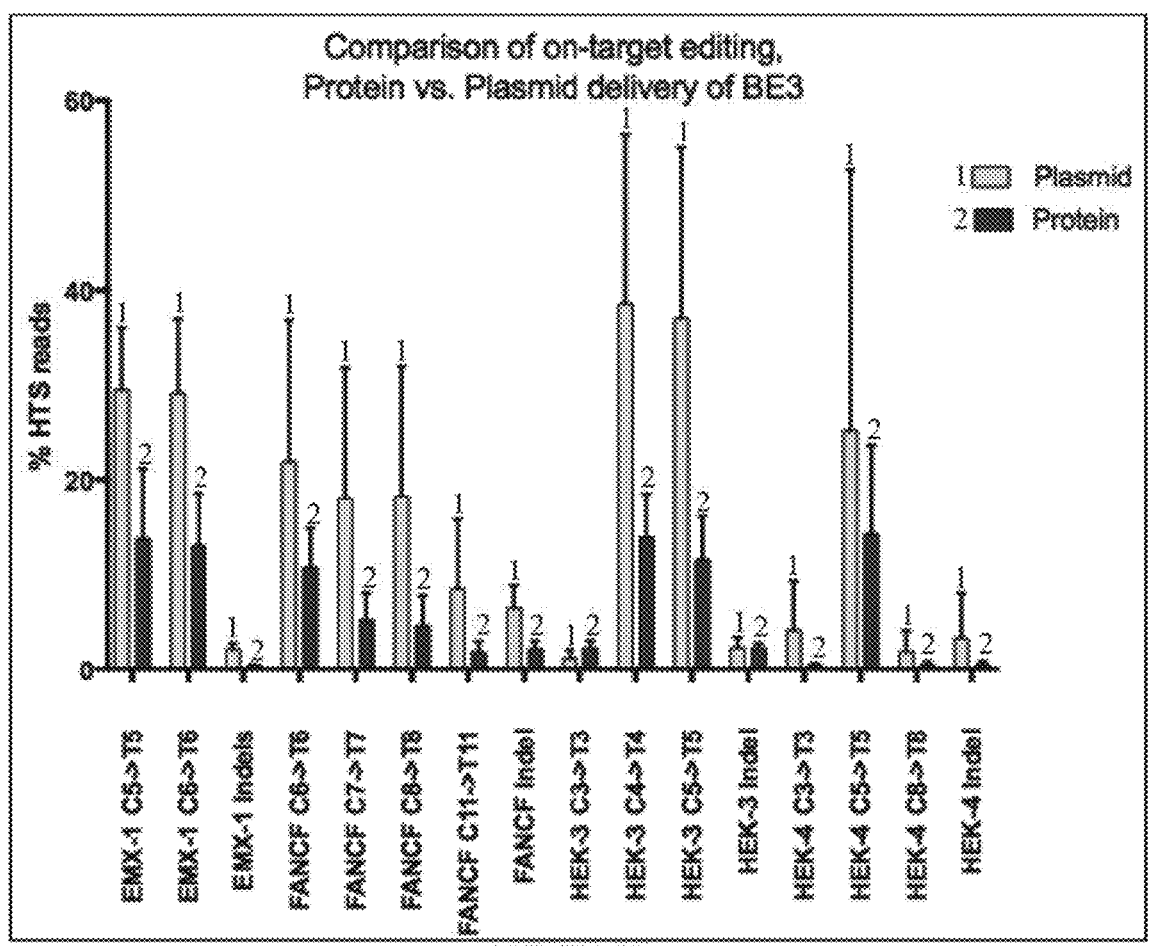

FIG. 100 shows a comparison of on-target editing in protein and plasma delivery of BE3.

Figure 101:
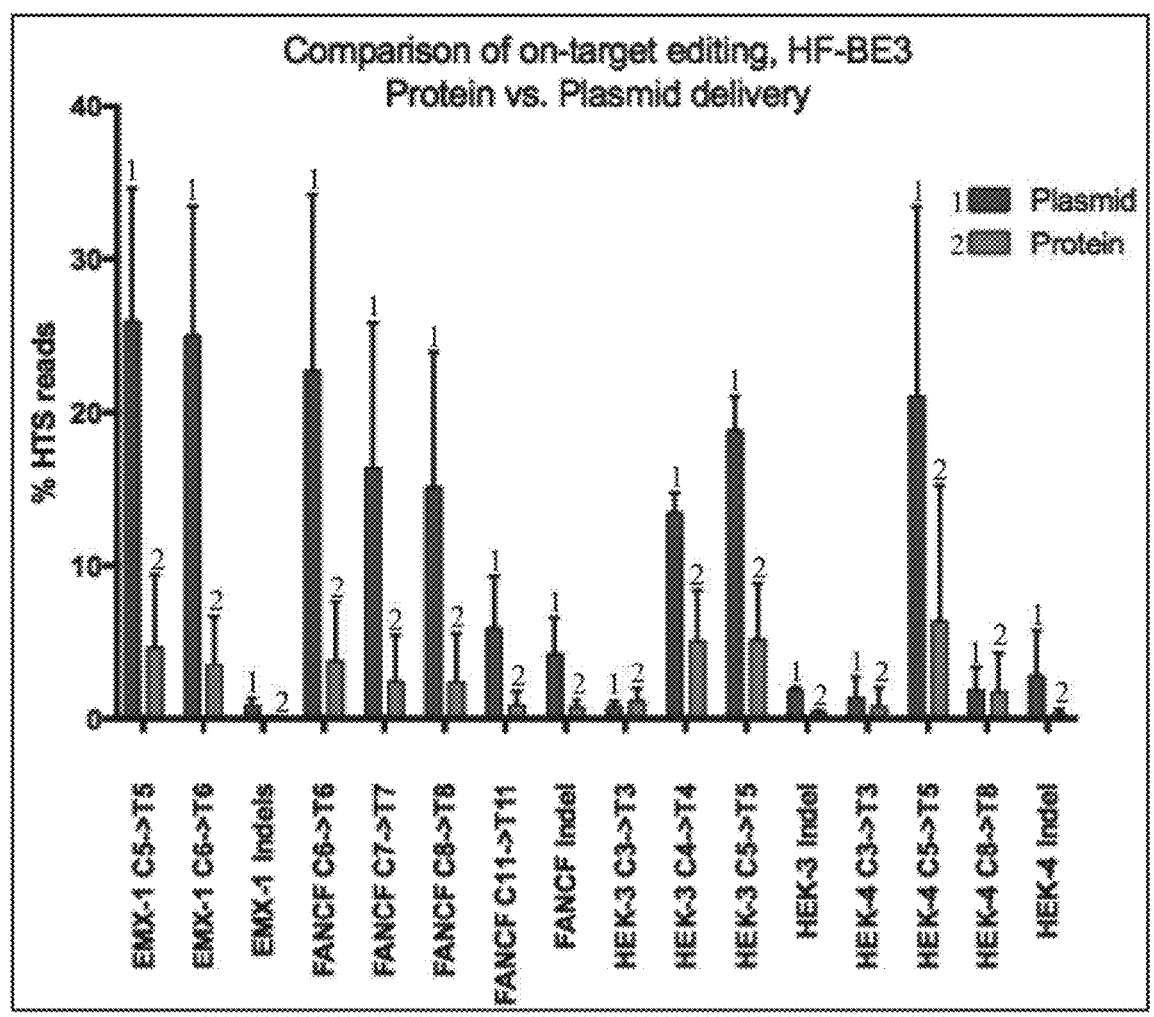

FIG. 101 shows a comparison of on-target editing in protein and plasma delivery of HF-BE3.

Figure 102:
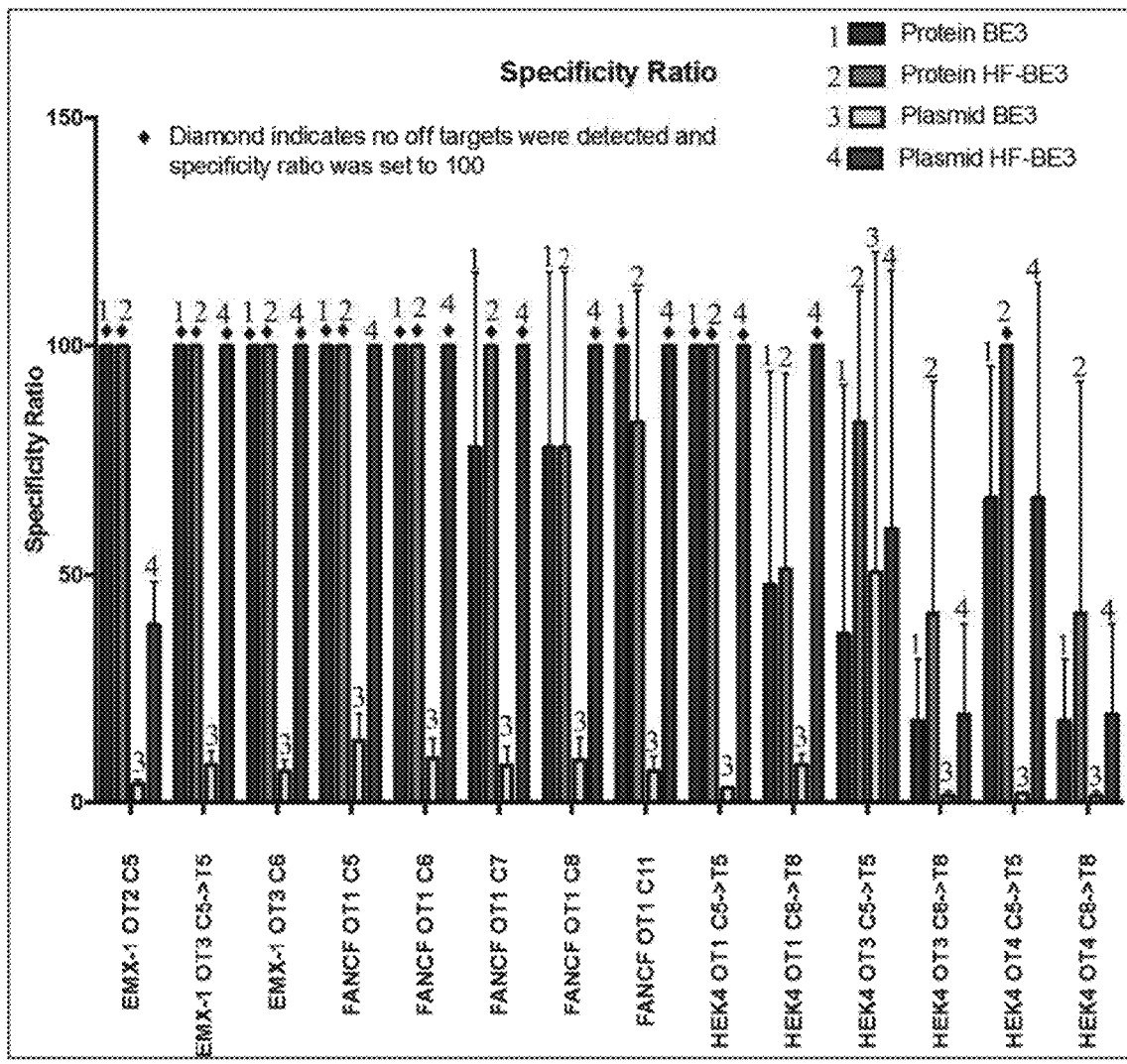

FIG. 102 shows that both lipofection and installing HF mutations decrease off-target deamination events. The diamond indicates no off targets were detected and the specificity ratio was set to 100.

Figure 103:
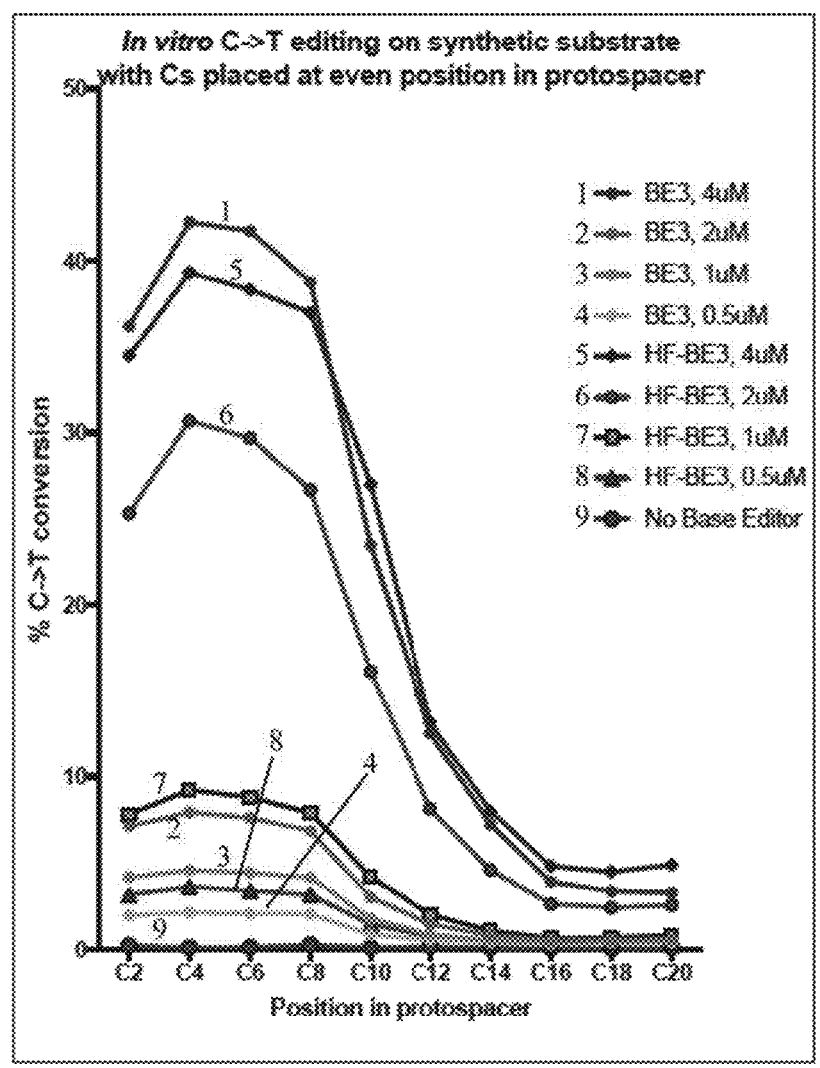

FIG. 103 shows in vitro C to T editing on a synthetic substrate with Cs placed at even positions in the protospacer (NNNNTC$_2$TC$_4$TC$_6$TC$_8$TC$_{10}$TC$_{12}$TC$_{14}$TC$_{16}$TC$_{18}$TC$_{20}$NGG, SEQ ID NO: 4272).

Figure 104:
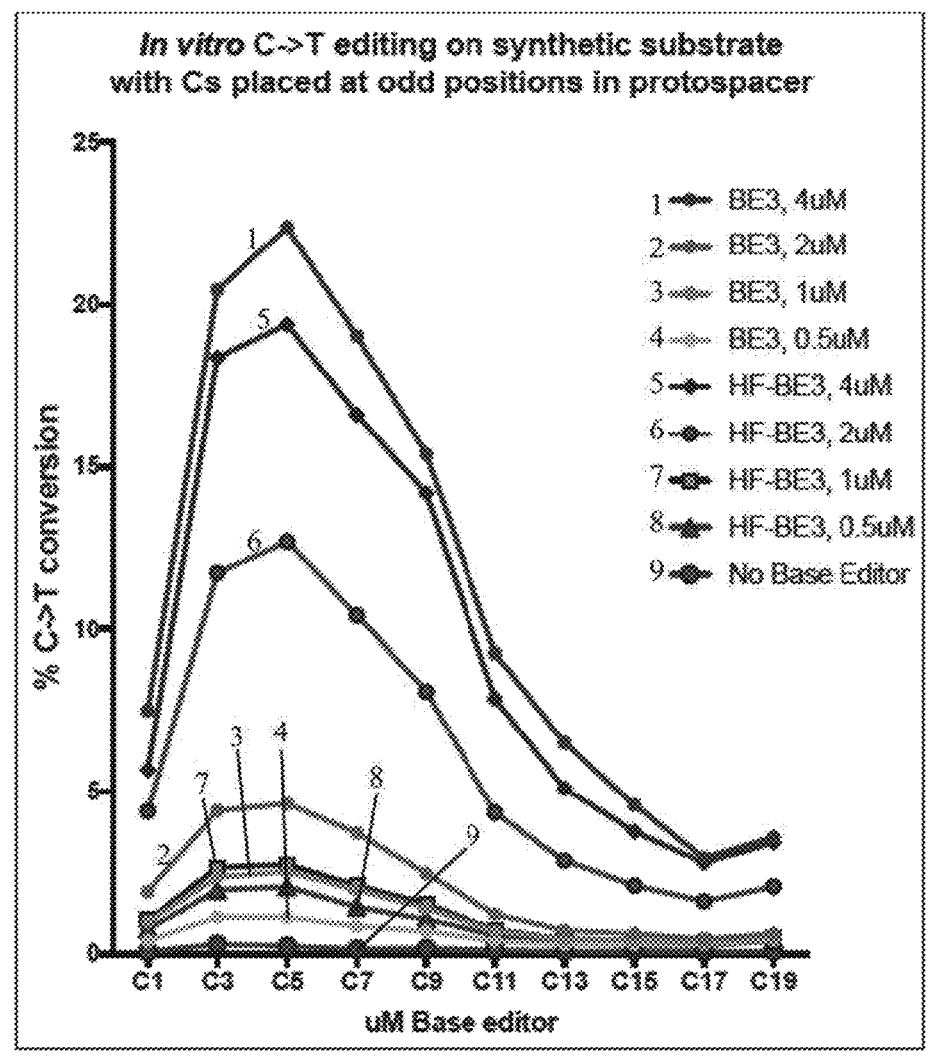

FIG. 104 shows in vitro C to T editing on a synthetic substrate with Cs placed at odd positions in the protospacer (NNNNTC$_2$TC$_4$TC$_6$TC$_8$TC$_{10}$TC$_{12}$TC$_{14}$TC$_{16}$TC$_{18}$TC$_{20}$NGG, SEQ ID NO: 4272).

Figure 105:
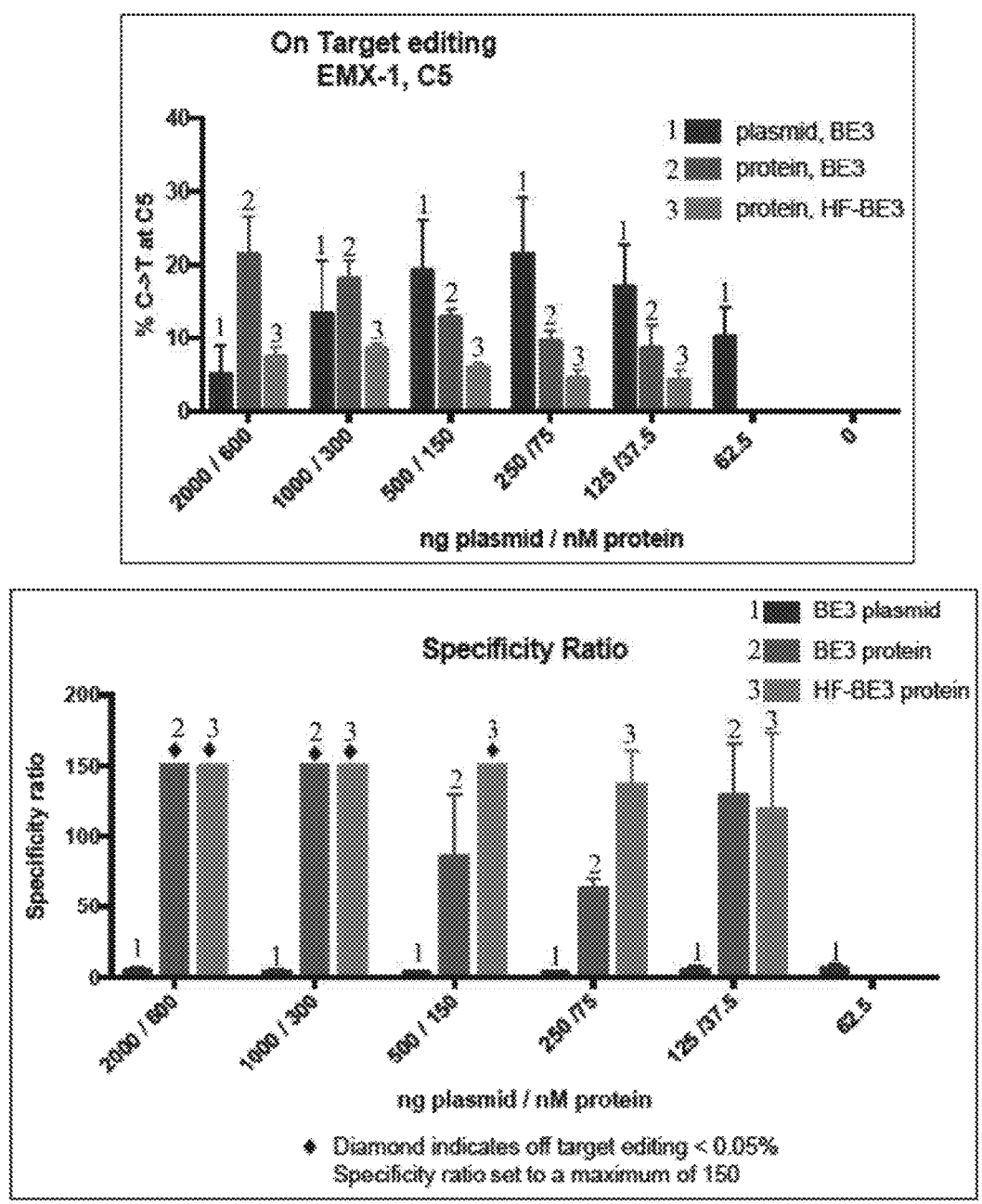

FIG. 105 includes two graphs depicting the specificity ratio of base editing with plasmid vs. protein delivery.

Figure 106A:
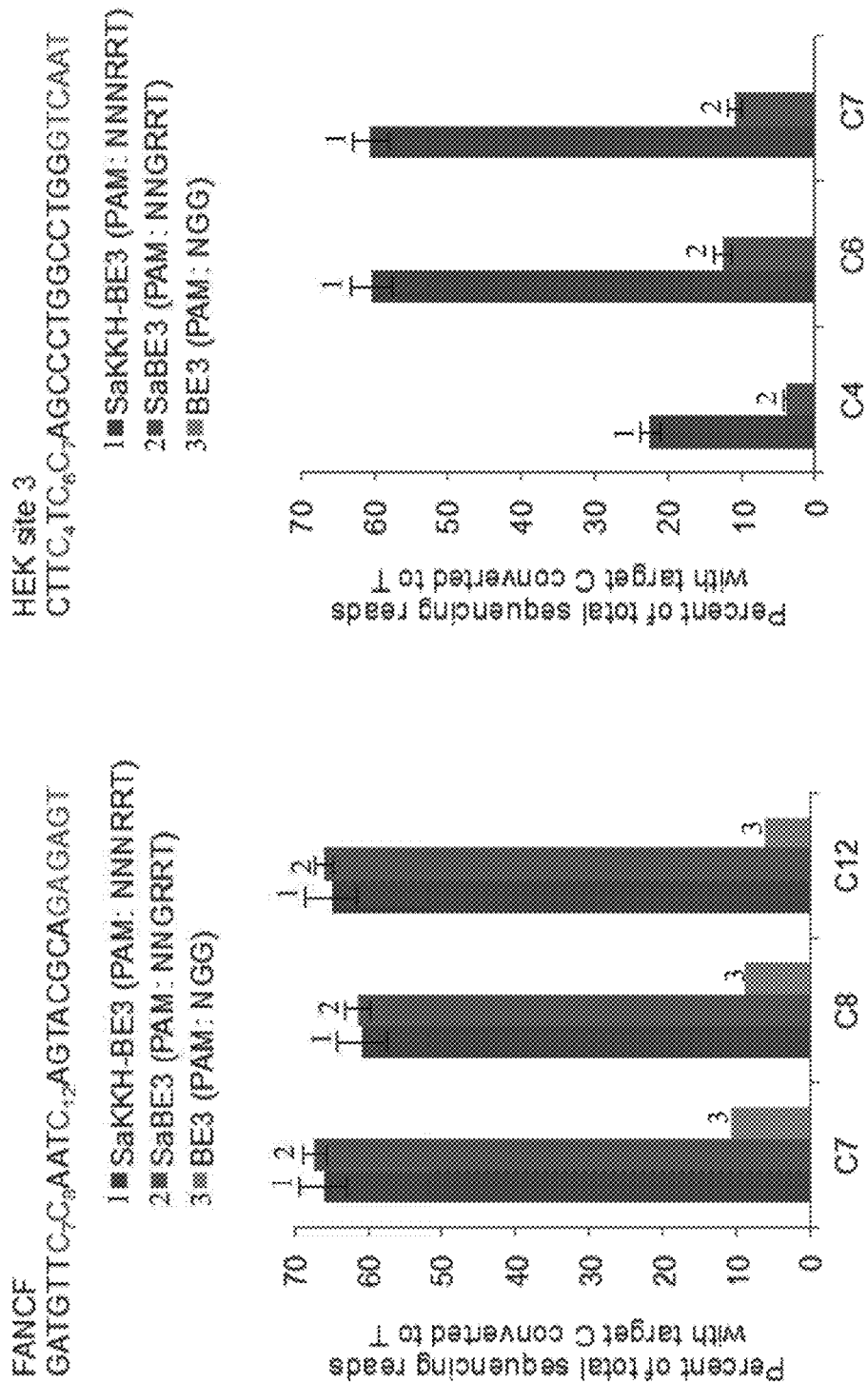
Figure 106B:
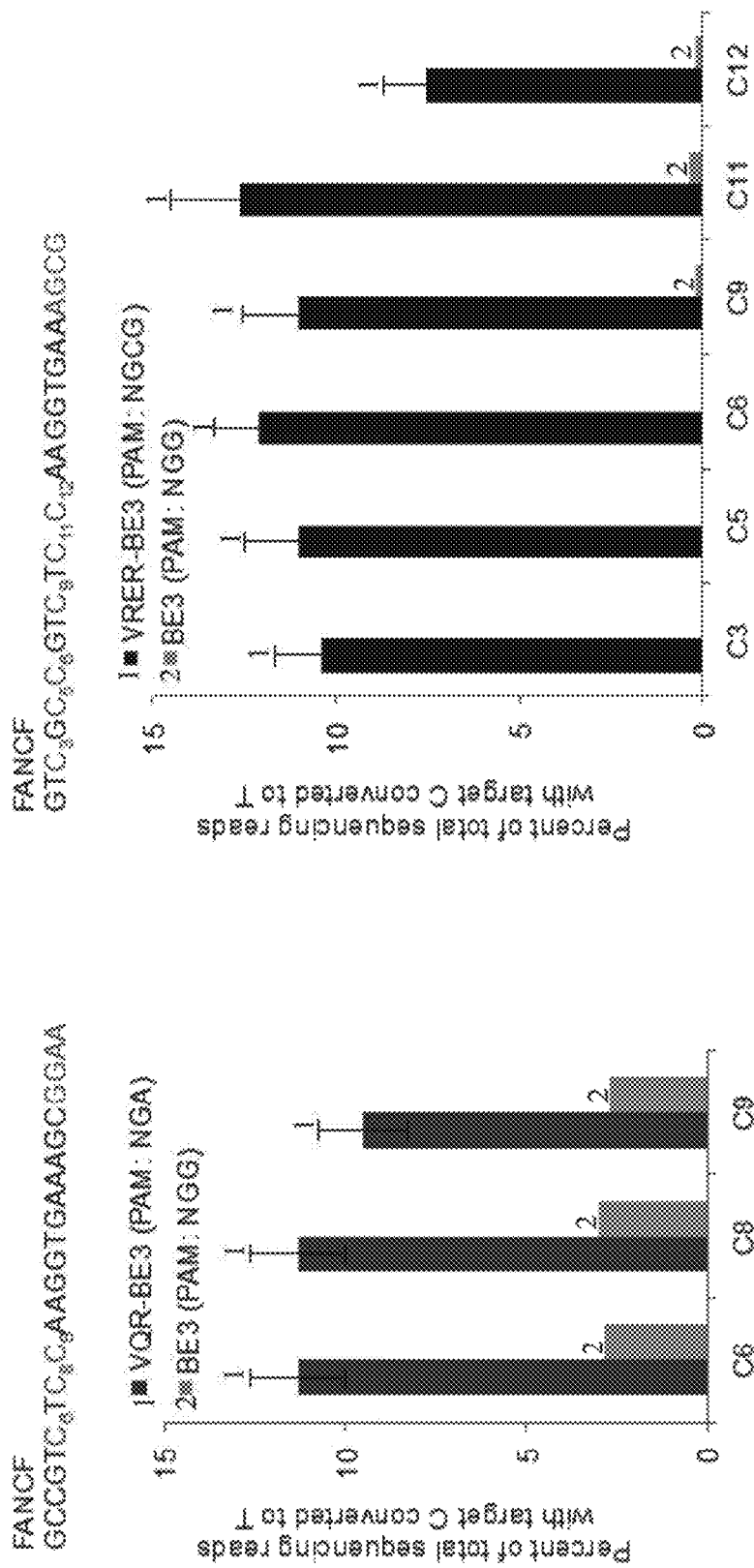

FIGS. 106A to 106B shows BE3 activity on non-NGG PAM sites. HEK293T cells were transfected with plasmids expressing BE3 and appropriate sgRNA. The treated cells were analyzed as described in the Examples. FIG. 106A shows BE3 activity on sites can be efficiently targeted by SaBE3 or SaKKH-BE3. BE3 shows low but significant activity on the NAG PAM. FIG. 106B shows BE3 has significantly reduced editing at sites with NGA or NGCG PAMs, in contrast to VQR-BE3 or VRER-BE3.

Figure 107A:
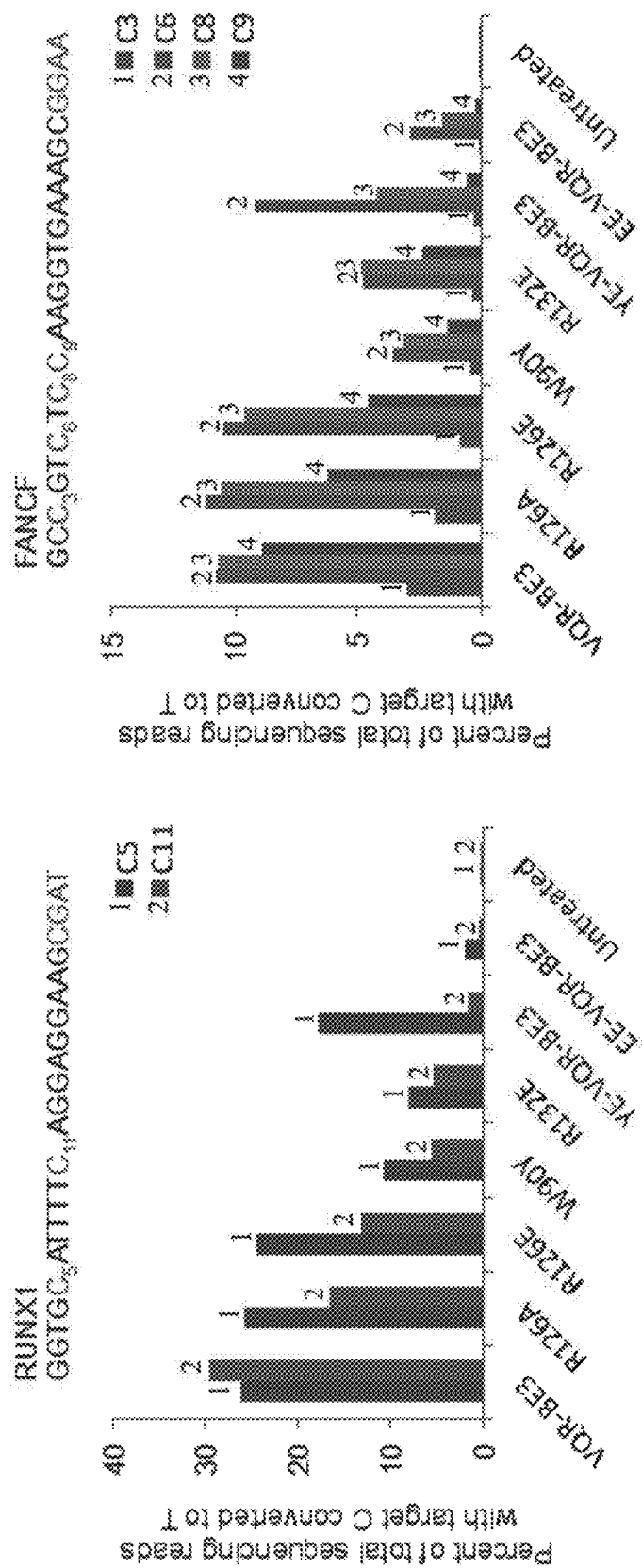
Figure 107B:
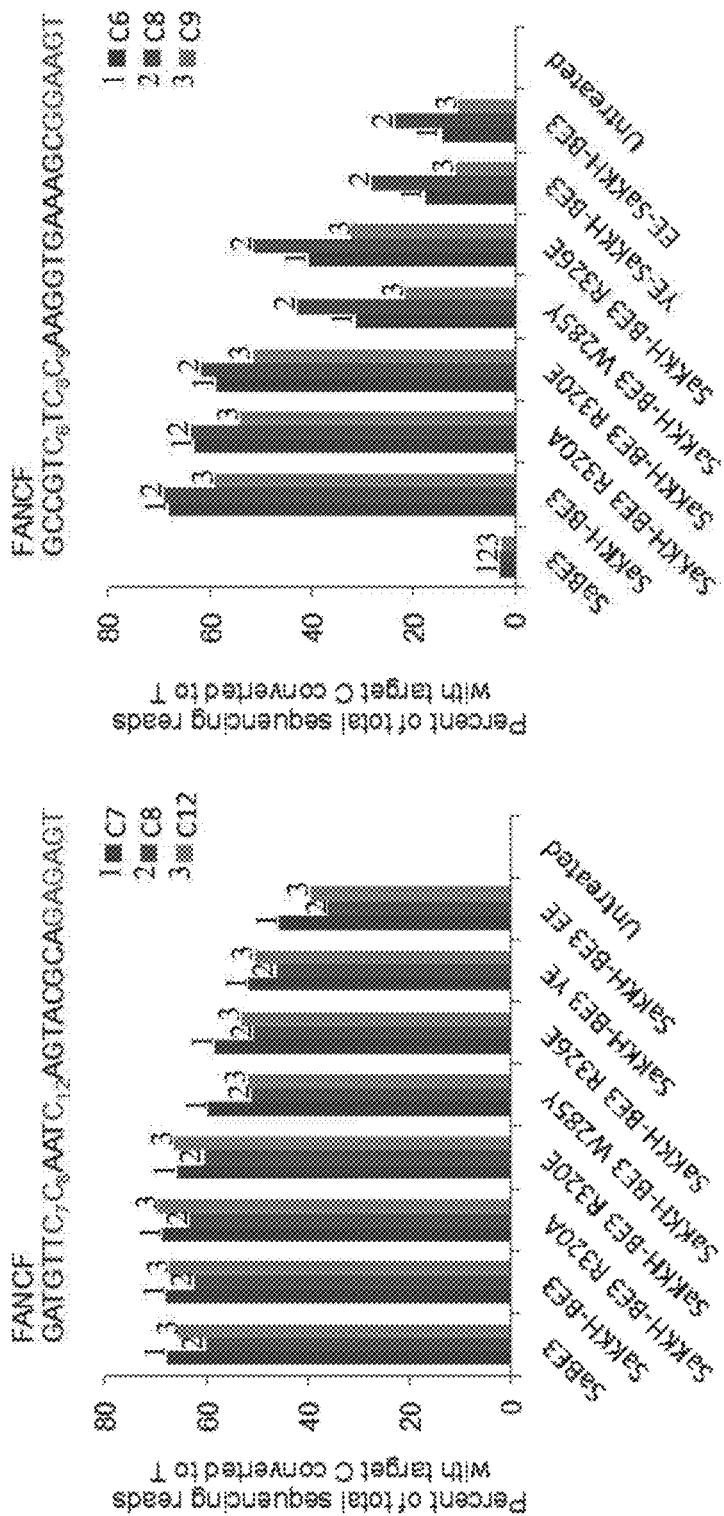

FIGS. 107A to 107B show the effect of APOBEC1 mutations on VQR-BE3 and SaKKH-BE3. HEK293T cells were transfected with plasmids expressing VQR-BE3, SaKKH-BE3 or its mutants and an appropriate sgRNAs. The treated cells were analyzed as described in the Methods. Cellular C to T conversion percentages, defined as the percentage of total DNA sequencing reads with Ts at the target positions indicated, are shown. FIG. 107A shows that the window-modulating mutations can be applied to VQR-BE3 to enable selective base editing at sites targetable by NGA PAM. FIG. 107B shows that, when applied to SaKKH-BE3, the mutations cause overall decrease in base editing efficiency without conferring base selectivity within the target window.

Figure 108:
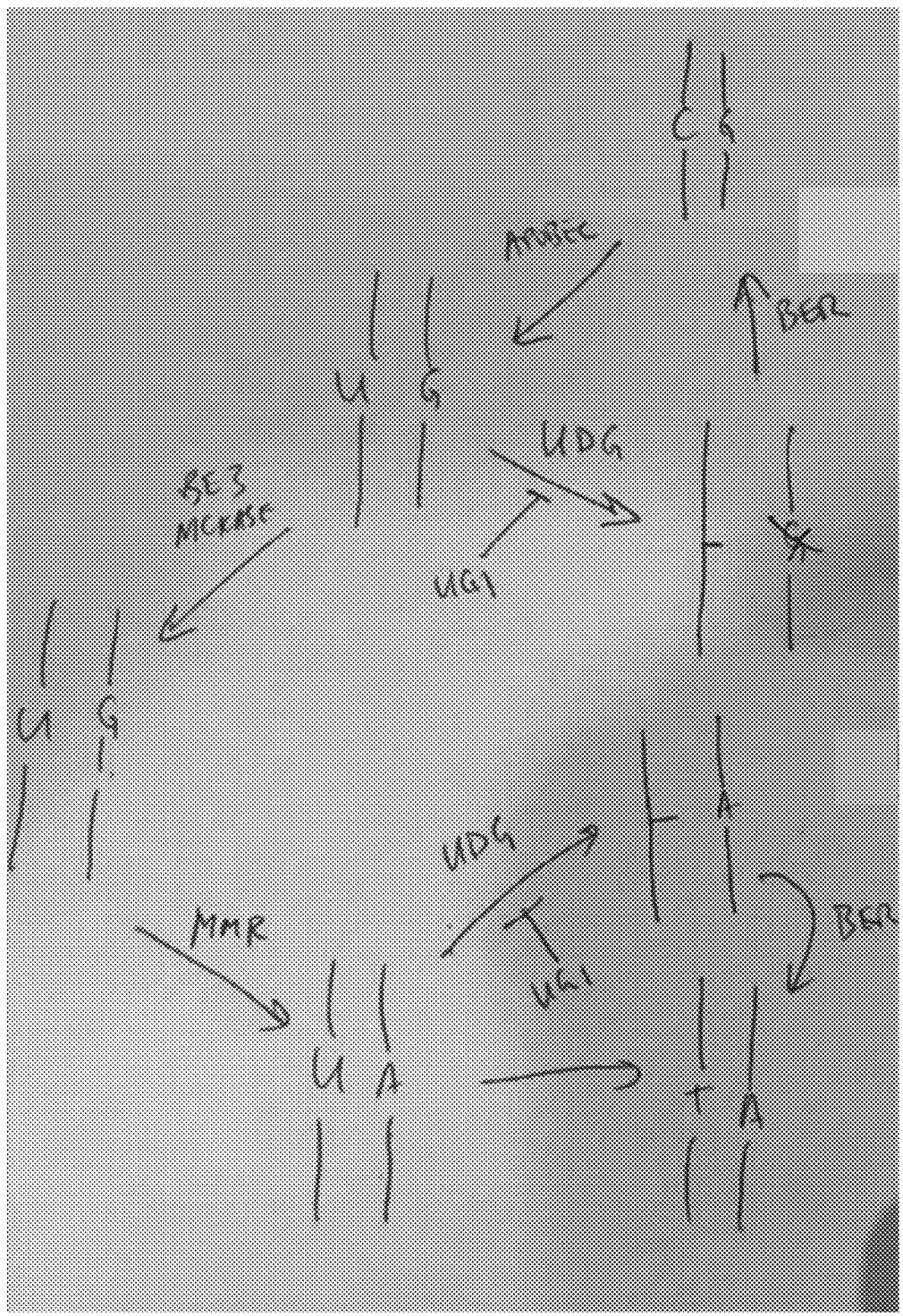

FIG. 108 shows a schematic representation of nucleotide editing. The following abbreviations are used: (MMR)—mismatch repair, (BE3 Nickase)—refers to base editor 3, which comprises a Cas9 nickase domain, (UGI)—uracil glycosylase inhibitor, UDG)—uracil DNA glycosylase, (APOBEC)—refers to an APOBEC cytidine deaminase.

DEFINITIONS

As used herein and in the claims, the singular forms "a," "an," and "the" include the singular and the plural reference unless the context clearly indicates otherwise. Thus, for example, a reference to "an agent" includes a single agent and a plurality of such agents.

The term "Cas9" or "Cas9 nuclease" refers to an RNA-guided nuclease comprising a Cas9 protein, or a fragment thereof (e.g., a protein comprising an active, inactive, or partially active DNA cleavage domain of Cas9, and/or the gRNA binding domain of Cas9). A Cas9 nuclease is also referred to sometimes as a casn1 nuclease or a CRISPR (clustered regularly interspaced short palindromic repeat)-associated nuclease. CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNAs. However, single guide RNAs ("sgRNA", or simply "gNRA") can be engineered so as to incorporate aspects of both the crRNA and tracrRNA into a single RNA species. See, e.g., Jinek M., Chylinski K., Fonfara I., Hauer M., Doudna J. A., Charpentier E. *Science* 337:816-821 (2012), the entire contents of which is hereby incorporated by reference. Cas9 recognizes a short motif in the CRISPR repeat sequences (the PAM or protospacer adjacent motif) to help distinguish self versus non-self. Cas9 nuclease sequences and structures are well known to those of skill in the art (see, e.g., "Complete genome sequence of an M1 strain of *Streptococcus pyogenes*." Ferretti et al., J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663 (2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607 (2011); and "A programmable dual-RNA-guided DNA endonuclease in adaptive bacterial immunity." Jinek M., Chylinski K., Fonfara I., Hauer M., Doudna J. A., Charpentier E. *Science* 337:816-821 (2012), the entire contents of each of which are incorporated herein by reference). Cas9 orthologs have been described in various species, including, but not limited to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737; the entire contents of which are incorporated herein by reference. In some embodiments, a Cas9 nuclease has an inactive (e.g., an inactivated) DNA cleavage domain, that is, the Cas9 is a nickase.

A nuclease-inactivated Cas9 protein may interchangeably be referred to as a "dCas9" protein (for nuclease-"dead" Cas9). Methods for generating a Cas9 protein (or a fragment thereof) having an inactive DNA cleavage domain are known (See, e.g., Jinek et al., *Science*. 337:816-821 (2012); Qi et al., "Repurposing CRISPR as an RNA-Guided Platform for Sequence-Specific Control of Gene Expression" (2013) *Cell*. 28; 152(5):1173-83, the entire contents of each of which are incorporated herein by reference). For example, the DNA cleavage domain of Cas9 is known to include two subdomains, the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H840A completely inactivate the nuclease activity of *S. pyogenes* Cas9 (Jinek et al., *Science*. 337:816-821 (2012); Qi et al., *Cell*. 28; 152(5):1173-83 (2013)). In some embodiments, proteins comprising fragments of Cas9 are provided. For example, in some embodiments, a protein comprises one of two Cas9 domains: (1) the gRNA binding domain of Cas9; or (2) the DNA cleavage domain of Cas9. In some embodiments, proteins comprising Cas9 or fragments thereof are referred to as "Cas9 variants." A Cas9 variant shares homology to Cas9, or a fragment thereof. For example a Cas9 variant is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to wild type Cas9. In some embodiments, the Cas9 variant may have 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50 or more amino acid changes compared to wild type Cas9. In some embodiments, the Cas9 variant comprises a fragment of Cas9 (e.g., a gRNA binding domain or a DNA-cleavage domain), such that the fragment is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to the corresponding fragment of wild type Cas9. In some embodiments, the fragment is is at least 30%, at least 35%, at least 40%, at least 45%, at least 50%, at least 55%, at least 60%, at least 65%, at least 70%, at least 75%, at least 80%, at least 85%, at least 90%, at least 95% identical, at least 96%, at least 97%, at least 98%, at least 99%, or at least 99.5% of the amino acid length of a corresponding wild type Cas9.

In some embodiments, the fragment is at least 100 amino acids in length. In some embodiments, the fragment is at least 100, 150, 200, 250, 300, 350, 400, 450, 500, 550, 600, 650, 700, 750, 800, 850, 900, 950, 1000, 1050, 1100, 1150, 1200, 1250, or at least 1300 amino acids in length. In some embodiments, wild type Cas9 corresponds to Cas9 from *Streptococcus pyogenes* (NCBI Reference Sequence: NC_017053.1, SEQ ID NO:1 (nucleotide); SEQ ID NO:2 (amino acid)).

```
                                                    (SEQ ID NO: 1)
ATGGATAAGAAATACTCAATAGGCTTAGATATCGGCACAAATAGCGTCGG

ATGGGCGGTGATCACTGATGATTATAAGGTTCCGTCTAAAAAGTTCAAGG

TTCTGGGAAATACAGACCGCCACAGTATCAAAAAAAATCTTATAGGGGCT

CTTTTATTTGGCAGTGGAGAGACAGCGGAAGCGACTCGTCTCAAACGGAC

AGCTCGTAGAAGGTATACACGTCGGAAGAATCGTATTTGTTATCTACAGG

AGATTTTTTCAAATGAGATGGCGAAAGTAGATGATAGTTTCTTTCATCGA

CTTGAAGAGTCTTTTTTGGTGGAAGAAGACAAGAAGCATGAACGTCATCC

TATTTTTGGAAATATAGTAGATGAAGTTGCTTATCATGAGAAATATCCAA

CTATCTATCATCTGCGAAAAAAATTGGCAGATTCTACTGATAAAGCGGAT

TTGCGCTTAATCTATTTGGCCTTAGCGCATATGATTAAGTTTCGTGGTCA

TTTTTTGATTGAGGGAGATTTAAATCCTGATAATAGTGATGTGGACAAAC

TATTTATCCAGTTGGTACAAATCTACAATCAATTATTTGAAGAAAACCCT

ATTAACGCAAGTAGAGTAGATGCTAAAGCGATTCTTTCTGCACGATTGAG

TAAATCAAGACGATTAGAAAATCTCATTGCTCAGCTCCCCGGTGAGAAGA

GAAATGGCTTGTTTGGGAATCTCATTGCTTTGTCATTGGGATTGACCCCT

AATTTTAAATCAAATTTTGATTTGGCAGAAGATGCTAAATTACAGCTTTC

AAAAGATACTTACGATGATGATTTAGATAATTTATTGGCGCAAATTGGAG

ATCAATATGCTGATTTGTTTTTGGCAGCTAAGAATTTATCAGATGCTATT

TTACTTTCAGATATCCTAAGAGTAAATAGTGAAATAACTAAGGCTCCCCT

ATCAGCTTCAATGATTAAGCGCTACGATGAACATCATCAAGACTTGACTC

TTTTAAAAGCTTTAGTTCGACAACAACTTCCAGAAAAGTATAAAGAAATC

TTTTTTGATCAATCAAAAAACGGATATGCAGGTTATATTGATGGGGGAGC

TAGCCAAGAAGAATTTTATAAATTTATCAAACCAATTTTAGAAAAAATGG

ATGGTACTGAGGAATTATTGGTGAAACTAAATCGTGAAGATTTGCTGCGC

AAGCAACGGACCTTTGACAACGGCTCTATTCCCCATCAAATTCACTTGGG

TGAGCTGCATGCTATTTTGAGAAGACAAGAAGACTTTTATCCATTTTTAA

AAGACAATCGTGAGAAGATTGAAAAAATCTTGACTTTTCGAATTCCTTAT

TATGTTGGTCCATTGGCGCGTGGCAATAGTCGTTTTGCATGGATGACTCG

GAAGTCTGAAGAAACAATTACCCCATGGAATTTTGAAGAAGTTGTCGATA

AAGGTGCTTCAGCTCAATCATTTATTGAACGCATGACAAACTTTGATAAA

AATCTTCCAAATGAAAAGTACTACCAAAACATAGTTTGCTTTATGAGTA

TTTTACGGTTTATAACGAATTGACAAAGGTCAAATATGTTACTGAGGGAA

TGCGAAAACCAGCATTTCTTTCAGGTGAACAGAAGAAAGCCATTGTTGAT

TTACTCTTCAAAACAAATCGAAAAGTAACCGTTAAGCAATTAAAAGAAGA

TTATTTCAAAAAAATAGAATGTTTTGATAGTGTTGAAATTTCAGGAGTTG

AAGATAGATTTAATGCTTCATTAGGCGCCTACCATGATTTGCTAAAAATT

ATTAAAGATAAAGATTTTTTGGATAATGAAGAAAATGAAGATATCTTAGA

GGATATTGTTTTAACATTGACCTTATTTGAAGATAGGGGGATGATTGAGG

AAAGACTTAAAACATATGCTCACCTCTTTGATGATAAGGTGATGAAACAG

CTTAAACGTCGCCGTTATACTGGTTGGGGACGTTTGTCTCGAAAATTGAT

TAATGGTATTAGGGATAAGCAATCTGGCAAAACAATATTAGATTTTTTGA

AATCAGATGGTTTTGCCAATCGCAATTTTATGCAGCTGATCCATGATGAT

AGTTTGACATTTAAAGAAGATATTCAAAAAGCACAGGTGTCTGGACAAGG

CCATAGTTTACATGAACAGATTGCTAACTTAGCTGGCAGTCCTGCTATTA

AAAAAGGTATTTTACAGACTGTAAAAATTGTTGATGAACTGGTCAAAGTA

ATGGGGCATAAGCCAGAAAATATCGTTATTGAAATGGCACGTGAAAATCA

GACAACTCAAAAGGGCCAGAAAAATTCGCGAGAGCGTATGAAACGAATCG

AAGAAGGTATCAAAGAATTAGGAAGTCAGATTCTTAAAGAGCATCCTGTT

GAAAATACTCAATTGCAAAATGAAAAGCTCTATCTCTATTATCTACAAAA

TGGAAGAGACATGTATGTGGACCAAGAATTAGATATTAATCGTTTAAGTG

ATTATGATGTCGATCACATTGTTCCACAAAGTTTCATTAAAGACGATTCA

ATAGACAATAAGGTACTAACGCGTTCTGATAAAAATCGTGGTAAATCGGA

TAACGTTCCAAGTGAAGAAGTAGTCAAAAAGATGAAAAACTATTGGAGAC

AACTTCTAAACGCCAAGTTAATCACTCAACGTAAGTTTGATAATTTAACG

AAAGCTGAACGTGGAGGTTTGAGTGAACTTGATAAAGCTGGTTTTATCAA

ACGCCAATTGGTTGAAACTCGCCAAATCACTAAGCATGTGGCACAAATTT

TGGATAGTCGCATGAATACTAAATACGATGAAAATGATAAACTTATTCGA

GAGGTTAAAGTGATTACCTTAAAATCTAAATTAGTTTCTGACTTCCGAAA

AGATTTCCAATTCTATAAAGTACGTGAGATTAACAATTACCATCATGCCC
```

```
ATGATGCGTATCTAAATGCCGTCGTTGGAACTGCTTTGATTAAGAAATAT
CCAAAACTTGAATCGGAGTTTGTCTATGGTGATTATAAAGTTTATGATGT
TCGTAAAATGATTGCTAAGTCTGAGCAAGAAATAGGCAAAGCAACCGCAA
AATATTTCTTTTACTCTAATATCATGAACTTCTTCAAAACAGAAATTACA
CTTGCAAATGGAGAGATTCGCAAACGCCCTCTAATCGAAACTAATGGGGA
AACTGGAGAAATTGTCTGGGATAAAGGGCGAGATTTTGCCACAGTGCGCA
AAGTATTGTCCATGCCCCAAGTCAATATTGTCAAGAAAACAGAAGTACAG
ACAGGCGGATTCTCCAAGGAGTCAATTTTACCAAAAAGAAATTCGGACAA
GCTTATTGCTCGTAAAAAGACTGGGATCCAAAAAATATGGTGGTTTTG
ATAGTCCAACGGTAGCTTATTCAGTCCTAGTGGTTGCTAAGGTGGAAAAA
GGGAAATCGAAGAAGTTAAAATCCGTTAAAGAGTTACTAGGGATCACAAT
TATGGAAAGAAGTTCCTTTGAAAAAAATCCGATTGACTTTTAGAAGCTA
AAGGATATAAGGAAGTTAAAAAAGACTTAATCATTAAACTACCTAAATAT
AGTCTTTTTGAGTTAGAAAACGGTCGTAAACGGATGCTGGCTAGTGCCGG
AGAATTACAAAAGGAAATGAGCTGGCTCTGCCAAGCAAATATGTGAATT
TTTTATATTTAGCTAGTCATTATGAAAAGTTGAAGGGTAGTCCAGAAGAT
AACGAACAAAAACAATTGTTTGTGGAGCAGCATAAGCATTATTTAGATGA
GATTATTGAGCAAATCAGTGAATTTTCTAAGCGTGTTATTTTAGCAGATG
CCAATTTAGATAAAGTTCTTAGTGCATATAACAAACATAGAGACAAACCA
ATACGTGAACAAGCAGAAAATATTATTCATTTATTTACGTTGACGAATCT
TGGAGCTCCCGCTGCTTTTAAATATTTTGATACAACAATTGATCGTAAAC
GATATACGTCTACAAAAGAAGTTTTAGATGCCACTCTTATCCATCAATCC
ATCACTGGTCTTTATGAAACACGCATTGATTTGAGTCAGCTAGGAGGTGA
CTGA
```

```
(SEQ ID NO: 2)
MDKKYSIGLDIGTNSVGWAVITDDYKVPSKKFKVLGNTDRHSIKKNLIGA
LLFGSGETAEATRLKRTARRRYTRRKNRICYLQEIFSNEMAKVDDSFFHR
LEESFLVEEDKKHERHPIFGNIVDEVAYHEKYPTIYHLRKKLADSTDKA
DLRLIYLALAHMIKFRGHFLIEGDLNPDNSDVDKLFIQLVQIYNQLFEE
NPINASRVDAKAILSARLSKSRRLENLIAQLPGEKRNGLFGNLIALSLG
LTPNFKSNFDLAEDAKLQLSKDTYDDDLDNLLAQIGDQYADLFLAAKNL
SDAILLSDILRVNSEITKAPLSASMIKRYDEHHQDLTLLKALVRQQLPE
KYKEIFFDQSKNGYAGYIDGGASQEEFYKFIKPILEKMDGTEELLVKLN
REDLLRKQRTFDNGSIPHQIHLGELHAILRRQEDFYPFLKDNREKIEKI
LTFRIPYYVGPLARGNSRFAWMTRKSEETITPWNFEEVVDKGASAQSFI
ERMTNFDKNLPNEKVLPKHSLLYEYFTVYNELTKVKYVTEGMRKPAFLS
GEQKKAIVDLLFKTNRKVTVKQLKEDYFKKIECFDSVEISGVEDRFNAS
LGAYHDLLKIIKDKDFLDNEENEDILEDIVLTLTLFEDRGMIEERLKTY
AHLFDDKVMKQLKRRRYTGWGRLSRKLINGIRDKQSGKTILDFLKSDGF
ANRNFMQLIHDDSLTFKEDIQKAQVSGQGHSLHEQIANLAGSPAIKK
GILQTVKIVDELVKVMGHKPENIVIEMARENQTTQKGQKNSRERMKRIE
EGIKELGSQILKEHPVENTQLQNEKLYLYYLQNGRDMYVDQELDINRLS
DYDVDHIVPQSFIKDDSIDNKVLTRSDKNRGKSDNVPSEEVVKKMKNYW
RQLLNAKLITQRKFDNLTKAERGGLSELDKAGFIKRQLVETRQITKHVA
QILDSRMNTKYDENDKLIREVKVITLKSKLVSDFRKDFQFYKVREI
NNYHHAHDAYLNAVVGTALIKKYPKLESEFVYGDYKVYDVRKMIAKSEQ
EIGKATAKYFFYSNIMNFFKTEITLANGEIRKRPLIETNGETGEIVWDK
GRDFATVRKVLSMPQVNIVKKTEVQTGGFSKESILPKRNSDKLIARKKD
WDPKKYGGFDSPTVAYSVLVVAKVEKGKSKKLKSVKELLGITIMERSSF
EKNPIDFLEAKGYKEVKKDLIIKLPKYSLFELENGRKRMLASAGELQKG
NELALPSKYVNFLYLASHYEKLKGSPEDNEQKQLFVEQHKHYLDEIIEQ
ISEFSKRVILADANLDKVLSAYNKHRDKPIREQAENIIHLFTLTNLGAP
AAFKYFDTTIDRKRYTSTKEVLDATLIHQSITGLYETRIDLSQLGGD
(single underline: HNH domain; double underline: RuvC domain)
```

In some embodiments, wild type Cas9 corresponds to, or comprises SEQ ID NO:3 (nucleotide) and/or SEQ ID NO: 4 (amino acid):

```
(SEQ ID NO: 3)
ATGGATAAAAAGTATTCTATTGGTTTAGACATCGGCACTAATTCCGTTGG
ATGGGCTGTCATAACCGATGAATACAAAGTACCTTCAAAGAAATTTAAGG
TGTTGGGGAACACAGACCGTCATTCGATTAAAAAGAATCTTATCGGTGCC
CTCCTATTCGATAGTGGCGAAACGGCAGAGGCGACTCGCCTGAAACGAAC
CGCTCGGAGAAGGTATACACGTCGCAAGAACCGAATATGTTACTTACAAG
AAATTTTTAGCAATGAGATGGCCAAAGTTGACGATTCTTTCTTCACCGT
TTGGAAGAGTCCTTCCTTGTCGAAGAGGACAAGAAACATGAACGGCACCC
CATCTTTGGAAACATAGTAGATGAGGTGGCATATCATGAAAAGTACCCAA
CGATTTATCACCTCAGAAAAAAGCTAGTTGACTCAACTGATAAAGCGGAC
CTGAGGTTAATCTACTTGGCTCTTGCCCATATGATAAAGTTCCGTGGGCA
CTTTCTCATTGAGGGTGATCTAAATCCGGACAACTCGGATGTCGACAAAC
TGTTCATCCAGTTAGTACAAACCTATAATCAGTTGTTTGAAGAACCCT
ATAAATGCAAGTGGCGTGGATGCGAAGGCTATTCTTAGCGCCCGCCTCTC
TAAATCCCGACGGCTAGAAAACCTGATCGCACAATTACCCGGAGAGAAGA
AAAATGGGTTGTTCGGTAACCTTATAGCGCTCTCACTAGGCCTGACACCA
AATTTTAAGTCGAACTTCGACTTAGCTGAAGATGCCAAATTGCAGCTTAG
TAAGGACACGTACGATGACGATCTCGACAATCTACTGGCACAAATTGGAG
ATCAGTATGCGGACTTATTTTTGGCTGCCAAAAACCTTAGCGATGCAATC
CTCCTATCTGACATACTGAGAGTTAATACTGAGATTACCAAGGCGCCGTT
ATCCGCTTCAATGATCAAAAGGTACGATGAACATCACCAAGACTTGACAC
TTCTCAAGGCCCTAGTCCGTCAGCAACTGCCTGAGAAATATAAGGAAATA
TTCTTTGATCAGTCGAAAACGGGTACGCAGGTTATATTGACGGCGGAGC
GAGTCAAGAGGAATTCTACAAGTTTATCAAACCCATATTAGAGAAGATGG
ATGGGACGGAAGAGTTGCTTGTAAAACTCAATCGCGAAGATCTACTGCGA
```

-continued

```
AAGCAGCGGACTTTCGACAACGGTAGCATTCCACATCAAATCCACTTAGG
CGAATTGCATGCTATACTTAGAAGGCAGGAGGATTTTTATCCGTTCCTCA
AAGACAATCGTGAAAAGATTGAGAAAATCCTAACCTTTCGCATACCTTAC
TATGTGGGACCCCTGGCCCGAGGGAACTCTCGGTTCGCATGGATGACAAG
AAAGTCCGAAGAAACGATTACTCCATGGAATTTTGAGGAAGTTGTCGATA
AAGGTGCGTCAGCTCAATCGTTCATCGAGAGGATGACCAACTTTGACAAG
AATTTACCGAACGAAAAGTATTGCCTAAGCACAGTTTACTTTACGAGTA
TTTCACAGTGTACAATGAACTCACGAAAGTTAAGTATGTCACTGAGGGCA
TGCGTAAACCCGCCTTTCTAAGCGGAGAACAGAAGAAAGCAATAGTAGAT
CTGTTATTCAAGACCAACCGCAAAGTGACAGTTAAGCAATTGAAAGAGGA
CTACTTTAAGAAAATTGAATGCTTCGATTCTGTCGAGATCTCCGGGGTAG
AAGATCGATTTAATGCGTCACTTGGTACGTATCATGACCTCCTAAAGATA
ATTAAAGATAAGGACTTCCTGGATAACGAAGAGAATGAAGATATCTTAGA
AGATATAGTGTTGACTCTTACCCTCTTTGAAGATCGGGAAATGATTGAGG
AAAGACTAAAAACATACGCTCACCTGTTCGACGATAAGGTTATGAAACAG
TTAAAGAGGCGTCGCTATACGGGCTGGGGACGATTGTCGCGGAAACTTAT
CAACGGGATAAGAGACAAGCAAAGTGGTAAAACTATTCTCGATTTTCTAA
AGAGCGACGGCTTCGCCAATAGGAACTTTATGCAGCTGATCCATGATGAC
TCTTTAACCTTCAAAGAGGATATACAAAAGGCACAGGTTTCCGGACAAGG
GGACTCATTGCACGAACATATTGCGAATCTTGCTGGTTCGCCAGCCATCA
AAAAGGGCATACTCCAGACAGTCAAAGTAGTGGATGAGCTAGTTAAGGTC
ATGGGACGTCACAAACCGGAAAACATTGTAATCGAGATGGCACGCGAAAA
TCAAACGACTCAGAAGGGGCAAAAAAACAGTCGAGAGCGGATGAAGAGAA
TAGAAGAGGGTATTAAAGAACTGGGCAGCCAGATCTTAAAGGAGCATCCT
GTGGAAAATACCCAATTGCAGAACGAGAAACTTTACCTCTATTACCTACA
AAATGGAAGGGACATGTATGTTGATCAGGAACTGGACATAAACCGTTTAT
CTGATTACGACGTCGATCACATTGTACCCCAATCCTTTTTGAAGGACGAT
TCAATCGACAATAAAGTGCTTACACGCTCGGATAAGAACCGAGGGAAAAG
TGACAATGTTCCAAGCGAGGAAGTCGTAAAGAAAATGAAGAACTATTGGC
GGCAGCTCCTAAATGCGAAACTGATAACGCAAAGAAAGTTCGATAACTTA
ACTAAAGCTGAGAGGGGTGGCTTGTCTGAACTTGACAAGGCCGGATTTAT
TAAACGTCAGCTCGTGGAAACCCGCCAAATCACAAAGCATGTTGCACAGA
TACTAGATTCCCGAATGAATACGAAATACGACGAGAACGATAAGCTGATT
CGGGAAGTCAAAGTAATCACTTTAAAGTCAAAATTGGTGTCGGACTTCAG
AAAGGATTTTCAATTCTATAAAGTTAGGGAGATAAATAACTACCACCATG
CGCACGACGCTTATCTTAATGCCGTCGTAGGGACCGCACTCATTAAGAAA
TACCCGAAGCTAGAAAGTGAGTTTGTGTATGGTGATTACAAAGTTTATGA
CGTCCGTAAGATGATCGCGAAAAGCGAACAGGAGATAGGCAAGGCTACAG
CCAAATACTTCTTTTATTCTAACATTATGAATTTCTTTAAGACGGAAATC
ACTCTGGCAAACGGAGAGATACGCAAACGACCTTTAATTGAACCAATGG
GGAGACAGGTGAAATCGTATGGGATAAGGGCCGGGACTTCGCGACGGTGA
GAAAAGTTTTGTCCATGCCCCAAGTCAACATAGTAAAGAAAACTGAGGTG
CAGACCGGAGGGTTTTCAAAGGAATCGATTCTTCCAAAAAGGAATAGTGA
TAAGCTCATCGCTCGTAAAAAGGACTGGGACCCGAAAAAGTACGGTGGCT
TCGATAGCCCTACAGTTGCCTATTCTGTCCTAGTAGTGGCAAAAGTTGAG
AAGGGAAAATCCAAGAAACTGAAGTCAGTCAAAGAATTATTGGGGATAAC
GATTATGGAGCGCTCGTCTTTTGAAAAGAACCCCATCGACTTCCTTGAGG
CGAAAGGTTACAAGGAAGTAAAAAAGGATCTCATAATTAAACTACCAAAG
TATAGTCTGTTTGAGTTAGAAAATGGCCGAAAACGGATGTTGGCTAGCGC
CGGAGAGCTTCAAAAGGGGAACGAACTCGCACTACCGTCTAAATACGTGA
ATTTCCTGTATTTAGCGTCCCATTACGAGAAGTTGAAAGGTTCACCTGAA
GATAACGAACAGAAGCAACTTTTTGTTGAGCAGCACAAACATTATCTCGA
CGAAATCATAGAGCAAATTTCGGAATTCAGTAAGAGAGTCATCCTAGCTG
ATGCCAATCTGGACAAAGTATTAAGCGCATACAACAAGCACAGGGATAAA
CCCATACGTGAGCAGGCGGAAAATATTATCCATTTGTTTACTCTTACCAA
CCTCGGCGCTCCAGCCGCATTCAAGTATTTTGACACAACGATAGATCGCA
AACGATACACTTCTACCAAGGAGGTGCTAGACGCGACACTGATTCACCAA
TCCATCACGGGATTATATGAAACTCGGATAGATTTGTCACAGCTTGGGGG
TGACGGATCCCCAAGAAGAAGAGGAAAGTCTCGAGCGACTACAAAGACC
ATGACGGTGATTATAAAGATCATGACATCGATTACAAGGATGACGATGAC
AAGGCTGCAGGA
                              (SEQ ID NO: 4)
KKYSIGLAIGTNSVGWAVITDEYKVPSKKFKVLGNTDRHSIKKNLIGAL
LFDSGETAEATRLKRTARRRYTRRKNRICYLQEIFSNEMAKVDDSFFHR
LEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENP
INASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLKI
IKDKDFLDNEEENEDILEDIVLTLTLFEDREMIEERLKTYAHLFDDKVMKQ
LKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVKV
MGRHKPENIVIEMARENQTTQKGQKNSRERMKRIEEGIKELGSQILKEHP
VENTQLQNEKLYLYYLQNGRDMYVDQELDINRLSDYDVDHIVPQSFLKDD
SIDNKVLTRSDKNRGKSDNVPSEEVVKKMKNYWRQLLNAKLITQRKFDNL
TKAERGGLSELDKAGFIKRQLVETRQITKHVAQILDSRMNTKYDENDKLI
REVKVITLKSKLVSDFRKDFQFYKVREINNYHHAHDAYLNAVVGTALIKK
YPKLESEFVYGDYKVYDVRKMIAKSEQEIGKATAKYFFYSNIMNFFKTEI
```

-continued

<u>TLANGEIRKRPLIETNGETGEIVWDKGRDFATVRKVLSMPQVNIVKKT</u>

<u>EVQT</u>GGFSKESILPKRNSDKLIARKKDWDPKKYGGFDSPTVAYSVLVVA

KVEKGKSKKLKSVKELLGITIMERSSFEKNPIDFLEAKGYKEVKKDLII

KLPKYSLFELENGRKRMLASAGELQKGNELALPSKYVNFLYLASHYEKLK

GSPEDNEQKQLFVEQHKHYLDEIIEQISEFSKRVILADANLDKVLSAYNK

-continued

HRDKPIREQAENIIHLFTLTNLGAPAAFKYFDTTIDRKRYTSTKEVLDAT

LIHQSITGLYETRIDLSQLGGD (single underline: HNH domain; double underline: RuvC domain)

In some embodiments, wild type Cas9 corresponds to Cas9 from *Streptococcus pyogenes* (NCBI Reference Sequence: NC_002737.2, SEQ ID NO: 8 (nucleotide); and Uniport Reference Sequence: Q99ZW2, SEQ ID NO: 10 (amino acid).

(SEQ ID NO: 8)
ATGGATAAGAAATACTCAATAGGCTTAGATATCGGCACAAATAGCGTCGGATGG

GCGGTGATCACTGATGAATATAAGGTTCCGTCTAAAAAGTTCAAGGTTCTGGGAA

ATACAGACCGCCACAGTATCAAAAAAATCTTATAGGGGCTCTTTTATTTGACAG

TGGAGAGACAGCGGAAGCGACTCGTCTCAAACGACAGCTCGTAGAAGGTATAC

ACGTCGGAAGAATCGTATTTGTTATCTACAGGAGATTTTTTCAAATGAGATGGCG

AAAGTAGATGATAGTTTCTTTCATCGACTTGAAGAGTCTTTTTTGGTGGAAGAAG

ACAAGAAGCATGAACGTCATCCTATTTTTGGAAATATAGTAGATGAAGTTGCTTA

TCATGAGAAATATCCAACTATCTATCATCTGCGAAAAAAATTGGTAGATTCTACT

GATAAAGCGGATTTGCGCTTAATCTATTTGGCCTTAGCGCATATGATTAAGTTTC

GTGGTCATTTTTTGATTGAGGGAGATTTAAATCCTGATAATAGTGATGTGGACAA

ACTATTTATCCAGTTGGTACAAACCTACAATCAATTATTTGAAGAAAACCCTATT

AACGCAAGTGGAGTAGATGCTAAAGCGATTCTTTCTGCACGATTGAGTAAATCA

AGACGATTAGAAAATCTCATTGCTCAGCTCCCCGGTGAGAAGAAAAATGGCTTA

TTTGGGAATCTCATTGCTTTGTCATTGGGTTTGACCCCTAATTTTAAATCAAATTT

TGATTTGGCAGAAGATGCTAAATTACAGCTTTCAAAAGATACTTACGATGATGAT

TTAGATAATTTATTGGCGCAAATTGGAGATCAATATGCTGATTTGTTTTTGGCAG

CTAAGAATTTATCAGATGCTATTTTACTTTCAGATATCCTAAGAGTAAATACTGA

AATAACTAAGGCTCCCCTATCAGCTTCAATGATTAAACGCTACGATGAACATCAT

CAAGACTTGACTCTTTTAAAAGCTTTAGTTCGACAACAACTTCCAGAAAAGTATA

AAGAAATCTTTTTTGATCAATCAAAAAACGGATATGCAGGTTATATTGATGGGGG

AGCTAGCCAAGAAGAATTTTATAAATTTATCAAACCAATTTTAGAAAAAATGGAT

GGTACTGAGGAATTATTGGTGAAACTAAATCGTGAAGATTTGCTGCGCAAGCAA

CGGACCTTTGACAACGGCTCTATTCCCCATCAAATTCACTTGGGTGAGCTGCATG

CTATTTTGAGAAGACAAGAAGACTTTTATCCATTTTTAAAAGACAATCGTGAGAA

GATTGAAAAAATCTTGACTTTTCGAATTCCTTATTATGTTGGTCCATTGGCGCGTG

GCAATAGTCGTTTTGCATGGATGACTCGGAAGTCTGAAGAAACAATTACCCCATG

GAATTTTGAAGAAGTTGTCGATAAAGGTGCTTCAGCTCAATCATTTATTGAACGC

ATGACAAACTTTGATAAAAATCTTCCAAATGAAAAAGTACTACCAAAACATAGT

TTGCTTTATGAGTATTTTACGGTTTATAACGAATTGACAAAGGTCAAATATGTTA

CTGAAGGAATGCGAAAACCAGCATTTCTTTCAGGTGAACAGAAGAAAGCCATTG

TTGATTTACTCTTCAAAACAAATCGAAAAGTAACCGTTAAGCAATTAAAAGAAG

ATTATTTCAAAAAAATAGAATGTTTTGATAGTGTTGAAATTTCAGGAGTTGAAGA

TAGATTTAATGCTTCATTAGGTACCTACCATGATTTGCTAAAAATTATTAAAGAT

-continued

```
AAAGATTTTTTGGATAATGAAGAAAATGAAGATATCTTAGAGGATATTGTTTTAA

CATTGACCTTATTTGAAGATAGGGAGATGATTGAGGAAAGACTTAAAACATATG

CTCACCTCTTTGATGATAAGGTGATGAAACAGCTTAAACGTCGCCGTTATACTGG

TTGGGGACGTTTGTCTCGAAAATTGATTAATGGTATTAGGGATAAGCAATCTGGC

AAAACAATATTAGATTTTTTGAAATCAGATGGTTTTGCCAATCGCAATTTTATGC

AGCTGATCCATGATGATAGTTTGACATTTAAAGAAGACATTCAAAAAGCACAAG

TGTCTGGACAAGGCGATAGTTTACATGAACATATTGCAAATTTAGCTGGTAGCCC

TGCTATTAAAAAAGGTATTTTACAGACTGTAAAAGTTGTTGATGAATTGGTCAAA

GTAATGGGGCGGCATAAGCCAGAAAATATCGTTATTGAAATGGCACGTGAAAAT

CAGACAACTCAAAAGGGCCAGAAAAATTCGCGAGAGCGTATGAAACGAATCGA

AGAAGGTATCAAAGAATTAGGAAGTCAGATTCTTAAAGAGCATCCTGTTGAAAA

TACTCAATTGCAAAATGAAAAGCTCTATCTCTATTATCTCCAAAATGGAAGAGAC

ATGTATGTGGACCAAGAATTAGATATTAATCGTTTAAGTGATTATGATGTCGATC

ACATTGTTCCACAAAGTTTCCTTAAAGACGATTCAATAGACAATAAGGTCTTAAC

GCGTTCTGATAAAAATCGTGGTAAATCGGATAACGTTCCAAGTGAAGAAGTAGT

CAAAAAGATGAAAAACTATTGGAGACAACTTCTAAACGCCAAGTTAATCACTCA

ACGTAAGTTTGATAATTTAACGAAAGCTGAACGTGGAGGTTTGAGTGAACTTGAT

AAAGCTGGTTTTATCAAACGCCAATTGGTTGAAACTCGCCAAATCACTAAGCATG

TGGCACAAATTTTGGATAGTCGCATGAATACTAAATACGATGAAAATGATAAAC

TTATTCGAGAGGTTAAAGTGATTACCTTAAAATCTAAATTAGTTTCTGACTTCCG

AAAAGATTTCCAATTCTATAAAGTACGTGAGATTAACAATTACCATCATGCCCAT

GATGCGTATCTAAATGCCGTCGTTGGAACTGCTTTGATTAAGAAATATCCAAAAC

TTGAATCGGAGTTTGTCTATGGTGATTATAAAGTTTATGATGTTCGTAAAATGATT

GCTAAGTCTGAGCAAGAAATAGGCAAAGCAACCGCAAAATATTTCTTTTACTCTA

ATATCATGAACTTCTTCAAAACAGAAATTACACTTGCAAATGGAGAGATTCGCAA

ACGCCCTCTAATCGAAACTAATGGGGAAACTGGAGAAATTGTCTGGGATAAAGG

GCGAGATTTTGCCACAGTGCGCAAAGTATTGTCCATGCCCCAAGTCAATATTGTC

AAGAAAACAGAAGTACAGACAGGCGGATTCTCCAAGGAGTCAATTTTACCAAAA

AGAAATTCGGACAAGCTTATTGCTCGTAAAAAAGACTGGGATCCAAAAAAATAT

GGTGGTTTTGATAGTCCAACGGTAGCTTATTCAGTCCTAGTGGTTGCTAAGGTGG

AAAAAGGGAAATCGAAGAAGTTAAAATCCGTTAAAGAGTTACTAGGGATCACAA

TTATGGAAAGAAGTTCCTTTGAAAAAAATCCGATTGACTTTTTAGAAGCTAAAGG

ATATAAGGAAGTTAAAAAAGACTTAATCATTAAACTACCTAAATATAGTCTTTTT

GAGTTAGAAAACGGTCGTAAACGGATGCTGGCTAGTGCCGGAGAATTACAAAAA

GGAAATGAGCTGGCTCTGCCAAGCAAATATGTGAATTTTTTATATTTAGCTAGTC

ATTATGAAAAGTTGAAGGGTAGTCCAGAAGATAACGAACAAAAACAATTGTTTG

TGGAGCAGCATAAGCATTATTTAGATGAGATTATTGAGCAAATCAGTGAATTTTC

TAAGCGTGTTATTTTAGCAGATGCCAATTTAGATAAAGTTCTTAGTGCATATAAC

AAACATAGAGACAAACCAATACGTGAACAAGCAGAAAATATTATTCATTTATTT

ACGTTGACGAATCTTGGAGCTCCCGCTGCTTTTAAATATTTTGATACAACAATTG

ATCGTAAACGATATACGTCTACAAAAGAAGTTTTAGATGCCACTCTTATCCATCA
```

```
                                                      -continued
ATCCATCACTGGTCTTTATGAAACACGCATTGATTTGAGTCAGCTAGGAGGTGAC

TGA
```

```
                                                      (SEQ ID NO: 10)
MDKKYSIGLDIGTNSVGWAVITDEYKVPSKKFKVLGNTDRHSIKKNLIGALLFDSGE

TAEATRLKRTARRRYTRRKNRICYLQEIFSNEMAKVDDSFFHRLEESFLVEEDKKHE

RHPIFGNIVDEVAYHEKYPTIYHLRKKLVDSTDKADLRLIYLALAHMIKFRGHFLIEG

DLNPDNSDVDKLFIQLVQTYNQLFEENPINASGVDAKAILSARLSKSRRLENLIAQLP

GEKKNGLFGNLIALSLGLTPNFKSNFDLAEDAKLQLSKDTYDDDLDNLLAQIGDQYA

DLFLAAKNLSDAILLSDILRVNTEITKAPLSASMIKRYDEHHQDLTLLKALVRQQLPE

KYKEIFFDQSKNGYAGYIDGGASQEEFYKFIKPILEKMDGTEELLVKLNREDLLRKQR

TFDNGSIPHQIHLGELHAILRRQEDFYPFLKDNREKIEKILTFRIPYYVGPLARGNSRFA

WMTRKSEETITPWNFEEVVDKGASAQSFIERMTNFDKNLPNEKVLPKHSLLYEYFTV

YNELTKVKYVTEGMRKPAFLSGEQKKAIVDLLFKTNRKVTVKQLKEDYFKKIECFD

SVEISGVEDRFNASLGTYHDLLKIIKDKDFLDNEENEDILEDIVLTLTLFEDREMIEERL

KTYAHLFDDKVMKQLKRRRYTGWGRLSRKLINGIRDKQSGKTILDFLKSDGFANRN

FMQLIHDDLTFKEDIQKAQVSGQGDSLHEHIANLAGSPAIKKGILQTVKVVDELVK

VMGRHKPENIVIEMARENQTTQKGQKNSRERMKRIEEGIKELGSQILKEHPVENTQL

QNEKLYLYYLQNGRDMYVDQELDINRLSDYDVDHIVPQSFLKDDSIDNKVLTRSDK

NRGKSDNVPSEEVVKKMKNYWRQLLNAKLITQRKFDNLTKAERGGLSELDKAGFIK

RQLVETRQITKHVAQILDSRMNTKYDENDKLIREVKVITLKSKLVSDFRKDFQFYKV

REINNYHHAHDAYLNAVVGTALIKKYPKLESEFVYGDYKVYDVRKMIAKSEQEIGK

ATAKYFFYSNIMNFFKTEITLANGEIRKRPLIETNGETGEIVWDKGRDFATVRKVLSM

PQVNIVKKTEVQTGGFSKESILPKRNSDKLIARKKDWDPKKYGGFDSPTVAYSVLVV

AKVEKGKSKKLKSVKELLGITIMERSSFEKNPIDFLEAKGYKEVKKDLIIKLPKYSLFE

LENGRKRMLASAGELQKGNELALPSKYVNFLYLASHYEKLKGSPEDNEQKQLFVEQ

HKHYLDEIIEQISEFSKRVILADANLDKVLSAYNKHRDKPIREQAENIIHLFTLTNLGA

PAAFKYFDTTIDRKRYTSTKEVLDATLIHQSITGLYETRIDLSQLGGD
(single underline: HNH domain; double underline: RuvC domain)
```

In some embodiments, Cas9 refers to Cas9 from: *Corynebacterium ulcerans* (NCBI Refs: NC_015683.1, NC_017317.1); *Corynebacterium diphtheria* (NCBI Refs: NC_016782.1, NC_016786.1); *Spiroplasma syrphidicola* (NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychroflexus torquisI* (NCBI Ref: NC_018721.1); *Streptococcus thermophilus* (NCBI Ref: YP_820832.1), *Listeria innocua* (NCBI Ref: NP_472073.1), *Campylobacter jejuni* (NCBI Ref: YP_002344900.1) or *Neisseria meningitidis* (NCBI Ref: YP_002342100.1) or to a Cas9 from any of the organisms listed in Example 5.

In some embodiments, dCas9 corresponds to, or comprises in part or in whole, a Cas9 amino acid sequence having one or more mutations that inactivate the Cas9 nuclease activity. For example, in some embodiments, a dCas9 domain comprises D10A and/or H840A mutation.

dCas9 (D10A and H840A):

```
                                                      (SEQ ID NO: 9)
MDKKYSIGLAIGTNSVGWAVITDEYKVPSKKFKVLGNTDRHSIKKNLIGALLFDS

GETAEATRLKRTARRRYTRRKNRICYLQEIFSNEMAKVDDSFFHRLEESFLVEEDKK

HERHPIFGNIVDEVAYHEKYPTIYHLRKKLVDSTDKADLRLIYLALAHMIKFRGHFLI

EGDLNPDNSDVDKLFIQLVQTYNQLFEENPINASGVDAKAILSARLSKSRRLENLIAQ

LPGEKKNGLFGNLIALSLGLTPNFKSNFDLAEDAKLQLSKDTYDDDLDNLLAQIGDQ
```

-continued

```
YADLFLAAKNLSDAILLSDILRVNTEITKAPLSASMIKRYDEHHQDLTLLKALVRQQL

PEKYKEIFFDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYYVGPLARGNSR

FAWMTRKSEETITPWNFEEVVDKGASAQSFIERMTNFDKNLPNEKVLPKHSLLYEYF

TVYNELTKVKYVTEGMRKPAFLSGEQKKAIVDLLFKTNRKVTVKQLKEDYFKKIEC

FDSVETSGVEDRFNASLGTYHDLLKIIKDKDFLDNEENEDILEDIVLTLTLFEDREMIEE

RLKTYAHLFDDKVMKQLKRRRYTGWGRLSRKLINGIRDKQSGKTILDFLKSDGFAN

RNFMQLIHDDSLTFKEDIQKAQVSGQQDSLHEHIANLAGSPAIKKGILQTVKVVDEL

VKVMGRHKPENIVIEMARENQTTQKGQKNSRERMKRIEEGIKELGSQILKEHPVE

NTQLONEKLYLYYLONGRDMYVDOELDINRLSDYDVDAIVPOSFLKDDSIDNKV

LTRSDKNRGKSDNVPSEEVVKKMKNYWRQLLNAKLITQRKFDNLTKAERGGLS

ELDKAGFIKRQLVETRQITKHVAQILDSRMNTKYDENDKLIREVKVITLKSKLVSDFR

KDFQFYKVREINNYHHAHDAYLNAVVGTALIKKYPKLESEFVYGDYKVYDVRKMI

AKSEQEIGKATAKYFFYSNIMNFFKTEITLANGEIRKRPLIETNGETGEIVWDKGRDF

ATVRKVLSMPQVNIVKKTEVQTGGFSKESILPKRNSDKLIARKKDWDPKKYGGFDSP

TVAYSVLVVAKVEKGKSKKLKSVKELLGITIMERSSFEKNPIDFLEAKGYKEVKKDLI

IKLPKYSLFELENGRKRMLASAGELQKGNELALPSKYVNFLYLASHYEKLKGSPEDN

EQKQLFVEQHKHYLDEIIEQISEFSKRVILADANLDKVLSAYNKHRDKP1REQAENIIH

LFTLTNLGAPAAFKYFDTTIDRKRYTSTKEVLDATLIHQSITGLYETRIDLSQLGGD
```

(single underline: HNH domain; double underline: RuvC domain).

In some embodiments, the Cas9 domain comprises a D10A mutation, while the residue at position 840 remains a histidine in the amino acid sequence provided in SEQ ID NO: 10, or at corresponding positions in any of the amino acid sequences provided in SEQ ID NOs: 11-260. Without wishing to be bound by any particular theory, the presence of the catalytic residue H840 restores the activity of the Cas9 to cleave the non-edited (e.g., non-deaminated) strand containing a G opposite the targeted C. Restoration of H840 (e.g., from A840) does not result in the cleavage of the target strand containing the C. Such Cas9 variants are able to generate a single-strand DNA break (nick) at a specific location based on the gRNA-defined target sequence, leading to repair of the non-edited strand, ultimately resulting in a G to A change on the non-edited strand. A schematic representation of this process is shown in FIG. 108. Briefly, the C of a C-G basepair can be deaminated to a U by a deaminase, e.g., an APOBEC deamonase. Nicking the non-edited strand, having the G, facilitates removal of the G via mismatch repair mechanisms. UGI inhibits UDG, which prevents removal of the U.

In other embodiments, dCas9 variants having mutations other than D10A and H840A are provided, which, e.g., result in nuclease inactivated Cas9 (dCas9). Such mutations, by way of example, include other amino acid substitutions at D10 and H820, or other substitutions within the nuclease domains of Cas9 (e.g., substitutions in the HNH nuclease subdomain and/or the RuvC1 subdomain). In some embodiments, variants or homologues of dCas9 (e.g., variants of SEQ ID NO: 10) are provided which are at least about 70% identical, at least about 80% identical, at least about 90% identical, at least about 95% identical, at least about 98% identical, at least about 99% identical, at least about 99.5% identical, or at least about 99.9% identical to SEQ ID NO: 10. In some embodiments, variants of dCas9 (e.g., variants of SEQ ID NO: 10) are provided having amino acid sequences which are shorter, or longer than SEQ ID NO: 10, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids or more.

In some embodiments, Cas9 fusion proteins as provided herein comprise the full-length amino acid sequence of a Cas9 protein, e.g., one of the Cas9 sequences provided herein. In other embodiments, however, fusion proteins as provided herein do not comprise a full-length Cas9 sequence, but only a fragment thereof. For example, in some embodiments, a Cas9 fusion protein provided herein comprises a Cas9 fragment, wherein the fragment binds crRNA and tracrRNA or sgRNA, but does not comprise a functional nuclease domain, e.g., in that it comprises only a truncated version of a nuclease domain or no nuclease domain at all. Exemplary amino acid sequences of suitable Cas9 domains and Cas9 fragments are provided herein, and additional suitable sequences of Cas9 domains and fragments will be apparent to those of skill in the art.

In some embodiments, Cas9 refers to Cas9 from: *Corynebacterium ulcerans* (NCBI Refs: NC_015683.1, NC_017317.1); *Corynebacterium diphtheria* (NCBI Refs: NC_016782.1, NC_016786.1); *Spiroplasma syrphidicola* (NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychroflexus torquisI* (NCBI Ref:

NC_018721.1); *Streptococcus thermophilus* (NCBI Ref: YP_820832.1); *Listeria innocua* (NCBI Ref: NP_472073.1); *Campylobacter jejuni* (NCBI Ref: YP_002344900.1); or *Neisseria meningitidis* (NCBI Ref: YP_002342100.1).

The term "deaminase" or "deaminase domain," as used herein, refers to a protein or enzyme that catalyzes a deamination reaction. In some embodiments, the deaminase or deaminase domain is a cytidine deaminase, catalyzing the hydrolytic deamination of cytidine or deoxycytidine to uridine or deoxyuridine, respectively. In some embodiments, the deaminase or deaminase domain is a cytidine deaminase domain, catalyzing the hydrolytic deamination of cytosine to uracil. In some embodiments, the deaminase or deaminase domain is a naturally-occurring deaminase from an organism, such as a human, chimpanzee, gorilla, monkey, cow, dog, rat, or mouse. In some embodiments, the deaminase or deaminase domain is a variant of a naturally-occurring deaminase from an organism, that does not occur in nature. For example, in some embodiments, the deaminase or deaminase domain is at least 50%, at least 55%, at least 60%, at least 65%, at least 70%, at least 75% at least 80%, at least 85%, at least 90%, at least 95%, at least 96%, at least 97%, at least 98%, at least 99%, or at least 99.5% identical to a naturally-occuring deaminase from an organism.

The term "effective amount," as used herein, refers to an amount of a biologically active agent that is sufficient to elicit a desired biological response. For example, in some embodiments, an effective amount of a nuclease may refer to the amount of the nuclease that is sufficient to induce cleavage of a target site specifically bound and cleaved by the nuclease. In some embodiments, an effective amount of a fusion protein provided herein, e.g., of a fusion protein comprising a nuclease-inactive Cas9 domain and a nucleic acid editing domain (e.g., a deaminase domain) may refer to the amount of the fusion protein that is sufficient to induce editing of a target site specifically bound and edited by the fusion protein. As will be appreciated by the skilled artisan, the effective amount of an agent, e.g., a fusion protein, a nuclease, a deaminase, a recombinase, a hybrid protein, a protein dimer, a complex of a protein (or protein dimer) and a polynucleotide, or a polynucleotide, may vary depending on various factors as, for example, on the desired biological response, e.g., on the specific allele, genome, or target site to be edited, on the cell or tissue being targeted, and on the agent being used.

The term "linker," as used herein, refers to a chemical group or a molecule linking two molecules or moieties, e.g., two domains of a fusion protein, such as, for example, a nuclease-inactive Cas9 domain and a nucleic acid editing domain (e.g., a deaminase domain). In some embodiments, a linker joins a gRNA binding domain of an RNA-programmable nuclease, including a Cas9 nuclease domain, and the catalytic domain of anucleic-acid editing protein. In some embodiments, a linker joins a dCas9 and a nucleic-acid editing protein. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

The term "mutation," as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Various methods for making the amino acid substitutions (mutations) provided herein are well known in the art, and are provided by, for example, Green and Sambrook, *Molecular Cloning: A Laboratory Manual* (4$^{th}$ ed., Cold Spring Harbor Laboratory Press, Cold Spring Harbor, N.Y. (2012)).

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, e.g., analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term "nucleic acid editing domain," as used herein refers to a protein or enzyme capable of making one or more modifications (e.g., deamination of a cytidine residue) to a nucleic acid (e.g., DNA or RNA). Exemplary nucleic acid editing domains include, but are not limited to a deaminase, a nuclease, a nickase, a recombinase, a methyltransferase, a methylase, an acetylase, an acetyltransferase, a transcriptional activator, or a transcriptional repressor domain. In some embodiments the nucleic acid editing domain is a deaminase (e.g., a cytidine deaminase, such as an APOBEC or an AID deaminase).

The term "proliferative disease," as used herein, refers to any disease in which cell or tissue homeostasis is disturbed in that a cell or cell population exhibits an abnormally elevated proliferation rate. Proliferative diseases include hyperproliferative diseases, such as pre-neoplastic hyperplastic conditions and neoplastic diseases. Neoplastic diseases are characterized by an abnormal proliferation of cells and include both benign and malignant neoplasias. Malignant neoplasia is also referred to as cancer.

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. The term "fusion protein" as used herein refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. A protein may comprise different domains, for example, a nucleic acid binding domain (e.g., the gRNA binding domain of Cas9 that directs the binding of the protein to a target site) and a nucleic acid cleavage domain or a catalytic domain of a nucleic-acid editing protein. In some embodiments, a protein comprises a proteinaceous part, e.g., an amino acid sequence constituting a nucleic acid binding domain, and an organic compound, e.g., a compound that can act as a nucleic acid cleavage agent. In some embodiments, a protein is in a complex with, or is in association with, a nucleic acid, e.g., RNA. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* (4$^{th}$ ed., Cold Spring Harbor Laboratory Press, Cold Spring Harbor, N.Y. (2012)), the entire contents of which are incorporated herein by reference.

The term "RNA-programmable nuclease," and "RNA-guided nuclease" are used interchangeably herein and refer to a nuclease that forms a complex with (e.g., binds or associates with) one or more RNA that is not a target for cleavage. In some embodiments, an RNA-programmable nuclease, when in a complex with an RNA, may be referred to as a nuclease:RNA complex. Typically, the bound RNA(s) is referred to as a guide RNA (gRNA). gRNAs can exist as a complex of two or more RNAs, or as a single RNA molecule. gRNAs that exist as a single RNA molecule may be referred to as single-guide RNAs (sgRNAs), though "gRNA" is used interchangeably to refer to guide RNAs that exist as either single molecules or as a complex of two or more molecules. Typically, gRNAs that exist as single RNA species comprise two domains: (1) a domain that shares homology to a target nucleic acid (e.g., and directs binding of a Cas9 complex to the target); and (2) a domain that binds a Cas9 protein. In some embodiments, domain (2) corresponds to a sequence known as a tracrRNA, and comprises a stem-loop structure. For example, in some embodiments, domain (2) is identical or homologous to a tracrRNA as provided in Jinek et al., *Science* 337:816-821 (2012), the entire contents of which is incorporated herein by reference. Other examples of gRNAs (e.g., those including domain 2) can be found in U.S. Provisional Patent Application, U.S. Ser. No. 61/874,682, filed Sep. 6, 2013, entitled "Switchable Cas9 Nucleases And Uses Thereof," and U.S. Provisional Patent Application, U.S. Ser. No. 61/874,746, filed Sep. 6, 2013, entitled "Delivery System For Functional Nucleases," the entire contents of each are hereby incorporated by reference in their entirety. In some embodiments, a gRNA comprises two or more of domains (1) and (2), and may be referred to as an "extended gRNA." For example, an extended gRNA will, e.g., bind two or more Cas9 proteins and bind a target nucleic acid at two or more distinct regions, as described herein. The gRNA comprises a nucleotide sequence that complements a target site, which mediates binding of the nuclease/RNA complex to said target site, providing the sequence specificity of the nuclease:RNA complex. In some embodiments, the RNA-programmable nuclease is the (CRISPR-associated system) Cas9 endonuclease, for example Cas9 (Csn1) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663 (2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607 (2011); and "A programmable dual-RNA-guided DNA endonuclease in adaptive bacterial immunity." Jinek M., Chylinski K., Fonfara I., Hauer M., Doudna J. A., Charpentier E. Science 337:816-821 (2012), the entire contents of each of which are incorporated herein by reference.

Because RNA-programmable nucleases (e.g., Cas9) use RNA:DNA hybridization to target DNA cleavage sites, these proteins are able to be targeted, in principle, to any sequence specified by the guide RNA. Methods of using RNA-programmable nucleases, such as Cas9, for site-specific cleavage (e.g., to modify a genome) are known in the art (see e.g., Cong, L. et al. Multiplex genome engineering using CRISPR/Cas systems. *Science* 339, 819-823 (2013); Mali, P. et al. RNA-guided human genome engineering via Cas9. *Science* 339, 823-826 (2013); Hwang, W. Y. et al. Efficient genome editing in zebrafish using a CRISPR-Cas system. *Nature biotechnology* 31, 227-229 (2013); Jinek, M. et al. RNA-programmed genome editing in human cells. *eLife* 2, e00471 (2013); Dicarlo, J. E. et al. Genome engineering in *Saccharomyces cerevisiae* using CRISPR-Cas systems. *Nucleic acids research* (2013); Jiang, W. et al. RNA-guided editing of bacterial genomes using CRISPR-Cas systems. *Nature biotechnology* 31, 233-239 (2013); the entire contents of each of which are incorporated herein by reference).

The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development.

The term "target site" refers to a sequence within a nucleic acid molecule that is deaminated by a deaminase or a fusion protein comprising a deaminase, (e.g., a dCas9-deaminase fusion protein provided herein).

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

The term "recombinant" as used herein in the context of proteins or nucleic acids refers to proteins or nucleic acids that do not occur in nature, but are the product of human engineering. For example, in some embodiments, a recombinant protein or nucleic acid molecule comprises an amino acid or nucleotide sequence that comprises at least one, at least two, at least three, at least four, at least five, at least six, or at least seven mutations as compared to any naturally occurring sequence.

The term "nucleobase editors (NBEs)" or "base editors (BEs)," as used herein, refers to the Cas9 fusion proteins described herein. In some embodiments, the fusion protein comprises a nuclease-inactive Cas9 (dCas9) fused to a deaminase. In some embodiments, the fusion protein comprises a Cas9 nickase fused to a deaminase. In some embodiments, the fusion protein comprises a nuclease-inactive Cas9 fused to a deaminase and further fused to a UGI domain. In some embodiments, the fusion protein comprises a Cas9 nickase fused to a deaminase and further fused to a UGI domain. In some embodiments, the dCas9 of the fusion protein comprises a D10A and a H840A mutation of SEQ ID NO: 10, or a corresponding mutation in any of SEQ ID NOs: 11-260, which inactivates nuclease activity of the Cas9 protein. In some embodiments, the fusion protein comprises a D10A mutation and comprises a histidine at residue 840 of SEQ ID NO: 10, or a corresponding mutation in any of SEQ ID NOs: 11-260, which renders Cas9 capable of cleaving only one strand of a nucleic acid duplex. An example of a Cas9 nickase is shown below in SEQ ID NO: 674. The terms "nucleobase editors (NBEs)" and "base editors (BEs)" may be used interchangeably.

The term "uracil glycosylase inhibitor" or "UGI," as used herein, refers to a protein that is capable of inhibiting a uracil-DNA glycosylase base-excision repair enzyme.

The term "Cas9 nickase," as used herein, refers to a Cas9 protein that is capable of cleaving only one strand of a duplexed nucleic acid molecule (e.g., a duplexed DNA molecule). In some embodiments, a Cas9 nickase comprises a D10A mutation and has a histidine at position H840 of SEQ ID NO: 10, or a corresponding mutation in any of SEQ ID NOs: 11-260. For example, a Cas9 nickase may comprise the amino acid sequence as set forth in SEQ ID NO: 674. Such a Cas9 nickase has an active HNH nuclease domain and is able to cleave the non-targeted strand of DNA, i.e., the strand bound by the gRNA. Further, such a Cas9 nickase has an inactive RuvC nuclease domain and is not able to cleave the targeted strand of the DNA, i.e., the strand where base editing is desired.

Exemplary Cas9 nickase (Cloning vector pPlatTET-gRNA2; Accession No. BAV54124).

```
                                            (SEQ ID NO: 674)
MDKKYSIGLAIGTNSVGWAVITDEYKVPSKKFKVLGNTDRHSIKKNLIG

ALLFDSGETAEATRLKRTARRRYTRRKNRICYLQEIFSNEMAKVDDSFF

HRLEESFLVEEDKKHERHPIFGNIVDEVAYHEKYPTIYHLRKKLVDSTD

KADLRLIYLALAHMIKFRGHFLIEGDLNPDNSDVDKLFIQLVQTYNQLF

EENPINASGVDAKAILSARLSKSRRLENLIAQLPGEKKNGLFGNLIALS

LGLTPNFKSNFDLAEDAKLQLSKDTYDDDLDNLLAQIGDQYADLFLAAK

NLSDAILLSDILRVNTEITKAPLSASMIKRYDEHHQDLTLLKALVRQQL

PEKYKEIFFDQSKNGYAGYIDGGASQEEFYKFIKPILEKMDGTEELLVK

LNREDLLRKQRTFDNGSIPHQIHLGELHAILRRQEDFYPFLKDNREKIE

KILTFRIPYYVGPLARGNSRFAWMTRKSEETITPWNFEEVVDKGASAQS

FIERMTNFDKNLPNEKVLPKHSLLYEYFTVYNELTKVKYVTEGMRKPAF

LSGEQKKAIVDLLFKTNRKVTVKQLKEDYFKKIECFDSVEISGVEDRFN

ASLGTYHDLLKIIKDKDFLDNEENEDILEDIVLTLTLFEDREMIEERLK

TYAHLFDDKVMKQLKRRRYTGWGRLSRKLINGIRDKQSGKTILDFLKSD

GFANRNFMQLIHDDSLTFKEDIQKAQVSGQGDSLHEHIANLAGSPAIKK

GILQTVKVVDELVKVMGRHKPENIVIEMARENQTTQKGQKNSRERMKRI

EEGIKELGSQILKEHPVENTQLQNEKLYLYYLQNGRDMYVDQELDINRL

SDYDVDHIVPQSFLKDDSIDNKVLTRSDKNRGKSDNVPSEEVVKKMKNY

WRQLLNAKLITQRKFDNLTKAERGGLSELDKAGFIKRQLVETRQITKHV

AQILDSRMNTKYDENDKLIREVKVITLKSKLVSDFRKDFQFYKVREINN
```

-continued

```
YHHAHDAYLNAVVGTALIKKYPKLESEFVYGDYKVYDVRKMIAKSEQEI

GKATAKYFFYSNIMNFFKTEITLANGEIRKRPLIETNGETGEIVWDKGR

DFATVRKVLSMPQVNIVKKTEVQTGGFSKESILPKRNSDKLIARKKDWD

PKKYGGFDSPTVAYSVLVVAKVEKGKSKKLKSVKELLGITIMERSSFEK

NPIDFLEAKGYKEVKKDLIIKLPKYSLFELENGRKRMLASAGELQKGNE

LALPSKYVNFLYLASHYEKLKGSPEDNEQKQLFVEQHKHYLDEIIEQIS

EFSKRVILADANLDKVLSAYNKHRDKPIREQAENIIHLFTLTNLGAPAA

FKYFDTTIDRKRYTSTKEVLDATLIHQSITGLYETRIDLSQLGGD
```

DETAILED DESCRIPTION OF CERTAIN EMBODIMENTS OF THE INVENTION

Some aspects of this disclosure provide fusion proteins that comprise a domain capable of binding to a nucleotide sequence (e.g., a Cas9, or a Cpf1 protein) and an enzyme domain, for example, a DNA-editing domain, such as, e.g., a deaminase domain. The deamination of a nucleobase by a deaminase can lead to a point mutation at the respective residue, which is referred to herein as nucleic acid editing. Fusion proteins comprising a Cas9 variant or domain and a DNA editing domain can thus be used for the targeted editing of nucleic acid sequences. Such fusion proteins are useful for targeted editing of DNA in vitro, e.g., for the generation of mutant cells or animals; for the introduction of targeted mutations, e.g., for the correction of genetic defects in cells ex vivo, e.g., in cells obtained from a subject that are subsequently re-introduced into the same or another subject; and for the introduction of targeted mutations, e.g., the correction of genetic defects or the introduction of deactivating mutations in disease-associated genes in a subject. Typically, the Cas9 domain of the fusion proteins described herein does not have any nuclease activity but instead is a Cas9 fragment or a dCas9 protein or domain. Methods for the use of Cas9 fusion proteins as described herein are also provided.

Cas9 Domains of Nucleobase Editors

Non-limiting, exemplary Cas9 domains are provided herein. The Cas9 domain may be a nuclease active Cas9 domain, a nuclease inactive Cas9 domain, or a Cas9 nickase. In some embodiments, the Cas9 domain is a nuclease active domain. For example, the Cas9 domain may be a Cas9 domain that cuts both strands of a duplexed nucleic acid (e.g., both strands of a duplexed DNA molecule). In some embodiments, the Cas9 domain comprises any one of the amino acid sequences as set forth in SEQ ID NOs: 10-263. In some embodiments the Cas9 domain comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of the amino acid sequences set forth in SEQ ID NOs: 10-263. In some embodiments, the Cas9 domain comprises an amino acid sequence that has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50 or more or more mutations compared to any one of the amino acid sequences set forth in SEQ ID NOs: 10-263. In some embodiments, the Cas9 domain comprises an amino acid sequence that has at least 10, at least 15, at least 20, at least 30, at least 40, at least 50, at least 60, at least 70, at least 80, at least 90, at least 100, at least 150, at least 200, at least 250, at least 300, at least 350, at least 400, at least 500, at least 600, at least 700, at least 800, at least 900, at least 1000, at least 1100, or at least 1200 identical contiguous amino acid residues as compared to any one of the amino acid sequences set forth in SEQ ID NOs: 10-263.

In some embodiments, the Cas9 domain is a nuclease-inactive Cas9 domain (dCas9). For example, the dCas9 domain may bind to a duplexed nucleic acid molecule (e.g., via a gRNA molecule) without cleaving either strand of the duplexed nucleic acid molecule. In some embodiments, the nuclease-inactive dCas9 domain comprises a D10X mutation and a H840X mutation of the amino acid sequence set forth in SEQ ID NO: 10, or a corresponding mutation in any of the amino acid sequences provided in SEQ ID NOs: 11-260, wherein X is any amino acid change. In some embodiments, the nuclease-inactive dCas9 domain comprises a D10A mutation and a H840A mutation of the amino acid sequence set forth in SEQ ID NO: 10, or a corresponding mutation in any of the amino acid sequences provided in SEQ ID NOs: 11-260. As one example, a nuclease-inactive Cas9 domain comprises the amino acid sequence set forth in SEQ ID NO: 263 (Cloning vector pPlatTET-gRNA2, Accession No. BAV54124).

```
                                              (SEQ ID NO:
MDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDAIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE
```

```
-continued
DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD
```

263; see, e.g., Qi et al., Repurposing CRISPR as an RNA-guided platform for sequence-specific control of gene expression. *Cell.* 2013; 152(5):1173-83, the entire contents of which are incorporated herein by reference).

Additional suitable nuclease-inactive dCas9 domains will be apparent to those of skill in the art based on this disclosure and knowledge in the field, and are within the scope of this disclosure. Such additional exemplary suitable nuclease-inactive Cas9 domains include, but are not limited to, D10A/H840A, D10A/D839A/H840A, and D10A/D839A/H840A/N863A mutant domains (See, e.g., Prashant et al., CAS9 transcriptional activators for target specificity screening and paired nickases for cooperative genome engineering. *Nature Biotechnology.* 2013; 31(9): 833-838, the entire contents of which are incorporated herein by reference). In some embodiments the dCas9 domain comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of the dCas9 domains provided herein. In some embodiments, the dCas9 domain comprises an amino acid sequences that has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50 or more or more mutations compared to any one of the amino acid sequences set forth in SEQ ID NOs: 10-263. In some embodiments, the Cas9 domain comprises an amino acid sequence that has at least 10, at least 15, at least 20, at least 30, at least 40, at least 50, at least 60, at least 70, at least 80, at least 90, at least 100, at least 150, at least 200, at least 250, at least 300, at least 350, at least 400, at least 500, at least 600, at least 700, at least 800, at least 900, at least 1000, at least 1100, or at least 1200 identical contiguous amino acid residues as compared to any one of the amino acid sequences set forth in SEQ ID NOs: 10-263.

In some embodiments, the Cas9 domain is a Cas9 nickase. The Cas9 nickase may be a Cas9 protein that is capable of cleaving only one strand of a duplexed nucleic acid molecule (e.g., a duplexed DNA molecule). In some embodiments the Cas9 nickase cleaves the target strand of a duplexed nucleic acid molecule, meaning that the Cas9 nickase cleaves the strand that is base paired to (complementary to) a gRNA (e.g., an sgRNA) that is bound to the Cas9. In some embodiments, a Cas9 nickase comprises a D10A mutation and has a histidine at position 840 of SEQ ID NO: 10, or a mutation in any of SEQ ID NOs: 11-260. For example, a Cas9 nickase may comprise the amino acid sequence as set forth in SEQ ID NO: 674. In some embodiments the Cas9 nickase cleaves the non-target, non-base-edited strand of a duplexed nucleic acid molecule, meaning that the Cas9 nickase cleaves the strand that is not base paired to a gRNA (e.g., an sgRNA) that is bound to the Cas9. In some embodiments, a Cas9 nickase comprises an H840A mutation and has an aspartic acid residue at position 10 of SEQ ID NO: 10, or a corresponding mutation in any of SEQ ID NOs: 11-260. In some embodiments the Cas9 nickase comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of the Cas9 nickases provided herein. Additional suitable Cas9 nickases will be apparent to those of skill in the art based on this disclosure and knowledge in the field, and are within the scope of this disclosure.

Cas9 Domains with Reduced PAM Exclusivity

Some aspects of the disclosure provide Cas9 domains that have different PAM specificities. Typically, Cas9 proteins, such as Cas9 from *S. pyogenes* (spCas9), require a canonical NGG PAM sequence to bind a particular nucleic acid region. This may limit the ability to edit desired bases within a genome. In some embodiments, the base editing fusion proteins provided herein may need to be placed at a precise location, for example where a target base is placed within a 4 base region (e.g., a "deamination window"), which is approximately 15 bases upstream of the PAM. See Komor, A. C., et al., "Programmable editing of a target base in genomic DNA without double-stranded DNA cleavage" *Nature* 533, 420-424 (2016), the entire contents of which are hereby incorporated by reference. Accordingly, in some embodiments, any of the fusion proteins provided herein may contain a Cas9 domain that is capable of binding a nucleotide sequence that does not contain a canonical (e.g., NGG) PAM sequence. Cas9 domains that bind to non-canonical PAM sequences have been described in the art and would be apparent to the skilled artisan. For example, Cas9 domains that bind non-canonical PAM sequences have been described in Kleinstiver, B. P., et al., "Engineered CRISPR-Cas9 nucleases with altered PAM specificities" *Nature* 523, 481-485 (2015); and Kleinstiver, B. P., et al., "Broadening the targeting range of *Staphylococcus aureus* CRISPR-Cas9 by modifying PAM recognition" *Nature Biotechnology* 33, 1293-1298 (2015); the entire contents of each are hereby incorporated by reference.

In some embodiments, the Cas9 domain is a Cas9 domain from *Staphylococcus aureus* (SaCas9). In some embodiments, the SaCas9 domain is a nuclease active SaCas9, a nuclease inactive SaCas9 (SaCas9d), or a SaCas9 nickase (SaCas9n). In some embodiments, the SaCas9 comprises the amino acid sequence SEQ ID NO: 4273. In some embodiments, the SaCas9 comprises a N579X mutation of SEQ ID NO: 4273, or a corresponding mutation in any of the amino acid sequences provided in SEQ ID NOs: 11-260, wherein X is any amino acid except for N. In some embodiments, the SaCas9 comprises a N579A mutation of SEQ ID NO: 4273, or a corresponding mutation in any of the amino acid sequences provided in SEQ ID NOs: 11-260. In some embodiments, the SaCas9 domain, the SaCas9d domain, or the SaCas9n domain can bind to a nucleic acid sequence having a non-canonical PAM. In some embodiments, the SaCas9 domain, the SaCas9d domain, or the SaCas9n domain can bind to a nucleic acid sequence having a NNGRRT PAM sequence. In some embodiments, the SaCas9 domain comprises one or more of a E781X, a N967X, and a R1014X mutation of SEQ ID NO: 4273, or a corresponding mutation in any of the amino acid sequences provided in SEQ ID NOs: 11-260, wherein X is any amino acid. In some embodiments, the SaCas9 domain comprises one or more of a E781K, a N967K, and a R1014H mutation of SEQ ID NO: 4273, or one or more corresponding mutation in any of the amino acid sequences provided in SEQ ID NOs: 11-260. In some embodiments, the SaCas9 domain comprises a E781K, a N967K, or a R1014H mutation of SEQ ID NO: 4273, or corresponding mutations in any of the amino acid sequences provided in SEQ ID NOs: 11-260.

In some embodiments, the Cas9 domain of any of the fusion proteins provided herein comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of SEQ ID NOs: 4273-4275. In some embodiments, the Cas9 domain of any of the fusion proteins provided herein comprises the amino acid sequence of any one of SEQ ID NOs: 4273-4275. In some embodiments, the Cas9 domain of any of the fusion proteins provided herein consists of the amino acid sequence of any one of SEQ ID NOs: 4273-4275.

```
Exemplary SaCas9 sequence
                                          (SEQ ID NO: 4273)
KRNYILGLDIGITSVGYGIIDYETRDVIDAGVRLFKEANVENNEGRRSKR

GARRLKRRRRHRIQRVKKLLFDYNLLTDHSELSGINPYEARVKGLSQKLS

EEEFSAALLHLAKRRGVHNVNEVEEDTGNELSTKEQISRNSKALEEKYVA

ELQLERLKKDGEVRGSINRFKTSDYVKEAKQLLKVQKAYHQLDQSFIDTY

IDLLETRRTYYEGPGEGSPFGWKDIKEWYEMLMGHCTYFPEELRSVKYAY

NADLYNALNDLNNLVITRDENEKLEYYEKFQIIENVFKQKKKPTLKQIAK

EILVNEEDIKGYRVTSTGKPEFTNLKVYHDIKDITARKEIIENAELLDQI

AKILTIYQSSEDIQEELTNLNSELTQEEIEQISNLKGYTGTHNLSLKAIN

LILDELWHTNDNQIAIFNRLKLVPKKVDLSQQKEIPTTLVDDFILSPVVK

RSFIQSIKVINAIIKKYGLPNDIIIELAREKNSKDAQKMINEMQKRNRQT

NERIEEIIRTTGKENAKYLIEKIKLHDMQEGKCLYSLEAIPLEDLLNNPF

NYEVDHIIPRSVSFDNSFNNKVLVKQEENSKKGNRTPFQYLSSSDSKISY

ETFKKHILNLAKGKGRISKTKKEYLLEERDINRFSVQKDFINRNLVDTRY

ATRGLMNLLRSYFRVNNLDVKVKSINGGFTSFLRRKWKFKKERNKGYKHH

AEDALIIANADFIFKEWKKLDKAKKVMENQMFEEKQAESMPEIETEQEYK

EIFITPHQIKHIKDFKDYKYSHRVDKKPNRELINDTLYSTRKDDKGNTLI

VNNLNGLYDKDNDKLKKLINKSPEKLLMYHHDPQTYQKLKLIMEQYGDEK

NPLYKYYEETGNYLTKYSKKDNGPVIKKIKYYGNKLNAHLDITDDYPNSR

NKVVKLSLKPYRFDVYLDNGVYKFVTVKNLDVIKKENYYEVNSKCYEEAK

KLKKISNQAEFIASFYNNDLIKINGELYRVIGVNNDLLNRIEVNMIDITY

REYLENMNDKRPPRIIKTIASKTQSIKKYSTDILGNLYEVKSKKHPQIIK

KG
```

Residue N579 of SEQ ID NO: 4273, which is underlined and in bold, may be mutated (e.g., to a A579) to yield a SaCas9 nickase.

```
Exemplary SaCas9n sequence
                                          (SEQ ID NO: 4274)
KRNYILGLDIGITSVGYGIIDYETRDVIDAGVRLFKEANVENNEGRRSKR

GARRLKRRRRHRIQRVKKLLFDYNLLTDHSELSGINPYEARVKGLSQKLS

EEEFSAALLHLAKRRGVHNVNEVEEDTGNELSTKEQISRNSKALEEKYVA

ELQLERLKKDGEVRGSINTRFKTSDYVKEAKQLLKVQKAYHQLDQSFIDT

YIDLLETRRTYYEGPGEGSPFGWKDIKEWYEMLMGHCTYFPEELRSVKYA

YNADLYNALNDLNNLVITRDENEKLEYYEKFQIIENVFKQKKKPTLKQIA

KEILVNEEDIKGYRVTSTGKPEFTNLKVYHDIKDITARKEIIENAELLDQ

IAKILTIYQSSEDIQEELTNLNSELTQEEIEQISNLKGYTGTHNLSLKAI

NLILDELWHTNDNQIAIFNRLKLVPKKVDLSQQKEIPTTLVDDFILSPVV

KRSFIQSIKVINAIIKKYGLPNDIIIELAREKNSKDAQKMINEMQKRNRQ

TNERIEEIIRTTGKENAKYLIEKIKLHDMQEGKCLYSLEAIPLEDLLNNP

FNYEVDHIIPRSVSFDNSFNNKVLVKQEEASKKGNRTPFQYLSSSDSKIS

YETFKKHILNLAKGKGRISKTKKEYLLEERDINRFSVQKDFINRNLVDTR

YATRGLMNLLRSYFRVNNLDVKVKSINGGFTSFLRRKWKFKKERNKGYKH

HAEDALIIANADFIFKEWKKLDKAKKVMENQMFEEKQAESMPEIETEQEY

KEIFITPHQIKHIKDFKDYKYSHRVDKKPNRELINDTLYSTRKDDKGNTL

IVNNLNGLYDKDNDKLKKLINKSPEKLLMYHHDPQTYQKLKLIMEQYGDE

KNPLYKYYEETGNYLTKYSKKDNGPVIKKIKYYGNKLNAHLDITDDYPNS

RNKVVKLSLKPYRFDVYLDNGVYKFVTVKNLDVIKKENYYEVNSKCYEEA

KKLKKISNQAEFIASFYNNDLIKINGELYRVIGVNNDLLNRIEVNMIDIT

YREYLENMNDKRPPRIIKTIASKTQSIKKYSTDILGNLYEVKSKKHPQII

KKG.
```

Residue A579 of SEQ ID NO: xx, which can be mutated from N579 of SEQ ID NO: 4274 to yield a SaCas9 nickase, is underlined and in bold.

```
Exemplary SaKKH Cas9
                                          (SEQ ID NO: 4275)
KRNYILGLDIGITSVGYGIIDYETRDVIDAGVRLFKEANVENNEGRRSKR

GARRLKRRRRHRIQRVKKLLFDYNLLTDHSELSGINPYEARVKGLSQKLS

EEEFSAALLHLAKRRGVHNVNEVEEDTGNELSTKEQISRNSKALEEKYVA

ELQLERLKKDGEVRGSINTRFKTSDYVKEAKQLLKVQKAYHQLDQSFIDT

YIDLLETRRTYYEGPGEGSPFGWKDIKEWYEMLMGHCTYFPEELRSVKYA

YNADLYNALNDLNNLVITRDENEKLEYYEKFQIIENVFKQKKKPTLKQIA

KEILVNEEDIKGYRVTSTGKPEFTNLKVYHDIKDITARKEIIENAELLDQ

IAKILTIYQSSEDIQEELTNLNSELTQEEIEQISNLKGYTGTHNLSLKAI

NLILDELWHTNDNQIAIFNRLKLVPKKVDLSQQKEIPTTLVDDFILSPVV

KRSFIQSIKVINAIIKKYGLPNDIIIELAREKNSKDAQKMINEMQKRNRQ

TNERIEEIIRTTGKENAKYLIEKIKLHDMQEGKCLYSLEAIPLEDLLNNP

FNYEVDHIIPRSVSFDNSFNNKVLVKQEEASKKGNRTPFQYLSSSDSKIS

YETFKKHILNLAKGKGRISKTKKEYLLEERDINRFSVQKDFINRNLVDTR

YATRGLMNLLRSYFRVNNLDVKVKSINGGFTSFLRRKWKFKKERNKGYKH

HAEDALIIANADFIFKEWKKLDKAKKVMENQMFEEKQAESMPEIETEQEY

KEIFITPHQIKHIKDFKDYKYSHRVDKKPNRKLINDTLYSTRKDDKGNTL

IVNNLNGLYDKDNDKLKKLINKSPEKLLMYHHDPQTYQKLKLIMEQYGDE

KNPLYKYYEETGNYLTKYSKKDNGPVIKKIKYYGNKLNAHLDITDDYPNS

RNKVVKLSLKPYRFDVYLDNGVYKFVTVKNLDVIKKENYYEVNSKCYEEA

KKLKKISNQAEFIASFYKNDLIKINGELYRVIGVNNDLLNRIEVNMIDIT

YREYLENMNDKRPPHIIKTIASKTQSIKKYSTDILGNLYEVKSKKHPQII

KKG.
```

Residue A579 of SEQ ID NO: 4275, which can be mutated from N579 of SEQ ID NO: 4275 to yield a SaCas9 nickase, is underlined and in bold. Residues K781, K967, and H1014 of SEQ ID NO: 4275, which can be mutated from E781, N967, and R1014 of SEQ ID NO: 4275 to yield a SaKKH Cas9 are underlined and in italics.

In some embodiments, the Cas9 domain is a Cas9 domain from Streptococcus pyogenes (SpCas9). In some embodiments, the SpCas9 domain is a nuclease active SpCas9, a nuclease inactive SpCas9 (SpCas9d), or a SpCas9 nickase (SpCas9n). In some embodiments, the SpCas9 comprises the amino acid sequence SEQ ID NO: 4276. In some embodiments, the SpCas9 comprises a D9X mutation of SEQ ID NO: 4276, or a corresponding mutation in any of the amino acid sequences provided in SEQ ID NOs: 11-260, wherein X is any amino acid except for D. In some embodiments, the SpCas9 comprises a D9A mutation of SEQ ID NO: 4276, or a corresponding mutation in any of the amino acid sequences provided in SEQ ID NOs: 11-260. In some embodiments, the SpCas9 domain, the SpCas9d domain, or the SpCas9n domain can bind to a nucleic acid sequence having a non-canonical PAM. In some embodiments, the SpCas9 domain, the SpCas9d domain, or the SpCas9n domain can bind to a nucleic acid sequence having a NGG, a NGA, or a NGCG PAM sequence. In some embodiments, the SpCas9 domain comprises one or more of a D1134X, a R1334X, and a T1336X mutation of SEQ ID NO: 4276, or a corresponding mutation in any of the amino acid sequences provided in SEQ ID NOs: 11-260, wherein X is any amino acid. In some embodiments, the SpCas9 domain comprises one or more of a D1134E, R1334Q, and T1336R mutation of SEQ ID NO: 4276, or a corresponding mutation in any of the amino acid sequences provided in SEQ ID NOs: 11-260. In some embodiments, the SpCas9 domain comprises a D1134E, a R1334Q, and a T1336R mutation of SEQ ID NO: 4276, or corresponding mutations in any of the amino acid sequences provided in SEQ ID NOs: 11-260. In some embodiments, the SpCas9 domain comprises one or more of a D1134X, a R1334X, and a T1336X mutation of SEQ ID NO: 4276, or a corresponding mutation in any of the amino acid sequences provided in SEQ ID NOs: 11-260, wherein X is any amino acid. In some embodiments, the SpCas9 domain comprises one or more of a D1134V, a R1334Q, and a T1336R mutation of SEQ ID NO: 4276, or a corresponding mutation in any of the amino acid sequences provided in SEQ ID NOs: 11-260. In some embodiments, the SpCas9 domain comprises a D1134V, a R1334Q, and a T1336R mutation of SEQ ID NO: 4276, or corresponding mutations in any of the amino acid sequences provided in SEQ ID NOs: 11-260. In some embodiments, the SpCas9 domain comprises one or more of a D1134X, a G1217X, a R1334X, and a T1336X mutation of SEQ ID NO: 4276, or a corresponding mutation in any of the amino acid sequences provided in SEQ ID NOs: 11-260, wherein X is any amino acid. In some embodiments, the SpCas9 domain comprises one or more of a D1134V, a G1217R, a R1334Q, and a T1336R mutation of SEQ ID NO: 4276, or a corresponding mutation in any of the amino acid sequences provided in SEQ ID NOs: 11-260. In some embodiments, the SpCas9 domain comprises a D1134V, a G1217R, a R1334Q, and a T1336R mutation of SEQ ID NO: 4276, or corresponding mutations in any of the amino acid sequences provided in SEQ ID NOs: 11-260.

In some embodiments, the Cas9 domain of any of the fusion proteins provided herein comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of SEQ ID NOs: 4276-4280. In some embodiments, the Cas9 domain of any of the fusion proteins provided herein comprises the amino acid sequence of any one of SEQ ID NOs: 4276-4280. In some embodiments, the Cas9 domain of any of the fusion proteins provided herein consists of the amino acid sequence of any one of SEQ ID NOs: 4276-4280.

Exemplary SpCas9
(SEQ ID NO: 4276)
DKKYSIGLDIGTNSVGWAVITDEYKVPSKKFKVLGNTDRHSIKKNLIGAL

LFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYY

VGPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVDL

LFKTNRKVTVKQLKEDYFKKIECFDSVETSGVEDRFNASLGTYHDLLKII

KDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDHIVPQSFLKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKRYTSTKEVLDATLIHQS

ITGLYETRIDLSQLGGD

Exemplary SpCas9n
(SEQ ID NO: 4277)
DKKYSIGLAIGTNSVGWAVITDEYKVPSKKFKVLGNTDRHSIKKNLIGAL

LFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

```
FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QQRTFDNGSIPHQIHLGELHAILRREDFYPFLKDNREKIEKILTFRIPYY

VGPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVDL

LFKTNRKVTVKQLKEDYFKKIECFDSVETSGVEDRFNASLGTYHDLLKII

KDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDHIVPQSFLKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKRYTSTKEVLDATLIHQS

ITGLYETRIDLSQLGGD

Exemplary SpEQR Cas9
                                       (SEQ ID NO: 4278)
DKKYSIGLAIGTNSVGWAVITDEYKVPSKKFKVLGNTDRHSIKKNLIGAL

LFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYY

VGPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVDL

LFKTNRKVTVKQLKEDYFKKIECFDSVETSGVEDRFNASLGTYHDLLKII

KDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDHIVPQSFLKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFESPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKQYR**STKEVLDATLIHQS

ITGLYETRIDLSQLGGD
```

Residues E1134, Q1334, and R1336 of SEQ ID NO: 4278, which can be mutated from D1134, R1334, and T1336 of SEQ ID NO: 4278 to yield a SpEQR Cas9, are underlined and in bold.

```
Exemplary SpVQR Cas9
                                       (SEQ ID NO: 4279)
DKKYSIGLAIGTNSVGWAVITDEYKVPSKKFKVLGNTDRHSIKKNLIGAL

LFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYY

VGPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVDL

LFKTNRKVTVKQLKEDYFKKIECFDSVETSGVEDRFNASLGTYHDLLKII

KDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDHIVPQSFLKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFVSPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED
```

-continued
NEQKQLFVEQHKHYLDEIIEQISEFSKRVILADANLDKVLSAYNKHRDKP

IREQAENIIHLFTLTNLGAPAAFKYFDTTIDRKQYRSTKEVLDATLIHQS

ITGLYETRIDLSQLGGD

Residues V1134, Q1334, and R1336 of SEQ ID NO: 4279, which can be mutated from D1134, R1334, and T1336 of SEQ ID NO: 4279 to yield a SpVQR Cas9, are underlined and in bold.

```
Exemplary SpVRER Cas9
                                     (SEQ ID NO: 4280)
DKKYSIGLAIGTNSVGWAVITDEYKVPSKKFKVLGNTDRHSIKKNLIGAL

LFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYY

VGPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVDL

LFKTNRKVTVKQLKEDYFKKIECFDSVETSGVEDRFNASLGTYHDLLKII

KDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDHIVPQSFLKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFVSPTVAYSVLVVAKVEK

GKSKKLKSVKELLGITIMERSSFEKNPIDFLEAKGYKEVKKDLIIKLPKY

SLFELENGRKRMLASARELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKEYRSTKEVLDATLIHQS

ITGLYETRIDLSQLGGD
```

Residues V1134, R1217, Q1334, and R1336 of SEQ ID NO: 4280, which can be mutated from D1134, G1217, R1334, and T1336 of SEQ ID NO: 4280 to yield a SpVRER Cas9, are underlined and in bold.

The following are exemplary fusion proteins (e.g., base editing proteins) capable of binding to a nucleic acid sequence having a non-canonical (e.g., a non-NGG) PAM sequence:

```
Exemplary SaBE3 (rAPOBEC1-XTEN-SaCas9n-UGI-NLS)
                                     (SEQ ID NO: 4281)
MSSETGPVAVDPTLRRRIEPHEFEVFFDPRELRKETCLLYEINWGGRHSI

WRHTSQNTNKHVEVNFIEKFTTERYFCPNTRCSITWFLSWSPCGECSRAI

TEFLSRYPHVTLFIYIARLYHHADPRNRQGLRDLISSGVTIQIMTEQESG

YCWRNFVNYSPSNEAHWPRYPHLWVRLYVLELYCIILGLPPCLNILRRKQ

PQLTFFTIALQSCHYQRLPPHILWATGLKSGSETPGTSESATPES<u>KRNYI</u>

<u>LGLDIGITSVGYGIIDYETRDVIDAGVRLFKEANVENNEGRRSKRGARRL</u>

<u>KRRRRHRIQRVKKLLFDYNLLTDHSELSGINPYEARVKGLSQKLSEEEFS</u>

<u>AALLHLAKRRGVHNVNEVEEDTGNELSTKEQISRNSKALEEKYVAELQLE</u>

<u>RLKKDGEVRGSINRFKTSDYVKEAKQLLKVQKAYHQLDQSFIDTYIDLLE</u>

<u>TRRTYYEGPGEGSPFGWKDIKEWYEMLMGHCTYFPEELRSVKYAYNADLY</u>

<u>NALNDLNNLVITRDENEKLEYYEKFQIIENVFKQKKKPTLKQIAKEILVN</u>

<u>EEDIKGYRVTSTGKPEFTNLKVYHDIKDITARKEIIENAELLDQIAKILT</u>

<u>IYQSSEDIQEELTNLNSELTQEEIEQISNLKGYTGTHNLSLKAINLILDE</u>

<u>LWHTNDNQIAIFNRLKLVPKKVDLSQQKEIPTTLVDDFILSPVVKRSFIQ</u>

<u>SIKVINAIIKKYGLPNDIIIELAREKNSKDAQKMINEMQKRNRQTNERIE</u>

<u>EIIRTTGKENAKYLIEKIKLHDMQEGKCLYSLEAIPLEDLLNNPFNYEVD</u>

<u>HIIPRSVSFDNSFNNKVLVKQEEASKKGNRTPFQYLSSSDSKISYETFKK</u>

<u>HILNLAKGKGRISKTKKEYLLEERDINRFSVQKDFINRNLVDTRYATRGL</u>

<u>MNLLRSYFRVNNLDVKVKSINGGFTSFLRRKWKFKKERNKGYKHHAEDAL</u>

<u>IIANADFIFKEWKKLDKAKKVMENQMFEEKQAESMPEIETEQEYKEIFIT</u>

<u>PHQIKHIKDFKDYKYSHRVDKKPNRELINDTLYSTRKDDKGNTLIVNNLN</u>

<u>GLYDKDNDKLKKLINKSPEKLLMYHHDPQTYQKLKLIMEQYGDEKNPLYK</u>

<u>YYEETGNYLTKYSKKDNGPVIKKIKYYGNKLNAHLDITDDYPNSRNKVVK</u>

<u>LSLKPYRFDVYLDNGVYKFVTVKNLDVIKKENYYEVNSKCYEEAKKLKKI</u>

<u>SNQAEFIASFYNNDLIKINGELYRVIGVNNDLLNRIEVNMIDITYREYLE</u>

<u>NMNDKRPPRIIKTIASKTQSIKKYSTDILGNLYEVKSKKHPQIIKKG</u>SGG

STNLSDIIEKETGKQLVIQESILMLPEEVEEVIGNKPESDILVHTAYDES

TDENVMLLTSDAPEYKPWALVIQDSNGENKIKMLSGGSPKKKRKV

Exemplary SaKKH-BE3 (rAPOBEC1-XTEN-SaCas9n-UGI-NLS)
                                     (SEQ ID NO: 4282)
MSSETGPVAVDPTLRRRIEPHEFEVFFDPRELRKETCLLYEINWGGRHSI

WRHTSQNTNKHVEVNFIEKFTTERYFCPNTRCSITWFLSWSPCGECSRAI

TEFLSRYPHVTLFIYIARLYHHADPRNRQGLRDLISSGVTIQIMTEQESG

YCWRNFVNYSPSNEAHWPRYPHLWVRLYVLELYCIILGLPPCLNILRRKQ

PQLTFFTIALQSCHYQRLPPHILWATGLKSGSETPGTSESATPES<u>KRNYI</u>

<u>LGLDIGITSVGYGIIDYETRDVIDAGVRLFKEANVENNEGRRSKRGARRL</u>

<u>KRRRRHRIQRVKKLLFDYNLLTDHSELSGINPYEARVKGLSQKLSEEEFS</u>

<u>AALLHLAKRRGVHNVNEVEEDTGNELSTKEQISRNSKALEEKYVAELQLE</u>

<u>RLKKDGEVRGSINRFKTSDYVKEAKQLLKVQKAYHQLDQSFIDTYIDLLE</u>

<u>TRRTYYEGPGEGSPFGWKDIKEWYEMLMGHCTYFPEELRSVKYAYNADLY</u>

<u>NALNDLNNLVITRDENEKLEYYEKFQIIENVFKQKKKPTLKQIAKEILVN</u>
```

-continued

EEDIKGYRVTSTGKPEFTNLKVYHDIKDITARKEIIENAELLDQIAKILT
IYQSSEDIQEELTNLNSELTQEEIEQISNLKGYTGTHNLSLKAINLILDE
LWHTNDNQIAIFNRLKLVPKKVDLSQQKEIPTTLVDDFILSPVVKRSFIQ
SIKVINAIIKKYGLPNDIIIELAREKNSKDAQKMINEMQKRNRQTNERIE
EIIRTTGKENAKYLIEKIKLHDMQEGKCLYSLEAIPLEDLLNNPFNYEVD
HIIPRSVSFDNSFNNKVLVKQEEASKKGNRTPFQYLSSSDSKISYETFKK
HILNLAKGKGRISKTKKEYLLEERDINRFSVQKDFINRNLVDTRYATRGL
MNLLRSYFRVNNLDVKVKSINGGFTSFLRRKWKFKKERNKGYKHHAEDAL
IIANADFIFKEWKKLDKAKKVMENQMFEEKQAESMPEIETEQEYKEIFIT
PHQIKHIKDFKDYKYSHRVDKKPNR*K*LINDTLYSTRKDDKGNTLIVNNLN
GLYDKDNDKLKKLINKSPEKLLMYHHDPQTYQKLKLIMEQYGDEKNPLYK
YYEETGNYLTKYSKKDNGPVIKKIKYYGNKLNAHLDITDDYPNSRNKVVK
LSLKPYRFDVYLDNGVYKFVTVKNLDVIKKENYYEVNSKCYEEAKKLKKI
SNQAEFIASFYKNDLIKINGELYRVIGVNNDLLNRIEVNMIDITYREYLE
NMNDKRPP*HI*IKTIASKTQSIKKYSTDILGNLYEVKSKKHPQIIKKGSGG
STNLSDIIEKETGKQLVIQESILMLPEEVEEVIGNKPESDILVHTAYDES
TDENVMLLTSDAPEYKPWALVIQDSNGENKIKMLSGGSPKKKRKV

Exemplary EQR-BE3 (rAPOBEC1-XTEN-Cas9n-UGI-NLS)
(SEQ ID NO: 4283)
MSSETGPVAVDPTLRRRIEPHEFEVFFDPRELRKETCLLYEINWGGRHSI
WRHTSQNTNKHVEVNFIEKFTTERYFCPNTRCSITWFLSWSPCGECSRAI
TEFLSRYPHVTLFIYIARLYHHADPRNRQGLRDLISSGVTIQIMTEQESG
YCWRNFVNYSPSNEAHWPRYPHLWVRLYVLELYCIILGLPPCLNILRRKQ
PQLTFFTIALQSCHYQRLPPHILWATGLKSGSETPGTSESATPESDKKYS
IGLAIGTNSVGWAVITDEYKVPSKKFKVLGNTDRHSIKKNLIGALLFDSG
ETAEATRLKRTARRRYTRRKNRICYLQEIFSNEMAKVDDSFFHRLEESFL
VEEDKKHERHPIFGNIVDEVAYHEKYPTIYHLRKKLVDSTDKADLRLIYL
ALAHMIKFRGHFLIEGDLNPDNSDVDKLFIQLVQTYNQLFEENPINASGV
DAKAILSARLSKSRRLENLIAQLPGEKKNGLFGNLIALSLGLTPNFKSNF
DLAEDAKLQLSKDTYDDDLDNLLAQIGDQYADLFLAAKNLSDAILLSDIL
RVNTEITKAPLSASMIKRYDEHHQDLTLLKALVRQQLPEKYKEIFFDQSK
NGYAGYIDGGASQEEFYKFIKPILEKMDGTEELLVKLNREDLLRKQRTFD
NGSIPHQIHLGELHAILRRQEDFYPFLKDNREKIEKILTFRIPYYVGPLA
RGNSRFAWMTRKSEETITPWNFEEVVDKGASAQSFIERMTNFDKNLPNEK
VLPKHSLLYEYFTVYNELTKVKYVTEGMRKPAFLSGEQKKAIVDLLFKTN
RKVTVKQLKEDYFKKIECFDSVETSGVEDRFNASLGTYHDLLKIIKDKDF
LDNEENEDILEDIVLTLTLFEDREMIEERLKTYAHLFDDKVMKQLKRRRY
TGWGRLSRKLINGIRDKQSGKTILDFLKSDGFANRNFMQLIHDDSLTFKE
DIQKAQVSGQGDSLHEHIANLAGSPAIKKGILQTVKVVDELVKVMGRHKP
ENIVIEMARENQTTQKGQKNSRERMKRIEEGIKELGSQILKEHPVENTQL
QNEKLYLYYLQNGRDMYVDQELDINRLSDYDVDHIVPQSFLKDDSIDNKV
LTRSDKNRGKSDNVPSEEVVKKMKNYWRQLLNAKLITQRKFDNLTKAERG GLSELDKAGFIKRQLVETRQITKHVAQILDSRMNTKYDENDKLIREVKVI
TLKSKLVSDFRKDFQFYKVREINNYHHAHDAYLNAVVGTALIKKYPKLES
EFVYGDYKVYDVRKMIAKSEQEIGKATAKYFFYSNIMNFFKTEITLANGE
IRKRPLIETNGETGEIVWDKGRDFATVRKVLSMPQVNIVKKTEVQTGGFS
KESILPKRNSDKLIARKKDWDPKKYGGFESPTVAYSVLVVAKVEKGKSKK
LKSVKELLGITIMERSSFEKNPIDFLEAKGYKEVKKDLIIKLPKYSLFEL
ENGRKRMLASAGELQKGNELALPSKYVNFLYLASHYEKLKGSPEDNEQKQ
LFVEQHKHYLDEIIEQISEFSKRVILADANLDKVLSAYNKHRDKPIREQA
ENIIHLFTLTNLGAPAAFKYFDTTIDRKQYRSTKEVLDATLIHQSITGLY
ETRIDLSQLGGDSGGSTNLSDIIEKETGKQLVIQESILMLPEEVEEVIGN
KPESDILVHTAYDESTDENVMLLTSDAPEYKPWALVIQDSNGENKIKMLS
GGSPKKKRKV VQR-BE3 (rAPOBEC1-XTEN-Cas9n-UGI-NLS)
(SEQ ID NO: 4284)
MSSETGPVAVDPTLRRRIEPHEFEVFFDPRELRKETCLLYEINWGGRHSI
WRHTSQNTNKHVEVNFIEKFTTERYFCPNTRCSITWFLSWSPCGECSRAI
TEFLSRYPHVTLFIYIARLYHHADPRNRQGLRDLISSGVTIQIMTEQESG
YCWRNFVNYSPSNEAHWPRYPHLWVRLYVLELYCIILGLPPCLNILRRKQ
PQLTFFTIALQSCHYQRLPPHILWATGLKSGSETPGTSESATPESDKKYS
IGLAIGTNSVGWAVITDEYKVPSKKFKVLGNTDRHSIKKNLIGALLFDSG
ETAEATRLKRTARRRYTRRKNRICYLQEIFSNEMAKVDDSFFHRLEESFL
VEEDKKHERHPIFGNIVDEVAYHEKYPTIYHLRKKLVDSTDKADLRLIYL
ALAHMIKFRGHFLIEGDLNPDNSDVDKLFIQLVQTYNQLFEENPINASGV
DAKAILSARLSKSRRLENLIAQLPGEKKNGLFGNLIALSLGLTPNFKSNF
DLAEDAKLQLSKDTYDDDLDNLLAQIGDQYADLFLAAKNLSDAILLSDIL
RVNTEITKAPLSASMIKRYDEHHQDLTLLKALVRQQLPEKYKEIFFDQSK
NGYAGYIDGGASQEEFYKFIKPILEKMDGTEELLVKLNREDLLRKQRTFD
NGSIPHQIHLGELHAILRRQEDFYPFLKDNREKIEKILTFRIPYYVGPLA
RGNSRFAWMTRKSEETITPWNFEEVVDKGASAQSFIERMTNFDKNLPNEK
VLPKHSLLYEYFTVYNELTKVKYVTEGMRKPAFLSGEQKKAIVDLLFKTN
RKVTVKQLKDYFKKIECFDSVETSGVEDRFNASLGTYHDLLKIIKDKDFL
DNEENEDILEDIVLTLTLFEDREMIEERLKTYAHLFDDKVMKQLKRRRYT
GWGRLSRKLINGIRDKQSGKTILDFLKSDGFANRNFMQLIHDDSLTFKED
IQKAQVSGQGDSLHEHIANLAGSPAIKKGILQTVKVVDELVKVMGRHKPE
NIVIEMARENQTTQKGQKNSRERMKRIEEGIKELGSQILKEHPVENTQLQ
NEKLYLYYLQNGRDMYVDQELDINRLSDYDVDHIVPQSFLKDDSIDNKVL
TRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVIT
LKSKLVSDFRKDFQFYKVREINNYHHAHDAYLNAVVGTALIKKYPKLESE
FVYGDYKVYDVRKMIAKSEQEIGKATAKYFFYSNIMNFFKTEITLANGEI
RKRPLIETNGETGEIVWDKGRDFATVRKVLSMPQVNIVKKTEVQTGGFSK
ESILPKRNSDKLIARKKDWDPKKYGGFVSPTVAYSVLVVAKVEKGKSKKL -continued

KSVKELLGITIMERSSFEKNPIDFLEAKGYKEVKKDLIIKLPKYSLFELE

NGRKRMLASAGELQKGNELALPSKYVNFLYLASHYEKLKGSPEDNEQKQL

FVEQHKHYLDEIIEQISEFSKRVILADANLDKVLSAYNKHRDKPIREQAE

NIIHLFTLTNLGAPAAFKYFDTTIDRKQYRSTKEVLDATLIHQSITGLYE

TRIDLSQLGGDSGGSTNLSDIIEKETGKQLVIQESILMLPEEVEEVIGNK

PESDILVHTAYDESTDENVMLLTSDAPEYKPWALVIQDSNGENKIKMLSG

GSPKKKRKV

VRER-BE3 (rAPOBEC1-XTEN-Cas9n-UGI-NLS)
(SEQ ID NO: 4285)
MSSETGPVAVDPTLRRRIEPHEFEVFFDPRELRKETCLLYEINWGGRHSI

WRHTSQNTNKHVEVNFIEKFTTERYFCPNTRCSITWFLSWSPCGECSRAI

TEFLSRYPHVTLFIYIARLYHHADPRNRQGLRDLISSGVTIQIMTEQESG

YCWRNFVNYSPSNEAHWPRYPHLWVRLYVLELYCIILGLPPCLNILRRKQ

PQLTFFTIALQSCHYQRLPPHILWATGLKSGSETPGTSESATPESDKKYS

IGLAIGTNSVGWAVITDEYKVPSKKFKVLGNTDRHSIKKNLIGALLFDSG

ETAEATRLKRTARRRYTRRKNRICYLQEIFSNEMAKVDDSFFHRLEESFL

VEEDKKHERHPIFGNIVDEVAYHEKYPTIYHLRKKLVDSTDKADLRLIYL

ALAHMIKFRGHFLIEGDLNPDNSDVDKLFIQLVQTYNQLFEENPINASGV

DAKAILSARLSKSRRLENLIAQLPGEKKNGLFGNLIALSLGLTPNFKSNF

DLAEDAKLQLSKDTYDDDLDNLLAQIGDQYADLFLAAKNLSDAILLSDIL

RVNTEITKAPLSASMIKRYDEHHQDLTLLKALVRQQLPEKYKEIFFDQSK

NGYAGYIDGGASQEEFYKFIKPILEKMDGTEELLVKLNREDLLRKQRTFD

NGSIPHQIHLGELHAILRRQEDFYPFLKDNREKIEKILTFRIPYYVGPLA

RGNSRFAWMTRKSEETITPWNFEEVVDKGASAQSFIERMTNFDKNLPNEK

VLPKHSLLYEYFTVYNELTKVKYVTEGMRKPAFLSGEQKKAIVDLLFKTN

RKVTVKQLKEDYFKKIECFDSVETSGVEDRFNASLGTYHDLLKIIKDKDF

LDNEENEDILEDIVLTLTLFEDREMIEERLKTYAHLFDDKVMKQLKRRRY

TGWGRLSRKLINGIRDKQSGKTILDFLKSDGFANRNFMQLIHDDSLTFKE

DIQKAQVSGQGDSLHEHIANLAGSPAIKKGILQTVKVVDELVKVMGRHKP

ENIVIEMARENQTTQKGQKNSRERMKRIEEGIKELGSQILKEHPVENTQL

QNEKLYLYYLQNGRDMYVDQELDINRLSDYDVDHIVPQSFLKDDSIDNKV

LTRSDKNRGKSDNVPSEEVVKKMKNYWRQLLNAKLITQRKFDNLTKAERG

GLSELDKAGFIKRQLVETRQITKHVAQILDSRMNTKYDENDKLIREVKVI

TLKSKLVSDFRKDFQFYKVREINNYHHAHDAYLNAVVGTALIKKYPKLES

EFVYGDYKVYDVRKMIAKSEQEIGKATAKYFFYSNIMNFFKTEITLANGE

IRKRPLIETNGETGEIVWDKGRDFATVRKVLSMPQVNIVKKTEVQTGGFS

KESILPKRNSDKLIARKKDWDPKKYGGFVSPTVAYSVLVVAKVEKGKSKK

LKSVKELLGITIMERSSFEKNPIDFLEAKGYKEVKKDLIIKLPKYSLFEL

ENGRKRMLASARELQKGNELALPSKYVNFLYLASHYEKLKGSPEDNEQKQ

LFVEQHKHYLDEIIEQISEFSKRVILADANLDKVLSAYNKHRDKPIREQA

ENIIHLFTLTNLGAPAAFKYFDTTIDRKEYRSTKEVLDATLIHQSITGLY

-continued

ETRIDLSQLGGDSGGSTNLSDIIEKETGKQLVIQESILMLPEEVEEVIGN

KPESDILVHTAYDESTDENVMLLTSDAPEYKPWALVIQDSNGENKIKMLS

GGSPKKKRKV

High Fidelity Base Editors

Some aspects of the disclosure provide Cas9 fusion proteins (e.g., any of the fusion proteins provided herein) comprising a Cas9 domain that has high fidelity. Additional aspects of the disclosure provide Cas9 fusion proteins (e.g., any of the fusion proteins provided herein) comprising a Cas9 domain with decreased electrostatic interactions between the Cas9 domain and a sugar-phosphate backbone of a DNA, as compared to a wild-type Cas9 domain. In some embodiments, a Cas9 domain (e.g., a wild type Cas9 domain) comprises one or more mutations that decreases the association between the Cas9 domain and a sugar-phosphate backbone of a DNA. In some embodiments, any of the Cas9 fusion proteins provided herein comprise one or more of a N497X, a R661X, a Q695X, and/or a Q926X mutation of the amino acid sequence provided in SEQ ID NO: 10, or a corresponding mutation in any of the amino acid sequences provided in SEQ ID NOs: 11-260, wherein X is any amino acid. In some embodiments, any of the Cas9 fusion proteins provided herein comprise one or more of a N497A, a R661A, a Q695A, and/or a Q926A mutation of the amino acid sequence provided in SEQ ID NO: 10, or a corresponding mutation in any of the amino acid sequences provided in SEQ ID NOs: 11-260. In some embodiments, the Cas9 domain comprises a D10A mutation of the amino acid sequence provided in SEQ ID NO: 10, or a corresponding mutation in any of the amino acid sequences provided in SEQ ID NOs: 11-260. In some embodiments, the Cas9 domain (e.g., of any of the fusion proteins provided herein) comprises the amino acid sequence as set forth in SEQ ID NO: 325. In some embodiments, the fusion protein comprises the amino acid sequence as set forth in SEQ ID NO: 285. Cas9 domains with high fidelity are known in the art and would be apparent to the skilled artisan. For example, Cas9 domains with high fidelity have been described in Kleinstiver, B. P., et al. "High-fidelity CRISPR-Cas9 nucleases with no detectable genome-wide off-target effects." *Nature* 529, 490-495 (2016); and Slaymaker, I. M., et al. "Rationally engineered Cas9 nucleases with improved specificity." *Science* 351, 84-88 (2015); the entire contents of each are incorporated herein by reference.

It should be appreciated that the base editors provided herein, for example base editor 2 (BE2) or base editor 3 (BE3), may be converted into high fidelity base editors by modifying the Cas9 domain as described herein to generate high fidelity base editors, for example high fidelity base editor 2 (HF-BE2) or high fidelity base editor 3 (HF-BE3). In some embodiments, base editor 2 (BE2) comprises a deaminase domain, a dCas9, and a UGI domain. In some embodiments, base editor 3 (BE3) comprises a deaminase domain an nCas9 domain and a UGI domain.

Cas9 domain where mutations relative to Cas9 of
SEQ ID NO: 10 are shown in bold and underlines
(SEQ ID NO: 325)
DKKYSIGLAIGTNSVGWAVITDEYKVPSKKFKVLGNTDRHSIKKNLIGAL

LFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADL

-continued

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYY

VGPLARGNSRFAWMTRKSEETITPWNFEEVVDKGASAQSFIERMTAFDKN

LPNEKVLPKHSLLYEYFTVYNELTKVKYVTEGMRKPAFLSGEQKKAIVDL

LFKTNRKVTVKQLKEDYFKKIECFDSVEISGVEDRFNASLGTYHDLLKII

KDKDFLDNEENEDILEDIVLTLTLFEDREMIEERLKTYAHLFDDKVMKQL

KRRRYTGWGALSRKLINGIRDKQSGKTILDFLKSDGFANRNFMALIHDDS

LTFKEDIQKAQVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDHIVPQSFLKDDS

IDNKVLTRSDKNRGKSDNVPSEEVVKKMKNYWRQLLNAKLITQRKFDNLT

KAERGGLSELDKAGFIKRQLVETRAITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKRYTSTKEVLDATLIHQS

ITGLYETRIDLSQLGGD

HF-BE3

(SEQ ID NO: 285)
msSETGPVAVDPTLRRRIEPHEFEVFFDPRELRKETCLLYEINWGGRHSI

WRHTSQNTNKHVEVNFIEKFTTERYFCPNTRCSITWFLSWSPCGECSRAI

TEFLSRYPHVTLFIYIARLYHHADPRNRQGLRDLISSGVTIQIMTEQESG

YCWRNFVNYSPSNEAHWPRYPHLWVRLYVLELYCIILGLPPCLNILRRKQ

PQLTFFTIALQSCHYQRLPPHILWATGLKSGSETPGTSESATPESDKKYS

IGLAIGTNSVGWAVITDEYKVPSKKFKVLGNTDRHSIKKNLIGALLFDSG

ETAEATRLKRTARRRYTRRKNRICYLQEIFSNEMAKVDDSFFHRLEESFL

VEEDKKHERHPIFGNIVDEVAYHEKYPTIYHLRKKLVDSTDKADLRLIYL

ALAHMIKFRGHFLIEGDLNPDNSDVDKLFIQLVQTYNQLFEENPINASGV

DAKAILSARLSKSRRLENLIAQLPGEKKNGLFGNLIALSLGLTPNFKSNF

DLAEDAKLQLSKDTYDDDLDNLLAQIGDQYADLFLAAKNLSDAILLSDIL

RVNTEITKAPLSASMIKRYDEHHQDLTLLKALVRQQLPEKYKEIFFDQSK

NGYAGYIDGGASQEEFYKFIKPILEKMDGTEELLVKLNREDLLRKQRTFD

NGSIPHQIHLGELHAILRRQEDFYPFLKDNREKIEKILTFRIPYVGPLA

RGNSRFAWMTRKSEETITPWNFEEVVDKGASAQSFIERMTAFDKNLPNEK

VLPKHSLLYEYFTVYNELTKVKYVTEGMRKPAFLSGEQKKAIVDLLFKTN

RKVTVKQLKEDYFKKIECFDSVEISGVEDRFNASLGTYHDLLKIIKDKDF

LDNEENEDILEDIVLTLTLFEDREMIEERLKTYAHLFDDKVMKQLKRRRY

TGWGALSRKLINGIRDKQSGKTILDFLKSDGFANRNFMALIHDDSLTFKE

DIQKAQVSGQGDSLHEHIANLAGSPAIKKGILQTVKVVDELVKVMGRHKP

ENIVIEMARENQTTQKGQKNSRERMKRIEEGIKELGSQILKEHPVENTQL

QNEKLYLYYLQNGRDMYVDQELDINRLSDYDVDHIVPQSFLKDDSIDNKV

LTRSDKNRGKSDNVPSEEVVKKMKNYWRQLLNAKLITQRKFDNLTKAERG

GLSELDKAGFIKRQLVETRAITKHVAQILDSRMNTKYDENDKLIREVKVI

TLKSKLVSDFRKDFQFYKVREINNYHHAHDAYLNAVVGTALIKKYPKLES

EFVYGDYKVYDVRKMIAKSEQEIGKATAKYFFYSNIMNFFKTEITLANGE

IRKRPLIETNGETGEIVWDKGRDFATVRKVLSMPQVNIVKKTEVQTGGFS

KESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFEL

ENGRKRMLASAGELQKGNELALPSKYVNFLYLASHYEKLKGSPEDNEQKQ

LFVEQHKHYLDEIIEQISEFSKRVILADANLDKVLSAYNKHRDKPIREQA

ENIIHLFTLTNLGAPAAFKYFDTTIDRKRYTSTKEVLDATLIHQSITGLY

ETRIDLSQLGGD

Cas9 Fusion Proteins

Any of the Cas9 domains (e.g., a nuclease active Cas9 protein, a nuclease-inactive dCas9 protein, or a Cas9 nickase protein) disclosed herein may be fused to a second protein, thus fusion proteins provided herein comprise a Cas9 domain as provided herein and a second protein, or a "fusion partner". In some embodiments, the second protein is fused to the N-terminus of the Cas9 domain. However, in other embodiments, the second protein is fused to the C-terminus of the Cas9 domain. In some embodiments, the second protein that is fused to the Cas9 domain is a nucleic acid editing domain. In some embodiments, the Cas9 domain and the nucleic acid editing domain are fused via a linker, while in other embodiments the Cas9 domain and the nucleic acid editing domain are fused directly to one another. In some embodiments, the linker comprises (GGGS)$_n$ (SEQ ID NO: 265), (GGGGS)$_n$ (SEQ ID NO: 5), (G)$_n$, (EAAAK)$_n$ (SEQ ID NO: 6), (GGS)$_n$, (SGGS)$_n$ (SEQ ID NO: 4288), SGSETPGTSESATPES (SEQ ID NO: 7), or (XP)$_n$ motif, or a combination of any of these, wherein n is independently an integer between 1 and 30, and wherein X is any amino acid. In some embodiments, the linker comprises a (GGS)$_n$ motif, wherein n is 1, 3, or 7. In some embodiments, the linker comprises a (GGS)$_n$ motif, wherein n is 1, 2, 3, 4, 5, 6, 7, 8, 9, 10, 11, 12, 13, 14, or 15. In some embodiments, the linker comprises an amino acid sequence of SGSETPGTSESAT-PES (SEQ ID NO: 7), also referred to as the XTEN linker in the Examples). The length of the linker can influence the base to be edited, as illustrated in the Examples. For example, a linker of 3-amino-acid long (e.g., (GGS)$_1$) may give a 2-5, 2-4, 2-3, 3-4 base editing window relative to the PAM sequence, while a 9-amino-acid linker (e.g., (GGS)$_3$ (SEQ ID NO: 596)) may give a 2-6, 2-5, 2-4, 2-3, 3-6, 3-5, 3-4, 4-6, 4-5, 5-6 base editing window relative to the PAM sequence. A 16-amino-acid linker (e.g., the XTEN linker) may give a 2-7, 2-6, 2-5, 2-4, 2-3, 3-7, 3-6, 3-5, 3-4, 4-7, 4-6, 4-5, 5-7, 5-6, 6-7 base window relative to the PAM sequence with exceptionally strong activity, and a 21-amino-acid linker (e.g., (GGS)$_7$ (SEQ ID NO: 597)) may give a 3-8, 3-7, 3-6, 3-5, 3-4, 4-8, 4-7, 4-6, 4-5, 5-8, 5-7, 5-6, 6-8, 6-7, 7-8 base editing window relative to the PAM sequence. The novel finding that varying linker length may allow the dCas9 fusion proteins of the disclosure to edit nucleobases different distances from the PAM sequence affords significant clinical importance, since a PAM sequence may be of varying distance to the disease-causing mutation to be corrected in a gene. It is to be understood that the linker lengths described as examples here are not meant to be limiting.

In some embodiments, the second protein comprises an enzymatic domain. In some embodiments, the enzymatic domain is a nucleic acid editing domain. Such a nucleic acid editing domain may be, without limitation, a nuclease, a nickase, a recombinase, a deaminase, a methyltransferase, a methylase, an acetylase, or an acetyltransferase. Non-limiting exemplary binding domains that may be used in accordance with this disclosure include transcriptional activator domains and transcriptional repressor domains.

Deaminase Domains

In some embodiments, second protein comprises a nucleic acid editing domain. In some embodiments, the nucleic acid editing domain can catalyze a C to U base change. In some embodiments, the nucleic acid editing domain is a deaminase domain. In some embodiments, the deaminase is a cytidine deaminase or a cytidine deaminase. In some embodiments, the deaminase is an apolipoprotein B mRNA-editing complex (APOBEC) family deaminase. In some embodiments, the deaminase is an APOBEC1 deaminase. In some embodiments, the deaminase is an APOBEC2 deaminase. In some embodiments, the deaminase is an APOBEC3 deaminase. In some embodiments, the deaminase is an APOBEC3A deaminase. In some embodiments, the deaminase is an APOBEC3B deaminase. In some embodiments, the deaminase is an APOBEC3C deaminase. In some embodiments, the deaminase is an APOBEC3D deaminase. In some embodiments, the deaminase is an APOBEC3E deaminase. In some embodiments, the deaminase is an APOBEC3F deaminase. In some embodiments, the deaminase is an APOBEC3G deaminase. In some embodiments, the deaminase is an APOBEC3H deaminase. In some embodiments, the deaminase is an APOBEC4 deaminase. In some embodiments, the deaminase is an activation-induced deaminase (AID). In some embodiments, the deaminase is a vertebrate deaminase. In some embodiments, the deaminase is an invertebrate deaminase. In some embodiments, the deaminase is a human, chimpanzee, gorilla, monkey, cow, dog, rat, or mouse deaminase. In some embodiments, the deaminase is a human deaminase. In some embodiments, the deaminase is a rat deaminase, e.g., rAPOBEC1. In some embodiments, the deaminase is a *Petromyzon marinus* cytidine deaminase 1 (pmCDA1). In some embodiments, the deminase is a human APOBEC3G (SEQ ID NO: 275). In some embodiments, the deaminase is a fragment of the human APOBEC3G (SEQ ID NO: 5740). In some embodiments, the deaminase is a human APOBEC3G variant comprising a D316R_D317R mutation (SEQ ID NO: 5739). In some embodiments, the deaminase is a frantment of the human APOBEC3G and comprising mutations corresponding to the D316R_D317R mutations in SEQ ID NO: 275 (SEQ ID NO: 5741).

In some embodiments, the nucleic acid editing domain is at least 80%, at least 85%, at least 90%, at least 92%, at least 95%, at least 96%, at least 97%, at least 98%, at least 99%, or at least 99.5% identical to the deaminase domain of any one of SEQ ID NOs: 266-284, 607-610, 5724-5736, or 5738-5741. In some embodiments, the nucleic acid editing domain comprises the amino acid sequence of any one of SEQ ID NOs: 266-284, 607-610, 5724-5736, or 5738-5741.

Deaminase Domains that Modulate the Editing Window of Base Editors

Some aspects of the disclosure are based on the recognition that modulating the deaminase domain catalytic activity of any of the fusion proteins provided herein, for example by making point mutations in the deaminase domain, affect the processivity of the fusion proteins (e.g., base editors). For example, mutations that reduce, but do not eliminate, the catalytic activity of a deaminase domain within a base editing fusion protein can make it less likely that the deaminase domain will catalyze the deamination of a residue adjacent to a target residue, thereby narrowing the deamination window. The ability to narrow the deaminataion window may prevent unwanted deamination of residues adjacent of specific target residues, which may decrease or prevent off-target effects.

In some embodiments, any of the fusion proteins provided herein comprise a deaminase domain (e.g., a cytidine deaminase domain) that has reduced catalytic deaminase activity. In some embodiments, any of the fusion proteins provided herein comprise a deaminase domain (e.g., a cytidine deaminase domain) that has a reduced catalytic deaminase activity as compared to an appropriate control. For example, the appropriate control may be the deaminase activity of the deaminase prior to introducing one or more mutations into the deaminase. In other embodiments, the appropriate control may be a wild-type deaminase. In some embodiments, the appropriate control is a wild-type apolipoprotein B mRNA-editing complex (APOBEC) family deaminase. In some embodiments, the appropriate control is an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, or an APOBEC3H deaminase. In some embodiments, the appropriate control is an activation induced deaminase (AID). In some embodiments, the appropriate control is a cytidine deaminase 1 from *Petromyzon marinus* (pmCDA1). In some embodiments, the deaminse domain may be a deaminase domain that has at least 1%, at least 5%, at least 15%, at least 20%, at least 25%, at least 30%, at least 40%, at least 50%, at least 60%, at least 70%, at least 80%, at least 90%, or at least 95% less catalytic deaminase activity as compared to an appropriate control.

In some embodiments, any of the fusion proteins provided herein comprise an APOBEC deaminase comprising one or more mutations selected from the group consisting of H121X, H122X, R126X, R126X, R118X, W90X, W90X, and R132X of rAPOBEC1 (SEQ ID NO: 284), or one or more corresponding mutations in another APOBEC deaminase, wherein X is any amino acid. In some embodiments, any of the fusion proteins provided herein comprise an APOBEC deaminase comprising one or more mutations selected from the group consisting of H121R, H122R, R126A, R126E, R118A, W90A, W90Y, and R132E of rAPOBEC1 (SEQ ID NO: 284), or one or more corresponding mutations in another APOBEC deaminase.

In some embodiments, any of the fusion proteins provided herein comprise an APOBEC deaminase comprising one or more mutations selected from the group consisting of D316X, D317X, R320X, R320X, R313X, W285X, W285X, R326X of hAPOBEC3G (SEQ ID NO: 275), or one or more corresponding mutations in another APOBEC deaminase, wherein X is any amino acid. In some embodiments, any of the fusion proteins provided herein comprise an APOBEC deaminase comprising one or more mutations selected from the group consisting of D316R, D317R, R320A, R320E, R313A, W285A, W285Y, R326E of hAPOBEC3G (SEQ ID NO: 275), or one or more corresponding mutations in another APOBEC deaminase.

In some embodiments, any of the fusion proteins provided herein comprise an APOBEC deaminase comprising a H121R and a H122R mutation of rAPOBEC1 (SEQ ID NO: 284), or one or more corresponding mutations in another APOBEC deaminase. In some embodiments, any of the fusion proteins provided herein comprise an APOBEC deaminase comprising a R126A mutation of rAPOBEC1 (SEQ ID NO: 284), or one or more corresponding mutations in another APOBEC deaminase. In some embodiments, any of the fusion proteins provided herein comprise an APOBEC deaminase comprising a R126E mutation of rAPOBEC1 (SEQ ID NO: 284), or one or more corresponding mutations in another APOBEC deaminase. In some embodiments, any of the fusion proteins provided herein comprise an APOBEC deaminase comprising a R118A mutation of rAPOBEC1 (SEQ ID NO: 284), or one or more corresponding mutations in another APOBEC deaminase. In some embodiments, any of the fusion proteins provided herein comprise an APOBEC deaminase comprising a W90A mutation of rAPOBEC1 (SEQ ID NO: 284), or one or more corresponding mutations in another APOBEC deaminase. In some embodiments, any of the fusion proteins provided herein comprise an APOBEC deaminase comprising a W90Y mutation of rAPOBEC1 (SEQ ID NO: 284), or one or more corresponding mutations in another APOBEC deaminase. In some embodiments, any of the fusion proteins provided herein comprise an APOBEC deaminase comprising a R132E mutation of rAPOBEC1 (SEQ ID NO: 284), or one or more corresponding mutations in another APOBEC deaminase. In some embodiments, any of the fusion proteins provided herein comprise an APOBEC deaminase comprising a W90Y and a R126E mutation of rAPOBEC1 (SEQ ID NO: 284), or one or more corresponding mutations in another APOBEC deaminase. In some embodiments, any of the fusion proteins provided herein comprise an APOBEC deaminase comprising a R126E and a R132E mutation of rAPOBEC1 (SEQ ID NO: 284), or one or more corresponding mutations in another APOBEC deaminase. In some embodiments, any of the fusion proteins provided herein comprise an APOBEC deaminase comprising a W90Y and a R132E mutation of rAPOBEC1 (SEQ ID NO: 284), or one or more corresponding mutations in another APOBEC deaminase. In some embodiments, any of the fusion proteins provided herein comprise an APOBEC deaminase comprising a W90Y, R126E, and R132E mutation of rAPOBEC1 (SEQ ID NO: 284), or one or more corresponding mutations in another APOBEC deaminase.

In some embodiments, any of the fusion proteins provided herein comprise an APOBEC deaminase comprising a D316R and a D317R mutation of hAPOBEC3G (SEQ ID NO: 275), or one or more corresponding mutations in another APOBEC deaminase. In some embodiments, any of the fusion proteins provided herein comprise an APOBEC deaminase comprising a R320A mutation of hAPOBEC3G (SEQ ID NO: 275), or one or more corresponding mutations in another APOBEC deaminase. In some embodiments, any of the fusion proteins provided herein comprise an APOBEC deaminase comprising a R320E mutation of hAPOBEC3G (SEQ ID NO: 275), or one or more corresponding mutations in another APOBEC deaminase. In some embodiments, any of the fusion proteins provided herein comprise an APOBEC deaminase comprising a R313A mutation of hAPOBEC3G (SEQ ID NO: 275), or one or more corresponding mutations in another APOBEC deaminase. In some embodiments, any of the fusion proteins provided herein comprise an APOBEC deaminase comprising a W285A mutation of hAPOBEC3G (SEQ ID NO: 275), or one or more corresponding mutations in another APOBEC deaminase. In some embodiments, any of the fusion proteins provided herein comprise an APOBEC deaminase comprising a W285Y mutation of hAPOBEC3G (SEQ ID NO: 275), or one or more corresponding mutations in another APOBEC deaminase. In some embodiments, any of the fusion proteins provided herein comprise an APOBEC deaminase comprising a R326E mutation of hAPOBEC3G (SEQ ID NO: 275), or one or more corresponding mutations in another APOBEC deaminase. In some embodiments, any of the fusion proteins provided herein comprise an APOBEC deaminase comprising a W285Y and a R320E mutation of hAPOBEC3G (SEQ ID NO: 275), or one or more corresponding mutations in another APOBEC deaminase. In some embodiments, any of the fusion proteins provided herein comprise an APOBEC deaminase comprising a R320E and a R326E mutation of hAPOBEC3G (SEQ ID NO: 275), or one or more corresponding mutations in another APOBEC deaminase. In some embodiments, any of the fusion proteins provided herein comprise an APOBEC deaminase comprising a W285Y and a R326E mutation of hAPOBEC3G (SEQ ID NO: 275), or one or more corresponding mutations in another APOBEC deaminase. In some embodiments, any of the fusion proteins provided herein comprise an APOBEC deaminase comprising a W285Y, R320E, and R326E mutation of hAPOBEC3G (SEQ ID NO: 275), or one or more corresponding mutations in another APOBEC deaminase.

Some aspects of this disclosure provide fusion proteins comprising (i) a nuclease-inactive Cas9 domain; and (ii) a nucleic acid editing domain. In some embodiments, a nuclease-inactive Cas9 domain (dCas9), comprises an amino acid sequence that is at least 80%, at least 85%, at least 90%, at least 92%, at least 95%, at least 96%, at least 97%, at least 98%, at least 99%, or at least 99.5% identical to the amino acid sequence of a Cas9 as provided by any one of SEQ ID NOs: 10-263, and comprises mutations that inactivate the nuclease activity of Cas9. Mutations that render the nuclease domains of Cas9 inactive are well-known in the art. For example, the DNA cleavage domain of Cas9 is known to include two subdomains, the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H840A completely inactivate the nuclease activity of *S. pyogenes* Cas9 (Jinek et al., *Science*. 337:816-821 (2012); Qi et al., *Cell*. 28; 152(5):1173-83 (2013)). In some embodiments, the dCas9 of this disclosure comprises a D10A mutation of the amino acid sequence provided in SEQ ID NO: 10, or a corresponding mutation in any of the amino acid sequences provided in SEQ ID NOs: 11-260. In some embodiments, the dCas9 of this disclosure comprises a H840A mutation of the amino acid sequence provided in SEQ ID NO: 10, or a corresponding mutation in any of the amino acid sequences provided in SEQ ID NOs: 11-260. In some embodiments, the dCas9 of this disclosure comprises both D10A and H840A mutations of the amino acid sequence provided in SEQ ID NO: 10, or a corresponding mutation in any of the amino acid sequences provided in SEQ ID NOs: 11-260. In some embodiments, the Cas9 further comprises a histidine residue at position 840 of the amino acid sequence provided in SEQ ID NO: 10, or a corresponding mutation in any of the amino acid sequences provided in SEQ ID NOs: 11-260. The presence of the catalytic residue H840 restores the activity of the Cas9 to cleave the non-edited strand containing a G opposite the targeted C. Restoration of H840 does not result in the cleavage of the target strand containing the C. In some embodiments, the dCas9 comprises an amino acid sequence of SEQ ID NO: 263. It is to be understood that other mutations that inactivate the nuclease domains of Cas9 may also be included in the dCas9 of this disclosure.

The Cas9 or dCas9 domains comprising the mutations disclosed herein, may be a full-length Cas9, or a fragment thereof. In some embodiments, proteins comprising Cas9, or fragments thereof, are referred to as "Cas9 variants." A Cas9 variant shares homology to Cas9, or a fragment thereof. For example a Cas9 variant is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% to wild type Cas9. In some embodiments, the Cas9 variant comprises a fragment of Cas9 (e.g., a gRNA binding domain or a DNA-cleavage domain), such that the fragment is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to the corresponding fragment of wild type Cas9, e.g., a Cas9 comprising the amino acid sequence of SEQ ID NO: 10.

Any of the Cas9 fusion proteins of this disclosure may further comprise a nucleic acid editing domain (e.g., an enzyme that is capable of modifying nucleic acid, such as a deaminase). In some embodiments, the nucleic acid editing domain is a DNA-editing domain. In some embodiments, the nucleic acid editing domain has deaminase activity. In some embodiments, the nucleic acid editing domain comprises or consists of a deaminase or deaminase domain. In some embodiments, the deaminase is a cytidine deaminase. In some embodiments, the deaminase is an apolipoprotein B mRNA-editing complex (APOBEC) family deaminase. In some embodiments, the deaminase is an APOBEC1 family deaminase. In some embodiments, the deaminase is an activation-induced cytidine deaminase (AID). Some nucleic-acid editing domains as well as Cas9 fusion proteins including such domains are described in detail herein. Additional suitable nucleic acid editing domains will be apparent to the skilled artisan based on this disclosure and knowledge in the field.

Some aspects of the disclosure provide a fusion protein comprising a Cas9 domain fused to a nucleic acid editing domain, wherein the nucleic acid editing domain is fused to the N-terminus of the Cas9 domain. In some embodiments, the Cas9 domain and the nucleic acid editing-editing domain are fused via a linker. In some embodiments, the linker comprises a $(GGGS)_n$ (SEQ ID NO: 265), a $(GGGGS)_n$ (SEQ ID NO: 5), a $(G)_n$, an $(EAAAK)_n$ (SEQ ID NO: 6), a $(GGS)_n$, $(SGGS)_n$ (SEQ ID NO: 4288), an SGSETPGTS-ESATPES (SEQ ID NO: 7) motif (see, e.g., Guilinger J P, Thompson D B, Liu D R. Fusion of catalytically inactive Cas9 to FokI nuclease improves the specificity of genome modification. *Nat. Biotechnol.* 2014; 32(6): 577-82; the entire contents are incorporated herein by reference), or an $(XP)_n$ motif, or a combination of any of these, wherein n is independently an integer between 1 and 30. In some embodiments, n is independently 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, or, if more than one linker or more than one linker motif is present, any combination thereof. In some embodiments, the linker comprises a $(GGS)_n$ motif, wherein n is 1, 2, 3, 4, 5, 6, 7, 8, 9, 10, 11, 12, 13, 14 or 15. In some embodiments, the linker comprises a $(GGS)_n$ motif, wherein n is 1, 3, or 7. In some embodiments, the linker comprises the amino acid sequence SGSETPGTSESATPES (SEQ ID NO: 7). Additional suitable linker motifs and linker configurations will be apparent to those of skill in the art. In some embodiments, suitable linker motifs and configurations include those described in Chen et al., Fusion protein linkers: property, design and functionality. *Adv Drug Deliv Rev.* 2013; 65(10):1357-69, the entire contents of which are incorporated herein by reference. Additional suitable linker sequences will be apparent to those of skill in the art based on the instant disclosure. In some embodiments, the general architecture of exemplary Cas9 fusion proteins provided herein comprises the structure:

[NH$_2$]-[nucleic acid editing domain]-[Cas9]-[COOH] or
[NH$_2$]-[nucleic acid editing domain]-[linker]-[Cas9]-[COOH], wherein NH$_2$ is the N-terminus of the fusion protein, and COOH is the C-terminus of the fusion protein.

The fusion proteins of the present disclosure may comprise one or more additional features. For example, in some embodiments, the fusion protein comprises a nuclear localization sequence (NLS). In some embodiments, the NLS of the fusion protein is localized between the nucleic acid editing domain and the Cas9 domain. In some embodiments, the NLS of the fusion protein is localized C-terminal to the Cas9 domain.

Other exemplary features that may be present are localization sequences, such as cytoplasmic localization sequences, export sequences, such as nuclear export sequences, or other localization sequences, as well as sequence tags that are useful for solubilization, purification, or detection of the fusion proteins. Suitable protein tags provided herein include, but are not limited to, biotin carboxylase carrier protein (BCCP) tags, myc-tags, calmodulin-tags, FLAG-tags, hemagglutinin (HA)-tags, polyhistidine tags, also referred to as histidine tags or His-tags, maltose binding protein (MBP)-tags, nus-tags, glutathione-S-transferase (GST)-tags, green fluorescent protein (GFP)-tags, thioredoxin-tags, S-tags, Softags (e.g., Softag 1, Softag 3), strep-tags, biotin ligase tags, FlAsH tags, V5 tags, and SBP-tags. Additional suitable sequences will be apparent to those of skill in the art. In some embodiments, the fusion protein comprises one or more His tags.

In some embodiments, the nucleic acid editing domain is a deaminase. For example, in some embodiments, the general architecture of exemplary Cas9 fusion proteins with a deaminase domain comprises the structure:

[NH$_2$]-[NLS]-[deaminase]-[Cas9]-[COOH],
[NH$_2$]-[Cas9]-[deaminase]-[COOH],
[NH$_2$]-[deaminase]-[Cas9]-[COOH], or
[NH$_2$]-[deaminase]-[Cas9]-[NLS]-[COOH]

wherein NLS is a nuclear localization sequence, NH$_2$ is the N-terminus of the fusion protein, and COOH is the C-terminus of the fusion protein. Nuclear localization sequences are known in the art and would be apparent to the skilled artisan. For example, NLS sequences are described in Plank et al., PCT/EP2000/011690, the contents of which are incorporated herein by reference for their disclosure of exemplary nuclear localization sequences. In some embodiments, a NLS comprises the amino acid sequence PKKKRKV (SEQ ID NO: 741) or MDSLLMNRRKFLYQFKNVRWAKGR-RETYLC (SEQ ID NO: 742). In some embodiments, a linker is inserted between the Cas9 and the deaminase. In some embodiments, the NLS is located C-terminal of the Cas9 domain. In some embodiments, the NLS is located N-terminal of the Cas9 domain. In some embodiments, the NLS is located between the deaminase and the Cas9 domain. In some embodiments, the NLS is located N-terminal of the deaminase domain. In some embodiments, the NLS is located C-terminal of the deaminase domain.

One exemplary suitable type of nucleic acid editing domain is a cytidine deaminase, for example, of the APOBEC family. The apolipoprotein B mRNA-editing complex (APOBEC) family of cytidine deaminase enzymes encompasses eleven proteins that serve to initiate mutagenesis in a controlled and beneficial manner.[29] One family member, activation-induced cytidine deaminase (AID), is responsible for the maturation of antibodies by converting cytosines in ssDNA to uracils in a transcription-dependent, strand-biased fashion.[30] The apolipoprotein B editing complex 3 (APOBEC3) enzyme provides protection to human cells against a certain HIV-1 strain via the deamination of cytosines in reverse-transcribed viral ssDNA.[31] These proteins all require a $Zn^{2+}$-coordinating motif (His-X-Glu-$X_{23-26}$-Pro-Cys-$X_{2-4}$-Cys; SEQ ID NO: 598) and bound water molecule for catalytic activity. The Glu residue acts to activate the water molecule to a zinc hydroxide for nucleophilic attack in the deamination reaction. Each family member preferentially deaminates at its own particular "hotspot", ranging from WRC (W is A or T, R is A or G) for hAID, to TTC for hAPOBEC3F.[32] A recent crystal structure of the catalytic domain of APOBEC3G revealed a secondary structure comprised of a five-stranded β-sheet core flanked by six α-helices, which is believed to be conserved across the entire family.[33] The active center loops have been shown to be responsible for both ssDNA binding and in determining "hotspot" identity.[34] Overexpression of these enzymes has been linked to genomic instability and cancer, thus highlighting the importance of sequence-specific targeting.[35]

Some aspects of this disclosure relate to the recognition that the activity of cytidine deaminase enzymes such as APOBEC enzymes can be directed to a specific site in genomic DNA. Without wishing to be bound by any particular theory, advantages of using Cas9 as a recognition agent include (1) the sequence specificity of Cas9 can be easily altered by simply changing the sgRNA sequence; and (2) Cas9 binds to its target sequence by denaturing the dsDNA, resulting in a stretch of DNA that is single-stranded and therefore a viable substrate for the deaminase. It should be understood that other catalytic domains, or catalytic domains from other deaminases, can also be used to generate fusion proteins with Cas9, and that the disclosure is not limited in this regard.

Figure 3:
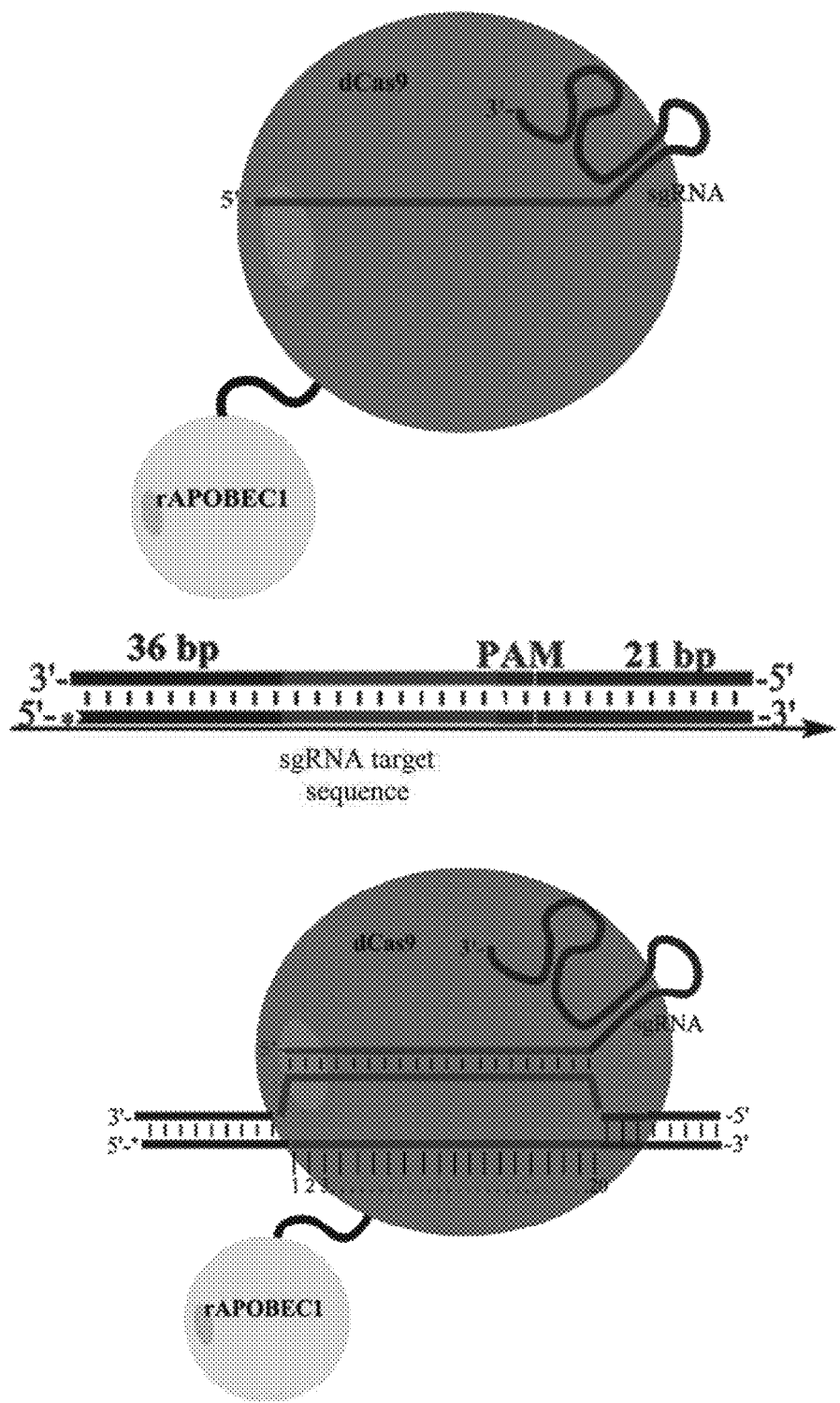
FIG. 3 illustrates double stranded DNA substrate binding by Cas9:deaminase:sgRNA complexes.

Some aspects of this disclosure are based on the recognition that Cas9:deaminase fusion proteins can efficiently deaminate nucleotides at positions 3-11 according to the numbering scheme in FIG. 3. In view of the results provided herein regarding the nucleotides that can be targeted by Cas9:deaminase fusion proteins, a person of skill in the art will be able to design suitable guide RNAs to target the fusion proteins to a target sequence that comprises a nucleotide to be deaminated.

In some embodiments, the deaminase domain and the Cas9 domain are fused to each other via a linker. Various linker lengths and flexibilities between the deaminase domain (e.g., AID) and the Cas9 domain can be employed (e.g., ranging from very flexible linkers of the form $(GGGGS)_n$, (SEQ ID NO: 5), $(GGS)_n$, and $(G)_n$ to more rigid linkers of the form $(EAAAK)_n$ (SEQ ID NO: 6), $(SGGS)_n$ (SEQ ID NO: 4288), SGSETPGTSESATPES (SEQ ID NO: 7) (see, e.g., Guilinger J P, Thompson D B, Liu D R. Fusion of catalytically inactive Cas9 to FokI nuclease improves the specificity of genome modification. *Nat. Biotechnol.* 2014; 32(6): 577-82; the entire contents are incorporated herein by reference) and $(XP)_n)^{36}$ in order to achieve the optimal length for deaminase activity for the specific application. In some embodiments, the linker comprises a $(GGS)_n$ motif, wherein n is 1, 3, or 7. In some embodiments, the linker comprises a (an SGSETPGTSESATPES (SEQ ID NO: 7) motif.

Some exemplary suitable nucleic-acid editing domains, e.g., deaminases and deaminase domains, that can be fused to Cas9 domains according to aspects of this disclosure are provided below. It should be understood that, in some embodiments, the active domain of the respective sequence can be used, e.g., the domain without a localizing signal (nuclear localization sequence, without nuclear export signal, cytoplasmic localizing signal).

```
Human AID:
                                                        (SEQ ID NO: 266)
MDSLLMNRRKFLYQFKNVRWAKGRRETYLCYVVKRRDSATSFSLDFGYLRNKNGC

HVELLFLRYISDWDLDPGRCYRVTWFTSWSPCYDCARHVADFLRGNPNLSLRIFTAR

LYFCEDRKAEPEGLRRLHRAGVQIAIMTFKDYFYCWNTFVENHERTFKAWEGLHEN

SVRLSRQLRRILLPLYEVDDLRDAFRTLGL (underline: nuclear localization sequence; double underline:

nuclear export signal)

Mouse AID:
                                                        (SEQ ID NO: 267)
MDSLLMKQKKFLYHFKNVRWAKGRHETYLCYVVKRRDSATSCSLDFGHLRNKSGC

HVELLFLRYISDWDLDPGRCYRVTWFTSWSPCYDCARHVAEFLRWNPNLSLRIFTAR

LYFCEDRKAEPEGLRRLHRAGVQIGIMTFKDYFYCWNTFVENRERTFKAWEGLHEN

SVRLTRQLRRILLPLYEVDDLRDAFRMLGF
```

-continued (underline: nuclear localization sequence; double underline: nuclear export signal)

Dog AID:
(SEQ ID NO: 268)
MDSLLMKQRKFLYHFKNVRWAKGRHETYLCYVVKRRDSATSFSLDFGHLRNKSGC
HVELLFLRYISDWDLDPGRCYRVTWFTSWSPCYDCARHVADFLRGYPNLSLRIFAAR
LYFCEDRKAEPEGLRRLHRAGVQIAIMTFKDYFYCWNTFVENREKTFKAWEGLHEN
SVRLSRQLRRILLPLYEVDDLRDAFRTLGL (underline: nuclear localization sequence; double underline: nuclear export signal)

Bovine AID:
(SEQ ID NO: 269)
MDSLLKKQRQFLYQFKNVRWAKGRHETYLCYVVKRRDSPTSFSLDFGHLRNKAGC
HVELLFLRYISDWDLDPGRCYRVTWFTSWSPCYDCARHVADFLRGYPNLSLRIFTAR
LYFCDKERKAEPEGLRRLHRAGVQIAIMTFKDYFYCWNTFVENHERTFKAWEGLHE
NSVRLSRQLRRILLPLYEVDDLRDAFRTLGL (underline: nuclear localization sequence; double underline: nuclear export signal)

Rat AID
(SEQ ID NO: 5725)
MAVGSKPKAALVGPHWERERIWCFLCSTGLGTQQTGQTSRWLRPAATQDPVSPPRS
LLMKQRKFLYHFKNVRWAKGRHETYLCYVVKRRDSATSFSLDFGYLRNKSGCHVE
LLFLRYISDWDLDPGRCYRVTWFTSWSPCYDCARHVADFLRGNPNLSLRIFTARLTG
WGALPAGLMSPARPSDYFYCWNTFVENHERTFKAWEGLHENSVRLSRRLRRILLPL
YEVDDLRDAFRTLGL (underline: nuclear localization sequence; double underline: nuclear export signal)

Mouse APOBEC-3:
(SEQ ID NO: 270)
MGPFCLGCSHRKCYSPIRNLISQETFKFHFKNLGYAKGRKDTFLCYEVTRKDCDSPVS
LHHGVFKNKDNI*HAEICFLYWFHDKVLKVLSPREEFKITWYMSWSPCFEC*AEQIVRFLA
THHNLSLDIFSSRLYNVQDPETQQNLCRLVQEGAQVAAMDLYEFKKCWKKFVDNG
GRRFRPWKRLLTNFRYQDSKLQEILRPCYIPVPSSSSSTLSNICLTKGLPETRFCVEGR
RMDPLSEEEFYSQFYNQRVKHLCYYHRMKPYLCYQLEQFNGQAPLKGCLLSEKGKQ
*HAEILFLDKIRSMELSQVTITCYLTWSPCPNC*AWQLAAFKRDRPDLILHIYTSRLYFHWK
RPFQKGLCSLWQSGILVDVMDLPQFTDCWTNFVNPKRPFWPWKGLEIISRRTQRRLR
RIKESWGLQDLVNDFGNLQLGPPMS (italic: nucleic acid editing domain)

Rat APOBEC-3:
(SEQ ID NO: 271)
MGPFCLGCSHRKCYSPIRNLISQETFKFHFKNLRYAIDRKDTFLCYEVTRKDCDSPVS
LHHGVFKNKDNI*HAEICFLYWFHDKVLKVLSPREEFKITWYMSWSPCFEC*AEQVLRFLA
THHNLSLDIFSSRLYNIRDPENQQNLCRLVQEGAQVAAMDLYEFKKCWKKFVDNGG
RRFRPWKKLLTNFRYQDSKLQEILRPCYIPVPSSSSSTLSNICLTKGLPETRFCVERRR
VHLLSEEEFYSQFYNQRVKHLCYYHGVKPYLCYQLEQFNGQAPLKGCLLSEKGKQ*H
AEILFLDKIRSMELSQVIITCYLTWSPCPNC*AWQLAAFKRDRPDLILHIYTSRLYFHWKR

-continued

PFQKGLCSLWQSGILVDVMDLPQFTDCWTNFVNPKRPFWPWKGLEIISRRTQRRLHR

IKESWGLQDLVNDFGNLQLGPPMS (italic: nucleic acid editing domain)

Rhesus macaque APOBEC-3G:
(SEQ ID NO: 272)

MVEPMDPRTFVSNFNNRPILSGLNTVWLCCEVKTKDPSGPPLDAKIFQGKVYSKAKY

HPEM*RFLRWFHKWRQLHHDQEYKVTWYVSWSPCTRC*ANSVATFLAKDPKVTLTIFVA

RLYYFWKPDYQQALRILCQKRGGPHATMKIMNYNEFQDCWNKFVDGRGKPFKPRN

NLPKHYTLLQATLGELLRHLMDPGTFTSNFNNKPWVSGQHETYLCYKVERLHNDT

WVPLNQHRGFLRNQAPNIHGFPKGR*HAELCFLDLIPFWKLDGQQYRVTCFTSWSPCFS*

*CAQEMAKFISNNEHVSLCIFAARIYDDQGRYQEGLRALHRDGAKIAMMNYSEFEYC*

*WDTFVDRQGRPFQPWDGLDEHSQALSGRLRAI*

(italic: nucleic acid editing domain; underline: cytoplasmic
localization signal)

Chimpanzee APOBEC-3G:
(SEQ ID NO: 273)

MKPHFRNPVERMYQDTFSDNFYNRPILSHRNTVWLCYEVKTKGPSRPPLDAKIFRGQ

VYSKLKY*HPEMRFFHWFSKWRKLHRDQEYEVIWYISWSPCTKC*TRDVATFLAEDPKV

TLTIFVARLYYFWDPDYQEALRSLCQKRDGPRATMKIMNYDEFQHCWSKFVYSQRE

LFEPWNNLPKYYILLHIMLGEILRHSMDPPTFTSNFNNELWVRGRHETYLCYEVERL

HNDTWVLLNQRRGFLCNQAPHKHGFLEGR*HAELCFLDVIPFWKLDLHQDYRVTCFTS*

*WSPCFS*CAQEMAKFISNNKHVSLCIFAARIYDDQGRCQEGLRTLAKAGAKISIMTYSE

FKHCWDTFVDHQGCPFQPWDGLEEHSQALSGRLRAILQNQGN (italic: nucleic acid editing domain; underline: cytoplasmic
localization signal)

Green monkey APOBEC-3G:
(SEQ ID NO: 274)

MNPQIRNMVEQMEPDIFVYYFNNRPILSGRNTVWLCYEVKTKDPSGPPLDANIFQGK

LYPEAKD*HPEMKFLHWFRKWRQLHRDQEYEVTWYVSWSPCTRC*ANSVATFLAEDPKV

TLTIFVARLYYFWKPDYQQALRILCQERGGPHATMKIMNYNEFQHCWNEFVDGQG

KPFKPRKNLPKHYTLLHATLGELLRHVMDPGTFTSNFNNKPWVSGQRETYLCYKVE

RSHNDTWVLLNQHRGFLRNQAPDRHGFPKGR*HAELCFLDLIPFWKLDDQQYRVTCFT*

*SWSPCFSC*AQKMAKFISNNKHVSLCIFAARIYDDQGRCQEGLRTLHRDGAKIAVMNY

SEFEYCWDTFVDRQGRPFQPWDGLDEHSQALSGRLRAI (italic: nucleic acid editing domain; underline: cytoplasmic
localization signal)

Human APOBEC-3G:
(SEQ ID NO: 275)

MKPHFRNTVERMYRDTFSYNFYNRPILSRRNTVWLCYEVKTKGPSRPPLDAKIFRGQ

VYSELKY*HPEMRFFHWFSKWRKLHRDQEYEVTWYISWSPCTKC*TRDMATFLAEDPKV

TLTIFVARLYYFWDPDYQEALRSLCQKRDGPRATMKIMNYDEFQHCWSKFVYSQRE

LFEPWNNLPKYYILLHIMLGEILRHSMDPPTFTFNFNNEPWVRGRHETYLCYEVERM

HNDTWVLLNQRRGFLCNQAPHKHGFLEGR*HAELCFLDVIPFWKLDLDQDYRVTCFTS*

*WSPCFS*CAQEMAKFISKNKHVSLCIFTARIYDDQGRCQEGLRTLAEAGAKISIMTYSE

FKHCWDTFVDHQGCPFQPWDGLDEHSQDLSGRLRAILQNQEN

-continued (italic: nucleic acid editing domain; underline: cytoplasmic localization signal)

Human APOBEC-3F:
(SEQ ID NO: 276)
MKPHFRNTVERMYRDTFSYNFYNRPILSRRNTVWLCYEVKTKGPSRPRLDAKIFRGQ

VYSQPEH*HAEMCFLSWFCGNQLPAYKCFQITWFVSWTPCPDC*VAKLAEFLAEHPNVTL

TISAARLYYYWERDYRRALCRLSQAGARVKIMDDEEFAYCWENFVYSEGQPFMPW

YKFDDNYAFLHRTLKEILRNPMEAMYPHIFYFHFKNLRKAYGRNESWLCFTMEVVK

HHSPVSWKRGVFRNQVDPETH*CHAERCFLSWFCDDILSPNTNYEVTWYTSWSPCPEC*A

GEVAEFLARHSNVNLTIFTARLYYFWDTDYQEGLRSLSQEGASVEIMGYKDFKYCW

ENFVYNDDEPFKPWKGLKYNFLFLDSKLQEILE (italic: nucleic acid editing domain)

Human APOBEC-3B:
(SEQ ID NO: 277)
MNPQRNPMERMYRDTFYDNFENEPILYGRSYTWLCYEVKIKRGRSNLLWDTGVFR

GQVYFKPQY*HAEMCFLSWFCGNQLPAYKCFQITWFVSWTPCPDC*VAKLAEFLSEHPN

VTLTISAARLYYYWERDYRRALCRLSQAGARVTIMDYEEFAYCWENFVYNEGQQF

MPWYKFDENYAFLHRTLKEILRYLMDPDTFTFNFNNDPLVLRRRQTYLCYEVERLD

NGTWVLMDQHMGFLCNEAKNLLCGFY*GRHAELRFLDLVPSLQLDPAQIYRWWFISWS

PCFSWGC*AGEVRAFLQENTHVRLRIFAARIYDYDPLYKEALQMLRDAGAQVSIMTY

DEFEYCWDTFVYRQGCPFQPWDGLEEHSQALSGRLRAILQNQGN (italic: nucleic acid editing domain)

Rat APOBEC-3B:
(SEQ ID NO: 5729)
MQPQGLGPNAGMGPVCLGCSHRRPYSPIRNPLKKLYQQTFYFHFKNVRYAWGRKN

NFLCYEVNGMDCALPVPLRQGVFRKQGHIHAELCFIYWFHDKVLRVLSPMEEFKVT

WYMSWSPCSKCAEQVARFLAAHRNLSLAIFSSRLYYYLRNPNYQQKLCRLIQEGVH

VAAMDLPEFKKCWNKFVDNDGQPFRPWMRLRINFSFYDCKLQEIFSRMNLLREDVF

YLQFNNSHRVKPVQNRYYRRKSYLCYQLERANGQEPLKGYLLYKKGEQHVEILFLE

KMRSMELSQVRITCYLTWSPCPNCARQLAAFKKDHPDLILRIYTSRLYFYWRKKFQK

GLCTLWRSGIHVDVMDLPQFADCWTNFVNPQRPFRPWNELEKNSWRIQRRLRRIKE

SWGL

Bovine APOBEC-3B:
(SEQ ID NO: 5730)
DGWEVAFRSGTVLKAGVLGVSMTEGWAGSGHPGQGACVWTPGTRNTMNLLREVL

FKQQFGNQPRVPAPYYRRKTYLCYQLKQRNDLTLDRGCFRNKKQRHAEIRFIDKINS

LDLNPSQSYKIICYITWSPCPNCANELVNFITRNNHLKLEIFASRLYFHWIKSFKMGLQ

DLQNAGISVAVMTHTEFEDCWEQFVDNQSRPFQPWDKLEQYSASIRRRLQRILTAPI

Chimpanzee APOBEC-3B :
(SEQ ID NO: 5731)
MNPQIRNPMEWMYQRTFYYNFENEPILYGRSYTWLCYEVKIRRGHSNLLWDTGVFR

GQMYSQPEHHAEMCFLSWFCGNQLSAYKCFQITWFVSWTPCPDCVAKLAKFLAEHP

NVTLTISAARLYYYWERDYRRALCRLSQAGARVKIMDDEEFAYCWENFVYNEGQPF

MPWYKFDDNYAFLHRTLKEIIRHLMDPDTFTFNFNNDPLVLRRHQTYLCYEVERLD

NGTWVLMDQHMGFLCNEAKNLLCGFYGRHAELRFLDLVPSLQLDPAQIYRVTWFIS

WSPCFSWGCAGQVRAFLQENTHVRLRIFAARIYDYDPLYKEALQMLRDAGAQVSIM

-continued

TYDEFEYCWDTFVYRQGCPFQPWDGLEEHSQALSGRLRAILQVRASSLCMVPHRPPP

PPQSPGPCLPLCSEPPLGSLLPTGRPAPSLPFLLTASFSFPPPASLPPLPSLSLSPGHLPVP

SFHSLTSCSIQPPCSSRIRETEGWASVSKEGRDLG

Human APOBEC-3C:
(SEQ ID NO: 278)
MNPQIRNPMKAMYPGTFYFQFKNLWEANDRNETWLCFTVEGIKRRSVVSWKTGVF

RNQVDSETH*CHAERCFLSWFCDDILSPNTKYQVIWYTSWSPCPDC*AGEVAEFLARHSN

VNLTIFTARLYYFQYPCYQEGLRSLSQEGVAVEIMDYEDFKYCWENFVYNDNEPFKP

WKGLKTNFRLLKRRLRESLQ (italic: nucleic acid editing domain)

Gorilla APOBEC3C
(SEQ ID NO: 5726)
MNPQIRNPMKAMYPGTFYFQFKNLWEANDRNETWLCFTVEGIKRRSVVSWKTGVF

RNQVDSETH*CHAERCFLSWFCDDILSPNTNYQVTWYTSWSPCPEC*AGEVAEFLARHSN

VNLTIFTARLYYFQDTDYQEGLRSLSQEGVAVKIMDYKDFKYCWENFVYNDDEPFK

PWKGLKYNFRFLKRRLQEILE (italic: nucleic acid editing domain)

Human APOBEC-3A:
(SEQ ID NO: 279)
MEASPASGPRHLMDPHIFTSNFNNGIGRHKTYLCYEVERLDNGTSVKMDQHRGFLH

NQAKNLLCGFYGR*HAELRFLDLVPSLQLDPAQIYRVTWFISWSPCFSWGC*AGEVRAFLQ

ENTHVRLRIFAARIYDYDPLYKEALQMLRDAGAQVSIMTYDEFKHCWDTFVDHQGC

PFQPWDGLDEHSQALSGRLRAILQNQGN (italic: nucleic acid editing domain)

Rhesus macaque APOBEC-3A:
(SEQ ID NO: 5727)
MDGSPASRPRHLMDPNTFTFNFNNDLSVRGRHQTYLCYEVERLDNGTWVPMDERR

GFLCNKAKNVPCGDYGC*HVELRFLCEVPSWQLDPAQTYRVTWFISWSPC*FRRGCAGQ

VRVFLQENKHVRLRIFAARIYDYDPLYQEALRTLRDAGAQVSIMTYEEFKHCWDTF

VDRQGRPFQPWDGLDEHSQALSGRLRAILQNQGN (italic: nucleic acid editing domain)

Bovine APOBEC-3A:
(SEQ ID NO: 5728)
MDEYTFTENFNNQGWPSKTYLCYEMERLDGDATIPLDEYKGFVRNKGLDQPEKP*CH*

*AELYFLGKIHSWNLDRNQHYRLTCFISWSPC*YDCAQKLTTFLKENHHISLHILASRIYTH

NRFGCHQSGLCELQAAGARITIMTFEDFKHCWETFVDHKGKPFQPWEGLNVKSQAL

CTELQAILKTQQN (italic: nucleic acid editing domain)

Human APOBEC-3H:
(SEQ ID NO: 280)
MALLTAETFRLQFNNKRRLRRPYYPRKALLCYQLTPQNGSTPTRGYFENKKKC*HAEI*

*CFINEIKSMGLDETQCYQVTCYLTWSPCSSC*AWELVDFIKAHDHLNLGIFASRLYYHWC

KPQQKGLRLLCGSQVPVEVMGFPKFADCWENFVDHEKPLSFNPYKMLEELDKNSRA

IKRRLERIKIPGVRAQGRYMDILCDAEV

-continued (italic: nucleic acid editing domain)

Rhesus macaque APOBEC-3H:
(SEQ ID NO: 5732)
MALLTAKTFSLQFNNKRRVNKPYYPRKALLCYQLTPQNGSTPTRGHLKNKKKDHAE

IRFINKIKSMGLDETQCYQVTCYLTWSPCPSCAGELVDFIKAHRHLNLRIFASRLYYH

WRPNYQEGLLLLCGSQVPVEVMGLPEFTDCWENFVDHKEPPSFNPSEKLEELDKNS

QAIKRRLERIKSRSVDVLENGLRSLQLGPVTPSSSIRNSR

Human APOBEC-3D:
(SEQ ID NO: 281)
MNPQIRNPMERMYRDTFYDNFENEPILYGRSYTWLCYEVKIKRGRSNLLWDTGVFR

GPVLPKRQSNHRQEVYFRFEN*HAEMCFLSWFCGNRLPANRRFQITWFVSWNPCLPCVV*

KVTKFLAEHPNVTLTISAARLYYYRDRDWRWVLLRLHKAGARVKIMDYEDFAYCW

ENFVCNEGQPFMPWYKFDDNYASLHRTLKEILRNPMEAMYPHIFYFHFKNLLKACG

RNESWLCFTMEVTKHHSAVFRKRGVFRNQVDPETHC*HAERCFLSWFCDDILSPNTNY*

*EVTWYTSWSPCPEC*AGEVAEFLARHSNVNLTIFTARLCYFWDTDYQEGLCSLSQEGAS

VKIMGYKDFVSCWKNFVYSDDEPFKPWKGLQTNFRLLKRRLREILQ (italic: nucleic acid editing domain)

Human APOBEC-1:
(SEQ ID NO: 282)
MTSEKGPSTGDPTLRRRIEPWEFDVFYDPRELRKEACLLYEIKWGMSRKIWRSSGKN

TTNHVEVNFIKKFTSERDFHPSMSCSITWFLSWSPCWECSQAIREFLSRHPGVTLVIYV

ARLFWHMDQQNRQGLRDLVNSGVTIQIMRASEYYHCWRNFVNYPPGDEAHWPQYP

PLWMMLYALELHCIILSLPPCLKISRRWQNHLTFFRLHLQNCHYQTIPPHILLATGLIH

PSVAWR

Mouse APOBEC-1:
(SEQ ID NO: 283)
MSSETGPVAVDPTLRRRIEPHEFEVFFDPRELRKETCLLYEINWGGRHSVWRHTSQN

TSNHVEVNFLEKFTTERYFRPNTRCSITWFLSWSPCGECSRAITEFLSRHPYVTLFIYIA

RLYHHTDQRNRQGLRDLISSGVTIQIMTEQEYCYCWRNFVNYPPSNEAYWPRYPHL

WVKLYVLELYCIILGLPPCLKILRRKQPQLTFFTITLQTCHYQRIPPHLLWATGLK

Rat APOBEC-1:
(SEQ ID NO: 284)
MSSETGPVAVDPTLRRRIEPHEFEVFFDPRELRKETCLLYEINWGGRHSIWRHTSQNT

NKHVEVNFIEKFTTERYFCPNTRCSITWFLSWSPCGECSRAITEFLSRYPHVTLFIYIAR

LYHHADPRNRQGLRDLISSGVTIQIMTEQESGYCWRNFVNYSPSNEAHWPRYPHLW

VRLYVLELYCIILGLPPCLNILRRKQPQLTFFTIALQSCHYQRLPPHILWATGLK

Human APOBEC-2:
(SEQ ID NO: 5733)
MAQKEEAAVATEAASQNGEDLENLDDPEKLKELIELPPFEIVTGERLPANFFKFQFRN

VE

YSSGRNKTFLCYVVEAQGKGGQVQASRGYLEDEHAAAHAEEAFFNTILPAFDPALR

YNVTWYVSSSPCAACADRIIKTLSKTKNLRLLILVGRLFMWEEPEIQAALKKLKEAG

CKLRIMKPQDFEYVWQNFVEQEEGESKAFQPWEDIQENFLYYEEKLADILK

Mouse APOBEC-2:
(SEQ ID NO: 5734)
MAQKEEAAEAAAPASQNGDDLENLEDPEKLKELIDLPPFEIVTGVRLPVNFFKFQFR

NVEYSSGRNKTFLCYVVEVQSKGGQAQATQGYLEDEHAGAHAEEAFFNTILPAFDP

ALKYNVTWYVSSSPCAACADRILKTLSKTKNLRLLILVSRLFMWEEPEVQAALKKLK

```
EAGCKLRIMKPQDFEYIWQNFVEQEEGESKAFEPWEDIQENFLYYEEKLADILK

Rat APOBEC-2:
                                                        (SEQ ID NO: 5735)
MAQKEEAAEAAAPASQNGDDLENLEDPEKLKELIDLPPFEIVTGVRLPVNFFKFQFR

NVEYSSGRNKTFLCYVVEAQSKGGQVQATQGYLEDEHAGAHAEEAFFNTILPAFDP

ALKYNVTWYVSSSPCAACADRILKTLSKTKNLRLLILVSRLFMWEEPEVQAALKKLK

EAGCKLRIMKPQDFEYLWQNFVEQEEGESKAFEPWEDIQENFLYYEEKLADILK

Bovine APOBEC-2:
                                                        (SEQ ID NO: 5736)
MAQKEEAAAAAEPASQNGEEVENLEDPEKLKELIELPPFEIVTGERLPAHYFKFQFRN

VE

YSSGRNKTFLCYVVEAQSKGGQVQASRGYLEDEHATNHAEEAFFNSIMPTFDPALR

YMVTWYVSSSPCAACADRIVKTLNKTKNLRLLILVGRLFMWEEPEIQAALRKLKEA

GCRLRIMKPQDFEYIWQNFVEQEEGESKAFEPWEDIQENFLYYEEKLADILK

Petromyzon marinus CDA1 (pmCDA1)
                                                        (SEQ ID NO: 5738)
MTDAEYVRIHEKLDIYTFKKQFFNNKKSVSHRCYVLFELKRRGERRACFWGYAVNK

PQSGTERGIHAEIFSIRKVEEYLRDNPGQFTINWYSSWSPCADCAEKILEWYNQELRG

NGHTLKIWACKLYYEKNARNQIGLWNLRDNGVGLNVMVSEHYQCCRKIFIQSSHNQ

LNENRWLEKTLKRAEKRRSELSIMIQVKILHTTKSPAV

Human APOBEC3G D316R_D317R
                                                        (SEQ ID NO: 5739)
MKPHFRNTVERMYRDTFSYNFYNRPILSRRNTVWLCYEVKTKGPSRPPLDAKIFRGQ

VYSELKYHPEMRFFHWFSKWRKLHRDQEYEVTWYISWSPCTKCTRDMATFLAEDP

KVTLTIFVARLYYFWDPDYQEALRSLCQKRDGPRATMKIMNYDEFQHCWSKFVYSQ

RELFEPWNNLPKYYILLHIMLGEILRHSMDPPTFTFNFNNEPWVRGRHETYLCYEVER

MHNDTWVLLNQRRGFLCNQAPHKHGFLEGRHAELCFLDVIPFWKLDLDQDYRVTC

FTSWSPCFSCAQEMAKFISKNKHVSLCIFTARIYRRQGRCQEGLRTLAEAGAKISIMT

YSEFKHCWDTFVDHQGCPFQPWDGLDEHSQDLSGRLRAILQNQEN

Human APOBEC3G chain A
                                                        (SEQ ID NO: 5740)
MDPPTFTFNFNNEPWVRGRHETYLCYEVERMHNDTWVLLNQRRGFLCNQAPHKHG

FLEGRHAELCFLDVIPFWKLDLDQDYRVTCFTSWSPCFSCAQEMAKFISKNKHVSLCI

FTARIYDDQGRCQEGLRTLAEAGAKISIMTYSEFKHCWDTFVDHQGCPFQPWDGLD

EHSQDLSGRLRAILQ

Human APOBEC3G chain A D120R_D121R
                                                        (SEQ ID NO: 5741)
MDPPTFTFNFNNEPWVRGRHETYLCYEVERMHNDTWVLLNQRRGFLCNQAPHKHG

FLEGRHAELCFLDVIPFWKLDLDQDYRVTCFTSWSPCFSCAQEMAKFISKNKHVSLCI

FTARIYRRQGRCQEGLRTLAEAGAKISIMTYSEFKHCWDTFVDHQGCPFQPWDGLDE

HSQDLSGRLRAILQ
```

In some embodiments, fusion proteins as provided herein comprise the full-length amino acid of a nucleic acid editing enzyme, e.g., one of the sequences provided above. In other embodiments, however, fusion proteins as provided herein do not comprise a full-length sequence of a nucleic acid editing enzyme, but only a fragment thereof. For example, in some embodiments, a fusion protein provided herein comprises a Cas9 domain and a fragment of a nucleic acid editing enzyme, e.g., wherein the fragment comprises a nucleic acid editing domain. Exemplary amino acid sequences of nucleic acid editing domains are shown in the sequences above as italicized letters, and additional suitable sequences of such domains will be apparent to those of skill in the art.

Additional suitable nucleic-acid editing enzyme sequences, e.g., deaminase enzyme and domain sequences, that can be used according to aspects of this invention, e.g., that can be fused to a nuclease-inactive Cas9 domain, will be apparent to those of skill in the art based on this disclosure. In some embodiments, such additional enzyme sequences include deaminase enzyme or deaminase domain sequences that are at least 70%, at least 75%, at least 80%, at least 85%, at least 90%, at least 95%, at least 96%, at least 97%, at least 98%, or at least 99% similar to the sequences provided herein. Additional suitable Cas9 domains, variants, and sequences will also be apparent to those of skill in the art. Examples of such additional suitable Cas9 domains include, but are not limited to, D10A, D10A/D839A/H840A, and D10A/D839A/H840A/N863A mutant domains (See, e.g., Prashant et al., CAS9 transcriptional activators for target specificity screening and paired nickases for cooperative genome engineering. Nature Biotechnology. 2013; 31(9): 833-838 the entire contents of which are incorporated herein by reference). In some embodiments, the Cas9 comprises a histidine residue at position 840 of the amino acid sequence provided in SEQ ID NO: 10, or a corresponding mutation in any of the amino acid sequences provided in SEQ ID NOs: 11-260. The presence of the catalytic residue H840 restores the activity of the Cas9 to cleave the non-edited strand containing a G opposite the targeted C. Restoration of H840 does not result in the cleavage of the target strand containing the C.

Additional suitable strategies for generating fusion proteins comprising a Cas9 domain and a deaminase domain will be apparent to those of skill in the art based on this disclosure in combination with the general knowledge in the art. Suitable strategies for generating fusion proteins according to aspects of this disclosure using linkers or without the use of linkers will also be apparent to those of skill in the art in view of the instant disclosure and the knowledge in the art. For example, Gilbert et al., CRISPR-mediated modular RNA-guided regulation of transcription in eukaryotes. *Cell.* 2013; 154(2):442-51, showed that C-terminal fusions of Cas9 with VP64 using 2 NLS's as a linker (SPKKKRKVEAS, SEQ ID NO: 599), can be employed for transcriptional activation. Mali et al., CAS9 transcriptional activators for target specificity screening and paired nickases for cooperative genome engineering. *Nat Biotechnol.* 2013; 31(9):833-8, reported that C-terminal fusions with VP64 without linker can be employed for transcriptional activation. And Maeder et al., CRISPR RNA-guided activation of endogenous human genes. *Nat Methods.* 2013; 10: 977-979, reported that C-terminal fusions with VP64 using a Gly$_4$Ser (SEQ ID NO: 5) linker can be used as transcriptional activators. Recently, dCas9-FokI nuclease fusions have successfully been generated and exhibit improved enzymatic specificity as compared to the parental Cas9 enzyme (In Guilinger J P, Thompson D B, Liu D R. Fusion of catalytically inactive Cas9 to FokI nuclease improves the specificity of genome modification. *Nat. Biotechnol.* 2014; 32(6): 577-82, and in Tsai S Q, Wyvekens N, Khayter C, Foden J A, Thapar V, Reyon D, Goodwin M J, Aryee M J, Joung J K. Dimeric CRISPR RNA-guided FokI nucleases for highly specific genome editing. *Nat Biotechnol.* 2014; 32(6):569-76. PMID: 24770325 a SGSETPGTSESATPES (SEQ ID NO: 7) or a GGGGS (SEQ ID NO: 5) linker was used in FokI-dCas9 fusion proteins, respectively).

Some aspects of this disclosure provide fusion proteins comprising (i) a Cas9 enzyme or domain (e.g., a first protein); and (ii) a nucleic acid-editing enzyme or domain (e.g., a second protein). In some aspects, the fusion proteins provided herein further include (iii) a programmable DNA-binding protein, for example, a zinc-finger domain, a TALE, or a second Cas9 protein (e.g., a third protein). Without wishing to be bound by any particular theory, fusing a programmable DNA-binding protein (e.g., a second Cas9 protein) to a fusion protein comprising (i) a Cas9 enzyme or domain (e.g., a first protein); and (ii) a nucleic acid-editing enzyme or domain (e.g., a second protein) may be useful for improving specificity of the fusion protein to a target nucleic acid sequence, or for improving specificity or binding affinity of the fusion protein to bind target nucleic acid sequence that does not contain a canonical PAM (NGG) sequence. In some embodiments, the third protein is a Cas9 protein (e.g., a second Cas9 protein). In some embodiments, the third protein is any of the Cas9 proteins provided herein. In some embodiments, the third protein is fused to the fusion protein N-terminal to the Cas9 protein (e.g., the first protein). In some embodiments, the third protein is fused to the fusion protein C-terminal to the Cas9 protein (e.g., the first protein). In some embodiments, the Cas9 domain (e.g., the first protein) and the third protein (e.g., a second Cas9 protein) are fused via a linker (e.g., a second linker). In some embodiments, the linker comprises a (GGGGS)n (SEQ ID NO: 5), a (G)n, an (EAAAK)n (SEQ ID NO: 6), a (GGS)n, (SGGS)$_n$ (SEQ ID NO: 4288), an SGSETPGTSESATPES (SEQ ID NO: 7), or an (XP)n motif, or a combination of any of these, wherein n is independently an integer between 1 and 30. In some embodiments, the general architecture of exemplary Cas9 fusion proteins provided herein comprises the structure:

[NH2]-[nucleic acid-editing enzyme or domain]-[Cas9]-[third protein]-[COOH];

[NH2]-[third protein]-[Cas9]-[nucleic acid-editing enzyme or domain]-[COOH];

[NH2]-[Cas9]-[nucleic acid-editing enzyme or domain]-[third protein]-[COOH];

[NH2]-[third protein]-[nucleic acid-editing enzyme or domain]-[Cas9]-[COOH];

[NH2]-[UGI]-[nucleic acid-editing enzyme or domain]-[Cas9]-[third protein]-[COOH];

[NH2]-[UGI]-[third protein]-[Cas9]-[nucleic acid-editing enzyme or domain]-[COOH];

[NH2]-[UGI]-[Cas9]-[nucleic acid-editing enzyme or domain]-[third protein]-[COOH];

[NH2]-[UGI]-[third protein]-[nucleic acid-editing enzyme or domain]-[Cas9]-[COOH];

[NH2]-[nucleic acid-editing enzyme or domain]-[Cas9]-[third protein]-[UGI]-[COOH];

[NH2]-[third protein]-[Cas9]-[nucleic acid-editing enzyme or domain]-[UGI]-[COOH];

[NH2]-[Cas9]-[nucleic acid-editing enzyme or domain]-[third protein]-[UGI]-[COOH]; or

[NH2]-[third protein]-[nucleic acid-editing enzyme or domain]-[Cas9]-[UGI]-[COOH];

wherein NH2 is the N-terminus of the fusion protein, and COOH is the C-terminus of the fusion protein. In some embodiments, the "]-[" used in the general architecture above indicates the presence of an optional linker sequence. In other examples, the general architecture of exemplary Cas9 fusion proteins provided herein comprises the structure:

[NH2]-[nucleic acid-editing enzyme or domain]-[Cas9]-[second Cas9 protein]-[COOH];

[NH2]-[second Cas9 protein]-[Cas9]-[nucleic acid-editing enzyme or domain]-[COOH];

[NH2]-[Cas9]-[nucleic acid-editing enzyme or domain]-[second Cas9 protein]-[COOH];

[NH2]-[second Cas9 protein]-[nucleic acid-editing enzyme or domain]-[Cas9]-[COOH];

[NH2]-[UGI]-[nucleic acid-editing enzyme or domain]-[Cas9]-[second Cas9 protein]-[COOH],

[NH2]-[UGI]-[second Cas9 protein]-[Cas9]-[nucleic acid-editing enzyme or domain]-[COOH];
[NH2]-[UGI]-[Cas9]-[nucleic acid-editing enzyme or domain]-[second Cas9 protein]-[COOH];
[NH2]-[UGI]-[second Cas9 protein]-[nucleic acid-editing enzyme or domain]-[Cas9]-[COOH];
[NH2]-[nucleic acid-editing enzyme or domain]-[Cas9]-[second Cas9 protein]-[UGI]-[COOH];
[NH2]-[second Cas9 protein]-[Cas9]-[nucleic acid-editing enzyme or domain]-[UGI]-[COOH];
[NH2]-[Cas9]-[nucleic acid-editing enzyme or domain]-[second Cas9 protein]-[UGI]-[COOH]; or
[NH2]-[second Cas9 protein]-[nucleic acid-editing enzyme or domain]-[Cas9]-[UGI]-[COOH];

wherein NH$_2$ is the N-terminus of the fusion protein, and COOH is the C-terminus of the fusion protein. In some embodiments, the "]-[" used in the general architecture above indicates the presence of an optional linker sequence. In some embodiments, the second Cas9 is a dCas9 protein. In some examples, the general architecture of exemplary Cas9 fusion proteins provided herein comprises a structure as shown in FIG. 3. It should be appreciated that any of the proteins provided in any of the general architectures of exemplary Cas9 fusion proteins may be connected by one or more of the linkers provided herein. In some embodiments, the linkers are the same. In some embodiments, the linkers are different. In some embodiments, one or more of the proteins provided in any of the general architectures of exemplary Cas9 fusion proteins are not fused via a linker. In some embodiments, the fusion proteins further comprise a nuclear targeting sequence, for example a nuclear localization sequence. In some embodiments, fusion proteins provided herein further comprise a nuclear localization sequence (NLS). In some embodiments, the NLS is fused to the N-terminus of the fusion protein. In some embodiments, the NLS is fused to the C-terminus of the fusion protein. In some embodiments, the NLS is fused to the N-terminus of the third protein. In some embodiments, the NLS is fused to the C-terminus of the third protein. In some embodiments, the NLS is fused to the N-terminus of the Cas9 protein. In some embodiments, the NLS is fused to the C-terminus of the Cas9 protein. In some embodiments, the NLS is fused to the N-terminus of the nucleic acid-editing enzyme or domain. In some embodiments, the NLS is fused to the C-terminus of the nucleic acid-editing enzyme or domain. In some embodiments, the NLS is fused to the N-terminus of the UGI protein. In some embodiments, the NLS is fused to the C-terminus of the UGI protein. In some embodiments, the NLS is fused to the fusion protein via one or more linkers. In some embodiments, the NLS is fused to the fusion protein without a linker Uracil Glycosylase Inhibitor Fusion Proteins Some aspects of the disclosure relate to fusion proteins that comprise a uracil glycosylase inhibitor (UGI) domain. In some embodiments, any of the fusion proteins provided herein that comprise a Cas9 domain (e.g., a nuclease active Cas9 domain, a nuclease inactive dCas9 domain, or a Cas9 nickase) may be further fused to a UGI domain either directly or via a linker. Some aspects of this disclosure provide deaminase-dCas9 fusion proteins, deaminase-nuclease active Cas9 fusion proteins and deaminase-Cas9 nickase fusion proteins with increased nucleobase editing efficiency. Without wishing to be bound by any particular theory, cellular DNA-repair response to the presence of U:G heteroduplex DNA may be responsible for the decrease in nucleobase editing efficiency in cells. For example, uracil DNA glycosylase (UDG) catalyzes removal of U from DNA in cells, which may initiate base excision repair, with reversion of the U:G pair to a C:G pair as the most common outcome. As demonstrated in the Examples below, Uracil DNA Glycosylase Inhibitor (UGI) may inhibit human UDG activity. Thus, this disclosure contemplates a fusion protein comprising dCas9-nucleic acid editing domain further fused to a UGI domain. This disclosure also contemplates a fusion protein comprising a Cas9 nickase-nucleic acid editing domain further fused to a UGI domain. It should be understood that the use of a UGI domain may increase the editing efficiency of a nucleic acid editing domain that is capable of catalyzing a C to U change. For example, fusion proteins comprising a UGI domain may be more efficient in deaminating C residues. In some embodiments, the fusion protein comprises the structure:

[deaminase]-[optional linker sequence]-[dCas9]-[optional linker sequence]-[UGI];
[deaminase]-[optional linker sequence]-[UGI]-[optional linker sequence]-[dCas9];
[UGI]-[optional linker sequence]-[deaminase]-[optional linker sequence]-[dCas9];
[UGI]-[optional linker sequence]-[dCas9]-[optional linker sequence]-[deaminase];
[dCas9]-[optional linker sequence]-[deaminase]-[optional linker sequence]-[UGI]; or
[dCas9]-[optional linker sequence]-[UGI]-[optional linker sequence]-[deaminase].

In other embodiments, the fusion protein comprises the structure:

[deaminase]-[optional linker sequence]-[Cas9 nickase]-[optional linker sequence]-[UGI];
[deaminase]-[optional linker sequence]-[UGI]-[optional linker sequence]-[Cas9 nickase];
[UGI]-[optional linker sequence]-[deaminase]-[optional linker sequence]-[Cas9 nickase];
[UGI]-[optional linker sequence]-[Cas9 nickase]-[optional linker sequence]-[deaminase];
[Cas9 nickase]-[optional linker sequence]-[deaminase]-[optional linker sequence]-[UGI]; or
[Cas9 nickase]-[optional linker sequence]-[UGI]-[optional linker sequence]-[deaminase].

In some embodiments, the fusion proteins provided herein do not comprise a linker sequence. In some embodiments, one or both of the optional linker sequences are present.

In some embodiments, the "-" used in the general architecture above indicates the presence of an optional linker sequence. In some embodiments, the fusion proteins comprising a UGI further comprise a nuclear targeting sequence, for example a nuclear localization sequence. In some embodiments, fusion proteins provided herein further comprise a nuclear localization sequence (NLS). In some embodiments, the NLS is fused to the N-terminus of the fusion protein. In some embodiments, the NLS is fused to the C-terminus of the fusion protein. In some embodiments, the NLS is fused to the N-terminus of the UGI protein. In some embodiments, the NLS is fused to the C-terminus of the UGI protein. In some embodiments, the NLS is fused to the N-terminus of the Cas9 protein. In some embodiments, the NLS is fused to the C-terminus of the Cas9 protein. In some embodiments, the NLS is fused to the N-terminus of the deaminase. In some embodiments, the NLS is fused to the C-terminus of the deaminase. In some embodiments, the NLS is fused to the N-terminus of the second Cas9. In some embodiments, the NLS is fused to the C-terminus of the second Cas9. In some embodiments, the NLS is fused to the fusion protein via one or more linkers. In some embodiments, the NLS is fused to the fusion protein without a linker. In some embodiments, the NLS comprises an amino acid sequence of any one of the NLS sequences provided or referenced herein. In some embodiments, the NLS comprises an amino acid sequence as set forth in SEQ ID NO: 741 or SEQ ID NO: 742.

In some embodiments, a UGI domain comprises a wild-type UGI or a UGI as set forth in SEQ ID NO: 600. In some embodiments, the UGI proteins provided herein include fragments of UGI and proteins homologous to a UGI or a UGI fragment. For example, in some embodiments, a UGI domain comprises a fragment of the amino acid sequence set forth in SEQ ID NO: 600. In some embodiments, a UGI fragment comprises an amino acid sequence that comprises at least 60%, at least 65%, at least 70%, at least 75%, at least 80%, at least 85%, at least 90%, at least 95%, at least 96%, at least 97%, at least 98%, at least 99%, or at least 99.5% of the amino acid sequence as set forth in SEQ ID NO: 600. In some embodiments, a UGI comprises an amino acid sequence homologous to the amino acid sequence set forth in SEQ ID NO: 600 or an amino acid sequence homologous to a fragment of the amino acid sequence set forth in SEQ ID NO: 600. In some embodiments, proteins comprising UGI or fragments of UGI or homologs of UGI or UGI fragments are referred to as "UGI variants." A UGI variant shares homology to UGI, or a fragment thereof. For example a UGI variant is at least 70% identical, at least 75% identical, at least 80% identical, at least 85% identical, at least 90% identical, at least 95% identical, at least 96% identical, at least 97% identical, at least 98% identical, at least 99% identical, at least 99.5% identical, or at least 99.9% identical to a wild type UGI or a UGI as set forth in SEQ ID NO: 600. In some embodiments, the UGI variant comprises a fragment of UGI, such that the fragment is at least 70% identical, at least 80% identical, at least 90% identical, at least 95% identical, at least 96% identical, at least 97% identical, at least 98% identical, at least 99% identical, at least 99.5% identical, or at least 99.9% to the corresponding fragment of wild-type UGI or a UGI as set forth in SEQ ID NO: 600. In some embodiments, the UGI comprises the following amino acid sequence:

```
>sp|P14739|UNGI_BPPB2 Uracil-DNA glycosylase
inhibitor
                                  (SEQ ID NO: 600)
MTNLSDIIEKETGKQLVIQESILMLPEEVEEVIGNKPESDILVHTAYDES
TDENVMLLTSDAPEYKPWALVIQDSNGENKIKML
```

Suitable UGI protein and nucleotide sequences are provided herein and additional suitable UGI sequences are known to those in the art, and include, for example, those published in Wang et al., Uracil-DNA glycosylase inhibitor gene of bacteriophage PBS2 encodes a binding protein specific for uracil-DNA glycosylase. J. Biol. Chem. 264: 1163-1171 (1989); Lundquist et al., Site-directed mutagenesis and characterization of uracil-DNA glycosylase inhibitor protein. Role of specific carboxylic amino acids in complex formation with *Escherichia coli* uracil-DNA glycosylase. J. Biol. Chem. 272:21408-21419 (1997); Ravishankar et al., X-ray analysis of a complex of *Escherichia coli* uracil DNA glycosylase (EcUDG) with a proteinaceous inhibitor. The structure elucidation of a prokaryotic UDG. Nucleic Acids Res. 26:4880-4887 (1998); and Putnam et al., Protein mimicry of DNA from crystal structures of the uracil-DNA glycosylase inhibitor protein and its complex with *Escherichia coli* uracil-DNA glycosylase. J. Mol. Biol. 287:331-346 (1999), the entire contents of each are incorporated herein by reference.

It should be appreciated that additional proteins may be uracil glycosylase inhibitors. For example, other proteins that are capable of inhibiting (e.g., sterically blocking) a uracil-DNA glycosylase base-excision repair enzyme are within the scope of this disclosure. Additionally, any proteins that block or inhibit base-excision repair as also within the scope of this disclosure. In some embodiments, a protein that binds DNA is used. In another embodiment, a substitute for UGI is used. In some embodiments, a uracil glycosylase inhibitor is a protein that binds single-stranded DNA. For example, a uracil glycosylase inhibitor may be a *Erwinia tasmaniensis* single-stranded binding protein. In some embodiments, the single-stranded binding protein comprises the amino acid sequence (SEQ ID NO: 322). In some embodiments, a uracil glycosylase inhibitor is a protein that binds uracil. In some embodiments, a uracil glycosylase inhibitor is a protein that binds uracil in DNA. In some embodiments, a uracil glycosylase inhibitor is a catalytically inactive uracil DNA-glycosylase protein. In some embodiments, a uracil glycosylase inhibitor is a catalytically inactive uracil DNA-glycosylase protein that does not excise uracil from the DNA. For example, a uracil glycosylase inhibitor is a UdgX. In some embodiments, the UdgX comprises the amino acid sequence (SEQ ID NO: 323). As another example, a uracil glycosylase inhibitor is a catalytically inactive UDG. In some embodiments, a catalytically inactive UDG comprises the amino acid sequence (SEQ ID NO: 324). It should be appreciated that other uracil glycosylase inhibitors would be apparent to the skilled artisan and are within the scope of this disclosure. In some embodiments, a uracil glycosylase inhibitor is a protein that is homologous to any one of SEQ ID NOs: 322-324. In some embodiments, a uracil glycosylase inhibitor is a protein that is at least 50% identical, at least 55% identical at least 60% identical, at least 65% identical, at least 70% identical, at least 75% identical, at least 80% identical at least 85% identical, at least 90% identical, at least 95% identical, at least 96% identical, at least 98% identical, at least 99% identical, or at least 99.5% identical to any one of SEQ ID NOs: 322-324.

```
Erwinia tasmaniensis SSB (themostable single-
stranded DNA binding protein)
                                  (SEQ ID NO: 322)
MASRGVNKVILVGNLGQDPEVRYMPNGGAVANITLATSESWRDKQTGETK

EKTEWHRVVLFGKLAEVAGEYLRKGSQVYIEGALQTRKWTDQAGVEKYTT

EVVVNVGGTMQMLGGRSQGGGASAGGQNGGSNNGWGQPQQPQGGNQFSGG

AQQQARPQQQPQQNNAPANNEPPIDFDDDIP

UdgX (binds to Uracil in DNA but does not excise)
                                  (SEQ ID NO: 323)
MAGAQDFVPHTADLAELAAAAGECRGCGLYRDATQAVFGAGGRSARIMMI

GEQPGDKEDLAGLPFVGPAGRLLDRALEAADIDRDALYVTNAVKHFKFTR

AAGGKRRIHKTPSRTEVVACRPWLIAEMTSVEPDVVVLLGATAAKALLGN

DFRVTQHRGEVLHVDDVPGDPALVATVHPSSLLRGPKEERESAFAGLVDD

LRVAADVRP

UDG (catalytically inactive human UDG, binds to
Uracil in DNA but does not excise)
                                  (SEQ ID NO: 324)
MIGQKTLYSFFSPSPARKRHAPSPEPAVQGTGVAGVPEESGDAAAIPAKK

APAGQEEPGTPPSSPLSAEQLDRIQRNKAAALLRLAARNVPVGFGESWKK
```

```
-continued
HLSGEFGKPYFIKLMGFVAEERKHYTVYPPPHQVFTWTQMCDIKDVKVVI

LGQEPYHGPNQAHGLCFSVQRPVPPPPSLENIYKELSTDIEDFVHPGHGD

LSGWAKQGVLLLNAVLTVRAHQANSHKERGWEQFTDAVVSWLNQNSNGLV

FLLWGSYAQKKGSAIDRKRHHVLQTAHPSPLSVYRGFFGCRHFSKTNELL

QKSGKKPIDWKEL
```

In some embodiments, the nucleic acid editing domain is a deaminase domain. In some embodiments, the deaminase is a cytosine deaminase or a cytidine deaminase. In some embodiments, the deaminase is an apolipoprotein B mRNA-editing complex (APOBEC) family deaminase. In some embodiments, the deaminase is an APOBEC1 deaminase. In some embodiments, the deaminase is an APOBEC2 deaminase. In some embodiments, the deaminase is an APOBEC3 deaminase. In some embodiments, the deaminase is an APOBEC3A deaminase. In some embodiments, the deaminase is an APOBEC3B deaminase. In some embodiments, the deaminase is an APOBEC3C deaminase. In some embodiments, the deaminase is an APOBEC3D deaminase. In some embodiments, the deaminase is an APOBEC3E deaminase. In some embodiments, the deaminase is an APOBEC3F deaminase. In some embodiments, the deaminase is an APOBEC3G deaminase. In some embodiments, the deaminase is an APOBEC3H deaminase. In some embodiments, the deaminase is an APOBEC4 deaminase. In some embodiments, the deaminase is an activation-induced deaminase (AID). In some embodiments, the demianse is a rat APOBEC1 (SEQ ID NO: 282). In some embodiments, the deminase is a human APOBEC1 (SEQ ID No: 284). In some embodiments, the deaminase is a *Petromyzon marinus* cytidine deaminase 1 (pmCDA1). In some embodiments, the deminase is a human APOBEC3G (SEQ ID NO: 275). In some embodiments, the deaminase is a fragment of the human APOBEC3G (SEQ ID NO: 5740). In some embodiments, the deaminase is a human APOBEC3G variant comprising a D316R_D317R mutation (SEQ ID NO: 5739). In some embodiments, the deaminase is a frantment of the human APOBEC3G and comprising mutations corresponding to the D316R_D317R mutations in SEQ ID NO: 275 (SEQ ID NO: 5741).

In some embodiments, the linker comprises a (GGGS)$_n$ (SEQ ID NO: 265), (GGGGS)$_n$ (SEQ ID NO: 5), a (G)$_n$, an (EAAAK)$_n$ (SEQ ID NO: 6), a (GGS)$_n$, an SGSETPGTS-ESATPES (SEQ ID NO: 7), or an (XP)$_n$ motif, or a combination of any of these, wherein n is independently an integer between 1 and 30.

Suitable UGI protein and nucleotide sequences are provided herein and additional suitable UGI sequences are known to those in the art, and include, for example, those published in Wang et al., Uracil-DNA glycosylase inhibitor gene of bacteriophage PBS2 encodes a binding protein specific for uracil-DNA glycosylase. *J. Biol. Chem.* 264: 1163-1171 (1989); Lundquist et al., Site-directed mutagenesis and characterization of uracil-DNA glycosylase inhibitor protein. Role of specific carboxylic amino acids in complex formation with *Escherichia coli* uracil-DNA glycosylase. *J. Biol. Chem.* 272:21408-21419 (1997); Ravishankar et al., X-ray analysis of a complex of *Escherichia coli* uracil DNA glycosylase (EcUDG) with a proteinaceous inhibitor. The structure elucidation of a prokaryotic UDG. *Nucleic Acids Res.* 26:4880-4887 (1998); and Putnam et al., Protein mimicry of DNA from crystal structures of the uracil-DNA glycosylase inhibitor protein and its complex with *Escherichia coli* uracil-DNA glycosylase. *J. Mol. Biol.* 287:331-346 (1999), the entire contents of which are incorporated herein by reference. In some embodiments, the optional linker comprises a (GGS)$_n$ motif, wherein n is 1, 2, 3, 4, 5, 6, 7, 8, 9, 19, 11, 12, 13, 14, 15, 16, 17, 18, 19, or 20. In some embodiments, the optional linker comprises a (GGS)n motif, wherein n is 1, 3, or 7. In some embodiments, the optional linker comprises the amino acid sequence SGSETPGTSESATPES (SEQ ID NO: 7), which is also referred to as the XTEN linker in the Examples.

In some embodiments, a Cas9 nickase may further facilitate the removal of a base on the non-edited strand in an organism whose genome is edited in vivo. The Cas9 nickase, as described herein, may comprise a D10A mutation in SEQ ID NO: 10, or a corresponding mutation in any of SEQ ID NOs: 11-260. In some embodiments, the Cas9 nickase of this disclosure may comprise a histidine at mutation 840 of SEQ ID NO: 10, or a corresponding residue in any of SEQ ID NOs: 11-260. Such fusion proteins comprising the Cas9 nickase, can cleave a single strand of the target DNA sequence, e.g., the strand that is not being edited. Without wishing to be bound by any particular theory, this cleavage may inhibit mis-match repair mechanisms that reverse a C to U edit made by the deaminase.

Cas9 Complexes with Guide RNAs

Some aspects of this disclosure provide complexes comprising any of the fusion proteins provided herein, and a guide RNA bound to a Cas9 domain (e.g., a dCas9, a nuclease active Cas9, or a Cas9 nickase) of fusion protein.

In some embodiments, the guide RNA is from 15-100 nucleotides long and comprises a sequence of at least 10 contiguous nucleotides that is complementary to a target sequence. In some embodiments, the guide RNA is 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides long. In some embodiments, the guide RNA comprises a sequence of 15, 16, 17, 18, 19, 20, 21, 22, 23, 24, 25, 26, 27, 28, 29, 30, 31, 32, 33, 34, 35, 36, 37, 38, 39, or 40 contiguous nucleotides that is complementary to a target sequence. In some embodiments, the target sequence is a DNA sequence. In some embodiments, the target sequence is a sequence in the genome of a mammal. In some embodiments, the target sequence is a sequence in the genome of a human. In some embodiments, the 3' end of the target sequence is immediately adjacent to a canonical PAM sequence (NGG). In some embodiments, the guide RNA is complementary to a sequence associated with a disease or disorder. In some embodiments, the guide RNA is complementary to a sequence associated with a disease or disorder having a mutation in a gene selected from the genes disclosed in any one of Tables 1-3. In some embodiments, the guide RNA comprises a nucleotide sequence of any one of the guide sequences provided in Table 2 or Table 3. Exemplary sequences in the human genome that may be targeted by the complexes of this disclosure are provided herein in Tables 1-3.

Methods of Using Cas9 Fusion Proteins

Some aspects of this disclosure provide methods of using the Cas9 proteins, fusion proteins, or complexes provided herein. For example, some aspects of this disclosure provide methods comprising contacting a DNA molecule (a) with any of the the Cas9 proteins or fusion proteins provided herein, and with at least one guide RNA, wherein the guide RNA is about 15-100 nucleotides long and comprises a sequence of at least 10 contiguous nucleotides that is complementary to a target sequence; or (b) with a Cas9 protein, a Cas9 fusion protein, or a Cas9 protein or fusion protein complex with at least one gRNA as provided herein.

In some embodiments, the 3' end of the target sequence is not immediately adjacent to a canonical PAM sequence (NGG). In some embodiments, the 3' end of the target sequence is immediately adjacent to an AGC, GAG, TTT, GTG, or CAA sequence.

In some embodiments, the target DNA sequence comprises a sequence associated with a disease or disorder. In some embodiments, the target DNA sequence comprises a point mutation associated with a disease or disorder. In some embodiments, the activity of the Cas9 protein, the Cas9 fusion protein, or the complex results in a correction of the point mutation. In some embodiments, the target DNA sequence comprises a T→C point mutation associated with a disease or disorder, and wherein the deamination of the mutant C base results in a sequence that is not associated with a disease or disorder. In some embodiments, the target DNA sequence encodes a protein and wherein the point mutation is in a codon and results in a change in the amino acid encoded by the mutant codon as compared to the wild-type codon. In some embodiments, the deamination of the mutant C results in a change of the amino acid encoded by the mutant codon. In some embodiments, the deamination of the mutant C results in the codon encoding the wild-type amino acid. In some embodiments, the contacting is in vivo in a subject. In some embodiments, the subject has or has been diagnosed with a disease or disorder. In some embodiments, the disease or disorder is cystic fibrosis, phenylketonuria, epidermolytic hyperkeratosis (EHK), Charcot-Marie-Toot disease type 4J, neuroblastoma (NB), von Willebrand disease (vWD), myotonia congenital, hereditary renal amyloidosis, dilated cardiomyopathy (DCM), hereditary lymphedema, familial Alzheimer's disease, HIV, Prion disease, chronic infantile neurologic cutaneous articular syndrome (CINCA), desmin-related myopathy (DRM), a neoplastic disease associated with a mutant PI3KCA protein, a mutant CTNNB1 protein, a mutant HRAS protein, or a mutant p53 protein.

Some embodiments provide methods for using the Cas9 DNA editing fusion proteins provided herein. In some embodiments, the fusion protein is used to introduce a point mutation into a nucleic acid by deaminating a target nucleobase, e.g., a C residue. In some embodiments, the deamination of the target nucleobase results in the correction of a genetic defect, e.g., in the correction of a point mutation that leads to a loss of function in a gene product. In some embodiments, the genetic defect is associated with a disease or disorder, e.g., a lysosomal storage disorder or a metabolic disease, such as, for example, type I diabetes. In some embodiments, the methods provided herein are used to introduce a deactivating point mutation into a gene or allele that encodes a gene product that is associated with a disease or disorder. For example, in some embodiments, methods are provided herein that employ a Cas9 DNA editing fusion protein to introduce a deactivating point mutation into an oncogene (e.g., in the treatment of a proliferative disease). A deactivating mutation may, in some embodiments, generate a premature stop codon in a coding sequence, which results in the expression of a truncated gene product, e.g., a truncated protein lacking the function of the full-length protein.

In some embodiments, the purpose of the methods provide herein is to restore the function of a dysfunctional gene via genome editing. The Cas9 deaminase fusion proteins provided herein can be validated for gene editing-based human therapeutics in vitro, e.g., by correcting a disease-associated mutation in human cell culture. It will be understood by the skilled artisan that the fusion proteins provided herein, e.g., the fusion proteins comprising a Cas9 domain and a nucleic acid deaminase domain can be used to correct any single point T→C or A→G mutation. In the first case, deamination of the mutant C back to U corrects the mutation, and in the latter case, deamination of the C that is base-paired with the mutant G, followed by a round of replication, corrects the mutation.

An exemplary disease-relevant mutation that can be corrected by the provided fusion proteins in vitro or in vivo is the H1047R (A3140G) polymorphism in the PI3KCA protein. The phosphoinositide-3-kinase, catalytic alpha subunit (PI3KCA) protein acts to phosphorylate the 3-OH group of the inositol ring of phosphatidylinositol. The PI3KCA gene has been found to be mutated in many different carcinomas, and thus it is considered to be a potent oncogene.[37] In fact, the A3140G mutation is present in several NCI-60 cancer cell lines, such as, for example, the HCT116, SKOV3, and T47D cell lines, which are readily available from the American Type Culture Collection (ATCC).[38]

In some embodiments, a cell carrying a mutation to be corrected, e.g., a cell carrying a point mutation, e.g., an A3140G point mutation in exon 20 of the PI3KCA gene, resulting in a H1047R substitution in the PI3KCA protein, is contacted with an expression construct encoding a Cas9 deaminase fusion protein and an appropriately designed sgRNA targeting the fusion protein to the respective mutation site in the encoding PI3KCA gene. Control experiments can be performed where the sgRNAs are designed to target the fusion enzymes to non-C residues that are within the PI3KCA gene. Genomic DNA of the treated cells can be extracted, and the relevant sequence of the PI3KCA genes PCR amplified and sequenced to assess the activities of the fusion proteins in human cell culture.

It will be understood that the example of correcting point mutations in PI3KCA is provided for illustration purposes and is not meant to limit the instant disclosure. The skilled artisan will understand that the instantly disclosed DNA-editing fusion proteins can be used to correct other point mutations and mutations associated with other cancers and with diseases other than cancer including other proliferative diseases.

The successful correction of point mutations in disease-associated genes and alleles opens up new strategies for gene correction with applications in therapeutics and basic research. Site-specific single-base modification systems like the disclosed fusions of Cas9 and deaminase enzymes or domains also have applications in "reverse" gene therapy, where certain gene functions are purposely suppressed or abolished. In these cases, site-specifically mutating Trp (TGG), Gln (CAA and CAG), or Arg (CGA) residues to premature stop codons (TAA, TAG, TGA) can be used to abolish protein function in vitro, ex vivo, or in vivo.

The instant disclosure provides methods for the treatment of a subject diagnosed with a disease associated with or caused by a point mutation that can be corrected by a Cas9 DNA editing fusion protein provided herein. For example, in some embodiments, a method is provided that comprises administering to a subject having such a disease, e.g., a cancer associated with a PI3KCA point mutation as described above, an effective amount of a Cas9 deaminase fusion protein that corrects the point mutation or introduces a deactivating mutation into the disease-associated gene. In some embodiments, the disease is a proliferative disease. In some embodiments, the disease is a genetic disease. In some embodiments, the disease is a neoplastic disease. In some embodiments, the disease is a metabolic disease. In some embodiments, the disease is a lysosomal storage disease. Other diseases that can be treated by correcting a point mutation or introducing a deactivating mutation into a disease-associated gene will be known to those of skill in the art, and the disclosure is not limited in this respect.

The instant disclosure provides methods for the treatment of additional diseases or disorders, e.g., diseases or disorders that are associated or caused by a point mutation that can be corrected by deaminase-mediated gene editing. Some such diseases are described herein, and additional suitable diseases that can be treated with the strategies and fusion proteins provided herein will be apparent to those of skill in the art based on the instant disclosure. Exemplary suitable diseases and disorders are listed below. It will be understood that the numbering of the specific positions or residues in the respective sequences depends on the particular protein and numbering scheme used. Numbering might be different, e.g., in precursors of a mature protein and the mature protein itself, and differences in sequences from species to species may affect numbering. One of skill in the art will be able to identify the respective residue in any homologous protein and in the respective encoding nucleic acid by methods well known in the art, e.g., by sequence alignment and determination of homologous residues. Exemplary suitable diseases and disorders include, without limitation, cystic fibrosis (see, e.g., Schwank et al., Functional repair of CFTR by CRISPR/Cas9 in intestinal stem cell organoids of cystic fibrosis patients. *Cell stem cell*. 2013; 13: 653-658; and Wu et. al., Correction of a genetic disease in mouse via use of CRISPR-Cas9. *Cell stem cell*. 2013; 13: 659-662, neither of which uses a deaminase fusion protein to correct the genetic defect); phenylketonuria—e.g., phenylalanine to serine mutation at position 835 (mouse) or 240 (human) or a homologous residue in phenylalanine hydroxylase gene (T>C mutation)—see, e.g., McDonald et al., *Genomics*. 1997; 39:402-405; Bernard-Soulier syndrome (BSS)—e.g., phenylalanine to serine mutation at position 55 or a homologous residue, or cysteine to arginine at residue 24 or a homologous residue in the platelet membrane glycoprotein IX (T>C mutation)—see, e.g., Noris et al., *British Journal of Haematology*. 1997; 97: 312-320, and Ali et al., *Hematol*. 2014; 93: 381-384; epidermolytic hyperkeratosis (EHK)—e.g., leucine to proline mutation at position 160 or 161 (if counting the initiator methionine) or a homologous residue in keratin 1 (T>C mutation)—see, e.g., Chipev et al., *Cell*. 1992; 70: 821-828, see also accession number P04264 in the UNIPROT database at www[dot]uniprot[dot]org; chronic obstructive pulmonary disease (COPD)—e.g., leucine to proline mutation at position 54 or 55 (if counting the initiator methionine) or a homologous residue in the processed form of $\alpha_1$-antitrypsin or residue 78 in the unprocessed form or a homologous residue (T>C mutation)—see, e.g., Poller et al., *Genomics*. 1993; 17: 740-743, see also accession number P01011 in the UNIPROT database; Charcot-Marie-Toot disease type 4J—e.g., isoleucine to threonine mutation at position 41 or a homologous residue in FIG4 (T>C mutation)—see, e.g., Lenk et al., *PLoS Genetics*. 2011; 7: e1002104; neuroblastoma (NB)—e.g., leucine to proline mutation at position 197 or a homologous residue in Caspase-9 (T>C mutation)—see, e.g., Kundu et al., 3 *Biotech*. 2013, 3:225-234; von Willebrand disease (vWD)—e.g., cysteine to arginine mutation at position 509 or a homologous residue in the processed form of von Willebrand factor, or at position 1272 or a homologous residue in the unprocessed form of von Willebrand factor (T>C mutation)—see, e.g., Lavergne et al., *Br. J. Haematol*. 1992, see also accession number P04275 in the UNIPROT database; 82: 66-72; myotonia congenital—e.g., cysteine to arginine mutation at position 277 or a homologous residue in the muscle chloride channel gene CLCN1 (T>C mutation)—see, e.g., Weinberger et al., *The J. of Physiology*. 2012; 590: 3449-3464; hereditary renal amyloidosis—e.g., stop codon to arginine mutation at position 78 or a homologous residue in the processed form of apolipoprotein AII or at position 101 or a homologous residue in the unprocessed form (T>C mutation)—see, e.g., Yazaki et al., *Kidney Int*. 2003; 64: 11-16; dilated cardiomyopathy (DCM)—e.g., tryptophan to Arginine mutation at position 148 or a homologous residue in the FOXD4 gene (T>C mutation), see, e.g., Minoretti et. al., *Int. J. of Mol. Med*. 2007; 19: 369-372; hereditary lymphedema—e.g., histidine to arginine mutation at position 1035 or a homologous residue in VEGFR3 tyrosine kinase (A>G mutation), see, e.g., Irrthum et al., *Am. J. Hum. Genet*. 2000; 67: 295-301; familial Alzheimer's disease—e.g., isoleucine to valine mutation at position 143 or a homologous residue in presenilin1 (A>G mutation), see, e.g., Gallo et. al., *J. Alzheimer's disease*. 2011; 25: 425-431; Prion disease—e.g., methionine to valine mutation at position 129 or a homologous residue in prion protein (A>G mutation)—see, e.g., Lewis et. al., *J. of General Virology*. 2006; 87: 2443-2449; chronic infantile neurologic cutaneous articular syndrome (CINCA)—e.g., Tyrosine to Cysteine mutation at position 570 or a homologous residue in cryopyrin (A>G mutation)—see, e.g., Fujisawa et. al. *Blood*. 2007; 109: 2903-2911; and desmin-related myopathy (DRM)—e.g., arginine to glycine mutation at position 120 or a homologous residue in $\alpha\beta$ crystallin (A>G mutation)—see, e.g., Kumar et al., *J. Biol. Chem*. 1999; 274: 24137-24141. The entire contents of all references and database entries is incorporated herein by reference.

The instant disclosure provides lists of genes comprising pathogenic T>C or A>G mutations. Provided herein, are the names of these genes, their respective SEQ ID NOs, their gene IDs, and sequences flanking the mutation site. (Tables 2 and 3). In some instances, the gRNA sequences that can be used to correct the mutations in these genes are disclosed (Tables 2 and 3).

In some embodiments, a Cas9-deaminase fusion protein recognizes canonical PAMs and therefore can correct the pathogenic T>C or A>G mutations with canonical PAMs, e.g., NGG (listed in Tables 2 and 3, SEQ ID NOs: 2540-2702 and 5084-5260), respectively, in the flanking sequences. For example, the Cas9 proteins that recognize canonical PAMs comprise an amino acid sequence that is at least 90% identical to the amino acid sequence of *Streptococcus pyogenes* Cas9 as provided by SEQ ID NO: 10, or to a fragment thereof comprising the RuvC and HNH domains of SEQ ID NO: 10.

It will be apparent to those of skill in the art that in order to target a Cas9:nucleic acid editing enzyme/domain fusion protein as disclosed herein to a target site, e.g., a site comprising a point mutation to be edited, it is typically necessary to co-express the Cas9:nucleic acid editing enzyme/domain fusion protein together with a guide RNA, e.g., an sgRNA. As explained in more detail elsewhere herein, a guide RNA typically comprises a tracrRNA framework allowing for Cas9 binding, and a guide sequence, which confers sequence specificity to the Cas9:nucleic acid editing enzyme/domain fusion protein. In some embodiments, the guide RNA comprises a structure 5'-[guide sequence]-guuuuagagcuagaaauagcaaguuaaaauaaaggcuagu-ccguuaucaacuugaaaaaguggcaccgagucggugcuuuuu-3' (SEQ ID NO: 601), wherein the guide sequence comprises a sequence that is complementary to the target sequence. The guide sequence is typically 20 nucleotides long. The sequences of suitable guide RNAs for targeting Cas9:nucleic acid editing enzyme/domain fusion proteins to specific genomic target sites will be apparent to those of skill in the art based on the instant disclosure. Such suitable guide RNA sequences typically comprise guide sequences that are complementary to a nucleic acid sequence within 50 nucleotides upstream or downstream of the target nucleotide to be edited. Some exemplary guide RNA sequences suitable for targeting Cas9:nucleic acid editing enzyme/domain fusion proteins to specific target sequences are provided below.

Base Editor Efficiency

Some aspects of the disclosure are based on the recognition that any of the base editors provided herein are capable of modifying a specific nucleotide base without generating a significant proportion of indels. An "indel", as used herein, refers to the insertion or deletion of a nucleotide base within a nucleic acid. Such insertions or deletions can lead to frame shift mutations within a coding region of a gene. In some embodiments, it is desirable to generate base editors that efficiently modify (e.g. mutate or deaminate) a specific nucleotide within a nucleic acid, without generating a large number of insertions or deletions (i.e., indels) in the nucleic acid. In certain embodiments, any of the base editors provided herein are capable of generating a greater proportion of intended modifications (e.g., point mutations or deaminations) versus indels. In some embodiments, the base editors provided herein are capable of generating a ratio of intended point mutations to indels that is greater than 1:1. In some embodiments, the base editors provided herein are capable of generating a ratio of intended point mutations to indels that is at least 1.5:1, at least 2:1, at least 2.5:1, at least 3:1, at least 3.5:1, at least 4:1, at least 4.5:1, at least 5:1, at least 5.5:1, at least 6:1, at least 6.5:1, at least 7:1, at least 7.5:1, at least 8:1, at least 10:1, at least 12:1, at least 15:1, at least 20:1, at least 25:1, at least 30:1, at least 40:1, at least 50:1, at least 100:1, at least 200:1, at least 300:1, at least 400:1, at least 500:1, at least 600:1, at least 700:1, at least 800:1, at least 900:1, or at least 1000:1, or more. The number of intended mutations and indels may be determined using any suitable method, for example the methods used in the below Examples.

In some embodiments, the base editors provided herein are capable of limiting formation of indels in a region of a nucleic acid. In some embodiments, the region is at a nucleotide targeted by a base editor or a region within 2, 3, 4, 5, 6, 7, 8, 9, or 10 nucleotides of a nucleotide targeted by a base editor. In some embodiments, any of the base editors provided herein are capable of limiting the formation of indels at a region of a nucleic acid to less than 1%, less than 1.5%, less than 2%, less than 2.5%, less than 3%, less than 3.5%, less than 4%, less than 4.5%, less than 5%, less than 6%, less than 7%, less than 8%, less than 9%, less than 10%, less than 12%, less than 15%, or less than 20%. The number of indels formed at a nucleic acid region may depend on the amount of time a nucleic acid (e.g., a nucleic acid within the genome of a cell) is exposed to a base editor. In some embodiments, an number or proportion of indels is determined after at least 1 hour, at least 2 hours, at least 6 hours, at least 12 hours, at least 24 hours, at least 36 hours, at least 48 hours, at least 3 days, at least 4 days, at least 5 days, at least 7 days, at least 10 days, or at least 14 days of exposing a nucleic acid (e.g., a nucleic acid within the genome of a cell) to a base editor.

Some aspects of the disclosure are based on the recognition that any of the base editors provided herein are capable of efficiently generating an intended mutation, such as a point mutation, in a nucleic acid (e.g. a nucleic acid within a genome of a subject) without generating a significant number of unintended mutations, such as unintended point mutations. In some embodiments, a intended mutation is a mutation that is generated by a specific base editor bound to a gRNA, specifically designed to generate the intended mutation. In some embodiments, the intended mutation is a mutation associated with a disease or disorder. In some embodiments, the intended mutation is a cytosine (C) to thymine (T) point mutation associated with a disease or disorder. In some embodiments, the intended mutation is a guanine (G) to adenine (A) point mutation associated with a disease or disorder. In some embodiments, the intended mutation is a cytosine (C) to thymine (T) point mutation within the coding region of a gene. In some embodiments, the intended mutation is a guanine (G) to adenine (A) point mutation within the coding region of a gene. In some embodiments, the intended mutation is a point mutation that generates a stop codon, for example, a premature stop codon within the coding region of a gene. In some embodiments, the intended mutation is a mutation that eliminates a stop codon. In some embodiments, the intended mutation is a mutation that alters the splicing of a gene. In some embodiments, the intended mutation is a mutation that alters the regulatory sequence of a gene (e.g., a gene promotor or gene repressor). In some embodiments, any of the base editors provided herein are capable of generating a ratio of intended mutations to unintended mutations (e.g., intended point mutations:unintended point mutations) that is greater than 1:1. In some embodiments, any of the base editors provided herein are capable of generating a ratio of intended mutations to unintended mutations (e.g., intended point mutations:unintended point mutations) that is at least 1.5:1, at least 2:1, at least 2.5:1, at least 3:1, at least 3.5:1, at least 4:1, at least 4.5:1, at least 5:1, at least 5.5:1, at least 6:1, at least 6.5:1, at least 7:1, at least 7.5:1, at least 8:1, at least 10:1, at least 12:1, at least 15:1, at least 20:1, at least 25:1, at least 30:1, at least 40:1, at least 50:1, at least 100:1, at least 150:1, at least 200:1, at least 250:1, at least 500:1, or at least 1000:1, or more. It should be appreciated that the characterstics of the base editors described in the "Base Editor Efficiency" section, herein, may be applied to any of the fusion proteins, or methods of using the fusion proteins provided herein.

Methods for Editing Nucleic Acids

Some aspects of the disclosure provide methods for editing a nucleic acid. In some embodiments, the method is a method for editing a nucleobase of a nucleic acid (e.g., a base pair of a double-stranded DNA sequence). In some embodiments, the method comprises the steps of: a) contacting a target region of a nucleic acid (e.g., a double-stranded DNA sequence) with a complex comprising a base editor (e.g., a Cas9 domain fused to a cytidine deaminase domain) and a guide nucleic acid (e.g., gRNA), wherein the target region comprises a targeted nucleobase pair, b) inducing strand separation of said target region, c) converting a first nucleobase of said target nucleobase pair in a single strand of the target region to a second nucleobase, and d) cutting no more than one strand of said target region, where a third nucleobase complementary to the first nucleobase base is replaced by a fourth nucleobase complementary to the second nucleobase; and the method results in less than 20% indel formation in the nucleic acid. It should be appreciated that in some embodiments, step b is omitted. In some embodiments, the first nucleobase is a cytosine. In some embodiments, the second nucleobase is a deaminated cytosine, or a uracil. In some embodiments, the third nucleobase is a guanine. In some embodiments, the fourth nucleobase is an adenine. In some embodiments, the first nucleobase is a cytosine, the second nucleobase is a deaminated cytosine, or a uracil, the third nucleobase is a guanine, and the fourth nucleobase is an adenine. In some embodiments, the method results in less than 19%, 18%, 16%, 14%, 12%, 10%, 8%, 6%, 4%, 2%, 1%, 0.5%, 0.2%, or less than 0.1% indel formation. In some embodiments, the method further comprises replacing the second nucleobase with a fifth nucleobase that is complementary to the fourth nucleobase, thereby generating an intended edited base pair (e.g., C:G→T:A). In some embodiments, the fifth nucleobase is a thymine. In some embodiments, at least 5% of the intended basepaires are edited. In some embodiments, at least 10%, 15%, 20%, 25%, 30%, 35%, 40%, 45%, or 50% of the intended basepaires are edited.

In some embodiments, the ratio of intended products to unintended products in the target nucleotide is at least 2:1, 5:1, 10:1, 20:1, 30:1, 40:1, 50:1, 60:1, 70:1, 80:1, 90:1, 100:1, or 200:1, or more. In some embodiments, the ratio of intended point mutation to indel formation is greater than 1:1, 10:1, 50:1, 100:1, 500:1, or 1000:1, or more. In some embodiments, the cut single strand (nicked strand) is hybridized to the guide nucleic acid. In some embodiments, the cut single strand is opposite to the strand comprising the first nucleobase. In some embodiments, the base editor comprises a Cas9 domain. In some embodiments, the first base is cytosine, and the second base is not a G, C, A, or T. In some embodiments, the second base is uracil. In some embodiments, the first base is cytosine. In some embodiments, the second base is not a G, C, A, or T. In some embodiments, the second base is uracil. In some embodiments, the base editor inhibits base escision repair of the edited strand. In some embodiments, the base editor protects or binds the non-edited strand. In some embodiments, the base editor comprises UGI activity. In some embodiments, the base editor comprises nickase activity. In some embodiments, the intended edited basepair is upstream of a PAM site. In some embodiments, the intended edited base pair is 1, 2, 3, 4, 5, 6, 7, 8, 9, 10, 11, 12, 13, 14, 15, 16, 17, 18, 19, or 20 nucleotides upstream of the PAM site. In some embodiments, the intended edited basepair is downstream of a PAM site. In some embodiments, the intended edited base pair is 1, 2, 3, 4, 5, 6, 7, 8, 9, 10, 11, 12, 13, 14, 15, 16, 17, 18, 19, or 20 nucleotides downstream stream of the PAM site. In some embodiments, the method does not require a canonical (e.g., NGG) PAM site. In some embodiments, the nucleobase editor comprises a linker. In some embodiments, the linker is 1-25 amino acids in length. In some embodiments, the linker is 5-20 amino acids in length. In some embodiments, linker is 10, 11, 12, 13, 14, 15, 16, 17, 18, 19, or 20 amino acids in length. In some embodiments, the target region comprises a target window, wherein the target window comprises the target nucleobase pair. In some embodiments, the target window comprises 1-10 nucleotides. In some embodiments, the target window is 1-9, 1-8, 1-7, 1-6, 1-5, 1-4, 1-3, 1-2, or 1 nucleotides in length. In some embodiments, the target window is 1, 2, 3, 4, 5, 6, 7, 8, 9, 10, 11, 12, 13, 14, 15, 16, 17, 18, 19, or 20 nucleotides in length. In some embodiments, the intended edited base pair is within the target window. In some embodiments, the target window comprises the intended edited base pair. In some embodiments, the method is performed using any of the base editors provided herein. In some embodiments, a target window is a deamination window In some embodiments, the disclosure provides methods for editing a nucleotide. In some embodiments, the disclosure provides a method for editing a nucleobase pair of a double-stranded DNA sequence. In some embodiments, the method comprises a) contacting a target region of the double-stranded DNA sequence with a complex comprising a base editor and a guide nucleic acid (e.g., gRNA), where the target region comprises a target nucleobase pair, b) inducing strand separation of said target region, c) converting a first nucleobase of said target nucleobase pair in a single strand of the target region to a second nucleobase, d) cutting no more than one strand of said target region, wherein a third nucleobase complementary to the first nucleobase base is replaced by a fourth nucleobase complementary to the second nucleobase, and the second nucleobase is replaced with a fifth nucleobase that is complementary to the fourth nucleobase, thereby generating an intended edited basepair, wherein the efficiency of generating the intended edited basepair is at least 5%. It should be appreciated that in some embodiments, step b is omitted. In some embodiments, at least 5% of the intended basepaires are edited. In some embodiments, at least 10%, 15%, 20%, 25%, 30%, 35%, 40%, 45%, or 50% of the intended basepaires are edited. In some embodiments, the method causes less than 19%, 18%, 16%, 14%, 12%, 10%, 8%, 6%, 4%, 2%, 1%, 0.5%, 0.2%, or less than 0.1% indel formation. In some embodiments, the ratio of intended product to unintended products at the target nucleotide is at least 2:1, 5:1, 10:1, 20:1, 30:1, 40:1, 50:1, 60:1, 70:1, 80:1, 90:1, 100:1, or 200:1, or more. In some embodiments, the ratio of intended point mutation to indel formation is greater than 1:1, 10:1, 50:1, 100:1, 500:1, or 1000:1, or more. In some embodiments, the cut single strand is hybridized to the guide nucleic acid. In some embodiments, the cut single strand is opposite to the strand comprising the first nucleobase. In some embodiments, the first base is cytosine. In some embodiments, the second nucleobase is not G, C, A, or T. In some embodiments, the second base is uracil. In some embodiments, the base editor inhibits base escision repair of the edited strand. In some embodiments, the base editor protects or binds the non-edited strand. In some embodiments, the nucleobase editor comprises UGI activity. In some embodiments, the nucleobase edit comprises nickase activity. In some embodiments, the intended edited basepair is upstream of a PAM site. In some embodiments, the intended edited base pair is 1, 2, 3, 4, 5, 6, 7, 8, 9, 10, 11, 12, 13, 14, 15, 16, 17, 18, 19, or 20 nucleotides upstream of the PAM site. In some embodiments, the intended edited basepair is downstream of a PAM site. In some embodiments, the intended edited base pair is 1, 2, 3, 4, 5, 6, 7, 8, 9, 10, 11, 12, 13, 14, 15, 16, 17, 18, 19, or 20 nucleotides downstream stream of the PAM site. In some embodiments, the method does not require a canonical (e.g., NGG) PAM site. In some embodiments, the nucleobase editor comprises a linker. In some embodiments, the linker is 1-25 amino acids in length. In some embodiments, the linker is 5-20 amino acids in length. In some embodiments, the linker is 10, 11, 12, 13, 14, 15, 16, 17, 18, 19, or 20 amino acids in length. In some embodiments, the target region comprises a target window, wherein the target window comprises the target nucleobase pair. In some embodiments, the target window comprises 1-10 nucleotides. In some embodiments, the target window is 1-9, 1-8, 1-7, 1-6, 1-5, 1-4, 1-3, 1-2, or 1 nucleotides in length. In some embodiments, the target window is 1, 2, 3, 4, 5, 6, 7, 8, 9, 10, 11, 12, 13, 14, 15, 16, 17, 18, 19, or 20 nucleotides in length. In some embodiments, the intended edited base pair occurs within the target window. In some embodiments, the target window comprises the intended edited base pair. In some embodiments, the nucleobase editor is any one of the base editors provided herein.

Kits, Vectors, Cells

Some aspects of this disclosure provide kits comprising a nucleic acid construct, comprising (a) a nucleotide sequence encoding a Cas9 protein or a Cas9 fusion protein as provided herein; and (b) a heterologous promoter that drives expression of the sequence of (a). In some embodiments, the kit further comprises an expression construct encoding a guide RNA backbone, wherein the construct comprises a cloning site positioned to allow the cloning of a nucleic acid sequence identical or complementary to a target sequence into the guide RNA backbone.

Some aspects of this disclosure provide polynucleotides encoding a Cas9 protein of a fusion protein as provided herein. Some aspects of this disclosure provide vectors comprising such polynucleotides. In some embodiments, the vector comprises a heterologous promoter driving expression of polynucleotide.

Some aspects of this disclosure provide cells comprising a Cas9 protein, a fusion protein, a nucleic acid molecule encoding the fusion protein, a complex comprise the Cas9 protein and the gRNA, and/or a vector as provided herein.

The description of exemplary embodiments of the reporter systems above is provided for illustration purposes only and not meant to be limiting. Additional reporter systems, e.g., variations of the exemplary systems described in detail above, are also embraced by this disclosure.

EXAMPLES

Example 1: Cas9 Deaminase Fusion Proteins

A number of Cas9:Deaminase fusion proteins were generated and deaminase activity of the generated fusions was characterized. The following deaminases were tested:

```
Human AID (hAID):
                                              (SEQ ID NO: 607)
MDSLLMNRRKFLYQFKNVRWAKGRRETYLCYVVKRRDSATSFSLDFGYLR

NKNGCHVELLFLRYISDWDLDPGRCYRVTWFTSWSPCYDCARHVADFLRG

NPYLSLRIFTARLYFCEDRKAEPEGLRRLHRAGVQIAIMTFKDYFYCWNT

FVENHERTFKAWEGLHENSVRLSRQLRRILLPLYEVDDLRDAFRTLGLLD

Human AID-DC (hAID-DC, truncated version of hAID
with 7-fold increased activity):
                                              (SEQ ID NO: 608)
MDSLLMNRRKFLYQFKNVRWAKGRRETYLCYVVKRRDSATSFSLDFGYLR

NKNGCHVELLFLRYISDWDLDPGRCYRVTWFTSWSPCYDCARHVADFLRG

NPNLSLRIFTARLYFCEDRKAEPEGLRRLHRAGVQIAIMTFKDYFYCWNT

FVENHERTFKAWEGLHENSVRLSRQLRRILL

Rat APOBEC1 (rAPOBEC1):
                                              (SEQ ID NO: 284)
MSSETGPVAVDPTLRRRIEPHEFEVFFDPRELRKETCLLYEINWGGRHSI

WRHTSQNTNKHVEVNFIEKFTTERYFCPNTRCSITWFLSWSPCGECSRAI

TEFLSRYPHVTLFIYIARLYHHADPRNRQGLRDLISSGVTIQIMTEQESG

YCWRNFVNYSPSNEAHWPRYPHLWVRLYVLELYCIILGLPPCLNILRRKQ

PQLTFFTIALQSCHYQRLPPHILWATGLK

Human APOBEC1 (hAPOBEC1)
                                              (SEQ ID NO: 5724)
MTSEKGPSTGDPTLRRRIEPWEFDVFYDPRELRKEACLLYEIKWGMSRKI

WRSSGKNTTNHVEVNFIKKFTSERDFHPSMSCSITWFLSWSPCWECSQAI

REFLSRHPGVTLVIYVARLFWHMDQQNRQGLRDLVNSGVTIQIMRASEYY

HCWRNFVNYPPGDEAHWPQYPPLWMMLYALELHCIILSLPPCLKISRRWQ

NHLTFFRLHLQNCHYQTIPPHILLATGLIHPSVAWR

Petromyzon marinus (Lamprey) CDA1 (pmCDA1):
                                              (SEQ ID NO: 609)
MTDAEYVRIHEKLDIYTFKKQFFNNKKSVSHRCYVLFELKRRGERRACFW

GYAVNKPQSGTERGIHAEIFSIRKVEEYLRDNPGQFTINWYSSWSPCADC

AEKILEWYNQELRGNGHTLKIWACKLYYEKNARNQIGLWNLRDNGVGLNV

MVSEHYQCCRKIFIQSSHNQLNENRWLEKTLKRAEKRRSELSIMIQVKIL

HTTKSPAV

Human APOBEC3G (hAPOBEC3G):
                                              (SEQ ID NO: 610)
MELKYHPEMRFFHWFSKWRKLHRDQEYEVTWYISWSPCTKCTRDMATFLA

EDPKVTLTIFVARLYYFWDPDYQEALRSLCQKRDGPRATMKIMNYDEFQH

CWSKFVYSQRELFEPWNNLPKYYILLHIMLGEILRHSMDPPTFTFNFNNE

PWVRGRHETYLCYEVERMHNDTWVLLNQRRGFLCNQAPHKHGFLEGRHAE

LCFLDVIPFWKLDLDQDYRVTCFTSWSPCFSCAQEMAKFISKNKHVSLCI

FTARIYDDQGRCQEGLRTLAEAGAKISIMTYSEFKHCWDTFVDHQGCPFQ

PWDGLDEHSQDLSGRLRAILQNQEN
```

Deaminase Activity on ssDNA. A USER (Uracil-Specific Excision Reagent) Enzyme-based assay for deamination was employed to test the activity of various deaminases on single-stranded DNA (ssDNA) substrates. USER Enzyme was obtained from New England Biolabs. An ssDNA substrate was provided with a target cytosine residue at different positions. Deamination of the ssDNA cytosine target residue results in conversion of the target cytosine to a uracil. The USER Enzyme excises the uracil base and cleaves the ssDNA backbone at that position, cutting the ssDNA substrate into two shorter fragments of DNA. In some assays, the ssDNA substrate is labeled on one end with a dye, e.g., with a 5' Cy3 label (the * in the scheme below). Upon deamination, excision, and cleavage of the strand, the substrate can be subjected to electrophoresis, and the substrate and any fragment released from it can be visualized by detecting the label. Where Cy5 is images, only the fragment with the label will be visible via imaging.

Figure 41:
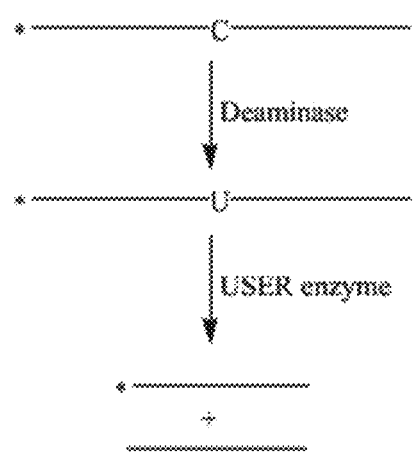
FIG. 41 shows a schematic representation of an exemplary USER (Uracil-Specific Excision Reagent) Enzyme-based assay, which may be used to test the activity of various deaminases on single-stranded DNA (ssDNA) substrates.

In one USER Enzyme assay, ssDNA substrates were used that matched the target sequences of the various deaminases tested. Expression cassettes encoding the deaminases tested were inserted into a CMV backbone plasmid that has been used previously in the lab (Addgene plasmid 52970). The deaminase proteins were expressed using a TNT Quick Coupled Transcription/Translation System (Promega) according to the manufacturers recommendations. After 90 min of incubation, 5 mL of lysate was incubated with 5' Cy3-labeled ssDNA substrate and 1 unit of USER Enzyme (NEB) for 3 hours. The DNA was resolved on a 10% TBE PAGE gel and the DNA was imaged using Cy-dye imaging. A schematic representation of the USER Enzyme assay is shown in FIG. 41.

Figure 1:
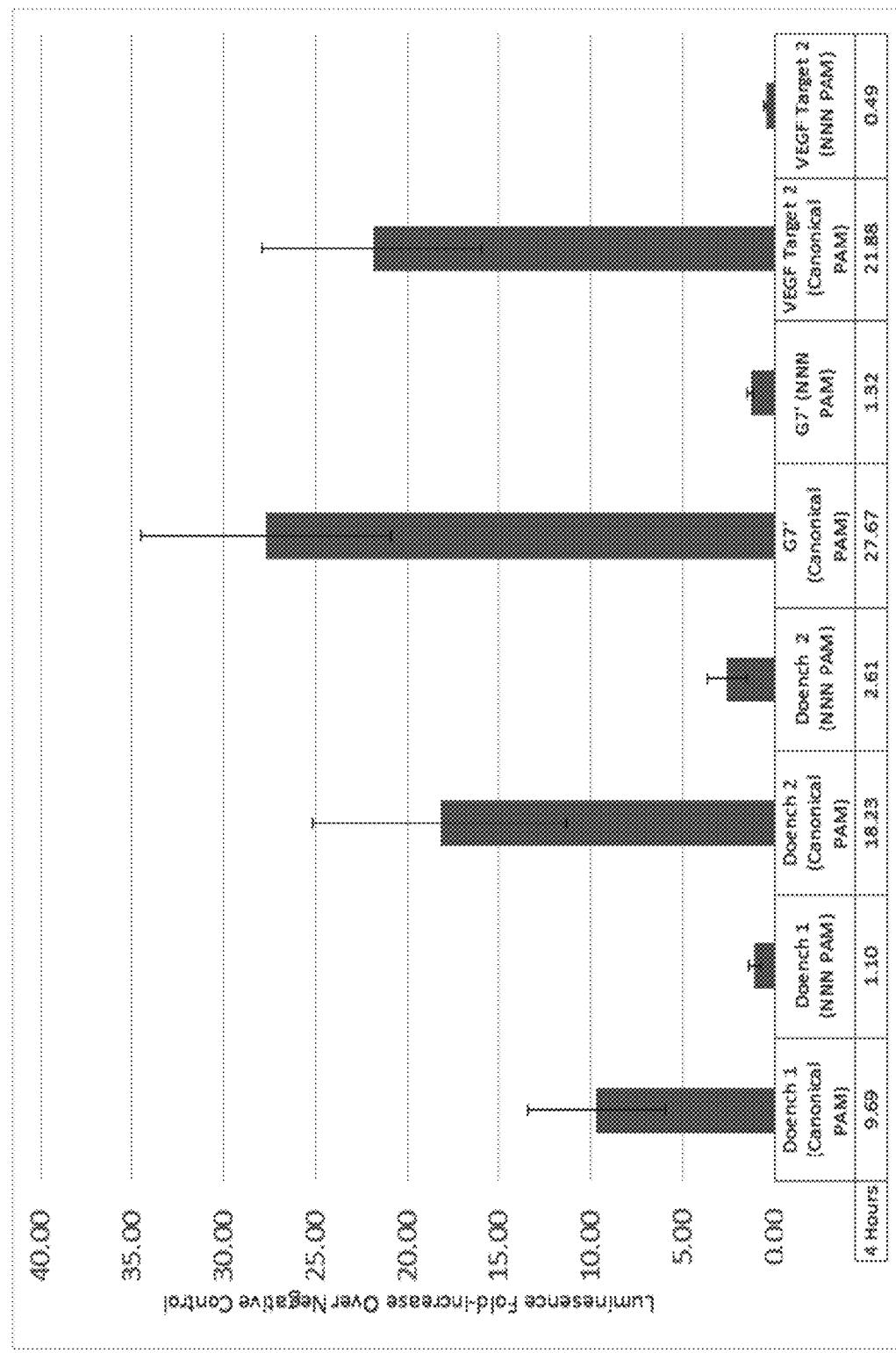
FIG. 1 shows the deaminase activity of deaminases on single stranded DNA substrates. Single stranded DNA substrates using randomized PAM sequences (NNN PAM) were used as negative controls. Canonical PAM sequences used (NGG PAM)

FIG. 1 shows the deaminase activity of the tested deaminases on ssDNA substrates, such as Doench 1, Doench 2, G7' and VEGF Target 2. The rAPOBEC1 enzyme exhibited a substantial amount of deamination on the single-stranded DNA substrate with a canonical NGG PAM, but not with a negative control non-canonical NNN PAM. Cas9 fusion proteins with APOBEC family deaminases were generated. The following fusion architectures were constructed and tested on ssDNA:

rAPOBEC1-GGS-dCas9 primary sequence
(SEQ ID NO: 611)

MSSETGPVAVDPTLRRRIEPHEFEVFFDPRELRKETCLLYEINWGGRHSIWRHTSQNT

NKHVEVNFIEKFTTERYFCPNTRCSITWFLSWSPCGECSRAITEFLSRYPHVTLFIYIAR

LYHHADPRNRQGLRDLISSGVTIQIMTEQESGYCWRNFVNYSPSNEAHWPRYPHLW

VRLYVLELYCIILGLPPCLNILRRKQPQLTFFTIALQSCHYQRLPPHILWATGLK`GGS`D

*KKYSIGLAIGTNSVGWAVITDEYKVPSKKFKVLGNTDRHSIKKNLIGALLFDSGETAE*

*ATREKRTARRRYTRRKNRICYLQEIFSNEMAKVDDSFFHRLEESFLVEEDKKHERHP*

*IFGNIVDEVAYHEKYPTIYHLRKKLVDSTDKADLRLIYLALAHMIKFRGHFLIEGDLN*

*PDNSDVDKLFIQLVQTYNQLFEENPINASGVDAKAILSARLSKSRRLENLIAQLPGEK*

*KNGLFGNLIALSLGLTPNFKSNFDLAEDAKLQLSKDTYDDDLDNLLAQIGDQYADLF*

*LAAKNLSDAILLSDILRVNTEITKAPLSASMIKRYDEHHQDLTLLKALVRQQLPEKYK*

*EIFFDQSKNGYAGYIDGGASQEEFYKFIKPILEKMDGTEELLVKLNREDLLRKQRTF*

*DNGSIPHQIHLGELHAILRRQEDFYPFLKDNREKIEKILTFRIPYYVGPLARGNSRFA*

*WMTRKSEETITPWNFEEVVDKGASAQSFIERMTNFDKNLPNEKVLPKHSLLYEYFT*

*VYNELTKVKYVTEGMRKPAFLSGEQKKAIVDLLFKTNRKVTVKQLKEDYFKKIECFD*

*SVEISGVEDRFNASLGTYHDLLKUKDKDFLDNEENEDILEDIVLTLTLFEDREMIEE*

*RLKTYAHLFDDKVMKQLKRRRYTGWGRLSRKLINGIRDKQSGKTILDFLKSDGFANR*

*NFMQLIHDDSLTFKEDIQKAQVSGQGDSLHEHIANLAGSPAIKKGILQTVKVVDELV*

*KVMGRHKPENIVIEMARENQTTQKGQKNSRERMKRIEEGIKELGSQILKEHPVENTQ*

*LQNEKLYLYYLQNGRDMYVDQELDINRLSDYDVDAIVPQSFLKDDSIDNKVLTRSDK*

*NRGKSDNVPSEEVVKKMKNYWRQLLNAKLITQRKFDNLTKAERGGLSELDKAGFIK*

*RQLVETRQITKHVAQILDSRMNTKYDENDKLIREVKVITLKSKLVSDFRKDFQFYKVR*

*EINNYHHAHDAYLNAVVGTALIKKYPKLESEFVYGDYKVYDVRKMIAKSEQEIGKAT*

*AKYFFYSNIMNFFKTEITLANGEIRKRPLIETNGETGEIVWDKGRDFATVRKVLSMP*

*QVNIVKKTEVQTGGFSKESILPKRNSDKLIARKKDWDPKKYGGFDSPTVAYSVLVVAK*

*VEKGKSKKLKSVKELLGITIMERSSFEKNPIDFLEAKGYKEVKKDLIIKLPKYSLFELE*

*NGRKRMLASAGELQKGNELALPSKYVNFLYLASHYEKLKGSPEDNEQKQLFVEQHK*

*HYLDEIIEQISEFSKRVILADANLDKVLSAYNKHRDKPIREQAENIIHLFTLTNLGAPA*

*AFKYFDTTIDRKRYTSTKEVLDATLIHQSITGLYETRIDLSQLGGD* rAPOBEC1-(GGS)₃-dCas9 primary sequence
(SEQ ID NO: 612)

MSSETGPVAVDPTLRRRIEPHEFEVFFDPRELRKETCLLYEINWGGRHSIWRHTSQNT

NKHVEVNFIEKFTTERYFCPNTRCSITWFLSWSPCGECSRAITEFLSRYPHVTLFIYIAR

LYHHADPRNRQGLRDLISSGVTIQIMTEQESGYCWRNFVNYSPSNEAHWPRYPHLW

VRLYVLELYCIILGLPPCLNILRRKQPQLTFFTIALQSCHYQRLPPHILWATGLK`GGSG`

`GSGGS`*MDKKYSIGLAIGTNSVGWAVITDEYKVPSKKFKVLGNTDRHSIKKNLIGALLF*

*DSGETAEATRLKRTARRRYTRRKNRICYLQEIFSNEMAKVDDSFFHRLEESFLVEED*

*KKHERHPIFGNIVDEVAYHEKYPTIYHLRKKLVDSTDKADLRLIYLALAHMIKFRGH*

*FLIEGDLNPDNSDVDKLFIQLVQTYNQLFEENPINASGVDAKAILSARLSKSRRLENLI*

*AQLPGEKKNGLFGNLIALSLGLTPNFKSNFDLAEDAKLQLSKDTYDDDLDNLLAQIG*

*DQYADLFLAAKNLSDAILLSDILRVNTEITKAPLSASMIKRYDEHHQDLTLLKALVRQ*

*QLPEKYKEIFFDQSKNGYAGYIDGGASQEEFYKFIKPILEKMDGTEELLVKLNREDLL*

*RKQRTFDNGSIPHQIHLGELHAILRRQEDFYPFLKDNREKIEKILTFRIPYYVGPLAR*

*GNSRFAWMTRKSEETITPWNFEEVVDKGASAQSFIERMTNFDKNLPNEKVLPKHSL*

LYEYFTVYNELTKVKYVTEGMRKPAFLSGEQKKAIVDLLFKTNRKVTVKQLKEDYFK

KIECFDSVEISGVEDRFNASLGTYHDLLKHKDKDFLDNEENEDILEDIVLTLTLFEDR

EMIEERLKTYAHLFDDKVMKQLKRRRYTGWGRLSRKLINGIRDKQSGKTILDFLKSD

GFANRNFMQLIHDDSLTFKEDIQKAQVSGQGDSLHEHIANLAGSPAIKKGILQTVKV

VDELVKVMGRHKPENIVIEMARENQTTQKGQKNSRERMKRIEEGIKELGSQILKEHP

VENTQLQNEKLYLYYLQNGRDMYVDQELDINRLSDYDVDAIVPQSFLKDDSIDNKVL

TRSDKNRGKSDNVPSEEVVKKMKNYWRQLLNAKLITQRKFDNLTKAERGGLSELDK

AGFIKRQLVETRQITKHVAQILDSRMNTKYDENDKLIREVKVITLKSKLVSDFRKDFQ

FYKVREINNYHHAHDAYLNAVVGTALIKKYPKLESEFVYGDYKVYDVRKMIAKSEQE

IGKATAKYFFYSNIMNFFKTEITLANGEIRKRPLIETNGETGEIVWDKGRDFATVRKV

LSMPQVNIVKKTEVQTGGFSKESILPKRNSDKLIARKKDWDPKKYGGFDSPTVAYSVL

VVAKVEKGKSKKLKSVKELLGITIMERSSFEKNPIDFLEAKGYKEVKKDLIIKLPKYSL

FELENGRKRMLASAGELQKGNELALPSKYVNFLYLASHYEKLKGSPEDNEQKQLFV

EQHKHYLDEHEQISEFSKRVILADANLDKVLSAYNKHRDKPIREQAENIIHLFTLTNL

GAPAAFKYFDTTIDRKRYTSTKEVLDATLIHQSITGLYETRIDLSQLGGD dCas9-GGS-rAPOBEC1

(SEQ ID NO: 613)

DKKYSIGLAIGTNSVGWAVITDEYKVPSKKFKVLGNTDRHSIKKNLIGALLFDSGETA

EATRLKRTARRRYTRRKNRICYLQEIFSNEMAKVDDSFFHRLEESFLVEEDKKHERH

PIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGE

KKNGLFGNLIALSLGLTPNFKSNFDLAEDAKLQLSKDTYDDDLDNLLAQIGDQYADL

FLAAKNLSDAILLSDILRVNTEITKAPLSASMIKRYDEHHQDLTLLKALVRQQLPEKY

KEIFFDQSKNGYAGYIDGGASQEEFYKFIKPILEKMDGTEELLVKLNREDLLRKQRT

FDNGSIPHQIHLGELHAILRRQEDFYPFLKDNREKIEKILTFRIPYYVGPLARGNSRF

AWMTRKSEETITPWNFEEVVDKGASAQSFIERMTNFDKNLPNEKVLPKHSLLYEYF

TVYNELTKVKYVTEGMRKPAFLSGEQKKAIVDLLFKTNRKVTVKQLKEDYFKKIECF

DSVEISGVEDRFNASLGTYHDLLKIIKDKDFLDNEENEDILEDIVLTLTLFEDREMIE

ERLKTYAHLFDDKVMKQLKRRRYTGWGRLSRKLINGIRDKQSGKTILDFLKSDGFAN

RNFMQLIHDDSLTFKEDIQKAQVSGQGDSLHEHIANLAGSPAIKKGILQTVKVVDEL

VKVMGRHKPENIVIEMARENQTTQKGQKNSRERMKRIEEGIKELGSQILKEHPVENT

QLQNEKLYLYYLQNGRDMYVDQELDINRLSDYDVDAIVPQSFLKDDSIDNKVLTRSD

KNRGKSDNVPSEEVVKKMKNYWRQLLNAKLITQRKFDNLTKAERGGLSELDKAGFI

KRQLVETRQITKHVAQILDSRMNTKYDENDKLIREVKVITLKSKLVSDFRKDFQFYKV

REINNYHHAHDAYLNAVVGTALIKKYPKLESEFVYGDYKVYDVRKMIAKSEQEIGKA

TAKYFFYSNIMNFFKTEITLANGEIRKRPLIETNGETGEIVWDKGRDFATVRKVLSMP

QVNIVKKTEVQTGGFSKESILPKRNSDKLIARKKDWDPKKYGGFDSPTVAYSVLVVAK

VEKGKSKKLKSVKELLGITIMERSSFEKNPIDFLEAKGYKEVKKDLIIKLPKYSLFELE

NGRKRMLASAGELQKGNELALPSKYVNFLYLASHYEKLKGSPEDNEQKQLFVEQHK

HYLDEHEQISEFSKRVILADANLDKVLSAYNKHRDKPIREQAENIIHLFTLTNLGAPA

AFKYFDTTIDRKRYTSTKEVLDATLIHQSITGLYETRIDLSQLGGDGGSMSSETGPVA

VDPTLRRRIEPHEFEVFFDPRELRKETCLLYEINWGGRHSIWRHTSQNTNKHVEVNFI

EKFTTERYFCPNTRCSITWFLSWSPCGECSRAITEFLSRYPHVTLFIYIARLYHHADPR

NRQGLRDLISSGVTIQIMTEQESGYCWRNFVNYSPSNEAHWPRYPHLWVRLYVLEL

YCIILGLPPCLNILRRKQPQLTFFTIALQSCHYQRLPPHILWATGLK dCas9-[GGS₃]-rAPOBEC1

(SEQ ID NO: 614)

DKKYSIGLAIGTNSVGWAVITDEYKVPSKKFKVLGNTDRHSIKKNLIGALLFDSGETA
EATRLKRTARRRYTRRKNRICYLQEIFSNEMAKVDDSFFHRLEESFLVEEDKKHERH
PIFGNIVDEVAYHEKYPTIYHLRKKLVDSTDKADLRLIYLALAHMIKFRGHFLIEGDL
NPDNSDVDKLFIQLVQTYNQLFEENPINASGVDAKAILSARLSKSRRLENLIAQLPGE
KKNGLFGNLIALSLGLTPNFKSNFDLAEDAKLQLSKDTYDDDLDNLLAQIGDQYADL
FLAAKNLSDAILLSDILRVNTEITKAPLSASMIKRYDEHHQDLTLLKALVRQQLPEKY
KEIFFDQSKNGYAGYIDGGASQEEFYKFIKPILEKMDGTEELLVKLNREDLLRKQRT
FDNGSIPHQIHLGELHAILRRQEDFYPFLKDNREKIEKILTFRIPYYVGPLARGNSRF
AWMTRKSEETITPWNFEEVVDKGASAQSFIERMTNFDKNLPNEKVLPKHSLLYEYF
TVYNELTKVKYVTEGMRKPAFLSGEQKKAIVDLLFKTNRKVTVKQLKEDYFKKIECF
DSVEISGVEDRFNASLGTYHDLLKIIKDKDFLDNEENEDILEDIVLTLTLFEDREMIE
ERLKTYAHLFDDKVMKQLKRRRYTGWGRLSRKLINGIRDKQSGKTILDFLKSDGFAN
RNFMQLIHDDSLTFKEDIQKAQVSGQGDSLHEHIANLAGSPAIKKGILQTVKVVDEL
VKVMGRHKPENIVIEMARENQTTQKGQKNSRERMKRIEEGIKELGSQILKEHPVENT
QLQNEKLYLYYLQNGRDMYVDQELDINRLSDYDVDAIVPQSFLKDDSIDNKVLTRSD
KNRGKSDNVPSEEVVKKMKNYWRQLLNAKLITQRKFDNLTKAERGGLSELDKAGFI
KRQLVETRQITKHVAQILDSRMNTKYDENDKLIREVKVITLKSKLVSDFRKDFQFYKV
REINNYHHAHDAYLNAVVGTALIKKYPKLESEFVYGDYKVYDVRKMIAKSEQEIGKA
TAKYFFYSNIMNFFKTEITLANGEIRKRPLIETNGETGEIVWDKGRDFATVRKVLSMP
QVNIVKKTEVQTGGFSKESILPKRNSDKLIARKKDWDPKKYGGFDSPTVAYSVLVVAK
VEKGKSKKLKSVKELLGITIMERSSFEKNPIDFLEAKGYKEVKKDLIIKLPKYSLFELE
NGRKRMLASAGELQKGNELALPSKYVNFLYLASHYEKLKGSPEDNEQKQLFVEQHK
HYLDEIIEQISEFSKRVILADANLDKVLSAYNKHRDKPIREQAENIIHLFTLTNLGAPA
AFKYFDTTIDRKRYTSTKEVLDATLIHQSITGLYETRIDLSQLGGD[GGSGGSGGS]MSS
ETGPVAVDPTLRRRIEPHEFEVFFDPRELRKETCLLYEINWGGRHSIWRHTSQNTNKH
VEVNFIEKFTTERYFCPNTRCSITWFLSWSPCGECSRAITEFLSRYPHVTLFIYIARLYH
HADPRNRQGLRDLISSGVTIQIMTEQESGYCWRNFVNYSPSNEAHWPRYPHLWVRL
YVLELYCIILGLPPCLNILRRKQPQLTFFTIALQSCHYQRLPPHILWATGLK rAPOBEC1-[XTEN]-dCas9 primary sequence (SEQ ID NO: 615)

MSSETGPVAVDPTLRRRIEPHEFEVFFDPRELRKETCLLYEINWGGRHSIWRHTSQNT
NKHVEVNFIEKFTTERYFCPNTRCSITWFLSWSPCGECSRAITEFLSRYPHVTLFIYIAR
LYHHADPRNRQGLRDLISSGVTIQIMTEQESGYCWRNFVNYSPSNEAHWPRYPHLW
VRLYVLELYCIILGLPPCLNILRRKQPQLTFFTIALQSCHYQRLPPHILWATGLKS[GSE
TPGTSESATPES]DKKYSIGLAIGTNSVGWAVITDEYKVPSKKFKVLGNTDRHSIKKNLI
GALLEDSGETAEATRLKRTARRRYTRRKNRICYLQEIESNEMAKVDDSFEHRLEESF
LVEEDKKHERHPIEGNIVDEVAYHEKYPTIYHLRKKLVDSTDKADLRLIYLALAHMIK
ERGHELIEGDLNPDNSDVDKLEIQLVQTYNQLFEENPINASGVDAKAILSARLSKSRR
LENLIAQLPGEKKNGLEGNLIALSLGLTPNEKSNEDLAEDAKLQLSKDTYDDDLDNL
LAQIGDQYADLELAAKNLSDAILLSDILRVNTEITKAPLSASMIKRYDEHHQDLTLLK

```
ALVRQQLPEKYKEIFEDQSKNGYAGYIDGGASQEEEYKEIKPILEKMDGTEELLVKLN
REDLLRKQRTEDNGSIPHQIHLGELHAILRRQEDEYPELKDNREKIEKILTERIPYYV
GPLARGNSRFAWMTRKSEETITPWNEEEVVDKGASAQSFIERMTNEDKNLPNEKVL
PKHSLLYEYETVYNELTKVKYVTEGMRKPAELSGEQKKAIVDLLEKTNRKVTVKQLK
EDYEKKIECEDSVEISGVEDRENASLGTYHDLLKIIKDKDELDNEENEDILEDIVLTLT
LEEDREMIEERLKTYAHLEDDKVMKQLKRRRYTGWGRLSRKLINGIRDKQSGKTILD
ELKSDGEANRNEMQLIHDDSLTEKEDIQKAQVSGQGDSLHEHIANLAGSPAIKKGIL
QTVKVVDELVKVMGRHKPENIVIEMARENQTTQKGQKNSRERMKRIEEGIKELGSQI
LKEHPVENTQLQNEKLYLYYLQNGRDMYVDQELDINRLSDYDVDAIVPQSELKDDSI
DNKVLTRSDKNRGKSDNVPSEEVVKKMKNYWRQLLNAKLITQRKEDNLTKAERGGL
SELDKAGFIKRQLVETRQITKHVAQILDSRMNTKYDENDKLIREVKVITLKSKLVSDF
RKDEQEYKVREINNYHHAHDAYLNAVVGTALIKKYPKLESEEVYGDYKVYDVRKMIA
KSEQEIGKATAKYFEYSNIMNEEKTEITLANGEIRKRPLIETNGETGEIVWDKGRDEA
TVRKVLSMPQVNIVKKTEVQTGGESKESILPKRNSDKLIARKKDWDPKKYGGEDSPT
VAYSVLVVAKVEKGKSKKLKSVKELLGITIMERSSEEKNPIDELEAKGYKEVKKDLHK
LPKYSLEELENGRKRMLASAGELQKGNELALPSKYVNELYLASHYEKLKGSPEDNEQ
KQLEVEQHKHYLDEHEQISEESKRVILADANLDKVLSAYNKHRDKPIREQAENHHLF
TLTNLGAPAAFKYEDTTIDRKRYTSTKEVLDATLIHQSITGLYETRIDLSQLGGD
```

Figure 2:
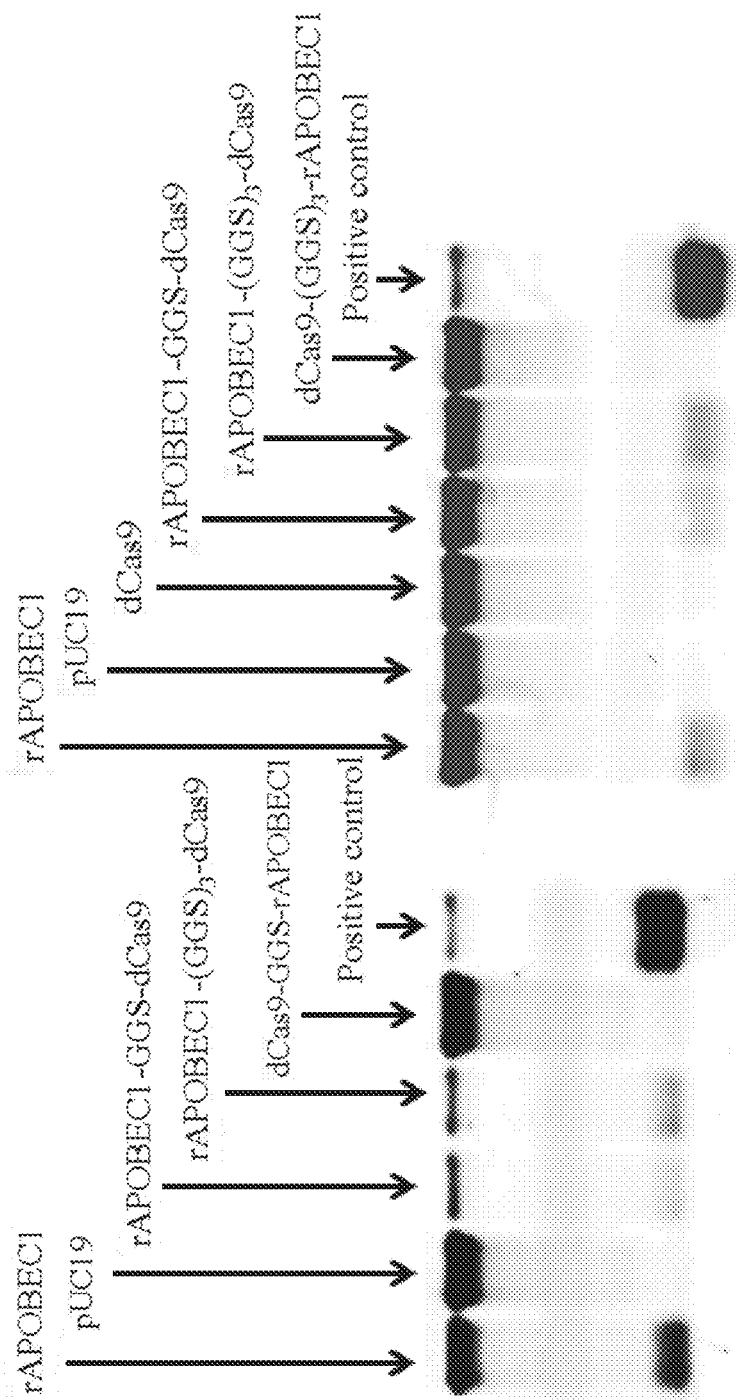
FIG. 2 shows activity of Cas9:deaminase fusion proteins on single stranded DNA substrates.

FIG. 2 shows that the N-terminal deaminase fusions showed significant activity on the single stranded DNA substrates. For this reason, only the N-terminal architecture was chosen for further experiments.

FIG. 3 illustrates double stranded DNA substrate binding by deaminase-dCas9:sgRNA complexes. A number of double stranded deaminase substrate sequences were generated. The sequences are provided below. The structures according to FIG. 3 are identified in these sequences (36 bp: underlined, sgRNA target sequence: bold; PAM: boxed; 21 bp: italicized). All substrates were labeled with a 5'-Cy3 label:

```
                                       (SEQ ID NO:616)
2:GTAGGTAGTTAGGATGAATGGAAGGTTGGTATAGTCCCGCGGATTT
ATTTATTTAATGGATGACCTCTGGATCCATGGAC-3'

(SEQ ID NO:617)
3:GTAGGTAGTTAGGATGAATGGAAGGTTGGTATAGCTTCCGCGGATT
TATTTATTTATGGATGACCTCTGGATCCATGGAC-3'

(SEQ ID NO:618)
4:GTAGGTAGTTAGGATGAATGGAAGGTTGGTATAGCCTTCCGCGGAT
TTATTTATTATGGATGACCTCTGGATCCATGGAC-3'

(SEQ ID NO:619)
5:GTAGGTAGTTAGGATGAATGGAAGGTTGGTATAGCCATTCCGCGGA
TTTATTTATTTGGATGACCTCTGGATCCATGGAC-3'

(SEQ ID NO:620)
6:GTAGGTAGTTAGGATGAATGGAAGGTTGGTATAGCCTATTCCGCGG
TTTATTTATTGGATGACCTCTGGATCCATGGAC-3'

(SEQ ID NO:621)
7:GTAGGTAGTTAGGATGAATGGAAGGTTGGTATAGCCTTATTCCGCG
GATTTATTTATGGATGACCTCTGGATCCATGGAC-3'

(SEQ ID NO:622)
8:GTAGGTAGTTAGGATGAATGGAAGGTTGGTATAGCCATTATTCCGC
GGATTTATTTTGGATGACCTCTGGATCCATGGAC-3'

(SEQ ID NO:623)
9:GTAGGTAGTTAGGATGAATGGAAGGTTGGTATAGCCTATTATTCCG
CGGATTTATTTGGATGACCTCTGGATCCATGGAC-3'

(SEQ ID NO:624)
10:GTAGGTAGTTAGGATGAATGGAAGGTTGGTATAGCCATTATATTCC
GCGGATTTATTGGATGACCTCTGGATCCATGGAC-3'

(SEQ ID NO:625)
11:GTAGGTAGTTAGGATGAATGGAAGGTTGGTATAGCCTATTATATTC
CGCGGATTTATGGATGACCTCTGGATCCATGGAC-3'

(SEQ ID NO:626)
12:GTAGGTAGTTAGGATGAATGGAAGGTTGGTATAGCCTTATTATATT
CCGCGGATTTTGGATGACCTCTGGATCCATGGAC-3'

(SEQ ID NO:627)
13:GTAGGTAGTTAGGATGAATGGAAGGTTGGTATAGCCATTATTATAT
TCCGCGGATTTGGATGACCTCTGGATCCATGGAC-3'

(SEQ ID NO:628)
14:GTAGGTAGTTAGGATGAATGGAAGGTTGGTATAGCCTATTATTATA
TTCCGCGGATTGGATGACCTCTGGATCCATGGAC-3'
```

-continued (SEQ ID NO:629)
15:GTAGGTAGTTAGGATGAATGGAAGGTTGGTATAGCCATTATTATTA
TTACCGCGGATGGATGACCTCTGGATCCATGGAC-3'

(SEQ ID NO:630)
18:GTAGGTAGTTAGGATGAATGGAAGGTTGGTATAGCCATTATTATTA
TTATTACCGCTGGATGACCTCTGGATCCATGGAC-3'

"-":

(SEQ ID NO:631)
GTAGGTAGTTAGGATGAATGGAAGGTTGGTATAGTAATATTAATTTAT
TTATTTAATGGATGACCTCTGGATCCATGGAC-3'

(SEQ ID NO:632)
8U:GTAGGTAGTTAGGATGAATGGAAGGTTGGTGTAGATTATTATCUG
CGGATTTATTGGATGACCTCTGGATCCATGGACAT-3'

*In all substrates except for "8U", the top strand in FIG. 3 is the complement of the sequence specified here. In the case of "8U", there is a "G" opposite the U.

Figure 4:
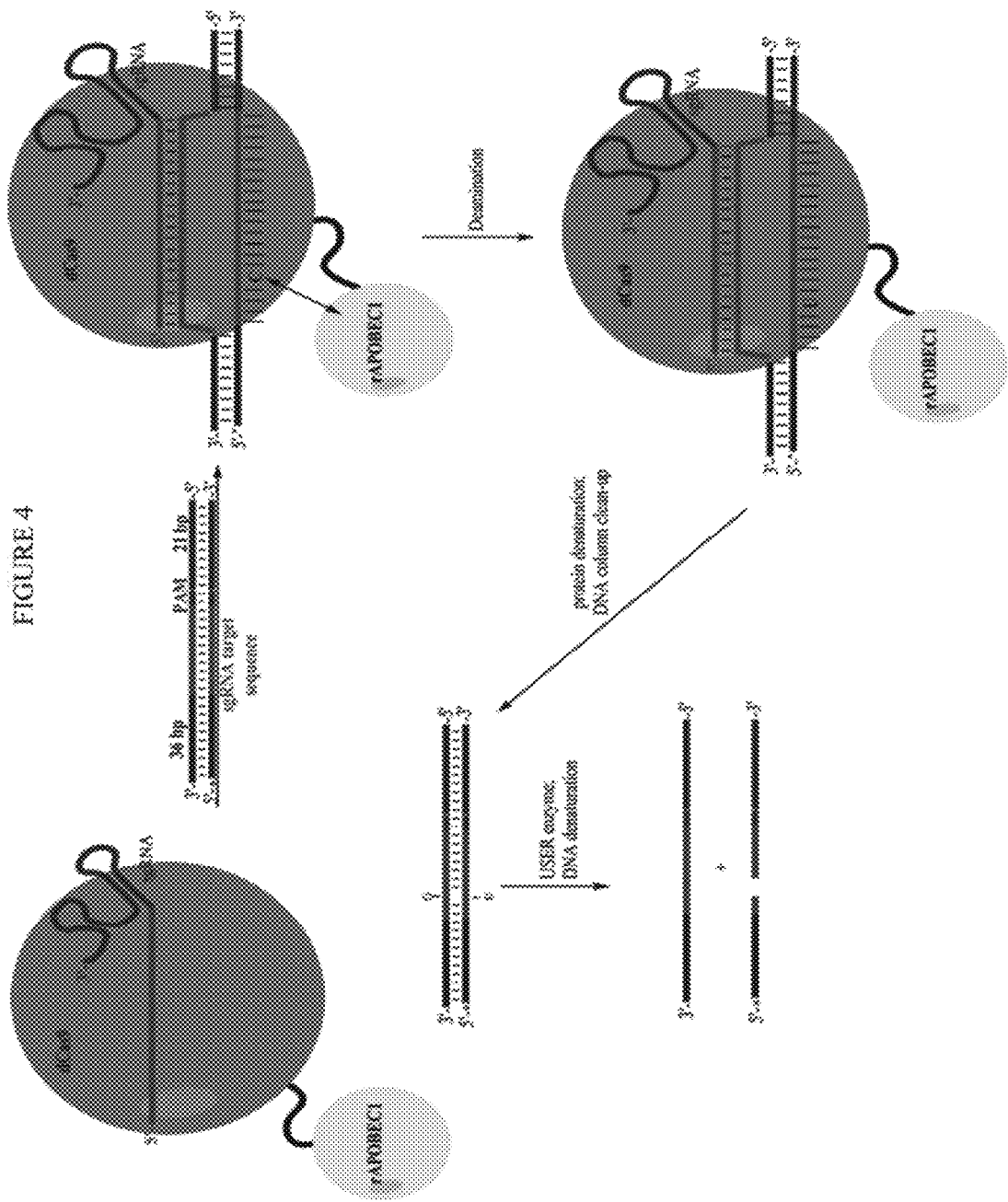
FIG. 4 illustrates a double stranded DNA deamination assay.

FIG. 4 shows the results of a double stranded DNA Deamination Assay. The fusions were expressed and purified with an N-terminal His6 tag via both Ni-NTA and sepharose chromatography. In order to assess deamination on dsDNA substrates, the various dsDNA substrates shown on the previous slide were incubated at a 1:8 dsDNA:fusion protein ratio and incubated at 37° C. for 2 hours. Once the dCas9 portion of the fusion binds to the DNA it blocks access of the USER enzyme to the DNA. Therefore, the fusion proteins were denatured following the incubation and the dsDNA was purified on a spin column, followed by incubation for 45 min with the USER Enzyme and resolution of the resulting DNA substrate and substrate fragments on a 10% TBE-urea gel.

Figure 5:
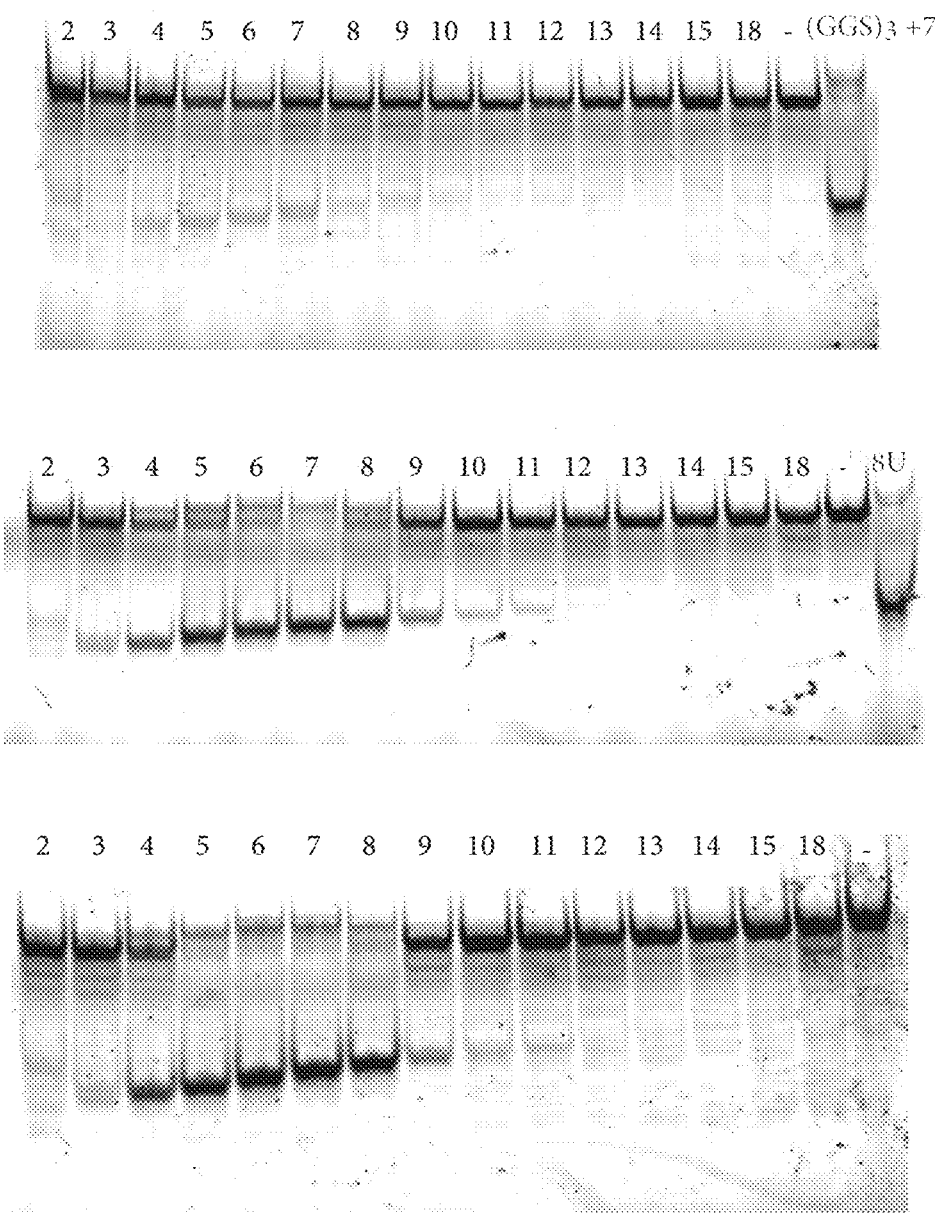
FIG. 5 demonstrates that Cas9 fusions can target positions 3-11 of double-stranded DNA target sequences (numbered according to the schematic in FIG. 5). Upper Gel: 1 µM rAPOBEC1-GGS-dCas9, 125 nM dsDNA, 1 equivalent sgRNA. Mid Gel: 1 µM rAPOBEC1-(GGS)$_3$(SEQ ID NO: 596)-dCas9, 125 nM dsDNA, 1 equivalent sgRNA. Lower Gel: 1.85 µM rAPOBEC1-XTEN-dCas9, 125 nM dsDNA, 1 equivalent sgRNA.

FIG. 5 demonstrates that Cas9 fusions can target positions 3-11 of double-stranded DNA target sequences (numbered according to the schematic in FIG. 3). Upper Gel: 1 µM rAPOBEC1-GGS-dCas9, 125 nM dsDNA, 1 eq sgRNA. Mid Gel: 1 µM rAPOBEC1-(GGS)$_3$-dCas9, 125 nM dsDNA, 1 eq sgRNA. Lower Gel: 1.85 µM rAPOBEC1-XTEN-dCas9, 125 nM dsDNA, 1 eq sgRNA. Based on the data from these gels, positions 3-11 (according to the numbering in FIG. 3) are sufficiently exposed to the activity of the deaminase to be targeted by the fusion proteins tested. Access of the deaminase to other positions is most likely blocked by the dCas9 protein.

The data further indicates that a linker of only 3 amino acids (GGS) is not optimal for allowing the deaminase to access the single stranded portion of the DNA. The 9 amino acid linker [(GGS)$_3$] (SEQ ID NO: 596) and the more structured 16 amino acid linker (XTEN) allow for more efficient deamination.

Figure 6:
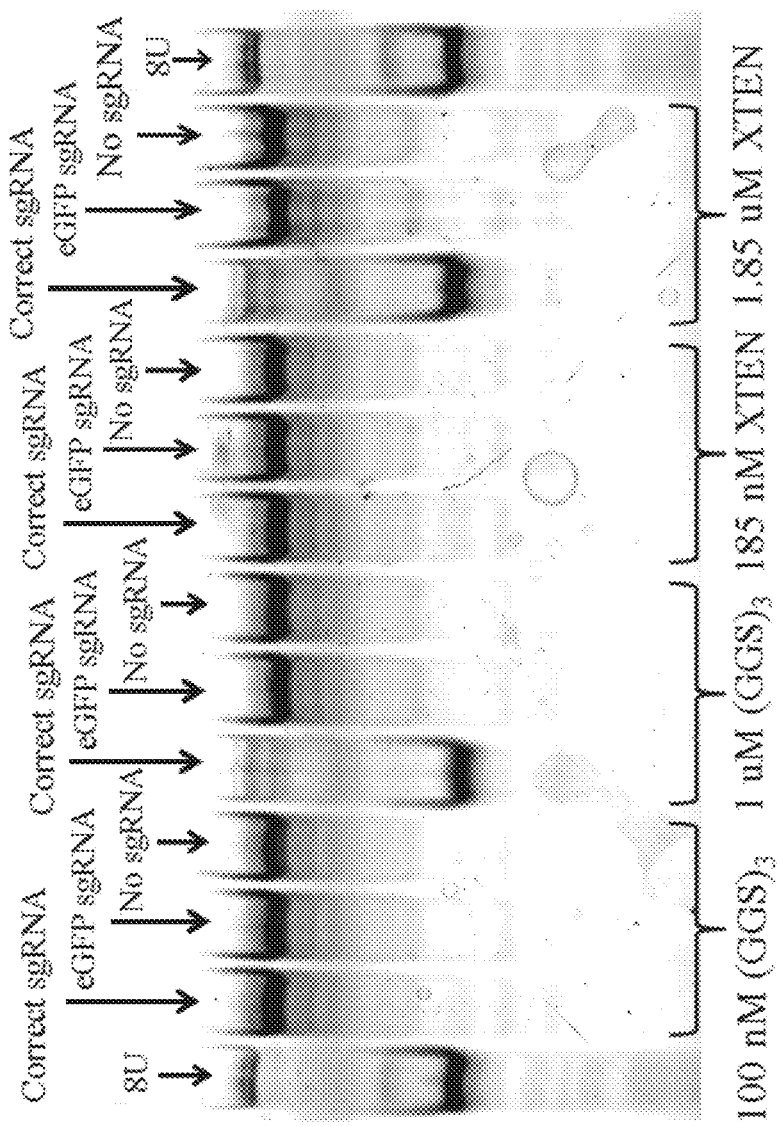
FIG. 6 demonstrates that the correct guide RNA, e.g., the correct sgRNA, is required for deaminase activity.

FIG. 6 demonstrates that the correct guide RNA, e.g., the correct sgRNA, is required for deaminase activity. The gel shows that fusing the deaminase to dCas9, the deaminase enzyme becomes sequence specific (e.g., using the fusion with an eGFP sgRNA results in no deamination), and also confers the capacity to the deaminase to deaminate dsDNA. The native substrate of the deaminase enzyme is ssDNA, and no deamination occurred when no sgRNA was added. This is consistent with reported knowledge that APOBEC deaminase by itself does not deaminate dsDNA. The data indicates that Cas9 opens the double-stranded DNA helix within a short window, exposing single-stranded DNA that is then accessible to the APOBEC deaminase for cytidine deamination. The sgRNA sequences used are provided below. sequences (36 bp: underlined, sgRNA target sequence: bold; PAM: boxed; 21 bp: italicized)

DNA sequence 8:

(SEQ ID NO: 633)
5'-Cy3-
GTAGGTAGTTAGGATGAATGGAAGGTTGGTATAGCCATTATTCCGCGGATTT
ATTTTGG*ATGACCTCTGGATCCATGGAC*-3'

(SEQ ID NO: 634)
Correct sgRNA sequence (partial 3' sequence):
5'-AUUAUUCCGCGGAUUUAUUUGUUUUAGAGCUAG...-3'

(SEQ ID NO: 635)
eGFP sgRNA sequence (partial 3'-sequence):
5'-CGUAGGCCAGGGUGGUCACGGUUUUAGAGCUAG...-3'

Example 2: Deamination of DNA Target Sequence

Exemplary deamination targets. The dCas9:deaminase fusion proteins described herein can be delivered to a cell in vitro or ex vivo or to a subject in vivo and can be used to effect C to T or G to A transitions when the target nucleotide is in positions 3-11 with respect to a PAM. Exemplary deamination targets include, without limitation, the following: CCR5 truncations: any of the codons encoding Q93, Q102, Q186, R225, W86, or Q261 of CCR5 can be deaminated to generate a STOP codon, which results in a non-functional truncation of CCR5 with applications in HIV treatment. APOE4 mutations: mutant codons encoding C11R and C57R mutant APOE4 proteins can be deaminated to revert to the wild-type amino acid with applications in Alzheimer's treatment. eGFP truncations: any of the codons encoding Q158, Q184, Q185 can be deaminated to generate a STOP codon, or the codon encoding M1 can be deaminated to encode I, all of which result in loss of eGFP fluorescence, with applications in reporter systems. eGFP restoration: a mutant codon encoding T65A or Y66C mutant GFP, which does not exhibit substantial fluorescence, can be deaminated to restore the wild-type amino acid and confer fluorescence. PIK3CA mutation: a mutant codon encoding K111E mutant PIK3CA can be deaminated to restore the wild-type amino acid residue with applications in cancer. CTNNB1 mutation: a mutant codon encoding T41A mutant CTNNB1 can be deaminated to restore the wild-type amino acid residue with applications in cancer. HRAS mutation: a mutant codon encoding Q61R mutant HRAS can be deaminated to restore the wild-type amino acid residue with applications in cancer. P53 mutations: any of the mutant codons encoding Y163C, Y236C, or N239D mutant p53 can be deaminated to encode the wild type amino acid sequence with applications in cancer.

Figure 7:
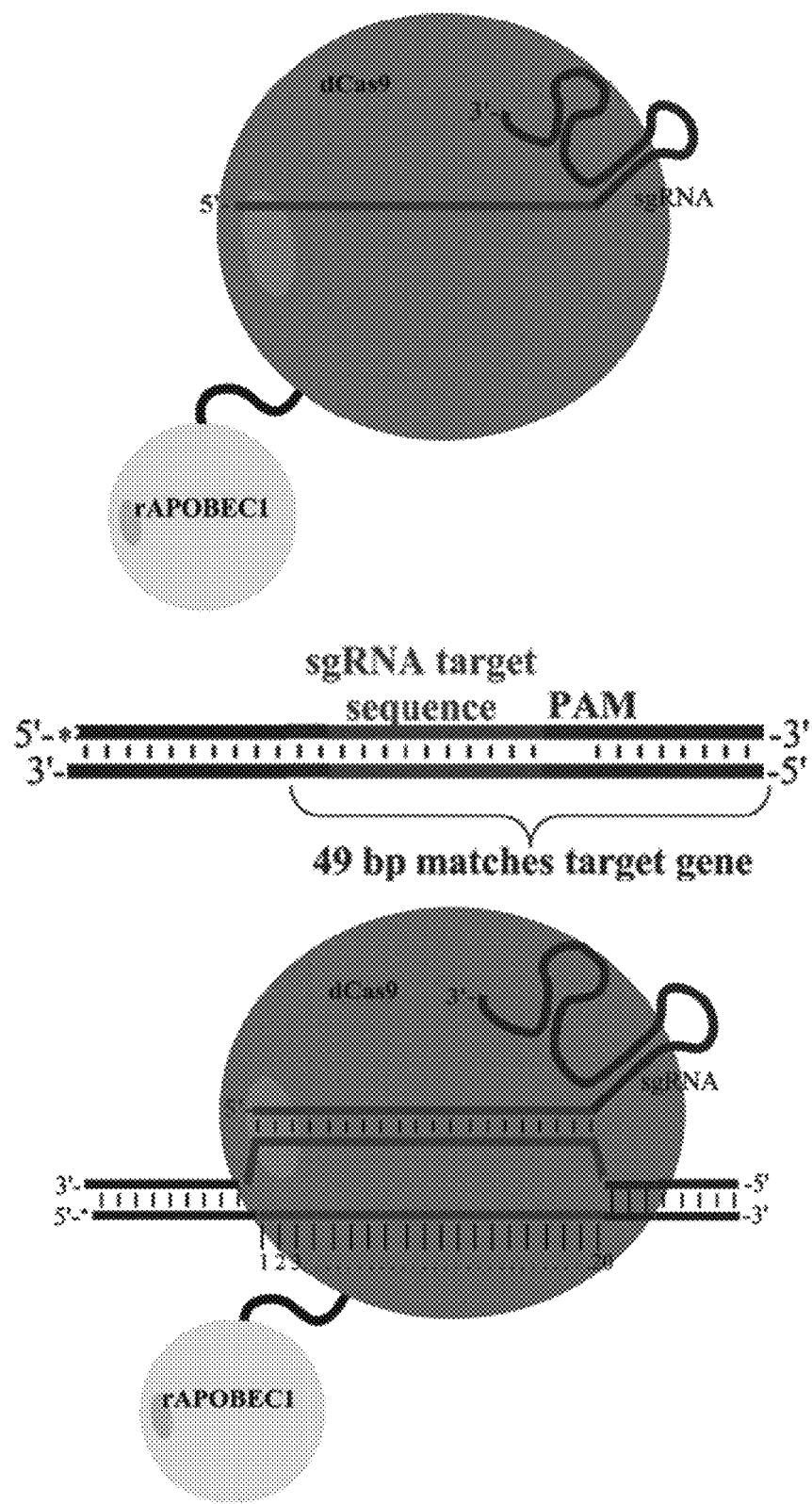
FIG. 7 illustrates the mechanism of target DNA binding of in vivo target sequences by deaminase-dCas9:sgRNA complexes.
Figure 8:
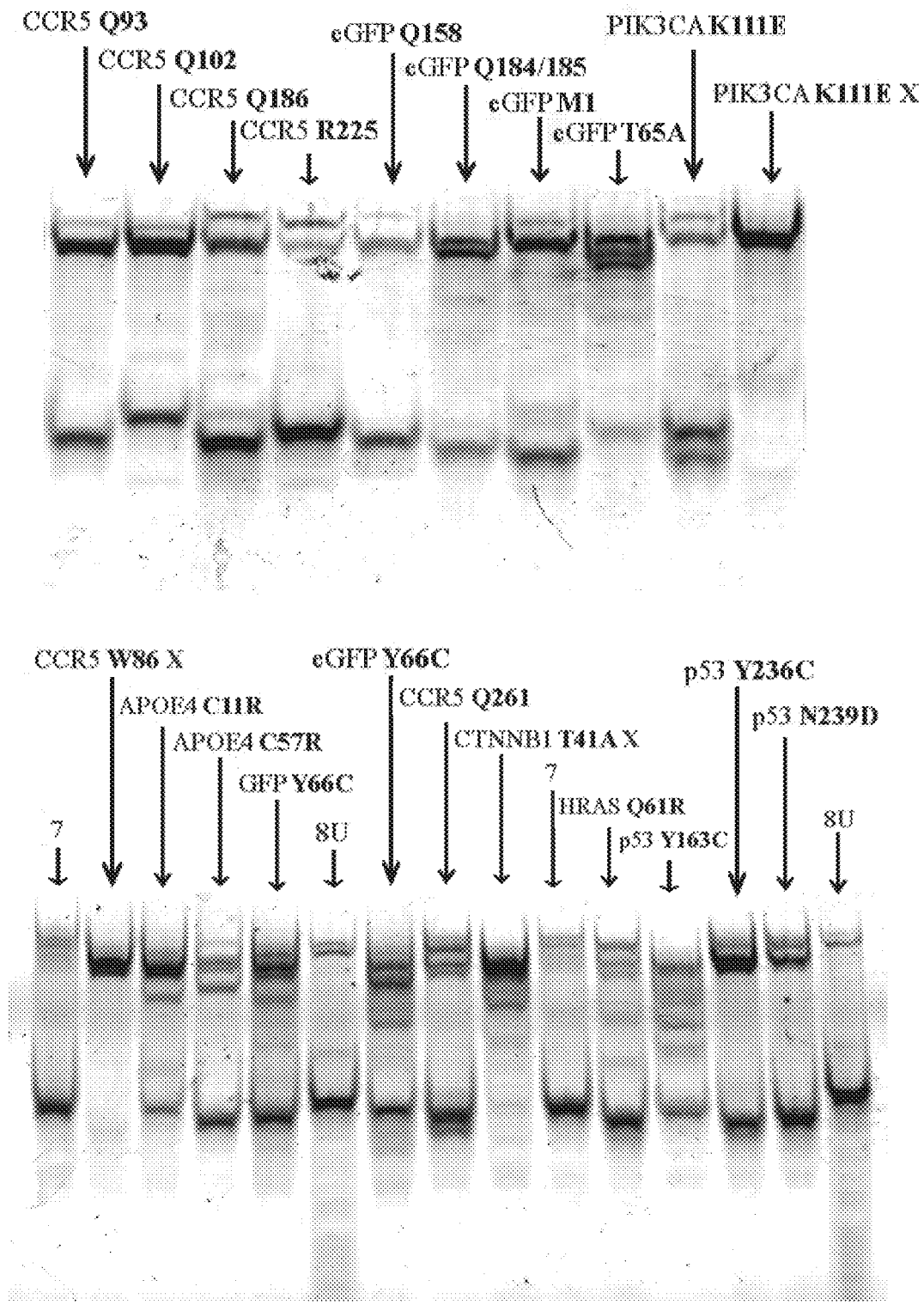
FIG. 8 shows successful deamination of exemplary disease-associated target sequences.

The feasibility of deaminating these target sequences in double-stranded DNA is demonstrated in FIGS. 7 and 8. FIG. 7 illustrates the mechanism of target DNA binding of in vivo target sequences by deaminase-dCas9:sgRNA complexes.

FIG. 8 shows successful deamination of exemplary disease-associated target sequences. Upper Gel: CCR5 Q93: coding strand target in pos. 10 (potential off-targets at positions 2, 5, 6, 8, 9); CCR5 Q102: coding strand target in pos. 9 (potential off-targets at positions 1, 12, 14); CCR5 Q186: coding strand target in pos. 9 (potential off-targets at positions 1, 5, 15); CCR5 R225: coding strand target in pos. 6 (no potential off-targets); eGFP Q158: coding strand target in pos. 5 (potential off-targets at positions 1, 13, 16); eGFP Q184/185: coding strand target in pos. 4 and 7 (potential off-targets at positions 3, 12, 14, 15, 16, 17, 18); eGFP M1: template strand target in pos. 12 (potential off-targets at positions 2, 3, 7, 9, 11) (targets positions 7 and 9 to small degree); eGFP T65A: template strand target in pos. 7 (potential off-targets at positions 1, 8, 17); PIK3CA K111E: template strand target in pos. 2 (potential off-targets at positions 5, 8, 10, 16, 17); PIK3CA K111E: template strand target in pos. 13 (potential off-targets at positions 11, 16, 19) X. Lower Gel: CCR5 W86: template strand target in pos. 2 and 3 (potential off-targets at positions 1, 13) X; APOE4 C11R: coding strand target in pos. 11 (potential off-targets at positions 7, 13, 16, 17); APOE4 C57R: coding strand target in pos. 5) (potential off-targets at positions 7, 8, 12); eGFP Y66C: template strand target in pos. 11 (potential off-targets at positions 1, 4, 6, 8, 9, 16); eGFP Y66C: template strand target in pos. 3 (potential off-targets at positions 1, 8, 17); CCR5 Q261: coding strand target in pos. 10 (potential off-targets at positions 3, 5, 6, 9, 18); CTNNB1 T41A: template strand target in pos. 7 (potential off-targets at positions 1, 13, 15, 16) X; HRAS Q61R: template strand target in pos. 6 (potential off-targets at positions 1, 2, 4, 5, 9, 10, 13); p53 Y163C: template strand target in pos. 6 (potential off-targets at positions 2, 13, 14); p53 Y236C: template strand target in pos. 8 (potential off-targets at positions 2, 4); p53 N239D: template strand target in pos. 4 (potential off-targets at positions 6, 8). Exemplary DNA sequences of disease targets are provided below (PAMs (5'-NGG-3') and target positions are boxed):

(SEQ ID NO: 636)
CCR5 Q93: 5'-Cy3-
GTAGGTAGTTAGGATGAATGGAAGGTTGGTAACTATGCTGCCGCC
CAGTGGGACTTTGGAAATACAATGTGTCAACTCTT-3'

(SEQ ID NO: 637)
CCR5 Q102: 5'-Cy3-
GTAGGTAGTTAGGATGAATGGAAGGTTGGTAAAATACAATGTGT
CAACTCTTGACAGGGCTCTATTTTATAGGCTTCTTC-3'

(SEQ ID NO: 638)
CCR5 Q186: 5'-Cy3-
GTAGGTAGTTAGGATGAATGGAAGGTTGGTATTTTCCATACAGT
CAGTATCAATTCTGGAAGAATTTCCAGACATTAAAG-3'

(SEQ ID NO: 639)
CCR5 R225: 5'-Cy3-
GTAGGTAGTTAGGATGAATGGAAGGTTGGTAGCTTCGGTGTCGA
AATGAGAAGAAGAGGCACAGGGCTGTGAGGCTTATC-3'

(SEQ ID NO: 640)
CCR5 W86: 5'-Cy3-
GTAGGTAGTTAGGATGAATGGAAGGTTGGTAGTGAGCCGAAGG
GGACAGTAAGAAGGAAAAACAGGTCAGAGATGGCC-3'

(SEQ ID NO: 641)
CCR5 Q261: 5'-Cy3-
GTAGGTAGTTAGGATGAATGGAAGGTTGGTATCCTGAACACCTT
CCAGGAATTCTTTGGCCTGAATAATTGCAGTAGCTC-3'

(SEQ ID NO: 642)
APOE4 C11R: 5'-Cy3-
GTAGGTAGTTAGGATGAATGGAAGGTTGGTAGACATGGAGGAC
GTGCGCGGCCGCCTGGTGCAGTACCGCGGCGAGGTGC-3'

(SEQ ID NO: 643)
APOE4 C57R: 5'-Cy3-
GTAGGTAGTTAGGATGAATGGAAGGTTGGTACTGCAGAAGCGC
CTGGCAGTGTACCAGGCCGGGGCCCGCGAGGGCGCCG-3'

(SEQ ID NO: 644)
eGFP Q158: 5'-Cy3-
GTAGGTAGTTAGGATGAATGGAAGGTTGGTAGCCGACAAGCAGA
AGAACGGCATCAAGGTGAACTTCAAGATCCGCCACA-3'

(SEQ ID NO: 645)
eGFP Q184/185: 5'-Cy3-
GTAGGTAGTTAGGATGAATGGAAGGTTGGTAACCACTACC
AGCAGAACACCCCCATTGGCGACGGCCCCGTGCTGCTGCC-3'

(SEQ ID NO: 646)
eGFP M1: 5'-Cy3-
GTAGGTAGTTAGGATGAATGGAAGGTTGGTACCTCGCCCTTGCTCA
CCATCTCGAGTCGGCCGCCAGTGTGATGGATATCT-3'

(SEQ ID NO: 647)
eGFP T65A: 5'-Cy3-
GTAGGTAGTTAGGATGAATGGAAGGTTGGTACACGCGTAGGCCA
GGGTGGTCACGAGGGTGGGCCAGGGCACGGGCAGC-3'

(SEQ ID NO: 648)
eGFP Y66C: 5'-Cy3-
GTAGGTAGTTAGGATGAATGGAAGGTTGGTAAAGCACTGCACTC
CGCAGGTCAGGGTGGTCACGAGGGTTGGCCAGGGCA-3'

(SEQ ID NO: 649)
eGFP Y66C: 5'-Cy3-
GTAGGTAGTTAGGATGAATGGAAGGTTGGTACACTCCGCAGGTC
AGGGTGGTCACGAGGGTTGGCCAGGGCACGGGCAGG-3'

(SEQ ID NO: 650)
PIK3CA K111E: 5'-Cy3-
GTAGGTAGTTAGGATGAATGGAAGGTTGGTAGGATCTCTTC
TTCACGGTTGCCTACTGGTTCAATTACTTTTAAAAATGG-3'

(SEQ ID NO: 651)
PIK3CA K111E: 5'-Cy3-
GTAGGTAGTTAGGATGAATGGAAGGTTGGTATTCTCGATTG
AGGATCTCTTCTTCACGGTTGCCTACTGGTTCAATTACT-3'

(SEQ ID NO: 652)
CTNNB1 T41A: 5'-Cy3-
GTAGGTAGTTAGGATGAATGGAAGGTTGGTAAGGAGCTGTGG
CAGTGGCACCAGAATGGATTCCAGAGTCCAGGTAAGAC-3'

(SEQ ID NO: 653)
HRAS Q61R: 5'-Cy3-
GTAGGTAGTTAGGATGAATGGAAGGTTGGTAGTACTCCTCCCGG
CCGGCGGTATCCAGGATGTCCAACAGGCACGTCTCC-3'

(SEQ ID NO: 654)
p53 Y163C: 5'-Cy3-
GTAGGTAGTTAGGATGAATGGAAGGTTGGTATGACTGCTTGCAG
ATGGCCATGGCGCGGACGCGGGTGCCGGGCGGGGT-3'

-continued (SEQ ID NO: 655)
p53 Y236C: 5'-Cy3-
GTAGGTAGTTAGGATGAATGGAAGGTTGGTACTGTTACACATGC
AGTTGTAGTGGATGG*TGGTACAGTCAGAGCCAACCT*-3'

(SEQ ID NO: 656)
p53 N239D: 5'-Cy3-
GTAGGTAGTTAGGATGAATGGAAGGTTGGTAGGAACTGTCACAC
ATGTAGTTGTAGTGG*ATGGTGGTACAGTCAGAGCCA*-3'

Example 3: Uracil Glycosylase Inhibitor Fusion Improves Deamination Efficiency Direct programmable nucleobase editing efficiencies in mammalian cells by dCas9:deaminase fusion proteins can be improved significantly by fusing a uracil glycosylase inhibitor (UGI) to the dCas9:deaminase fusion protein.

Figure 9:
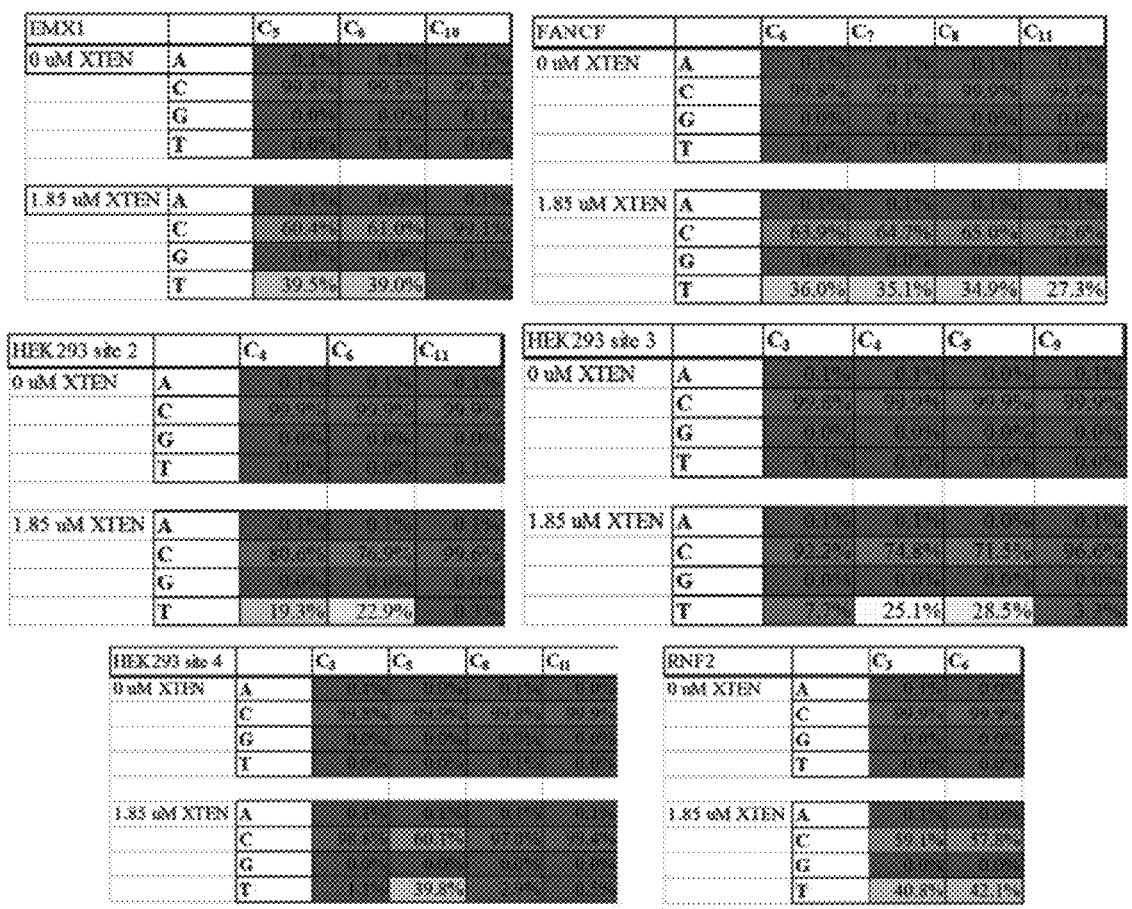
FIG. 9 shows in vitro C→T editing efficiencies using His6-rAPOBEC1-XTEN-dCas9.

FIG. 9 shows in vitro C→T editing efficiencies in human HEK293 cells using rAPOBEC1-XTEN-dCas9:

(SEQ ID NO: 657)
rAPOBEC1-XTEN-dCas9-*NLS* primary sequence

MSSETGPVAVDPTLRRRIEPHEFEVFFDPRELRKETCLLYEINWGGRHSIWRHTSQNT

NKHVEVNFIEKFTTERYFCPNTRCSITWFLSWSPCGECSRAITEFLSRYPHVTLFIYIAR

LYHHADPRNRQGLRDLISSGVTIQIMTEQESGYCWRNFVNYSPSNEAHWPRYPHLWV

RLYVLELYCIILGLPPCLNILRRKQPQLTFFTIALQSCHYQRLPPHILWATGLKSGSETP

GTSESATPESDKKYSIGLAIGTNSVGWAVITDEYKVPSKKFKVLGNTDRHSIKKNIG

ALLFDSGETAEATRLKRTARRRYTRRKNRICYLQEIFSNEMAKVDDSFFHRLEESFLV

EEDKKHERHPIFGNIVDEVAYHEKYPTIYHLRKKLVDSTDKADLRLIYLALAHMIKFR

GHFLIEGDLNPDNSDVDKLFIQLVQTYNQLFEENPINASGVDAKAILSARLSKSRRLE

NLIAQLPGEKKNGLFGNLIALSLGLTPNFKSNFDLAEDAKLQLSKDTYDDDLDNLLA

QIGDQYADLFLAAKNLSDAILLSDILRVNTEITKAPLSASMIKRYDEHHQDLTLLKALV

RQQLPEKYKEIFFDQSKNGYAGYIDGGASQEEFYKFIKPILEKMDGTEELLVKLNRED

LLRKQRTFDNGSIPHQIHLGELHAILRRQEDFYPFLKDNREKIEKILTFRIPYYVGPLAR

GNSRFAWMTRKSEETITPWNFEEVVDKGASAQSFIERMTNFDKNLPNEKVLPKHSLL

YEYFTVYNELTKVKYVTEGMRKPAFLSGEQKKAIVDLLFKTNRKVTVKQLKEDYFK

KIECFDSVETSGVEDRFNASLGTYHDLLKIIKDKDFLDNEENEDILEDIVLTLTLFEDRE

MIEERLKTYAHLFDDKVMKQLKRRRYTGWGRLSRKLINGIRDKQSGKTILDFLKSDG

FANRNFMQLIHDDSLTFKEDIQKAQVSGQGDSLHEHIANLAGSPAIKKGILQTVKVVD

ELVKVMGRHKPENIVIEMARENQTTQKGQKNSRERMKRIEEGIKELGSQILKEHPVE

NTQLQNEKLYLYYLQNGRDMYVDQELDINRLSDYDVDAIVPQSFLKDDSIDNKVLT

RSDKNRGKSDNVPSEEVVKKMKNYWRQLLNAKLITQRKFDNLTKAERGGLSELDK

AGFIKRQLVETRQITKHVAQILDSRMNTKYDENDKLIREVKVITLKSKLVSDFRKDFQ

FYKVREINNYHHAHDAYLNAVVGTALIKKYPKLESEFVYGDYKVYDVRKMIAKSEQ

EIGKATAKYFFYSNIMNFFKTEITLANGEIRKRPLIETNGETGEIVWDKGRDFATVRKV

LSMPQVNIVKKTEVQTGGFSKESILPKRNSDKLIARKKDWDPKKYGGFDSPTVAYSV

LVVAKVEKGKSKKLKSVKELLGITIMERSSFEKNPIDFLEAKGYKEVKKDLIIKLPKYS

LFELENGRKRMLASAGELQKGNELALPSKYVNFLYLASHYEKLKGSPEDNEQKQLF

VEQHKHYLDEIIEQISEFSKRVILADANLDKVLSAYNKHRDKPIREQAENIIHLFTLTNL

GAPAAFKYFDTTIDRKRYTSTKEVLDATLIHQSITGLYETRIDLSQLGGD*SGSPKKKR*

*KV*

Protospacer sequences were as follows:

(SEQ ID NO: 293)
EMX1:    5'- GAGTC$_5$C$_6$GAGC$_{10}$AGAAGAAGAA GGG -3'

(SEQ ID NO: 294)
FANCF:   5'- GGAATC$_6$C$_7$C$_8$TTC$_{11}$TGCAGCACC TGG -3'

(SEQ ID NO: 295)
HEK293 site 2: 5'-GAAC$_4$AC$_6$AAAGC$_{11}$ATAGACTGC GGG -3'

(SEQ ID NO: 296)
HEK293 site 3: 5'-GGC$_3$C$_4$C$_5$AGAC$_9$TGAGCACGTGA TGG -3'

(SEQ ID NO: 297)
HEK293 site 4: 5'-GGC$_3$AC$_5$TGC$_8$GGC$_{11}$TGGAGGTGG GGG -3'

(SEQ ID NO: 298)
RNF2:    5'- GTC$_3$ATC$_6$TTAGTCATTACCTG AGG -3'

*PAMs are boxed, C residues within target window (positions 3-11) are numbered and bolded.

Figure 10:
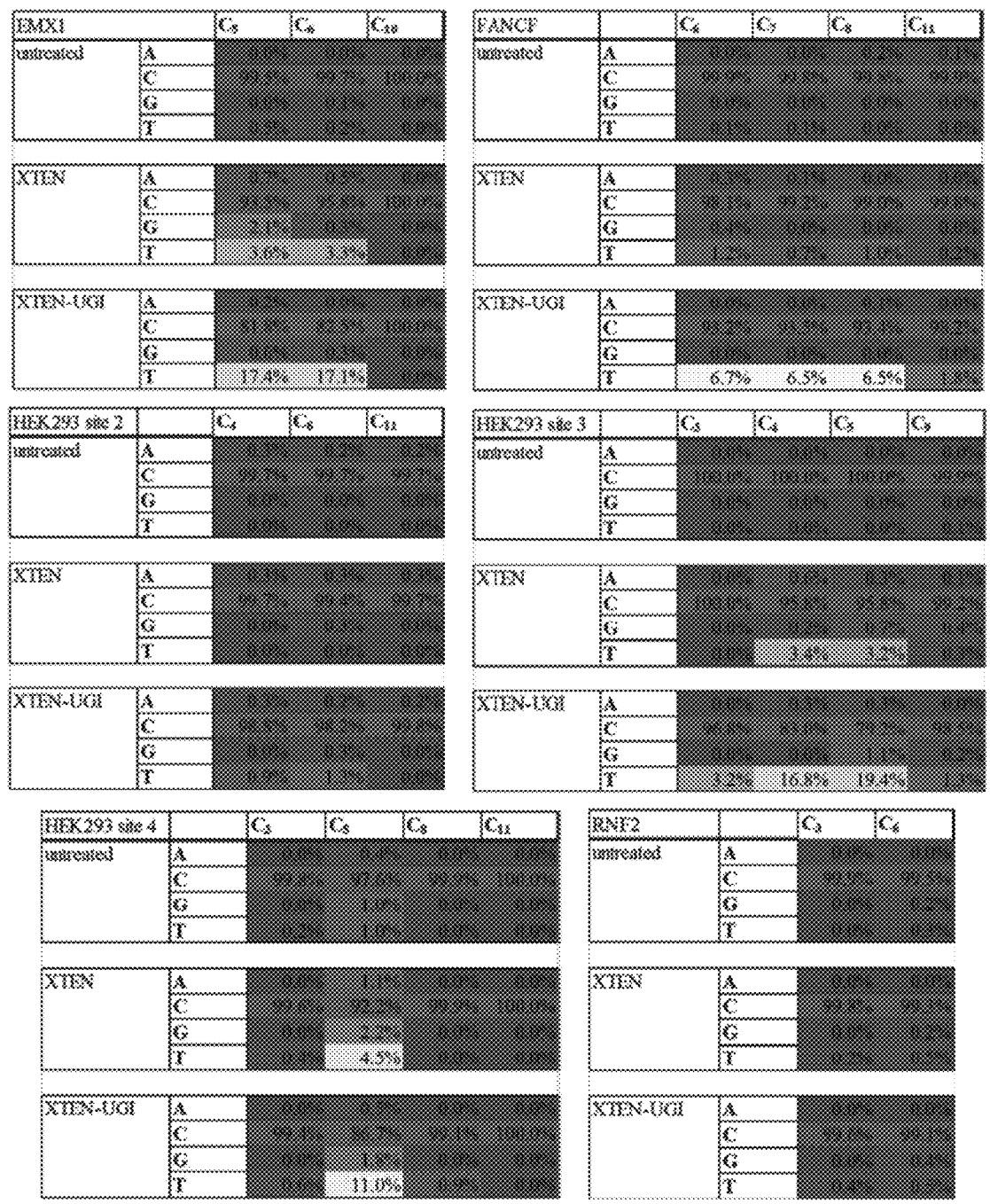
FIG. 10 shows C→T editing efficiencies in HEK293T cells is greatly enhanced by fusion with UGI.

FIG. 10 demonstrates that C→T editing efficiencies on the same protospacer sequences in HEK293T cells are greatly enhanced when a UGI domain is fused to the rAPOBEC1:dCas9 fusion protein.

rAPOBEC1-XTEX-dCas9-UGI-NLS primary sequence (SEQ ID NO: 658)
MSSETGPVAVDPTLRRRIEPHEFEVFFDPRELRKETCLLYEINWGGRHSIWRHTSQNT

NKHVEVNFIEKFTTERYFCPNTRCSITWFLSWSPCGECSRAITEFLSRYPHVTLFIYIAR

LYHHADPRNRQGLRDLISSGVTIQIMTEQESGYCWRNFVNYSPSNEAHWPRYPHLWV

RLYVLELYCIILGLPPCLNILRRKQPQLTFFTIALQSCHYQRLPPHILWATGLKSGSETP

GTSESATPESDKKYSIGLAIGTNSVGWAVITDEYKVPSKKFKVLGNTDRHSIKKNIG

ALLFDSGETAEATRLKRTARRRYTRRKNRICYLQEIFSNEMAKVDDSFFHRLEESFLV

EEDKKHERHPIFGNIVDEVAYHEKYPTIYHLRKKLVDSTDKADLRLIYLALAHMIKFR

GHFLIEGDLNPDNSDVDKLFIQLVQTYNQLFEENPINASGVDAKAILSARLSKSRRLE

NLIAQLPGEKKNGLFGNLIALSLGLTPNFKSNFDLAEDAKLQLSKDTYDDDLDNLLA

QIGDQYADLFLAAKNLSDAILLSDILRVNTEITKAPLSASMIKRYDEHHQDLTLLKALV

RQQLPEKYKEIFFDQSKNGYAGYIDGGASQEEFYKFIKPILEKMDGTEELLVKLNRED

LLRKQRTFDNGSIPHQIHLGELHAILRRQEDFYPFLKDNREKIEKILTFRIPYYVGPLAR

GNSRFAWMTRKSEETITPWNFEEVVDKGASAQSFIERMTNFDKNLPNEKVLPKHSLL

YEYFTVYNELTKVKYVTEGMRKPAFLSGEQKKAIVDLLFKTNRKVTVKQLKEDYFK

KIECFDSVETSGVEDRFNASLGTYHDLLKIIKDKDFLDNEENEDILEDIVLTLTLFEDRE

MIEERLKTYAHLFDDKVMKQLKRRRYTGWGRLSRKLINGIRDKQSGKTILDFLKSDG

FANRNFMQLIHDDSLTFKEDIQKAQVSGQGDSLHEHIANLAGSPAIKKGILQTVKVVD

ELVKVMGRHKPENIVIEMARENQTTQKGQKNSRERMKRIEEGIKELGSQILKEHPVE

NTQLQNEKLYLYYLQNGRDMYVDQELDINRLSDYDVDAIVPQSFLKDDSIDNKVLT

RSDKNRGKSDNVPSEEVVKKMKNYWRQLLNAKLITQRKFDNLTKAERGGLSELDK

AGFIKRQLVETRQITKHVAQILDSRMNTKYDENDKLIREVKVITLKSKLVSDFRKDFQ

FYKVREINNYHHAHDAYLNAVVGTALIKKYPKLESEFVYGDYKVYDVRKMIAKSEQ

EIGKATAKYFFYSNIMNFFKTEITLANGEIRKRPLIETNGETGEIVWDKGRDFATVRKV

LSMPQVNIVKKTEVQTGGFSKESILPKRNSDKLIARKKDWDPKKYGGFDSPTVAYSV

LVVAKVEKGKSKKLKSVKELLGITIMERSSFEKNPIDFLEAKGYKEVKKDLIIKLPKYS

LFELENGRKRMLASAGELQKGNELALPSKYVNFLYLASHYEKLKGSPEDNEQKQLF

VEQHKHYLDEIIEQISEFSKRVILADANLDKVLSAYNKHRDKPIREQAENIIHLFTLTNL

GAPAAFKYFDTTIDRKRYTSTKEVLDATLIHQSITGLYETRIDLSQLGGDSGGSTNLSD

IIEKETGKQLVIQESILMLPEEVEEVIGNKPESDILVHTAYDESTDENVMLLTSDAP

EYKPWALVIQDSNGENKIKMLSGGS*PKKKRKV*

The percentages in FIGS. 9 and 10 are shown from sequencing both strands of the target sequence. Because only one of the strands is a substrate for deamination, the maximum possible deamination value in this assay is 50%. Accordingly, the deamination efficiency is double the percentages shown in the tables. E.g., a value of 50% relates to deamination of 100% of double-stranded target sequences.

When a uracil glycosylase inhibitor (UGI) was fused to the dCas9:deaminase fusion protein (e.g., rAPOBEC1-XTEN-dCas9-[UGI]-NLS), a significant increase in editing efficiency in cells was observed. This result indicates that in mammalian cells, the DNA repair machinery that cuts out the uracil base in a U:G base pair is a rate-limiting process in DNA editing. Tethering UGI to the dVas9:deaminase fusion proteins greatly increases editing yields.

Without UGI, typical editing efficiencies in human cells were in the ~2-14% yield range (FIG. 9 and FIG. 10, "XTEN" entries). With UGI (FIG. 10, "UGI" entries) the editing was observed in the ~6-40% range. Using a UGI fusion is thus more efficient than the current alternative method of correcting point mutations via HDR, which also creates an excess of indels in addition to correcting the point mutation. No indels resulting from treatment with the cas9: deaminase:UGI fusions were observed.

Example 4: Direct, Programmable Conversion of a Target Nucleotide in Genomic DNA without Double-Stranded DNA Cleavage Current genome-editing technologies introduce double-stranded DNA breaks at a target locus of interest as the first step to gene correction.[39,40] Although most genetic diseases arise from mutation of a single nucleobase to a different nucleobase, current approaches to revert such changes are very inefficient and typically induce an abundance of random insertions and deletions (indels) at the target locus as a consequence of the cellular response to double-stranded DNA breaks.[39,40] Reported herein is the development of nucleobase editing, a new strategy for genome editing that enables the direct conversion of one target nucleobase into another in a programmable manner, without requiring double-stranded DNA backbone cleavage. Fusions of CRISPR/Cas9 were engineered and the cytidine deaminase enzyme APOBEC1 that retain the ability to be programmed with a guide RNA, do not induce double-stranded DNA breaks, and mediate the direct conversion of cytidine to uracil, thereby effecting a C→T (or G→A) substitution following DNA replication, DNA repair, or transcription if the template strand is targeted. The resulting "nucleobase editors" convert cytidines within a window of approximately five nucleotides, and can efficiently correct a variety of point mutations relevant to human disease in vitro. In four transformed human and murine cell lines, second- and third-generation nucleobase editors that fuse uracil glycosylase inhibitor (UGI), and that use a Cas9 nickase targeting the non-edited strand, respectively, can overcome the cellular DNA repair response to nucleobase editing, resulting in permanent correction of up to 37% or (~15-75%) of total cellular DNA in human cells with minimal (typically ≤1%) indel formation. In contrast, canonical Cas9-mediated HDR on the same targets yielded an average of 0.7% correction with 4% indel formation. Nucleobase editors were used to revert two oncogenic p53 mutations into wild-type alleles in human breast cancer and lymphoma cells, and to convert an Alzheimer's Disease associated Arg codon in ApoE4 into a non-disease-associated Cys codon in mouse astrocytes. Base editing expands the scope and efficiency of genome editing of point mutations.

The clustered regularly interspaced short palindromic repeat (CRISPR) system is a prokaryotic adaptive immune system that has been adapted to mediate genome engineering in a variety of organisms and cell lines.[41] CRISPR/Cas9 protein-RNA complexes localize to a target DNA sequence through base pairing with a guide RNA, and natively create a DNA double-stranded break (DSB) at the locus specified by the guide RNA. In response to DSBs, endogenous DNA repair processes mostly result in random insertions or deletions (indels) at the site of DNA cleavage through non-homologous end joining (NHEJ). In the presence of a homologous DNA template, the DNA surrounding the cleavage site can be replaced through homology-directed repair (HDR). When simple disruption of a disease-associated gene is sufficient (for example, to treat some gain-of-function diseases), targeted DNA cleavage followed by indel formation can be effective. For most known genetic diseases, however, correction of a point mutation in the target locus, rather than stochastic disruption of the gene, is needed to address or study the underlying cause of the disease.[68]

Motivated by this need, researchers have invested intense effort to increase the efficiency of HDR and suppress NHEJ. For example, a small-molecule inhibitor of ligase IV, an essential enzyme in the NHEJ pathway, has been shown to increase HDR efficiency.[42,43] However, this strategy is challenging in post-mitotic cells, which typically down-regulate HDR, and its therapeutic relevance is limited by the potential risks of inhibiting ligase IV in non-target cells. Enhanced HDR efficiency can also be achieved by the timed delivery of Cas9-guide RNA complexes into chemically synchronized cells, as HDR efficiency is highly cell-cycle dependent.[44] Such an approach, however, is limited to research applications in cell culture since synchronizing cells is highly disruptive. Despite these developments, current strategies to replace point mutations using HDR in most contexts are very inefficient (typically ~0.1 to 5%),[42,43,45,46,75] especially in unmodified, non-dividing cells. In addition, HDR competes with NHEJ during the resolution of double-stranded breaks, and indels are generally more abundant outcomes than gene replacement. These observations highlight the need to develop alternative approaches to install specific modifications in genomic DNA that do not rely on creating double-stranded DNA breaks. A small-molecule inhibitor of ligase IV, an essential enzyme in the NHEJ pathway, has been shown to increase HDR efficiency.[42,43] However, this strategy is challenging in post-mitotic cells, which typically down-regulate HDR, and its therapeutic relevance is limited by the potential risks of inhibiting ligase IV in non-target cells. Enhanced HDR efficiency can also be achieved by the timed delivery of Cas9-guide RNA complexes into chemically synchronized cells, as HDR efficiency is highly cell-cycle dependent.[44] Such an approach, however, is limited to research applications in cell culture since synchronizing cells is highly disruptive. In some cases, it is possible to design HDR templates such that the product of successful HDR contains mutations in the PAM sequence and therefore is no longer a substrate for subsequent Cas9 modification, increasing the overall yield of HDR products,[75] although such an approach imposes constraints on the product sequences. Recently, this strategy has been coupled to the use of ssDNA donors that are complementary to the non-target strand and high-efficiency ribonucleoprotein (RNP) delivery to substantially increase the efficiency of HDR, but even in these cases the ratio of HDR to NHEJ outcomes is relatively low (<2).[83]

It was envisioned that direct catalysis of the conversion of one nucleobase to another at a programmable target locus without requiring DNA backbone cleavage could increase the efficiency of gene correction relative to HDR without introducing undesired random indels at the locus of interest. Catalytically dead Cas9 (dCas9), which contains Asp10Ala and His840Ala mutations that inactivate its nuclease activity, retains its ability to bind DNA in a guide RNA-programmed manner but does not cleave the DNA backbone.[16, 47] In principle, conjugation of dCas9 with an enzymatic or chemical catalyst that mediates the direct conversion of one nucleobase to another could enable RNA-programmed nucleobase editing. The deamination of cytosine (C) is catalyzed by cytidine deaminases[29] and results in uracil (U), which has the base pairing properties of thymine (T). dCas9 was fused to cytidine deaminase enzymes in order to test their ability to convert C to U at a guide RNA-specified DNA locus. Most known cytidine deaminases operate on RNA, and the few examples that are known to accept DNA require single-stranded DNA.[48] Recent studies on the dCas9-target DNA complex reveal that at least nine nucleotides of the displaced DNA strand are unpaired upon formation of the Cas9:guide RNA:DNA "R-loop" complex.[12] Indeed, in the structure of the Cas9 R-loop complex the first 11 nucleotides of the protospacer on the displaced DNA strand are disordered, suggesting that their movement is not highly restricted.[76] It has also been speculated that Cas9 nickase-induced mutations at cytosines in the non-template strand might arise from their accessibility by cellular cytidine deaminase enzymes.[77] Recent studies on the dCas9-target DNA complex have revealed that at least 26 bases on the non-template strand are unpaired when Cas9 binds to its target DNA sequence.[49] It was reasoned that a subset of this stretch of single-stranded DNA in the R-loop might serve as a substrate for a dCas9-tethered cytidine deaminase to effect direct, programmable conversion of C to U in DNA (FIG. 11A).

Figure 36A:
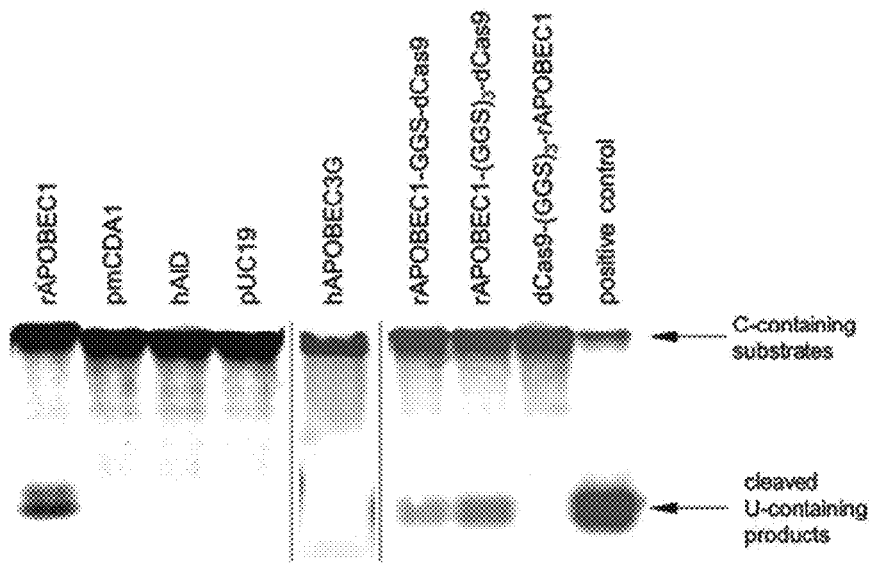
Figure 36B:
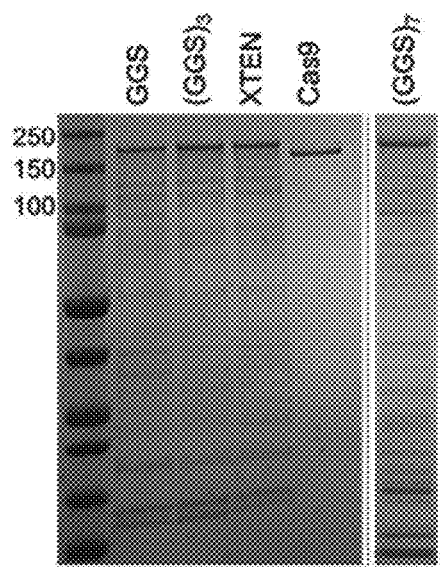
Figure 36C:
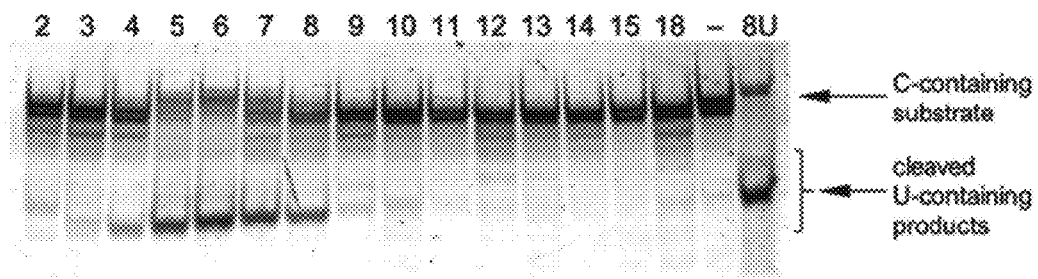

Four different cytidine deaminase enzymes (hAID, hAPOBEC3G, rAPOBEC1, and pmCDA1) were expressed in a mammalian cell lysate-derived in vitro transcription-translation system and evaluated for ssDNA deamination. Of the four enzymes, rAPOBEC1 showed the highest deaminase activity under the tested conditions and was chosen for dCas9 fusion experiments (FIG. 36A). Although appending rAPOBEC1 to the C-terminus of dCas9 abolishes deaminase activity, fusion to the N-terminus of dCas9 preserves deaminase activity on ssDNA at a level comparable to that of the unfused enzyme. Four rAPOBEC1-dCas9 fusions were expressed and purified with linkers of different length and composition (FIG. 36B), and evaluated each fusion for single guide RNA (sgRNA)-programmed dsDNA deamination in vitro (FIGS. 11A to 11C and FIGS. 15A to 15D).

Figure 11A:
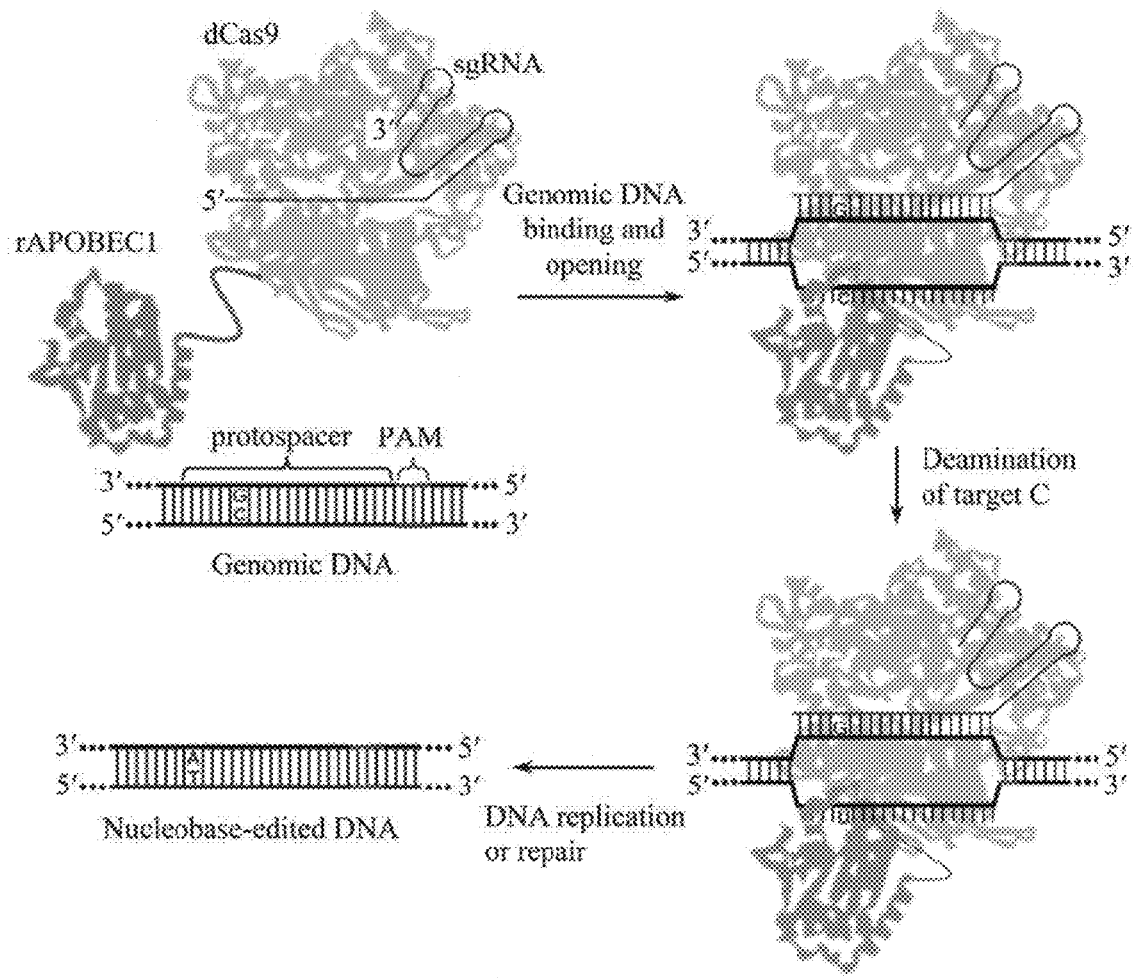
FIGS. 11A to 11C show NBE1 mediates specific, guide RNA-programmed C to U conversion in vitro.
Figure 11B:
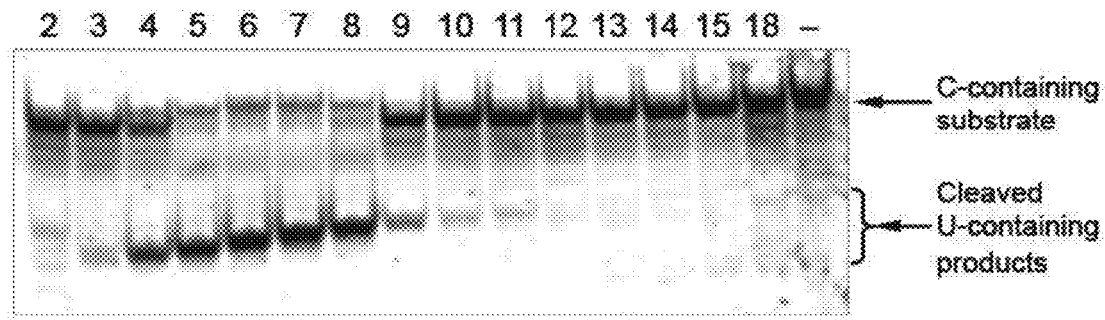
Figure 11C:
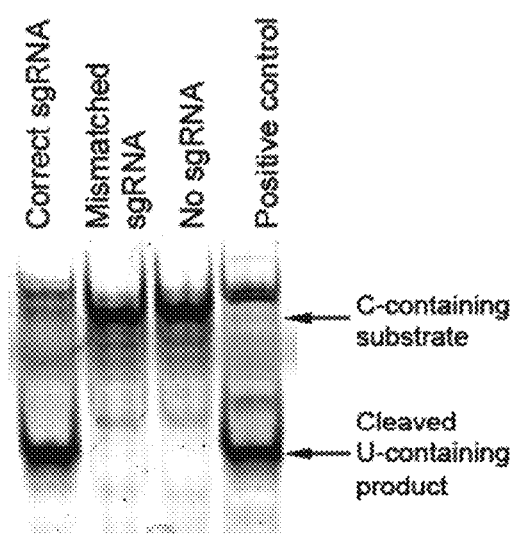

Efficient, sequence-specific, sgRNA-dependent C to U conversion was observed in vitro (FIGS. 11A to 11C). Conversion efficiency was greatest using rAPOBEC1-dCas9 linkers over nine amino acids in length. The number of positions susceptible to deamination (the deamination "activity window") increases with linker length was extended from three to 21 amino acids (FIGS. 36C to 36F 15A to 15D). The 16-residue XTEN linker[50] was found to offer a promising balance between these two characteristics, with an efficient deamination window of approximately five nucleotides, from positions 4 to 8 within the protospacer, counting the end distal to the protospacer-adjacent motif (PAM) as position 1. The rAPOBEC1-XTEN-dCas9 protein served as the first-generation nucleobase editor (NBE1).

Figure 12A:
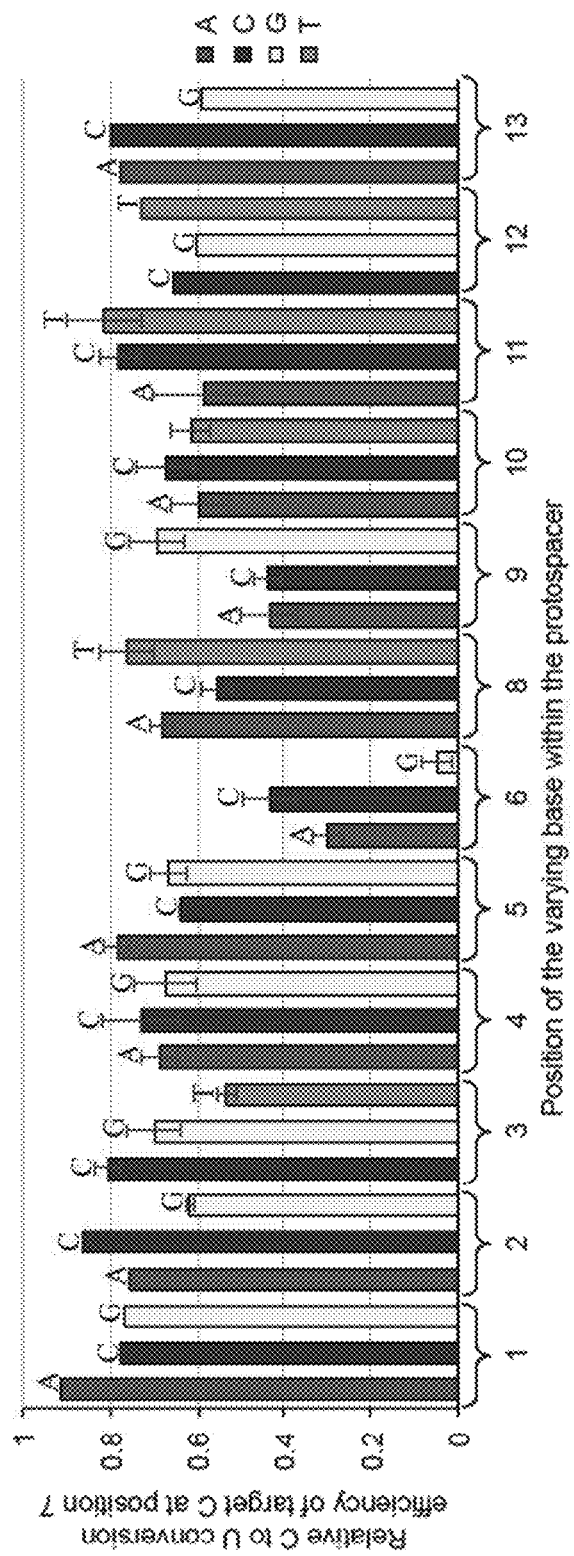
FIGS. 12A to 12B show effects of sequence context and target C position on nucleobase editing efficiency in vitro.
Figures 12B, 13A:
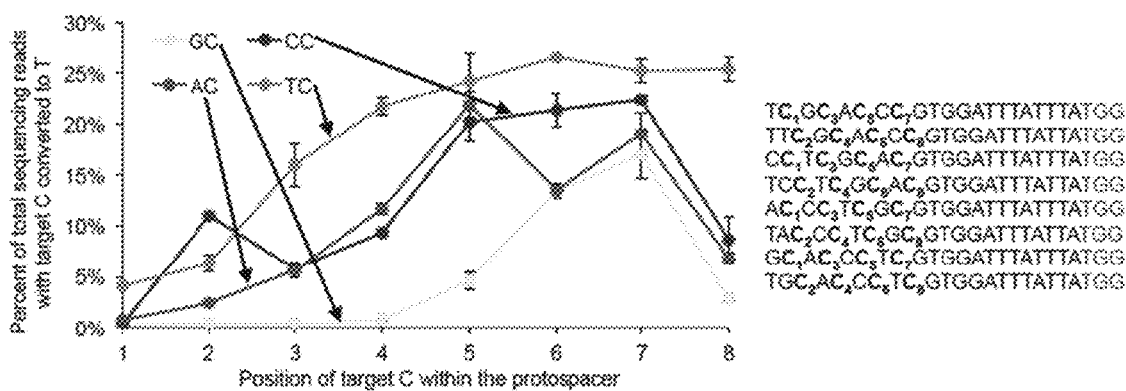
FIGS. 13A to 13C show nucleobase editing in human cells.

Elected were seven mutations relevant to human disease that in theory could be corrected by C to T nucleobase editing, synthesized double-stranded DNA 80-mers of the corresponding sequences, and assessed the ability of NBE1 to correct these mutations in vitro (FIGS. 16A to 16B). NBE1 yielded products consistent with efficient editing of the target C, or of at least one C within the activity window when multiple Cs were present, in six of these seven targets in vitro, with an average apparent editing efficiency of 44% (FIGS. 16A to 16B). In the three cases in which multiple Cs were present within the deamination window, evidence of deamination of some or all of these cytosines was observed. In only one of the seven cases tested were substantial yields of edited product observed (FIGS. 16A to 16B). Although the preferred sequence context for APOBEC1 substrates is reported to be CC or TC,[51] it was anticipated that the increased effective molarity of the deaminase and its single-stranded DNA substrate mediated by dCas9 binding to the target locus may relax this restriction. To illuminate the sequence context generality of NBE1, its ability to edit a 60-mer double-stranded DNA oligonucleotide containing a single fixed C at position 7 within the protospacer was assayed, as well as all 36 singly mutated variants in which protospacer bases 1-6 and 8-13 were individually varied to each of the other three bases. Each of these 37 sequences were treated with 1.9 µM NBE1, 1.9 µM of the corresponding sgRNA, and 125 nM DNA for 2 h, similar to standard conditions for in vitro Cas9 assays[52]. High-throughput DNA sequencing (HTS) revealed 50 to 80% C to U conversion of targeted strands (25 to 40% of total sequence reads arising from both DNA strands, one of which is not a substrate for NBE1) (FIG. 12A). The nucleotides surrounding the target C had little effect on editing efficiency was independent of sequence context unless the base immediately 5' of the target C is a G, in which case editing efficiency was substantially lower (FIGS. 12A to 12B). NBE1 activity in vitro was assessed on all four NC motifs at positions 1 through 8 within the protospacer (FIGS. 12A to 12B). In general NBE1 activity on substrates was observed to follow the order TC≥CC≥AC>GC, with maximum editing efficiency achieved when the target C is at or near position 7. In addition, it was observed that the nucleobase editor is highly processive, and will efficiently convert most of all Cs to Us on the same DNA strand within the 5-base activity window (FIG. 17).

Figures 28, 29A:
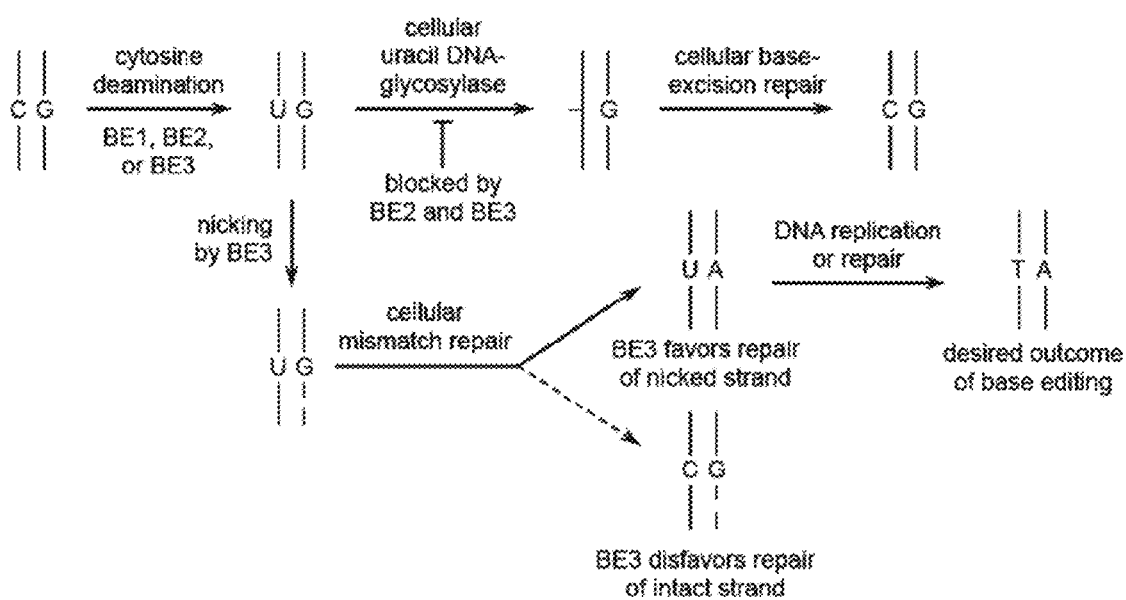
FIG. 28 shows non-target C mutation rates. Shown here are the C to T mutation rates at 2,500 distinct cytosines surrounding the six on-target and 34 off-target loci tested, representing a total of 14,700,000 sequence reads derived from approximately $1.8 \times 10^6$ cells.
FIGS. 29A to 29C show base editing in human cells.
Figure 37B:
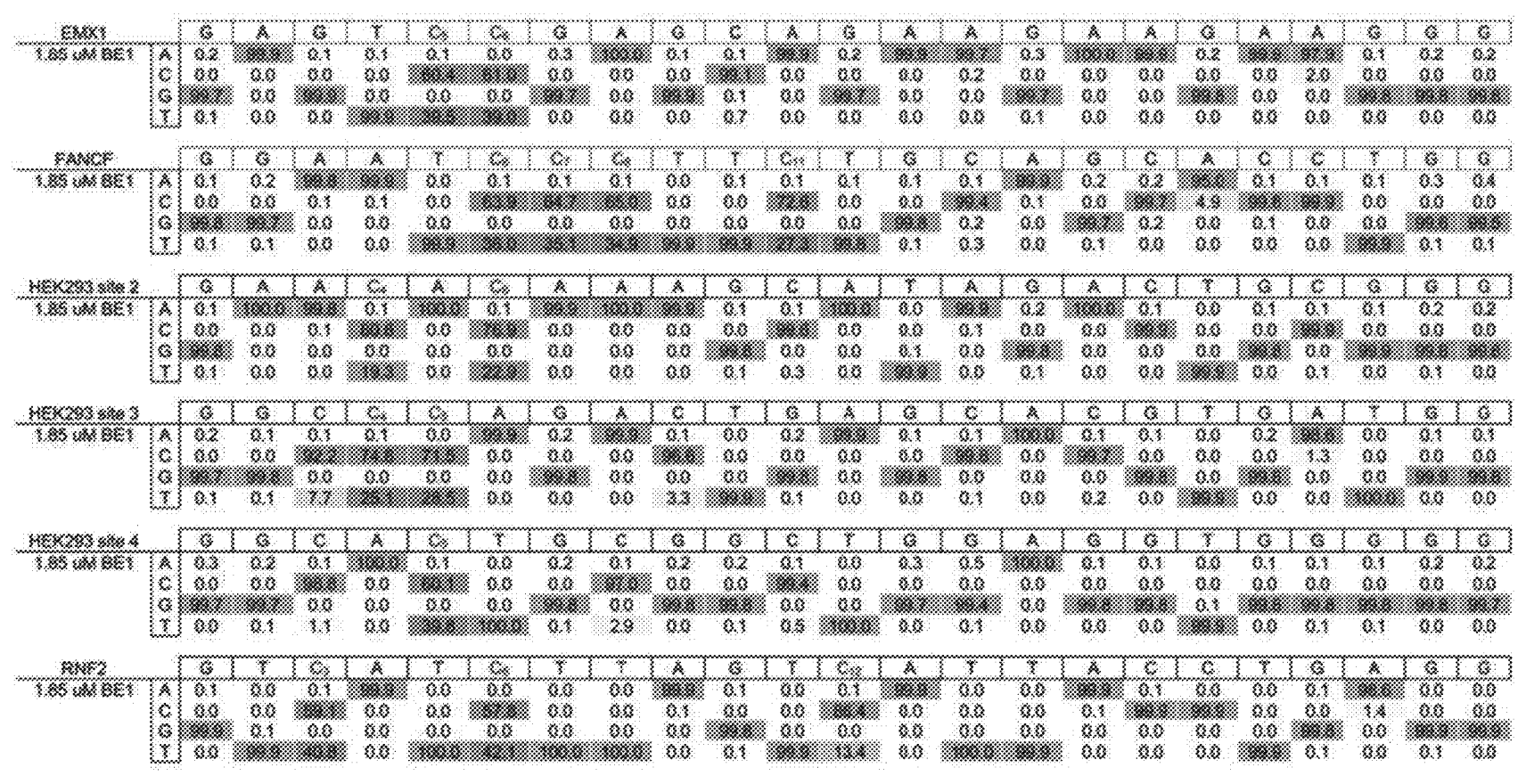
Figure 37C:
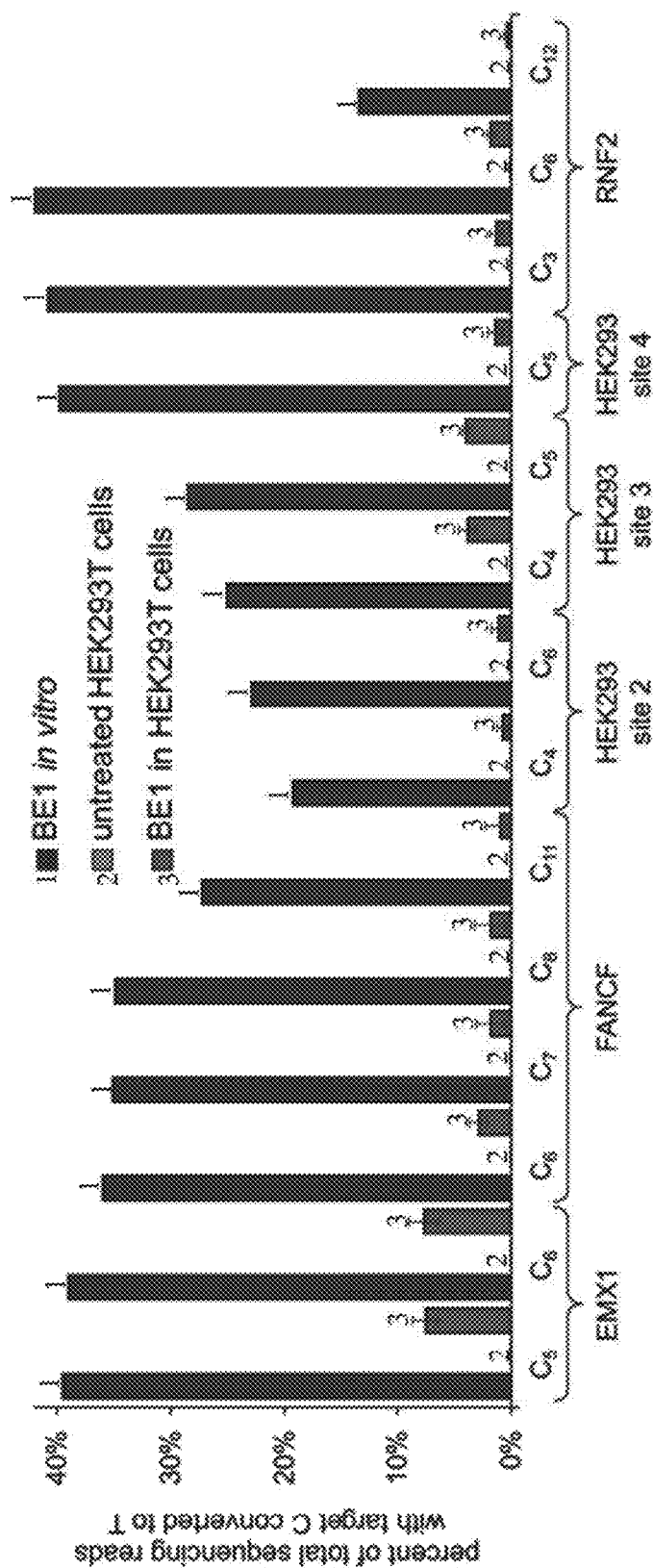

While BE1 efficiently processes substrates in a test tube, in cells a tree of possible DNA repair outcomes determines the fate of the initial U:G product of base editing (FIG. 29A). To test the effectiveness of nucleobase editing in human cells, NBE1 codon usage was optimized for mammalian expression, appended a C-terminal nuclear localization sequence (NLS),[53] and assayed its ability to convert C to T in human cells on 14Cs in six well-studied target sites throughout the human genome (FIG. 37A).[54] The editable Cs were confirmed within each protospacer in vitro by incubating NBE1 with synthetic 80-mers that correspond to the six different genomic sites, followed by HTS (FIGS. 13A to 13C, FIG. 29B and FIG. 25). Next, HEK293T cells were transfected with plasmids encoding NBE1 and one of the six target sgRNAs, allowed three days for nucleobase editing to occur, extracted genomic DNA from the cells, and analyzed the loci by HTS. Although C to T editing in cells at the target locus was observed for all six cases, the efficiency of nucleobase editing was 1.1% to 6.3% or 0.8%-7.7% of total DNA sequences (corresponding to 2.2% to 12.6% of targeted strands), a 6.3-fold to 37-fold or 5-fold to 36-fold decrease in efficiency compared to that of in vitro nucleobase editing (FIGS. 13A to 13C, FIG. 29B and FIG. 25). It was observed that some base editing outside of the typical window of positions 4 to 8 when the substrate C is preceded by a T, which we attribute to the unusually high activity of APOBEC1 for TC substrates.[48]

It was asked whether the cellular DNA repair response to the presence of U:G heteroduplex DNA was responsible for the large decrease in nucleobase editing efficiency in cells (FIG. 29A). Uracil DNA glycosylase (UDG) catalyzes removal of U from DNA in cells and initiates base excision repair (BER), with reversion of the U:G pair to a C:G pair as the most common outcome (FIG. 29A).[55] Uracil DNA glycosylase inhibitor (UGI), an 83-residue protein from *B. subtilis* bacteriophage PBS1, potently blocks human UDG activity ($IC_{50}$=12 μM).[56] UGI was fused to the C-terminus of NBE1 to create the second-generation nucleobase editor NBE2 and repeated editing assays on all six genomic loci. Editing efficiencies in human cells were on average 3-fold higher with NBE2 than with NBE1, resulting in gene conversion efficiencies of up to 22.8% of total DNA sequenced (up to 45.6% of targeted strands) (FIGS. 13A to 13C and FIG. 29B). To test base editing in human cells, BE1 codon usage was optimized for mammalian expression and appended a C-terminal nuclear localization sequence (NLS).[53]

Figure 19:
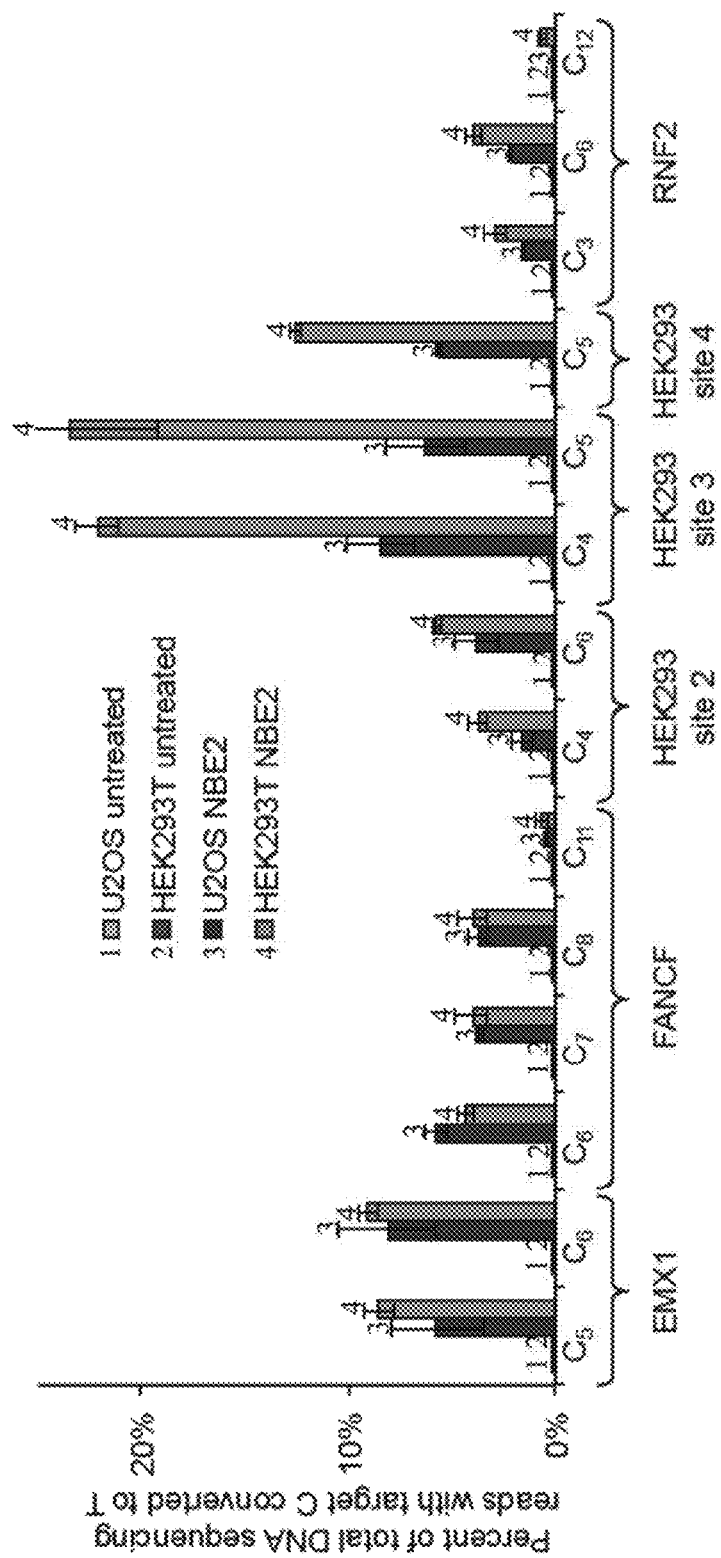
FIG. 19 shows nucleobase editing efficiencies of NBE2 in U2OS and HEK293T cells. Cellular C to T conversion percentages by NBE2 are shown for each of the six targeted genomic loci in HEK293T cells and U2OS cells. HEK293T cells were transfected using lipofectamine 2000, and U2OS cells were nucleofected. U2OS nucleofection efficiency was 74%. Three days after plasmid delivery, genomic DNA was extracted and analyzed for nucleobase editing at the six genomic loci by HTS. Values and error bars reflect the mean and standard deviation of at least two biological experiments done on different days.

Similar editing efficiencies were observed when a separate plasmid overexpressing UGI was co-transfected with NBE1 (FIGS. 18A to 18H). However, while the direct fusion of UGI to NBE1 resulted in no significant increase in C to T mutations at monitored non-targeted genomic locations, overexpression of unfused UGI detectably increased the frequency of C to T mutations elsewhere in the genome (FIGS. 18A to 18H). The generality of NBE2-mediated nucleobase editing was confirmed by assessing editing efficiencies on the same six genomic targets in U2OS cells, and observed similar results with those in HEK293T cells (FIG. 19). Importantly, NBE2 typically did not result in any detectable indels (FIG. 13C and FIG. 29C), consistent with the known mechanistic dependence of NHEJ on double-stranded DNA breaks.[57,78] Together, these results indicate that conjugating UGI to NBE1 can greatly increase the efficiency of nucleobase editing in human cells.

Figure 20:
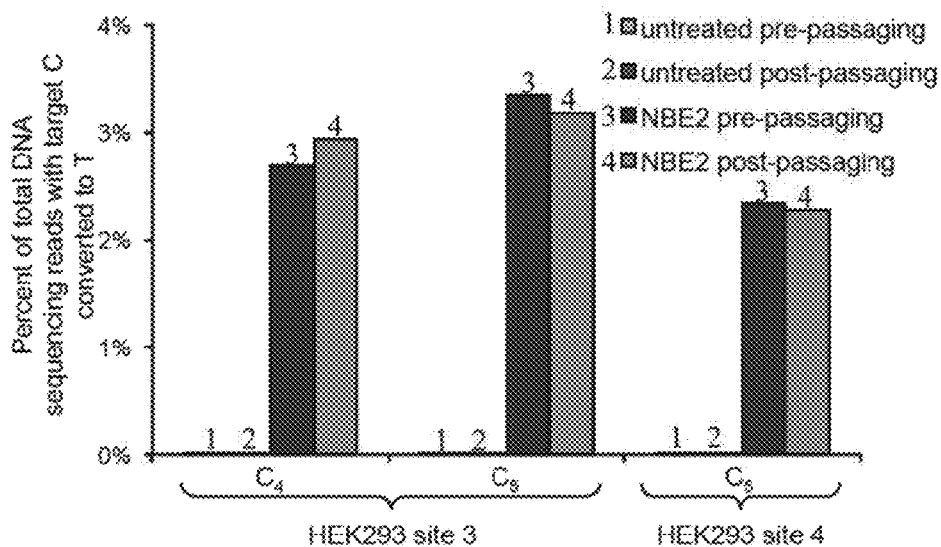
FIG. 20 shows nucleobase editing persists over multiple cell divisions. Cellular C to T conversion percentages by NBE2 are displayed at two genomic loci in HEK293T cells before and after passaging the cells. HEK293T cells were transfected using Lipofectamine 2000. Three days post transfection, the cells were harvested and split in half. One half was subjected to HTS analysis, and the other half was allowed to propagate for approximately five cell divisions, then harvested and subjected to HTS analysis.

The permanence of nucleobase editing in human cells was confirmed by monitoring editing efficiencies over multiple cell divisions in HEK293T cells at two of the tested genomic loci. Genomic DNA was harvested at two time points: three days after transfection with plasmids expressing NBE2 and appropriate sgRNAs, and after passaging the cells and growing them for four additional days (approximately five subsequent cell divisions). No significant change in editing efficiency was observed between the non-passaged cells (editing observed in 4.6% to 6.6% of targeted strands for three different target Cs) and passaged cells (editing observed in 4.6% to 6.4% of targeted strands for the same three target Cs), confirming that the nucleobase edits became permanent following cell division (FIG. 20). Indels will on rare occasion arise from the processing of U:G lesions by cellular repair processes, which involve single-strand break intermediates that are known to lead to indels.[84] Given that several hundred endogenous U:G lesions are generated every day per human cell from spontaneous cytidine deaminase,[85] it was anticipate that the total indel frequency from U:G lesion repair is unlikely to increase from BE1 or BE2 activity at a single target locus.

Figure 13B:
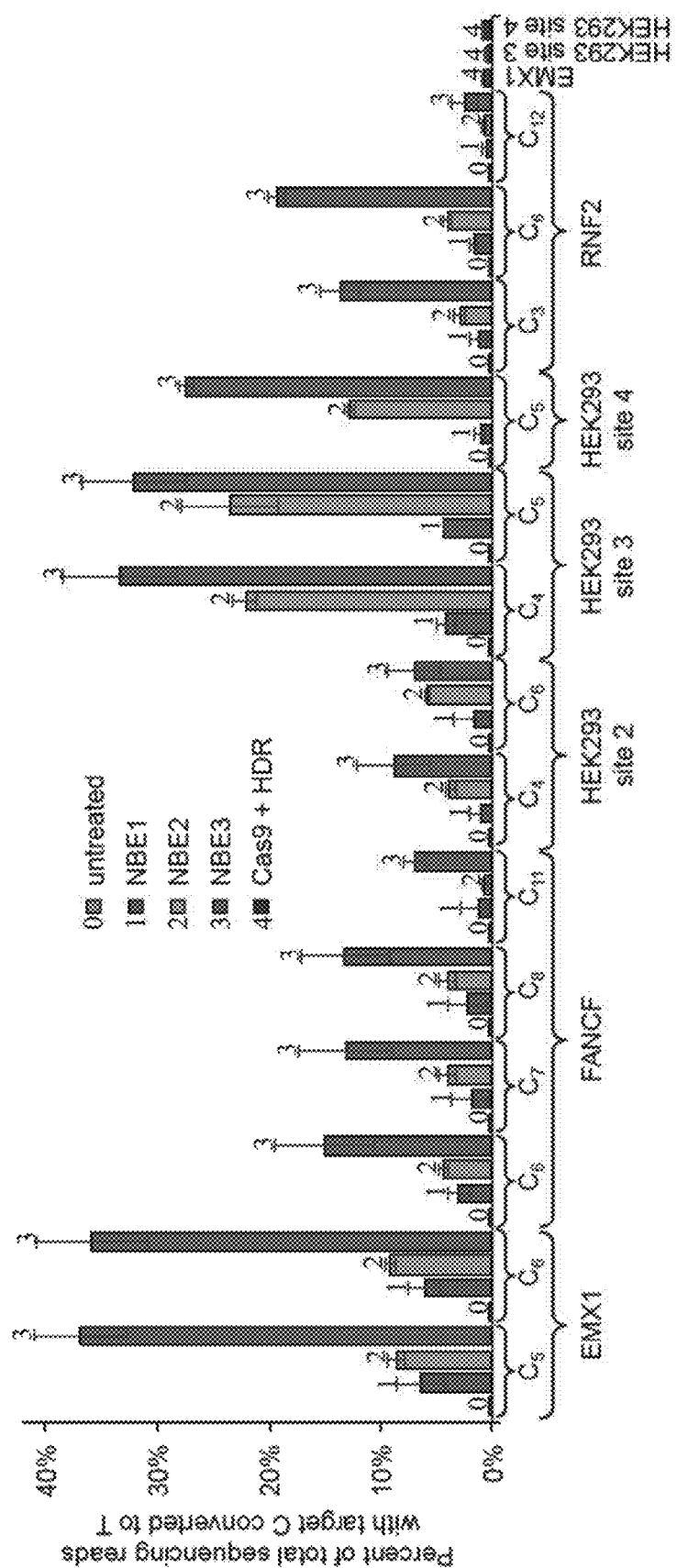
Figure 13C:
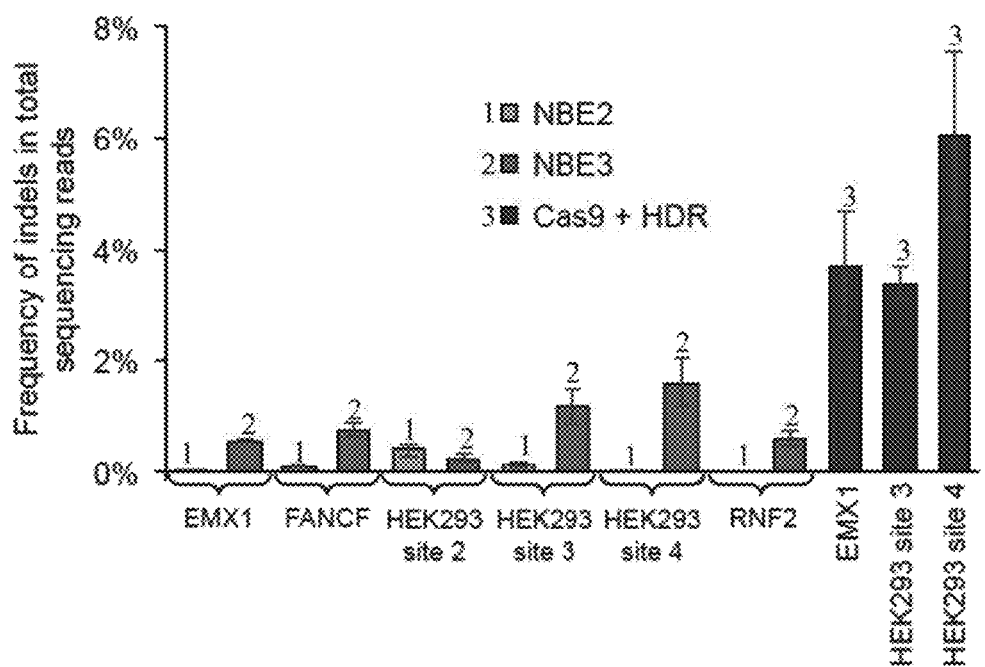
Figure 15A:
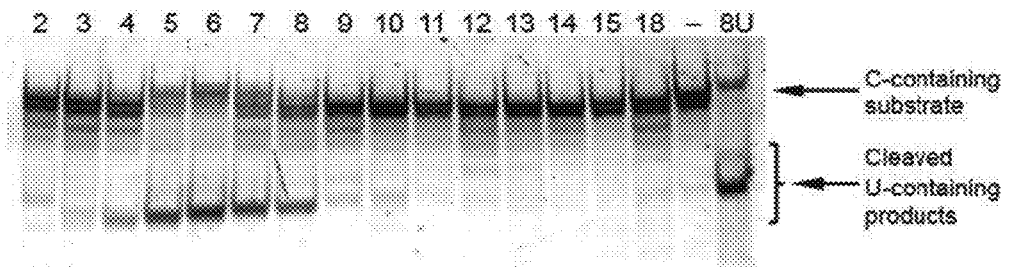
FIGS. 15A to 15D show effects of deaminase-dCas9 linker length and composition on nucleobase editing. Gel-based deaminase assay showing the deamination window of nucleobase editors with deaminase-Cas9 linkers of GGS (FIG. 15A), (GGS)$_3$ (SEQ ID NO: 596) (FIG. 15B), XTEN (FIG. 15C), or (GGS)$_7$ (SEQ ID NO: 597) (FIG. 15D). Following incubation of 1.85 μM editor-sgRNA complexes with 125 nM dsDNA substrates at 37° C. for 2 h, the dye-conjugated DNA was isolated and incubated with USER enzyme (uracil DNA glycosylase and endonuclease VIII) at 37° C. for an additional hour to cleave the DNA backbone at the site of any uracils. The resulting DNA was resolved on a denaturing polyacrylamide gel, and the dye-conjugated strand was imaged. Each lane is numbered according to the position of the target C within the protospacer, or with—if no target C is present. 8U is a positive control sequence with a U synthetically incorporated at position 8.
Figure 15B:
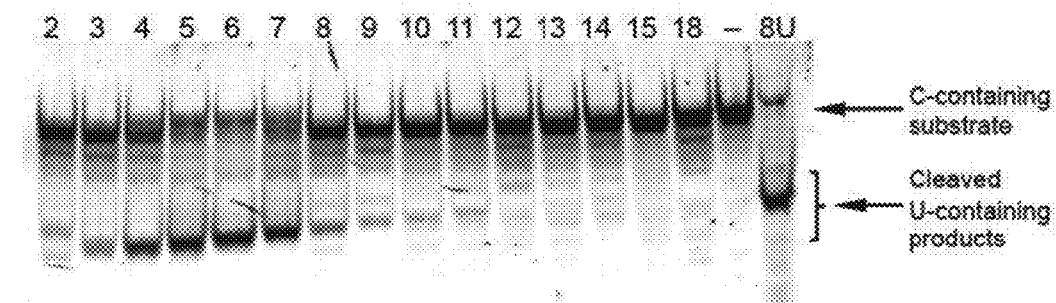
Figure 15C:
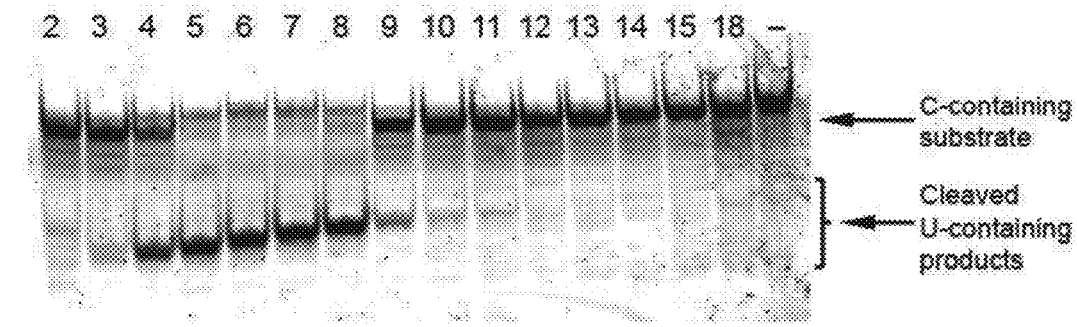
Figure 15D:
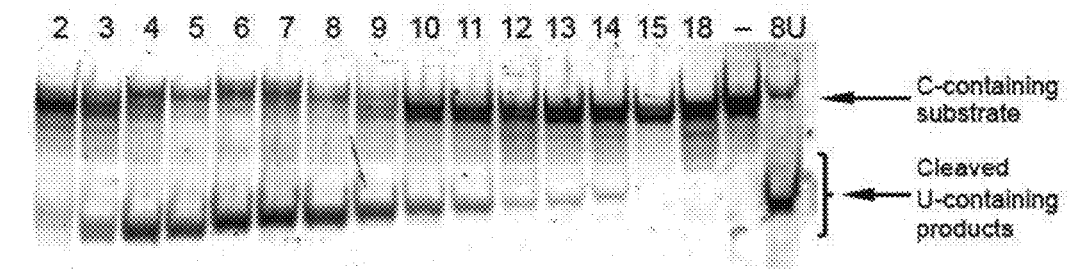
Figure 29B:
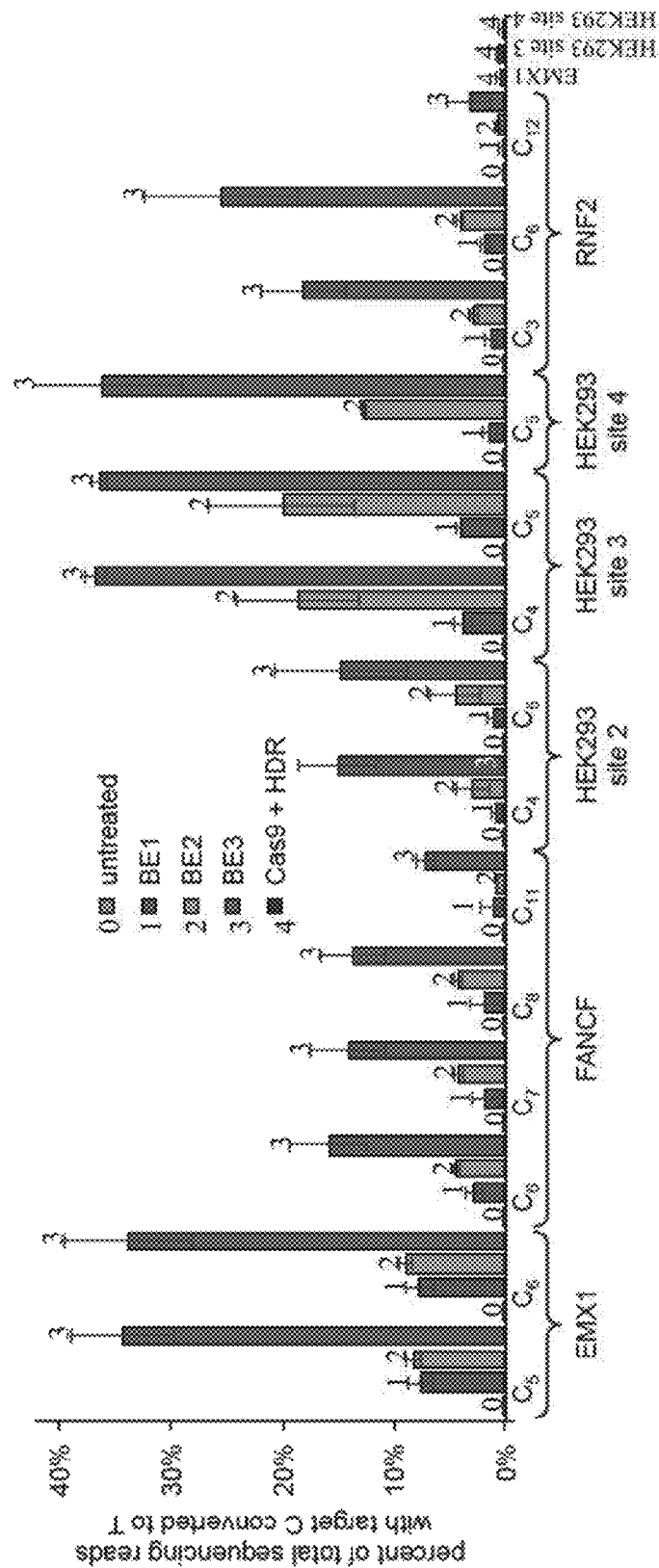
Figure 29C:
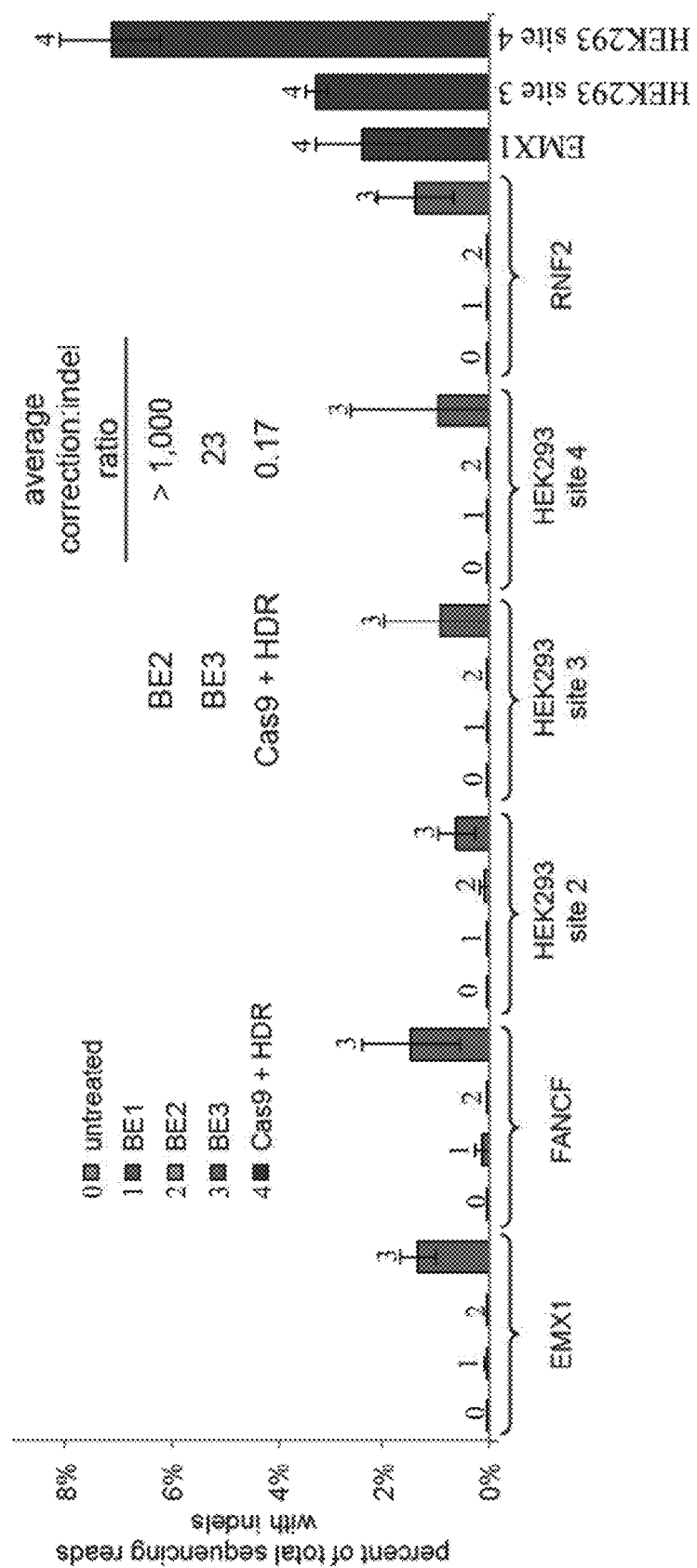
Figure 34:
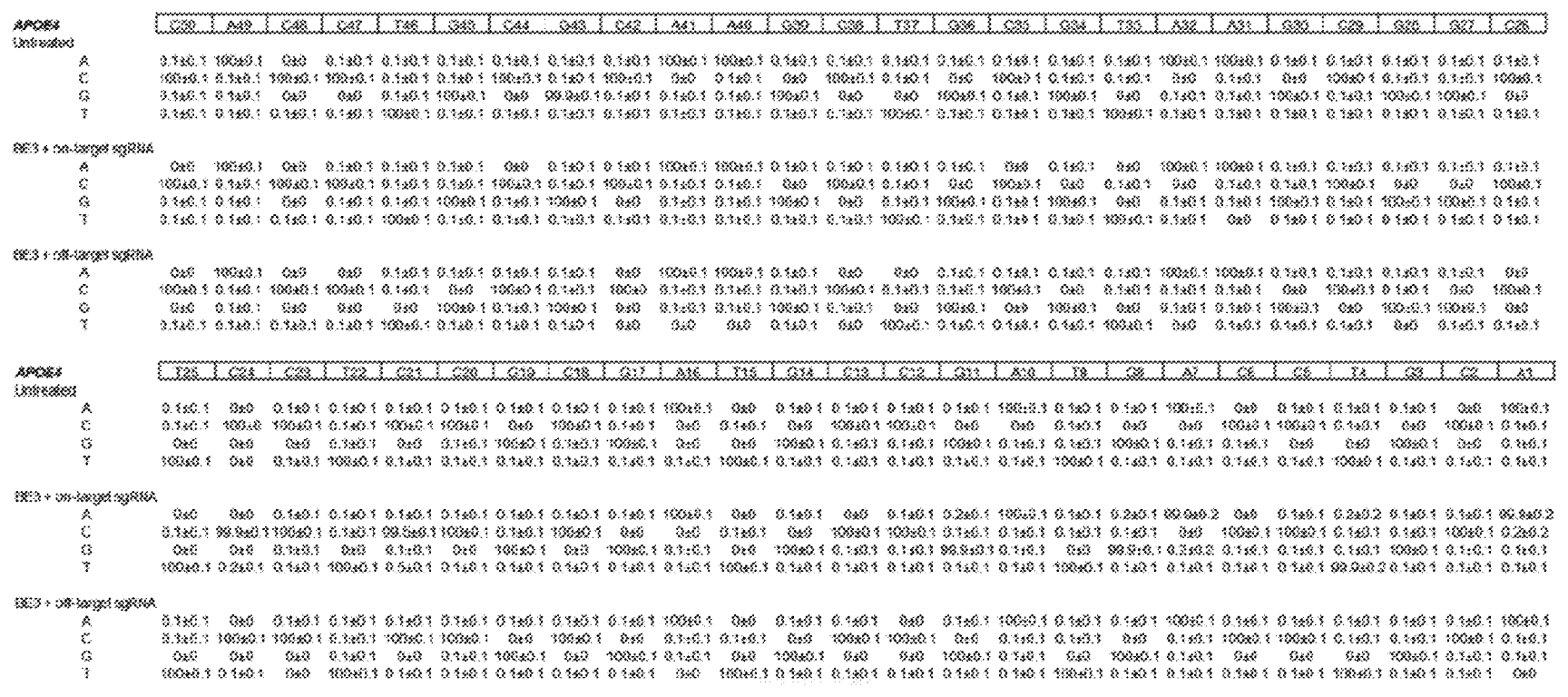
Figure 34:
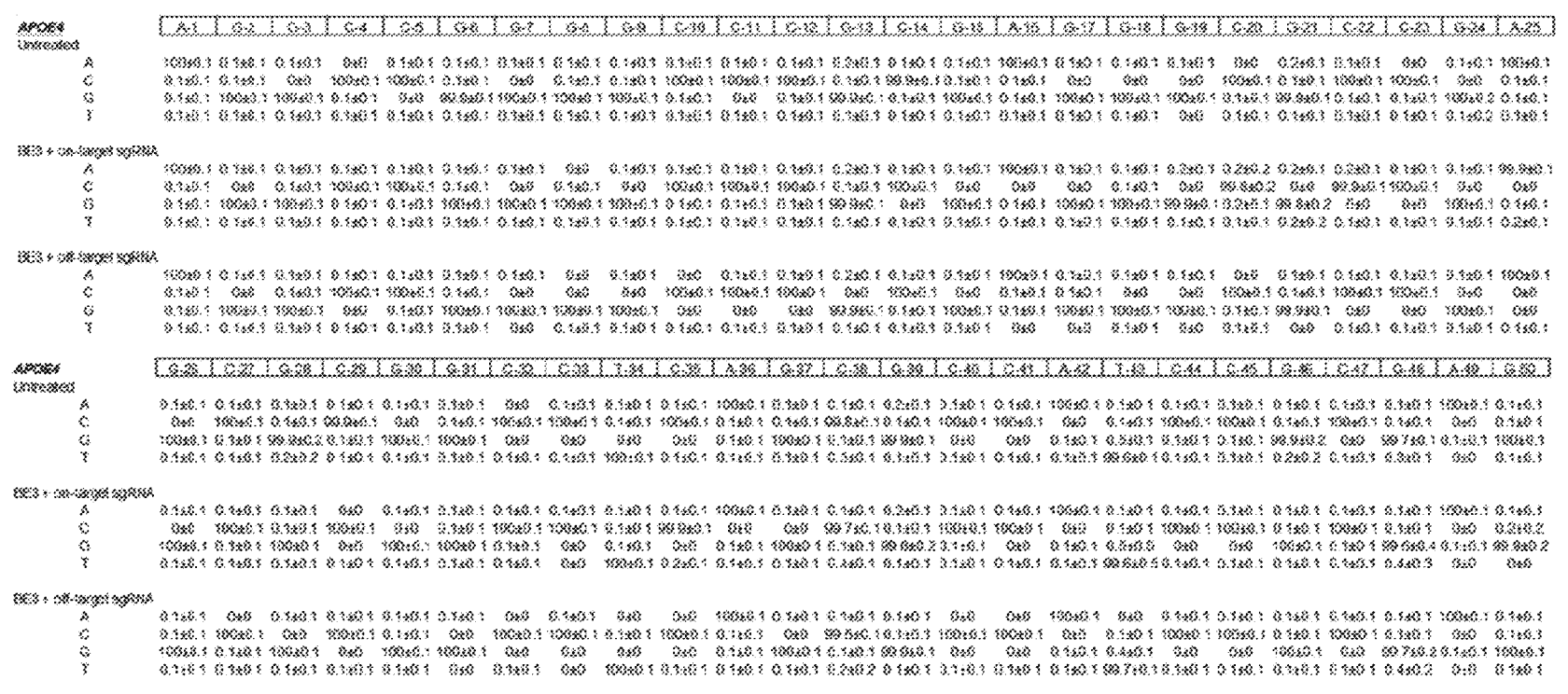
Figure 38:
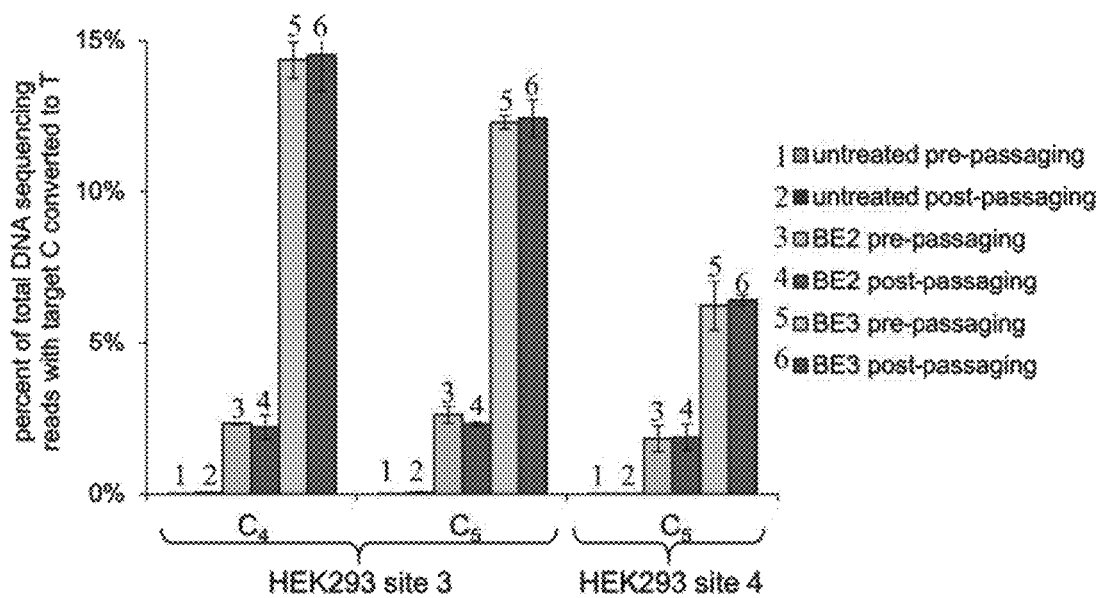
FIG. 38 shows base editing persists over multiple cell divisions. Cellular C to T conversion percentages by BE2 and BE3 are shown for HEK293 sites 3 and 4 in HEK293T cells before and after passaging the cells. HEK293T cells were nucleofected with plasmids expressing BE2 or BE3 and an sgRNA targeting HEK293 site 3 or 4. Three days after nucleofection, the cells were harvested and split in half. One half was subjected to HTS analysis, and the other half was allowed to propagate for approximately five cell divisions, then harvested and subjected to HTS analysis. Values and error bars reflect the mean and standard deviation of at least two biological experiments.
Figure 39A:
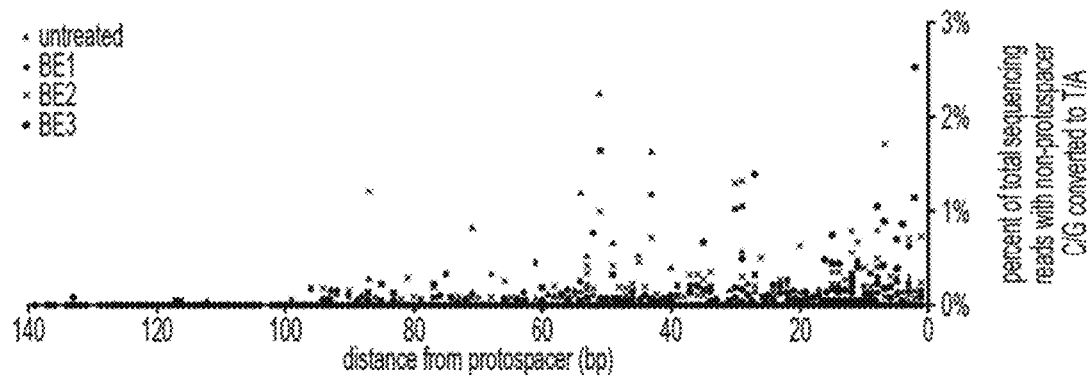
Figures 39B, 39C:
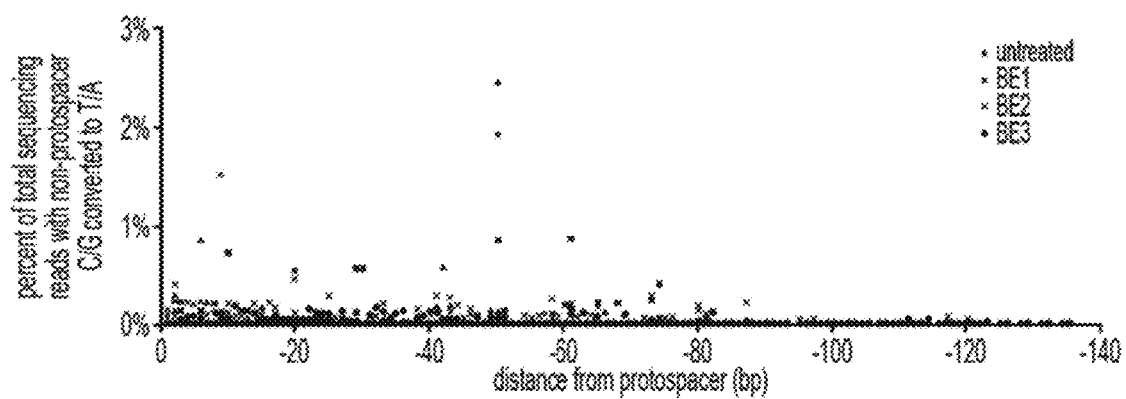

To further increase the efficiency of nucleobase editing in cells, it was anticipated that nicking the non-edited strand may result in a smaller fraction of edited Us being removed by the cell, since eukaryotic mismatch repair machinery uses strand discontinuity to direct DNA repair to any broken strand of a mismatched duplex (FIG. 29A).[58,79,80] The catalytic His residue was restored at position 840 in the Cas9 HNH domain,[47,59] resulting in the third-generation nucleobase editor NBE3 that nicks the non-edited strand containing a G opposite the targeted C, but does not cleave the target strand containing the C. Because NBE3 still contains the Asp10Ala mutation in Cas9, it does not induce double-stranded DNA cleavage. This strategy of nicking the non-edited strand augmented nucleobase editing efficiency in human cells by an additional 1.4- to 4.8-fold relative to NBE2, resulting in up to 36.3% of total DNA sequences containing the targeted C to T conversion on the same six human genomic targets in HEK293T cells (FIGS. 13A to 13C and FIG. 29B). Importantly, only a small frequency of indels, averaging 0.8% (ranging from 0.2% to 1.6% for the six different loci), was observed from NBE3 treatment (FIG. 13C, FIG. 29C, and FIG. 34). In contrast, when cells were treated with wild-type Cas9, sgRNA, and a single-stranded DNA donor template to mediate HDR at three of these loci C to T conversion efficiencies averaging only 0.7% were observed, with much higher relative indel formation averaging 3.9% (FIGS. 13A to 13C and FIG. 29C). The ratio of allele conversion to NHEJ outcomes averaged >1,000 for BE2, 23 for BE3, and 0.17 for wild-type Cas9 (FIG. 3c). We confirmed the permanence of base editing in human cells by monitoring editing efficiencies over multiple cell divisions in HEK293T cells at the HEK293 site 3 and 4 genomic loci (FIG. 38). These results collectively establish that nucleobase editing can effect much more efficient targeted single-base editing in human cells than Cas9-mediated HDR, and with much less (NBE3) or no (NBE2) indel formation.

Next, the off-target activity of NBE1, NBE2, and NBE3 in human cells was evaluated. The off-target activities of Cas9, dCas9, and Cas9 nickase have been extensively studied (FIGS. 23 to 24 and 31 to 33).[54,60-62] Because the sequence preference of rAPOBEC1 has been shown to be independent of DNA bases more than one base from the target C,[63] consistent with the sequence context independence observed in FIGS. 12A to 12B, it was assumed that potential off-target activity of nucleobase editors arises from off-target Cas9 binding. Since only a fraction of Cas9 off-target sites will have a C within the active window for nucleobase editing, off-target nucleobase editing sites should be a subset of the off-target sites of canonical Cas9 variants. For each of the six sites studied, the top ten known Cas9 off-target loci in human cells that were previously determined using the GUIDE-seq method were sequenced (FIGS. 23 to 27 and 31 to 33).[54,61] Detectable off-target nucleobase editing at only a subset (16/34, 47% for NBE1 and NBE2, and 17/34, 50% for NBE3) of known dCas9 off-target loci was observed. In all cases, the off-target base-editing substrates contained a C within the five-base target window. In general, off-target C to T conversion paralleled off-target Cas9 nuclease-mediated genome modification frequencies (FIGS. 23 to 27). Also monitored were C to T conversions at 2,500 distinct cytosines surrounding the six on-target and 34 off-target loci tested, representing a total of 14,700,000 sequence reads derived from approximately $1.8 \times 10^6$ cells, and observed no detectable increase in C to T conversions at any of these other sites upon NBE1, NBE2, or NBE3 treatment compared to that of untreated cells (FIG. 28). Taken together, these findings suggest that off-target substrates of nucleobase editors include a subset of Cas9 off-target substrates, and that nucleobase editors in human cells do not induce untargeted C to T conversion throughout the genome at levels that can be detected by the methods used here. No substantial change was observed in editing efficiency between non-passaged HEK293T cells (editing observed in 1.8% to 2.6% of sequenced strands for the three target Cs with BE2, and 6.2% to 14.3% with BE3) and cells that had undergone approximately five cell divisions after base editing (editing observed in 1.9% to 2.3% of sequenced strands for the same target Cs with BE2, and 6.4% to 14.5% with BE3), confirming that base edits in these cells are durable (Extended Data FIG. 6).

Figure 30A:
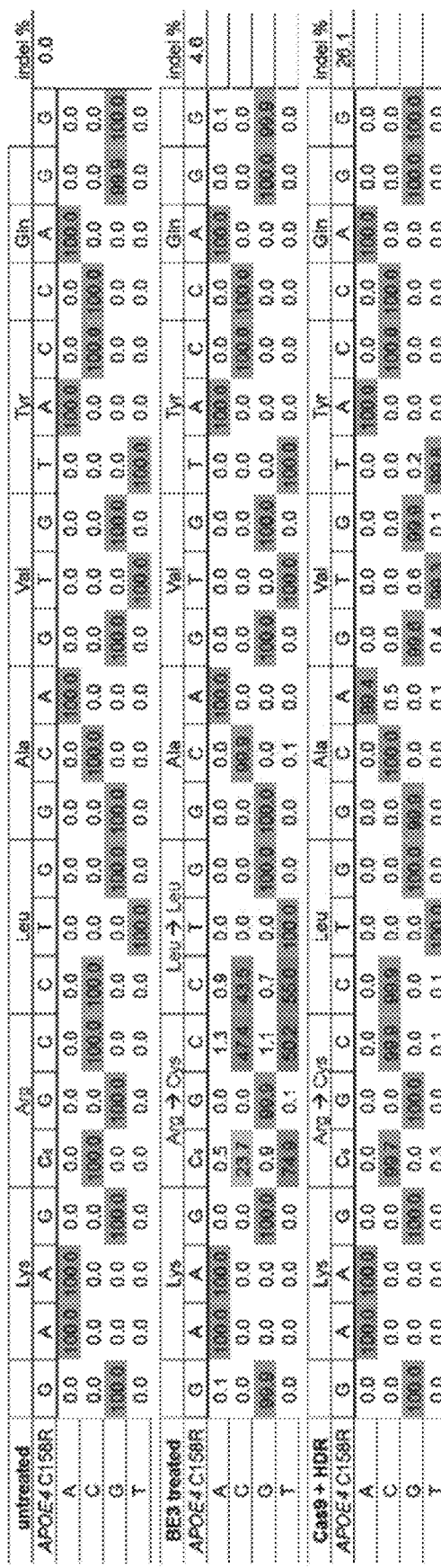
FIGS. 30A to 30B show BE3-mediated correction of two disease-relevant mutations in mammalian cells. The sequence of the protospacer is shown to the right of the mutation, with the PAM in blue and the target base in red with a subscripted number indicating its position within the protospacer. Underneath each sequence are the percentages of total sequencing reads with the corresponding base. Cells were treated as described in the Materials and Methods.
Figure 35:
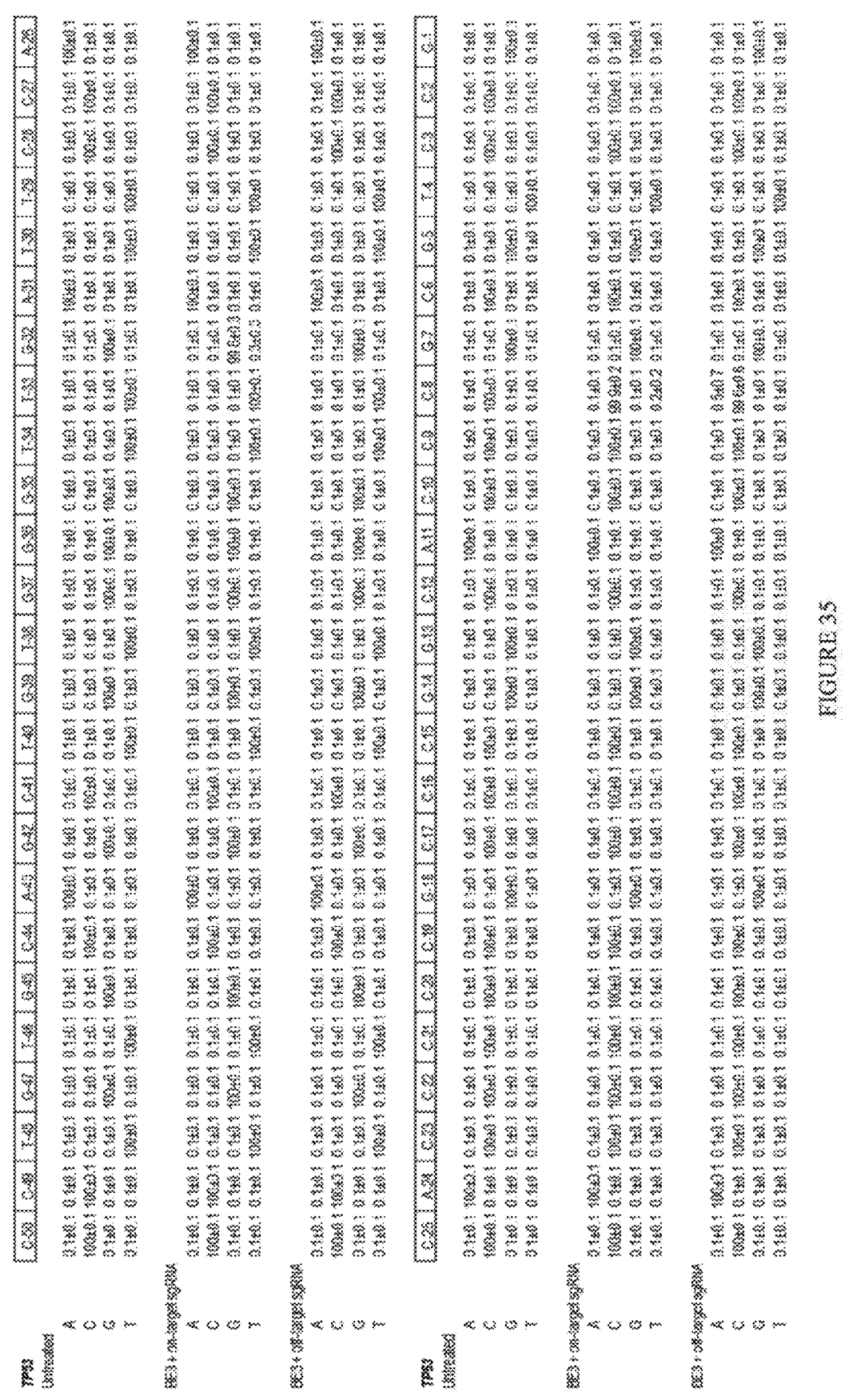
Figure 35:
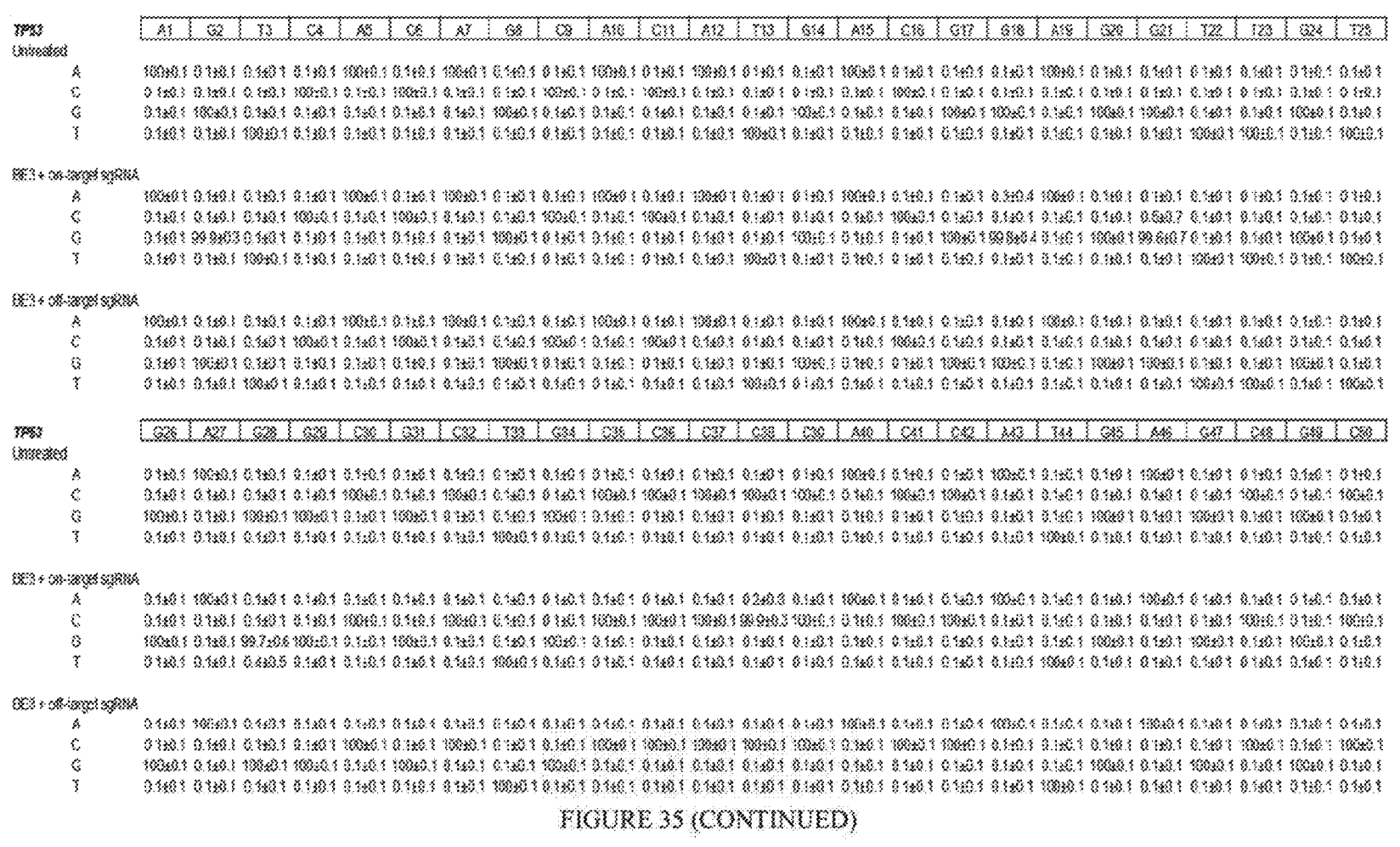
Figure 40A:
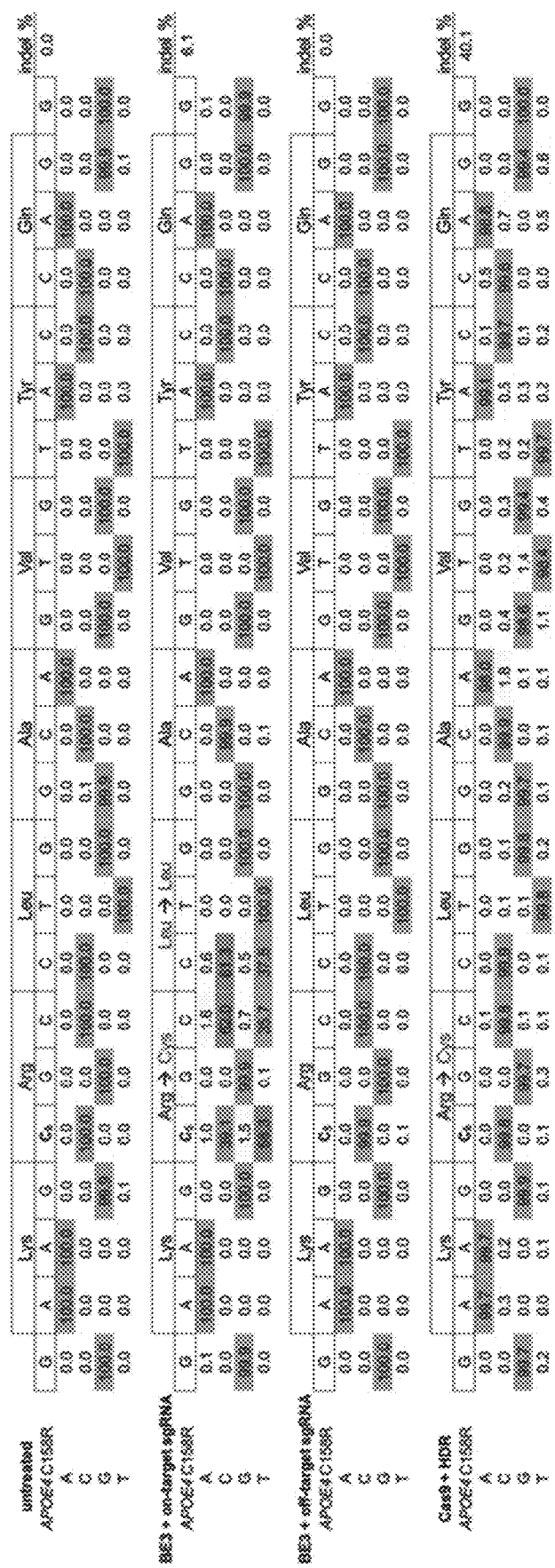
FIGS. 40A to 40B show additional data sets of BE3-mediated correction of two disease-relevant mutations in mammalian cells. For each site, the sequence of the protospacer is indicated to the right of the name of the mutation, with the PAM highlighted in blue and the base responsible for the mutation indicated in red bold with a subscripted number corresponding to its position within the protospacer. The amino acid sequence above each disease-associated allele is shown, together with the corrected amino acid sequence following base editing in green. Underneath each sequence are the percentages of total sequencing reads with the corresponding base. Cells were nucleofected with plasmids encoding BE3 and an appropriate sgRNA. Two days after nucleofection, genomic DNA was extracted from the nucleofected cells and analyzed by HTS to assess pathogenic mutation correction.

Finally, the potential of nucleobase editing to correct three disease-relevant mutations in mammalian cells was tested. The apolipoprotein E gene variant APOE4 encodes two Arg residues at amino acid positions 112 and 158, and is the largest and most common genetic risk factor for late-onset Alzheimer's disease.[64] ApoE variants with Cys residues in positions 112 or 158, including APOE2 (Cys112/Cys158), APOE3 (Cys112/Arg158), and APOE3' (Arg112/Cys158) have been shown[65] or are presumed[81] to confer substantially lower Alzheimer's disease risk than APOE4. Encouraged by the ability of NBE1 to convert APOE4 to APOE3' in vitro (FIGS. 16A to 16B), this conversion was attempted in immortalized mouse astrocytes in which the endogenous murine APOE gene has been replaced by human APOE4 (Taconic). DNA encoding NBE3 and an appropriate sgRNA was delivered into these astrocytes by nucleofection (nucleofection efficiency of 25%), extracted genomic DNA from all treated cells two days later, and measured editing efficiency by HTS. Conversion of Arg158 to Cys158 was observed in 58-75% of total DNA sequencing reads (44% of nucleofected astrocytes) (FIGS. 14A to 14C and FIG. 30A). Also observed was 36-50% editing of total DNA at the third position of codon 158 and 38-55% editing of total DNA at the first position of Leu159, as expected since all three of these Cs are within the active nucleobase editing window. However, neither of the other two C→T conversions results in a change in the amino acid sequence of the ApoE3' protein since both TGC and TGT encode Cys, and both CTG and TTG encode Leu. From >1,500,000 sequencing reads derived from $1 \times 10^6$ cells evidence of 1.7% indels at the targeted locus following NBE3 treatment was observed (FIG. 35). In contrast, identical treatment of astrocytes with wt Cas9 and donor ssDNA resulted in 0.1-0.3% APOE4 correction and 26-40% indels at the targeted locus, efficiencies consistent with previous reports of single-base correction using Cas9 and HDR[45,75] (FIG. 30A and FIG. 40A). Astrocytes treated identically but with an sgRNA targeting the VEGFA locus displayed no evidence of APOE4 base editing (FIG. 34 and FIG. 40A). These results demonstrate how nucleobase editors can effect precise, single-amino acid changes in the coding sequence of a protein as the major product of editing, even when their processivity results in more than one nucleotide change in genomic DNA. The off-target activities of Cas9, dCas9, and Cas9 nickase have been extensively studied.[54,60-62] In general, off-target C to T conversions by BE1, BE2, and BE3 paralleled off-target Cas9 nuclease-mediated genome modification frequencies.

Figure 30B:
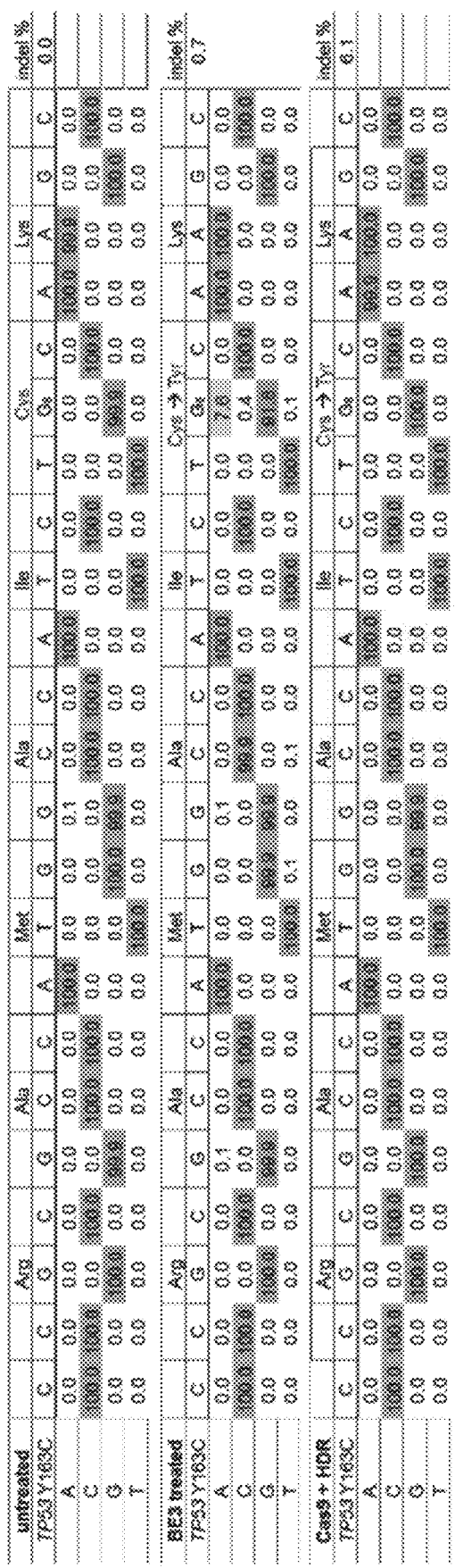
Figure 31:
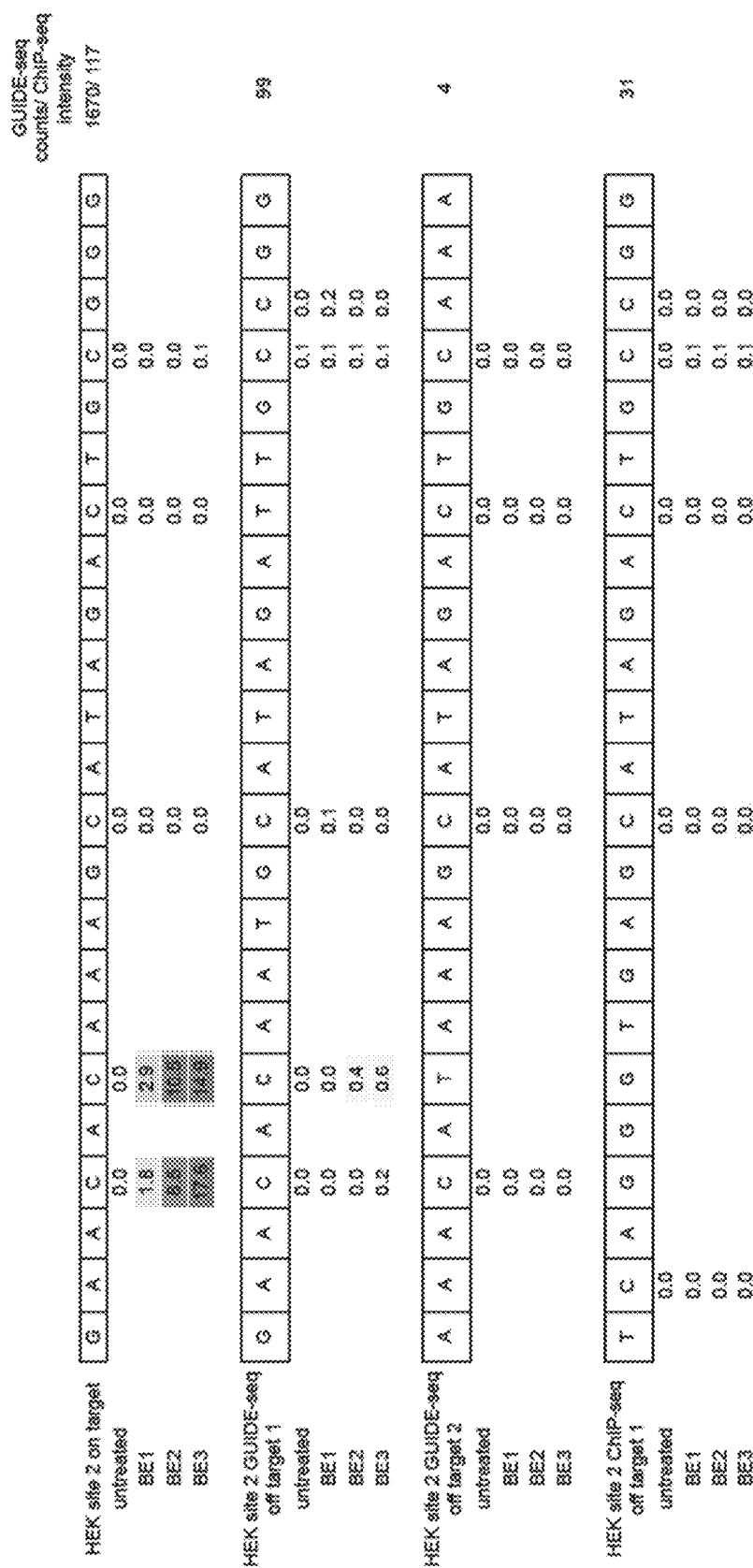
FIG. 31 shows activities of BE1, BE2, and BE3 at HEK293 site 2 off-targets. HEK293T cells were transfected with plasmids expressing BE1, BE2, or BE3 and a sgRNA matching the HEK293 site 2 sequence using Lipofectamine 2000. Three days after transfection, genomic DNA was extracted, amplified by PCR, and analyzed by high-throughput DNA sequencing at the on-target loci, plus all of the known Cas9 and dCas9 off-target loci for the HEK293 site 2 sgRNA, as previously determined by Joung and coworkers using the GUIDE-seq method (63), and Adli and coworkers using chromatin immunoprecipitation high-throughput sequencing (ChIP-seq) experiments (18). Sequences of the on-target and off-target protospacers and protospacer adjacent motifs (PAMs) are displayed. Cellular C to T conversion percentages, defined as the percentage of total DNA sequencing reads with T at each position of an original C within the protospacer, are shown for BE1, BE2, and BE3. On the far right are displayed the total number of sequencing reads reported, and the ChIP-seq signal intensity reported for each sequence. This figure depicts SEQ ID NOs: 681 to 688 from top to bottom, respectively.
Figure 40B:
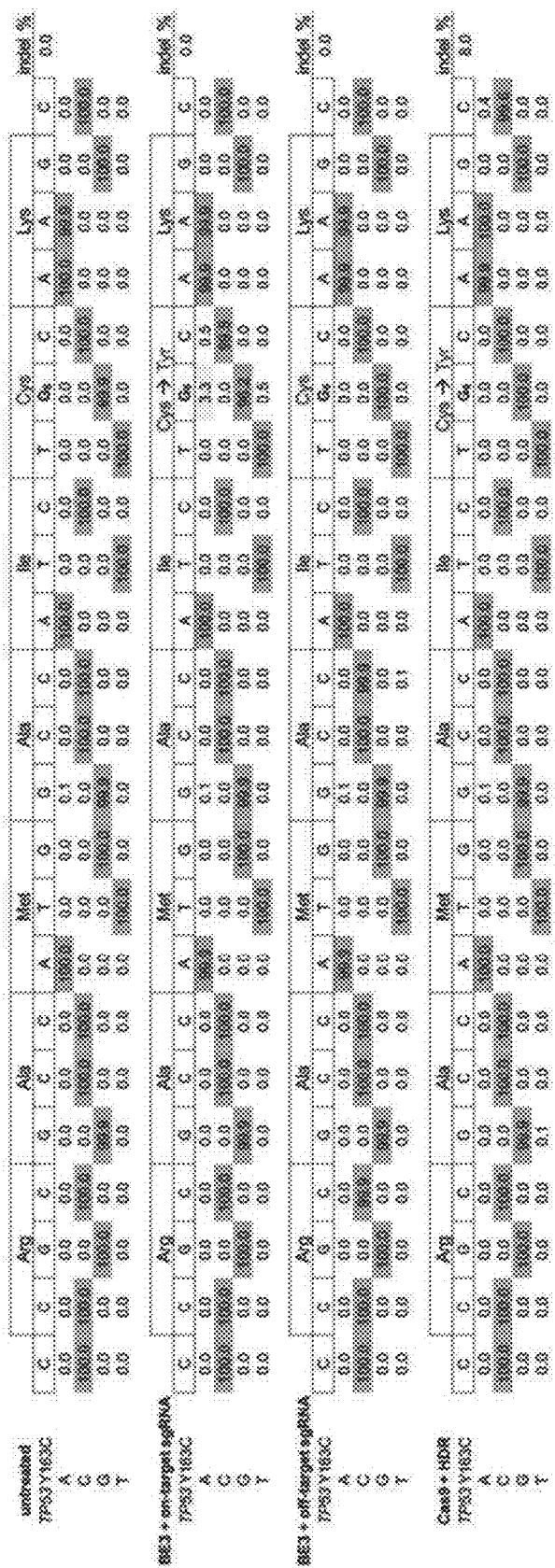

The dominant-negative p53 mutations Tyr163Cys and Asn239Asp are strongly associated with several types of cancer.[66-67] Both of these mutations can be corrected by a C to T conversion on the template strand (FIGS. 16A to 16B). A human breast cancer cell line homozygous for the p53 Tyr163Cys mutation (HCC1954 cells) was nucleofected with DNA encoding NBE3 and an sgRNA programmed to correct Tyr163Cys. Because the nucleofection efficiency of HCC1954 cells was <10%, a plasmid expressing IRFP was co-nucleofected into these cells to enable isolation of nucleofected cells by fluorescence-activated cell sorting two days after treatment. HTS of genomic DNA revealed correction of the Tyr163Cys mutation in 7.6% of nucleofected HCC1954 cells (FIG. 30B and FIG. 40A to 40B). Also nucleofected was a human lymphoma cell line that is heterozygous for p53 Asn239Asp (ST486 cells) with DNA encoding NBE2 and an sgRNA programmed to correct Asn239Asp with 92% nucleofection efficiency). Correction of the Asn239Asp mutation was observed in 11% of treated ST486 cells (12% of nucleofected ST486 cells). Consistent with the findings in HEK cells, no indels were observed from the treatment of ST486 cells with NBE2, and 0.6% indel formation from the treatment of HCC1954 cells with NBE3. No other DNA changes within at least 50 base pairs of both sides of the protospacer were detected at frequencies above that of untreated controls out of >2,000,000 sequencing reads derived from $2 \times 10^5$ cells (FIGS. 14A to 14C, FIG. 30B and Table 1). These results collectively represent the conversion of three disease-associated alleles in genomic DNA into their wild-type forms with an efficiency and lack of other genome modification events that is, to our knowledge, not currently achievable using other methods.

Figure 21:
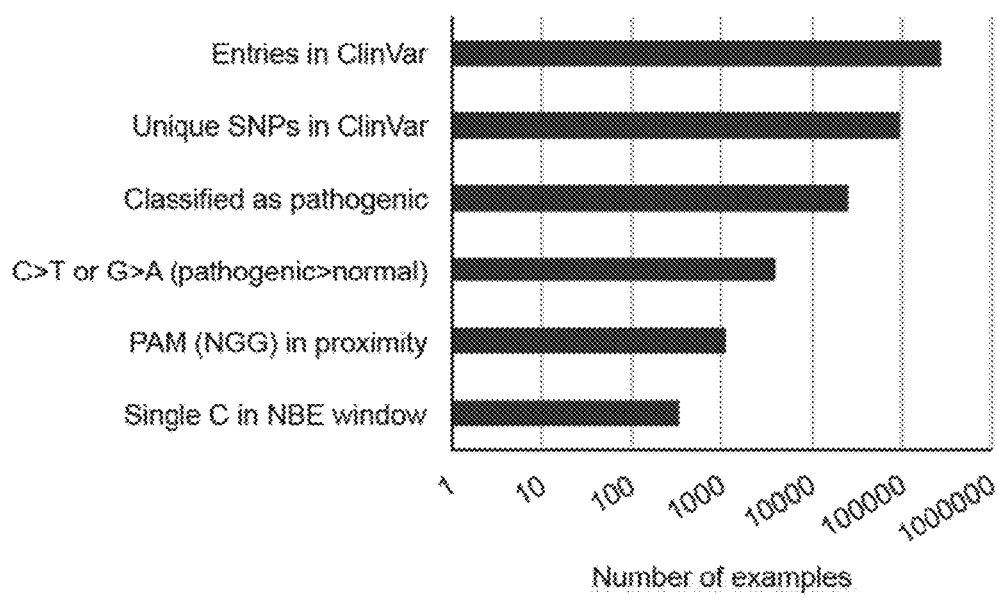
FIG. 21 shows genetic variants from ClinVar that can be corrected in principle by nucleobase editing. The NCBI ClinVar database of human genetic variations and their corresponding phenotypes[68] was searched for genetic diseases that can be corrected by current nucleobase editing technologies. The results were filtered by imposing the successive restrictions listed on the left. The x-axis shows the number of occurrences satisfying that restriction and all above restrictions on a logarithmic scale.
Figure 23:
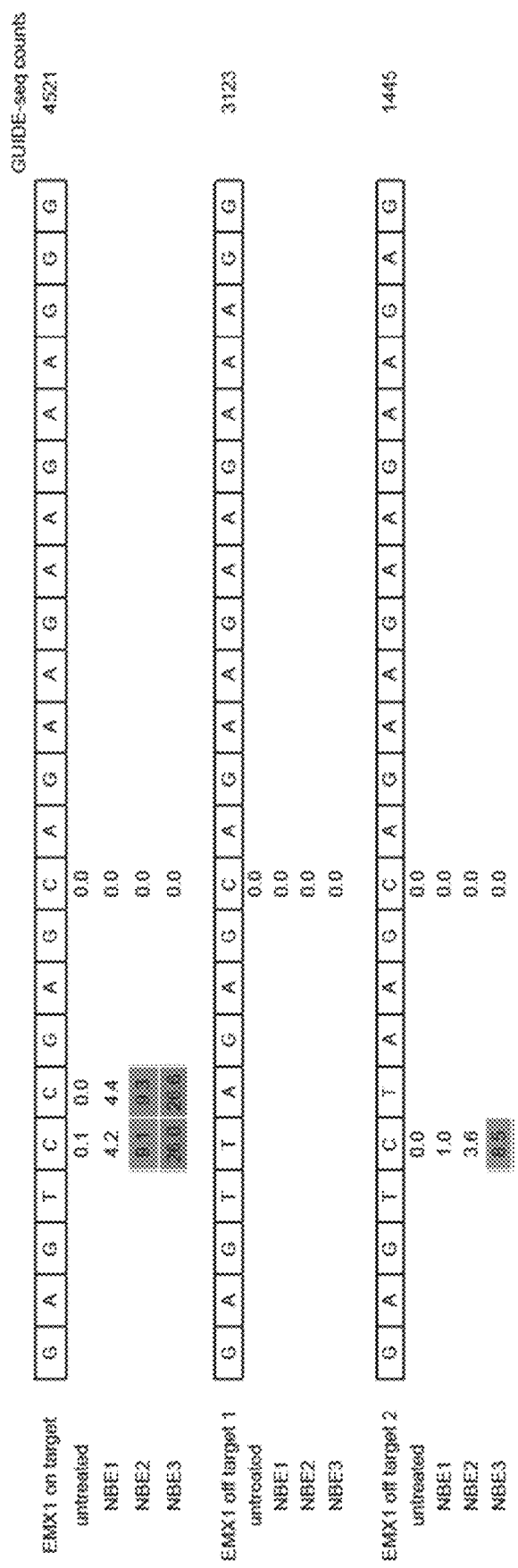
FIG. 23 shows activities of NBE1, NBE2, and NBE3 at EMX1 off-targets. HEK293T cells were transfected with plasmids expressing NBE1, NBE2, or NBE3 and a sgRNA matching the EMX1 sequence using Lipofectamine 2000. Three days after transfection, genomic DNA was extracted, amplified by PCR, and analyzed by high-throughput DNA sequencing at the on-target loci, plus the top ten known Cas9 off-target loci for the EMX1 sgRNA, as previously determined using the GUIDE-seq method[55]. EMX1 off-target 5 locus did not amplify and is not shown. Sequences of the on-target and off-target protospacers and protospacer adjacent motifs (PAMs) are displayed. Cellular C to T conversion percentages, defined as the percentage of total DNA sequencing reads with T at each position of an original C within the protospacer, are shown for NBE1, NBE2, and NBE3. On the far right are displayed the total number of sequencing reads reported for each sequence. This figure depicts SEQ ID NOs: 293, and 310 through 318 from top to bottom, respectively.
Figure 25:
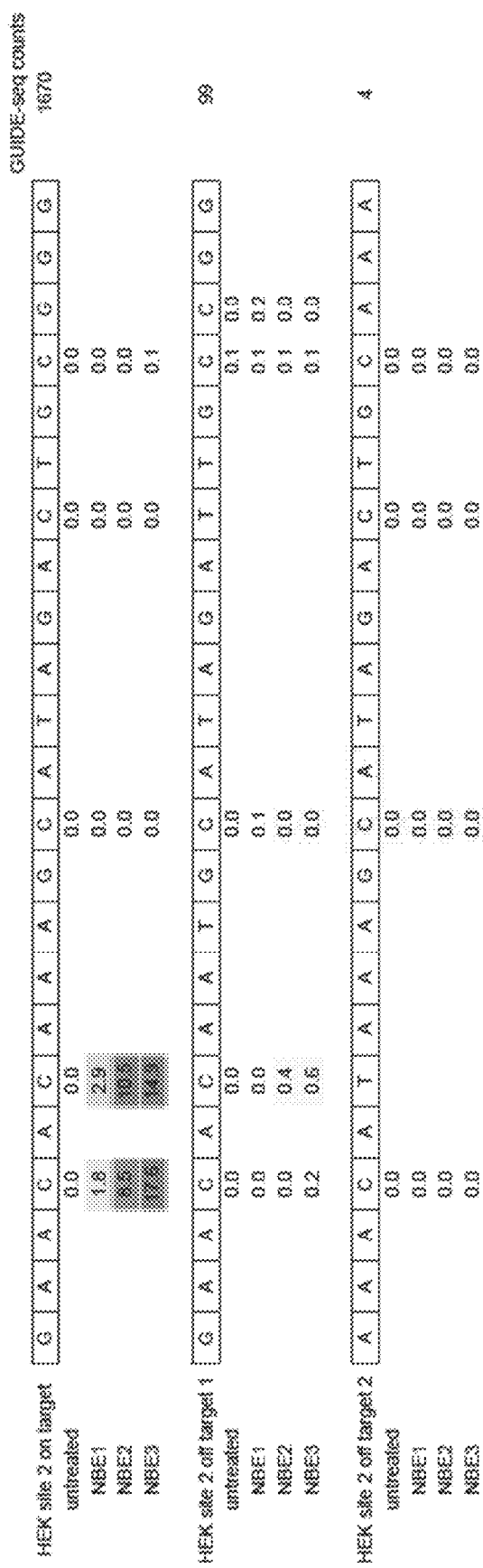
FIG. 25 shows activities of NBE1, NBE2, and NBE3 at HEK293 site 2 off-targets. HEK293T cells were transfected with plasmids expressing NBE1, NBE2, or NBE3 and a sgRNA matching the HEK293 site 2 sequence using Lipofectamine 2000. Three days after transfection, genomic DNA was extracted, amplified by PCR, and analyzed by high-throughput DNA sequencing at the on-target loci, plus all of the known Cas9 off-target loci for the HEK293 site 2 sgRNA, as previously determined using the GUIDE-seq method[55]. Sequences of the on-target and off-target protospacers and protospacer adjacent motifs (PAMs) are displayed. Cellular C to T conversion percentages, defined as the percentage of total DNA sequencing reads with T at each position of an original C within the protospacer, are shown for NBE1, NBE2, and NBE3. On the far right are displayed the total number of sequencing reads reported for each sequence. This figure depicts SEQ ID NOs: 295, 327, and 328 from top to bottom, respectively.

To illuminate the potential relevance of nucleobase editors to address human genetic diseases, the NCBI ClinVar database[68] was searched for known genetic diseases that could in principle be corrected by this approach. ClinVar was filtered by first examining only single nucleotide polymorphisms (SNPs), then removing any nonpathogenic variants. Out of the 24,670 pathogenic SNPs, 3,956 are caused by either a T to C, or an A to G, substitution. This list was further filtered to only include variants with a nearby NGG PAM that would position the SNP within the deamination activity window, resulting in 1,089 clinically relevant pathogenic gene variants that could in principle be corrected by the nucleobase editors described (FIG. 21 and Table 1). To illuminate the potential relevance of base editors to address human genetic diseases, the NCBI ClinVar database[68] was searched for known genetic diseases that could in principle be corrected by this approach. ClinVar was filtered by first examining only single nucleotide polymorphisms (SNPs), then removing any non-pathogenic variants. Out of the 24,670 pathogenic SNPs, 3,956 are caused by either a T to C, or an A to G, substitution. This list was further filtered to only include variants with a nearby NGG PAM that would position the SNP within the deamination activity window, resulting in 911 clinically relevant pathogenic gene variants that could in principle be corrected by the base editors described here. Of these, 284 contain only one C within the base editing activity window. A detailed list of these pathogenic mutations can be found in Table 1.

TABLE 1

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 755445790 | NM_000391.3(TPP1):c.887-10A > G | TTTYTTTTTTTTTTTTGAGG | Ceroid lipofuscinosis, neuronal, 2 |
| 113994167 | NM_000018.3(ACADVL):c.848T > C (p.Val283Ala) | TTTGYGGTGGAGAGGGGCTTCGG, TTGYGGTGGAGAGGGGCTTCGGG | Very long chain acyl-CoA dehydrogenase deficiency |
| 119470018 | NM_024996.5(GFM1):c.521A > G (p.Asn174Ser) | TTGYTAATAAAAGTTAGAAACGG | Combined oxidative phosphorylation deficiency 1 |
| 115650537 | NM_000426.3(LAMA2):c.8282T > C (p.Ile2761Thr) | TTGAYAGGGAGCAAGCAGTTCGG, TGAYAGGGAGCAAGCAGTTCGGG | Merosin deficient congenital muscular dystrophy |
| 587777752 | NM_014946.3(SPAST):c.1688- | TTCYGTAAAACATAAAAGTCAGG | Spastic paraplegia 4, autosomal dominant |
| 794726821 | NM_001165963.1(SCN1A):c.4055T > C (p.Leu1352Pro) | TTCYGGTTTGTCTTATATTCTGG | Severe myoclonic epilepsy in infancy |
| 397514745 | NM_001130089.1(KARS):c.517T > C (p.Tyr173His) | CTTCYATGATCTTCGAGGAGAGG, TTCYATGATCTTCGAGGAGAGGG | Deafness, autosomal recessive 89 |
| 376960358 | NM_001202.3(BMP4):c.362A > G (p.His121Arg) | TTCGTGCGYGGAAGCTCCTCACGG | Microphthalmia syndromic 6 |
| 606231280 | NM_001287223.1(SCN11A):c.1142T > C (p.Ile381Thr) | CTTCAYTGTGGTCATTTTCCTGG, TTCAYTGTGGTCATTTTCCTGGG | Episodic pain syndrome, familial, 3 |
| 387906735 | m.608A > G | TTCAGYGTATTGCTTTGAGGAGG |  |
| 199474663 | m.3260A > G | TTAAGTTYTATGCGATTACCCGGG | Cardiomyopathy with or without skeletal myopathy |
| 104894962 | NM_003413.3(ZIC3):c.1213A > G (p.Lys405Glu) | TGTGTTYGCGCAGGAGCTCGGG, ATGTGTTYGCGCAGGAGCTCGG | Heterotaxy, visceral, X-linked |
| 796053181 | NM_021007.2(SCN2A):c.1271T > C (p.Val424Ala) | TGTGYGGCCATGGCCTATGAGG | not provided |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base
to be edited, e.g., C. (SEQ ID NOs: 747 to 1868 appear from top to bottom below,
respectively)

| dbSNP # | Genotype | Protospacer and PAM sequence(s) | Associated uenetic disease |
|---|---|---|---|
| 267606788 | NM_000129.3(F13A1):c.728T > C (p.Met243Thr) | TGTGAYGGACAGAGCACAAATGG | Factor xiii a subunit, deficiency of |
| 397514503 | NM_003863.3(DPM2):c.68A > G (p.Tyr23Cys) | TGTAGYAGGTGAAGATGATCAGG | Congenital disorder of glycosylation type 1u |
| 104893973 | NM_000416.2(IFNGR1):c.260T > C (p.Ile87Thr) | TGTAATAYTTCTGATCATGTTGG | Disseminated atypical mycobacterial infection, Mycobacterium tuberculosis, susceptibility to |
| 121908466 | NM_005682.6(SDGRG1):c.263A > G (p.Tyr88Cys) | TGGYAGAGGCCCCTGGGGTCAGG | Polymicrogyria, bilateral frontoparietal |
| 147952488 | NM_002437.4(MPV17):c.186 + 2T > C | TGGYAAGTTCTCCCCTCAACAGG | Navajo neurohepatopathy |
| 21909537 | NM_001145.4(ANG):c.121A > G (p.Lys41Glu) | TGGTTYGGCATCATAGTGCTGGG, GTGGTTYGGCATCATAGTGCTG G | Amyotrophic lateral sclerosis type 9 |
| 121918489 | NM_000141.4(FGFR2):c.1018T > C (p.Tyr340His) | TGGGGAAYATACGTGCTTGGCGG, GGGGAAYATACGTGCTTGGCGGG | Crouzon syndrome |
| 121434463 | m.12320A > G | GAGTYGCACCAAAATTTTGGGG, GGAGTYGCACCAAAATTTTGGG, TGGAGTYGCACCAAAATTTTG G | Mitochondrial myopathy |
| 121908046 | NM_000403.3(GALE):c.101A > G (p.Asn34Ser) | TGGAAGYTATCGATGACCACAGG | UDPglucose-4-epimerase deficiency |
| 431905512 | NM_003764.3(STX11):c.173T > C (p.Leu58Pro) | TGCYGGTGGCCCACGTGAAGCCG | Hemophagocytic lymphohistiocytosis, familial, 4 |
| 121917905 | NM_000124.3(ERCC6):c.2960T > C (p.Leu987Pro) | TGCYAAAAGACCCAAAACAAAGG | Cerebro-oculo-facio-skeletal syndrome |
| 121918500 | NM_000141.4(FGFR2):c.874A > G (p.Lys292Glu) | TGCTYGATCCACTGGATGTGGGG, GTGCTYGATCCACTGGATGTGGG, CGTGCTYGATCCACTGATGTG G | Crouzon syndrome |
| 60431989 | NM_000053.3(ATP7B):c.3443T > C (p.Ile1148Thr) | TGCTGAYTGGAAACCGTGAGTGG | Wilson disease |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 78950939 | NM_000250.1(MPO):c.518A > G (p.Tyr173Cys) | GTGCGGYATTTGTCCTGCTCCGG, TGCGGYATTTGTCCTGCTCCGG | Myeloperoxidase deficiency |
| 115677373 | NM_201631.3(TGM5):c.763T > C (p.Trp255Arg) | TGCGGAGYGGACGGGCAGCGTGG | Peeling skin syndrome, acral type |
| 5030804 | NM_000551.3(VHL):c.233A > G (p.Asn78Ser) | GCGAYTGCAGAAGATGACCTGGG, TGCGAYTGCAGAAGATGACCTG | Von Hippel-Lindau syndrome |
| 397508328 | NM_000492.3(CHR):c.1A > G (p.Met1Val) | GCAYGGTCTCTCGGGCGCTGGGG, TGCAYGGTCTCTCGGCGCTGGG, CTGCAYGGTCTCTCGGGCGCTGG | Cystic fibrosis |
| 137853299 | NM_000362.4(TIMP3):c.572A > G (p.Tyr191Cys) | TGCAGYAGCCGCCCTTCTGCCGG | Sorsby fundus dystrophy |
| 121908549 | NM_000334.4(SCN4A):c.3478A > G (p.Ile1160Val) | TGAYGGAGGGGATGCGCCTAGG | |
| 121909337 | NM_001451.2(FOXF1):c.1138T > C (p.Ter380Arg) | TGATGYGAGGCTGCCGCCGCAGG | Alveolar capillary dysplasia with misalignment of pulmonary veins |
| 281875320 | NM_005359.5(SMAD4):c.1500A > G (p.Ile500Met) | TGAGYATGCATAAGCGACGAAGG | Myhre syndrome |
| 730880132 | NM_170707.3(LMNA):c.710T > C (p.Phe237Ser) | TGAGYTTGAGAGCCGCTGGCCGG | Primary dilated cardiomyopathy |
| 81875322 | NM_005359.5(SMAD4):c.1498A > G (p.Ile500Val) | TGAGTAYGCATAAGCGACGAAGG | Myhre syndrome |
| 72556283 | NM_000531.5(OTC):c.527A > G (p.Tyr176Cys) | TGAGGYAATCAGCCAGGATCTGG | not provided |
| 74315311 | NM_020435.3(MC2):c.857T > C (p.Met286Thr) | TGAGAYGGCCCACCTGGGCTTGG, GAGAYGGCCCACCTGGGCTTGG | Leukodystrophy, hypomyelinating, 2 |
| 121912495 | NM_170707.3(LMNA):c.1139T > C (p.Leu380Ser) | TCTYGGAGGGCGAGGAGGAGAGG | Congenital muscular dystrophy, LMNA-related |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base
to be edited, e.g., C. (SEQ ID NOs: 747 to 1868 appear from top to bottom below,
respectively)

| dbSNP # | Genotype | Protospacer and PAM sequence(s) | Associated uenetic disease |
|---|---|---|---|
| 128620184 | NM_000061.2(BTK):c.1288A > G (p.Lys430Glu) | TCTYGATGGCCACGTCGTACTGG | X-linked agammaglobulinemia |
| 118192252 | NM_004519.3(KCNQ3):c.1403A > G (p.Asn468Ser) | TCTTTAYTGTTTAAGCCAACAGG | Benign familial neonatal seizures 2, not specified |
| 121909142 | NM_001300.5(KLF6):c.190T > C (p.Trp64Arg) | TCTGYGGACCAAAATCATTCTGG | |
| 104895503 | NM_001127255.1(NLRP7):c.2738A > G (p.Asn913Ser) | TCTGGYTGATACTCAAGTCCAGG | Hydatidiform mole |
| 587783035 | NM_000038.5(APC):c.1744-2A > G | TCCYAGTAAGAAACAGAATATGG | Familial adenomatous polyposis 1 |
| 72556289 | NM_000531.5(OTC):c.541-2A > G | TCCYAAAAGGCACGGATGAAGG | not provided |
| 28937313 | NM_005502.3(ABCA1):c.2804A > G (p.Asn935Ser) | TCCAYTGTGGCCCAGGAAGGAGG, CGCTCCAYTGTGGCCCAGGAAGG | Tangier disease |
| 143246552 | NM_001003811.1(TEX11):c.511A > G (p.Met171Val) | TCCAYGGTCAAGTCAGTCAGCCTCAGG, CCAYGGTCAAGTCAGTCAGCCTCAGG | Spermatogenic failure, X-linked, 2 |
| 587776451 | NM_002049.3(GATA1):c.2T > C (p.Met1Thr) | CTTCAYGGAGTTCCCTGGCCTGG, CCAYGGAGTTCCCTGGCCTGGG, CCAYGGAGTTCCCTGGCCTGGG | GATA-1-related thrombocytopenia with dyserythropoiesis |
| 121908403 | NM_021102.3(SPINT2):c.488A > G (p.Tyr163Cys) | TCCAYAGATGAAGTTATTGCAGG | Diarrhea 3, secretory sodium, congenital, syndromic |
| 281874738 | NM_000495.4(COL4A5):c.438 + 2T > C | CTTCCAGYAAGTTATAAAATTTGG, TCCAGYAAGTTATAAAATTTGG | Alport syndrome, X-linked recessive |
| 730880279 | NM_030653.3(DDX11):c.2271 + 2T > C | TCCAGGYGCGGGCGTCATGCTGG, CCAGGYGCGGGCGTCATGCTGGG | Warsaw breakage syndrome |
| 28940272 | NM_017890.4(VPS13B):c.8978A > G (p.Asn2993Ser) | TCAYTGATAAGCAGGGCCCAGGG, TTCAYTGATAAGCAGGGCCCAGG | Cohen syndrome, not specified |
| 137852375 | NM_000132.3(F8):c.5372T > C (p.Met1791Thr) | TCAYGGTGAGTTAAGGACAGTGG | Hereditary factor VIII deficiency disease |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base
to be edited, e.g., C. (SEQ ID NOs: 747 to 1868 appear from top to bottom below,
respectively)

| dbSNP # | Genotype | Protospacer and PAM sequence(s) | Associated genetic disease |
|---|---|---|---|
| 11567847 | NM_021961.5(TEAD1):c.1261T > C (p.Tyr?His) | TCATATTYACAGGCTTGTAAAGG | |
| 786203989 | NM_016069.9(PAM16):c.226A > G (p.Asn76Asp) | CATAGTYCTGCAGAGAGAGAGGG, TCATAGTYCTGCAGAGAGAGGG | Chondrodysplasia, megarbane-dagher-melki type |
| 587776437 | NC_012920.1:m.9478T > C | TCAGAAGYTTTTTCTTCCGACG | Leigh disease |
| 121912474 | NM_000424.3(KRT5):c.20T > C (p.Val7Ala) | TCAAGTYGTCCTTCCGGAGCG, CAAGTYGTCCTTCCGGAGCGGG, AAGTYGTCCTTCCGGAGCGGGG, AGTYGTCCTTCCGGAGCGGGGG | Epidermolysis bullosa simplex, Koebner type |
| 104886461 | NM_020533.2(MCOLN1):c.406-2A > G | TACYGTGGGCAGAGAGGGGAG, AGGTACYGTGGGCAGAGAAGGGG, CAGGTACYGTGGGCAGAGAAGGG | Ganglioside sialidase deficiency |
| 104894275 | NM_000317.2(PTS):c.155A > G (p.Asn52Ser) | TAAYTGTGCCCATGGCCATTTGG | 6-pyruvoyl-tetrahydroptermsynthase deficiency |
| 587777562 | NM_015599.2(PGM3):c.737A > G (p.Asn246Ser) | TAAATGAYTGAGTTTGCCCCTTGG | Immunodeficiency 23 |
| 121964906 | NM_000027.3(AGA):c.916T > C (p.Cys306Arg) | GTTATAYGTGCCAATGTGACTGG | Aspartylglycosaminuria |
| 28941769 | NM_000356.3(TCOF1):c.149A > G (p.Tyr50Cys) | GTGTGTAYAGATGTCCAGAAGGG | Treacher collins syndrome 1 |
| 121134464 | m.12297T > C | GTCYTAGGCCCCCAAAAATTTTGG | Cardiomyopathy, mitochondrial |
| 121908407 | NM_054027.4(ANKH):c.143T > C (p.Met48Thr) | GTCGAGAYGCTGGCCAGCTACCG, TCGAGAYGCTGGCCAGCTACGGG | Chondrocalcinosis 2 |
| 59151893 | NM_000422.2(KRT17):c.275A > G (p.Asn92Ser) | GTCAYTGAGGTTCTGCATGGTGG, GCGGTCAYTGAGGTTCTGCATGG | Pachyonychia congenita type 2 |
| 121909499 | NM_002427.3(MMP13):c.272T > C (p.Met91Thr) | GTCAYGAAAAAGCCAAGATGCCG, TCAYGAAAAAGCCAAGATGCCGG | |
| 61748478 | NM_000552.3(VWF):c.2384A > G (p.Tyr795Cys) | GTCAYAGTTCTGGCACGTTTTGG | von Willebrand disease type 2N |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 387906889 | NM_006796.2(AFG3L2):c.1847A > G (p.Tyr616Cys) | GTAYAGAGGTATTGTTCTTTTGG | Spastic ataxia 5, autosomal recessive |
| 118203907 | NM_000130.4(F5):c.5189A > G (p.Tyr1730Cys) | GTAGYAGGCCCAAGCCCGACAGG | Factor V deficiency |
| 118203945 | NM_013319.2(UBIAD1):c.305A > G (p.Asn102Ser) | GTAAGTYGYTGACCAAATTACCCG | Schnyder crystalline corneal dystrophy |
| 267607080 | NM_005633.3(SOS1):c.1294T > C (p.Trp432Arg) | GGTYGGGAGGGAAAAGACATTGG | Noonan syndrome 4, Rasopathy |
| 137852953 | NM_012464.4(TLL1):c.1885A > G (p.Ile629Val) | GGTTAYGGTGCCGTTAAGTTTGG | Atrial septal defect 6 |
| 118203949 | NM_013319.2(UBIAD1):c.692A > G (p.Asn32Ser) | GGTGTTYGYTGGAATGGAGAATGG | Schnyder crystalline corneal dystrophy |
| 137852952 | NM_012464.4(TLL1):c.713T > C (p.Val238Ala) | GGGATTGYTGTTCATGAATTGG | Atrial septal defect 6 |
| 41460449 | m.3394T > C | GGCYATATACAACTACGCAAAGG | Leber optic atrophy |
| 80357281 | NM_007294.3(BRCA1):c.5291T > C (p.Leu1764Pro) | GGGCYAGAAATCTGTTGCTATGG, GGCYAGAAATCTGTTGCTATGG | Familial cancer of breast, Breast-ovarian cancer, familial 1 |
| 5030764 | NM_000174.4(GP9):c.182A > G (p.Asn61Ser) | GGCTGYTGTTGGCCAGCAGAAGG | Bernard-Soulier syndrome type C |
| 72556282 | NM_000531.5(OTC):c.526T > C (p.Tyr176His) | GGCTGATYACCTCACGCTCCAGG, GATYACCTCACGCTCCAGGTTGG | not provided |
| 121913594 | NM_000530.6(MPZ):c.242A > G (p.His81Arg) | GGCATAGYGGAAGATCTATGAGG | Charcot-Marie-Tooth disease type 1B |
| 587777736 | NM_017617.3(NOTCH1):c.1285T > C (p.Cys429Arg) | GGCAAGYGCATCAACACGCTGGG, GGGCAAGYGCATCAACACGCTGG | Adams-Oliver syndrome 1, Adams-Oliver syndrome 5 |
| 63750912 | NM_016835.4(MAPT):c.1839T > C (p.Asn613=) | GGATAAYATCAAACACGTCCCGG, GATAAYATCAAACACGTCCCGG | Frontotemporal dementia |
| 121918075 | NM_000371.3(TTR):c.401A > G (p.Tyr134Cys) | GGAGYAGGGCTCAGCAGGGCGG, ATAGGAGYAGGGCTCAGCAGGG | Amyloidogenic transthyretin amyloidosis |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 730882063 | NM_004523.3(KIF11):c.2547 + 2T > C | GGAGGYAATAACTTTGTAAGTGG | Microcephaly with or without chorioretinopathy, lymphedema, or mental retardation |
| 397516156 | NM_000257.3(MYH7):c.2546T > C (p.Met849Thr) | GGAGAYGGCCTCCATGAAGGAGG | Primary familial hypertrophic cardiomyopathy, |
| 118204430 | NM_000035.3(ALDOB):c.442T > C (p.Trp148Arg) | GGAAGYGGCYGTGCTGTGCTGAGG | Hereditary fructosuria |
| 200198778 | NM_013382.5(POMT2):c1997A > G (p.Tyr666Cys) | GGAAGYAGTGGTGGAAGTAGAGG | Congenital muscular dystrophy, Congenital muscular dystrophy-dystroglycanopathy with brain and eye anomalies, type A2, Muscular dystrophy, Congenital muscular dystrophy-dystroglycanopathy with mental retardation, type B2 |
| 754896795 | NM_004006.2(DMD):c.6982A > T (p.Lys2328Ter) | GCTTTYTTCAAGCTGCCCAAGG | Duchenne muscular dystrophy, Becker muscular dystrophy, Dilated cardiomyopathy 3B |
| 148924904 | NM_000546.5(TP53):c.488A > G (p.Tyr163Cys) | GCTTGYAGATGCCATGGCGCGG | Hereditary cancer-predisposing syndrome |
| 786204770 | NM_016035.4(COQ4):c.155T > C (p.Leu52Ser) | GCTGTYGGCCGCCGGCTCCGCGG | COENZYME Q10 DEFICIENCY, PRIMARY, 7 |
| 121909520 | NM_001100.3(ACTA1):c.350A > G (p.Asn117Ser) | CGGYTGGCCTTGGGATTGAGGGG, GCGGYTGGCCTTGGGATTGAGGG, CGCGGYTGGCCTTGGGATTGAGG | Nemaline myopathy 3 |
| 587776879 | NM_004656.3(BAP1):c.438-2A > G | GCCYGGGGAAAAACAGAGTCAGG | Tumor predisposition syndrome |
| 727504434 | NM_000501.3(ELN):c.890-2A > G | GCCYGAAAACAGCCACAGAGG | Supravalvar aortic stenosis |
| 119455953 | NM_000391.3(TPP1):c.1093T > C (p.Cys365Arg) | GCCGGGYGTTGGTCTGTCTCTGG | Ceroid lipofuscinosis, neuronal, 2 |
| 121964983 | NM_000481.3(AMT):c.125A > G (p.His42Arg) | GCCAGGYGGAAGTCATAGAGCGG | Non-ketotic hyperglycinemia |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 121908300 | NM_001005741.2(GBA):c.751T > C (p.Tyr251His) | GCCAGAYACTTTGTGAAGTAAGG, CCAGAYACTTTGTGAAGTAAGG | Gaucher disease, type 1 |
| 786205083 | NM_003494.3(DYSF):c.3443-33A > G | GCCAGAGYGAGTGGCTGGAGTGG | Limb-girdle muscular dystrophy, type 2B |
| 121908133 | NM_175073.2(APTX):c.602A > G (p.His201Arg) | GCCAAYGGTAACGGGCCTTTGGG, AGCCAAYGGTAACGGGCCTTTGG | Adult onset ataxia with oculomotor apraxia |
| 587777195 | NM_005017.3(PCYT1A):c.571T > C (p.Phe191Leu) | GCATGYTTGCTCCAACACAGAGG | Spondylometaphyseal dysplasia with cone-rod dystrophy |
| 431905520 | NM_014714.3(IFT140):c.4078T > C (p.Cys1360Arg) | CAAGCAGYGTGAGCTGCTCCTGG, GCAGYGTGAGCTGCTCCTGGAGG | Renal dysplasia, retinal pigmentary dystrophy, cerebellar ataxia and skeletal dysplasia |
| 121912889 | NM_001844.4(COL2A1):c.4172A > G (p.Tyr1391Cys) | GCAGTGGYAGGTGATGTTCTGGG | Spondyloperipheral dysplasia, Platyspondylic lethal skeletal dysplasia Torrance type |
| 137854492 | NM_001363.4(DKC1):c.I069A > G (p.Thr357Ala) | GCAGGYAGAGATGACCGCTGTGG | Dyskeratosis congenita X-linked |
| 121434362 | NM_152783.4(D2HGDH):c.1315A > G (p.Asn439Asp) | GCAGGYACCATCTCCTGGAGGG, TGCAGGYACCATCTCCTGGAGG | D-2-hydroxyglutaric aciduria 1 |
| 80338732 | NM_002764.3(PRPS1):c.344T > C (p.Met115Thr) | GCAAATAYGCTATCTGTAGCAGG | Charcot-Marie-Tooth disease, X-linked recessive, type 5 |
| 387906675 | NM_000313.3(PROS1):c.701A > G (p.Tyr234Cys) | GATTAYATCTGTAGCCTTCGGGG, AGATTAYATCTGTAGCCTTCGGG, GAGATTAYATCTGTAGCCTTCCGG | Thrombophilia due to protein S deficiency, autosomal recessive |
| 28935478 | NM_000061.2(BTK):c.1082A > G (p.Tyr361Cys) | GATGGYAGTTAATGAGCTCAGGG, TGATGGYAGTTAATGAGCTCAGG | |
| 201777056 | NM_005050.3(ABCD4):c.956A > G (p.Tyr319Cys) | GATGAGGYAGATGCACACAAAGG | METHYLMALONIC ACIDURIA AND HOMOCYSTINURIA, cblJ |
| 121918528 | NM_000098.2(CPT2):c.359A > G (p.Tyr120Cys) | GATAGGYACATATCAAACCAGGG, AGATAGGYACATATCAAACCAG | Carnitine palmitoyltransferase II deficiency, infantile |
| 267607014 | NM_002942.4(ROBO2):c.2834T > C (p.Ile945Thr) | GAGAYTGGAAATTTGCCCGTGG | Vesicoureteral reflux 2 |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 281865192 | NM_025114.3(CEP290):c.2991 + 1655 A > G | GATAYTCACAATTACAACTGGGG, AGATAYTCACAATTACAACTGGG, GAGATAYTCACAATTACAACTG | Leber congenital amaurosis 10 |
| 386833492 | NM_000112.3(SLC26A2):c.- 26 + 2T > C | GAGAGGYGAGAGAGAGGAAGCCGG | Diastrophic dysplasia |
| 587779773 | NM_001101.3(ACTB):c.356T > C (p.Met119Thr) | GAGAAGAYGACCCAGGTGAGTGG | Baraitser-Winter syndrome 1 |
| 121913512 | NM_000222.2(KIT):c.1924A > G (p.Lys642Glu) | GACTTYGAGTTCAGACATGAGGG, GGACTTYGAGTTCAGACATGAGG | |
| 28939072 | NM_006329.3(FBLN5):c.506T > C (p.Ile169Thr) | GACAYTGATGAATGTCGCTATGG | Age-related macular degeneration 3 |
| 104894248 | NM_000525.3(KCNJ11):c.776A > G (p.His259Arg) | GACAYGGTAGATGATCAGCGGGG, TGACAYGGTAGATGATCAGCGCGG, ATGACAYGGTAGATGATCAGCGG | Islet cell hyperplasia |
| 387907132 | NM_016464.4(TMEM138):c.287A > G (p.His96Arg) | GACAYGAAGGAGATGCTGAGGG, AGACAYGAAGGAGATGCTGAGG | Joubert syndrome 16 |
| 121918170 | NM_000275.2(OCA2):c.1465A > G (p.Asn489Asp) | GACATYTGGAGGGTCCCCGATGG | Tyrosinase-positive oculocutaneous albinism |
| 122467173 | NM_014009.3(FOXP3):c.970T > C (p.Phe324Leu) | GACAGAGYTCCTCCACAACATGG | Insulin-dependent diabetes mellitus secretory diarrhea syndrome |
| 137852268 | NM_000133.3(F9):c.1328T > C (p.Ile443Thr) | GAAYATATACCAAGGTATCCCCG | Hereditary factor IX deficiency disease |
| 149054177 | NM_001999.3(FBN2):c.3740T > C (p.Met1247Thr) | GAATGTAYGATAATGAACGAGGG | not specified, Macular degeneration, early-onset |
| 137854488 | NM_212482.1(FN1):c.2918A > G (p.Tyr973Cys) | GAAGTAYAGGTGACCCCAGGGG | Glomerulopathy with fibronectin deposits 2 |
| 786204027 | NM_005957.4(MTHFR):c.1530 + 2T > C | GAAGGYGTGGTAGGAGGCACGG, AAGGYGTGGTAGGGAGGCACGGG, AGGYGTGGTAGGGAGGCACGGGG | Homocysteinemia due to MTHFR deficiency |
| 104894223 | NM_012193.3(FZD4):c.766A > G (p.Ile256Val) | GAAATAYGATGGGGCCTCAGGG, AGAAATAYGATGGGGCCTCAGG | Retinopathy of prematurity |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 137854474 | NM_000138.4(FBN1):c.3793T > C (p.Cys1265Arg) | CTTGYGTTATGATGGATTCATGG | Madan syndrome |
| 587784418 | NM_006306.3(SMC1A):c.3254A > G (p.Tyr1085Cys) | CTTAYAGATCTTCATCAATGTTGG | Congenital muscular hypertrophy-cerebral syndrome |
| 81002805 | NM_000059.3(BRCA2):c.316 + 2T > C | CTTAGGYAAGTAATGCAATATGG | Familial cancer of breast, Breast-ovarian cancer, familial 2, Hereditary cancer-predisposing syndrome |
| 121909653 | NM_182925.4(FLT4):c.3104A > G (p.His1035Arg) | CTGYGGATGCACTGGGGTGCGGG, TCTGYGGATGCACTGGGGTGCGG | |
| 786205107 | NM_031226.2(CYP19A1):c.743 + 2T > C | CTGTGYAAGTAATACAACTTTGG | Aromatase deficiency |
| 587777037 | NM_001283009.1(RTEL1):c.3730T > C | CTGTGTGYGCCAGGGCTGTGGGG | Dyskeratosis congenita, autosomal recessive, 5 |
| 794728380 | NM_000238.3(KCNH2):c.1945 + 6T > C | CTGTGAGYGTGCCCAGGGGCGGG, TGAGYGTGCCCAGGGGCGGGCGG | Cardiac arrhythmia |
| 267607987 | NM_000251.2(MSH2):c.2005 + 2T > C | CTGGYAAAAACCTGGTTTTGG, TGGYAAAAACCTGGTTTTGG C | Hereditary Nonpolyposis Colorectal Neoplasms |
| 397509397 | NM_006876.2(B4GAT1):c.1168A > G (p.Asn390Asp) | TGATYTTCAGCCTCCTTTTGGGG, CTGATYTTCAGCCTCCTTTTGGG, GCTGATYTTCAGCCTCCTTTTGG | Congenital muscular dystrophy-dystroglycanopathy with brain and eye anomalies, type A13 |
| 121918381 | NM_000040.1(APOC3):c.280A > G (p.Thr94Ala) | CTGAAGYTGGTCTGACCTCAGGG, GCTGAAGYTGGTCTGACCTCAGG | |
| 104894919 | NM_001015877.1(PHF6):c.769A > G (p.Arg257Gly) | CTCYTGATGTTGTTGTGAGCTGG | Borjeson-Forssman-Lehmann syndrome |
| 267606869 | NM_005144.4(HR):c.-218A > G | CTCYAGGGCCCGCAGGTTGGAGGG, GCTCYAGGGCCGCAGGTTGGAGG, GGCGCTCYAGGGCCGCAGGTTGG | Marie Unna hereditary hypotrichosis 1 |
| 139732572 | NM_000146.3(FTL):c.1A > G (p.Met1Val) | CTCAYGGTTGGTTGGCAAGAGAGG | L-ferritin deficiency |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 397515418 | NM_018486.2(HDAC8):c.1001A > G (p.His334Arg) | CTCAYGATCTGGGATCTCAGAGG | Cornelia de Lange syndrome 5 |
| 372395294 | NM_198056.2(SCN5A):c.1247A > G (p.Tyr416Cys) | CTCAYAGGCCATTGCGACCACGG | not provided |
| 104895304 | NM_000431.3(MVK):c.803T > C (p.Ile268Thr) | CTCAAYAGATGCCATCTCCCTGG | Hyperimmunoglobulin D with periodic fever, Mevalonic aciduria |
| 587777188 | NM_001165899.1(PDE4D):c.1850T > C (p.Ile617Thr) | CTATAYTGTTCATCCCCTCTGGG, ACTATAYTGTTCATCCCCTCTGG | Acrodysostosis 2, with or without hormone resistance |
| 398123026 | NM_003867.3(FGF17):c.560A > G (p.Asn187Ser) | CGTGGYTGGGGAAGGGCAGCTGG | Hypogonadotropic hypogonadism 20 with or without anosmia |
| 121964924 | NM_001385.2(DPYS):c.1078T > C (p.Trp360Arg) | CGTAATAYGGGAAAAAGGCGTGG, AATAYGGGAAAAAGGCGTGGTGG, ATAYGGGAAAAAGGCGTGGTGGG | Dihydropyrimidinase deficiency |
| 587777301 | NM_199189.2(MATR3):c.1864A > G (p.Thr622Ala) | CGGYTGAACTCTCAGTCTTCTGG | Myopathy, distal, 2 |
| 200238879 | NM_000527.4(LDLR):c.694 + 2T > C | ACTGCGYATGGGCGGGGCCAGG, CTGCGYATGGGGCGGGGCCAGGG, CGGYATGGGCGGGGCCAGGGTGG | Familial hypercholesterolemia |
| 142951029 | NM_145046.4(CALR3):c.245A > G (p.Lys82Arg) | CGGTTYTGAAGCGTGCAGAGATGG | Arrhythmogenic right ventricular cardiomyopathy, Familial hypertrophic cardiomyopathy 19, Hypertrophic cardiomyopathy |
| 786200953 | NM_006785.3(MALT1):c.1019-2A > G | CGCYTTGAAAAAAAAGAAAGGG, TCGCYTTGAAAAAAAAAGAAAG | Combined immunodeficiency |
| 120074192 | NM_000218.2(KCNQ1):c.418A > G (p.Ser140Gly) | CGCYGAAGATGAGGCAGACCAGG | Atrial fibrillation, familial, 3, Atrial fibrillation |
| 267606887 | NM_005957.4(MTHFR):c.971A > G (p.Asn324Ser) | CGCGGYTGAGGGTGTAGAAGTGG | Homocystinuria due to MTHFR deficiency |
| 118192117 | NM_000540.2(RYR1):c.1205T > C (p.Met402Thr) | CGCAYGATCCACAGCACCAATGG | Congenital myopathy with fiber type disproportion, Central core disease |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base
to be edited, e.g., C. (SEQ ID NOs: 747 to 1868 appear from top to bottom below,
respectively)

| dbSNP # | Genotype | Protospacer and PAM sequence(s) | Associated genetic disease |
|---|---|---|---|
| 199473625 | NM_198056.2(SCN5A):c.4978A > G (p.Ile1660Val) | CGAYGTTGAAGAGGGCAGGCAGG, AGCCCGAYGTTGAAGAGGGCAGG | Brugada syndrome |
| 794726865 | NM_000921.4(PDE3A):c.1333A > G (p.Thr445Ala) | CGAGGYGGTGGTGGTCCAAGTGG | Brachydactyly with hypertension |
| 606231254 | NM_005740.2(DNAL4):c.153 + 2T > C | CGAGGYATTGCCAGCAGTGCAGG | Mirror movements 3 |
| 786204826 | NM_004771.3(MMP20):c.611A > G (p.His204Arg) | CGAAAYGTGTATCTCCTCCCAGG | Amelogenesis imperfecta, hypomaturation type, IIA2 |
| 796053139 | NM_021007.2(SCN2A):c.4308 + 2T > C | CGAAATGYAAGTCTAGTTAGAGG, GAAATGYAAGTCTAGTTAGAGG | not provided |
| 137854494 | NM_005502.3(ABCA1):c.4429T > C (p.Cys1477Arg) | CCTGTGYGTCCCCAGGGGCAGG, CTGTGYGTCCCCAGGGGCAGGG, TGTGYGTCCCCAGGGGCAGGGG, GTGYGTCCCCAGGGGCAGGGGG | Tangier disease |
| 786205144 | NM_001103.3(ACTN2):c.683T > C (p.Met228Thr) | CCTAAAAYGTTGGATGCTGAAGG | Dilated cardiomyopathy IAA |
| 199919568 | NM_007254.3(PNKP):c.1029 + 2T > C | CCGGYGAGGCCCTGGGCGGGG, TCCGGYGAGGCCCTGGGGCGGG, ATCCGGYGAGGCCCTGGGGCGG, GATCCGGYGAGGCCCTGGGCCG | not provided |
| 28939079 | NM_018965.3(TREM2):c.401A > G (p.Asp134Gly) | TGAYCCAGGGGGTCTATGGAGG, CGGTGAYCCAGGGGTCTATGG, CCGGTGAYCCAGGGGTCTATCG | Polycystic lipomembranous osteodysplasia with sclerosing leukoencephalopathy |
| 193302855 | NM_032520.4(GNPTG):c.610-2A > G | CCCYGAAGGTGGAGATGCAGGG, GCCCYGAAGGTGGAGATGCAGG | Mucolipidosis III Gamma |
| 111033708 | NM_000155.3(GALT):c.499T > C (p.Trp167Arg) | CCCTYGGGTGCAGGTTTGTGAGG | Deficiency of UDPglucose-hexose-1-phosphate uridylyltransferase |
| 28933378 | NM_000174.4(GP9):c.70T > C (p.Cys24Arg) | CCCAYGTACCTGCCGCCGCCCTGG | Bernard Soulier syndrome, Bernard-Soulier syndrome type C |
| 364897 | NM_000157.3(GBA):c.680A > G (p.Asn227Ser) | CCAYTGGTCTTGAGCCAAGTGGG, TCCAYTGGTCTTGAGCCAAGTGG | Gaucher disease, Subacute neuronopathic Gaucher disease, Gaucher disease, type 1 |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 796052551 | NM_000833.4(GRIN2A):c.2449A > G (p.Met817Val) | CCAYGTTGTCAATGTCCAGCTGG | not provided |
| 63751006 | NM_002087.3(GRN):c.2T > C (p.Met1Thr) | CCAYGTGGACCCTGGTGAGCTGG | Frontotemporal dementia, ubiquitin-positive |
| 786203997 | NM_001031.4(RPS28):c.1A > G (p.Met1Val) | TGTCCAYGATGGCGGCGGCGGCGG, CCAYGATGGCGGCGGCGGCGGCGG | Diamond-Blackfan anemia with microtia and cleft palate |
| 121908595 | NM_002755.3(MAP2K1):c.389A > G (p.Tyr130Cys) | CCAYAGAAGCCCACGATGATACGG | Cardiofaciocutaneous syndrome 3, Rasopathy |
| 398122910 | NM_000431.3(MVK):c.1039 + 2T > C | CCAGGYATCCCGGGGTAGGTGG, CAGGYATCCCGGGGTAGGTGGG | Porokeratosis, disseminated superficial actinic 1 |
| 119474039 | NM_020365.4(EIF2B3):c.1037T > C (p.Ile346Thr) | CCAGAYTGTCAGCAAACACCTGG | Leukoencephalopathy with vanishing white matter |
| 587777866 | NM_000076.2(CDKN1C):c.*5 + 2T > C | CCAAGYGAGTACAGCCACCTGG, CAAGYGAGTACAGCGCACCTGGG, AAGYGAGTACAGCGCACCTGGGG | Beckwith-Wiedemann syndrome |
| 121918530 | NM_005587.2(MEF2A):c.788A > G (p.Asn263Ser) | AGAYTACCACCACCTGTGAGG, CCAAGAYTACCACCACCTGTGG | |
| 483352818 | NM_000211.4(ITGB2):c1877 + 2T > C | CATGYGAGTGCAGGCGGAGCAGG | Leukocyte adhesion deficiency type 1 |
| 460184 | NM_000186.3(CFH):c.3590T > C (p.Val1197Ala) | CAGYTGAATTTGTGTGTAAACGG | Atypical hemolytic-urem c syndrome 1 |
| 121908423 | NM_004795.3(KL):c.578A > G (p.His193Arg) | CAGYGGTACAGGGTGACCACGG, CCAGYGGTACAGGGTGACCACGG | |
| 281860300 | NM_005247.2(FGF3):c.146A > G (p.Tyr49Cys) | CAGYAGAGCTTGCGGCGCCGGG, GCAGYAGAGCTTGCGGCGCCGG, CGCAGYAGAGCTTGCGCGCCGG | Deafness with labyrinthine aplasia microtia and microdontia (LAMM) |
| 28935488 | NM_000169.2(GLA):c.806T > C (p.Val269Ala) | CAGTTAGYGATTGGCAACTTTGG | Fabry disease |
| 587776514 | NM_173560.3(RFX6):c.380 + 2T > C | CAGTGGYGAGACTCGCCCGCAGG, AGTGGYGAGACTCGCCCGCAGGG | Mitchell-Riley syndrome |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 104894117 | NM_178138.4(LHX3):c.332A > G (p.Tyr111Cys) | CAGGTGGYACACGAAGTCCTGGG | Pituitary hormone deficiency, combined 3 |
| 34878913 | NM_000184.2(HBG2):c.125T > C (p.Phe42Ser) | CAGAGGTYCTTTGACAGCTTTGG | Cyanosis, transient neonatal |
| 120074124 | NM_000543.4(SMPD1):c.911T > C (p.Leu304Pro) | AGCACTGTGAGGAAGTTCCTGG, GCACTGTGAGGAAGTTCCTGG, CACYTGTGAGGAAGTTCCTGGGG | Sphingomyelin/cholesterol lipidosis, Niemann-Pick disease, type A, Niemann-Pick disease, type B |
| 281860272 | NM_005211.3(CSF1R):c.2320-2A > G | CACYGAGGGAAAGCACTGCAGGG, GCACYGAGGGAAAGCACTGCAGG | Hereditary diffuse leukoencephalopathy with spheroids |
| 128624216 | NM_000033.3(ABCD1):c.443A > G (p.Asn148Ser) | CACTGYTGACGAAGGTAGCAGGG, GCACTGYTGACGAAGGTAGCAGG | Adrenoleukodystrophy |
| 398124257 | NM_012463.3(ATP6V0A2):c.825 + 2T > C | CACTGYGAGTAAGCTGGAAGTGG | Cutis laxa with osteodystrophy |
| 267606679 | NM_004183.3(BEST1):c.704T > C (p.Val235Ala) | CACTGGYGTATACACAGGTGAGG | Vitreoretinochoroidopathy dominant |
| 397514518 | NM_000344.3(SMN1):c.388T > C (p.Tyr130His) | CACTGGAYATGAAATAGAGAGG | Kugelberg-Welander disease |
| 143946794 | NM_001946.3(DUSP6):c.566A > G (p.Asn189Ser) | CACTAYTGGGGTCTCCGTCAAGG | Hypogonadotropic hypogonadism 19 with or without anosmia |
| 397516076 | NM_000256.3(MYBPC3):c.821 + 2T > C | GCACGYGAGTGGCCATCCTCAGG, CACGYGAGTGGCCATCCTCAGGG | Familial hypertrophic cardiomyopathy 4, not specified |
| 149977726 | NM_001257988.1(TYMP):c.665A > G (p.Lys222Arg) | CACGAGTYTCTTTACTGAGAATGG, GAGTYTCTTACTGAGAATGGAGG | |
| 121917770 | NM_003361.3(UMOD):c.383A > G (p.Asn128Ser) | CACAYTGACACATGTGGCCAGGG, CCACAYTGACACATGTGGCCAGG | Familial juvenile gout |
| 121909008 | NM_000492.3(CFTR):c.2738A > G (p.Tyr913Cys) | CACATAAYACGAACTGGTGTGG | Cystic fibrosis |
| 137852819 | NM_003688.3(CASK):c.2740T > C (p.Trp914Arg) | CACAGYGGGTCCCTGTCTCCTGG, ACAGYGGGTCCCTGTCTCCTGGG | FG syndrome 4 |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 74315320 | NM_024009.2(GJB3):c.421A > G (p.Ile141Val) | CAAYGATGAGCTTGAAGATGAGG | Deafness, autosomal recessive |
| 80356747 | NM_001701.3(BAAT):c.967A > G (p.Ile323Val) | CAAYGAAGAGGAATTGCCCCTGG | Atypical hemolytic-uremic syndrome 1 |
| 180177324 | NM_012203.1(GRHPR):c.94A > G (p.Asn312Asp) | CAAGTYGTTAGCTGCCAACAAGG | Primary hyperoxaluria, type II |
| 281860274 | NM_005211.3(CSF1R):c.2381T > C (p.Ile794Thr) | CAAGAYTGGGGACTTCCGGCTGG | Hereditary diffuse leukoencephalopathy with spheroids |
| 398122908 | NM_005334.2(HCFC1):c.-970T > C | CAAGAYGGCGGCTCCCAGGGAGG | Mental retardation 3, X-linked |
| 548076633 | NM_002693.2(POLG):c.3470A > G (p.Asn1157Ser) | CAAGAGGYTGGTGATCTGCAAGG | not provided |
| 120074146 | NM_000019.3(ACAT1):c.935T > C (p.Ile312Thr) | CAAGAAYAGTAGGTAAGGCCAGG | Deficiency of acetyl-CoA acetyltransferase |
| 397514489 | NM_005340.6(HINT1):c.250T > C (p.Cys84Arg) | CAAGAAAYGTGCTGCTGATCTGG, AAGAAAYGTGCTGCTGATCTGGG | Gamstorp-Wohlfart syndrome |
| 587783539 | NM_178151.2(DCX):c.2T > C (p.Met1Thr) | CAAAATAYGGAACTTCGATTTTGG | Heterotopia |
| 104894765 | NM_005448.2(BMP15):c.704A > G (p.Tyr235Cys) | ATTGAAAYAGAGTAACAAGAAGG | Ovarian dysgenesis 2 |
| 137852429 | NM_000132.3(F8):c.1892A > G (p.Asn631Ser) | ATGYTGGAGGCTTGGAACTCTGG | Hereditary factor VIII deficiency disease |
| 72558441 | NM_000531.5(OTC):c.779T > C (p.Leu260Ser) | ATGTATYAATTACAGACACTTGG | not provided |
| 398123765 | NM_003494.3(DYSF):c.1284 + 2T > C | ATGGYAAGGAGCAAGGGAGCAGG | Limb-girdle muscular dystrophy, type 2B |
| 387906924 | NM_020191.2(MRPS22):c.644T > C (p.Leu215Pro) | ATCYTAGGGTAAGGTGACTTAGG | Combined oxidative phosphorylation deficiency 5 |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 397518039 | NM_206933.2(USH2A):c.8559-2A > G | ATCYAAAGCAAAAGACAAGCAGG | Retinitis pigmentosa, Usher syndrome, type 2A |
| 5742905 | NM_000071.2(CBS):c.833T > C (p.Ile278Thr) | ATCAYTGGGGTGGATCCCGAAGG, TCAYTGGGGTGGATCCCGAAGGG | Homocystinuria due to CBS deficiency, Homocystinuria, vridnxine-resnnnsiv |
| 397507473 | NM_004333.4(BRAF):c.1403T > C (p.Phe468Ser) | ATCATYTGGAACAGTCTACAAGG, TCATYTGGAACAGTCTACAAGG | Cardiofaciocutaneous syndrome, Rasopathy |
| 786204056 | NM_000264.3(PTCH1):c.3168 + 2T > C | ATCATTGYGAGTGTATTATAAGG, TCATTGYGAGTGTATTATAAGG, CATTGYGAGTGTATTATAAGG | Gorlin syndrome |
| 72558484 | NM_000531.5(OTC):c.1005 + 2T > C | ATCATGYAAGCAAGAAACAAGG | not provided |
| 199473074 | NM_000335.4(SCN5A):c.688A > G (p.Ile230Val) | ATAYAGTTTTCAGGGCCCGGAGG, CTGATAYAGTTTTCAGGGCCCGG | Brugada syndrome |
| 111033273 | NM_206933.2(USH2A):c.1606T > C (p.Cys536Arg) | ATATAGAYGCCTCTGCTCCCAGG | Usher syndrome, type 2A |
| 72556290 | NM000531.5(OTC):c.542A > G (p.Glu181Gly) | ATAGTGTYCCTAAAAGGCACGGG | not provided |
| 121918711 | NM_004612.3(TGFBR1):c.1199A > G (p.Asp400Gly) | ATAGATGYCAGCACGTTTGAAGG | Loeys-Dietz syndrome 1 |
| 104886288 | NM_000495.4(COL4A5):c.4699T > C (p.Cys1567Arg) | AGTAYGTGAAGCTCCAGCTGTGG | Alport syndrome, X-linked recessive |
| 144637717 | NM_016725.2(FOLR1):c.493 + 2T > C | CTTCAGGYGAGGGCTCGGGTGGG, AGGYGAGGGCTGGGGTGGGCAGG | not provided |
| 72558492 | NM_000531.5(OTC):c.1034A > G (p.Tyr345Cys) | AGGTGAGYAATCTGTCAGCAGGG | not provided |
| 62638745 | NM_000121.3(EPOR):c.1460A > G (p.Asn487Ser) | AGGGYTGGAGTAGGGGCCATCGG | Acute myeloid leukemia, M6 type, Familial erythrocytosis, 1 |
| 387907021 | NM_031427.3(DNAL1):c.449A > G (p.Asn150Ser) | AGGGAYTGCCTACAAACACCAGG | Kartagener syndrome, Ciliary dyskinesia, primary, 16 |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base
to be edited, e.g., C. (SEQ ID NOs: 747 to 1868 appear from top to bottom below,
respectively)

| dbSNP # | Genotype | Protospacer and PAM sequence(s) | Associated uenetic disease |
|---|---|---|---|
| 397514488 | NM_001161581.1(POC1A):c.398T > C (p.Leu133Pro) | AGCYGTGGACAAGAGAGCAGCCGG | Short stature, onychodysplasia, facial dysmorphism, and hypotrichosis |
| 154774633 | NM_017882.2(CLN6):c.200T > C (p.Leu67Pro) | AGCYGGTATTCCCTCCTCGAGTGG | Adult neuronal ceroid lipofuscinosis |
| 111033700 | NM_000155.3(GALT):c.482T > C (p.Leu161Pro) | AGCYGGGTGCCCAGTACCCTTGG | Deficiency of UDPglucose-hexose-1-phosphate uridylyltransferase |
| 128621198 | NM_000061.2(BTK):c.1223T > C (p.Leu408Pro) | GAGCYGGGGACTGGACAATTTGG, AGCYGGGGACTGGACAATTTGGG | X-linked agammaglobulinemia |
| 137852611 | NM_000211.4(ITGB2):c.446T > C (p.Leu149Pro) | AGCYAGGTGGCGACCTGCTCCGG | Leukocyte adhesion deficiency |
| 121908838 | NM_003722.4(TP63):c.697A > G (p.Lys233Glu) | AGCTYTTTTGTAGACAGGCATGG | Split-hand/foot malformation 4 |
| 397515869 | NM_000169.2(GLA):c.1153A > G (p.Thr385Ala) | AGCTGTGYGATGAAGCAGGCAGG | not specified |
| 118204064 | NM_000237.2(LPL):c.548A > G (p.Asp183Gly) | GCTGGAYCGAGGCCTTAAAAGGG, AGCTGGAYCGAGGCCTTAAAAGG | Hyperlipoproteinemia, type I |
| 128620186 | NM_000061.2(BTK):c.2T > C (p.Met1Thr) | AGCTAYGGCCCAGTGATTCTGG | X-linked agammaglobulinemia |
| 786204132 | NM_014946.3(SPAST):c.1165A > G (p.Thr389Ala) | ATTGYCTTCCCATTCCCAGGTGG, AGCATTGYCTTCCCATTCCCAGG | Spastic paraplegia 4, autosomal dominant |
| 199473661 | NM_000218.2(KCNQ1):c.550T > C (p.Tyr184His) | CAGCAAGBACGTGGGCCTCTGGG, AGCAAGBACGTGGGCCTCTGGGG, GCAAGBACGTGGGCCTCTGGGGG | Congenital long QT syndrome, Cardiac arrhythmia |
| 387907129 | NM_024599.5(RHBDF2):c.557T > C (p.Ile186Thr) | AGAYTGTGGATCCGCTGGCCCGG | Howel-Evans syndrome |
| 387906702 | NM_006306.3(SMC1A):c.2351T > C (p.Ile784Thr) | AGAYTGGTGTGCGCAACATCCGG | Congenital muscular hypertrophy-cerebral syndrome |
| 193929348 | NM_000525.3(KCNJ11):c.544A > G (p.Ile182Val) | AGAYGAGGGTCTCAGCCCTGCGG | Permanent neonatal diabetes mellitus |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 121908934 | NM_004086.2(COCH):c.1535T > C (p.Met512Thr) | AGATAYGGCTTCTAAACCGAAGG | Deafness, autosomal dominant 9 |
| 397514377 | NM_000060.3(BTD):c.641A > G (p.Asn214Ser) | AGAGGYTGTGTTTACGGTAGCGG | Biotinidase deficiency |
| 72552295 | NM_000531.5(OTC):c.2T > C (p.Met1Thr) | AGAAGAYGCTGTTTAATCTGAGG | not provided |
| 201893545 | NM_016247.3(IMPG2):c.370T > C (p.Phe124Leu) | ACTYTTTGGGATCGACTTCCTGG | Macular dystrophy, vitelliform, 5 |
| 121434469 | m.4290T > C | ACTYTGATAGAGTAAATAATAGG | |
| 121918733 | NM_006920.4(SCN1A):c.269T > C (p.Phe90Ser) | ACTTYTATAGTATTGAATAAAGG, CTTYTATAGTATTGAATAAAGG | Severe myoclonic epilepsy in infancy |
| 121434471 | m.4291T > C | ACTTYGATAGAGTAAATAATAGG | Hypertension, hypercholesterolemia, and hypomagnesemia, mitochondrial |
| 606231289 | NM_001302946.1(TRNT1):c.497T > C (p.Leu166Ser) | ACTTYATTTGACTACTTTAATGG | Sideroblastic anemia with B-cell immunodeficiency, periodic fevers, and developmental delay |
| 63750067 | NM_000517.4(HBA2):c*92A > G | CTTYATTCAAAGACCAGGAAGGG, ACTTYATTCAAAGACCAGGAAG | Hemoglobin H disease, nondeletional |
| 121918734 | NM_006920.4(SCN1A):c.272T > C (p.Ile91Thr) | ACTTTYAYAGTATTGAATAAAGG, CTTTYAYAGTATTGAATAAAGG C | Severe myoclonic epilepsy in infancy |
| 137854557 | NM_000267.3(NF1):c.1466A > G (p.Tyr489Cys) | ACTTAYAGCTTCTTGTCTCCAGG | Neurofibromatosis, type 1 |
| 397514626 | NM_018344.5(SLC29A3):c.607T > C (p.Ser203Pro) | ACTGATAYCAGGTGAGAGCCAGG, CTGATAYCAGGTGAGAGCCAGG | Histiocytoss-lymphadenopathy plus syndrome |
| 118204440 | NM_000512.4(GALNS):c.1460A > G (p.Asn487Ser) | ACGYTGAGCTGGGGCTGCGCGG, CACGYTGAGCTGGGGCTGCGCG | Mucopolysaccharidosis, MPS-IV-A |
| 587776843 | NG_012088.1:g.2209A > G | ACCYTATGATCCGCCCGCCTTGG | |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 137853033 | NM_001080463.1(DYNC2H1):c.4610A > G (p.Gln1537Arg) | ACCYGTGAAGGGAACAGAGATGG | Short-rib thoracic dysplasia 3 with or without polydactyly |
| 28933698 | NM_000435.2(NOTCH3):c.1363T > C (p.Cys455Arg) | TTCACCYGTATCTGTATGGCAGG, ACCYGTATCTGTATGGCAGTGG | Cerebral autosomal dominant arteriopathy with subcortical infarcts and leukoencephalopathy |
| 587776766 | NM_000463.2(UGT1A1):c.1085-2A > G | ACCYGAGATGCAAAATAGGAGG, GTGACCYGAGATGCAAAATAGGG, GGTGACCYGAGATGCAAAATAGG | Crigler Najjar syndrome, type 1 |
| 587781628 | NM_001128425.1(MUTYH):c.1187-2A > G | ACCYGAGGGAGGGCAGCCAGG | Hereditary cancer-predisposing syndrome, Carcinoma of colon |
| 61755817 | NM_000322.4(PRPH2):c.736T > C (p.Trp246Arg) | ACCTGYGGGTGCGTGGCTGCAGG, CCTGYGGGTGCGTGGCTGCAGGG | Retinitis pigmentosa |
| 121909184 | NM_001089.2(ABCA3):c.1702A > G (p.Asn568Asp) | ACCGTYGTGGCCCAGCAGGACGG | Surfactant metabolism dysfunction, pulmonary, 3 |
| 121434466 | m.4269A > G | ACAYATTTCTTAGGTTTGAGGGG, GACAYATTTCTTAGGTTTGAGGG, AGACAYATTCCTTAGGTTTGAGG | |
| 794726768 | NM_001165963.1(SCN1A):c.1048A > G (p.Met350Val) | ACAYATATCCCTCTGGACATTGG | Severe myoclonic epilepsy in infancy |
| 28934876 | NM_001382.3(DPAGT1):c.509A > G (p.Tyr170Cys) | ACAYAGTACAGATTCCTGCGGG, GACAYAGTACAGGATTCCTGCCG | Congenital disorder of glycosylation type 1J |
| 104894749 | NM_000054.4(AVPR2):c.614A > G (p.Tyr205Cys) | ACAYAGGTGCGACGGCCCAGGG, GACAYAGGTGCGACGGCCCAGG | Nephrogenic diabetes insipidus, Nephrogenic diabetes insipidus, X-linked |
| 128621205 | NM_000061.2(BTK):c.1741T > C (p.Trp581Arg) | ACATTYGGGCTTTTGGTAAGTGG | X-linked agammaglobulinemia |
| 28940892 | NM_000529.2(MC2R):c.761A > G (p.Tyr254Cys) | ACATGYAGCAGGCAGTAGGGG, GACATGYAGCAGGCGCAGTAGGG, AGACATGYAGCAGGCCAGTAGG | ACTH resistance |
| 794726844 | NM_001165963.1(SCN1A):c.1046A > G (p.Tyr349Cys) | ACATAYATCCCTCTGGACATTGG | Severe myoclonic epilepsy in infancy |
| 587783083 | NM_003159.2(CDKL5):c.449A > G (p.Lys150Arg) | ACAGTYTTAGGACATCATTGTGG | not provided |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 397514651 | NM_000108.4(DLD):c.140T > C (p.Ile47Thr) | ACAGTTAYAGGTTCTGTCCTGG, GTTAYAGGTTCTGGTCCTGGAGG | Maple syrup urine disease, type 3 |
| 794727060 | NM_001848.2(COL6A1):c.957 + 2T > C | ACAAGGYGAGCGTGGGCTGCTGG, CAAGGYGAGCGTGGGCTGCTGGG | Ullrich congenital muscular dystrophy, Bethlem myopathy |
| 72554346 | NM_000531.5(OTC):c.284T > C (p.Leu95Ser) | ACAAGATYGTCTACAGAAACAGG | not provided |
| 483353031 | NM_002136.2(HNRPA1):c.841T > C (p.Phe281Leu) | AATYTTCGAGGCAGAAGCTCTGG | Chronic progressive multiple sclerosis |
| 104894271 | NM_000315.2(PTH):c.52T > C (p.Cys18Arg) | AATTYTTTTCTTACAAAATCGG | Hypoparathyroidism familial isolated |
| 267608260 | NM_015599.2(PGM3):c.248T > C (p.Leu83Ser) | AATGTYGGCACCATCCTGGAGG | Immunodeficiency 23 |
| 267606900 | NM_018109.3(MTPAP):c.1432A > G (p.Asn478Asp) | AATGGAYCTCGAATGTACAGAGG | Ataxia, spastic, 4, autosomal recessive |
| 796053169 | NM_021007.2(SCN2A):c.387-2A > G | AATAAAGYAGAATATCGTCAAGG | not provided |
| 104894937 | NM_000116.4(TAZ):c.352T > C (p.Cys18Arg) | AAGYGTGTGCCTGTCGTGCCAGG | 3-Methylglutaconic aciduria type 2 |
| 104893911 | NM_001018077.1(NR3C1):c.1712T > C (p.Val571Ala) | AAGYGATTGCAGCAGTGAAATGG | Pseudohermaphroditism, female, with hypokalemia, due to glucocorticoid resistance |
| 397514472 | NM_004813.2(PEX16):c.992A > G (p.Tyr331Cys) | AAGYAGATTTTCTGCCAGGTGGG, GAAGYAGATTTTCTGCCAGGTGG, GTAGAAGYAGATTTTCTGCCAGG | Peroxisome biogenesis disorder 8B |
| 121918407 | NM_001083112.2(GPD2):c.1904T > C (p.Phe635Ser) | AAGYTYGATGCAGACCAGAAAGG | Diabetes mellitus type 2 |
| 63751110 | NM_000251.2(MSH2):c.595T > C (p.Cys199Arg) | AAGGAYGTGTTTTACCCGGAGG | Hereditary Nonpolyposis Colorectal Neoplasms |
| 119450945 | NM_000026.2(ADSL):c.674T > C (p.Met225Thr) | AAGAYGGTGACAGAAAAGGCAGG | Adenylosuccinate lyase deficiency |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 113993988 | NM_002863.4(PYGL):c.2461T > C (p.Tyr821His) | AAGAAYATGCCCAAAACATCTGG | Glycogen storage disease, type VI |
| 119485091 | NM_022041.3(GAN):c.1268T > C (p.Ile423Thr) | AAGAAAYCTACGCCATGGTGG, AAAAYCTACGCCATGGGTGGAGG | Giant axonal neuropathy |
| 137852419 | NM_000132.3(F8):c.1660A > G (p.Ser554Gly) | AACYAGAGTAATAGCGGGTCAGG | Hereditary factor VIII deficiency disease |
| 121964967 | NM_000071.2(CBS):c.1150A > G (p.Lys384Glu) | AACTYGGTCCTGCGGGATGGGGG, GAACTYGGTCCTGCGGGATGGGG, GGAACTYGGTCCTGCGGGATGGG, AGGAACTYGGTCCTGCGGGATGG | Homocystinuria, pyridoxine-responsive |
| 137852376 | NM_000132.3(F8):c.1754T > C (p.Ile585Thr) | AACAGAYAATGTCAGACAAGAGG | Hereditary factor VIII deficiency disease |
| 121917930 | NM_006920.4(SCN1A):c.3577T > C (p.Trp1193Arg) | AACAAYGGTGGAACCTGAGAAGG | Generalized epilepsy with febrile seizures plus, type 1, Generalized epilepsy with febrile seizures plus, type 2 |
| 28939717 | NM_003907.2(EIF2B5):c.271A > G (p.Thr91Ala) | AAATGYTTCCTGTACACCTGTGG | Leukoencephalopathy with vanishing white matter |
| 80357276 | NM_007294.3(BRCA1):c.122A > G (p.His41Arg) | AAATATGYGGTCACACTTTGTGG | Familial cancer of breast, Breast-ovarian cancer, familial 1 |
| 397515897 | NM_000256.3(MYBPC3):c.1351 + 2T > C | AAAGGYGGGCCTGGGACCTGAGG | Familial hypertrophic cardiomyopathy 4, Cardiomyopathy |
| 397514491 | NM_005340.6(HINT1):c.152A > G (p.His51Arg) | AAAAYGTGTTGTGCTTGAGGGG, GAAAAYGTGTTGGTGCTTGAGGG, AGAAAAYGTGTTGGTGCTTGAGG | Gamstorp-Wohlfart syndrome |
| 387907164 | NM_020894.2(UVSSA):c.94T > C (p.Cys32Arg) | AAAATTYGCAAGTATGTCTTAGG, AAATTYGCAAGTATGTCTTAGG | UV-sensitive syndrome 3 |
| 118161496 | NM_025152.2(NUBPL):c.815-27T > C | TGGTTCYAATGGATGTCTGCTGG, GGTTCYAATGGATGTCTGCTGGG | Mitochondrial complex I deficiency |
| 764313717 | NM_005609.2(PYGM):c.425_528del | TGGCTGYCAGGGACCCAGCAAGG, CTGYCAGGGACCCAGCAAGGAGG | |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base
to be edited, e.g., C. (SEQ ID NOs: 747 to 1868 appear from top to bottom below,
respectively)

| dbSNP # | Genotype | Protospacer and PAM sequence(s) | Associated genetic disease |
|---|---|---|---|
| 28934568 | NM_003242.5(TGFBR2):c.923T > C (p.Leu308Pro) | AGTTCCYGACGGCTGAGGAGCGG | Loeys-D etz syndrome 2 |
| 121913461 | NM_007313.2(ABL1):c.814T > C (p.Tyr272His) | CCAGYACGGGGAGGTGTACGAGG, CAGYACGGGGAGGTGTACGAGGG | |
| 377750405 | NM_173551.4(ANKS6):c.1322A > G (p.Gln441Arg) | AGGGCYGTCGGACCTTCGAGTGG, GGGCYGTCGGACCTTCGAGTGGG, GGCYGTCGGACCTTCGAGTGGGG | Nephronophthisis 16 |
| 57639980 | NM_001927.3(DES):c.1034T > C (p.Leu345Pro) | ATTCCCYGATGAGGCAGATGCGG, TTCCCYGATGAGGCAGATGCGGG | Myofibrillar myopathy 1 |
| 147391618 | NM_020320.3(RARS2):c.35A > G (p.Gln12Arg) | ATACCYGGCAAGCAATAGCGCGG | Pontocerebellar hypoplasia type 6 |
| 182650126 | NM_002977.3(SNC9A):c.2215A > G (p.Ile739Val) | GTAAYTGCAAGATCTACAAAAGG | Small fiber neuropathy |
| 80358278 | NM_004700.3(KCNQ4):c.842T > C (p.Leu281Ser) | ACATYGACAACCATCGGCTATGG | DFNA 2 Nonsyndromic Hearing Loss |
| 786204012 | NM_005957.4(MTHFR):c.388T > C (p.Cys130Arg) | GACCYGCTGCCGTCAGCGCCTGG | Homocysteinemia due to MTHFR deficiency |
| 786204037 | NM_005957.4(MTHFR):c.1883T > C (p.Leu628Pro) | TCCCAYGGACAACTGCCTCTGG | Homocysteinemia due to MTHFR deficiency |
| 202147607 | NM_000140.3(FECH):c.1137 + 3A > G | GTAGAYACCTTAGAGACAATGG | Erythropoietic protoporphyria |
| 122456136 | NM_005183.3(CACNA1F):c.2267T > C (p.Ile756Thr) | TGCCAYTGCTGTGGACAACCTGG | |
| 786204851 | NM_007374.2(SIX6):c.110T > C (p.Leu37Pro) | GTCGCYGCCCCGTGGCCCCTGCCG | Cataract, microphthalmia and nystagmus |
| 794728167 | NM_000138.4(FBN1):c.1468 + 2T > C | ATTGGYACGTGATCCATCCTAGG | Thoracic aortic aneurysms and aortic dissections |
| 121964909 | NM_000027.3(AGA):c.214T > C (p.Ser72Pro) | GACGGCYGTCGTAGGCTTTGGAGG | Aspartylglycosaminuria |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 121964978 | NM_000170.2(GLDC):c.2T > C (p.Met1Thr) | CGGCCAYGCAGTCCTGCCAGG, GGCCAYGCAGTCCTGTGCCAGGG | Non-ketotic hyperglycinemia |
| 121965008 | NM_000398.6(CYB5R3):c.446T > C (p.Leu149Pro) | CTGCYGGTCTACCAGGGCAAAGG | METHEMOGLOBINEMIA, TYPE I |
| 121965064 | NM_000128.3(F11):c.901T > C (p.Phe301Leu) | TGATYTCTTGGGAGAAGAACTGG | Hereditary factor XI deficiency disease |
| 45517398 | NM_000548.3(TSC2):c.5150T > C (p.Leu1717Pro) | GCCCYGACGCAAATGTGAGTGG, CCCYGCACGCAAATGTGAGTGGG | Tuberous sclerosis syndrome |
| 786205857 | NM_015662.2(IFT172):c.770T > C (p.Leu257Pro) | TTGTGCYAGGAAGTTATGACAGG | RETINITIS PIGMENTOSA 71 |
| 786205904 | NM_001135669.1(XPR1):c.653T > C (p.Leu218Ser) | GCGTTYACGTGTCCCCCTTTGG, CGTTYACGTGTCCCCCTTTGGG | BASAL GANGLIA CALCIFICATION, |
| 104893704 | NM_000388.3(CASR):c.2641T > C (p.Phe881Leu) | ACGCTYTCAAGTGGCTGCCCGG, CGCTYTCAAGTGGCTGCCCGGG | Hypercalciuric hypercalcemia |
| 104893747 | NM_198159.2(MITF):c.1195T > C (p.Ser399Pro) | ACTTYCCTTATTCCATCCACGG, CTTYCCCTTATTCCATCCACGGG | Waardenburg syndrome type 2A |
| 104893770 | NM_000539.3(RHO):c.133T > C (p.Phe45Leu) | CATGYTTCTGCTGATCGTGCTGG, ATGYTTCTGCTGATCGTGCTGGG | Retinitis pigmentosa 4 |
| 28937596 | NM_003907.2(EIF2B5):c.1882T > C (p.Trp628Arg) | AGGGCYGGAGCCCCTGTTTTAGG | Leukoencephalopathy with vanishing white matter |
| 104893876 | NM_001151.3(SLC25A4):c.293T > C (p.Leu98Pro) | GCAGCYCTTCTTAGGGGGTGTGG | Autosomal dominant progressive external ophthalmoplegia with mitochondrial DNA deletions 2 |
| 104893883 | NM_006005.3(WFS1):c.2486T > C (p.Leu829Pro) | ACCATCCYGGAGGGCCGCCTGG | WFS1-Related Disorders |
| 104893962 | NM_000165.4(GJA1):c.52T > C (p.Ser18Pro) | CTACYCAACTGCTGAGGGAAGG | Oculodentodigital dysplasia |
| 104893978 | NM_000434.3(NEU1):c.718T > C (p.Trp240Arg) | GCCTCCYGGCCTACGAAGTGG, CCTCCYGGCCGCTACGAAGTGGG, CTCCYGGCCGCTACGAAGTGGGG | Sialidosis, type II |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base
to be edited, e.g., C. (SEQ ID NOs: 747 to 1868 appear from top to bottom below,
respectively)

| dbSNP # | Genotype | Protospacer and PAM sequence(s) | Associated genetic disease |
|---|---|---|---|
| 104894092 | NM_002546.3(TNFRSF11B):c.349T > C (p.Phe17Leu) | TAGAGYTCTGCTTGAAACATAGG | Hyperphosphatasemia with bone disease |
| 104894135 | NM_000102.3(CYP17A1):c.316T > C (p.Ser106Pro) | CATCGCGYCCAACAACCGTAAGG, ATCGCGYCCAACAACCGTAAGGG | Complete combined 17-alpha-hydroxylase/17,20-lyase |
| 104894151 | NM_000102.3(CYP17A1):c.1358T > C (p.Phe453Ser) | AGCTCYCCTCATCATGGCCTGG | Combined partial 17-alpha-hydroxylase/17,20-lyase deficiency |
| 36015961 | NM_000518.4(HBB):c.344T > C (p.Leu115Pro) | TGTGTGCYGGCCCATCACTTTGG | Beta thalassemia intermedia |
| 104894472 | NM_152443.2(RDH12):c.523T > C (p.Ser175Pro) | TCCYCGGTGGCTCACCACATTGG | Leber congenital amaurosis 13 |
| 104894587 | NM_004870.3(MPDU1):c.356T > C (p.Leu119Pro) | TTCCYGGTCATGCACTACAGAGG | Congenital disorder of glycosylation type 1F |
| 104894588 | NM_004870.3(MPDU1):c.2T > C (p.Met1Thr) | AATAYGGCGGCCGAGGCGGACGG | Congenital disorder of glycosylation type 1F |
| 104894626 | NM_000304.3(PMP22):c.82T > C (p.Trp28Arg) | TAGCAAYGGATCTGGGCAATGG | Charcot-Marie-Tooth disease, type 1E |
| 104894631 | NM_018129.3(PNPO):c.784T > C (p.Ter262Gln) | ACCTYAACTCTGGGACCTGCTGG | "Pyridoxal 5-phosphate-dependent epilepsy" |
| 104894703 | NM_032551.4(KISS1R):c.305T > C (p.Leu102Pro) | GCCCTGCYGTACCCGCTGCCCGG, TGCYGTACCCGCTGCCCGGCTGG | |
| 104894826 | NM_000166.5(GJB1):c.407T > C (p.Val136Ala) | ATGYCATCAGCGTGGTTGTTCCGG | Dejerine-Sottas disease, X-linked hereditary motor and sensory neuropathy |
| 104894859 | NM_001222606.1(LAMP2):c.961T > C (p.Trp321Arg) | CAGCTACYGGGATGCCCCCCTGG, AGCTACYGGGATGCCCCCCTGGG | Danon disease |
| 104894931 | NM_006517.4(SLC16A2):c.1313T > C (p.Leu438Pro) | TGAGCYGGTGGGCCCAATGCAGG | Allan-Herndon-Dudley syndrome |
| 104894935 | NM_000330.3(RS1):c.38T > C (p.Leu13Pro) | TTACTTCYCTTTGGCTATGAAGG | Juvenile retinoschisis |
| 104895217 | NM_001065.3(TNFRSF1A):c.175T > C (p.Cys59Arg) | TGCYGTACCAAGTGCCACAAAGG | TNF receptor-associated periodic fever syndrome (TRAPS) |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 143889283 | NM_003793.3(CTSF):c.692A > G (p.Tyr231Cys) | CTCCAYACTGAGCTGTGCCACGG | Ceroid lipofuscinosis, neuronal, 13 |
| 122459147 | NM_001159702.2(FHL1):c.310T > C (p.Cys104Arg) | GGGGYGCTTCAAGGCCATTGTGG | Myopathy, reducing body, X-linked, childhood-onset |
| 74552543 | NM_020184.3(CNNM4):c.971T > C (p.Leu324Pro) | AAGCTCCYGGACTTTTTTCTGGG | Cone-rod dystrophy amelogenesis imperfecta |
| 199476117 | m.10158T > C | AAAYCCACCCCTTACGAGTGCCG | Leigh disease, Leigh syndrome due to mitochondrial complex I deficiency, Mitochondrial complex I deficiency |
| 794727808 | NM_020451.2(SEPN1):c.872 + 2T > C | TTCCGGYGAGTGGGCCACACTGG | Congenital myopathy with fiber type disproportion, Eichsfeld type congenital muscular dystrophy |
| 140547520 | NM_050022.3(PFN1):c.350A > G (p.Glu117Gly) | CACCTYCTTTGCCATCAGCAGG | Amyotrophic lateral sclerosis 18 |
| 397514359 | NM_000060.3(BTD):c.445T > C (p.Phe149Leu) | TCACCGGYTCAATGACACAGAGG | Biotinidase deficiency |
| 207460001 | m.15197T > C | CTAYCCGCCATCCCATACATTGG | Exercise intolerance |
| 397514406 | NM_000060.3(BTD):c.1214T > C (p.Leu405Pro) | TTCACCCYGGTCCCTGTCTGGGG | Biotinidase deficiency |
| 397514516 | NM_006177.3(NRL):c.287T > C (p.Met96Thr) | GAGGCCAYGGAGCTGCTGCAGGG | Retinitis pigmentosa 27 |
| 72554312 | NM_000531.5(OTC):c.134T > C (p.Leu45Pro) | CTCACTCYAAAAAACTTTACCGG | Ornithine carbamoyltransferase deficiency |
| 397514569 | NM_178012.4(TUBB2B):c.350T > C (p.Leu117Pro) | GGTCCYGGATGTGGTGAGGAAGG | Polymicrogyria, asymmetric |
| 397514571 | NM_000431.3(MVK):c.122T > C (p.Leu41Pro) | CGGCYTCAACCCCACAGCAATGG, GGCYTCAACCCCACAGCAATGGG | Porokeratosis, disseminated superficial actinic 1 |
| 794728390 | NM_000238.3(KCNH2):c.2396T > C (p.Leu799Pro) | GCCATCCYGGGTATGGGGTGGGG, CCATCCYGGGTATGGGGTGGGGG, CATCCYGGGTATGGGGTGGGGGG | Cardiac arrhythmia |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base
to be edited, e.g., C. (SEQ ID NOs: 747 to 1868 appear from top to bottom below,
respectively)

| dbSNP # | Genotype | Protospacer and PAM sequence(s) | Associated uenetic disease |
|---|---|---|---|
| 397514713 | NM_001199107.1(TBC1D24):c.686T > C (p.Phe229Ser) | GGTCTYTGACGTCTTCCTGGTGG | Early infantile epileptic encephalopathy 16 |
| 397514719 | NM_080605.3(B3GALT6):c.193A > G (p.Ser65Gly) | CGCYGGCCACCAGCACTGCCAGG | Spondyloepimetaphyseal dysplasia with joint laxity |
| 730880608 | NM_000256.3(MYBPC3):c.3796T > C (p.Cys1266Arg) | GAGYGCCGCCTGGAGGTGCGAGG | Cardiomyopathy |
| 397515329 | NM_001382.3(DPAGT1):c.503T > C (p.Leu168Pro) | AATCCYGTACTATGTCTACATGG, ATCCYGTACTATGTCTACATGGG, TCCYGTACTATGTCTACATGGGG | Congenital disorder of glycosylation type 1J |
| 397515465 | NM_018127.6(ELAC2):c.460T > C (p.Phe154Leu) | ATAYTTTCTGGTCCATTGAAAGG | Combined oxidative phosphorylation deficiency 17 |
| 397515557 | NM_005211.3(CSF1R):c.2483T > C (p.Phe828Ser) | CATCYTTGACTGTGTCTACACGG | Hereditary diffuse leukoencephalopathy with spheroids |
| 397515599 | NM_194248.2(OTOF):c.3413T > C (p.Leu1138Pro) | AGGTGCYGTTCTGGGGCCTACGG, GGTGCYGTTCTGGGGCCTACGGG | Deafness, autosomal recessive 9 |
| 397515766 | NM_000138.4(FBN1):c.2341T > C (p.Cys781Arg) | GGACAAVGTAGAAATACTCCTGG | Marfan syndrome |
| 565779970 | NM_001429.3(EP300):c.3573T > A (p.Tyr1191Ter) | CTTAYTACAGTTACCAGAACAGG | Rubinstein-Taybi syndrome 2 |
| 786200938 | NM_080605.3(B3GALT6):c.1A > G (p.Met1Val) | AGCTTCAYGGCGCCCCGCGCCGGG, TCAYGGCGCCCGCGCCGGGCCGG | Spondyloepimetaphyseal dysplasia with joint laxity |
| 28942087 | NM_000229.1(LCAT):c.698T > C (p.Leu233Pro) | ATCTCYTGGGGCTCCCTGGGG, TCTCYTGGGGCTCCCTGGGGTGG | Norum disease |
| 128621203 | NM_000061.2(BTK):c.1625T > C (p.Leu542Pro) | TCGGCCYGTCCAGGTGAGTGTGG | X-linked agammaglobulinemia with growth hormone deficiency |
| 397515412 | NM_006383.3(CIB2):c.368T > C (p.Ile123Thr) | CTTCAYCTGCAAGGAGGACCTGG | Deafness, autosomal recessive 48 |
| 193929364 | NM_000352.4(ABCC8):c.404T > C (p.Leu35Pro) | AAGCYGCTAATTGGTAGGTGAGG | Permanent neonatal diabetes mellitus |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base
to be edited, e.g., C. (SEQ ID NOs: 747 to 1868 appear from top to bottom below,
respectively)

| dbSNP # | Genotype | Protospacer and PAM sequence(s) | Associated uenetic disease |
|---|---|---|---|
| 730880872 | NM_000257.3(MYH7):c.1400T > C | TCGAGAYCTTCGATGTGAGTTGG, CGAGAYCTTCGATGTGAGTTGG | Cardiomyopathy |
| 80356474 | NM_002977.3(SCN9A):c.2543T > C (p.Ile848Thr) | AAGATCAYTGGTAACTCAGTAGG, AGATCAYTGGTAACTCAGTAGGG, GATCAYTGGTAACTCAGTAGGGG | Primary erythromelalgia |
| 80356489 | NM_001164277.1(SLC37A4):c.352T > C (p.Trp118Arg) | GGGCYGGCCCCATGTGGGAAGG | Glucose-6-phosphate transport defect |
| 80356536 | NM_152296.4(ATP1A3):c.2338T > C (p.Phe780Leu) | GCCCYTCCTGCTGTTCATCATGG | Dystonia 12 |
| 80356596 | NM_194248.2(OTOF):c.3032T > C (p.Leu1011Pro) | GATGCYGGTGTTCGACAAACCTGG | Deafness, autosomal recessive 9, Auditory neuropathy, autosomal recessive, 1 |
| 80356689 | NM_000083.2(CLCN1):c.857T > C (p.Val286Ala) | AGGAGYGCTATTTAGCATCGAGG | Myotonia congenita |
| 118203884 | m.4409T > C | AGGYCAGCTAAATAAGCTATCGG | Mitochondrial myopathy |
| 587777625 | NM_173596.2(SLC39A5):c.911T > C (p.Met304Thr) | AGAACAYGCTGGGGCTTTTGCGG | Myopia 24, autosomal dominant |
| 587783087 | NM_003159.2(CDKL5):c.602T > C (p.Leu201Pro) | ATTCYTGGGGAGCTTAGCGATGG | not provided |
| 118203951 | NM_013319.2(UBIAD1):c.511T > C (p.Ser171Pro) | TCTGGCYCCTTTCTCTACACAGG, GGCYCCTTTCTCTACACAGGAGG | Schnyder crystalline conical dystrophy |
| 118204017 | NM_000018.3(ACADVL):c.1372T > C (p.Phe458Leu) | TCGCATCYTCCGGATCTTTGAGG, CGCATCYTCCGGATCTTTGAGGG, GCATCYTCCGGATCTTTGAGGGG | Very long chain acyl-CoA dehydrogenase deficiency |
| 397518466 | NM_000833.4(GRIN2A):c.2T > C (p.Met1Thr) | CTAYGGGCAGAGTGGGCTATTGG | Focal epilepsy with speech disorder with or without mental retardation |
| 118204069 | NM_000237.2(LPL):c.337T > C (p.Trp113Arg) | GGACYGGCTGTCACGGGCTCAGG | Hyperlipoproteinemia, type I |
| 118204080 | NM_000237.2(LPL):c.755T > C (p.Ile252Thr) | GTGAYTGCAGAGAGGACTTGG | Hyperlipoprote nemia, type I |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base
to be edited, e.g., C. (SEQ ID NOs: 747 to 1868 appear from top to bottom below,
respectively)

| dbSNP # | Genotype | Protospacer and PAM sequence(s) | Associated uenetic disease |
|---|---|---|---|
| 118204111 | NM_000190.3(HMBS):c.739T > C (p.Cys247Arg) | GCTTCGYCGCATCGCTGAAAGGG | Acute intermittent porphyria |
| 80357438 | NM_007294.3(BRCA1):c.65T > C (p.Leu22Ser) | AAATCTYAGAGTGTCCATCTGG | Familial cancer of breast, Breast-ovarian cancer, familial 1, Hereditary cancer-predisposing syndrome |
| 139877390 | NM_001040431.2(COA3):c.215A > G (p.Tyr72Cys) | CCAYCTGGGAGGTAGGTTCAGG | |
| 793888527 | NM_005859.4(PURA):c.563T > C (p.Ile188Thr) | GACCAYTGCGCTGCCCGCGCAGG, ACCAYTGCGCTGCCCGCGCAGGG, CCAYTGCGCTGCCCGCGCAGGGG | not provided, Mental retardation, autosomal dominant 31 |
| 561425038 | NM_002878.3(RAD51D):c.1A > G (p.MetIVal) | CGCCCAYGTTCCCCGCAGGCCGG | Hereditary cancer-predisposing syndrome |
| 121907934 | NM_024105.3(ALG12):c.473T > C (p.Leu158Pro) | TCCYGCTGGCCCTCGCGGCCTGG | Congenital disorder of glycosylation type 1G |
| 80358207 | NM_153212.2(GM4):c.409T > C (p.Phe137Leu) | CCTCATCYTCAAGGCCGCCGTGG | Erythrokeratodermia variabilis |
| 80358228 | NM_002353.2(TACSTD2):c.557T > C (p.Leu186Pro) | TCGGCYGCACCCCAAGTTCGTGG | Lattice conical dystrophy Type III |
| 121908076 | NM_138691.2(TMC1):c.1543T > C (p.Cys515Arg) | AGGACCTYGCTGGGAAACAATGG, ACCTYGCTGGGAAACAATGGTGG, CCTYGCTGGGAAACAATGGTGGG | Deafness, autosomal recessive 7 |
| 121908089 | NM_017838.3(NHP2):c.415T > C (p.Tyr139His) | GGAGGCTYACGATGAGTGCCTGG, GGCTYACGATGAGTGCCTGAGG | Dyskeratosis congenita autosomal recessive 1, Dyskeratosis congenita, autosomal recessive 2 |
| 121908154 | NM_001243133.1(NLRP3):c.926T > C (p.Phe309Ser) | GGTGCCTYTGACGAGCACATAGG | Familial cold urticaria, Chronic infantile neurological, cutaneous and articular syndrome |
| 121908158 | NM_001033855.2(DCLRE1C):c.2T > C (p.Met1Thr) | GGCGCTAYGAGTTCTTTCGAGGG, GCGCTAYGAGTTCTTTCGAGGGG, CCCCAYGACGTGCTGGCTGCGG, | Histiocytic medullary reticulosis |
| 796052870 | NM_018129.3(PNPO):c.2T > C (p.Met1Thr) | CCCAYGACGTGCTGCTGGCTGCGGG, CCAYGACGTGCTGCTGGCTGCGGGG | not provided |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 121908318 | NM_020427.2(SLURP1):c.43T > C (p.Trp15Arg) | GCAGCCYGGAGCATGGGCTGTGG | Acroerythrokeratoderma |
| 121908352 | NM_022124.5(CDH23):c.5663T > C (p.Phe1888Ser) | CTCACCTYCAACATCACTGCGGG | Deafness, autosomal recessive 12 |
| 121908520 | NM_000030.2(AGXT):c.613T > C (p.Ser205Pro) | CCTGTACYCGGGCTCCCAGAAGG | Primary hyperoxaluria, type I |
| 121908618 | NM_004273.4(CHST3):c.920T > C (p.Leu307Pro) | CGTGCYGGCCTCGCGCATGGTGG | Spondyloepiphyseal dysplasia with congenital joint dislocations |
| 11694 | NM_006432.3(NPC2):c.199T > C (D.Ser67Pro) | TATTCAGYCTAAAAGCAGCAAGG | Niemann-Pick disease type C2 |
| 121908739 | NM_000022.2(ADA):c.320T > C (p.Leu107Pro) | CCTGCYGGCCAACTCCAAAGTGG | Severe combined immunodeficiency due to ADA deficiency |
| 80359022 | NM_000059.3(BRCA2):c.7958T > C (p.Leu2653Pro) | TGCYTCTTCAACTAAAATACAGG | Familial cancer of breast, Breast-ovarian cancer, familial 2 |
| 121908902 | NM_003880.3(WISP3):c.232T > C (p.Cys78Arg) | AAAATCYGTGCCAAGCAACCAGG, AAATCYGTGCCAAGCAACCAGGG, AATCYGTGCCAAGCAACCAGGGG | Progressive pseudorheumatoid dysplasia |
| 121908947 | NM_006892.3(DNMT3B):c.808T > C (p.Ser270Pro) | CAAGTTCYCCGAGGTGAGTCCGG, AAGTTCYCCGAGGTGAGTCCGG, | Centromeric instability of chromosomes 1, 9 and 16 and immunodeficiency |
| 121909028 | NM_000492.3(CFTR):c.3857T > C (p.Phe1286Ser) | AGTTCYCCGAGGTGAGTCCGGGG AGCCYTTGGAGTGATACCACAGG | Cystic fibrosis |
| 121909135 | NM_000085.4(CLCNKB):c.1294T > C (p.Tyr432His) | CTTTGTCYATGGTGAGTCTGGGG | Bartter syndrome type 3 |
| 121909143 | NM_001300.5(KLF6):c.506T > C (p.Leu169Pro) | GGAGCYGCCCTCGCCAGGGAAGG | |
| 121909182 | NM_001089.2(ABCA3):c.302T > C (p.Leu101Pro) | GCACYTGTGATCAACATGCGAGG | Surfactant metabolism dysfunction, pulmonary, 3 |
| 121909200 | NM_000503.5(EYA1):c.1459T > C (p.Ser487Pro) | CACTCYCGCTCATTCACTCCCGG | Melnick-Fraser syndrome |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 121909247 | NM_004970.2(IGFALS):c.1618T > C (p.Cys540Arg) | GGACYGTGGCTGCCCTCTCAAGG | Acid-labile subunit deficiency |
| 121909253 | NM_005570.3(LMAN1):c.2T > C (p.Met1Thr) | AGAYGGCGGGATCCAGGCAAAGG | Combined deficiency of factor V and factor VIII, 1 |
| 121909385 | NM_000339.2(SLC12A3):c.1868T > C (p.Leu623Pro) | CAACCYGGCCCTCAGCTACTCGG | Familialhypokalemia-hypomagnesemia |
| 121909497 | NM_002427.3(MMP13):c.224T > C (p.Phe75Ser) | TTCTYCGGCTTAGAGGTGACTGG | Spondyloepimetaphyseal dysplasia, Missouri type |
| 121909508 | NM_000751.2(CHRND):c.188T > C (p.Leu63Pro) | AACCYCATCTCCCTGGTGAGAGG | MYASTHENIC SYNDROME, CONGENITAL, 3B, FAST-CHANNEL |
| 121909519 | NM_001100.3(ACTA1):c.287T > C (p.Leu96Pro) | CGAGCYTCGCGTGGCTCCCGAGG | Nemaline myopathy 3 |
| 121909572 | NM_000488.3(SERPINC1):c.667T > C (p.Ser223Pro) | TGGGTGYCCAATAAGACCGAAGG | Antithrombin III deficiency |
| 121909677 | NM_000821.6(GGCX):c.896T > C (p.Phe299Ser) | TATGTYCTCCTACGTCATGCTGG | Pseudoxanthoma elasticum-like disorder with multiple coagulation factor deficiency |
| 121909727 | NM_001018077.1(NR3C1):c.2209T > C (p.Phe737Leu) | CTATTGCYTCCAAACATTTTTGG | Glucocorticoid resistance, generalized |
| 139573311 | NM_000492.3(CFTR):c.1400T > C (p.Leu467Pro) | TTCACYTCTAATGTGATTATGG, TCACYTCTAATGGTGATTATGGG | Cystic fibrosis |
| 121912441 | NM_000454.4(SOD1):c.341T > C (p.Ile114Thr) | CATCAYTGGCCGCACACTGGTGG | Amyotrophic lateral sclerosis type 1 |
| 121912446 | NM_000454.4(SOD1):c.434T > C (p.Leu145Ser) | CGTTYGGCTTGGTGTAATTGG, GTTYGGCTTGTGTGTAATTGGG | Amyotrophic lateral sclerosis type 1 |
| 121912463 | NM_000213.3(ITGB4):c.1684T > C (p.Cys562Arg) | GGCCAGYGTGTGTGTGAGCCTGG | Epidermolysis bullosa with pyloric atresia |
| 121912492 | NM_002292.3(LAMB2):c.961T > C (p.Cys321Arg) | CCTCAACYGCGAGCAGTGTCAGG | Nephrotic syndrome, type 5, with or without ocular abnormalities |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base
to be edited, e.g., C. (SEQ ID NOs: 747 to 1868 appear from top to bottom below,
respectively)

| dbSNP # | Genotype | Protospacer and PAM sequence(s) | Associated uenetic disease |
|---|---|---|---|
| 397516659 | NM_001399.4(EDA):c.2T > C (p.Met1Thr) | GGCCAYGGGCTACCCGGAGGTGG | Hypohidrotic X-linked ectodermal dysplasia |
| 111033589 | NM_021044.2(DHH):c.485T > C (p.Leu162Pro) | GTTGCYGGCGCGCCTCGCAGTGG | 46,XY gonadal dysgenesis, complete, dhh-related |
| 111033622 | NM_000206.2(IL2RG):c.343T > C (p.Cys115Arg) | TGGCYGTCAGTTGCAAAAAAAGG | X-linked severe combined immunodeficiency |
| 121912613 | NM_001041.3(SI):c.1859T > C (p.Leu620Pro) | ATGCYGGAGTTCAGTTTGTTTGG | Sucrase-isomaltase deficiency |
| 121912619 | NM_016180.4(SLC45A2):c.1082T > C (p.Leu361Pro) | GAGTTTCYCATCTACGAAAGAGG | Oculocutaneous albinism type 4 |
| 61750581 | NM_000552.3(VWF):c.4837T > C (p.Ser1613Pro) | CTGCCYCTGATGAGATCAAGAGG | von Willebrand disease, type 2a |
| 121912653 | NM_000546.5(TP53):c.755T > C (p.Leu252Pro) | CATCCYCACCATCATCACACTGG | Li-Fraumeni syndrome 1 |
| 111033683 | NM_000155.3(GALT):c.386T > C (p.Met129Thr) | AGGTCAYGTGCTTCCACCCCTGG | Deficiency of UDPglucose-hexose-1-phosphate uridylyltransferase |
| 111033752 | NM_000155.3(GALT):c.677T > C (p.Leu226Pro) | CAGGAGCYACTCAGGAAGGTGGG | Deficiency of UDPglucose-hexose-1-phosphate uridylyltransferase |
| 121912729 | NM_000039.1(APOA1):c.593T > C (p.Leu198Ser) | GCGCTYGGCCGCGCCCTTGAGG | Familial visceral amyloidosis, Ostertag type |
| 769452 | NM_000041.3(APOE):c.137T > C (p.Leu46Pro) | AACYGGCACTGGGTCGCTTTTGG | |
| 121912762 | NM_016124.4(RHD):c.329T > C (p.Leu110Pro) | ACACYGTTCAGGTATTGGGATGG | |
| 111033824 | NM_000155.3(GALT):c.1138T > C (p.Ter380Arg) | CGCCYGACCACGCCGACCAGAGG, GCCYGACCACGCCGACCACAGGG | Defic ency of UDPglucose-hexose-1-phosphate uridylyltransferase |
| 111033832 | NM_000155.3(GALT):c.980T > C (p.Leu327Pro) | TCCYGCGCCTCTGCCACTGTCCGG | Deficiency of UDPglucose-hexose-1-phosphate uridylyltransferase |
| 730881974 | NM_000455.4(STK11):c.545T > C (p.Leu182Pro) | GGGACCYGCTGCTCACCACCGG, AACCYGCTGCTCACCACCGTGG | Hereditary cancer-predisposing syndrome |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 1064644 | NM_000157.3(GBA):c.703T > C (p.Ser235Pro) | GGGYCACTCAAGGACAGCCCGG | Gaucher disease |
| 796052090 | NM_138413.3(HOGA1):c.533T > C (p.Leu178Pro) | GGACCYGCCTGTGGATGCAGTGG | Primary hyperoxaluria, type III |
| 121913141 | NM_000208.2(INSR):c.779T > C (p.Leu260Pro) | CTACCYGGACGGCAGGTGTGTGG | Leprechaunism syndrome |
| 121913272 | NM_006218.2(PIK3CA):c.1258T > C (p.Cys420Arg) | GGAACACYGTCCATTGGCATGGG, GAACACYGTCCATTGGCATGGGG | Congenital lipomatous overgrowth, vascular malformations, and epidermal nevi, Neoplasm of ovary, PIK3CA Related Overgrowth Spectrum |
| 61751310 | NM_000552.3(VWF):c.8317T > C (p.Cys2773Arg) | GCTCCYGCTGCTCTCCGACACGG | von Willebrand disease, type 2a |
| 312262799 | NM_024408.3(NOTCH2):c.1438T > C (p.Cys480Arg) | TTCACAYGTCTGTGCATGCCAGG | Alagille syndrome 2 |
| 121913570 | NM_000426.3(LAMA2):c.7691T > C (p.Leu2564Pro) | ATCATTCYTTTGGGAAGTGGAGG, TCATTCYTTTGGGAAGTGGAGGG | Merosin deficient congenital muscular dystrophy |
| 121913640 | NM_000257.3(MYH7):c.1046T > C (p.Met349Thr) | AACTCCAYGTATAAGCTGACAGG | Familial hypertrophic cardiomyopathy 1, Cardiomyopathy |
| 121913642 | NM_000257.3(MYH7):c.1594T > C (p.Ser532Pro) | CATCATGYCCATCCTGGAAGAGG | Dilated cardiomyopathy 1S |
| 119463996 | NM_001079802.1(FKTN):c.527T > C (p.Phe176Ser) | GTAGTCTYTCATGAGAGGAGTGG | Limb-girdle muscular dystrophy- |
| 587776456 | NM_002049.3(GATA1):c.1240T > C (p.Ter414Arg) | GCTCAYGAGGGCACAGAGCATGG | GATA-1-related thrombocytopenia with dyserythropoiesis |
| 63750654 | NM_000184.2(HBG2):c.-228T > C | ATGCAAAYATCTGTCTGAAACGG | Fetal hemoglobin quantitative trait locus 1 |
| 587776519 | NM_001999.3(FBN2):c.3725-15A > G | AGCAAYTGCAACCACATTGTCAGG | Congenital contractural arachnodactyly |
| 78365220 | NM_000402.4(G6PD):c.473T > C (p.Leu158Pro) | TGCCCYCCACCTGGGGTCACAGG | Anemia, nonspherocytic hemolytic, due to G6PD deficiency |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base
to be edited, e.g., C. (SEQ ID NOs: 747 to 1868 appear from top to bottom below,
respectively)

| dbSNP # | Genotype | Protospacer and PAM sequence(s) | Associated uenetic disease |
|---|---|---|---|
| 63750741 | NM_000179.2(MSH6):c.1346T > C (p.Leu449Pro) | CTGGGGCYGGTATTCATGAAAGG | Hereditary Nonpolyposis Colorectal Neoplasms |
| 587776914 | NM_017565.3(FAM20A):c.590-2A > G | GTAATCYGCAAAGGAGGAGAAGG, TAATCYGCAAAGGAGGAGAAGG | Enamel-renal syndrome |
| 5030809 | NM_000551.3(VHL):c.292T > C (p.Tyr98His) | CCCYACCCAACCCTGCCGCCTGG | Von Hippel-Lindau syndrome, Hereditary cancer-predisposing syndrome |
| 199476132 | m.5728T > C | CAATCYACTTCTCCCGCCGCCGG, AATCYACTTCTCCCGCCGCCGGG | Cytochrome-c oxidase deficiency, Mitochondrial complex I deficiency |
| 62637012 | NM_014336.4(AIPLI):c.715T > C (p.Cys239Arg) | CTGCCAGYGCCTGCTGAAGAGAGG, CCAGYGCCTGCTGAAGAAGAGGAGG | Leber congenital amaurosis 4 |
| 199476199 | NM_207352.3(CYP4V2):c.1021T > C (p.Ser341Pro) | AAACTGGYCCTTATACCTGTTGG, AACTGGYCCTTATACCTGTTGGG | Bietti crystalline corneoretinal dystrophy |
| 587777183 | NM_006702.4(PNPLA6):c.3053T > C (p.Phe1018Ser) | CCTYTAACCGCAGCATCCATCGG | Boucher Neuhauser syndrome |
| 199476389 | NM_000487.5(ARSA):c.899T > C (p.Leu300Ser) | GGTCTCYTGCGCGTGTGAAAGGG | Metachromatic leukodystrophy |
| 199476398 | NM_016599.4(MYOZ2):c.142T > C (p.Ser48Pro) | TTAYCCCATCCAGTAACCGTGG | Familial hypertrophic cardiomyopathy 16 |
| 119456967 | NM_001037633.1(SIL1):c1370T > C (p.Leu457Pro) | TTGCYGAAGAGCTGAGATGAGG | Marinesco-sj\xc3\xb6grensyndrome |
| 730882253 | NM_006888.4(CALM1):c.268T > C (p.Phe90Leu) | GGCAYTCCGAGTCTTTGACAAGG | Long QT syndrome 14 |
| 587777283 | NM_012338.3(TSPAN12):c.413A > G (p.Tyr138Cys) | TAATCCAYAATTTGTCATCCTGG | Exudative vitreoretinopathy 5 |
| 587777306 | NM_015884.3(MBTPS2):c.1391T > C (p.Phe464Ser) | GCTYTGCTTTGGATGGACAATGG | Palmoplantar keratoderma, mutilating, with periorificial keratotic plaques, X-linked |
| 56378716 | NM_000250.1(MPO):c.752T > C (p.Met251Thr) | TCACTCAYGTTCATGCAATGGGG | Myeloperoxidase deficiency |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base
to be edited, e.g., C. (SEQ ID NOs: 747 to 1868 appear from top to bottom below,
respectively)

| dbSNP # | Genotype | Protospacer and PAM sequence(s) | Associated uenetic disease |
|---|---|---|---|
| 587777390 | NM_005026.3(PIK3CD):c.1246T > C (p.Cys416Arg) | GCAGGACYGCCCATTGCCTGGG | Activated PI3K-delta syndrome |
| 587777480 | NM_003108.3(SOX11):c.I78T > C (p.Ser60Pro) | TATGGYCCAAGATCGAACGCAGG | Mental retardation, autosomal dominant 27 |
| 587777663 | NM_001288767.1(ARMC5):c.1379T > C (p.Leu460Pro) | GCCCGACYGCGGGATGCTGGTGG | Acth-independent macronodular adrenal hyperplasia 2 |
| 61753033 | NM_000350.2(ABCA4):c.5819T > C (p.Leu1940Pro) | AAGGCYACATGAACTAACCAAGG | Stargardt disease, Stargardt disease 1, Cone-rod dystrophy 3 |
| 200488568 | NM_002972.3(SBF1):c.4768A > G (p.Thr1590Ala) | CAGGCGYCCTCTTGCTCAGCCGG | Charcot-Marie-Tooth disease, type 4B3 |
| 132630274 | NM_000377.2(WAS):c.809T > C (p.Leu270Pro) | CGGAGTCYGTTCTCCAGGGCAGG | Severe congenital neutropenia X-linked |
| 132630308 | NM_001399.4(EDA):c.181T > C (p.Tyr61His) | CTGCYACCTAGAGTTGCGCTCGG | Hypohidrotic X-linked ectodermal dysplasia |
| 60934003 | NM_170707.3(LMNA):c.1589T > C (p.Leu530Pro) | ACGGCTYCATCAACTCCACTGG, CGGCTCYCATCAACTCCACTGGG, GGCTCYCATCAACTCCACTGGGG | Benign scapuloperoneal muscular dystrophy with cardiomyopathy |
| 180177160 | NM_000030.2(AGXT):c.1076T > C (p.Leu359Pro) | GGTGCYGCGGATCGGCCTGCTGG, GTGCYGCGGATCGGCCTGCTGGG | Primary hyperoxaluria, type I |
| 180177222 | NM_000030.2(AGXT):c.449T > C (p.Leu150Pro) | GTGCYGTGTTCTTAACCCACCGG, TGCYGTGTTCTTAACCCACGGG | Primary hyperoxalu a, type I |
| 180177254 | NM_000030.2(AGXT):c.661T > C (p.Ser221Pro) | GCTCATCYCCTTCAGTGACAAGG | Primary hyperoxaluria, type I |
| 180177264 | NM_000030.2(AGXT):c.757T > C (p.Cys253Arg) | GGGGCYGTGACGACCAGCCCAGG | Primary hyperoxaluria, type I |
| 180177293 | NM_000030.2(AGXT):c.893T > C (p.Leu298Pro) | GTATCYGCATGGGCGCCTGCAGG | Primary hyperoxaluria, type I |
| 376785840 | NM_001282227.1(CECR1):c.1232A > G (p.Tyr411Cys) | GAAATCAYAGGACAAGCCTTTGG | Polyarteritis nodosa |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 587779393 | NM_000257.3(MYH7):c.4937T > C (p.Leu1646Pro) | GAGCCYCCAGAGCTTGTTGAAGG | Myopathy, distal, 1 |
| 587779410 | NM_012434.4(SLC17A5):c.500T > C (p.Leu167Pro) | ATTGTACYCAGAGCACTAGAAGG | Sialic acid storage disease, severe infantile type |
| 587779513 | NM_000090.3(COL3A1):c.2337 + 2T > C (p.Gly762_Lys779del) | AGGYAACCCTTAATACTACCTGG | Ehlers-Danlos syndrome, type 4 |
| 777539013 | NM_020376.3(PNPLA2):c.757 + 2T > C | GAACGGYGCGCGGACCCGGGCGG, AACGGYGCGCGCGACCCGGGCGGG | Neutral lipid storage disease with myopathy |
| 34557412 | NM_012452.2(TNERSF13B):c.310T > C (p.Cys104Arg) | ACTTCYGTGAGAACAAGCTCAGG | Immunoglobulin A deficiency 2, Common variable |
| 796052970 | NM_001165963.1(SCN1A):c.1094T > C (p.Phe365Ser) | CAAGCTYTGATACCTTCAGTTGG, AAGCTYTGATACCTTCAGTTGGG | not provided |
| 724159989 | NC_012920.1:m.7505T > C | CCTCCAYGACTTTTCAAAAAGG | Deafness, nonsyndromic sensorineural, mitochondrial |
| 796053222 | NM_014191.3(SCN8A):c.4889T > C (p.Leu1630Pro) | CGTCYGATCAAAGGCGCCAAAGG, GTCYGATCAAAGGCGCCAAAGGG | not provided |
| 118192127 | NM_000540.2(RYR1):c.10817T > C (p.Leu3606Pro) | TACTACCYGGACCAGGTGGGTGG, ACTACCYGGACCAGGTGGGTGGG, CTACCYGGACCAGGTGGGTGGGG | Central core disease |
| 118192170 | NM_000540.2(RYR1):c.14693T > C (p.Ile4898Thr) | AGGCAYTGGGACGAGATCAGG | Malignant hyperthermia susceptibility type 1, Central core disease |
| 121917703 | NM_005247.2(FGF3):c.466T > C (p.Ser156Pro) | GTACGTGCYCTGTGAACGGCAAGG, TACGTGCYCTGTGAACGGCAAGGG | Deafness with labyrinthine aplasia microtia and microdontia (LAMM) |
| 690016549 | NM_005211.3(CSF1R):c.2450T > C (p.Leu817Pro) | CCGCCYGCCTGTGAAGTGGATGG | Hereditary diffuse leukoencephalopathy with spheroids |
| 690016552 | NM_005211.3(CSF1R):c.2566T > C (p.Tyr856His) | GAATCCCYACCCTGGCATCCTGG | Hereditary diffuse leukoencephalopathy with spheroids |
| 121917738 | NM_001098668.2(SFTPA2):c.593T > C (p.Phe198Ser) | GGAGACTYCCCTACTCAGATGG, GAGACTYCCGTACTCAGATGGG | Idiopathic fibrosing alveolitis, chronic form |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 690016559 | NM_005211.3(CSF1R):c.1957T > C (p.Cys653Arg) | AGCCYGTACCCATGGAGGTAAGG, GCCYGTACCCATGGAGGTAAGGG | Hereditary diffuse leukoencephalopathy with spheroids |
| 690016560 | NM_005211.3(CSF1R):c.2717T > C (p.Ile906Thr) | GCAGAYCTGCTCCTTCCTTCAGG | Hereditary diffuse leukoencephalopathy with spheroids |
| 121917769 | NM_003361.3(UMOD):c.376T > C (p.Cys126Arg) | GGCCACAYGTGTCAATGTGGTGG, GCCACAYGTGTCAATGTGGTGGG | Familial juvenile gout |
| 121917773 | NM_003361.3(UMOD):c.943T > C (p.Cys315Arg) | ATGGCACYGCCAGTGCAAACAGG | Glomerulocystic kidney disease with hyperuricemia and isosthenuria |
| 121917818 | NM_007255.2(B4GALT7):c.617T > C (p.Leu206Pro) | TGCYCTCCAAGCAGCACTACCGG | Ehlers-Danlos syndrome progeroid type |
| 121917824 | NM_021615.4(CHST6):c.827T > C (p.Leu276Pro) | GGACCYGGCGCGGGAGCCGCTGG | Macular conical dystrophy Type I |
| 121917848 | NM_000452.2(SLC10A2):c.728T > C (p.Leu243Pro) | TTTCYTCTGGCTAGAATTGCTGG | Bile acid malabsorption, primary |
| 121918006 | NM_000478.4(ALPL):c.1306T > C (p.Tyr436His) | TGGACYATGGTGAGACCTCCAGG | Infantile hypophosphatasia |
| 121918010 | NM_000478.4(ALPL):c.979T > C (p.Phe327Leu) | CAAAGGCYTCTTCTTCTGCTGGTGG, GGCYTCTTCTTCTGCTGGTGGAAGG | Infantile hypophosphatasia |
| 121918088 | NM_000371.3(TTR):c.400T > C (p.Tyr134His) | CCCCYACTCCTATTCCACCACGG | |
| 121918110 | NM_001042465.1(PSAP):c.1055T > C (p.Leu352Pro) | GAAGCYGCCGAAGTCCCTGTCGG | Gaucher disease, atypical, due to saposin C deficiency |
| 121918137 | NM_00370.4(RNASET2):c.550T > C (p.Cys184Arg) | CCAGYGCCTTCCACCAAGCCAGG | Leukoencephalopathy, cystic, without megalencephaly |
| 121918191 | NM_001127628.1(FBP1):c.581T > C (p.Phe194Ser) | GGAGTYCATTTTGGTGGACAAGG | Fructose-biphosphatase deficiency |
| 121918306 | NM_006946.2(SPTBN2):c.758T > C (p.Leu253Pro) | ACCAAGCYGCTGGATCCCGAAGG, AAGCYGCTGGATCCCGAAGGTGG, AGCYGCTGGATCCCGAAGGTGGG | Spinocerebellar ataxia 5 |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 121918505 | NM_000141.4(FGFR2):c.799T > C (p.Ser267Pro) | AATGCYCCACAGTGGTCGGAGG | Pfeiffer syndrome, Neoplasm of stomach |
| 121918643 | NM_003126.2(SPTA1):c.620T > C (p.Leu207Pro) | GTGGAGCYGGTAGCTAAAGAAGG, TGGAGCYGGTAGCTAAAGAAGGG | Hereditary pyropoikilocytoss, Elliptocytosis 2 |
| 121918646 | NM_001024858.2(SPTB):c.604T > C (p.Trp202Arg) | CTCCAGCYGGAAGGATGGCTTGG | Spherocytosis type 2 |
| 121918648 | NM_001024858.2(SPTB):c.6055T > C (p.Ser2019Pro) | ATGCCCYCTGTGGCTGAGGCGTGG | |
| 727504166 | NM_000543.4(SMPD1):c.4755T > C (p.Cys159Arg) | TGAGGCYGTGGCCTGCTCCTGG, GAGGCCYGTGGCCTGCTCCTGGG | Niemann-Pick disease, type A, Niemann-Pick disease, type B |
| 193922915 | NM_000434.3(NEU1):c.1088T > C (p.Leu363Pro) | CAGCYATGGCCAGGCCCCAGTGG | Sialidosis, type II |
| 727504419 | NM_000501.3(ELN):c.889 + 2T > C | CAGGYAACATCTGTCCCAGCAGG, AGGYAACATCTGTCCCAGCAGGG | Supravalvar aortic stenosis |
| 376395543 | NM_000256.3(MYBPC3):c.26-2A > G | GAGACYGAAGGGCCAGTGGAGG | Primary familial hypertrophic cardiomyopathy, Familial hypertrophic cardiomyopathy 4, Cardiomyopathy |
| 1169305 | NM_000545.6(HNF1A):c.1720G > A (p.Gly574Ser) | GATGCYGGCAGGGTCCTGGCTGG, ATGCYGGCAGGGTCCTGGCTGGG, TGCYGGCAGGGTCCTGGCTGGGG | Maturity-onset diabetes of the young, type 3 |
| 730880130 | NM_000527.4(LDLR):c.1468T > C (p.Trp490Arg) | CTACYGGACCGACTCTGTCCTGG, TACYGGACCGACTCTGTCCTGGG | Familial hypercholesterolemia |
| 281860286 | NM_018713.2(SLC30A10):c.500T > C (p.Phe167Ser) | GGCGCTTYCGGGGGGCCTCAGGG | Hypermanganesemia with dystonia, polycythemia and cirrhosis |
| 730880306 | NM_145693.2(LPIN1):c.1441 + 2T > C | AAGGYACCGCGGGCCTCGCGCGG, AGGYACCGCGGGCCTCGCGCGGG | Myoglobinuria, acute recurrent, autosomal recessive |
| 74315452 | NM_000454.4(SOD1):c.338T > C (p.Ile113Thr) | TTGCAYCATTGCCGCACACTGG | Amyotrophic lateral sclerosis type 1 |
| 730880455 | NM_000169.2(GLA):c.41T > C (p.Leu14Pro) | CGCGCYTGCGCTTCGCTTCCTGG | not provided |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 267606656 | NM_054027.4(ANKH):c.1015T > C (p.Cys339Arg) | AGCTCYGTTTCGTGATGTTTTGG | Craniometaphyseal dysplasia, autosomal dominant |
| 267606687 | NM_033409.3(SLC52A3):c.1238T > C (p.Val413Ala) | AGTTACGYCAAGGTGATGCTGGG | Brown-Vialetto-Van laere syndrome |
| 267606721 | NM_001928.2(CFD):c.640T > C (p.Cys214Arg) | GGTGYGCGGGGGCYGTGCTCGAGG, GTGYGCGGGGGCYGTGCTCGAGGG | Complement factor d deficiency |
| 267606747 | NM_001849.3(COL6A2):c.2329T > C (p.Cys777Arg) | CGCCYGCACAAGCCACAGCAGG | Ullrich congenital muscular dystrophy |
| 431905515 | NM_001044.4(SLC6A3):c.671T > C (p.Leu224Pro) | CTGCACCYCCACCAGAGCCATGG | Infantile Parkinsonism-dystonia |
| 267606857 | NM_000180.3(GUCY2D):c.2846T > C (p.Ile949Thr) | AGAGAYCGCCAACATGTCACTGG | Cone-rod dystrophy 6 |
| 267606880 | NM_022489.3(INF2):c.125T > C (p.Leu42Pro) | GCTGCYCCAGATGCCCTCTGTGG | Focal segmental glomerulosclerosis 5 |
| 515726191 | NM_015713.4(RRM2B):c.581A > G (p.Glu194Gly) | AACTCCYTCTACAGCAGCAAAGG | RRM2B-related mitochondrial disease |
| 267606917 | NM_004646.3(NPHS1):c.793T > C (p.Cys265Arg) | GCTGCCYGCGTGCCCGAGGGG, CTGCCGYGCGTGGCCCGAGGGGG | Finnish congenital nephrotic syndrome |
| 267607104 | NM_001199107.1(TBC1D24):c.751T > C (p.Phe251Leu) | CAAGTTCYTCCACAAGGTGAGGG, TTCYTCCACAAGGTGAGGGCCGG | Myoclonic epilepsy, familial infantile |
| 267607182 | NM_144631.5(ZNF513):c.1015T > C (p.Cys339Arg) | TGGGCCYGCATGCGAGGAGAGG, CGCYGCATGCGAGGAGGAGGCTGG | Retinitis pigmentosa 58 |
| 267607211 | NM_000229.1(LCAT):c.508T > C (p.Trp170Arg) | TATGACYGGCGGCTGGAGCCCGG | Norum disease |
| 267607215 | NM_016269.4(LEF1):c.181T > C (p.Ser61Pro) | GAACGAGYCTGAAATCATCCCGG | Sebaceous tumors, somatic |
| 587783580 | NM_178151.2(DCX):c.683T > C (p.Leu28Pro) | AAAAAACYCTACACTCTGGATGG | Heterotopia |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 587783644 | NM_004004.5(GM2):c.107T > C (p.Leu36Pro) | GATCCYCGTTGTGGCTGCAAAGG | Hearing impairment |
| 587783653 | NM_005682.6(ADGRG1):c.1460T > C (p.Leu487Pro) | CCCTGCYCACCTGCCTTTCCTGG | Polymicrogyria, bilateral frontoparietal |
| 587783863 | NM_000252.2(MTM1):c.958T > C (p.Ser320Pro) | GGAAYCTTTAAAAAAGTGAAGG | Severe X-linked myotubular myopathy |
| 267607751 | NM_000249.3(MLH1):c.453 + 2T > C | ATCACGYAAGAATGGTACATGG, TCACGGYAAGAATGGTACATGGG | Hereditary Nonpolyposis Colorectal Neoplasms |
| 119103227 | NM_000411.6(HLCS):c.710T > C (p.Leu237Pro) | CTATCYTTCTCAGGAGGGAAGG | Holocarboxylase synthetase deficiency |
| 119103237 | NM_005787.5(ALG3):c.211T > C (n.Trp71Arg) | GATTGACYGGAAGGCCTACATGG | Congenital disorder of glycosylation type 1D |
| 398122806 | NM_003172.3(SURF1):c.679T > C (p.Trp227Arg) | CCACYGGCATTATCGAGACCTGG | Congenital myasthenic syndrome, acetazolamide-responsive |
| 80338747 | NM_004525.2(LRP2):c.7564T > C (p.Tyr2522His) | GTACCTCYACTGGGCTGACTGGG | Donnai Barrow syndrome |
| 398122838 | NM_001271723.1(FBXO38):c.616T > C (p.Cys206Arg) | TTCCTYGTATCCCAATGCTAAGG | Distal hereditary motor neuronopathy 2D |
| 398122989 | NM_014495.3(ANGPTL3):c.883T > C (p.Phe295Leu) | ACAAAACYTCAATGAAACGTGGG | Hypobetalipoproteinemia, familial, 2 |
| 80338945 | NM_004004.5(GM2):c.269T > C (p.Leu90Pro) | GCTCCYAGTGGCCATGCACGTGG | Deafness, autosomal recessive 1A, Hearing impairment |
| 80338956 | NM_000334.4(SCN4A):c.2078T > C (p.Ile693Thr) | AAGATCAYTGGCAATTCAGTGGG, AGATCAYTGGCAATTCAGTGGGG, GATCAYTGGCAATTCAGTGGGGG | Hyperkalemic Periodic Paralysis Type 1, Paramyotonia congenita of von Eulenburg |
| 267608131 | NM_000179.2(MSH6):c.4001 + 2T > C | CGGYAACTAACTAACTATAATGG | Hereditary Nonpolyposis Colorectal Neoplasms |
| 587784573 | NM_004963.3(GUCY2C):c.2782T > C (p.Cys928Arg) | TCCCYGTGCTGCTGGAGTTGTGG, CCCYGTGCTGCTGGAGTTGTGGG | Meconium ileus |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 267608511 | NM_003159.2(CDKL5):c.659T > C (p.Leu220Pro) | CCAACYTTTACTATTCAGAAGG | Early infantile epileptic encephalopathy 2 |
| 373842615 | NM_000118.3(ENG):c.1273-2A > G | CCGCCYGCGGGGATAAAGCCAGG, CGCCYGCGGGGATAAAGCCAGGG | Haemorrhagic telangiectasia 1 |
| 185492581 | NM_000335.4(SCN5A):c.376A > G (p.Lys126Glu) | GAATCYTCACAGCCGCTCTCCGG | Brugada syndrome |
| 200533370 | NM_133499.2(SYN1):c.1699A > G (p.Thr567Ala) | GATGYCTGACGGGTAGCCTGTGG, ATGYCTGACGGGTAGCCTGTGGG | Epilepsy, X-linked, with variable learning disabilities and behavior disorders, not specified |
| 118203981 | NM_148960.2(CLDN19):c.269T > C (p.Leu90Pro) | GCTCCYGGGCTTCGTGGCCATGG | Hypomagnesemia 5, renal, with ocular involvement |
| 137853892 | NM_001235.3(SERPINH1):c.233T > C (p.Leu78Pro) | GTGCYAGGGCTCGTCGTCGCTGG, TCGCYAGGGCTCGTCGTCGCTGGG | Osteogenesis imperfecta type 10 |
| 118204024 | NM_000263.3(NAGLU):c.142T > C | GGCCGACYTCTCCGTCGTCGTGG | Mucopolysaccharidosis,MPS-III-B |
| 690016563 | NM_005211.3(CSF1R):c.1745T > C (p.Leu582Pro) | CAACCYGCAGTTTGGTGAGATGG | Hereditary diffuse leukoencephalopathy with spheroids |
| 58380626 | NM_000526.4(KRT14):c.1243T > C (p.Tyr415His) | CGCCACCYACCGCCGCCCTGCTGG, CACCYACCGCCGCCCTGCTGGAGG, ACCYACCGCCGCCCTGCTGGAGGG | Epidermolysis bullosa herpetiformis, Dowling-Meara |
| 113994151 | NM_207346.2(TSEN54):c.277T > C (p.Ser93Pro) | TTGAAGYCTCCCGCGGTGAGCCGG, AAGYCTCCCGCGGTGAGCGGCGG | Pontocerebellar hypoplasia type 4 |
| 113994206 | NM_004937.2(CTNS):c.473T > C (p.Leu158Pro) | TGGTCYGAGCTTCGACTTCGTGG | Cystinosis |
| 62516109 | NM_000277.1(PAH):c.638T > C (p.Leu213Pro) | CCACTTCYTGAAAAGTACTGTGG | Phenylketonuria |
| 370011798 | NM_001302946.1(TRNT1):c.668T > C (p.Ile223Thr) | GCAAYTGCAGAAAATGCAAAAGG | Sideroblastic anemia with B-cell immunodeficiency, periodic fevers, and developmental delay |
| 62517167 | NM_000277.1(PAH):c.293T > C (p.Leu98Ser) | AAGATCYTGAGGCATGACATTGG | Mild non-PKU hyperphenylalanemia |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 12021720 | NM_001918.3(DBT):c.1150G > A (p.Gly384Ser) | GACYCACAGAGCCCAATTCTGG | Intermediate maple syrup urine disease type 2 |
| 104886289 | NM_000495.4(COL4A5):c.4756T > C (p.Cys1586Arg) | TCCCCATYGTCCTCAGGGATGGG | Alport syndrome, X-linked recessive |
| 370471013 | NC_012920.1:m.5559A > G | CAACYTACTGAGGGGTTTGAAGG | Leigh disease |
| 121434215 | NM_000487.5(ARSA):c.410T > C (p.Leu137Pro) | GCCTTCCYGCCCCCCCATCAGGG | Metachromatic leukodystrophy, adult type |
| 386134128 | NM_000096.3(CP):c.1123T > C (p.Tyr375His) | ACACTACYACATTGCCGCTGAGG | Deficiency of ferroxidase |
| 121434275 | NM_001127328.2(ACADM):c.1136T > C (p.Ile379Thr) | GTGCAGAYACTTGGAGGCAATGG | Medium-chain acyl-coenzyme A dehydrogenase deficiency |
| 121434276 | NM_001127328.2(ACADM):c.742T >C (p.Cys248Arg) | CAGCGAYGTTCAGATACTAGAGG | Medium-chain acyl-coenzyme A dehydrogenase deficiency |
| 121434284 | NM_002225.3(IVD):c.134T > C (p.Leu45Pro) | ATGGGCYAAGCAGGAGGAGCAGAGG | ISOVALERIC ACIDEMIA, TYPE I |
| 121434334 | NM_005908.3(MANBA):c.1513T > C (p.Ser505Pro) | ATTACGYCCAGTCCTACACAAATGG, TTACGYCCAGTCCTACAAATGGG, TACGYCCAGTCCTACAAATGGGG | Beta-D-mannosidosis |
| 121434366 | NM_000159.3(GCDH):c.883T > C (p.Tyr295His) | CGCCCGYACGGCATCGCGTGGG, GCCCGYACGGCATCGCGTGGGG | Glutaric aciduria, type 1 |
| 60715293 | NM_000424.3(KRT5):c.541T > C (p.Ser181Pro) | GTTTGCYCCTTCATCGACAAGG | Epidermolysis bullosa herpetiformis, Dowling-Meara |
| 121434409 | NM_001003722.1(GLE1):c.2051T > C (p.Ile684Thr) | AAGGACAYTCTGTCCCCAAGGG | Lethal arthrogryposis with anterior horn cell disease |
| 121434434 | NM_001287.5(CLCN7):c.2297T > C (p.Leu766Pro) | GGGCCYGCGGCACCTGGTGGTGG | Osteopetrosis autosomal recessive 4 |
| 121434455 | NM_000466.2(PEX1):c.1991T > C (p.Leu64Pro) | GATGACCYTGACCTCATTGCTGG | Zellweger syndrome |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base
to be edited, e.g., C. (SEQ ID NOs: 747 to 1868 appear from top to bottom below,
respectively)

| dbSNP # | Genotype | Protospacer and PAM sequence(s) | Associated uenetic disease |
|---|---|---|---|
| 199422317 | NM_001099274.1(TINF2):c.862T > C (p.Phe288Leu) | CTGYTTCCCTTTAGGAATCTCGG | Aplastic anemia |
| 104895221 | NM_001065.3(TNFRSF1A):c.349T > C (p.Cys117Arg) | CTCTTCTYGCACAGTGGACCGGG | TNF receptor-associated periodic fever syndrome (TRAPS) |
| 137854459 | NM_000138.4(FBN1):c.4987T > C (p.Cys1663Arg) | GGGACAYGTTACAACACCGTTGG | Marfan syndrome |
| 387907075 | NM_024027.4(COLEC11):c.505T > C (p.Ser169Pro) | CAGCTGYCCTGCCAGGGCCGCGG, AGCTGYCCTGCCAGGGCCGCGGG, GCTGYCCTGCCAGGGCCGCGGGG, CTGYCCTGCCAGGGCCGCGGGGG | Carnevale syndrome |
| 1048095 | NM_000352.4(ABCC8):c.674T > C (p.Leu225Pro) | TGCYGTCCAAAGGCACCTACTGG | Permanent neonatal diabetes mellitus |
| 796065347 | NM_019074.3(DLL4):c.1168T > C (p.Cys390Arg) | GAAYGTCCCCCAACTTCACCGG | Adams-Oliver syndrome, ADAMS-OLIVER SYNDROME 6 |
| 137852347 | NM_000402.4(G6PD):c.1054T > C (p.Tyr352His) | AGGGYACCTGGACGACCCCACGG | Anemia, nonspherocytic hemolytic, due to G6PD deficiency |
| 74315327 | NM_213653.3(HFE2):c.302T > C (p.Leu101Pro) | GGACCYYGCCTTCCATTCGGCGG | Hemochromatosis type 2A |
| 137852579 | NM_000044.3(AR):c.2033T > C (p.Leu678Pro) | GTCCYGGAAGCCATTGAGCCAGG | |
| 137852636 | NM_001166107.1(HMGCS2):c.520T > C (p.Phe174Leu) | CCCTCYTCAATGCTGCCAACTGG | mitochondrial 3-hydroxy-3-methylglutaryl-CoA synthase deficiency |
| 137852661 | NM_033163.3(FGF8):c.118T > C (p.Phe40Leu) | TTCCCYGYTCCGGGCTGGCCGGG | Kallmann syndrome 6 |
| 121912967 | NM_005215.3(DCC):c.503T > C (p.Met168Thr) | AGCCCAYGCCAACAATCCACTGG | |
| 137852806 | NM_001039523.2(CHRNA1):c.901T > C (p.Phe301Leu) | TGTGYTCCTTCTGGTCATCGTGG | Myasthenic syndrome, congenital, fast-channel |
| 137852850 | NM_182760.3(SUMF1):c.463T > C (p.Ser155Pro) | GGCGACYCCTTTGTCTTTGAAGG | Multiple sulfatase deficiency |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base
to be edited, e.g., C. (SEQ ID NOs: 747 to 1868 appear from top to bottom below,
respectively)

| dbSNP # | Genotype | Protospacer and PAM sequence(s) | Associated uenetic disease |
|---|---|---|---|
| 137852886 | NM_000158.3(GBE1):c.671T > C (p.Leu224Pro) | AATGTACYACCAAGAATCAAAGG | Glycogen storage disease, type IV, GLYCOGEN STORAGE DISEASE IV, NONPROGRESSIVE HEPATIC |
| 137852911 | NM_000419.3(ITGA2B):c.641T > C (p.Leu214Pro) | CTGGTGCYTGGGCTCCTGGCGG | Glanzmann thrombasthenia |
| 137852948 | NM_138694.3(PKHD1):c.10658T > C (p.Ile3553Thr) | GAGCCCAYTGAAATACGCTCAGG | Polycystic kidney disease, infantile type |
| 137852964 | NM_024960.4(PANK2):c.178T > C (p.Ser60Pro) | ATTGACYCAGTCGGATTCAATGG | |
| 137853020 | NM_006899.3(IDH3B):c.395T > C (p.Leu132Pro) | TGCGGCYGAGGTAGGTGGTCTGG, GCGGCYGAGGTAGGTGGTCTGGG | Retinitis pigmentosa 46 |
| 137853249 | NM_033500.2(HK1):c.1550T > C (p.Leu517Ser) | GACTTCTYGGCCCTGGATCTTGG, TTCTYGGCCCTGGATCTTGGAGG | Hemolytic anemia due to hexokinase deficiency |
| 137853270 | NM_000444.5(PHEX):c.1664T > C (p.Leu555Pro) | AGCYCCAGAAGCCTTTCTTTTGG | Familial X-linked hypophosphatemic vitamin D refractory rickets |
| 137853325 | NM_003639.4(IKBKG):c.1249T > C (p.Cys417Arg) | TGGAGYGCATTGAGTAGGGCCGG | Hypohidrotic ectodermal dysplasia with immune deficiency, Hyper-IgM immunodeficiency, X-linked, with hypohidrotic ectodermal dysplasia |
| 28932769 | NM_002055.4(GFAP):c.1055T > C (p.Leu352Pro) | GGACCYGCTCAATGTCAAGCTGG | Alexander disease |
| 397507439 | NM_002769.4(PRSS1):c.116T > C (p.Val39Ala) | TACCAGGYGTCCCTGAATTCTGG | Hereditary pancreatitis |
| 387906446 | NM_000132.3(F8):c.1729T > C (p.Ser577Pro) | AAAGAAYCTGTAGATCAAAGAGG | Hereditary factor VIII deficiency disease |
| 387906482 | NM_000133.3(F9):c.1031T > C (p.Ile344Thr) | ACGAACAYCTTCCTCAAATTTGG | Hereditary factor IX deficiency disease |
| 387906508 | NM_000131.4(F7):c.983T > C (p.Phe328Ser) | GACGTYCTGAGAGGACGCTGG | Factor VII deficiency |
| 387906532 | NM_001040113.1(MYH11):c.3791T > C (p.Leu1264Pro) | GAAGCYGGAGGCGCAGGTGCAGG | Aortic aneurysm, familial thoracic 4 |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 387906658 | NM_002465.3(MYBPC1):c.2566T > C (p.Tyr856His) | CAAACCYATATCCGCAGAGTTGG | Distal arthrogryposis type 1B |
| 387906701 | NM_003491.3(NAA10):c.109T > C (p.Ser37Pro) | TGGCCTTYCCTGGCCCCAGGTGG, GGCCTTYCCTGGCCCCAGGTGGG | N-terinal acetyltransferase deficiency |
| 387906717 | NM_000377.2(WAS):c.881T > C (p.Ile294Thr) | GACTTCAYTGAGGACCAGGGTGG, ACTTCAYTGAGGACCAGGGTGGG | Severe congenital neutropenia X-linked |
| 387906809 | NM_000287.3(PEX6):c.1601T > C (p.Leu534Pro) | CTTCYGGGCCCGGGACCGTGATGG, TTCYGGGCCCGGGACCGTGATGGG | Peroxisome biogenesis disorder 4B |
| 387906965 | NM_024513.3(FYCO1):c.4127T > C (p.Leu1376Pro) | CAGCCYGATCCCCATCACTGTGG | Cataract, autosomal recessive congenital 2 |
| 387906967 | NM_006147.3(IRF6):c.65T > C (p.Leu22Pro) | GCCYCTACCCTGGGCTCATCTGG | Van der Woude syndrome, Popliteal pterygium syndrome |
| 387906982 | NM_025132.3(WDR19):c.20T > C (p.Leu7Pro) | TCTCACYGCTAGAAAAGACTTGG | Asphyxiating thoracic dystrophy 5 |
| 387907072 | NM_032446.2(MEGF10):c.2320T > C (p.Cys774Arg) | GGGCAGYGTACTTGCCGCACTGG | Myopathy, areflexia, respiratory distress, and dysphagia, early-onset, Myopathy, areflexia, respiratory distress, and dysphagia, early-onset, mild variant |
| 137854499 | NM_005502.3(ABCA1):c.6026T > C (p.Phe2009Ser) | GAGTYCTTTGCCCTTTTGAGAGG | Familial hypoalphalipoproteinemia |
| 387907117 | NM_000196.3(HSD11B2):c.1012T > C (p.Tyr338His) | CCGCCGYATTACCCCGGCCAGG, CGCCCGYATTACCCCGGCCAGGG | Apparent mineralocorticoid excess |
| 387907170 | NM_004453.3(ETFDH):c.1130T > C (p.Leu377Pro) | CCAAAACYCACCTTTCCTGGTGG | |
| 387907205 | NM_033360.3(KRAS):c.211T > C (p.Tyr71His) | GGACCAGYACATGAGGACTGGGG, CCAGYACATGAGGACTGGGAGG, CAGYACATGAGGACTGGGAGGG | Cardiofaciocutaneous syndrome 2 |
| 387907240 | NM_024110.4(CARD14):c.467T > C (p.Leu56Pro) | CAGCAGCYGCAGGAGCACCTGG | Pityriasis rubra pilaris |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base
to be edited, e.g., C. (SEQ ID NOs: 747 to 1868 appear from top to bottom below,
respectively)

| dbSNP # | Genotype | Protospacer and PAM sequence(s) | Associated uenetic disease |
|---|---|---|---|
| 387907282 | NM_152296.4(ATP1A3):c.2431T > C (p.Ser811Pro) | TGCCATYCCACTGGCGTACGAGG | Alternating hemiplegia of childhood 2 |
| 387907361 | NM_005120.2(MED12):c.3493T > C (p.Ser1165Pro) | AGGACYCTGAGCCAGGGGCCCGG | Ohdo syndrome, X-linked |
| 28933970 | NM_006194.3(PAX9):c.62T > C (p.Leu21Pro) | GGCCGCYGCCCAACGCCATCCGG | Tooth agenesis, selective, 3 |
| 137854472 | NM_000138.4(FBN1):c.3128A > G (p.Lys1043Arg) | TGCACYTGCCGTGGGTGCAGAGG | |
| 727504261 | NM_000257.3(MYH7):c.2708A > G (p.Glu903Gly) | AGCGCYCCTCAGCATCTGCCAGG | Cardiomyopathy, not specified |
| 81002853 | NM_000059.3(BRCA2):c.476- 2A > G | ACCACYGGGGTAAAAAAAGGGG, TACCACYGGGGTAAAAAAAGGGG | Familial cancer of breast, Breast-ovarian cancer, familial 2, Hereditary cancer-predisposing syndrome |
| 119473032 | NM_021020.3(LZTS1):c.355A > G (p.Lys119Glu) | CCCTYCTCGGAGCCCTGTAGAGG | |
| 193922801 | NM_000540.2(RYR1):c.7043A > G (p.Glu2348Gly) | TTCYCCTCCACGCTCTCGCCTGG | not provided |
| 36210419 | NM_000218.2(KCNQ1):c.652A > G (p.Lys218Glu) | GCCCCYTGGAGCCACGCAGAGG | Torsades de pointes, Cardiac arrhythmia |
| 121964989 | NM_000108.4(DLD):c.1483A > G (p.Arg495Gly) | TTCTCYAAAAGCTTCTGATAAGG | Maple syrup urine disease, type 3 |
| 28936669 | NM_000095.2(COMP):c.1418A > G (p.Asp473Gly) | ATTGYCGTCGTCGTCGCAGG | |
| 28936696 | NM_018488.2(TBX4):c.1592A > G (p.Gln531Arg) | GTACYGTAAGGAAGATTCTCGGG, GGTACYGTAAGGAAGATTCTCGG | Isch opatellar dysplas a |
| 121965077 | NM_000137.2(FAH):c.1141A > G (p.Arg381Gly) | TCCYGGTCTGACCATTCCCCAGG | Tyros nemia type I |
| 794728203 | NM_000138.4(FBN1):c.3344A > G (p.Asp1115Gly) | ACTCAYCAATATCTGCAAAATGG | Thoracic aortic aneurysms and aortic dissections |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 786205436 | NM_003002.3(SDHD):c.275A > G (p.Asp92Gly) | GAATAGYCCATCGCAGAGCAAGG | Fatal infantile mitochondrial cardiomyopathy |
| 72551317 | NM_000784.3(CYP27A1):c.776A > G (p.Lys259Arg) | AGTCCACYTGGGAGGAAGGTGG | Cholestanol storage disease |
| 786205687 | NM_016218.2(POLK):c.1385A > G (p.Asn462Ser) | ATTCACAYTCTTCAACTTAATCGG | Malignant tumor of prostate |
| 794728280 | NM_000138.4(FBN1):c.7916A > G (p.Tyr2639Cys) | TGTTCAYACTGAAGCCGGCGG, CTGTTCAYACTGGAAGCCGGCGG | Thoracic aortic aneurysms and aortic dissections |
| 28937317 | NM_000335.4(SCN5A):c.3971A > G (p.Asn1324Ser) | GCAYTGACCACCACCTCAAGTGG | Long QT syndrome 3, Congenital long QT syndrome |
| 786205854 | NM_144499.2(GNAT1):c.386A > G (p.Asp129Gly) | CGGAGYCCTTCCACAGCCGCTGG | NIGHT BLINDNESS, CONGENITAL |
| 104893776 | NM_000539.3(RHO):c.533A > G (p.Tyr178Cys) | GGATGYACCTGAGGACAGGCAGG | Retinitis pigmentosa 4 |
| 28937590 | NM_001257342.1(BCS1L):c.232A > G (p.Ser78Gly) | GACACYGAGGTGCTGAGTACGGG, CGACACYGAGGTGCTGAGTACGG | GRACILE syndrome |
| 104893866 | NM_000320.2(QDPR):c.449A > G (p.Tyr150Cys) | TGCCGYACCCGATCATACCTGGG, ATGCCGYACCCGATCATACCTGG | Dihydropteridine reductase deficiency |
| 587776590 | NM_015629.3(PRPF31):c.527 + 3A > G | GACAYACCCCTGGGTGTGGAGG, GCGGACAYACCCCTGGGTGTGG | Retinitis pigmentosa 11 |
| 104894015 | NM_000162.3(GCK):c.641A > G (p.Tyr214Cys) | GTAGYAGCAGGAGATCATCGTGG | Hyperinsulinemo c hypoglycemia familial 3 |
| 202247823 | NM_000532.4(PCCB):c.1606A > G (p.Asn536Asp) | ATATAYTGCATGTTTTCTCCAAGG | Propionic acidemia |
| 104894199 | NM_000073.2(CD3G):c.1A > G (p.MetIVal) | CCAYGTCAGTTCTCTGTCCTCCGG | Immunodeficiency 17 |
| 104894208 | NM_001814.4(CTSC):c.857A > G (p.Gln286Arg) | CTCCYGAGGGCTTAGGATTGGGG, CCTCCYGAGGGCTTAGGATTGGG, ACCTCCYGAGGGCTTAGGATTGG | Papillon-Lenf\xc3\xa8vre syndrome, Haim-Munk syndrome |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 104894211 | NM_001814.4(CTSC):c.1040A > G (p.Tyr347Cys) | TCCTACAYAGTGTACTCAGAGG | Papillon-Lenxc3\xa8vre syndrome, Periodontitis, |
| 104894290 | NM_000448.2(RAG1):c.2735A > G (p.Tyr912Cys) | CTGYACTGGCAGAGGGATTCTGG | Histiocytic medullary reticulosis |
| 104894354 | NM_000217.2(KCNA1):c.676A > G (p.Thr226Ala) | GCGYTTCCACGATGAAGAAGGGG, AGCGYTTCCACGATGAAGAAGGG, CAGCGYTTCCACGATGAAGAGG | Episodic ataxia type 1 |
| 104894425 | NM_014239.3(EIF2B2):c.638A > G (p.Glu213Gly) | AGTTGTCYCAATACCTGCTTTGG | Leukoencephalopathy with vanishing white matter, Ovarioleukodystrophy |
| 104894450 | NM_000270.3(PNP):c.383A > G (p.Asp128Gly) | ATAYCTCCAACCTCAAACTTGGG, GATAYCTCCAACCTCAAACTTGG | Purine-nucleoside phosphorylase deficiency |
| 147394623 | NM_024887.3(DHDDS):c.124A > G (p.Lys42Glu) | GGCACTYCTTGGCATAGCGACGG | Retinitis pigmentosa 59 |
| 60733330 | NM_005557.3(KRT16):c.374A > G (p.Asn125Ser) | GCGGTCAYTGAGGTTCTGCATGG | Pachyonychia congenita, type 1, Palmoplantar keratoderma, nonepidermolytic, focal |
| 104894634 | NM_030665.3(RAI1):c.4685A > G (p.Gln1562Arg) | CTGCTGCYGTCGTCGTCGCTTGG | Smith-Magenis syndrome |
| 104894730 | NM_000363.4(TNNI3):c.532A > G (p.Lys178Glu) | CCTYCTTCACCTGCTTGAGGTGG, CCTCCTYCTTCACCTGCTTGAGG | Familial restrictive cardiomyopathy 1 |
| 104894816 | NM_002049.3(GATA1):c.653A > G (p.Asp218Gly) | GTCCCTGCYCCCTCCGCCACAGTGG | GATA-1-related thrombocytopenia with dyserythropoiesis |
| 794726773 | NM_001165963.1(SCN1A):c.1662+303 A > G | GTGCCAYACCTGGTGTGGGAGG | Severe myoclonic epilepsy in infancy |
| 104894861 | NM_000202.6(IDS):c.404A > G (p.Lys135Arg) | AAAGACTYTTCCCACCGACATGG | Mucopolysaccharidosis, MPS-II |
| 104894874 | NM_000266.3(NDP):c.125A > G (p.His42Arg) | TGGYGCCTCATGCAGCGTCGAGG | |
| 191205969 | NM_002420.5(TRPM1):c.296T > C (p.Leu99Pro) | AAGCYTTAATATCTGTGCATGG | Congenital stationary night blindness, type 1C |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 794727073 | NM_019109.4(ALG1):c.1188-2A > G | TAAACYGCAGAGAGAACCAAGGG, GTAAACYGCAGAGAACCAAG G | Congenital disorder of glycosylation type 1K |
| 281875236 | NM_001004334.3(GPR179):c.659A > G (p.Tyr220Cys) | CCCACAYATCCATCCATCTGCCTGCGG | Congenital stationary night blindness, type 1E |
| 28939094 | NM_015915.4(ATL1):c.1222A > G (p.Met408Val) | CACCCAYCTCTTCACCCCTCGG | Spastic paraplegia 3 |
| 281875324 | NM_053359.5(SMAD4):c.989A > G (p.Glu330Gly) | ATCCATTYCAAAGTAAGCAATGG | Juvenile polyposis syndrome, Hereditary cancer-predisposing syndrome |
| 77173848 | NM_000037.3(ANK1):c.-108T > C | GGGCCYGGCCCGCACGTCACAGG | Spherocytosis, type 1, autosomal recessive |
| 150181226 | NM_001159772.1(CANT1):c.671T > C (p.Leu224Pro) | CGTCYGTACGTGGGCGGCGCCTGGG, GCGTCYGTACGTGGGCGGCCTGG | Desbuquois syndrome |
| 397514253 | NM_000041.3(APOE):c.237-2A > G | CGCCCYGCGGCCGGAGGGGCGGG, GCGCCCYGCGGCCGGAGAGGCGG | Familial type 3 hyperlipoproteinemia |
| 397514348 | NM_000060.3(BTD):c.278A > G (p.Tyr93Cys) | GTTCAYAGATGTCAAGGTTCTGG | Biotinidase deficiency |
| 397514415 | NM_000060.3(BTD):c.1313A > G (p.Tyr438Cys) | GGCAYACAGCTCTTTGGATAAGG | Biotinidase deficiency |
| 397514501 | NM_007171.3(POMT1):c.430A > G (p.Asn144Asp) | GAGCATYCTCTGTTTCAAAGAGG | Limb-girdle muscular dystrophy- |
| 370382601 | NM_174917.4(ACSF3):c.1A > G (D.Met1Val) | GGCAGCAYTGCACTGACAGGCGG | not provided |
| 72554332 | NM_000531.5(OTC):c.238A > G (p.Lys80Glu) | AAGGACTYCCCTTGCAATAAGG | Ornithine carbamoyltransferase deficiency |
| 397514599 | NM_033109.4(PNPT1):c.1424A > G (p.Glu475Gly) | GACTYCAGATGTAACTCTTATGG | Deafness, autosomal recessive 70 |
| 397514650 | NM_000108.4(DLD):c.1444A > G (p.Arg482Gly) | GACTCYAGCTATATCTTTCACAGG | Maple syrup urine disease, type 3 |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 397514675 | NM_003156.3(STIM1):c.251A > G (p.Asp84Gly) | TTCCACAYCCACATCACCATTGG | Myopathy with tubular aggregates |
| 794728378 | NM_000238.3(KCNH2):c.1913A > G (p.Lys638Arg) | ATCYTCTCTGAGTTGGTGTTGGG, GATCYTCTCTGAGTTGGTGTTGG | Cardiac arrhythmia |
| 397514711 | NM_002163.2(IRF8):c.238A > G (p.Thr80Ala) | AACCTCGYCTTCCAAGTGGCTGG | Autosomal dominant CD11C+/CD1C+ dendritic cell deficiency |
| 397514729 | NM_000388.3(CASR):c.85A > G (p.Lys29Glu) | CCCCCYCTTTTGGGCTCGCTGG | Hypocalcemia, autosomal dominant 1, with bartter syndrome |
| 397514743 | NM_022114.3(PRDM16):c.2447A > G (p.Asn816Ser) | GCCGCCYGTTTGGCTGCTGGCACGGG | Left ventricular noncompaction 8 |
| 397514757 | NM_005689.2(ABCB6):c.508A > G (p.Ser170Gly) | TGGGCYGTTCCAAGACACCAGGG, GTGGGCYGTTCCAAGACACCAGG | Dyschromatosis universalis hereditaria 3 |
| 28940313 | NM_152443.29RDH12):c.677A > G (p.Tyr226Cys) | CACTGCGYAGGTGGTGACCCCGG | Leber congenital amaurosis 13 |
| 794728538 | NM_000218.2(KCNQ1):c.1787A > G (p.Glu596Gly) | GTCTYCTACTCGGTTCAGGCGGG, TGTCTYCTACTCGGTTCAGGCGG | Cardiac arrhythmia |
| 794728569 | NM_000218.2(KCNQ1):c.605A > G (p.Asp202Gly) | AGGYCTGTGGAGTGCAGGAGAGG | Cardiac arrhythmia |
| 794728573 | NM_000218.2(KCNQ1):c.1515-2A > G | GCCYGCAGTGGAGAGGAGGAGG | Cardiac arrhythmia |
| 370874727 | NM_003494.3(DYSF):c.3349-2A > G | CCGCCCYGGAGACACGAAGCTGG | Limb-girdle muscular dystrophy, type 2B |
| 794728859 | NM_198056.2(SCN5A):c.2788-2A > G | ACCYGTCGAGATAATGGGTCAGG | not provided |
| 794728887 | NM_198056.2(SCN5A):c.4462A > G (p.Thr1488Ala) | CCTCTGYCATGAAGATGTCCTGG | not provided |
| 28940878 | NM_000372.4(TYR):c.125A > G (p.Asp42Gly) | CTCCTGYCCCCGCTCCACGGTGG | Tyrosinase-negative oculocutaneous albinism |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 397515420 | NM_172107.2(KCNQ2):c.1636A > G (p.Met546Val) | GCAYGACACTGCAGGGGGTGGG, CGCAYGACACTGCAGGGGGTGG, AACCGCAYGACACTGCAGGGGGG | Early infantile epileptic encephalopathy 7 |
| 397515428 | NM_001410.2(MEGF8):c.7099A > G (p.Ser2367Gly) | GACYCCCGTGAAATGATTCCCGG | Carpenter syndrome 2 |
| 143601447 | NM_201631.3(TGM5):c.122T > C (p.Leu41Pro) | TCAACCYCACCCTGTACTTCAGG | Peeling skin syndrome, acral type |
| 397515519 | NM_000207.2(INS):c..59A > G | GGGCYTTATTCCATCTCTCTCGG | Permanent neonatal diabetes mellitus |
| 397515523 | NM_000370.3(TTPA):c.191A > G (p.Asp64Gly) | CAGGYCCAGATCGAAATCCCGG, CCAGGYCCAGATCGAAATCCCGG | Ataxia with vitamin E deficiency |
| 397515891 | NM_000256.3(MYBPC3):c.1224-2A > G | TACTTGCYGTAGAACAGAAGGGG | Familial hypertrophic cardiomyopathy 4, Cardiomyopathy |
| 397516082 | NM_000256.3(MYBPC3):c.927-2A > G | GTCCCYGTGTCCCGCAGTCTAGG | Familial hypertrophic cardiomyopathy 4, Cardiomyopathy |
| 397516138 | NM_000257.3(MYH7):c.2206A > G (p.Ile736Val) | TATCAAYGAACTGTCCCTCAGGG, CTATCAAYGAACTGTCCCTCAGG | Familial hypertrophic cardiomyopathy 1, Cardiomyopathy, not specified |
| 1154510 | NM_002150.2(HPD):c.97G > A (p.Ala33Thr) | ATGACGYGGCCTGAATCACAGGG, AATGACGYGGCCTGAATCACAGG | 4-Alpha-hydroxyphenylpyruvate hydroxylase deficiency |
| 397516330 | NM_000260.3(MYO7A):c.6439-2A > G | ATATCCYGGGGGAGCAGAAGGG, GATATCCYGGGGGAGCAGAAACG | Usher syndrome, type 1 |
| 72556271 | NM_000531.5(OTC):c.482A > G (p.Asn161Ser) | CAGCCCAYTGATAATTGGGATGG | not provided |
| 606231260 | NM_023073.3(C5orf42):c.3290- | ATCYATCAAATACAAAAATTTGG | Orofac odigital syndrome 6 |
| 587777521 | NM_004817.3(TJP2):c.1992-2A > G | CAGCTCYGAGAAGAAACCACGGG, TCAGCTCYGAGAAGAAACCACGG | Progressive familial intrahepatic cholestasis 4 |
| 730880846 | NM_000257.3(MYH7):c.617A > G (p.Lys206Arg) | CTTCYTGCTGCGGTCCCAATGG | Cardiomyopathy |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base
to be edited, e.g., C. (SEQ ID NOs: 747 to 1868 appear from top to bottom below,
respectively)

| dbSNP # | Genotype | Protospacer and PAM sequence(s) | Associated genetic disease |
|---|---|---|---|
| 397517978 | NM_206933.2(USH2A):c.12067-2A > G | TTCCCYGTAAGAAAATTAACAGG | Usher syndrome, type 2A, Retinitis pigmentosa 39 |
| 606231409 | NM_000216.2(ANOS1):c.1A > G (p.Met1Val) | GCACCAYGGCTGCGGGTCGAGGG, GGCACCAYGGCTGCGGGTCGAGG | Kallmann syndrome 1 |
| 80356546 | NM_003334.3(UBA1):c.1639A > G (p.Ser547Gly) | TGGCYTGTCACCCGGATATGTGG | Arthrogryposis multiplex congenita, distal, X-linked |
| 80356584 | NM_194248.2(OTOF):c.766-2A > G | GACCYGCAGGCAGGAGAAGGGGG, TGACCYGCAGGCAGGAGAAGGGG, CTGACCYGCAGGCAGGAGAAGGG, GCTGACCYGCAGGCAGGAGAAGG | Deafness, autosomal recessive 9 |
| 730880930 | NM_000257.3(MYH7):c.1615A > G (p.Met539Val) | GGAACAYGCACTCCTCTTCCAGG | Cardiomyopathy |
| 118203947 | NM_013319.2(UBIAD1):c.355A > G (p.Arg119Gly) | TCCYGTCATCACTCTTTTTGTGG | Schnyder crystalline conical dystrophy |
| 60171927 | NM_000526.4(KRT14):c.368A > G (p.Asn123Ser) | GCGGTCAYTGAGGTTCTGCATGG | Epidermolysis bullosa herpetiformis, Dowling-Meara |
| 199422248 | NM_001363.4(DKC1):c.941A > G (p.Lys314Arg) | AATCYTGGCCCCATAGCAGATGG | Dyskeratosis congenita X-linked |
| 72558467 | NM_000531.5(OTC):c.929A > G (p.Glu310Gly) | TCCACTYCTTCTGGCTTTCTGGG, ATCCACTYCTTCTGGCTTTCTGG | not provided |
| 72558478 | NM_000531.5(OTC):c.988A > G (p.Arg330Gly) | ACTTTCYGTTTTCTGCCTCTGGG, CACTTTCYGTTTTCTGCCTCTGG | not provided |
| 118204455 | NM_000505.3(F12):c.158A > G (p.Tyr53Cys) | GGTGGYACTGGAAGGGGAAGTGG | Dyskeratosis congenita X-linked |
| 80357477 | NM_007294.3(BRCA1):c.5453A > G (p.Asp1818Gly) | TTGYCCTCTGTCCAGGCATCTGG | Familial cancer of breast, Breast-ovarian cancer, familial 1 |
| 121907908 | NM_024426.4(WT1):c.1021A > G (p.Ser341Gly) | CGCYCTCGTACCCTGTGCTGTGG | Mesothelioma |
| 121907926 | NM_000280.4(PAX6):c.1171A > G (p.Thr391Ala) | GTGGYGCCCGAGGTGCCCATTGG | Optic nerve aplasia, bilateral |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 121908023 | NM_024740.2(ALG9):c.860A > G (p.Tyr287Cys) | TTAYACAAAACAATGTTGAGTGG | Congenital disorder of glycosylation type 1L |
| 121908148 | NM_001243133.1(NLRP3):c.1180A > G (p.Glu627Gly) | ACAATYCCAGCTGGCTGGGCTGG | Familial cold urticaria |
| 121908166 | NM_006492.2(ALX3):c.608A > G (p.Asn203Ser) | CGGYTCTGGAACCAGACCTGGG, GCGGYTCTGGAACCAGACCTGGG, TGCGGYTCTGGAACCAGACCTGG | Frontonasal dysplasia |
| 121908184 | NM_020451.2(SEPN1):c. 1 A > G (p.Met1Val) | CCCAYGGCTGCGGCTGCGCGCGG, CGGCCCAYGGCTGCGGCTGGCGG | Eichsfeld type congenital muscular dystrophy |
| 121908258 | NM_130468.3(CHST14):c.878A > G (p.Tyr293Cys) | AAGTCAYAGTGCACGGCACAAGG | Ehlers-Danlos syndrome, musculocontractural type |
| 121908383 | NM_001128425.1(MUTYH):c.1241A > G (p.Gln414Arg) | AAGCYGCTCTGAGGGCTCCCAGG | Neoplasm of stomach |
| 121908580 | NM_004328.4(BCS1L):c.148A > G (p.Thr50Ala) | GTGYGATCATGTAATGCGCCGG | Mitochondrial complex III deficiency |
| 121908584 | NM_016417.2(GLRX5):c.294A > G (p.Gln98=) | CCTGACCYTGTCGGAGCTCCGGG | Anemia, sideroblastic, pyridoxine-refractory, autosomal recessive |
| 121908635 | NM_022817.2(PER2):c.1984A > G (p.Ser662Gly) | GCCACACYCTCTGCCTTGCCCGG | Advanced sleep phase syndrome, familial |
| 121908655 | NM_003839.3(TNFRSF11A):c.508A > G (p.Arg170Gly) | GGGCTYGCATTTGTCCGTGGAGG | Osteopetrosis autosomal recessive 7 |
| 29001653 | NM_000539.3(RHO):c.886A > G (p.Lys296Glu) | CGCTCTYGGCAAAGAACGCTGGG, GCGCTCTYGGCAAAGAACGCTGG | Retinitis pigmentosa 4 |
| 56307355 | NM_006502.2(POLH):c.1603A > G (p.Lys535Glu) | AGACTTTYCTGCTTAAAGAAGGG | Xeroderma pigmentosum, variant type |
| 121908919 | NM_002977.3(SCN9A):c.1964A > G (p.Lys655Arg) | CCTTTTCYTGTGTATTTGATTGG | Generalized epilepsy with febrile seizures plus, type 7, not specified |
| 121908939 | NM_006892.3(DNMT3B):c.2450A > G (p.Asp817Gly) | GACACGYCTGTGTAGTGCACAGG | Centomeric instability of chromosomes 1, 9 and 16 and immunodeficiency |

TABLE 1-continued

List of 911 base-editable gene variants associated with human disease
with an NGG PAM (SEQ ID NOs: 747 to 1868 appear from top to bottom below,
respectively). The "Y" in the protospacer and PAM sequences indicates the base
to be edited, e.g., C. (SEQ ID NOs: 747 to 1868 appear from top to bottom below,
respectively)

| dbSNP # | Genotype | Protospacer and PAM sequence(s) | Associated uenetic disease |
|---|---|---|---|
| 121909088 | NM_001005360.2(DNM2):c.1684A > G (p.Lys562Glu) | ACTYCTTCTCTTTCTTCCTGAGGG, TACTYCTTCTCTTTCTTCCTGAGG | Charcot-Marie-Tooth disease, dominant intermediate b, with neutropenia |
| 120074112 | NM_000483.4(APOC2):c.1A > G (p.Met1Val) | GCCCAYAGTGTCCAGAGACCTGG | Apolipoprotein C2 deficiency |
| 121909239 | NM_000314.6(PTEN):c.755A > G (p.Asp252Gly) | ATAYCCACCACACAGTAACCG | Macrocephaly/autism syndrome |
| 121909251 | NM_198217.2(ING1):c.515A > G (p.Asn172Ser) | TGGYTGCACAGACAGTACGTGGG, CTGGYTGCACACAGACAGTACGTGG | Squamous cell carcinoma of the head and neck |
| 121909396 | NM_001174089.1(SLC4A11):c.2518A > G (p.Met840Val) | GATCAYCTTCATGTAGGGCAGGG, AGATCAYCTTCATGTAGGGCAGG | Conical dystrophy and perceptive deafness |
| 121909533 | NM_000034.3(ALDOA):c.386A > G (p.Asp129Gly) | CCAYCCAACCTAAGAGAAGAGG | HNSHA due to aldolase A deficiency |
| 128627255 | NM_004006.2(DMD):c.835A > G (p.Thr279Ala) | TGACCGYGATCTGCAGAGAAGGG, CTGACCGYGATCTGCAGAGAAGG | Dilated cardiomyopathy 3B |
| 116929575 | NM_001085.4(SERPINA3):c.1240A > G (p.Met414Val) | GCTCAYGAAGAAGATGTTCTGGG, TGCTCAYGAAGAGATGTTCTGG | |
| 61748392 | NM_004992.3(MECP2):c.410A > G (p.Glu137Gly) | CAAYCCACTTTAGACGCGAAAGG | Mental retardation, X-linked, syndromic 13 |
| 61748906 | NM_001005741.2(GBA):c.667T > C (p.Trp223Arg) | CCCACTYGGCTCAAGACCAATCG | Gaucher disease, type 1 |
| 199473024 | NM_000238.3(KCNH2):c.3118A > G (p.Ser1040Gly) | CTGCYCTCCACGTCGCCCCGGGG, CCTGCYCTCCACGTCGCCCCGGG, GCCTGCYCTCCACGTCGCCCCGG | Sudden infant death syndrome |
| 794728365 | NM_000238.3(KCNH2):c.1129-2A > G | GGACCYGCACCCGGGGAAGGCGG | Cardiac arrhythmia |
| 72556293 | NM_000531.5(OTC):c.548A > G (p.Tyr183Cys) | AGAGCTAYAGTGTTCCTAAAAGG | not provided |
| 111033244 | NM_000441.1(SLC26A4):c.1151A > G (p.Glu384Gly) | TGAATYCCTAAGGAAGAGACTGG | Pendred syndrome, Enlarged vestibular aqueduct syndrome |
| 111033415 | NM_000260.3(MY07A):c.1344-2A > G | AGCYGCAGGGGCACAGGGATGGG, AAGCYGCAGGGGCACAGGGATGG | Usher syndrome, type 1 |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 121912439 | NM_000454.4(SOD1):c.302A > G (p.Glu101Gly) | AGAATCTYCAATAGACACATCGG | Amyotrophic lateral sclerosis type 1 |
| 111033567 | NM_002769.4(PRSS1):c.68A > G (p.Lys23Arg) | ATCYTGTCATCATCATCAAAGGG, GATCYTGTCATCATCATCAAAG G | Hereditary pancreatitis |
| 121912565 | NM_000901.4(NR3C2):c.2327A > G (p.Gln776Arg) | TCATCYGTTTGCCTGCTAAGCGG | Pseudohypoaldosteronism type 1 autosomal dominant |
| 121912574 | NM_000901.4(NR3C2):c.2915A > G (p.Glu972Gly) | CCGACYCCACCTTGGGCAGCTGG | Pseudohypoaldosteronism type 1 autosomal dominant |
| 121912589 | NM_001173464.1(KIF21A):c.2839A > G (p.Met947Val) | ATTCAYATCTGCCTCCATGTTGG | Fibrosis of extraocular muscles, congenital, 1 |
| 111033661 | NM_000155.3(GALT):c.253-2A > G | ATTCACCYACCGACAAGGATAGG | Deficiency of UDPglucose-hexose-1-phosphate uridylyltransferase |
| 111033669 | NM_000155.3(GALT):c.290A > G (p.Asn97Ser) | GAAGTGCYTGTCAAACAGGAGG | Deficiency of UDPglucose-hexose-1-phosphate uridylyltransferase |
| 111033682 | NM_000155.3(GALT):c.379A > G (p.Lys127Glu) | TGACCTYACTGGGTGGTGACGGG, ATGACCTYACTGGGTGGTGACGG | Deficiency of UDPglucose-hexose-1-phosphate uridylyltransferase |
| 111033786 | NM_000155.3(GALT):c.950A > G (p.Gln317Arg) | CAGCYGCCAATGGTTCCAGTTGG | Deficiency of UDPglucose-hexose-1-phosphate uridylyltransferase |
| 121912765 | NM_001202.3(BMP4):c.278A > G (p.Glu93Gly) | CCTCYCCCCAGACTGAAGCCGG | Microphthalmia syndromic 6 |
| 121912856 | NM_000094.3(COL7A1):c.425A > G (p.Lys142Arg) | CACCYTGGGACACACCAGGTCGGG, TCACCYTGGGGACACACCAGGTCGG | Epidermolysis bullosa dystrophica inversa, autosomal recessive |
| 199474715 | NM_152263.3(TPM3):c.505A > G (p.Lys169Glu) | CCAACTYACGAGCCACCTACAGG | Congenital myopathy with fiber type disproportion |
| 199474718 | NM_152263.3(TPM3):c.733A > G (p.Arg245Gly) | ATCYCTCAGCAAACTCAGCACGG | Congenital myopathy with fiber type disproportion |
| 121912895 | NM_001844.4(COL2A1):c.2974A > G (p.Arg992Gly) | CCTCYCTCACCACGTTGCCCAGG | Spondyloepimetaphyseal dysplasia Strudwick type |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated genetic disease |
|---|---|---|---|
| 121913074 | NM_000129.3(F13A1):c.851A > G (p.Tyr284Cys) | ATAGGCAYAGATATTGTCCCAGG | Factor xiii, a subunit, deficiency of |
| 121913145 | NM_000208.2(INSR):c.707A > G (p.His236Arg) | GCTGYGGCAACAGAGAGCCTTCGG | Leprechaunism syndrome |
| 312262745 | NM_025137.3(SPG11):c.2608A > G (p.Ile870Val) | ACTTAYCCTGGGAGAAGGATCG | Spastic paraplegia 11, autosomal recessive |
| 121913682 | NM_000222.2(KIT):c.2459A > G (p.Asp820Gly) | AGAAYCATTCTTGATGTCTCTGG | Mast cell disease, systemic |
| 587776757 | NM_000151.3(G6PC):c.230 + 4A > G | GTTCYTACCACTTAAAGACGAGG | Glycogen storage disease type 1A |
| 61752063 | NM_000330.3(RS1):c.286T > C (p.Trp96Arg) | TTCTTCGYGGACTGCAAACAAGG | Juvenile retinoschisis |
| 367543065 | NM_024549.5(TCTN1):c.221-2A > G | AGCAACYGCAGAAAAAGAGGGG, CAGCAACYGCAGAAAAAAGAGG | Joubert syndrome 13 |
| 5030773 | NM_000894.2(LHB):c.221A > G (p.Gln74Arg) | CCACCYGAGGCAGGGGCGGCAGG | Isolated lutropin deficiency |
| 199476092 | NM_000264.3(PTCH1):c.2479A > G (p.Ser827Gly) | CGTTACYGAAACTCCTGTGTAGG | Gorlin syndrome, Holoprosencephaly 7, not specified |
| 398123158 | NM_000117.2(EMD):c.450-2A > G | CGTTCCCYGAGGCAAAAGAGGGG | not provided |
| 199476103 | RMRP:n.71A > G | ACTTYCCCCTAGGCGGAAAGGGG, GACTTYCCCCTAGGCGGAAAGGG, GGACTTYCCCCTAGGCGGAAAGG | Metaphyseal chondrodysplasia, McKusick type, Metaphyseal dysplasia without hypotrichosis |
| 5030856 | NM_000277.1(PAH):c.1169A > G (p.Glu390Gly) | CTCYCTGCCACGTAATACAGGGG, ACTCYCTGCCACGTAATACAGGG, AACTCYCTGCCACGTAATACAGG | Phenylketonuria, Hyperphenylalaninemia, non-pku |
| 5030860 | NM_000277.1(PAH):c.1241A > G (p.Tyr414Cys) | GGGTCGYAGCGAACTGAGAAGGG, TGGGTCGYAGCGAACTGAGAAGG | Phenylketonuria, Hyperphenylalan nem a, non-pku |
| 87777055 | NM_020988.2(GNAO1):c.521A > G (p.Asp174Gly) | GGATGYCCTGCTCGGTGGCTGG | Early infantile epileptic encephalopathy 17 |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 587777223 | NM_024301.4(FKRP):c.1A > G (p.Met1Val) | CCGCAYGGGGCCGAAGTCTGGGG, GCCGAYGGGGCCGAAGTCTGGG, AGCCGCAYGGGGCCGAAGTCTGG | Congenital muscular dystrophy-dystroglycanopathy with brain and eye anomalies type AS |
| 587777479 | NM_003108.3(SOX11):c.347A > G (p.Tyr116Cys) | GTACTTGYAGTCGGGGTAGTCGG | Mental retardation, autosomal dominant 27 |
| 587777496 | NM_020435.3(GJC2):c.-170A > G | TTGYTCCCCCCTCGGCCTCAGGG, ATTGYTCCCCCCTCGGCCTCAGG | Leukodystrophy, hypomyelinating, 2 |
| 587777507 | NM_022552.4(DNMT3A):c.1943T > C (p.Leu648Pro) | CTCCYGGTGCTGAAGGACTTGGG, GCTCCYGGTGCTGAAGGACTTGG | Tatton-Brown-rahman syndrome |
| 587777557 | NM_018400.3(SCN3B):c.482T > C (p.Met161Thr) | AATCAYGATGTACATCCTTCTGG | Atrial fibrillation, familial, 16 |
| 587777569 | NM_001030001.2(RPS29):c.149T > C (p.Ile50Thr) | GATAYCGGTTCATTAAGGTAGG | Diamond-Blackfan anemia 13 |
| 587777657 | NM_153334.6(SCARF2):c.190T > C (p.Cys64Arg) | CCACGYGCTGCGCTGCTGAGG | Marden Walker like syndrome |
| 587777689 | NM_005726.5(TSFM):c.57 + 4A > G | ACTTCYCACCGGGTAGCTCCCGG | Combined oxidative phosphorylation deficiency 3 |
| 796052005 | NM_000255.3(MUT):c.329A > G (p.Tyr110Cys) | GCAYACTGGCGGATGGTCCAGGG, AGCAYACTGGCGGATGGTCCAGG | not provided |
| 587777809 | NM_144596.3(TTC8):c.115-2A > G | GTTCCYGGAAAGCATTAAGAAGG | Retinitis pigmentosa 51 |
| 587777878 | NM_000166.5(GJB1):c.580A > G (p.Met194Val) | TAGCAYGAAGACGGTGAAGACGG | X-linked hereditary motor and sensory neuropathy |
| 74315420 | NM_001029871.3(RSPO4):c.194A > G (p.Gln65Arg) | CGTACYGGCGGATGCCTTCCCGG | Anonychia |
| 180177219 | NM_000030.2(AGCT):c.424-2A > G (p.Gly_142Gln145del) | AGGCCCYGAGGAAGCAGGGACGG | Primary hyperoxaluria, type I |
| 367610201 | NM_002693.2(POLG):c.1808T > C (p.Met603Thr) | CTCAYGGCACTTACCTGGGATGG | not provided |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 180177319 | NM_012203.1(GRHPR):c.84-2A > G | TCACAGCYGCGGGAAAGGAGG | Primary hyperoxaluria, type II |
| 796052068 | NM_000030.2(AGXT):c.777-2A > G | GGTACCYGGAAGACACGAGGGGG, TGGTACCYGGAAGACACGAGGGG | Primary hyperoxaluria, type I |
| 61754010 | NM_000552.3(VWF):c.1583A > G (p.Asn528Ser) | TGCCAYTGTAATTCCCACACAGG | von Willebrand disease, type 2a |
| 587778866 | NM_000321.2(RB1):c.1927A > G (p.Lys643Glu) | ATTYCAATGGCTTCTGGGTCTGG | Retinoblastoma |
| 74435397 | NM_006331.7(EMG1):c.257A > G (p.Asp86Gly) | ATAYCTGGCCCGCTTCCCCAGG | Bowen-Conradi syndrome |
| 796052527 | NM_000156.5(GAMT):c.1A > G (p.MetIVal) | CGCTCAYGCTGCAGGCTGGACGG | not provided |
| 796052637 | NM_172107.2(KCNQ2):c.848A > G (p.Lys283Arg) | GTACYTGTCCCGTAGCCAATGG | not provided |
| 724159963 | NM_032228.5(FAR1):c.1094A > G (p.Asp365Gly) | GATAYCATACAGGAATGCTGGGG, AGATAYCATACAGGAATGCTGG, TAGATAYCATACAGGAATGCTGG | Peroxisomal fatty acyl-coa reductase 1 disorder |
| 587779722 | NM_000090.3(COL3A1):c.1762-2A > G (p.Gly588_Gln605del) | CACCCYAAAGAAGAAGTGGTCGG | Ehlers-Danlos syndrome, type 4 |
| 118192102 | m.8296A > G | TTTACAGYGGGCTCTAGAGGGGG | Diabetes-deafness syndrome maternally transmitted |
| 727502787 | NM_001077494.3(NFKB2):c.2594A > G (p.Asp865Gly) | CTGYCTTCCTTCACCTCTGCTGG | Common variable immunodeficiency 10 |
| 727503036 | NM_000117.2(EMD):c.266-2A > G | AGCCYTGGGAAGGGGGGCAGCGG | Emery-Dreifuss muscular dystrophy 1, X-linked |
| 690016544 | NM_005861.3(STUB1):c.194A > G (p.Asn65Ser) | GGCCCCGYTGGTGTAATACACGG | Spinocerebellar ataxia, autosomal recessive 16 |
| 690016554 | NM_005211.3(CSF1R):c.2655-2A > G | GTATCYGGGAGATAGGACAGAGG | Hereditary diffuse leukoencephalopathy with spheroids |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 118192185 | NM_172107.2(KCNQ2):c.1A > G (p.Met1Val) | GCACCAYGGTGCCTGGCGGGAGG | Benign familial neonatal seizures 1 |
| 121917869 | NM_012064.3(MIP):c.401A > G (p.Glu134Gly) | AGATCYCCACTGTGGTTGCCTGG | Cataract 15, multiple types |
| 121918014 | NM_000478.4(ALPL):c.1250A > G (p.Asn417Ser) | AGGCCCAYTGCCATACAGGATGG | Infantile hypophosphatasia |
| 121918036 | NM_000174.4(GP9):c.110A > G (p.Asp37Gly) | GCAGYCCACCACAGCCCCATGG | Bernard-Soulier syndrome type C |
| 121918089 | NM_000371.3(TTR):c.379A > G (p.Ile127Val) | CGGCAAYGGTGTAGCGCGGGGG, GCGGCAAYGGTGTAGCGCGGGGG | Amylo dogen c transthyretin amyloidosis |
| 121918121 | NM_000823.3(GHRHR):c.985A > G (p.Lys329Glu) | CGACTYGGAGAGACGCCTGCAGG | Isolated growth hormone deficiency type 1B |
| 121918333 | NM_015335.4(MED13L):c.6068A > G (p.Asp2023Gly) | ATATCAYCTAGAGGAAGGGGG, CATATCAYCTAGAGGGAAGGGGG | Transposition of great arteries |
| 121918605 | NM_001035.2(RYR2):c.12602A > G (p.Gln4201Arg) | CGCCAGYGCATTTCAAAGATGG | Catecholaminergic polymorphic ventricular tachycardia |
| 587781262 | NM_002764.3(PRPS1):c.343A > G (p.Met115Val) | TAGCAYATTTGCAACAAGCTTGG | Charcot-Marie-Tooth disease, X-linked recessive, type 5, Deafness, high-frequency sensorineural, X-linked |
| 121918608 | NM_001161766.1(AHCY):c.344A > G (p.Tyr115Cys) | GCGGGYACTTGGTGTGATGAGG | Hypermethioninemia with s-adenosylhomocysteine hydrolase deficiency |
| 121918613 | NM_000702.3(ATP1A2):c.1033A > G (p.Thr345Ala) | CTGYCAGGGTCAGGCACACCTGG | Familial hemiplegic migraine type 2 |
| 587781339 | NM_000535.5(PMS2):c.904-2A > G | GCAGACCYGCACAAAATACAAGG | Hereditary cancer-predisposing syndrome |
| 121918691 | NM_001128177.1(THRB):c.1324A > G (p.Met442Val) | CTTCAYGTGCAGGAAGCGGCTGG | Thyroid hormone resistance, generalized, autosomal dominant |
| 121918692 | NM_001128177.1(THRB):c.1327A > G (p.Lys443Glu) | CCACCTYCATGTGCAGGAAGCGG | Thyroid hormone resistance, generalized, autosomal dominant |

TABLE 1-continued

List of 911 base-editable gene variants associated with human disease with an NGG PAM (SEQ ID NOs: 747 to 1868 appear from top to bottom below, respectively). The "Y" in the protospacer and PAM sequences indicates the base to be edited, e.g., C. (SEQ ID NOs: 747 to 1868 appear from top to bottom below, respectively)

| dbSNP # | Genotype | Protospacer and PAM sequence(s) | Associated uenetic disease |
|---|---|---|---|
| 727504333 | NM_000256.3(MYBPC3):c.2906-2A > G | CCGTTCYGTGGGTATAGAGTGGG, GCCGTTCYGTGGGTATAGAGTGG | Familial hypertrophic cardiomyopathy 4 |
| 730880805 | NM_006204.3(PDE6C):c.1483-2A > G | CTTTCYGTTGAAATAAGGATGGG, TCTTTCYGTTGAAATAAGGATGG | Achromatopsia 5 |
| 281860296 | NM_000551.3(VHL):c.586A > T (p.Lys196Ter) | GGTCTTYCTGCACATTTGGGTGG | Von Hippel-Lindau syndrome |
| 730880444 | NM_000169.2(GLA):c.370-2A > G | GTGAACCYGAAATGAGAGGAGG | not provided |
| 756228339 | NM_000256.3(MYBPC3):c.1227-2A > G | GTACCYGGGTGGGGGCCCGCAGGG, TGTACCYGGGTGGGGGCCCGCAGG | Familial hypertrophic cardiomyopathy 4, Cardiomyopathy |
| 267606643 | NM_013411.4(AK2):c.494A > G (p.Asp165Gly) | TCAYCTTTCATGGGCTCTTTTGG | Reticular dysgenesis |
| 267606705 | NM_005188.3(CBL):c.1144A > G (p.Lys382Glu) | TATTTYACATAGTTGGAATGTGG | Noonan syndrome-like disorder with or without juvenile myelomonocytic leukemia |
| 62642934 | NM_000277.1(PAH):c.916A > G (p.Ile306Val) | GGCCAAYTTCCTGTAATTGGGGG, AGGCCAAYTTCCTGTAATTGGGG | Phenylketonuria, Hyperphenylalanem a non-pku |
| 267606782 | NM_000117.2(EMD):c.1A > G (p.MetlVal) | TCCAYGGCGGGTGCGGGCTCAGG | Emery-Dreifuss muscular dystrophy, X-linked |
| 267606820 | NM_014053.3(FlVCR1):c.361A > G (p.Asn121Asp) | AGGGCGTYGACCAGCGAGTACAGG | Posterior column ataxia with retinitis pigmentosa |

In some embodiments, any of the base editors provided herein may be used to treat a disease or disorder. For example, any base editors provided herein may be used to correct one or more mutations associated with any of the diseases or disorders provided herein. Exemplary diseases or disorders that may be treated include, without limitation, 3-Methylglutaconic aciduria type 2, 46,XY gonadal dysgenesis, 4-Alpha-hydroxyphenylpyruvate hydroxylase deficiency, 6-pyruvoyl-tetrahydropterin synthase deficiency, achromatopsia, Acid-labile subunit deficiency, Acrodysostosis, acroerythrokeratoderma, ACTH resistance, ACTH-independent macronodular adrenal hyperplasia, Activated PI3K-delta syndrome, Acute intermittent porphyria, Acute myeloid leukemia, Adams-Oliver syndrome 1/5/6, Adenylosuccinate lyase deficiency, Adrenoleukodystrophy, Adult neuronal ceroid lipofuscinosis, Adult onset ataxia with oculomotor apraxia, Advanced sleep phase syndrome, Age-related macular degeneration, Alagille syndrome, Alexander disease, Allan-Herndon-Dudley syndrome, Alport syndrome, X-linked recessive, Alternating hemiplegia of childhood, Alveolar capillary dysplasia with misalignment of pulmonary veins, Amelogenesis imperfecta, Amyloidogenic transthyretin amyloidosis, Amyotrophic lateral sclerosis, Anemia (nonspherocytic hemolytic, due to G6PD deficiency), Anemia (sideroblastic, pyridoxine-refractory, autosomal recessive), Anonychia, Antithrombin III deficiency, Aortic aneurysm, Aplastic anemia, Apolipoprotein C2 deficiency, Apparent mineralocorticoid excess, Aromatase deficiency, Arrhythmogenic right ventricular cardiomyopathy, Familial hypertrophic cardiomyopathy, Hypertrophic cardiomyopathy, Arthrogryposis multiplex congenital, Aspartylglycosaminuria, Asphyxiating thoracic dystrophy, Ataxia with vitamin E deficiency, Ataxia (spastic), Atrial fibrillation, Atrial septal defect, atypical hemolytic-uremic syndrome, autosomal dominant CD11C+/CD1C+ dendritic cell deficiency, Autosomal dominant progressive external ophthalmoplegia with mitochondrial DNA deletions, Baraitser-Winter syndrome, Bartter syndrome, Basa ganglia calcification, Beckwith-Wiedemann syndrome, Benign familial neonatal seizures, Benign scapuloperoneal muscular dystrophy, Bernard Soulier syndrome, Beta thalassemia intermedia, Beta-D-mannosidosis, Bietti crystalline corneoretinal dystrophy, Bile acid malabsorption, Biotinidase deficiency, Borjeson-Forssman-Lehmann syndrome, Boucher Neuhauser syndrome, Bowen-Conradi syndrome, Brachydactyly, Brown-Vialetto-Van laere syndrome, Brugada syndrome, Cardiac arrhythmia, Cardiofaciocutaneous syndrome, Cardiomyopathy, Carnevale syndrome, Carnitine palmitoyltransferase II deficiency, Carpenter syndrome, Cataract, Catecholaminergic polymorphic ventricular tachycardia, Central core disease, Centromeric instability of chromosomes 1,9 and 16 and immunodeficiency, Cerebral autosomal dominant arteriopathy, Cerebro-oculo-facio-skeletal syndrome, Ceroid lipofuscinosis, Charcot-Marie-Tooth disease, Cholestanol storage disease, Chondrocalcinosis, Chondrodysplasia, Chronic progressive multiple sclerosis, Coenzyme Q10 deficiency, Cohen syndrome, Combined deficiency of factor V and factor VIII, Combined immunodeficiency, Combined oxidative phosphorylation deficiency, Combined partial 17-alpha-hydroxylase/17,20-lyase deficiency, Complement factor d deficiency, Complete combined 17-alpha-hydroxylase/17,20-lyase deficiency, Cone-rod dystrophy, Congenital contractural arachnodactyly, Congenital disorder of glycosylation, Congenital lipomatous overgrowth, Neoplasm of ovary, PIK3CA Related Overgrowth Spectrum, Congenital long QT syndrome, Congenital muscular dystrophy, Congenital muscular hypertrophy-cerebral syndrome, Congenital myasthenic syndrome, Congenital myopathy with fiber type disproportion, Eichsfeld type congenital muscular dystrophy, Congenital stationary night blindness, Corneal dystrophy, Cornelia de Lange syndrome, Craniometaphyseal dysplasia, Crigler Najjar syndrome, Crouzon syndrome, Cutis laxa with osteodystrophy, Cyanosis, Cystic fibrosis, Cystinosis, Cytochrome-c oxidase deficiency, Mitochondrial complex I deficiency, D-2-hydroxyglutaric aciduria, Danon disease, Deafness with labyrinthine aplasia microtia and microdontia (LAMM), Deafness, Deficiency of acetyl-CoA acetyltransferase, Deficiency of ferroxidase, Deficiency of UDPglucose-hexose-1-phosphate uridylyltransferase, Dejerine-Sottas disease, Desbuquois syndrome, DFNA, Diabetes mellitus type 2, Diabetes-deafness syndrome, Diamond-Blackfan anemia, Diastrophic dysplasia, Dihydropteridine reductase deficiency, Dihydropyrimidinase deficiency, Dilated cardiomyopathy, Disseminated atypical mycobacterial infection, Distal arthrogryposis, Distal hereditary motor neuronopathy, Donnai Barrow syndrome, Duchenne muscular dystrophy, Becker muscular dystrophy, Dyschromatosis universalis hereditaria, Dyskeratosis congenital, Dystonia, Early infantile epileptic encephalopathy, Ehlers-Danlos syndrome, Eichsfeld type congenital muscular dystrophy, Emery-Dreifuss muscular dystrophy, Enamel-renal syndrome, Epidermolysis bullosa dystrophica inversa, Epidermolysis bullosa herpetiformis, Epilepsy, Episodic ataxia, Erythrokeratodermia variabilis, Erythropoietic protoporphyria, Exercise intolerance, Exudative vitreoretinopathy, Fabry disease, Factor V deficiency, Factor VII deficiency, Factor xiii deficiency, Familial adenomatous polyposis, breast cancer, ovarian cancer, cold urticarial, chronic infantile neurological, cutaneous and articular syndrome, hemiplegic migraine, hypercholesterolemia, hypertrophic cardiomyopathy, hypoalphalipoproteinemia, hypokalemia-hypomagnesemia, juvenile gout, hyperlipoproteinemia, visceral amyloidosis, hypophosphatemic vitamin D refractory rickets, FG syndrome, Fibrosis of extraocular muscles, Finnish congenital nephrotic syndrome, focal epilepsy, Focal segmental glomerulosclerosis, Frontonasal dysplasia, Frontotemporal dementia, Fructose-biphosphatase deficiency, Gamstorp-Wohlfart syndrome, Ganglioside sialidase deficiency, GATA-1-related thrombocytopenia, Gaucher disease, Giant axonal neuropathy, Glanzmann thrombasthenia, Glomerulocystic kidney disease, Glomerulopathy, Glucocorticoid resistance, Glucose-6-phosphate transport defect, Glutaric aciduria, Glycogen storage disease, Gorlin syndrome, Holoprosencephaly, GRACILE syndrome, Haemorrhagic telangiectasia, Hemochromatosis, Hemoglobin H disease, Hemolytic anemia, Hemophagocytic lymphohistiocytosis, Carcinoma of colon, Myhre syndrome, leukoencephalopathy, Hereditary factor IX deficiency disease, Hereditary factor VIII deficiency disease, Hereditary factor XI deficiency disease, Hereditary fructosuria, Hereditary Nonpolyposis Colorectal Neoplasm, Hereditary pancreatitis, Hereditary pyropoikilocytosis, Elliptocytosis, Heterotaxy, Heterotopia, Histiocytic medullary reticulosis, Histiocytosis-lymphadenopathy plus syndrome, HNSHA due to aldolase A deficiency, Holocarboxylase synthetase deficiency, Homocysteinemia, Howel-Evans syndrome, Hydatidiform mole, Hypercalciuric hypercalcemia, Hyperimmunoglobulin D, Mevalonic aciduria, Hyperinsulinemic hypoglycemia, Hyperkalemic Periodic Paralysis, Paramyotonia congenita of von Eulenburg, Hyperlipoproteinemia, Hypermanganesemia, Hypermethioninemia, Hyperphosphatasemia, Hypertension, hypomagnesemia, Hypobetalipoproteinemia, Hypocalcemia, Hypogonadotropic hypogonadism, Hypogonadotropic hypogonadism, Hypohidrotic ectodermal dysplasia, Hyper-IgM immunodeficiency, Hypohidrotic X-linked ectodermal dysplasia, Hypomagnesemia, Hypoparathyroidism, Idiopathic fibrosing alveolitis, Immunodeficiency, Immunoglobulin A deficiency, Infantile hypophosphatasia, Infantile Parkinsonism-dystonia, Insulin-dependent diabetes mellitus, Intermediate maple syrup urine disease, Ischiopatellar dysplasia, Islet cell hyperplasia, Isolated growth hormone deficiency, Isolated lutropin deficiency, Isovaleric acidemia, Joubert syndrome, Juvenile polyposis syndrome, Juvenile retinoschisis, Kallmann syndrome, Kartagener syndrome, Kugelberg-Welander disease, Lattice corneal dystrophy, Leber congenital amaurosis, Leber optic atrophy, Left ventricular noncompaction, Leigh disease, Mitochondrial complex I deficiency, Leprechaunism syndrome, Arthrogryposis, Anterior horn cell disease, Leukocyte adhesion deficiency, Leukodystrophy, Leukoencephalopathy, Ovarioleukodystrophy, L-ferritin deficiency, Li-Fraumeni syndrome, Limb-girdle muscular dystrophy-dystroglycanopathy, Loeys-Dietz syndrome, Long QT syndrome, Macrocephaly/autism syndrome, Macular corneal dystrophy, Macular dystrophy, Malignant hyperthermia susceptibility, Malignant tumor of prostate, Maple syrup urine disease, Marden Walker like syndrome, Marfan syndrome, Marie Unna hereditary hypotrichosis, Mast cell disease, Meconium ileus, Medium-chain acyl-coenzyme A dehydrogenase deficiency, Melnick-Fraser syndrome, Mental retardation, Merosin deficient congenital muscular dystrophy, Mesothelioma, Metachromatic leukodystrophy, Metaphyseal chondrodysplasia, Methemoglobinemia, methylmalonic aciduria, homocystinuria, Microcephaly, chorioretinopathy, lymphedema, Microphthalmia, Mild non-PKU hyperphenylalanemia, Mitchell-Riley syndrome, mitochondrial 3-hydroxy-3-methylglutaryl-CoA synthase deficiency, Mitochondrial complex I deficiency, Mitochondrial complex III deficiency, Mitochondrial myopathy, Mucolipidosis III, Mucopolysaccharidosis, Multiple sulfatase deficiency, Myasthenic syndrome, Mycobacterium tuberculosis, Myeloperoxidase deficiency, Myhre syndrome, Myoclonic epilepsy, Myofibrillar myopathy, Myoglobinuria, Myopathy, Myopia, Myotonia congenital, Navajo neurohepatopathy, Nemaline myopathy, Neoplasm of stomach, Nephrogenic diabetes insipidus, Nephronophthisis, Nephrotic syndrome, Neurofibromatosis, Neutral lipid storage disease, Niemann-Pick disease, Non-ketotic hyperglycinemia, Noonan syndrome, Noonan syndrome-like disorder, Norum disease, Macular degeneration, N-terminal acetyltransferase deficiency, Oculocutaneous albinism, Oculodentodigital dysplasia, Ohdo syndrome, Optic nerve aplasia, Ornithine carbamoyltransferase deficiency, Orofaciodigital syndrome, Osteogenesis imperfecta, Osteopetrosis, Ovarian dysgenesis, Pachyonychia, Palmoplantar keratoderma, nonepidermolytic, Papillon-Lef\xc3\xa8vre syndrome, Haim-Munk syndrome, Periodontitis, Peeling skin syndrome, Pendred syndrome, Peroxisomal fatty acylcoa reductase 1 disorder, Peroxisome biogenesis disorder, Pfeiffer syndrome, Phenylketonuria, Phenylketonuria, Hyperphenylalaninemia, non-PKU, Pituitary hormone deficiency, Pityriasis rubra pilaris, Polyarteritis nodosa, Polycystic kidney disease, Polycystic lipomembranous osteodysplasia, Polymicrogyria, Pontocerebellar hypoplasia, Porokeratosis, Posterior column ataxia, Primary erythromelalgia, hyperoxaluria, Progressive familial intrahepatic cholestasis, Progressive pseudorheumatoid dysplasia, Propionic acidemia, Pseudohermaphroditism, Pseudohypoaldosteronism, Pseudoxanthoma elasticum-like disorder, Purine-nucleoside phosphorylase deficiency, Pyridoxal 5-phosphate-dependent epilepsy, Renal dysplasia, retinal pigmentary dystrophy, cerebellar ataxia, skeletal dysplasia, Reticular dysgenesis, Retinitis pigmentosa, Usher syndrome, Retinoblastoma, Retinopathy, RRM2B-related mitochondrial disease, Rubinstein-Taybi syndrome, Schnyder crystalline corneal dystrophy, Sebaceous tumor, Severe congenital neutropenia, Severe myoclonic epilepsy in infancy, Severe X-linked myotubular myopathy, onychodysplasia, facial dysmorphism, hypotrichosis, Short-rib thoracic dysplasia, Sialic acid storage disease, Sialidosis, Sideroblastic anemia, Small fiber neuropathy, Smith-Magenis syndrome, Sorsby fundus dystrophy, Spastic ataxia, Spastic paraplegia, Spermatogenic failure, Spherocytosis, Sphingomyelin/cholesterol lipidosis, Spinocerebellar ataxia, Split-hand/foot malformation, Spondyloepimetaphyseal dysplasia, Platyspondylic lethal skeletal dysplasia, Squamous cell carcinoma of the head and neck, Stargardt disease, Sucrase-isomaltase deficiency, Sudden infant death syndrome, Supravalvar aortic stenosis, Surfactant metabolism dysfunction, Tangier disease, Tatton-Brown-rahman syndrome, Thoracic aortic aneurysms and aortic dissections, Thrombophilia, Thyroid hormone resistance, TNF receptor-associated periodic fever syndrome (TRAPS), Tooth agenesis, Torsades de pointes, Transposition of great arteries, Treacher Collins syndrome, Tuberous sclerosis syndrome, Tyrosinase-negative oculocutaneous albinism, Tyrosinase-positive oculocutaneous albinism, Tyrosinemia, UDPglucose-4-epimerase deficiency, Ullrich congenital muscular dystrophy, Bethlem myopathy Usher syndrome, UV-sensitive syndrome, Van der Woude syndrome, popliteal pterygium syndrome, Very long chain acyl-CoA dehydrogenase deficiency, Vesicoureteral reflux, Vitreoretinochoroidopathy, Von Hippel-Lindau syndrome, von Willebrand disease, Waardenburg syndrome, Warsaw breakage syndrome, WFS1-Related Disorders, Wilson disease, Xeroderma pigmentosum, X-linked agammaglobulinemia, X-linked hereditary motor and sensory neuropathy, X-linked severe combined immunodeficiency, and Zellweger syndrome.

The development of nucleobase editing advances both the scope and effectiveness of genome editing. The nucleobase editors described here offer researchers a choice of editing with virtually no indel formation (NBE2), or more efficient editing with a low frequency (here, typically ≤1%) of indel formation (NBE3). That the product of base editing is, by definition, no longer a substrate likely contributes to editing efficiency by preventing subsequent product transformation, which can hamper traditional Cas9 applications. By removing the reliance on double-stranded DNA cleavage and stochastic DNA repair processes that vary greatly by cell state and cell type, nucleobase editing has the potential to expand the type of genome modifications that can be cleanly installed, the efficiency of these modifications, and the type of cells that are amenable to editing. It is likely that recent engineered Cas9 variants[69,70,82] or delivery methods[71] with improved DNA specificity, as well as Cas9 variants with altered PAM specificities,[72] can be integrated into this strategy to provide additional nucleobase editors with improved DNA specificity or that can target an even wider range of disease-associated mutations. These findings also suggest that engineering additional fusions of dCas9 with enzymes that catalyze additional nucleobase transformations will increase the fraction of the possible DNA base changes that can be made through nucleobase editing. These results also suggest architectures for the fusion of other DNA-modifying enzymes, including methylases and demathylases, that mau enable additional types of programmable genome and epigenome base editing.

Materials and Methods

Cloning. DNA sequences of all constructs and primers used in this paper are listed in the Supplementary Sequences. Plasmids containing genes encoding NBE1, NBE2, and NBE3 will be available from Addgene. PCR was performed using VeraSeq ULtra DNA polymerase (Enzymatics), or Q5 Hot Start High-Fidelity DNA Polymerase (New England Biolabs). NBE plasmids were constructed using USER cloning (New England Biolabs). Deaminase genes were synthesized as gBlocks Gene Fragments (Integrated DNA Technologies), and Cas9 genes were obtained from previously reported plasmids.[18] Deaminase and fusion genes were cloned into pCMV (mammalian codon-optimized) or pET28b (E. coli codon-optimized) backbones. sgRNA expression plasmids were constructed using site-directed mutagenesis. Briefly, the primers listed in the Supplementary Sequences were 5' phosphorylated using T4 Polynucleotide Kinase (New England Biolabs) according to the manufacturer's instructions. Next, PCR was performed using Q5 Hot Start High-Fidelity Polymerase (New England Biolabs) with the phosphorylated primers and the plasmid pFYF1320 (EGFP sgRNA expression plasmid) as a template according to the manufacturer's instructions. PCR products were incubated with DpnI (20 U, New England Biolabs) at 37° C. for 1 h, purified on a QIAprep spin column (Qiagen), and ligated using QuickLigase (New England Biolabs) according to the manufacturer's instructions. DNA vector amplification was carried out using Mach1 competent cells (ThermoFisher Scientific).

In vitro deaminase assay on ssDNA. Sequences of all ssDNA substrates are listed in the Supplementary Sequences. All Cy3-labelled substrates were obtained from Integrated DNA Technologies (IDT). Deaminases were expressed in vitro using the TNT T7 Quick Coupled Transcription/Translation Kit (Promega) according to the manufacturer's instructions using 1 µg of plasmid. Following protein expression, 5 µL of lysate was combined with 35 µL of ssDNA (1.8 µM) and USER enzyme (1 unit) in CutSmart buffer (New England Biolabs) (50 mM potassium acetate, 29 mM Trisacetate, 10 mM magnesium acetate, 100 ug/mL BSA, pH 7.9) and incubated at 37° C. for 2 h. Cleaved U-containing substrates were resolved from full-length unmodified substrates on a 10% TBE-urea gel (Bio-Rad).

Expression and purification of His$_6$-rAPOBEC1-linker-dCas9 fusions. E. Coli BL21 STAR (DE3)-competent cells (ThermoFisher Scientific) were transformed with plasmids encoding pET28b-His$_6$-rAPOBEC-linker-dCas9 with GGS, (GGS)$_3$, (SEQ ID NO: 596) XTEN, or (GGS)$_7$ (SEQ ID NO: 597) linkers. The resulting expression strains were grown overnight in Luria-Bertani (LB) broth containing 100 µg/mL of kanamycin at 37° C. The cells were diluted 1:100 into the same growth medium and grown at 37° C. to OD$_{600}$=~0.6. The culture was cooled to 4° C. over a period of 2 h, and isopropyl-β-D-1-thiogalactopyranoside (IPTG) was added at 0.5 mM to induce protein expression. After ~16 h, the cells were collected by centrifugation at 4,000 g and resuspended in lysis buffer (50 mM tris(hydroxymethyl)-aminomethane (Tris)-HCl, pH 7.0, 1 M NaCl, 20% glycerol, 10 mM tris(2-carboxyethyl)phosphine (TCEP, Soltec Ventures)). The cells were lysed by sonication (20 s pulse-on, 20 s pulse-off for 8 min total at 6 W output) and the lysate supernatant was isolated following centrifugation at 25,000 g for 15 min. The lysate was incubated with His-Pur nickel-nitriloacetic acid (nickel-NTA) resin (ThermoFisher Scientific) at 4° C. for 1 h to capture the His-tagged fusion protein. The resin was transferred to a column and washed with 40 mL of lysis buffer. The His-tagged fusion protein was eluted in lysis buffer supplemented with 285 mM imidazole, and concentrated by ultrafiltration (Amicon-Millipore, 100-kDa molecular weight cut-off) to 1 mL total volume. The protein was diluted to 20 mL in low-salt purification buffer containing 50 mM tris(hydroxymethyl)-aminomethane (Tris)-HCl, pH 7.0, 0.1 M NaCl, 20% glycerol, 10 mM TCEP and loaded onto SP Sepharose Fast Flow resin (GE Life Sciences). The resin was washed with 40 mL of this low-salt buffer, and the protein eluted with 5 mL of activity buffer containing 50 mM tris(hydroxymethyl)-aminomethane (Tris)-HCl, pH 7.0, 0.5 M NaCl, 20% glycerol, 10 mM TCEP. The eluted proteins were quantified on a SDSPAGE gel.

In vitro transcription of sgRNAs. Linear DNA fragments containing the T7 promoter followed by the 20-bp sgRNA target sequence were transcribed in vitro using the primers listed in the Supplementary Sequences with the TranscriptAid T7 High Yield Transcription Kit (ThermoFisher Scientific) according to the manufacturer's instructions. sgRNA products were purified using the MEGAclear Kit (ThermoFisher Scientific) according to the manufacturer's instructions and quantified by UV absorbance.

Preparation of Cy3-conjugated dsDNA substrates. Sequences of 80-nucleotide unlabeled strands are listed in the Supplementary Sequences and were ordered as PAGE-purified oligonucleotides from IDT. The 25-nt Cy3-labeled primer listed in the Supplementary Sequences is complementary to the 3' end of each 80-nt substrate. This primer was ordered as an HPLC-purified oligonucleotide from IDT. To generate the Cy3-labeled dsDNA substrates, the 80-nt strands (5 µL of a 100 µM solution) were combined with the Cy3-labeled primer (5 µL of a 100 µM solution) in NEBuffer 2 (38.25 µL of a 50 mM NaCl, 10 mMTris-HCl, 10 mM MgCl$_2$, 1 mM DTT, pH 7.9 solution, New England Biolabs) with dNTPs (0.75 µL of a 100 mM solution) and heated to 95° C. for 5 min, followed by a gradual cooling to 45° C. at a rate of 0.1° C./s. After this annealing period, Klenow exo$^-$ (5 U, New England Biolabs) was added and the reaction was incubated at 37° C. for 1 h. The solution was diluted with Buffer PB (250 Qiagen) and isopropanol (50 µL) and purified on a QIAprep spin column (Qiagen), eluting with 50 µL of Tris buffer.

Deaminase assay on dsDNA. The purified fusion protein (20 µL of 1.9 µM in activity buffer) was combined with 1 equivalent of appropriate sgRNA and incubated at ambient temperature for 5 min. The Cy3-labeled dsDNA substrate was added to final concentration of 125 nM and the resulting solution was incubated at 37° C. for 2 h. The dsDNA was separated from the fusion by the addition of Buffer PB (100 µL, Qiagen) and isopropanol (25 µL) and purified on a EconoSpin micro spin column (Epoch Life Science), eluting with 20 µL of CutSmart buffer (New England Biolabs). USER enzyme (1 U, New England Biolabs) was added to the purified, edited dsDNA and incubated at 37° C. for 1 h. The Cy3-labeled strand was fully denatured from its complement by combining 5 µL of the reaction solution with 15 µL of a DMSO-based loading buffer (5 mM Tris, 0.5 mM EDTA, 12.5% glycerol, 0.02% bromophenol blue, 0.02% xylene cyan, 80% DMSO). The full-length C-containing substrate was separated from any cleaved, U-containing edited substrates on a 10% TBE-urea gel (Bio-Rad) and imaged on a GE Amersham Typhoon imager.

Preparation of in vitro-edited dsDNA for high-throughput sequencing (HTS). The oligonucleotides listed in the Supplementary Sequences were obtained from IDT. Complementary sequences were combined (5 µL of a 100 µM solution) in Tris buffer and annealed by heating to 95°

C. for 5 min, followed by a gradual cooling to 45° C. at a rate of 0.1° C./s to generate 60-bp dsDNA substrates. Purified fusion protein (20 µL of 1.9 µM in activity buffer) was combined with 1 equivalent of appropriate sgRNA and incubated at ambient temperature for 5 min. The 60-mer dsDNA substrate was added to final concentration of 125 nM and the resulting solution was incubated at 37° C. for 2 h. The dsDNA was separated from the fusion by the addition of Buffer PB (100 µL, Qiagen) and isopropanol (25 µL) and purified on a EconoSpin micro spin column (Epoch Life Science), eluting with 20 µL of Tris buffer. The resulting edited DNA (1 µL was used as a template) was amplified by PCR using the HTS primer pairs specified in the Supplementary Sequences and VeraSeq Ultra (Enzymatics) according to the manufacturer's instructions with 13 cycles of amplification. PCR reaction products were purified using RapidTips (Diffinity Genomics), and the purified DNA was amplified by PCR with primers containing sequencing adapters, purified, and sequenced on a MiSeq high-throughput DNA sequencer (Illumina) as previously described.[73]

Cell culture. HEK293T (ATCC CRL-3216), U2OS (ATCC-HTB-96) and ST486 cells (ATCC) were maintained in Dulbecco's Modified Eagle's Medium plus GlutaMax (ThermoFisher) supplemented with 10% (v/v) fetal bovine serum (FBS) and penicillin/streptomycin (1×, Amresco), at 37° C. with 5% $CO_2$. HCC1954 cells (ATCC CRL-2338) were maintained in RPMI-1640 medium (ThermoFisher Scientific) supplemented as described above. Immortalized rat astrocytes containing the ApoE4 isoform of the APOE gene (Taconic Biosciences) were cultured in Dulbecco's Modified Eagle's Medium plus GlutaMax (ThermoFisher Scientific) supplemented with 10% (v/v) fetal bovine serum (FBS) and 200 m/mL Geneticin (ThermoFisher Scientific).

Transfections. HEK293T cells were seeded on 48-well collagen-coated BioCoat plates (Corning) and transfected at approximately 85% confluency. Briefly, 750 ng of NBE and 250 ng of sgRNA expression plasmids were transfected using 1.5 µl of Lipofectamine 2000 (ThermoFisher Scientific) per well according to the manufacturer's protocol. Astrocytes, U2OS, HCC1954, HEK293T and ST486 cells were transfected using appropriate AMAXA NUCLEOFECTOR™ II programs according to manufacturer's instructions. 40 ng of infrared RFP (Addgene plasmid 45457)[74] was added to the nucleofection solution to assess nucleofection efficiencies in these cell lines. For astrocytes, U2OS, and ST486 cells, nucleofection efficiencies were 25%, 74%, and 92%, respectively. For HCC1954 cells, nucleofection efficiency was <10%. Therefore, following trypsinization, the HCC1954 cells were filtered through a 40 micron strainer (Fisher Scientific), and the nucleofected HCC1954 cells were collected on a Beckman Coulter MoFlo XDP Cell Sorter using the iRFP signal (abs 643 nm, em 670 nm). The other cells were used without enrichment of nucleofected cells.

High-throughput DNA sequencing of genomic DNA samples. Transfected cells were harvested after 3 d and the genomic DNA was isolated using the Agencourt DNAdvance Genomic DNA Isolation Kit (Beckman Coulter) according to the manufacturer's instructions. On-target and off-target genomic regions of interest were amplified by PCR with flanking HTS primer pairs listed in the Supplementary Sequences. PCR amplification was carried out with Phusion high-fidelity DNA polymerase (ThermoFisher) according to the manufacturer's instructions using 5 ng of genomic DNA as a template. Cycle numbers were determined separately for each primer pair as to ensure the reaction was stopped in the linear range of amplification (30, 28, 28, 28, 32, and 32 cycles for EMX1, FANCF, HEK293 site 2, HEK293 site 3, HEK293 site 4, and RNF2 primers, respectively). PCR products were purified using RapidTips (Diffinity Genomics). Purified DNA was amplified by PCR with primers containing sequencing adaptors. The products were gel-purified and quantified using the QUANT-IT™ PicoGreen dsDNA Assay Kit (ThermoFisher) and KAPA Library Quantification Kit-Illumina (KAPA Biosystems). Samples were sequenced on an Illumina MiSeq as previously described.[73]

Data analysis. Sequencing reads were automatically demultiplexed using MiSeq Reporter (Illumina), and individual FASTQ files were analyzed with a custom Matlab script provided in the Supplementary Notes. Each read was pairwise aligned to the appropriate reference sequence using the Smith-Waterman algorithm. Base calls with a Q-score below 31 were replaced with N's and were thus excluded in calculating nucleotide frequencies. This treatment yields an expected MiSeq base-calling error rate of approximately 1 in 1,000. Aligned sequences in which the read and reference sequence contained no gaps were stored in an alignment table from which base frequencies could be tabulated for each locus.

Indel frequencies were quantified with a custom Matlab script shown in the Supplementary Notes using previously described criteria[71]. Sequencing reads were scanned for exact matches to two 10-bp sequences that flank both sides of a window in which indels might occur. If no exact matches were located, the read was excluded from analysis. If the length of this indel window exactly matched the reference sequence the read was classified as not containing an indel. If the indel window was two or more bases longer or shorter than the reference sequence, then the sequencing read was classified as an insertion or deletion, respectively.

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

Supplementary Sequences

Primers used for generating sgRNA transfection plasmids. rev_sgRNA_plasmid was used in all cases. The pFYF1320 plasmid was used as template as noted in Materials and Methods section. SEQ ID NOs: 329-338 appear from top to bottom below, respectively.

```
rev_sgRNA_plasmid
GGTGTTTCGTCCTTTCCACAAG fwd_p53_Y163C
GCTTGCAGATGGCCATGGCGGTTTTAGAGCTAGAAATAGCAAGTTAAAAT
AAGGC fwd_p53_N239D
TGTCACACATGTAGTTGTAGGTTTTAGAGCTAGAAATAGCAAGTTAAAAT
AAGGC fwd_APOE4_C158R
GAAGCGCCTGGCAGTGTACCGTTTTAGAGCTAGAAATAGCAAGTTAAAAT
AAGGC fwd_EMX1
GAGTCCGAGCAGAAGAAGAAGTTTTAGAGCTAGAAATAGCAAGTTAAAAT
AAGGC
```

-continued

```
fwd_FANCF
GGAATCCCTTCTGCAGCACCGTTTTAGAGCTAGAAATAGCAAGTTAAAAT
AAGGC fwd_HEK293_2
GAACACAAAGCATAGACTGCGTTTTAGAGCTAGAAATAGCAAGTTAAAAT
AAGGC fwd_HEK293_3
GGCCCAGACTGAGCACGTGAGTTTTAGAGCTAGAAATAGCAAGTTAAAAT
AAGGC fwd_HEK293_4
GGCACTGCGGCTGGAGGTGGGTTTTAGAGCTAGAAATAGCAAGTTAAAAT
AAGGC fwd_RNF2
GTCATCTTAGTCATTACCTGGTTTAGAGCTAGAAATAGCAAGTTAAAATA
AGGC
```

Sequences of all ssDNA substrates used in in vitro deaminase assays. SEQ ID NOs: 339-341 appear from top to bottom below, respectively.

```
rAPOBEC1 substrate
Cy3-ATTATTATTATTCCGCGGATTTATTTATTTATTTATTT hAID/pmCDA1 substrate
Cy3-ATTATTATTATTAGCTATTTATTTATTTATTTATTTATTT hAPOBEC3G substrate
Cy3-ATTATTATTATTCCCGGATTTATTTATTATTTATTTATTT
```

Primers used for generating PCR products to serve as substrates for T7 transcription of sgRNAs for gel-based deaminase assay. rev_gRNA_T7 was used in all cases. The pFYF1320 plasmid was used as template as noted in Materials and Methods section. SEQ ID NOs: 342-365 appear from top to bottom below, respectively.

```
rev_sgRNA_T7              AAAAAAAGCACCGACTCGGTG fwd_sgRNA_T7_dsDNA_2      TAATACGACTCACTATAGGCCGCGGATTTATTTATTTAAGTTTTAGAGCTAGAAATAGCA fwd_sgRNA_T7_dsDNA_3      TAATACGACTCACTATAGGTCCGCGGATTTATTTATTTAGTTTTAGAGCTAGAAATAGCA fwd_sgRNA_T7_dsDNA_4      TAATACGACTCACTATAGGTTCCGCGGATTTATTTATTAGTTTTAGAGCTAGAAATAGCA fwd_sgRNA_T7_dsDNA_5      TAATACGACTCACTATAGGATTCCGCGGATTTATTTATTGTTTTAGAGCTAGAAATAGCA fwd_sgRNA_T7_dsDNA_6      TAATACGACTCACTATAGGTATTCCGCGGATTTATTTATGTTTTAGAGCTAGAAATAGCA fwd_sgRNA_T7_dsDNA_7      TAATACGACTCACTATAGGTTATTCCGCGGATTTATTTAGTTTTAGAGCTAGAAATAGCA fwd_sgRNA_T7_dsDNA_8      TAATACGACTCACTATAGGATTATTCCGCGGATTTATTTGTTTTAGAGCTAGAAATAGCA fwd_sgRNA_T7_dsDNA_9      TAATACGACTCACTATAGGTATTATTCCGCGGATTTATTGTTTTAGAGCTAGAAATAGCA fwd_sgRNA_T7_dsDNA_10     TAATACGACTCACTATAGGATTATTATCCGCGGATTTATGTTTTAGAGCTAGAAATAGCA fwd_sgRNA_T7_dsDNA_11     TAATACGACTCACTATAGGTATTATATTCCGCGATTTAGTTTTAGAGCTAGAAATAGCA fwd_sgRNA_T7_dsDNA_12     TAATACGACTCACTATAGGTTATTATATTCCGCGGATTTGTTTTAGAGCTAGAAATAGCA fwd_sgRNA_T7_dsDNA_13     TAATACGACTCACTATAGGATTATTATATTCCGCGGATTGTTTTAGAGCTAGAAATAGCA fwd_sgRNA_T7_dsDNA_14     TAATACGACTCACTATAGGTATTATTATATTCCGCGGATGTTTTAGAGCTAGAAATAGCA fwd_sgRNA_T7_dsDNA_15     TAATACGACTCACTATAGGATTATTATTATTACCGCGGAGTTTTAGAGCTAGAAATAGCA fwd_sgRNA_T7_dsDNA_18     TAATACGACTCACTATAGGATTATTATTATTATTACCGCGTTTTAGAGCTAGAAATAGCA fwd_sgRNA_T7_dsDNA_noC    TAATACGACTCACTATAGGATATTAATTTATTTATTTAAGTTTTAGAGCTAGAAATAGCA fwd_sgRNA_T7_dsDNA_       TAATACGACTCACTATAGGGGAGGACGTGCGCGGCCGCCGTTTTAGAGCTAGAAATAGCA
APOE4_C112R fwd_sgRNA_T7_dsDNA_       TAATACGACTCACTATAGGGAAGCGCCTGGCAGTGTACCGTTTTAGAGCTAGAAATAGCA
APOE4_C156R fwd_sgRNA_T7_dsDNA_       TAATACGACTCACTATAGGCTGTGGCAGTGGCACCAGAAGTTTTAGAGCTAGAAATAGCA
CTNNB1_T41A fwd_sgRNA_T7_dsDNA_       TAATACGACTCACTATAGGCCTCCCGGCCGGCGOTATCCGTTTTAGAGCTAGAAATAGCA
HRAS_Q61R fwd_sgRNA_T7_dsDNA_       TAATACGACTCACTATAGGGCTTGCAGATGGCCATGGCGGTTTTAGAGCTAGAAATAGCA
53_Y163C fwd_sgRNA_T7_dsDNA_       TAATACGACTCACTATAGGACACATGCAGTTGTAGTGGAGTTTTAGAGCTAGAAATAGCA
53_Y236C fwd_sgRNA_T7_dsDNA_       TAATACGACTCACTATAGGTGTCACACATGTAGTTGTAGGTTTTAGAGCTAGAAATAGCA
53_N239D
```

Sequences of 80-nucleotide unlabeled strands and Cy3-labeled universal primer used in gel-based dsDNA deaminase assays. SEQ ID NOs: 366-390 appear from top to bottom below, respectively.

```
Cy3-primer       Cy8-GTAGGTAGTTAGGATGAATGGAAGGTTGGTA dsDNA_2          GTCCATGGATCCAGAGGTCATCCATTAAATAAATAAATCCGCGGGGCTATACCAACCTTCCATTCATCCTAACTACCTAC dsDNA_3          GTCCATGGATCCAGAGGTCATCCATAAATAAATAAATCCGCGGAAGCTATACCAACCTTCCATTCATCCTAACTACCTAC dsDNA_4          GTCCATGGATCCAGAGGTCATCCATAATAAATAAATCCGCGGAAGGCTATACCAACCTTCCATTCATCCTAACTACCTAC dsDNA_5          GTCCATGGATCCAGAGGTCATCCAAATAAATAAATCCGCGGAATGGCTATACCAACCTTCCATTCATCCTAACTACCTAC dsDNA_6          GTCCATGGATCCAGAGGTCATCCAATAAATAAATCCGCGGAATAGGCTATACCAACCTTCCATTCATCCTAACTACCTAC dsDNA_7          GTCCATGGATCCAGAGGTCATCCATAAATAAATCCGCGGAATAAGGCTATACCAACCTTCCATTCATCCTAACTACCTAC dsDNA_8          GTCCATGGATCCAGAGGTCATCCAAAATAAATCCGCGGAATAATGGCTATACCAACCTTCCATTCATCCTAACTACCTAC dsDNA_9          GTCCATGGATCCAGAGGTCATCCAAATAAATCCGCGGAATAATAGGCTATACCAACCTTCCATTCATCCTAACTACCTAC dsDNA_10         GTCCATGGATCCAGAGGTCATCCAATAAATCCGCGGATAATAATGGCTATACCAACCTTCCATTCATCCTAACTACCTAC dsDNA_11         GTCCATGGATCCAGAGGTCATCCATAAATCCGCGGAATATAATAGGCTATACCAACCTTCCATTCATCCTAACTACCTAC dsDNA_12         GTCCATGGATCCAGAGGTCATCCAAAATCCGCGGAATATAATAAGGCTATACCAACCTTCCATTCATCCTAACTACCTAC dsDNA_13         GTCCATGGATCCAGAGGTCATCCAAATCCGCGGAATATAATAATGGCTATACCAACCTTCCATTCATCCTAACTACCTAC dsDNA_14         GTCCATGGATCCAGAGGTCATCCAATCCGCGGAATATAATAATAGGCTATACCAACCTTCCATTCATCCTAACTACCTAC dsDNA_15         GTCCATGGATCCAGAGGTCATCCATCCGCGGTAATAATAATAATGGCTATACCAACCTTCCATTCATCCTAACTACCTAC dsDNA_16         GTCCATGGATCCAGAGGTCATCCAGCGGTAATAATAATAATAATGGCTATACCAACCTTCCATTCATCCTAACTACCTAC dsDNA_noC        GTCCATGGATCCAGAGGTCATCATCCATTAAATAAATAAATTAATATTACTATACCAACCTTCCATTCCTAACTACCTAC DsDNA_8U         5Cy3-GTAGGTAGTTAGGATGAATGGAAGGTTGGTGTAGATTATTATCUGCGGATTTATTGGATGACCTCTGGATCCATGGACAT dsDNA_APCE_      GCACCTCGCCGCGGTACTGCACCAGGCGGCCGCGCACGTCCTCCATGTCTACCAACCTTCCATTCATCCTAACTACCTAC
C112R dsDNA_APOE_      CGGCGCCCTCGCGGGCCCCGGCCTGGTACACTGCCAGGCGCTTCTGCAGTACCAACCTTCCATTCATCCTAACTACCTAC
C158R dsDNA_CTNNB1_    GTCTTACCTGGACTCTGGAATCCATTCTGGTGCCACTGCCACAGCTCCTTACCAACCTTCCATTCATCCTAACTACCTAC
T41A dsDNA_HRAS_      GGAGACGTGCCTGTTGGACATCCTGGATACCGCCGGCCGGGAGGAGTACTACCAACCTTCCATTCATCCTAACTACCTAC
Q61R dsDNA_p53_       ACCCCCGCCCGGCACCCGCGTCCGCGCCATGGCCATCTGCAAGCAGTCATACCAACCTTCCATTCATCCTAACTACCTAC
Y163C dsDNA_P53_       AGGTTGGCTCTGACTGTACCACCATCCACTACAACTGCATGTGTAACAGTACCACCTTCCATTCATCCTAACTACCTAC
Y236C dsDNA_p53_       TGGCTCTGACTGTACCACCATCCACTACAACTACATGTGTGACAGTTCCTACCAACCTTCCATTCATCCTAACTACCTAC
N239D
```

Primers used for generating PCR products to serve as substrates for T7 transcription of sgRNAs for high-throughput sequencing. rev_gRNA_T7 (above) was used in all cases. The pFYF1320 plasmid was used as template as noted in Materials and Methods section. SEQ ID NOs: 391-442 appear from top to bottom below, respectively.

```
fwd_sgRNA_T7_HTS_base    TAATACGACTCACTATAGGTTATTTCGTGGATTTATTTAGTTTTAGAGCTAGAAATAGCA fwd_sgRNA_T7_HTS_1A      TAATACGACTCACTATAGGATATTTCGTGGATTTATTTAGTTTTAGAGCTAGAAATAGCA fwd_sgRNA_T7_HTS_1C      TAATACGACTCACTATAGGCTATTTCGTGGATTTATTTAGTTTTAGAGCTAGAAATAGCA fwd_sgRNA_T7_HTS_1G      TAATACGACTCACTATAGGGTATTTCGTGGATTTATTTAGTTTTAGAGCTAGAAATAGCA fwd_sgRNA_T7_HTS_2A      TAATACGACTCACTATAGGTAATTTCGTGGATTTATTTAGTTTTAGAGCTAGAAATAGCA
```

| | |
|---|---|
| fwd_sgRNA_T7_HTS_2C | TAATACGACTCACTATAGGTCATTTCGTGGATTTATTTAGTTTTAGAGCTAGAAATAGCA |
| fwd_sgRNA_T7_HTS_2G | TAATACGACTCACTATAGGTGATTTCGTGGATTTATTTAGTTTTAGAGCTAGAAATAGCA |
| fwd_sgRNA_T7_HTS_3T | TAATACGACTCACTATAGGTTTTTTCGTGGATTTATTTAGTTTTAGAGCTAGAAATAGCA |
| fwd_sgRNA_T7_HTS_3C | TAATACGACTCACTATAGGTTTTTTCGTGGATTTATTTAGTTTTAGAGCTAGAAATAGCA |
| fwd_sgRNA_T7_HTS_3G | TAATACGACTCACTATAGGTTCTTTCGTGGATTTATTTAGTTTTAGAGCTAGAAATAGCA |
| fwd_sgRNA_T7_HTS_4A | TAATACGACTCACTATAGGTTGTTTCGTGGATTTATTTAGTTTTAGAGCTAGAAATAGCA |
| fwd_sgRNA_T7_HTS_4C | TAATACGACTCACTATAGGTTAATTCGTGGATTTATTTAGTTTTAGAGCTAGAAATAGCA |
| fwd_sgRNA_T7_HTS_4G | TAATACGACTCACTATAGGTTACTTCGTGGATTTATTTAGTTTTAGAGCTAGAAATAGCA |
| fwd_sgRNA_T7_HTS_5A | TAATACGACTCACTATAGGTTAGTTCGTGGATTTATTTAGTTTTAGAGCTAGAAATAGCA |
| fwd_sgRNA_T7_HTS_5C | TAATACGACTCACTATAGGTTATATCGTGGATTTATTTAGTTTTAGAGCTAGAAATAGCA |
| fwd_sgRNA_T7_HTS_5G | TAATACGACTCACTATAGGTTATCTCGTGGATTTATTTAGTTTTAGAGCTAGAAATAGCA |
| fwd_sgRNA_T7_HTS_6A | TAATACGACTCACTATAGGTTATGTCGTGGATTTATTTAGTTTTAGAGCTAGAAATAGCA |
| fwd_sgRNA_T7_HTS_6C | TAATACGACTCACTATAGGTTATTACGTGGATTTATTTAGTTTTAGAGCTAGAAATAGCA |
| fwd_sgRNA_T7_HTS_6G | TAATACGACTCACTATAGGTTATTCCGTGGATTTATTTAGTTTTAGAGCTAGAAATAGCA |
| fwd_sgRNA_T7_HTS_8A | TAATACGACTCACTATAGGTTATTGCSTGGATTTATTTAGTTTTAGAGCTAGAAATAGCA |
| fwd_sgRNA_T7_HTS_8T | TAATACGACTCACTATAGGTTATTTCATGGATTTATTTAGITTTAGAGCTAGAAATAGCA |
| fwd_sgRNA_T7_HTS_8C | TAATACGACTCACTATAGGTTATTTCTTGGATTTATTTAGTTTTAGAGCTAGAAATAGCA |
| fwd_sgRNA_T7_HTS_9A | TAATACGACTCACTATAGGTTATTTCCTGGATTTATTTAGTTTTAGAGCTAGAAATAGCA |
| fwd_sgRNA_T7_HTS_9C | TAATACGACTCACTATAGGTTATTTCGAGGATTTATTTAGTTTTAGAGCTAGAAATAGCA |
| fwd_sgRNA_T7_HTS_9G | TAATACGACTCACTATAGGTTATTTCGCGGATTTATTTAGTTTTAGAGCTAGAAATAGCA |
| fwd_sgRNA_T7_HTS_10A | TAATACGACTCACTATAGGTTATTTCGGGGATTTATTTAGTTTTAGAGCTAGAAATAGCA |
| fwd_sgRNA_T7_HTS_10T | TAATACGACTCACTATAGGTTATTTCGTAGATTTATTTAGTTTTAGAGCTAGAAATAGCA |
| fwd_sgRNA_T7_HTS_10C | TAATACGACTCACTATAGGTTATTTCGTTGATTTATTTAGTTTTAGAGCTAGAAATAGCA |
| fwd_sgRNA_T7_HTS_11A | TAATACGACTCACTATAGGTTATTTCGTGAATTTATTTAGTTTTAGAGCTAGAAATAGCA |
| fwd_sgRNA_T7_HTS_11T | TAATACGACTCACTATAGGTTATTTCGTGTATTTATTTAGTTTTAGAGCTAGAAATAGCA |
| fwd_sgRNA_T7_HTS_11C | TAATACGACTCACTATAGGTTATTTCGTGCATTTATTTAGTTTTAGAGCTAGAAATAGCA |
| fwd_sgRNA_T7_HTS_12T | TAATACGACTCACTATAGGTTATTTCGTGGTTTATTTAGTTTTAGAGCTAGAAATAGCA |
| fwd_sgRNA_T7_HTS_12C | TAATACGACTCACTATAGGTTATTTCGTGGCTTTATTTAGTTTTAGAGCTAGAAATAGCA |
| fwd_sgRNA_T7_HTS_12G | TAATACGACTCACTATAGGTTATTTCGTGGCTTTATTTAGTTTTAGAGCTAGAAATAGCA |
| fwd_sgRNA_T7_HTS_13A | TAATACGACTCACTATAGGTTATTTCGTGGGTTTATTTAGTTTTAGAGCTAGAAATAGCA |
| fwd_sgRNA_T7_HTS_13C | TAATACGACTCACTATAGGTTATTTCGTGGAATTATTTAGTTTTAGAGCTAGAAATAGCA |
| fwd_sgRNA_T7_HTS_13G | TAATACGACTCACTATAGGTTATTTCGTGGACTTATTTAGTTTTAGAGCTAGAAATAGCA |
| fwd_sgRNA_T7_HTS_multiC | TAATACGACTCACTATAGGTTCCCCCCCCGATTTATTTAGTTTTAGAGCTAGAAATAGCA |
| fwd_sgRNA_T7_HTS_TCGCACCC_odd | TAATACGACTCACTATAGGCGCACCCGTGGATTTATTTAGTTTTAGAGCTAGAAATAGCA |
| fwd_sgRNA_T7_HTS_CCTCGCAC_odd | TAATACGACTCACTATAGGCTCGCACGTGGATTTATTTAGTTTTAGAGCTAGAAATAGCA |
| fwd_sgRNA_T7_HTS_ACCCTCGC_odd | TAATACGACTCACTATAGGCCCTCGCGTGGATTTATTTAGTTTTAGAGCTAGAAATAGCA |
| fwd_sgRNA_T7_HTS_GCACCCTC_odd | TAATACGACTCACTATAGGCACCCTCGTGGATTTATTTAGTTTTAGAGCTAGAAATAGCA |
| fwd_sgRNA_T7_HTS_TCGCACCC_even | TAATACGACTCACTATAGGTCGCACCCGTGGATTTATTTAGTTTTAGAGCTAGAAATAGCA |

```
fwd_sgRNA_T7_HTS_      TAATACGACTCACTATAGGCCTCGCACGTGGATTTATTAGTTTTAGAGCTAGAAATAGCA
CCTCGCAC_even fwd_sgRNA_T7_HTS_      TAATACGACTCACTATAGGACCCTCGCGTGGATTTATTAGTTTTAGAGCTAGAAATAGCA
ACCCTCGC_even fwd_sgRNA_T7_HTS_      TAATACGACTCACTATAGGGCACCCTCGTGGATTTATTAGTTTTAGAGCTAGAAATAGCA
GCACCCTC_even fwd_sgRNA_T7_HTS_      TAATACGACTCACTATAGGGAGTCCGAGCAGAAGAAGAAGTTTTAGAGCTAGAAATAGCA
EMX1 fwd_sgRNA_T7_HTS_      TATACGACTCACTATAGGGGAATCCCTTCTGCAGCACCGTTTTAGAGCTAGAAATAGCA
FANCF fwd_sgRNA_T7_HTS_      TAATACGACTCACTATAGGGAACACAAAGCATAGACTGCGTTTTAGAGCTAGAAATAGCA
HEK293_site2 fwd_sgRNA_T7_HTS_      TAATACGACTCACTATAGGGGCCCAGACTGAGCACGTGAGTTTTAGAGCTAGAAATAGCA
HEK293_site3 fwd_sgRNA_T7_HTS_      TAATACGACTCACTATAGGGGCACTGCGGCTGGAGGTGGGTTTTAGAGCTAGAAATAGCA
HEK293_site4 fwd_sgRNA_T7_HTS_      TAATACGACTCACTATAGGGTCATCTTAGTCATTACCTGGTTTTAGAGCTAGAAATAGCA
RNF2
```

Sequences of in vitro-edited dsDNA for high-throughput sequencing (HTS). Shown are the sequences of edited strands. Reverse complements of all sequences shown were also obtained. dsDNA substrates were obtained by annealing complementary strands as described in Materials and Methods. Oligonucleotides representing the EMX1, FANCF, HEK293 site 2, HEK293 site 3, HEK293 site 4, and RNF2 loci were originally designed for use in the gel-based deaminase assay and therefore have the same 25-nt sequence on their 5'-ends (matching that of the Cy3-primer). SEQ ID NOs: 443-494 appear from top to bottom below, respectively.

```
Base sequence    ACGTAAACGGCCACACAAGTTCTTATTTCGTGGATTTATTTATGGCATCTTCTTCAAGGACG

1A               ACGTAAACGGCCACAAGTTCATATTTCGTGGATTTATTTATGGCATCTTCTTCAAGGACG

1C               ACGTAAACGGCCACAAGTTCCTATTTCGTGGATTTATTTATGGCATCTTCTTCAAGGACG

1G               ACGTAAACGGCCACAAGTTCGTATTTCGTGGATTTATTTATGGCATCTTCTTCAAGGACG

2A               ACGTAAACGGCCACAAGTTCTAATTTCGTGGATTTATTTATGGCATCTTCTTCAAGGACG

2C               ACGTAAACGGCCACAAGTTCTCATTTCGTGGATTTATTTATGGCATCTTCTTCAAGGACG

2G               ACGTAAACGGCCACAAGTTCTGATTTCGTGGATTTATTTATGGCATCTTCTTCAAGGACG

3T               ACGTAAACGGCCACAAGTTCTTTTTTCGTGGATTTATTTATGGCATCTTCTTCAAGGACG

3C               ACGTAAACGGCCACAAGTTCTTCTTTCGTGGATTTATTTATGGCATCTTCTTCAAGGACG

3G               ACGTAAACGGCCACAAGTTCTTGTTTCGTGGATTTATTTATGGCATCTTCTTCAAGGACG

4A               ACGTAAACGGCCACAAGTTCTTAATTCGTGGATTTATTTATGGCATCTTCTTCAAGGACG

4C               ACGTAAACGGCCACAAGTTCTTACTTCGTGGATTTATTTATGGCATCTTCTTCAAGGACG

4G               ACGTAAACGGCCACAAGTTCTTAGTTCGTGGATTTATTTATGGCATCTTCTTCAAGGACG

5A               ACGTAAACGGCCACAAGTTCTTATATCGTGGATTTATTTATGGCATCTTCTTCAAGGACG

5C               ACGTAAACGGCCACAAGTTCTTATCTCGTGGATTTATTTATGGCATCTTCTTCAAGGACG

5G               ACGTAAACGGCCACAAGTTCTTATGTCGTGGATTTATTTATGGCATCTTCTTCAAGGACG

6A               ACGTAAACGGCCACAAGTTCTTATTACGTGGATTTATTTATGGCATCTTCTTCAAGGACG

6C               ACGTAAACGGCCACAAGTTCTTATTCCGTGGATTTATTTATGGCATCTTCTTCAAGGACG

6G               ACGTAAACGGCCACAAGTTCTTATTGCGTGGATTTATTTATGGCATCTTCTTCAAGGACG

8A               ACGTAAACGGCCACAAGTTCTTATTTCATGGATTTATTTATGGCATCTTCTTCAAGGACG

8T               ACGTAAACGGCCACAAGTTCTTATTTCTTGGATTTATTTATGGCATCTTCTTCAAGGACG

8C               ACGTAAACGGCCACAAGTTCTTATTTCCTGGATTTATTTATGGCATCTTCTTCAAGGACG
```

-continued

| | |
|---|---|
| Base sequence | ACGTAAACGGCCACAAGTTCTTATTTCGTGGATTTATTTATGGCATCTTCTTCAAGGACG |
| 9A | ACGTAAACGGCCACAAGTTCTTATTTCGAGGATTTATTTATGGCATCTTCTTCAAGGACG |
| 9C | ACGTAAACGGCCACAAGTTCTTATTTCGCGGATTTATTTATGGCATCTTCTTCAAGGACG |
| 9G | ACGTAAACGGCCACAAGTTCTTATTTCGGGGATTTATTTATGGCATCTTCTTCAAGGACG |
| 10A | ACGTAAACGGCCACAAGTTCTTATTTCGTAGATTTATTTATGGCATCTTCTTCAAGGACG |
| 10T | ACGTAAACGGCCACAAGTTCTTATTTCGTTGATTTATTTATGGCATCTTCTTCAAGGACG |
| 10C | ACGTAAACGGCCACAAGTTCTTATTTCGTCGATTTATTTATGGCATCTTCTTCAAGGACG |
| 11A | ACGTAAACGGCCACAAGTTCTTATTTCGTGAATTTATTTATGGCATCTTCTTCAAGGACG |
| 11T | ACGTAAACGGCCACAAGTTCTTATTTCGTGTATTTATTTATGGCATCTTCTTCAAGGACG |
| 11C | ACGTAAACGGCCACAAGTTCTTATTTCGTGCATTTATTTATGGCATCTTCTTCAAGGACG |
| 12T | ACGTAAACGGCCACAAGTTCTTATTTCGTGGTTTATTTATGGCATCTTCTTCAAGGACG |
| 12C | ACGTAAACGGCCACAAGTTCTTATTTCGTGGCTTTATTTATGGCATCTTCTTCAAGGACG |
| 12G | ACGTAAACGGCCACAAGTTCTTATTTCGTGGGTTTATTTATGGCATCTTCTTCAAGGACG |
| 13A | ACGTAAACGGCCACAAGTTCTTATTTCGTGGAATTATTTATGGCATCTTCTTCAAGGACG |
| 13C | ACGTAAACGGCCACAAGTTCTTATTTCGTGGACTTATTTATGGCATCTTCTTCAAGGACG |
| 13G | ACGTAAACGGCCACAAGTTCTTATTTCGTGGAGTTATTTATGGCATCTTCTTCAAGGACG |
| multiC | ACGTAAACGGCCACAAGTTCTTCCCCCCCGATTTATTTATGGCATCTTCTTCAAGGACG |
| TCGCACCC_odd | ACGTAAACGGCCACAAGTTTCGCACCCGTGGATTTATTTATGGCATCTTCTTCAAGGACG |
| CCTCGCAC_odd | ACGTAAACGGCCACAAGTTCCTCGCACGTGGATTTATTTATGGCATCTTCTTCAAGGACG |
| ACCCTCGC_odd | ACGTAAACGGCCACAAGTTACCCTCGCGTGGATTTATTTATGGCATCTTCTTCAAGGACG |
| GCACCCTC_odd | ACGTAAACGGCCACAAGTTGCACCCTCGTGGATTTATTTATGGCATCTTCTTCAAGGACG |
| TCGCACCC_even | ACGTAAACGGCCACAAGTATTCGCACCCGTGGATTTATTTATGGCATCTTCTTCAAGGACG |
| CCTCGCAC_even | ACGTAAACGGCCACAAGTATCCTCGCACGTGGATTTATTTATGGCATCTTCTTCAAGGACG |
| ACCCTCGC_even | ACGTAAACGGCCACAAGTATACCCTCGCGTGGATTTATTTATGGCATCTTCTTCAAGGACG |
| GCACCCTC_even | ACGTAAACGGCCACAAGTATGCACCCTCGTGGATTTATTTATGGCATCTTCTTCAAGGACG |
| EMX1_invitro | GTAGGTAGTTAGGATGAATGGAAGGTTGGTAGGCCTGAGTCCGAGCAGAAGAAGAAGGGCTCCCATCACATCAACCGGTG |
| FANCF_invitro | GTAGGTAGTTAGGATGAATGGAAGGTTGGTACTCATGGAATCCCTTCTGCAGCACCTGGATCGCTTTTCCGAGCTTCTGG |
| HEK293_site2_invitro | GTAGGTAGTTAGGATGAATGGAAGGTTGGTAAACTGGAACACAAAGCATAGACTGCGGGGCGGGCCAGCCTGAATAGCTG |
| HEK293_site3_invitro | GTAGGTAGTTAGGATGAATGGAAGGTTGGTACTTGGGGCCCAGACTGAGCACGTGATGGCAGAGGAAAGGAAGCCCTGCT |
| HEK293_site4_invitro | GTAGGTAGTTAGGATGAATGGAAGGTTGGTACCGGTGGCACTGCGGCTGGAGGTGGGGGTTAAAGCGGAGACTCTGGTGC |
| RNF2_invitro | GTAGGTAGTTAGGATGAATGGAAGGTTGGTATGGCAGTCATCTTAGTCATTACCTGAGGTGTTCGTTGTAACTCATATAA |

Primers for HTS of in vitro edited dsDNA. SEQ ID NOs: 495-503 appear from top to bottom below, respectively.

| | |
|---|---|
| fwd_invitro_HTS | ACACTCTTTCCCTACACGACGCTCTTCCGATCTNNNNACGTAAACGGCCACAA |
| rev_invitro_HTS | TGGAGTTCAGACGTGTGCTCTTCCGATCTCGTCCTTGAAGAAGATGC |
| fwd_invitro_HEK_targets | ACACTCTTTCCCTACACGACGCTCTTCCGATCTNNNNGTAGGTAGTTAGGATGAATGGAA |
| rev_EMX1_invitro | TGGAGTTCAGACGTGTGCTCTTCCGATCTCACCGGTTGATGTGATGG |

-continued

| | |
|---|---|
| rev_FANCF_invitro | TGGAGTTCAGACGTGTGCTCTTCCGATCTCCAGAAGCTCGGAAAAGC |
| rev_HEK293_site2_invitro | TGGAGTTCAGACGTGTGCTCTTCCGATCTCAGCTATTCAGGCTGGC |
| rev_HEK293_site3_invitro | TGGAGTTCAGACGTGTGCTCTTCCGATCTAGCAGGGCTTCCTTTC |
| rev_HEK293_site4_invitro | TGGAGTTCAGACGTGTGCTCTTCCGATCTGCACCAGAGTCTCCG |
| rev_RNF2_invitro | TGGAGTTCAGACGTGTGCTCTTCCGATCTTTATATGAGTTACAACGAACACC |

Primers for HTS of on-target and off-target sites from all mammalian cell culture experiments. SEQ ID NOs: 504-579 and 1869-1900 appear from top to bottom below, respectively.

| | |
|---|---|
| fwd_EMX1_HTS | ACACTCTTTCCCTACACGACGCTCTTCCGATCTNNNNCAGCTCAGCCTGAGTGTTGA |
| rev_EMX1_HTS | TGGAGTTCAGACGTGTGCTCTTCCGATCTCTCGTGGGTTTGTGGTTGC |
| fwd_FANCF_HTS | ACACTCTTTCCCTACACGACGCTCTTCCGATCTNNNNCATTGCAGAGAGGCGTATCA |
| rev_FANCF_HTS | TGGAGTTCAGACGTGTGCTCTTCCGATCTGGGTCCCAGGTGCTGAC |
| fwd_HEK293_site2_HTS | ACACTCTTTCCCTACACGACGCTCTTCCGATCTNNNNCCAGCCCATCTGTCAAACT |
| rev_HEK293_site2_HTS | TGGAGTTCAGACGTGTGCTCTTCCGATCTTGAATGGATTCCTTGGAAACAATGA |
| fwd_HEK293_site3_HTS | ACACTCTTTCCCTACACGACGCTCTTCCGATCTNNNNATGTGGGCTGCCTAGAAAGG |
| rev_HEK293_site3_HTS | TGGAGTTCAGACGTGTGCTCTTCCGATCTCCCAGCCAAACTTGTCAACC |
| fwd_HEK293_site4_HTS | ACACTCTTTCCCTACACGACGCTCTTCCGATCTNNNNGAACCCAGGTAGCCAGAGAC |
| rev_HEK293_site4_HTS | TGGAGTTCAGACGTGTGCTCTTCCGATCTTCCTTTCAACCCGAACGGAG |
| fwd_RNF2_HTS | ACACTCTTTCCCTACACGACGCTCTTCCGATCTNNNNCTCTTCTTTATTTCCAGCAATGT |
| rev_RNF2_HTS | TGGAGTTCAGACGTGTGCTCTTCCGATCTGTTTTCATGTTCTAAAAATGTATCCCA |
| fwd_p53_Y163C_HTS | ACACTCTTTCCCTACACGACGCTCTTCCGATCTNNNNTACAGTACTCCCCTGCCCTC |
| rev_p53_Y163C_HTS | TGGAGTTCAGACGTGTGCTCTTCCGATCTGCTGCTCACCATCGCTATCT |
| fwd_p53_N239D_HTS | ACACTCTTTCCCTACACGACGCTCTTCCGATCTNNNNCCTCATCTTGGGCCTGTGTT |
| rev_p53_N239D_HTS | TGGAGTTCAGACGTGTGCTCTTCCGATCTAAATCGGTAAGAGGTGGGCC |
| fwd_APOE4_C158R_HTS | ACACTCTTTCCCTACACGACGCTCTTCCGATCTNNNNGCGGACATGGAGGACGTG |
| rev_APOE4_C158R_HTS | TGGAGTTCAGACGTGTGCTCTTCCGATCTCTGTTCCACCAGGGGCCC |
| fwd_EMX1_off1_HIS | ACACTCTTTCCCTACACGACGCTCTTCCGATCTNNNNTGCCCAATCATTGATGCTTTT |
| rev_EMX1_off1_HTS | TGGAGTTCAGACGTGTGCTCTTCCGATCTAGAAACATTTACCATAGACTATCACCT |
| fwd_EMX1_off2_HTS | ACACTCTTTCCCTACACGACGCTCTTCCGATCTNNNNAGTAGCCTCTTTCTCAATGTGC |
| rev_EMX1_off2_HTS | TGGAGTTCAGACGTGTGCTCTTCCGATCTGCTTTCACAAGGATGCAGTCT |
| fwd_EMX1_off3_HTS | ACACTCTTTCCCTACACGACGCTCTTCCGATCTTNNNNGAGCTAGACTCCGAGGGGA |
| rev_EMX1_off3_HTS | TGGAGTTCAGACGTGTGCTCTTCCGATCTTCCTCGTCCTGCTCTCACTT |
| fwd_EMX1_off4_HTS | ACACTCTTTCCCTACACGACGCTCTTCCGATCTNNNNAGAGGCTGAAGAGGAAGACCA |
| rev_EMX1_off4_HTS | TGGAGTTCAGACGTGTGCTCTTCCGATCTGGCCCAGCTGTGCATTCTAT |
| fwd_EMX1_off5_HTS | ACACTCTTTCCCTACACGACGCTCTTCCGATCTNNNNCCAAGAGGGCCAAGTCCTG |
| rev_EMX1_off5_HTS | TGGAGTTCAGACGTGTGCTCTTCCGATCTCAGCGAGGAGTGACAGCC |
| fwd_EMX1_off7_HTS | ACACTCTTTCCCTACACGACGCTCTTCCGATCTNNNNCACTCCACCTGATCTCGGGG |
| rev_EMX1_off7_HTS | TGGAGTTCAGACGTGTGCTCTTCCGATCTCGAGGAGGGAGGGAGCAG |
| fwd_EMX1_off8_HTS | ACACTCTTTCCCTACACGACGCTCTTCCGATCTNNNNACCACAAATGCCCAAGAGAC |
| rev_EMX1_off8_HTS | TGGAGTTCAGACGTGTGCTCTTCCGATCTGACACAGTCAAGGGCCGG |

| | |
|---|---|
| fwd_EMX1_off9_HTS | ACACTCTTTCCCTACACGACGCTCTTCCGATCTNNNNCCCACCTTTGAGGAGGCAAA |
| rev_EMX1_off9_HTS | TGGAGTTCAGACGTGTGCTCTTCCGATCTTTCCATCTGAGAAGAGAGTGGT |
| fwd_EMX1_off10_HTS | ACACTCTTTCCCTACACGACGCTCTTCCGATCTNNNNGTCATACCTTGGCCCTTCCT |
| rev_EMX1_off10_HTS | TGGAGTTCAGACGTGTGCTCTTCCGATCTTCCCTAGGCCCACACCAG |
| fwd_FANCF_off1_HTS | ACACTCTTTCCCTACACGACGCTCTTCCGATCTNNNNAACCCACTGAAGAAGCAGGG |
| rev_FANCF_off1_HTS | TGGAGTTCAGACGTGTGCTCTTCCGATCTGGTGCTTAATCCGGCTCCAT |
| fwd_FANCF_off2_HTS | ACACTCTTTCCCTACACGACGCTCTTCCGATCTNNNNTCCAGTGTTTCCATCCCGAA |
| rev_FANCF_off2_HTS | TGGAGTTCAGACGTGTGCTCTTCCGATCTCCTCTGACCTCCACAACTCT |
| fwd_FANCF_off3_HTS | ACACTCTTTCCCTACACGACGCTCTTCCGATCTNNNNCTGGGTACAGTTCTGCGTGT |
| rev_FANCF_off3_HTS | TGGAGTTCAGACGTGTGCTCTTCCGATCTTCACTCTGAGCATCGCCAAG |
| fwd_FANCF_off4_HTS | ACACTCTTTCCCTACACGACGCTCTTCCGATCTNNNNGGTTTAGAGCCAGTGAACTAGAG |
| rev_FANCF_off4_HTS | TGGAGTTCAGACGTGTGCTCTTCCGATCTGCAAGACAAAATCCTCTTTATACTTTG |
| fwd_FANCF_off5_HTS | ACACTCTTTCCCTACACGACGCTCTTCCGATCTNNNNGGGAGGGGACGGCCTTAC |
| rev_FANCF_off5_HTS | TGGAGTTCAGACGTGTGCTCTTCCGATCTGCCTCTGGCGAACATGGC |
| fwd_FANCF_off6_HTS | ACACTCTTTCCCTACACGACGCTCTTCCGATCTNNNNTCCTGGTTAAGAGCATGGGC |
| rev_FANCF_off6_HTS | TGGAGTTCAGACGTGTGCTCTTCCGATCTGATTGAGTCCCCACAGCACA |
| fwd_FANCF_off7_HTS | ACACTCTTTCCCTACACGACGCTCTTCCGATCTNNNNCCAGTGTTTCCCATCCCAA |
| rev_FANCF_off7_HTS | TGGAGTTCAGACGTGTGCTCTTCCGATCTTGACCTCCACAACTGGAAAAT |
| fwd_FANCF_off8_HTS | ACACTCTTTCCCTACACGACGCTCTTCCGATCTNNNNGCTTCCAGACCCACCTGAAG |
| rev_FANCF_off9_HTS | TGGAGTTCAGACGTGTGCTCTTCCGATCTACCGAGGAAAATTGCTTGTCG |
| fwd_HEK293_site2_off1_HTS | ACACTCTTTCCCTACACGACGCTCTTCCGATCTNNNNGTGTGGAGAGTGAGTAAGCCA |
| rev_HEK293_site2_off1_HTS | TGGAGTTCAGACGTGTGCTCTTCCGATCTACGGTAGGATGATTTCAGGCA |
| fwd_HEK293_site2_off2_HTS | ACACTCTTTCCCTACACGACGCTCTTCCGATCTNNNNCACAAAGCAGTGTAGCTCAGG |
| rev_HEK293_site2_off2_HTS | TGGAGTTCAGACGTGTGCTCTTCCGATCTTTTTTGGTACTCGAGTGTTATTCAG |
| fwd_HEK293_site3_off1_HTS | ACACTCTTTCCCTACACGACGCTCTTCCGATCTNNNNTCCCTGTTGACCTGGAGAA |
| rev_HEK293_site3_off1_HTS | TGGAGTTCAGACGTGTGCTCTTCCGATCTCACTGTACTTGCCCTGACCA |
| fwd_HEK293_site3_off2_HTS | ACACTCTTTCCCTACACGACGCTCTTCCGATCTNNNNTGGTGTTGACAGGGAGCAA |
| rev_HEK293_site3_off2_HTS | TGGAGTTCAGACGTGTGCTCTTCCGATCTCTGAGATGTGGGCAGAAGGG |
| fwd_HEK293_site3_off3_HTS | ACACTCTTTCCCTACACGACGCTCTTCCGATCTNNNNTGAGAGGGAACAGAAGGGCT |
| rev_HEK293_site3_off3_HTS | TGGAGTTCAGACGTGTGCTCTTCCGATCTGTCCAAAGGCCCAAGAACCT |
| fwd_HEK293_site3_off4_HTS | ACACTCTTTCCCTACACGACGCTCTTCCGATCTNNNNTCCTAGCACTTTGGAAGGTCG |
| rev_HEK293_site3_off4_HTS | TGGAGTTCAGACGTGTGCTCTTCCGATCTGCTCATCTTAATCTGCTCAGCC |
| fwd_HEK293_site3_off5_HTS | ACACTCTTTCCCTACACGACGCTCTTCCGATCTNNNNAAAGGAGCAGCTCTTCCTGG |
| rev_HEK293_site3_off5_HTS | TGGAGTTCAGACGTGTGCTCTTCCGATCTGTCTGCACCATCTCCCACAA |
| fwd_HEK293_site4_off1_HTS | ACACTCTTTCCCTACACGACGCTCTTCCGATCTNNNNGGCATGGCTTCTGAGACTA |
| rev_HEK293_site4_off1_HTS | TGGAGTTCAGACGTGTGCTCTTCCGATCTGTCTCCCTTGCACTCCCTGTCTTT |
| fwd_HEK293_site4_off2_HTS | ACACTCTTTCCCTACACGACGCTCTTCCGATCTNNNNTTGGCAATGGAGGCATTGG |
| rev_HEK293_site4_off2_HTS | TGGAGTTCAGACGTGTGCTCTTCCGATCTGAAGAGGCTGCCCATGAGAG |
| fwd_HEK293_site4_off3_HTS | ACACTCTTTCCCTACACGACGCTCTTCCGATCTNNNNGGTCTGAGGCTCGAATCCTG |
| rev_HEK293_site4_off3_HTS | TGGAGTTCAGACGTGTGCTCTTCCGATCTCTGTGGCCTCCATATCCCTG |
| fwd_HEK293_site4_off4_HTS | ACACTCTTTCCCTACACGACGCTCTTCCGATCTNNNNTTTCCACCAGAACTCAGCCC |

-continued

| | |
|---|---|
| rev_HEK293_site4_off4_HTS | TGGAGTTCAGACGTGTGCTCTTCCGATCTCCTCGGTTCCTCCACAACAC |
| fwd_HEK293_site4_off5_HTS | ACACTCTTTCCCTACACGACGCTCTTCCGATCTNNNNCACGGGAAGGACAGGAGAAG |
| rev_HEK293_site4_off5_HTS | TGGAGTTCAGACGTGTGCTCTTCCGATCTGCAGGGGAGGGATAAAGCAG |
| fwd_HEK293_site4_off6_HTS | ACACTCTTTCCCTACACGACGCTCTTCCGATCTNNNNCCACGGGAGATGGCTTATGT |
| rev_HEK293_site4_off6_HTS | TGGAGTTCAGACGTGTGCTCTTCCGATCTCACATCCTCACTGTGCCACT |
| fwd_HEK293_site4_off7_HTS | ACACTCTTTCCCTACACGACGCTCTTCCGATCTNNNNGTCAGTCTCGGCCCCTCA |
| rev_HEK293_site4_off7_HTS | TGGAGTTCAGACGTGTGCTCTTCCGATCTGCCACTGTAAAGCTCTTGGG |
| fwd_HEK293_site4_off8_HTS | ACACTCTTTCCCTACACGACGCTCTTCCGATCTNNNNAGGGTAGAGGGACAGAGCTG |
| rev_HEK293_site4_off8_HTS | TGGAGTTCAGACGTGTGCTCTTCCGATCTGGACCCCACATAGTCAGTGC |
| fwd_HEK293_site4_off9_HTS | ACACTCTTTCCCTACACGACGCTCTTCCGATCTNNNNGCTGTCAGCCCTATCTCCATC |
| rev_HEK293_site4_off9_HTS | TGGAGTTCAGACGTGTGCTCTTCCGATCTTGGGCAATTAGGACAGGGAC |
| fwd_HEK293_site4_off10_HTS | ACACTCTTTCCCTACACGACGCTCTTCCGATCTNNNNGCAGCGGAGGAGGTAGATTG |
| rev_HEK293_site4_off10_HTS | TGGAGTTCAGACGTGTGCTCTTCCGATCTCTCAGTACCTGGAGTCCCGA |
| fwd_HEK2_ChIP_off1_HTS | ACACTCTTTCCCTACACGACGCTCTTCCGATCTNNNNGACAGGCTCAGGAAAGCTGT |
| rev_HEK2_ChIP_off1_HTS | TGGAGTTCAGACGTGTGCTCTTCCGATCTACACAAGCCTTTCTCCAGGG |
| fwd_HEK2_ChIP_off2_HTS | ACACTCTTTCCCTACACGACGCTCTTCCGATCTNNNNAATAGGGGGTGAGACTGGGG |
| rev_HEK2_ChIP_off2_HTS | TGGAGTTCAGACGTGTGCTCTTCCGATCTGCCTCAGACGAGACTTGAGG |
| fwd_HEK2_ChIP_off3_HTS | ACACTCTTTCCCTACACGACGCTCTTCCGATCTNNNNGGCCAGCAGGAAAGGAATCT |
| rev_HEK2_ChIP_off3_HTS | TGGAGTTCAGACGTGTGCTCTTCCGATCTTGACTGCACCTGTAGCCATG |
| fwd_HEK2_ChIP_off4_HTS | ACACTCTTTCCGTACACGACGCTCTTCCGATCTNNNNTCAAGGAAATCACCCTGCCC |
| rev_HEK2_ChIP_off4_HTS | TGGAGTTCAGACGTGTGGTCTTCCGATCTAACTTCCTTGGTGTGCAGCT |
| fwd_HEK2_ChIP_off5_HTS | ACACTCTTTCCGTACACGACGCTCTTCCGATCTNNNNATGGGCTCAGCTACGTCATG |
| rev HEK2 ChIP off5 HTS | TGGAGTTCAGACGTGTGCTCTTCCGATCTAATAGCAGTGTGGTGGGCAA |
| fwd_HEK3_ChIP_off1_HTS | ACACTCTTTCCCTACACGACGCTCTTCCGATCTNNNNCGCACATCCCTTGTCTCTCT |
| rev_HEK3_ChIP_off1_HTS | TGGAGTTCAGACGTGTGCTCTTCCGATCTCTACTGGAGCACACCCCAAG |
| fwd_HEK3_ChIP_off2_HTS | ACACTCTTTCCCTACACGACGCTCTTCCGATCTNNNNTGGGTCACGTAGCTTTGGTC |
| rev_HEK3_ChIP_off2_HTS | TGGAGTTCAGACGTGTGCTCTTCCGATCTTGGTGGCCATGTGCAACTAA |
| fwd_HEK3_ChIp_off3_HTS | ACACTCTTTCCCTACACGACGCTCTTCCGATCTNNNNCTACTACGTGCCAGCTCAGG |
| rev_HEK3_ChIP_off3_HTS | TGGAGTTCAGACGTGTGCTCTTCCGATCTACCTCCCCTCCTCACTAACC |
| fwd_HEK3_ChIP_off4_HTS | ACACTCTTTCCCTACACGACGCTCTTCCGATCTNNNNGCCTCAGCTCCATTTCCTGT |
| rev_HEK3_ChIP_off4_HTS | TGGAGTTCAGACGTGTGCTCTTCCGATCTAACCTTTATGGCACCAGGGG |
| fwd_HEK3_ChIP_off5_HTS | ACACTCTTTCCCTACACGACGCTCTTCCGATCTNNNNGAGCTCAGCATTAGCAGGCT |
| rev_HEK3_ChIP_off5_HTS | TGGAGTTCAGACGTGTGCTCTTCCGATCTTTCCTGGCTTTCCGATTCCC |
| fwd_HEK4_ChIP_off1_HTS | ACACTCTTTCCCTACACGACGCTCTTCCGATCTNNNNGTGCAATTGGAGGAGGAGCT |
| rev_HEK4_ChIP_off1_HTS | TGGAGTTCAGACGTGTGCTCTTCCGATCTCACCAGCTACAGGCAGAACA |
| fwd_HEK4_ChIP_off3_HTS | ACACTCTTTCCCTACACGACGCTCTTCCGATCTNNNNCCTACCCCAACAGAGATGG |
| rev_HEK4_ChIP_off3_HTS | TGGAGTTCAGACGTGTGCTCTTCCGATCTCCACACAACTCAGGTCCTCC |

Sequences of Single-Stranded Oligonucleotide Donor Templates (ssODNs) Used in HDR Studies.

EMX1 sense
(SEQ ID NO: 580)
TCATCTGTGCCCCTCCCTCCCTGGCCCAGGTGAAGGTGTGGTTCCAGAAC

CGGAGGACAAAGTACAAACGGCAGAAGCTGGAGGAGGAAGGGCCTGAGTT

TGAGCAGAAGAAGAAGGGCTCCCATCACATCAACCGGTGGCGCATTGCCA

CGAAGCAGGCCAATGGGAGGACATCGATGTCACCTCCAATGACTAGGGT

EMX1 antisense
(SEQ ID NO: 581)
ACCCTAGTCATTGGAGGTGACATCGATGTCCTCCCCATTGGCCTGCTTCG

TGGCAATGCGCCACCGGTTGATGTGATGGGAGCCCTTCTTCTTCTGCTCA

AACTGAGGCCGTTCCTCCTCCAGCTTCTGCCGTTTGTACTTTGTCCTCCG

GTTCTGGAACCACACCTTCACCTGGGCCAGGGAGGGAGGGGCACAGATGA

HEK293 site 3 sense
(SEQ ID NO: 582)
CATGCAATTAGTCTATTTCTGCTGCAAGTAAGCATGCATTTGTAGGCTTG

ATGCTTTTTTTCTGCTTCTCCAGCCCTGGCCTGGGTCAATCCTTGGGGCT

TAGACTGAGGACGTGATGGCAGAGGAAAGGAAGCCCTGCTTCCTCCAGAG

GGCGTCGCAGGACAGCTTTTCCTAGACAGGGGCTAGTATGTGCAGCTCCT

HEK293 site 3 antisense
(SEQ ID NO: 583)
AGGAGCTGCACATACTAGCCCCTGTCTAGGAAAAGCTGTCCTGGGACGCC

CTCTGGAGGAAGCAGGGCTTCCTTTCCTCTGCCATCACGTGCTCAGTCTA

AGCCCCAAGGATTGACCCAGGCCAGGGCTGGAGAAGCAGAAAAAAAGCAT

GAAGCCTACAAATGCATGCTTAGTTGCAGCAGAAATAGACTAATTGCATG

HEK site 4 sense
(SEQ ID NO: 584)
GGCTGACAAAGGCCGGGCTGGGTGGAAGGAAGGGAGGAAGGGCGAGGCAG

AGGGTCCAAAGCAGGATGACAGGCAGGGGCACCGCGGCGCCCCGGTGGCA

TTGCGGCTGGAGGTGGGGGTTAAAGCGGAGACTCTGGTGCTGTGTGACTA

CAGTGGGGGCCCTGCCCTCTCTGAGCCCCGCCTCCAGGCCTGTGTGTGT

HEK site 4 antisense
(SEQ ID NO: 585)
ACACACACAGGCCTGGAGGCGGGGGCTCAGAGAGGGCAGGGCCCCCACTG

TAGTCACACAGCACCAGAGTCTCCGCTTTAACCCCCACCTCCAGCCGCAA

TGCCACCGGGGCGCCGCGGTGCCCCTGCCTGTCATCCTGCTTTGGACCCT

CTGCCTCGCCCTTCCTCCCTTCCTTCCACCCAGCCCGGCCTTTGTCAGCC

APOE4 sense
(SEQ ID NO: 743)
AGCACCGAGGAGCTGCGGGTGCGCCTCGCCTCCCACCTGCGCAAGCTGCG

TAAGCGGCTCCTCCGCGATGCCGATGACCTGCAGAAGTGCCTGGCAGTGT

ACCAGGCCGGGGCCCGCGAGGGCGCCGAGCGCGGCCTCAGCGCCATCCGC

GAGCGCCTGGGGCCCCTGGTGGAACAGGGCCGCGTGCGGGCCGCCACTGT

APOE4 antisense
(SEQ ID NO: 744)
ACAGTGGCGGCCCGCACGCGGCCCTGTTCCACCAGGGGCCCCAGGCGCTC

GCGGATGGCGCTGAGGCCGCGCTCGGCGCCCTCGCGGGCCCCGGCCTGGT

ACACTGCCAGGCACTTCTGCAGGTCATCGGCATCGCGGAGGAGCCGCTTA

CGCAGCTTGCGCAGGTGGGAGGCGAGGCGCACCCGCAGCTCCTCGGTGCT p53 Y163C sense
(SEQ ID NO: 745)
ACTCCCCTGCCCTCAACAAGATGTTTTGCCAACTGGCCAAGACCTGCCCT

GTGCAGCTGTGGGTTGATTCCACACCCCCGCCCGGCACCCGCGTCCGCGC

CATGGCCATCTACAAGCAGTCACAGCACATGACGGAGGTTGTGAGGCGCT

GCCCCCACCATGAGCGCTGCTCAGATAGCGATGGTGAGCAGCTGGGGCTG p53 Y163C antisense
(SEQ ID NO: 746)
CAGCCCCAGCTGCTCACCATCGCTATCTGAGCAGCGCTCATGGTGGGGGC

AGCGCCTCACAACCTCCGTCATGTGCTGTGACTGCTTGTAGATGGCCATG

GCGCGGACGCGGGTGCCGGGCGGGGGTGTGGAATCAACCCACAGCTGCAC

AGGGCAGGTCTTGGCCAGTTGGCAAAACATCTTGTTGAGGGCAGGGGAGT

Deaminase Gene gBlocks Gene Fragments hAID
(SEQ ID NO: 586)
CATCCTTGGTACCGAGCTCGGATCCAGCCACCATGGATAGCCTCTTGATG

AATAGACGAAGTTCCTGTATCAGTTTAAAAACGTGAGATGGGCAAAAGG

CCGACGAGAGACATATCTGTGCTATGTCGTTAAGCGCAGAGATTCAGCCA

CCAGTTTCTCTCTCGACTTCGGCTACCTGCGGAACAAGAATGGTTGCCAT

GTTGAGCTCCTGTTCCTGAGGTATATCAGCGACTGGGATTTGGACCCAGG

GCGGTGCTATAGGGTGACATGGTTTACCTCCTGGTCACCTTGTTATGACT

GCGCGCGGCATGTTGCCGATTTTCTGAGAGGGAACCCTAACCTGTCTCTG

AGGATCTTCACCGCGCGACTGTACTTCTGTGAGGACCGGAAAGCCGAACC

CGAGGGACTGAGACGCCTCCACAGAGCGGGTGTGCAGATTGCCATAATGA

CCTTTAAGGACTACTTCTACTGCTGGAACACCTTCGTCGAAAATCACGAG

CGGACTTTCATGGCTTGGGAAGGATTGCATGAAAACAGCGTCAGGCTCCA

GGCAGCTTCGCCGCATTCTTCTCCCGTTGTACGAGGTTGATGACCTCAGA

GATGCCTTTAGAACACTGGGACTGTAGGCGGCCGCTCGATTGGTTTGGTG

TGGCTCTAA rAPOBEC1 (mammalian)
(SEQ ID NO: 587)
CATCCTTGGTACCGAGCTCGGATCCAGCCACCATGAGCTCAGAGACTGGC

CCAGTGGCTGTGGACCCCACATTGAGACGGCGGATCGAGCCCCATGAGTT

TGAGGTATTCTTCGATCCGAGAGAGCTCCGCAAGGAGACCTGCCTGCTTT

ACGAAATTAATTGGGGGGGCCGGCACTCCATTTGGCGACATACATCACAG

AACACTAACAAGCACGTCGAAGTCAACTTCATCGAGAAGTTCACGACAGA

AAGATATTTCTGTCCGAACACAAGGTGCAGCATTACCTGGTTTCTCAGCT

GGAGCCCATGCGGCGAATGTAGTAGGGCCATCACTGAATTCCTGTCAAGG

TATCCCCACGTCACTCTGTTTATTTACATCGCAAGGCTGTACCACCACGC

TGACCCCGCAATCGACAAGGCCTGCGGGATTTGATCTCTTCAGGTGTGA

CTATCCAAATTATGACTGAGCAGGAGTCAGGATACTGCTGGAGAAACTTT

GTGAATTATAGCCCGAGTAATGAAGCCCACTGGCCTAGGTATCCCCATCT

```
GTGGGTACGACTGTACGTTCTTGAACTGTACTGCATCATACTGGGCCTGC

CTCCTTGTCTCAACATTCTGAGAAGGAAGCAGCCACAGCTGACATTCTTT

ACCATCGCTCTTCAGTCTTGTCATTACCAGCGACTGCCCCCACACATTCT

CTGGGCCACCGGGTTGAAATGAGCGGCCGCTCGATTGGTTTGGTGTGGCT

CTAA pmCDA1
                                       (SEQ ID NO: 588)
CATCCTTGGTACCGAGCTCGGATCCAGCCACCATGACAGACGCTGAATAT

GTTAGGATCCATGAAAAACTGGATATCTATACATTTAAGAAGCAGTTCTT

CAATAACAAAAAGTCAGTATCTCACAGATGCTATGTCCTGTTCGAACTCA

AGAGAAGAGGAGAAAGGCGGGCCTGTTTCTGGGGGTACGCGGTTAATAAA

CCCCAGTCGGGACCGAGAGGGGGATTCACGCCGAGATCTTTTCAATTAG

GAAGGTTGAAGAGTATCTTCGCGACAATCCCGGTCAGTTCACAATTAACT

GGTACAGCTCCTGGAGCCCTTGCGCTGATTGCGCCGAGAAAATACTCGAA

TGGTACAACCAGGAGTTGAGAGGCAATGGCCACACTCTCAAGATTTGGGC

TTGCAAGCTTTACTACGAGAAGAACGCGAGAAATCAGATTGGCTTGTGGA

ACCTCAGGGACAACGGGGTCGGGTTGAATGTTATGGTGTCCGAACATTAC

CAGTGCTGTAGAAAGATCTTCATTCAGTCCAGTCACAATCAGCTGAACGA

GAACAGATGGCTGGAGAAAACACTGAAACGGGCAGAGAAAAGGCGCTCAG

AGCTGAGTATCATGATCCAGGTCAAAATCCTGCATACAACCAAAAGCCCG

GCTGTATAAGCGGCCGCTCGATTGGTTTGGTGTGGCTCTAA haPOBEC3G
                                       (SEQ ID NO: 589)
CATCCTTGGTACCGAGCTCGGATCCAGCCACCATGGAGCTGAAGTATCAC

CCTGAGATGCGGTTTTTCCACTGGTTTAGTAAGTGGCGCAAACTTCATCG

GGATCAGGAGTATGAAGTGACCTGGTATATCTCTTGGTCTCCCTGCACAA

AATGTACACGCGACATGGCCACATTTCTGGCCGAGGATCCAAAGGTGACG

CTCACAATCTTTGTGGCCCGCCTGTATTATTTCTGGGACCCGGATTATCA

GGAGGCACTTAGGTCATTGTGCCAAAAGCGCGACGGACCACGGGCGACTA

TGAAAATCATGAATTATGACGAATTCCAGCATTGCTGGAGTAAGTTTGTG

TACAGCCAGCGGGAGCTGTTCGAGCCCTGGAACAATCTTCCCAAGTACTA

CATACTGCTTCACATTATGTTGGGGGAGATCCTTCGGCACTCTATGGATC

CTCCTACCTTTACGTTTAACTTTAATAATGAGCCTTGGGTTCGCGGGCGC

CATGAAACCTATTTGTGCTACGAGGTCGAGCGGATGCATAATGATACGTG

GGTCCTGCTGAATCAGAGGAGGGGGTTTCTGTGTAACCAGGCTCCACATA

AACATGGATTTCTCGAGGGGCGGCACGCCGAACTGTGTTTCCTTGATGTG

ATACCTTTCTGGAAGCTCGACCTTGATCAAGATTACAGGGTGACGTGTTT

CACCTCCTGGTCACCCTGCTTCAGTTGCGCCCAAGAGATGGCTAAATTTA

TCAGTAAGAACAAGCATGTGTCCCTCTGTATTTTTACAGCCAGAATTTAT

GATGACCAGGGCCGGTGCCAGGAGGGGCTGCGGACACTCGCTGAGGCGGG

CGCGAAGATCAGCATAATGACATACTCCGAATTCAAACACTGTTGGGACA

CTTTTGTGGACCACCAGGGCTGCCCATTTCAGCCGTGGGATGGGCTCGAC

GAACATAGTCAGGATCTCTCAGGCCGGCTGCGAGCCATATTGCAGAACCA

GGAGAATTAGGCGGCCGCTCGATTGGTTTGGTGTGGCTCTAA rAPOBEC1 (E. Coli)
                                       (SEQ ID NO: 590)
GGCCGGGGATTCTAGAAATAATTTTGTTTAACTTTAAGAAGGAGATATAC

CATGGATGTCTTCTGAAACCGGTCCGGTTGCGGTTGACCCGACCCTGCGT

CGTCGTATCGAACCGCACGAATTCGAAGTTTTCTTCGACCCGCGTGAAC|

GCGTAAAGAAACCTGCCTGCTGTACGAAATCAACTGGGGTGGTCGTCACT

CTATCTGGCGTCACACCTCTCAGAACACCAACAAACACGTTGAAGTTAAC

TTCATCGAAAAATTCACCACCGAACGTTACTTCTGCCCGAACACCCGTTG

CTCTATCACCTGGTTCCTGTCTTGGTCTCCGTGCGGTGAATGCTCTCGTG

CGATCACCGAATTCCTGTCTCGTTACCCGCACGTTACCCTGTTCATCTAC

ATCGCGCGTCTGTACCACCACGCGGACCCGCGTAACCGTCAGGGTCTGCG

TGACCTGATCTCTTCTGGTGTTACCATCCAGATCATGACCGAACAGGAAT

CTGGTTACTGCTGGCGTAACTTCGTTAACTACTCTCCGTCTAACGAAGCG

CACTGGCCGCGTTACCCGCACCTGTGGGTTCGTCTGTACGTTCTGGAACT

GTACTGCATCATCCTGGGTCTGCCGCCGTGCCTGAACATCCTGCGTCGTA

AACAGCCGCAGCTGACCTTCTTCACCATCGCGCTGCAGTCTTGCCACTAC

CAGCGTCTGCCGCCGCACATCCTGTGGGCGACCGGTCTGAAAGGTGGTAG

TGGAGGGAGCGGCGGTTCAATGGATAAGAAATAC
```

Amino Acid Sequences of NBE1, NBE2, and NBE3.

```
NBE1 for E. Coli expression (His6-rAPOBEC1-XTEN-dCas9)
                                       (SEQ ID NO: 591)
MGSSHHHHHHMSSETGPVAVDPTLRRRIEPHEFEVFFDPRELRKETCLLYEINWGGRHSRNRHTSQNTN

KHVEVNFIEKFTTERYFCPNTRCSITWFLSWSPCGECSRAITEFLSRYPHVTLFIYIARLYHHADPRNRQGL

RDLISSGVTIQIMTEQESGYCWRNFVNYSPSNEAHWPRYPHLWVRLYVLELYCIILGLPPCLNILRRKQPQ

LTFFTIALQSCHYQRLPPHILWATGLKSGSETPGTSESATPESDKKYSIGLAIGTNSVGWAVITDEYKVPSK

KFKVLGNTDRHSIKKNLIGALLFDSGETAEATRLKRTARRRYTRRKNRICYLQEIFSNEMAKVDDSFFHRL

EESFLVEEDK|KHERHPIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGEKKNGLFGNLIALSL

GLTPNFKSNFDLAEDAKLQLSKDTYDDDLDNLLAQIGDQYADLFLAAKNLSDAILLSDILRVNTEITKAPLSA
```

-continued

SMIKRYDEHHQDLTLLKALVRQQLPEKYKEIFFDQSKNGYAGYIDGGASQEEFYKFIKPILEKMDGTEELL

VKLNREDLLRKQRTFDNGSIPHQIHLGELHAILRRQEDFYPFLKDNREKIEKILTFRIPYYVGPLARGNSRF

AWMTRKSEETITPWNFEEVVDKGASAQSFIERMTNFDKNLPNEKVLPKHSLLYEYFTVYNELTKVKYVTE

GMRKPAFLSGEQKKAIVDLLFKTNRKVTVQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWGRLSRKLINGIRDKQS

GKTILDFLKSDGFANRNFMQLIHDDSLTFKEDIQKAQVSGQGDSLHEHIANLAGSPAIKKGILQTVKVVDEL

VKVMGRHKPENIVIEMARENQTTQKGQKNSRERMKRIEEGIKELGSQILKEHPVENTQLQNEKLYLYYLQ

NGRDMYVDQELDINRLSDYDVDAIVPQSFLKDDSIDNKVLTRSDKNRGKSDNVPSEEVVKKMKNYWRQL

LNAKLITQRKFDNLTKAERGGLSELDKAGFIKRQLVETRQITKHVAQILDSRMNTKYDENDKLIREVKVITLK

SKLVSDFRKDFQFYKVREINNYHHAHDAYLNAVVGTALIKKYPKLESEFVYGDYKVYDVRKMIAKSEQEIG

KATAKYFFYSNIMNFFKTEITLANGEIRKRPLIETNGETGEIVWDKGRDFATVRKVLSMPQVNIVKKTEVQT

GGFSKESILPKRNSDKLIARKKDWDPKKYGGFDSPTVAYSVLVVAKVEKGKSKKLKSVKELLGITIMERSS

FEKNPIDFLEAKGYKEVKKDLIIKLPKYSLFELENGRKRMLASAGELQKGNELALPSKYVNFLYLASHYEKL

KGSPEDNEQKQLFVEQHKHYLDEIIEQISEFSKRVILADANLDKVLSAYNKHRDKPIREQAENIIHLFTLTNL

GAPAAFKYFDTTIDRKRYTSTKEVLDATLIHQSITGLYETRIDLSQLGGDSGGSPKKKRKV

NBE1 for Mammalian expression (rAPOBEC1-XTEN-dCas9-NLS)

(SEQ ID NO: 592)

MSSETGPVAVDPTLRRRIEPHEFEVFFDPRELRKETCLLYEINWGGRHSIWRHTSQNTNKHVEVNFIEKF

TTERYFCPNTRCSITWFLSWSPCGECSRAITEFLSRYPHVTLFIYIARLYHHADPRNRQGLRDLISSGVTIQ

IMTEQESGYCWRNFVNYSPSNEAHWPRYPHLWVRLYVLELYCIILGLPPCLNILRRKQPQLTFFTIALQSC

HYQRLPPHILWATGLKSGSETPGTSESATPESDKKYSIGLAIGTNSVGWAVITDEYKVPSKKFKVLGNTDR

HSIKKNLIGALLFDSGETAEAT|RLKRTARRRYTRRKNRICYLQEIFSNEMAKVDDSFFHRLEESFLVEEDKK

HERHPIFGNIVDEVAYHEKYPTIYHLRKKLVDSTDKADLRLIYLALAHMIKFRGHFLIEGDLNPDNSDVDKLF

IQLVQTYNQLFEENPINASGVDAKAILSARLSKSRRLENLIAQLPGEKKNGLFGNLIALSLGLTPNFKSNFDL

AEDAKLQLSKDTYDDDLDNLLAQIGDQYADLFLAAKNLSDAILLSDILRVNTEITKAPLSASMIKRYDEHHQ

DLTLLKALVRQQLPEKYKEIFFDQSKNGYAGYIDGGASQEEFYKFIKPILEKMDGTEELLVKLNREDLLRKQ

RTFDNGSIPHQIHLGELHAILRRQEDFYPFLKDNREKIEKILTFRIPYYVGPLARGNSRFAWMTRKSEETITP

WNFEEVVDKGASAQSFIERMTNFDKNLPNEKVLPKHSLLYEYFTVYNELTKVKYVTEGMRKPAFLSGEQ

KKAIVDLLFKTNRKVTVQLKEDYFKKIECFDSVEISGVEDRFNASLGTYHDLLKIIKDKDFLDNEENEDILE

DIVLTLTLFEDREMIEERLKTYAHLFDDKVMKQLKRRRYTGWGRLSRKLINGIRDKQSGKTILDFLKSDGFA

NRNFMQLIHDDSLTFKEDIQKAQVSGQGDSLHEHIANLAGSPAIKKGILQTVKVVDELVKVMGRHKPENIVI

EMARENQTTQKGQKNSRERMKRIEEGIKELGSQILKEHPVENTQLQNEKLYLYYLQNGRDMYVDQELDI

NRLSDYDVDAIVPQSFLKDDSIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLIREVKVITLKSKLVSDFRKDFQF

YKVREINNYHHAHDAYLNAVVGTALIKKYPKLESEFVYGDYKVYDVRKMIAKSEQEIGKATAKYFFYSNIM

NFFKTEITLANGEIRKRPLIETNGETGEIVWDKGRDFATVRKVLSMPQVNIVKKTEVQTGGFSKESILPKRN

SDKLIARKKDWDPKKYGGFDSPTVAYSVLVVAKVEKGKSKKLKSVKELLGITIMERSSFEKNPIDFLEAKG

YKEVKKDLIIKLPKYSLFELENGRKRMLASAGELQKGNELALPSKYVNFLYLASHYEKLKGSFEDNEQKQL

FVEQHKHYLDEIIEQISEFSKRVILADANLDKVLSAYNKHRDKPIREQAENIIHLFTLTNLGAPAAFKYFDTTI

DRKRYTSTKEVLDATLIHQSITGLYETRIDLSQLGGDSGGSPKKKRKV

-continued

Alternative NBE1 for Mammalian expression with human APOBEC1 (hAPOBEC1-XTEN-dCas9-NLS)

(SEQ ID NO: 5737)

MTSEKGPSTGDPTLRRRIEPWEFDVFYDPRELRKEACLLYEIKWGMSRKIWRSSGKNTTN

HVEVNFIKKFTSERDFHPSMSCSITWFLSWSPCWECSQAIREFLSRHPGVTLVIYVARLFW

HMDQQNRQGLRDLVNSGVTIQIMRASEYYHCWRNFVNYPPGDEAHWPQYPPLWMMLY

ALELHCIILSLPPCLKISRRWQNHLTFFRLHLQNCHYQTIPPHILLATGLIHPSVAWRGSETP

GTSESATPESDKKYSIGLAIGTNSVGWAVITDEYKVPSKKFKVLGNTDRHSIKKNLIGALL

FDSGETAEATRLKRTARRRYTRRKNRICYLQEIFSNEMAKVDDSFFHRLEESFLVEEDKK

HERHPIFGNIVDEVAYHEKYPTIYHLRKKLVDSTDKADLRLIYLALAHMIKFRGHFLIEGD

LNPDNSDVDKLFIQLVQTYNQLFEENPINASGVDAKAILSARLSKSRRLENLIAQLPGEKK

NGLFGNLIALSLGLTPNFKSNFDLAEDAKLQLSKDTYDDDLDNLLAQIGDQYADLFLAA

KNLSDAILLSDILRVNTEITKAPLSASMIKRYDEHHQDLTLLKALVRQQLPEKYKEIFFDQ

SKNGYAGYIDGGASQEEFYKFIKPILEKMDGTEELLVKLNREDLLRKQRTFDNGSIPHQIH

LGELHAILRRQEDFYPFLKDNREKIEKILTFRIPYYVGPLARGNSRFAWMTRKSEETITPW

NFEEVVDKGASAQSFIERMTNFDKNLPNEKVLPKHSLLYEYFTVYNELTKVKYVTEGMR

KPAFLSGEQKKAIVDLLFKTNRKVTVKQLKEDYFKKIECFDSVEISGVEDRFNASLGTYH

DLLKIIKDKDFLDNEENEDILEDIVLTLTLFEDREMIEERLKTYAHLFDDKVMKQLKRRRY

TGWGRLSRKLINGIRDKQSGKTILDFLKSDGFANRNFMQLIHDDSLTFKEDIQKAQVSGQ

GDSLHEHIANLAGSPAIKKGILQTVKVVDELVKVMGRHKPENIVIEMARENQTTQKGQK

NSRERMKRIEEGIKELGSQILKEHPVENTQLQNEKLYLYYLQNGRDMYVDQELDINRLSD

YDVDAIVPQSFLKDDSIDNKVLTRSDKNRGKSDNVPSEEVVKKMKNYWRQLLNAKLITQ

RKFDNLTKAERGGLSELDKAGFIKRQLVETRQITKHVAQILDSRMNTKYDENDKLIREVK

VITLKSKLVSDFRKDFQFYKVREINNYHHAHDAYLNAVVGTALIKKYPKLESEFVYGDY

KVYDVRKMIAKSEQEIGKATAKYFFYSNIMNFFKTEITLANGEIRKRPLIETNGETGEIVW

DKGRDFATVRKVLSMPQVNIVKKTEVQTGGFSKESILPKRNSDKLIARKKDWDPKKYGG

FDSPTVAYSVLVVAKVEKGKSKKLKSVKELLGITIMERSSFEKNPIDFLEAKGYKEVKKD

LIIKLPKYSLFELENGRKRMLASAGELQKGNELALPSKYVNFLYLASHYEKLKGSPEDNE

QKQLFVEQHKHYLDEIIEQISEFSKRVILADANLDKVLSAYNKHRDKPIREQAENIIHLFTL

TNLGAPAAFKYFDTTIDRKRYTSTKEVLDATLIHQSITGLYETRIDLSQLGGDSGGSPKKK

RKV

NBE2 (rAPOBEC1-XTEN-dCas9-UGI-NLS)

(SEQ ID NO: 593)

MSSETGPVAVDPTLRRRIEPHEFEVFFDPRELRKETCLLYEINWGGRHSIWRHTSQNTNKHVEVNFIEKF

TTERYFCPNTRCSITWFLSWSPCGECSRAITEFLSRYPHVTLFIYIARLYHHADPRNRQGLRDLISSGVTIQ

IMTEQESGYCWRNFVNYSPSNEAHWPRYPHLWVRLYVLELYCIILGLPPCLNILRRKQPQLTFFTIALQSC

HYQRLPPHILWATGLKSGSETPGTSESATPESDKKYSIGLAIGTNSVGWAVITDEYKVPSKKFKVLGNTDR

HSIKKNLIGALLFDSGETAEATRLKRTARRRYTRRKNRICYLQEIFSNEMAKVDDSFFHRLEESFLVEEDKK

HERHPIFGNIVDEVAYHEKYPTIYHLRKKLVDSTDKADLRLIYLALAHMIKFRGHFLIEGDLNPDNSDVDKLF

IQLVQTYNQLFEENPINASGVDAKAILSARLSKSRRLENLIAQLPGEKKNGLFGNLIALSLGLTPNFKSNFDL

AEDAKLQLSKDTYDDDLDNLLAQIGDQYADLFLAAKNLSDAILLSDILRVNTEITKAPLSASMIKRYDEHHQ

DLTLLKALVRQQLPEKYKEIFFDQSKNGYAGYIDGGASQEEFYKFIKPILEKMDGTEELLVKLNREDLLRKQ

RTFDNGSIPHQIHLGELHAILRRQEDFYPFLKDNREKIEKILTFRIPYYVGPLARGNSRFAWMTRKSEETITP

-continued

WNFEEVVDKGASAQSFIERMTNFDKNLPNEKVLPKHSLLYEYFTVYNELTKVKYVTEGMRKPAFLSGEQ

KKAIVDLLFKTNRKVTVKQLKEDYFKKIECFDSVEISGVEDRFNASLGTYHDLLKIIKDKDFLDNEENEDILE

DIVLTLTLFEDREMIEERLKTYAHLFDDKVMKQLKRRRYTGWGRLSRKLINGIRDKQSGKTILDFLKSDGFA

NRNFMQLIHDDSLTFKEDIQKAQVSGQGDSLHEHIANLAGSPAIKKGILQTVKVVDELVKVMGRHKPENIVI

EMARENQTTQKGQKNSRERMKRIEEGIKELGSQILKEHPVENTQLQNEKLYLYYLQNGRDMYVDQELDI

NRLSDYDVDAIVPQSFLKDDSIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLIREVKVITLKSKLVSDFRKDFQF

YKVREINNYHHAHDAYLNAVVGTALIKKYPKLESEFVYGDYKVYDVRKMIAKSEQEIGKATAKYFFYSNIM

NFFKTEITLANGEIRKRPLIETNGETGEIVWDKGRDFATVRKVLSMPQVNIVKKTEVQTGGFSKESILPKRN

SDKLIARKKDWDPKKYGGFDSPTVAYSVLVVAKVEKGKSKKLKSVKELLGITIMERSSFEKNPIDFLEAKG

YKEVKKDLIIKLPKYSLFELENGRKRMLASAGELQKGNELALPSKYVNFLYLASHYEKLKGSPEDNEQKQL

FVEQHKHYLDEIIEQISEFSKRVILADANLDKVLSAYNKHRDKPIREQAENIIHLFTLTNLGAPAAFKYFDTTI

DRKRYTSTKEVLDATLIHQSITGLYETRIDLSQLGGDSGGSTNLSDIIEKETGKQLVIQESILMLPEEVEEVIG

NKPESDILVHTAYDESTDENVMLLTSDAPEYKPWALVIQDSNGENKIKMLSGGSPKKKRKV

NBE3 (rAPOBEC1-XTEN-Cas9n-UGI-NLS)
(SEQ ID NO: 594)
MSSETGPVAVDPTLRRRIEPHEFEVFFDPRELRKETCLLYEINWGGRHSIWRHTSQNTNKHVEVNFIEKF

TTERYFCPNTRCSITWFLSWSPCGECSRAITEFLSRYPHVTLFIYIARLYHHADPRNRQGLRDLISSGVTTQ

IMTEQESGYCWRNFVNYSPSNEAHWPRYPHLWVRLYVLELYCIILGLPPCLNILRRKQPQLTFFTIALQSC

HYQRLPPHILWATGLKSGSETPGTSESATPESDKKYSIGLAIGTNSVGWAVITDEYKVPSKKFKVLGNTDR

HSIKKNLIGALLFDSGETAEATRLKRTARRRYTRRKNRICYLQEIFSNEMAKVDDSFFHRLEESFLVEEDKK

HERHPIFGNIVDEVAYHEKYPTIYHLRKKLVDSTDKADLRLIYLALAHMIKFRGHFLIEGDLNPDNSDVDKLF

IQLVQTYNQLFEENPINASGVDAKAILSARLSKSRRLENLIAQLPGEKKNGLFGNLIALSLGLTPNFKSNFDL

AEDAKLQLSKDTYDDDLDNLLAQIGDQYADLFLAAKNLSDAILLSDILRVNTEITKAPLSASMIKRYDEHHQ

DLTLLKALVRQQLPEKYKEIFFDQSKNGYAGYIDGGASQEEFYKFIKPILEKMDGTEELLVKLNREDLLRKQ

RTFDNGSIPHQIHLGELHAILRRQEDFYPFLKDNREKIEKILTFRIPYYVGPLARGNSRFAWMTRKSEETFP

WNFEEVVDKGASAQSFIERMTNFDKNLPNEKVLPKHSLLYEYFTVYNELTKVKYVTEGMRKPAFLSGEQ

KKAIVDLLFKTNRKVTVKQLKEDYFKKIECFDSVEISGVEDRFNASLGTYHDLLKIIKDKDFLDNEENEDILE

DIVLTLTLFEDREMIEERLKTYAHLFDDKVMKQLKRRRYTGWGRLSRKLINGIRDKQSGKTILDFLKSDGFA

NRNFMQLIHDDSLTFKEDIQKAQVSGQGDSLHEHIANLAGSPAIKKGILQTNKVVDELVKVMGRHKPENIVI

EMARENQTTQKGQKNSRERMKRIEEGIKELGSQILKEHPVENTQLQNEKLYLYYLQNGRDMYVDQELDI

NRLSDYDVDHIVPQSFLKDDSIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLIREVKVITLKSKLVSDFRKDFQF

YKVREINNYHHAHDAYLNAVVGTALIKKYPKLESEFVYGDYKVYDVRKMIAKSEQEIGKATAKYFFYSNIM

NFFKTEITLANGEIRKRPLIETNGETGEIVWDKGRDFATVRKVLSMPQVNIVKKTEVQTGGFSKESILPKRN

SDKLIARKKDWDPKKYGGFDSPTVAYSVLVVAKVEKGKSKKLKSVKELLGITIMERSSFEKNPIDFLEAKG

YKEVKKDLIIKLPKYSLFELENGRKRMLASAGELQKGNELALPSKYVNFLYLASHYEKLKGSPEDNEQKQL

FVEQHKHYLDEIIEQISEFSKRVILADANLDKVLSAYNKHRDKPIREQAENIIHLFTLTNLGAPAAFKYFDTTI

DRKRYTSTKEVLDATLIHQSITGLYETRIDLSQLGGDSGGSTNLSDIIEKETGKQLVIQESIMLPEEVEEVIG

NKPESDILVHTAYDESTDENVMLLTSDAPEYKPWALVIQDSNGENKIKMLSGGSPKKKRKV

-continued pmCDA1-XTEN-dCas9-UGI (bacteria)

(SEQ ID NO: 5742)

MTDAEYVRIHEKLDIYTFKKQFFNNKKSVSHRCYVLFELKRRGERRACFWGYAVNKPQS

GTERGIHAEIFSIRKVEEYLRDNPGQFTINWYSSWSPCADCAEKILEWYNQELRGNGHTL

KIWACKLYYEKNARNQIGLWNLRDNGVGLNVMVSEHYQCCRKIFIQSSHNQLNENRWL

EKTLKRAEKRRSELSIMIQVKILHTTKSPAVSGSETPGTSESATPESDKKYSIGLAIGTNSV

GWAVITDEYKVPSKKFKVLGNTDRHSIKKNLIGALLFDSGETAEATRLKRTARRRYTRRK

NRICYLQEIFSNEMAKVDDSFFHRLEESFLVEEDKKHERHPIFGNIVDEVAYHEKYPTIYH

LRKKLVDSTDKADLRLIYLALAHMIKFRGHFLIEGDLNPDNSDVDKLFIQLVQTYNQLFE

ENPINASGVDAKAILSARLSKSRRLENLIAQLPGEKKNGLFGNLIALSLGLTPNFKSNFDLA

EDAKLQLSKDTYDDDLDNLLAQIGDQYADLFLAAKNLSDAILLSDILRVNTEITKAPLSAS

MIKRYDEHHQDLTLLKALVRQQLPEKYKEIFFDQSKNGYAGYIDGGASQEEFYKFIKPILE

KMDGTEELLVKLNREDLLRKQRTFDNGSIPHQIHLGELHAILRRQEDFYPFLKDNREKIEK

ILTFRIPYYVGPLARGNSRFAWMTRKSEETITPWNFEEVVDKGASAQSFIERMTNFDKNLP

NEKVLPKHSLLYEYFTVYNELTKVKYVTEGMRKPAFLSGEQKKAIVDLLFKTNRKVTVK

QLKEDYFKKIECFDSVEISGVEDRFNASLGTYHDLLKIIKDKDFLDNEENEDILEDIVLTLT

LFEDREMIEERLKTYAHLFDDKVMKQLKRRRYTGWGRLSRKLINGIRDKQSGKTILDFLK

SDGFANRNFMQLIHDDSLTFKEDIQKAQVSGQGDSLHEHIANLAGSPAIKKGILQTVKVV

DELVKVMGRHKPENIVIEMARENQTTQKGQKNSRERMKRIEEGIKELGSQILKEHPVENT

QLQNEKLYLYYLQNGRDMYVDQELDINRLSDYDVDAIVPQSFLKDDSIDNKVLTRSDKN

RGKSDNVPSEEVVKKMKNYWRQLLNAKLITQRKFDNLTKAERGGLSELDKAGFIKRQL

VETRQITKHVAQILDSRMNTKYDENDKLIREVKVITLKSKLVSDFRKDFQFYKVREINNY

HHAHDAYLNAVVGTALIKKYPKLESEFVYGDYKVYDVRKMIAKSEQEIGKATAKYFFYS

NIMNFFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKKLKSV

KELLGITIMERSSFEKNPIDFLEAKGYKEVKKDLIIKLPKYSLFELENGRKRMLASAGELQ

KGNELALPSKYVNFLYLASHYEKLKGSPEDNEQKQLFVEQHKHYLDEIIEQISEFSKRVIL

ADANLDKVLSAYNKHRDKPIREQAENIIHLFTLTNLGAPAAFKYFDTTIDRKRYTSTKEV

LDATLIHQSITGLYETRIDLSQLGGDSGGSMTNLSDIIEKETGKQLVIQESILMLPEEVEEVI

GNKPESDILVHTAYDESTDENVMLLTSDAPEYKPWALVIQDSNGENKIKML pmCDA1-XTEN-nCas9-UGI-NLS (mammalian construct)

(SEQ ID NO: 5743)

MTDAEYVRIHEKLDIYTFKKQFFNNKKSVSHRCYVLFELKRRGERRACFWGYAVNKPQS

GTERGIHAEIFSIRKVEEYLRDNPGQFTINWYSSWSPCADCAEKILEWYNQELRGNGHTL

KIWACKLYYEKNARNQIGLWNLRDNGVGLNVMVSEHYQCCRKIFIQSSHNQLNENRWL

EKTLKRAEKRRSELSIMIQVKILHTTKSPAVSGSETPGTSESATPESDKKYSIGLAIGTNSV

GWAVITDEYKVPSKKFKVLGNTDRHSIKKNLIGALLFDSGETAEATRLKRTARRRYTRRK

NRICYLQEIFSNEMAKVDDSFFHRLEESFLVEEDKKHERHPIFGNIVDEVAYHEKYPTIYH

LRKKLVDSTDKADLRLIYLALAHMIKFRGHFLIEGDLNPDNSDVDKLFIQLVQTYNQLFE

ENPINASGVDAKAILSARLSKSRRLENLIAQLPGEKKNGLFGNLIALSLGLTPNFKSNFDLA

EDAKLQLSKDTYDDDLDNLLAQIGDQYADLFLAAKNLSDAILLSDILRVNTEITKAPLSAS

MIKRYDEHHQDLTLLKALVRQQLPEKYKEIFFDQSKNGYAGYIDGGASQEEFYKFIKPILE

KMDGTEELLVKLNREDLLRKQRTFDNGSIPHQIHLGELHAILRRQEDFYPFLKDNREKIEK

-continued

ILTFRIPYYVGPLARGNSRFAWMTRKSEETITPWNFEEVVDKGASAQSFIERMTNFDKNLP

NEKVLPKHSLLYEYFTVYNELTKVKYVTEGMRKPAFLSGEQKKAIVDLLFKTNRKVTVK

QLKEDYFKKIECFDSVEISGVEDRFNASLGTYHDLLKIIKDKDFLDNEENEDILEDIVLTLT

LFEDREMIEERLKTYAHLFDDKVMKQLKRRRYTGWGRLSRKLINGIRDKQSGKTILDFLK

SDGFANRNFMQLIHDDSLTFKEDIQKAQVSGQGDSLHEHIANLAGSPAIKKGILQTVKVV

DELVKVMGRHKPENIVIEMARENQTTQKGQKNSRERMKRIEEGIKELGSQILKEHPVENT

QLQNEKLYLYYLQNGRDMYVDQELDINRLSDYDVDHIVPQSFLKDDSIDNKVLTRSDKN

RGKSDNVPSEEVVKKMKNYWRQLLNAKLITQRKFDNLTKAERGGLSELDKAGFIKRQL

VETRQITKHVAQILDSRMNTKYDENDKLIREVKVITLKSKLVSDFRKDFQFYKVREINNY

HHAHDAYLNAVVGTALIKKYPKLESEFVYGDYKVYDVRKMIAKSEQEIGKATAKYFFYS

NIMNFFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKKLKSV

KELLGITIMERSSFEKNPIDFLEAKGYKEVKKDLIIKLPKYSLFELENGRKRMLASAGELQ

KGNELALPSKYVNFLYLASHYEKLKGSPEDNEQKQLFVEQHKHYLDEIIEQISEFSKRVIL

ADANLDKVLSAYNKHRDKPIREQAENIIHLFTLTNLGAPAAFKYFDTTIDRKRYTSTKEV

LDATLIHQSITGLYETRIDLSQLGGDSGGSTNLSDIIEKETGKQLVIQESILMLPEEVEEVIG

NKPESDILVHTAYDESTDENVMLLTSDAPEYKPWALVIQDSNGENKIKMLSGGSPKKKR

KV huAPOBEC3G-XTEN-dCas9-UGI (bacteria)     (SEQ ID NO: 5744)

MDPPTFTFNFNNEPWVRGRHETYLCYEVERMHNDTWVLLNQRRGFLCNQAPHKHGFLE

GRHAELCFLDVIPFWKLDLDQDYRVTCFTSWSPCFSCAQEMAKFISKNKHVSLCIFTARIY

DDQGRCQEGLRTLAEAGAKISIMTYSEFKHCWDTFVDHQGCPFQPWDGLDEHSQDLSGR

LRAILQSGSETPGTSESATPESDKKYSIGLAIGTNSVGWAVITDEYKVPSKKFKVLGNTDR

HSIKKNLIGALLFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADLRLIYLALAHMI

KFRGHFLIEGDLNPDNSDVDKLFIQLVQTYNQLFEENPINASGVDAKAILSARLSKSRRLE

NLIAQLPGEKKNGLFGNLIALSLGLTPNFKSNFDLAEDAKLQLSKDTYDDDLDNLLAQIG

DQYADLFLAAKNLSDAILLSDILRVNTEITKAPLSASMIKRYDEHHQDLTLLKALVRQQL

PEKYKEIFFDQSKNGYAGYIDGGASQEEFYKFIKPILEKMDGTEELLVKLNREDLLRKQRT

FDNGSIPHQIHLGELHAILRRQEDFYPFLKDNREKIEKILTFRIPYYVGPLARGNSRFAWMT

RKSEETITPWNFEEVVDKGASAQSFIERMTNFDKNLPNEKVLPKHSLLYEYFTVYNELTK

VKYVTEGMRKPAFLSGEQKKAIVDLLFKTNRKVTVKQLKEDYFKKIECFDSVEISGVEDR

FNASLGTYHDLLKIIKDKDFLDNEENEDILEDIVLTLTLFEDREMIEERLKTYAHLFDDKV

MKQLKRRRYTGWGRLSRKLINGIRDKQSGKTILDFLKSDGFANRNFMQLIHDDSLTFKED

IQKAQVSGQGDSLHEHIANLAGSPAIKKGILQTVKVVDELVKVMGRHKPENIVIEMAREN

QTTQKGQKNSRERMKRIEEGIKELGSQILKEHPVENTQLQNEKLYLYYLQNGRDMYVDQ

ELDINRLSDYDVDAIVPQSFLKDDSIDNKVLTRSDKNRGKSDNVPSEEVVKKMKNYWRQ

LLNAKLITQRKFDNLTKAERGGLSELDKAGFIKRQLVETRQITKHVAQILDSRMNTKYDE

NDKLIREVKVITLKSKLVSDFRKDFQFYKVREINNYHHAHDAYLNAVVGTALIKKYPKLE

SEFVYGDYKVYDVRKMIAKSEQEIGKATAKYFFYSNIMNFFKTEITLANGEIRKRPLIETN

GETGEIVWDKGRDFATVRKVLSMPQVNIVKKTEVQTGGFSKESILPKRNSDKLIARKKD

-continued

WDPKKYGGFDSPTVAYSVLVVAKVEKGKSKKLKSVKELLGITIMERSSFEKNPIDFLEAK

GYKEVKKDLIIKLPKYSLFELENGRKRMLASAGELQKGNELALPSKYVNFLYLASHYEKL

KGSPEDNEQKQLFVEQHKHYLDEIIEQISEFSKRVILADANLDKVLSAYNKHRDKPIREQA

ENIIHLFTLTNLGAPAAFKYFDTTIDRKRYTSTKEVLDATLIHQSITGLYETRIDLSQLGGD

SGGSMTNLSDIIEKETGKQLVIQESILMLPEEVEEVIGNKPESDILVHTAYDESTDENVMLL

TSDAPEYKPWALVIQDSNGENKIKML huAPOBEC3G-XTEN-nCas9-UGI-NLS (mammalian construct)
(SEQ ID NO: 5745)
MDPPTFTFNFNNEPWVRGRHETYLCYEVERMHNDTWVLLNQRRGFLCNQAPHKHGFLE

GRHAELCFLDVIPFWKLDLDQDYRVTCFTSWSPCFSCAQEMAKFISKNKHVSLCIFTARIY

DDQGRCQEGLRTLAEAGAKISIMTYSEFKHCWDTFVDHQGCPFQPWDGLDEHSQDLSGR

LRAILQSGSETPGTSESATPESDKKYSIGLAIGTNSVGWAVITDEYKVPSKKFKVLGNTDR

HSIKKNLIGALLFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADLRLIYLALAHMI

KFRGHFLIEGDLNPDNSDVDKLFIQLVQTYNQLFEENPINASGVDAKAILSARLSKSRRLE

NLIAQLPGEKKNGLFGNLIALSLGLTPNFKSNFDLAEDAKLQLSKDTYDDDLDNLLAQIG

DQYADLFLAAKNLSDAILLSDILRVNTEITKAPLSASMIKRYDEHHQDLTLLKALVRQQL

PEKYKEIFFDQSKNGYAGYIDGGASQEEFYKFIKPILEKMDGTEELLVKLNREDLLRKQRT

FDNGSIPHQIHLGELHAILRRQEDFYPFLKDNREKIEKILTFRIPYYVGPLARGNSRFAWMT

RKSEETITPWNFEEVVDKGASAQSFIERMTNFDKNLPNEKVLPKHSLLYEYFTVYNELTK

VKYVTEGMRKPAFLSGEQKKAIVDLLFKTNRKVTVKQLKEDYFKKIECFDSVEISGVEDR

FNASLGTYHDLLKIIKDKDFLDNEENEDILEDIVLTLTLFEDREMIEERLKTYAHLFDDKV

MKQLKRRRYTGWGRLSRKLINGIRDKQSGKTILDFLKSDGFANRNFMQLIHDDSLTFKED

IQKAQVSGQGDSLHEHIANLAGSPAIKKGILQTVKVVDELVKVMGRHKPENIVIEMAREN

QTTQKGQKNSRERMKRIEEGIKELGSQILKEHPVENTQLQNEKLYLYYLQNGRDMYVDQ

ELDINRLSDYDVDHIVPQSFLKDDSIDNKVLTRSDKNRGKSDNVPSEEVVKKMKNYWRQ

LLNAKLITQRKFDNLTKAERGGLSELDKAGFIKRQLVETRQITKHVAQILDSRMNTKYDE

NDKLIREVKVITLKSKLVSDFRKDFQFYKVREINNYHHAHDAYLNAVVGTALIKKYPKLE

SEFVYGDYKVYDVRKMIAKSEQEIGKATAKYFFYSNIMNFFKTEITLANGEIRKRPLIETN

GETGEIVWDKGRDFATVRKVLSMPQVNIVKKTEVQTGGFSKESILPKRNSDKLIARKKD

WDPKKYGGFDSPTVAYSVLVVAKVEKGKSKKLKSVKELLGITIMERSSFEKNPIDFLEAK

GYKEVKKDLIIKLPKYSLFELENGRKRMLASAGELQKGNELALPSKYVNFLYLASHYEKL

KGSPEDNEQKQLFVEQHKHYLDEIIEQISEFSKRVILADANLDKVLSAYNKHRDKPIREQA

ENIIHLFTLTNLGAPAAFKYFDTTIDRKRYTSTKEVLDATLIHQSITGLYETRIDLSQLGGD

SGGSTNLSDIIEKETGKQLVIQESILMLPEEVEEVIGNKPESDILVHTAYDESTDENVMLLT

SDAPEYKPWALVIQDSNGENKIKMLSGGSPKKKRKV huAPOBEC3G(D316R_D317R)-XTEN-nCas9-UGI-NLS (mammalian construct)
(SEQ ID NO: 5746)
MDPPTFTFNFNNEPWVRGRHETYLCYEVERMHNDTWVLLNQRRGFLCNQAPHKHGFLE

GRHAELCFLDVIPFWKLDLDQDYRVTCFTSWSPCFSCAQEMAKFISKNKHVSLCIFTARIY

RRQGRCQEGLRTLAEAGAKISIMTYSEFKHCWDTFVDHQGCPFQPWDGLDEHSQDLSGR

LRAILQSGSETPGTSESATPESDKKYSIGLAIGTNSVGWAVITDEYKVPSKKFKVLGNTDR

HSIKKNLIGALLFDSGETAEATRLKRTARRRYTRRKNRICYLQEIFSNEMAKVDDSFFHRL

-continued

EESFLVEEDKKHERHPIFGNIVDEVAYHEKYPTIYHLRKKLVDSTDKADLRLIYLALAHMI

KFRGHFLIEGDLNPDNSDVDKLFIQLVQTYNQLFEENPINASGVDAKAILSARLSKSRRLE

NLIAQLPGEKKNGLFGNLIALSLGLTPNFKSNFDLAEDAKLQLSKDTYDDDLDNLLAQIG

DQYADLFLAAKNLSDAILLSDILRVNTEITKAPLSASMIKRYDEHHQDLTLLKALVRQQL

PEKYKEIFFDQSKNGYAGYIDGGASQEEFYKFIKPILEKMDGTEELLVKLNREDLLRKQRT

FDNGSIPHQIHLGELHAILRRQEDFYPFLKDNREKIEKILTFRIPYYVGPLARGNSRFAWMT

RKSEETITPWNFEEVVDKGASAQSFIERMTNFDKNLPNEKVLPKHSLLYEYFTVYNELTK

VKYVTEGMRKPAFLSGEQKKAIVDLLFKTNRKVTVKQLKEDYFKKIECFDSVEISGVEDR

FNASLGTYHDLLKIIKDKDFLDNEENEDILEDIVLTLTLFEDREMIEERLKTYAHLFDDKV

MKQLKRRRYTGWGRLSRKLINGIRDKQSGKTILDFLKSDGFANRNFMQLIHDDSLTFKED

IQKAQVSGQGDSLHEHIANLAGSPAIKKGILQTVKVVDELVKVMGRHKPENIVIEMAREN

QTTQKGQKNSRERMKRIEEGIKELGSQILKEHPVENTQLQNEKLYLYYLQNGRDMYVDQ

ELDINRLSDYDVDHIVPQSFLKDDSIDNKVLTRSDKNRGKSDNVPSEEVVKKMKNYWRQ

LLNAKLITQRKFDNLTKAERGGLSELDKAGFIKRQLVETRQITKHVAQILDSRMNTKYDE

NDKLIREVKVITLKSKLVSDFRKDFQFYKVREINNYHHAHDAYLNAVVGTALIKKYPKLE

SEFVYGDYKVYDVRKMIAKSEQEIGKATAKYFFYSNIMNFFKTEITLANGEIRKRPLIETN

GETGEIVWDKGRDFATVRKVLSMPQVNIVKKTEVQTGGFSKESILPKRNSDKLIARKKD

WDPKKYGGFDSPTVAYSVLVVAKVEKGKSKKLKSVKELLGITIMERSSFEKNPIDFLEAK

GYKEVKKDLIIKLPKYSLFELENGRKRMLASAGELQKGNELALPSKYVNFLYLASHYEKL

KGSPEDNEQKQLFVEQHKHYLDEIIEQISEFSKRVILADANLDKVLSAYNKHRDKPIREQA

ENIIHLFTLTNLGAPAAFKYFDTTIDRKRYTSTKEVLDATLIHQSITGLYETRIDLSQLGGD

SGGSTNLSDIIEKETGKQLVIQESILMLPEEVEEVIGNKPESDILVHTAYDESTDENVMLLT

SDAPEYKPWALVIQDSNGENKIKMLSGGSPKKKRKV

Base Calling Matlab Script (SEQ ID NO: 595)
WTnuc = 'GCGGACATGGAGGACGTGCGCGGCCGCCTGGTGCAGTACCG

CGGCGAGGTGCAGGCCATGCTCGGCCAGAGCACCGAGGAGCTGCGGGTGC

GCCTCGCCTCCCACCTGCGCAAGCTGCGTAAGCGGCTCCTCCGCGATGCC

GATGACCTGCAGAAGCGCCTGGCAGTGTACCAGGCCGGGCCCGCGAGGG

CGCCGAGCGCGGCCTCAGCGCCATCCGCGAGCGCCTGGGGCCCCTGGTGG

AACAG';

```
%cycle through fastq files for different samples files=dir('*.fastq');
for d=1:20
filename=files(d).name;
%read fastq file
[header,seqs,qscore]=fastqread(filename);
seqsLength=length(seqs);                    % number of sequences seqsFile=
strrep(filename,'.fastq','');               % trims off .fastq
%create a directory with the same name as fastq file ifexist(seqsFile,'dir');
        error('Directory already exists. Please rename or move it before moving on.');
end
mkdir(seqsFile);                            % make directory
wtLength=length(WTnuc);                     % length of wildtype sequence
%% aligning back to the wildtype nucleotide sequence
%
% A1N is a matrix of the nucleotide alignment window=1:wtLength;
```

```
sBLength=length(seqs);                    % number of sequences
% counts number of skips nSkips = 0;
ALN=repmat(' ',[sBLengthwtLength]);
% iterate through each sequencing read for i = 1:sBLength
%If you only have forward read fastq files leave as is
%If you have R1 foward and R2 is reverse fastq files uncomment the
%next four lines of code and the subsequent end statement
%            ifmod(d,2)==0;
%                         reverse=seqrcomplement(seqs{i});
%                         [score,alignment,start]=
swalign(reverse,WTnuc,'Alphabet','NT');
%            else
[score,alignment,start]=swalign(seqs{i},WTnuc,'Alphabet','NT');
%            end
% length of the sequencing read len=
length(alignment(3,:));
% if there is a gap in the alignment, skip = 1 and we will
% throw away the entire read skip = 0;
for j = 1:len
if (alignment(3,j)=='-'||alignment(1,j)=='-') skip = 1;
                         break;
end
%in addition if the qscore for any given base in the read is
             %below 31 the nucleotide is turned into an N (fastq qscores that are not letters)
ifisletter(qscore{i}(start(1)+j-1)) else
alignment(1,j)='N';
      end
end
if skip == 0 && len>10
ALN(i, start(2):(start(2)+length(alignment)-1))=alignment(1,:);
      end
end
% with the alignment matrices we can simply tally up the occurrences of
% each nucleotide at each column in the alignment these
% tallies ignore bases annotated as N
% due to low qscores
TallyNTD=zeros(5,wtLength); fori=1:wtLength
TallyNTD(:,i)=[sum(ALN(:,i)=='A'),sum(ALN(:,i)=='C'),sum(ALN(:,i)=='G'),sum(A
LN(:,i)=='T'),sum(ALN(:,i)=='N')];
end
% we then save these tally matrices in the respective folder for
% further processing
save(strcat(seqsFile,'/TallyNTD'),'TallyNTD'); dlmwrite(strcat(seqsFile,'/TallyNTD.txt'),TallyNTD,'precision',
'%.3f','newline','pc'); end
```

INDEL Detection Matlab Script

```
                                                               (SEQ ID NO: 595)
WTnuc = 'GCGGACATGGAGGACGTGCGCGGCCGCCTGGTGCAGTACCG

CGGCGAGGTGCAGGCCATGCTCGGCCAGAGCACCGAGGAGCTGCGGGTGC

GCCTCGCCTCCCACCTGCGCAAGCTGCGTAAGCGGCTCCTCCGCGATGCC

GATGACCTGCAGAAGCGCCTGGCAGTGTACCAGGCCGGGGCCCGCGAGGG

CGCCGAGCGCGGCCTCAGCGCCATCCGCGAGCGCCTGGGGCCCCTGGTGG

AACAG';
```

```
%cycle through fastq files for different samples files=dir('*.fastq');
%specify start and width of indel window as well as length of each flank indelstart=154;
width=30; flank=10;
for d=1:3
filename=files(d).name;
%read fastq file
[header,seqs,qscore]=fastqread(filename);
seqsLength=length(seqs);                    % number of sequences seqsFile
=strcat(strrep(filename,'.fastq',''),'_INDELS');
%create a directory with the same name as fastq file+_INDELS ifexist(seqsFile,'dir');
          error('Directory already exists. Please rename or move it before moving on.');
end
mkdir(seqsFile);                            % make directory
wtLength = length(WTnuc);                   % length of wildtype sequence sBLength =
```

```
length(seqs);                          % number of sequences
% initialize counters and cell arrays
nSkips = 0; notINDEL=0;
ins={ };
dels={ }; NumIns=0;
NumDels=0;
% iterate through each sequencing read for i = 1:sBLength
      %search for 10BP sequences that should flank both sides of the "INDEL WINDOW"
   windowstart=strfind(seqs{i},WTnuc(indelstart-flank:indelstart));
                       windowend=strfind(seqs {i},WTnuc(indelstart+width:indelstart+width+flank
));
%if the flanks are found proceed
iflength(windowstart)==1 && length(windowend)==1
%if the sequence length matches the INDEL window length save as
%not INDEL
if windowend-windowstart==width+flank notINDEL=notINDEL+1;
   %if the sequence is two or more bases longer than the INDEL
   %window length save as an Insertion
elseif windowend-windowstart>=width+flank+2 NumIns=NumIns+1;
   ins {NumIns}=seqs{i};
   %if the sequence is two or more bases shorter than the INDEL
   %window length save as a Deletion
elseif windowend-windowstart<=width+flank-2 NumDels=NumDels+1;
   dels {NumDels}=seqs {i};
   %keep track of skipped sequences that are either one base
   %shorter or longer than the INDEL window width else
   nSkips=nSkips+1;
   end
   %keep track of skipped sequences that do not possess matching flank
   %sequences else
   nSkips=nSkips+1;
            end
   end
   fid=fopen(strcat(seqsFile,'/summary.txt'),'wt');
   fprintf(fid, 'Skipped reads %i\n not INDEL %i\n Insertions %i\n Deletions
%i\n', [nSkips, notINDEL, NumIns, NumDels]); fclose(fid);
   save(strcat(seqsFile,'/nSkips'),'nSkips'); save(strcat(seqsFile,'/notINDEL'),'notINDEL');
   save(strcat(seqsFile,'/NumIns'),'NumIns'); save(strcat(seqsFile,'/NumDels'),'NumDels');
   save(strcat(seqsFile,'/dels'),'dels');
   C = dels;
   fid = fopen(strcat(seqsFile,'/dels.txt'),'wt'); fprintf(fid,'"%s"\n',C{:});
   fclose(fid);
   save(strcat(seqsFile,'/ins'),'ins'); C = ins;
   fid = fopen(strcat(seqsFile, '/ins.txt'),'wt'); fprintf(fid,'"%s"\n',C{:});
   fclose(fid);
   end
```

Example 5: Cas9 Variant Sequences

The disclosure provides Cas9 variants, for example Cas9 proteins from one or more organisms, which may comprise one or more mutations (e.g., to generate dCas9 or Cas9 nickase). In some embodiments, one or more of the amino acid residues, identified below by an asterek, of a Cas9 protein may be mutated. In some embodiments, the D10 and/or H840 residues of the amino acid sequence provided in SEQ ID NO: 10, or a corresponding mutation in any of the amino acid sequences provided in SEQ ID NOs: 11-260, are mutated. In some embodiments, the D10 residue of the amino acid sequence provided in SEQ ID NO: 10, or a corresponding mutation in any of the amino acid sequences provided in SEQ ID NOs: 11-260, is mutated to any amino acid residue, except for D. In some embodiments, the D10 residue of the amino acid sequence provided in SEQ ID NO: 10, or a corresponding mutation in any of the amino acid sequences provided in SEQ ID NOs: 11-260, is mutated to an A. In some embodiments, the H840 residue of the amino acid sequence provided in SEQ ID NO: 10, or a corresponding residue in any of the amino acid sequences provided in SEQ ID NOs: 11-260, is an H. In some embodiments, the H840 residue of the amino acid sequence provided in SEQ ID NO: 10, or a corresponding mutation in any of the amino acid sequences provided in SEQ ID NOs: 11-260, is mutated to any amino acid residue, except for H. In some embodiments, the H840 residue of the amino acid sequence provided in SEQ ID NO: 10, or a corresponding mutation in any of the amino acid sequences provided in SEQ ID NOs: 11-260, is mutated to an A. In some embodiments, the D10 residue of the amino acid sequence provided in SEQ ID NO: 10, or a corresponding residue in any of the amino acid sequences provided in SEQ ID NOs: 11-260, is a D.

A number of Cas9 sequences from various species were aligned to determine whether corresponding homologous amino acid residues of D10 and H840 of SEQ ID NO: 10 or SEQ ID NO: 11 can be identified in other Cas9 proteins, allowing the generation of Cas9 variants with corresponding mutations of the homologous amino acid residues. The alignment was carried out using the NCBI Constraint-based Multiple Alignment Tool (COBALT (accessible at st-va.ncbi.nlm.nih.gov/tools/cobalt), with the following parameters. Alignment parameters: Gap penalties −11,−1; End-Gap penalties −5,−1. CDD Parameters: Use RPS BLAST on; Blast E-value 0.003; Find Conserved columns and Recompute on. Query Clustering Parameters: Use query clusters on; Word Size 4; Max cluster distance 0.8; Alphabet Regular.

An exemplary alignment of four Cas9 sequences is provided below. The Cas9 sequences in the alignment are:

Sequence 1 (S1): SEQ ID NO: 11|WP_010922251|gi 499224711|type II CRISPR RNA-guided endonuclease Cas9 [*Streptococcus pyogenes*]; Sequence 2 (S2): SEQ ID NO: 12|WP_039695303|gi 746743737|type II CRISPR RNA-guided endonuclease Cas9 [*Streptococcus gallolyticus*]; Sequence 3 (S3): SEQ ID NO: 13|WP_045635197|gi 782887988|type II CRISPR RNA-guided endonuclease Cas9 [*Streptococcus mitis*]; Sequence 4 (S4): SEQ ID NO: 14|5AXW_A|gi 924443546|*Staphylococcus aureus* Cas9. The HNH domain (bold and underlined) and the RuvC domain (boxed) are identified for each of the four sequences. Amino acid residues 10 and 840 in S1 and the homologous amino acids in the aligned sequences are identified with an asterisk following the respective amino acid residue.

```
S1     1    --MDKK-YSIGLD*IGTNSVGWAVITDEYKVPSKKFKVLGNTDRHSIKKNLI--GALLFDSG--ETAEATRLKRTARRRYT    73

S2     1    --MTKKNYSIGLD*IGTNSVGWAVITDDYKVPAKKMKVLGNTDKKYIKKNLL--GALLFDSG--ETAEATRLKRTARRRYT    74

S3     1    --M-KKGYSIGLD*IGTNSVGFAVITDDYKVPSKKMKVLGNTDKRFIKKNLI--GALLFDEG--TTAEARRLKRTARRRYT    73

S4     1    GSHMKRNYILGLD*IGITSVGYGII--DYET----------------RDVIDAGVRLFKEANVENNEGRRSKRGARRLKR    61

S1     74   RRKNRICYLQEIFSNEMAKVDDSFEHRLEESELVEEDKKHERHPIFGNIVDEVAYHEKYPTIYHLRKKLVDSTDKADLRL    153

S2     75   RRKNRLRYLQEIFANETAKVDESFFQRLDESFLTDDDKTEDSHPIFGNKAEEDAYHQKFPTIYHLRKHLADSSEKADLRL    154

S3     74   RRKNRLRYLQEIFSEEMSKVDSSFEHRLDDSFLIPEDKRESKYPIFATLTEEKEYHKQFPTIYHLRKQLADSKEKTDLRL    153

S4     62   RRRHRIQRVKKLL--------------FDYNLLTD------------------HSELSGINPYEARVKGLSQKLSEEE    107

S1     154  IYLALAHNIKERGHFLIEGDLNPDNSDVDKLFIQLVQTYNQLFEENPINASGVDAKAILSARLSKSRRLENLIAQLPGEK    233

S2     155  VYLALAHMIKERGHFLIEGELNAENTDVQKIFADFVGVYNRTFDDSHLSEITVDVASILTEKISKSRRLENLIKYYPTEK    234

S3     154  TYLALAHMIKYRGHFLYEEAFDIKNNDIQKIFNEFISIYDNTFEGSSLSGQNAQVEAIFTDKISKSAKRERVLKLEPDEK    233

S4     108  FSAALLHLAKRRG----------------------VHNVNEVEEDT--------------------------------    131

S1     234  KNGLFGNLIALSLGLTPNEKSNFDLAEDAKLQLSKDTYDDDLDNLLAQIGDQYADLFLAAKNLSDAILLSDILRVNTEIT    313

S2     235  KNTLFGNLIALALGLQPNEKTNFKLSEDAKLQFSKDTYEEDLEELLGKIGDDYADLFTSAKNLYDAILLSGILTVDDNST    314

S3     234  STGLFSEFLKLIVGNQADFKKHFDLEDKAPLQFSKDTYDEDLENLLGQIGDDFTDLFVSAKKLYDAILLSGILTVTDPST    313

S4     132  -----GNELS-----------------TKEQISRN-------------------------------------------    144

S1     314  KAPLSASMIKRYDEHHQDLTLLKALVRQQLPEKYKEIFFDQSKNGYAGYIDGGASQEEFYKFIKPILEKM--DGTEELLV    391

S2     315  KAPLSASMIKRYVEHHEDLEKLKEFIKANKSELYHDIFKDKNKNGYAGYIENGVKQDEFYKYLKNILSKIKIDGSDYFLD    394

S3     314  KAPLSASMIERYENHQNDLAALKQFIKNNLPEKYDEVFSDQSKDGYAGYIDGKTTQETFYKYIKNLLSKF--EGTDYFLD    391

S4     145  ----SKALEEKYVAELQ-------------------------------------------LERLKKDG------    165

S1     392  KLNREDLLRKQRTFDNGSIPHQIHLGELHAILRRQEDFYPFLKDNREKIEKILTFRIPYYVGPLARGNSRFAWMTRKSEE    471

S2     395  KIEREDFLRKQRTFDNGSIPHQIHLQEMHAILRRQGDYYPFLKEKQDRIEKILTFRIPYYVGPLVRKDSRFAWAEYRSDE    474

S3     392  KIEREDFLRKQRTFDNGSIPHQIHLQEMNAILRRQGEYYPFLKDNKEKIEKILTFRIPYYVGPLARGNRDFAWLTRNSDE    471

S4     166  --EVRGSINRFKTSD--------YVKEAKQLLKVQKAYHQLDQSFIDTYIDLLETRRTYYEGP--GEGSPFGW------K    227

S1     472  TITPWNFEEVVDKGASAQSFIERMTNFDKNLPNEKVLPKHSLLYEYFTVYNELTKVKYVTEGMRKPAFLSGEQKKAIVDL    551

S2     475  KITPWNFDKVIDKEKSAEKFITRMTLNDLYLPEEKVLPKHSHVYETYAVYNELTKIKYVNEQGKE-SFFDSNMKQEIFDH    553

S3     472  AIRPWNFEEIVDKASSAEDFINKMTNYDLYLPEEKVLPKHSLLYETFAVYNELTKVKFIAEGLRDYQFLDSGQKKQIVNQ    551

S4     228  DIKEW--------------YEMLMGHCTYFPEELRSVKYAYNADLYNALNDLNNLVITRDENEK---LEYYEKFQIIEN    289

S1     552  LEKTNRKVTVKQLKEDYFKKIECFDSVEISGVEDR---FNASLGTYHDLLKIIKDKDFLDNEENEDILEDIVLTLTLFED    628

S2     554  VFKENRKVTKEKLLNYLNKEFPEYRIKDLIGLDKENKSFNASLGTYHDLKKIL-DKAFLDDKVNEEVIEDIIKTLTLFED    632

S3     552  LEKENRKVTEKDIIHYLHN-VDGYDGIELKGIEKQ---FNASLSTYHDLLKIIKDKEEMDDAKNEAILENIVHTLTIFED    627

S4     290  VFKQKKKPTLKQIAKEILVNEEDIKGYRVTSTGKPEF---TNLKVYHDIKDITARKEII---ENAELLDQIAKILTIYQS    363

S1     629  REMIEERLKTYAHLFDDKVMKQLKR-RRYTGWGRLSRKLINGIRDKQSGKTILDFLKSDGFANRNFMQLIHDDSLTFKED    707

S2     633  KDMIHERLQKYSDIFTANQLKKLER-RHYTGWGRLSYKLINGIRNKENNKTILDYLIDDGSANRNFMQLINDDTLPFKQI    711

S3     628  REMIKQRLAQYDSLFDEKVIKALTR-RHYTGWGKLSAKLINGICDKQTGNTILDYLIDDGKINRNFMQLINDDGLSFKEI    706

S4     364  SEDIQEELTNLNSELTQEEIEQISNLKGYTGTHNLSLKAINLILDE------LWHTNDNQIAIFNRLKLVP--------    428
```

```
S1   708  IQKAQVSGQG DSLHEHIANLAGSPAIKKGILQTVKVVDELVKVMGRHKPENIVIEMA RENQTT------QK GQKNSRERM         781
S2   712  IQKSQVVGDV DDIEAVVHDLPGSPAIKKGILQSVKIVDELVKVMG-GNPDNIVIEMA RENQTT------NR GRSQSQQRL         784
S3   707  IQKAQVIGKT DDVKQVVQELSGSPAIKKGILQSIKIVDELVKVMG-HAPESIVIEMA RENQTT------AR GKKNSQQRY         779
S4   429  -KKVDLSQQK EIPTTLVDDFILSPVVKRSFIQSIKVINAIIKKYG--LPNDIIIELA REKNSKDAQKMINE MQKRNRQTN         505

S1   782  KRIEEGIKELGSQIL-------KEHPVENTQLQNEKLYLYYLQNGRDMYVDQELDINRLSD----YDVDH*IVPQSFLKDD         850
S2   785  KKLQNSLKELGSNILNEEKPSYIEDKVENSHLQNDQLFLYYIQNGKDMYTGDELDIDHLSD----YDIDH*IIPQAFIKDD         860
S3   780  KRIEDSLKILASGL---DSNILKENPTDNNQLQNDRLFLYYLQNGKDMYTGEALDINQLSS----YDIDH*IIPQAFIKDD         852
S4   506  ERIEEIIRTTGK--------------ENAKYLIEKIKLHDMQEGKCLYSLEAIPLEDLLNNPFNYEVDH*IIPRSVSFDN         570

S1   851  SIDNKVLTRSDKNRGKSDNVPSEEVVKKMKNYWRQLLNAKLITQRKEDN-LTK AERGGL-SELD------KAGFIKRQLV   922
S2   861  SIDNRVLTSSAKNRGKSDDVPSLDIVRARKAEWVRLYKSGLISKRKEDN-LTK AERGGL-TEAD------KAGFIKRQLV   932
S3   853  SLDNRVLTSSKDNRGKSDNVPSIEVVQKRKAFWQQLLDSKLISERKFNN-LTK AERGGL-DERD------KVGFIKRQLV   924
S4   571  SFNNKVLVKQEEASKKGNRTPFQYLSSSDSKISYETFKKHILNLAKGKGRISK TKKEYLLEERDINRFSVQKDFINRNLV   650

S1   923  ETRQITKHVAQILDSRMNTKYDENDKLIREVKVITLKSKLVSDFRKDFQFYKVREINNYHHAHDAYLNAVVGTALIKKYP   1002
S2   933  ETRQITKHVAQILDARFNTEHDENDKVIRDVKVITLKSNLVSQFRKDFEFYKVREINDYHHAHDAYLNAVVGTALLKKYP   1012
S3   925  ETRQITKHVAQILDARYNTEVNEKDKKNRTVKIITLKSNLVSNFRKEFRLYKVREINDYHHAHDAYLNAVVAKAILKKYP   1004
S4   651  DTRYATRGLMNLLRSYFRVN-------NLDVKVKSINGGFTSFLRRKWKFKKERNKGYKHHAEDALIIA----------   712

S1   1003 KLESEFVYGDYKVYDVRKMIAKSEQ--EIGKATAKYFFYSNIMNFFKTEITLANGEIRKRPLIETNGETGEIVWDKG---  1077
S2   1013 KLASEFVYGEYKKYDIRKFITNSSD-----KATAKYFFYSNLMNFFKTKVKYADGTVFERPIIETNAD-GEIAWNKQ---  1083
S3   1005 KLEPEFVYGEYQKYDLKRYISRSKDPKEVEKATEKYFFYSNLLNFFKEEVHYADGTIVKRENIEYSKDTGEIAWNKE---  1081
S4   713  --NADFIFKEWKKLDKAKKVMENQM----------------------FEEKQAESMPEIETEQEYKEIFITPHQIK    764

S1   1078 -----RDFATVRKVLSMPQVNIVKKTEVQT GGFSKESILPKRNSDKLIARKKD---WDPKKYGGFDSPTVAYSVLVVAKV  1149
S2   1084 -----IDFEKVRKVLSYPQVNIVKKVETQT GGFSKESILPKGDSDKLIPRKTKKVYWDTKKYGGFDSPTVAYSVFVVADV  1158
S3   1082 -----KDFAIIKKVLSLPQVNIVKKREVQT GGFSKESILPKGNSDKLIPRKTKDILLDTTKYGGFDSPVIAYSILLIADI  1156
S4   765  HIKDFKDYKYSHRVDKKPNRELINDTLYST RKDDKGNTLIVNNLNGLYDKDNDKL----KKLIN-KSP----EKLLMYHH   835

S1   1150 EKGKSKKLKSVKELLGITIMERSSFEKNPI-DFLEAKG-----YKEVKKDLIIKLPKYSLFELENGRKRMLASAGELQKG  1223
S2   1159 EKGKAKKLKTVKELVGISIMERSFFEENPV-EFLENKG-----YHNIREDKLIKLPKYSLFEFEGGRRRLLASASELQKG  1232
S3   1157 EKGKAKKLKTVKTLVGITIMEKAAFEENPI-TFLENKG-----YHNVRKENILCLPKYSLFELENGRRRLLASAKELQKG  1230
S4   836  DPQTYQKLK--------LIMEQYGDEKNPLYKYYEETGNYLTKYSKKDNGPVIKKIKYYGNKLNAHLDITDDYPNSRNKV   907

S1   1224 NELALPSKYVNFLYLASHYEKLKGSPEDNEQKQLFVEQHKYLDEITEQISEFSKRVILADANLDKVLSAYNKH------   1297
S2   1233 NEMVLPGYLVELLYHAHRADNF-----NSTEYLNYVSEHKKEFEKVLSCVEDFANLYVDVEKNLSKIRAVADSM------   1301
S3   1231 NEIVLPVYLTTLLYHSKNVHKL-----DEPGHLEYIQKHRNEFKDLLNVSEFSQKYVLADANLEKIKSLYADN------   1299
S4   908  VKLSLKPYRFD-VYLDNGVYKFV-----TVKNLDVIK--KENYYEVNSKAYEEAKKLKKISNQAEFIASFYNNDLIKING   979
```

```
S1  1298  RDKPIREQAENITHLFTLTNLGAPAAFKYFDTTIDRKRYTSTKEVLDATLIHQSIT--------GLYETRI----DLSQL  1365

S2  1302  DNFSIEEISNSFINLLTLTALGAPADFNFLGEKIPRKRYTSTKECLNATLIHQSIT--------GLYETRI----DLSKL  1369

S3  1300  EQADIEILANSFINLLTFTALGAPAAFKFFGKDIDRKRYTTVSEILNATLIHQSIT--------GLYETWI----DLSKL  1367

S4   980  ELYRVIGVNNDLLNRIEVNMIDITYR-EYLENMNDKRPPRIIKTIASKT---QSIKKYSTDILGNLYEVKSKKHPQIIKK  1055

S1  1366  GGD 1368

S2  1370  GEE 1372

S3  1368  GED 1370

S4  1056  G-- 1056
```

The alignment demonstrates that amino acid sequences and amino acid residues that are homologous to a reference Cas9 amino acid sequence or amino acid residue can be identified across Cas9 sequence variants, including, but not limited to Cas9 sequences from different species, by identifying the amino acid sequence or residue that aligns with the reference sequence or the reference residue using alignment programs and algorithms known in the art. This disclosure provides Cas9 variants in which one or more of the amino acid residues identified by an asterisk in SEQ ID NOs: 11-14 (e.g., S1, S2, S3, and S4, respectively) are mutated as described herein. The residues D10 and H840 in Cas9 of SEQ ID NO: 10 that correspond to the residues identified in SEQ ID NOs: 11-14 by an asterisk are referred to herein as "homologous" or "corresponding" residues. Such homologous residues can be identified by sequence alignment, e.g., as described above, and by identifying the sequence or residue that aligns with the reference sequence or residue. Similarly, mutations in Cas9 sequences that correspond to mutations identified in SEQ ID NO: 10 herein, e.g., mutations of residues 10, and 840 in SEQ ID NO: 10, are referred to herein as "homologous" or "corresponding" mutations. For example, the mutations corresponding to the D10A mutation in SEQ ID NO: 10 or 51 (SEQ ID NO: 11) for the four aligned sequences above are D11A for S2, D10A for S3, and D13A for S4; the corresponding mutations for H840A in SEQ ID NO: 10 or S1 (SEQ ID NO: 11) are H850A for S2, H842A for S3, and H560A for S4.

A total of 250 Cas9 sequences (SEQ ID NOs: 11-260) from different species were aligned using the same algorithm and alignment parameters outlined above. Amino acid residues homologous to residues 10, and 840 of SEQ ID NO: 10 were identified in the same manner as outlined above. The alignments are provided below. The HNH domain (bold and underlined) and the RuvC domain (boxed) are identified for each of the four sequences. Single residues corresponding to amino acid residues 10, and 840 in SEQ ID NO: 10 are boxed in SEQ ID NO: 11 in the alignments, allowing for the identification of the corresponding amino acid residues in the aligned sequences.

| Accession | Description | SEQ ID NO |
|---|---|---|
| WP_010922251.1 | type II CRISPR RNA-guided endonuclease Cas9 [Streptococcus pyogenes] | SEQ ID NO: 11 |
| WP_039695303.1 | type II CRISPR RNA-guided endonuclease Cas9 [Streptococcus gallolyticus] | SEQ ID NO: 12 |
| WP_045635197.1 | type II CRISPR RNA-guided endonuclease Cas9 [Streptococcus mitis] | SEQ ID NO: 13 |
| 5AXW_A | Cas9, Chain A, Crystal Structure [Staphylococcus Aureus] | SEQ ID NO: 14 |
| WP_009880683.1 | type II CRISPR RNA-guided endonuclease Cas9 [Streptococcus pyogenes] | SEQ ID NO: 15 |
| WP_010922251.1 | type II CRISPR RNA-guided endonuclease Cas9 [Streptococcus pyogenes] | SEQ ID NO: 16 |
| WP_011054416.1 | type II CRISPR RNA-guided endonuclease Cas9 [Streptococcus pyogenes] | SEQ ID NO: 17 |
| WP_011284745.1 | type II CRISPR RNA-guided endonuclease Cas9 [Streptococcus pyogenes] | SEQ ID NO: 18 |
| WP_011285506.1 | type II CRISPR RNA-guided endonuclease Cas9 [Streptococcus pyogenes] | SEQ ID NO: 19 |
| WP_011527619.1 | type II CRISPR RNA-guided endonuclease Cas9 [Streptococcus pyogenes] | SEQ ID NO: 20 |
| WP_012560673.1 | type II CRISPR RNA-guided endonuclease Cas9 [Streptococcus pyogenes] | SEQ ID NO: 21 |
| WP_014407541.1 | type II CRISPR RNA-guided endonuclease Cas9 [Streptococcus pyogenes] | SEQ ID NO: 22 |
| WP_020905136.1 | type II CRISPR RNA-guided endonuclease Cas9 [Streptococcus pyogenes] | SEQ ID NO: 23 |
| WP_023080005.1 | type II CRISPR RNA-guided endonuclease Cas9 [Streptococcus pyogenes] | SEQ ID NO: 24 |
| WP_023610282.1 | type II CRISPR RNA-guided endonuclease Cas9 [Streptococcus pyogenes] | SEQ ID NO: 25 |
| WP_030125963.1 | type II CRISPR RNA-guided endonuclease Cas9 [Streptococcus pyogenes] | SEQ ID NO: 26 |
| WP_030126706.1 | type II CRISPR RNA-guided endonuclease Cas9 [Streptococcus pyogenes] | SEQ ID NO: 27 |
| WP_031488318.1 | type II CRISPR RNA-guided endonuclease Cas9 [Streptococcus pyogenes] | SEQ ID NO: 28 |
| WP_032460140.1 | type II CRISPR RNA-guided endonuclease Cas9 [Streptococcus pyogenes] | SEQ ID NO: 29 |
| WP_032461047.1 | type II CRISPR RNA-guided endonuclease Cas9 [Streptococcus pyogenes] | SEQ ID NO: 30 |
| WP_032462016.1 | type II CRISPR RNA-guided endonuclease Cas9 [Streptococcus pyogenes] | SEQ ID NO: 31 |
| WP_032462936.1 | type II CRISPR RNA-guided endonuclease Cas9 [Streptococcus pyogenes] | SEQ ID NO: 32 |
| WP_032464890.1 | type II CRISPR RNA-guided endonuclease Cas9 [Streptococcus pyogenes] | SEQ ID NO: 33 |
| WP_033888930.1 | type II CRISPR RNA-guided endonuclease Cas9 [Streptococcus pyogenes] | SEQ ID NO: 34 |
| WP_038431314.1 | type II CRISPR RNA-guided endonuclease Cas9 [Streptococcus pyogenes] | SEQ ID NO: 35 |
| WP_038432938.1 | type II CRISPR RNA-guided endonuclease Cas9 [Streptococcus pyogenes] | SEQ ID NO: 36 |
| WP_038434062.1 | type II CRISPR RNA-guided endonuclease Cas9 [Streptococcus pyogenes] | SEQ ID NO: 37 |
| BAQ51233.1 | CRISPR-associated protein, Csn1 family [Streptococcus pyogenes] | SEQ ID NO: 38 |
| KGE60162.1 | hypothetical protein MGAS2111_0903 [Streptococcus pyogenes MGAS2111] | SEQ ID NO: 39 |
| KGE60856.1 | CRISPR-associated endonuclease protein [Streptococcus pyogenes SS1447] | SEQ ID NO: 40 |
| WP_002989955.1 | MULTISPECIES: type II CRISPR RNA-guided endonuclease Cas9 [Streptococcus] | SEQ ID NO: 41 |
| WP_003030001.1 | MULTISPECIES: type II CRISPR RNA-guided endonuclease Cas9 [Streptococcus] | SEQ ID NO: 42 |
| WP_003065552.1 | MULTISPECIES: type II CRISPR RNA-guided endonuclease Cas9 [Streptococcus] | SEQ ID NO: 43 |
| WP_001040076.1 | type II CRISPR RNA-guided endonuclease Cas9 [Streptococcus agalactiae] | SEQ ID NO: 44 |
| WP_001040078.1 | type II CRISPR RNA-guided endonuclease Cas9 [Streptococcus agalactiae] | SEQ ID NO: 45 |
| WP_001040080.1 | type II CRISPR RNA-guided endonuclease Cas9 [Streptococcus agalactiae] | SEQ ID NO: 46 |
| WP_001040081.1 | type II CRISPR RNA-guided endonuclease Cas9 [Streptococcus agalactiae] | SEQ ID NO: 47 |
| WP_001040083.1 | type II CRISPR RNA-guided endonuclease Cas9 [Streptococcus agalactiae] | SEQ ID NO: 48 |
| WP_001040085.1 | type II CRISPR RNA-guided endonuclease Cas9 [Streptococcus agalactiae] | SEQ ID NO: 49 |
| WP_001040087.1 | type II CRISPR RNA-guided endonuclease Cas9 [Streptococcus agalactiae] | SEQ ID NO: 50 |
| WP_001040088.1 | type II CRISPR RNA-guided endonuclease Cas9 [Streptococcus agalactiae] | SEQ ID NO: 51 |
| WP_001040089.1 | type II CRISPR RNA-guided endonuclease Cas9 [Streptococcus agalactiae] | SEQ ID NO: 52 |
| WP_001040090.1 | type II CRISPR RNA-guided endonuclease Cas9 [Streptococcus agalactiae] | SEQ ID NO: 53 |
| WP_001040091.1 | type II CRISPR RNA-guided endonuclease Cas9 [Streptococcus agalactiae] | SEQ ID NO: 54 |
| WP_001040092.1 | type II CRISPR RNA-guided endonuclease Cas9 [Streptococcus agalactiae] | SEQ ID NO: 55 |
| WP_001040094.1 | type II CRISPR RNA-guided endonuclease Cas9 [Streptococcus agalactiae] | SEQ ID NO: 56 |
| WP_001040095.1 | type II CRISPR RNA-guided endonuclease Cas9 [Streptococcus agalactiae] | SEQ ID NO: 57 |
| WP_001040096.1 | type II CRISPR RNA-guided endonuclease Cas9 [Streptococcus agalactiae] | SEQ ID NO: 58 |
| WP_001040097.1 | type II CRISPR RNA-guided endonuclease Cas9 [Streptococcus agalactiae] | SEQ ID NO: 59 |
| WP_001040098.1 | type II CRISPR RNA-guided endonuclease Cas9 [Streptococcus agalactiae] | SEQ ID NO: 60 |
| WP_001040099.1 | type II CRISPR RNA-guided endonuclease Cas9 [Streptococcus agalactiae] | SEQ ID NO: 61 |
| WP_001040100.1 | type II CRISPR RNA-guided endonuclease Cas9 [Streptococcus agalactiae] | SEQ ID NO: 62 |

-continued

| | | |
|---|---|---|
| WP_001040104.1 | type II CRISPR RNA-guided endonuclease Cas9 [Streptococcus agalactiae] | SEQ ID NO: 63 |
| WP_001040105.1 | type II CRISPR RNA-guided endonuclease Cas9 [Streptococcus agalactiae] | SEQ ID NO: 64 |
| WP_001040106.1 | type II CRISPR RNA-guided endonuclease Cas9 [Streptococcus agalactiae] | SEQ ID NO: 65 |
| WP_001040107.1 | type II CRISPR RNA-guided endonuclease Cas9 [Streptococcus agalactiae] | SEQ ID NO: 66 |
| WP_001040108.1 | type II CRISPR RNA-guided endonuclease Cas9 [Streptococcus agalactiae] | SEQ ID NO: 67 |
| WP_001040109.1 | type II CRISPR RNA-guided endonuclease Cas9 [Streptococcus agalactiae] | SEQ ID NO: 68 |
| WP_001040110.1 | type II CRISPR RNA-guided endonuclease Cas9 [Streptococcus agalactiae] | SEQ ID NO: 69 |
| WP_015058523.1 | type II CRISPR RNA-guided endonuclease Cas9 [Streptococcus agalactiae] | SEQ ID NO: 70 |
| WP_017643650.1 | type II CRISPR RNA-guided endonuclease Cas9 [Streptococcus agalactiae] | SEQ ID NO: 71 |
| WP_017647151.1 | type II CRISPR RNA-guided endonuclease Cas9 [Streptococcus agalactiae] | SEQ ID NO: 72 |
| WP_017648376.1 | type II CRISPR RNA-guided endonuclease Cas9 [Streptococcus agalactiae] | SEQ ID NO: 73 |
| WP_017649527.1 | type II CRISPR RNA-guided endonuclease Cas9 [Streptococcus agalactiae] | SEQ ID NO: 74 |
| WP_017771611.1 | type II CRISPR RNA-guided endonuclease Cas9 [Streptococcus agalactiae] | SEQ ID NO: 75 |
| WP_017771984.1 | type II CRISPR RNA-guided endonuclease Cas9 [Streptococcus agalactiae] | SEQ ID NO: 76 |
| CFQ25032.1 | CRISPR-associated protein [Streptococcus agalactiae] | SEQ ID NO: 77 |
| CFV16040.1 | CRISPR-associated protein [Streptococcus agalactiae] | SEQ ID NO: 78 |
| KLJ37842.1 | CRISPR-associated protein Csn1 [Streptococcus agalactiae] | SEQ ID NO: 79 |
| KLJ72361.1 | CRISPR-associated protein Csn1 [Streptococcus agalactiae] | SEQ ID NO: 80 |
| KLL20707.1 | CRISPR-associated protein Csn1 [Streptococcus agalactiae] | SEQ ID NO: 81 |
| KLL42645.1 | CRISPR-associated protein Csn1 [Streptococcus agalactiae] | SEQ ID NO: 82 |
| WP_047207273.1 | type II CRISPR RNA-guided endonuclease Cas9 [Streptococcus agalactiae] | SEQ ID NO: 83 |
| WP_047209694.1 | type II CRISPR RNA-guided endonuclease Cas9 [Streptococcus agalactiae] | SEQ ID NO: 84 |
| WP_050198062.1 | type II CRISPR RNA-guided endonuclease Cas9 [Streptococcus agalactiae] | SEQ ID NO: 85 |
| WP_050201642.1 | type II CRISPR RNA-guided endonuclease Cas9 [Streptococcus agalactiae] | SEQ ID NO: 86 |
| WP_050204027.1 | type II CRISPR RNA-guided endonuclease Cas9 [Streptococcus agalactiae] | SEQ ID NO: 87 |
| WP_050881965.1 | type II CRISPR RNA-guided endonuclease Cas9 [Streptococcus agalactiae] | SEQ ID NO: 88 |
| WP_050886065.1 | type II CRISPR RNA-guided endonuclease Cas9 [Streptococcus agalactiae] | SEQ ID NO: 89 |
| AHN30376.1 | CRISPR-associated protein Csn1 [Streptococcus agalactiae 138P] | SEQ ID NO: 90 |
| EAO78426.1 | reticulocyte binding protein [Streptococcus agalactiae H36B] | SEQ ID NO: 91 |
| CCW42055.1 | CRISPR-associated protein, SAG0894 family [Streptococcus agalactiae ILRI112] | SEQ ID NO: 92 |
| WP_003041502.1 | type II CRISPR RNA-guided endonuclease Cas9 [Streptococcus anginosus] | SEQ ID NO: 93 |
| WP_037593752.1 | type II CRISPR RNA-guided endonuclease Cas9 [Streptococcus anginosus] | SEQ ID NO: 94 |
| WP_049516684.1 | CRISPR-associated protein Csn1 [Streptococcus anginosus] | SEQ ID NO: 95 |
| GAD46167.1 | hypothetical protein ANG6_0662 [Streptococcus anginosus T5] | SEQ ID NO: 96 |
| WP_018363470.1 | type II CRISPR RNA-guided endonuclease Cas9 [Streptococcus caballi] | SEQ ID NO: 97 |
| WP_003043819.1 | type II CRISPR RNA-guided endonuclease Cas9 [Streptococcus canis] | SEQ ID NO: 98 |
| WP_006269658.1 | type II CRISPR RNA-guided endonuclease Cas9 [Streptococcus constellatus] | SEQ ID NO: 99 |
| WP_048800889.1 | type II CRISPR RNA-guided endonuclease Cas9 [Streptococcus constellatus] | SEQ ID NO: 100 |
| WP_012767106.1 | type II CRISPR RNA-guided endonuclease Cas9 [Streptococcus dysgalactiae] | SEQ ID NO: 101 |
| WP_014612333.1 | type II CRISPR RNA-guided endonuclease Cas9 [Streptococcus dysgalactiae] | SEQ ID NO: 102 |
| WP_015017095.1 | type II CRISPR RNA-guided endonuclease Cas9 [Streptococcus dysgalactiae] | SEQ ID NO: 103 |
| WP_015057649.1 | type II CRISPR RNA-guided endonuclease Cas9 [Streptococcus dysgalactiae] | SEQ ID NO: 104 |
| WP_048327215.1 | type II CRISPR RNA-guided endonuclease Cas9 [Streptococcus dysgalactiae] | SEQ ID NO: 105 |
| WP_049519324.1 | CRISPR-associated protein Csn1 [Streptococcus dysgalactiae] | SEQ ID NO: 106 |
| WP_012515931.1 | type II CRISPR RNA-guided endonuclease Cas9 [Streptococcus equi] | SEQ ID NO: 107 |
| WP_021320964.1 | type II CRISPR RNA-guided endonuclease Cas9 [Streptococcus equi] | SEQ ID NO: 108 |
| WP_037581760.1 | type II CRISPR RNA-guided endonuclease Cas9 [Streptococcus equi] | SEQ ID NO: 109 |
| WP_044232481.1 | type II CRISPR RNA-guided endonuclease Cas9 [Streptococcus equinus] | SEQ ID NO: 110 |
| WP_009854540.1 | type II CRISPR RNA-guided endonuclease Cas9 [Streptococcus gallolyticus] | SEQ ID NO: 111 |
| WP_012962174.1 | type II CRISPR RNA-guided endonuclease Cas9 [Streptococcus gallolyticus] | SEQ ID NO: 112 |
| WP_039695303.1 | type II CRISPR RNA-guided endonuclease Cas9 [Streptococcus gallolyticus] | SEQ ID NO: 113 |
| WP_014334983.1 | type II CRISPR RNA-guided endonuclease Cas9 [Streptococcus infantarius] | SEQ ID NO: 114 |
| WP_003099269.1 | type II CRISPR RNA-guided endonuclease Cas9 [Streptococcus iniae] | SEQ ID NO: 115 |

-continued

| Accession | Description | SEQ ID NO |
|---|---|---|
| AHY15608.1 | CRISPR-associated protein Csn1 [Streptococcus iniae] | SEQ ID NO: 116 |
| AHY17476.1 | CRISPR-associated protein Csn1 [Streptococcus iniae] | SEQ ID NO: 117 |
| ESR09100.1 | hypothetical protein IUSA1_08595 [Streptococcus iniae IUSA1] | SEQ ID NO: 118 |
| AGM98575.1 | CRISPR-associated protein Cas9/Csn1, subtype II/NMEMI [Streptococcus iniae SF1] | SEQ ID NO: 119 |
| ALF27331.1 | CRISPR-associated protein Csn1 [Streptococcus intermedius] | SEQ ID NO: 120 |
| WP_018372492.1 | type II CRISPR RNA-guided endonuclease Cas9 [Streptococcus massiliensis] | SEQ ID NO: 121 |
| WP_045618028.1 | type II CRISPR RNA-guided endonuclease Cas9 [Streptococcus mitis] | SEQ ID NO: 122 |
| WP_045635197.1 | type II CRISPR RNA-guided endonuclease Cas9 [Streptococcus mitis] | SEQ ID NO: 123 |
| WP_002263549.1 | type II CRISPR RNA-guided endonuclease Cas9 [Streptococcus mutans] | SEQ ID NO: 124 |
| WP_002263887.1 | type II CRISPR RNA-guided endonuclease Cas9 [Streptococcus mutans] | SEQ ID NO: 125 |
| WP_002264920.1 | type II CRISPR RNA-guided endonuclease Cas9 [Streptococcus mutans] | SEQ ID NO: 126 |
| WP_002269043.1 | type II CRISPR RNA-guided endonuclease Cas9 [Streptococcus mutans] | SEQ ID NO: 127 |
| WP_002269448.1 | type II CRISPR RNA-guided endonuclease Cas9 [Streptococcus mutans] | SEQ ID NO: 128 |
| WP_002271977.1 | type II CRISPR RNA-guided endonuclease Cas9 [Streptococcus mutans] | SEQ ID NO: 129 |
| WP_002272766.1 | type II CRISPR RNA-guided endonuclease Cas9 [Streptococcus mutans] | SEQ ID NO: 130 |
| WP_002273241.1 | type II CRISPR RNA-guided endonuclease Cas9 [Streptococcus mutans] | SEQ ID NO: 131 |
| WP_002275430.1 | type II CRISPR RNA-guided endonuclease Cas9 [Streptococcus mutans] | SEQ ID NO: 132 |
| WP_002276448.1 | type II CRISPR RNA-guided endonuclease Cas9 [Streptococcus mutans] | SEQ ID NO: 133 |
| WP_002277050.1 | type II CRISPR RNA-guided endonuclease Cas9 [Streptococcus mutans] | SEQ ID NO: 134 |
| WP_002277364.1 | type II CRISPR RNA-guided endonuclease Cas9 [Streptococcus mutans] | SEQ ID NO: 135 |
| WP_002279025.1 | type II CRISPR RNA-guided endonuclease Cas9 [Streptococcus mutans] | SEQ ID NO: 136 |
| WP_002279859.1 | type II CRISPR RNA-guided endonuclease Cas9 [Streptococcus mutans] | SEQ ID NO: 137 |
| WP_002280230.1 | type II CRISPR RNA-guided endonuclease Cas9 [Streptococcus mutans] | SEQ ID NO: 138 |
| WP_002281696.1 | type II CRISPR RNA-guided endonuclease Cas9 [Streptococcus mutans] | SEQ ID NO: 139 |
| WP_002282247.1 | type II CRISPR RNA-guided endonuclease Cas9 [Streptococcus mutans] | SEQ ID NO: 140 |
| WP_002282906.1 | type II CRISPR RNA-guided endonuclease Cas9 [Streptococcus mutans] | SEQ ID NO: 141 |
| WP_002283846.1 | type II CRISPR RNA-guided endonuclease Cas9 [Streptococcus mutans] | SEQ ID NO: 142 |
| WP_002287255.1 | type II CRISPR RNA-guided endonuclease Cas9 [Streptococcus mutans] | SEQ ID NO: 143 |
| WP_002288990.1 | type II CRISPR RNA-guided endonuclease Cas9 [Streptococcus mutans] | SEQ ID NO: 144 |
| WP_002289641.1 | type II CRISPR RNA-guided endonuclease Cas9 [Streptococcus mutans] | SEQ ID NO: 145 |
| WP_002290427.1 | type II CRISPR RNA-guided endonuclease Cas9 [Streptococcus mutans] | SEQ ID NO: 146 |
| WP_002295753.1 | type II CRISPR RNA-guided endonuclease Cas9 [Streptococcus mutans] | SEQ ID NO: 147 |
| WP_002296423.1 | type II CRISPR RNA-guided endonuclease Cas9 [Streptococcus mutans] | SEQ ID NO: 148 |
| WP_002304487.1 | type II CRISPR RNA-guided endonuclease Cas9 [Streptococcus mutans] | SEQ ID NO: 149 |
| WP_003305844.1 | type II CRISPR RNA-guided endonuclease Cas9 [Streptococcus mutans] | SEQ ID NO: 150 |
| WP_003307203.1 | type II CRISPR RNA-guided endonuclease Cas9 [Streptococcus mutans] | SEQ ID NO: 151 |
| WP_002310390.1 | type II CRISPR RNA-guided endonuclease Cas9 [Streptococcus mutans] | SEQ ID NO: 152 |
| WP_002352408.1 | type II CRISPR RNA-guided endonuclease Cas9 [Streptococcus mutans] | SEQ ID NO: 153 |
| WP_012997688.1 | type II CRISPR RNA-guided endonuclease Cas9 [Streptococcus mutans] | SEQ ID NO: 154 |
| WP_014677909.1 | type II CRISPR RNA-guided endonuclease Cas9 [Streptococcus mutans] | SEQ ID NO: 155 |
| WP_019312892.1 | type II CRISPR RNA-guided endonuclease Cas9 [Streptococcus mutans] | SEQ ID NO: 156 |
| WP_019313659.1 | type II CRISPR RNA-guided endonuclease Cas9 [Streptococcus mutans] | SEQ ID NO: 157 |
| WP_019314093.1 | type II CRISPR RNA-guided endonuclease Cas9 [Streptococcus mutans] | SEQ ID NO: 158 |
| WP_019315370.1 | type II CRISPR RNA-guided endonuclease Cas9 [Streptococcus mutans] | SEQ ID NO: 159 |
| WP_019803776.1 | type II CRISPR RNA-guided endonuclease Cas9 [Streptococcus mutans] | SEQ ID NO: 160 |
| WP_019805234.1 | type II CRISPR RNA-guided endonuclease Cas9 [Streptococcus mutans] | SEQ ID NO: 161 |
| WP_024783594.1 | type II CRISPR RNA-guided endonuclease Cas9 [Streptococcus mutans] | SEQ ID NO: 162 |
| WP_024784288.1 | type II CRISPR RNA-guided endonuclease Cas9 [Streptococcus mutans] | SEQ ID NO: 163 |
| WP_024784666.1 | type II CRISPR RNA-guided endonuclease Cas9 [Streptococcus mutans] | SEQ ID NO: 164 |
| WP_024784894.1 | type II CRISPR RNA-guided endonuclease Cas9 [Streptococcus mutans] | SEQ ID NO: 165 |
| WP_024786433.1 | type II CRISPR RNA-guided endonuclease Cas9 [Streptococcus mutans] | SEQ ID NO: 166 |
| WP_049473442.1 | CRISPR-associated protein Csn1 [Streptococcus mutans] | SEQ ID NO: 167 |
| WP_049474547.1 | CRISPR-associated protein Csn1 [Streptococcus mutans] | SEQ ID NO: 168 |

-continued

| Accession | Description | SEQ ID NO |
|---|---|---|
| EMC03581.1 | hypothetical protein SMU69_09359 [Streptococcus mutans NLML4] | SEQ ID NO: 169 |
| WP_000428812.1 | type II CRISPR RNA-guided endonuclease Cas9 [Streptococcus oralis] | SEQ ID NO: 170 |
| WP_000428613.1 | type II CRISPR RNA-guided endonuclease Cas9 [Streptococcus oralis] | SEQ ID NO: 171 |
| WP_049523028.1 | CRISPR-associated protein Csn1 [Streptococcus parasanguinis] | SEQ ID NO: 172 |
| WP_003107102.1 | type II CRISPR RNA-guided endonuclease Cas9 [Streptococcus parauberis] | SEQ ID NO: 173 |
| WP_054279288.1 | type II CRISPR RNA-guided endonuclease Cas9 [Streptococcus phocae] | SEQ ID NO: 174 |
| WP_049531101.1 | CRISPR-associated protein Csn1 [Streptococcus pseudopneumoniae] | SEQ ID NO: 175 |
| WP_049538452.1 | CRISPR-associated protein Csn1 [Streptococcus pseudopneumoniae] | SEQ ID NO: 176 |
| WP_049549711.1 | CRISPR-associated protein Csn1 [Streptococcus pseudopneumoniae] | SEQ ID NO: 177 |
| WP_007896501.1 | type II CRISPR RNA-guided endonuclease Cas9 [Streptococcus pseudoporcinus] | SEQ ID NO: 178 |
| EFR44625.1 | CRISPR-associated protein, Csn1 family [Streptococcus pseudoporcinus SPIN 20026] | SEQ ID NO: 179 |
| WP_002897477.1 | type II CRISPR RNA-guided endonuclease Cas9 [Streptococcus sanguinis] | SEQ ID NO: 180 |
| WP_002906454.1 | type II CRISPR RNA-guided endonuclease Cas9 [Streptococcus sanguinis] | SEQ ID NO: 181 |
| WP_009729476.1 | type II CRISPR RNA-guided endonuclease Cas9 [Streptococcus sp. F0441] | SEQ ID NO: 182 |
| CQR24647.1 | CRISPR-associated protein [Streptococcus sp. FF10] | SEQ ID NO: 183 |
| WP_000066813.1 | type II CRISPR RNA-guided endonuclease Cas9 [Streptococcus sp. M334] | SEQ ID NO: 184 |
| WP_009754323.1 | type II CRISPR RNA-guided endonuclease Cas9 [Streptococcus sp. taxon 056] | SEQ ID NO: 185 |
| WP_044674937.1 | type II CRISPR RNA-guided endonuclease Cas9 [Streptococcus suis] | SEQ ID NO: 186 |
| WP_044676715.1 | type II CRISPR RNA-guided endonuclease Cas9 [Streptococcus suis] | SEQ ID NO: 187 |
| WP_044680361.1 | type II CRISPR RNA-guided endonuclease Cas9 [Streptococcus suis] | SEQ ID NO: 188 |
| WP_044681799.1 | type II CRISPR RNA-guided endonuclease Cas9 [Streptococcus suis] | SEQ ID NO: 189 |
| WP_049533112.1 | CRISPR-associated protein Csn1 [Streptococcus suis] | SEQ ID NO: 190 |
| WP_029090905.1 | type II CRISPR RNA-guided endonuclease Cas9 [Brochothrix thermosphacta] | SEQ ID NO: 191 |
| WP_065066966.1 | type II CRISPR RNA-guided endonuclease Cas9 [Catenibacterium mitsuokai] | SEQ ID NO: 192 |
| AIT42264.1 | Cas9hc:NLS:HA [Cloning vector pYB196] | SEQ ID NO: 193 |
| WP_034440723.1 | type II CRISPR endonuclease Cas9 [Clostridiales bacterium S5-A11] | SEQ ID NO: 194 |
| AKQ21048.1 | Cas9 [CRISPR-mediated gene targeting vector p(bh5p68-Cas9)] | SEQ ID NO: 195 |
| WP_004636532.1 | type II CRISPR RNA-guided endonuclease Cas9 [Dolosigranulum pigrum] | SEQ ID NO: 196 |
| WP_002364836.1 | MULTISPECIES: type II CRISPR RNA-guided endonuclease Cas9 [Enterococcus] | SEQ ID NO: 197 |
| WP_016631044.1 | MULTISPECIES: type II CRISPR RNA-guided endonuclease Cas9 [Enterococcus] | SEQ ID NO: 198 |
| EMS75795.1 | hypothetical protein H318_06676 [Enterococcus durans IPLA 655] | SEQ ID NO: 199 |
| WP_002373311.1 | type II CRISPR RNA-guided endonuclease Cas9 [Enterococcus faecalis] | SEQ ID NO: 200 |
| WP_002378009.1 | type II CRISPR RNA-guided endonuclease Cas9 [Enterococcus faecalis] | SEQ ID NO: 201 |
| WP_002407324.1 | type II CRISPR RNA-guided endonuclease Cas9 [Enterococcus faecalis] | SEQ ID NO: 202 |
| WP_002413717.1 | type II CRISPR RNA-guided endonuclease Cas9 [Enterococcus faecalis] | SEQ ID NO: 203 |
| WP_010775580.1 | type II CRISPR RNA-guided endonuclease Cas9 [Enterococcus faecalis] | SEQ ID NO: 204 |
| WP_010818269.1 | type II CRISPR RNA-guided endonuclease Cas9 [Enterococcus faecalis] | SEQ ID NO: 205 |
| WP_010824395.1 | type II CRISPR RNA-guided endonuclease Cas9 [Enterococcus faecalis] | SEQ ID NO: 206 |
| WP_016622645.1 | type II CRISPR RNA-guided endonuclease Cas9 [Enterococcus faecalis] | SEQ ID NO: 207 |
| WP_033624816.1 | type II CRISPR RNA-guided endonuclease Cas9 [Enterococcus faecalis] | SEQ ID NO: 208 |
| WP_033625576.1 | type II CRISPR RNA-guided endonuclease Cas9 [Enterococcus faecalis] | SEQ ID NO: 209 |
| WP_033789179.1 | type II CRISPR RNA-guided endonuclease Cas9 [Enterococcus faecalis] | SEQ ID NO: 210 |
| WP_002310644.1 | type II CRISPR RNA-guided endonuclease Cas9 [Enterococcus faecium] | SEQ ID NO: 211 |
| WP_002312694.1 | type II CRISPR RNA-guided endonuclease Cas9 [Enterococcus faecium] | SEQ ID NO: 212 |
| WP_002314015.1 | type II CRISPR RNA-guided endonuclease Cas9 [Enterococcus faecium] | SEQ ID NO: 213 |
| WP_002320716.1 | type II CRISPR RNA-guided endonuclease Cas9 [Enterococcus faecium] | SEQ ID NO: 214 |
| WP_002330729.1 | type II CRISPR RNA-guided endonuclease Cas9 [Enterococcus faecium] | SEQ ID NO: 215 |
| WP_002335161.1 | type II CRISPR RNA-guided endonuclease Cas9 [Enterococcus faecium] | SEQ ID NO: 216 |
| WP_002345439.1 | type II CRISPR RNA-guided endonuclease Cas9 [Enterococcus faecium] | SEQ ID NO: 217 |
| WP_034867970.1 | type II CRISPR RNA-guided endonuclease Cas9 [Enterococcus faecium] | SEQ ID NO: 218 |
| WP_047937432.1 | type II CRISPR RNA-guided endonuclease Cas9 [Enterococcus faecium] | SEQ ID NO: 219 |
| WP_010720994.1 | type II CRISPR RNA-guided endonuclease Cas9 [Enterococcus hirae] | SEQ ID NO: 220 |
| WP_010737004.1 | type II CRISPR RNA-guided endonuclease Cas9 [Enterococcus hirae] | SEQ ID NO: 221 |

-continued

| | | | |
|---|---|---|---|
| WP_034700478.1 | type II CRISPR RNA-guided endonuclease Cas9 [Enterococcus hirae] | SEQ ID NO: | 222 |
| WP_007209003.1 | type II CRISPR RNA-guided endonuclease Cas9 [Enterococcus italicus] | SEQ ID NO: | 223 |
| WP_023519017.1 | type II CRISPR RNA-guided endonuclease Cas9 [Enterococcus mundtii] | SEQ ID NO: | 224 |
| WP_010770040.1 | type II CRISPR RNA-guided endonuclease Cas9 [Enterococcus phoeniculicola] | SEQ ID NO: | 225 |
| WP_048604708.1 | type II CRISPR RNA-guided endonuclease Cas9 [Enterococcus sp. AM1] | SEQ ID NO: | 226 |
| WP_010750235.1 | type II CRISPR RNA-guided endonuclease Cas9 [Enterococcus villorum] | SEQ ID NO: | 227 |
| AII16583.1 | Cas9 endonuclease [Expression vector pCas9] | SEQ ID NO: | 228 |
| WP_029073316.1 | type II CRISPR RNA-guided endonuclease Cas9 [Kandleria vitulina] | SEQ ID NO: | 229 |
| WP_031589969.1 | type II CRISPR RNA-guided endonuclease Cas9 [Kandleria vitulina] | SEQ ID NO: | 230 |
| KDA45870.1 | CRISPR-associated protein Cas9/Csn1, subtype II/NMEMI [Lactobacillus animalis] | SEQ ID NO: | 231 |
| WP_039099354.1 | type II CRISPR RNA-guided endonuclease Cas9 [Lactobacillus curvatus] | SEQ ID NO: | 232 |
| AKP02966.1 | hypothetical protein ABB45_04605 [Lactobacillus farciminis] | SEQ ID NO: | 233 |
| WP_010991369.1 | type II CRISPR RNA-guided endonuclease Cas9 [Listeria innocua] | SEQ ID NO: | 234 |
| WP_033838504.1 | type II CRISPR RNA-guided endonuclease Cas9 [Listeria innocua] | SEQ ID NO: | 235 |
| EHN60060.1 | CRISPR-associated protein, Csn1 family [Listeria innocua ATCC 33091] | SEQ ID NO: | 236 |
| EFR89594.1 | crispr-associated protein, Csn1 family [Listeria innocua FSL S4-378] | SEQ ID NO: | 237 |
| WP_038409211.1 | type II CRISPR RNA-guided endonuclease Cas9 [Listeria ivanovii] | SEQ ID NO: | 238 |
| EFR95520.1 | crispr-associated protein Csn1 [Listeria ivanovii FSL F6-596] | SEQ ID NO: | 239 |
| WP_003723650.1 | type II CRISPR RNA-guided endonuclease Cas9 [Listeria monocytogenes] | SEQ ID NO: | 240 |
| WP_003727705.1 | type II CRISPR RNA-guided endonuclease Cas9 [Listeria monocytogenes] | SEQ ID NO: | 241 |
| WP_003730785.1 | type II CRISPR RNA-guided endonuclease Cas9 [Listeria monocytogenes] | SEQ ID NO: | 242 |
| WP_003733029.1 | type II CRISPR RNA-guided endonuclease Cas9 [Listeria monocytogenes] | SEQ ID NO: | 243 |
| WP_003739838.1 | type II CRISPR RNA-guided endonuclease Cas9 [Listeria monocytogenes] | SEQ ID NO: | 244 |
| WP_014601172.1 | type II CRISPR RNA-guided endonuclease Cas9 [Listeria monocytogenes] | SEQ ID NO: | 245 |
| WP_023548323.1 | type II CRISPR RNA-guided endonuclease Cas9 [Listeria monocytogenes] | SEQ ID NO: | 246 |
| WP_031665337.1 | type II CRISPR RNA-guided endonuclease Cas9 [Listeria monocytogenes] | SEQ ID NO: | 247 |
| WP_031669209.1 | type II CRISPR RNA-guided endonuclease Cas9 [Listeria monocytogenes] | SEQ ID NO: | 248 |
| WP_033920898.1 | type II CRISPR RNA-guided endonuclease Cas9 [Listeria monocytogenes] | SEQ ID NO: | 249 |
| AKI42028.1 | CRISPR-associated protein [Listeria monocytogenes] | SEQ ID NO: | 250 |
| AKI50529.1 | CRISPR-associated protein [Listeria monocytogenes] | SEQ ID NO: | 251 |
| EFR83390.1 | crispr-associated protein Csn1 [Listeria monocytogenes FSL F2-208] | SEQ ID NO: | 252 |
| WP_046323366.1 | type II CRISPR RNA-guided endonuclease Cas9 [Listeria seeligeri] | SEQ ID NO: | 253 |
| AKE81011.1 | Cas9 [Plant multiplex genome editing vector pYLCRISPR/Cas9Pubi-H] | SEQ ID NO: | 254 |
| CU082355.1 | Uncharacterized protein conserved in bacteria [Roseburia hominis] | SEQ ID NO: | 255 |
| WP_033162887.1 | type II CRISPR RNA-guided endonuclease Cas9 [Sharpea azabuensis] | SEQ ID NO: | 256 |
| AGZ01981.1 | Cas9 endonuclease [synthetic construct] | SEQ ID NO: | 257 |
| AKA60242.1 | nuclease deficient Cas9 [synthetic construct] | SEQ ID NO: | 258 |
| AK540380.1 | Cas9 [Synthetic plasmid pFC330] | SEQ ID NO: | 259 |
| 4UN5_B | Cas9, Chain B, Crystal Structure | SEQ ID NO: | 260 |

| | | | |
|---|---|---|---|
| WP_010922251 | 1 | MDKK-YSIGLDIGTNSVGWAVITDEYKVPSKKFKVPSKKFKVLGNTDRHSIKKNLIGALLFDSGETA--EATRLKRTARRRYT | 73 |
| WP_039695303 | 1 | MTKKnYSIGLDIGTNSVGWAVITDDYKVPAKKMKVLGNTDKKYIKKNLLGALLFDSGETA--EATRLKRTARRRYT | 74 |
| WP_045635197 | 1 | K-KG-YSIGLDIGTNSVGFAVITDDYKVPSKKMKVLGNTDKRPIKKNLIGALLFDEGTTA--EARRLKRTARRRYT | 73 |
| 5AXW_A | 1 | MKRN-YIILGLDIGITSVGYGII--DYET-----------RDVIDA---GVRLFKEANVEmnEGRRSKRGARRLKR | 61 |
| WP_009880683 | 1 | ---------------------------------------------------------------------------- | |
| WP_010922251 | 1 | MDKK-YSIGLDIGTNSVGWAVITDDYKVPSKKFKVPSKKFKVLGNTDRHSIKKNLIGALLFDSGETA--EATRLKRTARRRYT | 73 |
| WP_011054416 | 1 | MDKK-YSIGLDIGTNSVGWAVITDDYKVPSKKLKGLGNTDRHGIKKNLIGALLFDSGETA--EATRLKRTARRRYT | 73 |
| WP_011284745 | 1 | MDKK-YSIGLDIGTNSVGWAVITDDYKVPSKKFKVLGNTDRHSIKKNLIGALLFDSGETA--EATRLKRTARRRYT | 73 |
| WP_011285506 | 1 | MDKK-YSIGLDIGTNSVGWAVITDDYKVPSKKFKVLGNTDRHSIKKNLIGALLFDSGETA--EATRLKRTARRRYT | 73 |
| WP_011527619 | 1 | MDKK-YSIGLDIGTNSVGWAVITDDYKVPSKKFKVLGNTDRHSIKKNLIGALLFDSGEIA--EATRLKRTARRRYT | 73 |
| WP_012560673 | 1 | MDKK-YSIGLDIGTNSVGWAVITDDYKVPSKKFKVLGNTDRHSIKKNLIGALLFDSGETA--EATRLKRTARRRYT | 73 |
| WP_014407541 | 1 | MDKK-YSIGLDIGTNSVGWAVITDDYKVPSKKFKVLGNTDRHSIKKNLIGALLFGSGETA--EATRLKRTARRRYT | 73 |
| WP_020905136 | 1 | MDKK-YSIGLDIGTNSVGWAVITDDYKVPSKKFKVLGNTDRHSIKKNLIGALLFDSGETA--EATRLKRTARRRYT | 73 |

```
WP_023080005    1  MDKK-YSIGLDIGTNSVGWAVITDDYKVPSKKLKVLGNTDRHGIKKNLIGALLFDSGETA--EATRLKRTARRRYT  73
WP_023610282    1  MDKK-YSIGLDIGTNSVGWAVITDDYKVPSKKLKVLGNTDRHGIKKNLIGALLFDSGETA--EATRLKRTARRRYT  73
WP_030125963    1  MDKK-YSIGLDIGTNSVGWAVITDDYKVPSKKFPKVLGNTDRHSIKKNLIGALLFDSGETA--EATRLKRTARRRYT  73
WP_030126706    1  MDKK-YSIGLDIGTNSVGWAVITDDYKVPSKKFPKVLGNTDRHSIKKNLIGALLFDSGETA--EATRLKRTARRRYT  73
WP_031488318    1  MDKK-YSIGLDIGTNSVGWAVITDDYKVPSKKFPKVLGNTDRHGIKKNLIGALLFDSGETA--EATRLKRTARRRYT  73
WP_032460140    1  MDKK-YSIGLDIGTNSVGWAVITDDYKVPSKKFPKVLGNTDRHSIKKNLIGALLFDSGETA--EATRLKRTARRRYT  73
WP_032461047    1  MDKK-YSIGLDIGTNSVGWAVITDDYKVPSKKFPKVLGNTERHSIKKNLIGALLFDSGETA--EATRLKRTARRRYT  73
WP_032462016    1  MDKK-YSIGLDIGTNSVGWAVITDDYKVPSKKFPKVLGNTERHSIKKNLIGALLFDSGETA--EATRLKRTARRRYT  73
WP_032462936    1  MDKK-YSIGLDIGTNSVGWAVITDDYKVPSKKFPKVLGNTERHSIKKNLIGALLFDSGETA--EATRLKRTARRRYT  73
WP_032464890    1  MDKK-YSIGLDIGTNSVGWAVITDDYKVPSKKFPKVLGNTERHSIKKNLIGALLFDSGEIA--EATRLKRTARRRYT  73
WP_033888930    1  ----------------------------------------------------------------------------
WP_038431314    1  MDKK-YSIGLDIGTNSVGWAVITDDYKVPSKKFPKVLGNTDRHSIKKNLIGALLFDSGETA--EATRLKRTARRRYT  73
WP_038432938    1  MDKK-YSIGLDIGTNSVGWAVITDDYKVPSKKFPKVLGNTDRHSIKKNLIGALLFDSGETA--EATRLKRTARRRYT  73
WP_038434062    1  MDKK-YSIGLDIGTNSVGWAVITDDYKVPSKKFPKVLGNTDRHSIKKNLIGALLFDSGETA--EATRLKRTARRRYT  73
BAQ51233        1  ----------------------------------------------------------------------------
KGE60162        1  ----------------------------------------------------------------------------
KGE60856        1  MDKK-YSIGLDIGTNSVGWAVITDDYKVPSKKFPKVLGNTDRHSIKKNLIGALLFDSGEIA--EATRLKRTARRRYT  73
WP_002989955    1  MDQK-YSIGLDIGTNSVGWAVVTDDYKVPAKKMKVLGNTDKQSIKKNLLGALLFDSGETA--EATRLKRTARRRYT  73
WP_003030002    1  MTKKnYSIGLDIGTNSVGWAVITDDYKKYIKGNTDKKYIKKNLIGALLFDSGETA--EATRLKRTARRRYT  74
WP_003065552    1  MNKP-YSIGLDIGTNSVGWSIITDDYKVPAKKIRVLGNTKEYIKKNLIGALLFDGGNTA--ADRRLKRTARRRYT  73
WP_001040076    1  MNKP-YSIGLDIGTNSVGWSIITDDYKVPAKMRVLGNTKEYIKKNLIGALLFDGGNTA--ADRRLKRTARRRYT  73
WP_001040078    1  MNKP-YSIGLDIGTNSVGWSIITDDYKVPAKMRVLGNTKEYIKKNLIGALLFDGGNTA--ADRRLKRTARRRYT  73
WP_001040080    1  MNKP-YSIGLDIGTNSVGWSIITDDYKVPAKMRVLGNTKEYIKKNLIGALLFDGGNTA--ADRRLKRTARRRYT  73
WP_001040081    1  MNKP-YSIGLDIGTNSVGWSIITDDYKVPAKMRVLGNTKEYIKKNLIGALLFDGGNTA--ADRRLKRTARRRYT  73
WP_001040083    1  MNKP-YSIGLDIGTNSVGWSIITDDYKVPAKMRVLGNTKEYIKKNLIGALLFDGGNTA--ADRRLKRTARRRYT  73
WP_001040085    1  MNKP-YSIGLDIGTNSVGWSIITDDYKVPAKMRVLGNTKEYIKKNLIGALLFDGGNTA--ADRRLKRTARRRYT  73
WP_001040087    1  MNKP-YSIGLDIGTNSVGWSIITDDYKVPAKMRVLGNTKEYIKKNLIGALLFDGGNTA--ADRRLKRTARRRYT  73
WP_001040088    1  MNKP-YSIGLDIGTNSVGWSIITDDYKVPAKMRVLGNTKEYIKKNLIGALLFDGGNTA--ADRRLKRTARRRYT  73
WP_001040089    1  MNKP-YSIGLDIGTNSVGWSIITDDYKVPAKMRVLGNTKEYIKKNLIGALLFDGGNTA--ADRRLKRTARRRYT  73
WP_001040090    1  MNKP-YSIGLDIGTNSVGWSIITDDYKVPAKMRVLGNTKEYIKKNLIGALLFDGGNTA--ADRRLKRTARRRYT  73
WP_001040091    1  MNKP-YSIGLDIGTNSVGWSIITDDYKVPAKMRVLGNTKEYIKKNLIGALLFDGGNTA--ADRRLKRTARRRYT  73
WP_001040092    1  MNKP-YSIGLDIGTNSVGWSIITDDYKVPAKMRVLGNTKEYIKKNLIGALLFDGGNTA--ADRRLKRTARRRYT  73
WP_001040094    1  MNKP-YSIGLDIGTNSVGWSIITDDYKVPAKMRVLGNTKEYIKKNLIGALLFDGGNTA--ADRRLKRTARRRYT  73
WP_001040095    1  MNKP-YSIGLDIGTNSVGWSIITDDYKVPAKMRVLGNTKEYIKKNLIGALLFDGGNTA--ADRRLKRTARRRYT  73
WP_001040096    1  MNKP-YSIGLDIGTNSVGWSIITDDYKVPAKMRVLGNTKEYIKKNLIGALLFDGGNTA--ADRRLKRTARRRYT  73
WP_001040097    1  MNKP-YSIGLDIGTNSVGWSIITDDYKVPAKMRVLGNTKEYIKKNLIGALLFDGGNTA--ADRRLKRTARRRYT  73
WP_001040098    1  MNKP-YSIGLDIGTNSVGWSIITDDYKVPAKMRVLGNTKEYIKKNLIGALLFDGGNTA--ADRRLKRTARRRYT  73
WP_001040099    1  MNKP-YSIGLDIGTNSVGWSIITDDYKVPAKMRVLGNTKEYIKKNLIGALLFDGGNTA--ADRRLKRTARRRYT  73
WP_001040100    1  MNKP-YSIGLDIGTNSVGWSIITDDYKVPAKMRVLGNTKEYIKKNLIGALLFDGGNTA--ADRRLKRTARRRYT  73
WP_001040104    1  MNKP-YSIGLDIGTNSVGWSIITDDYKVPAKMRVLGNTKEYIKKNLIGALLFDGGNTA--ADRRLKRTARRRYT  73
WP_001040105    1  MNKP-YSIGLDIGTNSVGWSIITDDYKVPAKMRVLGNTKEYIKKNLIGALLFDGGNTA--ADRRLKRTSRRRYT  73
WP_001040106    1  MNKP-YSIGLDIGTNSVGWSIITDDYKVPAKMRVLGNTKEYIKKNLIGALLFDGGNTA--ADRRLKRTARRRYT  73
WP_001040107    1  MNKP-YSIGLDIGTNSVGWSIITDDYKVPAKMRVLGNTKEYIKKNLIGALLFDGGNTA--ADRRLKRTARRRYT  73
WP_001040108    1  MNKP-YSIGLDIGTNSVGYSVVTDDYKVPAKMRVLGNTKEYIKKNLIGALLFDGGNTA--SDRRLKRTARRRYT  73
WP_001040109    1  MNKP-YSIGLDIGTNSVGYSVVTDDYKVPAKMRVLGNTKEYIKKNLIGALLFDGGNTA--SDRRLKRTARRRYT  73
WP_001040110    1  MNKP-YSIGLDIGTNSVGYSVVTDDYKVPAKMRVLGNTKEYIKKNLIGALLFDGGNTA--ADRRLKRTARRRYT  73
WP_015058523    1  MNKP-YSIGLDIGTNSVGWSIITDDYKVPAKMRVLGNTKEYIKKNLIGALLFDGGNTA--ADRRLKRTARRRYT  73
WP_017643650    1  MNKP-YSIGLDIGTNSVGWSIITDDYKVPAKMRVLGNTKEYIKKNLIGALLFDGGNTA--SDRRLKRTARRRYT  73
WP_017647151    1  MNKP-YSIGLDIGTNSVGWSIITDDYKVPAKMRVLGNTKEYIKKNLIGALLFDGGNTA--ADRRLKRTARRRYT  73
WP_017648376    1  MNKP-YSIGLDIGTNSVGWSIITDDYKVPAKMRVLGNTKEYIKKNLIGALLFDGGNTA--SDRRLKRTARRRYT  73
WP_017649527    1  MNKP-YSIGLDIGTNSVGYSVVTDDYKVPAKMRVLGNTKEYIKKNLIGALLFDGGNTA--ADRRLKRTARRRYT  73
WP_017771611    1  MNKP-YSIGLDIGTNSVGYSVVTDDYKVPAKMRVLGNTKEYIKKNLIGALLFDGGNTA--SDRRLKRTARRRYT  73
WP_017771984    1  MNKP-YSIGLDIGTNSVGWSIITDDYKVPAKMRVLGNTKEYIKKNLIGALLFDGGNTA--ADRRLKRTARRRYT  73
```

```
                      -continued

CFQ25032         1  MNKP-YSIGLDIGTNSVGWSIITDDYKVPAKKMRVLGNTDKEYIKKNLIGALLFDGGNTA--ADRRLKRTARRRYT  73
CFV16040         1  MNKP-YSIGLDIGTNSVGWSIITDDYKVPAKKMRVLGNTDKEYIKKNLIGALLFDGGNTA--ADRRLKRTARRRYT  73
KLJ37842         1  MNKP-YSIGLDIGTNSVGWSIITDDYKVPAKKMRVLGNTDKEYIKKNLIGALLFDGGNTA--ADRRLKRTARRRYT  73
KLJ72361         1  MNKP-YSIGLDIGTNSVGWSIITDDYKVPAKKMRVLGNTDKEYIKKNLIGALLFDGGNTA--ADRRLKRTARRRYT  73
KLL20707         1  MNKP-YSIGLDIGTNSVGWSIITDDYKVPAKKMRVLGNTDKEYIKKNLIGALLFDGGNTA--ADRRLKRTARRRYT  73
KLL42645         1  MNKP-YSIGLDIGTNSVGYSVVTDDYKVPAKKMRVLGNTDKEYIKKNLIGALLFDGGNTA--SDRRLKRTARRRYT  73
WP_047207273     1  MNKP-YSIGLDIGTNSVGWSIITDDYKVPAKKMRVLGNTDKEYIKKNLIGALLFDGRNTA--ADRRLKRTARRRYT  73
WP_047209694     1  MNKP-YSIGLDIGTNSVGWSIITDDYKVPAKKMRVLGNTDKEYIKKNLIGALLFDGGNTA--ADRRLKRTARRRYT  73
WP_050198062     1  MNKP-YSIGLDIGTNSVGWSIITDDYKVPAKKMRVLGNTDKEYIKKNLIGALLFDGGNTA--ADRRLKRTARRRYT  73
WP_050201642     1  MNKP-YSIGLDIGTNSVGWSIITDDYKVPAKKMRVLGNTDKEYIKKNLIGALLFDGGNTA--ADRRLKRTARRRYT  73
WP_050204027     1  MNKP-YSIGLDIGTNSVGWSIITDDYKVPAKKMRVLGNTDKEYIKKNLIGALLFDGGNTA--SDRRLKRTARRRYT  73
WP_050881965     1  MNKP-YSIGLDIGTNSVGYSVVTDDYKVPAKKMRVLGNTDKEYIKKNLIGALLFDGGNTA--ADRRLKRTARRRYT  73
WP_050886065     1  MNKP-YSIGLDIGTNSVGWSIITDDYKVPAKKMRVLGNTDKEYIKKNLIGALLFDGGNTA--ADRRLKRTARRRYT  73
AHN30376         1  MNKP-YSIGLDIGTNSVGWSIITDDYKVPAKKMRVLGNTDKEYIKKNLIGALLFDGGNTA--ADRRLKRTARRRYT  73
EAO78426         1  MNKP-YSIGLDIGTNSVGXDIGTNSVGWSIITDDYKVPAKKMRVLGNTDKEYIKKNLIGALLFDGGNTA--ADRRLKRIARRRYT  73
CCW42055         1  MNKP-YSIGLDIGTNSVGWSIITDDYKVPAKKMRVLGNTDKQSIKKNLIGALLFDGGNTA--EATRLKRTARRRYT  73
WP_003041502     1  MNQK-YSIGLDIGTNSVGWAVITDDYKVPAKKMKVLGNTDKQSIKKNLIGALLFDSGETA--EATRLKRTARRRYT  73
WP_037593752     1  MKKE-YSIGLDIGTNSVGWAVITDDYKVPAKKMKILGNTNKQYIKKNLIGALLFDSGETA--KATRLKRTARRRYT  74
WP_049516684     1  MKKE-YSIGLDIGTNSVGWAVITDDYKVPAKKMKVLGNTDKQSIKKNLIGALLFDSGETA--EATRLKRTARRRYT  74
GAD46167         1  MKKE-YSIGLDIGTNSVGWAVITDDYKVPAKKMKVLGNTDKQSIKKNLIGALLFDSGETA--EATRLKRTARRRYT  73
WP_018363470     1  MTKKnYSIGLDIGTNSVGWAVITDDYKVPSKKFKVLGNTNRHSIKKNLIGALLFDSGETA--EATRLKRTARRRYT  74
WP_003043819     1  MEKK-YSIGLDIGTNSVGWAVITDDYKVPSKKFKVLGNTNRKSIKKNLMGALLFDSGETA--EATRLKRTARRRYT  73
WP_066269658     1  MGKP-YSIGLDIGTNSVGWAVITDDYKVPSKKFKVLGNTDRHSIKKNLIGALLFDSGETA--EATRLKRTARRRYT  73
WP_048800089     1  MTQK-YSIGLDIGTNSVGWAVITDDYKVPAKKMKILGNTNKQYIKKNLIGALLFDSGETA--KATRLKRTARRRYT  73
WP_012767106     1  MDKK-YSIGLDIGTNSVGWAVITDDYKVPSKKFKVLGNTDRHSIKKNLIGALLFDSGETA--EATRLKRTARRRYT  73
WP_014612333     1  MDKK-YSIGLDIGTNSVGWAVITDDYKVPSKKFKVLGNTDRHSIKKNLIGALLFDSGETA--EATRLKRTARRRYT  73
WP_015017095     1  MDKK-YSIGLDIGTNSVGWAVITDDYKVPSKKFKVLGNTDRHSIKKNLIGALLFDSGETA--EATRLKRTARRRYT  73
WP_015057649     1  MDKK-YSIGLDIGTNSVGWAVITDDYKVPSKKFKVLGNTDRHSIKKNLIGALLFDSGETA--EATRLKRTARRRYT  73
WP_048327215     1  MDKK-YSIGLDIGTNSVGWAVITDDYKVPSKKFKVLGNTDRHSIKKNLIGALLFDSGETA--EATRLKRTARRRYT  73
WP_049519324     1  MDKK-YSIGLDIGTNSVGWAVITDDYKVPSKKFKVLGNTDRHSIKKNLIGALLFDSGETA--EGTRLKRTARRRYT  73
WP_012515931     1  MKKP-YTIALDIGTNSVGWVVTDDYKVPVPTKKMKVLGNTERKTIKKNLIGALLFDSGETA--EGTRLKRTARRRYT  73
WP_021320964     1  MKKP-YTIALDIGTNSVGWVVTDDYRVPTKKMKVLGNTERKTIKKNLIGALLFDSGETA--EGTRLKRTARPRYT  73
WP_037581760     1  M-EKtYSIGLDIGTNSVGWAVITDDYKVPTKKKMKVLGNTERKTIKKNLIGALLFDSGETA--EATRLKRAARRRYT  73
WP_004232481     1  MTKKnYSIGLDIGTNSVGWAVITDDYKVPAKKMKVLGNTDKKYIKKNLIGALLFDGNGETA--EATRLKRTARRRYT  74
WP_009854540     1  MTEKnYSIGLDIGTNSVGWAVITDDYKVPSKKMKVLGNTDKKYIKKNLIGALLFDNGETA--EATRLKRTARRRYT  73
WP_012962174     1  MTKKnYSIGLDIGTNSVGWAVITDDYKVPAKKMKVLGNTDKKYIKKNLIGALLFDSGETA--EATRLKRTARRRYT  74
WP_039695303     1  M-EKSYSIGLDIGTNSVGWAVITDDYKVPAKKMKVLGNTDKKYIKKNLIGALLFDEGTTA--EVTRLKRTARRRYT  74
WP_014334983     1  M-EKSYSIGLDIGTNSVGWAVITDDYKVPAKKMKVLGNTDKKYIKKNLIEKNLLGALLFDNGETA--EATRLKRTTRRRYT  73
WP_003099269     1  MRKP-YSIGLDIGTNSVGWAVITDDYKVPSKKMKVRIQGTTDRTSIKKNLIGALLFDNGETA--EATRLKRTTRRRYT  73
AHY15608         1  MRKP-YSIGLDIGTNSVGWAVITDDYKVPSKKMKVRIQGTTDRTSIKKNLIGALLFDNGETA--EATRLKRTTRRRYT  73
AHY17476         1  MRKP-YSIGLDIGTNSVGWAVITDDYKVPSKKMKVRIQGTTDRTSIKKNLIGALLFDNGETA--EATRLKRTTRRRYT  73
ESR09100         1  ----------------------------------------------------------------------------
AGM98575         1  MRKP-YSIGLDIGTNSVGWAVITDDYKVPSKKMKVLGNTDKSHIKKNLIGALLFDSGETA--EATRLKRTTRRRYT  73
ALF27331         1  MKKP-YSIGLDIGTNSVGWAVVTDDYKVPSKKMKVLGNTDKSHIKKNLIGALLFDSGETA--EATRLKRTTRRRYT  73
WP_018372492     1  MKKP-YSIGLDIGTNSVGWAVVMEDYKVPSKKMKVLGNTDKSHIKKNLIGALLFDSGETAv--ERRLNRTTSRRYD  73
WP_045618028     1  NNKP-YSIGLDIGTNSVGWAVVTDDYKVPSKKMKVLGNTDKSHIKKNLIGALLFDSGETA--ERRLNRTTSRRYD  74
WP_045635197     1  K-KG-YSIGLDIGTNSVGFAVITDDYKVPSKKMKVLGNTDKHFIKKNLIGALLFDEGTTA--EARRLKRTARRRYT  73
WP_002263549     1  MKKP-YSIGLDIGTNSVGWAVVTDDYKVPSKKMKVLGNTDKRFIKKNLIGALLFDSGETA--EARRLKRTARRRYT  73
WP_002263887     1  MKKP-YSIGLDIGTNSVGWAVVTDDYKVPSKKMKVLGNTDKSHIEKNLLGALLFDSGGNTA--EDRRLKRTARRRYT  73
WP_002264920     1  MKKP-YSIGLDIGTNSVGWAVVTDDYKVPAKKMKVLGNTDKSHIKKNLLGALLFDSGNTA--EDRRLKRTARRRYT  73
WP_002269043     1  MKKP-YSIGLDIGTNSVGWAVVTDDYKVPAKKMKVLGNTDKSHIKKNLLGALLFDSGNTA--EDRRLKRTARRRYT  73
WP_002269448     1  MKKP-YSIGLDIGTNSVGWAVVTDDYKVPAKKMKVLGNTDKSHIKKNLLGALLFDSGNTA--EDRRLKRTARRRYT  73
WP_002271977     1  MKKP-YSIGLDIGTNSVGWAVVTDDYKVPAKKMKVLGNTDKSHIKKNLLGALLFDSGNTA--EDRRLKRTARRRYT  73
```

| ID | Start | Sequence | End |
|---|---|---|---|
| WP_002272766 | 1 | MKKP-YSIGLDIGTNSVGWAVTDDYKVPAKKMKVLGNTDKSHIKKNLLGALLFDSGNTA-EDRRLKRTARRRYT | 73 |
| WP_002273241 | 1 | MKKP-YSIGLDIGTNSVGWAVTDDYKVPAKKMKVLGNTDKSHIKKNLLGALLFDSGNTA-EDRRLKRTARRRYT | 73 |
| WP_002275430 | 1 | MKKP-YSIGLDIGTNSVGWAVTDDYKVPAKKMKVLGNTDKSHIKKNLLGALLFDSGNTA-ADRRLKRTARRRYT | 73 |
| WP_002276448 | 1 | MKKP-YSIGLDIGTNSVGWAVTDDYKVPAKKMKVLGNTDKSHIKKNLLGALLFDSGNTA-EDRRLKRTARRRYT | 73 |
| WP_002277050 | 1 | MKKS-YSIGLDIGTNSVGWAVTDDYKVPAKKMKVLGNTDKSHIKKNLLGALLFDSGNTA-EDRRLKRTARRRYT | 73 |
| WP_002273364 | 1 | MKKS-YSIGLDIGTNSVGWAVTDDYKVSAKKMKVLGNTDKSHIKKNLLGALLFDSGNTA-EDRRLKRTARRRYT | 73 |
| WP_002279025 | 1 | MKKP-YSIGLDIGTNSVGWAVTDDYKVPAKKMKVLGNTDKSHIKKNLLGALLFDSGNTA-EDRRLKRTARRRYT | 73 |
| WP_002279859 | 1 | MKKP-YSIGLDIGTNSVGWAVTDDYKVPAKKMKVLGNTDKSHIKKNLLGALLFDSGNTA-EDRRLKRTARRRYT | 73 |
| WP_002280230 | 1 | MKKP-YSIGLDIGTNSVGWAVTDDYKVPAKKMKVLGNTDKSHIKKNLLGALLFDSGNTA-ADRRLKRTARRRYT | 73 |
| WP_002281696 | 1 | MKKP-YSIGLDIGTNSVGWAVTDDYKVPAKKMKVLGNTDKSHIKKNLLGALLFDSGNTA-EDRRLKRTARRRYT | 73 |
| WP_002282247 | 1 | MKKP-YSIGLDIGTNSVGWAVTDDYKVPAKKMKVLGNTDKSHIKKNLLGALLFDSGNTA-EDRRLKRTARRRYT | 73 |
| WP_002282906 | 1 | MKKP-YSIGLDIGTNSVGWAVTDDYKVPAKKMKVLGNTDKSHIKKNLLGALLFDSGNTA-EDRRLKRTARRRYT | 73 |
| WP_002283846 | 1 | MKKP-YSIGLDIGTNSVVTDDYKVPAKKMKVLGNTDKSHIKKNLLGALLFDSGNTA-EDRRLKRTARRRYT | 73 |
| WP_002288255 | 1 | MKKP-YSIGLDIGTNSVGWAVTDDYKVPAKKMKVLGNTDKSHIKKNLLGALLFDSGNTA-EDRRLKRTARRRYT | 73 |
| WP_002288990 | 1 | MKKP-YSIGLDIGTNSVGWAVTDDYKVPAKKMKVLGNTDKSHIKKNLLGALLFDSGNTA-EDRRLKRTARRRYT | 73 |
| WP_002289641 | 1 | MKKP-YSIGLDIGTNSVGWAVTDDYKVPAKKMKVLGNTDKSHIEKNLLGALLFDSGNTA-EDRRLKRTTRRRYT | 73 |
| WP_002290427 | 1 | MKKP-YSIGLDIGTNSVGWAVTDDYKVPAKKMKVLGNTDKSHIKKNLLGALLFDSGNTA-EDRRLKRTARRRYT | 73 |
| WP_002295753 | 1 | MKKP-YSIGLDIGTNSVGWAVTDDYKVPAKKMKVLGNTDKSHIKKNLLGALLFDSGNTA-ADRRLKRTARRRYT | 73 |
| WP_002296423 | 1 | MKKP-YSIGLDIGTNSVGWAVTDDYKVPAKKMKVLGNTDKSHIKKNLLGALLFDSGNTA-EDRRLKRTARRRYT | 73 |
| WP_002304487 | 1 | MKKP-YSIGLDIGTNSVGWAVTDDYKVPAKKMKVLGNTDKSHIKKNLLGALLFDSGNTA-EDRRLKRTARRRYT | 73 |
| WP_002305844 | 1 | MKKP-YSIGLDIGTNSVGWAVTDDYKVPAKKMKVLGNTDKSHIKKNLLGALLFDSGNTA-EDRRLKRTARRRYT | 73 |
| WP_002307203 | 1 | MKKP-YSIGLDIGTNSVGWAVTDDYKVPAKKMKVLGNTDKSHIKKNLLGALLFDSGNTA-EDRRLKRTARRRYT | 73 |
| WP_002310390 | 1 | MKKP-YSIGLDIGTNSVGWAVTDDYKVPAKKMKVLGNTDKSHIKKNLLGALLFDSGNTA-EDRRLKRTARRRYT | 73 |
| WP_002352408 | 1 | MKKP-YSIGLDIGTNSVGWAVTDDYKVPAKKMKVLGNTDKSHIEKNLLGALLFDSGNTA-EDRRLKRTARRRYT | 73 |
| WP_012997688 | 1 | MKKP-YSIGLDIGTNSVGWAVTDDYKVPAKKMKVLGNTDKSHIKKNLLGALLFDSGNTA-EDRRLKRTARRRYT | 73 |
| WP_014677909 | 1 | MKKP-YSIGLDIGTNSVGWAVTDDYKVPDKKMKVLGNTDKSHIKKNLLGALLFDSGNTA-EDRRLKRTARRRYT | 73 |
| WP_019312892 | 1 | MKKP-YSIGLDIGTNSVGWAVTDDYKVPAKKMKVLGNTDKSHIKKNLLGALLFDSGNTA-ADRRLKRTARRRYT | 73 |
| WP_019313659 | 1 | MKKP-YSIGLDIGTNSVGWAVTDDYKVPAKKMKVLGNTDKSHIKKNLLGALLFDSGNTA-EDRRLKRTARRRYT | 73 |
| WP_019314093 | 1 | MKKP-YSIGLDIGTNSVGWAVTDDYKVPAKKMKVLGNTDKSHIKKNLLGALLFDSGNTA-EDRRLKRTARRRYT | 73 |
| WP_019315370 | 1 | MKKP-YSIGLDIGTNSVGWAVTDDYKVPAKKMKVLGNTDKSHIKKNLLGALLFDSGNTA-ADRRLKRTARRRYT | 73 |
| WP_019803776 | 1 | MKKP-YSIGLDIGTNSVGWAVTDDYKVPAKKMKVLGNTDKSHIKKNLLGALLFDSGNTA-EDRRLKRTARRRYT | 73 |
| WP_019805234 | 1 | MKKP-YSIGLDIGTNSVGWAVTDDYKVPAKKMKVLGNTDKSHIEKNLLGALLFDSGNTA-EDRRLKRTARRRYT | 73 |
| WP_024783594 | 1 | MKKP-YSIGLDIGTNSVGWAVTDDYKVPAKKMKVLGNTDKSHIKKNLLGALLFDSGNTA-EDRRLKRTARRRYT | 73 |
| WP_024784288 | 1 | MKKP-YSIGLDIGTNSVGWAVTDDYKVPAKKMKVLGNTDKSHIKKNLLGALLFDSGNTA-ADRRLKRTARRRYT | 73 |
| WP_024784666 | 1 | MKKP-YSIGLDIGTNSVGWAVTDDYKVPAKKMKVLGNTDKSHIKKNLLGALLFDSGNTA-ADRRLKRTARRRYT | 73 |
| WP_024784894 | 1 | MKKP-YSIGLDIGTNSVGWAVTDDYKVPAKKMKVLGNTDKSHIKKNLLGALLFDSGNTA-EDRRLKRTTRRRYT | 73 |
| WP_024786433 | 1 | MKKP-YSIGLDIGTNSVGWAVTDDYKVPAKKMKVLGNTDKSHIKKNLLGALLFDSGNTA-ADRRLKRTARRRYT | 73 |
| WP_049473442 | 1 | MKKP-YSIGLDIGTNSVGWAVTDDYKVPAKKMKVLGNTDKSHIKKNLLGALLFDSGNTA-EDRRLKRTARRRYT | 73 |
| WP_049474547 | 1 | MKKP-YSIGLDIGTNSVGWAVTDDYKVPAKKMKVLGNTDKSHIKKNLLGALLFDSGNTA-ADRRLKRTARRRYT | 73 |
| EMC03581 | 1 | MDL------IGTNSVGWAVTDDYKVPAKKMKVLGNTDKSHIKKNLLGALLFDSGNTA-EDRRLKRTARRRYT | 66 |
| WP_000428612 | 1 | ENKN-YSIGLDIGTNSVGWAVITDDYKVPAKKMKVLGNTDKRPIKKNLLGALLFDEGTTA-EARRLKRTARRRYT | 74 |
| WP_000428613 | 1 | ENKN-YSIGLDIGTNSVGWAVITDDYKVPSKKMKVLGNTDKRFIKKNLLGALLFDEGTTA-EARRLKRTARRRYT | 74 |
| WP_049523028 | 1 | K-KP-YSIGLDIGTNSVGWAVITDDYKVPAKKMKVLGNTNKESIKKNLIGALLFDAGNTA-ADRRLKRTARRRYT | 73 |
| WP_003107102 | 1 | ------MKVLGNTDRQTVKKNMIGTLLFDSGETA-EARRLKRTARRRYT | 42 |
| WP_054279288 | 1 | -KKS-YSIGLDIGTNSVGWAVITDDYKVPAKKMKVLGNTSRQSIKNMIGALLFDEGPA-ASTVKRTTRRRYT | 75 |
| WP_049531101 | 1 | SNKP-YSIGLDIGTNSVGWAVITDDYKVPSKKMKVLGNTDKHFIKKNLLGALLFDEGTTA-EDRRLKRTARRRYT | 74 |
| WP_049538452 | 1 | SNKP-YSIGLDIGTNSVGWAVITDDYKVPSKKMKVLGNTDKHFIKKNLLGALLFDEGTTA-EDRRLKRTARRRYT | 74 |
| WP_049549711 | 1 | --YS-YSIGLDIGTNSVGWAVINEDYKVPAKKMTVFGNTDRKTIKKNLLGTVLFDSGETA-QARRLKRTNRRRYT | 75 |
| WP_007896501 | 1 | ---------MLGTVLFDSGETA-QARRLKRTNRRRYT | 27 |
| EFR44625 | 1 | K-KP-YSIGLDIGTNSVGWSVITDDYKVPSKKMKVLGNTDKHFIKKNLIGALLFDEGTTA-ESRRLKRTSRRRYT | 73 |
| WP_002897477 | 1 | K-KP-YSIGLDIGTNSVGWAVITDDYKVPSKKMKVLGNTDKHFIKKNLIGALLFDEGTTA-EDRRLKRTARRRYT | 73 |
| WP_002906454 | 1 | ENKN-YSIGLDIGTNSVGWSVITDDYKVPSKKMKVLGNTVFGNTDRKTIKKNLIGALLFDEGTTA-EARRLKRTARRRYT | 74 |
| WP_009729476 | 1 | ENKN-YSIGLDIGTNSVGWSVITDDYKVPSKKMKVLGNTDKHFIKKNLIGALLFDEGTTA-EARRLKRTARRRYT | 74 |

```
                  -continued

CQR24647         1 MKKKP-YSIGLDIGTNSVGWAVITDDYKVPAKKMKVLGNTDKEYIKKNLIGALLFDSGETA-EATRMKRTARRRYT    73
WP_000066813     1 SNKS-YSIGIDIGTNSVGWAVITDDYKVPSKKMKVLGNTDKHFIKKNLIGALLFDEGTTA-EDRRLKRTARRRYT    74
WP_009754323     1 NNNN-YSIGLDIGTNSVGWAVITDDYKVPSKKMRVLGNTDKRPIKKNLIGALLFDEGTTA-EDRRLKRTARRRYT    74
WP_044674937     1 MKKK-YAIGIDIGTNSVGWAVITDDYKVPSKKMRVLGNTEKRFIKKNLLGTLLFDEGNTA-ENRRLKRTARRRYT    73
WP_044676715     1 MKKK-YAIGIDIGTNSVGWSVVTDDYKVPSKKMKVFGNTEKRYIKKNLLGTLLFDEGNTA-ENRRLKRTARRRYT    73
WP_044680361     1 MKKK-YAIGIDIGTNSVGWAVITDDYKVPSKKMKVFGNTEKRYIKKNLLGTLLFDEGNTA-ENRRLKRTARRRYT    73
WP_044681799     1 MKKK-YAIGIDIGTNSVGWAVITDDYKVPSKKMKVFGNTEKRYIKKNLLGTLLFDEGNTA-ENRRLKRTARRRYT    73
WP_049533112     1 MDQK-YSIGLDIGTNSVGWAVVTDDYKVPAKKMKVLGNTDKQSIKKNLIGALLFDSGETA-EATRLKRTARRRYT    73
WP_029090905     1 -----------------------------------MWGVSLFEAGKTA--AERRGYRSTRRRLN             27
WP_065066696     1 I-VD-YCIGLDLGTGSVGWAVVDMNHRLMKRN---------GKHLWGSRLFSNAETA-ANRRASRSIRRRYN    60
AIT42264         1 MDKK-YSIGLDIGTNSVGWAVITDEYKVPSKKFKVLGNTDRHSIKKNLIGALLFDSGETA-EATRLKRTARRRYT    73
WP_034440723     1 -MKN-YTLGLDIGTNSVGWAVIKDDLTLVRKKVKISGNTDKKEVKKNLWGSFLFEQGGTA-QDTRVKRIARRRYE    72
AKQ21048         1 MDKK-YSIGLDIGTNSVGWAVITDEYKVPSKKFKVLGNTDRHSIKKNLIGALLFDEGGTA-EATRLKRTARRRYT    73
WP_004636532     1 MQKN-YTIGLDIGTNSVGWAVMKDDYTLLRKRMKVLGNTDIKKIKKNFWGVRLFDEGGTA-KETRLKRGTRRRYQ    73
WP_002364836     1 MKKD-YVIGLDIGTNSVGWAVMTEDYQLVKKKMPIYGNTEKKKIKKNFWGVRLFEEGHTA-EDRRLKRTARRRIS    73
WP_016631044     1 ----------------------------MRLFEEGHTA-EDRRLKRTARRRIS                         24
EMS75795         1 ----------------------------------------------------                          
WP_002373311     1 MKKD-YVIGLDIGTNSVGWAVMTEDYQLVKKKMPIYGNTEKKKIKKNFWGVRLFEEGHTA-EDRRLKRTARRRIS    73
WP_002378009     1 MKKD-YVIGLDIGTNSVGWAVMTEDYQLVKKKMPIYGNTEKKKIKKNFWGVRLFEEGHTA-EDRRLKRTARRRIS    73
WP_002407324     1 MKKD-YVIGLDIGTNSVGWAVMTEDYQLVKKKMPIYGNTEKKKIKKNFWGVRLFEEGHTA-EDRRLKRTARRRIS    73
WP_002413717     1 MKKD-YVIGLDIGTNSVGWAVMTEDYQLVKKKMPIYGNTEKKKIKKNFWGVRLFEEGHTA-EDRRLKRTARRRIS    73
WP_010775580     1 MKKD-YVIGLDIGTNSVGWAVMTEDYQLVKKKMPIYGNTEKKKIKKNFWGVRLFEEGHTA-EDRRLKRTARRRIS    73
WP_010818269     1 MKKD-YVIGLDIGTNSVGWAVMTEDYQLVKKKMPIYGNTEKKKIKKNFWGVRLFEEGHTA-EDRRLKRTARRRIS    73
WP_010824395     1 MKKD-YVIGLDIGSNSVGWAVMTEDYQLVKKKMPIYGNTEKKKIKKNFWGVRLFEEGHTA-EDRRLKRTARRRIS    73
WP_016622645     1 MKKD-YVIGLDIGTNSVGWAVMTEDYQLVKKKMPIYGNTEKKKIKKNFWGVRLFEEGHTA-EDRRLKRTARRRIS    73
WP_033624816     1 MKKD-YVIGLDIGTNSVGWAVMTEDYQLVKKKMPIYGNTEKKKIKKNFWGVRLFEEGHTA-EDRRLKRTARRRIS    73
WP_002625576     1 MKKD-YVIGLDIGTNSVGWAVMTEDYQLVKKKMPIYGNTEKKKIKKNFWGVRLFEEGHTA-EDRRLKRTARRRIS    73
WP_033789179     1 MKKD-YVIGLDIGTNSVGWAVMTEDYQLVKKKMPIYGNTEKKKIKKNFWGVRLFEEGHTA-EDRRLKRTARRRIS    73
WP_002310644     1 MKKE-YTIGLDIGTNSVGWSVLTDDYRLVSKKMKVAGNTEKSSTKKNFWGVRLFDEGQTA-EARRSKRTARRRLA    73
WP_002312694     1 MKKE-YTIGLDIGTNSVGWSVLTDDYRLVSKKMKVAGNTEKSSTKKNFWGVRLFDEGQTA-EARRSKRTARRRLA    73
WP_002314015     1 MKKE-YTIGLDIGTNSVGWSVLTDDYRLVSKKMKVAGNTEKSSTKKNFWGVRLFDEGQTA-EARRSKRTARRRLA    73
WP_002320716     1 MKKE-YTIGLDIGTNSVGWSVLTDDYRLVSKKMKVAGNTEKSSTKKNFWGVRLFDEGQTA-EARRSKRTARRRLA    73
WP_002330729     1 MKKE-YTIGLDIGTNSVGWSVLTDDYRLVSKKMKVAGNTEKSSTKKNFWGVRLFDEGQTA-EARRSKRTARRRLA    73
WP_002335161     1 MKKE-YTIGLDIGTNSVGWSVLTDDYRLVSKKMKVAGNTEKSSTKKNFWGVRLFDEGQTA-EARRSKRTARRRLA    73
WP_002345439     1 MKKE-YTIGLDIGTNSVGWAVLTDDYQLMKRRMSVHGNTEKKKIKKNFWGARLFDEGQTA-EFRRTKRTNRRRLA    73
WP_034867970     1 MTKD-YTIGLDIGTNSVGWAVLTDDYQLMKRMSVHGNTEKKKIKKNFWGARLFDEGQTA-EFRRTKRTNRRRLA    73
WP_047937432     1 MKKE-YTIGLDIGTNSVGWAVLTDDYRLVSKKMKVAGNTEKSSTKKNFWGVRLFDEGQTA-EARRSKRTARRRLA    73
WP_010720994     1 MTKD-YTIGLDIGTNSVGWAVLTDDYQLMKRMSVHGNTEKKKIKKNFWGARLFDEGQTA-EFRRTKRTNRRRLA    73
WP_010737004     1 MTKD-YTIGLDIGTNSVGWAVLTDDYQLMKRMSVHGNTEKKKIKKNFWGARLFDEGQTA-EFRRTKRTNRRRLA    73
WP_034700478     1 MTKD-YTIGLDIGTNSVGWAVLTDDYQLMKRMSVHGNTEKKKIKKNFWGARLFDEGQTA-EFRRTKRTNRRRLA    73
WP_072209003     1 MKND-YTIGLDIGTNSVGYSVVTDDYKVISKKNNVFGNTEKKSIKKNFWGARLFESGQTA-QEARMKRTSRRRIA    73
WP_023519017     1 MEKE-YTIGLDIGTNSVGWAVLTDDYRLVARKMSIQGDSNRKKIKKNFWGARLFEEGKTA-QFRRIKRTNRRRIA    73
WP_010770040     1 MGKE-YTIGLDIGTNSVGWAVLTENYDLVKKMKVYGNTETKYLKKNLWGVDLFDEGMTA-ADRRLKRTTRRRYS    73
WP_048604708     1 MGKE-YTIGLDIGTNSVGWAVLQEDLDIVRRKMKVYGNTEKNVLKKNFWGVLLFNEGQTA-KDTRLKRGARRRYT    73
WP_010750235     1 MNKA-YTLGLDIGTNSVGWAVLTDDYRLMAKMPVHSKMEKKKIKKNFWGARLFDEGQTA-EERRNKRATRRRLR    73
AII16583         1 ADKK-YSIGLDIGTNSVGWAVITDDYKVPSKKFKVLGNTDRHSIKKNLIGALLFDSGETA-EATRLKRTARRRIE   112
WP_029073316     1 NNKI-YNIGLDIGDASVGWAVVDEHYNLLKRH---------GKHMWGSRLFTQANTA-VERSSSRTRRRYN        65
WP_031589969     1 NNNI-YNIGLDIGDASVGWAVVDEHYNLLKRH---------GKHMWGSRLFTQANTA-VERSSRSTRRRYN        65
KDA45870         1 LKKD-YSIGLDIGTNSVGHAVVTDDYKVPTKMKVFGDTSKKTIKQNMLGVLLFNEGQTA-ADTRLKRGARRRYT    74
WP_039099354     1 MSRP-YNIGLDIGTSSIGWSVVDDQSKLVSVR---------GKYGYGVRLYDEGQTA-AERRSFRTTRRLK        61
AKP02966         1 KEQP-YNIGLDIGTGSVGWAVLTDQYDIVKRKMKIAGDSEKKQIKKNFWGVRLFEGAQTA-KETRLNRSTRRRYR    64
WP_010991369     1 MKKP-YTIGLDIGTNSVGWAVLTDQYDLVKRKMKIAGDSEKKQIKKNFWGVRLFDEGQTA-ADRRMARTARRRIE    73
WP_033838504     1 MKKP-YTIGLDIGTNSVGWAVLTDQYDLVKRKMKIAGDSEKKQIKKNFWGVRLFDEGQTA-ADRRMARTARRRIE    73
```

-continued

```
EHN60060            1 MKKP-YTIGLDIGTNSVGWAVLTDQYDLVKRMKIAGDSEKKQIKKQNFWGVRLFDEQGTA--ADRRMARTARRRIE        76
EFR89594            1 MRKP-YTIGLDIGTNSVGWAVLTDQYNLVKRMKVAGSAEKKQIKKQNFWGVRLFDEGEVA--AGRRMNRTTRRRIE        73
WP_038409211        1 MKNP-YTIGLDIGTNSVGWAVLTDQYDLVKRMKVAGNSDKKQIKKQNFWGVRLFDDQGTA--VDRRMNRTARRRIE        73
EFR95520            1 MKNP-YTIGLDIGTNSVGWAVLTDQYDLVKRMKVAGNSDKKQIKKQNFWGVRLFDDGQTA--VDRRMNRTARRRIE        73
WP_003723650        1 MKNP-YTIGLDIGTNSVGWAVLTDQYDLVKRMKVAGNSDKKQIKKQNFWGVRLFDDGQTA--VDRRMNRTARRRIE        73
WP_003727705        1 MKNP-YTIGLDIGTNSVGWAVLTDQYDLVKRMKVAGNSDKKQIKKQNFWGVRLFDDGQTA--VDRRMNRTARRRIE        73
WP_003730785        1 MKNP-YTIGLDIGTNSVGWAVLTDQYDLVKRMKVAGNSDKKQIKKQNFWGVRLFDDGQTA--AKRRMSRTARRRIE        73
WP_003733029        1 MKNP-YTIGLDIGTNSVGWAVLTDQYDLVKRMKVSGDSEKKQIKKQNFWGVRLFEKGETA--ADRRMNRTARRRIE        73
WP_003739838        1 MKNP-YTIGLDIGTNSVGWAVLTDQYDLVKRMKVAGNSDKKQIKKQNFWGVRLFDDGQTA--VDRRMNRTARRRIE        73
WP_014601172        1 MKNP-YTIGLDIGTNSVGWAVLTDQYDLVKRMKVAGNSDKKQIKKQNFWGVRLFDDGQTA--VDRRMNRTARRRIE        73
WP_023548323        1 MKNP-YTIGLDIGTNSVGWAVLTDQYDLVKRMKVAGNSDKKQIKKQNFWGVRLFDDGQTA--VDRRMNRTARRRIE        73
WP_031665337        1 MKKP-YTIGLDIGTNSVGWAVLTDQYDLVKRMKISGDSEKKQIKKQNFWGVRLFEKGETA--AKRRMSRTARRRIE        73
WP_031669209        1 MKNP-YTIGLDIGTNSVGWAVLTDQYDLVKRMKVAGNSDKKQIKKQNFWGVRLFDDGQTA--VDRRMNRTARRRIE        73
WP_033920898        1 MKNP-YTIGLDIGTNSVGWAVLTDQYDLVKRMKVAGNSDKKQIKKQNFWGVRLFDDGQTA--VDRRMNRTARRRIE        76
AKI42028            1 MKNP-YTIGLDIGTNSVGWAVLTDQYDLVKRMKVAGNSDKKQIKKQNFWGVRLFDDGQTA--VDRRMNRTARRRIE        76
AKI50529            1 MKNP-YTIGLDIGTNSVGWAVLTDQYDLVKRMKVAGNSDKKQIKKQNFWGVRLFDDGQTA--VDRRMNRTARRRIE        76
EFR83390            1 ---------------------------------------------------------------------------
WP_046323366        1 MKKP-YTIGLDIGTNSVGWAALTDQYDLVKRMKVSEKKQIKKNLWGVRLIVDEGKTA--AHRRVNRTTRRRIE          73
AKE81011            1 ADKK-YSIGLDIGTNSVGWAVITDEYKVPSKKFKVLGNTDRHSIKKNLIGALLFDSGETA--EATRLKRTARRRYT       89
CUO82355            1 I-VD-YCIGLDLGTSVGWAVVDMNHRLMKRN----------------GKHLWGSRLFSNAETA--ATRSRSRIRRRYN     64
WP_033162887        1 KDIR-YSIGLDIGTNSVGWAVMDEHYELLKKG---------------NHHMWGSRLFDAAEPA--ATRASRSIRRRYN     65
ADKK6242            1 ADKK-YSIGLDIGTNSVGWAVITDEYKVPSKKFKVLGNTDRHSIKKNLIGALLFDSGETA--EATRLKRTARRRYT      106
AGZ01981            1 ADKK-YSIGLDIGTNSVGWAVITDEYKVPSKKFKVLGNTDRHSIKKNLIGALLFDSGETA--EATRLKRTARRRYT       73
AKS40380            1 MDKK-YSIGLAIGTNSVGWAVITDEYKVPSKKFKVLGNTDRHSIKKNLIGALLFDSGETA--EATRLKRTARRRYT       73
4UN5_B              1 MDKK-YSIGLAIGTNSVGWAVITDEYKVPSKKFKVLGNTDRHSIKKNLIGALLFDSGETA--EATRLKRTARRRYT       77
WP_010922251       74 RRRQNRICYLQEIFSNEMAKVDDSFFHRLEE-SFLV--EEDKK----H ERHPIFGN[IV-DEVAYHEKYPTI[M]LRKKLV  143
WP_039695303       75 RRRQNRLRYLQEIFANEIAKVDESFFQRLDE-SFLT--DDDKT---F DSHPIFGNKA-EEDAYHQKFPTIYHLRKHLA    144
WP_045635197       74 RRRQNRLRYLQEIFSEEMSKVDSSFFHRLDD-SFLI--PEDKR---E SKYPIFATLT-EEKEYHKQPPTIYHLRKQLA    143
5AXW_A             62 RRRHRIQRVKKLLFD---------------------------G---- --NPYEARVK-------------GLSQKLS    104
WP_009880683       74 RRRKNRICYLQEIFSNEMAKVDDSFFHRLEE-SFLV--EEDKK----H ERHPIFGNIV-DEVAYHEKYPTIYHLRKKLV   143
WP_010922251       74 RRRKNRICYLQEIFSNEMAKVDDSFFHRLEE-SFLV--EEDKK----H ERHPIFGNIV-DEVAYHEKYPTIYHLRKKLA   143
WP_011054416       74 RRRKNRICYLQEIFSNEMAKVDDSFFHRLEE-SFLV--EEDKK----H ERHPIFGNIV-DEVAYHEKYPTIYHLRKKLA   143
WP_011284745       74 RRRKNRICYLQEIFSNEMAKVDDSFFHRLEE-SFLV--EEDKK----H ERHPIFGNIV-DEVAYHEKYPTIYHLRKKLV   143
WP_011285506       74 RRRKNRICYLQEIFSNEMAKVDDSFFHRLEE-SFLV--EEDKK----H ERHPIFGNIV-DEVAYHEKYPTIYHLRKKLA   143
WP_011527619       74 RRRKNRICYLQEIFSNEMAKVDDSFFHRLEE-SFLV--EEDKK----H ERHPIFGNIV-DEVAYHEKYPTIYHLRKKLV   143
WP_012560673       74 RRRKNRICYLQEIFSNEIAKVDDSFFHRLEE-SFLV--EEDKK----H ERHPIFGNIV-DEVAYHEKYPTIYHLRKKLA   143
WP_014407541       74 RRRKNRICYLQEIFSNEIAKVDDSFFHRLEE-SFLV--EEDKK----H ERHPIFGNIV-DEVAYHEKYPTIYHLRKKLA   143
WP_020905136       74 RRRKNRICYLQEIFSNEMAKVDDSFFHRLEE-SFLV--EEDKK----H ERHPIFGNIV-DEVAYHEKYPTIYHLRKKLA   143
WP_023080005       74 RRRKNRICYLQEIFSNEMAKVDDSFFHRLEE-SFLV--EEDKK----H ERHPIFGNIV-DEVAYHEKYPTIYHLRKKLA   143
WP_023610282       74 RRRKNRICYLQEIFSNEMAKVDDSFFHRLEE-SFLV--EEDKK----H ERHPIFGNIV-DEVAYHEKYPTIYHLRKKLA   143
WP_030125963       74 RRRKNRICYLQEIFSNEMAKVDDSFFHRLEE-SFLV--EEDKK----H ERHPIFGNIV-DEVAYHEKYPTIYHLRKKLV   143
WP_030126706       74 RRRKNRICYLQEIFSNEMAKVDDSFFHRLEE-SFLV--EEDKK----H ERHPIFGNIV-DEVAYHEKYPTIYHLRKKLA   143
WP_031488318       74 RRRKNRICYLQEIFSNEMAKVDDSFFHRLEE-SFLV--EEDKK----H ERHPIFGNIV-DEVAYHEKYPTIYHLRKKLA   143
WP_032460140       74 RRRKNRICYLQEIFSNEIAKVDDSFFHRLEE-SFLV--EEDKK----H ERHPIFGNIV-DEVAYHEKYPTIYHLRKKLA   143
WP_032461047       74 RRRKNRICYLQEIFSNEIAKVDDSFFHRLEE-SFLV--EEDKK----H ERHPIFGNIV-DEVAYHEKYPTIYHLRKKLA   143
WP_032462016       74 RRRKNRICYLQEIFSNEMAKVDDSFFHRLEE-SFLV--EEDKK----H ERHPIFGNIV-DEVAYHEKYPTIYHLRKKLA   143
WP_032462936       74 RRRKNRICYLQEIFSNEMAKVDDSFFHRLEE-SFLV--EEDKK----H ERHPIFGNIV-DEVAYHEKYPTIYHLRKKLA   143
WP_032464890       74 RRRKNRICYLQEIFSNEMAKVDDSFFHRLEE-SFLV--EEDKK----H ERHPIFGNIV-DEVAYHEKYPTIYHLRKKLA   143
WP_033888930        1 -------------MAKVDDSFFHRLEE-SFLV--EEDKK----H ERHPIFGNIV-DEVAYHEKYPTIYHLRKKLA       54
WP_038431314       74 RRRKNRICYLQEIFSNEMAKVDDSFFHRLEE-SFLV--EEDKK----H ERHPIFGNIV-DEVAYHEKYPTIYHLRKKLA   143
WP_038432938       74 RRRKNRICYLQEIFSNEMAKVDDSFFHRLEE-SFLV--EEDKK----H ERHPIFGNIV-DEVAYHEKYPTIYHLRKKLA   143
WP_038434062       74 RRRKNRICYLQEIFSNEMAKVDDSFFHRLEE-SFLV--EEDKK----H ERHPIFGNIV-DEVAYHEKYPTIYHLRKKLV   143
BAQ51233            1 ---------------------------------------------------------------------------
```

```
KGE60162        ----------------------------------------------------------------------
KGE60856        ----------------------------------------------------------------------
WP_002989955 74 RRXNRICYLQEIFSNEMAKVDDSFFHRLEE-SFLV--EEDKK---H ERHPIFGNIV-DEVAYHEKPTIYHLRKKLV 143
WP_003030002 74 RRXNRLRYLQEIFAEEMNKVDENFFQRLDD-SFLV--DEDKR---G ERHPIFGNIA-AEVKYHDDFPTIYHLRKHLA 143
WP_003065552 75 RRKNRLRYLQEIFAEEMTKVDDSFFQRLDE-SFLRwGDDNKK---L GRYPIFGNKA-DVVKYHQEFPTIYHLRKHLA 146
WP_001040076 74 RRRNRIRILYLQEIFAEEMSKVDDSFFHRLED-SFLV--EEDKR---G SKYPIFATLQ-EEKYHEKFPTIYHLRKELA 143
WP_001040078 74 RRRNRIRILYLQEIFAEEMSKVDDSFFHRLED-SFLV--EEDKR---G SKYPIFATLQ-EEKDYHEKFPTIYHLRKELA 143
WP_001040080 74 RRRNRIRILYLQEIFAEEMSKVDDSFFHRLED-SFLV--EEDKR---G SKYPIFATLQ-EEKDYHEKFSTIYHLRKELA 143
WP_001040081 74 RRRNRIRILYLQEIFAEEMSKVDDSFFHRLED-SFLV--EEDKR---G SKYPIFATLQ-EEKDYHEKFPTIYHLRKELA 143
WP_001040083 74 RRRNRIRILYLQEIFAEEMSKVDDSFFHRLED-SFLV--EEDKR---G SKYPIFATLQ-EEKDYHEKFSTIYHLRKELA 143
WP_001040085 74 RRRNRIRILYLQEIFAEEMSKVDDSFFHRLED-SFLV--EEDKR---G SKYPIFATLQ-EEKDYHEKFSTIYHLRKELA 143
WP_001040087 74 RRRNRIRILYLQEIFAEEMSKVDDSFFHRLED-SFLV--EEDKR---G SKYPIFATLQ-EEKDYHEKFSTIYHLRKELA 143
WP_001040088 74 RRRNRIRILYLQEIFAEEMSKVDDSFFHRLED-SFLV--EEDKR---G SKYPIFATLQ-EEKDYHEKFSTIYHLRKELA 143
WP_001040089 74 RRRNRIRILYLQEIFAEEMSKVDDSFFHRLED-SFLV--EEDKR---G SKYPIFATLQ-EEKYYHEKFSTIYHLRKELA 143
WP_001040090 74 RRRNRIRILYLQEIFAEEMSKVDDSFFHRLED-SFLV--EEDKR---G SKYPIFATLQ-EEKDYHEKFSTIYHLRKELA 143
WP_001040091 74 RRRNRIRILYLQEIFAEEMSKVDDSFFHRLED-SFLV--EEDKR---G SKYPIFATLQ-EEKYYHEKFSTIYHLRKELA 143
WP_001040092 74 RRRNRIRILYLQEIFAEEMSKVDDSFFHRLED-SFLV--EEDKR---G SKYPIFATLQ-EEKDYHEKFSTIYHLRKELA 143
WP_001040094 74 RRRNRIRILYLQEIFAEEMSKVDDSFFHRLED-SFLV--EEDKR---G SKYPIFATMQ-EEKYYHEKFSTIYHLRKELA 143
WP_001040095 74 RRRNRIRILYLQEIFAEEMSKVDDSFFHRLED-SFLV--EEDKR---G SKYPIFATMQ-EEKYYHEKFSTIYHLRKELA 143
WP_001040096 74 RRRNRIRILYLQEIFAEEMSKVDDSFFHRLED-SFLV--EEDKR---G SKYPIFATMQ-EEKYYHEKFSTIYHLRKELA 143
WP_001040097 74 RRRNRIRILYLQEIFAEEMSKVDDSFFHRLED-SFLV--EEDKR---G SKYPIFATMQ-EEKYYHEKFPTIYHLRKELA 143
WP_001040098 74 RRRNRIRILYLQEIFAEEMSKVDDSFFHRLED-SFLV--EEDKR---G SKYPIFATMQ-EEKYYHEKFPTIYHLRKELA 143
WP_001040099 74 RRRNRIRILYLQEIFAEEMSKVDDSFFHRLED-SFLV--EEDKR---G SKYPIFATMQ-EEKYYHEKFPTIYHLRKELA 143
WP_001040100 74 RRRNRIRILYLQEIFAEEMSKVDDSFFHRLED-SFLV--EEDKR---G SKYXIFATMQ-EEKYYHEKFPTIYHLRKELA 143
WP_001040104 74 RRRNRIRILYLQEIFAEEMSKVDDSFFHRLED-SFLV--EDDKR---G SKYPIFATMQ-EEKYYHEKFPTIYHLRKELA 143
WP_001040105 74 RRRNRIRILYLQEIFAEEMSKVDDSFFHRLED-SFLV--EDDKR---G SKYPIFATMQ-EEKYYHEKFPTIYHLRKELA 143
WP_001040106 74 CRRNRIRILYLQEIFAEEMSKVDDSFFHRLED-SFLV--EDDKR---G SKYPIFATMQ-EEKYYHEKFPTIYHLRKELA 143
WP_001040107 74 RRRNRIRILYLQEIFAEEMSKVDDSFFHRLED-SFLV--EDDKR---G SKYPIFATMQ-EEKYYHEKFPTIYHLRKELA 143
WP_001040108 74 RRRNRIRILYLQEIFAEEMSKVDDSFFHRLED-SFLV--EDDKR---G SKYPIFATMQ-EEKYYHEKFPTIYHLRKELA 143
WP_001040109 74 RRRNRIRILYLQEIFAEEMSKVDDSFFHRLED-SFLV--EDDKR---G SKYPIFATMQ-EEKYYHEKFPTIYHLRKELA 143
WP_001040110 74 RRRNRIRILYLQEIFAEEMSKVDDSFFHRLED-SFLV--EDDKR---G SKYPIFATMQ-EEKYYHEKFPTIYHLRKELA 143
WP_015058523 74 RRRNRIRILYLQEIFAEEMSKVDDSFFHRLED-SFLV--EEDKR---G SKYPIFATLQ-EEKYYHEKFPTIYHLRKELA 143
WP_017643650 74 RRRNRIRILYLQEIFAEEMSKVDDSFFHRLED-SFLV--EEDKR---G SKYPIFATLQ-EEKYYHEKFPTIYHLRKELA 143
WP_017647151 74 RRRNRIRILYLQEIFAEEMSKVDDSFFHRLED-SFLV--EEDKR---G SKYPIFATLQ-EEKDYHEKFPTIYHLRKELA 143
WP_017648376 74 RRRNRIRILYLQEIFAEEMSKVDDSFFHRLED-SFLV--EEDKR---G SKYPIFATLQ-EEKDYHEKFPTIYHLRKELA 143
WP_017649527 74 RRRNRIRILYLQEIFAEEMSKVDDSFFHRLED-SFLV--EEDKR---G SKYPIFATLQ-EEKDYHEKFPTIYHLRKELA 143
WP_017771611 74 RRRNRIRILYLQEIFAEEMSKVDDSFFHRLED-SFLV--EEDKR---G SKYPIFATLQ-EEKDYHEKFPTIYHLRKELA 143
WP_017771984 74 RRRNRIRILYLQEIFAEEMSKVDDSFFHRLED-SFLV--EEDKR---G SKYPIFATMQ-EEKDYHEKFPTIYHLRKELA 143
CFQ25032        74 RRRNRIRILYLQEIFAEEMSKVDDSFFHRLED-SFLV--EEDKR---G SKYPIFATLQ-EEKDYHEKFPTIYHLRKELA 143
CFV16040        74 RRRNRIRILYLQEIFAEEMSKVDDSFFHRLED-SFLV--EEDKR---G SKYPIFATLQ-EEKDYHEKFPTIYHLRKELA 143
KLJ37842        74 RRRNRIRILYLQEIFAEEMSKVDDSFFHRLED-SFLV--EEDKR---G SKYPIFATLQ-EEKDYHEKFPTIYHLRKELA 143
KLJ72361        74 RRRNRIRILYLQEIFAEEMSKVDDSFFHRLED-SFLV--EEDKR---G SKYPIFATLQ-EEKDYHEKFPTIYHLRKELA 143
KLL20707        74 RRRNRIRILYLQEIFAEEMSKVDDSFFHRLED-SFLV--EEDKR---G SKYPIFATLQ-EEKDYHEKFPTIYHLRKELA 143
KLL42645        74 RRRNRIRILYLQEIFAEEMSKVDDSFFHRLED-SFLV--EEDKR---G SKYPIFATMQ-EEKDYHEKFPTIYHLRKELA 143
WP_047207273 74 RRRNRIRILYLQEIFAEEMSKVDDSFFHRLED-SFLV--EEDKR---G SKYPIFATMQ-EEKDYHEKFPTIYHLRKELA 143
WP_047209694 74 RRRNRIRILYLQEIFAEEMSKVDDSFFHRLED-SFLV--EEDKR---G SKYPIFATMQ-EEKDYHEKFPTIYHLRKELA 143
WP_050198062 74 RRRNRIRILYLQEIFAEEMSKVDDSFFHRLED-SFLV--EEDKR---G SKYPIFATLQ-EEKDYHEKFPTIYHLRKELA 143
WP_050201642 74 RRRNRIRILYLQEIFAEEMSKVDDSFFHRLED-SFLV--EEDKR---G SKYPIFATLQ-EEKDYHEKFPTIYHLRKELA 143
WP_050204027 74 RRRNRIRILYLQEIFAEEMSKVDDSFFHRLED-SFLV--EEDKR---G SKYPIFATMQ-EEKDYHEKFPTIYHLRKELA 143
WP_050881965 74 RRRNRIRILYLQEIFAEEMSKVDDSFFHRLED-SFLV--EEDKR---G SKYPIFATLQ-EEKDYHEKFPTIYHLRKELA 143
WP_050886065 74 RRRNRIRILYLQEIFAEEMSKVDDSFFHRLED-SFLV--EEDKR---G SKYPIFATMQ-EEKDYHEKFPTIYHLRKELA 143
AHN30376        74 RRRNRIRILYLQEIFAEEMSKVDDSFFHRLED-SFLV--EEDKR---G SKYPIFATLQ-EEKDYHEKFPTIYHLRKELA 143
EAO78426        74 RRRNRIRILYLQEIFAEEMSKVDDSFFHRLED-SFLV--EEDKR---G SKYPIFATLQ-EEKDYHEKFPTIYHLRKELA 143
```

| ID | | Sequence | | |
|---|---|---|---|---|
| CCW42055 | 74 | RRRNRILYLQEIFAEEMKSKVDDSFFHRLED-SFLV-EEDKR---G | SKYPIFATLQ-EEKDYHEKPFTIYHLRKELA | 143 |
| WP_003041502 | 74 | RRRNRLRYLQEIFAEEMMQVDESFFQRLDD-SFLV-DEDKR---G | ERHPIFGNIA-AEVKYHDEFPTIYHLRKHLA | 143 |
| WP_037593752 | 75 | RRRNRLRYLQEIFTEEMNKVDENFFQRLDD-SFLV-EEDKQ---G | SKYPIFGTLK-EEKEYHKKKTIYHLREELA | 144 |
| WP_049516684 | 74 | RRRNRLRYLQEIFAEEMMQVDESFFQRLDD-SFLV-EEDKQ---G | SRYPIFGNIA-AEVKYHDDFPTIYHLREELA | 144 |
| GAD46167 | 75 | RRKRLRYLQDIFTEEMKVDESFFQRLDD-SFLV-EEDKQ---G | SKYPIFGTLK-EEKEYHKKKTIYHLREELA | 144 |
| WP_018363470 | 74 | RRRNRLRYLQEIFANEMAKLDDSFFQRLEE-SFLT-DNDKN---F | DSHPIFGNKA-EEDAYHQKPTIYHLRKHLA | 143 |
| WP_003043819 | 74 | RRRNRLRYLQEIFANEMAKLDDSFFQRLEE-SFLV-EEDKK---N | ERHPIFGNLA-DEVAYHRNYPTIYHLRKKLA | 144 |
| WP_006269658 | 74 | RRRNRLRYLQEIFTGEMNKVDENFFQRLDD-SFLV-DEDKR---G | ERHPIFGNLA-AEVKYHDDFPTIYHLRKKLA | 143 |
| WP_048800889 | 74 | RRRNRLRYLQEIFIEEMNKVDENFFQRLDD-SFLV-TEDKR---G | SKYPIFGTLK-EEKEYKEFETIYHLRKRLA | 143 |
| WP_012767106 | 74 | RRRNRIRYLQEIFSSEMMSVDDSFFHRLEE-SFLV-EEDKK---H | ERHPIFGNIV-DEVAYHEKYPTIYHLRKKLA | 143 |
| WP_014612333 | 74 | RRRNRIRYLQEIFSSEMMSVDDSFFHRLEE-SFLV-EEDKK---H | ERHPIFGNIV-DEVAYHEKYPTIYHLRKKLA | 143 |
| WP_015017095 | 74 | RRRNRIRYLQEIFSSEMMSVDDSFFHRLEE-SFLV-EEDKK---H | ERHPIFGNIV-DEVAYHEKYPTIYHLRKKLA | 143 |
| WP_015057649 | 74 | RRRNRIRYLQEIFSSEMMSVDDSFFHRLEE-SFLV-EEDKK---H | ERHPIFGNIV-DEVAYHEKYPTIYHLRKKLA | 143 |
| WP_048272215 | 74 | RRRNRLRYLQEIFSSEMMSKVDDSFFHRLEE-SFLV-EEDKK---H | NKHPIFANLA-DEVAYHKKYPTIYHLRKELV | 143 |
| WP_049519324 | 74 | RRRNRLRYLQEIFSSEMMSKVDDSFFHRLEE-SPYV-LEDKE---G | NKHPIFANLA-DEVAYHKKYPTIYHLRKELV | 143 |
| WP_012515931 | 74 | RRRNRLRYLKEIFTEEMAKVDDGFFQRLEDD-SPYV-LEDKE---G | DSHPIFGNKA-EEDTYHQEPFTIYHLRKELV | 143 |
| WP_021320964 | 74 | RRRNRLRPLKEIFTEEMAKVDDGFFQRLED-SFLT-DDDKT---F | DSHPIFGNKA-EEDAYHQKPTIYHLRNYLA | 143 |
| WP_037581760 | 74 | RRRNRLRYLQEIFAEEMAKVDESFFYRLDE-SFLT-DDDKT---F | DSHPIFGNKA-EEDAYHQKPTIYHLRKYLA | 143 |
| WP_044232481 | 74 | RRRNRLRYLQEIFAEEMAKVDESFFQRLEE-SFLT-DDDKT---F | DSHPIFGNKA-EEDAYHQKPTIYHLRKYLA | 143 |
| WP_009854540 | 74 | RRKRLRYLQEIFAKEMAKVDESFFYRLDE-SFLT-TDDKD---F | ERHPIFGNKA-DEIKYHQEFPTIYHLRKHLA | 144 |
| WP_012962174 | 74 | RRRNRLRYLQEIFAEEMAKVDESFFQRLEE-SFLT-DDDKT---F | DSHPIFGNKA-EEDAYHQKPTIYHLRKYLA | 144 |
| WP_039695303 | 74 | RRRNRLRYLQEIFANEIAKVDESFFQRLEE-SFLT-DDDKT---F | DSHPIFGNKA-EEDAYHQKPTIYHLRKYLA | 144 |
| WP_014334983 | 75 | RRKRIKELQKIFSSEMNELDIAFFPRLSE-SFLV-SDDKE---F | ERHPIFGNLK-DEITYHNDYPTIYHLRQTLA | 143 |
| WP_003099269 | 74 | RRKYRIKELQKIFSSEMNELDIAFFPRLSE-SFLV-SDDKE---F | ERHPIFGNLK-DEITYHNDYPTIYHLRQTLA | 143 |
| AHY15608 | 74 | RRKYRIKELQKIFSSEMNELDIAFFPRLSE-SFLV-SDDKE---F | ENHPIFGNLK-DEITYHNDYPTIYHLRQTLA | 143 |
| AHY17476 | 74 | RRKYRIKELQKIFSSEMNELDIAFFPRLSE-SFLV-SDDKE---F | ENHPIFGNLK-DEITYHNDYPTIYHLRQTLA | 143 |
| ESR09100 | | | | |
| AGM98575 | 74 | RRRNRILYLQKIFSSEEMGKIVDDSFFFPRLSE-SFLV-SDDKE---F | ENHPIFGNLE-EEVKYHENFPTIYHLRQTLA | 143 |
| ALF27331 | 74 | RRRNRILYLQEIFSEEEMGKIVDDSFFHRLED-SFLV-TEDKR---G | ERHPIFGNLE-EEVKYHENFPTIYHLRQTLA | 143 |
| WP_018372492 | 74 | RRRNRIRYLQHIFAEEMNRADENFFHRLKE-SFFV-EEDKT---Y | SKYPIFGTLE-EEKNYHKNYPTIYHLRKTLA | 143 |
| WP_045618028 | 75 | RRRNRLRYLQEIFAEEMMSKVDDISFFHRLDD-SFLI-PEDKR---G | SKYPIFATLE-EEKEYHKQPFTIYHLRKHLA | 144 |
| WP_045635197 | 74 | RRRNRILYLQEIFSEEEMGKIVDDSFFHRLDD-SFLI-PEDKR---E | SKYPIFATLI-EEKEYHKNQPPTIYHLRKQLA | 143 |
| WP_002263349 | 74 | RRRNRILYLQEIFSEEEMGKIVDDSFFHRLED-SFLV-TEDKR---G | ERHPIFGNLE-EEVKYHENFPTIYHLRQYLA | 143 |
| WP_002263887 | 74 | RRRNRILYLQEIFSEEEMGKIVDDSFFHRLDE-SFLT-DDDKN---F | DSYPIFGNKA-EEDAYHQKPTIYHLRKHLA | 143 |
| WP_002264920 | 74 | RRRNRILYLQEIFSEEEMGKIVDDSFFHRLED-SFLT-TEDKR---G | ERHPIFGNLE-EEDAYHQKPTIYHLRKHLA | 143 |
| WP_002269043 | 74 | RRRNRILYLQEIFSEEEMGKIVDDSFFHRLED-SFLV-TEDKR---G | ERHPIFGNLE-EEVKYHENFPTIYHLRQYLA | 143 |
| WP_002269448 | 74 | RRRNRILYLQEIFSEEEMGKIVDDSFFHRLED-SFLV-TEDKR---G | ERHPIFGNLE-EEVKYHENFPTIYHLRQYLA | 143 |
| WP_002271977 | 74 | RRRNRILYLQEIFSEEEMGKIVDDSFFHRLED-SFLV-TEDKR---G | ERHPIFGNLE-EEVKYHENFPTIYHLRQYLA | 143 |
| WP_002272766 | 74 | RRRNRILYLQEIFSEEEMGKIVDDSFFHRLED-SFLT-DDDKN---F | DSHPIFGNKA-EEDAYHQKPTIYHLRKHLA | 143 |
| WP_002273241 | 74 | RRRNRILYLQEIFSEEEMGKIVDDSFFHRLED-SFLV-TEDKR---G | ERHPIFGNLE-EEVKYHENFPTIYHLRQYLA | 143 |
| WP_002275430 | 74 | RRRNRILYLQEIFAEEEMSKVDDSFFHRLED-SFLV-TEDKR---G | DSHPIFGNKA-EEDAYHQKPTIYHLRKHLA | 143 |
| WP_002276448 | 74 | RRRNRILYLQEIFSEEEMGKIVDDSFFHRLDE-FFLV-TEDKR---G | ERHPIFGNLE-EEVKYHENFPTIYHLRQYLA | 143 |
| WP_002277050 | 74 | RRRNRILYLQEIFSEEEMGKIVDDSFFHRLED-SFLT-DDDKN---F | DSHPIFGNKA-EEDAYHQKPTIYHLRKHLA | 143 |
| WP_002277364 | 74 | RRRNRILYLQEIFSEEEMGKIVDDSFFHRLED-SFLV-TEDKR---G | ERHPIFGNLE-EEVKYHENFPTIYHLRQYLA | 143 |
| WP_002279025 | 74 | RRRNRILYLQEIFSEEEMGKIVDDSFFHRLED-SFLT-DDDKN---F | DSHPIFGNKA-EEDAYHQKPTIYHLRKHLA | 143 |
| WP_002279859 | 74 | RRRNRILYLQEIFSEEEMGKIVDDSFFHRLDE-SFLV-TEDKR---G | ERHPIFGNLE-EEVKYHENFPTIYHLRQYLA | 143 |
| WP_002280230 | 74 | RRRNRILYLQEIFAEEEMSKVDDSFFHRLED-SFLV-TEDKR---G | ERHPIFGNLE-EEVKYHENFPTIYHLRQYLA | 143 |
| WP_002281696 | 74 | RRRNRILYLQEIFSEEEMGKIVDDSFFHRLED-SFLV-TEDKR---G | ERHPIFGNLE-EEVKYHENFPTIYHLRQYLA | 143 |
| WP_002282247 | 74 | RRRNRILYLQEIFAEEEMSKVDDSFFHRLED-SFLT-DDDKN---F | DSHPIFGNKA-EEDAYHQKPTIYHLRKHLA | 143 |
| WP_002282906 | 74 | RRRNRILYLQEIFSEEEMGKIVDDSFFHRLED-SFLV-TEDKR---G | ERHPIFGNLE-EEVKYHENFPTIYHLRQYLA | 143 |
| WP_002283846 | 74 | RRRNRILYLQEIFSEEEMGKIVDDSFFHRLED-SFLV-TEDKR---G | ERHPIFGNLE-EEVKYHENFPTIYHLRQYLA | 143 |
| WP_002287255 | 74 | RRRNRILYLQEIFSEEEMGKIVDDSFFHRLED-SFLV-TEDKR---G | ERHPIFGNLE-EEVKYHENFPTIYHLRQYLA | 143 |
| WP_002288990 | 74 | RRRNRILYLQEIFSEEEMGKIVDDSFFHRLED-SFLV-TEDKR---G | ERHPIFGNLE-EEVKYHENFPTIYHLRQYLA | 143 |

-continued

```
WP_002289641    74  RRRNRILYLQEIFSEEMGKVDDSFFHRLED-SFLV--TEDKR----G ERHPIFGNLE-EEVKYHENFPTIYHLRQYLA 143
WP_002290427    74  RRRNRILYLQEIFSEEMGKVDDSFFHRLED-SFLV--TEDKR----G ERHPIFGNLE-EEVKYHENFPTIYHLRQYLA 143
WP_002295753    74  RRRNRILYLQEIFSEEMGKVNDSFFHRLED-SFLV--TEDKR----G ERHPIFGNLE-EEVKYHENFPTIYHLRQYLA 143
WP_002296423    74  RRRNRILYLQEIFSEEMGKVDDSFFHRLED-SFLV--TEDKR----G ERHPIFGNLE-EEVKYHENFPTIYHLRQYLA 143
WP_002304487    74  RRRNRILYLQEIFAEEMQDSFFHRLED-SFLV--EEDKR----G SRYPIFGTLK-EEKKYHKEFKTIYHLREKLA 143
WP_002305844    74  RRRNRILYLQEIFSEEMDKVDDSFFHRLED-SFLV--TEDKR----G ERHPIFGNLE-EEVKYHENFPTIYHLRQYLA 143
WP_002307203    74  RRRNRILYLQEIFSEEMGKVDDSFFHRLED-SFLV--TEDKR----G ERHPIFGNLE-EEVKYHENFPTIYHLRQYLA 143
WP_002310390    74  RRRNRILYLQEIFSEEMGKVDDSFFHRLED-SFLV--TEDKR----G ERHPIFGNLE-EEVKYHENFPTIYHLRQYLA 143
WP_002352408    74  RRRNRILYLQEIFAEEMSKVDDSFFHRLED-SFLV--TEDKR----G ERHPIFGNLE-EEVKYHENFPTIYHLRQYLA 143
WP_012997688    74  RRRNRILYLQEIFSEEMGKVDDSFFHRLED-SFLV--TEDKR----G ERHPIFGNLE-EEVKYHENFPTIYHLRQYLA 143
WP_014677909    74  RRRNRILYLQEIFAEEMSKVDDSFFHRLED-SFLV--TEDKR----G ERHPIFGNLE-EEVKYHENFPTIYHLRQYLA 143
WP_019312892    74  RRRNRILYLQEIFAEEMSKVDDSFFHRLED-SFLV--TEDKR----G ERHPIFGNLE-EEVKYHENFPTIYHLRQYLA 143
WP_019313659    74  RRRNRILYLQEIFSEEMGKVDDSFFHRLED-SFLV--TEDKR----G ERHPIFGNLE-EEVKYHENFPTIYHLRQYLA 143
WP_019314093    74  RRRNRILYLQEIFSEEMGKVDDSFFHRLED-SFLV--TEDKR----G ERHPIFGNLE-EEVKYHENFPTIYHLRQYLA 143
WP_019315370    74  RRRNRILYLQEIFSEEMGKVDDSFFHRLED-SFLV--TEDKR----G ECHPIFGNLE-EEVKYHENFPTIYHLRQYLA 143
WP_019803776    74  RRRNRILYLQEIFSEEMGKVDDSFFHRLED-SFLV--TEDKR----G ERHPIFGNLE-EEVKYHENFPTIYHLRQYLA 143
WP_019805234    74  RRRNRILYLQEIFSEEMGKVDDSFFHRLED-SFLV--TEDKR----G ERHPIFGNLE-EEVKYHENFPTIYHLRQYLA 143
WP_024783594    74  RRRNRILYLQEIFAEEMSKVDDSFFHRLED-SFLT--DDDKN----F DSHPIFGNKA-EEDAYHQKFPTIYHLRKHLA 143
WP_024784288    74  RRRNRILYLQEIFAEEMSKVDDSFFHRLED-SFLT--DDDKN----F DSHPIFGNKA-EEDAYHQKFPTIYHLRKHLA 143
WP_024784666    74  RRRNRILYLQEIFAEEMSKVDDSFFHRLED-SFLV--TEDKR----G ERHPIFGNLE-EEVKYHENFPTIYHLRQYLA 143
WP_024784894    74  RRRNRILYLQEIFAEEMNKVDDSFFHRLDE-SFLT--DDDKN----F DSHPIFGNKA-EEDAYHQKFPTIYHLRKHLA 143
WP_024786433    74  RRRNRILYLQEIFAEEMSKVDDSFFHRLED-SFLI--PEDKR----G ERHPIFGNLE-EEVKYHENFPTIYHLRQYLA 143
EMC03581        67  RRRNRILYLQEIFSEEMGKVDDSFFHRLED-SFLI--PEDKR----G SKYPIFATLI-EEKEYHKQPPTIYHLRKQLA 136
WP_000428612    75  RRKNRLRYLQEIFAEEMKVDDSFFHRLDD-SFLI--PEDKR----G SKYPIFATLQ-EEKEYHKQPPTIYHLRKQLA 144
WP_000428613    74  RRKNRLRYLQEIFAAEMNKVDESFFHRLDD-SFLV--PEDKR----G ERHPIFGTLE-EEKEYHKQPPTIYYLRKILA 144
WP_049523028    74  RRKNRLRYLQEIFSEEIGKVDSSFFHRLDD-SFLV--PEDKR----G SKHPIFGNIK-DEVDYHKNYPTIYHLRKKLA 143
WP_003107102    43  RRINRKYLQSIFDDEMSKIDSAFFQRIKD-SFLV--PDDKN----D DRHPIFGNLE-EEKAYHDNYPTIYHLRKALA 112
WP_054279288    76  RRKRNCYLRDIFESEMHTIDKHFFLRLED-SFLH--KSDKR----Y EAHPIFGTLQ-EEKAYHDNYPTIYHLRKALA 145
WP_049531101    75  RRKRNRLRYLQEIFSEEISKVDNSFFHRLDD-SFLV--PEDKR----G SKYPIFATLT-EEKEYHKQPPTIYHLRKQLA 144
WP_049538452    75  RRKNRLRYLQEIFAEEMNKVDSSFFHRLDD-SFLV--PEDKR----G SKYPIFATLA-EEKEYHKQPPTIYHLRKQLA 144
WP_049549711    76  RRKNRLRYLQEIFSGEMSKVDSSFFHRLDD-SFLV--PEDKR----G SKYPIFATLV-EEKEYHKQFPTIYHLRKQLA 145
WP_007896501    76  RRRYRLCQLQNIFATEMKVDDTFFQRLSE-SFFY--YQDKA----F DKHPIFGNSK-EERAYHKTYPTIYHLRKDLA 145
EFR44625        28  RRRYRLCQLQNIFTESMNEIDESFFHRLDD-SFLV--PEDKR----G SKYPIFATLQ-EEKEYHKQPPTIYHLRKQLA  97
WP_002897477    74  RRRNRILYLQEIFSEEISKLDSSFFHRLEE-SFLV--EEDKK---H ERHPIFGNIV-DEVAYHEKYPTIYHLRKHLA 143
WP_002906454    74  RRKNRILYLQEIFSNEMAKVDSSFFHRLEE-SFLV--EEDKK---H ERHPIFGNIV-DEVAYHEKYPTIYHLRKHLA 143
WP_009729476    73  RRKNRLRYLQEIFSEEIGKVDSSFFHRLDE-SFLV--EEDKE---Y SKYPIFSNEK-EDKNYDKYPTIYHLRKDLA 142
CQR24647        74  RRRNRILYLQDIFSPELNQVDESFLHRLDD-SFLVa--PEDKR---G ERHVIPGNIA-DEVKYHKEPPTIYHLREPHLA 143
WP_000066813    75  RRRNRILYLQEIFSQEISKVDSSFFHRLDD-SFLV--PEDKR----G SKYPIFATLV-EEKEYHKKKPPTIYHLRKHLA 144
WP_009754323    75  RRRNRILYLQEIFAEEMSKVDSSFFHRLDD-SFLV--PEDKS---G SKYPIFATLA-EEKEYHKQPPTIYHLRKHLA 144
WP_044674937    74  RRRNRILYLQEIFAEEINKIDSSFFHRLDD-SFLV--EDKQ----G SKHPIFGTLQ-EEKKYHKQPPTIYHLRKQLA 143
WP_044676715    74  RRRNRILYLQEIFAEEINKIDSFFQRLDD-SFLV--EDKQ----G SKHPIFGTLQ-EEKEYHKQPPTIYHLRKQLA 143
WP_044680361    74  RRRNRILYLQEIFAEEINKIDSSFFQRLDD-SFLIV--EDKQ---G SKHPIFGTLQ-EEKKYHKQPPTIYHLRKQLA 144
WP_044681799    74  RRRNRILYLQEIFAEEINKIDSSFFHRLDD-SFLIV--EDKQ---G SKHPIFGTLQ-EEKKYHKQPPTIYHLRKQLA 143
WP_049533112    74  RRRNRLRYLQEIFAEEMNKVDENFFQRLDD-SFLIV--DEDKR---G ERHPIFGNIA-AEVKYHDDFPTIYHLRKHLA 143
WP_029909905    28  HRKFPRLRLLEDMFEKEILSKDPSFFIRLKE-AFLSpkDEQKQ--F ---LFNDKDyTDADYYEQYKTIYHLRYDLI 100
WP_066506696    61  KRRERRILLRAILQDMVLEKDPTFFIRLEHt-SFLD--EEDKAKy1G DNYNLFIDEDfNDYTYYHKYPTIYHLRKALC 139
AIT42264        74  RRRNRICYLQEIFSNEMAKVDSSFFHRLEE-SFLV--EEDKK---H ERHPIFGNIV-DEVAYHEKYPTIYHLRKKLV 143
WP_034440723    73  RRRFPRIRELQKIFDKSMGEVDSNFFHRLDE-SFLV--EEDKE---Y SKYPIFSNEK-EDKNYDKYPTIYHLRKDLA 142
AKQ21048        74  RRRNRLIYLQDIFSNEMAKVDDSFFHRLEE-SFLV--EEDKK---H ERHPIFGNIV-DEVAYHEKYPTIYHLRKKLV 143
WP_004636532    74  RRRNRLIYLQAFFEEAMTDLDENFFARLQE-SFLV--PDDKS---Y DRHPIFGSLE-EEVAYHNTYPTIYHLRKKLV 143
WP_002364836    74  RRRNRLRYLQAFFEEAMTDLDENFFARLQE-SFLV--PEDKK---W HRHPIFAKLE-DEVAYHETYPTIYHLRKKLA 143
```

```
WP_016631044    25  RRRNRLRYLQAFFEEAMTDLDENFFARLQE-SFLV--PEDKK----W HRHPIFAKLE-DEVAYHETYPTIYHLRKKLA  94
EMS75795            
WP_002373311    74  RRRNRLRYLQAFFEEAMTDLDENFFARLQE-SFLV--PEDKK----W HRHPIFAKLE-DEVAYHETYPTIYHLRKKLA 143
WP_002378009    74  RRRNRLRYLQAFFEEAMTALDENFFARLQE-SFLV--PEDKK----W HRHPIFAKLE-DEVAYHETYPTIYHLRKKLA 143
WP_002407324    74  RRRNRLRYLQAFFEEAMTALDENFFARLQE-SFLV--PEDKK----W HRHPIFAKLE-DEVAYHETYPTIYHLRKKLA 143
WP_002413717    74  RRRNRLRYLQAFFEEAMTDLDENFFARLQE-SFLV--PEDKK----W HRHPIFAKLE-DEVAYHETYPTIYHLRKKLA 143
WP_010775580    74  RRRNRLRYLQAFFEEAMTALDENFFARLQE-SFLV--PEDKK----W HRHPIFAKLE-DEVAYHETYPTIYHLRKKLA 143
WP_010818269    74  RRRNRLRYLQAFFEEAMTALDENFFARLQE-SFLV--PEDKK----W HRHPIFAKLE-DEVAYHETYPTIYHLRKKLA 143
WP_010824395    74  RRRNRLRYLQAFFEEAMTDLDENFFARLQE-SFLV--PEDKK----W HRHPIFAKLE-DEVAYHETYPTIYHLRKKLA 143
WP_016622645    74  RRRNRLRYLQAFFEEAMTALDENFFARLQE-SFLV--PEDKK----W HRHPIFAKLE-DEVAYHETYPTIYHLRKKLA 143
WP_033624816    74  RRRNRLRYLQAFFEEAMTALDENFFARLQE-SFLV--PEDKK----W HRHPIFAKLE-DEVAYHETYPTIYHLRKKLA 143
WP_033625576    74  RRRNRLRYLQAFFEEAMTALDENFFARLQE-SFLV--PEDKK----W HRHPIFAKLE-DEVAYHETYPTIYHLRKKLA 143
WP_033789179    74  RRRNRLRYLQAFFEEAMTALDENFFARLQE-SFLV--PEDKK----W HRHPIFAKLE-DEVAYHETYPTIYHLRKKLA 143
WP_002310644    74  RRRQRILELQKIFAPEILKIDEHFFARLNE-SFLV--LDEKK----Q SRHPVFATIK-QEKSYHQTYPTIYHLRQALA 143
WP_002312694    74  RRRQRILELQKIFAPEILKIDEHFFARLNE-SFLV--PDEKK----Q SRHPVFATIK-QEKSYHQTYPTIYHLRQALA 143
WP_002314015    74  RRRQRILELQKIFAPEILKIDEHFFARLNE-SFLV--LDEKK----Q SRHPVFATIK-QEKSYHQTYPTIYHLRQALA 143
WP_002320716    74  RRRQRILELQKIFAPEILKIDEHFFARLNE-SFLV--LDEKK----Q SRHPVFATIK-QEKSYHQTYPTIYHLRQALA 143
WP_002330729    74  RRRQRILELQKIFAPEILKIDEHFFARLNE-SFLV--LDEKK----Q SRHPVFATIK-QEKSYHQTYPTIYHLRQALA 143
WP_002335161    74  RRRQRILELQKIFAPEILKIDEHFFARLNE-SFLV--LDEKK----Q SRHPVFATIK-QEKSYHQTYPTIYHLRQALA 143
WP_002345439    74  RRRQRILELQKIFAPEILKIDEHFFARLNE-SFLV--LDEKK----Q SRHPVFATIK-QEKSYHQTYPTIYHLRQALA 143
WP_034867970    74  RRKYRLSKIQDLFAEELCKQDDCFFVRLEE-SFLV--PEEKQ----Y KPASIFPTLE-EEKEYYQKYPTIYHLRQKLV 143
WP_047937432    74  RRRQRILELQKIFAPEILKIDEHFFARLNE-SFLV--LDEKK----Q SRHPVFATIK-QEKSYHQTYPTIYHLRQALA 143
WP_010720994    74  RRKYRLSKIQDLFAEELCKQDDCFFVRLEE-SFLI--PEEKQ----Y KPASIFPTLE-EEKEYYQKYPTIYHLRQKLV 143
WP_010737004    74  RRKYRLSKIQDLFAEELCKQDDCFFVRLEE-SFLV--PEEKQ----Y KPASIFPTLE-EEKEYYQKYPTIYHLRQKLV 143
WP_034700478    74  RRKYRLSKIQDLFAEELCKQDDCFFVRLEE-SFLV--PEEKQ----Y KPASIFPTLE-EEKEYYQKYPTIYHLRQKLV 143
WP_007209003    74  RRRNRICYLQEIFQPEMNHLDNNFFYRLNE-SFLVa--DDAK----Y DKHPIFGTLD-EEIHFHEQPPTIYHLRKYLA 143
WP_023519017    74  RRRQRVLAIQDIFAEEIHKKDPNFFAREE-GDRV--EADKR----F AKPPVFATLS-EEKNYHRQYPTIYHLRHDLA 143
WP_010770040    74  RRRNRLRCYLQDLFTEEMNQVDANFHRLQE-SFLV--PDEKE----F ERHAIFGKME-ERHAYYREFPTIYHLRKHLA 143
WP_048604708    74  RRRNRISYLQTFPQEEMNRIDPNFFNRLDE-SFLI--EEDKL----S ERHPIFGTIE-EEVAYHKNYATIYHLRKELA 143
WP_010750235    74  RRKYRILELQKIFSEEILKKDSHFFARLDE-SFLV--PEDKQ----Y ARFPIFPTLL-EEKAYYQNYPTIYHLRKKLV 143
AII16583       113  RRKYRILELQKIFSNENAKVDDSFFHRLEE-SFLV---QEDKDL-F ERHPIFGNIV-DEVAYHDKYPTIYHLREKLV 182
WP_029073316    66  KRRERIRLLRGIMEDMVLDVDPTFIRLEE-SFLD---QEDKKGylK SNYNLFIDKDfNDKTYDKYPTIYHLRKHLC 144
WP_031589969    66  KRRERIRLLREIMEDMVLDVDPTFFIRLANvSFLD-QEDKKGy1K SNYNLFIDKDENDKTYDKYPTIYHLRKHLC 144
KDA45870        75  RRRNRLRYLQEIFAPALAKVDPNFFYRLEE-SSLVa--EDKK----Y DVYPIFGKRE-EELLYHDTHKTIYHLRSELA 144
WP_039099354    62  RRKWRLGLLREIFEPYITPVDDTFFLRKKQ-SNLS--PKDQR----K -QTSLFNDRT--DRAFYDDYPTIYHLRYKLM 132
AKP02966        65  RRKNRINWLNEIFSEELANTDPSFLIRLQN-SWVSkkDPDRK----R DKYNLFIDNPyTDKEYYREPPTIFHLRKELI 137
WP_010991369    74  RRRNRISYLQGIFAEEMSKTDANFFCRLSD-SFYV--DNEKR----N SRHPFFATIE-EEVAYHKNYPTIYHLREELV 143
WP_033838504    74  RRRNRISYLQGIFAEEMSKTDANFFCRLSD-SFYV--DNEKR----N SRHPFFATIE-EEVAYHKNYPTIYHLREELV 143
EHN60060        77  RRRNRISYLQGIFAEEMSKTDANFFCRLSD-SFYV--DNEKR----N SRHPFFATIE-EEVAYHKNYPTIYHLREELV 146
EFR89594            
WP_038409211    74  RRRNRIAYLQEIFAAEMAEVDANFFYRLED-SFYI--ESEKR----H SRHPFFATIE-EEVAYHEEYKTIYHLREKLV 143
EFR95520            
WP_003723650    74  RRRNRISYLQEIFAVEMANIDANFFCRLND-SFYV--DSEKR----N SRHPFFATIE-EEVAYHDNYRTIYHLREKLV 143
WP_003727705    74  RRRNRISYLQEIFAVEMANIDANFFCRLND-SFYV--DSEKR----N SRHPFFATIE-EEVAYHKNYRTIYHLREELV 143
WP_003730785    74  RRRNRISYLQEIFAVEMANIDANFFCRLND-SFYV--DSEKR----N SRHPFFATIE-EEVAYHKNYRTIYHLREELV 143
WP_003733029    74  RRRNRISYLQEIFAIQMNEVDDNFFNRLKE-SFYA--ESDKK----Y NRHPFFGTVE-EEVAYYKDFPTIYHLREELV 143
WP_003739838    74  RRRNRISYLQEIFALEMANIDANFFCRLND-SFYV--DSEKR----N SRHPFFATIE-EEVAYHKNYRTIYHLREELV 143
WP_014601172    74  RRRNRISYLQEIFAVEMANIDANFFCRLND-SFYV--DSEKR----N SRHPFFATIE-EEVAYHKNYRTIYHLREELV 143
WP_023548323    74  RRRNRISYLQEIFAVEMANIDANFFCRLND-SFYV--DSEKR----N SRHPFFATIE-EEVAYHKNYRTIYHLREELV 143
WP_031665337    74  RRRNRISYLQEIFAIQMNEVDDNFFNRLKE-SFYA--ESDKK----Y NRHPFFGTVE-EEVAYYKDFPTIYHLREELI 143
WP_031669209    74  RRRNRISYLQEIFAIQMNEVDDNFFNRLKE-SFYV--DSEKR----N SRHPFFATIE-EEVAYHKNYRTIYHLREELV 143
WP_033920898    74  RRRNRISYLQEIFAVEMANIDANFFCRLND-SFYV--DSEKR----N SRHPFFATIE-EEVAYHKNYRTIYHLREELV 143
AKI42028        77  RRRNRISYLQEIFAVEMANIDANFFCRLND-SFYV--DSEKR----N SRHPFFATIE-EEVAYHKNYRTIYHLREELV 146
```

-continued

| | | | | |
|---|---|---|---|---|
| AKI50529 | 77 | RRRNRISYLQEIPAVEMANIDANFFCRLND-SFYV--DSEKR---N | SRHPFFATIE-EEVAYHKNYRTIYHLREELV | 146 |
| EFR83390 | 74 | RRRNRISYLQEIPTAEMPEVDANFFYRLED-SFYI--ESEKR---Q | SRHPFFATIE-EEVAYHENYRTIYHLREKLV | 143 |
| WP_046323366 | 90 | RRKNRICYLQEIFSNEMAKVDDSFFHRLEE-SFIV--EEDKK---H | ERHPIFGNIV-DEVAYHEKYPTIYHLRKKLV | 159 |
| AKE81011 | 65 | KRRERIRLLRALLQDMVLEKDPTFFIRLEHtSFLD--EEDKAkylG | DNYNLFIDEdfNDYTYYHKPTIYHLRKALC | 143 |
| CUO82355 | 66 | KRRERIRLLRDLLGDMVMEVDPTFFFIRLLNvSFLD--EEDKQkmlG | DNYNLFIEKDfNDKTYYDKPTIYHLRKELC | 144 |
| WP_033162887 | 107 | RRKNRICYLQEIFSNEMAKVDDSFFHRLEE-SFLV--EEDKK---H | ERHPIFGNIV-DEVAYHEKYPTIYHLRKKLV | 176 |
| AGZ01981 | 74 | RRKNRICYLQEIFSNEMAKVDDSFFHRLEE-SFLV--EEDKK---H | ERHPIFGNIV-DEVAYHEKYPTIYHLRKKLV | 143 |
| AKA60242 | 74 | RRKNRICYLQEIFSNEMAKVDDSFFHRLEE-SFLV--EEDKK---H | ERHPIFGNIV-DEVAYHEKYPTIYHLRKKLV | 143 |
| AKS40380 | 78 | RRKNRICYLQEIFSNEMAKVDDSFFHRLEE-SFLV--EEDKK---H | ERHPIFGNIV-DEVAYHEKYPTIYHLRKKLV | 147 |
| 4UN5_B | 144 | DSTDKADLRIYLALAHMIKFRGHFLIEGD-LNPDNSDⱽKL-FIQLVQTYNQL--FEEN--AI | INASGVDAK---AI | 211 |
| WP_010922251 | 145 | DSSEKADLRIVYLALAHMIKFRGHFLIEGE-LNAENTVQKI-FADFVGVYRT--FDDS-H | LSEITVDVA---SI | 212 |
| WP_039695303 | 144 | DSKEKTDLRIIYLALAHMIKYRGHFLYEEA-FDIKNNDIQKI-FNEFISIVDNT--FEGS-S | LSGQNAQVE---AI | 211 |
| WP_045635197 | 105 | EEEFSA------ALLHLAKRRG---VHNV----NEVE------EDT--GN-- | -------E-- | 134 |
| 5AXW_A | 144 | DSTDKADLRLIYLALAHMIKFRGHFLIEGD-LNPDNSDVDKL--FIQLVQTYNQL--FEEN--AI | INASGVDAK---AI | 211 |
| WP_009880683 | 144 | DSTDKADLRLIYLALAHMIKFRGHFLIEGD-LNPDNSDVDKL--FIQLVQTYNQL--FEEN--AI | INASGVDAK---AI | 211 |
| WP_010922251 | 144 | DSTDKVDLRLIYLALAHMIKFRGHFLIEGD-LNPDNSDVDKL--FIQLVQTYNQL--FEEN--AI | INASRVDAK---AI | 211 |
| WP_011054416 | 144 | DSTDKADLRLIYLALAHMIKFRGHFLIEGD-LNPDNSDVDKL--FIQLVQTYNQL--FEEN--AI | INASGVDAK---AI | 211 |
| WP_011284745 | 144 | DSTDKADLRLIYLALAHMIKFRGHFLIEGD-LNPDNSDVDKL--FIQLVQTYNQL--FEEN--AI | INASGVDAK---AI | 211 |
| WP_011285506 | 144 | DSTDKADLRLIYLALAHMIKFRGHFLIEGD-LNPDNSDVDKL--FIQLVQTYNQL--FEEN--AI | INASGVDAK---AI | 211 |
| WP_011527619 | 144 | DSTDKADLRLIYLALAHMIKFRGHFLIEGD-LNPDNSDVDKL--FIQLVQTYNQL--FEEN--AI | INASGVDAK---AI | 211 |
| WP_012560673 | 144 | DSTDKADLRLIYLALAHMIKFRGHFLIEGD-LNPDNSDVDKL--FIQLVQIYNQL--FEEN--AI | INASRVDAK---AI | 211 |
| WP_014407541 | 144 | DSTDKADLRLIYLALAHMIKFRGHFLIEGD-LNPDNSDVDKL--FIQLVQTYNQL--FEEN--AI | INASGVDAK---AI | 211 |
| WP_020905136 | 144 | DSTDKADLRLIYLALAHMIKFRGHFLIEGD-LNPDNSDVDKL--FIQLVQTYNQL--FEEN--AI | INASRVDAK---AI | 211 |
| WP_023080005 | 144 | DSTDKADLRLIYLALAHMIKFRGHFLIEGD-LNPDNSDVDKL--FIQLVQTYNQL--FEEN--AI | INASGVDAK---AI | 211 |
| WP_023610282 | 144 | DSTDKADLRLIYLALAHMIKFRGHFLIEGD-LNPDNSDVDKL--FIQLVQTYNQL--FEEN--AI | INASGVDAK---AI | 211 |
| WP_030125963 | 144 | DSTDKVDLRLIYLALAHMIKFRGHFLIEGD-LNPDNSDVDKL--FIQLVQTYNQL--FEEN--AI | INASRVDAK---AI | 211 |
| WP_030126706 | 144 | DSTDKADLRLIYLALAHMIKFRGHFLIEGD-LNPDNSDVDKL--FIQLVQTYNQL--FEEN--AI | INASGVDAK---AI | 211 |
| WP_031488318 | 144 | DSTDKADLRLIYLALAHMIKFRGHFLIEGD-LNPDNSDVDKL--FIQLVQTYNQL--FEEN--AI | INASGVDAK---AI | 211 |
| WP_032460140 | 144 | DSTDKADLRLIYLALAHMIKFRGHFLIEGD-LNPDNSDVDKL--FIQLVQTYNQL--FEEN--AI | INASRVDAK---AI | 211 |
| WP_032461047 | 144 | DSTDKADLRLIYLALAHMIKFRGHFLIEGG-LNPDNSDVDKL--FIQLVQTYNQL--FEEN--AI | INASGVDAK---AI | 211 |
| WP_032462016 | 144 | DSTDKADLRLIYLALAHMIKFRGHFLIEGD-LNPDNSDVDKL--FIQLVQTYNQL--FEEN--AI | INANGVDAK---AI | 211 |
| WP_032462936 | 144 | DSTDKADLRLIYLALAHMIKFRGHFLIEGD-LNPDNSDVDKL--FIQLVQTYNQL--FEEN--AI | INASRVDAK---AI | 211 |
| WP_032464890 | 1 | -----------------------------PDNSDVDKL--FIQLVQTYNQL--FEEN--AI | INASGVDAK---AI | 36 |
| WP_033888930 | 144 | DSTDKADLRLIYLALAHMIKFRGHFLIEGD-LNPDNSDVDKL--FIQLVQTYNQL--FEEN--AI | INASRVDAK---AI | 211 |
| WP_038431314 | 144 | DISQKADLRLIYLALAHMIKFRGHFLIEGQ-LNPDNSDVDKL-FKDFVEVVDKT--VEES-H | LSEMTVDAL---SI | 211 |
| WP_038432938 | 147 | DSSEKADLRLVYLALAHMIKFRGHFLIEGE-LNAENTVQKI-FADFVGVYDRT--FDDS-H | LSEITVDAA---SI | 214 |
| WP_038434062 | 144 | DSTDKADLRLIYLALAHMIKFRGHFLIEDD-LNPDNSDVDKL--FIQLVQTYNQL--FEEN--AI | INASGVDAK---AI | 211 |
| BAQ51233 | 55 | DSTDKADLRLIYLALAHMIKFRGHFLIEGD-LNPDNSDVDKL--FIQLVQTYNQL--FEEN--AI | INASGVDAK---AI | 122 |
| KGE60162 | | | | |
| KGE60856 | | | | |
| WP_029989955 | 144 | DSTDKADLRLIYLALAHIIKFRGHFLIEDDrFDVRNTDIQKQ-YQAPLEIFDTT--FENN-D | LLSQDVDVE---AI | 211 |
| WP_003030002 | 144 | DSTDKADLRLIYLALAHIIKFRGHFLIEDDrFDVRNTDIQKQ-YQAPLEIFDTT--FENN-D | LLSQDVDVE---AI | 211 |
| WP_003065552 | 147 | DKQEKADLRLIYLALAHIIKFRGHFLIEDDrFDVRNTDIQKQ-YQAPLEIFDTT--FENN-D | LLSQNVDVE---AI | 214 |
| WP_001040076 | 144 | DKKEKADLRLIYLALAHIIKFRGHFLIEDDsFDVRNTDISKQ-YQDFLEIFNTT--FENN-D | LLSQNVDVE---AI | 212 |
| WP_001040078 | 144 | DKKEKADLRLIYLALAHIIKFRGHFLIEDDsFDVRNTDISKQ-YQDFLEIFNTI--FENN-D | LLSQNVDVE---AI | 212 |
| WP_001040080 | 144 | DKKEKADLRLIYLALAHIIKFRGHFLIEDDsFDVRNTDISKQ-YQDFLEIFNTT--FENN-D | LLSQNVDVE---AI | 212 |
| WP_001040081 | 144 | DKKEKADLRLIYLALAHIIKFRGHFLIEDDsFDVRNTDISKQ-YQDFLEIFNTT--FENN-D | LLSQNVDVE---AI | 212 |
| WP_001040083 | 144 | DKKEKADLRLIYLALAHIIKFRGHFLIEDDsFDVRNTDISKQ-YQDFLEIFNTT--FENN-D | LLSQNVDVE---AI | 212 |
| WP_001040085 | 144 | DKKEKADLRLIYLALAHIIKFRGHFLIEDDsFDVRNTDISKQ-YQDFLEIFNTT--FENN-D | LLSQNVDVE---AI | 212 |
| WP_001040087 | 144 | DKKEKADLRLIYLALAHIIKFRGHFLIEDDsFDVRNTDISKQ-YQDFLEIFNTT--FENN-D | LLSQNVDVE---AI | 212 |
| WP_001040088 | 144 | DKKEKADLRLIYLALAHIIKFRGHFLIEDDsFDVRNTDISKQ-YQDFLEIFNTT--FENN-D | LLSQNVDVE---AI | 212 |
| WP_001040089 | 144 | DKKEKADLRLIYLALAHIIKFRGHFLIEDDsFDVRNTDISKQ-YQDFLEIFNTT--FENN-D | LLSQNVDVE---AI | 212 |
| WP_001040090 | 144 | DKKEKADLRLIYLALAHIIKFRGHFLIEDDsFDVRNTDISKQ-YQDFLEIFNTT--FENN-D | LLSQNVDVE---AI | 212 |

-continued

| | | | | |
|---|---|---|---|---|
| WP_001040091 | 144 | DKKEKADLRLIYLALAHIIKFRGHFLIEDDsFDVRNTDISKQ--YQDFLEIFDTT--FENN-D | LLSQNVDVE---- | AI | 212 |
| WP_001040092 | 144 | DKKEKADLRLIYLALAHIIKFRGHFLIEDDrFDVRNTDIQKQ--YQAFLEIFDTS--FENN-H | LLSQNVDVE---- | AI | 212 |
| WP_001040094 | 144 | DKKEKADLRLIYLALAHIIKFRGHFLIEDDrFDVRNTDIQKQ--YQAFLEIFDTT--FENN-D | LLSQNVDVE---- | AI | 212 |
| WP_001040095 | 144 | DKKEKADLRLIYLALAHIIKFRGHFLIEDDrFDVRNTDIQKQ--YQAFLEIFDTT--FENN-D | LLSQNVDVE---- | AI | 212 |
| WP_001040096 | 144 | DKKEKADLRLIYLALAHIIKFRGHFLIEDDrFDVRNTDIQKQ--YQAFLEIFDTT--FENN-D | LLSQNVDVE---- | AI | 212 |
| WP_001040097 | 144 | DKKEKADLRLIYLALAHIIKFRGHFLIEDDrFDVRNTDIQKQ--YQAFLEIFDTT--FENN-D | LLSQNVDVE---- | AI | 212 |
| WP_001040098 | 144 | DKKEKADLRLIYLALAHIIKFRGHFLIEDDrFDVRNTDIQKQ--YQAFLEIFDTT--FENN-D | LLSQNVDVE---- | AI | 212 |
| WP_001040099 | 144 | DKKEKADLRLIYLALAHIIKFRGHFLIEDDrFDVRNTDIQKQ--YQAFLEIFDTT--FENN-D | LLSQNVDVE---- | AI | 212 |
| WP_001040100 | 144 | DKKEKADLRLIYLALAHIIKFRGHFLIEDDsFDVRNTDISKQ--YQDFLEIFDTT--FENN-D | LLSQNVDVE---- | AI | 212 |
| WP_001040104 | 144 | DKKEKADLRLIYLALAHIIKFRGHFLIEDDsFDVRNTDISKQ--YQDFLEIFDTT--FENN-D | LLSQNVDVE---- | AI | 212 |
| WP_001040105 | 144 | DKKEKADLRLIYLALAHIIKFRGHFLIEDDsFDVRNTDISKQ--YQDFLEIFNTT--FENN-D | LLSQNVDVE---- | AI | 212 |
| WP_001040106 | 144 | DKKEKANLRLVYLALAHIIKFRGHFLIEDDsFDVRNTDISKQ--YQAFLEIFDTT--FENN-D | LLSQNIDVE---- | GI | 212 |
| WP_001040107 | 144 | DKKEKADLRLVYLALAHIIKFRGHFLIEDDsFDVRNTDIQKQ--YQAFLEIFDTT--FENN-D | LLSQNIDVE---- | GI | 212 |
| WP_001040108 | 144 | DKKEKADLRLVYLALAHIIKFRGHFLIEDDsFDVRNTDIQRQ--YQAFLEIFDTT--FENN-D | LLSQNIDVE---- | GI | 212 |
| WP_001040109 | 144 | DKKEKANLRLVYLALAHIIKFRGHFLIEDDsFDVRNTDIQRQ--YQAFLEIFDTT--FENN-D | LLSQNIDVE---- | GI | 212 |
| WP_001040110 | 144 | DKKEKADLRLIYLALAHIIKFRGHFLIEDDsFDVRNTDIQRQ--YQAFLEIFDTT--FENN-H | LLSQNIDVE---- | GI | 212 |
| WP_015058523 | 144 | DKKEKADLRLIYLALAHIIKFRGHFLIEDDsFDVRNTDIQRQ--YQAFLEIFDTS--FENN-D | LLSQNIDVE---- | GI | 212 |
| WP_017643650 | 144 | DKKEKADLRLIYLALAHIIKFRGHFLIEDDsFDVRNTDIQRQ--YQAFLEIFDTT--FENN-D | LLSQNIDVE---- | GI | 212 |
| WP_017647151 | 144 | DKKEKADLRLFYLALAHIIKFRGHFLIEDDsFDVRNTDIQRQ--YQAFLEIFDTT--FENN-H | LLSQNIDIE---- | GI | 212 |
| WP_017648376 | 144 | DKKEKADLRLIYLALAHIIKFRGHFLIEDDsFDVRNTDIQRQ--YQAFLEIFDTT--FENN-H | LLSQNIDVE---- | GI | 212 |
| WP_017649527 | 144 | DKKEKADLRLIYLALAHIIKFRGHFLIEDDsFDVRNTDIQRQ--YQDFLEIFDTT--FENN-D | LLSQNIDVE---- | GI | 212 |
| WP_017771611 | 144 | DKKEKADLRLVYLALAHIIKFRGHFLIEDDsFDVRNTDIQRQ--YQAFLEIFDTT--FENN-D | LLSQNIDVE---- | GI | 212 |
| WP_017771984 | 144 | DKKEKADLRLVYLALAHIIKFRGHFLIEDDsFDVRNTDISKQ--YQDFLEIENTT--FENN-D | LLSQNVDVE---- | AI | 212 |
| CFQ25032 | 144 | DKKEKADLRLVYLALAHIIKFRGHFLIEDDsFDVRNTDISKQ--YQDFLEIENTT--FENN-D | LLSQNVDVE---- | AI | 212 |
| CFV16040 | 144 | DKKEKADLRLVYLALAHIIKFRGHFLIEDDsFDVRNTDISKQ--YQDFLEIFDTT--FENN-D | LLSQNVDVE---- | AI | 212 |
| KLJ37842 | 144 | DKKEKADLRLIYLALAHIIKERGHFLIEDDsEDVRNTDIQKQ--YQDFLEIENTT--FENN-D | LLSQNVDVE---- | AI | 212 |
| KLJ72361 | 144 | DKKEKADLRLIVYLALAHIIKERGHFLIEDDsEDVRNTDIQKQ--YQAFLEIFDTT--FENN-D | LLSQNVDVE---- | AI | 212 |
| KLL20707 | 144 | DKKEKANLRLVVYLALAHMIKERGHFLIEDDsEDVRNTDISKQ--YQDFLEIENTT--FENN-D | LLSQNVDVE---- | AI | 212 |
| KLL42645 | 144 | DKKEKADLRLIYLALAHIIKERGHFLIEDDsEDVRNTDIQRQ--YQAFLEIFDTT--FENN-D | LLSQNVDVE---- | AI | 212 |
| WP_047207273 | 144 | DKKEKADLRLIYLALAHIIKERGHFLIEDDsEDVRNTDISKQ--YQDFLEIENTT--FENN-D | LLSQNVDVE---- | AI | 212 |
| WP_047209694 | 144 | DKKEKADLRLIVYLALAHIIKERGHFLIEDDsEDVRNTDIQKQ--YQAFLEIFDTT--FENN-D | LLSQNVDVE---- | AI | 212 |
| WP_050198062 | 144 | DKKEKANLRLVVYLALAHMIKERGHFLIEDDsEDVRNTDISKQ--YQDFLEIENTT--FENN-D | LLSQNVDVE---- | AI | 212 |
| WP_050201642 | 144 | DKKEKADLRLIYLALAHIIKERGHFLIEDDsEDVRNTDISKQ--YQDFLEIENTT--FENN-D | LLSQNVDVE---- | AI | 212 |
| WP_050204027 | 144 | DKKEKADLRLIYLALAHIIKERGHFLIEDDsEDVRNTDIQRQ--YQAFLEIFDTT--FENN-D | LLSQNIDVE---- | GI | 212 |
| WP_050881965 | 144 | DKKEKADLRLIYLALAHIIKERGHFLIEDDsEDVRNTDISKQ--YQDFLEIENTT--FENN-D | LLSQNVDVE---- | AI | 212 |
| WP_050886065 | 144 | DKKEKADLRLIYLALAHIIKERGHFLIEDDsEDVRNTDISKQ--YQAFLEIFDTS--FENN-D | LLSQNVDVE---- | AI | 212 |
| AHN30376 | 144 | DKKEKADLRLIYLALAHIIKERGHFLIEDDrEDVRNTDIQKQ--YQDFLEIFDTT--FENN-D | LLSQNVDVE---- | AI | 212 |
| EA078426 | 144 | DKKEKADLRLIYLALAHIIKERGHFLIEDDrEDVRNTDIQKQ--YQAFLEIFDTT--FENN-D | LLSQNVDVE---- | AI | 212 |
| CCW42055 | 144 | DISQKADLRLIYLALAHMIKERGHFLIEGQ--LKAENTNVQAL--FKDEVEVDKT--VEES-H | LSEITVDAL---- | SI | 211 |
| WP_003041502 | 145 | NSKEKADLRLIYLALAHMIKERGHFLYEGD--LKAENTNVQAL--FKDEVEEVDKT--IEES-S | LSEITVDAL---- | SI | 212 |
| WP_037593752 | 145 | DISQKADLRLIYLALAHMIKERGHFLYEGD--LKAENTNVQAL--FKDEVEVDKT--VEES-H | LSEMTVDAL---- | SI | 212 |
| WP_049516684 | 144 | NSKEKADLRLIYLALAHMIKERGHFLYEGD--LKAENTNVQAL--FKDEVEEYDKT--IEES-H | LSEITVDAA---- | SI | 212 |
| GAD46167 | 145 | DSTEKADLRLIYLALAHMIKERGHFLIEGE--LNAENTDVQKL--FTDEVGVDRT--FDDS-H | LSEITVDAA---- | SI | 212 |
| WP_018363470 | 144 | DSPEKADLRLIYLALAHMIKERGHFLIEGK--LNAENSDVAKL--FYQLIQTYNQL--FEES- | LDEIEVDAK---- | GI | 211 |
| WP_003043819 | 144 | DTSKKADLRLIYLALAHMIKERGHFLIEGD--LKAENTDVQAL--FYQLIQTYNQL--FEES- | LSEITVDAL---- | SI | 211 |
| WP_006299658 | 144 | DSTGKVDLRLIYLALAHMIKERGHFLIEGD--LNPDNSDMDKL--FYQLIQTYNQL--IEES-H | LARITVDAL---- | GI | 211 |
| WP_048800889 | 144 | DSTDKADLRLIYLALAHMIKERGHFLIEGD--LKAENTDVQTL--ENDEVEVDKT--IEES-H | LSEITVDAL---- | SI | 212 |
| WP_012767106 | 144 | DSTDKADLRLIYLALAHMIKERGHFLIEGD--LNPDNSDMDKL--FIQLVQTYNQL--FEEN- | INASRVDAK---- | AI | 211 |
| WP_146123333 | 144 | DSTDKADLRLIYLALAHMIKERGHFLIEGD--LNPDNSDMDKL--FIQLVQTYNQL--FEEK- | INASGVDAK---- | AI | 211 |
| WP_015017095 | 144 | DSTDKADLRLIYLALAHMIKERGHFLIEGD--LNPDNSDVDKL--FIQLVQTYNQL--FEEN- | INASRVDAK---- | AI | 211 |
| WP_015057649 | 144 | DSTDKADLRLIYLALAHMIKERGHFLIEGD--LNPDNSDVDKL--FIQLVQTYNQL--FEEN- | INASRVDAK---- | AI | 211 |
| WP_048272215 | 144 | DSTDKADLRLIYLALAHMIKERGHFLIEGD--LNPDNSDVDKL--FIQLVQTYNQL--FEEN- | INASRVDAK---- | AI | 211 |
| WP_049519324 | 144 | DSTDKADLRLIYLALAHMIKERGHFLIEGD--LNPDNSDVDKL--FIQLVQTYNQL--FEEN- | INASRVDAK---- | AI | 211 |

```
WP_012515931   144  DNPQKADLRLIYLAVAHIIKERGHFLIEGT-LSSKNNNLQKS--FDHLVDTYNLL--FEEQ--LLTEGINAK---EL  211
WP_021320964   144  DNPQKADLRLIYLAVAHIIKERGHFLIEGT-LSSKNNNLQKS--FDHLVDTYNLL--FEEQ--LLTEGINAK---EL  211
WP_037581760   144  DNPQKADLRLIYLAVAHIIKERGHFLIEGT-LSSKNNNLQKS--FDHLVDTYNLL--FEEQ--LLTEGINAK---EL  211
WP_004232481   144  DSPEKVDLRLIYLALAHMIKERGHFLIEGQ-LNAENTDVQKI--FADEGVYDRT--FDDS-H LSEITVDAA---SI  211
WP_009854540   144  DSSEKADLRLIYLALAHMIKERGHFLIEGK-LNAENTDVQKL--FTDEGVYDRT--FDDS-H LSEITVDVA---ST  212
WP_012962174   145  DSHEKADLRLIYLALAHMIKERGHFLIEGE-LNAENTDVQKI--FEAFVEVYDRS--FDDS-N LSEITVDAS---SI  212
WP_039695303   145  DSSEKADLRLIVYLALAHMIKFRGHFLIEGE-LNAENTDVQKI--FADFVGVNRT--FDDS-H LSEITVDVA---SI  212
WP_014334983   144  DSQEKADLRLIYLALAHMIKYRGHFLIEGE-LNAENTDVQKL--FNVFVETYDKI--VDES-H LSEIEVDAS---SI  211
WP_003099269   144  DSDQKADLRLIYLALAHIIKFRGHFLIEGN-LDSENTDVHVL--FLNLVNIYNNL--FEED--VETASIDAE---KI  211
AHY15608       144  DSDQKADLRLIYLALAHIIKFRGHFLIEGN-LDSENTDVHVL--FLNLVNIYNNL--FEED--VETASIDAE---KI  211
AHY17476       144  DSDQKADLRLIYLALAHIIKFRGHFLIEGN-LDSENTDVHVL--FLNLVNIYNNL--FEED--VETASIDAE---KI  211
ESR09100           --------------------------------------------------------------------------  
AGM98575       144  DSDQKADLRLIYLALAHIIKFRGHFLIEGN-LDSENTDVHVL--FLNLVNIYNNL--FEED--VETASIDAE---KI  211
ALF27331       144  DNPEKTDLRLVYLALAHIIKFRGHFLIEGK-FDTRNNDVQRL--FQEFLAVYDNT--FENS--LQEQNVQVE---EI  211
WP_018372492   144  DTPDKMDIRLIYLALAHIIKYRGHFLIEGD-LDIENIGIQDS--FKSFIEEVNTQ--FGTK--LDSTTKVE---AI  209
WP_045618028   145  DSKEKADFRLIYLALAHIIKYRGHFLYES--EDIKNNDIQKI--FNEFISIYDNT--FEGS-S LNGQNAQVE---AI  212
WP_045635197   144  DSKEKTDLRLIYLALAHMIKYRGHFLYEEA-FDIKNNDIQKI--FNEFISIYDNT--FEGS-S LSGQNAQVE---AI  211
WP_002263549   144  DNPEKVDLRLVYLALAHMIKFRGHFLIEGK-FDTRNNDVQRL--FQEFLAVYDNT--FENS-S LQEQNVQVE---EI  211
WP_002263887   144  DNPEKVDLRLVYLALAHIIKFRGHFLIEGK-FDTRNNDVQRL--FQEFLAVYDNT--FENS-S LQEQNVQVE---EI  211
WP_002264920   144  DSTEKADLRLVYLALAHIIKFRGHFLIEGK-FDTRNNDVQRL--FADFVGVYDRT--FDDS-H LSEITVDAS---SI  211
WP_002269043   144  DNPEKTDLRLVYLALAHIIKFRGHFLIEGN-FDTRNNDVQRL--FQEFLAVYDNT--FENS-S LQEQNVQVE---EI  211
WP_002269448   144  DNPEKTDLRLVYLALAHIIKFRGHFLIEGK-FDTRNNDVQRL--FQEFLAVYDNT--FENS-S LQEQNVQVE---EI  211
WP_002271977   144  DNPEKVDLRLVYLALAHIIKFRGHFLIEGK-FDTRNNDVQRL--FQEFLAVYDNT--FENS-S LQEQNVQVE---EI  211
WP_002272766   144  DNPEKTDLRLVYLALAHIIKFRGHFLIEGK-FDTRNNDVQRL--FQEFLAVYDNT--FENS-S LQEQNVQVE---SI  211
WP_002273241   144  DNPEKVDLRLVYLALAHIIKFRGHFLIEGK-FDTRNNDVQRL--FQEFLAVYDNT--FEGS-S LQEQNVQVE---EI  211
WP_002275430   144  DNPEKVDLRLVYLALAHMIKFRGHFLIEGK-FDTRNNDVQRL--FQEFLAVYDNT--FENS-S LQEQNVQVE---EI  211
WP_002276448   144  DNPEKVDLRLVYLALAHIIKFRGHFLIEGK-FDTRNNDVQRL--FQEFLAVYDNT--FENS-S LQEQNVQVE---EI  211
WP_002277050   144  DSTEKADLRLVYLALAHIIKFRGHFLIEGK-FDTRNNDVQRL--FQEFLAVYDNT--FDDS-H LSEITVDAS---SI  211
WP_002277364   144  DNPEKVDLRLVYLALAHIIKFRGHFLIEGK-LNAENTDVQKL--FQEFLAVYDNT--FENS-S LQEQNVQVE---EI  211
WP_002279025   144  DNPEKVDLRLVYLALAHIIKFRGHFLIEGE-FDTRNNDVQRL--FQEFLAVYDNT--FENS-S LQEQNVQVE---EI  211
WP_002279859   144  DSTEKADLRLVYLALAHIIKFRGHFLIEGK-FDTRNNDVQRL--FADFVGVYDRT--FDDS-H LSEITVDAS---SI  211
WP_002280230   144  DNPEKVDLRLVYLALAHIIKFRGHFLIEGE-LNAENTDVQKL--FADFVGVYDRT--FDDS-H LSEITVDAS---SI  211
WP_002281696   144  DNPEKTDLRLVYLALAHIIKFRGHFLIEGK-FDTRNNDVQRL--FQEFLAVYDNT--FENS-S LQEQNVQVE---EI  211
WP_002282247   144  DSTEKADLRLVYLALAHIIKFRGHFLIEGE-LNAENTDVQKL--FADFVGVYDRT--FDDS-H LSEITVDAS---SI  211
WP_002282906   144  DNPEKVDLRLVYLALAHIIKFRGHFLIEGK-FDTRNNDVQRL--FQEFLAVYDNT--FENS-S LQEQNVQVE---EI  211
WP_002283846   144  DNPEKVDLRLVYLALAHIIKFRGHFLIEGK-FDTRNNDVQRL--FQEFLAVYDNT--FENS-S LQEQNVQVE---EI  211
WP_002287255   144  DNPEKVDLRLVYLALAHIIKFRGHFLIEGK-FDTRNNDVQRL--FQEFLAVYDNT--FENS-S LQEQNVQVE---EI  211
WP_002288990   144  DNPEKVDLRLVYLALAHIIKFRGHFLIEGK-FDTRNNDVQRL--FQEFLAVYDNT--FENS-S LQEQNVQVE---EI  211
WP_002289641   144  DNPEKTDLRLVYLALAHIIKFRGHFLIEGK-FDTRNNDVQRL--FKDFVEVYDKT--VEES-H LSEMTVDAL---SI  211
WP_002290427   144  DNPEKVDLRLVYLALAHIIKFRGHFLIEGQ-LKAENTNVQAL--FQEFLAVYDNT--FENS-S LQEQNVQVE---EI  211
WP_002295753   144  DNPEKVDLRLVYLALAHIIKFRGHFLIEGK-FDTRNNDVQRL--FQEFLAVYDNT--FENS-S LQEQNVQVE---EI  211
WP_002296423   144  DNPEKTDLRLVYLALAHIIKFGGHFLIEGK-FDTRNNDVQRL--FQEFLAVYDNT--FENS-S LQEQNVQVE---EI  211
WP_003044487   144  NSTEKADLRLVYLSLAHMIKFRGHFLIEGQ-LKAENTNVQAL--FQEFLAVYDNT--FENS-S LQEQNVQVE---EI  211
WP_002304487   144  DNPEKVDLRLVYLALAHIIKFRGHFLIEGK-FDTRNNDVQRL--FQEFLAVYDNT--FENS-S LQEQNVQVE---EI  211
WP_002305844   144  DNPEKVDLRLVYLALAHIIKFRGHFLIEGK-FDTRNNDVQRL--FQEFLAVYDNT--FENS-S LQEQNVQVE---EI  211
WP_002307203   144  DNPEKVDLRLVYLALAHIIKFRGHFLIEGK-FDTRNNDVQRL--FQEFLAVYDNT--FENS-S LQEQNVQVE---EI  211
WP_002310390   144  DNPEKVDLRLVYLALAHIIKFRGHFLIEGK-FDTRNNDVQRL--FQEFLAVYDNT--FENS-S LQEQNVQVE---EI  211
WP_002352408   144  DNPEKTDLRLVYLALAHIIKFRGHFLIEGK-FDTRNNDVQRL--FQEFLAVYDNT--FENS-S LQEQNVQVE---EI  211
WP_012997688   144  DNPEKVDLRLVYLALAHIIKFRGHFLIEGK-FDTRNNDVQRL--FQEFLAVYDNT--FENS-S LQEQNVQVE---EI  211
WP_014677909   144  DNPEKTDLRLVYLALAHIIKFRGHFLIEGK-FDTRNNDVQRL--FQEFLAVYDNT--FENS-S LQEQNVQVE---EI  211
WP_019312892   144  DNPEKTDLRLVYLALAHIIKFRGHFLIEGK-FDTRNNDVQRL--FQEFLAVYDNT--FENS-S LQEQNVQVE---EI  211
WP_019313659   144  DNPEKTDLRLVYLALAHIIKFRGHFLIEGK-FDTRNNDVQRL--FQEFLAVYDNT--FENS-S LQEQNVQVE---EI  211
WP_019314093   144  DNPEKTDLRLVYLALAHIIKFRGHFLIEGK-FDTRNNDVQRL--FQEFLAVYDNT--FENS-S LQEQNVQVE---EI  211
WP_019315370   144  DNPEKTDLRLVYLALAHIIKFRGHFLIEGK-FDTRNNDVQRL--FQEFLAVYDNT--FENS-S LQEQNVQVE---EI  211
```

-continued

```
WP_019803776   144 DNPEKVDLRLIVYLALAHIIKFRGHFLIEGK-FDTRNNDVQRL--FQEFLAVYDNT--FENS-S  LQEQNVQVE---EI  211
WP_019805234   144 DNPEKTDLRLIVYLALAHIIKFRGHFLIEGK-FDTRNNDVQRL--FQEFLAVYDNT--FENS-S  LQEQNVQVE---EI  211
WP_024783594   144 DNPEKVDLRLIVYLALAHIIKFRGHFLIEGK-FDTRNNDVQRL--FQEFLAVYDNT--FENS-S  LQEQNVQVE---EI  211
WP_024784288   144 DSTEKADLRIVYLALAHMIKFRGHFLIEGE-LNAENTDVQKL--FADFVGVYDRT--FDDS-H  LSEITVDAS---SI  211
WP_024784666   144 DNPEKVDLRLVYLALAHIIKFRGHFLIEGK-FDTRNNDVQRL--FQEFLAVYDNT--FENS-S  LQEQNVQVE---EI  211
WP_024784894   144 DSTEKADLRLVYLALAHMIKFRGHFLIEGE-LNAENTDVQKL--FADFVGVYDRT--FDDS-H  LSEITVDAS---SI  211
WP_024786433   144 DNPEKVDLRLVYLALAHIIKFRGHFLIEGK-FDTRNNDVQRL--FQEFLAVYDNT--FENS-S  LQEQNVQVE---EI  211
WP_049473442   144 DNPEKTDLRLIVYLALAHIIKFRGHFLIEGK-FDTRNNDVQRL--FQEFLAVYDNT--FENS-S  LQEQNVQVE---EI  211
WP_049474547   144 DNPEKTDLRLIVYLALAHIIKFRGHFLIEGK-FDTRNNDVQRL--FQEFLAVYDNT--FEGN-S  LQEQNVQVE---EI  204
EMC03581       137 DSKEKTDLRLIIYLALAHMIKYRGHFLYEDT-FDIKNNDIQKI--FNEFISIYNNT--FEGN-S  LSGQNVQVE---AI  212
WP_000428612   145 DSKEKTDLRLIIYLALAHMIKYRGHFLYEDT-FDIKNNDIQKI--FNEFISIYNNT--FEGS-S  LSGQNAQVE---AI  212
WP_000428613   144 DSKEKVDLRLIIYLALAHMIKYRGHFLYEDS-FDIKNNDIQKI--FSEFISIYDNT--FEES-S  LSKGNAQVE---AI  211
WP_049523028   113 DSDEKADLRLIYLALAHIIKFRGHFLIEGD-LDSQNTDVNAL--FLKLVDTYNLM--FEDD--  IDTQTIDAT---VI  180
WP_003107102   146 DNTEKADLRLIYLTLAHMIKYRGHFLIEGA-VHALVDAYNIM--VHALVDAYNIM--FEED--  LDIEAIDVK---AI  213
WP_054279288   145 DSKEKADLRLIIYLALAHIIKYRGHFLYEES-FDIKNNDIQKI--FNEFISIYDNT--FEGS-S  LSGQNAQVE---AI  212
WP_049531101   145 DSKEKADLRLIIYLALAHMIKYRGHFLYEEA-FDIKNNDIQKI--FNEFINIYDNT--FEGS-S  LSGQNEQVE---AI  212
WP_049538452   145 DSKEKADLRLIIYLALAHMIKYRGHFLYEEA-FDIKNNDIQKI--FNEFISIYDNT--FEGS-S  LSGQNAQVE---TI  212
WP_049549711   146 DRDQKADLRLIIYLALSHIIKFRGHFLIEGK-LNSENTDVQKL--FIALVTVYNLL--FEEE--  IAGETCDAK---AL  213
WP_007896501    98 DRDQKADLRLIYLALSHIIKFRGHFLIEGK-LNSENTDVQKL--FIALVTVYNLL--FEEE--  IAGETCDAK---AL  165
EFR44625       144 DSKEKSDVRLIYLALAHIIKYRGHFLYEET-FDIKNNDIQKI--FNEFINIYDNT--FEGS-S  LSGQNAQVE---AI  211
WP_002897477   144 DSKEKTDLRLIYLALAHMIKYRGHFLYEES-FDIKNNDIQKI--FNEFISIYDNT--FEGS-S  LSGQNAQVE---AI  211
WP_002906454   145 DSKEKTDLRLIYLALAHMIKYRGHFLYEEA-FDIKNNDIQKI--FNEFISIYNNT--FEGN-S  LSGQNVQVE---AI  212
WP_009729476   144 DSSEKADLRLIVYLALAHIIKYRGHFLIDEP-IDIRNMNSQNL--FKEFLLAPDGI--QVDC-Y  LASKHTDIS---GI  211
CQR24647       145 DSSEKTDLRLIYLALAHIIKYRGHFLYEES-FDIKNNDIQKI--FSEFISIYDNT--FEGK-S  LSGQNAQVE---AI  212
WP_000066813   145 DSKEKADLRLIYLALAHIIKYRGHFLYEEA-FDIKNNDIQKI--FNEFINIYDNT--FEGS-S  LSGQNAQVE---AI  212
WP_009754323   144 DSKEKADIRLIYLALAHIIKYRGHELFEGD-LKSENKDVQHL--FNDEVEMFDKT--VEGS-Y  LSENLPNVA---DV  211
WP_044676715   144 DSSQKADIRLIYLALAHIIKYRGHELFEGD-LKSENKDVQHL--FNDEVEMFDKT--VEGS-Y  LSENLPNVA---DV  211
WP_044680361   144 DSSQKADIRLIYLALAHIIKYRGHELFEGD-LKSENKDVQHL--FNDEVEMFDKT--VEGS-Y  LSENLPNVA---DV  211
WP_044681799   144 DISQKADIRLVYLALAHIIHHLIKYRGHFLIEGQ-LKAENTNVQAL--FKDEVEVYDKT--VEES-H  LSEMTVDAL---SI  211
WP_049533112   101 SQHRQFDIREVYLAIHHLIKYRGHFLIYEDQtFTTDGNQLQHH--IKAIITMINST1---NR--  IIPETIDINvfeKI  171
WP_029090905   140 ESTEKADPDLKADIRLIYLALHHIVKYRGNFLYEGQkFNMDASNIEDK--LSDIFTQFTSFmnIPYEdD  --KKNLEIL---EI  210
WP_006506696   144 DSTDKADIRLIYLALAHMIKERGHFLIEGD-LNPDNSDVDKL--FIQLVQTYNQL--FEEN--  INASGVDAK---AI  211
AIT42264       143 DSTNQKADLRLIYLALAHMIKERGHFLIEGD-LKMDGISISES--FQEFIDSYNEVcaLEDE-N  NDELLTQIE---NI  217
AKQ21048       144 DSTDKADLRLIYLALAHIVKYRGHFLIEGD-LNPDNSDVDKL--FIQLVQTYNQL--FKEQ--  INASGVDAK---AI  211
WP_004636532   144 DNPEKADLRLIYLALAHIVKYRGHFLIEGE-LNTENTISET--FEQFLDTYSDI--FKEQ--  LVGDISKVE---EI  210
WP_002364836   144 DSSEQADLRLIYLALAHIVKYRGHFLIEGK-LSTENISVKEQ--FQQFMIIYNQT--FVNGeS  PLPESVLIE---EE  217
WP_016631044    95 DSSEQADLRLIYLALAHIVKYRGHFLIEGK-LSTENISVKEQ--FQQFMIIYNQT--FVNGeS  PLPESVLIE---EE  168
EMS75795       ---                                                                               
WP_002373311   144 DSSEQADLRLIYLALAHIVKYRGHFLIEGK-LSTENTSVKEQ--FQQFMVIYNQT--FVNGeS  PLPESVLIE---EE  217
WP_002378009   144 DSSEQADLRLIYLALAHIVKYRGHFLIEGK-LSTENISVKEQ--FQQFMIIYNQT--FVNGeS  PLPESVLIE---EE  217
WP_002407324   144 DSSEQADLRLIYLALAHIVKYRGHFLIEGK-LSTENISVKEQ--FQQFMIIYNQT--FVNGeS  PLPESVLIE---EE  217
WP_002413717   144 DSSEQADLRLIYLALAHIVKYRGHFLIEGK-LSTENISVKEQ--FQQFMIIYNQT--FVNGeS  PLPESVLIE---EE  217
WP_010775580   144 DSSEQADLRLIYLALAHIVKYRGHFLIEGK-LSTENTSVKEQ--FQQFMIIYNQT--FVNGeS  PLPESVLIE---EE  217
WP_010818269   144 DSSEQADLRLIYLALAHIVKYRGHFLIEGK-LSTENISVKEQ--FQQFMIIYNQT--FVNGeS  PLPESVLIE---EE  217
WP_010824395   144 DSSEQADLRLIYLALAHIVKYRGHFLIEGK-LSTENTSVKDQ--FQQFMVIYNQT--FVNGeS  PLPESVLIE---EE  217
WP_016622645   144 DSSEQADLRLIYLALAHIVKYRGHFLIEGK-LSTENISVKEK--FQQFMIIYNQT--FVNGeG  PLPESVLIE---EE  217
WP_033624816   144 DSSEQADLRLIYLALAHIVKYRGHFLIEGK-LSTENISVKDQ--FQQFMVIYNQT--FVNGeS  PLPESVLIE---EE  217
WP_033625576   144 DSSEQADLRLIYLALAHIVKYRGHFLIEGK-LSTENISVKEQ--FQQFMIIYNQT--FVNGeS  PLPESVLIE---EE  217
WP_033789179   144 DSSEKADIRLVYLAMAHLLKYRGHFLIEGE-LNTENSVTET--FRQFLSTYNQQ--FSEA-D  KLDEAVDCS---FV  216
WP_002310644   144 DSSEKADIRLVYLAMAHLLKYRGHFLIEGE-LNTENSVTET--FRQFLSTYNQQ--FSEA-G  KLDEAVDCS---FV  216
WP_002312694   144 DSSEKADIRLVYLAMAHLLKYRGHFLIEGE-LNTENSVTET--FRQFLSTYNQQ--FSEA-G  KLDEAVDCS---FV  216
```

```
WP_002314015   144 DSSEKADIRLVYLAMAHLLKYRGHFLIEGE-LNTENSSVTET--FRQFLSTNQQ--FSEA-D KLDEAVDCS---FV 216
WP_002320716   144 DSSEKADIRLVYLAMAHLLKYRGHFLIEGE-LNTENSSVTET--FRQFLSTNQQ--FSEA-D KLDEAVDCS---FV 216
WP_002330729   144 DSSEKADIRLVYLAMAHLLKYRGHFLIEGE-LNTENSSVTET--FRQFLSTNQQ--FSEA-D KLDEAVDCS---FV 216
WP_002335161   144 DSSEKADIRLVYLAMAHLLKYRGHFLIEGE-LNTENSSVTET--FRQFLSTNQQ--FSEA-D KLDEAVDCS---FV 216
WP_002345439   144 DSSEKADIRLVYLAMAHLLKYRGHFLIEGE-LNTENSSVTET--FRQFLSTNQQ--FSEA-D KLDEAVDCS---FV 216
WP_034867970   144 DSSEKEDIRLVYLALAHLLKYRGHFLIEGE-LDTKNTSVEES--FRVFLEQYSKQ--SDQP- -LIVHQPVL---TI 209
WP_047937432   144 DSSEKADIRLVYLAMAHLLKYRGHFLIEGE-LNTENSSVTET--FRQFLSTNQQ--FSEA-D KLDEAVDCS---FV 216
WP_010720994   144 DSTKGDIRLVYLALAHLLKYRGHFLFEGD-LDTKNTSIEES--FRVFLEQYGKQ--SDQP- -LIVHQPVL---TI 209
WP_010737004   144 DSTEKEDIRLVYLALAHLLKYRGHFLFEGD-LDTENTSIEES--FRVFLEQYGKQ--SDQP- -LIVHQPVL---TI 209
WP_010700478   144 DSTEKEDIRLVYLALAHLLKYRGHFLIEGE-LDTENTSIEES--FRVFLEQYGKQ--SDQP- -LIVHQPVL---TI 209
WP_007209003   144 DGDEKADIRLVYLAIAHCLKYRGHFLIEGE-LNTENNSVIELs--KVFVQLNQT1-SELE- FIDESIDFS---EV 214
WP_023519017   144 NSKEQADIRLVYLAIAHLIKFRGNFLIEGE-LDTENTSVTEN--YQQFLQAYQQF--FPEP- -IGDLDDAV---PI 209
WP_010770040   144 DTSEQADIRLVYLALAHLIKYRGHFLIEGE-LNTENSVSET--FRITFIQVNQI--FRENe PLAVPDNIE---EL 212
WP_048604708   144 DAEEKADIRLVYLALAHLIKYRGHFLIEGR-LSTENTSTEET--FKITFLQKTNQT--FN-- PVDETISIG---SI 208
WP_010750235   144 DSTEKADIRLIYLALAHMIKYRGHFLFEGE-LDTENTSVEET--FKEFIDIYNEQ--FEEG- -IIFYKDIP---LI 209
AII16583       183 DSTDKADIRLIYLALAHMIKYRGHFLIEGD-LNPDNSDVDKL--FIQLVQTYNQL--FEEN- INASGVDAK---AI 250
WP_029073316   145 ESEKEEDPRLIIYALMHHIVKYRGNFLYEGQkFSMDVSNIEDK--MIDVLRQFNEIn1FEYveD --KKIDEVL---NV 215
WP_031589969   145 ESEKEEDPRLIYLALHHIVKYRGNFLYEGQkFSMDVSNIEDK--MIDVLRQFNEIn1FEYveD --KKIDEVL---NV 215
KDA45870       145 NNDRPADLRLVYLALAHIIKYRGNELLEGE-IDLRTTDINKV--FAEFSETLNEN--SDEN1G --KLDVA----DI 209
WP_039099354   133 TEKRQFDIREIYLAMHHIVKYRGHFLNEAPvSSEKSSEINLVahFDRLNTIFADL-FSESgF -TDKLAEVK---AL 206
AKP02966       138 INKNKADIRLVYLALHNIIKYRGNFTYEHQkFNISTLNSNLS--KELIELNOQLikYDIS- -FPDNCDWNhisDI 208
WP_010991369   144 NSSEKADLRLVYLALAHIIKYRGHFLIEGA-LDTQNTSVDGI--YKQFIQTYNQV--FASGiE KLEDNKDVA---KI 217
WP_033838504   144 NSSEKADLRLVYLALAHIIKYRGHFLIEGA-LDTQNTSVDGI--YKQFIQTYNQV--FASGiE KLEDNKDVA---KI 217
EHN60060       147 NSSEKADLRLVYLALAHIIKYRGNELLIEGA-LDTQNTSVDGI--YKQFIQTYNQV--FASGiE KLEDNKDVA---KI 220
EFR89594       --- ------------------------------------------------------------ -------------- ---
WP_038409211   144 NSSDKADLRLVYLALHNIIKYRGNFLIEGM-LDTKNTSVDEV--FKQFIQTYNQI--FASDiE RLEENKEVA---EI 217
EFR95520       --- ------------------------------------------------------------ -------------- ---
WP_003723650   144 NSSDKADLRLVYLALAHIIKYRGNFLIEGA-LDTKNTSVDEV--YKQFIETYNQV--FMSNiE KVEENIEVA---NI 217
AKE81011       160 DSTDKADLRLIYLALAHIIKYRGNFLIEGA-LDTKNTSVDEV--YKQFIQTYNQV--FMSNiE KVEENTEVA---SI 227
CUO82355       144 ESTEKADPRLIIYALHHIVKYRGNFLIEGA-LDTKNTSVDEV--YKQFIQTYNQV--FMSNiE KVEENTEVA---EI 214
WP_033162887   145 ENKEKADPRLIIYALHHIVKYRGNFLYEGQsFTMDNSDIEER--LSDVFTQFADFnmIPYEdD --KKNLEIL---EI 215
AGZ01981       177 DSTDKADLRLIYLALAHMIKYRGHFLIEGA-LDPDNSDVDKL--FIQLVQTYNQL--FEEN- INASGVDAK---AV 244
AKA60242       144 DSTDKADLRLIYLALAHMIKYRGHFLIEGD-LNPDNSDVDKL--FIQLVQTYNQL--FEEN- INASGVDAK---AI 211
AKS40380       144 DSTDKADLRLIYLALAHMIKYRGHFLIEGD-LNPDNSDVDKL--FIQLVQTYNQL--FEEN- INASGVDAK---AI 211
4UN5_B         148 DSTDKADLRLIYLALAHMIKYRGHFLIEGD-LNPDNSDVDKL--FIQLVQTYNQL--FEEN- INASGVDAK---AI 215
WP_010922251   212 LSAR-LSKSRRLENLIAQ-L-PG EKKNGLFGNLIALSLGLTPNFKSNF--DLAED-A---KLQ--LSKDTYDDDLDN 277
WP_039695303   213 LTEK-ISKSRRLENLIKY-Y-PT EKKNTLFGNLIALALGLQPNFKTNF--KLSED-A---KLQ--FSKDTYBEDLEE 278
WP_045635197   212 FTDK-ISKSAKRERVLKL-F-PD EKSTGLFSEFLKLIVGNQADFKKHF--DLEDK-A---PLQ--FSKDTYDEDLEN 277
5AXW_A         135 LSTK-------EQISRN-S--K -------------- -LEEKyVa--ELQ-- 157
WP_009880683   --- ------------------------------------------------------------ -------------- ---
```

| | | | | |
|---|---|---|---|---|
| WP_010922251 | 212 | LSAR-LSKSRRLENLIAQ-L-PG | EKKNGLFGNLIALSLGLTPNFKSNF--DLAED-A---KLQ-LSKDTYDDDLDN | 277 |
| WP_011054416 | 212 | LSAR-LSKSRRLENLIAQ-L-PG | EKKNGLFGNLIALSLGLTPNFKSNF--DLAED-A---KLQ-LSKDTYDDDLDN | 277 |
| WP_011284745 | 212 | LSAR-LSKSRRLENLIAQ-L-PG | EKKNGLFGNLIALSLGLTPNFKSNF--DLAED-A---KLQ-LSKDTYDDDLDN | 277 |
| WP_011285506 | 212 | LSAR-LSKSRRLENLIAQ-L-PG | EKKNGLFGNLIALSLGLTPNFKSNF--DLAED-A---KLQ-LSKDTYDDDLDN | 277 |
| WP_011527619 | 212 | LSAR-LSKSRRLENLIAQ-L-PG | EKKNGLFGNLIALSLGLTPNFKSNF--DLAED-A---KLQ-LSKDTYDDDLDN | 277 |
| WP_012560673 | 212 | LSAR-LSKSRRLENLIAQ-L-PG | EKKNGLFGNLIALSLGLTPNFKSNF--DLAED-A---KLQ-LSKDTYDDDLDN | 277 |
| WP_014407541 | 212 | LSAR-LSKSRRLENLIAQ-L-PG | EKRNGLFGNLIALSLGLTPNFKSNF--DLAED-A---KLQ-LSKDTYDDDLDN | 277 |
| WP_020905136 | 212 | LSAR-LSKSRRLENLIAQ-L-PG | EKRNGLFGNLIALSLGLTPNFKSNF--DLAED-A---KLQ-LSKDTYDDDLDN | 277 |
| WP_023080005 | 212 | LSAR-LSKSRRLENLIAQ-L-PG | EKKNGLFGNLIALSLGLTPNFKSNF--DLAED-A---KLQ-LSKDTYDDDLDN | 277 |
| WP_023610282 | 212 | LSAR-LSKSRRLENLIAQ-L-PG | EKKNGLFGNLIALSLGLTPNFKSNF--DLAED-A---KLQ-LSKDTYDDDLDN | 277 |
| WP_030125963 | 212 | LSAR-LSKSRRLENLIAQ-L-PG | EKRNGLFGNLIALSLGLTPNFKSNF--DLAED-A---KLQ-LSKDTYDDDLDN | 277 |
| WP_030126706 | 212 | LSAR-LSKSRRLENLIAQ-L-PG | EKKNGLFGNLIALSLGLTPNFKSNF--DLAED-A---KLQ-LSKDTYDDDLDN | 277 |
| WP_031488318 | 212 | LSAR-LSKSRRLENLIAQ-L-PG | EKKNGLFGNLIALSLGLTPNFKSNF--DLAED-A---KLQ-LSKDTYDDDLDN | 277 |
| WP_032460140 | 212 | LSAR-LSKSRRLENLIAQ-L-PG | EKKNGLFGNLIALSLGLTPNFKSNF--DLAED-A---KLQ-LSKDTYDDDLDN | 277 |
| WP_032461047 | 212 | LSAR-LSKSRRLENLIAQ-L-PG | EKRNGLFGNLIALSLGLTPNFKSNF--DLAED-A---KLQ-LSKDTYDDDLDN | 277 |
| WP_032462016 | 212 | LSAR-LSKSRRLENLIAQ-L-PG | EKRNGLFGNLIALSLGLTPNFKSNF--DLAED-A---KLQ-LSKDTYDDDLDN | 277 |
| WP_032462936 | 212 | LSAR-LSKSRRLENLIAQ-L-PG | EKKNGLFGNLIALLLGLTPNFKSNF--DLAED-A---KLQ-LSKDTYDDDLDN | 277 |
| WP_032464890 | 212 | LSAR-LSKSRRLENLIAQ-L-PG | EKKNGLFGNLIALSLGLTPNFKSNF--DLAED-A---KLQ-LSKDTYDDDLDN | 277 |
| WP_033888930 | 37 | LSAR-LSKSRRLENLIAQ-L-PG | EKKNGLFGNLIALSLGLTPNFKSNF--DLAED-A---KLQ-LSKDTYDDDLDN | 102 |
| WP_038431314 | 212 | LSAR-LSKSRRLENLIAQ-L-PG | EKKNGLFGNLIALSLGLTPNFKSNF--DLAED-A---KLQ-LSKDTYDDDLDN | 277 |
| WP_038432938 | 212 | LSAR-LSKSRRLENLIAQ-L-PG | EKKNGLFGNLIALSLGLTPNFKSNF--DLAED-T---KLQ-LSKDTYDDDLDN | 277 |
| WP_038434062 | 123 | LSAR-LSKSRRLENLIAQ-L-PG | EKRNGLFGNLIALSLGLTPNFKSNF--DLAED-A---KLQ-LSKDTYDDDLDN | 188 |
| BAQ51233 | | | | |
| KGE60162 | | | | |
| KGE60856 | | | | |
| WP_002989955 | 212 | LSAR-LSKSRRLENLIAQ-L-PG | EKKNGLFGNLIALSLGLTPNFKSNF--DLAED-A---KLQ-LSKDTYDDDLDN | 277 |
| WP_003030002 | 212 | LTEK-VSKSRRLENLIAH-Y-PA | EKKNTLFGNLIALSLGLQPNFKTNF--QLSED-A---KLQ-FSKDTYEEDLEG | 277 |
| WP_003065552 | 215 | LTEK-ISKSRRLENLIKY-Y-PT | EKKNTLFGNLIALALGLQPNFKMNF--KLSED-A---KLQ-FSKDSYEEDLGE | 280 |
| WP_001040076 | 213 | LTDK-ISKSAKKDRILAQ-Y-PN | QKSTGIFAEFLKLIVGNQADFKKHF--NLEDK-T---PLQ-FAKDSYDEDLEN | 278 |
| WP_001040078 | 213 | LTDK-ISKSAKKDRILAQ-Y-PN | QKSTGIFAEFLKLIVGNQADFKKHF--NLEDK-T---PLQ-FAKDSYDEDLEN | 278 |
| WP_001040080 | 213 | LTDK-ISKSAKKDRILAQ-Y-PN | QKSTGIFAEFLKLIVGNQADFKKYF--NLEDK-T---PLQ-FAKDSYDEDLEN | 278 |
| WP_001040081 | 213 | LTDK-ISKSAKKDRILAQ-Y-PN | QKSTGIFAEFLKLIVGNQADFKKYF--NLEDK-T---PLQ-FAKDSYDEDLEN | 278 |
| WP_001040083 | 213 | LTDK-ISKSAKKDRILAQ-Y-PN | QKSTGIFAEFLKLIVGNQADFKKYF--NLEDK-T---PLQ-FAKDSYDEDLEN | 278 |
| WP_001040085 | 213 | LTDK-ISKSAKKDRILAQ-Y-PN | QKSTGIFAEFLKLIVGNQADFKKYF--NLEDK-T---PLQ-FAKDSYDEDLEN | 278 |
| WP_001040087 | 213 | LTDK-ISKSAKKDRILAQ-Y-PN | QKSTGIFAEFLKLIVGNQADFKKHF--NLEDK-T---PLQ-FAKDSYDEDLEN | 278 |
| WP_001040088 | 213 | LTDK-ISKSAKKDRILAR-Y-PN | QKSTGIFAEFLKLIVGNQADFKKYF--NLEDK-T---PLQ-FAKDSYDEDLEN | 278 |
| WP_001040089 | 213 | LTDK-ISKSAKKDRILAQ-Y-PN | QKSTGIFAEFLKLIVGNQADFKKYF--NLEDK-T---PLQ-FAKDSYDEDLEN | 278 |
| WP_001040090 | 213 | LTDK-ISKSAKKDRILAQ-Y-PN | QKSTGIFAEFLKLIVGNQADFKKHF--NLEDK-T---PLQ-FAKDSYDEDLEN | 278 |
| WP_001040091 | 213 | LTDK-ISKSAKKDRILAR-Y-PN | QKSTGIFAEFLKLIVGNQADFKKYF--NLEDK-T---PLQ-FAKDSYDEDLEN | 278 |
| WP_001040092 | 213 | LTDK-ISKSAKKDRILAR-Y-PN | QKSTGIFAEFLKLIVGNQADFKKHF--NLEDK-T---PLQ-FAKDSYDEDLEN | 278 |
| WP_001040094 | 213 | LTDK-ISKSAKKDRILAR-Y-PN | QKSTGIFAEFLKLIVGNQADFKKHF--NLEDK-T---PLQ-FAKDSYDEDLEN | 278 |
| WP_001040095 | 213 | LTDK-ISKSAKKDRILAR-Y-PN | QKSTGIFAEFLKLIVGNQADFKKHF--NLEDK-T---PLQ-FAKDSYDEDLEN | 278 |
| WP_001040096 | 213 | LTDK-ISKSAKKDRILAR-Y-PN | QKSTGIFAEFLKLIVGNQADFKKHF--NLEDK-T---PLQ-FAKDSYDEDLEN | 278 |
| WP_001040097 | 213 | LTDK-ISKSAKKDRILAR-Y-PN | QKSTGIFAEFLKLIVGNQADFKKHF--NLEDK-T---PLQ-FAKDSYDEDLEN | 278 |
| WP_001040098 | 213 | LTDK-ISKSAKKDRILAR-Y-PN | QKSTGIFAEFLKLIVGNQADFKKHF--NLEDK-T---PLQ-FAKDSYDEDLEN | 278 |
| WP_001040099 | 213 | LTDK-ISKSAKKDRILAR-Y-PN | QKSTGIFAEFLKLIVGNQADFKKHF--NLEDK-T---PLQ-FAKDSYDEDLEN | 278 |
| WP_001040100 | 213 | LTDK-ISKSAKKDRILAR-Y-PN | QKSTGIFAEFLKLIVGNQADFKKHF--NLEDK-T---PLQ-FAKDSYDEDLEN | 278 |
| WP_001040104 | 213 | LTDK-ISKSAKKDRILAR-Y-PN | QKSTGIFAEFLKLIVGNQADFKKYF--NLEDK-T---PLQ-FAKDSYDEDLEN | 278 |
| WP_001040105 | 213 | LTDK-ISKSAKKDRILAR-Y-PN | QKSTGIFAEFLKLIVGNQADFKKYF--NLEDK-T---PLQ-FAKDSYDEDLEN | 278 |
| WP_001040106 | 213 | LTDK-ISKSAKKDRILAR-Y-PN | QKSTGIFAEFLKLIVGNQADFKKHF--NLEDK-T---PLQ-FAKDSYDEDLEN | 278 |
| WP_001040107 | 213 | LTDK-ISKSAKKDRILAR-Y-PN | QKSTGIFAEFLKLIVGNQADFKKHF--NLEDK-T---PLQ-FAKDSYDEDLEN | 278 |
| WP_001040108 | 213 | LTDK-ISKSAKKDRILAR-Y-PN | QKSTGIFAEFLKLIVGNQADFKKHF--NLEDK-T---PLQ-FAKDSYDEDLEN | 278 |
| WP_001040109 | 213 | LTDK-ISKSAKKDRILAR-Y-PN | QKSTGIFAEFLKLIVGNQADFKKHF--NLEDK-T---PLQ-FAKDSYDEDLEN | 278 |

-continued

```
WP_001040110   213 LTDK-ISKSAKKDRILAQ-Y-PN QKSTGIFAEFLKLIVGNQADFKKHF--NLEDK-T---PLQ-FAKDSYDEDLEN 278
WP_015058523   213 LTDK-ISKSAKKDRILAQ-Y-PN QKSTGIFAEFLKLIVGNQADFKKHF--NLEDK-T---PLQ-FAKDSYDEDLEN 278
WP_017643650   213 LTDK-ISKSAKKDRILAR-Y-PN QKSTGIFAEFLKLIVGNQADFKKHF--NLEDK-T---PLQ-FAKDSYDEDLEN 278
WP_017647151   213 LTDK-ISKSAKKDRILAQ-Y-PN QKSTGIFAEFLKLIVGNQADFKKHF--NLEDK-T---PLQ-FAKDSYDEDLEN 278
WP_017648376   213 LTDK-ISKSAKKDRILAQ-Y-PN QKSTGIFAEFLKLIVGNQADFKKHF--NLEDK-T---PLQ-FAKDSYDEDLEN 278
WP_017649527   213 LTDK-ISKSAKKDRILAQ-Y-PN QKSTGIFAEFLKLIVGNQADFKKHF--NLEDK-T---PLQ-FAKDSYDEDLEN 278
WP_017771611   213 LTDK-ISKSAKKDRILAQ-Y-PN QKSTGIFAEFLKLIVGNQADFKKHF--NLEDK-T---PLQ-FAKDSYDEDLEN 278
WP_017771984   213 LTDK-ISKSAKKDRILAQ-Y-PN QKSTGIFAEFLKLIVGNQADFKKHF--NLEDK-T---PLQ-FAKDSYDEDLEN 278
CFQ25032       213 LTDK-ISKSAKKDRILAQ-Y-PN QKSTGIFAEFLKLIVGNQADFKKYF--NLEDK-T---PLQ-FAKDSYDEDLEN 278
CFV16040       213 LTDK-ISKSAKKDRILAQ-Y-PN QKSTGIFAEFLKLIVGNQADFKKYF--NLEDK-T---PLQ-FAKDSYDEDLEN 278
KLJ37842       213 LTDK-ISKSAKKDRILAR-Y-PN QKSTGIFAEFLKLIVGNQADFKKYF--NLEDK-T---PLQ-FAKDSYDEDLEN 278
KLJ72361       213 LTDK-ISKSAKKDRILAQ-Y-PN QKSTGIFAEFLKLIVGNQADFKKYF--NLEDK-T---PLQ-FAKDSYDEDLEN 278
KLL20707       213 LTDK-ISKSAKKDRILAQ-Y-PN QKSTGIFAEFLKLIVGNQADFKKYF--NLEDK-T---PLQ-FAKDSYDEDLEN 278
KLL42645       213 LTDK-ISKSAKKDRILAQ-Y-PN QKSTGIFAEFLKLIVGNQADFKKYF--NLEDK-T---PLQ-FAKDSYDEDLEN 278
WP_047207273   213 LTDK-ISKSAKKDRILAR-Y-PN QKSTGIFAEFLKLIVGNQADFKKYF--NLEDK-T---PLQ-FAKDSYDEDLEN 278
WP_047209694   213 LTDK-ISKSAKKDRILAR-Y-PN QKSTGIFAEFLKLIVGNQADFKKYF--NLEDK-T---PLQ-FAKDSYDEDLEN 278
WP_050198062   213 LTDK-ISKSAKKDRILAQ-Y-PN QKSTGIFAEFLKLIVGNQADFKKYF--NLEDK-T---PLQ-FAKDSYDEDLEN 278
WP_050201642   213 LTDK-ISKSAKKDRILAQ-Y-PN QKSTGIFAEFLKLIVGNQADFKKYF--NLEDK-T---PLQ-FAKDSYDEDLEN 278
WP_050204027   213 LTDK-ISKSAKKDRILAQ-Y-PN QKSTGIFAEFLKLIVGNQADFKKYF--NLEDK-T---PLQ-FAKDSYDEDLEN 278
WP_050881965   213 LTDK-ISKSAKKDRILAQ-Y-PN QKSTGIFAEFLKLIVGNQADFKKYF--NLEDK-T---PLQ-FAKDSYDEDLEN 278
WP_050886065   213 LTDK-ISKSAKKDRILAQ-Y-PN QKSTGIFAEFLKLIVGNQADFKKYF--NLEDK-T---PLQ-FAKDSYDEDLEN 278
AHN30376       213 LTDK-ISKSAKKDRILAQ-Y-PN QKSTGIFAEFLKLIVGNQADFKKYF--NLEDK-T---PLQ-FAKDSYDEDLEN 278
EA078426       213 LTDK-ISKSAKKDRILAQ-Y-PN QKSTGIFAEFLKLIVGNQADFKKYF--NLEDK-T---PLQ-FAKDSYDEDLEN 278
CCW42055       213 LTDK-ISKSAKKDRILAQ-Y-PD QKSTGIFAEFLKLIVGNQADFKKHF--NLEDK-T---PLQ-FAKDSYDEDLEN 278
WP_003041502   212 LTEK-VSKSRRLENLIAH-Y-PA EKKNTLFGNLIALFLGLGLQPNFKTNF--QLSED-A---KLQ-FSKDTYEDLEG 277
WP_037593752   213 LTEK-VSKSRRLENLIAH-Y-PT EKKNTLFGNLIALSLGLGLQPNFKTNF--QLSED-A---KLQ-FSKDTYEEDLEE 278
WP_049516684   213 LTEK-VSKSRRLENLVEC-Y-PT EKKNTLFGNLIALSLGLGLQPNFKTNF--QLSED-A---KLQ-FSKDTYEEDLEE 278
GAD46167       212 LTEK-VSKSRRLENLIAH-Y-PT EKKNTLFGNLIALSLGLGLQPNFKTNF--QLSED-A---KLQ-FSKDTYEEDLEE 277
WP_018363470   213 LTEK-ISKSRRLENLINN-Y-PK EKKNGLFGNIIALALGLTPNFKSNF--KLSED-A---KLQ-LSKDTYDDDLDE 278
WP_003043819   212 LSAR-LSKSKRLEKLIAV-F-PN EKKNGLFGNIIALALGLSLDLHPNFKTNF--DLTED-A---KLQ-LSKDTYDDDLDE 277
WP_062669658   212 LTEK-VSKSSRLENLIAH-Y-PT EKKNGLFGNIIALSLGLGLQPNFKTNF--QLSED-A---KLQ-FSKDTYEEDLEG 277
WP_048800889   212 LTEK-VSKSRRLENLVKC-Y-PT EKKNTLFGNLIALSLGLGLQPNFKTNF--QLSED-A---KLQ-FSKDTYEEDLEE 277
WP_012767106   212 LSAR-LSKSRRLENLIAQ-L-PG EKRNGLFGNLIALSLGLGLQPNFKSNF--DLAED-A---KLQ-LSKDTYDDDLDN 277
WP_014612333   212 LSAR-LSKSRRLENLIAQ-Y-PT EKKNGLFGNLIALSLGLTPNFKSNF--DLAED-A---KLQ-LSKDTYDDDLDN 277
WP_015017095   212 LSAR-LSKSRRLENLIAQ-L-PG EKRNGLFGNLIALSLGLGLQPNFKSNF--DLAED-A---KLQ-LSKDTYDDDLDN 277
WP_015057649   213 LSAR-LSKSRRLENLIAQ-L-PG EKRNGLFGNIVALALGLQPNFKMNF--KLSED-A---KLQ-FSKDTYDDDLDN 278
WP_048327215   212 LSAR-LSKSRRLENLIAQ-Y-PT EKKNTLFGNLIALSLGLGLQPNFKTSF--KLSED-A---KLQ-FSKDTYEEDLEE 277
WP_049519324   212 LSAR-LSKSRRLENLIAQ-L-PG EKRNGLFGNLIALSLGLTPNFKSNF--DLAED-A---KLQ-LSKDTYDDDLDN 277
WP_012515931   212 LSAA-LSKSKRLENLISL-I-PG QKKTGLFGNLIALSLDLHPNFKANF--GLSKD-V---KLQ-LAKDTYADDLDS 277
WP_012120964   212 LSAA-LSKSKRLENLISL-I-PG QKKTGLFGNLIALSLGLTPNFKANF--GLSKD-V---KLQ-LAKDTYADDLDS 277
WP_037581760   212 LSAA-LSKSRRLENLISL-I-PG EKKNTLFGNLIALGLQPNFKANF--GLSKD-V---KLQ-LAKDTYADDLDS 277
WP_004232481   212 LTEK-ISKSRRLENLIKQ-Y-PT EKKNGLFGNLIVALALGLQPNFKTNF--KLSED-A---KLQ-FSKDTYDEDLEE 278
WP_009854540   213 LTEK-FSKSRRLENLIKH-Y-PT EKKNTLFGNLIALALGLQPNFKTSF--KLSED-A---KLQ-FSKDTYEEDLEE 278
WP_012962174   212 LTEK-ISKSRRLENLIKY-Y-PT EKKNTLFGNLIALGLQPNFKTNF--KLSED-A---KLQ-FSKDTYEEDLEE 277
WP_039695303   213 LTEK-ISKSRRLENLIKY-Y-PT EKKNTLFGNLIALGLQPNFKTNF--KLSED-A---KLQ-FSKDTYEEDLEE 278
WP_014334983   212 LTEK-VSKSRRLENLIKQ-Y-PT EKKNGLFGNLIALGLQPNFKTNF--KLSED-A---KLQ-FSKDTYEEDLEE 277
WP_003099269   212 LSAA-LSKSKRLENLIAE-I-PN QKRNMLFGNLVSLALGLTPNFKTNF--ELLED-A---KLQ-ISKDSYEEDLDN 277
AHY15608       212 LTSK-TSKSRRLENLIAE-I-PN QKRNMLFGNLVSLALGLTPNFKTNF--ELLED-A---KLQ-ISKDSYEEDLDN 277
AHY17476       212 LTSK-TSKSRRLENLIAE-I-PG QKRNMLFGNLVSLALGLTPNFKTNF--ELLED-A---KLQ-ISKDSYEEDLDN 277
ESR09100       ---  ---------------------- -------------------------------- ---------- ---
AGM98575       212 LTSK-TSKSRRLENLIAE-I-PN QKRNMLFGNLVSLALGLTPNFKTNF--ELLED-A---KLQ-ISKDSYEEDLDN 277
ALF27331       210 LTBK-ISKSAKKDRVLKL-F-PN EKSNGRFAEFLKLIVGNQADFKKHF--ELEEK-A---PLQ-FSKDSYEEELEV 277
WP_018372492   210 FTEN-SSKAKRVETILGL-F-PD ETAAGNLDKFLKLMLGNQADFKKVF--DLEEK----A---iTLQ-FSKDSYEEDLEL 275
```

```
-continued

WP_045618028   213 FTDK-ISKSAKRERVLKL-F-PD EKSTGLFSEFLKLIVGNQADFKKHF--DLEEK-A----PLQ--FSKDTYDEDLEN   278
WP_045635197   212 FTDK-ISKSAKRERVLKL-F-PD EKSTGLFSEFLKLIVGNQADFKKHF--DLEDK-A----PLQ--FSKDTYDEDLEN   277
WP_002263549   212 LTDK-ISKSAKDRVLKL-F-PN EKSNGRFAEFLKLIVGNQADFKKHF--ELEEK-A----PLQ--FSKDTYEEELEV   277
WP_002263887   212 LTDK-ISKSRRLEKLINN-Y-PK EKKNTLFRNLVALSLGLQPNFKTNF--KLSED-A----KLQ--FSKDTYEEDLEE   277
WP_002264920   212 LTEK-ISKSRRLEKLINN-Y-PK EKKNTLFRNLVALSLGLQPNFKTNF--KLSED-A----KLQ--FSKDTYEEDLEE   277
WP_002269043   212 LTDK-ISKSAKDRVLKL-F-PN EKSNGRFAEFLKLIVGNQADFKKHF--ELEEK-A----PLQ--FSKDIYEEELEV   277
WP_002269448   212 LTDK-ISKSAKDRVLKL-F-PN EKSNGRFAEFLKLIVGNQADFKKHF--ELEEK-A----PLQ--FSKDTYEEELEV   277
WP_002271977   212 LTDK-ISKSAKDRVLKL-F-PN EKSNGRFAEFLKLIVGNQADFKKHF--ELEEK-A----PLQ--FSKDTYEEELEV   277
WP_002272766   212 LTDK-ISKSAKDRVLKL-F-PN EKSNGRFAEFLKLIVGNQADFKKHF--ELEEK-A----PLQ--FSKDTYEEELEV   277
WP_002273241   212 LTDK-ISKSAKDRVLKL-F-PN EKSNGRFAEFLKLIVGNQADFKKHF--ELEEK-A----PLQ--FSKDTYEEELEV   277
WP_002275430   212 LTDK-ISKSAKDRVLKL-F-PN EKSNGRFAEFLKLIVGNQADFKKHF--ELEEK-A----PLQ--FSKDTYEEELEV   277
WP_002276448   212 LTDK-ISKSAKDRVLKL-F-PN EKSNGRFAEFLKLIVGNQADFKKHF--ELEEK-A----PLQ--FSKDTYEEDLEE   277
WP_002277050   212 LTEK-ISKSRRLEKLINN-Y-PK EKKNTLFGNLIALSLGLQPNFKTNF--KLSED-A----KLQ--FSKDTYEEDLEE   277
WP_002277364   212 LTDK-ISKSAKDRVLKL-F-PN EKSNGRFAEFLKLIVGNQADFKKHF--ELEEK-A----PLQ--FSKDTYEEELEV   277
WP_002279025   212 LTDK-ISKSAKDRVLKL-F-PN EKSNGRFAEFLKLIVGNQADFKKHF--ELEEK-A----PLQ--FSKDTYEEELEV   277
WP_002279859   212 LTEK-ISKSRRLEKLINN-Y-PK EKKNTLFGNLIALSLGLQPNFKTNF--KLSED-A----KLQ--FSKDTYEEDLEE   277
WP_002280230   212 LTDK-ISKSAKDRVLKL-F-PN EKSNGRFAEFLKLIVGNQADFKKHF--ELEEK-A----PLQ--FSKDTYEEELEV   277
WP_002281696   212 LTDK-ISKSAKDRVLKL-F-PN EKSNGRFAEFLKLIVGNQADFKKHF--ELEEK-A----PLQ--FSKDTYEEELEV   277
WP_002282247   212 LTEK-ISKSRRLEKLINN-Y-PK EKKNTLFGNLIALSLGLQPNFKTNF--KLSED-A----KLQ--FSKDTYEEDLEE   277
WP_002282906   212 LTDK-ISKSAKDRVLKL-F-PN EKSNGRFAEFLKLIVGNQADFKKHF--ELEEK-A----PLQ--FSKDTYEEELEV   277
WP_002283846   212 LTDK-ISKSAKDRVLKL-F-PN EKSNGRFAEFLKLIVGNQADFKKHF--ELEEK-A----PLQ--FSKDTYEEELEV   277
WP_002287255   212 LTDK-ISKSAKDRVLKL-F-PN EKSNGRFAEFLKLIVGNQADFKKHF--ELEEK-A----PLQ--FSKDTYEEELEV   277
WP_002288990   212 LTDK-ISKSAKDRVLKL-F-PN EKSNGRFAEFLKLIVGNQADFKKHF--ELEEK-A----PLQ--FSKDTYEEELEV   277
WP_002289641   212 LTDK-ISKSAKDRVLKL-F-PN EKSNGCFAEFLKLIVGNQADFKKHF--ELEEK-A----PLQ--FSKDTYEEELEV   277
WP_002290427   212 LTDK-ISKSAKDRVLKL-F-PN EKSNGRFAEFLKLIVGNQADFKKHF--ELEEK-A----PLQ--FSKDTYEEELEV   277
WP_002295753   212 LTDK-ISKSAKDRVLKL-F-PN EKSNGRFAEFLKLIVGNQADFKKHF--ELEEK-A----PLQ--FSKDIYEEELEV   277
WP_002296423   212 LTEK-VSKSRRLENLVEC-Y-PT EKKNTLFGNLIALSLGLQPNFKTNF--QLSED-A----KLQ--FSKDTYEEDLEG   277
WP_002304487   212 LTDK-ISKSAKDRVLKL-F-PN EKSNGRFAEFLKLIVGNQADFKKHF--ELEEK-A----PLQ--FSKDTYEEELEV   277
WP_002305844   212 LTDK-ISKSAKDRVLKL-F-PN EKSNGRFAEFLKLIVGNQADFKKHF--ELEEK-A----PLQ--LSKDTYEEELEV   277
WP_002307203   212 LTDK-ISKSAKDRVLKL-F-PN EKSNGRFAEFLKLIVGNQADFKKHF--ELEEK-A----PLQ--FSKDTYEEELEV   277
WP_002310390   212 LTEK-ISKSRRLEKLINN-Y-PK EKKNTLFGNLIALSLGLQPNFKTNF--KLSED-A----KLQ--FSKDTYEEDLEE   277
WP_002352408   212 LTDK-ISKSAKDRVLKL-F-PN EKSNGRFAEFLKLIIGNQADFKKHF--ELEEK-A----PLQ--FSKDTYEEELEV   277
WP_012997688   212 LTDK-ISKSAKDRVLKL-F-PN EKSNGRFAEFLKLIVGNQADFKKHF--ELEEK-A----PLQ--FSKDTYEEELEV   277
WP_014677909   212 LTDK-ISKSAKDRVLKL-F-PN EKSNGRFAEFLKLIVGNQADFKKHF--ELEEK-A----PLQ--FSKDTYEEELEV   277
WP_019312892   212 LTDK-ISKSAKDRVLKL-F-PN EKSNGRFAEFLKLIVGNQADFKKHF--ELEEK-A----PLQ--FSKDTYEEELEV   277
WP_019313659   212 LTDK-ISKSAKDRVLKL-F-PN EKSNGRFAEFLKLIVGNQADFKKHF--ELEEK-A----PLQ--FSKDTYEEELEV   277
WP_019314093   212 LTEK-ISKSRRLEKLINN-Y-PK EKKNTLFGNLIALSLGLQPNFKTNF--KLSED-A----KLQ--LSKDTYEEDLEE   277
WP_019315370   212 LTDK-ISKSAKDRVLKL-F-PN EKSNGRFAEFLKLIVGNQADFKKHF--ELEEK-A----PLQ--FSKDTYEEELEV   277
WP_019803776   212 LTDK-ISKSAKDRVLKL-F-PN EKSNGRFAEFLKLIVGNQADFKKHF--ELEEK-V----PLQ--FSKDIYEEELEV   277
WP_019805234   212 LTDK-ISKSAKDRVLKL-F-PN EKSNGRFAEFLKLIVGNQADFKKHF--ELEEK-A----PLQ--FSKDTYEEELEV   277
WP_024783594   212 LTDK-ISKSAKDRVLKL-F-PN EKSNGRFAEFLKLIVGNQADFKKHF--ELEEK-A----PLQ--FSKDTYEEELEV   277
WP_024784288   212 LTEK-ISKSRRLEKLINN-Y-PK EKKNTLFGNLIALSLGLQPNFKTNF--KLSED-A----KLQ--FSKDTYEEDLEE   277
WP_024784666   212 LTDK-ISKSAKDRVLKL-F-PN EKSNGRFAEFLKLIVGNQADFKKHF--ELEEK-A----PLQ--FSKDTYEEELEV   277
WP_024784894   212 LTDK-ISKSAKDRVLKL-F-PN EKSNGRFAEFLKLIVGNQADFKKHF--ELEEK-A----PLQ--FSKDTYEEELEV   277
WP_024786433   212 LTEK-ISKSRRLEKLINN-Y-PK EKKNTLFGNLIALSLGLQPNFKTNF--KLSED-A----KLQ--FSKDTYEEDLEE   277
WP_049473442   212 LTDK-ISKSAKDRVLKL-F-PN EKSNGRFAEFLKLIVGNQADFKKHF--ELEEK-A----PLQ--FSKDTYEEELEV   277
WP_049474547   212 LTDK-ISKSAKDRVLKL-F-PN EKSNGRFAEFLKLIVGNQADFKKHF--ELEEK-A----PLQ--FSKDTYEEELEV   277
EMC03581       205 LTDK-ISKSAKDRVLKL-F-PN EKSNGRFAEFLKLIVGNQADFKKHF--ELEEK-A----PLQ--FSKDTYEEELEV   270
WP_000428612   213 FTDK-ISKSAKRERVLKL-F-PD EKSTGLFSEFLKLIVGNQADFKKHF--DLEEK-A----PLQ--FSRDTYDEDLEN   278
WP_000428613   213 FTDK-ISKSAKRERVLKL-F-PD EKSTGLFSEFLKLIVGNQADFKKHF--DLEEK-A----PLQ--FSKDTYDEDLEN   278
WP_049523028   212 FTDK-ISKSAKDRVLKL-F-PD EKSTGLFSEFLKLIVGNQADFKKHF--DLGEK-A----PLQ--FSKDTYEEDLES   277
WP_003107102   181 LTEK-MSKSRRLENLIAK-I-PN QKKNTLFGNLISLSLGLTPNFKANF--ELSED-A----KLQ--ISKESFEEDLDN   246
WP_054279288   214 LTEK-ISKTRRLENLISN-I-PG QKKNGLFGNLIALSLGLTPNFKSHF--NLPED-A----KLQ--LAKDTYDEELNN   279
```

| ID | Pos1 | Seq1 | Seq2 | Seq3 | Seq4 | Pos2 |
|---|---|---|---|---|---|---|
| WP_049531101 | 213 | FTDK-ISKSTKRERVLKL-F-PD | QKSTGLFSEFLKLIVGNQADFKKHF- | -DLEEK-A--- | -PLQ- | -FSKDTYDEDLEN | 278 |
| WP_049538452 | 213 | FSDK-ISKSAKRERVLKL-F-PD | EKSTGLFSEFLKLIVGNQADFKKHF- | -DLEEK-A--- | -PLQ- | -FSKDTYDEDLEN | 278 |
| WP_049549711 | 213 | FTDK-ISKSAKRERVLKL-F-PD | EKSTGLFSEFLKLIVGNQADFKKHF- | -DLGEK-A--- | -PLQ- | -FSKDTYDEDLEN | 278 |
| WP_007896501 | 214 | LTAK-TSKSKRLESLISE-F-PG | QKKNGLFGNLLALALGLRPNFKSNF- | -GLSED-A--- | -KLQ- | -ITKDTYEEELDN | 279 |
| EFR44625 | 166 | LTAK-TSKSKRLESLISE-F-PG | QKKNGLFGNLLALALGLRPNFKSNF- | -GLSED-A--- | -KLQ- | -ITKDTYEEELDN | 231 |
| WP_002897477 | 212 | FTDK-ISKSAKRERVLKL-F-PD | EKSTGLFSEFLKLIVGNQADFKKHF- | -DLEEK-A--- | -PLQ- | -FSKDTYDEELEN | 277 |
| WP_002906454 | 213 | FTDK-ISKSTKRERVLKL-F-SD | EKSTGLFSEFLKLIVGNQADFKKHF- | -DLEEK-A--- | -PLQ- | -FSKDTYDEELEN | 278 |
| WP_009729476 | 213 | FTDK-ISKSAKRERVLKL-F-PD | EKSTGLFSEFLKLIVGNQADFKKHF- | -DLEEK-A--- | -PLQ- | -FSRDTYDEDLEN | 278 |
| CQR24647 | 212 | ITAK-ISKSRKVEAVLEQ-F-PD | QKKNSFFGNMVSLVFGLMPNEKSNF- | -ELDED-A--- | -KLQ- | -FSRDSYDEDLEN | 277 |
| WP_000066813 | 213 | FTDK-ISKSTKRERVLKL-F-PD | EKSTGLFSEFLKLIVGNQADFKKHF- | -DLEEK-A--- | -PLQ- | -FSKDTYDEDLEN | 278 |
| WP_009754323 | 213 | FTGK-ISKSVKREHVLKL-F-PD | EKSTGLFSEFLKLIVGNQADFKKHF- | -DLGEK-A--- | -SLQ- | -FSKDTYDEDLEN | 278 |
| WP_044674937 | 212 | LVEK-VSKSRRLENILHY-F-PN | EKKNGLFGNLLALALGLQPNEKTNF- | -ELAED-A--- | -KIQ- | -FSKETYEEDLEE | 277 |
| WP_044676715 | 212 | LVEK-VSKSRRLENILHY-F-PN | EKKNGLFGNFLTLALGLQPNEKTNF- | -ELAED-A--- | -KIQ- | -FSKETYEEDLEE | 277 |
| WP_044680361 | 212 | LVEK-VSKSRRLENILHY-F-PN | EKKNGLFGNFLALALGLQPNEKTNF- | -ELAED-A--- | -KIQ- | -FSKETYEEDLEE | 277 |
| WP_044681799 | 212 | LVEK-VSKSRRLENILHY-F-PN | EKKNGLFGNFLALALGLQPNEKTNF- | -ELAED-A--- | -KIQ- | -FSKETYEEDLEE | 277 |
| WP_049533112 | 212 | LTEK-VSKSRRLENLIAH-Y-PA | EKKNTLFGNLIALSLGLQPNEKTNF- | -QLSED-A--- | -KLQ- | -FSKDTYDEDLEG | 277 |
| WP_029090905 | 172 | LLDRmMNRSSKVKFLIEL | -TG | KQDKPLLKELFNLIVGLKAKPASIFe- | --QENIAtiveTM-nMSTEQVQLDLLT | 243 |
| WP_006506696 | 211 | LKKP-LSKKAKVDEVMTL-IaPE | KDYKSAFKELVTGIAGNKMNVTKMIIcEPIKQ-Gds- | -EIK1kFSDSNYDDQFSE | | | 283 |
| AIT42264 | 212 | LSAR-LSKSRRLENLIAQ-L-PG | EKKNGLFGNLIALSLGLTPNEKSNF- | -DIAED-A--- | -KLQ- | -LSKDTYDDDLDN | 277 |
| WP_034440723 | 218 | FKQD-ISRSKKLDQAIAL-F-QG | -KRQSLFGIFLTLIVGNKANFQKIF- | -NLEDD--- | -iKLD- | -iKEEDYDENLEE | 283 |
| AKQ21048 | 212 | LSAR-LSKSRRLENLIAQ-L-PG | EKKNGLFGNLIALSLGLTPNEKSNF- | -DIAED-A--- | -KLQ- | -LSKDTYDDDLDN | 277 |
| WP_004636532 | 211 | LSSK-QSRSRKHEQIMAL-F-PN | ENKLGNFGRFMMLIVGNTSNFKPVF- | -DLDDE-Y--- | -KLK- | -LSDETYEEDLDT | 276 |
| WP_002378009 | 218 | LTEK-ASRTKKSSEKVLQQ-F-PQ | EKANGLFGQFLKLMVGNKADFKKVF- | -GLEEE-A--- | -KI-- | -tYASESYEEDLEG | 283 |
| WP_002407324 | 218 | LTEK-ASRTKKSSEKVLQQ-F-PQ | EKANGLFGQFLKLMVGNKADFKKVF- | -GLEEE-A--- | -KI-- | -tYASESYEEDLEG | 283 |
| WP_002413717 | 169 | LTEK-ASRTKKSSEKVLQQ-F-PQ | EKANGLFGQFLKLMVGNKADFKKVF- | -GLEEE-A--- | -KI-- | -tYASESYEEDLEG | 234 |
| EM575795 | 1 | --- | --- | -MDEE-A--- | --- | -LSKESYEEELES | 20 |
| WP_002373311 | 218 | LTEK-ASRTKKSSEKVLQQ-F-PQ | EKANGLFGQFLKLMVGNKADFKKVF- | -GLEEE-A--- | -KI-- | -tYASESYEEDLEG | 283 |
| WP_010818269 | 218 | LTEK-ASRTKKSSEKVLQQ-F-PQ | EKANGLFGQFLKLMVGNKADFKKVF- | -GLEEE-A--- | -KIKi | -tYASESYEEDLEG | 285 |
| WP_010824395 | 218 | LTEK-ASRTKKSSEKVLQQ-F-PQ | EKANGLFGQFLKLMVGNKADFKKVF- | -GLEEE-A--- | -KI-- | -tYASESYEEDLEG | 283 |
| WP_016622645 | 218 | LTEK-ASRTKKSSEKVLQQ-F-PQ | EKANGLFGQFLKLMVGNKADFKKVF- | -GLEEE-A--- | -KI-- | -tYASESYEEDLEG | 283 |
| WP_033624816 | 218 | LTEK-ASRTKKSSEKVLQQ-F-PQ | EKANGLFGQFLKLMVGNKADFKKVF- | -GLEEE-A--- | -KI-- | -tYASESYEEDLEG | 283 |
| WP_033625576 | 218 | LTEK-ASRTKKSSEKVLQQ-F-PQ | EKANGLFGQFLKLMVGNKADFKKVF- | -GLEEE-A--- | -KI-- | -tYASESYEEDLEG | 283 |
| WP_033789179 | 218 | LTEK-ASRTKKSSEKVLQQ-F-PQ | EKANGLFGQFLKLMVGNKADFKKVF- | -GLEEE-A--- | -KI-- | -tYASESYEEDLEG | 283 |
| WP_002310644 | 217 | FTEK-MSKTKKAETLLKY-F-PH | EKSNGYLSQFIKLMVGNQGNFKNVF- | -GL-EE-A--- | -KLQ- | -FSKETYEEDLEE | 281 |
| WP_002112694 | 218 | LTEK-ASRTKKSSEKVLQQ-F-PQ | EKANGLFGQFLKLMVGNKADFKKVF- | -GLEEE-A--- | -KLQ- | -FSKETYEEDLEE | 283 |
| WP_002314015 | 217 | FTEK-MSKTKKAETLLKY-F-PH | EKSNGYLSQFIKLMVGNQGNFKNVF- | -GL-EEeA--- | -KLQ- | -FSKETYEEDLEE | 282 |
| WP_002320716 | 217 | FTEK-MSKTKKAETLLKY-F-PH | EKSNGYLSQFIKLMVGNQGNFKNVF- | -GL-EEeA--- | -KLQ- | -FSKETYEEDLEE | 282 |
| WP_002330729 | 217 | FTEK-MSKTKKAETLLKY-F-PH | EKSNGYLSQFIKLMVGNQGNFKNVF- | -GL-EE-A--- | -KLQ- | -FSKETYEEDLEE | 281 |
| WP_002335161 | 217 | FTEK-MSKTKKAETLLKY-F-PH | EKSNGYLSQFIKLMVGNQGNFKNVF- | -GL-EEeA--- | -KLQ- | -FSKETYEEDLEE | 282 |
| WP_002345439 | 217 | FTEK-MSKTKKAETLLKY-F-PH | EKSNGYLSQFIKLMVGNQGNFKNVF- | -GL-EEeA--- | -KLQ- | -FSKETYEEDLEE | 282 |
| WP_034867970 | 210 | LDTK-LSKTKKVEEILKY-Y-PT | EKINSFFAQCLKLIVGNQANFKRIF- | -DLEAE-V--- | -KLQ- | -FSKETYEEDLES | 275 |
| WP_047937432 | 217 | FTEK-MSKTKKAETLLKY-F-PH | EKSNGYLSQFIKLMVGNQGNFKNVF- | -GL-EEeA--- | -KLQ- | -FSKETYEEDLEE | 282 |
| WP_010720994 | 210 | LTDK-LSKTKKVEEILKY-Y-PT | EKINSFFAQCLKLIVGNQANFKRIF- | -DLEAE-V--- | -KLQ- | -FSKETYEEDLES | 275 |
| WP_010737004 | 210 | LDTK-LSKTKKVEEILKY-Y-PT | EKINSFFAQCLKLIVGNQANFKRIF- | -DLEAE-V--- | -KLQ- | -FSKETYEEDLES | 275 |
| WP_034700478 | 210 | LDTK-LSKTKKVEEILKY-Y-PT | EKINSFFAQCLKLIVGNQANFKRIF- | -DLEAE-V--- | -KLQ- | -FSKETYEEDLES | 275 |
| WP_037200903 | 215 | LTQQ-LSKSERADNVLKL-F-PD | EKGTGIFAQFIKLIVGNQGNFKNVF- | -QLEED--- | -qKLQ- | -LSTDDYEENIEN | 280 |
| WP_023519017 | 210 | LTER-LSKAKRVEKVLAY-Y-PS | EKSTGNFAQFLKLMVGNQANFKKTF- | -DLEEE-M--- | -KLN- | -FTRDCYEDLNE | 275 |
| WP_010770040 | 213 | FSEK-VSRARKVEAILSV-Y-SE | EKSTGTLAQFLKLMVGNQRFKKTF- | -DLEEED-G-- | -IIQ- | -IPKEEYEEELET | 278 |
| WP_048604708 | 209 | FADK-VSRAKKAEGVLAL-F-PD | EKRNGTFDQFLKMIVGNQGNFKKTF- | -ELEED-A--- | -KLQ- | -FSKEEYDESLEA | 274 |
| WP_010750235 | 210 | LTDK-LSKSKKVEKILQY-Y-PK | EKTTGCLAQFLKLIVGNQGNFKQAF- | -HLDEE-V--- | -KIQ- | -ISKETYEEDLEK | 275 |

-continued

```
AII16583           251 LSAR-LSKSRRLENLIAQ-L-PG EKKNGLFGNLIALSLGLTPNEKSNF--DLAED-A---KLQ--LSKDTYDDDLDN                            316
WP_029073316       216 LKEP-LSKKHKADKAFAL-FdTT KDNKAAYKELCAALAGNKFNVTKMLkeaELHD-EdekDISfkFSDATFDDAFVE                            289
WP_031589969       216 LKEP-LSKKHKAEKAFAL-FdTT KDNKAAYKELCAALAGNKFNVTKMLkeaELHD-EdekDISfkFSDATFDDAFVE                            289
KDA45870           210 FKDNt FSKTKKSEELLKL---SG -KKNQLAHQLFKMVGNMGSFKKVL--GTDEE---hKLS-FGKDTYEDDLND                              275
WP_039099354       207 LLDNhQSASNRQRQALLLiYtPS KQNKAIATELLKEVINLILGNVAHLNTIFktSLTKDeE--KLS-FSGKDIESKLDD                          285
AKP02966           209 LIGR-GNATQKSSNILNN-F--T KETKKLLKEVINLILGNVAHLNTIFktSLTKDeE--KLS-FSGKDIESKLDD                              278
WP_010991369       218 LVEK-VTRKEKLERILKL-Y-PG EKSAGMFAQFISLIVGSKGNFQKPF--DLIEK-S---DIE--CAKDSYEEDLES                            283
WP_033838504       218 LVEK-VTRKEKERILKL-Y-PG EKSAGMFAQFISLIVGSKGNFQKPF--DLIEK-S---DIE--CAKDSYEEDLES                             283
EHN60060           221 LVEK-VTRKEKLERILKL-Y-PG EKSAGMFAQFISLIVGSKGNFQKPF--DLIEK-S---DIE--CAKDSYEEDLES                            286
EFR89594             1 ------------------- --- ---------------------------------------  ---CAKDSYEEDLES                          52
WP_038409211       218 LSEK-LTRREKLDKILKL-Y-TG EKSTGMFARFINLIGSKGDFKKVF--DLDEK-A---EIE--CAKDTYEEDLEA                             283
EFR95520             1 ------LKLI--------- --- ---------------------------------------  ---------------                           1
WP_003723650       218 LAGK-FTRREKFERILQL-Y-PG EKSTGMFAQFISLIVGSKGNFQKVF--DLIEK-T---DIE--CAKDSYEEDLET                            283
WP_003727705       218 LAGK-FTRREKFERILRL-Y-PG EKSTGMFAQFISLIVGNKGNFQKVF--NLVEK-T---DIE--CAKDSYEEDLEA                            283
WP_003730785       218 LAGK-FTRREKFERILRL-Y-PG EKSTGMFAQFISLIVGNKGNFQKVF--NLVEK-T---DIE--CAKDSYEEDLEA                            283
WP_003733029       218 LAEK-FTRKDKLDKILSL-Y-PG EKTTGVFAQFVNIIVGSTGKEKKHF--NLHEK-K---DIN--CAEDTYDTDLES                            283
WP_003739838       218 LAGK-FTRREKFERILQL-Y-PG EKSTGMFAQFISLIVGSKGNFQKVF--DLIVEK-T---DIE--CAKDSYEEDLEA                           283
WP_014601172       218 LAGK-FTRREKFERILQL-Y-PG EKSTGMFAQFISLIVGSKGNFQKVF--DLIEK-T---DIE--CAKDSYEEDLEA                            283
WP_023548323       218 LAGK-FTRREKFERILQL-Y-PG EKSTGMFAQFISLIVGSKGNFQKVF--DLIEK-T---DIE--CAKDSYEEDLEA                            283
WP_031665337       218 LAGK-FTRREKFERILQL-Y-PG EKSTGMFAQFISLIVGSKGNFQKVF--DLIEK-T---DIE--CAKDSYEEDLET                            283
WP_031669209       218 LAEK-FTRKDKLDKILSL-Y-PG EKTTGVFAQFVNI IVGSTGKEKKHF--NLHEK-K---DIN--CAEDTYDTDLES                           283
WP_033920898       218 LARK-FTRREKFERILQL-Y-PG EKSTGMFAQFISLIVGSKGNFQKVF--DLIEK-T---DIE--CAKDSYEEDLEA                            283
AKI42028           221 LARK-FTRREKFERILQL-Y-PG EKSTGMFAQFISLIVGSKGNFQKVF--DLIEK-T---DIE--CAKDSYEEDLEA                            286
AKI50529           221 LARK-FTRREKFERILQL-Y-PG EKSTGMFAQFISLIVGSKGNFQKVF--DLIEK-T---DIE--CAKDSYEEDLET                            286
EFR83390             1 ------------------- --- ---------------------------------------  ---------------                           1
WP_046323366       218 FSEK-LTKREKLDKILNL-Y-PN EKSTDLFAQFISLIIGSGNEKKPF--NLTEK-T---DIE--CAKDSYEEDLEV                              283
AKE81011           228 LSAR-LSKSRRLENLIAQ-L-PG EKKNGLEGNLIALSLGLTPNEKSNF--DLAED-A---KLQ--LSKDTYDDDLDN                            293
CUO82355           215 LKKP-LSKKAKVDEVMAL-IsPE KEFKSAYKELVTGIAGNKMNVTKMI1cESIKQ-Gds-EIK1kFSDSNYDDQFSE                             287
WP_033162887       216 LSKI-YQRSKKADDLLKI-MnPT KEBEKAAYKEFTKALVGLKFNISKMI1aQEVKK-Gdt-DIV1eFSNANYDSTIDE                            288
AGZ01981           245 LSAR-LSKSRRLENLIAQ-L-PG EKKNGLEGNLIALSLGLTPNEKSNF--DLAED-A---KLQ--LSKDTYDDDLDN                            310
AKA60242           212 LSAR-LSKSRRLENLIAQ-L-PG EKKNGLEGNLIALSLGLTPNEKSNF--DLIE--A---KLQ--LSKDTYDDDLDN                             277
AKS40380           216 LSAR-LSKSRRLENLIAQ-L-PG EKKNGLEGNLIALSLGLTPNEKSNF--DLAED-A---KLQ--LSKDTYDDDLDN                            281
4UN5_B             278 LLAQIGDQYADLFLA[mask]NLSDAILLSGILTVNTEITKAPLSASMIKRYDEHHQDLTLLKALVRQQ-LPEKYKEIFFDQSK                        356
WP_010922251       279 LLGKIGDDYADLFTSAKNLYDAILLSGILTVDDNSTKAPLSASMIKRYVEHHEDLEKLKEFIKAN-KSELYHDIFKDKNK                           357
WP_039695303       278 LLGQIGDDFTDLFVSAKKLYDAILLSGILTVDPSTKAPLSASMIERYENHQNDLAALKQFIKNN-LPEKYDEVFSDQSK                           356
WP_045635197       158 ------------------- --- ---------------------------------LERLKKDG-----EVR----                             168
5AXW_A               1 ---------------------- ------LSASMIKRYDEHHQDLTLLKALVRQQ-LPEKYKEIFFDQSK                                     40
WP_009880683       278 LLAQIGDQYADLFLAAKNLSDAILLSDILRVNTEITKAPLSASMIKRYDEHHQDLTLLKALVRQQ-LPEKYKEIFFDQSK                           356
WP_010922251       278 LLAQIGDQYADLFLAAKNLSDAILLSDILRVNSEITKAPLSASMIKRYDEHHQDLTLLKALVRQQ-LPEKYKEIFFDQSK                           356
WP_011054416       278 LLAQIGDQYADLFLAAKNLSDATLLSDILRVNSEITKAPLSASMIKRYDEHHQDLTLLKALVRQQ-LPEKYKEIFFDQSK                           356
WP_011284745       278 LLAQIGDQYADLFLAAKNLSDAILLSDILRVNSEITKAPLSASMIKRYDEHHQDLTLLKALVRQQ-LPEKYKEIFFDQSK                           356
WP_011285506       278 LLAQIGDQYADLFLAAKNLSDAILLSDILRVNSEITKAPLSASMIKRYDEHHQDLTLLKALVRQQ-LPEKYKEIFFDQSK                           356
WP_011527619       278 LLAQIGDQYADLFLAAKNLSDAILLSDILRLNSEITKAPLSASMIKRYDEHHQDLTLLKALVRQQ-LPEKYKEIFFDQSK                           356
WP_012560673       278 LLAQIGDQYADLFLAAKNLSDAILLSDILRVNSEITKAPLSASMIKRYDEHHQDLTLLKALVRQQ-LPEKYKEIFFDQSK                           356
WP_014407541       278 LLAQIGDQYADLFLAAKNLSDAILLSDILRVNSEITKAPLSASMIKRYDEHHQDLTLLKALVRQQ-LPEKYKEIFFDQSK                           356
WP_020905136       278 LLAQIGDQYADLFLAAKNLSDAILLSDILRLNSEITKAPLSASMIKRYDEHHQDLTLLKALVRQQ-LPEKYKEIFFDQSK                           356
WP_023080005       278 LLAQIGDQYADLFLAAKNLSDAILLSDILRVNSEITKAPLSASMIKRYDEHHQDLTLLKALVRQQ-LPEKYKEIFFDQSK                           356
WP_023610282       278 LLAQIGDQYADLFLAAKNLSDAILLSDILRVNSEITKASLSASMIKRYDEHHQDLTLLKALVRQQ-LPEKYKEIFFDQSK                           356
WP_030125963       278 LLAQIGDQYADLFLAAKNLSDAILLSDILRVNSEITKAPLSASMIKRYDEHHQDLTLLKALVRQQ-LPEKYKEIFFDQSK                           356
WP_030126706       278 LLAQIGDQYADLFLAAKNLSDATLLSDILRVNTEITKAPLSASMIKRYDEHHQDLTLLKALVRQQ-LPEKYKEIFFDQSK                           356
WP_031488318       278 LLAQIGDQYADLFLAAKNLSDAILLSDILRVNSEITKAPLSASMIKRYDEHHQDLTLLKALVRQQ-LPEKYKEIFFDQSK                           356
WP_032460140       278 LLAQIGDQYADLFLAAKNLSDAILLSDILRVNSEITKAPLSASMIKRYDEHHQDLTLLKALVRQQ-LPEKYKEIFFDQSK                           356
WP_032461047       278 LLAQIGDQYADLFLAAKNLSDAILLSDILRVNTEITKAPLSASMIKRYDEHHQDLTLLKALVRQQ-LPEKYKEIFFDQSK                           356
```

```
WP_032462016    278  LLAQIGDQYADLFLAAKNLSDAILLSDILRVNTEITKAPLSASMIKRYDEHHQDLTLLKALVRQQ-LPEKYKEIFFDQSK  356
WP_032462936    278  LLAQIGDQYADLFLAAKNLSDAILLSDILRVNSEITKAPLSASMIKRYDEHHQDLTLLKALVRQQ-LPEKYKEIFFDQSK  356
WP_032464890    278  LLAQIGDQYADLFLAAKNLSDAILLSDILRLNSEITKAPLSASMIKRYDEHHQDLTLLKALVRQQ-LPEKYKEIFFDQSK  356
WP_033888930    103  LLAQIGDQYADLFLAAKNLSDAILLSDILRVNSEITKAPLSASMIKRYDEHHQDLTLLKALVRQQ-LPEKYKEIFFDQSK  181
WP_038431314    278  LLAQIGDQYADLFLAAKNLSDAILLSDATLSDILRVNSEITKAPLSASMIKRYDEHHQDLTLLKALVRQQ-LPEKYKEIFFDQSK  356
WP_038432938    278  LLAQIGDQYADLFLAAKNLSDAILLSDILRVNSEITKAPLSASMIKRYDEHHQDLTLLKALVRQQ-LPEKYKEIFFDQSK  356
WP_038434062    278  LLAQIGDQYADLFLAAKNLSDAILLSDILRVNSEITKAPLSASMIKRYDEHHQDLTLLKALVRQQ-LPEKYKEIFFDQSK  356
BAQ51233        189  LLAQIGDQYADLFLAAKNLSDAILLSDILRVNTEITKAPLSASMIKRYDEHHQDLTLLKALVRQQ-LPEKYKEIFFDQSK  267
KGE60162             ----------------------------------------------------------------------------
KGE60856             ----------------------------------------------------------------------------
WP_002989955    278  LLAQIGDQYADLFLAAKNLSDAILLSDILRLNSEITKAPLSASMIKRYDEHHQDLTLLKALVRQQ-LPEKYKEIFFDQSK  356
WP_003030002    278  LLGEIGDEYADLFSAAKNLYDAILLSGILTVDDNSTKAPLSASMVKRYEEHQKDLKKLKDFIKVN-APDQYNAIFKDKNK  356
WP_003065552    281  LLGKIGDDYADLFTSAKNLYDAILLSGILIVDDNSTKAPLSASMIKRYVEHQEDLEKLKEFIKAN-KSELYHDIFKDKNK  359
WP_001040076    279  LLGQIGDEFADLFSAAKKLYDSVLLSGILTVIDLSTKAPLSASMIQRYDEHREDLKQLKQFVKAS-LPEKYQEIFADSSK  357
WP_001040078    279  LLGQIGDEFADLFSAAKKLYDSVLLSGILTVIDLSTKAPLSASMIQRYDEHREDLKQLKQFVKAS-LPEKYQEIFADSSK  357
WP_001040080    279  LLGQIGDEFADLFSAAKKLYDSVLLSGILTVIDLSTKAPLSASMIQRYDEHREDLKQLKQFVKAS-LPEKYQEIFADSSK  357
WP_001040081    279  LLGQIGDEFADLFSAAKKLYDSVLLSGILTVIDLSTKAPLSASMIQRYDEHREDLKQLKQFVKAS-LPEKYQEIFADSSK  357
WP_001040083    279  LLGQIGDEFADLFSAAKKLYDSVLLSGILTVIDLSTKAPLSASMIQRYDEHREDLKQLKQFVKAS-LPEKYQEIFADSSK  357
WP_001040085    279  LLGQIGDEFADLFSAAKKLYDSVLLSGILTVIDLSTKAPLSASMIQRYDEHREDLKQLKQFVKAS-LPEKYQEIFADSSK  357
WP_001040087    279  LLGQIGDEFADLFSAAKKLYDSVLLSGILTVIDLSTKAPLSASMIQRYDEHREDLKQLKQFVKAS-LPEKYQEIFADSSK  357
WP_001040088    279  LLGQIGDEFADLFSAAKKLYDSVLLSGILTVIDLSTKAPLSASMIQRYDEHREDLKQLKQFVKAS-LPEKYQEIFADSSK  357
WP_001040089    279  LLGQIGDEFADLFSAAKKLYDSVLLSGILTVIDLSTKAPLSASMIQRYDEHREDLKQLKQFVKAS-LPEKYQEIFADSSK  357
WP_001040090    279  LLGQIGDEFADLFSAAKKLYDSVLLSGILTVIDLSTKAPLSASMIQRYDEHREDLKQLKQFVKAS-LPEKYQEIFADSSK  357
WP_001040091    279  LLRQIGDEFADLFSAAKKLYDSVLLSGILTVIDLSTKAPLSASMIQRYDEHREDLKQLKQFVKAS-LPEKYQEIFADSSK  357
WP_001040092    279  LLGQIGDEFADLFSAAKKLYDSVLLSGILTVIDLSTKAPLSASMIQRYDEHREDLKQLKQFVKAS-LPEKYQEIFADSSK  357
WP_001040094    279  LLGQIGDEFADLFSAAKKLYDSVLLSGILTVIDLSTKAPLSASMIQRYDEHREDLKQLKQFVKAS-LPEKYQEIFADSSK  357
WP_001040095    279  LLGQIGDEFADLFSAAKKLYDSVLLSGILTVIDLSTKAPLSASMIQRYDEHREDLKQLKQFVKAS-LPEKYQEIFADSSK  357
WP_001040096    279  LLGQIGDEFADLFSAAKKLYDSVLLSGILTVIDLSTKAPLSASMIQHYDEHREDLKQLKQFVKAS-LPEKYQEIFADSSK  357
WP_001040097    279  LLGQIGDEFADLFSAAKKLYDSVLLSGILTVIDLSTKAPLSA VMIQRYDEHREDLKQLKQFVKAS-LPEKYQEIFADSSK  357
WP_001040098    279  LLGQIGDEFADLFSAAKKLYDSVLLSGILTVIDLSTKAPLSASMIQRYDEHREDLKQLKQFVKAS-LPEKYQEIFADSSK  357
WP_001040099    279  LLGQIGDEFADLFSAAKKLYDSVLLSGILTVIDLSTKAPLSASMIQRYDEHREDLKQLKQFVKAS-LPEKYQEIFADSSK  357
WP_001040100    279  LLGQIGDEFADLFSAAKKLYDSVLLSGILTVIDLSTKAPLSASMIQRYDEHREDLKQLKQFVKAS-LPEKYQEIFADSSK  357
WP_001040104    279  LLGQIGDEFADLFSAAKKLYDSVLLSGILTVIDLSTKAPLSASMIQRYDEHREDLKQLKQFVKAS-LPEKYQEIFADSSK  357
WP_001040105    279  LLGQIGDEFADLFSAAKKLYDSVLLSGILTVIDLSTKAPLSASMIQRYDEHREDLKQLKQFVKAS-LPEKYQEIFADSSK  357
WP_001040106    279  LLGQIGDEFADLFSVAKKLYDSVLLSGILTVIDLSTKAPLSASMIQRYDEHREDLKQLKQFVKAS-LPEKYQEIFTDSSK  357
WP_001040107    279  LLGQIGDEFADLFSVAKKLYDSVLLSGILTVIDLSTKAPLSASMIQRYDEHREDLKQLKQFVKAS-LPEKYQEIFTDSSK  357
WP_001040108    279  LLGQIGDEFADLFSVAKKLYDSVLLSGILTVIDLSTKAPLSASMIQRYDEHREDLKQLKQFVKAS-LPEKYQEIFTDSSK  357
WP_001040109    279  LLGQIGDEFADLFSVAKKLYDSVLLSGILTVIDLSTKAPLSASMIQRYDEHREDLKQLKQFVKAS-LPEKYQEIFTDSSK  357
WP_001040110    279  LLGQIGDEFADLFSVAKKLYDSVLLSGILTVIDLSTKAPLSASMIQRYDEHREDLKQLKQFVKAS-LPEKYQEIFADSSK  357
WP_015058523    279  LLGQIGDEFADLFSAAKKLYDSVLLSGILTVIDLSTKAPLSASMIQRYDEHREDLKQLKQFVKAS-LPEKYQEIFADSSK  357
WP_017643650    279  LLGQIGDEFADLFSAAKKLYDSVLLSGILTVIDLSTKAPLSASMIQRYDEHREDLKQLKQFVKAS-LPEKYQEIFADSSK  357
WP_017647151    279  LLGQIGDEFADLFSAAKKLYDSVLLSGILTVIDLSTKAPLSASMIQRYDEHREDLKQLKQFVKAS-LPEKYQEIFTDSSK  357
WP_017648376    279  LLGQIGDEFADLFSVAKKLYDSVLLSGILTVALSTKAPLSASMIQRYDEHREDLKQLKQFVKAS-LPEKYQEIFTDSSK  357
WP_017649527    279  LLGQIGDEFADLFSAAKKLYDSVLLSGILTVIDLSTKAPLSASMIQRYDEHREDLKQLKQFVKAS-LPEKYQEIFTDSSK  357
WP_017771611    279  LLGQIGDEFADLFSAAKKLYDSVLLSGILTVIDLSTKAPLSASMIQRYDEHREDLKQLKQFVKAS-LPEKYQEIFTDSSK  357
WP_017771984    279  LLGQIGDEFADLFSVAKKLYDSVLLSGILTVIDLSTKAPLSASMIQRYDEHREDLKQLKQFVKAS-LPEKYQEIFTDSSK  357
CFQ25032        279  LLGQIGDEFADLFSAAKKLYDSVLLSGILTVIDLSTKASLSDSMIQRYDEHREDLKQLKQFVKAS-LPEKYQEIFADSSK  357
CFV16040        279  LLGQIGDEFADLFSAAKKLYDSVLLSGILTVIDLSTKAPLSASMIQRYDEHREDLKQLKQFVKAS-LPEKYQEIFADSSK  357
KLJ37842        279  LLGQIGDEFADLFSAAKKLYDSVLLSGILTVIDLSTKAPLSASMIQRYDEHREDLKQLKQFVKAS-LPEKYQEIFADSSK  357
KLJ72361        279  LLGQIGDEFADLFSAAKKLYDSVLLSGILTVIDLSTKAPLSASMIQRYDEHREDLKQLKQFVKAS-LPEKYQEIFTDSSK  357
KLL20707        279  LLGQIGDEFADLFSAAKKLYDSVLLSGILTVIDLSTKAPLSASMIQRYDEHREDLKQLKQFVKAS-LPEKYQEIFADSSK  357
KLL42645        279  LLGQIGDEFADLFSVAKKLYDSVLLSGILTVIDLSTKAPLSASMIQRYDEHREDLKQLKQFVKAS-LPEKYQEIFTDSSK  357
WP_047207273    279  LLGQIGDEFADLFSAAKKLYDSVLLSGILTVIDLSTKAPLSASMIQRYDEHREDLKQLKQFVKAS-LPEKYQEIFADSSK  357
```

```
-continued

WP_47209694       279  LLGQIGDEFADLFSAAKKLYDSVLLSGILTVDLSTKAPLSASMIQRYDEHREDLKQLKQFVKAS-LPEKYQEIFADSSK  357
WP_050198062      279  LLGQIGDEFADLFSAAKKLYDSVLLSGILTVIDLSTKAPLSASMIQRYDEHREDLKQLKQFVKAS-LPEKYQEIFADSSK  357
WP_050201642      279  LLGQIGDEFADLFSAAKKLYDSVLLSGILTVIDLSTKAPLSASMIQRYDEHREDLKQLKQFVKAS-LPEKYQEIFADSSK  357
WP_050204027      279  LLGQIGDEFADLFVAKKLYDSVLLSGILTVTDLSTKAPLSASMIQRYDEHREDLKQLKQFVKAS-LPEKYQEIFTDSSK  357
WP_050881965      279  LLGQIGDEFADLFSAAKKLYDSVLLSGILTVIDLSTKAPLSASMIQRYDEHREDLKQLKQFVKAS-LPEKYQEIFADSSK  357
WP_050886065      279  LLGQIGDEFADLFSAAKKLYDSVLLSGILTVIDLSTKAPLSASMIQRYDEHREDLKQLKQFVKAS-LPEKYQEIFADSSK  357
AHN30376          279  LLGQIGDEFADLFSAAKKLYDSVLLSGILTVIDLSTKAPLSASMIQRYDEHREDLKQLKQFVKAS-LPEKYQEIFADSSK  357
EA078426          279  LLGQIGDEFADLFSAAKKLYDSVLLSGILTVDLSTKAPLSASMIQRYDEHREDLKQLKQFVKAS-LPEKYQEIFADSSK   357
CCW42055          279  LLGQIGDEFADLFSAAKNLYDAILLSGILTVDLSTKAPLSASMVKRYEEHQKDLKKKPEDFIKVN-ALDQYNAIFKDKNK  357
WP_003041502      279  LLGEVGDEYADLFASAKNLYDAILLSGILTVDDNSTKAPLSASMVKRYEEHQKDLKKKPEDFIKVN-ALDQYNAIFKDKNK 356
WP_037593752      279  LLGEIGDEFADLFSAAKNLYDAILLSGILAVDDNTTKAPLSASMVKRYEEHQKDLKKKLDFIKVN-APDQYNAIFKDKNK  357
WP_049516684      279  LLGEIGDEYADLFASAKNLYDAILLSGILAVDDNTTKAPLSASMVKRYEEHQKDLKKKLDFIKVN-APAQYDDIFKDETK  357
GAD46167          278  LLGEIGDEYADLFASAKNLYDAILLSGILTVDDNSTKAPLSASMVKRYEEHQKDLKKKLDFIKVN-APDQYNAIFKDKNK  356
WP_018363470      279  LLGKIGDDYADLFTSSKNLYDAILLSGILTVDDNSEVTKAPLSASMIKRYDEHHQDLALLIKTLVRQQ-FPEKYAEIFKDDTK 357
WP_003043819      278  LLAQIGDQYADLFSAAKNLSDAILLSDILRSNSNEVTKAPLSASMIKRYDEHHQDLALLIKTLVRQQ-FPEKYAEIFKDDTK 356
WP_006269658      278  FLGEVGDDYADLFASAKNLYDAILLSGILTVDDNSTKAPLSASMIKRYDEHHQDLKKLKDFIKVN-APDQYNAIFKDKNK   356
WP_048800889      278  LLGKIGDDYADLFTSAKNLYDTILLSGILTVDDNSTKALLSASMIKRYDEHHQDLKKLKDFIKVN-APAQYDDIFKDETK   356
WP_012767106      278  LLAQIGDQYADLFLAAKNLSDAILLSDILRVNSEITKAPLSASMIKRYDEHHQDLTLLKALVRQQ-LPEKYKEIFPDQSK   356
WP_014612333      278  LLAQIGNQYADLFLAAKNLSDAILLSDILRVNSEITKAPLSASMIKRYDEHHQDLTLLKALVRQQ-LPEKYKEIFPDQSK   356
WP_015017095      278  LLAQIGDQYADLFLAAKNLSDAILLSDILRVNSEITKAPLSASMIKRYDEHHQDLTLLKALVRQQ-LPEKYKEIFPDQSK   356
WP_015057649      278  LLAQIGDQYADLFLAAKNLSDAILLSDILRVNSEITKAPLSASMIKRYDEHHQDLTLLKALVRQQ-LPEKYKEIFPDQSK   356
WP_048327215      278  LLAQIGDQYADLFLAAKNLSDAILLSDILTESDEITKAPLSASMIKRYDEHHQDLVTLKTLIKDQ-LPEKYQEIFLDKTK   356
WP_049519324      278  LLAQIGDQYADLFLAAKNLSDAILLSDILTESDEITKAPLSASMIKRYREHHKDLVTLKTLIKDQ-LPEKYQEIFLDKTK   356
WP_012515931      278  LLAQIGDQYADLFLAAKNLSDAILLSDILTESDEITRAPLSASMVKRYREHHKDLVTLKTLIKDQ-LPEKYQEIFLDKTK   356
WP_021320964      278  LLAQIGDQYADLFLAAKNLSDAILLSDILTESDEITKAPLSASMIKRYREHHKDLVTLKTLIKDQ-LPEKYQEIFLDKTK   356
WP_037581760      278  LLAQIGDQYADLFLAAKNLSDAILLSDILTESDEITKAPLSASMIKRYREHHKDLVTLKTLIKDQ-LPEKYQEIFLDKTK   356
WP_044232481      279  LLGKIGDEYADLFTSAKNLYDAILLSGILTVDDNSTKAPLSASMIKRYEEHHEDLEKLKFTKIKVN-NFDKYHEIFKDKSK  357
WP_009854540      279  LLGKIGDEYADLFSAKNLYDAILLSGILTVDDNSTKAPLSASMIKRYVEHHEDLEKLKEFIKAN-KSELYHDIFKDKNK   357
WP_012962174      279  LIGKIGDEYADLFTSAKNLYDAILLSGILTVADNTTKAPLSASMIKRYNEHQVDLKKLKEFIKNN-ASDKYDEIFNDKDK  357
WP_039695303      279  LLGKIGDQYADLFSAKNLYDAILLSGILTVDDNSTKAPLSASMIKRYVEHHEDLEKLKEFIKAN-KSELYHDIFKDKNK   357
WP_014334983      278  LLGKVGDDYADLFSAKNLYDAILLSGILTVKGASTKAPLSASMVKRYEEHQQDLALLKNLVLKKQ-KLKLYHDIFKDKTK  356
WP_003099269      278  LLAQIGDQYADLFIAAKKLSDAILLSDIITVKGASTKAPLSASMVQRYEEHQQDLALLKNLVKKQ-IPEKYKEIFDNKEK  356
AHY15608          278  LLAQIGDQYADLFIAAKKLSDAILLSDIITVKGASTKAPLSASMVQRYEEHQQDLALLKNLVKKQ-IPEKYKEIFDNKEK   356
AHY17476          278  LLAQIGDQYADLFIAAKKLSDAILLSDIITVKGASTKAPLSASMVQRYEEHQQDLALLKNLVKKQ-IPEKYKEIFDNKEK   356
ESR09100          -----------------------------------------------------------------------------------
AGM98575          278  LLAQIGDQYADLFIAAKKLSDAILLSDIITVKGASTKAPLSASMVQRYEEHQQDLALLKNLVKKQ-IPEKYKEIFDNKEK   356
ALF27331          278  LLAQIGNYAELFLSAKKLYDSILLSGILTVTDVSTKAPLSASMIQRYNEHQMDLAQLKQFIRQK-LSDKYNEVFSDVSK    356
WP_018372492      276  LLSKIDEEYAALFDLAKKVYDAVLLSNILTVKEKNTKAPLSASMIKRYEEHKDDLKAPKRFPRER-LPEKYETMFKDLTK   354
WP_045618028      279  LIVQIGDDFADLFLVAKKLYDAILLSGILTVDPSTKAPLSASMIDRYENHQKDLAALKQFIKTN-LPEKYDEVFSDQSK    357
WP_045635197      278  LLGQIGDDFTDLFVSAKKLYDAILLSGILTVDGTKAPLSASMIERYENHQNDLAALKQFIKNN-LPEKYDEVFSDQSK     356
WP_022263549      278  LLAQIGDNYAELFLSAKKLYDSILLSGILTVTDVGTKAPLSASMIQRYNEHQMDLAQLKQFIRQK-LPEKYNEVFSDVSK   356
WP_022263887      278  LLGKIGDDYADLFTLAKNLYDAILLSGILTVTADSSTKAPLSASMIQRYAEHHEDLEKLKEFIKAN-KPELYHDIFKDETK  356
WP_022264920      278  LLGKIGDDYADLFLSAKKLYDSILLSGILTVTDVSTKAPLSASMIQRYNEHQMDLAQLKQFIRQK-LSDKYNEVFSDVSK   356
WP_022269043      278  LLAQIGDNYAELFLSAKKLYDSILLSGILTVTDVSTKAPLSASMIQRYNEHQMDLAQLKQFIRQK-LSDKYNEVFSDVSK   356
WP_022269448      278  LLAQIGDNYAELFLSAKKLYDSILLSGILTVTDVSTKAPLSASMIQRYNEHQMDLAQLKQFIRQK-LSDKYNEVFSDVSK   356
WP_002271977      278  LLGKIGDDYADLFTLAKNLYDAILLSGILTADDSSTKAPLSASMIQRYNEHQMDLAQLKQFIRQK-LSDKYNEVFSDVSK   356
WP_022272766      278  LLAQIGDNYAELFLSAKKLYDSILLSGILTVTDVSTKAPLSASMIQRYNEHQMDLAQLKQFIRQK-LSDKYNEVFSDVSK   356
WP_022273241      278  LLAQIGDNYAELFLSAKKLYDSILLSGILTVTDVSTKAPLSASMIQRYNEHQMDLAQLKQFIRQK-LSDKYNEVFSDVSK   356
WP_022275430      278  LLTQIGDNYAELFLSAKKLYDSILLSGILTVTDVSTKAPLSASMIQRYNEHQMDLAQLKQFIRQK-LSDKYNEVFSDVSK   356
WP_002276448      278  LLAQIGDNYAELFLSAKKLYDSILLSGILTVTDVSTKAPLSASMIQRYNEHQMDLAQLKQFIRQK-LSDKYNEVFSDVSK   356
WP_022277050      278  LLGKIGDNYADLFTLAKNLYDAILLSGILTADDSSTKAPLSASMIKRYAEHHEDLEKLKEFIKAN-KPELYHDIFKDETK   356
WP_022773364      278  LLAQIGDNYAELFLSAKKLYDSILLSGILTVTDVSTKAPLSASMIQRYNEHQMDLAQLKQFIRQK-LSDKYNEVFSDVSK   356
WP_022279025      278  LLAQIGDNYAELFLSAKKLYDSILLSGILTADDSSTKAPLSASMIQRYNEHQMDLAQLKQFIRQK-LSDKYNEVFSDVSK   356
```

| | | | |
|---|---|---|---|
| WP_002279859 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002280230 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002281696 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002282247 | 278 | LLGKIGDDYADLFTLAKNLYDAILLSGIILTADDSSTKAPLSASMIKRYAEHHEDLEKLKEFIKAN-KPELYHDIFKDETK | 356 |
| WP_002283906 | 278 | LLAQIGDNYAELFLSAKKLYDSILLSGILTVDGTKAPLSASMIQRYNEHQMDLAQLKQFIRQK-LSDKYNEVFSDVSK | 356 |
| WP_002283846 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002287255 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002288990 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002289641 | 278 | LLAQIGDNYAELFLSAKKLYDSILLSGILTVTDVSTKAPLSASMIQRYNEHQMDLTQLKQFIRQK-LSDKYNEVFSDVSK | 356 |
| WP_002290427 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002295753 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002296423 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002304487 | 278 | LLGEIGDEYADLFRASAKNLYDAILLSGILAVDNTTKAPLSASMVKRYKEHKEELAAFKRFIKEK-LPKKYEEIFKDDTK | 356 |
| WP_002305844 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002307203 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002310390 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_002352408 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_012997688 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_014677909 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_019312892 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_019313659 | 278 | LLAQIGDNYAELFLSAKKLYDSILLSGILTVTDVGTQAPLSASMIQRYNEHQMDLAQLKQFIRQK-LSDKYNEVFSDVSK | 356 |
| WP_019314093 | 278 | LLAQIGDNYAELFLSAKKLYDSILLSGILTVTDVSTKAPLSASMIQRYNEHQMDLTQLKQFIRQK-LSDKYNEVFSDVSK | 356 |
| WP_019315370 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_019803776 | 278 | LLAQIGDNYAELFLSAKKLYDSILLSGILTVDGTKAPLSASMIQRYNEHQMDLAQLKQFIRQK-LSDKYNEVFSDVSK | 356 |
| WP_019805234 | 278 | LLAQIGDNYAELFLSAKKLYDSILLSGILTVTDVSTKAPLSASMIQRYNEHQMDLAQLKQFIRQK-LSDKYNEVFSDVSK | 356 |
| WP_024783594 | 278 | LLAQIGDNYAELFLSAKKLYDSILLSGILTADDSSTKAPLSASMIKRYAEHHEDLEKLKEFIKAN-KPELYHDIFKDETK | 356 |
| WP_024784288 | 278 | LLAQIGDNYAELFLSAKKLYDSILLSGILTVTDVSTKAPLSASMIQRYNEHQMDLVQLKQFIRQK-LSDKYNEVFSDVSK | 356 |
| WP_024784666 | 278 | LLAQIGDNYAELFLSAKKLYDSILLSGILTVTDVSTKAPLSASMIQRYNEHQMDLTQLKQFIRQK-LSDKYNEVFSDVSK | 356 |
| WP_024784894 | 278 | LLAQIGDNYAELFLSAKKLYDSILLSGILTADDSSTKAPLSASMIKRYAEHHEDLEKLKEFIKAN-KPELYHDIFKDETK | 356 |
| WP_024786433 | 278 | LLGKIGDDYADLFTLAKNLYDAILLSGILLAGILSDILTVKGVNTKAPLSASMIQRYNEHQMDLAQLKQFIRQK-LSDKYNEVFSDVSK | 356 |
| WP_049473442 | 278 | LLAQIGDNYAELFLSAKKLYDSILLSGILTVTDVSTKAPLSASMIQRYNEHQMDLTQLKQFIRQK-LSDKYNEVFSDVSK | 356 |
| WP_049474547 | 271 | LLAQIGDNYAELFLSAKKLYDSILLSGILTVTDVSTKAPLSASMIQRYNEHQMDLAQLKQFIRQK-LSDKYNEVFSDVSK | 349 |
| EMC03581 | 279 | LLGQIGDDFADLFVAAKKLYDSILLSGILTVTDPSTKAPLSASMIERYENHQKDLATLKQFIKTN-LPEKYDEVFSDQSK | 357 |
| WP_000428612 | 279 | LLGQIGDDFADLFVAKKLYDSILLSGILTVTDPSTKAPLSASMIERYENHQKDLAVLKQFIKNN-LPEKYDEVFSDQSK | 357 |
| WP_000428613 | 278 | LLGQIGDGFADLFVAKKLYDSILLAGILSVKDPGTKAPLSASMIERYDNHQNDLSALKQFVRRN-LSEKYAEVFSDDSK | 356 |
| WP_049523028 | 247 | LLAQIGDVYADLFVVAKKLYDAILLAGILSDALLSDILTVKGVNTKAPLSASMVQRFNEHQDDLKLLKLKLVKVQ-LPEKYKEIFDIDK | 325 |
| WP_003107102 | 280 | LLTQIGDEYADLFSAKNLSDAILLSDILTVNGDGTQAPLSASLIKRYEEHRQDLALLLKQMFKEQ-LPDLYRDVFTDENK | 358 |
| WP_054279288 | 279 | LLGQIGDDFADLFVAKKLYDAILLSGILTVTDPSTKAPLSASMIERYENHQKDLAALKQFIKNN-LPEKYDEVFSDQSK | 357 |
| WP_049531101 | 279 | LLGQIGDGFADLFVAKKLYDAILLSGILTVTDPSTKAPLSASMIERYENHQNHQNDLASLKQFIKNN-LPEKYDEVFSDQSK | 357 |
| WP_049538452 | 279 | LLGQIGDDFADLFVAKKLYDAILLSGILTVTDPSTKAPLSASMIERYENHQKDLTTLKQFIKNN-LPEKYDEVFSDQSK | 357 |
| WP_049549711 | 280 | LLAEIGDHYADLFLAAKNLSDAILLSDILTLSDENTRAPLSASMIKRYEEHQEDLALLKKLVKEQ-MPEKYWEIFSNAKK | 358 |
| WP_007896501 | 232 | LLAEIGDHYADLFLAAKNLSDAILLSDILTLSDENTRAPLSASMIKRYEEHQEDLALLKKLVKEQ-MPEKYWEIFSNAKK | 310 |
| EFR44625 | 278 | LLGQIGDFADLFIAKKLYDAILLSGILTVTDPSTKAPLSASMIERYENHQKDLAALKQFIKNN-LPEKYVEVFSDQSK | 356 |
| WP_002897477 | 278 | LLGQIGDGFADLFVAKKLYDAILLSGILTVTDPSTKAPLSASMIERYENHQEDLAALKQFIKNN-LSEKYAEVFSDQSK | 356 |
| WP_002906454 | 279 | LLGQIGDDFADLFVAKKLYDAILLSGILTVTDPSTKAPLSASMIERYENHQKDLAALKQFIKNN-LPEKYDEVFSDQSE | 357 |
| WP_009729476 | 278 | LLGIIGDEYADVFVAAKVYDSILLSGILTTNNHSTKAPLSASMIDRYDEHNSDKKLLRDFIRTN1GKEVFKEVFYDTSK | 356 |
| CQR24647 | 279 | LLGQIGDDFADLFVAKKLYDAILLSGILTVKDLSTKAPLSASMIERYENHQKDLAALKQFIQNN-LPEKYDEVFSDQSK | 357 |
| WP_000066813 | 279 | LLGQIGDDFADLFVAKKLYDAILLSGILTVTDPSTKAPLSASMIERYENHQKDLAALKQFIQNN-LPEKYDEVFSDQSK | 357 |
| WP_009754323 | 278 | LLGKIGDDYADLFIATKSLYDGILLAGILSTTDSTTKAPLSSSMVNRYEEHKDLALLKNFIHQN-LSDSYKEVENDKLK | 356 |
| WP_044674937 | 278 | LLGKIGDDYADLFIATKSLYDGILLAGILSTTDSTTKAPLSSSMVNRYEEHKDLALLKNFIHQN-LSDSYKEVENDKLK | 356 |
| WP_044676715 | 278 | LLGKIGDDYADLFIATKSLYDGILLAGILSTTDSTTKAPLSSSMVNRYEEHKDLALLKNFIHQN-LSDSYKEVENDKLK | 356 |
| WP_044680361 | 278 | LLGKIGDDYADLFIATKSLYDGILLAGILSTTDSTTKAPLSSSMVNRYEEHKDLALLKNFIHQN-LSDSYKEVENDKLK | 356 |
| WP_044681799 | 278 | LLGKIGDDYADLFIATKSLYDGILLAGILSTTDSTTKAPLSSSMVNRYEEHKDLALLKNFIHQN-LSDSYKEVENDKLK | 356 |

-continued

```
WP_049533112  278 LLGEIGDEYADLFASAKNLYDAILLSGILTVDDNSTKAPLSASMVKRYEEHQKDLKKLKDFIKVN-APDQYNAIFKDKNK 356
WP_029090905  244 LADVLADEYDLLLTAQKIYSAIILDESMDGYEYFA-----EAKKESYRKHQEELVLVKKMLKSNaITNDERAKF---EY 315
WP_006506696  284 VEKDLGE-YVEFVDALHNVYSWVELQTIMGATHTD-NASISEAMVSRYNKHHDDLKLLKLLKDCIKNN-VPNKYFDMFRNDSE 360
AIT42264      278 LLAQIGDQYADLFLAAKNLSDAILLSDILRVNTEITKAPLSASMIKRYDEHHQDLTLLKALVRQQ-LPEKYKEIFFDQSK 356
WP_034440723  284 LLSNIDEGYRDVFLQAKNVYNAIELSKILKTDGKETKAPLSAQMVELYNQHREDLKKYKDYIKAY-LPEKYGETFKDATK 362
AKQ21048      278 LLAQIGDQYADLFLAAKNLSDAILLSDILRVNTEITKAPLSASMIKRYDEHHQDLTLLKALVRQQ-LPEKYKEIFFDQSK 356
WP_004636532  277 LLGMTDDVFLDVFMAAKNVYDAVEMSAIISTDTGNSKAVLSNQMINFYDEHKVDLAQLKQFKTH-LPDKYYECFSDPSK 355
WP_002364836  284 LLGMTDDVFLDVFMAAKNVYDAVEMSAIISTDTGNSKAVLSNQMINFYDEHKVDLAQLKQFKTH-LPDKYYECFSDPSK 362
WP_016631044  235 ILAKVGDEYSDVFLAAKNVYDAVELSTILADSDKKSHAKLSSSMIVRFTEHQEDLKKFKPKRF IREN-CPDEYDNLFKNEQK 313
EMS75795       21 LLEKSGEEFRDVFLQAKKVYDAILLSTKKQNSKAKLSLGMIERYDSHKKDLEELKQFVKAN-LPEKTAIFFKDSSK 99
WP_002373311  284 ILAKVGDEYSDVFLAAKNVYDAVELSTILADSDKKSHAKLSSSMIVRFTEHQEDLKKFKPKRF IREN-CPDEYDNLFKNEQK 362
WP_002378009  284 ILAKVGDEYSDVFLAAKNVYDAVELSTILADSDKKSHAKLSSSMIVRFTEHQEDLKKFKPKRF IREN-CPDEYDNLFKNEQK 362
WP_002407324  284 ILAKVGDEYSDVFLAAKNVYDAVELSTILADSDKKSHAKLSSSMIVRFTEHQEDLKKFKPKRF IREN-CPDEYDNLFKNEQK 362
WP_002413717  286 ILAKVGDEYSDVFLAAKNVYDAVELSTILADSDKKSHAKLSSSMIVRFTEHQEDLKKFKPKRF IREN-CPDEYDNLFKNEQK 364
WP_010775580  284 ILAKVGDEYSDVFLAAKNVYDAVELSTILADSDKKSHAKLSSSMIVRFTEHQEDLKKFKPKRF IREN-CPDEYDNLFKNEQK 362
WP_010818269  284 ILAKVGDEYSDVFLAAKNVYDAVELSTILADSDKKSHAKLSSSMIVRFTEHQEDLKKFKPKRF IREN-CPDEYDNLFKNEQK 362
WP_010824395  284 ILAKVGDEYSDVFLAAKNVYDAVELSTILADSDKKSYAKLSSSMIVRFTEHQEDLKKFKPKRF IREN-CPDEYDNLFKNEQK 362
WP_016622645  284 ILAKVGDEYSDVFLAAKNVYDAVELSTILADSDKKSHAKLSSSMIVRFTEHQEDLKKFKPKRF IREN-CPDEYDNLFKNEQK 362
WP_033624816  284 ILAKVGDEYSDVFLAAKNVYDAVELSTILADSDKKSHAKLSSSMIVRFTEHQEDLKKFKPKRF IREN-CPDEYDNLFKNEQK 362
WP_033625576  284 ILAKVGDEYSDVFLAAKNVYDAVELSTILADSDKKSHAKLSSSMIVRFTEHQEDLKKFKPKRF IREN-CPDEYDNLFKNEQK 362
WP_033789179  284 ILAKVGDEYSDVFLAAKNVYDAVELSTILADSDKKSHAKLSSSMIVRFTEHQEDLKKFKPKRF IREN-CPDEYDNLFKNEQK 362
WP_002310644  282 LLEKIGDDYIDLFVQAKNVYDAVLLSEILSDSTKNTRAKLSAGMIRRYDAHKEDLVLLKRFVKEN-LPKKYRAFFGDNSV 360
WP_002312694  283 LLEKIGDDYIDLFVQAKNVYDAVLLSEILSDSTKNTRAKLSAGMIRRYDAHKEDLVLLKRFVKEN-LPKKYRAFFGDNSV 361
WP_002314015  283 LLEKIGDDYIDLFVQAKNVYDAVLLSEILSDSTKNTRAKLSAGMIRRYDAHKEDLVLLKRFVKEN-LPKKYRAFFGDNSV 361
WP_002320716  283 LLEKIGDDYIDLFVQAKNVYDAVLLSEILSDSTKNTRAKLSAGMIRRYDAHKEDLVLLKRFVKEN-LPKKYRAFFGDNSV 361
WP_002330729  282 LLEKIGDDYIDLFVQAKNVYDAVLLSEILSDSTKNTRAKLSAGMIRRYDAHKEDLVLLKRFVKEN-LPKKYRAFFGDNSV 360
WP_002335161  283 LLEKIGDDYIDLFVQAKNVYDAVLLSEILSDSTKNTRAKLSAGMIRRYDAHKEDLVLLKRFVKEN-LPKKYRAFFGDNSV 361
WP_002345439  283 LLEKIGDDYIDLFVQAKNVYDAVLLSEILSDSTKNTRAKLSAGMIRRYDAHKEDLVLLKRFVKEN-LPKKYRAFFGDNSV 361
WP_034867970  276 LLEKIGDEYLDIFLFVQAKNVYDAILLSEILSSTVKHTAKLSSGMVERYERHKADLAKFKQFVKEN-VPQKATVFFKDTTK 354
WP_047937432  283 LLEKIGDDYIDLFVQAKNVYDAVLLSEILSDSTKNTRAKLSAGMIRRYDAHKEDLVLLKRFVKEN-LPKKYRAFFGDNSV 361
WP_002310994  276 LLEKIGDEYLDIFLQAKKVYHDAILLSEIISSTVKHTQAKLSSGMVERYERHKADLAKFKQFVKEN-VPQKATVFFKDTTK 354
WP_010737004  276 LLEKIGDEYLDIFLQAKKVYHDAILLSEIISSTVKHTQAKLSSGMVERYERHKADLAKFKQFVKEN-VPQKATVFFKDTTK 354
WP_010737478  276 LLEKIGDEYLDIFLQAKKVYHDAILLSEIISSTVKHTQAKLSSGMVERYERHKADLAKFKQFVKEN-VPQKATVFFKDTTK 354
WP_007209003  281 LLAIIGDEYGDIFVAAQNLYQAILLAGILTSTEK-TRAKLSASMIQRYEEHAKDLKLLKRFVKEH-IPDKYAEIFNDATK 358
WP_023519017  276 LLEKTSDDYAELFLKAKGVYDAILLSGILSKSDDETKAKLSANMKLRFEEHQRDLKQLKELVRRD-LPKKYDFFKNRSK 354
WP_010770040  279 LLAIIGDEYAELFSATKSVYDAVALSGILSVTDGDTKAKLSASMVERYEAHQDKLVQFKQFIRKE-LPEMYAPIFRDNSV 357
WP_010770040  275 LLGEIGDEYADLFVEAAKNVYAVELSGILTVTDNSTKAKLSAMIKRYEDHKTDKLKLFKEFIRKN-LPEKYHEIFNDKNT 353
WP_048604708  276 LLRKSNEEMIDVFLQVKKVYDAILLSDILSTKMKDTKAKLSAGMIERYQNHKKDLEELKQFVRAH-LHEKVTVFFKDSSK 354
WP_010750235  317 LLAQIGDQYADLFLAAKNLSDAILLSDILRVNTEITKAPLSASMIKRYDEHHQDLTLLKALVRQQ-LPEKYKEIFFDQSK 395
AII16583      290 KQPLLGD-CVEFIDLLLHDIYSWVELQNILGSAHTS-EPSISAAMIQRYEDHKNDLKLLKDVIRKY-LPKKYFEVFRDEKS 366
WP_029073316  290 KQPLLGD-CVEFIDLLLHDIYSWVELQNILGSAHTS-EPSISAAMIQRYEDHKNDLKLLKDVIRKY-LPKKYFEVFRDEKS 366
WP_031589969  276 LLAEAGDQYLDIFVAAKKVYDAAILASILDVKDTQTKTVFSQAMIERYEEHQKDLIELKRVFKKY-LPEKCHDFFSE-PK 353
KDA45870      286 LESSLDDNAHQIIESLQELYSGVLLAGIVPEMQSLS-----NGESYFSMAKVNQYENHAIDLCKLRDMWHTT---KNEKAV-GLSR 359
WP_039099354  279 LDSILDDDQFTVLDTANRIYSTITLNEIL-----NGESYFSMAKVNQYENHAIDLCKLRDMWHTT---KNEKAV-GLSR 348
AKP02966      284 LLALIGDEYAELFVAAKNAYSAVLSSIITVAETETNAKLSASMIERPDTHEEDLGELKAFIKLH-LPKHYEIFSNTEK 362
WP_010991369  284 LLALIGDEYAELFVAAKNAYSAVLSSIITVAETETNAKLSASMIERPDTHEEDLGELKAFIKLH-LPKHYEIFSNTEK 362
WP_033838504  287 LLALIGDEYAELFVAAKNAYSAVVLSSIITVAFTETNAKLSASMIERPDTHEEDLGELKAFIKLH-LPKHYEIFSNTEK 365
EHN60060       53 LLAIGDEYAELFVAAKNAYSAVVLSSIITVAFTETNAKLSASMIERPDTHEEDLGELKAFIKLH-LPKHYEIFSNTEK 131
WP_038409211  284 LLAKIGDEYAEIFVAAKSTYNAVVLSNIITVDTETKAKLSASMIERRDKAKDLKRLKAFFKMQ-LPEKFNEVFNDIEK 362
EFR95520          --
WP_003723650  284 LLAIIGDEYAELFVAAKNTYNAVVLSSIITVTATETNAKLSASMIERPDAHEKELGELKAFIKLH-LPKQYEIFSNAAI 362
WP_003727705  284 LLAIIGDEYAELFVAAKNTYNAVVLSSIITVTATETNAKLSASMIERPDAHEKELGELKAFIKLH-LPKQYQEIFNNAEI 362
WP_003730785  284 LLAIIGDEYAELFVAAKNTYNAVVLSSIITVTATETNAKLSASMIERPDAHEKELGELKAFIKLH-LPKQYQEIFNNAEI 362
```

-continued

| | | | |
|---|---|---|---|
| WP_003733029 | 284 | LLAIIGDEFAEVFVAAKNAYNAVVLSNIIITVDSTTRAKLSASLIERPENHKEDLKKMKRFVRTY-LPEKYDEIFDDTEK | 362 |
| WP_003739838 | 284 | LLAIIGDEYAELFVAAKNTYNAVVLSSIITVTDTETNAKLSASMIERPDAHEKDLSELKAFIKLH-LPKQYEBIFSNVAI | 362 |
| WP_014601172 | 284 | LLAIIGDEYAELFVAAKNTYNAVVLSSIITVTATETNAKLSASMIERPDAHEKDLGELKAFIKLN-LPKQYQEIFNNAAI | 362 |
| WP_023548323 | 284 | LLAIIGDEYAELFVAAKNTYNAVVLSSIITVTDTETNAKLSASMIERPDAHEKDLVELKAFIKLN-LPKQYQEIFSNAAI | 362 |
| WP_031665337 | 284 | LLAIIGDEYAELFVAAKNTYNAVVLSSIITVNDTETNAKLSASMIERPDAHEKDLVELKAFIKLN-LPKQYEIFSNAAI | 362 |
| WP_031669209 | 284 | LLAIIGDEFAEVFVAAKNAYNAVVLSNIIITVDSTTRAKLSASLIERPENHKEDLKKMKRFVRTY-LPEKYDEIFDDTEK | 362 |
| WP_033920898 | 284 | LLAIIGDEYAELFVAAKNTYNAVVLSSIITVTDTETNAKLSASMIERPDAHEKDLVELKAFIKLN-LPKQYEBIFSNAAI | 362 |
| AKI42028 | 287 | LLAIIGDEYAELFVAAKNTYNAVVLSSIITVTATETNAKLSASMIERPDAHEKDLGELKAFIKLH-LPKQYQEIFNNAAI | 365 |
| AKI50529 | 287 | LLAIIGDEYAELFVAAKNTYNAVVLSSIITVTDTETNAKLSASMIERPDAHEKDLVELKAFIKLN-LPKQYEBIFSNAAI | 365 |
| EFR83390 | | | |
| WP_046323366 | 284 | LLARVGDEYAEIFVAAKNAYNAVVLSSIITVSNTETKAKLSASMIERPDKHDKDLKRMKAFFKVR-LPENFNEVFRNDVEK | 362 |
| AKE81011 | 294 | LLAQIGDQYADLFLAAKNLSDAILLSDILRVNTEITKAPLSASMIKRYDEHHQDLTLLKALVRQQ-LPEKYKEIFFDQSK | 372 |
| CUO82355 | 288 | VENDLGE-YVEFIDSLHNIYSWVELQTIMGATHTD-NASISEAMVSRYNKHHEDLQLLKKCIKDN-VPKKYFDMFRNDSE | 364 |
| WP_033162887 | 289 | LQSELGE-YIEFIEMLHNIYSWELQAILGATHTD-NPSISAMVERYEEHKKDLRVLKKVIREE-LPDKYNEVFRKDNR | 365 |
| AGZ01981 | 311 | LLAQIGDQYADLFLAAKNLSDAILLSDILRVNTEITKAPLSASMIKRYDEHHQDLTLLKALVRQQ-LPEKYKEIFFDQSK | 389 |
| AKA60242 | 278 | LLAQIGDQYADLFLAAKNLSDAILLSDILRVNTEITKAPLSASMIKRYDEHHQDLTLLKALVRQQ-LPEKYKEIFFDQSK | 356 |
| AKS40380 | 278 | LLAQIGDQYADLFLAAKNLSDAILLSDILRVNTEITKAPLSASMIKRYDEHHQDLTLLKALVRQQ-LPEKYKEIFFDQSK | 356 |
| 4UN5_B | 282 | LLAQIGDQYADLFLAAKNLSDAILLSDILRVNTEITKAPLSASMIKRYDEHHQDLTLLKALVRQQ-LPEKYKEIFFDQSK | 360 |
| WP_010922251 | 357 | -NGYAG YIDG G ASQEEFYKFIKPILEK-M--DGTEELLv--KLNREDLLRKQRTFDNGSIPHQIHLGEL | 419 |
| WP_039695303 | 358 | -NGYAG YIDG G ASQEEFYKFIKPILEK-M--DGTEELLv--KLNREDLLRKQRTFDNGSIPHQIHLQEM | 422 |
| WP_045635197 | 357 | -DGYAG YIDG K TTQETFYKIKNLLSK-F--EGTDYFL--DKIEREDFLRKQRTFDNGSIPYQIHLGEL | 419 |
| 5AXW_A | 169 | ----G SINR - ---------------K.---TSDYVk---------EA | 183 |
| WP_009880683 | 41 | -NGYAG YIDG G ASQEEFYKFIKPILEK-M--DGTEELLa--KLNREDLLRKQRTFDNGSIPYQIHLGEL | 103 |
| WP_010922251 | 357 | -NGYAG YIDG G ASQEEFYKFIKPILEK-M--DGTEELLv--KLNREDLLRKQRTFDNGSIPYQIHLGEL | 419 |
| WP_011488318 | 357 | -NGYAG YIDG G ASQEEFYKFIKPILEK-M--DGTEELLa--KLNREDLLRKQRTFDNGSIPHQIHLGEL | 419 |
| WP_011054416 | 357 | -NGYAG YIDG G ASQEEFYKFIKPILEK-M--DGTEELLa--KLNREDLLRKQRTFDNGSIPHQIHLGEL | 419 |
| WP_011284745 | 357 | -NGYAG YIDG G ASQEEFYKFIKPILEK-M--DGTEELLa--KLNREDLLRKQRTFDNGSIPHQIHLGEL | 419 |
| WP_011285506 | 357 | -NGYAG YIDG G ASQEEFYKFIKPILEK-M--DGTEELLa--KLNREDLLRKQRTFDNGSIPHQIHLGEL | 419 |
| WP_011527619 | 357 | -NGYAG YIDG G ASQEEFYKFIKPILEK-M--DGTEELLv--KLNREDLLRKQRTFDNGSIPHQIHLGEL | 419 |
| WP_012560673 | 357 | -NGYAG YIDG G ASQEEFYKFIKPILEK-M--DGTEELLa--KLNREDLLRKQRTFDNGSIPHQIHLGEL | 419 |
| WP_014407541 | 357 | -NGYAG YIDG G ASQEEFYKFIKPILEK-M--DGTEELLv--KLNREDLLRKQRTFDNGSIPHQIHLGEL | 419 |
| WP_020905136 | 357 | -NGYAG YIDG G ASQEEFYKFIKPILEK-M--DGTEELLa--KLNREDLLRKQRTFDNGSIPHQIHLGEL | 419 |
| WP_023080005 | 357 | -NGYAG YIDG G ASQEEFYKFIKPILEK-M--DGTEELLa--KLNREDLLRKQRTFDNGSIPHQIHLGEL | 419 |
| WP_023610282 | 357 | -NGYAG YIDG G ASQEEFYKFIKPILEK-M--DGTEELLa--KLNREDLLRKQRTFDNGSIPYQIHLGEL | 419 |
| WP_030125963 | 357 | -NGYAG YIDG G ASQEEFYKFIKPILEK-M--DGTEELLv--KLNREDLLRKQRTFDNGSIPYQIHLGEL | 419 |
| WP_030126706 | 357 | -NGYAG YIDG G ASQEEFYKFIKPILEK-M--DGTEELLa--KLNREDLLRKQRTFDNGSIPYQIHLGEL | 419 |
| WP_031488318 | 357 | -NGYAG YIDG G ASQEEFYKFIKPILEK-M--DGTEELLa--KLNREDLLRKQRTFDNGSIPYQIHLGEL | 419 |
| WP_032460140 | 357 | -NGYAG YIDG G ASQEEFYKFIKPILEK-M--DGTEELLa--KLNREDLLRKQRTFDNGSIPHQIHLGEL | 419 |
| WP_032461047 | 357 | -NGYAG YIDG G ASQEEFYKFIKPILEK-M--DGTEELLa--KLNREDLLRKQRTFDNGSIPHQIHLGEL | 419 |
| WP_032462016 | 357 | -NGYAG YIDG G ASQEEFYKFIKPILEK-M--DGTEELLv--KLNREDLLRKQRTFDNGSIPHQIHLGEL | 419 |
| WP_032462936 | 357 | -NGYAG YIDG G ASQEEFYKFIKPILEK-M--DGTEELLa--KLNREDLLRKQRTFDNGSIPHQIHLGEL | 419 |
| WP_032464890 | 357 | -NGYAG YIDG G ASQEEFYKFIKPILEK-M--DGTEELLa--KLNRKDLLRKQRTFDNGSIPHQIHLGEL | 419 |
| WP_033888930 | 182 | -NGYAG YIDG G ASQEEFYKFIKPILEK-M--DGTEELLa--KLNREDLLRKQRTFDNGSIPHQIHLGEL | 244 |
| WP_038431314 | 357 | -NGYAG YIDG G ASQEEFYKFIKPILEK-M--DGTEELLv--KLNREDLLRKQRTFDNGSIPHQIHLGEL | 419 |
| WP_038432938 | 357 | -NGYAG YIDG G ASQEEFYKFIKPILEK-M--DGTEELLa--KLNREDLLRKQRTFDNGSIPYQIHLGEL | 419 |
| WP_038434062 | 357 | -NGYAG YIDG G ASQEEFYKFIKPILEK-M--DGTEELLa--KLNREDLLRKQRTFDNGSIPHQIHLGEL | 419 |
| BAQ51233 | 268 | -NGYAG YIDG G ASQEEFYKFIKPILEK-M--DGTEELLv--KLNREDLLRKQRTFDNGSIPHQIHLGEL | 330 |
| KGE60162 | | | |
| KGE60856 | | | |
| WP_002989955 | 357 | -NGYAG YIDG G ASQEEFYKFIKPILEK-M--DGTEELLa--KLNREDLLRKQRTFDNGSIPHQIHLGEL | 419 |
| WP_003030002 | 357 | -KGYAG YIEN G VKQDEFYKYLKGIILLQ-I--NGSGDFL--DKIDREDFLRKQRTFDNGSIPHQIHLQEM | 419 |
| WP_003065552 | 360 | -NGYAG YIEN G VKQDEFYKYLKNTLSK-Ia--GSDYFL--DKIEREDFLRKQRTFDNGSIPHQVHLGEL | 422 |
| WP_001040076 | 358 | -DGYAG YIEG K TNQEAFYKYLSKLLTK-Q--EGSEYFL--EKIKNEDFLRKQRTFDNGSIPHQVHLTEL | 420 |
| WP_001040078 | 358 | -DGYAG YIEG K TNQEAFYKYLSKLLTK-q--EDSENFL--EKIKNEDFLRKQRTFDNGSIPHQVHLTEL | 420 |

-continued

| ID | Start | Sequence | End |
|---|---|---|---|
| WP_001040080 | 358 | -DGYAG YIEG K TNQEAFYKYLSKLLTK-Q--EDSENFL---EKIKNEDFLRKQRTFDNGSIPHQVHLTEL | 420 |
| WP_001040081 | 358 | -DGYAG YIEG K TNQEAFYKYLSKLLTK-Q--EDSENFL---EKIKNEDFLRKQRTFDNGSIPHQVHLTEL | 420 |
| WP_001040083 | 358 | -DGYAG YIEG K TNQEAFYKYLSKLLTK-Q--EDSENFL---EKIKNEDFLRKQRTFDNGSIPHQVHLTEL | 420 |
| WP_001040085 | 358 | --DGYAG YIEG K TNQEAFYKYLSKLLTK-Q--EDSENFL---EKIKNEDFLRKQRTFDNGSIPHQVHLTEL | 420 |
| WP_001040087 | 358 | -DGYAG YIEG K TNQEAFYKYLSKLLTK-Q--EDSENFL---EKIKNEDFLRKQRTFDNGSIPHQVHLTEL | 420 |
| WP_001040088 | 358 | -DGYAG YIEG K TNQEAFYKYLSKLLTK-Q--EDSENFL---EKIKNEDFLRKQRTFDNGSIPHQVHLTEL | 420 |
| WP_001040089 | 358 | -DGYAG YIEG K TNQEAFYKYLSKLLTK-Q--EDSENFL---EKIKNEDFLRKQRTFDNGSIPHQVHLTEL | 420 |
| WP_001040090 | 358 | -DGYAG YIEG K TNQEAFYKYLSKLLTK-Q--EDSENFL---EKIKNEDFLRKQRTFDNGSIPHQVHLTEL | 420 |
| WP_001040091 | 358 | -DGYAG YIEG K TNQEAFYKYLSKLLTK-Q--EDSENFL---EKIKNEDFLRKQRTFDNGSIPHQVHLTEL | 420 |
| WP_001040092 | 358 | -DGYAG YIEG K TNQEAFYKYLSKLLTK-Q--EDSEYLL---EKIKNEDFLRKQRTFDNGSIPHQVHLTEL | 420 |
| WP_001040094 | 358 | -DGYAG YIEG K TNQEAFYKYLSKLLTK-Q--EDSEYLL---EKIKNEDFLRKQRTFDNGSIPHQVHLTEL | 420 |
| WP_001040095 | 358 | -DGYAG YIEG K TNQEAFYKYLSKLLTK-Q--EGSEYLL---EKIKNEDFLRKQRTFDNGSIPHQVHLTEL | 420 |
| WP_001040096 | 358 | -DGYAG YIEG K TNQEAFYKYLSKLLTK-Q--EGSEYLL---EKIKNEDFLRKQRTFDNGSIPHQVHLTEL | 420 |
| WP_001040097 | 358 | -DGYAG YIEG K TNQEAFYKYLSKLLTK-Q--EGSEYLL---EKIKNEDFLRKQRTFDNGSIPHQVHLTEL | 420 |
| WP_001040098 | 358 | -DGYAG YIEG K TNQEAFYKYLSKLLTK-Q--EGSEYLL---EKIKNEDFLRKQRTFDNGSIPHQVHLTEL | 420 |
| WP_001040099 | 358 | -DGYAG YIEG K TNQEAFYKYLSKLLTK-Q--EGSEYLL---EKIKNEDFLRKQRTFDNGSIPHQVHLTEL | 420 |
| WP_001040100 | 358 | -DGYAG YIEG K TNQEAFYKYLSKLLTK-Q--EGSEYFL---EKIKNEDFLRKQRTFDNGSIPHQVHLTEL | 420 |
| WP_001040104 | 358 | -DGYAG YIEG K TNQGAFYKYLSKLLTK-Q--EGSEYFL---EKIKNEDFLRKQRTFDNGSIPHQVHLTEL | 420 |
| WP_001040105 | 358 | -DGYAG YIEG K TNQGAFYKYLSKLLTK-Q--EGSEYFL---EKIKNEDFLRKQRTFDNGSIPHQVHLTEL | 420 |
| WP_001040106 | 358 | -DGYAG YIEG K TNQGAFYKYLSKLLTK-Q--EGSEYFL---EKIKNEDFLRKQRTFDNGSIPHQVHLTEL | 420 |
| WP_001040107 | 358 | -DGYAG YIEG K TNQGAFYKYLSKLLTK-Q--EGSEYFL---EKIKNEDFLRKQRTFDNGSIPHQVHLTEL | 420 |
| WP_001040108 | 358 | -DGYAG YIEG K TNQGAFYKYLSKLLTK-Q--EDSEYFL---EKIKNEDFLRKQRTFDNGSIPHQVHLTEL | 420 |
| WP_001040109 | 358 | -DGYAG YIEG K TNQEAFYKYLSKLLTK-Q--EDSEYFL---EKIKNEDFLRKQRTFDNGSIPHQVHLTEL | 420 |
| WP_001040110 | 358 | -DGYAG YIEG K TNQEAFYKYLSKLLTK-Q--EDSEYFL---EKIKNEDFLRKQRTFDNGSIPHQVHLTEL | 420 |
| WP_015058523 | 358 | -DGYAG YIEG K TNQEAFYKYLSELLTK-Q--EDSEYFL---EKIKNEDFLREQRTEDNGSIPHQVHLTEL | 420 |
| WP_017643650 | 358 | -DGYAG YIEG K TNQEAFYKYLSELLTK-Q--EDSENFL---EKIKNEDFLREQRTEDNGSIPHQVHLTEL | 420 |
| WP_017647151 | 358 | -DGYAG YIEG K TNQEAFYKYLSELLTK-Q--EDSENFL---EKIKNEDFLREQRTEDNGSIPHQVHLTEL | 420 |
| WP_017648376 | 358 | -DGYAG YIEG K TNQEAFYKYLSELLTK-Q--EDSENFL---EKIKNEDFLREQRTEDNGSIPHQVHLTEL | 420 |
| WP_017649527 | 358 | -DGYAG YIEG K TNQEAFYKYLSELLTK-Q--EDSENFL---EKIKNEDFLREQRTEDNGSIPHQVHLTEL | 420 |
| WP_017771611 | 358 | -DGYAG YIEG K TNQEAFYKYLSELLTK-Q--EDSENFL---EKIKNEDFLREQRTEDNGSIPHQVHLTEL | 420 |
| WP_017771984 | 358 | -DGYAG YIEG K TNQEAFYKYLSELLTK-Q--EDSENFL---EKIKNEDFLREQRTEDNGSIPHQVHLTEL | 420 |
| CFQ25032 | 358 | -DGYAG YIEG K TNQEAFYKYLSELLTK-Q--EDSEYLL---EKIKNEDFLREQRTEDNGSIPHQVHLTEL | 420 |
| CFV16040 | 358 | -DGYAG YIEG K TNQEAFYKYLSKLLTK-Q--EDSENFL---EKIKNEDFLRKQRTFDNGSIPHQVHLTEL | 420 |
| KLJ37842 | 358 | -DGYAG YIEG G VKQDEFYKYLEGILLQ-I--NGSGDFL---DKIDREDFLREQRTEDNGSIPHIHLQEM | 420 |
| KLJ72361 | 357 | -KGYAG YIES G VKQDEFYKYLEGILLK-I--NGSGDFL---DKIDCEDFLREQRTEDNGSIPHIHLQEM | 419 |
| ELL20707 | 358 | -KGYAG YIES G VKQDEFYKYLEGILLK-I--NGSGDFL---DKIDCEDFLREQRTEDNGSIPHIHLQEM | 420 |
| KLL42645 | 358 | -NGYAG YIEN G VKQDEFYKYLENTLSK-I--DGSDYFL---DKIDREDFLREQRTEDNGSIPHIHLQEM | 420 |
| WP_047207273 | 357 | -KGYAG YIES G VKQDEFYKYLEGILLK-I--NGSGDFL---DKIDCEDFLREQRTEDNGSIPHIHLQEM | 419 |
| WP_047209694 | 358 | -NGYAG YIES G VKQDEFYKYLEGIITK-I--NGSDYFL---DKIEREDFLREQRTEDNGSIPHIHLQEM | 420 |
| WP_050198062 | 358 | -NGYAG YIES G VKQDEFYKYLEGIITK-I--NGSDYFL---DKIEREDFLREQRTEDNGSIPHIHLQEM | 420 |
| WP_050201642 | 358 | -NGYAG YIES G VKQDEFYKYLEGIITK-I--NGSDYFL---DKIEREDFLREQRTEDNGSIPHIHLQEM | 420 |
| WP_050204027 | 358 | -NGYAG YIES G VKQDEFYKYLEGIITK-I--NGSDYFL---DKIEREDFLREQRTEDNGSIPHIHLQEM | 420 |
| WP_050881965 | 358 | -NGYAG YIES G VKQDEFYKYLEGIITK-I--NGSDYFL---DKIEREDFLREQRTEDNGSIPHIHLQEM | 420 |
| WP_050886065 | 358 | -NGYAG YIES G VKQDEFYKYLEGIITK-I--NGSDYFL---DKIEREDFLREQRTEDNGSIPHIHLQEM | 420 |
| AHN30376 | 358 | -NGYAG YIES G VKQDEFYKYLEGIITK-I--NGSDYFL---DKIEREDFLREQRTEDNGSIPHIHLQEM | 420 |
| EA078426 | 358 | -NGYAG YIEG G VKQDEFYKYLEGIITK-I--NGSGDFL---DKIDREDFLREQRTEDNGSIPHIHLQEM | 420 |
| CCW42055 | 357 | -KGYAG YIES G VKQDEFYKYLEGILLQ-I--NGSGDFL---DKIDREDFLREQRTEDNGSIPHIHLQEM | 419 |
| WP_003041502 | 358 | -KGYAG YIES G VKQDEFYKYLEGILLK-I--NGSGDFL---DKIDCEDFLREQRTEDNGSIPHIHLQEM | 420 |
| WP_037593752 | 358 | -KGYAG YIES G VKQDEFYKYLEGILLK-I--NGSGDFL---DKIDCEDFLREQRTEDNGSIPHIHLQEM | 420 |
| WP_049516684 | 358 | -NGYAG YIEN G VKQDEFYKYLENTLSK-I--DGSDYFL---DKIDREDFLREQRTEDNGSIPHIHLQEM | 420 |
| GAD46167 | 357 | -KGYAG YIES G VKQDEFYKYLEGILLK-I--NGSGDFL---DKIDCEDFLREQRTEDNGSIPHIHLQEM | 419 |
| WP_018363470 | 358 | -NGYAG YIES G VKQDEFYKYLEGIITK-I--NGSDYFL---DKIEREDFLREQRTEDNGSIPHQIHLKEL | 420 |
| WP_003043819 | 357 | -NGYAG YVGI G ATQEEFYKFIKPILEK-M--DGAEELLa--KLNRDDLLREQRTEDNGSIPHQIHLKEL | 429 |

-continued

```
WP_006269658    357 -KGYAS YIES G VKQDEFYKYLEGILLK-I--NSGDFL---DKIDREDFLREQRTEDNGSIPHQIHLQEM 419
WP_048800889    357 -NGYAG YIEN G VKQDEFYKYLENTLSK-I--DGSGYFL---DKIEREDFLREQRTEDNGSIPHQIHLQEM 419
WP_012767106    357 -NGYAG YIDG G ASQEEFYKFIKPILEK-M--DGTEELLa---KLNREDLLREQRTEDNGSIPHQIHLGEL 419
WP_014612333    357 -NGYAG YIDG G ASQEEFYKFIKPILEK-M--DGTEELLa---KLNREDLLREQRTEDNGSIPHQIHLGEL 419
WP_015017095    357 -NGYAG YIDG G ASQEEFYKFIKPILEK-M--DGTEELLa---KLNREDLLREQRTEDNGSIPHQIHLGEL 419
WP_015057649    357 -NGYAG YIDG G ASQEEFYKFIKPILEK-M--DGTEELLa---KLNREDLLREQRTEDNGSIPHQIHLGEL 419
WP_048327215    357 -NGYAG YIDG G ASQEEFYKFIKPILEK-M--DGTEELLa---KLNREDLLREQRTEDNGSIPHQIHLGEL 419
WP_049519324    357 -NGYAG YIDG G ASQEEFYKFIKPILEK-M--DGTEELLa---KLNREDLLREQRTEDNGSIPHQIHLGEL 419
WP_012515931    357 -NGYAG YIEG Q VSQEEFYKYLKPILAR-L--DGSEPLLl---KIDREDFLREQRTEDNGSIPHQIHLEEL 419
WP_021320964    357 -NGYAG YIEG Q VSQEEFYKYLKPILAR-L--DGSEPLLl---KIDREDFLREQRTEDNGSIPHQIHLEEL 419
WP_037581760    357 -NGYAG YIEG Q VSQEEFYKYLKPILAR-L--DGSEPLLl---KIDREDFLREQRTEDNGSIPHQIHLEEL 419
WP_004232481    357 -NGYAG YIEN G VKQDIFYCHLKSIISE-K--NGGQYFL---DKIEREDFLREQRTEDNGSIPYQIHLQEM 419
WP_009854540    358 -NGYAG YIEN G VKQDEFYKYLENTLSK-I--DGSDYFL---DKIEREDFLRKQRTFDNGSIPHQIHLQEM 420
WP_012962174    358 -NGYAG YIEN G VKQDEFYKYLETTLSK-I--DGSDYFL---DKIEREDFLRKQRTFDNGSIPHQIHLQEM 420
WP_039695303    358 -NGYAG YIEN G VKQDEFYKYLKNILSK-IkiDGSDYFL---DKIEREDFLRKQRTFDNGSIPHQIHLQEM 422
WP_014334983    357 -NGYAG YIDN G VKQDEFYKYLKTILTK-I--DDSDYFL---DKIERDDFLRKQRTFDNGSIPHQIHLQEM 419
WP_003099269    357 -NGYAG YIDG K TSQEEFYKYIKPILLK-L--DGTEKLIs---KLEREDFLRKQRTFDNGSIPHQIHLNEL 419
AHY15608        357 -NGYAG YIDG K TSQEEFYKYIKPILLK-L--DGTEKLIs---KLEREDFLRKQRTFDNGSIPHQIHLNEL 419
AHY17476        357 -NGYAG YIDG K TSQEEFYKYIKPILLK-L--DGTEKLIs---KLEREDFLRKQRTFDNGSIPHQIHLNEL 419
ESR09100            -------  ---  ---------------- ---  --------- ---------------------------
AGM98575        357 -NGYAG YIDG K TSQEEFYKYIKPILLK-L--DGTEKLIs---KLEREDFLRKQRTFDNGSIPHQIHLNEL 419
ALF27331        357 -DGYAG YIDG K TNQEAFYKYLKGLLNK-I--EGSGYFL---DKIEREDFLRKQRTFDNGSIPHQIHLQEM 419
WP_018372492    355 -PSYAA YVSG A VTEDDFYKFSKGLLID-V--EGAEYFL---EKIEREDFLRKQRTFDNGAIPNQVHVKEL 432
WP_045618028    358 -DGYAG YIDG K TTQEAFYKYIKNLLSK-I--EGADYFL---DKIEREDFLRKQRTFDNGSIPHQIHLQEM 420
WP_045635197    357 -DGYAG YIDG K TTQETFYKYIKNLLSK-F--EGTDYFL---DKIEREDFLRKQRTFDNGSIPHQIHLQEM 419
WP_002263549    357 -DGYAG YIDG K TNQEAFYKYLKGLLNK-I--EGSGYFL---DKIEREDFLRKQRTFDNGSIPHQIHLQEM 419
WP_002263887    357 -NGYAG YIEN G VKQDEFYKYLKNTLSK-I--AGSDYFL---DKIEREDFLRKQRTFDNGSIPHQIHLQEM 419
WP_002264920    357 -DGYAG YIEN G TNQEAFYKYLKNTLSK-I--AGSDYFL---DKIEREDFLRKQRTFDNGSIPHQIHLQEM 419
WP_002269043    357 -DGYAG YIDG K TNQEAFYKYLKGLLNK-I--EGSGYFL---DKIEREDFLRKQRTFDNGSIPHQIHLQEM 419
WP_002269448    357 -DGYAG YIDG K TNQEAFYKYLKGLLNK-I--EGSGYFL---DKIEREDFLRKQRTFDNGSIPHQIHLQEM 419
WP_002271977    357 -DGYAG YIDG K TNQEAFYKYLKGLLNK-I--EGSGYFL---DKIEREDFLRKQRTFDNGSIPHQIHLQEM 419
WP_002272766    357 -DGYAG YIDG K TNQEAFYKYLKGLLNK-I--EGSGYFL---DKIEREDFLRKQRTFDNGSIPHQIHLQEM 419
WP_002273241    357 -DGYAG YIDG K TNQEAFYKYLKGLLNK-I--EGSGYFL---DKIEREDFLRKQRTFDNGSIPHQIHLQEM 419
WP_002275430    357 -DGYAG YIDG K TNQEAFYKYLKGLLNK-I--EGSGYFL---DKIEREDFLRKQRTFDNGSIPHQIHLQEM 419
WP_002276448    357 -DGYAG YIDG K TNQEAFYKYLKGLLNK-I--EGSGYFL---DKIEREDFLRKQRTFDNGSIPHQIHLQEM 419
WP_002277050    357 -NGYAG YIEN G VKQDEFYKYLKNTLSK-I--AGSDYFL---DKIEREDFLRKQRTFDNGSIPHQIHLQEM 419
WP_002277364    357 -DGYAG YIDG K TNQEAFYKYLKGLLNK-I--EGSGYFL---DKIEREDFLRKQRTFDNGSIPHQIHLQEM 419
WP_002279025    357 -DGYAG YIDG K TNQEAFYKYLKGLLNK-I--EGSGYFL---DKIEREDFLRKQRTFDNGSIPHQIHLQEM 419
WP_002279859    357 -DGYAG YIDG K TNQEAFYKYLKGLLNK-I--EGSGYFL---DKIEREDFLRKQRTFDNGSIPHQIHLQEM 419
WP_002280230    357 -DGYAG YIDG K TNQEAFYKYLKGLLNK-I--TGSDYFL---DQIEREDFLRKQRTFDNGSIPHQIHLQEM 419
WP_002281696    357 -DGYAG YIDG K TNQEAFYKYLKGLLNK-I--EGSGYFL---DKIEREDFLRKQRTFDNGSIPHQIHLQEM 419
WP_002282247    357 -NGYAG YIEN G VKQDEFYKYLKNTLSK-I--TGSDYFL---DQIEREDFLRKQRTFDNGSIPHQIHLQEM 419
WP_002282906    357 -DGYAG YIDG K TNQEAFYKYLKGLLNK-I--EGSGYFL---DKIEREDFLRKQRTFDNGSIPHQIHLQEM 419
WP_002283846    357 -DGYAG YIDG K TNQEAFYKYLKGLLNK-I--EGSGYFL---DKIEREDFLRKQRTFDNGSIPHQIHLQEM 419
WP_002287255    357 -DGYAG YIDG K TNQEAFYKYLKGLLNK-I--EGSGYFL---DKIEREDFLRKQRTFDNGSIPHQIHLQEM 419
WP_002288990    357 -DGYAG YIDG K TNQEAFYKYLKGLLNK-I--EGSGYFL---DKIEREDFLRKQRTFDNGSIPHQIHLQEM 419
WP_002289641    357 -DGYAG YIDG K TNQEAFYKYLKGLLNK-I--EGSGYFL---DKIEREDFLRKQRTFDNGSIPHQIHLQEM 419
WP_002290427    357 -DGYAG YIDG K TNQEAFYKYLKGLLNK-I--EGSGYFL---DKIEREDFLRKQRTFDNGSIPHQIHLQEM 419
WP_002295753    357 -DGYAG YIDG K TNQEAFYKYLKGLLNK-I--EGSGYFL---DKIEREDFLRKQRTFDNGSIPHQIHLQEM 419
WP_002296423    357 -NGYAG YIDG K TNQEAFYKYLKGLLNK-I--EGSGYFL---DKIEREDFLRKQRTFDNGSIPHQIHLQEM 419
WP_002304487    357 -DGYAG YVGA D ATEEEFYKYVKGILNK-V--EGADVWL---DKIDREDFLRKQRTFDNGSIPHQIHLQEM 429
WP_002305844    357 -DGYAG YIDG K TNQEAFYKYLKGLLNK-I--EGSGYFL---DKIEREDFLRKQRTFDNGSIPHQIHLQEM 419
WP_002307203    357 -DGYAG YIDG K TNQEAFYKYLKGLLNK-I--EGSGYFL---DKIEREDFLRKQRTFDNGSIPHQIHLQEM 419
```

-continued

```
WP_002310390   357 --DGYAG YIDG K TNQEAFYKYLKGLLNK-I--EGSGYFL--DKIEREDFLRKQRTFDNGSIPHQIHLQEM 419
WP_002352408   357 --DGYAG YIDG K TNQEAFYKYLKGLLNK-I--EGSGYFL--DKIEREDFLRKQRTFDNGSIPHQIHLQEM 419
WP_012997688   357 --DGYAG YIDG K TNQEAFYKYLKGLLNK-I--EGSGYFL--DKIEREDFLRKQRTFDNGSIPHQIHLQEM 419
WP_014677909   357 --DGYAG YIDG K TNQEAFYKYLKGLLNK-I--EGSGYFL--DKIEREDFLRKQRTFDNGSIPHQIHLQEM 419
WP_019312892   357 --DGYAG YIDG K TNQEAFYKYLKGLLNK-I--EGSGYFL--DKIEREDFLRKQRTFDNGSIPHQIHLQEM 419
WP_019313659   357 --DGYAG YIDG K TNQEAFYKYLKGLLNK-I--EGSGYFL--DKIEREDFLRKQRTFDNGSIPHQIHLQEM 419
WP_019314093   357 --DGYAG YIDG K TNQEAFYKYLKGLLNK-I--EGSGYFL--DKIEREDFLRKQRTFDNGSIPHQIHLQEM 419
WP_019315370   357 --DGYAG YIDG K TNQEAFYKYLKGLLNK-I--EGNGYFL--DKIEREDFLRKQRTFDNGSIPHQIHLQEM 419
WP_019803776   357 --DGYAG YIDG K TNQEAFYKYLKGLLNK-I--EGSGYFL--DKIEREDFLRKQRTFDNGSIPHQIHLQEM 419
WP_019805234   357 --DGYAG YIDG K TNQEAFYKYLKGLLNK-I--EGSGYFL--DKIEREDFLRKQRTFDNGSIPHQIHLQEM 419
WP_024783594   357 --DGYAG YIDG K TNQEAFYKYLKGLLNK-I--EGSGYFL--DKIEREDFLRKQRTFDNGSIPHQIHLQEM 419
WP_024784288   357 --NGYAG YIEN G VKQDEFYKYLKNTLSK-I--TGSDYFL--DQIEREDFLRKQRTFDNGSIPHQIHLQEM 419
WP_024784666   357 --DGYAG YIDG K TNQEAFYKYLKGLLNK-I--EGSGYFL--DKIEREDFLRKQRTFDNGSIPHQIHLQEM 419
WP_024784894   357 --DGYAG YIEN G VKQDEFYKYLKNTLSK-I--AGSDYFL--DKIEREDFLRKQRTFDNGSIPHQIHLQEM 419
WP_024786433   357 --NGYAG YIEN G VKQDEFYKYLKNTLSK-I--AGSDYFL--DKIEREDFLRKQRTFDNGSIPHQIHLQEM 419
WP_049473442   357 --DGYAG YIDG K TNQEAFYKYLKGLLNK-I--EGSGYFL--DKIEREDFLRKQRTFDNGSIPHQIHLQEM 419
WP_049474547   357 --DGYAG YIDG K TNQEAFYKYLKGLLNK-I--EGSGYFL--DKIEREDFLRKQRTFDNGSIPHQIHLQEM 419
EMC03581       350 --DGYAG YIDG K TNQESFYKYIKNLLSK-F--EGADYFL--EKIEREDFLRKQRTFDNGSIPHQIHLQEM 412
WP_000428612   358 --DGYAG YIDG K TTQEAFYKYIKNLLSK-F--EGTDYFL--EKIEREDFLRKQRTFDNGSIPHQIHLQEM 420
WP_000428613   358 --DGYAG YIDG K TNQEAFYKYIKNLLSK-I--EGAEYFL--EKIEREDFLRKQRTFDNGSIPHQIHLQEM 420
WP_049523028   357 --DGYAG YIDG K TNQEAFYKYIKNLLSK-I--KGAESLls--KLEREDFLRKQRTFDNGSIPHQIHLNEL 419
WP_003107102   326 --NGYAG YING K TSQEDFYKYIKPILSK-L--DGAEDFLt--KINREDFLRKQRTFDNGSIPHQIHLGEL 388
WP_054279288   359 --EGYAG YISG K TSQEAFYKYIKPILET-L--DGADYLL--DKIEREDFLKKQRTFDNGSIPHQIHLGEL 421
WP_049531101   358 --DGYAG YIDS K TTQEAFYKYIKNLLSK-F--EGADYFL--EKIEREDFLRKQRTFDNGSIPHQIHLQEM 420
WP_049538452   358 --DGYAG YVDG K TTQEAFYKYIKNLLSK-F--EGTDYFL--EKIEREDFLRKQRTFDNGSIPHQIHLQEM 420
WP_049549711   359 --DGYAG YIEG K VSQDDFYRYIKPILSR-L--KGGDEFLa--KIDRDDFLRKQRTFDNGSIPHQIHLKEL 421
WP_007896501   311 --NGYAG YIEG K VSQDEFYRYIKPILSR-L--KGGDEFLa--KIDRDDFLRKQRTFDNGSIPHQIHLKEL 373
EFR44625       357 --DGYAG YIDG K TTQEAFYKYIKNLLSK-F--EGADYFL--DKIEREDFLRKQRTFDNGSIPHQIHLQEM 419
WP_002897477   357 --DGYAG FIDG K TTQEAFYKYIKNLLSK-L--EGADYFL--NKIEREDFLRKQRTFDNGSIPHQIHLQEM 419
WP_002906454   358 --DGYAG YIDG K TTQETFYKYIKNLLSK-F--DGADYFL--DKIEREDFLRKQRTFDNGSIPHQIHLQEM 420
WP_009729476   358 --NGYAG YIDG K TNQEDFYKYLKNLLQK-V--DGGDYFI--EKIEREDFLRKQRTFDNGSIPHQVHLDEM 420
CQR24647       358 --DGYAG YIDG K TTQEAFYKYIKNLLSK-F--EGADYFL--DKIEREDFLKKQRTFDNGSIPHQIHLQEM 420
WP_000066813   358 --DGYAG YIEG K TTQEAFYKYIKNLLSK-F--EGADYFI--DKIEREDFLRKQRTFDNGSIPHQIHLQEM 420
WP_009754323   358 --DGYAG YIEG K TTQENFYRFIKKAIEK-I--EGSNYFI--DKIDREDFLRKQRTFDNGSIPHQIHLQEM 420
WP_044674937   357 --DGYAG YIEG K TTQENFYRFIKKAIEK-I--EGSNYFI--DKIDREVFLRKQRSFYNGVIPHQIHLQEM 419
WP_044676715   357 --DGYAG YIEG K TTQENFYRFIKKAIEK-I--EGSNYFI--DKIDREVFLRKQRSFYNSVIPHQIHLQEM 419
WP_044680361   357 --DGYAG YIEG K TTQENFYRFIKKAIEK-I--EGSNYFI--DKIDREDFLRKQRTFDNGSIPHQIHLQEM 419
WP_044681799   357 --DGYAG YIEG K TTQENFYRFIKKAIEK-I--EGSDYFI--NGSGDFL--DKIDREDFLRKQRTFDNGSIPHQIHLQEM 419
WP_049533112   357 --KGYAG YIEN G VKQDEFYKYLKGILLQ-I--NGSGDFL--DKIDREDFLRKQRTFDNGSIPHQIHLQEM 419
WP_029090905   316 fyTDYIG YEES K SKEERLFKHIELLLAKeNv1TTVEHAL1eKNITFASLLPLQRSSRNAVIPYQVHEKEL 403
WP_006506696   361 ksKGYYN YINR K APVDEFYKYVKKCIEK-vdtPEAKQIln--DIFLENFLLKQNSRTNGVPYQMQLDEM 429
AIT42264       357 --NGYAG YIDG G ASQEEFYKFIKPILEK-M--DGTEELLv--KLNREDLLRKQRSFYNGVIPYQIHLGEL 419
WP_034440723   363 --NGYAG YIDG K TSQEDFYKFVKAQLKG---eENGEYFL--EAIENENFLRKQRSFYNGVIPYQIHLGEL 425
AKQ21048       357 --DGYAG YIDG G ASQEEFYKFIKPILEK-M--DGTEELLv--DKLNREDFLRKQRSFYNGVIPHQIHLGEL 419
WP_002436532   356 --NGYAG YIDG K TTQENFYKYIEKVMKT-IksDKKDYFL--EKIAQENFLRKQRTFDNGVIPHQIHLQEM 420
WP_002364836   363 --DGYAG YIAH A VSQLKFYQVVKKIIQD-I--AGAEYFL--EKIAQENFLRKQRTFDNGVIPHQIHLAEL 427
WP_016631044   314 --DGYAG YIAH A VSQLKFYQVVKKIIQD-I--AGAEYFL--EKVDQENFLLKQRTTANGVIPHQVHLTEL 378
EMS75795       100 --NGYAG YIDG K TTQEDFYKFLKKELNG-I--AGSERFM--EKVDQENFLLKQRTTANGVIPHQVHLTEL 162
WP_002373311   363 --DGYAG YIAH A VSQLKFYQVVKKIIQD-I--AGAEYFL--EKIAQENFLRKQRTFDNGVIPHQIHLAEL 427
WP_002378009   363 --DGYAG YITH A VSQLKFYQVVKKIIQD-I--AGAEYFL--EKIAQENFLRKQRTFDNGVIPHQIHLAEL 427
WP_002407324   363 --DGYAG YITH A VSQLKFYQVVKKIIQD-I--AGAEYFL--EKIAQENFLRKQRTFDNGVIPHQIHLAEL 427
WP_002413717   363 --DGYAG YIAH A VSQLKFYQVVKKIIQD-I--AGAEYFL--EKIAQENFLRKQRTFDNGVIPHQIHLAEL 427
WP_010775580   365 --DGYAG YIAH A VSQLKFYQVVKKIIQD-I--AGAEYFL--EKIAQENFLRKQRTFDNGVIPHQIHLAEL 429
```

-continued

```
WP_010818269   363 --DGYAG YIAH A VSQLKFYQYVKKIIQD-I--AGAEYFL---EKIAQENFLRKQRTFDNGVIPHQIHLAEL 427
WP_010824395   363 --DGYAG YITH A VSQLKFYQYVKKIIQD-I--AGAEYFL---EKIAQENFLRKQRTFDNGVIPHQIHLAEL 427
WP_016622645   363 --DGYAG YIAH A VSQLKFYQYVKKIIQD-I--AGAEYFL---EKIAQENFLRKQRTFDNGVIPHQIHLAEL 427
WP_033625576   363 --DGYAG YIAH A VSQLKFYQYVKKIIQD-I--AGAEYFL---EKIAQENFLRKQRTFDNGVIPHQIHLAEL 427
WP_033789179   363 --DGYAG YIAH A VSQLKFYQYVKKIIQD-I--AGAEYFL---EKIAQENFLRKQRTFDNGVIPHQIHLAEL 427
WP_002310644   361 --NGYAG YIEG H ATQEDFYKFVKKELTG-I--RGSEVFL---TKIEQENFLRKQRTFDNGVIPHQIHLTEL 423
WP_002312694   362 --NGYAG YIEG H ATQDAFYKFVKKELTG-I--RGSEVFL---TKIEQENFLRKQRTFDNGVIPHQIHLTEL 424
WP_002314015   362 --NGYAG YIEG H ATQEDFYKFVKKELTG-I--RGSEVFL---TKIEQENFLRKQRTFDNGVIPHQIHLTEL 424
WP_002320716   362 --NGYAG YIEG H ATQEDFYKFVKKELTG-I--RGSEVFL---TKIEQENFLRKQRTFDNGVIPHQIHLTEL 424
WP_002330729   361 --NGYAG YIEG H ATQEDFYKFVKKELTG-I--RGSEVFL---TKIEQENFLRKQRTFDNGVIPHQIHLTEL 423
WP_002335161   362 --NGYAG YIEG H ATQEDFYKFVKKELTG-I--RGSEVFL---TKIEQENFLRKQRTFDNGVIPHQIHLTEL 424
WP_002345439   362 --NGYAG YIEG H ATQEDFYKFVKKELTG-I--RGSEVFL---TKIEQENFLRKQRTFDNGVIPHQIHLTEL 424
WP_034867970   355 --NGYAG YIKG K TTQEEFYKFVKKELSG-V--VGSEPFL---EKIDQETFLLKQRTYTNGVIPHQVHLIEL 417
WP_047937432   362 --NGYAG YIKG K TTQEEFYKFVKKELTG-I--RGSEVFL---TKIEQENFLRKQRTFDNGVIPHQIHLTEL 424
WP_010720994   355 --NGYAG YIKG K TTQEEFYKFVKKELSG-V--VGSEPFL---EKIDQETFLLKQRTYTNGVIPHQVHLIEL 417
WP_010737004   355 --NGYAG YIKG K TTQEEFYKFVKKELTG-I--RGSEPFL---EKIDQETFLLKQRTYTNGVIPHQVHLIEL 417
WP_034700478   355 --NGYAG YIKG K TTQEEFYKFVKKELSG-V--VGSEPFL---EKIDQETFLLKQRTYTNGVIPHQVHLIEL 417
WP_007209003   359 --NGYAG YIDG K TKEEFYKYLKTTLVQ----kSGYQYFI---EKIEQENFLRKQRIYDNGVIPHQVHAEEL 421
WP_023519017   355 --NGYAG YVKG K ATQEEFYKFLRTELAG-L--EESQSIM---EKIDLEIYLLKQRTFANGVIPHQIHLVEM 417
WP_010770040   358 --SGYAG YVEN S VTQAEFYKYIKKAIEK-V--PGAEYFL---EKIEQETFLDKQRTFNNGVIPHQIHLEEL 422
WP_048604708   354 --DGYAG YIDN S TSQEKFYKYITNLIEK-I--DGAEYFL---KKIENEDFLRKQRTFDNGIIPHQIHLEEL 418
WP_010750235   355 --DGYAG YIDG F TKQADFYKFLKKELTG-V--PGSEPML---AKIDQENFLLKQRTPTNGVIPHQVHLTEF 417
AII16583       396 --NGYAG YIDG G ASQEEFYKFIKPILEK-M--DGTEELLv--KLNREDLLRKQRTEDNGSIPHQLHLGEL 458
WP_029073316   367 kkNNYCN YINH K TPVDEFYKYIKKLIEK-IdaPDVKTILn--KIELESFMLKQNSRTNGAVPYQMQLDEL 435
WP_031589969   367 kkNNYCN YINH K TPVDEFYKYIKKLIEK-IdaPDVKTILn--KIELESFMLKQNSRTNGAVPYQMQLDEL 435
KDA45870       354 -iSGYAG YIDG K VSEEDFYKYTKKTLKG-I--PETEEILq--KIDANNYLRKQRTFDNGAIPHQVHLKEL 417
WP_039099354   360 ------- YVDG K -SKEDFYCGDITKALKNnPdhPIVSEIKk-LIELDQFMPKQRTKDNGAIPHQLHQQEL 425
AKP02966       349 ------- YINK K --KELYTSLKKFKLKVaLp-TNlAKEAe-EKISKGTYLVKPRNSENGVVPYQLNKIEM 415
WP_010991369   363 --HGYAG YIDG - TKQADFYKYMKMTLEN-I--EGADYFI---AKIEKENFLRKQRTFDNGAIPHQLHLEEL 425
WP_033838504   363 --HGYAG YIDG - TKQADFYKYMKMTLEN-I--EGADYFI---TKIEEENFLRKQRTFDNGVIPHQLHLEEL 425
EHN60060       366 --HGYAG YIDG - TKQADFYKYMKMTLEN-V--EGADYFI---AKIEKENFLRKQRTFDNGAIPHQLHLEEL 428
EFR89594       132 ------- YIDG - TKQADFYKYMKTTLEN-I--EGADYFI---AKIEKENFLRKQRTFDNGAIPHQLHLEEL 194
WP_038409211   363 --DGYAG YIDG - TTQEKFYKYMKKMLAN-I--DGADYFI---DQIEEENFLRKQRTFDNGTIPHQLHLEEL 425
EFR95520         1 ------- ---- - --MKKMLAN-I--DGADYFI---DQIEEENFLRKQRTFDNGAIPHQLHLEEL 44
WP_003723650   363 --DGYAG YIEG - TKQVDFYKYLKTILEN-I--EGSDYFI---AKIEEENFLRKQRTFDNGAIPHQLHLEEL 425
WP_003727705   363 --DGYAG YIDG - TKQADFYKYLKTTLEN-V--EGADYFI---TKIEEENFLRKQRTFDNGVIPHQLHLEEL 425
WP_003730785   363 --DGYAG YIDG - TKQVDFYKYLKTTLEN-V--EGADYFI---TKIEEENFLRKQRTFDNGVIPHQLHLEEL 425
WP_003733029   363 --HGYAG YISG - TKQVDFYKYMKATLEK-I--EGADYFI---AKIEEENFLRKQRTFDNGAIPHQLHLEEL 425
WP_003739838   363 --DGYAG YIDG - TKQVDFYKYLKTILEN-I--EGADYFI---AKIEEENFLRKQRTFDNGAIPHQLHLEEL 425
WP_014601172   363 --DGYAG YIDG - TKQVDFYKYLKTILEN-I--EGADYFI---AKIEEENFLRKQRTFDNGAIPHQLHLEEL 425
WP_023548323   363 --DGYAG YIDG - TKQVDFYKYLKTILEN-V--EGSDYFI---TKIEEENFLRKQRTFDNGAIPHQLHLEEL 425
WP_031665337   363 --DGYAG YISG - TKQVDFYKYMKATLEK-I--EGADYFI---AKIEEENFLRKQRTFDNGVIPHQLHLEEL 425
WP_031669209   363 --HGYAG YIDG - TKQVDFYKYLKTILEN-I--EGADYFI---AKIEEENFLRKQRTFDNGAIPHQLHLEEL 425
WP_033920898   363 --DGYAG YIDG - TKQVDFYKYLKTILEN-I--EGADYFI---AKIEEENFLRKQRTFDNGVIPHQLHLEEL 425
AKI42028       366 --DGYAG YIDG - TKQVDFYKYLKTILEN-I--EGADYFI---AKIEEENFLRKQRTFDNGAIPHQLHLEEL 428
AKI50529       366 --DGYAG YIDG - TKQVDFYKYLKTILEN-I--EGADYFI---AKIEEENFLRKQRTFDNGAIPHQLHLEEL 428
EFR83390       363 --DGYAG YIEG - TKQEAFYKYMKMLEH-V--EGADYFI---NQIEEENFLRKQRTFDNGAIPHQLHLEEL 425
WP_046323366   373 --NGYAG YIDG G ASQEEFYKFIKPILEK-M--DGTEELLv--KLNREDLLRKQRTFDNGSIPHQIHLGEL 435
AKE81011       365 kvKGYYN YINR K APVDEFYKFVKKCIEK-VdtPEAKQILh--DIELENFLLKQNSRTNGSVPYQMQLDEM 433
CUO82355       366 kIHNYLG YIKY D TPVEEFYKYIKGILLAK-VdtDEAREILe--RIDLEKFMLKQNSRTNGSIPYQMQKDEM 434
WP_033162887   390 --NGYAG YIDG G ASQEEFYKFIKPILEK-M--DGTEELLv--KLNREDLLRKQRTFDNGSIPHQLHLGEL 452
AGZ01981
```

```
AKA60242         357 --NGYAG YIDG G ASQEEFYKFIKPILEK-M--DGTEELLv--KLNREDLLRKQRTFDNGSIPHQIHLGEL                     419
AKS40380         357 --NGYAG YIDG G ASQEEFYKFIKPILEK-M--DGTEELLv--KLNREDLLRKQRTFDNGSIPHQIHLGEL                     419
4UN5_B           361 --NGYAG YIDG G ASQEEFYKFIKPILEK-M--DGTEELLv--KLNREDLLRKQRTFDNGSIPHQIHLGEL                     423
WP_010922251     420 HAILRRQEDFYPFLKD--NRE KIEKILTFRIPYYVGPL ARG-n-SRFAWMTR---KSEETITPWNFE[]VDKGA                 486
WP_039695303     423 HAILRRQGDYYPPLKE--KQD RIEKILTFRIPYYVGPL VRKD-SRFAWAEY--RSDEKITPWNFDKVIDKEK                   489
WP_045635197     420 NAILRRQGEYYPFLKD--NKE KIEKILTFRIPYYVGPL ARGN--RDFAWLTR---NSDEAIRPWNFEEIVDKAS                 486
5AXW_A           184 KQLLKVQKAYHQLDQSfi--D TYIDLLETRRTYYEGPG ---Eg--SPFGWKDI---                                   229
WP_009880683     104 HAILRRQEDFYPFLKD--NRE KIEKILTFRIPYYVGPL ARG-n-SRFAWMTR---KSEETITPWNFEEVVDKGA                 170
WP_010922251     420 HAILRRQEDFYPFLKD--NRE KIEKILTFRIPYYVGPL ARG-n-SRFAWMTR---KSEETITPWNFEEVVDKGA                 486
WP_011054416     420 HAILRRQEDFYPFLKD--NRE KIEKILTFRIPYYVGPL ARG-n-SRFAWMTR---KSEETITPWNFEEVVDKGA                 486
WP_011284745     420 HAILRRQEDFYPFLKD--NRE KIEKILTFRIPYYVGPL ARG-n-SRFAWMTR---KSEETITPWNFEEVVDKGA                 486
WP_011285506     420 HAILRRQEDFYPFLKD--NRE KIEKILTFRIPYYVGPL ARG-n-SRFAWMTR---KSEETITPWNFEEVVDKGA                 486
WP_011527619     420 HAILRRQEDFYPFLKD--NRE KIEKILTFRIPYYVGPL ARG-n-SRFAWMTR---KSEETITPWNFEEVVDKGA                 486
WP_012560673     420 HAILRRQEDFYPFLKD--NRE KIEKILTFRIPYYVGPL ARG-n-SRFAWMTR---KSEETITPWNFEEVVDKGA                 486
WP_014407541     420 HAILRRQEDFYPFLKD--NRE KIEKILTFRIPYYVGPL ARG-n-SRFAWMTR---KSEETITPWNFEEVVDKGA                 486
WP_020905136     420 HAILRRQEDFYPFLKD--NRE KIEKILTFRIPYYVGPL ARG-n-SRFAWMTR---KSEETITPWNFEEVVDKGA                 486
WP_023080005     420 HAILRRQEDFYPFLKD--NRE KIEKILTFRIPYYVGPL ARG-n-SRFAWMTR---KSEETITPWNFEEVVDKGA                 486
WP_023610282     420 HAILRRQEDFYPFLKD--NRE KIEKILTFRIPYYVGPL ARG-n-SRFAWMTR---KSEETITPWNFEEVVDKGA                 486
WP_030125963     420 HAILRRQEDFYPFLKD--NRE KIEKILTFRIPYYVGPL ARG-n-SRFAWMTR---KSEETITPWNFEEVVDKGA                 486
WP_030126706     420 HAILRRQEDFYPFLKD--NRE KIEKILTFRIPYYVGPL ARG-n-SRFAWMTR---KSEETITPWNFEEVVDKGA                 486
WP_031488318     420 HAILRRQEDFYPFLKD--NRE KIEKILTFRIPYYVGPL ARG-n-SRFAWMTR---KSEETITPWNFEEVVDKGA                 486
WP_032460140     420 HAILRRQEDFYPFLKD--NRE KIEKILTFRIPYYVGPL ARG-n-SRFAWMTR---KSEETITPWNFEEVVDKGA                 486
WP_032461047     420 HAILRRQEDFYPFLKD--NRE KIEKILTFRIPYYVGPL ARG-n-SRFAWMTR---KSEETITPWNFEEVVDKGA                 486
WP_032462016     420 HAILRRQEDFYPFLKD--NRE KIEKILTFRIPYYVGPL ARG-n-SRFAWMTR---KSEETITPWNFEEVVDKGA                 486
WP_032462936     420 HAILRRQEDFYPFLKD--NRE KIEKILTFRIPYYVGPL ARG-n-SRFAWMTR---KSEETITPWNFEEVVDKGA                 486
WP_032464890     420 HAILRRQEDFYPFLKD--NRE KIEKILTFRIPYYVGPL ARG-n-SRFAWMTR---KSEETITPWNFEEVVDKGA                 486
WP_033889930     245 HAILRRQEDFYPFLKD--NRE KIEKILTFRIPYYVGPL ARG-n-SRFAWMTR---KSEETITPWNFEEVVDKGA                 311
WP_038431314     420 HAILRRQEDFYPFLKD--NRE KIEKILTFRIPYYVGPL ARG-n-SRFAWMTR---KSEETITPWNFEEVVDKGA                 486
WP_038432938     420 HAILRRQEDFYPFLKD--NRE KIEKILTFRIPYYVGPL ARG-n-SRFAWMTR---KSEETITPWNFEEVVDKGA                 486
WP_038434062     420 HAILRRQEDFYPFLKD--NRE KIEKILTFRIPYYVGPL ARG-n-SRFAWMTR---KSEETITPWNFEEVVDKGA                 486
BAQ51233         331 HAILRRQEDFYPFLKD--NRE KIEKILTFRIPYYVGPL ARG-n-SRFAWMTR---KSEETITPWNFEEVVDKGA                 397
KGE60856         --- -------------------- ------------------ ------------- --------------------                ---
KGE60162         --- -------------------- ------------------ ------------- --------------------                ---
WP_002989955     420 HAILRRQEDFYPFLKD--NRE KIEKILTFRIPYYVGPL ARG-n-SRFAWMTR---KSEETITPWNFEEVVDKGA                 486
WP_003030002     420 HAILRRQEHYPFLKE--NQD KIEKILTFRIPYYVGPL ARKG--SRFAWAEY---KADEKITPWNFDDILDKEK                  486
WP_003065552     423 HAILRRQGDYYPPLKE--NQD RIEKILTFRIPYYVGPL ARKD--SRFSWAEY---HSDEKITPWNFDKVIDKEK                 489
WP_001040076     421 RAILRRQSEYYPFLKE--NLD RIEKILTFRIPYYIGPL AREK--SDFAWMTR---KTDDSIRPWNFEDLVDKEK                 487
WP_001040078     421 KAILRRQSEYYPFLKE--NQD RIEKILTFRIPYYIGPL AREK--SDFAWMTR---KTDDSIRPWNFEDLVDKEK                 487
WP_001040080     421 KAILRRQSEYYPFLKE--NQD RIEKILTFRIPYYIGPL AREK--SDFAWMTR---KTDDSIRPWNFEDLVDKEK                 487
WP_001040081     421 KAILRRQSEYYPFLKE--NQD RIEKILTFRIPYYIGPL AREK--SDFAWMTR---KTDDSIRPWNFEDLVDKEK                 487
WP_001040083     421 KAIIRRQSEYYPFLKE--NQD RIEKILTFRIPYYIGPL AREK--SDFAWMTR---KTDDSIRPWNFEDLVDKEK                 487
WP_001040085     421 KAIIRRQSEYYPFLKE--NQD RIEKILTFRIPYYIGPL AREK--SDFAWMTR---KTDDSIRPWNFEDLVDKEK                 487
WP_001040087     421 KAIIRRQSEYYPFLKE--NQD RIEKILTFRIPYYIGPL AREK--SDFAWMTR---KTDDSIRPWNFEDLVDKEK                 487
WP_001040088     421 KAIIRRQSEYYPFLKE--NQD RIEKILTFRIPYYIGPL AREK--SDFAWMTR---KTDDSIRPWNFEDLVDKEK                 487
WP_001040089     421 KAIIRRQSEYYPFLKE--NQD RIEKILTFRIPYYIGPL AREK--SDFAWMTR---KTDDSIRPWNFEDLVDKEK                 487
WP_001040090     421 KAIIRRQSEYYPFLKE--NQD RIEKILTFRIPYYIGPL AREK--SDFAWMTR---KTDDSIRPWNFEDLVDKEK                 487
WP_001040091     421 KAIIRRQSEYYPFLKE--NQD RIEKILTFRIPYYIGPL AREK--SDFAWMTR---KTDDSIRPWNFEDLVDKEK                 487
WP_001040092     421 KAIIRRQSEYYPFLKE--NQD RIEKILTFRIPYYIGPL AREK--SDFAWMTR---KTDDSIRPWNFEDLVDKEK                 487
WP_001040094     421 KAIIRRQSEYYPFLKE--NQD RIEKILTFRIPYYIGPL AREK--SDFAWMTR---KTDDSIRPWNFEDLVDKEK                 487
WP_001040095     421 RAIIRRQSEYYPFLKE--NLD RIEKILTFRIPYYVGPL ARGN--SDFAWMTR---KTDDSIRPWNFEDLVDKEK                 487
WP_001040096     421 RAIIRRQSEYYPFLKE--NLD RIEKILTFRIPYYVGPL AREK--SDFAWMTR---KTDDSIRPWNFEDLVDKEK                 487
WP_001040097     421 RAIIRRQSEYYPFLKE--NLD RIEKILTFRIPYYVGPL AREK--SDFAWMTR---KTDDSIRPWNFEDLVDKEK                 487
WP_001040098     421 RAIIRRQSEYYPFLKE--NLD RIEKILTFRIPYYVGPL AREK--SDFAWMTR---KTDDSIRPWNFEDLVDKEK                 487
```

-continued

```
WP_001040099   421 RAIIRRQSEYYPPLKE--NLD RIEKILTFRIPYYVGPL AREK--SDFAWMTR---KTDDSIRPWNFEDLVDKEK 487
WP_001040100   421 RAIIRRQSEYYPPLKE--NLD RIEKILTFRIPYYIGPL AREK--SDFAWMTR---KTDDSIRPWNFEDLVDKEK 487
WP_001040104   421 KAIIRRQSEYYPPLKE--NQD RIEKILTFRIPYYIGPL AREK--SDFAWMTR---KTDDSIRPWNFEELVDKEA 487
WP_001040105   421 KAIIRRQSEYYPPLKE--NLD RIEKILTFRIPYYIGPL AREK--SDFAWMTR---KTDDSIRPWNFEELVDKEA 487
WP_001040106   421 KAIIRRQSEYYPPLKE--NLD RIEKILTFRIPYYVGPL AREK--SDFAWMTR---KTDDSIRPWNFEELVDKEA 487
WP_001040107   421 KAIIRRQSEYYPPLKE--NLD RIEKILTFRIPYYVGPL AREK--SDFAWMTR---KTDDSIRPWNFEELVDKEA 487
WP_001040108   421 KAIIRRQSEYYPPLKE--NLD RIEKILTFRIPYYVGPL AREK--SDFAWMTR---KTDDSIRPWNFEELVDKEA 487
WP_001040109   421 KAIIRRQSEYYPPLKE--NLD RIEKILTFRIPYYVGPL AREK--SDFAWMTR---KTDDSIRPWNFEELVDKEA 487
WP_001040110   421 KAIIRRQSEYYPPLKE--NLD RIEKILTFRIPYYVGPL AREK--SDFAWMTR---KTDDSIRPWNFEELVDKEA 487
WP_015058523   421 RAIIRRQSEYYPPLKE--NQD RIEKILTFRIPYYIGPL ARGN--SDFAWMTR---KTDDSIRPWNFEDLVDKEK 487
WP_017643650   421 RAIIRRQSEYYPPLKE--NLD RIEKILTFRIPYYIGPL AREK--SDFAWMTR---KTDDSIRPWNFEDLVDKEK 487
WP_017647151   421 KAIIRRQSEYYPPLKE--NLD RIEKILTFRIPYYVGPL AREK--SDFAWMTR---KTDDSIRPWNFEELVDKEK 487
WP_017648376   421 KAIIRRQSEYYPPLKE--NLD RIEKILTFRIPYYVGPL AREK--SDFAWMTR---KTDDSIRPWNFEELVDKEK 487
WP_017649527   421 KAIIRRQSEYYPPLKE--NQD RIEKILTFRIPYYIGPL AREK--SDFAWMTR---KTDDSIRPWNFEELVDKEA 487
WP_017771611   421 KAIIRRQSEYYPPLKE--NLD RIEKILTFRIPYYVGPL AREK--SDFAWMTR---KTDDSIRPWNFEELVDKEA 487
WP_017771984   421 KAIIRRQSEYYPPLKE--NLD RIEKILTFRIPYYVGPL AREK--SDFAWMTR---KTDDSIRPWNFEELVDKEA 487
CFQ25032       421 KAIIRRQSEYYPPLKE--NQD RIEKILTFRIPYYVGPL AREK--SDFAWMTR---KTDDSIRPWNFEELVDKEA 487
CFV16040       421 KAIIRRQSEYYPPLKE--NQD RIEKILTFRIPYYIGPL AREK--SDFAWMTR---KTDDSIRPWNFEDLVDKEK 487
KLJ37842       421 KAIIRRQSEYYPPLKE--NQD RIEKILTFRIPYYIGPL AREK--SDFAWMTR---KTDDSIRPWNFEDLVDKEK 487
KLJ72361       421 KAIIRRQSEYYPPLKE--NQD RIEKILTFRIPYYIGPL AREK--SDFAWMTR---KTDDSIRPWNFEDLVDKEK 487
KLL20707       421 KAIIRRQSEYYPPLKE--NLD RIEKILTFRIPYYIGPL AREK--SDFAWMTR---KTDDSIRPWNFEDLVDKEK 487
KLL42645       421 KAIIRRQSEYYPPLKE--NQD RIEKILTFRIPYYIGPL AREK--SDFAWMTR---KTDDSIRPWNFEELVDKEA 487
WP_047207273   421 KAIIRRQSEYYPPLKE--NQD RIEKILTFRIPYYIGPL AREK--SDFAWMTR---KADEKITPWNFDDILDKEK 487
WP_047209694   421 RAIIRRQSEYYPPLKE--NQD RIEKILTFRIPYYIGPL ARKG--SDFAWAEY---KADEKITPWNFDDILDKEK 487
WP_049516684   421 KAIIRRQSEYYPPLKE--NQD RIEKILTFRIPYYVGPL ARKG--SRFAWAEY---KADEKITPWNFDDILDKEK 487
GAD46167       420 KAIIRRQSEYYPPLKE--NQD RIEKILTFRIPYYVGPL ARKG--SRFAWAEY---KADEKITPWNFDDILDKEK 486
WP_050198062   420 KAIIRRQSEYYPPLKE--NQD RIEKILTFRIPYYVGPL ARKD--SRFAWAEY---RSDEKITPWNFDKVIDKEK 486
WP_050201642   421 KAIIRRQEFYPPLKE--NQE EIEKILTFRIPYYVGPL ARG-n-SRFAWLTR---KSEEAITPWNFEEVVDKGA 487
WP_050204027   430 KAIIRRQGEHYPPLKE--NQD KIEKILTFRIPYYVGPL ARKG--SRFAWAEY---KADEKITPWNFDDILDKEK 496
WP_050881965   420 KDIIRRQSEYYPPLKE--NQD RIEKILTFRIPYYIGPL AREK--SDFAWMTR---KTDDSIRPWNFEELVDKEA 486
WP_050886065   420 KAIIRRQSEYYPPLKE--NQD RIEKILTFRIPYYIGPL AREK--SDFAWMTR---KTDDSIRPWNFEELVDKEA 486
AHN30376       421 RAIIRRQSEYYPPLKE--NLD RIEKILTFRIPYYIGPL ARGN--SDFAWMTR---KTDDSIRPWNFEELVDKEA 487
EA078426       421 KAIIRRQSEYYPPLKE--NLD KIEKILTFRIPYYIGPL AREK--SDFAWMTR---KTDDSIRPWNFEELVDKEA 487
CCW42055       421 HAILRRQGEHYPPLKE--NQD RIEKILTFRIPYYVGPL AREK--SDFAWAEY---KADEKITPWNFEELVDKEA 487
WP_003041502   421 HAILRRQGEHYPPLKE--NQD KIEKILTFRIPYYVGPL ARKG--SRFAWAEY---KADEKITPWNFEEVVDKGA 486
WP_037593752   420 HAILRRQGEHYPPLKE--NQD KIEKILTFRIPYYVGPL ARKG--SRFAWAEY---KADEKITPWNFEEVVDKGA 486
GAD46167       420 HAILRRQGDFYPPLKE--NQE KIEKILTFRIPYYVGPL ARKD--SRFAWAEY---RSDEKITPWNFDKVIDKEK 486
WP_018363470   421 HAILRRQEFYPPLKE--NQE EIEKILTFRIPYYVGPL ARG-n-SRFAWLTR---KSEEAITPWNFEEVVDKGA 487
WP_003043819   430 HAILRRQGEHYPPLKE--NQD KIEKILTFRIPYYVGPL ARKG--SRFAWAEY---KADEKITPWNFDDILDKEK 496
WP_006269658   420 HAILRRQEDFYPPLKD--NRE KIESLLTFRIPYYVGPL VRKG--SRFAWVKR---KSEETITPWNFEEVVDKGA 486
WP_048800889   420 HAILRRQEDFYPPLKD--NRE KIESLLTFRIPYYVGPL ARG-n-SRFAWMTR---KSEETITPWNFEEVVDKGA 486
WP_012767106   420 HAILRRQEDFYPPLKD--NRE KIESLLTFRIPYYVGPL ARG-n-SRFAWMTR---KSEETITPWNFEEVVDKGA 486
WP_014612333   420 HAILRRQEDFYPPLKD--NRE KIESLLTFRIPYYVGPL ARG-n-SRFAWMTR---KSEETITPWNFEEVVDKGA 486
WP_015017095   420 HAILRRQEDFYPPLKD--NRE KIESLLTFRIPYYVGPL ARG-n-SRFAWMTR---KSEETITPWNFEEVVDKGA 486
WP_015057649   420 HAILRRQEDFYPPLKD--NRK KIESLLTFRIPYYVGPL ARG-n-SRFAWMTR---KSEETITPWNFEEVVDKGA 486
WP_048327215   420 HAILRRQEDFYPPLKD--NRK KIESLLTFRIPYYVGPL ARG-h-SRFAWVKR---KPDGAIRPWNFEEIVDEEA 486
WP_049519324   420 HAILRRQEVEYPPLKE--NRK KIESLLTFRIPYYVGPL ARG-h-SRFAWVKR---KPDGAIRPWNFEEIVDEEA 486
WP_012515931   420 HAILRRQEVEYPPLKE--NRK KIESLLTFRIPYYVGPL ARG-h-SRFAWAEY---KPDGAIRPWNFEEIVDEEA 486
WP_021320964   420 HAILRRQEVEYPPLKE--NRK KIESLLTFRIPYYVGPL ARG-h-SRFAWVKR---KPDGAIRPWNFEEIVDEEA 486
WP_037581760   420 HAILRRQEVEYPPLKE--NRK KIESLLTFRIPYYVGPL ARG-h-SRFAWVKR---KPDGAIRPWNFEEIVDEEA 486
WP_004232481   421 RTILRRQGEHYPPLKE--NQA KIEKILTFRIPYYVGPL ARKN--SRFAWAKY---HSDEPITPWNFDEVVDKEK 487
WP_009854540   421 HAILRRQGDYYPPLKE--KQD RIEKILTFRIPYYVGPL VRKD--SRFAWAEY---RSDEKITPWNFDKVIDKEK 487
WP_012962174   421 HAILRRQGEHYAFLKE--NQA KIEKILTFRIPYYVGPL ARKN--SRFAWAEY---HSDEKITPWNFDEIIDKEK 487
WP_039695303   423 HAILRRQGDYYPPLKE--KQD RIEKILTFRIPYYVGPL VRKD--SRFAWAEY---RSDEKITPWNFDKVIDKEK 489
```

-continued

```
WP_014334983   420 HSILRRQGDYYPPLKE--NQA KIEKILTFRIPYYVGPL ARKD--SRFAWANY--HSDEPITPWNFDEVVDKEK 486
WP_003092269   420 KAIIRRQEKFYPPLKE--NQK KIEKILTFKIPYYVGPL ANG-q-SSFAWLKR--QSNESITPWNFEEVVDQEA 486
AHY15608       420 KAIIRRQEKFYPPLKE--NQK KIEKLFTFKIPYYVGPL ANG-q-SSFAWLKR--QSNESITPWNFEEVVDQEA 486
AHY17476       420 KAIIRRQEKFYPPLKE--NQK KIEKLFTFKIPYYVGPL ANG-q-SSFAWLKR--QSNESITPWNFEEVVDQEA 486
ESR09100           ------------------- ----------------- ---------------- ---------------------
AGM98575       420 KAIIRRQEKFYPPLKE--NQK KIEKILTFKIPYYVGPL ANG-q-SSFAWLKR--QSNESITPWNFEEVVDQEA 486
ALF27331       420 RAIIRRQAEFYPPLAD--NQD KIEKILTFRIPYYVGPL ARGK--SDFSWLSR--KSADKITPWNFDEIVDKES 486
WP_018372492   433 QAIILNQSKYYPPLAE--NKE KIEKILTFRIPYYVGPL ARGN--SSFAWLQR--KSDEAIRPWNFEQVVDMET 499
WP_045618028   421 NAIIRRQGEHYPPLQE--NKE KIEKILTFRIPYYVGPL ARGN--RDFAWLTR--NSDQAIRPWNFEEIVDKAS 487
WP_045635197   420 NAIIRRQGEYYPPLKD--NKE KIEKILTFRIPYYVGPL ARGN--RDFAWLTR--NSDEAIRPWNFEEIVDKAS 486
WP_002263549   420 RAIIRRQAEFYPPLAD--NQD RIEKILTFRIPYYVGPL ARGK--SDFAWLSR--KSADKITPWNFDEIVDKES 486
WP_002263887   420 RAIIRRQAEFYPPLAD--NQD RIEKILTFRIPYYVGPL ARGK--SDFAWLSR--KSADKITPWNFDEIVDKES 486
WP_002264920   420 HAIIRRQGDYYPPLKE--NQD RIEKILTFRIPYYVGPL ARGK--SDFAWLSR--KSADKITPWNFDEIVDKES 486
WP_002269043   420 RAIIRRQAEFYPPLAD--NQD RIEKLLTFRIPYYVGPL ARGK--SDFAWLSR--KSADKITPWNFDEIVDKES 486
WP_002269448   420 RAIIRRQAEFYPPLAD--NQD RIEKILTFRIPYYVGPL ARGK--SDFAWLSR--KSADKITPWNFDEIVDKES 486
WP_002271977   420 RAIIRRQAEFYPPLAD--NQD RIEKILTFRIPYYVGPL ARGK--SDFAWLSR--KSADKITPWNFDEIVDKES 486
WP_002272766   420 RAIIRRQAEFYPPLAD--NQD RIEKILTFRIPYYVGPL ARGK--SDFAWLSR--KSADKITPWNFDEIVDKES 486
WP_002273241   420 RAIIRRQAEFYPPLAD--NQD RIEKILTFRIPYYVGPL ARGK--SDFAWLSR--KSADKITPWNFDEIVDKES 486
WP_002275430   420 RAIIRRQSEFYPPLAD--NQD RIEKILTFRIPYYVGPL ARGK--SDFAWLSR--KSADKITPWNFDEIVDKES 486
WP_002276448   420 RAIIRRQAEFYPPLAD--NQD RIEKILTFRIPYYVGPL ARGK--SDFAWLSR--KSADKITPWNFDEIVDKES 486
WP_002277050   420 HAIIRRQGDYYPPLKE--NQD RIEKILTFRIPYYVGPL ARKN--SRFAWAEY--HSDEAVMPWNFDQVIDKES 486
WP_002277364   420 RAIIRRQAEFYPPLAD--NQD RIEKILTFRIPYYVGPL ARGK--SDFAWLSR--KSADKITPWNFDEIVDKES 486
WP_002279025   420 RAIIRRQAEFYPPLAD--NQD RIEKILTFRIPYYVGPL ARGK--SDFAWLSR--KSADKITPWNFDEIVDKES 486
WP_002279859   420 RAIIRRQAEFYPPLAD--NQD RIEKILTFRIPYYVGPL ARGK--SDFAWLSR--KSADKITPWNFDEIVDKES 486
WP_002280230   420 RAIIRRQAEFYPPLAD--NQD RIEKILTFRIPYYVGPL ARGK--SDFAWLSR--KSADKITPWNFDEIVDKES 486
WP_002281696   420 RAIIRRQAEFYPPLAD--NQD RIEKILTFRIPYYVGPL ARGK--SDFAWLSR--KSADKITPWNFDEIVDKES 486
WP_002282247   420 HAIIRRQGDYYPPLKE--NQD RIEKILTFRIPYYVGPL ARKN--SRFAWAEY--HSDEAVTPWNFDQVIDKES 486
WP_002282906   420 RAIIRRQAEFYPPLAD--NQD RIEKILTFRIPYYVGPL ARGK--SDFAWLSR--KSADKITPWNFDEIVDKES 486
WP_002283846   420 RAIIRRQAEFYPPLAD--NQD RIEKLLTFRIPYYVGPL ARGK--SDFAWLSR--KSADKITPWNFDEIVDKES 486
WP_002287255   420 RAIIRRQAEFYPPLAD--NQD RIEKILTFRIPYYVGPL ARGK--SDFAWLSR--KSADKITPWNFDEIVDKES 486
WP_002288990   420 RAIIRRQAEFYPPLAD--NQD RIEKILTFRIPYYVGPL ARGK--SDFAWLSR--KSADKITPWNFDEIVDKES 486
WP_002289641   420 RAIIRRQAEFYPPLAD--NQD RIEKILTFRIPYYVGPL ASGK--SDFAWLSR--KSADKITPWNFDEIVDKES 486
WP_002290427   420 RAIIRRQAEFYPPLAD--NQD RIEKILTFRIPYYVGPL ARGK--SDFAWLSR--KSADKITPWNFDEIVDKES 486
WP_002295753   420 RAIIRRQAEFYPPLAD--NQD RIEKILTFRIPYYVGPL ARGK--SDFAWLSR--KSADKITPWNFDEIVDKES 486
WP_002296423   420 RAIIRRQAEFYPPLAD--NQD RIEKILTFRIPYYVGPL ARGK--SDFAWLSR--KADEKITPWNFDDILDKEK 496
WP_002304487   430 HAIIRRQGEHYPPLKE--NQD RIEKILTFRIPYYVGPL VRKG--SRFAWAEY--HSDEAVTPWNFDQVIDKES 496
WP_002305844   420 RAIIRRQAEFYPPLAD--NQD KIEKILTFRIPYYVGPL ARGK--SDFAWLSR--KSADKITPWNFDEIVDKES 486
WP_002307203   420 RAIIRRQAEFYPPLAD--NQD RIEKILTFRIPYYVGPL ARGK--SDFAWLSR--KSADKITPWNFDEIVDKES 486
WP_002310390   420 RAIIRRQAEFYPPLAD--NQD RIEKILTFRIPYYVGPL ARGK--SDFAWLSR--KSADKITPWNFDEIVDKES 486
WP_002352408   420 RAIIRRQAEFYPPLAD--NQD RIEKILTFRIPYYVGPL ARGK--SDFAWLSR--KSADKITPWNFDEIVDKES 486
WP_012997688   420 RAIIRRQAEFYPPLAD--NQD RIEKILTFRIPYYVGPL ARGK--SDFAWLSR--KSADKITPWNFDEIVDKES 486
WP_014677909   420 RAIIRRQAEFYPPLAD--NQD RIEKILTFRIPYYVGPL ARGK--SDFAWLSR--KSADKITPWNFDEIVDKES 486
WP_019312892   420 RAIIRRQAEFYPPLAD--NQD RIEKILTFRIPYYVGPL ARGK--SDFAWLSR--KSADKITPWNFDEIVDKES 486
WP_019313659   420 RAIIRRQAEFYPPLAD--NQD RIEKILTFRIPYYVGPL ARGK--SDFAWLSR--KSADKITPWNFDEIVDKES 486
WP_019314093   420 RAIIRRQAEFYPPLAD--NQD RIEKILTFRIPYYVGPL ARGK--SDFAWLSR--KSADKITPWNFDEIVDKES 486
WP_019315370   420 HAIIRRQGDYYPPLKE--NQD RIEKILTFRIPYYVGPL ARKN--SRFAWAEY--HSDEAVTPWNFDQVIDKES 486
WP_019803776   420 RAIIRRQAEFYPPLAD--NQD RIEKILTFRIPYYVGPL ARGK--SDFAWLSR--KSADKITPWNFDEIVDKES 486
WP_019805234   420 RAIIRRQAEFYPPLAD--NQD RIEKILTFRIPYYVGPL ARGK--SDFAWLSR--KSADKITPWNFDEIVDKES 486
WP_024783594   420 RAIIRRQAEFYPPLAD--NQD RIEKILTFRIPYYVGPL ARGK--SDFAWLSR--KSADKITPWNFDEIVDKES 486
WP_024784288   420 HAIIRRQGDYYPPLKE--NQD RIEKILTFRIPYYVGPL ARKN--SRFAWAEY--HSDEAVTPWNFDQVIDKES 486
WP_024784666   420 RAIIRRQAEFYPPLAD--NQD RIEKILTFRIPYYVGPL ARGK--SDFAWLSR--KSADKITPWNFDEIVDKES 486
WP_024784894   420 RAIIRRQAEFYPPLAD--NQD RIEKILTFRIPYYVGPL ASGK--SDFAWLSR--KSADKITPWNFDEIVDKES 486
WP_024786433   420 HAIIRRQGDYYPPLKE--NQD RIEKILTFRIPYYVGPL ARKN--SRFAWAEY--HSDEAVTPWNFDQVIDKES 486
```

```
WP_049473442   420 RAIIRRQAEFYPPLAD--NQD RIEKLLTFRIPYYVGPL ARGK--SDFAWlSR---KSADKITPWNFDEIVDKES 486
WP_049474547   420 RAIIRRQAEFYPPLAD--NQD RIEKLLTFRIPYYVGPL ASGK--SDFAWlSR---KSADKITPWNFDEIVDKES 486
EMC03581       413 RAIIRRQAEFYPPLAD--NQD RIEKLLTFRIPYYVGPL ARGK--SDFAWLSR---KSADKITPWNFDEIVDKES 479
WP_000428612   421 NAILRRQGEHYPFLKE--NKE KIEKILTFRIPYYVGPL ARGN--RDFAWLTR---NSDQAIRPWNFEEIVDKAS 487
WP_000428613   421 NAILRRQGEHYPFLKD--NKE KIEKILTFRIPYYVGPL ARGN--RDFAWLTR---NSDEAIRPWNFEEIVDKAS 487
WP_049523028   420 NAILRHQGEYYPFLKE--NKD KIEKILTFRIPYYVGPL ARGN--SDFAWLSR---NSDEAIRPWNFEEMVDKSS 486
WP_003107102   389 KSIIRRQEKYPFLKD--KQV RIEKIFTFRIPYFVGPL ANG-n-SSFAWVKR---RSNESITPWNFEEVVEQEA 455
WP_054279288   422 QAILERQQAYYPFLKE--NQE KIEKILTFRIPYYVGPL ARG-n-SRFAWLTR---TSDQKITPWNFDEMVDQEA 488
WP_049531101   421 NAILRRQGEHYPFLKE--NRE KIEKILTFRIPYYVGPL ARGN--RDFAWLTR---NSDQAIRPWNFEEIVDKAS 487
WP_049538452   421 NAILRRQGEHYPFLKE--NKE KIEKILTFRIPYYVGPL ARGN--RDFAWLTR---NSDQAIRPWNFEEIVDKAS 487
WP_049549711   421 NAILRRQGEHYPFLKE--NKE KIEKILTFRIPYYVGPL ARGN--RDFAWLTR---NSDQAIRPWNFEEIVDKAS 487
WP_007896501   422 HAILRRQEKYYPFLAE--QKE KIEQLLCFRIPYYVGPL AKGGn-SSFAWLKR---RSDEPITPWNFKDVVDEEA 489
EFR44625       374 HAILRRQEKYYPFLAE--QKE KIEQLLCFRIPYYVGPL AKGGn-SSFAWLKR---RSDEPITPWNFKDVVDEEA 441
WP_002897477   420 NAILRRQGEHYPFLKE--NRE KIEKILTFRIPYYVGPL ARDN--RDFSWLTR---NSDEPIRPWNFEEVVDKAR 486
WP_002906454   420 NAILRRQGEHYLFLKE--NKE KIEKILAFRIPYYVGPL ARGN--RDFAWLTR---NSDQAIRPWNFEEIVDKAS 486
WP_009729476   421 NAILRRQGEHYIPFLKE--NKE KIEKILTFRIPYYVGPL ARGN--RDFAWLTR---NSDQAIRPWNFEEIVDKAS 487
CQR24647       421 KAILRRQGEFYPFLKE--NAE KIQQILTFKIPYYVGPL ARGN--SRFAWASY---NSNEKMTPWNFDNVIDKTS 487
WP_000066813   421 NAILRRQGEHYPFLQE--NKE KIEKILTFRIPYYVGPL ARGN--GDFAWLTR---NSDQAIRPWNFEEIVDQAS 487
WP_009754323   421 NAILRRQGEHYPLLKE--NKE KIEKILTFRIPYYVGPL ARGN--RDFAWLTR---NSDQAIRPWNFEEIVDKAS 487
WP_044674937   420 HAILRRQGEHYPFLVE--NQD KIEKILTFRIPYYVGPL ARGN--SEFAWLNR---KSDEKIRPWNFDEMVDKET 486
WP_044676715   420 HAILRRQAEFYPFLVE--NQD KIEKILTFRIPYYVGPL ARGK--SEFAWLNR---KSDEKIRPWNFDEMVDKET 486
WP_044680361   420 HAILRRQAEFYPFLVE--NQD KIEKILTFRIPYYVGPL ARGK--SEFAWLNR---KSDEKIRPWNFDEMVDKET 486
WP_044681799   420 HAILRRQAEFYPFLVE--NQD KIEKILTFRIPYYVGPL ARGN--SEFAWLNR---KSDEKIRPWNFDEMVDKET 486
WP_049533112   420 HAILRRQGEHYPFLKE--NQD KIEKILTFRIPYYVGPL ARKG--SRFAWAEY---KADEKITPWNFDDILDKEK 486
WP_029090905   404 VAILENQATYYPELLE--QKD NIHKLLTFRIPYYVGPL ADQKd-SEFAWMVR---KQAGKITPFNFEEMVDIDA 471
WP_006506696   430 IKIIDNQAEYYPILKE--KRE QLLSLLTFRIPYFGPL ETSEh---AWIKRlegKENQRILPWNYQDIVDVDA 498
AIT42264       420 TAVLDQQERKHYSPLKE--NRD KIISLLTFRIPYYVGPL ARG-n-SRFAWMTR---KSEETITPWNFEEVVDKGA 486
WP_034440723   426 HAILRRQEDFYPFLKD--NRE KIEKILTFRIPYYVGPL ARGE--SRFAWLKR---sNSEEKIKPWNEDKIVDIDK 493
AKQ21048       420 HAILRRQEDFYPFLKD--NRE KIEKILTFRIPYYVGPL ARG-n-SRFAWMTR---KSEETITPWNFEEVVDKGA 486
WP_004636532   421 QAILDRQSQYYPFLAE--NRD KIESLVTFRIPYYVGPL TVSDq-SEFAWMER---QSDEPIRPWNFDEIVNKER 488
WP_002364836   428 QAIHRQAYYPFLKE--NQE KIEQLVTFRIPYYVGPL SKGDA--STFAWLKR---QSEEPIRPWNLQETVDLDQ 495
WP_002407324   428 QAIHRQAYYPFLKE--NQE KIEQLVTFRIPYYVGPL SKGDa--NTFAWLKR---QSEEPIRPWNLQETVDLDQ 495
WP_002413717   428 QAIHRQAYYPFLKE--NQE KIEQLVTFRIPYYVGPL SKGDa--STFAWLKR---QSEEPIRPWNLQETVDLDQ 495
WP_016631044   379 QAIHRQAYYPFLKE--NQE KIEQLVTFRIPYYVGPL SKGDa--STFAWLKR---QSEEPIRPWNLQETVDLDQ 446
WP_010775580   430 KAIIERQKPYYPSLEE--ARD KMIRLLTFRIPYYVGPL AQGEet-SSFAWLER---KTPEKVTPWNATEVIDYSA 497
EMS75795       163 KAIIERQKPYYPSLEE--ARD KMIRLLTFRIPYYVGPL AQGEet-SSFAWLER---KTPEKVTPWNATEVIDYSA 231
WP_002373311   428 QAIHRQAYYPFLKE--NQE KIEQLVTFRIPYYVGPL SKGDA--STFAWLKR---QSEEPIRPWNLQETVDLDQ 495
WP_002378009   428 QAIHRQAYYPFLKE--NQE KIEQLVTFRIPYYVGPL SKGDa--NTFAWLKR---QSEEPIRPWNLQETVDLDQ 495
WP_010818269   428 QAIHRQAYYPFLKE--NQE KIEQLVTFRIPYYVGPL SKGDa--STFAWLKR---QSEEPIRPWNLQETVDLDQ 495
WP_010824395   428 QAIHRQAYYPFLKE--NQE KIEQLVTFRIPYYVGPL SKGDa--STFAWLKR---QSEEPIRPWNLQETVDLDQ 495
WP_016622645   428 QAIHRQAYYPFLKE--NQE KIEQLVTFRIPYYVGPL SKGDa--STFAWLKR---QSEEPIRPWNLQETVDLDQ 495
WP_033624816   428 QAIHRQAYYPFLKE--NQK KIEQLVTFRIPYYVGPL SKGDa--STFAWLKR---QSEEPIRPWNLQETVDLDQ 495
WP_033625576   428 QAIHRQAYYPFLKE--NQE KIEQLVTFRIPYYVGPL SKGDa--STFAWLKR---QNEKPIRPWNLQETVDLDQ 495
WP_033789179   428 QAIHRQAYYPFLKE--EQE KIESLLTFKIPYYVGPL SKGDa--STFAWLKR---QSEEPIRPWNLPEIVDMEG 495
WP_023106044   424 RAIANQKKHYPFLKE--EQE KLESLLTFKIPYYVGPL AKKQen-SPFAWLIR---KSEEKIKPWNLPEIVDMEG 492
WP_002312694   425 RAIANQKKHYPFLKE--EQE KLESLLTFKIPYYVGPL AKKQen-SPFAWLIR---KSEEKIKPWNLPEIVDMEG 493
WP_002314015   425 RAIANQKKHYPFLKE--EQE KLESLLTFKIPYYVGPL AKKQen-SPFAWLIR---KSEEKIKPWNLPEIVDMEG 493
WP_002320716   425 RAIANQKKHYPFLKE--EQE KLESLLTFKIPYYVGPL AKKQen-SPFAWLIR---KSEEKIKPWNLPEIVDMEG 493
WP_002330729   424 RAIANQKKHYPFLKE--EQE KLESLLTFKIPYYVGPL AKKQen-SPFAWLIR---KSEEKIKPWNLPEIVDMEG 492
WP_002335161   425 RAIANQKKHYPFLKE--EQE KLESLLTFKIPYYVGPL AKKQen-SPFAWLIR---KSEEKIKPWNLPEIVDMEG 493
WP_002345439   425 RAIANQKKHYPFLKE--EQE KIIALPKFRIPYYVGPL AKKQeaSSFAWIER---KTAEKINPWNFSEVVDIEK 493
WP_034867970   418 KAIIDQQKQHYPFLEE--AGP KLESLLTFKIPYYVGPL AKKQeaSSFAWIER---KTAEKINPWNFSEVVDIEK 486
WP_047937432   425 RAIIANQKKHYPFLKE--EQE KLESLLTFKIPYYVGPL AKKQen-SPFAWLIR---KSEEKIKPWNLPEIVDMEG 493
```

-continued

| | | | | | | |
|---|---|---|---|---|---|---|
| WP_010720994 | 418 | KAIIDQQKQHYPPLEE--AGP | KIIALFKFRIPYYVGPL | AKEQeaSSFAWIER--- | KTAEKINPWNFSEVDIEK | 486 |
| WP_010737004 | 418 | KAIIDQQKQHYPPLEE--AGP | KIIALFKFRIPYYVGPL | AKEQeaSSFAWIER--- | KTAEKINPWNFSEVDIEK | 486 |
| WP_034700478 | 418 | KAIIDQQKQHYPPLEE--AGP | KIIALFKFRIPYYVGPL | AKEQeaSSFAWIER--- | KTAEKINPWNFSEVDIEK | 486 |
| WP_007209003 | 422 | RAILRKQEKYYSFIKE--NHE | KIEQIFKVRIPYYVGPL | AKHNeqSRFAWNIR--- | KSDEPIRPWNMNDVVDENA | 490 |
| WP_023519017 | 418 | REIMDRQKRFYPPLKG--AQG | KIEKLLTFRIPYYVGPL | AQEGq-SPFAWLER--- | KSPSQITPWNFAEVVDKEN | 485 |
| WP_010770040 | 423 | EAIIQKQATYYPPFLAD--NKE | EMKQLVTFRIPYYVGPL | ADGN--SPFAWLER--- | ISSEPIRPGNLAEVVDIKK | 489 |
| WP_048604708 | 419 | KAILHHQAMYYPPFLQE--KFS | NFVDLLTFRIPYYVGPL | ANGN--SRFSWLSR--- | KSDEPIRPWNLAEVVDLSK | 485 |
| WP_010750235 | 418 | KAIIDQQKQYYPPFLEK--SKE | KMIQLLTFRIPYYVGPL | AQDKetSSFAWLER--- | KTTEKIKPWNAKDVIDYGA | 486 |
| AII16583 | 459 | HAILRRQEDFYPPLKD--NRE | KIEKLLTFRIPYYVGPL | ARG-n-SRFAWMTR--- | KSEETITPWNFEEVVDKGA | 525 |
| WP_029073316 | 436 | NKILENQSVYYSDLKD--NED | KIRSILTFRIPYYFGPL | ITKDr-QFDWIIKegKENERILPWNANEIVDVDK | | 506 |
| WP_031589969 | 436 | NKILENQSVYYSDLKD--NED | KIRSILTFRIPYYFGPL | ITKDr-QFDWIIKegKENERILPWNANEIVDVDK | | 506 |
| KDA45870 | 418 | VAIVENQGKYYPFLNE--NKD | KFEKILNFRIPYYVGPL | ARGN--SKFAWLTR--a-GEGKITPYNFDEMIDKET | | 484 |
| WP_039099354 | 426 | DRIIENQQQYYPWLAE-1NPN | KLDELVAFRVPYYVGPL | QQQSsdAKFAWMIR--- | KAEBGQITPWNFDDKVDRQA | 509 |
| AKP02966 | 416 | EKIIDNQSQYYPPLKE--NKE | KLLSIISFRIPYYVGPL | -QSSekNPFAWMER--- | KSNGHARPWNFDEIVDREK | 483 |
| WP_010991369 | 426 | EAILHQQAKYYPPLKE--NYD | KIKSLVTFRIPYFVGPL | ANGQ--SEFAWLTR--- | KADGEIRPWNIEEKVDFGK | 492 |
| WP_033838504 | 426 | EAILHQQAKYYPPLKE--NYD | KIKSLVTFRIPYFVGPL | ANGQ--SEFAWLTR--- | KADGEIRPWNIEEKVDFGK | 492 |
| EHN60060 | 429 | EAILHQQAKYYPPLKE--NYD | KIKSLVTFRIPYFVGPL | ANGQ--SEFAWLTR--- | KADGEIRPWNIEEKVDFGK | 495 |
| EFR89594 | 195 | EAILHQQAKYYPPLKE--NYD | KIKSLVTFRIPYFVGPL | ANGQ--SEFAWLTR--- | KADGEIRPWNIEEKVDFGK | 261 |
| WP_038409211 | 426 | EAILHQQAKYYPPLRK--DYE | KIRSLVTFRIPYFIGPL | ANGQ--SDFAWLTR--- | KADGEIRPWNIEEKVDFGK | 492 |
| EFR95520 | 45 | EAILHQQAKYYPPLRK--DYE | KIRSLVTFRIPYFIGPL | ANGQ--SDFAWLTR--- | KADGEIRPWNIEEKVDFGK | 111 |
| WP_003723650 | 426 | EAILHQQAKYYPPLKE--DYD | KIKSLVTFRIPYFVGPL | ANGQ--SEFAWLTR--- | KADGEIRPWNIEEKVDFGK | 492 |
| WP_003727705 | 426 | EAILHQQAKYYPPLRE--GYD | KIKSLVTFRIPYFVGPL | ANGQ--SEFAWLTR--- | KDDGEIRPWNIEEKVDFGK | 492 |
| WP_003730785 | 426 | EAILHQQAKYYPPLRE--DYE | KIKSLVTFRIPYFVGPL | ANGQ--SEFAWLTR--- | KADGEIRPWNIEEKVDFGK | 492 |
| WP_003733029 | 426 | EAILHQQAKYYPPLRE--DYE | KIKSLVTFRIPYFVGPL | AKGQ--SDFAWLTR--- | KADGEIRPWNIEEKVDFGK | 492 |
| WP_003739838 | 429 | EAILHQQAKYYPPLKE--AYD | KIKSLVTFRIPYFVGPL | ANGQ--SEFAWLTR--- | KADGEIRPWNIEEKVDFGK | 495 |
| WP_014601172 | 426 | EAILHQQAKYYPPLRE--DYE | KIKSLVTFRIPYFVGPL | AKGQ--SEFAWLTR--- | KADGEIRPWNIEEKVDFGK | 492 |
| WP_023548323 | 426 | EAILHQQAKYYTFPLKE--DYD | KIKSLVTFRIPYFVGPL | ANGQ--SEFAWLTR--- | KADGEIRPWNIEEKVDFGK | 492 |
| WP_031665337 | 426 | EAILHQQAKYYPPLRE--DYE | KIKSLVTFRIPYFVGPL | AKGQ--SEFAWLTR--- | KADGEIRPWNIEEKVDFGK | 492 |
| WP_031669209 | 426 | EAILHQQAKYYPPLRE--DYE | KIKSLVTFRIPYFVGPL | AKGQ--SEFAWLTR--- | KADGEIRPWNIEEKVDFGK | 492 |
| WP_033920898 | 426 | EAILHQQAKYYPPLRE--DYE | KIKSLVTFRIPYFVGPL | AKGQ--SEFAWLTR--- | KADGEIRPWNIEEKVDFGK | 492 |
| AKI42028 | 426 | EAILHQQAKYYPPLRE--DYE | KIKSLVTFRIPYFVGPL | AKGQ--SEFAWLTR--- | KADGEIRPWNIEEKVDFGK | 492 |
| AKI50529 | 429 | EAILHQQAKYYPPLRE--DYE | KIKSLVTFRIPYFVGPL | AKGQ--SEFAWLTR--- | KADGEIRPWNIEEKVDFGK | 495 |
| EFR83390 | | | | | | |
| WP_046323366 | 426 | EAILHQQAKYYPPLKV--DYE | KIKSLVTFRIPYFVGPL | ANGQ--SEFSWLTR--- | KADGEIRPWNIEEKVDFGK | 492 |
| AKE81011 | 436 | HAILRRQEDFYPPLKD--NRE | KIEKILTFRIPYYVGPL | ARG-n-SRFAWMTR--- | KSEETITPWNFEEVVDKGA | 502 |
| CUO82355 | 434 | IKIIDNQAKYYPVLKE--KRE | QLLSILTFRIPYYFGPL | ETSEh--AWIKRlegKENQRILPWNYQDTVDVDA | | 502 |
| WP_033162887 | 435 | SAEDFINKMTNYDLYLPEEKVLPEEKVLPKSHVYETYAVYNELTKIKYVN | | | -EQGKES-FPDSNMKQEIFDHVFK--ENR-KVTK | | 503 |
| 5AXW_A | 230 | -KEWYEMLMGHCTYFFEELRSVKYAYNADLYNALNDLNNLVLTR- | | | -EGLRDYqFLDSGQKKQIVNQLFK--ENR-KVTE | | 519 |
| AGZ01981 | 171 | IQIIDNQSVYYPQLKE--NRD | KLISILEFRIPYYFGPL | AHSE--FAWIKKfedKQKERILPWNYVCPTVDIDA | | 245 |
| AKA60242 | 487 | SAQSFIERMTNFDKNLPDKNLPNEKVLPKHSLLYEYFTVYNELTKVKVYT- | | | -EGMRKPaFLSGEQKKAIVDLLFK--KFQIIENVFK--QKK-KPTL | | 561 |
| AKS40380 | 487 | SAQSFIERMTNFDKNLPNEKVLPKHSLLYEYFTVYNELTKVKVYT- | | | -EGMRKPaFLSGEQKKAIVDLLFK--TNR-KVTV | | 561 |
| 4UN5_B | 487 | SAQSFIERMTNFDKNLPNEKVLPKHSLLYEYFTVYNELTKVKVYT- | | | -EGMRKPaFLSG@QKKAIVDLLFK--TNR-KVTV | | 561 |
| WP_010922251 | 487 | SAQSFIERMTNFDKNLPNEKVLPKHSLLYEYFTVYNELTKVKVYT- | | | -EGMRKPaFLSGEQKKAIVDLLFK--TNR-KVTV | | 561 |
| WP_039695303 | 487 | SAEKFITRMTLNDLYLPEEKVLPKSHVYETYAVYNELTKIKYVN | | | -EQGKES-FPDSNMKQEIFDHVFK--ENR-KVTK | | 563 |
| WP_045635197 | 487 | SAEDFINKMTNYDLYLPEEKVLPKHSLLYETFAVYNELTKVKFIA | | | -EGLRDYqFLDSGQKKQIVNQLFK--ENR-KVTE | | 561 |
| 5AXW_A | 230 | --KEWYEMLMGHCTYFFEELRSVKYAYNADLYNALNDLNNLVLTR- | | | -DENEKLeYYE---KFQIIENVFK--QKK-KPTL | | 299 |
| WP_009880683 | 171 | SAQSFIERMTNFDKNLPNEKVLPKHSLLYEYFTVYNELTKVKVYT- | | | -EGMRKPaFLSGEQKKAIVDLLFK--TNR-KVTV | | 245 |
| WP_010922251 | 487 | SAQSFIERMTNFDKNLPNEKVLPKHSLLYEYFTVYNELTKVKVYT- | | | -EGMRKPaFLSGEQKKAIVDLLFK--TNR-KVTV | | 561 |
| WP_011054416 | 487 | SAQSFIERMTNFDKNLPNEKVLPKHSLLYEYFTVYNELTKVKVYT- | | | -EGMRKPaFLSGEQKKAIVDLLFK--TNR-KVTV | | 561 |
| WP_011284745 | 487 | SAQSFIERMTNFDKNLPNEKVLPKHSLLYEYFTVYNELTKVKVYT- | | | -EGMRKPaFLSGEQKKAIVDLLFK--TNR-KVTV | | 561 |
| WP_011285506 | 487 | SAQSFIERMTNFDKNLPNEKVLPKHSLLYEYFTVYNELTKVKVYT- | | | -EGMRKPaFLSGEQKKAIVDLLFK--TNR-KVTV | | 561 |
| WP_011527619 | 487 | SAQSFIERMTNFDKNLPNEKVLPKHSLLYEYFTVYNELTKVKVYT- | | | -EGMRKPaFLSGEQKKAIVDLLFK--TNR-KVTV | | 561 |
| WP_012560673 | 487 | SAQSFIERMTNFDKNLPNEKVLPKHSLLYEYFTVYNELTKVKVYT- | | | -EGMRKPaFLSGEQKKAIVDLLFK--TNR-KVTV | | 561 |
| WP_014407541 | 487 | SAQSFIERMTNFDKNLPNEKVLPKHSLLYEYFTVYNELTKVKVYT- | | | -EGMRKPaFLSGEQKKAIVDLLFK--TNR-KVTV | | 561 |

| | | | |
|---|---|---|---|
| WP_020905136 | 487 | SAQSFIERMTNFDKNLPNEKVLPKHSLLYEYFTVYNELTKVKYVT--EGMRKPaFLSGEQKKAIVDLLFK--TNR-KVTV | 561 |
| WP_023080005 | 487 | SAQSFIERMTNFDKNLPNEKVLPKHSLLYEYFTVYNELTKVKYVT--EGMRKPaFLSGEQKKAIVDLLFK--TNR-KVTV | 561 |
| WP_023610282 | 487 | SAQSFIERMTNFDKNLPNEKVLPKHSLLYEYFTVYNELTKVKYVT--EGMRKPaFLSGEQKKAIVDLLFK--TNR-KVTV | 561 |
| WP_030125963 | 487 | SAQSFIERMTNFDKNLPNEKVLPKHSLLYEYFTVYNELTKVKYVT--EGMRKPaFLSGEQKKAIVDLLFK--TNR-KVTV | 561 |
| WP_030126706 | 487 | SAQSFIERMTNFDKNLPNEKVLPKHSLLYEYFTVYNELTKVKYVT--EGMRKPaFLSGEQKKAIVDLLFK--TNR-KVTV | 561 |
| WP_031488318 | 487 | SAQSFIERMTNFDKNLPNEKVLPKHSLLYEYFTVYNELTKVKYVT--EGMRKPeFLSGEQKKAIVDLLFK--TNR-KVTV | 561 |
| WP_032460140 | 487 | SAQSFIERMTNFDKNLPNEKVLPKHSLLYEYFTVYNELTKVKYVT--EGMRKPaFLSGEQKKAIVDLLFK--TNR-KVTV | 561 |
| WP_032461047 | 487 | SAQSFIERMTNFDKNLPNEKVLPKHSLLYEYFTVYNELTKVKYVT--EGMRKPaFLSGEQKKAIVDLLFK--TNR-KVTV | 561 |
| WP_032462016 | 487 | SAQSFIERMTNFDKNLPNEKVLPKHSLLYEYFTVYNELTKVKYVT--EGMRKPaFLSGEQKKAIVDLLFK--TNR-KVTV | 561 |
| WP_032462936 | 487 | SAQSFIERMTNFDKNLPNEKVLPKHSLLYEYFTVYNELTKVKYVT--EGMRKPaFLSGEQKKAIVDLLFK--TNR-KVTV | 561 |
| WP_032464890 | 487 | SAQSFIERMTNFDKNLPNEKVLPKHSLLYEYFTVYNELTKVKYVT--EGMRKPaFLSGEQKKAIVDLLFK--TNR-KVTV | 561 |
| WP_033888930 | 312 | SAQSFIERMTNFDKNLPNEKVLPKHSLLYEYFTVYNELTKVKYVT--EGMRKPaFLSGEQKKAIVDLLFK--TNR-KVTV | 386 |
| WP_038431314 | 487 | SAQSFIERMTNFDKNLPNEKVLPKHSLLYEYFTVYNELTKVKYVT--EGMRKPaFLSGEQKKAIVDLLFK--TNR-KVTV | 561 |
| WP_038432938 | 487 | SAQSFIERMTNFDKNLPNEKVLPKHSLLYEYFTVYNELTKVKYVT--EGMRKPaFLSGEQKKAIVDLLFK--TNR-KVTV | 561 |
| WP_038434062 | 398 | SAQSFIERMTNFDKNLPNEKVLPKHSLLYEYFTVYNELTKVKYVT--EGMRKPaFLSGEQKKAIVDLLFK--TNR-KVTV | 472 |
| BAQ51233 | | ---------------------------------------------------------------------- | |
| KGE60162 | | ---------------------------------------------------------------------- | |
| KGE60856 | | ---------------------------------------------------------------------- | |
| WP_002989955 | 487 | SAQSFIERMTNFDKNLPNEKVLPKHSLLYEYFTVYNELTKVKYVT--EGMRKPaFLSGEQKKAIVDLLFK--TNR-KVTV | 561 |
| WP_003030002 | 487 | SAEKFITRMTLNDLYLPEEKVLPKHSLLYETFTVYNELTKVYVN--EQGEAK-FFDANMKQEIFDHVFK--ENR-KVTK | 560 |
| WP_003065552 | 490 | SAEKFITRMTLNDLYLPEEKVLPKHSHVYETYAVYNELTKIKVN--EQGKDS-FFDSNMKQEIFNSLFK--EKR-KVTE | 563 |
| WP_001040076 | 488 | SAEAFIHRMTNNDLYLPEEKVLPKHSLLYEKFTVYEKFTVYNELTKVRFLA--EGFKDFqFLNRKQKETIENSLFK--EKR-KVTE | 562 |
| WP_001040078 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_001040080 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_001040081 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_001040083 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_001040085 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_001040087 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_001040088 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_001040089 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_001040090 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_001040091 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_001040092 | 488 | SAEAFIHRMTNNDFYLPEEKVLPKHSLLYEKFTVYNELTKVRFLA--EGFKDFqFLNRKQKETIENSLEK--EKR-KVTE | 562 |
| WP_001040094 | 488 | SAEAFIHRMTNNDFYLPEEKVLPKHSLLYEKFTVYNELTKVRFLA--EGFKDFqFLNRKQKETIENSLEK--EKR-KVTE | 562 |
| WP_001040095 | 488 | SAEAFIHRMTNNDFYLPEEKVLPKHSLLYEKFTVYNELTKVRFLA--EGFKDFqFLNRKQKETIENSLEK--EKR-KVTE | 562 |
| WP_001040096 | 488 | SAEAFIHRMTNNDFYLPEEKVLPKHSLLYEKFTVYNELTKVRFLA--EGFKDFqFLNRKQKETIENSLEK--EKR-KVTE | 562 |
| WP_001040097 | 488 | SAEAFIHRMTNNDFYLPEEKVLPKHSLLYEKFTVYNELTKVRFLA--EGFKDFqFLNRKQKETIENSLEK--EKR-KVTE | 562 |
| WP_001040098 | 488 | SAEAFIHRMTNNDFYLPEEKVLPKHSLLYEKFTVYNELTKVRFLA--EGFKDFqFLNRKQKETIENSLEK--EKR-KVTE | 562 |
| WP_001040099 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_001040100 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_001040104 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_001040105 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_001040106 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_001040107 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_001040108 | 488 | SAEAFIHRMTNNDFYLPEEKVLPKHSLLYEKFTVYNELTKVRFLA--EGFKDFqFLNRKQKETIENSLEK--EKR-KVTE | 562 |
| WP_001040109 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_001040110 | 488 | SAEAFIHRMTNNDFYLPEEKVLPKHSLLYEKFTVYNELTKVRYKN--EQGETY-FFDSNVKQEIFDGVFK--EHR-KVSK | 561 |
| WP_015058523 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_017643650 | 488 | SAEAFIHRMTNNDFYLPEEKVLPKHSLLYEKFTVYNELTKVRFLA--EGFKDFqFLNRKQKETIENSLEK--EKR-KVTE | 562 |
| WP_017647151 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_017648376 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_017649527 | 488 | SAEAFIHRMTNNDFYLPEEKVLPKHSLLYEKFTVYNELTKVRYKN--EQGETY-FFDSNIKQEIFDGVFK--EHR-KVSK | 561 |
| WP_017771611 | 488 | SAEAFIHRMTNNDFYLPEEKVLPKHSLLYEKFTVYNELTKVRYKN--EQGETY-FFDSNIKQEIFDGVFK--EHR-KVSK | 561 |

```
-continued

WP_017771984  488  SAEAFIHRMTNNDFYLPEEKVLPKHSLIYEKFTVYNELTKVRYKN--EQGETY-FFDSNIKQEIFDGVFK--EHR-KVSK  561
CFQ25032      488  SAEAFIHRMTNNDFYLPEEKVLPKHSLIYEKFTVYNELTKVRYKN--EQGETY-FFDSNIKQEIFDGVFK--EHR-KVSK  561
CFV16040      488  SAEAFIHRMTNNDFYLPEEKVLPKHSLIYEKFTVYNELTKVRYKN--EQGETY-FFDSNIKQEIFDGVFK--EHR-KVSK  561
KLJ37842      488  SAEAFIHRMTNNDFYLPEEKVLPKHSLIYEKFTVYNELTKVRYKN--EQGETY-FFDSNIKQEIEDGVEK--EHR-KVSK  561
KLJ72361      488  SAEAFIHRMTNNDFYLPEEKVLPKHSLIYEKFTVYNELTKVRYKN--EQGETY-FFDSNIKQEIEDGVEK--EHR-KVSK  561
KLL20707      488  SAEAFIHRMTNNDLYLPEEKVLPKHSLIYEKFTVYNELTKVRYKN--EQGETY-FFDSNIKQEIEDGVEK--EHR-KVSK  561
KLL42645      488  SAEAFIHRMTNNDLYLPEEKVLPKHSLIYEKFTVYNELTKVRYKN--EQGETY-FFDSNIKQEIEDGVEK--EHR-KVSK  561
WP_047207273  488  SAEAFIHRMTNNDLYLPEEKVLPKHSLIYEKFTVYNELTKVRFLA--EGFKDFqFLNRKQKETIFNLFK--EKR-KVTE  562
WP_047209694  488  SAEAFIHRMTNNDLYLPEEKVLPKHSLIYEKFTVYNELTKVRYKN--EQGETY-FFDSNIKQEIEDGVEK--EHR-KVSK  561
WP_050198062  488  SAEAFIHRMTNNDFYLPEEKVLPKHSLIYEKFTVYNELTKVRYKN--EQGETY-FFDSNIKQEIEDGVEK--EHR-KVSK  561
WP_050201642  488  SAEAFIHRMTNNDFYLPEEKVLPKHSLIYEKFTVYNELTKVRYKN--EQGETY-FFDSNIKQEIFDGVFK--EHR-KVSK  561
WP_050204027  488  SAEAFIHRMTNNDFYLPEEKVLPKHSLIYEKFTVYNELTKVRYKN--EQGETY-FFDSNIKQEIFDGVFK--EHR-KVSK  561
WP_050881965  488  SAEAFIHRMTNNDLYLPEEKVLPKHSLIYEKFTVYNELTKVRYKN--EQGETY-FFDSNIKQEIEDGVEK--EHR-KVSK  561
WP_050886065  488  SAEAFIHRMTNNDLYLPEEKVLPKHSLIYEKFTVYNELTKVRYKN--EQGETY-FFDSNIKQEIEDGVEK--EHR-KVSK  561
AHN30376      488  SAEAFIHRMTNNDLYLPEEKVLPKHSLIYEKFTVYNELTKVRYKN--EQGETY-FFDENVKQEIEDGVEK--EHR-KVSK  561
EAO78426      488  SAEAFIHRMTNNDLYLPEEKVLPKHSLIYEKFTVYNELTKVRYKN--EQGETY-FFDSNIKQEIEDGVEK--EHR-KVSK  561
CCW42055      488  SAEAFIHCMTNNDLYLPEEKVLPKHSLIYEKFTVYNELTKVKVN---EQGETY-FFDSNIKQEIFDGVEK--EYR-KVSK  561
WP_003041502  488  SAEKFITRMTLNDLYLPEEKVLPKHELLYETFTVYNELTKVKVN---EQGEAK-FFDANMKQEIFDHVFK--ENR-KVTK  560
WP_037593752  488  SAEKFITRMTLNDLYLPEEKVLPKHSPLYETFTVYNELTKVKVN---EQGEAK-FFDTNMKQEIFDHVFK--ENR-KVTK  561
WP_049516684  488  SAEKFITRMTLNDLYLPEEKVLPKHSPLYETFTVYNELTKVKVN---EQGEAK-FFDTNMKQEIFDHVFK--ENR-KVTK  561
GAD46167      487  SAEKFITRMTLNDLYLPEEKVLPKHSPLYETFTVYNELTKVKVN---EQGEAK-FFDTNMKQEIFDHVEK--ENP-KVTK  560
WP_018363470  488  SAEKFITRMTLNDLYLPEEKVLPKHSHVYETFAVYNELTKVKVN---EQGKDS-FFDSNMKQEIFDHVFK--ENR-KVTK  561
WP_003043819  497  SAQSFIERMTNEDEQLPNKKVLPNEKVLPKHELLYEYFTVYNELTKVKVT--ERMRKPeFLSGEQKKAIVDLLFK--TNR-KVTK  571
WP_006269658  487  SAQSFIERMTNEDKNLPNEKVLPKHELLYEYFTVYNELTKVKVT---EGMRKPeFLEGKQKEAIVDLLFK--TNR-KVTV  560
WP_048800889  487  SAQSFIERMTNEDKNLPNEKVLPKHELLYEYFTVYNELTKVKVT---EGMRKPeFLEGKQKEAIVDLLFK--TNR-KVTV  560
WP_012767106  487  SAQSFIERMTNEDKNLPNEKVLPKHELLYEYFTVYNELTKVKVT---EGMRKPeFLEGKQKEAIVDLLFK--TNR-KVTV  560
WP_014612333  488  SAQSFIERMTNEDKNLPNEKVLPKHELLYEIFTVYNELTKVKVT---EGMRKPeFLEGKQKEAIVDLLFK--TNR-KVTV  561
WP_015017095  487  SAQSFIERMTNEDKNLPNEKVLPKHELLYEYFTVYNELTKVKVT---EGMRKPeFLEGKQKEAIVDLLFK--TNR-KVTV  560
WP_015057649  487  SAQSFIERMTNEDKNLPNEKVLPKHELLYEYFTVYNELTKVKVT---EGMRKPeFLEGKQKEAIVDLLFK--TNR-KVTV  560
WP_048327215  487  SAQSFIERMTNEDKNLPNEKVLPKHELLYEYFTVYNELTKVKVT---EGMRKPaELSGEQKKAIVDLLFK--TNR-KVTV  560
WP_049519324  487  SAQSFIERMTNEDKNLPNEKVLPKHELLYEYFTVYNELTKVKVT---EGMTRPqFLEADQKQAIVDLLFK--TNR-KVTV  561
WP_012515931  487  SAQIFIEKMTKNDLYLPNEKVLPKHELLYEYFTVYNELTKVKVAT---EGMTRPqFLEADQKQAIVDLLFK--TNR-KVTV  561
WP_021320964  487  SAQIFIEKMTKNDLYLPNEKVLPKHELLYEYFTVYNELTKVKVAT---EGMTRPqFLEADQKQAIVDLLFK--TNR-KVTV  561
WP_037581760  487  SAQIFIEKMTKNDLYLPNEKVLPKHELLYEYFTVYNELTKVKVAT---EGMTRPqFLEADQKQAIVDLLFK--TNR-KVTV  561
WP_004232481  487  SAEKFITRMTLNDLYLPEEKVLPKHELLYEVVETFAVYNELTKIKVN---EQGKSF-FFDANMKQEIFDHVFK--ENR-KVTK  560
WP_009854540  488  SAEKFITRMTLNDLYLPEEKVLPKHELLYEVVETFAVYNELTKIKVN---EQGKSF-FFDSNMKQEIFDHVFK--ENR-KVTK  561
WP_012962174  488  SAEKFITRMTLNDLYLPEEKVLPKHELVYETFAVYNELTKVKVN---EQGKEN-FFDANMKQEIPEHVFK--ENR-KVTK  561
WP_039695303  490  SAEKFIERMTLNDLYLPEEKVLPKHSHVYETFAVYNELTKVKVN---EQGKES-FFDSNMKQEIFDHVFK--ENR-KVTK  563
WP_014334983  487  SAEKFITRMTLNDLYLPEEKVLPKHSPLYEMFMVYNELTKVKVQT---EQGESF-FFDANMKQEIFDHVFK--ENR-KVTK  560
WP_030992269  487  SAEAFIERMTNFPTYLPEEKVLPKHSPLYEMFMVYNELTKVKVQT---EGMKRPvFLSSEDKEEIVNLLFK--KER-KVTV  560
AHY15608      487  SARAFIERMTNFPTYLPEEKVLPKHSPLYEMFMVYNELTKVKVQT---EGMKRPvFLSSEDKEEIVNLLFK--KER-KVTV  561
AHY17476      487  SARAFIERMTNFPTYLPEEKVLPKHSPLYEMFMVYNELTKVKVQT---EGMKRPvFLSSEDKEEIVNLLFK--KER-KVTV  561
ESR09100      ---  --------------------------------------------------------------------------------
AGM98575      487  SARAFIERMTNFPTYLPEEKVLPKHSPLYEMFMVYNELTKVKVQT---EGMKRPvFLSSEDKEEIVNLLFK--KER-KVTK  561
ALF27331      487  SAERAFIERMTNYDLYLPNQKVLPRHSLLYEKFTVYNELTKVKYKT--EQGKTA-FFDANMKQEIFDGVFK--VYR-KVTK  560
WP_018372492  500  SASRFIERMTLHDLYLPNQKVLPRHSLLYEKFTVYNELTKVKVRFTP--EGGKEV-YFSKTDKENIFDSLFK--RYR-KVTK  573
WP_045618028  488  SAEDFINKMTNYDLYLPEEKVLPKHELLYEKFTVETFAVYNELTKVKVFIA--EGLRDYqFLDSGQKQIVTQLFK--EKR-KVTE  562
WP_045635197  487  SAEDFINKMTNYDLYLPEEKVLPKHELLYEKFTVETFAVYNELTKVKVFIA--EGLRDYqFLDSGQKQIVNQLFK--ENR-KVTE  561
WP_002263549  488  SAEAFINRMTNYDLYLPNQKVLPKHSLLYEKFTVYNELTKVKVKT---EQGKTA-FFDANMKQEIFDGVFK--VYR-KVTK  561
WP_002263887  487  SAEAFINRMTNYDLYLPNQKVLPKHSLLYEKFTVYNELIKVKVKT---EQGKTA-FFDANMKQEIFDGVFK--VYR-KVTK  560
WP_002264920  487  SVEAFINRMTNYDLYLPNQKVLPKHSLLYEKFTVYNELTKVKVKT---EQGKTA-FFDANMKQEIFDGVFK--VYR-KVTK  560
WP_002269043  487  SVEAFINRMTNYDLYLPNQKVLPKHSLLYEKFTVYNELTKVKVKT---EQGKTA-FFDANMKQEIFDGVFK--VYR-KVTK  560
WP_002269448  487  SAEAFINRMTNYDLYLPNQKVLPKHSLLYEKFTVYNELTKVKVKT---EQGKTA-FFDANMKQEIFDGVFK--VYR-KVTK  560
```

-continued

```
WP_002271977   487 SAEAFIINRMTNDLYLPNQKVLPKHSLLYEKFTVYNELTKVYKT--EQGKTA-FFDANMKQEIFDGVFK--VYR-KVTK  560
WP_002272766   487 SAEAFIINRMTNDLYLPNQKVLPKHSLLYEKFTVYNELTKVYKT--EQGKTA-FFDANMKQEIFDGVFK--VYR-KVTK  560
WP_002273241   487 SAEAFIINRMTNDLYLPNQKVLPKHSLLYEKFTVYNELTKVYKT--EQGKTA-FFDANMKQEIFDGVFK--VYR-KVTK  560
WP_002275430   487 SAEAFIINRMTNDLYLPNQKVLPKHSLLYEKFTVYNELTKVYKT--EQGKTA-FFDANMKQEIFDGVFK--VYR-KVTK  560
WP_002276448   487 SAEAFIINRMTNDLYLPNQKVLPKHSLLYEKFTVYNELTKVYKT--EQGKTA-FFDANMKQEIFDGVFK--VYR-KVTK  560
WP_002277050   487 SAQAFIEHMTNDLYLPNQKVLPKHSLLYEKFTVYNELTKIKYKT--EIGEAK-FFDANLKQEIFDGLFK--HER-KVTK  560
WP_002277364   487 SAEAFIINRMTNDLYLPNQKVLPKHSLLYEKFTVYNELTKVYKT--EQGKTA-FFDANLKQEIFDGVFK--VYR-KVTK  560
WP_002279025   487 SAEAFIINRMTNDLYLPNQKVLPKHSLLYEKFTVYNELTKVYKT--EQGETA-FFDANMKQEIFDGVFK--VYR-KVTK  560
WP_002279859   487 SVEAFIINRMTNDLYLPNQKVLPKHSLLYEKFTVYNELTKVYKT--EQGKTA-FFDANMKQEIFDGVFK--VYR-KVTK  560
WP_002280230   487 SAEAFIINRMTNDLYLPNQKVLPKHSLLYEKFTVYNELTKVYKT--EQGKTA-FFDANMKQEIFDGVFK--VYR-KVTK  560
WP_002281696   487 SAEAFIINRMTNDLYLPNQKVLPKHSLLYEKFTVYNELTKVYKT--EQGKTA-FFDANMKQEIFDGVFK--VYR-KVTK  560
WP_002282247   487 SAQAFIEHMTNNDLYLPNEKVLPKHSPLYEKYTVYNELTKIKYVT--EIGEAK-FFDANLKQEIFDGLFK--HER-KVTK  560
WP_002282906   487 SAEAFIINRMTNDLYLPNQKVLPKHSLLYEKFTVYNELTKVYKT--EQGKTA-FFDANMKQEIFDGVFK--VYR-KVTK  560
WP_002283846   487 SVEAFIINRMTNDLYLPNQKVLPKHSLLYEKFTVYNELTKVYKT--EQGKTA-FFDANMKQEIFDGVFK--VYR-KVTK  560
WP_002287255   487 SVEAFIINRMTNDLYLPNQKVLPKHSLLYEKFTVYNELTKVYKT--EQGKTA-FFDANMKQEIFDGVFK--VYR-KVTK  560
WP_002288990   487 SVEAFIINRMTNDLYLPNQKVLPKHSLLYEKFTVYNELTKVYKT--EQGKTA-FFDANMKQEIFDGVFK--VYR-KVTK  560
WP_002289641   487 SAEAFIINRMTNDLYLPNQKVLPKHSLLYEKFTVYNELTKVYKT--EQGKTA-FFDANMKQEIFDGVFK--VYR-KVTK  560
WP_002290427   487 SVEAFIINRMTNDLYLPNQKVLPKHSLLYEKFTVYNELTKVYKT--EQGKTA-FFDANMKQEIFDGVFK--VYR-KVTK  560
WP_002295753   487 SVEAFIINRMTNDLYLPNQKVLPKHSLLYEKFTVYNELTKVYKT--EQGKTA-FFDANMKQEIFDGVFK--VYR-KVTK  560
WP_002296423   487 SAEAFIINRMTNDLYLPNQKVLPKHSLLYEKFTVYNELTKVYKT--EQGKTA-FFDANMKQEIFDGVFK--VYR-KVTK  560
WP_002304487   497 SAEKFITRMTLNDLYLPEEKVLPKHSLLYETFTVYNELTKVYKVN--EQGEAK-FFDANMKQEIFDHVFK--ENR-KVTK  570
WP_002305844   487 SAEAFIINRMTNDLYLPNQKVLPKHSLLYEKFTVYNELTKVYKT--EQGKTA-FFDANMKQEIFDGVFK--VYR-KVTK  560
WP_002307203   487 SAEAFIINRMTNDLYLPNQKVLPKHSLLYEKFTVYNELTKVYKT--EQGKTA-FFDANMKQEIFDGVFK--VYR-KVTK  560
WP_002310390   487 SAEAFIINRMTNDLYLPNQKVLPKHSLLYEKFTVYNELTKVYKT--EQGKTA-FFDANMKQEIFDGVFK--VYR-KVTK  560
WP_002352408   487 SAEAFIINRMTNDLYLPNQKVLPKHSLLYEKFTVYNELTKVYKT--EQGKTA-FFDANMKQEIFDGVFK--VYR-KVTK  560
WP_012997688   487 SAEAFIINRMTNDLYLPNQKVLPKHSLLYEKFTVYNELTKVYKT--EQGKTA-FFDANMKQEIFDGVFK--VYR-KVTK  560
WP_014677909   487 SAEAFIINRMTNDLYLPNQKVLPKHSPLYEKYTVYNELTKVYKT--EIGEAK-FFDANLKQEIFDGLFK--HER-KVTK  560
WP_019312892   487 SVEAFIINRMTNDLYLPNQKVLPKHSLLYEKFTVYNELTKVYKT--EQGKTA-FFDANMKQEIFDGVFK--VYR-KVTK  560
WP_019313659   487 SAEAFIINRMTNDLYLPNQKVLPKHSLLYEKFTVYNELTKVYKT--EQGKTA-FFDANMKQEIFDGVFK--VYR-KVTK  560
WP_019314093   487 SVEAFIINRMTNDLYLPNQKVLPKHSLLYEKFTVYNELTKVYKT--EQGKTA-FFDANMKQEIFDGVFK--VYR-KVTK  560
WP_019315370   487 SAEAFIINRMTNDLYLPNQKVLPKHSLLYEKFTVYNELTKVYKT--EQGKTA-FFDANMKQEIFDGVFK--VYR-KVTK  560
WP_019803776   487 SAEAFIINRMTNDLYLPNQKVLPKHSLLYEKFTVYNELTKVYKT--EQGKTA-FFDANMKQEIFDGVFK--VYR-KVTK  560
WP_019805234   487 SAEAFIINRMTNDLYLPNQKVLPKHSLLYEKFTVYNELTKVYKT--EQGKTA-FFDANMKQEIFDGVFK--VYR-KVTK  560
WP_024783594   487 SAEAFIINRMTNDLYLPNQKVLPKHSLLYEKFTVYNELTKVYKT--EQGKTA-FFDANMKQEIFDGVFK--VYR-KVTK  560
WP_024784288   487 SAQAFIEHMTNDLYLPNEKVLPKHSPLYEKYTVYNELTKIKYVT--EIGEAK-FFDANLKQEIFDGLFK--HER-KVTK  560
WP_024784666   487 SAEAFIINRMTNDLYLPNQKVLPKHSLLYEKFTVYNELTKVYKT--EQGKTA-FFDANMKQEIFDGVFK--VYR-KVTK  560
WP_024784894   487 SAEAFIINRMTNDLYLPNQKVLPKHSLLYEKFTVYNELTKVYKT--EQGKTA-FFDANMKQEIFDGVFK--VYR-KVTK  560
WP_024786433   487 SAQAFIEHMTNDLYLPNQKVLPKHSLLYEKFTVYNELTKVYKT--EIGEAK-FFDANLKQEIFDGLFK--HER-KVTK  560
WP_049473442   487 SAEAFIINRMTNDLYLPNQKVLPKHSLLYEKFTVYNELTKVYKT--EQGKTA-FFDANMKQEIFDGVFK--VYR-KVTK  560
WP_049745547   480 SAEAFIINRMTNDLYLPNQKVLPKHSLLYEKFTVYNELTKVYKT--EQGKTA-FFDANMKQEIFDGVFK--VYR-KVTK  553
EMC03581       488 SAESFIINKMTNDLYLPEEKVLPKHSLLYETFAVYNELTKVKFIA--EGLRDYqFLDSRQKDIFYTLFKaeDKR-KVTE  564
WP_000428612   488 SAEDFIHRMTNKMTNDLYLPEEKVLPKHSLLYETFAVYNELTKVKFIA--EGLRDYqFLDSGQKKQIVTQLFK--EKR-KVTE  562
WP_000428613   487 SAEDFIINKMTNDLYLPEEKVLPKHSLLYETFAVYNELTKVKFIA--EGMKDYqFLDSGQKKQIVNQLFK--EKR-KVTE  561
WP_049525028   456 SAKVFIERMTNFPTYLPEEKVLPKHSLLYEMFTVYNELTKVKYQA--EGMRKPeFLSSEEKIRIVSNLFK--TER-KVTE  530
WP_003107102   489 SAQAFIERMTNKMTNDFEYLPQEKVLPKHSLLYETFAVYNELTKVKVT--EGMTKPeFLSAGQKEQIVELLFK--KYR-KVTV  563
WP_054279288   488 SAEAFIINKMTNDLYLPEEKVLPKHSLLYETFAVYNELTKVKFIA--EGLRDYqFLDSGQKKKIINQLFK--EKR-KVTE  562
WP_049531101   488 SAEDFIINKMTNDLYLPEEKVLPKHSLLYETFAVYNELTKVKFIA--EGLRDYqFLDSGQKKQIVNQLFK--EKR-KVTE  562
WP_049538452   488 SAEDFIINKMTNDLYLPEEKVLPKHSLLYETFAVYNELTKVKFIA--EGLRDYqFLDSGQKKQIVNQLFK--EKR-KVTE  562
WP_049549711   490 SAQAFIEGMTNDLYLPEEKVLPKHSLLYETFAVYNELTKVKFIA--ENMTKPlYLSAEQKEATIDHLFK--QTR-KVTV  564
WP_007896501   442 SAQAFIEGMTNKMTNDTYLPEEKVLPKHSLLYEMFTVYNELTKVKYIA--ENMTKPlYLSAEQKEATIDHLFK--QTR-KVTV  516
EFR44625       487 SAEDFIHRMTNKMTNDLYLPEEKVLPKHSLLYETFAVYNELTKVKFIA--EGLRDYqFLDSGQKKQIVNQLFK--EKR-KVTE  561
WP_002897477   487 SAEDFIINKMTNDLYLPEEKVLPKHSLLYETFAVYNELTKVKFIA--EGLRDYqFLDSGQKKQIVNQLFK--DKR-KVTE  561
WP_002906454   487 SAEDFIINKMTNDLYLPEEKVLPKHSLLYETFAVYNELTKVKFIA--EGLRDYqFLDSGQKKQIVNQLFK--DKR-KVTE  561
```

-continued

```
WP_009729476    488  SAEDFINKMTNDLYLPEEKVLPKHSLLYETFAVYNELTKVFIA-EGLRDYqFLDSGQKKQIVTQLFK--EKR-KVTE      562
CQR24647        488  SAQAFIERMTNNDLYLPDQKVLPKHSLLYQKFAVYNELTKIKYVT-ETGEAR-LEDVFLKKEIFDGLEK--KER-KVTK     561
WP_000066813    488  SAEDFINKMTNTNDLYLPEEKVLPKHSLLYETFAVYNELTKVFIA-EGLTRYqFLDKKQKKDIFDTFFKaeNKR-KVTE    564
WP_009754323    487  SAESFINKMTNYDLYLPEEKVLPKHSLLYETFAVYNELTKVKFIA-EGLRDYqFFDSGQKKQIVNQLFK--EKR-KVTE    562
WP_044674937    487  SAENFINKMTNTNDQYLPDQKVLPKHSLLYEKFAVYNELTKVRYVT-EGMRDYqFLDSGQKKDIVKTLFK--TKR-KVTA   561
WP_044676715    487  SAENFITRMTNTNDQYLPDQKVLPKHSLLYEKFAVYNELTKVRYVT-EQGKSF-FFDANMKQEIFDGVEK--VYR-KVTK   560
WP_044680361    487  SAENFITRMTNTNDQYLPDQKVLPKHSLLYEKFAVYNELTKVRYVT-EQGKSF-FFDANMKQEIFDGVEK--VYR-KVTK   560
WP_044681799    487  SAENFITRMTNTNDQYLPDQKVLPKHSLLYEKFAVYNELTKVKFIA-EGMRDYqFLDSGQKKDIVKTLFK--TKR-KVTA   561
WP_049533112    487  SAEKFITRMTLNDLYLPEEKVLPKHSLLYETFTVYNELTKVKYVN-EQGEAK-FFDANMKQEIFDHVEK--ENR-KVTK   560
WP_029090905    472  TSEAFITRMTNKCTYLIHEDVIPKHSFSYAKFEVLNELANKIRLDG------KP--IDIPLKKRIFEGLFL--EKtKVTQ   540
WP_050606696    499  TAEGFIKRMRSYCTYFPDDEVLPKNSLLVSKYEVLNELNKIRVDD-------kLLEVDVKNDIYNELFM-KNK-TVTE    567
AIT42264        487  SAQSFIERMTNEDKNLPNEKVLPKHSLLYEYFTVYNELTKVKVT--EGMRKPaELSGEQKKAIVDLLFK--TNR-KVTK   561
WP_034440723    494  SAELFIENLTSRDTYLPDEPVLPKRSLLIYQKFTIFNELTKISYID-NFSSREKIAIENDLFK---NKsKVTK        567
AKQ21048        487  SAQSFIERMTNEDKNLPNEKVLLEEKVLPKHSLLYQTFEVYNELTKVRYTN-EQGKTE-KLNRQQKAEIIETLFK-qKNR-VRE 561
WP_004636532    489  SAEKFIERMTNMDTYLLEEKVLPKHSLLYQTFEVYNELTKVRYTN-EQGKTE-KLNRQQKAEIIETLFK-qKNR-VRE   562
WP_002364836    496  SATAFIERMTNEDTYLPSEKVLPKHSLLYEKFMVFNELTKTKISTD-DRGIKA-NFSGKEKEKIFDYLFK--TRR-KVKK  569
WP_016631044    447  SATAFIERMTNEDTYLPSEKVLPKHSLLYEKFMVFNELTKTKISYTD-DRGIKA-NFSGKEKEKIFDYLFK--TRR-KVKK  520
EMS75795        232  SAMKFIQRMINYDTYLPTEKVLPKHSLLYQKYTIFNELTKVAYKD--ERGIKH-QESSKEKEREIFKELFQ--KQR-KVTV  305
WP_002373311    496  SATAFIERMTNEDTYLPSEKVLPKHSLLYEKFMVFNELTKTKISTD-DRGIKA-NFSGKEKEKIFDYLFK--TRR-KVKK  569
WP_002378009    496  SATAFIERMTNEDTYLPSEKVLPKHSLLYEKFMVFNELTKTKISTD-DRGIKA-NFSGKEKEKIFDYLFK--TRR-KVKK  569
WP_002407324    496  SATAFIERMTNEDTYLPSEKVLPKHSLLYEKFMVFNELTKTKISTD-DRGIKA-NFSGKEKEKIFDYLFK--TRR-KVKK  569
WP_002413717    498  SATAFIERMTNEDTYLPSEKVLPKHSLLYEKFMVFNELTKTKISTD-DRGIKA-NFSGKEKEKIFDYLFK--TRR-KVKK  571
WP_010777580    496  SATAFIERMTNEDTYLPSEKVLPKHSLLYEKFMVFNELTKTKISTD-DRGIKA-NFSGKEKEKIFDYLFK--TRR-KVKK  569
WP_010818269    496  SATAFIERMTNEDTYLPSEKVLPKHSLLYEKFMVFNELTKTKISTD-DRGIKA-NFSGKEKEKIFDYLFK--TRR-KVKK  569
WP_010824395    496  SATAFIERMTNEDTYLPSEKVLPKHSLLYEKFMVFNELTKTKISTD-DRGIKA-NFSGKEKEKIFDYLFK--TRR-KVKK  569
WP_016622645    496  SATAFIERMTNEDTYLPSEKVLPKHSLLYEKFMVFNELTKTKISTD-DRGIKA-NFSGKEKEKIFDYLFK--TRR-KVKK  569
WP_033624816    496  SATAFIERMTNEDTYLPSEKVLPKHSLLYEKFMVFNELTKTKISTD-DRGIKA-NFSGKEKEKIFDYLFK--TRR-KVKK  569
WP_033625576    496  SATAFIERMTNEDTYLPSEKVLPKHSLLYEKFMVFNELTKTKISTD-DRGIKA-NFSGKEKEKIFDYLFK--TRR-KVKK  569
WP_033789179    496  SATAFIERMTNEDTYLPSEKVLPKHSLLYEKFMVFNELTKTKISTD-DRGIKA-NFSGKEKEKIFDYLFK--TRR-KVKK  569
WP_002310644    493  SAVRFIERMINTDMYMPHNKVLPKNSLLYQKFSIYNELTKVRYQD--ERGQMN-YFSSIEKKEIFHELFE--KNR-KVTK  566
WP_002312694    494  SAVRFIERMINTDMYMPHNKVLPKNSLLYQKFSIYNELTKVRYQD--ERGQMN-YFSSIEKKEIFHELFE--KNR-KVTK  567
WP_002314015    494  SAVRFIERMNNTDMYIPHNKVLPKNSLLYQKFSIYNELTKVRYQD--ERGQMN-YFSSIEKKEIFHELFE--KNR-KVTK  567
WP_002320716    494  SAVRFIERMINTDMYIPHNKVLPKNSLLYQKFSIYNELTKVRYQD--ERGQMN-YFSSIEKKEIFHELFE--KNR-KVTK  567
WP_002330729    493  SAVRFIERMINTDMYIPHNKVLPKNSLLYQKFSIYNELTKVRYQD--ERGQMN-YESSIEKKEIFHELFE--KNR-KVTK  566
WP_002335161    494  SAVRFIERMINTDMYMPHNKVLPKNSLLYQKFSIYNELTKVRYQD--ERGQMN-YESSIEKKEIFHELFE--KNR-KVTK  567
WP_002345439    494  SAVRFIERMINTDMYMPHNKVLPKNSLLYQKFSIYNELTKVRYQD--ERGQMN-YESSIEKKEIFHELFE--KNR-KVTK  567
WP_034867970    487  SAMRFIQRMTKQDTYLPTEKVLPKNSLLYQKMIFNELTKVSYKD--ERGVKQ-YFSGDEKQQIFKQLFQ--KERgKITV  561
WP_047937432    494  SAVRFIERMINTDMYMPHNKVLPKNSLLYQKFSIYNELTKVSYKD--ERGVKQ-YFSGDEKQQIFKQLFQ--KERgKITV  567
WP_010720994    487  SAMRFIQRMTKQDTYLPTEKVLPKNSLLYQKMIFNELTKVSYKD--ERGVKQ-YFSGDEKQQIFKQLFQ--KERgKITV  561
WP_010737004    487  SAMRFIQRMTKQDTYLPTEKVLPKNSLLYQKMIFNELTKVSYKD--ERGVKQ-YFSGDEKQQIFKQLFQ--KERgKITV  561
WP_034700478    487  SAMRFIQRMTKQDTYLPTEKVLPKNSLLYQKMIFNELTKVSYKD--ERGVKQ-YFSGDEKQQIFKQLFQ--KERgKITV  561
WP_007209003    491  SAVAFIERMTIKDIYL-NENVLPRHSLLYQKFTVFNELTKVLAD--DRGVFQ-RFSAEEKEDIFEKLFK--SER-KVTK  563
WP_023519917    486  SAIEFIERMTNQDTYLPKEKVLPKHSLLIYQRFMIFNELTKVSYTD--ERGKSH-YFSSEQKRKIFNELFK--QHP-RVTE  559
WP_010770040    490  SATKFIERMTNEDTYLPSEKVLPKHSMIYEKYMVYKMVSKVSVD--ERGMNQ-RFSGEEKKQIVEELFK--QSR-KVTK  563
WP_048604708    486  SAELFIERMTNFDLYLPSEKVLPKNSLLYQKMIFNELTKVSVD--EQGKVQ-NFSSEEKERIFIDLFK--QHR-KVTK  559
WP_010750235    487  SATKFIQRMINYDTYLPTEKVLPKMFMLYQKYTIFNELTKVAYKD--DRGIKH-QFSSEEKLRIFQELFK--KQR-RVTK  560
AII16583        526  SAQSFIERMTNFDKNLPNEKVLPKHSLLYEYFTVSKYEVLNEINKLRIND---------hLIKRDIKDKMLHTLFM-TNR-KVTV  600
WP_029073316    507  TADEFIKRMRNFCTYFPDEPVMAKNSLTVSKYEVLNEINKLRIND---------hLIKRDMKDKMLHTLFM-DHK-SISA  575
WP_031589969    507  TADEFIKRMRNFCTYFPDEPVMAKNSLTVSKYEVLNEINKLRIND---------hLIKRDMKDKMLHTLFM-DHK-SISA  575
KDA45870        485  SAEDFIKRMTINDLYLPTEPVLPKHSLLYERYTIFNELAGVRVT--ENGEAK-YEDAQTKRSIFE-LFK1--DR-KVSE  557
WP_039099354    510  SANEFIKRMTTDTYLLAEDVLPKQSLLYQRFEVLNELNGLKIDD---------LKQAIFTDLFM-QKtSVTV  578
AKP02966        484  SSNKFIRRMTVDSYLVGEPVLPKNSLIYQRYEVLNELNIRITEniKTNPTGsRLTVETKQHIYNELFK--NYK-KITV  560
WP_010991369    493  SAVDFIEKMTNKDTYLPKENVLPKHSLCYQKYLVYNELTKVRYIN--DQGKTS-YFSSQEKEQIENDLFK--QKR-KVKK  566
```

```
-continued

WP_033838504   493  SAVDFIEKMTNKDTYLPKENVLPKHSLCYQKLVYNELTKVRYIN--DQGKTS-YFSGQEKEQIENDLFK--QKR-KVKK   566
EHN60060       496  SAVDFIEKMTNKDTYLPKENVLPKHSLCYQKLVYNELTKVRYIN--DQGKTS-YFSGQEKEQIENDLFK--QKR-KVKK   569
EFR89594       262  SAVDFIEKMTNKDTYLPKENVLPKHSLCYQKLVYNELTKVRYIN--DQGKTS-YFSGQEKEQIENDLFK--QKR-KVKK   335
WP_038409211   493  SAIDFIEKMTNKDTYLPKENVLPKHSLCYQKLVYNELTKVRYIN--DQGKTS-HFSGQEKEQIENDLFK--QQR-KVKK   566
EFR95520       112  SAIDFIEKMTNKDTYLPKENVLPKHSLCYQKMVYNELTKIRYID--DQGKTH-HFSGQEKQQIFNGLFK--QKR-KVKK   185
WP_003723650   493  SAVDFIEKMTNKDTYLPKENVLPKHSLCYQKMVYNELTKIRYID--DQGKTN-YFSGQEKQQVFNDLFK--QKR-KVKK   566
WP_003727705   493  SAVDFIEKMTNKDTYLPKENVLPKHSLCYQKMVYNELTKIRYID--DQGKTN-YFSGREKQQIENDLFK--QKR-KVKK   566
WP_003730785   493  SAVDFIEKMTNKDTYLPKENVLPKHSLCYQKMVYNELTKIRYID--DQGKTN-YFSGREKQQIENDLFK--QKR-KVKK   566
WP_003733029   493  SAVDFIEKMTNKDTYLPKENVLPKHSLCYQKMVYNELTKIRYID--DQGKTN-YFSGQEKQQIENDLFK--QKR-KVKK   566
WP_003739838   493  SAVDFIEKMTNKDTYLPKENVLPKHSLCYQKMVYNELTKIRYID--DQGKTN-YFSGQEKQQIENDYFK--QKR-KVSK   566
WP_014601172   493  SAVDFIEKMTNKDTYLPKENVLPKHSLCYQKMVYNELTKIRYID--DQGKTN-YFSGQEKQQIENDLFK--QKR-KVKK   566
WP_023548323   493  SAVDFIEKMTNKDTYLPKENVLPKHSLCYQKMVYNELTKIRYID--DQGKTN-YFSGQEKQQIENDLFK--QKR-KVKK   566
WP_031665337   493  SAVDFIEKMTNKDTYLPKENVLPKHSLCYQKMVYNELTKIRYID--DQGKTN-YFSGQEKQQIENDLFK--QKR-KVKK   566
WP_031669209   493  SAVDFIEKMTNKDTYLPKENVLPKHSLCYQKMVYNELTKIRYID--DQGKTN-YFSGQEKQQIENDLFK--QKR-KVKK   566
WP_033920898   493  SAVDFIEKMTNKDTYLPKENVLPKHSLCYQKMVYNELTKIRYID--DQGKTN-YESGQEKQQIENDLEK--QKR-KVKK   566
AKI42028       496  SAVDFIEKMTNKDTYLPKENVLPKHSLCYQKMVYNELTKIRYID--DQGKTN-YESGQEKQQIENDLFK--QKR-KVKK   569
AKI50529       496  SAVDFIEKMTNKDTYLPKENVLPKHSLCYQKMVYNELTKIRYID--DQGKTN-YESGQEKQQIENDLEK--QKR-KVKK   569
EFR83390         1  ---------------------------------------------------IFNDLEK--QKR-KVKK            14
WP_046323366   493  SAIDFIEKMTNKDTYLPKENVLPKHSLCYQKMVYNELTKIRYTD--DQGKTH-YESGQEKQQIENDLEK--QKR-KVKK   566
AKE81011       503  SAQSFIERMTNEDKNLPNEKVLPKHSLLYEFFVYNELTKVYVT--EGMRKPaELSGEQKAIVDLLKKIL-DK AFLDDKVNEEVIEDIIKTLTLFEDKDMIH   577
CUO82355       503  TAEGFIKRMRSYCTYFPDEEVLPKNSLIVSKYEVYNELNLNKIRVDD------kLLEVDKNDIYNELFM--KQNK-TVTE   571
WP_033162887   504  TAEGFIERMKNTGTYFPDEPVMAKNSLTVSKFEVLNELNKIRING-----kLIAVETKKELLSDLFM--KNK-TITD   572
AGZ01981       520  SAQSFIERMTNEDKNLPNEKVLPKHSLLYEFFVYNELTKVYVT--EGMRKPaELSGEQKKAIVDLLFK--TNR-KVTV   594
AKA60242       487  SAQSFIERMTNEDKNLPNEKVLPKHSLLYEFFVYNELTKVKVT--EGMRKP aELSGEQKKAIVDLLFK--TNR-KVTV   561
AKS40380       487  SAQSFIERMTNEDKNLPNEKVLPKHSLLYEFFVYNELTKVKVT--EGMRKPaELSGEQKKAIVDLLFK--TNR-KVTV   561
4UN5_B         491  SAQSFIERMTNEDKNLPNEKVLPKHSLLYEFFVYNELTKVKVT--EGMRKPaELSGEQKKAIVDLLFK--TNR-KVTV   565
WP_010922251   562  KQLKEDYFKK--IECFDSVEISGVEDR---FNASLGTYHDLLKIIKDK DFLDNEENEDILEDIVLTLFEDREMIE      633
WP_010922251   564  EKLLNYLNKE--FPEYRIKDLIGLDKEnkSFNASLGTYHDLKKIL-DK AFLDDKVNEEVIEDIIKTLTLFEDKDMIH    637
WP_039695303   562  KDIIHYLHN---VDGYDGIELKGIEKQ--FNASLSTYHDLLKIIKDK FNTSLGTYHDLLKIIKDK DFLDNEENEDILEDIVLTLFEDKEMIE   632
WP_045635197   300  KQIAKEILVNe--EDIKGYRVTSTGKPe---FTNLKVYHDIKDITARK ------ENAELLDQIAKILTIYQSSEDIQ   368
5AXW_A         246  KQLKEDYFKK--IECFDSVEISGVEDR---FNASLGTYHDLLKIIKDK DFLDNEENEDILEDIVLTLFEDREMIE     317
WP_009880683   562  KQLKEDYFKK--IECFDSVEISGVEDR---FNASLGTYHDLLKIIKDK DFLDNEENEDILEDIVLTLFEDREMIE     633
WP_010922251   562  KQLKEDYFKK--IECFDSVEISGVEDR---FNASLGTYHDLLKIIKDK DFLDNEENEDILEDIVLTLFEDREMIE     633
WP_011054416   562  KQLKEDYFKK--IECFDSVEISGVEDR---FNASLGTYHDLLKIIKDK DFLDNEENEDILEDIVLTLFEDREMIE     633
WP_011284745   562  KQLKEDYFKK--IECFDSVEISGVEDR---FNASLGTYHDLLKIIKDK DFLDNEENEDILEDIVLTLFEDREMIE     633
WP_011285506   562  KQLKEDYFKK--IECFDSVEISGVEDR---FNASLGTYHDLLKIIKDK DFLDNEENEDILEDIVLTLFEDREMIE     633
WP_011527619   562  KQLKEDYFKK--IECFDSVEISGVEDR---FNASLGTYHDLLKIIKDK DFLDNEENEDILEDIVLTLFEDREMIE     633
WP_012560673   562  KQLKEDYFKK--IECFDSVEISGVEDR---FNASLGTYHDLLKIIKDK DFLDNEENEDILEDIVLTLFEDREMIE     633
WP_014407541   562  KQLKEDYFKK--IECFDSVEISGVEDR---FNASLGAYHDLLKIIKDK DFLDNEENEDILEDIVLTLFEDRGMIE     633
WP_020905136   562  KQLKEDYFKK--IECFDSVEISGVEDR---FNASLGTYHDLLKIIKDK DFLDNEENEDILEDIVLTLFEDKEMIE     633
WP_023080005   562  KQLKEDYFKK--IECFDSVEISGVEDR---FNASLGTYHDLLKIIKDK DFLDNEENEDILEDIVLTLFEDKEMIE     633
WP_023610282   562  KQLKEDYFKK--IECFDSVEISGVEDR---FNASLGTYHDLLKIIKDK DFLDNEENEDILEDIVLTLFEDKEMIE     633
WP_030125963   562  KQLKEDYFKK--IECFDSVEISGVEDR---FNTSLGTYHDLLKIIKDK DFLDNEENEDILEDIVLTLFEDKEMIE     633
WP_030126706   562  KQLKEDYFKK--IECFDSVEISGVEDR---FNASLGTYHDLLKIIKDK DFLDNEENEDILEDIVLTLFEDREMIE     633
WP_031488318   562  KQLKEDYFKK--IECFDSVEISGVEDR---FNASLGTYHDLLKIIKDK DFLDNEENEDILEDIVLTLFEDREMIE     633
WP_032460140   562  KQLKEDYFKK--IECFDSVEISGVEDR---FNASLGTYHDLLKIIKDK DFLDNEENEDILEDIVLTLFEDREMIE     633
WP_032461047   562  KQLKEDYFKK--IECFDSVEISGVEDR---FNASLGTYHDLLKIIKDK DFLDNEENEDILEDIVLTLFEDREMIE     633
WP_032462016   562  KQLKEDYFKK--IECFDSVEISGVEDR---FNASLGTYHDLLKIIKDK DFLDNEENEDILEDIVLTLFEDREMIE     633
WP_032462936   562  KQLKEDYFKK--IECFDSVEISGVEDR---FNASLGTYHDLLKIIKDK DFLDNEENEDILEDIVLTLFEDREMIE     633
WP_032464890   562  KQLKEDYFKK--IECFDSVEISGVEDR---FNASLGTYHDLLKIIKDK DFLDNEENEDILEDIVLTLFEDREMIE     633
WP_033888930   387  KQLKEDYFKK--IECFDSVEISGVEDR---FNASLGTYHDLLKIIKDK DFLDNEENEDILEDIVLTLFEDREMIE     458
WP_038431314   562  KQLKEDYFKK--IECFDSVEISGVEDR---FNASLGTYHDLLKIIKDK DFLDNEENEDILEDIVLTLFEDREMIE     633
WP_038432938   562  KQLKEDYFKK--IECFDSVEISGVEDR---FNTSLGTYHDLLKIIKDK DFLDNEENEDILEDIVLTLFEDREMIE     633
WP_038434062   562  KQLKEDYFKK--IECFDSVEISGVEDR---FNASLGTYHDLLKIIKDK DFLDNEENEDILEDIVLTLFEDREMIE     633
```

-continued

```
BAQ51233         473 KQLKEDYFKK--IECFDSVEISGVEDR---FNASLGTYHDLLKIIKDK DFLDNEENEDILEDIVLTLFEDREMIE     544
KGE60162             ------------------------------------------------ ------------------------
KGE60856             ------------------------------------------------ ------------------------
WP_002989955     562 KQLKEDYFKK--IECFDSVEISGVEDR---FNASLGTYHDLLKIIKDK DFLDNEENEDILEDIVLTLFEDREMIE     633
WP_003030002     561 DKLLNYLNKE-FEEFRIVNLTGLDKEnkAFNSSLGTYHDLRKIL-DK  SFLDDKANEKTIEDIIQTLTLFEDREMIR   634
WP_003065552     564 EKLNYLNKE--FPEYRIKDLIGLDKErnkAFNSLGTYHDLRKIL-DK  AFLDDKVNEEVIEDIIKTLTLFEDKDMIH   637
WP_001040076     563 KDIISFLNK---VDGYEGIAIKGIEKQ---FNASLSTYHDLKKIL-GK DFLDNTDNELILEDIVQTLTLFEDREMIK   635
WP_001040078     562 KKLLDFLAKE-YEEFRIVDVIGLDKEhkAFNASLGTYHDLEKIL-DK  DFLDNPDNESILEDIVQTLTLFEDREMIK   635
WP_001040080     562 KKLLDFLAKE-YEEFRIVDVIGLDKEhkAFNASLGTYHDLEKIL-DK  DFLDNPDNESILEDIVQTLTLFEDREMIK   635
WP_001040081     562 KKLLDFLAKE-YEEFRIVDVIGLDKEhkAFNASLGTYHDLEKIL-DK  DFLDNPDNESILEDIIQTLTLFEDREMIK   635
WP_001040083     562 KKLLDFLAKE-YEEFRIVDVIGLDKEhkAFNASLGTYHDLEKIL-DK  DFLDNPDNESILEDIIQTLTLFEDREMIK   635
WP_001040085     562 KKLLDFLAKE-YEEFRIVDVIGLDKEhkAFNASLGTYHDLEKIL-DK  DFLDNPDNESILEDIVQTLTLFEDREMIK   635
WP_001040087     562 KKLLDFLAKE-YEEFRIVDVIGLDKEhkAFNASLGTYHDLEKIL-DK  DFLDNPDNESILEDIVQTLTLFEDREMIK   635
WP_001040088     562 KKLLDFLAKE-YEEFRIVDVIGLDKEhkAFNASLGTYHDLEKIL-DK  DFLDNPDNESILEDIVQTLTLFEDREMIR   635
WP_001040089     562 KKLLDFLAKE-YEEFRIVDVIGLDKEhkAFNASLGTYHDLEKIL-DK  DFLDNPDNESILEDIVQTLTLFEDREMIR   635
WP_001040090     562 KKLLDFLAKE-YEEFRIVDVIGLDKEhkAFNASLGTYHDLEKIL-DK  DFLDNPDNESILEDIVQTLTLFEDREMIK   635
WP_001040091     562 KKLLDFLAKE-FEEFRIVDVIGLDKErnkAFNASLGTYHDLEKIL-DK DFLDNPDNESILEDIVQTLTLFEDREMIK   635
WP_001040092     562 KQLLDFLAKE-YEEFRIVDVTGLDKEhkAFNASLGTYHDLEKIL-DK  DFLDNTDNELILEDIVQTITLFEDREMIK   635
WP_001040094     562 KDIISFLNK---VDGYEGIAIKGIEKQ---FNASLSTYHDLKKIL-GK DFLDNTDNELILEDIVQTLTLFEDREMIR   632
WP_001040095     563 KDIISFLNK---VDGYEGIAIKGIEKQ---FNASLSTYHDLKKIL-GK DFLDNTDNELILEDIVQTLTLFEDREMIR   632
WP_001040096     563 KDIISFLNK---VDGYEGIAIKGIEKQ---FNASLSTYHDLKKIL-GK DFLDNTDNELILEDIVQTLTLFEDREMIR   632
WP_001040097     563 KDIISFLNK---VDGYEGIAIKGIEKQ---FNASLSTYHDLKKIL-GK DFLDNTDNELILEDIVQTLTLFEDREMIR   632
WP_001040098     563 KDIISFLNK---VDGYEGIAIKGIEKQ---FNASLSTYHDLKKIL-GK DFLDNTDNELILEDIVQTLTLFEDREMIR   632
WP_001040099     563 KDIISFLNK---VDGYEGIAIKGIEKQ---FNASLSTYHDLKKIL-GK DFLDNTDNELILEDIVQTLTLFEDREMIR   632
WP_001040100     562 KKLLDFLAKE-YEEFRIVDVIGLDKEhkAFNASLGTYHDLEKIL-DK  DFLDNPDNESILEDIVQTLTLFEDREMIK   635
WP_001040104     562 KKLLDFLAKE-YEEFRIVDVIGLDKEhkAFNASLGTYHDLEKIL-DK  DFLDNPDNESILEDIVQTLTLFEDREMIK   635
WP_001040105     562 KKLLDFLAKE-YEEFRIVDVIGLDKEhkAFNASLGTYHDLEKIL-DK  DFLDNPDNESILEDIVQTLTLFEDREMIK   635
WP_001040106     562 KKLLDFLAKE-YEEFRIVDVIGLDKEhkAFNASLGTYHDLEKIL-DK  DFLDNPDNESILEDIVQTLTLFEDREMIK   635
WP_001040107     562 KKLLDFLAKE-YEEFRIVDVIGLDKEhkAFNASLGTYHDLEKIL-DK  DFLDNPDNESILEDIVQTLTLFEDREMIK   635
WP_001040108     562 KKLLDFLAKE-YEEFRIVDVIGLDKEhkAFNASLGTYHDLEKIL-DK  DFLDNPDNESILEDIVQTITLFEDREMIK   635
WP_001040109     562 KKLLDFLAKE-YEEFRIVDVIGLDKEhkAFNASLGTYHDLEKIL-DK  DFLDNPDNESILEDIVQTLTLFEDREMIK   635
WP_001040110     562 KKLLDFLAKE-YEEFRIVDVIGLDKEhkAFNASLGTYHDLEKIL-DK  DFLDNPDNESILEDIVQTLTLFEDREMIK   635
WP_015058523     562 KQLLDFLAKE-FEEFRIVDVTGLDKEhkAFNASLGTYHDLKKIL-DK  DFLDNTDNELILEDIVQTITLFEDREMIK   632
WP_017643650     563 KDIISFLNK---VDGYEGIAIKGIEKQ---FNASLSTYHDLKKIL-GK DFLDNTDNELILEDIVQTLTLFEDREMIR   632
WP_017647151     562 KKLLDFLAKE-YEEFRIVDVIGLDKEhkAFNASLGTYHDLEKIL-DK  DFLDNPDNESILEDIVQTLTLFEDREMIR   635
WP_017648376     562 KKLLDFLAKE-YEEFRIVDVIGLDKEhkAFNASLGTYHDLEKIL-DK  DFLDNPDNESILEDIVQTLTLFEDREMIK   635
WP_017649527     562 KKLLDFLAKE-YEEFRIVDVIGLDKEhkAFNASLGTYHDLEKIL-DK  DFLDNPDNESILEDIVQTLTLFEDREMIK   635
WP_017771611     562 KKLLDFLAKE-YEEFRIVDVIGLDKEhkAFNASLGTYHDLEKIL-DK  DFLDNPDNESILEDIVQTLTLFEDREMIK   635
WP_017771984     562 KKLLDFLAKE-YEEFRIVDVIGLDKEhkAFNASLGTYHDLEKIL-DK  DFLDNPDNESILEDIVQTLTLFEDREMIK   635
CFQ25032         562 KKLLDFLAKE-YEEFRIVDVIGLDKEhkAFNASLGTYHDLEKIL-DK  DFLDNPDNESILEDIVQTLTLFEDREMIK   635
CFV16040         562 KKLLDFLAKE-YEEFRIVDVIGLDKEhkAFNASLGTYHDLEKIL-DK  DFLDNPDNESILEDIVQTLTLFEDREMIK   635
KLJ37842         562 KKLLDFLAKE-YEEFRIVDVIGLDKEhkAFNASLGTYHDLEKIL-DK  DFLDNPDNESILEDIVQTLTLFEDREMIK   635
KLJ72361         562 KKLLDFLAKE-YEEFRIVDVIGLDKEhkAFNASLGTYHDLEKIL-DK  DFLDNPDNESILEDIVQTLTLFEDREMIK   635
KLL20707         562 KKLLDFLAKE-YEEFRIVDVIGLDKEhkAFNASLGTYHDLEKIL-DK  DFLDNPDNESILEDIVQTLTLFEDREMIK   635
KLL42645         562 KKLLDFLAKE-YEEFRIVDVIGLDKEhkAFNASLGTYHDLEKIL-DK  DFLDNPDNESILEDIVQTLTLFEDREMIK   635
WP_047207273     562 KKLLDFLAKE-YEEFRIVDVIGLDKEhkAFNASLGTYHDLEKIL-DK  DFLDNPDNESILEDIVQTLTLFEDREMIK   635
WP_047209694     563 KDIISELNK---VDGYEGIAIKGIEKQ---FNASLSTYHDLKKIL-GK DFLDNTDNELILEDIVQTLTLFEDREMIR   632
WP_050198062     562 KKLLDFLAKE-YEEFRIVDVIGLDKEhkAFNASLGTYHDLEKIL-DK  DFLDNPDNESILEDIVQTLTLFEDREMIK   635
WP_050201642     562 KKLLDFLAKE-YEEFRIVDVIGLDKEhkAFNASLGTYHDLEKIL-DK  DFLDNPDNESILEDIVQTLTLFEDREMIK   635
WP_050204027     562 KKLLDFLAKE-YEEFRIVDVIGLDKEhkAFNASLGTYHDLEKIL-DK  DFLDNPDNESILEDIVQTLTLFEDREMIK   635
WP_050881965     562 KKLLDFLAKE-YEEFRIVDVIGLDKEhkAFNASLGTYHDLEKIL-DK  DFLDNPDNESILEDIVQTLTLFEDREMIK   635
WP_050886065     562 KKLLDFLAKE-YEEFRIVDVIGLDKEhkAFNASLGTYHDLEKIL-DK  DFLDNPDNESILEDIVQTLTLFEDREMIK   635
AHN30376         562 KQLLDFLAKE-FEEFRIVDVTGLDKEhkAFNASLGTYHDLEKIL-DK  DFLDNPDNESILEDIVQTITLFEDREMIK   635
```

-continued

```
EA078426         562  KKLLDFLAKE- -YEEEFRIVDVIGLDKEnkAFNASLGTYHDLEKIL-DK  DFLDNPDNESILEDIVQTLTLFEDREMIK  635
CCW42055         562  KQLLDFLAKE- -FEEEFRIVDVTGLDKEnkAFNASLGTYHDLEKIL-GK  DFLDNPDNESILEDIVQTLTLFEDREMIK  635
WP_003041502     561  DKLLNYLNKE- -FEEEFRIVNLTGLDKEmkVENSSLGTYHDLRKIL-NK  SFLDNKENAQIIEDIIQTLTLFEDREMIR  634
WP_037593752     562  DKLLNYLNKE- -FEEEFRIVNLTGLDKEnkAENSSLGTYHDLRKIL-DK  SFLDNKANEKTIEDIIQTLTLFEDREMIR  635
WP_049516684     562  DKLLNYLNKE- -FEEEFRIVNLTGLDKEnkAFNASLGTYHDLRKIL-DK  SFLDNKVNEKIIEDIIQTLTLFEDREMIR  635
GAD46167         561  EKLLNYLDKE- -FPEYRIQDLVGLDKEnkSFNASLGTYHDLKKIL-DK  SFLDDKVNEEVIEDIIKTLTLFEDREMIQ  634
WP_018363470     572  KQLKEDYFKK- -IECEDSVEIIGVEDR---FNASLGTYHDLLKIIKDK  DFLDNEENEDILEDIVLTLTLFEDKEMIE  643
WP_003043819     561  DKLLNYLNKE- -FEEEFRIVNLTGLDKEnkAENSSLGTYHDLRKIL-DK  SFLDDKANEKTIEDIIQTLTLFEDREMIR  634
WP_006269658     562  KQLKEDYFKK- -IECEDSVEISGVEDR---FNASLGTYHDLLKIIKDK  DFLDNEENEDILEDIVLTLTLFEDKEMIE  633
WP_048800889     562  DKLLNYLDKE- -FEEEFRIVDLTGLDKEnkAFNASLGTYHDLRKIL-DK  DFLDNEENEDILEDIVLTLTLFEDKEMIE  634
WP_012767106     562  KQLKEDYFKK- -IECEDSVEISGVEDR---FNASLGTYHDLLKIIKDK  DFLDNEENEDILEDIVLTLTLFEDKEMIE  633
WP_014612333     562  KQLKEDYFKK- -IECEDSVEISGVEDR---FNASLGTYHDLLKIIKDK  DFLDNEENEDILEDIVLTLTLFEDKEMIE  633
WP_015017095     562  KQLKEDYFKK- -IECEDSVEISGVEDR---FNASLGTYHDLLKIIKDK  DFLDNEENEDILEDIVLTLTLFEDKEMIE  633
WP_015057649     562  KQLKEDYFKK- -IECEDSVEISGVEDR---FNASLGTYHDLLKIIKDK  DFLDNEENEDILEDIVLTLTLFEDKEMIE  633
WP_048327215     562  KQLKEDYFKK- -IECEDSVEISGVEDR---FNASLGTYHDLLKIIKDK  DFLDNEENEDILEDIVLTLTLFEDKEMIE  633
WP_049519324     562  KQLKENYFKK- -IECEDSVEISGVEDR---FNASLGTYHDLLKIIQDK  DFLDNEENEDILEDIVLTLTLFEDKEMIE  633
WP_012515931     562  KQLKENYFKK- -IECWDSVEITGVEDS---FNASLGTYHDLLKIIQDK  DFLDNPDNQKIIEDIILTLTLFEDKKMIS  633
WP_021320964     562  KQLKENYFKK- -IECWDSVEITGVEDS---FNASLGTYHDLLKIIQDK  DFLDNPDNQKIIEDIILTLTLFEDKKMIS  633
WP_037581760     562  KQLKENYFKK- -IECWDSVEITGVEDS---FNASLGTYHDLLKIIQDK  SFLDDKTNEQIIEDIVLTLTLFEDRDMIH  633
WP_004232481     561  AKLLSYLNNE- -FEEFRINDLIGLDKDskSFNASLGTYHDLKKIL-DK  AFLDDKVNEEVIEDIIKTLTLFEDKDMIH  635
WP_009854540     562  EKLLNYLNKE- -FPEYRIKDLIGLDKEnkSFNASLGTYHDLKKIL-DK  SFLDDKTNETIEDIIQTLTLFEDRDMIR  635
WP_012962174     562  DKPLNYLNKE- -FPEYRIQDLIGLDKEnkSFNASLGTYHDLKKIL-DK  AFLDDKVNEEVIEDIIKTLTLFEDKDMIH  637
WP_039695303     564  EKLLNYLNKE- -FEEEFRINDLIGLDKDskSFNASLGTYHDLKKIL-DK  AFLDDKVNEEVIEDIIKTLTLFEDKDMIH  637
WP_004334983     561  AKLLSYLNNE- -MKCFHTVTILGVEDR---FNASLGTYHDLLKFKDK  AFLDDEANQDILEEIWTLTLFEDQAMIE  634
WP_003099269     562  KQLKEEYESK- -MKCFHTVTILGVEDR---FNASLGTYHDLLKFKDK  AFLDDEANQDILEEIWTLTLFEDQAMIE  633
AHY15608         562  KQLKEEYESK- -MKCFHTVTILGVEDR---FNASLGTYHDLLKIFKDK  AFLDDEANQDILEEIWTLTLFEDQAMIE  633
AHY17476         562  KQLKEEYESK- -MKCFHTVTILGVEDR---FNASLGTYHDLLKIFKDK  AFLDDEANQDILEEIWTLTLFEDQAMIE  633
ESR09100              ----------  --------------------------------  ------------------------------
AGM98575         562  KQLKEEYESK- -MKCFHTVTILGVEDR---FNASLGTYHDLLKIFKDK  AFLDDEANQDILEEIWTLTLFEDQAMIE  633
ALF27331         561  DKLMDFLEKE- -FDEFRIVDLTGLDKEnkAFNASYGTYHDLRKIL-DK  DFLDNSKNEKILEDIVLTLTLFEDREMIR  634
WP_018372492     574  RKLKDFIEKElgYGYIDIDnkIKGVEEQ- -FNASYTTYQDLLKIIGDK  EFLDEENKDLLEEIIYILTVFEDRKMIE  647
WP_045618028     563  KDIIQYLHN--- -VDSYDGIELKGIEKQ- -FNASLSTYHDLLKIIKDK  EFMDDSKNEAILENIVHTLTIFEDRKMIK  633
WP_045635197     562  AKLLSYLNNE- -FEEFRIKDLIGLDKDskSFNASLGTYHDLKKIL-DK  EFMDDAKNEAILENIVHTLTIFEDREMIK  632
WP_002263549     561  DKLMDFLEKE- -FDEFRIVDLTGLDKEnkAFNASYGTYHDLCKIL-DK  DFLDNSKNEKILEDIVLTLTLFEDREMIR  634
WP_002263887     561  DKLMDFLEKE- -FDEFRIVDLTGLDKEnkAFNASYGTYHDLCKIL-DK  DFLDNSKNEKILEDIVLTLTLFEDREMIR  634
WP_002264920     561  DKLMDFLEKE- -FDEFRIVDLTGLDKEnkAFNASYGTYHDLCKIL-DK  DFLDNSKNEKILEDIVLTLTLFEDREMIR  634
WP_002269043     561  DKLMDFLEKE- -FDEFRIVDLTGLDKEnkAFNASYGTYHDLCKIL-DK  DFLDNSKNEKILEDIVLTLTLFEDREMIR  634
WP_002269448     561  DKLMDFLEKE- -FDEFRIVDLTGLDKEnkAFNASYGTYHDLCKIL-DK  DFLDNSKNEKILEDIVLTLTLFEDREMIR  634
WP_002271977     561  DKLMDFLEKE- -FDEFRIVDLTGLDKEnkAFNASYGTYHDLCKIL-DK  DFLDNSKNEKILEDIVLTLTLFEDREMIR  634
WP_002272766     561  DKLMDFLEKE- -FDEFRIVDLTGLDKEnkAFNASYGTYHDLCKIL-DK  DFLDNSKNEKILEDIVLTLTLFEDREMIR  634
WP_002273241     561  DKLMDFLEKE- -FDEFRIVDLTGLDKEnkAFNASYGTYHDLCKIL-DK  DFLDNSKNEKILEDIVLTLTLFEDREMIR  634
WP_002275430     561  DKLMDFLEKE- -FDEFRIVDLTGLDKEnkAFNASYGTYHDLCKIL-DK  DFLDNSKNEKILEDIVLTLTLFEDREMIR  634
WP_002276448     561  KKLLRTFLDKN- -FDEFRIVDIQGLDKEteTENASYATYQDLLKVIKDK  VFMDNPENAEILENIVLTLTLFEDREMIK  635
WP_002277050     561  DKLMDFLEKE- -FDEFRIVDLTGLDKEnkAFNASYGTYHDLLKIL-DK  DFLDNSKNEKILEDIVLTLTLFEDREMIR  634
WP_002277364     561  DKLMDFLEKE- -FDEFRIVDLTGLDKEnkAFNASYGTYHDLLRKIL-DK  DFLDNSKNEKILEDIVLTLTLFEDREMIR  634
WP_002279025     561  DKLMDFLEKE- -FDEFRIVDLTGLDKEnkAFNASYGTYHDLRKIL-DK  DFLDNSKNEKILEDIVLTLTLFEDREMIR  634
WP_002279859     561  DKLMDFLEKE- -FDEFRIVDLTGLDKEnkAFNASYGTYHDLRKIL-DK  DFLDNSKNEKILEDIVLTLTLFEDREMIR  634
WP_002280230     561  DKLMDFLEKE- -FDEFRIVDLTGLDKEnkAFNASYGTYHDLCKIL-DK  DFLDNSKNEKILEDIVLTLTLFEDREMIR  634
WP_002281696     561  DKLMDFLEKE- -FDEFRIVDLTGLDKEnkAFNASYGTYHDLRKIL-DK  DFLDNSKNEKILEDIVLTLTLFEDREMIR  634
WP_002282247     561  KKLRTFLDKN- -FDEFRIVDIQGLDKEteTENASYATYQDLLKVIKDK  VFMDNPENAEILENIVLTLTLFEDREMIK  635
WP_002282906     561  DKLMDFLEKE- -FDEFRIVDLTGLDKEnkAFNASYGTYHDLRKIL-DK  DFLDNSKNEKILEDIVLTLTLFEDREMIR  634
WP_002283846     561  DKLMDFLEKE- -FDEFRIVDLTGLDKEnkAFNASYGTYHDLRKIL-DK  DFLDNSKNEKILEDIVLTLTLFEDREMIR  634
WP_002287255     561  DKLMDFLEKE- -FDEFRIVDLTGLDKEnkAFNASYGTYHDLRKIL-DK  DFLDNSKNEKILEDIVLTLTLFEDREMIR  634
```

| | | | |
|---|---|---|---|
| WP_002288990 | 561 DKLMDFLEKE--FDEFRIVDLTGLDKEmkAFNASYGTYHDLRKIL-DK | DFLDNSKNEKILEDIVLTLTLFEDREMIR | 634 |
| WP_002289641 | 561 DKLMDFLEKE--FDEFRIVDLTGLDKEmkAFNASYGTYHDLCKIL-DK | DFLDNSKNEKILEDIVLTLTLFEDREMIR | 634 |
| WP_002290427 | 561 DKLMDFLEKE--FDEFRIVDLTGLDKEmkAFNASYGTYHDLRKIL-DK | DFLDNSKNEKILEDIVLTLTLFEDREMIR | 634 |
| WP_002295753 | 561 DKLMDFLEKE--FDEFRIVDLTGLDKEmkAFNASYGTYHDLRKIL-DK | DFLDNSKNEKILEDIVLTLTLFEDREMIR | 634 |
| WP_002296423 | 561 DKLMDFLEKE--FEEFRIVNLTGLDKEmkVENSSLGTYHDLRKIL-NK | SFLDNKENEQIIEDIQTLTLFEDREMIR | 644 |
| WP_002304487 | 571 DKLNYLNKE---FDEFRIVDLTGLDKEmkVFNASYGTYHDLCKIL-DK | DFLDNSKNEKILEDIVLTLTLFEDREMIR | 634 |
| WP_002305844 | 561 DKLMDFLEKE--FDEFRIVDLTGLDKEmkAFNASYGTYHDLCKIL-DK | DFLDNSKNEKILEDIVLTLTLFEDREMIR | 634 |
| WP_002307203 | 561 DKLMDFLEKE--FDEFRIVDLTGLDKEmkAFNASYGTYHDLRKIL-DK | DFLDNSKNEKILEDIVLTLTLFEDREMIR | 634 |
| WP_002310390 | 561 DKLMDFLEKE--FDEFRIVDLTGLDKEmkAFNASYGTYHDLRKIL-DK | DFLDNSKNEKILEDIVLTLTLFEDREMIR | 634 |
| WP_002352408 | 561 DKLMDFLEKE--FDEFRIVDLTGLDKEmkAFNASYGTYHDLRKIL-DK | DFLDNSKNEKILEDIVLTLTLFEDREMIR | 634 |
| WP_012997688 | 561 DKLMDFLEKE--FDEFRIVDLTGLDKEmkAFNASYGTYHDLRKIL-DK | DFLDNSKNEKILEDIVLTLTLFEDREMIR | 634 |
| WP_014677909 | 561 DKLMDFLEKE--FDEFRIVDLTGLDKEmkAFNASYGTYHDLRKIL-DK | DFLDNSKNEKILEDIVLTLTLFEDREMIR | 634 |
| WP_019312892 | 561 DKLMDFLEKE--FDEFRIVDLTGLDKEmkAFNASYGTYHDLRKIL-DK | DFLDNSKNEKILEDIVLTLTLFEDREMIR | 634 |
| WP_019313659 | 561 DKLMDFLEKE--FDEFRIVDLTGLDKEmkVFNASYGTYHDLCKIL-DK | DFLDNSKNEKILEDIVLTLTLFEDREMIR | 634 |
| WP_019314093 | 561 DKLMDFLEKE--FDEFRIVDLTGLDKEmkAFNASYGTYHDLCKIL-DK | DFLDNSKNEKILEDIVLTLTLFEDREMIR | 634 |
| WP_019315370 | 561 DKLMDFLEKE--FDEFRIVDLTGLDKEmkVFNASYGTYHDLCKIL-DK | DFLDNSKNEKILEDIVLTLTLFEDREMIR | 634 |
| WP_019803776 | 561 DKLMDFLEKE--FDEFRIVDLTGLDKEmkAFNASYGTYHDLRKIL-DK | DFLDNSKNEKILEDIVLTLTLFEDREMIR | 634 |
| WP_019805234 | 561 DKLMDFLEKE--FDEFRIVDLTGLDKEmkAFNASYGTYHDLRKIL-DK | DFLDNSKNEKILEDIVLTLTLFEDREMIR | 634 |
| WP_024783594 | 561 DKLMDFLEKE--FDEFRIVDIQGLDKEtETFNASYATYQDLLKVIKDK | VFMDNPENAEILENIVLTLTLFEDREMIK | 635 |
| WP_024784288 | 561 KKLRTFLDKN--FDEFRIVDIQGLDKEtETFNASYATYQDLLKVIKDK | VFMDNPENAEILENIVLTLTLFEDREMIK | 635 |
| WP_024784666 | 561 DKLMDFLEKE--FDEFRIVDLTGLDKEmkAFNASYGTYHDLRKIL-DK | DFLDNSKNEKILEDIVLTLTLFEDREMIR | 634 |
| WP_024784894 | 561 KKLRTFLDKN--FDEFRIVDLTGLDKEmkETETFNASYATYQDLLKVIKDK | VFMDNPENAEILENIVLTLTLFEDREMIK | 635 |
| WP_024784433 | 561 DKLMDFLEKE--FDEFRIVDLTGLDKEmkVFNASYGTYHDLCKIL-DK | DFLDNSKNEKILEDIVLTLTLFEDREMIR | 634 |
| WP_049473442 | 561 DKLMDFLEKE--FDEFRIVDLTGLDKEmkAFNASYGTYHDLCKIL-DK | DFLDNSKNEKILEDIVLTLTLFEDREMIR | 634 |
| WP_049474547 | 554 DKLMDFLEKE--FDEFRIVDLTGLDKEmkAFNASYGTYHDLRKIL-DK | DFLDNSKNEKILEDIVLTLTLFEDREMIR | 627 |
| EMC03581 | 565 KDIIQYLHT---VDGYDGIELKGIEKQ----FNASLSTYHDLLKIIKDK | EFMDDPNNEEILENIVHTLTIFEDREMIK | 635 |
| WP_000428612 | 563 KDIIQFLHN---VDGYDGIELKGIEKQ----FNASLSTYHDLLKIIKDK | EFMDDSKNEEILENIVHTLTIFEDREMIK | 633 |
| WP_000428613 | 562 KDIIHYLHN---VDGYDGIELKGIEKH----FNSSLSTYHDLLKIIKDK | EFMDDPKQNEEILENIVHTLTIFEDREMIK | 632 |
| WP_049523028 | 531 KQLKENYFNK--IRCLDSITISGVEDK----FNASLGTYHDLLNIIKNQ | EFMDDPKNGEILENIIHTLTIFEDRVMIK | 602 |
| WP_003107102 | 564 WP_000428613 563 KDLIHYLHN---VDGYDGIELKGIEKQ----FNASLGTYHDLLKIIKDK | KILDDEQNQDSLEDIVLTLTLFEDEKMIA | 635 |
| WP_0542792288 | 565 KDIIQYLHN---VDGYDGIELKGIEKQ----FNASLGTYHDLLKIIKDK | AFLDNSENENIIEDIILTLTLFEDREMIA | 635 |
| WP_049531101 | 563 KDLIHYLHN---VDGYDGIELKGIEKQ----FNASLGTYHDLLKIIKDK | RFMDEPKNQEILENIVHTLTLFEDREMIK | 633 |
| WP_049538452 | 563 KDIIQYLHN---VDGYDGIELKGIEKQ----FNASLGTYHDLLKIIKDK | EFMDDSKNEEILENIVHTLTIFEDREMIK | 633 |
| WP_049549711 | 565 KDIIHYLHT---VDGYDGIELKGIEKQ----FNASLGTYHDLLKIIKDK | EFMDDSKNEAILENIVHTLTIFEDREMIK | 636 |
| WP_007896501 | 517 KDLKEKYPSQ--IEGLENVDVTGVEGA----FNASLGTYNDLLKIIKDK | AFLDDEANAEILEDIVLLITLFQDEKLIE | 588 |
| EFR44625 | 562 KDIIHYLHN---VDGYDGIELKGIEKQ----FNANLSTYHDLLKITKDK | AFLDDEANAEILEDIVLLITLFQDEKLIE | 632 |
| WP_002897477 | 563 KDIIHYLHN---VDGYDGIELKGIEKQ----FNASLSTYHDLLKIIKDK | EFMDDPKQNEEILENIVHTLTIFEDREMIK | 633 |
| WP_002906454 | 562 KDIIQFLHN---VDGYDGIELKGIEKQ----FNASLSTYHDLLKIIKDK | EFMDNPKQNGEILENIIHTLTIFEDREMIK | 636 |
| WP_009729476 | 565 KKILNFLDKN--PDEFRITDIQGLDNEtgNENASYGTYHDLLKIIGDK | AFMDDAKNEAILENIVHTLTIFEDREMIK | 636 |
| CQR24647 | 565 KDLIHYLHN---VDGYDGIELKGIEKQ----FNASLSTYHDLLKIIKDK | EFMDSSDNVDVLEDIVLSLTLFEDREMIK | 636 |
| WP_000066813 | 563 KDIIHYLHN---VDGYDGIELKGIEKQ----FNASLSTYHDLLKIIKDK | AFMDDSKNEEILENIIHTLTIFEDREMIK | 635 |
| WP_009754323 | 562 KDIKAYL-EN--SNGYAGVELKGLEEQ----FNASLPTYHDLLKILRDK | AFIDAEENQEILEDIVLTLTLFEDREMIK | 632 |
| WP_044674937 | 562 EKLMDFLGKE--FDEFRIVDLLGLDKDnkSFNASLGTYHDLKKIV-SK | DLLDNPENEDILENVVLTLTLFEDREMIK | 634 |
| WP_044676715 | 561 EKLMDFLGKE--FDEFRIVDLLGLDKDnkSFNASLGTYHDLKKIV-SK | DLLDNPENEDILENVVLTLTLFEDREMIK | 634 |
| WP_044680361 | 561 KDIKAYL-EN--SNGYAGVELKGLEEQ----FNASLPTYHDLLKILRDK | AFIDAEENQEILEDIVLTLTLFEDREMIR | 632 |
| WP_044681799 | 562 DKLLNYLGKE--FDEFRIVDLTGLDKEmkVENSSLGTYHDLRKIL-DR | SFLDNKENEQIIEDIQTLTLFEDREMIR | 634 |
| WP_049533112 | 541 TSLKKWLAEH--EHMTVSVVQGTQKEt-EFATSLQAEHREVKIF-DR | ETVSNPANEEMFEKIIYWSTVFEDKKIMR | 612 |
| WP_029090905 | 568 KKLKNWLVNNqcCS--KDAEIKGFQKEh-QESTSLTPWIDETNIFGKI | ---DQSNFDLIENIIYDLTVFEDKKIMK | 637 |
| WP_006506696 | 562 KQLKEDYFKK--IECEDSVEISGVEDR----FNSNYSTYIDLSKIPDMK | DFLDNEENEDILENIVLTLTLFEDREMIK | 633 |
| AIT42264 | 568 NQLVKYIENK---EQIIAPEIKGIEDS----FNSNYSTYIDLSKIPDMK | -LLEKDEDEILEEIIKILTIFEDREMKR | 637 |
| WP_034440723 | 562 KQLKEDYFKK--IECEDSVEISGVEDR----FNASLGTYHDLLKIIKDK | DFLDNEENEDILENIVLTLTLFEDREMIE | 633 |
| AKQ21048 | 563 KDIANYLEQ---YGYVDGTDIKGVEDK----FNASLSTYNDLAKIDGAK | AYLDDPEYADVWEDIIKILTIFEDKAMRK | 633 |

-continued

| | | | | |
|---|---|---|---|---|
| WP_002364836 | 570 | KDIIQFYRNE-YN-TEIVTLSGLEED--QFNASFSTYQDLLKCGLTR | AELDHPDNAEKLEDIIKILTIFEDRQRIR | 641 |
| WP_016631044 | 521 | KDIIQFYRNE-YN-TEIVTLSGLEED--QFNASFSTYQDLLKCGLTR | AELDHPDNAEKLEDIIKILTIFEDRQRIR | 592 |
| EMS75795 | 306 | KKLQQFLSAN-YN-IEDAEILGVDKA--FNSSYATYHDFLDLAKPN | ELLEQPEMNAMFEDIVKILTIFEDREMIR | 381 |
| WP_002373311 | 570 | KDIIQFYRNE-YN-TEIVTLSGLEED--QFNASFSTYQDLLKCGLTR | AELDHPDNAEKLEDIIKILTIFEDRQRIR | 641 |
| WP_002378009 | 570 | KDIIQFYRNE-YN-TEIVTLSGLEED--QFNASFSTYQDLLKCGLTR | AELDHPDNAEKLEDIIKILTIFEDRQRIR | 641 |
| WP_002407324 | 570 | KDIIQFYRNE-YN-TEIVTLSGLEED--QFNASFSTYQDLLKCGLTR | AELDHPDNAEKLEDIIKILTIFEDRQRIR | 641 |
| WP_002413717 | 570 | KDIIQFYRNE-YN-TEIVTLSGLEED--QFNASFSTYQDLLKCGLTR | AELDHPDNAEKLEDIIKILTIFEDRQRIR | 641 |
| WP_010775580 | 572 | KDIIQFYRNE-YN-TEIVTLSGLEED--QFNASFSTYQDLLKCGLTR | AELDHPDNAEKLEDIIKILTIFEDRQRIR | 643 |
| WP_010818269 | 570 | KDIIQFYRNE-YN-TEIVTLSGLEED--QFNASFSTYQDLLKCGLTR | AELDHPDNAEKLEDIIKILTIFEDRQRIR | 641 |
| WP_010824395 | 570 | KDIIQFYRNE-YN-TEIVTLSGLEED--QFNASFSTYQDLLKCGLTR | AELDHPDNAEKLEDIIKILTIFEDRQRIR | 641 |
| WP_016622645 | 570 | KDIIQFYRNE-YN-TEIVTLSGLEED--QFNASFSTYQDLLKCGLTR | AELDHPDNAEKLEDIIKILTIFEDRQRIR | 641 |
| WP_033624816 | 570 | KDIIQFYRNE-YN-TEIVTLSGLEED--QFNASFSTYQDLLKCGLTR | AELDHPDNAEKLEDIIKILTIFEDRQRIR | 641 |
| WP_033625576 | 570 | KDIIQFYRNE-YN-TEIVTLSGLEED--QFNASFSTYQDLLKCGLTR | AELDHPDNAEKLEDIIKILTIFEDRQRIR | 641 |
| WP_033789179 | 570 | KDIIQFYRNE-YN-TEIVTLSGLEED--QFNASFSTYQDLLKCGLTR | AELDHPDNAEKLEDIIKILTIFEDRQRIR | 641 |
| WP_002310644 | 567 | KDLQEFLYLK-YD-IKHAELSGIEKA--FNASYTTYHDFLTMSENK | QWLEDPELASMFBEIIKTLTVFEDREMIK | 641 |
| WP_002312694 | 568 | KDLQEFLYLK-YD-IKHAELSGIEKA--FNASYTTYHDFLTMSENK | QWLEDPELASMFBEIIKTLTVFEDREMIK | 642 |
| WP_002314015 | 568 | KDLQEFLYLK-YD-IKHAELSGIEKA--FNASYTTYHDFLTMSENK | QWLEDPELASMFBEIIKTLTVFEDREMIK | 642 |
| WP_002320716 | 568 | KDLQEFLYLK-YD-IKHAELSGIEKA--FNASYTTYHDFLTMSENK | QWLEDPELASMFBEIIKTLTVFEDRQMIK | 642 |
| WP_002330729 | 567 | KDLQEFLYLK-YD-IKHAELSGIEKA--FNASYTTYHDFLTMSENK | QWLEDPELASMFBEIIKTLTVFEDRQMIK | 641 |
| WP_002335161 | 568 | KDLQEFLYLK-YD-IKHAELSGIEKA--FNASYTTYHDFLTMSENK | QWLEDPELASMFBEIIKTLTVFEDREMIK | 642 |
| WP_002345439 | 568 | KDLQEFLYLK-YD-IKHAELSGIEKA--FNASYTTYHDFLTMSENK | QWLEDPELASMFBEIIKTLTVFEDRQMIK | 642 |
| WP_034867970 | 562 | KKLQNFLYTH-YH-IENAQIFGIEKA--FNASYSTYHDFMKLAKTN | EWLEQPEMEPIFEDIVKILTIFEDRQMIK | 637 |
| WP_047937432 | 568 | KDLQEFLYLK-YD-IKHAELSGIEKA--FNASYTTYHDFLTMSENK | QWLEDPELASMFBEIIKTLTVFEDREMIK | 642 |
| WP_010720994 | 562 | KKLQNFLYTH-YH-IENAQIFGIEKA--FNASYSTYHDFMKLAKTN | EWLEQPEMEPIFEDIVKILTIFEDRQMIK | 637 |
| WP_010737004 | 562 | KKLQNFLYTH-YH-IENAQIFGIEKA--FNASYSTYHDFMKLAKTN | EWLEQPEMEPIFEDIVKILTIFEDRQMIK | 637 |
| WP_034700478 | 562 | KKLQNFLYTH-YH-IENAQIFGIEKA--FNASYSTYHDFMKLAKTN | EWLEQPEMEPIFEDIVKILTIFEDRQMIK | 637 |
| WP_007029003 | 564 | KKLENYLRIE1---SISSPSVKGIEEQ--FNANFGTYLDLKKFDELH | PYLDDEKYQDTLEEVIKVLTVFEDRSMIQ | 634 |
| WP_023519017 | 560 | KQLRKFLELN-EQ-IDSTEIKGIETS--FNASYSTYHDLLKLS-- | TLLDDPDMTTMFBEIIKILTVFEDREMIR | 631 |
| WP_010770040 | 564 | KLLEKFLSNE-PG-LVDVAIKGIE-T-SFNAGYGTYHDFLKIGITR | EQLDKEENSETLBEIVKILTVFEDRKMIR | 634 |
| WP_048604708 | 560 | KDLSNFLRNE-YN-LDDVIIDGIE-N-KFNASFNTYHDFLKLKIDP | KVLDDPANEPMFBEIVKILTIFEDRKMLR | 630 |
| WP_010750235 | 601 | KKLQHFLSAN-YN-IECFDSVEISGVEDR--FNSSYATYHDFLBLAKPY | ELLEQPEMEEMFEDIVLILTLFEDREMVR | 636 |
| AII6583 | 601 | KQLKEDYFKK-IECFDSVEISGVEDR--FNSSYATYHDFLBLAKPY | DFLDNEENEDILEDIVLIITIFEDREMIE | 672 |
| WP_029073316 | 647 | NAMKKWLVKNqyFSNTDDIKIEGFQKEn-ACSTSLTPWIDFTKIFGEI | ---NNSNVELIEKIIYDVTVFEDKKILR | 647 |
| WP_031589969 | 576 | NAMKKWLVKNqyFSNTDDIKIEGFQKEn-ACSTSLTPWIDFTKIFGKI | ---NESNYDFIEKIIYDVTVFEDKLKLR | 647 |
| KDA45870 | 558 | KMVIKHLKVV--MPAIRIQALKGLDNGk--FNASYGTYKDLVDMGVAP | ELLNDEVNSEKWEDIIKILTIFBGRKLIK | 630 |
| WP_039099354 | 579 | KNIQDYLVSEk--RYASRPAITGLSDEnk-FNSRLSTYHDLKTIVGDA | --VDDVDKQADLEKCIEWSTIFEDGKIYS | 650 |
| AKP02966 | 561 | KKLTKWLIAQg---YYKNPILIGLSQKq-EFNSTLTTYLDMKKIFGSS | -FMENNKNYNQIEELIEWLTIFEDKQILN | 632 |
| WP_010991369 | 567 | KDLELFLRNM--SH-VESPTIEGLE-D-SFNNSYSTYHDLLKVGIKQ | EIILDNPVNTEMLENIVKILTVFEDKRMIK | 637 |
| WP_033838504 | 567 | KDLELFLRNM--SH-VESPTIEGLE-D-SFNNSYSTYHDLLKVGIKQ | EIILDNPVNTEMLENIVKILTVFEDKRMIK | 637 |
| EHN60060 | 570 | KDLEQFLRNM--SH-VESPTIEGLE-D-SFNNSYSTYHDLLKVGIKQ | EIILDNPVNTEMLENIVKILTVFEDKRMIK | 640 |
| EFR89594 | 336 | KDLELFLRNI--SH-IESPTIEGLE-D-SFNNSYSTYHDLLKVGIKQ | EIILDNPVNTEMLENIVKILTVFEDKRMIK | 406 |
| WP_038409211 | 567 | KDLERFLYTI--NH-IESPTIEGVE-D-AFNSSFATYHDLQKGGVTQ | EIILDNPLNADMLBEIVKILTVFEDKRMIK | 637 |
| EFR95520 | 186 | KDLERFLYTI--NH-IESPTIEGVE-D-AFNSSFATYHDLQKGGVTQ | EIILDNPLNADMLBEIVKILTVFEDKRMIK | 256 |
| WP_003723650 | 567 | KDLELFLRNI--NH-IESPTIEGLE-D-SFNASYATYHDLLKVGLKQ | EIILDNPLNTEMLEDIVKILTVFEDKRMIK | 637 |
| WP_003727705 | 567 | KDLELFLRNI--NH-IESPTIEGLE-D-SFNASYATYHDLLKVGMKQ | EIILDNPLNTEILEDIVKILTVFEDKRMIK | 637 |
| WP_003730785 | 567 | KDLELFLRNI--NH-IESPTIEGLE-D-SFNASYATYHDLLKVGLKQ | EIILDNPLNTEILEDIVKILTVFEDKRMIK | 637 |
| WP_003733029 | 567 | KDLELFLRNI--NQ-IESPTIEGLE-D-SFNASYATYHDLLKVGMKQ | EIILDNPLNTEMLEDIVKILTVFEDKRMIK | 637 |
| WP_003739838 | 567 | KDLEQFLRNM--SH-IESPTIEGLE-D-SFNASYATYHDLLKVGMKQ | EVLENPLNTEMLEDIVKILTVFEDKRMIK | 637 |
| WP_014601172 | 567 | KDLELFLRNI--NH-IESPTIEGLE-D-SFNASYATYHDLLKVGMKQ | EIILDNPLNTEMLEDIVKILTVFEDKRMIK | 637 |
| WP_023548323 | 567 | KDLELFLRNI--NQ-IESPTIEGLE-D-SFNASYATYHDLLKVGMKQ | EIILDNPLNTEMLEDIVKILTVFEDKRMIK | 637 |
| WP_031665337 | 567 | KDLELFLRNI--NH-VESPTIEGLE-D-SFNASYATYHDLMKVGIKQ | EIILDNPLNTEMLEDIVKILTVFEDKRMIK | 637 |
| WP_031669209 | 567 | KDLELFLRNI--NH-VESPTIEGLE-D-SFNASYATYHDLMKVGIKQ | EIILDNPLNTEMLEDIVKILTVFEDKRMIK | 637 |
| WP_033920898 | 567 | KDLELFLRNI--NH-VESPTIEGLE-D-SFNASYATYHDLMKVGIKQ | EIILDNPLNTEMLEDIVKILTVFEDKRMIK | 637 |

```
-continued

AKI42028         570 KDLELFLRNI--NH-IESPTIEGLE-D--SFNASYATYHDLLKVGMKQ EILDNPLNTEMLEDIVKLILTVFEDKPMIK    640
AKI50529         570 KDLELFLRNI--NH-VESPTIEGLE-D--SFNASYATYHDLMKVGIKQ EILDNPLNTEMLEDIVKLILTVFEDKRMIK    640
EFR83390          15 KDLELFLRNI--NQ-IESPTIEGLE-D--SFNASYATYHDLLKVGMKQ EILDNPLNTEMLEDIVKLILTVFEDKRMIK     85
WP_046323366     567 KDLELFLYNM--NH-VESPTVEGVE-D--AFNSSETTYHDLQKVGVPQ EILDDPLNTEMLEEIKILTLFEDKRMIN     637
AKE81011         578 KQLKEDYFKK--IECEDSVEISGVEDR--FNASLGTYHDLLKIIKDK DFLDNEENEDILEDIVLTLTLFEDKKIMK      649
CUO82355         572 KKLKNWLVNNqCCR--KDAEIKGFQKEh-QESTSLTPWIDETNIFGKI ----DQSNFDLIEKIIYDLTVFEDKKIMK     641
WP_033162887     573 KKLKDWLVTHqYTDINEELKIEGYQKDI-QESTSLAPWIDETKIFGEI ----NASNYQLIEKIIYDISIFEDKKILK    644
AGZ01981         595 KQLKEDYFKK--IECEDSVEISGVEDR--FNASLGTYHDLLKIIKDK DFLDNEENEDILEDIVLTLTLFEDREMIE      666
AKA60242         562 KQLKEDYFKK--IECEDSVEISGVEDR--FNASLGTYHDLLKIIKDK DFLDNEENEDILEDIVLTLTLFEDREMIE      633
AKS40380         562 KQLKEDYFKK--IECEDSVEISGVEDR--FNASLGTYHDLLKIIKDK DFLDNEENEDILEDIVLTLTLFEDREMIE      633
4UN5_B           566 KQLKEDYFKK--IECEDSVEISGVEDR--FNASLGTYHDLLKIIKDK DFLDNEENEDILEDIVLTLTLFEDREMIE      637
WP_010922251     634 ERLKTYAHLFDDKVMKQLKR-RRYTGWGRLSRKLINGIRDK QSGKTILDFLK -DGf---ANRNFMQLIHDDSL        702
WP_039695303     638 ERLQKYSDIFTANQLKKLER-RHYTGWGRLSYKLINGIRNK ENNKTILDYLI DDG--SANRNFMQLINDDTL         706
WP_045635197     633 QRLAQYDSLFPDERVIKALTR-RHYTGWGKLSAKLINGICDK QTGNTILDYLI DDG--KINRNFMQLINDDGL       701
5AXW_A           369 EELTNLNSELTQEEIEQLSN1KGYTGTHNLSLKAINLILDE -------LW -------TNDNQIAIFNRLKL          426
WP_009880683     318 ERLKTYAHLFDDKVMKQLKR-RRYTGWGRLSRKLINGIRDK QSGKTILDFLK -DGf---ANRNFMQLIHDDSL       386
WP_010922251     634 ERLKTYAHLFDDKVMKQLKR-RRYTGWGRLSRKLINGIRDK QSGKTILDFLK -DGf---ANRNFMQLIHDDSL        702
WP_011054416     634 ERLKTYAHLFDDKVMKQLKR-RRYTGWGRLSRKLINGIRDK QSGKTILDFLK -DGf---ANRNFMQLIHDDSL        702
WP_011284745     634 ERLKTYAHLFDDKVMKQLKR-RRYTGWGRLSRKLINGIRDK QSGKTILDFLK -DGf---ANRNFMQLIHDDSL        702
WP_011285506     634 ERLKTYAHLFDDKVMKQLKR-RRYTGWGRLSRKLINGIRDK QSGKTILDFLK -DGf---ANRNFMQLIHDDSL        702
WP_011527619     634 ERLKTYAHLFDDKVMKQLKR-RRYTVWGRLSRKLINGIRDK QSGKTILDFLK -DGf---ANRNFMQLIHDDSL        702
WP_012560673     634 ERLKTYAHLFDDKVMKQLKR-RRYTGWGRLSRKLINGIRDK QSGKTILDFLK -DGf---ANRNFMQLIHDDSL        702
WP_014407541     634 ERLKTYAHLFDDKVMKQLKR-RRYTGWGRLSRKLINGIRDK QSGKTILDFLK -DGf---ANRNFMQLIHDDSL        702
WP_020905136     634 ERLKTYAHLFDDKVMKQLKR-RHYTGWGKLSAKLINGICDK QSGKTILDFLK -DGf---ANRNFMQLIHDDSL       702
WP_023080005     634 ERLKTYANLFDDKVMKQLKR-RRYTGWGRLSRKLINGIRDK QSGKTILDFLK -DGf---ANRNFMQLIHDDSL        702
WP_023610282     634 ERLKTYAHLFDDKVMKQLKR-RRYTGWGRLSRKLINGIRDK QSGKTILDFLK -DGf---ANRNFMQLIHDDSL        702
WP_030125963     634 ERLKTYAHLFDDKVMKQLKR-RRYTGWGRLSRKLINGIRDK QSGKTILDFLK -DGf---ANRNFMQLIHDDSL        702
WP_030126706     634 ERLKTYAHLFDDKVMKQLKR-RRYTGWGRLSRKLINGIRDK QSGKTILDFLK -DGf---ANRNFMQLIHDDSL        702
WP_031488318     634 ERLKKYAHLFDDKVMKQLKR-RRYTGWGRLSRKLINGIRDK QSGKTILDFLK -DGf---ANRNFMQLIHDDSL        702
WP_032460140     634 ERLKTYAHLFDDKVMKQLKR-RRYTGWGRLSRKLINGIRDK QSGKTILDFLK -DGf---ANRNFMQLIHDDSL        702
WP_032461047     634 ERLKTYAHLFDDKVMKQLKR-RRYTGWGRLSRKLINGIRDK QSGKTILDFLK -DGf---ANRNFMQLIHDDSL        702
WP_032462016     634 ERLKTYAHLFDDKVMKQLKR-RRYTGWGRLSRKLINGIRDK QSGKTILDFLK -DGf---ANRNFMQLIHDDSL        702
WP_032462936     634 ERLKTYAHLFDDKVMKQLKR-RRYTGWGRLSRKLINGIRDK QSGKTILDFLK -DGf---ANRNFMQLIHDDSL        702
WP_032464890     634 ERLKTYAHLFDDKVMKQLKR-RRYTGWGRLSRKLINGIRDK QSGKTILDFLK -DGf---ANRNFMQLIHDDSL        702
WP_033888930     459 ERLKTYAHLFDDKVMKQLKR-RRYTGWGRLSRKLINGIRDK QSGKTILDFLK -DGf---ANRNFMQLIHDDSL        527
WP_038431314     634 ERLKKYANLFDDKVMKQLKR-RRYTGWGRLSRKLINGIRDK ENQKTILDYLI DDG--SANRNFMQLINDDSL        702
WP_038432938     634 ERLKKYANLFDDKVMKQLKR-RRYTGWGRLSRKLINGIRDK ENQKTILDYLI DDG--SANRNFMQLINDDSL        702
WP_038434062     634 ERLKTYAHLFDDKVMKQLKR-RRYTGWGRLSRKLINGIRDK QSGKTILDFLK -DGf---ANRNFMQLIHDDSL        702
BAQ51233         545 ERLKTYAHLFDDKVMKQLKR-RRYTGWGRLSRKLINGIRDK QSGKTILDFLK -DGf---ANRNFMQLIHDDSL         613
KGE60162             ------------------------------------------------ ------- ------------------
KGE60856             ------------------------------------------------ ------- ------------------
WP_002989955     634 ERLKTYAHLFDDKVMKQLKR-RHYTGWGRLSYKLYR--RRYTGWGRLS YKLINGIRNK ENKKTILDYLI DDG--YANRNFMQLINDDAL   702
WP_003030002     635 QRLQKYSDIFTKAQLKKLER-RHYTGWGRLSYKLYR--RHYTGWGRLS YKLINGIRNK ENKKTILDYLI DDG--YANRNFMQLINDDAL    703
WP_003065552     638 ERLQKYSDIFTADQLKKLER-RHYTGWGRLSYKLYR--RHYTGWGRLS YKLINGIRNK ENKKTILDYLI DDG--SANRNFMQLINDDTL   706
WP_001040076     633 KRLDIYKDFFTESQLKKLYR-RHYTGWGRLSAKLYR--RHYTGWGRLS AKLINGIRDK ENQKTILDYLI DDG--SANRNFMQLIKDAGL   701
WP_001040078     636 KRLENYKDLFTESQLKKLYR-RHYTGWGRLSAKLYR--RHYTGWGRLS AKLINGIRDK ESQKTILDYLI DDG--RSNRNFMQLINDDGL    704
WP_001040080     636 KRLENYKDLFTESQLKKLYR-RHYTGWGRLSAKLYR--RHYTGWGRLS AKLINGIRDK ESQKTILDYLI DDG--RSNRNFMQLINDDGL    704
WP_001040081     636 KRLENYKDLFTESQLKKLYR-RHYTGWGRLSAKLYR--RHYTGWGRLS AKLINGIRDK ESQKTILDYLI DDG--RSNRNFMQLINDDGL    704
WP_001040083     636 KRLENYKDLFTESQLKKLYR-RHYTGWGRLSAKLYR--RHYTGWGRLS AKLINGIRDK ESQKTILDYLI DDG--RSNRNFMQLINDDGL    704
WP_001040085     636 KRLENYKDLFTESQLKKLYR-RHYTGWGRLSAKLYR--RHYTGWGRLS AKLINGIRDK ESQKTILDYLI DDG--RSNRNFMQLINDDGL    704
WP_001040087     636 KRLENYKDLFTESQLKKLYR-RHYTGWGRLSAKLYR--RHYTGWGRLS AKLINGIRDK ESQKTILDYLI DDG--RSNRNFMQLINDDGL    704
WP_001040088     636 KRLENYKDLFTESQLKKLYR-RHYTGWGRLSAKLYR--RHYTGWGRLS AKLINGIRDK ESQKTILDYLI DDG--RSNRNFMQLINDDGL    704
WP_001040089     636 KRLENYKDLFTESQLKKLYR-RHYTGWGRLSAKLYR--RHYTGWGRLS AKLINGIRDK ESQKTILDYLI DDG--RSNRNFMQLINDDGL    704
```

| | | | |
|---|---|---|---|
| WP_001040090 | 636 | KRLENYKDLFTESQLKKLYR-RHYTGWGRLSAKLINGIRDK ESQKTILDYLI DDG---RSNRNFMQLINDDGL | 704 |
| WP_001040091 | 636 | KRLENYKDLFTESQLKKLYR-RHYTGWGRLSAKLINGIRDK ESQKTILDYLI DDG---RSNRNFMQLINDDGL | 704 |
| WP_001040092 | 636 | KRLENYKDLFTESQLKKLYR-RHYTGWGRLSAKLINGIRDR SDG---RANRNFMQLINDDGL | 704 |
| WP_001040094 | 633 | KRLDIYKDFFTESQLKKLYR-RHYTGWGRLSAKLINGIRNK ENQKTILDYLI DDG---SANRNFMQLIKDAGL | 701 |
| WP_001040095 | 633 | KRLDIYKDFFTESQLKKLYR-RHYTGWGERLSAKLINGIRNK ENQKTILDYLI DDG---SANRNFMQLIKDAGL | 701 |
| WP_001040096 | 633 | KRLDIYKDFFTESQLKKLYR-RHYTGWGRLSAKLINGIRNK ENQKTILDYLI DDG---SANRNFMQLIKDAGL | 701 |
| WP_001040097 | 633 | KRLDIYKDFFTESQLKKLYR-RHYTGWGRLSAKLINGIRNK ENQKTILDYLI DDG---SANRNFMQLIKDAGL | 701 |
| WP_001040098 | 633 | KRLDIYKDFFTESQLKKLYR-RHYTGWGRLSAKLINGIRNK ENQKTILDYLI DDG---SANRNFMQLIKDAGL | 701 |
| WP_001040099 | 633 | KRLDIYKDFFTESQLKKLYR-RHYTGWGRLSAKLINGIRNK ENQKTILDYLI DDG---SANRNFMQLINDDGL | 701 |
| WP_001040100 | 636 | KRLENYKDLFTESQLKKLYR-RHYTGWGRLSAKLINGIRDK ESQKTILDYLI DDG---SANRNFMQLINDDGL | 704 |
| WP_001040104 | 636 | KRLENYKDLFTESQLKKLYR-RHYTGWGRLSAKLINGIRDK ESQKTILDYLI DDG---RSNRNFMQLINDDGL | 704 |
| WP_001040105 | 636 | KRLENYKDLFTESQLKKLYR-RHYTGWGRLSAKLINGIRDK ESQKTILDYLI DDG---RSNRNFMQLINDDGL | 704 |
| WP_001040106 | 636 | KRLENYKDLFTESQLKKLYR-RHYTGWGRLSAKLINGIRNK ESQKTILDYLI SDG---RANRNFMQLIHDDGL | 704 |
| WP_001040107 | 636 | KRLENYKDLFTESQLKKLYR-RHYTGWGRLSAKLINGIRNK ENQKTILDYLI SDG---RANRNFMQLIHDDGL | 704 |
| WP_001040108 | 636 | KRLDIYKDFFTESQLKKLYR-RHYTGWGRLSAKLINGIRNK ENQKTILDYLI DDG---SANRNFMQLIHDDGL | 704 |
| WP_001040109 | 636 | KRLENYKDLFTESQLKKLYR-RHYTGWGRLSAKLINGIRNK ESQKTILDYLI SDG---RANRNFMQLIHDDGL | 704 |
| WP_001040110 | 636 | KRLENYKDLFTESQLKKLYR-RHYTGWGRLSAKLINGIRNK ESQKTILDYLI DDG---RANRNFMQLINDDGL | 704 |
| WP_015058523 | 636 | KRLENYKDLFTESQLKKLYR-RHYTGWGRLSAKLINGIRDR ESQKTILDYLI SDG---RSNRNFMQLINDDGL | 704 |
| WP_017643650 | 636 | KRLENYKDLFTESQLKKLYR-RHYTGWGRLSAKLINGIRDK ENQKTILDYLI DDG---SANRNFMQLINDDGL | 701 |
| WP_017647151 | 636 | KRLENYKDLFTESQLKKLYR-RHYTGWGRLSAKLINGIRDK ESQKTILDYLI DDG---RSNRNFMQLIHDDGL | 704 |
| WP_017648376 | 636 | KRLENYKDLFTESQLKKLYR-RHYTGWGRLSAKLINGIRDK ESQKTILDYLI DDG---KSNRNFMQLIHDDGL | 704 |
| WP_017649527 | 636 | KRLENYKDLFTESQLKKLYR-RHYTGWGRLSAKLINGIRDK ESQKTILDYLI SDG---RANRNFMQLINDDGL | 704 |
| WP_017771611 | 636 | KRLENYKDLFTESQLKKLYR-RHYTGWGRLSAKLINGIRDK ESQKTILDYLI DDG---RSNRNFMQLINDDGL | 704 |
| WP_017771984 | 636 | KRLENYKDLFTESQLKKLYR-RHYTGWGRLSAKLINGIRDK ESQKTILDYLI DDG---RANRNFMQLINDDGL | 704 |
| CFQ25032 | 636 | KRLENYKDLFTESQLKKLYR-RHYTGWGRLSAKLINGIRDK ESQKTILDYLI DDG---RSNRNFMQLINDDGL | 704 |
| CFV16040 | 636 | KRLENYKDLFTESQLKKLYR-RHYTGWGRLSAKLINGIRDK ESQKTILDYLI DDG---RSNRNFMQLINDDGL | 704 |
| KLJ37842 | 636 | KRLENYKDLFTESQLKKLYR-RHYTGWGRLSAKLINGIRDK ESQKTILDYLI DDG---RANRNFMQLINDDGL | 704 |
| KLJ72361 | 636 | KRLENYKDLFTESQLKKLYR-RHYTGWGRLSAKLINGIRDK ESQKTILDYLI DDG---RSNRNFMQLINDDGL | 704 |
| KLL20707 | 636 | KRLENYKDLFTESQLKKLYR-RHYTGWGRLSAKLINGIRDK ESQKTILDYLI DDG---RSNRNFMQLINDDGL | 718 |
| KLL42645 | 636 | KRLENYKDLFTESQLKKLYR-RHYTGWGRLSAKLINGIRDR SDG---RANRNFMQLINDDGL | 704 |
| WP_047207273 | 636 | KRLENYKDLFTESQLKKLYR-RHYTGWGRLSAKLINGIRDK ESQKTILDYLI DDG---SANRNFMQLIKDAGL | 704 |
| WP_047209694 | 633 | KRLDIYKDFFTESQLKKLYR-RHYTGWGRLSAKLINGIRNK ENQKTILDYLI DDG---SANRNFMQLIKDAGL | 701 |
| WP_050198062 | 636 | KRLENYKDLFTESQLKKLYR-RHYTGWGRLSAKLINGIRDK ESQKTILDYLI SDG---RSNRNFMQLINDDGL | 704 |
| WP_050201642 | 636 | KRLENYKDLFTESQLKKLYR-RHYTGWGRLSAKLINGIRDK ESQKTILDYLI DDG---RSNRNFMQLINDDGL | 704 |
| WP_050204027 | 636 | KRLENYKDLFTESQLKKLYR-RHYTGWGRLSAKLINGIRDK ESQKTILDYLI DDG---RANRNFMQLIHDDGL | 704 |
| WP_050881965 | 636 | KRLENYKDLFTESQLKKLYR-RHYTGWGRLSAKLINGIRDK ESQKTILDYLI DDG---RSNRNFMQLINDDGL | 704 |
| WP_050886065 | 636 | KRLENYKDLFTESQLKKLYR-RHYTGWGRLSAKLINGIRDK ESQKTILDYLI DDG---RANRNFMQLINDDGL | 704 |
| AHN30376 | 636 | KRLENYKDLFTESQLKKLYR-RHYTGWGRLSAKLINGIRDK ESQKTILDYLI DDG---RSNRNFMQLINDDGL | 704 |
| EA078426 | 636 | KRLENYKDLFTESQLKKLYR-RHYTGWGRLSAKLINGIRDK ESQKTILDYLI DDG---RSNRNFMQLINDDGL | 704 |
| CCW42055 | 636 | KRLDIYKDLFTESQLKKLER-RHYTGWGRLSYKLINGIRNK ENKKTILDYLI DDG---YANRNFMQLINDDAL | 703 |
| WP_003041502 | 635 | QRLQKYSDIFTKAQLKKLER-RHYTGWGRLSYKLINGIRNK ENKKTILDYLI DDG---YANRNFMQLINDDAL | 703 |
| WP_037593752 | 636 | QRLQKYSDIFTKAQLKKLER-RHYTGWGRLSYKLINGIRNK ENKKTILDYLI DDG---YANRNFMQLINDDAL | 703 |
| WP_049516684 | 636 | QRLQKYSDIFTTQQLKKLER-RHYTGWGRLSYKLINGIRNK ENKKTILDYLI DDG---YANRNFMQLINDDTL | 703 |
| GAD46167 | 635 | QRLQKYSDIFTKQQLKKLER-RHYTGWGRLSYKLINGIRNK ENNKTILEYLV DDG---SNRNFMQLINDDAL | 704 |
| WP_018363470 | 636 | ERLKTYAHLFDDKVMKQLKR-RHYTGWGRLSRKMINGIRDK QSGKTILDFLK -DGf---ANRNFIQLIHDDSL | 712 |
| WP_003043819 | 644 | KRLKTYAHLFDDKVMKQLER-RHYTGWGRLSYKLINGIRDK ENKKTILDYLI DDG---YANRNFMQLINDDAL | 712 |
| WP_006269658 | 635 | QRLQKYSDIFTKAQLKKLER-RHYTGWGRLSYKLINGIRDK ENKKTILEYLV DDG---YANRNFMQLINDDTL | 703 |
| WP_048800889 | 635 | QRLQKYSDIFTKAQLKKLKR-RHYTGWGRLSYKLINGIRNK ENNKTILEYLV DDG---YANRNFMQLINDDTL | 703 |
| WP_012767106 | 634 | ERLKKYANLFDDKVMKQLKR-RHYTGWGRLSRKLINGIRDK QSGKTILDFLK -DGf---ANRNFIQLIHDDSL | 702 |
| WP_014612333 | 634 | ERLKTYAHLFDDKVMKQLKR-RHYTGWGRLSRKLINGIRDK QSGKTILDFLK -DGf---ANRNFIQLIHDDSL | 702 |
| WP_015017095 | 634 | ERLKTYAHLFDDKVMKQLKR-RHYTGWGRLSRKLINGIRDK QSGKTILDFLK -DGf---ANRNFIQLIHDDSL | 702 |
| WP_015057649 | 634 | ERLKTYAHLFDDKVMKQLKR-RHYTGWGRLSRKLINGIRDK QSGKTILDFLK -DGf---ANRNFIQLIHDDSL | 702 |
| WP_048327215 | 634 | ERLKTYAHLFDDKVMKQLKR-RHYTGWGRLSRKLINGIRDK QSGKTILDFLK -DGf---ANRNFIQLIHDDSL | 702 |

-continued

| ID | Start | Sequence | End |
|---|---|---|---|
| WP_049519324 | 634 | ERLKTYAHLFDDKVMKQLKR-RHYTGWGRLSRKLINGIRDK QSGKTILDFLK -DGf---ANRNFIQLIHDDSL | 702 |
| WP_012515931 | 634 | KRLDQYAHLFDDKVVLNKLER-HHYTGWGRLSGKLINGIRDK QSGKTILDFLK -DGf---ANRNFMQLIHDSEL | 702 |
| WP_021320964 | 634 | KRLDQYAHLFDKVVLNKLER-HHYTGWGRLSGKLINGIRDK QSGKTILDFLK -DGf---ANRNFMQLIHDSEL | 702 |
| WP_037581760 | 634 | KRLDQYAHLFDKVVLNKLER-RHYTGWGRLSGKLINGIRDK QSGKTILDFLK -DGf---ANRNFMQLIHDSEL | 702 |
| WP_004232481 | 635 | ERLQKYSDIFTSQQLKKLER-RHYTGWGRLSYKLINGIRNK ENNKTILDFLI DDG---DANRNFMQLINDDSL | 703 |
| WP_009854540 | 636 | ERLQKYSDIFTANQLKKLER-RHYTGWGRLSYKLINGIRNK ENNKTILDYLI DDG---SANRNFMQLINDDTL | 704 |
| WP_012962174 | 636 | QRLQKYSDIFTPQQLKKLER-RHYTGWGRLSYKLINGIRNK ENGKSILDYLI DDG---YANRNFMQLISDDTL | 704 |
| WP_039695303 | 638 | ERLQKYSDIFTANQLKKLER-RHYTGWGRLSYKLINGIRNK ENNKTILDYLI DDG---SANRNFMQLINDDTL | 706 |
| WP_014334983 | 635 | ERLQKYSDFFTSQQLKKLER-RHYTGWGRLSQKLINGIKDK ENNKTILDFLI DDG---HANRNFMQLINDESL | 703 |
| WP_030099269 | 634 | RRLVKYADVFEKSVLKKLKR-RHYTGWGRLSQKLINGIKDK QTGKTILDFLK -DGy---ANRNFMQLINDSSL | 702 |
| AHY15608 | 634 | RRLVKYADVFEKSVLKKLKK-RHYTGWGRLSQKLINGIKDK QTGKTILGFLK -DGv---ANRNFMQLINDSSL | 702 |
| AHY17476 | 634 | RRLVKYADVFEKSVLKKLKK-RHYTGWGRLSQKLINGIKDK QTGKTILGFLK -DGv---ANRNFMQLINDSSL | 702 |
| ESR09100 | | | |
| AGM98575 | 634 | RRLVKYADVFEKSVLKKLKK-RHYTGWGRLSQKLINGIKDK QTGKTILGFLK -DGy---ANRNFMQLINDSSL | 702 |
| ALF27331 | 635 | KRLENYSDLLTKEQVKNLER-RHYTGWGRLSAELIHGIRNK ESRKTILDYLI DDG---NSNRNFMQLINDDAL | 703 |
| WP_018372492 | 648 | KRLSELNIPFENKIIKKLAR-KKYTGWGRLSRKLIDGIRNK ETNRTILGHLI DDG---SNRNLMQLINDDGL | 716 |
| WP_045618028 | 634 | QRLAHYASIFDEKVIKALTR-RHYTGWGKLSAKLINGIYDK QSKKTILDYLI DDG---EINRNFMQLINDDGL | 702 |
| WP_045635197 | 633 | QRLAQYDSLFDERVIKALTR-RHYTGWGKLSAKLINGICDK QTGNTILDYLI DDG---KINRNFMQLINDDGL | 701 |
| WP_002263549 | 635 | KRLENYSDLLTKEQVKKLER-RHYTGWGRLSAELIHGIRNK ESRKTILDYLI DDG---NSNRNFMQLINDDAL | 703 |
| WP_002263887 | 635 | KRLENYSDLLTKEQVKKLER-RHYTGWGRLSAELIHGIRNK ESRKTILDYLI DDG---NSNRNFMQLINDDAL | 703 |
| WP_002264920 | 636 | QRLAKYSDLLTKEQVKKVIDQLAR-RHYTGWGRLSAKLLNGIRDK QSCKTIMDYLI DDA---QSNRNLMQLITDNL | 704 |
| WP_002269043 | 635 | KRLENYSDLLTKEQLKKLER-RHYTGWGRLSAELIHGIRNK ESRKTILDYLI DDG---NSNRNFMQLINDDAL | 703 |
| WP_002269448 | 635 | KRLENYSDLLTKEQVKKLER-RHYTGWGRLSAELIHGIRNK ESRKTILDYLI DDG---NSNRNFMQLINDDAL | 703 |
| WP_002271977 | 635 | KRLENYSDLLTKEQVKKLER-RHYTGWGRLSAELIHGIRNK ESRKTILDYLI DDG---NSNRNFMQLINDDAL | 703 |
| WP_002272766 | 635 | KRLENYSDLLTKEQVKKLER-RHYTGWGRLSAELIHGIRNK ESRKTILDYLI DDG---NSNRNFMQLINDDAL | 703 |
| WP_002273241 | 635 | KRLENYSDLLTKEQVKKLER-RHYTGWGRLSAELIHGIRNK ESRKTILDYLI DDG---NSNRNFMQLINDDAL | 703 |
| WP_002275430 | 635 | KRLENYSDLLTKEQVKKLER-RHYTGWGRLSAELIHGIRNK ESRKTILDYLI DDG---NSNRNFMQLINDDAL | 703 |
| WP_002276448 | 635 | KRLENYSDLLTKEQVKKLER-RHYTGWGRLSAELIHGIRNK ESRKTILDYLI DDG---NSNRNFMQLINDDAL | 703 |
| WP_002277050 | 636 | QRLAKYADVFDKKVIDQLAR-RHYTGWGRLSAKLLNGIRDK QSCKTIMDYLI DDA---QSNRNLMQLINDDNL | 704 |
| WP_002277364 | 635 | KRLENYSDLLTKEQVKKLER-RHYTGWGRLSAELIHGIRNK ESRKTILDYLI DDG---NSNRNFMQLINDDAL | 703 |
| WP_002279025 | 635 | KRLENYSDLLTKEQVKKLER-RHYTGWGRLSAELIHGIRNK ESRKTILDYLI DDG---NSNRNFMQLINDDAL | 703 |
| WP_002279859 | 635 | KRLENYSDLLTKEQVKKLER-RHYTGWGRLSAELIHGIRNK ESRKTILDYLI DDG---NSNRNFMQLINDDAL | 703 |
| WP_002280230 | 635 | KRLENYSDLLTKEQVKKLER-RHYTGWGRLSAELIHGIRNK ESRKTILDYLI DDG---NSNRNFMQLINDDAL | 703 |
| WP_002281696 | 635 | KRLENYSDLLTKEQVKKLER-RHYTGWGRLSAELIHGIRNK ESRKTILDYLI DDG---NSNRNFMQLINDDAL | 703 |
| WP_002282247 | 636 | QRLAKYADVFDKKVIDQLAR-RHYTGWGRLSAKLLNGIRDK QSCKTILDYLI DDA---QSNRNLMQLITDDNL | 704 |
| WP_002282906 | 635 | KRLENYSDLLTKEQVKKLER-RHYTGWGRLSAELIHGIRNK ESRKTILDYLI DDG---NSNRNFMQLINDDAL | 703 |
| WP_002283846 | 635 | KRLENYSDLLTKEQVKKLER-RHYTGWGRLSAELIHGIRNK ESRKTILDYLI DDG---NSNRNFMQLINDDAL | 703 |
| WP_002287255 | 635 | KRLENYSDLLTKEQVKKLER-RHYTGWGRLSAELIHGIRNK ESRKTILDYLI DDG---NSNRNFMQLINDDAL | 703 |
| WP_002288990 | 635 | KRLENYSDLLTKEQVKKLER-RHYTGWGRLSAELIHGIRNK ESRKTILDYLI DDG---NSNRNFMQLINDDAL | 703 |
| WP_002289641 | 635 | KRLENYSDLLTKEQVKKLER-RHYTGWGRLSAELIHGIRNK ESRKTILDYLI DDG---NSNRNFMQLINDDAL | 703 |
| WP_002290427 | 635 | KRLENYSDLLTKEQVKKLER-RHYTGWGRLSAELIHGIRNK ESRKTILDYLI DDG---NSNRNFMQLINDDAL | 703 |
| WP_002295753 | 635 | KRLENYSDLLTKEQVKKLER-RHYTGWGRLSAELIHGIRNK ESRKTILDYLI DDG---NSNRNFMQLINDDAL | 703 |
| WP_002296423 | 635 | KRLENYSDLLTKEQVKKLER-RHYTGWGRLSAELIHGIRNK ESRKTILDYLI DDG---NSNRNFMQLINDDAL | 703 |
| WP_002304487 | 645 | QRLQKYSDIFTKAQLKKLER-RHYTGWGRLSYKLINGIRNK QSNKTILDYLI DDG---YSNRNFMQLINDDAL | 713 |
| WP_002305844 | 635 | KRLENYSDLLTKEQLKKLER-RHYTGWGRLSAELIHGIRNK ESRKTILDYLI DDG---NSNRNFMQLINDDAL | 703 |
| WP_002307203 | 635 | KRLENYSDLLTKEQVKKLER-RHYTGWGRLSAELIHGIRNK ESRKTILDYLI DDG---NSNRNFMQLINDDAL | 703 |
| WP_002310390 | 635 | KRLENYSDLLTKEQVKKLER-RHYTGWGRLSAELIHGIRNK ESRKTILDYLI DDG---NSNRNFMQLINDDAL | 703 |
| WP_002352408 | 635 | KRLENYSDLLTKEQVKKLER-RHYTGWGRLSAELIHGIRNK ESRKTILDYLI DDG---NSNRNFMQLINDDAL | 703 |
| WP_012997688 | 635 | KRLENYSDLLTKEQVKKLER-RHYTGWGRLSAELIHGIRNK ESRKTILDYLI DDG---NSNRNFMQLINDDAL | 703 |
| WP_014677909 | 635 | KRLENYSDLLTKEQVKKLER-RHYTGWGRLSAELIHGIRNK ESRKTILDYLI DDG---NSNRNFMQLINDDAL | 703 |
| WP_019312892 | 635 | KRLENYSDLLTKEQVKKLER-RHYTGWGRLSAELIHGIRNK ESRKTILDYLI DDG---NSNRNFMQLINDDAL | 703 |
| WP_019313659 | 635 | KRLENYSDLLTKEQVKKLER-RHYTGWGRLSAELIHGIRNK ESRKTILDYLI DDG---NSNRNFMQLINDDAL | 703 |
| WP_019314093 | 635 | KRLENYSDLLTKEQVKKLER-RHYTGWGRLSAELIHGIRNK ESRKTILDYLI DDG---NSNRNFMQLINDDAL | 703 |

-continued

| ID | start | sequence | end |
|---|---|---|---|
| WP_019315370 | 635 | KRLENYSDLLTKEQVKKLER-RHYTGWGRLSAELIHGIRNK ESRKTLLDYLI DDG---NSNRNFMQLINDDAL | 703 |
| WP_019803776 | 635 | KRLENYSDLLTKEQVKKLER-RHYTGWGRLSAELIHGIRNK ESRKTILDYLI DDG---NSNRNFMQLINDDAL | 703 |
| WP_019805234 | 635 | KRLKNYSDLLTKEQLKKLER-RHYTGWGRLSAELIHGIRNK ESRKTILDYLI DDG---NSNRNFMQLINDDAL | 703 |
| WP_024783594 | 635 | KRLENYSDLLTKEQVKKLER-RHYTGWGRLSAELIHGIRNK ESRKTILDYLI DDG---NSNRNFMQLINDDAL | 703 |
| WP_024784288 | 636 | QRLAKYADVFDKKVIDQLAR-RHYTGWGRLSAKLLNGIRDK QSCKTIMDYLI DDA---QSNRNLMQLITDDNL | 704 |
| WP_024784666 | 635 | KRLENYSDLLTKEQVKKLER-RHYTGWGRLSAELIHGIRNK ESRKTILDYLI DDG---NSNRNFMQLINDDAL | 703 |
| WP_024784894 | 635 | KRLENYSDLLTKEQVKKLER-RHYTGWGRLSAELIHGIRNK ESRKTILDYLI DDG---NSNRNFMQLINDDAL | 703 |
| WP_024786433 | 636 | QRLAKYADVFDKKVIDQLAR-RHYTGWGRLSAKLLNGIRDK QSCKTIMDYLI DDA---QSNRNLMQLITDDNL | 704 |
| WP_049473442 | 635 | KRLENYSDLLTKEQVKKLER-RHYTGWGRLSAELIHGIRNK ESRKTILDYLI DDG---NSNRNFMQLINDDAL | 703 |
| WP_049474547 | 635 | KRLENYSDLLTKEQLKKLER-RHYTGWGRLSAELIHGIRNK ESRKTILDYLI DDG---NSNRNFMQLINDDAL | 703 |
| EMC03581 | 628 | KRLENYSDLLTKEQVKKLER-RHYTGWGRLSAELIHGIRNK ESRKTILDYLI DDG---NSNRNFMQLINDDEL | 696 |
| WP_000428612 | 636 | QRLAQYDSLFDEKVIKALTR-RHYTGWGKLSSKLINGIRDK QTGNTILDYLI DDG---YNNRNFMQLINDDEL | 704 |
| WP_000428613 | 634 | QRLAQYDSLFDEKVIKALTR-RHYTGWGKLSAKLIDGICDK QTGNTILDYLI DDG---KNNRNFMQLINDDGL | 702 |
| WP_049523028 | 633 | QRLNQYDSIFDEKVIKALTR-RHYTGWGKLSAKLINGIRDK KTSKTILDYLI DDG---YSNRNFMQLINDDGL | 701 |
| WP_003107102 | 636 | KRLSKYESLFDPSILKKLKK-RHYTGWGRLSQKLINGIRDK QTGKTILDFLI -DGq---ANRNFMQLINDFLI | 704 |
| WP_054279288 | 603 | NRLAVYEDLFDQNVLKQLKR-RHYTGWGKLSAKLINGMRDK HTGKTILDYLI -DGf---INRNRNFMQLINDDNL | 671 |
| WP_049531101 | 636 | QRLAQYASIFDEKVIKTLTR-RHYTGWGKLSAKLINCIRDR KTGKTILDYLI DDG---YNNRNFMQLINDDGL | 704 |
| WP_049538452 | 634 | QRLAQYDSIFDEKVIKALTR-RHYTGWGKLSAKLINGIRDK QTGKTILDYLI DDG---YSNRNFMQLINDDGL | 702 |
| WP_049549711 | 634 | QRLAQYDSLFDEKVIKALTR-RHYTGWGKLSAKLINGIRDK QTGNTILDYLI DDG---EINRNFMQLINDDGL | 702 |
| WP_007896501 | 637 | KRLAKYANLFEKSVLKKLRK-RHYRGWGRLSRQLIDGMKDK ASGKTILDFLK -DDf---ANRNFIQLINDSSL | 705 |
| EFR44625 | 589 | KRLAKYANLFEKSVLKKLRK-RHYRGWGRLSRQLIDGMKDK ASGKTILDFLK -DDf---ANRNFIQLINDSSL | 657 |
| WP_002897477 | 633 | QRLAQYDTLFDEKVIKALTR-RHYTGWGKLSAKLINGIRDK QSGKTILDYLI DDD---KINRNFMQLINDDGL | 701 |
| WP_002906454 | 633 | QRLAQYDTLFDEKVIKALTR-RHYTGWGKLSAKLINGIRDK QTGKTILEYLI DDG---DCNRNFMQLINDDGL | 701 |
| WP_009729476 | 634 | QRLAQYDSLFDEKVIKALTR-RHYTGWGKLSAKLINGISDK QTGKTILDFLK -DGf---ANRNFMQLINDDSL | 702 |
| CQR24647 | 637 | QRLLKYEDIFSKKVIANLTR-RHYTGWGKLSAKLINGIKDK HSRKTILDYLI DDG---HSNRNFMQLINDDNL | 705 |
| WP_000066813 | 636 | QRLAQYDSLFDEKVIKALTR-RHYTGWGKLSAKLINGIRDK KSGKTILDYLI DDG---EINRNFMQLIHDDGL | 704 |
| WP_009754323 | 634 | QRLAQYDSIFDEKVIKALTR-RHYTGWGRLSAKLINGICDK KTGKTILDYLI DDG---YNNRNFMQLINDDGL | 702 |
| WP_044674937 | 633 | KRLEKYKDILTEEQRKKLER-RHYTGWGRLSAKLINGILDK VTGKTILDYLI DDG---KYHNRNFMQLINDDTL | 701 |
| WP_044676715 | 635 | KRLEKYKDVLTEEQRKKLER-RHYTGWGRLSAKLINGIRDK VTRKTILDYLI DDG---TSNRNFMQLINDDTL | 703 |
| WP_044680361 | 633 | KRLEKYKDVLTEEQRKKLER-RHYTGWGRLSAKLINGIRDK VTRKTILDYLI DDG---TSNRNFMQLINDDTL | 701 |
| WP_044681799 | 635 | QRLQKYSDIFTKAQLKKLKR-CHYTGWGRLSYKLINGIRNK ENKKTILDYLI DDG---YANRNFMQLINDDTL | 703 |
| WP_029090905 | 613 | RKLSEYPQLTEQQQVQLAQV-RFRGWGRLSQRLINRIKTP EDHKLSINEIL ------QTNENFMQIIRNKDY | 682 |
| WP_006506696 | 638 | RRLKKKYALPDDKVKQIIKL--KYKDWSRLSKKLLDGIVAD SV--TVLDVLE ------SRLNLMEIINDKDL | 705 |
| AIT42264 | 634 | ERLKTYAHLFDDKVMKQLKR-RRYTGWGLSRKLINGIRDE QSGKTILDFLK -DGf---ANRNFMQLIHDDSL | 702 |
| WP_034440723 | 638 | RQLMKFKDKLSEKAINQLSK-KHYTGWGQLSEKLINGIRDE QSNKTILDYLI DNGcpkNMNRNFMQLINDDTL | 710 |
| AKQ21048 | 634 | ERLKTYAHLFDDKVMKQLKR-RRYTGWGRLSRKLINGIRDK QSGKTILDFLK -DGf---ANRNFMQLIHDDSL | 702 |
| WP_004636532 | 644 | KQLQTYSDTLSPEILKKLER-RHYTGWGRFSKKLINGLRDE GSNKTILDYLK DEGssgPTNRNFMQLIRDNTL | 706 |
| WP_002364836 | 642 | TQLSTFKGQFSAEVLKKLER-KHYTGWGRLSKKLINGIYDK ESGKTILGYLI DDGvskHYNRNFMQLINDSQL | 714 |
| WP_016631044 | 593 | TQLSTFKGQFSAEVLKKLER-KHYTGWGRLSKKLINGIYDK ESGKTILDYLI DDGvskHYNRNFMQLINDDSL | 665 |
| EMS75795 | 382 | TQLKKYQSVLGDGFEKKLVK-KHYTGWGRLSERLINGIYDK KTNKTILDYLI DDGvskHYNRNFMQLINDDSL | 454 |
| WP_002373311 | 642 | TQLSTFKGQFSAEVLKKLER-KHYTGWGRLSKKLINGIYDK ESGKTILGYLI DDGvskHYNRNFMQLINDSQL | 714 |
| WP_002378009 | 642 | TQLSTFKGQFSAEVLKKLER-KHYTGWGRLSKKLINGIYDK ESGKTILDYLI DDGvskHYNRNFMQLINDSQL | 714 |
| WP_002407324 | 642 | TQLSTFKGQFSAEVLKKLER-KHYTGWGRLSKKLINGIYDK ESGKTILDYLV DDGvskHYNRNFMQLINDSQL | 714 |
| WP_002413717 | 642 | TQLSTFKGQFSAEVLKKLER-KHYTGWGRLSKKLINGIYDK ESGKTILDYLV DDGvskHYNRNFMQLIHDDSL | 714 |
| WP_010775580 | 644 | TQLSTFKGQFSEEVLKKLER-KHYTGWGRLSKKLINGIYDK ESGKTILDYLI DDGvskHYNRNFMQLINDSQL | 716 |
| WP_010182269 | 642 | TQLSTFKGQFSAEVLKKLER-KHYTGWGRLSKKLINGIYDK ESGKTILDYLI DDDfpyNRNRNFMQLINDDSL | 714 |
| WP_010824395 | 642 | TQLSTFKGQFSAEVLKKLER-KHYTGWGRLSKKLINGIYDK ESGKTILDYLI DDGvskHYNRNFMQLINDSQL | 714 |
| WP_016622645 | 642 | TQLSTFKGQFSAEVLKKLER-KHYTGWGRLSKKLINGIYDK ESGKTILDYLV DDGvskHYNRNFMQLINDSQL | 714 |
| WP_033624816 | 642 | TQLSTFKGQFSAEVLKKLER-KHYTGWGRLSKKLINGIYDK ESGKTILDYLI DDGvskHYNRNFMQLINDSQL | 714 |
| WP_033625576 | 642 | TQLSTFKGQFSAEVLKKLER-KHYTGWGRLSKKLINGIYDK ESGKTILDYLI DDGvskHYNRNFMQLINDSQL | 714 |
| WP_033789179 | 642 | TQLSTFKGQFSEEVLKKLER-KHYTGWGRLSKELIQGIRDK QSNKTILDYLI DDGvskHYNRNFMQLINDSQL | 714 |
| WP_002310644 | 642 | TRLSHHEATLGKHIIKKLTK-KHYTGWGRLSKKLLTKK-RNFTGWGRLSKELIQGIRDK QSNKTILDYLI DDDfphHRNRNFMQLINDDSL | 714 |

-continued

```
WP_002312694   643  TRLSHHEATLGKHIIKKLTK-KHYTGWGRLSKELIQGIRDK QSNKTILDYLI DDDfphHRNRNFMQLINDDSL  715
WP_002314015   643  TRLSHHEATLGKHIIKKLTK-KHYTGWGRLSKELIQGIRDK QSNKTILDYLI DDDfphHRNRNFMQLINDDSL  715
WP_002320716   643  TRLSHHEATLGKHIIKKLTK-KHYTGWGRLSKELIQGIRDK QSNKTILDYLI DDDfphHRNRNFMQLINDDSL  715
WP_002330729   642  TRLSHHEATLGKHIIKKLTK-KHYTGWGRLSKELIQGIRDK QSNKTILDYLI DDDfphHRNRNFMQLINDDSL  714
WP_002335161   643  TRLSHHEATLGKHIIKKLTK-KHYTGWGRLSKELIQGIRDK QSNKTILDYLI DDDfphHRNRNFMQLINDDSL  715
WP_002345439   643  TRLSHHEATLGKHIIKKLTK-KHYTGWGRLSKELIQGIRDK QSNKTILDYLI DDDfphHRNRNCMQLINDDSL  715
WP_034867970   638  HQLSKYQEVFGEKLLKEFAR-KHYTGWGRLSKELIQGIRDK QSNKTILDYLI DDDvpaNRNRNLMQLINDEHL  710
WP_047937432   643  TRLSHHEATLGKHIIKKLTK-KHYTGWGRLSKELIQGIRDK QSNKTILDYLI DDDfphHRNRNFMQLINDDSL  715
WP_010720994   638  HQLSKYQEVFGEKLLKEFAR-KHYTGWGRFSAKLIHGIRDR KTNKTILDYLI DDDvpaNRNRNLMQLINDEHL  710
WP_014073004   638  HQLSKYQEVFGEKLLKEFAR-KHYTGWGRFSAKLIHGIRDR KTNKTILDYLI DDDvpaNRNRNLMQLINDEHL  710
WP_034700478   638  HQLSKYQEVFGEKLLKEFAR-KHYTGWGRFSAKLIHGIRDR KTNKTILDYLI DDDvpaNRNRNLMQLINDEHL  710
WP_007209003   635  NQLEQLPLNLSTKTIKAlSR-RKYTGWGRLSARLIDGIHDK NSGKTILDYLI DESdsyIVNRNRFMQLINDDSL  707
WP_023519017   632  EQLKPYETVLGLPAIKKLAK-KHYTGWGRLSEKMIQGMREK QSRKTILDYLI DDDfpcNRNRNFMQLINDDHL  704
WP_010770040   635  EQLKKYTYLFDEEVLKKLER-RHYTGWGRLSAKLLIGIKEK RTHKTILDYLI DDGgkqPINRNLMQLINDSDL  707
WP_048604708   631  EQLSKFSDRLSEKTIKDLER-RHYTGWGRLSAKLINGIHDK QSHLTILDYLM DDApkKNINRNRFMQLINDNRL  703
WP_010750235   637  TQLKKYQRILGEEIFKKLVK-KCYTGWGRLSRKLINGIRDQ KTNKTILDYLI DDDfpyNRNRNFMQLINDDSL  709
AII16583       673  ERLKTYAHLFDDKVMKQLKR-RRYTGWGRLSRKLINGIRDK QSGKTILDFLK -DGf---ANRNFMQLIHDDSL  741
WP_029073316   648  RRLKKEYDLDEEKIKKILKL--KYSGWGRSLSKKLLSGIKTK RTPETVLEVME ----------TMMNLMQVINDEKL  717
WP_031589969   648  RRLKKEYDLDEEKIKKILKL--KYSGWGSRLSKKLLSGIKTK RTPETVLEVME ----------TNMNLMQVINDEKL  717
KDA45870       631  RRLENYRDFLGEDILRKLSR-KKYTGWGRLSAKLIHGIRDR KTHKTILDCLM EDYs-----QNFMQLINDDTY  698
WP_039099354   651  AKLNEIDWLTDQQRVQLAAK--RYRGWGRLSAKLLTQIVN- ANGQRIMDLLW ------------TTDNFMRIVHSE-  712
AKP02966       633  EKLHSSNYSYTSDQIKKISN-MREYKGWGRLSKKILTCITTE TNTPKSLQLSN -DLm-wTTNNNFISIISNDKY  706
WP_010991369   638  EQLQQFSDVLDGVVLKKLER-RHYTGWGRLSAKLLMGIRDK QSHLTILDYLM DDG-------LNRNLMQLINDSNL  706
WP_033838504   638  EQLQQFSDVLDGVVLKKLER-RHYTGWGRLSAKLLMGIRDK QSHLTILDYLM DDG-------LNRNLMQLINDSNL  706
EHN60060       641  EQLQQFSDVLDGVVLKKLER-RHYTGWGRLSAKLLVGIRDK QSHLTILDYLM DDG-------LNRNLMQLINDSNL  709
EFR89594       407  EQLQSFSDVLDGVVLKKLER-RHYTGWGRLSAKLLTGIRDK QSHLTILDYLM DDG-------LNRNLMQLINDSNL  475
WP_038409211   638  EQLQSFSDVLDGTILKKLER-RHYTGWGRLSAKLLTGIRDK HSHLTILDYLM DDG-------LNRNLMQLINDSNL  706
EFR95520       257  EQLQSFSDVLDGTILKKLER-RHYTGWGRLSAKLLTGIRDK HSHLTILDYLM DDG-------LNRNLMQLINDSNL  325
WP_003723650   638  EQLQQFSDVLDGGVVLKKLER-RHYTGWGRLSAKLLVGIRDK QSHLTILDYLM DDG-------LNRNLMQLINDSNL  706
WP_003727705   638  EQLQQFSDVLDGVVLKKLER-RHYTGWGRLSAKLLVGIRDK QSHLTILDYLM DDG-------LNRNLMQLINDSNL  706
WP_003730785   638  EQLEQFSDVLDGVVLKKLER-RHYTGWGRLSAKLLVGIRDK QSHLTILDYLM DDG-------LNRNLMQLINDSNL  706
WP_003733029   638  EQLQQFSDVLDGVVLKKLER-RKYDWSRLSKKLLDGIVAD SV--TVLDVLE ------SRLNLMEIINDEKL  706
WP_003739838   638  EQLQQFSDVLDGAVLKKLER-RHYTGWGRLSAKLLVGIRDK QSHLTILDYLM DDG-------LNRNLMQLINDSNL  706
WP_014601172   638  EQLQQFSDVLDGGVLKKLER-RHYTGWGRLSAKLLVGIREK QSHLTILDYLM DDG-------LNRNLMQLINDSNL  706
WP_023548323   638  EQLQQFSDVLDGTVLKKLER-RHYTGWGRLSAKLLVGIRDK QSHLTILDYLM DDG-------LNRNLMQLINDSNL  706
WP_031665337   638  EQLQQFSDVLDGTVLKKLER-RHYTGWGRLSAKLLVGIRDK QSHLTILEYLM DDG-------LNRNLMQLINDSNL  706
WP_031669209   638  EQLQQFSDVLDGTVLKKLER-RHYTGWGRLSAKLLVGIRDK QSHLTILEYLM DDG-------LNRNLMQLINDSNL  706
WP_033920898   638  EQLQQFSDVLDGTVLKKLER-RHYTGWGRLSAKLLVGIRDK QSHLTILDYLM DDG-------LNRNLMQLINDSNL  706
AKI42028       641  EQLQQFSDVLDGTVLKKLER-RHYTGWGRLSAKLLVGIRDK QSHLTILDYLM DDG-------LNRNLMQLINDSNL  709
AKI50529       641  EQLQQFSDVLDGTVLKKLER-RHYTGWGRLSAKLLVGIRDK QSHLTILEYLM DDG-------LNRNLMQLINDSNL  709
EFR83390        86  EQLQQFSDVLDGTVLKKLER-RHYTGWGRLSAKLLVGIRDK QSHLTILEYLM DDG-------LNRNLMQLINDSNL  154
WP_046323366   638  ERLQEFSNVLDEAVLKKLER-RHYTGWGRLSAKLLIGIRDK ESHLTILDYLM DDK-------HNRNLMQLINDSNL  706
AKE81011       650  ERLKTYAHLFDDKVMKQLKR-RRYTGWGRLSRKLINGIRDK QSGKTILDFLK -DGf--------ANRNFMQLINDFLK  718
CUO02355       642  RRLKKKYALPDDKIKQILKL--KYKDWSRLSKKLLDGIVAD SV--TVLDVLE ---------SV--TVLDVLE  709
WP_033162887   645  RRLKKVYQLDDLLVDKILKL-NYTGWSRLSEKLLTGWTAD KA--TVLFVLE ------SNKNLMEIINDEKL  712
AGZ01981       667  ERLKTYAHLFDDKVMKQLKR-RRYTGWGRLSRKLINGIRDK QSGKTILDFLK -DGf--------ANRNFMQLIHDDSL  735
AKA60242       634  ERLKTYAHLFDDKVMKQLKR-RRYTGWGRLSRKLINGIRDK QSGKTILDFLK -DGf--------ANRNFMQLIHDDSL  702
AKS40380       634  ERLKTYAHLFDDKVMKQLKR-RRYTGWGRLSRKLINGIRDK QSGKTILDFLK -DGf--------ANRNFMQLIHDDSL  702
4UN5_B         638  ERLKTYAHLFDDKVMKQLKR-RRYTGWGRLSRKLINGIRDK QSGKTILDFLK -DGf--------ANRNFMQLIHDDSL  706
WP_010922251   703  TFKEDIQKAQVSG-QGDS-LHEHIANLAGSPAIKKGILQTVKVVDELVKVMG-HKPENIVIEMARENQ TTQKGQKNS  777
WP_039695303   707  PFKQIIQKSQVVG-DVDD-IEAVVHDLPGSPAIKKGILQSVSKIVDELVKVMG-GNPDNIVIEMARENQ TTNRGRSQS  780
WP_045635197   702  SFKEIIQKAQVIG-KTDD-VKQVVQELSGSPAIKKGILQSIKIVDELVKVMG-HAPSIVIEMARENQ TTARGKKNS  775
5AXW_A         427  VPKKVDLSQQKEI---PT--TLVDDFILSPVVKRSFIQSIKVINAIIKKYG--LPNDIIIELAREKN -------S  487
```

-continued

| | | | |
|---|---|---|---|
| WP_009880683 | 387 TFKEDLQKAQVSG-QGDS-LHEHIANLAGSPAIKKGILQTVKVVDELVKVMGrHKPENIVIEMARENQ TTQKGQKNS | 461 |
| WP_010922251 | 703 TFKEDIQKAQVSG-QGDS-LHEHIANLAGSPAIKKGILQTVKVVDELVKVMGrHKPENIVIEMARENQ TTQKGQKNS | 777 |
| WP_011054416 | 703 TFKEDIQKAQVSG-QGDS-LHEHIANLAGSPAIKKGILQTVKVVDELVKVMGrHKPENIVIEMARENQ TTQKGQKNS | 777 |
| WP_011284745 | 703 TFKEDIQKAQVSG-QGDS-LHEHIANLAGSPAIKKGILQTVKVVDELVKVMGrHKPENIVIEMARENQ TTQKGQKNS | 777 |
| WP_011285506 | 703 TFKEDIQKAQVSG-QGDS-LHEHIANLAGSPAIKKGILQTVKVVDELVKVMGrHKPENIVIEMARENQ TTQKGQKNS | 777 |
| WP_011527619 | 703 TFKEDIQKAQVSG-QGDS-LHEHIANLAGSPAIKKGILQTVKVVDELVKVMGrHKPENIVIEMARENQ TTQKGQKNS | 777 |
| WP_012560673 | 703 TFKEDLQKAQVSG-QGDS-LHEHIANLAGSPAIKKGILQTVKVVDELVKVMGrHKPENIVIEMARENQ TTQKGQKNS | 777 |
| WP_014407541 | 703 TFKEDIQKAQVSG-QGHS-LHEQIANLAGSPAIKKGILQTVKVVDELVKVMG-HKPENIVIEMARENQ TTQKGQKNS | 776 |
| WP_020905136 | 703 TFKEAIQKAQVSG-QGDS-LHEQIANLAGSPAIKKGILQTVKVVDELVKVMG-HKPENIVIEMARENQ TTQKGQKNS | 776 |
| WP_023080005 | 703 TFKEDIQKAQVSG-QGDS-LHEHIANLAGSPAIKKGILQTVKVVDELVKVMGrHKPENIVIEMARENQ TTQKGQKNS | 777 |
| WP_023610282 | 703 TFKEDIQKAQVSG-QGHS-LHEQIANLAGSPAIKKGILQTVKVVDELVKVMG-HKPENIVIEMARENQ TTQKGQKNS | 776 |
| WP_030125963 | 703 TFKEDIQKAQVSG-QGDS-LHEHIANLAGSPAIKKGILQTVKVVDELVKVMGrHKPENIVIEMARENQ TTQKGQKNS | 777 |
| WP_030126706 | 703 TFKEDIQKAQVSG-QGDS-LHEHIANLAGSPAIKKGILQTVKVVDELVKVMGrHKPENIVIEMARENQ TTQKGQKNS | 777 |
| WP_031488318 | 703 TFKEDIQKAQVSG-QGDS-LHEHIANLAGSPAIKKGILQTVKVVDELVKVMGrHKPENIVIEMARENQ TTQKGQKNS | 777 |
| WP_032460140 | 703 TFKEDIQKAQVSG-QGDS-LHEHIANLAGSPAIKKGILQTVKVVDELVKVMGrHKPENIVIEMARENQ TTQKGQKNS | 777 |
| WP_032461047 | 703 TFKEDIQKAQVSG-QGDS-LHEHIANLAGSPAIKKGILQTVKVVDELVKVMGrHKPENIVIEMARENQ TTQKGQKNS | 777 |
| WP_032462016 | 703 TFKEDIQKAQVSG-QGDS-LHEHIANLAGSPAIKKGILQTVKVVDELVKVMGrHKPENIVIEMARENQ TTQKGQKNS | 777 |
| WP_032462936 | 703 TFKEDIQKAQVSG-QGDS-LHEHIANLAGSPAIKKGILQTVKVVDELVKVMGrHKPENIVIEMARENQ TTQKGQKNS | 777 |
| WP_032464890 | 703 TFKEDIQKAQVSG-QGDS-LHEHIANLAGSPAIKKGILQTVKVVDELVKVMGrHKPENIVIEMARENQ TTQKGQKNS | 777 |
| WP_033888930 | 528 TFKEDIQKAQVSG-QGDS-LHEHIANLAGSPAIKKGILQTVKIVDELVKVMGrHKPENIVIEMARENQ TTQKGQKNS | 602 |
| WP_038431314 | 703 TFKEDIQKAQVSG-QGDS-LHEHIANLAGSPAIKKGILQTVKVVDELVKVMGrHKPENIVIEMARENQ TTQKGQKNS | 777 |
| WP_038432938 | 703 TFKEAIQKAQVSG-QGHS-LHEQIANLAGSPAIKKGILQTVKIVDELVKVMG-HKPENIVIEMARENQ TTQKGQKNS | 776 |
| WP_038434062 | 703 TFKEDIQKAQVSG-QGDS-LHEHIANLAGSPAIKKGILQTVKVVDELVKVMGrHKPENIVIEMARENQ TTQKGQKNS | 777 |
| BAQ51233 | 614 TFKEDIQKAQVSG-QGDS-LHEHIANLAGSPAIKKGILQTVKVVDELVKVMGrHKPENIVIEMARENQ TTQKGQKNS | 688 |
| KGE60162 | ---------------------------------------------------------------------- ---------- | |
| KGE60856 | 703 TFKEDIQKAQVSG-QGDS-LHEHIANLAGSPAIKKGILQTVKVVDELVKVMGrHKPENIVIEMARENQ TTQKGQKNS | 777 |
| WP_002989955 | 704 SFKEEIARAQIIG-DVDD-IANVHDLPGSPAIKKGILQSVKIVDELVKVMG-HKPENIIIEMARENQ MTDKGRRNS | 777 |
| WP_003030002 | 707 PFKQIIQKSQVVG-DVDD-IEAVVHDLPGSPAIKKGILQSVKIVDELVKVMG-DNPDNIVIEMARENQ TTNRGRSQS | 780 |
| WP_003065552 | 702 SFKPIIDKARTGS-HSDN-LKEVIGELAGSPAIKKGILQSLKIVDELVKVMG-YEPEQIVVEMARENQ TTAKGLSRS | 775 |
| WP_001040076 | 705 SFKSIISKAQAGS-HSDN-LKEVVGELAGSPAIKKGILQSLKIVDELVKVMG-YEPEQIVVEMARENQ TTNQGRRNS | 778 |
| WP_001040078 | 705 SFKSIISKAQAGS-HSDN-LKEVVGELAGSPAIKKGILQSLKIVDELVKVMG-YEPEQIVVEMARENQ TTNQGRRNS | 778 |
| WP_001040080 | 705 SFKSIISKAQAGS-HSDN-LKEVVGELAGSPAIKKGILQSLKIVDELVKVMG-YEPEQIVVEMARENQ TTNQGRRNS | 778 |
| WP_001040081 | 705 SFKSIISKAQAGS-HSDN-LKEVVGELAGSPAIKKGILQSLKIVDELVKVMG-YEPEQIVVEMARENQ TTNQGRRNS | 778 |
| WP_001040083 | 705 SFKSIISKAQAGS-HSDN-LKEVVGELAGSPAIKKGILQSLKIVDELVKVMG-YEPEQIVVEMARENQ TTNQGRRNS | 778 |
| WP_001040085 | 705 SFKSIISKAQAGS-HSDN-LKEVVGELAGSPAIKKGILQSLKIVDELVKVMG-YEPEQIVVEMARENQ TTNQGRRNS | 778 |
| WP_001040087 | 705 SFKSIISKAQSGS-HSDN-LKEVVGELAGSPAIKKGILQSLKIVDELVKVMG-YEPEQIVVEMARENQ TTNQGRRNS | 778 |
| WP_001040088 | 705 SFKSIISKAQAGS-HSDN-LKEVVGELAGSPAIKKGILQSLKIVDELVKVMG-YEPEQIVVEMARENQ TTNQGRRNS | 778 |
| WP_001040089 | 705 SFKSIISKAQAGS-HSDN-LKEVVGELAGSPAIKKGILQSLKIVDELVKVMG-YEPEQIVVEMARENQ TTNQGRRNS | 778 |
| WP_001040090 | 702 SFKPIIDKARTGS-HLDN-LKEVVGELAGSPAIKKGILQSLKIVDELVKVMG-YEPEQIVVEMARENQ TTAKGLSRS | 775 |
| WP_001040091 | 702 SFKPIIDKARTGS-HLDN-LKEVVGELAGSPAIKKGILQSLKIVDELVKVMG-YEPEQIVVEMARENQ TTAKGLSRS | 775 |
| WP_001040092 | 705 SFKSIISKAQAGS-HSDN-LKEVVGELAGSPAIKKGILQSLKIVDELVKVMG-YEPEQIVVEMARENQ TTNQGRRNS | 778 |
| WP_001040094 | 702 SFKPIIDKARTGS-HSDN-LKEVVGELAGSPAIKKGILQSLKIVDELVKVMG-YEPEQIVVEMARENQ TTAKGLSRS | 775 |
| WP_001040095 | 702 SFKPIIDKARTGS-HLDN-LKEVVGELAGSPAIKKGILQSLKIVDELVKVMG-YEPEQIVVEMARENQ TTAKGLSRS | 775 |
| WP_001040096 | 702 SFKPIIDKARTGS-HLDN-LKEVVGELAGSPAIKKGILQSLKIVDELVKVMG-YEPEQIVVEMARENQ TTAKGLSRL | 775 |
| WP_001040097 | 702 SFKPIIDKARTGS-HSDN-LKEVVGELAGSPAIKKGILQSLKIVDELVKVMG-YEPEQIVVEMARENQ TTAKGLSRS | 775 |
| WP_001040098 | 705 SFKPIIDKAQAGS-HSDN-LKEVVGELAGSPAIKKGILQSLKIVDELVKVMG-YEPEQIVVEMARENQ TTNQGRRNS | 778 |
| WP_001040099 | 705 SFKPIIDKAQAGS-HSDN-LKEVVGELAGSPAIKKGILQSLKIVDELVKVMG-YEPEQIVVEMARENQ TTNQGRRNS | 778 |
| WP_001040100 | 705 SFKPIIDKAQAGS-HSDN-LKEVVGELAGSPAIKKGILQSLKIVDELVKVMG-YEPEQIVVEMARENQ TTNQGRRNS | 778 |
| WP_001040104 | 705 SFKPIIDKAQAGS-HSDN-LKEVVGELAGSPAIKKGILQSLKIVDELVKVMG-YEPEQIVVEMARENQ TTNQGRRNS | 778 |
| WP_001040105 | 705 SFKPIIDKAQAGS-HSDN-LKEVVGELAGSPAIKKGILQSLKIVDELVKVMG-YEPEQVVVEMARENQ TTNQGRRNT | 778 |
| WP_001040106 | 705 SFKPIIDKAQAGS-HSDN-LKEVVGELAGSPAIKKGILQSLKIVDELVKVMG-YEPEQVVVEMARENQ TTNQGRRNT | 778 |
| WP_001040107 | 705 SFKPIIDKAQAGS-HSDN-LKEVVGELAGSPAIKKGILQSLKIVDELVKVMG-YEPEQVVVEMARENQ TTNQGRRNT | 778 |
| WP_001040108 | 705 SFKPIIDKAQAGS-HSDN-LKEVVGELAGSPAIKKGILQSLKIVDELVKVMG-YEPEQVVVEMARENQ TTNQGRRNT | 778 |

| | | | | |
|---|---|---|---|---|
| WP_001040109 | 705 | SFKPIIDKAQAGS-HSDN-LKEVVGELAGSPAIKKGILQSLKIVDELVKVMG-YEPEQVVVEMARENQ | TTNQGRRNT | 778 |
| WP_001040110 | 705 | SFKPIIDKAQAGS-HSDN-LKEVVGELAGSPAIKKGILQSLKIVDELVKVMG-YEPEQVVVEMARENQ | TTNQGRRNT | 778 |
| WP_015058523 | 705 | SFKSIISKAQSGS-HSDN-LKEVVGELAGSPAIKKGILQSLKIVDELVKVMG-YEPEQIVVEMARENQ | TTNQGRRNS | 778 |
| WP_017643650 | 702 | SFKPIIDKARTGS-HSDN-LKEVVGELAGSPAIKKGILQSLKIVDELVKVMG-YEPEQIVVEMARENQ | TTAKGLSRL | 775 |
| WP_017647151 | 705 | SFKSIISKAQAGS-HSDN-LKEVVGELAGSPAIKKGILQSLKIVDELVKVMG-YEPEQIVVEMARENQ | TTNQGRRNS | 778 |
| WP_017648376 | 705 | SFKSIISKAQAGS-HSDN-LKEVVGELAGSPAIKKGILQSLKIVDELVKVMG-YEPEQIVVEMARENQ | TTNQGRRNS | 778 |
| WP_017649527 | 705 | SFKSIISKAQAGS-HSDN-LKEVVGELAGSPAIKKGILQSLKIVDELVKVMG-YEPEQIVVEMARENQ | TTNQGRRNS | 778 |
| WP_017771611 | 705 | SFKPIIDKAQAGS-HSDN-LKEVVGELAGSPAIKKGILQSLKIVDELVKVMG-YEPEQVVVEMARENQ | TTNQGRRNT | 778 |
| WP_017771984 | 705 | SFKSIISKAQAGS-HSDN-LKEVVGELAGSPAIKKGILQSLKIVDELVKVMG-YEPEQIVVEMARENQ | TTNQGRRNS | 778 |
| CFQ25032 | 705 | SFKSIISKAQAGS-HSDN-LKEVVGELAGSPAIKKGILQSLKIVDELVKVMG-YEPEQIVVEMARENQ | TTNQGRRNS | 778 |
| CFV16040 | 705 | SFKSIISKAQAGS-HSDN-LKEVVGELAGSPAIKKGILQSLKIVDELVKVMG-YEPEQIVVEMARENQ | TTNQGRRNS | 778 |
| KLJ37842 | 705 | SFKSIISKAQSGS-HSDN-LKEVVGELAGSPAIKKGILQSLKIVDELVKVMG-YEPEQIVVEMARENQ | TTNQGRRNS | 778 |
| KLJ72361 | 719 | SFKSIISKAQAGS-HSDN-LKEVVGELAGSPAIKKGILQSLKIVDELVKVMG-YEPEQVVVEMARENQ | TTNKGRRNT | 792 |
| KLL20707 | 705 | SFKSIISKAQAGS-HSDN-LKEVVGELAGSPAIKKGILQSLKIVDELVKVMG-YEPEQIVVEMARENQ | TTNQGRRNS | 778 |
| KLL42645 | 702 | SFKPIIDKARTGS-HSDN-LKEVVGELAGSPAIKKGILQSLKIVDELVKVMG-YEPEQIVVEMARENQ | TTAKGLSRS | 775 |
| WP_047207273 | 705 | SFKSIISKAQAGS-HSDN-LKEVVGELAGSPAIKKGILQSLKIVDELVKVMG-YEPEQIVVEMARENQ | TTNQGRRNS | 778 |
| WP_047209694 | 705 | SFKPIIDKAQAGS-HSDN-LKEVVGELAGSPAIKKGILQSLKIVDELVKVMG-YEPEQVVVEMARENQ | TTNQGRRNT | 778 |
| WP_049516684 | 705 | SFKSIISKAQAGS-HSDN-LKEVVGELAGSPAIKKGILQSLKIVDELVKVMG-YEPEQIVVEMARENQ | TTNQGRRNS | 778 |
| WP_050198062 | 705 | SFKSIISKAQAGS-HSDN-LKEVVGELAGSPAIKKGILQSLKIVDELVKVMG-YEPEQIVVEMARENQ | TTNQGRRNS | 778 |
| WP_050201642 | 705 | SFKSIISKAQAGS-HSDN-LKEVVGELAGSPAIKKGILQSLKIVDELVKVMG-YEPEQIVVEMARENQ | TTNQGRRNS | 778 |
| WP_050204027 | 705 | SFKPIIDKAQAGS-HSDN-LKEVVGELAGSPAIKKGILQSLKIVDELVKVMG-YEPEQVVVEMARENQ | TTNQGRRNT | 778 |
| WP_050881965 | 705 | SFKSIISKAQAGS-HSDN-LKEVVGELAGSPAIKKGILQSLKIVDELVKVMG-YEPEQIVVEMARENQ | TTNQGRRNS | 778 |
| WP_050886065 | 705 | SFKSIISKAQAGS-HSDN-LKEVVGELAGSPAIKKGILQSLKIVDELVKVMG-YEPEQIVVEMARENQ | TTNQGRRNS | 778 |
| AHN30376 | 705 | SFKSIISKAQSGS-HSDN-LKEVVGELAGSPAIKKGILQSLKIVDELVKVMG-YEPEQIVVEMARENQ | TTNQGRRNS | 778 |
| EA078426 | 705 | SFKSIISKAQAGS-HSDN-LKEVVGELAGSPAIKKGILQSLKIVDELVKVMG-YEPEQIVVEMARENQ | TTNQGRRNS | 778 |
| CCW42055 | 705 | SFKSIISKAQSGS-HSDN-LKEVSELAGSPAIKKGILQSLKIVDELVKVMG-YKPEQIVVEMARENQ | TTNQGRRNS | 778 |
| WP_003041502 | 704 | SFKEEIAKAQIIG-DVDD-IANVHDLPGSPAIKKGILQSVKIVDELVKVMG-HNPANIIIEMARENQ | TDRGRRNS | 777 |
| WP_037593752 | 705 | SFKEEIARAQIIG-DVDD-IANVHDLPGSPAIKKGILQSVKIVDELVKVMG-HNPANIIIEMARENQ | TTDKGRRNS | 778 |
| WP_049516684 | 705 | SFKEEIARAQIIG-DVDD-IANVHDLPGSPAIKKGILQSVKIVDELVKVMG-HNPANIIIEMARENQ | TTDKGRRNS | 778 |
| GAD46167 | 704 | SFKEEIARAQIIG-DVDD-IANVHDLPGSPAIKKGILQSVKIVDELVKVMG-HNPANIIIEMARENQ | TTDKGRRNS | 777 |
| WP_018363470 | 705 | SFKQIIQEAQVVG-DVDD-IETVHDLPGSPAIKKGILQSVKIVDELIKVMG-DNPDNIVIEMARENQ | TTNRGRSQS | 778 |
| WP_003043819 | 713 | TFKEEIEKAQVSG-QGDS-LHEQIADLAGSPAIKKGILQTVKIVDELVKVMG-HKPENIVIEMARENQ | TTTKGLQQS | 786 |
| WP_006269658 | 704 | TFKEEIARAQIIG-DVDD-IANVHDLPGSASSPAIKKGILQSVKIVDELVKVMG-HNPANIIIEMARENQ | TTDKGRRNS | 777 |
| WP_048800889 | 704 | PFKQIIKDAQAID-DVDD-IELIVHDLPGSPAIKKGILQSVKIVDELVKVMG-YNPDNIVIEMARENQ | TTTKGRRNS | 777 |
| WP_012767106 | 703 | TFKEAIQKAQVSG-QGHS-LHEQIANLAGSPAIKKGILQSVKIVDELVKVMG-HKPENIVIEMARENQ | TTQKGQKNS | 776 |
| WP_014612333 | 703 | TFKEAIQKAQVSG-QGHS-LHEQIANLAGSPAIKKGILQSVKIVDELVKVMG-HKPENIVIEMARENQ | TTQKGQKNS | 776 |
| WP_015017095 | 703 | TFKEAIQKAQVSG-QGHS-LHEQIANLAGSPAIKKGILQSVKIVDELVKVMG-HKPENIVIEMARENQ | TTQKGQKNS | 776 |
| WP_015057649 | 703 | TFKEAIQKAQVSG-QGHS-LHEQIANLAGSPAIKKGILQSVKIVDELVKVMG-HKPENIVIEMARENQ | TTQKGQKNS | 776 |
| WP_048272215 | 703 | SFKEAIQKAQVSG-QGHS-LHEQIANLAGSPAIKKGILQSVKIVDELVKVMG-HKPENIVIEMARENQ | TTQKGQKNS | 776 |
| WP_049515931 | 703 | SFIDEIAKAQVIG-KTEY-SKDLVGNLAGSPAIKKGILQSTIKIVDELVKIMG-YLPQQIVIEMARENQ | TTAQGIKNA | 776 |
| WP_021320964 | 703 | SFIDEIAKAQVIG-KTEY-SKDLVGNLASSPAIKKGILQSTIKIVDELVKIMG-YLPQQIVIEMARENQ | TTAQGIKNA | 776 |
| WP_037581760 | 703 | SFIDEIAKAQVIG-KTEY-SKDLVGNLAGSPAIKKGILQSTIKIVDELVKIMG-YLPQQIVIEMARENQ | TTAQGIKNA | 776 |
| WP_004232481 | 704 | SFKTTIQEAQVVG-DVDD-IEAVVHDLPGSPAIKKGILQSVKIVDELVKVMG-HNPQNIVIEMARENQ | ITGYGRRNS | 777 |
| WP_009854540 | 705 | PFKQIIQKSQVVG-DVDD-IEAVVHDLPGSPAIKKGILQSVKIVDELVKVMG-DNPDNIVIEMARENQ | TTNRGRRNS | 778 |
| WP_012962174 | 703 | PFKQIIKDAQIIG-DIDD-VTSVVRELPGSPAIKKGILQSVKIVDELVKIMG-HNPDNIVIEMARENQ | TTNRGRNQS | 777 |
| WP_039695303 | 707 | PFKQIIQKSQVVG-DVDD-IEAVVHDLPGSPAIKKGILQSVKIVDELVKVMG-GNPDNIVIEMARENQ | TTNRGRRNS | 780 |
| WP_014334983 | 704 | SFKTIIQEAQVVG-DVDD-IEAVVHDLPGSPAIKKGILQSVKIVDELVKVMG-DNPDNIVIEMARENQ | TTGYGRNKS | 777 |
| WP_030099269 | 703 | DFAKIIKNEQEKTiKNES-LEETIANLAGSPAIKKGILQSIKIVDELVKIMG-QNPDNIVIEMARENQ | STMQGIKNS | 777 |
| AHY15608 | 703 | DFAKIIKNEQEKTiKNES-LEETIANLAGSPAIKKGILQSIKIVDELVKIMG-QNPDNIVIEMARENQ | STMQGIKNS | 777 |
| AHY17476 | 704 | DFAKIIKNEQEKTiKNES-LEETIANLAGSPAIKKGILQSIKIVDELVKIMG-QNPDNIVIEMARENQ | STMQGIKNS | 777 |
| ESR09100 | | | | |
| AGM98575 | 703 | DFAKIIKNEQEKTiKNES-LNQVVSDIAGSPAIKKGILQSIKIVDEIVKIMG-QNPDNIVIEMARENQ | STMQGIKNS | 777 |
| ALF27331 | 704 | SFKEEIAKAQVIG-ETDN-LNQVVSDIAGSPAIKKGILQSLKIVDELVKIMG-HQPENIVIEMARENQ | FTNQGRRNS | 777 |

```
WP_018372492  717  DFKEIIRKAQTIE-NIDT-NQALVSSLPGSPAIKKGILQSLNIVDEIIAIMG-YAPTNIVIEMARENQ TTQKGRDNS  790
WP_045618028  703  SFKEIIQKAQVVG-KTND-VKQVQELPGSPAIKKGILQSIKIVDELVKIMG-HAPESIVIEMARENQ TTARGKKNS  776
WP_045635197  702  SFKEIIQKAQVIG-KTDD-VKQVQELSGSPAIKKGILQSIKIVDELVKVMG-HAPESIVIEMARENQ TTARGKKNS  775
WP_002263549  704  SFKEEIAKAQVIG-ETDN-LNQVVSDIAGSPAIKKGILQSLKIVDELVKIMG-HQPENIVVEMARENQ FTNQGRRNS  777
WP_002263887  704  SFKEEIAKAQVIG-ETDN-LNQVVSDIAGSPAIKKGILQSLKIVDELVKIMG-HQPENIVVEMARENQ FTNQGRRNS  777
WP_002264920  704  SFKEEIAKAQVIG-ETDN-LNQVVSDIAGSPAIKKGILQSLKIVDELVKIMG-HQPENIVVEMARENQ FTNQGRRNS  777
WP_002269043  704  SFKEEIAKAQVIG-ETDN-LNQVVSDIAGSPAIKKGILQSLKIVDELVKIMG-HQPENIVVEMARENQ FTNQGRRNS  777
WP_002269448  704  SFKEEIAKAQVIG-ETDN-LNQVVSDIAGSPAIKKGILQSLKIVDELVKIMG-HQPENIVVEMARENQ FTNQGRQNS  777
WP_002271977  704  SFKEEIAKAQVIG-ETDN-LNQVVSDIAGSPAIKKGILQSLKIVDELVKIMG-HQPENIVVEMARENQ FTNQGRRNS  777
WP_002272766  704  SFKEEIAKAQVIG-ETDN-LNQVVSDIAGSPAIKKGILQSLKIVDELVKIMG-HQPENIVVEMARENQ FTKQGRRNS  777
WP_002273241  704  SFKEEIAKAQVIG-ETDN-LNQVVSDIAGSPAIKKGILQSLKIVDELVKVMG-HAPESIVIEMARENQ FTNQGRRNS  777
WP_002275430  704  SFKEEIAKAQVIG-ETDN-LNQVVSDIAGSPAIKKGILQSLKIVDELVKIMG-HQPENIVVEMARENQ FTNQGRRNS  777
WP_002276448  704  SFKEEIAKAQVIG-ETDN-LNQVVSDIAGSPAIKKGILQSLKIVDELVKIMG-HQPENIVVEMARENQ FTNQGRRNS  777
WP_002277050  705  TFKDDIVKAQYVD-NSDD-LHQVVQSLAGSPAIKKGILQSLKIVDELVKVMG-KEPEQIVVEMARENQ TTAKGRRNS  778
WP_002277364  704  SFKEEIAKAQVIG-ETDN-LNQVVSDIAGSPAIKKGILQSLKIVDELVKIMG-HQPENIVVEMARENQ FTNQGRRNS  777
WP_002279025  704  SFKEEIAKAQVIG-ETDN-LNQVVSDIAGSPAIKKGILQSLKIVDELVKIMG-HQPENIVVEMARENQ FTNQGRRNS  777
WP_002279859  704  SFKEEIAKAQVIG-ETDN-LNQVVSDIAGSPAIKKGILQSLKIVDELVKIMG-HQPENIVVEMARENQ FTKQGRRNS  777
WP_002280230  704  SFKEEIAKAQVIG-ETDN-LNQVVSDIAGSPAIKKGILQSLKIVDELVKIMG-HQPENIVVEMARENQ FTNQGRRNS  777
WP_002281696  704  SFKEEIAKAQVIG-ETDN-LNQVVSDIAGSPAIKKGILQSLKIVDELVKIMG-HQPENIVVEMARENQ FTNQGRRNS  777
WP_002282247  705  TFKDDIVKAQYVD-NSDD-LHQVVSLAGSPAIKKGILQSLKIVDELVKVMG-KEPEQIVVEMARENQ TTAKGRRNS  778
WP_002282906  704  SFKEEIAKAQVIG-ETDN-LNQVVSDIAGSPAIKKGILQSLKIVDELVKIMG-HNPANIVIEMARENQ TTAKGRSS  777
WP_002283846  704  SFKEEIAKAQVIG-ETDN-LNQVVSDIAGSPAIKKGILQSLKIVDELVKIMG-HQPENIVVEMARENQ FTKQGRRNS  777
WP_002287255  704  SFKEEIAKAQVIG-ETDN-LNQVVSDIAGSPAIKKGILQSLAIKKGILQSLKIVDELVKIMG-HQPENIVVEMARENQ FTNQGRRNS  777
WP_002288990  704  SFKEEIAKAQVIG-ETDN-LNQVVSDIAGSPAIKKGILQSLAIKKGILQSLKIVDELVKIMG-HQPENIVVEMARENQ FTNQGRRNS  777
WP_002289641  704  SFKEEIAKAQVIG-ETDN-LNQVVSDIAGSPAIKKGILQSLKIVDELVKIMG-HQPENIVVEMARENQ FTNQGRRNS  777
WP_002290427  704  SFKEEIAKAQVIG-ETDN-LNQVVSDIAGSPAIKKGILQSLKIVDELVKIMG-HQPENIVVEMARENQ FTNQGRRNS  777
WP_002295753  704  SFKEEIAKAQVIG-ETDN-LNQVVSDIAGSPAIKKGILQSLKIVDELVKIMG-HQPENIVVEMARENQ FTNQGRRNS  777
WP_002296423  704  SFKEEIAKAQVIG-ETDN-LNQVVSDIAGSPAIKKGILQSLKIVDELVKIMG-HQPENIVVEMARENQ FTNQGRRNS  777
WP_002304487  714  SFKEEIAKAQVIG-EMDG-LNQVVSDIAGSPAIKKGILQSLKIVDELVKIMG-HQPENIVVEMARENQ FTNQGRRNS  787
WP_002305844  704  SFKEEIAKAQVIG-ETDN-LNQVVSDIAGSPAIKKGILQSLKIVDELVKIMG-HQPENIVVEMARENQ FTKQGRRNS  777
WP_002307203  704  SFKEEIAKAQVIG-ETDN-LNQVVSDIAGSPAIKKGILQSLAIKKGILQSLKIVDELVKIMG-HQPENIVVEMARENQ FTNQGRRNS  777
WP_002310390  704  SFKEEIAKAQVIG-ETDN-LNQVVSDIAGSPAIKKGILQSLKIVDELVKIMG-HQPENIVVEMARENQ FTNQGRRNS  777
WP_002352408  704  SFKEEIAKAQVIG-ETDN-LNQVVSDIAGSPAIKKGILQSLKIVDELVKIMG-HQPENIVVEMARENQ FTNQGQRNS  777
WP_012997688  704  SFKEEIAKAQVIG-ETDN-LNQVVSDIAGSPAIKKGILQSLKIVDELVKIMG-HQPENIVVEMARENQ FTNQGRRNS  777
WP_014677909  705  TFKDDIVKAQYVD-NSDD-LHQVVQSLAGSPAIKKGILQSLKIVDELVKVMG-KEPEQIVVEMARENQ TTAKGRRNS  778
WP_019312892  704  SFKEEIAKAQVIG-ETDN-LNQVVSDIAGSPAIKKGILQSLKIVDELVKIMG-HQPENIVVEMARENQ FTNQGRRNS  777
WP_019313659  704  SFKEEIAKAQVIG-ETDN-LNQVVSDIAGSPAIKKGILQSLKIVDELVKIMG-HQPENIVVEMARENQ FTNQGRRNS  777
WP_019314093  705  TFKDDIVKAQYVD-NSDD-LHQVVQSLAGSPAIKKGILQSLKIVDELVKVMG-KEPEQIVVEMARENQ TTAKGRRNS  778
WP_019315370  704  SFKEEIAKAQVIG-ETDN-LNQVVSDIAGSPAIKKGILQSLKIVDELVKIMG-HQPENIVVEMARENQ FTNQGRRNS  777
WP_019803776  704  SFKEEIAKAQVIG-ETDN-LNQVVSDIAGSPAIKKGILQSLKIVDELVKIMG-HQPENIVVEMARENQ FTNQGRRNS  777
WP_019805234  704  SFKEEIAKAQVIG-ETDN-LNQVVSDIAGSLAIKKGILQNLKIVDELVKIMG-HQPENIVVEMARENQ FTNQGRRNS  777
WP_024783594  704  SFKEEIAKAQVIG-ETDN-LNQVVSDIAGSLAIKKGILQSLKIVDELVKIMG-HQPENIVVEMARENQ FTNQGRRNS  777
WP_024784288  705  TFKDDIVKAQYVD-NSDD-LHQVVQSLAGSPAIKKGILQSLKIVDELVKVMG-KEPEQIVVEMARENQ TTAKGRRNS  778
WP_024784666  704  SFKEEIAKAQVIG-ETDN-LNQVVSDIAGSPAIKKGILQSLKIVDELVKIMG-HEPESIVIEMARENQ FTNQGRRNS  777
WP_024784894  704  SFKEEIAKAQVIG-ETDN-LNQVVSDIAGSPAIKKGILQSLKIVDELVKIMG-HTPESIVIEMARENQ FTNQGRRNS  777
WP_024786433  705  TFKDDIVKAQYVD-NSDD-LHQVVQSLAGSPAIKKGILQSLKIVDELVKVMG-KEPEQIVVEMARENQ TTAKGRRNS  778
WP_049473442  704  SFKEEIAKAQVIG-ETDN-LNQVVSDIAGSPAIKKGILQSLKIVDELVKIMG-HQPENIVVEMARENQ FTNQGRRNS  777
WP_049474547  704  SFKEEIAKAQVIG-ETDN-LNQVVSDIAGSPAIKKGILQSLKIVDELVKIMG-HQPENIVVEMARENQ FTNQGRRNS  777
EMC03581      697  SFKEEIAKAQVIG-ETDN-LNQVVSDIAGSPAIKKGILQSLKIVDELVKIMG-HQPENIVVEMARENQ FTNQGRRNS  770
WP_000428612  705  TFKDDIVKAQYVD-NSDD-LHQVVQSLAGSPAIKKGILQSLKIVDELVKVMG-HEPESIVIEMARENQ TTARGKKNS  778
WP_000428613  703  SFKEITQKAQVVG-KTDD-VKQVQELPGSPAIKKGILQSIKIVDELVKIMG-HAPESIVIEMARENQ TTARGKKNS  776
WP_049523028  702  SFKEIIQKAQVIG-ETND-VKQVQELSGSPAIKKGILQSIKIVDELVKIMG-HAPESVIVEMARENQ TTNKGKSKS  775
WP_003107102  672  DFASIIKEAQEKTIKSEK-LEETIANLAGSPAIKKGILQSVKIVDEVVKIVG-YEPSNIVIEMARENQ STQRGINNS  746
```

| | | | |
|---|---|---|---|
| WP_054279288 | 705 | SFKEEIKAQEGG-LKDS-INDQIRDLAGSPAIKKGLLQTINIVDEIVKIMG-KAPQHIVVEMARDVQ | KTDIGVKQS | 778 |
| WP_049531101 | 703 | SFKEIIQESQVVG-KPDD-VKQIVQELPGSSAIKKGILQSIKIVDELVKVMG-HDPESIVIEMARENQ | TTARGKKNS | 776 |
| WP_049538452 | 703 | SFKEIIQKAQVFG-KTND-VKQVVQELPGSPAIKKGILQSIKIVDEELVKVMG-HEPESIVIEMARENQ | TTTRGKKNS | 776 |
| WP_049549711 | 703 | SFKEIIQKSQVVG-ETDD-VKQVVRELPGSPAIKKGILQSIKIVDELVKIMG-HAPESIVIEMARENQ | TTARGKKNS | 776 |
| WP_007896501 | 706 | DFEKLIDDAQKKAiKRES-LTEAVANLAGSPAIKKGILQSLKVVDEIVKVMG-HNPDNIVIEMSRENQ | TTAQGLKNA | 780 |
| EFR44625 | 658 | DFEKLIDDAQKKAiKRES-LTEAVANLAGSPAIKKGILQSLKVVDEIVKVMG-HNPDNIVIEMSRENQ | TTAQGLKNA | 732 |
| WP_002897477 | 702 | SFKEIIQKAQVVG-KTDD-VKQVVQELPGSPAIKKGILQSIKIVDELVKVMG-YALESIVIEMARENQ | TTARGKKNS | 775 |
| WP_002906454 | 703 | SFKEIIQKAQVVG-KTDD-VKQVVPGSPAIKKGILQSIKIVDELVKVMG-HNPESIVIEMARENQ | TTAKGKKNS | 775 |
| WP_009729476 | 703 | SFKEIIQKAQVVG-KTND-VKQVVQELPGSPAIKKGILQSIKIVDELVKVMG-HAPESIVIEMARENQ | TTARGKKNS | 776 |
| CQR24647 | 706 | SFKDEIANSQVIG-DGDD-LHQVQELAGSPAIKKGILQSIKIVDELVKVMG-YNPEQIVVEMARENQ | TTARGRNNS | 779 |
| WP_000066813 | 705 | SFKEIIQKAQVFG-KTND-VKQVVQELPGSPAIKKGILQSIKIVDELVKIMG-HAPESIVIEMARENQ | TTARGKKNS | 778 |
| WP_009754323 | 703 | SFKEIIQKAQVVG-KTND-LTQVRELSGSPAIKKGILQSIKIVEELKVMG-YAPESIVIEMARENQ | TTAKGKKNS | 776 |
| WP_044674937 | 702 | SFVDEIRLAQGSG-EAED-YRAEVQNLAGSPAIKKGILQSLKIVDELIEVMG-YDPBHIVVEMARENQ | FTNQGRRNS | 775 |
| WP_044676715 | 704 | SFVDEIRLAQGSG-EAED-YRAEVQNLAGSPAIKKGILQSLKIVDELIEVMG-YDPEHIVVEMARENQ | FTNQGRRNS | 777 |
| WP_044680361 | 704 | SFVDEIRLAQGSG-EAED-YRAEVQNLAGSPAIKKGILQSLKIVDELIEVMG-YDPEHIVVEMARENQ | FTNQGRRNS | 777 |
| WP_044681799 | 702 | SFVDEIRLAQGSG-EAED-YRAEVQNLAGSPAIKKGILQSLKIVDELVKVMG-YDPEHIVVEMARENQ | FTNQGRRNS | 775 |
| WP_049533112 | 704 | SEKEETAKAQVIG-ETDD-LNQVVSDIAGSPAIKKGILQSLKIVDELVKVMG-YNPANIVIEMARENQ | TTDKGRRNS | 777 |
| WP_029090905 | 683 | LFKKIIEEQFENEtALLN--KQRIDELAASPANKKGIWQATKIVKELEKVLQ-QPAENIFIEFARSDE | ES----KRS | 752 |
| WP_006506696 | 706 | GYAQMIEEATSCPeDGKE-TYEEVERLAGSPALKRGIWQSLQIVEEITKVMK-CRPKYIYIEFERSEE | ----KERT | 776 |
| AIT42264 | 703 | TEKEDIQAVSG-QGDS-LHEHIANLAGSPAIKKGILQTVKVVDELVKVMGrHKPENIVIEMARENQ | TTQKGQKNS | 777 |
| WP_034440723 | 711 | SFKEKIRKAQDIN-QVND-IKEIVKDLPGSPAIKKGIYQSIRIVDEIIRKMK-DRPKNIVIEMARENQ | TTQEGKNKS | 784 |
| AKQ21048 | 703 | TEKEDIQAVSG-QGDS-LHEHIANLAGSPAIKKGILQTVKVVDELVKVMGrHKPENIVIEMARESQ | TTKKGKDLS | 777 |
| WP_004636532 | 707 | SFKKKIEDAQTIE-DTTH-IYDTVAELPGSPAIKKGIRQALKIVEEIIDIIG-YEPENIVVEMAREEQ | TTSTGKRRS | 780 |
| WP_002364836 | 715 | SFKNAIQKAQSSE-HEET-LSETVNELAGSPAIKKGIWQSLKIVDELVAIMG-YAPKRIVVEMARENQ | TTSTGKRRS | 788 |
| WP_016631044 | 666 | SFKNAIQKAQSSE-HEET-LSETVNELAGSPAIKKGIYQSLKIVDELVAIMG-YAPKRIVVEMARENQ | TTSTGKRRS | 739 |
| EMS75795 | 455 | SFKEELANELALA-GNQS-LLEVVEALLGSPAIKKGILQSLKIVDELVAIMG-YAPKRIVVEMARENQ | RT---NRS | 524 |
| WP_002373311 | 715 | SFKNAIQKAQSSE-HEET-LSETVNELAGSPAIKKGIWQTLKIVEELIEIIG-YNPKNIVVEMARENQ | TTSTGKRRS | 788 |
| WP_002378009 | 715 | SFKNAIQKAQSSE-HEET-LSETVNELAGSPAIKKGIYQSLKIVDELVAIMG-YAPKRIVVEMARENQ | TTSTGKRRS | 788 |
| WP_002407324 | 715 | SFKNAIQKAQSSE-HEET-LSETVNELAGSPAIKKGIYQSLKIVDELVAIMG-YAPKRIVVEMARENQ | TTSTGKRRS | 788 |
| WP_002413717 | 717 | SFKNAIQKAQSSE-HEET-LSETVNELAGSPAIKKGIYQSLKIVDELVAIMG-YAPKRIVVEMARENQ | TTSTGKRRS | 790 |
| WP_010775580 | 715 | SFKNAIQKAQSSE-HEET-LSETVNELAGSPAIKKGIYQSLKIVDELVAIMG-YAPKRIVVEMARENQ | TTSTGKRRS | 788 |
| WP_010818269 | 715 | SFKNAIQKAQSSE-HEET-LSETVNELAGSPAIKKGIYQSLKIVDELVAIMG-YAPKRIVVEMARENQ | TTSTGKRRS | 788 |
| WP_010824395 | 715 | SFKNAIQKAQSSE-HEET-LSETVNELAGSPAIKKGIYQSLKIVDELVAIMG-YAPKRIVVEMARENQ | TTSTGKRRS | 788 |
| WP_016622645 | 715 | SFKNAIQKAQSSE-HEET-LSETVNELAGSPAIKKGIYQSLKIVDELVAIMG-YAPKRIVVEMARENQ | TTSTGKRRS | 788 |
| WP_033624816 | 715 | SFKKEIKKAQMIT-DTEN-LEEIVKELTGSPAIKKGILQSLKIVDEIVGIMG-YEPANIVVEMARENQ | TTGRLKSS | 788 |
| WP_033625576 | 715 | SFKKEIKKAQMIT-DTEN-LEEIVKELTGSPAIKKGILQSLKIVDEIVGIMG-YEPANIVVEMARENQ | TTGRLKSS | 788 |
| WP_033789179 | 715 | SFKKEIKKAQMIT-DTEN-LEEIVKELTGSPAIKKGILQSLKIVDEIVGIMG-YEPANIVVEMARENQ | TTGRLKSS | 788 |
| WP_002310644 | 715 | SFKKEIKKAQMIT-DTEN-LEEIVKELTGSPAIKKGILQSLKIVDEIVGIMG-YEPANIVVEMARENQ | TTGRLKSS | 788 |
| WP_002312694 | 716 | SFKKEIKKAQMIT-DTEN-LEEIVKELTGSPAIKKGILQSLKIVDEIVGIMG-YEPANIVVEMARENQ | TTGRLKSS | 789 |
| WP_002314015 | 716 | SFKKEIKKAQMIT-DTEN-LEEIVKELTGSPAIKKGILQSLKIVDEIVGIMG-YEPANIVVEMARENQ | TTGRLKSS | 789 |
| WP_002320716 | 716 | SFKKEIKKAQMIT-DTEN-LEEIVKELTGSPAIKKGILQSLKIVDEIVGIMG-YEPANIVVEMARENQ | TTGRLKSS | 789 |
| WP_002330729 | 715 | SFKKEIKKAQMIT-DTEN-LEEIVKELTGSPAIKKGILQSLKIVEELIAIIG-YKPKNIVIEMARENQ | TTGRLKSS | 788 |
| WP_002335161 | 716 | SFKKEIKKAQMIT-DTEN-LEEIVKELTGSPAIKKGILQSLKIVEELIAIIG-YKPKNIVIEMARENQ | TTGRLKSS | 789 |
| WP_002345439 | 716 | SFKKEIAKATVFS-KHKS-LVDVIQDLPGSPAIKKGIWQSLKIVEELIAIIG-YKPKNIVIEMARENQ | TTGRLKSS | 789 |
| WP_034867970 | 716 | SFKKEIAKATVFS-KHKS-LVDVIQDLPGSPAIKKGIWQSLKIVEELIAIIG-YKPKNIVIEMARENQ | TTGRLKSS | 789 |
| WP_047937432 | 716 | SFKKEIAKATVFS-KHKS-LVDVIQDLPGSPAIKKGIWQSLKIVEELIAIIG-YKPKNIVIEMARENQ | TTGRLKSS | 789 |
| WP_010720994 | 711 | SFKEEIKAQMIT-DTEN-LEEIVKELTGSPAIKKGILQSLKIVDELVAIMG-YKPKNIVIEMARENQ | KT----HRT | 780 |
| WP_010737004 | 711 | SFKEEIAKATVFS-KHKS-LVDVIQDLPGSPAVKKGIWQSIKIVEELIGIIG-KAPKNIVIEMARENQ | KT----HRT | 780 |
| WP_034700478 | 711 | SFKKIEDSQPYK-EQQS-AEEIVSELSGSPAIKKGILQSLKIVDELVAIMG-YKPKNIVIEMARENQ | KT----HRT | 780 |
| WP_007209003 | 708 | SFKETIANELIMS-DSNV-LLDQVKAIPGSPAVKKGIWQSIKIVEELIGIIG-KAPKNIVIEMARENQ | TTGRGKQNS | 781 |
| WP_023519017 | 705 | SFKSEIAEAQSDM-NTED-LHEVVQNLAGSPAIKKGILQSLKIVDELVDIMG-SLPKNIVIEMARENQ | RTSR----S | 774 |
| WP_010770040 | 708 | SFKSEIAEAQSDM-NTED-LHEVVQNLAGSPAIKKGILQSLKIVDELVDIMG-SLPKNIVIEMARENQ | TTSRGRTNS | 781 |
| WP_048604708 | 704 | TFKEEIBEKEQLKA-NSEESLIEIVQNLAGSPAIKKGIFQSLKIVDELVEIMG-YAPTNIVVEMARENQ | TTANGRRNS | 778 |

-continued

```
WP_010750235   710  SFKEEIAKELTLS-DKQS-LLEVVEAIPGSPAIKKGIWQTLKIVEELIAIIG-YKPKNIVIEMARENQ TTTGGKNRS  783
AII16583       742  TFKEDIQKAQVSG-QGDS-LHEHIANLAGSPAIKKGILQTVKVVDELVKVMGrHKPENIVIEMARENQ TTQKGQKNS  816
WP_029073316   718  GFKKTIDDANSTSvSGKF-SYAEVQELAGSPAIKRGIWQALLIVDEIKKIMK-HEPAHVYIEFARNED -----KERK  788
WP_031589969   718  GFKKTIDDANSTSvSGKF-SYAEVQELAGSPAIKRGIWQALLIVDEIKKIMK-HEPAHVYIEFARNED -----KERK  788
KDA45870       699  SPKETIKNAQVIE-KEET-LAKTVQELPGSPAIKKGILQSLEIVDEIIKVMG-YKPKSIVVEMARETQ --THGTRKR  771
WP_039099354   713  DFDKLITEANQMM-LAENdVQDVINDLYTSPQNKKALRQILLVVNDIQKAMKgQAPERILIEFAREDE VNPRLSVQR  788
AKP02966       719  DFKNYIENHNLNKnEDQN-ISNLVNDIHVSPALKRGITQSIKIVQEIVKFMG-HAPKYIFIEVTRETK TTSRGKRIQ  785
WP_010991369   707  SFKSIIEKEQVTT-ADKD-IQSIVADLAGSPAIKKGIIQSLKIVDELVSVMG-YPPQTIVVEMARENQ TTGKGKNNS  780
WP_033838504   707  SFKSIIEKEQVTT-ADKD-IQSIVADLAGSPAIKKGILQSLKIVDELVSVMG-YPPQTIVVEMARENQ TTGKGKNNS  780
EHN60060       710  SFKSIIEKEQVTT-ADKD-IQSIVADLAGSPAIKKGILQSLKIVDELVSVMG-YPPQTIVVEMARENQ TTGKGKNNS  783
EFR89594       476  SFKSIIEKEQVTT-ADKD-IQSIVADLAGSPAIKKGILQSLKIVDELVSVMG-YPPQTIVVEMARENQ TTGKGKNNS  549
WP_038409211   707  SFKSIIEKEQVST-ADKG-IQSIVAELAGSPAIKKGILQSLKIVDELVGIMG-YPPQTIVVEMARENQ TTGKGKNNS  780
EFR95520       326  SFKSIIEKEQVST-ADKD-LQSIVADLAGSPAIKKGILQSLKIVDELVSIMG-YPPQTIVVEMARENQ TTGKGKNNS  399
WP_003723650   707  SFKSIIEKEQVST-TDKD-LQSIVADLAGSPAIKKGILQSLKIVDELVSIMG-YPPQTIVVEMARENQ TTGKGKNNS  780
WP_003727705   707  SFKSIIEKEQVST-TDKD-LQSIVADLAGSPAIKKGILQSLKIVDELVSIMG-YPPQTIVVEMARENQ TTGKGKNNS  780
WP_003730785   707  SFKSIIEKEQVST-TDKD-LQSIVADLAGSPAIKKGILQSLKIVDELVSIMG-YPPQTIVVEMARENQ TTGKGKNNS  780
WP_003733029   707  SFKSIIEKEQVST-ADKD-LQSIVADLAGSPAIKKGILQSLKIVDELVSVMG-YPPQTIVVEMARENQ TTGKGKNNS  780
WP_003739838   707  SFKSIIEKEQVST-TDKD-LQSIVADLAGSPAIKKGIIQSLKIVDELVSIMG-YPPQTIVVEMARENQ TTVKGKNNS  780
WP_014601172   707  SFKSIIEKEQVST-ADKD-LQSIVADLAGSPAIKKGILQSLKIVDELVSVMG-YPPQTIVVEMARENQ TTGKGKNNS  780
WP_023548323   707  SFKSIIEKEQVST-ADKD-LQSIVADLAGSPAIKKGILQSLKVVEELVSVMG-YPPQTIVVEMARENQ TTNKGKNNS  780
WP_031665337   707  SFKSIIEKEQVST-TDKD-LQSIVAELAGSPAIKKGILQSLKIVDELVSIMG-YPPQTIVVEMARENQ TTNKGKNNS  780
WP_031669209   707  SFKSIIEKEQVST-ADKD-LQSIVADLAGSPAIKKGILQSLKIVDELVSIMG-YPPQTIVVEMARENQ TTGKGKNNS  780
WP_033920898   707  SFKSIIEKEQVST-ADKD-LQSIVADLAGSPAIKKGILQSLKIVDELVSIMG-YPPQTIVVEMARENQ TTGKGKNNS  780
AKI42028       710  SFKSIIEKEQVST-ADKD-LQSIVADLAGSPAIKKGILQSLKVVEELVSVMG-YPPQTIVVEMARENQ TTGKGKNNS  783
AKI50529       710  SFKSIIEKEQVST-ADKD-LQSIVADLAGSPAIKKGILQSLKVVEELVSIMG-YPPQTIVVEMARENQ TTGKGKNNS  783
EFR83390       155  SFKSIIEKEQVST-ADKD-IQSIVADLAGSPAIKKGILQSLKIVDELVGIMG-YPPQTIVVEMARENQ TTVKGKNNS  228
WP_046323366   707  SFKSIIEKEQVST-ADKD-LQSIVADLAGSPAIKKGILQSLKIVDELVSVMG-YPPQTIVVEMARENQ TTGKGKNNS  780
AKE81011       719  TFKEDIQKAQVSG-QGDS-LHEHIANLAGSPAIKKGILQTVKVVDELVKVMGrHKPENIVIEMARENQ TTQKGQKNS  793
CUO82355       710  GYAQMIEEASSCPkDGKF-TYEEVAKLAGSPALKRGIWQSLQIVEEITKVMK-CRPKYIYIEFERSEE ------KERT  780
WP_033162887   713  GYKQIIEESNMQDiEGPF-KYDEVKKLAGSPAIKKGIWQALLVVREITKFMK-HEPSHIYIEFAREEQ ------KVRK  783
AGZ01981       736  TFKEDIQKAQVSG-QGDS-LHEHIANLAGSPAIKKGILQTVKVVDELVKVMGrHKPENIVIEMARENQ TTQKGQKNS  810
AKA60242       703  TFKEDIQKAQVSG-QGDS-LHEHIANLAGSPAIKKGILQTVKVVDELVKVMGrHKPENIVIEMARENQ TTQKGQKNS  777
AKS40380       703  TFKEDIQKAQVSG-QGDS-LHEHIANLAGSPAIKKGILQTVKVVDELVKVMGrHKPENIVIEMARENQ TTQKGQKNS  777
4UN5_B         707  TFKEDIQKAQVSG-QGDS-LHEHIANLAGSPAIKKGILQTVKVVDELVKVMGrHKPENIVIEMARENQ TTQKGQKNS  781
WP_010922251   778  RERMKRIEEGIK ELGS QILKEHP--VE---NTQLQNEKLYLYYLQNGRDMYYDQEL--D--INRLSDYDVDHI  841
WP_039695303   781  QQRLKKLQNSLK PSYI E---DK--VE---NSHLQNDQLFLYYIQNGKDMYTGDEL--D--IDHLSDYDIDHI  851
WP_045635197   776  QQRYKRIEDSLK ILAS NILKENP--TD---NNQLQNDRLFLYYLQNGKDMYTGEAL--D--INQLSYDIDHI  843
5AXW_A         488  KDAQKMINEMQK QTNE EIIRTTGk--E---NAKYLIEKILKHDMQGKCLYSLEAIpIEGilANNPNYEVDHI  561
WP_009880683   462  RERMKRIEEGIK ELGS DILKEYP--VE---NTQLQNEKLYLYYLQNGRDMYVDQEL--D--INRLSDYDVDHI  525
WP_010922251   778  RERMKRIEEGIK ELGS DILKEYP--VE---NTQLQNEKLYLYYLQNGRDMYVDQEL--D--INRLSDYDVDHI  841
WP_011054416   778  RERMKRIEEGIK ELGS DILKEYP--VE---NTQLQNEKLYLYYLQNGRDMYVDQEL--D--INRLSDYDVDHI  841
WP_011284745   778  RERMKRIEEGIK ELGS QILKEHP--VE---NTQLQNEKLYLYYLQNGRDMYVDQEL--D--INRLSDYDVDHI  841
WP_011285506   778  RERMKRIEEGIK ELGS QILKEHP--VE---NTQLQNEKLYLYYLQNGRDMYVDQEL--D--INRLSDYDVDHI  841
WP_011527619   778  RERMKRIEEGIK ELGS QILKEHP--VE---NTQLQNEKLYLYYLQNGRDMYVDQEL--D--INRLSDYDVDHI  841
WP_012560673   777  RERMKRIEEGIK ELGS DILKEYP--VE---TTQLQNEKLYLYYLQNGRDMYVDQEL--D--INRLSDYDVDHI  840
WP_014407541   778  RERMKRIEEGIK ELGS QILKEHP--VE---NTQLQNEKLYLYYLQNGRDMYVDQEL--D--INRLSDYDVDHI  841
WP_020905136   778  RERMKRIEEGIK ELGS QILKEHP--VE---NTQLQNEKLYLYYLQNGRDMYVDQEL--D--INRLSDYDVDHI  841
WP_023080005   777  RERMKRIEEGIK ELGS QILKEHP--VE---NTQLQNEKLYLYYLQNGRDMYVDQEL--D--INRLSDYDVDHI  840
WP_023610282   777  RERMKRIEEGIK ELGS QILKEHP--VE---NTQLQNEKLYLYYLQNGRDMYVDQEL--D--INRLSDYDVDHI  840
WP_030125963   778  RERMKRIEEGIK ELGS DILKEYP--VE---NTQLQNEKLYLYYLQNGRDMYVDQEL--D--INRLSDYDVDHI  841
WP_030126706   778  RERMKRIEEGIK ELGS DILKEYP--VE---NTQLQNEKLYLYYLQNGRDMYVDQEL--D--INRLSDYDVDHI  841
WP_031488318   778  RERMKRIEEGIK ELGS DILKEYP--VE---NTQLQNEKLYLYYLQNGRDMYVDQEL--D--INRLSDYDVDHI  841
WP_032460140   778  RERMKRIEEGIK ELGS DILKEYP--VE---NTQLQNEKLYLYYLQNGRDMYVDQEL--D--INRLSDYDVDHI  841
```

| ID | Start | Sequence | End |
|---|---|---|---|
| WP_032461047 | 778 | RERMKRIEEGIK ELGS DILKEYP-VE---NTQLQNEKLYLYYLQNGRDMVDQEL--D---INRLSDYDVDHI | 841 |
| WP_032462016 | 778 | RERMKRIEEGIK ELGS QILKEHP-VE---NTQLQNEKLYLYYLQNGRDMVDQEL--D---INRLSDYDVDHI | 841 |
| WP_032462936 | 778 | RERMKRIEEGIK ELGS DILKEYP-VE---NTQLQNEKLYLYYLQNGRDMVDQEL--D---INRLSDYDVDHI | 841 |
| WP_032464890 | 603 | RERMKRIEEGIK ELGS QILKEYP-VE---NTQLQNEKLYLYYLQNGRDMVDQEL--D---INRLSDYDVDHI | 666 |
| WP_033888930 | 778 | RERMKRIEEGIK ELGS DILKEYP-VE---NTQLQNEKLYLYYLQNGRDMVDQEL--D---INRLSDYDVDHI | 841 |
| WP_038431314 | 777 | RERMKRIEEGIK ELGS QILKEYP-VE---NTQLQNEKLYLYYLQNGRDMVDQEL--D---INRLSDYDVDHI | 840 |
| WP_038432938 | 778 | RERMKRIEEGIK ELGS DILKEYP-VE---NTQLQNEKLYLYYLQNGRDMVDQEL--D---INRLSDYDVDHI | 841 |
| WP_038434062 | 689 | RERMKRIEEGIK ELGS QILKEHP-VE---NTQLQNEKLYLYYLQNGRDMVDQEL--D---INRLSDYDVDHI | 752 |
| BAQ51233 | 1 | ------------ ---- --------------------------------QEL--D---INRLSGYDVDHI | 16 |
| KGE60162 | | | |
| KGE60856 | | | |
| WP_002989955 | 778 | RERMKRIEEGIK ELGS QILKEHP-VE---NTQLQNEKLYLYYLQNGRDMVDQEL--D---INRLSDYDVDHI | 841 |
| WP_003030002 | 778 | QQRLKLLQDSLK PVNI K----N--VE---NQQLQNDRLFLYIQNGKDMYTGETL--D---INNLSDYDIDHI | 840 |
| WP_003065552 | 781 | QQRLKKLQNSLK PSYI E---DK--VE---NSHLQNDQLFLYIQNGKDMYTGDEL--D---IDHLSDYDIDHI | 851 |
| WP_001040076 | 776 | RQRLTTLRESLA NLKS EKKPKYV-KDqveNHHLSDDRLFLYIQNGKDMYTDDEL--D---IDNLSQYDIDHI | 846 |
| WP_001040078 | 779 | RQRYKLLDDGVK NLAS NILKEYP-TD---NQALQNERLFLYIQNGKDMYTGEAL--D---IDNLSQYDIDHI | 846 |
| WP_001040080 | 779 | RQRYKLLDDGVK NLAS NILKEYP-TD---NQALQNERLFLYIQNGKDMYTGEAL--D---IDNLSQYDIDHI | 846 |
| WP_001040081 | 779 | RQRYKLLDDGVK NLAS NILKEYP-TD---NQALQNERLFLYIQNGKDMYTGEAL--D---IDNLSQYDIDHI | 846 |
| WP_001040083 | 779 | RQRYKLLDDGVK NLAS NILKEYP-TD---NQALQNERLFLYIQNGKDMYTGEAL--D---IDDLSQYDIDHI | 846 |
| WP_001040085 | 779 | RQRYKLLDDGVK NLAS NILKEYP-TD---NQALQNERLFLYIQNGKDMYTGEAL--D---IDNLSQYDIDHI | 846 |
| WP_001040087 | 779 | RQRYKLLDDGVK NLAS NILKEYP-TD---NQALQNERLFLYIQNGKDMYTGEAL--D---IDNLSQYDIDHI | 846 |
| WP_001040088 | 779 | RQRYKLLDDGVK NLAS NILKEYP-TD---NQALQNERLFLYIQNGKDMYTGEAL--D---IDNLSQYDIDHI | 846 |
| WP_001040089 | 779 | RQRYKLLDDGVK NLAS NILKEYP-TD---NQALQNERLFLYIQNGKDMYTGEAL--D---IDNLSQYDIDHI | 846 |
| WP_001040090 | 779 | RQRYKLLDDGVK NLAS NILKEYP-TD---NQALQNERLFLYIQNGKDMYTGEAL--D---IDNLSQYDIDHI | 846 |
| WP_001040091 | 779 | RQRYKLLDDGVK NLAS NILKEYP-TD---NQALQNERLFLYIQNGKDMYTGEAL--D---IDNLSQYDIDHI | 846 |
| WP_001040092 | 779 | RQRYKLLEDGVK NLAS DILKEYP-TD---NQALQNERLFLYIQNGKDMYTGEAL--D---IDNLSQYDIDHI | 846 |
| WP_001040094 | 776 | RQRLTTLRESLA NLKS EKKPKYV-KDqveNHHLSDDRLFLYIQNGKDMYTDDEL--D---IDNLSQYDIDHI | 846 |
| WP_001040095 | 776 | RQRLTTLRESLA NLKS EKKPKYV-KDqveNHHLSDDRLFLYIQNGKDMYTDDEL--D---IDNLSQYDIDHI | 846 |
| WP_001040096 | 776 | RQRLTTLRESLA NLKS EKKPKYV-KDqveNHHLSDDRLFLYIQNGKDMYTDDEL--D---IDNLSQYDIDHI | 846 |
| WP_001040097 | 779 | RQRYKLLDDGVK NLKS EKKPKYV-KDqveNHHLSDDRLFLYIQNGKDMYTDDEL--D---IDNLSQYDIDHI | 846 |
| WP_001040098 | 779 | RQRYKLLDDGVK NLAS NILKEYP-TD---NQALQNERLFLYIQNGKDMYTGEAL--D---IDNLSQYDIDHI | 846 |
| WP_001040099 | 779 | RQRYKLLDDGVK NLAS NILKEYP-TD---NQALQNERLFLYIQNGKDMYTGEAL--D---IDNLSQYDIDHI | 846 |
| WP_001040100 | 779 | RQRYKLLEDGVK NLAS NILKEYP-TD---NQALQNERLFLYIQNGKDMYTGEAL--D---IDNLSQYDIDHI | 846 |
| WP_001040104 | 776 | RQRLTTLRESLA NLKS EKKPKYV-KDqveNHHLSDDRLFLYIQNGKDMYTGEAL--D---IDNLSQYDIDHI | 846 |
| WP_001040105 | 779 | RQRYKLLDDGVK NLAS NILKEYP-TD---NQALQNERLFLYIQNGKDMYTGEAL--D---IDNLSQYDIDHI | 846 |
| WP_001040106 | 779 | RQRYKLLEEGVK NLAS NILKEYP-TD---NQALQNERLFLYIQNGKDMYTGEAL--D---IDNLSQYDIDHI | 846 |
| WP_001040107 | 779 | RQRYKLLEEGVK NLAS NILKEYP-TD---NQALQNERLFLYIQNGKDMYTGEAL--D---IDNLSQYDIDHI | 846 |
| WP_001040108 | 779 | RQRYKLLDDGVK NLAS NILKEYP-TD---NQALQNERLFLYIQNGKDMYTGETL--D---IDNLSQYDIDHI | 846 |
| WP_001040109 | 779 | RQRYKLLEEGVK NLAS NILKEYP-TD---NQALQNERLFLYIQNGKDMYTGEAL--D---IDNLSQYDIDHI | 846 |
| WP_001040110 | 779 | RQRYKLLDDGVK NLAS DILKEYP-TD---NQALQNERLFLYIQNGKDMYTGEAL--D---IDNLSQYDIDHI | 846 |
| WP_015058523 | 779 | RQRYKLLEEGVK NLAS NILKEYP-TD---NQALQNERLFLYIQNGKDMYTGEAL--D---IDNLSQYDIDHI | 846 |
| WP_017643650 | 776 | RQRLTTLRESLA NLKS EKKPKYV-KDqveNHHLSDDRLFLYIQNGKDMYTGEAL--D---IDNLSQYDIDHI | 846 |
| WP_017647151 | 779 | RQRYKLLDDGVK NLAS NILKEYP-TD---NQALQNERLFLYIQNGKDMYTGKAL--D---IDNLSQYDIDHI | 846 |
| WP_017648376 | 779 | RQRYKLLDDGVK NLAS NILKEYP-TD---NQALQNERLFLYIQNGKDMYTGEAL--D---IDNLSQYDIDHI | 846 |
| WP_017649527 | 779 | RQRYKLLEEGVK NLAS NILKEYP-TD---NQALQNERLFLYIQNGKDMYTGEAL--D---IDNLSQYDIDHI | 846 |
| WP_017771611 | 779 | RQRYKLLEEGVK NLAS NILKEYP-TD---NQALQNERLFLYIQNGKDMYTGEAL--D---IDNLSQYDIDHI | 846 |
| WP_017771984 | 779 | RQRYKLLDDGVK NLAS NILKEYP-TD---NQALQNERLFLYIQNGKDMYTGEAL--D---IDNLSQYDIDHI | 846 |
| CFQ25032 | 779 | RQRYKLLDDGVK NLAS NILKEYP-TD---NQALQNERLFLYIQNGKDMYTGEAL--D---IDNLSQYDIDHI | 846 |
| CFV16040 | 779 | RQRYKLLDDGVK NLAS NILKEYP-TD---NQALQNERLFLYIQNGKDMYTGEAL--D---IDNLSQYDIDLI | 846 |
| KLJ37842 | 779 | RQRYKLLDDGVK NLAS NILKEYP-TD---NQALQNERLFLYIQNGKDMYTGEAL--D---IDNLSQYDIDHI | 846 |
| KLJ72361 | 779 | RQRYKLLDDGVK NLAS NILKEYP-TD---NQALQNERLFLYIQNGKDMYTGEAL--D---IDNLSQYDIDHI | 846 |
| KLL20707 | 793 | RQRYKLLDDGVK NLAS NILKEYP-TD---NQALQNERLFLYIQNGKDMYTGEAL--D---IDNLSQYDIDHI | 860 |
| KLL42645 | 779 | RQRYKLLEEGVK NLAS NILKEYP-TD---NQALQNERLFLYIQNGKDMYTGEAL--D---IDNLSQYDIDHI | 846 |

```
WP_047202273  RQRYKLLDDGVK NLAS NILKEYP-TD---NQALQNERLFLYYLQNGRDMYTGEAL--D--IDNLSQYDIDHI  846
WP_047209694  RQRLTTLRESLA NLKS EKKPKYV-KDqveNHHLSDDRLFLYYLQNGKDMYTDDEL--D--IDNLSQYDIDHI  846
WP_050198062  RQRYKLLDDGVK NLAS NILKEYP-TD---NQALQNERLFLYYLQNGRDMYTGEAL--D--IDNLSQYDIDHI  846
WP_050201642  RQRYKLLDDGVK NLAS NILKEYP-TD---NQALQNERLFLYYLQNGRDMYTGEAL--D--IDNLSQYDIDHI  846
WP_050204027  RQRYKLLEEGVK NLAS NILKEYP-TD---NQALQNERLFLYYLQNGRDMYTGEAL--D--IDNLSQYDIDHI  846
WP_050811965  RQRYKLLDDGVK NLAS NILKEYP-TD---NQALQNERLFLYYLQNGRDMYTGEAL--D--IDNLSQYDIDHI  846
WP_050886065  RQRYKLLDDGVK NLAS NILKEYP-TD---NQALQNERLFLYYLQNGRDMYTGEAL--D--IDNLSQYDIDHI  846
AHN30376      RQRYKLLEDGVK NLAS DILKEYP-TD---NQALQNERLFLYYLQNGRDMYTGEAL--D--IDSLSQYDIDHI  846
EA078426      RQRYKLLDDGVK NLAS NILKEYP-TD---NQALQNERLFLYYLQNGRDMYTEKAL--D--IDNLSQYDIDHI  846
CCW42055      RQRYKLLDDGVR NLAS NILKEYP-TD---NQALQNERLFLYYLQNGRDMYTGETL--D--INNLSQYDIDHI  846
WP_003041502  QQRLKLLQDSLK PVNI K------N--VE---NQQLQNDRLFLYIQNGKDMYTGETL--D--INNLSQYDIDHI  840
WP_037593752  QQRLKLLQDSLK PVNI K------N--VE---NQQLQNDRLFLYIQNGKDMYTGEEL--D--INNLSQYDIDHI  841
WP_049516684  QQRLKLLQDSLK PVNI K------N--VE---NQQLQNDRLFLYIQNGKDMYTGETL--D--INNLSQYDIDHI  841
GAD46167      QQRLKLLQDSLK PVSI K------N--VE---NQQLQNDRLFLYIQNGKDMYTGETL--D--IDNLSQYDIDHI  840
WP_018363470  RERKKRIEGIK  ELES QILKENP-E---DK--VE---NSHLQNDQLFLYIQNGKDMYTGDEL--D--IDHLSDYDVDHI  849
WP_003043819  RERKKRIEGIK  ELES QILKENP-E-------VE---NTQLQNEKLYLYYLQNGRDMYVDQEL--D--INRLSDYDVDHI  850
WP_006269658  QQRLKLLQDSLK PVNI K------N--VE---NQQLQNDRLFLYIQNGKDMYVDQEL--D--INNLSQYDIDHI  840
WP_048800889  QQRLKLLQDSLT PVSI K------N--VE---NQQLQNDRLFLYIQNGKDMYTGETL--D--IHHLSDYDIDHI  840
WP_012767106  RERMKRIEGIK  ELGS QILKEHP-------VE---NTQLQNEKLYLYYLQNGRDMYVDQEL--D--INRLSDYDVDHI  840
WP_014612333  RERMKRIEGIK  ELGS QILKEHP-------VE---NTQLQNEKLYLYYLQNGRDMYVDQEL--D--INRLSDYDVDHI  840
WP_015017095  RERMKRIEGIK  ELGS QILKEHP-------VE---NTQLQNDRLYLYYLQNGRDMYVDQEL--D--INRLSDYDVDHI  840
WP_015057649  RERMKRIEGIK  ELGS QILKEHP-------VE---NTQLQNDRLYLYYLQNGRDMYVDQEL--D--IDYLSDYDVDHI  840
WP_048277215  RERMKRIEGIK  ELGS QILKEHP-------VE---NTQLQNDRLFLYYLQNGRDMYVDQEL--D--IDYLSDYDVDHI  840
WP_049519324  RQRMRKLEETAK KLGS NILKEHP-------VD---NSQLQNDKRYLYYLQNGRDMYTGDDL--D--IDYLSSYDIDHI  840
WP_012515931  RQRMRKLEETAK KLGS NILKEHP-------VD---NSQLQNDKRYLYYLQNGRDMYTGDDL--D--IDYLSSYDIDHI  840
WP_021320964  RQRMRKLEETAK KLGS NILKEHP-------VD---NSHLQNDQLFLYYLQNGKDMYTGDDL--D--IDHLSDYDIDHI  840
WP_037581760  NQRLKRLQDSLK PSYV D------SK--VE---NSHLQNDQLFLYYLQNGKDMYTGDEL--D--IDRLSDYDIDHI  848
WP_009854540  RQRLKKLQSSLK PSYI E------DK--VE---NSHLQNDQLFLYYLQNGKDMYTGDEL--D--IDHLSDYDIDHI  849
WP_012962174  QQRLKKLQDSLK PSYI E------GK--VE---NSHLQNDQLFLYYLQNGKDMYTGDEL--D--IDRLSDYDIDHI  849
WP_039699303  NQRLKRLQDSLK PSYV D------SK--VE---NSHLQNDRLFLYYLQNGKDMYTGEEL--D--INQLSSYDIDHI  851
WP_014334983  RQRLKLEEVHK NTGS KILKEYN-VS----NTQLQSDRLYLYLLQDGKDMYTGKEL--D--YDNLSQYDIDHI  848
WP_003099269  RQRLKLEEVHK NTGS KILKEYN-VS----NTQLQSDRLYLYLLQDGKDMYTGKEL--D--YDNLSQYDIDHI  841
AHY15608      RQRLRKLEEVHK NTGS KILKEYN-VS----NTQLQSDRLFLYLYLLQDGKDMYTGKEL--D--YDNLSQYDIDHI  841
AHY17476      -----------  ----  ---------    ------------------------------  ---  -----------
ESR09100      RQRLRKLEVHK NTGS KILKEYN-VS----NTQLQSDRLFLYYLQNGKDMYTGEEL--D--IDYLSQYDIDHI  841
AGM98575      QQRLKGLTDSIK EFGS -LGS---DLLKQNP-IQd--NKDLQKEKLFLYYMQNGIDLYTGQPlncD--PDSLAFYDVDHI  857
ALF27331      AQRLKKIEDGIK NLAH NILKEHP-TD----NIQLQNDRLFLYYQNGKDMYTGKSL--D--INQLSSCDIDHI  844
WP_018372492  QQRYKRIEDALK ILAS NILKEHP-VE---NNQLQNDRLFLYYLQNGKDMYTGEAL--D--INQLSSYDIDHI  843
WP_045618028  QQRLKGLTDSIK EFGS NILKEHP-VE---NSQLQNDRLFLYYLQNGKDMYTGEEL--D--IDYLSQYDIDHI  841
WP_045635197  QQRLKGLTDSIK EFGS QILKEHP-VE---NSQLQNDRLFLYYLQNGKDMYTGEEL--D--IDYLSQYDIDHI  841
WP_002263549  QQRLKGLTDSIK EFGS QILKEHP-VE---NSQLQNDRLFLYYLQNGKDMYTGEEL--D--IDYLSQYDIDHI  841
WP_002263887  QQRLKGLTDSIK EFGS QILKEHP-VE---NSQLQNDRLFLYYLQNGKDMYTGEEL--D--IDYLSQYDIDHI  841
WP_002264920  QQRLKGLTDSIK EFGS QILKEHP-VE---NSQLQNDRLFLYYLQNGKDMYTGEEL--D--IDYLSQYDIDHI  841
WP_002269043  QQRLKGLTDSIK EFGS QILKEHP-VE---NSQLQNDRLFLYYLQNGKDMYTGEEL--D--IDYLSQYDIDHI  841
WP_002269448  QQRLKGLTDSIK EFGS QILKEHP-VE---NSQLQNDRLFLYYLQNGKDMYTGEEL--D--IDYLSQYDIDHI  841
WP_002271977  QQRLKGLTDSIK EFGS QILKEHP-VE---NSQLQNDRLFLYYLQNGKDMYTGEEL--D--IDYLSQYDIDHI  841
WP_002272766  QQRLKGLTDSIK EFGS QILKEHP-VE---NSQLQNDRLFLYYLQNGKDMYTGEEL--D--IDYLSQYDIDHI  841
WP_002273241  QQRLKGLTDSIK EFGS QILKEHP-VE---NSQLQNDRLFLYYLQNGKDMYTGEEL--D--IDYLSQYDIDHI  841
WP_002275430  QQRLKGLTDSIK EFGS QILKEHP-VE---NSQLQNDRLFLYYLQNGKDMYTGEEL--D--IDYLSQYDIDHI  841
WP_002276448  QQRLKGLTDSIK EFGS QILKEHP-VE---NSQLQNDRLFLYYLQNGKDMYTGEEL--D--IDYLSQYDIDHI  841
WP_002277050  QQRLKRLKEAIK DLNH KILKEHP-TD---NQALQNNRLFLYYLQNGRDMYTGESL--D--INRLSDYDIDHV  846
WP_002277364  QQRLKGLTDSIK EFGS QILKEHP-VE---HSQLQNDRLFLYYLQNGKDMYTGEEL--D--IDYLSQYDIDHI  841
```

```
WP_002279025  778 QQRLKGLTDSIK EFGS QILKEHP-VE--NSQLQNDRLFLYYLQNGRDMYTGEEL--D--IDYLSQYDIDHI  841
WP_002279859  778 QQRLKGLTDSIK EFGS QILKEHP-VE--NSQLQNDRLFLYYLQNGRDMYTGEEL--D--IDYLSQYDIDHI  841
WP_002280230  778 QQRLKGLTDSIK EFGS QILKEHP-VE--NSQLQNDRLFLYYLQNGRDMYTGEEL--D--IDYLSQYDIDHI  841
WP_002281696  778 QQRLKGLTDSIK DLNH KILKEHP-TD--NQALQNDRLFLYYLQNGRDMYTGEEL--D--INRLSDYDIDHV  846
WP_002282247  779 QQRYKRLKEAIK EFGS QILKEHP-VE--NSQLQNDRLFLYYLQNGRDMYTGEEL--D--IDYLSQYDIDHI  841
WP_002282906  778 QQRLKGLTDSIK EFGS QILKEHP-VE--NSQLQNDRLFLYYLQNGRDMYTGEEL--D--IDYLSQYDIDHI  841
WP_002283846  778 QQRLKGLTDSIK EFGS QILKEHP-VE--NSQLQNDRLFLYYLQNGRDMYTGEEL--D--IDYLSQYDIDHI  841
WP_002287255  778 QQRLKGLTDSIK EFGS QILKEHP-VE--HSQLQNDRLFLYYLQNGRDMYTGEEL--D--IDYLSQYDIDHI  841
WP_002288990  778 QQRLKGLTDSIK EFGS QILKEHP-VE--NSQLQNDRLFLYYLQNGRDMYTGEEL--D--IDYLSQYDIDHI  841
WP_002289641  778 QQRLKGLTDSIK EFGS QILKEHP-VE--NSQLQNDRLFLYYLQNGRDMYTGEEL--D--IDYLSQYDIDHI  841
WP_002290427  778 QQRLKGLTDSIK EFGS QILKEHP-VE--NSQLQNDRLFLYYLQNGRDMYTGEEL--D--IDYLSQYDIDHI  841
WP_002295753  778 QQRLKGLTDSIK EFGS QILKEHP-VE--NSQLQNDRLFLYYLQNGRDMYTGEEL--D--IDYLSQYDIDHI  841
WP_002296423  778 QKRYKRLEEAIK DLNH KILKEHP-TD--NQALQNDRLFLYYLQNGRDMYTEDPL--D--INRLSDYDIDHI  855
WP_002304487  788 QQRLKGLTDSIK EFGS QILKEHP-VE--NSQLQNDRLFLYYLQNGRDMYTGEEL--D--IDYLSQYDIDHI  841
WP_002305844  778 QQRLKGLTDSIK EFGS QILKEHP-VE--NSQLQNDRLFLYYLQNGRDMYTGEEL--D--IDYLSQYDIDHI  841
WP_002307203  778 QQRLKGLTDSIK EFGS QILKEHP-VE--NSQLQNDRLFLYYLQNGRDMYTGEEL--D--IDYLSQYDIDHI  841
WP_002310390  778 QQRLKGLTDSIK EFGS QILKEHP-VE--NSQLQNDRLFLYYLQNGRDMYTGEEL--D--IDYLSQYDIDHI  841
WP_002352408  778 QQRLKGLTDSIK EFGS QILKEHP-VE--NSQLQNDRLFLYYLQNGRDMYTGEEL--D--IDYLSQYDIDHI  841
WP_012997688  778 QQRLKGLTDSIK EFGS QILKEHP-VK--NSQLQNDRLFLYYLQNGRDMYTGEEL--D--IDYLSQYDIDHI  841
WP_014677909  778 QQRLKGLTDSIK EFGS QILKEHP-VE--HSQLQNDRLFLYYLQNGRDMYTGEEL--D--IDYLSQYDIDHI  841
WP_019312892  778 QQRLKGLTDSIK EFGS QILKEHP-VE--NSQLQNDRLFLYYLQNGRDMYTGEEL--D--IDYLSQYDIDHI  841
WP_019313659  778 QQRLKGLTDSIK EFGS QILKEHP-VE--NSQLQNDRLFLYYLQNGRDMYTGESL--D--IDYLSQYDIDHI  841
WP_019314093  778 QQRLKGLTDSIK EFGS QILKEHP-VE--NSQLQNDRLFLYYLQNGRDMYTGEEL--D--INRLSDYDIDHV  841
WP_019315370  778 QQRLKGLTDSIK EFGS QILKEHP-VE--NSQLQNDRLFLYYLQNGRDMYTGEEL--D--IDYLSQYDIDHI  841
WP_019803776  778 QQRLKGLTDSIK DLNH KILKEHP-TD--NQALQNDRLFLYYLQNGRDMYTGEEL--D--IDYLSQYDIDHI  846
WP_019805234  778 QQRLKGLTDSIK EFGS QILKEHP-VE--NSQLQNDRLFLYYLQNGRDMYTGEEL--D--IDYLSQYDIDHI  841
WP_024783594  778 QQRLKGLTDSIK EFGS QILKEHP-VE--NSQLQNDRLFLYYLQNGRDMYTGEEL--D--IDYLSQYDIDHI  841
WP_024784288  779 QQRLKRLKEAIK DLNH KILKEHP-TD--NQALQNDRLFLYYLQNGRDMYTGESL--D--INRLSDYDIDHV  846
WP_024784666  778 QQRLKGLTDSIK EFGS QILKEHP-VE--NSQLQNDRLFLYYLQNGRDMYTGEEL--D--IDYLSQYDIDHI  841
WP_024784894  778 QQRLKGLTDSIK EFGS QILKEHP-VE--HSQLQNDRLFLYYLQNGRDMYTGEEL--D--IDYLSQYDIDHI  841
WP_024786433  778 QQRLKGLTDSIK EFGS QILKEHP-VE--NSQLQNDRLFLYYLQNGRDMYTGEEL--D--INRLSDYDIDHV  846
WP_049473442  779 QQRLKRLKEAIK DLNH KILKEHP-TD--NQALQNDRLFLYYLQNGRDMYTGEEL--D--INRLSDYDIDHV  841
WP_049474547  778 QQRLKGLTDSIK EFGS QILKEHP-VE--NSQLQNDRLFLYYLQNGRDMYTGEEL--D--IDYLSQYDIDHI  841
EMC03581      771 RERLRKLEEVHK NIGS KILKEHE-IS--NAQLQSDRVYLYLLQDGKDMYTGKDL--D--ISNLSHYDIDHI  834
WP_000428612  779 QQRYKRIEDSLK NLAS KILKEHP-TD--NIQLQNDRLFLYYLQNGKDMYTGKPL--D--INQLSSYDIDHI  846
WP_000428613  777 QQRYKRIEDALK NLAS NILKEHP-TN--NIQLQNDRLFLYYLQNGKDMYTGKPL--D--INQLSSYDIDHI  844
WP_049523028  776 QQRLKTLSDAIS ELG- NILKEHP-TD--NIQLQNDRLFLYYLQNGKDMYTGEAL--D--INQLSNYDIDHI  839
WP_003107102  747 RERLRKLEEVHK NIGS KILKEHE-IS--NAQLQSDRVYLYLLQDGKDMYTGKDL--D--FDRLSQYDIDHI  810
WP_054279288  779 RERMKRVQEVLK KLGS QLLKEHP-VE--NFQLQNDQLYLYLYLQNGKDMYTGEEL--S--ISNLSHYDIDHI  842
WP_049531101  777 QQRYKRIEDSLK ILAS NILKEHP-TD--NNQLQNDRLFLYYLQNGKDMYTGNPL--D--INHLSSYDIDHI  844
WP_049538452  777 QQRYKRIENSLK ILAS NILKEHP-TD--NNQLQNDRLFLYYLQNGKDMYTGEAL--D--INQLSSCDIDHI  844
WP_049549711  778 QQRYKRIEDSLK ILAS NILKEHP-VE--NSQLQNDRLFLYYLQNGKDMYTGEAL--D--INQLSSYDIDHI  846
WP_007896501  781 RQRLKKIKEVHK KTGS RILEDNSerIT--NLTLQDNRLYLYLLQDGKDMYTGQDL--D--INNLSQYDIDHI  846
EFR44625      733 RQRLKKIKEVHK KTGS RILEDNSerIT--NLTLQDNRLYLYLLQDGKDMYTGQDL--D--INNLSQYDIDHI  798
WP_002974477  776 QQRYKRIEDALK NLAP NILKEHP-TD--NIQLQNDRLFLYYLQNGKDMYTGKPL--D--INQLSSYDIDHI  843
WP_002906454  777 QQRYKRIEDALK NLAP NILKEHP-TD--NIQLQNDRLFLYYLQNGKDMYTGKAI--D--INQLSNYDIDHI  844
WP_009729476  780 QQRYKRIEDSLK ILAS KILKEHP-TD--NIQLQNDRLFLYYLQNGKDMYTGEAL--D--INQLSSCDIDHI  843
CQR24647      779 QQRIGSLITKAIQ DFGS DILKRYP-VE--NNQLQNDQLYLYLYLQNGKDMYTGDTL--D--INHLSQYDIDHI  844
WP_009754323  777 QQRLKRIEDSLK NLAS NILKEHP-TD--NIQLQNDRLFLYYLQNGKDMYTGKPL--E--INQLSNYDIDHI  846
WP_044674937  776 QQRYKKIENAIK NLNS KILKEYP-TN--NQALQNDRLFLYYLQNGKDMYTDEEL--D--IDQLSQYDIDHI  843
WP_044676715  778 QQRYKKIENAIK NLNS KILKEYP-TN--NQALQNDRLFLYYLQNGKDMYTDEEL--D--IDQLSQYDIDHI  845
WP_044680361  778 QQRYKKIENAIK NLNS KILKEYP-TN--NQALQNDRLFLYYLQNGKDMYTDEEL--D--IDQLSQYDIDHI  845
```

```
                                                          -continued

WP_044681799   776 QQRYKKIENAIK NLNS KILKEYP-TN---NQALQNDRLFLYYLQNGKDMYTDEEL--D---IDQLSQYDIDHI 843
WP_049533112   778 QQRLKLLQDSLK PVNI K-----N--VE---NQQLQNDRLFLYYIQNGKDMYTGETL--D---INNLSQYDIDHI 840
WP_029090905   753 TPRDKFIEKAYA ETDT EHLKELK---Qr--SKQLSSQRLFLYFIQNGKDMYTGEHL--D---IERLDSYEVDHI 823
WP_006506696   777 ESKIKKLENVYK DEQT SVLEELKg-FDn--TKKISSDSLFLYFTQLGKCMYSGKKL--D---IDSLDKYQIDHI 849
AIT42264       778 RERMKRIEEGIK ELGS QILKEHP-VE---NTQLQNEKLYLYLQNGRDMVDQEL--D---INRLSDYDVDHI 841
WP_034440723   785 KARLKKQEGLE NLDS HVEKQAL--D---EEMLKSPKYYLYCLQNGKDIYTGKDL--D---IGQLQTYDIDHI 848
AKQ21048       778 RERMKRIEEGIK ELGS QILKEHP-VE---NTQLQNEKLYLYLQNGRDMVDQEL--D---INRLSDYDVDHI 841
WP_004636532   781 KERIEKLTEAIK EFDG --VKVKD--LK---NENLRNDRLYLYYLQNGRDMYTNEPL--D---INNLSKYDIDHI 845
WP_002364836   789 IQRLKIVEKAMA EIGS NLLKEQP-TT---NEQLRDTRLFLYYMQNGKDMYTGDEL--S---LHRLSHYDIDHI 852
WP_016663044   740 IQRLKIVEKAMA EIGS NLLKEQP-TT---NEQLRDTRLFLYYIQNGKDMYTGDEL--S---LHRLSHYDIDHI 803
EMS75795       525 KPRLKALEEALK SFDS PLLKEQP-VD---NQALQDRLYLYLQNGKDMYTGEAL--D---IDRLSEYDIDHI 588
WP_002373311   789 IQRLKIVEKAMA EIGS NLLKEQP-TT---NEQLRDTRLFLYYMQNGKDMYTGDEL--S---LHRLSHYDIDHI 852
WP_033789179   789 IQRLKIVEKAMA EIGS NLLKEQP-TT---NEQLRDTRLFLYYMQNGKDMYTGDEL--S---LHRLSHYDIDHI 852
WP_002378009   789 IQRLKIVEKAMA EIGS NLLKEQP-TT---NEQLRDTRLFLYYMQNGKDMYTGDEL--S---LHRLSHYDIDHI 852
WP_002407324   789 IQRLKIVEKAMA EIGS NLLKEQP-TT---NEQLRDTRLFLYYMQNGKDMYTGDEL--S---LHRLSHYDIDHI 852
WP_002413717   789 IQRLKIVEKAMA EIGS NLLKEQP-TT---NEQLRDTRLFLYYMQNGKDMYTGDEL--S---IHRLSHYDIDHI 852
WP_010775580   791 IQRLKIVEKAMA EIGS NLLKEQP-TT---NEQLRDTRLFLYYMQNGKDMYTGDEL--S---LHRLSHYDIDHI 854
WP_010818269   789 IQRLKIVEKAMA EIGS NLLKEQP-TT---NEQLRDTRLFLYYMQNGKDMYTGDEL--S---LHRLSHYDIDHI 852
WP_010824395   789 IQRLKIVEKAMA EIGS NLLKEQP-TT---NEQLRDTRLFLYYMQNGKDMYTGDEL--S---LHRLSHYDIDHI 852
WP_016622645   789 IQRLKIVEKAMA EIGS NLLKEQP-TT---NEQLRDTRLFLYYMQNGKDMYTGDEL--S---LHRLSHYDIDHI 852
WP_033624816   789 IQRLKIVEKAMA EIGS NLLKEQP-TT---NEQLRDTRLFLYYMQNGKDMYTGDEL--S---LHRLSHYDIDHI 852
WP_033625576   789 IQRLKIVEKAMA EIGS NLLKEQP-TT---NEQLRDTRLFLYYMQNGKDMYTGDEL--S---LHRLSHYDIDHI 852
WP_033789179   789 IQRLKIVEKAMA EIGS NLLKEQP-TT---NEQLRDTRLFLYYMQNGKDMYTGDEL--S---IHRLSDYDIDHI 852
WP_002310644   789 RPRLKALEESLK DFGS QLLKEYP-TD---NSSLQKDRLYLYLQNGRDMYTGAPL--D---IHRLSDYDIDHI 852
WP_002312694   790 RPRLKALEESLK DFGS QLLKEYP-TD---NSSLQKDRLYLYLQNGRDMYTGAPL--D---IHRLSDYDIDHI 853
WP_002314015   790 RPRLKALEESLK DFGS QLLKEYP-TD---NSSLQKDRLYLYLQNGRDMYTGAPL--D---IHRLSDYDIDHI 853
WP_002320716   790 RPRLKALEESLK DFGS QLLKEYP-TD---NSSLQKDRLYLYLQNGRDMYTGAPL--D---IHRLSDYDIDHI 853
WP_002330729   789 RPRLKALEESLK DFGS QLLKEYP-TD---NSSLQKDRLYLYLQNGRDMYTGAPL--D---IHRLSDYDIDHI 852
WP_002335161   790 RPRLKALEESLK DFGS QLLKEYP-TD---NSSLQKDRLYLYLQNGRDMYTGAPL--D---IHRLSDYDIDHI 853
WP_002345439   790 RPRLKALEESLK DFGS QLLKEYP-TD---NSSLQKDRLYLYLQNGRDMYTGAPL--D---IHRLSDYDIDHI 853
WP_034867970   781 SPRLKALENGLK QIGS TLLKEQP-TD---NKALQKERLYLYLQNGRDMYTGEPL--E---IENLHQYEVDHI 844
WP_047937432   790 KPRLKALEESLK QIGS QLLKEYP-TD---NSSLQKDRLYLYLQNGRDMYTGAPL--D---IHRLSDYDIDHI 853
WP_010720994   781 KPRLKALENGLK QIGS TLLKEQP-TD---NKALQKERLYLYLQNGRDMYTGEPL--E---IENLHQYEVDHI 844
WP_010737004   781 SPRLKALENGLK QIGS TLLKEQP-TD---NKALQKERLYLYLQNGRDMYTGEPL--E---IENLHQYEVDHI 844
WP_034700478   781 KPRLKALENGLK QIGS TLLKEQP-TD---NKALQKERLYLYLQNGRDMYTGEPL--E---IENLHQYEVDHI 844
WP_007209003   782 KPRLKGIENGLK EFSD SVLKGSS-ID---NKQLQNDRLYLYLQNGKDMYTGHEL--D---IDHLSTYDIDHI 845
WP_023519017   775 RPRLKALEEALK NIDS PLLKDYP-TD---NQALQDNRLYLYFLQNGKSLYSEESL--E---INKLSDYQVDHI 838
WP_010770040   782 NPRMKALEEAMR NLRS NLLKEYP-TD---NQALQNDRLYLYLQNGKDMYTGKEL--D---LHNLSSYDIDHI 845
WP_048604708   779 RPRLKNLEKAID DLDS EILKKHP-VD---NKALQKERLYLYLQNGKDMYTNEEL--D---IHKLSTYDIDHI 842
WP_010750235   784 KPRLKSLEEALK NFDS QLLKERP-VD---NQSLQKDRLYLYLQNGKDMYTGESL--D---IDRLSEYDIDHI 847
AII16583       817 RERMKRIEEGIK ELGS QILKEHP-VE---NTQLQNEKLYLYLQNGRDMVDQEL--D---INRLSDYDVDHI 880
WP_029073316   789 DSFVNQMLKLYK DFED EANKHLKg-EDa--KSKIRSERLKLYYTQMGKCMYTGKSL--D---IDRLDTYQVDHI 860
WP_031589969   789 DSFVNQMLKLYK DFED EANKHLKg-EDa--KSKIRSERLKLYYTQMGKCMYTGKSL--D---IDRLDTYQVDHI 860
KDA45870       772 EDRVQQIVKNLK ELPK ------P--S---NAELSDERKYLYCLQNGRDMYTGAPL--D---YDHLQFYDVDHI 833
WP_039099354   789 KRQVEQVVQNIS EL-- EIRNELK---D---LSSERIMYFLQNGKSLYSEESL--N---INKLSDYQVDHI 856
AKP02966       786 RLQSKLLNKANG -LVP EELKKHKn-D---LSSERIMYFLQNGKSLYSEESL--N---INKLSDYQVDHI 858
WP_010991369   781 RPRYKSLEKAIK EFGS QILKEHP-TD---NQELRNNRLYLYLYLQNGKDMYTGQDL--D---IHNLSNYDIDHI 844
WP_033838504   781 RPRYKSLEKAIK EFGS QILKEHP-TD---NQELRNNRLYLYLYLQNGKDMYTGQDL--D---IHNLSNYDIDHI 844
EHN60060       784 RPRYKSLEKAIK EFGS QILKEHP-TD---NQELRNNRLYLYLYLQNGKDMYTGQDL--D---LHNLSSYDIDHI 847
EFR89594       550 RPRYKSLEKAIK EFGS QILKEHP-TD---NQELRNNRLYLYLYLQNGKDMYTGQDL--D---IHNLSNYDIDHI 613
WP_038409211   781 KPRFISLEKAIK EFGS QILKEHP-TD---NQCLKNDRLYLYLYLQNGKDMYTGKEL--D---IHNLSNYDIDHI 844
EFR95520       400 KPRFISLEKAIK EFGS QILKEHP-TD---NQCLKNDRLYLYLYLQNGKDMYTGKEL--D---IHNLSNYDIDHI 463
WP_003723650   781 KPRYKSLEKAIK EFGS QILKEHP-TD---NQELKNNRLYLYLYLQNGKDMYTGQEL--D---IHNLSNYDIDHI 844
WP_003727705   781 KPRYKSLEKAIK DFGS QILKEHP-TD---NQELKNNRLYLYLYLQNGKDIYTGQEL--D---IHNLSNYDIDHI 844
```

-continued

| | | | |
|---|---|---|---|
| WP_003730785 | 781 | KPRYKSLEKAIK DFGS QILKEHP--TD---NQELKNNRLYLYYLQNGKDIYTGQEL--D--IHNLSNYDIDHI | 844 |
| WP_003733029 | 781 | KPRYKSLEKAIK EFGS QILKEHP--TD---NQELKNNRLYLYYLQNGKDMYTGQEL--D--IHNLSNYDIDHI | 844 |
| WP_003739838 | 781 | RPRYKSLEKAIK EFGS QILKEHP--TD---NQELRNNRLYLYYLQNGKDMYTGQEL--D--IHNLSNYDIDHI | 844 |
| WP_014601172 | 781 | KPRYKSLEKAIK EFGS KILKEHP--TD---NQELKNNRLYLYYLQNGKDMYTGQEL--D--IHNLSNYDIDHI | 844 |
| WP_023548323 | 781 | KPRYKSLEKAIK EFGS QILKEHP--TD---NQELKNNRLYLYYLQNGKDMYTGQEL--D--IHNLSNYDIDHI | 844 |
| WP_031665337 | 781 | KPRYKSLEKAIK EFGS QILKEHP--TD---NQELKNNRLYLYYLQNGKDMYTGQEL--D--IHNLSNYDIDHI | 844 |
| WP_031669209 | 781 | KPRYKSLEKAIK EFGS QILKEHP--TD---NQELKNNRLYLYYLQNGKDMYTGQEL--D--IHNLSNYDIDHI | 844 |
| WP_033920898 | 781 | KPRYKSLEKAIK EFGS QILKEHP--TD---NQELKNNRLYLYYLQNGKDMYTGQEL--D--IHNLSNYDIDHI | 844 |
| AKI42028 | 784 | KPRYKSLEKAIK EFGS KILKEHP--TD---NQELKNNRLYLYYLQNGKDMYTGQEL--D--IHNLSNYDIDHI | 847 |
| AKI50529 | 784 | KPRYKSLEKAIK EFGS QILKEHP--TD---NQELKNNRLYLYYLQNGKDMYTGQEL--D--IHNLSNYDIDHI | 847 |
| EFR83390 | 229 | RPRYKSLEKAIK EFGS QILKEHP--TD---NQELKNNRLYLYYLQNGKDIYTGQEL--D--IHNLSNYDIDHI | 292 |
| WP_046323366 | 781 | KPRFTSLEKAIK ELGS QILKEHP--TD---NQGLKNDRLYLYYLQNGKDMYTGQEL--D--IHNLSNYDIDHV | 844 |
| AKE81011 | 794 | RERMKRIEEGIK ELGS QILKEHP--VE---NTQLQNEKLYLYYLQNGRDMYVDQEL--D--INRLSDYDVDHI | 857 |
| CUO82355 | 781 | ESKIKKLENVYK DEQT SVLEELKg-FDn--TKKISSDSLFLYFTQLGKCMYSGKKL--D--IDSLDKYQIDHI | 853 |
| WP_033162887 | 784 | ESKIAKLQKIYE NLQT QVYESLKk-EDa--KKRMETDALYLYYLQMGKSMYSGKPL--D--IDKLSTYQIDHI | 855 |
| AGZ01981 | 811 | RERMKRIEEGIK ELGS QILKEHP--VE---NTQLQNEKLYLYYLQNGRDMYVDQEL--D--INRLSDYDVDHI | 874 |
| AKA60242 | 778 | RERMKRIEEGIK ELGS QILKEHP--VE---NTQLQNEKLYLYYLQNGRDMYVDQEL--D--INRLSDYDVDAI | 841 |
| AKS40380 | 778 | RERMKRIEEGIK ELGS QILKEHP--VE---NTQLQNEKLYLYYLQNGRDMYVDQEL--D--INRLSDYDVDHI | 841 |
| 4UN5_B | 782 | RERMKRIEEGIK ELGS QILKEHP--VE---NTQLQNEKLYLYYLQNGRDMYVDQEL--D--INRLSDYDVDAI | 845 |
| WP_010922251 | 842 | VPQSFLKDDSIDNKVLTRSDKNRG-KSDN--VP S--EEVVKKMKN-YWRQLLNAKLITQRKEDNLTKA--ERGGLSE | 910 |
| WP_039695303 | 852 | IPQAFIKDDSIDNRVLTSSAKNRG-KSDD--VP S--LDIVRARKA-EWVRLYKSGLISKRKFDNLTKA--ERGGLTE | 920 |
| WP_045635197 | 844 | IPQAFIKDDSLDNRVLTSSKDNRG-KSDN--VP S--IEVVQKRKA-FWQQLLDSKLISERKFNNLTKA--ERGGLDE | 912 |
| 5AXW_A | 562 | IPRSVSFDNSFNNKVLVKQEEASK-KGNR--TP Fqy-LSSSDSKI-SYETFKKHILNLAKGKGRISKTk-KEYLLEE | 632 |
| WP_009880683 | 526 | VPQSFLKDDSIDNKVLTRSDKNRG-KSDN--VP S--EEVVKKMKN-YWKQLLNAKLITQRKFDNLTKA--ERGGLSE | 594 |
| WP_010922251 | 842 | VPQSFLKDDSIDNKVLTRSDKNRG-KSDN--VP S--EEVVKKMKN-YWRQLLNAKLITQRKFDNLTKA--ERGGLSE | 910 |
| WP_011054416 | 842 | VPQSFLKDDSIDNKVLTRSDKNRG-KSDN--VP S--EEVVKKMKN-YWRQLLNAKLITQRKFDNLTKA--ERGGLSE | 910 |
| WP_011284745 | 842 | VPQSFIKDDSIDNKVLTRSDKNRG-KSNN--VP S--EEVVKKMKN-YWRQLLNAKLITQRKFDNLTKA--ERGGLSE | 910 |
| WP_011285506 | 842 | VPQSFLKDDSIDNKVLTRSDKNRG-KSDN--VP S--EEVVKKMKN-YWRQLLNAKLITQRKFDNLTKA--ERGGLSE | 910 |
| WP_011527619 | 842 | VPQSFIKDDSIDNKVLTRSDKNRG-KSDN--VP S--EEVVKKMKN-YWRQLLNAKLITQRKFDNLTKA--ERGGLSE | 910 |
| WP_012560673 | 842 | VPQSFLKDDSIDNKVLTRSDKNRG-KSDN--VP S--EEVVKKMKN-YWKQLLNAKLITQRKFDNLTKA--ERGGLSE | 910 |
| WP_014407541 | 841 | VPQSFIKDDSIDNKVLTRSDKNRG-KSDN--VP S--EEVVKKMKN-YWRQLLNAKLITQRKFDNLTKA--ERGGLSE | 909 |
| WP_020905136 | 842 | VPQSFIKDDSIDNKVLTRSDKNRG-KSDN--VP S--EEVVKKMKN-YWRQLLNAKLITQRKFDNLTKA--ERGGLSE | 910 |
| WP_023080005 | 841 | VPQSFLKDDSIDNKVLTRSDKNRG-KSDN--VP S--EEVVKKMKN-YWRQLLNAKLITQRKFDNLTKA--ERGGLSE | 909 |
| WP_023610282 | 841 | VPQSFLKDDSIDNKVLTRSDKNRG-KSDN--VP S--EEVVKKMKN-YWRQLLNAKLITQRKFDNLTKA--ERGGLSE | 909 |
| WP_030125963 | 842 | VPQSFIKDDSIDNKVLTRSDKNRG-KSDN--VP S--EEVVKKMKN-YWRQLLNAKLITQRKFDNLTKA--ERGGLSE | 910 |
| WP_030126706 | 842 | VPQSFLKDDSIDNKVLTRSDKNRG-KSDN--VP S--EEVVKKMKN-YWRQLLNAKLITQRKFDNLTKA--ERGGLSE | 910 |
| WP_031488318 | 842 | VPQSFIKDDSIDNKVLTRSDKNRG-KSDN--VP S--EEVVKKMKN-YWKQLLNAKLITQRKFDNLTKA--ERGGLSE | 910 |
| WP_032460140 | 842 | VPQSFLKDDSIDNKVLTRSDKNRG-KSDN--VP S--EEVVKKMKN-YWKQLLNAKLITQRKFDNLTKA--ERGGLSE | 910 |
| WP_032461047 | 842 | VPQSFLKDDSIDNKVLTRSDKNRG-KSDN--VP S--EEVVKKMKN-YWKQLLNAKLITQRKFDNLTKA--ERGGLSE | 910 |
| WP_032462016 | 842 | VPQSFLKDDSIDNKVLTRSDKNRG-KSDN--VP S--EEVVKKMKN-YWRQLLNAKLITQRKFDNLTKA--ERGGLSE | 910 |
| WP_032462936 | 842 | VPQSFLKDDSIDNKVLTRSDKNRG-KSDN--VP S--EEVVKKMKN-YWKQLLNAKLITQRKFDNLTKA--ERGGLSE | 910 |
| WP_032464890 | 842 | VPQSFIKDDSIDNKVLTRSDKNRG-KSDN--VP S--EEVVKKMKN-YWRQLLNAKLITQRKFDNLTKA--ERGGLSE | 910 |
| WP_033888930 | 667 | VPQSFLKDDSIDNKVLTRSDKNRG-KSDN--VP S--EEVVKKMKN-YWRQLLNAKLITQRKFDNLTKA--ERGGLSE | 735 |
| WP_038431314 | 842 | VPQSFLKDDSIDNKVLTRSDKNRG-KSDN--VP S--EEVVKKMKN-YWRQLLNAKLITQRKFDNLTKA--ERGGLSE | 910 |
| WP_038432938 | 841 | VPQSFLKDDSIDNKVLTRSDKNRG-KSDN--VP S--EEVVKKMKN-YWRQLLNAKLITQRKFDNLTKA--ERGGLSE | 909 |
| WP_038434062 | 842 | VPQSFLKDDSIDNKVLTRSDKNRG-KSDN--VP S--EEVVKKMKN-YWKQLLNAKLITQRKFDNLTKA--ERGGLSE | 910 |
| BAQ51233 | 753 | VPQSFLKDDSIDNKVLTRSDKNRG-KSDN--VP S--EEVVKKMKN-YWRQLLNAKLITQRKFDNLTKA--ERGGLSE | 821 |
| KGE60162 | 17 | VPQSFLKDDSIDNKVLTRSDKNRG-KSDN--VP S--EEVVKKMKN-YWRQLLNAKLITQRKFDNLTKA--ERGGLSE | 85 |
| KGE60856 | | --------------------------------- ------------------------------------------- | |
| WP_002989955 | 842 | VPQSFIKDDSIDNKVLTRSDKNRG-KSDN--VP S--EEVVKKMKN-YWRQLLNAKLITQRKFDNLTKA--ERGGLSE | 910 |
| WP_003030002 | 841 | IPQAFIKDNSLDNRVLTRSDKNRG-KSDD--VP S--IEVVHEMKS-FWSKLLSVKLITQRKFDNLTKA--ERGGLTE | 909 |
| WP_003065552 | 852 | IPQAFIKDDSIDNRVLTSSAKNRG-KSDD--VP S--LDIVRARKA-EWVRLYKSGLISKRKFDNLTKA--ERGGLTE | 920 |
| WP_001040076 | 847 | IPQAFIKDDSIDNRVLVSSAKNRG-KSDD--VP S--LEIVKDCKV-FWKKLLDAKLMSQRKYDNLTKA--ERGGLTS | 915 |

```
WP_001040078   847 IPQAFIKDDSIDNRVLVSSAKNRG-KSDD--VP-S--LEIVKDCKV-FWKKLLDAKLMSQRKYDNLTKA--ERGGLTS 915
WP_001040080   847 IPQAFIKDDSIDNRVLVSSAKNRG-KSDD--VP-S--LEIVKDCKV-FWKKLLDAKLMSQRKYDNLTKA--ERGGLTS 915
WP_001040081   847 IPQAFIKDDSIDNRVLVSSAKNRG-KSDD--VP-S--LEIVKDCKV-FWKKLLDAKLMSQRKYDNLTKA--ERGGLTS 915
WP_001040083   847 IPQAFIKDDSIDNRVLVSSAKNRG-KSDD--VP-S--LEIVKDCKV-FWKKLLDAKLMSQRKYDNLTKA--ERGGLTS 915
WP_001040085   847 IPQAFIKDDSIDNRVLVSSAKNRG-KSDD--VP-S--LEIVKDCKV-FWKKLLDAKLMSQRKYDNLTKA--ERGGLTS 915
WP_001040087   847 IPQAFIKDDSIDNRVLVSSAKNRG-KSDD--VP-S--LEIVKDCKV-FWKKLLDAKLMSQRKYDNLTKA--ERGGLTS 915
WP_001040088   847 IPQAFIKDDSIDNRVLVSSAKNRG-KSDD--VP-S--LEIVKDCKV-FWKKLLDAKLMSQRKYDNLTKA--ERGGLTS 915
WP_001040089   847 IPQAFIKDDSIDNRVLVSSAKNRG-KSDD--VP-S--LEIVKDCKV-FWKKLLDAKLMSQRKYDNLTKA--ERGGLTS 915
WP_001040090   847 IPQAFIKDDSIDNRVLVSSAKNRG-KSDD--VP-S--LEIVKDCKV-FWKKLLDAKLMSQRKYDNLTKA--ERGGLTS 915
WP_001040091   847 IPQAFIKDDSIDNRVLVSSAKNRG-KSDD--VP-S--LEIVKDCKV-FWKKLLDAKLMSQRKYDNLTKA--ERGGLTS 915
WP_001040092   847 VPQAFIKDDSIDNRVLVSSAKNRG-KSDD--VP-S--LEIVKDCKV-FWKKLLDAKLISQRKYDNLTKA--ERGGLTP 915
WP_001040094   847 IPQAFIKDDSIDNRVLVSSAKNRG-KSDD--VP-S--VEIVKDCKV-FWKKLLDAKLMSQRKYDNLTKA--ERGGLTS 915
WP_001040095   847 IPQAFIKDDSIDNRVLVSSAKNRG-KSDD--VP-S--LEIVKDCKV-FWKKLLDAKLMSQRKYDNLTKA--ERGGLTS 915
WP_001040096   847 IPQAFIKDDSIDNRVLVSSAKNRG-KSDD--VP-S--LEIVKDCKV-FWKKLLDAKLMSQRKYDNLTKA--ERGGLTS 915
WP_001040097   847 VPQAFIKDDSIDNRVLVSSAKNRG-KSDD--VP-S--VEIVKDCKV-FWKKLLDAKLMSQRKYDNLTKA--ERGGLTS 915
WP_001040098   847 VPQAFIKDDSIDNRVLVSSAKNRG-KSDD--VP-S--VEIVKDCKV-FWKKLLDAKLMSQRKYDNLTKA--ERGGLTS 915
WP_001040099   847 IPQAFIKDDSIDNRVLVSSAKNRG-KSDD--VP-S--LEIVKDCKV-FWKKLLDAKLMSQRKYDNLTKA--ERGGLTS 915
WP_001040100   847 IPQAFIKDDSIDNRVLVSSAKNRG-KSDD--VP-S--VEIVKDCKV-FWKKLLDAKLMSQRKYDNLTKA--ERGGLTS 915
WP_001040104   847 IPQAFIKDDSIDNRVLVSSAKNRG-KSDD--VP-S--LEIVKDCKV-FWKKLLDAKLMSQRKYDNLTKA--ERGGLTS 915
WP_001040105   847 IPQAFIKDDSIDNRVLVSSAKNRG-KSDD--VP-S--IDIVKARKA-FWKKLLDAKLISQRKYDNLTKA--ERGGLTS 915
WP_001040106   847 IPQAFIKDDSIDNRVLVSSAKNRG-KSDD--VP-S--IDIVKARKA-FWKKLLDAKLMSQRKYDNLTKA--ERGGLTS 915
WP_001040107   847 IPQAFIKDDSIDNRVLVSSAKNRG-KSDN--VP-S--LEIVKDCKV-FWKKLLDAKLMSQRKYDNLTKA--ERGGLTS 915
WP_001040108   847 IPQAFIKDDSIDNRVLVSSAKNRG-KSDN--VP-S--IDIVKARKA-FWKKLLDAKLMSQRKYDNLTKA--ERGGLTS 915
WP_001040109   847 IPQAFIKDDSIDNRVLVSSAKNRG-KSDD--VP-S--IDIVKARKA-FWKKLLDAKLMSQRKYDNLTKA--ERGGLTS 915
WP_001040110   847 VPQAFIKDDSIDNRVLVSSAKNRG-KSDN--VP-S--VEIVKDCKV-FWKKLLDAKLMSQRKYDNLTKA--ERGGLTS 915
WP_015058523   847 VPQAFIKDDSIDNRVLVSSAKNRG-KSDD--VP-S--VEIVKDCKV-FWKKLLDAKLMSQRKYDNLTKA--ERGGLTS 915
WP_017643650   847 IPQAFIKDDSIDNRVLVSSAKNRG-KSDD--VP-S--IDIVKARKA-FWKKLLDAKLISQRKYDNLTKA--ERGGLTP 915
WP_017647151   847 IPQAFIKDDSIDNRVLVSSAKNRG-KSDD--VP-S--IDIVKARKA-FWKKLLDAKLMSQRKYDNLTKA--ERGGLTS 915
WP_017648376   847 IPQAFIKDDSIDNRVLVSSAKNRG-KSDD--VP-S--VEIVKDCKV-FWKKLLDAKLMSQRKYDNLTKA--ERGGLTS 915
WP_017649527   847 IPQAFIKDDSIDNRVLVSSAKNRG-KSDD--VP-S--IDIVKARKA-FWKKLLDAKLMSQRKYDNLTKA--ERGGLTS 915
WP_017771611   847 IPQAFIKDDSIDNRVLVSSAKNRG-KSDN--VP-S--LEIVKDCKV-FWKKLLDAKLMSQRKYDNLTKA--ERGGLTS 915
WP_017771984   847 IPQAFIKDDSIDNRVLVSSAKNRG-KSDD--VP-S--LEIVKDCKV-FWKKLLDAKLMSQRKYDNLTKA--ERGGLTS 915
CFQ25032       847 IPQAFIKDDSIDNRVLVSSAKNRG-KSDD--VP-S--LEIVKDCKV-FWKKLLDAKLMSQRKYDNLTKA--ERGGLTS 915
CFV16040       847 IPQAFIKDDSIDNRVLVSSAKNRG-KSDN--VP-S--LEIVKDCKV-FWKKLLDAKLMSQRKYDNLTKA--ERGGLTS 915
KLJ37842       847 IPQAFIKDDSIDNRVLVSSAKNRG-KSDN--VP-S--LEIVKDCKV-FWKKLLDAKLMSQRKYDNLTKA--ERGGLTS 915
KLJ72361       847 IPQAFIKDDSIDNRVLVSSAKNRG-KSDD--VP-S--LEIVKDCKV-FWKKLLDAKLMSQRKYDNLTKA--ERGGLTS 915
KLL20707       861 IPQAFIKDDSIDNRVLVSSAKNRG-KSDD--VP-S--LEIVKDCKV-FWKKLLDAKLMSQRKYDNLTKA--ERGGLTS 929
KLL42645       847 IPQAFIKDDSIDNRVLVSSAKNRG-KSDD--VP-S--IDIVKARKA-FWKKLLDAKLMSQRKYDNLTKA--ERGGLTS 915
WP_047207273   847 VPQAFIKDDSIDNRVLVSSAKNRG-KSDD--VP-S--LEIVKDCKV-FWKKLLDAKLMSQRKYDNLTKA--ERGGLTS 915
WP_047209694   847 IPQAFIKDDSIDNRVLVSSAKNRG-KSDD--VP-S--LEIVKDCKV-FWKKLLDAKLMSQRKYDNLTKA--ERGGLTS 915
WP_050198062   847 IPQAFIKDDSIDNRVLVSSENRG-KSDN--VP-S--LEIVKDCKV-FWKKLLDAKLMSQRKYDNLTKA--ERGGLTS 915
WP_050201642   847 IPQAFIKDDSIDNRVLTRSDKNRG-KSDD--VP-S--IDIVKARKA-FWKKLLDAKLMSQRKYDNLTKA--ERGGLTS 915
WP_050204027   847 IPQAFIKDDSIDNRVLTRSDKNRG-KSDD--VP-S--LEIVKDCKV-FWKKLLDAKLMSQRKYDNLTKA--ERGGLTS 915
WP_050881965   847 IPQAFIKDDSIDNRVLTRSDKNRG-KSDD--VP-S--LEIVKDCKV-FWKKLLDAKLMSQRKYDNLTKA--ERGGLTS 915
WP_050886065   847 IPQAFIKDDSIDNRVLTRSDKNRG-KSDD--VP-S--IDIVKARKA-FWKKLLDAKLMSQRKYDNLTKA--ERGGLTP 915
AHN30376       847 IPQAFIKDDSIDNRVLTRSDKNRG-KSDN--VP-S--LEIVKDCKV-FWKKLLDAKLMSQRKYDNLTKA--ERGGLTS 915
EA078426       847 IPQAFIKDDSIDNRVLVSSAKNRG-KSDD--VP-S--LEIVKDCKV-FWKKLLDAKLMSQRKYDNLTKA--ERGGLTE 915
CCW42055       847 IPQAFIKDDSIDNRVLVSSAKNRG-KSDD--VP-S--LEIVKDCKV-FWKKLLDAKLMSQRKYDNLTKA--ERGGLTE 915
WP_003041502   841 IPQAYIKDDSFDNRVLTSSENRG-KSDN--VP-S--IEVVCARKA-DWMRLRKAGLISQRKFDNLTKA--ERGGLTS 909
WP_037593752   842 IPQAFIKDNSLDNRVLTRSDKNRG-KSDD--VP-S--IEVVHEMKS-FWSKLLSVKLITQRKFDNLTKA--ERGGLTE 910
WP_049516684   842 IPQAFIKDNSLDNRVLTRSDKNRG-KSDD--VP-S--IEVVHEMKS-FWSKLLSVKLITQRKFDNLTKA--ERGGLTE 910
GAD46167       841 IPQAFIKDDSIDNRVLTRSDKNRG-KSDD--VP-S--IEVVHEMKS-FWSKLLSVKLITQRKFDNLTKA--ERGGLTE 909
WP_018363470   850 IPQAFIKDDSIDNRVLTRSDKNRG-KSDD--VP-S--LGIVRARKA-EWVRLYKSGLISKRKFDNLTKA--ERGGLTE 918
```

-continued

| | | | | | |
|---|---|---|---|---|---|
| WP_003043819 | 851 | VPQSFIKDDSIDNKVLTRSVENRG-KSDN--VP | S--EEVVKKMKN-YWRQLLNAKLITQRKFDNLTKA--ERGGLSE | 919 |
| WP_066269658 | 841 | IPQAFIKDNSLDNRVLTRSDKNRG-KSDD--VP | S--IEVVHEMKS-FWSKLLSVKLITQRKFPDNLTKA--ERGGLTE | 909 |
| WP_048800089 | 841 | IPQAFIKDDSIDNRVLTSSAKNRG-KSDN--VP | N--LEVVCDRKA-DWIRLREAGLISQRKFPDNLTKA--ERGGLTE | 909 |
| WP_012767106 | 841 | VPQSFIKDDSIDNKILTRSDKNRG-KSDN--VP | S--EEVVKKMKN-YWRQLLNAKLITQRKFPDNLTKA--ERGGLSE | 909 |
| WP_014612333 | 841 | VPQSFIKDDSIDNKVLTRSDKNRG-KSDD--VP | S--EEVVKKMKN-YWRQLLNAKLITQRKFPDNLTKA--ERGGLSE | 909 |
| WP_015017095 | 841 | VPQSFIKDDSIDNKVLTRSDKNRG-KSDD--VP | S--EEVVKKMKN-YWRQLLNAKLITQRKFPDNLTKA--ERGGLSE | 909 |
| WP_015057649 | 841 | VPQSFIKDDSIDNKVLTRSDKNRG-KSDD--VP | S--EEVVKKMKN-YWRQLLNAKLITQRKFPDNLTKA--ERGGLSE | 909 |
| WP_048327215 | 841 | VPQSFIKDDSIDNKVLTRSDKNRG-KSDN--VP | S--EEVVKKMKN-YWRQLLNAKLITQRKFPDNLTKA--ERGGLSE | 909 |
| WP_049519324 | 841 | VPQSFIKDDSIDNKVLTRSDKNRG-KSDN--VP | S--EEVVKKMKN-YWRQLLNAKLITQRKFPDNLTKA--ERGGLSE | 909 |
| WP_012515931 | 841 | IPQSFIKNNSIDNKVLTSQGANRG-KLDN--VP | S--EAIVRKMKG-YWQSLLRAGAISKQKFPDNLTKA--ERGGLTQ | 909 |
| WP_021320964 | 841 | IPQSFIKNNSIDNKVLTSQGANRG-KLDN--VP | S--EAIVRKMKG-YWQSLLRAGAISKQKFPDNLTKA--ERGGLTQ | 909 |
| WP_037581760 | 841 | IPQSFIKNNSIDNKVLTSQGANRG-KLDN--VP | S--EAIVRKMKG-YWQSLLRAGAISKQKFPDNLTKA--ERGGLTQ | 909 |
| WP_004232481 | 849 | IPQAFIKDNSIDNRVLTSSAKNRG-KSDD--VP | S--IEIVRNRKS-VWYKLYKSGLISKRKFPDNLTKA--ERGGLTE | 917 |
| WP_009854540 | 850 | IPQAFIKDDSIDNRVLTRSDKNRG-KSDD--VP | S--LDIVRARKA-EMVRLYKSGLISKRKFPDNLTKA--ERGGLTE | 918 |
| WP_012962174 | 850 | IPQAFIKDDSIDNRVLTSSAKNRG-KSDD--VP | S--LDIVHDRKA-DWIRLYKSGLISKRKFPDNLTKA--ERGGLTE | 918 |
| WP_039695303 | 852 | IPQAFIKDNSIDNRVLTSSAKNRG-KSDD--VP | S--LDIVRARKA-EMVRLYKSGLISKRKFPDNLTKA--ERGGLTE | 920 |
| WP_014334983 | 849 | IPQAFIKDNSIDNRVLTSSAKNRG-KSDD--VP | S--IEIVRNRRS-VWYKLYKSGLISKRKFPDNLTKA--ERGGLTE | 917 |
| WP_003099269 | 842 | IPQSFIKDNSIDNTVLTTQASNRG-KSDN--VP | N--IETVNKMKS-FWYKQLKSGAISQRKFPDHLTKA--ERGALSD | 910 |
| AHY15608 | 842 | IPQAFIKDNSIDNTVLTTQASNRG-KSDN--VP | N--IETVNKMKS-FWYKQLKSGAISQRKFPDHLTKA--ERGALSD | 910 |
| AHY17476 | | | | |
| ESR09100 | | | | |
| AGM98575 | 842 | IPQSFIKDNSIDNTVLTTQASNRG-KSDN--VP | N--IETVNKMKS-FWYKQLKSGAISQRKFPDHLTKA--ERGALSD | 910 |
| ALF27331 | 842 | IPQAFIKDNSIDNRVLTSSKENRG-KSDD--VP | S--KDVVRKMKS-YWSKLLSAKLITQRKFPDNLTKA--ERGGLTD | 910 |
| WP_018372492 | 858 | VPRSYIKNDSFDNKVLTSSKGNRK-KLDD--VP | A--KEVVEKMEN-TWRRLHAAGLISDIKLSYLMKGe----LTE | 923 |
| WP_045618028 | 845 | IPQAFIKDNSIDNRVLTSSKDNRG-KSDN--VP | S--LEIVQKRKA-FWQQLLDSKLISERKFPNNLTKA--ERGGLDE | 913 |
| WP_045635197 | 844 | IPQAFIKDNSLDNRVLTSSKENRG-KSDN--VP | S--IEVVQKRKA-FWQKLLDSKLISERKFPNNLTKA--ERGGLTE | 912 |
| WP_002263549 | 842 | IPQAFIKDNSIDNRVLTSSKENRG-KSDD--VP | S--KDVVRKMKS-YWSKLLSAKLITQRKFPDNLTKA--ERGGLTD | 910 |
| WP_002263887 | 842 | IPQAFIKDNSIDNRVLTSSKENRG-KSDD--VP | S--KDVVRKMKS-YWSKLLSAKLITQRKFPDNLTKA--ERGGLTD | 910 |
| WP_002264920 | 842 | IPQAFIKDNSIDNRVLTSSKENRG-KSDD--VP | S--KDVVRKMKS-YWSKLLSAKLITQRKFPDNLTKA--ERGGLTD | 910 |
| WP_002269043 | 842 | IPQAFIKDNSIDNRVLTSSKENRG-KSDD--VP | S--KDVVRKMKS-YWSKLLSAKLITQRKFPDNLTKG--ERGGLTD | 910 |
| WP_002269448 | 842 | IPQAFIKDNSIDNRVLTSSKENRG-KSDD--VP | S--BDVVRKMKS-YWSKLLSAKLITQRKFPDNLTKA--ERGGLTD | 910 |
| WP_002271977 | 842 | IPQAFIKDNSIDNRVLTSSKENRG-KSDD--VP | S--KDVVRKMKS-YWSKLLSAKLITQRKFPDNLTKA--ERGGLTD | 910 |
| WP_002272766 | 842 | IPQAFIKDNSIDNRVLTSSKENRG-KSDD--VP | S--KDVVRKMKP-YWSKLLSAKLITQRKFPDNLTKA--ERGGLTD | 910 |
| WP_002273241 | 842 | IPQAFIKDNSIDNRVLTSSKENRG-KSDD--VP | S--KDVVRKMKP-YWSKLLSAKLITQRKFPDNLTKA--ERGGLTD | 910 |
| WP_002275430 | 847 | IPQAFIKDNSIDNRVLTSSKANRG-KSDN--VP | S--EDVVNRMRP-FWNKLLSSGLISQRKYNNLTKA--ERGGLTD | 912 |
| WP_002276448 | 842 | IPQAFIKDNSIDNRVLTSSKENRG-KSDD--VP | S--KDVVRKMKP-YWSKLLSAKLITQRKFPDNLTKA--ERGGLTD | 910 |
| WP_002277050 | 847 | IPQAFIKDNSIDNRVLTSSKANRG-KSDN--VP | S--KNVVRKMKS-YWNKLLSSGLISQRKYNNLTKK--E---LTP | 912 |
| WP_002277364 | 842 | IPQAFIKDNSIDNRVLTSSKENRG-KSDD--VP | S--BDVVNRMRP-FWNKLLSSGLISQRKYNNLTKK--E---LTP | 910 |
| WP_002279025 | 842 | IPQAFIKDNSIDNRVLTSSKENRG-KSDD--VP | S--KDVVRKMKP-YWSKLLSAKLITQRKFPDNLTKG--ERGGLTD | 910 |
| WP_002279859 | 842 | IPQAFIKDNSIDNRVLTSSKENRG-KSDD--VP | S--KDVVRKMKS-YWSKLLSAKLITQRKFPDNLTKA--ERGGLTD | 910 |
| WP_002280230 | 842 | IPQAFIKDNSIDNRVLTSSKENRG-KSDD--VP | S--KDVVRKMKP-YWSKLLSAKLITQRKFPDNLTKG--ERGGLTD | 910 |
| WP_002281696 | 842 | IPQAFIKDNSIDNRVLTSSKENRG-KSDD--VP | S--KNVVRKMKS-YWSKLLSAKLITQRKFPDNLTKA--ERGGLTD | 910 |
| WP_002282247 | 847 | IPQAFIKDNSIDNRVLTSSKANRG-KSDN--VP | S--EDVVNRMRP-FWNKLLSSGLISQRKYNNLTKK--E---LTL | 912 |
| WP_002282906 | 842 | IPQAFIKDNSIDNRVLTSSKENRG-KSDD--VP | S--KDVVRKMKS-YWSKLLSAKLITQRKFPDNLTKA--ERGGLTD | 910 |
| WP_002283846 | 842 | IPQAFIKDNSIDNRVLTSSKENRG-KSDD--VP | S--KNVVRKMKS-YWSKLLSAKLITQRKFPDNLTKA--ERGGLTD | 910 |
| WP_002287255 | 842 | IPQAFIKDNSIDNRVLTSSKENRG-KSDD--VP | S--KNVVRKMKS-YWSKLLSAKLITQRKFPDNLTKA--ERGGLTD | 910 |
| WP_002288990 | 842 | IPQAFIKDNSIDNRVLTSSKENRG-KSDD--VP | S--KDVVRKMKS-YWSKLLSAKLITQRKFPDNLTKA--ERGGLTD | 910 |
| WP_002289641 | 842 | IPQAFIKDNSIDNRVLTSSKENRG-KSDD--VP | S--KDVVRKMKP-YWSKLLSAKLITQRKFPDNLTKA--ERGGLTD | 910 |
| WP_002290427 | 842 | IPQAFIKDNSIDNRVLTSSKENRG-KSDD--VP | S--KDVVRKMKS-YWSKLLSAKLITQRKFPDNLTKA--ERGGLTD | 910 |
| WP_002295753 | 842 | IPQAFIKDNSIDNRVLTSSKENRG-KSDD--VP | S--KNVVRKMKS-YWSKLLSAKLITQRKFPDNLTKA--ERGGLTD | 910 |
| WP_002296423 | 842 | IPQAFIKDNSIDNRVLTSSKENRG-KSDD--VP | S--EEVVHKMKP-FWSKLLSAKLITQRKFPDNLTKA--ERGGLTD | 910 |
| WP_002304487 | 856 | IPQAFIKDNSIDNRVLTSSKENRG-KSDD--VP | S--KDVVRKMKS-YWSKLLSAKLITQRKFPDNLTKA--ERGGLTD | 924 |
| WP_002305844 | 842 | IPQAFIKDNSIDNRVLTSSKENRG-KSDD--VP | S--KDVVRKMKS-YWSKLLSAKLITQRKFPDNLTKA--ERGGLTD | 910 |

-continued

| | | | | |
|---|---|---|---|---|
| WP_002307203 | 842 | IPQAFIKDNSIDNRVLTSSKENRG-KSDD--VP | S--KDVVRKMKS-YWSKLLSAKLITQRKFPDNLTKA- | -ERGGLTD | 910 |
| WP_002310390 | 842 | IPQAFIKDNSIDNRVLTSSKENRG-KSDD--VP | S--KDVVRKMKS-YWSKLLSAKLITQRKFPDNLTKA- | -ERGGLTD | 910 |
| WP_002352408 | 842 | IPQAFIKDNSIDNRVLTSSKENRG-KSDD--VP | S--KDVVRKMKS-YWSKLLSAKLITQRKFPDNLTKA- | -ERGGLTD | 910 |
| WP_012997688 | 842 | IPQAFIKDNSIDNRVLTSSKENRG-KSDD--VP | S--KNVVRKMKS-YWSKLLSAKLITQRKFPDNLTKA- | -ERGGLTD | 910 |
| WP_014677909 | 842 | IPQAFIKDNSIDNRVLTSSKENRG-KSDD--VP | S--KDVVRKMKS-YWSKLLSAKLITQRKFPDNLTKA- | -ERGGLTD | 910 |
| WP_019312892 | 842 | IPQAFIKDNSIDNRVLTSSKENRG-KSDD--VP | S--KNVVRKMKS-YWSKLLSAKLITQRKFPDNLTKA- | -ERGGLTD | 910 |
| WP_019313659 | 842 | IPQAFIKDNSIDNRVLTSSKENRG-KSDD--VP | S--KDVVRKMKS-YWSKLLSAKLITQRKFPDNLTKA- | -ERGGLTD | 910 |
| WP_019314093 | 842 | IPQAFIKDNSIDNRVLTSSKENRG-KSDD--VP | S--KDVVRKMKS-YWSKLLSAKLITQRKFPDNLTKA- | -ERGGLTD | 910 |
| WP_019315370 | 842 | IPQAFIKDNSIDNRVLTSSKENRG-KSDD--VP | S--KDVVRKMKP-YWSKLLSAKLITQRKFPDNLTKA- | -ERGGLTD | 910 |
| WP_019803776 | 842 | IPQAFIKDNSIDNRVLTSSKENRG-KSDD--VP | S--KDVVRKMKS-YWSKLLSAKLITQRKFPDNLTKA- | -ERGGLTD | 910 |
| WP_019805234 | 842 | IPQAFIKDNSIDNRVLTSSKENRG-KSDD--VP | S--KDVVRKMKS-YWSKLLSAKLITQRKFPDNLTKG- | -ERGGLTD | 910 |
| WP_024783594 | 842 | IPQAFIKDNSIDNRVLTSSKENRG-KSDD--VP | S--KDVVRKMKS-YWSKLLSAKLITQRKFPDNLTKG- | -ERGGLTD | 910 |
| WP_024784288 | 847 | IPQAFIKDNSIDNRVLTSSKANRG-KSDD--VP | S--EDVVNRMRP-FWNKLLSSGLISQRKYNNLTKK- | -E---LTL | 912 |
| WP_024784666 | 842 | IPQAFIKDNSIDNRVLTSSKENRG-KSDD--VP | S--KNVVRKMKS-YWSKLLSAKLITQRKFPDNLTKA- | -ERGGLTD | 910 |
| WP_024784894 | 842 | IPQAFIKDNSIDNRVLTSSKANRG-KSDD--VP | S--KDVVRKMKS-YWSKLLSSGLISQRKYNNLTKA- | -ERGGLTD | 910 |
| WP_024786433 | 842 | IPQAFIKDNSIDNRVLTSSKENRG-KSDD--VP | S--SDVVNRMRP-FWNKLLSSGLISQRKYNNLTKK- | -E---LTL | 912 |
| WP_049473442 | 847 | IPQAFIKDNSIDNRVLTSSKANRG-KSDD--VP | S--KDVVRKMKP-YWSKLLSAKLITQRKFPDNLTKA- | -ERGGLTD | 912 |
| WP_049474547 | 842 | IPQAFIKDNSIDNRVLTSSKENRG-KSDD--VP | S--KDVVRKMKS-YWSKLLSAKLITQRKFPDNLTKA- | -ERGGLTD | 910 |
| EMC03581 | 835 | IPQAFIKDNSIDNRVLTSKDNRG-KSDN--VP | S--KNVVRKMKS-YWSKLLSAKLITQRKFPDNLTKA- | -ERGGLTD | 903 |
| WP_000428612 | 847 | VPQAFIKDDSLDNRVLTSLKDNRG-KSDN--VP | S--LEVVEKMKT-FWQQLLDSKLISYRKFPNNLTKA- | -ERGGLTDE | 915 |
| WP_000428613 | 845 | IPQAFIKDDSLDNRVLTSSKDNRG-KSDN--VP | S--LEVVQKRKA-FWQQLLDSKLISERKFPNNLTKA- | -ERGGLDE | 913 |
| WP_049523028 | 840 | IPQAFIKDDSLDNRVLTSSKDNRG-KSDN--VP | S--LEIVEKMKG-FWQQLLDSKLISERKFPNNLTKA- | -KRGGLDE | 908 |
| WP_003107102 | 811 | IPQAFIKDDSIDNKVLTSQESNRG-KSDN--VP | Y--IAIVNKMKS-YWQHQLKSGAISQRKEDNLTKA- | -ERGGLSE | 879 |
| WP_054279288 | 843 | IPRSFIKDDSIDNKVLTRSEHNRG-KTDN--VP | S--LEVVQKRKA-FWQKLLDTKVISQRKFPNNLTKA- | -ERGGLQE | 911 |
| WP_049531101 | 845 | IPQAFIKDDSLDNRVLTKSAKNRG-KSDD--VP | S--LEVVQKRKA-FWQQLLESKLISERKFPNNLTKA- | -ERGGLNE | 913 |
| WP_049538452 | 845 | IPQAFIKDDSLDNRVLTKSAKNRG-KSDN--VP | C--LEVVDKMKV-FWQQLLDFKLISYRKFPNNLTKA- | -ERGGLDE | 913 |
| WP_049549711 | 845 | IPQAFIKDDSLDNRVLTKSAKNRG-KSDN--VP | S--LEVVRDMKD-FWRRQLANGAISRQKFDHLTKAer | ERDGLNE | 915 |
| WP_007896501 | 847 | IPQAFIKDDSFDNRVLTSSENRG-KSDN--VP | S--IEVVRDMKD-rWRRQLANGAISRQKFDHLTKA- | -ERGGLAD | 916 |
| EFR44625 | 799 | IPQSFIKDNSIDNLVLTTQKANRG-KSDN--VP | S--IEVVRDMKD-rVWRRQLANGA1SRQKFDHLTKA- | -ERGGLAD | 868 |
| WP_002897477 | 844 | IPQAFIKDDSIDNRVLTSSKDNRG-KSDN--VP | S--LEVVQKRKA-FWQQLLDSKLISERKFPNNLTKA- | -ERGGLDE | 912 |
| WP_002906454 | 844 | IPQAFIKDDSLDNRVLTSSKDNRG-KSDN--VP | S--IEVVQKRKA-FWQQLLDSKLISERKFPNNLTKA- | -KRGGLDE | 912 |
| WP_009729476 | 845 | IPQAFIKDDSLDNRVLTSSKANRG-KSDD--VP | S--LEVVDKMKV-FWQQLLDSQLISQRKFPNNLTKA- | -ERGGLNE | 913 |
| CQR24647 | 844 | IPQSFIKDNSLDNRVLTNSKSNRG-KSDN--VP | S--NEVVEKMKA-FWQQLLDSKLISERKFPNNLTKAer | ERGGLNE | 912 |
| WP_000066813 | 847 | IPQSFIKDNSLDNRVLTSSKDNRG-KSDN--VP | S--LEVVEKMKA-FWKQLLDSKLISERKFPNNLTKAer | ERGGLNE | 917 |
| WP_009754323 | 845 | IPQAFIKDDSLDNRVLTSSKDNRG-KSDN--VP | S--LEVVKRKA-FWKQLLDSQLISERKFPNNLTKA- | -ERGGLDE | 913 |
| WP_044674937 | 844 | IPQAFIKDDSLDNRVLTKSAKNRG-KSDD--VP | S--LEIVHCKKN-YWRQLLNAKLITQRKFPNNLTKA- | -ERGGLTN | 912 |
| WP_044676715 | 846 | IPQAFIKDDSLDNRVLTKSAKNRG-KSDD--VP | S--LEIVHCKKN-FWKQLLDSQLISERKFPNNLTKA- | -ERGGLTN | 914 |
| WP_044680361 | 846 | IPQAFIKDDSLDNRVLTKSAKNRG-KSDN--VP | S--LEIVHKKN-FWKQLLDSQLISQRKFPNNLTKA- | -ERGGLTN | 914 |
| WP_044681799 | 844 | IPQAFIKDDSLDNRVLTKSAKNRG-KSDN--VP | S--LEIVHCKKN-FWKQLLDSQLISQRKFPNNLTKA- | -ERGGLTN | 912 |
| WP_049533112 | 841 | IPQAFIKDDSFDNRVLVSSKENRL-KMDD--VP | S--IEVVRARKA-DWMRLRKAGLISERKFPAYLTKLe | ---LTP | 909 |
| WP_029090905 | 824 | LPQSYIKDNSIENLALVKKVENQR-KKDS11LN | S--SIINQNYS-RWEQLKNAGLIGEKKFPNLTRTk- | --ITD | 890 |
| WP_006506696 | 850 | VPQSLVKDDSEDNRVLVVPSENQR-KLDD1vVP | --FDIRDKMYR-FWKLLPDHELISPKKFYSLIKTe- | --YTE | 916 |
| AIT42264 | 842 | IPQSFLKDDSIDNKVLTRSDKNRG-KSDN--VP | S--BEVVKKMKN-YWRQLLNAKLITQRKFPDNLTKA- | -ERGGLSE | 910 |
| WP_034440723 | 849 | IPRSFITDNSEDNLVLTSSTVNRG-KLLDN--VP | Sp--DIVRQQKG-FWKQLLRAGLMSQRKFNNLTKGk- | ---LTD | 914 |
| AKQ21048 | 842 | VPQSFLKDDSIDNRVLTSDHNRG-KSDN--VP | S--BEVVKKMKN-YWRQLLNAKLITQRKFPDNLTKA- | -ERGGLSE | 914 |
| WP_004636532 | 846 | IPQSFTTDNSIDNKVLSRTKNQGnKSDD--VP | S--INIVHKMKP-FWRQLHKAGLISDRKFKNLTKA- | -EHGGLTE | 915 |
| WP_002364836 | 853 | IPQSFMKDDSLDNLVLNLVLVGSTENRG-VP | S--KEVVKDMKA-YWEKLYAAGLISQRKFQRLTKG- | -EQGGLTL | 921 |
| WP_016631044 | 804 | IPQSFMKDDSLDNLVLDNKVLVGSTENRG-VP | S--KEVVKDMKA-YWEKLYAAGLISQRKFQRLTKG- | -EQGGLTL | 872 |
| EMS75795 | 589 | IPRSFIVDNSIDNKVLVSSKENRL-KMDD--VP | D--QKVVIRMRR-YWEKLRANLISERKFAYLTKLe- | ---LTP | 654 |
| WP_002373311 | 853 | IPQSFMKDDSLDNLVLVLVGSTENRG-VP | S--KKVVKKMKA-YWEKLYAAGLISQRKFQRLTKG- | -EQGGLTL | 921 |
| WP_002378009 | 853 | IPQSFMKDDSLDNLVLVLVGSTENRG-VP | S--KEVVKDMKA-YWEKLYAAGLISQRKFQRLTKG- | -EQGGLTL | 921 |
| WP_002407324 | 853 | IPQSFMKDDSLDNLVLVLVGSTENRG-VP | S--KEVVKDMKA-YWEKLYAAGLISQRKFQRLTKG- | -EQGGLTL | 921 |
| WP_002413717 | 853 | IPQSFMKDDSLDNLVLVLVGSTENRG-VP | S--KEVVKDMKA-YWEKLYAAGLISQRKFQRLTKG- | -EQGGLTL | 921 |

-continued

| ID | Seq start | Sequence | Seq end |
|---|---|---|---|
| WP_010775580 | 855 | IPQSFMKDDSLDNLVLVGSTENRG-KSDD--VP S--KEVVKKMKA-YWEKLYAAGLISQRKFQRLTKG--EQGGLTL | 923 |
| WP_010818269 | 853 | IPQSFMKDDSLDNLVLVGSTENRG-KSDD--VP S--KEVVKDMKA-YWEKLYAAGLISQRKFQRLTKG--EQGGLTL | 921 |
| WP_010824395 | 853 | IPQSFMKDDSLDNLVLVGSTENRG-KSDD--VP S--KEVVKDMKA-YWEKLYAAGLISQRKFQRLTKG--EQGGLTL | 921 |
| WP_016622645 | 853 | IPQSFMKDDSLDNLVLVGSTENRG-KSDD--VP S--KEVVKDMKA-YWEKLYAAGLISQRKFQRLTKG--EQGGLTL | 921 |
| WP_033625576 | 853 | IPQSFMKDDSLDNLVLVGSTENRG-KSDD--VP S--KEVVKDMKA-YWEKLYAAGLISQRKFQRLTKG--EQGGLTL | 921 |
| WP_033789179 | 853 | IPQSFMKDDSLDNLVLVGSTENRG-KSDD--VP S--KEVVKDMKA-YWEKLYAAGLISQRKFQRLTKG--EQGGLTL | 921 |
| WP_002110644 | 853 | IPQSFMKDDSLDNLVLVGSTENRG-KKDD--VP S--BKVVKKMRS-FWYDLYSSKLISKRKLDNLTKIk----LTE | 918 |
| WP_002112694 | 854 | IPRSFFTDNSIDNKVLVSSKENRL-KKDD--VP S--EKVVKKMRS-FWYDLYSSKLISKRKLDNLTKIk----LTE | 919 |
| WP_002314015 | 853 | IPRSFFTDNSIDNKVLVSSKENRL-KKDD--VP S--EKVVKKMRS-FWYDLYSSKLISKRKLDNLTKIk----LTE | 919 |
| WP_002320716 | 854 | IPRSFFTDNSIDNKVLVSSKENRL-KKDD--VP S--EKVVKKMRS-FWYDLYSSKLISKRKLDNLTKIk----LTE | 919 |
| WP_002330729 | 853 | IPRSFFTDNSIDNKVLVSSKENRL-KKDD--VP S--EKVVKKMRS-FWYDLYSSKLISKRKLDNLTKIk----LTE | 918 |
| WP_002335161 | 854 | IPRSFFTDNSIDNKVLVSSKENRL-KKDD--VP S--EKVVKKMRS-FWYDLYSSKLISKRKLDNLTKIk----LTE | 919 |
| WP_002345439 | 854 | IPRSFFTDNSIDNKVLVSSKENRL-KKDD--VP S--EKVVKKMRS-FWYDLYSSKLISTKKYAYLTKIe----LTP | 919 |
| WP_034867970 | 845 | IPRSFIVDNSIDDKVLVASKQNQK-KRDD--VP K--KQIVNEQRI-FWNQLKEAKLISPKKYAYLTKIe----LTP | 910 |
| WP_047937432 | 854 | IPRSFIVDNSIDNKVLVASKQNQK-KRDD--VP K--KQIVNEQRI-FWNQLKEAKLISPKKYAYLTKIe----LTE | 919 |
| WP_010720994 | 845 | IPRSFIVDNSIDNKVLVASKQNQK-KRDD--VP K--KQIVNEQRI-FWNQLKEAKLISPKKYAYLTKIe----LTP | 910 |
| WP_010073004 | 845 | IPRSFIVDNSIDNRVLTSKNPSG-KRDD--VP K--KQIVNEQRI-FWNQLKEAKLISPKKYAYLTKIe----LTP | 910 |
| WP_034700478 | 845 | IPRSFIVDNSIDNRVLTSKNPSG-KRDD--VP N--KQIVNEQRI-FWKLLNAKLISERKYTNLTKKe----LTP | 910 |
| WP_007209003 | 846 | IPQSFLTDNSIDNRVLTSKNPSG-KLDD--VP S--BERVYTMDR-PWRKLLNAKLISERKYTNLTKe----LTE | 911 |
| WP_023519017 | 839 | IPRSFIVDNSLDNKVLVSSKVNRG-KLDN--AP D--PLVVKRMRS-HWEKLHQAKLISDKKLANLTKQn----LTE | 904 |
| WP_010770040 | 846 | VPQSFTDNSLDNRVLVSSKENRG-KKDD--VP S--KEVVQKNIT-LWETLKNSNLISQKYDNLTKG--LRGGLTE | 914 |
| WP_048604708 | 843 | IPQSFIVDHSLDNKVLVSSKNRG-KLDD--VP S--KVVVRKMRA-FWESLYRSGLISKKKKFDNLVKA--ESGGLSE | 911 |
| WP_010750235 | 848 | IPRSFIVDHSLDNKVLVSSKNRG-KLDD--VP D--SKVVVRKMRA-YWEKLLRANLISERKFSYLTKIe----LTD | 913 |
| AII16583 | 881 | VPQSFLKDDSIDNKVLTRSDKNRG-KSDN--VP S--BEVVKKMKN-YWRQLLNAKLITQRKFDNLTKA--ERGGLSE | 949 |
| WP_029073316 | 861 | VPQSLLKDDSIDNKVLVLSSENQR-KLDD1vIP ---EMIRNKMFG-FWNKLYENKISPKKFYSLIKSe----YSD | 927 |
| WP_031589969 | 861 | VPQSLLKDDSIDNKVLVLSSENQR-KLDD1vIP ---SSIRNKMYG-FWEKLFNNKISPKKFYSLIKTe----FNE | 927 |
| KDA45870 | 834 | IPQSFLKDDSIENKVLTIKKENVR-KTNG--LP S--EAVIQKMGS-FWKLLDAGAMTNKKYDNLRRNl-HGGLNE | 902 |
| WP_039099354 | 857 | LPQSFLKDNSLDNRVLSQRMNRS-KADQ--VP S--VELGQKMQI-QWEQMLRAGLITKKKYDNLTLNp------ | 923 |
| AKP02966 | 859 | LPRTYIPDDSLENKALVLAKENQR-KADD11LN S--NVIDKNLE-RWTYMLNNNMGLKKFKNLTRRv---ITD | 925 |
| WP_010991369 | 845 | VPQSFITDNSIDNLVLTSSAGNRE-KGDD--VP P--LEIVRKRKA-FWEKLYQGNLMSKRKFPDYLTKA--ERGGLTE | 913 |
| WP_003838504 | 845 | VPQSFITDNSIDNLVLTSSAGNRE-KGDD--VP P--LEIVRKRKA-FWEKLYQGNLMSKRKFPDYLTKA--ERGGLTE | 913 |
| EHN60060 | 848 | VPQSFITDNSIDNLVLTSSAGNRE-KGDN--VP P--LEIVRKRKA-FWEKLYQGNLMSKRKFPDYLTKA--ERGGLTE | 916 |
| EFR89594 | 614 | VPQSFITDNSIDNLVLTSSAGNRE-KGND--VP P--LEIVQKRKV-FWEKLYQGNLMSKRKFPDYLTKA--ERGGLTE | 682 |
| WP_038409211 | 845 | IPQSFITDNSIDNRVLVSSTANRE-KGDN--VP L--LEIVRKRKA-FWEKLYQAKLMSKRKFPDYLTKA--ERGGLTE | 913 |
| EFR95520 | 464 | VPQSFITDNSIDNLVLTSSAGNRE-KGDN--VP L--LEIVRKRKA-FWEKLYQAKLMSKRKFPDYLTKA--ERGGLTE | 532 |
| WP_003723650 | 845 | VPQSFITDNSIDNLVLTSSAGNRE-KGDN--VP P--LEIVRKRKI-FWEKLYQGNLMSKRKFPDYLTKA--ERGGLTE | 913 |
| WP_003727705 | 845 | VPQSFITDNSIDNLVLTSSAGNRE-KGGD--VP P--LEIVRKRKI-FWEKLYQGNLMSKRKFPDYLTKA--ERGGLTE | 913 |
| WP_003730785 | 845 | VPQSFITDNSIDNLVLTSSAGNRE-KGGD--VP P--LEIVRKRKI-FWEKLYQGNLMSKRKFPDYLTKA--ERGGLTE | 913 |
| WP_003733029 | 845 | VPQSFITDNSIDNSVLVLTSSAGNRE-KGGD--VP P--LEIVRKRKI-FWEKLYQGNLMSKRKFPDYLTKA--ERGGLTE | 913 |
| WP_003739838 | 845 | VPQSFITDNSIDNLVLTSSAGNRE-KGGD--VP P--LEIVRKRKI-FWEKLFQGNLMSKRKFPDYLTKA--ERGGLTE | 913 |
| WP_014601172 | 845 | VPQSFITDNSIDNLVLTSSAGNRE-KGGD--VP P--LEIVQKRKI-FWEKLFQGNLMSKRKFPDYLTKA--ERGGLTE | 913 |
| WP_023548323 | 848 | VPQSFITDNSIDNLVLTSSAGNRE-KGGD--VP P--LEIVQKRKI-FWEKLYQGNLMSKRKFPDYLTKA--ERGGLTD | 916 |
| WP_031665337 | 848 | VPQSFITDNSIDNLVLTSSAGNRE-KGDN--VP P--LEIVQKRKI-FWEKLYQGNLMSKRKFPDYLTKA--ERGGLTE | 916 |
| WP_031669209 | 845 | VPQSFITDNSVDNLVLTSSAANRE-KGDN--VP P--LEIVQKRKI-FWEKLYQGNLMSKRKFPDYLTKA--ERGGLTE | 913 |
| WP_033920898 | 845 | VPQSFITDNSIDNLVLTSSAANRE-KGDN--VP S--LEVVRKRKI-FWEKLYQGNLMSKRKFPDYLTKA--ERGGLTE | 913 |
| AKI42028 | 848 | VPQSFITDNSIDNLVLTSSAANRE-KGDN--VP P--LEIVQKRKI-FWEKLYQAKLITQRKFDNLTKA--ERGGLTD | 916 |
| AKI50529 | 848 | VPQSFITDNSIDNLVLTSSAANRE-KGDN--VP S--LEVVRKRKN-YWRQLLNAKLITQRKFDNLTKA--ERGGLTE | 916 |
| EFR83390 | 293 | VPQSFITDNSIDNLVLTSSAANRE-KGDN--VP S--LEVVRKRKN-YWRQLLNAKLITQRKFDNLTKA--ERGGLTE | 361 |
| WP_046323366 | 845 | VPQSFLKDDSIDNKVLTRSDKNRG-KSDN--VP S--BEEVVKKMKN-YWRQLLNAKLITQRKFDNLTKA--ERGGLTE | 913 |
| AKE81011 | 858 | VPQSLVKDDSFDNRVLVLPSENQR-KLDD1vVP ---FDIRDKMYR-FWKLLFPDHELISPKKFYSLIKTe----YTE | 926 |
| CU082355 | 854 | VPQSLVKDDSFDNRVLVLPEENQW-KLDSetVP ---FEIRNKMIG-FWQMLHENGLMSNKFFSLIRTd----FSD | 920 |
| WP_033162887 | 856 | LPQSLIKDDSFDNRVLVLPEENQW-KLDSetVP ---FEIRNKMIG-FWQMLHENGLMSNKFFSLIRTd----FSD | 922 |

-continued

```
AGZ01981        875 VPQSFLKDDSIDNKVLTRSDKNRG-KSDN--VP S--EEVVKKMKN-YWRQLLNAKLITQRKFPDNLTKA--ERGGLSE 943
AKA60242        842 VPQSFLKDDSIDNKVLTRSDKNRG-KSDN--VP S--EEVVKKMKN-YWRQLLNAKLITQRKFPDNLTKA--ERGGLSE 910
AKS40380        842 VPQSFLKDDSIDNKVLTRSDKNRG-KSDN--VP S--EEVVKKMKN-YWRQLLNAKLITQRKFPDNLTKA--ERGGLSE 910
4UN5_B          846 VPQSFLKDDSIDNKVLTRSDKNRG-KSDN--VP S--EEVVKKMKN-YWRQLLNAKLITQRKFPDNLTKA--ERGGLSE 914
WP_010922251    911 LD KAGFIKRQLVETRQITKHVAQILDSRMNTKYDENDKLIR--EVKVITLKSKLVSDFRKDF QFYKVREINNY 981
WP_039695303    921 AD KVGFIKRQLVETRQITKHVAQILDARFNTEHDENDKVIR--DVKVITLKSNLVSQFRKDF EFYKVREINDY 991
WP_045635197    913 RD KVGFIKRQLVETRQITKHVAQILDARYNTEVNEKDKKNR--TVKIITLKSNLVSNERKEF RLYKVREINDY 983
5AXW_A          633 RD QKDFINRNLVDTRYATRGLMNLLRSYFR---------VNnlDVKVKSINGGFTSPLRRKW KFFKKERNKGYK 702
WP_009880683    595 LD KAGFIKRQLVETRQITKHVAQILDSRMNTKYDENDKLIR--EVKVITLKSKLVSDERKDF QFYKVREINNY 665
WP_010922251    911 LD KAGFIKRQLVETRQITKHVAQILDSRMNTKYDENDKLIR--EVKVITLKSKLVSDERKDF QFYKVREINNY 981
WP_011054416    911 LD KAGFIKRQLVETRQITKHVAQILDSRMNTKYDENDKLIR--EVKVITLKSKLVSDERKDF QFYKVREINNY 981
WP_011284745    911 LD KAGFIKRQLVETRQITKHVAQILDSRMNTKYDENDKLIR--EVKVITLKSKLVSDERKDF QFYKVREINNY 981
WP_011285506    911 LD KAGFIKRQLVETRQITKHVAQILDSRMNTKYDENDKLIR--EVKVITLKSKLVSDERKDF QFYKVREINNY 981
WP_011527619    911 LD KAGFIKRQLVETRQITKHVAQILDSRMNTKYDENDKLIR--EVKVITLKSKLVSDERKDF QFYKVREINNY 981
WP_012560673    911 LD KAGFIKRQLVETRQITKHVAQILDSRMNTKYDENDKLIR--EVKVITLKSKLVSDERKDF QFYKVREINNY 981
WP_014407541    910 LD KAGFIKRQLVETRQITKHVAQILDSRMNTKYDENDKLIR--EVKVITLKSKLVSDERKDF QFYKVREINNY 980
WP_020905136    910 LD KAGFIKRQLVETRQITKHVAQILDSRMNTKYDENDKLIR--EVKVITLKSKLVSDERKDF QFYKVREINNY 980
WP_023080005    911 LD KAGFIKRQLVETRQITKHVAQILDSRMNTKYDENDKLIR--EVKVITLKSKLVSDERKDF QFYKVREINNY 981
WP_023610282    910 LD KAGFIKRQLVETRQITKHVAQILDSRMNTKYDENDKLIR--EVKVITLKSKLVSDERKDF QFYKVREINNY 980
WP_030125963    910 LD KAGFIKRQLVETRQITKHVAQILDSRMNTKYDENDKLIR--EVKVITLKSKLVSDERKDF QFYKVREINNY 980
WP_030126706    911 LD KAGFIKRQLVETRQITKHVAQILDSRMNTKYDENDKLIR--EVKVITLKSKLVSDERKDF QFYKVREINNY 981
WP_031488318    911 LD KAGFIKRQLVETRQITKHVAQILDSRMNTKYDENDKLIR--EVKVITLKSKLVSDERKDF QFYKVREINNY 981
WP_032460140    911 LD KAGFIKRQLVETRQITKHVAQILDSRMNTKYDENDKLIR--EVKVITLKSKLVSDERKDF QFYKVREINNY 981
WP_032461047    911 LD KAGFIKRQLVETRQITKHVAQILDSRMNTKYDENDKLIR--EVKVITLKSKLVSDERKDF QFYKVREINNY 981
WP_032462016    911 LD KAGFIKRQLVETRQITKHVAQILDSRMNTKYDENDKLIR--EVKVITLKSKLVSDERKDF QFYKVREINNY 981
WP_032462936    911 LD KAGFIKRQLVETRQITKHVAQILDSRMNTKYDENDKLIR--EVKVITLKSKLVSDERKDF QFYKVREINNY 981
WP_032464890    911 LD KAGFIKRQLVETRQITKHVAQILDSRMNTKYDENDKLIR--EVKVITLKSKLVSDERKDF QFYKVREINNY 981
WP_033888930    736 LD KAGFIKRQLVETRQITKHVAQILDSRMNTKYDENDKLIR--EVKVITLKSKLVSDERKDF QFYKVREINNY 806
WP_038431314    911 LD KAGFIKRQLVETRQITKHVAQILDSRMNTKYDENDKLIR--EVKVITLKSKLVSDERKDF QFYKVREINNY 981
WP_038432938    910 LD KAGFIKRQLVETRQITKHVAQILDSRMNTKYDENDKLIR--EVKVITLKSKLVSDERKDF QFYKVREINNY 980
WP_038434062    911 LD KAGFIKRQLVETRQITKHVAQILDSRMNTKYDENDKLIR--EVKVITLKSKLVSDERKDF QFYKVREINNY 981
BAQ51233        822 LD KAGFIKRQLVETRQITKHVAQILDSRMNTKYDENDKLIR--EVKVITLKSKLVSDERKDF QFYKVREINNY 892
KGE60162         86 LD KVGFIKRQLVETRQITKHVAQILDSRMNTKYDENDKLIR--EVKVITLKSKLVSDERKDF QFYKVREINNY 156
KGE60856         -- --------------------------------------------------------- ---------- ---
WP_002989955    911 LD KAGFIKRQLVETRQITKHVAQILDSRMNTKYDENDKLIR--EVKVITLKSKLVSDERKDF QFYKVREINNY 981
WP_003030002    910 ED KAGFIKRQLVETRQITKHVAQILDSRMNTKYDENDKLIR--NVKIITLKSNLVSNFRKEF ELYKVREINNY 980
WP_003065552    921 AD KAGFIKRQLVETRQITKHVAQILDARFNTSDENDKVIR--DVKVITLKSNLVSQFRKDF EFYKVREINDY 991
WP_001040076    916 DD KARFIQRQLVETRQITKHVAR ILDERFNNELDSKGRRIR--KVKIVTLKSNLVSNFRKEF VFYKVREVNDY 986
WP_001040078    916 DD KARFIQRQLVETRQITKHVAR ILDERFNNELDSKGRRIR--KVKIVTLKSNLVSNFRKEF GFYKVREVNDY 986
WP_001040080    916 DD KARFIQRQLVETRQITKHVAR ILDERFNNELDSKGRRIR--KVKIVTLKSNLVSNFRKEF GFYKIREVNNY 986
WP_001040081    916 DD KARFIQRQLVETRQITKHVAR ILDERFNNELDSKGRRIR--KVKIVTLKSNLVSNFRKEF GFYKIREVNNY 986
WP_001040083    916 DD KARFIQRQLVETRQITKHVAR ILDERFNNELDSKGRRIR--KVKIVTLKSNLVSNFRKEF GFYKIREVNNY 986
WP_001040085    916 DD KARFIQRQLVETRQITKHVAR ILDERFNNELDSKGRRIR--KVKIVTLKSNLVSNFRKEF GFYKIREVNNY 986
WP_001040087    916 DD KARFIQRQLVETRQITKHVAR ILDERFNNELDSKGRRIR--KVKIVTLKSNLVSNFRKEF GFYKIREVNNY 986
WP_001040088    916 DD KARFIQRQLVETRQITKHVAR ILDERFNNKLDSKGRRIR--KVKIVTLKSNLVSNFRKEF GFYKIREVNNY 986
WP_001040089    916 DD KARFIQRQLVETRQITKHVAR ILDERFNNELDSKGRRIR--KVKIVTLKSNLVSNFRKEF GFYKIREVNNY 986
WP_001040090    916 DD KARFIQRQLVETRQITKHVAR ILDERFNNELDSKGRRIR--KVKIVTLKSNLVSNFRKEF GFYKIREVNNY 986
WP_001040091    916 DD KARFIQRQLVETRQITKHVAR ILDERFNNELDSKGRRIR--KVKIVTLKSNLVSNFRKEF GFYKIREVNNY 986
WP_001040092    916 DD KARFIQRQLVETRQITKHVAR ILDERFNNELDSKGRRIR--KVKIVTLKSNLVSNFRKEF GFYKIREVNNY 986
WP_001040094    916 DD KARFIQRQLVETRQITKHVAR ILDERFNNELDSKGRRIR--KVKIVTLKSNLVSNFRKEF GFYKIREVNNY 986
WP_001040095    916 DD KARFIQRQLVETRQITKHVAR ILDERFNNELDSKGRRIR--KVKIVTLKSNLVSNFRKEF GFYKIREVNNY 986
WP_001040096    916 DD KARFIQRQLVETRQITKHVAR ILDERFNNELDSKGRRIR--KVKIVTLKSNLVSNFRKEF GFYKIREVNNY 986
WP_001040097    916 DD KARFIQRQLVETRQITKHVAR ILDERFNNELDSKGRRIR--KVKIVTLKSNLVSNFRKEF GFYKIREVNNY 986
```

-continued

| | | | | |
|---|---|---|---|---|
| WP_001040098 | 916 DD | KARFIQRQLVETRQITKHVARILDERFNNELDSKGRRIR-- | KVKIVTLKSNLVSNFRKEF | GFYKIREVNNY 986 |
| WP_001040099 | 916 DD | KARFIQRQLVETRQITKHVARILDERFNNELDSKGRRIR-- | KVKIVTLKSNLVSNFRKEF | GFYKIREVNNY 986 |
| WP_001040100 | 916 DD | KARFIQRQLVETRQITKHVARILDERFNNELDSKGRRIR-- | KVKIVTLKSNLVSNFRKEF | GFYKIREVNNY 986 |
| WP_001040104 | 916 DD | KARFIQRQLVETRQITKHVARILDERFNNELDSKGRRIR-- | KVKIVTLKSNLVSNFRKEF | GFYKIREVNNY 986 |
| WP_001040105 | 916 DD | KARFIQRQLVETRQITKHVARILDERFNNELDSKGRRIR-- | KVKIVTLKSNLVSNFRKEF | GFYKIREVNNY 986 |
| WP_001040106 | 916 DD | KARFIQRQLVETRQITKHVARILDERFNNELDSKGRRIR-- | KVKIVTLKSNLVSNFRKEF | GFYKIREVNDY 986 |
| WP_001040107 | 916 DD | KARFIQRQLVETRQITKHVARILDERFNNELDSKGRRIR-- | KVKIVTLKSNLVSNFRKEF | GFYKIREVNDY 986 |
| WP_001040109 | 916 DD | KARFIQRQLVETRQITKHVARILDERFNNELDSKGRRIR-- | KVKIVTLKSNLVSNFRKEF | GFYKIREVNDY 986 |
| WP_001040110 | 916 DD | KAGFIQRQLVETRQITKHVARILDERFNNELDSKGRRIR-- | KVKIVTLKSNLVSNFRKEF | GFYKIREVNNY 986 |
| WP_015058523 | 916 DD | KARFIQRQLVETRQITKHVARILDERFNNKVDDNNKPIR-- | KVKIVTLKSNLVSNFRKEF | GFYKIREVNNY 986 |
| WP_017643650 | 916 DD | KARFIQRQLVETRQITKHVARILDELFNNELDSKGRRIR-- | KVKIVTLKSNLVSNFRKEF | GFYKIREVNNY 986 |
| WP_017647151 | 916 DD | KARFIQRQLVETRQITKHVARILDERFNNELDSKGRRIR-- | KVKIVTLKSNLVSNFRKEF | GFYKIREVNNY 986 |
| WP_017648376 | 916 DD | KARFIQRQLVETRQITKHVARILDERFNNELDSKGRRIR-- | KVKIVTLKSNLVSNFRKEF | GFYKIREVNNY 986 |
| WP_017649527 | 916 DD | KARFIQRQLVETRQITKHVARILDERFNNELDSKGRRIR-- | KVKIVTLKSNLVSNFRKEF | GFYKIREVNDY 986 |
| WP_017771611 | 916 DD | KARFIQRQLVETRQITKHVARILDERFNNELDSKGRRIR-- | KVKIVTLKSNLVSNFRKEF | GFYKIREVNDY 986 |
| WP_017771984 | 916 DD | KARFIQRQLVETRQITKHVARILDERFNNELDSKGRRIR-- | KVKIVTLKSNLVSNFRKEF | GFYKIREVNDY 986 |
| CFQ25032 | 916 DD | KARFIQRQLVEIRQITKHVARILDERFNNELDSKGRRIR-- | KVKIVTLKSNLVSNFRKEF | GFYKIREVNNY 986 |
| CFV16040 | 916 DD | KARFIQRQLVETRQITKHVARILDERFNNELDSKGRRIR-- | KVKIVTVKSNLVSNFRKEF | GFYKIREVNNY 986 |
| KLJ37842 | 916 DD | KARFIQRQLVETRQITKHVARILDERFNNELDSKGRRIR-- | KVKIVTLKSNLVSNFRKEF | GFYKIREVNNY 986 |
| KLJ72361 | 930 DD | KARFIQRQLVETRQITKHVARILDERFNNELDSKGRRIR-- | KVKIVTLKSNLVSNFRKEF | GFYKIREVNNY 1000 |
| KLL20707 | 916 DD | KARFIQRQLVETRQITKHVARILDERFNNELDSKGRRIR-- | KVKIVTLKSNLVSNFRKEF | GFYKIREVNNY 986 |
| KLL42645 | 916 DD | KARFIQRQLVETRQITKHVARILDERFNNELDSKGRRIR-- | KVKIVTLKSNLVSNFRKEF | GFYKIREVNNY 986 |
| WP_047207273 | 916 DD | KARFIQRQLVETRQITKHVARILDERFNNELDSKGRRIR-- | KVKIVTLKSNLVSNFRKEF | GFYKIREVNNY 986 |
| WP_047209694 | 916 DD | KARFIQRQLVETRQITKHVASILDERFNNELDSKGRRIR-- | KVKIVTLKSNLVSNFRKEF | GFYKIREVNNY 986 |
| WP_050198062 | 916 DD | KARFIQRQLVETRQITKHVARILDERFNNELDSKGRRIR-- | KVKIVTLKSNLVSNFRKEF | GFYKIREVNNY 986 |
| WP_050201642 | 916 DD | KARFIQRQLVETRQITKHVARILDERFNNELDSKGRRIR-- | KVKIVTLKSNLVSNFRKEF | GFYKIREVNNY 986 |
| WP_050204027 | 916 DD | KARFIQRQLVETRQITKHVARILDERFNNELDSKGRRIR-- | KVKIVTLKSNLVSNFRKEF | GFYKIREVNNY 986 |
| WP_050881965 | 916 DD | KARFIQRQLVETRQITKHVARILDERFNNELDSKGRRIR-- | KVKIVTLKSNLVSNFRKEF | GFYKIREVNNY 986 |
| WP_050886065 | 916 DD | KARFIQRQLVETRQITKHVARILDERFNNKVDDNNKPIR-- | KVKIVTLKSNLVSNFRKEF | GFYKIREVNNY 986 |
| AHN30376 | 916 DD | KARFIQRQLVETRQITKHVARILDERFNNELDSKGRRIR-- | KVKIVTLKSNLVSNFRKEF | GFYKIREVNNY 986 |
| EA078426 | 916 DD | KARFIQRQLVETRQITKHVARILDERFNNELDSKGRRIR-- | KVKIVTLKSNLVSNFRKEF | GFYKIREVNDY 986 |
| CCW42055 | 916 ND | KARFIQRQLVETRQITKHVARILDERFNAKHDENKKVIR-- | DVKIITLKSNLVSQFRKDF | KFYKVREINDY 980 |
| WP_003041502 | 910 ED | KAGFIKRQLVETRQITKHVAQILDERFNTEFDGAQRRIR-- | NVKIITLKSNLVSNFRKEF | ELYKVREINDY 981 |
| WP_037593752 | 911 ED | KAGFIKRQLVETRQITKHVAQILDERFNTEFDGAQRRIR-- | NVKIITLKSNLVSNFRKEF | ELYKVREINDY 981 |
| WP_049516684 | 910 AD | KAGFIKRQLVETRQITKHVAQILDERFNTERDENDKVIR-- | DVKVITLKSNLVSQFRKDF | KFYKVREINDY 980 |
| GAD46167 | 919 AD | KAGFIKRQLVETRQITKHVAQILDARFNTERDENDKVIR-- | DVKVITLKSNLVSQFRKDF | KFYKVREINDY 989 |
| WP_018363470 | 920 AD | KAGFIKRQLVETRQITKHVAQILDSRMNTKRDKNDKPIR-- | EVKVITLKSKLVSDFRKDF | QLYKVRDINNY 990 |
| WP_003043819 | 910 ED | KAGFIKRQLVETRQITKHVAQILDERFNTEFDGNKRRIR-- | NVKIITLKSNLVSNFRKEF | ELYKVREINDY 980 |
| WP_066269658 | 910 ND | KAGFIKRQLVETRQITKHVAQILDARFNPKRDDNKKVIR-- | DVKIITLKSNLVSQFPRRDF | KLYKVREINDY 980 |
| WP_048800089 | 910 LD | KAGFIHRQLVETRQITKHVAQILDSRMNTKYDENDKLIR-- | EVKVITLKSKLVSDFRKDF | QFYKVREINDY 980 |
| WP_012767106 | 910 LD | KAGFIKRQLVETRQITKHVAQILDSRMNTKYDENDKLIR-- | EVKVITLKSKLVSDFRKDF | QFYKVREINDY 980 |
| WP_014612333 | 910 LD | KAGFIKRQLVETRQITKHVAQILDSRMNTKYDENDKLIR-- | EVKVITLKSKLVSDFRKDF | QFYKVREINDY 980 |
| WP_015017095 | 910 LD | KAGFIKRQLVETRQITKHVAQILDSRMNTKYDENDKLIR-- | KVHIITLKSNLVSDFRKDF | GLYKIRDINHY 980 |
| WP_015057649 | 910 LD | KAGFIKRQLVETRQITKHVAQILDSRFNTEFDDHNKRIR-- | KVHIITLKSNLVSDFRKDF | GLYKIRDINHY 980 |
| WP_048327215 | 910 LD | KAGFIQRQLVETRQITKHVAQILDSRFNTEFDDHNKRIR-- | KVHIITLKSKLVSDFRKDF | GLYKIRDINHY 980 |
| WP_049519324 | 910 VD | KAGFIKRQLVETRQITKHVAQILDSRFNTEFDDHNKRIR-- | KVHIITLKSKLVSDFRKDF | GLYKIRDINHY 980 |
| WP_012515931 | 910 VD | KAGFIKRQLVETRQITKHVAQILDSRFNTEFDDHNKRIR-- | KVHIITLKSKLVSDFRKDF | GLYKIRDINHY 980 |
| WP_021320964 | 910 VD | KAGFIKRQLVETRQITKHVAQILDSRFNTEFDDHNKRIR-- | KVHIITLKSKLVSDFRKDF | GLYKIRDINHY 980 |
| WP_037581760 | 910 VD | KAGFIQLQLVETRQITKHVAQILDSRFNTERDENDKVIR-- | DVKVITLKSSLVSQFRKDF | KFYKVREINDY 980 |
| WP_044232481 | 918 TD | KAGFIKRQLVETRQITKHVAQILDARFNTKCCDENDKVIR-- | DVKVITLKSNLVSQFRKEF | KFYKVREINDY 988 |
| WP_099854540 | 919 AD | KAGFIKRQLVETRQITKHVAQILDSRFNTEHDENDKVIR-- | DVKVITLKSNLVSQFRKDF | EFYKVREINDY 989 |
| WP_012962174 | 919 ND | KAGFIKRQLVETRQITKHVAQILDSRFNTERDENDKVIR-- | NVKVITLKSNLVSQFRKDF | KFYKVREINDY 989 |

```
WP_039695303   921 AD KAGFIKRQLVETRQITKHVAQILDARFNTEHDENDKVIR--DVKVITLKSNLVSQFRKDF EFYKVREINDY 991
WP_014334983   918 AD KAGFIKRQLVETRQITKHVAQILDARFNTKRDENDKVIR--DVKVITLKSNLVSQFRKEF KFYKLREVNDY 988
WP_003099269   911 FD KAGFIKRQLVETRQITKHVAQILDSRFNSNLTEDSKSNR--NVKIITLKSKMVSDFRKDF GFYKLREVNDY 981
AHY15608       911 FD KVGFIKRQLVETRQITKHVAQILDSRFNSNLTEDSKSNR--NVKIITLKSKMVSDFRKDF GFYKLREVNDY 981
AHY17476       911 FD KAGFIKRQLVETRQITKHVAQILDSRFNSNLTEDSKSNR--NVKIITLKSKMVSDFRKDF GFYKLREVNDY 981
ESR09100       -- -- ----------------------------------------------------------- ----------- ---
AGM98575       911 FD KAGFIKRQLVETRQITKHVAQILDSRFNSNLTEDSKSNR--NVKIITLKSKMVSDFRKDF GFYKLREVNDY 981
ALF27331       911 DD KAGFIKRQLVETRQITKHVARILDERFNTETDENNKKIR--QVKIVTLKSNLVSNFRKEF ELYKVREINDY 981
WP_018372492   924 ED KAGFIRRQLVETRQITKHVARLLDEKLNRKKNENGEKLR--TTKIITLKSVFASRFRANF DLYKLRELNHY 994
WP_045618028   914 RD KVGFIKRQLVETRQITKHVAQILDARFNTEVTEKDKKDR--SVKIITLKSNLVSNFRKEF RLYKVREINDY 984
WP_045635197   913 RD KAGFIKRQLVETRQITKHVAQILDARYNTEVNEKDKKNR--TVKIITLKSNLVSNFRKEF RLYKVREINDY 983
WP_002263549   911 DD KAGFIKRQLVETRQITKHVARILDERFNTETDENNKKIR--QVKIVTLKSNLVSNFRKEF ELYKVREINDY 981
WP_002263887   911 DD KAGFIKRQLVETRQITKHVARILDERFNTETDENNKKIR--QVKIVTLKSNLVSNFRKEF ELYKVREINDY 981
WP_002264920   911 DD KAGFIKRQLVETRQITKHVARILDERFNTETDENNKKIR--QVKIVTLKSNLVSNFRKEF ELYKVREINDY 981
WP_002269043   911 DD KAGFIKRQLVETRQITKHVARILDERFNTETDENNKKIR--QVKIVTLKSNLVSNFRKEF ELYKVREINDY 981
WP_002269448   911 DD KAGFIKRQLVETRQITKHVARILDERFYTETDENNKKIR--QVKIVTLKSNLVSNFRKEF ELYKVREINDY 981
WP_002271977   911 DD KAGFIKRQLVETRQITKHVARILDERFYTETDENNKKIR--QVKIVTLKSNLVSNFRKEF ELYKVREINDY 981
WP_002272766   911 DD KAGFIKRQLVETRQITKHVARILDERFNTETDENNKKIR--QVKIVTLKSNLVSNFRKEF ELYKVREINDY 981
WP_002273241   911 DD KAGFIKRQLVETRQITKHVARILDERFNTETDENNKKIR--QVKIVTLKSNLVSNFRKEF ELYKVREINDY 981
WP_002275430   911 DD KAGFIKRQLVETRQITKHVARILDERFNTETDENNKKIR--QVKIVTLKSNLVSNFRKEF ELYKVREINDY 981
WP_002276448   911 DD KAGFIKRQLVETRQITKHVARMLDERFNKEFDDNNKKIR--RVKIVTLKSNLVSSFRKEF ELYKVREINDY 983
WP_002277050   911 DD KAGFIKRQLVETRQITKHVARILDERFHTETDENNKKIR--QVKIVTLKSNLVSNFRKEF ELYKVREINDY 981
WP_002277364   911 DD KAGFIKRQLVETRQITKHVARILDERFHTETDENNKKIR--QVKIVTLKSNLVSNFRKEF ELYKVREINDY 981
WP_002279025   911 DD KAGFIKRQLVETRQITKHVARILDERFNTETDENNKKIR--QVKIVTLKSNLVSNFRKEF ELYKVREINDY 981
WP_002279859   911 DD KAGFIKRQLVETRQITKHVARILDERFYTETDENNKKIR--QVKIVTLKSNLVSNFRKEF ELYKVREINDY 981
WP_002280230   913 DD KAGFIKRQLVETRQITKHVARILDERFHTETDENNKKIR--QVKIVTLKSNLVSNFRKEF ELYKVREINDY 983
WP_002281696   911 DD KAGFIKRQLVETRQITKHVARILDERFNTETDENNKKIR--QVKIVTLKSNLVSNFRKEF ELYKVREINDY 981
WP_002282247   913 DD KAGFIKRQLVETRQITKHVARILDERFNKEFDDNNKKIR--RVKIVTLKSNLVSSFRKEF ELYKVREINDY 983
WP_002282906   911 DD KAGFIKRQLVETRQITKHVARILDERFNTETDENNKKIR--QVKIVTLKSNLVSNFRKEF ELYKVREINDY 981
WP_002283846   911 DD KAGFIKRQLVETRQITKHVARILDERFHTETDENNKKIR--QVKIVTLKSNLVSNFRKEF ELYKVREINDY 981
WP_002287255   911 DD KAGFIKRQLVETRQITKHVARILDERFHTETDENNKKIR--QVKIVTLKSNLVSNFRKEF ELYKVREINDY 981
WP_002288990   911 DD KAGFIKRQLVETRQITKHVARILDERFNTETDENNKKIR--QVKIVTLKSNLVSNFRKEF ELYKVREINDY 981
WP_002289641   911 DD KAGFIKRQLVETRQITKHVARILDERFNTETDENNKKIR--QVKIVTLKSNLVSNFRKEF ELYKVREINDY 981
WP_002290427   911 DD KAGFIKRQLVETRQITKHVARILDERFNTETDENNKKIR--QVKIVTLKSNLVSNFRKEF ELYKVREINDY 981
WP_002295753   911 DD KAGFIKRQLVETRQITKHVARILDERFNTETDENNKKIR--QVKIVTLKSNLVSNFRKEF ELYKVREINDY 981
WP_002296423   911 DD KAGFIKRQLVETRQITKHVARILDERFHTETDENNKKIR--QVKIVTLKSNLVSNFRKEF ELYKVREINDY 981
WP_002304487   925 DD KAGFIKRQLVETRQITKHVARILDERFNTETDENNKKIR--QVKIVTLKSNLVSNFRKEF ELYKVREINDY 995
WP_002305844   911 DD KAGFIKRQLVETRQITKHVARILDERFNTETDENNKKIR--QVKIVTLKSNLVSNFRKEF ELYKVREINDY 981
WP_002307203   911 DD KAGFIKRQLVETRQITKHVARILDERFNTETDENNKKIR--QVKIVTLKSNLVSNFRKEF ELYKVREINDY 981
WP_002310390   911 DD KAGFIKRHQLVETRQITKHVARILDERFNTETDENNKKIR--QVKIVTLKSNLVSNFRKEF ELYKVREINDY 981
WP_023352408   911 DD KAGFIKRQLVETRQITKHVARILDERFNTETDENNKKIR--QVKIVTLKSNLVSNFRKEF ELYKVREINDY 981
WP_012997688   911 DD KAGFIKRQLVETRQITKHVARILDERFNTETDENNKKIR--QVKIVTLKSNLVSNFRKEF ELYKVREINDY 981
WP_014677909   911 DD KAGFIKRQLVETRQITKHVARILDERFNTETDENNKKIR--QVKIVTLKSNLVSNFRKEF ELYKVREINDY 981
WP_019312892   911 DD KAGFIKRQLVETRQITKHVARILDERFHTETDENNKKIR--QVKIVTLKSNLVSNFRKEF ELYKVREINDY 981
WP_019313659   911 DD KAGFIKRQLVETRQITKHVARILDERFHTETDENNKKIR--QVKIVTLKSNLVSNFRKEF ELYKVREINDY 981
WP_019314093   911 DD KAGFIKRQLVETRQITKHVARILDERFNTETDENNKKIR--QVKIVTLKSNLVSNFRKEF ELYKVREINDY 981
WP_019315370   911 DD KAGFIKRQLVETRQITKHVARILDERFNTETDENNKKIR--QVKIVTLKSNLVSNFRKEF ELYKVREINDY 981
WP_019803776   911 DD KAGFIKRQLVETRQITKHVARILDERFNTETDENNKKIR--QVKIVTLKSNLVSNFRKEF ELYKVREINDY 981
WP_019805234   911 DD KAGFIKRQLVETRQITKHVARMLDERFHTETDENNKKIR--RVKIVTLKSNLVSNFRKEF ELYKVREINDY 981
WP_024784288   913 DD KAGFIKRQLVETRQITKHVARILDERFNTETDENNKKIR--QVKIVTLKSNLVSSFRKEF ELYKVREINDY 983
WP_024784666   911 DD KAGFIKRQLVETRQITKHVARILDERFNTETDENNKKIR--QVKIVTLKSNLVSNFRKEF ELYKVREINDY 981
WP_024784894   911 DD KAGFIKRQLVETRQITKHVARILDERFNTETDENNKKIR--QVKIVTLKSNLVSNFRKEF ELYKVREINDY 981
```

```
                     -continued
WP_024786433  913 DD KAGFIKRQLVETRQITKHVARMLDERFNKEFDDNNKRIR--RVKIVTLKSNLVSSFRKEF ELYKVREINDY 983
WP_049473442  911 DD KAGFIKRQLVETRQITKHVARILDERFNTETDENNKKIR--QVKIVTLKSNLVSNFRKEF ELYKVREINDY 981
WP_049474547  911 DD KAGFIKRQLVETRQITKHVARILDERFNTETDENNKKIR--QVKIVTLKSNLVSNFRKEF ELYKVREINDY 981
EMC03581      904 DD KAGFIKRQLVETRQITKHVARILDERFHTETDENNKKIR--QVKIVTLKSNLVSNFRKEF ELYKVREINDY 974
WP_000428612  916 RD KVGFIKRQLVETRQITKHVAQILDARYNTEVNEKDKKNR--TVKIITLKSNLVSNFRKEF RLYKIREINDY 986
WP_002364836  914 RD KVGFIKRQLVETRQITKHVAQILDARFNKEVNEKDKKNR--TVKIITLKSNLVSNFRKEF RLYKIREINDY 984
WP_049523028  909 RD KVGFIKRQLVETRQITKHVAQILDDRFNAEVNEKNQKLR--SVKIITLKSNLVSNFRKEF GLYKVREINDY 979
WP_003107102  880 YD KAGFIKRQLVETRQITKHVAQILNNRFNNNVDDSSKNKR--PVKIITLKSKMVSDFRKEF GFYKIREVNDY 950
WP_054279288  912 SD KANFIQRQLVETRQITKHVAQILDSRFNTERDEKDRPIR--RVKVITLKSKFVSDFRQDF GFYKLREINDY 982
WP_049531101  914 RD KVGFIRRQLVETRQITKHVAQILDDRFNTKVNEKNQKIR--TVKIITLKSNLVSNFRKEF RLYKVREINDY 984
WP_049538452  914 RD KVGFIRRQLVETRQITKHVAQILDSRFNTEVTEKDKKNR--NVKIITLKSNLVSNFRKEF GLYKVREINDY 984
WP_049549711  916 LD KVGFIKRQLVETRQITKHVAQILDARFNKEVTEKDKKNR--NVKIITLKSKIVSDFRKDF RLYKVREINDY 986
WP_007896501  917 SD KARFLRRQLVETRQITKHVAQLLDDSRFNSKSNQNKKLAR-NVKIITLKSKIVSDFRKDF GLYKLREVNNY 987
EFR44625      869 SD KARFIRRQLVETRQITKHVAQLLDDSRFNSKSNQNKKLAR-NVKIITLKSKIVSDFRKDF GLYKLREVNNY 939
WP_002897477  913 ED KVGFIRRQLVETRQITKNVAQILDARFNTEVKEKNQKIR--TVKIITLKSNLVSNFRKEF GFYKVREINDY 983
WP_002906454  913 RD KVGFIKRQLVETRQITKHVAQLLDTRENTVNEENQKIR---TVKIITLKSNLVSNFRKEF GLYKVREINDY 983
WP_009729476  914 LD KVGFIKRQLVETRQITKHVAQILDARFNKEVTEKDKKNR--NVKIITLKSNLVSNFRKEF ELYKVREINDY 984
CQR24647      913 ED KAGFIKRQLVETRQITKHVAQILDERFNRDFDKNDKRIR--NVKIVTLKSNLVSNFRKEF GFYKVREINNF 983
WP_000066813  918 LD KVGFIRRQLVETRQITKHVAQFLDARFNMEVSEKNQKIR--NVKIITLKSNLVSNFRKEF GLYKVREINDY 988
WP_009754323  914 RD KVGFIKRQLVETRQITKHVARILDARENTEVSEKNQKIR--SVKIITLKSNLVSNFRKEF KLYKVREINDY 984
WP_044674937  913 ED KARFIQRQLVETRQITKHVAQILDTRENTKLDEAGNRIRdpKVNIITLKSNLVSQFRKDY QLYKVREINNY 985
WP_044676715  915 ED KARFIQRQLVETRQITKHVAQILDTRENTKLDEAGNRIRdpKVNIITLKSNLVSQFRKDY QLYKVREINNY 987
WP_044680361  915 ED KARFIQRQLVETRQITKHVAQILDTRENTKLDEAGNRIRdpKVNIITLKSNLVSQFRKDY QLYKVREINNY 987
WP_044681799  913 ED KVGFIKRQLVETRQITKHVARILDARFNKEVTEKDKKNR--KVNIITLKSNLVSQFRKDY GLYKVREINDY 985
WP_049533112  910 ND KAGFIKRQLVETRQITKHVAQVLDARFANKHDENKKVIR--DVKIITLKSNLVSQFRKDF KFYKVREINDY 980
WP_029090905  891 RD KEGFIARQLVETRQITKHVTQLLQQEY--------K-dTTKVFAIKATLVSGLRRKF EFIKNRNVNDY 951
WP_066506696  917 ED EERFINRQLVETRQITKNVTQIIEDHYST--------TKVAAIRANLSHEFRVKN HIYKNRDINDY 976
AIT42264      911 LD KAGFIQRQLVETRQITKHVQILDSRMNTKYDENDKLIR--EVKVITLKSKLVSDERKDF QLYKVREINNY 981
WP_034440723  915 RD RQQFINRQLVETRQITKHVANLLSHHLNEK----KEVG--EINIVLLKSALTSQFRKKE DFYKVREVNDY 980
AKQ21048      911 LD KAGFIKRQLVETRQITKHVAQILDSRMNTKYDENDKLIR--EVKVITLKSKLVSDERKDF QFYKVREINNY 981
WP_004636532  916 AD RAHFLNRQLVETRQITKHVANLLDSQYNTAEEQ--R---INIVLLKSSMTSRFRKEF KLYKVREINDY 980
WP_002364836  922 ED KAHFIQRQLVETRQITKHVAQILDQRYNAKSE------K--KVQIITLKASLTSQFRSIF GLYKVREVNDY 987
WP_016631044  873 ED KAHFIQRQLVETRQITKHVAQILDQRYNAKSE------K--KVQIITLKASLTSQFRSIF GLYKVREVNDY 938
EMS75795      655 ED KARFIQRQLVETRQITKHVAGILDQYFN-QPEE-SK-NK--GIRIITLKSSLVSQFRKTF GINKVREINNH 722
WP_002373311  922 ED KAHFIQRQLVETRQITKHVAQILDQRYNAKSE------K--KVQIITLKASLTSQFRSIF GLYKVREVNDY 987
WP_002378009  922 ED KAHFIQRQLVETRQITKHVAGILDQRYNAKSE------K--KVQIITLKASLTSQFRSIF GLYKVREVNDY 987
WP_002407324  922 ED KAHFIQRQLVETRQITKHVAGILDQRYNAKSE------K--KVQIITLKASLTSQFRSIF GLYKVREVNDY 987
WP_002413717  922 ED KAHFIQRQLVETRQITKHVAGILDQRYNAKSE------K--KVQIITLKASLTSQFRSIF GLYKVREVNDY 987
WP_010775580  924 ED KAHFIQRQLVETRQITKHVAGILNQRYNANSE------K--KVQIITLKASLTSQFRSIF GLYKVREVNDY 989
WP_010818269  920 ED KAHFIQRQLVETRQITKHVAGILDQRYNAKSE------K--KVQIITLKASLTSQFRSIF GLYKVREVNDY 987
WP_010824395  922 ED KAHFIQRQLVETRQITKHVAGILDLYNAKSE-------K--KVQIITLKASLTSQFRSIF GLYKVREVNDY 987
WP_016622645  922 ED KAHFIQRQLVETRQITKHVAGILDQRYNAKSE------K--KVQIITLKASLTSQFRSIF GLYKVREVNDY 987
WP_033624816  922 ED KAHFIQRQLVETRQITKHVAGILDQRYNAKSE------K--KVQIITLKASLTSQFRSIF GLYKVREVNDY 987
WP_002362576  920 ED KAHFIQRQLVETRQITKHVAGILHREN-KAEDTNEPIR---KVRIITLKSALVSQFRNRF GLYKVREVNDY 987
WP_337789179  920 ED KAHFIQRQLVETRQITKHVAGILHHREN-KAEDTNEPIR--KVRIITLKSALVSQFRNRF GIYKVREINEY 988
WP_002310644  919 ED KAHFIQRQLVETRQITKHVAGILHHREN-KAEDTNEPIR--KVRIITLKSALVSQFRNRF GIYKVREVNDY 987
WP_002312694  920 ED KAHFIQRQLVETRQITKHVAGILHHREN-KAEDTNEPIR--KVRIITLKSALVSQFRNRF GIYKVREVNDY 988
WP_002314015  920 ED KAHFIQRQLVETRQITKHVAGILHHREN-KAEDTNEPIR--KVRIITLKSALVSQFRNRF GIYKVREINEY 989
WP_002320716  920 ED KAHFIQRQLVETRQITKHVAGILHHREN-KAEDTNEPIR--KVRIITLKSALVSQFRNRF GIYKVREINEY 989
WP_002330729  919 ED KAHFIQRQLVETRQITKHVAGILHHREN-KAEDTNEPIR--KVRIITLKSALVSQFRNRF GIYKVREINEY 988
WP_002335161  920 ED KAGFIQRQLVETRQITKHVAGILHHREN-KAEDTNEPIR--KVRIITLKSALVSQFRNRF GIYKVREINEY 989
WP_002345439  920 ED KAGFIQRQLVETRQITKHVAGILHHREN-KAEDTNEPIR--KVRIITLKSALVSQFRNRF GIYKVREINEY 989
WP_034867970  911 ED KARFIQRQLVETRQITKHVANILHQSFN-QEEEGTD-CD--GVQIITLKATLTSQFRQTF GLYKVREINPH 979
```

```
WP_047937432    920 ED KAGFIKRQLVETRQITKHVAGILHHRFN-KAEDTNEPIR--KVRIITLKSALVSQFRNRF GIYKVREINEY  989
WP_010720994    911 ED KARFIQRQLVETRQITKHVANILHQSFN-QEEEGTD-CD--GVQITLKATLTSQFRQTF GLYKVREINPH  979
WP_010737004    911 ED KARFIQRQLVETRQITKHVANILHQSFN-QEEEGTD-CD--GVQITLKATLTSQFRQTF GLYKVREINPH  979
WP_034700478    911 ED KARFIQRQLVETRQITKHVANILHQSFN-QEEEGTD-CD--GVQITLKATLTSQFRQTF GLYKVREINPH  979
WP_007209003    912 SD KAGFLKRQLVETRQITKHVATILDSKFNE--DSNNRDVQ----IITLKSALVSEFRKTF NLYKVREINDL  977
WP_023519017    905 AD KARFIQRQLVETRQITKHVANLLHQHFN-LPEEVSA-TE--KTSIITLKSTLTSQFRQMF DIYKVREINHH  973
WP_010770040    915 DD RAHFIKRQLVETRQITKHVARILDQRFNSQKDEEGKTIR--AVRVVTLKSSLTSQFRKQF AIHKVREINDY  985
WP_048604708    912 DD KAGFIHRQLVETRQITKHVARILHQRFNSEKDEEGNLIR--KVRIITLKSALTSQFRKNY GIYKIREINDY  982
WP_010750235    914 DD KARFIHRQLVETRQITKHVAAILHQYFN-QTQELEK-EK--DIRIITLKSSLVSQFRQVF GIHKVREINHH  982
AII16583        950 LD KAGFIKRQLVETRQITKHVAQILDSRMNTKYDENDKLIR--EVKVITLKSKLVSDERKDF QFYKVREINNY  1020
WP_029073316    928 KD KERFINRQIVETRQITKHVAQIISNHYET--------------TKVVTVRADLSHAFRERY HIYKNRDINDF  987
WP_015899969    928 KD QERFINRQIVETRQITKHVAQIIDNHYEN----------------TKVVTVRADLSHQFRERY HIYQNRDINDF  987
KDA45870        903 KL KERFIERQLVETRQITKVAQLLDQRLN--YDNGVELD-eKIAIVTLKAQLASQFRSEF KLRKVRALNNL  972
WP_039099354    924 -D MKGFINRQLVETRQVIKLATNLLMEQYGED--------------NIELITVKSGLTHQMRTEF DFPKNRNLANNH  990
AKP02966        926 KD KLGFIHRQLVQTSQMVKGVANILNSMYK---NQGTTCIQ------ARANLSTAFRKAL ELVKRNINDF  999
WP_010991369    914 AD KARFIHRQLVETRQITKHVANILHQRFNYEKDHGNTMK--QVRIVTLKSALVSQFRKQF QLYKVRDVNDY  984
WP_033388504    914 AD KARFIHRQLVETRQITKHVANILHQRFNYEKDHGNTMK--QVRIVTLKSALVSQFRKQF QLYKVRDVNDY  984
EHN60060        917 AD KARFIHRQLVETRQITKHVANILHQRFNYEKDHGNTMK--QVRIVTLKSALVSQFRKQF QLYKVRDVNDY  987
EFR89594        683 AD KATFIHRQLVETRQITKVANILHQRFNYGKDHGNTMK--QVRIVMLKSALVSQFRKQF QLYKVRGVNDY  753
WP_038409211    914 AD KANFIQRQLVETRQITKVANILYQRFNCKQDENGNEVE--QVRIVTLKSTLVSQFRKQF QLYKVREVNDY  984
EFR95520        533 AD KANFIQRQLVETRQITKNVANILYQRFNCKQDENGNEVE--QVRIVTLKSTLVSQFRKQF QLYKVREVNDY  603
WP_003723650    914 AD KARFIHRQLVETRQITKNVANILYQRFNKETDNHGNTME--QVRIVTLKSALVSQFRKQF QLYKVREVNGY  984
WP_003727705    914 AD KARFIHRQLVETRQITKNVANILHQRFNKETDNHGNTME--QVRIVTLKSALVSQFRKQF QLYKVREVNDY  984
WP_003730785    914 AD KARFIHRQLVETRQITKNVANILHQRFNKETDNHGNTME--QVRIVTLKSALVSQFRKQF QLYKVREVNDY  984
WP_003733029    914 AD KARFIHRQLVETRQITKNVANILHQRFNYKTDGNKDTME--TVRIVTLKSALVSQFRKQF QLYKVREVNDY  984
WP_003739838    917 AD KARFIHRQLVETRQITKNVANILHQRFNNETDNHGNNME--QVRIVMLKSALVSQFRKQF QLYKVREVNDY  987
WP_014601172    914 AD KARFIHRQLVETRQITKNVANILHQRFNNETDNHGNTME--EVKVITLKSKLVSDFRKDF QFYKVREINNY  984
WP_023548323    914 AD KARFIHRQLVETRQITKNVANILHQRFNNETDDNEDTME--PVRIVTLKSALVSQFRKQF QLYKVREVNDY  984
WP_031665337    914 AD KARFIHRQLVETRQITKNVANILHQRFNNETDGNKDTME--TVRIVTLKSALVSQFRKQF QLYKVREVNDY  984
WP_031669209    914 AD KARFIHRQLVETRQITKNVANILHQRFNNETDDNEDTME--QVRIVTLKSALVSQFRKQF QLYKVREVNDY  984
WP_033920898    917 AD KARFIHRQLVETRQITKNVANILHQRFNNETDDNEDTME--PVRIVTLKSALVSQFRKQF QLYKVREVNDY  987
AKI42028        917 AD KARFIHRQLVETRQITKNVANILHQRFNNETDNHGNTME--QVRIVTLKSALVSQFRKQF QLYKVREVNDY  987
AKI50529        362 AD KARFIHRQLVETRQITKNVANILHQRFNCKKDESGNVIE--QVRIVTLKAALVSQFRKQF QLYKVREVNDY  432
EFR83390        914 AD KARFIHRQLVETRQITKNVANILHQRFNCKKDESGNVIE--QVRIVTLKAALVSQFRKQF QLYKVREVNDY  984
WP_046323366    927 LD KARFIHRQLVETRQITKNVANILHQRFNYKTDEKDKLIR--EVKVITLKSKLVSDFRKDF QFYKVREINNY  997
AKE81011        921 RD EERFINRQLVETRQITKNVTQIIEDHYST---------------TKVAAIRANLSHEFRVKN HIYKNRDINDY  980
CUO82355        923 KD KERFINRQLVETRQITKNVIIKNVAVIINDHYTN----------TNIVTVRAELSHQFRERY KIYKNRDINDF  982
WP_033162887    944 LD KAGFIKRQLVETRQITKHVAQILDSRMNTKYDENDKLIR--EVKVITLKSKLVSDFRKDF QFYKVREINNY  1014
AGZ01981        911 LD KAGFIKRQLVETRQITKHVAQILDSRMNTKYDENDKLIR--EVKVITLKSKLVSDFRKDF QFYKVREINNY  981
AKA60242        911 LD KAGFIKRQLVETRQITKHVAQILDSRMNTKYDENDKLIR--EVKVITLKSKLVSDFRKDF QFYKVREINNY  981
AKS40380        915 LD KAGFIKRQLVETRQITKHVAQILDSRMNTKYDENDKLIR--EVKVITLKSKLVSDFRKDF QFYKVREINNY  985
4UN5_B          982 LD KAGFIKRQLVETRQITKHVAQILDSRMNTKYDENDKLIR--EVKVITLKSKLVSDFRKDF QFYKVREINNY  1051
WP_010922251    982 HHAHDAYLNAVVGTALIKKYPKL-ESEFVYGDYKVYDV S---EQEi--GK ATAKY--F-FYSNIM-NFFKTEIT  1051
WP_039695303    992 HHAHDAYLNAVVGTALLKKYPKL-ASEFVYGEYKKYDI S---SD---KATAK-YfFYSNLM-NFFKTKVK  1058
WP_045635197    984 HHAHDAYLNAVVAKAILKKYPKL-EPEFVYGEYQKYDL SkdpKEV--EK ATEKEY-ATEKEY-FYSNLL-NFFKEEVH  1055
5AXW_A          703 HHAEDALI-----------------IaNADFIFKEWKKLDK Nq-mFE---EK ETEQEy-KEiFITPHQiKHIKDFKD  771
WP_009880683    666 HHAEDALI--------------------------------------------------------  735
WP_010922251    982 HHAHDAYLNAVVGTALIKKYPKL-ESEFVYGDYKVYDI S---EQEi-GK ATAKY--F-FYSNIM-NFFKTEIT  1051
WP_011054416    982 HHAHDAYLNAVVGTALIKKYPKL-ESEFVYGDYKVYDV S---EQEi-GK ATAKY--F-FYSNIM-NFFKTEIT  1051
WP_011284745    982 HHAHDAYLNAVVGTALIKKYPKL-ESEFVYGDYKVYDV S---EQEi-GK ATAKY--F-FYSNIM-NFFKTEIT  1051
WP_011285506    982 HHAHDAYLNAVVGTALIKKYPKL-ESEFVYGDYKVYDV S---EQEi-GK ATAKY--F-FYSNIM-NFFKTEIT  1051
WP_011527619    982 HHAHDAYLNAVVGTALIKKYPKL-ESEFVYGDYKVYDV S---EQEi-GK ATAKY--F-FYSNIM-NFFKTEIT  1051
WP_012560673    982 HHAHDAYLNAVVGTALIKKYPKL-ESEFVYGDYKVYDI S---EQEi-GK ATAKY--F-FYSNIM-NFFKTEIT  1051
```

-continued

| | | | | |
|---|---|---|---|---|
| WP_014407541 | 981 | HHAHDAYLNAVVGTALIKKYPKL-ESEFVYGDYKVYDV | S---EQEi--GK ATAKY--F-FYSNIM-NFFKTEIT | 1050 |
| WP_020905136 | 982 | HHAHDAYLNAVVGTALIKKYPKL-ESEFVYGDYKVYDV | S---EQEi-GK ATAKY--F-FYSNIM-NFFKTEIT | 1051 |
| WP_023080005 | 981 | HHAHDAYLNAVVGTALIKKYPKL-ESEFVYGDYKVYDV | S---EQEi--GK ATAKY--F-FYSNIM-NFFKTEIT | 1050 |
| WP_023610282 | 982 | HHAHDAYLNAVVGTALIKKYPKL-ESEFVYGDYKVYDV | S---EQEi-GK ATAKY--F-FYSNIM-NFFKTEIT | 1051 |
| WP_030125963 | 982 | HHAHDAYLNAVVGTALIKKYPKL-ESEFVYGDYKVYDV | S---EQEi-GK ATAKY--F-FYSNIM-NFFKTEIT | 1051 |
| WP_030126706 | 982 | HHAHDAYLNAVVGTALIKKYPKL-ESEFVYGDYKVYDV | S---EQEi-GK ATAKY--F-FYSNIM-NFFKTEIT | 1051 |
| WP_031488318 | 982 | HHAHDAYLNAVVGTALIKKYPKL-ESEFVYGDYKVYDV | S---EQEi-GK ATAKY--F-FYSNIM-NFFKTEIT | 1051 |
| WP_032460140 | 982 | HHAHDAYLNAVVGTALIKKYPKL-ESEFVYGDYKVYDV | S---EQEi-GK ATAKY--F-FYSNIM-NFFKTEIT | 1051 |
| WP_032461047 | 982 | HHAHDAYLNAVVGTALIKKYPKL-ESEFVYGDYKVYDI | S---EQEi-GK ATAKY--F-FYSNIM-NFFKTEIT | 1051 |
| WP_032462016 | 982 | HHAHDAYLNAVVGTALIKKYPKL-ESEFVYGDYKVYDV | S---EQEi-GK ATAKY--F-FYSNIM-NFFKTEIT | 1051 |
| WP_032462936 | 982 | HHAHDAYLNAVVGTALIKKYPKL-ESEFVYGDYKVYDV | S---EQEi-GK ATAKY--F-FYSNIM-NFFKTEIT | 1051 |
| WP_032464890 | 982 | HHAHDAYLNAVVGTALIKKYPKL-ESEFVYGDYKVYDV | S---EQEi-GK ATAKY--F-FYSNIM-NFFKTEIT | 1051 |
| WP_033888930 | 807 | HHAHDAYLNAVVGTALIKKYPKL-ESEFVYGDYKVYDV | S---EQEi-GK ATAKY--F-FYSNIM-NFFKTEIT | 876 |
| WP_038431314 | 982 | HHAHDAYLNAVVGTALIKKYPKL-ESEFVYGDYKVYDV | S---EQEi-GK ATAKY--F-FYSNIM-NFFKTEIT | 1051 |
| WP_038432938 | 981 | HHAHDAYLNAVVGTALIKKYPKL-ESEFVYGDYKVYDV | S---EQEi-GK ATAKY--F-FYSNIM-NFFKTEIT | 1050 |
| WP_038434062 | 982 | HHAHDAYLNAVVGTALIKKYPKL-ESEFVYGDYKVYDV | S---EQEi-GK ATAKY--F-FYSNIM-NFFKTEIT | 1051 |
| BAQ51233 | 893 | HHAHDAYLNAVVGTALIKKYPKL-ESEFVYGDYKVYDV | S---EQEi-GK ATAKY--F-FYSNIM-NFFKTEIT | 962 |
| KGE60162 | 157 | HHAHDAYLNAVVGTALIKKYPKL-ESEFVYGDYKVYDV | S---EQEi-GK ATAKY--F-FYSNIM-NFFKTEIT | 226 |
| KGE60856 | | ------------------------------------- | ------------------------------------- | |
| WP_002989955 | 982 | HHAHDAYLNAVVGTALIKKYPKL-ESEFVYGDYKVYDV | S---EQEi-GK ATAKY--F-FYSNIM-NFFKTEIT | 1051 |
| WP_003030002 | 981 | HHAHDAYLNAVVGNALLLKKYPKL-EPEFVYGEYPKYN | S---YR---sRK SATEK-F1FYSNIL-RFFKKE-- | 1041 |
| WP_003065552 | 992 | HHAHDAYLNAVVGTALIKKYPKL-ASEFVYGEYKKYDI | S---SD----- KATAK-YfFYSNLM-NFFKRVIR | 1058 |
| WP_001040076 | 987 | HHAHDAYLNAVVAKAILTKYPQL-EPEFVYGLYRRKK- | L---SKI---VR ATRKM--F-FYSNLM-NMFKRVVR | 1057 |
| WP_001040078 | 987 | HHAHDAYLNAVVAKAILTKYPQL-EPEFVYGDYPKYN | S---YKT---RK ATEKL--F-FYSNIM-NFFKTKVT | 1049 |
| WP_001040080 | 987 | HHAHDAYLNAVVAKAILTKYPQL-EPEFVYGDYPKYN | S---YKT---RK ATEKL--F-FYSNIM-NFFKTKVT | 1049 |
| WP_001040081 | 987 | HHAHDAYLNAVVAKAILTKYPQL-EPEFVYGDYPKYN | S---YKT---RK ATEKL--F-FYSNIM-NFFKTKVT | 1049 |
| WP_001040083 | 987 | HHAHDAYLNAVVAKAILTKYPQL-EPEFVYGDYPKYN | S---YKT---RK ATEKL--F-FYSNIM-NFFKTKVT | 1049 |
| WP_001040085 | 987 | HHAHDAYLNAVVAKAILTKYPQL-EPEFVYGDYPKYN | S---YKT---RK ATEKL--F-FYSNIM-NFFKTKVT | 1049 |
| WP_001040087 | 987 | HHAHDAYLNAVVAKAILTKYPQL-EPEFVYGDYPKYN | S---YKT---RK ATEKL--F-FYSNIM-NFFKTKVT | 1049 |
| WP_001040088 | 987 | HHAHDAYLNAVVAKAILTKYPQL-EPEFVYGDYPKYN | S---YKT---RK ATEKL--F-FYSNIM-NFFKTKVT | 1049 |
| WP_001040089 | 987 | HHAHDAYLNAVVAKAILTKYPQL-EPEFVYGDYPKYN | S---YKT---RK ATEKL--F-FYSNIM-NFFKTKVT | 1049 |
| WP_001040090 | 987 | HHAHDAYLNAVVAKAILTKYPQL-EPEFVYGDYPKYN | S---YKT---RK ATEKL--F-FYSNIM-NFFKTKVT | 1049 |
| WP_001040091 | 987 | HHAHDAYLNAVVAKAILTKYPQL-EPEFVYGDYPKYN | S---YKT---RK ATEKL--F-FYSNIM-NFFKTKVT | 1049 |
| WP_001040092 | 987 | HHAHDAYLNAVVAKAILTKYPQL-EPEFVYGDYPKYN | S---YKT---RK ATEKL--F-FYSNIM-NFFKTKVT | 1049 |
| WP_001040094 | 987 | HHAHDAYLNAVVAKAILTKYPQL-EPEFVYGDYPKYN | S---YKT---RK ATEKL--F-FYSNIM-NFFKTKVT | 1049 |
| WP_001040095 | 987 | HHAHDAYLNAVVAKAILTKYPQL-EPEFVYGDYPKYN | S---YKT---RK ATEKL--F-FYSNIM-NFFKTKVT | 1049 |
| WP_001040096 | 987 | HHAHDAYLNAVVAKAILTKYPQL-EPEFVYGDYPKYN | S---YKT---RK ATEKL--F-FYSNIM-NFFKTKVT | 1049 |
| WP_001040097 | 987 | HHAHDAYLNAVVAKAILTKYPQL-EPEFVYGDYPKYN | S---YKT---RK ATEKL--F-FYSNIM-NFFKTKVT | 1049 |
| WP_001040098 | 987 | HHAHDAYLNAVVAKAILTKYPQL-EPEFVYGDYPKYN | S---YKT---RK ATEKL--F-FYSNIM-NFFKTKVT | 1049 |
| WP_001040099 | 987 | HHAHDAYLNAVVAKAILTKYPQL-EPEFVYGDYPKYN | S---YKT---RK ATEKL--F-FYSNIM-NFFKTKVT | 1049 |
| WP_001040100 | 987 | HHAHDAYLNAVVAKAILTKYPQL-EPEFVYGDYPKYN | S---YKT---RK ATEKL--F-FYSNIM-NFFKTKVT | 1049 |
| WP_001040104 | 987 | HHAHDAYLNAVVAKAILTKYPQL-EPEFVYGDYPKYN | S---YKT---RK ATEKL--F-FYSNIM-NFFKTKVT | 1049 |
| WP_001040105 | 987 | HHAHDAYLNAVVAKAILTKYPQL-EPEFVYGDYPKYN | S---YKT---RK ATEKL--F-FYSNIM-NFFKTKVT | 1049 |
| WP_001040106 | 987 | HHAHDAYLNAVVAKAILTKYPQL-EPEFVYGDYPKYN | S---YKT---RK ATEKL--F-FYSNIM-NFFKTKVT | 1049 |
| WP_001040107 | 987 | HHAHDAYLNAVVAKAILTKYPQL-EPEFVYGDYPKYN | S---YKT---RK ATEKL--F-FYSNIM-NFFKTKVT | 1049 |
| WP_001040108 | 987 | HHAHDAYLNAVVAKAILTKYPQL-EPEFVYGDYPKYN | S---YKT---RK ATEKL--F-FYSNIM-NFFKTKVT | 1049 |
| WP_001040109 | 987 | HHAHDAYLNAVVAKAILTKYPQL-EPEFVYGDYPKYN | S---YKT---RK ATEKL--F-FYSNIM-NFFKTKVT | 1049 |
| WP_001040110 | 987 | HHAHDAYLNAVVAKAILTKYPQL-EPEFVYGDYPKYN | S---YKT---RK ATEKL--F-FYSNIM-NFFKTKVT | 1049 |
| WP_015058523 | 987 | HHAHDAYLNAVVAKAILTKYPQL-EPEFVYGDYPKYN | S---YKT---RK ATEKL--F-FYSNIM-NFFKTKVT | 1049 |
| WP_017643650 | 987 | HHAHDAYLNAVVAKAILTKYPQL-EREFVYGDYPKYN | S---YKT---RK ATEKL--F-FYSNIM-NFFKTKVT | 1049 |
| WP_017647151 | 987 | HHAHDAYLNAVVAKAILTKYPQL-EPEFVYGDYPKYN | S---YKT---RK ATEKL--F-FYSNIM-NFFKTKVT | 1049 |
| WP_017648376 | 987 | HHAHDAYLNAVVAKAILTKYPQL-EPEFVYGDYPKYN | S---YKT---RK ATEKL--F-FYSNIM-NFFKTKVT | 1049 |
| WP_017649527 | 987 | HHAHDAYLNAVVAKAILTKYPQL-EPEFVYGDYPKYN | S---YKT---RK ATEKL--F-FYSNIM-NFFKTKVT | 1049 |

```
WP_017771611   987 HHAHDAYLNAVLNAVVAKAILTKYPQL-EPEFVYGDYPKYN-S---YKT---RK ATEKL--F-FYSNIM-NFFKTKVT 1049
WP_017771984   987 HHAHDAYLNAVLNAVVAKAILTKYPQL-EPEFVYGDYPKYN-S---YKT---RK ATEKL--F-FYSNIM-NFFKTKVT 1049
CFQ25032       987 HHAHDAYLNAVLNAVVAKAILTKYPQL-EPEFVYGDYPKYN-S---YKT---RK ATEKL--F-FYSNIM-NFFKTKVT 1049
CFV16040       987 HHAHDAYLNAVLNAVVAKAILTKYPQL-EPEFVYGDYPKYN-S---YKT---RK ATEKL--F-FYSNIM-NFFKTKVT 1049
KLJ37842       987 HHAHDAYLNAVLNAVVAKAILTKYPQL-EPEFVYGDYPKYN-S---YKT---RK ATEKL--F-FYSNIM-NFFKTKVT 1049
KLJ72361       987 HHAHDAYLNAVLNAVVAKAILTKYPQL-EPEFVYGDYPKYN-S---YKT---RK ATEKL--F-FYSNIM-NFFKTKVT 1049
KLL20707      1001 HHAHDAYLNAVLNAVVAKAILTKYPQL-EPEFVYGDYPKYN-S---YKT---RK ATEKL--F-FYSNIM-NFFKTKVT 1063
KLL42645       987 HHAHDAYLNAVLNAVVAKAILTKYPQL-EPEFVYGDYPKYN-S---YKT---RK ATEKL--F-FYSNIM-NFFKTKVT 1049
WP_047207273   987 HHAHDAYLNAVLNAVVAKAILTKYPQL-EPEFVYGDYPKYN-S---YKT---RK ATEKL--F-FYSNIM-NFFKTKVT 1049
WP_047209694   987 HHAHDAYLNAVLNAVVAKAILTKYPQL-EPEFVYGDYPKYN-S---YKT---RK ATEKL--F-FYSNIM-NFFKTKVT 1049
WP_050198062   987 HHAHDAYLNAVLNAVVAKAILTKYPQL-EPEFVYGDYPKYN-S---YKT---RK ATEKL--F-FYSNIM-NFFKTKVT 1049
WP_050201642   987 HHAHDAYLNAVLNAVVAKAILTKYPQL-EPEFVYGDYPKYN-S---YKT---RK ATEKL--F-FYSNIM-NFFKTKVT 1049
WP_050204027   987 HHAHDAYLNAVLNAVVAKAILTKYPQL-EPEFVYGDYPKYN-S---YKT---RK ATEKL--F-FYSNIM-NFFKTKVT 1049
WP_050881965   987 HHAHDAYLNAVLNAVVAKAILTKYPQL-EPEFVYGDYPKYN-S---YKT---RK ATEKL--F-FYSNIM-NFFKTKVT 1049
WP_050886065   987 HHAHDAYLNAVLNAVVAKAILTKYPQL-EPEFVYGDYPKYN-S---YKT---RK ATEKL--F-FYSNIM-NFFKTKVT 1049
AHN30376       987 HHAHDAYLNAVLNAVVAKAILTKYPQL-EPEFVYGDYPKYN-S---YKT---RK ATEKL--F-FYSNIM-NFFKTKVT 1049
EA078426       987 HHAHDAYLNAVLNAVVAKAILTKYPQL-EPEFVYGDYPKYN-S---YKT---RK ATEKL--F-FYSNIM-NFFKTKVT 1049
CCW42055       981 HHAHDAYLNAVLNAVIGTALLKKYPKL-ASEFVYGEFKKYDV S---DK---eIG KATAK--YfFYSNLM-NFFKKEVK 1050
WP_003041502   982 HHAHDAYLNAVVGNALLLKYPKL-EPEFVYGDYPKYN-S---sRK SATEK--F1FYSNIL-RFFKKE-- 1042
WP_037593752   982 HHAHDAYLNAVVGNALLLKYPKL-EPEFVYGDYPKYN-S---YR---sRK SATEK--F1FYSNIL-RFFKKE-- 1041
WP_049516684   981 HHAHDAYLNAVVGNALLLKYPKL-EPEFVYGEYPKYN-S---YR---sRK SATEK--F1FYSNIL-RFFKKE-- 1041
GAD46167       990 HHAHDAYLNAVVGTALLKKYPKL-APEFVYGDYKKYDV S---SDDhseMG KATAK--YfFYSNLM-NFFKRVIR 1062
WP_018363470   991 HHAHDAYLNAVVGTALLKKYPKL-EPEFVYGDYKKYDV S---EQEi--GK ATAKR--F-FYSNLM-NFFKTEVK 1060
WP_003043819   981 HHAHDAYLNAVVGTALLKKYPKL-EPEFVYGDYKKYDV S---YR---sRK SATEK--F1FYSNIL-RFFKKE-- 1041
WP_006269858   981 HHAHDAYLNAVVGTALLKKYPKL-TSEFVYGEYKKYDV S---DND---eIG KATAK--YfFYSNLM-NFFKTEVK 1051
WP_048800889   981 HHAHDAYLNAVVGTALIKKYPKL-ESEFVYGDYKVYDV S---EQEi--GK ATAKR--F-FYSNLM-NFFKTEIT 1050
WP_012767106   981 HHAHDAYLNAVVGTALIKKYPKL-ESEFVYGDYKVYDV S---EQEi--GK ATAKR--F-FYSNLM-NFFKTEIT 1050
WP_014612333   981 HHAHDAYLNAVVGTALIKKYPKL-ESEFVYGDYKVYDV S---EQEi--GK ATAKR--F-FYSNLM-NFFKTEIT 1050
WP_015017095   981 HHAHDAYLNAVVGTALIKKYPKL-ESEFVYGDYKVYDV S---EQEi--GK ATAKR--F-FYSNLM-NFFKTEIT 1050
WP_015057649   981 HHAHDAYLNAVVGTALIKKYPKL-ESEFVYGDYKVYDV S---EQEi--GK ATAKR--F-FYSNLM-NFFKTEIT 1050
WP_048327215   981 HHAHDAYLNAVVAKAILGKYPKL-APEFVYGDYPKYN-S---EQEi--GK ATAKR--F-FYSNLM-NFFKTEIT 1050
WP_049519324   981 HHAHDAYLNAVVAKAILGKYPKL-APEFVYGDYPKYN-S---FKEi--QK ATQKM--L-FYSNIL-KFFKDQES 1043
WP_012515931   981 HHAHDAYLNAVVAKAILGKYPKL-APEFVYGDYPKYN-S---FKEi--QK ATQKT--L-FYSNIL-KFFKDQES 1043
WP_021320964   981 HHAHDAYLNAVVAKAILGKYPKL-APEFVYGDYPKYN-S---FKEr--QK ATQKT--L-FYSNIL-KFFKDQES 1043
WP_037581760   989 HHAHDAYLNAVVAKAILKKYPKL-APEFVYGEYKKKYDV S---SDNhseLG KATAK--YfFYSNLM-NFFKTEVK 1061
WP_042322481   990 HHAHDAYLNAVVAKAILKKYPKL-APEFVYGEYQKKYDL TkdpKEV---EK ATEKY--F-FYSNLL-NFFKEEVH 1056
WP_009854540   990 HHAHDAYPYLNAVVAKAILKKYPKL-APEFVYGEYQKKYDL SkdpKEV---EK ATEKY--F-FYSNLL-NFFKEEVH 1056
WP_012962174   992 HHAHDAYLNAVVGTALLKKYPKL-ASEFVYGEYKKYDI S---GD------ KATAK--YfFYSNLM-NFFKRVIR 1058
WP_039695303   989 HHAHQDAYLNAVVGTALLKKYPKL-ASEFVYGEYKKYDI S---SD----- KATAK--YfFYSNLM-NFFKTKVK 1061
WP_014334983   989 HHAHQDAYLNAVVGTALLKKYPKL-TPEFVYGDYKHYDL S---SDDyseMG KATAK--YfFYSNLM-NFFKTEVK 1061
WP_003099269   982 HHAHQDAYLNAVVGTALLKKYPKL-EAEFVYGDYKHYDL P---DSS1--GK ATTRM--F-FYSNLM-NFFKKEIK 1051
AHY15608       982 HHAHDAYLNAVVGTALLKKYPKL-EAEFVYGDYKHYDL P---DSS1--GK ATTRM--F-FYSNLM-NFFKKEIK 1051
AHY17476       982 HHAHQDAYLNAVVGTALLKKYPKL-EAEFVYGDYKHYDL P---DSS1--GK ATTRM--F-FYSNLM-NFFKKEIK 1051
ESR09100
AGM98575       982 HHAHDAYLNAVVGTALLKKYPKL-EABFVYGDYKHYDL P---DSS1--GK ATTRM--F-FYSNLM-NFFKKEIK 1051
ALF27331       982 HHAHDAYLNAVIGKALLGVYPQL-EPEFVYGDYPHFH--G---HK----eNK ATAKK--F-FYSNIM-NFFKKD-- 1041
WP_018372492   995 HHAHDAYPYLNAVVAQALLKVYPKP-ERELVYGSYVKESI G---HK----eNK ATAKK--F-FYSNIM-NFFKKD-- 1055
WP_045618028   985 HHAHDAYPYLNAVVAKAILKKYPKL-EPEFVYGDYQKYDL G---FS----RK ATERM--F-rMNNIL-KFISKD-- 1056
WP_045635197   984 HHAHDAYLNAVVAKAILKKYPKL-EPEFVYGDYQKYDL G---HK----EK ATEKY--F-FYSNLL-NFFKEEVH 1055
WP_012962549   982 HHAHDAYLNAVIGKALLGVYPQL-EPEFVYGDYPHFH--G---HK----eNK ATAKK--F-FYSNIM-NFFKKD-- 1041
WP_002263887   982 HHAHDAYLNAVIGKALLGVYPQL-EPEFVYGDYPHFH--G---HK----eNK ATAKK--F-FYSNIM-NFFKKD-- 1041
WP_002264920   982 HHAHDAYLNAVIGKALLGVYPQL-EPEFVYGDYPHFH--G---HK----eNK ATAKK--F-FYSNIM-NFFKKD-- 1041
WP_002269043   982 HHAHDAYLNAVIGKALLGVYPQL-EPEFVYGDYPHFH--G---HK----eNK ATAKK--F-FYSNIM-NFFKKD-- 1041
```

-continued

| | | | | | | |
|---|---|---|---|---|---|---|
| WP_002269448 | 982 | HHAHDAYLNAVIGKALLGVYPQL-EPEFVYGDYPHFH | G---HK---eNK | ATAKK- | -F-FYSNIM-NFFKKD-- | 1041 |
| WP_002271977 | 982 | HHAHDAYLNAVIGKALLGVYPQL-EPEFVYGDYPHFH | G---HK---eNK | ATAKK- | -F-FYSNIM-NFFKKD-- | 1041 |
| WP_002272766 | 982 | HHAHDAYLNAVIGKALLGVYPQL-EPEFVYGDYPHFH | G---HE---eNK | ATAKK- | -F-FYSNIM-NFFKKD-- | 1041 |
| WP_002273241 | 982 | HHAHDAYLNAVIGKALLGVYPQL-EPEFVYGDYPHFH | G---HK---eNK | ATAKK- | -F-FYSNIM-NFFKKD-- | 1041 |
| WP_002275430 | 982 | HHAHDAYLNAVIGKALLGVYPQL-EPEFVYGDYPHFH | G---HE---eNK | ATAKK- | -F-FYSNIM-NFFKKD-- | 1041 |
| WP_002276448 | 982 | HHAHDAYLNAVIGKALLGVYPQL-EPEFVYGDYPHFH | G---HK---eNK | ATAKK- | -F-FYSNIM-NFFKKD-- | 1041 |
| WP_002277050 | 984 | HHAHDAYLNAVVVKALLVKYPKL-EPEFVYGEYPKYN | S---YR---eRK | ATQKM- | -F-FYSNIM-NMFKSKVK | 1046 |
| WP_002277364 | 982 | HHAHDAYLNAVIGKALLGVYPQL-EPEFVYGDYPHFH | G---HK---eNK | ATAKK- | -F-FYSNIM-NFFKKD-- | 1041 |
| WP_002279025 | 982 | HHAHDAYLNAVIGKALLGVYPQL-EPEFVYGDYPHFH | G---HE---eNK | ATAKK- | -F-FYSNIM-NFFKKD-- | 1041 |
| WP_002279859 | 982 | HHAHDAYLNAVIGKALLGVYPQL-EPEFVYGDYPHFH | G---HK---eNK | ATAKK- | -F-FYSNIM-NFFKKD-- | 1041 |
| WP_002280230 | 982 | HHAHDAYLNAVIGKALLGVYPQL-EPEFVYGDYPHFH | G---HE---eNK | ATAKK- | -F-FYSNIM-NFFKKD-- | 1041 |
| WP_002281696 | 982 | HHAHDAYLNAVIGKALLGVYPQL-EPEFVYGDYPHFH | G---HK---eNK | ATAKK- | -F-FYSNIM-NFFKKD-- | 1041 |
| WP_002282247 | 984 | HHAHDAYLNAVIGKALLVKYPKL-EPEFVYGEYPKYN | S---YR---eRK | ATQKM- | -F-FYSNIM-NMFKSKVK | 1046 |
| WP_002282906 | 982 | HHAHDAYLNAVIGKALLGVYPQL-EPEFVYGDYPHFH | G---HK---eNK | ATAKK- | -F-FYSNIM-NFFKKD-- | 1041 |
| WP_002283846 | 982 | HHAHDAYLNAVIGKALLGVYPQL-EPEFVYGDYPHFH | G---HK---eNK | ATAKK- | -F-FYSNIM-NFFKKD-- | 1041 |
| WP_002287255 | 982 | HHTHDAYLNAVIGKALLGVYPQL-EPEFVYGDYPHFH | G---HK---eNK | ATAKK- | -F-FYSNIM-NFFKKD-- | 1041 |
| WP_002288990 | 982 | HHAHDAYLNAVIGKALLGVYPQL-EPEFVYGDYPHFH | G---HK---eNK | ATAKK- | -F-FYSNIM-NFFKKD-- | 1041 |
| WP_002289641 | 982 | HHAHDAYLNAVIGKALLGVYPQL-EPEFVYGDYPHFH | G---HE---eNK | ATAKK- | -F-FYSNIM-NFFKKD-- | 1041 |
| WP_002290427 | 982 | HHAHDAYLNAVIGKALLGVYPQL-EPEFVYGDYPHFH | G---HK---eNK | ATAKK- | -F-FYSNIM-NFFKKD-- | 1041 |
| WP_002295753 | 982 | HHAHDAYLNAVIGKALLGVYPQL-EPEFVYGDYPHFH | G---HK---eNK | ATAKK- | -F-FYSNIM-NFFKKD-- | 1041 |
| WP_002296423 | 982 | HHAHDAYLNAVIGKALLGVYPQL-EPEFVYGDYPHFH | G---HK---eNK | ATAKK- | -F-FYSNIM-NFFKKD-- | 1041 |
| WP_002304487 | 996 | HHAHDAYLNAVIGKALLGVYPQL-EPEFVYGDYPHFH | G---HK---eNK | ATAKK- | -F-FYSNIM-NFFKKG-- | 1055 |
| WP_002305844 | 982 | HHAHDAYLNAVIGKALLGVYPQL-EPEFVYGDYPHFH | G---HK---eNK | ATAKK- | -F-FYSNIM-NFFKKD-- | 1041 |
| WP_002307203 | 982 | HHAHDAYLNAVIGKALLGVYPQL-EPEFVYGDYPHFH | G---HK---eNK | ATAKK- | -F-FYSNIM-NFFKKD-- | 1041 |
| WP_002310390 | 982 | HHAHDAYLNAVIGKALLGVYPQL-EPEFVYGDYPHFH | G---HK---eNK | ATAKK- | -F-FYSNIM-NFFKKD-- | 1041 |
| WP_002352408 | 982 | HHAHDAYLNAVIGKALLGVYPQL-EPEFVYGDYPHFH | G---HK---eNK | ATAKK- | -F-FYSNIM-NFFKKD-- | 1041 |
| WP_012997688 | 982 | HHAHDAYLNAVIGKALLGVYPQL-EPEFVYGDYPHFH | G---HK---eNK | ATAKK- | -F-FYSNIM-NFFKKD-- | 1041 |
| WP_014677909 | 982 | HHAHDAYLNAVIGKALLGVYPQL-EPEFVYGDYPHFH | G---HK---eNK | ATAKK- | -F-FYSNIM-NFFKKD-- | 1041 |
| WP_019312892 | 982 | HHAHDAYLNAVIGKALLGVYPQL-EPEFVYGDYPHFH | G---HK---eNK | ATAKK- | -F-FYSNIM-NFFKKD-- | 1041 |
| WP_019313659 | 982 | HHAHDAYLNAVIGKALLGVYPQL-EPEFVYGDYPHFH | G---HK---eNK | ATAKK- | -F-FYSNIM-NFFKKD-- | 1041 |
| WP_019314093 | 982 | HHAHDAYLNAVIGKALLGVYPQL-EPEFVYGDYPHFH | G---HK---eNK | ATAKK- | -F-FYSNIM-NFFKKD-- | 1041 |
| WP_019315370 | 982 | HHAHDAYLNAVIGKALLGVYPQL-EPEFVYGDYPHFH | G---HK---eNK | ATAKK- | -F-FYSNIM-NFFKKD-- | 1041 |
| WP_019803776 | 982 | HHAHDAYLNAVIGKALLGVYPQL-EPEFVYGDYPHFH | G---HK---eNK | ATAKK- | -F-FYSNIM-NFFKKD-- | 1041 |
| WP_019805234 | 982 | HHAHDAYLNAVIGKALLGVYPQL-EPEFVYGDYPHFH | G---HK---eNK | ATAKK- | -F-FYSNIM-NFFKKD-- | 1041 |
| WP_024783594 | 982 | HHAHDAYLNAVIGKALLGVYPQL-EPEFVYGDYPHFH | G---HK---eNK | ATAKK- | -F-FYSNIM-NFFKKD-- | 1041 |
| WP_024784288 | 984 | HHAHDAYLNAVVVKALLVKYPKL-EPEFVYGEYPKYN | S---YR---eRK | ATQKM- | -F-FYSNIM-NMFKSKVK | 1046 |
| WP_024784666 | 982 | HHAHDAYLNAVIGKALLGVYPQL-EPEFVYGDYPHFH | G---HK---eNK | ATAKK- | -F-FYSNIM-NFFKKD-- | 1041 |
| WP_024784894 | 982 | HHAHDAYLNAVIGKALLGVYPQL-EPEFVYGDYPHFH | G---HK---eNK | ATAKK- | -F-FYSNIM-NFFKKD-- | 1041 |
| WP_024786433 | 984 | HHAHDAYLNAVVVKALLVKYPKL-EPEFVYGEYPKYN | S---YR---eRK | ATQKM- | -F-FYSNIM-NMFKSKVK | 1046 |
| WP_049473442 | 982 | HHAHDAYLNAVIGKALLGVYPQL-EPEFVYGDYPHFH | G---HE---eNK | ATAKK- | -F-FYSNIM-NFFKKD-- | 1041 |
| WP_049474547 | 982 | HHAHDAYLNAVIGKALLGVYPQL-EPEFVYGDYPHFH | G---HK---eNK | ATAKK- | -F-FYSNIM-NFFKKD-- | 1041 |
| EMC03581 | 975 | HHAHDAYLNAVIGKALLGVYPQL-EPEFVYGDYPHFH | G---HK---eNK | ATAKK- | -F-FYSNIM-NFFKKD-- | 1034 |
| WP_000428612 | 987 | HHAHDAYLNAVAKAILKKYPKL-EPEFVYGDYQKYDL | SkdpKEI-EK | ATEKY- | -F-FYSNLL-NFFKEEVH | 1058 |
| WP_000428613 | 985 | HHAHDAYLNAVAKAILKKYPKL-EPEFVYGDYQKYDL | SmpKEV-EK | ATEKY- | -F-FYSNLL-NFFKEEVH | 1056 |
| WP_049523028 | 980 | HHAHDAYLNAVAILKKYPKL-EPEFVYGDYQKYDL | TkdpKEI-EK | ATEKY- | -F-FYSNLL-NFFKDKVY | 1051 |
| WP_003107102 | 951 | HHAHDAYLNAVVGTALLKKYPKL-EAEFVYGDYKHYDL | S---DTS1-GK | ATAKM- | -F-FYSNIM-NFFKKEVR | 1020 |
| WP_054279288 | 983 | HHAHDAYLNAVGTALLKMYPKL-ASEFVYGDYQKYDL | S---GKAS-GH | ATAKY- | -F-FYSNIM-NFFKSEVK | 1052 |
| WP_049531101 | 985 | HHAHDAYLNAVAKAILKKYPKL-EPEFVYGDYQKYDL | SrdpKEI-EK | ATEKY- | -F-FYSNLL-NFFKEEVH | 1056 |
| WP_049538452 | 985 | HHAHDAYLNAVAKAILKKYPKL-EPEFVYGDYQKYDL | SkdpKDI-EK | ATEKY- | -F-FYSNLL-NFFKEEVH | 1056 |
| WP_049549711 | 987 | HHAHDAYLNAVAKAILKKYPKL-EPEFVYGDYQKNDL | SkdpKDI-EK | ATEKY- | -F-FYSNLL-NFFKEEVH | 1058 |
| WP_007896501 | 988 | HHAHDAYLNAVVGTALLKKYPKL-EAEFVYGDYKHFDL | S---DPS1-GK | ATAKV- | -F-FYSNIM-NFFKEELS | 1057 |
| EFR44625 | 940 | HHAHDAYLNAVVGTALLKKYPKL-EAEFVYGDYKHFDL | S---DPS1-GK | ATAKV- | -F-FYSNIM-NFFKEELS | 1009 |
| WP_002897477 | 984 | HHAHDAYLNAVVAKAILKKYPKL-EPEFVYGDYQKYDL | FkpsKEI-EK | ATEKV- | -F-FYSNLL-NFFKEEVL | 1055 |

-continued

| ID | Start | Sequence | End |
|---|---|---|---|
| WP_002906454 | 984 | HHAHDAYLNAVVAKAILKKYPKL-EPEFVYGDYQKYDL SkasNTI---DK ATEKY-F-FYSNLL-NFFKEKVR | 1055 |
| WP_009729476 | 985 | HHAHDAYLNAVVAKAILKKYPKL-EPEFVYGDYQKYDL SkdpKEI---EK ATEKY-F-FYSNLL-NFFKEEVH | 1056 |
| CQR24647 | 984 | HHAHDAYLNAVVAKALLIRYPKL-EPEFVYGEYPKYN- S---YRE--RK ATEKM-F-FYSNIM-NMFKTTIK | 1046 |
| WP_000066813 | 989 | HHAHDAYLNAVLAKAILKKYPKL-EPEFVYGEYPKYN- srepKEV--EK ATQKY-F-FYSNIL-NFFKEEVH | 1060 |
| WP_009754323 | 985 | HHAHDAYLNAVVAKAILKKYPQL-APEFVYGDYQKYDL SkdpKEV--EK ATEKY-F-FYSNLL-NFFKEEVH | 1056 |
| WP_044674937 | 986 | HHAHDAYLNAVVATALLKKYPQL-APEFVYGDYPKYN- S---YKS--RK ATEKV-L-FYSNIM-NFFRRVLV | 1048 |
| WP_044676715 | 988 | HHAHDAYLNAVVATALLKKYPQL-APEFVYGDYPKYN- S---YKS--RK ATEKV-L-FYSNIM-NFFRRVLV | 1050 |
| WP_044680361 | 986 | HHAHDAYLNAVVATALLKKYPQL-APEFVYGDYPKYN- S---YKS--RK ATEKV-L-FYSNIM-NFFRRVLV | 1048 |
| WP_044681799 | 988 | HHAHDAYLNAVVATALLKKYPQL-APEFVYGEFKKYDV S---DK--eIG KATAK-YfFYSNLM-NFFKKEVK | 1050 |
| WP_049533112 | 981 | HHAHDAYLNAVIGTALLKKYPKL-ASEFVYGEFKKYDV S---DK--eIG KATAK-YfFYSNLM-NFFKKEVK | 1050 |
| WP_029090905 | 952 | HHAHQDAFLVAFLGTNITSNYPKI-EMEYLFKGYQHYLN ----Ev--GK AAKPKftF-IVENLS------- | 1007 |
| WP_006506696 | 977 | HHAHQDAFIVALIGGFMRDRYPNMhDSKAVYSEYMKMFR -----NKNd--QK ---g---FVINSM-NYPY-EV- | 1038 |
| AIT42264 | 982 | HHAHDAYLNAVVGTALIKKYPKL-ESEFVYGDYKVYDV S---EQEi--GK ATAKY-F-FYSNIM-NFFKTEIT | 1051 |
| WP_034440723 | 981 | HHGHDAYLNGVIALKLELYPYM-AKDLIYGKYSYHRK G------NK ATQAK-Y-KMSNII-ERFSQDL- | 1041 |
| AKQ21048 | 982 | HHAHDAYLNAVVGTALIKKYPKL-ESEFVYGDYKVYDV S---EQEi--GK ATAKY-F-FYSNIM-NFFKTEIT | 1051 |
| WP_004636532 | 981 | HHAHDAYLNAVVATTIMKVYPNL-KPQFVYGQYKKTSM S---FKE--EK ATARK-H-FYSNIT-KFFKKEKV | 1047 |
| WP_002364836 | 988 | HHGQDAYLNCVVATTLLKVYPNL-APEFVYGEYPKFQT --FKE--NK ATAKA-I-IYTNLL-RFFTED-- | 1047 |
| WP_016631044 | 939 | HHGQDAYLNCVVATTLLKVYPNL-APEFVYGEYPKFQT --FKE--NK ATAKA-I-IYTNLL-RFFTED-- | 998 |
| EMS75795 | 723 | HHGQDAYLNCVAIALLKKYPKL-EPEFVYGNYTKFNL --AT--eNK ATAKK-E-FYSNIL-RFFBEKE-- | 782 |
| WP_002373311 | 988 | HHGQDAYLNCVVATTLLKYPNL-APEFVYGEYPKFQA --FKE--NK ATAKT-I-IYTNLM-RFFTED-- | 1047 |
| WP_002378009 | 988 | HHGQDAYLNCVVATTLLKVYPNL-APEFVYGEYPKFQT --FKE--NK ATAKA-I-IYTNLL-RFFTED-- | 1047 |
| WP_002407324 | 988 | HHGQDAYLNCVVATTLLKVYPNL-APEFVYGEYPKFQT --FKE--NK ATAKA-I-IYTNLL-RFFTED-- | 1047 |
| WP_002413717 | 988 | HHGQDAYLNCVVATTLLKVYPNL-APEFVYGEYPKFQT --FKE--NK ATAKA-I-IYTNLL-RFFTED-- | 1047 |
| WP_010775580 | 990 | HHGQDAYLNCVVATTLLKVYPNL-APEFVYGEYPKFQT --FKE--NK ATAKA-I-IYTNLL-RFFTED-- | 1049 |
| WP_002364835 | 988 | HHGQDAYLNCVVATTLLKVYPNL-APEFVYGEYPKFQT --FKE--NK ATAKA-I-IYTNLL-RFFTED-- | 1047 |
| WP_010818269 | 990 | HHGQDAYLNCVVATTLLKVYPNL-APEFVYGEYPKFQT --FKE--NK ATAKA-I-IYTNLL-RFFTED-- | 1049 |
| WP_010824395 | 988 | HHGQDAYLNCVVATTLLKVYPNL-APEFVYGEYPKFQT --FKE--NK ATAKA-I-IYTNLL-RFFTED-- | 1047 |
| WP_016622645 | 988 | HHGQDAYLNCVVATTLLKVYPNL-APEFVYGEYPKFQA --FKE--NK ATAKA-I-IYTNLL-RFFTED-- | 1047 |
| WP_033624816 | 988 | HHGQDAYLNCVVATTLLKVYPNL-APEFVYGEYPKFQA --FKE--NK AMAKA-I-IYTNLL-RFFTED-- | 1047 |
| WP_033625576 | 988 | HHGQDAYLNCVVATTLLKVYPNL-APEFVYGEYPKFQA --FKE--NK ATAKA-I-IYTNLL-RFFTED-- | 1047 |
| WP_033789179 | 988 | HHGQDAYLNCVVATTLLKVYPNL-APEFVYGEYPKFQA --FKE--NK ATAKA-I-IYTNLM-RFFTEV-- | 1047 |
| WP_002310644 | 989 | HHAHDAYLNGVVALALLKKYPNL-APEFVYGEYLKFNA --HK--aNK ATVKK-E-FYSNIM-KFFESD-- | 1048 |
| WP_002312694 | 990 | HHAHDAYLNGVVALALLKKYPNL-APEFVYGEYLKFNA --HK--aNK ATVKK-E-FYSNIM-KFFESD-- | 1049 |
| WP_002314015 | 990 | HHAHDAYLNGVVALALLKKYPNL-APEFVYGEYLKFNA --HK--aNK ATVKK-E-FYSNIM-KFFESD-- | 1049 |
| WP_002320716 | 990 | HHAHDAYLNGVVALALLKKYPQL-APEFVYGEYLKFNA --HK--aNK ATVKK-E-FYSNIM-KFFESD-- | 1049 |
| WP_002330729 | 990 | HHAHDAYLNGVVALALLKKYPQL-APEFVYGEYLKFNA --HK--aNK ATVKK-E-FYSNIM-KFFESD-- | 1049 |
| WP_002335161 | 990 | HHAHDAYLNGVVALALLKKYPQL-APEFVYGEYLKFNA --HK--aNK ATVKK-E-FYSNIM-KFFESD-- | 1049 |
| WP_002345439 | 990 | HHAHDAYLNGVVALALLKKYPQL-APEFVYGEYLKFNA --HK--aNK ATVKK-E-FYSNIM-KFFESD-- | 1049 |
| WP_034867970 | 980 | HHAHDAYLNGFIANVLLKRYPKL-APEFVYGKVKYSL --AR--eNK ATAKK-E-FYSNIL-KFLESD-- | 1039 |
| WP_047937432 | 990 | HHGQDAYLNCVIALALLKKYPNL-APEFVYGEYLKFNA --HK--aNK ATVKK-E-FYSNIM-KFFESD-- | 1049 |
| WP_010720994 | 980 | HHAHDAYLNGFIANVLLKRYPKL-APEFVYGKVKYSL --AR--eNK ATAKK-E-FYSNIL-KFLESD-- | 1039 |
| WP_010737004 | 980 | HHAHDAYLNGFIANVLLKRYPKL-APEFVYGKVKYSL --AR--eNK ATAKK-E-FYSNIL-KFLESD-- | 1039 |
| WP_034700478 | 980 | HHAHDAYLNGFIANVLLKRYPKL-APEFVYGKVKYSL --AR--eNK ATAKK-E-FYSNIL-KFLESD-- | 1039 |
| WP_007209003 | 978 | HHAHDAYLNAVVALSLLRVYPQL-KPEFVYGKNS- --IHDq--NK ATIKK-qFYSNIT-RYFASK- | 1037 |
| WP_023591017 | 974 | HHAHDAYLNGVVAMTLLKKYPKL-APEFVYGSYIKGDI --NQ---iNK ATAKK-E-FYSNIM-KFFAEI- | 1033 |
| WP_010770040 | 986 | HHGHDAYLNGVVANSLLRVYPQL-QPEFVYGDYPKFNA --YKA--NK ATAKK-Q-LYTNIM-KFFABD-- | 1045 |
| WP_048604708 | 983 | HHAHDAYLNGVVATALLKIYPNL-EPEFVYGEFHRFNA --FKE--NK ATAKK-Q-FYSNLM-EFSKSD-- | 1042 |
| WP_010750235 | 983 | HHAHDAYLNAVALALLKKYPRL-APEFVYGSFAKFHL --VK--eNK ATAKK-F-FYSNIL-KFFBKE-- | 1042 |
| AII16583 | 1021 | HHAHDAYIATILGTYIGHRFESL-DAKYIYGEYQKIFR S---EQEi--GK ATAKY-F-FYSNIM-NFFKTEIT | 1090 |
| WP_029073316 | 988 | HHAHDAYIATILGTYIGHRFESL-DAKYIYGEYQKIFR ---KDg---FILNSM-RNLYADK- | 1052 |
| WP_031589969 | 988 | HHAHDAYIATILGTYIGHRFESL-DAKYIYGEYKRIFR ---NKNk--DK ---KDg---FILNSM-RNLYADK- | 1052 |
| KDA45870 | 973 | HHAHDAYLNAVVANLIMAKYPEL-EPEFVYGKYRTK- ---QKNK--GK ATAKN---NDg---FILNSM-RNIYADK- | 1034 |
| WP_039099354 | 991 | HHAFDAYLTAFVGLYLHKRYPKL-KPYPVYGEYQKAS- ---FKG1--GK ATAKN---NDg---FILNSM-RNIYADK- | 1043 |
| AKP02966 | 1000 | ----QQ---DK ----RN--F---NFL-NGLKKD--- | |
| | | ----KEIysKK -SRKN-gF-IISPLV------- | 1062 |

-continued

| ID | Start | Sequence | End |
|---|---|---|---|
| WP_010991369 | 985 | HHAHDAYLNGVVANTLLKVYPQL-EPEFVYGDYHQFDW----FKA---NK ATAKK--Q-FYTNIM LFFAQK- | 1044 |
| WP_033838504 | 985 | HHAHDAYLNGVVANTLLKVYPQL-EPEFVYGDYHQFDW----FKA---NK ATAKK--Q-FYTNIM LFFAQK- | 1044 |
| EHN60060 | 988 | HHAHDAYLNGVVANTLLKVYPQL-EPEFVYGDYHQFDW----FKA---NK ATAKK--Q-FYTNIM LFFAQK- | 1047 |
| EFR89594 | 754 | HHAHDAYLNGVVANTLLKVYPQL-EPEFVYGDYHQFDW----FKA---NK ATAKK--Q-FYTNIM LFFAQK- | 813 |
| WP_038409211 | 985 | HHAHDAYLNGVVANTLLKVYPQL-EPEFVYGDYHQFDW----FKA---NK ATAKK--Q-FYTNIM RFFAKE- | 1044 |
| EFR95520 | 604 | HHAHDAYLNGVVANTLLKVYPQL-EPEFVYGDYHQFDW----FKA---NK ATAKK--Q-FYTNIM RFFAKE- | 663 |
| WP_003723650 | 985 | HHAHDAYLNGVVANTLLKVYPQL-EPEFVYGDYHQFDW----FKA---NK ATAKK--Q-FYTNIM LFFAQK- | 1044 |
| WP_003727705 | 985 | HHAHDAYLNGVVANTLLKVYPQL-EPEFVYGEYHQFDW----FKA---NK ATAKK--Q-FYTNIM LFFAQK- | 1044 |
| WP_003730785 | 985 | HHAHDAYLNGVVANTLLKVYPQL-EPEFVYGEYHQFDW----FKA---NK ATAKK--Q-FYTNIM LFFAQK- | 1044 |
| WP_003733029 | 985 | HHAHDAYLNGVVANTLLKVYPQL-EPEFVYGEYHQFDW----FKA---NK ATAKK--Q-FYTNIM LFFAQK- | 1044 |
| WP_003739838 | 985 | HHAHDAYLNGVVANTLLKVYPQL-EPEFVYGEYHQFGW----FKA---NK ATAKK--Q-FYTNIM LFFGQK- | 1044 |
| WP_014601172 | 985 | HHAHDAYLNGVVANTLLKVYPQL-EPEFVYGEYHQFDW----FKA---NK ATAKK--Q-FYTNIM LFFGQK- | 1044 |
| WP_023548323 | 985 | HHAHDAYLNGVVANTLLKVYPQL-EPEFVYGEYHQFDW----FKA---NK ATAKK--Q-FYTNIM LFFAQK- | 1044 |
| WP_031665337 | 985 | HHAHDAYLNGVVANTLLKVYPQL-EPEFVYGEYHQFDW----FKA---NK ATAKK--Q-FYTNIM LFFAQK- | 1044 |
| WP_031669209 | 985 | HHAHDAYLNGVVANTLLKVYPQL-EPEFVYGEYHQFDW----FKA---NK ATAKK--Q-FYTNIM LFFAQK- | 1044 |
| WP_033920898 | 985 | HHAHDAYLNGVVANTLLKVYPQL-EPEFVYGEYHQFDW----FKA---NK ATAKK--Q-FYTNIM LFFAQK- | 1044 |
| AKI42028 | 988 | HHAHDAYLNGVVANTLLKVYPQL-EPEFVYGEYHQFDW----FKA---NK ATAKK--Q-FYTNIM LFFAQK- | 1047 |
| AKI50529 | 988 | HHAHDAYLNGVVANTLLKVYPQL-EPEFVYGEYHQFDW----FKA---NK ATAKK--Q-FYTNIM LFFGQK- | 1047 |
| EFR83390 | 433 | HHAHDAYLNGVVANTLLKVYPQL-EPEFVYGEYHQFDW----FKA---NK ATAKK--Q-FYTNIM LFFAKK- | 492 |
| WP_046323366 | 985 | HHAHDAYLNCVVANTLLKVYPQL-EPEFVYGDYHQFDW----FKA---NK ATAKK--Q-FYTNIM LFFAQK- | 1044 |
| AKE81011 | 998 | HHAHDAYLNAVVGTALIKKYPKL-ESEFVYGDYKVYDV S---EQEi-GK ATAKY--F-FYSNIM NFFKTEIT | 1067 |
| CUO82355 | 981 | HHAHDAYIVALIGGFMRDRYPNMhDSKAVYSEYMKMFR------NKNd--QK-----g----FVINSM-NYPY-EV- | 1042 |
| WP_033162887 | 983 | HHAHDAYIACIVGQFMHQNFEHL-DAKIIYGQYK-------KNy--KK---NYg----FILNSM-NHLQSDI- | 1042 |
| AGZ01981 | 1015 | HHAHDAYLNAVVGTALIKKYPKL-ESEFVYGDYKVYDV S---EQEi-GK ATAKY--F-FYSNIM NFFKTEIT | 1084 |
| AKA60242 | 982 | HHAHDAYLNAVVGTALIKKYPKL-ESEFVYGDYKVYDV S---EQEi-GK ATAKY--F-FYSNIM NFFKTEIT | 1051 |
| AK540380 | 982 | HHAHDAYLNAVVGTALIKKYPKL-ESEFVYGDYKVYDV S---EQEi-GK ATAKY--F-FYSNIM NFFKTEIT | 1051 |
| 4UN5_B | 986 | HHAHDAYLNAVVGTALIKKYPKL-ESEFVYGDYKVYDV S---EQEi-GK ATAKY--F-FYSNIM NFFKTEIT | 1055 |
| WP_010922251 | 1052 | LAN-GEIRKRPLIE TNGET-GE-IVWDKGRDFATVRKVLS-MPQVNIVKKTEVQT GGFSK ESIL-PKR- | 1114 |
| WP_039695303 | 1059 | YAD-GTVFERPLIE T-NAD-GE-IAWNKQIDFEKVRKVLS-YPQVNIVKKVETQT GGFSK ESIL-PKG- | 1120 |
| WP_045635197 | 1056 | YAD-GTIVKRENIE Y-SKDLGE-IAWNKEKDFAIIKKVLS-LPQVNIVKKREVQT GGFSK ESIL-PKG- | 1118 |
| 5AXW_A | 772 | YKYsHRVDKKPNRE VNNLN-GL---YDKDND--KLKKLINkSPEKLLMYHHDPQT --YQK KLIMeQYGd | 852 |
| WP_009880683 | 736 | LAN-GEIRKRPLIE TNGET-GE-IVWDKGRDFATVRKVLS-MPQVNIVKKTEVQT GGFSK ESIL-PKR- | 798 |
| WP_010922251 | 1052 | LAN-GEIRKRPLIE TNGET-GE-IVWDKGRDFATVRKVLS-MPQVNIVKKTEVQT GGFSK ESIL-PKR- | 1114 |
| WP_011054416 | 1052 | LAN-GEIRKRPLIE TNGET-GE-IVWDKGRDFATVRKVLS-MPQVNIVKKTEVQT GGFSK ESIL-PKR- | 1114 |
| WP_011284745 | 1052 | LAN-GEIRKRPLIE TNGET-GE-IVWDKGRDFATVRKVLS-MPQVNIVKKTEVQT GGFSK ESIL-PKR- | 1114 |
| WP_011285506 | 1052 | LAN-GEIRKRPLIE TNGET-GE-IVWDKGRDFATVRKVLS-MPQVNIVKKTEVQT GGFSK ESIL-PKR- | 1114 |
| WP_011527619 | 1052 | LAN-GEIRKRPLIE TNGET-GE-IVWDKGRDFATVRKVLS-MPQVNIVKKTEVQT GGFSK ESIL-PKR- | 1114 |
| WP_012560673 | 1051 | LAN-GEIRKRPLIE TNGET-GE-IVWDKGRDFATVRKVLS-MPQVNIVKKTEVQT GGFSK ESIL-PKR- | 1113 |
| WP_014407541 | 1052 | LAN-GEIRKRPLIE TNGET-GE-IVWDKGRDFATVRKVLS-MPQVNIVKKTEVQT GGFSK ESIL-PKR- | 1114 |
| WP_020905136 | 1052 | LAN-GEIRKRPLIE TNGET-GE-IVWDKGRDFATVRKVLS-MPQVNIVKKTEVQT GGFSK ESIL-PKR- | 1114 |
| WP_023080005 | 1051 | LAN-GEIRKRPLIE TNGET-GE-IVWDKGRDFATVRKVLS-MPQVNIVKKTEVQT GGFSK ESIL-PKR- | 1113 |
| WP_023610282 | 1052 | LAN-GEIRKRPLIE TNGET-GE-IVWDKGRDFATVRKVLS-MPQVNIVKKTEVQT GGFSK ESIL-PKR- | 1114 |
| WP_030125963 | 1052 | LAN-GEIRKRPLIE TNGET-GE-IVWDKGRDFATVRKVLS-MPQVNIVKKTEVQT GGFSK ESIL-PKR- | 1114 |
| WP_030126706 | 1052 | LAN-GEIRKRPLIE TNGET-GE-IVWDKGRDFATVRKVLS-MPQVNIVKKTEVQT GGFSK ESIL-PKR- | 1114 |
| WP_031488318 | 1052 | LAN-GEIRKRPLIE TNGET-GE-IVWDKGRDFATVRKVLS-MPQVNIVKKTEVQT GGFSK ESIL-PKR- | 1114 |
| WP_032460140 | 1052 | LAN-GEIRKRPLIE TNGET-GE-IVWDKGRDFATVRKVLS-MPQVNIVKKTEVQT GGFSK ESIL-PKR- | 1114 |
| WP_032461047 | 1052 | LAN-GEIRKRPLIE TNGET-GE-IVWDKGRDFATVRKVLS-MPQVNIVKKTEVQT GGFSK ESIL-PKR- | 1114 |
| WP_032462016 | 1052 | LAN-GEIRKRPLIE TNGET-GE-IVWDKGRDFATVRKVLS-MPQVNIVKKTEVQT GGFSK ESIL-PKR- | 1114 |
| WP_032462936 | 1052 | LAN-GEIRKRPLIE TNGET-GE-IVWDKGRDFATVRKVLS-MPQVNIVKKTEVQT GGFSK ESIL-PKR- | 1114 |
| WP_032464890 | 1052 | LAN-GEIRKRPLIE TNGET-GE-IVWDKGRDFATVRKVLS-MPQVNIVKKTEVQT GGFSK ESIL-PKR- | 1114 |
| WP_033888930 | 877 | LAN-GEIRKRPLIE TNGET-GE-IVWDKGRDFATVRKVLS-MPQVNIVKKTEVQT GGFSK ESIL-PKR- | 939 |
| WP_038431314 | 1052 | LAN-GEIRKRPLIE TNGET-GE-IVWDKGRDFATVRKVLS-MPQVNIVKKTEVQT GGFSK ESIL-PKR- | 1114 |
| WP_038432938 | 1051 | LAN-GEIRKRPLIE TNGET-GE-IVWDKGRDFATVRKVLS-MPQVNIVKKTEVQT GGFSK ESIL-PKR- | 1113 |

| | | | | | | |
|---|---|---|---|---|---|---|
| WP_038434062 | 1052 | LAN-GEIRKRPLIE | TNGET-GE | IWDKGRDFATVRKVLS-MPQVNIVKKTEVQT | GGFSK | ESIL-PKR- | 1114 |
| BAQ51233 | 963 | LAN-GEIRKRPLIE | TNGET-GE | IWDKGRDFATVRKVLS-MPQVNIVKKTEVQT | GGFSK | ESIL-PKR- | 1025 |
| KGE60162 | 227 | LAN-GEIRKRPLIE | TNGET-GE | IWDKGRDFATVRKVLS-MPQVNIVKKTEVQT | GGFSK | ESIL-PKR- | 289 |
| KGE60856 | 1 | ------------IE | TNGET-GE | IWDKGRDFATVRKVLS-MPQVNIVKKTEVQT | GGFSK | ESIL-PKR- | 52 |
| WP_002989955 | 1052 | LAN-GEIRKRPLIE | TNGET-GE | IWDKGRDFATVRKVLS-MPQVNIVKKTEEQT | GGFSK | ESIL-PKR- | 1114 |
| WP_003030002 | 1042 | ------------DIQ | T-NED-GE | IAWNKEKHIKILRKVLS-YPQVNIVKKTEQT | GGFSK | ESIL-PKG- | 1093 |
| WP_003065552 | 1059 | YSN-GKVIVRPVVE | Y-SKD-TEdIAWDKKKSNERTICKVLS-YPQVNIVKKVETQT | | GGFSK | ESIL-PKG- | 1121 |
| WP_001040076 | 1050 | LAD-GTVVVKDDIE | VNNDT-GE | IWDKKKKHFATVRKVLS-YPQVNIVKKTEQT | GGFSK | ESIL-AHG- | 1120 |
| WP_001040078 | 1058 | LAD-GSIVVRPVIE | TGRYM-GK-TAWDKKKHFATVRKVLS-YPQVNIVKKTEIQT | | GGFSK | ESIL-AHG- | 1112 |
| WP_001040080 | 1050 | LAD-GTVVVKDDIE | VNNDT-GE | IWDKKKKHFATVRKVLS-YPQNNIVKKTEIQT | GGFSK | ESIL-AHG- | 1112 |
| WP_001040081 | 1050 | LAD-GTVVVKDDIE | VNNDT-GE | IWDKKKKHFATVRKVLS-YPQNNIVKKTEIQT | GGFSK | ESIL-AHG- | 1112 |
| WP_001040083 | 1050 | LAD-GTVVVKDDIE | VNNDT-GE | IWDKKKKHFATVRKVLS-MPQVNIVKKTEVQT | GGFSK | ESIL-AHG- | 1112 |
| WP_001040085 | 1050 | LAD-GTVVVKDDIE | VNNDT-GE | IWDKKKKHFATVRKVLS-YPQVNIVKKTEIQT | GGFSK | ESIL-AHG- | 1112 |
| WP_001040087 | 1050 | LAD-GTVVVKDDIE | VNNDT-GE | IWDKKKKHFATVRKVLS-YPQNNIVKKTEIQT | GGFSK | ESIL-AHG- | 1112 |
| WP_001040088 | 1050 | LAD-GTVVVKDDIE | VNNDT-GE | IWDKKKKHFATVRKVLS-YPQNNIVKKTEIQT | GGFSK | ESIL-AHG- | 1112 |
| WP_001040089 | 1050 | LAD-GTVVVKDDIE | VNNDT-GE | IWDKKKKHFATVRKVLS-YPQNNIVKKTEIQT | GGFSK | ESIL-AHG- | 1112 |
| WP_001040090 | 1050 | LAD-GTVVVKDDIE | VNNDT-GE | IWDKKKKHFATVRKVLS-YPQNNIVKKTEIQT | GGFSK | ESIL-AHG- | 1112 |
| WP_001040091 | 1050 | LAD-GTVVVKDDIE | VNNET-GE | IAWDKKKHFATVRKVLS-YPQNNIVKKTEIQT | GGFSK | ESIL-AHG- | 1112 |
| WP_001040092 | 1050 | LAD-ETVVVKDDIE | VNNDT-GE | IWDKKKKHFATVRKVLS-YPQNNIVKKTEIQT | GGFSK | ESIL-AHS- | 1112 |
| WP_001040094 | 1050 | LAD-GTVVVKDDIE | VNNDT-GE | IWDKKKKHFATVRKVLS-YPQNNIVKKTEIQT | GGFSK | ESIL-AHG- | 1112 |
| WP_001040095 | 1050 | LAD-GTVVVKDDIE | VNNDT-GE | IWDKKKKHFATVRKVLS-YPQVNIVKKTEVQT | GGFSK | ESIL-AHG- | 1112 |
| WP_001040096 | 1050 | LAD-GTVVVKDDIE | VNNDT-GE | IWDKKKKHFATVRKVLS-YPQVNIVKKTEVQT | GGFSK | ESIL-AHG- | 1112 |
| WP_001040097 | 1050 | LAD-GTVVVKDDIE | VNNDT-GE | IWDKKKKHFATVRKVLS-YPQNNIVKKTEIQT | GGFSK | ESIL-AHG- | 1112 |
| WP_001040098 | 1050 | LAD-GTVVVKDDIE | VNNDT-GE | IWDKKKKHFATVRKVLS-YPQNNIVKKTEIQT | GGFSK | ESIL-AHG- | 1112 |
| WP_001040099 | 1050 | LAD-GTVVVKDDIE | VNNDT-GE | IWDKKKKHFATVRKVLS-YPQNNIVKKTEIQT | GGFSK | ESIL-AHG- | 1112 |
| WP_001040100 | 1050 | LAD-GTVVVKDDIE | VNNDT-GE | IWDKKKKHFATVRKVLS-YPQNNIVKKTEIQT | GGFSK | ESIL-AHG- | 1112 |
| WP_001040104 | 1050 | LAD-GTVVVKDDIE | VNNDT-GE | IWDKKKKHFATVRKVLS-YPQNNIVKKTEIQT | GGFSK | ESIL-AHG- | 1112 |
| WP_001040105 | 1050 | LAD-GTVVVKDDIE | VNNDT-GE | IWDKKKKHFATVRKVLS-YPQNNIVKKTEIQT | GGFSK | ESIL-AHG- | 1112 |
| WP_001040106 | 1050 | LAD-GTVVVKDDIE | VNNDT-GE | IWDKKKKHFATVRKVLS-YPQNNIVKKTEIQT | GGFSK | ESIL-AHG- | 1112 |
| WP_001040107 | 1050 | LAD-GTVVVKDDIE | VNNDT-GE | IWDKKKKHFATVRKVLS-YPQNNIVKKTEIQT | GGFSK | ESIL-AHG- | 1112 |
| WP_001040108 | 1050 | LAD-GTVVVKDDIE | VNNDT-GE | IWDKKKKHFATVRKVLS-YPQNNIVKKTEIQT | GGFSK | ESIL-AHG- | 1112 |
| WP_001040109 | 1050 | LAD-GTVVVKDDIE | VNNDT-GE | IWDKKKKHFATVRKVLS-YPQNNIVKKTEIQT | GGFSK | ESIL-AHG- | 1112 |
| WP_001040110 | 1050 | LAD-GTVVVKDDIE | VNNDT-GE | IWDKKKKHFATVRKVLS-YPQNNIVKKTEIQT | GGFSK | ESIL-AHG- | 1112 |
| WP_015058523 | 1050 | LAD-GTVVVKDDIE | VNNET-GE | IAWDKKKKHFATVRKVLS-YPQNNIVKKTEIQT | GGFSK | ESIL-AHS- | 1112 |
| WP_017643650 | 1050 | LAD-GTVVVKDDIE | VNNDT-GE | IWDKKKKHFATVRKVLS-YPQNNIVKKTEIQT | GGFSK | ESIL-AHG- | 1112 |
| WP_017647151 | 1050 | LAD-GTVVVKDDIE | VNNDT-GE | IWDKKKKHFATVRKVLS-YPQNNIVKKTEIQT | GGFSK | ESIL-AHG- | 1112 |
| WP_017648376 | 1050 | LAD-GTVVVKDDIE | VNNDT-GE | IWDKKKKHFATVRKVLS-YPQNNIVKKTEIQT | GGFSK | ESIL-AHG- | 1112 |
| WP_017649527 | 1050 | LAD-GTVVIKDDIE | VNNDT-GE | IWDKKKKHFATVRKVLS-YPQNNIVKKTEIQT | GGFSK | ESIL-AHG- | 1112 |
| WP_017771611 | 1050 | LAD-GTVVVKDDIE | VNNDT-GE | IWDKKKKHFATVRKVLS-YPQNNIVKKTEIQT | GGFSK | ESIL-AHG- | 1112 |
| WP_017771984 | 1050 | LAD-GTVVVKDDIE | VNNDT-GE | IWDKKKKHFATVRKVLS-YPQNNIVKKTEIQT | GGFSK | ESIL-AHG- | 1112 |
| CFQ25032 | 1050 | LAD-GTVVVKDDIE | VNNDT-GE | IWDKKKKHFATVRKVLS-YPQNNIVKKTEIQT | GGFSK | ESIL-AHG- | 1112 |
| CFV16040 | 1050 | LAD-GTVVVKDDIE | VNNDT-GE | IWDKKKKHFATVRKVLS-YPQNNIVKKTEIQT | GGFSK | ESIL-AHG- | 1112 |
| KLJ37842 | 1050 | LAD-GTVVVKDDIE | VNNDT-GE | IWDKKKKHFATVRKVLS-YPQNNIVKKTEIQT | GGFSK | ESIL-AHG- | 1112 |
| KLJ72361 | 1064 | LAD-GTVVVKDDIE | VNNDT-GE | IWDKKKKHFATVRKVLS-YPQNNIVKKTEIQT | GGFSK | ESIL-AHG- | 1126 |
| KLL20707 | 1050 | LAD-GTVVVKDDIE | VNNDT-GE | IWDKKKKHFATVRKVLS-YPQNNIVKKTEIQT | GGFSK | ESIL-AHG- | 1112 |
| KLL42645 | 1050 | LAD-GTVVVKDDIE | VNNDT-GE | IWDKKKKHFATVRKVLS-YPQNNIVKKTEIQT | GGFSK | ESIL-AHG- | 1112 |
| WP_047207273 | 1050 | LAD-GTVVVKDDIE | VNNDT-GE | IWDKKKKHFATVRKVLS-YPQNNIVKKTEIQT | GGFSK | ESIL-AHG- | 1112 |
| WP_047209694 | 1050 | LAD-GTVVVKDDIE | VNNDT-GE | IWDKKKKHFATVRKVLS-YPQNNIVKKTEIQT | GGFSK | ESIL-AHG- | 1112 |
| WP_050198062 | 1050 | LAD-GTVVVKDDIE | VNNDT-GE | IWDKKKKHFATVRKVLS-YPQNNIVKKTEIQT | GGFSK | ESIL-AHG- | 1112 |
| WP_050201642 | 1050 | LAD-GTVVVKDDIE | VNNDT-GE | IWDKKKKHFATVRKVLS-YPQNNIVKKTEIQT | GGFSK | ESIL-AHG- | 1112 |
| WP_050204027 | 1050 | LAD-GTVVVKDDIE | VNNDT-GE | IWDKKKKHFATVRKVLS-YPQNNIVKKTEIQT | GGFSK | ESIL-AHG- | 1112 |
| WP_050881965 | 1050 | LAD-GTVVVKDDIE | VNNDT-GE | IWDKKKKHFATVRKVLS-YPQNNIVKKTEIQT | GGFSK | ESIL-AHG- | 1112 |
| WP_050886065 | 1050 | LAD-GTVVVKDDIE | VNNDT-GE | IWDKKKKHFATVRKVLS-YPQNNIVKKTEIQT | GGFSK | ESIL-AHG- | 1112 |

-continued

```
AHN30376          1050 LAD-ETVVVKDDIE VNNET-GE-IAWDKKKHFATVRKVLS-YPQVNIVKKTEVQT GGFSK ESIL-AHS- 1112
EA078426          1050 LAD-GTVVVKDDIE VNNDT-GE-IVWDKKKHFATVRKVLS-YPQNNIVKKTEIQT GGFSK ESIL-AHG- 1112
CCW42055          1050 LAD-GTVVVKDDIE VNNDT-GE-IVWDKKKHFATVRKVLS-YPQNNIVKKTEIQT GGFSK ESIL-AHG- 1112
WP_003041502      1051 FAD-GTVVERPDIE T-SED-GE-IAWNKQTDFKIVRKVLS-YPQVNIVKKTEVQT HGLDR PSPK-PKP- 1122
WP_037593752      1043 ---------DIQ   T-NED-GE-IAWNKEKHIKILRKVLS-YPQVNIVKKEEQT  GGFSK ESIL-PKG- 1094
WP_049516684      1042 ---------DIQ   T-NED-GE-IAWNKEKHIKILRKVLS-YPQVNIVKKEEQT  GGFSK ESIL-PKG- 1093
GAD46167          1042 ---------DIQ   T-NED-GE-IAWNKEKHIKILRKVLS-YPQVNIVKKEEQT  GGFSK ESIL-PKG- 1093
WP_018363470      1063 YSN-GKVIVRPVVE Y-SKDtGE-IAWNKRTDFEKVRKVLA-MPQVNIVKKTEVQT GGFSK ESIL-SKR- 1125
WP_003043819      1061 LAN-GEIRKRPLIE TNGET-GE-VVWNKEKDFATVRKVLS-YPQVNIVKKEEQT  GGFSK ESIL-PKG- 1123
WP_066269658      1042 ---------DIQ   T-NED-GE-IAWNKEKHIKILRKVLS-YPQVNIVKKEEQT  GGFSK ESIL-PKG- 1093
WP_048800889      1052 FAD-GTVVERPDIE T-SED-GE-IVWDKGTDFKIVRKVLS-YPQVNIVKKEVQT  GRFSK ESIY-ARG- 1113
WP_012767106      1051 LAN-GEIRKRPLIE TNEET-GE-IVWDKGRDFATVRKVLS-MPQVNIVKKTEVQT GALTN ESIY-ARG- 1113
WP_014612333      1051 LAN-GEIRKRPLIE TNEET-GE-IVWDKGRDFATVRKVLS-MPQVNIVKKTEVQT GALTN ESIY-ARG- 1113
WP_015017095      1051 LAN-GEIRKRPLIE TNEET-GE-IVWDKGRDFATVRKVLS-MPQVNIVKKTEVQT GALTN ESIY-ARG- 1113
WP_015057649      1051 LAN-GEIRKRPLIE TNEET-GE-IVWDKGRDFATVRKVLS-MPQVNIVKKTEVQT GALTN ESIY-ARG- 1113
WP_048327215      1051 LAN-GEIRKRPLIE TNEET-GE-IVWDKGRDFATVRKVLS-MPQVNIVKKTEVQT GALTN ESIY-ARG- 1113
WP_049519324      1051 LAN-GEIRKRPLIE TNEET-GE-IVWDKGRDFATVRKVLS-MPQVNIVKKTEVQT GALTN ESIY-ARG- 1113
WP_012515931      1044 L-------H      VNSD--GE-EIWNANKHLPIIKNVLS-IPQVNIVKKTEVQT  GGFYK ESIL-SKG- 1094
WP_021320964      1044 L-------H      VNSD--GE-EIWNANKHLPIIKNVLS-IPQVNIVKKTEVQT  GGFYK ESIL-SKG- 1094
WP_037581760      1044 L-------H      VNSD--GE-EIWNANKHLPIIKNVLS-IPQVNIVKKTEVQT  GGFYK ESIL-PKG- 1094
WP_004324281      1062 YAD-GRVFERPDIE T-NAD-GE-VVWNKQRDFNIVRKVLS-YPQVNIVKKVEVQT  GGFSK ESIL-PKG- 1123
WP_009854540      1057 YAD-GTVFERPIIE T-NAD-GE-IAWNKQIDFEKVRKVLS-IPQVNIVKKVETQT  GGFSK ESIL-PKG- 1118
WP_012962174      1059 YSN-GKVVRPVIE  C-SKDtGE-IAWNKQTDFEKVRKVLS-YPQVNIVKKVETQT  GGFSK ESIL-PKG- 1119
WP_039695303      1062 YAD-GRVFERPDIE T-NAD-GE-VVWNKQKDFDIVRKVLS-YPQVNIVKKEAQT   GGFSK ESIL-SKG- 1120
WP_014334983      1052 LAD-DTIFTRPQIE VNTET-GE-IVWDKVKDMQTIRKVMS-YPQVNIVMKTEVQT  GGFSK ESIW-PKG- 1123
WP_003099269      1052 LAD-DTIFTRPQIE VNTET-GE-IVWDKVKDMQTIRKVMS-YPQVNIVMKTEVQT  GGFSK ESIW-PKG- 1114
AHY17476          1052 LAD-DTIFTRPQIE VNTET-GE-IVWDKVKDMQTIRKVMS-YPQVNIVMKTEVQT  GGFSK ESIW-PKG- 1114
ESR09100          1052 LAD-DTIFTRPQIE VNTET-GE-IVWDKVKDMQTIRKVMS-YPQVNIVMKTEVQT  ----- --------  1114
AGM98575          1052 LAD-DTIFTRPQIE VNTET-GE-IIWKKDEHISNIKKVLS-YPQVNIVKKVEEQT  GGFSK ESIW-PKG- 1114
ALF27331          1056 -K-------K     -DQEtGE-IVWDKKEIENIVKKVIY-SSPVNIVKKREEQS   GALFK QSNM-AVGy 1093
WP_018372492      1056 YAD-GTIVKRENIE Y-SKDtGE-IVWDKKEIENIVKKVIY-SSPVNIVKKREEQS   GALFK QSNM-AVGy 1108
WP_045618028      1057 YAD-GTIVKRENIE Y-SKDtGE-IAWNKEKDFATIKKVLS-LPQVNIVKKTEEQT   GGLFD NNIV-SKKk 1124
WP_045635197      1056 YAD-GTIVKRENIE Y-SKDtGE-IAWNKEKDFAIIKKVLS-LPQVNIVKKKREVQT  GGFSK ESIL-PKG- 1118
WP_002263549      1042 ---------DVR   T-DKN-GE-IIWKKDEHISNIKKVLS-YPQVNIVKKVEEQT   GGFSK ESIL-PKG- 1093
WP_002263887      1042 ---------DVR   T-DKN-GE-IIWKKDEHISNIKKVLS-YPQVNIVKKVEEQT   GGFSK ESIL-PKG- 1093
WP_002264920      1042 ---------DVR   T-DKN-GE-IIWKKDEYISNIKKVLS-YPQVNIVKKVEEQT   GGFSK ESIL-PKG- 1093
WP_002269043      1042 ---------DVR   T-DRN-GE-IIWKKDEHISNIKKVLS-YPQVNIVKKVEEQT   GGFSK ESIL-PKG- 1093
WP_002269448      1042 ---------DVR   T-DKN-GE-IIWKKDEHISNIKKVLS-YPQVNIVKKVEEQT   GGFSK ESIL-PKG- 1093
WP_002271977      1042 ---------DVR   T-DKN-GE-IIWKKDEHISNIKKVLS-YPQVNIVKKVEEQT   GGFSK ESIL-PKG- 1093
WP_002272766      1042 ---------DVR   T-DKN-GE-IIWKKDEHISNIKKVLS-YPQVNIVKKVEEQT   GGFSK ESIL-PKG- 1093
WP_002273241      1042 ---------DVR   T-DKN-GE-IIWKKDEHISNIKKVLS-YPQVNIVKKVEEQT   GGFSK ESIL-PKG- 1093
WP_002275430      1042 ---------DVR   T-DKN-GE-IIWKKDEHISNIKKVLS-YPQVNIVKKVEEQT   GGFSK ESIL-PKG- 1093
WP_002276448      1042 ---------DVR   T-DKN-GE-IIWKKDEHISNIKKVLS-YPQVNIVKKVEEQT   GGFSK ESIL-PKG- 1093
WP_002777050      1047 LAD-DQIVERPMIE VNDET-GE-IAWDKTKHITTVKKVLS-YPQVNIVKKVEEQT   GGLFD ----PKS-  1111
WP_002777364      1042 ---------DVR   T-DKN-GE-IIWKKDEHISNIKKVLS-YPQVNIVKKVEEQT   GGFSK ESIL-PKG- 1093
WP_002779025      1042 ---------DVR   T-DKN-GE-IIWKKDEYISNIKKVLS-YPQVNIVKKVEEQT   GGFSK ESIL-PKG- 1093
WP_002279859      1042 ---------DVR   T-DKN-GE-IIWKKDEHISNIKKVLS-YPQVNIVKKVEEQT   GGFSK ESIL-PKG- 1093
WP_002280230      1042 ---------DVR   T-DKN-GE-IIWKKDEHISNIKKVLS-YPQVNIVKKVEEQT   GGFSK ESIL-PKG- 1093
WP_002281696      1047 LAD-DQIVERPMIE VNDET-GE-IAWDKTKHITTVKKVLS-YPQVNIVKKVEEQT   GGLFD ----PKS-  1111
WP_002282247      1042 ---------DVR   I-DKN-GE-IIWKKDEHISNIKKVLS-YPQVNIVKKVEEQT   GGLFD ESIL-PKG- 1093
WP_002282906      1042 ---------DVR   T-DKN-GE-IIWKKDEHISNIKKVLS-YPQVNIVKKVEEQT   GGFSK ESIL-PKG- 1093
WP_002283846      1042 ---------DVR   T-DKN-GE-IIWKKDEHISNIKKVLS-YPQVNIVKKVEEQT   GGFSK ESIL-PKG- 1093
```

| | | | | |
|---|---|---|---|---|
| WP_002872255 | 1042 | ------DVR | T-DKN-GE-IIWKKDEHISNIKKVLS-YPQVNIVKKVEEQT | GGFSK ESIL-PKG- | 1093 |
| WP_002288990 | 1042 | ------DVR | T-DKN-GE-IIWKKDEHISNIKKVLS-YPQVNIVKKVEEQT | GGFSK ESIL-PKG- | 1093 |
| WP_002289641 | 1042 | ------DVR | T-DKN-GE-IIWKKDEHISNIKKVLS-YPQVNIVKKVEEQT | GGFSK ESIL-PKG- | 1093 |
| WP_002290427 | 1042 | ------DVR | T-DKN-GE-IIWKKDEHISNIKKVLS-YPQVNIVKKVEEQT | GGFSK ESIL-PKG- | 1093 |
| WP_002295753 | 1042 | ------DVR | T-DKN-GE-IIWKKDEYISNIKKVLS-YPQVNIVKKVEEQT | GGFFK ESIL-PKG- | 1093 |
| WP_002296423 | 1042 | ------DVR | T-DKN-GE-IIWKKDEHISNIKKVLS-YPQVNIVKKVEEQT | GGFSK ESIL-PKG- | 1093 |
| WP_002304487 | 1056 | ------DVR | T-DKN-GE-IIWKKDEHISNIKKVLS-YPQVNIVKKVEEQT | GGFSK ESIL-PKG- | 1107 |
| WP_002305844 | 1056 | ------DVR | T-DKN-GE-IIWKKDEHISNIKKVLS-YPQVNIVKKVEEQT | GGFSK ESIL-PKG- | 1107 |
| WP_002307203 | 1042 | ------DVR | T-DKN-GE-IIWKKDEHISNIKKVLS-YPQVNIVKKVEEQT | GGFSK ESIL-PKG- | 1093 |
| WP_002310390 | 1042 | ------DVR | T-DKN-GE-IIWKKDEYISNIKKVLS-YPQVNIVKKVEEQT | GGFSK ESIL-PKG- | 1093 |
| WP_002352408 | 1042 | ------DVR | T-DKN-GE-IIWKKDEHISNIKKVLS-YPQVNIVKKVEEQT | GGFSK ESIL-PKG- | 1093 |
| WP_012997688 | 1042 | ------DVR | T-DKN-GE-IIWKKDEHISNIKKVLS-YPQVNIVKKVEEQT | GGFSK ESIL-PKG- | 1093 |
| WP_014677909 | 1042 | ------DVR | T-DKN-GE-IIWKKDEHISNIKKVLS-YPQVNIVKKVEEQT | GGFSK ESIL-PKG- | 1093 |
| WP_019312892 | 1042 | ------DVR | T-DKN-GE-IIWKKDEYISNIKKVLS-YPQVNIVKKVEEQT | GGFSK ESIL-PKG- | 1093 |
| WP_019313659 | 1042 | ------DVR | T-DKN-GE-IIWKKDEHISNIKKVLS-YPQVNIVKKVEEQT | GGFSK ESIL-PKG- | 1093 |
| WP_019314093 | 1042 | ------DVR | T-DKN-GE-IIWKKDEYISNIKKVLS-YPQVNIVKKVEEQT | GGFSK ESIL-PKG- | 1093 |
| WP_019315370 | 1042 | ------DVR | T-DKN-GE-IIWKKDEHISNIKKVLS-YPQVNIVKKVEEQT | GGFFK ESIL-PKG- | 1093 |
| WP_019803776 | 1042 | ------DVR | T-DKN-GE-IIWKKDEHISNIKKVLS-YPQVNIVKKVEEQT | GGFSK ESIL-PKG- | 1093 |
| WP_019805234 | 1042 | ------DVR | T-DKN-GE-IIWKKDEHISNIKKVLS-YPQVNIVKKVEEQT | GGFFK ESIL-PKG- | 1093 |
| WP_024783594 | 1042 | ------DVR | T-DKN-GE-IIWKKDEHISNIKKVLS-YPQVNIVKKVEEQT | GGFSK ESIL-PKG- | 1093 |
| WP_024784288 | 1047 | LAD-DQIVERPMIE | VNDET-GE-IAWDKTKHITTVKKVLS-YPQVNIVKKVEEQT | GGLFD ----- PKS- | 1111 |
| WP_024784666 | 1042 | ------DVR | T-DKN-GE-IIWKKDEHISNIKKVLS-YPQVNIVKKVEEQT | GGFSK ESIL-PKG- | 1093 |
| WP_024784894 | 1042 | ------DVR | T-DKN-GE-IIWKKDEHISNIKKVLS-YPQVNIVKKVEEQT | GGFSK ESIL-PKG- | 1093 |
| WP_024786433 | 1047 | LAD-DQIVERPMIE | VNDET-GE-IAWDKTKHITTVKKVLS-YPQVNIVKKVEEQT | GGLFD ----- PKS- | 1111 |
| WP_049473442 | 1053 | LAN-GNIIKRSPIE | VNEET-GE-IVWDKVKDIKTIRKVLS-IPQINVVKKTEIQT | GGFSN ETIL-SKR- | 1115 |
| WP_049474547 | 1042 | ------DVR | T-DKN-GE-IIWKKDEHISNIKKVLS-YPQVNIVKKVEEQT | GGFSK ESIL-PKG- | 1093 |
| EMC03581 | 1035 | ------DVR | T-DKN-GE-IIWKKDEHISNIKKVLS-YPQVNIVKKVEEQT | GGFSK ESIL-PKG- | 1086 |
| WP_000428612 | 1059 | YAD-GTIVKRENIE | Y-SKDtGE-IAWNKEKDFATIKKVLS-LPQVNIVKKVEEQT | GGLFD NNIV-SKKk | 1121 |
| WP_000428613 | 1057 | YAD-GTIVKRENIE | Y-SKDtGE-IAWNKEKDFATIKKVLS-YPQVNIVKKVEEQT | GGLFD NNIV-SKKk | 1114 |
| WP_049523028 | 1052 | YAD-GTIIQRGNVE | Y-SKDtGE-IAWNNKKRDFAIVRKVLS-YPQVNIVKKTEEQT | GGLFD NNIV-SKEk | 1114 |
| WP_003107102 | 1021 | LAD-GTVITRPQIE | TNTET-GE-IVWDKVKDIKTTRKVLS-IPQINVVKKTEVQT | GAFSK ESIL-SKR- | 1083 |
| WP_054279288 | 1053 | LAN-GNIIKRSPIE | VNEET-GE-IVWDKTKDFGTVRKVLS-APQVNIVKKTEIQT | GGFSN ETIL-SKR- | 1115 |
| WP_049531101 | 1057 | YAD-GTIVKRENIE | Y-SKDtGE-IAWNKEIDFATIRKILS-LPQVNIVKKTEEQT | GGLFD NNIV-SKKk | 1124 |
| WP_049538452 | 1059 | YAD-GTIVKRENIE | Y-SKDtGE-IAWNKEKDFATIKKILS-LPQVNIVKKTEEQT | GGLFD NNIV-SKKk | 1124 |
| WP_049549711 | 1058 | YAD-GTIVKRENIE | Y-SKDtGE-IAWNKEKDFKTIRKVLS-YPQVNIVKKTEIQS | GGLFD NNIV-SKEk | 1126 |
| WP_007896501 | 1010 | LAD-GTLMKRPVIE | TNTET-GE-VVWDKVKDFKTIRKVLS-YPQVNIVKKTEIQS | GAFSK ESVL-SKG- | 1120 |
| EFR44625 | 1056 | LAD-GTLMKRPVIE | TNTET-GE-IAWDKTKHFANVKKVLS-YPQVSIVKKREVQT | GGFSN ESVL-SKG- | 1072 |
| WP_002897477 | 1056 | YAD-GTIRKRENIE | Y-SNDtGE-IAWNKEKDFATIKKVLS-LPQVNIVKKREVQT | GGFSK ESIL-PKG- | 1118 |
| WP_002906454 | 1056 | YAD-GTIVKRENIE | Y-SKDtGE-IAWNKEKDFVTIKKVLS-LPQVNIVKKREVQT | GGLFD NNIV-SKKk | 1123 |
| WP_009729476 | 1057 | YAD-GTIVKRENIE | Y-SKDtGE-IAWNKEKDFATIKKVLS-YPQVNIVKKREVQT | GGFSK ESIL-PKG- | 1119 |
| CQR24647 | 1047 | LAD-GRVVEKPVIE | ANEET-GE-IAWDKTKHFANVKKVLS-YPQVSIVKKVEVQT | GGFSK ESIL-PKG- | 1109 |
| WP_000666813 | 1061 | YAD-GTIVKRENIE | Y-SKDtGE-IAWNKEKDFVTIKKVLS-LPQVNIVKKREVQT | GGFSK ESIL-PKG- | 1123 |
| WP_009754323 | 1057 | YAD-GTIVKRENIE | Y-SKDtGE-IAWNKEKDFATIKKVLS-YPQVNIVKKREVQT | GGFSK ESIL-PKG- | 1119 |
| WP_044674937 | 1049 | YSktGEVRIRPVIE | VNKET-GE-IVWDKKSDFRTVRKVLS-YPQVNVVKKVEMQT | GGFSK ESIL-QHG- | 1112 |
| WP_044676715 | 1051 | YSktGEVRIRPVIE | VNKET-GE-IVWDKKSDFRTVRKVLS-YPQVNVVKKVEMQT | GGFSK ESIL-QHG- | 1114 |
| WP_044680361 | 1051 | YSktGEVRIRPVIE | VNKET-GE-IVWDKKSDFKTVRKVLS-YPQVNNVVKKVEMQT | GGFSK ESIL-QHG- | 1114 |
| WP_044681799 | 1049 | YSktGEVRIRPVIE | VNKET-GE-IVWDKKSDFKTVRKVLS-YPQVNVVKKVEMQT | GGFSK ESIL-QHG- | 1112 |
| WP_049533112 | 1051 | FAD-GTVVERPDIE | T-SED-GE-IAWNKQTDFKIVRKVLS-YPQVNIVRKVEEQS | HGLDR PSPK-PKP- | 1122 |
| WP_029090905 | 1008 | -KQ------ | -------Q-------NSTtGE-VKWNPEVDIAKLKRILN-FKQCNIVRKVEEQS | GALFK ETIY-PVEe | 1061 |
| WP_006506696 | 1039 | -D------ | ------GK-LIWNP-DLINEIKKCFY-YKDCYCTTKLDQKS | GQLFN -TVL-SNDa | 1084 |
| AIT42264 | 1052 | LAN-GEIRKRPLIE | TNGET-GE-IVWDKGRDFATVRKVLS-MPQVNIVKKTEVQT | GGFSK ESIL-PKR- | 1114 |
| WP_034440723 | 1042 | --NPD-GE-IAWEKDKDLNTIRKVLS-SKQINIIKKABEGK | ------LA | GRLFK ETIN-SRPs | 1092 |
| AKQ21048 | 1052 | LAN-GEIRKRPLIE | TNGET-GE-IVWDKGRDFATVRKVLS-MPQVNIVKKTEVQT | GGFSK ESIL-PKR- | 1114 |

-continued

```
WP_004636532   1043 ----------------- VNEET-GE- ILWDTERHLSTIKRVLS-WKQMNIVKKVEKQK GQLWK ETIY-PKG- 1092
WP_002364836   1048 --E------------ P RFTKD-GE- ILWSN-SYLKTIKKELN-YHQMNIVKKVEVQK GGFSK ESIK-PKG- 1098
WP_016631044   999  --E------------ P RFTKD-GE- ILWSN-SYLKTIKKELN-YHQMNIVKKVEVQK GGFSK ESIK-PKG- 1049
EMS75795       783  --E------------ Y SYDEN-GE- IFWDKARHIPQIKKVIS-SHQVNIVKKVEVQT GGFSK ETVN-PKG- 834
WP_002373311   1048 --E------------ P RFTKD-SE- ILWSN-SYLKTIKKELN-YHQMNIVKKVEVQK GGFSK ESIK-PKG- 1098
WP_002378009   1048 --E------------ P RFTKD-GE- ILWSN-SYLKTIKKELN-YHQMNIVKKVEVQK GGFSK ESIK-PKG- 1098
WP_002407324   1048 --E------------ P RFTKD-GE- ILWSN-SYLKTIKKELN-YHQMNIVKKVEVQK GGFSK ESIK-PKG- 1098
WP_002413717   1048 --E------------ P RFTKD-GE- ILWSN-SYLKTIKKELN-YHQMNIVKKVEVQK GGFSK ESIK-PKG- 1098
WP_010775580   1050 --E------------ P RFTKD-GE- ILWSN-SYLKTIKKELN-YHQMNIVKKVEVQK GGFSK ESIK-PKG- 1100
WP_010818269   1048 --E------------ P RFTKD-GE- ILWSN-SYLKTIKKELN-YHQMNIVKKVEVQK GGFSK ESIK-PKG- 1098
WP_010824395   1048 --E------------ P RFTKD-GE- ILWSN-SYLKTIKKELN-YHQMNIVKKVEVQK GGFSK ESIK-PKG- 1098
WP_016622645   1048 --E------------ P RFTKD-GE- ILWSN-SYLKTIKKELN-YHQMNIVKKVEVQK GGFSK ESIK-PKG- 1098
WP_033624816   1048 --E------------ P RFTKD-GE- ILWSN-SYLKTIKKELN-YHQMNIVKKVEVQK GGFSK ESIK-PKG- 1098
WP_033625576   1048 --E------------ P RFTKD-GE- ILWSN-SYLKTIKKELN-YHQMNIVKKVEVQK GGFSK ESIK-PKG- 1098
WP_033789179   1048 --E------------ P RFTKD-GE- ILWSN-SYLKTIKKELN-YHQMNIVKKVEVQK GGFSK ESIK-PKG- 1098
WP_002310644   1049 --T------------ P VCDEN-GE- IFWDKSKSIAQVKKVIN-HHHMNIVKKTEIQK GGFSK ETVE-PKK- 1100
WP_002112694   1050 --T------------ P VCDEN-GE- IFWDKSKSIAQVKKVIN-HHHMNIVKKTEIQK GGFSK ETVE-PKK- 1101
WP_002314015   1050 --T------------ P VCDEN-GE- IFWDKSKSIAQVKKVIN-HHHMNIVKKTEIQK GGFSK ETVE-PKK- 1101
WP_002345439   1050 --T------------ P VCDEN-GE- IFWDKSKSIAQVKKVIN-HHHMNIVKKTEIQK GGFSK ETVE-PKK- 1101
WP_034867970   1050 --T------------ P VCDEN-GE- IFWDKSKSIAQVKKVIN-HHHMNIVKKTEIQK GGFSE ETVE-PKK- 1100
WP_002320716   1049 --T------------ P VCDEN-GE- IFWDKSKSIAQVKKVIN-HHHMNIVKKTEIQK GGFSK ETVE-PKK- 1100
WP_002330729   1050 --T------------ P VCDEN-GE- IFWDKSKSIAQVKKVIN-HHHMNIVKKTEIQK GGFSK ETVE-PKK- 1101
WP_002335161   1050 --T------------ P VCDEN-GE- IFWDKSKSIAQVKKVIN-HHHMNIVKKTEIQK GGFSK ETVE-PKK- 1101
WP_047937432   1050 --T------------ P FCDEN-GE- IYWEKSHHLPRIKKVLS-SHQVNVVKKVEQQK GGFYK ETVN-SKE- 1101
WP_010720994   1040 --T------------ P FCDEN-GE- IYWEKSHHLPRIKKVLS-SHQVNVVKKVEQQK GGFYK ETVN-SKE- 1091
WP_010737004   1040 --T------------ P FCDEN-GE- IYWEKSHHLPRIKKVLS-SHQVNVVKKVEQQK GGFYK ETVN-SKE- 1091
WP_034700478   1040 --E------------ P FCDEN-GE- IYWEKSHHLPRIKKVLS-SHQVNVVKKVEQQK GGFYK ETVN-SKE- 1091
WP_007209003   1038 --D------------ I INDD-GE- ILNNKQETIAQVIKTLG-MHQVNVVKKVEIQK GGFYK ESIQ-PKG- 1089
WP_023519017   1046 --E------------ I ICDEQ-GE- VIWNKKRDLSTIKKTIG-AHQVNIVKKVEKQK GGFYK ETIN-SKA- 1096
WP_010770040   1046 --A------------ V IIDEN-GE- ILWDK-KNIATVKKVMS-YPQMNIVKKPEIQT GSFSK ETIK-PKG- 1096
WP_048604708   1043 --K------------ V IIDEN-GE- ILWNQ-KKIVTVKKVMN-YRQMNIVKKVEIQK GGFSK ESIL-PKG- 1093
WP_010750235   1043 --E------------ Q FCDEN-GE- IFWDKRKHIQQIKKVIS-SHQVNIVKKVEVQT GGFYK ETVN-TKE- 1094
AII16583       1091 LAN-GEIRKRPLIE TNGET-GE- IVWDKGRDFATVRKVLS-MPQVNIVKKTEVQT GGFSK ESIL-PKR- 1153
WP_029073316   1053 --D------------ -------T-GE- EWISRIKKCFY-YKDCFVTKKLEENN GSFFN -TVR-PNDe 1099
WP_031589969   1053 --D------------ -------T-GE- IVWDP-NYIDRIKKCFY-YKDCFVTKKLEENN GTFFN -TVL-PNDt 1099
KDA45870       1035 --D------------ -------WDKARDLPTIKRYLY-RAQVNKVRKAERQT GGFSD EMLV-PKS- 1078
WP_039099354   1044 --E------------ -E LVDEN-TEaVIWNKESGLAYLNKIYQ-FKKILVTREVHENS GALFN QTLYaAKDd 1097
AKP02966       1063 --N------------ GTTQ --DRNtGE-IIWNVG- FRDKILKIFN-YHQCNVTRKTEIKT GQFYD QTIYsPKNp 1118
WP_010991369   1045 --D------------ R IIDEN-GE- ILWDK-KYLDTVKKVMS-YRQMNIVKKTEIQK GEFSN ATIK-PKG- 1095
WP_033838504   1045 --D------------ R IIDEN-GE- ILWDK-KYLDTVKKVMS-YRQMNIVKKTEIQK GEFSN ATIK-PKG- 1095
EHN60060       1048 --E------------ R IIDEN-GE- ILWDK-KYLDTVKKVMS-YRQMNIVKKTEIQK GEFSN ATIK-PKG- 1098
EFR89594       814  --B------------ R IIDEN-GE- ILWDK-KYLDTVKKVMS-YRQMNIVKKTEIQK GEFSN ATIK-PKG- 864
WP_038409211   1045 --N------------ Q IIDKN-GE- ILWDN-RYLDTIKKVLS-YRQMNIVKKTEIQK GEFSN ATVN-PKG- 1095
EFR95520       664  --N------------ Q IIDKN-GE- ILWDN-RYLDTIKKVLS-YRQMNIVKKTEIQK GEFSN ATVN-PKG- 714
WP_037223650   1045 --E------------ R IIDEN-GE- ILWDK-KYLETIKKVLD-KYLETIKKVLD-YRQMNIVKKTEIQK GEFSK ATIK-PKG- 1095
WP_037227705   1045 --E------------ R IIDEN-GE- ILWDK-KYLETIKKVLD-YRQMNIVKKTEIQK GEFSK ATIK-PKG- 1095
WP_003730785   1045 --E------------ R IIDEN-GE- ILWDK-KYLETIKKVLG-YRQINIVKKTEIQK GEFSK ATIK-PKG- 1095
WP_003730329   1045 --E------------ R IIDEN-GE- ILWDK-KYLETIKKVLG-YRQMNIVKKTEIQK GEFSK VTPN-PKG- 1095
WP_003739838   1045 --E------------ R IIDEN-GE- ILWDK-KYLETIKKVLD-YRQMNIVKKTEIQK GEFSK ATIK-PKG- 1095
WP_014601172   1045 --B------------ R IIDEN-GE- ILWDK-KYLETIKKVLD-YRQMNIVKKTEIQK GEFSK ATIK-PKG- 1095
WP_023548323   1045 --E------------ R IIDEN-GE- ILWDK-KYLETIKKVLN-YRQMNIVKKTEIQK GEFSN QNPK-PRG- 1095
WP_031665337   1045 --E------------ R IIDEN-GE- ILWDK-KYLETIKKVLD-YRQMNIVKKTEIQK GEFSK ATIK-PKG- 1095
WP_031669209   1045 --D------------ R IIDEN-GE- ILWDK-RYLETVKVLG-YRQMNIVKKTEIQK GEFSN VTPN-PKG- 1095
```

```
WP_033920898   1045  -E-------------R  IIDEN-GE-ILWDK-KYLETIKKVLN-YRQMNIVKKTEIQK  GEFSN  QNPK-PRG-                                                          1095
AKI42028       1048  -E-------------R  IIDEN-GE-ILWDK-KYLETIKKVLN-YRQMNIVKKTEIQK  GEFSK  ATIK-PKG-                                                          1098
AKI50529       1048  -E-------------R  IIDEN-GE-ILWDK-KYLETIKKVLN-YRQMNIVKKTEIQK  GEFSN  QNPK-PRG-                                                          1098
EFR83390        493  -E-------------R  IIDEN-GE-ILWDK-KYLETIKKVLN-YRQMNIVKKTEIQK  GEFSK  ATIK-PKG-                                                           543
WP_046323366   1045  -D-------------R  IIDEN-GE-ILWDK-KYLDTIKKVLN-YRQMNIVKKTEIQK  GEFSN  ATAN-PKG-                                                          1095
AKE81011       1068  LAN-GEIRKRPLIE  TNGET-GE-IVWDKGRDFATVRKVLS-MPQVNIVKKTEVQT  GGFSK  ESIL-PKR-                                                              130
CUO82355       1043  -D--------------    ------GK-LIWNP-DLINEIKKCFY-YKDCYCTTKLDQKS  GQMFN  -TVL-PNDa                                                        1088
WP_033162887   1085  -D---------------   -----T-GE-VMWDP-AKIGKIKSCFY-YKDVVVTKKLEQNS  GTLFN  -TVL-PNDa                                                        1089
AGZ01981       1052  LAN-GEIRKRPLIE  TNGET-GE-IVWDKGRDFATVRKVLS-MPQVNIVKKTEVQT  GGFSK  ESIL-PKR-                                                             1147
AKA60242       1052  LAN-GEIRKRPLIE  TNGET-GE-IVWDKGRDFATVRKVLS-MPQVNIVKKTEVQT  GGFSK  ESIL-PKR-                                                             1114
AKS40380       1056  LAN-GEIRKRPLIE  TNGET-GE-IVWDKGRDFATVRKVLS-MPQVNIVKKTEVQT  GGFSK  ESIL-PKR-                                                             1114
4UN5_B         1115  -NSD  KLIA----  RKKDW-DPKKYGGFDSPTVAYSV-LVVAK--VE--KGKSKKLKSVKELLGITIME  RSSFEK                                                          1118
WP_010922251   1121  -DSD  KLIPRKTkKV-YW-DTKKYGGFDSPTVAYSV-FVVAD--VE--KGKAKKLKTVKELVGISIME  RSFFEE                                                             1176
WP_039695303   1119  -NSD  KLIPRKT-KDILL-DTTKYGGFDSPVIAYSI-LLIAD--IE--KGKAKKLKTVKELVGISIME  KAAFEE                                                             1185
WP_045635197    853  -EKN  -LYKYrEeTGNYL---TKYSKKDNGPVIKKI-------------KYYGNKLNAHLDITDDYPNS  -VKLSL                                                            1183
5AXW_A          799  -NSD  KLIA----  RKKDW-DPKKYGGFDSPTVAYSV-LVVAK--VE--KGKSKKLKSVKELLVGITIME  RSSFEK                                                              912
WP_009880683   1115  -NSD  KLIA----  RKKDW-DPKKYGGFDSPTVAYSV-LVVAK--VE--KGKSKKLKSVKELLGITIME  RSSFEK                                                              860
WP_010922251   1115  -NSD  KLIA----  RKKDW-DPKKYGGFDSPTVAYSV-LVVAK--VE--KGKSKKLKSVKELLGITIME  RSSFEK                                                             1176
WP_011054416   1115  -NSD  KLIA----  RKKDW-DPKKYGGFDSPTVAYSV-LVVAK--VE--KGKSKKLKSVKELLGITIME  RSSFEK                                                             1176
WP_011284745   1115  -NSD  KLIA----  RKKDW-DPKKYGGFDSPTVAYSV-LVVAK--VE--KGKSKKLKSVKELLGITIME  RSSFEK                                                             1176
WP_011285506   1115  -NSD  KLIA----  RKKDW-DPKKYGGFDSPTVAYSV-LVVAK--VE--KGKSKKLKSVKELLGITIME  RSSFEK                                                             1176
WP_011527619   1115  -NSD  KLIA----  RKKDW-DPKKYGGFDSPTVAYSV-LVVAK--VE--KGKSKKLKSVKELLGITIME  RSSFEK                                                             1176
WP_012560673   1115  -NSD  KLIA----  RKKDW-DPKKYGGFDSPTVAYSV-LVVAK--VE--KGKSKKLKSVKELLGITIME  RSSFEK                                                             1176
WP_014407541   1114  -NSD  KLIA----  RKKDW-DPKKYGGFDSPTVAYSV-LVVAK--VE--KGKSKKLKSVKELLGLTIME  RSSFEK                                                             1175
WP_020905136   1115  -NSD  KLIA----  RKKDW-DPKKYGGFDSPTVAYSV-LVVAK--VE--KGKSKKLKSVKELLGITIME  RSSFEK                                                             1176
WP_023080005   1115  -NSD  KLIA----  RKKDW-DPKKYGGFDSPTVAYSV-LVVAK--VE--KGKSKKLKSVKELLGITIME  RSSFEK                                                             1175
WP_023610282   1114  -NSD  KLIA----  RKKDW-DPKKYGGFDSPTVAYSV-LVVAK--VE--KGKSKKLKSVKELLGITIME  RSSFEK                                                             1175
WP_030125963   1115  -NSD  KLIA----  RKKDW-DPKKYGGFDSPTVAYSV-LVVAK--VE--KGKSKKLKSVKELLGITIME  RSSFEK                                                             1176
WP_030126706   1115  -NSD  KLIA----  RKKDW-DPKKYGGFDSPTVAYSV-LVVAK--VE--KGKSKKLKSVKELLGITIME  RSSFEK                                                             1176
WP_031488318   1115  -NSD  KLIA----  RKKDW-DPKKYGGFDSPTVAYSV-LVVAK--VE--KGKSKKLKSVKELLGITIME  RSSFEK                                                             1176
WP_032460140   1115  -NSD  KLIA----  RKKDW-DPKKYGGFDSPTVAYSV-LVVAK--VE--KGKSKKLKSVKELVGITIME  RSSFEK                                                             1176
WP_032461047   1115  -NSD  KLIA----  RKKDW-DPKKYGGFDSPTVAYSV-LVVAK--VE--KGKSKKLKSVKELVGITIME  RSSFEK                                                             1176
WP_032462016   1115  -NSD  KLIA----  RKKDW-DPKKYGGFDSPTVAYSV-LVVAK--VE--KGKSKKLKSVKELLGITIME  RSSFEK                                                             1176
WP_032462936   1115  -NSD  KLIA----  RKKDW-DPKKYGGFDSPTVAYSV-LVVAK--VE--KGKSKKLKSVKELLGITIME  RSSFEK                                                             1176
WP_032464890   1115  -NSD  KLIA----  RKKDW-DPKKYGGFDSPTVAYSV-LVVAK--VE--KGKSKKLKSVKELLGITIME  RSSFEK                                                             1176
WP_033888930    940  -NSD  KLIA----  RKKDW-DPKKYGGFDSPTVAYSV-LVVAK--VE--KGKSKKLKSVKELLGITIME  RSSFEK                                                             1001
WP_038431314   1115  -NSD  KLIA----  RKKDW-DPKKYGGFDSPTVAYSV-LVVAK--VE--KGKSKKLKSVKELLGISIME  RSSFEK                                                             1176
WP_038432938   1114  -NSD  KLIA----  RKKDW-DPKKYGGFDSPTVAYSV-LVVAK--VE--KGKSKKLKSVKELLGITIME  RSSFEK                                                             1175
WP_038434062   1115  -NSD  KLIA----  RKKDW-DPKKYGGFDSPTVAYSV-LVVAK--VE--KGKSKKLKSVKELLGITIME  RSSFEK                                                             1176
BAQ51233       1026  -NSD  KLIA----  RKKDW-DPKKYGGFDSPTVAYSV-LVVAK--VE--KGKSKKLKSVKELLGITIME  RSSFEK                                                             1087
KGE60162        290  -NSD  KLIA----  RKKDW-DPKKYGGFDSPTVAYSV-LVVAK--VE--KGKSKKLKSVKELLGITIME  RSSFEK                                                              351
KGE60856         53  -NSD  KLIA----  RKKDW-DPKKYGGFDSPTVAYSV-LVVAK--VE--KGKSKKLKSVKELLGITIME  RSSFEK                                                              114
WP_002989955   1115  -NSD  KLIPRKT-KNSYW-NPKKYGGFDSPVVAYSI-LVFAD--VE--KGKSKKLKRKVQDMVGITIME  KRRFEK                                                             1176
WP_003030002   1094  -ESD  KLIPRKT-KDIYL-DPKKYGGFDSPIVAYSV-LVVAD--IK--KGKAQKLKTVTELLGITIME  RSKFEK                                                             1158
WP_003065552   1122  -DSD  KLIPRKTkKA-YW-DTTKYGGFDSPTVAYSV-LVVAD--VE--KGKAKKLKTVKELVGISIME  RSFFEE                                                             1186
WP_001040076   1113  -NSD  KLIPRKT-KDIYL-DPKKYGGFDSPIVAYSV-LVVAD--IK--KGKAQKLKTVTELLGITIME  RSRFEK                                                             1177
WP_001040078   1121  -NSD  KLIPRKT-KDIYL-DPKKYGGFDSPIVAYSV-LVVAD--IK--KGKAQKLKTVTELLGITIME  RSKFEK                                                             1185
WP_001040080   1113  -NSD  KLIPRKT-KDIYL-DPKKYGGFDSPIVAYSV-LVVAD--IK--KGKAQKLKTVTELLGITIME  RSRFEK                                                             1177
WP_001040081   1113  -NSD  KLIPRKT-KDIYL-DPKKYGGFDSPIVAYSV-LVVAD--IK--KGKAQKLKTVTELLGITIME  RSRFEK                                                             1177
WP_001040083   1113  -NSD  KLIPRKT-KDIYL-DPKKYGGFDSPIVAYSV-LVVAD--IK--KGKAQKLKTVTELLGITIME  RSRFEK                                                             1177
WP_001040085   1113  -NSD  KLIPRKT-KDIYL-DPKKYGGFDSPIVAYSV-LVVAD--IK--KGKAQKLKTVTELLGITIME  RSRFEK                                                             1177
WP_001040087   1113  -NSD  KLIPRKT-KDIYL-DPKKYGGFDSPIVAYSV-LVVAD--IK--KGKAQKLKTVTELLGITIME  RSRFEK                                                             1177
WP_001040088   1113  -NSD  KLIPRKT-KDIYL-DPKKYGGFDSPIVAYSV-LVVAD--IK--KGKAQKLKTVTELLGITIME  RSRFEK                                                             1177
```

```
WP_001040089  1113  -NSD KLIPRKT-KDIYL-DPKKYGGFDSPIVAYSV-LVVAD--IK--KGKAQKLKTVTELLGITIME RSRFEK  1177
WP_001040090  1113  -NSD KLIPRKT-KDIYL-DPKKYGGFDSPIVAYSV-LVVAD--IK--KGKAQKLKTVTELLGITIME RSRFEK  1177
WP_001040091  1113  -NSD KLIPRKT-KDIYL-DPKKYGGFDSPIVAYSV-LVVAD--IK--KGKAQKLKTVTELLGITIME RERFEK  1177
WP_001040092  1113  -NSD KLIPRKT-KDIYL-DPKKYGGFDSPIVAYSV-LVLAD--IK--KGKAQKLKTVTELLGITIME RSRFEK  1177
WP_001040094  1113  -NSD KLIPRKT-KDIYL-DPKKYGGFDSPIVAYSV-LVVAD--IK--KGKAQKLKTVKELLGITIME RSRFEK  1177
WP_001040095  1113  -NSD KLIPRKT-KDIYL-DPKKYGGFDSPIVAYSV-LVVAD--IK--KGKAQKLKTVTELLGITIME RSRFEK  1177
WP_001040096  1113  -NSD KLIPRKT-KDIYL-DPKKYGGFDSPIVAYSV-LVVAD--IK--KGKAQKLKTVTELLGITIME RSRFEK  1177
WP_001040097  1113  -NSD KLIPRKT-KDIYL-DPKKYGGFDSPIVAYSV-LVVAD--IK--KGKAQKLKTVTELLGITIME RSRFEK  1177
WP_001040098  1113  -NSD KLIPRKT-KDIYL-DPKKYGGFDSPKVAYSV-LVVAD--IK--KGKAQKLKTVTELLGITIME RSRFEK  1177
WP_001040099  1113  -NSD KLIPRKT-KDIYL-DPKKYGGFDSPIVAYSV-LVVAD--IK--KGKAQKLKTVTELLGITIME RSRFEK  1177
WP_001040100  1113  -NSD KLIPRKT-KDIYL-DPKKYGGFDSPIVAYSV-LVVAD--IK--KGKAQKLKTVTELLGITIME RSRFEK  1177
WP_001040104  1113  -NSD KLIPRKT-KDIYL-DPKKYGGFDSPIVAYSV-LVVAD--IK--KGKAQKLKTVTELLGITIME RPRFEK  1177
WP_001040105  1113  -NSD KLIPRKT-KDIYL-DPKKYGGFDSPIVAYSV-LVVAD--IK--KGKAQKLKTVTELLGITIME RPRFEK  1177
WP_001040106  1113  -NSD KLIPRKT-KDIYL-DPKKYGGFDSPIVAYSV-LVVAD--IK--KGKAQKLKTVTELLGITIME RPRFEK  1177
WP_001040107  1113  -NSD KLIPRKT-KDIYL-DPKKYGGFDSPIVAYSV-LVVAD--IK--KGKAQKLKTVTELLGITIME RPRFEK  1177
WP_001040108  1113  -NSD KLIPRKT-KDIYL-DPKKYGGFDSPIVAYSV-LVVAD--IK--KGKAQKLKTVTELLGITIME RPRFEK  1177
WP_001040109  1113  -NSD KLIPRKT-KDIYL-DPKKYGGFDSPIVAYSV-LVVAD--IK--KGKAQKLKTVTELLGITIME RPRFEK  1177
WP_001040110  1113  -NSD KLIPRKT-KDIYL-DPKKYGGFDSPIVAYSV-LVLAD--IK--KGKAQKLKTVTELLGITIME RPRFEK  1177
WP_015058523  1113  -NSD KLIPRKT-KDIYL-DPKKYGGFDSPIVAYSV-LVVAD--IK--KGKAQKLKTVKELLGITIME RERFEK  1177
WP_017643650  1113  -NSD KLIPRKT-KDIYL-DPKKYGGFDSPIVAYSV-LVVAD--IK--KGKAQKLKTVTELLGITIME RSRFEK  1177
WP_017647151  1113  -NSD KLIPRKT-KDIYL-DPKKYGGFDSPIVAYSV-LVVAD--IK--KGKAQKLKTVTELLGITIME RSRFEK  1177
WP_017648376  1113  -NSD KLIPRKT-KDIYL-DPKKYGGFDSPIVAYSV-LVVAD--IK--KGKAQKLKTVTELLGITIME RSRFEK  1177
WP_017649527  1113  -NSD KLIPRKT-KDIYL-DPKKYGGFDSPIVAYSV-LVVAD--IK--KGKAQKLKTVTELLGITIME RPRFEK  1177
WP_017771611  1113  -NSD KLIPRKT-KDIYL-DPKKYGGFDSPIVAYSV-LVVAD--IK--KGKAQKLKTVTELLGITIME RPRFEK  1177
WP_017771984  1113  -NSD KLIPRKT-KDIYL-DPKKYGGFDSPIVAYSV-LVVAD--IK--KGKAQKLKTVTELLGITIME RSRFEK  1177
CFQ25032      1113  -NSD KLIPRKT-KDIYL-DPKKYGGFDSPIVAYSV-LVVAD--IK--KGKAQKLKTVTELLGITIME RSRFEK  1177
CFV16040      1113  -NSD KLIPRKT-KDIYL-DPKKYGGFDSPIVAYSV-LVVAD--IK--KGKAQKLKTVTELLGITIME RSRFEK  1177
KLJ37842      1113  -NSD KLIPRKT-KDIYL-DPKKYGGFDSPIVAYSV-LVVAD--IK--KGKAQKLKTVTELLGITIME RSRFEK  1177
KLJ72361      1113  -NSD KLIPRKT-KDIYL-DPKKYGGFDSPIVAYSV-LVVAD--IK--KGKAQKLKTVTELLGITIME RSRFEK  1177
KLL20707      1127  -NSD KLIPRKT-KDIYL-DPKKYGGFDSPIVAYSV-LVVAD--IK--KGKAQKLKTVTELLGITIME RPRFEK  1191
KLL42645      1113  -NSD KLIPRKT-KDIYL-DPKKYGGFDSPIVAYSV-LVVAD--IK--KGKAQKLKTVTELLGITIME RSRFEK  1177
WP_047207273  1113  -NSD KLIPRKT-KDIYL-DPKKYGGFDSPIVAYSV-LVVAD--IK--KGKAQKLKTVTELLGITIME RSRFEK  1177
WP_047209694  1113  -NSD KLIPRKT-KDIYL-DPKKYGGFDSPIVAYSV-LVVAD--IK--KGKAQKLKTVTELLGITIME RSRFEK  1177
WP_050198062  1113  -NSD KLIPRKT-KDIYL-DPKKYGGFDSPIVAYSV-LVAAD--IK--KGKAQKLKTVTELLGITIME RSRFEK  1177
WP_050201642  1113  -NSD KLIPRKT-KDIYL-DPKKYGGFDSPIVAYSV-LVVAD--IK--KGKAQKLKTVTELLGITIME RPRFEK  1177
WP_050204027  1113  -NSD KLIPRKT-KDIYL-DPKKYGGFDSPIVAYSV-LVVAD--IK--KGKAQKLKTVTELLGITIME RPRFEK  1177
WP_050881965  1113  -NSD KLIPRKT-KDIYL-DPKKYGGFDSPIVAYSV-LVVAD--IK--KGKAQKLKTVTELLGITIME RSRFEK  1177
WP_050886065  1113  -NSD KLIPRKT-KDIYL-DPKKYGGFDSPIVAYSV-LVLAD--IK--KGKAQKLKTVKELLGITIME RERFEK  1177
AHN30376      1113  -NSD KLIPRKT-KDIYL-DPKKYGGFDSPIVAYSV-LVVAD--IK--KGKAQKLKTVTELLGITIME RSRFEK  1177
EA078426      1113  -NSD KLIPRKT-KDIYL-DPKKYGGFDSPIVAYSV-LVVAD--IK--KGKAQKLKTVTELLGITIME RSRFEK  1177
CCW42055      1113  -NSD KLIPRKT-KDIYL-DPKKYGGFDSPIVAYSV-LVVAD--IK--KGKAQKLKTVTELLGITIME RSRFEK  1177
WP_003041502  1123  -DSS ENLVGVK-RNL---DPKKYGYAGISNSYAV-LVKAI--IE--KGVKKETMVLEFQGISILD RITFEK  1185
WP_037593752  1095  -ESD KLIPRKT-KNSYW-NPKKYGGFDSPVVAYSI-LVFAD--VE--KGKSKKLRKVQDMVGITIME KKRFEK  1159
WP_049516684  1095  -ESD KLIPRKT-KNSYW-NPKKYGGFDSPVVAYSI-LVFAD--VE--KGKSKKLRKVQDMVGITIME KKRFEK  1159
GAD46167      1094  -ESD KLIPRKT-KNSYW-NPKKYGGFDSPVVAYSI-LVFAD--VE--KGKSKKLRKVQDMVGITIME KLRFEK  1158
WP_018363470  1126  -DSD KLIPRKTkKV-LW-EPKKYGGEDSPTVAYSV-LVVAK--VE--KGKTKKLKTVKELVGISIME RSFFEK  1190
WP_003043819  1124  -ESA KLIP---RKKGW-DTRKYGGFGSPTVAYSI-LVVAK--VE--KGKAKKLSVKVLVGITIME KGSYEK  1185
WP_066269658  1094  -ESD KLIP---RKKGW-KNSYW-DTRKYGGFGSPTVAYSI-LVFAD--VE--KGKSKKLRKVQDMVGITIME RPRFEK  1158
WP_048800089  1114  -DSD KLIARKTkEN-YW-DTRKYGGEDSPTVAYSV-LVKAK--IK--KGKAKKLKTVKELVGISIME RPFFEK  1178
WP_012767106  1114  -SFD KLIS----RKHRF-ESSKYGGEGSPTVTYSV-LVVAKskVQ-DGKVKKIKTGKELIGMTLLD KLVFEK  1177
WP_014612333  1114  -SFD KLIS----RKHRF-ESSKYGGEGSPTVTYSV-LVVAKskVQ-DGKVKKIKTGKELIGITLLD KLVFEK  1177
WP_015017095  1114  -SFD KLIS----RKHRF-ESSKYGGEGSPTVTYSV-LVVAKskVQ-DGKVKKIKTGKELIGITLLD KLVFEK  1177
WP_015057649  1114  -SFD KLIS----RKHRF-ESSKYGGEGSPTVTYSV-LVVAKskVQ-DGKVKKIKTGKELIGITLLD KLVFEK  1177
```

-continued

| | | | |
|---|---|---|---|
| WP_048327215 | 1114 | -SFD KLIS----RKHRF-ESSKYGGEGSPTVTYSV-LVVAKcKVQ--DGKVKIKTGKELIGITLLD KLVFEK | 1177 |
| WP_049519324 | 1114 | -SFD KLIS----RKHRF-ESSKYGGEGSPTVTYSV-LVVAKsKVQ--DGKVKIKTGKELIGITLLD KLVFEK | 1177 |
| WP_012515931 | 1095 | -NSD KLIP----RKNNW-DTRKYGGFDSPTVAYSV-LVIAK--ME--KGKAKVLKPVKEMVGITIME RTAFEE | 1156 |
| WP_021320964 | 1095 | -NSD KLIP----RKNNW-DTRKYGGFDSPTVAYSV-LVIAK--ME--KGKAKVLKPVKEMVGITIME RTAFEE | 1156 |
| WP_037581760 | 1124 | -DSD KLIP----RKNNW-DTRKYGGFDSPTVAYSV-LVIAK--ME--KGKAKVLKPVKEMVGITIME RIAFEE | 1188 |
| WP_044232481 | 1124 | -DSD KLIP----RKNNW-DTRKYGGFDSPTVAYSV-LVIAK--ME--KGKAKVLKPVKEMVGITIME RIAFEE | 1188 |
| WP_009854540 | 1119 | -DSD KLIPRKTkKL-QW-ETQKYGGEDSPTVAYSV-LVVAD--VE--KGKTRKLKTVKELVGISIME RSFFEE | 1183 |
| WP_012962174 | 1121 | -NSD KLIPRKTkKV-YW-DTKKYGGEDSPTVAYSV-FVVAD--VE--KGKAKKLKTVKELVGISIME RSFFEE | 1184 |
| WP_039695303 | 1124 | -DSD KLIPRKTkKV-YW-DTKKYGGEDSPTVAYSV-FVVAD--VE--KGKAKKLKTVKELVGISIME RSFFEE | 1185 |
| WP_014334983 | 1124 | -DSD KLIPRKTkKV-YW-NTKKYGFDSPTVAYSV-LVVAD--IE--KGKAKKLKTVKELVGISIME RSFFEE | 1188 |
| WP_003099269 | 1115 | -DSD KLIA----RKKSW-DPKKYGGFDSPIIAYSV-LVVAK--IA--KGKTQKLKTIKELVGIKIME QDEFEK | 1176 |
| AHY15608 | 1115 | -DSD KLIA----RKKSW-DPKKYGGFDSPIIAYSV-LVVAK--IA--KGKTQKLKTIKELVGIKIME QDEFEK | 1176 |
| AHY17476 | 1115 | -DSD KLIA----RKKSW-DPKKYGGFDSPIIAYSV-LVIAD--IA--KGKTQKLKTIKELVGIKIME QDEFEK | 1176 |
| ESR09100 | 1 | -- | ME QDEFEK | 8 |
| AGM98575 | 1115 | -DSD KLIA----RKKSW-DPKKYGGFDSPIIAYSV-LVVAK--IA--KGKTQKLKTIKELVGIKIME QDEFEK | 1176 |
| ALF27331 | 1094 | -NSD KLIPRKT-KKFYW-DTKKYGGFDSPIVAYSI-LVIAD--IE--KGKSKKLKLVKDLVGITIME RTIFEK | 1158 |
| WP_018372492 | 1109 | -NN KLIP----RKKDW-SVDKYGGFIEPAESYSLaIFYTD--IN---GKKPKKKSTIIAISRME KKDYEK | 1167 |
| WP_045618028 | 1125 | vvDAS KLTPIKS-G---L-SPEKYGGYARPTIAYSV-LVIAD--IE--KGKAKKLRIKEMVGITVQD KKKFEA | 1188 |
| WP_045635197 | 1119 | -NSD KLIPRKT-KDILL-DTTKYGGFDSPVIAYSI-LLIAD--IE--KGKAKKLKTVKTLVGITIME KAAFEE | 1183 |
| WP_002263549 | 1094 | -NSD KLIPRKT-KKFYW-DTKKYGGFDSPIVAYSI-LVIAD--IE--KGKSKKLKTVKALVGVTIME KMTFER | 1158 |
| WP_002263887 | 1094 | -DSD KLIPRKT-KKFYW-DTKKYGGFDSPIVAYSI-LVIAD--IE--KGKSKKLKTVKALVGVTIME KMTFER | 1158 |
| WP_002264920 | 1094 | -NSD KLIPRKT-KKFYW-DTKKYGGFDSPIVAYSI-LVIAD--IE--KGKSKKLKTVKALVGVTIME KMTFER | 1158 |
| WP_002269043 | 1094 | -NSD KLIPRKT-KKFYW-DTKKYGGFDSPIVAYSI-LVIAD--IE--KGKSKKLKTVKALVGVTIME KMTFER | 1158 |
| WP_002269448 | 1094 | -NSD KLIPRKT-KKFYW-DTKKYGGFDSPIVAYSI-LVIAD--IE--KGKSKKLKTVKALVGVTIME KMTFER | 1158 |
| WP_002271977 | 1094 | -NSD KLIPRKT-KKFYW-DTKKYGGFDSPIVAYSI-LVIAD--IE--KGKSKKLKTVKALVGVTIME KMTFER | 1158 |
| WP_002272766 | 1094 | -NSD KLIPRKT-KKFYW-DTKKYGGFDSPIVAYSI-LVIAD--IE--KGKSKKLKTVKALVGVTIME KMTFER | 1158 |
| WP_002273241 | 1094 | -NSD KLIPRKT-KKFYW-DTKKYGGFDSPIVAYSI-LVIAD--IE--KGKSKKLKTVKALVGVTIME KMTFER | 1158 |
| WP_002275430 | 1094 | -NSD KLIPRKT-KKFYW-DTKKYGGFDSPIVAYSI-LVIAD--IE--KGKSKKLKTVKALVGVTIME KMTFER | 1158 |
| WP_002276448 | 1094 | -NSD KLIPRKT-KKFYW-DTKKYGGFDSPIVAYSI-LVIAD--IE--KGKSKKLKTVKALVGVTIME KMTFER | 1158 |
| WP_002277050 | 1112 | -PLE KLVPLKK---AL-NPEKYGGYQKPTTAYPI-LLIVD-------TKQLIPISVMD KKRFEQ | 1166 |
| WP_002773364 | 1094 | -NSD KLIPRKT-KKFYW-DTKKYGGFDSPIVAYSI-LVIAD--IE--KGKSKKLKTVKALVGVTIME KMTFER | 1158 |
| WP_002282247 | 1112 | -PLE KLVPLKK---AL-NPEKYGGYQKPTTAYPI-LLIVD-------TKQLIPISVMD KKRFEQ | 1166 |
| WP_002282906 | 1094 | -NSD KLIPRKT-KKFYW-DTKKYGGFDSPIVAYSI-LVIAD--IE--KGKSKKLKTVKALVGVTIME KMTFER | 1158 |
| WP_002283846 | 1094 | -NSD KLIPRKT-KKFYW-DTKKYGGFDSPIVAYSI-LVIAD--IE--KGKSKKLKTVKALVGVTIME KMTFER | 1158 |
| WP_002279025 | 1094 | -NSD KLIPRKT-KKFYW-DTKKYGGFDSPIVAYSI-LVIAD--IE--KGKSKKLKTVKALVGVTIME KMTFER | 1158 |
| WP_002279859 | 1094 | -DSD KLIPRKT-KKFYW-DTKKYGGFDSPIVAYSI-LVIAD--IE--KGKSKKLKTVKALVGVTIME KMTFER | 1158 |
| WP_002280230 | 1094 | -NSD KLIPRKT-KKFYW-DTKKYGGFDSPIVAYSI-LVIAD--IE--KGKSKKLKTVKALVGVTIME KMTFER | 1158 |
| WP_002281696 | 1094 | -NSD KLIPRKT-KKFYW-DTKKYGGFDSPIVAYSI-LVIAD--IE--KGKSKKLKTVKALVGVTIME KMTFER | 1158 |
| WP_002288990 | 1094 | -NSY KLIPRKT-KKFYW-DTKKYGGFDSPIVAYSI-LVIAD--IE--KGKSKKLKTVKALVGVTIME KMTFER | 1158 |
| WP_002289641 | 1094 | -NSD KLIPRKT-KKFYW-DTKKYGGFDSPIVAYSI-LVIAD--IE--KGKSKKLKTVKALVGVTIME KMTFER | 1158 |
| WP_002290427 | 1094 | -DSD KLIPRKT-KKFYW-DTKKYGGFDSPIVAYSI-LVIAD--IE--KGKSKKLKTVKALVGVTIME KMTFER | 1158 |
| WP_002295753 | 1094 | -NSD KLIPRKT-KKFYW-DTKKYGGFDSPIVAYSI-LVIAD--IE--KGKSKKLKTVKALVGVTIME KMTFER | 1158 |
| WP_002296423 | 1108 | -NSD KLIPRKT-KKFYW-DTKKYGGFDSPIVAYSI-LVIAD--IE--KGKSKKLKTVKALVGVTIME KMTFER | 1172 |
| WP_003044487 | 1094 | -NSD KLIPRKT-KKFYW-DTKKYGGFDSPIVAYSI-LVIAD--IE--KGKSKKLKTVKALVGVTIME KMTFER | 1158 |
| WP_003305844 | 1094 | -NSD KLIPRKT-KKFYW-DTKKYGGFDSPIVAYSI-LVIAD--IE--KGKSKKLKTVKALVGVTIME KMTFER | 1158 |
| WP_003072203 | 1094 | -NSD KLIPRKT-KKFYW-DTKKYGGFDSPIVAYSI-LVIAD--IE--KGKSKKLKTVKALVGVTIME KMTFER | 1158 |
| WP_003210390 | 1094 | -DSD KLIPRKT-KKFYW-DTKKYGGFDSPIVAYSI-LVIAD--IE--KGKSKKLKTVKALVGVTIME KMTFER | 1158 |
| WP_003252408 | 1094 | -NSD KLIPRKT-KKFYW-DTKKYGGFDSPIVAYSI-LVIAD--IE--KGKSKKLKTVKALVGVTIME KMTFER | 1158 |
| WP_012997688 | 1094 | -NSD KLIPRKT-KKFYW-DTKKYGGFDSPIVAYSI-LVIAD--IE--KGKSKKLKTVKALVGVTIME KMTFER | 1158 |
| WP_014677909 | 1094 | -NSD KLIPRKT-KKFYW-DTKKYGGFDSPIVAYSI-LVIAD--IE--KGKSKKLKTVKALVGVTIME KMTFER | 1158 |
| WP_019312892 | 1094 | -NSD KLIPRKT-KKFYW-DTKKYGGFDSPIVAYSI-LVIAD--IE--KGKSKKLKTVKALVGVTIME KMTFER | 1158 |
| WP_019313659 | 1094 | -NSD KLIPRKT-KKFYW-DTKKYGGFDSPIVAYSI-LVIAD--IE--KGKSKKLKTVKALVGVTIME KMTFER | 1158 |

```
WP_019314093   1094  --NSD KLIPRKT-KKFYW-DTKKYGGFDSPIVAYSI-LVIAD--IE--KGKSKKLKTVKALVGVTIME KMTFER  1158
WP_019315370   1094  --NSD KLIPRKT-KKFYW-DTKKYGGFDSPIVAYSI-LVIAD--IE--KGKSKKLKTVKALVGVTIME KMTFER  1158
WP_019803776   1094  --NSD KLIPRKT-KKFYW-DTKKYGGFDSPIVAYSI-LVIAD--IE--KGKSKKLKTVKALVGVTIME KMTFER  1158
WP_019805234   1094  --DSD KLIPRKT-KKFYW-DTKKYGGFDSPIVAYSI-LVIAD--IE--KGKSKKLKTVKALVGVTIME KMTFER  1158
WP_024783594   1094  --NSD KLIPRKT-KKFYW-DTKKYGGFDSPIVAYSI-LVIAD--IE--KSKSKKLKTVKALVGVTIME KMTFER  1158
WP_024784288   1112  --PLE KLVPLKK----AL-NPEKYGGYQKPTTAYPI-LLIVD----------TKQLPISVMD KKRFEQ  1166
WP_024784666   1094  --NSD KLIPRKT-KKFYW-DTKKYGGFDSPIVAYSI-LVIAD--IE--KGKSKKLKTVKALVGVTIME KMTFER  1158
WP_024784894   1094  --NSD KLIPRKT-KKFYW-DTKKYGGFDSPIVAYSI-LVIAD--IE--KGKSKKLKTVKALVGVTIME KMTFER  1158
WP_024786433   1112  --PLE KLVPLKK----AL-NPEKYGGYQKPTTAYPI-LLIVD----------TKQLPISVMD KKRFEQ  1166
WP_049473442   1094  --NSD KLIPRKT-KKFYW-DTKKYGGFDSPIVAYSI-LVIAD--IE--KGKSKKLKTVKALVGVTIME KMTFER  1158
WP_049474547   1094  --NSD KLIPRKT-KKFYW-DTKKYGGFDSPIVAYSI-LVIAD--IE--KGKSKKLKTVKALVGVTIME KMTFER  1158
EMC03581       1087  --NSD KLIPRKT-KKFYW-DTKKYGGFDSPIVAYSI-LVIAD--IE--KGKAKRLKTVKTLVGITIME KATFEK  1151
WP_000428612   1122  --NSD KLIPRKT-KDILW-DTTKYGGFDSPIVAYSI-LLIAD--IE--KGKAKKLKTVKTLVGITIME KAAFEE  1186
WP_000428613   1120  --NSD KLIPRKT-KDILW-ETTKYGGFDSPIVAYSI-LLIAD--IE--KGKAKKLKTVKTLVGITIME KAAFEE  1184
WP_049523028   1115  --NSD KLIPRKT-KNVQL-DTTKYGGFDSPIVAYSI-LVVAD--VE--KGKSQKTKSVKELVGITIME KVKFEA  1179
WP_003107102   1084  --DSD KLIP----RKNNW-DPKKYGGFDSPIIAYSV-LVVAK--VT--KGKSQKTKSVKELVGITIME QNEFEK  1145
WP_054279288   1116  --KSS KLIP----RKNKWrDTTKYGGFNTPTVAYSV-LVVAK--VE--KGKAKKLKPVKELVGITIME RTKFEA  1178
WP_049531101   1125  vvDAS KLIPIKS-G---L-SPEKYGGYARPTIAYSV-LVIAD--IE--KGKAKKLKRIKEMVGITIQD KKKFEA  1188
WP_049538452   1125  vvDAS KLIPIKS-G---L-SPEKYGGYARPTIAYSV-LVIAD--IE--KGKTKKLKRIKEMIGITVQD KKIFES  1188
WP_049549711   1127  vvDAS KLIPIKS-G---L-SPEKYGGYARPTIAYSV-LVIAD--IE--KGKTKKLKRIKEMVGITIQD KKKFEA  1190
WP_007896501   1121  --NSD KLIE----RKKGW-DPKKYGGFDSPNTAYSI-FVVAK--VA--KRKAQKLKTVKEIVGITIME QAEYEK  1182
EFR44625       1073  --NSD KLIE----RKKGW-DPKKYGGFDSPNTAYSI-FVVAK--VA--KRKAQKLKTVKEIVGITIME QAEYEK  1134
WP_002897477   1119  --NSD KLIPRKT-KDILW-DTTKYGGFDSPIVAYSI-LVIAD--IE--KGKAKKLKTVKTLVGITIME KAAFEE  1183
WP_002906454   1124  vvDAS KLIPIKS-S---L-SPEKYGGYARPTIAYSV-LVIAD--IEkGKGKAKKLKRIKEIVGITIQD KKKFES  1189
WP_009729476   1120  --NSD KLIPRKT-KDILW-DTTKYGGFDSPIVAYSI-LLIAD--IE--KGKAKKLKTVKTLVGITIME KDAFEK  1184
CQR24647       1110  --GSD KLIARKT-KNNYL-STQKYGGFDSPTVAYSI-MFVAD--IE--KGKSRKLKTVKEMIGITIME RSRFES  1174
WP_000066813   1124  --NSD KLIP----KEILW-DTTKYGGFDSPIVAYSI-LLIAD--IE--KGKAKKLKTVKTLVGITIME KATFEK  1188
WP_009754323   1120  --NSD KLIP----KDILW-DTTKYGGFDSPIVAYSI-LLIAD--IE--KGKAKKLKTVKTLVGITIME KAAFEK  1184
WP_044674937   1113  --DSD KLIP----EKFYL-DTKKYGGFDSPTIAYSV-LLIAD--IE--KGKAKKLKRVKELIGITIME RMAFEK  1177
WP_044676715   1115  --DSD KLIP----EKFYL-DTKKYGGFDSPTIAYSV-LLIAD--IE--KGKAKKLKRVKELIGITIME RMAFEK  1179
WP_044680361   1115  --DSD KLIP----EKFYL-DTKKYGGFDSPTIAYSV-LLIAD--IE--KGKAKKLKRVKELIGITIME RMAFEK  1179
WP_044681799   1113  --DSD KLIP----EKFYL-DTKKYGGFDSPTIAYSV-LLIAD--IE--KGKAKKLKRVKELIGITIME RMAFEK  1177
WP_049533112   1123  --DSS ENLVGVK-RNL--DPKKYGGYAGISNSYAV-LVKA1--IE--KGVKKKETMVLEFQGISILD RITFEK  1185
WP_029090905   1062  --SSS KTIP----LKKHL-DTAIYGGYTAVNYASYA---LIQ--FK--KGRKLK--REIIGIPLAV QTRIDN  1117
WP_006506696   1085  haDKG AVVP----vNKNRS-DVHKYGGFSG--LQYTI----VA--IEggKKKGKKTELVKKISGVPLHL KAASIN  1149
AIT42264       1115  --NSD KLIA----RKKDW-DPKKYGGFDSPTVAYSV-LVVAK--VE--KGKSKKLKSVKEILGITIME RSSFEK  1176
WP_034440723   1093  k-KTE KRIP----IKNNL-DPNIYGGYIEEKMAYYI---AInyLE-NGKTKK--AIVGISIKD KDFEG  1149
AKQ21048       1115  --NSD KLIA----RKKDW-DPKKYGGFDSPTVAYSV-LVVAK--VE--KGKSKKLKSVKEILGITIME RSSFEK  1176
WP_004636532   1093  --DSS KLIP----VKEGM-DPQKYGGLSQVSEAFAV-VIT----HE--KGKKKQLK--SDLISIPIVD QKAYEQ  1150
WP_002364836   1099  --PSN KLIP----VKNGL-DPQKYGGFDSPIVAYTV-LF----T--HE--KGK-KPL-IKQEILGITIME KTRFEQ  1156
WP_016631044   1050  --PSN KLIP----VKNGL-DPQKYGGFDSPIVAYTV-LF----T--HE--KGK-KPL-IKQEILGITIME KTRFEQ  1107
EMS75795       835   --KPD KLIQ----RKAGW-DVSKYGGFGSPVVAYAV-AFI----YE--KGKAR--KKAKAIEGITIME QSLFEQ  892
WP_002373311   1099  --PSN KLIP----VKNGL-DPQKYGGFDSPIVAYTV-LF----T--HE--KGK-KPL-IKQEILGITIME KTRFEQ  1156
WP_002378009   1099  --PSN KLIP----VKNGL-DPQKYGGFDSPIVAYTV-LF----T--HE--KGK-KPL-IKQEILGITIME KTRFEQ  1156
WP_002407324   1099  --PSN KLIP----VKNGL-DPQKYGGFDSPVVAYTV-LF----T--HE--KGK-KPL-IKQEILGITIME KTRFEQ  1156
WP_002413717   1101  --PSN KLIP----VKNGL-DPQKYGGFDSPVVAYTV-LF----T--HE--KGK-KPL-IKQEILGITIME KTRFEQ  1158
WP_010775580   1099  --PSN KLIP----VKNGL-DPQKYGGFDSPVVAYTV-LF----T--HE--KGK-KPL-IKQEILGITIME KTRFEQ  1156
WP_010818269   1099  --PSN KLIP----VKNGL-DPQKYGGFDSPVVAYTV-LF----T--HE--KGK-KPL-IKQEILGITIME KTRFEQ  1156
WP_010824395   1099  --PSN KLIP----VKNGL-DPQKYGGFDSPVVAYTV-LF----T--HE--KGK-KPL-IKQEILGITIME KTRFEQ  1156
WP_016622645   1099  --PSN KLIP----VKNGL-DPQKYGGFDSPVVAYTV-LF----T--HE--KGK-KPL-IKQEILGITIME KTRFEQ  1156
WP_033624816   1099  --PSN KLIP----VKNGL-DPQKYGGFDSPVVAYTV-LF----T--HE--KGK-KPL-IKQEILGITIME KTKFEQ  1156
WP_033625576   1099  --PSN KLIP----VKNGL-DPQKYGGFDSPVVAYTV-LF----T--HE--KGK-KPL-IKQEILGITIME KTRFEQ  1156
WP_033789179   1099  --PSN KLIP----VKNGL-DPQKYGGFDSPVVAYTV-LF----T--HE--KGK-KPL-IKQEILGITIME KTRFEQ  1156
```

| | | | | | | |
|---|---|---|---|---|---|---|
| WP_002310644 | 1101 | -DSS KLLP- | ---RKNNW-DPAKYGGLGSPNVAYTV-AFT- | ---YE- | KGKAR- | -KRTNALEGITIME REAFEQ 1158 |
| WP_002312694 | 1102 | -DSS KLLP- | ---RKNNW-DPAKYGGLGSPNVAYTV-AFT- | ---YE- | KGKAR- | -KRTNALEGITIME REAFEQ 1159 |
| WP_002314015 | 1102 | -DSS KLLP- | ---RKNNW-DPAKYGGLGSPNVAYTV-AFT- | ---YE- | KGKAR- | -KRTNALEGITIME REAFEQ 1159 |
| WP_002320716 | 1102 | -DSS KLLP- | ---RKNNW-DPAKYGGLGSPNVAYTV-AFT- | ---YE- | KGKAR- | -KRTNALEGITIME REAFEQ 1159 |
| WP_002330729 | 1101 | -DSS KLLP- | ---RKNNW-DPAKYGGLGSPNVAYTV-AFT- | ---YE- | KGKAR- | -KRTNALEGITIME REAFEQ 1158 |
| WP_002335161 | 1102 | -DSS KLLP- | ---RKNNW-DPAKYGGLGSPNVAYTV-AFT- | ---YE- | KGKAR- | -KRTNALEGITIME REAFEQ 1159 |
| WP_002345439 | 1102 | -DSS KLLP- | ---RKNNW-DPTKYGGLGSPNVAYTV-AFT- | ---YE- | KGKAR- | -KRTNALEGITIME REAFEQ 1159 |
| WP_034867970 | 1092 | -KPD KLIE- | ---RKNNW-DVTKYGGFGSPVIAYAI-AFV- | ---YA- | KGKTQ- | -KKTRAIEGITIME QAAFEK 1149 |
| WP_047937432 | 1102 | -DSS KLLP- | ---RKNNW-DPAKYGGLGSPNVAYTV-AFT- | ---YE- | KGKAR- | -KRTNALEGITIME REAFEQ 1159 |
| WP_010720994 | 1092 | -KPD KLIE- | ---RKNNW-DVTKYGGFGSPVIAYAI-AFV- | ---YA- | KGKTQ- | -KKTKAIEGITIME QAAFEK 1149 |
| WP_010737004 | 1092 | -KPD KLIE- | ---RKNNW-DVTKYGGFGSPVIAYAI-AFV- | ---YA- | KGKTQ- | -KKTRAIEGITIME QAAFEK 1149 |
| WP_034700478 | 1092 | -KPD KLIE- | ---RKNNW-DVTKYGGFGSPVIAYAI-AFV- | ---YA- | KGKTQ- | -KKTRAIEGITIME QAAFEK 1149 |
| WP_007209003 | 1090 | -ESQ KLIR- | ---RKQQW-NTKKYGGFDSPVVAYAI- | ---LLS- | FD- | -RKARSFK-IVGITIQD RESFEG 1147 |
| WP_023351917 | 1086 | -NPE KLIP- | ---RKASL-DPLKYGGYGSPLVAYTV-IFI- | ---FE- | KGKQK- | -KVTKGIEGITVME QLRFEQ 1143 |
| WP_010770040 | 1097 | -DSD KLIS- | ---RKTNW-SPKLYGGFDSPQVAYSV-II- | ---T- | YE- | KGK-KKVRA-KAIVGITIME QSLFKK 1154 |
| WP_048604708 | 1094 | -DSD KLIS- | ---RKKEW-DTTKYGGFDSPNMAYAV-VI- | ---R- | YE- | KGK-TRKLV-KTIVGITIME RAAFEK 1151 |
| WP_010750235 | 1095 | -KPD KLIK- | ---RKNNW-DVTKYGGFGSPVVAYAV-VFT- | ---YE- | KGKNH- | -KKAKAIEGITIME QALFEK 1152 |
| AII16583 | 1154 | -NSD KLIA- | ---RKKDW-DPKKYGGFDSPTVAYSV-LVVAK- | ---VE- | KGKSKKLKSVKELLGITIME RSSFEK 1215 |
| WP_029073316 | 1100 | hsEKG AKVP- | -vNKLRS-NVHKYGGPEG--LKYSI- | ---VA- | IKgkKKKGKKIIDVNKLVGIPLMY KNVDDE 1164 |
| WP_031589969 | 1100 | nsDKD ATVP- | -vNKYRS-NVHKYGPSG--VNSFI- | ---VA- | IKgkKKKGKKVIEVNKLTGIPLMY KNADEE 1164 |
| KDA45870 | 1079 | -DSG KLLP- | ---RKEGL-DPVKYGYAKAVESYAV-LITAD- | eVK- | GKTKKKVT--LVNIPIID SKKYEA 1138 |
| WP_039099354 | 1098 | k-ASG QLIPAKqdRPTAL- | --QKKDM-DPNIYGGFSGDNKSSIT- | ---IVK- | ID- | ---NNKIKPVA--IPIRLIN ---DK 1172 |
| AKP02966 | 1119 | k---- KLIA- | ---QKKDM-DPNIYGGFSGDNKSSIT- | ---IVK- | ID- | ---NNKIKPVA--IPIRLIN ---DK 1172 |
| WP_010991369 | 1096 | -NSS KLIP- | ---RKTNW-DPMKYGGLDSPNMAYAV-VI- | ---E- | YA- | KGK-NKLVFEKKIIRVTIME RKAFEK 1154 |
| WP_033838504 | 1099 | -NSS KLIS- | ---RKTNW-DPMKYGGLDSPNMAYAV-VI- | ---E- | YA- | KGK-NKLVFEKKIIRVTIME RKAFEK 1157 |
| EHN60060 | 865 | -NSS KLIS- | ---RKTNW-DPMKYGGLDSPNMAYAV-VI- | ---E- | YA- | KGK-NKLVFEKKIIRVTIME RKAFEK 923 |
| WP_038409211 | 1096 | -NSS KLIS- | ---RKADW-DPMKYGGFDGSNMAYSI-VI- | ---E- | YE- | KRK-KKTVIKKELIQINIME RVAFEK 1154 |
| EFR95520 | 715 | -NSS KLIS- | ---RKADW-NPIKYGGFDGSNMAYSI-VI- | ---E- | YE- | KRK-KKTVIKKELIQINIME RVAFEK 773 |
| WP_003723650 | 1096 | -NSS KLIP- | ---RKENW-DPMKYGGLDSPNMAYAV-II- | ---E- | HA- | KGK-KKIVIEKKLIQINIME RKMFEK 1154 |
| WP_003727705 | 1096 | -NSS KLIP- | ---RKENW-DPMKYGGLDSPNMAYAV-III- | ---E- | HA- | KGK-KKIVIEKKLIQINIME RKMFEK 1154 |
| WP_003730785 | 1096 | -NSS KLIP- | ---RKENW-DPMKYGGLDSPNMAYAV-VI- | ---E- | HA- | KGK-KKIVIEKKLIQINIME RKMFEK 1154 |
| WP_003733029 | 1096 | -KSN KLIP- | ---RKTNW-DPIKYGGFDGSKMAYAI-III- | ---E- | YE- | KQK-RKVRIEKKLIQINIME REAFEK 1154 |
| WP_003739838 | 1096 | -NSS KLIP- | ---RKENW-DPMKYGGLDSPNMAYAV-III- | ---E- | HA- | KGK-KKVFEKKIIRITIME RKAFEK 1154 |
| WP_014601172 | 1096 | -NSS KLIP- | ---RKENW-DPMKYGGLDSPNMAYAV-II- | ---E- | HE- | KGK-KKLIPEKKIRITIME RKAFEK 1154 |
| WP_023548323 | 1096 | -DSS KLIP- | ---KKTNL-NPIKYGGFEGSNMAYAV-II- | ---E- | HE- | KRK-KKTVIEKKLIQINIME RKMFEK 1154 |
| WP_031665337 | 1096 | -NSS KLIP- | ---RKENW-DPMKYGGLDSPNMAYAV-III- | ---E- | HA- | KGK-KRIVIEKKLIQINIME RKMFEK 1154 |
| WP_031669209 | 1096 | -KSN KLIP- | ---RKKDW-DPIKYGGFDGSKMAYAI-III- | ---E- | YE- | KQK-RKVRIEKKLIRITIME REAFEK 1154 |
| WP_033920898 | 1096 | -NSS KLIP- | ---RKENW-DPMKYGGLDSPNMAYAI-II- | ---E- | HE- | KGK-KKLIPEKKIRITIME RKAFEK 1154 |
| AKI42028 | 1099 | -DSS KLIP- | ---KKTNL-NPIKYGGFEGSNMAYAV-II- | ---E- | HE- | KRK-KKTVIEKKLIQINIME RKMFEK 1157 |
| AKI50529 | 1099 | -NSS KLIP- | ---RKENW-DPMKYGGLDSPNMAYAI-III- | ---E- | HA- | KGK-KKIVIEKKLIQINIME RKMFEK 1157 |
| EFR83390 | 544 | -NSS KLIP- | ---RKADW-DPIKYGGFDGSNMAYAI-VI- | ---E- | HE- | KRK-KKTVIKKELLGITIME RTAFEK 602 |
| WP_046323366 | 1096 | -NSD KLIA- | ---RKTNW-DPMKYGGLDSPSTVAYSV-LVVAK- | ---VE- | KGKSKKLKSVKELLGITIME RSSFEK 1154 |
| AKE81011 | 1131 | hsAKG AVIP- | -vNKNRK-DVNKYGGFSG--LQYVI- | ---AA- | IEgtKKKGKKLVKRKLSGIPLYL KQADIK 1192 |
| CUO82355 | 1089 | ATVP- | -1NKYRA-DVHKYGGFGN--VQSII- | ---VA- | IEgkKKKGKKLIDVRKLTSIPLHL KNAPVE 1153 |
| WP_033162887 | 1090 | -NSD KLIA- | ---RKKDW-DPKKYGGFDSPTVAYSV-LVVAK- | ---VE- | KGKSKKLKSVKELLGITIME RSSFEK 1154 |
| AGZ01981 | 1148 | -NSD KLIA- | ---RKKDW-DPKKYGGFDSPTVAYSV-LVVAK- | ---VE- | KGKSKKLKSVKELLGITIME RSSFEK 1209 |
| AKA60242 | 1115 | -NSD KLIA- | ---RKKDW-DPKKYGGFDSPTVAYSV-LVVAK- | ---VE- | KGKSKKLKSVKELLGITIME RSSFEK 1176 |
| AKS40380 | 1115 | -NSD KLIA- | ---RKKDW-DPKKYGGFDSPTVAYSV-LVVAK- | ---VE- | KGKSKKLKSVKELLGITIME RSSFEK 1176 |
| 4UN5_B | 1119 | -NSD KLIA- | ---RKKDW-DPKKYGGFDSPTVAYSV-LVVAK- | ---VE- | KGKSKKLKSVKELLGITIME RSSFEK 1180 |
| WP_010922251 | 1177 | NPI--- -DFLE- | ---AKGYKE-V-KKDLIIK--LPKYSLFE- | ---LENGRKRMLAS -dLQKGNELALPSKYVNFLYLA 1239 |
| WP_039695303 | 1186 | NPV--- -EFLE- | ---NKGYHN--I-REDKLIK--LPKYSLFE- | ---FEGGRRRLLAS ASELQKGNEMVLPGYLVELLYHA 1248 |
| WP_045635197 | 1184 | NPI--- -TFLE- | ---NKGYHN--V-RKENILC--LPKYSLFE- | ---LENGRRRLLAS AKELQKGNEIVLPVYLTTLLYHS 1246 |

| | | | | | |
|---|---|---|---|---|---|
| 5AXW_A | 913 | KPYrfdVVLD---NGVVKFvtV-KNLDVIK---KENYYE---VNSKAYEEAKK | -KKISNQAEFIASFYNNDLIKIN | 978 |
| WP_009880683 | 861 | DPV----DFLE---AKGYKE--V-RKDLIIK---LPKYSLFE---LENGRKRMLAS | -GELQKGNELALPSKYVNFLYLA | 923 |
| WP_010922251 | 1177 | NPI----DFLE---AKGYKE--V-KKDLIIK---LPKYSLFE---LENGRKRMLAS | -GELQKGNELALPSKYVNFLYLA | 1239 |
| WP_011054416 | 1177 | DPI----DFLE---AKGYKE--V-RKDLIVK---LPKYSLFE---LENGRKRMLAS | -GELQKGNELALPSKYVNFLYLA | 1239 |
| WP_011284745 | 1177 | NPI----DFLE---AKGYKE--V-RKDLIIK---LPKYSLFE---LENGRKRMLAS | -GELQKGNELALPSKYVNFLYLA | 1239 |
| WP_011285506 | 1177 | DFLE----DFLE---AKGYKE--V-KKDLIIK---LPKYSLFE---LENGRKRMLAS | -GELQKGNELALPSKYVNFLYLA | 1239 |
| WP_011527619 | 1177 | DPV----DFLE---AKGYKE--V-RKDLIIK---LPKYSLFE---LENGRKRMLAS | -GELQKGNELALPSKYVNFLYLA | 1239 |
| WP_012560673 | 1177 | DPV----DFLE---AKGYKE--V-KKDLIIK---LPKYSLFE---LENGRKRMLAS | -GELQKGNELALPSKYVNFLYLA | 1239 |
| WP_014407541 | 1176 | NPI----DFLE---AKGYKE--V-KKDLIIK---LPKYSLFE---LENGRKRMLAS | -GELQKGNELALPSKYVNFLYLA | 1238 |
| WP_020905136 | 1177 | NPI----DFLE---AKGYKE--V-RKDLIIK---LPKYSLFE---LENGRKRMLAS | -GELQKGNELALPSKYVNFLYLA | 1239 |
| WP_023080005 | 1176 | NPI----DFLE---AKGYKE--V-RKDLIIK---LPKYSLFE---LENGRKRMLAS | -GELQKGNELALPSKYVNFLYLA | 1238 |
| WP_023610282 | 1176 | NPI----DFLE---AKGYKE--V-RKDLIIK---LPKYSLFE---LENGRKRMLAS | -GELQKGNELALPSKYVNFLYLA | 1238 |
| WP_030125963 | 1177 | NPI----DFLE---AKGYKE--V-RKDLIIK---LPKYSLFE---LENGRKRMLAS | -GELQKGNELALPSKYVNFLYLA | 1239 |
| WP_030126706 | 1177 | NPI----DFLE---AKGYKE--V-RKDLIIK---LPKYSLFE---LENGRKRMLAS | -GELQKGNELALPSKYVNFLYLA | 1239 |
| WP_031488318 | 1177 | NPI----DFLE---AKGYKE--V-RKDLIIK---LPKYSLFE---LENGRKRMLAS | -GELQKGNELALPSKYVNFLYLA | 1239 |
| WP_032460140 | 1177 | DPV----DFLE---AKGYKE--V-RKDLIIK---LPKYSLFE---LENGRKRMLAS | -GELQKGNELALPSKYVNFLYLA | 1239 |
| WP_032461047 | 1177 | DPV----DFLE---AKGYKE--V-KKDLIIK---LPKYSLFE---LENGRKRMLAS | -GELQKGNELALPSKYVNFLYLA | 1239 |
| WP_032462016 | 1177 | NPI----DFLE---AKGYKE--V-KKDLIIK---LPKYSLFE---LENGRKRMLAS | -GELQKGNELALPSKYVNFLYLA | 1239 |
| WP_032462936 | 1177 | NPI----DFLE---AKGYKE--V-KKDLIIK---LPKYSLFE---LENGRKRMLAS | -GELQKGNELALPSKYVNFLYLA | 1239 |
| WP_032464890 | 1177 | NPI----DFLE---AKGYKE--V-RKDLIIK---LPKYSLFE---LENGRKRMLAS | -GELQKGNELALPSKYVNFLYLA | 1239 |
| WP_033888930 | 1002 | NPI----DFLE---AKGYKE--V-KKDLIIK---LPKYSLFE---LENGRKRMLAS | -GELQKGNELALPSKYVNFLYLA | 1064 |
| WP_038431314 | 1177 | NPI----DFLE---AKGYKE--V-RKDLIIK---LPKYSLFE---LENGRKRMLAS | -GELQKGNELALPSKYVNFLYLA | 1239 |
| WP_038432938 | 1176 | NPI----DFLE---AKGYKE--V-RKDLIIK---LPKYSLFE---LENGRKRMLAS | -GELQKGNELALPSKYVNFLYLA | 1238 |
| WP_038434062 | 1177 | NPI----DFLE---AKGYKE--V-RKDLIIK---LPKYSLFE---LENGRKRMLAS | -GELQKGNELALPSKYVNFLYLA | 1239 |
| BAQ51233 | 1088 | DPI----DFLE---AKGYKE--V-RKDLIIK---LPKYSLFE---LENGRKRMLAS | -GELQKGNELALPSKYVNFLYLA | 1150 |
| KGE60162 | 352 | DPI----DFLE---AKGYKE--V-RKDLIIK---LPKYSLFE---LENGRKRMLAS | -GELQKGNELALPSKYVNFLYLA | 414 |
| KGE60856 | 115 | NPI----DFLE---AKGYKE--V-RKDLIIK---LPKYSLFE---LENGRKRMLAS | -GELQKGNELALPSKYVNFLYLA | 177 |
| WP_002989955 | 1177 | NPI----DFLE---QRGYRN---V-RLEKIIK---LPKYSLFE---LENKRRLLAS | ARELQKGNELVIPQRFTTLLYHS | 1239 |
| WP_003030002 | 1159 | HPV----DFLE---NKGYHN--I-REDKLIK---LPKYSLFE---FEGGKRRLLAS | ASELQKGNEMVIPGHLVKLLYHA | 1221 |
| WP_003065552 | 1187 | NPV----EFLE---SKGYLN--I-RTDKLII---LPKYSLFE---LENGRRRLLAS | AGELQKGNELALPTQFMKFLYLA | 1249 |
| WP_001040076 | 1178 | NPS----AFLE---SKGYLN--I-RDDKLMI---LPKYSLFE---LENGRRRLLAS | AGELQKGNELALPTQFMKFLYLA | 1240 |
| WP_001040078 | 1186 | NPS----AFLE---SKGYLN--I-RADKLII---LPKYSLFE---LENGRRRLLAS | AGELQKGNELALPTQFMKFLYLA | 1248 |
| WP_001040080 | 1178 | NPS----AFLE---SKGYLN--I-RADKLII---LPKYSLFE---LENGRRRLLAS | AGETIDRLQKGNELALPTQFMKFLYLA | 1240 |
| WP_001040081 | 1178 | NPS----AFLE---SKGYLN--I-RDDKLII---LPKYSLFE---LENGRRRLLAS | AGELQKGNELALPTQFMKFLYLA | 1240 |
| WP_001040083 | 1178 | NPS----AFLE---SKGYLN--I-RADKLII---LPKYSLFE---LENGRRRLLAS | AGELQKGNELALPTQFMKFLYLA | 1240 |
| WP_001040085 | 1178 | NPS----AFLE---SKGYLN--I-RADKLII---LPKYSLFE---LENGRRRLLAS | AGELQKGNELALPTQFMKFLYLA | 1240 |
| WP_001040087 | 1178 | NPS----AFLE---SKGYLN--I-RADKLII---LPKYSLFE---LENGRRRLLAS | AGELQKGNELALPTQFMKFLYLA | 1240 |
| WP_001040088 | 1178 | NPS----AFLE---SKGYLN--I-RDDKLMI---LPKYSLFE---LENGRRRLLAS | AGELQKGNELALPTQFMKFLYLA | 1240 |
| WP_001040089 | 1178 | NPS----AFLE---SKGYLN--I-RDDKLMI---LPKYSLFE---LENGRRRLLAS | AGELQKGNELALPTQFMKFLYLA | 1240 |
| WP_001040090 | 1178 | NPS----AFLE---SKGYLN--I-RADKLII---LPKYSLFE---LENGRRRLLAS | AGELQKGNELALPTQFMKFLYLA | 1240 |
| WP_001040091 | 1178 | NPS----AFLE---SKGYLN--I-RADKLII---LPKYSLFE---LENGRRRLLAS | AGELQKGNELALPTQFMKFLYLA | 1240 |
| WP_001040092 | 1178 | NPS----AFLE---SKGYLN--I-RTDKLII---LPKYSLFE---LENGRRRLLAS | AGELQKGNELALPTQYMKFLYLA | 1240 |
| WP_001040094 | 1178 | NPS----AFLE---SKGYLN--I-RTDKLII---LPKYSLFE---LENGRRRLLAS | AGELQKGNELALPTQFMKFLYLA | 1240 |
| WP_001040095 | 1178 | NPS----AFLE---SKGYLN--I-RDDKLII---LPKYSLFE---LENGRRRLLAS | AGELQKGNELALPTQFMKFLYLA | 1240 |
| WP_001040096 | 1178 | NPS----AFLE---SKGYLN--I-RDDKLMI---LPKYSLFE---LENGRRRLLAS | AGELQKGNELALPTQYMKFLYLA | 1240 |
| WP_001040097 | 1178 | NPS----AFLE---SKGYLN--I-RDDKLMI---LPKYSLFE---LENGRRRLLAS | AGELQKGNELALPTQFMKFLYLA | 1240 |
| WP_001040098 | 1178 | NPS----AFLE---SKGYLN--I-RADKLII---LPKYSLFE---LENGRRRLLAS | ADELQKGNELALPTQFMKFLYLA | 1240 |
| WP_001040099 | 1178 | NPS----AFLE---SKGYLN--I-RDDKLMI---LPKYSLFE---LENGRRRLLAS | AGELQKGNELALPTQFMKFLYLA | 1240 |
| WP_001040100 | 1178 | NPS----AFLE---SKGYLD--I-RDDKLMI---LPKYSLFE---LENGRRRLLAS | AGELQKGNELALPTQFMKFLYLA | 1240 |
| WP_001040104 | 1178 | NPS----AFLE---SKGYLN--I-RADKLII---LPKYSLFE---LENGRRRLLAS | AGELQKGNELALPTQFMKFLYLA | 1240 |
| WP_001040105 | 1178 | NPS----AFLE---SKGYLN--I-RDDKLMI---LPKYSLFE---LENGRRRLLAS | AGELQKGNELALPTQFMKFLYLA | 1240 |
| WP_001040106 | 1178 | NPS----AFLE---SKGYLN--I-RDDKLMI---LPKYSLFE---LENGRRRLLAS | AGELQKGNELALPTQYMKFLYLA | 1240 |
| WP_001040107 | 1178 | NPS----AFLE---SKGYLN--I-RDDKLMI---LPKYSLFE---LENGRRRLLAS | AGELQKGNELALPTQYMKFLYLA | 1240 |

-continued

| | | | | | |
|---|---|---|---|---|---|
| WP_001040108 | 1178 | NPS---AFLE---SKGYLN--I-RDDKLMI--LPKYSLFE---LENGRRRLLAS | AGELQKGNELALPTQYMKFLYLA | 1240 |
| WP_001040109 | 1178 | NPS---AFLE---SKGYLN--I-RDDKLMI--LPKYSLFE---LENGRRRLLAS | AGELQKGNELALPTQYMKFLYLA | 1240 |
| WP_001040110 | 1178 | NPS---AFLE---SKGYLN--I-RDDKLMI--LPKYSLFE---LENGRRRLLAS | AGELQKGNELALPTQYMKFLYLA | 1240 |
| WP_015058523 | 1178 | NPS---AFLE---SKGYLN--I-RTDKLJI--LPKYSLFE---LENGRRRLLAS | AGELQKGNELALPTQYMKFLYLA | 1240 |
| WP_017643650 | 1178 | NPS---AFLE---SKGYLN--I-RDDKLMI--LPKYSLFE---LENGRRRLLAS | ADELQKGNELALPTQFMKFLYLA | 1240 |
| WP_017647151 | 1178 | NPS---AFLE---SKGYLN--I-RDDKLMI--LPKYSLFE---LENGRRRLLAS | AGELQKGNELALPTQFMKFLYLA | 1240 |
| WP_017648376 | 1178 | NPS---AFLE---SKGYLN--I-RDDKLMI--LPKYSLFE---LENGRRRLLAS | AGELQKGNELALPTQFMKFLYLA | 1240 |
| WP_017649527 | 1178 | NPS---AFLE---SKGYLN--I-RADKLJI--LPKYSLFE---LENGRRRLLAS | AGELQKGNELALPTQYMKFLYLA | 1240 |
| WP_017771611 | 1178 | NPS---AFLE---SKGYLN--I-RDDKLMI--LPKYSLFE---LENGRRRLLAS | AGELQKGNELALPTQFMKFLYLA | 1240 |
| WP_017771984 | 1178 | NPS---AFLE---SKGYLN--I-RADKLJI--LPKYSLFE---LENGRRRLLAS | AGELQKGNELALPTQFMKFLYLA | 1240 |
| CFQ25032 | 1178 | NPS---AFLE---SKGYLN--I-RADKLJI--LPKYSLFE---LENGRRRLLAS | AGELQKGNELALPTQFMKFLYLA | 1240 |
| CFV16040 | 1178 | NPS---AFLE---SKGYLN--I-RADKLJI--LPKYSLFE---LENGRRRLLAS | AGELQKGNELALPTQYMKFLYLA | 1240 |
| KLJ37842 | 1178 | NPS---AFLE---SKGYLN--I-RADKLJI--LPKYSLFE---LENGRRRLLAS | AGELQKGNELALPTQFMKFLYLA | 1240 |
| KLJ72361 | 1192 | NPS---AFLE---SKGYLN--I-RDDKLJI--LPKYSLFE---LENGRRRLLAS | AGELQKGNELALPTQYMKFLYLA | 1254 |
| KLL20707 | 1178 | NPS---AFLE---SKGYLN--I-RDDKLMI--LPKYSLFE---LENGRRRLLAS | AGELQKGNELALPTQFMKFLYLA | 1240 |
| KLL42645 | 1178 | NPS---AFLE---SKGYLN--I-RDDKLJI--LPKYSLFE---LENGRRRLLAS | AGELQKGNELALPTQFMKFLYLA | 1240 |
| WP_047207273 | 1178 | NPS---AFLE---SKGYLN--I-RDDKLMI--LPKYSLFE---LENGRRRLLAS | AGELQKGNELALPTQYMKFLYLA | 1240 |
| WP_047209694 | 1178 | NPS---AFLE---SKGYLN--I-RDDKLMI--LPKYSLFE---LENGRRRLLAS | AGELQKGNELALPTQFMKFLYLA | 1240 |
| WP_050198062 | 1178 | NPS---AFLE---SKGYLN--I-RDDKLJI--LPKYSLFE---LENGRRRLLAS | AGELQKGNELALPTQFMKFLYLA | 1240 |
| WP_050201642 | 1178 | NPS---AFLE---SKGYLN--I-RADKLJI--LPKYSLFE---LENGRRRLLAS | AGELQKGNELALPTQFMKFLYLA | 1240 |
| WP_050204027 | 1178 | NPS---AFLE---SKGYLN--I-RDDKLMI--LPKYSLFE---LENGRRRLLAS | AGELQKGNELALPTQYMKFLYLA | 1240 |
| WP_050881965 | 1178 | NLS---AFLE---SKGYLN--I-RADKLJI--LPKYSLFE---LENGRRRLLAS | AGELQKGNELALPTQFMKFLYLA | 1240 |
| WP_050886065 | 1178 | NPS---AFLE---SKGYLN--I-RTDKLJI--LPKYSLFE---LENGRRRLLAS | AGELQKGNELALPTQYMKFLYLA | 1240 |
| AHN30376 | 1178 | NPS---AFLE---SKGYLN--I-RADKLJI--LPKYSLFE---LENGRRRLLAS | AGELQKGNELALPTQFMKFLYLA | 1240 |
| EA078426 | 1178 | NPS---AFLE---SKGYLN--I-RADKLJI--LPKYSLFE---LENGRRRLLAS | AGELQKGNELALPTQFMKFLYLA | 1240 |
| CCW42055 | 1186 | DKR---AFIL---GKGYKD--I-K--KIIE--LKDGSRRMLAS | RGEIHKGNELFVPQKFTTLLYHS | 1253 |
| WP_003041502 | 1160 | DPLE---QRGYRN--V-RLEKIIK--LPKYSLFE---LENKRRRLLAS | ARELQKGNELVIPQRFTTLLYHS | 1222 |
| WP_037593752 | 1160 | DFLE---QRGYRN--V-RLEKIIK--LPKYSLFE---LENKRRRLLAS | ARELQKGNELVIPQRFTTLLYHS | 1222 |
| WP_049516684 | 1159 | HPV---DFLE---QRGYRN--V-RLEKIIK--LPKYSLFE---LENKRRRLLAS | ARELQKGNELVIPQRFTTLLYHS | 1221 |
| GAD46167 | 1191 | NPV---DFLE---QRGYRN--V-RLEKIIK--LPKYSLFE---LENKRRRLLAS | ATELQKGNEIMLSAHLVALLYHA | 1253 |
| WP_018363470 | 1186 | EFIK---NKGYQN--V-QEDKLMK--LPKYSLFE---FEGGRRRLLAS | --ELQKANELVLPQHLVRLLYYT | 1248 |
| WP_003043819 | 1159 | DPI---GFLE---AKGYKD--I-KKELIFK--LPKYSLFE---LENGRRRMLAS | AKELQKGNELVIPQRFTTLLYHS | 1221 |
| WP_006269658 | 1179 | NPV---DFLE---QRGYRN--V-RLEKIIK--LPKYSLFE---LENKRRRLLAS | AVELQKGNEMVLPQYLNNLLYHA | 1241 |
| WP_048800889 | 1178 | NPI---MFLE---SKGYRN--I-QKDKLIK--LPKYSLFE---FEGGRRRLLAS | RGDLQKANEMFLPAKLVTLLY-- | 1245 |
| WP_012767106 | 1178 | NPL---KFIE---DKGYGN--V-QIDKCIK--LPKYSLFE---FENGTRRMLAS | RGDLQKANEMFLPAKLVTLLY-- | 1245 |
| WP_014612333 | 1178 | NPL---KFIE---DKGYGN--V-QIDKCIK--LPKYSLFE---FENGTRRMLAS | RGDLQKANEMFLPAKLVTLLY-- | 1245 |
| WP_015017095 | 1178 | NPL---KFIE---DKGYGN--V-QIDKCIK--LPKYSLFE---FENGTRRMLAS | RGDLQKANEMFLPAKLVTLLY-- | 1245 |
| WP_015057649 | 1178 | NPL---KFIE---DKGYGN--V-QIDKCIK--LPKYSLFE---FENGTRRMLAS | RGDLQKANEMFLPAKLVTLLY-- | 1245 |
| WP_048277215 | 1178 | NPL---KFIE---DKGYGN--V-QIDKCIK--LPKYSLFE---FENGTRRMLAS | RGDLQKANEMFLPAKLVTLLY-- | 1245 |
| WP_049519324 | 1178 | NPV---KFIE---DKGYGN--V-QIDKCIK--LPKYSLFE---FENGTRRMLAS | RGDLQKANEMFLPAKLVTLLY-- | 1245 |
| WP_012515931 | 1157 | NPV---VFLE---ARGYRE--I-QEHLIIK--LPKYSLFE---LENGRRRLLAS | -SELQKGNELFLPVDYMTFLYLA | 1219 |
| WP_021320964 | 1157 | NPV---VFLE---AKGYRE--I-QEHLIIK--LPKYSLFE---LENGRRRLLAS | -SELQKGNELFLPVDYMTFLYLA | 1219 |
| WP_037581760 | 1189 | NPV---VFLE---AKGYHN--V-QEHLIIK--LPKYSLFE---LENGRRRLLAS | -SELQKGNELFLPVDYMTFLYLA | 1251 |
| WP_044232481 | 1184 | NPV---SFLE---NKGYHN--V-REDKLIK--LPKYSLFE---LENGRRRLLAS | ATELQKGNEVVLPGYLVELLYHS | 1246 |
| WP_009854540 | 1185 | NPV---VFLE---EFLE---VFLE---NKGYQN--V-QEDNLIK--LPKYSLFE---LENGRRRLLAS | ASELQKGNEMVLPGYLVELLYHA | 1247 |
| WP_012962174 | 1186 | NPV---EFLE---NKGYHN--I-REDKLIK--LPKYSLFE---LENGRRRLLAS | ASELQKGNEMVLPGYLVELLYHA | 1248 |
| WP_039695303 | 1186 | NPV---SFLE---KKGYHN--V-QEDKLIK--LPKYSLFE---LENGRRRLLAS | ATELQKGNEVMLPAHLVELLYHA | 1248 |
| WP_014334983 | 1189 | NPV---SFLE---KKGYHN--V-QEDKLIK--LPKYSLFE---LENGRRRLLAS | ATELQKGNEVMLPAHLVELLYHA | 1251 |
| WP_003099269 | 1177 | DPI---AFLE---KKGYQD--I-QTSSIIK--LPKYSLFE---LENGRKRLLAS | -ELQKGNELALPNKYVKFLYLA | 1239 |
| AHY15608 | 1177 | DPI---AFLE---KKGYQD--I-QTSSIIK--LPKYSLFE---LENGRKRLLAS | -ELQKGNELALPNKYVKFLYLA | 1239 |
| AHY17476 | 1177 | DPI---AFLE---KKGYQD--I-QTSSIIK--LPKYSLFE---LENGRKRLLAS | -KELQKGNELALPNKYVKFLYLA | 1239 |
| ESR09100 | 9 | DPI---AFLE---KKGYQD--I-QTSSIIK--LPKYSLFE---LENGRKRLLAS | -ELQKGNELALPNKYVKFLYLA | 71 |
| AGM98575 | 1177 | DPI---AFLE---KKGYQD--I-QTSSIIK--LPKYSLFE---LENGRKRLLAS | -ELQKGNELALPNKYVKFLYLA | 1239 |

-continued

```
ALF27331        1159 NPV---AFLE---RKGYRN--V-QEENIVK--LPKYSLFE---LENGRRRLLAS ARELQKGNEIVLPNHLGTMLYHA 1221
WP_018372492    1168 EPEr---FLA---QKGFER--V-EKT--IK--LPKYSLFE----MEKGRRRLLAS SGELQKGNQVLLPEHLIRLLSYA 1228
WP_045618028    1189 NPI---AYLE---ECGYKN--I-NPNLIIK--LPKYSLFE---FNNGQRRLLAS SIELQKGNELIVPYHFTALLYHA 1251
WP_045635197    1184 NPI---TFIE---NKGYHN--V-RKENILC--LPKYSLFE---LENGRRRLLAS AKELQKGNEIVLPVYLTTLLYHS 1246
WP_002263549    1159 DPV---AFLE---RKGYRN--V-QEENIIK--LPKYSLFK---LENGRKRLLAS ARELQKGNEIVLPNHLGTLLYHA 1221
WP_002263887    1159 DPV---AFLE---RKGYRN--V-QEENIIK--LPKYSLFK---LENGRKRLLAS ARELQKGNEIVLPNHLGTLLYHA 1221
WP_002264920    1159 DPV---AFLE---RKGYRN--V-QEENIIK--LPKYSLFK---LENGRKRLLAS ARELQKGNEIVLPNHLGTLLYHA 1221
WP_002269043    1159 DPV---AFLE---RKGYRN--V-QEENIIK--LPKYSLFK---LENGRKRLLAS ARELQKGNEIVLPNHLGTLLYHA 1221
WP_002269448    1159 DPV---AFLE---RKGYRN--V-QEENIIK--LPKYSLFK---LENGRKRLLAS ARELQKGNEIVLPNHLGTLLYHA 1221
WP_002271977    1159 DPV---AFLE---RKGYRN--V-QEENIIK--LPKYSLFK---LENGRKRLLAS ARELQKGNEIVLPNHLGTLLYHA 1221
WP_002272766    1159 DPV---AFLE---RKGYRN--V-QEENIIK--LPKYSLFK---LENGRKRLLAS ARELQKGNEIVLPNHLGTLLYHA 1221
WP_002273241    1159 DPV---AFLE---RKGYRN--V-QEENIIK--LPKYSLFK---LENGRKRLLAS ARELQKGNEIVLPNHLGTLLYHA 1221
WP_002275430    1159 DPV---AFLE---RKGYRN--V-QEENIIK--LPKYSLFK---LENGRKRLLAS ARELQKGNEIVLPNHLGTLLYHA 1221
WP_002276448    1159 DPV---AFLE---RKGYRN--V-QEENIIK--LPKYSLFK---LENGRKRLLAS ARELQKGNEIVLPNHLGTLLYHA 1221
WP_002277050    1167 NPV---KFLK---DKGYQQ--I-EKNNFVK--LPKYTLVD---IGNGIKRLWAS SKEVHKGNQLVVSKKSQDLLYHA 1229
WP_002277364    1159 DPV---AFLE---RKGYRN--V-QEENIIK--LPKYSLFK---LENGRKRLLAS ARELQKGNEIVLPNHLGTLLYHA 1221
WP_002279025    1159 DPV---AFLE---RKGYRN--V-QEENIIK--LPKYSLFK---LENGRKRLLAS ARELQKGNEIVLPNHLGTLLYHA 1221
WP_002279859    1159 DPV---AFLE---RKGYRN--V-QEENIIK--LPKYSLFK---LENGRKRLLAS ARELQKGNEIVLPNHLGTLLYHA 1221
WP_002280230    1159 DPV---AFLE---RKGYRN--V-QEENIIK--LPKYSLFK---LENGRKRLLAS ARELQKGNEIVLPNHLGTLLYHA 1221
WP_002281696    1159 DPV---AFLE---RKGYRN--V-QEENIIK--LPKYSLFK---LENGRKRLLAS ARELQKGNEIVLPNHLGTLLYHA 1221
WP_002282247    1167 NPV---KFIK---DKGYQQ--I-EKNNFVK--LPKYTLVD---IGNGIKRLWAS SKEVHKGNQLVVSKKSQDLLYHA 1229
WP_002282906    1159 DPV---AFLE---RKGYRN--V-QEENIIK--LPKYSLFK---LENGRKRLLAS ARELQKGNEIVLPNHLGTLLYHA 1221
WP_002283846    1159 DPV---AFLE---RKGYRN--V-QEENIIK--LPKYSLFK---LENGRKRLLAS ARELQKGNEIVLPNHLGTLLYHA 1221
WP_002287255    1159 DPV---AFLE---RKGYRN--V-QEENIIK--LPKYSLFK---LENGRKRLLAS ARELQKGNEIVLPNHLGTLLYHA 1221
WP_002288990    1159 DPV---AFLE---RKGYRN--V-QEENIIK--LPKYSLFK---LENGRKRLLAS ARELQKGNEIVLPNHLGTLLYHA 1221
WP_002289641    1159 DPV---AFLE---RKGYRN--V-QEENIIK--LPKYSLFK---LENGRKRLLAS ARELQKGNEIVLPNHLGTLLYHA 1221
WP_002290427    1159 DPI---AFLE---RKGYRN--V-QEENIIK--LPKYSLFK---LENGRKRLLAS ARELQKGNEIVLPNHLGTLLYHA 1221
WP_002295753    1159 DPV---AFLE---RKGYRN--V-QEENIIK--LPKYSLFK---LENGRKRLLAS ARELQKGNEIVLPNHLGTLLYHA 1221
WP_002296423    1173 DPV---AFLE---RKGYRN--V-QEENIIK--LPKYSLFK---LENGRKRLLAS ARELQKGNEIVLPNHLETLLYHA 1235
WP_002304487    1159 DPV---AFLE---RKGYRN--V-QEENIIK--LPKYSLFK---LENGRKRLLAS ARELQKGNEIVLPNHLGTLLYHA 1221
WP_002305844    1159 DPI---AFLE---RKGYRN--V-QEENIIK--LPKYSLFK---LENGRKRLLAS ARELQKGNEIVLPNHLGTLLYHA 1221
WP_002307203    1159 DPV---AFLE---RKGYRN--V-QEENIIK--LPKYSLFK---LENGRKRLLAS ARELQKGNEIVLPDHLGTLLYHA 1221
WP_002310390    1159 DPV---AFLE---RKGYRN--V-QEENIIK--LPKYSLFK---LENGRKRLLAS ARELQKGNEIVLPNHLGTLLYHA 1221
WP_002352408    1159 DPV---AFLE---RKGYRN--V-QEENIIK--LPKYSLFK---LENGRKRLLAS ARELQKGNEIVLPNHLGTLLYHA 1221
WP_012997688    1167 NPV---KFLK---DKGYQQ--I-EKNNFVK--LPKYTLVD---IGNGIKRLWAS SKEVHKGNQLVVSKKSQDLLYHA 1229
WP_014677909    1159 DPV---AFLE---RKGYRN--V-QEENIIK--LPKYSLFK---LENGRKRLLAS ARELQKGNEIVLPNHLGTLLYHA 1221
WP_019312892    1159 DPV---AFLE---RKGYRN--V-QEENIIK--LPKYSLFK---LENGRKRLLAS ARELQKGNEIVLPNHLGTLLYHA 1221
WP_019313659    1159 DPV---AFLE---RKGYRN--V-QEENIIK--LPKYSLFK---LENGRKRLLAS ARELQKGNEIVLPNHLGTLLYHA 1221
WP_019314093    1167 DPI---AFLE---RKGYRN--V-QEENIIK--LPKYSLFK---LENGRKRLLAS ARELQKGNEIVLPNHLGTLLYHA 1229
WP_019315370    1167 DPI---AFLE---RKGYRN--V-QEENIIK--LPKYSLFK---LENGRKRLLAS ARELQKGNEIVLPNHLGTLLYHA 1229
WP_019803776    1159 DPV---AFLE---RKGYRN--V-QEENIIK--LPKYSLFK---LENGRKRLLAS ARELQKGNEIVLPNHLGTLLYHA 1221
WP_019805234    1159 DPV---AFLE---RKGYRN--V-QEENIIK--LPKYSLFK---LENGRKRLLAS ARELQKGNEIVLPNHLGTLLYHA 1221
WP_024783594    1167 NPV---KFLK---DKGYQQ--I-EKNNFVK--LPKYTLVD---IGNGIKRLWAS SKEVHKGNQLVVSKKSQDLLYHA 1229
WP_024784288    1159 DPV---AFLE---RKGYRN--V-QEENIIK--LPKYSLFK---LENGRKRLLAS ARELQKGNEIVLPNHLGTLLYHA 1221
WP_024784666    1159 DPV---AFLE---RKGYRN--V-QEENIIK--LPKYSLFK---LENGRKRLLAS ARELQKGNEIVLPNHLGTLLYHA 1221
WP_024784894    1159 DPV---AFLE---RKGYRN--V-QEENIIK--LPKYSLFK---LENGRKRLLAS ARELQKGNEIVLPNHLGTLLYHA 1221
WP_024786433    1167 NPV---KFLK---DKGYQQ--I-EKNNFVK--LPKYTLVD---IGNGIKRLWAS SKEVHKGNQLVVSKKSQDLLYHA 1229
WP_049473442    1167 NPV---KFLK---DKGYQQ--I-EKNNFVK--LPKYTLVD---IGNGIKRLWAS SKEVHKGNQLVVSKKSQDLLYHA 1229
WP_049474547    1159 DPV---AFLE---RKGYRN--V-QEENIIK--LPKYSLFK---LENGRKRLLAS ARELQKGNEIVLPNHLGTLLYHA 1221
EMC03581        1152 DPV---AFLE---RKGYRN--V-QEENIIK--LPKYSLFK---LKNGRKRRMLAS AKELQKGNEIVLPVHLTTLLYHA 1214
WP_000428612    1187 SPI---AFLE---NKGYHN--V-RKENILC--LPKYSLFE---LPKYSLFE---LKNGRRRMLAS AKELQKGNEIVLPVYLTTLLYHS 1249
WP_000428613    1185 NPI---TFIE---NKGYHN--V-RKENILC--LPKYSLFE---LENGRRRLLAS AKELQKGNEMVLPSYLIALLYHA 1247
WP_049523028    1180 NPV---AFLE---GKGYQN--V-VEENIIR--LPKYSLFE---LENGRRRMLAS AKELQKGNEMVLPSYLIALLYHA 1242
```

```
WP_003107102   1146 DRI---TFLE---KKGYQD--I-QESLIIK--LPKFSLFE---LENGKRLLAS --ELQKGNELSLPNKYIQFLYLA 1208
WP_054272288   1179 NPI---AFLE---SKGYHD--I-QEHLMIT--LPKYSLFE---LENGRRLLAS --ELQKGNEMVLPQHLVTFLYRV 1241
WP_049531101   1189 NPI---AYLE---EYGYKN--I-NPNLIIK--LPKYSLFK---FNDGQRLLAS SIELQKGNELILPYHFTLLLYHA 1251
WP_049538452   1191 NPI---AYLE---ECGYKN--I-NPNLIIK--LPKYSLFE---FNGGQRLLAS SIELQKGNELILPYHFTALLYHT 1253
WP_049549711   1183 DNI---AFLE---ECGYKN--I-QEKLLIK--LPKYSLFE---LENGRRLLAS --EFQKGNELALSGKYMKFLYLA 1245
WP_007896501   1135 DNI---AFLE---KKGYQD--I-QEKLLIK--LPKYSLFE---LENGRRLLAS --EFQKGNELALSGKYMKFLYLA 1197
EFR44625       1184 NPI---TFLE---NKGYHN--V-RKENILC--LPKYSLFE---LENGRRLLAS AKELQKGNEIVLPVCLTLLYHS 1246
WP_002897477   1190 NPV---TYLE---ECGYKN--I-NSNLIIK--LPKYSLFE---FNDGQRLLAS SIELQKGNELILPYHLTALLYHS 1252
WP_002906454   1185 NPI---AFLE---NKGYHN--V-CKENILC--LPKYSLFE---LENGRRLLAS AIELQKGNEMFLPQQFVNLLYHA 1247
WP_009729476   1175 NSV---TFLE---EKGYRN--I-RENTLIK--FPKYSLFE---LESGRRRMLAS AKELQKGNEIVLPVYLTLLYHS 1237
CQR24647       1189 NPI---TFLE---NKGYHN--I-LEKNILC--LPKYSLFE---LENGRRLLAS AKELQKGNEIVLPVYLTLLYHS 1251
WP_000066813   1185 NPI---EFLE---HKGYKN--I-LEKNIIK--LPKYSLFE---LENGRRLLAS AKELQKGNEMILPPHLVTLLYHS 1247
WP_009754323   1178 NPI---EFLE---HKGYKN--I-LEKNIIK--LPKYSLFE---LENGRRLLAS AKELQKGNEMILPPHLVTLLYHS 1240
WP_044674937   1180 NPI---EFLE---HKGYKN--I-LEKNIIK--LPKYSLFE---LENGRRLLAS AKELQKGNEMILPPHLVTLLYHS 1242
WP_044676715   1180 NPI---EFLE---HKGYKN--I-LEKNIIK--LPKYSLFE---LENGRRLLAS AKELQKGNEMILPPHLVTLLYHS 1242
WP_044680361   1178 NPI---EFLE---HKGYKN--I-LEKNIIK--LPKYSLFE---LENGRRLLAS AKELQKGNEMILPPHLVTLLYHS 1240
WP_044681799   1186 DKR---AFLL---GKGYKD--I-K--KIIE--LPKYSLFE---LKDGSRRMLAS RGEIHKGNELFVPQKFTTLLYHA 1253
WP_049533112   1118 SETslqAYIA---EQIKSE--VeILN---grILkYQLIS---NNNGNRLYIAG --SERHNARQLIVSDEAAKVIWLI 1181
WP_029090905   1150 EKI---NYIE---eKEGLSD--VrIIK---Dn-IPVNQMIEm---DGGEYLLTS --EYVNARQLVLNEKQCALIADI 1211
WP_006506696   1177 NPI---DFLE---AKGYKE--V-KKDLIIK--LPKYSLFE---LENGKRMLAS -GELQKGNELALPSKYVNFLYLA 1239
AIT42264       1150 QTT---EYLG---KIGFNK--ASIIN----S-FKNYTLFE---LENGSRRMIVG KGELQKGNQMVLPQNLLEFVYHL 1217
WP_034440723   1177 NPI---DFLE---EAGYKE--V-KKDLIIK--LPKYSLFE---LENGRRMLAS -GELQKGNELALPSKYVNFLYLA 1239
AKQ21048       1151 HPT---AYLE---EAGYNN--P-TV--LHE--LPKYQLFE---LEDGSRRMIAS AKEFQKGNQMVLPLELVELLYHA 1211
WP_002364836   1157 NPI---LFLE---EKGFLR--P-RV--LMK--LPKYTLYE---LPKYTLYE--- AKEAQKGNQMVLPEHLLTLLYHA 1217
WP_016631044   1108 NPI---LFLE---EKGFLR--P-RV--LMK--LPKYTLYE---FPEGRRRLLAS AKEAQKGNQMVLPEHLLTLLYHA 1168
EM575795        893 DPI---GFLS---NKGYSN--V-TKF--IK--LsKYTLYE---LENGRKRMVAS -KEAQKGNQMVLPEHLLTLLYHA  953
WP_002373311   1157 NPI---LFLE---EKGFLR--P-RV--LMK--LPKYTLYQ---FPEGRRRLLAS AKEAQKGNQMVLPEHLLTLLYHA 1217
WP_002378009   1157 NPI---LFLE---EKGFLR--P-RV--LMK--LPKYTLYE---FPEGRRRLLAS AKEAQKGNQMVLPEHLLTLLYHA 1217
WP_002407324   1157 NPI---LFLE---EKGFLR--P-RV--LMK--LPKYTLYE---FPEGRRRLLAS AKEAQKGNQMVLPEHLLTLLYHA 1217
WP_002413717   1157 NPI---LFLE---EKGFLR--P-RV--LMK--LPKYTLYE---FPEGRRRLLAS AKEAQKGNQMVLPEHLLTLLYHA 1217
WP_010775580   1159 NPI---LFLE---EKGFLR--P-RV--LMK--LPKYTLYE---FPEGRRRLLAS AKEAQKGNQMVLPEHLLTLLYHA 1219
WP_010818269   1157 NPI---LFLE---EKGFLR--P-RV--LMK--LPKYTLYE---FPEGRRRLLAS AKEAQKGNQMVLPEHLLTLLYHA 1217
WP_010824395   1157 NPI---LFLE---EKGFLR--P-RV--LMK--LPKYTLYE---FPEGRRRLLAS AKEAQKGNQMVLPEHLLTLLYHA 1217
WP_016622645   1159 NPI---LFLE---EKGFLR--P-RV--LMK--LPKYTLYE---LENGRKRMVAS -KEAQKGNQMVLPEHLLTLLYHA 1219
WP_002312694   1160 SPV---LFLK---NKGYEQ--A-EIE--MK--LPKYALFE---LENGRKRMVAS -KEAQKANSFLLPEHLVTLLYHA 1220
WP_033624816   1160 SPV---LFLK---NKGYEQ--A-EIE--MK--LPKYALFE---LENGRKRMVAS -KEAQKANSFLLPERLLTLLYHA 1220
WP_002314015   1160 SPV---LFLK---NKGYEQ--A-EIE--MK--LPKYALFE---LENGRKRMVAS -KEAQKANSFLLPEHLVTLLYHA 1220
WP_033625576   1160 SPV---LFLK---NKGYEQ--A-EIE--MK--LPKYALFE---LENGRKRMVAS -KEAQKANSFLLPEHLLTLLYHA 1220
WP_033789179   1160 SPV---LFLK---NKGYEQ--A-EIE--MK--LPKYALFE---LENGRKRMVAS -KEAQKANSFLLPEHLVTLLYHA 1220
WP_002310644   1159 SPV---LFLK---NKGYEQ--A-EIE--MK--LPKYALFE---LENGRKRMVAS -KEAQKANSFLLPEHLVTLLYHA 1219
WP_002320716   1160 SPV---LFLK---NKGYEQ--A-EIE--MK--LPKYALFE---LENGRKRMVAS -KEAQKANSFLLPEHLVTLLYHA 1220
WP_002330729   1159 SPV---LFLK---NKGYEQ--A-EIE--MK--LPKYALFE---LENGRKRMVAS -KEAQKANSFLLPEHLVTLLYHA 1219
WP_002335161   1160 SPV---LFLK---NKGYEQ--A-EIE--MK--LPKYALFE---LENGRKRMVAS -KEAQKANSFLLPEHLVTLLYHA 1220
WP_002345439   1160 SPV---LFLK---NKGYEQ--A-EIE--MK--LPKYALFE---LENGRKRMVAS -KEAQKANSFLLPEHLVTLLYHA 1220
WP_034686970   1150 DPT---TFLK---NKGYEQ--V-TEF--IK--LPKYTLFE---FDNGRRRLLAS -KESQKGNPFILSDQLVTLLYHA 1210
WP_047937432   1160 SPV---LFLK---NKGYEQ--A-EIE--MK--LPKYALFE---LENGRKRMVAS -KEAQKANSFLLPEHLVTLLYHA 1220
WP_010720994   1150 DPT---TFLK---DKGFPQ--V-TEF--IK--LPKYTLFE---FDNGRRRLLAS -KESQKGNPFILSDQLVTLLYHA 1210
WP_010737004   1150 DPT---TFLK---DKGFPQ--V-TEF--IK--LPKYTLFE---FDNGRRRLLAS -KESQKGNPFILSDQLVTLLYHA 1210
WP_034700478   1150 DPT---TFLK---DKGFPH--V-TEF--IK--LPKYTLFE---FDNGRRRLLAS -KESQKGNPFILSDQLVTLLYHA 1210
WP_007209003   1148 NPI1--YLS---KKDYHN--pKVEAI---LPKYSLFE---FENGRRRMVAS -SETQKGNQLIIPGHLMELLYHS 1208
WP_023519017   1144 DPR---EFLK---TKGYBG--V-KQW--LI--LPKYILFE---AQGGYRRMIAS -QBTQKANSLIILPENLVTLLYHA 1204
WP_010770040   1155 DPV---SLLE---EKGYAN--P-EV--LIH--LPKYTLYE---LENGRRLLAS ANEAQKGNQLVLPASLVTLLYHA 1215
```

```
                                                                                                                                  -continued WP_048604708    1152  NER----EFLK---NKGYQN--P-QI--CMK-LPKYSLYE---LPKYTLFE----FDDGRRRLLaS   AKEAQKGNQMVLPAHLVTFLYHA       1212
WP_010750235    1153  DPI----SFlI---EKGYSN--V-NQF--IK--LPKYTLFE---LPKYTLFE----LANGQRRMLAS   -QELQKANSFILPEKLVTLLYHA       1213
AII16583        1216  NPI----DFlE---AKGYKE--V-KKDLIIK--LPKYSLFE---LPKYSLFE----LENGRKRMLAS   -GELQKGNELALPSKYVNFLYLA       1278
WP_029073316    1165  TKI----NYIK--eSEGLEE--VklIK----E--ILKNQlIET---E--ILKNQlIEk----NGGLFYVTS   -EIVNARQLILDFNCTRIIDGI        1225
WP_031589969    1165  IKI----NYLK--qAEDLEE--VqIGK----E--ILKNQlIEk----PKYSLLEq---DGGLYYIVA     -EIINAKQLlINESQTKLVCEI        1225
KDA45870        1139  DPT----AYLA--SRGYTNvtNsFIL------PKYSLLEq---PEGRRRYLAS    -KEFQKANELILPQHLVELLYWV       1199
WP_039099354    1171  QKI-spQPTKv--KKQKGtiV-KVVEDFEv-IAPHILINqrfFDNGQELTLGS   ---HNEQELIlDKTAVKLlNGA       1241
AKP02966        1173  KTL-qNWLE---ENVKHKsIqlIK--Nn-VPIGQlIY-----SKKvGLlS     -REIANRQQLlILPPEHSALLRIL      1237
WP_010991369    1155  DEK----AFlE---EQGYRQ--P-KV--LAK-LPKYTLYE---CEEGRRRMLAS   ANEAQKGNQQVLPNHLVTLLHHA       1215
WP_033838504    1155  DEK----AFlE---EQGYRQ--P-KV--LAK-LPKYTLYE---CEEGRRRMLAS   ANEAQKGNQQVLPNHLVTLLHHV       1215
EHN60060        1158  NPI----DFlE---AKGYKE--V-KKDLIIK--LPKYSLFE---LENGRKRMLAS   -GELQKGNELALPSKYVNFLYLA       1218
EFR89594        924   DEK----AFlE---EQGYRQ--P-KV--LAK-LPKYTLYE---CEEGRRRMLAS   ANEAQKGNQQVLPNHLVTLLHHV       984
WP_038409211    1155  DQK----AFlE---EKGYYS--P-KV--LTK-IPKYTLYE---CENGRRRMLGS   ANEAQKGNQMVLPNHLMTLLYHA       1215
EFR95520        774   DQK----AFlE---EKGYYS--P-KV--LTK-IPKYTLYE---CENGRRRMLAS   ANEAQKGNQMVLPNHLVTLLYHA       834
WP_003723650    1155  DEE----AFlE---EKGYRH--P-KV--LTK-LPKYTLYE---CEKGRRRMLAS   ANEAQKGNQLVLSNHLVSLLYHA       1215
WP_003727705    1155  DEE----AFlE---EKGYKE--P-KV--LTK-LPKYTLYE---CEKGRRRMLSS   ANEAQKGNQLVLSNHLVSLLYHA       1215
WP_003730785    1155  DEE----AFlE---EKGYHQ--P-KV--LTK-LPKYTLYE---CEKGRRRMLAS   ANEAQKGNQLVLSNHLVSLLYHA       1215
WP_003733029    1155  DEK----TFlE---EKGYHQ--P-KV--LIK-VPKYTLYE---CKNGRRRMLGS   ANEAHKGNQMLLPNHLMALLYHA       1215
WP_003739838    1155  DEE----SFlE---KQGYRQ--P-KV--LTK-LPKYTLYE---CENGRRRMLAS   ANEAQKGNQQVLKGQLITLLHHA       1215
WP_014601172    1155  DEE----AFlE---EKGYRQ--P-KV--LTK-LPKYTLYE---CEKGRRRMLAS   ANEAQKGNQLVLSNHLVSLLYHA       1215
WP_023548323    1155  DEK----VFlE---GKGYHQ--P-KV--LTK-IPKYALYE---CENGRRRMLGS   ANEVHKGNQMLLPNHLMTLLYHA       1215
WP_031665337    1155  DEK----AFlE---EKGYRH--P-KV--LTK-LPKYTLYE---CEKGRRRMLAS   ANEAQKGNQLVLSNHLVSLLYHA       1215
WP_031669209    1155  DEK----TFlE---GKGYHQ--P-KV--LIK--VPKYTLYE---CEKGRRRMLGS   ANEAHKGNQMLLPNHLMALLYHA       1215
WP_033920898    1155  DEK----VFlE---GKGYHQ--P-KV--LTK-LPKYTLYE---CENGRRRMLGS   ANEVHKGNQMLLPNHLVSLLYHA       1215
AKI42028        1158  DEE----AFlE---EKGYRH--P-KV--LTK-LPKYTLYE---CEKGRRRMLGS   ANEAQKGNQLVLSNHLVSLLYHA       1218
AKI50529        1158  DEK----VFlE---GKGYHQ--P-KV--LTK-LPKYTLYE---CENGRRRMLGS   ANEVHKGNQMLLPNHLMTLLYHA       1218
EFR83390        603   DQK----EFlE---GKGYRN--P-KV--ITK-IPKYTLYE---CENGRRRMLGS   ANEAQKGNQMVLPNHLMTLLYHA       663
WP_046323366    1155  NPI----DFlE---AKGYKE--V-KKDLIIK--LPKYSLFE---LENGRKRMLAS   -GELQKGNELALPSKYVNFLYLA       1215
AKE81011        1193  HRAD---NFNS--TEYLN--YVSEHKKFEKVLsCVEDFANLYDVE-KNLsKIR-A VAD-SM--DNFSIEE--             1255
CUO82355        1154  EQI----EYVE--kEEKLsD--VkIIK---Nn-IPLNQLIEi---DGRQYLLTS   -ECVNAMQLVLNEEQCKLISEI        1215
WP_045635197    1210  EQL----SYIAspeHEDLID--VrIVK----E--ILKNQlIEi---DGGLYYVTS   -EYVTARQLSLNEQSCKLIEI        1217
WP_033162887    1210  NPI----DFlE---AKGYKE--V-KKDLIIK--LPKYSLFE---LENGRKRMLAS   -GELQKGNELALPSKYVNFLYLA       1272
AGZ01981        1177  NPI----DFlE---AKGYKE--V-KKDLIIK--LPKYSLFE---LENGRKRMLAS   -GELQKGNELALPSKYVNFLYLA       1239
AKA60242        1177  NPI----DFlE---AKGYKE--V-KKDLIIK--LPKYSLFE---LENGRKRMLAS   -GELQKGNELALPSKYVNFLYLA       1239
AK540380        1181  NPI----DFlE---AKGYKE--V-KKDLIIK--LPKYSLFE---LENGRKRMLAS   -GELQKGNELALPSKYVNFLYLA       1243
4UN5_B          1247  KNVH---KLDE-PGHLE-YIQKHRNEFKDLLNLVSEFSQKVLAD--ANLEKIK-S LYA-DN--EQADIEI--             1305
5AXW_A          979   GELYRVIgVNNDILNRIE--VNMIDITYREYLENMDKRPPRIIKTIAsKTQsIK-K LYbvKSk--KHPQIIKg             1056
WP_009880683    924   SHYEKLkgSPEDnEQKQL-FVEQHKHYLDEIIEQISEFSKRVILAD--ANLDKVL-S AYN-KH--RDKPIREq--           989
WP_010922251    1240  SHYEKLkgSPEDnEQKQL-FVEQHKHYLDEIIEQISEFSKRVILAD--ANLDKVL-S AYN-KH--RDKPIREq--           1305
WP_039695303    1249  SHYEKLkgSPEDnEQKQL-FVEQHKHYLDEIIEQISEFSKRVILAD--ANLDKVL-S AYN-KH--RDKPIREq--           1308
WP_010922251    1240  SHYEKLkgSPEDnEQKQL-FVEQHKHYLDEIIEQISEFSKRVILAD--ANLDKVL-S AYN-KH--RDKPIREq--           1305
WP_011054416    1240  SHYEKLkgSPEDnEQKQL-FVEQHKHYLDEIIEQISEFSKRVILAD--ANLDKVL-S AYN-KH--RDKPIREq--           1305
WP_011284745    1240  SHYEKLkgSPEDnEQKQL-FVEQHKHYLDEIIEQISEFSKRVILAD--ANLDKVL-S AYN-KH--RDKPIREq--           1305
WP_011285506    1240  SHYEKLkgSPEDnEQKQL-FVEQHKHYLDEIIEQISEFSKRVILAD--ANLDKVL-S AYN-KH--RDKPIREq--           1305
WP_011527619    1240  SHYEKLkgSPEDnEQKQL-FVEQHKHYLDEIIEQISEFSKRVILAD--ANLDKVL-S AYN-KH--RDKPIREq--           1305
WP_012560673    1239  SHYEKLkgSPEDnEQKQL-FVEQHKHYLDEIIEQISEFSKRVILAD--ANLDKVL-S AYN-KH--RDKPIREq--           1304
WP_014407541    1239  SHYEKLkgSPEDnEQKQL-FVEQHKHYLDEIIEQISEFSKRVILAD--ANLDKVL-S AYN-KH--RDKPIREq--           1304
WP_020905136    1240  SHYEKLkgSPEDnEQKQL-FVEQHKHYLDEIIEQISEFSKRVILAD--ANLDKVL-S AYN-KH--RDKPIREq--           1305
WP_023080005    1239  SHYEKLkgSPEDnEQKQL-FVEQHKHYLDEIIEQISEFSKRVILAD--ANLDKVL-S AYN-KH--RDKPIREq--           1304
WP_023610282    1239  SHYEKLkgSPEDnEQKQL-FVEQHKHYLDEIIEQISEFSKRVILAD--ANLDKVL-S AYN-KH--RDKPIREq--           1304
WP_030125963    1240  SHYEKLkgSPEDnEQKQL-FVEQHKHYLDEIIEQISEFSKRVILAD--ANLDKVL-S AYN-KH--RDKPIREq--           1305
WP_030126706    1240  SHYEKLkgSPEDnEQKQL-FVEQHKHYLDEIIEQISEFSKRVILAD--ANLDKVL-S AYN-KH--RDKPIREq--           1305
WP_031488318    1240  SHYEKLkgSPEDnEQKQL-FVEQHKHYLDEIIEQISEFSKRVILAD--ANLDKVL-S AYN-KH--RDKPIREq--           1305
```

| | | | | |
|---|---|---|---|---|
| WP_032460140 | 1240 | SHYEKLkgSPEDnEQKQL--FVEQHKHYLDEIIEQISEFSKRVILAD--ANLDKVL-S | AYN-KH---RDKPIREq | 1305 |
| WP_032461047 | 1240 | SHYEKLkgSPEDnEQKQL--FVEQHKHYLDEIIEQISEFSKRVILAD--ANLDKVL-S | AYN-KH---RDKPIREq | 1305 |
| WP_032462016 | 1240 | SHYEKLkgSPEDnEQKQL--FVEQHKHYLDEIIEQISEFSKRVILAD--ANLDKVL-S | AYN-KH---RDKPIREq | 1305 |
| WP_032462936 | 1240 | SHYEKLkgSPEDnEQKQL--FVEQHKHYLDEIIEQISEFSKRVILAD--ANLDKVL-S | AYN-KH---RDKPIREq | 1305 |
| WP_032464890 | 1240 | SHYEKLkgSPEDnEQKQL--FVEQHKHYLDEIIEQISEFSKRVILAD--ANLDKVL-S | AYN-KH---RDKPIREq | 1305 |
| WP_033888930 | 1065 | SHYEKLkgSPEDnEQKQL--FVEQHKHYLDEIIEQISEFSKRVILAD--ANLDKVL-S | AYN-KH---RDKPIREq | 1130 |
| WP_038431314 | 1240 | SHYEKLkgSPEDnEQKQL--FVEQHKHYLDEIIEQISEFSKRVILAD--ANLDKVL-S | AYN-KH---RDKPIREq | 1305 |
| WP_038432938 | 1239 | SHYEKLkgSPEDnEQKQL--FVEQHKHYLDEIIEQISEFSKRVILAD--ANLDKVL-S | AYN-KH---RDKPIREq | 1304 |
| WP_038434062 | 1240 | SHYEKLkgSPEDnEQKQL--FVEQHKHYLDEIIEQISEFSKRVILAD--ANLDKVL-S | AYN-KH---RDKPIREq | 1305 |
| BAQ51233 | 1151 | SHYEKLkgSPEDnEQKQL--FVEQHKHYLDEIIEQISEFSKRVILAD--ANLDKVL-S | AYN-KH---RDKPIREq | 1216 |
| KGE60162 | 415 | SHYEKLkgSPEDnEQKQL--FVEQHKHYLDEIIEQISEFSKRVILAD--ANLDKVL-S | AYN-KH---RDKPIREq | 480 |
| KGE60856 | 178 | SHYEKLkgSPEDnEQKQL--FVEQHKHYLDEIIEQISEFSKRVILAD--ANLDKVL-S | AYN-KH---RDKPIREq | 243 |
| WP_002989955 | 1240 | SHYEKLkgSPEDnEQKQL--FVEQHKHYLDEIIEQISEFSKRVILAD--ANLDKVL-S | AYN-KH---RDKPIREq | 1305 |
| WP_003030002 | 1222 | YQIE----KNYE-PEHRE--YVEKHKDEFKELLEYISVFSRKVLAD--NNLTKIE-M | LFS-KN---KDAEVSS- | 1281 |
| WP_003065552 | 1250 | QRIN----SENS-TKYLD--YVSAHKKEFEKVLSCVEDFANLYVDVE-KNLSKIR-A | VAD-SM---DNFSIEE- | 1309 |
| WP_001040076 | 1249 | SRYNESKgKPEEiEKKQE--FVNQHVSYFDDILQLINDFSKRVILAD--ANLEKIN-R | LYQ-DNk--ENIPVDE- | 1314 |
| WP_001040078 | 1241 | SRYNESKgKPEEiEKKQE--FVNQHVSYFDDILQLINDFSKRVILAD--ANLEKIN-K | LYQ-DNk--ENISVDE- | 1306 |
| WP_001040080 | 1241 | SRYNESKgKPEEiEKKQE--FVNQHVSYFDDILQLINDFSKRVILAD--ANLEKIN-K | LYQ-DNk--ENISVDE- | 1306 |
| WP_001040081 | 1241 | SRYNESKgKPEEiEKKQE--FVNQHVSYFDDILQLINDFSKRVILAD--ANLEKIN-K | LYQ-DNk--ENISVDE- | 1306 |
| WP_001040083 | 1241 | SRYNESKgKPEEiEKKQE--FVNQHVSYFDDILQLINDFSNRVILAD--ANLEKIN-K | LYQ-DNk--ENIPVDE- | 1306 |
| WP_001040085 | 1241 | SRYNESKgKPEEiEKKQE--FVNQHISYFDDILQLINDFSNRVILAD--ANLEKIN-K | LYS-DNk--DNTPVDE- | 1306 |
| WP_001040087 | 1241 | SRYNELKgKPEEiEKKQE--FVVQHVSYFDDILQLINDFSNRVILAD--ANLEKIN-K | LYQ-DNk--ENIPVDE- | 1306 |
| WP_001040088 | 1241 | SRYNELKgKPEEiEQKQE--FVVQHVSYFDDILQLINDFSNRVILAD--ANLEKIN-K | LYQ-DNk--ENIPVDE- | 1306 |
| WP_001040089 | 1241 | SRYNELKgKPEEiEKKQE--FVVQHVSYFDDILQLINDFSKRVILAD--ANLEKIN-K | LYQ-DNk--ENIPVDE- | 1306 |
| WP_001040090 | 1241 | SRYNESKgKPEEiEKKQE--FVVQHVSYFDDILQLINDFSKRVILAD--ANLEKIN-K | LYQ-DNk--ENIPVDE- | 1306 |
| WP_001040091 | 1241 | SRYNESKgKPEEiEKKQE--FVNQHVSYFDDILQLINDFSNRVILAD--ANLEKIN-K | LYQ-DNk--ENISVDE- | 1306 |
| WP_001040092 | 1241 | SRYNESKgKPEEiEKKQE--FVNQHVSYFDDILQLINDFSNRVILAD--ANLEKIN-K | LYQ-DNk--ENISVDE- | 1306 |
| WP_001040094 | 1241 | SRYNESKgKPEEiEKKQE--FVNQHVSYFDDILQLINDFSNRVILAD--ANLEKIN-K | LYQ-DNk--ENISVDE- | 1306 |
| WP_001040095 | 1241 | SRYNELKgKPEEiEKKQE--FVVQHVSYFDDILQLINDFSNRVILAD--ANLEKIN-K | LYQ-DNk--ENISVDE- | 1306 |
| WP_001040096 | 1241 | SRYNELKgKPEEiEKKQE--FVVQHVSYFDDILQLINDFSNRVILAD--ANLEKIN-K | LYQ-DNk--ENISVDE- | 1306 |
| WP_001040097 | 1241 | SRYNELKgKPEEiEQKQE--FVVQHVSYFDDILQLINDFSNRVILAD--ANLEKIN-K | LYQ-DNk--ENIPVDE- | 1306 |
| WP_001040098 | 1241 | SRYNELKgKPEEiEKKQE--FVVQHVSYFDDILQLINDFSNRVILAD--ANLEKIN-K | LYQ-DNk--ENIPVDE- | 1306 |
| WP_001040099 | 1241 | SRYNESKgKPEEiEKKQE--FVVQHVSYFDDILQLINDFSNRVILAD--ANLEKIN-K | LYQ-DNk--ENIPVDE- | 1306 |
| WP_001040100 | 1241 | SRYNESKgKPEEiEKKQE--FVNQHVSYFDDILQLINDFSKRVILAD--ANLEKIN-K | LYQ-DNk--ENISVDE- | 1306 |
| WP_001040104 | 1241 | SRYNESKgKPEEiEKKQE--FVNQHVSYFDDILQLINDFSKRVILAD--ANLEKIN-K | LYQ-DNk--ENISVDE- | 1306 |
| WP_001040105 | 1241 | SRYNESKgKPEEiEKKQE--FVNQHVSYFDDILQLINDFSKRVILAD--ANLEKIN-K | LYQ-DNk--ENISVDE- | 1306 |
| WP_001040106 | 1241 | SRYNESKgKPEEiEKKQE--FVNQHVSYFDDILQLINDFSNRVILAD--ANLEKIN-K | LYQ-DNk--ENISVDE- | 1306 |
| WP_001040107 | 1241 | SRYNESKgKPEEiEKKQE--FVNQHVSYFDDILQLINDFSNRVILAD--ANLEKIN-K | LYQ-DNk--ENISVDE- | 1306 |
| WP_001040108 | 1241 | SRYNELKgKPEEiEKKQE--FVNQHVSYFDDILQLINDFSNRVILAD--ANLEKIN-K | LYQ-DNk--ENISVDE- | 1306 |
| WP_001040109 | 1241 | SRYNESKgKPEEiEKKQE--FVVQHVSYFDDILQLINDFSNRVILAD--ANLEKIN-K | LYS-DNk--DNTPVDE- | 1306 |
| WP_001040110 | 1241 | SRYNESKgKPEEiEKKQE--FVNQHVSYFDDILQLINDFSNRVILAD--ANLEKIN-K | LYQ-DNk--ENISVDE- | 1306 |
| WP_015058523 | 1241 | SRYNESKgKPEEiEKKQE--FVNQHVSYFDDILQLINDFSKRVILAD--ANLEKIN-K | LYQ-DNk--ENISVDE- | 1306 |
| WP_017643650 | 1241 | SRYNESKgKPEEiEKKQE--FVNQHVSYFDDILQLINDFSKRVILAD--ANLEKIN-K | LYQ-DNk--ENISVDE- | 1306 |
| WP_017647151 | 1241 | SRYNESKgKPEEiEKKQE--FVNQHVSYFDDILQLINDFSKRVILAD--ANLEKIN-K | LYQ-DNk--ENISVDE- | 1306 |
| WP_017648376 | 1241 | SRYNESKgKPEEiEKKQE--FVNQHVSYFDDILQLINDFSKRVILAD--ANLEKIN-K | LYQ-DNk--ENISVDE- | 1306 |
| WP_017649527 | 1241 | SRYNESKgKPEEiEKKQE--FVNQHVSYFDDILQLINDFSKRVILAD--ANLEKIN-K | LYQ-DNk--ENISVDE- | 1306 |
| WP_017771611 | 1241 | SRYNESKgKPEEiEKKQE--FVNQHVSYFDDILQLINDFSKRVILAD--ANLEKIN-K | LYQ-DNk--ENISVDE- | 1306 |
| WP_017771984 | 1241 | SRYNESKgKPEEiEKKQE--FVNQHVSYFDDILQLINDFSKRVILAD--ANLEKIN-K | LYQ-DNk--ENISVDE- | 1306 |
| CFQ25032 | 1241 | SRYNESKgKPEEiEKKQE--FVNQHVSYFDDILQLINDFSKRVILAD--ANLEKIN-K | LYQ-DNk--ENISVDE- | 1306 |
| CFV16040 | 1241 | SRYNESKgKPEEiEKKQE--FVNQHVSYFDDILQLINDFSKRVILAD--ANLEKIN-K | LYS-DNk--DNTPVDE- | 1306 |
| KLJ37842 | 1241 | SRYNESKgKPEEiEKKQE--FVNQHVSYFDDILQLINDFSKRVILAD--ANLEKIN-K | LYQ-DNk--ENISVDE- | 1306 |
| KLJ72361 | 1241 | SRYNESKgKPEEiEKKQE--FVNQHVSYFDDILQLINDFSKRVILAD--ANLEKIN-K | LYQ-DNk--ENISVDE- | 1306 |
| KLL20707 | 1255 | SRYNESKgKPEEiEKKQE--FVNQHVSYFDDILQLINDFSKRVILAD--ANLEKIN-K | LYQ-DNk--ENISVDE- | 1320 |

```
KLL42645            1241 SRYNELkgKPEEiEQKQE- FVVQHVSyFDDILQIINDFSNRVILAD- -ANLEKIN-K LYQ-DNk- -ENISVDE-        1306
WP_047207273        1241 SRYNESkgKPEEiEKKQE- FVNQHVSyFDDILQIINDFSKRVILAD- -ANLEKIN-K LYQ-DNk- -ENISVDE-        1306
WP_047209694        1241 SRYNELkgKPEEiEQKQE- FVNQHVSyFDDILQIINDFSNRVILAD- -ANLEKIN-K LYQ-DNk- -ENIPVDE-        1306
WP_050198062        1241 SRYNESkgKPEEiEKKQE- FVNQHVSyFDDILQIINDFSKRVILAD- -ANLEKIN-K LYQ-DNk- -ENISVDE-        1306
WP_050201642        1241 SRYNESkgKPEEiEKKQE- FVVQHVSyFDDILQIINDFSKRVILAD- -ANLEKIN-K LYQ-DNk- -ENISVDE-        1306
WP_050204027        1241 SRYNELkgKPEEiEQKQE- FVVQHVSyFDDILQIINDFSKRVILAD- -ANLEKIN-K LYQ-DNk- -ENISVDE-        1306
WP_050881965        1241 SRYNESkgKPEEiEKKQE- FVVQHVSyFDDILQIINDFSKRVILAD- -ANLEKIN-K LYQ-DNk- -ENISVDE-        1306
WP_050886065        1241 SRYNESkgKPEEiEKKQE- FVNQHVSyFDDILQIINDFSKRVILAD- -ANLEKIN-K LYS-DNk- -DNTPVDE-        1306
AHN30376            1241 SRYNESkgKPEEiEKKQE- FVNQHVSyFDDILQIINDFSKRVILAD- -ANLEKIN-K LYQ-DNk- -ENISVDE-        1306
EA078426            1241 SRYNESkgKPEEiEKKQE- FVNQHVSyFDDILQIINDFSNRVILAD- -ANLEKIN-K LYQ-DNk- -ENISVDE-        1306
CCW42055            1241 SRYNESkgKPEEiEKKQE- FVNQHVSyFDDILQIINDFSNRVILAD- -ANLEKIN-K LYQ-DNk- -ENISVDE-        1306
WP_003041502        1254 KRIN- - -NPIN-KDHIE- YVKKHRDDFKELLNYVLEFNEKVGAT- KNGGRLK- E AVA-DF- -DSKSNEE-       1313
WP_037593752        1223 YQIE- - - - -KNYE-PEHRE- YVEKHKDEFKELLEYISVFSRKVLAD- NNLTKIE-M LFS-KN- -KDAEVSS-       1282
WP_037591684        1223 YRIE- - - - -KDYE-PEHRE- YVEKHKDEFKELLEYISVFSRKVLAD- NNLTKIE-M LFS-KN- -KDAEVSS-       1282
GAD46167            1222 YQIE- - - - -KNYE-PEHRE- YVEKHKDEFKELLEYISVFSRKVLAD- NNLTKIE-M LFS-KN- -KDAEVSS-       1281
WP_018363470        1254 HRIG- - - -NFNS-AEHLK- YVSEHKKEFFEEVLSCVENFANVVDVE- KNLsKIR-A AAD-SM- -DNFSIEE-       1313
WP_003043819        1249 QNISATTgSNNLg- - - - - YIEQHREEFKEIFEKIIDFSEKYILKN- KVNSNLK-S SFD-EQfavSDSIL- -1        1310
WP_006269658        1222 YRIE- - - - -KDYE-PEHRE- YVEKHKDEFKELLEYISVFSRKVLAD- NNLTKIE-M LFS-KN- -KDAEVSS-       1281
WP_048800889        1242 HRID- - - -NSDN-SEHLK- YITEHKEEFGKLLSYIENFAKSVDVD- KNLEKIQ-L AVE-KI- -DSFSVKE-       1301
WP_012767106        1246 -HAHKIEsSKE- -LEHEA- YILDHYNDLYQLLSYIERFASLYVDVE- KNISKVK-E LFS-NI- -ESYSISEi       1308
WP_014612333        1246 -HAHKIEsSKE- -LEHEA- YILDHYNDLYQLLSYIERFASLYVDVE- KNISKVK-E LFS-NI- -ESYSISEi       1308
WP_015017095        1246 -HAHKIEsSKE- -LEHEA- YILDHYNDLYQLLSYIERFASLYVDVE- KNISKVK-E LFS-NI- -ESYSISEi       1308
WP_015057649        1246 -HAHKIEsSKE- -LEHEA- YILDHYNDLYQLLSYIERFASLYVDVE- KNISKVK-E LFS-NI- -ESYSISEi       1308
WP_048277215        1246 -HAHKIEsSKE- -LEHEA- YILDHYNDLYQLLSYIERFASLYVDVE- KNISKVK-E LFS-NI- -ESYSISEi       1308
WP_049519324        1246 -HAHKIEsSKE- -LEHEA- YILDHYNDLYQLLSYIERFASLYVDVE- KNISKVK-E LFS-NI- -ESYSISEi       1308
WP_012515931        1220 AHYHELTgsSEDvLRKKY- FVDRHLHYFDDIIQMINDFAERHILAS- SNLEKIN-H TYH-NN- -SDLPINEr       1285
WP_021320964        1220 AHYHELTgsSEDvLRKKY- FVERHLHYFDDIIQMINDFAERHILAS- SNLEKIN-H TYH-NN- -SDLPINEr       1285
WP_037581760        1220 AHYHELTgSSEDvLRKKY- FVERHLHYFDDIIQMINDFAERHILAS- SNLEKIN-H TYH-NN- -SDLPVNEr       1285
WP_004232481        1252 QHVN- - - -NSHK-PEHLN- YVKQHKDEFKDIFPNLIISIARINILKP- KVVDNL- - -IN EF- -TEYGQED-       1308
WP_009854540        1247 HRAD- - - -NFNS-TEYLN- YVSEHKKEFEKVLSCVEDFANLYVDVE- KNLSKIR-A VAD-SM- -DNFSIEE-       1306
WP_012962174        1248 HRVN- - - -SFNN-SEHLK- YVSEHKKEFGEVLSCVENFAKSVDVE- KNLGKIR-A VAD-KI- -DTFSIED-       1307
WP_039695303        1249 HRAD- - - -NENS-TEYLN- YVSEHKKEFEKVLSCVEDFANLYVDVE- KNLSKIR-A VAD-SM- -DNFSIEE-       1308
WP_014334983        1252 HRID- - - -SFNS-TEHLK- YVSEHKKKEFEKVLSCVENFSNLYVDVE- KNLSKVR-A AAE-SM- -TNFSLEE-       1311
WP_003099269        1240 SHYTKFTgKEEDrEKKRS- YVESHLYFFDEIMQIIVEYSNRYILAD- SNLIKIQ-N LYK-EKq- -NFSIEEq      1305
AHY15608            1240 SHYTKFTgKEEDrEKKRS- YVESHLYFFDEIMQIIVEYSNRYILAD- SNLIKIQ-N LYK-EKq- -NFSIEEq      1273
AHY17476            1240 SHYTKFTgKEEDrEKKRS- YVESHLYXFX- - - - - - - - - - - - - - - - - - - - - - - - - - - - - -        1267
ESR09100              72 SHYTKFTgkEEDrEKKRS- YVESHLYYFDEIMQIIVEYSNRYILAD- SNLIKIQ-N LYK- -Ek- -DNFSIEEg-        137
AGM98575            1240 SHYTKFTgkEEDrEKKRS- YVESHLYYFDVRLSQVFRVTNVEF- - - - - - - - - - - - - - - - - - - -        1281
ALF27331            1222 KKVDVLVkSKDD- - -DYD- -LEEHRAEFAEELLDCIKKFNDMYILAS- SNMSKIE-E LYA-QN- -NNKDITE-       1289
WP_018372492        1229 KKVDVLVkSKDD- - -DYD- -LEEHRAEFAEELLDCIKKFNDMYILAS- SNMSKIE-E IYQ-KNi- -DAPIEE-       1281
WP_045618028        1252 QRIN- - - -KISE-PIHKQ- YVETHQSEFKELLTAIIISLSKKYI-QK- PNVESL- - LQQ-AF- -DQSDKDIyq      1310
WP_045635197        1247 KNVH- - - -KLDE-PGHLE- YIQKHRNEFKDLLNLVSEFSQKVLAD- ANLEKIK-S LYA-DN- -EQADIEI-       1306
WP_002263549        1222 KNIH- - - - -KVDE-PKHLD- YVDKHKDEFKKELLDVVSNFSKKYTLAE- GNLEKIK-E LYA-QN- -NGEDLKE-       1281
WP_002263887        1222 KNIH- - - - -KVDE-PKHLD- YVDKHKDEFKKELLDVVSNFSKKYTLAE- GNLEKIK-E LYA-QN- -NGEDLKE-       1281
WP_002264920        1222 KNIH- - - - -KVDE-PKHLD- YVDKHKDEFKKELLDVVSNFSKKYTLAE- GNLEKIK-E LYA-QN- -NGEDLKE-       1281
WP_002269043        1222 KNIH- - - - -KVDE-PKHLD- YVDKHKDEFKKELLDVVSNFSKKYTLAE- GNLEKIK-E LYA-QN- -NGEDLKE-       1281
WP_002269448        1222 KNIH- - - - -KVDE-PKHLD- YVDKHKDEFKKELLDVVSNFSKKYTLAE- GNLEKIK-E LYA-QN- -NGEDLKE-       1281
WP_002271977        1222 KNIH- - - - -KVDE-PKHLD- YVDKHKDEFKKELLDVVSNFSKKYTLAE- GNLEKIK-E LYA-QN- -NGEDLKE-       1281
WP_002272766        1222 KNIH- - - - -KVDE-PKHLD- YVDKHKDEFKKELLDVVSNFSKKYTLAE- GNLEKIK-E LYA-QN- -NGEDLKE-       1281
WP_002273241        1222 KNIH- - - - -KVDE-PKHLD- YVDKHKDEFKKELLDVVSNFSKKYTLAE- GNLEKIK-E LYA-QN- -NGEDLKE-       1281
WP_002275430        1222 KNIH- - - - -KVDE-PKHLD- YVDKHKDEFKKELLDVVSNFSKKYTLAE- GNLEKIK-E LYA-QN- -NGEDLKE-       1281
WP_002276448        1222 KNIH- - - - -KVDE-PKHLD- YVDKHKDEFKKELLDVVSNFSKKYTLAE- GNLEKIK-E EHIQKIE-E AYSkER- -DSASIEE-       1281
WP_002277050        1230 HHL- - - - - - -DN-DYSNE- YVKNHYQQFDILFNEITSFSKKCKLGK- EHIQKIE-E AYSkER- -DSASIEE-       1287
```

-continued

```
WP_002273364  1222  KNIH----KVDE-PKHLD--YVDKHKDEFKELLDVVSNFSKKYTLAE--GNLEKIK-E  LYA-QN---NGEDLKE-  1281
WP_002279025  1222  KNIH----KVDE-PKHLD--YVDKHKDEFKELLDVVSNFSKKYTLAE--GNLEKIK-E  LYA-QN---NGEDLKE-  1281
WP_002279859  1222  KNIH----KVDE-PKHLD--YVDKHKDEFKELLDVVSNFSKKYTLAE--GNLEKIK-E  LYA-QN---NGEDLKE-  1281
WP_002280230  1222  KNIH----KVDE-PKHLD--YVDKHKDEFKELLDVVSNFSKKYTLAE--GNLEKIK-E  LYA-QN---NGEDLKE-  1281
WP_002281696  1222  KNIH----KVDE-PKHLD--YVDKHKDEFKELLDVVSNFSKKYTLAE--GNLEKIK-E  LYA-QN---NGEDLKE-  1281
WP_002282247  1230  HHL-------DN-DYSNE--YVKNHYQQFDILFNEITSFSKKCKLGK--EHIQKIE-E  AYSkER---DFASIEE-  1287
WP_002282906  1222  KNIH----KVDE-PKHLD--YVDKHKDEFKELLDVVSNFSKKYTLAE--GNLEKIK-E  LYA-QN---NGEDLKE-  1281
WP_002283846  1222  KNIH----KVDE-PKHLD--YVDKHKDEFKELLDVVSNFSKKYTLAE--GNLEKIK-E  LYA-QN---NGEDLKE-  1281
WP_002287255  1222  KNIH----KVDE-PKHLD--YVDKHKDEFKELLDVVSNFSKKYTLAE--GNLEKIK-E  LYA-QN---NGEDLKE-  1281
WP_002288990  1222  KNIH----KVDE-PKHLD--YVDKHKDEFKELLDVVSNFSKKYTLAE--GNLEKIK-E  LYA-QN---NGEDLKE-  1281
WP_002289641  1222  KNIH----KVDE-PKHLD--YVDKHKDEFKELLDVVSNFSKKYTLAE--GNLEKIK-E  LYA-QN---NGEDLKE-  1281
WP_002290427  1222  KNIH----KVDE-PKHLD--YVDKHKDEFKELLDVVSNFSKKYTLAE--GNLEKIK-E  LYA-QN---NGEDLKE-  1281
WP_002295753  1222  KNIH----KVDE-PKHLD--YVDKHKDEFKELLDVVSNFSKKYTLAE--GNLEKIK-E  LYA-QN---NGEDLKE-  1281
WP_002296423  1222  KNIH----KVDE-PKHLD--YVDKHKDEFKELLDVVSNFSKKYTLAE--GNLEKIK-E  LYA-QN---NGEDLKE-  1281
WP_002304487  1236  KNIH----KVDE-PKHLD--YVDKHKDEFKELLDVVSNFSKKYTLAE--GNLEKIK-E  LYA-QN---NGEDLKE-  1295
WP_002305844  1222  KNIH----KVDE-PKHLD--YVDKHKDEFKELLDVVSNFSKKYTLAE--GNLEKIK-E  LYA-QN---NGEDLKE-  1281
WP_002307203  1222  KNIH----KVDE-PKHLD--YVDKHKDEFKELLDVVSNFSKKYTLAE--GNLEKIK-E  LYA-QN---NGEDLKE-  1281
WP_002310390  1222  KNIH----KVDE-PKHLD--YVDKHKDEFKELLDVVSNFSKKYTLAE--GNLEKIK-E  LYA-QN---NGEDLKE-  1281
WP_002352408  1222  KNIH----KVDE-PKHLD--YVDKHKDEFKELLDVVSNFSKKYTLAE--GNLEKIK-E  LYA-QN---NGEDLKE-  1281
WP_012997688  1222  KNIH----KVDE-PKHLD--YVDKHKDEFKELLDVVSNFSKKYTLAE--GNLEKIK-E  LYA-QN---NGEDLKE-  1281
WP_014677909  1222  KNIH----KVDE-PKHLD--YVDKHKDEFKELLDVVSNFSKKYTLAE--GNLEKIK-E  LYA-QN---NGEDLKE-  1281
WP_019312892  1222  KNIH----KVDE-PKHLD--YVDKHKDEFKELLDVVSNFSKKYTLAE--GNLEKIK-E  LYA-QN---NGEDLKE-  1281
WP_019313659  1222  KNIH----KVDE-PKHLD--YVDKHKDEFKELLDVVSNFSKKYTLAE--GNLEKIK-E  LYA-QN---NGEDLKE-  1281
WP_019314093  1222  KNIH----KVDE-PKHLD--YVDKHKDEFKELLDVVSNFSKKYTLAE--GNLEKIK-E  LYA-QN---NGEDLKE-  1281
WP_019315370  1222  KNIH----KVDE-PKHLD--YVDKHKDEFKELLDVVSNFSKKYTLAE--GNLEKIK-E  LYA-QN---NGEDLKE-  1281
WP_019803776  1222  KNIH----KVDE-PKHLD--YVDKHKDEFKELLDVVSNFSKKYTLAE--GNLEKIK-E  LYA-QN---NGEDLKE-  1281
WP_019805234  1222  KNIH----KVDE-PKHLD--YVDKHKDEFKELLDVVSNFSKKYTLAE--GNLEKIK-E  LYA-QN---NGEDLKE-  1281
WP_024783594  1222  KNIH----KVDE-PKHLD--YVDKHKDEFKELLDVVSNFSKKYTLAE--GNLEKIK-E  LYA-QN---NGEDLKE-  1281
WP_024784288  1230  HHL-------DN-DYSNE--YVKNHYQQFDILFNEITSFSKKCKLGK--EHIQKIE-E  AYSkER---DFASIEE-  1287
WP_024784666  1222  KNIH----KVDE-PKHLD--YVDKHKDEFKELLDVVSNFSKKYTLAE--GNLEKIK-E  LYA-QN---NGEDLKE-  1281
WP_024784894  1222  KNIH----KVDE-PKHLD--YVDKHKDEFKELLDVVSNFSKKYTLAE--GNLEKIK-E  LYA-QN---NGEDLKE-  1281
WP_024786433  1230  HHL-------DN-DYSNE--YVKNHYQQFDILFNEITSFSKKCKLGK--EHIQKIE-E  AYSkER---DSASIEE-  1287
WP_049473442  1222  KNIH----KVDE-PKHLD--YVDKHKDEFKELLDVVSNFSKKYTLAE--GNLEKIK-E  LYA-QN---NGEDLKE-  1281
WP_049474547  1222  KNIH----KVDE-PKHLD--YVDKHKDEFKELLDVVSNFSKKYTLAE--GNLEKIK-E  LYA-QN---NGEDLKE-  1281
EMC03581      1215  KNIH----KVDE-PEHLE--YIQKHRNEFKGLLNLVSEFSQKTVLAD--ANLEKIK-N  LYA-QN---NGEDLKE-  1274
WP_000428612  1250  KNIH----RLDE-PEHLE--YVETHQSFEELLTTIISLSKKYI-QK--PIVESL---  LQQ-AF---EQADKDIyq 1309
WP_000428613  1248  KNVH----KLDE-PEHLE--YIQKHRNEFKDLLNLVSEFSQKYVLAD--ANLEKIQ-N  LYA-DN---EQADIEI-  1307
WP_049523028  1243  KRIQ----KKDE-PEHLE--YIKQHHSEFNDLLNFVSEFSQKVLAE--SNLEKIK-N  LYI-DN---EQTNMEE-  1302
WP_003107102  1209  SRYTSFSgKEEDrEKHRH--FVESHLHYFDEIKDIIADFSRRYILAD--ANLEKIL-T  LYN-EKn--QFSIEEq-  1274
WP_054279288  1242  SKRDK--gTQSEnME-----YISNHVEKFIEIFPHYIIRYAEKNVIKP-KVIERLN-D  TENqKF---NDSDLTEl-  1303
WP_049531101  1252  QRIN----KISE-PIHKQ--YVETHQSFEELLTTIISLSKKYI-QK--PIVESL---  LQQ-AF---EQADKDIyq 1310
WP_049538452  1252  QRIN----KISE-PIHKQ--YVEAHQNEFKELLTTIIISLSKKYI-QK--PNVESL---  LHQ-AF---EQADNDIyq 1310
WP_049549711  1254  QRIN----KFSE-PIHKQ--YVEAHQNEFKELLTTIIISLSKKYI-QK--PNVESL---  LYK-KK---EAYSINEq- 1312
WP_007896501  1246  SRYDKLSsKIESeQQKKL--FVEQHLHYFDEILDIVKHATCYIKAE--NNLKKII-S  LYK-KK---EAYSINEq- 1311
EFR44625      1198  SRYDKLSsKIESeQQKKL--FVEQHLHYFDEILDIVKHATCYIKAE--NNLKKII-S  LYK-KK---EAYSINEq- 1263
WP_002897477  1247  KNLH----KLDE-PEHLE--YIQKHRNEFKDLLNLVSEFSQKYLAE--ANLEKIK-D  LYA-DN---EQADIEI-  1306
WP_002906454  1253  QRIN----KISE-PIHKQ--YVEAHQNEFKELLTTIISLSKKYI-QK--PNVELL---  LQQ-AF---DQADKDIyq 1311
WP_009729476  1248  KNVH----KLDE-PGHLE--YIQKHRNEFKDLLNLVSEFSQKYVLAD--ANLEKIK-N  LYA-QN---EQADIEI-  1307
CQR24647      1238  QHAN----KEDS----VI--YLEKHRHLSELFHHIIGVSEKTILKP--KVEMTLN-N  AFE-KHf--EFDEVSE-  1295
WP_000666813  1252  KNVH-------VI--YLEKHRYEFKDLLNLVSEFSQKYVLAD--ANLEKIK-N  LYA-DN---EQADIEI-  1311
WP_009754323  1248  KNVH----KLDE-PEHLE--YIQKHRYEFKDLLNLVSEFSQKYVLAD--ANLEKIK-S  LYV-DN---EQADIEI-  1307
WP_044674937  1241  SNIH----KITE-PIHLN--YVNKNKHEFKELLRHISDFSTRYILAQ--DRLSKIE-E  LYD-KN---DGDDISD-  1300
WP_044676715  1243  SNIH----KITE-PIHLN--YVNKNKHEFKELLRHISDFSTRYILAQ--DRLSKIE-E  LYD-KN---DGDDISD-  1302
```

```
                                     -continued

WP_044680361  1243  SNIH----KITE-PIHLN--YVNKNKHEFKELLRHISDFSTRYILAQ--DRLSKIE-E LYD-KN---DGDDISD-   1302
WP_044681799  1241  SNIH----KITE-PIHLN--YVNKNKHEFKELLRHISDFSTRYILAQ--DRLSKIE-E LYD-KN---DGDDISD-   1300
WP_049533112  1254  KRIN----NPIN-KDHIE--YVKKHRDDFKELLNYVLEFNEKYVGAT--KNGERLK-E AVA-DF---DSKSNEE-   1313
WP_029909905  1182  STKQA-----DE-AMFLKyyRLEHLEAVFEEL---IRKQAADYQIFE--KLIKKIEvN FYS--c----TYNEk-   1240
WP_006506696  1212  YNAIYKQ-DYDNlDDIlMi------------QLYIELTNKMKVLYPAY-rGIAEKFE-S YVV---i----SKEEk    1268
AIT42264      1240  SHYEKLKgSPEDrEQKQL--FVEQHKHYLDEIIEQISEFSKRVILAD--ANLDKVL-S AYN-KH---RDKPIREq    1305
WP_034440723  1218  KHYNE----DE-TSHK---FIVEHKAYFDELLNYIVEFANKYLELE--NSIEKIK-D LYH-----gKGPDVEEKe   1276
AKQ21048      1240  SHYEKLKgSPEDrEQKQL--FVEQHKHYLDEIIEQISEFSKRVILAD--ANLDKVL-S AYN-KH---RDKPIREq-   1305
WP_004636532  1212  NRYDKVK-----fPDSIE--YVHDNLAKFDDLLEYVIDFSNKYINAD--KNVQKIQ-K IYK-EH---GTEDVEL-   1271
WP_002364836  1218  KQCLL-----PNQ-SESLA--YVEQHQPEFQEILERVVDFAEVHTLAK--SKVQQIV-K LFE-AN---QTADVKE-   1277
WP_016631044  1169  KQCLL-----PNQ-SESLA--YVEQHQPEFQEILERVVDFAEVHTLAK--SKVQQIV-K LFE-AN---QTADVKE-   1228
EM575795       954  QHYDEIAhKESF------D--YVNDHLSFREILDQVIDFSNRYTIA--KNTEKIA-E LFE-AN---QESTVQs-   1013
WP_002373311  1218  KQCLL-----PNQ-SESLA--YVEQHQPEFQEILERVVDFAEVHTLAK--SKVQQIV-K LFE-AN---QTADVKE-   1277
WP_002378009  1218  KQCLL-----PNQ-SESLA--YVEQHQPEFQEILERVVDFAEVHTLAK--SKVQQIV-K LFE-AN---QTADVKE-   1277
WP_002407324  1218  KQCLL-----PNQ-SESLA--YVEQHQPEFQEILERVVDFAEVHTLAK--SKVQQIV-K LFE-AN---QTADVKE-   1277
WP_002413717  1218  KQCLL-----PNQ-SESLA--YVEQHQPEFQEILERVVDFAEVHTLAK--SKVQQIV-K LFE-AN---QTADVKE-   1277
WP_010775580  1220  KQCLL-----PNQ-SESLA--YVEQHQPEFQEILERVVDFAEVHTLAK--SKVQQIV-K LFE-AN---QTADVKE-   1279
WP_010818269  1218  KQCLL-----PNQ-SESLA--YVEQHQPEFQEILERVVDFAEVHTLAK--SKVQQIV-K LFE-AN---QTADVKE-   1277
WP_010824395  1218  KQCLL-----PNQ-SESLA--YVEQHQPEFQEILERVVDFAEVHTLAK--SKVQQIV-K LFE-AN---QTADVKE-   1277
WP_016222645  1218  KQCLL-----PNQ-SESLA--YVEQHQPEFQEILERVVDFAEVHTLAK--SKVQQIV-K LFE-AN---QTADVKE-   1277
WP_033624816  1218  KQCLL-----PNQ-SESLA--YVEQHQPEFQEILERVVDFAEVHTLAK--SKVQQIV-K LFE-AN---QTADVKE-   1277
WP_033625576  1218  KQCLL-----PNQ-SESLA--YVEQHQPEFQEILERVVDFAEVHTLAK--SKVQQIV-K LFE-TN---QTADVKE-   1277
WP_033789179  1218  KQCLL-----PNQ-SESLA--YVEQHQPEFQEILERVVDFAEVHTLAK--SKVQQIV-K LFE-AN---QTDDLAK-   1277
WP_002310644  1220  KQYDEISHKESF------D--YVNEHHKEFSEVFARVLEFAGKYTLAE--KNIEKLE-K IYK-EN---QTDDLAK-   1279
WP_002312694  1221  KQYDEISHKESF------D--YVNEHHKEFSEVFARVLEFAGKYTLAE--KNIEKLE-K IYK-EN---QTDDLAK-   1280
WP_002314015  1221  KQYDEISHKESF------D--YVNEHHKEFSEVFARVLEFAGKYTLAE--KNIEKLE-K IYK-EN---QTDDLAK-   1280
WP_002320716  1220  KQYDEISHKESF------D--YVNEHHKEFSEVFARVLEFAGKYTLAE--KNIEKLE-K IYK-EN---QTDDLAK-   1279
WP_002330729  1221  KQYDEISHKESF------D--YVNEHHKEFSEVFARVLEFAGKYTLAE--KNIEKLE-K IYK-EN---QTDDLAK-   1280
WP_002335161  1221  KQYDEISHKESF------D--YVNEHHKEFSEVFARVLEFAGKYTLAE--KNIEKLE-K IYK-EN---QTDDLAK-   1280
WP_002345439  1221  KQYDEISHKESF------D--YVNEHHKEFSEVFARVLEFAGKYTLAE--KNIEKLE-K IYK-EN---QTDDLAK-   1280
WP_034867970  1211  QHYDKITyQESF------D--YVNTHLSDFSAILTEVLAFAEKYTLAD--KNIERIQ-E LYE-EN---KYGETSM-   1270
WP_034937432  1221  QHYDKITyQESF------D--YVNTHLSDFSAILTEVLAFAEKYTLAD--KNIERIQ-E LYE-EN---QTDDLAK-   1280
WP_010720994  1211  QHYDKITyQESF------D--YVNTHLSDFSAILTEVLAFAEKYTLAD--KNIERIQ-E LYE-EN---KYGETSM-   1270
WP_010737004  1211  QHYDKITyQESF------D--YVNTHLSDFSAILTEVLAFAEKYTLAD--KNIERIQ-E LYE-EN---KYGEISM-   1270
WP_034700478  1211  QHYDKITyQESF------D--YVNTHLSDFSAILTEVLAFAEKYTLAD--KNIERIQ-K LYE-EN---KYGEISM-   1270
WP_072090003  1209  KKLIN--gKNSD----SVS--YIQNNKEKFREIFEYIVDFSSKYISAD--ANLNKIE-K IFE-NNfh---KASEqe   1269
WP_023519017  1205  RHYDEINhKVSF------D--YVNAHKEGENDIPDFISDEGVRYILAP--QHLEKIK-V AYE-EN---KEVDLKE-   1264
WP_010770040  1216  KQVDE-----DS-GKSEE--YVREHRAEFAEHLNYVQAFSETKILAN--KNLQTIL-K LYE-EN---KEADIKE-   1274
WP_048604708  1213  KHCNE-----KP-D-SLK--YVTEHQSGFSEIMAHVKDFAEKYTLVD--KNLEKIL-S LYA-KN---MDSEVKE-   1270
WP_010750235  1214  NHYDEIAyKDSY------D--YIESNREMFAELLAHVSEFAKRYTSAP--QKLNQII-A TYE-KN---QEADRKI-   1273
AII16583      1279  SHYEKLKgSPEDrEQKQL--FVEQHKHYLDEIIEQISEFSKRVILAD--ANLDKVL-S AYN-KH---RDKPIREq-   1344
WP_029073316  1226  YKAMKYK-NYSElSQEEIm------------NVVDIFVEKLKLYYPTY-kNIATNFE-N FEN---i---SDEEk-   1282
WP_031589969  1200  YKAMKYK-NYDNlDSEKTi------------DLYRLLINKMELYYPEnFADKYVVAP--KNSEKIR-R LYE-ENq---SIEEk-   1283
KDA45870      1242  NAKDG-----EQKLE----DHKAEFKELPDKIMEFADKYVVAP--KNSEKIR-R LYE-ENq---DATPme   1253
WP_039099354  1238  LPLTQ-----SELAEQV---YDEILDQVMHYFPLYDTNQFrAKLSAGKaA DGN-KMv----QVGOqv   1306
AKP02966      1216  QIPDE-----DpDQILAf--YDKNILVEILQELITKMKKFYPFY--KNEQEFLaS FNQ-------ATTSEk-   1296
WP_010991369  1216  ANCEV-----SD-GKSLD--YIESNREMFAELLAHVSEFAKRYTLAE--ANLNKIN-Q LFE-QN---KEGDIKA-   1274
WP_033838504  1219  ANCEV-----SD-GKSLD--YIESNREMFAELLAHVSEFAKRYTLAE--ANLNKIN-Q LFE-QN---KEGDIKA-   1277
EHN60060       985  ANCEV-----SD-GKSLD--YIESNREMFAELLAHVSEFAKRYTLAE--ANLNKIN-Q LFE-QN---KEGDIKA-   1043
EFR89594      1216  KNCEA-----ND-GESLA--YIEMHREMFAELLAYISEFAKRYTLAN--DRLEKIN-M FFE-QN---KKGDIKV-   1274
WP_038409211   835  KNCEA-----ND-GESLA--YIEMHREMFAELLAYISEFAKRYTLAN--DRLEKIN-M FFE-QN---KKGDIKV-    893
EFR95520      1216  KNCEA-----SD-GKSLK--YIEAHRETFSELLAQVSEFATRYTLAD--ANLSKIN-N LFE-QN---KEGDIKA-   1274
WP_003723650
```

-continued

| | | | | |
|---|---|---|---|---|
| WP_003727705 | 1216 | KNCEA------SD-GKSLK--YIEAHRETFSELLAQVSEFATKYTLAD--ANlSKIN-N LFE-QN---KEGDIKA-- | 1274 |
| WP_003730785 | 1216 | KNCEA------SD-GKSLK--YIEAHRETFSELLAQVSEFATKYTLAD--ANlSKIN-N LFE-QN---KEGDIKA-- | 1274 |
| WP_003733029 | 1216 | EKYEA------ID-GESLA--YIEVHRALFDELLAYISEFARKYTLSN--DRLDEIN-M LYE-RN---KDGDVKS-- | 1274 |
| WP_003739838 | 1216 | KNCEA------SD-GKSLD--YIESNREMFGELLAHVSEFATKYTLAD--ANlSKIN-Q LFE-QN---KDNDIKV-- | 1274 |
| WP_014601172 | 1216 | KNCEA------SD-GKSLK--YIEAHRETFSELLAQVSEFATRYTLAD--ANlSKIN-N LFE-QN---KEGDIQA-- | 1274 |
| WP_023548323 | 1216 | EKREA------ID-GESLA--YIEAHKAVFGELLAHISEFARKYTLAN--DKLDEIN-M LYE-RN---KEGDIKA-- | 1274 |
| WP_031665337 | 1216 | KNCEA------SD-GKSLK--YIEAHRETFSELLAQVSEFATRYTLAN--ANlSKIN-N LFE-QN---KEGDIKA-- | 1274 |
| WP_031669209 | 1216 | EKYEA------ID-GESLA--YIEAHKAVFGELLAHISEFARKYTLSN--DRLDEIN-M LYE-RN---KDGDVKS-- | 1274 |
| WP_033920898 | 1216 | EKREA------ID-GESLA--YIEAHRETFSELLAQVSEFATRYTLAD--DKLDEIN-M LYE-RN---KDGDVKS-- | 1274 |
| AKI42028 | 1216 | KNCEA------SD-GKSLK--YIEAHRETFSELLAQVSEFATRYTLAD--ANlSKIN-N LFE-QN---KEGDIQA-- | 1277 |
| AKI50529 | 1219 | EKREA------SD-GKSLK--YIEAHKAVFGELLAHISEFARKYTLAN--DKLDEIN-M LYE-RN---KDGDVKS-- | 1277 |
| EFR83390 | 664 | | 722 |
| WP_046323366 | 1216 | KNCEA------SD-GKSLA--YIESHREMFAEILLDSISEFASRYTLAD--ANLEKIN-T IFE-QN---KSGDVKV-- | 1274 |
| AKE81011 | 1256 | SHYEKLkgSPEDnEQKQL-FVEQHKHYLDEIIEQISEFSKKVILAD--ANlDKVL-S AYN-KH--RDKPIREq | 1321 |
| CUO82355 | 1216 | YNAIYKQ-DFDGlDNMLMi-----QLYLQLLQKMDTLYPAY-kGIAKRFF-K FVS--i----SKEEk | 1272 |
| WP_031285506 | 1218 | YAAMLKK--RYEYiDEEEIf-------DlYLQLLQKMDTLYPAY-KFKN------DVVEk | 1274 |
| AGZ01981 | 1273 | SHYEKLkgSPEDnEQKQL-FVEQHKHYLDEIIEQISEFSKKVILAD--ANlDKVL-S AYN-KH--RDKPIREq | 1338 |
| AKA60242 | 1240 | SHYEKLkgSPEDnEQKQL-FVEQHKHYLDEIIEQISEFSKKVILAD--ANlDKVL-S AYN-KH--RDKPIREq | 1305 |
| AK540380 | 1240 | SHYEKLkgSPEDnEQKQL-FVEQHKHYLDEIIEQISEFSKKVILAD--ANlDKVL-S AYN-KH--RDKPIREq | 1305 |
| 4UN5_B | 1244 | SHYEKLkgSPEDnEQKQL-FVEQHKHYLDEIIEQISEFSKKVILAD--ANlDKVL-S AYN-KH-S RDKPIREq | 1309 |
| WP_010922251 | | -AE---NII HLFFTLTNLGAP-AAFKYFD--TTI--DRK--R-YTSTKEVL DATLIHQSITGLYETRIDLSQL-- | 1365 |
| WP_039695303 | | ISN---SFI NLLTLTALGAP-ADFNFLG--EKI--PRK--R-YTSTKECL NATLIHQSITGLYETRIDLSKL-- | 1369 |
| WP_045635197 | | LAN---SFI NLLTFTALGAP-AAFKFPG--KDI--DRK--R-YTTVSEIL NATLIHQSITGLYETWIDLSKL-- | 1367 |
| 5AXW_A | | | |
| WP_009880683 | 990 | -AE---NII HLFFTLTNLGAP-AAFKCFD--TTI--GRN--R-YKSIKEVL DATLIHQSITGLYETRIDLSQL-- | 1049 |
| WP_010922251 | 1306 | -AE---NII HLFFTLTNLGAP-AAFKYFD--TTI--DRK--R-YTSTKEVL DATLIHQSITGLYETRIDLSQL-- | 1365 |
| WP_011054416 | 1306 | -AE---NII HLFFTLTNLGAP-AAFKYFD--TTI--DRK--R-YTSTKEVL DATLIHQSITGLYETRIDLSQL-- | 1365 |
| WP_011284745 | 1306 | -AE---NII HLFFTLTNLGAP-AAFKYFD--TTI--DRK--R-YTSTKEVL DATLIHQSITGLYETRIDLSQL-- | 1365 |
| WP_011285506 | 1306 | -AE---NII HLFFTLTNLGAP-AAFKYFD--TTI--DRK--R-YKSIKEVL DATLIHQSITGLYETRIDLSQL-- | 1365 |
| WP_011527619 | 1306 | -AE---NII HLFFTLTNLGAP-TAFKYFD--TTI--DRK--R-YTSTKEVL DATLIHQSITGLYETRIDLSQL-- | 1365 |
| WP_012560673 | 1306 | -AE---NII HLFFTLTNLGAP-AAFKCFD--TTI--GRN--R-YKSIKEVL DATLIHQSITGLYETRIDLSQL-- | 1365 |
| WP_014407541 | 1305 | -AE---NII HLFFTLTNLGAP-AAFKYFD--TTI--DRK--R-YTSTKEVL DATLIHQSITGLYETRIDLSQL-- | 1364 |
| WP_020905136 | 1306 | -AE---NII HLFFTLTNLGAP-AAFKYFD--TTI--DRK--R-YTSTKEVL DATLIHQSITGLYETRIDLSQL-- | 1365 |
| WP_023080005 | 1305 | -AK---NII HLFFTLTNLGAP-AAFKYFD--TTI--ERN--R-YKSIKEVL DATLIHQSITGLYETRIDLSQL-- | 1364 |
| WP_023610282 | 1305 | -AK---NII HLFFTLTNLGAP-AAFKYFD--TTI--DRK--R-YTSTKEVL DATFIHQSITGLYETRIDLSQL-- | 1364 |
| WP_023612963 | 1306 | -AE---NII HLFFTLTNLGAP-AAFKYFD--TTI--DRK--R-YKSIKEVL DATLIHQSITGLYETRIDLSQL-- | 1365 |
| WP_030126706 | 1306 | -AE---NII HLFFTLTNLGAP-AAFKYFD--TTI--DRK--R-YTSTKEVL DATLIHQSITGLYETRIDLSQL-- | 1365 |
| WP_031488318 | 1306 | -AE---NII HLFFTLTNFGAP-AAFIYFD--TTI--GRN--R-YKSIKEVL DATLIHQSITGLYETRIDLSQL-- | 1365 |
| WP_032460140 | 1306 | -AE---NII HLFFTLTNLGAP-AAFKYFD--TTI--GRN--R-YKSIKEVL DATLIHQSITGLYETRIDLSQL-- | 1365 |
| WP_032461047 | 1306 | -AE---NII HLFFTLTNLGAP-AAFKYFD--TTI--DRK--R-YTSTKEVL DATLIHQSITGLYETRIDLSQL-- | 1365 |
| WP_032462016 | 1306 | -AE---NII HLFFTLTNLGAP-AAFKYFD--TTI--DRK--R-YTSTKEVL DATLIHQSITGLYETRIDLSQL-- | 1365 |
| WP_032462936 | 1305 | -AE---NII HLFFTLTNLGAP-AAFKYFD--TTI--DRK--R-YTSTKEVL DATLIHQSITGLYETRIDLSQL-- | 1364 |
| WP_032464890 | 1305 | -AE---NII HLFFTLTNLGAP-AAFKYFD--TTI--DRK--R-YTSTKEVL DATLIHQSITGLYETRIDLSQL-- | 1365 |
| WP_033888930 | 1131 | -AE---NII HLFFTLTNLGAP-TAFKYFD--TTI--DRK--R-YTSTKEVL DATLIHQSITGLYETRIDLSQL-- | 1190 |
| WP_038431314 | 1306 | -AE---NII HLFFTLTNLGAP-AAFKYFD--TTI--DRK--R-YTSTKEVL DATLIHQSITGLYETRIDLSQL-- | 1365 |
| WP_038432938 | 1305 | -AK---NII HLFFTLTNLGAP-AAFIYFD--TTI--ERN--R-YKSIKEVL DATLIHQSITGLYETRIDLSQL-- | 1364 |
| WP_038434062 | 1306 | -AE---NII HLFFTLTNLGAP-AAFKYFD--TTI--GRN--R-YKSIKEVL DATLIHQSITGLYETRIDLSQL-- | 1365 |
| BAQ51233 | 1217 | -AE---NII HLFFTLTNLGAP-AAFKYFD--TTI--DRK--R-YTSTKEVL DATLIHQSITGLYETRIDLSQL-- | 1276 |
| KGE60162 | 481 | -AE---NII HLFFTLTNLGAP-AAFKYFD--TTI--DRK--R-YTSTKEVL DATLIHQSITGLYETRIDLSQL-- | 540 |
| KGE60856 | 244 | | 303 |
| WP_002989955 | 1306 | -AE---NII HLFFTLTNLGAP-AAFKYFD--TTI--DRK--R-YTSTKEVL DATFIHQSITGLYETRIDLSQL-- | 1365 |
| WP_003030002 | 1282 | LAK---SFI SLLTFTAFGAP-AAFNFFG--ENI--DRK--R-YTSVTECL NATLIHQSITGLYETRIDLSKL-- | 1342 |
| WP_003065552 | 1310 | ISN---SFI NLLTLTALGAP-ADFNFLG--EKI--PRK--R-YTSTKECL NATLIHQSITGLYETRIDLSKI-- | 1370 |

-continued

```
WP_001040076    1307  LAN---NII  NLFTFTSLGAP-AAFKFFD--KIV--DRK--R-YTSTKEVL  NSTLIHQSITGLYETRIDLGKL--  1367
WP_001040078    1315  LAN---NII  NLFTFTSLGAP-AAFKFFD--KIV--DRK--R-YTSTKEVL  NSTLIHQSITGLYETRIDLSKL--  1375
WP_001040080    1307  LAN---NII  NLFTFTSLGAP-AAFKFFD--KIV--DRK--R-YTSTKEVL  NSTLIHQSITGLYETRIDLGKL--  1367
WP_001040081    1307  LAN---NII  NLFTFTSLGAP-AAFKFFD--KIV--DRK--R-YTSTKEVL  NSTLIHQSITGLYETRIDLGKL--  1367
WP_001040083    1307  LAN---NII  NLFTFTSLGAP-AAFKFFD--KIV--DRK--R-YTSTKEVL  NSTLIHQSITGLYETRIDLGKL--  1367
WP_001040085    1307  LAN---NII  NLFTFTSLGAP-AAFKFFD--KIV--DRK--R-YTSTKEVL  NSTLIHQSITGLYETRIDLGKL--  1367
WP_001040087    1307  LAN---NII  NLFTFTSLGAP-AAFKFFD--KIV--DRK--R-YTSTKEVL  NSTLIHQSITGLYETRIDLGKL--  1367
WP_001040088    1307  LAN---NII  NLFTFTSLGAP-AAFKFFD--KIV--DRK--R-YTSTKEVL  NSTLIHQSITGLYETRIDLGKL--  1367
WP_001040089    1307  LAN---NII  NLFTFTSLGAP-AAFKFFD--KIV--DRK--R-YTSTKEVL  NSTLIHQSITGLYETRIDLGKL--  1367
WP_001040090    1307  LAN---NII  NLFTFTSLGAP-AAFKFFD--KIV--DRK--R-YTSTKEVL  NSTLIHQSITGLYETRIDLGKL--  1367
WP_001040091    1307  LAN---NII  NLFTFTSLGAP-AAFKFFD--KIV--DRK--R-YTSTKEVL  NSTLIHQSITGLYETRIDLGKL--  1367
WP_001040092    1307  LAK---NII  NLFTFTSLGAP-AAFKFFD--KSV--DRK--R-YTSTKEVL  DSTLIHQSITGLYETRIDLGKL--  1367
WP_001040094    1307  LAN---NII  NLFTFTSLGAP-AAFKFFD--KIV--DRK--R-YTSTKEVL  NSTLIHQSITGLYETRIDLGKL--  1367
WP_001040095    1307  LAN---NII  NLFTFTSLGAP-AAFKFFD--KIV--DRK--R-YTSTKEVL  NSTLIHQSITGLYETRIDLGKL--  1367
WP_001040096    1307  LAN---NII  NLFTFTSLGAP-AAFKFFD--KIV--DRK--R-YTSTKEVL  NSTLIHKSITGLYETRIDLGKL--  1367
WP_001040097    1307  LAN---NII  NLFTFTSLGAP-AAFKFFD--KIV--DRK--R-YTSTKEVL  NSTLIHQSITGLYETRIDLGKL--  1367
WP_001040098    1307  LAN---NII  NLFTFTSLGAP-AAFKFFD--KIV--DRK--R-YTSTKEVL  NSTLIHQSITGLYETRIDLGKL--  1367
WP_001040099    1307  LAN---NII  NLFTFTSLGAP-AAFKFFD--KIV--DRK--R-YTSTKEVL  NSTLIHQFITGLYETRIDLGKL--  1367
WP_001040100    1307  LAN---NII  NLFTFTSLGAP-AAFKFFD--KIV--DRK--R-YTSTKEVL  DSTLIHQSITGLYETRIDLGKL--  1367
WP_001040104    1307  LAK---NII  NLFTFTSLGAP-AAFKFFD--KSV--DRK--R-YTSTKEVL  NSTLIHQSITGLYETRIDLGKL--  1367
WP_001040105    1307  LAN---NII  NLFTFTSLGAP-AAFKFFD--KIV--DRK--R-YTSTKEVL  NSTLIHQSITGLYETRIDLGKL--  1367
WP_001040106    1307  LAN---NII  NLFTFTSLGAP-AAFKFFD--KIV--DRK--R-YTSTKEVL  NSTLIHQSITGLYETRIDLGKL--  1367
WP_001040107    1307  LAN---NII  NLFTFTSLGAP-AAFKFFD--KIV--DRK--R-YTSTKEVL  NSTLIHQSITGLYETRIDLGKL--  1367
WP_001040108    1307  LAN---NII  NLFTFTSLGAP-AAFKFFD--KIV--DRK--R-YTSTKEVL  NSTLIHQSITGLYETRIDLGKL--  1367
WP_001040109    1307  LAN---NII  NLFTFTSLGAP-AAFKFFD--KIV--DRK--R-YTSTKEVL  NSTLIHQSITGLYETRIDLGKL--  1367
WP_001040110    1307  LAN---NII  NLFTFTSLGAP-AAFKFFD--KIV--DRK--R-YTSTKEVL  NSTLIHQSITGLYETRIDLGKL--  1367
WP_015058523    1307  LAK---NII  NLFTFTSLGAP-AAFKFFD--KSV--DRK--R-YTSTKEVL  NSTLIHQSITGLYETRIDLGKL--  1367
WP_017643650    1307  LAN---NII  NLFTFTSLGAP-AAFKFFD--KIV--DRK--R-YTSTKEVL  DSTLIHQSITGLYETRIDLGKL--  1367
WP_017647151    1307  LAN---NII  NLFTFTSLGAP-AAFKFFD--KIV--DRK--R-YTSTKEVL  NSTLIHQSITGLYETRIDLGKL--  1367
WP_017648376    1307  LAN---NII  NLFTFTSLGAP-AAFKFFD--KIV--DRK--R-YTSTKEVL  NSTLIHQSITGLYETRIDLGKL--  1367
WP_017649527    1307  LAN---NII  NLFTFTSLGAP-AAFKFFD--KIV--DRK--R-YTSTKEVL  NSTLIHQSITGLYETRIDLGKL--  1367
WP_017771611    1307  LAN---NII  NLFTFTSLGAP-AAFKFFD--KIV--DRK--R-YTSTKEVL  NSTLIHQSITGLYETRIDLGKL--  1367
WP_017771984    1307  LAN---NII  NLFTFTSLGAP-AAFKFFD--KIV--DRK--R-YTSTKEVL  NSTLIHQSITGLYETRIDLGKL--  1367
CFQ25032        1307  LAN---NII  NLFTFTSLGAP-AAFKFFD--KIV--DRK--R-YTSTKEVL  NSTLIHQSITGLYETRIDLGKL--  1367
CFV16040        1307  LAN---NII  NLFTFTSLGAP-AAFKFFD--KIV--DRK--R-YTSTKEVL  DSTLIHQSITGLYETRIDLGKL--  1367
KLJ37842        1307  LAN---NII  NLFTFTSLGAP-AAFKFFD--KIV--DRK--R-YTSTKEVL  NSTLIHQSITGLYETRIDLGKL--  1367
KLJ72361        1307  LAN---NII  NLFTFTSLGAP-AAFKFFD--KIV--DRK--R-YTSTKEVL  NSTLIHQSITGLYETRIDLGKL--  1367
KLL20707        1321  LAN---NII  NLFTFTSLGAP-AAFKFFD--KIV--DRK--R-YTSTKEVL  NSTLIHQSITGLYETRIDLGKL--  1381
KLL42645        1307  LAN---NII  NLFTFTSLGAP-AAFKFFD--KIV--DRK--R-YTSTKEVL  NSTLIHQSITGLYETRIDLGKL--  1367
WP_047207273    1307  LAN---NII  NLFTFTSLGAP-AAFKFFD--KIV--DRK--R-YTSTKEVL  NSTLIHQSITGLYETRIDLGKL--  1367
WP_047209694    1307  LAN---NII  NLFTFTSLGAP-AAFKFFD--KIV--DRK--R-YTSTKEVL  NSTLIHKSITGLYETRIDLGKL--  1367
WP_050198062    1307  LAN---NII  NLFTFTSLGAP-AAFKFFD--KIV--DRK--R-YTSTKEVL  NSTLIHQSITGLYETRIDLGKL--  1367
WP_050201642    1307  LAN---NII  NLFTFTSLGAP-AAFKFFD--KIV--DRK--R-YTSTKEVL  NSTLIHQSITGLYETRIDLGKL--  1367
WP_050204027    1307  LAN---NII  NLFTFTSLGAP-AAFKFFD--KII--DRK--R-YTSTKEVL  NSTLIHQSITGLYETRIDLGKL--  1367
WP_050881965    1307  LAN---NII  NLFTFTSLGAP-AAFKFFD--KIV--DRK--R-YTSTKEVL  NSTLIHQSITGLYETRIDLGKL--  1367
WP_050886065    1307  LAK---NII  NLFTFTSLGAP-AAFKFFD--KSV--DRK--R-YTSTKEVL  DSTLIHQSITGLYETRIDLGKL--  1367
AHN30376        1307  LAN---NII  NLFTFTSLGAP-AAFKFFD--KIV--DRK--R-YTSTKEVL  NSTLIHQSITGLYETRIDLGKL--  1367
EA078426        1307  LAN---NII  NLFTFTSLGAP-AAFKFFD--KIV--DRK--R-YTSTKEVL  NSTLIHQSITGLYETRIDLGKL--  1367
CCW42055        1314  ICT---SFL  GLFELTSLGSA-SDFEFLG--VKI--PRY--RAYTPSSLLK  DSTLIHQSITGLYETRIDLSKL--  1383
WP_003041502    1283  LAK---SFI  SLLTFTAFGAP-AAFNFFG--ENI--DRK--R-YTSVTECL  NATLIHQSITGLYETRIDLSKL--  1343
WP_037593752    1283  LAK---SFI  SLLTFTAFGAP-AAFNFFG--ENI--DRK--R-YTSVTECL  NATLIHQSITGLYETRIDLSKL--  1343
WP_049516684    1282  LAK---SFI  SLLTFTAFGAP-AAFNFFG--ENI--DRK--R-YTSVTECL  NATLIHQSITGLYETRIDLSKL--  1342
GAD46167
```

-continued

```
WP_018363470   1314 ISD---SFI NLLTLTALGAP-ADFNFLG--BKI--PRK--R-YNSTKECL NATLIHQSITGLYETRIDLSKL-- 1374
WP_003043819   1311 -SN---SFV SLLKYTSFGAS-GGFTFLD--LDVkqGRLj--R-YQTVTEVL DATLIYQSITGLYETRTDLSQL-- 1372
WP_006269658   1282 LAK---SFI SLLTFTAFGAP-AAFNFFG--ENI--DRK--R-YTSVTECL NATLIHQSITGLYETRIDLSKL-- 1342
WP_048800889   1302 ISN---SFI HLLLTLALGAP-ADFNFLG--EKI--PRK--R-YTSTKECL NATLIHQSITGLYETRIDLSKL-- 1362
WP_012767106   1309 -CS---SVI NLLLTLTASGAP-ADFKFLG--TTI--PRK--R-YGSPQSIL SSTLIHQSITGLYETRIDLSQL-- 1368
WP_014613333   1309 -CS---SVI NLLLTLTASGAP-ADFKFLG--TTI--PRK--R-YGSPQSIL SSTLIHQSITGLYETRIDLSQL-- 1368
WP_015017095   1309 -CS---SVI NLLLTLTASGAP-ADFKFLG--TTI--PRK--R-YGSPQSIL SSTLIHQSITGLYETRIDLSQL-- 1368
WP_015057649   1309 -CS---SVI NLLLTLTASGAP-ADFKFLG--TTI--PRK--R-YGSPQSIL SSTLIHQSITGLYETRIDLSQL-- 1368
WP_048272215   1309 -CS---SVI NLLLTLTASGAP-ADFKFLG--TTI--PRK--R-YGSPQSIL SSTLIHQSITGLYETRIDLSQL-- 1368
WP_049519324   1309 -CS---SVI NLLLTLTASGAP-ADFKFLG--TTI--PRK--R-YGSPQSIL NATLIHQSVTGLYETRIDLSQL-- 1368
WP_012515931   1286 -AE---NII NVFTFVALGAP-AAFKFFD--ATI--DRK--R-YTSTKECL NATLIHQSVTGLYETRIDLSKL-- 1345
WP_021320964   1286 -AE---NII NVFTFVALGAP-AAFKFFD--ATI--DRK--R-YTSTKEVL NATLIHQSVTGLYETRIDLSKL-- 1345
WP_037581760   1286 -AE---NII NVFTFVALGAP-AAFKFFD--ATI--DRK--R-YTSTKEVL NATLIHQSVTGLYETRIDLSKL-- 1345
WP_004232481   1309 ISSlseSFI NLLKFISPGAP-GAFKFLK--LDV--KQSnlR--YKSTTEAL SATLIHQSVTGLYETRIDLSKL-- 1374
WP_009854540   1307 ISN---SFI NLLTLTALGAP-ADFNFLG--EKI--PRK--R-YTSTKECL TATLIHQSITGLYETRIDLSKL-- 1367
WP_012962174   1308 ISI---SFV NLLTLTASGAP-ADFKFLG--TTI--PRK--R-YGSPQSIL SSTLIHQSITGLYETRIDLSKL-- 1368
WP_039695303   1309 ISN---SFI NLLTLTALGAP-ADFNFLG--EKI--PRK--R-YTSTKECL NATLIHQSITGLYETRIDLSKL-- 1369
WP_014334983   1312 ISA---SFI NLLTLTALGAP-ADFNFLG--EKI--PRK--R-YTSTKECL SATLIHQSVTGLYETRIDLSKL-- 1372
WP_030992269   1306 -AI---NML NLPTFTDLGAP-SAFKFFN--GDI--DRK--R-YSSTNEII NSTLIYQSPTGLYETRIDLSKL-- 1365
AHY17476            ---------- --------------------  ---  ---  ---  -------- ---------------------- 
AHY17476        138 -AI---NML NLPTFTDLGAP-SAFKFFNg--DI--DRK--R-YSSTNEII NSTLIYQSPTGLYETRIDLSRL-- 197
ESR09100            ---------- --------------------  ---  ---  ---  -------- ---------------------- 
AGM98575       1282 LAS---SFI NLLTFTAIGAP-AAFKFFD--NNI--DRK--R-YTSTTEIL NATLIHQSITGLYETRIDLSKL-- 1342
ALF27331       1290 -SFV SFV -LLNFTMMGAA-TDFKFPG--QII--PRK--R-YPSTTECL KSTLIHQSITGLYETRIDLSKL-- 1350
WP_018372492   1311 LSE---SFI SLLKLISPGAP-GTFKFLG--VEI--SQSnvR--YQSVSSCF NATLIHQSITGLYETRIDLSRL-- 1373
WP_045618028   1307 LAN---SFI NLLTFTAIGAP-AAFKFPG--KDI--DRK--R-YTTVSEIL NATLIHQSITGLYETWIDLSKL-- 1367
WP_045635197   1282 LAS---SFI NLLTFTAIGAP-ATFKFFD--KNI--DRK--R-YTSTTEIL NATLIHQSITGLYETRIDLNKL-- 1342
WP_002263549   1282 LAS---SFI NLLTFTAIGAP-ATFKFFD--KNI--DRK--R-YTSTTEIL NATLIHQSITGLYETRIDLSKL-- 1342
WP_002263887   1282 LAS---SFI NLLTFTAIGAP-ATFKFFD--KNI--DRK--R-YTSTTEIL NATLIHQSITGLYETRIDLSKL-- 1342
WP_002264920   1282 LAS---SFI NLLTFTAIGAP-ATFKFFD--KNI--DRK--R-YTSTTEIL NATLIHQSITGLYETRIDLSKL-- 1342
WP_002269043   1282 LAS---SFI NLLTFTAIGAP-ATFKFFD--KNI--DRK--R-YTSTTEIL NATLIHQSITGLYETRIDLSKL-- 1342
WP_002269448   1282 LAS---SFI NLLTFTAIGAP-ATFKFFD--KNI--DRK--R-YTSTTEIL NATLIHQSITGLYETRIDLSKL-- 1342
WP_002271977   1282 LAS---SFI NLLTFTAIGAP-ATFKFFD--KNI--DRK--R-YTSTTEIL NATLIHQSITGLYETRIDLSKL-- 1342
WP_002272766   1282 LAS---SFI NLLTFTAIGAP-ATFKFFD--KNI--DRK--R-YTSTTEIL NATLIHQSITGLYETRIDLSKL-- 1342
WP_002273241   1282 LAS---SFI NLLTFTAIGAP-ATFKFFD--KNI--DRK--R-YTSTTEIL NATLIHQSITGLYETRIDLSKL-- 1342
WP_002275430   1282 LAS---SFI NLLTFTAIGAP-AAFKFFD--KNI--DRK--R-YTSTTEIL NATLIHQSITGLYETRIDLSKL-- 1342
WP_002276448   1282 LAS---SFI NLLTFTAIGAP-ATFKFFD--KNI--DRK--R-YTSTTEIL NATLIHQSITGLYETRIDLNKL-- 1342
WP_002277050   1288 LAD---GFI KLLGFTQLGAT-SPFSFLG--IKL--NQK--Q-YTGKKDYL EATLIHQSITGLYETRIDLNKL-- 1352
WP_002773364   1282 LAS---SFI NLLTFTAIGAP-ATFKFFD--KNI--DRK--R-YTSTTEIL NATLIHQSITGLYETRIDLSKL-- 1342
WP_002779025   1282 LAS---SFI NLLTFTAIGAP-ATFKFFD--KNI--DRK--R-YTSTTEIL NATLIHQSITGLYETRIDLSKL-- 1342
WP_002279859   1282 LAS---SFI NLLTFTAIGAP-ATFKFFD--KNI--DRK--R-YTSTTEIL NATLIHQSITGLYETRIDLSKL-- 1342
WP_002280230   1282 LSS---SFI NLLTFTAIGAP-ATFKFFD--KNI--DRK--R-YTSTTEIL NATLIHQSITGLYETRIDLSKL-- 1342
WP_002281696   1288 LAD---GFI KLLGFTQLGAT-SPFSFLG--IKL--NQK--Q-YTGKKDYL EATLIHQSITGLYETRIDLSKL-- 1352
WP_002282247   1282 LAS---SFI NLLTFTAIGAP-ATFKFFD--KNI--DRK--R-YTSTTEIL NATLIHQSITGLYETRIDLSKL-- 1342
WP_002282906   1282 LAS---SFI NLLTFTAIGAP-ATFKFFD--KNI--DRK--R-YTSTTEIL NATLIHQSITGLYETRIDLSKL-- 1342
WP_002283846   1282 LAS---SFI NLLTFTAIGAP-ATFKFFD--KNI--DRK--R-YTSTTEIL NATLIHQSITGLYETRIDLSKL-- 1342
WP_002287255   1282 LAS---SFI NLLTFTAIGAP-ATFKFFD--KNI--DRK--R-YTSTTEIL NATLIHQSITGLYETRIDLSKL-- 1342
WP_002288990   1282 LAS---SFI NLLTFTAIGAP-ATFKFFD--KNI--DRK--R-YTSTTEIL NATLIHQSITGLYETRIDLSKL-- 1342
WP_002289641   1282 LAS---SFI NLLTFTAIGAP-ATFKFFD--KNI--DRK--R-YTSTTEIL NATLIHQSITGLYETRIDLSKL-- 1342
WP_002290427   1282 LAS---SFI NLLTFTAIGAP-ATFKFFD--KNI--DRK--R-YTSTTEIL NATLIHQSITGLYETRIDLSKL-- 1342
WP_002295753   1282 LAS---SFI NLLTFTAIGAP-ATFKFFD--KNI--DRK--R-YTSTTEIL NATLIHQSITGLYETRIDLSKL-- 1342
WP_002296423   1282 LAS---SFI NLLTFTAIGAP-ATFKFFD--KNI--DRK--R-YTSTTEIL NATLIHQSITGLYETRIDLSKL-- 1342
WP_002304487   1296 LAS---SFI NLLTFTAIGAP-AAFKFFD--KNI--DRK--R-YTSTTEIL NATLIHQSITGLYETRIDLNKL-- 1356
```

| ID | | | | | | | |
|---|---|---|---|---|---|---|---|
| WP_002305844 | 1282 | LAS---SFI | NLLTFTAIGAP-ATFKFFD--KNI--DRK--R-YTSTTEIL | NATLIHQSITGLYETRIDLSKL-- | 1342 |
| WP_002307203 | 1282 | LAS---SFI | NLLTFTAIGAP-ATFKFFD--KNI--DRK--R-YTSTTEIL | NATLIHQSITGLYETRIDLSKL-- | 1342 |
| WP_002310390 | 1282 | LAS---SFI | NLLTFTAIGAP-ATFKFFD--KNI--DRK--R-YTSTTEIL | NATLIHQSITGLYETRIDLSKL-- | 1342 |
| WP_002352408 | 1282 | LAS---SFI | NLLTFTAIGAP-ATFKFFD--KNI--DRK--R-YTSTTEIL | NATLIHQSITGLYETRIDLSKL-- | 1342 |
| WP_012997688 | 1282 | LAS---SFI | NLLTFTAIGAP-ATFKFFD--KNI--DRK--R-YTSTTEIL | NATLIHQSITGLYETRIDLSKL-- | 1342 |
| WP_014677909 | 1282 | LAS---SFI | NLLTFTAIGAP-ATFKFFD--KNI--DRK--R-YTSTTEIL | NATLIHQSITGLYETRIDLSKL-- | 1342 |
| WP_019312892 | 1282 | LAS---SFI | NLLTFTAIGAP-ATFKFFD--KNI--DRK--R-YTSTTEIL | NATLIHQSITGLYETRIDLSKL-- | 1342 |
| WP_019313659 | 1282 | LAS---SFI | NLLTFTAIGAP-ATFKFFD--KNI--DRK--R-YTSTTEIL | NATLIHQSITGLYETRIDLSKL-- | 1342 |
| WP_019314093 | 1282 | LAS---SFI | NLLTFTAIGAP-AAFKFFD--KNI--DRK--R-YTSTTEIL | NATLIHQSITGLYETRIDLSKL-- | 1342 |
| WP_019315370 | 1282 | LSS---SFI | NLLTFTAIGAP-AAFKFFD--KNI--DRK--R-YTSTTEIL | NATLIHQSITGLYETRIDLSKL-- | 1342 |
| WP_019803776 | 1282 | LAS---SFI | NLLTFTAIGAP-ATFKFFD--KNI--DRK--R-YTSTTEIL | NATLIHQSITGLYETRIDLNKL-- | 1342 |
| WP_019805234 | 1282 | LAS---SFI | NLLTFTAIGAP-ATFKFFD--KNI--DRK--R-YTSTTEIL | NATLIHQSITGLYETRIDLNKL-- | 1342 |
| WP_024783594 | 1282 | LAS---SFI | NLLTFTAIGAP-ATFKFFD--KNI--DRK--R-YTSTTEIL | NATLIHQSITGLYETRIDLSKL-- | 1342 |
| WP_024784288 | 1288 | LAD---GFI | KLLGFTQLGAT-SPFSFLG--IKL--NQK--Q-YTGKKDYL | EATLIHQSITGLYETRIDLSKL-- | 1352 |
| WP_024784666 | 1282 | LAS---SFI | NLLTFTAIGAP-ATFKFFD--KNI--DRK--R-YTSTTEIL | NATLIHQSITGLYETRIDLSKL-- | 1342 |
| WP_024784894 | 1282 | LAS---SFI | NLLTFTAIGAP-ATFKFFD--KNI--DRK--R-YTSTTEIL | NATLIHQSITGLYETRIDLSKL-- | 1342 |
| WP_024786433 | 1288 | LAD---GFI | KLLGFTQLGAT-SPFSFLG--IKL--NQK--Q-YTGKKDYL | EATLIHQSITGLYETRIDLSKL-- | 1352 |
| WP_049473442 | 1282 | LAS---SFI | NLLTFTAIGAP-ATFKFFD--KNI--DRK--R-YTSTTEIL | NATLIHQSITGLYETRIDLSKL-- | 1342 |
| WP_049474547 | 1282 | LAS---SFI | NLLTFTAIGAP-ATFKFFD--KNI--DRK--R-YTSTTEIL | KATLIHQSITGLYETRIDLSKL-- | 1342 |
| EMC03581 | 1275 | LAS---SFI | NLLTFTAIGAP-ATFKFPG--KNI--DRK--R-YTSTTEIL | NATLIHQSITGLYETRIDLSKL-- | 1335 |
| WP_000428612 | 1310 | LAN---SFI | NLLTFTSLGAP-AAFKFPG--KDV--DRK--R-YTTVSEIL | NATLIHQSLTGLYETRIDLSKL-- | 1370 |
| WP_000428613 | 1308 | LSE---SFI | SLLKLTSFGAP-AAFKFPG--VEI--SQSsvR-YKPNSQFL | DTTLIHQSITGLYETRIDLSKL-- | 1368 |
| WP_049523028 | 1303 | IAN---SFI | NLLTFTAPGAP-AVFKFPG--KDI--ERK--R-YSTVTEIL | KATLIHQSLTGLYETRIDLSKL-- | 1363 |
| WP_003107102 | 1275 | -AT---NML | NLPFTFTGLGAP-ATLKFFN--VDI--DRK--R-YTSSTEIL | NSTLIRQSITGLYETRIDLSKL-- | 1334 |
| WP_054279288 | 1304 | -SI---SFL | NLPFKFTSFGAP-BKFTFLN--SEIkqDDV--R-YRSTKECL | NSTLIHQSVTGLYETRIDLSQF-- | 1365 |
| WP_049531101 | 1311 | LSE---SFI | SLLKLTSFGAP-GAFRFLG--VEI--SQSnvR-YQSVSSCF | NATLIHQSITGLYETRIDLSKL-- | 1373 |
| WP_049538452 | 1311 | LSE---SFI | SLLKLTSFGAP-GAFKFLG--VEI--SQSsvR-YKPNSQFL | DATLIHQSITGLYETRIDLSKL-- | 1373 |
| WP_049549711 | 1313 | LSE---SFI | SLLKLTSFGAP-GAFKFLG--AEI--SQSsvR-YKPNSQFL | DTTLIHQSITGLYETRIDLSKL-- | 1375 |
| WP_007896501 | 1312 | -AL---NML | NLFIFTSLGAP-STFVFFD--ETI--DRK--R-YTTSDVL | NGILIQQSITGLYETRIDLSRP-- | 1371 |
| EFR44625 | 1264 | -AL---NML | NLFIFTSLGAP-STFVFFD--ETI--DRK--R-YTTSDVL | NGILIQQSITGLYETRIDLSRF-- | 1323 |
| WP_002897477 | 1307 | LAN---SFI | NLLTFTAIGAP-AAFKFPG--KDV--DRK--R-YTTVSEIL | DTTLIHQSITGLYETRIDLSKL-- | 1367 |
| WP_002906454 | 1312 | LSE---SFI | SLLKLTSFGAP-GAFKFLG--VEI--SQSsvR-YKPNSQFL | DATLIHQSITGLYETRIDLSKL-- | 1374 |
| WP_009729476 | 1308 | LAN---SFI | NLLTFTAIGAP-AAFKFPG--KDV--DRK--R-YTTVSEIL | NATLIHQSITGLYETRIDLSKL-- | 1368 |
| CQR24647 | 1296 | LAQ---SFI | SLLKFTAPGAP-GGFKFLD--ADI--KQSnlR-YQTVTEVL | SSTLIHQSVTGLYETRIDLSKL-- | 1358 |
| WP_000066813 | 1312 | LAN---SFI | NLLTFTAIGAP-AAFKFLG--KDV--DRK--R-YTTVSEIL | NATLIHQSITGLYETRIDLSKL-- | 1372 |
| WP_009754323 | 1308 | LAN---SFI | NLLTFTAIGAP-AAFKFPG--KDV--DRK--R-YTTVSEIL | NATLIHQSITGLYETRIDLSKL-- | 1368 |
| WP_044674937 | 1301 | LTS---SFV | NLLTFTAIGAP-AAFKFLG--SVI--DRK--R-YTSIAEIL | EATLIHQSVTGLYETRIDLSKL-- | 1361 |
| WP_044676715 | 1303 | LTS---SFV | NLLTFTAIGAP-AAFKFLG--SVI--DRK--R-YTSIAEIL | EATLIHQSVTGLYETRIDLSKL-- | 1363 |
| WP_044680361 | 1301 | LTS---SFV | NLLTFTAIGAP-AAFKFLG--SVI--DRK--R-YTSIAEIL | EATLIHQSVTGLYETRIDLSKL-- | 1361 |
| WP_044681799 | 1301 | LTS---SFV | NLLTFTAIGAP-AAFKFLG--SVI--DRK--R-YTSIAEIL | EATLIHQSVTGLYETRIDLSKL-- | 1361 |
| WP_049533112 | 1314 | ICT---SFL | GLPELTSLGSA-SDFEFLG--VKI--PRY--RdYTPSSLLK | DSTLIHQSITGLYETRIDLSKL-- | 1383 |
| WP_029090905 | 1241 | -VK---VI | ELLKITQANATnGDLKLLK---M-sNREg-R-LGSVSVAL | DFKIINQSVTGLYQSIEDYNN-- | 1300 |
| WP_006506696 | 1269 | -AN---II | QMLIVMHRGPQnGNIVYDDf-KI-sDRIg-R-LKTKNHNL | NIVFISQSPTGIYTKKYKL--- | 1329 |
| AIT42264 | 1306 | -AE---NII | HLPFLTNLGAP-AAFKYFD--TTI--DRK--R-YTSTKEVL | DATLIHQSITGLYETRIDLSQL-- | 1365 |
| WP_034440723 | 1277 | LVE---SFI | NLLAITKCGPA-ADITFLG--EKI--SRK--R-YRSTNCLW | GSEVIFQSPTGLYETRLRLE--- | 1335 |
| AKQ21048 | 1306 | -AE---NII | HLPFLTNLGAP-AAFKYFD--TTI--DRK--R-YTSTKEVL | DATLIHQSITGLYETRIDLSQL-- | 1365 |
| WP_004636532 | 1272 | TVE---SFV | NLMTFTAMGAP-ATFKYFG--ESI--TRS--R-YTSITEFR | GSTLIFQSITGLYETRYKL---- | 1329 |
| WP_002636836 | 1278 | IAA---SFI | QLMQFNAMGAP-STFKFFQ--KDI--ERA--R-YTSIKEIF | DATIIYQSPTGLYETRRKV---- | 1335 |
| WP_016631044 | 1229 | IAA---SFI | QLMQFNAMGAP-STFKFFQ--KDI--ERA--R-YTSIKEIF | DATIIYQSPTGLYETRRKV---- | 1286 |
| EM575795 | 1014 | LSQ---SFI | NLMQLNAMGAP-ADFKFFD--VII--PRK--R-YPSLTEIW | ESTITYQSTTGLRETRTRMATLwd | 1076 |
| WP_002373311 | 1278 | IAA---SFI | QLMQFNAMGAP-STFKFFQ--KDI--ERA--R-YTSIKEIF | DATIIYQSTTGLYETRRKV---- | 1335 |
| WP_002378009 | 1278 | IAA---SFI | QLMQFNAMGAP-STFKFFQ--KDI--ERA--R-YTSIKEIF | DATIIYQSTTGLYETRRKV---- | 1335 |
| WP_002407324 | 1278 | IAA---SFI | QLMQFNAMGAP-STFKFFQ--KDI--ERA--R-YTSIKEIF | DATIIYQSTTGLYETRRKV---- | 1335 |

-continued

```
WP_002413717   1278 IAA---SFI QLMQFNAMGAP-STFKFFQ--KDI--ERA--R-YTSIKEIF DATIIYQSTTGLYETRRKV----  1335
WP_010775580   1280 IAA---SFI QLMQFNAMGAP-STFKFFQ--KDI--ERA--R-YTSIKEIF DATIIYQSTTGLYETRRKV----  1337
WP_010818269   1278 IAA---SFI QLMQFNAMGAP-STFKFFQ--KDI--ERA--R-YTSIKEIF DATIIYQSTTGLYETRRKV----  1335
WP_010824395   1278 IAA---SFI QLMQFNAMGAP-STFKFFQ--KDI--ERA--R-YTSIKEIF DATIIYQSTTGLYETRRKV----  1335
WP_016622645   1278 IAA---SFI QLMQFNAMGAP-STFKFFQ--KDI--ERA--R-YTSIKEIF DATIIYQSTTGLYETRRKV----  1335
WP_033625576   1278 IAA---SFI QLMQFNAMGAP-STFKFFQ--KDI--ERA--R-YTSIKEIF DATIIYQSTTGLYETRRKV----  1335
WP_033789179   1278 IAA---SFI QLMQFNAMGAP-STFKFFQ--KDI--ERA--R-YTSIKEIF DATIIYQSTTGLYETRRKV----  1335
WP_002310644   1280 LAS---SFV NLMQFNAMGAP-ADFKFFD--VTI--PRK--R-YTSLTEIW QSTIIHQSITGLYETRIRMGK--  1339
WP_002312694   1281 LAS---SFV NLMQFNAMGAP-ADFKFFD--VTI--PRK--R-YTSLTEIW QSTIIHQSITGLYETRIRMGK--  1340
WP_002314015   1281 LAS---SFV NLMQFNAMGAP-ADFKFFD--VTI--PRK--R-YTSLTEIW QSTIIHQSITGLYETRIRMGK--  1340
WP_002320716   1281 LAS---SFV NLMQFNAMGAP-ADFKFFD--VTI--PRK--R-YTSLTEIW QSTIIHQSITGLYETRIRMGK--  1340
WP_002330729   1280 LAS---SFV NLMQFNAMGAP-ADFKFFD--VTI--PRK--R-YTSLTEIW QSTIIHQSITGLYETRIRMGK--  1339
WP_002335161   1281 LAS---SFV NLMQFNAMGAP-ADFKFFD--VTI--PRK--R-YTSLTEIW QSTIIHQSITGLYETRIRMGK--  1340
WP_002345439   1281 LAS---SFV NLMQFNAMGAP-ADFKFFD--VTI--PRK--R-YTSLTEIW QSTIIHQSITGLYETRIRMGK--  1340
WP_034867970   1281 IAQ---SFL QLLQFNAIGAP-ADFKFFG--VTI--PRK--R-YTSLTEIW DATIIYQSVTGLYETRIRMGDLwa  1340
WP_047937432   1271 LAS---SFV NLMQFNAMGAP-ADFKFFD--VTI--PRK--R-YTSLTEIW QSTIIHQSITGLYETRIRMGK--  1333
WP_010720994   1271 IAQ---SFL QLLQFNAIGAP-ADFKFFG--VTI--PRK--R-YTSLTEIW DATIIYQSVTGLYETRIRMGDLwa  1333
WP_010737004   1271 IAQ---SFL QLLQFNAIGAP-ADFKFFG--ETI--PRS--R-YTSVNELL EATINQSITGLYETRRKL----  1333
WP_034700478   1271 IAQ---SFL QLLQFNAIGAP-ADFKFFG--VTI--PRK--R-YTSLTEIW DATIIYQSVTGLYETRIRMGDLwa  1333
WP_007209003   1270 IAK---SFI NLLTFTAMGAP-ADFEFFG--EKI--PKK--R-YVSISEII DAVFIHQSITGLYETRVRLTEV-  1330
WP_023519017   1265 MID---AIL SLLKFTLFGAS-VEFKFFD--IKI--LK--R-YKSLTDIW EATIIYQSVTGLYERRVEVRKLwd  1326
WP_010770040   1275 IAE---SFV NLMKFSAYGAP-MDFKFFG--ETI--PRS--R-YTSVGELL SATINQSITGLYETRRKL----  1332
WP_048604708   1271 IAQ---SFV DLMQLNAMGAP-ADFKFFE--ETI--PRK--R-YTSVNELL EATINQSITGLYETRRKL----  1328
WP_010750235   1274 MAH---SFV NLMQFNALGAP-ADFKFFD--TTI--TRK--R-YTSLTEIW QSTIIYQSVTGLYETRRRMADLwd  1336
AII6583        1345 -AE---NII HLFLTLTNLGAP-AAFKYFD--TTI--DRK--R-YTSTKEVL DATLIHQSITGLYETRIDLSQL-  1404
WP_029073316   1283 -CE---VI QMLVVMHAGPQnGNITFDDf--KL-sNRIg--R-LNCKTISL TTVFIADSPTGMYSKKYKL--  1343
WP_031589969   1284 -CN----II QILATLHCNSSiGKIMYSDf--KI-sTTIg--R-LNGRTISL DISFIAESPTGMYSKKYKL--  1344
KDA45870       1254 LGK---NFV ELLRYTADGAA-SDFKFFG--ENI--PRK--R-YNSAGSLL NGTLIYQSKTGLYETRIDLGKL-  1314
WP_039099354   1307 ILDr--V -LIGLHANAAV-SDLGVLKisTPL-GKM--Q---QPSGIS DTQIIYQSPTGLFERRVALRDL-  1368
AKP02966       1297 INS1-eELI TLLHANSTSAH-LIFNNIE-kKAP--GRK-------THGLT DTDFIYQSVTGLYETRIHIE--  1356
WP_010991369   1275 IAQ---SFV DLMAFNAMGAP-ASFKFFE--BRK--DRK--R-YNNLKELL NSTIIYQSITGLYESRKRL----  1332
WP_033838504   1275 IAQ---SFV DLMAFNAMGAP-ASFKFFE--BRK--DRK--R-YNNLKELL NSTIIYQSITGLYESRKRL----  1332
EHN60060       1278 IAQ---SFV DLMAFNAMGAP-ASFKFFE--BRK--DRK--R-YNNLKELL SATIIYQSITGLYESRKRL----  1335
EFR89594       1044 IAQ---SFV DLMAFNAMGAP-ASFKFFE--TTI--ERK--R-YNNLKELL NSTIIYQSITGLYESRKRL----  1101
WP_038409211   1275 IAK---SFD KLKVFNAFGAP-RDFEFFE--TTI--KRK--R-YYNIKELL NATIIYQSITGLYEARKRL----  1332
EFR95520       894  IAK---SFD KLKVFNAFGAP-KDFNFFG--TTI--KRK--R-YYNIKELL NATIIYQSITGLYEARKRL----  951
WP_003723650   1275 IAQ---SFV DLMAFNAMGAP-ASFKFFE--ATI--DRK--R-YTNLKELL SSTIIYQSITGLYESRKRL----  1332
WP_003727705   1275 IAQ---SFV DLMAFNAMGAP-ASFKFFE--ATI--DRK--R-YTNLKELL SSTIIYQSITGLYESRKRL----  1332
WP_003730785   1275 IAQ---SFV DLMAFNAMGAP-ASFKFFE--ATI--DRK--R-YTNLKELL SSTIIYQSITGLYESRKRL----  1332
WP_003733029   1275 IAE---SFV DLMAFNAPGVH-QDFSFFG--TKI--DRK--R-DRKLNELL NSTIIYQSITGLYESRKRL----  1332
WP_003739838   1275 NLMAFNAMGAP-ASFKFFE--ATI--ERK--R-YTNLKELL SATIIYQSITGLYEARKRL----  1332
WP_014601172   1275 IAQ---SFV DLMAFNAMGAP-ASFKFFE--TTI--DRK--R-YNNLKELL SSTIIYQSITGLYESRKRL----  1332
WP_023548323   1275 IAQ---SFV DLMAFNAMGAP-ASFKFFE--TTI--KRK--R-DRKLKELL SSTIIYQSITGLYEARKRL----  1332
WP_031665337   1275 IAQ---SFV DLMAFNAMGAP-ASFKFFE--ATI--DRK--R-YTNLKELL SSTIIYQSITGLYESRKRL----  1332
WP_031669209   1275 IAE---SFV DLMAFNAPGVH-KDFNFFG--TTI--KRK--R-DRKLKELL SSTIIYQSITGLYESRKRL----  1332
WP_033920898   1275 IAE---SFV SLKKFNAFGVH-QDFSFFG--TKI--ERK--R-DRKLNELL NSTIIYQSITGLYESRKRL----  1332
AKI42028       1278 IAE---SFV SLKKFNAFGVH-QDFSFFG--ATI--DRK--R-YTNLKELL SATIIYQSITGLYESRKRL----  1335
AKI50529       723  -AE---NII DLMVFNAMGAP-ASFKYFE--TNI--ERK--R-YNNLKELL NATIIYQSITGLYESRKRL----  780
EFR83390       1275 IAQ---SFV NLLEFNAMGAP-ASFKFFE--TTI--DRK--R-YTNLKELL NSTIIYQSITGLYEARKRL----  1332
WP_046323366   1322 -AE---NII HLFLTLTNLGAP-AAFKYFD--TTI--ERK--R-YTSTKEVL DATLIHQSITGLYETRIDLSQL-  1381
AKE81011       1273 -AN----VI QMLIIMHKGPQnGNIIYDDf--NV-gKRIg--R-LNGRTFYL NIEFISQSPTGIYTKKYL----  1333
CU082355       1273
```

-continued

```
WP_033162887   1275  -CD-----VI QLLIMHAGPMnGNIMYDDf--KF-tNRIg-R-FTHKNIDL KTTFISTSVTGLFSKKYKL-----  1335
AGZ01981       1339  -AE----NII HLFTLTNLGAP-AAFKYFD--TTI--DRK--R-YTSTKEVL DATLIHQSITGLYETRIDLSQL--  1398
AKA60242       1306  -AE----NII HLFTLTNLGAP-AAFKYFD--TTI--DRK--R-YTSTKEVL DATLIHQSITGLYETRIDLSQL--  1365
AKS40380       1306  -AE----NII HLFTLTNLGAP-AAFKYFD--TTI--DRK--R-YTSTKEVL DATLIHQSITGLYETRIDLSQL--  1365
4UN5_B         1310  -AE----NII HLFTLTNLGAP-AAFKYFD--TTI--DRK--R-YTSTKEVL DATLIHQSITGLYETRIDLSQL--  1369

WP_010922251   1366  GGD   1368
WP_010922251   1370  GEE   1372
WP_039695303   1368  GED   1370
WP_045635197   ---         
5AXW_A         1050  GGD   1052
WP_009880683   1366  GGD   1368
WP_011054416   1366  GGD   1368
WP_011284745   1366  GGD   1368
WP_011285506   1366  GGD   1368
WP_011527619   1366  GGD   1368
WP_012560673   1365  GGD   1367
WP_012566673   1365  GGD   1367
WP_014407541   1365  GGD   1367
WP_020905136   1366  GGD   1368
WP_023080005   1366  GGD   1368
WP_023610282   1366  GGD   1368
WP_030125963   1366  GGD   1368
WP_030126706   1366  GGD   1368
WP_031488318   1366  GGD   1368
WP_032460140   1366  GGD   1368
WP_032461047   1366  GGD   1368
WP_032462016   1366  GGD   1368
WP_032462936   1366  GGD   1368
WP_032464890   1366  GGD   1368
WP_033888930   1191  GGD   1193
WP_038431314   1366  GGD   1368
WP_038432938   1365  GGD   1367
WP_038434062   1366  GGD   1368
BAQ51233       1277  GGD   1279
KGE60162       541   GGD   543
KGE60856       304   GGD   306
WP_002989955   1366  GGD   1368
WP_003030002   1343  GED   1345
WP_003065552   1371  GEE   1373
WP_001040076   1368  GGD   1370
WP_001040078   1376  GGD   1378
WP_001040080   1368  GED   1370
WP_001040081   1368  GED   1370
WP_001040083   1368  GED   1370
WP_001040085   1368  GED   1370
WP_001040087   1368  GED   1370
WP_001040088   1368  GED   1370
WP_001040089   1368  GED   1370
WP_001040090   1368  GED   1370
WP_001040091   1368  GED   1370
WP_001040092   1368  GED   1370
WP_001040094   1368  GED   1370
WP_001040095   1368  GEG   1370
```

-continued

| | | |
|---|---|---|
| WP_001040096 | 1368 GEG | 1370 |
| WP_001040097 | 1368 GED | 1370 |
| WP_001040098 | 1368 GED | 1370 |
| WP_001040099 | 1368 GED | 1370 |
| WP_001040100 | 1368 GED | 1370 |
| WP_001040104 | 1368 GED | 1370 |
| WP_001040105 | 1368 GED | 1370 |
| WP_001040106 | 1368 GED | 1370 |
| WP_001040107 | 1368 GED | 1370 |
| WP_001040108 | 1368 GED | 1370 |
| WP_001040109 | 1368 GED | 1370 |
| WP_001040110 | 1368 GED | 1370 |
| WP_015058523 | 1368 GED | 1370 |
| WP_017643650 | 1368 GED | 1370 |
| WP_017647151 | 1368 GED | 1370 |
| WP_017648376 | 1368 GED | 1370 |
| WP_017649527 | 1368 GED | 1370 |
| WP_017771611 | 1368 GED | 1370 |
| WP_017771984 | 1368 GED | 1370 |
| CFQ25032 | 1368 GED | 1370 |
| CFV16040 | 1368 GED | 1370 |
| KLJ37842 | 1368 GGD | 1370 |
| KLJ72361 | 1382 GED | 1384 |
| KLL20707 | 1368 GED | 1370 |
| KLL42645 | 1368 GED | 1370 |
| WP_047207273 | 1368 GED | 1370 |
| WP_047209694 | 1368 GED | 1370 |
| WP_050198062 | 1368 GED | 1370 |
| WP_050201642 | 1368 GED | 1370 |
| WP_050204027 | 1368 GED | 1370 |
| WP_050881965 | 1368 GED | 1370 |
| WP_050886065 | 1368 GED | 1370 |
| AHN30376 | 1368 GED | 1370 |
| EA078426 | 1368 GED | 1370 |
| CCW42055 | 1384 GED | 1386 |
| WP_003041502 | 1344 GED | 1346 |
| WP_037593752 | 1344 GED | 1346 |
| WP_049516684 | 1343 GED | 1345 |
| GAD46167 | 1375 GEE | 1377 |
| WP_018363470 | 1373 GEE | 1375 |
| WP_003043819 | 1343 GED | 1345 |
| WP_006269658 | 1363 GED | 1365 |
| WP_048800889 | 1369 GGD | 1371 |
| WP_012767106 | 1369 GGD | 1371 |
| WP_014612333 | 1369 GGD | 1371 |
| WP_015017095 | 1369 GGD | 1371 |
| WP_015057649 | 1346 GEN | 1348 |
| WP_048272215 | 1346 GEN | 1348 |
| WP_049519324 | 1346 GEN | 1348 |
| WP_012515931 | 1375 GEE | 1377 |
| WP_021320964 | | |
| WP_037581760 | | |
| WP_004232481 | | |

-continued

| | | |
|---|---|---|
| WP_009854540 | GEE | 1370 |
| WP_012962174 | GEE | 1371 |
| WP_039695303 | GEE | 1372 |
| WP_014334983 | GEE | 1375 |
| WP_003099269 | GGK | 1368 |
| AHY15608 | --- | |
| AHY17476 | --- | |
| ESR09100 | GGK | 198 200 |
| AGM98575 | --- | |
| ALF27331 | GGD | 1345 |
| WP_018372492 | GGD | 1353 |
| WP_045618028 | GEN | 1376 |
| WP_045635197 | GED | 1370 |
| WP_002263549 | GGD | 1345 |
| WP_002263887 | GGD | 1345 |
| WP_002264920 | GGD | 1345 |
| WP_002269043 | GGD | 1345 |
| WP_002269448 | GGD | 1345 |
| WP_002271977 | GGD | 1345 |
| WP_002272766 | GGD | 1345 |
| WP_002273241 | GGD | 1345 |
| WP_002275430 | GGD | 1345 |
| WP_002276448 | GGD | 1345 |
| WP_002277050 | GGD | 1355 |
| WP_002277364 | GGD | 1345 |
| WP_002279025 | GGD | 1345 |
| WP_002279859 | GGD | 1345 |
| WP_002280230 | GGD | 1345 |
| WP_002281696 | GGD | 1345 |
| WP_002282247 | GGD | 1355 |
| WP_002282906 | GGD | 1345 |
| WP_002283846 | GGD | 1345 |
| WP_002287255 | GGD | 1345 |
| WP_002288990 | GGD | 1345 |
| WP_002289641 | GGD | 1345 |
| WP_002290427 | GGD | 1345 |
| WP_002295753 | GGD | 1345 |
| WP_002296423 | GGD | 1345 |
| WP_002304487 | GGD | 1359 |
| WP_002305844 | GGD | 1345 |
| WP_002307203 | GGD | 1345 |
| WP_002310390 | GGD | 1345 |
| WP_002352408 | GGD | 1345 |
| WP_012997688 | GGD | 1345 |
| WP_014677909 | GGD | 1345 |
| WP_019312892 | GGD | 1345 |
| WP_019313659 | GGD | 1345 |
| WP_019314093 | GGD | 1345 |
| WP_019315370 | GGD | 1345 |
| WP_019803776 | GGD | 1345 |
| WP_019805234 | GGD | 1345 |
| WP_024783594 | GGD | 1345 |
| WP_024784288 | GGD | 1355 |

-continued

| | | |
|---|---|---|
| WP_024784666 | 1343 GGD | 1345 |
| WP_024784894 | 1343 GGD | 1345 |
| WP_024786433 | 1353 GGD | 1355 |
| WP_049473442 | 1343 GGD | 1345 |
| WP_049474547 | 1343 GGD | 1345 |
| EMC03581 | 1336 GGD | 1338 |
| WP_000428612 | 1371 GED | 1373 |
| WP_000428613 | 1369 GED | 1371 |
| WP_049523028 | 1364 GEE | 1366 |
| WP_003107102 | 1335 GGD | 1337 |
| WP_054279288 | 1366 GGD | 1368 |
| WP_049531101 | 1374 GED | 1376 |
| WP_049538452 | 1374 GED | 1376 |
| WP_049549711 | 1376 GED | 1378 |
| WP_007896501 | 1372 GED | 1374 |
| EFR44625 | 1324 GGD | 1326 |
| WP_002897477 | 1368 GEE | 1370 |
| WP_002906454 | 1375 GED | 1377 |
| WP_009729476 | 1369 GED | 1371 |
| CQR24647 | 1359 GGE | 1361 |
| WP_000066813 | 1373 GED | 1375 |
| WP_009754323 | 1369 GED | 1371 |
| WP_044674937 | 1362 GGD | 1364 |
| WP_044676715 | 1364 GGD | 1366 |
| WP_044680361 | 1364 GGD | 1366 |
| WP_044681799 | 1362 GGD | 1364 |
| WP_049533112 | 1384 GED | 1386 |
| WP_029090905 | - - - | |
| WP_006506696 | - - - | |
| A1T42264 | 1366 GGD | 1389 |
| WP_034440723 | | |
| AKQ21048 | 1366 GGD | 1384 |
| WP_004636532 | 1330 -ED | 1332 |
| WP_002364836 | 1336 -VD | 1337 |
| WP_016631044 | 1287 GEQ | 1288 |
| EMS75795 | 1077 -VD | 1079 |
| WP_002373311 | 1336 -VD | 1337 |
| WP_002378009 | 1336 -VD | 1337 |
| WP_002407324 | 1336 -VD | 1337 |
| WP_002413717 | 1338 -VD | 1339 |
| WP_010775580 | 1336 -VD | 1337 |
| WP_010818269 | 1336 -VD | 1337 |
| WP_010824395 | 1336 -VD | 1337 |
| WP_016622645 | 1336 -VD | 1337 |
| WP_033624816 | 1336 -VD | 1337 |
| WP_033789179 | 1336 -VD | 1337 |
| WP_002310644 | - - - | |
| WP_002312694 | - - - | |
| WP_002314015 | - - - | |
| WP_002320716 | - - - | |
| WP_002330729 | - - - | |
| WP_002335161 | - - - | |

-continued

| | | |
|---|---|---|
| WP_002345439 | | |
| WP_034867970 | | |
| WP_047937432 | | |
| WP_010720994 | 1334 | --- |
| WP_010737004 | 1334 | GEQ |
| WP_034700478 | 1334 | GEQ |
| WP_007209003 | 1334 | GEQ |
| WP_023519017 | 1327 | GER |
| WP_010770040 | 1333 | -VD |
| WP_048604708 | 1329 | -GD |
| WP_010750235 | 1337 | GVQ |
| AII16583 | 1405 | GGD |
| WP_029073316 | | |
| WP_031589969 | | |
| KDA45870 | | |
| WP_039099354 | | |
| AKP02966 | | |
| WP_010991369 | 1333 | -DD |
| WP_033838504 | 1333 | -DD |
| EHN60060 | 1336 | -DD |
| EFR89594 | 1102 | -DD |
| WP_038409211 | 1333 | -ED |
| EFR95520 | 952 | -ED |
| WP_003723650 | 1333 | -DD |
| WP_003727705 | 1333 | -DD |
| WP_003730785 | 1333 | -DD |
| WP_003733029 | 1333 | -DN |
| WP_003739838 | 1333 | -DG |
| WP_014601172 | 1333 | -DD |
| WP_023548323 | 1333 | -DS |
| WP_031665337 | 1333 | -DD |
| WP_031669209 | 1333 | -DN |
| WP_033920898 | 1333 | -DS |
| AKI42028 | 1336 | -DD |
| AKI50529 | 1336 | -DS |
| EFR83390 | 781 | -DD |
| WP_046323366 | 1333 | -DD |
| AKE81011 | 1382 | GGD |
| CUO82355 | | |
| WP_033162887 | | |
| AGZ01981 | 1399 | GGD |
| AKA60242 | 1366 | GGD |
| AKS40380 | 1366 | GGD |
| 4UN5_B | 1370 | GGD |

| 1336 |
| 1336 |
| 1336 |
| 1336 |
| 1330 |
| 1334 |
| 1330 |
| 1339 |
| 1424 |
| 1334 |
| 1334 |
| 1337 |
| 1103 |
| 1334 |
| 953 |
| 1334 |
| 1334 |
| 1334 |
| 1334 |
| 1334 |
| 1334 |
| 1334 |
| 1334 |
| 1334 |
| 1334 |
| 1337 |
| 1337 |
| 782 |
| 1334 |
| 1400 |
| 1417 |
| 1368 |
| 1376 |
| 1372 |

TABLE 2

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_000071.2 (CBS):c.833T>C (p.Ile278Thr) | 875 | CBS | 2540 | ['CTGAAGCCGCGCCCTCTGCAGATCAYTGGGGTGGGATCCCGAAGGGTCCATC'] | 2703-2704 | ['ATCAYTGGGGTGGATCCCGAAGG', 'TCAYTGGGGTGGATCCCGAAGGG'] | 2907-2908 | ['ATCAYTGGGGTGGATCCCGAAGG', 'TCAYTGGGGTGGATCCCGAAGGG'] |
| NM_001385.2 (DPYS):c.1078T>C (p.Trp360Arg) | 1807 | DPYS | 2541 | ['TGTTGAAGATCGGATGTCCGTAATAYGGGAAAAAGGCGTGGTGGGTTTCAC'] | 2705-2707 | ['CGTAATAYGGGAAAAAGGCGTGG', 'AATAYGGGAAAAAGGCGTGGTGG', 'ATAYGGGAAAAAGGCGTGGTGGG'] | 2909-2911 | ['CGTAATAYGGGAAAAAGGCGTGG', 'AATAYGGGAAAAAGGCGTGGTGG', 'ATAYGGGAAAAAGGCGTGGTGGG'] |
| NM_000027.3 (AGA):c.916T>C (p.Cys306Arg) | 175 | AGA | 2542 | ['TCCAGAATTCTTTGGGGCTGTTATAYGTGCCAATGTGACTGGAAGTTACGG'] | 2708 | ['GTTATAYGTGCCAATGTGACTGG'] | 2912 | ['GTTATAYGTGCCAATGTGACTGG'] |
| NM_000035.3 (ALDOB):c.442T>C (p.Trp148Arg) | 229 | ALDOB | 2543 | ['GAAAGATGGTGTTGACTTTGGGAAGYGGCGTGCTGTGCTGAGGATTGCCGA'] | 2709 | ['GGAAGYGGCGTGCTGTGCTGAGG'] | 2913 | ['GGAAGYGGCGTGCTGTGCTGAGG'] |
| NM_173560.3 (RFX6):c.380+2T>C | 222546 | RFX6 | 2544 | ['GCAGACACAGCTCACGCTGCAGTGGYGAGACTCGCCCGCAGGGTACACTGA'] | 2710-2711 | ['CAGTGGYGAGACTCGCCCGCAGG', 'AGTGGYGAGACTCGCCCGCAGGG'] | 2914-2915 | ['CAGTGGYGAGACTCGCCCGCAGG', 'AGTGGYGAGACTCGCCCGCAGGG'] |
| NM_153704.5 (TMEM67):c.1843T>C (p.Cys615Arg) | 91147 | TMEM67 | 2545 | ['AGAACGTTTTGTCACTTATGTTGGAHGTGCCTTTGCTCTGAAGGTAAGTTT'] | 2712 | ['TGGAHGTGCCTTTGCTCTGAAGG'] | 2916 | ['TGGAHGTGCCTTTGCTCTGAAGG'] |
| NM_000124.3 (ERCC6):c.2960T>C (p.Leu987Pro) | 2074 | ERCC6 | 2546 | ['AAGCAGTTTTTGACAAATAGAGTGCYAAAAGACCCAAAACAAAGGCGGTTT'] | 2713 | ['TGCYAAAAGACCCAAAACAAAGG'] | 2917 | ['TGCYAAAAGACCCAAAACAAAGG'] |
| NM_020435.3 (GJC2):c.857T>C (p.Met286Thr) | 57165 | GJC2 | 2547 | ['TGCCTGCTGCTCAACCTCTGTGAGAYGGCCCACCTGGGCTTGGGCAGCGCG'] | 2714 | ['TGAGAYGGCCCACCTGGGCTTGG'] | 2918-2919 | ['TGAGAYGGCCCACCTGGGCTTGG', 'GAGAYGGCCCACCTGGGCTTGGG'] |
| NM_000920.3 (PC):c.434T>C (p.Val145Ala) | 5091 | PC | 2548 | ['CGGTTTATTGGGCCAAGCCCAGAAGBGGTCCGCAAGATGGGAGACAAGGTG'] | 2715 | ['CCAGAAGBGGTCCGCAAGATGGG'] | 2920 | ['CCAGAAGBGGTCCGCAAGATGGG'] |
| NM_000026.2 (ADSL):c.674T>C (p.Met225Thr) | 158 | ADSL | 2549 | ['TCCAAGGTAGAGCAGCTTGACAAGAYGGTGACAGAAAAGGCAGGATTTAAG'] | 2716 | ['AAGAYGGTGACAGAAAAGGCAGG'] | 2921 | ['AAGAYGGTGACAGAAAAGGCAGG'] |
| NM_000391.3 (TPP1):c.1093T>C (p.Cys365Arg) | 1200 | TPP1 | 2550 | ['TCTCTCAGGTGACAGTGGGGCCGGGYGTTGGTCTGTCTCTGGAAGACACCA'] | 2717 | ['GCCGGGYGTTGGTCTGTCTCTGG'] | 2922 | ['GCCGGGYGTTGGTCTGTCTCTGG'] |
| NM_004183.3 (BEST1):c.704T>C (p.Val235Ala) | 7439 | BEST1 | 2551 | ['TACGACTGGATTAGTATCCCACTGGYGTATACACAGGTGAGGACTAGGCTG'] | 2718 | ['CACTGGYGTATACACAGGTGAGG'] | 2923 | ['CACTGGYGTATACACAGGTGAGG'] |
| NM_000019.3 (ACAT1):c.935T>C (p.Ile312Thr) | 38 | ACAT1 | 2552 | ['CTCAATGTTACACCACTGGCAAGAAYAGTAGGTAAGGCCAGGCGAGGTGGC'] | 2719 | ['CAAGAAYAGTAGGTAAGGCCAGG'] | 2924 | ['CAAGAAYAGTAGGTAAGGCCAGG'] |

TABLE 2-continued

T to C changes with NGG PAM. Table 2 shows a list of T to C mutations that may
be corrected using any of the base editors provided herein. GRNAs and gRNAall indicate the
protospacer and PAM sequence, where the PAM sequence is the last 3 nucleotides of each of
the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_000543.4 (SMPD1):c.911T>C (p.Leu304Pro) | 6609 | SMPD1 | 2553 | ['CGGGCCCTGACCACCGTCACAGCACYTGTGAGGAAGTTCCTGGGGCCAGTG'] | 2720 | ['CACYTGTGAGGAAGTTCCTGGGG'] | 2925-2927 | ['AGCACYTGTGAGGAAGTTCCTGG', 'GCACYTGTGAGGAAGTTCCTGGG', 'CACYTGTGAGGAAGTTCCTGGGG'] |
| NM_000527.4 (LDLR):c.694+2T>C | 3949 | LDLR | 2554 | ['ACAAATCTGACGAGGAAAACTGCGGYATGGGCGGGGCCAGGGTGGGGGCGG'] | 2721 | ['CGGYATGGGCGGGGCCAGGGTGG'] | 2928-2930 | ['ACTGCGGYATGGGCGGGGCCAGG', 'CTGCGGYATGGGCGGGGCCAGGG', 'CGGYATGGGCGGGGCCAGGGTGG'] |
| NM_012464.4 (TLL1):c.713T>C (p.Val238Ala) | 7092 | TLL1 | 2555 | ['AAGAACTGTGATAAATTTGGGATTGYTGTTCATGAATTGGGTCATGTGATA'] | 2722 | ['GGGATTGYTGTTCATGAATTGGG'] | 2931 | ['GGGATTGYTGTTCATGAATTGGG'] |
| NM_000112.3 (SLC26A2):c.-26+2T>C | 1836 | SLC26A2 | 2556 | ['CCTGCAGCGGCCCGGACCCGAGAGGYGAGAAGAGGGAAGCGGACCAGGGAA'] | 2723 | ['GAGAGGYGAGAAGAGGGAAGCGG'] | 2932 | ['GAGAGGYGAGAAGAGGGAAGCGG'] |
| NM_001005741.2 (GBA):c.751T>C (p.Tyr251His) | 2629 | GBA | 2557 | ['CATCTACCACCAGACCTGGGCCAGAYACTTTGTGAAGTAAGGGATCAGCAA'] | 2724 | ['GCCAGAYACTTTGTGAAGTAAGG'] | 2933-2934 | ['GCCAGAYACTTTGTGAAGTAAGG', 'CCAGAYACTTTGTGAAGTAAGGG'] |
| NM_020365.4 (EIF2B3):c.1037T>C (p.Ile346Thr) | 8891 | EIF2B3 | 2558 | ['CCACCAGTCCATTCGTCAGCCCAGAYTGTCAGCAAACACCTGGTAAGTGCT'] | 2725 | ['CCAGAYTGTCAGCAAACACCTGG'] | 2935 | ['CCAGAYTGTCAGCAAACACCTGG'] |
| NM_022041.3 (GAN):c.1268T>C (p.Ile423Thr) | 8139 | GAN | 2559 | ['TGCTATGCAGCTATGAAAAAGAAAAYCTACGCCATGGGTGGAGGCTCCTAC'] | 2726 | ['AAGAAAAYCTACGCCATGGGTGG'] | 2936-2937 | ['AAGAAAAYCTACGCCATGGGTGG', 'AAAAYCTACGCCATGGGTGGAGG'] |
| NM_054027.4 (ANKH):c.143T>C (p.Met48Thr) | 56172 | ANKH | 2560 | ['GCTGTCAAGGAGGATGCAGTCGAGAYGCTGGCCAGCTACGGGCTGGCGTAC'] | 2727-2728 | ['GTCGAGAYGCTGGCCAGCTACGG', 'TCGAGAYGCTGGCCAGCTACGGG'] | 2938-2939 | ['GTCGAGAYGCTGGCCAGCTACGG', 'TCGAGAYGCTGGCCAGCTACGGG'] |
| NM_006329.3 (FBLN5):c.506T>C (p.Ile169Thr) | 10516 | FBLN5 | 2561 | ['TTGCTTGCATTTCTGTTTCCAGACAYTGATGAATGTCGCTATGGTTACTGC'] | 2729 | ['GACAYTGATGAATGTCGCTATGG'] | 2940 | ['GACAYTGATGAATGTCGCTATGG'] |
| NM_004086.2 (COCH):c.1535T>C (p.Met512Thr) | −1 | — | 2562 | ['GCACCTCTGGATGACCTGAAAGATAYGGCTTCTAAACCGAAGGAGTCTCAT'] | 2730 | ['AGATAYGGCTTCTAAACCGAAGG'] | 2941 | ['AGATAYGGCTTCTAAACCGAAGG'] |
| NM_002942.4 (ROBO2):c.2834T>C (p.Ile945Thr) | 6092 | ROBO2 | 2563 | ['AATAGCAACAGTGGCCCAAATGAGAYTGGAAATTTTGGCCGTGGAGGTAAG'] | 2731 | ['GAGAYTGGAAATTTTGGCCGTGG'] | 2942 | ['GAGAYTGGAAATTTTGGCCGTGG'] |
| NM_001300.5 (KLF6):c.190T>C (p.Trp64Arg) | 1316 | KLF6 | 2564 | ['CAAATTTGACAGCCAGGAAGATCTGYGGACCAAAATCATTCTGGCTCGGGA'] | 2732 | ['TCTGYGGACCAAAATCATTCTGG'] | 2943 | ['TCTGYGGACCAAAATCATTCTGG'] |
| NM_030653.3 (DDX11):c.2271+2T>C | 1663 | DDX11 | 2565 | ['CTGGCATATTCCAGGTGCATCCAGGYGCGGGCGTCATGCTGGGCTTGGGTC'] | 2733 | ['TCCAGGYGCGGGCGTCATGCTGG'] | 2944-2945 | ['TCCAGGYGCGGGCGTCATGCTGG', 'CCAGGYGCGGGCGTCATGCTGGG'] |

TABLE 2-continued

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_001451.2 (FOXF1):c.1138T>C (p.Ter380Arg) | 2294 | FOXF1 | 2566 | ['CCAAGACATC AAGCCTTGCGT GATGYGAGGC TGCCGCCGCAG GCCCTCCTG'] | 2734 | ['TGATGYGAGGCT GCCGCCGCAGG'] | 2946 | ['TGATGYGAGGCT GCCGCCGCAGG'] |
| NM_000435.2 (NOTCH3):c.1363T>C (p.Cys455Arg) | 4854 | NOTCH3 | 2567 | ['CCTCGACCGC ATAGGCCAGTT CACCYGTATCT GTATGGCAGGT GGGTGGTG'] | 2735 | ['ACCYGTATCTGTA TGGCAGGTGG'] | 294-72948 | ['TTCACCYGTATC TGTATGGCAGG', 'ACCYGTATCTGTA TGGCAGGTGG'] |
| NM_002427.3 (MMP13):c.272T>C (p.Met91Thr) | 4322 | MMP13 | 2568 | ['CTTGACGATA ACACCTTAGAT GTCAYGAAAAA AGCCAAGATG CGGGGTTCCT'] | 2736-2737 | ['GTCAYGAAAAAG CCAAGATGCGG', 'TCAYGAAAAAGCC AAGATGCGGG'] | 2949-2950 | ['GTCAYGAAAAA GCCAAGATGCGG', 'TCAYGAAAAAGC CAAGATGCGGG'] |
| NM_000211.4 (ITGB2):c.446T>C (p.Leu149Pro) | 3689 | ITGB2 | 2569 | ['GATGACCTCA GGAATGTCAA GAAGCYAGGT GGCGACCTGCT CCGGGCCCTC'] | 2738 | ['AGCYAGGTGGCG ACCTGCTCCGG'] | 2951 | ['AGCYAGGTGGCG ACCTGCTCCGG'] |
| NM_005502.3 (ABCA1):c.4429T>C (p.Cys1477Arg) | 19 | ABCA1 | 2570 | ['CAAAATCAAG AAGATGCTGCC TGTGYGTCCCC CAGGGGCAGG GGGGCTGCC'] | 2739-2740 | ['CCTGTGYGTCCCC CAGGGGCAGG', 'CTGTGYGTCCCCC AGGGGCAGGG'] | 2952-2955 | ['CCTGTGYGTCCC CCAGGGGCAGG', 'CTGTGYGTCCCCC AGGGGCAGGG', 'TGTGYGTCCCCCA GGGGCAGGGG', 'GTGYGTCCCCCA GGGGCAGGGGG'] |
| m.12297T>C | 4568 | MT-TL2 | 2571 | ['AAAGGATAAC AGCTATCCATT GGTCYTAGGCC CCAAAAATTTT GGTGCAAC'] | 2741 | ['GTCYTAGGCCCC AAAAATTTTGG'] | 2956 | ['GTCYTAGGCCCC AAAAATTTTGG'] |
| m.4290T>C | 4565 | MT-TI | 2572 | ['AAATATGTCT GATAAAAGAG TTACTYTGATA GAGTAAATAA TAGGAGCTTA'] | 2742 | ['ACTYTGATAGAG TAAATAATAGG'] | 2957 | ['ACTYTGATAGAG TAAATAATAGG'] |
| m.4291T>C | 4565 | MT-TI | 2573 | ['AATATGTCTG ATAAAAGAGT TACTTYGATAG AGTAAATAAT AGGAGCTTAA'] | 2743 | ['ACTTYGATAGAG TAAATAATAGG'] | 2958 | ['ACTTYGATAGAG TAAATAATAGG'] |
| m.3394T>C | 4535 | MT-ND1 | 2574 | ['GCTTACCGAA CGAAAAATTCT AGGCYATATA CAACTACGCA AAGGCCCCAA'] | 2744 | ['GGCYATATACAA CTACGCAAAGG'] | 2959 | ['GGCYATATACAA CTACGCAAAGG'] |
| NM_002764.3 (PRPS1):c.344T>C (p.Met115Thr) | 5631 | PRPS1 | 2575 | ['ATCTCAGCCA AGCTTGTTGCA AATAYGCTATC TGTAGCAGGTG CAGATCAT'] | 2745 | ['GCAAATAYGCTA TCTGTAGCAGG'] | 2960 | ['GCAAATAYGCTA TCTGTAGCAGG'] |
| NM_000132.3 (F8):c.5372T>C (p.Met1791Thr) | 2157 | F8 | 2576 | ['AGAGCAGAA GTTGAAGATA ATATCAYGGTG AGTTAAGGAC AGTGGAATTAC'] | 2746 | ['TCAYGGTGAGTT AAGGACAGTGG'] | 2961 | ['TCAYGGTGAGTT AAGGACAGTGG'] |
| NM_000132.3 (F8):c.1754T>C (p.Ile585Thr) | 2157 | F8 | 2577 | ['CCTTTCAATA TATGTAATTAA CAGAYAATGT CAGACAAGAG GAATGTCATC'] | 2747 | ['AACAGAYAATGT CAGACAAGAGG'] | 2962 | ['AACAGAYAATGT CAGACAAGAGG'] |
| NM_000133.3 (F9):c.1328T>C (p.Ile443Thr) | 2158 | F9 | 2578 | ['TGTGCAATGA AAGGCAAATA TGGAAYATAT ACCAAGGTATC CCGGTATGTC'] | 2748 | ['GAAYATATACCA AGGTATCCCGG'] | 2963 | ['GAAYATATACCA AGGTATCCCGG'] |

TABLE 2-continued

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_000169.2 (GLA):c.806T>C (p.Val269Ala) | −1 | — | 2579 | ['TTATTTCATTC TTTTTCTCAGT TAGYGATTGGC AACTTTGGCCT CAGCTGG'] | 2749 | ['CAGTTAGYGATT GGCAACTTTGG'] | 2964 | ['CAGTTAGYGATT GGCAACTTTGG'] |
| NM_000116.4 (TAZ):c.352T>C (p.Cys118Arg) | 6901 | TAZ | 2580 | ['CTCCCACTTC TTCAGCTTGGG CAAGYGTGTG CCTGTGTGCCG AGGTGAGCT'] | 2750 | ['AAGYGTGTGCCT GTGTGCCGAGG'] | 2965 | ['AAGYGTGTGCCT GTGTGCCGAGG'] |
| NM_000061.2 (BTK):c.2T>C (p.Met1Thr) | 695 | BTK | 2581 | ['GGTGAACTCC AGAAAGAAGA AGCTAYGGCC GCAGTGATTCT GGAGAGCATC'] | 2751 | ['AGCTAYGGCCGC AGTGATTCTGG'] | 2966 | ['AGCTAYGGCCGC AGTGATTCTGG'] |
| NM_000061.2 (BTK):c.1223T>C (p.Leu408Pro) | 695 | BTK | 2582 | ['AAGGACCTGA CCTTCTTGAAG GAGCYGGGGA CTGGACAATTT GGGGTAGTG'] | 2752 | ['AGCYGGGGACTG GACAATTTGGG'] | 2967-2968 | ['GAGCYGGGGACT GGACAATTTGG', 'AGCYGGGGACTG GACAATTTGGG'] |
| NM_000061.2 (BTK):c.1741T>C (p.Trp581Arg) | 695 | BTK | 2583 | ['CAAGTTCAGC AGCAAATCTG ACATTYGGGCT TTTGGTAAGTG GATAAGATT'] | 2753 | ['ACATTYGGGCTTT TGGTAAGTGG'] | 2969 | ['ACATTYGGGCTT TTGGTAAGTGG'] |
| NM_014009.3 (FOXP3):c.970T>C (p.Phe324Leu) | 50943 | FOXP3 | 2584 | ['GATTCATCCC CACCCTCTGAC AGAGYTCCTCC ACAACATGGA CTACTTCAA'] | 2754 | ['GACAGAGYTCCT CCACAACATGG'] | 2970 | ['GACAGAGYTCCT CCACAACATGG'] |
| NM_003688.3 (CASK):c.2740T>C (p.Trp914Arg) | 8573 | CASK | 2585 | ['TGAGCTCGTG TGCACAGCCCC ACAGYGGGTC CTGTCTCCTG GGTCTATTA'] | 2755-2756 | ['CACAGYGGGTCC CTGTCTCCTGG', 'ACAGYGGGTCCCT GTCTCCTGGG'] | 2971-2972 | ['CACAGYGGGTCC CTGTCTCCTGG', 'ACAGYGGGTCCC TGTCTCCTGGG'] |
| NM_004992.3 (MECP2):c.464T>C (p.Phe155Ser) | 4204 | MECP2 | 2586 | ['GACACATCCC TGGACCCTAAT GATTBTGACTT CACGGTAACTG GGAGAGGG'] | 2757 | ['GATTBTGACTTCA CGGTAACTGG'] | 2973-2974 | ['GATTBTGACTTC ACGGTAACTGG', 'ATTBTGACTTCAC GGTAACTGGG'] |
| NM_000431.3 (MVK):c.803T>C (p.Ile268Thr) | 4598 | MVK | 2587 | ['ATCGTGGCCC CCCTCCTGACC TCAAYAGATG CCATCTCCCTG GAGTGTGAG'] | 2758 | ['CTCAAYAGATGC CATCTCCCTGG'] | 2975 | ['CTCAAYAGATGC CATCTCCCTGG'] |
| NM_021961.5 (TEAD1):c.1261T>C (p.Tyr?His) | 7003 | TEAD1 | 2588 | ['TGAACACGGA GCACAACATC ATATTYACAGG CTTGTAAAGGA CTGAACATG'] | 2759 | ['TCATATTYACAG GCTTGTAAAGG'] | 2976 | ['TCATATTYACAG GCTTGTAAAGG'] |
| NM_005633.3 (SOS1):c.1294T>C (p.Trp432Arg) | 6654 | SOS1 | 2589 | ['CGAGATTCAG AAGAATATTG ATGGTYGGGA GGGAAAAGAC ATTGGACAGTG'] | 2760 | ['GGTYGGGAGGGA AAAGACATTGG'] | 2977 | ['GGTYGGGAGGG AAAAGACATTGG'] |
| NM_006920.4 (SCN1A):c.3577T>C (p.Trp1193Arg) | −1 | — | 2590 | ['TGTGGAAGAA GGCAGAGGAA AACAAYGGTG GAACCTGAGA AGGACGTGTTT'] | 2761 | ['AACAAYGGTGGA ACCTGAGAAGG'] | 2978 | ['AACAAYGGTGG AACCTGAGAAGG'] |
| NM_000141.4 (FGFR2):c.1018T>C (p.Tyr340His) | 2263 | FGFR2 | 2591 | ['TGTAACTTTT GAGGACGCTG GGGAAYATAC GTGCTTGGCGG GTAATTCTAT'] | 2762-2763 | ['TGGGGAAYATAC GTGCTTGGCGG', 'GGGGAAYATACGT GCTTGGCGGG'] | 2979-2980 | ['TGGGGAAYATAC GTGCTTGGCGG', 'GGGGAAYATACG TGCTTGGCGGG'] |
| NM_000174.4 (GP9):c.70T>C (p.Cys24Arg) | 2815 | GP9 | 2592 | ['GGCCACCAAG GACTGCCCCAG CCCAYGTACCT GCCGCGCCCTG GAAACCAT'] | 2764 | ['CCCAYGTACCTG CCGCGCCCTGG'] | 2981 | ['CCCAYGTACCTG CCGCGCCCTGG'] |

TABLE 2-continued

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_000175.3 (GPI):c.1574T>C (p.Ile525Thr) | 2821 | GPI | 2593 | ['CTGGGAAAGC AGCTGGCTAA GAAAABAGAG CCTGAGCTTGA TGGCAGTGCT'] | 2765 | ['AAAABAGAGCCT GAGCTTGATGG'] | 2982 | ['AAAABAGAGCCT GAGCTTGATGG'] |
| NM_000315.2 (PTH):c.52T>C (p.Cys18Arg) | 5741 | PTH | 2594 | ['AGTTATGATT GTCATGTTGGC AATTYGTTTTC TTACAAAATCG GATGGGAA'] | 2766 | ['AATTYGTTTTCTT ACAAAATCGG'] | 2983 | ['AATTYGTTTTCTT ACAAAATCGG'] |
| NM_000222.2 (KIT):c.1676T>C (p.Val559Ala) | 3815 | KIT | 2595 | ['CCCATGTATG AAGTACAGTG GAAGGNTGTT GAGGAGATAA ATGGAAACAAT'] | 2767 | ['AAGGNTGTTGAG GAGATAAATGG'] | 2984 | ['AAGGNTGTTGAG GAGATAAATGG'] |
| NM_016835.4 (MAPT):c.1839T>C (p.Asn613=) | 4137 | MAPT | 2596 | ['AGTCCAAGTG TGGCTCAAAG GATAAYATCA AACACGTCCCG GGAGGCGGCA'] | 2768-2769 | ['GGATAAYATCAA ACACGTCCCGG', 'GATAAYATCAAAC ACGTCCCGGG'] | 2985-2986 | ['GGATAAYATCAA ACACGTCCCGG', 'GATAAYATCAAA CACGTCCCGGG'] |
| NM_170707.3 (LMNA):c.1139T>C (p.Leu380Ser) | 4000 | LMNA | 2597 | ['GAGATCCACG CCTACCGCAAG CTCTYGGAGG GCGAGGAGGA GAGGTGGGCT'] | 2770 | ['TCTYGGAGGGCG AGGAGGAGAGG'] | 2987 | ['TCTYGGAGGGCG AGGAGGAGAGG'] |
| NM_000424.3 (KRT5):c.20T>C (p.Val7Ala) | 3852 | KRT5 | 2598 | ['GCCACCATGT CTCGCCAGTCA AGTGYGTCCTT CCGGAGCGGG GGCAGTCGT'] | 2771-2773 | ['TCAAGTGYGTCCT TCCGGAGCGG', 'CAAGTGYGTCCTT CCGGAGCGGG', 'AAGTGYGTCCTTC CGGAGCGGGG'] | 2988-2991 | ['TCAAGTGYGTCC TTCCGGAGCGG', 'CAAGTGYGTCCTT CCGGAGCGGG', 'AAGTGYGTCCTTC CGGAGCGGGG', 'AGTGYGTCCTTCC GGAGCGGGG'] |
| NM_000184.2 (HBG2):c.125T>C (p.Phe42Ser) | 3048 | HBG2 | 2599 | ['GTTGTCTACC CATGGACCCA GAGGTYCTTTG ACAGCTTTGGC AACCTGTCC'] | 2774 | ['CAGAGGTYCTTT GACAGCTTTGG'] | 2992 | ['CAGAGGTYCTTT GACAGCTTTGG'] |
| NM_000515.4 (GH1):c.291+6T>C | 2688 | GH1 | 2600 | ['AGGAAACAC AACAGAAATC CGTGAGYGGA TGCCTTCTCCC CAGGCGGGGAT'] | 2775 | ['TGAGYGGATGCC TTCTCCCCAGG'] | 2993 | ['TGAGYGGATGCC TTCTCCCCAGG'] |
| NM_002087.3 GRN):c.2T>C (p.Met1Thr) | 2896 | GRN | 2601 | ['TCCTTGGTAC TTTGCAGGCAG ACCAYGTGGA CCCTGGTGAGC TGGGTGGCC'] | 2776 | ['CCAYGTGGACCC TGGTGAGCTGG'] | 2994 | ['CCAYGTGGACCC TGGTGAGCTGG'] |
| NM_001083112.2 (GPD2):c.1904T>C (p.Phe635Ser) | 2820 | GPD2 | 2602 | ['AGGTATAAGA AGAGATTTCAT AAGTYTGATGC AGACCAGAAA GGCTTTATT'] | 2777 | ['AAGTYTGATGCA GACCAGAAAGG'] | 2995 | ['AAGTYTGATGCA GACCAGAAAGG'] |
| NM_00101807 7.1(NR3C1):c.1712T>C (p.Val571Ala) | 2908 | NR3C1 | 2603 | ['CTCAACATGT TAGGAGGGCG GCAAGYGATT GCAGCAGTGA AATGGGCAAAG'] | 2778 | ['AAGYGATTGCAG CAGTGAAATGG'] | 2996 | ['AAGYGATTGCAG CAGTGAAATGG'] |
| NM_006306.3 (SMC1A):c.2351T>C (p.Ile784Thr) | 8243 | SMC1A | 2621 | ['GTGTTTGAAG AGTTTTGTCGG GAGAYTGGTG TGCGCAACATC CGGGAGTTT'] | 2798 | ['AGAYTGGTGTGC GCAACATCCGG'] | 3017 | ['AGAYTGGTGTGC GCAACATCCGG'] |
| NM_002242.4 (KCN.113):c.722T>C (p.Leu241Pro) | −1 | — | 2622 | ['TGGTGTAATG GAGTGATAGT ACGTTDGTGGA AAGATGAAGA ATGGACATTC'] | 2799 | ['GTTDGTGGAAAG ATGAAGAATGG'] | 3018 | ['GTTDGTGGAAAG ATGAAGAATGG'] |

TABLE 2-continued

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_000199.3 (SGSH):c.892T>C (p.Ser298Pro) | 6448 | SGSH | 2623 | ['CCCCAGCGTT TTGGGTGCTCC GGGGRTGACA CCAGTAAGGG TTCAGCAGTG'] | 2800 | ['TCCGGGGRTGAC ACCAGTAAGGG'] | 3019 | ['TCCGGGGRTGAC ACCAGTAAGGG'] |
| NM_020191.2 (MRPS22):c.644T>C (p.Leu215Pro) | 56945 | MRPS22 | 2624 | ['CCAATAATTT TCAAGGAAGA AAATCYTAGG GTAAGGTGACT TAGGTTTTAT'] | 2801 | ['ATCYTAGGGTAA GGTGACTTAGG'] | 3020 | ['ATCYTAGGGTAA GGTGACTTAGG'] |
| NM_017882.2 (CLN6):c.200T>C (p.Leu67Pro) | 54982 | CLN6 | 2625 | ['CCCATTCTTC CATTTGCTCCG CAGCYGGTATT CCCTCTCGAGT GGTTTCCA'] | 2802 | ['AGCYGGTATTCC CTCTCGAGTGG'] | 3021 | ['AGCYGGTATTCC CTCTCGAGTGG'] |
| NM_014874.3 (MFN2):c.1392+2T>C | 9927 | MFN2 | 2626 | ['GTAGTCCTCA AGGTTTATAAG AATGWGAGTC ATGGAGCAAC AGGTCCTCTT'] | 2803 | ['AATGWGAGTCAT GGAGCAACAGG'] | 3022 | ['AATGWGAGTCA TGGAGCAACAGG'] |
| NM_024599.5 (RHBDF2):c.557T>C (p.11e186Thr) | 79651 | RHBDF2 | 2627 | ['GCTTACCGCC CCCCTCCCTTC CAGAYTGTGG ATCCGCTGGCC CGGGGCCGG'] | 2804 | ['AGAYTGTGGATC CGCTGGCCCGG'] | 3023 | ['AGAYTGTGGATC CGCTGGCCCGG'] |
| NM_020894.2 (UVSSA):c.94T>C (p.Cys32Arg) | 57654 | UVSSA | 2628 | ['GAAAATGAA GGAACTGAAG AAAATTYGCA AGTATGTCTTA GGGTTCAGTAA'] | 2805 | ['AAAATTYGCAAG TATGTCTTAGG'] | 3024-3025 | ['AAAATTYGCAAG TATGTCTTAGG', 'AAAATTYGCAAGT ATGTCTTAGGG'] |
| NM_001161581.1 (POC1A):c.398T>C (p.Leu133Pro) | 25886 | POC1A | 2629 | ['GCCAGTGATG ACAAGACTGTT AAGCYGTGGG ACAAGAGCAG CCGGGAATGT'] | 2806 | ['AGCYGTGGGACA AGAGCAGCCGG'] | 3026 | ['AGCYGTGGGACA AGAGCAGCCGG'] |
| NM_005340.6 (HINT1):c.250T>C (p.Cys84Arg) | 3094 | HINT1 | 2630 | ['ACACTTAATG ATTGTTGGCAA GAAAYGTGCT GCTGATCTGGG CCTGAATAA'] | 2807-2808 | ['CAAGAAAYGTGC TGCTGATCTGG', 'AAGAAAYGTGCTG CTGATCTGGG'] | 3027-3028 | ['CAAGAAAYGTGC TGCTGATCTGG', 'AAGAAAYGTGCT GCTGATCTGGG'] |
| NM_000495 (COL4A5):c.438+2T>C | 1287 | COL4A5 | 2631 | ['TTTCCTGGTT ACAGGGTCCTC CAGYAAGTTAT AAAATTTGGG ATTATGAT'] | 2809 | ['TCCAGYAAGTTA TAAAATTTGGG'] | 3029-3030 | ['CTCCAGYAAGTT ATAAAATTTGG', 'TCCAGYAAGTTA TAAAATTTGGG'] |
| NM_000344.3 (SMN1):c.388T>C (p.Tyr130His) | 6606 | SMN1 | 2632 | ['AACCTGTGTT GTGGTTACAC TGGAYATGGA AATAGAGAGG AGCAAAATCT'] | 2810 | ['CACTGGAYATGG AAATAGAGAGG'] | 3031 | ['CACTGGAYATGG AAATAGAGAGG'] |
| NM_005334.2 (HCFC1):c.-970T>C | 3054 | HCFC1 | 2633 | ['TTAGTTGTTA CTTCTTCACAC AAGAYGGCGG CTCCCAGGGA GGAGGCATGA'] | 2811 | ['CAAGAYGGCGGC TCCCAGGGAGG'] | 3032 | ['CAAGAYGGCGG CTCCCAGGGAGG'] |
| NM_000431.3 (MVK):c.1039+2T>C | 4598 | MVK | 2634 | ['GTGGCATCAC ACTCCTCAAGC CAGGYATCCC GGGGTAGGT GGGCCAGGCT'] | 2812 | ['CCAGGYATCCCG GGGTAGGTGG'] | 3033-3034 | ['CCAGGYATCCCG GGGTAGGTGG', 'CAGGYATCCCGG GGTAGGTGGG'] |
| NM_018344.5 (SLC29A3):c.607T>C (p.Ser203Pro) | 55315 | SLC29A3 | 2635 | ['TATGAGGAAC TCCCAGGCACT GATAYCAGGT GAGAGCCAGG GTCCGGGCAG'] | 2813 | ['ACTGATAYCAGG TGAGAGCCAGG'] | 3035-3036 | ['ACTGATAYCAGG TGAGAGCCAGG', 'CTGATAYCAGGT GAGAGCCAGGG'] |
| NM_000108.4 (DLD):c.140T>C (p.Ile47Thr) | 1738 | DLD | 2636 | ['GTAGTTGATG CTGATGTAACA GTTAYAGGTTC TGGTCCTGGAG GATATATGTT'] | 2815 | ['ACAGTTAYAGGT TCTGGTCCTGG', 'GTTAYAGGTTCTG GTCCTGGAGG'] | 3037-3038 | ['ACAGTTAYAGGT TCTGGTCCTGG', 'GTTAYAGGTTCTG GTCCTGGAGG'] |

TABLE 2-continued

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_004333.4 (BRAF):c.1403T>C (p.Phe468Ser) | 673 | BRAF | 2637 | ['GGACAAAGA ATTGGATCTGG ATCATYTGGAA CAGTCTACAAG GGAAAGTGG'] | 2816-2817 | ['ATCATYTGGAAC AGTCTACAAGG', 'TCATYTGGAACAG TCTACAAGGG'] | 3039-3040 | ['ATCATYTGGAAC AGTCTACAAGG', 'TCATYTGGAACA GTCTACAAGGG'] |
| NM_000540.2 (RYR1):c.1205T>C (p.Met402Thr) | 6261 | RYR1 | 2638 | ['CAGGAGGAGT CCCAGGCCGCC CGCAYGATCC ACAGCACCAA TGGCCTATAC'] | 2818 | ['CGCAYGATCCAC AGCACCAATGG'] | 3041 | ['CGCAYGATCCAC AGCACCAATGG'] |
| NM_000256.3 (MYBPC3):c.1351+2T>C | 4607 | MYBPC3 | 2639 | ['GTAGCACGGA GCTCTTTGTGA AAGGYGGGCC TGGGACCTGA GGATGTGGGA'] | 2819 | ['AAAGGYGGGCCT GGGACCTGAGG'] | 3042 | ['AAAGGYGGGCCT GGGACCTGAGG'] |
| NM_000256.3 (MYBPC3):c.821+2T>C | 4607 | MYBPC3 | 2640 | ['CCTCCTATCA GCCTTCCGCCG CACGYGAGTG GCCATCCTCAG GGCCTGGGG'] | 2820 | ['CACGYGAGTGGC CATCCTCAGGG'] | 3043-3044 | ['CCATCCTCAGG', 'CACGYGAGTGGC CATCCTCAGGG'] |
| NM_000257.3 (MYH7):c.2546T>C (p.Met849Thr) | 4625 | MYH7 | 2641 | ['AAGAGTGCAG AAAGAGAGAA GGAGAYGGCC TCCATGAAGG AGGAGTTCACA'] | 2821 | ['GGAGAYGGCCTC CATGAAGGAGG'] | 3045 | ['GGAGAYGGCCTC CATGAAGGAGG'] |
| NM_206933.2 (USH2A):c.1606T>C (p.Cys536Arg) | 7399 | USH2A | 2642 | ['CGACACAACA AGCCAGCCAT ATAGAYGCCTC TGCTCCCAGGA GAGCTTCAC'] | 2822 | ['ATATAGAYGCCT CTGCTCCCAGG'] | 3046 | ['ATATAGAYGCCT CTGCTCCCAGG'] |
| NM_000059.3 (BRCA2):c.316+2T>C | 675 | BRCA2 | 2643 | ['TAGATAAATT CAAATTAGACT TAGGYAAGTA ATGCAATATGG TAGACTGGG'] | 2823 | ['CTTAGGYAAGTA ATGCAATATGG'] | 3047 | ['CTTAGGYAAGTA ATGCAATATGG'] |
| NM_007294.3 (BRCA1):c.5291T>C (p.Leu1764Pro) | 672 | BRCA1 | 2644 | ['CTCTTCTTCC AGATCTTCAGG GGGCYAGAAA TCTGTTGCTAT GGGCCCTTC'] | 2824 | ['GGCYAGAAATCT GTTGCTATGGG'] | 3048-3049 | ['GGGCYAGAAATC TGTTGCTATGG', 'GGCYAGAAATCT GTTGCTATGGG'] |
| NM_001130089.1(KARS):c.517T>C (p.Tyr173His) | 3735 | KARS | 2645 | ['AGCTTCTGGG GGAAAGCTCA TCTTCYATGAT CTTCGAGGAG AGGGGGTGAA'] | 2825 | ['TTCYATGATCTTC GAGGAGAGGG'] | 3050-3051 | ['CTTCYATGATCT TCGAGGAGAGG', 'TTCYATGATCTTC GAGGAGAGGG'] |
| NM_001283009.1(RTEL1):c.3730T>C (p.Cys1244Arg) | -1 | — | 2646 | ['CGGGCCCCTC TCAGCAGGCT TGTGYGCCAG GGCTGTGGGG CAGAGGACGT'] | 2826 | ['CTGTGTGYGCCA GGGCTGTGGGG'] | 3052 | ['CTGTGTGYGCCA GGGCTGTGGGG'] |
| NM_005554.3 (KRT6A):c.1406T>C (p.Leu469Pro) | 3853 | KRT6A | 2647 | ['GAGATCGCCA CCTACCGCAAG CTGCBGGAGG GTGAGGAGTG CAGGTGGGTA'] | 2827 | ['TGCBGGAGGGTG AGGAGTGCAGG'] | 3053 | ['TGCBGGAGGGTG AGGAGTGCAGG'] |
| NM_000218.2 (KCNQ1):c.550T>C (p.Tyr184His) | 3784 | KCNQ1 | 2648 | ['CTGGTCCGCC GGCTGCCGCA GCAAGBACGT GGGCCTCTGGG GGCGGCTGCG'] | 2828 | ['AGCAAGBACGTG GGCCTCTGGGG'] | 3054-3056 | ['CAGCAAGBACGT GGGCCTCTGGG', 'AGCAAGBACGTG GGCCTCTGGGG', 'GCAAGBACGTGG GCCTCTGGGG'] |
| NM_198056.2 (SCN5A):c.5624T>C (p.Met1875Thr) | 6331 | SCN5A | 2649 | ['GAGATGGACG CCCTGAAGATC CAGAHGGAGG AGAAGTTCATG GCAGCCAAC'] | 2829 | ['CCAGAHGGAGGA GAAGTTCATGG'] | 3057 | ['CCAGAHGGAGG AGAAGTTCATGG'] |
| NM_006920.4 (SCN1A):c.269T>C (p.Phe90Ser) | 6323 | SCN1A | 2650 | ['TGTTGTGTTC CTGTCTTACAG ACTTYTATAGT ATTGAATAAA GGGAAGGCC'] | 2830-2831 | ['ACTTYTATAGTAT TGAATAAAGG', 'CTTYTATAGTATT GAATAAAGGG'] | 3058-3059 | ['ACTTYTATAGTA TTGAATAAAGG', 'CTTYTATAGTATT GAATAAAGGG'] |

TABLE 2-continued

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_006920.4 (SCN1A):c.272T>C (p.Ile91Thr) | 6323 | SCN1A | 2651 | ['TGTGTTCCTG TCTTACAGACT TTTAYAGTATT GAATAAAGGG AAGGCCATC'] | 2832-2833 | ['ACTTTTAYAGTAT TGAATAAAGG', 'CTTTTAYAGTATT GAATAAAGGG'] | 3060-3061 | ['ACTTTTAYAGTA TTGAATAAAGG', 'CTTTTAYAGTATT GAATAAAGGG'] |
| NM_006514.3 (SCN10A):c.1661T>C (p.Leu554Pro) | 6336 | SCN10A | 2652 | ['GGAGTCAGGG TTGCTGGGTTG AGGARGAGGG CTTCTAGGGAG GGGGCCTTG'] | 2834-2836 | ['GAGGARGAGGGC TTCTAGGGAGG', 'AGGARGAGGGCTT CTAGGGAGGG', 'GGARGAGGGCTTC TAGGGAGGGG'] | 3062-3064 | ['GAGGARGAGGG CTTCTAGGGAGG', 'AGGARGAGGGCT TCTAGGGAGGG', 'GGARGAGGGCTT CTAGGGAGGGG'] |
| NM_000251.2 (MSH2):c.2005+2T>C | 4436 | MSH2 | 2653 | ['AACAGATGTT CCACATCATTA CTGGYAAAAA ACCTGGTTTTT GGGCTTTGT'] | 2837-2838 | ['CTGGYAAAAAAC CTGGTTTTTGG', 'TGGYAAAAAACCT GGTTTTTGGG'] | 3065-3066 | ['CTGGYAAAAAAC CTGGTTTTTGG', 'TGGYAAAAAACC TGGTTTTTGGG'] |
| NM_000251.2 (MSH2):c.595T>C (p.Cys199Arg) | 4436 | MSH2 | 2654 | ['CCTCATCCAG ATTGGACCAA AGGAAYGTGT TTACCCGGAG GAGAGACTGC'] | 2839 | ['AAGGAAYGTGTT TTACCCGGAGG'] | 3067 | ['AAGGAAYGTGTT TTACCCGGAGG'] |
| NM_001005741.2 (GBA):c.667T>C (p.Trp223Arg) | 2629 | GBA | 2655 | ['TTCACCGCTC CATTGGTCTTG AGCCRAGTGG GTGATGTCCAG GGGCTGGCA'] | 2840 | ['GCCRAGTGGGTG ATGTCCAGGGG'] | 3068-3070 | ['GAGCCRAGTGGG TGATGTCCAGG', 'AGCCRAGTGGGT GATGTCCAGG', 'GCCRAGTGGGTG ATGTCCAGGGG'] |
| NM_003494.3 (DYSF):c.1284+2T>C | 8291 | DYSF | 2656 | ['GAGGTCAGCT TTGCGGGGAA AATGGYAAGG AGCAAGGGAG CAGGAGGGTTC'] | 2841 | ['ATGGYAAGGAGC AAGGGAGCAGG'] | 3071 | ['ATGGYAAGGAG CAAGGGAGCAGG'] |
| NM_012463.3 (ATP6V0A2):c.825+2T>C | 2354 | ATP6V50A2 | 2657 | ['ACCCGCATCC AGGATCTCTAC ACTGYGAGTA AGCTGGAAGT GGATTGCCTC'] | 2842 | ['CACTGYGAGTAA GCTGGAAGTGG'] | 3072 | ['CACTGYGAGTAA GCTGGAAGTGG'] |
| NM_016725.2 (FOLR1):c.493+2T>C | 2348 | FOLR1 | 2658 | ['ACAAGGGCTG GAACTGGACTT CAGGYGAGGG CTGGGGTGGG CAGGAATGGA'] | 2843 | ['AGGYGAGGGCTG GGGTGGGCAGG'] | 3073-3074 | ['CTTCAGGYGAGG GCTGGGGTGGG', 'AGGYGAGGGCTG GGGTGGGCAGG'] |
| NM_003764.3 (STX11):c.173T>C (p.Leu58Pro) | 8676 | STX11 | 2659 | ['GACATTCAGG ATGAAAACCA GCTGCYGGTG GCCGACGTGA AGCGGCTGGGA'] | 2844 | ['TGCYGGTGGCCG ACGTGAAGCGG'] | 3075 | ['TGCYGGTGGCCG ACGTGAAGCGG'] |
| NM_014714.3 (1FT140):c.4078T>C (p.Cys1360Arg) | 9742 | IFT140 | 2660 | ['GGACCCCAAG GAGTCCATCAA GCAGYGTGAG CTGCTCCTGGA GGAACCAGA'] | 2845 | ['GCAGYGTGAGCT GCTCCTGGAGG'] | 3076-3077 | ['CAAGCAGYGTGA GCTGCTCCTGG', 'GCAGYGTGAGCT GCTCCTGGAGG'] |
| NM_000531.5 (OTC):c.1005+2T>C | 5009 | OTC | 2661 | ['GAAAACAGA AAGTGGACAA TCATGGYAAG CAAGAAACAA GGAATGGAGGAT'] | 2846 | ['ATCATGGYAAGC AAGAAACAAGG'] | 3078 | ['ATCATGGYAAGC AAGAAACAAGG'] |
| NM_000531.5 (OTC):c.158T>C (p.Ile53Thr) | 5009 | OTC | 2662 | ['CTAAAAAACT TACCGGAGA AGAAABTAAA TATATGCTATG GCTATCAGCA'] | 2847 | ['AAGAAABTAAAT ATATGCTATGG'] | 3079 | ['AAGAAABTAAAT ATATGCTATGG'] |
| NM_000531.5 (OTC):c.284T>C (p.Leu95Ser) | 5009 | OTC | 2663 | ['GAGAAAAGA AGTACTCGAAC AAGATYGTCTA CAGAAACAGG TAAGTCCACT'] | 2848 | ['ACAAGATYGTCT ACAGAAACAGG'] | 3080 | ['ACAAGATYGTCT ACAGAAACAGG'] |

TABLE 2-continued

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_000531.5 (OTC):c.2T>C (p.Met1Thr) | 5009 | OTC | 2664 | ['CGTCCTTTAC ACAATTAAAA GAAGAYGCTG TTTAATCTGAG GATCCTGTTA'] | 2849 | ['AGAAGAYGCTGT TTAATCTGAGG'] | 3081 | ['AGAAGAYGCTGT TTAATCTGAGG'] |
| NM_000531.5 (OTC):c.526T>C (p.Tyr176His) | 5009 | OTC | 2665 | ['CCATCCTATC CAGATCCTGGC TGATYACCTCA CGCTCCAGGTT GGTTTATT'] | 2850 | ['GGCTGATYACCT CACGCTCCAGG'] | 3082-3083 | ['GGCTGATYACCT CACGCTCCAGG', 'GATYACCTCACG CTCCAGGTTGG'] |
| NM_000531.5 (OTC):c.779T>C (p.Leu260Ser) | 5009 | OTC | 2666 | ['GAAGCAGCGC ATGGAGGCAA TGTATYAATTA CAGACACTTGG ATAAGCATG'] | 2851 | ['ATGTATYAATTAC AGACACTTGG'] | 3084 | ['ATGTATYAATTA CAGACACTTGG'] |
| NM_000322.4 (PRPH2):c.736T>C (p.Trp246Arg) | 5961 | PRPH2 | 2667 | ['CCACCAGACG GAGGAGCTCA ACCTGYGGGT GCGTGGCTGCA GGGCTGCCCT'] | 2852-2853 | ['ACCTGYGGGTGC GTGGCTGCAGG', 'CCTGYGGGTGCGT GGCTGCAGGG'] | 3085-3086 | ['ACCTGYGGGTGC GTGGCTGCAGG', 'CCTGYGGGTGCG TGGCTGCAGGG'] |
| NM_000211.4 (ITGB2):c.1877+2T>C | 3689 | ITGB2 | 2668 | ['CCCCTCACCC TGTGGCAAGTA CATGYGAGTG CAGGCGGAGC AGGCAGGGCG'] | 2854 | ['CATGYGAGTGCA GGCGGAGCAGG'] | 3087 | ['CATGYGAGTGCA GGCGGAGCAGG'] |
| NM_015474.3 (SAMHD1):c.1106T>C (p.Leu369Ser) | 25939 | SAMHD1 | 2669 | ['TTTGTGTTGA TAAGCTCTACG GTGTRAAGAGT TGCGAGTGTGG AACATGTC'] | 2855 | ['GGTGTRAAGAGT TGCGAGTGTGG'] | 3088 | ['GGTGTRAAGAGT TGCGAGTGTGG'] |
| NM_001101.3 (ACTB):c.356T>C (p.Met119Thr) | 60 | ACTB | 2670 | ['AACCCCAAGG CCAACCGCGA GAAGAYGACC CAGGTGAGTG GCCCGCTACCT'] | 2856 | ['GAGAAGAYGACC CAGGTGAGTGG'] | 3089 | ['GAGAAGAYGAC CCAGGTGAGTGG'] |
| NM_015713.4 (RRM2B):c.368T>C (p.Phe123Ser) | 50484 | RRM2B | 2671 | ['CTCGATGAGA ATTTGAAAGCC ATAGRAACAG CGAGCCTCTGG AACCTGCAC'] | 2857 | ['CCATAGRAACAG CGAGCCTCTGG'] | 3090 | ['CCATAGRAACAG CGAGCCTCTGG'] |
| NM_015599.2 (PGM3):c.248T>C (p.Leu83Ser) | 5238 | PGM3 | 2672 | ['TTGGTTGATC CTTTGGGTGAA ATGTYGGCACC ATCCTGGGAG GAACATGCC'] | 2858 | ['AATGTYGGCACC ATCCTGGGAGG'] | 3091 | ['AATGTYGGCACC ATCCTGGGAGG'] |
| NM_002136.2 (HNRNPA1):c.817T>C (p.Phe273Leu) | 3178 | HNRNPA1 | 2673 | ['GAATTACAAC AATCAGTCTTC AAATBTTGGAC CCATGAAGGG AGGAAATTT'] | 2859-2861 | ['TTCAAATBTTGGA CCCATGAAGG', 'TCAAATBTTGGAC CCATGAAGGG', 'AATBTTGGACCCA TGAAGGGAGG'] | 3092-3094 | ['TTCAAATBTTGG ACCCATGAAGG', 'TCAAATBTTGGAC CCATGAAGGG', 'AATBTTGGACCC ATGAAGGGAGG'] |
| NM_002136.2 (HNRNPA1):c.841T>C (p.Phe281Leu) | 3178 | HNRNPA1 | 2674 | ['TTTTGGACCC ATGAAGGGAG GAAATYTTGG AGGCAGAAGC TCTGGCCCCTA'] | 2862 | ['AATYTTGGAGGC AGAAGCTCTGG'] | 3095 | ['AATYTTGGAGGC AGAAGCTCTGG'] |
| NM_022552.4 (DNMT3A):c.2705T>C (p.Phe902Ser) | 1788 | DNMT3A | 2675 | ['CGCAAAATAC TCCTTCAGCGG AGCGRAGAGG TGGCGGATGA CTGGCACGCT'] | 2863 | ['GCGRAGAGGTGG CGGATGACTGG'] | 3096 | ['GCGRAGAGGTGG CGGATGACTGG'] |
| NM_000076.2 (CDKN1C):c.*5+2T>C | 1028 | CDKN1C | 2676 | ['GCGCAAGAG GCTGCGGTGA GCCAAGYGAG TACAGCGCACC TGGGGGGGCGC'] | 2864-2866 | ['CCAAGYGAGTAC AGCGCACCTGG', 'CAAGYGAGTACA GCGCACCTGGG', 'AAGYGAGTACAG CGCACCTGGGG'] | 3097-3099 | ['CCAAGYGAGTAC AGCGCACCTGG', 'CAAGYGAGTACA GCGCACCTGGG', 'AAGYGAGTACAG CGCACCTGGGG'] |

TABLE 2-continued

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NC_012920.1:m.9478T>C | 4514 | MTCO3 | 2677 | ['ATAATCCTAT TTATTACCTCA GAAGYTTTTT CTTCGCAGGAT TTTTCTGA'] | 2867 | ['TCAGAAGYTTTTT TCTTCGCAGG'] | 3100 | ['TCAGAAGYTTTT TTCTTCGCAGG'] |
| NM_002049.3 (GATA1):c.2T>C (p.Met1Thr) | 2623 | GATA1 | 2678 | ['CGCAGGTTAA TCCCCAGAGGC TCCAYGGAGTT CCCTGGCCTGG GGTCCCTG'] | 2868-2869 | ['TCCAYGGAGTTC CCTGGCCTGGG', 'CCAYGGAGTTCCC TGGCCTGGGG'] | 3101-3103 | ['CTCCAYGGAGTT CCCTGGCCTGG', 'TCCAYGGAGTTC CCTGGCCTGGG', 'CCAYGGAGTTCC CTGGCCTGGGG'] |
| NM_005740.2 (DNAL4):c.153+2T>C | 10126 | DNAL4 | 2679 | ['GAGAAATTCT CCAACAACAA CGAGGYATTG CCAGCAGTGC AGGCGGCCCCT'] | 2870 | ['CGAGGYATTGCC AGCAGTGCAGG'] | 3104 | ['CGAGGYATTGCC AGCAGTGCAGG'] |
| NM_001287223.1 (SCN11A):c.1142T>C (p.Ile381Thr) | 11280 | SCN11A | 2680 | ['GGGCTCTACT CAGTCTTCTTC TTCAYTGTGGT CATTTTCCTGG GCTCCTTC'] | 2871 | ['TTCAYTGTGGTCA TTTTCCTGGG'] | 3105-3106 | ['CTTCAYTGTGGT CATTTTCCTGG', 'TTCAYTGTGGTCA TTTTCCTGGG'] |
| NM_001302946.1 (TRNT1):c.497T>C (p.Leu166Ser) | 51095 | TRNT1 | 2681 | ['TAATGAATAG GTTTTGATGGC ACTTYATTTGA CTACTTTAATG GTTATGAA'] | 2872 | ['ACTTYATTTGACT ACTTTAATGG'] | 3107 | ['ACTTYATTTGAC TACTTTAATGG'] |
| NM_178151.2 (DCX):c.2T>C (p.Met1Thr) | 1641 | DCX | 2682 | ['AGGTCTCTGA GGTTCCACCAA AATAYGGAAC TTGATTTTGGA CACTTTGAC'] | 2873 | ['CAAAATAYGGAA CTTGATTTTGG'] | 3108 | ['CAAAATAYGGA ACTTGATTTTGG'] |
| NM_000169.2 (GLA):c.758T>C (p.Ile253Thr) | −1 | — | 2683 | ['TGGACATCTT TTAACCAGGA GAGAAYTGTT GATGTTGCTGG ACCAGGGGT'] | 2874 | ['GAGAGAAYTGTT GATGTTGCTGG'] | 3109 | ['GAGAGAAYTGTT GATGTTGCTGG'] |
| NM_170707.3 (LMNA):c.710T>C (p.Phe237Ser) | 4000 | LMNA | 2684 | ['ATTGACAATG GGAAGCAGCG TGAGTYTGAG AGCCGGCTGG CGGATGCGCTG'] | 2875 | ['TGAGTYTGAGAG CCGGCTGGCGG'] | 3110 | ['TGAGTYTGAGAG CCGGCTGGCGG'] |
| NM_000256.3 (MYBPC3):c.3330+2T>C | 4607 | MYBPC3 | 2685 | ['CAGAAAGCCG ACAAGAAGAC CATGGBGAGC CCAGGGTCTGG GGTCCCCACG'] | 2876-2878 | ['ACCATGGBGAGC CCAGGGTCTGG', 'CCATGGBGAGCCC AGGGTCTGGG', 'CATGGBGAGCCCA GGGTCTGGGG'] | 3111-3113 | ['ACCATGGBGAGC CCAGGGTCTGG', 'CCATGGBGAGCC CAGGGTCTGGG', 'CATGGBGAGCCC AGGGTCTGGGG'] |
| NM_005957.4 (MTHFR):c.1530+2T>C | 4524 | MTHFR | 2686 | ['AGCGGGGGCT ATGTCTTCCAG AAGGYGTGGT AGGGAGGCAC GGGGTGCCCC'] | 2879-2881 | ['GAAGGYGTGGTA GGGAGGCACGG', 'AAGGYGTGGTAG GGAGGCACGGG', 'AGGYGTGGTAGG GAGGCACGGGG'] | 3114-3116 | ['GAAGGYGTGGTA GGGAGGCACGG', 'AAGGYGTGGTAG GGAGGCACGGG', 'AGGYGTGGTAGG GAGGCACGGGG'] |
| NM_000264.3 (PTCH1):c.3168+2T>C | 5727 | PTCH1 | 2687 | ['AACCCCTGGA CGGCCGGGAT CATTGYGAGTG TATTATAAGGG GCTTTGTGG'] | 2882-2884 | ['ATCATTGYGAGT GTATTATAAGG', 'TCATTGYGAGTGT ATTATAAGGG', 'CATTGYGAGTGTA TTATAAGGGG'] | 3117-3119 | ['ATCATTGYGAGT GTATTATAAGG', 'TCATTGYGAGTGT ATTATAAGGG', 'CATTGYGAGTGT ATTATAAGGGG'] |
| NM_000030.2 (AGXT):c.322T>C (p.Trp108Arg) | 189 | AGXT | 2688 | ['CTTCCTGGTT GGGGCCAATG GCATTYGGGG GCAGCGAGCC GTGGACATCGG'] | 2885 | ['CATTYGGGGGCA GCGAGCCGTGG'] | 3120 | ['CATTYGGGGGCA GCGAGCCGTGG'] |
| NM_000023.2 (SGCA):c.371T>C (p.Ile124Thr) | 6442 | SGCA | 2689 | ['ACTCGGCAGA GGCTGGTGCTG GAGAYTGGGG ACCCAGAAGG TACCTCTAGC'] | 2886 | ['CTGGAGAYTGGG GACCCAGAAGG'] | 3121 | ['CTGGAGAYTGGG GACCCAGAAGG'] |

TABLE 2-continued

T to C changes with NGG PAM. Table 2 shows a list of T to C mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_001103.3 (ACTN2):c.683T>C (p.Met228Thr) | 88 | ACTN2 | 2690 | ['GAGAAGCACC TGGATATTCCT AAAAYGTTGG ATGCTGAAGGT GAGATGAAA'] | 2887 | ['CCTAAAAYGTTG GATGCTGAAGG'] | 3122 | ['CCTAAAAYGTTG GATGCTGAAGG'] |
| NM_001165963.1 (SCN1A):c.4055T>C (p.Leu1352Pro) | −1 | — | 2691 | ['ATTCCATCCA TCATGAATGTG CTTCYGGTTTG TCTTATATTCT GGCTAATT'] | 2888 | ['TTCYGGTTTGTCT TATATTCTGG'] | 3123 | ['TTCYGGTTTGTC TTATATTCTGG'] |
| NM_001165963.1 (SCN1A):c.1265T>C (p.Val422Ala) | 6323 | SCN1A | 2692 | ['CTAATAAATT TGATCCTGGCT GTGGHGGCCA TGGCCTACGAG GAACAGAAT'] | 2889 | ['TGTGGHGGCCAT GGCCTACGAGG'] | 3124 | ['TGTGGHGGCCAT GGCCTACGAGG'] |
| NM_000426.3 (LAMA2):c.8282T>C (p.Ile2761Thr) | 3908 | LAMA2 | 2693 | ['GCAGAATCAG AACCAGCTCTT TTGAYAGGGA GCAAGCAGTTC GGGCTTTCA'] | 2890-2891 | ['TTGAYAGGGAGC AAGCAGTTCGG', 'TGAYAGGGAGCA AGCAGTTCGGG'] | 3125-3126 | ['TTGAYAGGGAGC AAGCAGTTCGG', 'TGAYAGGGAGCA AGCAGTTCGGG'] |
| NM_000257.3 (MYH7):c.5117T>C (p.Leu1706Pro) | −1 | — | 2694 | ['TCCCGGAAGC TGGCGGAGCA GGAGCYGATT GAGACTAGTG AGCGGGTGCAG'] | 2892 | ['AGCYGATTGAGA CTAGTGAGCGG'] | 3127 | ['AGCYGATTGAGA CTAGTGAGCGG'] |
| NM_001399.4 (EDA):c.396+2T>C | 1896 | EDA | 2695 | ['TCTGACTCCC AGGACGGGCA CCAGGKGAGT CACCTAGTAGG GGCGGCGGCG'] | 2893-2894 | ['ACCAGGKGAGTC ACCTAGTAGGG', 'CCAGGKGAGTCAC CTAGTAGGGG'] | 3128-3130 | ['CACCAGGKGAGT CACCTAGTAGG', 'ACCAGGKGAGTC ACCTAGTAGGG', 'CCAGGKGAGTCA CCTAGTAGGGG'] |
| NM_001848.2 (COL6A1):c.957+2T>C | 1291 | COL6A1 | 2696 | ['TCCAGGGGAC CCAAGGGCTA CAAGGYGAGC GTGGGCTGCTG GGAGGGGGA'] | 2895-2896 | ['ACAAGGYGAGCG TGGGCTGCTGG', 'CAAGGYGAGCGT GGGCTGCTGGG'] | 3131-3132 | ['ACAAGGYGAGC GTGGGCTGCTGG', 'CAAGGYGAGCGT GGGCTGCTGGG'] |
| NM_000238.3 (KCNH2):c.1945+6T>C | 3757 | KCNH2 | 2697 | ['CTGCGTCATG CTCATTGGCTG TGAGYGTGCCC AGGGGCGGGC GGCGGGGAG'] | 2897-2898 | ['CTGTGAGYGTGC CCAGGGGCGGG', 'TGAGYGTGCCCAG GGGCGGGCGG'] | 3133-3134 | ['CTGTGAGYGTGC CCAGGGGCGGG', 'TGAGYGTGCCCA GGGGCGGGCGG'] |
| NM_021007.2 (SCN2A):c.1271T>C (p.Val424Ala) | 6326 | SCN2A | 2698 | ['CTAATAAATT TGATCTTGGCT GTGGYGGCCA TGGCCTATGAG GAACAGAAT'] | 2899 | ['TGTGGYGGCCAT GGCCTATGAGG'] | 3135 | ['TGTGGYGGCCAT GGCCTATGAGG'] |
| NM_021007.2 (SCN2A):c.4308+2T>C | 6326 | SCN2A | 2699 | ['TATGCAGCTG TTGATTCACGA AATGYAAGTCT AGTTAGAGGG AAATTGTTT'] | 2900-2901 | ['CGAAATGYAAGT CTAGTTAGAGG', 'GAAATGYAAGTCT AGTTAGAGGG'] | 3136-3137 | ['CGAAATGYAAGT CTAGTTAGAGG', 'GAAATGYAAGTC TAGTTAGAGGG'] |
| NM_000083.2 (CLCN1):c.1283T>C (p.Phe428Ser) | 1180 | CLCN1 | 2700 | ['CCCCGCGAAG CCATCAGTACT TTGTYTGACAA CAATACATGG GTGAAACAC'] | 2902-2903 | ['CTTTGTYTGACAA CAATACATGG', 'TTTGTYTGACAAC AATACATGGG'] | 3138-3139 | ['CTTTGTYTGACA ACAATACATGG', 'TTTGTYTGACAAC AATACATGGG'] |
| NM_004550.4 (NDUFS2):c.875T>C (p.Met292Thr) | 4720 | NDUFS2 | 2701 | ['CATTATGCTC TCCACAGTGGA GTGAYGCTTCG GGGCTCAGGC ATCCAGTGG'] | 2904 | ['GGAGTGAYGCTT CGGGGCTCAGG'] | 3140 | ['GGAGTGAYGCTT CGGGGCTCAGG'] |
| NM_000546.5 (TP53):c.584T>C (p.Ile195Thr) | 7157 | TP53 | 2702 | ['CACACGCAAA TTTCCTTCCAC TCGGRTAAGAT GCTGAGGAGG GGCCAGACC'] | 2905-2906 | ['CTCGGRTAAGAT GCTGAGGAGGG', 'TCGGRTAAGATGC TGAGGAGGGG'] | 3141-3143 | ['ACTCGGRTAAGA TGCTGAGGAGG', 'CTCGGRTAAGAT GCTGAGGAGGG', 'TCGGRTAAGATG CTGAGGAGGGG'] |

TABLE 3

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_017547.3 (FOXRED1):c.1289A>G (p.Asn430Ser) | 55572 | FOXRED1 | 5084 | ['GTGGGCCCCCACC CGCTAGTTGTCAVC ATGTACTTTGCTACT GGCTTCAGT'] | 5261 | ['CCACCCGCTAGT TGTCAVCATGT'] | 5464-5466 | ['CCCACCCGCTAG TTGTCAVCATG', 'CCACCCGCTAGTT GTCAVCATGT', 'CCCGCTAGTTGTC AVCATGTACT'] |
| NM_000071.2 (CBS):c.1150A>G (p.Lys384Glu) | 875 | CBS | 5085 | ['GGTGACTCCCCCAT CCCGCAGGACCRAG TTCCTGAGCGACAG GTGGATGCT'] | 5262 | ['CCCCATCCCGCA GGACCRAGTTC'] | 5467-5470 | ['CCCCCATCCCGC AGGACCRAGTT', 'CCCCATCCCGCA GGACCRAGTTC', 'CCCATCCCGCAG GACCRAGTTCC', 'CCATCCCGCAGG ACCRAGTTCCT'] |
| NM_000552.3 (VWF):c.2384A>G (p.Tyr795Cys) | 7450 | VWF | 5086 | ['GAGTGTACCAAAA CGTGCCAGAACTRT GACCTGGAGTGCAT GAGCATGGGC'] | 5263 | ['CCAAAACGTGCC AGAACTRTGAC'] | 5471 | ['CCAAAACGTGCC AGAACTRTGAC'] |
| NM_000552.3 (VWF):c.1583A>G (p.Asn528Ser) | 7450 | VWF | 5087 | ['ACCTGCGGCCTGT GTGGGAATTACART GGCAACCAGGGCGA CGACTTCCTT'] | 5264 | ['CCTGTGTGGGAA TTACARTGGCA'] | 5472 | ['CCTGTGTGGGAA TTACARTGGCA'] |
| NM_000308.2 (CTSA):c.1238A>G (p.Tyr413Cys) | 5476 | CTSA | 5088 | ['CTTTAGAAATACC AGATCCTATTATRTA ATGGAGATGTAGAC ATGGCCTGC'] | 5265 | ['CCAGATCCTATT ATRTAATGGAG'] | 5473 | ['CCAGATCCTATT ATRTAATGGAG'] |
| NM_000277.1 (PAH):c.916A>G (p.Ile306Val) | 5053 | PAH | 5089 | ['TTCTATTTTCCCCC AATTACAGGAARTT GGCCTTGCCTCTCTG GGTGCACC'] | 5266 | ['CCCCCAATTACA GGAARTTGGCC'] | 5474-5476 | ['CCCCCAATTACA GGAARTTGGCC', 'CCCCAATTACAG GAARTTGGCCT', 'CCCAATTACAGG AARTTGGCCTT'] |
| NM_000512.4 (GALNS):c.1460A>G (p.Asn487Ser) | 2588 | GALNS | 5090 | ['TTGGTCCCCGCGCA GCCCCAGCTCARCG TGTGCAACTGGGCG GTCATGGTA'] | 5267 | ['CCGCGCAGCCCC AGCTCARCGTG'] | 5477 | ['CCGCGCAGCCCC AGCTCARCGTG'] |
| NM_013319.2 (UBIAD1):c.305A>G (p.Asn102Ser) | 29914 | UBIAD1 | 5091 | ['GTGCACGGGGCCG GTAATTTGGTCARC ACTTACTATGACTTT TCCAAGGGC'] | 5268 | ['CCGGTAATTTGG TCARCACTTAC'] | 5478 | ['CCGGTAATTTGG TCARCACTTAC'] |
| NM_013319.2 (UBIAD1):c.695A>G (p.Asn232Ser) | 29914 | UBIAD1 | 5092 | ['AGCACCGAGGCCA TTCTCCATTCCARCA ACACCAGGGACATG GAGTCCGAC'] | 5269 | ['CCATTCTCCATT CCARCAACACC'] | 5479 | ['CCATTCTCCATT CCARCAACACC'] |
| NM_000275.2 (OCA2):c.1465A>G (p.Asn489Asp) | 4948 | OCA2 | 5093 | ['TGCCACTGCCATCG GGGACCCTCCARAT GTCATTATTGTTTCC AACCAAGA'] | 5270 | ['CCATCGGGGACC CTCCARATGTC'] | 5480 | ['CCATCGGGGACC CTCCARATGTC'] |
| NM_001127255.1 (NLRP7):c.2738A>G (p.Asn913Ser) | −1 | — | 5094 | ['CTCACAAACCTGG ACTTGAGTATCARC CAGATAGCTCGTGG ATTGTGGATT'] | 5271 | ['CCTGGACTTGAG TATCARCCAGA'] | 5481 | ['CCTGGACTTGAG TATCARCCAGA'] |
| NM_152783.4 (D2HGDH):c.1315A>G (p.Asn439Asp) | 728294 | D2HGDH | 5095 | ['TGCCCTTGTCCCTC CAGGAGATGGTRAC CTGCACCTCAATGT GACGGCGA'] | 5272 | ['CCTCCAGGAGAT GGTRACCTGCA'] | 5482-5483 | ['CCCTCCAGGAGA TGGTRACCTGC', 'CCTCCAGGAGAT GGTRACCTGCA'] |
| NM_022132.4 (MCCC2):c.1309A>G (p.Ile437Val) | 64087 | MCCC2 | 5096 | ['TGTGGCCTGTGCCC AAGTGCCTAAGDTA ACCCTCATCATTGG GGGCTCCTA'] | 5273 | ['CCCAAGTGCCTA AGDTAACCCTC'] | 5484 | ['CCCAAGTGCCTA AGDTAACCCTC'] |
| NM_000022.2 (ADA):c.219-2A>G | 100 | ADA | 5097 | ['TTCCCAACCCCTTT CTTCCCTTCCCRGGG GCTGCCGGGAGGCT ATCAAAAG'] | 5274 | ['CCCCTTTCTTCCC TTCCCRGGGG'] | 5485-5487 | ['CCCCTTTCTTCCC TTCCCRGGGG', 'CCCTTTCTTCCCT TCCCRGGGGC', 'CCTTTCTTCCCTT CCCRGGGGCT'] |
| NM_017780.3 (CHD7):c.3082A>G (p.Ile1028Val) | 55636 | CHD7 | 5098 | ['TTTAGTAATTGCCC CATTGTCCACARTC CCCAACTGGGAAAG GGAATTCCG'] | 5275 | ['CCCCATTGTCCA CARTCCCCAAC'] | 5488 | ['CCCCATTGTCCA CARTCCCCAAC'] |

TABLE 3-continued

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_000483.4 (APOC2):c.1A>G (p.MetlVal) | −1 | — | 5099 | ['TCAATGTTCCAGGTCTCTGGACACTRTGGGCACACGACTCCTCCCAGCTCT'] | 5276 | ['CCAGGTCTCTGGACACTRTGGGC'] | 5489 | ['CCAGGTCTCTGGACACTRTGGGC'] |
| NM_000391.3 (TPP1):c.887-10A>G | 1200 | TPP1 | 5100 | ['TGTCCCTCATGCCGGCCTGGATTTTYTTTTTTTTTTTTTTGAGGGATGGG'] | 5277 | ['CCGGCCTGGATTTTYTTTTTTTT'] | 5490 | ['CCGGCCTGGATTTTYTTTTTTTT'] |
| NM_017890.4 (VPS13B):c.8978A>G (p.Asn2993Ser) | 157680 | VPS13B | 5101 | ['CTTCTGCCCTGGGCCCTGCTTATCARTGAATCCAAATGGGACCTCTGGCTA'] | 5278 | ['CCTGGGCCCTGCTTATCARTGAA'] | 5491 | ['CCTGGGCCCTGCTTATCARTGAA'] |
| NM_000226.3 (KRT9):c.482A>G (p.Asn161Ser) | 3857 | KRT9 | 5102 | ['GAGAAGAGCACCATGCAGGAACTCADTTCTCGGCTGGCCTCTTACTTGGAT'] | 5279 | ['CCATGCAGGAACTCADTTCTCGG'] | 5492 | ['CCATGCAGGAACTCADTTCTCGG'] |
| NM_000529.2 (MC2R):c.761A>G (p.Tyr254Cys) | 4158 | MC2R | 5103 | ['CCAAGTAACCCCTACTGCGCCTGCTRCATGTCTCTCTTCCAGGTGAACGGC'] | 5280-5281 | ['CCCCTACTGCGCCTGCTRCATGTC', 'CCTACTGCGCCTGCTRCATGTCT'] | 5493-5495 | ['CCCCTACTGCGCCTGCTRCATGT', 'CCCTACTGCGCCTGCTRCATGTC', 'CCTACTGCGCCTGCTRCATGTCT'] |
| NM_005957.4 (MTHFR):c.971A>G (p.Asn324Ser) | 4524 | MTHFR | 5104 | ['CCAGGCCTCCACTTCTACACCCTCARCCGCGAGATGGCTACCACAGAGGTG'] | 5282 | ['CCACTTCTACACCCTCARCCGCG'] | 5496 | ['CCACTTCTACACCCTCARCCGCG'] |
| NM_000403.3 (GALE):c.101A>G (p.Asn34Ser) | 2582 | GALE | 5105 | ['GGCTACTTGCCTGTGGTCATCGATARCTTCCATAATGCCTTCCGTGGTGAG'] | 5283 | ['CCTGTGGTCATCGATARCTTCCA'] | 5497 | ['CCTGTGGTCATCGATARCTTCCA'] |
| NM_000356.3 (TCOF1):c.149A>G (p.Tyr50Cys) | 6949 | TCOF1 | 5106 | ['CAGCCCGTAACCCTTCTGGACATCTRTACACACTGGCAACAGTAAGTGGTG'] | 5284-5285 | ['CCCTTCTGGACATCTRTACACAC', 'CCTTCTGGACATCTRTACACACT'] | 5498-5499 | ['CCCTTCTGGACATCTRTACACAC', 'CCTTCTGGACATCTRTACACACT'] |
| NM_012464.4 (TLL1):c.1885A>G (p.Ile629Val) | 7092 | TLL1 | 5107 | ['ACTTCTTACCAAACTTAACGGCACCRTAACCACCCCTGGCTGGCCCAAGGA'] | 5286 | ['CCAAACTTAACGGCACCRTAACC'] | 5500 | ['CCAAACTTAACGGCACCRTAACC'] |
| NM_000112.3 (SLC26A2):c.1273A>G (p.Asn425Asp) | 1836 | SLC26A2 | 5108 | ['GGAAATGTATGCCATTGGCTTTTGTRATATCATCCCTTCCTTCTTCCACTG'] | 5287 | ['CCATTGGCTTTTGTRATATCATC'] | 5501 | ['CCATTGGCTTTTGTRATATCATC'] |
| NM_000157.3 (GBA):c.680A>G (p.Asn227Ser) | 2629 | GBA | 5109 | ['ACATCACCCACTTGGCTCAAGACCARTGGAGCGGTGAATGGGAAGGGGTCA'] | 5288 | ['CCACTTGGCTCAAGACCARTGGA'] | 5502 | ['CCACTTGGCTCAAGACCARTGGA'] |
| NM_175073.2 (APTX):c.602A>G (p.His201Arg) | 54840 | APTX | 5110 | ['GATAAATACCCAAAGGCCCGTTACCRTTGGCTGGTCTTACCGTGGACCTCC'] | 5289-5290 | ['CCCAAAGGCCCGTTACCRTTGGC', 'CCAAAGGCCCGTTACCRTTGGCT'] | 5503-5504 | ['CCCAAAGGCCCGTTACCRTTGGC', 'CCAAAGGCCCGTTACCRTTGGCT'] |
| NM_020638.2 (FGF23):c.211A>G (p.Ser71Gly) | 8074 | FGF23 | 5111 | ['TGGCGCACCCCATCAGACCATCTACRGTGAGTAGGGCTTCAGGCTGGGAAG'] | 5291 | ['CCCCATCAGACCATCTACRGTGA'] | 5505-5507 | ['CCCCATCAGACCATCTACRGTGA', 'CCCATCAGACCATCTACRGTGAG', 'CCATCAGACCATCTACRGTGAGT'] |
| NM_021102.3 (SPINT2):c.488A>G (p.Tyr163Cys) | 10653 | SPINT2 | 5112 | ['AGGAACTCCTGCAATAACTTCATCTRTGGAGGCTGCCGGGGCAATAAGAAC'] | 5292 | ['CCTGCAATAACTTCATCTRTGGA'] | 5508 | ['CCTGCAATAACTTCATCTRTGGA'] |
| NM_004795.3 (KL):c.578A>G (p.His193Arg) | 9365 | KL | 5113 | ['GTGCAGCCCGTGGTCACCCTGTACCRCTGGGACCTGCCCCAGCGCCTGCAG'] | 5293 | ['CCGTGGTCACCCTGTACCRCTGG'] | 5509 | ['CCGTGGTCACCCTGTACCRCTGG'] |
| NM_012193.3 (FZD4):c.766A>G (p.Ile256Val) | −1 | — | 5114 | ['GTTTTCCTACCCTGAGCGCCCCATCRTATTTCTTTCTCAGTATGTGCTATAATAT'] | 5294-5295 | ['CCCTGAGCGCCCCATCRTATTTC', 'CCTGAGCGCCCCATCRTATTTCT'] | 5510-5511 | ['CCCTGAGCGCCCCATCRTATTTC', 'CCTGAGCGCCCCATCRTATTTCT'] |

TABLE 3-continued

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: Flanks | Flanks | SEQ ID NO: GRNAs | GRNAs | SEQ ID NO: gRNAall | gRNAall |
|---|---|---|---|---|---|---|---|---|
| NM_001099274.1 (TINF2):c.838A>G (p.Lys280Glu) | 26277 | TINF2 | 5115 | ['ATGGGCCTCCACT AGGGGAGGCCATDA GGAGCGCCCCACAG TCATGCTGTT'] | 5296 | ['CCACTAGGGGAG GCCATDAGGAG'] | 5512 | ['CCACTAGGGGAG GCCATDAGGAG'] |
| NM_005682.6 (ADGRG1):c.263A>G (p.Tyr88Cys) | 9289 | ADGRG1 | 5116 | ['TCCTTCCCTGACCC CAGGGGCCTCTRCC ACTTCTGCCTCTACT GGAACCGA'] | 5297 | ['CCCCAGGGGCCT CTRCCACTTCT'] | 5513 | ['CCCCAGGGGCCT CTRCCACTTCT'] |
| NM_000369.2 (TSHR):c.1856A>G (p.Asp619Gly) | 7253 | TSHR | 5117 | ['CCGCAGTACAACC CAGGGGACAAAGRT ACCAAAATTGCCAA GAGGATGGCT'] | 5298 | ['CCCAGGGGACAA AGRTACCAAAA'] | 5514 | ['CCCAGGGGACAA AGRTACCAAAA'] |
| NM_024009.2 (GJB3):c.497A>G (p.Asn166Ser) | 2707 | GJB3 | 5118 | ['ATGCCGCGCCTGG TGCAGTGTGCCADC GTGGCCCCCTGCCC CAACATCGTG'] | 5299 | ['CCTGGTGCAGTG TGCCADCGTGG'] | 5515 | ['CCTGGTGCAGTG TGCCADCGTGG'] |
| NM_003722.4 (TP63):c.697A>G (p.Lys233Glu) | 8626 | TP63 | 5119 | ['TATCCGCGCCATGC CTGTCTACAAARAA GCTGAGCACGTCAC GGAGGTGGT'] | 5300 | ['CCATGCCTGTCT ACAAARAAGCT'] | 5516 | ['CCATGCCTGTCT ACAAARAAGCT'] |
| NM_003494.3 (DYSF):c.3443-33A>G | 8291 | DYSF | 5120 | ['CAGCTCTTAACCAC TCCAGCCACTCRCT CTGGCACCTCTGTTT TTTCCCTT'] | 5301 | ['CCACTCCAGCCA CTCRCTCTGGC'] | 5517 | ['CCACTCCAGCCA CTCRCTCTGGC'] |
| NM_003494.3 (DYSF):c.1285-2A>G | 8291 | DYSF | 5121 | ['AACTTGTCCCCTCC CTGTGTCTTCTRGCT GTGCAGCAAGATCT TGGAGAAG'] | 5302 | ['CCCCTCCCTGTG TCTTCTRGCTG'] | 5518-5520 | ['CCCCTCCCTGTG TCTTCTRGCTG', 'CCCTCCCTGTGTC TTCTRGCTGT', 'CCTCCCTGTGTCT TCTRGCTGTG'] |
| NM_002408.3 (MGAT2):c.785A>G (p.His262Arg) | 4247 | MGAT2 | 5122 | ['CTTATACTTTTCCT AGAAGAGGATCRCT ACTTAGCCCCAGAC TTTTACCAT'] | 5303 | ['CCTAGAAGAGGA TCRCTACTTAG'] | 5521 | ['CCTAGAAGAGGA TCRCTACTTAG'] |
| NM_000492.3 (CFTR):c.2738A>G (p.Tyr913Cys) | 1080 | CFTR | 5123 | ['GTGATTATCACCA GCACCAGTTCGTRT TATGTGTTTTACATT TACGTGGGA'] | 5304 | ['CCAGCACCAGTT CGTRTTATGTG'] | 5522 | ['CCAGCACCAGTT CGTRTTATGTG'] |
| NM_001814.4 (CTSC):c.857A>G (p.Gln286Arg) | 1075 | CTSC | 5124 | ['TCTCAGACCCCAAT CCTAAGCCCTCRGG AGGTTGTGTCTTGTA GCCAGTAT'] | 5305 | ['CCCCAATCCTAA GCCCTCRGGAG'] | 5523-5525 | ['CCCCAATCCTAA GCCCTCRGGAG', 'CCCAATCCTAAG CCCTCRGGAGG', 'CCAATCCTAAGC CCTCRGGAGGT'] |
| NM_005144.4 (HR):c.-218A>G | 55806 | HR | 5125 | ['TCCGACCCCTCCAA CCTGCGGCCCTRGA GCGCCCCGCCGCC CCGGGGAA'] | 5306 | ['CCTCCAACCTGC GGCCCTRGAGC'] | 5526-5527 | ['CCTCCAACCTGC GGCCCTRGAGC', 'CCAACCTGCGGC CCTRGAGCGCC'] |
| NM_018488.2 (TBX4):c.1592A>G (p.Gln531Arg) | 9496 | TBX4 | 5126 | ['TCCTTGTCCCGAGA ATCTTCCTTACRGTA CCATTCAGGAATGG GGACTGTG'] | 5307 | ['CCCGAGAATCTT CCTTACRGTAC'] | 5528-5529 | ['CCCGAGAATCTT CCTTACRGTAC', 'CCGAGAATCTTCC TTACRGTACC'] |
| NM_001089.2 (ABCA3):c.1702A>G (p.Asn568Asp) | 21 | ABCA3 | 5127 | ['ACAGATCACCGTC CTGCTGGGCCACRA CGGTGCCGGGAAGA CCACCACCCT'] | 5308 | ['CCGTCCTGCTGG GCCACRACGGT'] | 5530 | ['CCGTCCTGCTGG GCCACRACGGT'] |
| NM_000525.3 (KCNDJ11):c.776A>G (p.His259Arg) | 37671 | KCNJ1 | 5128 | ['CTGGTGGCCCCGCT GATCATCTACCRTG TCATTGATGCCAAC AGCCCACTC'] | 5309-5310 | ['CCCCGCTGATCA TCTACCRTGTC', 'CCCGCTGATCATC TACCRTGTCA'] | 5531-5533 | ['CCCCGCTGATCA TCTACCRTGTC', 'CCCGCTGATCATC TACCRTGTCA', 'CCGCTGATCATCT ACCRTGTCAT'] |
| NM_005587.2 (MEF2A):c.788A>G (p.Asn263Ser) | 4205 | MEF2A | 5129 | ['TCTCCCCCTCCACC AGGTGGTGGTARTC TTGGAATGAACAGT AGGAAACCA'] | 5311 | ['CCACCAGGTGGT GGTARTCTTGG'] | 5534 | ['CCACCAGGTGGT GGTARTCTTGG'] |
| NM_000098.2 (CPT2):c.359A>G (p.Tyr120Cys) | 1376 | CPT2 | 5130 | ['TTTTTAGGACCCTG GTTTGATATGTRCCT ATCTGCTCGAGACT CCGTTGTT'] | 5312 | ['CCTGGTTTGATA TGTRCCTATCT'] | 5535-5536 | ['CCCTGGTTTGAT ATGTRCCTATC', 'CCTGGTTTGATAT GTRCCTATCT'] |

TABLE 3-continued

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_178138.4 (LHX3):c.332A>G (p.Tyr111Cys) | 8022 | LHX3 | 5131 | ['GTGCGCCGCGCCC AGGACTTCGTGTRC CACCTGCACTGCTTT GCCTGCGTC'] | 5313-5314 | ['CCCAGGACTTCG TGTRCCACCTG', 'CCAGGACTTCGT GTRCCACCTGC'] | 5537-5538 | ['CCCAGGACTTCG TGTRCCACCTG', 'CCAGGACTTCGT GTRCCACCTGC'] |
| NM_005502.3 (ABCA1):c.2804A>G (p.Asn935Ser) | 19 | ABCA1 | 5132 | ['CAGATCACCTCCTT CCTGGGCCACARTG GAGCGGGGAAGAC GACCACCATG'] | 5315 | ['CCTCCTTCCTGG GCCACARTGGA'] | 5539-5540 | ['CCTCCTTCCTGG GCCACARTGGA', 'CCTTCCTGGGCCA CARTGGAGCG'] |
| m.3260A>G | 4567 | MT-TL1 | 5133 | ['GATGGCAGAGCCC GGTAATCGCATARA ACTTAAAACTTTAC AGTCAGAGGT'] | 5316-5317 | ['CCCGGTAATCGC ATARAACTTAA', 'CCGGTAATCGCA TARAACTTAAA'] | 5541-5542 | ['CCCGGTAATCGC ATARAACTTAA', 'CCGGTAATCGCA TARAACTTAAA'] |
| m.4269A>G | 4565 | MT-TI | 5134 | ['GCATTCCCCCTCAA ACCTAAGAAATRTG TCTGATAAAAGAGT TACTTTGAT'] | 5318-5319 | ['CCCTCAAACCTA AGAAATRTGTC', 'CCTCAAACCTAA GAAATRTGTCT'] | 5543-5544 | ['CCCTCAAACCTA AGAAATRTGTC', 'CCTCAAACCTAA GAAATRTGTCT'] |
| m.14495A>G | 4541 | MT-ND6 | 5135 | ['TCCAAAGACAACC ATCATTCCCCCTRA ATAAATTAAAAAAA CTATTAAACC'] | 5320 | ['CCATCATTCCCC CTRAATAAATT'] | 5545 | ['CCATCATTCCCC CTRAATAAATT'] |
| NM_002764.3 (PRPS1):c.341A>G (p.Asn114Ser) | 5631 | PRPS1 | 5136 | ['CCAATCTCAGCCA AGCTTGTTGCAART ATGCTATCTGTAGC AGGTGCAGAT'] | 5321 | ['CCAAGCTTGTTG CAARTATGCTA'] | 5546 | ['CCAAGCTTGTTG CAARTATGCTA'] |
| NM_000054.4 (AVPR2):c.614A>G (p.Tyr205Cys) | 554 | AVPR2 | 5137 | ['GCGGAGCCCTGGG GCCGTCGCACCTRT GTCACCTGGATTGC CCTGATGGTG'] | 5322 | ['CCTGGGGCCGTC GCACCTRTGTC'] | 5547 | ['CCTGGGGCCGTC GCACCTRTGTC'] |
| NM_000033.3 (ABCD1):c.443A>G (p.Asn148Ser) | 215 | ABCD1 | 5138 | ['ATCGCCCTCCCTGC TACCTTCGTCARCA GTGCCATCCGTTAC CTGGAGGGC'] | 5323-5324 | ['CCCTGCTACCTT CGTCARCAGTG', 'CCTGCTACCTTCG TCARCAGTGC'] | 5548-5549 | ['CCCTGCTACCTT CGTCARCAGTG', 'CCTGCTACCTTCG TCARCAGTGC'] |
| NM_000061.2 (BTK):c.1082A>G (p.Tyr361Cys) | 695 | BTK | 5139 | ['AGCACCATCCCTG AGCTCATTAACTRC CATCAGCACAACTC TGCAGGTGAG'] | 5325-5326 | ['CCCTGAGCTCAT TAACTRCCATC', 'CCTGAGCTCATTA ACTRCCATCA'] | 5550-5551 | ['CCCTGAGCTCAT TAACTRCCATC', 'CCTGAGCTCATTA ACTRCCATCA'] |
| NM_003413.3 (ZIC3):c.1213A>G (p.Lys405Glu) | 7547 | ZIC3 | 5140 | ['CTACACGCACCCG AGCTCCCTGCGCRA ACACATGAAGGTAA TTACCTCTTT'] | 5327 | ['CCCGAGCTCCCTG CGCRAACACAT'] | 5552-5553 | ['CCCGAGCTCCCT GCGCRAACACA', 'CCGAGCTCCCTGC GCRAACACAT'] |
| NM_005448.2 (BMP15):c.704A>G (p.Tyr235Cys) | 9210 | BMP15 | 5141 | ['TTGGACATTGCCTT CTTGTTACTCTRTTT CAATGATACTCATA AAAGCATT'] | 5328 | ['CCTTCTTGTTACT CTRTTTCAAT'] | 5554 | ['CCTTCTTGTTACT CTRTTTCAAT'] |
| NM_001363.4 (DKC1):c.1069A>G (p.Thr357Ala) | 1736 | DKC1 | 5142 | ['ATTAATGACCACA GCGGTCATCTCTRC CTGCGACCATGGTA TAGTAGCCAA'] | 5329 | ['CCACAGCGGTCA TCTCTRCCTGC'] | 5555 | ['CCACAGCGGTCA TCTCTRCCTGC'] |
| NM_000481.3 (AMT):c.125A>G (p.His42Arg) | 275 | AMT | 5143 | ['CGCAGGACACCGC TCTATGACTTCCRCC TGGCCCACGGCGGG AAAATGGTG'] | 5330 | ['CCGCTCTATGAC TTCCRCCTGGC'] | 5556 | ['CCGCTCTATGAC TTCCRCCTGGC'] |
| NM_003361.3 (UMOD):c.383A>G (p.Asn128Ser) | 7369 | UMOD | 5144 | ['TGCCACGCCCTGG CCACATGTGTCART GTGGTGGGCAGCTA CTTGTGCGTA'] | 5331 | ['CCTGGCCACATG TGTCARTGTGG'] | 5557-5558 | ['CCCTGGCCACAT GTGTCARTGTG', 'CCTGGCCACATGT GTCARTGTGG'] |
| NM_001382.3 (DPAGT1):c.509A>G (p.Tyr170Cys) | 1798 | DPAGT1 | 5145 | ['TCTCTCCCCGCAGG AATCCTGTACTRTGT CTACATGGGGCTGC TGGCAGTG'] | 5332 | ['CCGCAGGAATCC TGTACTRTGTC'] | 5559 | ['CCGCAGGAATCC TGTACTRTGTC'] |
| NM_001128177.1 (THRB):c.1324A>G (p.Met442Val) | 7068 | THRB | 5146 | ['CTGCCATGCCAGC CGCTTCCTGCACRT GAAGGTGGAATGCC CCACAGAACT'] | 5333 | ['CCAGCCGCTTCC TGCACRTGAAG'] | 5560 | ['CCAGCCGCTTCC TGCACRTGAAG'] |
| NM_000141.4 (FGFR2):c.874A>G (p.Lys292Glu) | 2263 | FGFR2 | 5147 | ['TGCCCAGCCCCAC ATCCAGTGGATCRA GCACGTGGAAAAGA ACGGCAGTAA'] | 5334 | ['CCCACATCCAGT GGATCRAGCAC'] | 5561-5563 | ['CCCCACATCCAG TGGATCRAGCA', 'CCCACATCCAGT GGATCRAGCAC', 'CCACATCCAGTG GATCRAGCACG'] |

TABLE 3-continued

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_000371.3 (TTR):c.401A>G (p.Tyr134Cys) | 7276 | TTR | 5148 | ['ACCATTGCCGCCCT GCTGAGCCCCTRCT CCTATTCCACCACG GCTGTCGTC'] | 5335-5337 | ['CCGCCCTGCTGA GCCCCTRCTCC', 'CCCTGCTGAGCCC CTRCTCCTAT', 'CCTGCTGAGCCCC TRCTCCTATT'] | 5564-5566 | ['CCGCCCTGCTGA GCCCCTRCTCC', 'CCCTGCTGAGCCC CTRCTCCTAT', 'CCTGCTGAGCCCC TRCTCCTATT'] |
| NM_000371.3 (TTR):c.379A>G (p.Ile127Val) | 7276 | TTR | 5149 | ['CGACTCCGGCCCC CGCCGCTACACCRT TGCCGCCCTGCTGA GCCCCTACTC'] | 5338 | ['CCCCCGCCGCTA CACCRTTGCCG'] | 5567-5569 | ['CCCCCGCCGCTA CACCRTTGCCG', 'CCCCGCCGCTAC ACCRTTGCCGC', 'CCCGCCGCTACA CCRTTGCCGCC'] |
| NM_000174.4 (GP9):c.182A>G (p.Asn61Ser) | 2815 | GP9 | 5150 | ['ACCCGCCACCTTCT GCTGGCCAACARCA GCCTTCAGTCCGTG CCCCCGGGA'] | 5339 | ['CCTTCTGCTGGC CAACARCAGCC'] | 5570 | ['CCTTCTGCTGGC CAACARCAGCC'] |
| NM_000222.2 (KIT):c.1924A>G (p.Lys642Glu) | 3815 | KIT | 5151 | ['ACGGGAAGCCCTC ATGTCTGAACTCRA AGTCCTGAGTTACC TTGGTAATCA'] | 5340-5341 | ['CCCTCATGTCTG AACTCRAAGTC', 'CCTCATGTCTGAA CTCRAAGTCC'] | 5571-5572 | ['CCCTCATGTCTG AACTCRAAGTC', 'CCTCATGTCTGAA CTCRAAGTCC'] |
| NM_000530.6 (MPZ):c.242A>G (p.His81Arg) | 4359 | MPZ | 5152 | ['TCCCCTCATTCCTC ATAGATCTTCCRCT ATGCCAAGGGACAA CCCTACATT'] | 5342 | ['CCTCATAGATCT TCCRCTATGCC'] | 5573 | ['CCTCATAGATCT TCCRCTATGCC'] |
| NM_000233.3 (LHCGR):c.1733A>G (p.Asp578Gly) | −1 | — | 5153 | ['AAAATGGCAATCC TCATCTTCACCGRTT TCACCTGCATGGCA CCTATCTCT'] | 5343 | ['CCTCATCTTCAC CGRTTTCACCT'] | 5574 | ['CCTCATCTTCAC CGRTTTCACCT'] |
| NM_000421.3 (KRT10):c.1374-2A>G | −1 | — | 5154 | ['CCGCCGCGTCCGC CGCCTCCGGAACYA AACGGGGTGAGGTC ACATTCGGTT'] | 5344 | ['CCGCCGCCTCCG GAACYAAACGG'] | 5575 | ['CCGCCGCCTCCG GAACYAAACGG'] |
| NM_000422.2 (KRT17):c.274A>G (p.Asn92Asp) | 3872 | KRT17 | 5155 | ['TGAGAAGGCCACC ATGCAGAACCTCVA TGACCGCCTGGCCT CCTACCTGGA'] | 5345 | ['CCACCATGCAGA ACCTCVATGAC'] | 5576-5577 | ['CCACCATGCAGA ACCTCVATGAC', 'CCATGCAGAACC TCVATGACCGC'] |
| NM_000422.2 (KRT17):c.275A>G (p.Asn92Ser) | 3872 | KRT17 | 5156 | ['GAGAAGGCCACCA TGCAGAACCTCART GACCGCCTGGCCTC CTACCTGGAC'] | 5346 | ['CCACCATGCAGA ACCTCARTGAC'] | 5578-5579 | ['CCACCATGCAGA ACCTCARTGAC', 'CCATGCAGAACC TCARTGACCGC'] |
| NM_000823.3 (GHRHR):c.985A>G (p.Lys329Glu) | 2692 | GHRHR | 5157 | ['TTGTCTTTCCTGCA GGCGTCTCTCCRAG TCGACACTTTTCCTG ATCCCACT'] | 5347 | ['CCTGCAGGCGTC TCTCCRAGTCG'] | 5580 | ['CCTGCAGGCGTC TCTCCRAGTCG'] |
| NM_000407.4 (GP1BB):c.338A>G (p.Tyr113Cys) | −1 | — | 5158 | ['GCCGGCCGCCCCG AGCGTGCGCCCTDC CGCGACCTGCGTTG CGTGGCGCCC'] | 5348-5349 | ['CCCCGAGCGTGC GCCCTDCCGCG', 'CCCGAGCGTGCG CCCTDCCGCGA'] | 5581-5583 | ['CCCCGAGCGTGC GCCCTDCCGCG', 'CCCGAGCGTGCG CCCTDCCGCGA', 'CCGAGCGTGCGC CCTDCCGCGAC'] |
| NM_001146040.1 (GLRA1):c.920A>G (p.Tyr307Cys) | 2741 | GLRA1 | 5159 | ['CCTCCACCCCCACT CTAGGTGTCCTVTGT GAAAGCCATTGACA TTTGGATG'] | 5350-5351 | ['CCCCACTCTAGG TGTCCTVTGTG', 'CCCACTCTAGGTG TCCTVTGTGA'] | 5584-5586 | ['CCCCACTCTAGG TGTCCTVTGTG', 'CCCACTCTAGGTG TCCTVTGTGA', 'CCACTCTAGGTGT CCTVTGTGAA'] |
| NM_182925.4 (FLT4):c.3104A>G (p.His1035Arg) | 2324 | FLT4 | 5160 | ['CGCCTCCCCGCACC CCAGTGCATCCRCA GAGACCTGGCTGCT CGGAACATT'] | 5352 | ['CCGCACCCCAGT GCATCCRCAGA'] | 5587 | ['CCGCACCCCAGT GCATCCRCAGA'] |
| NM_212482.1 (FN1):c.2918A>G (p.Tyr973Cys) | 2335 | FN1 | 5161 | ['ACCGGGCTGTCCC CTGGGGTCACCTRT TACTTCAAAGTCTTT GCAGTGAGC'] | 5353-5354 | ['CCCCTGGGGTCA CCTRTTACTTC', 'CCCTGGGGTCAC CTRTTACTTCA'] | 5588-5589 | ['CCCCTGGGGTCA CCTRTTACTTC', 'CCCTGGGGTCAC CTRTTACTTCA'] |
| NM_000121.3 (EPOR):c.1460A>G (p.Asn487Ser) | 2057 | EPOR | 5162 | ['GGCTTATCCGATG GCCCCTACTCCARC CCTTATGAGAACAG CCTTATCCCA'] | 5355 | ['CCGATGGCCCCT ACTCCARCCCT'] | 5590 | ['CCGATGGCCCCT ACTCCARCCCT'] |

TABLE 3-continued

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_001735.2 (C5):c.1115A>G (p.Lys372Arg) | 727 | C5 | 5163 | ['CGTCTACCCCCTCA CCCAATCTACCYTG ATGGGATATGGAAT CCCAGGCTT'] | 5356-5357 | ['CCCCTCACCCAA TCTACCYTGAT', 'CCCTCACCCAATC TACCYTGATG'] | 5591-5593 | ['CCCCTCACCCAA TCTACCYTGAT', 'CCCTCACCCAATC TACCYTGATG', 'CCTCACCCAATCT ACCYTGATGG'] |
| NM_001844.4 (COL2A1):c.4172A>G (p.Tyr1391Cys) | 1280 | COL2A1 | 5164 | ['ACGGAAGGCTCCC AGAACATCACCTRC CACTGCAAGAACAG CATTGCCTAT'] | 5358-5359 | ['CCCAGAACATCA CCTRCCACTGC', 'CCAGAACATCAC CTRCCACTGCA'] | 5594-5595 | ['CCCAGAACATCA CCTRCCACTGC', 'CCAGAACATCAC CTRCCACTGCA'] |
| NM_001904.3 (CTNNB1):c.121A>G (p.Thr41Ala) | 1499 | CTNNB1 | 5165 | ['CTCTGGAATCCATT CTGGTGCCACTNCC ACAGCTCCTTCTCTG AGTGGTAA'] | 5360 | ['CCATTCTGGTGC CACTNCCACAG'] | 5596 | ['CCATTCTGGTGC CACTNCCACAG'] |
| NM_000040.1 (APOC3):c.280A>G (p.Thr94Ala) | 345 | APOC3 | 5166 | ['GGATTTGGACCCT GAGGTCAGACCARC TTCAGCCGTGGCTG CCTGAGACCT'] | 5361-5362 | ['CCCTGAGGTCAG ACCARCTTCAG', 'CCTGAGGTCAGA CCARCTTCAGC'] | 5597-5598 | ['CCCTGAGGTCAG ACCARCTTCAG', 'CCTGAGGTCAGA CCARCTTCAGC'] |
| NM_000488.3 (SERPINC1):c.655A>G (p.Asn219Asp) | 462 | SERPINC1 | 5167 | ['TGCAGAGCAATCC AGAGCGGCCATCRA CAAATGGGTGTCCA ATAAGACCGA'] | 5363 | ['CCAGAGCGGCCA TCRACAAATGG'] | 5599 | ['CCAGAGCGGCCA TCRACAAATGG'] |
| NM_001085.4 (SERPINA3):c.1240A>G (p.Met414Val) | 12 | SERPINA3 | 5168 | ['TACAGACACCCAG AACATCTTCTTCRTG AGCAAAGTCACCAA TCCCAAGCA'] | 5364 | ['CCCAGAACATCT TCTTCRTGAGC'] | 5600-5601 | ['CCCAGAACATCT TCTTCRTGAGC', 'CCAGAACATCTTC TTCRTGAGCA'] |
| NM_001145.4 (ANG):c.121A>G (p.Lys41Glu) | −1 | — | 5169 | ['CTTCCTGACCCAGC ACTATGATGCCRAA CCACAGGGCCGGGA TGACAGATA'] | 5365 | ['CCAGCACTATGA TGCCRAACCAC'] | 5602-5603 | ['CCCAGCACTATG ATGCCRAACCA', 'CCAGCACTATGA TGCCRAACCAC'] |
| NM_001100.3 (ACTA1):c.350A>G (p.Asn117Ser) | 58 | ACTA1 | 5170 | ['GAGGCCCCCCTCA ATCCCAAGGCCARC CGCGAGAAGATGAC CCAGATCATG'] | 5366 | ['CCTCAATCCCAA GGCCARCCGCG'] | 5604-5605 | ['CCCTCAATCCCA AGGCCARCCGC', 'CCTCAATCCCAA GGCCARCCGCG'] |
| NM_014053.3 (FLVCR1):c.361A>G (p.Asn121Asp) | 28982 | FLVCR1 | 5171 | ['GATCTTCAGCCTGT ACTCGCTGGTCRAC GCCTTTCAGTGGAT CCAGTACAG'] | 5367 | ['CCTGTACTCGCT GGTCRACGCCT'] | 5606 | ['CCTGTACTCGCT GGTCRACGCCT'] |
| NM_000334.4 (SCN4A):c.4078A>G (p.Met1360Val) | 6329 | SCN4A | 5172 | ['GAAGCAGGCCTTC GACATCACCATCRT GATCCTCATCTGCCT CAACATGGT'] | 5368 | ['CCTTCGACATCA CCATCRTGATC'] | 5607 | ['CCTTCGACATCA CCATCRTGATC'] |
| NM_004519.3 (KCNQ3):c.1403A>G (p.Asn468Ser) | 3786 | KCNQ3 | 5173 | ['GAACCAAAGCCTG TTGGCTTAAACART AAAGAGCGTTTCCG CACGGCCTTC'] | 5369 | ['CCTGTTGGCTTA AACARTAAAGA'] | 5608 | ['CCTGTTGGCTTA AACARTAAAGA'] |
| NM_007375.3 (TARDBP):c.800A>G (p.Asn267Ser) | 23435 | TARDBP | 5174 | ['AATGCCGAACCTA AGCACAATAGCART AGACAGTTAGAAAG AAGTGGAAGA'] | 5370 | ['CCTAAGCACAAT AGCARTAGACA'] | 5609 | ['CCTAAGCACAAT AGCARTAGACA'] |
| NM_032520.4 (GNPTG):c.6102A>G | 84572 | GNPTG | 5175 | ['TGCTGCCCCTGCAT CCTCCACCTTCRGG GCCATGAGAAGTTG CTGAGGACA'] | 5371 | ['CCTGCATCCTCC ACCTTCRGGGC'] | 5610 | ['CCTGCATCCTCC ACCTTCRGGGC'] |
| NM_000495.4 (COL4A5):c.466-2A>G | 1287 | COL4A5 | 5176 | ['AGAACTTCCATTG ATGGCTTCTTTTRGG GTGAACCAGGTAGT ATAATTATG'] | 5372 | ['CCATTGATGGCT TCTTTTRGGGT'] | 5611 | ['CCATTGATGGCT TCTTTTRGGGT'] |
| NM_000495.4 (COL4A5):c.1340-2A>G | 12875 | COMA | 5177 | ['TTGCTATCCTTTCT TTATCTTACTCRGGT GATGAGATATGTGA ACCAGGCC'] | 5373 | ['CCTTTCTTTATCT TACTCRGGTG'] | 5612 | ['CCTTTCTTTATCT TACTCRGGTG'] |
| NM_000060.3 (BTD):c.278A>G (p.Tyr93Cys) | 686 | BTD | 5178 | ['CTCATGAACCAGA ACCTTGACATCTRT GAACAGCAAGTGAT GACTGCAGCC'] | 5374 | ['CCAGAACCTTGA CATCTRTGAAC'] | 5613 | ['CCAGAACCTTGA CATCTRTGAAC'] |
| NM_000060.3 (BTD):c.641A>G (p.Asn214Ser) | 686 | BTD | 5179 | ['CTTGTTGACCGCTA CCGTAAACACARCC TCTACTTTGAGGCA GCATTCGAT'] | 5375 | ['CCGCTACCGTAA ACACARCCTCT'] | 5614 | ['CCGCTACCGTAA ACACARCCTCT'] |

TABLE 3-continued

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_000094.3 (COL7A1):c.425A>G (p.Lys142Arg) | 1294 | COL7A1 | 5180 | ['CAGCTGGCCCGAC CTGGTGTCCCCARG GTGATCCCTACCCC TACCATGCCT'] | 5376 | ['CCCGACCTGGTG TCCCCARGGTG'] | 5615-5616 | ['CCCGACCTGGTG TCCCCARGGTG', 'CCGACCTGGTGTC CCCARGGTGA'] |
| NM_005247.2 (FGF3):c.146A>G (p.Tyr49Cys) | 2248 | FGF3 | 5181 | ['GGGGCGCCCCGGC GCCGCAAGCTCTRC TGCGCCACGAAGTA CCACCTCCAG'] | 5377-5378 | ['CCCGGCGCCGCA AGCTCTRCTGC', 'CCGGCGCCGCAA GCTCTRCTGCG'] | 5617-5618 | ['CCCGGCGCCGCA AGCTCTRCTGC', 'CCGGCGCCGCAA GCTCTRCTGCG'] |
| NM_000313.3 (PROS1):c.701A>G (p.Tyr234Cys) | 5627 | PROS1 | 5182 | ['TGTGAATGCCCCG AAGGCTACAGATRT AATCTCAAATCAAA GTCTTGTGAA'] | 5379-5380 | ['CCCGAAGGCTAC AGATRTAATCT', 'CCGAAGGCTACA GATRTAATCTC'] | 5619-5621 | ['CCCCGAAGGCTA CAGATRTAATCT', 'CCCGAAGGCTAC AGATRTAATCT', 'CCGAAGGCTACA GATRTAATCTC'] |
| NM_004612.3 (TGFBR1):c.134A>G (p.Asn45Ser) | 7046 | TGFBR1 | 5183 | ['TTCTGCCACCTCTG TACAAAAGACARTT TTACTTGTGTGACA GATGGGCTC'] | 5381 | ['CCTCTGTACAAA AGACARTTTTA'] | 5622 | ['CCTCTGTACAAA AGACARTTTTA'] |
| m.608A>G | 4558 | MT-TF | 5184 | ['GTAGCTTACCTCCT CAAAGCAATACRCT GAAAATGTTTAGAC GGGCTCACA'] | 5382 | ['CCTCCTCAAAGC AATACRCTGAA'] | 5623-5624 | ['CCTCCTCAAAGC AATACRCTGAA', 'CCTCAAAGCAAT ACRCTGAAAAT'] |
| NM_001376.4 (DYNC1H1):c.2909A>G (p.Tyr970Cys) | 1778 | DYNC1H1 | 5185 | ['CTAAGAATAACCA ATCAGGTAATCTRC TTGAATCCACCAAT TGAAGAGTGC'] | 5383 | ['CCAATCAGGTAA TCTRCTTGAAT'] | 5625 | ['CCAATCAGGTAA TCTRCTTGAAT'] |
| NM_000459.4 (TEK):c.2690A>G (p.Tyr897Cys) | 7010 | TEK | 5186 | ['ATGCTCTCTTCCTT CCCTCCAGGCTVCT TGTACCTGGCCATT GAGTACGCG'] | 5384 | ['CCTTCCCTCCAG GCTVCTTGTAC'] | 5626 | ['CCTTCCCTCCAG GCTVCTTGTAC'] |
| NM_014191.3 (SCN8A):c.5302A>G (p.Asn1768Asp) | 6334 | SCN8A | 5187 | ['CATGTACATTGCCA TCATCCTGGAGRAC TTCAGTGTAGCCAC AGAGGAAAG'] | 5385 | ['CCATCATCCTGG AGRACTTCAGT'] | 5627 | ['CCATCATCCTGG AGRACTTCAGT'] |
| NM_002552.4 (ORC4):c.521A>G (p.Tyr174Cys) | 5000 | ORC4 | 5188 | ['CATCATAAAAACC AAACACTTCTCTRT AATCTTTTTGACATT TCTCAGTCT'] | 5386 | ['CCAAACACTTCT CTRTAATCTTT'] | 5628 | ['CCAAACACTTCT CTRTAATCTTT'] |
| NM_004813.2 (PEX16):c.992A>G (p.Tyr331Cys) | 9409 | PEX16 | 5189 | ['TACTTGCCCACCTG GCAGAAAATCTRCT TCTACAGTTGGGGC TGACAGACC'] | 5387-5388 | ['CCACCTGGCAGA AAATCTRCTTC', 'CCTGGCAGAAAA TCTRCTTCTAC'] | 5629-5630 | ['CCACCTGGCAGA AAATCTRCTTC', 'CCTGGCAGAAAA TCTRCTTCTAC'] |
| NM_016952.4 (CDON):c.2368A>G (p.Thr790Ala) | 50937 | CDON | 5190 | ['GTTTTTGTTTTCCC TCAAAGGTTCARCA TACAAATTTAGGGT CATTGCCAT'] | 5389 | ['CCCTCAAAGGTT CARCATACAAA'] | 5631 | ['CCCTCAAAGGTT CARCATACAAA'] |
| NM_016464.4 (TMEM138):c.287A>G (p.His96Arg) | 51524 | TMEM138 | 5191 | ['TACTTTGCCCTCAG CATCTCCCTTCRTGT CTGGGTCATGGTAA GAGTGGCA'] | 5390-5391 | ['CCCTCAGCATCT CCCTTCRTGTC', 'CCTCAGCATCTCC CTTCRTGTCT'] | 5632-5633 | ['CCCTCAGCATCT CCCTTCRTGTC', 'CCTCAGCATCTCC CTTCRTGTCT'] |
| NM_005022.3 (PFN1):c.350A>G (p.Glu117Gly) | 5216 | PFN1 | 5192 | ['GTTGATCAAACCA CCGTGGACACCTYC TTTGCCCATCAGCA GGACTAGCGC'] | 5392 | ['CCACCGTGGACA CCTYCTTTGCC'] | 5634 | ['CCACCGTGGACA CCTYCTTTGCC'] |
| NM_022787.3 (NMNAT1):c.817A>G (p.Asn273Asp) | 64802 | NMNAT1 | 5193 | ['GGTCATCCTGGCCC CTTTGCAGAGARAC ACTGCAGAAGCTAA GACATAGGA'] | 5393 | ['CCCCTTTGCAGA GARACACTGCA'] | 5635 | ['CCCCTTTGCAGA GARACACTGCA'] |
| NM_005340.6 (HINT1):c.152A>G (p.His51Arg) | 3094 | HINT1 | 5194 | ['GACATTTCCCCTCA AGCACCAACACRTT TTCTGGTGATACCC AAGAAACAT'] | 5394-5396 | ['CCCCTCAAGCAC CAACACRTTTT', 'CCCTCAAGCACC AACACRTTTTC', 'CCTCAAGCACCA ACACRTTTTCT'] | 5636-5638 | ['CCCCTCAAGCAC CAACACRTTTT', 'CCCTCAAGCACC AACACRTTTTC', 'CCTCAAGCACCA ACACRTTTTCT'] |
| NM_005211.3 (CSF1R):c.2320-2A>G | 1436 | CSF1R | 5195 | ['GACTAACCCTGCA GTGCTTTCCCTCRGT GCATCCACCGGGAC GTGGCAGCG'] | 5397 | ['CCTGCAGTGCTT TCCCTCRGTGC'] | 5639 | ['CCTGCAGTGCTT TCCCTCRGTGC'] |

TABLE 3-continued

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_001039958.1 (MESP2):c.271A>G (p.Lys91Glu) | 145873 | MESP2 | 5196 | ['GCGGCAGAGCGCCAGCGAGCGGGAGRAACTGCGCATGCGCACGCTGGCCCG'] | 5398 | ['CCAGCGAGCGGGAGRAACTGCGC'] | 5640 | ['CCAGCGAGCGGGAGRAACTGCGC'] |
| NM_001099274.1 (TINF2):c.850A>G (p.Thr284Ala) | 26277 | TINF2 | 5197 | ['TAGGGGAGGCCATAAGGAGCGCCCCRCAGTCATGCTGTTTCCCTTTAGGAA'] | 5399 | ['CCATAAGGAGCGCCCCRCAGTCA'] | 5641 | ['CCATAAGGAGCGCCCCRCAGTCA'] |
| NM_003863.3 (DPM2):c.68A>G (p.Tyr23Cys) | 8818 | DPM2 | 5198 | ['GCCGTTAGCCTGATCATCTTCACCTRCTACACCCGCCTGGGTGATTCTCTTG'] | 5400 | ['CCTGATCATCTTCACCTRCTACA'] | 5642 | ['CCTGATCATCTTCACCTRCTACA'] |
| NM_000530.6 (MPZ):c.347A>G (p.Asn116Ser) | 4359 | MPZ | 5199 | ['AAGGATGGCTCCATTGTCATACACARCCTAGACTACAGTGACAATGGCACG'] | 5401 | ['CCATTGTCATACACARCCTAGAC'] | 5643 | ['CCATTGTCATACACARCCTAGAC'] |
| NM_000138.4 (FBN1):c.3058A>G (p.Thr1020Ala) | 2200 | FBN1 | 5200 | ['ACCCGGATTTGCCACAAAAGAAATTRCAAATGGAAAGCCTTTCTTCAAAGG'] | 5402 | ['CCACAAAAGAAATTRCAAATGGA'] | 5644 | ['CCACAAAAGAAATTRCAAATGGA'] |
| NM_000169.2 (GLA):c.1153A>G (p.Thr385Ala) | −1 | — | 5201 | ['GGCCTGTAATCCTGCCTGCTTCATCRCACAGCTCCTCCCTGTGAAAAGGAA'] | 5403 | ['CCTGCCTGCTTCATCRCACAGCT'] | 5645 | ['CCTGCCTGCTTCATCRCACAGCT'] |
| NM_000257.3 (MYH7):c.2206A>G (p.Ile736Val) | 4625 | MYH7 | 5202 | ['AGCGGCCATCCCTGAGGGACAGTTCRTTGATAGCAGGAAGGGGGCAGAGAA'] | 5404 | ['CCCTGAGGGACAGTTCRTTGATA'] | 5646-5647 | ['CCCTGAGGGACAGTTCRTTGATA', 'CCTGAGGGACAGTTCRTTGATAG'] |
| NM_018972.2 (GDAP1):c.368A>G (p.His123Arg) | 54332 | GDAP1 | 5203 | ['AGCATGTATTACCCACGGGTACAACRTTACCGAGAGCTGCTTGACTCCTTG'] | 5405 | ['CCCACGGGTACAACRTTACCGAG'] | 5648 | ['CCCACGGGTACAACRTTACCGAG'] |
| NM_001946.3 (DUSP6):c.566A>G (p.Asn189Ser) | 1848 | DUSP6 | 5204 | ['ACTACCATCCGAGTCTGTTGCACTAYTGGGGTCTCGGTCAAGGTCAGACTC'] | 5406 | ['CCGAGTCTGTTGCACTAYTGGGG'] | 5649 | ['CCGAGTCTGTTGCACTAYTGGGG'] |
| NM_003867.3 (FGF17):c.560A>G (p.Asn187Ser) | 8822 | FGF17 | 5205 | ['TACCAAGGCCAGCTGCCCTTCCCCARCCACGCCGAGAAGCAGAAGCAGTTC'] | 5407 | ['CCAGCTGCCCTTCCCCARCCACG'] | 5650 | ['CCAGCTGCCCTTCCCCARCCACG'] |
| NM_015560.2 (OPA1):c.1146A>G (p.Ile382Met) | 4976 | OPA1 | 5206 | ['TTTTTATTTTTCCTGAGTAGACCATRTCCTTAAATGTAAAAGGCCCTGGAC'] | 5408 | ['CCTGAGTAGACCATRTCCTTAAA'] | 5651 | ['CCTGAGTAGACCATRTCCTTAAA'] |
| NM_002972.3 (SBF1):c.1249A>G (p.Met417Val) | 6305 | SBF1 | 5207 | ['AAGGCCATGCCCTCCAGCACCTTCAYCAGGAAATCGTCCTTACCAGCCCA'] | 5409 | ['CCCTCCAGCACCTTCAYCAGGAA'] | 5652-5653 | ['CCCTCCAGCACCTTCAYCAGGAA', 'CCTCCAGCACCTTCAYCAGGAAA'] |
| NM_006876.2 (B4GAT1):c.1168A>G (p.Asn390Asp) | 11041 | B4GAT1 | 5208 | ['GTTCCATCCCCAAAAGGAGGCTGAAATCAGCACAATAAGATCCTATATCG'] | 5410 | ['CCAAAAGGAGGCTGAARATCAGC'] | 5654-5656 | ['CCCCAAAAGGAGGCTGAARATCA', 'CCCAAAAGGAGGCTGAARATCAG', 'CCAAAAGGAGGCTGAARATCAGC'] |
| NM_000218.2 (KCNQ1):c.332A>G (p.Tyr111Cys) | 3784 | KCNQ1 | 5209 | ['CGCACCCACGTCCAGGGCCGCGTCTRCAACTTCCTCGAGCGTCCCACCGGC'] | 5411 | ['CCAGGGCCGCGTCTRCAACTTCC'] | 5657 | ['CCAGGGCCGCGTCTRCAACTTCC'] |
| NM_000492.3 (CFTR):c.1A>G (p.Met1Val) | 1080 | CFTR | 5210 | ['CAGGGACCCCAGCGCCCGAGAGACCRTGCAGAGGTCGCCTTGGAAAAGGC'] | 5412 | ['CCAGCGCCCGAGAGACCRTGCAG'] | 5658-5659 | ['CCCAGCGCCCGAGAGACCRTGCA', 'CCAGCGCCCGAGAGACCRTGCAG'] |
| NM_007294.3 (BRCA1):c.122A>G (p.His41Arg) | 672 | BRCA1 | 5211 | ['GAACCTGTCTCCACAAAGTGTGACCRCATATTTTGCAAGTAAGTTTGAATG'] | 5413 | ['CCACAAAGTGTGACCRCATATTT'] | 5660 | ['CCACAAAGTGTGACCRCATATTT'] |
| NM_007294.3 (BRCA1):c.44852A>G | 672 | BRCA1 | 5212 | ['GTTTTCTCCTTCCATTTATCTTTCTRGGTCATCCCCTTCTAAATGCCCATC'] | 5414 | ['CCTTCCATTTATCTTTCTRGGTC'] | 5661-5662 | ['CCTTCCATTTATCTTTCTRGGTC', 'CCATTTATCTTTCTRGGTCATCC'] |

TABLE 3-continued

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_014795.3 (ZEB2):c.3134A>G (p.His1045Arg) | 9839 | ZEB2 | 5213 | ['AAACACAAGCACC ACCTTATCGAGCRC TCAAGGCTTCACTC GGGCGAGAAG'] | 5415 | ['CCACCTTATCGA GCRCTCAAGGC'] | 5663 | ['CCACCTTATCGA GCRCTCAAGGC'] |
| NM_001287.5 (CLCN7):c.296A>G (p.Tyr99Cys) | 1186 | CLCN7 | 5214 | ['TGTCCCGGCCTGCA GAGCTTGGACTRTG ACAACAGTGAGAAC CAGCTGTTC'] | 5416 | ['CCTGCAGAGCTT GGACTRTGACA'] | 5664 | ['CCTGCAGAGCTT GGACTRTGACA'] |
| NM_080605.3 (B3GALT6):c.1A>G (p.MetlVal) | 126792 | B3GALT6 | 5215 | ['CGCCACGCCCGCC GCAGCAGCTTCAYG GCGCCCGCGCCGGG CCGGCGGCCC'] | 5417 | ['CCCGCCGCAGCA GCTTCAYGGCG'] | 5665-5667 | ['CCCGCCGCAGCA GCTTCAYGGCG', 'CCGCCGCAGCAG CTTCAYGGCGC', 'CCGCAGCAGCTT CAYGGCGCCCG'] |
| NM_000207.2 (1NS):c.*59A>G | −1 | — | 5216 | ['TCCTGCACCGAGA GAGATGGAATAARG CCCTTGAACCAGCC CTGCTGTGCC'] | 5418 | ['CCGAGAGAGATG GAATAARGCCC'] | 5668 | ['CCGAGAGAGATG GAATAARGCCC'] |
| NM_000784.3 (CYP27A1):c.1061A>G (p.Asp354Gly) | 1593 | CYP27A1 | 5217 | ['TGGGCCCTGTACC ACCTCTCAAAGGRC CCTGAGATCCAGGA GGCCTTGCAC'] | 5419 | ['CCACCTCTCAAA GGRCCCTGAGA'] | 5669 | ['CCACCTCTCAAA GGRCCCTGAGA'] |
| NM_000540.2 (RYRO:c.14572A>G (p.Asn4858Asp) | 6261 | RYR1 | 5218 | ['CTACCTGTACACCG TGGTGGCCTTCRAC TTCTTCCGCAAGTTC TACAACAA'] | 5420 | ['CCGTGGTGGCCT TCRACTTCTTC'] | 5670 | ['CCGTGGTGGCCT TCRACTTCTTC'] |
| NM_000238.3 (KCNH2):c.1478A>G (p.Tyr493Cys) | 3757 | KCNH2 | 5219 | ['CACCCCGGCCGCA TCGCCGTCCACTNC TTCAAGGGCTGGTT CCTCATCGAC'] | 5421 | ['CCGCATCGCCGT CCACTNCTTCA'] | 5671 | ['CCGCATCGCCGT CCACTNCTTCA'] |
| NM_000335.4 (SCN5A):c.688A>G (p.Ile230Val) | 6331 | SCN5A | 5220 | ['CCGAGTCCTCCGG GCCCTGAAAACTRT ATCAGTCATTTCAG GTGAAAATCA'] | 5422 | ['CCGGGCCCTGAA AACTRTATCAG'] | 5672 | ['CCGGGCCCTGAA AACTRTATCAG'] |
| NM_000169.2 (GLA):c.548-2A>G | −1 | — | 5221 | ['TATTTTACCCATTG TTTTCTCATACRGGT TATAAGCACATGTC CTTGGCCC'] | 5423 | ['CCCATTGTTTTCT CATACRGGTT'] | 5673-5674 | ['CCCATTGTTTTCT CATACRGGTT', 'CCATTGTTTTCTC ATACRGGTTA'] |
| NM_000146.3 (FTL):c.1A>G (p.MetlVal) | 2512 | FTL | 5222 | ['GTTAGCTCCTTCTT GCCAACCAACCRTG AGCTCCCAGATTCG TCAGAATTA'] | 5424 | ['CCTTCTTGCCAA CCAACCRTGAG'] | 5675 | ['CCTTCTTGCCAA CCAACCRTGAG'] |
| NM_000531.5 (OTC):c.1034A>G (p.Tyr345Cys) | 5009 | OTC | 5223 | ['GTCATGGTGTCCCT GCTGACAGATTRCT CACCTCAGCTCCAG AAGCCTAAA'] | 5425-5426 | ['CCCTGCTGACAG ATTRCTCACCT', 'CCTGCTGACAGA TTRCTCACCTC'] | 5676-5677 | ['CCCTGCTGACAG ATTRCTCACCT', 'CCTGCTGACAGA TTRCTCACCTC'] |
| NM_000531.5 (OTC):c.350A>G (p.His117Arg) | 5009 | OTC | 5224 | ['TGTTTTCTTACCAC ACAAGATATTCDTT TGGGTGTGAATGAA AGTCTCACG'] | 5427 | ['CCACACAAGATA TTCDTTTGGGT'] | 5678 | ['CCACACAAGATA TTCDTTTGGGT'] |
| NM_000531.5 (OTC):c.524A>G (p.Asp175Gly) | 5009 | OTC | 5225 | ['TACCATCCTATCCA GATCCTGGCTGDTT ACCTCACGCTCCAG GTTGGTTTA'] | 5428 | ['CCAGATCCTGGC TGDTTACCTCA'] | 5679 | ['CCAGATCCTGGC TGDTTACCTCA'] |
| NM_000531.5 (OTC):c.527A>G (p.Tyr176Cys) | 5009 | OTC | 5226 | ['CATCCTATCCAGAT CCTGGCTGATTRCCT CACGCTCCAGGTTG GTTTATTT'] | 5429 | ['CCAGATCCTGGC TGATTRCCTCA'] | 5680 | ['CCAGATCCTGGC TGATTRCCTCA'] |
| NM_000531.5 (OTC):c.542A>G (p.Glu181Gly) | 5009 | OTC | 5227 | ['TCTCCTTCATCCCG TGCCTTTTAGGRAC ACTATAGCTCTCTG AAAGGTCTT'] | 5430 | ['CCGTGCCTTTTA GGRACACTATA'] | 5681-5682 | ['CCGTGCCTTTT AGGRACACTAT', 'CCGTGCCTTTTAG GRACACTATA'] |
| NM_024301.4 (FKRP):c.1A>G (p.MetlVal) | 79147 | FKRP | 5228 | ['CCAGCTAGCCCCA GACTTCGGCCCCRT GCGGCTCACCCGCT GCCAGGCTGC'] | 5431 | ['CCCCAGACTTCG GCCCCRTGCGG'] | 5683-5685 | ['CCCCAGACTTCG GCCCCRTGCGG', 'CCCAGACTTCGG CCCCRTGCGGC', 'CCAGACTTCGGC CCCRTGCGGCT'] |

TABLE 3-continued

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_000321.2 (RBO:c.1927A>G (p.Lys643Glu) | 5925 | RB1 | 5229 | ['AGCCTTCCAGACC CAGAAGCCATTGRA ATCTACCTCTCTTTC ACTGTTTA'] | 5432 | ['CCCAGAAGCCAT TGRAATCTACC'] | 5686 | ['CCCAGAAGCCAT TGRAATCTACC'] |
| NM_015713.4 (RRM2B):c.581A>G(p.Glu194Gly) | 50484 | RRM2B | 5230 | ['AAAAGATCCTGAG AAGAAAACTCCTYC TACAGCAGCAAAGG CCACCACTCT'] | 5433 | ['CCTGAGAAGAAA ACTCCTYCTAC'] | 5687 | ['CCTGAGAAGAAA ACTCCTYCTAC'] |
| NM_000219.5 (KCNE1):c.242A>G (p.Tyr81Cys) | 3753 | KCNE1 | 5231 | ['CACTCGAACGACC CATTCAACGTCTDC ATCGAGTCCGATGC CTGGCAAGAG'] | 5434 | ['CCCATTCAACGT CTDCATCGAGT'] | 5688 | ['CCCATTCAACGT CTDCATCGAGT'] |
| NM_003108.3 (SOX11):c.347A>G (p.Tyr116Cys) | 6664 | SOX11 | 5232 | ['AAGCACATGGCCG ACTACCCCGACTRC AAGTACCGGCCCCG GAAAAAGCCC'] | 5435 | ['CCGACTACCCCG ACTRCAAGTAC'] | 5689 | ['CCGACTACCCCG ACTRCAAGTAC'] |
| NM_002764.3 (PRPSO:c.343A>G (p.Met115Val) | 5631 | PRPS1 | 5233 | ['AATCTCAGCCAAG CTTGTTGCAAATRTG CTATCTGTAGCAGG TGCAGATCA'] | 5436 | ['CCAAGCTTGTTG CAAATRTGCTA'] | 5690 | ['CCAAGCTTGTTG CAAATRTGCTA'] |
| NM_000546.5 (TP53):c.1101-2A>G | 7157 | TP53 | 5234 | ['TCTCCTCCCTGCTT CTGTCCTACRGCC ACCTGAAGTCCAAA AAGGGTCA'] | 5437 | ['CCTGCTTCTGTCT CCTACRGCCA'] | 5691 | ['CCTGCTTCTGTCT CCTACRGCCA'] |
| NM_000166.5 (GJB1):c.580A>G (p.Met194Val) | 2705 | GJB1 | 5235 | ['CGAGAAAACCGTC TTCACCGTCTTCRTG CTAGCTGCCTCTGG CATCTGCAT'] | 5438 | ['CCGTCTTCACCG TCTTCRTGCTA'] | 5692 | ['CCGTCTTCACCG TCTTCRTGCTA'] |
| NM_003159.2 (CDKL5):c.449A>G (p.Lys150Arg) | 6792 | CDKL5 | 5236 | ['TTAATCAGCCACA ATGATGTCCTAARA CTGTGTGACTTTGGT AAGTTAAAA'] | 5439 | ['CCACAATGATGT CCTAARACTGT'] | 5693 | ['CCACAATGATGT CCTAARACTGT'] |
| NM_000053.3 (ATP7B):c.122A>G (p.Asn41Ser) | 540 | ATP7B | 5237 | ['ATCCAGACCACCTT CATAGCCAACAYTG TCAAAAGCAAAACT CTTCTTCAT'] | 5440 | ['CCACCTTCATAG CCAACAYTGTCT'] | 5694-5695 | ['CCACCTTCATAG CCAACAYTGTC', 'CCTTCATAGCCAA CAYTGTCAAA'] |
| NM_006306.3 (SMC1A):c.3254A>G (p.Tyr1085Cys) | 8243 | SMC1A | 5238 | ['GTGGCTACCAACA TTGATGAGATCTRT AAGGCCCTGTCCCG CAATAGCAGT'] | 5441 | ['CCAACATTGATG AGATCTRTAAG'] | 5696 | ['CCAACATTGATG AGATCTRTAAG'] |
| NM_005154.4 (USP8):c.2150A>G (p.Tyr717Cys) | 9101 | USP8 | 5239 | ['GAACCTTCCAAAC TGAAGCGCTCCTDC TCCTCCCAGATAT AACCCAGGCT'] | 5442 | ['CCAAACTGAAGC GCTCCTDCTCC'] | 5697 | ['CCAAACTGAAGC GCTCCTDCTCC'] |
| NM_000117.2 (EMD):c.266-2A>G | 2010 | EMD | 5240 | ['TCTGCTACCGCTGC CCCCCTTCCCARGG CTACAATGACGACT ACTATGAAG'] | 5443 | ['CCGCTGCCCCCC TTCCCARGGCT'] | 5698 | ['CCGCTGCCCCCC TTCCCARGGCT'] |
| NM_207352.3 (CYP4V2):c.1393A>G (p.Arg465Gly) | 285440 | CYP4V2 | 5241 | ['CTACGTGCCCTTCT CTGCTGGCCCCRGG AACTGTATAGGTTT GTATCCATC'] | 5444 | ['CCCTTCTCTGCT GGCCCCRGGAA'] | 5699-5700 | ['CCCTTCTCTGCT GGCCCCRGGAA', 'CCTTCTCTGCTGG CCCCRGGAAC'] |
| NM_000546.5 (TP53):c.709A>G (p.Met237Val) | 7157 | TP53 | 5242 | ['CTGTACCACCATCC ACTACAACTACRTG TGTAACAGTTCCTG CATGGGCGG'] | 5445 | ['CCATCCACTACA ACTACRTGTGT'] | 5701 | ['CCATCCACTACA ACTACRTGTGT'] |
| NM_016069.9 (PAM16):c.226A>G (p.Asn76Asp) | −1 | — | 5243 | ['CTCACCCGTCCCCT CTCCTCTGCAGRAC TATGAACACTTATTT AAGGTGAA'] | 5446 | ['CCTCTCCTCTGC AGRACTATGAA'] | 5702-5704 | ['CCCCTCTCCTCT GCAGRACTATG', 'CCCTCTCCTCTGC AGRACTATGA', 'CCTCTCCTCTGCA GRACTATGAA'] |
| NM_006785.3 (MALT1):c.1019-2A>G | 10892 | MALT1 | 5244 | ['AACACCCCCTTTCT TTTTTTTCAARGCG AAGGACAAGGTTGC CCTTTTGA'] | 5447 | ['CCTTTCTTTTTTT TCAARGCGA'] | 5705 | ['CCTTTCTTTTTTT TCAARGCGA'] |
| NM_004771.3 (MMP20):c.611A>G (p.His204Arg) | 9313 | MMP20 | 5245 | ['GGAGAAGGCCTGG GAGGAGATACACRT TTCGACAATGCTGA GAAGTGGACT'] | 5448 | ['CCTGGGAGGAGA TACACRTTTCG'] | 5706 | ['CCTGGGAGGAGA TACACRTTTCG'] |

TABLE 3-continued

A to G with NGG PAM. Table 2 shows a list of A to G mutations that may be corrected using any of the base editors provided herein. GRNAs and gRNAall indicate the protospacer and PAM sequence, where the PAM sequence is the last 3 nucleotides of each of the sequences in GRNAs and gRNAall.

| Name | Gene ID | Gene Symbol | SEQ ID NO: | Flanks | SEQ ID NO: | GRNAs | SEQ ID NO: | gRNAall |
|---|---|---|---|---|---|---|---|---|
| NM_003159.2 (CDKL5):c.458A>G (p.Asp153Gly) | 6792 | CDKL5 | 5246 | ['CACAATGATGTCCT AAAACTGTGTGRCT TTGGTAAGTTAAAA AGAAATTAA'] | 5449 | ['CCTAAAACTGTG TGRCTTTGGTA'] | 5707 | ['CCTAAAACTGTG TGRCTTTGGTA'] |
| NM_001204830.1 (LIPT1):c.535A>G (p.Thr179Ala) | −1 | — | 5247 | ['CCGGACTACTGCCT ATCACCATTGCRCTT TATTATGTAGTACTG ATGGGAC'] | 5450 | ['CCTATCACCATT GCRCTTTATTA'] | 5708 | ['CCTATCACCATT GCRCTTTATTA'] |
| NM_000921.4 (PDE3A):c.1333A>G (p.Thr445Ala) | 5139 | PDE3A | 5248 | ['AGTTTCTTCCACTT GGACCACCACCRCC TCGGCCACAGGTCT ACCCACCTT'] | 5451 | ['CCACTTGGACCA CCACCRCCTCG'] | 5709 | ['CCACTTGGACCA CCACCRCCTCG'] |
| NM_000182.4 (HADHA):c.9192A>G | 3030 | HADHA | 5249 | ['TTGCTCAATTCCAG TCTTTACCACCYAA AAAACATATAAAGC ACTTGCTCA'] | 5452 | ['CCAGTCTTTACC ACCYAAAAAAC'] | 5710 | ['CCAGTCTTTACC ACCYAAAAAAC'] |
| NM_000169.2 (GLA):c.620A>G (p.Tyr207Cys) | −1 | — | 5250 | ['GTGTACTCCTGTGA GTGGCCTCTTTRTAT GTGGCCCTTTCAAA AGGTGAGA'] | 5453 | ['CCTGTGAGTGGC CTCTTTRTATG'] | 5711 | ['CCTGTGAGTGGC CTCTTTRTATG'] |
| NM_000238.3 (KCNH2):c.2582A>G (p.Asn861Ser) | 3757 | KCNH2 | 5251 | ['TGGTCCAGCCTGG AGATCACCTTCANC CTGCGAGATGTGAG TTGGCTGCCC'] | 5454 | ['CCTGGAGATCAC CTTCANCCTGC'] | 5712 | ['CCTGGAGATCAC CTTCANCCTGC'] |
| NM_000218.2 (KCNQ1):c.605A>G (p.Asp202Gly) | 3784 | KCNQ1 | 5252 | ['GCTCCCCCTCTCCT GCACTCCACAGRCC TCATCGTGGTCGTG GCCTCCATG'] | 5455 | ['CCTGCACTCCAC AGRCCTCATCG'] | 5713 | ['CCTGCACTCCAC AGRCCTCATCG'] |
| NM_012203.1 (GRHPR):c.934A>G (p.Asn312Asp) | 9380 | GRHPR | 5253 | ['CACCATGTCCTTGT TGGCAGCTAACRAC TTGCTGGCTGGCCT GAGAGGGGA'] | 5456 | ['CCTTGTTGGCAG CTAACRACTTG'] | 5714 | ['CCTTGTTGGCAG CTAACRACTTG'] |
| NM_021007.2 (SCN2A):c.3872A>G | 6326 | SCN2A | 5254 | ['ACTTTGTCTTCCTT GACGATATTCTRCTT TATTCAATATGCTCA TTATGTG'] | 5457 | ['CCTTGACGATAT TCTRCTTTATT'] | 5715 | ['CCTTGACGATAT TCTRCTTTATT'] |
| NM_002693.2 (POLG):c.2840A>G (p.Lys947Arg) | 8542 | POLG | 5255 | ['GTGGGCATCAGCC GTGAGCATGCCARA ATCTTCAACTACGG CCGCATCTAT'] | 5458 | ['CCGTGAGCATGC CARAATCTTCA'] | 5716 | ['CCGTGAGCATGC CARAATCTTCA'] |
| NM_020533.2 (MCOLN1):c.1406A>G (p.Asn469Ser) | 57192 | MCOLN1 | 5256 | ['TCTGAGTGCCTGTT CTCGCTCATCARTG GGGACGACATGTTT GTGACGTTC'] | 5459 | ['CCTGTTCTCGCT CATCARTGGGG'] | 5717 | ['CCTGTTCTCGCT CATCARTGGGG'] |
| NM_000069.2 (CACNA1S):c.3526-2A>G | 779 | CACNA1S | 5257 | ['TCGCTTTCCCATCC TTTTCCTTCCCRGGG | 5460 | ['CCCATCCTTTTCC TTCCCRGGGC'] ['CTACTTTGGAGACC CCTGGAAT'] | 5718- 5719 | ['CCCATCCTTTTCC TTCCCRGGGC', 'CCATCCTTTTCCT TCCCRGGGCT'] |
| NM_017662.4 (TRPM6):c.3173A>G (p.Tyr1058Cys) | 140803 | TRPM6 | 5258 | ['CAAGCTGTCTACCT CTTCGTGCAATRTAT CATCATGGTGAACC TGTTGATT'] | 5461 | ['CCTCTTCGTGCA ATRTATCATCA'] | 5720 | ['CCTCTTCGTGCA ATRTATCATCA'] |
| NM_006642.3 (SDCCAG8):c.2212A>G | 10806 | SDCCAG8 | 5259 | ['AATAAACCCTCTG CTTTTGCTCTATRGT TAATCAGCTCAAAG ATTTGTTGC'] | 5462 | ['CCTCTGCTTTTGC TCTATRGTTA'] | 5721 | ['CCTCTGCTTTTGC TCTATRGTTA'] |
| NM_003560.2 (PLA2G6):c.1349-2A>G | 8398 | PLA2G6 | 5260 | ['CAGCATGCCCTGCT CTGTGCCTCACRGA ACTACAGGATCTCA TGCACATCT'] | 5463 | ['CCCTGCTCTGTG CCTCACRGAAC'] | 5722- 5723 | ['CCCTGCTCTGTG CCTCACRGAAC', 'CCTGCTCTGTGCC TCACRGAACT'] |

Example 6: Next Generation C to T Editors

Other families of cytidine deaminases as alternatives to base etitor 3 (BE3) constructs were examined. The different C to T editors were developed to have a narrow or different editing window, alternate sequence specificity to expand targetable substrates, and to have higher activity.

Figure 42:
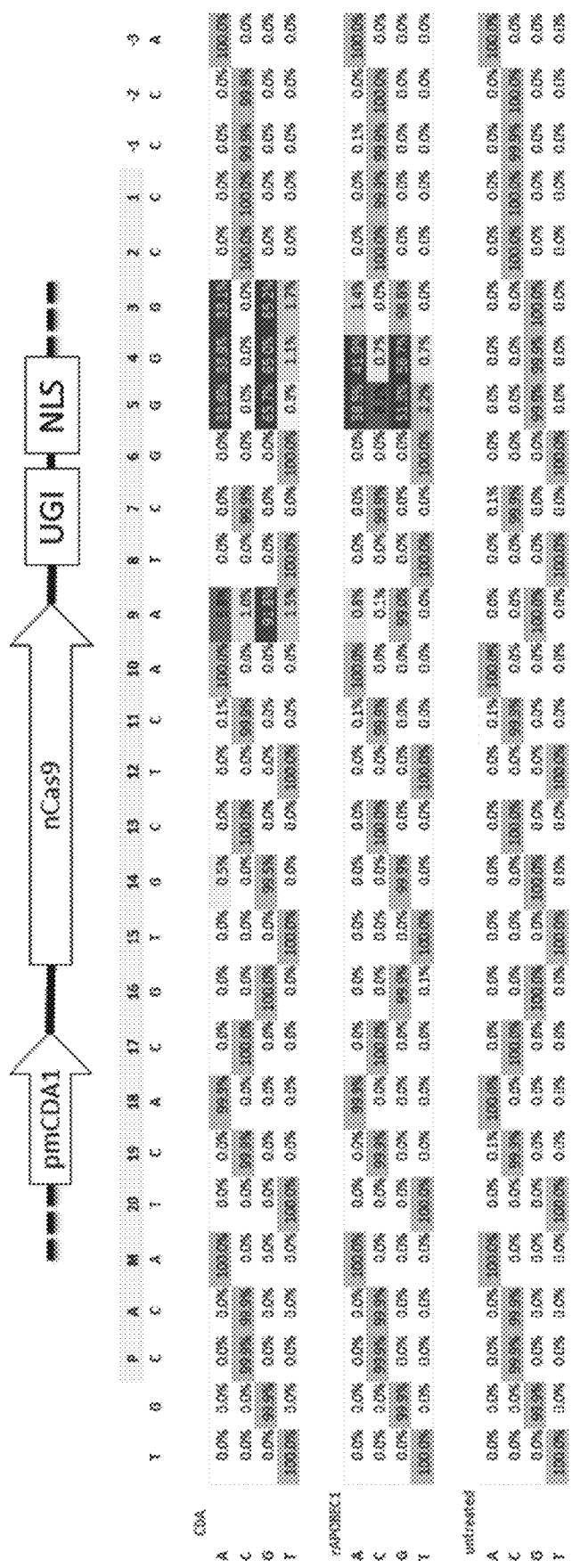
FIG. 42 is a schematic of the pmCDA-nCas9-UGI-NLS construct and its activity at the HeK-3 site relative to the base editor (rAPOBEC1) and the negative control (untreated).

Using the methods described in Example 4, the pmCDA1 (cytidine deaminase 1 from *Petromyzon marinus*) activity at the HeK-3 site is evaluated (FIG. 42). The pmCDA1-nCas9-UGI-NLS (nCas9 indicates the Cas9 nickase described herein) construct is active on some sites (e.g., the C bases on the complementary strand at position 9, 5, 4, and 3) that are not accessible with rAPOBEC1 (BE3).

Figure 43:
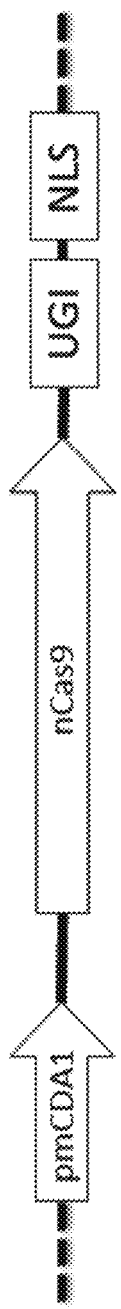
FIG. 43 is a schematic of the pmCDA1-XTEN-nCas9-UGI-NLS construct and its activity at the HeK-3 site relative to the base editor (rAPOBEC1) and the negative control (untreated).

The pmCDA1 activity at the HeK-2 site is given in FIG. 43. The pmCDA1-XTEN-nCas9-UGI-NLS construct is active on sites adjacent to "G," while rAPOBEC1 analog (BE3 construct) has low activity on "C"s that are adjacent to "G"s, e.g., the C base at position 11 on the complementary strand.

Figures 44, 45:
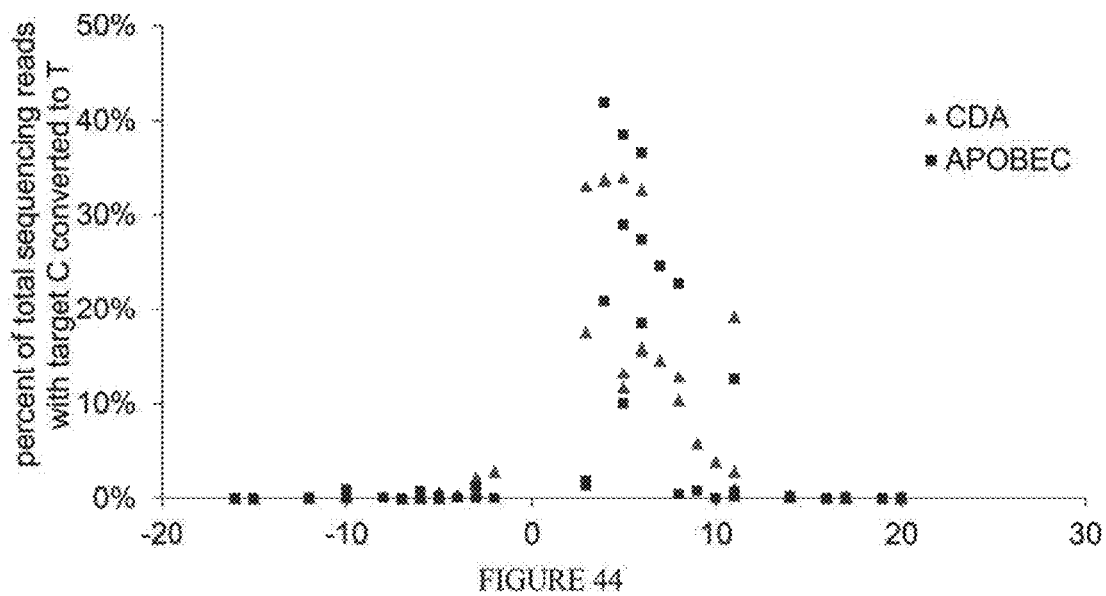
FIG. 44 shows the percent of total sequencing reads with target C converted to T using cytidine deaminases (CDA) or APOBEC.
FIG. 45 shows the percent of total sequencing reads with target C converted to A using deaminases (CDA) or APOBEC.
Figure 46:
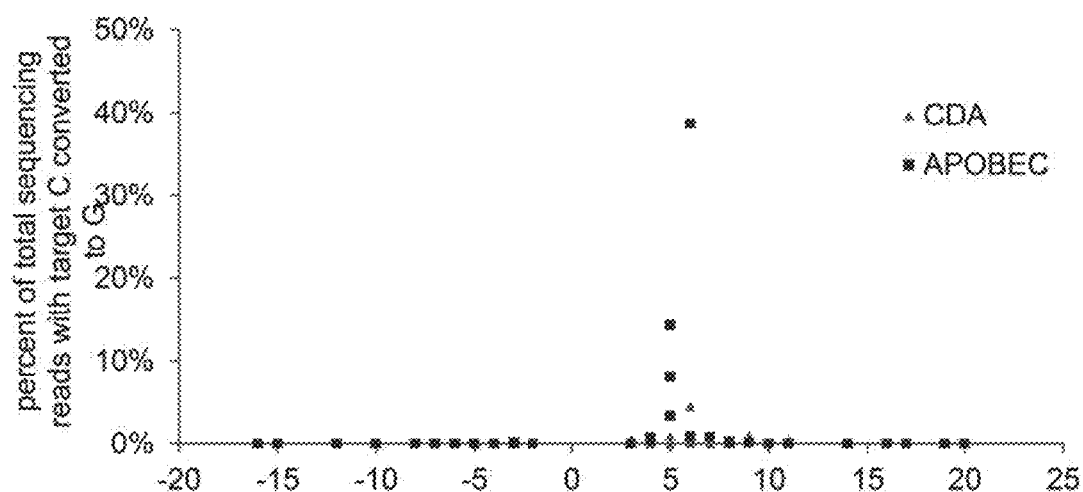
FIG. 46 shows the percent of total sequencing reads with target C converted to G using deaminases (CDA) or APOBEC.

The percent of total sequencing reads with target C converted to T (FIG. 44), C converted to A (FIG. 45), and C converted to G (FIG. 46) are shown for CDA and APOBEC1 (the BE3 construct).

Figure 47:
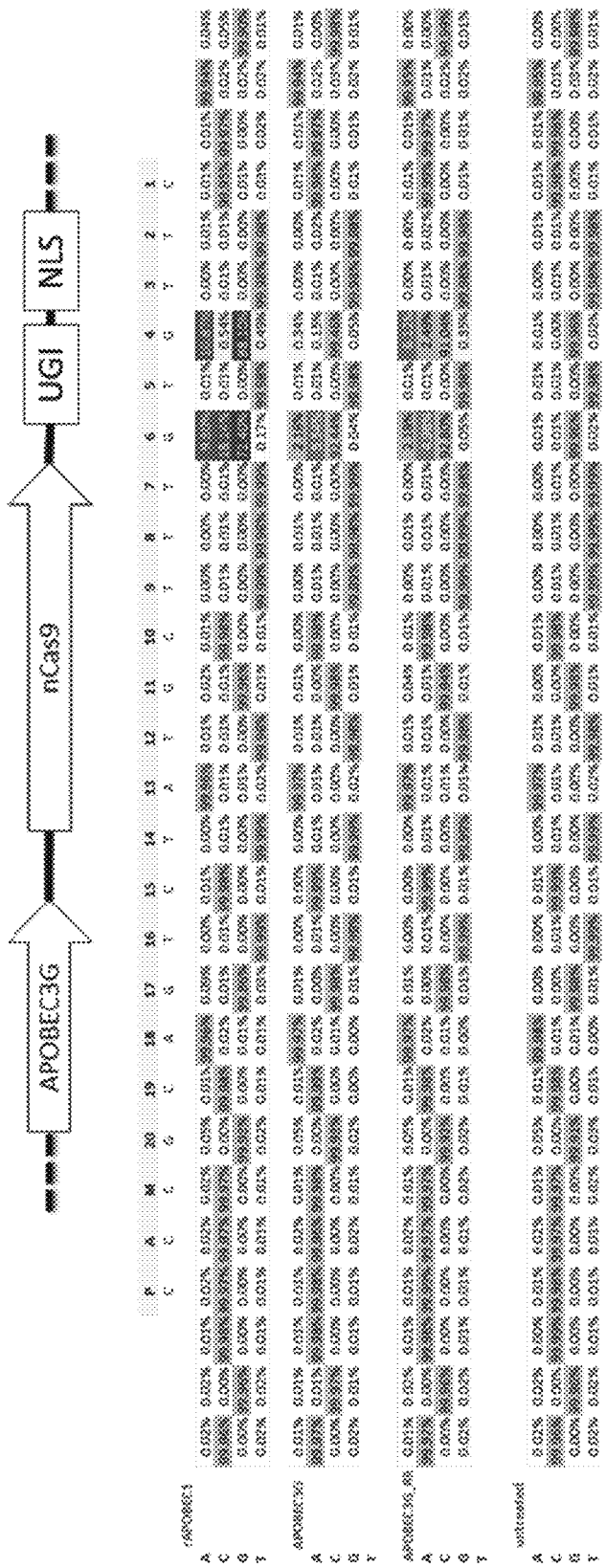
FIG. 47 is a schematic of the huAPOBEC3G-XTEN-nCas9-UGI-NLS construct and its activity at the HeK-2 site relative to a mutated form (huAPOBEC3G* (D316R_D317R)-XTEN-nCas9-UGI-NLS, the base editor (rAPOBEC1) and the negative control (untreated).

The huAPOBEC3G activity at the HeK-2 site is shown in FIG. 47. Two constructs were used: huAPOBEC3G-XTEN-nCas9-UGI-NLS and huAPOBEC3G*(D316R_D317R)-XTEN-nCas9-UGI-NLS. The huAPOBEC3G-XTEN-nCas9-UGI-NLS construct has different sequence specificity than rAPOBEC1 (BE3), as shown in FIG. 47, the editing window appears narrow, as indicated by APOBEC3G's decreased activity at position 4 compared to APOBEC1. Mutations made in huAPOBEC3G (D316R and D317R) increased ssDNA binding and resulted in an observable effect on expanding the sites which were edited (compare APOBEC3G with APOBEC3G_RR in FIG. 47). Mutations were chosen based on APOBEC3G crystal structure, see: Holden et al., Crystal structure of the anti-viral APOBEC3G catalytic domain and functional implication. *Nature*. (2008); 121-4, the entire contents of which are incorporated herein by reference.

Example 7: pmCDA1/huAPOBEC3G/rAPOBEC1 Work in *E. coli*

Figure 48:
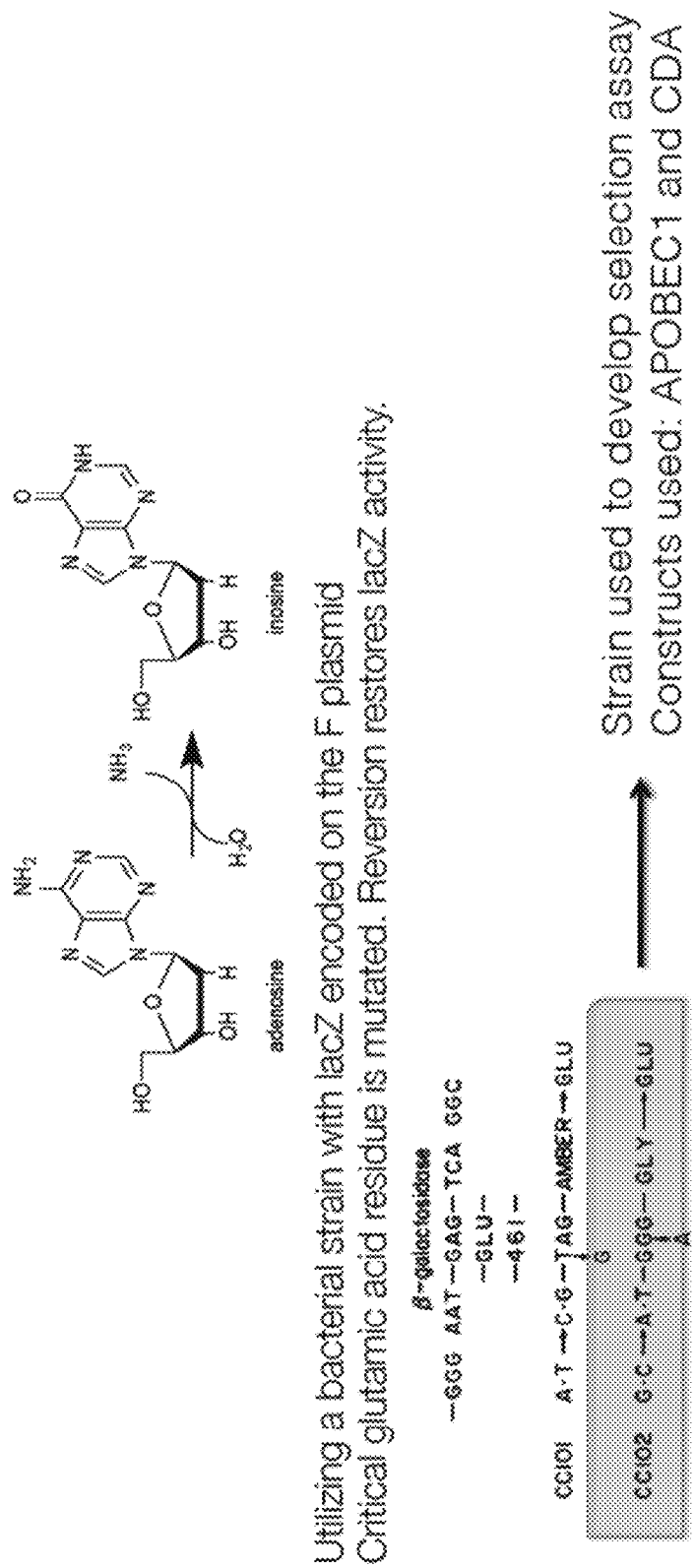
FIG. 48 shows the schematic of the LacZ construct used in the selection assay of Example 7.

LacZ selection optimization for the A to I conversion was performed using a bacterial strain with lacZ encoded on the F plasmid. A critical glutamic acid residue was mutated (e.g., GAG to GGG, Glu to Gly mutation) so that G to A by a cytidine deaminase would restore lacZ activity (FIG. 48). Strain CC102 was selected for the selection assay. APOBEC1 and CDA constructs were used in a selection assay to optimize G to A conversion.

Figure 49:
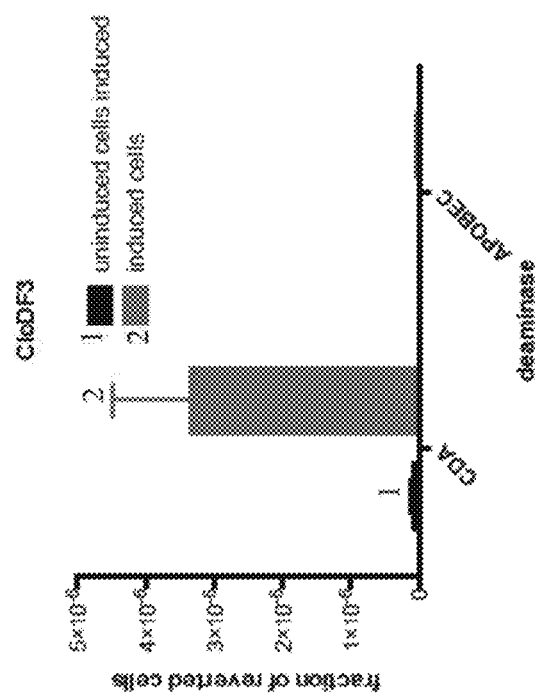
FIG. 49 shows reversion data from different plasmids and constructs.

To evaluate the effect of copy number of the plasmids encoding the deaminase constructs on lacZ reversion frequency, the CDA and APOBEC1 deaminases were cloned into 4 plasmids with different replication origins (hence different copy numbers), SC101, CloDF3, RSF1030, and PUC (copy number: PUC>RSF1030>CloDF3>SC101) and placed under an inducible promoter. The plasmids were individually transformed into *E. coli* cells harboring F plasmid containing the mutated LacZ gene. The expression of the deaminases were induced and LacZ activity was detected for each construct (FIG. 49). As shown in FIG. 49, CDA exhibited significantly higher activity than APOBEC1 in all instances, regardless of the plasmid copy number the deaminases were cloned in. Further, In terms of the copy number, the deaminase activity was positively correlated with the copy number of the plasmid they are cloned in, i.e., PUC>CloDF3>SC101.

Figure 50:
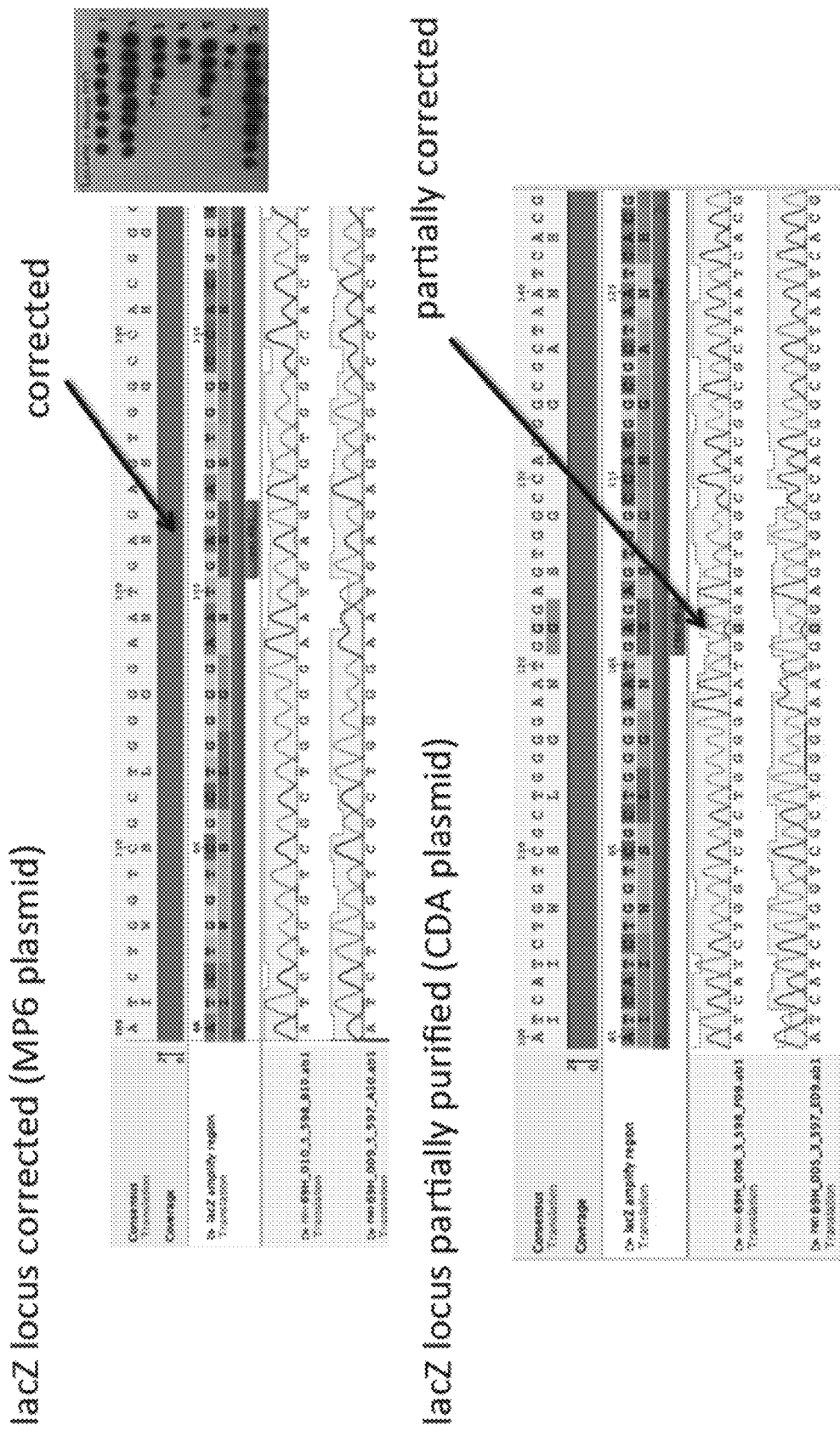
FIG. 50 shows the verification of lacZ reversion and the purification of reverted clones.

LacZ reversions were confirmed by sequencing of the genomic DNA at the lacZ locus. To obtain the genomic DNA containing the corrected LacZ gene, cells were grown media containing X-gal, where cells having LacZ activity form blue colonies. Blue colonies were selected and grown in minimal media containing lactose. The cells were spun down, washed, and re-plated on minimal media plates (lactose). The blue colony at the highest dilution was then selected, and its genomic DNA was sequenced at the lacZ locus (FIG. 50).

Figure 51:
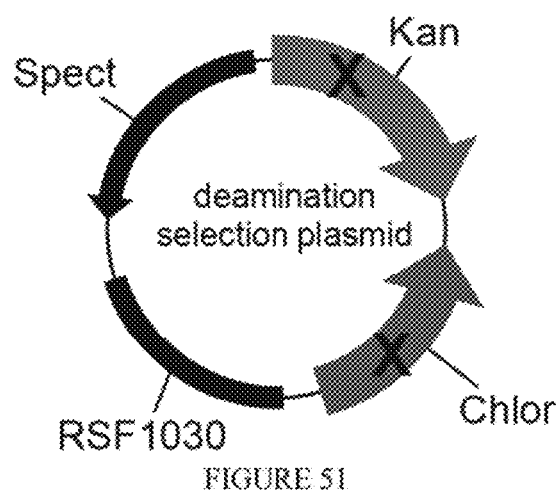
FIG. 51 is a schematic depicting a deamination selection plasmid used in Example 7.
Figure 52:
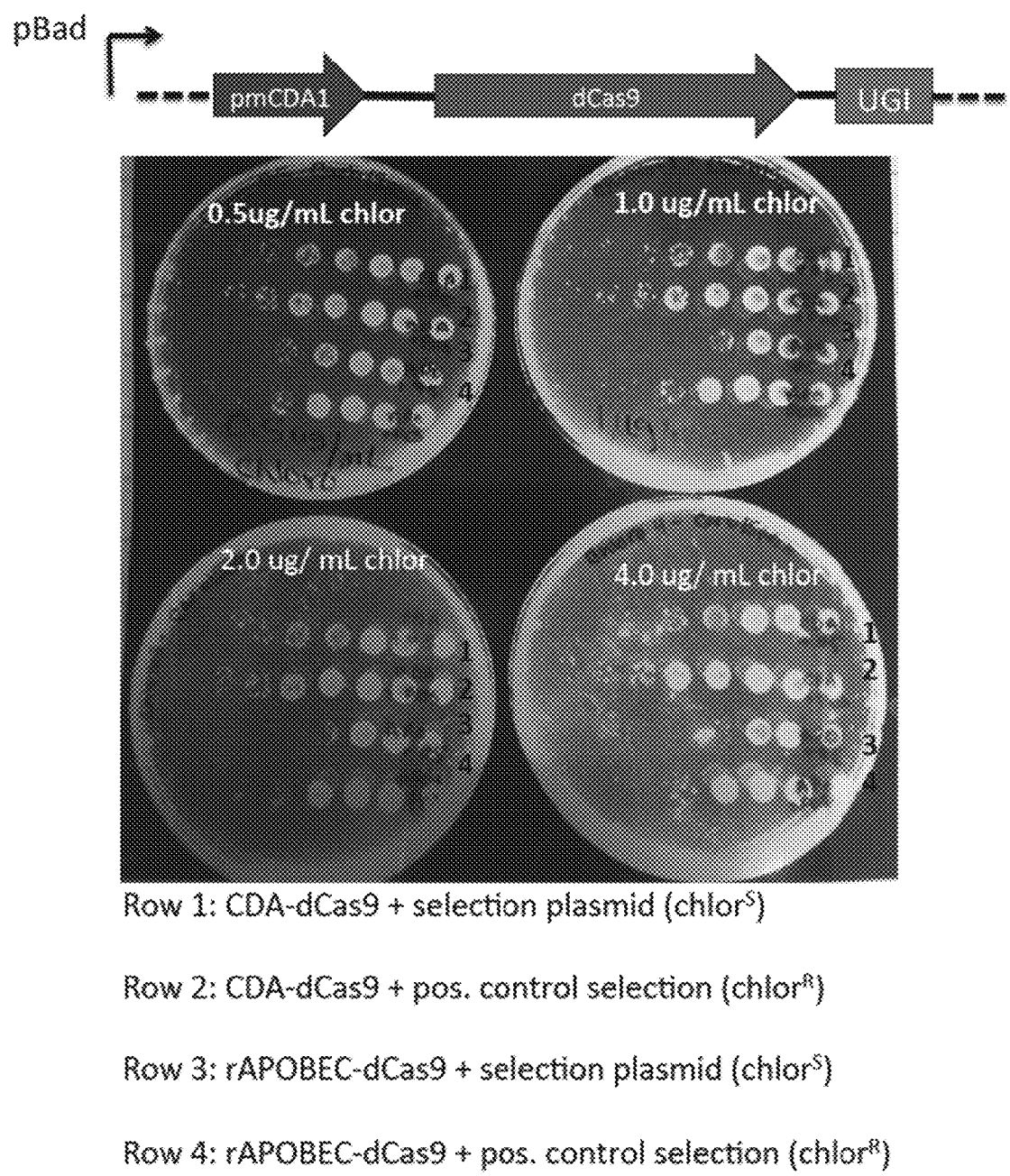
FIG. 52 shows the results of a chloramphenicol reversion assay (pmCDA1 fusion).
Figure 53A:
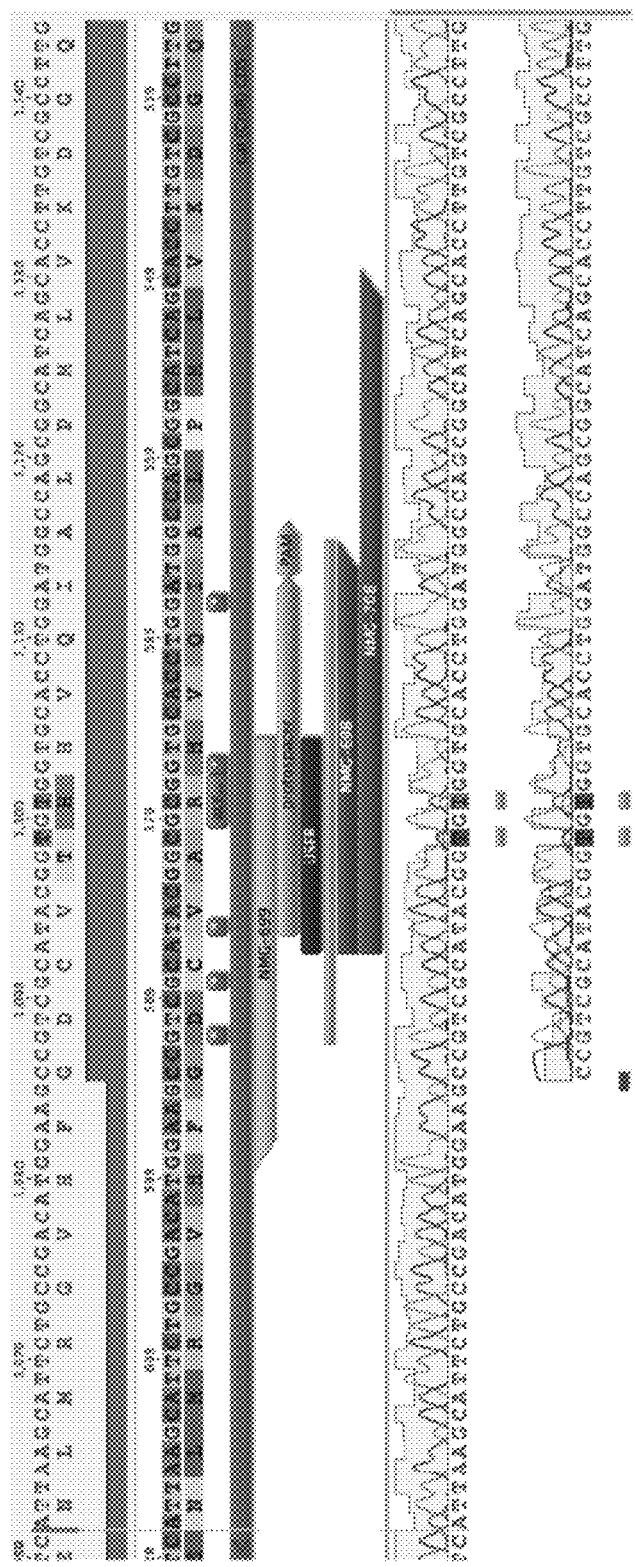

A chloramphenicol reversion assay was designed to test the activity of different cytidine deaminases (e.g., CDA, and APOBEC1). A plasmid harboring a mutant CAT1 gene which confers chloramphenicol resistance to bacteria is constructed with RSF1030 as the replication origin. The mutant CAT1 gene encodings a CAT1 protein that has a H195R (CAC to CGC) mutation, rendering the protein inactive (FIG. 51). Deamination of the C base-paired to the G base in the CGC codon would convert the codon back to a CAC codon, restoring the activity of the protein. As shown in FIG. 52, CDA outperforms rAPOBEC in *E. coli* in restoring the activity of the chloramphenicol resistance gene. The minimum inhibitory concentration (MIC) of chlor in S1030 with the selection plasmid (pNMG_ch_5) was approximately 1 µg/mL. Both rAPOBEC-XTEN-dCas9-UGI and CDA-XTEN-dCas9-UGI induced DNA correction on the selection plasmid (FIG. 53).

Figure 54:
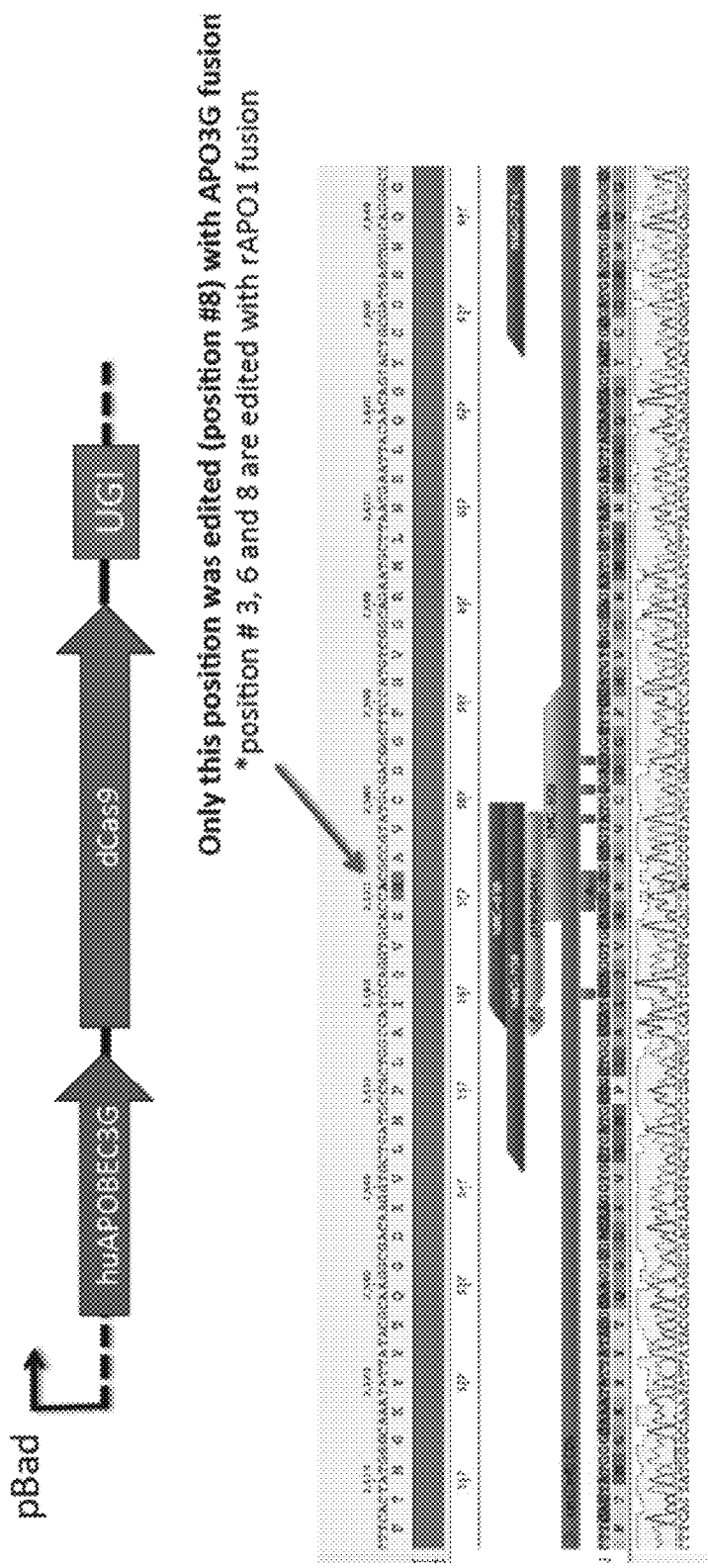
FIG. 54 shows the results of a chloramphenicol reversion assay (huAPOBEC3G fusion).

Next, the huAPOBEC3G-XTEN-dCas9-UGI protein was tested in the same assay. Interestingly, huAPOBEC3G-XTEN-dCas9-UGI exhibited different sequence specificity than the rAPOBEC1-XTEN-dCas9-UGI fusion protein. Only position 8 was edited with APOBEC3G-XTEN-dCas9-UGI fusion, as compared to the rAPOBEC11-XTEN-dCas9-UGIfusion (in which positions 3, 6, and 8 were edited) (FIG. 54).

Example 8: C to T Base Editors with Less Off Target Editing

Current base editing technologies allow for the sequence-specific conversion of a C:G base pair into a T:A base pair in genomic DNA. This is done via the direct catalytic conversion of cytosine to uracil by a cytidine deaminase enzyme and thus, unlike traditional genome editing technologies, does not introduce double-stranded DNA breaks (DSBs) into the DNA as a first step. See, Komor, A. C., Kim, Y. B., Packer, M. S., Zuris, J. A., and Liu, D. R. (2016), "Programmable editing of a target base in genomic DNA without double-stranded DNA cleavage." Nature 533, 420-424; the entire contents of which are incorporated by reference herein. Instead, catalytically dead SpCas9 (dCas9) or a SpCas9 nickase (dCas9(A840H)) is tethered to a cytidine deaminase enzyme such as rAPOBEC1, pmCDA1, or hAPOBEC3G. The genomic locus of interest is encoded by an sgRNA, and DNA binding and local denaturation is facilitated by the dCas9 portion of the fusion. However, just as wt dCas9 and wt Cas9 exhibit off-target DNA binding and cleavage, current base editors also exhibit C to T editing at Cas9 off-target loci, which limits their therapeutic usefulness.

It has been reported that the introduction of just three to four mutations into SpCas9 that neutralize nonspecific electrostatic interactions between the protein and the sugar-phosphate backbone of its target DNA, increases the DNA binding specificity of SpCas9. See, Kleinstiver, B. P., Pattanayak, V., Prew, M. S., Tsai, S. Q., Nguyen, N. T., Zheng, Z., and Joung, J. K. (2016) "High-fidelity CRISPR-Cas9 nucleases with no detectable genome-wide off-target effects." Nature 529, 490-495; and Slaymaker, I. M., Gao, L., Zetsche, B., Scott, D. A., Yan, W. X., and Zhang, F. (2015) "Rationally engineered Cas9 nucleases with improved specificity. Science 351, 84-88; the entire contents of each are hereby incorporated by reference herein. Four reported neutralizing mutations were therefore incorporated into the initially reported base editor BE3 (SEQ ID NO:

285), and found that off-target C to T editing of this enzyme is also drastically reduced (FIG. 55), with no decrease in on-target editing (FIG. 56).

Figure 55:
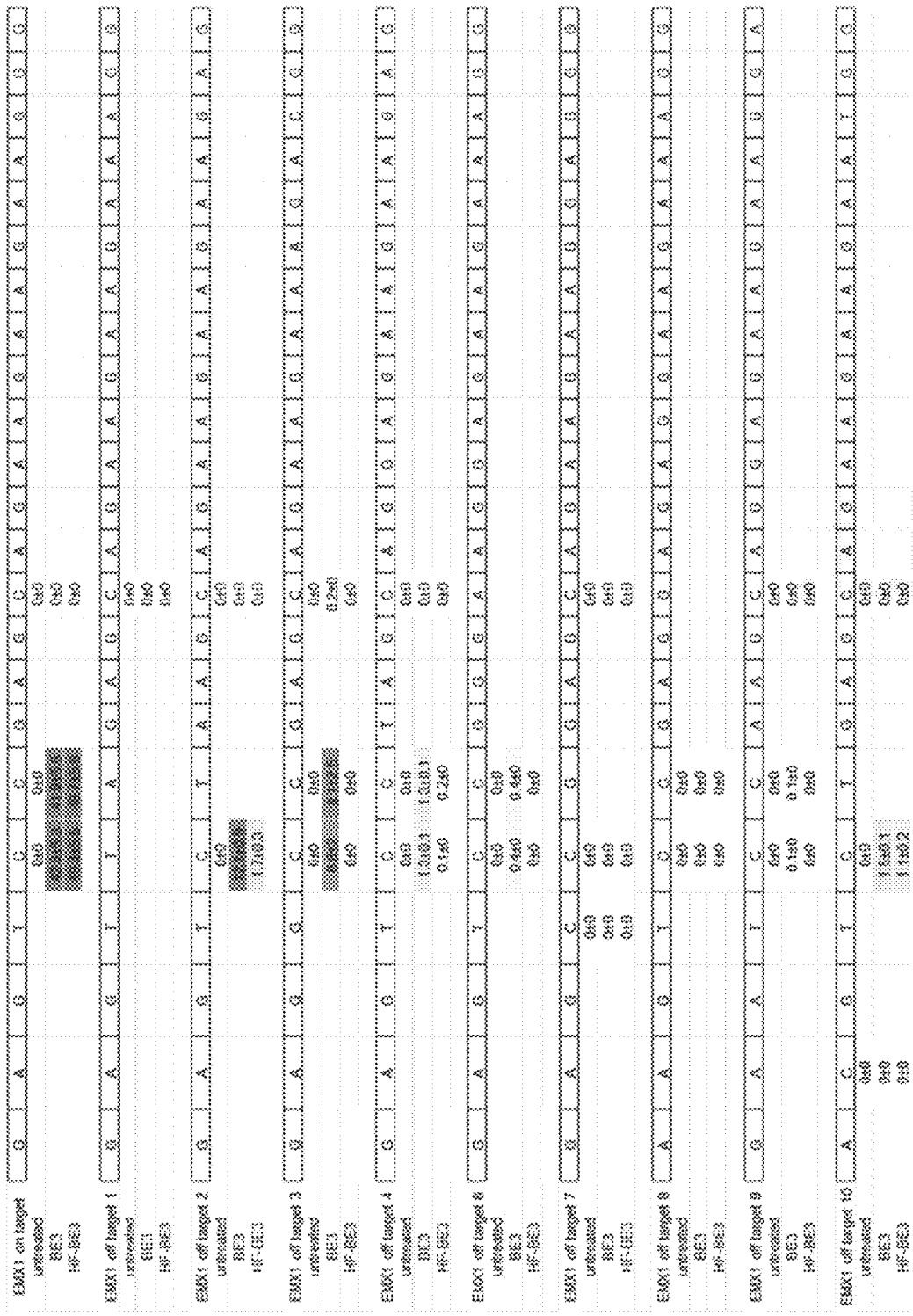
FIG. 55 shows the activities of BE3 and HF-BE3 at EMX1 off-targets. The sequences, from top to bottom, correspond to SEQ ID NOs: 286-292, 299-301.

As shown in FIG. 55, HEK293T cells were transfected with plasmids expressing BE3 or HF-BE3 and a sgRNA matching the EMX1 sequence using Lipofectamine 2000. Three days after transfection, genomic DNA was extracted, amplified by PCR, and analyzed by high-throughput DNA sequencing at the on-target locus, plus the top ten known Cas9 off-target loci for the EMX1 sgRNA, as previously determined by Joung and coworkers using the GUIDE-seq method. See Tsai, S. Q., Zheng, Z., Nguyen, N. T., Liebers, M., Topkar, V. V., Thapar, V., Wyvekens, N., Khayter, C., Iafrate, A. J., Le, L. P., et al. (2015) "GUIDE-seq enables genome-wide profiling of off-target cleavage by CRISPR-Cas nucleases." Nat Biotech 33, 187-197; the entire contents of which are incorporated by reference herein. EMX1 off-target 5 locus did not amplify and is not shown. Sequences of the on-target and off-target protospacers and protospacer adjacent motifs (PAMs) are displayed (FIG. 55). Cellular C to T conversion percentages, defined as the percentage of total DNA sequencing reads with T at each position of an original C within the protospacer, are shown for BE3 and HF-BE3.

In FIG. 56, HEK293T cells were transfected with plasmids expressing BE3 or HF-BE3 and sgRNAs matching the genomic loci indicated using Lipofectamine 2000. Three days after transfection, genomic DNA was extracted, amplified by PCR, and analyzed by high-throughput DNA sequencing at the on-target loci. The percentage of total DNA sequencing reads with all four bases at the target Cs within each protospacer are shown for treatment with BE3 or HF-BE3 (FIG. 56). Frequencies of indel formation are shown as well.

Primary Protein Sequence of HF-BE3 (SEQ ID NO: 285):

```
MSSETGPVAVDPTLRRRIEPHEFEVFFDPRELRKETCLLYEINWGGRHSI
WRHTSQNTNKHVEVNFIEKFTTERYFCPNTRCSITWFLSWSPCGECSRAI
TEFLSRYPHVTLFIYIARLYHHADPRNRQGLRDLISSGVTIQIMTEQESG
YCWRNFVNYSPSNEAHWPRYPHLWVRLYVLELYCIILGLPPCLNILRRKQ
PQLTFFTIALQSCHYQRLPPHILWATGLKSGSETPGTSESATPESDKKYS
IGLAIGTNSVGWAVITDEYKVPSKKFKVLGNTDRHSIKKNLIGALLFDSG
ETALATRLKRTARRRYTRRKNRICYLQEIFSNEMAKVDDSFFHRLEESFL
VEEDKKHERHPIFGNIVDEVAYHEKYPTIYHLRKKLVDSTDKADLRLIYL
ALAHMIKFRGHFLIEGDLNPDNSDVDKLFIQLVQTYNQLFEENPINASGV
DAKAILSARLSKSRRLENLIAQLPGEKKNGLFGNLIALSLGLTPNFKSNF
DLAEDAKLQLSKDTYDDDLDNLLAQIGDQYADLFLAAKNLSDAILLSDIL
RVNTEITKAPLSASMIKRYDEHHQDLTLLKALVRQQLPEKYKEIFFDQSK
NGYAGYIDGGASQLEFYKFIKPILEKMDGTEELLVKLNREDLLRKQRTFD
NGSIPHQIHLGELHAILRRQEDFYPFLKDNREKIEKILTFRIPYYVGPLA
RGNSRFAWMTRKSEETITPWNFEEVVDKGASAQSFIERMTAFDKNLPNEK
VLPKHSLLYEYFTVYNELTKVKYVTEGMRKPAFLSGEQKKAIVDLLFKTN
RKVTVKQLKEDYFKKIECFDSVEISGVEDRFNASLGTYHDLLKIIKDKDF
LDNEENEDILEDIVLTLTLFEDREMIEERLKTYAHLFDDKVMKQLKRRRY
TGWGALSRKLINGIRDKQSGKTILDFLKSDGFANRNFMALIHDDSLTFKE
DIQKAQVSGQGDSLHEHIANLAGSPAIKKGILQTVKVVDELVKVMGRHKP
ENIVIEMARENQTTQKGQKNSRERMKRIEEGIKELGSQILKEHPVENTQL
QNEKLYLYYLQNGRDMYVDQELDINRLSDYDVDHIVPQSFLKDDSIDNKV
LTRSDKNRGKSDNVPSEEVVKKMKNYWRQLLNAKLITQRKFDNLTKAERG
GLSELDKAGFIKRQLVETRAITKHVAQILDSRMNTKYDENDKLIREVKVI
TLKSKLVSDFRKDFQFYKVREINNYHHAHDAYLNAVVGTALIKKYPKLES
EFVYGDYKVYDVRKMIAKSEQEIGKATAKYFFYSNIMNFFKTEITLANGE
IRKRPLIETNGETGEIVWDKGRDFATVRKVLSMPQVNIVKKTEVQTGGFS
KESILPKRNSDKLIARKKDWDPKKYGGFDSPTVAYSVLVVAKVEKGKSKK
LKSVKELLGITIMERSSFEKNPIDFLEAKGYKEVKKDLIIKLPKYSLFEL
ENGRKRMLASAGELQKGNELALPSKYVNFLYLASHYEKLKGSPEDNEQKQ
LFVEQHKHYLDEIIEQISEFSKRVILADANLDKVLSAYNKHRDKPIREQA
ENIIHLFTLTNLGAPAAFKYFDTTIDRKRYTSTKEVLDATLIHQSITGLY
ETRIDLSQLGGDSGGSTNLSDIIEKETGKQLVIQESILMLPEEVEEVIGN
KPESDILVHTAYDESTDENVMLLTSDAPEYKPWALVIQDSNGENKIKMLS
GGSPKKKRKV
```

Example 9: Development of Base Editors that Use Cas9 Variants and Modulation of the Base Editor Processivity to Increase the Target Range and Precision of the Base Editing Technology Unlike traditional genome editing platforms, base editing technology allows precise single nucleotide changes in the DNA without inducing double-stranded breaks (DSBs). See, Komor, A. C. et al. Nature 533, 420-424 (2016). The current generation of base editor uses the NGG PAM exclusively. This limits its ability to edit desired bases within the genome, as the base editor needs to be placed at a precise location where the target base is placed within a 4-base region (the 'deamination window'), approximately 15 bases upstream of the PAM. See, Komor, A. C. et al. Nature 533, 420-424 (2016). Moreover, due to the high processivity of cytidine deaminase, the base editor may convert all cytidines within its deamination window into thymidines, which could induce amino acid changes other than the one desired by the researcher. See, Komor, A. C. et al. Nature 533, 420-424 (2016).

Expanding the Scope of Base Editing Through the Development of Base Editors with Cas9 Variants Cas9 homologs and other RNA-guided DNA binders that have different PAM specificities were incorporated into the base editor architecture. See, Kleinstiver, B. P. et al. Nature 523, 481-485 (2015); Kleinstiver, B. P. et al. Nature Biotechnology 33, 1293-1298 (2015); and Zetsche, B. et al. Cell 163, 759-771 (2015); the entire contents of each are incorporated by reference herein. Furthermore, innovations that have broadened the PAM specificities of various Cas9 proteins were also incorporated to expand the target reach of the base editor even more. See, Kleinstiver, B. P. et al. Nature 523, 481-485 (2015); and Kleinstiver, B. P. et al. Nature Biotechnology 33, 1293-1298 (2015). The current palette of base editors is summarized in Table 4.

| Species | PAM | Base Editor Name | Reference for Cas9 variant |
|---|---|---|---|
| S. pyogenes | ...NGG | BE3 | Wild-type |
| | ...NGA | VQR BE3 or EQR BE3 | Kleinstiver, B. P. et al. |
| | ...NGCG | VRER BE3 | Kleinstiver, B. P. et al. |
| S. aureus | ...NNGRRT | SaBE3 | Wild-type |
| | ...NNNRRT | SaKKH BE3 | Kleinstiver, B. P. et al. |
| L. bacterium | TTTN... | dCpf1 BE2 | Zetsche, B. et al. |

Modulating Base Editor's Processivity Through Site-Directed Mutagenesis of rAPOBEC1

Figure 57:
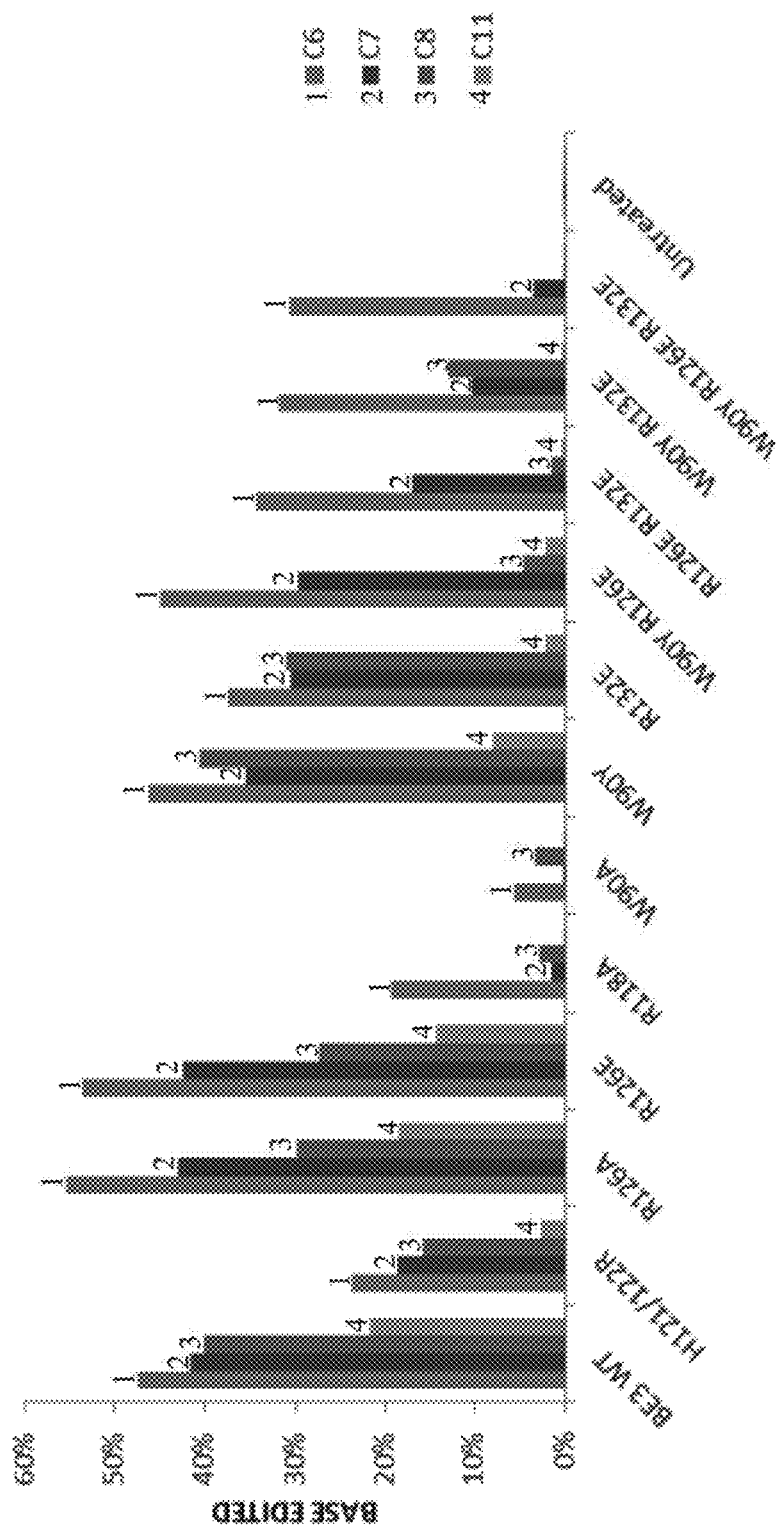
FIG. 57 is a graph demonstrating that mutations affect cytidine deamination with varying degrees. Combinations of mutations that each slightly impairs catalysis allow selective deamination at one position over others. The FANCF site was $$\text{GGAATC}_6\text{C}_7\text{C}_8\text{TTC}_{11}\text{TGCAGCACCTGG}. \quad \text{(SEQ ID NO: 303)}$$

It was reasoned that the processivity of the base editor could be modulated by making point mutations in the deaminase enzyme. The incorporation of mutations that slightly reduce the catalytic activity of deaminase in which the base editor could still catalyze on average one round of cytidine deamination but was unlikely to access and catalyze another deamination within the relevant timescale were pursued. In effect, the resulting base editor would have a narrower deamination window.

rAPOBEC1 mutations probed in this work are listed in Table 5. Some of the mutations resulted in slight apparent impairment of rAPOBEC1 catalysis, which manifested as preferential editing of one cytidine over another when multiple cytidines are found within the deamination window. Combining some of these mutations had an additive effect, allowing the base editor to discriminate substrate cytidines with higher stringency. Some of the double mutants and the triple mutant allowed selective editing of one cytidine among multiple cytidines that are right next to one another (FIG. 57).

TABLE 5 rAPOBEC1 Point Mutations Investigated

| rAPOBEC1 mutation studied in this work | Corresponding mutation in APOBEC3G | Reference |
|---|---|---|
| H121R/H122R | D315R/D316R | Holden, L. G. et al. |
| R126A | R320A | Chen, K-M. et al. |
| R126E | R320E | Chen, K-M. et al. |
| R118A | R313A | Chen, K-M. et al. |
| W90A | W285A | Chen, K-M. et al. |
| W90Y | W285Y | |
| R312E | R326E | |

Base Editor PAM Expansion and Processivity Modulation

Figure 58:
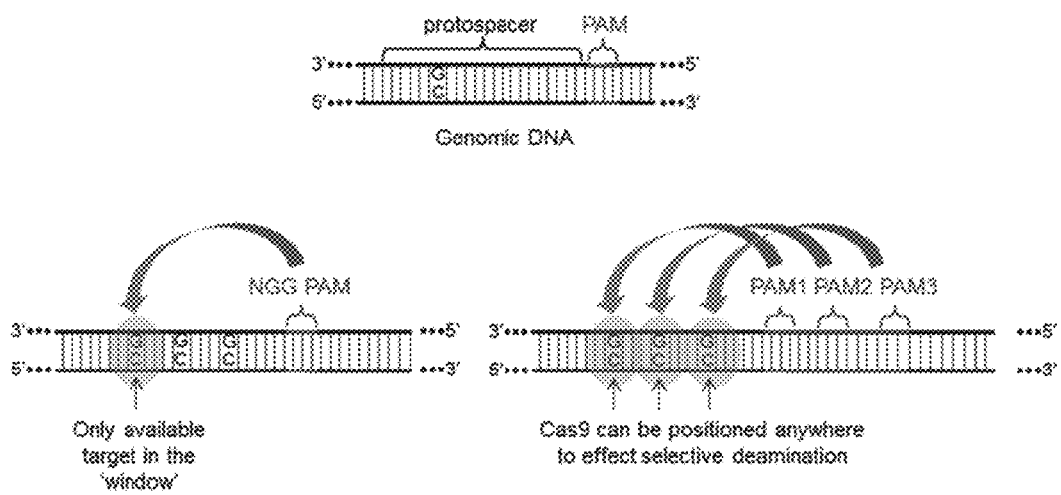
FIG. 58 is a schematic depicting next generation base editors.
Figure 59:
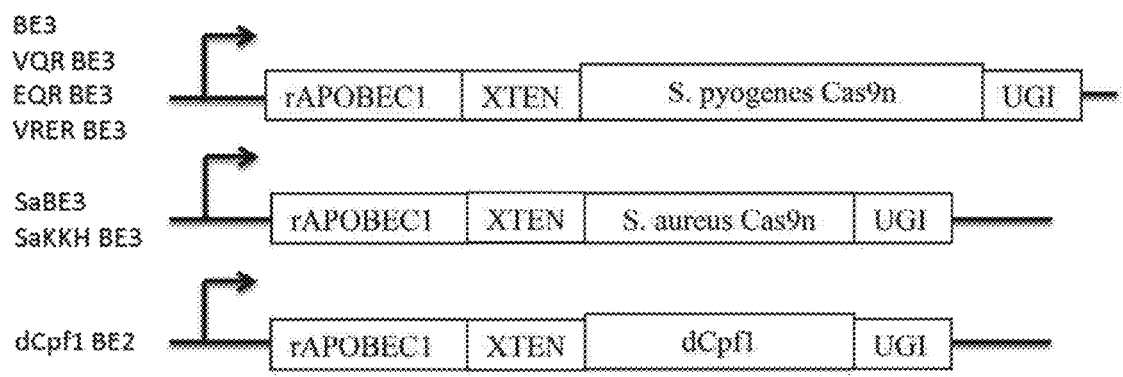
FIG. 59 is a schematic illustrating new base editors made from Cas9 variants.
Figure 60:
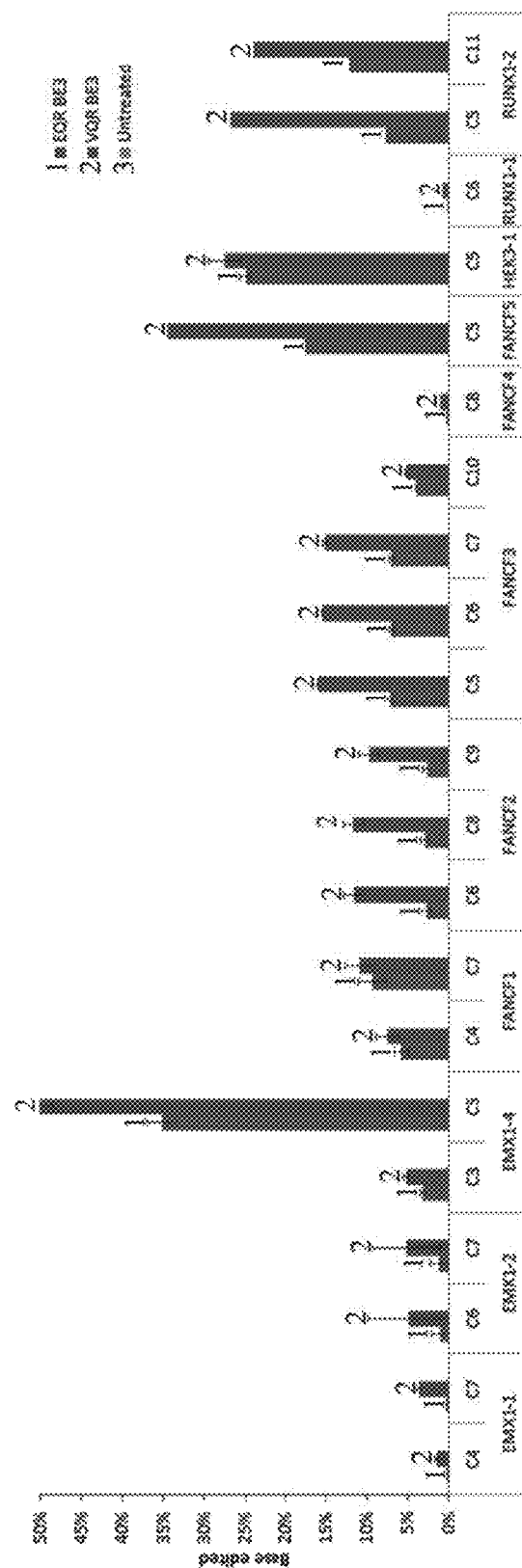
FIG. 60 shows the base-edited percentage of different NGA PAM sites.
Figure 61:
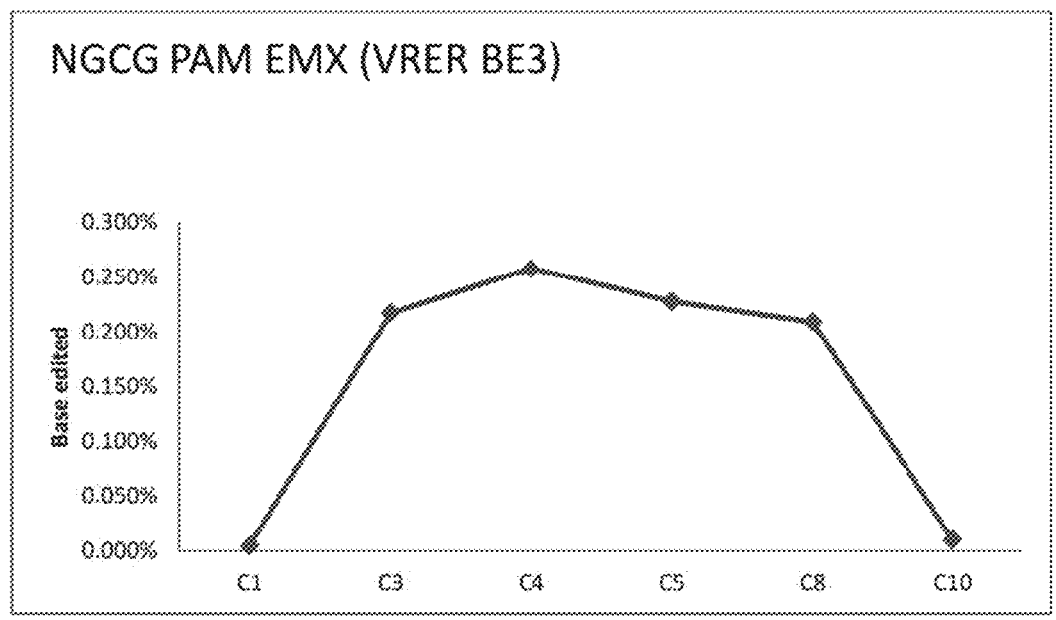
FIG. 61 shows the base-edited percentage of cytidines using NGCG PAM EMX (VRER BE3) and the $C_1TC_3C_4C_5ATC_8AC_{10}ATCAACCGGT$ (SEQ ID NO: 304) spacer.
Figure 62:
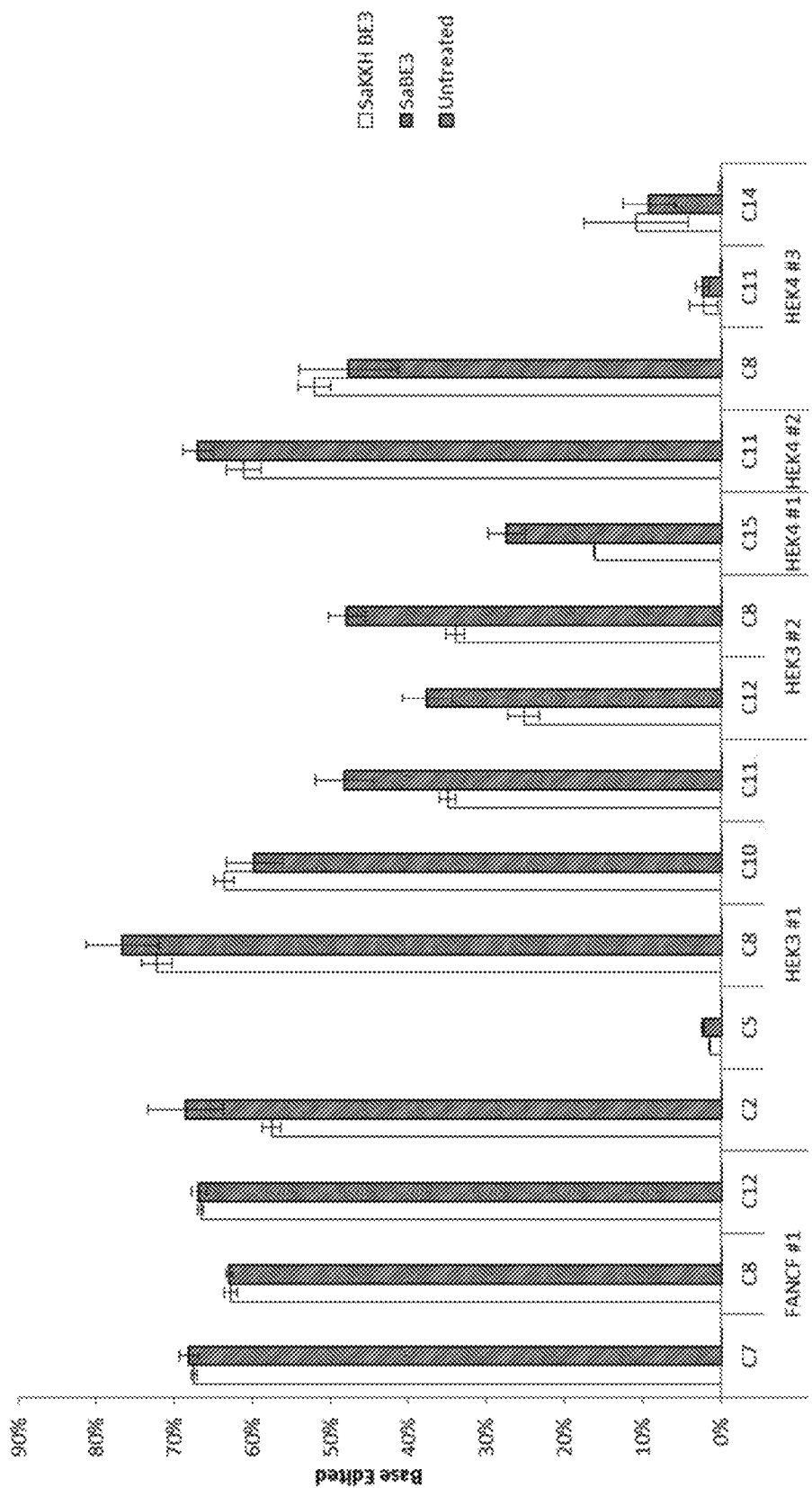
FIG. 62 shows the based-edited percentages resulting from different NNGRRT PAM sites.
Figure 63:
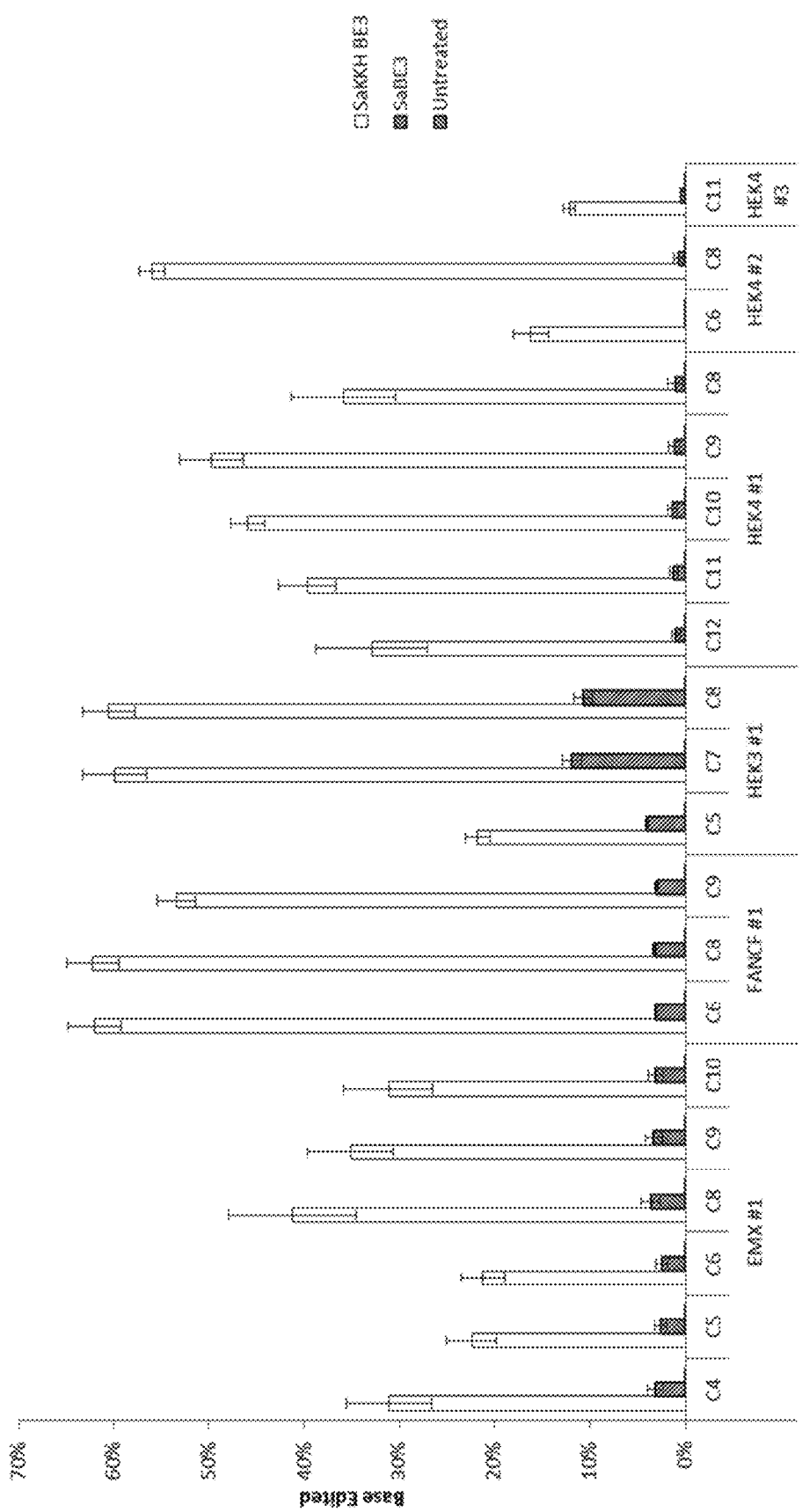
FIG. 63 shows the based-edited percentages resulting from different NNHRRT PAM sites.

The next generation of base editors were designed to expand editable cytidines in the genome by using other RNA-guided DNA binders (FIG. 58). Using a NGG PAM only allows for a single target within the "window" whereas the use of multiple different PAMs allows for Cas9 to be positioned anywhere to effect selective deamination. A variety of new base editors have been created from Cas9 variants (FIG. 59 and Table 4). Different PAM sites (NGA, FIG. 60; NGCG, FIG. 61; NNGRRT, FIG. 62; and NNHRRT, FIG. 63) were explored. Selective deamination was successfully achieved through kinetic modulation of cytidine deaminase point mutagenesis (FIG. 65 and Table 5).

The effect of various mutations on the deamination window was then investigated in cell culture using spacers with multiple cytidines (FIGS. 66 and 67).

Further, the effect of various mutations on different genomic sites with limited numbers of cytidines was examined (FIGS. 68 to 71). It was found that approximately one cytidine will be edited within the deamination window in the spacer, while the rest of the cytidines will be left intact. Overall, the preference for editing is as follows: $C_6 > C_5 \gg C_7 \approx C_4$.

Base Editing Using Cpf1

Figure 64A:
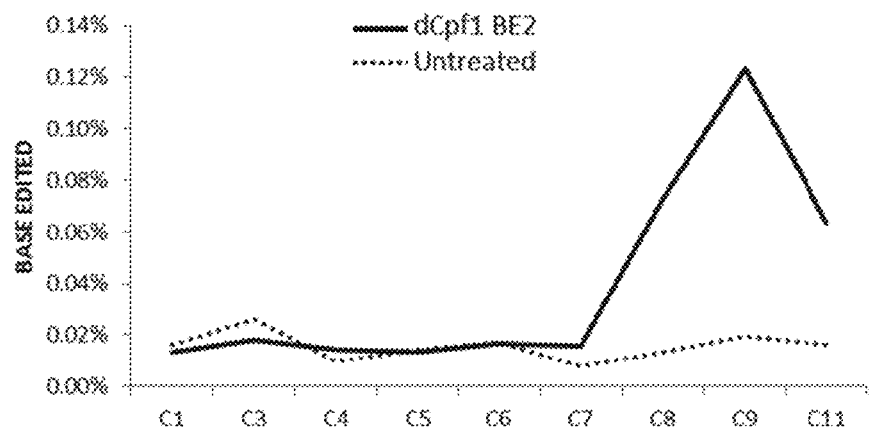
FIGS. 64A to 64C show the base-edited percentages resulting from different TTTN PAM sites using Cpf1 BE2. The spacers used were.
Figure 64B:
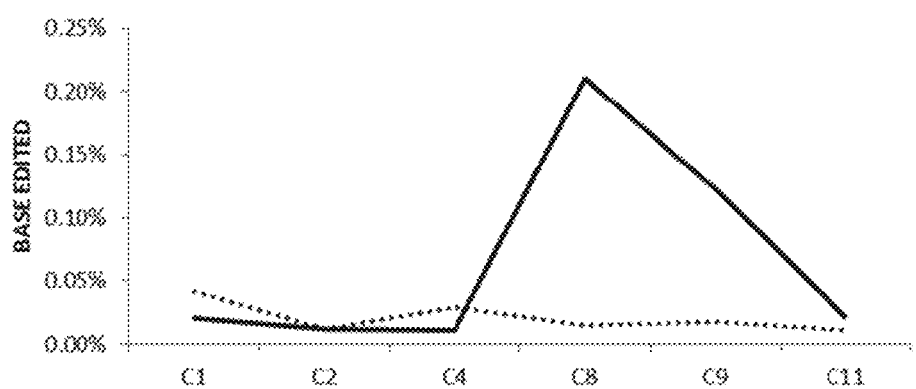
Figure 64C:
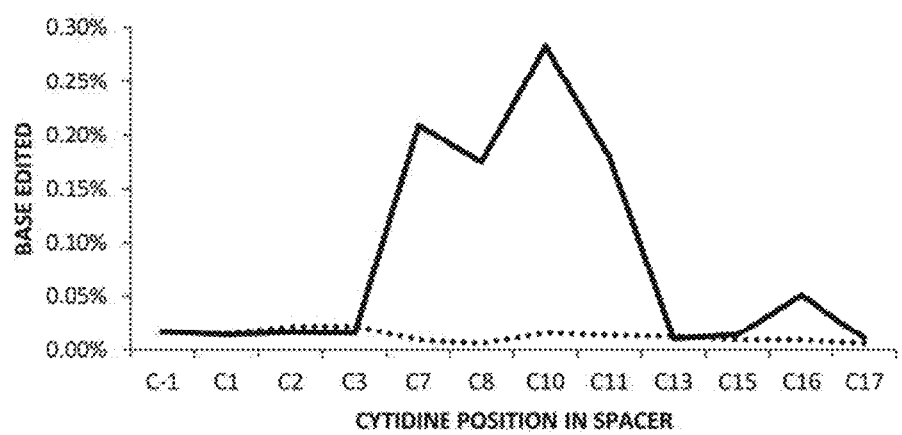

Cpf1, a Cas9 homolog, can be obtained as AsCpf1, LbCpf1, or from any other species. Schematics of fusion constructs, including BE2 and BE3 equivalents, are shown in FIG. 73. The BE2 equivalent uses catalytically inactive Cpf2 enzyme (dCpf1) instead of Cas9, while the BE3 equivalent includes the Cpf1 mutant, which nicks the target strand. The bottom schematic depicts different fusion architectures to combine the two innovations illustrated above it (FIG. 73). The base editing results of HEK293T cell TTTN PAM sites using Cpf1 BE2 were examined with different spacers (FIGS. 64A to 64C). In some embodiments, Cpf1 may be used in place of a Cas9 domain in any of the base editors provided herein. In some embodiments, the Cpf1 is a protein that is at least 50%, 55%, 60%, 65%, 70%, 75%, 80%, 85%, 90%, 95%, 98%, 99%, or 99.5% identical to SEQ ID NO 313.

Full Protein Sequence of Cpf1 (SEQ ID NO: 313):

MSIYQEFVNKYSLSKTLRFELIPQGKTLENIKARGLILDDEKRAKDYKKA

KQIIDKYHQFFIEEILSSVCISEDLLQNYSDVYFKLKKSDDDNLQKDFKS

AKDTIKKQISEYIKDSEKFKNLFNQNLIDAKKGQESDLILWLKQSKDNGI

ELFKANSDITDIDEALEIIKSFKGWTTYFKGFHENRKNVYSSNDIPTSII

YRIVDDNLPKFLENKAKYESLKDKAPEAINYEQIKKDLAELLTFDIDYKT

SEVNQRVFSLDEVFEIANFNNYLNQSGITKFNTIIGGKFVNGENTKRKGI

NEYINLYSQQINDKTLKKYKMSVLFKQILSDTESKSFVIDKLEDDSDVVT

TMQSFYEQIAAFKTVEEKSIKETLSLLFDDLKAQKLDLSKIYFKNDKSLT

DLSQQVFDDYSVIGTAVLEYITQQIAPKNLDNPSKKEQELIAKKTEKAKY

LSLETIKLALEEFNKHRDIDKQCRFEEILANFAAIPMIFDEIAQNKDNLA

QISIKYQNQGKKDLLQASAEDDVKAIKDLLDQTNNLLHKLKIFHISQSED

KANILDKDEHFYLVFEECYFELANIVPLYNKIRNYITQKPYSDEKFKLNF

ENSTLANGWDKNKEPDNTAILFIKDDKYYLGVMNKKNNKIFDDKAIKENK

GEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSI

DEFYREVENQGYKLTFENISESYIDSVVNQGKLYLFQIYNKDFSAYSKGR

PNLHTLYWKALFDERNLQDVVYKLNGEAELFYRKQSIPKKITHPAKEAIA

NKNKDNPKKESVFEYDLIKDKRFTEDKFFFHCPITINFKSSGANKFNDEI

NLLLKEKANDVHILSIDRGERHLAYYTLVDGKGNIIKQDTFNIIGNDRMK

TNYHDKLAAIEKDRDSARKDWKKINNIKEMKEGYLSQVVHEIAKLVIEYN

AIVVFEDLNFGFKRGRFKVEKQVYQKLEKMLIEKLNYLVFKDNEFDKTGG

VLRAYQLTAPFETFKKMGKQTGIIYYVPAGFTSKICPVTGFVNQLYPKYE

SVSKSQEFFSKFDKICYNLDKGYFEFSFDYKNFGDKAAKGKWTIASFGSR

LINFRNSDKNHNWDTREVYPTKELEKLLKDYSIEYGHGECIKAAICGESD

KKFFAKLTSVLNTILQMRNSKTGTELDYLISPVADVNGNFFDSRQAPKNM

PQDADANGAYHIGLKGLMLLGRIKNNQEGKKLNLVIKNEEYFEFVQNRNN

Example 10: Increased Fidelity of Base Editing

Examining the difference between plasmid delivery of BE3 and HF-BE3, it was found that the two edit on-target loci with comparable efficiency (FIGS. 74 and 75). However, HF-BE3 edited off-target loci much less than BE3, meaning that HF-BE3 has a much higher DNA specificity than BE3 (FIG. 76). Deaminase protein lipofection to HEK cells demonstrated that protein delivery of BE3 results in comparable on-target activity, but much better specificity, than plasmid DNA delivery of BE3. Using improved transfection procedures and better plasmids (n=2), the experiment used the following conditions: protein delivery was 125 nM Cas9:sgRNA complex, plasmid delivery was 750 ng BE3/HF-BE3 plasmid+250 ng sgRNA plasmid, and lipofection was with 1.5 μL of Lipofectamine 2000 per well. EMX-1 off target site 2 and FANCF off-target site 1 showed the most off-target editing with BE3, compared to all of the off-targets assayed (FIGS. 77 and 78), while HEK-3 showed no significant editing at off-targets for any of the delivery methods (FIG. 79). HEK-4 shows some C-to-G editing on at the on-target site, while its off-target sites 1, 3, and 4 showed the most off-target editing of all the assayed sites (FIG. 80). Delivery of BE3 Protein via Micro-Injection to Zebrafish TYR guide RNAs were tested in an in vitro assay for sgRNA activity (FIGS. 81 and 82). The % HTS reads shows how many C residues were converted to T residues during a 2 h incubation with purified BE3 protein and PCR of the resulting product. Experiments used an 80-mer synthetic DNA substrate with the target deamination site in 60 bp of its genomic context. This is not the same as % edited DNA strands because only one strand was nicked, so the product is not amplified by PCR. The proportion of HTS reads edited is equal to x/(2−x), where x is the actual proportion of THS reads edited. For 60% editing, the actual proportion of bases edited is 75%. "Off target" is represents BE3 incubated with the same DNA substrate, while bound to an off-target sgRNA. It was found sgRNAs sgRH_13, sgHR_17, and possibly sgHR_16 appeared to be promising targets for in vivo injection experiments.

The delivery of BE3 protein in was tested in vivo in zebrafish. Zebrafish embryos (n=16-24) were injected with either scrambled sgRNA, sgHR_13, sgHR_16, or sgHR_17 and purified BE3. Three embryos from each condition were analyzed independently (single embryo) and for each condition, all of the injected embryos were pooled and sequenced as a pool. The results are shown in FIGS. 83 to 85.

Example 11: Uses of Base Editors to Treat Disease

Base editors or complexes provided herein (e.g., BE3) may be used to modify nucleic acids. For example, base editors may be used to change a cytosine to a thymine in a nucleic acid (e.g., DNA). Such changes may be made to, inter alia, alter the amino acid sequence of a protein, to destroy or create a start codon, to create a stop codon, to disrupt splicing donors, to disrupt splicing acceptors or edit regulatory sequences. Examples of possible nucleotide changes are shown in FIG. 86.

Base editors or complexes provided herein (e.g., BE3) may be used to edit an isoform of Apolipoprotein E in a subject. For example, an Apolipoprotein E isoform may be edited to yield an isoform associated with a lower risk of developing Alzheimer's disease. Apolipoprotein E has four isoforms that differ at amino acids 112 and 158. APOE4 is the largest and most common genetic risk factor for late-onset Alzheimer's disease. Arginine residue 158 of APOE4, encoded by the nucleic acid sequence CGC, may be changed to a cysteine by using a base editor (e.g., BE3) to change the CGC nucleic acid sequence to TGC, which encodes cysteine at residue 158. This change yields an APOE3r isoform, which is associated with lower Alzheimer's disease risk. See FIG. 87.

It was tested whether base editor BE3 could be used to edit APOE4 to APOE3r in mouse astrocytes (FIG. 88). APOE 4 mouse astrocytes were nucleofected with Cas9+template or BE3, targeting the nucleic acid encoding Arginine 158 of APOE4. The Cas9+template yielded only 0.3% editing with 26% indels, while BE3 yielded 75% editing with 5% indels. Two additional base-edited cytosines are silent and do not yield changes to the amino acid sequence (FIG. 88).

Base editors or complexes provided herein may be used to treat prion protein diseases such as Creutzfeldt-Jakob disease and fatal familial insomnia, for example, by introducing mutations into a PRNP gene. Reverting PRNP mutations may not yield therapeutic results, and intels in PRNP may be pathogenic. Accordingly, it was tested whether PRNP could be mutated using base editors (e.g., BE3) to introduce a premature stop codon in the PRNP gene. BE3, associated with its guide RNA, was introduced into HEK cells or glioblastoma cells and was capable of editing the PRNP gene to change the encoded arginine at residue 37 to a stop codon. BE3 yielded 41% editing (FIG. 89).

Additional genes that may be edited include the following: APOE editing of Arg 112 and Arg 158 to treat increased Alzheimer's risk; APP editing of Ala 673 to decrease Alzheimer's risk; PRNP editing of Arg 37 to treat fatal familial insomnia and other prion protein diseases; DMD editing of the exons 23 and 51 splice sites to treat Duchenne muscular dystrophy; FTO editing of intron 1 to treat obesity risk; PDS editing of exon 8 to treat Pendred syndrome (genetic deafness); TMC1 editing of exon 8 to treat congenital hearing loss; CYBB editing of various patient-relevant mutations to treat chronic granulomatous disease. Additional diseases that may be treated using the base editors provided herein are shown in Table 6, below.

UGI also plays a key role. Knocking out UDG (which UGI inhibits) was shown to dramatically improve the cleanliness and efficiency of C to T base editing (FIG. 90). Furthermore, base editors with nickase and without UGI were shown to produce a mixture of outcomes, with very high indel rates (FIG. 91).

Example 12: Expanding the Targeting Scope of Base Editing

Base editing is a new approach to genome editing that uses a fusion protein containing a catalytically defective *Streptococcus pyogenes* Cas9, a cytidine deaminase, and an inhibitor of base excision repair to induce programmable, single-nucleotide C→T (or G→A) changes in DNA without generating double-strand DNA breaks, without requiring a donor DNA template, and without inducing an excess of stochastic insertions and deletions[1]. The development of five new C→T (or G→A) base editors that use natural and engineered Cas9 variants with different protospacer-adjacent motif (PAM) specificities to expand the number of sites that can be targeted by base editing by 2.5-fold are described herein. Additionally, new base editors containing mutated cytidine deaminase domains that narrow the width of the apparent editing window from approximately 5 nucleotides to 1 or 2 nucleotides were engineered, enabling the discrimination of neighboring C nucleotides that would previously be edited with comparable efficiency. Together, these developments substantially increase the targeting scope of base editing.

CRISPR-Cas9 nucleases have been widely used to mediate targeted genome editing[2]. In most genome editing applications, Cas9 forms a complex with a single guide RNA (sgRNA) and induces a double-stranded DNA break (DSB) at the target site specified by the sgRNA sequence. Cells primarily respond to this DSB through the non-homologous end-joining (NHEJ) repair pathway, which results in stochastic insertions or deletions (indels) that can cause frameshift mutations that disrupt the gene. In the presence of a donor DNA template with a high degree of homology to the sequences flanking the DSB, gene correction can be achieved through an alternative pathway known as homology directed repair (HDR).[3,4] Unfortunately, under most non-perturbative conditions HDR is inefficient, dependent on cell state and cell type, and dominated by a larger frequency of indels.[3,4] As most of the known genetic variations associated with human disease are point mutations, methods that can more efficiently and cleanly make precise point mutations are needed.

Base editing, which enables targeted replacement of a C:G base pair with a T:A base pair in a programmable manner without inducing DSBs[1], has been recently described. Base editing uses a fusion protein between a catalytically inactivated (dCas9) or nickase form of *Streptococcus pyogenes* Cas9 (SpCas9), a cytidine deaminase such as APOBEC1, and an inhibitor of base excision repair such as uracil glycosylase inhibitor (UGI) to convert cytidines into uridines within a five-nucleotide window specified by the sgRNA.[1] The third-generation base editor, BE3, converts C:G base pairs to T:A base pairs, including disease-relevant point mutations, in a variety of cell lines with higher efficiency and lower indel frequency than what can be achieved using other genome editing methods[1]. Subsequent studies have validated the deaminase-dCas9 fusion approach in a variety of settings[6,7].

Efficient editing by BE3 requires the presence of an NGG PAM that places the target C within a five-nucleotide window near the PAM-distal end of the protospacer (positions 4-8, counting the PAM as positions 21-23)[1]. This PAM requirement substantially limits the number of sites in the human genome that can be efficiently targeted by BE3, as many sites of interest lack an NGG 13- to 17-nucleotides downstream of the target C. Moreover, the high activity and processivity of BE3 results in conversion of all Cs within the editing window to Ts, which can potentially introduce undesired changes to the target locus. Herein, new C:G to T:A base editors that address both of these limitations are described.

It was thought that any Cas9 homolog that binds DNA and forms an "R-loop" complex[8] containing a single-stranded DNA bubble could in principle be converted into a base editor. These new base editors would expand the number of targetable loci by allowing non-NGG PAM sites to be edited. The Cas9 homolog from *Staphylococcus aureus* (SaCas9) is considerably smaller than SpCas9 (1053 vs. 1368 residues), can mediate efficient genome editing in mammalian cells, and requires an NNGRRT PAM[9]. SpCas9 was replaced with SaCas9 in BE3 to generate SaBE3 and transfected HEK293T cells with plasmids encoding SaBE3 and sgRNAs targeting six human genomic loci (FIGS. 92A and 92B). After 3 d, the genomic loci were subjected to high-throughput DNA sequencing (HTS) to quantify base editing efficiency. SaBE3 enabled C to T base editing of target Cs at a variety of genomic sites in human cells, with very high conversion efficiencies (approximately 50-75% of total DNA sequences converted from C to T, without enrichment for transfected cells) arising from targeting Cs at positions 6-11. The efficiency of SaBE3 on NNGRRT-containing target sites in general exceeded that of BE3 on NGG-containing target sites[1]. Perhaps due to its higher average efficiency, SaBE3 can also result in detectable base editing at target Cs at positions outside of the canonical BE3 activity window (FIG. 92C). In comparison, BE3 showed significantly reduced editing under the same conditions (0-11%), in accordance with the known SpCas9 PAM preference (FIG. 106A)[10]. These data show that SaBE3 can facilitate very efficient base editing at sites not accessible to BE3.

The targeting range of base editors was further expanded by applying recently engineered Cas9 variants that expand or alter PAM specificities. Joung and coworkers recently reported three SpCas9 mutants that accept NGA (VQR-Cas9), NGAG (EQR-Cas9), or NGCG(VRER-Cas9) PAM sequences[11]. In addition, Joung and coworkers engineered a SaCas9 variant containing three mutations (SaKKH-Cas9) that relax its PAM requirement to NNNRRT[12]. The SpCas9 portion of BE3 was replaced with these four Cas9 variants to produce VQR-BE3, EQR-BE3, VRER-BE3, and SaKKH-BE3, which target NNNRRT,NGA, NGAG, and NGCG PAMs respectively. HEK293T cells were transfected with plasmids encoding these constructs and sgRNAs targeting six genomic loci for each new base editor, and measured C to T base conversions using HTS.

SaKKH-BE3 edited sites with NNNRRT PAMs with efficiencies up to 62% of treated, non-enriched cells (FIG. 92D). As expected, SaBE3 was unable to efficiently edit targets containing PAMs that were NNNHRRT (where H=A, C, or T) (FIG. 92D). VQR-BE3, EQR-BE3, and VRER-BE3 exhibited more modest, but still substantial base editing efficiencies of up to 50% of treated, non-enriched cells at genomic loci with the expected PAM requirements with an editing window similar to that of BE3 (FIGS. 92E and 92F). Base editing efficiencies of VQR-BE3, EQR-BE3, and VRER-BE3 in general closely paralleled the reported PAM requirements of the corresponding Cas9 nucleases; for example, EQR-BE3 was unable to efficiently edit targets containing NGAH PAM sequences (FIG. 92F). In contrast, BE3 was unable to edit sites with NGA or NGCG PAMs efficiently (0-3%), likely due to its PAM restrictions (FIG. 106B).

Collectively, the properties of SaBE3, SaKKH-BE3, VQR-BE3, EQR-BE3, and VRER-BE3 establish that base editors exhibit a modularity that facilitates their ability to exploit Cas9 homologs and engineered variants.

Next, base editors with altered activity window widths were developed. All Cs within the activity window of BE3 can be efficiently converted to Ts[1]. The ability to modulate the width of this window would be useful in cases in which it is important to edit only a subset of Cs present in the BE3 activity window.

The length of the linker between APOBEC1 and dCas9 was previously observed to modulate the number of bases that are accessible by APOBEC1 in vitro[1]. In HEK293T cells, however, varying the linker length did not significantly modulate the width of the editing window, suggesting that in the complex cellular milieu, the relative orientation and flexibility of dCas9 and the cytidine deaminase are not strongly determined by linker length (FIG. 96). Next, it was thought that truncating the 5' end of the sgRNA might narrow the base editing window by reducing the length of single-stranded DNA accessible to the deaminase upon formation of the RNA-DNA heteroduplex. HEK293T cells were co-transfected with plasmids encoding BE3 and sgRNAs of different spacer lengths targeting a locus with multiple Cs in the editing window. No consistent changes in the width of base editing when using truncated sgRNAs with 17- to 19-base spacers were observed (FIGS. 95A to 95C). Truncating the sgRNA spacer to fewer than 17 bases resulted in large losses in activity (FIG. 95A).

As an alternative approach, it was thought that mutations to the deaminase domain might narrow the width of the editing window through multiple possible mechanisms. First, some mutations may alter substrate binding, the conformation of bound DNA, or substrate accessibility to the active site in ways that reduce tolerance for non-optimal presentation of a C to the deaminase active site. Second, because the high activity of APOBEC1 likely contributes to the deamination of multiple Cs per DNA binding event,[1,13,14] mutations that reduce the catalytic efficiency of the deaminase domain of a base editor might prevent it from catalyzing successive rounds of deamination before dissociating from the DNA. Once any C:G to T:A editing event has taken place, the sgRNA no longer perfectly matches the target DNA sequence and re-binding of the base editor to the target locus should be less favorable. Both strategies were tested in an effort to discover new base editors that distinguish among multiple cytidines within the original editing window.

Given the absence of an available APOBEC1 structure, several mutations previously reported to modulate the catalytic activity of APOBEC3G, a cytidine deaminase from the same family that shares 42% sequence similarity of its active site-containing domain to that of APOBEC1, were identified[15]. Corresponding APOBEC1 mutations were incorporated into BE3 and evaluated their effect on base editing efficiency and editing window width in HEK293T cells at two C-rich genomic sites containing Cs at positions 3, 4, 5, 6, 8, 9, 10, 12, 13, and 14 (site A); or containing Cs at positions 5, 6, 7, 8, 9, 10, 11, and 13 (site B).

The APOBEC1 mutations R118A and W90A each led to dramatic loss of base editing efficiency (FIG. 97C). R132E led to a general decrease in editing efficiency but did not change the substantially narrow the shape of the editing window (FIG. 97C). In contrast, several mutations that narrowed the width of the editing window while maintaining substantial editing efficiency were found (FIGS. 93A and 97C). The "editing window width" was defined to represent the artificially calculated window width within which editing efficiency exceeds the half-maximal value for that target. The editing window width of BE3 for the two C-rich genomic sites tested was 5.0 (site A) and 6.1 (site B) nucleotides.

R126 in APOBEC1 is predicted to interact with the phosphate backbone of ssDNA[13]. Previous studies have shown that introducing the corresponding mutation into APOBEC3G decreased catalysis by at least 5-fold[14]. Interestingly, when introduced into APOBEC1 in BE3, R126A and R126E increased or maintained activity relative to BE3 at the most strongly edited positions (C5, C6, and C7), while decreasing editing activity at other positions (FIGS. 93A and 97C). Each of these two mutations therefore narrowed the width of the editing window at site A and site B to 4.4 and 3.4 nucleotides (R126A), or to 4.2 and 3.1 nucleotides (R126E), respectively (FIGS. 93A and 97C).

W90 in APOBEC1 (corresponding to W285 in APOBEC3G) is predicted to form a hydrophobic pocket in the APOBEC3G active site and assist in substrate binding[13]. Mutating this residue to Ala abrogated APOBEC3G's catalytic activity[13]. In BE3, W90A almost completely abrogated base editing efficiency (FIG. 97C). In contrast, it was found that W90Y only modestly decreased base editing activity while narrowing the editing window width at site A and site B to 3.8 and 4.9 nucleotides, respectively (FIG. 93A). These results demonstrate that mutations to the cytidine deaminase domain can narrow the activity window width of the corresponding base editors.

W90Y, R126E, and R132E, the three mutations that narrowed the editing window without drastically reducing base editing activity, were combined into doubly and triply mutated base editors. The double mutant W90Y+R126E resulted in a base editor (YE1-BE3) with BE3-like maximal editing efficiencies, but substantially narrowed editing window width (width at site A and site B=2.9 and 3.0 nucleotides, respectively (FIG. 93A). The W90Y+R132E base editor (YE2-BE3) exhibited modestly lower editing efficiencies (averaging 1.4-fold lower maximal editing yields across the five sites tested compared with BE3), and also substantially narrowed editing window width (width at site A and site B=2.7 and 2.8 nucleotides, respectively) (FIG. 97C). The R126E+R132E double mutant (EE-BE3) showed similar maximal editing efficiencies and editing window width as YE2-BE3 (FIG. 97C). The triple mutant W90Y+R126E+R132E (YEE-BE3) exhibited 2.0-fold lower average maximal editing yields but very little editing beyond the C6 position and an editing window width of 2.1 and 1.4 nucleotides for site A and site B, respectively (FIG. 97C). These data taken together indicate that mutations in the cytidine deaminase domain can strongly affect editing window widths, in some cases with minimal or only modest effects on editing efficiency.

The base editing outcomes of BE3, YE1-BE3, YE2-BE3, EE-BE3, and YEE-BE3 were further compared in HEK293T cells targeting four well-studied human genomic sites that contain multiple Cs within the BE3 activity window[1]. These target loci contained target Cs at positions 4 and 5 (HEK site 3), positions 4 and 6 (HEK site 2), positions 5 and 6 (EMX1), or positions 6, 7, 8, and 11 (FANCF). BE3 exhibited little (<1.2-fold) preference for editing any Cs within the position 4-8 activity window. In contrast, YE1-BE3, exhibited a 1.3-fold preference for editing C5 over C4 (HEK site 3), 2.6-fold preference for C6 over C4 (HEK site 2), 2.0-fold preference for C5 over C6 (EMX1), and 1.5-fold preference for C6 over C7 (FANCF) (FIG. 93B). YE2-BE3 and EE-BE3 exhibited somewhat greater positional specificity (narrower activity window) than YE1-BE3, averaging 2.4-fold preference for editing C5 over C4 (HEK site 3), 9.5-fold preference for C6 over C4 (HEK site 2), 2.9-fold preference for C5 over C6 (EMX1), and 2.6-fold preference for C7 over C6 (FANCF) (FIG. 93B). YEE-BE3 showed the greatest positional selectivity, with a 2.9-fold preference for editing C5 over C4 (HEK site 3), 29.7-fold preference for C6 over C4 (HEK site 2), 7.9-fold preference for C5 over C6 (EMX1), and 7.9-fold preference for C7 over C6 (FANCF) (FIG. 93B). The findings establish that mutant base editors can discriminate between adjacent C5, even when both nucleotides are within the BE3 editing window.

The product distributions of these four mutants and BE3 were further analyzed by HTS to evaluate their apparent processivity. BE3 generated predominantly T4-T5 (HEK site 3), T4-T6 (HEK site 2), and T5-T6 (EMX1) products in treated HEK293T cells, resulting in, on average, 7.4-fold more products containing two Ts, than products containing a single T. In contrast, YE1-BE3, YE2-BE3, EE-BE3, and YEE-BE3 showed substantially higher preferences for singly edited C4-T5, C4-T6, and T5-C6 products (FIG. 93C).

YE1-BE3 yielded products with an average single-T to double-T product ratio of 1.4. YE2-BE3 and EE-BE3 yielded products with an average single-T to double-T product ratio of 4.3 and 5.1, respectively (FIG. 93C). Consistent with the above results, the YEE-BE3 triple mutant favored single-T products by an average of 14.3-fold across the three genomic loci. (FIG. 93C). For the target site in which only one C is within the target window (HEK site 4, at position C5), all four mutants exhibited comparable editing efficiencies as BE3 (FIG. 98). These findings indicate that these BE3 mutants have decreased apparent processivity and can favor the conversion of only a single C at target sites containing multiple Cs within the BE3 editing window. These data also suggest a positional preference of C5>C6>C7≈C4 for these mutant base editors, although this preference could differ depending on the target sequence.

The window-modulating mutations in APOBEC1 were applied to VQR-BE3, allowing selective base editing of substrates at sites targeted by NGA PAM (FIG. 107A). However, when these mutations were applied to SaKKH-BE3, a linear decrease in base editing efficiency was observed without the improvement in substrate selectivity, suggesting a different kinetic equilibrium and substrate accessibility of this base editor than those of BE3 and its variants (FIG. 107B).

The five base editors with altered PAM specificities described in this study together increase the number of disease-associated mutations in the ClinVar database that can in principle be corrected by base editing by 2.5-fold (FIGS. 94A and 94B). Similarly, the development of base editors with narrowed editing windows approximately doubles the fraction of ClinVar entries with a properly positioned NGG PAM that can be corrected by base editing without comparable modification of a non-target C (from 31% for BE3 to 59% for YEE-BE3) (FIGS. 94A and 94B).

In summary, the targeting scope of base editing was substantially expanded by developing base editors that use Cas9 variants with different PAM specificities, and by developing a collection of deaminase mutants with varying editing window widths. In theory, base editing should be possible using other programmable DNA-binding proteins (such as Cpf1[16]) that create a bubble of single-stranded DNA that can serve as a substrate for a single-strand-specific nucleotide deaminase enzyme.

Materials and Methods

Cloning. PCR was performed using Q5 Hot Start High-Fidelity DNA Polymerase (New England Biolabs). Plasmids for BE and sgRNA were constructed using USER cloning (New England Biolabs), obtained from previously reported plasmids[1]. DNA vector amplification was carried out using NEB 10beta competent cells (New England Biolabs).

Cell culture. HEK293T (ATCC CRL-3216) were cultured in Dulbecco's Modified Eagle's Medium plus GlutaMax (ThermoFisher) supplemented with 10% (v/v) fetal bovine serum (FBS), at 37° C. with 5% $CO_2$. Immortalized rat astrocytes containing the ApoE4 isoform of the APOE gene (Taconic Biosciences) were maintained in Dulbecco's Modified Eagle's Medium plus GlutaMax (ThermoFisher Scientific) supplemented with 10% (v/v) fetal bovine serum (FBS) and 200 µg/mL Geneticin (ThermoFisher Scientific).

Transfections. HEK293T cells were seeded on 48-well collagen-coated BioCoat plates (Corning) and transfected at approximately 85% confluency. 750 ng of BE and 250 ng of sgRNA expression plasmids were transfected using 1.5 µl of Lipofectamine 2000 (ThermoFisher Scientific) per well according to the manufacturer's protocol.

High-throughput DNA sequencing of genomic DNA samples. Transfected cells were harvested after 3 d and the genomic DNA was isolated using the Agencourt DNAdvance Genomic DNA Isolation Kit (Beckman Coulter) according to the manufacturer's instructions. Genomic regions of interest were amplified by PCR with flanking HTS primer pairs listed in the Supplementary Sequences. PCR amplification was carried out with Phusion hot-start II DNA polymerase (ThermoFisher) according to the manufacturer's instructions. PCR products were purified using RapidTips (Diffinity Genomics). Secondary PCR was performed to attach sequencing adaptors. The products were gel-purified and quantified using the KAPA Library Quantification Kit-Illumina (KAPA Biosystems). Samples were sequenced on an Illumina MiSeq as previously described[1].

Data analysis. Nucleotide frequencies were assessed using a previously described MATLAB script [1]. Briefly, the reads were aligned to the reference sequence via the Smith-Waterman algorithm. Base calls with Q-scores below 30 were replaced with a placeholder nucleotide (N). This quality threshold results in nucleotide frequencies with an expected theoretical error rate of 1 in 1000.

Analyses of base editing processivity were performed using a custom python script. This program trims sequencing reads to the 20 nucleotide protospacer sequence as determined by a perfect match for the 7 nucleotide sequences that should flank the target site. These targets were then consolidated and sorted by abundance to assess the frequency of base editing products.

Bioinformatic analysis of the ClinVar database of human disease-associated mutations was performed in a manner similar to that previously described but with small adjustments[1]. These adjustments enable the identification of targets with PAMs of customizable length and sequence. In addition, this improved script includes a priority ranking of target C positions (C5>C6>C7>C8≈C4), thus enabling the identification of target sites in which the on-target C is either the only cytosine within the window or is placed at a position with higher predicted editing efficiency than any off-target C within the editing window.

REFERENCES FOR EXAMPLE 12

1 Komor, A. C. et al. Programmable editing of a target base in genomic DNA without double-stranded DNA cleavage. *Nature* 533, 420-424 (2016).
2 Sander, J. D. & Joung, J. K. CRISPR-Cas systems for editing, regulating and targeting genomes. *Nature biotechnology* 32, 347-355 (2014).
3 Cong, L. et al. Multiplex genome engineering using CRISPR/Cas systems. *Science* 339, 819-823 (2013).
4 Ran, F. A. et al. Genome engineering using the CRISPR-Cas9 system. *Nat. Protocols* 8, 2281-2308 (2013).
5 Landrum, M. J. et al. ClinVar: public archive of interpretations of clinically relevant variants. *Nucleic Acids Res.* 44, D862-D868 (2015).
6 Nishida, K. et al. Targeted nucleotide editing using hybrid prokaryotic and vertebrate adaptive immune systems. *Science* 353, aaf8729-1-8 (2016).
7 Ma, Y. et al. Targeted AID-mediated mutagenesis (TAM) enables efficient genomic diversification in mammalian cells. *Nat. Methods* doi:10.1038/nmeth.4027 (2016).
8 Jiang, F. et al. Structures of a CRISPR-Cas9 R-loop complex primed for DNA cleavage. *Science* 351, 867-71 (2016).
9 Ran, F. A. et al. In vivo genome editing using *Staphylococcus aureus* Cas9. *Nature* 520, 186-191 (2015).

10 Zhang, Y. et al. Comparison of non-canonical PAMs for CRISPR/Cas9-mediated DNA cleavage in human cells. *Sci. Rep.* 4, (2014).
11 Kleinstiver, B. P. et. al. Engineered CRISPR-Cas9 nucleases with altered PAM specificities. *Nature* 523, 481-485 (2015).
12 Kleinstiver, B. P. et. al. Broadening the targeting range of *Staphylococcus aureus* CRISPR-Cas9 by modifying PAM recognition. *Nat. Biotechnol.* 33, 1293-1298 (2015).
13 Holden, L. G. et al. Crystal structure of the anti-viral APOBEC3G catalytic domain and functional implications. *Nature* 452, 121-124 (2008).
14 Chen, K.-M. et al. Structure of the DNA deaminase domain of the HIV-1 restriction factor APOBEC3G. *Nature* 452, 116-119 (2008).
15 Harris, R. S., Petersen-Mahrt, S. K. & Neuberger, M. S. RNA Editing Enzyme APOBEC1 and Some of Its Homologs Can Act as DNA Mutators. *Molecular Cell* 10, 1247-1253 (2002).
16 Zetsche, B. et al. Cpf1 Is a Single RNA-Guided Endonuclease of a Class 2 CRISPR-Cas System. *Cell* 163, 759-771 (2015).

Example 13

Using improved transfection procedures and better plasmids, biological replicates (n=3) were used to install the four HF mutations into the Cas9 portion of BE3. The mutations do not significantly effect on-targeting editing with plasmid delivery (FIG. 99). At the tested concentration, BE3 protein delivery works; however, the on-target editing is lower than for plasmid delivery (FIG. 100). Protein delivery of BE3 with the HF mutations installed reduces on-targeting editing efficiency but still yields some edited cells (FIG. 101).

Both lipofection and installing HF mutations were shown to decrease off-target deamination events. For the four sites shown in FIG. 102, the off-target sites (OT) with the highest GUIDE-Seq reads and deamination events were assayed (Komor et al., *Nature*, 2016). The specificity ratio was calculated by dividing the off-target editing by the on-target editing at the closest corresponding C. In cases where off-target editing was not detectable, the ratio was set to 100. Thus, a higher specificity ratio indicates a more specific construct. BE3 plasmid delivery showed much higher off-target/on-target editing than protein delivery of BE3, plasmid delivery of HF-BE3, or protein delivery of HF-BE3 (FIGS. 102 and 105).

Purified proteins HF-BE3 and BE3 were analyzed in vitro for their capabilities to convert C to T residues at different positions in the spacer with the most permissive motif. Both BE3 and HF-BE3 proteins were found to have the same "window" for base editing (FIGS. 103 and 104).

A list of the disease targets is given in Table 9. The base to be edited in Table 9 is indicated in bold and underlined.

TABLE 9

Base Editor Disease Targets

| GENE | DISEASE | SPACER | PAM | EDITOR | DEFECT | CELL |
|---|---|---|---|---|---|---|
| RB1 | RETINOBLASTOMA | AATCTAGTAAATAAATTGATGT | AAAAGT | SAKKH-BE3 | SPLICING IMPAIRMENT | J82 |
| PTEN | CANCER | GACCAACGGCTAAGTGAAGA | TGA | VQR-BE3 | W111R | MC116 |
| PIK3CA | CANCER | TCCTTTCTTCACGGTTGCCT | ACTGGT | SAKKH-BE3 | K111R | CRL-5853 |
| PIK3CA | CANCER | CTCCTGCTCAGTGATTTCAG | AGA | VQR-BE3 | Q546R | CRL-2505 |
| TP53 | CANCER | TGTCACACATGTAGTTGTAG | TGG | YEE-BE3 | N239E | SNU475 |
| HRAS | CANCER | CCTCCCGGCCGGCGGTATCC | AGG | YEE-BE3 | Q61R | MC/CAR |

TABLE 6

Exemplary diseases that may be treated using base editors. The protospacer and PAM sequences are shown in the sgRNA (PAM) column. The PAM sequence is shown in parentheses and with the base to be edited indicated by underlining.

| Disease target | gene symbol | Base changed | sgRNA (PAM) | Base editor |
|---|---|---|---|---|
| Prion disease | PRNP | R37* | GGCAGCCGATACCCGGGGCA(GGG)<br>GGGCAGCCGATACCCGGGGC(AGG) | BE3 |
| Pendred syndrome | Slc26a4 | c.919-2A > | TTATTGTCCGAAATAAAAGA(AGA)<br>ATTGTCCGAAATAAAAGAAG(AGG)<br>TTGTCCGAAATAAAAGAAGA(GGA)<br>GTCCGAAATAAAAGAAGAGGAAAA(AAT)<br>GTCCGAAATAAAAGAAGAGGAAAAA(ATT) | BE3<br>(VQR SaCas9) |
| Congenital deafness | Tmc1 | c.545A > G | CAGGAAGCACGAGGCCACTG(AGG)<br>AACAGGAAGCACGAGGCCAC(TGA)<br>AGGAAGCACGAGGCCACTGA(GGA) | BE3<br>YE-BE3<br>YEE-BE3 |
| Acquired deafness | SNHL | S33F | TTGGATTCTGGAATCCATTC(TGG) | BE3 |
| Alzheimer's Disease | APP | A673T | TCTGCATCCATCTTCACTTC(AGA) | BE3 VQR |

TABLE 6-continued

Exemplary diseases that may be treated using base editors. The protospacer and PAM sequences are shown in the sgRNA (PAM) column. The PAM sequence is shown in parentheses and with the base to be edited indicated by underlining.

| Disease target | gene symbol | Base changed | sgRNA (PAM) | Base editor |
|---|---|---|---|---|
| Niemann-Pick Disease Type C | NPC1 | 1061T | CTTACAGCCAGTAATGTCAC(CGA) | BE3 VQR |

Additional exemplary genes in the human genome that may be targeted by the base editors or complexes of this disclosure are provided herein in Tables 7 and 8. Table 7 includes gene mutations that may be correcteded by changing a cytosine (C) to a thymine (T), for example, using a BE3 nucleobase editor. Table 8 includes gene mutations that may be corrected by changing a guanine (G) to an adenine (A), for example, using a BE3 nucleobase editor.

TABLE 7

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000138.4(FBN1): c.3220T > C (p.Cys1074Arg) | 137854465 | FBN1 | [ ] | [ ] | [ ] |
| NM_001927.3(DES): c.1154T > C (p.Leu385Pro) | 57955682 | DES | [ ] | [ ] | ['Myofibrillar myopathy 1', 'not provided'] |
| NM_025152.2(NUBPL): c.815-27T > C | 118161496 | NUBPL | [ ] | ['TGGTTCYAATGG ATGTCTGCTGG', 'GGTTCYAATGGA TGTCTGCTGGG'] | ['Mitochondrial complex I deficiency', 'not provided'] |
| NM_003000.2(SDHB): c.574T > C (p.Cys192Arg) | 786202732 | SDHB | [ ] | [ ] | ['Hereditary cancer-predisposing syndrome'] |
| NM_004586.2(RPS6KA3): c.803T > C (p.Phe268Ser) | 122454131 | RPS6KA3 | [ ] | [ ] | ['Coffin-Lowry syndrome'] |
| NM_005609.2(PYGM): c.425_528del | 764313717 | PYGM | [ ] | ['TGGCTGYCAGG GACCCAGCAAGG', 'CTGYCAGGGACC CAGCAAGGAGG'] | [ ] |
| NM_000124.3(ERCC6): c.2830-2A > G | 373227647 | ERCC6 | [ ] | [ ] | ['Cockayne syndrome, type B'] |
| NM_000059.3(BRCA2): c.316 + 2T > C | 81002805 | BRCA2 | ['CTTAG GYAAG TAATG CAATA TGG'] | ['CTTAGGYAAGTA ATGCAATATGG'] | ['Familial cancer of breast', 'Breast-ovarian cancer, familial 2', 'Hereditary cancer-predisposing syndrome'] |
| NM_003242.5(TGFBR2): c.923T > C (p.Leu308Pro) | 28934568 | TGFBR2 | [ ] | ['AGTTCCYGACGG CTGAGGAGCGG'] | ['Loeys-Dietz syndrome 2'] |
| NM_000410.3(HFE): c.314T > C (p.Ile105Thr) | 28934596 | HFE | [ ] | [ ] | ['Hemochromatosis type 1'] |
| NM_000308.2(CTSA): c.247T > C (p.Trp83Arg) | 28934603 | CTSA | [ ] | [ ] | ['Combined deficiency of sialidase AND beta galactosidase'] |
| NM_033290.3(MID1): c.1877T > C (p.Leu626Pro) | 28934611 | MID1 | [ ] | [ ] | ['Opitz-Frias syndrome'] |
| NM_000329.2(RPE65): c.1102T > C (p.Tyr368His) | 62653011 | RPE65 | [ ] | [ ] | ['Leber congenital amaurosis 2', 'Retinitis pigmentosa 20', 'not provided'] |
| NM_007313.2(ABL1): c.814T > C (p.Tyr272His) | 121913461 | ABL1 | [ ] | ['CCAGYACGGGG AGGTGTACGAGG', 'CAGYACGGGGAG GTGTACGAGGG'] | [ ] |
| NM_000546.5(TP53): c.398T > C (p.Met133Thr) | 28934873 | TP53 | [ ] | [ ] | ['Li-Fraumeni syndrome 1'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000490.4(AVP): c.200T > C (p.Val67Ala) | 28934878 | AVP | [ ] | [ ] | ['Neurohypophyseal diabetes insipidus'] |
| NM_021961.5(TEAD1): c.1261T > C (p.Tyr?His) | 11567847 | TEAD1 | ['TCATATTYACAGGCTTGTAAAGG'] | ['TCATATTYACAGGCTTGTAAAGG'] | [ ] |
| NM_002609.3(PDGFRB): c.1973T > C (p.Leu658Pro) | 397509381 | PDGFRB | [ ] | [ ] | ['Basal ganglia calcification, idiopathic, 4'] |
| NM_005236.2(ERCC4): c.689T > C (p.Leu230Pro) | 397509402 | ERCC4 | [ ] | [ ] | ['Fanconi anemia, complementation group Q'] |
| NM_005236.2(ERCC4): c.706T > C (p.Cys236Arg) | 397509403 | ERCC4 | [ ] | [ ] | ['XERODERMA PIGMENTOSUM, TYPE F/COCKAYNE SYNDROME'] |
| NM_173551.4(ANKS6): c.1322A > G (p.Gln441Arg) | 377750405 | ANKS6 | [ ] | ['AGGGCYGTCGGACCTTCGAGTGG', 'GGGCYGTCGGACCTTCGAGTGGG', 'GGCYGTCGGACCTTCGAGTGGGG1 | ['Nephronophthisis 16'] |
| NM_000142.4(FGFR3): c.1612A > G (p.Ile538Val) | 80053154 | FGFR3 | [ ] | [ ] | ['Hypochondroplasia'] |
| NM_000441.1(SLC26A4): c.707T > C (p.Leu236Pro) | 80338848 | SLC26A4 | [ ] | [ ] | ['Pendred syndrome', 'Enlarged vestibular aqueduct syndrome'] |
| NM_000518.4(HBB): c.337T > C (p.Cys113Arg) | 35849199 | HBB | [ ] | [ ] | [ ] |
| NM_000104.3(CYP1B1): c.2T > C (p.Met1Thr) | 72549389 | CYP1B1 | [ ] | [ ] | ['Irido-corneo-trabecular dysgenesis'] |
| NM_000169.2(GLA): c.484T > C (p.Trp162Arg) | 28935196 | — | [ ] | [ ] | ['Fabry disease'] |
| NM_001927.3(DES): c.1034T > C (p.Leu345Pro) | 57639980 | DES | [ ] | ['ATTCCCYGATGAGGCAGATGCGG', 'TTCCCYGATGAGGCAGATGCGGG] | ['Myofibrillar myopathy 1', 'not provided'] |
| NM_006517.4(SLC16A2): c.1190T > C (p.Leu397Pro) | 122455132 | SLC16A2 | [ ] | [ ] | ['Allan-Herndon-Dudley syndrome'] |
| NM_020320.3(RARS2): c.35A > G (p.Gln12Arg) | 147391618 | RARS2 | [ ] | ['ATACCYGGCAAGCAATAGCGCGG'] | ['Pontocerebellar hypoplasia type 6'] |
| NM_000239.2(LYZ): c.221T > C (p.Ile74Thr) | 121913547 | LYZ | [ ] | [ ] | ['Familial visceral amyloidosis, Ostertag type'] |
| NM_002977.3(SCN9A): c.2215A > G (p.Ile739Val) | 182650126 | — | [ ] | ['GTAAYTGCAAGATCTACAAAAGG'] | ['Small fiber neuropathy', 'not provided'] |
| NM_004700.3(KCNQ4): c.842T > C (p.Leu281Ser) | 80358278 | KCNQ4 | [ ] | ['ACATYGACAACCATCGGCTATGG'] | ['DFNA 2 Nonsyndromic Hearing Loss'] |
| NM_000169.2(GLA):c.806T > C (p.Val269Ala) | 28935488 | — | ['CAGTTAGYGATTGGCAACTTTGG'] | ['CAGTTAGYGATTGGCAACTTTGG'] | ['Fabry disease'] |
| NM_000228.2(LAMB3): c.565-2A > G | 370148688 | LAMB3 | [ ] | [ ] | ['Junctional epidermolysis bullosa gravis of Herlitz'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_052867.2(NALCN): c.1526T > C (p.Leu509Ser) | 786203987 | NALCN | [ ] | [ ] | ['CONGENITAL CONTRACTURES OF THE LIMBS AND FACE, HYPOTONIA, AND DEVELOPMENTAL DELAY'] |
| NM_001031.4(RP528): c.1A > G (p.Met1Val) | 786203997 | RP528 | ['CCAYGATGGCGGCGCGGCGGCGG'] | ['TGTCCAYGATGGCGGCGCGGCGG', 'CCAYGATGGCGGCGCGGCGGCGG'] | ['Diamond-Blackfan anemia with microtia and cleft palate'] |
| NM_005957.4(MTHFR): c.388T > C (p.Cys130Arg) | 786204012 | MTHFR | [ ] | ['GACCYGCTGCCGTCAGCGCCTGG'] | ['Homocysteinemia due to MTHFR deficiency'] |
| NM_005957.4(MTHFR): c.1530 + 2T > C | 786204027 | MTHFR | ['GAAGGYGTGGTAGGGAGGCACGG', 'AAGGYGTGGTAGGGAGGCACGGG', 'AGGYGTGGTAGGGAGGCACGGG'] | ['GAAGGYGTGGTAGGGAGGCACGG', 'AAGGYGTGGTAGGGAGGCACGGG', 'AGGYGTGGTAGGGAGGCACGGG'] | ['Homocysteinemia due to MTHFR deficiency'] |
| NM_005957.4(MTHFR): c.1793T > C (p.Leu598Pro) | 786204034 | MTHFR | [ ] | [ ] | ['Homocysteinemia due to MTHFR deficiency'] |
| NM_005957.4(MTHFR): c.1883T > C (p.Leu628Pro) | 786204037 | MTHFR | [ ] | ['TCCCACYGGACAACTGCCTCTGG'] | ['Homocysteinemia due to MTHFR deficiency'] |
| NM_000264.3(PTCH1): c.3168 + 2T > C | 786204056 | PTCH1 | ['ATCATTGYGAGTGTATTATAAGG', 'TCATTGYGAGTGTATTATAAGGG', 'CATTGYGAGTGTATTATAAGGGG'] | ['ATCATTGYGAGTGTATTATAAGG', 'TCATTGYGAGTGTATTATAAGGG', 'CATTGYGAGTGTATTATAAGGGG'] | ['Gorlin syndrome'] |
| NM_000182.4(HADHA): c.919-2A > G | 200017313 | HADHA | [ ] | [ ] | ['Mitochondrial trifunctional protein deficiency', 'Long-chain 3-hydroxyacyl-CoA dehydrogenase deficiency', 'not provided'] |
| NM_000030.2(AGXT): c.806T > C (p.Leu269Pro) | 180177271 | AGXT | [ ] | [ ] | ['Primary hyperoxaluria, type I'] |
| NM_006121.3(KRT1): c.1436T > C (p.Ile479Thr) | 57837128 | KRT1 | [ ] | [ ] | ['Ichthyosis, cyclic, with epidermolytic hyperkeratosis', 'not provided'] |
| NM_000521.3(HEXB): c.185C > T (p.Ser62Leu) | 820878 | HEXB | [ ] | [ ] | ['Sandhoff disease, infantile type'] |
| NM_000140.3(FECH): c.1137 + 3A > G | 202147607 | FECH | [ ] | ['GTAGAYACCTTAGAGAACAATGG'] | ['Erythropoietic protoporphyria'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_015046.5(SETX): c.1166T > C (p.Leu389Ser) | 29001584 | SETX | [ ] | [ ] | ['Amyotrophic lateral sclerosis type 4'] |
| NM_020365.4(EIF2B3): c.1037T > C (p.Ile346Thr) | 119474039 | EIF2B3 | ['CCAGAYTGTCAGCAAACACCTGG'] | ['CCAGAYTGTCAGCAAACACCTGG'] | ['Leukoencephalopathy with vanishing white matter'] |
| NM_139058.2(ARX): c.98T > C (p.Leu33Pro) | 28936077 | ARX | [ ] | [ ] | ['Mental retardation, with or without seizures, ARX-related, X-linked'] |
| NM_005183.3(CACNA1F): c.2267T > C (p.Ile756Thr) | 122456136 | CACNA1F | [ ] | ['TGCCAYTGCTGTGGACAACCTGG'] | [ ] |
| NM_007374.2(SIX6): c.110T > C (p.Leu37Pro) | 786204851 | SIX6 | [ ] | [GTCGCYGCCCGTGGCCCCTGCGG] | ['Cataract, microphthalmia and nystagmus'] |
| NM_000339.2(SLC12A3): c.1261T > C (p.Cys421Arg) | 28936387 | SLC12A3 | [ ] | [ ] | ['Familial hypokalemia-hypomagnesemia'] |
| NM_003865.2(HESX1): c.77T > C (p.Ile26Thr) | 28936416 | HESX1 | [ ] | [ ] | ['Pituitary hormone deficiency, combined 5'] |
| NM_022114.3(PRDM16): c.2660T > C (p.Leu887Pro) | 202115331 | PRDM16 | [ ] | [ ] | ['Dilated cardiomyopathy 1LL'] |
| NM_001159287.1(TPI1): c.832T > C (p.Phe278Leu) | 121964847 | TPI1 | [ ] | [ ] | ['Triosephosphate isomerase deficiency'] |
| NM_001692.3(ATP6V1B1): c.242T > C (p.Leu81Pro) | 121964880 | ATP6V1B1 | [ ] | [ ] | [ ] |
| NM_000490.4(AVP): c.61T > C (p.Tyr21His) | 121964893 | AVP | [ ] | [ ] | ['Neurohypophyseal diabetes insipidus'] |
| NM_000027.3(AGA): c.916T > C (p.Cys306Arg) | 121964906 | AGA | ['GTTATAYGTGCCAATGTGACTGG'] | ['GTTATAYGTGCCAATGTGACTGG'] | ['Aspartylglycosaminuria'] |
| NM_000138.4(FBN1): c.1468 + 2T > C | 794728167 | FBN1 | [ ] | ['ATTGGYACGTGATCCATCCTAGG'] | ['Thoracic aortic aneurysms and aortic dissections'] |
| NM_000027.3(AGA): c.214T > C (p.Ser72Pro) | 121964909 | AGA | [ ] | ['GACGGCYCTGTAGGCTTTGGAGG'] | ['Aspartylglycosaminuria'] |
| NM_004453.3(ETFDH): c.1001T > C (p.Leu334Pro) | 377686388 | ETFDH | [ ] | [ ] | ['Glutaric aciduria, type 2'] |
| NM_001385.2(DPYS): c.1078T > C (p.Trp360Arg) | 121964924 | DPYS | ['CGTAATAYGGGAAAAAGGCGTGG', 'AATAYGGGAAAAAGGCGTGGTGG', 'ATAYGGGAAAAAGGCGTGGTGGG'] | ['CGTAATAYGGGAAAAAGGCGTGG', 'AATAYGGGAAAAAGGCGTGGTGG', 'ATAYGGGAAAAAGGCGTGGTGGG'] | ['Dihydropyrimidinase deficiency'] |
| NM_004453.3(ETFDH): c.2T > C (p.Met1Thr) | 121964953 | ETFDH | [ ] | [ ] | ['Glutaric acidemia IIC'] |
| NM_000071.2(CBS): c.1616T > C (p.Leu539Ser) | 121964968 | CBS | [ ] | [ ] | ['Homocystinuria, pyridoxine-responsive'] |
| NM_000170.2(GLDC): c.2T > C (p.Met1Thr) | 121964978 | GLDC | [ ] | ['CGGCCAYGCAGTCCTGTGCCAGG', 'GGCCAYGCAGTCCTGTGCCAGGG'] | ['Non-ketotic hyperglycinemia'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000108.4(DLD):<br>c.1178T > C<br>(p.Ile393Thr) | 121964991 | DLD | [ ] | [ ] | ['Maple syrup urine disease, type 3'] |
| NM_014425.3(INVS):<br>c.1478T > C<br>(p.Leu493Ser) | 121964995 | INVS | [ ] | [ ] | ['Infantile nephronophthisis'] |
| NM_000398.6(CYB5R3):<br>c.382T > C<br>(p.Ser128Pro) | 121965006 | CYB5R3 | [ ] | [ ] | ['Methemoglobinemia type 2'] |
| NM_000398.6(CYB5R3):<br>c.446T > C<br>(p.Leu149Pro) | 121965008 | CYB5R3 | [ ] | ['CTGCYGGTCTACCAGGGCAAAGG'] | ['METHEMOGLOBINEMIA, TYPE I'] |
| NM_000398.6(CYB5R3):<br>c.610T > C<br>(p.Cys204Arg) | 121965011 | CYB5R3 | [ ] | [ ] | ['Methemoglobinemia type 2'] |
| NM_000398.6(CYB5R3):<br>c.218T > C<br>(p.Leu73Pro) | 121965013 | CYB5R3 | [ ] | [ ] | ['METHEMOGLOBINEMIA, TYPE I'] |
| NM_001103.3(ACTN2):<br>c.683T > C<br>(p.Met228Thr) | 786205144 | ACTN2 | ['CCTAAAAYGTTGGATGCTGAAGG'] | ['CCTAAAAYGTTGGATGCTGAAGG'] | ['Dilated cardiomyopathy 1AA'] |
| NM_000548.3(TSC2):<br>c.3106T > C<br>(p.Ser1036Pro) | 45517281 | TSC2 | [ ] | [ ] | ['Tuberous sclerosis syndrome', 'Tuberous sclerosis 2'] |
| NM_000203.4(IDUA):<br>c.1469T > C<br>(p.Leu490Pro) | 121965027 | IDUA | [ ] | [ ] | ['Mucopolysaccharidosis, MPS-I-H/S', 'Hurler syndrome', 'not provided'] |
| NM_001122764.1(PPOX):<br>c.35T > C<br>(p.Ile12Thr) | 28936677 | PPOX | [ ] | [ ] | ['Variegate porphyria'] |
| NM_000525.3(KCNJ11):<br>c.440T > C<br>(p.Leu147Pro) | 28936678 | KCNJ11 | [ ] | [ ] | ['Islet cell hyperplasia'] |
| NM_001025107.2(ADAR):<br>c.1883T > C<br>(p.Leu628Pro) | 28936680 | ADAR | [ ] | [ ] | ['Symmetrical dyschromatosis of extremities'] |
| NM_001025107.2(ADAR):<br>c.2609T > C<br>(p.Phe870Ser) | 28936681 | ADAR | [ ] | [ ] | ['Symmetrical dyschromatosis of extremities'] |
| NM_000557.4(GDF5):<br>c.1322T > C<br>(p.Leu441Pro) | 28936683 | — | [ ] | [ ] | ['Brachydactyly type A2', 'Fibular hypoplasia and complex brachydactyly'] |
| NM_000274.3(OAT):<br>c.163T > C (p.Tyr55His) | 121965037 | OAT | [ ] | [ ] | [Ornithine aminotransferase deficiency'] |
| NM_000274.3(OAT):<br>c.1205T > C<br>(p.Leu402Pro) | 121965043 | OAT | [ ] | [ ] | [Ornithine aminotransferase deficiency'] |
| NM_000223.3(KRT12):<br>c.386T > C<br>(p.Met129Thr) | 28936695 | KRT12 | [ ] | [ ] | ['Meesman corneal dystrophy', 'not provided'] |
| NM_000128.3(F11):<br>c.901T > C<br>(p.Phe301Leu) | 121965064 | F11 | [ ] | ['TGATYTCTTGGGAGAAGAACTGG'] | ['Hereditary factor XI deficiency disease'] |
| NM_000128.3(F11):<br>c.166T > C (p.Cys56Arg) | 121965069 | F11 | [ ] | [ ] | ['Hereditary factor XI deficiency disease'] |
| NM_000235.3(LIPA):<br>c.599T > C<br>(p.Leu200Pro) | 121965086 | LIPA | [ ] | [ ] | ['Lysosomal acid lipase deficiency'] |
| NM_001199.3(BMP1):<br>c.*241T > C | 786205217 | BMP1 | [ ] | [ ] | ['Osteogenesis imperfecta type 13'] |
| NM_004974.3(KCNA2):<br>c.788T > C<br>(p.Ile263Thr) | 786205231 | KCNA2 | [ ] | [ ] | ['EPILEPTIC ENCEPHALOPATHY, EARLY INFANTILE, 32'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000548.3(TSC2): c.5150T > C (p.Leu1717Pro) | 45517398 | TSC2 | [ ] | ['GCCCYGCACGC AAATGTGAGTGG', 'CCCYGCACGCAA ATGTGAGTGG'] | ['Tuberous sclerosis syndrome', 'not provided'] |
| NM_000212.2(ITGB3): c.176T > C (p.Leu59Pro) | 5918 | ITGB3 | [ ] | [ ] | ['Myocardial infarction', 'Posttransfusion purpura', 'Thrombocytopenia, neonatal alloimmune', 'Fracture, hip, susceptibility to'] |
| m.9191T > C | 386829069 | MT-ATP6 | [ ] | [ ] | ['Leigh disease'] |
| NM_000419.3(ITGA2B): c.1787T > C (p.Ile596Thr) | 76811038 | ITGA2B | [ ] | [ ] | ['Glanzmann thrombasthenia'] |
| NM_002294.2(LAMP2): c.864 + 2T > C | 730880485 | LAMP2 | [ ] | [ ] | ['Cardiomyopathy', 'Danon disease'] |
| NM_000138.4(FBN1): c.7111T > C (p.Trp2371Arg) | 794728264 | FBN1 | [ ] | [ ] | ['Thoracic aortic aneurysms and aortic dissections'] |
| NM_000531.5(OTC): c.143T > C (p.Phe48Ser) | 72554315 | OTC | [ ] | [ ] | ['not provided'] |
| NM_178454.4(DRAM2): c.79T > C (p.Tyr27His) | 786205662 | DRAM2 | [ ] | [ ] | ['Retinal dystrophy'] |
| NM_000138.4(FBN1): c.7531T > C (p.Cys2511Arg) | 794728272 | FBN1 | [ ] | [ ] | ['Thoracic aortic aneurysms and aortic dissections'] |
| NM_016218.2(POLK): c.609T > C (p.Asn203=) | 786205684 | POLK | [ ] | [ ] | ['Malignant tumor of prostate'] |
| NM_016218.2(POLK): c.*66T > C | 786205688 | POLK | [ ] | [ ] | ['Malignant tumor of prostate'] |
| NM_000354.5(SERPINA7): c.740T > C (p.Leu247Pro) | 28937312 | SERPINA7 | [ ] | [ ] | [ ] |
| NM_000531.5(OTC): c.284T > C (p.Leu95Ser) | 72554346 | OTC | ['ACAA GATYG TCTAC AGAAA CAGG'] | ['ACAAGATYGTCT ACAGAAACAGG'] | ['not provided'] |
| NM_015662.2(IFT172): c.770T > C (p.Leu257Pro) | 786205857 | IFT172 | [ ] | ['TTGTGCYAGGAA GTTATGACAGG'] | ['RETINITIS PIGMENTOSA 71'] |
| NM_000531.5(OTC): c.386 + 2T > C | 72554359 | OTC | [ ] | [ ] | ['not provided'] |
| NM_001135669.1(XPR1): c.434T > C (p.Leu145Pro) | 786205901 | XPR1 | [ ] | [ ] | ['BASAL GANGLIA CALCIFICATION, IDIOPATHIC, 6'] |
| NM_001135669.1(XPR1): c.419T > C (p.Leu140Pro) | 786205903 | XPR1 | [ ] | [ ] | ['BASAL GANGLIA CALCIFICATION, IDIOPATHIC, 6'] |
| NM_001135669.1(XPR1): c.653T > C (p.Leu218Ser) | 786205904 | XPR1 | [ ] | ['GCGTTYACGTGT CCCCCCTTTGG', 'CGTTYACGTGTC CCCCCTTTGGG'] | ['BASAL GANGLIA CALCIFICATION, IDIOPATHIC, 6'] |
| NM_181457.3(PAX3): c.268T > C (p.Tyr90His) | 104893654 | PAX3 | [ ] | [ ] | ['Klein-Waardenberg syndrome'] |
| NM_001987.4(ETV6): c.1046T > C (p.Leu349Pro) | 786205155 | ETV6 | [ ] | [ ] | ['Thrombocytopenia', 'LEUKEMIA, ACUTE LYMPHOBLASTIC; ALL'] |
| NM_000055.2(BCHE): c.1004T > C (p.Leu335Pro) | 104893684 | BCHE | [ ] | [ ] | ['Deficiency of butyrylcholine esterase'] |
| NM_000388.3(CASR): c.382T > C (p.Phe128Leu) | 104893696 | CASR | [ ] | [ ] | ['Hypocalcemia, autosomal dominant 1'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000388.3(CASR): c.1835T > C (p.Phe612Ser) | 104893698 | CASR | [ ] | [ ] | ['Hypocalcemia, autosomal dominant 1'] |
| NM_000388.3(CASR): c.2641T > C (p.Phe881Leu) | 104893704 | CASR | [ ] | ['ACGCTYTCAAGG TGGCTGCCCGG', 'CGCTYTCAAGGT GGCTGCCCGGG'] | ['Hypercalciuric hypercalcemia'] |
| NM_000388.3(CASR): c.374T > C (p.Leu125Pro) | 104893708 | CASR | [ ] | [ ] | ['Hypocalcemia, autosomal dominant 1', 'Hypocalcemia, autosomal dominant 1, with bartter syndrome'] |
| NM_000388.3(CASR): c.2362T > C (p.Phe788Leu) | 104893711 | CASR | [ ] | [ ] | ['Hypocalcemia, autosomal dominant 1'] |
| NM_000388.3(CASR): c.38T > C (p.Leu13Pro) | 104893717 | CASR | [ ] | [ ] | ['Hypocalciuric hypercalcemia, familial, type 1'] |
| NM_006580.3(CLDN16): c.500T > C (p.Leu167Pro) | 104893725 | CLDN16 | [ ] | [ ] | ['Primary hypomagnesemia'] |
| NM_006580.3(CLDN16): c.434T > C (p.Leu145Pro) | 104893731 | CLDN16 | [ ] | [ ] | ['Primary hypomagnesemia'] |
| NM_000041.3(APOE): c.388T > C (p.Cys130Arg) | 429358 | APOE | [ ] | [ ] | ['Familial type 3 hyperlipoproteinemia'] |
| NM_198159.2(MITF): c.1051T > C (p.Ser351Pro) | 104893744 | MITF | [ ] | [ ] | ['Waardenburg syndrome type 2A'] |
| NM_198159.2(MITF): c.1195T > C (p.Ser399Pro) | 104893747 | MITF | [ ] | ['ACTTYCCCTTAT TCCATCCACGG', 'CTTYCCCTTATTC CATCCACGGG'] | ['Waardenburg syndrome type 2A'] |
| NM_001122757.2(POU1F1): c.655T > C (p.Trp219Arg) | 104893758 | POU1F1 | [ ] | [ ] | ['Pituitary hormone deficiency, combined 1'] |
| NM_000539.1(RHO): c.133T > C (p.Phe45Leu) | 104893770 | RHO | [ ] | ['CATGYTTCTGCT GATCGTGCTGG', 'ATGYTTCTGCTG ATCGTGCTGGG'] | ['Retinitis pigmentosa 4'] |
| NM_003106.3(SOX2): c.290T > C (p.Leu97Pro) | 104893802 | — | [ ] | [ ] | ['Microphthalmia syndromic 3'] |
| NM_024009.2(GJB3): c.101T > C (p.Leu34Pro) | 28937583 | GJB3 | [ ] | [ ] | ['Erythrokeratodermia variabilis'] |
| NM_003907.2(EIF2B5): c.1882T > C (p.Trp628Arg) | 28937596 | EIF2B5 | [ ] | [AGGCCYGGAGC CCTGTTTTTAGG] | ['Leukoencephalopathy with vanishing white matter'] |
| NM_000551.3(VHL): c.188T > C (p.Leu63Pro) | 104893827 | VHL | [ ] | [ ] | ['Pheochromocytoma'] |
| NM_000320.2(QDPR): c.106T > C (p.Trp36Arg) | 104893865 | QDPR | [ ] | [ ] | ['Dihydropteridine reductase deficiency'] |
| NM_001151.3(SLC25A4): c.293T > C (p.Leu98Pro) | 104893876 | SLC25A4 | [ ] | ['GCAGCYCTTCTT AGGGGGTGTGG'] | ['Autosomal dominant progressive external ophthalmoplegia with mitochondrial DNA deletions 2'] |
| NM_006005.3(WFS1): c.2486T > C (p.Leu829Pro) | 104893883 | WFS1 | [ ] | ['ACCATCCYGGA GGGCCGCCTGGG'] | ['WFS1-Related Disorders'] |
| NM_001018077.1(NR3C1): c.1712T > C (p.Val571Ala) | 104893911 | NR3C1 | ['AAGY GATTG CAGCA GTGAA ATGG'] | ['AAGYGATTGCA GCAGTGAAATGG'] | ['Pseudohermaphroditism, female, with hypokalemia, due to glucocorticoid resistance'] |
| NM_001018077.1(NR3C1): c.2318T > C (p.Leu773Pro) | 104893912 | NR3C1 | [ ] | [ ] | ['Glucocorticoid resistance, generalized'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_003122.4(SPINK1): c.2T > C (p.Met1Thr) | 104893938 | SPINK1 | [ ] | [ ] | ['Hereditary pancreatitis'] |
| NM_000165.4(GJA1): c.52T > C (p.Ser18Pro) | 104893962 | GJA1 | [ ] | ['CTACYCAACTGC TGGAGGGAAGG'] | ['Oculodentodigital dysplasia'] |
| NM_000416.2(IFNGR1): c.260T > C (p.Ile87Thr) | 104893973 | IFNGR1 | ['TGTA ATAYT TCTGA TCATG TTGG'] | ['TGTAATAYTTCT GATCATGTTGG'] | ['Disseminated atypical mycobacterial infection', 'Mycobacterium tuberculosis, susceptibility to'] |
| NM_000434.3(NEU1): c.718T > C (p.Trp240Arg) | 104893978 | NEU1 | [ ] | ['GCCTCCYGGCGC TACGGAAGTGG', 'CCTCCYGGCGCT ACGGAAGTGGG', 'CTCCYGGCGCTA CGGAAGTGGGG'] | ['Sialidosis, type II'] |
| NM_153704.5(TMEM67): c.755T > C (p.Met252Thr) | 202149403 | TMEM67 | [ ] | [ ] | ['Joubert syndrome 6'] |
| NM_000162.3(GCK): c.391T > C (p.Ser131Pro) | 104894010 | GCK | [ ] | [ ] | ['Maturity-onset diabetes of the young, type 2'] |
| NM_004577.3(PSPH): c.155T > C (p.Met52Thr) | 104894036 | PSPH | [ ] | [ ] | ['Deficiency of phosphoserine phosphatase'] |
| NM_000193.3(SHH): c.995T > C (p.Val332Ala) | 104894052 | SHH | [ ] | [ ] | ['Single upper central incisor'] |
| NM_000282.3(PCCA): c.491T > C (p.Ile164Thr) | 202247815 | PCCA | [ ] | [ ] | ['Propionic acidemia'] |
| NM_002546.3(TNFRSF11B): c.349T > C (p.Phe117Leu) | 104894092 | TNFRSF11B | [ ] | ['TAGAGYTCTGCT TGAAACATAGG'] | ['Hyperphosphatasemia with bone disease'] |
| NM_000532.4(PCCB): c.1556T > C (p.Leu519Pro) | 202247822 | PCCB | [ ] | [ ] | ['Propionic acidemia'] |
| NM_006412.3(AGPAT2): c.683T > C (p.Leu228Pro) | 104894100 | AGPAT2 | [ ] | [ ] | ['Congenital generalized lipodystrophy type 1'] |
| NM_000238.3(KCNH2): c.2366T > C (p.Ile789Thr) | 794728388 | KCNH2 | [ ] | [ ] | ['Cardiac arrhythmia'] |
| NM_001243133.1(NLRP3): c.1058T > C (p.Leu353Pro) | 28937896 | NLRP3 | [ ] | [ ] | ['Familial cold urticaria'] |
| NM_021020.3(LZTS1): c.85T > C (p.Ser29Pro) | 28937897 | LZTS1 | [ ] | [ ] | [ ] |
| NM_000102.3(CYP17A1): c.316T > C (p.Ser106Pro) | 104894135 | CYP17A1 | [ ] | [CATCGCGYCCAA CAACCGTAAGG', 'ATCGCGYCCAAC AACCGTAAGGG'] | ['Complete combined 17-alpha-hydroxylase/17,20-lyase deficiency'] |
| NM_000102.3(CYP17A1): c.1216T > C (p.Trp406Arg) | 104894143 | CYP17A1 | [ ] | [ ] | ['Complete combined 17-alpha-hydroxylase/17,20-lyase deficiency'] |
| NM_000102.3(CYP17A1): c.1358T > C (p.Phe453Ser) | 104894151 | CYP17A1 | [ ] | [AGCTCTYCCTCA TCATGGCCTGG'] | ['Combined partial 17-alpha-hydroxylase/17,20-lyase deficiency'] |
| NM_005097.3(LGI1): c.136T > C (p.Cys46Arg) | 104894166 | LGI1 | [ ] | [ ] | ['Epilepsy, lateral temporal lobe, autosomal dominant'] |
| NM_005097.3(LGI1): c.695T > C (p.Leu232Pro) | 104894167 | LGI1 | [ ] | [ ] | ['Epilepsy, lateral temporal lobe, autosomal dominant'] |
| NM_000281.3(PCBD1): c.244T > C (p.Cys82Arg) | 104894177 | PCBD1 | [ ] | [ ] | ['Hyperphenylalaninemia, BH4-deficient, D'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_003476.4(CSRP3): c.131T > C (p.Leu44Pro) | 104894205 | CSRP3 | [ ] | [ ] | ['Familial hypertrophic cardiomyopathy 12', 'not specified'] |
| NM_000315.2(PTH):c. 67T > C (p.Ser23Pro) | 104894272 | PTH | [ ] | [ ] | ['Hypoparathyroidism familial isolated'] |
| NM_005055.4(RAPSN): c.848T > C (p.Leu283Pro) | 104894293 | RAPSN | [ ] | [ ] | ['Myasthenic syndrome, congenital, associated with acetylcholine receptor deficiency', 'MYASTHENIC SYNDROME, CONGENITAL, 11, ASSOCIATED WITH ACETYLCHOLINE RECEPTOR DEFICIENCY'] |
| NM_000518.4(HBB):c. 344T > C (p.Leu115Pro) | 36015961 | HBB | [ ] | [IGTGTGCYGGCC CATCACTTTGG] | ['Beta thalassemia intermedia'] |
| NM_005055.4(RAPSN): c.41T > C (p.Leu14Pro) | 104894300 | RAPSN | [ ] | [ ] | ['MYASTHENIC SYNDROME, CONGENITAL, 11, ASSOCIATED WITH ACETYLCHOLINE RECEPTOR DEFICIENCY'] |
| NM_000531.5(OTC):c. 2T > C (p.Met1Thr) | 72552295 | OTC | ['AGAA GAYGC TGTTT AATCT GAGG'] | ['AGAAGAYGCTG TTTAATCTGAGG'] | ['not provided'] |
| NM_020661.2(AICDA): c.238T > C (p.Trp80Arg) | 104894320 | AICDA | [ ] | [ ] | ['Immunodeficiency with hyper IgM type 2'] |
| NM_020661.2(AICDA): c.317T > C (p.Leu106Pro) | 104894321 | AICDA | [ ] | [ ] | ['Immunodeficiency with hyper IgM type 2'] |
| NM_020661.2(AICDA): c.452T > C (p.Phe151Ser) | 104894327 | AICDA | [ ] | [ ] | ['Immunodeficiency with hyper IgM type 2'] |
| NM_000486.5(AQP2): c.646T > C (p.Ser216Pro) | 104894329 | — | [ ] | [ ] | [ ] |
| NM_020638.2(FGF23): c.287T > C (p.Met96Thr) | 104894343 | FGF23 | [ ] | [ ] | ['Tumoral calcinosis, familial, hyperphosphatemic'] |
| NM_021044.2(DHH):c. 2T > C (p.Met1Thr) | 104894346 | DHH | [ ] | [ ] | ['46,XY gonadal dysgenesis, partial, with minifascicular neuropathy'] |
| NM_000217.2(KCNA1): c.1223T > C (p.Val408Ala) | 104894352 | KCNA1 | [ ] | [ ] | ['Episodic ataxia type 1'] |
| NM_000432.3(MYL2): c.52T > C (p.Phe18Leu) | 104894370 | MYL2 | [ ] | [ ] | ['Familial hypertrophic cardiomyopathy 10'] |
| NM_080911.2(UNG):c. 752T > C (p.Phe251Ser) | 104894380 | UNG | [ ] | [ ] | ['Immunodeficiency with hyper IgM type 5'] |
| NM_000192.3(TBX5): c.161T > C (p.Ile54Thr) | 104894384 | TBX5 | [ ] | [ ] | ['Holt-Oram syndrome'] |
| NM_175929.2(FGF14): c.449T > C (p.Phe150Ser) | 104894393 | FGF14 | [ ] | [ ] | ['Spinocerebellar ataxia 27'] |
| NM_007262.4(PARK7): c.497T > C (p.Leu166Pro) | 28938172 | PARK7 | [ ] | [ ] | ['Parkinson disease 7'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_004004.5(GJB2): c.229T > C (p.Trp77Arg) | 104894397 | GJB2 | [ ] | [ ] | ['Deafness, autosomal recessive 1A', 'not provided'] |
| NM_001130089.1(KARS): c.517T > C (p.Tyr173His) | 397514745 | KARS | ['TTCYATGATC TTCGAGGAGAGGG'] | ['CTTCYATGATCT TCGAGGAGAGG', 'TTCYATGATCTTC GAGGAGAGGG'] | ['Deafness, autosomal recessive 89'] |
| NM_000161.2(GCH1): c.662T > C (p.Met221Thr) | 104894434 | GCH1 | [ ] | [ ] | ['Dystonia, dopa-responsive, with or without hyperphenylalaninemia, autosomal recessive'] |
| NM_032409.2(PINK1): c.1040T > C (p.Leu347Pro) | 28940285 | — | [ ] | [ ] | ['Parkinson disease 6, autosomal recessive early-onset'] |
| NM_006177.3(NRL): c.479T > C (p.Leu160Pro) | 104894463 | NRL | [ ] | [ ] | ['Retinal degeneration, autosomal recessive, clumped pigment type'] |
| NM_152443.2(RDH12): c.523T > C (p.Ser175Pro) | 104894472 | RDH12 | [ ] | [CCYCGGTGGCT CACCACATTGG'] | ['Leber congenital amaurosis 13'] |
| NM_002435.2(MPI): c.413T > C (p.Met138Thr) | 104894495 | MPI | [ ] | [ ] | ['Congenital disorder of glycosylation type 1B'] |
| NM_001159702.2(FHL1): c.457T > C (p.Cys153Arg) | 122458144 | FHL1 | [ ] | [ ] | ['Myopathy, reducing body, X-linked, childhood-onset'] |
| NM_183235.2(RAB27A): c.389T > C (p.Leu130Pro) | 104894498 | RAB27A | [ ] | [ ] | ['Griscelli syndrome type 2'] |
| NM_001018005.1(TPM1): c.284T > C (p.Val95Ala) | 104894504 | TPM1 | [ ] | [ ] | ['Familial hypertrophic cardiomyopathy 3', 'Cardiomyopathy'] |
| NM_000485.2(APRT): c.329T > C (p.Leu110Pro) | 104894508 | APRT | [ ] | [ ] | ['Adenine phosphoribosyltransferase deficiency'] |
| NM_000303.2(PMM2): c.131T > C (p.Val44Ala) | 104894534 | PMM2 | [ ] | [ ] | ['Carbohydrate-deficient glycoprotein syndrome type I'] |
| NM_024006.5(VKORC1): c.134T > C (p.Val45Ala) | 104894540 | VKORC1 | [ ] | [ ] | ['Warfarin response'] |
| NM_001614.3(ACTG1): c.1109T > C (p.Val370Ala) | 104894547 | ACTG1 | [ ] | [ ] | ['Deafness, autosomal dominant 20'] |
| NM_001128085.1(ASPA): c.454T > C (p.Cys152Arg) | 104894548 | — | [ ] | [ ] | ['Spongy degeneration of central nervous system'] |
| NM_004870.3(MPDU1): c.356T > C (p.Leu119Pro) | 104894587 | MPDU1 | [ ] | ['TCCYGGTCATG CACTACAGAGG'] | ['Congenital disorder of glycosylation type 1F'] |
| NM_004870.3(MPDU1): c.2T > C (p.Met1Thr) | 104894588 | MPDU1 | [ ] | ['AATAYGGCGGC CGAGGCGGACGG'] | ['Congenital disorder of glycosylation type 1F'] |
| NM_004870.3(MPDU1): c.221T > C (p.Leu74Ser) | 104894589 | MPDU1 | [ ] | [ ] | ['Congenital disorder of glycosylation type 1F'] |
| NM_153006.2(NAGS): c.1289T > C (p.Leu430Pro) | 104894605 | — | [ ] | [ ] | ['Hyperammonemia, type III'] |
| NM_000304.3(PMP22): c.47T > C (p.Leu16Pro) | 104894617 | PMP22 | [ ] | [ ] | [Charcot-Marie-Tooth disease, type IA'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000304.3(PMP22): c.82T > C (p.Trp28Arg) | 104894626 | PMP22 | [ ] | [TAGCAAYGGAT CGTGGGCAATGG'] | [Charcot-Marie-Tooth disease, type IE'] |
| NM_018129.3(PNPO): c.784T > C (p.Ter262Gln) | 104894631 | PNPO | [ ] | [ACCTYAACTCTG GGACCTGCTGG'] | ["Pyridoxal 5'-phosphate-dependent epilepsy"] |
| NM_173477.4(USH1G): c.143T > C (p.Leu48Pro) | 104894651 | USH1G | [ ] | [ ] | ['Usher syndrome, type 1G'] |
| NM_000371.3(TTR):c. 191T > C (p.Phe64Ser) | 104894665 | TTR | [ ] | [ ] | ['Amyloidogenic transthyretin amyloidosis', 'AMYLOIDOSIS, LEPTOMENINGEAL, TRANSTHYRETIN-RELATED'] |
| NM_024301.4(FKRP): c.899T > C (p.Val300Ala) | 104894691 | FKRP | [ ] | [ ] | ['Limb-girdle muscular dystrophy-dystroglycanopathy, type C5'] |
| NM_032551.4(KISS1R): c.305T > C (p.Leu102Pro) | 104894703 | KISS1R | [ ] | ['GCCCTGCYGTAC CCGCTGCCCGG', 'TGCYGTACCCGC TGCCCGGCTGG'] | [ ] |
| NM_000660.5(TGFB1): c.673T > C (p.Cys225Arg) | 104894719 | TGFB1 | [ ] | [ ] | ['Diaphyseal dysplasia'] |
| NM_000229.1(LCAT): c.524-22T > C | 794726664 | LCAT | [ ] | [ ] | ['Fish-eye disease'] |
| NM_003332.3(TYROBP): c.2T > C (p.Met1Thr) | 104894732 | TYROBP | [ ] | [ ] | ['Polycystic lipomembranous osteodysplasia with sclerosing leukoencephalopathy'] |
| NM_000074.2(CD40LG): c.464T > C (p.Leu155Pro) | 104894769 | CD40LG | [ ] | [ ] | ['Immunodeficiency with hyper IgM type 1'] |
| NM_000495.4(COL4A5): c.438 + 2T > C | 281874738 | COL4A5 | ['TCCA GYAAG TTATA AAATT TGGG'] | ['CTCCAGYAAGTT ATAAAATTTGG', 'TCCAGYAAGTTA TAAAATTTGGG'] | ['Alport syndrome, X-linked recessive'] |
| NM_000495.4(COL4A5): c.4690T > C (p.Cys1564Arg) | 281874745 | COL4A5 | [ ] | [ ] | ['Alport syndrome, X-linked recessive'] |
| NM_178152.2(DCX):c. 373T > C (p.Tyr125His) | 104894781 | DCX | [ ] | [ ] | ['Lissencephaly, X-linked', 'Subcortical laminar heterotopia, X-linked'] |
| NM_006579.2(EBP):c. 53T > C (p.Leu18Pro) | 104894795 | EBP | [ ] | [ ] | ['MEND SYNDROME'] |
| NM_001097642.2(GJB1): c.397T > C (p.Trp133Arg) | 104894813 | GJB1 | [ ] | [ ] | ['X-linked hereditary motor and sensory neuropathy'] |
| NM_001165963.1(SCN1A): c.2690T > C (p.Leu897Ser) | 794726761 | SCN1A | [ ] | [ ] | ['Severe myoclonic epilepsy in infancy'] |
| NM_000166.5(GJB1): c.407T > C (p.Val136Ala) | 104894826 | GJB1 | [ ] | ['ATGYCATCAGCG TGGTGTTCCGG'] | ['Dejerine-Sottas disease', 'X-linked hereditary motor and sensory neuropathy'] |
| NM_001165963.1(SCN1A): c.769T > C (p.Cys257Arg) | 794726771 | SCN1A | [ ] | [ ] | ['Severe myoclonic epilepsy in infancy', 'not provided'] |
| NM_001165963.1(SCN1A): c.1033T > C (p.Cys345Arg) | 794726782 | SCN1A | [ ] | [ ] | ['Severe myoclonic epilepsy in infancy'] |
| NM_001122606.1(LAMP2): c.961T > C (p.Trp321Arg) | 104894859 | LAMP2 | [ ] | [CAGCTACYGGG ATGCCCCCTGG', 'AGCTACYGGGAT GCCCCCTGGG'] | ['Danon disease'] |
| m.10237T > C | 193302927 | MT-ND3 | [ ] | [ ] | ['Leber optic atrophy'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_033290.3(MID1): c.884T > C (p.Leu295Pro) | 104894866 | MID1 | [ ] | [ ] | ['Opitz-Frias syndrome'] |
| m.10663T > C | 193302933 | MT-ND4L | [ ] | [ ] | ['Leber optic atrophy'] |
| NM_001165963.1(SCN1A):c.4055T > C (p.Leu1352Pro) | 794726821 | — | ['TTCYGGTTTGTCTTATATTCTGG'] | ['TTCYGGTTTGTCTTATATTCTGG'] | ['Severe myoclonic epilepsy in infancy'] |
| NM_000475.4(NR0B1): c.890T > C (p.Leu297Pro) | 104894907 | NR0B1 | [ ] | [ ] | ['Congenital adrenal hypoplasia, X-linked'] |
| NM_022567.2(NYX): c.302T > C (p.Ile101Thr) | 104894911 | NYX | [ ] | [ ] | ['Congenital stationary night blindness, type 1A'] |
| NM_000513.2(OPN1MW): c.607T > C (p.Cys203Arg) | 104894914 | OPN1MW | [ ] | [ ] | ['Colorblindness, partial, deutan series', 'Cone monochromatism'] |
| NM_006517.4(SLC16A2): c.1313T > C (p.Leu438Pro) | 104894931 | SLC16A2 | [ ] | ['TGAGCYGGTGGGCCCAATGCAGG'] | ['Allan-Herndon-Dudley syndrome'] |
| NM_000330.3(RS1):c.38T > C (p.Leu13Pro) | 104894935 | RS1 | [ ] | ['TTACTTCYCTTTGGCTATGAAGG'] | ['Juvenile retinoschisis', 'not provided'] |
| NM_000116.4(TAZ):c.352T > C (p.Cys118Arg) | 104894937 | TAZ | ['AAGYGTGTGCCTGTGTGCCGAGG'] | ['AAGYGTGTGCCTGTGTGCCGAGG'] | ['3-Methylglutaconic aciduria type 2'] |
| NM_006517.4(SLC16A2): c.1481T > C (p.Leu494Pro) | 104894938 | SLC16A2 | [ ] | [ ] | ['Allan-Herndon-Dudley syndrome'] |
| NM_001109878.1(TBX22): c.641T > C (p.Leu214Pro) | 104894946 | TBX22 | [ ] | [ ] | ['Cleft palate with ankyloglossia'] |
| NM_001011658.3(TRAPPC2): c.248T > C (p.Phe83Ser) | 104894948 | — | [ ] | [ ] | ['Spondyloepiphyseal dysplasia tarda'] |
| NM_003140.2(SRY):c.326T > C (p.Phe109Ser) | 104894956 | SRY | [ ] | [ ] | ['46,XY sex reversal, type 1'] |
| NM_003140.2(SRY):c.203T > C (p.Ile68Thr) | 104894968 | SRY | [ ] | [ ] | ['46,XY sex reversal, type 1'] |
| NM_201269.2(ZNF644): c.1759A > G (p.Ile587Val) | 146936371 | ZNF644 | [ ] | [ ] | ['Myopia 21, autosomal dominant'] |
| NM_001004434.2(SLC30A2): c.161A > G (p.His54Arg) | 587776926 | SLC30A2 | [ ] | [ ] | ['Reduced zinc in breast milk'] |
| NM_000492.3(CFTR): c.3469-20T > C | 373002889 | CFTR | [ ] | [ ] | ['Cystic fibrosis'] |
| NM_001848.2(COL6A1) c.957 + 2T > C | 794727060 | COL6A1 | ['ACAAGGYGAGCGTGGGCTGCTGG', 'CAAGGYGAGCGTGGGCTGCTGGG'] | ['ACAAGGYGAGCGTGGGCTGCTGG', 'CAAGGYGAGCGTGGGCTGCTGGG'] | ['Ullrich congenital muscular dystrophy', 'Bethlem myopathy'] |
| m.4336T > C | 41456348 | MT-TQ | [ ] | [ ] | [ ] |
| NM_001065.3(TNFRSF1A): c.175T > C (p.Cys59Arg) | 104895217 | TNFRSF1A | [ ] | ['TGCYGTACCAAGTGCCACAAAGG'] | ['TNF receptor-associated periodic fever syndrome (TRAPS)'] |
| NM_003072.3(SMARCA4): c.3032T > C (p.Met1011Thr) | 281875229 | SMARCA4 | [ ] | [ ] | ['Mental retardation, autosomal dominant 16', 'not provided'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_019885.3(CYP26B1): c.436T > C (p.Ser146Pro) | 281875232 | CYP26B1 | [ ] | [ ] | ['Radiohumeral fusions with other skeletal and craniofacial anomalies', 'not provided'] |
| NM_000182.4(HADHA): c.180 + 3A > G | 781222705 | HADHA | [ ] | [ ] | ['Mitochondrial trifunctional protein deficiency', 'Long-chain 3-hydroxyacyl-CoA dehydrogenase deficiency', 'not provided'] |
| NM_000208.2(INSR): c.1124-2A > G | 587776819 | INSR | [ ] | [ ] | ['Pineal hyperplasia AND diabetes mellitus syndrome'] |
| NM_006329.3(FBLN5): c.506T > C (p.Ile169Thr) | 28939072 | FBLN5 | ['GACAYTGATGAATGTCGCTATGG'] | ['GACAYTGATGAATGTCGCTATGG'] | ['Age-related macular degeneration 3'] |
| NM_000431.3(MVK): c.803T > C (p.Ile268Thr) | 104895304 | MVK | ['CTCAAYAGATGCCATCTCCCTGG'] | ['CTCAAYAGATGCCATCTCCCTGG'] | ['Hyperimmunoglobulin D with periodic fever', 'Mevalonic aciduria'] |
| NM_024960.4(PANK2): c.437T > C (p.Met146Thr) | 28939088 | PANK2 | [ ] | [ ] | ['Hypoprebetalipo-proteinemia, acanthocytosis, retinitis pigmentosa, and pallidal degeneration'] |
| NM_005359.5(SMAD4): c.1499T > C (p.Ile500Thr) | 281875321 | SMAD4 | [ ] | [ ] | ['Myhre syndrome', 'not provided'] |
| NM_003793.3(CTSF): c.692A > G (p.Tyr231Cys) | 143889283 | CTSF | [ ] | ['CTCCAYACTGAGCTGTGCCACGG'] | ['Ceroid lipofuscinosis, neuronal, 13'] |
| NM_001159702.2(FHL1): c.310T > C (p.Cys104Arg) | 122459147 | FHL1 | [ ] | ['GGGGYGCTTCAAGGCCATTGTGG'] | ['Myopathy, reducing body, X-linked, childhood-onset'] |
| NM_001159702.2(FHL1): c.625T > C (p.Cys209Arg) | 122459149 | FHL1 | [ ] | [ ] | ['Emery-dreifuss muscular dystrophy 6'] |
| NM_006214.3(PHYH): c.135-2A > G | 201578674 | PHYH | [ ] | [ ] | ['Refsum disease, adult, 1'] |
| NM_006329.3(FBLN5): c.679T > C (p.Ser227Pro) | 28939370 | FBLN5 | [ ] | [ ] | ['Autosomal recessive cutis laxa type IA'] |
| NM_004329.2(BMPR1A): c.1409T > C (p.Met470Thr) | 199476089 | BMPR1A | [ ] | [ ] | ['Juvenile polyposis syndrome'] |
| NM_005154.4(USP8): c.2152T > C (p.Ser718Pro) | 672601307 | USP8 | [ ] | [ ] | ['Pituitary dependent hypercortisolism'] |
| NM_020184.3(CNNM4): c.971T > C (p.Leu324Pro) | 74552543 | CNNM4 | [ ] | ['AAGCTCCYGGACTTTTTTCTGGG'] | ['Cone-rod dystrophy amelogenesis imperfecta'] |
| NM_000734.3(CD247): c.2T > C (p.Met1Thr) | 672601318 | CD247 | [ ] | [ ] | ['Immunodeficiency due to defect in cd3-zeta'] |
| NM_016042.3(EXOSC3): c.712T > C (p.Trp238Arg) | 672601332 | EXOSC3 | [ ] | [ ] | ['Pontocerebellar hypoplasia, type 1b'] |
| NC_012920.1:m.14484T > C | 199476104 | MT-ND6 | [ ] | [ ] | ['Leber optic atrophy', 'Leigh disease'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| m.10158T > C | 199476117 | MT-ND3 | [ ] | ['AAAYCCACCCCT TACGAGTGCGG'] | ['Leigh disease', 'Leigh syndrome due to mitochondrial complex I deficiency', 'Mitochondrial complex I deficiency'] |
| NM_020451.2(SEPN1): c.872 + 2T > C | 794727808 | SEPN1 | [ ] | ['TCCGGYGAGTG GGCCACACTGG'] | ['Congenital myopathy with fiber type disproportion', 'Eichsfeld type congenital muscular dystrophy'] |
| NM_005022.3(PFN1): c.350A > G (p.Glu117Gly) | 140547520 | PFN1 | [ ] | ['CACCTYCTTTGC CCATCAGCAGG'] | ['Amyotrophic lateral sclerosis 18'] |
| NM_032551.4(KISS1R): c.443T > C (p.Leu148Ser) | 28939719 | KISS1R | [ ] | [ ] | [ ] |
| NM_000084.4(CLCN5): c.674T > C (p.Leu225Pro) | 273585645 | CLCN5 | [ ] | [ ] | ['Dent disease 1'] |
| NM_000030.2(AGXT): c.605T > A (p.Ile202Asn) | 536352238 | AGXT | [ ] | [ ] | ['Primary hyperoxaluria, type I'] |
| NM_000060.3(BTD): c.212T > C (p.Leu71Pro) | 397514333 | BTD | [ ] | [ ] | ['Biotinidase deficiency'] |
| NM_000060.3(BTD): c.248T > C (p.Leu83Ser) | 397514347 | BTD | [ ] | [ ] | ['Biotinidase deficiency'] |
| NM_000060.3(BTD): c.445T > C (p.Phe149Leu) | 397514359 | BTD | [ ] | ['TCACCGCYTCAA TGACACAGAGG'] | ['Biotinidase deficiency'] |
| NM_000060.3(BTD): c.743T > C (p.Ile248Thr) | 397514382 | BTD | [ ] | [ ] | ['Biotinidase deficiency'] |
| NM_000060.3(BTD): c.764T > C (p.Ile255Thr) | 397514384 | BTD | [ ] | [ ] | ['Biotinidase deficiency'] |
| NM_000060.3(BTD): c.833T > C (p.Leu278Pro) | 397514389 | BTD | [ ] | [ ] | ['Biotinidase deficiency'] |
| NM_000061.2(BTK): c.2T > C (p.Met1Thr) | 128620186 | BTK | ['AGCT AYGGC CGCAG TGATT CTGG'] | ['AGCTAYGGCCG CAGTGATTCTGG'] | ['X-linked agammaglobulinemia'] |
| m.15572T > C | 207459996 | MT-CYB | [ ] | [ ] | ['Familial colorectal cancer'] |
| NM_000060.3(BTD): c.1096T > C (p.Ser366Pro) | 397514399 | BTD | [ ] | [ ] | ['Biotinidase deficiency'] |
| m.15197T > C | 207460001 | MT-CYB | [ ] | ['CTAYCCGCCATC CCATACATTGG'] | ['Exercise intolerance'] |
| m.14849T > C | 207460004 | MT-CYB | [ ] | [ ] | [ ] |
| NM_000060.3(BTD): c.1214T > C (p.Leu405Pro) | 397514406 | BTD | [ ] | ['TTCACCCYGGTC CCTGTCTGGGG'] | ['Biotinidase deficiency'] |
| NM_000060.3(BTD): c.1252T > C (p.Cys418Arg) | 397514408 | BTD | [ ] | [ ] | ['Biotinidase deficiency'] |
| NM_000060.3(BTD): c.1267T > C (p.Cys423Arg) | 397514412 | BTD | [ ] | [ ] | ['Biotinidase deficiency'] |
| NM_001128177.1(THRB): c.1336T > C (p.Cys446Arg) | 121918703 | THRB | [ ] | [ ] | ['Thyroid hormone resistance, generalized, autosomal dominant'] |
| NM_000060.3(BTD): c.1459T > C (p.Trp487Arg) | 397514422 | BTD | [ ] | [ ] | ['Biotinidase deficiency'] |
| NM_198056.2(SCN5A): c.3963 + 2T > C | 397514447 | SCN5A | [ ] | [ ] | ['Progressive familial heart block type 1A'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_020461.3(TUBGCP6): c.2546A > G (p.Glu849Gly) | 368449236 | TUBGCP6 | [ ] | [ ] | ['Microcephaly with chorioretinopathy, autosomal recessive'] |
| NM_006225.3 (PLCD1): c.562T > C (p.Cys188Arg) | 397514471 | PLCD1 | [ ] | [ ] | ['Leukonychia totalis'] |
| NM_001161581.1(POC1A): c.398T > C (p.Leu133Pro) | 397514488 | POC1A | ['AGCYGTGGGACAAGAGCAGCCGG'] | ['AGCYGTGGGACAAGAGCAGCCGG'] | ['Short stature, onychodysplasia, facial dysmorphism, and hypotrichosis'] |
| NM_005340.6(HINT1): c.250T > C (p.Cys84Arg) | 397514489 | HINT1 | ['CAAGAAAYGTGCTGCTGATCTGG', 'AAGAAAYGTGCTGCTGATCTGGG'] | ['CAAGAAAYGTGCTGCTGATCTGG', 'AAGAAAYGTGCTGCTGATCTGGG'] | ['Gamstorp-Wohlfart syndrome'] |
| NM_000051.3(ATM): c.2T > C (p.Met1Thr) | 786203606 | ATM | [ ] | [ ] | ['Ataxia-telangiectasia syndrome', 'Hereditary cancer-predisposing syndrome'] |
| NM_004281.3(BAG3): c.1385T > C (p.Leu462Pro) | 397514507 | BAG3 | [ ] | [ ] | ['Dilated cardiomyopathy 1HH'] |
| NM_183075.2(CYP2U1): c.784T > C (p.Cys262Arg) | 397514515 | CYP2U1 | [ ] | [ ] | ['Spastic paraplegia 56, autosomal recessive'] |
| NM_006177.3(NRL): c.287T > C (p.Met96Thr) | 397514516 | NRL | [ ] | MAGGCCAYGGAGCTGCTGCAGGG'] | ['Retinitis pigmentosa 27'] |
| NM_000344.3(SMN1): c.388T > C (p.Tyr130His) | 397514518 | SMN1 | ['CACTGGAYATGGAAATAGAGAGG'] | ['CACTGGAYATGGAAATAGAGAGG'] | ['Kugelberg-Welander disease'] |
| NM_152692.4(C1GALT1C1): c.577T > C (p.Ser193Pro) | 397514537 | C1GALT1C1 | [ ] | [ ] | ['Polyagglutinable erythrocyte syndrome'] |
| NM_024531.4(SLC52A2): c.368T > C (p.Leu123Pro) | 397514538 | SLC52A2 | [ ] | [ ] | [Brown-Vialetto-Van Laere syndrome 2'] |
| NM_000138.4(FBN1): c.5746T > C (p.Cys1916Arg) | 794728238 | FBN1 | [ ] | [ ] | ['Thoracic aortic aneurysms and aortic dissections'] |
| NM_000138.4(FBN1): c.6274T > C (p.Trp2092Arg) | 794728246 | FBN1 | [ ] | [ ] | ['Thoracic aortic aneurysms and aortic dissections'] |
| NM_017802.3(DNAAF5): c.2384T > C (p.Leu795Pro) | 397514561 | DNAAF5 | [ ] | [ ] | ['Ciliary dyskinesia, primary, 18'] |
| NM_206933.2(USH2A): c.12295-2A > G | 151148854 | USH2A | [ ] | [ ] | ['Usher syndrome, type 2A'] |
| NM_000531.5 (OTC): c.134T > C (p.Leu45Pro) | 72554312 | OTC | [ ] | ['CTCACTCYAAAAAACTTTACCGG'] | ['Ornithine carbamoyltransferase deficiency', 'not provided'] |
| NM_178012.4(TUBB2B): c.350T > C (p.Leu117Pro) | 397514569 | TUBB2B | [ ] | ['GGTCCYGGATGTGGGTGAGGAAGG'] | ['Polymicrogyria, asymmetric'] |
| NM_000431.3(MVK): c.764T > C (p.Leu255Pro) | 397514570 | MVK | [ ] | [ ] | ['Porokeratosis, disseminated superficial actinic 1'] |
| NM_000431.3(MVK): c.122T > C (p.Leu41Pro) | 397514571 | MVK | [ ] | ['CGGCYTCAACCCCACAGCAATGG', 'GGCYTCAACCCCACAGCAATGGG'] | ['Porokeratosis, disseminated superficial actinic 1'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000531.5 (OTC): c.167T > C (p.Met56Thr) | 72554320 | OTC | [ ] | [ ] | ['not provided'] |
| NM_000531.5 (OTC): c.188T > C (p.Leu63Pro) | 72554324 | OTC | [ ] | [ ] | ['not provided'] |
| NM_000531.5 (OTC): c.227T > C (p.Leu76Ser) | 72554328 | OTC | [ ] | [ ] | ['not provided'] |
| NM_004055.4(CAPN5): c.731T > C (p.Leu244Pro) | 397514602 | CAPN5 | [ ] | [ ] | ['Vitreoretinopathy, neovascular inflammatory'] |
| NM_133497.3(KCNV2): c.491T > C (p.Phe164Ser) | 397514604 | KCNV2 | [ ] | [ ] | ['Retinal cone dystrophy 3B'] |
| NM_006567.3(FARS2): c.986T > C (p.Ile329Thr) | 397514611 | FARS2 | [ ] | [ ] | ['Combined oxidative phosphorylation deficiency 14'] |
| NM_018344.5(SLC29A3): c.607T > C (p.Ser203Pro) | 397514626 | SLC29A3 | ['ACTGATAYCAGGTGAGAGCCAGG'] | ['ACTGATAYCAGGTGAGAGCCAGG', 'CTGATAYCAGGTGAGAGCCAGG'] | ['Histiocytosis-lymphadenopathy plus syndrome'] |
| NM_000108.4(DLD): c.140T > C (p.Ile47Thr) | 397514651 | DLD | ['ACAGTTAYAGGTTCTGGTCCTGG', 'GTTAYAGGTTCTGGTCCTGGAGG'] | ['ACAGTTAYAGGTTCTGGTCCTGG', 'GTTAYAGGTTCTGGTCCTGGAGG'] | ['Maple syrup urine disease, type 3'] |
| NM_020632.2(ATP6V0A4): c.1739T > C (p.Met580Thr) | 3807153 | ATP6V0A4 | [ ] | [ ] | ['Renal tubular acidosis, distal, autosomal recessive'] |
| NM_000238.3(KCNH2): c.1945 + 6T > C | 794728380 | KCNH2 | ['CTGTGAGYGTGCCCAGGGGCGGG', 'TGAGYGTGCCCAGGGGCGGGCGG'] | ['CTGTGAGYGTGCCAGGGGCGGG', 'TGAGYGTGCCCAGGGGCGGGCGG'] | ['Cardiac arrhythmia'] |
| NM_001033053.2(NLRP1): c.230T > C (p.Met77Thr) | 397514692 | NLRP1 | [ ] | [ ] | ['Corneal intraepithelial dyskeratosis and ectodermal dysplasia'] |
| NM_000238.3(KCNH2): c.2396T > C (p.Leu799Pro) | 794728390 | KCNH2 | [ ] | ['GCCATCCYGGGTATGGGGTGGGG', 'CCATCCYGGGTATGGGGTGGGGG', 'CATCCYGGGTATGGGGTGGGGGG'] | ['Cardiac arrhythmia'] |
| NM_014845.5(FIG4): c.524T > C (p.Leu175Pro) | 397514707 | FIG4 | [ ] | [ ] | ['Yunis Varon syndrome'] |
| NM_001199107.1(TBC1D24): c.686T > C (p.Phe229Ser) | 397514713 | TBC1D24 | [ ] | ['GGTCTYTGACGTCTTCCTGGTGG'] | ['Early infantile epileptic encephalopathy 16'] |
| NM_080605.3(B3GALT6): c.193A > G (p.Ser65Gly) | 397514719 | B3GALT6 | [ ] | ['CGCYGGCCACCAGCACTGCCAGG'] | ['Spondyloepimetaphyseal dysplasia with joint laxity'] |
| NM_004183.3(BEST1): c.253T > C (p.Tyr85His) | 28940274 | BEST1 | [ ] | [ ] | ['Vitelliform dystrophy', 'not provided'] |
| NM_005689.2(ABCB6): c.1067T > C (p.Leu356Pro) | 397514756 | ABCB6 | [ ] | [ ] | ['Dyschromatosis universalis hereditaria 3'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000551.3(VHL): c.488T > C (p.Leu163Pro) | 28940297 | VHL | [ ] | [ ] | [ ] |
| NM_000218.2(KCNQ1): c.1025T > C (p.Leu342Pro) | 794728522 | KCNQ1 | [ ] | [ ] | ['Cardiac arrhythmia'] |
| NM_000218.2(KCNQ1): c.1251 + 2T > C | 794728528 | KCNQ1 | [ ] | [ ] | ['Cardiac arrhythmia'] |
| NM_000498.3(CYP11B2): c.1382T > C (p.Leu461Pro) | 72554627 | — | [ ] | [ ] | ['Corticosterone methyloxidase type 1 deficiency'] |
| NM_130799.2(MEN1): c.547T > C (p.Trp183Arg) | 794728649 | MEN1 | [ ] | [ ] | ['not provided'] |
| NM_213653.3(HFE2): c.238T > C (p.Cys80Arg) | 28940586 | HFE2 | [ ] | [ ] | ['Hemochromatosis type 2A'] |
| NM_198056.2(SCN5A): c.4299 + 6T > C | 794728934 | SCN5A | [ ] | [ ] | ['not provided'] |
| NM_000548.3(TSC2): c.1946 + 2T > C | 397515247 | TSC2 | [ ] | [ ] | ['Tuberous sclerosis syndrome'] |
| NM_000256.3(MYBPC3): c.3796T > C (p.Cys1266Arg) | 730880608 | MYBPC3 | [ ] | MAGYGCCGCCT GGAGGTGCGAGG'] | ['Cardiomyopathy'] |
| NM_016381.5(TREX1): c.530T > C (p.Val177Ala) | 79993407 | TREX1 | [ ] | [ ] | ['Aicardi Goutieres syndrome 1'] |
| NM_001382.3(DPAGT1): c.503T > C (p.Leu168Pro) | 397515329 | DPAGT1 | [ ] | ['AATCCYGTACTA TGTCTACATGG', 'ATCCYGTACTAT GTCTACATGGG', 'TCCYGTACTATG TCTACATGGGG'] | ['Congenital disorder of glycosylation type 1J'] |
| NM_000372.4(TYR): c.265T > C (p.Cys89Arg) | 28940877 | TYR | [ ] | [ ] | ['Tyrosinase-negative oculocutaneous albinism', 'not provided'] |
| NM_000375.2(UROS): c.-26-177T > C | 397515348 | UROS | [ ] | [ ] | ['Congenital erythropoietic porphyria'] |
| NM_015102.4(NPHP4): c.2972T > C (p.Phe991Ser) | 28940891 | NPHP4 | [ ] | [ ] | ['Nephronophthisis 4'] |
| NM_020822.2(KCNT1): c.2386T > C (p.Tyr796His) | 397515406 | KCNT1 | [ ] | [ ] | ['Epilepsy, nocturnal frontal lobe, 5'] |
| NM_000061.2(BTK): c.1516T > C (p.Cys506Arg) | 128621200 | BTK | [ ] | [ ] | ['X-linked agammaglobulinemia'] |
| NM_006383.3(CIB2): c.272T > C (p.Phe91Ser) | 397515411 | CIB2 | [ ] | [ ] | ['Deafness, autosomal recessive 48'] |
| NM_000061.2(BTK): c.1741T > C (p.Trp581Arg) | 128621205 | BTK | ['ACATT YGGGC TTTTG GTAAG TGG'] | ['ACATTYGGGCTT TTGGTAAGTGG'] | ['X-linked agammaglobulinemia'] |
| NM_018127.6(ELAC2): c.460T > C (p.Phe154Leu) | 397515465 | ELAC2 | [ ] | ['ATAYTTTCTGGT CCATTGAAAGG'] | ['Combined oxidative phosphorylation deficiency 17'] |
| NM_199355.2(ADAMTS18): c.605T > C (p.Leu202Pro) | 397515468 | ADAMTS18 | [ ] | [ ] | ['Microcornea, myopic chorioretinal atrophy, and telecanthus'] |
| NM_023110.2(FGFR1): c.494T > C (p.Leu165Ser) | 397515481 | FGFR1 | [ ] | [ ] | ['Hartsfield syndrome'] |
| NM_001059.2(TACR3): c.766T > C (p.Tyr256His) | 397515483 | TACR3 | [ ] | [ ] | ['Hypogonadotropic hypogonadism 11 with or without anosmia'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| m.14325T > C | 397515505 | MT-ND6 | [ ] | [ ] | ['Leber optic atrophy'] |
| NM_004333.4(BRAF): c.1783T > C (p.Phe595Leu) | 794729219 | BRAF | [ ] | [ ] | ['Cardiofaciocutaneous syndrome'] |
| NM_000370.3(TTPA): c.548T > C (p.Leu183Pro) | 397515525 | TTPA | [ ] | [ ] | ['Ataxia with vitamin E deficiency'] |
| NM_000375.2(UROS): c.139T > C (p.Ser47Pro) | 397515527 | UROS | [ ] | [ ] | ['Congenital erythropoietic porphyria'] |
| NM_001006657.1(WDR35): c.1592T > C (p.Leu531Pro) | 397515533 | WDR35 | [ ] | [ ] | ['Cranioectodermal dysplasia 2'] |
| NM_004595.4(SMS): c.449T > C (p.Ile150Thr) | 397515552 | SMS | [ ] | [ ] | ['Snyder Robinson syndrome'] |
| NM_005211.3(CSF1R): c.2483T > C (p.Phe828Ser) | 397515557 | CSF1R | [ ] | ['CATCTYTGACTG TGTCTACACGG'] | ['Hereditary diffuse leukoencephalopathy with spheroids'] |
| NM_000026.2(ADSL): c.1339T > C (p.Ser447Pro) | 777821034 | ADSL | [ ] | [ ] | ['not provided'] |
| NM_194248.2(OTOF): c.3413T > C (p.Leu1138Pro) | 397515599 | OTOF | [ ] | ['AGGTGCYGTTCT GGGGCCTACGG', 'GGTGCYGTTCTG GGGCCTACGGG'] | ['Deafness, autosomal recessive 9'] |
| NM_002608.2(PDGFB): c.356T > C (p.Leu119Pro) | 397515632 | PDGFB | [ ] | [ ] | ['Idiopathic basal ganglia calcification 5'] |
| NM_000404.2(GLB1): c.152T > C (p.Ile51Thr) | 72555390 | GLB1 | [ ] | [ ] | ['Gangliosidosis GM1 type 3'] |
| NM_000116.4(TAZ): c.310T > C (p.Phe104Leu) | 397515741 | TAZ | [ ] | [ ] | ['3-Methylglutaconic aciduria type 2'] |
| NM_000138.4(FBN1): c.2341T > C (p.Cys781Arg) | 397515766 | FBN1 | [ ] | ['GGACAAYGTAG AAATACTCCTGG'] | ['Marfan syndrome'] |
| NM_000138.4(FBN1): c.4222T > C (p.Cys1408Arg) | 397515802 | FBN1 | [ ] | [ ] | ['Marfan syndrome'] |
| NM_000112.3(SLC26A2): c.-26 + 2T > C | 386833492 | SLC26A2 | ['GAGA GGYGA GAAGA GGGAA GCGG'] | ['GAGAGGYGAGA AGAGGGAAGCGG'] | ['Diastrophic dysplasia'] |
| NM_000256.3(MYBPC3): c.1351 + 2T > C | 397515897 | MYBPC3 | ['AAAG GYGGG CCTGG GACCT GAGG'] | ['AAAGGYGGGCC TGGGACCTGAGG'] | ['Familial hypertrophic cardiomyopathy 4', 'Cardiomyopathy'] |
| NM_000045.3(ARG1): c.32T > C (p.Ile11Thr) | 28941474 | ARG1 | [ ] | [ ] | ['Arginase deficiency'] |
| NM_004820.3(CYP7B1): c.889A > G (p.Thr297Ala) | 587777222 | CYP7B1 | [ ] | [ ] | ['Spastic paraplegia', 'Spastic paraplegia 5A'] |
| NM_017909.3(RMND1): c.713A > G (p.Asn238Ser) | 144972972 | RMND1 | [ ] | [ ] | ['Combined oxidative phosphorylation deficiency 11'] |
| NM_000314.6(PTEN): c.545T > C (p.Leu182Ser) | 794729664 | PTEN | [ ] | [ ] | ['Macrocephaly/autism syndrome'] |
| NM_000256.3(MYBPC3): c.821 + 2T > C | 397516076 | MYBPC3 | ['CACG YGAGT GGCCA TCCTC AGGG'] | ['GCACGYGAGTG GCCATCCTCAGG', 'CACGYGAGTGGC CATCCTCAGGG'] | ['Familial hypertrophic cardiomyopathy 4', 'not specified'] |
| NM_000257.3(MYH7): c.1370T > C (p.Ile457Thr) | 397516103 | MYH7 | [ ] | [ ] | [Cardiomyopathy', 'not specified'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
| --- | --- | --- | --- | --- | --- |
| NM_000257.3(MYH7):<br>c.2093T > C<br>(p.Val698Ala) | 397516130 | MYH7 | [ ] | [ ] | ['Familial<br>hypertrophic<br>cardiomyopathy 1',<br>'not specified'] |
| NM_000257.3(MYH7):<br>c.2546T > C<br>(p.Met849Thr) | 397516156 | MYH7 | ['GGAG<br>AYGGC<br>CTCCA<br>TGAAG<br>GAGG'] | ['GGAGAYGGCCT<br>CCATGAAGGAGG'] | ['Primary familial<br>hypertrophic<br>cardiomyopathy',<br>'Cardiomyopathy'] |
| NM_000271.4(NPC1):<br>c.1133T > C<br>(p.Val378Ala) | 120074134 | NPC1 | [ ] | [ ] | ['Niemann-Pick<br>disease type C1'] |
| NM_000520.4(HEXA):<br>c.538T > C<br>(p.Tyr180His) | 28941771 | HEXA | [ ] | [ ] | [ ] |
| NM_024426.4(WT1):<br>c.1351T > C<br>(p.Phe451Leu) | 28941777 | WT1 | [ ] | [ ] | ['Diffuse mesangial<br>sclerosis'] |
| NM_024426.4(WT1):<br>c.1378T > C<br>(p.Phe460Leu) | 28941779 | WT1 | [ ] | [ ] | ['Frasier syndrome'] |
| NM_000257.3(MYH7):<br>c.602T > C<br>(p.Ile201Thr) | 397516258 | MYH7 | [ ] | [ ] | ['Dilated<br>cardiomyopathy 1S',<br>'Cardiomyopathy'] |
| NM_000257.3(MYH7):<br>c.788T > C<br>(p.Ile263Thr) | 397516269 | MYH7 | [ ] | [ ] | ['Primary familial<br>hypertrophic<br>cardiomyopathy',<br>'Familial<br>hypertrophic<br>cardiomyopathy 1',<br>'Cardiomyopathy'] |
| NM_001429.3(EP300):<br>c.3573T > A<br>(p.Tyr1191Ter) | 565779970 | EP300 | [ ] | ['CTTAYTACAGTT<br>ACCAGAACAGG'] | ['Rubinstein-Taybi<br>syndrome 2'] |
| NM_080605.3(B3GALT6):<br>c.1A > G<br>(p.Met1Val) | 786200938 | B3GALT6 | [ ] | [AGCTTCAYGGCG<br>CCCGCGCCGGG',<br>'TCAYGGCGCCCG<br>CGCCGGGCCGG'] | ['Spondyloepimetaphyseal<br>dysplasia with<br>joint laxity'] |
| NM_032551.4(KISS1R):<br>c.937T > C<br>(p.Tyr313His) | 587777844 | KISS1R | [ ] | [ ] | [ ] |
| NM_000257.3(MYH7):<br>c.5326A > G<br>(p.Ser1776Gly) | 369437262 | MYH7 | [ ] | [ ] | ['Familial<br>hypertrophic<br>cardiomyopathy 1',<br>'Cardiomyopathy',<br>'not specified'] |
| NM_000441.1(SLC26A4):<br>c.164 + 2T > C | 397516420 | SLC26A4 | [ ] | [ ] | ['Pendred syndrome',<br>'Enlarged vestibular<br>aqueduct syndrome'] |
| NM_000441.1(SLC26A4):<br>c.765 + 2T > C | 397516432 | SLC26A4 | [ ] | [ ] | ['Pendred syndrome',<br>'Enlarged vestibular<br>aqueduct syndrome'] |
| NM_000551.3(VHL):<br>c.497T > C<br>(p.Val166Ala) | 397516445 | VHL | [ ] | [ ] | ['Von Hippel-Lindau<br>syndrome',<br>'Hereditary cancer-<br>predisposing<br>syndrome'] |
| NM_000256.3(MYBPC3):<br>c.709T > C<br>(p.Tyr237His) | 730880624 | MYBPC3 | [ ] | [ ] | ['Cardiomyopathy'] |
| NM_000531.5(OTC):<br>c.392T > C<br>(p.Leu131Ser) | 72556252 | OTC | [ ] | [ ] | ['not provided'] |
| NM_000531.5(OTC):<br>c.394T > C<br>(p.Ser132Pro) | 72556253 | OTC | [ ] | [ ] | ['not provided'] |
| NM_000531.5(OTC):<br>c.416T > C<br>(p.Leu139Ser) | 72556259 | OTC | [ ] | [ ] | ['not provided'] |
| NM_000531.5(OTC):<br>c.476T > C (p.Ile159Thr) | 72556269 | OTC | [ ] | [ ] | ['not provided'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000531.5(OTC): c.490T > C (p.Ser164Pro) | 72556273 | OTC | [ ] | [ ] | ['not provided'] |
| NM_000531.5(OTC): c.526T > C (p.Tyr176His) | 72556282 | OTC | ['GGCTGATYACCTCACGCTCCAGG'] | ['GGCTGATYACCTCACGCTCCAGG', 'GATYACCTCACGCTCCAGGTTGG'] | ['not provided'] |
| NM_000531.5(OTC): c.536T > C (p.Leu179Pro) | 72556286 | OTC | [ ] | [ ] | ['not provided'] |
| NM_000229.1(LCAT): c.698T > C (p.Leu233Pro) | 28942087 | LCAT | [ ] | ['ATCTCTCYTGGGGCTCCCTGGGG', 'TCTCYTGGGGCTCCCTGGGGTGG'] | ['Norum disease'] |
| NM_174936.3(PCSK9): c.646T > C (p.Phe216Leu) | 28942112 | PCSK9 | [ ] | [ ] | ['Hypercholesterolemia, autosomal dominant, 3'] |
| NM_004572.3(PKP2): c.2386T > C (p.Cys796Arg) | 794729098 | PKP2 | [ ] | [ ] | ['not provided'] |
| NM_000061.2(BTK): c.1223T > C (p.Leu408Pro) | 128621198 | BTK | ['AGCYGGGGACTGGACAATTTGGG'] | ['GAGCYGGGGACTGGACAATTTGG', 'AGCYGGGGACTGGACAATTTGGG'] | ['X-linked agammaglobulinemia'] |
| NM_000061.2(BTK): c.1625T > C (p.Leu542Pro) | 128621203 | BTK | [ ] | [ICGGCCYGTCCAGGTGAGTGTGG'] | ['X-linked agammaglobulinemia with growth hormone deficiency'] |
| NM_006383.3(CIB2): c.368T > C (p.Ile123Thr) | 397515412 | CIB2 | [ ] | ['CTTCAYCTGCAAGGAGGACCTGG'] | ['Deafness, autosomal recessive 48'] |
| NM_001943.3(DSG2): c.523 + 2T > C | 397516709 | DSG2 | [ ] | [ ] | ['Arrhythmogenic right ventricular cardiomyopathy, type 10', 'Cardiomyopathy'] |
| NM_032575.2(GLIS2): c.523T > C (p.Cys175Arg) | 587777353 | GLIS2 | [ ] | [ ] | ['Nephronophthisis 7'] |
| NM_000492.3(CFTR): c.3230T > C (p.Leu1077Pro) | 139304906 | CFTR | [ ] | [ ] | ['Cystic fibrosis'] |
| NM_000492.3(CFTR): c.1853T > C (p.Ile618Thr) | 139468767 | CFTR | [ ] | [ ] | ['Cystic fibrosis', 'not provided'] |
| NM_002755.3(MAP2K1): c.388T > C (p.Tyr130His) | 397516793 | MAP2K1 | [ ] | [ ] | ['Cardiofaciocutaneous syndrome 3'] |
| NM_000525.3(KCNJ11): c.755T > C (p.Val252Ala) | 193929352 | KCNJ11 | [ ] | [ ] | ['Permanent neonatal diabetes mellitus'] |
| NM_000352.4(ABCC8): c.404T > C (p.Leu135Pro) | 193929364 | ABCC8 | [ ] | ['AAGCYGCTAATTGGTAGGTGAGG'] | ['Permanent neonatal diabetes mellitus'] |
| NM_000071.2(CBS): c.833T > C (p.Ile278Thr) | 5742905 | CBS | ['ATCAYTGGGGTGGATCCCGAAGG', 'TCAYTGGGGTGGATCCCGAAGGG'] | ['ATCAYTGGGGTGGATCCCGAAGG', 'TCAYTGGGGTGGATCCCGAAGGG'] | ['Homocystinuria due to CBS deficiency', 'Homocystinuria, pyridoxine-responsive', 'not provided'] |
| NM_001038.5(SCNN1A): c.1477T > C (p.Trp493Arg) | 5742912 | SCNN1A | [ ] | [ ] | ['Bronchiectasis with or without elevated sweat chloride 2', 'not specified'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
| --- | --- | --- | --- | --- | --- |
| NM_000030.2(AGXT): c.2T > C (p.Met1Thr) | 138584408 | AGXT | [ ] | [ ] | ['Primary hyperoxaluria, type I'] |
| NM_005633.3(SOS1): c.1649T > C (p.Leu550Pro) | 397517153 | SOS1 | [ ] | [ ] | ['Noonan syndrome 4', 'Rasopathy'] |
| NM_014714.3(IFT140): c.4078T > C (p.Cys1360Arg) | 431905520 | IFT140 | ['GCAG YGTGA GCTGC TCCTG GAGG'] | [CAAGCAGYGTG AGCTGCTCCTGG', 'GCAGYGTGAGCT GCTCCTGGAGG'] | ['Renal dysplasia, retinal pigmentary dystrophy, cerebellar ataxia and skeletal dysplasia'] |
| NM_022168.3(IFIH1): c.1009A > G (p.Arg337Gly) | 587777447 | IFIH1 | [ ] | [ ] | ['Aicardi-goutieres syndrome 7'] |
| NG_012123.1:g.2493 A > G | 1024611 | CCL2 | [ ] | [ ] | ['Coronary artery disease, modifier of', 'Coronary artery disease, development of, in hiv', 'Mycobacterium tuberculosis, susceptibility to'] |
| m.3394T > C | 41460449 | MT-ND1 | ['GGCY ATATA CAACT ACGCA AAGG'] | ['GGCYATATACA ACTACGCAAAGG'] | ['Leber optic atrophy'] |
| NM_001127328.2(ACADM): c.997A > G (p.Lys333Glu) | 77931234 | ACADM | [ ] | [ ] | ['Medium-chain acyl-coenzyme A dehydrogenase deficiency', 'not provided'] |
| NM_005859.4(PURA): c.299T > C (p.Leu100Pro) | 587782995 | PURA | [ ] | [ ] | ['Neonatal hypotonia', 'Intellectual disability', 'Seizures', 'Delayed speech and language development', 'Global developmental delay', 'Mental retardation, autosomal dominant 31'] |
| NM_000368.4(T5C1): c.539T > C (p.Leu180Pro) | 118203396 | TSC1 | [ ] | [ ] | ['Tuberous sclerosis syndrome', 'Tuberous sclerosis 1'] |
| NM_000256.3(MYBPC3): c.1696T > C (p.Cys566Arg) | 730880695 | MYBPC3 | [ ] | [ ] | ['Cardiomyopathy'] |
| m.7275T > C | 267606884 | MT-CO1 | [ ] | [ ] | ['Familial colorectal cancer'] |
| NM_000257.3(MYH7): c.1400T > C (p.Ile467Thr) | 730880872 | MYH7 | [ ] | ['TCGAGAYCTTCG ATGTGAGTTGG', 'CGAGAYCTTCGA TGTGAGTTGGG'] | ['Cardiomyopathy'] |
| NM_002977.3(SCN9A): c.647T > C (p.Phe216Ser) | 80356469 | SCN9A | [ ] | [ ] | ['Primary erythromelalgia'] |
| NM_002977.3(SCN9A): c.2543T > C (p.Ile848Thr) | 80356474 | — | [ ] | ['AAGATCAYTGGT AACTCAGTAGG', 'AGATCAYTGGTA ACTCAGTAGGG', 'GATCAYTGGTAA CTCAGTAGGGG'] | ['Primary erythromelalgia'] |
| NM_001164277.1(SLC37A4): c.352T > C (p.Trp118Arg) | 80356489 | SLC37A4 | [ ] | ['GGGCYGGCCCC CATGTGGGAAGG'] | ['Glucose-6-phosphate transport defect', 'not provided'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_001457.3(FLNB):<br>c.4804T > C<br>(p.Ser1602Pro) | 80356501 | FLNB | [ ] | [ ] | [ ] |
| NM_152296.4(ATP1A3):<br>c.2338T > C<br>(p.Phe780Leu) | 80356536 | ATP1A3 | [ ] | ['GCCCYTCCTGCT<br>GTTCATCATGG'] | ['Dystonia 12'] |
| NM_206933.2(USH2A):<br>c.5857 + 2T > C | 397518022 | — | [ ] | [ ] | ['Usher syndrome,<br>type 2A'] |
| NM_194248.2(OTOF):<br>c.1544T > C<br>(p.Ile515Thr) | 80356586 | OTOF | [ ] | [ ] | ['Deafness,<br>autosomal recessive<br>9', 'Auditory<br>neuropathy,<br>autosomal recessive,<br>1'] |
| NM_000335.4(SCN5A):<br>c.3745T > C<br>(p.Phe1249Leu) | 45589741 | SCN5A | [ ] | [ ] | ['Acquired long QT<br>syndrome'] |
| NM_194248.2(OTOF):<br>c.3032T > C<br>(p.Leu1011Pro) | 80356596 | OTOF | [ ] | [GATGCYGGTGTT<br>CGACAACCTGG'] | ['Deafness,<br>autosomal recessive<br>9', 'Auditory<br>neuropathy,<br>autosomal recessive,<br>1'] |
| NM_000525.3(KCNJ11):<br>c.124T > C<br>(p.Cys42Arg) | 80356610 | KCNJ11 | [ ] | [ ] | ['Permanent neonatal<br>diabetes mellitus',<br>'Transient neonatal<br>diabetes mellitus 3',<br>'MATURITY-<br>ONSET DIABETES<br>OF THE YOUNG,<br>TYPE 13'] |
| NM_000257.3(MYH7):<br>c.2723T > C<br>(p.Leu908Pro) | 730880900 | MYH7 | [ ] | [ ] | ['Cardiomyopathy'] |
| NM_152296.4(ATP1A3):<br>c.1112T > C<br>(p.Leu371Pro) | 606231433 | ATP1A3 | [ ] | [ ] | ['Alternating<br>hemiplegia of<br>childhood 2'] |
| NM_000083.2(CLCN1):<br>c.857T > C<br>(p.Val286Ala) | 80356689 | CLCN1 | [ ] | [AGGAGYGCTATT<br>TAGCATCGAGG'] | ['Myotonia<br>congenita'] |
| NM_000083.2(CLCN1):<br>c.920T > C<br>(p.Phe307Ser) | 80356701 | CLCN1 | [ ] | [ ] | ['Myotonia<br>congenita'] |
| NM_007375.3(TARDBP):<br>c.*83T > C | 80356744 | TARDBP | [ ] | [ ] | ['Amyotrophic<br>lateral sclerosis type<br>10'] |
| NM_152296.4(ATP1A3):<br>c.1250T > C<br>(p.Leu417Pro) | 606231449 | ATP1A3 | [ ] | [ ] | ['Dystonia 12'] |
| NM_001876.3(CPT1A):<br>c.1451T > C<br>(p.Leu484Pro) | 80356793 | CPT1A | [ ] | [ ] | [Carnitine<br>palmitoyltransferase<br>I deficiency'] |
| NM_000088.3(COL1A1):<br>c.4391T > C<br>(p.Leu1464Pro) | 72656353 | COL1A1 | [ ] | [ ] | ['Osteogenesis<br>imperfecta type III'] |
| NM_000089.3(COL1A2):<br>c.279 + 2T > C | 72656357 | COL1A2 | [ ] | [ ] | ['Ehlers-Danlos<br>syndrome, type 7B'] |
| NM_015046.5(SETX):<br>c.1807A > G<br>(p.Asn603Asp) | 116205032 | SETX | [ ] | [ ] | ['Spinocerebellar<br>ataxia autosomal<br>recessive 1'] |
| m.4409T > C | 118203884 | MT-TM | [ ] | ['AGGYCAGCTAA<br>ATAAGCTATCGG'] | ['Mitochondrial<br>myopathy'] |
| m.5874T > C | 118203891 | MT-TY | [ ] | [ ] | [ ] |
| NM_000130.4(F5):<br>c.1160T > C (p.Ile387Thr) | 118203911 | F5 | [ ] | [ ] | ['Thrombophilia due<br>to activated protein<br>C resistance'] |
| NM_173596.2(SLC39A5):<br>c.911T > C<br>(p.Met304Thr) | 587777625 | SLC39A5 | [ ] | ['AGAACAYGCTG<br>GGGCTTTTGCGG'] | ['Myopia 24,<br>autosomal<br>dominant'] |
| NM_024120.4(NDUFAF5):<br>c.686T > C<br>(p.Leu229Pro) | 118203929 | NDUFAF5 | [ ] | [ ] | ['Mitochondrial<br>complex I<br>deficiency'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_003159.2(CDKL5): c.602T > C (p.Leu201Pro) | 587783087 | CDKL5 | [ ] | ['ATTCYTGGGGAG CTTAGCGATGG'] | ['not provided'] |
| NM_000046.3(ARSB): c.349T > C (p.Cys117Arg) | 118203939 | ARSB | [ ] | [ ] | ['MUCOPOLYSAC CHARIDOSIS, TYPE VI, SEVERE'] |
| NM_000046.3(ARSB): c.707T > C (p.Leu236Pro) | 118203940 | ARSB | [ ] | [ ] | ['MUCOPOLYSAC CHARIDOSIS, TYPE VI, MILD'] |
| NM_013319.2(UBIAD1): c.511T > C (p.5er171Pro) | 118203951 | UBIAD1 | [ ] | ['TCTGGCYCCTTT CTCTACACAGG', 'GGCYCCTTTCTCT ACACAGGAGG'] | ['Schnyder crystalline corneal dystrophy'] |
| NM_138387.3(G6PC3): c.554T > C (p.Leu185Pro) | 118203969 | G6PC3 | [ ] | [ ] | ['Severe congenital neutropenia 4, autosomal recessive'] |
| NM_006364.2(5EC23A): c.1144T > C (p.Phe382Leu) | 118204000 | SEC23A | [ ] | [ ] | ['Craniolenticulosutural dysplasia'] |
| NM_000429.2(MAT1A): c.914T > C (p.Leu305Pro) | 118204004 | MAT1A | [ ] | [ ] | ['Methionine adenosyltransferase deficiency, autosomal recessive'] |
| NM_000018.3(ACADVL): c.1372T > C (p.Phe458Leu) | 118204017 | ACADVL | [ ] | ['TCGCATCYTCCG GATCTTTGAGG', 'CGCATCYTCCGG ATCTTTGAGGG', 'GCATCYTCCGGA TCTTTGAGGGG'] | ['Very long chain acyl-CoA dehydrogenase deficiency'] |
| NM_000833.4(GRIN2A): c.2T > C (p.Met1Thr) | 397518466 | GRIN2A | [ ] | ['CTAYGGGCAGA GTGGGCTATTGG'] | ['Focal epilepsy with speech disorder with or without mental retardation'] |
| NM_015702.2(MMADHC): c.776T > C (p.Leu259Pro) | 118204044 | MMADHC | [ ] | [ ] | ['Homocystinuria, cblD type, variant 1'] |
| NM_018077.2(RBM28): c.1052T > C (p.Leu351Pro) | 118204055 | RBM28 | [ ] | [ ] | ['Alopecia, neurologic defects, and endocrinopathy syndrome'] |
| NM_000237.2(LPL): c.662T > C (p.Ile221Thr) | 118204061 | LPL | [ ] | [ ] | ['Hyperlipoproteinemia, type I'] |
| NM_000237.2(LPL): c.337T > C (p.Trp113Arg) | 118204069 | LPL | [ ] | ['GGACYGGCTGTC ACGGGCTCAGG'] | ['Hyperlipoproteinemia, type I'] |
| NM_000237.2(LPL): c.755T > C (p.Ile252Thr) | 118204080 | LPL | [ ] | ['GTGAYTGCAGA GAGAGGACTTGG'] | ['Hyperlipoproteinemia, type I'] |
| NM_000155.3(GALT): c.580T > C (p.Phe194Leu) | 111033726 | GALT | [ ] | [ ] | ['Deficiency of UDPglucose-hexose-1-phosphate uridylyltransferase'] |
| NM_000190.3(HMBS): c.739T > C (p.Cys247Arg) | 118204111 | HMBS | [ ] | ['GCTTCGCYGCAT CGCTGAAAGGG'] | ['Acute intermittent porphyria'] |
| NM_000190.3(HMBS): c.242T > C (p.Leu81Pro) | 118204119 | HMBS | [ ] | [ ] | ['Acute intermittent porphyria'] |
| NM_001363.4(DKC1): c.1193T > C (p.Leu398Pro) | 199422253 | DKC1 | [ ] | [ ] | ['Dyskeratosis congenita X-linked'] |
| NM_004278.3(PIGL): c.500T > C (p.Leu167Pro) | 145303331 | PIGL | [ ] | [ ] | ['Zunich neuroectodermal syndrome'] |
| NM_000531.5(OTC): c.602T > C (p.Leu201Pro) | 72558407 | OTC | [ ] | [ ] | ['not provided'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000531.5(OTC): c.779T > C (p.Leu260Ser) | 72558441 | OTC | ['ATGTATYAATTACAGACACTTGG'] | ['ATGTATYAATTACAGACACTTGG'] | ['not provided'] |
| NM_000531.5(OTC): c.803T > C (p.Met268Thr) | 72558449 | OTC | [ ] | [ ] | ['not provided'] |
| NM_000256.3(MYBPC3): c.1814A > G (p.Asp605Gly) | 372371774 | MYBPC3 | [ ] | [ ] | ['Primary dilated cardiomyopathy', 'Cardiomyopathy', 'not specified'] |
| NM_000531.5(OTC): c.947T > C (p.Phe316Ser) | 72558471 | OTC | [ ] | [ ] | ['not provided'] |
| NM_000531.5(OTC): c.1005 + 2T > C | 72558484 | OTC | ['ATCATGGYAAGCAAGAAACAAGG'] | ['ATCATGGYAAGCAAGAAACAAGG'] | ['not provided'] |
| NM_000531.5(OTC): c.1018T > C (p.Ser340Pro) | 72558489 | OTC | [ ] | [ ] | ['not provided'] |
| NM_000531.5(OTC): c.1022T > C (p.Leu341Pro) | 72558490 | OTC | [ ] | [ ] | ['not provided'] |
| NM_007294.3(BRCA1): c.5291T > C (p.Leu1764Pro) | 80357281 | BRCA1 | ['GGCYAGAAATCTGTTGCTATGGG'] | ['GGGCYAGAAATCTGTTGCTATGG', 'GGCYAGAAATCTGTTGCTATGGG'] | ['Familial cancer of breast', 'Breast-ovarian cancer, familial 1'] |
| NM_000035.3(ALDOB): c.442T > C (p.Trp148Arg) | 118204430 | ALDOB | ['GGAAGYGGCGTGCTGTGCTGAGG'] | ['GGAAGYGGCGTGCTGTGCTGAGG'] | ['Hereditary fructosuria'] |
| NM_000512.4(GALNS): c.413T > C (p.Val138Ala) | 118204436 | GALNS | [ ] | [ ] | ['Mucopolysaccharidosis, MPS-IV-A'] |
| NM_024782.2(NHEJ1): c.367T > C (p.Cys123Arg) | 118204452 | NHEJ1 | [ ] | [ ] | ['Severe combined immunodeficiency with microcephaly, growth retardation, and sensitivity to ionizing radiation'] |
| NM_007294.3(BRCA1): c.65T > C (p.Leu22Ser) | 80357438 | BRCA1 | [ ] | ['AAATCTYAGAGTGTCCCATCTGG'] | ['Familial cancer of breast', 'Breast-ovarian cancer, familial 1', 'Hereditary cancer-predisposing syndrome'] |
| m.12297T > C | 121434464 | MT-TL2 | ['GTCYTAGGCCCCAAAAATTTTGG'] | ['GTCYTAGGCCCCAAAAATTTTGG'] | ['Cardiomyopathy, mitochondrial'] |
| NM_001040431.2(COA3): c.215A > G (p.Tyr72Cys) | 139877390 | COA3 | [ ] | ['CCAYCTGGGGAGGTAGGTTCAGG'] | [ ] |
| m.10010T > C | 121434476 | MT-TG | [ ] | [ ] | ['Exercise intolerance'] |
| NM_000860.5(HPGD): c.577T > C (p.Ser193Pro) | 121434481 | HPGD | [ ] | [ ] | ['Digital clubbing, isolated congenital'] |
| NM_024915.3(GRHL2): c.1192T > C (p.Tyr398His) | 587777737 | GRHL2 | [ ] | [ ] | ['Ectodermal dysplasia/short stature syndrome'] |
| NM_032374.4(APOPT1): c.353T > C (p.Phe118Ser) | 587777786 | APOPT1 | [ ] | [ ] | ['Cytochrome-c oxidase deficiency'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_001605.2(AARS): c.2251A > G (p.Arg751Gly) | 143370729 | AARS | [ ] | [ ] | ['EPILEPTIC ENCEPHALOPATHY, EARLY INFANTILE, 29'] |
| NM_000257.3(MYH7): c.2479T > C (p.Trp827Arg) | 730880744 | MYH7 | [ ] | [ ] | ['Cardiomyopathy'] |
| NM_017415.2(KLHL3): c.1160T > C (p.Leu387Pro) | 199469630 | KLHL3 | | | ['Pseudohypoaldosteronism, type 2'] |
| NM_017415.2(KLHL3): c.1280T > C (p.Met427Thr) | 199469642 | KLHL3 | | | ['Pseudohypoaldosteronism, type 2'] |
| NM_005859.4(PURA): c.563T > C (p.Ile188Thr) | 793888527 | PURA | [ ] | ['GACCAYTGCGCT GCCCGCGCAGG', 'ACCAYTGCGCTG CCCGCGCAGGG', 'CCAYTGCGCTGC CCGCGCAGGGG'] | ['not provided', 'Mental retardation, autosomal dominant 31'] |
| NM_007294.3(BRCA1): c.212 + 2T > C | 80358026 | BRCA1 | [ ] | [ ] | ['Familial cancer of breast', 'Breast-ovarian cancer, familial 1'] |
| NM_002878.3(RAD51D): c.1A > G (p.Met1Val) | 561425038 | — | [ ] | ['CGCCCAYGTTCC CCGCAGGCCGG'] | ['Hereditary cancer-predisposing syndrome'] |
| NM_018960.4(GNMT): c.149T > C (p.Leu50Pro) | 121907888 | GNMT | [ ] | [ ] | ['Glycine N-methyltransferase deficiency'] |
| NM_007294.3(BRCA1): c.5074 + 2T > C | 80358089 | BRCA1 | [ ] | [ ] | ['Breast-ovarian cancer, familial 1'] |
| NC_012920.1:m.1198 4T > C | 200911567 | MT-ND4 | [ ] | [ ] | ['Leigh disease'] |
| NM_000280.4(PAX6): c.773T > C (p.Phe258Ser) | 121907925 | PAX6 | [ ] | [ ] | ['Congenital ocular coloboma', 'Coloboma of optic disc'] |
| NM_020117.9(LARS): c.1118A > G (p.Tyr373Cys) | 201861847 | LARS | [ ] | [ ] | ['Infantile liver failure syndrome 1'] |
| NM_024105.3(ALG12): c.473T > C (p.Leu158Pro) | 121907934 | ALG12 | [ ] | ['TCCYGCTGGCCC TCGCGGCCTGG'] | ['Congenital disorder of glycosylation type 1G'] |
| NM_000152.3(GAA): c.953T > C (p.Met318Thr) | 121907936 | GAA | [ ] | [ ] | ['Glycogen storage disease type II, infantile'] |
| NM_000520.4(HEXA): c.1453T > C (p.Trp485Arg) | 121907968 | HEXA | [ ] | [ ] | ['Tay-Sachs disease'] |
| NM_000520.4(HEXA): c.632T > C (p.Phe211Ser) | 121907974 | HEXA | [ ] | [ ] | ['Tay-Sachs disease'] |
| NM_000053.3(ATP7B): c.2123T > C (p.Leu708Pro) | 121908000 | ATP7B | [ ] | [ ] | ['Wilson disease'] |
| NM_000375.2(UROS): c.217T > C (p.Cys73Arg) | 121908012 | UROS | [ ] | [ ] | ['Congenital erythropoietic porphyria'] |
| NM_153212.2(GJB4): c.409T > C (p.Phe137Leu) | 80358207 | GJB4 | [ ] | ['CCTCATCYTCAA GGCCGCCGTGG'] | ['Erythrokeratodermia variabilis'] |
| NM_000403.3(GALE): c.548T > C (p.Leu183Pro) | 121908045 | GALE | [ ] | [ ] | ['UDPglucose-4-epimerase deficiency'] |
| NM_002353.2(TACSTD2): c.557T > C (p.Leu186Pro) | 80358228 | TACSTD2 | [ ] | [CGGCYGCACCC CAAGTTCGTGG] | ['Lattice corneal dystrophy Type III'] |
| NM_001563.3(IMPG1): c.461T > C (p.Leu154Pro) | 713993047 | IMPG1 | [ ] | [ ] | ['Macular dystrophy, vitelliform, 4'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_138691.2(TMC1): c.1543T > C (p.Cys515Arg) | 121908076 | TMC1 | [ ] | ['AGGACCTYGCTG GGAAACAATGG', 'ACCTYGCTGGGA AACAATGGTGG', 'CCTYGCTGGGAA ACAATGGTGGG'] | ['Deafness, autosomal recessive 7'] |
| NM_000271.4(NPC1): c.3182T > C (p.Ile1061Thr) | 80358259 | NPC1 | [ ] | [ ] | ['Niemann-Pick disease type C1'] |
| NM_006432.3(NPC2): c.295T > C (p.Cys99Arg) | 80358264 | NPC2 | [ ] | [ ] | ['Niemann-Pick disease type C2'] |
| NM_017838.3(NHP2): c.415T > C (p.Tyr139His) | 121908089 | NHP2 | [ ] | ['GGAGGCTYACG ATGAGTGCCTGG', 'GGCTYACGATGA GTGCCTGGAGG'] | ['Dyskeratosis congenita autosomal recessive 1', 'Dyskeratosis congenita, autosomal recessive 2'] |
| NM_005857.4(ZMPSTE24): c.1018T > C (p.Trp340Arg) | 121908093 | ZMPSTE24 | [ ] | [ ] | ['Mandibuloacral dysplasia with type B lipodystrophy', 'not provided'] |
| NM_001195794.1(CLRN1): c.488T > C (p.Leu163Pro) | 121908142 | CLRN1 | [ ] | [ ] | ['Usher syndrome, type 3'] |
| NM_057176.2(BSND): c.35T > C (p.Ile12Thr) | 121908144 | BSND | [ ] | [ ] | ['Sensorineural deafness with mild renal dysfunction'] |
| NM_001243133.1(NLRP3): c.1718T > C (p.Phe573Ser) | 121908152 | NLRP3 | [ ] | [ ] | ['Familial cold urticaria', 'Chronic infantile neurological, cutaneous and articular syndrome'] |
| NM_001243133.1(NLRP3): c.926T > C (p.Phe309Ser) | 121908154 | NLRP3 | [ ] | ['GGTGCCTYTGAC GAGCACATAGG'] | ['Familial cold urticaria', 'Chronic infantile neurological, cutaneous and articular syndrome'] |
| NM_153741.1(DPM3): c.254T > C (p.Leu85Ser) | 121908155 | DPM3 | [ ] | [ ] | ['Congenital disorder of glycosylation type 1O'] |
| NM_001033855.2(DCLRE1C): c.2T > C (p.Met1Thr) | 121908158 | DCLRE1C | [ ] | ['GGCGCTAYGAG TTCTTTCGAGGG', 'GCGCTAYGAGTT CTTTCGAGGGG'] | ['Histiocytic medullary reticulosis'] |
| NM_017696.2(MCM9): c.1732 + 2T > C | 587777871 | MCM9 | [ ] | [ ] | ['Premature ovarian failure 1', 'Ovarian dysgenesis 4'] |
| NM_031433.3(MFRP): c.545T > C (p.Ile182Thr) | 121908190 | — | [ ] | [ ] | ['Nanophthalmos 2'] |
| NM_001127221.1(CACNA1A): c.2141T > C (p.Val714Ala) | 121908213 | CACNA1A | [ ] | [ ] | ['Familial hemiplegic migraine type 1'] |
| NM_001127221.1(CACNA1A): c.4469T > C (p.Phe1490Ser) | 121908233 | CACNA1A | [ ] | [ ] | ['Episodic ataxia type 2'] |
| NM_133459.3(CCBE1): c.520T > C (p.Cys174Arg) | 121908254 | CCBE1 | [ ] | [ ] | ['Hennekam lymphangiectasia-lymphedema syndrome'] |
| NM_018129.3(PNPO): c.2T > C (p.Met1Thr) | 796052870 | PNPO | [ ] | ['CCCCCAYGACGT GCTGGCTGCGG', 'CCCCAYGACGTG CTGGCTGCGGG', 'CCCAYGACGTGC TGGCTGCGGGG'] | ['not provided'] |
| NM_014845.5(FIG4): c.122T > C (p.Ile41Thr) | 121908287 | FIG4 | [ ] | [ ] | ['Charcot-Marie-Tooth disease, type 4J', 'not provided'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_001005741.2(GBA): c.751T > C (p.Tyr251His) | 121908300 | GBA | ['GCCAGAYACTTTGTGAAGTAAGG'] | ['GCCAGAYACTTTGTGAAGTAAGG', 'CCAGAYACTTTGTGAAGTAAGGG'] | ['Gaucher disease, type 1'] |
| NM_020427.2(SLURP1): c.43T > C (p.Trp15Arg) | 121908318 | SLURP1 | [ ] | ['GCAGCCYGGAGCATGGGCTGTGG'] | [Acroerythrokeratoderma'] |
| NM_020427.2(SLURP1): c.229T > C (p.Cys77Arg) | 121908319 | SLURP1 | [ ] | [ ] | ['Acroerythrokeratoderma'] |
| NM_000787.3(DBH): c.339 + 2T > C | 74853476 | DBH | [ ] | [ ] | ['Dopamine beta hydroxylase deficiency'] |
| NM_017882.2(CLN6): c.200T > C (p.Leu67Pro) | 154774633 | CLN6 | ['AGCYGGTATTCCCTCTCGAGTGG'] | ['AGCYGGTATTCCCTCTCGAGTGG'] | ['Adult neuronal ceroid lipofuscinosis', 'not provided'] |
| NM_022124.5(CDH23): c.5663T > C (p.Phe1888Ser) | 121908352 | CDH23 | [ ] | ['CTCACCTYCAACATCACTGCGGG'] | ['Deafness, autosomal recessive 12'] |
| NM_054027.4(ANKH): c.143T > C (p.Met48Thr) | 121908407 | ANKH | ['GTCGAGAYGCTGGCCAGCTACGG', 'TCGAGAYGCTGGCCAGCTACGGG'] | ['GTCGAGAYGCTGGCCAGCTACGG', 'TCGAGAYGCTGGCCAGCTACGGG'] | ['Chondrocalcinosis 2'] |
| NM_004924.4(ACTN4): c.784T > C (p.Ser262Pro) | 121908417 | ACTN4 | [ ] | [ ] | ['Focal segmental glomerulosclerosis 1'] |
| NM_014384.2(ACAD8): c.455T > C (p.Met152Thr) | 121908418 | ACAD8 | [ ] | [ ] | ['Deficiency of isobutyryl-CoA dehydrogenase'] |
| NM_153717.2(EVC): c.919T > C (p.Ser307Pro) | 121908426 | EVC | [ ] | [ ] | ['Chondroectodermal dysplasia', 'Curry-Hall syndrome'] |
| NM_001040108.1(MLH3): c.3826T > C (p.Trp1276Arg) | 121908439 | MLH3 | [ ] | [ ] | ['Hereditary nonpolyposis colorectal cancer type 7'] |
| NM_013339.3(ALG6): c.1432T > C (p.Ser478Pro) | 121908444 | ALG6 | [ ] | [ ] | ['Congenital disorder of glycosylation type 1C'] |
| NM_003835.3(RGS9): c.895T > C (p.Trp299Arg) | 121908449 | RGS9 | [ ] | [ ] | ['Prolonged electroretinal response suppression'] |
| NM_022336.3(EDAR): c.259T > C (p.Cys87Arg) | 121908451 | EDAR | [ ] | [ ] | ['Autosomal recessive hypohidrotic ectodermal dysplasia syndrome'] |
| NM_014270.4(SLC7A9): c.131T > C (p.Ile44Thr) | 121908485 | SLC7A9 | [ ] | [ ] | ['Cystinuria'] |
| NM_000030.2(AGXT): c.613T > C (p.Ser205Pro) | 121908520 | AGXT | [ ] | ['CCTGTACYCGGGCTCCCAGAAGG'] | ['Primary hyperoxaluria, type I'] |
| NM_000030.2(AGXT): c.731T > C (p.Ile244Thr) | 121908525 | AGXT | [ ] | [ ] | ['Primary hyperoxaluria, type I'] |
| NM_000026.2(ADSL): c.1312T > C (p.Ser438Pro) | 119450940 | ADSL | [ ] | [ ] | ['Adenylosuccinate lyase deficiency'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000026.2(ADSL): c.674T > C (p.Met225Thr) | 119450945 | ADSL | ['AAGA YGGTG ACAGA AAAGG CAGG'] | ['AAGAYGGTGAC AGAAAAGGCAGG'] | ['Adenylosuccinate lyase deficiency'] |
| NM_014985.3(CEP152): c.2000A > G (p.Lys667Arg) | 200879436 | CEP152 | [ ] | [ ] | ['Seckel syndrome 5', 'not specified'] |
| NM_002755.3(MAP2K1): c.158T > C (p.Phe53Ser) | 121908594 | MAP2K1 | [ ] | [ ] | ['Cardiofaciocutaneous syndrome 3', 'Rasopathy'] |
| NM_004820.3(CYP7B1): c.647T > C (p.Phe216Ser) | 121908612 | CYP7B1 | [ ] | [ ] | ['Spastic paraplegia 5A'] |
| NM_004273.4(CHST3): c.776T > C (p.Leu259Pro) | 121908616 | CHST3 | [ ] | [ ] | ['Spondyloepiphyseal dysplasia with congenital joint dislocations'] |
| NM_004273.4(CHST3): c.920T > C (p.Leu307Pro) | 121908618 | CHST3 | [ ] | ['CGTGCYGGCCTC GCGCATGGTGG'] | ['Spondyloepiphyseal dysplasia with congenital joint dislocations'] |
| NM_004273.4(CHST3): c.857T > C (p.Leu286Pro) | 121908620 | CHST3 | [ ] | [ ] | ['Spondyloepiphyseal dysplasia with congenital joint dislocations'] |
| NM_000050.4(ASS1): c.535T > C (p.Trp179Arg) | 121908646 | ASS1 | [ ] | [ ] | [ ] |
| NM_030761.4(WNT4): c.35T > C (p.Leu12Pro) | 121908653 | WNT4 | [ ] | [ ] | ['Mullerian aplasia and hyperandrogenism'] |
| NM_006432.3(NPC2): c.199T > C (p.Ser67Pro) | 11694 | NPC2 | [ ] | ['TATTCAGYCTAA AAGCAGCAAGG'] | ['Niemann-Pick disease type C2'] |
| NM_003839.3(TNFRSF11A): c.523T > C (p.Cys175Arg) | 121908656 | TNFRSF11A | [ ] | [ ] | ['Osteopetrosis autosomal recessive 7'] |
| NM_000022.2(ADA): c.320T > C (p.Leu107Pro) | 121908739 | ADA | [ ] | ['CCTGCYGGCCAA CTCCAAAGTGG'] | ['Severe combined immunodeficiency due to ADA deficiency'] |
| NM_000140.3(FECH): c.315-48T > C | 2272783 | FECH | [ ] | [ ] | ['Erythropoietic protoporphyria'] |
| NM_000059.3(BRCA2): c.7529T > C (p.Leu2510Pro) | 80358979 | BRCA2 | [ ] | [ ] | ['Familial cancer of breast', 'Breast-ovarian cancer, familial 2', 'Fanconi anemia, complementation group D1'] |
| NM_003722.4(TP63): c.1033T > C (p.Cys345Arg) | 121908837 | TP63 | [ ] | [ ] | ['Ectrodactyly, ectodermal dysplasia, and cleft lip/palate syndrome 3'] |
| NM_003722.4(TP63): c.1646T > C (p.Ile549Thr) | 121908845 | TP63 | [ ] | [ ] | ['Hay-Wells syndrome of ectodermal dysplasia', 'Rapp-Hodgkin ectodermal dysplasia syndrome'] |
| NM_000059.3(BRCA2): c.7958T > C (p.Leu2653Pro) | 80359022 | BRCA2 | [ ] | ['TGCYTCTTCAAC TAAAATACAGG'] | ['Familial cancer of breast', 'Breast-ovarian cancer, familial 2'] |
| NM_000369.2(TSHR): c.1891T > C (p.Phe631Leu) | 121908861 | TSHR | [ ] | [ ] | ['Hyperthyroidism, nonautoimmune', 'Thyroid adenoma, hyperfunctioning'] |
| NM_000369.2(TSHR): c.1358T > C (p.Met453Thr) | 121908864 | TSHR | [ ] | [ ] | ['Hyperthyroidism, nonautoimmune'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000369.2(TSHR): c.1526T > C (p.Val509Ala) | 121908874 | TSHR | [ ] | [ ] | ['Hyperthyroidism, nonautoimmune'] |
| NM_000369.2(TSHR): c.1798T > C (p.Cys600Arg) | 121908884 | TSHR | [ ] | [ ] | ['Hypothyroidism, congenital, nongoitrous, 1'] |
| NM_000369.2(TSHR): c.1400T > C (p.Leu467Pro) | 121908885 | TSHR | [ ] | [ ] | ['Hypothyroidism, congenital, nongoitrous, 1'] |
| NM_001457.3(FLNB): c.703T > C (p.Ser235Pro) | 121908896 | FLNB | [ ] | [ ] | ['Boomerang dysplasia'] |
| NM_003880.3(WISP3): c.232T > C (p.Cys78Arg) | 121908902 | WISP3 | [ ] | ['AAAATCYGTGCC AAGCAACCAGG', 'AAATCYGTGCCA AGCAACCAGGG', 'AATCYGTGCCAA GCAACCAGGGG'] | ['Progressive pseudorheumatoid dysplasia'] |
| NM_003880.3(WISP3): c.1000T > C (p.Ser334Pro) | 121908903 | WISP3 | [ ] | [ ] | ['Progressive pseudorheumatoid dysplasia'] |
| NM_002977.3(SCN9A): c.4382T > C (p.Ile1461Thr) | 121908914 | — | [ ] | [ ] | ['Paroxysmal extreme pain disorder'] |
| NM_004086.2(COCH): c.349T > C (p.Trp117Arg) | 121908929 | — | [ ] | [ ] | ['Deafness, autosomal dominant 9'] |
| NM_004086.2(COCH): c.1535T > C (p.Met512Thr) | 121908934 | — | ['AGAT AYGGC TTCTA AACCG AAGG'] | ['AGATAYGGCTTC TAAACCGAAGG'] | ['Deafness, autosomal dominant 9'] |
| NM_006892.3(DNMT3B): c.808T > C (p.Ser270Pro) | 121908947 | DNMT3B | [ ] | ['CAAGTTCYCCGA GGTGAGTCCGG', 'AAGTTCYCCGAG GTGAGTCCGGG', 'AGTTCYCCGAGG TGAGTCCGGGG'] | ['Centromeric instability of chromosomes 1,9 and 16 and immunodeficiency'] |
| NM_000226.3(KRT9): c.503T > C (p.Leu168Ser) | 61157095 | KRT9 | [ ] | [ ] | ['Epidermolytic palmoplantar keratoderma', 'not provided'] |
| NM_000051.3(ATM): c.8584 + 2T > C | 730881326 | — | [ ] | [ ] | ['Hereditary cancer-predisposing syndrome'] |
| NM_000492.3(CFTR): c.3857T > C (p.Phe1286Ser) | 121909028 | CFTR | [ ] | ['AGCCTYTGGAGT GATACCACAGG'] | ['Cystic fibrosis'] |
| NM_000492.3(CFTR): c.3763T > C (p.Ser1255Pro) | 121909041 | CFTR | [ ] | [ ] | ['Cystic fibrosis'] |
| NM_001040667.2(HSF4): c.341T > C (p.Leu114Pro) | 121909048 | HSF4 | [ ] | [ ] | ['Cataract, zonular'] |
| NM_005025.4(SERPINI1): c.145T > C (p.Ser49Pro) | 121909051 | SERPINI1 | [ ] | [ ] | ['Familial encephalopathy with neuroserpin inclusion bodies'] |
| NM_002700.2(POU4F3): c.668T > C (p.Leu223Pro) | 121909057 | POU4F3 | [ ] | [ ] | ['Deafness, autosomal dominant 15'] |
| NM_003322.4(TULP1): c.1471T > C (p.Phe491Leu) | 121909074 | TULP1 | [ ] | [ ] | ['Retinitis pigmentosa 14'] |
| NM_003322.4(TULP1): c.1145T > C (p.Phe382Ser) | 121909076 | TULP1 | [ ] | [ ] | ['Retinitis pigmentosa', 'Retinitis pigmentosa 14'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_003000.2(SDHB): c.487T > C (p.Ser163Pro) | 33927012 | SDHB | [ ] | [ ] | ['Pheochromocytoma', 'Hereditary Paraganglioma-Pheochromocytoma Syndromes', 'Hereditary cancer-predisposing syndrome', 'Cowden syndrome 2', 'not specified', 'not provided'] |
| NM_005603.4(ATP8B1): c.863T > C (p.Leu288Ser) | 121909099 | ATP8B1 | [ ] | [ ] | ['Progressive intrahepatic cholestasis'] |
| NM_005603.4(ATP8B1): c.1982T > C (p.Ile661Thr) | 121909100 | ATP8B1 | [ ] | [ ] | ['Progressive intrahepatic cholestasis', 'Benign recurrent intrahepatic cholestasis 1'] |
| NM_000483.4(APOC2): c.142T > C (p.Trp48Arg) | 120074115 | — | [ ] | [ ] | ['Apolipoprotein C2 deficiency'] |
| NM_000543.4(SMPD1): c.911T > C (p.Leu304Pro) | 120074124 | SMPD1 | ['CACYTGTGAGGAAGTTCCTGGGG1 | [AGCACYTGTGAGGAAGTTCCTGG', 'GCACYTGTGAGGAAGTTCCTGGG', 'CACYTGTGAGGAAGTTCCTGGGG'] | ['Sphingomyelin/cholesterol lipidosis', 'Niemann-Pick disease, type A', 'Niemann-Pick disease, type B', 'not provided'] |
| NM_000085.4(CLCNKB): c.1294T > C (p.Tyr432His) | 121909135 | CLCNKB | [ ] | ['CTTTGTCYATGGTGAGTCTGGGG'] | ['Bartter syndrome type 3'] |
| NM_001300.5(KLF6): c.346T > C (p.Ser116Pro) | 121909139 | KLF6 | [ ] | [ ] | [ ] |
| m.12338T > C | 201863060 | MT-ND5 | [ ] | [ ] | ['Leber optic atrophy'] |
| NM_001300.5(KLF6): c.190T > C (p.Trp64Arg) | 121909142 | KLF6 | ['TCTGYGGACCAAAATCATTCTGG'] | ['TCTGYGGACCAAAATCATTCTGG'] | [ ] |
| NM_001300.5(KLF6): c.506T > C (p.Leu169Pro) | 121909143 | KLF6 | [ ] | ['GGAGCYGCCCTCGCCAGGGAAGG'] | [ ] |
| NM_000271.4(NPC1): c.337T > C (p.Cys113Arg) | 120074136 | NPC1 | [ ] | [ ] | ['Niemann-Pick disease type C1'] |
| NM_000019.3(ACAT1): c.935T > C (p.Ile312Thr) | 120074146 | ACAT1 | ['CAAGAAYAGTAGGTAAGGCAGG'] | ['CAAGAAYAGTAGGTAAGGCCAGG'] | ['Deficiency of acetyl-CoA acetyltransferase'] |
| NM_017890.4(VPS13B): c.8459T > C (p.Ile2820Thr) | 120074155 | VPS13B | [ ] | [ ] | ['Cohen syndrome'] |
| NM_017653.3(DYM): c.1624T > C (p.Cys542Arg) | 120074165 | DYM | [ ] | [ ] | ['Smith McCort dysplasia'] |
| NM_001089.2(ABCA3): c.302T > C (p.Leu101Pro) | 121909182 | ABCA3 | [ ] | ['GCACYTGTGATCAACATGCGAGG'] | ['Surfactant metabolism dysfunction, pulmonary, 3'] |
| NM_001089.2(ABCA3): c.4658T > C (p.Leu1553Pro) | 121909183 | ABCA3 | [ ] | [ ] | ['Surfactant metabolism dysfunction, pulmonary, 3'] |
| NM_001089.2(ABCA3): c.977T > C (p.Leu326Pro) | 121909185 | ABCA3 | [ ] | [ ] | ['Surfactant metabolism dysfunction, pulmonary, 3'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000474.3(TWIST1): c.392T > C (p.Leu131Pro) | 121909189 | TWIST1 | [ ] | [ ] | ['Saethre-Chotzen syndrome'] |
| NM_000503.5(EYA1): c.1459T > C (p.Ser487Pro) | 121909200 | EYA1 | [ ] | ['CACTCYCGCTCA TTCACTCCCGG'] | ['Melnick-Fraser syndrome'] |
| NM_000358.2(TGFBI): c.1619T > C (p.Phe540Ser) | 121909214 | TGFBI | [ ] | [ ] | ['Lattice corneal dystrophy type 3A'] |
| NM_000426.3(LAMA2): c.8282T > C (p.Ile2761Thr) | 115650537 | LAMA2 | ['TTGA YAGGG AGCAA GCAGT TCGG', 'TGAYA GGGAG CAAGC AGTTC GGG'] | ['TTGAYAGGGAG CAAGCAGTTCGG', 'TGAYAGGGAGCA AGCAGTTCGGG'] | ['Merosin deficient congenital muscular dystrophy'] |
| NM_000314.6(PTEN): c.209T > C (p.Leu70Pro) | 121909226 | PTEN | [ ] | [ ] | ['Cowden syndrome 1', 'Hereditary cancer-predisposing syndrome'] |
| NM_000314.6(PTEN): c.335T > C (p.Leu112Pro) | 121909230 | PTEN | [ ] | [ ] | ['Lhermitte-Duclos disease'] |
| NM_000314.6(PTEN): c.722T > C (p.Phe241Ser) | 121909240 | PTEN | [ ] | [ ] | ['Macrocephaly/autism syndrome'] |
| NM_004970.2(IGFALS): c.1618T > C (p.Cys540Arg) | 121909247 | IGFALS | [ ] | ['GGACYGTGGCT GCCCTCTCAAGG'] | ['Acid-labile subunit deficiency'] |
| NM_005570.3(LMAN1): c.2T > C (p.Met1Thr) | 121909253 | LMAN1 | [ ] | [AGAYGGCGGGA TCCAGGCAAAGG'] | ['Combined deficiency of factor V and factor VIII, 1'] |
| NM_005055.4(RAPSN): c.416T > C (p.Phe139Ser) | 121909256 | RAPSN | [ ] | [ ] | ['Pena-Shokeir syndrome type I'] |
| NM_000391.3(TPP1): c.887-10A > G | 755445790 | TPP1 | ['TTTYT TTTTTT TTTTTT TTGAG G'] | ['TTTYTTTTTTTT TTTTTTGAGG'] | ['Ceroid lipofuscinosis, neuronal, 2', 'not provided'] |
| NM_006302.2(MOGS): c.1954T > C (p.Phe652Leu) | 121909292 | MOGS | [ ] | [ ] | ['Congenital disorder of glycosylation type 2B'] |
| NM_005379.3(MYO1A): c.2728T > C (p.Ser910Pro) | 121909306 | MYO1A | [ ] | [ ] | ['Deafness, autosomal dominant 48'] |
| NM_178151.2(DCX): c.128T > C (p.Leu43Ser) | 587783521 | DCX | [ ] | [ ] | ['Heterotopia'] |
| NM_001127221.1(CACNA1A): c.5126T > C (p.Ile1709Thr) | 121909326 | CACNA1A | [ ] | [ ] | ['Spinocerebellar ataxia 6', 'Familial hemiplegic migraine type 1', 'Episodic ataxia type 2'] |
| NM_001451.2(FOXF1): c.1138T > C (p.Ter380Arg) | 121909337 | FOXF1 | ['TGAT GYGAG GCTGC CGCCG CAGG'] | ['TGATGYGAGGCT GCCGCCGCAGG'] | ['Alveolar capillary dysplasia with misalignment of pulmonary veins'] |
| NM_000163.4(GHR): c.341T > C (p.Phe114Ser) | 121909357 | GHR | [ ] | [ ] | ['Laron-type isolated somatotropin defect'] |
| NM_000163.4(GHR): c.512T > C (p.Ile171Thr) | 121909367 | GHR | [ ] | [ ] | ['Laron-type isolated somatotropin defect'] |
| NM_000339.2(SLC12A3): c.1868T > C (p.Leu623Pro) | 121909385 | SLC12A3 | [ ] | ['CAACCYGGCCCT CAGCTACTCGG'] | ['Familial hypokalemia-hypomagnesemia'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_001174089.1(SLC4A11): c.2480T > C (p.Leu827Pro) | 121909394 | SLC4A11 | [ ] | [ ] | ['Corneal dystrophy and perceptive deafness'] |
| NM_001174089.1(SLC4A11): c.589T > C (p.Ser197Pro) | 121909395 | SLC4A11 | [ ] | [ ] | ['Corneal dystrophy and perceptive deafness'] |
| NM_000519.3(HBD): c.-127T > C | 34975911 | HBD | [ ] | [ ] | ['delta Thalassemia'] |
| NM_002427.3(MMP13): c.224T > C (p.Phe75Ser) | 121909497 | MMP13 | [ ] | ['TTCTYCGGCTTA GAGGTGACTGG'] | ['Spondyloepimetap hyseal dysplasia, Missouri type'] |
| NM_002427.3(MMP13): c.221T > C (p.Phe74Ser) | 121909498 | MMP13 | [ ] | [ ] | [ ] |
| NM_002427.3(MMP13): c.272T > C (p.Met91Thr) | 121909499 | MMP13 | ['GTCA YGAAA AAGCC AAGAT GCGG', 'TCAYG AAAAA GCCAA GATGC GGG'] | ['GTCAYGAAAAA GCCAAGATGCGG', 'TCAYGAAAAAGC CAAGATGCGGGG'] | [ ] |
| NM_000751.2(CHRND): c.283T > C (p.Phe95Leu) | 121909506 | CHRND | [ ] | [ ] | ['Lethal multiple pterygium syndrome'] |
| NM_000751.2(CHRND): c.188T > C (p.Leu63Pro) | 121909508 | CHRND | [ ] | ['AACCYCATCTCC CTGGTGAGAGG'] | ['MYASTHENIC SYNDROME, CONGENITAL, 3B, FAST-CHANNEL'] |
| NM_001100.3(ACTA1): c.287T > C (p.Leu96Pro) | 121909519 | ACTA1 | [ ] | ['CGAGCYTCGCGT GGCTCCCGAGG'] | ['Nemaline myopathy 3'] |
| NM_001100.3(ACTA1): c.668T > C (p.Leu223Pro) | 121909530 | ACTA1 | [ ] | [ ] | ['Congenital myopathy with fiber type disproportion'] |
| NM_000488.3(SERPINC1): c.1141T > C (p.Ser381Pro) | 121909565 | SERPINC1 | [ ] | [ ] | ['Antithrombin III deficiency'] |
| NM_000488.3(SERPINC1): c.442T > C (p.Ser148Pro) | 121909569 | SERPINC1 | [ ] | [ ] | ['Antithrombin III deficiency'] |
| NM_000488.3(SERPINC1): c.667T > C (p.Ser223Pro) | 121909572 | SERPINC1 | [ ] | ['TGGGTGYCCAAT AAGACCGAAGG'] | ['Antithrombin III deficiency'] |
| NM_000488.3(SERPINC1): c.379T > C (p.Cys127Arg) | 121909573 | SERPINC1 | [ ] | [ ] | ['Antithrombin III deficiency'] |
| NM_023110.2(FGFR1): c.899T > C (p.Ile300Thr) | 121909633 | FGFR1 | [ ] | [ ] | ['Interfrontal craniofaciosynostosis'] |
| NM_023110.2(FGFR1): c.1141T > C (p.Cys381Arg) | 121909634 | FGFR1 | [ ] | [ ] | ['Osteoglophonic dysplasia'] |
| NM_182925.4(FLT4): c.3131T > C (p.Leu1044Pro) | 121909651 | FLT4 | [ ] | [ ] | ['Hereditary lymphedema type I'] |
| NM_182925.4(FLT4): c.3257T > C (p.Ile1086Thr) | 121909655 | FLT4 | [ ] | [ ] | ['Hereditary lymphedema type I'] |
| NM_000145.3(FSHR): c.479T > C (p.Ile160Thr) | 121909659 | FSHR | [ ] | [ ] | ['Ovarian dysgenesis 1'] |
| NM_000145.3(FSHR): c.1634T > C (p.Ile545Thr) | 121909664 | FSHR | [ ] | [ ] | ['Ovarian hyperstimulation syndrome'] |
| NM_000821.6(GGCX): c.896T > C (p.Phe299Ser) | 121909677 | GGCX | [ ] | ['TATGTYCTCCTA CGTCATGCTGG'] | ['Pseudoxanthoma elasticum-like disorder with multiple coagulation factor deficiency'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_001018077.1(NR3C1): c.2209T > C (p.Phe737Leu) | 121909727 | NR3C1 | [ ] | ['CTATTGCYTCCA AACATTTTTGG'] | ['Glucocorticoid resistance, generalized'] |
| NM_005271.3(GLUD1): c.1501T > C (p.Ser501Pro) | 121909732 | GLUD1 | [ ] | [ ] | ['Hyperinsulinism-hyperammonemia syndrome'] |
| NM_004614.4(TK2): c.278A > G (p.Asn93Ser) | 142291440 | TK2 | [ ] | [ ] | ['Mitochondrial DNA depletion syndrome 2'] |
| NM_032977.3(CASP10): c.440T > C (p.Met147Thr) | 121909776 | CASP10 | [ ] | [ ] | ['Neoplasm of stomach'] |
| NM_000250.1(MPO): c.518A > G (p.Tyr173Cys) | 78950939 | MPO | ['TGCG GYATT TGTCC TGCTC CGGG'] | ['GTGCGGYATTTG TCCTGCTCCGG', 'TGCGGYATTTGT CCTGCTCCGGG'] | ['Myeloperoxidase deficiency'] |
| NM_001139.2(ALOX12B): c.1562A > G (p.Tyr521Cys) | 199766569 | ALOX12B | [ ] | [ ] | ['Autosomal recessive congenital ichthyosis 2'] |
| NM_022041.3(GAN): c.1268T > C (p.Ile423Thr) | 119485091 | GAN | ['AAGA AAAYC TACGC CATGG GTGG'] | ['AAGAAAAYCTA CGCCATGGGTGG', 'AAAAYCTACGCC ATGGGTGGAGG'] | ['Giant axonal neuropathy'] |
| NM_014009.3(FOXP3): c.970T > C (p.Phe324Leu) | 122467173 | FOXP3 | ['GACA GAGYT CCTCC ACAAC ATGG'] | ['GACAGAGYTCCT CCACAACATGG'] | ['Insulin-dependent diabetes mellitus secretory diarrhea syndrome'] |
| NM_014009.3(FOXP3): c.1099T > C (p.Phe367Leu) | 122467175 | FOXP3 | [ ] | [ ] | ['Insulin-dependent diabetes mellitus secretory diarrhea syndrome'] |
| NM_004239.3(TRIP11): c.2102A > G (p.Asn701Ser) | 139539448 | TRIP11 | [ ] | [ ] | ['Achondrogenesis, type IA'] |
| NM_001104.3(ACTN3): c.1729C > T (p.Arg577Ter) | 1815739 | ACTN3 | [ ] | [ ] | ['Sprinting performance', 'Actn3 deficiency'] |
| NM_002693.2(POLG): c.2636A > G (p.Gln879Arg) | 368587966 | POLG | [ ] | [ ] | ['not provided'] |
| NM_000552.3(VWF): c.3178T > C (p.Cys1060Arg) | 61748497 | VWF | [ ] | [ ] | ['von Willebrand disease type 2N', 'not provided'] |
| NM_000552.3(VWF): c.3445T > C (p.Cys1149Arg) | 61748511 | VWF | [ ] | [ ] | ['von Willebrand disease type 1', 'not provided'] |
| NM_000184.2(HBG2): c.125T > C (p.Phe42Ser) | 34878913 | HBG2 | ['CAGA GGTYC TTTGA CAGCT TTGG'] | ['CAGAGGTYCTTT GACAGCTTTGG'] | ['Cyanosis, transient neonatal'] |
| NM_000371.3(TTR): c.190T > C (p.Phe64Leu) | 138065384 | TTR | [ ] | [ ] | ['Cardiomyopathy', 'not specified'] |
| NM_000402.4(G6PD): c.1058T > C (p.Leu353Pro) | 76723693 | G6PD | [ ] | [ ] | ['Glucose 6 phosphate dehydrogenase deficiency', 'Anemia, nonspherocytic hemolytic, due to G6PD deficiency', 'not provided'] |
| NM_177405.2(CECR1): c.355A > G (p.Thr119Ala) | 775440641 | CECR1 | [ ] | [ ] | ['Idiopathic livedo reticularis with systemic involvement'] |
| NM_000218.2(KCNQ1): c.401T > C (p.Leu134Pro) | 199472685 | KCNQ1 | | | ['Congenital long QT syndrome', 'Cardiac arrhythmia'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000218.2(KCNQ1):<br>c.625T > C<br>(p.Ser209Pro) | 199472705 | KCNQ1 | | | ['Atrial fibrillation, familial, 3', 'Atrial fibrillation'] |
| NM_000218.2(KCNQ1):<br>c.752T > C<br>(p.Leu251Pro) | 199472716 | KCNQ1 | | | ['Congenital long QT syndrome', 'Cardiac arrhythmia', 'Long QT syndrome, LQT1 subtype'] |
| NM_000218.2(KCNQ1):<br>c.824T > C<br>(p.Phe275Ser) | 199472729 | KCNQ1 | | | ['Congenital long QT syndrome', 'Long QT syndrome, LQT1 subtype'] |
| NM_000218.2(KCNQ1):<br>c.832T > C<br>(p.Tyr278His) | 199472731 | KCNQ1 | | | ['Congenital long QT syndrome'] |
| NM_000218.2(KCNQ1):<br>c.845T > C<br>(p.Leu282Pro) | 199472733 | KCNQ1 | | | ['Congenital long QT syndrome'] |
| NM_000257.3(MYH7):<br>c.730T > C<br>(p.Phe244Leu) | 730880849 | MYH7 | [ ] | [ ] | ['Cardiomyopathy'] |
| NM_000218.2(KCNQ1):<br>c.908T > C<br>(p.Leu303Pro) | 199472740 | KCNQ1 | | | ['Congenital long QT syndrome'] |
| NM_000218.2(KCNQ1):<br>c.913T > C<br>(p.Trp305Arg) | 199472741 | KCNQ1 | | | ['Congenital long QT syndrome', 'Long QT syndrome, LQT1 subtype'] |
| NM_000218.2(KCNQ1):<br>c.1045T > C<br>(p.Ser349Pro) | 199472764 | KCNQ1 | | | ['Congenital long QT syndrome', 'Long QT syndrome, LQT1 subtype'] |
| NM_000218.2(KCNQ1):<br>c.1117T > C<br>(p.Ser373Pro) | 199472766 | KCNQ1 | | | ['Congenital long QT syndrome'] |
| NM_000218.2(KCNQ1):<br>c.1165T > C<br>(p.Ser389Pro) | 199472772 | KCNQ1 | | | ['Congenital long QT syndrome'] |
| NM_000218.2(KCNQ1):<br>c.1174T > C<br>(p.Trp392Arg) | 199472774 | KCNQ1 | | | ['Congenital long QT syndrome'] |
| NM_000218.2(KCNQ1):<br>c.1541T > C<br>(p.Ile514Thr) | 199472786 | KCNQ1 | | | ['Congenital long QT syndrome', 'Long QT syndrome, LQT1 subtype'] |
| NM_000218.2(KCNQ1):<br>c.1696T > C<br>(p.Ser566Pro) | 199472803 | KCNQ1 | | | ['Congenital long QT syndrome'] |
| NM_000218.2(KCNQ1):<br>c.1805T > C<br>(p.Leu602Pro) | 199472818 | — | | | ['Congenital long QT syndrome'] |
| NM_000218.2(KCNQ1):<br>c.608T > C<br>(p.Leu203Pro) | 199472823 | KCNQ1 | | | ['Congenital long QT syndrome', 'Cardiac arrhythmia'] |
| NM_000238.3(KCNH2):<br>c.65T > C<br>(p.Phe22Ser) | 199472826 | KCNH2 | | | ['Congenital long QT syndrome'] |
| NM_000238.3(KCNH2):<br>c.86T > C<br>(p.Phe29Ser) | 199472831 | KCNH2 | | | ['Congenital long QT syndrome'] |
| NM_000238.3(KCNH2):<br>c.89T > C<br>(p.Ile30Thr) | 199472832 | KCNH2 | | | ['Congenital long QT syndrome'] |
| NM_000238.3(KCNH2):<br>c.160T > C<br>(p.Tyr54His) | 199472843 | KCNH2 | | | ['Congenital long QT syndrome'] |
| NM_001165963.1(SCN1A):<br>c.662T > C<br>(p.Leu221Pro) | 796052961 | SCN1A | [ ] | [ ] | ['not provided'] |
| NM_000238.3(KCNH2):<br>c.287T > C<br>(p.Ile96Thr) | 199472853 | KCNH2 | | | ['Congenital long QT syndrome'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000238.3(KCNH2):<br>c.322T > C<br>(p.Cys108Arg) | 199472859 | KCNH2 | | | ['Congenital long<br>QT syndrome'] |
| NM_000238.3(KCNH2):<br>c.872T > C<br>(p.Met291Thr) | 199472881 | KCNH2 | | | ['Congenital long<br>QT syndrome'] |
| NM_000238.3(KCNH2):<br>c.1238T > C<br>(p.Leu413Pro) | 199472893 | KCNH2 | | | ['Congenital long<br>QT syndrome'] |
| NM_000238.3(KCNH2):<br>c.1279T > C<br>(p.Tyr427His) | 199472898 | KCNH2 | | | ['Congenital long<br>QT syndrome'] |
| NM_000238.3(KCNH2):<br>c.1387T > C<br>(p.Phe463Leu) | 199472904 | KCNH2 | | | ['Congenital long<br>QT syndrome'] |
| NM_000238.3(KCNH2):<br>c.1655T > C<br>(p.Leu552Ser) | 199472918 | KCNH2 | [ ] | [ ] | ['Congenital long<br>QT syndrome',<br>'Cardiac arrhythmia'] |
| NM_000061.2(BTK):<br>c.1955T > C<br>(p.Leu652Pro) | 128622212 | BTK | [ ] | [ ] | ['X-linked<br>agammaglobulinemi<br>a'] |
| NM_000238.3(KCNH2):<br>c.1691T > C<br>(p.Leu564Pro) | 199472924 | KCNH2 | | | ['Congenital long<br>QT syndrome'] |
| NM_000238.3(KCNH2):<br>c.1702T > C<br>(p.Trp568Arg) | 199472927 | KCNH2 | | | ['Congenital long<br>QT syndrome'] |
| NM_000138.4(FBN1):<br>c.5726T > C<br>(p.Ile1909Thr) | 794728333 | FBN1 | [ ] | [ ] | ['Thoracic aortic<br>aneurysms and<br>aortic dissections'] |
| NM_015884.3(MBTPS2):<br>c.1424T > C<br>(p.Phe475Ser) | 122468179 | MBTPS2 | [ ] | [ ] | ['IFAP syndrome<br>with or without<br>BRESHECK<br>syndrome'] |
| NM_000238.3(KCNH2):<br>c.1985T > C<br>(p.Ile662Thr) | 199472980 | KCNH2 | | | ['Congenital long<br>QT syndrome'] |
| NM_000238.3(KCNH2):<br>c.2033T > C<br>(p.Leu678Pro) | 199472981 | KCNH2 | | | ['Congenital long<br>QT syndrome'] |
| NM_000238.3(KCNH2):<br>c.2078T > C<br>(p.Leu693Pro) | 199472983 | KCNH2 | | | ['Congenital long<br>QT syndrome',<br>'Cardiac arrhythmia'] |
| NM_000238.3(KCNH2):<br>c.2309T > C<br>(p.Val770Ala) | 199472994 | KCNH2 | | | ['Congenital long<br>QT syndrome'] |
| NM_000238.3(KCNH2):<br>c.3146T > C<br>(p.Leu1049Pro) | 199473026 | KCNH2 | | | ['Congenital long<br>QT syndrome'] |
| NM_000335.4(SCN5A):<br>c.278T > C<br>(p.Phe93Ser) | 199473052 | SCN5A | | | ['Brugada<br>syndrome'] |
| NM_000335.4(SCN5A):<br>c.544T > C<br>(p.Cys182Arg) | 199473066 | SCN5A | | | ['Brugada<br>syndrome'] |
| NM_000335.4(SCN5A):<br>c.689T > C<br>(p.Ile230Thr) | 199473073 | SCN5A | | | ['Cardiac conduction<br>defect, nonspecific'] |
| NM_000335.4(SCN5A):<br>c.1187T > C<br>(p.Val396Ala) | 199473103 | SCN5A | | | ['Brugada<br>syndrome'] |
| NM_000335.4(SCN5A):<br>c.1190T > C<br>(p.Ile397Thr) | 199473105 | SCN5A | | | ['Congenital long<br>QT syndrome'] |
| NM_000335.4(SCN5A):<br>c.2018T > C<br>(p.Leu673Pro) | 199473141 | SCN5A | | | ['Congenital long<br>QT syndrome'] |
| NM_000335.4(SCN5A):<br>c.2516T > C<br>(p.Leu839Pro) | 199473164 | SCN5A | | | ['Brugada<br>syndrome'] |
| NM_000335.4(SCN5A):<br>c.2783T > C<br>(p.Leu928Pro) | 199473178 | SCN5A | | | ['Brugada<br>syndrome'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000335.4(SCN5A): c.2804T > C (p.Leu935Pro) | 199473179 | SCN5A | | | ['Brugada syndrome'] |
| NM_198056.2(SCN5A): c.3010T > C (p.Cys1004Arg) | 199473183 | SCN5A | [ ] | [ ] | ['Congenital long QT syndrome', 'not specified', 'not provided'] |
| NM_000335.4(SCN5A): c.3679T > C (p.Tyr1227His) | 199473205 | SCN5A | [ ] | [ ] | ['Brugada syndrome'] |
| NM_000335.4(SCN5A): c.3713T > C (p.Leu1238Pro) | 199473210 | SCN5A | | | ['Brugada syndrome'] |
| NM_000492.3(CFTR): c.1400T > C (p.Leu467Pro) | 139573311 | CFTR | [ ] | ['TTCACYTCTAATGGTGATTATGGG', 'TCACYTCTAATGGTGATTATGGG'] | ['Cystic fibrosis'] |
| NM_000335.4(SCN5A): c.3929T > C (p.Leu1310Pro) | 199473219 | SCN5A | | | ['Brugada syndrome'] |
| NM_000335.4(SCN5A): c.4027T > C (p.Phe1343Leu) | 199473228 | SCN5A | | | ['Brugada syndrome'] |
| NM_000335.4(SCN5A): c.4028T > C (p.Phe1343Ser) | 199473229 | SCN5A | | | ['Brugada syndrome'] |
| NM_000335.4(SCN5A): c.4034T > C (p.Leu1345Pro) | 199473231 | SCN5A | | | ['Brugada syndrome'] |
| NM_000335.4(SCN5A): c.4340T > C (p.Ile1447Thr) | 199473251 | SCN5A | | | ['Brugada syndrome'] |
| NM_198056.2(SCN5A): c.4493T > C (p.Met1498Thr) | 199473263 | SCN5A | | | ['Congenital long QT syndrome', 'not provided'] |
| NM_000335.4(SCN5A): c.4742T > C (p.Leu1581Pro) | 199473275 | SCN5A | | | ['Brugada syndrome'] |
| NM_000335.4(SCN5A): c.4778T > C (p.Phe1593Ser) | 199473277 | SCN5A | | | ['Congenital long QT syndrome'] |
| NM_000335.4(SCN5A): c.5179T > C (p.Cys1727Arg) | 199473302 | SCN5A | | | ['Brugada syndrome'] |
| NM_000219.5(KCNE1): c.158T > C (p.Phe53Ser) | 199473355 | KCNE1 | | | ['Congenital long QT syndrome'] |
| NM_000219.5(KCNE1): c.259T > C (p.Trp87Arg) | 199473361 | KCNE1 | | | ['Congenital long QT syndrome'] |
| NM_000891.2(KCNJ2): c.301T > C (p.Cys101Arg) | 199473374 | KCNJ2 | | | ['Ventricular tachycardia'] |
| NM_000218.2(KCNQ1): c.560T > C (p.Leu187Pro) | 199473399 | KCNQ1 | [ ] | [ ] | ['Congenital long QT syndrome', 'Cardiac arrhythmia', 'Long QT syndrome, LQT1 subtype'] |
| NM_000218.2(KCNQ1): c.572T > C (p.Leu191Pro) | 199473401 | KCNQ1 | | | ['Congenital long QT syndrome', 'Long QT syndrome, LQT1 subtype'] |
| NM_000218.2(KCNQ1): c.1052T > C (p.Phe351Ser) | 199473402 | KCNQ1 | | | ['Congenital long QT syndrome', 'Long QT syndrome, LQT1 subtype'] |
| NM_000218.2(KCNQ1): c.1058T > C (p.Leu353Pro) | 199473403 | KCNQ1 | | | ['Congenital long QT syndrome', 'Cardiac arrhythmia', 'Long QT syndrome, LQT1 subtype'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000238.3(KCNH2): c.202T > C (p.Phe68Leu) | 199473417 | KCNH2 | | | ['Congenital long QT syndrome', 'Cardiac arrhythmia'] |
| NM_000218.2(KCNQ1): c.341T > C (p.Leu114Pro) LQT1 | 199473448 | KCNQ1 | | | ['Congenital long QT syndrome', 'Long QT syndrome, subtype'] |
| NM_000218.2(KCNQ1): c.716T > C (p.Leu239Pro) LQT1 | 199473458 | KCNQ1 | | | ['Congenital long QT syndrome', 'Long QT syndrome, subtype'] |
| NM_000218.2(KCNQ1): c.742T > C (p.Trp248Arg) | 199473459 | KCNQ1 | | | ['Congenital long QT syndrome', 'Cardiac arrhythmia'] |
| NM_000218.2(KCNQ1): c.797T > C (p.Leu266Pro) | 199473460 | KCNQ1 | | | ['Long QT syndrome', 'Congenital long QT syndrome', 'Cardiac arrhythmia'] |
| NM_000218.2(KCNQ1): c.829T > C (p.Ser277Pro) | 199473461 | KCNQ1 | | | ['Congenital long QT syndrome'] |
| NM_000218.2(KCNQ1): c.910T > C (p.Trp304Arg) | 199473466 | KCNQ1 | | | ['Congenital long QT syndrome', 'Long QT syndrome, LQT1 subtype'] |
| NM_000218.2(KCNQ1): c.1550T > C (p.Ile517Thr) | 199473478 | KCNQ1 | | | ['Congenital long QT syndrome'] |
| NM_000218.2(KCNQ1): c.1661T > C (p.Val554Ala) | 199473481 | KCNQ1 | | | ['Congenital long QT syndrome', 'Long QT syndrome, LQT1 subtype'] |
| NM_000218.2(KCNQ1): c.2T > C (p.Met1Thr) | 199473485 | KCNQ1 | | | ['Congenital long QT syndrome', 'KCNQ1-related Jervell and Lange-Nielsen syndrome'] |
| NM_000238.3(KCNH2): c.260T > C (p.Leu87Pro) | 199473495 | KCNH2 | | | ['Congenital long QT syndrome'] |
| NM_000238.3(KCNH2): c.1700T > C (p.Ile567Thr) | 199473519 | KCNH2 | | | ['Congenital long QT syndrome'] |
| NM_000238.3(KCNH2): c.1705T > C (p.Tyr569His) | 199473520 | KCNH2 | | | ['Congenital long QT syndrome'] |
| NM_000238.3(KCNH2): c.1816T > C (p.Ser606Pro) | 199473523 | KCNH2 | | | ['Congenital long QT syndrome'] |
| NM_000238.3(KCNH2): c.1889T > C (p.Val630Ala) | 199473526 | KCNH2 | | | ['Congenital long QT syndrome'] |
| NM_000238.3(KCNH2): c.1945T > C (p.Ser649Pro) | 199473530 | KCNH2 | | | ['Congenital long QT syndrome'] |
| NM_000238.3(KCNH2): c.2452T > C (p.Ser818Pro) | 199473537 | KCNH2 | | | ['Congenital long QT syndrome'] |
| NM_000238.3(KCNH2): c.2573T > C (p.Ile858Thr) | 199473539 | KCNH2 | | | ['Congenital long QT syndrome'] |
| NM_000335.4(SCN5A): c.407T > C (p.Leu136Pro) | 199473557 | SCN5A | | | ['Brugada syndrome'] |
| NM_020166.4(MCCC1): c.1310T > C (p.Leu437Pro) | 119103215 | MCCC1 | [ ] | [ ] | ['3 Methylcrotonyl-CoA carboxylase 1 deficiency'] |
| NM_198056.2(SCN5A): c.944T > C (p.Leu315Pro) | 199473564 | SCN5A | | | ['Brugada syndrome', 'not provided'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_002972.3(SBF1): c.1249A > G (p.Met417Val) | 587776986 | SBF1 | [ ] | [ ] | ['Charcot-Marie-Tooth disease, type 4B3'] |
| NM_000335.4(SCN5A): c.2551T > C (p.Phe851Leu) | 199473586 | SCN5A | | | ['Brugada syndrome'] |
| NM_000335.4(SCN5A): c.2743T > C (p.Cys915Arg) | 199473588 | SCN5A | | | ['Brugada syndrome'] |
| NM_000335.4(SCN5A): c.4046T > C (p.Ile1349Thr) | 199473607 | SCN5A | | | ['Brugada syndrome'] |
| NM_000335.4(SCN5A): c.4453T > C (p.Phe1485Leu) | 199473615 | SCN5A | | | ['Sudden infant death syndrome'] |
| NM_000335.4(SCN5A): c.5111T > C (p.Phe1704Ser) | 199473627 | SCN5A | | | ['Sudden infant death syndrome'] |
| NM_000891.2(KCNJ2): c.650T > C (p.Leu217Pro) | 199473656 | KCNJ2 | | | ['Congenital long QT syndrome'] |
| NM_000218.2(KCNQ1): c.550T > C (p.Tyr184His) | 199473661 | KCNQ1 | ['AGCAAGBACGTGGGCCTCTGGGG'] | ['CAGCAAGBACGTGGGCCTCTGGG', 'AGCAAGBACGTGGCCTCTGGGG', 'GCAAGBACGTGGGCCTCTGGGGG'] | ['Congenital long QT syndrome', 'Cardiac arrhythmia'] |
| NM_000238.3(KCNH2): c.206T > C (p.Leu69Pro) | 199473665 | KCNH2 | | | ['Congenital long QT syndrome'] |
| NM_001130823.1(DNMT1): c.1531T > C (p.Tyr511His) | 199473692 | DNMT1 | | | ['Hereditary sensory neuropathy type IE'] |
| NM_031226.2(CYP19A1): c.743 + 2T > C | 786205107 | — | ['CTGTGYAAGTAATACAACTTTGG'] | ['CTGTGYAAGTAATACAACTTTGG'] | ['Aromatase deficiency'] |
| NM_016373.3(WW0X): c.872T > C (p.Leu291Pro) | 119487098 | WWOX | [ ] | [ ] | [ ] |
| NM_001287223.1(SCN11A): c.1142T > C (p.Ile381Thr) | 606231280 | SCN11A | ['TTCAYTGTGGTCATTTTCCTGGG'] | ['CTTCAYTGTGGTCATTTTCCTGG', 'TTCAYTGTGGTCATTTTCCTGGG'] | ['Episodic pain syndrome, familial, 3'] |
| NM_003640.3(IKBKAP): c.2204 + 6T > C | 111033171 | IKBKAP | [ ] | [ ] | ['Familial dysautonomia', 'not provided'] |
| NM_000238.3(KCNH2): c.1282T > C (p.Ser428Pro) | 794728368 | KCNH2 | [ ] | [ ] | ['Cardiac arrhythmia'] |
| NM_000441.1(SLC26A4): c.1588T > C (p.Tyr530His) | 111033254 | SLC26A4 | [ ] | [ ] | ['Pendred syndrome', 'Enlarged vestibular aqueduct syndrome'] |
| NM_206933.2(USH2A): c.10561T > C (p.Trp3521Arg) | 111033264 | USH2A | [ ] | [ ] | ['Usher syndrome, type 2A'] |
| NM_206933.2(USH2A): c.1606T > C (p.Cys536Arg) | 111033273 | USH2A | ['ATATAGAYGCCTCTGCTCCCAGG'] | ['ATATAGAYGCCTCTGCTCCCAGG'] | ['Usher syndrome, type 2A'] |
| NM_001363.4(DKC1): c.1049T > C (p.Met350Thr) | 121912300 | DKC1 | [ ] | [ ] | ['Dyskeratosis congenita X-linked'] |
| NM_000274.3(OAT): c.1180T > C (p.Cys394Arg) | 121965054 | OAT | [ ] | [ ] | [Ornithine aminotransferase deficiency'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_001302946.1(TRNT1): c.497T > C (p.Leu166Ser) | 606231289 | TRNT1 | ['ACTTYATTTGACTACTTTAATGG'] | ['ACTTYATTTGACTACTTTAATGG'] | ['Sideroblastic anemia with B-cell immunodeficiency, periodic fevers, and developmental delay'] |
| NM_000454.4(SOD1): c.341T > C (p.Ile114Thr) | 121912441 | SOD1 | [ ] | ['CATCAYTGGCCGCACACTGGTGG'] | ['Amyotrophic lateral sclerosis type 1'] |
| NM_000454.4(SOD1): c.434T > C (p.Leu145Ser) | 121912446 | SOD1 | [ ] | ['CGTTYGGCTTGTGGTGTAATTGG', 'GTTYGGCTTGTGGTGTAATTGGG'] | ['Amyotrophic lateral sclerosis type 1'] |
| NM_000454.4(SOD1): c.455T > C (p.Ile152Thr) | 121912449 | SOD1 | [ ] | [ ] | ['Amyotrophic lateral sclerosis type 1'] |
| NM_000213.3(ITGB4): c.467T > C (p.Leu156Pro) | 121912461 | ITGB4 | [ ] | [ ] | ['Epidermolysis bullosa with pyloric atresia'] |
| NM_000213.3(ITGB4): c.1684T > C (p.Cys562Arg) | 121912463 | ITGB4 | [ ] | ['GGCCAGYGTGTGTGTGAGCCTGG'] | ['Epidermolysis bullosa with pyloric atresia'] |
| NM_000213.3(ITGB4): c.112T > C (p.Cys38Arg) | 121912465 | ITGB4 | [ ] | [ ] | ['Epidermolysis bullosa with pyloric atresia'] |
| NM_002198.2(IRF1): c.31T > C (p.Trp11Arg) | 121912470 | IRF1 | [ ] | [ ] | ['Non-small cell lung cancer'] |
| NM_000424.3(KRT5): c.20T > C (p.Val7Ala) | 121912474 | KRT5 | ['TCAAGTGYGTCCTTCCGGAGCGG', 'CAAGTGYGTCCTTCCGGAGCGGG', 'AAGTGYGTCCTTCCGGAGCGGGG'] | ['TCAAGTGYGTCCTTCCGGAGCGG', 'CAAGTGYGTCCTCCGGAGCGGG', 'AAGTGYGTCCTTCCGGAGCGGGG', 'AGTGYGTCCTTCCGGAGCGGGGG'] | ['Epidermolysis bullosa simplex, Koebner type'] |
| NM_002292.3(LAMB2): c.961T > C (p.Cys321Arg) | 121912492 | LAMB2 | [ ] | ['CCTCAACYGCGAGCAGTGTCAGG'] | ['Nephrotic syndrome, type 5, with or without ocular abnormalities'] |
| NM_170707.3(LMNA): c.1139T > C (p.Leu380Ser) | 121912495 | LMNA | ['TCTYGGAGGGCGAGGAGGAGAGG'] | ['TCTYGGAGGGCGAGGAGGAGAGG'] | ['Congenital muscular dystrophy, LMNA-related', 'not provided'] |
| NM_001399.4(EDA): c.2T > C (p.Met1Thr) | 397516659 | EDA | [ ] | ['GGCCAYGGGCTACCCGGAGGTGG'] | ['Hypohidrotic X-linked ectodermal dysplasia'] |
| NM_000493.3(COL10A1): c.1951T > C (p.Trp651Arg) | 111033549 | — | [ ] | [ ] | ['Metaphyseal chondrodysplasia, Schmid type'] |
| NM_000233.3(LHCGR): c.1193T > C (p.Met398Thr) | 121912526 | — | [ ] | [ ] | ['Gonadotropin-independent familial sexual precocity'] |
| NM_000233.3(LHCGR): c.391T > C (p.Cys131Arg) | 121912527 | — | [ ] | [ ] | ['Leydig cell hypoplasia, partial'] |
| NM_000493.3(COL10A1): c.1798T > C (p.Ser600Pro) | 111033555 | — | [ ] | [ ] | ['Metaphyseal chondrodysplasia, Schmid type'] |
| NM_000233.3(LHCGR): c.1103T > C (p.Leu368Pro) | 121912533 | — | [ ] | [ ] | ['Gonadotropin-independent familial sexual precocity'] |
| NM_000233.3(LHCGR): c.1627T > C (p.Cys543Arg) | 121912537 | — | [ ] | [ ] | ['Leydig cell agenesis'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000233.3(LHCGR): c.1505T > C (p.Leu502Pro) | 121912538 | — | [ ] | [ ] | ['Leydig cell agenesis'] |
| NM_000901.4(NR3C2): c.2771T > C (p.Leu924Pro) | 121912563 | NR3C2 | [ ] | [ ] | ['Pseudohypoaldosteronism type 1 autosomal dominant'] |
| NM_021044.2(DHH): c.485T > C (p.Leu162Pro) | 111033589 | DHH | [ ] | ['GTTGCYGGCGCG CCTCGCAGTGG'] | ['46,XY gonadal dysgenesis, complete, dhh-related'] |
| NM_000901.4(NR3C2): c.2936T > C (p.Leu979Pro) | 121912567 | NR3C2 | [ ] | [ ] | ['Pseudohypoaldosteronism type 1 autosomal dominant'] |
| NM_000517.4(HBA2): c.2T > C (p.Met1Thr) | 111033603 | HBA2 | [ ] | [ ] | ['alpha Thalassemia'] |
| NM_000762.5(CYP2A6): c.670T > C (p.Ser224Pro) | 111033610 | — | [ ] | [ ] | ['Tegafur response'] |
| NM_000660.5(TGFB1): c.241T > C (p.Tyr81His) | 111033611 | TGFB1 | [ ] | [ ] | ['Diaphyseal dysplasia'] |
| NM_001173464.1(KIF21A): c.1067T > C (p.Met356Thr) | 121912588 | KIF21A | [ ] | [ ] | ['Fibrosis of extraocular muscles, congenital, 1'] |
| NM_000206.2(IL2RG): c.343T > C (p.Cys115Arg) | 111033622 | IL2RG | [ ] | ['TGGCYGTCAGTT GCAAAAAAAGG'] | ['X-linked severe combined immunodeficiency'] |
| NM_001041.3(SI): c.1859T > C (p.Leu620Pro) | 121912613 | SI | [ ] | ['ATGCYGGAGTTC AGTTTGTTTGG'] | ['Sucrase-isomaltase deficiency'] |
| NM_016180.4(SLC45A2): c.1082T > C (p.Leu361Pro) | 121912619 | SLC45A2 | [ ] | ['GAGTTTCYCATC TACGAAAGAGG'] | ['Oculocutaneous albinism type 4', 'not provided'] |
| NM_000552.3(VWF): c.4837T > C (p.Ser1613Pro) | 61750581 | VWF | [ ] | ['CTGCCYCTGATG AGATCAAGAGG'] | ['von Willebrand disease, type 2a', 'not provided'] |
| NM_000552.3(VWF): c.4883T > C (p.Ile1628Thr) | 61750584 | VWF | [ ] | [ ] | ['von Willebrand disease, type 2a', 'not provided'] |
| NM_000180.3(GUCY2D): c.1694T > C (p.Phe565Ser) | 61749755 | GUCY2D | [ ] | [ ] | ['Leber congenital amaurosis 1', 'not provided'] |
| NM_003235.4(TG): c.3733T > C (p.Cys1245Arg) | 121912647 | TG | [ ] | [ ] | ['Iodotyrosyl coupling defect'] |
| NM_000546.5(TP53): c.755T > C (p.Leu252Pro) | 121912653 | TP53 | [ ] | ['CATCCYCACCAT CATCACACTGG'] | ['Li-Fraumeni syndrome 1'] |
| NM_000155.3(GALT): c.350T > C (p.Phe117Ser) | 111033679 | GALT | [ ] | [ ] | ['Deficiency of UDPglucose-hexose- 1-phosphate uridylyltransferase'] |
| NM_000155.3(GALT): c.374T > C (p.Val125Ala) | 111033680 | GALT | [ ] | [ ] | ['Deficiency of UDPglucose-hexose- 1-phosphate uridylyltransferase'] |
| NM_000155.3(GALT): c.386T > C (p.Met129Thr) | 111033683 | GALT | [ ] | ['AGGTCAYGTGCT TCCACCCCTGG'] | ['Deficiency of UDPglucose-hexose- 1-phosphate uridylyltransferase'] |
| NM_000546.5(TP53): c.1031T > C (p.Leu344Pro) | 121912662 | TP53 | [ ] | [ ] | ['Li-Fraumeni syndrome 1'] |
| NM_000155.3(GALT): c.416T > C (p.Leu139Pro) | 111033687 | GALT | [ ] | [ ] | ['Deficiency of UDPglucose-hexose- 1-phosphate uridylyltransferase'] |
| NM_000155.3(GALT): c.452T > C (p.Val151Ala) | 111033701 | GALT | [ ] | [ ] | ['Deficiency of UDPglucose-hexose- 1-phosphate uridylyltransferase'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000155.3(GALT): c.499T > C (p.Trp167Arg) | 111033708 | GALT | ['CCCTYGGGTGCAGGTTTGTGAGG'] | ['CCCTYGGGTGCAGGTTTGTGAGG'] | ['Deficiency of UDPglucose-hexose-1-phosphate uridylyltransferase'] |
| NM_000155.3(GALT): c.507 + 2T > C | 111033710 | GALT | [ ] | [ ] | ['Deficiency of UDPglucose-hexose-1-phosphate uridylyltransferase'] |
| NM_000155.3(GALT): c.512T > C (p.Phe171Ser) | 111033715 | GALT | [ ] | [ ] | ['Deficiency of UDPglucose-hexose-1-phosphate uridylyltransferase'] |
| NM_000341.3(SLC3A1): c.2033T > C (p.Leu678Pro) | 121912693 | — | [ ] | [ ] | ['Cystinuria'] |
| NM_000540.2(RYR1): c.9242T > C (p.Met3081Thr) | 147012990 | RYR1 | [ ] | [ ] | ['Minicore myopathy with external ophthalmoplegia'] |
| NM_000155.3(GALT): c.584T > C (p.Leu195Pro) | 111033728 | GALT | [ ] | [ ] | ['Deficiency of UDPglucose-hexose-1-phosphate uridylyltransferase'] |
| NM_000155.3(GALT): c.650T > C (p.Leu217Pro) | 111033741 | GALT | [ ] | [ ] | ['Deficiency of UDPglucose-hexose-1-phosphate uridylyltransferase'] |
| NM_000155.3(GALT): c.687 + 2T > C | 111033748 | GALT | [ ] | [ ] | ['Deficiency of UDPglucose-hexose-1-phosphate uridylyltransferase'] |
| NM_000039.1(APOA1): c.220T > C (p.Trp74Arg) | 121912726 | — | [ ] | [ ] | ['Familial visceral amyloidosis, Ostertag type'] |
| NM_000155.3(GALT): c.677T > C (p.Leu226Pro) | 111033752 | GALT | [ ] | ['CAGGAGCYACTCAGGAAGGTGGG'] | ['Deficiency of UDPglucose-hexose-1-phosphate uridylyltransferase'] |
| NM_000039.1(APOA1): c.593T > C (p.Leu198Ser) | 121912729 | APOA1 | [ ] | ['GCGCTYGGCCGCGCGCCTTGAGG'] | ['Familial visceral amyloidosis, Ostertag type'] |
| NM_000155.3(GALT): c.745T > C (p.Trp249Arg) | 111033757 | GALT | [ ] | [ ] | ['Deficiency of UDPglucose-hexose-1-phosphate uridylyltransferase'] |
| NM_001681.3(ATP2A2): c.1678T > C (p.Cys560Arg) | 121912734 | ATP2A2 | [ ] | [ ] | ['Keratosis follicularis'] |
| NM_000041.3(APOE): c.137T > C (p.Leu46Pro) | 769452 | APOE | [ ] | ['AACYGGCACTGGGTCGCTTTTGG'] | [ ] |
| NM_000342.3(SLC4A1): c.2317T > C (p.Ser773Pro) | 121912753 | SLC4A1 | [ ] | [ ] | ['Renal tubular acidosis, distal, with normal red cell morphology'] |
| NM_003002.3(SDHD): c.284T > C (p.Leu95Pro) | 80338846 | SDHD | [ ] | [ ] | ['Hereditary Paraganglioma-Pheochromocytoma Syndromes'] |
| NM_016124.4(RHD): c.329T > C (p.Leu110Pro) | 121912762 | RHD | [ ] | ['ACACYGTTCAGGTATTGGGATGG'] | [ ] |
| NM_003002.3(SDHD): c.416T > C (p.Leu139Pro) | 80338847 | SDHD | [ ] | [ ] | ['Hereditary Paraganglioma-Pheochromocytoma Syndromes', 'Paragangliomas 1'] |
| NM_001822.5(CHN1): c.427T > C (p.Tyr143His) | 121912794 | CHN1 | [ ] | [ ] | ['Duane syndrome type 2'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000155.3(GALT):<br>c.1138T > C<br>(p.Ter380Arg) | 111033824 | GALT | [ ] | ['CGCCYGACCAC<br>GCCGACCACAGG',<br>'GCCYGACCACGC<br>CGACCACAGGG'] | ['Deficiency of<br>UDPglucose-<br>hexose-1-phosphate<br>uridylyltransferase'] |
| m.3271T > C | 199474658 | MT-TL1 | [ ] | [ ] | ['Juvenile myopathy,<br>encephalopathy,<br>lactic acidosis AND<br>stroke'] |
| NM_000155.3(GALT):<br>c.980T > C<br>(p.Leu327Pro) | 111033832 | GALT | [ ] | ['TCCYGCGCTCTG<br>CCACTGTCCGG'] | ['Deficiency of<br>UDPglucose-<br>hexose-1-phosphate<br>uridylyltransferase'] |
| m.3290T > C | 199474665 | MT-TL1 | [ ] | [ ] | ['Sudden infant<br>death syndrome'] |
| NM_020549.4(CHAT):<br>c.629T > C<br>(p.Leu210Pro) | 121912820 | CHAT | [ ] | [ ] | ['Familial infantile<br>myasthenia'] |
| NM_020549.4(CHAT):<br>c.1007T > C<br>(p.Ile336Thr) | 121912823 | CHAT | [ ] | [ ] | ['Familial infantile<br>myasthenia'] |
| NM_000155.3(GALT):<br>c.328 + 2T > C | 111033849 | GALT | [ ] | [ ] | ['Deficiency of<br>UDPglucose-<br>hexose-1 -phosphate<br>uridylyltransferase'] |
| NM_000267.3(NF1):<br>c.1595T > C<br>(p.Leu532Pro) | 199474737 | NF1 | [ ] | [ ] | ['Neurofibromatosis,<br>type 1', 'not<br>provided'] |
| NM_000455.4(STK11):<br>c.545T > C<br>(p.Leu182Pro) | 730881974 | STK11 | [ ] | ['GGGAACCYGCT<br>GCTCACCACCGG',<br>'AACCYGCTGCTC<br>ACCACCGGTGG'] | ['Hereditary cancer-<br>predisposing<br>syndrome'] |
| NM_001042492.2(NF1):<br>c.2288T > C<br>(p.Leu763Pro) | 199474762 | NF1 | [ ] | [ ] | ['Hereditary cancer-<br>predisposing<br>syndrome', 'not<br>provided'] |
| NM_001042492.2(NF1):<br>c.5858T > C<br>(p.Leu1953Pro) | 199474792 | NF1 | [ ] | [ ] | ['Neurofibromatosis,<br>type 1', 'not<br>provided'] |
| m.7512T > C | 199474817 | MT-TS1 | [ ] | [ ] | ['MERRF/MELAS<br>overlap syndrome'] |
| m.7510T > C | 199474820 | MT-TS1 | [ ] | [ ] | ['Deafness,<br>nonsyndromic<br>sensorineural,<br>mitochondrial'] |
| m.7511T > C | 199474821 | MT-TS1 | [ ] | [ ] | ['Deafness,<br>nonsyndromic<br>sensorineural,<br>mitochondrial'] |
| m.2991T > C | 199474823 | MT-RNR2 | [ ] | [ ] | ['Chloramphenicol<br>resistance'] |
| NM_201253.2(CRB1):<br>c.3122T > C<br>(p.Met1041Thr) | 62635656 | CRB1 | [ ] | [ ] | ['Retinitis<br>pigmentosa 12', 'not<br>provided'] |
| m.7587T > C | 199474825 | MT-OO2 | [ ] | [ ] | ['Cytochrome-c<br>oxidase deficiency'] |
| NM_000400.3(ERCC2):<br>c.1454T > C<br>(p.Leu485Pro) | 121913025 | ERCC2 | [ ] | [ ] | ['Xeroderma<br>pigmentosum, group<br>D'] |
| NM_000157.3(GBA):<br>c.703T > C<br>(p.Ser235Pro) | 1064644 | GBA | [ ] | ['GGGYCACTCAA<br>GGGACAGCCCGG'] | ['Gaucher disease'] |
| NM_001113755.2(TYMP):<br>c.854T > C<br>(p.Leu285Pro) | 121913042 | TYMP | [ ] | [ ] | [ ] |
| NM_000122.1(ERCC3):<br>c.296T > C<br>(p.Phe99Ser) | 121913045 | ERCC3 | [ ] | [ ] | ['Xeroderma<br>pigmentosum,<br>complementation<br>group b'] |
| NM_000186.3(CFH):<br>c.1606T > C<br>(p.Cys536Arg) | 121913052 | CFH | [ ] | [ ] | ['Factor H<br>deficiency'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_138413.3(HOGA1): c.533T > C (p.Leu178Pro) | 796052090 | HOGA1 | [ ] | ['GGACCYGCCTGT GGATGCAGTGG'] | ['Primary hyperoxaluria, type III'] |
| NM_004370.5(COL12A1): c.7001T > C (p.Ile2334Thr) | 796052093 | COL12A1 | [ ] | [ ] | ['BETHLEM MYOPATHY 2'] |
| NM_000043.4(FAS): c.532T > C (p.Cys178Arg) | 121913084 | FAS | [ ] | [ ] | [ ] |
| NM_000208.2(INSR): c.779T > C (p.Leu260Pro) | 121913141 | INSR | [ ] | [CTACCYGGACG GCAGGTGTGTGG'] | ['Leprechaunism syndrome'] |
| NM_000208.2(INSR): c.164T > C (p.Val55Ala) | 121913152 | INSR | [ ] | [ ] | ['Leprechaunism syndrome'] |
| NM_000026.2(ADSL): c.340T > C (p.Tyr114His) | 374259530 | ADSL | [ ] | [ ] | ['Adenylosuccinate lyase deficiency', 'not provided'] |
| NM_153490.2(KRT13): c.356T > C (p.Leu119Pro) | 60440396 | KRT13 | [ ] | [ ] | ['White sponge nevus 2', 'not provided'] |
| NM_022455.4(NSD1): c.5885T > C (p.Ile1962Thr) | 587784162 | NSD1 | [ ] | [ ] | ['Sotos syndrome 1'] |
| NM_006218.2(PIK3CA): c.1258T > C (p.Cys420Arg) | 121913272 | PIK3CA | [ ] | ['GGAACACYGTC CATTGGCATGGG', 'GAACACYGTCCA TTGGCATGGGG'] | ['Congenital lipomatous overgrowth, vascular malformations, and epidermal nevi', 'Neoplasm of ovary', 'PIK3CA Related Overgrowth Spectrum'] |
| NM_000552.3(VWF): c.8317T > C (p.Cys2773Arg) | 61751310 | VWF | [ ] | ['GCTCCYGCTGCT CTCCGACACGG'] | ['von Willebrand disease, type 2a', 'not provided'] |
| NM_000335.4(SCN5A): c.5504T > C (p.Ile1835Thr) | 45563942 | SCN5A | [ ] | [ ] | ['Primary dilated cardiomyopathy', 'Dilated cardiomyopathy 1E', 'not provided'] |
| NM_183415.2(UBE3B): c.1741 + 2T > C | 398123020 | UBE3B | [ ] | [ ] | ['Kaufman oculocerebrofacial syndrome'] |
| NM_000021.3(PSEN1): c.1175T > C (p.Leu392Pro) | 63750218 | PSEN1 | [ ] | [ ] | ['Alzheimer disease, type 3', 'not provided'] |
| NM_000350.2(ABCA4): c.1622T > C (p.Leu541Pro) | 61751392 | ABCA4 | [ ] | [ ] | ['Stargardt disease 1', 'Cone-rod dystrophy 3', 'not provided'] |
| NM_007313.2(ABL1): c.1109T > C (p.Met370Thr) | 121913457 | ABL1 | [ ] | [ ] | [ ] |
| NM_024408.3(NOTCH2): c.1117T > C (p.Cys373Arg) | 312262793 | NOTCH2 | [ ] | [ ] | ['Alagille syndrome 2'] |
| NM_024408.3(NOTCH2): c.1438T > C (p.Cys480Arg) | 312262799 | NOTCH2 | [ ] | ['TTCACAYGTCTG TGCATGCCAGG'] | ['Alagille syndrome 2'] |
| NM_003611.2(OFD1): c.111 + 2T > C | 312262809 | OFD1 | [ ] | [ ] | ['Oral-facial-digital syndrome', 'not provided'] |
| NM_003611.2(OFD1): c.274T > C (p.Ser92Pro) | 312262819 | OFD1 | [ ] | [ ] | ['Oral-facial-digital syndrome'] |
| NM_020631.4(PLEKHG5): c.1940T > C (p.Phe647Ser) | 63750315 | PLEKHG5 | [ ] | [ ] | ['Distal spinal muscular atrophy, autosomal recessive 4'] |
| NM_001288953.1(TTC7A): c.1912T > C (p.Ser638Pro) | 149602485 | TTC7A | [ ] | [ ] | ['Multiple gastrointestinal atresias'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000391.3(TPP1): c.1093T > C (p.Cys365Arg) | 119455953 | TPP1 | ['GCCGGGYGTTGGTCTGTCTCTGG'] | ['GCCGGGYGTTGGTCTGTCTCTGG'] | ['Ceroid lipofuscinosis, neuronal, 2', 'not provided'] |
| NM_000426.3(LAMA2): c.7691T > C (p.Leu2564Pro) | 121913570 | LAMA2 | [ ] | ['ATCATTCYTTTGGAAGTGGAGG', 'TCATTCYTTTGGGAAGTGGAGGG'] | ['Merosin deficient congenital muscular dystrophy'] |
| NM_000426.3(LAMA2): c.2584T > C (p.Cys862Arg) | 121913573 | LAMA2 | [ ] | [ ] | ['Congenital muscular dystrophy due to partial LAMA2 deficiency'] |
| NM_000530.6(MPZ): c.404T > C (p.Ile135Thr) | 121913587 | MPZ | [ ] | [ ] | ['Charcot-Marie-Tooth disease type 1B'] |
| NM_201253.2(CRB1): c.3541T > C (p.Cys1181Arg) | 62636291 | CRB1 | [ ] | [ ] | ['Retinitis pigmentosa 12', 'not provided'] |
| NM_000257.3(MYH7): c.1046T > C (p.Met349Thr) | 121913640 | MYH7 | [ ] | ['AACTCCAYGTATAAGCTGACAGG'] | ['Familial hypertrophic cardiomyopathy 1', 'Cardiomyopathy'] |
| NM_000257.3(MYH7): c.1594T > C (p.Ser532Pro) | 121913642 | MYH7 | [ ] | ['CATCATGYCCATCCTGGAAGAGG'] | ['Dilated cardiomyopathy 1S'] |
| NM_000257.3(MYH7): c.5378T > C (p.Leu1793Pro) | 121913654 | MYH7 | [ ] | [ ] | ['Familial hypertrophic cardiomyopathy 1', 'Myosin storage myopathy', 'Left ventricular noncompaction 5', 'Cardiomyopathy'] |
| NM_001127500.1(MET): c.3446T > C (p.Met1149Thr) | 121913668 | MET | [ ] | [ ] | ['Renal cell carcinoma, papillary, 1'] |
| NM_002443.3(MSMB): c.-89T= | 10993994 | MSMB | [ ] | [ ] | ['Prostate cancer, hereditary, 13'] |
| NM_001079802.1(FKTN): c.527T > C (p.Phe176Ser) | 119463996 | FKTN | [ ] | ['GTAGTCTYTCATGAGAGGAGTGG'] | ['Limb-girdle muscular dystrophy-dystroglycanopathy, type C4'] |
| NM_000169.2(GLA): c.865A > T (p.Ile289Phe) | 140329381 | — | [ ] | [ ] | ['Fabry disease'] |
| NM_000420.2(KEL): c.1790T > C (p.Leu597Pro) | 8176038 | KEL | [ ] | [ ] | [ ] |
| NM_003999.2(OSMR): c.2072T > C (p.Ile691Thr) | 63750567 | OSMR | [ ] | [ ] | ['Primary localized cutaneous amyloidosis 1'] |
| NC_012920.1:m.9478T > C | 587776437 | MT-003 | ['TCAGAAGYTTTTTCTTCGCAGG'] | ['TCAGAAGYTTTTTCTTCGCAGG'] | ['Leigh disease'] |
| NM_002775.4(HTRA1): c.1091T > C (p.Leu364Pro) | 587776447 | HTRA1 | [ ] | [ ] | ['Cerebral autosomal recessive arteriopathy with subcortical infarcts and leukoencephalopath 3'] |
| NM_002049.3(GATA1): c.2T > C (p.Met1Thr) | 587776451 | GATA1 | ['TCCAYGGAGTTCCCTGGCCTGGG', 'CCAYGGAGTTCCCTGGCCTGGG'] | ['CTCCAYGGAGTTCCCTGGCCTGG', 'TCCAYGGAGTTCCTGGCCTGGG', 'CCAYGGAGTTCCCTGGCCTGGGG'] | ['GATA-1-related thrombocytopenia with dyserythropoiesis'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000021.3(PSEN1): c.254T > C (p.Leu85Pro) | 63750599 | PSEN1 | [ ] | [ ] | ['Alzheimer disease, familial, 3, with spastic paraparesis and apraxia', 'not provided'] |
| NM_002049.3(GATA1): c.1240T > C (p.Ter414Arg) | 587776456 | GATA1 | [ ] | ['GCTCAYGAGGG CACAGAGCATGG'] | ['GATA-1-related thrombocytopenia with dyserythropoiesis'] |
| NM_006158.4(NEFL): c.281T > C (p.Leu94Pro) | 62636505 | NEFL | [ ] | [ ] | ['Charcot-Marie-Tooth disease type 2E', 'not provided'] |
| NM_000184.2(HBG2): c.-228T > C locus 1'] | 63750654 | HBG2 | [ ] | ['ATGCAAAYATCT GTCTGAAACGG'] | ['Fetal hemoglobin quantitative trait |
| NM_000353.2(TAT): c.236-5A > G | 587776512 | TAT | [ ] | [ ] | ['Tyrosinemia type 2'] |
| NM_173560.3(RFX6): c.380 + 2T > C | 587776514 | RFX6 | ['CAGT GGYGA GACTC GCCCG CAGG', 'AGTGG YGAGA CTCGC CCGCA GGG'] | ['CAGTGGYGAGA CTCGCCCGCAGG', 'AGTGGYGAGACT CGCCCGCAGGG'] | ['Mitchell-Riley syndrome'] |
| NM_001999.3(FBN2): c.3725-15A > G | 587776519 | FBN2 | [ ] | ['AGCAYTGCAAC CACATTGTCAGG'] | ['Congenital contractural arachnodactyly'] |
| NM_000404.2(GLB1): c.1480-2A > G | 587776526 | GLB1 | [ ] | [ ] | ['GM1-GANGLIOSIDOSIS, TYPE I, WITH CARDIAC INVOLVEMENT'] |
| NM_000402.4(G6PD): c.473T > C (p.Leu158Pro) | 78365220 | G6PD | [ ] | ['TGCCCYCCACCT GGGGTCACAGG'] | ['Anemia, nonspherocytic hemolytic, due to G6PD deficiency', 'not provided'] |
| NM_000179.2(MSH6): c.1346T > C (p.Leu449Pro) | 63750741 | MSH6 | [ ] | ['CTGGGGCYGGT ATTCATGAAAGG'] | ['Hereditary Nonpolyposis Colorectal Neoplasms'] |
| NM_145046.4(CALR3): c.245A > G (p.Lys82Arg) | 142951029 | CALR3 | ['CGGT YTGAA GCGTG CAGAG ATGG'] | ['CGGTYTGAAGC GTGCAGAGATGG'] | ['Arrhythmogenic right ventricular cardiomyopathy', 'Familial hypertrophic cardiomyopathy 19', 'Hypertrophic cardiomyopathy'] |
| NM_000260.3(MY07A): c.5573T > C (p.Leu1858Pro) | 368657015 | MY07A | [ ] | [ ] | ['Usher syndrome, type 1'] |
| NM_024753.4(TTC21B): c.2758-2A > G | 766132877 | TTC21B | [ ] | [ ] | ['Nephronophthisis 12'] |
| NM_001195129.1(PRSS56): c.1183T > C (p.Cys395Arg) | 730882161 | PRSS56 | [ ] | [ ] | ['Microphthalmia, isolated 6'] |
| NM_001184.3(ATR): c.2022A > G (p.Gly674=) | 587776690 | ATR | [ ] | [ ] | ['Seckel syndrome 1'] |
| NM_000354.5(SERPINA7): c.623-2A > G | 587776720 | SERPINA7 | [ ] | [ ] | [ ] |
| NM_000133.3(F9):c.2 77 + 2T > C | 587776735 | F9 | [ ] | [ ] | ['Hereditary factor IX deficiency disease'] |
| NM_004006.2(DMD): c.9225-285A > G | 587776747 | DMD | [ ] | [ ] | ['Becker muscular dystrophy'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_016835.4(MAPT): c.1839T > C (p.Asn613=) | 63750912 | MAPT | ['GGATAAYATCAAACACGTCCCGG', 'GATAAYATCAAACACGTCCCGGG'] | ['GGATAAYATCAAACACGTCCCGG', 'GATAAYATCAAACACGTCCCGGG'] | ['Frontotemporal dementia', 'not provided'] |
| NM_000321.2(RB1): c.1960 + 2T > C | 587776780 | RB1 | [ ] | [ ] | ['Retinoblastoma'] |
| NM_006517.4(SLC16A2): c.1253T > C (p.Leu418Pro) | 367543059 | SLC16A2 | [ ] | [ ] | ['Allan-Herndon-Dudley syndrome'] |
| NM_000421.3(KRT10): c.1374-2A > G | 587776815 | — | [ ] | [ ] | ['Erythroderma, ichthyosiform, congenital reticular'] |
| NM_000251.2(MSH2): c.2089T > C (p.Cys697Arg) | 63750961 | MSH2 | [ ] | [ ] | ['Hereditary Nonpolyposis Colorectal Neoplasms'] |
| NM_002618.3(PEX13): c.977T > C (p.Ile326Thr) | 61752115 | PEX13 | [ ] | [ ] | ['Peroxisome biogenesis disorder 11B'] |
| NM_001079867.1(PEX2): c.739T > C (p.Cys247Arg) | 61752128 | PEX2 | [ ] | [ ] | ['Peroxisome biogenesis disorder 5A'] |
| NM_017929.5(PEX26): c.134T > C (p.Leu45Pro) | 61752132 | PEX26 | [ ] | [ ] | ['Peroxisome biogenesis disorder 7B'] |
| NG_012088.1:g.2209 A > G | 587776843 | IL10 | ['ACCYTATGATCCGCCCGCCTTGG'] | ['ACCYTATGATCCGCCCGCCTTGG'] | [ ] |
| NM_001735.2(C5): c.1115A > G (p.Lys372Arg) | 587776846 | C5 | [ ] | [ ] | ['Leiner disease'] |
| NM_002087.3(GRN): c.2T > C (p.Met1Thr) | 63751006 | GRN | ['CCAYGTGGACCCTGGTGAGCTGG'] | ['CCAYGTGGACCCTGGTGAGCTGG'] | ['Frontotemporal dementia, ubiquitin-positive', 'not provided'] |
| NM_004656.3(BAP1): c.2057-2A > G | 587776878 | BAP1 | [ ] | [ ] | ['Tumor predisposition syndrome'] |
| NM_004656.3(BAP1): c.438-2A > G | 587776879 | BAP1 | ['GCCYGGGGAAAACAGAGTCAGG'] | ['GCCYGGGGAAAACAGAGTCAGG'] | ['Tumor predisposition syndrome'] |
| NM_004329.2(BMPR1A): c.370T > C (p.Cys124Arg) | 199476087 | BMPR1A | [ ] | [ ] | ['Juvenile polyposis syndrome', 'Hereditary cancer-predisposing syndrome'] |
| NM_000510.2(FSHB): c.298T > C (p.Cys100Arg) | 5030777 | FSHB | [ ] | [ ] | ['Follicle-stimulating hormone deficiency, isolated'] |
| NM_001009944.2(PKD1): c.2534T > C (p.Leu845Ser) | 199476100 | PKD1 | [ ] | [ ] | ['Polycystic kidney disease, adult type'] |
| NM_004963.3(GUCY2C): c.1160A > G (p.Asp387Gly) | 587776905 | GUCY2C | [ ] | [ ] | ['Meconium ileus'] |
| m.14487T > C | 199476109 | MT-ND6 | [ ] | [ ] | ['Leigh disease', 'Leigh syndrome due to mitochondrial complex I deficiency'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_017565.3(FAM20A): c.813-2A > G | 587776912 | — | [ ] | [ ] | ['Enamel-renal syndrome'] |
| NM_017565.3(FAM20A): c.590-2A > G | 587776914 | FAM20A | [ ] | ['GTAATCYGCAA AGGAGGAGAAGG', 'TAATCYGCAAAG GAGGAGAAGGG'] | ['Enamel-renal syndrome'] |
| NM_014165.3(NDUFAF4): c.194T > C (p.Leu65Pro) | 63751061 | NDUFAF4 | [ ] | [ ] | ['Mitochondrial complex I deficiency'] |
| m.4160T > C | 199476119 | MT-ND1 | [ ] | [ ] | ['Leber optic atrophy'] |
| NM_000551.3(VHL): c.292T > C (p.Tyr98His) | 5030809 | VHL | [ ] | ['CCCYACCCAACG CTGCCGCCTGG'] | ['Von Hippel-Lindau syndrome', 'Hereditary cancer-predisposing syndrome'] |
| m.3949T > C | 199476124 | MT-ND1 | [ ] | [ ] | ['Juvenile myopathy, encephalopathy, lactic acidosis AND stroke'] |
| m.6742T > C | 199476126 | MT-CO1 | [ ] | [ ] | [ ] |
| m.6721T > C | 199476127 | MT-CO1 | [ ] | [ ] | [ ] |
| m.5692T > C | 199476131 | MT-TN | [ ] | [ ] | [ ] |
| m.5728T > C | 199476132 | MT-TN | [ ] | ['CAATCYACTTCT CCCGCCGCCGG', 'AATCYACTTCTC CCGCCGCCGGG'] | ['Cytochrome-c oxidase deficiency', 'Mitochondrial complex ] deficiency'] |
| m.9101T > C | 199476134 | MT-ATP6 | [ ] | [ ] | ['Leber optic atrophy'] |
| m.8851T > C | 199476136 | MT-ATP6 | [ ] | [ ] | ['Leigh disease', 'Striatonigral degeneration, infantile, mitochondrial'] |
| m.9185T > C | 199476138 | MT-ATP6 | [ ] | [ ] | ['Leigh disease'] |
| NM_000277.1(PAH): c.143T > C (p.Leu48Ser) | 5030841 | PAH | [ ] | [ ] | ['Phenylketonuria', 'not provided'] |
| NM_000277.1(PAH): c.691T > C (p.Ser231Pro) | 5030845 | PAH | [ ] | [ ] | ['Phenylketonuria', 'not provided'] |
| NM_000251.2(MSH2): c.595T > C (p.Cys199Arg) | 63751110 | MSH2 | ['AAGG AAYGT GTTTT ACCCG GAGG'] | ['AAGGAAYGTGT TTACCCGGAGG'] | ['Hereditary Nonpolyposis Colorectal Neoplasms'] |
| NM_000039.1(AP0A1): c.341T > C (p.Leu114Pro) | 28931575 | — | [ ] | [ ] | [ ] |
| NM_001288953.1(TTC7A): c.2366T > C (p.Leu789Pro) | 587776972 | TTC7A | [ ] | [ ] | ['Multiple gastrointestinal atresias'] |
| NM_014336.4(AIPL1): c.715T > C (p.Cys239Arg) | 62637012 | AIPL1 | [ ] | [CTGCCAGYGCCT GCTGAAGAAGG', 'CCAGYGCCTGCT GAAGAAGGAGG'] | ['Leber congenital amaurosis 4', 'not provided'] |
| NM_000155.3(GALT): c.336T > C (p.Ser112=) | 367543254 | GALT | [ ] | [ ] | ['Deficiency of UDPglucose-hexose-1-phosphate uridylyltransferase'] |
| NM_207352.3(CYP4V2): c.655T > C (p.Tyr219His) | 199476191 | CYP4V2 | [ ] | [ ] | ['Bietti crystalline corneoretinal dystrophy'] |
| NM_207352.3(CYP4V2): c.1021T > C (p.Ser341Pro) | 199476199 | CYP4V2 | [ ] | [AAACTGGYCCTT ATACCTGTTGG', 'AACTGGYCCTTA TACCTGTTGGG'] | ['Bietti crystalline corneoretinal dystrophy'] |
| NM_001142519.1(FAM111A): c.1531T > C (p.Tyr511His) | 587777012 | FAM111A | [ ] | [ ] | ['Kenny-Caffey syndrome type 2'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000435.2(NOTCH3): c.4556T > C (p.Leu1519Pro) | 367543285 | NOTCH3 | [ ] | [ ] | ['Infantile myofibromatosis 1', 'Infantile myofibromatosis 2'] |
| NM_000021.3(PSEN1): c.749T > C (p.Leu250Ser) | 63751163 | PSEN1 | [ ] | [ ] | ['Alzheimer disease, type 3', 'not provided'] |
| NM_001283009.1(RTEL1): c.3730T > C (p.Cys1244Arg) | 587777037 | — | ['CTGTGTGYGCCAGGGCTGTGGGG'] | ['CTGTGTGYGCCAGGGCTGTGGGG'] | ['Dyskeratosis congenita, autosomal recessive, 5'] |
| NM_001135021.1(ELMOD3): c.794T > C (p.Leu265Ser) | 587777040 | ELMOD3 | [ ] | [ ] | ['Deafness, autosomal recessive 88'] |
| NM_001001557.2(GDF6): c.866T > C (p.Leu289Pro) | 63751220 | GDF6 | [ ] | [ ] | ['Klippel-Feil syndrome 1, autosomal dominant'] |
| NM_014754.2(PTDSS1): c.794T > C (p.Leu265Pro) | 587777090 | PTDSS1 | [ ] | [ ] | [Lenz-Majewski hyperostosis syndrome'] |
| NM_052844.3(WDR34): c.1307A > G (p.Lys436Arg) | 587777098 | WDR34 | [ ] | [ ] | ['Short-rib thoracic dysplasia 11 with or without polydactyly'] |
| NM_001290048.1(ATL3): c.521A > G (p.Tyr174Cys) | 587777108 | ATL3 | [ ] | [ ] | ['Hereditary sensory neuropathy type IF'] |
| NM_001018005.1(TPM1): c.515T > C (p.Ile172Thr) | 199476312 | TPM1 | [ ] | [ ] | ['Primary familial hypertrophic cardiomyopathy', 'Cardiomyopathy', 'not provided'] |
| NM_018849.2(ABCB4): c.523A > G (p.Thr175Ala) | 58238559 | ABCB4 | [ ] | [ ] | ['Cholecystitis'] |
| NM_001018005.1(TPM1): c.842T > C (p.Met281Thr) | 199476321 | TPM1 | [ ] | [ ] | ['Cardiomyopathy', 'not specified', 'not provided'] |
| NM_005763.3(AASS): c.874A > G (p.Ile292Val) | 587777122 | AASS | [ ] | [ ] | ['Hyperlysinemia'] |
| NM_194442.2(LBR): c.1639A > G (p.Asn547Asp) | 587777171 | LBR | [ ] | [ ] | ['Greenberg dysplasia'] |
| NM_006702.4(PNPLA6): c.3053T > C (p.Phe1018Ser) | 587777183 | PNPLA6 | [ ] | ['CCTYTAACCGCAGCATCCATCGG'] | ['Boucher Neuhauser syndrome'] |
| NM_000487.5(ARSA): :c.899T > C (p.Leu300Ser) | 199476389 | ARSA | [ ] | ['GGTCTCTYGCGGTGTGGAAAGGG'] | ['Metachromatic leukodystrophy', 'not provided'] |
| NM_016599.4(MYOZ): c.142T > C (p.Ser48Pro) | 199476398 | MYOZ2 | [ ] | ['TTAYCCCATCTCAGTAACCGTGG'] | ['Familial hypertrophic cardiomyopathy 16', 'not provided'] |
| NM_014740.3(EIF4A3): c.809A > G (p.Asp270Gly) | 587777204 | EIF4A3 | [ ] | [ ] | ['Richieri Costa Pereira syndrome'] |
| NM_001040436.2(YARS2): c.1303A > G (p.Ser435Gly) | 587777215 | YARS2 | [ ] | [ ] | ['Myopathy, lactic acidosis, and sideroblastic anemia 2'] |
| NM_001278503.1(STT3A): c.1877T > C (p.Val626Ala) | 587777216 | STT3A | [ ] | [ ] | ['Congenital disorder of glycosylation type 1w'] |
| NM_001037633.1(SIL1): c.1370T > C (p.Leu457Pro) | 119456967 | SIL1 | [ ] | ['TTGCYGAAGGAGCTGAGATGAGG'] | [Marinesco-Sj\xc3\xb6gren syndrome'] |
| NM_006888.4(CALM1): c.268T > C (p.Phe90Leu) | 730882253 | CALM1 | [ ] | ['GGCAYTCCGAGTCTTTGACAAGG'] | ['Long QT syndrome 14'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_001003811.1(TEX11): c.511A > G (p.Met171Val) | 143246552 | TEX11 | ['TCCAYGGTCAAGTCAGCCTCAGG'] | ['TCCAYGGTCAAGTCAGCCTCAGG', 'CCAYGGTCAAGTCAGCCTCAGGG'] | ['Spermatogenic failure, X-linked, 2'] |
| NM_033419.4(PGAP3): c.914A > G (p.Asp305Gly) | 587777252 | PGAP3 | [ ] | [ ] | ['Hyperphosphatasia with mental retardation syndrome 4'] |
| NM_000021.3(PSEN1): c.338T > C (p.Leu113Pro) | 63751399 | PSEN1 | [ ] | [ ] | ['Alzheimer disease, type 3', 'Frontotemporal dementia', 'not provided'] |
| NM_000097.5(CPOX): c.980A > G (p.His327Arg) | 587777271 | CPOX | [ ] | [ ] | ['Harderoporphyria'] |
| NM_005654.5(NR2F1): c.755T > C (p.Leu252Pro) | 587777276 | NR2F1 | [ ] | [ ] | ['Bosch-boonstra-schaaf optic atrophy syndrome'] |
| NM_012338.3(TSPAN12): c.413A > G (p.Tyr138Cys) | 587777283 | TSPAN12 | [ ] | ['TAATCCAYAATTTGTCATCCTGG'] | ['Exudative vitreoretinopathy 5'] |
| NM_003181.3(T): c.512A > G (p.His171Arg) | 587777303 | T | [ ] | [ ] | ['Sacral agenesis with vertebral anomalies'] |
| NM_015884.3(MBTPS2): c.1391T > C (p.Phe464Ser) | 587777306 | MBTPS2 | [ ] | ['GCTYTGCTTTGGATGGACAATGG'] | ['Palmoplantar keratoderma, mutilating, with periorificial keratotic plaques, X-linked'] |
| NM_020435.3(GJC2): c.857T > C (p.Met286Thr) | 74315311 | GJC2 | ['TGAGAYGGCCCACCTGGGCTTGG'] | ['TGAGAYGGCCCACCTGGGCTTGG', 'GAGAYGGCCCACCTGGGCTTGG'] | ['Leukodystrophy, hypomyelinating, 2'] |
| NM_005356.4(LCK): c.1022T > C (p.Leu341Pro) | 587777335 | LCK | [ ] | [ ] | ['Immunodeficiency 22'] |
| NM_005861.3(STUB1): c.719T > C (p.Met240Thr) | 587777345 | — | [ ] | [ ] | ['Spinocerebellar ataxia, autosomal recessive 16'] |
| NM_000250.1(MPO): c.752T > C (p.Met251Thr) | 56378716 | MPO | [ ] | ['TCACTCAYGTTCATGCAATGGGG'] | ['Myeloperoxidase deficiency'] |
| NM_017890.4(VPS13B): c.11119 + 2T > C | 587777382 | VPS13B | [ ] | [ ] | ['Cohen syndrome'] |
| NM_005026.3(PIK3CD): c.1246T > C (p.Cys416Arg) | 587777390 | PIK3CD | [ ] | ['GCAGGACYGCCCCATTGCCTGGG'] | ['Activated PI3K-delta syndrome'] |
| NM_002633.2(PGM1): c.1547T > C (p.Leu516Pro) | 587777401 | PGM1 | [ ] | [ ] | ['Congenital disorder of glycosylation type it'] |
| NM_000261.1(MYOC): c.1309T > C (p.Tyr437His) | 74315328 | MYOC | [ ] | [ ] | ['Primary open angle glaucoma juvenile onset 1'] |
| NM_001159287.1(TPI1): c.833T > C (p.Phe278Ser) | 587777440 | TPI1 | [ ] | [ ] | ['Triosephosphate isomerase deficiency'] |
| NM_000414.3(HSD17B4): c.1547T > C (p.Ile516Thr) | 587777443 | HSD17B4 | [ ] | [ ] | ['Gonadal dysgenesis with auditory dysfunction, autosomal recessive inheritance'] |
| NM_005359.5(SMAD4): c.970T > C (p.Cys324Arg) | 377767339 | SMAD4 | [ ] | [ ] | ['Juvenile polyposis syndrome'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000211.4(ITGB2): c.1877 + 2T > C | 483352818 | ITGB2 | ['CATG YGAGT GCAGG CGGAG CAGG'] | ['CATGYGAGTGC AGGCGGAGCAGG'] | ['Leukocyte adhesion deficiency type 1'] |
| NM_005359.5(SMAD4): c.1087T > C (p.Cys363Arg) | 377767348 | SMAD4 | [ ] | [ ] | ['Juvenile polyposis syndrome'] |
| NM_001128159.2(VPS53): c.2084A > G (p.Gln695Arg) | 587777465 | VPS53 | [ ] | [ ] | ['Pontocerebellar hypoplasia, type 2e'] |
| NM_000249.3(MLH1): c.1745T > C (p.Leu582Pro) | 63751616 | MLH1 | [ ] | [ ] | ['Hereditary Nonpolyposis Colorectal Neoplasms'] |
| NM_003108.3(SOX11): c.178T > C (p.Ser60Pro) | 587777480 | SOX11 | [ ] | ['TATGGYCCAAG ATCGAACGCAGG'] | ['Mental retardation, autosomal dominant 27'] |
| NM_020630.4(RET): c.1888T > C (p.Cys630Arg) | 377767404 | RET | [ ] | [ ] | [ ] |
| NM_017565.3(FAM20A): c.720-2A > G | 587777530 | — | [ ] | [ ] | ['Enamel-renal syndrome'] |
| NM_015599.2(PGM3): c.737A > G (p.Asn246Ser) | 587777562 | PGM3 | ['TAAA TGAYT GAGTT TGCCC TTGG'] | ['TAAATGAYTGA GTTTGCCCTTGG'] | ['Immunodeficiency 23'] |
| NM_015599.2(PGM3): c.1352A > G (p.Gln451Arg) | 587777565 | PGM3 | [ ] | [ ] | ['Immunodeficiency 23'] |
| NM_000206.2(IL2RG): c.452T > C (p.Leu151Pro) | 137852511 | IL2RG | [ ] | [ ] | ['X-linked severe combined immunodeficiency'] |
| NM_198282.3(TMEM173): c.461A > G (p.Asn154Ser) | 587777609 | TMEM173 | [ ] | [ ] | ['Sting-associated vasculopathy, infantile-onset'] |
| NM_000329.2(RPE65): c.1022T > C (p.Leu341Ser) | 61752909 | RPE65 | [ ] | [ ] | ['Retinitis pigmentosa 20', 'not provided'] |
| NM_001127899.3(CLCN5): c.1768T > C (p.Ser590Pro) | 151340623 | CLCN5 | [ ] | [ ] | ['Dent disease 1'] |
| NM_005027.3(PIK3R2): c.1202T > C (p.Leu401Pro) | 587777624 | PIK3R2 | [ ] | [ ] | ['Megalencephaly polymicrogyria-polydactyly hydrocephalus syndrome'] |
| NM_007315.3(STAT1): c.854A > G (p.Gln285Arg) | 587777629 | STAT1 | [ ] | [ ] | ['Immunodeficiency 31C'] |
| NM_139276.2(STAT3): c.1175A > G (p.Lys392Arg) | 587777648 | STAT3 | [ ] | [ ] | ['Autoimmune disease, multisystem, infantile-onset'] |
| NM_001037811.2(HSD17B10): c.257A > G (p.Asp86Gly) | 587777651 | HSD17B10 | [ ] | [ ] | ['2-methyl-3-hydroxybutyric aciduria'] |
| NM_001288767.1(ARMC5): c.1928T > C (p.Leu643Pro) | 587777661 | ARMC5 | [ ] | [ ] | ['Acth-independent macronodular adrenal hyperplasia 2'] |
| NM_001288767.1(ARMC5): c.1379T > C (p.Leu460Pro) | 587777663 | ARMC5 | [ ] | ['GCCCGACYGCG GGATGCTGGTGG'] | ['Acth-independent macronodular adrenal hyperplasia 2'] |
| NM_007315.3(STAT1): c.2018A > G (p.Lys673Arg) | 587777704 | STAT1 | [ ] | [ ] | ['Immunodeficiency 31a'] |
| NM_007315.3(STAT1): c.1909A > G (p.Lys637Glu) | 587777705 | STAT1 | [ ] | [ ] | ['Immunodeficiency 31a'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_014845.5(FIG4): c.50T > C (p.Leu17Pro) | 587777713 | FIG4 | [ ] | [ ] | ['Charcot-Marie-Tooth disease, type 4J'] |
| NM_000350.2(ABCA4): c.5819T > C (p.Leu1940Pro) | 61753033 | ABCA4 | [ ] | ['AAGGCYACATG AACTAACCAAGG'] | ['Stargardt disease', 'Stargardt disease 1', 'Cone-rod dystrophy 3', 'not provided'] |
| NM_002972.3(SBF1): c.4768A > G (p.Thr1590Ala) | 200488568 | SBF1 | [ ] | [CAGGCGYCCTCT TGCTCAGCCGG'] | [Charcot-Marie-Tooth disease, type 4B3'] |
| NM_000377.2(WAS): c.244T > C (p.Ser82Pro) | 132630272 | WAS | [ ] | [ ] | [ ] |
| NM_000377.2(WAS): c.809T > C (p.Leu270Pro) | 132630274 | WAS | [ ] | ['CGGAGTCYGTTC TCCAGGGCAGG'] | ['Severe congenital neutropenia X-linked'] |
| NM_001128834.2(PLP1): c.487T > C (p.Trp163Arg) | 132630279 | PLP1 | [ ] | [ ] | ['Pelizaeus-Merzbacher disease', 'not provided'] |
| NM_001128834.2(PLP1): c.671T > C (p.Leu224Pro) | 132630283 | PLP1 | [ ] | [ ] | ['Pelizaeus-Merzbacher disease'] |
| NM_001128834.2(PLP1): c.560T > C (p.Ile187Thr) | 132630288 | PLP1 | [ ] | [ ] | ['Spastic paraplegia 2'] |
| NM_001128834.2(PLP1): c.710T > C (p.Phe237Ser) | 132630291 | PLP1 | [ ] | [ ] | ['Spastic paraplegia 2'] |
| NM_001015877.1(PHF6): c.2T > C (p.Met1Thr) | 132630300 | PHF6 | [ ] | [ ] | ['Borjeson-Forssman-Lehmann syndrome'] |
| NM_001399.4(EDA): c.181T > C (p.Tyr61His) | 132630308 | EDA | [ ] | ['CTGCYACCTAGA GTTGCGCTCGG'] | ['Hypohidrotic X-linked ectodermal dysplasia'] |
| NM_001205019.1(GK): c.1525T > C (p.Trp509Arg) | 132630330 | GK | [ ] | [ ] | ['Deficiency of glycerol kinase'] |
| NM_000076.2(CDKN1C): c.*5 + 2T > C | 587777866 | CDKN1C | ['CCAA GYGAG TACAG CGCAC CTGG', 'CAAGY GAGTA CAGCG CACCT GGG', 'AAGYG AGTAC AGCGC ACCTG GGG'] | ['CCAAGYGAGTA CAGCGCACCTGG', 'CAAGYGAGTACA GCGCACCTGGG', 'AAGYGAGTACAG CGCACCTGGGG'] | ['Beckwith-Wiedemann syndrome'] |
| NM_000271.4(NPC1): c.2054T > C (p.Ile685Thr) | 483352888 | NPC1 | [ ] | [ ] | ['Niemann-Pick disease type C1'] |
| NM_170707.3(LMNA): c.1589T > C (p.Leu530Pro) | 60934003 | LMNA | [ ] | [ACGGCTCYCATC AACTCCACTGG', 'CGGCTCYCATCA ACTCCACTGGG', 'GGCTCYCATCAA CTCCACTGGGG'] | ['Benign scapuloperoneal muscular dystrophy with cardiomyopathy', 'not provided'] |
| NM_001165963.1(SCN1A): c.5536A > T (p.Lys1846Ter) | 372098964 | — | [ ] | [ ] | ['Severe myoclonic epilepsy in infancy'] |
| NM_130838.1(UBE3A): c.2485T > C (p.Tyr829His) | 587784526 | UBE3A | [ ] | [ ] | ['Angelman syndrome'] |
| NM_014588.5(VSX1): c.50T > C (p.Leu17Pro) | 74315436 | VSX1 | [ ] | [ ] | ['Keratoconus 1'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000404.2(GLB1):<br>c.457 + 2T > C | 398123354 | GLB1 | [ ] | [ ] | ['Mucopolysaccharidosis, MPS-IV-B', 'Infantile GM1 gangliosidosis', 'Juvenile GM > 1< gangliosidosis', 'Gangliosidosis GM1 type 3', 'not provided'] |
| NM_003159.2(CDKL5):<br>c.145 + 2T > C | 267608430 | CDKL5 | [ ] | [ ] | ['Atypical Rett syndrome', 'not provided'] |
| NM_002764.3(PRPS1):<br>c.869T > C<br>(p.Ile290Thr) | 180177153 | PRPS1 | [ ] | [ ] | ['Deafness, high-frequency sensorineural, X-linked'] |
| NM_000030.2(AGXT):<br>c.1076T > C<br>(p.Leu359Pro) | 180177160 | AGXT | [ ] | ['GGTGCYGCGGATCGGCCTGCTGG', 'GTGCYGCGGATCGGCCTGCTGGG'] | ['Primary hyperoxaluria, type I'] |
| NM_000030.2(AGXT):<br>c.1151T > C<br>(p.Leu384Pro) | 180177165 | AGXT | [ ] | [ ] | ['Primary hyperoxaluria, type I'] |
| NM_000030.2(AGXT):<br>c.449T > C<br>(p.Leu150Pro) | 180177222 | AGXT | [ ] | [GTGCYGCTGTTCTTAACCCACGG', 'TGCYGCTGTTCTTAACCCACGGG'] | ['Primary hyperoxaluria, type I'] |
| NM_000268.3(NF2):<br>c.1079T > C<br>(p.Leu360Pro) | 74315492 | NF2 | [ ] | [ ] | ['Neurofibromatosis, type 2'] |
| NM_000030.2(AGXT):<br>c.661T > C<br>(p.Ser221Pro) | 180177254 | AGXT | [ ] | ['GCTCATCYCCTTCAGTGACAAGG'] | ['Primary hyperoxaluria, type I'] |
| NM_000030.2(AGXT):<br>c.757T > C<br>(p.Cys253Arg) | 180177264 | AGXT | [ ] | ['GGGGCYGTGACGACCAGCCCAGG'] | ['Primary hyperoxaluria, type I'] |
| NM_000030.2(AGXT):<br>c.77T > C (p.Leu26Pro) | 180177268 | AGXT | [ ] | [ ] | ['Primary hyperoxaluria, type I'] |
| NM_000030.2(AGXT):<br>c.851T > C<br>(p.Leu284Pro) | 180177287 | AGXT | [ ] | [ ] | ['Primary hyperoxaluria, type I'] |
| NM_000030.2(AGXT):<br>c.893T > C<br>(p.Leu298Pro) | 180177293 | AGXT | [ ] | [GTATCYGCATGGGCGCCTGCAGG'] | ['Primary hyperoxaluria, type I'] |
| NM_012203.1(GRHPR):<br>c.203T > C<br>(p.Leu68Pro) | 180177305 | GRHPR | [ ] | [ ] | ['Primary hyperoxaluria, type II'] |
| NM_000017.3(ACADS):<br>c.1057T > C<br>(p.Ser353Pro) | 796051904 | ACADS | [ ] | [ ] | ['not provided'] |
| NM_000406.2(GNRHR):<br>c.392T > C<br>(p.Met131Thr) | 606231406 | GNRHR | [ ] | [ ] | ['Hypogonadotropic hypogonadism'] |
| NM_000255.3(MUT):<br>c.842T > C<br>(p.Leu281Ser) | 796052007 | MUT | [ ] | [ ] | ['not provided'] |
| NM_000030.2(AGXT):<br>c.947T > C<br>(p.Leu316Pro) | 796052063 | AGXT | [ ] | [ ] | ['Primary hyperoxaluria, type I'] |
| NM_138413.3(HOGA1):<br>c.875T > C<br>(p.Met292Thr) | 796052087 | HOGA1 | [ ] | [ ] | ['Primary hyperoxaluria, type III'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_013382.5(POMT2): c.1997A > G (p.Tyr666Cys) | 200198778 | POMT2 | ['GGAAGYAGTGGTGGAAGTAGAGG'] | ['GGAAGYAGTGGTGGAAGTAGAGG'] | ['Congenital muscular dystrophy', 'Congenital muscular dystrophy-dystroglycanopathy with brain and eye anomalies, type A2', 'Muscular dystrophy', 'Congenital muscular dystrophy-dystroglycanopathy with mental retardation, type B2', 'not provided'] |
| NM_015909.3(NBAS): c.3164T > C (p.Leu1055Pro) | 796052121 | NBAS | [ ] | [ ] | ['Infantile liver failure syndrome 2'] |
| NM_000263.3(NAGLU): c.1208T > C (p.Ile403Thr) | 796052122 | NAGLU | [ ] | [ ] | ['Charcot-Marie-Tooth disease, axonal type 2V'] |
| NM_203290.2(POLR1C): c.436T > C (p.Cys146Arg) | 796052125 | POLR1C | [ ] | [ ] | ['LEUKODYSTROPHY, HYPOMYELINATING, 11'] |
| NM_018359.3(UFSP2): c.868T > C (p.Tyr290His) | 796052130 | — | [ ] | [ ] | ['Hip dysplasia, beukes type'] |
| NM_000053.3(ATP7B): c.122A > G (p.Asn41Ser) | 201738967 | ATP7B | [ ] | [ ] | ['Wilson disease'] |
| NM_001356.4(DDX3X): c.704T > C (p.Leu235Pro) | 796052224 | DDX3X | [ ] | [ ] | ['not provided'] |
| NM_001356.4(DDX3X): c.1541T > C (p.Ile514Thr) | 796052226 | DDX3X | [ ] | [ ] | ['not provided'] |
| NM_001356.4(DDX3X): c.1175T > C (p.Leu392Pro) | 796052232 | DDX3X | [ ] | [ ] | ['not provided'] |
| NM_000321.2(RB1): c.2663 + 2T > C | 587778839 | RB1 | [ ] | [ ] | ['Retinoblastoma'] |
| NM_000321.2(RB1): c.1472T > C (p.Leu491Pro) | 587778848 | RB1 | [ ] | [ ] | ['Retinoblastoma'] |
| NM_006894.5(FMO3): c.1079T > C (p.Leu360Pro) | 28363581 | FMO3 | [ ] | [ ] | ['Trimethylaminuria'] |
| NM_172107.2(KCNQ2): c.583T > C (p.Ser195Pro) | 796052620 | KCNQ2 | [ ] | [ ] | ['not provided'] |
| NM_001282227.1(CECR1): c.1232A > G (p.Tyr411Cys) | 376785840 | CECR1 | [ ] | ['GAAATCAYAGGACAAGCCTTTGG'] | ['Polyarteritis nodosa'] |
| NM_170707.3(LMNA): c.644T > C (p.Leu215Pro) | 61295588 | LMNA | [ ] | [ ] | ['Dilated cardiomyopathy 1A', 'not provided'] |
| NM_005249.4(FOXG1): c.673T > C (p.Trp225Arg) | 796052482 | FOXG1 | [ ] | [ ] | ['not provided'] |
| NM_000806.5(GABRA1): c.788T > C (p.Met263Thr) | 796052491 | GABRA1 | [ ] | [ ] | ['not provided'] |
| NM_000251.2(MSH2): c.1319T > C (p.Leu440Pro) | 587779084 | MSH2 | [ ] | [ ] | ['Hereditary Nonpolyposis Colorectal Neoplasms'] |
| NM_003401.3(XRCC4): c.127T > C (p.Trp43Arg) | 587779351 | XRCC4 | [ ] | [ ] | ['Ateleiotic dwarfism'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_198056.2(SCN5A): c.1247A > G (p.Tyr416Cys) | 372395294 | SCN5A | ['CTCAYAGGCCATTGCGACCACGG'] | ['CTCAYAGGCCATTGCGACCACGG'] | ['not provided'] |
| NM_000257.3(MYH7): c.4835T > C (p.Leu1612Pro) | 587779392 | — | [ ] | [ ] | ['Myopathy, distal, 1'] |
| NM_000257.3(MYH7): c.4937T > C (p.Leu1646Pro) | 587779393 | — | [ ] | ['GAGCCYCCAGAGCTTGTTGAAGG'] | ['Myopathy, distal, 1'] |
| NM_000404.2(GLB1): c.922T > C (p.Phe308Leu) | 587779404 | GLB1 | [ ] | [ ] | ['Infantile GM1 gangliosidosis'] |
| NM_012434.4(SLC17A5): c.500T > C (p.Leu167Pro) | 587779410 | SLC17A5 | [ ] | ['ATTGTACYCAGAGCACTAGAAGG'] | ['Sialic acid storage disease, severe infantile type'] |
| NM_000257.3(MYH7): c.4442T > C (p.Leu1481Pro) | 587779414 | — | [ ] | [ ] | ['Myopathy, distal, 1'] |
| NM_000090.3(COL3A1): c.2022 + 2T > C (p.Gly660_Lys674del) | 587779429 | COL3A1 | [ ] | [ ] | ['Ehlers-Danlos syndrome, type 4'] |
| NM_004453.3(ETFDH): c.1852T > C (p.Ter618Gln) | 765742496 | ETFDH | [ ] | [ ] | ['not provided'] |
| NM_000090.3(COL3A1): c.2337 + 2T > C (p.Gly762_Lys779del) | 587779513 | COL3A1 | [ ] | ['AGGYAACCCTTAATACTACCTGG'] | ['Ehlers-Danlos syndrome, type 4'] |
| NM_000310.3(PPT1): c.2T > C (p.Met1Thr) | 796052927 | PPT1 | [ ] | [ ] | ['not provided'] |
| NM_020376.3(PNPLA2): c.757 + 2T > C | 777539013 | PNPLA2 | [ ] | ['GAACGGYGCGCGGACCCGGGCGG', 'AACGGYGCGCGGACCCGGGCGGG'] | ['Neutral lipid storage disease with myopathy'] |
| NM_000090.3(COL3A1): c.3039 + 6T > C (p.Asp1013_Gly1014insVSSSFYSTSQ) | 587779532 | COL3A1 | [ ] | [ ] | ['Ehlers-Danlos syndrome, type 4'] |
| NM_012452.2(TNFRSF13B): c.310T > C (p.Cys104Arg) | 34557412 | TNFRSF13B | [ ] | ['ACTTCYGTGAGAACAAGCTCAGG'] | ['Immunoglobulin A deficiency 2', 'Common variable immunodeficiency 2'] |
| NM_000570.4(FCGR3B): c.244A= (p.Asn82=) | 147574249 | FCGR3B | [ ] | [ ] | [ ] |
| NM_001165963.1(SCN1A): c.1094T > C (p.Phe365Ser) | 796052970 | SCN1A | [ ] | ['CAAGCTYTGATACCTTCAGTTGG', 'AAGCTYTGATACCTTCAGTTGGG'] | ['not provided'] |
| NC_012920.1:m.7505 T > C | 724159989 | MT-TS1 | [ ] | ['CCTCCAYGACTTTTTCAAAAAGG'] | ['Deafness, nonsyndromic sensorineural, mitochondrial'] |
| NM_000663.4(ABAT): c.1433T > C (p.Leu478Pro) | 724159991 | ABAT | [ ] | [ ] | ['Gamma-aminobutyric acid transaminase deficiency'] |
| NM_153818.1(PEX10): c.890T > C (p.Leu297Pro) | 724160000 | PEX10 | [ ] | [ ] | ['Peroxisome biogenesis disorder 6B'] |
| NM_153818.1(PEX10): c.2T > C (p.Met1Thr) | 724160002 | PEX10 | [ ] | [ ] | ['Peroxisome biogenesis disorder 6B'] |
| NM_000090.3(COL3A1): c.4399T > C (p.Ter1467Gln) | 587779618 | COL3A1 | [ ] | [ ] | ['Ehlers-Danlos syndrome, type 4'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_002485.4(NBN): c.511A > G (p.Ile171Val) | 61754966 | NBN | [ ] | [ ] | ['Microcephaly, normal intelligence and immunodeficiency', 'Aplastic anemia', 'Hereditary cancer-predisposing syndrome', 'Leukemia, acute lymphoblastic, susceptibility to', 'not specified', 'not provided'] |
| NM_000090.3(COL3A1): c.2553 + 2T > C (p.Gly816_Ala851del) | 587779684 | COL3A1 | [ ] | [ ] | ['Ehlers-Danlos syndrome, type 4'] |
| NM_021007.2(SCN2A): c.4308 + 2T > C | 796053139 | SCN2A | ['CGAAATGYAAGTCTAGTTAGAGG', 'GAAATGYAAGTCTAGTTAGAGGG'] | ['CGAAATGYAAGTCTAGTTAGAGG', 'GAAATGYAAGTCTAGTTAGAGGG'] | ['not provided'] |
| NM_021007.2(SCN2A): c.4718T > C (p.Leu1573Pro) | 796053152 | SCN2A | [ ] | [ ] | ['not provided'] |
| NM_001101.3(ACTB): c.356T > C (p.Met119Thr) | 587779773 | ACTB | ['GAGAAGAYGACCCAGGTGAGTGG'] | ['GAGAAGAYGACCCAGGTGAGTGG'] | ['Baraitser-Winter syndrome 1'] |
| NM_021007.2(SCN2A): c.2306T > C (p.Ile769Thr) | 796053191 | SCN2A | [ ] | [ ] | ['not provided'] |
| NM_014191.3(SCN8A): c.4889T > C (p.Leu1630Pro) | 796053222 | SCN8A | [ ] | ['CGTCYGATCAAAGGCGCCAAAGG', 'GTCYGATCAAAGGCGCCAAAGGG'] | ['not provided'] |
| NM_012415.3(RAD54B): c.1778A > G (p.Asn593Ser) | 114216685 | RAD54B | [ ] | [ ] | ['Malignant lymphoma, non-Hodgkin'] |
| NM_007215.3(POLG2): c.1105A > G (p.Arg369Gly) | 201936720 | POLG2 | [ ] | [ ] | ['Autosomal dominant progressive external ophthalmoplegia with mitochondrial DNA deletions 4', 'not specified'] |
| NM_004006.2(DMD): c.6982A > T (p.Lys2328Ter) | 754896795 | DMD | ['GCTTTTYTTCAAGCTGCCCAAGG'] | ['GCTTTTYTTCAAGCTGCCCAAGG'] | ['Duchenne muscular dystrophy', 'Becker muscular dystrophy', 'Dilated cardiomyopathy 3B'] |
| NM_001061.4(TBXAS1): c.248T > C (p.Leu83Pro) | 140005285 | TBXAS1 | [ ] | [ ] | ['not provided'] |
| NM_000540.2(RYR1): c.10817T > C (p.Leu3606Pro) | 118192127 | RYR1 | [ ] | ['TACTACCYGGACCAGGTGGGTGG', 'ACTACCYGGACCAGGTGGGTGGG', 'CTACCYGGACCAGGTGGGTGGGG'] | ['Central core disease', 'not provided'] |
| NM_000138.4(FBN1): c.7754T > C (p.Ile2585Thr) | 727503054 | FBN1 | [ ] | [ ] | ['Thoracic aortic aneurysms and aortic dissections', 'Marfan syndrome'] |
| NM_001128227.2(GNE): c.2228T > C (p.Met743Thr) | 28937594 | GNE | [ ] | [ ] | ['Inclusion body myopathy 2', 'Nonaka myopathy'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000540.2(RYR1): c.14693T > C (p.Ile4898Thr) | 118192170 | RYR1 | [ ] | ['AGGCAYTGGGG ACGAGATCGAGG'] | ['Malignant hyperthermia susceptibility type 1', 'Central core disease', 'not provided'] |
| NM_005247.2(FGF3): c.466T > C (p.Ser156Pro) | 121917703 | FGF3 | [ ] | ['GTACGTGYCTGT GAACGGCAAGG', 'TACGTGYCTGTG AACGGCAAGGG'] | ['Deafness with labyrinthine aplasia microtia and microdontia (LAMM)'] |
| NM_005247.2(FGF3): c.17T > C (p.Leu6Pro) | 121917706 | FGF3 | [ ] | [ ] | ['Deafness with labyrinthine aplasia microtia and microdontia (LAMM)'] |
| NM_005211.3(CSF1R): c.2450T > C (p.Leu817Pro) | 690016549 | CSF1R | [ ] | ['CCGCCYGCCTGT GAAGTGGATGG'] | ['Hereditary diffuse leukoencephalopathy with spheroids'] |
| NM_005211.3(CSF1R): c.2480T > C (p.Ile827Thr) | 690016550 | CSF1R | [ ] | [ ] | ['Hereditary diffuse leukoencephalopathy with spheroids'] |
| NM_005211.3(CSF1R): c.2566T > C (p.Tyr856His) | 690016552 | CSF1R | [ ] | ['GAATCCCYACCC TGGCATCCTGG'] | ['Hereditary diffuse leukoencephalopathy with spheroids'] |
| NM_001098668.2(SFTPA2): c.593T > C (p.Phe198Ser) | 121917738 | SFTPA2 | [ ] | ['GGAGACTYCCG CTACTCAGATGG', 'GAGACTYCCGCT ACTCAGATGGM | ['Idiopathic fibrosing alveolitis, chronic form'] |
| NM_005211.3(CSF1R): c.1957T > C (p.Cys653Arg) | 690016559 | CSF1R | [ ] | ['AGCCYGTACCCA TGGAGGTAAGG', 'GCCYGTACCCAT GGAGGTAAGGG'] | ['Hereditary diffuse leukoencephalopathy with spheroids'] |
| NM_005211.3(CSF1R): c.2717T > C (p.Ile906Thr) | 690016560 | CSF1R | [ ] | ['GCAGAYCTGCTC CTTCCTTCAGG'] | ['Hereditary diffuse leukoencephalopathy with spheroids'] |
| NM_000540.2(RYR1): c.14378T > C (p.Leu4793Pro) | 118192179 | RYR1 | [ ] | [ ] | ['Central core disease', 'not provided'] |
| NM_199292.2(TH): c.707T > C (p.Leu236Pro) | 121917763 | TH | [ ] | [ ] | ['Segawa syndrome, autosomal recessive'] |
| NM_000256.3(MYBPC3): c.2994 + 2T > C | 727503176 | MYBPC3 | [ ] | [ ] | ['Familial hypertrophic cardiomyopathy 4'] |
| NM_003361.3(UMOD): c.376T > C (p.Cys126Arg) | 121917769 | UMOD | [ ] | ['GGCCACAYGTGT CAATGTGGTGG', 'GCCACAYGTGTC AATGTGGTGGG'] | ['Familial juvenile gout'] |
| NM_003361.3(UMOD): c.943T > C (p.Cys315Arg) | 121917773 | UMOD | [ ] | ['ATGGCACYGCC AGTGCAAACAGG'] | ['Glomerulocystic kidney disease with hyperuricemia and isosthenuria'] |
| NM_024649.4(BBS1): c.1553T > C (p.Leu518Pro) | 121917778 | — | [ ] | [ ] | ['Bardet-Biedl syndrome 1'] |
| NM_172107.2(KCNQ2): c.2T > C (p.Met1Thr) | 118192186 | KCNQ2 | [ ] | [ ] | ['Benign familial neonatal seizures 1'] |
| NM_014324.5(AMACR): c.154T > C (p.Ser52Pro) | 121917814 | — | [ ] | [ ] | ['Alpha-methylacyl-CoA racemase deficiency', 'Bile acid synthesis defect, congenital, 4'] |
| NM_014324.5(AMACR): c.320T > C (p.Leu107Pro) | 121917816 | — | [ ] | [ ] | ['Bile acid synthesis defect, congenital, 4'] |
| NM_007255.2(B4GALT7): c.617T > C (p.Leu206Pro) | 121917818 | B4GALT7 | [ ] | ['TGCYCTCCAAGC AGCACTACCGG'] | ['Ehlers-Danlos syndrome progeroid type'] |
| NM_021615.4(CHST6): c.827T > C (p.Leu276Pro) | 121917824 | CHST6 | [ ] | ['GGACCYGGCGC GGGAGCCGCTGG'] | ['Macular corneal dystrophy Type I'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_006261.4(PROP1): c.263T > C (p.Phe88Ser) | 121917841 | PROP1 | [ ] | [ ] | ['Pituitary hormone deficiency, combined 2'] |
| NM_000452.2(SLC10A2): c.728T > C (p.Leu243Pro) | 121917848 | SLC10A2 | [ ] | ['TTTCYTCTGGCT AGAATTGCTGG'] | ['Bile acid malabsorption, primary'] |
| NM_000322.4(PRPH2): c.637T > C (p.Cys213Arg) | 61755802 | PRPH2 | [ ] | [ ] | ['Patterned dystrophy of retinal pigment epithelium', 'not provided', 'Leber congenital amaurosis 18'] |
| NM_000517.4(HBA2): c.89T > C (p.Leu30Pro) | 41341344 | HBA2 | [ ] | [ ] | ['Hemoglobin H disease, nondeletional'] |
| NM_002181.3(IHH): c.569T > C (p.Val190Ala) | 121917857 | IHH | [ ] | [ ] | ['Acrocapitofemoral dysplasia'] |
| NM_000322.4(PRPH2): c.736T > C (p.Trp246Arg) | 61755817 | PRPH2 | ['ACCTGYGGGTGCGTGGCTGCAGG', 'CCTGYGGGTGCGTGGCTGCAGGG'] | ['ACCTGYGGGTGCGTGGCTGCAGG', 'CCTGYGGGTGCGTGGCTGCAGGG'] | ['Retinitis pigmentosa', 'not provided'] |
| NM_005413.3(SIX3): c.749T > C (p.Val250Ala) | 121917880 | SIX3 | [ ] | [ ] | ['Holoprosencephaly 2'] |
| NM_000124.3(ERCC6): c.2960T > C (p.Leu987Pro) | 121917905 | ERCC6 | ['TGCYAAAAGACCCAAAACAAAGG'] | ['TGCYAAAAGACCCAAAACAAAGG'] | [Cerebro-oculo-facio-skeletal syndrome'] |
| NM_006920.4(SCN1A): c.4729T > C (p.Cys1577Arg) | 121917919 | — | [ ] | [ ] | ['Severe myoclonic epilepsy in infancy', 'not provided'] |
| NM_006920.4(SCN1A): c.5113T > C (p.Cys1705Arg) | 121917926 | — | [ ] | [ ] | ['Severe myoclonic epilepsy in infancy', 'not provided'] |
| NM_006920.4(SCN1A): c.3577T > C (p.Trp1193Arg) | 121917930 | — | ['AACAAYGGTGGAACCTGAGAAGG'] | ['AACAAYGGTGGAACCTGAGAAGG'] | ['Generalized epilepsy with febrile seizures plus, type 1', 'Generalized epilepsy with febrile seizures plus, type 2'] |
| NM_006920.4(SCN1A): c.838T > C (p.Trp280Arg) | 121917938 | SCN1A | [ ] | [ ] | ['Severe myoclonic epilepsy in infancy'] |
| NM_000478.4(ALPL): c.1306T > C (p.Tyr436His) | 121918006 | ALPL | [ ] | [IGGACYATGGTGAGACCTCCAGG'] | ['Infantile hypophosphatasia'] |
| NM_000478.4(ALPL): c.979T > C (p.Phe327Leu) | 121918010 | ALPL | [ ] | [CAAAGGCYTCTTCTTGCTGGTGG', 'GGCYTCTTCTTGCTGGTGGAAGG'] | ['Infantile hypophosphatasia'] |
| NM_000301.3(PLG): c.1771T > C (p.Ser591Pro) | 121918029 | PLG | [ ] | [ ] | ['Dysplasminogenemia'] |
| NM_000174.4(GP9): c.20T > C (p.Leu7Pro) | 121918038 | GP9 | [ ] | [ ] | ['Bernard-Soulier syndrome type C'] |
| NM_000371.3(TTR): c.224T > C (p.Leu75Pro) | 121918079 | TTR | [ ] | [ ] | ['Amyloidogenic transthyretin amyloidosis'] |
| NM_000371.3(TTR): c.88T > C (p.Cys30Arg) | 121918083 | TTR | [ ] | [ ] | ['Amyloidogenic transthyretin amyloidosis', 'Cardiomyopathy'] |
| NM_000371.3(TTR): c.272T > C (p.Val91Ala) | 121918084 | TTR | [ ] | [ ] | ['Amyloidogenic transthyretin amyloidosis'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000371.3(TTR): c.400T > C (p.Tyr134His) | 121918088 | TTR | [ ] | ['TCCCYACTCCTA TTCCACCACGG'] | [ ] |
| NM_012275.2(IL36R N):c.115 + 6T > C | 148755083 | IL36RN | [ ] | [ ] | ['Pustular psoriasis, generalized'] |
| NM_000371.3(TTR): c.95T > C (p.Leu32Pro) | 121918094 | TTR | [ ] | [ ] | ['Amyloidogenic transthyretin amyloidosis'] |
| NM_000371.3(TTR): c.265T > C (p.Tyr89His) | 121918100 | TTR | [ ] | [ ] | ['AMYLOIDOSIS, LEPTOMENINGEA L, TRANSTHYRETIN -RELATED'] |
| NM_001042465.1(PSAP): c.1055T > C (p.Leu352Pro) | 121918110 | PSAP | [ ] | ['GAAGCYGCCGA AGTCCCTGTCGG'] | ['Gaucher disease, atypical, due to saposin C deficiency'] |
| NM_013251.3(TAC3): c.269T > C (p.Met90Thr) | 121918123 | TAC3 | [ ] | [ ] | ['not provided'] |
| NM_199069.1(NDUFAF3): c.2T > C (p.Met1Thr) | 121918136 | NDUFAF3 | [ ] | [ ] | ['Mitochondrial complex I deficiency'] |
| NM_003730.4(RNASET2): c.550T > C (p.Cys184Arg) | 121918137 | RNASET2 | [ ] | [CCAGYGCCTTCC ACCAAGCCAGG'] | ['Leukoencephalopat hy, cystic, without megalencephaly'] |
| NM_203395.2(IYD): c.347T > C (p.Ile116Thr) | 121918139 | IYD | [ ] | [ ] | ['Iodotyrosine deiodination defect'] |
| NM_001127628.1(FBP1): c.581T > C (p.Phe194Ser) | 121918191 | FBP1 | [ ] | ['GGAGTYCATTTT GGTGGACAAGG'] | ['Fructose-biphosphatase deficiency'] |
| NM_015506.2(MMACHC): c.347T > C (p.Leu116Pro) | 121918240 | MMACHC | [ ] | [ ] | ['Methylmalonic acidemia with homocystinuria'] |
| NM_000255.3(MUT): c.313T > C (p.Trp105Arg) | 121918249 | MUT | [ ] | [ ] | ['METHYLMALON IC ACIDURIA, mut(0) TYPE'] |
| NM_022370.3(ROBO3): c.14T > C (p.Leu5Pro) | 121918275 | ROB03 | [ ] | [ ] | ['Gaze palsy, familial horizontal, with progressive scoliosis'] |
| NM_018400.3(SCN3B): c.29T > C (p.Leu10Pro) | 121918282 | SCN3B | [ ] | [ ] | ['Brugada syndrome', 'Brugada syndrome 7', 'Cardiac arrhythmia', 'Atrial fibrillation, familial, 16'] |
| NM_004183.3(BEST1): c.122T > C (p.Leu41Pro) | 121918288 | BEST1 | [ ] | [ ] | ['Bestrophinopathy, autosomal recessive', 'not provided'] |
| NM_020166.4(MCCC1): c.640-2A > G | 772395858 | MCCC1 | [ ] | [ ] | ['3 Methylcrotonyl-CoA carboxylase 1 deficiency'] |
| NM_004817.3(TJP2): c.143T > C (p.Val48Ala) | 121918299 | TJP2 | [ ] | [ ] | ['Hypercholanemia, familial'] |
| NM_006946.2(SPTBN2): c.758T > C (p.Leu253Pro) | 121918306 | SPTBN2 | [ ] | ['ACCAAGCYGCT GGATCCCGAAGG', 'AAGCYGCTGGAT CCCGAAGGTGG', 'AGCYGCTGGATC CCGAAGGTGGG'] | ['Spinocerebellar ataxia 5'] |
| NM_000214.2(JAG1): c.110T > C (p.Leu37Ser) | 121918352 | JAG1 | [ ] | [ ] | ['Alagille syndrome 1'] |
| NM_007194.3(CHEK2): c.470T > C (p.Ile157Thr) | 17879961 | CHEK2 | [ ] | [ ] | ['Familial cancer of breast', 'Hereditary cancer-predisposing syndrome', 'Li-Fraumeni syndrome 2', 'not specified'] |
| NM_015384.4(NIPBL): c.7637T > C (p.Leu2546Pro) | 727503772 | NIPBL | [ ] | [ ] | ['Cornelia de Lange syndrome 1'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_001083112.2(GPD2):<br>c.1904T > C<br>(p.Phe635Ser) | 121918407 | GPD2 | ['AAGT<br>YTGAT<br>GCAGA<br>CCAGA<br>AAGG'] | ['AAGTYTGATGCA<br>GACCAGAAAGG'] | ['Diabetes mellitus<br>type 2'] |
| NM_021957.3(GYS2):<br>c.1447T > C<br>(p.Ser483Pro) | 121918424 | GYS2 | [ ] | [ ] | ['Hypoglycemia with<br>deficiency of<br>glycogen synthetase<br>in the liver'] |
| NM_018849.2(ABCB4):<br>c.1207T > C<br>(p.Tyr403His) | 121918443 | ABCB4 | [ ] | [ ] | ['Progressive<br>familial intrahepatic<br>cholestasis 3'] |
| NM_000212.2(ITGB3):<br>c.2332T > C<br>(p.Ser778Pro) | 121918447 | — | [ ] | [ ] | ['Glanzmann<br>thrombasthenia'] |
| NM_000506.3(F2):<br>c.1139T > C<br>(p.Met380Thr) | 121918481 | F2 | [ ] | [ ] | ['Hereditary factor II<br>deficiency disease'] |
| NM_000141.4(FGFR2):<br>c.1018T > C<br>(p.Tyr340His) | 121918489 | FGFR2 | ['TGGG<br>GAAYA<br>TACGT<br>GCTTG<br>GCGG',<br>'GGGGA<br>AYATA<br>CGTGC<br>TTGGC<br>GGG'] | ['TGGGGAAYATA<br>CGTGCTTGGCGG',<br>'GGGGAAYATACG<br>TGCTTGGCGGG'] | ['Crouzon<br>syndrome'] |
| NM_000141.4(FGFR2):<br>c.799T > C<br>(p.Ser267Pro) | 121918505 | FGFR2 | [ ] | ['AATGCCYCCACA<br>GTGGTCGGAGG'] | ['Pfeiffer syndrome',<br>'Neoplasm of<br>stomach'] |
| NM_002739.3(PRKCG):<br>c.355T > C<br>(p.Ser119Pro) | 121918512 | PRKCG | [ ] | [ ] | ['Spinocerebellar<br>ataxia 14'] |
| NM_002739.3(PRKCG):<br>c.1927T > C<br>(p.Phe643Leu) | 121918516 | PRKCG | [ ] | [ ] | ['Spinocerebellar<br>ataxia 14'] |
| NM_015107.2(PHF8):<br>c.836T > C<br>(p.Phe279Ser) | 121918524 | PHF8 | [ ] | [ ] | [Siderius X-linked<br>mental retardation<br>syndrome'] |
| NM_000311.3(PRNP):<br>c.593T > C<br>(p.Phe198Ser) | 74315405 | PRNP | [ ] | [ ] | ['Gerstmann-<br>Straussler-Scheinker<br>syndrome', 'Genetic<br>prion diseases'] |
| NM_015665.5(AAAS):<br>c.787T > C<br>(p.Ser263Pro) | 121918550 | AAAS | [ ] | [ ] | [Glucocorticoid<br>deficiency with<br>achalasia'] |
| NM_003018.3(SFTPC):<br>c.581T > C<br>(p.Leu194Pro) | 121918560 | SFTPC | [ ] | [ ] | ['Surfactant<br>metabolism<br>dysfunction,<br>pulmonary, 2'] |
| NM_000322.4(PRPH2):<br>c.554T > C<br>(p.Leu185Pro) | 121918563 | PRPH2 | [ ] | [ ] | ['Patterned<br>dystrophy of retinal<br>pigment epithelium',<br>'Retinitis pigmentosa<br>7, digenic', 'not<br>provided', 'Leber<br>congenital<br>amaurosis 181 |
| NM_000322.4(PRPH2):<br>c.2T > C (p.Met1Thr) | 121918565 | PRPH2 | [ ] | [ ] | ['Macular dystrophy,<br>vitelliform, adult-<br>onset', 'not<br>provided'] |
| NM_001035.2(RYR2):<br>c.1298T > C<br>(p.Leu433Pro) | 121918602 | RYR2 | [ ] | [ ] | ['Arrhythmogenic<br>right ventricular<br>cardiomyopathy,<br>type 2',<br>'Catecholaminergic<br>polymorphic<br>ventricular<br>tachycardia', 'Long<br>QT syndrome'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_001199138.1(NLRC4): c.1022T > C (p.Val341Ala) | 587781260 | NLRC4 | [ ] | [ ] | ['Syndrome of entercolitis and autoinflmmation caused by mutation of NLRC4 (SCAN4)', 'Autoinflammation with infantile enterocolitis'] |
| NM_000702.3(ATP1A2): c.857T > C (p.Ile286Thr) | 121918617 | ATP1A2 | [ ] | [ ] | ['Familial hemiplegic migraine type 2'] |
| NM_006920.4(SCN1A): c.4250T > C (p.Val1417Ala) | 121918627 | — | [ ] | [ ] | ['Generalized epilepsy with febrile seizures plus, type 1', 'Generalized epilepsy with febrile seizures plus, type 2'] |
| NM_006920.4(SCN1A): c.434T > C (p.Met145Thr) | 121918631 | SCN1A | [ ] | [ ] | ['Generalized epilepsy with febrile seizures plus, type 2'] |
| NM_006920.4(SCN1A): c.4462T > C (p.Phe1488Leu) | 121918632 | — | [ ] | [ ] | ['Familial hemiplegic migraine type 3'] |
| NM_003126.2(SPTA1): c.781T > C (p.Ser261Pro) | 121918636 | SPTA1 | [ ] | [ ] | ['Elliptocytosis 2'] |
| NM_003126.2(SPTA1): c.620T > C (p.Leu207Pro) | 121918643 | SPTA1 | [ ] | ['GTGGAGCYGGT AGCTAAAGAAGG', 'TGGAGCYGGTAG CTAAAGAAGGG'] | ['Hereditary pyropoikilocytosis', 'Elliptocytosis 2'] |
| NM_001024858.2(SPTB): c.604T > C (p.Trp202Arg) | 121918646 | SPTB | [ ] | [CTCCAGCYGGA AGGATGGCTTGG'] | ['Spherocytosis type 2'] |
| NM_001024858.2(SPTB): c.6055T > C (p.Ser2019Pro) | 121918648 | SPTB | [ ] | ['ATGCCYCTGTGG CTGAGGCGTGG'] | [ ] |
| NM_001128177.1(THRB): c.929T > C (p.Met310Thr) | 121918699 | THRB | [ ] | [ ] | [ ] |
| NM_001128177.1(THRB): c.1373T > C (p.Val458Ala) | 121918704 | THRB | [ ] | [ ] | ['Thyroid hormone resistance, generalized, autosomal recessive'] |
| NM_000421.3(KRT10): c.482T > C (p.Leu161Ser) | 60118264 | — | [ ] | [ ] | ['Bullous ichthyosiform erythroderma', 'not provided'] |
| NM_006920.4(SCN1A): c.269T > C (p.Phe90Ser) | 121918733 | SCN1A | ['ACTTY TATAG TATTG AATAA AGG', 'CTTYT ATAGT ATTGA ATAAA GGG'] | ['ACTTYTATAGTA TTGAATAAAGG', 'CTTYTATAGTATT GAATAAAGGG'] | ['Severe myoclonic epilepsy in infancy'] |
| NM_006920.4(SCN1A): c.272T > C (p.Ile91Thr) | 121918734 | SCN1A | ['ACTTT TAYAG TATTG AATAA AGG', 'CTTTT AYAGT ATTGA ATAAA GGG'] | ['ACTTTTAYAGTA TTGAATAAAGG', 'CTTTTAYAGTATT GAATAAAGGAG'] | ['Severe myoclonic epilepsy in infancy'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_006920.4(SCN1A): c.3827T > C (p.Leu1276Pro) | 121918740 | — | [ ] | [ ] | ['Severe myoclonic epilepsy in infancy'] |
| NM_000543.4(SMPD1): c.475T > C (p.Cys159Arg) | 727504166 | SMPD1 | [ ] | [IGAGGCCYGTG GCCTGCTCCTGG', 'GAGGCCYGTGGC CTGCTCCTGGG'] | ['Niemann-Pick disease, type A', 'Niemann-Pick disease, type B'] |
| NM_006920.4(SCN1A): c.568T > C (p.Trp190Arg) | 121918773 | SCN1A | [ ] | [ ] | ['Severe myoclonic epilepsy in infancy'] |
| NM_006920.4(SCN1A): c.5522T > C (p.Met1841Thr) | 121918783 | — | [ ] | [ ] | ['Severe myoclonic epilepsy in infancy', 'Generalized epilepsy with febrile seizures plus, type 1'] |
| NM_002538.3(OCLN): c.656T > C (p.Phe219Ser) | 267606926 | OCLN | [ ] | [ ] | ['Band-like calcification with simplified gyration and polymicrogyria'] |
| NM_000434.3(NEU1): c.1088T > C (p.Leu363Pro) | 193922915 | NEU1 | [ ] | [CAGCYATGGCC AGGCCCCAGTGG] | [Sialidosis, type II'] |
| NM_198578.3(LRRK2): c.6059T > C (p.Ile2020Thr) | 35870237 | LRRK2 | [ ] | [ ] | ['Parkinson disease 8, autosomal dominant'] |
| NM_000501.3(ELN): c.889 + 2T > C | 727504419 | ELN | [ ] | ['CAGGYAACATCT GTCCCAGCAGG', 'AGGYAACATCTG TCCCAGCAGGG'] | [Supravalvar aortic stenosis'] |
| NM_001085.4(SERPINA3): c.233T > C (p.Leu78Pro) | 1800463 | SERPINA3 | [ ] | [ ] | [ ] |
| NM_000238.3(KCNH2): c.1736T > C (p.Met579Thr) | 199473425 | KCNH2 | | | ['Congenital long QT syndrome'] |
| NM_001211.5(BUB1B): c.3035T > C (p.Leu1012Pro) | 28989185 | — | [ ] | [ ] | ['Mosaic variegated aneuploidy syndrome', 'Premature chromatid separation trait'] |
| NM_000256.3(MYBPC3): c.26-2A > G | 376395543 | MYBPC3 | [ ] | ['GAGACYGAAGG GCCAGGTGGAGG'] | ['Primary familial hypertrophic cardiomyopathy', 'Familial hypertrophic cardiomyopathy 4', 'Cardiomyopathy'] |
| NM_000051.3(ATM): c.4776 + 2T > C | 587781927 | ATM | [ ] | [ ] | ['Ataxia-telangiectasia syndrome', 'Hereditary cancer-predisposing syndrome'] |
| NM_006412.3(AGPAT2): c.589-2A > G | 116807569 | AGPAT2 | [ ] | [ ] | ['Congenital generalized lipodystrophy type 1'] |
| NM_000545.6(HNF1A): c.1720G > A (p.Gly574Ser) | 1169305 | HNF1A | [ ] | [GATGCYGGCAG GGTCCTGGCTGG', 'ATGCYGGCAGGG TCCTGGCTGGG', 'TGCYGGCAGGGT CCTGGCTGGGG'] | ['Maturity-onset diabetes of the young, type 3'] |
| NM_024514.4(CYP2R1): c.296T > C (p.Leu99Pro) | 61495246 | CYP2R1 | [ ] | [ ] | ['Vitamin d hydroxylation-deficient rickets, type 1b'] |
| NM_012213.2(MLYCD): c.119T > C (p.Met40Thr) | 28937908 | MLYCD | [ ] | [ ] | ['Deficiency of malonyl-CoA decarboxylase'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_001101.3(ACTB): c.224T > C (p.Ile75Thr) | 587779771 | ACTB | [ ] | [ ] | ['Baraitser-Winter syndrome 1'] |
| NM_021007.2(SCN2A): c.1271T > C (p.Val424Ala) | 796053181 | SCN2A | ['TGTGGYGGCCATGGCCTATGAGGl] | ['TGTGGYGGCCAT GGCCTATGAGG'] | ['not provided'] |
| NM_002880.3(RAF1): c.769T > C (p.Ser257Pro) | 727505017 | RAF1 | [ ] | [ ] | ['Rasopathy', 'not specified'] |
| NM_000527.4(LDLR): c.1468T > C (p.Trp490Arg) | 730880130 | LDLR | [ ] | [CTACYGGACCG ACTCTGTCCTGG', 'TACYGGACCGAC TCTGTCCTGGG] | ['Familial hypercholesterolemial |
| NM_170707.3(LMNA): c.710T > C (p.Phe237Ser) | 730880132 | LMNA | ['TGAGTYTGA GAGCC GGCTG GCGG'] | ['TGAGTYTGAGA GCCGGCTGGCGG'] | ['Primary dilated cardiomyopathy'] |
| NM_000080.3(CHRNE): c.223T > C (p.Trp75Arg) | 193919341 | — | [ ] | [ ] | ['MYASTHENIC SYNDROME, CONGENITAL, 4B, FAST-CHANNEL'] |
| NM_005211.3(CSF1R): c.2297T > C (p.Met766Thr) | 281860270 | CSF1R | [ ] | [ ] | ['Hereditary diffuse leukoencephalopath y with spheroids'] |
| NM_005211.3(CSF1R): c.2381T > C (p.Ile794Thr) | 281860274 | CSF1R | ['CAAG AYTGG GGACT TCGGG CTGG'] | ['CAAGAYTGGGG ACTTCGGGCTGG'] | ['Hereditary diffuse leukoencephalopathy with spheroids'] |
| NM_005211.3(CSF1R): c.2546T > C (p.Phe849Ser) | 281860277 | CSF1R | [ ] | [ ] | ['Hereditary diffuse leukoencephalopath y with spheroids'] |
| NM_005211.3(CSF1R): c.2624T > C (p.Met875Thr) | 281860279 | CSF1R | [ ] | [ ] | ['Hereditary diffuse leukoencephalopath y with spheroids'] |
| NM_018713.2(SLC30A10): c.266T > C (p.Leu89Pro) | 281860284 | SLC30A10 | [ ] | [ ] | ['Hypermanganesem ia with dystonia, polycythemia and cirrhosis'] |
| NM_018713.2(SLC30A10): c.500T > C (p.Phe167Ser) | 281860286 | SLC30A10 | [ ] | ['GGCGCTTYCGGG GGGCCTCAGGG'] | ['Hypermanganesem ia with dystonia, polycythemia and cirrhosis'] |
| NM_018713.2(SLC30A10): c.1046T > C (p.Leu349Pro) | 281860291 | SLC30A10 | [ ] | [ ] | ['Hypermanganesem ia with dystonia, polycythemia and cirrhosis'] |
| NM_016218.2(POLK): c.2287T > A (p.Tyr763Asn) | 772307321 | POLK | [ ] | [ ] | ['Malignant tumor of prostate'] |
| NM_000570.4(FCGR3B): c.194A > G (p.Asn65Ser) | 448740 | FCGR3B | [ ] | [ ] | [ ] |
| NM_030653.3(DDX11): c.2271 + 2T > C | 730880279 | DDX11 | ['TCCA GGYGC GGGCG TCATG CTGG'] | ['TCCAGGYGCGG GCGTCATGCTGG', 'CCAGGYGCGGGC GTCATGCTGGG'] | ['Warsaw breakage syndrome'] |
| NM_145693.2(LPIN1): c.1441 + 2T > C | 730880306 | LPIN1 | [ ] | [AAGGYACCGCG GGCCTCGCGCGG', 'AGGYACCGCGGG CCTCGCGCGGG'] | ['Myoglobinuria, acute recurrent, autosomal recessive'] |
| NM_002546.3(TNFRSH1B): c.226A > C (p.Thr76Pro) | 200071478 | TNFRSF11B | [ ] | [ ] | ['Hyperphosphatase mia with bone disease'] |
| NM_000166.5(GJB1): c.145T > C (p.Ser49Pro) | 116840817 | GJB1 | [ ] | [ ] | ['X-linked hereditary motor and sensory neuropathy'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_005159.4(ACTC1):<br>c.755T > C<br>(p.Ile252Thr) | 730880398 | — | [ ] | [ ] | ['Cardiomyopathy'] |
| NM_020166.4(MCCC1):<br>c.205A > T<br>(p.Lys69Ter) | 147741073 | MCCC1 | [ ] | [ ] | ['3 Methylcrotonyl-<br>CoA carboxylase 1<br>deficiency'] |
| NM_000454.4(SOD1):<br>c.338T > C<br>(p.Ile113Thr) | 74315452 | SOD1 | [ ] | ['TTGCAYCATTGG<br>CCGCACACTGG'] | ['Amyotrophic<br>lateral sclerosis type<br>1'] |
| NM_000169.2(GLA):<br>c.41T > C (p.Leu14Pro) | 730880455 | — | [ ] | ['CGCGCYTGCGCT<br>TCGCTTCCTGG'] | ['not provided'] |
| NM_152743.3(BRAT1):<br>c.176T > C<br>(p.Leu59Pro) | 727505363 | BRAT1 | [ ] | [ ] | ['Rigidity and<br>multifocal seizure<br>syndrome, lethal<br>neonatal'] |
| NM_005633.3(SOS1):<br>c.2104T > C<br>(p.Tyr702His) | 727505381 | SOS1 | [ ] | [ ] | ['Noonan syndrome',<br>'Rasopathy'] |
| m.1095T > C | 267606618 | MT-RNR1 | [ ] | [ ] | ['Aminoglycoside-<br>induced deafness',<br>'Auditory<br>neuropathy',<br>'Deafness,<br>nonsyndromic<br>sensorineural,<br>mitochondrial', 'not<br>specified'] |
| m.1291T > C | 267606620 | MT-RNR1 | [ ] | [ ] | ['Deafness,<br>nonsyndromic<br>sensorineural,<br>mitochondrial'] |
| NM_020247.4(ADCK3):<br>c.1398 + 2T > C | 606231138 | ADCK3 | [ ] | [ ] | ['Coenzyme Q10<br>deficiency, primary,<br>4'] |
| NM_000256.3(MYBPC3):<br>c.467T > C<br>(p.Leu156Pro) | 730880616 | MYBPC3 | [ ] | [ ] | ['Cardiomyopathy'] |
| NM_022458.3(LMBR1):<br>c.423 + 4842T > C | 606231149 | LMBR1 | [ ] | [ ] | ['Triphalangeal<br>thumb', 'Preaxial<br>polydactyly 2'] |
| NM_022458.3(LMBR1):<br>c.423 + 4808T > C | 606231152 | LMBR1 | [ ] | [ ] | ['Triphalangeal<br>thumb', 'Preaxial<br>polydactyly 2'] |
| NM_021102.3(SPINT2):<br>c.337 + 2T > C | 606231155 | SPINT2 | [ ] | [ ] | ['Diarrhea 3,<br>secretory sodium,<br>congenital,<br>syndromic'] |
| NM_001004127.2(ALG11):<br>c.257T > C<br>(p.Leu86Ser) | 267606652 | ALG11 | [ ] | [ ] | ['Congenital disorder<br>of glycosylation type<br>1P'] |
| NM_054027.4(ANKH):<br>c.1015T > C<br>(p.Cys339Arg) | 267606656 | ANKH | [ ] | ['AGCTCYGTTTCG<br>TGATGTTTTGG'] | ['Craniometaphyseal<br>dysplasia, autosomal<br>dominant'] |
| NM_054027.4(ANKH):<br>c.1172T > C<br>(p.Leu391Pro) | 267606658 | — | [ ] | [ ] | ['Craniometaphyseal<br>dysplasia, autosomal<br>dominant'] |
| NM_175073.2(APTX):<br>c.668T > C<br>(p.Leu223Pro) | 267606665 | APTX | [ ] | [ ] | ['Adult onset ataxia<br>with oculomotor<br>apraxia'] |
| NM_004183.3(BEST1):<br>c.704T > C<br>(p.Val235Ala) | 267606679 | BEST1 | ['CACT<br>GGYGT<br>ATACA<br>CAGGT<br>GAGG'] | ['CACTGGYGTATA<br>CACAGGTGAGG'] | ['Vitreoretinochoroid<br>opathy dominant'] |
| NM_004183.3(BEST1):<br>c.614T > C<br>(p.Ile205Thr) | 267606680 | BEST1 | [ ] | [ ] | ['Retinitis<br>pigmentosa 50'] |
| NM_033409.3(SLC52A3):<br>c.670T > C<br>(p.Phe224Leu) | 267606685 | SLC52A3 | [ ] | [ ] | [Brown-Vialetto-<br>Van laere<br>syndrome'] |
| NM_033409.3(SLC52A3):<br>c.1238T > C<br>(p.Val413Ala) | 267606687 | SLC52A3 | [ ] | ['AGTTACGYCAA<br>GGTGATGCTGGG'] | [Brown-Vialetto-<br>Van laere<br>syndrome'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_004056.4(CA8): c.298T > C (p.Ser100Pro) | 267606695 | CA8 | [ ] | [ ] | ['Cerebellar ataxia, mental retardation, and dysequilibrium syndrome 3'] |
| NM_000256.3(MYBPC3): c.3713T > C (p.Leu1238Pro) | 730880702 | MYBPC3 | [ ] | [ ] | ['Cardiomyopathy'] |
| NM_001928.2(CFD): c.640T > C (p.Cys214Arg) | 267606721 | CFD | [ ] | ['GGTGYGCGGGG GCGTGCTCGAGG', 'GTGYGCGGGGGC GTGCTCGAGGM | ['Complement factor d deficiency'] |
| NM_005740.2(DNAL4): c.153 + 2T > C | 606231254 | DNAL4 | ['CGAG GYATT GCCAG CAGTG CAGG'] | ['CGAGGYATTGCC AGCAGTGCAGG'] | ['Mirror movements 3'] |
| NM_020975.4(RET): c.2753T > C (p.Met918Thr) | 74799832 | RET | [ ] | [ ] | ['Multiple endocrine neoplasia, type 2a', 'Multiple endocrine neoplasia, type 2b', 'Multiple endocrine neoplasia, type 2', 'Pheochromocytoma', 'not provided'] |
| NM_001849.3(COL6A2): c.2329T > C (p.Cys777Arg) | 267606747 | COL6A2 | [ ] | ['CGCCYGCGACA AGCCACAGCAGG'] | ['Ullrich congenital muscular dystrophy'] |
| NM_001006657.1(WDR35): c.781T > C (p.Trp261Arg) | 431905505 | WDR35 | [ ] | [ ] | ['Short rib polydactyly syndrome 5'] |
| NM_003764.3(STX11): c.173T > C (p.Leu58Pro) | 431905512 | STX11 | ['TGCY GGTGG CCGAC GTGAA GCGG'] | ['TGCYGGTGGCCG ACGTGAAGCGG'] | ['Hemophagocytic lymphohistiocytosis, familial, 4'] |
| NM_001044.4(SLC6A3): c.671T > C (p.Leu224Pro) | 431905515 | SLC6A3 | [ ] | ['CTGCACCYCCAC CAGAGCCATGG'] | ['Infantile Parkinsonism-dystonia'] |
| NM_000277.1(PAH): c.764T > C (p.Leu255Ser) | 62642930 | PAH | [ ] | [ ] | ['Phenylketonuria', 'not provided'] |
| NM_000277.1(PAH): c.932T > C (p.Leu311Pro) | 62642936 | PAH | [ ] | [ ] | ['Phenylketonuria', 'not provided'] |
| NM_000118.3(ENG): c.2T > C (p.Met1Thr) | 267606783 | ENG | [ ] | [ ] | ['Osler hemorrhagic telangiectasia syndrome'] |
| NM_000129.3(F13A1): c.728T > C (p.Met243Thr) | 267606788 | F13A1 | ['TGTG AYGGA CAGAG CACAA ATGG'] | ['TGTGAYGGACA GAGCACAAATGG'] | ['Factor xiii, a subunit, deficiency of'] |
| NM_000257.3(MYH7): c.1952A > G (p.His651Arg) | 606231328 | MYH7 | [ ] | [ ] | ['Familial cardiomyopathy'] |
| NM_014053.3(FLVCR1): c.574T > C (p.Cys192Arg) | 267606821 | FLVCR1 | [ ] | [ ] | ['Posterior column ataxia with retinitis pigmentosa'] |
| NM_005249.4(FOXG1): c.643T > C (p.Phe215Leu) | 267606828 | FOXG1 | [ ] | [ ] | ['Rett syndrome, congenital variant'] |
| NM_015474.3(SAMHD1): c.1153A > G (p.Met385Val) | 515726140 | SAMHD1 | [ ] | [ ] | ['Aicardi Goutieres syndrome 5'] |
| NM_015474.3(SAMHD1): c.1411-2A > G | 515726141 | SAMHD1 | [ ] | [ ] | ['Aicardi Goutieres syndrome 5'] |
| NM_000180.3(GUCY2D): c.2846T > C (p.Ile949Thr) | 267606857 | GUCY2D | [ ] | ['AGAGAYCGCCA ACATGTCACTGG'] | ['Cone-rod dystrophy 6'] |
| NM_022489.3(INF2): c.556T > C (p.Ser186Pro) | 267606877 | INF2 | [ ] | [ ] | ['Focal segmental glomerulosclerosis 5'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000257.3(MYH7): c.1048T > C (p.Tyr350His) | 730880863 | MYH7 | [ ] | [ ] | ['Cardiomyopathy'] |
| NM_022489.3(INF2): c.125T > C (p.Leu42Pro) | 267606880 | INF2 | [ ] | ['GCTGCYCCAGAT GCCCTCTGTGG'] | ['Focal segmental glomerulosclerosis 5'] |
| m.4681T > C | 267606889 | MT-ND2 | [ ] | [ ] | ['Leigh disease', 'Leigh syndrome due to mitochondrial complex I deficiency'] |
| m.10191T > C | 267606890 | MT-ND3 | [ ] | [ ] | ['Leigh disease', 'Mitochondrial complex I deficiency'] |
| m.10563T > C | 267606892 | MT-ND4L | [ ] | [ ] | ['Familial colorectal cancer'] |
| m.12706T > C | 267606893 | MT-NDS | [ ] | [ ] | ['Leigh disease', 'Leigh syndrome due to mitochondrial complex I deficiency'] |
| NM_015713.4(RRM2B): c.556A > G (p.Arg186Gly) | 515726190 | RRM2B | [ ] | [ ] | ['RRM2B-related mitochondrial disease'] |
| NM_015713.4(RRM2B): c.581A > G (p.Glu194Gly) | 515726191 | RRM2B | [ ] | ['AACTCCTYCTAC AGCAGCAAAGG'] | ['RRM2B-related mitochondrial disease'] |
| NM_000315.2(PTH): c.52T > C (p.Cys18Arg) | 104894271 | PTH | ['AATT YGTTT TCTTA CAAAA TCGG'] | ['AATTYGTTTTCT TACAAAATCGG'] | ['Hypoparathyroidism familial isolated'] |
| NM_001136271.2(NKX2-6): c.451T > C (p.Phe151Leu) | 267606914 | NKX2-6 | [ ] | [ ] | ['Persistent truncus arteriosus'] |
| NM_004646.3(NPHS1): c.793T > C (p.Cys265Arg) | 267606917 | NPHS1 | [ ] | ['GCTGCCGYGCGT GGCCCGAGGGG', 'CTGCCGYGCGTG GCCCGAGGGGG'] | ['Finnish congenital nephrotic syndrome'] |
| NM_000406.2(GNRHR): c.94A > G (p.Thr32Ala) | 515726219 | GNRHR | [ ] | [ ] | ['Hypogonadotropic hypogonadism'] |
| NM_152296.4(ATP1A3): c.2270T > C (p.Leu757Pro) | 606231436 | ATP1A3 | [ ] | [ ] | ['Alternating hemiplegia of childhood 2'] |
| NM_000513.2(OPN1MW): c.529T > C (p.Trp177Arg) | 267606927 | OPN1MW | [ ] | [ ] | ['Cone dystrophy 5, X-linked'] |
| NM_152296.4(ATP1A3): c.1144T > C (p.Trp382Arg) | 606231448 | ATP1A3 | [ ] | [ ] | ['Dystonia 12'] |
| NM_024411.4(PDYN): c.632T > C (p.Leu211Ser) | 267606940 | PDYN | [ ] | [ ] | ['Spinocerebellar ataxia 23'] |
| NM_000444.5(PHEX): c.755T > C (p.Phe252Ser) | 267606945 | PHEX | [ ] | [ ] | ['Familial X-linked hypophosphatemic vitamin D refractory rickets'] |
| NM_001543.4(NDST1): c.1918T > C (p.Phe640Leu) | 606231458 | NDST1 | [ ] | [ ] | ['Mental retardation, autosomal recessive 46'] |
| NM_013382.5(POMT2): c.2242T > C (p.Trp748Arg) | 267606964 | POMT2 | [ ] | [ ] | ['Congenital muscular dystrophy-dystroglycanopathy with mental retardation, type B2'] |
| NM_006121.3(KRT1): c.482T > C (p.Leu161Pro) | 57695159 | KRT1 | [ ] | [ ] | ['Bullous ichthyosiform erythroderma', 'not provided'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_016203.3(PRKAG2): c.1459T > C (p.Tyr487His) | 267606976 | PRKAG2 | [ ] | [ ] | ['Familial hypertrophic cardiomyopathy 6', 'not provided'] |
| NM_016203.3(PRKAG2): c.1642T > C (p.Ser548Pro) | 267606979 | PRKAG2 | [ ] | [ ] | ['Familial hypertrophic cardiomyopathy 6', 'not provided'] |
| NM_198965.1(PTHLH): c.179T > C (p.Leu60Pro) | 267606985 | PTHLH | [ ] | [ ] | ['Brachydactyly type E2'] |
| NM_198965.1(PTHLH): c.131T > C (p.Leu44Pro) | 267606986 | PTHLH | [ ] | [ ] | ['Brachydactyly type E2'] |
| NM_004990.3(MARS): c.1108T > C (p.Phe370Leu) | 140467171 | MARS | [ ] | [ ] | ['Interstitial lung and liver disease'] |
| NM_173560.3(RFX6): c.649T > C (p.Ser217Pro) | 267607012 | RFX6 | [ ] | [ ] | ['Mitchell-Riley syndrome'] |
| NM_002942.4(ROBO2): c.2834T > C (p.Ile945Thr) | 267607014 | ROB02 | ['GAGAYTGGAAATTTGGCCGTGG'] | ['GAGAYTGGAAATTTTGGCCGTGG'] | ['Vesicoureteral reflux 2'] |
| NM_178857.5(RP1L1): c.2878T > C (p.Trp960Arg) | 267607018 | RP1L1 | [ ] | [ ] | ['Occult macular dystrophy'] |
| NM_002880.3(RAF1): c.1423T > C (p.Phe475Leu) | 730881003 | RAF1 | [ ] | [ ] | ['Rasopathy'] |
| NM_015272.3(RPGRIP1L): c.1975T > C (p.Ser659Pro) | 267607020 | RPGRIP1L | [ ] | [ ] | ['Joubert syndrome 7', 'COACH syndrome'] |
| NM_015559.2(SETBP1): c.2612T > C (p.Ile871Thr) | 267607038 | SETBP1 | [ ] | [ ] | ['Schinzel-Giedion syndrome'] |
| NM_000433.3(NCF2): c.481A > G (p.Lys161Glu) | 137878529 | NCF2 | [ ] | [ ] | ['Chronic granulomatous disease, autosomal recessive cytochrome b-positive, type 2'] |
| NM_001041.3(SI): c.1022T > C (p.Leu341Pro) | 267607049 | SI | [ ] | [ ] | ['Sucrase-isomaltase deficiency'] |
| NM_005633.3(SOS 1): c.1294T > C (p.Trp432Arg) | 267607080 | SOS 1 | ['GGTYGGGAGGGGGAAAAGACATTGG'] | ['GGTYGGGAGGGAAAAGACATTGG'] | ['Noonan syndrome 4', 'Rasopathy'] |
| NM_018136.4(ASPM): c.2419 + 2T > C | 587783225 | ASPM | [ ] | [ ] | ['Primary autosomal recessive microcephaly 5'] |
| NM_001199107.1(TBC1D24): c.751T > C (p.Phe251Leu) | 267607104 | TBC1D24 | [ ] | ['CAAGTTCYTCCACAAGGTGAGGG', 'TTCYTCCACAAGGTGAGGGCCGG'] | ['Myoclonic epilepsy, familial infantile'] |
| NM_153704.5(TMEM67): c.1769T > C (p.Phe590Ser) | 267607115 | TMEM67 | [ ] | [ ] | ['Joubert syndrome 6', 'COACH syndrome'] |
| NM_153704.5(TMEM67): c.2498T > C (p.Ile833Thr) | 267607119 | TMEM67 | [ ] | [ ] | ['Joubert syndrome 6', 'COACH syndrome'] |
| NM_133378.4(TTN): c.100163T > C (p.Leu33388Pro) | 267607156 | — | [ ] | [ ] | ['Distal myopathy Markesbery-Griggs type'] |
| m.12811T > C | 199974018 | MT-ND5 | [ ] | [ ] | ['Leber optic atrophy'] |
| NM_144631.5(ZNF513): c.1015T > C (p.Cys339Arg) | 267607182 | ZNF513 | [ ] | ['TGGGCGCYGCATGCGAGGAGAGG', 'CGCYGCATGCGAGGAGAGGCTGG'] | ['Retinitis pigmentosa 58'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_004737.4(LARGE): c.1483T > C (p.Trp495Arg) | 267607209 | LARGE | [ ] | [ ] | ['Congenital muscular dystrophy-dystroglycanopathy with brain and eye anomalies, type A6'] |
| NM_000229.1(LCAT): c.508T > C (p.Trp170Arg) | 267607211 | LCAT | [ ] | ['TATGACYGGCG GCTGGAGCCCGG'] | ['Norum disease'] |
| NM_016269.4(LEF1): c.181T > C (p.Ser61Pro) | 267607215 | — | [ ] | ['GAACGAGYCTG AAATCATCCCGG'] | ['Sebaceous tumors, somatic'] |
| NM_139248.2(LIPH): c.322T > C (p.Trp108Arg) | 267607219 | LIPH | [ ] | [ ] | ['Woolly hair, autosomal recessive 2, with or without hypotrichosis'] |
| NM_004268.4(MED17): c.1112T > C (p.Leu371Pro) | 267607232 | MED17 | [ ] | [ ] | ['Microcephaly, postnatal progressive, with seizures and brain atrophy'] |
| NM_000530.6(MPZ): c.341T > C (p.Ile114Thr) | 267607241 | MPZ | [ ] | [ ] | [ ] |
| NM_000489.4(ATRX): :c.4840T > C (p.Cys1614Arg) | 122445094 | ATRX | [ ] | [ ] | ['ATR-X syndrome'] |
| NM_000489.4(ATRX): c.6250T > C (p.Tyr2084His) | 122445097 | ATRX | [ ] | [ ] | ['ATR-X syndrome'] |
| NM_000489.4(ATRX): c.1226T > C (p.Leu409Ser) | 122445109 | ATRX | [ ] | [ ] | [ ] |
| NM_000489.4(ATRX): c.6149T > C (p.Ile2050Thr) | 122445110 | ATRX | [ ] | [ ] | ['Multiple congenital anomalies'] |
| NM_178151.2(DCX): c.272T > C (p.Leu91Pro) | 587783536 | DCX | [ ] | [ ] | ['Heterotopia'] |
| NM_178151.2(DCX): c.2T > C (p.Met1Thr) | 587783539 | DCX | ['CAAA ATAYG GAACT TGATT TTGG'] | ['CAAAATAYGGA ACTTGATTTTGG'] | ['Heterotopia'] |
| NM_178151.2(DCX): c.412T > C (p.Tyr138His) | 587783551 | DCX | [ ] | [ ] | ['Heterotopia'] |
| NM_000212.2(ITGB3): c.2231T > C (p.Leu744Pro) | 398122374 | — | [ ] | [ ] | ['Platelet-type bleeding disorder 16'] |
| NM_178151.2(DCX): c.641T > C (p.Ile214Thr) | 587783574 | DCX | [ ] | [ ] | ['Heterotopia'] |
| NM_178151.2(DCX): c.683T > C (p.Leu228Pro) | 587783580 | DCX | [ ] | ['AAAAAACYCTA CACTCTGGATGG'] | ['Heterotopia'] |
| NM_001005360.2(DNM2): c.1862T > C (p.Leu621Pro) | 587783597 | DNM2 | [ ] | [ ] | ['Myopathy, centronuclear'] |
| NM_006579.2(EBP): c.310T > C (p.Tyr104His) | 587783609 | EBP | [ ] | [ ] | ['Chondrodysplasia punctata 2 X-linked dominant'] |
| NM_004004.5(GJB2): c.107T > C (p.Leu36Pro) | 587783644 | GJB2 | [ ] | ['GATCCYCGTTGT GGCTGCAAAGG'] | ['Hearing impairment'] |
| NM_005682.6(ADGRG1): c.1460T > C (p.Leu487Pro) | 587783653 | ADGRG1 | [ ] | [VCCTGCYCACCT GCCTTTCCTGG'] | ['Polymicrogyria, bilateral frontoparietal'] |
| NM_000525.3(KCNJ11): c.988T > C (p.Tyr330His) | 587783675 | KCNJ11 | [ ] | [ ] | ['Diabetes mellitus'] |
| NM_170707.3(LMNA): c.799T > C (p.Tyr267His) | 267607593 | LMNA | [ ] | [ ] | ['Dilated cardiomyopathy 1A', 'not provided'] |
| NM_000252.2(MTM1): c.1353 + 2T > C | 587783780 | MTM1 | [ ] | [ ] | ['Severe X-linked myotubular myopathy'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000252.2(MTM1):<br>c.1367T > C<br>(p.Phe456Ser) | 587783783 | MTM1 | [ ] | [ ] | ['Severe X-linked myotubular myopathy'] |
| NM_000252.2(MTM1):<br>c.1433T > C<br>(p.Phe478Ser) | 587783794 | MTM1 | [ ] | [ ] | ['Severe X-linked myotubular myopathy'] |
| NM_000252.2(MTM1):<br>c.1495T > C<br>(p.Trp499Arg) | 587783801 | MTM1 | [ ] | [ ] | ['Severe X-linked myotubular myopathy'] |
| NM_000252.2(MTM1):<br>c.260T > C<br>(p.Leu87Pro) | 587783816 | MTM1 | [ ] | [ ] | ['Severe X-linked myotubular myopathy'] |
| NM_000252.2(MTM1):<br>c.683T > C<br>(p.Leu228Pro) | 587783851 | MTM1 | [ ] | [ ] | ['Severe X-linked myotubular myopathy'] |
| NM_000252.2(MTM1):<br>c.958T > C<br>(p.Ser320Pro) | 587783863 | MTM1 | [ ] | ['GGAAYCTTTAAA AAAAGTGAAGG'] | ['Severe X-linked myotubular myopathy'] |
| NM_000526.4(KRT14):<br>c.1151T > C<br>(p.Leu384Pro) | 59629244 | KRT14 | [ ] | [ ] | ['Epidermolysis bullosa simplex, Koebner type', 'not provided'] |
| NM_000249.3(MLH1):<br>c.453 + 2T > C | 267607751 | MLH1 | [ ] | [ATCACGGYAAG AATGGTACATGG', 'TCACGGYAAGAA TGGTACATGGG'] | ['Hereditary Nonpolyposis Colorectal Neoplasms'] |
| NM_002764.3(PRPS1):<br>c.455T > C<br>(p.Leu152Pro) | 80338676 | PRPS1 | [ ] | [ ] | ['Arts syndrome', 'not provided'] |
| NM_022132.4(MCCC2):<br>c.499T > C<br>(p.Cys167Arg) | 119103222 | MCCC2 | [ ] | [ ] | ['3-methylcrotonyl CoA carboxylase 2 deficiency'] |
| NM_000411.6(HLCS):<br>c.710T > C<br>(p.Leu237Pro) | 119103227 | HLCS | [ ] | ['CTATCYTTCTCA GGGAGGGAAGG'] | ['Holocarboxylase synthetase deficiency'] |
| NM_005787.5(ALG3):<br>c.211T > C<br>(p.Trp71Arg) | 119103237 | ALG3 | [ ] | MATTGACYGGA AGGCCTACATGG'] | ['Congenital disorder of glycosylation type 1D'] |
| NM_005609.2(PYGM):<br>c.1187T > C<br>(p.Leu396Pro) | 119103254 | PYGM | [ ] | [ ] | ['Glycogen storage disease, type V'] |
| m.3250T > C | 199474664 | MT-TL1 | [ ] | [ ] | [ ] |
| NM_002764.3(PRPS1):<br>:c.344T > C<br>(p.Met115Thr) | 80338732 | PRPS1 | ['GCAA ATAYG CTATC TGTAG CAGG'] | ['GCAAATAYGCT ATCTGTAGCAGG'] | [Charcot-Marie-Tooth disease, X-linked recessive, type 5'] |
| NM_003172.3(SURF1):<br>c.679T > C<br>(p.Trp227Arg) | 398122806 | SURF1 | [ ] | ['CCACYGGCATTA TCGAGACCTGG'] | ['Congenital myasthenic syndrome, acetazolamide-responsive'] |
| NM_004525.2(LRP2):<br>c.7564T > C<br>(p.Tyr2522His) | 80338747 | LRP2 | [ ] | ['GTACCTGYACTG GGCTGACTGGG'] | ['Donnai Barrow syndrome'] |
| NM_006329.3(FBLN5):<br>c.649T > C<br>(p.Cys217Arg) | 80338766 | FBLN5 | [ ] | [ ] | ['Autosomal recessive cutis laxa type IA'] |
| NM_001271723.1(FBXO38):<br>c.616T > C<br>(p.Cys206Arg) | 398122838 | FBXO38 | [ ] | ['TTCCTYGTATCC CAATGCTAAGG'] | ['Distal hereditary motor neuronopathy 2D'] |
| NM_133433.3(NIPBL):<br>c.7062 + 2T > C | 587784032 | NIPBL | [ ] | [ ] | ['Cornelia de Lange syndrome 1'] |
| NM_000334.4(SCN4A):<br>c.4468T > C<br>(p.Phe1490Leu) | 80338790 | SCN4A | [ ] | [ ] | ['Hyperkalemic Periodic Paralysis Type 1'] |
| NM_058216.2(RAD51C):<br>c.404 + 2T > C | 730881931 | RAD51C | [ ] | [ ] | ['Hereditary cancer-predisposing syndrome'] |
| NM_001111.4(ADAR):<br>c.2615T > C<br>(p.Ile872Thr) | 398122897 | ADAR | [ ] | [ ] | ['Aicardi-goutieres syndrome 6'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_005334.2(HCFC1): c.-970T > C | 398122908 | HCFC1 | ['CAAG AYGGC GGCTC CCAGG GAGG'] | ['CAAGAYGGCGG CTCCCAGGGAGG'] | ['Mental retardation 3, X-linked'] |
| NM_000431.3(MVK): c.1039 + 2T > C | 398122910 | MVK | ['CCAG GYATC CCGGG GGTAG GTGG'] | ['CCAGGYATCCCG GGGTAGGTGG', 'CAGGYATCCCGG GGGTAGGTGGG'] | ['Porokeratosis, disseminated superficial actinic 1'] |
| NM_000431.3(MVK): c.1094T > C (p.Phe365Ser) | 398122911 | MVK | [ ] | [ ] | ['Porokeratosis, disseminated superficial actinic 1'] |
| NM_005050.3(ABCD4): c.956A > G (p.Tyr319Cys) | 201777056 | ABCD4 | ['GATG AGGYA GATGC ACACA AAGG'] | ['GATGAGGYAGA TGCACACAAAGG'] | ['METHYLMALONIC ACIDURIA AND HOMOCYSTINURI A, cb1J TYPE', 'not provided'] |
| NM_000251.2(MSH2): c.2005 + 2T > C | 267607987 | MSH2 | ['CTGG YAAAA AACCT GGTTT TTGG', 'TGGYA AAAAA CCTGG TTTTTG GG'] | ['CTGGYAAAAAA CCTGGTTTTTGG', 'TGGYAAAAAACC TGGTTTTTGGG'] | ['Hereditary Nonpolyposis Colorectal Neoplasms'] |
| NM_000518.4(HBB): c.257T > C (p.Phe86Ser) | 35693898 | HBB | [ ] | [ ] | ['Hemoglobinopathy'] |
| NM_001194998.1(CEP152): c.3149T > C (p.Leu1050Pro) | 398122977 | CEP152 | [ ] | [ ] | ['Primary autosomal recessive microcephaly 9'] |
| NM_022455.4(NSD1): c.5989T > C (p.Tyr1997His) | 587784171 | NSD1 | [ ] | [ ] | ['Sotos syndrome 1'] |
| NM_014495.3(ANGPTL3): c.883T > C (p.Phe295Leu) | 398122989 | — | [ ] | ['ACAAAACYTCA ATGAAACGTGGG'] | ['Hypobetalipoprotei nemia, familial, 2'] |
| NM_024577.3(SH3TC2): c.1982T > C (p.Leu661Pro) | 80338927 | SH3TC2 | [ ] | [ ] | ['Charcot-Marie-Tooth disease, type 4C'] |
| NM_000551.3(VHL): c.227T > C (p.Phe76Ser) | 730882033 | VHL | [ ] | [ ] | ['Hereditary cancer-predisposing syndrome'] |
| NM_004004.5(GJB2): c.269T > C (p.Leu90Pro) | 80338945 | GJB2 | [ ] | ['GCTCCYAGTGGC CATGCACGTGG'] | ['Deafness, autosomal recessive 1A', 'Hearing impairment', 'not provided'] |
| NM_000334.4(SCN4A): c.2078T > C (p.Ile693Thr) | 80338956 | SCN4A | [ ] | ['AAGATCAYTGG CAATTCAGTGGG', 'AGATCAYTGGCA ATTCAGTGGGG', 'GATCAYTGGCAA TTCAGTGGGGG'] | ['Hyperkalemic Periodic Paralysis Type 1', 'Paramyotonia congenita of von Eulenburg'] |
| NM_004523.3(KIF11): c.2547 + 2T > C | 730882063 | KIF11 | ['GGAG GYAAT AACTT TGTAA GTGG'] | ['GGAGGYAATAA CTTTGTAAGTGG'] | ['Microcephaly with or without chorioretinopathy, lymphedema, or mental retardation'] |
| NM_003060.3(SLC22A5): c.1051T > C (p.Trp351Arg) | 68018207 | SLC22A5 | [ ] | [ ] | ['Renal carnitine transport defect'] |
| NM_001070.4(TUBG1): c.1160T > C (p.Leu387Pro) | 398123045 | TUBG1 | [ ] | [ ] | ['Cortical dysplasia, complex, with other brain malformations 4'] |
| NM_000441.1(SLC26A4): c.-103T > C | 60284988 | — | [ ] | [ ] | ['Pendred syndrome', 'Enlarged vestibular aqueduct syndrome'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000016.5(ACADM):<br>c.233T > C<br>(p.Ile78Thr) | 398123074 | ACADM | [ ] | [ ] | ['Medium-chain acyl-coenzyme A dehydrogenase deficiency', 'not provided'] |
| NM_000179.2(MSH6):<br>c.4001 + 2T > C | 267608131 | MSH6 | [ ] | [VGGYAACTAACT AACTATAATGG'] | ['Hereditary Nonpolyposis Colorectal Neoplasms'] |
| NM_000019.3(ACAT1):<br>c.730 + 2T > C | 398123096 | ACAT1 | [ ] | [ ] | ['Deficiency of acetyl-CoA acetyltransferase', 'not provided'] |
| NM_000430.3(PAFAH1B1):<br>c.841T > C<br>(p.Cys281Arg) | 587784288 | PAFAH1B1 | [ ] | [ ] | ['Lissencephaly 1'] |
| NM_000899.4(KITLG):<br>c.98T > C<br>(p.Val33Ala) | 730882156 | KITLG | [ ] | [ ] | ['Familial progressive hyperpigmentation with or without hypopigmentation'] |
| NM_015599.2(PGM3):<br>c.248T > C<br>(p.Leu83Ser) | 267608260 | PGM3 | ['AATG TYGGC ACCAT CCTGG GAGG'] | ['AATGTYGGCACC ATCCTGGGAGG'] | ['Immunodeficiency 23'] |
| NM_000169.2(GLA):<br>c.899T > C<br>(p.Leu300Pro) | 398123223 | — | [ ] | [ ] | ['Fabry disease'] |
| NM_001256047.1(C19orf12):<br>c.391A > G<br>(p.Lys131Glu) | 146170087 | C19orf12 | [ ] | [ ] | ['Neurodegeneration with brain iron accumulation 4'] |
| NM_172337.2(0TX2):<br>c.674A > G<br>(p.Asn225Ser) | 370761964 | OTX2 | [ ] | [ ] | ['Pituitary hormone deficiency, combined 6'] |
| NM_000202.6(IDS):<br>c.587T > C (p.Leu196Ser) | 398123250 | IDS | [ ] | [ ] | ['Mucopolysacchar idosis, MPS-II', 'not provided'] |
| NM_000252.2(MTM1):<br>c.688T > C<br>(p.Trp230Arg) | 398123274 | MTM1 | [ ] | [ ] | ['Severe X-linked myotubular myopathy', 'not provided'] |
| NM_022445.3(TPK1):<br>c.656A > G<br>(p.Asn219Ser) | 371271054 | TPK1 | [ ] | [ ] | ['THIAMINE METABOLISM DYSFUNCTION SYNDROME 5 (EPISODIC ENCEPHALOPATHY TYPE)'] |
| NM_014139.2(SCN11A):<br>c.2432T > C<br>(p.Leu811Pro) | 483352920 | SCN11A | [ ] | [ ] | ['NEUROPATHY, HEREDITARY SENSORY AND AUTONOMIC, TYPE VII'] |
| NM_000733.3(CD3E):<br>c.520 + 2T > C | 483352928 | CD3E | [ ] | [ ] | ['Immunodeficiency 18'] |
| NM_017653.3(DYM):<br>c.621-2A > G | 775414124 | DYM | [ ] | [ ] | ['Dyggve-Melchior-Clausen syndrome'] |
| NM_001253816.1(SL052A2):<br>c.1016T > C<br>(p.Leu339Pro) | 148234606 | 5LC52A2 | [ ] | [ ] | [Brown-Vialetto-Van Laere syndrome 2'] |
| NM_004963.3(GUCY2C):<br>c.2782T > C<br>(p.Cys928Arg) | 587784573 | — | [ ] | ['TCCCYGTGCTGC TGGAGTTGTGG', 'CCCYGTGCTGCT GGAGTTGTGGG'] | ['Meconium ileus'] |
| NM_003159.2(CDKL5):<br>c.659T > C<br>(p.Leu220Pro) | 267608511 | CDKL5 | [ ] | ['CCAACYTTTTAC TATTCAGAAGG'] | ['Early infantile epileptic encephalopathy 2'] |
| NM_000528.3(MAN2B1):<br>c.2436 + 2T > C | 398123457 | MAN2B1 | [ ] | [ ] | ['not provided'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_002136.2(HNRNPA1): c.841T > C (p.Phe281Leu) | 483353031 | HNRNPA1 | ['AATYTTGGAGGCAGAAGCTCTGG'] | ['AATYTTGGAGGCAGAAGCTCTGG'] | ['Chronic progressive multiple sclerosis'] |
| NM_006920.4(SCN1A): c.4251 + 2T > C | 398123595 | — | [ ] | [ ] | ['Severe myoclonic epilepsy in infancy', 'Generalized epilepsy with febrile seizures plus, type 2'] |
| NM_002225.3(IVD): c.465 + 2T > C | 398123683 | IVD | [ ] | [ ] | ['Isovaleryl-CoA dehydrogenase deficiency', 'not provided'] |
| NM_000118.3(ENG): c.1273-2A > G | 373842615 | ENG | [ ] | ['CCGCCYGCGGGGATAAAGCCAGG', 'CGCCYGCGGGGATAAAGCCAGGG'] | ['Haemorrhagic telangiectasia 1'] |
| NM_005859.4(PURA): c.218T > C (p.Phe73Ser) | 793888535 | PURA | [ ] | [ ] | ['not provided'] |
| NM_003494.3(DYSF): c.1284 + 2T > C | 398123765 | DYSF | ['ATGGYAAGGAGCAAGGGAGCAGG'] | ['ATGGYAAGGAGCAAGGGAGCAGG'] | ['Limb-girdle muscular dystrophy, type 2B', 'not provided'] |
| NM_004006.2(DMD): c.2380 + 2T > C | 398123885 | DMD | [ ] | [ ] | ['Dilated cardiomyopathy 3B'] |
| NM 006364.2(SEC23A): c.2104A > G (p.Met702Val) | 138568622 | SEC23A | [ ] | [ ] | ['Craniolenticulosutural dysplasia'] |
| NM_000335.4(SCN5A): c.376A > G (p.Lys126Glu) | 185492581 | SCN5A | [ ] | ['GAATCTYCACAGCCGCTCTCCGG'] | ['Brugada syndrome'] |
| NM_015865.6(SLC14Al): c.871T > C (p.Ser291Pro) | 78242949 | SLC14A1 | [ ] | [ ] | [ ] |
| NM_003995.3(NPR2): c.226T > C (p.Ser76Pro) | 796065355 | NPR2 | [ ] | [ ] | ['SHORT STATURE WITH NONSPECIFIC SKELETAL ABNORMALITIES'] |
| NM_012463.3(ATP6V0A2): c.825 + 2T > C | 398124257 | ATP6V0A2 | ['CACTGYGAGTAAGCTGGAAGTGG'] | ['CACTGYGAGTAAGCTGGAAGTGG'] | ['Cutis laxa with osteodystrophy', 'not provided'] |
| NM_014795.3(ZEB2): c.73 + 2T > C | 398124282 | ZEB2 | [ ] | [ ] | ['Mowat-Wilson syndrome'] |
| NM_000424.3(KRT5): c.1388T > C (p.Leu463Pro) | 57599352 | KRT5 | [ ] | [ ] | ['Epidermolysis bullosa simplex, Koebner type', 'not provided'] |
| NM_133499.2(SYN1): c.1699A > G (p.Thr567Ala) | 200533370 | SYN1 | [ ] | ['GATGYCTGACGGGTAGCCTGTGG', 'ATGYCTGACGGGTAGCCTGTGGG'] | ['Epilepsy, X-linked, with variable learning disabilities and behavior disorders', 'not specified'] |
| NM_148960.2(CLDN19): c.269T > C (p.Leu90Pro) | 118203981 | CLDN19 | [ ] | ['GCTCCYGGGCTTCGTGGCCATGG'] | ['Hypomagnesemia 5, renal, with ocular involvement'] |
| NM_018006.4(TRMU): c.229T > C (p.Tyr77His) | 118203990 | TRMU | [ ] | [ ] | ['Liver failure acute infantile'] |
| NM_000056.3(BCKDHB): c.752T > C (p.Val251Ala) | 398124593 | BCKDHB | [ ] | [ ] | ['Maple syrup urine disease', 'not provided'] |
| NM_182680.1(AMELX): c.2T > C (p.Met1Thr) | 104894737 | — | [ ] | [ ] | ['Amelogenesis imperfecta, type 1E'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_018105.2(THAP1): c.241T > C (p.Phe81Leu) | 118204013 | THAP1 | [ ] | [ ] | ['Dystonia 6, torsion'] |
| NM_001235.3(SERPINH1): c.233T > C (p.Leu78Pro) | 137853892 | SERPINH1 | [ ] | ['GTCGCYAGGGCT CGTGTCGCTGG', 'TCGCYAGGGCTC GTGTCGCTGGG'] | ['Osteogenesis imperfecta type 10'] |
| NM_004482.3(GALNT3): c.516_688del | 761396172 | GALNT3 | [ ] | [ ] | ['Tumoral calcinosis, familial, hyperphosphatemic'] |
| NM_000263.3(NAGLU): c.142T > C (p.Phe48Leu) | 118204024 | NAGLU | [ ] | ['GGCCGACYTCTC CGTGTCGGTGG'] | ['Mucopolysaccharid osis, MPS-III-B'] |
| NM_000559.2(HBG1): c.-251T > C | 35710727 | HBG1 | [ ] | [ ] | ['Fetal hemoglobin quantitative trait locus 1'] |
| NM_000527.4(LDLR): c.694 + 2T > C | 200238879 | LDLR | ['CGGY ATGGG CGGGG CCAGG GTGG'] | ['ACTGCGGYATG GGCGGGGCCAGG', 'CTGCGGYATGGG CGGGGCCAGGG', 'CGGYATGGGCGG GGCCAGGGTGG'] | ['Familial hypercholesterolemia'] |
| NM_001012515.2(FECH): c.1268T > C (p.Phe423Ser) | 118204039 | FECH | [ ] | [ ] | ['Erythropoietic protoporphyria'] |
| NM_005211.3(CSF1R): c.1745T > C (p.Leu582Pro) | 690016563 | CSF1R | [ ] | ['CAACCYGCAGTT TGGTGAGATGG'] | ['Hereditary diffuse leukoencephalopathy with spheroids'] |
| NM_000526.4(KRT14): c.1243T > C (p.Tyr415His) | 58380626 | KRT14 | [ ] | ['CGCCACCYACCG CCGCCTGCTGG', 'CACCYACCGCCG CCTGCTGGAGG', 'ACCYACCGCCGC CTGCTGGAGGG'] | ['Epidermolysis bullosa herpetiformis, Dowling-Meara', 'not provided'] |
| NM_006493.2(CLN5): c.2T > C (p.Met1Thr) | 201615354 | CLN5 | [ ] | [ ] | ['not provided'] |
| NM_002863.4(PYGL): c.2461T > C (p.Tyr821His) | 113993988 | PYGL | ['AAGA AYATG CCCAA AACAT CTGG'] | ['AAGAAYATGCC CAAAACATCTGG'] | ['Glycogen storage disease, type VI'] |
| NM_016038.2(SBDS): c.258 + 2T > C | 113993993 | SBDS | [ ] | [ ] | ['Shwachman syndrome', 'Aplastic anemia, susceptibility to'] |
| NM_000110.3(DPYD): c.85T > C (p.Cys29Arg) | 1801265 | DPYD | [ ] | [ ] | ['Dihydropyrimidine dehydrogenase deficiency'] |
| NM_001034116.1(EIF2B4): c.1393T > C (p.Cys465Arg) | 113994038 | EIF2B4 | [ ] | [ ] | ['Ovarioleukodystrophy'] |
| NM_001165963.1(SCN1A): c.323T > C (p.Leu108Pro) | 794726793 | SCN1A | [ ] | [ ] | ['Severe myoclonic epilepsy in infancy'] |
| NM_001034116.1(EIF2B4): c.1465T > C (p.Tyr489His) | 113994040 | EIF2B4 | [ ] | [ ] | ['Ovarioleukodystrophy'] |
| NM_004304.4(ALK): c.3749T > C (p.Ile1250Thr) | 113994092 | ALK | [ ] | [ ] | ['Neuroblastoma 3'] |
| NM_207346.2(TSEN54): c.277T > C (p.Ser93Pro) | 113994151 | TSEN54 | [ ] | ['TTGAAGYCTCCC GCGGTGAGCGG', 'AAGYCTCCCGCG GTGAGCGGCGG'] | ['Pontocerebellar hypoplasia type 4'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000018.3(ACADVL): c.848T > C (p.Val283Ala) | 113994167 | ACADVL | ['TTTGYGGTGGAGAGGGGCTTCGG', 'TTGYGGTGGAGAGGGCTTCGG'] | ['TTTGYGGTGGAGAGGGGCTTCGG', 'TTGYGGTGGAGAGGGGCTTCGG'] | ['Very long chain acyl-CoA dehydrogenase deficiency', 'not provided'] |
| NM_000430.3(PAFAH1B1): c.569-10T > C | 113994202 | PAFAH1B1 | [ ] | [ ] | ['Lissencephaly 1'] |
| NM_004937.2(CTNS): c.473T > C (p.Leu158Pro) | 113994206 | CTNS | [ ] | ['TGGTCYGAGCTTCGACTTCGTGG'] | ['Cystinosis'] |
| NM_000546.5(TP53): c.488A > G (p.Tyr163Cys) | 148924904 | TP53 | ['GCTTGYAGATGGCCATGGCGCGG'] | ['GCTTGYAGATGGCCATGGCGCGG'] | ['Hereditary cancer-predisposing syndrome'] |
| NM_004211.3(SLC6A5): c.1444T > C (p.Trp482Arg) | 281864925 | SLC6A5 | [ ] | [ ] | ['Hyperekplexia 3'] |
| NM_024312.4(GNPTAB): c.1208T > C (p.Ile403Thr) | 281864973 | GNPTAB | [ ] | [ ] | ['Pseudo-Hurler polydystrophy'] |
| NM_024312.4(GNPTAB): c.3002T > C (p.Leu1001Pro) | 281865006 | GNPTAB | [ ] | [ ] | ['I cell disease'] |
| NM_000540.2(RYR1): c.7358T > C (p.Ile2453Thr) | 118192123 | RYR1 | [ ] | [ ] | ['Central core disease', 'not provided'] |
| NM_000748.2(CHRNB2): c.923T > C (p.Val308Ala) | 281865070 | CHRNB2 | [ ] | [ ] | ['Epilepsy, nocturnal frontal lobe, type 3'] |
| NM_000526.4(KRT14): c.356T > C (p.Met119Thr) | 28928893 | KRT14 | [ ] | [ ] | ['Epidermolysis bullosa herpetiformis, Dowling-Meara', 'not provided'] |
| NM_000093.4(COL5A1): c.5137-11T > A | 183495554 | — | [ ] | [ ] | ['Ehlers-Danlos syndrome, classic type'] |
| NM_000277.1(PAH): c.638T > C (p.Leu213Pro) | 62516109 | PAH | [ ] | [CCACTTCYTGAAAAGTACTGTGG'] | ['Phenylketonuria', 'not provided'] |
| NM_000531.5 (OTC): c.663 + 2T > C | 72558427 | OTC | [ ] | [ ] | ['not provided'] |
| NM_000531.5 (OTC): c.717 + 2T > C | 72558431 | OTC | [ ] | [ ] | [Ornithine carbamoyltransferase deficiency', 'not provided'] |
| NM_000531.5 (OTC): c.793T > C (p.Trp265Arg) | 72558445 | OTC | [ ] | [ ] | ['not provided'] |
| NM_000493.3(COL10A1): c.1841T > C (p.Leu614Pro) | 111033545 | — | [ ] | [ ] | ['Metaphyseal chondrodysplasia, Schmid type'] |
| NM_000493.3(COL10A1): c.1771T > C (p.Cys591Arg) | 111033546 | — | [ ] | [ ] | ['Metaphyseal chondrodysplasia, Schmid type'] |
| NM_000493.3(COL10A1): c.2011T > C (p.Ser671Pro) | 111033552 | — | [ ] | [ ] | ['Metaphyseal chondrodysplasia, Schmid type'] |
| NM_004614.4(TK2): c.173A > G (p.Asn58Ser) | 138439950 | TK2 | [ ] | [ ] | ['Mitochondrial DNA depletion syndrome 2'] |
| NM_004614.4(TK2): c.644T > C (p.Leu215Pro) | 281865497 | TK2 | [ ] | [ ] | ['Mitochondrial DNA depletion syndrome 2'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_004614.4(TK2): c.156 + 2T > C | 281865499 | TK2 | [ ] | [ ] | ['Mitochondrial DNA depletion syndrome 2'] |
| NM_153026.2(PRICKLE1): c.1414T > C (p.Tyr472His) | 281865564 | PRICKLE1 | [ ] | [ ] | ['Progressive myoclonus epilepsy with ataxia'] |
| NM_017882.2(CLN6): c.767A > G (p.Asp256Gly) | 143781303 | CLN6 | [ ] | [ ] | ['not provided'] |
| NM_130838.1(UBE3A): c.389T > C (p.Ile130Thr) | 111033597 | UBE3A | [ ] | [ ] | ['Angelman syndrome'] |
| NM_001198799.2(ASCC1): c.953A > G (p.Asn318Ser) | 146370051 | ASCC1 | [ ] | [ ] | [ ] |
| NM_000174.4(GP9): c.70T > C (p.Cys24Arg) | 28933378 | GP9 | ['CCCAYGTACCTGCCGCGCCCTGG'] | [VCCAYGTACCTGCCGCGCCCTGG] | ['Bernard Soulier syndrome', 'Bernard-Soulier syndrome type C'] |
| NM_001173464.1(KIF21A): c.3029T > C (p.Ile1010Thr) | 121912587 | KIF21A | [ ] | [ ] | ['Fibrosis of extraocular muscles, congenital, 1'] |
| NM_001302946.1(TRNT1): c.668T > C (p.Ile223Thr) | 370011798 | TRNT1 | [ ] | ['GCAAYTGCAGAAAATGCAAAAGG'] | ['Sideroblastic anemia with B-cell immunodeficiency, periodic fevers, and developmental delay'] |
| NM_000371.3(TTR): c.250T > C (p.Phe84Leu) | 121918091 | TTR | [ ] | [ ] | ['Amyloidogenic transthyretin amyloidosis'] |
| m.5814T > C | 200077222 | MT-TC | [ ] | [ ] | ['Juvenile myopathy, encephalopathy, lactic acidosis AND stroke'] |
| NM_000277.1(PAH): c.293T > C (p.Leu98Ser) | 62517167 | PAH | [ ] | ['AAGATCTYGAGGCATGACATTGG'] | ['Mild non-PKU hyperphenylalanemia', 'not provided'] |
| NM_017882.2(CLN6): c.486 + 2T > C | 796052355 | CLN6 | [ ] | [ ] | ['not provided'] |
| NM_001813.2(CENPE): c.4063A > G (p.Lys1355Glu) | 141488085 | CENPE | [ ] | [ ] | ['Primary autosomal recessive microcephaly 13'] |
| NM_001918.3(DBT): c.1150G > A (p.Gly384Ser) | 12021720 | DBT | [ ] | ['GACYCACAGAGCCCAATTTCTGG'] | ['Intermediate maple syrup urine disease type 2'] |
| NM_000495.4(COL4A5): c.4699T > C (p.Cys1567Arg) | 104886288 | COL4A5 | ['AGTAYGTGAAGCTCCAGCTGTGG'] | ['AGTAYGTGAAGCTCCAGCTGTGG'] | ['Alport syndrome, X-linked recessive'] |
| NM_000495.4(COL4A5): c.4756T > C (p.Cys1586Arg) | 104886289 | COL4A5 | [ ] | ['TCCCCATYGTCCTCAGGGATGGG'] | ['Alport syndrome, X-linked recessive'] |
| NM_000495.4(COL4A5): c.5032T > C (p.Cys1678Arg) | 104886310 | COL4A5 | [ ] | [ ] | ['Alport syndrome, X-linked recessive'] |
| NM_000155.3(GALT): c.482T > C (p.Leu161Pro) | 111033700 | GALT | ['AGCYGGGTGCCCAGTACCCTTGG'] | ['AGCYGGGTGCCCAGTACCCTTGG'] | ['Deficiency of UDPglucose-hexose-1-phosphate uridylyltransferase'] |
| NM_001199252.2(SGOL1): c.67A > G (p.Lys23Glu) | 199815268 | — | [ ] | [ ] | ['Chronic atrial and intestinal dysrhythmia'] |
| NC_012920.1:m.5559 A > G | 370471013 | MT-TW | [ ] | ['CAACYTACTGAGGGCTTTGAAGG'] | ['Leigh disease'] |
| NM_000487.5(ARSA): c.410T > C (p.Leu137Pro) | 121434215 | ARSA | [ ] | ['GCCTTCCYGCCCCCCATCAGGG'] | ['Metachromatic leukodystrophy, adult type'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000051.3(ATM): c.7967T > C (p.Leu2656Pro) | 121434218 | — | [ ] | [ ] | [ ] |
| NM_000096.3(CP): c.650T > C (p.Phe217Ser) | 386134125 | CP | [ ] | [ ] | ['Deficiency of ferroxidase'] |
| NM_000096.3(CP): c.1123T > C (p.Tyr375His) | 386134128 | CP | [ ] | ['ACACTACYACAT TGCCGCTGAGG'] | ['Deficiency of ferroxidase'] |
| NM_000268.3(NF2): c.185T > C (p.Phe62Ser) | 121434261 | NF2 | [ ] | [ ] | ['Neurofibromatosis, type 2'] |
| NM_000495.4(COL4A5): c.4803 + 121T > C | 104886423 | COL4A5 | [ ] | [ ] | ['Alport syndrome, X-linked recessive'] |
| NM_024529.4(CDC73): c.191T > C (p.Leu64Pro) | 121434264 | CDC73 | [ ] | [ ] | ['Hyperparathyroidism 1'] |
| NM_001061.4(TBXAS1): c.1463T > C (p.Leu488Pro) | 199422114 | TBXAS1 | [ ] | [ ] | [ ] |
| NM_001127328.2(ACADM): c.1136T > C (p.Ile379Thr) | 121434275 | ACADM | [ ] | ['GTGCAGAYACTT GGAGGCAATGG'] | ['Medium-chain acyl-coenzyme A dehydrogenase deficiency'] |
| NM_001127328.2(ACADM): c.742T > C (p.Cys248Arg) | 121434276 | ACADM | [ ] | [CAGCGAYGTTCA GATACTAGAGG] | ['Medium-chain acyl-coenzyme A dehydrogenase deficiency'] |
| NM_000016.5(ACADM): c.199T > C (p.Tyr67His) | 121434280 | ACADM | [ ] | [ ] | ['Medium-chain acyl-coenzyme A dehydrogenase deficiency', 'not provided'] |
| NM_002225.3(IVD): c.134T > C (p.Leu45Pro) | 121434284 | IVD | [ ] | [ATGGGCYAAGC GAGGAGCAGAGG] | ['ISOVALERIC ACIDEMIA, TYPE I'] |
| NM_005957.4(MTHFR): c.968T > C (p.Leu323Pro) | 121434297 | MTHFR | [ ] | [ ] | ['Homocystinuria due to MTHFR deficiency'] |
| NM_000136.2(FANCC): c.1661T > C (p.Leu554Pro) | 104886458 | — | [ ] | [ ] | ['Fanconi anemia, complementation group C', 'not provided'] |
| NM_005908.3(MANBA): c.1513T > C (p.Ser505Pro) | 121434334 | MANBA | [ ] | ['ATTACGYCCAGT CCTACAAATGG', 'TTACGYCCAGTC CTACAAATGGG', 'TACGYCCAGTCC TACAAATGGGG'] | [Beta-D-mannosidosis] |
| NM_000244.3(MEN1): c.518T > C (p.Leu173Pro) | 386134256 | MEN1 | [ ] | [ ] | ['Multiple endocrine neoplasia, type 1'] |
| NM_199242.2(UNC13D): c.1208T > C (p.Leu403Pro) | 121434353 | UNC13D | [ ] | [ ] | ['Hemophagocytic lymphohistiocytosis, familial, 3'] |
| NM_152783.4(D2HGDH): c.1331T > C (p.Val444Ala) | 121434360 | D2HGDH | [ ] | [ ] | ['D-2-hydroxyglutaric aciduria 1'] |
| NM_207118.2(GTF2H5): c.62T > C (p.Leu21Pro) | 121434365 | GTF2H5 | [ ] | [ ] | ['Photosensitive trichothiodystrophy'] |
| NM_000159.3(GCDH): c.883T > C (p.Tyr295His) | 121434366 | GCDH | [ ] | ['CGCCCGGYACG GCATCGCGTGGG', 'GCCCGGYACGGC ATCGCGTGGGG'] | ['Glutaric aciduria, type 1'] |
| NM_018668.4(VPS33B): c.89T > C (p.Leu30Pro) | 121434385 | VPS33B | [ ] | [ ] | ['Arthrogryposis renal dysfunction cholestasis syndrome'] |
| NM_000424.3(KRT5): c.541T > C (p.Ser181Pro) | 60715293 | KRT5 | [ ] | [GTTTGCCYCCTT CATCGACAAGG] | ['Epidermolysis bullosa herpetiformis, Dowling-Meara', 'not provided'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_001003722.1(GLE1): c.2051T > C (p.Ile684Thr) | 121434409 | GLE1 | [ ] | ['AAGGACAYTCCT GTCCCCAAGGG'] | ['Lethal arthrogryposis with anterior horn cell disease'] |
| NM_003659.3(AGPS): c.1406T > C (p.Leu469Pro) | 121434413 | AGPS | [ ] | [ ] | ['Rhizomelic chondrodysplasia punctata type 3'] |
| NM_004550.4(NDUFS2): c.1237T > C (p.Ser413Pro) | 121434429 | NDUFS2 | [ ] | [ ] | ['Mitochondrial complex I deficiency', 'not provided'] |
| NM_001287.5(CLCN7): c.2297T > C (p.Leu766Pro) | 121434434 | CLCN7 | [ ] | ['GGGCCYGCGGC ACCTGGTGGTGG'] | ['Osteopetrosis autosomal recessive 4'] |
| m.14709T > C | 121434453 | MT-TE | [ ] | [ ] | ['Diabetes-deafness syndrome maternally transmitted'] |
| NM_000466.2(PEX1): c.1991T > C (p.Leu664Pro) | 121434455 | PEX1 | [ ] | ['GATGACCYTGAC CTCATTGCTGG'] | ['Zellweger syndrome'] |
| NM_198253.2(TERT): c.3043T > C (p.Cys1015Arg) | 199422307 | TERT | [ ] | [ ] | ['Aplastic anemia'] |
| m.4290T > C | 121434469 | MT-TI | ['ACTYT GATAG AGTAA ATAAT AGG'] | ['ACTYTGATAGAG TAAATAATAGG'] | [ ] |
| m.4291T > C | 121434471 | MT-TI | ['ACTTY GATAG AGTAA ATAAT AGG'] | ['ACTTYGATAGAG TAAATAATAGG'] | ['Hypertension, hypercholesterolemia, and hypomagnesemia, mitochondrial'] |
| m.9997T > C | 121434475 | MT-TG | [ ] | [ ] | ['Primary familial hypertrophic cardiomyopathy'] |
| NM_001099274.1(TINF2): c.860T > C (p.Leu287Pro) | 199422316 | TINF2 | [ ] | [ ] | ['Dyskeratosis congenita autosomal dominant'] |
| NM_001099274.1(TINF2): c.862T > C (p.Phe288Leu) | 199422317 | TINF2 | [ ] | ['CTGYTTCCCTTT AGGAATCTCGM | ['Aplastic anemia'] |
| NM_000430.3(PAFAH1B1): c.505T > C (p.Ser169Pro) | 121434484 | PAFAH1B1 | [ ] | [ ] | ['Subcortical band heterotopia'] |
| NM_000430.3(PAFAH1B1): c.92T > C (p.Phe31Ser) | 121434486 | PAFAH1B1 | [ ] | [ ] | ['Lissencephaly 1'] |
| NM_005535.2(IL12RB1): c.592T > C (p.Cys198Arg) | 121434495 | IL12RB1 | [ ] | [ ] | ['Immunodeficiency 301] |
| NM_030662.3(MAP2K2): c.400T > C (p.Tyr134His) | 121434499 | MAP2K2 | [ ] | [ ] | ['Cardiofaciocutaneo us syndrome 4', 'Rasopathy', 'Noonan syndrome and Noonan-related syndrome'] |
| NM_001065.3(TNFRSF1A): c.349T > C (p.Cys117Arg) | 104895221 | TNFRSF1A | [ ] | ['CTCTTCTYGCAC AGTGGACCGGG'] | ['TNF receptor-associated periodic fever syndrome (TRAPS)'] |
| NM_000123.3(ERCC5): c.2573T > C (p.Leu858Pro) | 121434575 | — | [ ] | [ ] | ['Xeroderma pigmentosum, group G'] |
| NM_001493.2(GDI1): c.275T > C (p.Leu92Pro) | 121434607 | GDI1 | [ ] | [ ] | ['X-Linked Mental Retardation 41'] |
| NM_020061.5(OPN1LW): c.607T > C (p.Cys203Arg) | 121434621 | OPN1LW | [ ] | [ ] | ['Cone monochromatism'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_024420.2(PLA2G4A): c.331T > C (p.Ser111Pro) | 121434634 | PLA2G4A | [ ] | [ ] | [ ] |
| NM_005557.3(KRT16): c.395T > C (p.Leu132Pro) | 60944949 | KRT16 | [ ] | [ ] | ['Pachyonychia congenita, type 1', 'not provided'] |
| NM_000485.2(APRT): c.407T > C (p.Met136Thr) | 28999113 | APRT | [ ] | [ ] | ['Adenine phosphoribosyltransferase deficiency', 'APRT deficiency, Japanese type'] |
| NM_005270.4(GLI2): c.4663T > C (p.Ser1555Pro) | 144372453 | GLI2 | [ ] | [ ] | ['Holoprosencephaly 9', 'not specified'] |
| NM_024753.4(TTC21B): c.2384T > C (p.Leu795Pro) | 387907060 | TTC21B | [ ] | [ ] | ['Asphyxiating thoracic dystrophy 4'] |
| NM_000155.3(GALT): c.680T > C (p.Leu227Pro) | 111033846 | GALT | [ ] | [ ] | ['Deficiency of UDPglucose-hexose-1-phosphate uridylyltransferase'] |
| NM_000138.4(FBN1): c.4987T > C (p.Cys1663Arg)10): | 137854459 | FBN1 | [ ] | ['GGGACAYGTTA CAACACCGTTGG'] | ['Marfan syndrome'] |
| NM_032446.2(MEGF c.976T > C (p.Cys326Arg) | 387907073 | MEGF10 | [ ] | [ ] | ['Myopathy, areflexia, respiratory distress, and dysphagia, early-onset, mild variant'] |
| NM_024027.4(COLEC11): c.505T > C (p.Ser169Pro) | 387907075 | COLEC11 | [ ] | [CAGCTGYCCTGC CAGGGGCCGCGG', 'AGCTGYCCTGCC AGGGCCGCGGG', 'GCTGYCCTGCCA GGGCCGCGGGG', 'CTGYCCTGCCAG GGCCGCGGGGG'] | ['Carnevale syndrome'] |
| NM_001946.3(DUSP6): c.566A > G (p.Asn189Ser) | 143946794 | DUSP6 | ['CACT AYTGG GGTCT CGGTC AAGG'] | ['CACTAYTGGGGT CTCGGTCAAGG'] | ['Hypogonadotropic hypogonadism 19 with or without anosmia'] |
| NM_000138.4(FBN1): c.3793T > C (p.Cys1265Arg) | 137854474 | FBN1 | ['CTTGY GTTAT GATGG ATTCA TGG'] | ['CTTGYGTTATGA TGGATTCATGG'] | ['Marfan syndrome'] |
| NM_022068.3(PIEZO2): c.2134A > G (p.Met712Val) | 587777453 | PIEZO2 | [ ] | [ ] | ['Oculomelic amyoplasia'] |
| NM_000570.4(FCGR3B): c.316A= (p.Ile106=) | 2290834 | FCGR3B | [ ] | [ ] | [ ] |
| NM_000352.4(ABCC8): c.674T > C (p.Leu225Pro) | 1048095 | ABCC8 | [ ] | ['TGCYGTCCAAAG GCACCTACTGG'] | ['Permanent neonatal diabetes mellitus'] |
| NM_153490.2(KRT13): c.332T > C (p.Leu111Pro) | 59897026 | KRT13 | [ ] | [ ] | ['White sponge nevus 2', 'not provided'] |
| NM_000132.3(F8): c.1174T > C (p.Ser392Pro) | 28933669 | F8 | [ ] | [ ] | ['Hereditary factor VIII deficiency disease'] |
| NM_000492.3(CFTR): c.1021T > C (p.Ser341Pro) | 397508144 | CFTR | [ ] | [ ] | ['Cystic fibrosis'] |
| NM_000133.3(F9): c.1058T > C (p.Val353Ala) | 137852255 | F9 | [ ] | [ ] | ['Hereditary factor IX deficiency disease'] |
| NM_001202.3(BMP4): c.362A > G (p.His121Arg) | 376960358 | BMP4 | ['TTCGT GGYGG AAGCT CCTCA CGG'] | ['TTCGTGGYGGAA GCTCCTCACGG'] | ['Microphthalmia syndromic 6'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000133.3(F9): c.1328T > C (p.Ile443Thr) | 137852268 | F9 | ['GAAYATATACCAAGGTATCCCGG'] | ['GAAYATATACCAAGGTATCCCGG'] | ['Hereditary factor IX deficiency disease'] |
| NM_000133.3(F9): c.1357T > C (p.Trp453Arg) | 137852269 | F9 | [ ] | [ ] | ['Hereditary factor IX deficiency disease'] |
| NM_000435.2(NOTCH3): c.1363T > C (p.Cys455Arg) | 28933698 | NOTCH3 | ['ACCYGTATCTGTATGGCAGGTGG'] | ['TTCACCYGTATCTGTATGGCAGG', 'ACCYGTATCTGTATGGCAGGTGG'] | ['Cerebral autosomal dominant arteriopathy with subcortical infarcts and leukoencephalopath 3'] |
| NM_019074.3(DLL4): c.1168T > C (p.Cys390Arg) | 796065347 | DLL4 | [ ] | ['GAAYGTCCCCCCAACTTCACCGG'] | ['Adams-Oliver syndrome', 'ADAMS-OLIVER SYNDROME 6'] |
| NM_000032.4(ALAS2): c.595T > C (p.Tyr199His) | 137852310 | ALAS2 | [ ] | [ ] | ['Hereditary sideroblastic anemia'] |
| NM_019074.3(DLL4): c.583T > C (p.Phe195Leu) | 796065351 | DLL4 | [ ] | [ ] | ['Adams-Oliver syndrome'] |
| NM_000402.4(G6PD): c.1054T > C (p.Tyr352His) | 137852347 | G6PD | [ ] | ['AGGGYACCTGGACGACCCCACGG'] | ['Anemia, nonspherocytic hemolytic, due to G6PD deficiency'] |
| NM_007325.4(GRIA3): c.2117T > C (p.Met706Thr) | 137852352 | GRIA3 | [ ] | [ ] | ['Mental retardation, X-linked, syndromic, wu type'] |
| NM_000132.3(F8): c.6554T > C (p.Leu2185Ser) | 137852365 | F8 | [ ] | [ ] | ['Hereditary factor VIII deficiency disease'] |
| NM_000132.3(F8): c.5372T > C (p.Met1791Thr) | 137852375 | F8 | ['TCAYGGTGAGTTAAGGACAGTGG'] | ['TCAYGGTGAGTTAAGGACAGTGG'] | ['Hereditary factor VIII deficiency disease'] |
| NM_000132.3(F8): c.1754T > C (p.Ile585Thr) | 137852376 | F8 | ['AACAGAYAATGTCAGACAAGAGG'] | ['AACAGAYAATGTCAGACAAGAGG'] | ['Hereditary factor VIII deficiency disease'] |
| NM_001127695.1(CTSA): c.707T > C (p.Leu236Pro) | 137854546 | CTSA | [ ] | [ ] | ['Galactosialidosis, early infantile'] |
| NM_000132.3(F8): c.935T > C (p.Phe312Ser) | 137852405 | F8 | [ ] | [ ] | ['Hereditary factor VIII deficiency disease'] |
| NM_000132.3(F8): c.980T > C (p.Leu327Pro) | 137852407 | F8 | [ ] | [ ] | ['Hereditary factor VIII deficiency disease'] |
| NM_000308.2(CTSA): c.1271T > C (p.Met424Thr) | 137854548 | CTSA | [ ] | [ ] | ['Galactosialidosis, late infantile'] |
| NM_000132.3(F8): c.1481T > C (p.Ile494Thr) | 137852413 | F8 | [ ] | [ ] | ['Hereditary factor VIII deficiency disease'] |
| NM_001250.5(CD40): c.247T > C (p.Cys83Arg) | 28931586 | CD40 | [ ] | [ ] | ['Immunodeficiency with hyper IgM type 3'] |
| NM_000165.4(GJA1): c.32T > C (p.Leu11Pro) | 121912969 | GJA1 | [ ] | [ ] | ['Oculodentodigital dysplasia'] |
| NM_000132.3(F8): c.1958T > C (p.Val653Ala) | 137852430 | F8 | [ ] | [ ] | ['Hereditary factor VIII deficiency disease'] |
| NM_001972.2(ELANE): c.211T > C (p.Cys71Arg) | 28931611 | ELANE | [ ] | [ ] | ['Severe congenital neutropenia autosomal dominant'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000098.2(CPT2): c.1342T > C (p.Phe448Leu) | 74315297 | CPT2 | [ ] | [ ] | ['CARNITINE PALMITOYLTRA NSFERASE II DEFICIENCY, LATE-ONSET', 'not provided'] |
| NM_213653.3(HFE2): c.842T > C (p.Ile281Thr) | 74315326 | HFE2 | [ ] | [ ] | ['Hemochromatosis type 2A'] |
| NM_213653.3(HFE2): c.302T > C (p.Leu101Pro) | 74315327 | HFE2 | [ ] | ['GGACCYCGCCTT CCATTCGGCGG'] | ['Hemochromatosis type 2A'] |
| NM_000194.2(HPRT1): c.122T > C (p.Leu41Pro) | 137852480 | HPRT1 | [ ] | [ ] | ['Lesch-Nyhan syndrome'] |
| NM_000261.1(MY0C): c.1297T > C (p.Cys433Arg) | 74315338 | MYOC | [ ] | [ ] | ['Primary open angle glaucoma juvenile onset 1'] |
| NM_000194.2(HPRT1): c.170T > C (p.Met57Thr) | 137852495 | HPRT1 | [ ] | [ ] | ['Lesch-nyhan syndrome, neurologic variant'] |
| NM_000267.3(NF1): c.3728T > C (p.Leu1243Pro) | 137854564 | NF1 | [ ] | [ ] | ['Neurofibromatosis, type 1'] |
| NM_000291.3(PGK1): c.263T > C (p.Leu88Pro) | 137852531 | PGK1 | [ ] | [ ] | ['Phosphoglycerate kinase 1 deficiency'] |
| NM_000291.3(PGK1): c.946T > C (p.Cys316Arg) | 137852533 | PGK1 | [ ] | [ ] | ['Phosphoglycerate kinase 1 deficiency'] |
| NM_000291.3(PGK1): c.758T > C (p.Ile253Thr) | 137852534 | PGK1 | [ ] | [ ] | ['Phosphoglycerate kinase 1 deficiency'] |
| NM_170784.2(MKKS): c.830T > C (p.Leu277Pro) | 74315398 | MKKS | [ ] | [ ] | ['Bardet-Biedl syndrome 6', 'not provided'] |
| NM_000451.3(SHOX): c.877T > C (p.Ter293Arg) | 137852559 | SHOX | [ ] | [ ] | [Leri Weill dyschondrosteosis'] |
| NM_001029871.3(RSPO4): c.319T > C (p.Cys107Arg) | 74315421 | RSPO4 | [ ] | [ ] | ['Anonychia'] |
| NM_000044.3(AR): c.2033T > C (p.Leu678Pro) | 137852579 | AR | [ ] | ['GTCCYGGAAGC CATTGAGCCAGG'] | [ ] |
| NM_000044.3(AR): c.2423T > C (p.Met808Thr) | 137852592 | AR | [ ] | [ ] | ['Reifenstein syndrome'] |
| NM_000044.3(AR): c.2596T > C (p.Ser866Pro) | 137852597 | AR | [ ] | [ ] | ['Androgen resistance syndrome'] |
| NM_172201.1(KCNE2): c.161T > C (p.Met54Thr) | 74315447 | KCNE2 | [ ] | [ ] | ['Long QT syndrome 6', 'Congenital long QT syndrome', 'Cardiac arrhythmia'] |
| NM_172201.1(KCNE2): c.170T > C (p.Ile57Thr) | 74315448 | KCNE2 | [ ] | [ ] | ['Long QT syndrome 6', 'Cardiac arrhythmia', 'not provided'] |
| NM_000211.4(ITGB2): c.446T > C (p.Leu149Pro) | 137852611 | ITGB2 | ['AGCY AGGTG GCGAC CTGCT CCGG'] | ['AGCYAGGTGGC GACCTGCTCCGG'] | ['Leukocyte adhesion deficiency'] |
| NM_000211.4(ITGB2): c.412T > C (p.Ser138Pro) | 137852617 | ITGB2 | [ ] | [ ] | ['Leukocyte adhesion deficiency'] |
| NM_000023.2(SGCA): c.524T > C (p.Val175Ala) | 137852622 | SGCA | [ ] | [ ] | ['Limb-girdle muscular dystrophy, type 2D'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_001166107.1(HMGCS2): c.520T > C (p.Phe174Leu) | 137852636 | HMGCS2 | [ ] | ['CCCTCYTCAATG CTGCCAACTGG'] | ['mitochondrial 3-hydroxy-3-methylglutaryl-CoA synthase deficiency'] |
| NM_001886.2(CRYBA4): c.281T > C (p.Phe94Ser) | 74315486 | CRYBA4 | [ ] | [ ] | ['Cataract 23'] |
| NM_001886.2(CRYBA4): c.206T > C (p.Leu69Pro) | 74315487 | CRYBA4 | [ ] | [ ] | ['Cataract 23'] |
| NM_002047.2(GARS): c.548T > C (p.Leu183Pro) | 137852644 | GARS | [ ] | [ ] | ['Distal hereditary motor neuronopathy type 5'] |
| NM_000268.3(NF2): c.1604T > C (p.Leu535Pro) | 74315493 | NF2 | [ ] | [ ] | ['Neurofibromatosis, type 2'] |
| NM_000095.2(COMP): c.982T > C (p.Cys328Arg) | 137852653 | COMP | [ ] | [ ] | ['Pseudo-achondroplastic spondyloepiphyseal dysplasia syndrome'] |
| NM_000095.2(COMP): c.1042T > C (p.Cys348Arg) | 137852656 | COMP | [ ] | [ ] | ['Pseudo-achondroplastic spondyloepiphyseal dysplasia syndrome'] |
| NM_017929.5(PEX26): c.2T > C (p.Met1Thr) | 74315506 | PEX26 | [ ] | [ ] | ['Peroxisome biogenesis disorder 7B'] |
| NM_033163.3(FGF8): c.118T > C (p.Phe40Leu) | 137852661 | FGF8 | [ ] | ['TTCCCTGYTCCG GGCTGGCCGGG'] | ['Kallmann syndrome 6'] |
| NM_007315.3(STAT1): c.2117T > C (p.Leu706Ser) | 137852677 | STAT1 | [ ] | [ ] | ['Immunodeficiency 31a'] |
| NM_007315.3(STAT1): c.1799T > C (p.Leu600Pro) | 137852678 | STAT1 | [ ] | [ ] | ['Mycobacterial and viral infections, susceptibility to, autosomal recessive'] |
| NM_000336.2(SCNN1B): c.1858T > C (p.Tyr620His) | 137852707 | SCNN1B | [ ] | [ ] | ['Pseudoprimary hyperaldosteronism'] |
| NM_005215.3(DCC): c.503T > C (p.Met168Thr) | 121912967 | DCC | [ ] | ['AGCCCAYGCCA ACAATCCACTGG'] | [ ] |
| NM_001034850.2(FAM134B): c.873 + 2T > C | 137852738 | FAM134B | [ ] | [ ] | ['Hereditary sensory and autonomic neuropathy type IIA'] |
| NM_000182.4(HADHA): c.1025T > C (p.Leu342Pro) | 137852772 | HADHA | [ ] | [ ] | ['Mitochondrial trifunctional protein deficiency'] |
| NM_001165974.1(UROC1): c.209T > C (p.Leu70Pro) | 137852796 | UROC1 | [ ] | [ ] | ['Urocanate hydratase deficiency'] |
| NM_000405.4(GM2A): c.412T > C (p.Cys138Arg) | 137852797 | GM2A | [ ] | [ ] | ['Tay-Sachs disease, variant AB'] |
| NM_001039523.2(CHRNA1): c.901T > C (p.Phe301Leu) | 137852806 | CHRNA1 | [ ] | ['TGTGYTCCTTCT GGTCATCGTGG'] | ['Myasthenic syndrome, congenital, fast-channel'] |
| NM_003688.3(CASK): c.802T > C (p.Tyr268His) | 137852817 | CASK | [ ] | [ ] | ['FG syndrome 4'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
| --- | --- | --- | --- | --- | --- |
| NM_003688.3(CASK): c.2740T > C (p.Trp914Arg) | 137852819 | CASK | ['CACAGYGGGTCCCTGTCTCCTGG', 'ACAGYGGGTCCCTGTCTCCTGGG'] | ['CACAGYGGGTCCCTGTCTCCTGG', 'ACAGYGGGTCCCTGTCTCCTGGG'] | ['FG syndrome 4'] |
| NM_182760.3(SUMF1): c.1006T > C (p.Cys336Arg) | 137852848 | SUMF1 | [ ] | [ ] | ['Multiple sulfatase deficiency'] |
| NM_182760.3(SUMF1): c.463T > C (p.Ser155Pro) | 137852850 | SUMF1 | [ ] | ['GGCGACYCCTTTGTCTTTGAAGG'] | ['Multiple sulfatase deficiency', 'not provided'] |
| NM_000158.3(GBE1): c.671T > C (p.Leu224Pro) | 137852886 | GBE1 | [ ] | ['AATGTACYACCAAGAATCAAAGG'] | ['Glycogen storage disease, type IV', 'GLYCOGEN STORAGE DISEASE IV, NONPROGRESSIVE HEPATIC'] |
| m.8356T > C | 118192099 | MT-TK | [ ] | [ ] | ['Myoclonus with epilepsy with ragged red fibers', 'MERRF/MELAS overlap syndrome'] |
| NM_024312.4(GNPTAB): c.1120T > C (p.Phe374Leu) | 137852900 | GNPTAB | [ ] | [ ] | ['Pseudo-Hurler polydystrophy', 'I cell disease'] |
| NM_031924.4(RSPH3): c.631-2A > G | 142800871 | RSPH3 | [ ] | [ ] | ['Kartagener syndrome'] |
| NM_058172.5(ANTXR2): c.566T > C (p.Ile189Thr) | 137852905 | ANTXR2 | [ ] | [ ] | ['Hyaline fibromatosis syndrome'] |
| NM_000419.3(ITGA2B): c.641T > C (p.Leu214Pro) | 137852911 | ITGA2B | [ ] | [CTGGTGCYTGGGGCTCCTGGCGG] | ['Glanzmann thrombasthenia'] |
| NM_001171507.2(MCFD2): c.407T > C (p.Ile136Thr) | 137852914 | MCFD2 | [ ] | [ ] | ['Factor v and factor viii, combined deficiency of, 2'] |
| NM_000540.2(RYR1): c.1205T > C (p.Met402Thr) | 118192117 | RYR1 | ['CGCAYGATCCACCACAGCACCAATGG'] | ['CGCAYGATCCACAGCACCAATGG'] | ['Congenital myopathy with fiber type disproportion', 'Central core disease', 'not provided'] |
| NM_000540.2(RYR1): c.13703T > C (p.Leu4568Pro) | 118192131 | RYR1 | [ ] | [ ] | ['Central core disease', 'not provided'] |
| NM_000540.2(RYR1): c.13949T > C (p.Leu4650Pro) | 118192138 | RYR1 | [ ] | [ ] | ['Central core disease', 'not provided'] |
| NM_138694.3(PKHD1): c.10658T > C (p.Ile3553Thr) | 137852948 | PKHD1 | [ ] | ['GAGCCCAYTGAAATACGCTCAGG'] | ['Polycystic kidney disease, infantile type'] |
| NM_012464.4(TLL1): c.713T > C (p.Val238Ala) | 137852952 | TLL1 | ['GGGATTGYTGTTCATGAATTGGG'] | ['GGGATTGYTGTTCATGAATTGGG'] | ['Atrial septal defect 6'] |
| NM_000540.2(RYR1): c.14762T > C (p.Phe4921Ser) | 118192156 | RYR1 | [ ] | [ ] | ['Central core disease', 'not provided'] |
| NM_024960.4(PANK2): c.178T > C (p.Ser60Pro) | 137852964 | PANK2 | [ ] | ['ATTGACYCAGTCGGATTCAATGG'] | [ ] |
| NM_001001486.1(ATP2C1): c.1751T > C (p.Leu584Pro) | 137853015 | ATP2C1 | [ ] | [ ] | ['Familial benign pemphigus'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_014363.5(SACS): c.5836T > C (p.Trp1946Arg) | 137853017 | SACS | [ ] | [ ] | ['Spastic ataxia Charlevoix-Saguenay type'] |
| NM_014363.5(SACS): c.9742T > C (p.Trp3248Arg) | 137853018 | SACS | [ ] | [ ] | ['Spastic ataxia Charlevoix-Saguenay type'] |
| NM_014363.5(SACS): c.3161T > C (p.Phe1054Ser) | 137853019 | SACS | [ ] | [ ] | ['Spastic ataxia Charlevoix-Saguenay type'] |
| NM_006899.3(IDH3B): c.395T > C (p.Leu132Pro) | 137853020 | IDH3B | [ ] | ['TGCGGCYGAGG TAGGTGGTCTGG', 'GCGGCYGAGGTA GGTGGTCTGGG'] | ['Retinitis pigmentosa 46'] |
| NM_001139.2(ALOX12B): c.1277T > C (p.Leu426Pro) | 137853023 | ALOX12B | [ ] | [ ] | ['Autosomal recessive congenital ichthyosis 2'] |
| NM_001080463.1(DYNC2H1): c.3719T > C (p.Ile1240Thr) | 137853028 | DYNC2H1 | [ ] | [ ] | ['Short-rib thoracic dysplasia 3 with or without polydactyly'] |
| NM_006009.3(TUBA1A): c.1190T > C (p.Leu397Pro) | 137853048 | TUBA1A | [ ] | [ ] | ['Lissencephaly 3'] |
| NM_004519.3(KCNQ3): c.925T > C (p.Trp309Arg) | 118192249 | KCNQ3 | [ ] | [ ] | ['Benign familial neonatal seizures 2'] |
| NM_000531.5 (OTC): c.332T > C (p.Leu111Pro) | 1800324 | OTC | [ ] | [ ] | [Ornithine carbamoyltransferase deficiency'] |
| NM_001172567.1(MYD88): c.317T > C (p.Leu106Pro) | 137853065 | MYD88 | [ ] | [ ] | ['Myd88 deficiency'] |
| NM_002241.4(KCNJ10): c.418T > C (p.Cys140Arg) | 137853068 | KCNJ10 | [ ] | [ ] | [SeSAME syndrome'] |
| NM_000455.4(STK11): c.200T > C (p.Leu67Pro) | 137853077 | STK11 | [ ] | [ ] | ['Peutz-Jeghers syndrome'] |
| NM_000518.4(HBB): c.332T > C (p.Leu111Pro) | 35256489 | HBB | [ ] | [ ] | ['Beta thalassemia major'] |
| NM_005094.3(5LC27A4): c.739T > C (p.Ser247Pro) | 137853133 | 5LC27A4 | [ ] | [ ] | ['Ichthyosis prematurity syndrome'] |
| NM_001145308.4(LRTOMT): c.313T > C (p.Trp105Arg) | 137853186 | LRTOMT | [ ] | [ ] | ['Deafness, autosomal recessive 631 |
| NM_178012.4(TUBB2B): c.514T > C (p.Ser172Pro) | 137853194 | TUBB2B | [ ] | [ ] | ['Polymicrogyria, asymmetric'] |
| NM_178012.4(TUBB2B): c.683T > C (p.Leu228Pro) | 137853195 | TUBB2B | [ ] | [ ] | ['Polymicrogyria, asymmetric'] |
| NM_178012.4(TUBB2B): c.793T > C (p.Phe265Leu) | 137853196 | TUBB2B | [ ] | [ ] | ['Polymicrogyria, asymmetric'] |
| NM_001082971.1(DDC): c.925T > C (p.Phe309Leu) | 137853209 | DDC | [ ] | [ ] | ['Deficiency of aromatic-L-amino-acid decarboxylase'] |
| NM_006121.3(KRT1): c.1424T > C (p.Leu475Pro) | 137853225 | KRT1 | [ ] | [ ] | ['Bullous ichthyosiform erythroderma'] |
| NM_033500.2(HK1): c.1550T > C (p.Leu517Ser) | 137853249 | HK1 | [ ] | ['GACTTCTYGGCC CTGGATCTTGG', 'TTCTYGGCCCTG GATCTTGGAGG'] | ['Hemolytic anemia due to hexokinase deficiency'] |
| NM_000249.3(MLH1): c.229T > C (p.Cys77Arg) | 63749859 | MLH1 | [ ] | [ ] | ['Hereditary Nonpolyposis Colorectal Neoplasms'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000444.5(PHEX): c.1664T > C (p.Leu555Pro) | 137853270 | PHEX | [ ] | ['AGCYCCAGAAG CCTTTCTTTTGG'] | ['Familial X-linked hypophosphatemic vitamin D refractory rickets'] |
| NM_000321.2(RB1): c.2134T > C (p.Cys712Arg) | 137853296 | RB1 | [ ] | [ ] | ['Retinoblastoma'] |
| NM_007313.2(ABL1): c.988T > C (p.Phe330Leu) | 137853304 | ABL1 | [ ] | [ ] | [ ] |
| NM_003639.4(IKBKG): c.1249T > C (p.Cys417Arg) | 137853325 | IKBKG | [ ] | ['TGGAGYGCATTG AGTAGGGCCGG'] | ['Hypohidrotic ectodermal dysplasia with immune deficiency', 'Hyper-IgM immunodeficiency, X-linked, with hypohidrotic ectodermal dysplasia'] |
| NM_017534.5(MYH2): c.5609T > C (p.Leu1870Pro) | 786201023 | — | [ ] | [ ] | ['Inclusion body myopathy 3'] |
| NM_000314.6(PTEN): c.406T > C (p.Cys136Arg) | 786201044 | PTEN | [ ] | [ ] | ['Hereditary cancer-predisposing syndrome'] |
| NM_001257988.1(TYMP): c.665A > G (p.Lys222Arg) | 149977726 | TYMP | ['CACG AGTYT CTTAC TGAGA ATGG'] | ['CACGAGTYTCTT ACTGAGAATGG', 'GAGTYTCTTACT GAGAATGGAGG'] | [ ] |
| NM_016725.2(FOLR1): c.493 + 2T > C | 144637717 | FOLR1 | ['AGGY GAGGG CTGGG GTGGG CAGG'] | ['CTTCAGGYGAG GGCTGGGGTGGG', 'AGGYGAGGGCTG GGGTGGGCAGG'] | ['not provided'] |
| NM_002225.3(IVD): c.295 + 2T > C | 748026507 | IVD | [ ] | [ ] | ['not provided'] |
| NM_000175.3(GPI): c.1016T > C (p.Leu339Pro) | 137853587 | GPI | [ ] | [ ] | [ ] |
| NM_002055.4(GFAP): c.1055T > C (p.Leu352Pro) | 28932769 | GFAP | [ ] | ['GGACCYGCTCA ATGTCAAGCTGG'] | ['Alexander disease', 'not provided'] |
| NM_020921.3(NIN): c.3665A > G (p.Gln1222Arg) | 187464517 | NIN | [ ] | [ ] | ['Seckel syndrome 7'] |
| NM_005603.4(ATP8B1) :c.2097 + 2T > C | 387906381 | ATP8B1 | [ ] | [ ] | ['Progressive intrahepatic cholestasis'] |
| NM_005144.4(HR): c.-320T > C | 387906382 | HR | [ ] | [ ] | ['Marie Unna hereditary hypotrichosis 1'] |
| NM_001303.3(COX10): c.2T > C (p.Met1Thr) | 387906383 | COX10 | [ ] | [ ] | ['Congenital myasthenic syndrome, acetazolamide-responsive'] |
| NM_004415.2(DSP): c.4961T > C (p.Leu1654Pro) | 749730642 | DSP | [ ] | [ ] | ['not provided'] |
| NM_000392.4(ABCC2): c.1967 + 2T > C | 387906396 | ABCC2 | [ ] | [ ] | ['Dubin-Johnson syndrome'] |
| NM_002769.4(PRSS1): c.116T > C (p.Val39Ala) | 397507439 | — | [ ] | [TACCAGGYGTCC CTGAATTCTGG] | ['Hereditary pancreatitis'] |
| NM_130439.3(MXI1): c.552 + 2T > C | 387906417 | MXI1 | [ ] | [ ] | ['Malignant tumor of prostate'] |
| m.8528T > C | 387906422 | — | [ ] | [ ] | ['Cardiomyopathy, infantile hypertrophic'] |
| NM_000132.3(F8): c.985T > C (p.Cys329Arg) | 387906430 | F8 | [ ] | [ ] | ['Hereditary factor VIII deficiency disease'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_000132.3(F8): c.1417T > C (p.Tyr473His) | 387906443 | F8 | [ ] | [ ] | ['Hereditary factor VIII deficiency disease'] |
| NM_000132.3(F8): c.1729T > C (p.Ser577Pro) | 387906446 | F8 | [ ] | ['AAAGAAYCTGT AGATCAAAGAGG'] | ['Hereditary factor VIII deficiency disease'] |
| NM_004333.4(BRAF): c.1403T > C (p.Phe468Ser) | 397507473 | BRAF | ['ATCAT YTGGA ACAGT CTACA AGG', 'TCATY TGGAA CAGTC TACAA GGG'] | ['ATCATYTGGAAC AGTCTACAAGG', 'TCATYTGGAACA GTCTACAAGGG'] | ['Cardiofaciocutaneo us syndrome', 'Rasopathy'] |
| NM_004333.4(BRAF): c.1454T > C (p.Leu485Ser) | 397507475 | BRAF | [ ] | [ ] | ['Cardiofaciocutaneo us syndrome', 'Rasopathy'] |
| NM_005188.3(CBL): c.1201T > C (p.Cys401Arg) | 397507492 | CBL | [ ] | [ ] | ['Rasopathy'] |
| NM_000133.3(F9): c.52T > C (p.Cys18Arg) | 387906474 | F9 | [ ] | [ ] | ['Hereditary factor IX deficiency disease'] |
| NM_005249.4(FOXG1): c.700T > C (p.Ser234Pro) | 786205008 | FOXG1 | [ ] | [ ] | ['Rett syndrome, congenital variant', 'not provided'] |
| NM_000133.3(F9): c.82T > C (p.Cys28Arg) | 387906481 | F9 | [ ] | [ ] | ['Hereditary factor IX deficiency disease'] |
| NM_000133.3(F9): c.1031T > C (p.Ile344Thr) | 387906482 | F9 | [ ] | ['ACGAACAYCTTC CTCAAATTTGG'] | ['Hereditary factor IX deficiency disease'] |
| m.11253T > C | 200145866 | MT-ND4 | [ ] | [ ] | ['Leber optic atrophy'] |
| NM_000131.4(F7): c.38T > C (p.Leu13Pro) | 387906507 | F7 | [ ] | [ ] | ['Factor VII deficiency'] |
| NM_000131.4(F7): c.983T > C (p.Phe328Ser) | 387906508 | F7 | [ ] | ['GACGTYCTCTGA GAGGACGCTGG'] | ['Factor VII deficiency'] |
| NM_000422.2(KRT17): c.296T > C (p.Leu99Pro) | 28933089 | KRT17 | [ ] | [ ] | ['Pachyonychia congenita type 2', 'not provided'] |
| NM_001040113.1(MYH11): c.3791T > C (p.Leu1264Pro) | 387906532 | MYH11 | [ ] | ['GAAGCYGGAGG CGCAGGTGCAGG'] | ['Aortic aneurysm, familial thoracic 4'] |
| NM_013246.2(CLCF1): c.46T > C (p.Cys16Arg) | 137853934 | — | [ ] | [ ] | ['Cold-induced sweating syndrome 2'] |
| NM_013246.2(CLCF1): c.676T > C (p.Ter226Arg) | 137853935 | — | [ ] | [ ] | ['Cold-induced sweating syndrome 2'] |
| NM_001077620.2(PRCD): c.2T > C (p.Met1Thr) | 527236092 | — | [ ] | [ ] | ['Retinitis pigmentosa'] |
| NM_000488.3(SERPINC1): c.68T > C (p.Leu23Pro) | 387906575 | SERPINC1 | [ ] | [ ] | ['Antithrombin III deficiency'] |
| NM_206933.2(USH2A): c.9751T > C (p.Cys3251Arg) | 527236118 | USH2A | [ ] | [ ] | ['Retinitis pigmentosa'] |
| NM_001458.4(FLNC): c.752T > C (p.Met251Thr) | 387906586 | FLNC | [ ] | [ ] | ['Myopathy, distal, 4'] |
| NM_000781.2(CYP11A1): c.665T > C (p.Leu222Pro) | 387906601 | CYP11A1 | [ ] | [ ] | ['Adrenal insufficiency, congenital, with 46,XY sex reversal, partial or complete'] |
| NM_000548.3(TSC2): c.2410T > C (p.Cys804Arg) | 137853995 | TSC2 | [ ] | [ ] | ['Tuberous sclerosis syndrome', 'Tuberous sclerosis 2', 'not provided'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_001145661.1(GATA2): c.1117T > C (p.Cys373Arg) | 387906633 | GATA2 | [ ] | [ ] | ['Lymphedema, primary, with myelodysplasia'] |
| NM_002693.2(POLG): c.3470A > G (p.Asn1157Ser) | 548076633 | POLG | ['CAAGAGGYTGGTGATCTGCAAGG'] | ['CAAGAGGYTGGTGATCTGCAAGG'] | ['not provided'] |
| NM_002465.3(MYBPC1): c.706T > C (p.Trp236Arg) | 387906657 | MYBPC1 | [ ] | [ ] | ['Distal arthrogryposis type 1B'] |
| NM_002465.3(MYBPC1): c.2566T > C (p.Tyr856His) | 387906658 | MYBPC1 | [ ] | ['CAAACCYATATCCGCAGAGTTGG'] | ['Distal arthrogryposis type 1B'] |
| NM_003392.4(WNT5A): c.544T > C (p.Cys182Arg) | 387906663 | WNT5A | [ ] | [ ] | ['Robinow syndrome'] |
| NM_005188.3(CBL): c.1186T > C (p.Cys396Arg) | 387906665 | CBL | [ ] | [ ] | ['Rasopathy'] |
| NM_006902.4(PRRX1): c.338T > C (p.Phe113Ser) | 387906667 | PRRX1 | [ ] | [ ] | ['Dysgnathia complex'] |
| NM_001111035.1(ACP5): c.602T > C (p.Leu201Pro) | 387906672 | — | [ ] | [ ] | ['Spondyloenchondrodysplasia with immune dysregulation'] |
| NM_002734.4(PRKAR1A): c.1117T > C (p.Tyr373His) | 387906693 | PRKAR1A | [ ] | [ ] | ['Acrodysostosis 1 with or without hormone resistance'] |
| NM_002734.4(PRKAR1A): c.980T > C (p.Ile327Thr) | 387906695 | PRKAR1A | [ ] | [ ] | ['Acrodysostosis 1 with or without hormone resistance'] |
| NM_003491.3(NAA10): c.109T > C (p.Ser37Pro) | 387906701 | NAA10 | [ ] | ['TGGCCTTYCCTGGCCCCAGGTGG', 'GGCCTTYCCTGGCCCCAGGTGGG'] | ['N-terminal acetyltransferase deficiency'] |
| NM_006306.3(SMC1A): c.2351T > C (p.Ile784Thr) | 387906702 | SMC1A | ['AGAYTGGTGTGCGCAACATCCGG'] | ['AGAYTGGTGTGCGCAACATCCGG'] | ['Congenital muscular hypertrophy-cerebral syndrome'] |
| NM_000377.2(WAS): c.814T > C (p.Ser272Pro) | 387906716 | WAS | [ ] | [ ] | ['Severe congenital neutropenia X-linked'] |
| NM_000377.2(WAS): c.881T > C (p.Ile294Thr) | 387906717 | WAS | [ ] | ['GACTTCAYTGAGGACCAGGGTGG', 'ACTTCAYTGAGGACCAGGGTGGG'] | ['Severe congenital neutropenia X-linked'] |
| m.12201T > C | 387906733 | MT-TH | [ ] | [ ] | ['Deafness, nonsyndromic sensorineural, mitochondrial'] |
| NM_139125.3(MASP1): c.1888T > C (p.Cys630Arg) | 387906753 | MASP1 | [ ] | [ ] | ['Michels syndrome'] |
| NM_007315.3(STAT1): c.520T > C (p.Cys174Arg) | 387906763 | STAT1 | [ ] | [ ] | ['Immunodeficiency 31C'] |
| NM_053025.3(MYLK): c.5275T > C (p.Ser1759Pro) | 387906781 | — | [ ] | [ ] | ['Aortic aneurysm, familial thoracic 7'] |
| NM_000287.3(PEX6): c.1601T > C (p.Leu534Pro) | 387906809 | PEX6 | [ ] | ['CTTCYGGGCCGGGACCGTGATGG', 'TTCYGGGCCGGGACCGTGATGGG'] | ['Peroxisome biogenesis disorder 4B'] |
| NM_000174.4(GP9): c.167T > C (p.Leu56Pro) | 28933377 | GP9 | [ ] | [ ] | ['Bernard-Soulier syndrome type C'] |
| NM_004153.3(ORC1): c.266T > C (p.Phe89Ser) | 387906827 | ORC1 | [ ] | [ ] | ['Meier-Gorlin syndrome 1'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_021252.4(RAB18): c.619T > C (p.Ter207Gln) | 387906833 | RAB18 | [ ] | [ ] | ['Warburg micro syndrome 3'] |
| NM_000702.3(ATP1A2): c.2291T > C (p.Leu764Pro) | 28933398 | ATP1A2 | [ ] | [ ] | ['Familial hemiplegic migraine type 2'] |
| NM_000702.3(ATP1A2): c.2659T > C (p.Trp887Arg) | 28933399 | ATP1A2 | [ ] | [ ] | ['Familial hemiplegic migraine type 2'] |
| NM_000702.3(ATP1A2): c.2192T > C (p.Met731Thr) | 28933400 | ATP1A2 | [ ] | [ ] | ['Familial hemiplegic migraine type 2'] |
| NM_020433.4(JPH2): c.421T > C (p.Tyr141His) | 387906897 | JPH2 | [ ] | [ ] | ['Familial hypertrophic cardiomyopathy 17'] |
| NM_173170.1(IL36RN): c.80T > C (p.Leu27Pro) | 387906914 | IL36RN | [ ] | [ ] | ['Pustular psoriasis, generalized'] |
| NM_004990.3(MARS): c.1568T > C (p.Ile523Thr) | 201555303 | MARS | [ ] | [ ] | ['Interstitial lung and liver disease'] |
| NM_020191.2(MRPS22): c.644T > C (p.Leu215Pro) | 387906924 | MRPS22 | ['ATCYTAGGGTAAGGTGACTTAGG'] | ['ATCYTAGGGTAAGGTGACTTAGG'] | ['Combined oxidative phosphorylation deficiency 5'] |
| NM_022445.3(TPK1): c.119T > C (p.Leu40Pro) | 387906936 | TPK1 | [ ] | [ ] | ['THIAMINE METABOLISM DYSFUNCTION SYNDROME 5 (EPISODIC ENCEPHALOPATHY TYPE)'] |
| NM_020634.1(GDF3): c.914T > C (p.Leu305Pro) | 387906945 | GDF3 | [ ] | [ ] | ['Congenital ocular coloboma', 'Microphthalmia, isolated 7'] |
| NM_024513.3(FYCO1): c.4127T > C (p.Leu1376Pro) | 387906965 | FYCO1 | [ ] | [CAGCCYGATCCCCATCACTGTGG] | ['Cataract, autosomal recessive congenital 2'] |
| NM_006147.3(IRF6): c.65T > C (p.Leu22Pro) | 387906967 | IRF6 | [ ] | ['GCCYCTACCCTGGGCTCATCTGG'] | ['Van der Woude syndrome', 'Popliteal pterygium syndrome'] |
| NM_025132.3(WDR19): c.2129T > C (p.Leu710Ser) | 387906980 | WDR19 | [ ] | [ ] | ['Cranioectodermal dysplasia 4', 'SENIOR-LOKEN SYNDROME 8'] |
| NM_025132.3(WDR19): c.20T > C (p.Leu7Pro) | 387906982 | WDR19 | [ ] | ['TCTCACYGCTAGAAAAGACTTGG'] | ['Asphyxiating thoracic dystrophy 5'] |
| NM_014874.3(MFN2): c.647T > C (p.Phe216Ser) | 387906990 | MFN2 | [ ] | [ ] | [ ] |
| NM_016097.4(IER3IP1): c.233T > C (p.Leu78Pro) | 387907012 | IER3IP1 | [ ] | [ ] | ['Microcephaly, epilepsy, and diabetes syndrome'] |
| NM_022489.3(INF2): c.310T > C (p.Cys104Arg) | 387907034 | INF2 | [ ] | [ ] | ['Charcot-Marie-Tooth disease, dominant intermediate E'] |
| NM_022489.3(INF2): c.383T > C (p.Leu128Pro) | 387907037 | INF2 | [ ] | [ ] | ['Charcot-Marie-Tooth disease, dominant intermediate E'] |
| NM_003235.4(TG): c.3229T > C (p.Cys1077Arg) | 137854433 | TG | [ ] | [ ] | ['Iodotyrosyl coupling defect'] |
| NM_058246.3(DNAJB6): c.277T > C (p.Phe93Leu) | 387907046 | DNAJB6 | [ ] | [ ] | ['Limb-girdle muscular dystrophy, type 1E'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_032446.2(MEGF10): c.2320T > C (p.Cys774Arg) | 387907072 | MEGF10 | [ ] | ['GGGCAGYGTAC TTGCCGCACTGG'] | ['Myopathy, areflexia, respiratory distress, and dysphagia, early-onset', 'Myopathy, areflexia, respiratory distress, and dysphagia, early-onset, mild variant'] |
| NM_005502.3(ABCA1): c.4429T > C (p.Cys1477Arg) | 137854494 | ABCA1 | ['CCTGT GYGTC CCCCA GGGGC AGG', 'CTGTG YGTCC CCCAG GGGCA GGG'] | ['CCTGTGYGTCCC CCAGGGGCAGG', 'CTGTGYGTCCCC CAGGGGCAGGG', 'TGTGYGTCCCCC AGGGGCAGGGG', 'GTGYGTCCCCCA GGGGCAGGGGG'] | ['Tangier disease'] |
| NM_005502.3(ABCA1): c.6026T > C (p.Phe2009Ser) | 137854499 | ABCA1 | [ ] | ['GAGTYCTTTGCC CTTTTGAGAGG'] | ['Familial hypoalphalipoprotei nemia'] |
| NM_015175.2(NBEAL2): c.1163T > C (p.Leu388Pro) | 387907113 | NBEAL2 | [ ] | [ ] | ['Gray platelet syndrome'] |
| NM_000196.3(HSD11B2): c.1012T > C (p.Tyr338His) | 387907117 | HSD11B2 | [ ] | ['CCGCCGCYATTA CCCCGGCCAGG', 'CGCCGCYATTAC CCCGGCCAGGG'] | ['Apparent mineralocorticoid excess'] |
| NM_024599.5(RHBDF2): c.557T > C (p.Ile186Thr) | 387907129 | RHBDF2 | ['AGAY TGTGG ATCCG CTGGC CCGG'] | ['AGAYTGTGGATC CGCTGGCCCGG'] | ['Howel-Evans syndrome'] |
| NM_001077488.3(GNAS): c.299T > C (p.Leu100Pro) | 137854531 | GNAS | [ ] | [ ] | ['Pseudohypoparathy roidism type 1A'] |
| NM_001256714.1(DNAAF3): c.386T > C (p.Leu129Pro) | 387907151 | DNAAF3 | [ ] | [ ] | ['Kartagener syndrome', 'Ciliary dyskinesia, primary, 2'] |
| NM_020894.2(UVSSA): c.94T > C (p.Cys32Arg) | 387907164 | UVSSA | ['AAAA TTYGC AAGTA TGTCTT AGG'] | ['AAAATTYGCAA GTATGTCTTAGG', 'AAATTYGCAAGT ATGTCTTAGGG'] | ['UV-sensitive syndrome 3'] |
| NM_000267.3(NF1): c.1523T > C (p.Leu508Pro) | 137854558 | NF1 | [ ] | [ ] | ['Neurofibromatosis, type 1'] |
| NM_000267.3(NF1): c.6200T > C (p.Leu2067Pro) | 137854561 | NF1 | [ ] | [ ] | ['Neurofibromatosis, familial spinal'] |
| NM_004453.3(ETFDH): c.1130T > C (p.Leu377Pro) | 387907170 | ETFDH | [ ] | ['CCAAAACYCAC CTTTCCTGGTGG'] | [ ] |
| NM_000267.3(NF1): c.1070T > C (p.Leu357Pro) | 137854563 | NF1 | [ ] | [ ] | ['Neurofibromatosis, type 1', 'Neurofibromatosis, familial spinal'] |
| NM_024306.4(FA2H): c.707T > C (p.Phe236Ser) | 387907172 | FA2H | [ ] | [ ] | ['Spastic paraplegia 35'] |
| NM_001004127.2(ALG11): c.1142T > C (p.Leu381Ser) | 387907182 | — | [ ] | [ ] | ['Congenital disorder of glycosylation type 1P'] |
| NM_021167.4(GATAD1): c.304T > C (p.Ser102Pro) | 387907188 | GATAD1 | [ ] | [ ] | ['Cardiomyopathy, dilated, 2b'] |

TABLE 7-continued

Human gene mutations that may be corrected by changing a cytosine (C) to a thymine (T). The gene name, gene symbol, and dbSNP database reference number (RS#) are indicated. Also indicated are exemplary protospacers with their PAM sequences (gRNAs and gRNAall) and the base to be edited, e.g., a C, indicated by a "Y". The "gRNAs" sequences, from top to bottom, correspond to SEQ ID NOs: 1914-2091. The "gRNA all" sequences, from top to bottom, correspond to SEQ ID NOs: 2192-2540, 3144-3433.

| Name | RS# (dbSNP) | GeneSymbol | gRNAs | gRNAall | Phenotypes |
|---|---|---|---|---|---|
| NM_033360.3(KRAS):<br>c.211T > C<br>(p.Tyr71His) | 387907205 | KRAS | [ ] | ['GGACCAGYACA<br>TGAGGACTGGGG',<br>'CCAGYACATGAG<br>GACTGGGGAGG',<br>'CAGYACATGAGG<br>ACTGGGGAGGG'] | ['Cardiofaciocutaneous<br>syndrome 2'] |
| NM_006265.2(RAD21):<br>c.1753T > C<br>(p.Cys585Arg) | 387907213 | — | [ ] | [ ] | ['Cornelia de Lange<br>syndrome 4'] |
| NM_000222.2(KIT):<br>c.1859T > C<br>(p.Val620Ala) | 387907217 | KIT | [ ] | [ ] | [ ] |
| NM_000335.4(SCN5A):<br>c.5380T > C<br>(p.Tyr1794His) | 137854615 | SCN5A | [ ] | [ ] | ['Brugada<br>syndrome', 'Brugada<br>syndrome 1'] |
| NM_000076.2(CDKN1C):<br>c.827T > C<br>(p.Phe276Ser) | 387907224 | CDKN1C | [ ] | [ ] | ['Intrauterine growth<br>retardation,<br>metaphyseal<br>dysplasia, adrenal<br>hypoplasia<br>congenita, and<br>genital anomalies'] |
| NM_005691.3(ABCC9):<br>c.3058T > C<br>(p.Ser1020Pro) | 387907229 | ABCC9 | [ ] | [ ] | ['Hypertrichotic<br>osteochondrodysplas<br>ia'] |
| NM_012343.3(NNT):<br>c.2930T > C<br>(p.Leu977Pro) | 387907233 | NNT | [ ] | [ ] | ['Glucocorticoid<br>deficiency 4'] |
| NM_024110.4(CARD14):<br>c.467T > C<br>(p.Leu156Pro) | 387907240 | CARD14 | [ ] | ['CAGCAGCYGCA<br>GGAGCACCTGGG'] | ['Pityriasis rubra<br>pilaris'] |
| NM_002501.3(NFIX):<br>c.179T > C<br>(p.Leu60Pro) | 387907254 | NFIX | [ ] | [ ] | ['Sotos syndrome 2'] |
| NM_001165963.1(SCN1A):<br>c.121A > T<br>(p.Lys41Ter) | 764444350 | SCN1A | [ ] | [ ] | ['Severe myoclonic<br>epilepsy in infancy'] |
| NM_005022.3(PFN1):<br>c.341T > C<br>(p.Met114Thr) | 387907265 | PFN1 | [ ] | [ ] | ['Amyotrophic<br>lateral sclerosis 18'] |
| NM_001172567.1(MYD88):<br>c.818T > C<br>(p.Leu273Pro) | 387907272 | MYD88 | [ ] | [ ] | ['Macroglobulinemia,<br>waldenstrom,<br>somatic'] |
| NM_152296.4(ATP1A3):<br>c.2431T > C<br>(p.Ser811Pro) | 387907282 | ATP1A3 | [ ] | ['TGCCATCYCACT<br>GGCGTACGAGG'] | ['Alternating<br>hemiplegia of<br>childhood 2'] |
| NM_022787.3(NMNAT1):<br>c.838T > C<br>(p.Ter280Gln) | 387907290 | NMNAT1 | [ ] | [ ] | ['Leber congenital<br>amaurosis 9'] |
| NM_005120.2(MED12):<br>c.3493T > C<br>(p.Ser1165Pro) | 387907361 | MED12 | [ ] | ['AGGACYCTGAG<br>CCAGGGGCCCGG'] | ['Ohdo syndrome,<br>X-linked'] |
| NM_006194.3(PAX9):<br>c.62T > C (p.Leu21Pro) | 28933970 | PAX9 | [ ] | ['GGCCGCYGCCC<br>AACGCCATCCGG'] | ['Tooth agenesis,<br>selective, 3'] |
| NM_000492.3(CFTR):<br>c.2780T > C<br>(p.Leu927Pro) | 397508435 | CFTR | [ ] | [ ] | ['Cystic fibrosis'] |
| NM_177976.2(ARL6):<br>c.272T > C (p.Ile91Thr) | 137854907 | ARL6 | [ ] | [ ] | ['Bardet-Biedl<br>syndrome'] |

TABLE 8

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000138.4 (FBN1):c.3128A>G (p.Lys1043Arg) | 137854472 | FBN1 | [ ] | ['TGCACYTGCCGT GGGTGCAGAGG'] | [ ] |
| NM_000237.2 (LPL):c.953A>G (p.Asn318Ser) | 268 | LPL | [ ] | [ ] | ['Hyperlipidemia, familial combined'] |
| NM_000257.3 (MYH7):c.2708A>G (p.Glu903Gly) | 727504261 | MYH7 | [ ] | ['AGCGCYCCTCAG CATCTGCCAGG'] | ['Cardiomyopathy', 'not specified'] |
| NM_000059.3 (BRCA2):c.476-2A>G | 81002853 | BRCA2 | [ ] | ['ACCACYGGGGG TAAAAAAAGGGG', 'TACCACYGGGGG TAAAAAAAGGG', 'ATACCACYGGGG GTAAAAAAAGG'] | ['Familial cancer of breast', 'Breast-ovarian cancer, familial 2', 'Hereditary cancer-predisposing syndrome'] |
| NM_000059.3 (BRCA2):c.9118-2A>G | 81002862 | BRCA2 | [ ] | [ ] | ['Familial cancer of breast', 'Breast-ovarian cancer, familial 2'] |
| NM_000059.3 (BRCA2):c.9649-2A>G | 81002895 | BRCA2 | [ ] | [ ] | ['Familial cancer of breast', 'Breast-ovarian cancer, familial 2'] |
| NM_000387.5 (SLC25A20):c.713A>G (p.Gln238Arg) | 28934589 | SLC25A20 | [ ] | [ ] | ['Carnitine acylcarnitine translocase deficiency', 'not provided'] |
| NM_000060.3 (BTD):c.755A>G (p.Asp252Gly) | 28934601 | BTD | [ ] | [ ] | ['Biotinidase deficiency'] |
| NM_172107.2 (KCNQ2):c.851A>G (p.Tyr284Cys) | 28939683 | KCNQ2 | [ ] | [ ] | ['Benign familial neonatal seizures 1'] |
| NM_006158.4 (NEFL):c.293A>G (p.Asn98Ser) | 58982919 | NEFL | [ ] | [ ] | ['Charcot-Marie-Tooth disease, type 1F', 'not provided'] |
| NM_000019.3 (ACAT1):c.473A>G (p.Asn158Ser) | 199524907 | ACAT1 | [ ] | [ ] | ['Deficiency of acetyl-CoA acetyltransferase'] |
| NM_007294.3 (BRCA1):c.4987-2A>G | 397509212 | BRCA1 | [ ] | [ ] | ['Familial cancer of breast'] |
| NM_007294.3 (BRCA1):c.213-12A>G | 80358163 | BRCA1 | [ ] | [ ] | ['Familial cancer of breast', 'Hereditary breast and ovarian cancer syndrome', 'Breast-ovarian cancer, familial 1', 'Hereditary cancer-predisposing syndrome'] |
| NM_001382.3 (DPAGT1):c.509A>G (p.Tyr170Cys) | 28934876 | DPAGT1 | ['ACAYAGT ACAGGATT CCTGCGGG', 'GACAYAG TACAGGAT TCCTGCGG'] | ['ACAYAGTACAG GATTCCTGCGGG', 'GACAYAGTACAG GATTCCTGCGG'] | ['Congenital disorder of glycosylation type 1J'] |
| NM_032237.4 (POMK):c.773A>G (p.Gln258Arg) | 397509386 | POMK | [ ] | [ ] | ['Congenital muscular dystrophy-dystroglycanopathy with brain and eye anomalies, type A12'] |
| NM_201647.2 (STAMBP):c.125A>G (p.Glu42Gly) | 397509387 | STAMBP | [ ] | [ ] | ['Microcephaly-capillary malformation syndrome'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_006876.2 (B4GAT1):c.1168A>G (p.Asn390Asp) | 397509397 | B4GAT1 | ['CTGATYTTCAGCCTCCTTTTGGG', 'GCTGATYTTCAGCCTCCTTTTGG'] | ['TGATYTTCAGCCTCCTTTTGGGG', 'CTGATYTTCAGCCTCCTTTTGGG', 'GCTGATYTTCAGCCTCCTTTTGG'] | ['Congenital muscular dystrophy-dystroglycanopathy with brain and eye anomalies, type A13'] |
| NM_004315.4 (ASAH1):c.965+4A>G | 397509415 | ASAH1 | [ ] | [ ] | ['Farber lipogranulomatosis'] |
| NM_000257.3 (MYH7):c.1477A>G (p.Met493Val) | 730880875 | MYH7 | [ ] | [ ] | ['Cardiomyopathy'] |
| NM_021020.3 (LZTS1):c.355A>G (p.Lys119Glu) | 119473032 | LZTS1 | [ ] | ['CCCTYCTCGGAGCCCTGTAGAGG'] | [ ] |
| NM_022455.4 (NSD1):c.5893-2A>G | 587784163 | NSD1 | [ ] | [ ] | ['Sotos syndrome 1'] |
| NM_006894.5 (FMO3):c.182A>G (p.Asn61Ser) | 72549322 | FMO3 | [ ] | [ ] | ['Trimethylaminuria'] |
| NM_000403.3 (GALE):c.101A>G (p.Asn34Ser) | 121908046 | GALE | ['TGGAAGYTATCGATGACCACAGG'] | ['TGGAAGYTATCGATGACCACAGG'] | ['UDPglucose-4-epimerase deficiency'] |
| NM_000314.6 (PTEN):c.527A>G (p.Tyr176Cys) | 757498880 | PTEN | [ ] | [ ] | ['Hereditary cancer-predisposing syndrome'] |
| NM_000053.3 (ATP7B):c.2305A>G (p.Met769Val) | 193922103 | ATP7B | [ ] | [ ] | ['Wilson disease', 'not specified', 'not provided'] |
| NM_000173.6 (GP1BA):c.763A>G (p.Met255Val) | 121908064 | GP1BA | [ ] | [ ] | ['Pseudo von Willebrand disease'] |
| NM_000422.2 (KRT17):c.275A>G (p.Asn92Ser) | 59151893 | KRT17 | ['GTCAYTGAGGTTCTGCATGGTGG'] | ['GTCAYTGAGGTTCTGCATGGTGG', 'GCGGTCAYTGAGGTTCTGCATGG'] | ['Pachyonychia congenita type 2', 'not provided'] |
| NM_000288.3 (PEX7):c.854A>G (p.His285Arg) | 62653611 | PEX7 | [ ] | [ ] | ['Rhizomelic chondrodysplasia punctata type 1'] |
| NM_003742.2 (ABCB11):c.890A>G (p.Glu297Gly) | 11568372 | ABCB11 | [ ] | [ ] | ['Progressive familial intrahepatic cholestasis 2', 'Benign recurrent intrahepatic cholestasis 2'] |
| NM_012243.2 (SLC35A3):c.886A>G (p.Ser296Gly) | 141952252 | SLC35A3 | [ ] | [ ] | ['Arthrogryposis, mental retardation, and seizures'] |
| NM_000061.2 (BTK):c.1082A>G (p.Tyr361Cys) | 28935478 | BTK | ['GATGGYAGTTAATGAGCTCAGGG', 'TGATGGYAGTTAATGAGCTCAGG'] | ['GATGGYAGTTAATGAGCTCAGGG', 'TGATGGYAGTTAATGAGCTCAGG'] | [ ] |
| NM_000169.2 (GLA):c.815A>G (p.Asn272Ser) | 28935495 | — | [ ] | [ ] | ['Fabry disease'] |
| NM_016069.9 (PAM16):c.226A>G (p.Asn76Asp) | 786203989 | — | ['TCATAGTYCTGCAGAGGAGAGGG'] | ['CATAGTYCTGCAGAGGAGAGGGG', 'TCATAGTYCTGCAGAGGAGAGGG'] | ['Chondrodysplasia, megarbane-dagher-melki type'] |
| NM_058163.1 (TSR2):c.191A>G (p.Glu64Gly) | 786203996 | TSR2 | [ ] | [ ] | ['Diamond-Blackfan anemia with microtia and cleft palate', 'DIAMOND-BLACKFAN ANEMIA 14 WITH MANDIBULOFACIAL DYSOSTOSIS'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_001098398.1 (COPA):c.728A>G (p.Asp243Gly) | 794727994 | — | [ ] | [ ] | [ ] |
| NM_005957.4 (MTHFR):c.1114A>G (p.Lys372Glu) | 786204024 | MTHFR | [ ] | [ ] | ['Homocysteinemia due to MTHFR deficiency'] |
| NM_012193.3 (FZD4):c.1024A>G (p.Met342Val) | 80358293 | — | [ ] | [ ] | ['Exudative vitreoretinopathy 1'] |
| NM_000186.3 (CFH):c.3590T>C (p.Val1197Ala) | 460184 | CFH | ['CAGYTGA ATTTGTGT GTAAACGG'] | ['CAGYTGAATTTG TGTGTAAACGG'] | ['Atypical hemolytic-uremic syndrome 1'] |
| NM_014846.3 (KIAA0196):c.1411A>G (p.Asn471Asp) | 80338865 | KIAA0196 | [ ] | [ ] | ['Spastic paraplegia 8'] |
| NM_014946.3 (SPAST):c.1165A>G (p.Thr389Ala) | 786204132 | SPAST | ['AGCATTG YCTTCCCA TTCCCAGG'] | ['ATTGYCTTCCCA TTCCCAGGTGG', 'AGCATTGYCTTC CCATTCCCAGG'] | ['Spastic paraplegia 4, autosomal dominant'] |
| NM_000925.3 (PDHB):c.395A>G (p.Tyr132Cys) | 28935769 | PDHB | [ ] | [ ] | ['Pyruvate dehydrogenase E1-beta deficiency'] |
| NM_000090.3 (COL3A1):c.2338-2A>G | 794728050 | COL3A1 | [ ] | [ ] | ['Thoracic aortic aneurysms and aortic dissections'] |
| NM_000540.2 (RYR1):c.97A>G (p.Lys33Glu) | 193922746 | RYR1 | [ ] | [ ] | ['King Denborough syndrome', 'not provided'] |
| NM_000540.2 (RYR1):c.7043A>G (p.Glu2348Gly) | 193922801 | RYR1 | [ ] | ['TTCYCCTCCACG CTCTCGCCTGG'] | ['not provided'] |
| NM_000218.2 (KCNQ1):c.652A>G (p.Lys218Glu) | 36210419 | KCNQ1 | [ ] | ['GCCCCTYGGAGC CCACGCAGAGG'] | ['Torsades de pointes', 'Cardiac arrhythmia'] |
| NM_000540.2 (RYR1):c.14647-1449A>G | 193922886 | RYR1 | [ ] | [ ] | ['Minicore myopathy with external ophthalmoplegia', 'not provided'] |
| NM_004429.4 (EFNB1):c.472A>G (p.Met158Val) | 28936071 | EFNB1 | [ ] | [ ] | ['Craniofrontonasal dysplasia'] |
| NM_007254.3 (PNKP):c.1029+2T>C | 199919568 | PNKP | ['CCGGYGA GGCCCTGG GGCGGGGG', 'TCCGGYG AGGCCCTG GGGCGGG G'] | ['CCGGYGAGGCC CTGGGGCGGGGG', 'TCCGGYGAGGCC CTGGGGCGGGG', 'ATCCGGYGAGGC CCTGGGGCGGG', 'GATCCGGYGAGG CCCTGGGGCGG'] | ['not provided'] |
| NM_005448.2 (BMP15):c.704A>G (p.Tyr235Cys) | 104894765 | BMP15 | ['ATTGAAA YAGAGTAA CAAGAAGG'] | ['ATTGAAAYAGA GTAACAAGAAGG'] | ['Ovarian dysgenesis 2'] |
| NM_004415.2 (DSP):c.1141-2A>G | 794728111 | DSP | [ ] | [ ] | ['not provided'] |
| NM_016035.4 (COQ4):c.155T>C (p.Leu52Ser) | 786204770 | COQ4 | ['GCTGTYG GCCGCCGG CTCCGCGG'] | ['GCTGTYGGCCGC CGGCTCCGCGG'] | ['COENZYME Q10 DEFICIENCY, PRIMARY, 7'] |
| NM_015717.4 (CD207):c.790T>C (p.Trp264Arg) | 200837270 | CD207 | [ ] | [ ] | ['Birbeck granule deficiency'] |
| NM_004771.3 (MMP20):c.611A>G (p.His204Arg) | 786204826 | MMP20 | ['CGAAAYG TGTATCTC CTCCCAGG'] | ['CGAAAYGTGTAT CTCCTCCCAGG'] | ['Amelogenesis imperfecta, hypomaturation type, IIA2'] |
| NM_003392.4 (WNT5A):c.257A>G (p.Tyr86Cys) | 786204836 | WNT5A | [ ] | [ ] | ['Robinow syndrome'] |
| NM_000918.3 (P4HB):c.1178A>G (p.Tyr393Cys) | 786204843 | P4HB | [ ] | [ ] | ['Cole Carpenter syndrome'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000314.6 (PTEN):c.139A>G (p.Arg47Gly) | 786204855 | PTEN | [ ] | [ ] | ['Hereditary cancer-predisposing syndrome'] |
| NM_000314.6 (PTEN):c.320A>G (p.Asp107Gly) | 786204858 | PTEN | [ ] | [ ] | ['Hereditary cancer-predisposing syndrome'] |
| NM_000447.2 (PSEN2):c.715A>G (p.Met239Val) | 28936379 | PSEN2 | [ ] | [ ] | ['Alzheimer disease, type 4', 'not provided'] |
| NM_005263.3 (GFI1):c.1145A>G (p.Asn382Ser) | 28936381 | GFI1 | [ ] | [ ] | ['Severe congenital neutropenia 2, autosomal dominant'] |
| NM_005263.3 (GFI1):c.1208A>G (p.Lys403Arg) | 28936382 | GFI1 | [ ] | [ ] | ['Neutropenia, nonimmune chronic idiopathic, of adults'] |
| NM_000314.6 (PTEN):c.512A>G (p.Gln171Arg) | 786204865 | PTEN | [ ] | [ ] | ['Hereditary cancer-predisposing syndrome'] |
| NM_000314.6 (PTEN):c.254-2A>G | 786204926 | PTEN | [ ] | [ ] | ['Hereditary cancer-predisposing syndrome'] |
| NM_001103.3 (ACTN2):c.1883A>G (p.Glu628Gly) | 786204951 | ACTN2 | [ ] | [ ] | ['Familial hypertrophic cardiomyopathy 23'] |
| NM_003159.2 (CDKL5):c.-162-2A>G | 786204973 | CDKL5 | [ ] | [ ] | ['Early infantile epileptic encephalopathy 2'] |
| NM_001159287.1 (TPI1):c.622A>G (p.Ile208Val) | 121964849 | TPI1 | [ ] | [ ] | ['Triosephosphate isomerase deficiency'] |
| NM_003159.2 (CDKL5):c.2277-2A>G | 786204979 | CDKL5 | [ ] | [ ] | ['Early infantile epileptic encephalopathy 2'] |
| NM_003159.2 (CDKL5):c.458A>G (p.Asp153Gly) | 786204985 | CDKL5 | [ ] | [ ] | ['Early infantile epileptic encephalopathy 2'] |
| NM_003159.2 (CDKL5):c.91A>G (p.Arg31Gly) | 786204991 | CDKL5 | [ ] | [ ] | ['Early infantile epileptic encephalopathy 2'] |
| NM_001007792.1 (NTRK1):c.986A>G (p.Tyr329Cys) | 121964869 | NTRK1 | [ ] | [ ] | ['Hereditary insensitivity to pain with anhidrosis'] |
| NM_001007792.1 (NTRK1):c.1651A>G (p.Met551Val) | 121964870 | NTRK1 | [ ] | [ ] | ['Hereditary insensitivity to pain with anhidrosis'] |
| NM_004360.3 (CDH1):c.2512A>G (p.Ser838Gly) | 121964872 | CDH1 | [ ] | [ ] | ['Hereditary diffuse gastric cancer', 'Hereditary cancer-predisposing syndrome', 'Neoplasm of ovary'] |
| NM_003122.4 (SPINK1):c.101A>G (p.Asn34Ser) | 17107315 | SPINK1 | [ ] | [ ] | ['Hereditary pancreatitis', 'Tropical calcific pancreatitis', 'Pancreatitis, chronic, susceptibility to'] |
| NM_021098.2 (CACNA1H):c.4645A>G (p.Met1549Val) | 786205050 | CACNA1H | [ ] | [ ] | ['Primary hyperaldosteronism'] |
| NM_001385.2 (DPYS):c.1001A>G (p.Gln334Arg) | 121964923 | DPYS | [ ] | [ ] | ['Dihydropyrimidinase deficiency'] |
| NM_003494.3 (DYSF):c.3443-33A>G | 786205083 | DYSF | ['GCCAGAGYGAGTGGCTGGAGTGG'] | ['GCCAGAGYGAGTGGCTGGAGTGG'] | ['Limb-girdle muscular dystrophy, type 2B'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_003816.2 (ADAM9):c.411-8A>G | 786205086 | ADAM9 | [ ] | [ ] | [ ] |
| NM_000532.4 (PCCB):c.1304A>G (p.Tyr435Cys) | 121964961 | PCCB | [ ] | [ ] | ['Propionic acidemia'] |
| NM_000071.2 (CBS):c.1150A>G (p.Lys384Glu) | 121964967 | CBS | ['AACTYGG TCCTGCGG GATGGGGG'] | ['AACTYGGTCCTG CGGGATGGGGG', 'GAACTYGGTCCT GCGGGATGGGG', 'GGAACTYGGTCC TGCGGGATGGG', 'AGGAACTYGGTC CTGCGGGATGG'] | ['Homocystinuria, pyridoxine-responsive'] |
| NM_000093.4 (COL5A1):c.655-2A>G | 786205101 | COL5A1 | [ ] | [ ] | ['Ehlers-Danlos syndrome, classic type'] |
| NM_000481.3 (AMT):c.125A>G (p.His42Arg) | 121964983 | AMT | ['GCCAGGY GGAAGTCA TAGAGCGG'] | ['GCCAGGYGGAA GTCATAGAGCGG'] | ['Non-ketotic hyperglycinemia'] |
| NM_000108.4 (DLD):c.214A>G (p.Lys72Glu) | 121964987 | DLD | [ ] | [ ] | ['Maple syrup urine disease, type 3'] |
| NM_000108.4 (DLD):c.1483A>G (p.Arg495Gly) | 121964989 | DLD | [ ] | ['TTCTCYAAAAGC TTCTGATAAGG'] | ['Maple syrup urine disease, type 3'] |
| NM_000108.4 (DLD):c.1081A>G (p.Met361Val) | 121964993 | DLD | [ ] | [ ] | ['Maple syrup urine disease, type 3'] |
| NM_001918.3 (DBT):c.1355A>G (p.His452Arg) | 121965002 | DBT | [ ] | [ ] | [ ] |
| NM_030813.5 (CLPB):c.1850A>G (p.Tyr617Cys) | 786205138 | CLPB | [ ] | [ ] | [3-METHYLGLUTACONIC ACIDURIA WITH CATARACTS, NEUROLOGIC INVOLVEMENT, AND NEUTROPENIA'] |
| NM_006610.3 (MASP2):c.359A>G (p.Asp120Gly) | 72550870 | MASP2 | [ ] | [ ] | ['MASP2 deficiency'] |
| NM_000398.6 (CYB5R3):c.719A>G (p.Asp240Gly) | 121965018 | CYB5R3 | [ ] | [ ] | ['METHEMO-GLOBINEMIA, TYPE I'] |
| NM_000095.2 (COMP):c.1358A>G (p.Asn453Ser) | 28936668 | COMP | [ ] | [ ] | [ ] |
| NM_000095.2 (COMP):c.1418A>G (p.Asp473Gly) | 28936669 | COMP | [ ] | ['ATTGYCGTCGTC GTCGTCGCAGG'] | [ ] |
| NM_003816.2 (ADAM9):c.1396-2A>G | 786205151 | ADAM9 | [ ] | [ ] | [ ] |
| NM_001204830.1 (LIPT1):c.535A>G (p.Thr179Ala) | 786205156 | — | [ ] | [ ] | ['LIPOYL-TRANSFERASE 1 DEFICIENCY'] |
| NM_000274.3 (OAT):c.734A>G (p.Tyr245Cys) | 121965046 | OAT | [ ] | [ ] | ['Ornithine aminotransferase deficiency'] |
| NM_018488.3 (TBX4):c.1592A>G (p.Gln531Arg) | 28936696 | TBX4 | [ ] | ['GTACYGTAAGG AAGATTCTCGGG', 'GGTACYGTAAGG AAGATTCTCGG'] | ['Ischiopatellar dysplasia'] |
| NM_001110556.1 (FLNA):c.1829-2A>G | 786205183 | FLNA | [ ] | [ ] | ['X-linked periventricular heterotopia'] |
| NM_003865.2 (HESX1):c.541A>G (p.Thr181Ala) | 28936704 | HESX1 | [ ] | [ ] | ['Growth hormone deficiency with pituitary anomalies'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000137.2 (FAH):c.1141A>G (p.Arg381Gly) | 121965077 | FAH | [ ] | ['TCCYGGTCTGAC CATTCCCCAGG'] | ['Tyrosinemia type I'] |
| NM_000137.2 (FAH):c.836A>G (p.Gln279Arg) | 121965078 | FAH | [ ] | [ ] | ['Tyrosinemia type I'] |
| NM_006129.4 (BMP1):c.808A>G (p.Met270Val) | 786205219 | BMP1 | [ ] | [ ] | ['Osteogenesis imperfecta type 13'] |
| NM_001987.4 (ETV6):c.1252A>G (p.Arg418Gly) | 786205226 | ETV6 | [ ] | [ ] | ['Thrombocytopenia 5'] |
| NM_014423.3 (AFF4):c.760A>G (p.Thr254Ala) | 786205233 | AFF4 | [ ] | [ ] | ['CHOPS SYNDROME'] |
| NM_000140.3 (FECH):c.68_194del | 786205247 | FECH | [ ] | [ ] | ['Erythropoietic protoporphyria'] |
| NM_000138.4 (FBN1):c.3344A>G (p.Asp1115Gly) | 794728203 | FBN1 | [ ] | ['ACTCAYCAATAT CTGCAAAATGG'] | ['Thoracic aortic aneurysms and aortic dissections'] |
| NM_198270.3 (NHS):c.853-2A>G | 786205257 | NHS | [ ] | [ ] | ['Nance-Horan syndrome'] |
| NM_005502.3 (ABCA1):c.1790A>G (p.Gln597Arg) | 2853578 | ABCA1 | [ ] | [ ] | ['Tangier disease'] |
| NM_003002.3 (SDHD):c.275A>G (p.Asp92Gly) | 786205436 | SDHD | [ ] | ['GAATAGYCCATC GCAGAGCAAGG'] | ['Fatal infantile mitochondrial cardiomyopathy'] |
| NM_005259.2 (MSTN):c.458A>G (p.Lys153Arg) | 1805086 | — | [ ] | [ ] | [ ] |
| NM_198056.2 (SCN5A):c.1673A>G (p.His558Arg) | 1805124 | SCN5A | [ ] | [ ] | ['Progressive familial heart block type 1A', 'not specified', 'not provided'] |
| NM_000784.3 (CYP27A1):c.776A>G (p.Lys259Arg) | 72551317 | CYP27A1 | [ ] | ['AGTCCACYTGGG GAGGAAGGTGG'] | ['Cholestanol storage disease'] |
| NM_000784.3 (CYP27A1):c.1061A>G (p.Asp354Gly) | 72551320 | CYP27A1 | [ ] | [ ] | ['Cholestanol storage disease'] |
| NM_000463.2 (UGT1A1):c.992A>G (p.Gln331Arg) | 72551348 | — | [ ] | [ ] | ['Crigler-Najjar syndrome, type II'] |
| NM_000463.2 (UGT1A1):c.1070A>G (p.Gln357Arg) | 72551351 | — | [ ] | [ ] | ['Crigler Najjar syndrome, type 1'] |
| NM_016218.2 (POLK):c.1385A>G (p.Asn462Ser) | 786205687 | POLK | [ ] | ['ATTCACAYTCTT CAACTTAATGG'] | ['Malignant tumor of prostate'] |
| NM_016218.2 (POLK):c.181A>G (p.Asn61Asp) | 786205689 | POLK | [ ] | [ ] | ['Malignant tumor of prostate'] |
| NM_016218.2 (POLK):c.1477A>G (p.Lys493Glu) | 786205692 | POLK | [ ] | [ ] | ['Malignant tumor of prostate'] |
| NM_000138.4 (FBN1):c.7916A>G (p.Tyr2639Cys) | 794728280 | FBN1 | [ ] | ['TGTTCAYACTGG AAGCCGGCGGG', 'CTGTTCAYACTG GAAGCCGGCGG'] | ['Thoracic aortic aneurysms and aortic dissections'] |
| NM_000132.3 (F8):c.1331A>G (p.Lys444Arg) | 28937272 | F8 | [ ] | [ ] | ['Hereditary factor VIII deficiency disease'] |
| NM_000531.5 (OTC):c.268A>G (p.Ser90Gly) | 72554340 | OTC | [ ] | [ ] | ['not provided'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_005502.3 (ABCA1):c.2804A>G (p.Asn935Ser) | 28937313 | ABCA1 | ['TCCAYTG TGGCCCAG GAAGGAG G'] | ['TCCAYTGTGGCC CAGGAAGGAGG', 'CGCTCCAYTGTG GCCCAGGAAGG'] | ['Tangier disease'] |
| NM_004380.2 (CREBBP):c.3524A>G (p.Tyr1175Cys) | 28937315 | CREBBP | [ ] | [ ] | ['Rubinstein-Taybi syndrome'] |
| NM_000335.4 (SCN5A):c.3971A>G (p.Asn1324Ser) | 28937317 | SCN5A | [ ] | ['GCAYTGACCACC ACCTCAAGTGG'] | ['Long QT syndrome 3', 'Congenital long QT syndrome'] |
| NM_000891.2 (KCNJ2):c.901A>G (p.Met301Val) | 786205818 | KCNJ2 | [ ] | [ ] | ['Cardiac arrhythmia'] |
| NM_144499.2 (GNAT1):c.386A>G (p.Asp129Gly) | 786205854 | GNAT1 | [ ] | ['CGGAGYCCTTCC ACAGCCGCTGG'] | ['NIGHT BLINDNESS, CONGENITAL STATIONARY, TYPE 1G'] |
| NM_000523.3 (HOXD13):c.974A>G (p.Gln325Arg) | 104893635 | HOXD13 | [ ] | [ ] | ['Syndactyly type 5'] |
| NM_013953.3 (PAX8):c.160A>G (p.Ser54Gly) | 104893660 | — | [ ] | [ ] | ['Thyroid agenesis'] |
| NM_014585.5 (SLC40A1):c.470A>G (p.Asp157Gly) | 104893663 | SLC40A1 | [ ] | [ ] | ['Hemochromatosis type 4'] |
| NM_003124.4 (SPR):c.448A>G (p.Arg150Gly) | 104893665 | SPR | [ ] | [ ] | ['Sepiapterin reductase deficiency'] |
| NM_000258.2 (MYL3):c.445A>G (p.Met149Val) | 104893748 | MYL3 | [ ] | [ ] | ['Familial hypertrophic cardiomyopathy 8', 'Cardiomyopathy', 'Hypertrophic cardiomyopathy'] |
| NM_000539.3 (RHO):c.533A>G (p.Tyr178Cys) | 104893776 | RHO | [ ] | ['GGATGYACCTG AGGACAGGCAGG'] | ['Retinitis pigmentosa 4'] |
| NM_000539.3 (RHO):c.569A>G (p.Asp190Gly) | 104893777 | RHO | [ ] | [ ] | ['Retinitis pigmentosa 4'] |
| NM_000539.3 (RHO):c.44A>G (p.Asn15Ser) | 104893786 | RHO | [ ] | [ ] | ['Retinitis pigmentosa', 'Retinitis pigmentosa 4'] |
| NM_001814.4 (CTSC):c.1235A>G (p.Tyr412Cys) | 28937571 | CTSC | [ ] | [ ] | ['Periodontitis, aggressive, 1'] |
| NM_001701.3 (BAAT):c.226A>G (p.Met76Val) | 28937579 | BAAT | [ ] | [ ] | ['Hypercholanemia, familial'] |
| NM_001257342.1 (BCS1L):c.232A>G (p.Ser78Gly) | 28937590 | BCS1L | [ ] | ['GACACYGAGGT GCTGAGTACGGG', 'CGACACYGAGGT GCTGAGTACGG'] | ['GRACILE syndrome'] |
| NM_004407.3 (DMP1):c.1A>G (p.Met1Val) | 104893834 | DMP1 | [ ] | [ ] | ['Autosomal recessive hypophosphatemic vitamin D refractory rickets'] |
| NM_000406.2 (GNRHR):c.317A>G (p.Gln106Arg) | 104893836 | GNRHR | [ ] | [ ] | ['Hypogonadotropic hypogonadism'] |
| NM_172250.2 (MMAA):c.620A>G (p.Tyr207Cys) | 104893849 | MMAA | [ ] | [ ] | ['Methylmalonic aciduria cblA type'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000320.2 (QDPR):c.449A>G (p.Tyr150Cys) | 104893866 | QDPR | [ ] | ['TGCCGYACCCGA TCATACCTGGG', 'ATGCCGYACCCG ATCATACCTGG'] | ['Dihydropteridine reductase deficiency'] |
| NM_015629.3 (PRPF31):c.527+3A>G | 587776590 | PRPF31 | [ ] | ['GACAYACCCCTG GGTGGTGGAGG', 'GCGGACAYACCC CTGGGTGGTGG'] | ['Retinitis pigmentosa 11'] |
| NM_000112.3 (SLC26A2):c.1273A>G (p.Asn425Asp) | 104893920 | SLC26A2 | [ ] | [ ] | ['Diastrophic dysplasia', 'Achondrogenesis, type IB'] |
| NM_000344.3 (SMN1):c.815A>G (p.Tyr272Cys) | 104893922 | SMN1 | [ ] | [ ] | ['Werdnig-Hoffmann disease'] |
| NM_000344.3 (SMN1):c.784A>G (p.Ser262Gly) | 104893932 | SMN1 | [ ] | [ ] | ['Kugelberg-Welander disease'] |
| NM_000409.3 (GUCA1A):c.296A>G (p.Tyr99Cys) | 104893967 | GUCA1A | [ ] | [ ] | ['Cone dystrophy 3'] |
| NM_182548.3 (LHFPL5):c.380A>G (p.Tyr127Cys) | 104893975 | LHFPL5 | [ ] | [ ] | ['Deafness, autosomal recessive 67'] |
| NM_001024630.3 (RUNX2):c.598A>G (p.Thr200Ala) | 104893993 | RUNX2 | [ ] | [ ] | ['Cleidocranial dysostosis', 'Cleidocranial dysplasia, forme fruste, dental anomalies only'] |
| NM_000162.3 (GCK):c.641A>G (p.Tyr214Cys) | 104894015 | GCK | [ ] | ['GTAGYAGCAGG AGATCATCGTGG'] | ['Hyperinsulinemic hypoglycemia familial 3'] |
| NM_001002010.2 (NT5C3A):c.686A>G (p.Asn229Ser) | 104894028 | NT5C3A | [ ] | [ ] | ['Uridine 5-prime monophosphate hydrolase deficiency, hemolytic anemia due to'] |
| NM_203288.1 (RP9):c.509A>G (p.Asp170Gly) | 104894039 | RP9 | [ ] | [ ] | ['Retinitis pigmentosa 9'] |
| NM_000474.3 (TWIST1):c.466A>G (p.Ile156Val) | 104894059 | TWIST1 | [ ] | [ ] | ['Saethre-Chotzen syndrome'] |
| NM_000532.4 (PCCB):c.1606A>G (p.Asn536Asp) | 202247823 | PCCB | [ ] | ['ATATYTGCATGT TTTCTCCAAGG'] | ['Propionic acidemia', 'not provided'] |
| NM_021615.4 (CHST6):c.521A>G (p.Lys174Arg) | 28937877 | CHST6 | [ ] | [ ] | ['Macular corneal dystrophy Type I'] |
| NM_178138.4 (LHX3):c.332A>G (p.Tyr111Cys) | 104894117 | LHX3 | ['CAGGTGG YACACGAA GTCCTGGG'] | ['CAGGTGGYACA CGAAGTCCTGGG'] | ['Pituitary hormone deficiency, combined 3'] |
| NM_004897.4 (MINPP1):c.809A>G (p.Gln270Arg) | 104894171 | MINPP1 | [ ] | [ ] | ['Thyroid cancer, follicular'] |
| NM_000073.2 (CD3G):c.1A>G (p.Met1Val) | 104894199 | CD3G | [ ] | ['CCAYGTCAGTCT CTGTCCTCCGG'] | ['Immunodeficiency 17'] |
| NM_001885.2 (CRYAB):c.358A>G (p.Arg120Gly) | 104894201 | CRYAB | [ ] | [ ] | ['Alpha-B crystallinopathy'] |
| NM_001814.4 (CTSC):c.857A>G (p.Gln286Arg) | 104894208 | CTSC | [ ] | ['CTCCYGAGGGCT TAGGATTGGGG', 'CCTCCYGAGGGC TTAGGATTGGG', 'ACCTCCYGAGGG CTTAGGATTGG'] | ['Papillon-Lef\xc3\xa8vre syndrome', 'Haim-Munk syndrome'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_001814.4 (CTSC):c.1040A>G (p.Tyr347Cys) | 104894211 | CTSC | [ ] | ['TCCTACAYAGTG GTACTCAGAGG'] | ['Papillon-Lef\xc3\xa8vre syndrome', 'Periodontitis, aggressive, 1'] |
| NM_012193.3 (FZD4):c.766A>G (p.Ile256Val) | 104894223 | — | ['GAAATAY GATGGGGC GCTCAGGG', 'AGAAATA YGATGGGG CGCTCAGG'] | ['GAAATAYGATG GGGCGCTCAGGG', 'AGAAATAYGATG GGGCGCTCAGG'] | ['Retinopathy of prematurity'] |
| NM_005343.2 (HRAS):c.350A>G (p.Lys117Arg) | 104894227 | — | [ ] | [ ] | ['Costello syndrome'] |
| NM_145014.2 (HYLS1):c.632A>G (p.Asp211Gly) | 104894232 | — | [ ] | [ ] | ['Hydrolethalus syndrome'] |
| NM_000525.3 (KCNJ11):c.776A>G (p.His259Arg) | 104894248 | KCNJ11 | ['GACAYGG TAGATGAT CAGCGGGG'] | ['GACAYGGTAGA TGATCAGCGGGG', 'TGACAYGGTAGA TGATCAGCGGG', 'ATGACAYGGTAG ATGATCAGCGG'] | ['Islet cell hyperplasia'] |
| NM_000317.2 (PTS):c.155A>G (p.Asn52Ser) | 104894275 | PTS | ['TAAYTGT GCCCATGG CCATTTGG'] | ['TAAYTGTGCCCA TGGCCATTTGG'] | ['6-pyruvoyl-tetrahydropterin synthase deficiency'] |
| NM_000317.2 (PTS):c.139A>G (p.Asn47Asp) | 104894278 | PTS | [ ] | [ ] | ['Hyperphenyl-alaninemia, bh4-deficient, a, due to partial pts deficiency'] |
| NM_000317.2 (PTS):c.347A>G (p.Asp116Gly) | 104894279 | PTS | [ ] | [ ] | ['Hyperphenyl-alaninemia, bh4-deficient, a, due to partial pts deficiency'] |
| NM_022051.2 (EGLN1):c.1121A>G (p.His374Arg) | 119476045 | EGLN1 | [ ] | [ ] | ['Erythrocytosis, familial, 3'] |
| NM_015915.4 (ATL1):c.773A>G (p.His258Arg) | 119476048 | ATL1 | [ ] | [ ] | ['Spastic paraplegia 3'] |
| NM_000448.2 (RAG1):c.2735A>G (p.Tyr912Cys) | 104894290 | RAG1 | [ ] | ['CTGYACTGGCAG AGGGATTCTGG'] | ['Histiocytic medullary reticulosis'] |
| NM_000448.2 (RAG1):c.1286A>G (p.Asp429Gly) | 104894292 | RAG1 | [ ] | [ ] | ['Histiocytic medullary reticulosis'] |
| NM_003002.3 (SDHD):c.341A>G (p.Tyr114Cys) | 104894304 | SDHD | [ ] | [ ] | ['Hereditary Paraganglioma-Pheochromocytoma Syndromes', 'Paragangliomas 1'] |
| NM_015141.3 (GPD1L):c.370A>G (p.Ile124Val) | 72552293 | GPD1L | [ ] | [ ] | ['Brugada syndrome 2', 'Primary familial hypertrophic cardiomyopathy', 'Long QT syndrome', 'Sudden infant death syndrome', 'Cardiomyopathy'] |
| NM_020661.2A (AICDA):c.415A>G (p.Met139Val) | 104894322 | AICDA | [ ] | [ ] | ['Immunodeficiency with hyper IgM type 2'] |
| NM_014365.2 (HSPB8):c.421A>G (p.Lys141Glu) | 104894351 | HSPB8 | [ ] | [ ] | ['Charcot-Marie-Tooth disease', 'Distal hereditary motor neuronopathy type 2A'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000217.2 (KCNA1):c.676A>G (p.Thr226Ala) | 104894354 | KCNA1 | [ ] | ['GCGYTTCCACGA TGAAGAAGGGG', 'AGCGYTTCCACG ATGAAGAAGGG', 'CAGCGYTTCCAC GATGAAGAAGG'] | ['Episodic ataxia type 1'] |
| NM_014239.3 (EIF2B2):c.638A>G (p.Glu213Gly) | 104894425 | EIF2B2 | [ ] | ['AGTTGTCYCAAT ACCTGCTTTGG'] | ['Leukoencephalopathy with vanishing white matter', 'Ovarioleuko-dystrophy'] |
| NM_002408.3 (MGAT2):c.785A>G (p.His262Arg) | 104894447 | MGAT2 | [ ] | [ ] | ['Carbohydrate-deficient glycoprotein syndrome type II'] |
| NM_002408.3 (MGAT2):c.952A>G (p.Asn318Asp) | 104894448 | MGAT2 | [ ] | [ ] | ['Carbohydrate-deficient glycoprotein syndrome type II'] |
| NM_000270.3 (PNP):c.383A>G (p.Asp128Gly) | 104894450 | PNP | [ ] | ['ATAYCTCCAACC TCAAACTTGGG', 'GATAYCTCCAAC CTCAAACTTGG'] | ['Purine-nucleoside phosphorylase deficiency'] |
| NM_000270.3 (PNP):c.575A>G (p.Tyr192Cys) | 104894452 | PNP | [ ] | [ ] | ['Purine-nucleoside phosphorylase deficiency'] |
| NM_005982.3 (SIX1):c.386A>G (p.Tyr129Cys) | 104894478 | SIX1 | [ ] | [ ] | ['Melnick-Fraser syndrome', 'Branchiootic syndrome 3'] |
| NM_000101.3 (CYBA):c.281A>G (p.His94Arg) | 104894510 | CYBA | [ ] | [ ] | ['Granulomatous disease, chronic, autosomal recessive, cytochrome b-negative'] |
| NM_024887.3 (DHDDS):c.124A>G (p.Lys42Glu) | 147394623 | DHDDS | [ ] | ['GGCACTYCTTGG CATAGCGACGG'] | ['Retinitis pigmentosa 59'] |
| NM_024006.5 (VKORC1):c.172A>G (p.Arg58Gly) | 104894541 | VKORC1 | [ ] | [ ] | ['Warfarin response'] |
| NM_001128085.1 (ASPA):c.692A>G (p.Tyr231Cys) | 104894550 | — | [ ] | [ ] | ['Spongy degeneration of central nervous system'] |
| NM_001128085.1 (ASPA):c.71A>G (p.Glu24Gly) | 104894551 | — | [ ] | [ ] | ['Spongy degeneration of central nervous system'] |
| NM_000019.3 (ACAT1):c.472A>G (p.Asn158Asp) | 148639841 | ACAT1 | [ ] | [ ] | ['Deficiency of acetyl-CoA acetyltransferase', 'not provided'] |
| NM_014254.2 (TMEM5):c.1016A>G (p.Tyr339Cys) | 150736997 | TMEM5 | [ ] | [ ] | ['Congenital muscular dystrophy-dystroglycanopathy with brain and eye anomalies, type A10'] |
| NM_005557.3 (KRT16):c.374A>G (p.Asn125Ser) | 60723330 | KRT16 | [ ] | ['GCGGTCAYTGA GGTTCTGCATGG'] | ['Pachyonychia congenita, type 1', 'Palmoplantar keratoderma, nonepidermolytic, focal', 'not provided'] |
| NM_005450.4 (NOG):c.665A>G (p.Tyr222Cys) | 104894602 | NOG | [ ] | [ ] | ['Tarsal carpal coalition syndrome', 'Cushing symphalangism'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_030665.3 (RAI1):c.4685A>G (p.Gln1562Arg) | 104894634 | RAI1 | [ ] | ['CTGCTGCYGTCG TCGTCGCTTGG'] | ['Smith-Magenis syndrome'] |
| NM_000346.3 (SOX9):c.517A>G (p.Lys173Glu) | 104894647 | SOX9 | [ ] | [ ] | ['Acampomelic campomelic dysplasia'] |
| NM_024301.4 (FKRP):c.926A>G (p.Tyr309Cys) | 104894679 | FKRP | [ ] | [ ] | ['Congenital muscular dystrophy-dystroglycanopathy without mental retardation, type B5'] |
| NM_000495.4 (COL4A5):c.2394A>G (p.Lys798=) | 281874691 | COL4A5 | [ ] | [ ] | ['Alport syndrome, X-linked recessive'] |
| NM_001604.5 (PAX6):c.1075-2A>G | 794726661 | PAX6 | [ ] | [ ] | ['Congenital aniridia'] |
| NM_000363.4 (TNNI3):c.569A>G (p.Asp190Gly) | 104894728 | TNNI3 | [ ] | [ ] | ['Familial restrictive cardiomyopathy 1', 'Familial hypertrophic cardiomyopathy 7'] |
| NM_000363.4 (TNNI3):c.532A>G (p.Lys178Glu) | 104894730 | TNNI3 | [ ] | ['CCTYCTTCACCT GCTTGAGGTGG', 'CCTCCTYCTTCAC CTGCTTGAGG'] | ['Familial restrictive cardiomyopathy 1'] |
| NM_000054.4 (AVPR2):c.839A>G (p.Tyr280Cys) | 104894752 | AVPR2 | [ ] | [ ] | ['Nephrogenic diabetes insipidus, X-linked'] |
| NM_000074.2 (CD40LG):c.386A>G (p.Glu129Gly) | 104894772 | CD40LG | [ ] | [ ] | ['Immunodeficiency with hyper IgM type 1'] |
| NM_000495.4 (COL4A5):c.4977-2A>G | 281874752 | COL4A5 | [ ] | [ ] | ['Alport syndrome, X-linked recessive'] |
| NM_001165963.1 (SCN1A):c.5264A>G (p.Asp1755Gly) | 794726722 | — | [ ] | [ ] | ['Severe myoclonic epilepsy in infancy'] |
| NM_000495.4 (COL4A5):c.547-2A>G | 281874756 | COL4A5 | [ ] | [ ] | ['Alport syndrome, X-linked recessive'] |
| NM_000495.4 (COL4A5):c.610-2A>G | 281874758 | COL4A5 | [ ] | [ ] | ['Alport syndrome, X-linked recessive'] |
| NM_032520.4 (GNPTG):c.610-2A>G | 193302855 | GNPTG | ['CCCYGAA GGTGGAGG ATGCAGGG'] | ['CCCYGAAGGTG GAGGATGCAGGG', 'GCCCYGAAGGTG GAGGATGCAGG'] | ['Mucolipidosis III Gamma'] |
| NM_002049.3 (GATA1):c.653A>G (p.Asp218Gly) | 104894816 | GATA1 | [ ] | ['GTCCTGYCCCTC CGCCACAGTGG'] | ['GATA-1-related thrombocytopenia with dyserythropoiesis'] |
| NM_000157.3 (GBA):c.680A>G (p.Asn227Ser) | 364897 | GBA | ['CCAYTGG TCTTGAGC CAAGTGGG', 'TCCAYTGG TCTTGAGC CAAGTGG'] | ['CCAYTGGTCTTG AGCCAAGTGGG', 'TCCAYTGGTCTT GAGCCAAGTGG'] | ['Gaucher disease', 'Subacute neuronopathic Gaucher disease', 'Gaucher disease, type 1'] |
| NM_001097642.2 (GJB1):c.194A>G (p.Tyr65Cys) | 104894819 | GJB1 | [ ] | [ ] | ['X-linked hereditary motor and sensory neuropathy'] |
| NM_000166.5 (GJB1):c.614A>G (p.Asn205Ser) | 104894822 | GJB1 | [ ] | [ ] | ['X-linked hereditary motor and sensory neuropathy'] |
| NM_001165963.1 (SCN1A):c.747T>G (p.Asp249Glu) | 773407463 | SCN1A | [ ] | [ ] | ['Severe myoclonic epilepsy in infancy'] |
| NM_000169.2 (GLA):c.886A>G (p.Met296Val) | 104894830 | — | [ ] | [ ] | ['Fabry disease', 'Fabry disease, cardiac variant'] |
| NM_000169.2 (GLA):c.101A>G (p.Asn34Ser) | 104894835 | — | [ ] | [ ] | ['Fabry disease'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_001165963.1 (SCN1A):c.1662+3A>G | 794726773 | SCN1A | [ ] | ['GTGCCAYACCTG GTGTGGGGAGG'] | ['Severe myoclonic epilepsy in infancy'] |
| NM_000169.2 (GLA):c.1228A>G (p.Thr410Ala) | 104894852 | — | [ ] | [ ] | ['Fabry disease'] |
| NM_000202.6 (IDS):c.404A>G (p.Lys135Arg) | 104894861 | IDS | [ ] | ['AAAGACTYTTCC CACCGACATGG'] | ['Mucopolysaccharidosis, MPS-II'] |
| NM_001165963.1 (SCN1A):c.383+1A>G | 794726803 | SCN1A | [ ] | [ ] | ['Severe myoclonic epilepsy in infancy'] |
| NM_000266.3 (NDP):c.131A>G (p.Tyr44Cys) | 104894870 | NDP | [ ] | [ ] | ['Atrophia bulborum hereditaria'] |
| NM_000266.3 (NDP):c.125A>G (p.His42Arg) | 104894874 | NDP | [ ] | ['TGGYGCCTCATG CAGCGTCGAGG'] | [ ] |
| NM_001128227.2 (GNE):c.604A>G (p.Met202Val) | 121908634 | GNE | [ ] | [ ] | ['Inclusion body myopathy 2'] |
| NM_001165963.1 (SCN1A):c.3880-2A>G | 794726816 | — | [ ] | [ ] | ['Severe myoclonic epilepsy in infancy'] |
| NM_001165963.1 (SCN1A):c.1046A>G (p.Tyr349Cys) | 794726844 | SCN1A | ['ACATAYA TCCCTCTG GACATTGG'] | ['ACATAYATCCCT CTGGACATTGG'] | ['Severe myoclonic epilepsy in infancy'] |
| NM_001015877.1 (PHF6):c.700A>G (p.Lys234Glu) | 104894917 | PHF6 | [ ] | [ ] | ['Borjeson-Forssman-Lehmann syndrome'] |
| NM_001015877.1 (PHF6):c.686A>G (p.His229Arg | 104894918 | PHF6 | [ ] | [ ] | ['Borjeson—Forssman-Lehmann syndrome'] |
| NM_001015877.1 (PHF6):c.769A>G (p.Arg257Gly) | 104894919 | PHF6 | ['CTCYTGA TGTTGTTG TGAGCTGG'] | ['CTCYTGATGTTG TTGTGAGCTGG'] | [Borjeson-Forssman-Lehmann syndrome'] |
| NM_000307.4 (POU3F4):c.1000A>G (p.Lys334Glu) | 104894922 | POU3F4 | [ ] | [ ] | ['Deafness, X-linked 2'] |
| NM_000330.3 (RS1):c.667T>C (p.Cys223Arg) | 104894929 | — | [ ] | [ ] | ['Juvenile retinoschisis'] |
| NM_003413.3 (ZIC3):c.1213A>G (p.Lys405Glu) | 104894962 | ZIC3 | ['TGTGTTY GCGCAGGG AGCTCGGG', 'ATGTGTTY GCGCAGGG AGCTCGG'] | ['TGTGTTYGCGCA GGGAGCTCGGG', 'ATGTGTTYGCGC AGGGAGCTCGG'] | ['Heterotaxy, visceral, X-linked'] |
| NM_002420.5 (TRPM1):c.296T>C (p.Leu99Pro) | 191205969 | TRPM1 | [ ] | ['AAGCYCTTAATA TCTGTGCATGG'] | ['Congenital stationary night blindness, type 1C'] |
| NM_004006.2 (DMD):c.1150-2A>G | 794727030 | DMD | [ ] | [ ] | ['Duchenne muscular dystrophy', 'Becker muscular dystrophy'] |
| NM_203290.2 (POLR1C):c.221A>G (p.Asn74Ser) | 371802902 | POLR1C | [ ] | [ ] | ['LEUKODYSTROPHY, HYPOMYELINATING, 11'] |
| NM_019109.4 (ALG1):c.1188-2A>G | 794727073 | ALG1 | [ ] | ['TAAACYGCAGA GAGAACCAAGGG', 'GTAAACYGCAGA GAGAACCAAGG'] | ['Congenital disorder of glycosylation type 1K'] |
| NM_004463.2 (FGD1):c.2016-2A>G | 794727099 | FGD1 | [ ] | [ ] | ['Aarskog syndrome'] |
| NM_024110.4 (CARD14):c.425A>G (p.Glu142Gly) | 281875213 | CARD14 | [ ] | [ ] | ['Psoriasis susceptibility 2', 'not provided'] |
| NM_001004334.3 (GPR179):c.659A>G (p.Tyr220Cys) | 281875236 | GPR179 | [ ] | ['CCCACAYATCCA TCTGCCTGCGG'] | ['Congenital stationary night blindness, type 1E', 'not provided'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_018965.3 (TREM2):c.401A>G (p.Asp134Gly) | 28939079 | TREM2 | ['CCGGTGA YCCAGGGG GTCTATGG'] | ['TGAYCCAGGGG GTCTATGGGAGG', 'CGGTGAYCCAGG GGGTCTATGGG', 'CCGGTGAYCCAG GGGGTCTATGG'] | ['Polycystic lipomembranous osteodysplasia with sclerosing leukoencephalopathy'] |
| NM_015915.4 (ATL1):c.1222A>G (p.Met408Val) | 28939094 | ATL1 | [ ] | ['CACCCAYCTTCT TCACCCCTCGG'] | ['Spastic paraplegia 3'] |
| NM_002437.4 (MPV17):c.186+2T>C | 147952488 | MPV17 | ['TGGYAAG TTCTCCCC TCAACAGG'] | ['TGGYAAGTTCTC CCCTCAACAGG'] | ['Navajo neurohepatopathy', 'not provided'] |
| NM_005359.5 (SMAD4):c.1500A>G (p.Ile500Met) | 281875320 | SMAD4 | ['TGAGYAT GCATAAGC GACGAAG G'] | ['TGAGYATGCATA AGCGACGAAGG'] | ['Myhre syndrome', 'not provided'] |
| NM_005359.5 (SMAD4):c.1498A>G (p.Ile500Val) | 281875322 | SMAD4 | ['TGAGTAY GCATAAGC GACGAAG G'] | ['TGAGTAYGCATA AGCGACGAAGG'] | ['Hereditary cancer-predisposing syndrome', 'Myhre syndrome', 'not provided'] |
| NM_005359.5 (SMAD4):c.989A>G (p.Glu330Gly) | 281875324 | SMAD4 | [ ] | ['ATCCATTYCAAA GTAAGCAATGG'] | ['Juvenile polyposis syndrome', 'Hereditary cancer-predisposing syndrome', 'not provided'] |
| NM_000342.3 (SLC4A1):c.166A>G (p.Lys56Glu) | 5036 | SLC4A1 | [ ] | [ ] | [ ] |
| NM_000518.4 (HBB):c.*113A>G | 33985472 | HBB | [ ] | [ ] | [ ] |
| NM_001127255.1 (NLRP7):c.2738A>G (p.Asn913Ser) | 104895503 | — | ['TCTGGYT GATACTCA AGTCCAGG'] | ['TCTGGYTGATAC TCAAGTCCAGG'] | ['Hydatidiform mole'] |
| NM_000037.3 (ANK1):c.-108T>C | 77173848 | ANK1 | [ ] | ['GGGCCYGGCCC GCACGTCACAGG'] | ['Spherocytosis, type 1, autosomal recessive'] |
| NM_201631.3 (TGM5):c.763T>C (p.Trp255Arg) | 115677373 | TGM5 | ['TGCGGAG YGGACGG GCAGCGTG G'] | ['TGCGGAGYGGA CGGGCAGCGTGG'] | ['Peeling skin syndrome, acral type'] |
| NM_020435.3 (GJC2):c.-167A>G | 587776888 | GJC2 | [ ] | [ ] | ['Leukodystrophy, hypomyelinating, 2'] |
| NM_130466.3 (UBE3B):c.1A>G (p.Met1Val) | 672601304 | UBE3B | [ ] | [ ] | ['Kaufman oculocerebrofacial syndrome'] |
| NM_022124.5 (CDH23):c.146-2A>G | 794727649 | — | [ ] | [ ] | ['Usher syndrome, type 1D'] |
| NM_014191.3 (SCN8A):c.667A>G (p.Arg223Gly) | 672601319 | SCN8A | [ ] | [ ] | ['Early infantile epileptic encephalopathy 13'] |
| NM_001164405.1 (BHLHA9):c.211A>G (p.Asn71Asp) | 672601337 | BHLHA9 | [ ] | [ ] | ['Syndactyly type 9'] |
| NM_021830.4 (C10orf2):c.1754A>G (p.Asn585Ser) | 672601360 | C10orf2 | [ ] | [ ] | ['Perrault syndrome 5'] |
| NM_002887.3 (RARS):c.5A>G (p.Asp2Gly) | 672601372 | RARS | [ ] | [ ] | ['Leukodystrophy, hypomyelinating, 9'] |
| NM_002887.3 (RARS):c.1A>G (p.Met1Val) | 672601375 | RARS | [ ] | [ ] | ['Leukodystrophy, hypomyelinating, 9'] |
| NM_001943.3 (DSG2):c.1880-2A>G | 397514038 | DSG2 | [ ] | [ ] | ['Arrhythmogenic right ventricular cardiomyopathy, type 10', 'Cardiomyopathy'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_024422.4 (DSC2):c.631-2A>G | 397514042 | DSC2 | [ ] | [ ] | ['Arrhythmogenic right ventricular cardiomyopathy, type 11', 'Cardiomyopathy'] |
| NM_001159772.1 (CANT1):c.671T>C (p.Leu224Pro) | 150181226 | CANT1 | [ ] | ['CGTCYGTACGTG GGCGGCCTGGG', 'GCGTCYGTACGT GGGCGGCCTGG'] | ['Desbuquois syndrome'] |
| NM_031418.2 (ANO3):c.2053A>G (p.Ser685Gly) | 587776923 | ANO3 | [ ] | [ ] | ['Dystonia 24'] |
| NM_014191.3 (SCN8A):c.5302A>G (p.Asn1768Asp) | 202151337 | SCN8A | [ ] | [ ] | ['Early infantile epileptic encephalopathy 13'] |
| NM_000367.3 (TPMT):c.719A>G (p.Tyr240Cys) | 1142345 | TPMT | [ ] | [ ] | ['Thiopurine methyltransferase deficiency'] |
| NM_003907.2 (EIF2B5):c.271A>G (p.Thr91Ala) | 28939717 | EIF2B5 | ['AAATGYT TCCTGTAC ACCTGTGG'] | ['AAATGYTTCCTG TACACCTGTGG'] | ['Leukoencephalopathy with vanishing white matter'] |
| NM_004006.2 (DMD):c.10554-2A>G | 794727890 | DMD | [ ] | [ ] | ['Duchenne muscular dystrophy', 'Becker muscular dystrophy', 'Dilated cardiomyopathy 3B'] |
| NM_000084.4 (CLCN5):c.815A>G (p.Tyr272Cys) | 273585644 | CLCN5 | [ ] | [ ] | ['Dent disease 1'] |
| NM_000084.4 (CLCN5):c.1637A>G (p.Lys546Arg) | 273585649 | CLCN5 | [ ] | [ ] | ['Dent disease 1'] |
| NM_000041.3 (APOE):c.237-2A>G | 397514253 | APOE | [ ] | ['CGCCCYGCGGCC GAGAGGGCGGG', 'GCGCCCYGCGGC CGAGAGGGCGG'] | ['Familial type 3 hyperlipoproteinemia'] |
| NM_000155.3 (GALT):c.940A>G (p.Asn314Asp) | 2070074 | GALT | [ ] | [ ] | ['Deficiency of UDPglucose-hexose-1-phosphate uridylyltransferase', 'not provided'] |
| NM_005045.3 (RELN):c.2288A>G (p.Asp763Gly) | 794727998 | RELN | [ ] | [ ] | ['EPILEPSY, FAMILIAL TEMPORAL LOBE, 7'] |
| NM_001914.3 (CYB5A):c.130-2A>G | 794728010 | CYB5A | [ ] | [ ] | ['Methemoglobinemia type 4'] |
| NM_001613.2 (ACTA2):c.1A>G (p.Met1Val) | 794728019 | ACTA2 | [ ] | [ ] | ['Thoracic aortic aneurysms and aortic dissections'] |
| NM_000109.3 (DMD):c.1700T>C (p.Leu567Pro) | 370644567 | DMD | [ ] | [ ] | ['Becker muscular dystrophy', 'Exertional myalgia, muscle stiffness and myoglobinuria', 'not provided'] |
| NM_000060.3 (BTD):c.194A>G (p.His65Arg) | 397514341 | BTD | [ ] | [ ] | ['Biotinidase deficiency'] |
| NM_000060.3 (BTD):c.278A>G (p.Tyr93Cys) | 397514348 | BTD | [ ] | ['GTTCAYAGATGT CAAGGTTCTGG'] | ['Biotinidase deficiency'] |
| NM_000060.3 (BTD):c.356A>G (p.Asn119Ser) | 397514353 | BTD | [ ] | [ ] | ['Biotinidase deficiency'] |
| NM_000060.3 (BTD):c.364A>G (p.Arg122Gly) | 397514354 | BTD | [ ] | [ ] | ['Biotinidase deficiency'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000060.3 (BTD):c.515A>G (p.Asn172Ser) | 397514366 | BTD | [ ] | [ ] | ['Biotinidase deficiency'] |
| NM_000060.3 (BTD):c.583A>G (p.Asn195Asp) | 397514370 | BTD | [ ] | [ ] | ['Biotinidase deficiency'] |
| NM_000060.3 (BTD):c.584A>G (p.Asn195Ser) | 397514371 | BTD | [ ] | [ ] | ['Biotinidase deficiency', 'not provided'] |
| NM_000060.3 (BTD):c.641A>G (p.Asn214Ser) | 397514377 | BTD | ['AGAGGYT GTGTTTAC GGTAGCGG'] | ['AGAGGYTGTGTT TACGGTAGCGG'] | ['Biotinidase deficiency'] |
| NM_000061.2 (BTK):c.1288A>G (p.Lys430Glu) | 128620184 | BTK | ['TCTYGAT GGCCACGT CGTACTGG'] | ['TCTYGATGGCCA CGTCGTACTGG'] | ['X-linked agammaglobulinemia'] |
| NM_001002294.2 (FMO3):c.923A>G (p.Glu308Gly) | 2266780 | FMO3 | [ ] | [ ] | ['Trimethylaminuria'] |
| m.15579A>G | 207460002 | MT-CYB | [ ] | [ ] | ['Multisystem disorder'] |
| NM_000060.3 (BTD):c.1313A>G (p.Tyr438Cys) | 397514415 | BTD | [ ] | ['GGCAYACAGCT CTTTGGATAAGG'] | ['Biotinidase deficiency'] |
| NM_000060.3 (BTD):c.1619A>G (p.Tyr540Cys) | 397514431 | BTD | [ ] | [ ] | ['Biotinidase deficiency'] |
| NM_000023.2 (SGCA):c.410A>G (p.Glu137Gly) | 397514451 | SGCA | [ ] | [ ] | ['Limb-girdle muscular dystrophy, type 2D'] |
| NM_004813.2 (PEX16):c.992A>G (p.Tyr331Cys) | 397514472 | PEX16 | ['AAGYAGA TTTTCTGC CAGGTGGG', 'GAAGYAG ATTTTCTG CCAGGTGG', 'GTAGAAG YAGATTTT CTGCCAGG'] | ['AAGYAGATTTTC TGCCAGGTGGG', 'GAAGYAGATTTT CTGCCAGGTGG', 'GTAGAAGYAGAT TTTCTGCCAGG'] | ['Peroxisome biogenesis disorder 8B'] |
| NM_000933.3 (PLCB4):c.1868A>G (p.Tyr623Cys) | 397514480 | PLCB4 | [ ] | [ ] | ['Auriculocondylar syndrome 1', 'Auriculocondylar syndrome 2'] |
| NM_005340.6 (HINT1):c.152A>G (p.His51Arg) | 397514491 | HINT1 | ['AAAAYGT GTTGGTGC TTGAGGGG', 'GAAAAYG TGTTGGTG CTTGAGGG', 'AGAAAAY GTGTTGGT GCTTGAGG'] | ['AAAAYGTGTTG GTGCTTGAGGGG', 'GAAAAYGTGTTG GTGCTTGAGGG', 'AGAAAAYGTGTT GGTGCTTGAGG'] | ['Gamstorp-Wohlfart syndrome'] |
| NM_007171.3 (POMT1):c.430A>G (p.Asn144Asp) | 397514501 | POMT1 | [ ] | ['GAGCATYCTCTG TTTCAAAGAGG'] | ['Limb-girdle muscular dystrophy-dystroglycanopathy, type C1'] |
| NM_003863.3 (DPM2):c.68A>G (p.Tyr23Cys) | 397514503 | DPM2 | ['TGTAGYA GGTGAAGA TGATCAGG'] | ['TGTAGYAGGTG AAGATGATCAGG'] | ['Congenital disorder of glycosylation type 1u'] |
| NM_174917.4 (ACSF3):c.1A>G (p.Met1Val) | 370382601 | ACSF3 | [ ] | ['GGCAGCAYTGC ACTGACAGGCGG'] | ['not provided'] |
| NM_183075.2 (CYP2U1):c.1139A>G (p.Glu380Gly) | 397514514 | CYP2U1 | [ ] | [ ] | ['Spastic paraplegia 56, autosomal recessive'] |
| NM_000344.3 (SMN1):c.389A>G (p.Tyr130Cys) | 397514517 | SMN1 | [ ] | [ ] | ['Kugelberg-Welander disease'] |
| NM_000138.4 (FBN1):c.4337-2A>G | 794728216 | FBN1 | [ ] | [ ] | ['Thoracic aortic aneurysms and aortic dissections'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_012082.3 (ZFPM2):c.2209A>G (p.Lys737Glu) | 397514521 | — | [ ] | [ ] | ['Double outlet right ventricle'] |
| NM_001168272.1 (ITPR1):c.1759A>G (p.Asn587Asp) | 397514536 | ITPR1 | [ ] | [ ] | ['Spinocerebellar ataxia 29'] |
| NM_178012.4 (TUBB2B):c.767A>G (p.Asn256Ser) | 397514568 | TUBB2B | [ ] | [ ] | ['Polymicrogyria, asymmetric'] |
| NM_000531.5 (OTC):c.155A>G (p.Glu52Gly) | 72554317 | OTC | [ ] | [ ] | ['not provided'] |
| NM_001866.2 (COX7B):c.41-2A>G | 397514584 | COX7B | [ ] | [ ] | ['Aplasia cutis congenita, reticulolinear, with microcephaly, facial dysmorphism, and other congenital anomalies'] |
| NM_001099922.2 (ALG13):c.339A>G (p.Ala113=) | 397514587 | ALG13 | [ ] | [ ] | ['Congenital disorder of glycosylation type 1s'] |
| NM_000531.5 (OTC):c.238A>G (p.Lys80Glu) | 72554332 | OTC | [ ] | ['AAGGACTYCCCT TGCAATAAAGG'] | ['Ornithine carbamoyltransferase deficiency', 'not provided'] |
| NM_001083614.1 (EAR52):c.502A>G (p.Arg168Gly) | 397514591 | EARS2 | [ ] | [ ] | ['Combined oxidative phosphorylation deficiency 12'] |
| NM_001083614.1 (EARS2):c.193A>G (p.Lys65Glu) | 397514595 | EARS2 | [ ] | [ ] | ['Combined oxidative phosphorylation deficiency 12'] |
| NM_198578.3 (LRRK2):c.3364A>G (p.Ile1122Val) | 34805604 | LRRK2 | [ ] | [ ] | ['Parkinson disease 8, autosomal dominant'] |
| NM_033109.4 (PNPT1):c.1160A>G (p.Gln387Arg) | 397514598 | PNPT1 | [ ] | [ ] | ['Combined oxidative phosphorylation deficiency 13'] |
| NM_033109.4 (PNPT1):c.1424A>G (p.Glu475Gly) | 397514599 | PNPT1 | [ ] | ['GACTYCAGATGT AACTCTTATGG'] | ['Deafness, autosomal recessive 70'] |
| NM_000531.5 (OTC):c.277A>G (p.Thr93Ala) | 72554344 | OTC | [ ] | [ ] | ['not provided'] |
| NM_000390.2 (CHM):c.1520A>G (p.His507Arg) | 397514603 | CHM | [ ] | [ ] | ['Choroideremia'] |
| NM_181690.2 (AKT3):c.686A>G (p.Asn229Ser) | 397514605 | AKT3 | [ ] | [ ] | ['Megalencephaly-polymicrogyria-polydactyly-hydrocephalus syndrome 2'] |
| NM_006567.3 (FARS2):c.431A>G (p.Tyr144Cys) | 397514610 | FARS2 | [ ] | [ ] | ['Mitochondrial encephalomyopathy', 'Combined oxidative phosphorylation deficiency 14', 'Global developmental delay'] |
| NM_000531.5 (OTC):c.377A>G (p.Asp126Gly) | 72554358 | OTC | [ ] | [ ] | ['not provided'] |
| NM_005609.2 (PYGM):c.152A>G (p.Asp51Gly) | 397514631 | PYGM | [ ] | [ ] | ['Glycogen storage disease, type V'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000130.4 (F5):c.1601G>A (p.Arg534Gln) | 6025 | F5 | [ ] | [ ] | ['Recurrent abortion', 'Thrombophilia due to factor V Leiden'] |
| NM_000108.4 (DLD):c.1444A>G (p.Arg482Gly) | 397514650 | DLD | [ ] | ['GACTCYAGCTAT ATCTTCACAGG'] | ['Maple syrup urine disease, type 3'] |
| NM_138554.4 (TLR4):c.896A>G (p.Asp299Gly) | 4986790 | TLR4 | [ ] | [ ] | ['Endotoxin hyporesponsiveness'] |
| NM_003156.3 (STIM1):c.251A>G (p.Asp84Gly) | 397514675 | STIM1 | [ ] | ['TTCCACAYCCAC ATCACCATTGG'] | ['Myopathy with tubular aggregates'] |
| NM_003156.3 (STIM1):c.326A>G (p.His109Arg) | 397514677 | STIM1 | [ ] | [ ] | ['Myopathy with tubular aggregates'] |
| NM_000238.3 (KCNH2):c.1900A>G (p.Thr634Ala) | 794728377 | KCNH2 | [ ] | [ ] | ['Cardiac arrhythmia'] |
| NM_000238.3 (KCNH2):c.1913A>G (p.Lys638Arg) | 794728378 | KCNH2 | [ ] | ['ATCYTCTCTGAG TTGGTGTTGGG', 'GATCYTCTCTGA GTTGGTGTTGG'] | ['Cardiac arrhythmia'] |
| NM_001457.3 (FLNB):c.604A>G (p.Met202Val) | 121908895 | FLNB | [ ] | [ ] | ['Atelosteogenesis type 1'] |
| NM_001893.4 (CSNK1D):c.137A>G (p.His46Arg) | 397514693 | CSNK1D | [ ] | [ ] | ['Advanced sleep phase syndrome, familial, 2'] |
| NM_002163.2 (IRF8):c.322A>G (p.Lys108Glu) | 397514710 | IRF8 | [ ] | [ ] | ['Monocyte and dendritic cell deficiency, autosomal recessive'] |
| NM_002163.2 (IRF8):c.238A>G (p.Thr80Ala) | 397514711 | IRF8 | [ ] | ['AACCTCGYCTTC CAAGTGGCTGG'] | ['Autosomal dominant CD11C+/CD1C+ dendritic cell deficiency'] |
| NM_001127217.2 (SMAD9):c.127A>G (p.Lys43Glu) | 397514715 | SMAD9 | [ ] | [ ] | ['Primary pulmonary hypertension 2'] |
| NM_001035.2 (RYR2):c.12290A>G (p.Asn4097Ser) | 794728784 | RYR2 | [ ] | [ ] | ['not provided'] |
| NM_000388.3 (CASR):c.85A>G (p.Lys29Glu) | 397514729 | CASR | [ ] | ['CCCCCTYCTTTT GGGCTCGCTGG'] | ['Hypocalcemia, autosomal dominant 1, with bartter syndrome'] |
| NM_003793.3 (CTSF):c.962A>G (p.Gln321Arg) | 397514731 | CTSF | [ ] | [ ] | ['Ceroid lipofuscinosis, neuronal, 13'] |
| NM_173076.2 (ABCA12):c.4139A>G (p.Asn1380Ser) | 28940269 | ABCA12 | [ ] | [ ] | ['Autosomal recessive congenital ichthyosis 4A'] |
| NM_017890.4 (VPS13B):c.8978A>G (p.Asn2993Ser) | 28940272 | VPS13B | ['TCAYTGA TAAGCAGG GCCCAGGG', 'TTCAYTGA TAAGCAGG GCCCAGG'] | ['TCAYTGATAAGC AGGGCCCAGGG', 'TTCAYTGATAAG CAGGGCCCAGG'] | ['Cohen syndrome', 'not specified'] |
| NM_022114.3 (PRDM16):c.2447A>G (p.Asn816Ser) | 397514743 | PRDM16 | [ ] | ['GCCGCCGYTTTG GCTGGCACGGG'] | ['Left ventricular noncompaction 8'] |
| NM_005689.2 (ABCB6):c.508A>G (p.Ser170Gly) | 397514757 | ABCB6 | [ ] | ['TGGGCYGTTCCA AGACACCAGGG', 'GTGGGCYGTTCC AAGACACCAGG'] | ['Dyschromatosis universalis hereditaria 3'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_015335.4 (MED13L):c.752A>G (p.Glu251Gly) | 28940309 | MED13L | [ ] | [ ] | ['Transposition of great arteries'] |
| NM_152443.2 (RDH12):c.677A>G (p.Tyr226Cys) | 28940313 | RDH12 | [ ] | ['CACTGCGYAGGT GGTGACCCCGG'] | ['Leber congenital amaurosis 13'] |
| NM_000517.4 (HBA2):c.96-2A>G | 41457746 | HBA2 | [ ] | [ ] | [ ] |
| NM_000218.2 (KCNQ1):c.1787A>G (p.Glu596Gly) | 794728538 | KCNQ1 | [ ] | ['GTCTYCTACTCG GTTCAGGCGGG', 'TGTCTYCTACTCG GTTCAGGCGG'] | ['Cardiac arrhythmia'] |
| NM_000218.2 (KCNQ1):c.605A>G (p.Asp202Gly) | 794728569 | KCNQ1 | [ ] | ['AGGYCTGTGGA GTGCAGGAGAGG'] | ['Cardiac arrhythmia'] |
| NM_000218.2 (KCNQ1):c.1515-2A>G | 794728573 | KCNQ1 | [ ] | ['GCCYGCAGTGG AGAGAGGAGAGG'] | ['Cardiac arrhythmia'] |
| NM_000498.3 (CYP11B2):c.1492A>G (p.Thr498Ala) | 72554626 | — | [ ] | [ ] | ['Corticosterone methyloxidase type 2 deficiency'] |
| NM_000169.2 (GLA):c.644A>G (p.Asn215Ser) | 28935197 | — | [ ] | [ ] | ['Fabry disease', 'not provided'] |
| NM_000218.2 (KCNQ1):c.1085A>G (p.Lys362Arg) | 12720458 | KCNQ1 | [ ] | [ ] | ['Congenital long QT syndrome', 'Cardiac arrhythmia', 'Long QT syndrome, LQT1 subtype'] |
| NM_001035.2 (RYR2):c.12533A>G (p.Asn4178Ser) | 794728787 | RYR2 | [ ] | [ ] | ['not provided'] |
| NM_003494.3 (DYSF):c.3349-2A>G | 370874727 | DYSF | [ ] | ['CCGCCCYGGAG ACACGAAGCTGG'] | ['Limb-girdle muscular dystrophy, type 2B'] |
| NM_001035.2 (RYR2):c.568A>G (p.Arg190Gly) | 794728814 | RYR2 | [ ] | [ ] | ['not provided'] |
| NM_198056.2 (SCN5A):c.2788-2A>G | 794728859 | SCN5A | [ ] | ['ACCYGTCGAGAT AATGGGTCAGG'] | ['not provided'] |
| NM_198056.2 (SCN5A):c.4453A>G (p.Ile1485Val) | 794728886 | SCN5A | [ ] | [ ] | ['not provided'] |
| NM_198056.2 (SCN5A):c.4462A>G (p.Thr1488Ala) | 794728887 | SCN5A | [ ] | ['CCTCTGYCATGA AGATGTCCTGG'] | ['not provided'] |
| NM_001927.3 (DES):c.1324A>G (p.Thr442Ala) | 794728995 | DES | [ ] | [ ] | ['not provided'] |
| NM_001613.2 (ACTA2):c.145A>G (p.Met49Val) | 397515325 | ACTA2 | [ ] | [ ] | ['Aortic aneurysm, familial thoracic 6'] |
| NM_000782.4 (CYP24A1):c.1226T>C (p.Leu409Ser) | 6068812 | CYP24A1 | [ ] | [ ] | ['Idiopathic hypercalcemia of infancy'] |
| NM_000372.4 (TYR):c.125A>G (p.Asp42Gly) | 28940878 | TYR | [ ] | ['CTCCTGYCCCCG CTCCACGGTGG'] | ['Tyrosinase-negative oculocutaneous albinism', 'not provided'] |
| NM_000372.4 (TYR):c.1A>G (p.Met1Val) | 28940881 | TYR | [ ] | [ ] | ['Tyrosinase-negative oculocutaneous albinism', 'Oculocutaneous albinism type 1B', 'not provided'] |
| NM_000403.3 (GALE):c.770A>G (p.Lys257Arg) | 28940884 | GALE | [ ] | [ ] | ['UDPglucose-4-epimerase deficiency'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000529.2 (MC2R):c.761A>G (p.Tyr254Cys) | 28940892 | MC2R | ['ACATGYAGCAGGCGCAGTAGGGG', 'GACATGYAGCAGGCGCAGTAGGG'] | ['ACATGYAGCAGGCGCAGTAGGGG', 'GACATGYAGCAGGCGCAGTAGGG', 'AGACATGYAGCAGGCGCAGTAGG'] | ['ACTH resistance'] |
| NM_000061.2 (BTK):c.919A>G (p.Arg307Gly) | 128621195 | BTK | [ ] | [ ] | ['X-linked agammaglobulinemia'] |
| NM_000061.2 (BTK):c.1766A>G (p.Glu589Gly) | 128621206 | BTK | [ ] | [ ] | ['X-linked agammaglobulinemia'] |
| NM_018486.2 (HDAC8):c.539A>G (p.His180Arg) | 397515416 | HDAC8 | [ ] | [ ] | ['Cornelia de Lange syndrome 5'] |
| NM_018486.2 (HDAC8):c.1001A>G (p.His334Arg) | 397515418 | HDAC8 | ['CTCAYGATCTGGGATCTCAGAGG'] | ['CTCAYGATCTGGGATCTCAGAGG'] | ['Cornelia de Lange syndrome 5'] |
| NM_172107.2 (KCNQ2):c.1636A>G (p.Met546Val) | 397515420 | KCNQ2 | [ ] | ['GCAYGACACTGCAGGGGGGTGGG', 'CGCAYGACACTGCAGGGGGGTGG', 'AACCGCAYGACACTGCAGGGGGG'] | ['Early infantile epileptic encephalopathy 7'] |
| NM_001410.2 (MEGF8):c.7099A>G (p.Ser2367Gly) | 397515428 | MEGF8 | [ ] | ['GACYCCCGTGAAATGATTCCCGG'] | ['Carpenter syndrome 2'] |
| NM_004247.3 (EFTUD2):c.623A>G (p.His208Arg) | 397515431 | EFTUD2 | [ ] | [ ] | ['Growth and mental retardation, mandibulofacial dysostosis, microcephaly, and cleft palate'] |
| NM_004572.3 (PKP2):c.1171-2A>G | 794729133 | PKP2 | [ ] | [ ] | ['not provided'] |
| NM_018972.2 (GDAP1):c.368A>G (p.His123Arg) | 397515442 | GDAP1 | [ ] | [ ] | ['Charcot-Marie-Tooth disease type 2K'] |
| NM_014795.3 (ZEB2):c.3134A>G (p.His1045Arg) | 397515449 | ZEB2 | [ ] | [ ] | ['Mowat-Wilson syndrome'] |
| NM_002336.2 (LRP6):c.1298A>G (p.Asn433Ser) | 397515473 | LRP6 | [ ] | [ ] | ['Coronary artery disease, autosomal dominant 2'] |
| NM_001015879.1 (AURKC):c.379-2A>G | 397515484 | AURKC | [ ] | [ ] | ['Infertility associated with multi-tailed spermatozoa and excessive DNA'] |
| NM_000495.4 (COL4A5):c.3107-4A>G | 397515497 | COL4A5 | [ ] | [ ] | ['Alport syndrome, X-linked recessive'] |
| NM_201631.3 (TGM5):c.122T>C (p.Leu41Pro) | 143601447 | TGM5 | [ ] | ['TCAACCYCACCCTGTACTTCAGG'] | ['Peeling skin syndrome, acral type'] |
| NM_013254.3 (TBK1):c.1201A>G (p.Lys401Glu) | 756751089 | TBK1 | [ ] | [ ] | ['FRONTOTEMPORAL DEMENTIA AND/OR AMYOTROPHIC LATERAL SCLEROSIS 4'] |
| NM_000207.2 (INS):c.*59A>G | 397515519 | — | [ ] | ['GGGCYTTATTCCATCTCTCTCGG'] | ['Permanent neonatal diabetes mellitus'] |
| NM_000370.3 (TTPA):c.191A>G (p.Asp64Gly) | 397515523 | TTPA | [ ] | ['CAGGYCCAGATCGAAATCCCGGG', 'CCAGGYCCAGATCGAAATCCCGG'] | ['Ataxia with vitamin E deficiency'] |
| NM_001006657.1 (WDR35):c.2912A>G (p.Tyr971Cys) | 397515535 | WDR35 | [ ] | [ ] | ['Cranioectodermal dysplasia 2'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000424.3 (KRT5):c.1424A>G (p.Glu475Gly) | 61348633 | KRT5 | [ ] | [ ] | ['Epidermolysis bullosa herpetiformis, Dowling-Meara', 'not provided'] |
| NM_004595.4 (SMS):c.443A>G (p.Gln148Arg) | 397515551 | SMS | [ ] | [ ] | ['Snyder Robinson syndrome'] |
| NM_001256850.1 (TTN):c.45629-2A>G | 794729266 | — | [ ] | [ ] | ['not provided'] |
| NM_000404.2 (GLB1):c.947A>G (p.Tyr316Cys) | 72555361 | GLB1 | [ ] | [ ] | ['Infantile GM1 gangliosidosis'] |
| NM_000404.2 (GLB1):c.1498A>G (p.Thr500Ala) | 72555368 | GLB1 | [ ] | [ ] | ['Mucopolysaccharidosis, MPS-IV-B'] |
| NM_000404.2 (GLB1):c.1772A>G (p.Tyr591Cys) | 72555371 | GLB1 | [ ] | [ ] | ['GM1-GANGLIOSIDOSIS, TYPE I, WITH CARDIAC INVOLVEMENT'] |
| NM_000487.5 (ARSA):c.1055A>G (p.Asn352Ser) | 2071421 | ARSA | [ ] | [ ] | ['Metachromatic leukodystrophy', 'not provided'] |
| NM_001037811.2 (HSD17B10):c.713A>G (p.Asn238Ser) | 122461163 | HSD17B10 | [ ] | [ ] | ['2-methyl-3-hydroxybutyric aciduria'] |
| NM_000138.4 (FBN1):c.1148-2A>G | 397515756 | FBN1 | [ ] | [ ] | ['Marfan syndrome'] |
| NM_001875.4 (CPS1):c.1010A>G (p.His337Arg) | 28940283 | CPS1 | [ ] | [ ] | ['Congenital hyperammonemia, type I'] |
| NM_000169.2 (GLA):c.1153A>G (p.Thr385Ala) | 397515869 | — | ['AGCTGTG YGATGAAG CAGGCAGG'] | ['AGCTGTGYGATG AAGCAGGCAGG'] | ['not specified', 'not provided'] |
| NM_000256.3 (MYBPC3):c.1224-2A>G | 397515891 | MYBPC3 | [ ] | ['TACTTGCYGTAG AACAGAAGGGG'] | ['Familial hypertrophic cardiomyopathy 4', 'Cardiomyopathy'] |
| NM_000048.3 (ASL):c.857A>G (p.Gln286Arg) | 28941472 | ASL | [ ] | [ ] | ['Argininosuccinate lyase deficiency', 'not provided'] |
| NM_000256.3 (MYBPC3):c.1928-2A>G | 397515937 | MYBPC3 | [ ] | [ ] | ['Primary familial hypertrophic cardiomyopathy', 'Familial hypertrophic cardiomyopathy 4', 'Cardiomyopathy'] |
| NM_002693.2 (POLG):c.1283T>C (p.Leu428Pro) | 774610098 | POLG | [ ] | [ ] | ['not provided'] |
| NM_004628.4 (XPC):c.413-24A>G | 794729657 | XPC | [ ] | [ ] | ['Xeroderma pigmentosum, group C'] |
| NM_030973.3 (MED25):c.116A>G (p.Tyr39Cys) | 794729668 | MED25 | [ ] | [ ] | ['BASEL-VANAGAITE-SMIRIN-YOSEF SYNDROME'] |
| NM_001955.4 (EDN1):c.271A>G (p.Lys91Glu) | 587777231 | EDN1 | [ ] | [ ] | ['Auriculocondylar syndrome 3'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_003002.3 (SDHD):c.149A>G (p.His50Arg) | 11214077 | SDHD | [ ] | [ ] | ['Pheochromocytoma', 'Merkel cell carcinoma', 'Hereditary cancer-predisposing syndrome', 'Carcinoid tumor of intestine', 'Cowden syndrome 3', 'not specified', 'not provided'] |
| NM_001003722.1 (GLE1):c.433-10A>G | 386833693 | GLE1 | [ ] | [ ] | ['Lethal arthrogryposis with anterior horn cell disease'] |
| NM_000371.3 (TTR):c.185A>G (p.Glu62Gly) | 11541796 | TTR | [ ] | [ ] | ['Amyloidogenic transthyretin amyloidosis'] |
| NM_000256.3 (MYBPC3):c.927-2A>G | 397516082 | MYBPC3 | [ ] | ['GTCCCYGTGTCC CGCAGTCTAGG'] | ['Familial hypertrophic cardiomyopathy 4', 'Cardiomyopathy'] |
| NM_001148.4 (ANK2):c.4373A>G (p.Glu1458Gly) | 72544141 | ANK2 | [ ] | [ ] | ['Long QT syndrome', 'Congenital long QT syndrome', 'Long QT syndrome 4', 'Cardiac arrhythmia, ankyrin B-related', 'Cardiac arrhythmia'] |
| NM_000257.3 (MYH7):c.2206A>G (p.Ile736Val) | 397516138 | MYH7 | [ ] | ['TATCAAYGAACT GTCCCTCAGGG', 'CTATCAAYGAAC TGTCCCTCAGG'] | ['Familial hypertrophic cardiomyopathy 1', 'Cardiomyopathy', 'not specified'] |
| NM_000356.3 (TCOF1):c.149A>G (p.Tyr50Cys) | 28941769 | TCOF1 | ['GTGTGTA YAGATGTC CAGAAGGG'] | ['GTGTGTAYAGAT GTCCAGAAGGG'] | ['Treacher collins syndrome 1'] |
| NM_002150.2 (HPD):c.97G>A (p.Ala33Thr) | 1154510 | HPD | [ ] | ['ATGACGYGGCCT GAATCACAGGG', 'AATGACGYGGCC TGAATCACAGG'] | [4-Alpha—hydroxyphenylpyruvate hydroxylase deficiency'] |
| NM_000375.2 (UROS):c.184A>G (p.Thr62Ala) | 28941775 | UROS | [ ] | [ ] | ['Congenital erythropoietic porphyria'] |
| NM_001008216.1 (GALE):c.308A>G (p.Asp103Gly) | 28940883 | GALE | [ ] | [ ] | ['UDPglucose-4-epimerase deficiency'] |
| NM_000260.3 (MYO7A):c.6439-2A>G | 397516330 | MYO7A | [ ] | ['ATATCCYGGGG GAGCAGAAAGGG', 'GATATCCYGGGG GAGCAGAAAGG'] | ['Usher syndrome, type 1'] |
| NM_033071.3 (SYNE1):c.15705-12A>G | 606231134 | SYNE1 | [ ] | [ ] | ['Spinocerebellar ataxia, autosomal recessive 8'] |
| NM_000187.3 (HGD):c.1112A>G (p.His371Arg) | 120074172 | HGD | [ ] | [ ] | ['Alkaptonuria'] |
| NM_000053.3 (ATP7B1:c.3443T>C (p.Ile1148Thr) | 60431989 | ATP7B | ['TGCTGAY TGGAAACC GTGAGTGG'] | ['TGCTGAYTGGAA ACCGTGAGTGG'] | ['Wilson disease'] |
| NM_000441.1 (SLC26A4):c.-3-2A>G | 397516411 | — | [ ] | [ ] | ['Pendred syndrome', 'Enlarged vestibular aqueduct syndrome'] |
| NM_003041.3 (SLC5A2):c.1961A>G (p.Asn654Ser) | 61742739 | — | [ ] | [ ] | ['Familial renal glucosuria'] |
| NM_000551.3 (VHL):c.467A>G (p.Tyr156Cys) | 397516441 | VHL | [ ] | [ ] | ['Von Hippel-Lindau syndrome'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000531.5 (OTC):c.481A>G (p.Asn161Asp) | 72556270 | OTC | [ ] | [ ] | ['not provided'] |
| NM_000531.5 (OTC):c.482A>G (p.Asn161Ser) | 72556271 | OTC | [ ] | ['CAGCCCAYTGAT AATTGGGATGG'] | ['not provided'] |
| NM_000531.5 (OTC):c.541-2A>G | 72556289 | OTC | ['TCCYAAA AGGCACGG GATGAAGG'] | ['TCCYAAAAGGC ACGGGATGAAGG'] | ['not provided'] |
| NM_000531.5 (OTC):c.542A>G (p.Glu181Gly) | 72556290 | OTC | ['ATAGTGT YCCTAAAA GGCACGGG'] | ['ATAGTGTYCCTA AAAGGCACGGG'] | ['not provided'] |
| NM_000527.4 (LDLR):c.2483A>G (p.Tyr828Cys) | 28942085 | LDLR | [ ] | [ ] | ['Familial hypercholesterolemia', 'not provided'] |
| NM_000271.4 (NPC1):c.3467A>G (p.Asn1156Ser) | 28942105 | NPC1 | [ ] | [ ] | ['Niemann-Pick disease type C1'] |
| NM_000271.4 (NPC1):c.3263A>G (p.Tyr1088Cys) | 28942106 | NPC1 | [ ] | [ ] | ['NIEMANN-PICK DISEASE, TYPE C1, JUVENILE FORM'] |
| NM_020247.4 (ADCK3):c.1541A>G (p.Tyr514Cys) | 119468008 | ADCK3 | [ ] | [ ] | ['Coenzyme Q10 deficiency, primary, 4'] |
| NM_001063.3 (TF):c.956A>G (p.His319Arg) | 41295774 | TF | [ ] | [ ] | [ ] |
| NM_172201.1 (KCNE2):c.281A>G (p.Glu94Gly) | 74424227 | KCNE2 | [ ] | [ ] | ['Congenital long QT syndrome'] |
| NM_002294.2 (LAMP2):c.65-2A>G | 397516743 | LAMP2 | [ ] | [ ] | ['Danon disease'] |
| NM_002880.3 (RAF1):c.524A>G (p.His175Arg) | 397516822 | RAF1 | [ ] | [ ] | ['Noonan syndrome 5'] |
| NM_033360.3 (KRAS):c.13A>G (p.Lys5Glu) | 193929331 | KRAS | [ ] | [ ] | ['Noonan syndrome 3', 'Rasopathy'] |
| NM_000525.3 (KCNJ11):c.155A>G (p.Gln52Arg) | 193929337 | KCNJ11 | [ ] | [ ] | ['Permanent neonatal diabetes mellitus'] |
| NM_000525.3 (KCNJ11):c.544A>G (p.Ile182Val) | 193929348 | KCNJ11 | ['AGAYGAG GGTCTCAG CCCTGCGG'] | ['AGAYGAGGGTC TCAGCCCTGCGG'] | ['Permanent neonatal diabetes mellitus'] |
| NM_000525.3 (KCNJ11):c.989A>G (p.Tyr330Cys) | 193929356 | KCNJ11 | [ ] | [ ] | ['Permanent neonatal diabetes mellitus', 'Neonatal insulin-dependent diabetes mellitus'] |
| NM_001288953.1 (TTC7A):c.1715A>G (p.Lys572Arg) | 139010200 | TTC7A | [ ] | [ ] | ['Multiple gastrointestinal atresias'] |
| NM_024809.4 (TCTN2):c.1506-2A>G | 374349989 | TCTN2 | [ ] | [ ] | ['Meckel syndrome type 8'] |
| NM_012275.2 (IL36RN):c.104A>G (p.Lys35Arg) | 187015338 | IL36RN | [ ] | [ ] | ['Pustular psoriasis, generalized'] |
| NM_178517.3 (PIGW):c.499A>G (p.Met167Val) | 200024253 | PIGW | [ ] | [ ] | ['Hyperphosphatasia with mental retardation syndrome 5'] |
| NM_015662.2 (IFT172):c.5179T>C (p.Cys1727Arg) | 149614625 | — | [ ] | [ ] | ['Short-rib thoracic dysplasia 10 with or without polydactyly'] |
| NM_000226.3 (KRT9):c.469A>G (p.Met157Val) | 58597584 | KRT9 | [ ] | [ ] | ['Epidermolytic palmoplantar keratoderma', 'not provided'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_023073.3 (C5orf42):c.3290-2A>G | 606231260 | C5orf42 | [ ] | ['ATCYATCAAATA CAAAAATTTGG'] | ['Orofaciodigital syndrome 6'] |
| NM_005633.3 (SOS1):c.508A>G (p.Lys170Glu) | 397517172 | SOS1 | [ ] | [ ] | ['Noonan syndrome 4', 'Rasopathy', 'not provided'] |
| NM_006306.3 (SMC1A):c.3254A>G (p.Tyr1085Cys) | 587784418 | SMC1A | ['CTTAYAG ATCTCATC AATGTTGG'] | ['CTTAYAGATCTC ATCAATGTTGG'] | ['Congenital muscular hypertrophy-cerebral syndrome'] |
| NM_006218.2 (PIK3CA):c.1637A>G (p.Gln546Arg) | 397517201 | PIK3CA | [ ] | [ ] | ['Neoplasm of ovary'] |
| NM_006218.2 (PIK3CA):c.3073A>G (p.Thr1025Ala) | 397517202 | PIK3CA | [ ] | [ ] | ['Non-small cell lung cancer'] |
| NM_002354.2 (EPCAM):c.492-2A>G | 606231281 | EPCAM | [ ] | [ ] | ['Diarrhea 5, with tufting enteropathy, congenital'] |
| NM_033056.3 (PCDH15):c.1998-2A>G | 397517452 | PCDH15 | [ ] | [ ] | ['Usher syndrome, type 1F'] |
| NM_000301.3 (PLG):c.112A>G (p.Lys38Glu) | 73015965 | PLG | [ ] | [ ] | ['Plasminogen deficiency, type I'] |
| NM_000155.3 (GALT):c.424A>G (p.Met142Val) | 111033692 | GALT | [ ] | [ ] | ['Deficiency of UDPglucose-hexose-1-phosphate uridylyltransferase'] |
| NM_000096.3 (CP):c.2953A>G (p.Met985Val) | 386134132 | CP | [ ] | [ ] | ['Deficiency of ferroxidase'] |
| NM_000197.1 (HSD17B3):c.703A>G (p.Met235Val) | 119481074 | HSD17B3 | [ ] | [ ] | ['Testosterone 17-beta-dehydrogenase deficiency'] |
| NM_000197.1 (HSD17B3):c.389A>G (p.Asn130Ser) | 119481079 | HSD17B3 | [ ] | [ ] | ['Testosterone 17-beta-dehydrogenase deficiency'] |
| NM_015474.3 (SAMHD1):c.1106T>C (p.Leu369Ser) | 515726139 | SAMHD1 | [ ] | [ ] | ['Aicardi Goutieres syndrome 5'] |
| NM_004817.3 (TJP2):c.1992-2A>G | 587777521 | TJP2 | [ ] | ['CAGCTCYGAGA AGAAACCACGGG', 'TCAGCTCYGAGA AGAAACCACGG'] | ['Progressive familial intrahepatic cholestasis 4'] |
| NM_000257.3 (MYH7):c.617A>G (p.Lys206Arg) | 730880846 | MYH7 | [ ] | ['CTTCYTGCTGCG GTCCCCAATGG'] | ['Cardiomyopathy'] |
| NM_020919.3 (ALS2):c.2980-2A>G | 386134184 | ALS2 | [ ] | [ ] | ['Juvenile primary lateral sclerosis'] |
| m.10044A>G | 41362547 | MT-TG | [ ] | [ ] | ['Sudden death'] |
| NM_002977.3 (SCN9A):c.406A>G (p.Ile136Val) | 80356468 | SCN9A | [ ] | [ ] | ['Primary erythromelalgia'] |
| NM_001128425.1 (MUTYH):c.536A>G (p.Tyr179Cys) | 34612342 | MUTYH | [ ] | [ ] | ['MYH-associated polyposis', 'Hereditary cancer-predisposing syndrome', 'Endometrial carcinoma', 'Carcinoma of colon', 'not specified', 'not provided'] |
| NM_206933.2 (USH2A):c.12067-2A>G | 397517978 | USH2A | [ ] | ['TTCCCYGTAAGA AAATTAACAGG'] | ['Usher syndrome, type 2A', 'Retinitis pigmentosa 39'] |
| NM_000216.2 (ANOS1):c.1A>G (p.Met1Val) | 606231409 | ANOS1 | [ ] | ['GCACCAYGGCT GCGGGTCGAGGG', 'GGCACCAYGGCT GCGGGTCGAGG'] | ['Kallmann syndrome 1'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_206933.2 (USH2A):c.1841-2A>G | 397518003 | USH2A | [ ] | [ ] | ['Usher syndrome, type 2A'] |
| NM_000368.4 (TSC1):c.1760A>G (p.Lys587Arg) | 118203576 | TSC1 | [ ] | [ ] | ['Tuberous sclerosis syndrome', 'Tuberous sclerosis 1', 'Hereditary cancer-predisposing syndrome', 'not specified'] |
| NM_021830.4 (C10orf2):c.1523A>G (p.Tyr508Cys) | 80356540 | C10orf2 | [ ] | [ ] | ['Mitochondrial DNA depletion syndrome 7 (hepatocerebral type)', 'not provided'] |
| NM_003334.3 (UBA1):c.1639A>G (p.Ser547Gly) | 80356546 | UBA1 | [ ] | ['TGGCYTGTCACC CGGATATGTGG'] | ['Arthrogryposis multiplex congenita, distal, X-linked'] |
| NM_206933.2 (USH2A):c.8559-2A>G | 397518039 | USH2A | ['ATCYAAA GCAAAAG ACAAGCAGG'] | ['ATCYAAAGCAA AAGACAAGCAGG'] | ['Retinitis pigmentosa', 'Usher syndrome, type 2A'] |
| NM_000038.5 (APC):c.1744-2A>G | 587783035 | APC | ['TCCYAGT AAGAAAC AGAATATGG'] | ['TCCYAGTAAGA AACAGAATATGG'] | ['Familial adenomatous polyposis 1'] |
| NM_194248.2 (OTOF):c.766-2A>G | 80356584 | OTOF | [ ] | ['GACCYGCAGGC AGGAGAAGGGGG', 'TGACCYGCAGGC AGGAGAAGGGG', 'CTGACCYGCAGG CAGGAGAAGGG', 'GCTGACCYGCAG GCAGGAGAAGG'] | ['Deafness, autosomal recessive 9'] |
| NM_000525.3 (KCNJ11):c.509A>G (p.Lys170Arg) | 80356621 | KCNJ11 | [ ] | [ ] | ['Permanent neonatal diabetes mellitus'] |
| NM_000352.4 (ABCC8):c.215A>G (p.Asn72Ser) | 80356634 | ABCC8 | [ ] | [ ] | ['Permanent neonatal diabetes mellitus'] |
| NM_000352.4 (ABCC8):c.4270A>G (p.Ile1424Val) | 80356653 | ABCC8 | [ ] | [ ] | ['Permanent neonatal diabetes mellitus'] |
| NM_000207.2 (INS):c.323A>G (p.Tyr108Cys) | 80356672 | — | [ ] | [ ] | ['Permanent neonatal diabetes mellitus'] |
| NM_000083.2 (CLCN1):c.382A>G (p.Met128Val) | 80356699 | CLCN1 | [ ] | [ ] | ['Myotonia congenita', 'Congenital myotonia, autosomal dominant form'] |
| NM_001008211.1 (OPTN):c.1433A>G (p.Glu478Gly) | 267606929 | OPTN | [ ] | [ ] | ['Amyotrophic lateral sclerosis type 12'] |
| NM_007375.3 (TARDBP):c.506A>G (p.Asp169Gly) | 80356717 | TARDBP | [ ] | [ ] | ['Amyotrophic lateral sclerosis type 10'] |
| NM_007375.3 (TARDBP):c.1009A>G (p.Met337Val) | 80356730 | TARDBP | [ ] | [ ] | ['Amyotrophic lateral sclerosis type 10'] |
| NM_007375.3 (TARDBP):c.1028A>G (p.Gln343Arg) | 80356731 | TARDBP | [ ] | [ ] | ['Amyotrophic lateral sclerosis type 10'] |
| NM_001701.3 (BAAT):c.967A>G (p.Ile323Val) | 80356747 | BAAT | ['CAAYGAA GAGGAATT GCCCCTGG'] | ['CAAYGAAGAGG AATTGCCCCTGG'] | ['Atypical hemolytic-uremic syndrome 1'] |
| NM_012463.3 (ATP6V0A2):c.732-2A>G | 80356753 | ATP6V0A2 | [ ] | [ ] | ['Cutis laxa with osteodystrophy'] |
| NM_001876.3 (CPT1A):c.1361A>G (p.Asp454Gly) | 80356778 | CPT1A | [ ] | [ ] | ['Carnitine palmitoyltransferase I deficiency'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_001876.3 (CPT1A):c.1079A>G (p.Glu360Gly) | 80356787 | CPT1A | [ ] | [ ] | ['Carnitine palmitoyltransferase I deficiency'] |
| NM_001876.3 (CPT1A):c.1493A>G (p.Tyr498Cys) | 80356791 | CPT1A | [ ] | [ ] | ['Carnitine palmitoyltransferase I deficiency'] |
| NM_003159.2 (CDKL5):c.211A>G (p.Asn71Asp) | 587783072 | CDKL5 | [ ] | [ ] | ['Atypical Rett syndrome', 'not provided'] |
| NM_000257.3 (MYH7):c.1615A>G (p.Met539Val) | 730880930 | MYH7 | [ ] | ['GGAACAYGCAC TCCTCTTCCAGG'] | ['Cardiomyopathy'] |
| m.5843A>G | 118203894 | MT-TY | [ ] | [ ] | [ ] |
| NM_000130.4 (F5):c.1000A>G (p.Arg334Gly) | 118203905 | F5 | [ ] | [ ] | [ ] |
| NM_000130.4 (F5):c.5189A>G (p.Tyr1730Cys) | 118203907 | F5 | ['GTAGYAG GCCCAAGC CCGACAGG'] | ['GTAGYAGGCCC AAGCCCGACAGG'] | ['Factor V deficiency'] |
| NM_000052.6 (ATP7A):c.3911A>G (p.Asn1304Ser) | 151340632 | ATP7A | [ ] | [ ] | ['Menkes kinky-hair syndrome', 'Cutis laxa, X-linked'] |
| NM_007294.3 (BRCA1):c.5053A>G (p.Thr1685Ala) | 80356890 | BRCA1 | [ ] | [ ] | ['Familial cancer of breast', 'Breast-ovarian cancer, familial 1', 'Hereditary cancer-predisposing syndrome'] |
| NM_000046.3 (ARSB):c.629A>G (p.Tyr210Cys) | 118203943 | ARSB | [ ] | [ ] | ['Mucopolysaccharidosis type VI', 'not provided'] |
| NM_013319.2 (UBIAD1):c.305A>G (p.Asn102Ser) | 118203945 | UBIAD1 | ['GTAAGTG YTGACCAA ATTACCGG'] | ['GTAAGTGYTGAC CAAATTACCGG'] | ['Schnyder crystalline corneal dystrophy'] |
| NM_013319.2 (UBIAD1):c.355A>G (p.Arg119Gly) | 118203947 | UBIAD1 | [ ] | ['TCCYGTCATCAC TCTTTTTGTGG'] | ['Schnyder crystalline corneal dystrophy'] |
| NM_013319.2 (UBIAD1):c.695A>G (p.Asn232Ser) | 118203949 | UBIAD1 | ['GGTGTTG YTGGAATG GAGAATGG'] | ['GGTGTTGYTGGA ATGGAGAATGG'] | ['Schnyder crystalline corneal dystrophy'] |
| NM_013319.2 (UBIAD1):c.335A>G (p.Asp112Gly) | 118203950 | UBIAD1 | [ ] | [ ] | ['Schnyder crystalline corneal dystrophy'] |
| NM_024334.2 (TMEM43):c.271A>G (p.Ile91Val) | 144811578 | TMEM43 | [ ] | [ ] | ['Emery-Dreifuss muscular dystrophy 7, autosomal dominant', 'not provided'] |
| NM_012073.4 (CCT5):c.440A>G (p.His147Arg) | 118203986 | CCT5 | [ ] | [ ] | ['Neuropathy, hereditary sensory, with spastic paraplegia, autosomal recessive'] |
| NM_000033.3 (ABCD1):c.443A>G (p.Asn148Ser) | 128624216 | ABCD1 | ['CACTGYT GACGAAG GTAGCAGG G'] | ['CACTGYTGACGA AGGTAGCAGGG', 'GCACTGYTGACG AAGGTAGCAGG'] | ['Adrenoleukodystrophy'] |
| NM_000146.3 (FTL):c.1A>G (p.Met1Val) | 139732572 | FTL | ['CTCAYGG TTGGTTGG CAAGAAGG'] | ['CTCAYGGTTGGT TGGCAAGAAGG'] | ['L-ferritin deficiency'] |
| NM_000785.3 (CYP27B1):c.566A>G (p.Glu189Gly) | 118204012 | CYP27B1 | [ ] | [ ] | ['Vitamin D-dependent rickets, type 1'] |
| NM_000252.2 (MTM1):c.1261-10A>G | 397518445 | MTM1 | [ ] | [ ] | ['Severe X-linked myotubular myopathy'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_139281.2 (WDR36):c.1064A>G (p.Asn355Ser) | 118204022 | WDR36 | [ ] | [ ] | ['Glaucoma 1, open angle, G'] |
| NM_000392.4 (ABCC2):c.4145A>G (p.Gln1382Arg) | 72558202 | ABCC2 | [ ] | [ ] | ['Dubin-Johnson syndrome'] |
| NM_000165.4 (GJA1):c.617A>G (p.Lys206Arg) | 397518464 | GJA1 | [ ] | [ ] | ['Oculodentodigital dysplasia'] |
| NM_000833.4 (GRIN2A):c.1123-2A>G | 397518469 | GRIN2A | [ ] | [ ] | ['Focal epilepsy with speech disorder with or without mental retardation'] |
| NM_015702.2 (MMADHC):c.746A>G (p.Tyr249Cys) | 118204046 | MMADHC | [ ] | [ ] | ['Homocystinuria, cblD type, variant 1'] |
| NM_000526.4 (KRT14):c.368A>G (p.Asn123Ser) | 60171927 | KRT14 | [ ] | ['GCGGTCAYTGA GGTTCTGCATGG'] | ['Epidermolysis bullosa herpetiformis, Dowling-Meara', 'not provided'] |
| NM_000237.2 (LPL):c.548A>G (p.Asp183Gly) | 118204064 | LPL | ['AGCTGGA YCGAGGCC TTAAAAGG'] | ['GCTGGAYCGAG GCCTTAAAAGGG', 'AGCTGGAYCGAG GCCTTAAAAGG'] | ['Hyperlipoproteinemia, type I'] |
| NM_016247.3 (IMPG2):c.370T>C (p.Phe124Leu) | 201893545 | IMPG2 | ['ACTYTTT GGGATCGA CTTCCTGG'] | ['ACTYTTTGGGAT CGACTTCCTGG'] | ['Macular dystrophy, vitelliform, 5'] |
| NM_004035.6 (ACOX1):c.832A>G (p.Met278Val) | 118204090 | ACOX1 | [ ] | [ ] | ['Pseudoneonatal adrenoleukodystrophy'] |
| NM_004035.6 (ACOX1):c.926A>G (p.Gln309Arg) | 118204092 | ACOX1 | [ ] | [ ] | ['Pseudoneonatal adrenoleukodystrophy'] |
| NM_000190.3 (HMBS):c.1A>G (p.Met1Val) | 118204118 | HMBS | [ ] | [ ] | ['Porphyria, acute intermittent, nonerythroid variant'] |
| NM_001363.4 (DKC1):c.941A>G (p.Lys314Arg) | 199422248 | DKC1 | [ ] | ['AATCYTGGCCCC ATAGCAGATGG'] | ['Dyskeratosis congenita X-linked'] |
| NM_000078.2 (CETP):c.1376A>G (p.Asp459Gly) | 2303790 | CETP | [ ] | [ ] | ['Hyperalphalipo-proteinemia'] |
| NM_000531.5 (OTC):c.595A>G (p.Asn199Asp) | 72558405 | OTC | [ ] | [ ] | ['not provided'] |
| NM_000531.5 (OTC):c.596A>G (p.Asn199Ser) | 72558406 | OTC | [ ] | [ ] | ['not provided'] |
| NM_000531.5 (OTC):c.613A>G (p.Met205Val) | 72558411 | OTC | [ ] | [ ] | ['not provided'] |
| NM_000531.5 (OTC):c.717+3A>G | 72558432 | OTC | [ ] | [ ] | ['not provided'] |
| NM_000531.5 (OTC):c.718-2A>G | 72558433 | OTC | [ ] | [ ] | ['not provided'] |
| NM_000531.5 (OTC):c.788A>G (p.Asp263Gly) | 72558443 | OTC | [ ] | [ ] | ['not provided'] |
| NM_000531.5 (OTC):c.790A>G (p.Thr264Ala) | 72558444 | OTC | [ ] | [ ] | ['not provided'] |
| NM_000531.5 (OTC):c.929A>G (p.Glu310Gly) | 72558467 | OTC | [ ] | ['TCCACTYCTTCT GGCTTTCTGGG', 'ATCCACTYCTTCT GGCTTTCTGG'] | ['not provided'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000531.5 (OTC):c.988A>G (p.Arg330Gly) | 72558478 | OTC | [ ] | ['ACTTTCYGTTTT CTGCCTCTGGG', 'CACTTTCYGTTTT CTGCCTCTGG'] | ['not provided'] |
| NM_000488.3 (SERPINC1):c.655A>G (p.Asn219Asp) | 121909571 | SERPINC1 | [ ] | [ ] | ['Antithrombin III deficiency'] |
| NM_007294.3 (BRCA1):c.122A>G (p.His41Arg) | 80357276 | BRCA1 | ['AAATATG YGGTCACA CTTTGTGG'] | ['AAATATGYGGTC ACACTTTGTGG'] | ['Familial cancer of breast', 'Breast-ovarian cancer, familial 1'] |
| NM_007294.3 (BRCA1):c.1A>G (p.Met1Val) | 80357287 | BRCA1 | [ ] | [ ] | ['Familial cancer of breast', 'Breast-ovarian cancer, familial 1', 'Hereditary cancer-predisposing syndrome'] |
| NM_198056.2 (SCN5A):c.1134T>A (p.Tyr378Ter) | 373172185 | SCN5A | [ ] | [ ] | ['not provided'] |
| m.7526A>G | 121434454 | MT-TD | [ ] | [ ] | [ ] |
| NM_007294.3 (BRCA1):c.211A>G (p.Arg71Gly) | 80357382 | BRCA1 | [ ] | [ ] | ['Familial cancer of breast', 'Hereditary breast and ovarian cancer syndrome', 'Breast-ovarian cancer, familial 1', 'Hereditary cancer-predisposing syndrome'] |
| NM_000512.4 (GALNS):c.1460A>G (p.Asn487Ser) | 118204440 | GALNS | ['ACGYTGA GCTGGGGC TGCGCGGG', 'CACGYTG AGCTGGGG CTGCGCGG'] | ['ACGYTGAGCTG GGGCTGCGCGGG', 'CACGYTGAGCTG GGGCTGCGCGG'] | ['Mucopolysaccharidosis, MPS-IV-A'] |
| NM_000505.3 (F12):c.158A>G (p.Tyr53Cys) | 118204455 | F12 | [ ] | ['GGTGGYACTGG AAGGGGAAGTGG'] | [ ] |
| NM_007294.3 (BRCA1):c.5453A>G (p.Asp1818Gly) | 80357477 | BRCA1 | [ ] | ['TTGYCCTCTGTC CAGGCATCTGG'] | ['Familial cancer of breast', 'Breast-ovarian cancer, familial 1'] |
| NM_032492.3 (JAGN1):c.485A>G (p.Gln162Arg) | 587777730 | JAGN1 | [ ] | [ ] | ['Severe congenital neutropenia', 'Severe congenital neutropenia 6, autosomal recessive'] |
| NM_000257.3 (MYH7):c.2087A>G (p.Asn696Ser) | 730880732 | MYH7 | [ ] | [ ] | ['Cardiomyopathy'] |
| NM_000430.3 (PAFAH1B1):c.446A>G (p.His149Arg) | 121434482 | PAFAH1B1 | [ ] | [ ] | ['Lissencephaly 1'] |
| NM_000363.4 (TNNI3):c.547A>G (p.Lys183Glu) | 730881077 | TNNI3 | [ ] | [ ] | ['Cardiomyopathy'] |
| NM_018105.2 (THAP1):c.266A>G (p.Lys89Arg) | 267607111 | THAP1 | [ ] | [ ] | ['Dystonia 6, torsion'] |
| NM_016599.4 (MYOZ2):c.738A>G (p.Ile246Met) | 140126678 | MYOZ2 | [ ] | [ ] | ['Familial hypertrophic cardiomyopathy 16', 'not specified', 'not provided'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000161.2 (GCH1):c.671A>G (p.Lys224Arg) | 41298442 | GCH1 | [ ] | [ ] | ['Dystonia 5, Dopa-responsive type', 'Dystonia, dopa-responsive, with or without hyperphenylalaninemia, autosomal recessive'] |
| NM_017415.2 (KLHL3):c.926A>G (p.Gln309Arg) | 199469627 | KLHL3 | | | ['Pseudohypo-aldosteronism, type 2'] |
| NM_017415.2 (KLHL3):c.1670A>G (p.Tyr557Cys) | 199469645 | KLHL3 | | | ['Pseudohypo-aldosteronism, type 2', 'Pseudohypo aldosteronism type 2D'] |
| NM_003590.4 (CUL3):c.1207-26A>G | 199469650 | CUL3 | | | ['Pseudohypo-aldosteronism, type 2'] |
| NM_003590.4 (CUL3):c.1238A>G (p.Asp413Gly) | 199469656 | CUL3 | | | ['Pseudohypo-aldosteronism, type 2', 'Pseudohypo aldosteronism type 2E'] |
| NM_003590.4 (CUL3):c.1376A>G (p.Lys459Arg) | 199469658 | CUL3 | | | ['Pseudohypo-aldosteronism, type 2'] |
| NM_003590.4 (CUL3):c.1377+3A>G | 199469661 | CUL3 | | | ['Pseudohypo-aldosteronism, type 2'] |
| NM_007294.3 (BRCA1):c.4096+3A>G | 80358015 | BRCA1 | [ ] | [ ] | ['Hereditary breast and ovarian cancer syndrome', 'Breast-ovarian cancer, familial 1', 'Hereditary cancer-predisposing syndrome'] |
| NM_007294.3 (BRCA1):c.135-2A>G | 80358065 | BRCA1 | [ ] | [ ] | ['Breast-ovarian cancer, familial 1'] |
| NM_024426.4 (WT1):c.1391A>G (p.Asp464Gly) | 121907902 | WT1 | [ ] | [ ] | ['Drash syndrome'] |
| NM_007294.3 (BRCA1):c.212+3A>G | 80358083 | BRCA1 | [ ] | [ ] | ['Familial cancer of breast', 'Breast-ovarian cancer, familial 1'] |
| NM_024426.4 (WT1):c.1021A>G (p.Ser341Gly) | 121907908 | WT1 | [ ] | ['CGCYCTCGTACC CTGTGCTGTGG'] | ['Mesothelioma'] |
| NM_007294.3 (BRCA1):c.4676-2A>G | 80358096 | BRCA1 | [ ] | [ ] | ['Breast-ovarian cancer, familial 1', 'Hereditary cancer-predisposing syndrome'] |
| NM_000280.4 (PAX6):c.1171A>G (p.Thr391Ala) | 121907926 | PAX6 | [ ] | ['GTGGYGCCCGA GGTGCCCATTGG'] | ['Optic nerve aplasia, bilateral'] |
| NM_000520.4 (HEXA):c.611A>G (p.His204Arg) | 121907976 | HEXA | [ ] | [ ] | ['Tay-Sachs disease'] |
| NM_000159.3 (GCDH):c.1213A>G (p.Met405Val) | 141437721 | GCDH | [ ] | [ ] | ['Glutaric aciduria, type 1'] |
| NM_024740.2 (ALG9):c.860A>G (p.Tyr287Cys) | 121908023 | ALG9 | [ ] | ['TTAYACAAAAC AATGTTGAGTGG'] | ['Congenital disorder of glycosylation type 1L'] |
| NM_003051.3 (SLC16A1):c.610A>G (p.Lys204Glu) | 80358222 | SLC16A1 | [ ] | [ ] | ['Erythrocyte lactate transporter defect'] |
| NM_000229.1 (LCAT):c.463A>G (p.Asn155Asp) | 121908057 | LCAT | [ ] | [ ] | ['Fish-eye disease'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000639.2 (FASLG):c.466A>G (p.Arg156Gly) | 80358238 | FASLG | [ ] | [ ] | ['Autoimmune lymphoproliferative syndrome'] |
| NM_001369.2 (DNAH5):c.1121T>C (p.Ile374Thr) | 147499872 | DNAH5 | [ ] | [ ] | ['Ciliary dyskinesia, primary, 3'] |
| NM_138691.2 (TMC1):c.1960A>G (p.Met654Val) | 121908074 | TMC1 | [ ] | [ ] | ['Deafness, autosomal recessive 7'] |
| NM_024301.4 (FKRP):c.1387A>G (p.Asn463Asp) | 121908110 | FKRP | [ ] | [ ] | ['Congenital muscular dystrophy-dystroglycanopathy (with or without mental retardation) type B5', 'Limb-girdle muscular dystrophy-dystroglycanopathy, type C5', 'Muscular dystrophy', 'Congenital muscular dystrophy-dystroglycanopathy with brain and eye anomalies type A5', 'Congenital muscular dystrophy-dystroglycanopathy without mental retardation, type B5', 'not provided'] |
| NM_175073.2 (APTX):c.602A>G (p.His201Arg) | 121908133 | APTX | ['GCCAAYG GTAACGGG CCTTTGGG'] | ['GCCAAYGGTAA CGGGCCTTTGGG', 'AGCCAAYGGTAA CGGGCCTTTGG'] | ['Adult onset ataxia with oculomotor apraxia'] |
| NM_001243133.1 (NLRP3):c.1880A>G (p.Glu627Gly) | 121908148 | NLRP3 | [ ] | ['ACAATYCCAGCT GGCTGGGCTGG'] | ['Familial cold urticaria'] |
| NM_006492.2 (ALX3):c.608A>G (p.Asn203Ser) | 121908166 | ALX3 | [ ] | ['CGGYTCTGGAAC CAGACCTGGGG', 'GCGGYTCTGGAA CCAGACCTGGG', 'TGCGGYTCTGGA ACCAGACCTGG'] | ['Frontonasal dysplasia 1'] |
| NM_020451.2 (SEPN1):c.1A>G (p.Met1Val) | 121908184 | SEPN1 | [ ] | ['CCCAYGGCTGCG GCTGGCGGCGG', 'CGGCCCAYGGCT GCGGCTGGCGG'] | ['Eichsfeld type congenital muscular dystrophy'] |
| NM_001127221.1 (CACNA1A):c.4151A>G (p.Tyr1384Cys) | 121908219 | CACNA1A | [ ] | [ ] | ['Familial hemiplegic migraine type 1'] |
| NM_005249.4 (FOXG1):c.686T>A (p.Ile229Asn) | 199502880 | FOXG1 | [ ] | [ ] | ['not provided'] |
| NM_130468.3 (CHST14):c.878A>G (p.Tyr293Cys) | 121908258 | CHST14 | [ ] | ['AAGTCAYAGTG CACGGCACAAGG'] | ['Ehlers-Danlos syndrome, musculocontractural type'] |
| NM_013391.3 (DMGDH):c.326A>G (p.His109Arg) | 121908331 | DMGDH | [ ] | [ ] | ['Dimethylglycine dehydrogenase deficiency'] |
| NM_015166.3 (MLC1):c.422A>G (p.Asn141Ser) | 121908344 | MLC1 | [ ] | [ ] | ['Megalencephalic leukoencephalopathy with subcortical cysts 1'] |
| NM_000441.1 (SLC26A4):c.1105A>G (p.Lys369Glu) | 121908361 | SLC26A4 | [ ] | [ ] | ['Enlarged vestibular aqueduct syndrome'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000441.1 (SLC26A4):c.2168A>G (p.His723Arg) | 121908362 | SLC26A4 | [ ] | [ ] | ['Pendred syndrome', 'Enlarged vestibular aqueduct syndrome'] |
| NM_015560.2 (OPA1):c.1745A>G (p.Tyr582Cys) | 121908376 | OPA1 | [ ] | [ ] | ['Optic Atrophy Type 1'] |
| NM_001128425.1 (MUTYH):c.1241A>G (p.Gln414Arg) | 121908383 | MUTYH | [ ] | ['AAGCYGCTCTGA GGGCTCCCAGG'] | ['Neoplasm of stomach'] |
| NM_015247.2 (CYLD):c.2240A>G (p.Glu747Gly) | 121908389 | CYLD | [ ] | [ ] | ['Familial multiple trichoepitheliomata', 'Spiegler-Brooke syndrome'] |
| NM_021102.3 (SPINT2):c.488A>G (p.Tyr163Cys) | 121908403 | SPINT2 | ['TCCAYAG ATGAAGTT ATTGCAGG'] | ['TCCAYAGATGA AGTTATTGCAGG'] | ['Diarrhea 3, secretory sodium, congenital, syndromic'] |
| NM_004924.4 (ACTN4):c.763A>G (p.Lys255Glu) | 121908415 | ACTN4 | [ ] | [ ] | ['Focal segmental glomerulosclerosis 1'] |
| NM_004795.3 (KL):c.578A>G (p.His193Arg) | 121908423 | KL | ['CAGYGGT ACAGGGTG ACCACGG', 'CCAGYGG TACAGGGT GACCACGG'] | ['CAGYGGTACAG GGTGACCACGGG', 'CCAGYGGTACAG GGTGACCACGG'] | [ ] |
| NM_005682.6 (ADGRG1):c.263A>G (p.Tyr88Cys) | 121908466 | ADGRG1 | ['TGGYAGA GGCCCCTG GGGTCAGG'] | ['TGGYAGAGGCC CCTGGGGTCAGG'] | ['Polymicrogyria, bilateral frontoparietal'] |
| NM_139025.4 (ADAMTS13):c.1582A>G (p.Arg528Gly) | 121908473 | ADAMTS13 | [ ] | [ ] | ['Upshaw-Schulman syndrome'] |
| NM_014270.4 (SLC7A9):c.695A>G (p.Tyr232Cys) | 121908487 | SLC7A9 | [ ] | [ ] | ['Cystinuria'] |
| NM_004211.3 (SLC6A5):c.1472A>G (p.Tyr491Cys) | 121908494 | SLC6A5 | [ ] | [ ] | ['Hyperekplexia 3'] |
| NM_004211.3 (SLC6A5):c.1526A>G (p.Asn509Ser) | 121908497 | SLC6A5 | [ ] | [ ] | ['Hyperekplexia 3'] |
| NM_182643.2 (DLC1):c.2875A>G (p.Thr959Ala) | 121908500 | DLC1 | [ ] | [ ] | ['Carcinoma of colon'] |
| NM_014946.3 (SPAST):c.1322A>G (p.Asp441Gly) | 121908512 | SPAST | [ ] | [ ] | ['Spastic paraplegia 4, autosomal dominant'] |
| NM_014946.3 (SPAST):c.1157A>G (p.Asn386Ser) | 121908514 | SPAST | [ ] | [ ] | ['Spastic paraplegia 4, autosomal dominant'] |
| NM_000026.2 (ADSL):c.736A>G (p.Lys246Glu) | 119450944 | ADSL | [ ] | [ ] | ['Adenylosuccinate lyase deficiency'] |
| NM_000334.4 (SCN4A):c.3478A>G (p.Ile1160Val) | 121908549 | SCN4A | ['TGAYGGA GGGGATGG CGCCTAGG'] | ['TGAYGGAGGGG ATGGCGCCTAGG'] | [ ] |
| NM_000334.4 (SCN4A):c.421A>G (p.Ile141Val) | 121908561 | SCN4A | [ ] | [ ] | ['Paramyotonia congenita of von Eulenburg'] |
| NM_004328.4 (BCS1L):c.148A>G (p.Thr50Ala) | 121908580 | BCS1L | [ ] | ['GTGYGATCATGT AATGGCGCCGG'] | ['Mitochondrial complex III deficiency'] |
| NM_152384.2 (BBS5):c.547A>G (p.Thr183Ala) | 121908582 | BBS5 | [ ] | [ ] | ['Bardet-Biedl syndrome 5'] |
| NM_016417.2 (GLRX5):c.294A>G (p.Gln98=) | 121908584 | GLRX5 | [ ] | ['CCTGACCYTGTC GGAGCTCCGGG'] | ['Anemia, sideroblastic, pyridoxine-refractory, autosomal recessive'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_006206.4 (PDGFRA):c.1664A>G (p.Tyr555Cys) | 121908589 | PDGFRA | [ ] | [ ] | [ ] |
| NM_002755.3 (MAP2K1):c.389A>G (p.Tyr130Cys) | 121908595 | MAP2K1 | ['CCAYAGAAGCCCACGATGTACGG'] | ['CCAYAGAAGCCCACGATGTACGG'] | ['Cardiofaciocutaneous syndrome 3', 'Rasopathy'] |
| NM_012082.3 (ZFPM2):c.89A>G (p.Glu30Gly) | 121908601 | ZFPM2 | [ ] | [ ] | ['Double outlet right ventricle', 'Tetralogy of Fallot', 'Diaphragmatic hernia 3'] |
| NM_012082.3 (ZFPM2):c.2527A>G (p.Thr843Ala) | 121908604 | — | [ ] | [ ] | ['Diaphragmatic hernia 3'] |
| NM_022817.2 (PER2):c.1984A>G (p.Ser662Gly) | 121908635 | PER2 | [ ] | ['GCCACACYCTCTGCCTTGCCCGG'] | ['Advanced sleep phase syndrome, familial'] |
| NM_030761.4 (WNT4):c.647A>G (p.Glu216Gly) | 121908650 | WNT4 | [ ] | [ ] | ['Mullerian aplasia and hyperandrogenism'] |
| NM_003839.3 (TNFRSF11A):c.508A>G (p.Arg170Gly) | 121908655 | TNFRSF11A | [ ] | ['GGGTCYGCATTTGTCCGTGGAGG'] | ['Osteopetrosis autosomal recessive 7'] |
| NM_000539.3 (RHO):c.886A>G (p.Lys296Glu) | 29001653 | RHO | [ ] | ['CGCTCTYGGCAAAGAACGCTGGG', 'GCGCTCTYGGCAAGAACGCTGG'] | ['Retinitis pigmentosa 4'] |
| NM_004006.2 (DMD):c.2317A>G (p.Lys773Glu) | 128626244 | DMD | [ ] | [ ] | ['Duchenne muscular dystrophy'] |
| NM_003722.4 (TP63):c.697A>G (p.Lys233Glu) | 121908838 | TP63 | ['AGCTTYTTTGTAGACAGGCATGG'] | ['AGCTTYTTTGTAGACAGGCATGG'] | ['Split-hand/foot malformation 4'] |
| NM_003722.4 (TP63):c.1052A>G (p.Asp351Gly) | 121908844 | TP63 | [ ] | [ ] | ['Ectrodactyly, ectodermal dysplasia, and cleft lip/palate syndrome 3'] |
| NM_003722.4 (TP63):c.1054A>G (p.Arg352Gly) | 121908847 | TP63 | [ ] | [ ] | ['ADULT syndrome', 'Orofacial cleft 8'] |
| NM_000369.2 (TSHR):c.1856A>G (p.Asp619Gly) | 121908859 | TSHR | [ ] | [ ] | ['Thyroid adenoma, hyperfunctioning'] |
| NM_000369.2(TSHR): c.548A>G (p.Lys183Arg) | 121908879 | TSHR | [ ] | [ ] | ['Hyperthyroidism, familial gestational'] |
| NM_003060.3 (SLC22A5):c.632A>G (p.Tyr211Cys) | 121908888 | SLC22A5 | [ ] | [ ] | ['Renal carnitine transport defect', 'not provided'] |
| NM_006502.2 (POLH):c.1603A>G (p.Lys535Glu) | 56307355 | POLH | [ ] | ['AGACTTTYCTGCTTAAAGAAGGG'] | ['Xeroderma pigmentosum, variant type'] |
| NM_002977.3 (SCN9A):c.1964A>G (p.Lys655Arg) | 121908919 | — | [ ] | ['CCTTTTCYTGTGTATTTGATTGG'] | ['Generalized epilepsy with febrile seizures plus, type 7', 'not specified'] |
| NM_002977.3 (SCN9A):c.184A>G (p.Ile62Val) | 121908920 | SCN9A | [ ] | [ ] | ['Febrile seizures, familial, 3b'] |
| NM_006892.3 (DNMT3B):c.2450A>G (p.Asp817Gly) | 121908939 | DNMT3B | [ ] | ['GACACGYCTGTGTAGTGCACAGG'] | ['Centromeric instability of chromosomes 1,9 and 16 and immunodeficiency'] |
| NM_001130978.1 (DYSF):c.3892A>G (p.Ile1298Val) | 121908954 | DYSF | [ ] | [ ] | ['Miyoshi muscular dystrophy 1', 'Limb-girdle muscular dystrophy, type 2B', 'not specified'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_001130978.1 (DYSF):c.5264A>G (p.Glu1755Gly) | 121908961 | DYSF | [ ] | [ ] | ['Limb-girdle muscular dystrophy, type 2B'] |
| NM_016203.3 (PRKAG2):c.1148A>G (p.His383Arg) | 121908988 | PRKAG2 | [ ] | [ ] | ['Familial hypertrophic cardiomyopathy 6'] |
| NM_000492.3 (CFTR):c.2738A>G (p.Tyr913Cys) | 121909008 | CFTR | ['CACATAA YACGAACT GGTGCTGG'] | ['CACATAAYACG AACTGGTGCTGG'] | ['Cystic fibrosis'] |
| NM_000492.3 (CFTR):c.326A>G (p.Tyr109Cys) | 121909031 | CFTR | [ ] | [ ] | ['Cystic fibrosis'] |
| NM_000492.3 (CFTR):c.650A>G (p.Glu217Gly) | 121909046 | CFTR | [ ] | [ ] | ['Cystic fibrosis'] |
| NM_001040667.2 (HSF4):c.256A>G (p.Ile86Val) | 121909050 | HSF4 | [ ] | [ ] | ['Cataract, zonular'] |
| NM_005025.4 (SERPINI1):c.1013A>G (p.His338Arg) | 121909052 | SERPINI1 | [ ] | [ ] | ['Familial encephalopathy with neuroserpin inclusion bodies'] |
| NM_005422.2 (TECTA):c.5609A>G (p.Tyr1870Cys) | 121909058 | TECTA | [ ] | [ ] | ['Deafness, autosomal dominant 12'] |
| NM_170695.3 (TGIF1):c.838A>G (p.Thr280Ala) | 121909068 | TGIF1 | [ ] | [ ] | ['Holoprosencephaly 4'] |
| NM_001005360.2 (DNM2):c.1684A>G (p.Lys562Glu) | 121909088 | DNM2 | [ ] | ['ACTYCTTCTCTT TCTCCTGAGGG', 'TACTYCTTCTCTT TCTCCTGAGG'] | ['Charcot-Marie-Tooth disease, dominant intermediate b, with neutropenia'] |
| NM_000483.4 (APOC2):c.1A>G (p.Met1Val) | 120074112 | — | [ ] | ['GCCCAYAGTGTC CAGAGACCTGG'] | ['Apolipoprotein C2 deficiency'] |
| NM_000543.4 (SMPD1):c.1154A>G (p.Asn385Ser) | 120074123 | SMPD1 | [ ] | [ ] | ['Niemann-Pick disease, type B'] |
| NM_000019.3 (ACAT1):c.278A>G (p.Asn93Ser) | 120074145 | ACAT1 | [ ] | [ ] | ['Deficiency of acetyl-CoA acetyltransferase'] |
| NM_138477.2 (CDAN1):c.1796A>G (p.Asn599Ser) | 120074166 | CDAN1 | [ ] | [ ] | ['Congenital dyserythropoietic anemia, type I'] |
| NM_000187.3 (HGD):c.1102A>G (p.Met368Val) | 120074173 | HGD | [ ] | [ ] | ['Alkaptonuria'] |
| NM_001089.2 (ABCA3):c.1702A>G (p.Asn568Asp) | 121909184 | ABCA3 | ['ACCGTYG TGGCCCAG CAGGACGG'] | ['ACCGTYGTGGCC CAGCAGGACGG'] | ['Surfactant metabolism dysfunction, pulmonary, 3'] |
| NM_000503.5 (EYA1):c.1639A>G (p.Arg547Gly) | 121909197 | EYA1 | [ ] | [ ] | [ ] |
| NM_000218.2 (KCNQ1):c.418A>G (p.Ser140Gly) | 120074192 | KCNQ1 | ['CGCYGAA GATGAGGC AGACCAGG'] | ['CGCYGAAGATG AGGCAGACCAGG'] | ['Atrial fibrillation, familial, 3', 'Atrial fibrillation'] |
| NM_000314.6 (PTEN):c.368A>G (p.His123Arg) | 121909222 | PTEN | [ ] | [ ] | ['Cowden syndrome 1'] |
| NM_000314.6 (PTEN):c.278A>G (p.His93Arg) | 121909238 | PTEN | [ ] | [ ] | ['Hereditary cancer-predisposing syndrome', 'Macrocephaly/autism syndrome'] |
| NM_000314.6 (PTEN):c.755A>G (p.Asp252Gly) | 121909239 | PTEN | [ ] | ['ATAYCACCACAC ACAGGTAACGG'] | ['Macrocephaly/autism syndrome'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_198217.2 (ING1):c.515A>G (p.Asn172Ser) | 121909251 | ING1 | [ ] | ['TGGYTGCACAG ACAGTACGTGGG', 'CTGGYTGCACAG ACAGTACGTGG'] | ['Squamous cell carcinoma of the head and neck'] |
| NM_012338.3 (TSPAN12):c.734T>C (p.Leu245Pro) | 200519776 | TSPAN12 | [ ] | [ ] | ['Exudative vitreoretinopathy 5'] |
| NM_001001557.2 (GDF6):c.1271A>G (p.Lys424Arg) | 121909353 | GDF6 | [ ] | [ ] | ['Klippel-Feil syndrome 1, autosomal dominant'] |
| NM_000163.4 (GHR):c.594A>G (p.Glu198=) | 121909360 | GHR | [ ] | [ ] | ['Laron-type isolated somatotropin defect'] |
| NM_000256.3 (MYBPC3):c.175A>G (p.Thr59Ala) | 121909375 | MYBPC3 | [ ] | [ ] | ['Familial hypertrophic cardiomyopathy 4'] |
| NM_001174089.1 (SLC4A11):c.2518A>G (p.Met840Val) | 121909396 | SLC4A11 | [ ] | ['GATCAYCTTCAT GTAGGGCAGGG', 'AGATCAYCTTCA TGTAGGGCAGG'] | ['Corneal dystrophy and perceptive deafness'] |
| NM_001100.3 (ACTA1):c.350A>G (p.Asn117Ser) | 121909520 | ACTA1 | ['GCGGYTG GCCTTGGG ATTGAGGG', 'CGCGGYT GGCCTTGG GATTGAGG'] | ['CGGYTGGCCTTG GGATTGAGGGG', 'GCGGYTGGCCTT GGGATTGAGGG', 'CGCGGYTGGCCT TGGGATTGAGG'] | ['Nemaline myopathy 3'] |
| NM_000034.3 (ALDOA):c.386A>G (p.Asp129Gly) | 121909533 | ALDOA | [ ] | ['CCAYCCAACCCT AAGAGAAGAGG'] | ['HNSHA due to aldolase A deficiency'] |
| NM_000495.4 (COL4A5):c.3455-9A>G | 104886388 | COL4A5 | [ ] | [ ] | ['Alport syndrome, X-linked recessive'] |
| NM_001145.4 (ANG):c.208A>G (p.Ile70Val) | 121909541 | — | [ ] | [ ] | ['Amyotrophic lateral sclerosis type 9'] |
| NM_000051.3 (ATM):c.3118A>G (p.Met1040Val) | 3092857 | ATM | [ ] | [ ] | ['Hereditary cancer-predisposing syndrome', 'not specified'] |
| NM_023110.2 (FGFR1):c.1121A>G (p.Tyr374Cys) | 121909631 | FGFR1 | [ ] | [ ] | ['Osteoglophonic dysplasia'] |
| NM_182925.4 (FLT4):c.3104A>G (p.His1035Arg) | 121909653 | FLT4 | ['CTGYGGA TGCACTGG GGTGCGGG', 'TCTGYGG ATGCACTG GGGTGCGG'] | ['CTGYGGATGCAC TGGGGTGCGGG', 'TCTGYGGATGCA CTGGGGTGCGG'] | [ ] |
| NM_000145.3 (FSHR):c.1345A>G (p.Thr449Ala) | 121909663 | FSHR | [ ] | [ ] | ['Ovarian hyperstimulation syndrome'] |
| NM_001017420.2 (ESCO2):c.1132-7A>G | 80359862 | ESCO2 | [ ] | [ ] | ['Roberts-SC phocomelia syndrome'] |
| NM_001017420.2 (ESCO2):c.1674-2A>G | 80359869 | ESCO2 | [ ] | [ ] | ['Roberts-SC phocomelia syndrome'] |
| NM_024577.3 (SH3TC2):c.505T>C (p.Tyr169His) | 80359890 | SH3TC2 | [ ] | [ ] | ['Charcot-Marie-Tooth disease, type 4C', 'Charcot-Marie-Tooth disease, type IV', 'Mononeuropathy of the median nerve, mild'] |
| NM_032119.3 (ADGRV1):c.18131A>G (p.Tyr6044Cys) | 121909763 | ADGRV1 | [ ] | [ ] | ['Usher syndrome, type 2C'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_001360.2 (DHCR7):c.839A>G (p.Tyr280Cys) | 121909766 | DHCR7 | [ ] | [ ] | ['Smith-Lemli-Opitz syndrome'] |
| NM_000517.4 (HBA2):c.1A>G (p.Met1Val) | 121909803 | HBA2 | [ ] | [ ] | ['Hemoglobin H disease, nondeletional'] |
| NM_004006.2 (DMD):c.835A>G (p.Thr279Ala) | 128627255 | DMD | [ ] | ['TGACCGYGATCT GCAGAGAAGGG', 'CTGACCGYGATC TGCAGAGAAGG'] | ['Dilated cardiomyopathy 3B'] |
| NM_015896.3 (ZMYND10):c.797T>C (p.Leu266Pro) | 200913791 | ZMYND10 | [ ] | [ ] | ['Kartagener syndrome', 'Ciliary dyskinesia, primary, 22'] |
| NM_001085.4 (SERPINA3):c.1240A>G (p.Met414Val) | 116929575 | SERPINA3 | [ ] | ['GCTCAYGAAGA AGATGTTCTGGG', 'TGCTCAYGAAGA AGATGTTCTGG'] | [ ] |
| NM_058216.2 (RAD51C):c.1027-2A>G | 587780835 | RAD51C | [ ] | [ ] | ['Fanconi anemia, complementation group O'] |
| NM_006231.3 (POLE):c.4444+3A>G | 398122515 | POLE | [ ] | [ ] | ['Facial dysmorphism, immunodeficiency, livedo, and short stature'] |
| NM_002769.4 (PRSS1):c.161A>G (p.Asn54Ser) | 144422014 | — | [ ] | [ ] | ['Hereditary pancreatitis'] |
| NM_001204316.1 (PRLR):c.635A>G (p.His212Arg) | 398122522 | PRLR | [ ] | [ ] | ['Hyperprolactinemia'] |
| NM_004992.3 (MECP2):c.410A>G (p.Glu137Gly) | 61748392 | MECP2 | [ ] | ['CAACYCCACTTT AGAGCGAAAGG'] | ['Mental retardation, X-linked, syndromic 13'] |
| NM_020366.3 (RPGRIP1):c.3749-2A>G | 376517859 | RPGRIP1 | [ ] | [ ] | ['Cone-rod dystrophy 13'] |
| NM_000552.3 (VWF):c.2384A>G (p.Tyr795Cys) | 61748478 | VWF | ['GTCAYAG TTCTGGCA CGTTTTGG'] | ['GTCAYAGTTCTG GCACGTTTTGG'] | ['von Willebrand disease type 2N', 'not provided'] |
| NM_001040613.2 (TMEM70):c.*7-2A>G | 183973249 | TMEM70 | [ ] | [ ] | ['Nuclearly-encoded mitochondrial complex V (ATP synthase) deficiency 2'] |
| NM_001005741.2 (GBA):c.1049A>G (p.His350Arg) | 78198234 | GBA | [ ] | [ ] | ['Gaucher disease, perinatal lethal'] |
| NM_000218.2 (KCNQ1):c.332A>G (p.Tyr111Cys) | 199472678 | KCNQ1 | [ ] | [ ] | ['Congenital long QT syndrome', 'Cardiac arrhythmia', 'Long QT syndrome, LQT1 subtype'] |
| NM_000218.2 (KCNQ1):c.344A>G (p.Glu115Gly) | 199472679 | KCNQ1 | | | ['Congenital long QT syndrome', 'Long QT syndrome, LQT1 subtype'] |
| NM_000218.2 (KCNQ1):c.440A>G (p.Gln147Arg) | 199472689 | KCNQ1 | | | ['Atrial fibrillation'] |
| NM_000218.2 (KCNQ1):c.592A>G (p.Ile198Val) | 199472700 | KCNQ1 | [ ] | [ ] | ['Congenital long QT syndrome'] |
| NM_001943.3 (DSG2):c.880A>G (p.Lys294Glu) | 752432726 | DSG2 | [ ] | [ ] | ['Cardiomyopathy'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000218.2 (KCNQ1):c.820A>G (p.Ile274Val) | 199472728 | KCNQ1 | [ ] | [ ] | ['Sudden infant death syndrome', 'Congenital long QT syndrome', 'Cardiac arrhythmia'] |
| NM_000218.2 (KCNQ1):c.842A>G (p.Tyr281Cys) | 199472732 | KCNQ1 | | | ['Congenital long QT syndrome'] |
| NM_000218.2 (KCNQ1):c.950A>G (p.Asp317Gly) | 199472750 | KCNQ1 | | | ['Congenital long QT syndrome'] |
| NM_000218.2 (KCNQ1):c.964A>G (p.Thr322Ala) | 199472754 | KCNQ1 | | | ['Congenital long QT syndrome', 'Cardiac arrhythmia', 'Long QT syndrome, LQT1 subtype'] |
| NM_000218.2 (KCNQ1):c.1138A>G (p.Arg380Gly) | 199472770 | KCNQ1 | | | ['Congenital long QT syndrome'] |
| NM_000218.2 (KCNQ1):c.1193A>G (p.Lys398Arg) | 199472777 | KCNQ1 | | | ['Congenital long QT syndrome', 'Cardiac arrhythmia'] |
| NM_000218.2 (KCNQ1):c.1640A>G (p.Gln547Arg) | 199472798 | KCNQ1 | | | ['Congenital long QT syndrome'] |
| NM_000218.2 (KCNQ1):c.1669A>G (p.Lys557Glu) | 199472801 | KCNQ1 | | | ['Congenital long QT syndrome'] |
| NM_000218.2 (KCNQ1):c.1705A>G (p.Lys569Glu) | 199472808 | KCNQ1 | | | ['Congenital long QT syndrome'] |
| NM_001005741.2 (GBA):c.667T>C (p.Trp223Arg) | 61748906 | GBA | [ ] | ['CCACTYGGCTC AAGACCAATGG'] | ['Gaucher disease, type 1', 'not provided'] |
| NM_000218.2 (KCNQ1):c.1756A>G (p.Asn586Asp) | 199472812 | KCNQ1 | | | ['Congenital long QT syndrome', 'Long QT syndrome, LQT1 subtype'] |
| NM_000218.2 (KCNQ1):c.1793A>G (p.Lys598Arg) | 199472817 | KCNQ1 | | | ['Sudden infant death syndrome'] |
| NM_000238.3 (KCNH2):c.82A>G (p.Lys28Glu) | 199472829 | KCNH2 | | | ['Congenital long QT syndrome'] |
| NM_000238.3 (KCNH2):c.128A>G (p.Tyr43Cys) | 199472836 | KCNH2 | | | ['Congenital long QT syndrome', 'Cardiac arrhythmia'] |
| NM_000238.3 (KCNH2):c.301A>G (p.Lys101Glu) | 199472856 | KCNH2 | [ ] | [ ] | ['Congenital long QT syndrome', 'Cardiac arrhythmia'] |
| NM_000238.3 (KCNH2):c.652A>G (p.Met218Val) | 199472869 | KCNH2 | | | ['Congenital long QT syndrome'] |
| NM_000238.3 (KCNH2):c.1424A>G (p.Tyr475Cys) | 199472907 | KCNH2 | | | ['Congenital long QT syndrome'] |
| NM_000238.3 (KCNH2):c.1777A>G (p.Ile593Val) | 199472930 | KCNH2 | | | ['Congenital long QT syndrome'] |
| NM_000238.3 (KCNH2):c.1783A>G (p.Lys595Glu) | 199472932 | KCNH2 | | | ['Congenital long QT syndrome'] |
| NM_000238.3 (KCNH2):c.1790A>G (p.Tyr597Cys) | 199472934 | KCNH2 | | | ['Long QT syndrome', 'Congenital long QT syndrome'] |
| NM_000238.3 (KCNH2):c.1826A>G (p.Asp609Gly) | 199472940 | KCNH2 | | | ['Congenital long QT syndrome'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000238.3 (KCNH2):c.1847A>G (p.Tyr616Cys) | 199472946 | KCNH2 | | | ['Long QT syndrome', 'Congenital long QT syndrome', 'Cardiac arrhythmia'] |
| NM_000238.3 (KCNH2):c.1885A>G (p.Asn629Asp) | 199472956 | KCNH2 | | | ['Congenital long QT syndrome', 'Cardiac arrhythmia'] |
| NM_000238.3 (KCNH2):c.1897A>G (p.Asn633Asp) | 199472960 | KCNH2 | | | ['Congenital long QT syndrome'] |
| NM_000238.3 (KCNH2):c.1903A>G (p.Asn635Asp) | 199472963 | KCNH2 | | | ['Congenital long QT syndrome'] |
| NM_000238.3 (KCNH2):c.1910A>G (p.Glu637Gly) | 199472967 | KCNH2 | | | ['Congenital long QT syndrome'] |
| NM_000238.3 (KCNH2):c.2510A>G (p.Asp837Gly) | 199473004 | KCNH2 | | | ['Congenital long QT syndrome', 'Cardiac arrhythmia'] |
| NM_000238.3 (KCNH2):c.2591A>G (p.Asp864Gly) | 199473008 | KCNH2 | | | ['Congenital long QT syndrome'] |
| NM_000238.3 (KCNH2):c.3118A>G (p.Ser1040Gly) | 199473024 | KCNH2 | [ ] | ['CTGCYCTCCACG TCGCCCCGGGG', 'CCTGCYCTCCAC GTCGCCCCGGG', 'GCCTGCYCTCCA CGTCGCCCCGG'] | ['Sudden infant death syndrome'] |
| NM_000238.3 (KCNH2):c.3233A>G (p.Tyr1078Cys) | 199473029 | KCNH2 | | | ['Congenital long QT syndrome'] |
| NM_000335.4 (SCN5A):c.343A>G (p.Ser115Gly) | 199473057 | SCN5A | | | ['Congenital long QT syndrome'] |
| m.827A>G | 28358569 | MT-RNR1 | [ ] | [ ] | ['Aminoglycoside-induced deafness', 'Deafness, nonsyndromic sensorineural, mitochondrial'] |
| NM_000335.4 (SCN5A):c.688A>G (p.Ile230Val) | 199473074 | SCN5A | ['ATAYAGT TTTCAGGG CCCGGAGG', 'CTGATAY AGTTTTCA GGGCCCGG'] | ['ATAYAGTTTTCA GGGCCCGGAGG', 'CTGATAYAGTTT TCAGGGCCCGG'] | ['Brugada syndrome'] |
| NM_000335.4 (SCN5A):c.715A>G (p.Ile239Val) | 199473075 | SCN5A | | | ['Congenital long QT syndrome'] |
| NM_000252.2 (MTM1):c.575A>G (p.Tyr192Cys) | 587783838 | MTM1 | [ ] | [ ] | ['Severe X-linked myotubular myopathy'] |
| NM_004572.3 (PKP2):c.275T>A (p.Leu92Ter) | 763639737 | PKP2 | [ ] | [ ] | ['not provided'] |
| NM_000335.4 (SCN5A):c.1502A>G (p.Asp501Gly) | 199473117 | SCN5A | | | ['Brugada syndrome'] |
| NM_000335.4 (SCN5A):c.2249A>G (p.Gln750Arg) | 199473152 | SCN5A | | | ['Congenital long QT syndrome'] |
| NM_198056.2 (SCN5A):c.2527A>G (p.Thr843Ala) | 199473165 | SCN5A | | | ['Congenital long QT syndrome', 'not provided'] |
| NM_001165963.1 (SCN1A):c.1277A>G (p.Tyr426Cys) | 796052973 | SCN1A | [ ] | [ ] | ['not provided'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000335.4 (SCN5A):c.3755A>G (p.Glu1252Gly) | 199473214 | SCN5A | | | ['Brugada syndrome'] |
| NM_198056.2 (SCN5A):c.4000A>G (p.Ile1334Val) | 199473226 | SCN5A | [ ] | [ ] | ['Congenital long QT syndrome', 'not provided'] |
| NM_000335.4 (SCN5A):c.4252A>G (p.Lys1418Glu) | 199473242 | SCN5A | | | ['Brugada syndrome'] |
| NM_000335.4 (SCN5A):c.4291A>G (p.Arg1431Gly) | 199473245 | SCN5A | | | ['Brugada syndrome'] |
| NM_000335.4 (SCN5A):c.4412A>G (p.Asn1471Ser) | 199473255 | SCN5A | | | ['Congenital long QT syndrome'] |
| NM_198056.2 (SCN5A):c.4478A>G (p.Lys1493Arg) | 199473260 | SCN5A | [ ] | [ ] | ['Atrial fibrillation', 'Congenital long QT syndrome', 'not provided'] |
| NM_000335.4 (SCN5A):c.4489A>G (p.Met1497Val) | 199473264 | SCN5A | | | ['Congenital long QT syndrome'] |
| NM_000335.4 (SCN5A):c.4577A>G (p.Lys1526Arg) | 199473270 | SCN5A | | | ['Brugada syndrome'] |
| NM_000335.4 (SCN5A):c.5161A>G (p.Asn1721Asp) | 199473299 | SCN5A | | | ['Brugada syndrome'] |
| NM_198056.2 (SCN5A):c.5302A>G (p.Ile1768Val) | 199473311 | SCN5A | | | ['Congenital long QT syndrome', 'not provided'] |
| NM_000335.4 (SCN5A):c.5318A>G (p.Asn1773Ser) | 199473313 | SCN5A | | | ['Brugada syndrome'] |
| NM_000335.4 (SCN5A):c.5366A>G (p.Asp1789Gly) | 199473317 | SCN5A | | | ['Congenital long QT syndrome'] |
| NM_000335.4 (SCN5A):c.5402A>G (p.Asp1801Gly) | 199473318 | SCN5A | | | ['Congenital long QT syndrome'] |
| NM_000335.4 (SCN5A):c.5513A>G (p.Asp1838Gly) | 199473321 | SCN5A | | | ['Congenital long QT syndrome'] |
| NM_198056.2 (SCN5A):c.5726A>G (p.Gln1909Arg) | 199473326 | SCN5A | | | ['Congenital long QT syndrome', 'not provided'] |
| NM_172201.1 (KCNE2):c.269A>G (p.Glu90Gly) | 199473366 | KCNE2 | | | ['Atrial fibrillation'] |
| NM_000891.2 (KCNJ2):c.223A>G (p.Thr75Ala) | 199473370 | KCNJ2 | | | ['Congenital long QT syndrome'] |
| NM_000891.2 (KCNJ2):c.233A>G (p.Asp78Gly) | 199473371 | KCNJ2 | | | ['Andersen Tawil syndrome', 'Congenital long QT syndrome'] |
| NM_000891.2 (KCNJ2):c.574A>G (p.Thr192Ala) | 199473382 | KCNJ2 | | | ['Congenital long QT syndrome'] |
| NM_000218.2 (KCNQ1):c.548A>G (p.Lys183Arg) | 199473396 | KCNQ1 | | | ['Congenital long QT syndrome'] |
| NM_000218.2 (KCNQ1):c.1061A>G (p.Lys354Arg) | 199473404 | KCNQ1 | | | ['Congenital long QT syndrome'] |
| NM_000218.2 (KCNQ1):c.1070A>G (p.Gln357Arg) | 199473405 | KCNQ1 | | | ['Congenital long QT syndrome', 'Cardiac arrhythmia', 'Long QT syndrome, LQT1 subtype'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000218.2 (KCNQ1):c.1078A>G (p.Arg360Gly) | 199473406 | KCNQ1 | [ ] | [ ] | ['Congenital long QT syndrome'] |
| NM_000238.3 (KCNH2):c.209A>G (p.His70Arg) | 199473419 | KCNH2 | | | ['Congenital long QT syndrome', 'Cardiac arrhythmia'] |
| NM_000238.3 (KCNH2):c.1724A>G (p.Glu575Gly) | 199473424 | KCNH2 | | | ['Congenital long QT syndrome'] |
| NM_000238.3 (KCNH2):c.1747A>G (p.Ile583Val) | 199473427 | KCNH2 | | | ['Congenital long QT syndrome'] |
| NM_000238.3 (KCNH2):c.1762A>G (p.Asn588Asp) | 199473431 | KCNH2 | | | ['Congenital long QT syndrome'] |
| NM_000218.2 (KCNQ1):c.430A>G (p.Thr144Ala) | 199473451 | KCNQ1 | | | ['Congenital long QT syndrome'] |
| NM_000218.2 (KCNQ1):c.931A>G (p.Thr311Ala) | 199473469 | KCNQ1 | | | ['Congenital long QT syndrome'] |
| NM_000238.3 (KCNH2):c.286A>G (p.Ile96Val) | 199473496 | KCNH2 | | | ['Congenital long QT syndrome'] |
| NM_000238.3 (KCNH2):c.1205A>G (p.His402Arg) | 199473506 | KCNH2 | | | ['Congenital long QT syndrome'] |
| NM_000238.3 (KCNH2):c.1259A>G (p.Tyr420Cys) | 199473507 | KCNH2 | | | ['Congenital long QT syndrome'] |
| NM_000238.3 (KCNH2):c.1502A>G (p.Asp501Gly) | 199473513 | KCNH2 | | | ['Congenital long QT syndrome', 'Cardiac arrhythmia'] |
| NM_000238.3 (KCNH2):c.1912A>G (p.Lys638Glu) | 199473528 | KCNH2 | | | ['Congenital long QT syndrome'] |
| NM_000238.3 (KCNH2):c.2131A>G (p.Ile711Val) | 199473532 | KCNH2 | [ ] | [ ] | ['Long QT syndrome', 'Congenital long QT syndrome', 'Cardiac arrhythmia'] |
| NM_000238.3 (KCNH2):c.2266A>G (p.Met756Val) | 199473534 | KCNH2 | | | ['Acquired long QT syndrome'] |
| NM_000238.3 (KCNH2):c.3343A>G (p.Met1115Val) | 199473546 | KCNH2 | | | ['Congenital long QT syndrome', 'Cardiac arrhythmia'] |
| NM_000335.4 (SCN5A):c.89A>G (p.Glu30Gly) | 199473551 | SCN5A | | | ['Congenital long QT syndrome'] |
| NM_000335.4 (SCN5A):c.1217A>G (p.Asn406Ser) | 199473568 | SCN5A | | | ['Brugada syndrome'] |
| NM_000249.3 (MLH1):c.791-2A>G | 267607794 | MLH1 | [ ] | [ ] | ['Hereditary Nonpolyposis Colorectal Neoplasms', 'Hereditary cancer-predisposing syndrome'] |
| NM_000335.4 (SCN5A):c.2780A>G (p.Asn927Ser) | 199473589 | SCN5A | | | ['Brugada syndrome'] |
| NM_000335.4 (SCN5A):c.3164A>G (p.Asp1055Gly) | 199473593 | SCN5A | | | ['Brugada syndrome'] |
| NM_000335.4 (SCN5A):c.4223A>G (p.Tyr1408Cys) | 199473610 | SCN5A | | | ['Brugada syndrome'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_198056.2 (SCN5A):c.4346A>G (p.Tyr1449Cys) | 199473613 | SCN5A | | | ['Brugada syndrome', 'not provided'] |
| NM_198056.2 (SCN5A):c.4978A>G (p.Ile1660Val) | 199473625 | SCN5A | ['CGAYGTT GAAGAGG GCAGGCAG G'] | ['CGAYGTTGAAG AGGGCAGGCAGG', 'AGCCCGAYGTTG AAGAGGGCAGG'] | ['Brugada syndrome', 'not provided'] |
| NM_000335.4 (SCN5A):c.5138A>G (p.Asp1713Gly) | 199473628 | SCN5A | | | ['Brugada syndrome'] |
| NM_000335.4 (SCN5A):c.5297A>G (p.Tyr1766Cys) | 199473632 | SCN5A | | | ['Congenital long QT syndrome'] |
| NM_000335.4 (SCN5A):c.5317A>G (p.Asn1773Asp) | 199473633 | SCN5A | | | ['Congenital long QT syndrome'] |
| NM_000531.5 (OTC):c.527A>G (p.Tyr176Cys) | 72556283 | OTC | ['TGAGGYA ATCAGCCA GGATCTGG'] | ['TGAGGYAATCA GCCAGGATCTGG'] | ['not provided'] |
| NM_001130823.1 (DNMT1):c.1532A>G (p.Tyr511Cys) | 199473690 | DNMT1 | | | ['Hereditary sensory neuropathy type IE'] |
| NM_000303.2 (PMM2):c.563A>G (p.Asp188Gly) | 80338704 | PMM2 | [ ] | [ ] | ['Carbohydrate-deficient glycoprotein syndrome type I', 'not provided'] |
| NM_000051.3 (ATM):c.8030A>G (p.Tyr2677Cys) | 28942103 | — | [ ] | [ ] | ['Ataxia-telangiectasia variant'] |
| NM_175053.3 (KRT74):c.821T>C (p.Phe274Ser) | 147962513 | KRT74 | [ ] | [ ] | ['"Ectodermal dysplasia, \'pure\' hair-nail type"', 'Ectodermal dysplasia 7, hair/nail type'] |
| NM_000059.3 (BRCA2):c.426-2A>G | 398122779 | BRCA2 | [ ] | [ ] | ['Familial cancer of breast', 'Breast-ovarian cancer, familial 2'] |
| NM_133433.3 (NIPBL):c.5428-2A>G | 587783974 | NIPBL | [ ] | [ ] | ['Cornelia de Lange syndrome 1'] |
| NM_000238.3 (KCNH2):c.1129-2A>G | 794728365 | KCNH2 | [ ] | ['GGACCYGCACC CGGGGAAGGCGG'] | ['Cardiac arrhythmia'] |
| NM_000260.3 (MYO7A):c.6029A>G (p.Asp2010Gly) | 111033175 | MYO7A | [ ] | [ ] | ['Usher syndrome, type 1'] |
| NM_000531.5 (OTC):c.548A>G (p.Tyr183Cys) | 72556293 | OTC | [ ] | ['AGAGCTAYAGT GTTCCTAAAAGG'] | ['not provided'] |
| NM_000441.1 (SLC26A4):c.1151A>G (p.Glu384Gly) | 111033244 | SLC26A4 | [ ] | ['TGAATYCCTAAG GAAGAGACTGG'] | ['Pendred syndrome', 'Enlarged vestibular aqueduct syndrome'] |
| NM_004004.5 (GJB2):c.617A>G (p.Asn206Ser) | 111033294 | GJB2 | [ ] | [ ] | ['Deafness, autosomal recessive 1A', 'Hearing impairment'] |
| NM_000441.1 (SLC26A4):c.919-2A>G | 111033313 | SLC26A4 | [ ] | [ ] | ['Pendred syndrome', 'Enlarged vestibular aqueduct syndrome'] |
| NM_001363.4 (DKC1):c.115A>G (p.Lys39Glu) | 121912296 | DKC1 | [ ] | [ ] | ['Dyskeratosis congenita X-linked'] |
| NM_001363.4 (DKC1):c.196A>G (p.Thr66Ala) | 121912297 | DKC1 | [ ] | [ ] | ['Dyskeratosis congenita X-linked'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_001363.4 (DKC1):c.361A>G (p.Ser121Gly) | 121912305 | DKC1 | [ ] | [ ] | ['Dyskeratosis congenita X-linked', 'Hoyeraal Hreidarsson syndrome'] |
| NM_178151.2 (DCX):c.413A>G (p.Tyr138Cys) | 587783552 | DCX | [ ] | [ ] | ['Heterotopia'] |
| NM_024675.3 (PALB2):c.212-2A>G | 730881879 | PALB2 | [ ] | [ ] | ['Hereditary cancer-predisposing syndrome'] |
| NM_000260.3 (MYO7A):c.1344-2A>G | 111033415 | MYO7A | [ ] | ['AGCYGCAGGGG CACAGGGATGGG', 'AAGCYGCAGGGG CACAGGGATGG'] | ['Usher syndrome, type 1'] |
| NM_000454.4 (SOD1):c.131A>G (p.His44Arg) | 121912435 | SOD1 | [ ] | [ ] | ['Amyotrophic lateral sclerosis type 1'] |
| NM_000454.4 (SOD1):c.302A>G (p.Glu101Gly) | 121912439 | SOD1 | [ ] | ['AGAATCTYCAAT AGACACATCGG'] | ['Amyotrophic lateral sclerosis type 1'] |
| NM_000454.4 (SOD1):c.140A>G (p.His47Arg) | 121912443 | SOD1 | [ ] | [ ] | ['Amyotrophic lateral sclerosis type 1'] |
| NM_133433.3 (NIPBL):c.737A>G (p.Asp246Gly) | 587784042 | NIPBL | [ ] | [ ] | ['Cornelia de Lange syndrome 1'] |
| NM_000454.4(SOD1): c.242A>G (p.His81Arg) | 121912458 | SOD1 | [ ] | [ ] | ['Amyotrophic lateral sclerosis type 1'] |
| NM_001754.4 (RUNX1):c.328A>G (p.Lys110Glu) | 121912498 | RUNX1 | [ ] | [ ] | ['Familial platelet disorder with associated myeloid malignancy'] |
| NM_000238.3 (KCNH2):c.1408A>G (p.Asn470Asp) | 121912505 | KCNH2 | [ ] | [ ] | ['Long QT syndrome 2', 'Congenital long QT syndrome'] |
| NM_000233.3 (LHCGR):c.1733A>G (p.Asp578Gly) | 121912518 | — | [ ] | [ ] | ['Gonadotropin-independent familial sexual precocity'] |
| NM_000493.3 (COL10A1):c.1790A>G (p.Tyr597Cys) | 111033554 | — | [ ] | [ ] | ['Metaphyseal chondrodysplasia, Schmid type'] |
| NM_000233.3 (LHCGR):c.1691A>G (p.Asp564Gly) | 121912540 | — | [ ] | [ ] | ['Gonadotropin-independent familial sexual precocity'] |
| NM_002769.4 (PRSS1):c.68A>G (p.Lys23Arg) | 111033567 | — | [ ] | ['ATCYTGTCATCA TCATCAAAGGG', 'GATCYTGTCATC ATCATCAAAGG'] | ['Hereditary pancreatitis'] |
| NM_004999.3 (MYO6):c.737A>G (p.His246Arg) | 121912560 | MYO6 | [ ] | [ ] | ['Sensorineural deafness with hypertrophic cardiomyopathy'] |
| NM_000901.4 (NR3C2):c.2327A>G (p.Gln776Arg) | 121912565 | NR3C2 | [ ] | ['TCATCYGTTTGC CTGCTAAGCGG'] | ['Pseudohypoaldosteronism type 1 autosomal dominant'] |
| NM_000901.4 (NR3C2):c.2915A>G (p.Glu972Gly) | 121912574 | NR3C2 | [ ] | ['CCGACYCCACCT TGGGCAGCTGG'] | ['Pseudohypo-aldosteronism type 1 autosomal dominant'] |
| NM_001173464.1 (KIF21A):c.2839A>G (p.Met947Val) | 121912589 | KIF21A | [ ] | ['ATTCAYATCTGC CTCCATGTTGG'] | ['Fibrosis of extraocular muscles, congenital, 1'] |
| NM_000155.3 (GALT):c.67A>G (p.Thr23Ala) | 111033635 | GALT | [ ] | [ ] | ['Deficiency of UDPglucose-hexose-1-phosphate uridylyltransferase'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_001041.3 (SI):c.350A>G (p.Gln117Arg) | 121912612 | SI | [ ] | [ ] | ['Sucrase-isomaltase deficiency'] |
| NM_000155.3 (GALT):c.1A>G (p.Met1Val) | 111033639 | GALT | [ ] | [ ] | ['Deficiency of UDPglucose-hexose-1-phosphate uridylyltransferase'] |
| NM_021625.4 (TRPV4):c.998A>G (p.Asp333Gly) | 121912634 | TRPV4 | [ ] | [ ] | ['Spondylometaphyseal dysplasia, Kozlowski type'] |
| NM_000155.3 (GALT):c.253-2A>G | 111033661 | GALT | [ ] | ['ATTCACCYACCG ACAAGGATAGG'] | ['Deficiency of UDPglucose-hexose-1-phosphate uridylyltransferase', 'not provided'] |
| NM_000155.3 (GALT):c.290A>G (p.Asn97Ser) | 111033669 | GALT | [ ] | ['GAAGTCGYTGTC AAACAGGAAGG'] | ['Deficiency of UDPglucose-hexose-1-phosphate uridylyltransferase'] |
| NM_000155.3 (GALT):c.379A>G (p.Lys127Glu) | 111033682 | GALT | [ ] | ['TGACCTYACTGG GTGGTGACGGG', 'ATGACCTYACTG GGTGGTGACGG'] | ['Deficiency of UDPglucose-hexose-1-phosphate uridylyltransferase'] |
| NM_000343.3 (SLC5A1):c.83A>G (p.Asp28Gly) | 121912669 | SLC5A1 | [ ] | [ ] | ['Congenital glucose-galactose malabsorption'] |
| NM_005159.4 (ACTC1):c.1088A>G (p.Glu363Gly) | 121912674 | — | [ ] | [ ] | ['Dilated cardiomyopathy 1R'] |
| NM_005159.4 (ACTC1):c.373A>G (p.Met125Val) | 121912677 | — | [ ] | [ ] | ['Atrial septal defect 5'] |
| NM_000155.3 (GALT):c.565-2A>G | 111033731 | GALT | [ ] | [ ] | ['Deficiency of UDPglucose-hexose-1-phosphate uridylyltransferase'] |
| NM_001681.3 (ATP2A2):c.2300A>G (p.Asn767Ser) | 121912732 | ATP2A2 | [ ] | [ ] | ['Darier disease, acral hemorrhagic type'] |
| NM_000155.3 (GALT):c.821-2A>G | 111033767 | GALT | [ ] | [ ] | ['Deficiency of UDPglucose-hexose-1-phosphate uridylyltransferase'] |
| NM_000342.3 (SLC4A1):c.2509A>G (p.Thr837Ala) | 121912750 | SLC4A1 | [ ] | [ ] | ['Spherocytosis type 4'] |
| NM_000155.3 (GALT):c.950A>G (p.Gln317Arg) | 111033786 | GALT | [ ] | ['CAGCYGCCAAT GGTTCCAGTTGG'] | ['Deficiency of UDPglucose-hexose-1-phosphate uridylyltransferase'] |
| NM_001202.3 (BMP4):c.278A>G (p.Glu93Gly) | 121912765 | BMP4 | [ ] | ['CCTCCYCCCCAG ACTGAAGCCGG'] | ['Microphthalmia syndromic 6'] |
| NM_000155.3 (GALT):c.1001A>G (p.Lys334Arg) | 111033809 | GALT | [ ] | [ ] | ['Deficiency of UDPglucose-hexose-1-phosphate uridylyltransferase'] |
| NM_000155.3 (GALT):c.1048A>G (p.Thr350Ala) | 111033817 | GALT | [ ] | [ ] | ['Deficiency of UDPglucose-hexose-1-phosphate uridylyltransferase'] |
| NM_000155.3 (GALT):c.1132A>G (p.Ile378Val) | 111033819 | GALT | [ ] | [ ] | ['Deficiency of UDPglucose-hexose-1-phosphate uridylyltransferase'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| m.3243A>G | 199474657 | MT-TL1 | [ ] | [ ] | ['Leigh disease', 'Cyclical vomiting syndrome', 'Juvenile myopathy, encephalopathy, lactic acidosis AND stroke', 'Myoclonus with epilepsy with ragged red fibers', 'Cytochrome-c oxidase deficiency', 'Diabetes-deafness syndrome maternally transmitted', '3-Methylglutaconic aciduria', 'Age-related macular degeneration 2', 'MERRF/MELAS overlap syndrome'] |
| m.3252A>G | 199474661 | MT-TL1 | [ ] | [ ] | ['Mitochondrial encephalomyopathy'] |
| m.3251A>G | 199474662 | MT-TL1 | [ ] | [ ] | [ ] |
| NM_000258.2 (MYL3):c.517A>G (p.Met173Val) | 199474708 | MYL3 | [ ] | [ ] | ['Cardiomyopathy', 'not specified', 'not provided'] |
| NM_000094.3 (COL7A1):c.425A>G (p.Lys142Arg) | 121912856 | COL7A1 | [ ] | ['CACCYTGGGGA CACCAGGTCGGG', 'TCACCYTGGGGA CACCAGGTCGG'] | ['Epidermolysis bullosa dystrophica inversa, autosomal recessive'] |
| NM_152263.3 (TPM3):c.505A>G (p.Lys169Glu) | 199474715 | TPM3 | [ ] | ['CCAACTYACGA GCCACCTACAGG'] | ['Congenital myopathy with fiber type disproportion', 'not provided'] |
| NM_152263.3 (TPM3):c.733A>G (p.Arg245Gly) | 199474718 | TPM3 | [ ] | ['ATCYCTCAGCAA ACTCAGCACGG'] | ['Congenital myopathy with fiber type disproportion', 'not provided'] |
| NM_001844.4 (COL2A1):c.4172A>G (p.Tyr1391Cys) | 121912889 | COL2A1 | ['GCAGTGG YAGGTGAT GTTCTGGG'] | ['GCAGTGGYAGG TGATGTTCTGGG'] | [Spondyloperipheral dysplasia', 'Platyspondylic lethal skeletal dysplasia Torrance type'] |
| NM_001844.4 (COL2A1):c.2974A>G (p.Arg992Gly) | 121912895 | COL2A1 | [ ] | ['CCTCYCTCACCA CGTTGCCCAGG'] | ['Spondyloepimeta-physeal dysplasia Strudwick type'] |
| NM_001848.2 (COL6A1):c.362A>G (p.Lys121Arg) | 121912936 | COL6A1 | [ ] | [ ] | [Ullrich congenital muscular dystrophy', 'Bethlem myopathy', 'not provided'] |
| NM_004004.5 (GJB2):c.218A>G (p.His73Arg) | 121912968 | GJB2 | [ ] | [ ] | ['Keratoderma palmoplantar deafness'] |
| NM_000941.2 (POR):c.1733A>G (p.Tyr578Cys) | 121912975 | POR | [ ] | [ ] | ['Antley-Bixler syndrome with genital anomalies and disordered steroidogenesis'] |
| NM_001943.3 (DSG2):c.797A>G (p.Asn266Ser) | 121913011 | DSG2 | [ ] | [ ] | ['Arrhythmogenic right ventricular cardiomyopathy, type 10'] |
| NM_000129.3 (F13A1):c.851A>G (p.Tyr284Cys) | 121913074 | F13A1 | [ ] | ['ATAGGCAYAGA TATTGTCCCAGG'] | ['Factor xiii, a subunit, deficiency of'] |
| NM_000043.4 (FAS):c.695A>G (p.Tyr232Cys) | 121913079 | FAS | [ ] | [ ] | ['Autoimmune lymphoproliferative syndrome, type 1a'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000043.4 (FAS):c.763A>G (p.Asn255Asp) | 121913082 | FAS | [ ] | [ ] | [ ] |
| NM_000043.4 (FAS):c.353A>G (p.Asn118Ser) | 121913083 | FAS | [ ] | [ ] | [ ] |
| NM_206933.2 (USH2A):c.14020A>G (p.Arg4674Gly) | 80338904 | USH2A | [ ] | [ ] | ['Retinitis pigmentosa', 'Retinitis pigmentosa 39'] |
| NM_000142.4 (FGFR3):c.833A>G (p.Tyr278Cys) | 121913115 | FGFR3 | [ ] | [ ] | ['Hypochondroplasia'] |
| NM_000183.2 (HADHB):c.788A>G (p.Asp263Gly) | 121913131 | HADHB | [ ] | [ ] | ['Mitochondrial trifunctional protein deficiency'] |
| NM_001079817.1 (INSR):c.1459A>G (p.Lys487Glu) | 121913136 | INSR | [ ] | [ ] | ['Leprechaunism syndrome'] |
| NM_000208.2 (INSR):c.707A>G (p.His236Arg) | 121913145 | INSR | [ ] | ['GCTGYGGCAAC AGAGGCCTTCGG'] | ['Leprechaunism syndrome'] |
| NM_000208.2 (INSR):c.1466A>G (p.Asn489Ser) | 121913147 | INSR | [ ] | [ ] | ['Insulin-resistant diabetes mellitus AND acanthosis nigricans'] |
| NM_000208.2 (INSR):c.1372A>G (p.Asn458Asp) | 121913160 | INSR | [ ] | [ ] | ['Leprechaunism syndrome'] |
| NM_000016.5 (ACADM):c.797A>G (p.Asp266Gly) | 201375579 | ACADM | [ ] | [ ] | ['not provided'] |
| NM_024577.3 (SH3TC2):c.530-2A>G | 80338920 | SH3TC2 | [ ] | [ ] | ['Charcot-Marie-Tooth disease, type 4C'] |
| NM_001127500.1 (MET):c.3743A>G (p.Tyr1248Cys) | 121913246 | MET | [ ] | [ ] | ['Renal cell carcinoma, papillary, 1'] |
| NM_000517.4 (HBA2):c.*92A>G | 63750067 | HBA2 | ['ACTTYAT TCAAAGAC CAGGAAG G'] | ['CTTYATTCAAAG ACCAGGAAGGG', 'ACTTYATTCAAA GACCAGGAAGG'] | ['Hemoglobin H disease, nondeletional'] |
| NM_199440.1 (HSPD1):c.86A>G (p.Asp29Gly) | 72466451 | HSPD1 | [ ] | [ ] | ['Leukodystrophy, hypomyelinating, 4'] |
| NM_000249.3 (MLH1):c.544A>G (p.Arg182Gly) | 63750211 | MLH1 | [ ] | [ ] | ['Hereditary Nonpolyposis Colorectal Neoplasms'] |
| NM_025137.3 (SPG11):c.1457-2A>G | 312262726 | SPG11 | [ ] | [ ] | ['Spastic paraplegia 11, autosomal recessive'] |
| NM_025137.3 (SPG11):c.2608A>G (p.Ile870Val) | 312262745 | SPG11 | [ ] | ['ACTTAYCCTGGG GAGAAGGATGG'] | ['Spastic paraplegia 11, autosomal recessive'] |
| NM_025137.3 (SPG11):c.2833A>G (p.Arg945Gly) | 312262748 | SPG11 | [ ] | [ ] | ['Spastic paraplegia 11, autosomal recessive'] |
| NM_003867.3 (FGF17):c.560A>G (p.Asn187Ser) | 398123026 | FGF17 | ['CGTGGYT GGGGAAG GCAGCTG G'] | ['CGTGGYTGGGG AAGGGCAGCTGG'] | ['Hypogonadotropic hypogonadism 20 with or without anosmia'] |
| NM_025137.3 (SPG11):c.6477+4A>G | 312262780 | SPG11 | [ ] | [ ] | ['Spastic paraplegia 11, autosomal recessive'] |
| NM_000141.4 (FGFR2):c.1124A>G (p.Tyr375Cys) | 121913478 | FGFR2 | [ ] | [ ] | ['Cutis Gyrata syndrome of Beare and Stevenson', 'Endometrial carcinoma'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000142.4 (FGFR3):c.1118A>G (p.Tyr373Cys) | 121913485 | FGFR3 | [ ] | [ ] | ['Thanatophoric dysplasia type 1'] |
| NM_003611.2 (OFD1):c.290A>G (p.Glu97Gly) | 312262820 | OFD1 | [ ] | [ ] | ['Oral-facial-digital syndrome'] |
| NM_000222.2 (KIT):c.1924A>G (p.Lys642Glu) | 121913512 | KIT | ['GACTTYG AGTTCAGA CATGAGGG'] | ['GACTTYGAGTTC AGACATGAGGG', 'GGACTTYGAGTT CAGACATGAGG'] | [ ] |
| NM_003611.2 (OFD1):c.382-2A>G | 312262829 | OFD1 | [ ] | [ ] | ['Oral-facial-digital syndrome'] |
| NM_000391.3 (TPP1):c.857A>G (p.Asn286Ser) | 119455958 | TPP1 | [ ] | [ ] | ['Ceroid lipofuscinosis, neuronal, 2'] |
| NM_005912.2 (MC4R):c.508A>G (p.Ile170Val) | 121913560 | MC4R | [ ] | [ ] | ['Obesity'] |
| NM_005912.2 (MC4R):c.821A>G (p.Asn274Ser) | 121913561 | MC4R | [ ] | [ ] | ['Obesity'] |
| NM_005912.2 (MC4R):c.289A>G (p.Asn97Asp) | 121913565 | MC4R | [ ] | [ ] | ['Obesity'] |
| NM_005912.2 (MC4R):c.185A>G (p.Asn62Ser) | 121913566 | MC4R | [ ] | [ ] | ['Obesity'] |
| NM_000530.6 (MPZ):c.286A>G (p.Lys96Glu) | 121913583 | MPZ | [ ] | [ ] | ['Charcot-Marie-Tooth disease type 1B'] |
| NM_000095.2 (COMP):c.1760A>G (p.His587Arg) | 312262901 | COMP | [ ] | [ ] | ['Pseudoachondroplastic spondyloepiphyseal dysplasia syndrome'] |
| NM_000530.6 (MPZ):c.242A>G (p.His81Arg) | 121913594 | MPZ | ['GGCATAG YGGAAGAT CTATGAGG'] | ['GGCATAGYGGA AGATCTATGAGG'] | ['Charcot-Marie-Tooth disease type 1B'] |
| NM_000484.3 (APP):c.2146A>G (p.Ile716Val) | 63750399 | APP | [ ] | [ ] | ['Alzheimer disease, type 1', 'not provided'] |
| NM_000329.2 (RPE65):c.1292A>G (p.Tyr431Cys) | 62636300 | RPE65 | [ ] | [ ] | ['Leber congenital amaurosis 2', 'not provided'] |
| NM_002470.3 (MYH3):c.1385A>G (p.Asp462Gly) | 121913622 | MYH3 | [ ] | [ ] | ['Distal arthrogryposis type 2B'] |
| NM_000257.3 (MYH7):c.2333A>G (p.Asp778Gly) | 121913634 | MYH7 | [ ] | [ ] | ['Familial hypertrophic cardiomyopathy 1', 'not specified'] |
| NM_001127500.1 (MET):c.3785A>G (p.Lys1262Arg) | 121913677 | MET | [ ] | [ ] | ['Childhood hepatocellular carcinoma'] |
| NM_000222.2 (KIT):c.2459A>G (p.Asp820Gly) | 121913682 | KIT | [ ] | ['AGAAYCATTCTT GATGTCTCTGG'] | ['Mast cell disease, systemic'] |
| NM_000222.2 (KIT):c.2386A>G (p.Arg796Gly) | 121913684 | KIT | [ ] | [ ] | [ ] |
| NM_006005.3 (WFS1):c.1385A>G (p.Glu462Gly) | 398123066 | WFS1 | [ ] | [ ] | ['Cataract, nuclear total'] |
| NM_000495.4 (COL4A5):c.3925-2A>G | 587776400 | COL4A5 | [ ] | [ ] | ['Alport syndrome, X-linked recessive'] |
| NC_012920.1: m.13514A>G | 587776440 | MT-NDS | [ ] | [ ] | ['Leigh disease'] |
| NM_000021.3 (PSEN1):c.488A>G (p.His163Arg) | 63750590 | PSEN1 | [ ] | [ ] | ['Alzheimer disease, type 3', 'not provided'] |

TABLE 8-continued

Human gene mutations that may be corrected by changing a guanine (G) to an
adenine (A). The gene name, gene symbol, and dbSNP database reference number (RS#) are
indicated. Also indicated are exemplary protospacers with their PAM sequences (gRNAs and
gRNAall) and the base to be edited e.g., a C, indicated by a "Y". The "gRNAs" sequences,
from top to bottom, correspond to SEQ ID NOs: 3434-3601. The "gRNA all" sequences,
from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000484.3 (APP):c.2140A>G (p.Thr714Ala) | 63750643 | APP | [ ] | [ ] | ['Alzheimer disease, type 1', 'not provided'] |
| NM_173560.3 (RFX6):c.224-12A>G | 587776515 | RFX6 | [ ] | [ ] | ['Mitchell-Riley syndrome'] |
| NM_014043.3 (CHMP2B):c.85A>G (p.Ile29Val) | 63750818 | CHMP2B | [ ] | [ ] | ['Frontotemporal Dementia, Chromosome 3-Linked', 'Amyotrophic lateral sclerosis 17', 'not provided'] |
| NM_000057.3 (BLM):c.1088-2A>G | 367543015 | BLM | [ ] | [ ] | ['Bloom syndrome'] |
| NM_001011658.3 (TRAPPC2):c.238+4T>C | 587776753 | — | [ ] | [ ] | ['Spondyloepiphyseal dysplasia tarda'] |
| NM_000151.3 (G6PC):c.230+4A>G | 587776757 | G6PC | [ ] | ['GTTCYTACCACT TAAAGACGAGG'] | ['Glycogen storage disease type 1A'] |
| NM_000463.2 (UGT1A1):c.1085-2A>G | 587776766 | — | ['ACCYGAG ATGCAAAA TAGGGAGG'] | ['ACCYGAGATGC AAAATAGGGAGG', 'GTGACCYGAGAT GCAAAATAGGG', 'GGTGACCYGAGA TGCAAAATAGG'] | ['Crigler Najjar syndrome, type 1'] |
| NM_000330.3 (RS1):c.286T>C (p.Trp96Arg) | 61752063 | — | [ ] | ['TTCTTCGYGGAC TGCAAACAAGG'] | ['Juvenile retinoschisis', 'not provided'] |
| NM_001024847.2 (TGFBR2):c.1472-2A>G | 587776770 | TGFBR2 | [ ] | [ ] | ['Loeys-Dietz syndrome 2'] |
| NM_000257.3 (MYH7):c.5807A>G (p.Ter1936Trp) | 367543053 | MYH7 | [ ] | [ ] | ['Congenital myopathy with fiber type disproportion'] |
| NM_000321.2 (RB1):c.2490-1398A>G | 587776791 | RB1 | [ ] | [ ] | ['Retinoblastoma'] |
| NM_024549.5 (TCTN1):c.221-2A>G | 367543065 | TCTN1 | [ ] | ['AGCAACYGCAG AAAAAAGAGGGG', 'CAGCAACYGCAG AAAAAAGAGGG'] | ['Joubert syndrome 13'] |
| NM_000228.2 (LAMB3):c.565-3T>C | 587776813 | LAMB3 | [ ] | [ ] | ['Adult junctional epidermolysis bullosa'] |
| NM_015884.3 (MBTPS2):c.1523A>G (p.Asn508Ser) | 587776867 | MBTPS2 | [ ] | [ ] | ['Keratosis pilaris decalvans'] |
| NM_000174.4 (GP9):c.182A>G (p.Asn61Ser) | 5030764 | GP9 | ['GGCTGYT GTTGGCCA GCAGAAG G'] | ['GGCTGYTGTTGG CCAGCAGAAGG'] | ['Bernard-Soulier syndrome type C'] |
| NM_000894.2 (LHB):c.221A>G (p.Gln74Arg) | 5030773 | LHB | [ ] | ['CCACCYGAGGC AGGGGCGGCAGG'] | ['Isolated lutropin deficiency'] |
| NM_000264.3 (PTCH1):c.2479A>G (p.Ser827Gly) | 199476092 | — | [ ] | ['CGTTACYGAAAC TCCTGTGTAGG'] | ['Gorlin syndrome', 'Holoprosencephaly 7', 'not specified', 'not provided'] |
| NM_000021.3 (PSEN1):c.415A>G (p.Met139Val) | 63751037 | PSEN1 | [ ] | [ ] | ['Alzheimer disease, type 3', 'not provided'] |
| NM_000484.3 (APP):c.2078A>G (p.Glu693Gly) | 63751039 | APP | [ ] | [ ] | ['Alzheimer disease', 'Alzheimer disease, type 1', 'Cerebral amyloid angiopathy, APP-related', 'not provided'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000117.2 (EMD):c.450-2A>G | 398123158 | EMD | [ ] | ['CGTTCCCYGAGG CAAAAGAGGGG'] | ['not provided'] |
| RMRP:n.71A>G | 199476103 | RMRP | [ ] | ['ACTTYCCCCTAG GCGGAAAGGGG', 'GACTTYCCCCTA GGCGGAAAGGG', 'GGACTTYCCCCT AGGCGGAAAGG'] | ['Metaphyseal chondrodysplasia, McKusick type', 'Metaphyseal dysplasia without hypotrichosis'] |
| m.14495A>G | 199476106 | MT-ND6 | [ ] | [ ] | ['Leber optic atrophy'] |
| m.11084A>G | 199476113 | MT-ND4 | [ ] | [ ] | ['Juvenile myopathy, encephalopathy, lactic acidosis AND stroke'] |
| NM_000551.3 (VHL):c.233A>G (p.Asn78Ser) | 5030804 | VHL | ['TGCGAYT GCAGAAG ATGACCTG G'] | ['GCGAYTGCAGA AGATGACCTGGG', 'TGCGAYTGCAGA AGATGACCTGG'] | ['Von Hippel-Lindau syndrome'] |
| m.3397A>G | 199476120 | MT-ND1 | [ ] | [ ] | ['Alzheimer disease', 'Parkinson disease, late-onset'] |
| m.4136A>G | 199476121 | MT-ND1 | [ ] | [ ] | ['Leber optic atrophy'] |
| NM_003094.3 (SNRPE):c.1A>G (p.Met1Val) | 587776924 | SNRPE | [ ] | [ ] | ['Hypotrichosis 11'] |
| NM_001310338.1 (MGME1):c.743A>G (p.Tyr248Cys) | 587776944 | MGME1 | [ ] | [ ] | ['Mitochondrial DNA depletion syndrome 11'] |
| NM_000249.3 (MLH1):c.122A>G (p.Asp41Gly) | 63751094 | MLH1 | [ ] | [ ] | ['Hereditary Nonpolyposis Colorectal Neoplasms'] |
| NM_138425.3 (C12orf57):c.1A>G (p.Met1Val) | 587776954 | C12orf57 | [ ] | [ ] | ['Temtamy syndrome', 'Seizures', 'Corpus callosum abnormalities', 'Colobomatous microphthalmia', 'Global developmental delay'] |
| NM_000277.1 (PAH):c.1169A>G (p.Glu390Gly) | 5030856 | PAH | [ ] | ['CTCYCTGCCACG TAATACAGGGG', 'ACTCYCTGCCAC GTAATACAGGG', 'AACTCYCTGCCA CGTAATACAGG'] | ['Phenylketonuria', 'Hyperphenylalaninemia, non-pku', 'not provided'] |
| NM_000277.1 (PAH):c.1241A>G (p.Tyr414Cys) | 5030860 | PAH | [ ] | ['GGGTCGYAGCG AACTGAGAAGGG', 'TGGGTCGYAGCG AACTGAGAAGG'] | ['Phenylketonuria', 'Hyperphenylalaninemia, non-pku', 'not provided'] |
| NM_000155.3 (GALT):c.308A>G (p.Gln103Arg) | 367543252 | GALT | [ ] | [ ] | ['Deficiency of UDPglucose-hexose-1-phosphate uridylyltransferase'] |
| NM_207352.3 (CYP4V2):c.1091-2A>G | 199476183 | CYP4V2 | [ ] | [ ] | ['Bietti crystalline corneoretinal dystrophy'] |
| NM_000518.4 (HBB):c.*111A>G | 63751128 | HBB | [ ] | [ ] | [ ] |
| NM_000155.3 (GALT):c.857A>G (p.Tyr286Cys) | 367543262 | GALT | [ ] | [ ] | ['Deficiency of UDPglucose-hexose-1-phosphate uridylyltransferase'] |
| NM_000155.3 (GALT):c.854A>G (p.Lys285Arg) | 367543263 | GALT | [ ] | [ ] | ['Deficiency of UDPglucose-hexose-1-phosphate uridylyltransferase'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_207352.3 (CYP4V2):c.761A>G (p.His254Arg) | 199476193 | CYP4V2 | [ ] | [ ] | ['Bietti crystalline corneoretinal dystrophy'] |
| NM_000155.3 (GALT):c.968A>G (p.Tyr323Cys) | 367543267 | GALT | [ ] | [ ] | ['Deficiency of UDPglucose-hexose-1-phosphate uridylyltransferase'] |
| NM_001142519.1 (FAM111A):c.1012A>G (p.Thr338Ala) | 587777014 | FAM111A | [ ] | [ ] | ['Gracile bone dysplasia'] |
| NM_000132.3 (F8):c.1660A>G (p.Ser554Gly) | 137852419 | F8 | ['AACYAGA GTAATAGC GGGTCAGG'] | ['AACYAGAGTAA TAGCGGGTCAGG'] | ['Hereditary factor VIII deficiency disease'] |
| NM_020988.2 (GNAO1):c.521A>G (p.Asp174Gly) | 587777055 | GNAO1 | [ ] | ['GGATGYCCTGCT CGGTGGGCTGG'] | ['Early infantile epileptic encephalopathy 17'] |
| NM_000155.3 (GALT):c.905-2A>G | 398123187 | GALT | [ ] | [ ] | ['Deficiency of UDPglucose-hexose-1-phosphate uridylyltransferase'] |
| NM_015662.2 (IFT172):c.4607T>C (p.Leu1536Pro) | 587777080 | IFT172 | [ ] | [ ] | [ ] |
| NM_014754.2 (PTDSS1):c.1058A>G (p.Gln353Arg) | 587777088 | PTDSS1 | [ ] | [ ] | [Lenz-Majewski hyperostosis syndrome'] |
| NM_003859.1 (DPM1):c.742T>C (p.Ser248Pro) | 587777114 | — | [ ] | [ ] | ['Congenital disorder of glycosylation type 1E'] |
| NM_001018005.1 (TPM1):c.742A>G (p.Lys248Glu) | 199476319 | TPM1 | [ ] | [ ] | ['Left ventricular noncompaction 9', 'not provided'] |
| NM_004826.3 (ECEL1):c.2278T>C (p.Cys760Arg) | 587777129 | ECEL1 | [ ] | [ ] | ['Arthrogryposis, distal, type 5d'] |
| NM_014908.3 (DOLK):c.2T>C (p.Met1Thr) | 587777137 | DOLK | [ ] | [ ] | ['Congenital disorder of glycosylation type 1M'] |
| NM_000350.2 (ABCA4):c.4540-2A>G | 61752435 | ABCA4 | [ ] | [ ] | ['Stargardt disease 1', 'not provided'] |
| NM_001128085.1 (ASPA):c.433-2A>G | 63751297 | — | [ ] | [ ] | ['Spongy degeneration of central nervous system'] |
| NM_176787.4 (PIGN):c.808T>C (p.Ser270Pro) | 587777186 | PIGN | [ ] | [ ] | ['Multiple congenital anomalies-hypotonia-seizures syndrome 1'] |
| NM_001165899.1 (PDE4D):c.1850T>C (p.Ile617Thr) | 587777188 | PDE4D | ['CTATAYT GTTCATCC CCTCTGGG', 'ACTATAYT GTTCATCC CCTCTGG'] | ['CTATAYTGTTCA TCCCCTCTGGG', 'ACTATAYTGTTC ATCCCCTCTGG'] | ['Acrodysostosis 2, with or without hormone resistance'] |
| NM_005017.3 (PCYT1A):c.571T>C (p.Phe191Leu) | 587777195 | PCYT1A | ['GCATGYT TGCTCCAA CACAGAGG'] | ['GCATGYTTGCTC CAACACAGAGG'] | ['Spondylometaphyseal dysplasia with cone-rod dystrophy'] |
| NM_024301.4 (FKRP):c.1A>G (p.Met1Val) | 587777223 | FKRP | [ ] | ['CCGCAYGGGGC CGAAGTCTGGGG', 'GCCGCAYGGGGC CGAAGTCTGGG', 'AGCCGCAYGGGG CCGAAGTCTGG'] | ['Congenital muscular dystrophy—dystroglycanopathy with brain and eye anomalies type A5'] |
| NM_198947.3 (FAM111B):c.1879A>G (p.Arg627Gly) | 587777237 | FAM111B | [ ] | [ ] | ['Poikiloderma, hereditary fibrosing, with tendon contractures, myopathy, and pulmonary fibrosis'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_003638.2 (ITGA8):c.2982+2T>C | 587777279 | ITGA8 | [ ] | [ ] | ['Renal adysplasia'] |
| NM_199189.2 (MATR3):c.1864A>G (p.Thr622Ala) | 587777301 | MATR3 | ['CGGYTGAACTCTCAGTCTTCTGG'] | ['CGGYTGAACTCTCAGTCTTCTGG'] | ['Myopathy, distal, 2'] |
| NM_001739.1 (CA5A):c.697T>C (p.Ser233Pro) | 587777316 | CA5A | [ ] | [ ] | ['Carbonic anhydrase VA deficiency, hyperammonemia due to'] |
| NM_005051.2 (QARS):c.169T>C (p.Tyr57His) | 587777333 | QARS | [ ] | [ ] | ['Microcephaly, progressive, with seizures and cerebral and cerebellar atrophy'] |
| NM_002234.3 (KCNA5):c.143A>G (p.Glu48Gly) | 587777336 | KCNA5 | [ ] | [ ] | ['Atrial fibrillation, familial, 7'] |
| NM_021803.3 (IL21):c.146T>C (p.Leu49Pro) | 587777338 | IL21 | [ ] | [ ] | ['Common variable immunodeficiency 11'] |
| NM_000132.3 (F8):c.6794A>G (p.Gln2265Arg) | 137852470 | F8 | [ ] | [ ] | ['Hereditary factor VIII deficiency disease'] |
| NM_178014.3 (TUBB):c.895A>G (p.Met299Val) | 587777355 | TUBB | [ ] | [ ] | ['Cortical dysplasia, complex, with other brain malformations 6'] |
| NM_005957.4 (MTHFR):c.1969T>C (p.Ter657Arg) | 768434408 | MTHFR | [ ] | [ ] | ['Homocysteinemia due to MTHFR deficiency'] |
| NM_005359.5 (SMAD4):c.425-6A>G | 377767327 | SMAD4 | [ ] | [ ] | ['Juvenile polyposis syndrome'] |
| NM_022068.3 (PIEZO2):c.8215T>C (p.Ser2739Pro) | 587777454 | PIEZO2 | [ ] | [ ] | ['Oculomelic amyoplasia'] |
| NM_003108.3 (SOX11):c.347A>G (p.Tyr116Cys) | 587777479 | SOX11 | [ ] | ['GTACTTGYAGTCGGGGTAGTCGG'] | ['Mental retardation, autosomal dominant 27'] |
| NM_021072.3 (HCN1):c.814T>C (p.Ser272Pro) | 587777493 | HCN1 | [ ] | [ ] | ['Epileptic encephalopathy, early infantile, 24'] |
| NM_020435.3 (GJC2):c.-170A>G | 587777496 | GJC2 | [ ] | ['TTGYTCCCCCCTCGGCCTCAGGG', 'ATTGYTCCCCCCTCGGCCTCAGG'] | ['Leukodystrophy, hypomyelinating, 2'] |
| NM_022552.4 (DNMT3A):c.1943T>C (p.Leu648Pro) | 587777507 | DNMT3A | [ ] | ['CTCCYGGTGCTGAAGGACTTGGG', 'GCTCCYGGTGCTGAAGGACTTGG'] | ['Tatton-Brown-rahman syndrome'] |
| NM_022552.4 (DNMT3A):c.2705T>C (p.Phe902Ser) | 587777510 | DNMT3A | [ ] | [ ] | ['Tatton-Brown-rahman syndrome'] |
| NM_000223.3 (KRT12):c.403A>G (p.Arg135Gly) | 58410481 | KRT12 | [ ] | [ ] | ['Meesman corneal dystrophy', 'not provided'] |
| NM_000232.4 (SGCB):c.1A>G (p.Met1Val) | 398123262 | SGCB | [ ] | [ ] | ['Limb-girdle muscular dystrophy, type 2E', 'not provided'] |
| NM_020630.4 (RET):c.2342A>G (p.Gln781Arg) | 377767416 | RET | [ ] | [ ] | ['MEN2 phenotype: Unclassified'] |
| NM_018400.3 (SCN3B):c.482T>C (p.Met161Thr) | 587777557 | SCN3B | [ ] | ['AATCAYGATGTACATCCTTCTGG'] | ['Atrial fibrillation, familial, 16'] |
| NM_001030001.2 (RPS29):c.149T>C (p.Ile50Thr) | 587777569 | RPS29 | [ ] | ['GATAYCGGTTTCATTAAGGTAGG'] | ['Diamond-Blackfan anemia 13'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_177550.4 (SLC13A5):c.1463T>C (p.Leu488Pro) | 587777578 | SLC13A5 | [ ] | [ ] | ['Epileptic encephalopathy, early infantile, 25'] |
| NM_002880.3 (RAF1):c.1808T>C (p.Leu603Pro) | 587777586 | RAF1 | [ ] | [ ] | ['Cardiomyopathy, dilated, 1NN'] |
| NM_025150.4 (TARS2):c.695+3A>G | 587777594 | TARS2 | [ ] | [ ] | ['Combined oxidative phosphorylation deficiency 21'] |
| NM_001759.3 (CCND2):c.838A>G (p.Thr280Ala) | 587777618 | CCND2 | [ ] | [ ] | Negalencephaly-polymicrogyria-polydactyly-hydrocephalus syndrome 3'] |
| NM_153334.6 (SCARF2):c.190T>C (p.Cys64Arg) | 587777657 | SCARF2 | [ ] | ['CCACGYGCTGCG CTGGCTGGAGG'] | ['Marden Walker like syndrome'] |
| NM_005726.5 (TSFM):c.57+4A>G | 587777689 | TSFM | [ ] | ['ACTTCYCACCGG GTAGCTCCCGG'] | ['Combined oxidative phosphorylation deficiency 3'] |
| NM_000255.3 (MUT):c.329A>G (p.Tyr110Cys) | 796052005 | MUT | [ ] | ['GCAYACTGGCG GATGGTCCAGGG', 'AGCAYACTGGCG GATGGTCCAGG'] | ['not provided'] |
| NM_021870.2 (FGG):c.1210T>C (p.Ser404Pro) | 587777720 | FGG | [ ] | [ ] | ['Hypodysfibrinogenemia'] |
| NM_017617.3 (NOTCH1):c.1285T>C (p.Cys429Arg) | 587777736 | NOTCH1 | ['GGCAAGY GCATCAAC ACGCTGGG'] | ['GGCAAGYGCAT CAACACGCTGGG', 'GGGCAAGYGCAT CAACACGCTGG'] | ['Adams-Oliver syndrome 1', 'Adams-Oliver syndrome 5'] |
| NM_014946.3 (SPAST):c.1688-2A>G | 587777752 | SPAST | ['TTCYGTA AAACATAA AAGTCAGG'] | ['TTCYGTAAAACA TAAAAGTCAGG'] | ['Spastic paraplegia 4, autosomal dominant'] |
| NM_014946.3 (SPAST):c.1245+4A>G | 587777755 | SPAST | [ ] | [ ] | ['Spastic paraplegia 4, autosomal dominant'] |
| NM_014946.3 (SPAST):c.1216A>G (p.Ile406Val) | 587777757 | SPAST | [ ] | [ ] | ['Spastic paraplegia 4, autosomal dominant'] |
| NM_144596.3 (TTC8):c.115-2A>G | 587777809 | TTC8 | [ ] | ['GTTCCYGGAAA GCATTAAGAAGG'] | ['Retinitis pigmentosa 51'] |
| NM_170784.2 (MKKS):c.110A>G (p.Tyr37Cys) | 74315396 | MKKS | [ ] | [ ] | ['Bardet-Biedl syndrome 6', 'McKusick Kaufman syndrome'] |
| NM_000252.2 (MTM1):c.566A>G (p.Asn189Ser) | 132630302 | MTM1 | [ ] | [ ] | ['Severe X-linked myotubular myopathy'] |
| NM_000252.2 (MTM1):c.1190A>G (p.Tyr397Cys) | 132630303 | MTM1 | [ ] | [ ] | ['Severe X-linked myotubular myopathy'] |
| NM_152384.2(BBS5): c.522+3A>G | 587777828 | BBS5 | [ ] | [ ] | ['Bardet-Biedl syndrome 5'] |
| NM_001205019.1 (GK):c.880A>G (p.Asn294Asp) | 132630331 | GK | [ ] | [ ] | ['Deficiency of glycerol kinase'] |
| NM_000166.5 (GJB1):c.580A>G (p.Met194Val) | 587777878 | GJB1 | [ ] | ['TAGCAYGAAGA CGGTGAAGACGG'] | ['X-linked hereditary motor and sensory neuropathy'] |
| NM_000311.3 (PRNP):c.547A>G (p.Thr183Ala) | 74315411 | PRNP | [ ] | [ ] | ['Genetic prion diseases', 'Spongiform encephalopathy with neuropsychiatric features'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_144773.2 (PROKR2):c.629A>G (p.Gln210Arg) | 74315417 | PROKR2 | [ ] | [ ] | ['Kallmann syndrome 3'] |
| NM_000531.5 (OTC):c.919A>G (p.Lys307Glu) | 796052013 | OTC | [ ] | [ ] | ['not provided'] |
| NM_001029871.3 (RSPO4):c.194A>G (p.Gln65Arg) | 74315420 | RSPO4 | [ ] | ['CGTACYGGCGG ATGCCTTCCCGG'] | ['Anonychia'] |
| NM_004333.4 (BRAF):c.770A>G (p.Gln257Arg) | 180177035 | BRAF | [ ] | [ ] | ['Noonan syndrome 7', 'Cardiofaciocutaneous syndrome', 'Rasopathy', 'not provided'] |
| NM_004333.4 (BRAF):c.1495A>G (p.Lys499Glu) | 180177037 | BRAF | [ ] | [ ] | ['Cardiofaciocutaneous syndrome', 'Rasopathy'] |
| NM_198056.2 (SCN5A):c.5297T>A (p.Met1766Lys) | 752476527 | SCN5A | [ ] | [ ] | ['not provided'] |
| NM_000030.2 (AGXT):c.248A>G (p.His83Arg) | 180177186 | AGXT | [ ] | [ ] | ['Primary hyperoxaluria, type I'] |
| NM_000030.2 (AGXT):c.424-2A>G (p.Gly_142Gln145del) | 180177219 | AGXT | [ ] | ['AGGCCCYGAGG AAGCAGGGACGG'] | ['Primary hyperoxaluria, type I'] |
| NM_198578.3 (LRRK2):c.5096A>G (p.Tyr1699Cys) | 35801418 | LRRK2 | [ ] | [ ] | ['Parkinson disease 8, autosomal dominant'] |
| NM_002693.2 (POLG):c.1808T>C (p.Met603Thr) | 367610201 | POLG | [ ] | ['CTCAYGGCACTT ACCTGGGATGG'] | ['not provided'] |
| NM_000030.2 (AGXT):c.596-2A>G | 180177245 | AGXT | [ ] | [ ] | ['Primary hyperoxaluria, type I'] |
| NM_020223.3 (FAM20C):c.1364-2A>G | 796051853 | FAM20C | [ ] | [ ] | ['Raine syndrome'] |
| NM_012203.1 (GRHPR):c.84-2A>G | 180177319 | GRHPR | [ ] | ['TCACAGCYGCG GGGAAAGGGAGG'] | ['Primary hyperoxaluria, type II'] |
| NM_006017.2 (PROM1):c.2077-521A>G | 796051882 | PROM1 | [ ] | [ ] | ['Cone-rod dystrophy 2'] |
| NM_012203.1 (GRHPR):c.934A>G (p.Asn312Asp) | 180177324 | GRHPR | ['CAAGTYG TTAGCTGC CAACAAGG'] | ['CAAGTYGTTAGC TGCCAACAAGG'] | ['Primary hyperoxaluria, type II'] |
| NM_000016.5 (ACADM):c.329A>G (p.Glu110Gly) | 796051900 | ACADM | [ ] | [ ] | ['not provided'] |
| NM_004453.3 (ETFDH):c.929A>G (p.Tyr310Cys) | 796051958 | ETFDH | [ ] | [ ] | ['not provided'] |
| NM_000255.3 (MUT):c.1885A>G (p.Arg629Gly) | 796052004 | MUT | [ ] | [ ] | ['not provided'] |
| NM_012434.4 (SLC17A5):c.548A>G (p.His183Arg) | 119491109 | SLC17A5 | [ ] | [ ] | ['Sialic acid storage disease, severe infantile type'] |
| NM_000328.2 (RPGR):c.155-2A>G | 62638632 | RPGR | [ ] | [ ] | ['Retinitis pigmentosa 15', 'not provided'] |
| NM_005557.3 (KRT16):c.373A>G (p.Asn125Asp) | 58608173 | KRT16 | [ ] | [ ] | ['Pachyonychia congenita, type 1', 'not provided'] |
| NM_000532.4 (PCCB):c.655-2A>G | 796052020 | PCCB | [ ] | [ ] | ['not provided'] |
| NM_000030.2 (AGXT):c.777-2A>G | 796052068 | AGXT | [ ] | ['GGTACCYGGAA GACACGAGGGGG', 'TGGTACCYGGAA GACACGAGGGG'] | ['Primary hyperoxaluria, type I'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000121.3 (EPOR):c.1460A>G (p.Asn487Ser) | 62638745 | EPOR | ['AGGGYTG GAGTAGGG GCCATCGG'] | ['AGGGYTGGAGT AGGGGCCATCGG'] | ['Acute myeloid leukemia, M6 type', 'Familial erythrocytosis, 1'] |
| NM_000552.3 (VWF):c.1583A>G (p.Asn528Ser) | 61754010 | VWF | [ ] | ['TGCCAYTGTAAT TCCCACACAGG'] | ['von Willebrand disease, type 2a', 'not provided'] |
| NM_001918.3 (DBT): c.1017_1018insNC_000001.11: g.100207187_100207312 | 796052135 | DBT | [ ] | [ ] | ['Intermediate maple syrup urine disease type 2'] |
| NM_001243473.1 (B9D1):c.400+2T>C | 143149764 | B9D1 | [ ] | [ ] | ['Meckel syndrome, type 9', 'not provided'] |
| NM_001165963.1 (SCN1A):c.4766T>G (p.Val1589Gly) | 764037830 | — | [ ] | [ ] | ['Severe myoclonic epilepsy in infancy'] |
| NM_000321.2 (RB1):c.1927A>G (p.Lys643Glu) | 587778866 | RB1 | [ ] | ['ATTYCAATGGCT TCTGGGTCTGG'] | ['Retinoblastoma'] |
| NM_006331.7 (EMG1):c.257A>G (p.Asp86Gly) | 74435397 | EMG1 | [ ] | ['ATAYCTGGCCGC GCTTCCCCAGG'] | ['Bowen-Conradi syndrome'] |
| NM_000249.3 (MLH1):c.113A>G (p.Asn38Ser) | 587778888 | MLH1 | [ ] | [ ] | ['Hereditary Nonpolyposis Colorectal Neoplasms'] |
| NM_017777.3 (MKS1):c.1382A>G (p.Tyr461Cys) | 730882120 | MKS1 | [ ] | [ ] | ['Bardet-Biedl syndrome 13'] |
| NM_000261.1 (MYOC):c.1010A>G (p.Gln337Arg) | 74315335 | MYOC | [ ] | [ ] | ['Primary open angle glaucoma juvenile onset 1'] |
| NM_152515.4 (CKAP2L):c.2T>C (p.Met1Thr) | 548949031 | CKAP2L | [ ] | [ ] | ['Filippi syndrome'] |
| NM_000156.5 (GAMT):c.1A>G (p.Met1Val) | 796052527 | GAMT | [ ] | ['CGCTCAYGCTGC AGGCTGGACGG'] | ['not provided'] |
| NM_000833.4 (GRIN2A):c.1930A>G (p.Ser644Gly) | 796052544 | GRIN2A | [ ] | [ ] | ['not provided'] |
| NM_000144.4 (FXN):c.385-2A>G | 140987490 | FXN | [ ] | [ ] | ['Friedreich ataxia'] |
| NM_172107.2 (KCNQ2):c.297-2A>G | 796052615 | KCNQ2 | [ ] | [ ] | ['not provided'] |
| NM_172107.2 (KCNQ2):c.611A>G (p.Gln204Arg) | 796052624 | KCNQ2 | [ ] | [ ] | ['not provided'] |
| NM_172107.2 (KCNQ2):c.848A>G (p.Lys283Arg) | 796052637 | KCNQ2 | [ ] | ['GTACYTGTCCCC GTAGCCAATGG'] | ['not provided'] |
| NM_052859.3 (RFT1):c.887T>A (p.Ile296Lys) | 772820136 | RFT1 | [ ] | [ ] | ['Congenital disorder of glycosylation type 1N'] |
| NM_000553.4 (WRN):c.561A>G (p.Lys187=) | 775802030 | WRN | [ ] | [ ] | ['Werner syndrome'] |
| NM_194277.2 (FRMD7):c.556A>G (p.Met186Val) | 786205896 | FRMD7 | [ ] | [ ] | ['Infantile nystagmus, X-linked'] |
| NM_000535.5 (PMS2):c.989-2A>G | 587779347 | PMS2 | [ ] | [ ] | ['Hereditary Nonpolyposis Colorectal Neoplasms', 'Hereditary cancer-predisposing syndrome'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000203.4 (IDUA):c.1874A>G (p.Tyr625Cys) | 587779401 | IDUA | [ ] | [ ] | ['Hurler syndrome'] |
| NM_001105243.1 (PCDH19):c.1019A>G (p.Asn340Ser) | 796052839 | PCDH19 | [ ] | [ ] | ['not provided'] |
| NM_002693.2 (POLG):c.2840A>G (p.Lys947Arg) | 796052891 | POLG | [ ] | [ ] | ['not provided'] |
| NM_032228.5 (FAR1):c.1094A>G (p.Asp365Gly) | 724159963 | FAR1 | [ ] | ['GATAYCATACA GGAATGCTGGGG', 'AGATAYCATACA GGAATGCTGGG', 'TAGATAYCATAC AGGAATGCTGG'] | ['Peroxisomal fatty acyl-coa reductase 1 disorder'] |
| NM_000090.3 (COL3A1):c.2284-2A>G (p.Gly762_Lys779del) | 587779558 | COL3A1 | [ ] | [ ] | ['Ehlers-Danlos syndrome, type 4'] |
| NM_014305.3 (TGDS):c.269A>G (p.Glu90Gly) | 724160004 | TGDS | [ ] | [ ] | ['Catel Manzke syndrome'] |
| NM_014305.3 (TGDS):c.892A>G (p.Asn298Asp) | 724160005 | TGDS | [ ] | [ ] | ['Catel Manzke syndrome'] |
| NM_000090.3 (COL3A1):c.997-2A>G (p.Gly333_Lys350del+) | 587779602 | COL3A1 | [ ] | [ ] | ['Ehlers-Danlos syndrome, type 4'] |
| NM_002185.3 (IL7R):c.197T>C (p.Ile66Thr) | 1494558 | IL7R | [ ] | [ ] | ['Severe combined immunodeficiency, autosomal recessive, T cell-negative, B cell-positive, NK cell-positive', 'not specified'] |
| NM_000277.1 (PAH):c.974A>G (p.Tyr325Cys) | 62508578 | PAH | [ ] | [ ] | ['Phenylketonuria', 'not provided'] |
| NM_000090.3 (COL3A1):c.997-10A>G (p.Pro332_Gly333insFFQ) | 587779670 | COL3A1 | [ ] | [ ] | ['Ehlers-Danlos syndrome, type 4'] |
| NM_000090.3 (COL3A1):c.3202-2A>G (p.Gly1068_Pro1085del) | 587779682 | COL3A1 | [ ] | [ ] | ['Ehlers-Danlos syndrome, type 4'] |
| NM_000090.3 (COL3A1):c.1762-2A>G (p.Gly588_Gln605del) | 587779722 | COL3A1 | [ ] | ['CACCCYAAAGA AGAAGTGGTCGG'] | ['Ehlers-Danlos syndrome, type 4'] |
| NM_021007.2 (SCN2A):c.4036A>G (p.Ile1346Val) | 796053135 | SCN2A | [ ] | [ ] | ['not provided'] |
| m.13637A>G | 200855215 | MT-ND5 | [ ] | [ ] | ['Leber optic atrophy'] |
| NM_021007.2 (SCN2A):c.387-2A>G | 796053169 | SCN2A | ['AATAAAG YAGAATAT CGTCAAGG'] | ['AATAAAGYAGA ATATCGTCAAGG'] | ['not provided'] |
| NM_021007.2 (SCN2A):c.851A>G (p.Asp284Gly) | 796053173 | SCN2A | [ ] | [ ] | ['not provided'] |
| NM_006516.2 (SLC2A1):c.848A>G (p.Gln283Arg) | 796053251 | SLC2A1 | [ ] | [ ] | ['not provided'] |
| NM_006516.2 (SLC2A1):c.19-2A>G | 796053272 | SLC2A1 | [ ] | [ ] | ['not provided'] |
| NM_000136.2 (FANCC):c.-78-2A>G | 587779898 | FANCC | [ ] | [ ] | ['Hereditary cancer-predisposing syndrome'] |
| m.8296A>G | 118192102 | MT-TK | [ ] | ['TTTACAGYGGGC TCTAGAGGGGG'] | ['Diabetes-deafness syndrome maternally transmitted'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_005360.4 (MAF):c.172A>G (p.Thr58Ala) | 727502767 | MAF | [ ] | [ ] | ['Cataracts, congenital, with sensorineural deafness, down syndrome-like facial appearance, short stature, and mental retardation'] |
| NM_001145901.1 (SARS2):c.1175A>G (p.Asp392Gly) | 727502784 | SARS2 | [ ] | [ ] | ['Hyperuricemia, pulmonary hypertension, renal failure, and alkalosis'] |
| NM_001077494.3 (NFKB2):c.2594A>G (p.Asp865Gly) | 727502787 | NFKB2 | [ ] | ['CTGYCTTCCTTC ACCTCTGCTGG'] | ['Common variable immunodeficiency 10'] |
| NM_002238.3 (KCNH1):c.1399A>G (p.Ile467Val) | 727502819 | KCNH1 | [ ] | [ ] | ['Zimmermann-Laband syndrome', 'Temple-Baraitser syndrome'] |
| NM_172362.2 (KCNH1):c.1508A>G (p.Gln503Arg) | 727502821 | KCNH1 | [ ] | [ ] | ['Temple-Baraitser syndrome'] |
| NM_000546.5 (TP53):c.701A>G (p.Tyr234Cys) | 587780073 | TP53 | [ ] | [ ] | ['Li-Fraumeni syndrome', 'Hereditary cancer-predisposing syndrome'] |
| NM_003060.3 (SLC22A5):c.694A>C (p.Thr232Pro) | 188698686 | SLC22A5 | [ ] | [ ] | ['not provided'] |
| NM_000540.2 (RYR1):c.14591A>G (p.Tyr4864Cys) | 118192146 | RYR1 | [ ] | [ ] | ['Central core disease', 'not provided'] |
| NM_058216.2 (RAD51C):c.706-2A>G | 587780259 | RAD51C | [ ] | [ ] | ['Hereditary cancer-predisposing syndrome'] |
| NM_000501.3 (ELN):c.800-2A>G | 727503027 | ELN | [ ] | [ ] | ['Supravalvar aortic stenosis', 'not provided'] |
| NM_000117.2 (EMD):c.266-2A>G | 727503036 | EMD | [ ] | ['AGCCYTGGGAA GGGGGGCAGCGG'] | [Emery-Dreifuss muscular dystrophy 1, X-linked'] |
| NM_003242.5 (TGFBR2):c.1273A>G (p.Met425Val) | 104893817 | TGFBR2 | [ ] | [ ] | ['Loeys-Dietz syndrome 2'] |
| NM_153638.2 (PANK2):c.700A>G (p.Thr234Ala) | 137852965 | PANK2 | [ ] | [ ] | [ ] |
| NM_005861.3 (STUB1):c.194A>G (p.Asn65Ser) | 690016544 | STUB1 | [ ] | ['GGCCCGGYTGGT GTAATACACGG'] | ['Spinocerebellar ataxia, autosomal recessive 16'] |
| NM_005360.4 (MAF):c.890A>G (p.Lys297Arg) | 121917736 | MAF | [ ] | [ ] | ['Cataract, pulverulent, juvenile-onset'] |
| NM_005211.3 (CSF1R):c.2655-2A>G | 690016554 | CSF1R | [ ] | ['GTATCYGGGAG ATAGGACAGAGG'] | ['Hereditary diffuse leukoencephalopathy with spheroids'] |
| NM_003361.3 (UMOD):c.383A>G (p.Asn128Ser) | 121917770 | UMOD | ['CACAYTG ACACATGT GGCCAGGG'] | ['CACAYTGACAC ATGTGGCCAGGG', 'CCACAYTGACAC ATGTGGCCAGG'] | ['Familial juvenile gout'] |
| NM_000256.3 (MYBPC3):c.2234A>G (p.Asp745Gly) | 727503190 | MYBPC3 | [ ] | [ ] | ['Familial hypertrophic cardiomyopathy 4', 'Familial hypertrophic cardiomyopathy 1', 'not specified'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_172107.2 (KCNQ2):c.1A>G (p.Met1Val) | 118192185 | KCNQ2 | [ ] | ['GCACCAYGGTG CCTGGCGGGAGG'] | ['Benign familial neonatal seizures 1'] |
| NM_000256.3 (MYBPC3):c.1213A>G (p.Met405Val) | 727503207 | MYBPC3 | [ ] | [ ] | ['Cardiomyopathy', 'not specified'] |
| NM_000021.3 (PSEN1):c.998A>G (p.Asp333Gly) | 121917809 | PSEN1 | [ ] | [ ] | ['Primary dilated cardiomyopathy', 'Cardiomyopathy, dilated, 1u', 'Heart failure'] |
| NM_021954.3 (GJA3):c.188A>G (p.Asn63Ser) | 121917823 | GJA3 | [ ] | [ ] | ['Zonular pulverulent cataract 3'] |
| NM_000322.4 (PRPH2):c.422A>G (p.Tyr141Cys) | 61755781 | PRPH2 | [ ] | [ ] | ['Macular dystrophy, vitelliform, adult-onset', 'Patterned dystrophy of retinal pigment epithelium', 'not provided'] |
| NM_007035.3 (KERA):c.740A>G (p.Asn247Ser) | 121917858 | KERA | [ ] | [ ] | ['Cornea plana 2'] |
| NM_002181.3 (IHH):c.284A>G (p.Glu95Gly) | 121917859 | IHH | [ ] | [ ] | ['Brachydactyly type A1'] |
| NM_000257.3 (MYH7):c.1157A>G (p.Tyr386Cys) | 727503269 | MYH7 | [ ] | [ ] | ['Primary familial hypertrophic cardiomyopathy'] |
| NM_000097.5 (CPOX):c.1210A>G (p.Lys404Glu) | 121917868 | CPOX | [ ] | [ ] | ['Harderoporphyria'] |
| NM_012064.3 (MIP):c.401A>G (p.Glu134Gly) | 121917869 | MIP | [ ] | ['AGATCYCCACTG TGGTTGCCTGG'] | ['Cataract 15, multiple types'] |
| NM_025243.3 (SLC19A3):c.1264A>G (p.Thr422Ala) | 121917884 | SLC19A3 | [ ] | [ ] | ['Basal ganglia disease, biotin-responsive'] |
| NM_000373.3 (UMPS):c.286A>G (p.Arg96Gly) | 121917890 | UMPS | [ ] | [ ] | ['Orotic aciduria'] |
| NM_000536.3 (RAG2):c.115A>G (p.Arg39Gly) | 121917897 | RAG2 | [ ] | [ ] | ['Histiocytic medullary reticulosis'] |
| NM_130838.1 (UBE3A):c.1694-2A>G | 587780579 | UBE3A | [ ] | [ ] | ['Angelman syndrome'] |
| NM_016335.4 (PRODH):c.1322T>C (p.Leu441Pro) | 2904551 | PRODH | [ ] | [ ] | ['Proline dehydrogenase deficiency', 'Schizophrenia 4'] |
| NM_006920.4 (SCN1A):c.4352A>G (p.Tyr1451Cys) | 121917962 | — | [ ] | [ ] | ['Severe myoclonic epilepsy in infancy', 'not provided'] |
| NM_006920.4 (SCN1A):c.1876A>G (p.Ser626Gly) | 121917990 | SCN1A | [ ] | [ ] | ['Severe myoclonic epilepsy in infancy', 'Generalized epilepsy'] |
| NM_000478.4 (ALPL):c.1250A>G (p.Asn417Ser) | 121918014 | ALPL | [ ] | ['AGGCCCAYTGCC ATACAGGATGG'] | ['Infantile hypophosphatasia'] |
| NM_000174.4 (GP9):c.110A>G (p.Asp37Gly) | 121918036 | GP9 | [ ] | ['GCAGYCCACCC ACAGCCCCATGG'] | ['Bernard-Soulier syndrome type C'] |
| NM_002693.2 (POLG):c.2591A>G (p.Asn864Ser) | 121918050 | POLG | [ ] | [ ] | ['Mitochondrial DNA depletion syndrome 4B, MNGIE type'] |
| NM_000374.4 (UROD):c.932A>G (p.Tyr311Cys) | 121918061 | UROD | [ ] | [ ] | ['Hepatoerythropoietic porphyria'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOS: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000217.2 (KCNA1):c.763A>G (p.Asn255Asp) | 121918067 | KCNA1 | [ ] | [ ] | [ ] |
| NM_000371.3 (TTR):c.238A>G (p.Thr80Ala) | 121918070 | TTR | [ ] | [ ] | ['Amyloidogenic transthyretin amyloidosis', 'Cardiomyopathy'] |
| NM_000371.3 (TTR):c.401A>G (p.Tyr134Cys) | 121918075 | TTR | ['GGAGYAGGGGCTCAGCAGGGCGG', 'ATAGGAGYAGGGGCTCAGCAGGG'] | ['GGAGYAGGGGCTCAGCAGGGCGG', 'ATAGGAGYAGGGGCTCAGCAGGG'] | ['Amyloidogenic transthyretin amyloidosis'] |
| NM_000371.3 (TTR):c.205A>G (p.Thr69Ala) | 121918081 | TTR | [ ] | [ ] | ['Amyloidogenic transthyretin amyloidosis'] |
| NM_000371.3 (TTR):c.379A>G (p.Ile127Val) | 121918089 | TTR | [ ] | ['CGGCAAYGGTGTAGCGGCGGGGG', 'GCGGCAAYGGTGTAGCGGCGGGG'] | ['Amyloidogenic transthyretin amyloidosis'] |
| NM_000371.3 (TTR):c.113A>G (p.Asp38Gly) | 121918098 | TTR | [ ] | [ ] | ['Amyloidogenic transthyretin amyloidosis', 'AMYLOIDOSIS, LEPTOMENINGEAL, TRANSTHYRETIN-RELATED'] |
| NM_000823.3 (GHRHR):c.985A>G (p.Lys329Glu) | 121918121 | GHRHR | [ ] | ['CGACTYGGAGAGACGCCTGCAGG'] | ['Isolated growth hormone deficiency type 1B'] |
| NM_000275.2 (OCA2):c.1465A>G (p.Asn489Asp) | 121918170 | OCA2 | ['GACATYTGGAGGGTCCCCGATGG'] | ['GACATYTGGAGGGTCCCCGATGG'] | ['Tyrosinase-positive oculocutaneous albinism'] |
| NM_000181.3 (GUSB):c.1484A>G (p.Tyr495Cys) | 121918178 | GUSB | [ ] | [ ] | ['Mucopolysaccharidosis type VII'] |
| NM_018122.4 (DARS2):c.133A>G (p.Ser45Gly) | 121918209 | DARS2 | [ ] | [ ] | ['Leukoencephalopathy with Brainstem and Spinal Cord Involvement and Lactate Elevation'] |
| NM_015697.7 (COQ2):c.890A>G (p.Tyr297Cys) | 121918230 | COQ2 | [ ] | [ ] | ['Coenzyme Q10 deficiency, primary 1'] |
| NM_015697.7 (COQ2):c.683A>G (p.Asn228Ser) | 121918232 | COQ2 | [ ] | [ ] | ['Coenzyme Q10 deficiency, primary 1'] |
| NM_015384.4 (NIPBL):c.7289A>G (p.Tyr2430Cys) | 121918265 | NIPBL | [ ] | [ ] | ['Cornelia de Lange syndrome 1'] |
| NM_004183.3 (BEST1):c.707A>G (p.Tyr236Cys) | 121918291 | BEST1 | [ ] | [ ] | ['Vitreoretinochoroidopathy dominant'] |
| NM_014362.3 (HIBCH):c.365A>G (p.Tyr122Cys) | 121918329 | HIBCH | [ ] | [ ] | [Beta-hydroxyisobutyryl-CoA deacylase deficiency'] |
| NM_015335.4 (MED13L):c.6068A>G (p.Asp2023Gly) | 121918333 | MED13L | [ ] | ['ATATCAYCTAGAGGGAAGGGGGG', 'CATATCAYCTAGAGGGAAGGGGG'] | ['Transposition of great arteries'] |
| NM_015040.3 (PIKFYVE):c.3308A>G (p.Lys1103Arg) | 121918336 | PIKFYVE | [ ] | [ ] | ['Fleck corneal dystrophy'] |
| NM_006306.3 (SMC1A):c.2974-2A>G | 727503774 | SMC1A | [ ] | [ ] | ['Congenital muscular hypertrophy-cerebral syndrome'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_002633.2 (PGM1):c.343A>G (p.Thr115Ala) | 121918371 | PGM1 | [ ] | [ ] | ['Congenital disorder of glycosylation type 1t'] |
| NM_000040.1 (APOC3):c.280A>G (p.Thr94Ala) | 121918381 | APOC3 | ['CTGAAGYTGGTCTGACCTCAGGG', 'GCTGAAGYTGGTCTGACCTCAGG'] | ['CTGAAGYTGGTCTGACCTCAGGG', 'GCTGAAGYTGGTCTGACCTCAGG'] | [ ] |
| NM_000040.1 (APOC3):c.232A>G (p.Lys78Glu) | 121918382 | APOC3 | [ ] | [ ] | ['Hyperalphalipo-proteinemia 2'] |
| NM_001146040.1 (GLRA1):c.910A>G (p.Lys304Glu) | 121918412 | GLRA1 | [ ] | [ ] | ['Hyperekplexia hereditary'] |
| NM_000171.3 (GLRA1):c.523A>G (p.Met175Val) | 121918414 | GLRA1 | [ ] | [ ] | ['Hyperekplexia hereditary'] |
| NM_021957.3 (GYS2):c.116A>G (p.Asn39Ser) | 121918423 | GYS2 | [ ] | [ ] | ['Hypoglycemia with deficiency of glycogen synthetase in the liver'] |
| NM_002834.3 (PTPN11):c.188A>G (p.Tyr63Cys) | 121918459 | PTPN11 | [ ] | [ ] | ['Noonan syndrome', 'Noonan syndrome 1', 'Rasopathy', 'not provided'] |
| NM_013382.5 (POMT2):c.1726-2A>G | 727503873 | POMT2 | [ ] | [ ] | ['not provided'] |
| NM_002834.3 (PTPN11):c.236A>G (p.Gln79Arg) | 121918466 | PTPN11 | [ ] | [ ] | ['Noonan syndrome', 'Noonan syndrome 1', 'Rasopathy', 'not provided'] |
| NM_000313.3 (PROS1):c.773A>G (p.Asn258Ser) | 121918473 | PROS1 | [ ] | [ ] | ['Protein S deficiency'] |
| NM_000313.3 (PROS1):c.586A>G (p.Lys196Glu) | 121918474 | PROS1 | [ ] | [ ] | ['Protein S deficiency'] |
| NM_000141.4 (FGFR2):c.983A>G (p.Tyr328Cys) | 121918493 | FGFR2 | [ ] | [ ] | ['Crouzon syndrome'] |
| NM_000141.4 (FGFR2):c.874A>G (p.Lys292Glu) | 121918500 | FGFR2 | ['TGCTYGATCCACTGGATGTGGGG'] | ['TGCTYGATCCACTGGATGTGGGG', 'GTGCTYGATCCACTGGATGTGGG', 'CGTGCTYGATCCACTGGATGTGG'] | ['Crouzon syndrome'] |
| NM_000141.4 (FGFR2):c.1576A>G (p.Lys526Glu) | 121918507 | FGFR2 | [ ] | [ ] | ['Crouzon syndrome', 'Scaphocephaly, maxillary retrusion, and mental retardation'] |
| NM_002739.3 (PRKCG):c.380A>G (p.Gln127Arg) | 121918515 | PRKCG | [ ] | [ ] | ['Spinocerebellar ataxia 14'] |
| NM_002739.3 (PRKCG):c.1081A>G (p.Ser361Gly) | 121918517 | PRKCG | [ ] | [ ] | ['Spinocerebellar ataxia 14'] |
| NM_000098.2 (CPT2):c.359A>G (p.Tyr120Cys) | 121918528 | CPT2 | ['GATAGGYACATATCAAACCAGGG', 'AGATAGGYACATATCAAACCAGG'] | ['GATAGGYACATATCAAACCAGGG', 'AGATAGGYACATATCAAACCAGG'] | ['Carnitine palmitoyltransferase II deficiency, infantile'] |
| NM_005587.2 (MEF2A):c.788A>G (p.Asn263Ser) | 121918530 | MEF2A | ['CCAAGAYTACCACCACCTGGTGG'] | ['AGAYTACCACCACCTGGTGGAGG', 'CCAAGAYTACCACCACCTGGTGG'] | [ ] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_006204.3 (PDE6C):c.1363A>G (p.Met455Val) | 121918539 | PDE6C | [ ] | [ ] | ['Achromatopsia 5'] |
| NM_017654.3 (SAMD9):c.4483A>G (p.Lys1495Glu) | 121918554 | SAMD9 | [ ] | [ ] | ['Tumoral calcinosis, familial, normophosphatemic'] |
| NM_000191.2 (HMGCL):c.698A>G (p.His233Arg) | 727503963 | HMGCL | [ ] | [ ] | ['not provided'] |
| NM_020166.4 (MCCC1):c.137-2A>G | 727504006 | MCCC1 | [ ] | [ ] | ['3 Methylcrotonyl-CoA carboxylase 1 deficiency', 'not provided'] |
| NM_001035.2 (RYR2):c.12602A>G (p.Gln4201Arg) | 121918605 | RYR2 | [ ] | ['CGCCAGCYGCAT TCAAAGATGG'] | ['Catecholaminergic polymorphic ventricular tachycardia'] |
| NM_002764.3 (PRPS1):c.343A>G (p.Met115Val) | 587781262 | PRPS1 | [ ] | ['TAGCAYATTTGC AACAAGCTTGG'] | ['Charcot-Marie-Tooth disease, X-linked recessive, type 5', 'Deafness, high-frequency sensorineural, X-linked'] |
| NM_001161766.1 (AHCY):c.344A>G (p.Tyr115Cys) | 121918608 | AHCY | [ ] | ['GCGGGYACTTG GTGTGGATGAGG'] | ['Hypermethioninemia with s-adenosylhomocysteine hydrolase deficiency'] |
| NM_000702.3 (ATP1A2):c.1033A>G (p.Thr345Ala) | 121918613 | ATP1A2 | [ ] | ['CTGYCAGGGTCA GGCACACCTGG'] | ['Familial hemiplegic migraine type 2'] |
| NM_003126.2 (SPTA1):c.143A>G (p.Lys48Arg) | 121918644 | SPTA1 | [ ] | [ ] | ['Hereditary pyropoikilocytosis'] |
| NM_001024858.2 (SPTB):c.1A>G (p.Met1Val) | 121918651 | SPTB | [ ] | [ ] | ['Elliptocytosis 3'] |
| NM_000899.4 (KITLG):c.107A>G (p.Asn36Ser) | 121918653 | KITLG | [ ] | [ ] | ['Familial progressive hyperpigmentation with or without hypopigmentation'] |
| NM_198253.2 (TERT):c.2315A>G (p.Tyr772Cys) | 121918663 | TERT | [ ] | [ ] | ['Aplastic anemia', 'PULMONARY FIBROSIS AND/OR BONE MARROW FAILURE, TELOMERE-RELATED, 1'] |
| NM_001063.3 (TF):c.1936A>G (p.Lys646Glu) | 121918678 | TF | [ ] | [ ] | [ ] |
| NM_000535.5 (PMS2):c.904-2A>G | 587781339 | PMS2 | [ ] | ['GCAGACCYGCA CAAAATACAAGG'] | ['Hereditary cancer-predisposing syndrome'] |
| NM_001128177.1 (THRB):c.1324A>G (p.Met442Val) | 121918691 | THRB | [ ] | ['CTTCAYGTGCAG GAAGCGGCTGG'] | ['Thyroid hormone resistance, generalized, autosomal dominant'] |
| NM_001128177.1 (THRB):c.1327A>G (p.Lys443Glu) | 121918692 | THRB | [ ] | ['CCACCTYCATGT GCAGGAAGCGG'] | ['Thyroid hormone resistance, generalized, autosomal dominant'] |
| NM_001128177.1 (THRB):c.1009A>G (p.Thr337Ala) | 121918709 | THRB | [ ] | [ ] | ['Thyroid hormone resistance, selective pituitary'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_004612.3 (TGFBR1):c.1199A>G (p.Asp400Gly) | 121918711 | TGFBR1 | ['ATAGATG YCAGCACG TTTGAAGG'] | ['ATAGATGYCAG CACGTTTGAAGG'] | ['Loeys-Dietz syndrome 1'] |
| NM_000359.2 (TGM1):c.1469A>G (p.Asp490Gly) | 121918724 | TGM1 | [ ] | [ ] | ['Autosomal recessive congenital ichthyosis 1'] |
| NM_000257.3 (MYH7):c.1727A>G (p.His576Arg) | 727504238 | MYH7 | [ ] | [ ] | ['Familial hypertrophic cardiomyopathy 1', 'Cardiomyopathy', 'not specified'] |
| NM_000257.3 (MYH7):c.1954A>G (p.Arg652Gly) | 727504239 | MYH7 | [ ] | [ ] | ['Primary familial hypertrophic cardiomyopathy', 'Familial hypertrophic cardiomyopathy 1'] |
| NM_000257.3 (MYH7):c.1496A>G (p.Glu499Gly) | 727504270 | MYH7 | [ ] | [ ] | ['Cardiomyopathy', 'not specified'] |
| NM_000257.3 (MYH7):c.2539A>G (p.Lys847Glu) | 727504310 | MYH7 | [ ] | [ ] | ['Familial hypertrophic cardiomyopathy 1', 'Cardiomyopathy', 'not specified'] |
| NM_000256.3 (MYBPC3):c.2906-2A>G | 727504333 | MYBPC3 | [ ] | ['CCGTTCYGTGGG TATAGAGTGGG', 'GCCGTTCYGTGG GTATAGAGTGG'] | ['Familial hypertrophic cardiomyopathy 4'] |
| NM_001128425.1 (MUTYH):c.1187-2A>G | 587781628 | MUTYH | ['ACCYGAG AGGGAGG GCAGCCAG G'] | ['ACCYGAGAGGG AGGGCAGCCAGG'] | ['Hereditary cancer-predisposing syndrome', 'Carcinoma of colon'] |
| NM_005188.3 (CBL):c.1228-2A>G | 727504426 | CBL | [ ] | [ ] | ['Juvenile myelomonocytic leukemia', 'Noonan syndrome-like disorder with or without juvenile myelomonocytic leukemia', 'Rasopathy'] |
| NM_000501.3 (ELN):c.890-2A>G | 727504434 | ELN | ['GCCYGAA AACACAGC CACAGAGG'] | ['GCCYGAAAACA CAGCCACAGAGG'] | ['Supravalvar aortic stenosis'] |
| NM_001165963.1 (SCN1A):c.2877T>A (p.Cys959Ter) | 775214722 | SCN1A | [ ] | [ ] | ['not provided'] |
| NM_000833.4 (GRIN2A):c.2449A>G (p.Met817Val) | 796052551 | GRIN2A | ['CCAYGTT GTCAATGT CCAGCTGG'] | ['CCAYGTTGTCAA TGTCCAGCTGG'] | ['not provided'] |
| NM_000314.6 (PTEN):c.493-2A>G | 587781784 | PTEN | [ ] | [ ] | ['Hereditary cancer-predisposing syndrome'] |
| NM_000498.3 (CYP11B2):c.1157T>C (p.Val386Ala) | 61757294 | — | [ ] | [ ] | ['Corticosterone methyloxidase type 2 deficiency', 'Corticosterone methyloxidase type 1 deficiency'] |
| NM_006204.3 (PDE6C):c.1483-2A>G | 786200910 | PDE6C | [ ] | ['CTTTCYGTTGAA ATAAGGATGGG', 'TCTTTCYGTTGAA ATAAGGATGG'] | ['Achromatopsia 5'] |
| NM_003588.3 (CUL4B):c.901-2A>G | 786200913 | CUL4B | [ ] | [ ] | ['Syndromic X-linked mental retardation, Cabezas type'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000397.3 (CYBB):c.302A>G (p.His101Arg) | 137854591 | CYBB | [ ] | [ ] | ['Granulomatous disease, chronic, X-linked, variant', 'not provided'] |
| NM_000311.3 (PRNP):c.385A>G (p.Met129Val) | 1799990 | PRNP | [ ] | [ ] | ['Jakob-Creutzfeldt disease', 'Genetic prion diseases', 'Fatal familial insomnia', 'not specified'] |
| NM_000051.3 (ATM):c.3994-2A>G | 587782276 | ATM | [ ] | [ ] | ['Ataxia-telangiectasia syndrome', 'Hereditary cancer-predisposing syndrome'] |
| NM_005211.3 (CSF1R):c.1754-2A>G | 281860267 | CSF1R | [ ] | [ ] | ['Hereditary diffuse leukoencephalopathy with spheroids'] |
| NM_004646.3 (NPHS1):c.1756A>G (p.Arg586Gly) | 730880174 | NPHS1 | [ ] | [ ] | ['Finnish congenital nephrotic syndrome'] |
| NM_005211.3 (CSF1R):c.2320-2A>G | 281860272 | CSF1R | ['CACYGAGGGAAAGCACTGCAGGG'] | ['CACYGAGGGAAAGCACTGCAGGG', 'GCACYGAGGGAAAGCACTGCAGG'] | ['Hereditary diffuse leukoencephalopathy with spheroids'] |
| NM_000256.3 (MYBPC3):c.3392T>C (p.Ile1131Thr) | 370890951 | MYBPC3 | [ ] | [ ] | ['Cardiomyopathy', 'Cardiac arrest', 'not specified'] |
| NM_000551.3 (VHL):c.586A>T (p.Lys196Ter) | 281860296 | VHL | [ ] | ['GGTCTTYCTGCACATTTGGGTGG'] | ['Von Hippel-Lindau syndrome'] |
| NM_005247.2 (FGF3):c.146A>G (p.Tyr49Cys) | 281860300 | FGF3 | ['CAGYAGAGCTTGCGGCGCCGGGG', 'GCAGYAGAGCTTGCGGCGCCGGG', 'CGCAGYAGAGCTTGCGGCGCCGG'] | ['CAGYAGAGCTTGCGGCGCCGGGG', 'GCAGYAGAGCTTGCGGCGCCGGG', 'CGCAGYAGAGCTTGCGGCGCCGG'] | ['Deafness with labyrinthine aplasia microtia and microdontia (LAMM)'] |
| NM_005247.2 (FGF3):c.317A>G (p.Tyr106Cys) | 281860306 | FGF3 | [ ] | [ ] | ['Deafness with labyrinthine aplasia microtia and microdontia (LAMM)'] |
| NM_000314.6 (PTEN):c.403A>G (p.Ile135Val) | 587782360 | PTEN | [ ] | [ ] | ['Hereditary cancer-predisposing syndrome'] |
| NM_004990.3 (MARS):c.1031A>G (p.Tyr344Cys) | 766466297 | MARS | [ ] | [ ] | ['Pulmonary alveolar proteinosis', 'Interstitial lung and liver disease'] |
| NM_006343.2 (MERTK):c.1605-2A>G | 730880273 | MERTK | [ ] | [ ] | ['Retinitis pigmentosa 38'] |
| NM_003611.2 (OFD1):c.935+706A>G | 730880283 | OFD1 | [ ] | [ ] | ['Retinitis Pigmentosa 23'] |
| NM_004793.3 (LONP1):c.2353A>G (p.Arg785Gly) | 730880293 | LONP1 | [ ] | [ ] | ['CODAS syndrome'] |
| NM_001698.2 (AUH):c.263-2A>G | 730880311 | AUH | [ ] | [ ] | ['3-Methylglutaconic aciduria'] |
| NM_001698.2 (AUH):c.943-2A>G | 730880312 | AUH | [ ] | [ ] | ['3-Methylglutaconic aciduria'] |
| NM_000169.2 (GLA):c.370-2A>G | 730880444 | — | [ ] | ['GTGAACCYGAAATGAGAGGGAGG'] | ['not provided'] |
| NM_001110792.1 (MECP2):c.520A>G (p.Arg174Gly) | 727505391 | MECP2 | [ ] | [ ] | ['Rett disorder'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_030662.3 (MAP2K2):c.181A>G (p.Lys61Glu) | 730880517 | MAP2K2 | [ ] | [ ] | ['Cardiofaciocutaneous syndrome', 'Rasopathy'] |
| NM_000256.3 (MYBPC3):c.1227-2A>G | 730880531 | MYBPC3 | [ ] | ['GTACCYGGGTG GGGGCCGCAGGG', 'TGTACCYGGGTG GGGGCCGCAGG'] | ['Familial hypertrophic cardiomyopathy 4', 'Cardiomyopathy'] |
| NM_000642.2 (AGL):c.4260-12A>G | 369973784 | AGL | [ ] | [ ] | ['Glycogen storage disease type III', 'Glycogen storage disease IIIa', 'Glycogen storage disease IIIb'] |
| NM_000267.3 (NF1):c.1642-8A>G | 267606602 | NF1 | [ ] | [ ] | ['Neurofibromatosis, type 1', 'Juvenile myelomonocytic leukemia'] |
| NM_000267.3 (NF1):c.5944-5A>G | 267606604 | NF1 | [ ] | [ ] | ['Neurofibromatosis, type 1', 'Neurofibromatosis, familial spinal'] |
| m.1555A>G | 267606617 | MT-RNR1 | [ ] | [ ] | ['Aminoglycoside-induced deafness', 'Cardiomyopathy, restrictive', 'Deafness, nonsyndromic sensorineural, mitochondrial'] |
| NM_022458.3 (LMBR1):c.423+5252A>G | 606231150 | LMBR1 | [ ] | [ ] | ['Triphalangeal thumb', 'Preaxial polydactyly 2'] |
| NM_000642.2 (AGL):c.3439A>G (p.Arg1147Gly) | 267606639 | AGL | [ ] | [ ] | ['Glycogen storage disease IIIc'] |
| NM_013411.4 (AK2):c.494A>G (p.Asp165Gly) | 267606643 | AK2 | [ ] | ['TCAYCTTTCATG GGCTCTTTTGG'] | ['Reticular dysgenesis'] |
| NM_001142800.1 (EYS):c.9209T>C (p.Ile3070Thr) | 183589498 | EYS | [ ] | [ ] | ['Retinitis pigmentosa'] |
| NM_004183.3 (BEST1):c.680A>G (p.Tyr227Cys) | 267606677 | BEST1 | [ ] | [ ] | ['Vitelliform dystrophy', 'Retinitis pigmentosa, concentric', 'not provided'] |
| NM_005188.3 (CBL):c.1144A>G (p.Lys382Glu) | 267606705 | CBL | [ ] | ['TATTTYACATAG TTGGAATGTGG'] | ['Noonan syndrome-like disorder with or without juvenile myelomonocytic leukemia'] |
| NM_001017361.2 (KHDC3L):c.1A>G (p.Met1Val) | 606231235 | KHDC3L | [ ] | [ ] | ['Hydatidiform mole, recurrent, 2'] |
| NM_144577.3 (CCDC114):c.487-2A>G | 606231239 | CCDC114 | [ ] | [ ] | ['Ciliary dyskinesia, primary, 20'] |
| NM_000277.1 (PAH):c.916A>G (p.Ile306Val) | 62642934 | PAH | [ ] | ['GGCCAAYTTCCT GTAATTGGGGG', 'AGGCCAAYTTCC TGTAATTGGGG'] | ['Phenylketonuria', 'Hyperphenylalanine mia, non-pku', 'not provided'] |
| NM_000257.3 (MYH7):c.2792A>G (p.Glu931Gly) | 730880760 | MYH7 | [ ] | [ ] | ['Cardiomyopathy'] |
| NM_207034.2 (EDN3):c.335A>G (p.His112Arg) | 267606778 | EDN3 | [ ] | [ ] | ['Waardenburg syndrome type 4B'] |
| NM_000117.2 (EMD):c.1A>G (p.Met1Val) | 267606782 | EMD | [ ] | ['TCCAYGGCGGGT GCGGGCTCAGG'] | ['Emery-Dreifuss muscular dystrophy, X-linked'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_003937.2 (KYNU):c.592A>G (p.Thr198Ala) | 606231307 | KYNU | [ ] | [ ] | ['Hydroxykynureninuria'] |
| NM_004387.3 (NKX2-5):c.461A>G (p.Glu154Gly) | 587782928 | NKX2-5 | [ ] | [ ] | ['Atrial septal defect 7 with or without atrioventricular conduction defects'] |
| NM_000142.4 (FGFR3):c.1454A>G (p.Gln485Arg) | 267606808 | FGFR3 | [ ] | [ ] | ['Thanatophoric dysplasia type 1'] |
| NM_014053.3 (FLVCR1):c.361A>G (p.Asn121Asp) | 267606820 | FLVCR1 | [ ] | ['AGGCGTYGACC AGCGAGTACAGG'] | ['Posterior column ataxia with retinitis pigmentosa'] |
| NM_000257.3 (MYH7):c.4664A>G (p.Glu1555Gly) | 730880805 | — | [ ] | ['GCCCYCCTCGTG CTCCAGGGAGG', 'CTTGCCCYCCTC GTGCTCCAGGG'] | ['Cardiomyopathy'] |
| NM_138387.3 (G6PC3):c.346A>G (p.Met116Val) | 267606834 | G6PC3 | [ ] | ['TGATCAYGCAGT GTCCAGAAGGG', 'GTGATCAYGCAG TGTCCAGAAGG'] | ['Dursun syndrome'] |
| NM_020347.3 (LZTFL1):c.260T>C (p.Leu87Pro) | 515726135 | LZTFL1 | [ ] | [ ] | ['Bardet-Biedl syndrome', 'Bardet-Biedl syndrome 17'] |
| NM_000175.3 (GPI):c.1028A>G (p.Gln343Arg) | 267606851 | GPI | [ ] | ['GTACYGGTCATA GGGCAGCATGG'] | ['Hemolytic anemia, nonspherocytic, due to glucose phosphate isomerase deficiency'] |
| NM_005859.4 (PURA):c.289A>G (p.Lys97Glu) | 587782994 | PURA | [ ] | [ ] | ['Neonatal hypotonia', 'Intellectual disability', 'Seizures', 'Delayed speech and language development', 'Global developmental delay', 'Mental retardation, autosomal dominant 31'] |
| NM_005144.4 (HR):c.-218A>G | 267606869 | HR | ['CTCYAGG GCCGCAGG TTGGAGGG'] | ['CTCYAGGGCCGC AGGTTGGAGGG', 'GCTCYAGGGCCG CAGGTTGGAGG', 'GGCGCTCYAGGG CCGCAGGTTGG'] | ['Marie Unna hereditary hypotrichosis 1'] |
| NM_000257.3 (MYH7):c.789A>G (p.Ile263Met) | 730880855 | MYH7 | [ ] | [ ] | ['Cardiomyopathy'] |
| NM_000060.3 (BTD):c.683A>G (p.Asp228Gly) | 587783004 | BTD | [ ] | [ ] | ['Biotinidase deficiency'] |
| NM_000257.3 (MYH7):c.1051A>G (p.Lys351Glu) | 730880864 | MYH7 | [ ] | [ ] | ['Cardiomyopathy'] |
| NM_015713.4 (RRM2B):c.190T>C (p.Trp64Arg) | 515726182 | RRM2B | [ ] | ['TTCCTTCYGGAC AGCAGAAGAGG'] | ['RRM2B-related mitochondrial disease'] |
| NM_005957.4 (MTHFR):c.971A>G (p.Asn324Ser) | 267606887 | MTHFR | ['CGCGGYT GAGGGTGT AGAAGTGG'] | ['CGCGGYTGAGGG TGTAGAAGTGG'] | ['Homocystinuria due to MTHFR deficiency'] |
| NM_015713.4 (RRM2B):c.368T>C (p.Phe123Ser) | 515726187 | RRM2B | [ ] | [ ] | ['RRM2B-related mitochondrial disease'] |
| m.12770A>G | 267606894 | MT-ND5 | [ ] | [ ] | ['Juvenile myopathy, encephalopathy, lactic acidosis AND stroke'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000257.3 (MYH7):c.1805A>G (p.Asn602Ser) | 730880880 | MYH7 | [ ] | [ ] | ['Cardiomyopathy'] |
| NM_018109.3 (MTPAP):c.1432A>G (p.Asn478Asp) | 267606900 | MTPAP | ['AATGGAT YCTGAATG TACAGAGG'] | ['AATGGATYCTGA ATGTACAGAGG'] | ['Ataxia, spastic, 4, autosomal recessive'] |
| NM_000257.3 (MYH7):c.2717A>G (p.Asp906Gly) | 267606908 | MYH7 | [ ] | [ ] | ['Primary familial hypertrophic cardiomyopathy', 'Familial hypertrophic cardiomyopathy 1', 'Cardiomyopathy'] |
| NM_003122.4 (SPINK1):c.160T>C (p.Tyr54His) | 515726207 | SPINK1 | [ ] | [ ] | ['Hereditary pancreatitis'] |
| NM_003159.2 (CDKL5):c.404-2A>G | 587783080 | CDKL5 | [ ] | [ ] | ['not provided'] |
| NM_003159.2 (CDKL5):c.449A>G (p.Lys150Arg) | 587783083 | CDKL5 | ['ACAGTYT TAGGACAT CATTGTGG'] | ['ACAGTYTTAGGA CATCATTGTGG'] | ['not provided'] |
| NM_016203.3 (PRKAG2):c.1589A>G (p.His530Arg) | 267606977 | PRKAG2 | [ ] | [ ] | ['Familial hypertrophic cardiomyopathy 6', 'not provided'] |
| NM_198965.1 (PTHLH):c.534A>G (p.Ter178Trp) | 267606987 | PTHLH | [ ] | [ ] | ['Brachydactyly type E2'] |
| NM_000531.5 (OTC):c.122A>G (p.Asp41Gly) | 74518351 | OTC | [ ] | [ ] | ['not provided'] |
| NM_001134363.2 (RBM20):c.1909A>G (p.Ser637Gly) | 267607005 | RBM20 | [ ] | [ ] | ['Dilated cardiomyopathy 1DD'] |
| NM_000553.4 (WRN):c.403A>G (p.Lys135Glu) | 267607008 | WRN | [ ] | [ ] | ['Werner syndrome'] |
| NM_002880.3 (RAF1):c.1279A>G (p.Ser427Gly) | 730881002 | RAF1 | [ ] | ['GCTGCYGCCCTC GCACCACTGGG', 'GGCTGCYGCCCT CGCACCACTGG'] | ['Rasopathy'] |
| NM_002977.3 (SCN9A):c.29A>G (p.Gln10Arg) | 267607030 | SCN9A | [ ] | ['AAGCTCYGAGG TCCTGGGGGAGG'] | ['Primary erythromelalgia'] |
| NM_016955.3 (SEPSECS):c.1001A>G (p.Tyr334Cys) | 267607036 | SEPSECS | [ ] | [ ] | ['Pontocerebellar hypoplasia type 2D'] |
| NM_007373.3 (SHOC2):c.4A>G (p.Ser2Gly) | 267607048 | SHOC2 | [ ] | ['TACYCATGGTGA CTCAAGCCTGG'] | ['Noonan-like syndrome with loose anagen hair', 'Rasopathy'] |
| NM_005633.3 (SOS1):c.1430A>G (p.Gln477Arg) | 730881044 | SOS1 | [ ] | [ ] | ['Rasopathy'] |
| NM_007375.3 (TARDBP):c.787A>G (p.Lys263Glu) | 267607102 | TARDBP | [ ] | [ ] | ['FRONTOTEMPORAL DEMENTIA WITH TDP43 INCLUSIONS, TARDBP-RELATED'] |
| NM_003286.2 (TOP1):c.1598A>G (p.Asp533Gly) | 267607131 | — | [ ] | [ ] | [ ] |
| NM_021625.4 (TRPV4):c.1805A>G (p.Tyr602Cys) | 267607150 | TRPV4 | [ ] | [ ] | ['Spondyloepiphyseal dysplasia Maroteaux type'] |
| NM_000551.3 (VHL):c.491A>G (p.Gln164Arg) | 267607170 | VHL | [ ] | [ ] | ['Von Hippel-Lindau syndrome'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_001006657.1 (WDR35):c.1877A>G (p.Glu626Gly) | 267607174 | WDR35 | [ ] | [ ] | ['Cranioectodermal dysplasia 2'] |
| NM_024884.2 (L2HGDH):c.293A>G (p.His98Arg) | 267607206 | L2HGDH | [ ] | [ ] | ['L-2-hydroxyglutaric aciduria'] |
| NM_002437.4 (MPV17):c.262A>G (p.Lys88Glu) | 267607256 | MPV17 | [ ] | [ ] | ['Navajo neurohepatopathy'] |
| NM_006888.4 (CALM1):c.293A>G (p.Asn98Ser) | 267607277 | CALM1 | [ ] | [ ] | ['Catecholaminergic polymorphic ventricular tachycardia', 'Ventricular tachycardia, catecholaminergic polymorphic, 4'] |
| NM_000487.5 (ARSA):c.*96A>G | 6151429 | ARSA | [ ] | [ ] | ['Metachromatic leukodystrophy', 'Arylsulfatase A pseudodeficiency', 'not provided'] |
| NM_003122.4 (SPINK1):c.194+2T>C | 148954387 | SPINK1 | [ ] | [ ] | ['Hereditary pancreatitis'] |
| NM_000552.3 (VWF):c.3437A>G (p.Tyr1146Cys) | 267607326 | VWF | [ ] | [ ] | ['von Willebrand disease type 2', 'not provided'] |
| NM_000489.4 (ATRX):c.4826A>G (p.His1609Arg) | 122445093 | ATRX | [ ] | [ ] | ['ATR-X syndrome'] |
| NM_000489.4 (ATRX):c.6488A>G (p.Tyr2163Cys) | 122445098 | ATRX | [ ] | [ ] | ['ATR-X syndrome'] |
| NM_000489.4 (ATRX):c.6811A>G (p.Arg2271Gly) | 122445112 | ATRX | [ ] | [ ] | [ ] |
| NM_004380.2 (CREBBP):c.3983-2A>G | 587783486 | CREBBP | [ ] | ['GCAGCCCYAGG AAGTCCAGAAGG'] | ['Rubinstein-Taybi syndrome'] |
| NM_004380.2 (CREBBP):c.4508A>G (p.Tyr1503Cys) | 587783497 | CREBBP | [ ] | [ ] | ['Rubinstein-Taybi syndrome'] |
| NM_000051.3 (ATM):c.3154-2A>G | 730881357 | ATM | [ ] | ['AGCCYACGGGA AAAGAACTGTGG'] | ['Hereditary cancer-predisposing syndrome'] |
| NM_178151.2 (DCX):c.1027-2A>G | 587783518 | DCX | [ ] | [ ] | ['Heterotopia'] |
| NM_178151.2 (DCX):c.520A>G (p.Lys174Glu) | 587783557 | DCX | [ ] | [ ] | ['Heterotopia'] |
| NM_178151.2 (DCX):c.538A>G (p.Lys180Glu) | 587783560 | DCX | [ ] | [ ] | ['Heterotopia'] |
| NM_178151.2 (DCX):c.607A>G (p.Thr203Ala) | 587783570 | DCX | [ ] | [ ] | ['Heterotopia'] |
| NM_001257235.1 (ALG13):c.8A>G (p.Asn3Ser) | 398122394 | ALG13 | [ ] | [ ] | ['Congenital disorder of glycosylation type 1s'] |
| NM_001256864.1 (DNAJC6):c.801-2A>G | 398122404 | DNAJC6 | [ ] | ['AGGTATCYGAA ACAGAAGGTTGG'] | ['Parkinson disease 19, juvenile-onset'] |
| NM_001927.3 (DES):c.1024A>G (p.Asn342Asp) | 267607482 | DES | [ ] | ['GAATCGTYCTGC AGGAGAGGGGG'] | ['Myofibrillar myopathy 1', 'not provided'] |
| NM_001927.3 (DES):c.735+3A>G | 267607483 | DES | [ ] | [ ] | ['Myofibrillar myopathy 1', 'not provided'] |
| NM_001927.3 (DES):c.1333A>G (p.Thr445Ala) | 267607498 | DES | [ ] | [ ] | ['not provided'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_005249.4 (FOXG1):c.757A>G (p.Asn253Asp) | 587783641 | FOXG1 | [ ] | [ ] | ['Rett syndrome, congenital variant'] |
| NM_000252.2 (MTM1):c.1406A>G (p.His469Arg) | 587783789 | MTM1 | [ ] | [ ] | ['Severe X-linked myotubular myopathy'] |
| NM_000391.3 (TPP1):c.833A>G (p.Gln278Arg) | 796053439 | TPP1 | [ ] | ['CAGGTACYGCA CATCTAGACTGG'] | ['not provided'] |
| NM_000252.2 (MTM1):c.301A>G (p.Ser101Gly) | 587783818 | MTM1 | [ ] | [ ] | ['Severe X-linked myotubular myopathy'] |
| NM_000252.2 (MTM1):c.343-2A>G | 587783821 | MTM1 | [ ] | [ ] | ['Severe X-linked myotubular myopathy'] |
| NM_000252.2 (MTM1):c.529-2A>G | 587783831 | MTM1 | [ ] | [ ] | ['Severe X-linked myotubular myopathy'] |
| NM_000252.2 (MTM1):c.550A>G (p.Arg184Gly) | 587783835 | MTM1 | [ ] | ['GTTATTCYCCAA TGGTGATTGGG'] | ['Severe X-linked myotubular myopathy'] |
| NM_000158.3 (GBE1):c.691+2T>C | 192044702 | GBE1 | [ ] | [ ] | ['Glycogen storage disease, type IV'] |
| NM_000252.2 (MTM1):c.629A>G (p.Asp210Gly) | 587783842 | MTM1 | [ ] | ['TCATCAYCTGAG GCACGATACGG'] | ['Severe X-linked myotubular myopathy'] |
| NM_000249.3 (MLH1):c.545+3A>G | 267607760 | MLH1 | [ ] | [ ] | ['Hereditary Nonpolyposis Colorectal Neoplasms'] |
| NM_000249.3 (MLH1):c.589-2A>G | 267607767 | MLH1 | [ ] | [ ] | ['Hereditary Nonpolyposis Colorectal Neoplasms', 'Hereditary cancer-predisposing syndrome'] |
| NM_000249.3 (MLH1):c.884+4A>G | 267607777 | MLH1 | [ ] | ['TGCTACAYTACC TGAGGTACAGG'] | ['Hereditary Nonpolyposis Colorectal Neoplasms'] |
| NM_000081.3 (LYST):c.10127A>G (p.Asn3376Ser) | 80338669 | LYST | [ ] | [ ] | ['Ch\xc3\xa9diak-Higashi syndrome'] |
| NM_000528.3 (MAN2B1):c.1831-2A>G | 80338678 | MAN2B1 | [ ] | [ ] | ['Deficiency of alpha-mannosidase'] |
| NM_022132.4 (MCCC2):c.569A>G (p.His190Arg) | 119103225 | MCCC2 | [ ] | [ ] | ['3-methylcrotonyl CoA carboxylase 2 deficiency'] |
| m.3260A>G | 199474663 | MT-TL1 | ['TTAAGTT YTATGCGA TTACCGGG'] | ['TTAAGTTYTATG CGATTACCGGG'] | ['Cardiomyopathy with or without skeletal myopathy'] |
| NM_014874.3 (MFN2):c.827A>G (p.Gln276Arg) | 119103264 | MFN2 | [ ] | [ ] | ['Hereditary motor and sensory neuropathy with optic atrophy'] |
| NM_004525.2 (LRP2):c.770-2A>G | 80338743 | LRP2 | [ ] | [ ] | ['Donnai Barrow syndrome'] |
| NM_005120.2 (MED12):c.3020A>G (p.Asn1007Ser) | 80338759 | MED12 | [ ] | [ ] | ['X-linked mental retardation with marfanoid habitus syndrome'] |
| NM_000834.3 (GRIN2B):c.2172-2A>G | 398122824 | GRIN2B | [ ] | [ ] | ['Mental retardation, autosomal dominant 6'] |
| NM_000249.3 (MLH1):c.1990-2A>G | 267607883 | MLH1 | [ ] | [ ] | ['Hereditary Nonpolyposis Colorectal Neoplasms', 'not provided'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000518.4 (HBB):c.59A>G (p.Asn20Ser) | 33972047 | HBB | [ ] | ['CACGYTCACCTT GCCCCACAGGG', 'CCACGYTCACCT TGCCCCACAGG'] | ['alpha Thalassemia'] |
| NM_003688.3 (CASK):c.2168A>G (p.Tyr723Cys) | 398122844 | CASK | [ ] | [ ] | ['FG syndrome 4', 'Mental retardation and microcephaly with pontine and cerebellar hypoplasia'] |
| NM_024675.3 (PALB2):c.109-2A>G | 730881897 | PALB2 | [ ] | [ ] | ['Hereditary cancer-predisposing syndrome'] |
| NM_000251.2 (MSH2):c.1511-2A>G | 267607962 | MSH2 | [ ] | [ ] | ['Hereditary Nonpolyposis Colorectal Neoplasms'] |
| NM_003124.4 (SPR):c.596-2A>G | 398122922 | SPR | [ ] | [ ] | [Sepiapterin reductase deficiency'] |
| NM_022455.4 (NSD1):c.4498-3A>G | 587784120 | NSD1 | [ ] | [ ] | ['Sotos syndrome 1'] |
| NM_000455.4 (STK11):c.889A>G (p.Arg297Gly) | 730881978 | STK11 | [ ] | [ ] | ['Hereditary cancer-predisposing syndrome'] |
| NM_001927.3 (DES):c.1289-2A>G | 398122940 | DES | [ ] | [ ] | ['Muscular dystrophy, limb-girdle, type 2r'] |
| NM_000546.5 (TP53):c.709A>G (p.Met237Val) | 730882004 | TP53 | [ ] | ['ACACAYGTAGTT GTAGTGGATGG'] | ['Li-Fraumeni syndrome', 'Hereditary cancer-predisposing syndrome'] |
| NM_024876.3 (ADCK4):c.857A>G (p.Asp286Gly) | 398122979 | ADCK4 | [ ] | [ ] | ['Nephrotic syndrome, type 9'] |
| NM_022455.4 (NSD1):c.6059A>G (p.Asn2020Ser) | 587784178 | NSD1 | [ ] | [ ] | ['Sotos syndrome 1'] |
| NM_022455.4 (NSD1):c.6356A>G (p.Asp2119Gly) | 587784191 | NSD1 | [ ] | [ ] | ['Sotos syndrome 1'] |
| NM_007332.2 (TRPA1):c.2564A>G (p.Asn855Ser) | 398123010 | — | [ ] | [ ] | ['Familial episodic pain syndrome 1'] |
| NM_001231.4 (CASQ1):c.731A>G (p.Asp244Gly) | 730882052 | CASQ1 | [ ] | ['GGCTTGYCTGGG ATGGTCACAGG'] | ['Myopathy, vacuolar, with casq1 aggregates'] |
| NM_004004.5 (GJB2):c.487A>G (p.Met163Val) | 80338949 | GJB2 | [ ] | [ ] | ['Deafness, autosomal recessive 1A', 'not specified'] |
| NM_130466.3 (UBE3B):c.545-2A>G | 398123022 | UBE3B | [ ] | [ ] | ['Kaufman oculocerebrofacial syndrome'] |
| NM_000334.4 (SCN4A):c.4078A>G (p.Met1360Val) | 80338959 | SCN4A | [ ] | ['GATCAYGATGGT GATGTCGAAGG'] | ['Hyperkalemic Periodic Paralysis Type 1'] |
| NM_000334.4 (SCN4A):c.4108A>G (p.Met1370Val) | 80338960 | SCN4A | [ ] | ['CCATCAYGGTGA CCATGTTGAGG'] | ['Hyperkalemic Periodic Paralysis Type 1'] |
| NM_000334.4 (SCN4A):c.4774A>G (p.Met1592Val) | 80338962 | SCN4A | [ ] | ['TGTACAYGTTGA CCACGATGAGG'] | ['Hyperkalemic Periodic Paralysis Type 1', 'Familial hyperkalemic periodic paralysis'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_015250.3 (BICD2):c.2321A>G (p.Glu774Gly) | 398123030 | BICD2 | [ ] | [ ] | ['Spinal muscular atrophy, lower extremity predominant 2, autosomal dominant'] |
| NM_006012.2 (CLPP):c.270+4A>G | 398123035 | CLPP | [ ] | [ ] | ['Autosomal recessive hearing impairment with normal menstrual cycles'] |
| NM_000179.2 (MSH6):c.3439-2A>G | 267608098 | MSH6 | [ ] | [ ] | ['Hereditary Nonpolyposis Colorectal Neoplasms', 'Hereditary cancer-predisposing syndrome', 'not provided'] |
| NM_002246.2 (KCNK3):c.575A>G (p.Tyr192Cys) | 398123043 | KCNK3 | [ ] | [ ] | ['Primary pulmonary hypertension 4'] |
| NM_001070.4 (TUBG1):c.275A>G (p.Tyr92Cys) | 398123046 | TUBG1 | [ ] | [ ] | ['Cortical dysplasia, complex, with other brain malformations 4'] |
| NM_000383.3 (AIRE):c.254A>G (p.Tyr85Cys) | 179363882 | AIRE | [ ] | [ ] | ['Polyglandular autoimmune syndrome, type 1', 'not provided'] |
| NM_001651.3 (AQP5):c.367A>G (p.Asn123Asp) | 398123057 | AQP5 | [ ] | [ ] | ['Diffuse palmoplantar keratoderma, Bothnian type'] |
| NM_012160.4 (FBXL4):c.1694A>G (p.Asp565Gly) | 398123062 | FBXL4 | [ ] | ['TATGYCCAGCTG CTGTAACCTGG'] | ['Mitochondrial DNA depletion syndrome 13 (encephalomyopathic type)'] |
| NM_024531.4 (SLC52A2):c.914A>G (p.Tyr305Cys) | 398123068 | SLC52A2 | [ ] | [ ] | [Brown-Vialetto-Van Laere syndrome 2'] |
| NM_001039550.1 (DNAJB2):c.14A>G (p.Tyr5Cys) | 730882140 | DNAJB2 | [ ] | ['GATCTCGYAGTA GGATGCCATGG'] | ['Charcot-Marie-Tooth disease', 'Charcot-Marie-Tooth disease, axonal, type 2T'] |
| NM_052859.3 (RFT1):c.1222A>G (p.Met408Val) | 796053522 | RFT1 | [ ] | ['GCAYCACAAAA TTGTACCTGGGG', 'AGCAYCACAAAA TTGTACCTGGG', 'CAGCAYCACAAA ATTGTACCTGG'] | ['Congenital disorder of glycosylation type 1N'] |
| NM_007294.3 (BRCA1):c.5057A>G (p.His1686Arg) | 730882166 | BRCA1 | [ ] | [ ] | ['Breast-ovarian cancer, familial 1'] |
| NM_000050.4 (ASS1):c.496-2A>G | 398123130 | ASS1 | [ ] | [ ] | ['Citrullinemia type I'] |
| NM_012233.2 (RAB3GAP1):c.649-2A>G | 730882183 | RAB3GAP1 | [ ] | [ ] | ['Warburg micro syndrome 1'] |
| NM_000159.3 (GCDH):c.542A>G (p.Glu181Gly) | 398123194 | GCDH | [ ] | [ ] | ['Glutaric aciduria, type 1', 'not provided'] |
| NM_000288.3 (PEX7):c.340-10A>G | 267608255 | PEX7 | [ ] | [ ] | ['Phytanic acid storage disease', 'Peroxisome biogenesis disorder 9B'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000038.5 (APC):c.221-2A>G | 786201291 | APC | [ ] | [ ] | ['Hereditary cancer-predisposing syndrome'] |
| NM_000169.2 (GLA):c.509A>G (p.Asp170Gly) | 398123210 | — | [ ] | [ ] | ['Fabry disease'] |
| NM_000169.2 (GLA):c.548-2A>G | 398123211 | — | [ ] | ['AACCYGTATGA GAAAACAATGGG', 'TAACCYGTATGA GAAAACAATGG'] | ['Fabry disease'] |
| NM_006888.4 (CALM1):c.389A>G (p.Asp130Gly) | 730882252 | CALM1 | [ ] | [ ] | ['Long QT syndrome 14'] |
| NM_000169.2 (GLA):c.647A>G (p.Tyr216Cys) | 398123217 | — | [ ] | [ ] | ['Fabry disease'] |
| NM_006306.3 (SMC1A):c.616-2A>G | 587784423 | SMC1A | [ ] | ['AGCCYGTGCAA ACAGGGGAATGG'] | ['Congenital muscular hypertrophy-cerebral syndrome'] |
| NM_000255.3 (MUT):c.1445-2A>G | 398123276 | MUT | [ ] | [ ] | ['Methylmalonic aciduria due to methylmalonyl-CoA mutase deficiency', 'not provided'] |
| NM_001083962.1 (TCF4):c.991-2A>G | 587784470 | TCF4 | [ ] | [ ] | ['Pitt-Hopkins syndrome'] |
| NM_000060.3 (BTD):c.1205A>G (p.Asn402Ser) | 201023772 | BTD | [ ] | [ ] | ['Biotinidase deficiency'] |
| NC_000007.14: g.62535490A>G | 483352872 | — | [ ] | [ ] | ['Isolated growth hormone deficiency type 1B'] |
| NM_000271.4 (NPC1):c.1832A>G (p.Asp611Gly) | 483352887 | NPC1 | [ ] | [ ] | ['Niemann-Pick disease type C1'] |
| NM_152419.2 (HGSNAT):c.372-2A>G | 483352896 | HGSNAT | [ ] | [ ] | ['Mucopolysaccharidosis, MPS-III-C'] |
| NM_001199397.1 (NEK1):c.869-2A>G | 483352906 | NEK1 | [ ] | [ ] | ['Short rib-polydactyly syndrome, Majewski type'] |
| NM_000350.2 (ABCA4):c.67-2A>G | 398123339 | ABCA4 | [ ] | [ ] | ['Stargardt disease 1'] |
| NM_004992.3 (MECP2):c.27-2A>G | 267608412 | MECP2 | [ ] | [ ] | ['Rett disorder', 'not provided'] |
| NM_003159.2 (CDKL5):c.100-2A>G | 267608423 | CDKL5 | [ ] | [ ] | ['Early infantile epileptic encephalopathy 2', 'not provided'] |
| NM_003159.2 (CDKL5):c.125A>G (p.Lys42Arg) | 267608429 | CDKL5 | [ ] | [ ] | ['Early infantile epileptic encephalopathy 2', 'not provided'] |
| NM_000487.5 (ARSA):c.1108-2A>G | 398123411 | ARSA | [ ] | ['GGCTCYGGGGG CAGAGTCAGGGG', 'GGGCTCYGGGGG CAGAGTCAGGG', 'AGGGCTCYGGGG GCAGAGTCAGG'] | ['Metachromatic leukodystrophy'] |
| NM_003159.2 (CDKL5):c.380A>G (p.His127Arg) | 267608468 | CDKL5 | [ ] | [ ] | ['Atypical Rett syndrome', 'not provided'] |
| NM_000489.4 (ATRX):c.134-2A>G | 398123420 | ATRX | [ ] | [ ] | ['not provided'] |
| NM_003159.2 (CDKL5):c.464-2A>G | 267608480 | CDKL5 | [ ] | [ ] | ['Early infantile epileptic encephalopathy 2', 'not provided'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000489.4 (ATRX):c.536A>G (p.Asn179Ser) | 398123425 | ATRX | [ ] | [ ] | ['not provided'] |
| NM_000512.4 (GALNS):c.1171A>G (p.Met391Val) | 398123429 | GALNS | [ ] | ['CCGCCAYCAGC GTGTCGCCACGG'] | ['Mucopolysaccharidosis, MPS-IV-A', 'not provided'] |
| NM_003159.2 (CDKL5):c.578A>G (p.Asp193Gly) | 267608500 | CDKL5 | [ ] | ['ATGYCCACGGA CTTTCCATAGGG', 'CATGYCCACGGA CTTTCCATAGG'] | ['Early infantile epileptic encephalopathy 2'] |
| NM_000521.3 (HEXB):c.1243-2A>G | 398123446 | HEXB | [ ] | [ ] | ['Sandhoff disease', 'not provided'] |
| NM_003159.2 (CDKL5):c.978-2A>G | 267608553 | CDKL5 | [ ] | [ ] | ['Early infantile epileptic encephalopathy 2', 'not provided'] |
| NM_001164342.2 (ZBTB20):c.1787A>G (p.His596Arg) | 483353066 | ZBTB20 | [ ] | [ ] | ['Primrose syndrome'] |
| NM_000402.4 (G6PD):c.188T>C (p.Ile63Thr) | 398123552 | — | [ ] | ['ACACACAYATTC ATCATCATGGG'] | ['Anemia, nonspherocytic hemolytic, due to G6PD deficiency', 'not provided'] |
| NM_001893.4 (CSNK1D):c.130A>G (p.Thr44Ala) | 104894561 | CSNK1D | [ ] | [ ] | ['Advanced sleep phase syndrome, familial, 2'] |
| NM_000155.3 (GALT):c.563A>G (p.Gln188Arg) | 75391579 | GALT | [ ] | ['TTACCYGGCAGT GGGGGTGGGGG', 'CTTACCYGGCAG TGGGGGTGGGG', 'CCTTACCYGGCA GTGGGGGTGGG'] | ['Deficiency of UDPglucose-hexose-1-phosphate uridylyltransferase', 'not provided'] |
| NM_007055.3 (POLR3A):c.2554A>G (p.Met852Val) | 267608671 | POLR3A | [ ] | [ ] | ['Hypomyelinating leukodystrophy 7'] |
| NM_001848.2 (COL6A1):c.805-2A>G | 398123639 | COL6A1 | [ ] | ['TTCTCCCYGGAA CACAAAACAGG'] | ['Ullrich congenital muscular dystrophy', 'Bethlem myopathy', 'not provided'] |
| NM_001918.3 (DBT):c.773-2A>G | 398123674 | DBT | [ ] | [ ] | ['Maple syrup urine disease', 'not provided'] |
| NM_001999.3 (FBN2):c.3740T>C (p.Met1247Thr) | 149054177 | FBN2 | ['GAATGTA YGATAATG AACGGAG G'] | ['GAATGTAYGAT AATGAACGGAGG'] | ['not specified', 'Macular degeneration, early-onset'] |
| NM_003482.3 (KMT2D):c.5645-2A>G | 398123750 | KMT2D | [ ] | ['GCAGTTCYGTGG GGGAATGAAGG'] | ['Kabuki make-up syndrome', 'not provided'] |
| NM_003494.3 (DYSF):c.1398-2A>G | 398123769 | DYSF | [ ] | [ ] | ['Limb-girdle muscular dystrophy, type 2B', 'not provided'] |
| NM_015560.2 (OPA1):c.1146A>G (p.Ile382Met) | 143319805 | OPA1 | [ ] | [ ] | ['Dominant hereditary optic atrophy', 'Optic Atrophy Type 1', 'not specified', 'not provided'] |
| NM_203447.3 (DOCK8):c.1418A>G (p.Lys473Arg) | 112321280 | DOCK8 | [ ] | [ ] | ['Hyperimmunoglobulin E recurrent infection syndrome, autosomal recessive'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_001145.4 (ANG):c.121A>G (p.Lys41Glu) | 121909537 | — | ['TGGTTYG GCATCATA GTGCTGGG, 'GTGGTTYG GCATCATA GTGCTGG'] | ['TGGTTYGGCATC ATAGTGCTGGG', 'GTGGTTYGGCAT CATAGTGCTGG'] | ['Amyotrophic lateral sclerosis type 9'] |
| NM_004006.2 (DMD):c.3432+3A>G | 398123938 | DMD | [ ] | [ ] | ['Dilated cardiomyopathy 3B'] |
| NM_006514.3 (SCN10A):c.1661T>C (p.Leu554Pro) | 138404783 | SCN10A | [ ] | [ ] | ['Episodic pain syndrome, familial, 2'] |
| NM_004006.2 (DMD):c.6763-2A>G | 398124033 | DMD | [ ] | [ ] | ['Dilated cardiomyopathy 3B'] |
| NM_001079802.1 (FKTN):c.1112A>G (p.Tyr371Cys) | 119464998 | FKTN | [ ] | [ ] | [ ] |
| NM_004006.2 (DMD):c.9224+61934A>G | 398124084 | DMD | [ ] | [ ] | ['Dilated cardiomyopathy 3B'] |
| NM_004006.2 (DMD):c.9225-647A>G | 398124091 | DMD | [ ] | [ ] | ['Duchenne muscular dystrophy', 'Becker muscular dystrophy', 'Dilated cardiomyopathy 3B'] |
| NM_004006.2 (DMD):c.9650-2A>G | 398124100 | DMD | [ ] | [ ] | ['Duchenne muscular dystrophy', 'Becker muscular dystrophy', 'Dilated cardiomyopathy 3B'] |
| NM_198578.3 (LRRK2):c.3342A>G (p.Leu1114=) | 35808389 | LRRK2 | [ ] | [ ] | ['Parkinson disease 8, autosomal dominant'] |
| NM_031229.2 (RBCK1):c.1160A>G (p.Asn387Ser) | 566912235 | RBCK1 | [ ] | [ ] | ['Polyglucosan body myopathy 1 with or without immunodeficiency'] |
| NM_000178.2 (GSS):c.656A>G (p.Asp219Gly) | 28938472 | GSS | [ ] | [ ] | ['Glutathione synthetase deficiency of erythrocytes, hemolytic anemia due to'] |
| NM_025132.3 (WDR19):c.407-2A>G | 374400438 | WDR19 | [ ] | [ ] | [SENIOR-LOKEN SYNDROME 8'] |
| NM_144997.5 (FLCN):c.1433-2A>G | 398124528 | FLCN | [ ] | ['CCCACYGGGGA GAAGGGCAGGGG', 'GCCCACYGGGGA GAAGGGCAGGG', 'GGCCCACYGGGG AGAAGGGCAGG'] | ['Hereditary cancer-predisposing syndrome', 'not provided'] |
| NM_144997.5 (FLCN):c.250-2A>G | 398124533 | FLCN | [ ] | [ ] | ['not provided'] |
| NM_000146.3 (FTL):c.-160A>G | 398124633 | FTL | [ ] | [ ] | [Hyperferritinemia cataract syndrome'] |
| NM_003184.3 (TAF2):c.1945T>C (p.Trp649Arg) | 398124645 | TAF2 | [ ] | [ ] | ['Mental retardation, autosomal recessive 40'] |
| NM_013281.3 (FLRT3):c.1016A>G (p.Lys339Arg) | 398124654 | — | [ ] | [ ] | ['Hypogonadotropic hypogonadism 21 with or without anosmia'] |
| NM_002834.3 (PTPN11):c.767A>G (p.Gln256Arg) | 397507523 | PTPN11 | [ ] | [ ] | ['Noonan syndrome 1', 'Rasopathy', 'not provided'] |
| NM_000054.4 (AVPR2):c.614A>G (p.Tyr205Cys) | 104894749 | AVPR2 | ['ACAYAGG TGCGACGG CCCCAGGG, 'GACAYAG GTGCGACG GCCCCAGG'] | ['ACAYAGGTGCG ACGGCCCCAGGG', 'GACAYAGGTGCG ACGGCCCCAGG'] | ['Nephrogenic diabetes insipidus', 'Nephrogenic diabetes insipidus, X-linked'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_031157.2 (HNRNPA1):c.956A>G (p.Asn319Ser) | 397518454 | HNRNPA1 | [ ] | [ ] | ['Amyotrophic lateral sclerosis 20'] |
| NM_000277.1 (PAH):c.662A>G (p.Glu221Gly) | 62514934 | PAH | [ ] | [ ] | ['Phenylketonuria', 'not provided'] |
| NM_000219.5 (KCNE1):c.176T>C (p.Leu59Pro) | 141813529 | KCNE1 | [ ] | [ ] | ['Congenital long QT syndrome'] |
| NM_001165963.1 (SCN1A):c.1076A>G (p.Asn359Ser) | 794726713 | SCN1A | [ ] | [ ] | ['Severe myoclonic epilepsy in infancy'] |
| NM_013339.3 (ALG6):c.391T>C (p.Tyr131His) | 35383149 | ALG6 | [ ] | [ ] | ['Congenital disorder of glycosylation type 1C', 'not specified'] |
| NM_153767.3 (KCNJ1):c.1013T>C (p.Met338Thr) | 59172778 | KCNJ1 | [ ] | [ ] | ['Bartter syndrome antenatal type 2'] |
| NM_176824.2 (BBS7):c.968A>G (p.His323Arg) | 119466001 | BBS7 | [ ] | [ ] | ['Bardet-Biedl syndrome 7'] |
| NM_000199.3 (SGSH):c.892T>C (p.Ser298Pro) | 138504221 | SGSH | [ ] | [ ] | ['Mucopolysaccharidosis, MPS-III-A', 'not provided'] |
| NM_000891.2 (KCNJ2):c.220A>G (p.Thr74Ala) | 199473652 | KCNJ2 | [ ] | [ ] | ['Congenital long QT syndrome'] |
| NM_001165963.1 (SCN1A):c.1048A>G (p.Met350Val) | 794726768 | SCN1A | ['ACAYATA TCCCTCTG GACATTGG'] | ['ACAYATATCCCT CTGGACATTGG'] | ['Severe myoclonic epilepsy in infancy'] |
| NM_002863.4 (PYGL):c.1016A>G (p.Asn339Ser) | 113993976 | PYGL | [ ] | [ ] | ['Glycogen storage disease, type VI'] |
| NM_001165963.1 (SCN1A):c.2537A>G (p.Glu846Gly) | 794726794 | SCN1A | [ ] | [ ] | ['Severe myoclonic epilepsy in infancy'] |
| NM_002693.2 (POLG):c.2864A>G (p.Tyr955Cys) | 113994099 | POLG | [ ] | [ ] | ['Autosomal dominant progressive external ophthalmoplegia with mitochondrial DNA deletions 1'] |
| NM_000920.3 (PC):c.1705A>G (p.Thr569Ala) | 113994144 | PC | [ ] | [ ] | ['Pyruvate carboxylase deficiency'] |
| NM_025265.3 (TSEN2):c.926A>G (p.Tyr309Cys) | 113994149 | TSEN2 | [ ] | ['CAGAGCAYAGA CCAAGAAAAAGG'] | ['Pontocerebellar hypoplasia type 2B'] |
| NM_001039958.1 (MESP2):c.271A>G (p.Lys91Glu) | 113994156 | MESP2 | [ ] | [ ] | ['Spondylocostal dysostosis 2'] |
| NM_024649.4 (BBS1):c.1340-2A>G | 113994180 | — | [ ] | [ ] | ['Bardet-Biedl syndrome'] |
| NM_033028.4 (BBS4):c.157-2A>G | 113994192 | BBS4 | [ ] | [ ] | ['Bardet-Biedl syndrome', 'Bardet-Biedl syndrome 4'] |
| NM_212472.2 (PRKAR1A):c.1A>G (p.Met1Val) | 281864779 | PRKAR1A | [ ] | [ ] | ['Carney complex, type 1'] |
| NM_212472.2 (PRKAR1A):c.178-2A>G | 281864796 | PRKAR1A | [ ] | [ ] | ['Carney complex, type 1'] |
| NM_212472.2 (PRKAR1A):c.891+3A>G | 281864799 | PRKAR1A | [ ] | [ ] | ['Carney complex, type 1'] |
| NM_001165963.1 (SCN1A):c.433A>G (p.Met145Val) | 794726849 | SCN1A | [ ] | [ ] | ['Severe myoclonic epilepsy in infancy'] |
| NM_005710.2 (PQBP1):c.194A>G (p.Tyr65Cys) | 121917899 | PQBP1 | [ ] | [ ] | ['Renpenning syndrome 1'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000921.4 (PDE3A):c.1333A>G (p.Thr445Ala) | 794726865 | PDE3A | ['CGAGGYG GTGGTGGT CCAAGTGG'] | ['CGAGGYGGTGG TGGTCCAAGTGG'] | ['Brachydactyly with hypertension'] |
| NM_024312.4 (GNPTAB):c.1285-2A>G | 281864974 | GNPTAB | [ ] | [ ] | ['Pseudo-Hurler polydystrophy'] |
| NM_024312.4 (GNPTAB):c.2783A>G (p.Lys928Arg) | 281865003 | GNPTAB | [ ] | [ ] | ['I cell disease'] |
| NM_024312.4 (GNPTAB):c.2867A>G (p.His956Arg) | 281865005 | GNPTAB | [ ] | [ ] | ['Pseudo-Hurler polydystrophy'] |
| NM_024312.4 (GNPTAB):c.3053A>G (p.Asp1018Gly) | 281865007 | GNPTAB | [ ] | [ ] | ['I cell disease'] |
| NM_024312.4 (GNPTAB):c.3458A>G (p.Asn1153Ser) | 281865019 | GNPTAB | [ ] | [ ] | ['Pseudo-Hurler polydystrophy'] |
| NM_024312.4 (GNPTAB):c.118-2A>G | 281865023 | GNPTAB | [ ] | [ ] | ['I cell disease'] |
| NM_198578.3 (LRRK2):c.5605A>G (p.Met1869Val) | 281865052 | LRRK2 | [ ] | ['TCAACAYAATAT TTCTAGGCAGG'] | ['Parkinson disease 8, autosomal dominant'] |
| NM_139241.3 (FGD4):c.1762-2A>G | 281865065 | FGD4 | [ ] | [ ] | ['Charcot-Marie-Tooth disease, type 4H'] |
| NM_006121.3 (KRT1):c.1445A>G (p.Tyr482Cys) | 58420087 | KRT1 | [ ] | [ ] | ['Bullous ichthyosiform erythroderma', 'not provided'] |
| NM_000195.4 (HPS1):c.716T>C (p.Leu239Pro) | 281865080 | HPS1 | [ ] | [ ] | ['Hermansky-Pudlak syndrome 1'] |
| NM_000195.4 (HPS1):c.2003T>C (p.Leu668Pro) | 281865090 | HPS1 | [ ] | [ ] | ['Hermansky-Pudlak syndrome 1'] |
| NM_022081.5(HPS4): c.461A>G (p.His154Arg) | 281865098 | HPS4 | [ ] | [ ] | ['Hermansky-Pudlak syndrome 4'] |
| NM_000277.1 (PAH):c.1157A>G (p.Tyr386Cys) | 62516141 | PAH | [ ] | [ ] | ['Phenylketonuria', 'not provided'] |
| NM_025114.3 (CEP290):c.2991+1655A>G | 281865192 | CEP290 | ['GAGATAY TCACAATT ACAACTGG'] | ['GATAYTCACAAT TACAACTGGGG', 'AGATAYTCACAA TTACAACTGGG', 'GAGATAYTCACA ATTACAACTGG'] | ['Leber congenital amaurosis 10', 'not provided'] |
| NM_018319.3 (TDP1):c.1478A>G (p.His493Arg) | 119467003 | TDP1 | [ ] | [ ] | ['Spinocerebellar ataxia autosomal recessive with axonal neuropathy'] |
| NM_000051.3 (ATM): c.5762_5763insNG_009830.1: g.91138_91274 | 774925473 | ATM | [ ] | [ ] | ['Ataxia-telangiectasia variant'] |
| NM_004614.4 (TK2):c.562A>G (p.Thr188Ala) | 281865495 | TK2 | [ ] | ['AAGYCTCAGGA TTGGTCCGAAGG'] | ['Mitochondrial DNA depletion syndrome 2'] |
| NM_003494.3 (DYSF):c.3041A>G (p.Tyr1014Cys) | 756328339 | DYSF | [ ] | ['CTAYACTCCCAG CCTGGGGGAGG', 'ATGCTAYACTCC CAGCCTGGGGG', 'GATGCTAYACTC CCAGCCTGGGG'] | ['Limb-girdle muscular dystrophy, type 2B'] |
| NM_000531.5 (OTC):c.1034A>G (p.Tyr345Cys) | 72558492 | OTC | ['AGGTGAG YAATCTGT CAGCAGGG'] | ['AGGTGAGYAAT CTGTCAGCAGGG'] | ['not provided'] |
| NM_000518.4 (HBB):c.199A>G (p.Lys67Glu) | 34165323 | HBB | [ ] | [ ] | ['Hemoglobinopathy'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_153427.2 (PITX2):c.262A>G (p.Lys88Glu) | 387906810 | PITX2 | [ ] | ['TCTYGAACCAAA CCTGGGGGCGG', 'GATTCTYGAACC AAACCTGGGGG', 'CGATTCTYGAAC CAAACCTGGGG'] | ['Axenfeld-Rieger syndrome type 1'] |
| NM_030964.3 (SPRY4):c.530A>G (p.Lys177Arg) | 78310959 | SPRY4 | [ ] | ['AGTGCYTGTCCA GCTCGGGTGGG', 'AAGTGCYTGTCC AGCTCGGGTGG'] | ['Hypogonadotropic hypogonadism 17 with or without anosmia'] |
| NM_002834.3 (PTPN11):c.922A>G (p.Asn308Asp) | 28933386 | PTPN11 | [ ] | [ ] | ['Noonan syndrome', 'Noonan syndrome 1', 'Rasopathy', 'not provided'] |
| NM_000518.4 (HBB):c.-50-29A>G | 34598529 | HBB | [ ] | [ ] | ['alpha Thalassemia', 'Beta thalassemia intermedia'] |
| NM_207352.3 (CYP4V2):c.1393A>G (p.Arg465Gly) | 144109267 | CYP4V2 | [ ] | ['TTCCYGGGGCCA GCAGAGAAGGG', 'GTTCCYGGGGCC AGCAGAGAAGG'] | ['Bietti crystalline corneoretinal dystrophy'] |
| NM_001360.2 (DHCR7):c.1A>G (p.Met1Val) | 104886033 | DHCR7 | [ ] | [ ] | ['Smith-Lemli-Opitz syndrome'] |
| NM_000495.4 (COL4A5):c.1A>G (p.Met1Val) | 104886050 | COL4A5 | [ ] | [ ] | ['Alport syndrome, X-linked recessive'] |
| NM_000495.4 (COL4A5):c.2692A>G (p.Met898Val) | 104886192 | COL4A5 | [ ] | [ ] | ['Alport syndrome, X-linked recessive'] |
| NM_000495.4 (COL4A5):c.2746A>G (p.Ser916Gly) | 104886193 | COL4A5 | [ ] | [ ] | ['Alport syndrome, X-linked recessive'] |
| NM_004572.3 (PKP2):c.2062T>C (p.Ser688Pro) | 144601090 | PKP2 | [ ] | [ ] | ['Arrhythmogenic right ventricular cardiomyopathy', 'not specified', 'not provided'] |
| NM_000495.4 (COL4A5):c.4790A>G (p.Tyr1597Cys) | 104886298 | COL4A5 | [ ] | [ ] | ['Alport syndrome, X-linked recessive'] |
| NM_000495.4 (COL4A5):c.1340-2A>G | 104886319 | COL4A5 | [ ] | ['CACCYGAGTAA GATAAAGAAAGG'] | ['Alport syndrome, X-linked recessive'] |
| NM_000495.4 (COL4A5):c.2042-18A>G | 104886341 | COL4A5 | [ ] | [ ] | ['Alport syndrome, X-linked recessive'] |
| NM_000495.4 (COL4A5):c.2147-2A>G | 104886344 | COL4A5 | [ ] | [ ] | ['Alport syndrome, X-linked recessive'] |
| NM_000495.4 (COL4A5):c.2510-33A>G | 104886358 | COL4A5 | [ ] | [ ] | ['Alport syndrome, X-linked recessive'] |
| NM_000495.4 (COL4A5):c.3107-2A>G | 104886379 | COL4A5 | [ ] | [ ] | ['Alport syndrome, X-linked recessive'] |
| NM_000051.3 (ATM):c.7268A>G (p.Glu2423Gly) | 121434221 | ATM | [ ] | [ ] | ['Mantle cell lymphoma'] |
| NM_000495.4 (COL4A5):c.3605-2A>G | 104886385 | COL4A5 | [ ] | [ ] | ['Alport syndrome, X-linked recessive'] |
| NM_000096.3 (CP):c.1209-2A>G | 386134137 | CP | [ ] | [ ] | ['Deficiency of ferroxidase'] |
| NM_000348.3 (SRD5A2):c.692A>G (p.His231Arg) | 121434251 | SRD5A2 | [ ] | [ ] | ['3-Oxo-5 alpha-steroid delta 4-dehydrogenase deficiency'] |
| NM_002739.3 (PRKCG):c.76A>G (p.Arg26Gly) | 386134157 | PRKCG | [ ] | [ ] | ['Spinocerebellar ataxia 14'] |
| NM_000383.3 (AIRE):c.247A>G (p.Lys83Glu) | 121434255 | AIRE | [ ] | [ ] | ['AUTOIMMUNE POLYENDOCRIN-OPATHY SYNDROME, TYPE I'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
| --- | --- | --- | --- | --- | --- |
| NM_000495.4 (COL4A5):c.466-2A>G | 104886416 | COL4A5 | [ ] | ['ACCCYAAAAGA AGCCATCAATGG'] | ['Alport syndrome, X-linked recessive'] |
| NM_001127328.2 (ACADM):c.589A>G (p.Thr197Ala) | 121434279 | ACADM | [ ] | [ ] | ['Medium-chain acyl-coenzyme A dehydrogenase deficiency'] |
| NM_000495.4 (COL4A5):c.892-2A>G | 104886453 | COL4A5 | [ ] | [ ] | ['Alport syndrome, X-linked recessive'] |
| NM_020533.2 (MCOLN1):c.406-2A>G | 104886461 | MCOLN1 | ['TACYGTG GGCAGAG AAGGGGA GG'] | ['TACYGTGGGCA GAGAAGGGGAGG', 'AGGTACYGTGGG CAGAGAAGGGG', 'CAGGTACYGTGG GCAGAGAAGGG'] | ['Ganglioside sialidase deficiency', 'not provided'] |
| NM_018136.4 (ASPM):c.2761-25A>G | 199422149 | ASPM | [ ] | [ ] | ['Primary autosomal recessive microcephaly 5'] |
| NM_017780.3 (CHD7):c.3082A>G (p.Ile1028Val) | 121434338 | CHD7 | [ ] | [ ] | ['CHARGE association', 'not provided'] |
| NM_017780.3 (CHD7):c.164A>G (p.His55Arg) | 121434345 | CHD7 | [ ] | [ ] | ['Kallmann syndrome 5'] |
| NM_152783.4 (D2HGDH):c.1315A>G (p.Asn439Asp) | 121434362 | D2HGDH | ['GCAGGTY ACCATCTC CTGGAGGG', 'TGCAGGT YACCATCT CCTGGAGG'] | ['GCAGGTYACCAT CTCCTGGAGGG', 'TGCAGGTYACCA TCTCCTGGAGG'] | [D-2-hydroxyglutaric aciduria 1'] |
| NM_005006.6 (NDUFS1):c.755A>G (p.Asp252Gly) | 199422224 | NDUFS1 | [ ] | [ ] | ['Mitochondrial complex I deficiency', 'not provided'] |
| NM_002894.2 (RBBP8):c.1009A>G (p.Lys337Glu) | 121434388 | RBBP8 | [ ] | [ ] | ['Carcinoma of pancreas'] |
| NM_004621.5 (TRPC6):c.428A>G (p.Asn143Ser) | 121434391 | TRPC6 | [ ] | [ ] | ['Focal segmental glomerulosclerosis 2'] |
| NM_003705.4 (SLC25A12):c.1769A>G (p.Gln590Arg) | 121434396 | SLC25A12 | [ ] | [ ] | ['Hypomyelination, global cerebral'] |
| NM_001363.4 (DKC1):c.127A>G (p.Lys43Glu) | 199422243 | DKC1 | [ ] | [ ] | ['Dyskeratosis congenita X-linked'] |
| NM_001084.4 (PLOD3):c.668A>G (p.Asn223Ser) | 121434414 | PLOD3 | [ ] | [ ] | ['Bone fragility with contractures, arterial rupture, and deafness'] |
| NM_006702.4 (PNPLA6):c.3034A>G (p.Met1012Val) | 121434415 | PNPLA6 | [ ] | [ ] | ['Spastic paraplegia 39'] |
| NR_001566.1 (TERC):n.48A>G | 199422262 | TERC | [ ] | [ ] | ['Dyskeratosis congenita autosomal dominant'] |
| NM_004984.2 (KIF5A):c.767A>G (p.Asn256Ser) | 121434441 | KIF5A | [ ] | [ ] | ['Spastic paraplegia 10'] |
| NM_004984.2 (KIF5A):c.827A>G (p.Tyr276Cys) | 121434443 | KIF5A | [ ] | ['GAACAYAGCTTT TCTGGGGGAGG'] | ['Spastic paraplegia 10'] |
| m.10438A>G | 121434456 | MT-TR | [ ] | [ ] | ['Mitochondrial encephalomyopathy'] |
| NM_198253.2 (TERT):c.2537A>G (p.Tyr846Cys) | 199422302 | TERT | [ ] | [ ] | ['Aplastic anemia'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| m.12320A>G | 121434463 | MT-TL2 | ['TGGAGTY GCACCAAA ATTTTTGG'] | ['GAGTYGCACCA AAATTTTTGGGG', 'GGAGTYGCACCA AAATTTTTGGG', 'TGGAGTYGCACC AAAATTTTTGG'] | ['Mitochondrial myopathy'] |
| m.4317A>G | 121434465 | MT-TI | [ ] | [ ] | [ ] |
| m.4269A>G | 121434466 | MT-TI | ['ACAYATT TCTTAGGT TTGAGGGG', 'GACAYAT TTCTTAGG TTTGAGGG'] | ['ACAYATTTCTTA GGTTTGAGGGG', 'GACAYATTTCTT AGGTTTGAGGG', 'AGACAYATTTCT TAGGTTTGAGG'] | [ ] |
| m.4295A>G | 121434467 | MT-TI | [ ] | [ ] | ['Primary familial hypertrophic cardiomyopathy', 'Deafness, nonsyndromic sensorineural, mitochondrial'] |
| m.4300A>G | 121434470 | MT-TI | [ ] | [ ] | ['Primary familial hypertrophic cardiomyopathy'] |
| NM_001099274.1 (TINF2):c.850A>G (p.Thr284Ala) | 199422314 | TINF2 | [ ] | ['TGACTGYGGGG CGCTCCTTATGG'] | ['Dyskeratosis congenita autosomal dominant'] |
| NM_004044.6 (ATIC):c.1277A>G (p.Lys426Arg) | 121434478 | ATIC | [ ] | ['AGTGTACYTGAC AGCAATGGTGG'] | ['AICAR transformylase/IMP cyclohydrolase deficiency'] |
| NM_001099274.1 (TINF2):c.871A>G (p.Arg291Gly) | 199422319 | TINF2 | [ ] | [ ] | ['Dyskeratosis congenita autosomal dominant'] |
| NM_015474.3 (SAMHD1):c.760A>G (p.Met254Val) | 121434521 | SAMHD1 | [ ] | [ ] | ['Aicardi Goutieres syndrome 5'] |
| NM_001103.3 (ACTN2):c.26A>G (p.Gln9Arg) | 121434525 | ACTN2 | [ ] | [ ] | ['Dilated cardiomyopathy 1AA', 'Cardiomyopathy', 'Dilated cardiomyopathy', 'not specified'] |
| NM_000155.3 (GALT):c.812A>G (p.Glu271Gly) | 111033765 | GALT | [ ] | ['CGCYCAGCAGG GGTCAGCTCAGG'] | ['Deficiency of UDPglucose-hexose-1-phosphate uridylyltransferase', 'not provided'] |
| NM_000316.2 (PTH1R):c.668A>G (p.His223Arg) | 121434597 | PTH1R | [ ] | [ ] | ['Metaphyseal chondrodysplasia, Jansen type'] |
| NM_006006.4 (ZBTB16):c.1849A>G (p.Met617Val) | 121434606 | ZBTB16 | [ ] | ['GATCAYGGCCG AGTAGTCCCGGG', 'TGATCAYGGCCG AGTAGTCCCGG'] | ['Skeletal defects, genital hypoplasia, and mental retardation'] |
| NM_014305.3 (TGDS):c.700T>C (p.Tyr234His) | 544436734 | TGDS | [ ] | [ ] | ['Catel Manzke syndrome'] |
| NM_002835.3 (PTPN12):c.182A>G (p.Lys61Arg) | 121434623 | PTPN12 | [ ] | [ ] | ['Carcinoma of colon'] |
| NM_000035.3 (ALDOB):c.1027T>C (p.Tyr343His) | 369586696 | ALDOB | [ ] | [ ] | ['Hereditary fructosuria'] |
| NM_006180.4 (NTRK2):c.2165A>G (p.Tyr722Cys) | 121434633 | NTRK2 | [ ] | [ ] | ['Obesity, hyperphagia, and developmental delay'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000107.2 (DDB2):c.730A>G (p.Lys244Glu) | 121434639 | DDB2 | [ ] | [ ] | ['Xeroderma pigmentosum, group E'] |
| NM_000017.3 (ACADS):c.1108A>G (p.Met370Val) | 566325901 | ACADS | [ ] | ['AGCCCAYGCCG CCCAGGATCTGG'] | ['not provided'] |
| NM_001151.3 (SLC25A4):c.311A>G (p.Asp104Gly) | 28999114 | SLC25A4 | [ ] | [ ] | ['Autosomal dominant progressive external ophthalmoplegia with mitochondrial DNA deletions 2'] |
| NM_012079.5 (DGAT1):c.751+2T>C | 148665132 | DGAT1 | [ ] | ['ACCGCGGYGAG GACCTCTGTGGG'] | ['Diarrhea 7'] |
| NM_002036.3 (ACKR1):c.-67T>C | 2814778 | ACKR1 | [ ] | [ ] | ['White blood cell count quantitative trait locus 1'] |
| NM_000492.3 (CFTR):c.1666A>G (p.Ile556Val) | 75789129 | CFTR | [ ] | [ ] | ['Cystic fibrosis', 'not specified'] |
| NM_000155.3 (GALT):c.574A>G (p.Ser192Gly) | 111033830 | GALT | [ ] | ['TGCYGGCCCATA CCTGTCAAGGG', 'CTGCYGGCCCAT ACCTGTCAAGG'] | ['Deficiency of UDPglucose-hexose-1-phosphate uridylyltransferase'] |
| NM_174916.2 (UBR1):c.407A>G (p.His136Arg) | 119477054 | UBR1 | [ ] | [ ] | ['Johanson-Blizzard syndrome'] |
| m.3274A>G | 199474666 | MT-TL1 | [ ] | [ ] | [ ] |
| NM_000060.3 (BTD):c.128A>G (p.His43Arg) | 146011150 | BTD | [ ] | [ ] | ['Biotinidase deficiency'] |
| NM_172107.2 (KCNQ2):c.635A>G (p.Asp212Gly) | 118192202 | KCNQ2 | [ ] | [ ] | ['Benign familial neonatal seizures 1'] |
| NM_006493.2 (CLN5):c.1121A>G (p.Tyr374Cys) | 148862100 | CLN5 | [ ] | [ ] | ['Ceroid lipofuscinosis neuronal 5'] |
| NM_000060.3 (BTD):c.880A>G (p.Ile294Val) | 35976361 | BTD | [ ] | [ ] | ['Biotinidase deficiency'] |
| NM_000132.3 (F8):c.1226A>G (p.Glu409Gly) | 28933671 | F8 | [ ] | [ ] | ['Hereditary factor VIII deficiency disease'] |
| NM_000132.3 (F8):c.5600A>G (p.His1867Arg) | 28933679 | F8 | [ ] | ['GAGYGCACATCT TTTTCCTAGGG', 'TGAGYGCACATC TTTTTCCTAGG'] | ['Hereditary factor VIII deficiency disease'] |
| NM_000266.3 (NDP):c.1A>G (p.Met1Val) | 28933685 | NDP | [ ] | [ ] | ['Atrophia bulborum hereditaria'] |
| NM_000133.3 (F9):c.278A>G (p.Asp93Gly) | 137852230 | F9 | [ ] | [ ] | ['Hereditary factor IX deficiency disease'] |
| NM_000133.3 (F9):c.329A>G (p.Asp110Gly) | 137852234 | F9 | [ ] | [ ] | ['Hereditary factor IX deficiency disease'] |
| NM_000133.3 (F9):c.917A>G (p.Asn306Ser) | 137852251 | F9 | [ ] | ['GCTGCAYTGTAG TTGTGGTGAGG'] | ['Hereditary factor IX deficiency disease'] |
| NM_000133.3 (F9):c.1180A>G (p.Met394Val) | 137852262 | F9 | [ ] | [ ] | ['Hereditary factor IX deficiency disease'] |
| NM_000133.3 (F9):c.1231A>G (p.Ser411Gly) | 137852277 | F9 | [ ] | [ ] | ['Hereditary factor IX deficiency disease'] |
| NM_000292.2 (PHKA2):c.896A>G (p.Asp299Gly) | 137852289 | PHKA2 | [ ] | [ ] | ['Glycogen storage disease type IXa1'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000292.2 (PHKA2):c.565A>G (p.Lys189Glu) | 137852295 | PHKA2 | [ ] | [ ] | ['Glycogen storage disease IXa2'] |
| NM_000032.4 (ALAS2):c.1702A>G (p.Ser568Gly) | 137852306 | ALAS2 | [ ] | [ ] | ['Hereditary sideroblastic anemia'] |
| NM_001287223.1 (SCN11A):c.3473T>C (p.Leu1158Pro) | 141686175 | SCN11A | [ ] | ['CGTGCGCYGTCC CAGTTTGAAGG'] | ['Episodic pain syndrome, familial, 3'] |
| NM_000402.4 (G6PD):c.583A>G (p.Asn195Asp) | 137852331 | G6PD | [ ] | ['ATGCGGTYCCAG CCTCTGCTGGG'] | ['Favism, susceptibility to', 'Anemia, nonspherocytic hemolytic, due to G6PD deficiency'] |
| NM_000132.3 (F8):c.872A>G (p.Glu291Gly) | 137852359 | F8 | [ ] | [ ] | ['Hereditary factor VIII deficiency disease'] |
| NM_018718.2 (CEP41):c.107T>C (p.Met36Thr) | 368178632 | CEP41 | [ ] | [ ] | ['Joubert syndrome 9/15, digenic'] |
| NM_000132.3 (F8):c.5183A>G (p.Tyr1728Cys) | 137852362 | F8 | [ ] | [ ] | ['Hereditary factor VIII deficiency disease'] |
| NM_000132.3 (F8):c.5821A>G (p.Asn1941Asp) | 137852369 | F8 | [ ] | ['TAGCCATYGATT GCTGGAGAAGG'] | ['Hereditary factor VIII deficiency disease'] |
| NM_000132.3 (F8):c.328A>G (p.Met110Val) | 137852385 | F8 | [ ] | [ ] | ['Hereditary factor VIII deficiency disease'] |
| NM_000132.3 (F8):c.398A>G (p.Tyr133Cys) | 137852389 | F8 | [ ] | ['TCAYATTCAGCT CCTATAGCAGG'] | ['Hereditary factor VIII deficiency disease'] |
| NM_000132.3 (F8):c.404A>G (p.Asp135Gly) | 137852390 | F8 | [ ] | [ ] | ['Hereditary factor VIII deficiency disease'] |
| NM_000132.3 (F8):c.940A>G (p.Thr314Ala) | 137852406 | F8 | [ ] | ['TGAGCAGYAAG GAAAGTTATTGG'] | ['Hereditary factor VIII deficiency disease'] |
| NM_000041.3 (APOE):c.178A>G (p.Thr60Ala) | 28931576 | APOE | [ ] | ['ACAGTGYCTGCA CCCAGCGCAGG'] | [ ] |
| NM_000132.3 (F8):c.1682A>G (p.Asp561Gly) | 137852420 | F8 | [ ] | [ ] | ['Hereditary factor VIII deficiency disease'] |
| NM_000132.3 (F8):c.1892A>G (p.Asn631Ser) | 137852429 | F8 | ['ATGYTGG AGGCTTGG AACTCTGG'] | ['ATGYTGGAGGCT TGGAACTCTGG'] | ['Hereditary factor VIII deficiency disease'] |
| NM_012082.3 (ZFPM2):c.1969A>G (p.Ser657Gly) | 28374544 | — | [ ] | [ ] | ['Tetralogy of Fallot'] |
| NM_000098.2 (CPT2):c.638A>G (p.Asp213Gly) | 74315300 | CPT2 | [ ] | [ ] | ['CARNITINE PALMITOYL-TRANSFERASE II DEFICIENCY, LATE-ONSET'] |
| NM_000396.3 (CTSK):c.990A>G (p.Ter330Trp) | 74315301 | CTSK | [ ] | ['GAGYCACATCTT GGGGAAGCTGG'] | ['Pyknodysostosis'] |
| NM_000132.3 (F8):c.6113A>G (p.Asn2038Ser) | 137852454 | F8 | [ ] | [ ] | ['Hereditary factor VIII deficiency disease'] |
| NM_000132.3 (F8):c.6278A>G (p.Asp2093Gly) | 137852457 | F8 | [ ] | [ ] | ['Hereditary factor VIII deficiency disease'] |
| NM_024009.2 (GJB3):c.421A>G (p.Ile141Val) | 74315320 | GJB3 | ['CAAYGAT GAGCTTGA AGATGAGG'] | ['CAAYGATGAGC TTGAAGATGAGG'] | ['Deafness, autosomal recessive'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000132.3 (F8):c.104A>G (p.Tyr35Cys) | 137852476 | F8 | [ ] | [ ] | ['Hereditary factor VIII deficiency disease'] |
| NM_000194.2 (HPRT1):c.602A>G (p.Asp201Gly) | 137852479 | HPRT1 | [ ] | [ ] | ['Partial hypoxanthine-guanine phosphoribosyl-transferase deficiency'] |
| NM_000261.1 (MYOC):c.1267A>G (p.Lys423Glu) | 74315336 | MYOC | [ ] | [ ] | ['Primary open angle glaucoma juvenile onset 1'] |
| NM_014625.3 (NPHS2):c.479A>G (p.Asp160Gly) | 74315346 | NPHS2 | [ ] | [ ] | ['Nephrotic syndrome, idiopathic, steroid-resistant'] |
| NM_000194.2 (HPRT1):c.155A>G (p.Asp52Gly) | 137852502 | HPRT1 | [ ] | [ ] | ['Partial hypoxanthine-guanine phosphoribosyl-transferase deficiency'] |
| NM_002764.3 (PRPS1):c.341A>G (p.Asn114Ser) | 137852540 | PRPS1 | [ ] | ['TAGCATAYTTGC AACAAGCTTGG'] | ['Phosphoribosyl-pyrophosphate synthetase superactivity'] |
| NM_000055.2 (BCHE):c.293A>G (p.Asp98Gly) | 1799807 | BCHE | [ ] | [ ] | ['Postanesthetic apnea'] |
| NM_170784.2 (MKKS):c.169A>G (p.Thr57Ala) | 74315399 | MKKS | [ ] | [ ] | ['Bardet-Biedl syndrome 6'] |
| NM_000311.3 (PRNP):c.650A>G (p.Gln217Arg) | 74315406 | PRNP | [ ] | [ ] | ['Gerstmann-Straussler-Scheinker syndrome', 'Genetic prion diseases'] |
| NM_000311.3 (PRNP):c.560A>G (p.His187Arg) | 74315413 | PRNP | [ ] | [ ] | ['Gerstmann-Straussler-Scheinker syndrome', 'Genetic prion diseases', 'Spongiform encephalopathy with neuropsychiatric features'] |
| NM_000044.3 (AR):c.2291A>G (p.Tyr764Cys) | 137852567 | AR | [ ] | [ ] | ['Reifenstein syndrome'] |
| NM_000044.3 (AR):c.2362A>G (p.Met788Val) | 137852570 | AR | [ ] | [ ] | [ ] |
| NM_000044.3 (AR):c.2632A>G (p.Thr878Ala) | 137852578 | AR | [ ] | [ ] | ['Malignant tumor of prostate'] |
| NM_020436.3 (SALL4):c.2663A>G (p.His888Arg) | 74315429 | SALL4 | [ ] | [ ] | ['Duane-radial ray syndrome'] |
| NM_000044.3 (AR):c.2708A>G (p.Gln903Arg) | 137852582 | AR | [ ] | [ ] | ['Malignant tumor of prostate'] |
| NM_000211.4 (ITGB2):c.1052A>G (p.Asn351Ser) | 137852613 | ITGB2 | [ ] | [ ] | ['Leukocyte adhesion deficiency'] |
| NM_000215.3 (JAK3):c.299A>G (p.Tyr100Cys) | 137852624 | JAK3 | [ ] | ['AATCCTGYACAG CAGGACTTGGG'] | ['Severe combined immunodeficiency, autosomal recessive, T cell-negative, B cell-positive, NK cell-negative'] |
| NM_001166107.1 (HMGCS2):c.500A>G (p.Tyr167Cys) | 137852640 | HMGCS2 | [ ] | ['ACCACCGYAGC AGGCATTGGTGG'] | ['mitochondrial 3-hydroxy-3-methylglutaryl-CoA synthase deficiency'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_002047.2 (GARS):c.374A>G (p.Glu125Gly) | 137852645 | GARS | [ ] | [ ] | ['Charcot-Marie-Tooth disease type 2D', 'Distal hereditary motor neuronopathy type 5'] |
| NM_033163.3 (FGF8):c.298A>G (p.Lys100Glu) | 137852662 | FGF8 | [ ] | [ ] | ['Kallmann syndrome 6'] |
| NM_002180.2 (IGHMBP2):c.638A>G (p.His213Arg) | 137852666 | IGHMBP2 | [ ] | [ ] | ['Werdnig-Hoffmann disease'] |
| NM_004387.3 (NKX2-5):c.896A>G (p.Asp299Gly) | 137852683 | NKX2-5 | [ ] | [ ] | ['Atrial septal defect 7 with or without atrioventricular conduction defects'] |
| NM_004387.3 (NKX2-5):c.547A>G (p.Lys183Glu) | 137852686 | NKX2-5 | [ ] | [ ] | [ ] |
| NM_000310.3 (PPT1):c.236A>G (p.Asp79Gly) | 137852697 | PPT1 | [ ] | [ ] | ['Ceroid lipofuscinosis neuronal 1'] |
| NM_000336.2 (SCNN1B):c.863A>G (p.Asn288Ser) | 137852712 | SCNN1B | [ ] | [ ] | ['Bronchiectasis'] |
| NM_000579.3 (CCR5):c.-301+246A>G | 1799987 | — | [ ] | [ ] | ['Human immunodeficiency virus type 1, susceptibility to'] |
| NM_001204.6 (BMPR2):c.1454A>G (p.Asp485Gly) | 137852745 | BMPR2 | [ ] | [ ] | ['Primary pulmonary hypertension'] |
| NM_005591.3 (MRE11A):c.350A>G (p.Asn117Ser) | 137852760 | MRE11A | [ ] | [ ] | ['Hereditary cancer-predisposing syndrome', 'Ataxia-telangiectasia-like disorder'] |
| NM_003476.4 (CSRP3):c.206A>G (p.Lys69Arg) | 137852764 | CSRP3 | [ ] | [ ] | ['Dilated cardiomyopathy 1M', 'Cardiomyopathy', 'Familial hypertrophic cardiomyopathy 12'] |
| NM_000519.3 (HBD):c.-81A>G | 35518301 | HBD | [ ] | [ ] | [ ] |
| NM_005633.3 (SOS1):c.1654A>G (p.Arg552Gly) | 137852814 | SOS1 | [ ] | ['GCATCCYTTCCAGTGTACTCCGG'] | ['Noonan syndrome', 'Noonan syndrome 4', 'Rasopathy', 'not provided'] |
| NM_003688.3 (CASK):c.2129A>G (p.Asp710Gly) | 137852818 | CASK | [ ] | [ ] | ['FG syndrome 4'] |
| NM_031443.3 (CCM2):c.1A>G (p.Met1Val) | 137852842 | CCM2 | [ ] | [ ] | ['Cerebral cavernous malformations 2'] |
| NM_182760.3 (SUMF1):c.1A>G (p.Met1Val) | 137852855 | SUMF1 | [ ] | [ ] | ['Multiple sulfatase deficiency'] |
| NM_001171993.1 (HPD):c.362A>G (p.Tyr121Cys) | 137852865 | HPD | [ ] | ['CCTCAYATCCAGGCAAGAATTGG'] | [4-Hydroxyphenyl-pyruvate dioxygenase deficiency'] |
| NM_024996.5 (GFM1):c.521A>G (p.Asn174Ser) | 119470018 | GFM1 | ['TTGYTAATAAAAGTTAGAAACGG'] | ['TTGYTAATAAAAGTTAGAAACGG'] | ['Combined oxidative phosphorylation deficiency 1'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000158.3 (GBE1):c.1634A>G (p.His545Arg) | 137852889 | GBE1 | [ ] | [ ] | ['Glycogen storage disease, type IV', 'GLYCOGEN STORAGE DISEASE IV, FATAL PERINATAL NEUROMUSCULAR'] |
| NM_000158.3 (GBE1):c.1883A>G (p.His628Arg) | 137852891 | GBE1 | [ ] | [ ] | ['Glycogen storage disease, type IV', 'GLYCOGEN STORAGE DISEASE IV, CHILDHOOD NEUROMUSCULAR] |
| m.8344A>G | 118192098 | MT-TK | [ ] | [ ] | ['Parkinson disease, mitochondrial', 'Leigh disease', 'Myoclonus with epilepsy with ragged red fibers'] |
| NM_000540.2 (RYR1):c.10100A>G (p.Lys3367Arg) | 118192126 | RYR1 | [ ] | [ ] | ['Central core disease', 'not provided'] |
| NM_000540.2 (RYR1):c.14572A>G (p.Asn4858Asp) | 118192144 | RYR1 | [ ] | [ ] | ['Central core disease', 'not provided'] |
| NM_012464.4 (TLL1):c.1885A>G (p.Ile629Val) | 137852953 | TLL1 | ['GGTTAYG GTGCCGTT AAGTTTGG'] | ['GGTTAYGGTGCC GTTAAGTTTGG'] | ['Atrial septal defect 6'] |
| NM_025243.3 (SLC19A3):c.130A>G (p.Lys44Glu) | 137852957 | SLC19A3 | [ ] | [ ] | ['Basal ganglia disease, biotin-responsive'] |
| NM_138691.2 (TMC1):c.1763+3A>G | 370898981 | TMC1 | [ ] | ['TGGCCYACCAG ATCATGCCTTGG'] | ['Deafness, autosomal recessive 7'] |
| NM_000540.2 (RYR1):c.13909A>G (p.Thr4637Ala) | 118192166 | RYR1 | [ ] | [ ] | ['Central core disease', 'not provided'] |
| NM_000540.2 (RYR1):c.14387A>G (p.Tyr4796Cys) | 118192167 | RYR1 | [ ] | ['CCATAYACCAGC CCAGGTACAGG'] | ['Malignant hyperthermia susceptibility type 1', 'Central core disease', 'not provided'] |
| NM_032667.6 (BSCL2):c.263A>G (p.Asn88Ser) | 137852972 | — | [ ] | ['CGAGACAYTGG CAACAGGGAAGG'] | ['Distal hereditary motor neuronopathy type 5', 'Silver spastic paraplegia syndrome', 'Charcot-Marie-Tooth disease, type 2'] |
| NM_014795.3 (ZEB2):c.3356A>G (p.Gln1119Arg) | 137852983 | ZEB2 | [ ] | [ ] | ['Mowat-Wilson syndrome'] |
| NM_000540.2 (RYR1):c.14740A>G (p.Arg4914Gly) | 118192184 | RYR1 | [ ] | [ ] | ['Central core disease', 'not provided'] |
| NM_172107.2 (KCNQ2):c.356A>G (p.Glu119Gly) | 118192193 | KCNQ2 | [ ] | ['CTTCYCATACTC CTTGATGGTGG', 'GCTCTTCYCATA CTCCTTGATGG'] | ['Benign familial neonatal seizures 1'] |
| NM_172107.2 (KCNQ2):c.622A>G (p.Met208Val) | 118192201 | KCNQ2 | [ ] | ['GGATCAYCCGC AGAATCTGCAGG'] | ['Benign familial neonatal seizures 1'] |
| NM_172107.2 (KCNQ2):c.773A>G (p.Asn258Ser) | 118192207 | KCNQ2 | [ ] | [ ] | ['Benign familial neonatal seizures 1'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_004006.2 (DMD):c.8734A>G (p.Asn2912Asp) | 1800278 | DMD | [ ] | [ ] | ['Duchenne muscular dystrophy', 'not specified'] |
| NM_004006.2 (DMD):c.8762A>G (p.His2921Arg) | 1800279 | DMD | [ ] | [ ] | ['Becker muscular dystrophy', 'not specified'] |
| NM_001080463.1 (DYNC2H1):c.11284A>G (p.Met3762Val) | 137853026 | DYNC2H1 | [ ] | [ ] | ['Short-rib thoracic dysplasia 3 with or without polydactyly'] |
| NM_001080463.1 (DYNC2H1):c.9044A>G (p.Asp3015Gly) | 137853027 | DYNC2H1 | [ ] | ['ATAYCTCTAATT ACATCAGGTGG', 'AGAATAYCTCTA ATTACATCAGG'] | ['Short-rib thoracic dysplasia 3 with or without polydactyly'] |
| NM_001080463.1 (DYNC2H1):c.4610A>G (p.Gln1537Arg) | 137853033 | DYNC2H1 | ['ACCYGTG AAGGGAA CAGAGATG G'] | ['ACCYGTGAAGG GAACAGAGATGG'] | ['Short-rib thoracic dysplasia 3 with or without polydactyly'] |
| NM_001080463.1 (DYNC2H1):c.5959A>G (p.Thr1987Ala) | 137853035 | DYNC2H1 | [ ] | [ ] | ['Short-rib thoracic dysplasia 3 with or without polydactyly'] |
| NM_001430.4 (EPAS1):c.1603A>G (p.Met535Val) | 137853037 | EPAS1 | [ ] | [ ] | ['Erythrocytosis, familial, 4'] |
| NM_172107.2 (KCNQ2):c.1764-2A>G | 118192238 | KCNQ2 | [ ] | [ ] | ['Benign familial neonatal seizures 1'] |
| NM_004519.3 (KCNQ3):c.914A>G (p.Asp305Gly) | 118192248 | KCNQ3 | [ ] | [ ] | ['Benign familial neonatal seizures 2'] |
| NM_004519.3 (KCNQ3):c.1403A>G (p.Asn468Ser) | 118192252 | KCNQ3 | ['TCTTTAY TGTTTAAG CCAACAGG'] | ['TCTTTAYTGTTT AAGCCAACAGG'] | ['Benign familial neonatal seizures 2', 'not specified', 'not provided'] |
| NM_004519.3 (KCNQ3):c.2462A>G (p.Asn821Ser) | 118192254 | KCNQ3 | [ ] | [ ] | ['Benign familial neonatal seizures 2', 'not specified', 'not provided'] |
| NM_138701.3 (MPLKIP):c.430A>G (p.Met144Val) | 137853117 | MPLKIP | [ ] | [ ] | ['Trichothiodystrophy, nonphotosensitive 1'] |
| NM_005094.3 (SLC27A4):c.899A>G (p.Gln300Arg) | 137853134 | SLC27A4 | [ ] | [ ] | ['Ichthyosis prematurity syndrome'] |
| NM_194456.1 (KRIT1):c.410A>G (p.Asp137Gly) | 137853139 | KRIT1 | [ ] | [ ] | ['Cerebral cavernous malformations 1'] |
| NM_000351.4 (STS):c.1331A>G (p.His444Arg) | 137853169 | STS | [ ] | [ ] | ['X-linked ichthyosis with steryl-sulfatase deficiency'] |
| NM_152416.3 (NDUFAF6):c.296A>G (p.Gln99Arg) | 137853184 | NDUFAF6 | [ ] | [ ] | ['Leigh syndrome due to mitochondrial complex I deficiency'] |
| NM_144573.3 (NEXN):c.1955A>G (p.Tyr652Cys) | 137853197 | NEXN | [ ] | ['ATAYACTCTCCT CCATCTTCTGG'] | ['Dilated cardiomyopathy 1CC', 'Cardiomyopathy', 'not specified'] |
| NM_000476.2 (AK1):c.491A>G (p.Tyr164Cys) | 137853203 | AK1 | [ ] | ['TTCTCAYAGAAG GCGATGACGGG', 'TTTCTCAYAGAA GGCGATGACGG'] | ['Adenylate kinase deficiency, hemolytic anemia due to'] |
| NM_013411.4 (AK2):c.1A>G (p.Met1Val) | 137853206 | AK2 | [ ] | [ ] | ['Reticular dysgenesis'] |
| NM_000308.2 (CTSA):c.746+3A>G | 786200859 | CTSA | [ ] | ['TCCCAYACCTGT TCCCCAGAAGG'] | ['Galactosialidosis, adult'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_002890.2 (RASA1):c.1198A>G (p.Lys400Glu) | 137853215 | RASA1 | [ ] | [ ] | [ ] |
| NM_002890.2 (RASA1):c.1201A>G (p.Ile401Val) | 137853216 | RASA1 | [ ] | [ ] | [ ] |
| NM_000515.4 (GH1):c.413A>G (p.Asp138Gly) | 137853221 | GH1 | [ ] | [ ] | ['Kowarski syndrome'] |
| NM_017636.3 (TRPM4):c.2741A>G (p.Lys914Arg) | 172151858 | TRPM4 | [ ] | [ ] | ['Progressive familial heart block type 1B'] |
| NM_000545.6 (HNF1A):c.365A>G (p.Tyr122Cys) | 137853237 | HNF1A | [ ] | [ ] | ['Maturity-onset diabetes of the young, type 3'] |
| NM_003494.3 (DYSF):c.1285-2A>G | 786200897 | DYSF | [ ] | ['CAGCYAGAAGA CACAGGGAGGGG', 'ACAGCYAGAAGA CACAGGGAGGG', 'CACAGCYAGAAG ACACAGGGAGG'] | ['Limb-girdle muscular dystrophy, type 2B'] |
| NM_005055.4 (RAPSN):c.-210A>G | 786200905 | RAPSN | [ ] | [ ] | ['MYASTHENIC SYNDROME, CONGENITAL, 11, ASSOCIATED WITH ACETYLCHOLINE RECEPTOR DEFICIENCY'] |
| NM_000276.3 (OCRL):c.1436A>G (p.Tyr479Cys) | 137853262 | OCRL | [ ] | [ ] | ['Dent disease 2'] |
| NM_004463.2 (FGD1):c.1396A>G (p.Met466Val) | 137853267 | FGD1 | [ ] | [ ] | ['Aarskog syndrome'] |
| NM_153252.4 (BRWD3):c.4786A>G (p.Lys1596Glu) | 137853272 | BRWD3 | [ ] | [ ] | ['Mental retardation, X-linked 93'] |
| NM_206933.2 (USH2A):c.7595-2144A>G | 786200928 | USH2A | [ ] | ['CTCTTAYCTTGG GAAAGGAGAGG'] | ['Usher syndrome, type 2A'] |
| NM_000362.4 (TIMP3):c.572A>G (p.Tyr191Cys) | 137853299 | — | ['TGCAGYA GCCGCCCT TCTGCCGG'] | ['TGCAGYAGCCG CCCTTCTGCCGG'] | ['Sorsby fundus dystrophy'] |
| NM_006785.3 (MALT1):c.1019-2A>G | 786200953 | MALT1 | ['CGCYTTG AAAAAAA AAGAAAG GG'] | ['CGCYTTGAAAA AAAAAGAAAGGG', 'TCGCYTTGAAAA AAAAAGAAAGG'] | ['Combined immunodeficiency'] |
| NM_003639.4 (IKBKG):c.1259A>G (p.Ter420Trp) | 137853321 | IKBKG | [ ] | [ ] | ['Incontinentia pigmenti syndrome', 'Ectodermal dysplasia, anhidrotic, with immunodeficiency, osteopetrosis, and lymphedema'] |
| NM_003639.4 (IKBKG):c.1219A>G (p.Met407Val) | 137853322 | IKBKG | [ ] | ['CCAYATCAGGG GCCTGATACTGG'] | ['Incontinentia pigmenti syndrome'] |
| NM_001014797.2 (KCNMA1):c.1301A>G (p.Asp434Gly) | 137853333 | KCNMA1 | [ ] | [ ] | ['Generalized epilepsy and paroxysmal dyskinesia'] |
| NM_016218.2 (POLK):c.1679A>T (p.Glu560Val) | 757103131 | POLK | [ ] | [ ] | ['Malignant tumor of prostate'] |
| NM_003000.2 (SDHB):c.541-2A>G | 786201161 | SDHB | [ ] | [ ] | ['Hereditary cancer-predisposing syndrome'] |
| NM_032383.4 (HPS3):c.2482-2A>G | 397507168 | — | [ ] | [ ] | ['Hermansky-Pudlak syndrome 3'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000060.3 (BTD):c.968A>G (p.His323Arg) | 397507176 | BTD | [ ] | [ ] | ['Biotinidase deficiency', 'not provided'] |
| NM_004315.4 (ASAH1):c.155A>G (p.Tyr52Cys) | 137853595 | ASAH1 | [ ] | [ ] | ['Farber lipogranulomatosis'] |
| NM_004315.4 (ASAH1):c.1006A>G (p.Asn336Asp) | 137853596 | ASAH1 | [ ] | [ ] | ['Farber lipogranulomatosis'] |
| NM_000059.3 (BRCA2):c.1799A>G (p.Tyr600Cys) | 397507276 | BRCA2 | [ ] | [ ] | ['Breast-ovarian cancer, familial 2'] |
| NM_022912.2 (REEP1):c.183-2A>G | 387906264 | REEP1 | [ ] | [ ] | ['Spastic paraplegia 31, autosomal dominant'] |
| NM_000022.2 (ADA):c.219-2A>G | 387906267 | ADA | [ ] | ['CCCCYGGGAAG GGAAGAAAGGGG', 'GCCCCYGGGAAG GGAAGAAAGGG', 'AGCCCCYGGGAA GGGAAGAAAGG'] | ['Severe combined immunodeficiency due to ADA deficiency'] |
| NM_018249.5 (CDK5RAP2):c.4005-15A>G | 387906274 | CDK5RAP2 | [ ] | [ ] | ['Primary autosomal recessive microcephaly 3'] |
| NM_032119.3 (ADGRV1):c.14973-2A>G | 371981035 | ADGRV1 | [ ] | [ ] | ['Usher syndrome, type 2C'] |
| NM_020366.3 (RPGRIP1):c.3341A>G (p.Asp1114Gly) | 17103671 | RPGRIP1 | [ ] | [ ] | ['Leber congenital amaurosis 6', 'not specified'] |
| NM_000492.3 (CFTR):c.3717+4A>G | 387906362 | CFTR | [ ] | ['TCAAATCYCACC CTCTGGCCAGG'] | ['Cystic fibrosis'] |
| NM_000492.3 (CFTR):c.273+4A>G | 387906374 | CFTR | [ ] | [ ] | ['Cystic fibrosis'] |
| NM_002769.4 (PRSS1):c.65A>G (p.Asp22Gly) | 397507442 | — | [ ] | ['CTTGYCATCATC ATCAAAGGGGG', 'TCTTGYCATCATC ATCAAAGGGG', 'ATCTTGYCATCA TCATCAAAGGG', 'GATCTTGYCATC ATCATCAAAGG'] | ['Hereditary pancreatitis'] |
| NM_004006.2 (DMD):c.4675-2A>G | 794727575 | DMD | [ ] | [ ] | ['Duchenne muscular dystrophy', 'Becker muscular dystrophy'] |
| NM_000132.3 (F8):c.1418A>G (p.Tyr473Cys) | 387906444 | F8 | [ ] | [ ] | ['Hereditary factor VIII deficiency disease'] |
| NM_004333.4 (BRAF):c.2126A>G (p.Gln709Arg) | 397507486 | BRAF | [ ] | [ ] | ['Rasopathy'] |
| NM_002834.3 (PTPN11):c.124A>G (p.Thr42Ala) | 397507501 | PTPN11 | [ ] | [ ] | ['Noonan syndrome', 'Noonan syndrome 1', 'Rasopathy', 'not provided'] |
| NM_000834.3 (GRIN2B):c.1238A>G (p.Glu413Gly) | 527236034 | GRIN2B | [ ] | [ ] | ['Mental retardation, autosomal dominant 6'] |
| NM_004830.3 (MED23):c.3638A>G (p.His1213Arg) | 527236035 | MED23 | [ ] | [ ] | ['Mental retardation, autosomal recessive 18'] |
| NM_002834.3 (PTPN11):c.844A>G (p.Ile282Val) | 397507529 | PTPN11 | [ ] | [ ] | ['Noonan syndrome 1', 'Rasopathy', 'not provided'] |
| NM_000406.2 (GNRHR):c.851A>G (p.Tyr284Cys) | 28933074 | GNRHR | [ ] | [ ] | [ ] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_002834.3 (PTPN11):c.1510A>G (p.Met504Val) | 397507547 | PTPN11 | [ ] | [ ] | ['Noonan syndrome', 'Noonan syndrome 1', 'Rasopathy', 'not provided'] |
| NM_004629.1 (FANCG):c.925-2A>G | 397507561 | FANCG | [ ] | [ ] | ['Fanconi anemia, complementation group G'] |
| NM_000492.3 (CFTR):c.3140-26A>G | 76151804 | CFTR | [ ] | [ ] | ['Cystic fibrosis'] |
| NM_024598.3 (USB1):c.502A>G (p.Arg168Gly) | 137853971 | USB1 | [ ] | ['CCACCYGGTTTT CTCTTGATTGG'] | ['Poikiloderma with neutropenia'] |
| NM_000067.2 (CA2):c.754A>G (p.Asn252Asp) | 2228063 | CA2 | [ ] | ['TGTYCTTCAGTG GCTGAGCTGGG', 'CTGTYCTTCAGT GGCTGAGCTGG'] | [ ] |
| NM_000138.4 (FBN1):c.5096A>G (p.Tyr1699Cys) | 387906622 | FBN1 | [ ] | [ ] | ['Geleophysic dysplasia 2'] |
| NM_001194958.2 (KCNJ18):c.1097A>G (p.Lys366Arg) | 527236159 | KCNJ18 | [ ] | [ ] | ['Thyrotoxic periodic paralysis', 'Thyrotoxic periodic paralysis 2'] |
| NM_000138.4 (FBN1):c.5087A>G (p.Tyr1696Cys) | 387906625 | FBN1 | [ ] | [ ] | ['Geleophysic dysplasia 2'] |
| NM_000138.4 (FBN1):c.5099A>G (p.Tyr1700Cys) | 387906626 | FBN1 | [ ] | [ ] | [ ] |
| NM_001244710.1 (GFPT1):c.43A>G (p.Thr15Ala) | 387906638 | GFPT1 | [ ] | [ ] | ['Congenital myasthenic syndrome with tubular aggregates 1'] |
| NM_002292.3 (LAMB2):c.440A>G (p.His147Arg) | 387906644 | LAMB2 | [ ] | [ ] | ['Nephrotic syndrome, type 5, with or without ocular abnormalities'] |
| NM_005188.3 (CBL):c.1112A>G (p.Tyr371Cys) | 387906666 | CBL | [ ] | [ ] | [ ] |
| NM_000313.3 (PROS1):c.701A>G (p.Tyr234Cys) | 387906675 | PROS1 | ['GATTAYA TCTGTAGC CTTCGGGG', 'AGATTAY ATCTGTAG CCTTCGGG', 'GAGATTA YATCTGTA GCCTTCGG'] | ['GATTAYATCTGT AGCCTTCGGGG', 'AGATTAYATCTG TAGCCTTCGGG', 'GAGATTAYATCT GTAGCCTTCGG'] | ['Thrombophilia due to protein S deficiency, autosomal recessive'] |
| NM_032018.6 (SPRTN):c.350A>G (p.Tyr117Cys) | 527236213 | SPRTN | [ ] | [ ] | ['Ruijs-aalfs syndrome'] |
| NM_022464.4 (SIL1):c.645+2T>C | 548535414 | SIL1 | [ ] | [ ] | ['Marinesco-Sj\xc3\xb6gren syndrome'] |
| NM_001040142.1 (SCN2A):c.4419A>G (p.Ile1473Met) | 387906685 | SCN2A | [ ] | [ ] | ['Early infantile epileptic encephalopathy 11'] |
| NM_001040142.1 (SCN2A):c.754A>G (p.Met252Val) | 387906687 | SCN2A | [ ] | [ ] | ['Benign familial neonatal-infantile seizures'] |
| m.10450A>G | 387906731 | MT-TR | [ ] | [ ] | ['Mitochondrial encephalomyopathy'] |
| m.5816A>G | 387906732 | MT-TC | [ ] | [ ] | [ ] |
| m.608A>G | 387906735 | MT-TF | ['TTCAGYG TATTGCTT TGAGGAGG'] | ['TTCAGYGTATTG CTTTGAGGAGG'] | [ ] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_001376.4 (DYNC1H1):c.917A>G (p.His306Arg) | 387906738 | DYNC1H1 | [ ] | [ ] | ['Charcot-Marie-Tooth disease, axonal, type 2O', 'Charcot-Marie-Tooth disease', 'Spinal muscular atrophy, lower extremity predominant 1, autosomal dominant'] |
| NM_001376.4 (DYNC1H1):c.2011A>G (p.Lys671Glu) | 387906742 | DYNC1H1 | [ ] | [ ] | ['Spinal muscular atrophy, lower extremity predominant 1, autosomal dominant'] |
| NM_001376.4 (DYNC1H1):c.2909A>G (p.Tyr970Cys) | 387906743 | DYNC1H1 | [ ] | ['ATTCAAGYAGAT TACCTGATTGG'] | ['Spinal muscular atrophy, lower extremity predominant 1, autosomal dominant'] |
| NM_001354.5 (AKR1C2):c.235A>G (p.Ile79Val) | 387906750 | AKR1C2 | [ ] | [ ] | ['46,XY sex reversal 8'] |
| NM_007315.3 (STAT1):c.604A>G (p.Met202Val) | 387906762 | STAT1 | [ ] | [ ] | ['Immunodeficiency 31C'] |
| NM_007315.3 (STAT1):c.494A>G (p.Asp165Gly) | 387906764 | STAT1 | [ ] | [ ] | ['Immunodeficiency 31C'] |
| NM_007315.3 (STAT1):c.862A>G (p.Thr288Ala) | 387906765 | STAT1 | [ ] | [ ] | ['Immunodeficiency 31C'] |
| NM_002052.4 (GATA4):c.928A>G (p.Met310Val) | 387906772 | GATA4 | [ ] | ['TCCGCAYTGCAA GAGGCCTGGGG', 'TTCCGCAYTGCA AGAGGCCTGGG'] | ['Atrial septal defect 2'] |
| NM_021615.4 (CHST6):c.329A>G (p.Tyr110Cys) | 72547544 | CHST6 | [ ] | [ ] | ['Macular corneal dystrophy Type I'] |
| NM_000209.3 (PDX1):c.533A>G (p.Glu178Gly) | 387906777 | PDX1 | [ ] | [ ] | ['Pancreatic agenesis, congenital'] |
| NM_000890.3 (KCNJ5):c.472A>G (p.Thr158Ala) | 387906778 | KCNJ5 | [ ] | [ ] | ['Andersen Tawil syndrome', 'Familial hyperaldosteronism type 3'] |
| NM_001184.3 (ATR):c.6431A>G (p.Gln2144Arg) | 387906797 | ATR | [ ] | [ ] | ['Cutaneous telangiectasia and cancer syndrome, familial'] |
| NM_000382.2 (ALDH3A2):c.1157A>G (p.Asn386Ser) | 72547575 | ALDH3A2 | [ ] | [ ] | ['Sj\xc3\xb6gren-Larsson syndrome'] |
| NM_001005862.2 (ERBB2):c.2480A>G (p.Asn827Ser) | 28933370 | ERBB2 | [ ] | [ ] | ['Neoplasm of ovary'] |
| NM_006194.3 (PAX9):c.271A>G (p.Lys91Glu) | 28933373 | PAX9 | [ ] | [ ] | ['Tooth agenesis, selective, 3'] |
| NM_001083116.1 (PRF1):c.755A>G (p.Asn252Ser) | 28933375 | PRF1 | [ ] | [ ] | ['Hemophagocytic lymphohistiocytosis, familial, 2', 'Malignant lymphoma, non-Hodgkin'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_005257.5 (GATA6):c.1354A>G (p.Thr452Ala) | 387906817 | GATA6 | [ ] | [ ] | ['Pancreatic agenesis and congenital heart disease'] |
| NM_000414.3 (HSD17B4):c.650A>G (p.Tyr217Cys) | 387906825 | HSD17B4 | [ ] | ['TGCCACAYACTC TGGCTTCAGGG'] | ['Gonadal dysgenesis with auditory dysfunction, autosomal recessive inheritance'] |
| NM_004153.3 (ORC1):c.380A>G (p.Glu127Gly) | 387906826 | ORC1 | [ ] | [ ] | ['Meier-Gorlin syndrome 1'] |
| NM_002552.4 (ORC4):c.521A>G (p.Tyr174Cys) | 387906847 | ORC4 | [ ] | [ ] | ['Meier-Gorlin syndrome 2'] |
| NM_004544.3 (NDUFA10):c.1A>G (p.Met1Val) | 387906872 | NDUFA10 | [ ] | [ ] | ['Leigh syndrome due to mitochondrial complex I deficiency'] |
| NM_004544.3 (NDUFA10):c.425A>G (p.Gln142Arg) | 387906873 | NDUFA10 | [ ] | [ ] | ['Leigh syndrome due to mitochondrial complex I deficiency'] |
| NM_006796.2 (AFG3L2):c.1847A>G (p.Tyr616Cys) | 387906889 | AFG3L2 | ['GTAYAGA GGTATTGT TCTTTTGG'] | ['GTAYAGAGGTA TTGTTCTTTTGG'] | ['Spastic ataxia 5, autosomal recessive'] |
| NM_006587.3 (CORIN):c.949A>G (p.Lys317Glu) | 387906894 | CORIN | [ ] | [ ] | ['Preeclampsia/ eclampsia 5'] |
| NM_006587.3 (CORIN):c.1414A>G (p.Ser472Gly) | 387906895 | CORIN | [ ] | ['GGATAACYTGTA CTGTTGTAGGG'] | ['Preeclampsia/ eclampsia 5'] |
| NM_015560.2 (OPA1):c.1294A>G (p.Ile432Val) | 387906899 | OPA1 | [ ] | [ ] | ['Optic Atrophy Type 1'] |
| NM_021625.4 (TRPV4):c.590A>G (p.Lys197Arg) | 387906903 | TRPV4 | [ ] | [ ] | ['Metatrophic dysplasia'] |
| NM_021625.4 (TRPV4):c.826A>G (p.Lys276Glu) | 387906907 | TRPV4 | [ ] | [ ] | ['Metatrophic dysplasia'] |
| NM_024022.2 (TMPRSS3):c.308A>G (p.Asp103Gly) | 387906915 | TMPRSS3 | [ ] | [ ] | ['Deafness, autosomal recessive 8'] |
| NM_019109.4 (ALG1):c.1129A>G (p.Met377Val) | 387906925 | ALG1 | [ ] | [ ] | ['Congenital disorder of glycosylation type 1K'] |
| NM_006886.3 (ATP5E):c.35A>G (p.Tyr12Cys) | 387906929 | — | [ ] | [ ] | ['Nuclearly-encoded mitochondrial complex V (ATP synthase) deficiency 3'] |
| NM_032578.3 (MYPN):c.59A>G (p.Tyr20Cys) | 140148105 | MYPN | [ ] | [ ] | ['Primary dilated cardiomyopathy', 'Cardiomyopathy', 'Dilated cardiomyopathy 1KK', 'Familial hypertrophic cardiomyopathy 22', 'not provided'] |
| NM_016013.3 (NDUFAF1):c.758A>G (p.Lys253Arg) | 387906957 | NDUFAF1 | [ ] | ['ACCYTGACCTCC TGCCAGTAGGG', 'TACCYTGACCTC CTGCCAGTAGG'] | ['Mitochondrial complex I deficiency'] |
| NM_032580.3 (HES7):c.172A>G (p.Ile58Val) | 387906979 | HES7 | [ ] | [ ] | ['Spondylocostal dysostosis 5'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_024700.3 (SNIP1):c.1097A>G (p.Glu366Gly) | 387906986 | SNIP1 | [ ] | [ ] | ['Psychomotor retardation, epilepsy, and craniofacial dysmorphism'] |
| NM_016952.4 (CDON):c.2368A>G (p.Thr790Ala) | 387906997 | CDON | [ ] | [ ] | ['Holoprosencephaly 11'] |
| NM_031427.3 (DNAL1):c.449A>G (p.Asn150Ser) | 387907021 | DNAL1 | ['AGGGAYT GCCTACAA ACACCAGG'] | ['AGGGAYTGCCT ACAAACACCAGG'] | ['Kartagener syndrome', 'Ciliary dyskinesia, primary, 16'] |
| NM_020320.3 (RARS2):c.1024A>G (p.Met342Val) | 387907048 | RARS2 | [ ] | [ ] | ['Pontocerebellar hypoplasia type 6'] |
| NM_000138.4 (FBN1):c.6431A>G (p.Asn2144Ser) | 137854461 | FBN1 | [ ] | [ ] | ['Marfan syndrome'] |
| NM_000138.4 (FBN1):c.2261A>G (p.Tyr754Cys) | 137854479 | FBN1 | [ ] | [ ] | ['Marfan syndrome'] |
| NM_212482.1 (FN1):c.2918A>G (p.Tyr973Cys) | 137854488 | FN1 | ['GAAGTAA YAGGTGAC CCCAGGGG'] | ['GAAGTAAYAGG TGACCCCAGGGG'] | ['Glomerulopathy with fibronectin deposits 2'] |
| NM_198994.2 (TGM6):c.980A>G (p.Asp327Gly) | 387907098 | TGM6 | [ ] | [ ] | ['Spinocerebellar ataxia 35'] |
| NM_001363.4 (DKC1):c.1069A>G (p.Thr357Ala) | 137854492 | DKC1 | ['GCAGGYA GAGATGAC CGCTGTGG'] | ['GCAGGYAGAGA TGACCGCTGTGG'] | ['Dyskeratosis congenita X-linked'] |
| NM_052873.2 (IFT43):c.1A>G (p.Met1Val) | 387907107 | IFT43 | [ ] | [ ] | ['Cranioectodermal dysplasia 3'] |
| NM_201269.2 (ZNF644):c.2014A>G (p.Ser672Gly) | 387907109 | ZNF644 | [ ] | [ ] | ['Myopia 21, autosomal dominant'] |
| NM_018699.3 (PRDM5):c.320A>G (p.Tyr107Cys) | 387907111 | PRDM5 | [ ] | [ ] | ['Brittle cornea syndrome 2'] |
| NM_000132.3 (F8):c.5822A>G (p.Asn1941Ser) | 28933682 | F8 | [ ] | ['TAGCCAYTGATT GCTGGAGAAGG'] | ['Hereditary factor VIII deficiency disease'] |
| NM_016464.4 (TMEM138):c.287A>G (p.His96Arg) | 387907132 | TMEM138 | ['GACAYGA AGGGAGAT GCTGAGGG'] | ['GACAYGAAGGG AGATGCTGAGGG', 'AGACAYGAAGGG AGATGCTGAGG'] | ['Joubert syndrome 16'] |
| NM_016464.4 (TMEM138):c.389A>G (p.Tyr130Cys) | 387907135 | TMEM138 | [ ] | ['CAGYACAACAC TGCTGCTGTGGG', 'GCAGYACAACAC TGCTGCTGTGG'] | ['Joubert syndrome 16'] |
| NM_177965.3 (C8orf37):c.545A>G (p.Gln182Arg) | 387907137 | C8orf37 | [ ] | [ ] | ['Retinitis pigmentosa 64'] |
| NM_001077488.3 (GNAS):c.1A>G (p.Met1Val) | 137854530 | GNAS | [ ] | ['GCCCAYGGCGG CGGCGGCGGCGG'] | ['Pseudohypopara- thyroidism type 1A'] |
| NM_006920.4 (SCN1A):c.2557-2A>G | 727504140 | SCN1A | [ ] | [ ] | ['Severe myoclonic epilepsy in infancy', 'Generalized epilepsy with febrile seizures plus, type 2'] |
| NM_000308.2 (CTSA):c.200A>G (p.Gln67Arg) | 137854541 | CTSA | [ ] | [ ] | ['Combined deficiency of sialidase AND beta galactosidase'] |
| NM_000308.2 (CTSA):c.1238A>G (p.Tyr413Cys) | 137854543 | CTSA | [ ] | [ ] | ['Combined deficiency of sialidase AND beta galactosidase'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_000308.2 (CTSA):c.1411A>G (p.Lys471Glu) | 137854549 | CTSA | [ ] | [ ] | ['Galactosialidosis, late infantile'] |
| NM_000267.3 (NF1):c.4267A>G (p.Lys1423Glu) | 137854550 | NF1 | [ ] | [ ] | ['Neurofibromatosis, type 1'] |
| NM_000267.3 (NF1):c.1466A>G (p.Tyr489Cys) | 137854557 | NF1 | ['ACTTAYAGCTTCTTGTCTCCAGG'] | ['ACTTAYAGCTTCTTGTCTCCAGG'] | ['Neurofibromatosis, type 1'] |
| NM_018105.2 (THAP1):c.70A>G (p.Lys24Glu) | 387907176 | THAP1 | [ ] | ['CCTCACTYGTGGAAAGAAACGGG'] | ['Dystonia 6, torsion'] |
| NM_000492.3 (CFTR):c.1393-2A>G | 397508201 | CFTR | [ ] | [ ] | ['Cystic fibrosis'] |
| NM_001172646.1 (PLCB4):c.986A>G (p.Asn329Ser) | 387907179 | PLCB4 | [ ] | [ ] | ['Auriculocondylar syndrome 2'] |
| NM_005850.4 (SF3B4):c.1A>G (p.Met1Val) | 387907185 | SF3B4 | [ ] | [ ] | ['Nager syndrome'] |
| NM_014714.3 (IFT140):c.932A>G (p.Tyr311Cys) | 387907193 | IFT140 | [ ] | [ ] | ['Renal dysplasia, retinal pigmentary dystrophy, cerebellar ataxia and skeletal dysplasia'] |
| NM_005006.6 (NDUFS1):c.1783A>G (p.Thr595Ala) | 387907199 | NDUFS1 | [ ] | [ ] | ['Mitochondrial complex I deficiency'] |
| NM_000397.3 (CYBB):c.1499A>G (p.Asp500Gly) | 137854593 | CYBB | [ ] | ['TCACAYCTTTCTCCTCATCATGG'] | ['Chronic granulomatous disease, X-linked', 'not provided'] |
| NM_033360.3 (KRAS):c.439A>G (p.Lys147Glu) | 387907206 | KRAS | [ ] | [ ] | ['Cardiofaciocutaneous syndrome 2'] |
| NM_000335.4 (SCN5A):c.5381A>G (p.Tyr1794Cys) | 137854614 | SCN5A | [ ] | [ ] | ['Long QT syndrome 3', 'Congenital long QT syndrome'] |
| NM_000076.2 (CDKN1C):c.832A>G (p.Lys278Glu) | 387907226 | CDKN1C | [ ] | ['CGCTYGGCGAAGAAATCTGCGG', 'GCGCTYGGCGAAGAAATCTGCGG'] | ['Intrauterine growth retardation, metaphyseal dysplasia, adrenal hypoplasia congenita, and genital anomalies'] |
| NM_022912.2 (REEP1):c.304-2A>G | 387907242 | REEP1 | [ ] | ['TCCYGTCAAAGGAAAAACAGAGG'] | ['Distal hereditary motor neuronopathy type 5B'] |
| NM_198253.2 (TERT):c.2705A>G (p.Lys902Arg) | 387907250 | TERT | [ ] | [ ] | ['PULMONARY FIBROSIS AND/OR BONE MARROW FAILURE, TELOMERE-RELATED, 1'] |
| NM_005349.3 (RBPJ):c.188A>G (p.Glu63Gly) | 387907270 | RBPJ | [ ] | [ ] | ['Adams-Oliver syndrome 3'] |
| NM_005349.3 (RBPJ):c.505A>G (p.Lys169Glu) | 387907271 | RBPJ | [ ] | [ ] | ['Adams-Oliver syndrome 3'] |
| NM_022787.3 (NMNAT1):c.817A>G (p.Asn273Asp) | 387907291 | NMNAT1 | [ ] | ['TGTYTCTCTGCAAAGGGGCCAGG'] | ['Leber congenital amaurosis 9'] |
| NM_000492.3 (CFTR):c.1A>G (p.Met1Val) | 397508328 | CFTR | ['TGCAYGGTCTCTCGGGCGCTGGG'] | ['GCAYGGTCTCTCGGGCGCTGGGG', 'TGCAYGGTCTCTCGGGCGCTGGG', 'CTGCAYGGTCTCTCGGGCGCTGG'] | ['Cystic fibrosis'] |

TABLE 8-continued

Human gene mutations that may be corrected by changing a guanine (G) to an adenine (A). The gene name, gene symbol, and dbSNP database reference number (RS#) are indicated. Also indicated are exemplary protospacers with their PAM sequences (gRNAs and gRNAall) and the base to be edited e.g., a C, indicated by a "Y". The "gRNAs" sequences, from top to bottom, correspond to SEQ ID NOs: 3434-3601. The "gRNA all" sequences, from top to bottom, correspond to SEQ ID NOs: 3602-4266.

| Name | RS# (dbSNP) | GeneSymbol | gRNAs | gRNAall | Phenotypes |
|---|---|---|---|---|---|
| NM_020921.3 (NIN):c.5126A>G (p.Asn1709Ser) | 387907308 | NIN | [ ] | [ ] | ['Seckel syndrome 7'] |
| NM_021629.3 (GNB4):c.265A>G (p.Lys89Glu) | 387907341 | GNB4 | [ ] | [ ] | ['Charcot-Marie-Tooth disease, dominant intermediate F'] |
| NM_000355.3 (TCN2):c.580+624A>T | 372866837 | TCN2 | [ ] | [ ] | [ ] |
| NM_032415.5 (CARD11):c.401A>G (p.Glu134Gly) | 387907351 | CARD11 | [ ] | [ ] | ['B-CELL EXPANSION WITH NFKB AND T-CELL ANERGY'] |
| NM_005430.3 (WNT1):c.624+4A>G | 387907354 | WNT1 | [ ] | [ ] | ['Osteogenesis imperfecta type 15'] |
| NM_207352.3 (CYP4V2):c.367A>G (p.Met123Val) | 149684063 | CYP4V2 | [ ] | [ ] | ['Bietti crystalline corneoretinal dystrophy', 'not provided'] |
| NM_031885.3 (BBS2):c.472-2A>G | 137854887 | BBS2 | [ ] | [ ] | ['Bardet-Biedl syndrome 2'] |
| NM_015268.3(DNAJC13):c.2564A>G (p.Asn855Ser) | 387907571 | DNAJC13 | [ ] | [ ] | ['Parkinson disease, late-onset', 'Essential tremor', 'PARKINSON DISEASE 21'] |
| NM_001287.5 (CLCN7):c.296A>G (p.Tyr99Cys) | 387907576 | CLCN7 | [ ] | ['TGTCAYAGTCCAAGCTCTGCAGG'] | ['Osteopetrosis autosomal dominant type 2', 'Osteopetrosis autosomal recessive 4'] |

REFERENCES

1. Humbert O, Davis L, Maizels N. Targeted gene therapies: tools, applications, optimization. *Crit Rev Biochem Mol.* 2012; 47(3):264-81. PMID: 22530743.
2. Perez-Pinera P, Ousterout D G, Gersbach C A. Advances in targeted genome editing. *Curr Opin Chem Biol.* 2012; 16(3-4):268-77. PMID: 22819644.
3. Urnov F D, Rebar E J, Holmes M C, Zhang H S, Gregory P D. Genome editing with engineered zinc finger nucleases. *Nat Rev Genet.* 2010; 11(9):636-46. PMID: 20717154.
4. Joung J K, Sander J D. TALENs: a widely applicable technology for targeted genome editing. *Nat Rev Mol Cell Biol.* 2013; 14(1):49-55. PMID: 23169466.
5. Charpentier E, Doudna J A. Biotechnology: Rewriting a genome. *Nature.* 2013; 495, (7439):50-1. PMID: 23467164.
6. Pan Y, Xia L, Li A S, Zhang X, Sirois P, Zhang J, Li K. Biological and biomedical applications of engineered nucleases. *Mol Biotechnol.* 2013; 55(1):54-62. PMID: 23089945.
7. De Souza, N. Primer: genome editing with engineered nucleases. *Nat Methods.* 2012; 9(1):27. PMID: 22312638.
8. Santiago Y, Chan E, Liu P Q, Orlando S, Zhang L, Urnov F D, Holmes M C, Guschin D, Waite A, Miller J C, Rebar E J, Gregory P D, Klug A, Collingwood T N. Targeted gene knockout in mammalian cells by using engineered zinc-finger nucleases. *Proc Natl Acad Sci USA.* 2008; 105(15):5809-14. PMID: 18359850.
9. Cargill M, Altshuler D, Ireland J, Sklar P, Ardlie K, Patil N, Lane C R, Lim E P, Kalyanaraman N, Nemesh J, Ziaugra L, Friedland L, Rolfe A, Warrington J, Lipshutz R, Daley G Q, Lander E S. Characterization of single-nucleotide polymorphisms in coding regions of human genes. *Nat Genet.* 1999; 22(3):231-8. PMID: 10391209.
10. Jansen R, van Embden J D, Gaastra W, Schouls L M. Identification of genes that are associated with DNA repeats in prokaryotes. *Mol Microbiol.* 2002; 43(6):1565-75. PMID: 11952905.
11. Mali P, Esvelt K M, Church G M. Cas9 as a versatile tool for engineering biology. *Nat Methods.* 2013; 10(10):957-63. PMID: 24076990.
12. Jore M M, Lundgren M, van Duijin E, Bultema J B, Westra E R, Waghmare S P, Wiedenheft B, Pul U, Wurm R, Wagner R, Beijer M R, Barendregt A, Shou K, Snijders A P, Dickman M J, Doudna J A, Boekema E J, Heck A J, van der Oost J, Brouns S J. Structural basis for CRISPR RNA-guided DNA recognition by Cascade. *Nat Struct Mol Biol.* 2011; 18(5):529-36. PMID: 21460843.
13. Horvath P, Barrangou R. CRISPR/Cas, the immune system of bacteria and archaea. *Science.* 2010; 327(5962):167-70. PMID: 20056882.
14. Wiedenheft B, Sternberg S H, Doudna J A. RNA-guided genetic silencing systems in bacteria and archaea. *Nature.* 2012; 482(7385):331-8. PMID: 22337052.

15. Gasiunas G, Siksnys V. RNA-dependent DNA endonuclease Cas9 of the CRISPR system: Holy Grail of genome editing? *Trends Microbiol.* 2013; 21(11):562-7. PMID: 24095303.
16. Qi L S, Larson M H, Gilbert L A, Doudna J A, Weissman J S, Arkin A P, Lim W A. Repurposing CRISPR as an RNA-guided platform for sequence-specific control of gene expression. *Cell.* 2013; 152(5):1173-83. PMID: 23452860.
17. Perez-Pinera P, Kocak D D, Vockley C M, Adler A F, Kabadi A M, Polstein L R, Thakore P I, Glass K A, Ousterout D G, Leong K W, Guilak F, Crawford G E, Reddy T E, Gersbach C A. RNA-guided gene activation by CRISPR-Cas9-based transcription factors. *Nat Methods.* 2013; 10(10):973-6. PMID: 23892895.
18. Mali P, Aach J, Stranges P B, Esvelt K M, Moosburner M, Kosuri S, Yang L, Church G M. CAS9 transcriptional activators for target specificity screening and paired nickases for cooperative genome engineering. *Nat Biotechnol.* 2013; 31(9):833-8. PMID: 23907171.
19. Gilbert L A, Larson M H, Morsut L, Liu Z, Brar G A, Torres S E, Stern-Ginossar N, Brandman O, Whitehead E H, Doudna J A, Lim W A, Weissman J S, Qi L S. CRISPR-mediated modular RNA-guided regulation of transcription in eukaryotes. *Cell.* 2013; 154(2):442-51. PMID: 23849981.
20. Larson M H, Gilbert L A, Wang X, Lim W A, Weissman J S, Qi L S. CRISPR interference (CRISPRi) for sequence-specific control of gene expression. *Nat Protoc.* 2013; 8(11):2180-96. PMID: 24136345.
21. Mali P, Yang L, Esvelt K M, Aach J, Guell M, DiCarlo J E, Norville J E, Church G M. RNA-guided human genome engineering via Cas9. *Science.* 2013; 339(6121): 823-6. PMID: 23287722.
22. Cole-Strauss A, Yoon K, Xiang Y, Byrne B C, Rice M C, Gryn J, Holloman W K, Kmiec E B. Correction of the mutation responsible for sickle cell anemia by an RNA-DNA oligonucleotide. *Science.* 1996; 273(5280):1386-9. PMID: 8703073.
23. Tagalakis A D, Owen J S, Simons J P. Lack of RNA-DNA oligonucleotide (chimeraplast) mutagenic activity in mouse embryos. *Mol Reprod Dev.* 2005; 71(2):140-4. PMID: 15791601.
24. Ray A, Langer M. Homologous recombination: ends as the means. *Trends Plant Sci.* 2002; 7(10):435-40. PMID 12399177.
25. Britt A B, May G D. Re-engineering plant gene targeting. *Trends Plant Sci.* 2003; 8(2):90-5. PMID: 12597876.
26. Vagner V, Ehrlich S D. Efficiency of homologous DNA recombination varies along the *Bacillus subtilis* chromosome. *J Bacteriol.* 1988; 170(9):3978-82. PMID: 3137211.
27. Saleh-Gohari N, Helleday T. Conservative homologous recombination preferentially repairs DNA double-strand breaks in the S phase of the cell cycle in human cells. *Nucleic Acids Res.* 2004; 32(12):3683-8. PMID: 15252152.
28. Lombardo A, Genovese P, Beausejour C M, Colleoni S, Lee Y L, Kim K A, Ando D, Urnov F D, Galli C, Gregory P D, Holmes M C, Naldini L. Gene editing in human stem cells using zinc finger nucleases and integrase-defective lentiviral vector delivery. *Nat Biotechnol.* 2007; 25(11): 1298-306. PMID: 17965707.
29. Conticello S G. The AID/APOBEC family of nucleic acid mutators. *Genome Biol.* 2008; 9(6):229. PMID: 18598372.
30. Reynaud C A, Aoufouchi S, Faili A, Weill J C. What role for AID: mutator, or assembler of the immunoglobulin mutasome? *Nat Immunol.* 2003; 4(7):631-8.
31. Bhagwat A S. DNA-cytosine deaminases: from antibody maturation to antiviral defense. *DNA Repair (Amst).* 2004; 3(1):85-9. PMID: 14697763.
32. Navaratnam N, Sarwar R. An overview of cytidine deaminases. *Int J Hematol.* 2006; 83(3):195-200. PMID: 16720547.
33. Holden L G, Prochnow C, Chang Y P, Bransteitter R, Chelico L, Sen U, Stevens R C, Goodman M F, Chen X S. Crystal structure of the anti-viral APOBEC3G catalytic domain and functional implications. *Nature.* 2008; 456 (7218):121-4. PMID: 18849968.
34. Chelico L, Pham P, Petruska J, Goodman M F. Biochemical basis of immunological and retroviral responses to DNA-targeted cytosine deamination by activation-induced cytidine deaminase and APOBEC3G. *J Biol Chem.* 2009; 284(41). 27761-5. PMID: 19684020.
35. Pham P, Bransteitter R, Goodman M F. Reward versus risk: DNA cytidine deaminases triggering immunity and disease. *Biochemistry.* 2005; 44(8):2703-15. PMID 15723516.
36. Chen X, Zaro J L, Shen W C. Fusion protein linkers: property, design and functionality. *Adv Drug Deliv Rev.* 2013; 65(10):1357-69. PMID: 23026637.
37. Lee J W, Soung Y H, Kim S Y, Lee H W, Park W S, Nam S W, Kim S H, Lee J Y, Yoo N J, Lee S H. PIK3CA gene is frequently mutated in breast carcinomas and hepatocellular carcinomas. *Oncogene.* 2005; 24(8):1477-80. PMID: 15608678.
38. Ikediobi O N, Davies H, Bignell G, Edkins S, Stevens C, O'Meara S, Santarius T, Avis T, Barthorpe S, Brackenbury L, Buck G, Butler A, Clements J, Cole J, Dicks E, Forbes S, Gray K, Halliday K, Harrison R, Hills K, Hinton J, Hunter C, Jenkinson A, Jones D, Kosmidou V, Lugg R, Menzies A, Mironenko T, Parker A, Perry J, Raine K, Richardson D, Shepherd R, Small A, Smith R, Solomon H, Stephens P, Teague J, Tofts C, Varian J, Webb T, West S, Widaa S, Yates A, Reinhold W, Weinstein J N, Stratton M R, Futreal P A, Wooster R. Mutation analysis of 24 known cancer genes in the NCI-60 cell line set. *Mol Cancer Ther.* 2006; 5(11):2606-12. PMID: 17088437.
39. Cox, D. B., Platt, R. J. & Zhang, F. Therapeutic genome editing: prospects and challenges. *Nature medicine* 21, 121-131, doi:10.1038/nm.3793 (2015).
40. Hilton, I. B. & Gersbach, C. A. Enabling functional genomics with genome engineering. *Genome research* 25, 1442-1455, doi:10.1101/gr.190124.115 (2015).
41. Sander, J. D. & Joung, J. K. CRISPR-Cas systems for editing, regulating and targeting genomes. *Nature biotechnology* 32, 347-355, doi:10.1038/nbt.2842 (2014).
42. Maruyama, T. et al. Increasing the efficiency of precise genome editing with CRISPR-Cas9 by inhibition of non-homologous end joining. *Nature biotechnology* 33, 538-542, doi:10.1038/nbt.3190 (2015).
43. Chu, V. T. et al. Increasing the efficiency of homology-directed repair for CRISPR-Cas9-induced precise gene editing in mammalian cells. *Nature biotechnology* 33, 543-548, doi:10.1038/nbt.3198 (2015).
44. Lin, S., Staahl, B. T., Alla, R. K. & Doudna, J. A. Enhanced homology-directed human genome engineering by controlled timing of CRISPR/Cas9 delivery. *eLife* 3, e04766, doi:10.7554/eLife.04766 (2014).
45. Cong, L. et al. Multiplex genome engineering using CRISPR/Cas systems. *Science* 339, 819-823, doi: 10.1126/science.1231143 (2013).

46. Rong, Z., Zhu, S., Xu, Y. & Fu, X. Homologous recombination in human embryonic stem cells using CRISPR/Cas9 nickase and a long DNA donor template. *Protein & cell* 5, 258-260, doi:10.1007/s13238-014-0032-5 (2014).
47. Jinek, M. et al. A Programmable Dual-RNA-Guided DNA Endonuclease in Adaptive Bacterial Immunity. *Science* 337, 816-821, doi:10.1126/science.1225829 (2012).
48. Harris, R. S., Petersen-Mahrt, S. K. & Neuberger, M. S. RNA Editing Enzyme APOBEC1 and Some of Its Homologs Can Act as DNA Mutators. *Molecular Cell* 10, 1247-1253 (2002).
49. Jinek, M. et al. Structures of Cas9 endonucleases reveal RNA-mediated conformational activation. *Science* 343, 1247997, doi:10.1126/science.1247997 (2014).
50. Schellenberger, V. et al. A recombinant polypeptide extends the in vivo half-life of peptides and proteins in a tunable manner. *Nature biotechnology* 27, 1186-1190, doi:10.1038/nbt.1588 (2009).
51. Saraconi, G., Severi, F., Sala, C., Mattiuz, G. & Conticello, S. G. The RNA editing enzyme APOBEC1 induces somatic mutations and a compatible mutational signature is present in esophageal adenocarcinomas. *Genome biology* 15, 417-(2014).
52. Anders, C., Niewoehner, O., Duerst, A. & Jinek, M. Structural basis of PAM-dependent target DNA recognition by the Cas9 endonuclease. *Nature* 513, 569-573, doi:10.1038/nature13579 (2014).
53. Cong, L. et al. Multiplex genome engineering using CRISPR/Cas systems. *Science* 339, 819-823 (2013).
54. Tsai, S. Q. et al. GUIDE-seq enables genome-wide profiling of off-target cleavage by CRISPR-Cas nucleases. *Nature biotechnology* 33, 187-197, doi:10.1038/nbt.3117 (2015).
55. Kunz, C., Saito, Y. & Schar, P. DNA Repair in mammalian cells: Mismatched repair: variations on a theme. *Cellular and molecular life sciences: CMLS* 66, 1021-1038, doi:10.1007/s00018-009-8739-9 (2009).
56. D., M. C. et al. Crystal structure of human uracil-DNA glycosylase in complex with a protein inhibitor: protein mimicry of DNA. *Cell* 82, 701-708 (1995).
57. Caldecott, K. W. Single-strand break repair and genetic disease. *Nature reviews. Genetics* 9, 619-631, doi:10.1038/nrg2380 (2008).
58. Fukui, K. DNA mismatch repair in eukaryotes and bacteria. *Journal of nucleic acids* 2010, doi:10.4061/2010/260512 (2010).
59. Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences* 109, E2579-E2586, doi:10.1073/pnas.1208507109 (2012).
60. Ran, F. A. et al. In vivo genome editing using *Staphylococcus aureus* Cas9. *Nature* 520, 186-191, doi:10.1038/nature14299 (2015).
61. Kuscu, C., Arslan, S., Singh, R., Thorpe, J. & Adli, M. Genome-wide analysis reveals characteristics of off-target sites bound by the Cas9 endonuclease. *Nature biotechnology* 32, 677-683, doi:10.1038/nbt.2916 (2014).
62. Wu, X. et al. Genome-wide binding of the CRISPR endonuclease Cas9 in mammalian cells. *Nature biotechnology* 32, 670-676, doi:10.1038/nbt.2889 (2014).
63. Beale, R. C. L. et al. Comparison of the Differential Context-dependence of DNA Deamination by APOBEC Enzymes: Correlation with Mutation Spectra in Vivo. *Journal of Molecular Biology* 337, 585-596, doi:10.1016/j.jmb.2004.01.046 (2004).
64. Kim, J., Basak, J. M. & Holtzman, D. M. The role of apolipoprotein E in Alzheimer's disease. *Neuron* 63, 287-303, doi:10.1016/j.neuron.2009.06.026 (2009).
65. Liu, C. C., Kanekiyo, T., Xu, H. & Bu, G. Apolipoprotein E and Alzheimer disease: risk, mechanisms and therapy. *Nature reviews. Neurology* 9, 106-118, doi:10.1038/nrneurol.2012.263 (2013).
66. Sjöblom, T. et al. The Consensus Coding Sequences of Human Breast and Colorectal Cancers. *Science* 314, 268-274, doi:10.1126/science.1133427 (2006).
67. Stephens, P. J. et al. The landscape of cancer genes and mutational processes in breast cancer. *Nature* 486, 400-404, doi:10.1038/nature11017 (2012).
68. Landrum, M. J. et al. ClinVar: public archive of interpretations of clinically relevant variants. *Nucleic Acids Research, doi:*10.1093/nar/gkv1222 (2015).
69. Slaymaker, I. M. et al. Rationally engineered Cas9 nucleases with improved specificity. *Science, doi:* 10.1126/science.aad5227 (2015).
70. Davis, K. M., Pattanayak, V., Thompson, D. B., Zuris, J. A. & Liu, D. R. Small molecule-triggered Cas9 protein with improved genome-editing specificity. *Nature chemical biology* 11, 316-318, doi:10.1038/nchembio.1793 (2015).
71. Zuris, J. A. et al. Cationic lipid-mediated delivery of proteins enables efficient protein-based genome editing in vitro and in vivo. *Nature biotechnology* 33, 73-80, doi:10.1038/nbt.3081 (2015).
72. Kleinstiver, B. P. et al. Engineered CRISPR-Cas9 nucleases with altered PAM specificities. *Nature* 523, 481-485, doi:10.1038/nature14592 (2015).
73. Pattanayak, V. et al. High-throughput profiling of off-target DNA cleavage reveals RNA-programmed Cas9 nuclease specificity. *Nature Biotechnology* 31, 839-843, doi:10.1038/nbt.2673 (2013).
74. Shcherbakova, D. M. & Verkhusha, V. V. Near-infrared fluorescent proteins for multicolor in vivo imaging. *Nature Methods* 10, 751-754, doi:10.1038/nmeth.2521 (2013).
75. Ran, F. A. et al. Genome engineering using the CRISPR-Cas9 system. *Nat. Protocols* 8, 2281-2308, doi:10.1038/nprot.2013.143 (2013).
76. Jiang, F. et al. Structures of a CRISPR-Cas9 R-loop complex primed for DNA cleavage. *Science, doi:*10.1126/science.aad8282 (2016).
77. Tsai, S. Q. et al. Dimeric CRISPR RNA-guided FokI nucleases for highly specific genome editing. *Nat Biotech* 32, 569-576, doi:10.1038/nbt.2908 (2014).
78. Lieber, M. R., Ma, Y., Pannicke, U. & Schwarz, K. Mechanism and regulation of human non-homologous DNA end-joining. *Nat Rev Mol Cell Biol* 4, 712-720 (2003).
79. Heller, R. C. & Marians, K. J. Replisome assembly and the direct restart of stalled replication forks. *Nat Rev Mol Cell Biol* 7, 932-943 (2006).
80. Pluciennik, A. et al. PCNA function in the activation and strand direction of MutLα endonuclease in mismatch repair. *Proceedings of the National Academy of Sciences of the United States of America* 107, 16066-16071, doi:10.1073/pnas.1010662107 (2010).
81. Seripa, D. et al. The missing ApoE allele. *Annals of human genetics* 71, 496-500, doi:10.1111/j.1469-1809.2006.00344.x (2007).
82. Kleinstiver, B. P. et al. High-fidelity CRISPR-Cas9 nucleases with no detectable genome-wide off-target effects. *Nature* 529, 490-495, doi:10.1038/nature16526 (2016).

83. Richardson, C. D., Ray, G. J., DeWitt, M. A., Curie, G. L. & Corn, J. E. Enhancing homology-directed genome editing by catalytically active and inactive CRISPR-Cas9 using asymmetric donor DNA. *Nat Biotech* 34, 339-344, doi:10.1038/nbt.3481 (2016).
84. Simonelli, V., Narciso, L., Dogliotti, E. & Fortini, P. Base excision repair intermediates are mutagenic in mammalian cells. *Nucleic acids research* 33, 4404-4411, doi: 10.1093/nar/gki749 (2005).
85. Barnes, D. E. & Lindahl, T. Repair and Genetic Consequences of Endogenous DNA Base Damage in Mammalian Cells. *Annual Review of Genetics* 38, 445-476, doi: doi:10.1146/annurev.genet.38.072902.092448 (2004).

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the invention encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11214780B2). An electronic copy of the "Sequence Listing" will also be available from the USPTO upon request and payment of the fee set forth in 37 CFR 1.19(b)(3).

What is claimed is:

1. A fusion protein comprising:
   (i) a Cpf1 domain, wherein the Cpf1 domain, when in conjunction with a bound guide RNA (gRNA), specifically binds to a target nucleic acid sequence;
   (ii) a cytidine deaminase domain, wherein the cytidine deaminase domain deaminates a cytosine base in a single-stranded portion of the target nucleic acid sequence when in conjunction with the Cpf1 domain and the gRNA; and
   (iii) a uracil glycosylase inhibitor (UGI) domain, wherein the UGI domain inhibits a uracil-DNA glycosylase.

2. The fusion protein of claim 1, wherein at least a portion of the target nucleic acid sequence is double-stranded.

3. The fusion protein of claim 1, wherein the Cpf1 domain is a catalytically inactive Cpf1 (dCpf1) domain.

4. The fusion protein of claim 3, wherein the guide RNA nucleic acid binds the single-stranded portion of the target nucleic acid sequence.

5. The fusion protein of claim 4, wherein the guide RNA nucleic acid is a single-stranded guide RNA.

6. The fusion protein of claim 1, wherein deamination of the cytosine base generates a uracil base.

7. The fusion protein of claim 6, wherein the UGI domain inhibits excision of the uracil base from the target nucleic acid sequence.

8. The fusion protein of claim 1, wherein the cytidine deaminase domain comprises an activation-induced deaminase (AID).

9. The fusion protein of claim 1, wherein the cytidine deaminase domain comprises a deaminase from the apolipoprotein B mRNA-editing complex (APOBEC) family deaminase.

10. The fusion protein of claim 9, wherein the APOBEC family deaminase is selected from the group consisting of apolipoprotein B mRNA-editing complex 1 (APOBEC1), apolipoprotein B mRNA-editing complex 2 (APOBEC2), apolipoprotein B mRNA-editing complex 3 (APOBEC3), apolipoprotein B mRNA-editing complex 3A (APOBEC3A), apolipoprotein B mRNA-editing complex 3B (APOBEC3B), apolipoprotein B mRNA-editing complex 3C (APOBEC3C), apolipoprotein B mRNA-editing complex 3D (APOBEC3D), apolipoprotein B mRNA-editing complex 3E (APOBEC3E), apolipoprotein B mRNA-editing complex 3F (APOBEC3F), apolipoprotein B mRNA-editing complex 3G (APOBEC3G), apolipoprotein B mRNA-editing complex 3H (APOBEC3H), and apolipoprotein B mRNA-editing complex 4 (APOBEC4).

11. A complex comprising the fusion protein of claim 1 and a guide RNA (gRNA).

12. A composition comprising the complex of claim 11 and the target nucleic acid sequence.

13. The composition of claim 12, wherein the target nucleic acid sequence comprises a target DNA sequence.

14. The fusion protein of claim 1, wherein the UGI domain comprises an amino acid sequence that is at least 85% identical to SEQ ID NO: 600.

15. The fusion protein of claim 1, wherein the UGI domain comprises the amino acid sequence of SEQ ID NO: 600.

16. The fusion protein of claim 1, wherein the Cpf1 domain comprises an amino acid sequence that is at least 90% identical to SEQ ID NO: 5807.

17. The fusion protein of claim 1, wherein the Cpf1 domain comprises the amino acid sequence of SEQ ID NO: 5807.

18. A method comprising contacting the fusion protein of claim 1 with a guide RNA and the target nucleic acid sequence.

19. The method of claim 18, wherein the guide RNA comprises a sequence of at least 10 contiguous nucleotides that are complementary to at least 10 contiguous nucleotides of the target nucleic acid sequence.

20. The method of claim 19, wherein the target nucleic acid sequence comprises a point mutation associated with a disease or disorder.

21. The method of claim 18, wherein the target nucleic acid sequence comprises an RNA sequence.

22. The method of claim 18, wherein the target nucleic acid sequence comprises a DNA sequence.

23. The method of claim 18, wherein the guide RNA comprises a sequence of at least 10 contiguous nucleotides that are complementary to at least 18-20 contiguous nucleotides of the target nucleic acid sequence.

* * * * *

UNITED STATES PATENT AND TRADEMARK OFFICE
CERTIFICATE OF CORRECTION

PATENT NO. : 11,214,780 B2
APPLICATION NO. : 15/960171
DATED : January 4, 2022
INVENTOR(S) : David R. Liu et al.

Page 1 of 1

It is certified that error appears in the above-identified patent and that said Letters Patent is hereby corrected as shown below:

In the Claims

In Claim 4, at Column 921, Line 18, the text:
"nucleic acid binds the single-stranded portion of the target"

Should be replaced with:
-- binds the single-stranded portion of the target --.

In Claim 5, at Column 921, Line 21, the text:
"nucleic acid is a single-stranded guide RNA"

Should be replaced with:
-- is a single-stranded guide RNA --.

In Claim 9, at Column 921, Lines 32-33, the text:
"apolipoprotein B mRNA-editing complex (APOBEC) family deaminase"

Should be replaced with:
-- apolipoprotein B mRNA-editing complex (APOBEC) family --.

Signed and Sealed this
Twenty-second Day of February, 2022

Drew Hirshfeld
*Performing the Functions and Duties of the
Under Secretary of Commerce for Intellectual Property and
Director of the United States Patent and Trademark Office*